US008518686B2

(12) United States Patent
Beck et al.

(10) Patent No.: US 8,518,686 B2
(45) Date of Patent: Aug. 27, 2013

(54) THREE-DIMENSIONAL STRUCTURE OF ISOPRENE SYNTHASE AND ITS USE THEREOF FOR GENERATING VARIANTS

(75) Inventors: Zachary Quinn Beck, Palo Alto, CA (US); Richard R. Bott, Burlingame, CA (US); Christopher Lee Rife, Redwood City, CA (US); Derek H. Wells, Palo Alto, CA (US); Jeffrey V. Miller, Menlo Park, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 170 days.

(21) Appl. No.: 12/765,825

(22) Filed: Apr. 22, 2010

(65) Prior Publication Data

US 2011/0076743 A1 Mar. 31, 2011

Related U.S. Application Data

(60) Provisional application No. 61/172,199, filed on Apr. 23, 2009, provisional application No. 61/255,831, filed on Oct. 28, 2009.

(51) Int. Cl.

| | |
|---|---|
| ***C12N 1/20*** | (2006.01) |
| ***C12N 9/88*** | (2006.01) |
| ***C12N 1/00*** | (2006.01) |
| ***C12N 15/00*** | (2006.01) |
| ***C12P 5/02*** | (2006.01) |
| ***C07H 21/04*** | (2006.01) |

(52) U.S. Cl.
USPC ... 435/252.33; 435/167; 435/232; 435/254.2; 435/254.21; 435/320.1; 435/471; 536/23.2

(58) Field of Classification Search
None
See application file for complete search history.

(56) References Cited

U.S. PATENT DOCUMENTS

| | | | | |
|---|---|---|---|---|
| 1,344,713 | A | 6/1920 | Peters | |
| 3,686,349 | A | 8/1972 | Schliebs et al. | |
| 4,570,029 | A | 2/1986 | Kulprathipanja et al. | |
| 4,647,344 | A | 3/1987 | Lindner et al. | |
| 4,683,195 | A | 7/1987 | Mullis et al. | |
| 4,683,202 | A | 7/1987 | Mullis | |
| 4,703,007 | A | 10/1987 | Mulholland et al. | |
| 4,846,872 | A | 7/1989 | Kamuro et al. | |
| 4,965,188 | A | 10/1990 | Mullis et al. | |
| 5,322,770 | A | 6/1994 | Gelfand | |
| 5,349,126 | A | 9/1994 | Chappell et al. | |
| 5,380,831 | A | 1/1995 | Adang et al. | |
| 5,436,391 | A | 7/1995 | Fujimoto et al. | |
| 5,545,816 | A | 8/1996 | Ausich et al. | |
| 5,849,970 | A | 12/1998 | Fall et al. | |
| 5,874,276 | A | 2/1999 | Fowler et al. | |
| 6,022,725 | A | 2/2000 | Fowler et al. | |
| 6,106,888 | A | 8/2000 | Dale et al. | |
| 6,176,176 | B1 | 1/2001 | Dale et al. | |
| 6,268,328 | B1 | 7/2001 | Mitchinson et al. | |
| 6,270,739 | B1 | 8/2001 | Barnicki et al. | |
| 6,294,653 | B1 | 9/2001 | Mayfield | |
| 6,582,914 | B1 | 6/2003 | Caldwell et al. | |
| 6,806,076 | B1 | 10/2004 | Miyake et al. | |
| 6,989,257 | B2 | 1/2006 | Berry et al. | |
| 6,998,471 | B2 | 2/2006 | Hallahan et al. | |
| 7,129,392 | B2 | 10/2006 | Hahn et al. | |
| 7,132,268 | B2 | 11/2006 | Miyake et al. | |
| 7,132,527 | B2 | 11/2006 | Payne et al. | |
| 7,172,886 | B2 | 2/2007 | Keasling et al. | |
| 7,183,089 | B2 | 2/2007 | Keasling et al. | |
| 7,208,298 | B2 | 4/2007 | Miyake et al. | |
| 7,241,587 | B2 | 7/2007 | Dodge et al. | |
| 7,262,041 | B2 | 8/2007 | Baldwin et al. | |
| 7,364,885 | B2 | 4/2008 | Miyake et al. | |
| 7,531,333 | B2 | 5/2009 | Miyake et al. | |
| 2002/0095818 | A1 | 7/2002 | Jain et al. | |
| 2003/0033626 | A1 | 2/2003 | Hahn et al. | |
| 2004/0005678 | A1 | 1/2004 | Kleasling et al. | |
| 2004/0219629 | A1 | 11/2004 | Cheng et al. | |
| 2005/0287655 | A1 | 12/2005 | Tabata et al. | |
| 2006/0009647 | A1 | 1/2006 | Yeates et al. | |
| 2006/0020095 | A1 | 1/2006 | Gandon-Pain | |
| 2008/0038805 | A1 * | 2/2008 | Melis | 435/167 |
| 2008/0178354 | A1 | 7/2008 | Chappell | |
| 2009/0155874 | A1 | 6/2009 | Clark et al. | |
| 2009/0203102 | A1 | 8/2009 | Cervin et al. | |

(Continued)

FOREIGN PATENT DOCUMENTS

| | | |
|---|---|---|
| DE | 196 29 568 C1 | 1/1998 |
| EP | 0 215 594 A2 | 3/1987 |

(Continued)

OTHER PUBLICATIONS

Albrecht, M. et al. (Aug. 2000). "Novel Hydroxycarotenoids with Improved Antioxidative Properties Produced by Gene Combination in *Escherichia coli*," *Nature Biotechnology* 18:843-846.
Alexopoulos, C.J. (1962). *Introductory Mycology*, Wiley: New York, NY, pp. ix-x, (Table of Contents Only).
Allison, R. et al. (1986). "The Nucleotide Sequence of the Coding Region of Tobacco Etch Virus Genomic RNA: Evidence for the Synthesis of a Single Polyprotein," *Virology* 154:9-20.
Alper, H. et al. (2008). "Uncovering the Gene Knockout Landscape for Improved Lycopene Production in *E. coli*," *Appl. Microbiol. Biotechnol.* 10 pages.
Alterthum, F. et al. (Aug. 1989). "Efficient Ethanol Production from Glucose, Lactose, and Xylose by Recombinant *Escherichia coli*," *Applied Environmental Microbiology* 55(8):1943-1948.
Altschul, S.F. et al. (1990). "Basic Local Alignment Search Tool," *J Mol Biol.* 215:403-410.

(Continued)

*Primary Examiner* — Robert Mondesi
*Assistant Examiner* — Iqbal H Chowdhury
(74) *Attorney, Agent, or Firm* — Morrison & Foerster LLP

(57) ABSTRACT

The present invention provides a three-dimensional structures of *P. tremuloides* isoprene synthase and *P. alba* isoprene synthase. The invention also provides methods of using the three-dimensional structure to design isoprene synthases with improved activity for increased isoprene production in microbial host cells. Biosynthetically produced isoprene of the present invention finds use in the manufacture of rubber and elastomers.

15 Claims, 92 Drawing Sheets

(56) References Cited

U.S. PATENT DOCUMENTS

| | | | |
|---|---|---|---|
| 2010/0003716 | A1 | 1/2010 | Cervin et al. |
| 2010/0048964 | A1 | 2/2010 | Calabria et al. |
| 2010/0086978 | A1 | 4/2010 | Beck et al. |
| 2010/0113846 | A1 | 5/2010 | McAuliffe et al. |
| 2010/0196982 | A1 | 8/2010 | Anderson |
| 2011/0045563 | A1 | 2/2011 | Melis |

FOREIGN PATENT DOCUMENTS

| | | | |
|---|---|---|---|
| EP | 0 215 594 | A3 | 3/1987 |
| EP | 0 215 594 | B1 | 3/1987 |
| EP | 0 215 594 | B2 | 3/1987 |
| EP | 0 238 023 | A2 | 9/1987 |
| EP | 0 238 023 | A3 | 9/1987 |
| EP | 0 238 023 | B1 | 9/1987 |
| EP | 0 238 023 | B2 | 9/1987 |
| EP | 0 244 234 | A2 | 11/1987 |
| EP | 0 244 234 | A3 | 11/1987 |
| EP | 0 244 234 | B1 | 11/1987 |
| EP | 0 244 234 | B2 | 11/1987 |
| EP | 1 118 855 | A2 | 7/2001 |
| EP | 1 118 855 | A3 | 7/2001 |
| JP | 2008-035831 | A | 2/2008 |
| JP | 2008-182950 | A | 8/2008 |
| JP | 2009-207402 | A | 9/2009 |
| KR | 2001-0084864 | A | 9/2001 |
| WO | WO-95/04134 | A1 | 2/1995 |
| WO | WO-96/35796 | A1 | 11/1996 |
| WO | WO-98/02550 | A2 | 1/1998 |
| WO | WO-98/02550 | A3 | 1/1998 |
| WO | WO-00/17327 | A2 | 3/2000 |
| WO | WO-00/17327 | A3 | 3/2000 |
| WO | WO-00/17327 | C2 | 3/2000 |
| WO | WO-01/58839 | A1 | 8/2001 |
| WO | WO-02/099095 | A2 | 12/2002 |
| WO | WO-02/099095 | A3 | 12/2002 |
| WO | WO-2004/033646 | A2 | 4/2004 |
| WO | WO-2004/033646 | A3 | 4/2004 |
| WO | WO-2004/111214 | A1 | 12/2004 |
| WO | WO-2005/001036 | A2 | 1/2005 |
| WO | WO-2005/001036 | C1 | 1/2005 |
| WO | WO-2005/007682 | A2 | 1/2005 |
| WO | WO-2005/007682 | A3 | 1/2005 |
| WO | WO-2005/078074 | A2 | 8/2005 |
| WO | WO-2005/078074 | A3 | 8/2005 |
| WO | WO-2006/063752 | A1 | 6/2006 |
| WO | WO-2006/085899 | A2 | 8/2006 |
| WO | WO-2006/085899 | A3 | 8/2006 |
| WO | WO-2007/018062 | A1 | 2/2007 |
| WO | WO-2007/136847 | A2 | 11/2007 |
| WO | WO-2007/136847 | A3 | 11/2007 |
| WO | WO-2007/140339 | A2 | 12/2007 |
| WO | WO-2007/140339 | A3 | 12/2007 |
| WO | WO-2007/140339 | A8 | 12/2007 |
| WO | WO-2008/003078 | A2 | 1/2008 |
| WO | WO-2008/003078 | A3 | 1/2008 |
| WO | WO-2008/003078 | A8 | 1/2008 |
| WO | WO-2008/137092 | A2 | 11/2008 |
| WO | WO-2008/137092 | A3 | 11/2008 |
| WO | WO-2008/153925 | A2 | 12/2008 |
| WO | WO-2008/153925 | A3 | 12/2008 |
| WO | WO-2008/153925 | A9 | 12/2008 |
| WO | WO-2008/153934 | A2 | 12/2008 |
| WO | WO-2008/153934 | A3 | 12/2008 |
| WO | WO-2008/153935 | A2 | 12/2008 |
| WO | WO-2008/153935 | A3 | 12/2008 |
| WO | WO-2009/036067 | A2 | 3/2009 |
| WO | WO-2009/064910 | A2 | 5/2009 |
| WO | WO-2009/076676 | A2 | 6/2009 |
| WO | WO-2009/076676 | A3 | 6/2009 |
| WO | WO-2009/132220 | A2 | 10/2009 |
| WO | WO-2009/132220 | A3 | 10/2009 |
| WO | WO-2009/132220 | A9 | 10/2009 |
| WO | WO-2010/003007 | A2 | 1/2010 |
| WO | WO-2010/003007 | A3 | 1/2010 |
| WO | WO-2010/005525 | A1 | 1/2010 |
| WO | WO-2010/031062 | A1 | 3/2010 |
| WO | WO-2010/031068 | A1 | 3/2010 |
| WO | WO-2010/031076 | A2 | 3/2010 |
| WO | WO-2010/031076 | A3 | 3/2010 |
| WO | WO-2010/031077 | A1 | 3/2010 |
| WO | WO-2010/031079 | A1 | 3/2010 |
| WO | WO-2010/078457 | A2 | 7/2010 |
| WO | WO-2010/078457 | A3 | 7/2010 |
| WO | WO-2010/124146 | A2 | 10/2010 |

OTHER PUBLICATIONS

Altschul, S.F. et al. (1996). "Local Alignment Statistics," Chapter 27 in *Multiple Alignment and Phylogenetic Trees*, American Press, Inc. 266:460-480.

Alves, R. et al. (Nov. 2000). "Effect of Overall Feedback Inhibition in Unbranched Biosynthetic Pathways," *Biophysical Journal* 79(5):2290-2304.

Anderson, M.S. et al. (Nov. 15, 1989). "Isopentenyl Diphosphate: Dimethylallyl Diphosphate Isomerare. An Improved Purification of the Enzyme and Isolation of the Gene From *Saccharomyces cerevisia," J. Biol. Chem.* 264(32):19169-19175.

Andreassi, J.L. et al. (2004, e-pub. Dec. 4, 2004). "*Streptococcus pneumoniae* Isoprenoid Biosynthesis Is Downregulated by Diphosphomevalonate: An Antimicrobial Target," *Biochemistry* 43(51):16461-16466.

Andreassi, J.L. et al. (2007, e-pub. Mar. 30, 2007). "Crystal Structure of the *Streptococcus pneumoniae* Mevalonate Kinase in Complex with Diphosphomevalonate," *Protein Science* 16:983-989.

Aon, J.C. et al. (Feb. 2008, e-pub. Dec. 14, 2007). "Suppressing Posttranslational Gluconoylation of Heterologous Proteins by Metabolic Engineering of *Escherichia coli," Applied and Environmental Microbiology* 74(4):950-958.

Arai, Y. et al. (2004). "Production of Polyhydroxybutyrate by Polycistronic Expression of Bacterial Genes in Tobacco Plastid," *Plant Cell Physiol* 45(9):1176-1184.

Ashby, M.N. et al. (Aug. 5, 1990). "Elucidation of the Deficiency in Two Yeast Coenzyme Q Mutants: Characterization of the Structural Gene Encoding Hexaprenyl Pyrophosphate Synthetase," *The Journal of Biological Chemistry* 265(22):13157-13164.

Ausubel, F.M. et al. eds. (1994). *Current Protocols in Molecular Biology*, John Wiley and Sons, Inc., pp. 1-7, (Table of Contents Only).

Ausubel, F.M. et al. eds. (1987). *Current Protocols in Molecular Biology*, John Wiley and Sons, Inc., pp. 1-13, (Table of Contents Only).

Baba, T. et al. (Feb. 21, 2006). "Construction of *Escherichia coli* K-12 In-Frame, Single-Gene Knockout Mutants: The Keio Collection," *Molecular Systems Biology* pp. 1-11.

Ballas, N. et al. (1989). "Efficient Functioning of Plant Promoters and Poly(A) Sites in *Xenopus* Oocytes," *Nucleic Acids Research* 17(19):7891-7903.

Barkovich, R. et al. (2001, e-pub. Dec. 1, 2000). "Metabolic Engineering of Isoprenoids," *Metabolic Engineering* 3:27-29.

Beaucage, S.L. et al. (1981). "Deoxynucleoside Phosphoramidites—A New Class of Key Intermediates for Deoxypolynucleotide Synthesis," *Tetrahedron Letters* 22(20):1859-1862.

Bellion, E. et al. (1993). "Methylamine Utilization in Yeast and Bacteria: Studies Using in vivo NMR," Chapter 32 in *Microbial Growth $C_1$ Compounds*, Muerrell, J.C. et al. eds, Intercept Ltd: Andover, UK, pp. 415-432.

Bennett, J.W. et al. eds. (1991). "Gene Cloning and Analysis," Chapter 3 in *More Gene Manipulations in Fungi*, Academic Press, San Diego, CA pp. 70-76.

Berman, H. et al. (2007, e-published Nov. 16, 2006). "The Worldwide Protein Data Bank (wwPDB): Ensuring a Single, Uniform Archive of PDB Data," *Nucleic Acids Research* 35:D301-D303.

Beytia, E. et al. (Oct. 25, 1970). "Purification and Mechanism of Action of Hog Liver Mevalonic Kinase," *The Journal of Biological Chemistry* 245(20):5450-5458.

Bock, R. (2001). "Transgenic Plastids in Basic Research and Plant Biotechnology," *J. Mol. Biol.* 312:425-438.

Bock, R. et al. (2000). "Extranuclear Inheritance: Plastid Genetic: Manipulation of Plastid Genomes and Biotechnological Application," *Progress in Botany* 61:76-90.

Bock, R. et al. (Jun. 2004). "Taming Plastids for a Green Future," *Trends Biotechnology* 22(6):311-318.
Boel, E. et al. (1984). "Two Different Types of Intervening Sequences in the Glucoamylase Gene from *Aspergillus niger," The EMBO Journal* 3(7):1581-1585.
Bouvier, F. et al. (2005). "Biogenesis, Molecular Regulation and Function of Plant Isoprenoids," *Progress in Lipid Res.* 44:357-429.
Boynton, J.E. et al. (1993). "Chloroplast Transformation in *Chlamydomonas," Methods in Enzymology* 217(37):510-536.
Broun, P. et al. (Nov. 13, 1998). "Catalytic Plasticity of Fatty Acid Modification Enzymes Underlying Chemical Diversity of Plant Lipids," *Science* 282:1315-1317.
Brünger, A.T. et al. (1998). "*Crystallography & NMR System*: A New Software Suite for Macromolecular Structure Determination," *Acta Cryst.* D54:905-921.
Bubunenko, M. et al. (Apr. 2007). "Essentiality of Ribosomal and Transcription Antitermination Proteins Analyzed by Systemic Gene Replacement in *Escherichia coli," Journal of Bacteriology* 189(7):2844-2853.
Campbell, E.I. et al. (1989). "Improved Transformation Efficiency of *Aspergillus niger* Using the Homologus *nia*D Gene for Nitrate Reductase," *Curr. Genet.* 16:53-56.
Campbell, J.W. et al. (Oct. 2001). "*Escherichia coli* FadR Positively Regulates Transcription of the *fab*B Fatty Acid Biosynthetic Gene," *J. Bacteriol.* 183(20):5982-5990.
Campos, N. et al. (2001). "*Escherichia coli* Engineering to Synthesize Isopentenyl Diphosphate and Dimethylallyl Diphosphate from Mevalonate: A Novel System for the Genetic Analysis of the 2-*C*-Methyl-D-Erythritol 4-Phospate Pathway for Isoprenoid Biosynthesis," *Biochem. J.* 353:59-67.
Cao, Q-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.
Chamberlin, M. et al. (Oct. 17, 1970). "New RNA Polymerase from *Escherichia coli* Infected with Bacteriophase T7," *Nature* 228:227-231.
Champenoy, S. et al. (1998). "Expression of the Yeast Mevalonate Kinase Gene in Transgenic Tobacco," *Molecular Breeding* 4:291-300.
Chan, W. et al. (2007, e-pub. Apr. 10, 2007). "A Recombineering Based Approach for High-Throughput Conditional Knockout Targeting Vector Construction," *Nucleic Acids Research* 35(8):e64, 13 pages.
Chappell J. et al. (1995). "Is the Reaction Catalyzed by 3-Hydroxy-3-Methylglutaryl-Coenzyme A Reductase a Rate-Limiting Step for Isoprenoid Biosynthesis in Plants?" *Plant Physiology* (109):1337-1343.
Chemler, J.A. et al. (May 23, 2006). "Biosynthesis of Isoprenoids, Polyunsaturated Fatty Acids and Flavonoids in *Saccharomyces cerevisia," Microbial Cell Factories* 5:20, 9 pages.
Chica, R.A. et al. (2005). "Semi-Rational Approaches to Engineering Enzyme Activity: Combining the Benefits of Directed Evolution and Rational Design," *Curr. Opi. Biotechnol.* 16: 378-384.
Cho, H-J. et al. (1995). "Expression Pattern of Bacterial Polycistronic Genes in Tobacco Cells," *Journal of Fermentation and Bioengineering* 80(2):111-117.
Clarke, S. (1992). "Protein Isoprenylation and Methylation at Carboxyl-Terminal Cysteine Residues," *Annu. Rev. Biochem.* 61:355-386.
Clough, S.J. et al. (1998). "Floral Dip: Simplified Method for *Agrobacterium*-Mediated Transformation of *Arabidopsis thaliana," The Plant Journal* 16(6):735-743.
Collaborative Computational Project, No. 4. (1994). "The *CCP*4 Suite: Programs for Protein Crystallography," *Acta Cryst.* D50:760-763.
Cordier, H. et al. (1999). "Heterologous Expression in *Saccharomyces cerevisiae* of an *Arabidopsis thaliana* cDNA Encoding Mevalonate Diphosphate Decarboxylase," *Plant Molecular Biology* 39:953-967.
Crueger, W. et al. (1989). *Biotechnology: A Textbook of Industrial Microbiology*, Second Edition, Brock, T.D. ed., Sinauer Associates, Inc.: Sunderland, MA, pp. vii-x, (Table of Contents Only).
Cunningham, F.X. et al. (1998). "Genes and Enzymes of Carotenoid Biosynthesis in Plants," *Ann. Rev. Plant Mol. Biol.* 49:557-583.
Cunningham, F.X. et al. (Oct. 2000). "Evidence of a Role for LytB in the Nonmevalonate Pathway of Isoprenoid Biosynthesis," *Journal of Bacteriology* 182(20):5841-5848.
Dale, P. J. (1992). "Spread of Engineered Genes to Wild Relatives," *Plant Physiol.* 100:13-15.
Dale, G.E. et al. (2003). "The Protein as a Variable in Protein Crystallization," *J. Struct. Biol.* 142:88-97.
Daniell, H. (1997). "'Transformation and Foreign Gene Expression in Plants Mediated by Microprojectile Bombardment," Chapter 35 in *Methods in Molecular Biology, Recombinant Gene Expression Protocols*, Tuan, R S. ed., Humana Press: Totowa, NJ, 62:463-489.
Daniell, H. et al. (Apr. 1998) "Containment of Herbicide Resistance Through Genetic Engineering of the Chloroplast Genome," *Nature Biotechnology* 16:345-348.
Datsenko, K.A. et al. (Jun. 6, 2000). "One-Step Inactivation of Chromosomal Genes in *Escherichia coli* K-12 Using PCR Products," *PNAS* 97(12):6640-6645.
Datta, S. et al. (2006). "A Set of Recombineering Plasmids for Gram-Negative Bacteria," *Gene* 379:109-115.
Datukishvili, N. T. et al. (2001). "Isolation and Purification of Protein Responsible for the Conversion of Dimethylallylpyrophosphate from Poplar Leaves into Isoprene," *Russian Journal of Plant Physiology* 48(2):222-225.
Davidson, S. (Oct.-Dec. 2003). "Light Factories," located at <http://www.publish.csiro.au/?act=view_file&file_id=EC117p10.pdf>, last visited on Oct. 2, 2008.
Davis, I.W. et al. (2007). "MolProbity: All-Atom Contacts and Structure Validation for Proteins and Nucleic Acids," *Nucleic Acids Research* 35:W375-W383.
De Cosa, B. et al. (Jan. 2001). "Overexpression of the *Bt cry*2Aa2 Operon in Chloroplasts Leads to Formation of Insecticidal Crystals," *Nature Biotechnology* 19:71-74.
Del Campo, E. M. et al. (1997). "Plastid *ndhD* Gene of Barley, Sequence and Transcript Editing (Accesion No. Y12258) (PGR 97-090)," *Plant Physiol.* 114:747-749.
Della-Cioppa, G. et al. (1987). "Protein Trafficking in Plant Cells," *Plant Physiol.* 84:965-968.
Deppenmeier, U. et al. (2002). "The Genome of *Methanosarcina mazei*: Evidence for Lateral Gene Transfer Between Bacteria and Archaea," *J. Mol. Microbiol. Biotechnol.* 4(4):453-461.
Deroles, S.C. et al. (1988). "Expression and Inheritance of Kanamycin Resistance in a Large Number of Transgenic Petunias Generated by *Agrobacteriu*-Mediated Transformation," *Plant Molecular Biology* 11:355-364.
Dettmer, K. et al. (2000). "Stability of Reactive Low Boiling Hydrocarbons on Carbon Based Dsorbents Typically Used for Adsorptive Enrichment and Thermal Desorption," *Fresenius J. Anal. Chem.* 366:70-78.
Devereux, J. et al. (1984). "A Comprehensive Set of Sequence Analysis Programs for the VAX," *Nucleic Acids Research* 12(1):387-395.
Devos, D. et al. (2000). "Practical Limits of Function Prediction," *Proteins: Structure, Function, and Genetics* 41:98-107.
Dewick, P.M. et al. (2002, e-pub. Jan. 22, 2002). "The Biosynthesis of $C_5$-$C_{25}$ Terpenoid Compounds," *Nat. Prod. Rep.* 19:181-222.
Dhe-Paganon, S. et al. (1994). "Mechanism of Mevalonate Pyrophosphate Decarboxylase: Evidence for a Carbocationic Transition State," *Biochemistry* 33(45):13355-13362.
Dorsey, J.K. et al. (Sep. 25, 1968). "The Inhibition of Mevalonic Kinase by Geranyl and Farnesyl Pyrophosphates," *The Journal of Biological Chemistry* 243(18):4667-4670.
Doumith, M. et al. (2000, e-pub. Aug. 25, 2000). "Analysis of Genes Involved in 6-Deoxyhexose Biosynthesis and Transfer in *Saccharopolyspora erythraea," Mol. Gen Genet.* 264:477-485.
Dynan, W.S. et al. (Aug. 29, 1985). "Control of Eukaryotic Messenger RNA Synthesis by Sequence-Specific DNA-Binding Proteins," *Nature* 316:774-778.
Eisenreich, W. et al, (Feb. 2001). "Deoxyxylulose Phosphate Pathway to Terpenoids," *Trends in Plant Science* 6(2):78-84.
Eisenreich, W. et al. (Sep. 1998). "The Deoxyxylulose Phosphate Pathway of Terpenoid Biosynthesis in Plants and Microorganisms," *Chemistry and Biology* 5(9):R221-R233.

Elroy-Stein, O. et al. (Aug. 1989). "Cap-Independent Translation of mRNA Conferred by Encephalomyocarditis Virus 5' Sequence Improves the Performance of the Vaccinia Virus/Bacteriophage T7 Hybrid Expression System," *PNAS USA* 86:6126-6130.

EMBL-EBI Accession No. A0PFK2, last updated on Mar. 2, 2010, located at <http://srs.ebi.ac.uk/srsbin/cgi-bin/wgetz?-e+[UNIPROT:A0PFK2_POPNI]+-newId>, last visited on Jun. 2, 2010, 2 pages.

EMBL-EBI Accession No. A9PGR5, last updated on Mar. 2, 2010, located at <http://srs.ebi.ac.uk/srsbin/cgi-bin/wgetz?-e+[UNIPROT:A9PGR5_POPTR]+-newId>, last visited on Jun. 2, 2010, 2 pages.

EMBL-EBI Accession No. AB198180, last updated May 10, 2005, located at <http://www.ebi.ac.uk/cgi-bin/dbfetch?db=embl&id=ab198180&Subm . . . >, last visited on Aug. 7, 2009, 2 pages.

EMBL-EBI Accession No. AY341431, last updated Apr. 16, 2005, located at <http://www.ebi.ac.uk/cgi-bin/dbfetch?db=embl&id=AY341431&Sub . . . >, last visited on Nov. 26, 2009, 2 pages.

Emsley, P. et al. (2004). "*Coot*: Model-Building Tools for Molecular Graphics," *Acta Crystallographica* D60:2126-2132.

Extended European Search Report mailed on Jun. 14, 2011, for EP Patent Application No. 08860589.4, filed on Dec. 15, 2008, 10 pages.

Fall, R. (Sep. 12, 2003). "Final Technical Report: DE-FG03-97ER20274, 'Microbial Production of Isoprene'," located at <http://www.osti.gov/bridge/product.biblio.jsp?query_id=1&page=0&osti_id=814920>, last visited on May 26, 2010, 4 pages.

Farmer, W.R. et al. (May 2000). "Improving Lycopene Production in *Escherichia coli* by Engineering Metabolic Control," *Nature Biotechnology* 18:533-537.

Feng, D-F. et al. (1987). "Progressive Sequence Alignment as a Prerequisite to Correct Phylogenetic Trees," *Journal of Molecular Evolution* 25:351-360.

Finkelstein, D.B. (1992). "Transformation," Chapter 6 in *Biotechnology of Filamentous Fungi*, Butterworth-Heinemann: Boston, MA, pp. 113-156.

Flores, S. et al. (Aug. 20, 2004, e-pub. Jul. 23, 2004). "Growth-Rate Recovery of *Escherichia coli* Cultures Carrying a Multicopy Plasmid, by Engineering of the Pentose-Phosphate Pathway," *Biotechnology and Bioengineering* 87(4):485-494.

Fu, Z. et al. (2008, e-pub. Feb. 27, 2008). "Biochemical and Structural Basis for Feedback Inhibition of Mevalonate Kinase and Isoprenoid Metabolism," *Biochemistry* 47:3715-3724.

Gallie, D.R. et al. (1989). "Eukaryotic Viral 5'-Leader Sequences Act as Translational Enhancers in Eukaryotes and Prokaryotes," in *Molecular Biology of RNA*, Cech, T.R. ed. Alan R. Liss, Inc: New York, NY, pp. 237-256.

Garret, T.A. et al. (May 15, 1998). "Accumulation of a Lipid a Precursor Lacking the 4'-Phosphate Following Inactivation of the *Escherichia coli IpxK* Gene," *The Journal of Biological Chemistry* 273(20):12457-12465.

GenBank Accession No. AB198180, last updated on May 10, 2005, located at <http://www.ncbi.nlm.nih.gov/nuccore/63108309>, last visited on Jun. 2, 2010, 2 pages.

GenBank Accession No. AJ294819.1, last updated Apr. 15, 2005, located at <http://www.ncbi.nlm.nih.gov/nuccore/AJ294819.1>, last visited on Dec. 7, 2011, 2 pages.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AM410988.1, last updated Aug. 14, 2008, located at <http://www.ncbi.nlm.nih.gov/nuccore/AM410988.1>, last visited on Dec. 7, 2011, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30984014>, last visited on Jun. 2, 2010, 2 pages.

GenBank Accession No. AY316691, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/33358228>, last visited on Jun. 2, 2010, 3 pages.

GenBank Accession No. EF147555.1, last updated Mar. 24, 2009, located at <http://www.ncbi.nlm.nih.gov/nuccore/EF147555.1>, last visited on Dec. 7, 2011, 2 pages.

GenBank Accession No. EF638224.1, last updated May 3, 2010, located at <http://www.ncbi.nlm.nih.gov/nuccore/EF638224.1>, last visited on Dec. 7, 2011, 2 pages.

GenBank Accession No. EU693027, last updated on May 27, 2008, located at <http://www.ncbi.nlm.nih.gov/nuccore/189017053>, last visited on Jun. 2, 2010, 2 pages.

GenBank Accession No. CAC35696, last updated Apr. 15, 2005, located at <http://www.ncbi.nlm.nih.gov/protein/CAC35696>, last visited on Apr. 6, 2011, 1 page.

Gerhardt, P. et al. eds. (1994). *Methods for General and Molecular Bacteriology*, American Society for Microbiology: Washington, D.C., p. v, (Table of Contents Only).

Goedegebuur, F. et al. (2002, e-pub. May 7, 2002). "Cloning and Relational Analysis of 15 Novel Fungal Endoglucanases form Family 12 Glycosyl Hydrolase," *Curr. Genet.* 41:89-98.

Goldschmidt-Clermont, M. (1991). "Transgenic Expression of Aminoglycoside Adenine Transferase in the Chloroplast: A Selectable Marker for Site-Directed Transformation of Chlamydomonas," *Nucleic Acids Res.* 19(15):4083-4089.

Goodwin, T.W. (1971). "Biosynthesis of Carotenoids and Plant Triterpenes: The Fifth CIBA Medal Lecture," *Biochem. J.* 123(3):293-329.

Gottschalk, G. (1986). *Bacterial Metabolism*, Second Edition, Springer Verlag: New York, NY, pp. xi-xiii, (Table of Contents Only).

Gräwert, T. et al. (2004, e-pub. Sep. 21, 2004). "IspH Protein of *Escherichia coli*: Studies on Iron-Sulfur Cluster Implementation and Catalysis," *Journal American Chemistry Society* 126:12847-12855.

Greenberg, J.P. et al. (1993). "Sub-Parts Per Billion Detection of Isoprene Using a Reduction Gas Detector with a Portable Gas Chormatograph," *Atmos. Environ.* 27A(16):2689-2692.

Grochowski, L.L. et al. (May 2006). "*Methanocaldococcus jannaschii* Uses a Modified Mevalonate Pathway for Biosynthesis of Isopentenyl Diphosphate," *Journal of Bacteriology* 188(9):3192-3198.

Guda, C. et al. (2000). "Stable Expression for a Biodegradable Protein-Based Polymer in Tobacco Chloroplasts," *Plant Cell Reports* 19:257-262.

Guerineau, F. et al. (1991). "Effect of Deletions in the Cauliflower Mosaic Virus Polyadenylation Sequence on the Choice of the Polyadenylation Sites in Tobacco Protoplasts," *Mol. Gen. Genet* 226:141-144.

Guo, D-A. et al. (1995). "Developmental Regulation of Sterol Biosynthesis in *Zea mays," Lipids* 30(3):203-219.

Hahn, F.M. et al. (Aug. 1999). "*Escherichia coli* Open Reading Frame 696 Is *idi*, a Nonessential Gene Encoding Isopentenyl Diphosphate Isomerase," *Journal of Bacteriology* 181(15):4499-4504.

Hahn, F.M. et al. (Feb. 1996). "Open Reading Frame 176 in the Photosynthesis Gene Cluster of *Rhodobacter capsulatus* Encodes *idi*, a Gene for Isopentenyl Diphosphate Isomerase," *Journal of Bacteriology* 178(3):619-624.

Hahn, F.M. et al. (Jan. 2001). "1-Deoxy D-Xylulose 5-Phosphate Synthase, the Gene Product of Open Reading Frame (ORF) 2816 and ORF 2895 in *Rhodobacter capsulatus," Journal of Bacteriology* 183(1):1-11.

Hahn, F.M. et al. (May 12, 1995). "Isolation of *Schizosaccharomyces pombe* Isopentenyl Diphosphate Isomerase in cDNA Clones by Complementation and Synthesis of the Enzyme in *Escherichia coli," The Journal of Biological Chemistry* 270(19):11298-11303.

Hale, W.G. et al. (1991). *The Harper Collins Dictionary of Biology*, Ehrlich, E. ed., Harper Perennial: New York, NY, 2 pages.

Hamano, Y. et al. (2001). "Cloning of a Gene Cluster Encoding Enzymes Responsible for the Mevalonate Pathway from a Terpenoid-Antibiotic-Producing *Streptomyces* Strain," *Biosci. Biotechnol. Biochem.* 65(7):1627-1635.

Hamilton, C.M. et al. (Sep. 1989). "New Method for Generating Deletions and Gene Replacements in *Escherichia coli," Journal of Bacteriology* 171(9):4617-4622.
Hanai, T. et al. (Dec. 2007). "Engineered Synthetic Pathway for Isopropanol Production in *Escherichia coli," Applied and Environmental Microbiology* 73(24):7814-7818.
Harker, M. et al. (1999). "Expression of Prokaryotic 1-Deoxy-D-Xylulose-5-Phosphatases in *Escherichia coli* Increases Cartenoid and Ubiquinone Biosynthesis," *FEBS Letters* 448:115-119.
Harkki, A. et al. (Jun. 1989). "A Novel Fungal Expression System: Secretion of Active Calf Chymosin From the Filamentous Fungus *Trichoderma ressei," Bio. Technol.*7:596-603.
Hedl, M. et al. (Apr. 2002). "*Enterococcus faecalis* Acetoacetyl-Coenzyme A Thiolase/3-Hydroxy-3-Methylglutaryl-Coenzyme A Reductase, A Dual-Function Protein of Isopentenyl Diphosphate Biosynthesis," *J. Bacteriol.* 184(8):2116-2122.
Hedl, M. et al. (Apr. 2004). "Class II 3-Hydroxy-3-Methylglutaryl Coenzyme A Reductases," *Journal of Bacteriology* 186(7):1927-1932.
Hellman, U. et al. (1995). "Improvement of an "In-Gel" Digestion Procedure for the Micropreparation of Internal Protein Fragments for Amino Acid Fragments for Amino Acid Sequencing," *Analytical Biochemistry* 224:451-455.
Herbers, K. et al. (Jun. 1996). "Manipulating Metabolic Partitioning in Transgenic Plants", *TIBTECH* 14:198-205.
Herz, S. et al. (Mar. 14, 2000). "Biosynthesis of Terpenoids: YgbB Protein Converts 4-Diphosphocytidyl -2C-Methyl-D-Erythritol 2-Phosphate to 2C-Methyl-D-Erythritol 2,4-Cyclodiphosphate," *Proc. Natl. Acad. Sci. USA* 97(6):2486-2490.
Higgins, D.G. et al. (1989). "Fast and Sensitive Multiple Sequence Alignments on a Microcomputer," *Cabios Communications* 5(2):151-153.
Hinson, D.D. et al. (1997). "Post-Translation Regulation of Mevalonate Kinase by Intermediates of the Cholesterol and Nonsterol Isoprene Biosynthetic Pathways," *Journal of Lipid Research* 38:2216-2223.
Hoeffler, J-F. et al. (2002). "Isoprenoid Biosynthesis via the Methylerythritol Phosphate Pathway. Mechanistic Investigations of the 1-Deoxy-$_D$-Xylulose 5-Phosphate Reductiosimerase," *Eur. J. Biochem.* 269:4446-4457.
Huang, K-X. et al. (1999). "Overexpression, Purification, and Characterization of the Thermostable Mevalonate Kinase from *Methanococcus jannaschii," Protein Expression and Purification* 17:33-40.
Hunter, B.K. (1985). "Formaldehyde Metabolism by *Escherichia coli.* Carbon and Solvent Deuterium Incoproration into Glycerol, 1,2-Propanediol, and 1,3-Propanediol," *Biochemistry* 24(15):4148-4155.
Hyatt, D.C. et al. (Mar. 27, 2007). "Structure of Limonene synthase, A Simple Model for Terpenoid Cyclase Catalysis," *PNAS* 104(13):5360-5365.
Ilmen, M. et al. (Apr. 1997). "Regulation of Cellulase Gene Expression in the Filamentous Fungus *Trichoderma reesei," Appl. Environ. Microbiol.* 63(4):1298-1306.
Innis, M.A. et al. (Apr. 5, 1985). "Expression, Glycosylation, and Secretion of an *Aspergillus* Glucoamylase by *Saccharomyces cerevisiae," Science* 228:21-26.
International Search Report mailed on Jun. 18, 2009, for PCT Patent Application No. PCT/US08/86869, filed on Dec. 15, 2008, 1 page.
Jenkins, L.S. et al. (Jan. 1987). "Genetic and Molecular Characterization of the Genes Involved in Short-Chain Fatty Acid Degradation in *Escherichia coli*: The *ato* System," *Journal of Bacteriology* 169(1):42-52.
Jeong, S.-W. et al. (2004, e-published Jan. 21, 2004). "Dicistronic Expression of the Green Fluorescent Protein and Antibiotic Resistance Genes in the Plastid for Selection and Tracking of Plastid-Transformed Cells in Tobacco," *Plant Cell Rep* 22:747-751.
Jobling, S.A. et al. (Feb. 12, 1987). "Enhanced Translation of Chimaeric Messenger RNAs Containing a Plant Viral Untranslated Leader Sequence," *Nature* 235:622-625.
Jones, K.L. et al. (2000). "Low-Copy Plasmids Can Perform as Well as or Better Than High-Copy Plasmids for Metabolic Engineering of Bacteria," *Metabolic Engineering* 2:238-338.
Jones, E.Y. et al. (1991). "Methodology Employed for the Structure Determination of Tumour Necrosis Factor, a Case of High Non-Crystallographic Symmetry," *Acta Crystallogr.* A47:753-770.
Joshi, C.P. (1987). "Putative Polyadenylation Signals in Nuclear Genes of Higher Plants: A Compilation and Analysis," *Nucleic Acid Research* 15(23):9627-9640.
Julsing, M.K. et al. (2007). "Functional Analysis of Genes Involved in the Biosynthesis of Isoprene in *Bacillus subtilis," Applied Microbiol. Biotechnol.*75:1377-1384.
Kacian, D.L. et al. (Oct. 1972). "A Replicating RNA Molecule Suitable for a Detailed Analysis of Extracellular Evolution and Replication," *Proc Nat! Acad Sci USA* 69(10):3038-3042.
Kajiwara, S. et al. (1997). "Expression of an Exogenous Isopentenyl Diphosphate Isomerase Gene Enhances Isoprenoid Biosynthesis in *Escherichia coli," Biochem. J.* 324:421-426.
Kampranis, S.C. et al. (Jun. 2007). "Rational Conversion of Substrate and Product Specificity in a *Salvia* Monoterpene Synthase: Structural Insights into the Evolution of Terpene Synthase Function," *The Plant Cell* 19:1994-2005.
Kaneda, K. et al. (Jan. 30, 2001). "An Unusual Isopentenyl Diphosphate Isomerase Found in the Mevalonate Pathway Gene Cluster from *Streptomyces* sp. Strain CL190," *PNAS* 98(3):932-937.
Karl, T. et al. (2003). "Dynamic Measurements of Partition Coefficients Using Proton-Transfer-Reaction Mass Spectrometry (PTR-MS)," *International Journal of Mass Spectrometry* 223-224:383-295.
Karlin, S. (Jun. 1993). "Applications and Statistics for Muliple High-Scoring Segments in Molecular Sequences," *Proc Natl Acad Sci USA* 90:5873-5787.
Kavanagh, T.A. et al. (Jul. 1999). "Homeologous Plastid DNA Transformation in Tobacco is Mediated by Multiple Recombination Events," *Genetics* 52:1111-1122.
Keasling, J.D. (Mar. 29, 2004). "Genetic Tools for Metabolic Enzyme Production in *Escherichia coli*," presented at NIGMS 2004 PSI Protein Production & Crystallization Workshop, Bethesda, MD, Mar. 29-31, 2004, located at <http://www-nmr.cabm.rutgers.edu/labdocuments/workshops/psi_ppcw_32904/ppcw_32904.html>, last visited on Jun. 4, 2010, 66 pages.
Keasling, J.D. (May 7, 2005). "Drugs from Bugs: Engineering Microorganisms to Produce New Drugs," presented at Engineering a Better World: *Our Environment, Our Health*, Berkeley, CA, May 7, 2005, 62 pages.
Keasling, J.D. (Sep. 23, 2007). "Engineering Microbes for Production of Low-Cost, Effective, Anti-Malarial Drugs," *presented at Enzyme Engineering XIX*, Harrison Hot Springs, British Columbia, Canada, Sep. 23-28, 2007, 152 pages.
Keegan, R.M. et al. (2007). "Automated Search-Model Discovery and preparation for Structure Solution by Molecular Replacement," *Acta Crystallographica* D63:447-457.
Keeler, K.H. et al. (1996). "Movement of Crop Transgenes into Wild Plants," Chapter 20 in *Herbicide Resistant Crops: Agricultural, Economic, Environmental, RegUlatory and Technological Aspects*, Duke, S.O. ed., Lewis Publishers: Boca Raton, FL., pp. 303-330.
Kelly, J.M. et al. (1985). "Transformation of *Aspergillus niger* by the *amdS* Gene of *Asperfillus nidulans," The EMBO Journal* 4(2):475-479.
Khan, M.S. et al. (Sep. 1999). "Fluorescent Antibiotic Resistance Marker for Tracking Plastid Transformation in Higher Plants," *Nature Biotechnology* 17:910-914.
Kieser, T. eds. et al. (Jul. 2000). "Introduction of DNA into *Streptomyces*," Chapter 10 in *Practical Streptomyces Genetics*, pp. 229-252.
Kinghorn, J.R. et al. (1992). *Applied Molecular Genetics of Filamentous Fungi*, Blackie Academic Professional and Chapman and Hall: London, 3 pages, (Table of Contents Only).
Kisselev, L. (Jan. 2002). "Polypeptide Release Factors in Prokaryotes and Eukaryotes: Same Function, Different Structure," *Structure* 10:8-9.
Klein-Marcuschamer, D. et al. (2007, e-pub. Aug. 2, 2007). "Engineering Microbial cell Factories for Biosynthesis of Isoprenoid Molecules: Beyond Lycopene," *TRENDS in Biotechnology* 25(9):417-424.

Klein-Marcuschamer, D. et al. (Feb. 19, 2008). "Assessing the Potential of Mutational Strategies to Elicit New Phenotypes in Industrial Strains," *Proc. Natl. Acad. Sci.* 105(7):2319-2324.
Koga, Y. et al. (Mar. 2007). "Biosynthesis of Ether-Type Polar Lipids in Archaea and Evolutionary Considerations," *Microbiology and Molecular Biology Reviews* 71(1):97-120.
Köksal, M. et al. (2010, e-pub. Jul. 17, 2010). "Structure of Isoprene Synthase Illuminates the Chemical Mechanism of Teragram Atmospheric Carbon Emission," *J. Mol. Biol.* pp. 1-11.
Kooter, J. M., et al. (Sep. 1999). "Listening to the Silent Genes: Transgene Silencing, Gene Regulation and Pathogen Control," *Trends in Plant Science* 4(9):340-347.
Kota, M. et al. (Mar. 1999). "Overexpression of the *Bacililus thuringiensis* (Bt) Cry2Aa2 Protein in Chloroplasts Confers Resistance to Plants Against Susceptible and Bt-Resistant Insects," *Proc. Natl. Acad. Sci. USA* 96:1840-1845.
Kozak, M. (Oct. 25, 1991). "Structural Features in Eukaryotic mRNAs That Modulate the Initiation of Translation," *The Journal of Biological Chemistry* 266(30):19867-19870.
Kozak, M. (1999). "Initiation of Translation in Prokaryotes and Eukaryotes," *Gene* 234:187-208.
Kreigler, M. (1990). *Gene Transfer and Expression: A Laboratory Manual*, W.H. Freeman and Company: New York, NY, pp. vii-x, (Table of Contents Only.).
Kunkel, T. A. (Jan. 1985). "Rapid and Efficient Site-Specific Mutagenesis without Phenotypic Selection," *Proc. Natl. Acad. Sci. USA* 82:488-492.
Kuzma, J. et al. (1995). "Bacteria Produce the Volatile Hydrocarbon Isoprene," *Current Microbiology* 30:97-103.
Kuzuyama, T. et al. (1998). "Direct Formation of 2-*C* Methyl-D-Erythritoi 4-Phosphate by 1-Deoxy-D-Xylulose 5-Phosphate Reductoisomerase, a New Enzyme in the Non-Mevalonate Pathway to Isopentenyl Diphosphate," *Tetrahedron Letters* 39:4509-4512.
Kuzuyama, T. et al. (1998). "Fosmidomycin, a Specific Inhibitor of 1-Deoxy-D-Xylulose 5-Phosphate Reductoisomerase in the Nonmevalonate Pathway for Terpenoid Biosynthesis," *Tetrahedron Letters* 39:7913-7916.
Lange, B.M. et al. (Nov. 23, 1999). "Isopentenyl Diphosphate Biosynthesis via a Mevalonate-Independent Pathway: Isopentenyl Monophosphate Kinase Catalyzes the Terminal Enzymatic Step," *PNAS* 96(24):13714-13719.
Lange, B.M. et al. (Sep. 2001). "Isoprenoid Biosynthesis. Metabolite Profiling of Peppermint Oil Gland Secretory Cells and Application to Herbicide Target Analysis," *Plant Physiology* 127:305-314.
Law, C.K. (1984). "Heat and Mass Transfer in Combustion: Fundamental Concepts and Analytical Techniques," *Progress in Energy and Combustion Science* 10:295-318.
Lehning, A. et al. (1999). "Isoprene Synthase Activity and Its Relation to Isoprene Emission in *Quercus robur* L. Leaves," *Plant, Cell and Environment* 22:495-504.
Learner, C.G. et al. (1990). "Low Copy Number Plasmids for Regulated Low-Level Expression of Cloned Genes in *Escherichia coli* with Blue/White Insear Screening Capability," *Nucl Acids Res* 18(15):4631.
Li, W. et al. (2010, e-pub. Nov. 1, 2009). "Non-Redundant Patent Sequence Databases with Value-Added Annotations at Two Levels," *Nucleic Acids Research* 38:D52-D56.
Lichtenthaler, H. K. (1999). "The 1-Deoxy-D-Xylulose-5-Phosphate Pathway of Isopenoid Bosynthesis in Plants," *Annu Rev Plant Physiol Plant Mol Biol.* 50:47-65.
Lichtenthaler, H.K. et al. (1997). "Biosynthesis of Isoprenoids in Higher Plant Chloroplasts Proceeds Via a Mevalonate-Independent Pathway," *FEBS Letters* 400:271-274.
Lin, X-M. et al. (2008, e-pub. Apr. 26, 2008). "Proteomic Analysis of Nalidixic Acid Resistance in *Escherichia coli*: Identification and Functional Characterization of OM Proteins," *Journal of Proteome Research* pp. A-G.
Lluch, M.A. et al. (2000). "Molecular Cloning and Expression Analysis of the Mevalonate Kinase Gene from *Arobidopsis thallana," Plant Molecular Biology* 42:365-376.
Lois, L.M. et al. (Mar. 1998). "Cloning and Characterization of a Gene from *Escherichia coli* Encoding a Transketolase-Like Enzyme that Catalyzes the Synthesis of D-1-Deoxyxylulose 5-Phosphate, a Common Precursor for Isoprenoid, Thiamin, and Pyridoxal Biosynthesis," *Proc. Natl. Acad. Sci. USA* 95:2105-2110.
Loivamäki, M. et al. (Jun. 2007). "Arabidopsis, A Model to Study Biological Functions of Isoprene Emission?" *Plant Physiology* 144:1066-1078.
Lommel, S.A. et al. (1991). "Identification of the Maize Chlorotic Mottle Virus Capsid Protein Cistron and Characterization of its Subgenomic Messenger RNA," *Virolog* 181:382-385.
Lücker, J. et al. (2002). "Monoterpene Biosynthesis in Lemon (*Citrus limon*). cDNA Isolation and Functional Analysis of Four Monoterpene Synthases," *European Journal of Biochemistry* 269:3160-3171.
Luli, G.W. et al. (Apr. 1990). "Comparison of Growth, Acetate Production, and Acetate Inhibition of *Escherichia coli* in Batch and Fed-Batch Fermentations," *Applied and Environmental Microbiology* 56(4):1004-1011.
Lüttgen, H. et al. (Feb. 1, 2000). "Biosynthesis of Terpenoids: YchB Protein *Escherichia coli* Phosphorylates the 2-Hydroxy Group of 4-Diphosphocytidyl-2C-Methyl-$_D$-Erythritol," *PNAS* 97(3):1062-1067.
Macejak, D.G. et al. (Sep. 5, 1991). "Internal Initiation of Translation Mediated by the 5' Leader of a Cellular mRNA," *Nature* 353:90-94.
Mahmoud, S.S. et al. (Jul. 17, 2001). "Metabolic Engineering of Essential Oil Yield and Composition in Mint by Altering Expression of Deoxyxylulose Phosphate Reductoisomerase and Menthofuran Synthase," *PNAS* 98(15):8915-8920.
Maldonado-Mendoza, I.E. et al. (1997). "Molecular Characterization of Three Differentially Expressed Members of the *Camptotheca acuminate* 3-Hydroxy-3-Methylglutaryl CoA Reductase (HMGR) Gene Family," *Plant Molecular Biology* 134:781-790.
Mann, V. et al. (Aug. 2000). "Metabolic Engineering of Astaxanthin Production in Tobacco Flowers," *Nature Biotechnology* 18:888-892.
Martin, V.J.J. et al. (Dec. 5, 2001). "The In Vivo Synthesis of Plant Sesquiterpenes by *Escherichia coli," Biotechnology and Bioengineering* 75(5):497-503.
Martin, V.J.J. et al. (Jul. 2003). "Engineering a Mevalonate Pathway in *Escherichia coli* for Production of Terpenoids," *Nature Biotechnology* 21(7):796-802.
Martin, W. et al. (May 14, 1998). "Gene Transfer to the Nucleus and the Evolution of Chloroplasts," *Nature* 393:162-165.
Mashego, M.R. et al. (2007, e-pub. Nov. 8, 2006). "Microbial Metabolomics: Past, Present and Future Methodologies," *Biotechnol. Lett.* 29:1-16.
Matsuoka, S. et al. (Feb. 25, 1991). "Variable Product Specificity of Microsomal Dehydrodolichyl Diphosphate Synthase from Rat Liver," *The Journal of Biological Chemistry* 266(6):3464-3468.
Matteucci, M.D. et al. (1981). "Synthesis of Deoxyoligonucleotides on a Polymer Support," *J. American Chemical Society* 103(11):3185-3191.
Matthews, P.D. et al. (2000). "Metabolic Engineering of Carotenoid Accumulation in *Escherichia coli* by Modulation of the Isoprenoid Precursor Pool with Expression of Deoxyxylulose Phosphate Synthase," *Appl Microbiol Biotechnol* 53:396-400.
Maury, J. et al. (2005, e-pub. Jul. 5, 2005). "Microbial Isoprenoid Production: An Example of Green Chemistry through Metabolic Engineering," *Adv. Biochem. Engin/Biotechnol.* 100:19-51.
McPherson, A. (2004). "Introduction to Protein Crystallization," *Methods* 34:254-265.
Meinkoth, J. et al. (1984). "Hybridization of Nucleic Acids Immobilized on Solid Supports," *Analytical Biochemistry* 138:267-284.
Meyer, P. et al. (1996). "Homology-Dependent Gene Silencing in Plants," *Ann. Rev. Plat. Physiol. Mol. Biol.* 47:23-48.
Millen, R.S. et al. (Mar. 2001). "Many Parallel Losses of *infA* from Choloroplast DNA During Angiosperm Evolution with Multiple Independent Transfers to the Nucleus," *The Plant Cell* 13:645-658.
Miller, B. (2001). "Erstmalige Isolierung Eines Isoprenysthase-Gens und Heterologe Expression Des Aus Der Pappel Stammenden Gens Sowie Charakterisierung der Eingangsgene des Mevalonateunabhängigen Isoprenoidbiosyntheseweges aus dem Cyanobakterium *Synechococcus leopoliensis*," located at <http://kups.ub.uni-koeln.de/883/>, last visited on Jun. 23, 2011, English Translation included, 2 pages.

Miller, B. et al. (2001, e-pub. May 10, 2001). "First Isolation of an Isoprene Synthase Gene from Poplar and Successful Expression of the Gene in *Escherichia coli," Planta*213:483-487.
Milne, P.J. et al. (1995). "Measurement of Vertical Distribution of Isoprene in Surface Seawater, Its Chemical Fate, and Its Emission from Several Phytoplankton Monocultures," *Marine Chemistry* 48:237-244.
Mo, H. et al. (2004). "Studies of the Isoprenoid-Mediated Inhibition of Mevaloante Synthesis Applied to Cancer Chemotherapy and Chemoprevention," *Exp. Biol. Med.* 229:567-585.
Mogen, B.D. et al. (Dec. 1990). "Upstream Sequences Other than AAUAAA are Required for Efficient Messenger RNA 3'-End Formation in Plants," *The Plant Cell* 2:1261-1272.
Monson, R.K. et al. (1992). "Relationships Among Isoprene Emission Rate, Photosynthesis, and Isoprene Synthase Activity as Influenced by Temperature," *Plant Physiol.* 98:1175-1180.
Munroe, D. et al. (1990). "Tales of Poly(A): a Review," *Gene* 91:151-158.
Murray, E.E. et al. (1989). "Codon Usage in Plant Genes," Nucleic Acids Research 17(2): 477-498.
Nakamura, C.E. et al. (2003). "Metabolic Engineering for the Microbial Production of 1,3-Propanediol," *Current Opinion in Biotechnology* 14:454-459.
Nanchen, A. et al. (Apr. 2008, e-pub. Jan. 25, 2008). "Cyclic AMP-Dependent Catabolite Repression Is the Dominant Control Mechanism for Metabolic Fluxes under Glucose Limitation in *Escherichia coli," Journal of Bacteriology* 190(7):2323-2330.
Nawrath, C. et al. (Dec. 1994). "Targeting of the Polyhydroxybutyrate Biosynthetic Pathway to the Plastids of *Arabidopsis thaliana* Results in High Levels of Polymer Accumulation," *Proc. Natl. Acad. Sci. USA* 91:12760-12764.
Needleman, S. B. et al. (1970). "A General Method Applicable to the Search for Similarities in the Amino Acid Sequence of Two Proteins," *J. Mol. Biol.* 48:443-453.
Neidhardt, F.C. et al. (Sep. 1974). "Culture Medium for Enterobacteria," *J. Bacteriology* 119(3):736-747.
Neidhardt, F.C. et al. (1990). "Table 1. Overall Macromolecular COmpositon of an Average *E. coli* B/r Cell[3]," in Chapter 1 in *Physiology of the Bacterial Cell: A Molecular Approach*, Sinauer Associates, Inc.: Sunderland, MA, pp. 4.
Nevalainen, K.M.H. et al. (1992). "The Molecular Biology of *Trichoderma* and Its Application to the Expression of Both Homologous and Heterologous Genes," Chapter 6 in *Molecular Industrial Mycology, Systems and Applications for Filamentous Fungi*, Leong, S.A. et al. eds., Marcel Dekker Inc.: New York, NY, pp. 129-148.
Newman, J.D. et al. (Nov. 5, 2006, e-pub. Jul. 28, 2006). "High-Level Production of Amorpha-4,11-Diene in a Two-Phase Partitioning Bioreactor of Metabolically Engineered *Escherichia coli," Biotechnology and Bioengineering* 95(4):684-691.
Newman, T. et al. (1994). "Genes Galore: A Summary of Methods for Accessing Results from Large-Scale Partial Sequencing of Anonymous *Arabidopsis* cDNA Clones," *Plant Physiology* 106:1241-1255.
Nielsen, K.M. et al. (1997). "Analysis and Developmental Profile of Carotenoid Pigments in Petals of Three Yellow Petunia Cultivars," *Scientia Horticulturae* 71:257-266.
Niinements, Ü. et al. (Nov. 2002). "Stomatal Constraints May Affect Emission of Oxygenated Monoterpenoids from the Foliage of *Pinus pinea," Plant Physiology* 130:1371-1385.
Noronha, S.B. et al. (May 5, 2000). "Investigation of the TCA Cycle and the Glyoxylate Shunt in *Escherichia coli* BL21 and JM109 Using $^{13}$C-NMR/MS," *Biotechnol. Bioeng.* 68(3):316-327.
Nunberg, J.H. et al. (Nov. 1984). "Molecular Cloning and Characterization of the Glucoamylase Gene of *Aspergillus awamori," Mol. Cell. Biol.* 4(11):2306-2315.
Oh, M-K. et al. (Apr. 12, 2002). "Global Expression Profiling of Acetate-Grown *Escherichia coli," The Journal of Biological Chemistry* 277(15):13175-13183.
Ondrey, G. et al. (Oct. 2008). "Bio-Based Isoprene," *Chemical Engineering, Access Intelligence Association*, Rockville, MA, 115(1):14.
Oulmouden, A. et al. (1991). "Nucleotide Sequence of the *ERG12* Gene of *Saccharomyces cerevisiae* Encoding Mevalonate Kinase," *Curr. Genet.* 19:9-14.
Pachuk, C.J. et al. (2000). "Chain Reaction Cloning: A One-Step Method for Directional Ligation of Multiple DNA Fragments," *Gene* 243:19-25.
Pearson, W.R. et al. (Apr. 1988). "Improved Tools for Biological Sequence Comparison," *Proc. Natl. Acad. Sci.* 85:2444-2448.
Pegg, S.C-H. et al. (2006). "Leveraging Enzyme Structure-Function Relationships for Functional Inference and Experimental Design: The Structure-Function Linkage Database," *Biochemistry* 45:2545-2555.
Penttila, M. et al. (1987). "A Versatile Transformation System for the Cellulolytic Filamentous Fungus *Trichoderma reesei," Gene* 61:155-164.
Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein et al. eds., American Society for Microbiology: Washington, D.C., pp. 615-624.
Phan, R.M. et al. (2001, e-pub. Sep. 13, 2001). "Synthesis of (*S*)-Isoprenoid Thiodiphosphates as Substrates and Inhibitors," *J. Org. Chem.* 66(20):6705-6710.
Phillips, T.A. et al. (Jul. 1984). "*Ion* Gene Product of *Escherichia coli* Is a Heat-Shock Protein," *Journal of Bacteriology* 159(1):283-287.
Phue, J-N. et al. (2004). "Transcription Levels of Key Metabolic Genes are the Cause for Different Glucose Utilization Pathways in *E. coli* B (BL21) and *E. coli* K (JM109)," *Journal of Biotechnology* 109:21-30.
Phue, J-N. et al. (2005, e-pub. Aug. 11, 2005). "Impact of Dissolved Oxygen Concentration on Acetate Accumulation and Physiology of *E. coli* BL21, Evaluating Transcription Levels of Key Genes at Different Dissolved Oxygen Conditions," *Metabolic Engineering* 7:353-363.
Pillof, D. et al. (Feb. 14, 2003). "The Kinetic Mechanism of Phosphomevalonate Kinase," *The Journal of Biological Chemistry* 278(7):4510-4515.
Pitera, D.J. et al. (2007, e-pub. Nov. 23, 2006). "Balancing a Heterologous Mevalonate Pathway for Improved Isoprenoid Production in *Escherichia coli," Metabolic Engineering* 9:193-207.
Pommer, H. et al. (1975). "Industrial Synthesis of Terpene Compounds," *Pure and Applied Chemistry* 43(3-4):527-551.
Potter, D. et al. (Oct. 10, 1997). "Identification of Catalytic Residues in Human Mevalonate Kinase," *The Journal of Biological Chemistry* 272(41):25449-25454.
Pourquie, J. et al. (1988). "Scale Up of Cellulase Production and Utilization," in *Biochemistry and Genetics of Cellulose Degradation*, Aubert, J.-P. et al. eds., Academic Press: San Diego, CA, pp. 71-86.
Proudfoot, N. (Feb. 22, 1991). "Poly(A) Signals," *Cell* 64:671-674.
Ramos-Valdivia, A.C. et al. (1997). "Isopentenyl Diphosphate Isomerase: A Core Enzyme in Isoprenoid Biosynthesis: A Review of its Biochemistry and Function," *Nature Product Report* 6:591-603.
Raschke, M. et al. (2004, e-pub. Oct. 28, 2004). "A High-Performance Liquid Chromatography Methods for the Analysis of Intermediates of the Deoxyxylulose Phosphate Pathway," *Analytical Biochemistry* 335:235-243.
Re, E.B. et al. (1995). "Co-Expression of Native and Introduced Genes Reveals Cryptic Regulation of HMG CoA Reductase Expression in *Arabidopsis," The Plant Journal* 7(5):771-789.
Reiling, K.K. et al. (Jul. 20, 2004). "Mono and Diterpene Production in *Escherichia coli," Biotechnology and Bioengineering* 87(2):200-212.
Rodriguez-Concepción, M. et al. (2000). "Genetic Evidence of Branching in the Isoprenoid Pathway for the Production of Isopentenyl Diphosphate and Dimethyl Diphosphate in *Escherichia coli.," FES Letters* 473:328-332.
Rodriguez-Concepción, M. et al. (Nov. 2002). "Elucidation of the Methylerythritol Phosphate Pathway for Isoprenoid Biosynthesis in Bacteria and Plastids. A Metabolic Milestone Achieved Through Genomics," *Plant Physiology* 130:1079-1089.
Rodríguez-Villalón, A. et al. (2008). "Cartenoid Accumulation in Bacteria with Enhanced Supply of Isoprenoid Precursors by Upregulation of Exogenous or Endogenous Pathways," *Journal of Biotechnology* 135:78-84.
Rohdich, F. et al. (Oct. 12, 1999). "Cytidine 5'-Triphosphate-Dependent Biosynthesis of Isoprenoids: YgbP Protein of *Escherichia coli*

Catalyzes the Formation of 4-Diphosphocytidyl-2-*C*-Methylerythritol," *PNAS* 96(21):11758-11763.
Rohdih, F. et al. (Jun. 6, 2000). "Biosynthesis of Terpenoids: 4-Diphosphocytidyl-2C-Methyl-$_D$-Erythritol Synthase of *Arabidopsis thaliana," PNAS* 97(12):6451-6456.
Rohmer, M. (1998). "Isoprenoid Biosynthesis Via the Mevalonate-Independent Route, a Novel Target for Antibacterial Drugs?" *Progress in Drug Research* 50:137-154.
Röhrich, R.C. et al. (2005, e-pub. Nov. 2, 2005). "Reconstitution of an Apicoplast-Localised Electron Transfer Pathway Involved in the Isoprenoid Biosynthesis of *Plasmodium falciparum," FEBS Letters* 579:6433-6439.
Rondon, M.R. et al. (May 1999). "Toward Functional Genomics in Bacteria: Analysis of Gene Expression in *Escherichia coli* from a Bacterial Artificial Chromosome Library of *Bacillus cereus," Proc. Natl. Acad. Sci. USA* 96:6451-6455.
Rosenfeld, J. et al. (1992). "In-Gel Digestion of Proteins for Internal Sequence Analysis After One- or Two-Dimensional Gel Electrophoresis," *Analytical Biochemistry* 203:173-179.
Rost, B. et al. (2004). "The PredictProtein Server," *Nucleic Acids Research* 32:W321-W326.
Sambrook, J. et al. (1982). *Molecular Cloning: A Laboratory Manual*, 2$^{nd}$ edition, Cold Spring Harbor Laboratory Press: New York, NY, pp. xi-xxxviii (Table of Contents Only).
Sambrook, J. et al. (1989). *Molecular Cloning: A Laboratory Manual*, 2$^{nd}$ edition, Cold Spring Harbor Laboratory Press: New York, NY, pp. xi-xxxviii (Table of Contents Only).
Sánchez, C. et al. (Apr. 2002). "The Biosynthetic Gene Cluster for the Antitumor Rebeccamycin: Characterization and Generation of Indolocarbazole Derivatives," *Chem. Biol.* 9(4):519-531.
Sander, R. (Apr. 8, 1999). *Compilation of Henry's Law Constants for Inorganic and Organic Species of Potential Importance in Environmental Chemistry*, 3:1-107.
Sanfaçon, H. et al. (1991). "A Discussion of the Cauliflower Mosaic Virus Polyadenylation Signal," *Genes & Development* 5:141-149.
Sasaki, K. et al. (2005, e-pub. Apr. 7, 2005). "Gene Expression and Characterization of Isoprene Synthase from *Populas alba," FEBS Letters* 579:2514-2518.
Schneider, D. et al. (2002). "Genomic Comparisons Among *Escherichia coli* Strains B. K-12, and O157:H7 Using IS Elements as Molecular Markers," *BMC Microbiology* 2:18, 8 pages.
Schnitzler, J.-P. et al. (2005, e-pub. Jul. 29, 2005). "Biochemical Properties of Isoprene Synthase in Poplar (*Populus x canescens*)," *Planta* 222(5):777-786.
Schöller, C. et al. (1997). "Volatile Metabolites from some Gram-Negative Bacteria," *Chemosphere* 35(7):1487-1495.
Scott, E. et al. (2007, e-pub. Mar. 27, 2007). "Biomass in the Manufacture of Industrial Products—The Use of Proteins and Amino Acids," *Appl. Microbiol. Biotehcnol.* 75:751-762.
Sen, S. et al. (2007). "Developments in Directed Evolution for Improving Enzyme Functions," *Appl. Biochem. Biotechnol*, 143:212-223.
Serino, G. et al. (1997). "A Negative Selection Scheme Based in the Expression of Cytosine Deaminase in Plastids," *The Plant Journal* 12(3): 697-701.
Sharkey, T.D. et al. (Feb. 1, 2005). "Supplemental data for: Evolution of the Isoprene Biosynthetic Pathway in Kudzu," *Plant Physiology* 137(2):700-712.
Sharkey, T.D. et al. (Feb. 2005). "Evolution of the Isoprene Biosynthetic Pathway in Kudzu," *Plant Physiology* 137:700-712.
Sheir-Neiss, G. et al. (Jul. 1984). "Characterization of the Secreted Ceullulases of *Trichoderma ressei* Wild Type and Mutants During Controlled Fermentations," *Appl. Microbiol. Biotechnol.* 20(1):46-53.
Shelton, D. et al. (2004, e-pub. Nov. 26, 2004). "Isolation and Partial Characterization of a Putative Monoterpene Synthase from *Melalecua alternifolia," Plant Physiology and Biochemistry* 42:875-882.
Shinozaki, K. et al. (1986). "The Complete Nucleotide Sequence of the Tobacco Chloroplast Genome: its Gene Organization and Expression," *The EMBO Journal* 5(9):2043-2049.
Shirk, M.C. et al. (2002, e-pub. Jul. 27, 2002). "Isoprene Formation in *Bacillus subtilis*: A Barometer of Central Carbon Assimilation in a Bioreactor?" *Bitoechnol. Prog.* 18(5):1109-1115.
Silver, G.M. et al. (1991). "Enzymatic Synthesis of Isoprene from Dimethylallyl Diphosphate in Aspen Leaf Extracts," *Plant Physiol.* 97:1588-1591.
Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.
Sivy, T.L. et al. (2002). "Isoprene Synthase Activity Parallels Fluctuations of Isoprene Release During Growth of *Bacillus subtilis," Biochemical and Biophysical Research Communications* 294:71-75.
Siwko, M.E. et al. (2007, e-published Oct. 4, 2006). "Does Isoprene Protect Plant Membranes from Thermal Shock? A Molecular Dynamics Study," *Biochimica et Biophysica Acta* 1768:198-206.
Slabinski, L. et al. (2007). "The Challenge of Protein Structure Determination—Lessons from Structural Genomics," *Protein Science* 16:2472-2482.
Slater, S. et al. (1999). "Metabolic Engineering of *Arabidopsis* and *Brassica* for Poly(3-Hydroxybutyrate-*co*-3-Hydroxyvalerate) Copolymer Production," *Nature Biotechnology* 17:1011-1016.
Slater, S. et al. (Apr. 1992). "Production of Poly-(3-Hydroxybutyrate-co-3-Hydroxyvalerate) in a Recombinant *Escherichia coli* Strain," *Applied and Environmental Microbiology* 58(4):1089-1094.
Smit, A. et al. (2000). "Biosynthesis of Isoprenoids via Mevalonate in Archaea: The Lost Pathway," *Genome Research* 10:1468-1484.
Smith, T. et al. (1981). "Comparison of Biosequences." *Advances in Applied Mathematics* 2:482-489.
Sprenger, G.A. et al. (Nov. 1997). "Identification of a Thiamin-Dependent Synthase in *Escherichia coli* Required for the Formation of the 1-Deoxy-$_D$-Xylulose 5-Phosphate Precursor to Isoprenoids, Thiamin, and Pyridoxol," *PNAS* 94:12857-12862.
Starks, C.M. et al. (Sep. 10, 1997). "Structural Basis for Cyclic Terpene Biosynthesis by Tobacco 5-Epi-Aristolochene Synthase," *Science* 277:1815-1820.
Staub, J. M. et al. (1995). "Expression of a Chimeric *uidA* Gene Indicates that Polycistronic mRNAs are Efficiently Translated in Tobacco Plastids," *The Plant Journal* 7(5):845-848.
Staub, J. M. et al. (Mar. 2000). "High-Yield Production of a Human Therapeutic Protein in Tobacco Chloroplast," *Nature Biotechnology* 18:333-338.
Steibüchel, A. (2003). "Production of Rubber-Like Polymers by Microorganisms," *Current Opinion in Microbiology* 6:261-270.
Steller, I. et al. (1997). "An Algorithm for Automatic Indexing of Oscillation Images using Fourier Analysis," *Journal of Applied Crystallography* 30:1036.1040.
Stermer, B. A. et al. (1994). "Regulation of HMG-CoA Reductase Activity in Plants," *Journal of Lipid Research* 35:1133-1140.
Stevens, D.R. et al. (1997). "Genetic Engineering of Eukaryotic Algae: Progress and Prospects," *J. Phycol.* 33:713-722.
Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.
Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *J. Bacteriol.* 184(15):4065-4070.
Takagi, M. et al. (Aug. 2000). "A Gene Cluster for the Mevalonate Pathway from *Streptomyces* sp. Strain CL190," *Journal of Bacteriology* 182(15)4153-4157.
Takahashi, S. et al. (Feb. 1999). "Purification, Characterization, and Cloning of a Eubacterial 3-Hydroxy-3-Methylglutaryl Coenzyme A Reductase, a Key Enzyme Involved in Biosynthesis of Terpenoids," *Journal of Bacteriology* 181(4):1256-1263.
Takara Bio Inc. (Feb. 2008). "Chaperon Plasmid Set," Cat. # 3340, pp. 1-8.
Teymouri, F. et al. (2005, e-pub. Feb. 24, 2005). "Optimization of the Ammonia Fiber Explosion (AFEX) Treatment Parameters for Enzymeatic Hydrolysis of Corn Stover," *Bioresource Technology* 96:2014-2018.

Thomas, F. et al. (1988). "Expression of the *rp123, rp12* and *rps19* Genes in Spinach Chloroplasts," *Nucleic Acids Research* 16(6):2461-2472.
Thomason, L.C. et al. (2007, e-pub. Apr. 16, 2007). "Multicopy Plasmid Modification with Phage λ Red Recombineering," *Plasmid* 58:148-158.
Thouvenot, B. et al. (2004). "The Strong Efficiency of the *Escherichia coli gapA* P1 Promoter Depends on a Complex Combination of Functional Determinants," *Biochem. J.* 383:371-382.
Timberlake, W.E. (1991). "Gene Cloning and Analysis" in Chapter 3 in *More Gene Manipulations in Fungi*, Bennett et al. eds., Academic Press: San Diego, CA, pp. 70-76.
Toriyama, K. et al. (1985). "Cell Suspension and Protoplast Culture in Rice," *Plant Science* 41:179-183.
Tsay, Y.H. et al. (Feb. 1991). "Cloning and Characterization of *ERG8*, an Essential Gene of *Saccharomyces cerevisiae* That Encodes Phosphomevalonate Kinase," *Mol. Cell Biol.* 11(2):620-631.
Tsudsuki, T. (Apr. 24, 1988) "Direct submission, bases 1-155939", *Data Processing Center*, 1998, Aichi-Gakuin University, Aixhi, Japan, 12 pages.
UniProt Database Accession No. A2XGY9, last updated Jul. 27, 2011, located at <http://www.uniprot.org/jobs/201109112CDIG8GYZL.txt>, last visited on Sep. 11, 2011, 2 pages.
UniProt Database Accession No. A5AR04, last updated Jul. 27, 2011, located at <http://www.uniprot.org/jobs/20110911315BAWWKZ7.txt>, last visited on Sep. 11, 2011, 1 page.
UniProt Database Accession No. A5B7V4, last updated Jul. 27, 2011, located at <http://www.uniprot.org/jobs/2011091150O6CWCI3L.txt>, last visited on Sep. 11, 2011, 1 page.
UniProt Database Accession No. A5BKK1, last updated Jul. 27, 2011, located at <http://www.uniprot.org/jobs/20110911315BB1QWK6.txt>, last visited on Sep. 11, 2011, 1 page.
UniProt Database Accession No. A5BLS5, last updated Jul. 27, 2011, located at <http://www.uniprot.org/jobs/201109112CDIFUU28L.txt>, last visited on Sep. 11, 2011, 1 page.
UniProt Database Accession No. A9PGR5, last updated Jul. 27, 2011, located at <http://www.uniprot.org/jobs/201109112CDIFTO6PL.txt>, last visited on Sep. 11, 2011, 1 page.
UniProt Database Accession No. B1P189, last updated Jul. 27, 2011, located at <http://www.uniprot.org/jobs/201109112CDIFXI7BK.txt>, last visited on Sep. 11, 2011, 1 page.
UniProt Database Accession No. B3GEM8, last updated Jul. 27, 2011, located at <http://www.uniprot.org/jobs/20110911315BAG9N17.txt>, last visited on Sep. 11, 2011, 1 page.
UniProt Database Accession No. B7FLI6, last updated Jul. 27, 2011, located at <http://www.uniprot.org/jobs/20110911315BAXCRQU.txt>, last visited on Sep. 11, 2011, 1 page.
UniProt Database Accession No. B9HE95, last updated Jul. 27, 2011, located at <http://www.uniprot.org/jobs/201109112CDIFY9X6U.txt>, last visited on Sep. 11, 2011, 2 pages.
UniProt Database Accession No. B9MXU1, last updated Jul. 27, 2011, located at <http://www.uniprot.org/jobs/201109112CDIFV8DIC.txt>, last visited on Sep. 11, 2011, 2 pages.
UniProt Database Accession No. B9PAP5, last updated Jul. 27, 2011, located at <http://www.uniprot.org/jobs/201109112CDIG1HNFH.txt>, last visited on Sep. 11, 2011, 2 pages.
UniProt Database Accession No. B9T537, last updated Nov. 30, 2010, located at <http://www.uniprot.org/jobs/20110911315BB065GR.txt>, last visited on Sep. 11, 2011, 1 page.
UniProt Database Accession No. B9T825, last updated Jul. 27, 2011, located at <http://www.uniprot.org/jobs/20110911315BALANC9.txt>, last visited on Sep. 11, 2011, 1 page.
UniProt Database Accession No. Q0PCI3, last updated Jul. 27, 2011, located at <http://www.uniprot.org/jobs/20110911315BAPL92C.txt>, last visited on Sep. 11, 2011, 1 page.
UniProt Database Accession No. Q0PCI4, last updated Jul. 27, 2011, located at <http://www.uniprot.org/jobs/20110911315BAQURQ8.txt>, last visited on Sep. 11, 2011, 1 page.
UniProt Database Accession No. Q50L36, last updated May 31, 2011, located at <http://www.uniprot.org/jobs/201109112CDIGBF1M4.txt>, last visited on Sep. 11, 2011, 2 pages.
UniProt Database Accession No. Q5SBP1, last updated Apr. 5 2011, located at <http://www.uniprot.org/jobs/201109112CDIGFFR1Q.txt>, last visited on Sep. 11, 2011, 2 pages.
UniProt Database Accession No. Q5SBP2, last updated Apr. 5, 2011, located at <http://www.uniprot.org/jobs/201109112CDIG4W1U8.txt>, last visited on Sep. 11, 2011, 2 pages.
UniProt Database Accession No. Q5SBP4, last updated Jul. 27, 2011, located at <http://www.uniprot.org/jobs/2011091140O0OYGHJF.txt>, last visited on Sep. 11, 2011, 2 pages.
UniProt Database Accession No. Q5UB07, last updated Jul. 27, 2011, located at <http://www.uniprot.org/jobs/201109112CDIFZCWUC.txt>, last visited on Sep. 11, 2011, 1 page.
UniProt Database Accession No. Q672F7, last updated Jul. 27, 2011, located at <http://www.uniprot.org/jobs/201109112CDIFWBP6O.txt >, last visited on Sep. 11, 2011, 1 page.
UniProt Database Accession No. Q6EJ97, last updated Apr. 5, 2011, located at <http://www.uniprot.org/jobs/20110911315BARZM8D.txt>, last visited on Sep. 11, 2011, 2 pages.
UniProt Database Accession No. Q7Y1V1, last updated Jul. 27, 2011, located at <http://www.uniprot.org/jobs/201109112CDIG0LK2O.txt>, last visited on Sep. 11, 2011, 1 page.
UniProt Database Accession No. Q941H1, last updated Jul. 27, 2011, located at <http://www.uniprot.org/jobs/201109112CDIG6PW6Y.txt>, last visited on Sep. 11, 2011, 1 page.
UniProt Database Accession No. Q9AR86, last updated May 31, 2011, located at <http://www.uniprot.org/jobs/2011091140O0P1KMN7.txt>, last visited on Sep. 11, 2011, 2 pages.
UniProt Database Accession No. Q9LIA1; Q84UU7, last updated Jul. 27, 2011, located at <http://www.uniprot.org/jobs/20110911315BB4RI8G.txt>, last visited on Sep. 11, 2011, 3 pages.
UniProt Database Accession No. Q7XAS7, last updated Apr. 5, 2011, located at <http://www.uniprot.org/jobs/201109112CDIGCK99G.txt>, last visited on Sep. 11, 2011, 2 pages.
UniProt Database Accession No. Q9FQ26, last updated Jul. 27, 2011, located at <http://www.uniprot.org/jobs/20110911315BB3SH2Y.txt>, last visited on Sep. 11, 2011, 1 page.
Vadali, R.V. et al. (2005, e-published Sep. 2, 2005). "Enhanced Lycopene Productivity by Manipulation of Carbon Flow to Isopentenyl Diphosphate in *Escherichia coli," Biotechnol. Prog.* 21(5):1558-1561.
Vagin, A. et al. (1997). "MOLREP: An Automated Program for Molecular Replacement," *Journal of Applied Crystallography* 30:1022-1025.
Van De Walle, M. et al. (Jan. 5, 1998). "Proposed Mechanism of Acetate Accumulation in Two Recombinant *Escherichia coli* Strains During High Density Fermentation," *Biotechnol. Bioeng.* 57(1):71-78.
Van Den Hondel, C.A.M.J.J. et al. (1991). "Heterologous Gene Expression in Filamentous Fungi," Chapter 18 in *More Gene Manipulations in Fungi*, Bennet, J.W. et al. eds., Academic Press, Inc.: San Diego, CA, pp. 396-428.
Van Hylckama, J.E.T. et al. (Apr. 2000). "Characterization of the Gene Cluster Involved in Isoprene Metabolism in *Rhodococcus* sp. Strain AD45," *Journal of Bacteriology* 182(7):1956-1963.
Vandamme, E.J. et al. (2002, e-pub. 2002). "Bioflavours and Fragrances via Fermentation and Biocatalysis," *Journal of Chemical Technology and Biotechnology* 77:1323-1332.
Vane, L.M. (2005, e-pub. Apr. 21, 2005). "A Review of Pervaporation for Product Recovery from Biomass Fermentation Processes," *Journal of Chemical Technology and Biotechnology* 80:603-629.
Velikova, V. et al. (2005). "Consequences of Inhibition of Isoprene Synthesis in *Phragmites australis* Leaves Exposed to Elevated Temperatures," *Agriculture Ecosystems & Environment* 106:209-217.
Vidal, M. et al. (2006, e-pub. Nov. 23, 2005). "Evaluation of Lower Flammability Limits of Fuel-Air-Diluent Mixtures Using Calculated Adiabatic Flame Temperatures," *Journal of Hazardous Materials* 130:21-27.
Voss, S. et al. (1997). "Mutagenesis of a Flexible Loop in Streptavidin Leads to Higher Affinity for the *Strep*-tag II Peptide and Improved Performance in Recombinant Protein Purification," *Protein Engineering* 10(8):975-982.

Voynova, N.E. et al. (Jan. 2004). "*Staphylococcus aureus* Mevalonate Kinase: Isolation and Characterization of an Enzyme of the Isoprenoid Biosyntheitc Pathway," *Journal of Bacteriology* 186(1):61-67.
Wagner, W.P. et al. (Aug. 1999). "Three Distinct Phases of Isoprene Formation During Growth and Sporulation of *Bacillus subtilis,*" *Journal of Bacteriology* 181(15):4700-4703.
Wagner, W.P. et al. (Jan. 2000, e-pub. Nov. 18, 1999). "Isoprene Biosynthesis in *Bacillus subtilis* via the Methylerythritol Phosphate Pathway," *J. Nat. Prod.* 63(1):37-40.
Wang, C-W. et al. (Jan. 20, 1999). "Engineered Isoprenoid Pathway Enhances Astaxanthin Production in *Escherichia coli," Biotechnol. Bioeng.* 62(2):235-241.
Ward, M. et al. (Aug. 1993). "Use of *Aspergillus* Overproducing Mutants, Cured for Intergrated Plasmid, to Overproduce Heterologous Proteins," *Appl. Microbiol. Biotechnol.* 39(6):738-743.
Weissermel, K. et al. (2003). *Industrial Organic Chemistry, 4th, Completely Revised Edition*, translated by Lindley, C.R. et al., Wiley-VCH GmbH & Co. KGaA, Weinheim, Germany, pp. 117-222.
Whisstock, J.C. et al. (2003). "Prediction of Protein Function from Protein Sequence and Structure," *Quarterly Reviews of Biophysics* 36(3):307-340.
Whittington, D.A. et al. (Nov. 26, 2002). "Bornyl Diphosphate Synthase: Structure and Strategy for Carbocation Manipulation by a Terpenoid Cyclase," *PNAS* 99(24):15375-15380.
Wildermuth, M.C. et al. (1998). "Biochemical Characterization of Stromal and Thylakoid-Bound Isoforms of Isoprene Synthase in Willow Leaves," *Plant Physiology* 116:1111-1123.
Wilding, E.I. et al. (Aug. 2000). "Identification, Evolution, and Essentiality of the Mevalonate Pathway for Isopentenyl Diphosphate Biosynthesis in Gram-Positive Cocci," *Journal of Bacteriology* 182(15):4319-4327.
Wilkins, K. (1996). "Volatile Metabolites from Actinomycetes," *Chemosphere* 32(7):1427-1434.
Williams, D.C. et al. (1998). "Truncation of Limonene Synthase Preprotein Provides a Fully Active 'Pseudomature' Form of This Monoterpene Cyclase and Reveals the Function of the Amino-Terminal Arginine Pair," *Biochemistry* 37(35):12213-12220.
Wishart, M.J. et al. (Nov. 10, 1995). "A Single Mutation Converts a Novel Phosphotyrosine Binding Domain into a Dual-Specificity Phosphatase," *The Journal of Biological Chemistry* 270(45):26782-26785.
Withers, S.T. et al. (Oct. 2007, e-pub. Aug. 10, 2007). "Identification of Isopentenol Biosynthetic from *Bacillus subtilis* by a Screening Method Based on Isorpenoid Precursor Toxicity," *Appl. Environ Microbiol.* 73(19):6277-6283.
Witkowski, A. et al. (1999, e-published Aug. 18, 1999). "Conversion of β-Ketoacyl Synthase to a Malonyl Decarboxylase by Replacement of the Active Cysteine with Glutamine," *Biochemistry* 38(36):11643-11650.
Wolfertz, M. et al. (2003). "Biochemical Regulation of Isoprene Emission," *Plant, Cell and Environment* 26:1357-1364.
Wolfertz, M. et al. (Aug. 2004). "Rapid Regulation of the Methylerythritol 4-Phosphate Pathway during Isoprene Synthesis," *Plant Physiology* 135:1939-1945.
Wu, D.Y. et al. (1989). "The Ligation Amplification Reaction (LAR)-Amplification of Specific DNA Sequences Using Sequential Rounds of Template-Dependent Ligation," *Genomics* 4:560-569.
Xia, X-X. et al. (2008). "Comparison of the Extracellular Proteomes of *Escherichia coli* B and K-12 Strains During High Cell Density Cultivation," *Proteomics* 8:1-15.
Yamada, K. et al. (1989). "Production of Glycerol from Methanol by a Mutant Strain of *Candida boidinii* No. 2201," *Agric. Biol. Chem.* 53(2):541-543.
Yang, D. et al. (Mar. 15, 2002, published ahead of print Dec. 19, 2001). "Structure of the *Methanococcus jannaschii* Mevalonate Kinase, a Member of the GHMP Kinase Superfamily," *The Journal of Biological Chemistry* 277(11):9462-9467.
Ye, X. et al. (Jan. 14, 2000). "Engineering the Provitamin A (β-Carotene) Biosynthetic Pathway into (Carotenoid-Free) Rice Endosperm," *Science* 287:303-305.
Yelton, M.M. et al. (Mar. 1984). "Transformation of *Aspergillus nidulans* by Using a *trpC* Plasmid," *PNAS* 81:1470-1474.
Yoon, S-H. et al. (2007, e-pub. May 15, 2007). "Increased β-Carotene Production in Recombinant *Escherichia coli* Harboring an Engineered Isoprenoid Precursor Pathway with Mevalonate Addition," *Biotechnol. Prog.* 23(3):599-605.
Yoon, S-H. et al. (2009). "Combinatorial Expression of Bacterial Whole Mevalonate Pathway for the Production of β-Carotene in *E. coli," Journal of Biotechnology* 140:218-226.
Zepeck, F. et al. (2005, e-pub. Oct. 14, 2005). "Biosynthesis of Isoprenoids. Purification and Properties of IspG Protein from *Escherichia coli," J. Org. Chem.* 70:9168-9174.
Geneseq Database Accession No. AFB74822, "Monoterpene synthetase protein SEQ ID No. 4." Retrieved from EBI accession No. GSP:AFB74822 (Apr. 19, 2007.).
UniProt Database Accession No. B3TPQ7, "SubName: Full=Alpha-terpineol synthase." Retrieved from EBI accession No. UNIPROT:B3TPQ7 (Sep. 2, 2008.).
UniProt Database Accession No. B9RPM0, "SubName: Full=(R)-limonene synthase." Retrieved from EBI accession No. UNIPROT:B9RPM0 (Mar. 24, 2009.).
UniProt Database Accession No. Q6PWU1, "SubName: Full=(−)-a-terpineol synthase." Retrieved from EBI accession No. UNIPROT:Q6PWU1 (Jul. 5, 2004.).
UniProt Database Accession No. Q9LRZ6, "RecName: Full=Beta-myrcene/(E)-beta-ocimene synthase 2, chloroplastic; EC=4.2.3.15; AltName: Full=Terpenoid synthase 24; Short=AtTpS24; Flags: Precursor." Retrieved from EBI accession No. UNIPROT:Q9LRZ6 (Oct. 1, 2000.).

* cited by examiner

Figure 3A (Seq. ID 1: Sequence of p9795)

tagaaaaactcatcgagcatcaaatgaaactgcaatttattcatatcaggattatcaat
accatatttttgaaaaagccgtttctgtaatgaaggagaaaactcaccgaggcagttcc
ataggatggcaagatcctggtatcggtctgcgattccgactcgtccaacatcaatacaa
cctattaatttcccctcgtcaaaaataaggttatcaagtgagaaatcaccatgagtgac
gactgaatccggtgagaatggcaaaagtttatgcatttctttccagacttgttcaacag
gccagccattacgctcgtcatcaaaatcactcgcatcaaccaaaccgttattcattcgt
gattgcgcctgagcgaggcgaaatacgcgatcgctgttaaaaggacaattacaaacagg
aatcgagtgcaaccggcgcaggaacactgccagcgcatcaacaatattttcacctgaat
caggatattcttctaatacctggaacgctgtttttccggggatcgcagtggtgagtaac
catgcatcatcaggagtacggataaaatgcttgatggtcggaagtggcataaattccgt
cagccagtttagtctgaccatctcatctgtaacatcattggcaacgctacctttgccat
gtttcagaaacaactctggcgcatcgggcttcccatacaagcgatagattgtcgcacct
gattgcccgacattatcgcgagcccatttatacccatataaatcagcatccatgttgga
atttaatcgcggcctcgacgtttcccgttgaatatggctcatattcttcctttttcaat
attattgaagcatttatcagggttattgtctcatgagcggatacatatttgaatgtatt
tagaaaaataaacaaataggggtcagtgttacaaccaattaaccaattctgaacattat
cgcgagcccatttatacctgaatatggctcataacaccccttgtttgcctggcggcagt
agcgcggtggtcccacctgaccccatgccgaactcagaagtgaaacgccgtagcgccga
tggtagtgtggggactccccatgcgagagtagggaactgccaggcatcaaataaaacga
aaggctcagtcgaaagactgggcctttcgcccgggctaattagggggtgtcgccctttc
gattgacgctgcagttagacatacatcagctggttaatcgggaaagggtcaatcagcag
cagtttgatgcggttttcagtcgcgtagtctgggcgacccagaccatcgccatactggt
aggtgcagtgggaaacacgtgccatgttaactgcgatttccatgaacgctttaggcagc
agggtggagtcgctaacgcgttcacgattcatctttttccattcggcgtcgatcagttt
acgcagttcttcgcgggcctgttcctcgctggtaccatcgttttcgtgcatgtagctaa
tgatagaattggtagtctcgccacgttccagctccgccgcagaggtggccagatcgttg
cacaggcggaagataacgcagctagaacgcaccagaccatggaagtcggtcagggaacg
cagcgcgtggtcggagatgtcttcctgctgctggcatacggaaaagtaagacggcgcca
gcagcgctacaccggaggaggaaacgctggcgttttccaggtacttggagaaagccggg
ataatttgttgttggaccatttcgcctcttgcagaaaggctttgcacagttcacgcca
gcttttcgtcagataggacaggttgttatgacctttctctttcagaatagaataggacg
tgtcgttaacggtgttgtacagtgccaggaaacacagtttcatatagtccggcagggtg
ttaatagcgttaacgtcccagcgctctacagcatcggtgaacagttgcagttcgtccag
agtgccataaacgtcatacacgtcatcgatgatcgtcaccagaccaaacattttagtaa
cagctttgcgacattcaccaaactgcgggtctggcgccatacccagtgcccagaaataa
acttccatcaggcggtcgcgtacaaaatccagtttgctagccaggcccatctcggtcca
ccagcgggacagatcttgcagctctttctggtgcagggtctgtaccatgttaaaatcca
gcttcgccagctccagcagcagctggtgatgcggttctttcggttcgtatttatccagg
aaccaacgtgcctccagacggtgcagacgctggtgatatggcagttccagggcgtggct
cacttgttctgcaaccttggtattaatgccttctttcaggttgttcttcaggtgggtga
tggaaaaggtacgcgcctcctccagcaggttctcaccctcgaaacccaggtaagacgct
tcatacaggctcagcaggccttggacgtcacctttcagttcaccgctgaaaccaccttc
tttatccttgaaacgctcaaaaacatcctgagaaacctcgaaaccgtgctgacgcagca
gacggaaagacagagcggttgcgtgcaggtcagatttgttctttttgttttcgtccagc
agtacgatgttttccagggctttaatgatgtctttttcaaatttgtaggtcagacccag Figure 3B (Seq. ID 1: Sequence of p9795)

gcgctgcacatcgtcgatcagctccagcagggacagcggctgggtgtctacacggttga
tcatgcagcgaacttcttcctccagtttggtcgctttctcctccagcttttccactttc
aggtcgttctccagggattgcaggaattcgaaattccacaggtttggctgatagtttgc
ggaacgacgggaattatgctcggtaatctgagtaaattgagaagaggtcgcacacatgt
tcagcgacaagggcgacacaaaatttattctaaatgcataataaatactgataacatct
tatagtttgtattatattttgtattatcgttgacatgtataattttgatatcaaaaact
gattttccctttattattttcgagatttattttcttaattctctttaacaaactagaaa
tattgtatatacaaaaaatcataaataatagatgaatagtttaattataggtgttcatc
aatcgaaaaagcaacgtatcttatttaaagtgcgttgctttttctcatttataaggtt
aaataattctcatatatcaagcaaagtgacaggcgcccttaaatattctgacaaatgct
ctttccctaaactccccccataaaaaaacccgccgaagcgggtttttacgttatttgcg
gattaacgattactcgttatcagaaccgcccagggggcccgagcttaagactggccgtc
gttttacaacacagaaagagtttgtagaaacgcaaaaaggccatccgtcaggggccttc
tgcttagtttgatgcctggcagttccctactctcgccttccgcttcctcgctcactgac
tcgctgcgctcggtcgttcggctgcggcgagcggtatcagctcactcaaaggcggtaat
acggttatccacagaatcaggggataacgcaggaaagaacatgtgagcaaaaggccagc
aaaaggccaggaaccgtaaaaaggccgcgttgctggcgtttttccataggctccgcccc
cctgacgagcatcacaaaaatcgacgctcaagtcagaggtggcgaaacccgacaggact
ataaagataccaggcgtttccccctggaagctccctcgtgcgctctcctgttccgaccc
tgccgcttaccggatacctgtccgcctttctcccttcgggaagcgtggcgctttctcat
agctcacgctgtaggtatctcagttcggtgtaggtcgttcgctccaagctgggctgtgt
gcacgaaccccccgttcagcccgaccgctgcgccttatccggtaactatcgtcttgagt
ccaacccggtaagacacgacttatcgccactggcagcagccactggtaacaggattagc
agagcgaggtatgtaggcggtgctacagagttcttgaagtggtggcctaactacggcta
cactagaagaacagtatttggtatctgcgctctgctgaagccagttaccttcggaaaaa
gagttggtagctcttgatccggcaaacaaaccaccgctggtagcggtggtttttttgtt
tgcaagcagcagattacgcgcagaaaaaaaggatctcaagaagatcctttgatcttttc
tacggggtctgacgctcagtggaacgacgcgcgcgtaactcacgttaagggattttggt
catgagcttgcgccgtcccgtcaagtcagcgtaatgctctgcttt Figure 5A (Seq. ID 2: Sequence of pTrcKudzu)

gtttgacagcttatcatcgactgcacggtgcaccaatgcttctggcgtcaggcagccat
cggaagctgtggtatggctgtgcaggtcgtaaatcactgcataattcgtgtcgctcaag
gcgcactcccgttctggataatgttttttgcgccgacatcataacggttctggcaaata
ttctgaaatgagctgttgacaattaatcatccggctcgtataatgtgtggaattgtgag
cggataacaatttcacacaggaaacagcgccgctgagaaaaagcgaagcggcactgctc
tttaacaatttatcagacaatctgtgtgggcactcgaccggaattatcgattaacttta
ttattaaaaattaaagaggtatatattaatgtatcgattaaataaggaggaataaacca
tgtgtgcgacctcttctcaatttactcagattaccgagcataattcccgtcgttccgca
aactatcagccaaacctgtggaatttcgaattcctgcaatccctggagaacgacctgaa
agtggaaaagctggaggagaaagcgaccaaactggaggaagaagttcgctgcatgatca
accgtgtagacacccagccgctgtccctgctggagctgatcgacgatgtgcagcgcctg
ggtctgacctacaaatttgaaaaagacatcattaaagccctggaaaacatcgtactgct
ggacgaaaacaaaaagaacaaatctgacctgcacgcaaccgctctgtctttccgtctgc
tgcgtcagcacggtttcgaggtttctcaggatgtttttgagcgtttcaaggataaagaa
ggtggtttcagcggtgaactgaaaggtgacgtccaaggcctgctgagcctgtatgaagc
gtcttacctgggtttcgagggtgagaacctgctggaggaggcgcgtacctttttccatca
cccacctgaagaacaacctgaaagaaggcattaataccaaggttgcagaacaagtgagc
cacgccctggaactgccatatcaccagcgtctgcaccgtctggaggcacgttggttcct
ggataaatacgaaccgaaagaaccgcatcaccagctgctgctggagctggcgaagctgg
attttaacatggtacagaccctgcaccagaaagagctgcaagatctgtcccgctggtgg
accgagatgggcctggctagcaaactggattttgtacgcgaccgcctgatggaagttta
tttctgggcactgggtatggcgccagacccgcagtttggtgaatgtcgcaaagctgtta
ctaaaatgtttggtctggtgacgatcatcgatgacgtgtatgacgtttatggcactctg
gacgaactgcaactgttcaccgatgctgtagagcgctgggacgttaacgctattaacac
cctgccggactatatgaaactgtgtttcctggcactgtacaacaccgttaacgacacgt
cctattctattctgaaagagaaaggtcataacaacctgtcctatctgacgaaaagctgg
cgtgaactgtgcaaagcctttctgcaagaggcgaaatggtccaacaacaaaattatccc
ggctttctccaagtacctggaaaacgccagcgtttcctcctccggtgtagcgctgctgg
cgccgtcttacttttccgtatgccagcagcaggaagacatctccgaccacgcgctgcgt
tccctgaccgacttccatggtctggtgcgttctagctgcgttatcttccgcctgtgcaa
cgatctggccacctctgcggcggagctggaacgtggcgagactaccaattctatcatta
gctacatgcacgaaaacgatggtaccagcgaggaacaggcccgcgaagaactgcgtaaa
ctgatcgacgccgaatggaaaaagatgaatcgtgaacgcgttagcgactccaccctgct
gcctaaagcgttcatggaaatcgcagttaacatggcacgtgtttcccactgcacctacc
agtatggcgatggtctgggtcgcccagactacgcgactgaaaaccgcatcaaactgctg
ctgattgaccctttcccgattaaccagctgatgtatgtctaactgcagctggtaccata
tgggaattcgaagctttctagaacaaaaactcatctcagaagaggatctgaatagcgcc
gtcgaccatcatcatcatcatcattgagtttaaacggtctccagcttggctgttttggc
ggatgagagaagattttcagcctgatacagattaaatcagaacgcagaagcggtctgat
aaaacagaatttgcctggcggcagtagcgcggtggtcccacctgaccccatgccgaact
cagaagtgaaacgccgtagcgccgatggtagtgtggggtctccccatgcgagagtaggg
aactgccaggcatcaaataaaacgaaaggctcagtcgaaagactgggcctttcgtttta
tctgttgtttgtcggtgaacgctctcctgagtaggacaaatccgccgggagcggatttg
aacgttgcgaagcaacggcccggagggtggcgggcaggacgcccgccataaactgccag
gcatcaaattaagcagaaggccatcctgacggatggcctttttgcgtttctacaaactc Figure 5B (Seq. ID 2: Sequence of pTrcKudzu)

tttttgtttatttttctaaatacattcaaatatgtatccgctcatgagacaataaccct
gataaatgcttcaataatattgaaaaaggaagagtatgagtattcaacatttccgtgtc
gcccttattcccttttttgcggcattttgccttcctgtttttgctcacccagaaacgct
ggtgaaagtaaaagatgctgaagatcagttgggtgcacgagtgggttacatcgaactgg
atctcaacagcggtaagatccttgagagttttcgccccgaagaacgttttccaatgatg
agcacttttaaagttctgctatgtggcgcggtattatcccgtgttgacgccgggcaaga
gcaactcggtcgccgcatacactattctcagaatgacttggttgagtactcaccagtca
cagaaaagcatcttacggatggcatgacagtaagagaattatgcagtgctgccataacc
atgagtgataacactgcggccaacttacttctgacaacgatcggaggaccgaaggagct
aaccgcttttttgcacaacatgggggatcatgtaactcgccttgatcgttgggaaccgg
agctgaatgaagccataccaaacgacgagcgtgacaccacgatgcctgtagcaatggca
acaacgttgcgcaaactattaactggcgaactacttactctagcttcccggcaacaatt
aatagactggatggaggcggataaagttgcaggaccacttctgcgctcggcccttccgg
ctggctggtttattgctgataaatctggagccggtgagcgtgggtctcgcggtatcatt
gcagcactggggccagatggtaagccctcccgtatcgtagttatctacacgacggggag
tcaggcaactatggatgaacgaaatagacagatcgctgagataggtgcctcactgatta
agcattggtaactgtcagaccaagtttactcatatatactttagattgatttaaaactt
catttttaatttaaaaggatctaggtgaagatcctttttgataatctcatgaccaaaat
cccttaacgtgagttttcgttccactgagcgtcagaccccgtagaaaagatcaaaggat
cttcttgagatcctttttttctgcgcgtaatctgctgcttgcaaacaaaaaaaccaccg
ctaccagcggtggtttgtttgccggatcaagagctaccaactctttttccgaaggtaac
tggcttcagcagagcgcagataccaaatactgtccttctagtgtagccgtagttaggcc
accacttcaagaactctgtagcaccgcctacatacctcgctctgctaatcctgttacca
gtggctgctgccagtggcgataagtcgtgtcttaccgggttggactcaagacgatagtt
accggataaggcgcagcggtcgggctgaacggggggttcgtgcacacagcccagcttgg
agcgaacgacctacaccgaactgagatacctacagcgtgagctatgagaaagcgccacg
cttcccgaagggagaaaggcggacaggtatccggtaagcggcagggtcggaacaggaga
gcgcacgagggagcttccagggggaaacgcctggtatctttatagtcctgtcgggtttc
gccacctctgacttgagcgtcgatttttgtgatgctcgtcaggggggcggagcctatgg
aaaaacgccagcaacgcggcctttttacggttcctggccttttgctggccttttgctca
catgttctttcctgcgttatcccctgattctgtggataaccgtattaccgcctttgagt
gagctgataccgctcgccgcagccgaacgaccgagcgcagcgagtcagtgagcgaggaa
gcggaagagcgcctgatgcggtattttctccttacgcatctgtgcggtatttcacaccg
catatggtgcactctcagtacaatctgctctgatgccgcatagttaagccagtatacac
tccgctatcgctacgtgactgggtcatggctgcgccccgacacccgccaacacccgctg
acgcgccctgacgggcttgtctgctcccggcatccgcttacagacaagctgtgaccgtc
tccgggagctgcatgtgtcagaggttttcaccgtcatcaccgaaacgcgcgaggcagca
gatcaattcgcgcgcgaaggcgaagcggcatgcatttacgttgacaccatcgaatggtg
caaaacctttcgcggtatggcatgatagcgcccggaagagagtcaattcagggtggtga
atgtgaaaccagtaacgttatacgatgtcgcagagtatgccggtgtctcttatcagacc
gtttcccgcgtggtgaaccaggccagccacgtttctgcgaaaacgcgggaaaaagtgga
agcggcgatggcggagctgaattacattcccaaccgcgtggcacaacaactggcgggca
aacagtcgttgctgattggcgttgccacctccagtctggccctgcacgcgccgtcgcaa
attgtcgcggcgattaaatctcgcgccgatcaactgggtgccagcgtggtggtgtcgat
ggtagaacgaagcggcgtcgaagcctgtaaagcggcggtgcacaatcttctcgcgcaac Figure 5C (Seq. ID 2: Sequence of pTrcKudzu)

gcgtcagtgggctgatcattaactatccgctggatgaccaggatgccattgctgtggaa
gctgcctgcactaatgttccggcgttatttcttgatgtctctgaccagacacccatcaa
cagtattattttctcccatgaagacggtacgcgactgggcgtggagcatctggtcgcat
tgggtcaccagcaaatcgcgctgttagcgggcccattaagttctgtctcggcgcgtctg
cgtctggctggctggcataaatatctcactcgcaatcaaattcagccgatagcggaacg
ggaaggcgactggagtgccatgtccggttttcaacaaaccatgcaaatgctgaatgagg
gcatcgttcccactgcgatgctggttgccaacgatcagatggcgctgggcgcaatgcgc
gccattaccgagtccgggctgcgcgttggtgcggatatctcggtagtgggatacgacga
taccgaagacagctcatgttatatcccgccgtcaaccaccatcaaacaggattttcgcc
tgctggggcaaaccagcgtggaccgcttgctgcaactctctcagggccaggcggtgaag
ggcaatcagctgttgcccgtctcactggtgaaaagaaaaaccaccctggcgcccaatac
gcaaaccgcctctccccgcgcgttggccgattcattaatgcagctggcacgacaggttt
cccgactggaaagcgggcagtgagcgcaacgcaattaatgtgagttagcgcgaattgat
ctg Figure 7A (Seq ID 3: Sequence of pMAL-C4X)

ccgacaccatcgaatggtgcaaaacctttcgcggtatggcatgatagcgcccggaagag
agtcaattcagggtggtgaatgtgaaaccagtaacgttatacgatgtcgcagagtatgc
cggtgtctcttatcagaccgtttcccgcgtggtgaaccaggccagccacgtttctgcga
aaacgcgggaaaaagtggaagcggcgatggcggagctgaattacattcccaaccgcgtg
gcacaacaactggcgggcaaacagtcgttgctgattggcgttgccacctccagtctggc
cctgcacgcgccgtcgcaaattgtcgcggcgattaaatctcgcgccgatcaactgggtg
ccagcgtggtggtgtcgatggtagaacgaagcggcgtcgaagcctgtaaagcggcggtg
cacaatcttctcgcgcaacgcgtcagtgggctgatcattaactatccgctggatgacca
ggatgccattgctgtggaagctgcctgcactaatgttccggcgttatttcttgatgtct
ctgaccagacacccatcaacagtattattttctcccatgaagacggtacgcgactgggc
gtggagcatctggtcgcattgggtcaccagcaaatcgcgctgttagcgggcccattaag
ttctgtctcggcgcgtctgcgtctggctggctggcataaatatctcactcgcaatcaaa
ttcagccgatagcggaacgggaaggcgactggagtgccatgtccggttttcaacaaacc
atgcaaatgctgaatgagggcatcgttcccactgcgatgctggttgccaacgatcagat
ggcgctgggcgcaatgcgcgccattaccgagtccgggctgcgcgttggtgcggatatct
cggtagtgggatacgacgataccgaagacagctcatgttatatcccgccgttaaccacc
atcaaacaggattttcgcctgctggggcaaaccagcgtggaccgcttgctgcaactctc
tcagggccaggcggtgaagggcaatcagctgttgcccgtctcactggtgaaaagaaaaa
ccaccctggcgcccaatacgcaaaccgcctctccccgcgcgttggccgattcattaatg
cagctggcacgacaggtttcccgactggaaagcgggcagtgagcgcaacgcaattaatg
taagttagctcactcattaggcacaattctcatgtttgacagcttatcatcgactgcac
ggtgcaccaatgcttctggcgtcaggcagccatcggaagctgtggtatggctgtgcagg
tcgtaaatcactgcataattcgtgtcgctcaaggcgcactcccgttctggataatgttt
tttgcgccgacatcataacggttctggcaaatattctgaaatgagctgttgacaattaa
tcatcggctcgtataatgtgtggaattgtgagcggataacaatttcacacaggaaacag
ccagtccgtttaggtgttttcacgagcacttcaccaacaaggaccatagcatatgaaaa
tcgaagaaggtaaactggtaatctggattaacggcgataaaggctataacggtctcgct
gaagtcggtaagaaattcgagaaagataccggaattaaagtcaccgttgagcatccgga
taaactggaagagaaattcccacaggttgcggcaactggcgatggccctgacattatct
tctgggcacacgaccgctttggtggctacgctcaatctggcctgttggctgaaatcacc
ccggacaaagcgttccaggacaagctgtatccgtttacctgggatgccgtacgttacaa
cggcaagctgattgcttacccgatcgctgttgaagcgttatcgctgatttataacaaag
atctgctgccgaacccgccaaaaacctgggaagagatcccggcgctggataaagaactg
aaagcgaaaggtaagagcgcgctgatgttcaacctgcaagaaccgtacttcacctggcc
gctgattgctgctgacggggggttatgcgttcaagtatgaaaacggcaagtacgacatta
aagacgtgggcgtggataacgctggcgcgaaagcgggtctgaccttcctggttgacctg
attaaaaacaaacacatgaatgcagacaccgattactccatcgcagaagctgcctttaa
taaaggcgaaacagcgatgaccatcaacggcccgtgggcatggtccaacatcgacacca
gcaaagtgaattatggtgtaacggtactgccgaccttcaagggtcaaccatccaaaccg
ttcgttggcgtgctgagcgcaggtattaacgccgccagtccgaacaaagagctggcaaa
agagttcctcgaaaactatctgctgactgatgaaggtctggaagcggttaataaagaca
aaccgctgggtgccgtagcgctgaagtcttacgaggaagagttggtgaaagatccgcgg
attgccgccactatggaaaacgcccagaaaggtgaaatcatgccgaacatcccgcagat
gtccgctttctggtatgccgtgcgtactgcggtgatcaacgccgccagcggtcgtcaga
ctgtcgatgaagccctgaaagacgcgcagactaattcgagctcgaacaacaacaacaat Figure 7B (Seq ID 3: Sequence of pMAL-C4X)

aacaataacaacaacctcgggatcgagggaaggatttcagaattcggatcctctagagt
cgacctgcaggcaagcttggcactggccgtcgttttacaacgtcgtgactgggaaaacc
ctggcgttacccaacttaatcgccttgcagcacatcccccttcgccagctggcgtaat
agcgaagaggcccgcaccgatcgcccttcccaacagttgcgcagcctgaatggcgaatg
gcagcttggctgttttggcggatgagataagattttcagcctgatacagattaaatcag
aacgcagaagcggtctgataaaacagaatttgcctggcggcagtagcgcggtggtccca
cctgaccccatgccgaactcagaagtgaaacgccgtagcgccgatggtagtgtggggtc
tccccatgcgagagtagggaactgccaggcatcaaataaaacgaaaggctcagtcgaaa
gactgggcctttcgttttatctgttgtttgtcggtgaacgctctcctgagtaggacaaa
tccgccgggagcggatttgaacgttgcgaagcaacggcccggagggtggcgggcaggac
gcccgccataaactgccaggcatcaaattaagcagaaggccatcctgacggatggcctt
tttgcgtttctacaaactctttttgtttatttttctaaatacattcaaatatgtatccg
ctcatgagacaataaccctgataaatgcttcaataatattgaaaaaggaagagtatgag
tattcaacatttccgtgtcgcccttattcccttttttgcggcattttgccttcctgttt
ttgctcacccagaaacgctggtgaaagtaaaagatgctgaagatcagttgggtgcacga
gtgggttacatcgaactggatctcaacagcggtaagatccttgagagttttcgccccga
agaacgttctccaatgatgagcacttttaaagttctgctatgtggcgcggtattatccc
gtgttgacgccgggcaagagcaactcggtcgccgcatacactattctcagaatgacttg
gttgagtactcaccagtcacagaaaagcatcttacggatggcatgacagtaagagaatt
atgcagtgctgccataaccatgagtgataacactgcggccaacttacttctgacaacga
tcggaggaccgaaggagctaaccgcttttttgcacaacatgggggatcatgtaactcgc
cttgatcgttgggaaccggagctgaatgaagccataccaaacgacgagcgtgacaccac
gatgcctgtagcaatggcaacaacgttgcgcaaactattaactggcgaactacttactc
tagcttcccggcaacaattaatagactggatggaggcggataaagttgcaggaccactt
ctgcgctcggcccttccggctggctggtttattgctgataaatctggagccggtgagcg
tgggtctcgcggtatcattgcagcactggggccagatggtaagccctcccgtatcgtag
ttatctacacgacggggagtcaggcaactatggatgaacgaaatagacagatcgctgag
ataggtgcctcactgattaagcattggtaactgtcagaccaagtttactcatatatact
ttagattgatttaccccggttgataatcagaaaagccccaaaaacaggaagattgtata
agcaaatatttaaattgtaaacgttaatattttgttaaaattcgcgttaaatttttgtt
aaatcagctcattttttaaccaataggccgaaatcggcaaaatcccttataaatcaaaa
gaatagaccgagatagggttgagtgttgttccagtttggaacaagagtccactattaaa
gaacgtggactccaacgtcaaagggcgaaaaaccgtctatcagggcgatggcccactac
gtgaaccatcacccaaatcaagttttttggggtcgaggtgccgtaaagcactaaatcgg
aaccctaaagggagcccccgatttagagcttgacggggaaagccggcgaacgtggcgag
aaaggaagggaagaaagcgaaaggagcgggcgctagggcgctggcaagtgtagcggtca
cgctgcgcgtaaccaccacacccgccgcgcttaatgcgccgctacagggcgcgtaaaag
gatctaggtgaagatcctttttgataatctcatgaccaaaatcccttaacgtgagtttt
cgttccactgagcgtcagaccccgtagaaaagatcaaaggatcttcttgagatcctttt
tttctgcgcgtaatctgctgcttgcaaacaaaaaaaccaccgctaccagcggtggtttg
tttgccggatcaagagctaccaactctttttccgaaggtaactggcttcagcagagcgc
agataccaaatactgtccttctagtgtagccgtagttaggccaccacttcaagaactct
gtagcaccgcctacatacctcgctctgctaatcctgttaccagtggctgctgccagtgg
cgataagtcgtgtcttaccgggttggactcaagacgatagttaccggataaggcgcagc
ggtcgggctgaacggggggttcgtgcacacagcccagcttggagcgaacgacctacacc Figure 7C (Seq ID 3: Sequence of pMAL-C4X)

gaactgagatacctacagcgtgagctatgagaaagcgccacgcttcccgaagggagaaa
ggcggacaggtatccggtaagcggcagggtcggaacaggagagcgcacgagggagcttc
cagggggaaacgcctggtatctttatagtcctgtcgggtttcgccacctctgacttgag
cgtcgatttttgtgatgctcgtcaggggggcggagcctatggaaaaacgccagcaacgc
ggcctttttacggttcctggccttttgctggccttttgctcacatgttctttcctgcgt
tatcccctgattctgtggataaccgtattaccgcctttgagtgagctgataccgctcgc
cgcagccgaacgaccgagcgcagcgagtcagtgagcgaggaagcggaagagcgcctgat
gcggtattttctccttacgcatctgtgcggtatttcacaccgcatatatggtgcactct
cagtacaatctgctctgatgccgcatagttaagccagtatacactccgctatcgctacg
tgactgggtcatggctgcgccccgacacccgccaacacccgctgacgcgccctgacggg
cttgtctgctcccggcatccgcttacagacaagctgtgaccgtctccgggagctgcatg
tgtcagaggttttcaccgtcatcaccgaaacgcgcgaggcagctgcggtaaagctcatc
agcgtggtcgtgcagcgattcacagatgtctgcctgttcatccgcgtccagctcgttga
gtttctccagaagcgttaatgtctggcttctgataaagcgggccatgttaagggcggtt
ttttcctgtttggtcactgatgcctccgtgtaagggggatttctgttcatgggggtaat
gataccgatgaaacgagagaggatgctcacgatacgggttactgatgatgaacatgccc
ggttactggaacgttgtgagggtaaacaactggcggtatggatgcggcgggaccagaga
aaaatcactcagggtcaatgccagcgcttcgttaatacagatgtaggtgttccacaggg
tagccagcagcatcctgcgatgcagatccggaacataatggtgcagggcgctgacttcc
gcgtttccagactttacgaaacacggaaaccgaagaccattcatgttgttgctcaggtc
gcagacgttttgcagcagcagtcgcttcacgttcgctcgcgtatcggtgattcattctg
ctaaccagtaaggcaaccccgccagcctagccgggtcctcaacgacaggagcacgatca
tgcgcacccgtggccaggacccaacgctgcccgaaatt Figure 9A (Seq ID 4: Sequence of pMAL-C4X Kudzu)

ccgacaccatcgaatggtgcaaaacctttcgcggtatggcatgatagcgcccggaagag
agtcaattcagggtggtgaatgtgaaaccagtaacgttatacgatgtcgcagagtatgc
cggtgtctcttatcagaccgtttcccgcgtggtgaaccaggccagccacgtttctgcga
aaacgcgggaaaaagtggaagcggcgatggcggagctgaattacattcccaaccgcgtg
gcacaacaactggcgggcaaacagtcgttgctgattggcgttgccacctccagtctggc
cctgcacgcgccgtcgcaaattgtcgcggcgattaaatctcgcgccgatcaactgggtg
ccagcgtggtggtgtcgatggtagaacgaagcggcgtcgaagcctgtaaagcggcggtg
cacaatcttctcgcgcaacgcgtcagtgggctgatcattaactatccgctggatgacca
ggatgccattgctgtggaagctgcctgcactaatgttccggcgttatttcttgatgtct
ctgaccagacacccatcaacagtattattttctcccatgaagacggtacgcgactgggc
gtggagcatctggtcgcattgggtcaccagcaaatcgcgctgttagcgggcccattaag
ttctgtctcggcgcgtctgcgtctggctggctggcataaatatctcactcgcaatcaaa
ttcagccgatagcggaacgggaaggcgactggagtgccatgtccggttttcaacaaacc
atgcaaatgctgaatgagggcatcgttcccactgcgatgctggttgccaacgatcagat
ggcgctgggcgcaatgcgcgccattaccgagtccgggctgcgcgttggtgcggatatct
cggtagtgggatacgacgataccgaagacagctcatgttatatcccgccgttaaccacc
atcaaacaggattttcgcctgctggggcaaaccagcgtggaccgcttgctgcaactctc
tcagggccaggcggtgaagggcaatcagctgttgcccgtctcactggtgaaaagaaaaa
ccaccctggcgcccaatacgcaaaccgcctctccccgcgcgttggccgattcattaatg
cagctggcacgacaggtttcccgactggaaagcgggcagtgagcgcaacgcaattaatg
taagttagctcactcattaggcacaattctcatgtttgacagcttatcatcgactgcac
ggtgcaccaatgcttctggcgtcaggcagccatcggaagctgtggtatggctgtgcagg
tcgtaaatcactgcataattcgtgtcgctcaaggcgcactcccgttctggataatgttt
tttgcgccgacatcataacggttctggcaaatattctgaaatgagctgttgacaattaa
tcatcggctcgtataatgtgtggaattgtgagcggataacaatttcacacaggaaacag
ccagtccgtttaggtgttttcacgagcacttcaccaacaaggaccatagcatatgaaaa
tcgaagaaggtaaactggtaatctggattaacggcgataaaggctataacggtctcgct
gaagtcggtaagaaattcgagaaagataccggaattaaagtcaccgttgagcatccgga
taaactggaagagaaattcccacaggttgcggcaactggcgatggccctgacattatct
tctgggcacacgaccgctttggtggctacgctcaatctggcctgttggctgaaatcacc
ccggacaaagcgttccaggacaagctgtatccgtttacctgggatgccgtacgttacaa
cggcaagctgattgcttacccgatcgctgttgaagcgttatcgctgatttataacaaag
atctgctgccgaacccgccaaaaacctgggaagagatcccggcgctggataaagaactg
aaagcgaaaggtaagagcgcgctgatgttcaacctgcaagaaccgtacttcacctggcc
gctgattgctgctgacggggggttatgcgttcaagtatgaaaacggcaagtacgacatta
aagacgtgggcgtggataacgctggcgcgaaagcgggtctgaccttcctggttgacctg
attaaaaacaaacacatgaatgcagacaccgattactccatcgcagaagctgcctttaa
taaaggcgaaacagcgatgaccatcaacggcccgtgggcatggtccaacatcgacacca
gcaaagtgaattatggtgtaacggtactgccgaccttcaagggtcaaccatccaaaccg
ttcgttggcgtgctgagcgcaggtattaacgccgccagtccgaacaaagagctggcaaa
agagttcctcgaaaactatctgctgactgatgaaggtctggaagcggttaataaagaca
aaccgctgggtgccgtagcgctgaagtcttacgaggaagagttggtgaaagatccgcgg
attgccgccactatggaaaacgcccagaaaggtgaaatcatgccgaacatcccgcagat
gtccgctttctggtatgccgtgcgtactgcggtgatcaacgccgccagcggtcgtcaga
ctgtcgatgaagccctgaaagacgcgcagactaattcgagctcgaacaacaacaacaat Figure 9B (Seq ID 4: Sequence of pMAL-C4X Kudzu)

aacaataacaacaacctcgggatcgagggaaggatttcagaattctgtgcgacctcttc
tcaatttactcagattaccgagcataattcccgtcgttccgcaaactatcagccaaacc
tgtggaatttcgaattcctgcaatccctggagaacgacctgaaagtggaaaagctggag
gagaaagcgaccaaactggaggaagaagttcgctgcatgatcaaccgtgtagacaccca
gccgctgtccctgctggagctgatcgacgatgtgcagcgcctgggtctgacctacaaat
ttgaaaaagacatcattaaagccctggaaaacatcgtactgctggacgaaaacaaaaag
aacaaatctgacctgcacgcaaccgctctgtctttccgtctgctgcgtcagcacggttt
cgaggtttctcaggatgtttttgagcgtttcaaggataaagaaggtggtttcagcggtg
aactgaaaggtgacgtccaaggcctgctgagcctgtatgaagcgtcttacctgggtttc
gagggtgagaacctgctggaggaggcgcgtaccttttccatcacccacctgaagaacaa
cctgaaagaaggcattaataccaaggttgcagaacaagtgagccacgccctggaactgc
catatcaccagcgtctgcaccgtctggaggcacgttggttcctggataaatacgaaccg
aaagaaccgcatcaccagctgctgctggagctggcgaagctggattttaacatggtaca
gaccctgcaccagaaagagctgcaagatctgtcccgctggtggaccgagatgggcctgg
ctagcaaactggattttgtacgcgaccgcctgatggaagtttatttctggcactgggt
atggcgccagacccgcagtttggtgaatgtcgcaaagctgttactaaaatgtttggtct
ggtgacgatcatcgatgacgtgtatgacgtttatggcactctggacgaactgcaactgt
tcaccgatgctgtagagcgctgggacgttaacgctattaacaccctgccggactatatg
aaactgtgtttcctggcactgtacaacaccgttaacgacacgtcctattctattctgaa
agagaaaggtcataacaacctgtcctatctgacgaaaagctggcgtgaactgtgcaaag
cctttctgcaagaggcgaaatggtccaacaacaaaattatcccggctttctccaagtac
ctggaaaacgccagcgtttcctcctccggtgtagcgctgctggcgccgtcttacttttc
cgtatgccagcagcaggaagacatctccgaccacgcgctgcgttccctgaccgacttcc
atggtctggtgcgttctagctgcgttatcttccgcctgtgcaacgatctggccacctct
gcggcggagctggaacgtggcgagactaccaattctatcattagctacatgcacgaaaa
cgatggtaccagcgaggaacaggcccgcgaagaactgcgtaaactgatcgacgccgaat
ggaaaaagatgaatcgtgaacgcgttagcgactccaccctgctgcctaaagcgttcatg
gaaatcgcagttaacatggcacgtgtttcccactgcacctaccagtatggcgatggtct
gggtcgcccagactacgcgactgaaaaccgcatcaaactgctgctgattgacccctttcc
cgattaaccagctgatgtatgtctaagcttggcactggccgtcgttttacaacgtcgtg
actgggaaaaccctggcgttacccaacttaatcgccttgcagcacatcccccctttcgcc
agctggcgtaatagcgaagaggcccgcaccgatcgcccttcccaacagttgcgcagcct
gaatggcgaatggcagcttggctgttttggcggatgagataagattttcagcctgatac
agattaaatcagaacgcagaagcggtctgataaaacagaatttgcctggcggcagtagc
gcggtggtcccacctgaccccatgccgaactcagaagtgaaacgccgtagcgccgatgg
tagtgtggggtctccccatgcgagagtagggaactgccaggcatcaaataaaacgaaag
gctcagtcgaaagactgggcctttcgttttatctgttgtttgtcggtgaacgctctcct
gagtaggacaaatccgccgggagcggatttgaacgttgcgaagcaacggcccggagggt
ggcgggcaggacgcccgccataaactgccaggcatcaaattaagcagaaggccatcctg
acggatggcctttttgcgtttctacaaactctttttgtttatttttctaaatacattca
aatatgtatccgctcatgagacaataaccctgataaatgcttcaataatattgaaaaag
gaagagtatgagtattcaacatttccgtgtcgcccttattcccttttttgcggcatttt
gccttcctgtttttgctcacccagaaacgctggtgaaagtaaaagatgctgaagatcag
ttgggtgcacgagtgggttacatcgaactggatctcaacagcggtaagatccttgagag
ttttcgccccgaagaacgttctccaatgatgagcactttttaaagttctgctatgtggcg Figure 9C (Seq ID 4: Sequence of pMAL-C4X Kudzu)

cggtattatcccgtgttgacgccgggcaagagcaactcggtcgccgcatacactattct
cagaatgacttggttgagtactcaccagtcacagaaaagcatcttacggatggcatgac
agtaagagaattatgcagtgctgccataaccatgagtgataacactgcggccaacttac
ttctgacaacgatcggaggaccgaaggagctaaccgcttttttgcacaacatgggggat
catgtaactcgccttgatcgttgggaaccggagctgaatgaagccataccaaacgacga
gcgtgacaccacgatgcctgtagcaatggcaacaacgttgcgcaaactattaactggcg
aactacttactctagcttcccggcaacaattaatagactggatggaggcggataaagtt
gcaggaccacttctgcgctcggcccttccggctggctggtttattgctgataaatctgg
agccggtgagcgtgggtctcgcggtatcattgcagcactggggccagatggtaagccct
cccgtatcgtagttatctacacgacggggagtcaggcaactatggatgaacgaaataga
cagatcgctgagataggtgcctcactgattaagcattggtaactgtcagaccaagttta
ctcatatatactttagattgatttaccccggttgataatcagaaaagccccaaaaacag
gaagattgtataagcaaatatttaaattgtaaacgttaatattttgttaaaattcgcgt
taaatttttgttaaatcagctcattttttaaccaataggccgaaatcggcaaaatccct
tataaatcaaaagaatagaccgagatagggttgagtgttgttccagtttggaacaagag
tccactattaaagaacgtggactccaacgtcaaagggcgaaaaaccgtctatcagggcg
atggcccactacgtgaaccatcacccaaatcaagttttttggggtcgaggtgccgtaaa
gcactaaatcggaaccctaaagggagcccccgatttagagcttgacggggaaagccggc
gaacgtggcgagaaaggaagggaagaaagcgaaaggagcgggcgctagggcgctggcaa
gtgtagcggtcacgctgcgcgtaaccaccacacccgccgcgcttaatgcgccgctacag
ggcgcgtaaaaggatctaggtgaagatcctttttgataatctcatgaccaaaatccctt
aacgtgagttttcgttccactgagcgtcagaccccgtagaaaagatcaaaggatcttct
tgagatcctttttttctgcgcgtaatctgctgcttgcaaacaaaaaaaccaccgctacc
agcggtggtttgtttgccggatcaagagctaccaactctttttccgaaggtaactggct
tcagcagagcgcagataccaaatactgtccttctagtgtagccgtagttaggccaccac
ttcaagaactctgtagcaccgcctacatacctcgctctgctaatcctgttaccagtggc
tgctgccagtggcgataagtcgtgtcttaccgggttggactcaagacgatagttaccgg
ataaggcgcagcggtcgggctgaacggggggttcgtgcacacagcccagcttggagcga
acgacctacaccgaactgagatacctacagcgtgagctatgagaaagcgccacgcttcc
cgaagggagaaaggcggacaggtatccggtaagcggcagggtcggaacaggagagcgca
cgagggagcttccagggggaaacgcctggtatctttatagtcctgtcgggtttcgccac
ctctgacttgagcgtcgatttttgtgatgctcgtcaggggggcggagcctatggaaaaa
cgccagcaacgcggcctttttacggttcctggccttttgctggccttttgctcacatgt
tctttcctgcgttatcccctgattctgtggataaccgtattaccgcctttgagtgagct
gataccgctcgccgcagccgaacgaccgagcgcagcgagtcagtgagcgaggaagcgga
agagcgcctgatgcggtattttctccttacgcatctgtgcggtatttcacaccgcatat
atggtgcactctcagtacaatctgctctgatgccgcatagttaagccagtatacactcc
gctatcgctacgtgactgggtcatggctgcgccccgacacccgccaacacccgctgacg
cgccctgacgggcttgtctgctcccggcatccgcttacagacaagctgtgaccgtctcc
gggagctgcatgtgtcagaggttttcaccgtcatcaccgaaacgcgcgaggcagctgcg
gtaaagctcatcagcgtggtcgtgcagcgattcacagatgtctgcctgttcatccgcgt
ccagctcgttgagtttctccagaagcgttaatgtctggcttctgataaagcgggccatg
ttaagggcggttttttcctgtttggtcactgatgcctccgtgtaagggggatttctgtt
catgggggtaatgataccgatgaaacgagagaggatgctcacgatacgggttactgatg
atgaacatgcccggttactggaacgttgtgagggtaaacaactggcggtatggatgcgg Figure 9D (Seq ID 4: Sequence of pMAL-C4X Kudzu)

cgggaccagagaaaaatcactcagggtcaatgccagcgcttcgttaatacagatgtagg
tgttccacagggtagccagcagcatcctgcgatgcagatccggaacataatggtgcagg
gcgctgacttccgcgtttccagactttacgaaacacggaaaccgaagaccattcatgtt
gttgctcaggtcgcagacgttttgcagcagcagtcgcttcacgttcgctcgcgtatcgg
tgattcattctgctaaccagtaaggcaaccccgccagcctagccgggtcctcaacgaca
ggagcacgatcatgcgcacccgtggccaggacccaacgctgcccgaaatt Figure 10
A.
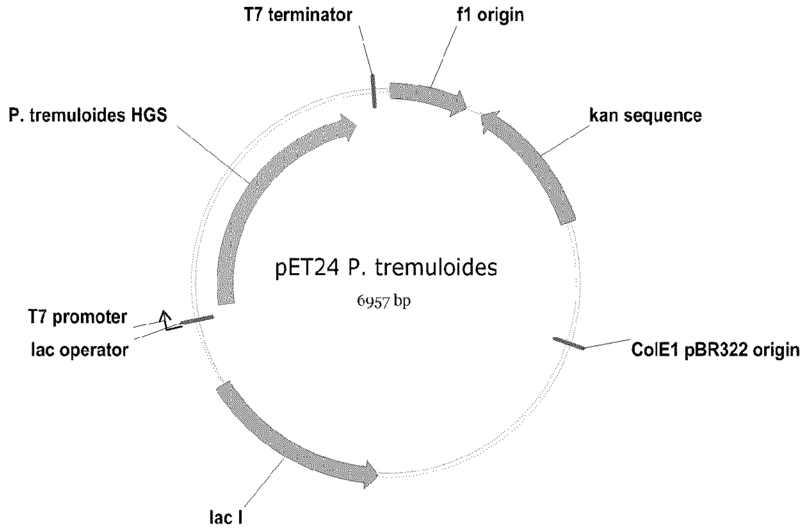
B.
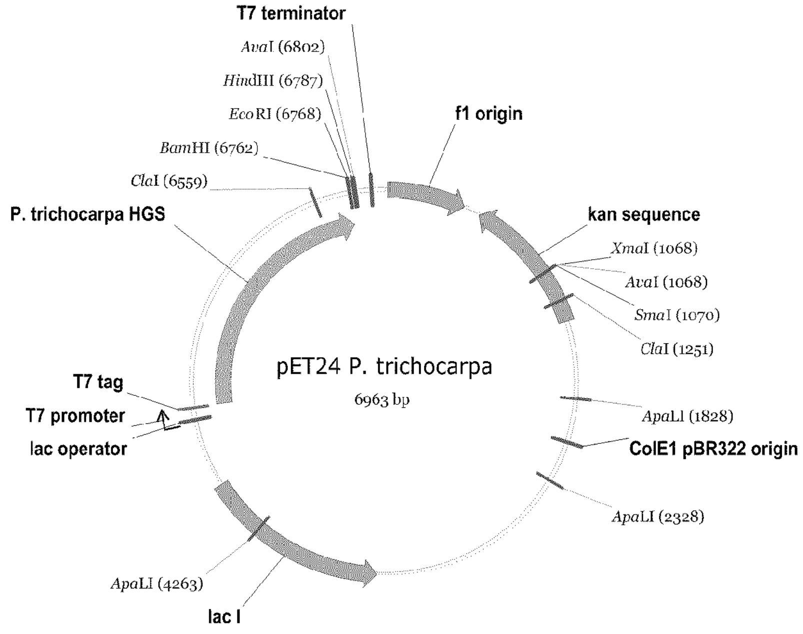

Figure 11 (Amino Acid Sequence of P. tremuloides IspS (in P. tremuloides pET24a))

MRCSVSTENVSFSETETETRRSANYEPNSWDYDYLLSSDTDESIEVHKDKAKKLEAEVR
REINNEKAEFLTLLELIDNVQRLGLGYRFESDIRRALDRFVSSGGFDGVTKTSLHGTAL
SFRLLRQHGFEVSQEAFSGFKDQNGNFLENLKEDIKAILSLYEASFLALEGENILDEAK
VFAISHLKELSEEKIGKELAEQVSHALELPLHRRTQRLEAVWSIEAYRKKEDANQVLLE
LAILDYNMIQSVYQRDLRETSRWWRRVGLATKLHFARDRLIESFYWAVGVAFEPQYSDC
RNSVAKMFSFVTIIDDIYDVYGTLDELELFTDAVERWDVNAINDLPDYMKLCFLALYNT
INEIAYDNLKDKGENILPYLTKAWADLCNAFLQEAKWLYNKSTPTFDDYFGNAWKSSSG
PLQLIFAYFAVVQNIKKEEIENLQKYHDIISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFER

Figure 12A (DNA Sequence of P. tremuloides pET24a)

tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctcccttt
agggttccgatttagtgctttacggcacctcgaccccaaaaaacttgattagggtgatg
gttcacgtagtgggccatcgccctgatagacggtttttcgccctttgacgttggagtcc
acgttctttaatagtggactcttgttccaaactggaacaacactcaaccctatctcggt
ctattcttttgatttataagggattttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatatttttgaaaaagccgtttctgtaa
tgaaggagaaaactcaccgaggcagttccataggatggcaagatcctggtatcggtctg
cgattccgactcgtccaacatcaatacaacctattaatttcccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttcccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacaccccttgtattactgtttatgtaagcagacagtttta
ttgttcatgaccaaaatcccttaacgtgagttttcgttccactgagcgtcagaccccgt
agaaaagatcaaaggatcttcttgagatcctttttttctgcgcgtaatctgctgcttgc
aaacaaaaaaaccaccgctaccagcggtggtttgtttgccggatcaagagctaccaact
ctttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccagggggaaacgcctggtatcttta
tagtcctgtcgggtttcgccacctctgacttgagcgtcgatttttgtgatgctcgtcag
gggggcggagcctatggaaaaacgccagcaacgcggcctttttacggttcctggccttt
tgctggccttttgctcacatgttctttcctgcgttatcccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag
atgtctgcctgttcatccgcgtccagctcgttgagtttctccagaagcgttaatgtctg Figure 12B (DNA Sequence of P. tremuloides pET24a)

gcttctgataaagcgggccatgttaagggcggttttttcctgtttggtcactgatgcct
ccgtgtaagggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgcccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggtttttcttttcaccagtgagacgggcaacagctgattgccctt
caccgcctggccctgagagagttgcagcaagcggtccacgctggtttgccccagcaggc
gaaaatcctgtttgatggtggttaacggcgggatataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
actttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctcccttatgcgactcctgcattaggaagc
agcccagtagtaggttgaggccgttgagcaccgccgccgcaaggaatggtgcatgcaag
gagatggcgcccaacagtcccccggccacggggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactataggggaattgtgagcg
gataacaattcccctctagaaataattttgtttaactttaagaaggagatatacatatg
cgttgtagcgtgtccaccgaaaatgtgtctttctctgaaactgaaaccgaaacgcgtcg
ttctgcgaactacgaacctaacagctgggactatgattacctgctgtcctccgacacgg
acgagtccatcgaagtacacaaagacaaagcgaaaaagctggaagccgaagttcgtcgc
gagattaataacgaaaaagcagaatttctgaccctgctggaactgattgacaacgtcca Figure 12C (DNA Sequence of P. tremuloides pET24a)

gcgcctgggcctgggttaccgtttcgagtctgatatccgtcgtgcgctggatcgcttcg
tttcctccggcggcttcgatggcgtaaccaagacttccctgcacggtacggcactgtct
ttccgtctgctgcgtcaacacggttttgaggtttctcaggaagcgttcagcggcttcaa
agaccaaaacggcaacttcctggagaacctgaaggaagatatcaaagctatcctgagcc
tgtacgaggccagcttcctggctctggaaggcgaaaacatcctggacgaggcgaaggtt
ttcgcaatctctcatctgaaagaactgtctgaagaaaagatcggtaaagagctggcaga
acaggtgtcccatgcactggaactgccactgcatcgccgtactcagcgtctggaagcag
tatggtctatcgaggcctaccgtaaaaggaggacgcgaaccaggttctgctggagctg
gcaattctggattacaacatgatccagtctgtataccagcgtgatctgcgtgaaacgtc
ccgttggtggcgtcgtgtgggtctggcgaccaaactgcactttgctcgtgaccgcctga
ttgagagcttctactgggccgtgggtgtagcattcgaaccgcaatactccgactgccgt
aactccgtcgcaaaaatgtttctttcgtaaccattatcgacgatatctacgatgtata
cggcaccctggacgaactggagctgtttactgatgcagttgagcgttgggacgtaaacg
ccatcaacgacctgccggattacatgaaactgtgctttctggctctgtataacactatt
aacgaaatcgcctacgacaacctgaaagataaaggtgagaacatcctgccgtatctgac
caaagcctgggctgacctgtgcaacgctttcctgcaagaagccaagtggctgtacaaca
aatctactccgacctttgacgactacttcggcaacgcatggaaatcctcttctggcccg
ctgcaactgatcttcgcttacttcgctgtcgtgcagaacattaaaaaggaagagatcga
aaacctgcaaaaataccatgacatcatctctcgtccttcccatatcttccgtctgtgca
atgacctggctagcgcgtctgcggaaattgcgcgtggtgaaaccgcaaatagcgtttct
tgttacatgcgcactaaaggtatctccgaagaactggctaccgaaagcgtgatgaatct
gatcgatgaaacctggaaaaagatgaacaaggaaaaactgggtggtagcctgttcgcga
aaccgttcgtggaaaccgcgatcaacctggcacgtcaatctcactgcacttatcataac
ggcgacgcgcatacctctccggatgagctgacccgcaaacgcgttctgtctgtaatcac
tgaaccgattctgccgtttgaacgctaaggatccgaattcgagctccgtcgacaagctt
gcggccgcactcgagcaccaccaccaccaccactgagatccggctgctaacaaagcccg
aaaggaagctgagttggctgctgccaccgctgagcaataactagcataaccccttgggg
cctctaaacgggtcttgaggggttttttgctgaaaggaggaactatatccggat Figure 13 (Amino Acid Sequence of P. trichocharpa IspS (in P. trichocharpa pET24a))

MRCSVSTENVSFTETETETRRSANYEPNSWDYDYLLSSDTDESIEVYKDKAKKLEAEVR
REINNEKAEFLTLLELIDNVQRLGLGYRFESDIRRALDRFVSSGGFDAVTKTSLHATAL
SFRLLRQHGFEVSQEAFSGFKDQNGNFLENLKEDIKAILSLYEASFLALEGENILDEAK
VFAISHLKELSEEKIGKDLAEQVNHALELPLHRRTQRLEAVLSIEAYRKKEDADQVLLE
LAILDYNMIQSVYQRDLRETSRWWRRVGLATKLHFARDRLIESFYWAVGVAFEPQYSDC
RNSVAKMFSFVTIIDDIYDVYGTLDELELFTNAVERWDVNAIDDLPDYMKLCFLALYNT
INEIAYDNLKEKGENILPYLTKAWADLCNAFLQEAKWLYNKSTPTFDEYFGNAWKSSSG
PLQLVFAYFAVVQNIKKEEIENLQKYHDIISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFER

Figure 14A (DNA sequence of P. trichocharpa pET24a)

tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctcccttt
agggttccgatttagtgctttacggcacctcgaccccaaaaaacttgattagggtgatg
gttcacgtagtgggccatcgccctgatagacggtttttcgccctttgacgttggagtcc
acgttctttaatagtggactcttgttccaaactggaacaacactcaaccctatctcggt
ctattcttttgatttataagggattttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatatttttgaaaaagccgtttctgtaa
tgaaggagaaaactcaccgaggcagttccataggatggcaagatcctggtatcggtctg
cgattccgactcgtccaacatcaatacaacctattaatttcccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttcccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacaccccttgtattactgtttatgtaagcagacagtttta
ttgttcatgaccaaaatcccttaacgtgagttttcgttccactgagcgtcagaccccgt
agaaaagatcaaaggatcttcttgagatcctttttttctgcgcgtaatctgctgcttgc
aaacaaaaaaaccaccgctaccagcggtggtttgtttgccggatcaagagctaccaact
ctttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccagggggaaacgcctggtatcttta
tagtcctgtcgggtttcgccacctctgacttgagcgtcgatttttgtgatgctcgtcag
gggggcggagcctatggaaaaacgccagcaacgcggcctttttacggttcctggccttt
tgctggccttttgctcacatgttctttcctgcgttatcccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag
atgtctgcctgttcatccgcgtccagctcgttgagtttctccagaagcgttaatgtctg Figure 14B (DNA sequence of P. trichocharpa pET24a)

gcttctgataaagcgggccatgttaagggcggtttttcctgtttggtcactgatgcct
ccgtgtaagggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgcccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggtttttcttttcaccagtgagacgggcaacagctgattgccctt
caccgcctggccctgagagagttgcagcaagcggtccacgctggtttgccccagcaggc
gaaaatcctgtttgatggtggttaacggcgggatataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
actttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctcccttatgcgactcctgcattaggaagc
agcccagtagtaggttgaggccgttgagcaccgccgccgcaaggaatggtgcatgcaag
gagatggcgcccaacagtcccccggccacggggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactataggggaattgtgagcg
gataacaattcccctctagaaataattttgtttaactttaagaaggagatatacatatg
catatgcgttgtagcgtgtccaccgaaaatgtgtctttcaccgaaactgaaaccgaaac
gcgtcgttctgcgaactacgaacctaacagctgggactatgattacctgctgtcctccg
acacggacgagtccatcgaagtatacaaagacaaagcgaaaaagctggaagccgaagtt
cgtcgcgagattaataacgaaaaagcagaatttctgaccctgctggaactgattgacaa Figure 14C (DNA sequence of P. trichocharpa pET24a)

cgtccagcgcctgggcctgggttaccgtttcgagtctgatatccgtcgtgcgctggatc
gcttcgtttcctccggcggcttcgatgcggtaaccaagacttccctgcacgcgacggca
ctgtctttccgtctgctgcgtcaacacggttttgaggtttctcaggaagcgttcagcgg
cttcaaagaccaaaacggcaacttcctggagaacctgaaggaagatatcaaagctatcc
tgagcctgtacgaggccagcttcctggctctggaaggcgaaaacatcctggacgaggcg
aaggttttcgcaatctctcatctgaaagaactgtctgaagaaaagatcggtaaagatct
ggcagaacaggtgaaccatgcactggaactgccactgcatcgccgtactcagcgtctgg
aagcagtactgtctatcgaggcctaccgtaaaaaggaggacgcggatcaggttctgctg
gagctggcaattctggattacaacatgatccagtctgtataccagcgtgatctgcgtga
aacgtcccgttggtggcgtcgtgtgggtctggcgaccaaactgcactttgctcgtgacc
gcctgattgagagcttctactgggccgtgggtgtagcattcgaaccgcaatactccgac
tgccgtaactccgtcgcaaaaatgttttctttcgtaaccattatcgacgatatctacga
tgtatacggcaccctggacgaactggagctgtttactaacgcagttgagcgttgggacg
taaacgccatcgacgatctgccggattacatgaaactgtgctttctggctctgtataac
actattaacgaaatcgcctacgacaacctgaaagaaaaaggtgagaacatcctgccgta
tctgaccaaagcctgggctgacctgtgcaacgctttcctgcaagaagccaagtggctgt
acaacaaatctactccgacctttgacgaatacttcggcaacgcatggaaatcctcttct
ggcccgctgcaactggtgttcgcttacttcgctgtcgtgcagaacattaaaaaggaaga
gatcgaaaacctgcaaaaataccatgacatcatctctcgtccttcccatatcttccgtc
tgtgcaatgacctggctagcgcgtctgcggaaattgcgcgtggtgaaaccgcaaatagc
gtttcttgttacatgcgcactaaaggtatctccgaagaactggctaccgaaagcgtgat
gaatctgatcgatgaaacctggaaaaagatgaacaaggaaaaactgggtggtagcctgt
tcgcgaaaccgttcgtggaaaccgcgatcaacctggcacgtcaatctcactgcacttat
cataacggcgacgcgcatacctctccggatgagctgacccgcaaacgcgttctgtctgt
aatcactgaaccgattctgccgtttgaacgctaaggatccgaattcgagctccgtcgac
aagcttgcggccgcactcgagcaccaccaccaccaccactgagatccggctgctaacaa
agcccgaaaggaagctgagttggctgctgccaccgctgagcaataactagcataacccc
ttggggcctctaaacgggtcttgaggggttttttgctgaaaggaggaactatatccgga
t Figure 15
A.
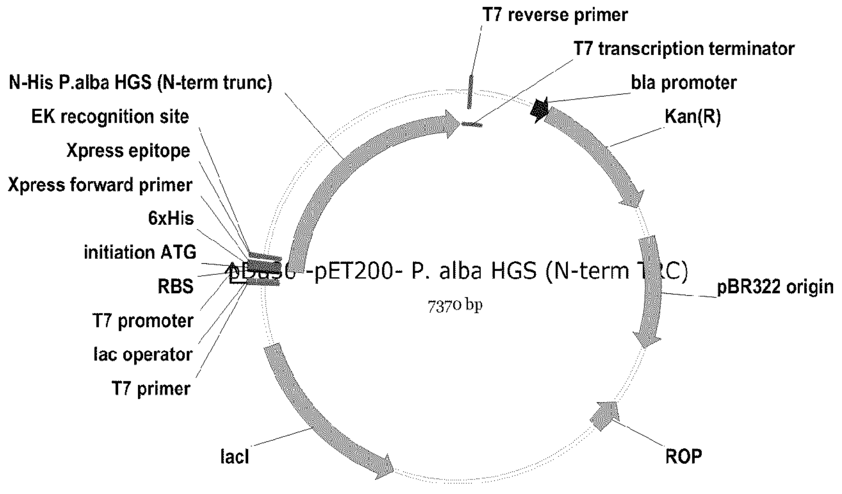
B.
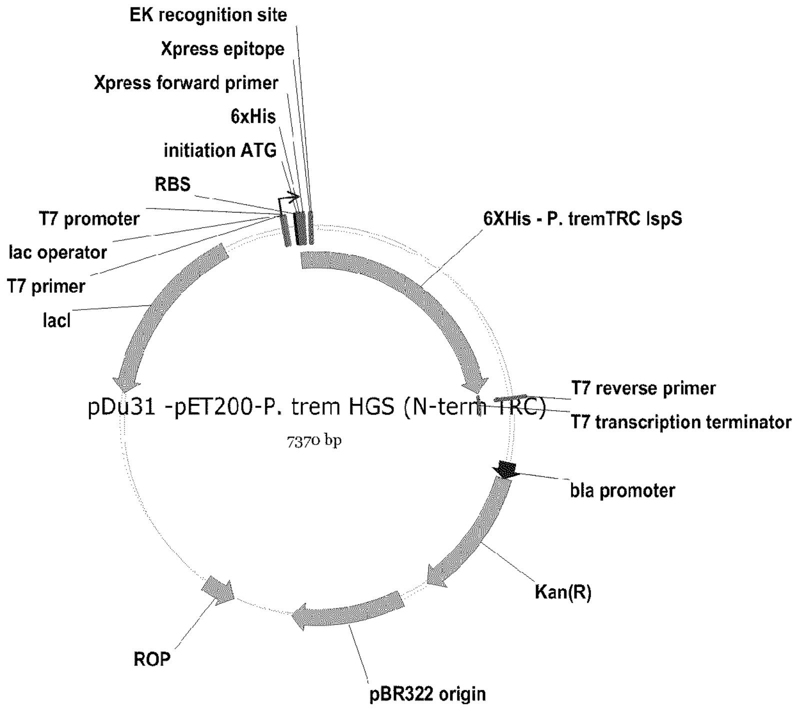

Figure 16 (Amino Acid Sequence of IspS variant P. albaTRC-pET200 (in pDu30))

MRGSHHHHHHGMASMTGGQQMGRDLYDDDDKDHPFTMRRSANYEPNSWDYDYLLSSDTD
ESIEVYKDKAKKLEAEVRREINNEKAEFLTLLELIDNVQRLGLGYRFESDIRGALDRFV
SSGGFDAVTKTSLHGTALSFRLLRQHGFEVSQEAFSGFKDQNGNFLENLKEDIKAILSL
YEASFLALEGENILDEAKVFAISHLKELSEEKIGKELAEQVNHALELPLHRRTQRLEAV
WSIEAYRKKEDANQVLLELAILDYNMIQSVYQRDLRETSRWWRRVGLATKLHFARDRLI
ESFYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNK
STPTFDDYFGNAWKSSSGPLQLVFAYFAVVQNIKKEEIENLQKYHDTISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER

Figure 17A (DNA Sequence of pDu30)

aagggcgagctcaacgatccggctgctaacaaagcccgaaaggaagctgagttggctgc
tgccaccgctgagcaataactagcataaccccttggggcctctaaacgggtcttgagga
gttttttgctgaaaggaggaactatatccggatatcccgcaagaggcccggcagtaccg
gcataaccaagcctatgcctacagcatccagggtgacggtgccgaggatgacgatgagc
gcattgttagatttcatacacggtgcctgactgcgttagcaatttaactgtgataaact
accgcattaaagcttatcgatgataagctgtcaaacatgagaattaattcttgaagacg
aaagggcctcgtgatacgcctatttttataggttaatgtcatgataataatggtttctt
agacgtcaggtggcacttttcggggaaatgtgcgcggaacccctatttgtttatttttc
taaatacattcaaatatgtatccgctcatgagacaataaccctgataaatgcttcaata
atattgaaaaaggaagagtatgattgaacaagatggattgcacgcaggttctccggccg
cttgggtggagaggctattcggctatgactgggcacaactgacaatcggctgctctgat
gccgccgtgttccggctgtcagcgcaggggcgcccggttctttttgtcaagaccgacct
gtccggtgccctgaatgaactgcaggacgaggcagcgcggctatcgtggctggccacga
cgggcgttccttgcgcagctgtgctcgacgttgtcactgaagcgggaagggactggctg
ctattgggcgaagtgccggggcaggatctcctgtcatctcaccttgctcctgccgagaa
agtatccatcatggctgatgcaatgcggcggctgcatacgcttgatccggctacctgcc
cattcgaccaccaagcgaaacatcgcatcgagcgggcacgtactcggatggaagccggt
cttgtcgatcaggatgatctggacgaagagcatcaggggctcgcgccagccgaactgtt
cgccaggctcaaggcgcgcatgcccgacggcgaggatctcgtcgtgacacatggcgatg
cctgcttgccgaatatcatggtggaaaatggccgcttttctggattcatcgactgtggc
cggctgggtgtggcggaccgctatcaggacatagcgttggctacccgtgatattgctga
agagcttggcggcgaatgggctgaccgcttcctcgtgctttacggtatcgccgctcccg
attcgcagcgcatcgccttctatcgccttcttgacgagttcttctgagcgggactctgg
ggttcgaaatgaccgaccaagcgacgcctaactgtcagaccaagtttactcatatatac
tttagattgatttaaaacttcatttttaatttaaaaggatctaggtgaagatcctttttt
gataatctcatgaccaaaatcccttaacgtgagttttcgttccactgagcgtcagaccc
cgtagaaaagatcaaaggatcttcttgagatcctttttttctgcgcgtaatctgctgct
tgcaaacaaaaaaaccaccgctaccagcggtggtttgtttgccggatcaagagctacca
actctttttccgaaggtaactggcttcagcagagcgcagataccaaatactgtccttct
agtgtagccgtagttaggccaccacttcaagaactctgtagcaccgcctacatacctcg
ctctgctaatcctgttaccagtggctgctgccagtggcgataagtcgtgtcttaccggg
ttggactcaagacgatagttaccggataaggcgcagcggtcgggctgaacggggggttc
gtgcacacagcccagcttggagcgaacgacctacaccgaactgagatacctacagcgtg
agctatgagaaagcgccacgcttcccgaagggagaaaggcggacaggtatccggtaagc
ggcagggtcggaacaggagagcgcacgagggagcttccagggggaaacgcctggtatct
ttatagtcctgtcgggtttcgccacctctgacttgagcgtcgatttttgtgatgctcgt
caggggggcggagcctatggaaaaacgccagcaacgcggcctttttacggttcctggcc
ttttgctggccttttgctcacatgttctttcctgcgttatcccctgattctgtggataa
ccgtattaccgcctttgagtgagctgataccgctcgccgcagccgaacgaccgagcgca
gcgagtcagtgagcgaggaagcggaagagcgcctgatgcggtattttctccttacgcat
ctgtgcggtatttcacaccgcaatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag Figure 17B (DNA Sequence of pDu30)

atgtctgcctgttcatccgcgtccagctcgttgagtttctccagaagcgttaatgtctg
gcttctgataaagcgggccatgttaagggcggtttttcctgtttggtcactgatgcct
ccgtgtaagggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggccaggacccaac
gctgcccgagatgcgccgcgtgcggctgctggagatggcggacgcgatggatatgttct
gccaagggttggtttgcgcattcacagttctccgcaagaattgattggctccaattctt
ggagtggtgaatccgttagcgaggtgccgccggcttccattcaggtcgaggtggcccgg
ctccatgcaccgcgacgcaacgcggggaggcagacaaggtatagggcggcgcctacaat
ccatgccaacccgttccatgtgctcgccgaggcggcataaatcgccgtgacgatcagcg
gtccaatgatcgaagttaggctggtaagagccgcgagcgatccttgaagctgtccctga
tggtcgtcatctacctgcctggacagcatggcctgcaacgcgggcatcccgatgccgcc
ggaagcgagaagaatcataatggggaaggccatccagcctcgcgtcgcgaacgccagca
agacgtagcccagcgcgtcggccgccatgccggcgataatggcctgcttctcgccgaaa
cgtttggtggcgggaccagtgacgaaggcttgagcgagggcgtgcaagattccgaatac
cgcaagcgacaggccgatcatcgtcgcgctccagcgaaagcggtcctcgccgaaaatga
cccagagcgctgccggcacctgtcctacgagttgcatgataaagaagacagtcataagt
gcggcgacgatagtcatgccccgcgcccaccggaaggagctgactgggttgaaggctct
caagggcatcggtcgagatcccggtgcctaatgagtgagctaacttacattaattgcgt
tgcgctcactgcccgctttccagtcgggaaacctgtcgtgccagctgcattaatgaatc
ggccaacgcgcggggagaggcggtttgcgtattgggcgccagggtggtttttcttttca
ccagtgagacgggcaacagctgattgcccttcaccgcctggccctgagagagttgcagc
aagcggtccacgctggtttgccccagcaggcgaaaatcctgtttgatggtggttaacgg
cgggatataacatgagctgtcttcggtatcgtcgtatcccactaccgagatatccgcac
caacgcgcagcccggactcggtaatggcgcgcattgcgcccagcgccatctgatcgttg
gcaaccagcatcgcagtgggaacgatgccctcattcagcatttgcatggtttgttgaaa
accggacatggcactccagtcgccttcccgttccgctatcggctgaatttgattgcgag
tgagatatttatgccagccagccagacgcagacgcgccgagacagaacttaatgggccc
gctaacagcgcgatttgctggtgacccaatgcgaccagatgctccacgcccagtcgcgt
accgtcttcatgggagaaaataatactgttgatgggtgtctggtcagagacatcaagaa
ataacgccggaacattagtgcaggcagcttccacagcaatggcatcctggtcatccagc
ggatagttaatgatcagcccactgacgcgttgcgcgagaagattgtgcaccgccgcttt
acaggcttcgacgccgcttcgttctaccatcgacaccaccacgctggcacccagttgat
cggcgcgagatttaatcgccgcgacaatttgcgacggcgcgtgcagggccagactggag
gtggcaacgccaatcagcaacgactgtttgcccgccagttgttgtgccacgcggttggg
aatgtaattcagctccgccatcgccgcttccactttttcccgcgttttcgcagaaacgt
ggctggcctggttcaccacgcgggaaacggtctgataagagacaccggcatactctgcg
acatcgtataacgttactggtttcacattcaccaccctgaattgactctcttccgggcg
ctatcatgccataccgcgaaaggttttgcgccattcgatggtgtccgggatctcgacgc
tctcccttatgcgactcctgcattaggaagcagcccagtagtaggttgaggccgttgag Figure 17C (DNA Sequence of pDu30)

caccgccgccgcaaggaatggtgcatgcaaggagatggcgcccaacagtcccccggcca
cggggcctgccaccatacccacgccgaaacaagcgctcatgagcccgaagtggcgagcc
cgatcttccccatcggtgatgtcggcgatataggcgccagcaaccgcacctgtggcgcc
ggtgatgccggccacgatgcgtccggcgtagaggatcgagatctcgatcccgcgaaatt
aatacgactcactataggggaattgtgagcggataacaattcccctctagaaataattt
tgtttaactttaagaaggagatatacatatgcggggttctcatcatcatcatcatcatg
gtatggctagcatgactggtggacagcaaatgggtcgggatctgtacgacgatgacgat
aaggatcatcccttcaccatgcgtcgttctgcgaactacgaacctaacagctgggacta
tgattacctgctgtcctccgacacggacgagtccatcgaagtatacaaagacaaagcga
aaaagctggaagccgaagttcgtcgcgagattaataacgaaaaagcagaatttctgacc
ctgctggaactgattgacaacgtccagcgcctgggcctgggttaccgtttcgagtctga
tatccgtggtgcgctggatcgcttcgtttcctccggcggcttcgatgcggtaaccaaga
cttccctgcacggtacggcactgtctttccgtctgctgcgtcaacacggttttgaggtt
tctcaggaagcgttcagcggcttcaaagaccaaaacggcaacttcctggagaacctgaa
ggaagatatcaaagctatcctgagcctgtacgaggccagcttcctggctctggaaggcg
aaaacatcctggacgaggcgaaggttttcgcaatctctcatctgaaagaactgtctgaa
gaaaagatcggtaaagagctggcagaacaggtgaaccatgcactggaactgccactgca
tcgccgtactcagcgtctggaagcagtatggtctatcgaggcctaccgtaaaaaggagg
acgcgaatcaggttctgctggagctggcaattctggattacaacatgatccagtctgta
taccagcgtgatctgcgtgaaacgtcccgttggtggcgtcgtgtgggtctggcgaccaa
actgcactttgctcgtgaccgcctgattgagagcttctactgggccgtgggtgtagcat
tcgaaccgcaatactccgactgccgtaactccgtcgcaaaaatgtttctttcgtaacc
attatcgacgatatctacgatgtatacggcaccctggacgaactggagctgtttactga
tgcagttgagcgttgggacgtaaacgccatcaacgacctgccggattacatgaaactgt
gctttctggctctgtataacactattaacgaaatcgcctacgacaacctgaaagataaa
ggtgagaacatcctgccgtatctgaccaaagcctgggctgacctgtgcaacgctttcct
gcaagaagccaagtggctgtacaacaaatctactccgacctttgacgactacttcggca
acgcatggaaatcctcttctggcccgctgcaactggtgttcgcttacttcgctgtcgtg
cagaacattaaaaaggaagagatcgaaaacctgcaaaaataccatgacaccatctctcg
tccttcccatatcttccgtctgtgcaatgacctggctagcgcgtctgcggaaattgcgc
gtggtgaaaccgcaaatagcgtttcttgttacatgcgcactaaaggtatctccgaagaa
ctggctaccgaaagcgtgatgaatctgatcgatgaaacctggaaaaagatgaacaagga
aaaactgggtggtagcctgttcgcgaaaccgttcgtggaaaccgcgatcaacctggcac
gtcaatctcactgcacttatcataacggcgacgcgcatacctctccggatgagctgacc
cgcaaacgcgttctgtctgtaatcactgaaccgattctgccgtttgaacgctaa Figure 18 (Amino Acid Sequence of IspS variant P.tremTRC-pET200 (in pDu31))

MRGSHHHHHHGMASMTGGQQMGRDLYDDDDKDHPFTMRRSANYEPNSWDYDYLLSSDTD
ESIEVHKDKAKKLEAEVRREINNEKAEFLTLLELIDNVQRLGLGYRFESDIRRALDRFV
SSGGFDGVTKTSLHGTALSFRLLRQHGFEVSQEAFSGFKDQNGNFLENLKEDIKAILSL
YEASFLALEGENILDEAKVFAISHLKELSEEKIGKELAEQVSHALELPLHRRTQRLEAV
WSIEAYRKKEDANQVLLELAILDYNMIQSVYQRDLRETSRWWRRVGLATKLHFARDRLI
ESFYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNK
STPTFDDYFGNAWKSSSGPLQLIFAYFAVVQNIKKEEIENLQKYHDIISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER

Figure 19A (DNA Sequence of pDu31)

cgtcgttctgcgaactacgaacctaacagctgggactatgattacctgctgtcctccga
cacggacgagtccatcgaagtacacaaagacaaagcgaaaaagctggaagccgaagttc
gtcgcgagattaataacgaaaaagcagaatttctgaccctgctggaactgattgacaac
gtccagcgcctgggcctgggttaccgtttcgagtctgatatccgtcgtgcgctggatcg
cttcgtttcctccggcggcttcgatggcgtaaccaagacttccctgcacggtacggcac
tgtctttccgtctgctgcgtcaacacggttttgaggtttctcaggaagcgttcagcggc
ttcaaagaccaaaacggcaacttcctggagaacctgaaggaagatatcaaagctatcct
gagcctgtacgaggccagcttcctggctctggaaggcgaaaacatcctggacgaggcga
aggttttcgcaatctctcatctgaaagaactgtctgaagaaaagatcggtaaagagctg
gcagaacaggtgtcccatgcactggaactgccactgcatcgccgtactcagcgtctgga
agcagtatggtctatcgaggcctaccgtaaaaaggaggacgcgaaccaggttctgctgg
agctggcaattctggattacaacatgatccagtctgtataccagcgtgatctgcgtgaa
acgtcccgttggtggcgtcgtgtgggtctggcgaccaaactgcactttgctcgtgaccg
cctgattgagagcttctactgggccgtgggtgtagcattcgaaccgcaatactccgact
gccgtaactccgtcgcaaaaatgttttctttcgtaaccattatcgacgatatctacgat
gtatacggcaccctggacgaactggagctgtttactgatgcagttgagcgttgggacgt
aaacgccatcaacgacctgccggattacatgaaactgtgctttctggctctgtataaca
ctattaacgaaatcgcctacgacaacctgaaagataaaggtgagaacatcctgccgtat
ctgaccaaagcctgggctgacctgtgcaacgctttcctgcaagaagccaagtggctgta
caacaaatctactccgacctttgacgactacttcggcaacgcatggaaatcctcttctg
gcccgctgcaactgatcttcgcttacttcgctgtcgtgcagaacattaaaaaggaagag
atcgaaaacctgcaaaaataccatgacatcatctctcgtccttcccatatcttccgtct
gtgcaatgacctggctagcgcgtctgcggaaattgcgcgtggtgaaaccgcaaatagcg
tttcttgttacatgcgcactaaaggtatctccgaagaactggctaccgaaagcgtgatg
aatctgatcgatgaaacctggaaaaagatgaacaaggaaaaactgggtggtagcctgtt
cgcgaaaccgttcgtggaaaccgcgatcaacctggcacgtcaatctcactgcacttatc
ataacggcgacgcgcatacctctccggatgagctgacccgcaaacgcgttctgtctgta
atcactgaaccgattctgccgtttgaacgctaaaagggcgagctcaacgatccggctgc
taacaaagcccgaaaggaagctgagttggctgctgccaccgctgagcaataactagcat
aaccccttggggcctctaaacgggtcttgaggagttttttgctgaaaggaggaactata
tccggatatcccgcaagaggcccggcagtaccggcataaccaagcctatgcctacagca
tccagggtgacggtgccgaggatgacgatgagcgcattgttagatttcatacacggtgc
ctgactgcgttagcaatttaactgtgataaactaccgcattaaagcttatcgatgataa
gctgtcaaacatgagaattaattcttgaagacgaaagggcctcgtgatacgcctatttt
tataggttaatgtcatgataataatggtttcttagacgtcaggtggcacttttcgggga
aatgtgcgcggaacccctatttgtttatttttctaaatacattcaaatatgtatccgct
catgagacaataaccctgataaatgcttcaataatattgaaaaaggaagagtatgattg
aacaagatggattgcacgcaggttctccggccgcttgggtggagaggctattcggctat
gactgggcacaactgacaatcggctgctctgatgccgccgtgttccggctgtcagcgca
ggggcgcccggttctttttgtcaagaccgacctgtccggtgccctgaatgaactgcagg
acgaggcagcgcggctatcgtggctggccacgacgggcgttccttgcgcagctgtgctc
gacgttgtcactgaagcgggaagggactggctgctattgggcgaagtgccggggcagga
tctcctgtcatctcaccttgctcctgccgagaaagtatccatcatggctgatgcaatgc
ggcggctgcatacgcttgatccggctacctgcccattcgaccaccaagcgaaacatcgc
atcgagcgggcacgtactcggatggaagccggtcttgtcgatcaggatgatctggacga Figure 19B (DNA Sequence of pDu31)

agagcatcaggggctcgcgccagccgaactgttcgccaggctcaaggcgcgcatgcccg
acggcgaggatctcgtcgtgacacatggcgatgcctgcttgccgaatatcatggtggaa
aatggccgcttttctggattcatcgactgtggccggctgggtgtggcggaccgctatca
ggacatagcgttggctacccgtgatattgctgaagagcttggcggcgaatgggctgacc
gcttcctcgtgctttacggtatcgccgctcccgattcgcagcgcatcgccttctatcgc
cttcttgacgagttcttctgagcgggactctggggttcgaaatgaccgaccaagcgacg
cctaactgtcagaccaagtttactcatatatactttagattgatttaaaacttcatttt
taatttaaaaggatctaggtgaagatcctttttgataatctcatgaccaaaatccctta
acgtgagttttcgttccactgagcgtcagaccccgtagaaaagatcaaaggatcttctt
gagatcctttttttctgcgcgtaatctgctgcttgcaaacaaaaaaaccaccgctacca
gcggtggtttgtttgccggatcaagagctaccaactctttttccgaaggtaactggctt
cagcagagcgcagataccaaatactgtccttctagtgtagccgtagttaggccaccact
tcaagaactctgtagcaccgcctacatacctcgctctgctaatcctgttaccagtggct
gctgccagtggcgataagtcgtgtcttaccgggttggactcaagacgatagttaccgga
taaggcgcagcggtcgggctgaacggggggttcgtgcacacagcccagcttggagcgaa
cgacctacaccgaactgagatacctacagcgtgagctatgagaaagcgccacgcttccc
gaagggagaaaggcggacaggtatccggtaagcggcagggtcggaacaggagagcgcac
gagggagcttccagggggaaacgcctggtatctttatagtcctgtcgggtttcgccacc
tctgacttgagcgtcgatttttgtgatgctcgtcaggggggcggagcctatggaaaaac
gccagcaacgcggcctttttacggttcctggccttttgctggccttttgctcacatgtt
ctttcctgcgttatcccctgattctgtggataaccgtattaccgcctttgagtgagctg
ataccgctcgccgcagccgaacgaccgagcgcagcgagtcagtgagcgaggaagcggaa
gagcgcctgatgcggtattttctccttacgcatctgtgcggtatttcacaccgcaatgg
tgcactctcagtacaatctgctctgatgccgcatagttaagccagtatacactccgcta
tcgctacgtgactgggtcatggctgcgccccgacacccgccaacacccgctgacgcgcc
ctgacgggcttgtctgctcccggcatccgcttacagacaagctgtgaccgtctccggga
gctgcatgtgtcagaggttttcaccgtcatcaccgaaacgcgcgaggcagctgcggtaa
agctcatcagcgtggtcgtgaagcgattcacagatgtctgcctgttcatccgcgtccag
ctcgttgagtttctccagaagcgttaatgtctggcttctgataaagcgggccatgttaa
gggcggtttttcctgtttggtcactgatgcctccgtgtaagggggatttctgttcatg
gggtaatgataccgatgaaacgagagaggatgctcacgatacgggttactgatgatga
acatgcccggttactggaacgttgtgagggtaaacaactggcggtatggatgcggcggg
accagagaaaaatcactcagggtcaatgccagcgcttcgttaatacagatgtaggtgtt
ccacagggtagccagcagcatcctgcgatgcagatccggaacataatggtgcagggcgc
tgacttccgcgtttccagactttacgaaacacggaaaccgaagaccattcatgttgttg
ctcaggtcgcagacgttttgcagcagcagtcgcttcacgttcgctcgcgtatcggtgat
tcattctgctaaccagtaaggcaaccccgccagcctagccgggtcctcaacgacaggag
cacgatcatgcgcacccgtggccaggacccaacgctgcccgagatgcgccgcgtgcggc
tgctggagatggcggacgcgatggatatgttctgccaagggttggtttgcgcattcaca
gttctccgcaagaattgattggctccaattcttggagtggtgaatccgttagcgaggtg
ccgccggcttccattcaggtcgaggtggcccggctccatgcaccgcgacgcaacgcggg
gaggcagacaaggtatagggcggcgcctacaatccatgccaacccgttccatgtgctcg
ccgaggcggcataaatcgccgtgacgatcagcggtccaatgatcgaagttaggctggta
agagccgcgagcgatccttgaagctgtccctgatggtcgtcatctacctgcctggacag
catggcctgcaacgcgggcatcccgatgccgccggaagcgagaagaatcataatgggga Figure 19C (DNA Sequence of pDu31)

aggccatccagcctcgcgtcgcgaacgccagcaagacgtagcccagcgcgtcggccgcc
atgccggcgataatggcctgcttctcgccgaaacgtttggtggcgggaccagtgacgaa
ggcttgagcgagggcgtgcaagattccgaataccgcaagcgacaggccgatcatcgtcg
cgctccagcgaaagcggtcctcgccgaaaatgacccagagcgctgccggcacctgtcct
acgagttgcatgataaagaagacagtcataagtgcggcgacgatagtcatgccccgcgc
ccaccggaaggagctgactgggttgaaggctctcaagggcatcggtcgagatcccggtg
cctaatgagtgagctaacttacattaattgcgttgcgctcactgcccgctttccagtcg
ggaaacctgtcgtgccagctgcattaatgaatcggccaacgcgcggggagaggcggttt
gcgtattgggcgccagggtggtttttcttttcaccagtgagacgggcaacagctgattg
cccttcaccgcctggccctgagagagttgcagcaagcggtccacgctggtttgccccag
caggcgaaaatcctgtttgatggtggttaacggcgggatataacatgagctgtcttcgg
tatcgtcgtatcccactaccgagatatccgcaccaacgcgcagcccggactcggtaatg
gcgcgcattgcgcccagcgccatctgatcgttggcaaccagcatcgcagtgggaacgat
gccctcattcagcatttgcatggtttgttgaaaaccggacatggcactccagtcgcctt
cccgttccgctatcggctgaatttgattgcgagtgagatatttatgccagccagccaga
cgcagacgcgccgagacagaacttaatgggcccgctaacagcgcgatttgctggtgacc
caatgcgaccagatgctccacgcccagtcgcgtaccgtcttcatgggagaaaataatac
tgttgatgggtgtctggtcagagacatcaagaaataacgccggaacattagtgcaggca
gcttccacagcaatggcatcctggtcatccagcggatagttaatgatcagcccactgac
gcgttgcgcgagaagattgtgcaccgccgctttacaggcttcgacgccgcttcgttcta
ccatcgacaccaccacgctggcacccagttgatcggcgcgagatttaatcgccgcgaca
atttgcgacggcgcgtgcagggccagactggaggtggcaacgccaatcagcaacgactg
tttgcccgccagttgttgtgccacgcggttgggaatgtaattcagctccgccatcgccg
cttccactttttcccgcgttttcgcagaaacgtggctggcctggttcaccacgcgggaa
acggtctgataagagacaccggcatactctgcgacatcgtataacgttactggtttcac
attcaccaccctgaattgactctcttccgggcgctatcatgccataccgcgaaaggttt
tgcgccattcgatggtgtccgggatctcgacgctctcccttatgcgactcctgcattag
gaagcagcccagtagtaggttgaggccgttgagcaccgccgccgcaaggaatggtgcat
gcaaggagatggcgcccaacagtcccccggccacggggcctgccaccatacccacgccg
aaacaagcgctcatgagcccgaagtggcgagcccgatcttccccatcggtgatgtcggc
gatataggcgccagcaaccgcacctgtggcgccggtgatgccggccacgatgcgtccgg
cgtagaggatcgagatctcgatcccgcgaaattaatacgactcactataggggaattgt
gagcggataacaattcccctctagaaataattttgtttaactttaagaaggagatatac
atatgcggggttctcatcatcatcatcatcatggtatggctagcatgactggtggacag
caaatgggtcgggatctgtacgacgatgacgataaggatcatcccttcaccatg Figure 20 (Amino Acid Sequence of IspS variant P.trichTRC-pET200 (in pDu32))

MRGSHHHHHHGMASMTGGQQMGRDLYDDDDKDHPFTMRRSANYEPNSWDYDYLLSSDTD
ESIEVYKDKAKKLEAEVRREINNEKAEFLTLLELIDNVQRLGLGYRFESDIRRALDRFV
SSGGFDAVTKTSLHATALSFRLLRQHGFEVSQEAFSGFKDQNGNFLENLKEDIKAILSL
YEASFLALEGENILDEAKVFAISHLKELSEEKIGKDLAEQVNHALELPLHRRTQRLEAV
LSIEAYRKKEDADQVLLELAILDYNMIQSVYQRDLRETSRWWRRVGLATKLHFARDRLI
ESFYWAVGVAFEPQYSDCRNSVAKMFSFVTIIDDIYDVYGTLDELELFTNAVERWDVNA
IDDLPDYMKLCFLALYNTINEIAYDNLKEKGENILPYLTKAWADLCNAFLQEAKWLYNK
STPTFDEYFGNAWKSSSGPLQLVFAYFAVVQNIKKEEIENLQKYHDIISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER

Figure 21A (DNA Sequence of pDu32)

cgtcgttctgcgaactacgaacctaacagctgggactatgattacctgctgtcctccga
cacggacgagtccatcgaagtatacaaagacaaagcgaaaaagctggaagccgaagttc
gtcgcgagattaataacgaaaaagcagaatttctgaccctgctggaactgattgacaac
gtccagcgcctgggcctgggttaccgtttcgagtctgatatccgtcgtgcgctggatcg
cttcgtttcctccggcggcttcgatgcggtaaccaagacttccctgcacgcgacggcac
tgtctttccgtctgctgcgtcaacacggttttgaggtttctcaggaagcgttcagcggc
ttcaaagaccaaaacggcaacttcctggagaacctgaaggaagatatcaaagctatcct
gagcctgtacgaggccagcttcctggctctggaaggcgaaaacatcctggacgaggcga
aggttttcgcaatctctcatctgaaagaactgtctgaagaaaagatcggtaaagatctg
gcagaacaggtgaaccatgcactggaactgccactgcatcgccgtactcagcgtctgga
agcagtactgtctatcgaggcctaccgtaaaaaggaggacgcggatcaggttctgctgg
agctggcaattctggattacaacatgatccagtctgtataccagcgtgatctgcgtgaa
acgtcccgttggtggcgtcgtgtgggtctggcgaccaaactgcactttgctcgtgaccg
cctgattgagagcttctactgggccgtgggtgtagcattcgaaccgcaatactccgact
gccgtaactccgtcgcaaaaatgtttctttcgtaaccattatcgacgatatctacgat
gtatacggcaccctggacgaactggagctgtttactaacgcagttgagcgttgggacgt
aaacgccatcgacgatctgccggattacatgaaactgtgctttctggctctgtataaca
ctattaacgaaatcgcctacgacaacctgaaagaaaaaggtgagaacatcctgccgtat
ctgaccaaagcctgggctgacctgtgcaacgctttcctgcaagaagccaagtggctgta
caacaaatctactccgacctttgacgaatacttcggcaacgcatggaaatcctcttctg
gcccgctgcaactggtgttcgcttacttcgctgtcgtgcagaacattaaaaaggaagag
atcgaaaacctgcaaaaataccatgacatcatctctcgtccttcccatatcttccgtct
gtgcaatgacctggctagcgcgtctgcggaaattgcgcgtggtgaaaccgcaaatagcg
tttcttgttacatgcgcactaaaggtatctccgaagaactggctaccgaaagcgtgatg
aatctgatcgatgaaacctggaaaaagatgaacaaggaaaaactgggtggtagcctgtt
cgcgaaaccgttcgtggaaaccgcgatcaacctggcacgtcaatctcactgcacttatc
ataacggcgacgcgcatacctctccggatgagctgacccgcaaacgcgttctgtctgta
atcactgaaccgattctgccgtttgaacgctaaaaggcgagctcaacgatccggctgc
taacaaagcccgaaaggaagctgagttggctgctgccaccgctgagcaataactagcat
aaccccttggggcctctaaacgggtcttgaggagttttttgctgaaaggaggaactata
tccggatatcccgcaagaggcccggcagtaccggcataaccaagcctatgcctacagca
tccagggtgacggtgccgaggatgacgatgagcgcattgttagatttcatacacggtgc
ctgactgcgttagcaatttaactgtgataaactaccgcattaaagcttatcgatgataa
gctgtcaaacatgagaattaattcttgaagacgaaagggcctcgtgatacgcctatttt
tataggttaatgtcatgataataatggtttcttagacgtcaggtggcacttttcgggga
aatgtgcgcggaacccctatttgtttatttttctaaatacattcaaatatgtatccgct
catgagacaataaccctgataaatgcttcaataatattgaaaaaggaagagtatgattg
aacaagatggattgcacgcaggttctccggccgcttgggtggagaggctattcggctat
gactgggcacaactgacaatcggctgctctgatgccgccgtgttccggctgtcagcgca
ggggcgcccggttctttttgtcaagaccgacctgtccggtgccctgaatgaactgcagg
acgaggcagcgcggctatcgtggctggccacgacgggcgttccttgcgcagctgtgctc
gacgttgtcactgaagcgggaagggactggctgctattgggcgaagtgccggggcagga
tctcctgtcatctcaccttgctcctgccgagaaagtatccatcatggctgatgcaatgc
ggcggctgcatacgcttgatccggctacctgcccattcgaccaccaagcgaaacatcgc
atcgagcgggcacgtactcggatggaagccggtcttgtcgatcaggatgatctggacga Figure 21B (DNA Sequence of pDu32)

agagcatcaggggctcgcgccagccgaactgttcgccaggctcaaggcgcgcatgcccg
acggcgaggatctcgtcgtgacacatggcgatgcctgcttgccgaatatcatggtggaa
aatggccgcttttctggattcatcgactgtggccggctgggtgtggcggaccgctatca
ggacatagcgttggctacccgtgatattgctgaagagcttggcggcgaatgggctgacc
gcttcctcgtgctttacggtatcgccgctcccgattcgcagcgcatcgccttctatcgc
cttcttgacgagttcttctgagcgggactctggggttcgaaatgaccgaccaagcgacg
cctaactgtcagaccaagtttactcatatatactttagattgatttaaaacttcatttt
taatttaaaaggatctaggtgaagatcctttttgataatctcatgaccaaaatccctta
acgtgagttttcgttccactgagcgtcagaccccgtagaaaagatcaaaggatcttctt
gagatcctttttttctgcgcgtaatctgctgcttgcaaacaaaaaaaccaccgctacca
gcggtggtttgtttgccggatcaagagctaccaactctttttccgaaggtaactggctt
cagcagagcgcagataccaaatactgtccttctagtgtagccgtagttaggccaccact
tcaagaactctgtagcaccgcctacatacctcgctctgctaatcctgttaccagtggct
gctgccagtggcgataagtcgtgtcttaccgggttggactcaagacgatagttaccgga
taaggcgcagcggtcgggctgaacggggggttcgtgcacacagcccagcttggagcgaa
cgacctacaccgaactgagatacctacagcgtgagctatgagaaagcgccacgcttccc
gaagggagaaaggcggacaggtatccggtaagcggcagggtcggaacaggagagcgcac
gagggagcttccagggggaaacgcctggtatctttatagtcctgtcgggtttcgccacc
tctgacttgagcgtcgatttttgtgatgctcgtcaggggggcggagcctatggaaaaac
gccagcaacgcggcctttttacggttcctggccttttgctggccttttgctcacatgtt
ctttcctgcgttatcccctgattctgtggataaccgtattaccgcctttgagtgagctg
ataccgctcgccgcagccgaacgaccgagcgcagcgagtcagtgagcgaggaagcggaa
gagcgcctgatgcggtattttctccttacgcatctgtgcggtatttcacaccgcaatgg
tgcactctcagtacaatctgctctgatgccgcatagttaagccagtatacactccgcta
tcgctacgtgactgggtcatggctgcgccccgacacccgccaacacccgctgacgcgcc
ctgacgggcttgtctgctcccggcatccgcttacagacaagctgtgaccgtctccggga
gctgcatgtgtcagaggttttcaccgtcatcaccgaaacgcgcgaggcagctgcggtaa
agctcatcagcgtggtcgtgaagcgattcacagatgtctgcctgttcatccgcgtccag
ctcgttgagtttctccagaagcgttaatgtctggcttctgataaagcgggccatgttaa
gggcggttttttcctgtttggtcactgatgcctccgtgtaagggggatttctgttcatg
ggggtaatgataccgatgaaacgagagaggatgctcacgatacgggttactgatgatga
acatgcccggttactggaacgttgtgagggtaaacaactggcggtatggatgcggcggg
accagagaaaaatcactcagggtcaatgccagcgcttcgttaatacagatgtaggtgtt
ccacagggtagccagcagcatcctgcgatgcagatccggaacataatggtgcaggcgc
tgacttccgcgtttccagactttacgaaacacggaaaccgaagaccattcatgttgttg
ctcaggtcgcagacgttttgcagcagcagtcgcttcacgttcgctcgcgtatcggtgat
tcattctgctaaccagtaaggcaaccccgccagcctagccgggtcctcaacgacaggag
cacgatcatgcgcacccgtggccaggacccaacgctgcccgagatgcgccgcgtgcggc
tgctggagatggcggacgcgatggatatgttctgccaagggttggtttgcgcattcaca
gttctccgcaagaattgattggctccaattcttggagtggtgaatccgttagcgaggtg
ccgccggcttccattcaggtcgaggtggcccggctccatgcaccgcgacgcaacgcggg
gaggcagacaaggtatagggcggcgcctacaatccatgccaacccgttccatgtgctcg
ccgaggcggcataaatcgccgtgacgatcagcggtccaatgatcgaagttaggctggta
agagccgcgagcgatccttgaagctgtccctgatggtcgtcatctacctgcctggacag
catggcctgcaacgcgggcatcccgatgccgccggaagcgagaagaatcataatgggga Figure 21C (DNA Sequence of pDu32)

aggccatccagcctcgcgtcgcgaacgccagcaagacgtagcccagcgcgtcggccgcc
atgccggcgataatggcctgcttctcgccgaaacgtttggtggcgggaccagtgacgaa
ggcttgagcgagggcgtgcaagattccgaataccgcaagcgacaggccgatcatcgtcg
cgctccagcgaaagcggtcctcgccgaaaatgacccagagcgctgccggcacctgtcct
acgagttgcatgataaagaagacagtcataagtgcggcgacgatagtcatgccccgcgc
ccaccggaaggagctgactgggttgaaggctctcaagggcatcggtcgagatcccggtg
cctaatgagtgagctaacttacattaattgcgttgcgctcactgcccgctttccagtcg
ggaaacctgtcgtgccagctgcattaatgaatcggccaacgcgcggggagaggcggttt
gcgtattgggcgccagggtggtttttcttttcaccagtgagacgggcaacagctgattg
cccttcaccgcctggccctgagagagttgcagcaagcggtccacgctggtttgccccag
caggcgaaaatcctgtttgatggtggttaacggcgggatataacatgagctgtcttcgg
tatcgtcgtatcccactaccgagatatccgcaccaacgcgcagcccggactcggtaatg
gcgcgcattgcgcccagcgccatctgatcgttggcaaccagcatcgcagtgggaacgat
gccctcattcagcatttgcatggtttgttgaaaaccggacatggcactccagtcgcctt
cccgttccgctatcggctgaatttgattgcgagtgagatatttatgccagccagccaga
cgcagacgcgccgagacagaacttaatgggcccgctaacagcgcgatttgctggtgacc
caatgcgaccagatgctccacgcccagtcgcgtaccgtcttcatgggagaaaataatac
tgttgatgggtgtctggtcagagacatcaagaaataacgccggaacattagtgcaggca
gcttccacagcaatggcatcctggtcatccagcggatagttaatgatcagcccactgac
gcgttgcgcgagaagattgtgcaccgccgctttacaggcttcgacgccgcttcgttcta
ccatcgacaccaccacgctggcacccagttgatcggcgcgagatttaatcgccgcgaca
atttgcgacggcgcgtgcagggccagactggaggtggcaacgccaatcagcaacgactg
tttgcccgccagttgttgtgccacgcggttgggaatgtaattcagctccgccatcgccg
cttccactttttcccgcgttttcgcagaaacgtggctggcctggttcaccacgcgggaa
acggtctgataagagacaccggcatactctgcgacatcgtataacgttactggtttcac
attcaccaccctgaattgactctcttccgggcgctatcatgccataccgcgaaaggttt
tgcgccattcgatggtgtccgggatctcgacgctctcccttatgcgactcctgcattag
gaagcagcccagtagtaggttgaggccgttgagcaccgccgccgcaaggaatggtgcat
gcaaggagatggcgcccaacagtcccccggccacggggcctgccaccatacccacgccg
aaacaagcgctcatgagcccgaagtggcgagcccgatcttccccatcggtgatgtcggc
gatataggcgccagcaaccgcacctgtggcgccggtgatgccggccacgatgcgtccgg
cgtagaggatcgagatctcgatcccgcgaaattaatacgactcactataggggaattgt
gagcggataacaattcccctctagaaataattttgtttaactttaagaaggagatatac
atatgcggggttctcatcatcatcatcatcatggtatggctagcatgactggtggacag
caaatgggtcgggatctgtacgacgatgacgataaggatcatcccttcaccatg Figure 22A (DNA sequence of pDu27)

aagggcgagctcaacgatccggctgctaacaaagcccgaaaggaagctgagttggctgc
tgccaccgctgagcaataactagcataaccccttggggcctctaaacgggtcttgagga
gttttttgctgaaaggaggaactatatccggatatcccgcaagaggcccggcagtaccg
gcataaccaagcctatgcctacagcatccagggtgacggtgccgaggatgacgatgagc
gcattgttagatttcatacacggtgcctgactgcgttagcaatttaactgtgataaact
accgcattaaagcttatcgatgataagctgtcaaacatgagaattaattcttgaagacg
aaagggcctcgtgatacgcctatttttataggttaatgtcatgataataatggtttctt
agacgtcaggtggcacttttcggggaaatgtgcgcggaacccctatttgtttatttttc
taaatacattcaaatatgtatccgctcatgagacaataaccctgataaatgcttcaata
atattgaaaaaggaagagtatgattgaacaagatggattgcacgcaggttctccggccg
cttgggtggagaggctattcggctatgactgggcacaactgacaatcggctgctctgat
gccgccgtgttccggctgtcagcgcaggggcgcccggttctttttgtcaagaccgacct
gtccggtgccctgaatgaactgcaggacgaggcagcgcggctatcgtggctggccacga
cgggcgttccttgcgcagctgtgctcgacgttgtcactgaagcgggaagggactggctg
ctattgggcgaagtgccggggcaggatctcctgtcatctcaccttgctcctgccgagaa
agtatccatcatggctgatgcaatgcggcggctgcatacgcttgatccggctacctgcc
cattcgaccaccaagcgaaacatcgcatcgagcgggcacgtactcggatggaagccggt
cttgtcgatcaggatgatctggacgaagagcatcaggggctcgcgccagccgaactgtt
cgccaggctcaaggcgcgcatgcccgacggcgaggatctcgtcgtgacacatggcgatg
cctgcttgccgaatatcatggtggaaaatggccgcttttctggattcatcgactgtggc
cggctgggtgtggcggaccgctatcaggacatagcgttggctacccgtgatattgctga
agagcttggcggcgaatgggctgaccgcttcctcgtgctttacggtatcgccgctcccg
attcgcagcgcatcgccttctatcgccttcttgacgagttcttctgagcgggactctgg
ggttcgaaatgaccgaccaagcgacgcctaactgtcagaccaagtttactcatatatac
tttagattgatttaaaacttcatttttaatttaaaaggatctaggtgaagatcctttt
gataatctcatgaccaaaatcccttaacgtgagttttcgttccactgagcgtcagaccc
cgtagaaaagatcaaaggatcttcttgagatcctttttttctgcgcgtaatctgctgct
tgcaaacaaaaaaaccaccgctaccagcggtggtttgtttgccggatcaagagctacca
actctttttccgaaggtaactggcttcagcagagcgcagataccaaatactgtccttct
agtgtagccgtagttaggccaccacttcaagaactctgtagcaccgcctacatacctcg
ctctgctaatcctgttaccagtggctgctgccagtggcgataagtcgtgtcttaccggg
ttggactcaagacgatagttaccggataaggcgcagcggtcgggctgaacggggggttc
gtgcacacagcccagcttggagcgaacgacctacaccgaactgagatacctacagcgtg
agctatgagaaagcgccacgcttcccgaagggagaaaggcggacaggtatccggtaagc
ggcagggtcggaacaggagagcgcacgagggagcttccagggggaaacgcctggtatct
ttatagtcctgtcgggtttcgccacctctgacttgagcgtcgatttttgtgatgctcgt
caggggggcggagcctatggaaaaacgccagcaacgcggcctttttacggttcctggcc
ttttgctggccttttgctcacatgttctttcctgcgttatcccctgattctgtggataa
ccgtattaccgcctttgagtgagctgataccgctcgccgcagccgaacgaccgagcgca
gcgagtcagtgagcgaggaagcggaagagcgcctgatgcggtattttctccttacgcat
ctgtgcggtatttcacaccgcaatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag Figure 22B (DNA sequence of pDu27)

atgtctgcctgttcatccgcgtccagctcgttgagtttctccagaagcgttaatgtctg
gcttctgataaagcgggccatgttaagggcggtttttcctgtttggtcactgatgcct
ccgtgtaagggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggccaggacccaac
gctgcccgagatgcgccgcgtgcggctgctggagatggcggacgcgatggatatgttct
gccaagggttggtttgcgcattcacagttctccgcaagaattgattggctccaattctt
ggagtggtgaatccgttagcgaggtgccgccggcttccattcaggtcgaggtggcccgg
ctccatgcaccgcgacgcaacgcggggaggcagacaaggtatagggcggcgcctacaat
ccatgccaacccgttccatgtgctcgccgaggcggcataaatcgccgtgacgatcagcg
gtccaatgatcgaagttaggctggtaagagccgcgagcgatccttgaagctgtccctga
tggtcgtcatctacctgcctggacagcatggcctgcaacgcgggcatcccgatgccgcc
ggaagcgagaagaatcataatggggaaggccatccagcctcgcgtcgcgaacgccagca
agacgtagcccagcgcgtcggccgccatgccggcgataatggcctgcttctcgccgaaa
cgtttggtggcgggaccagtgacgaaggcttgagcgagggcgtgcaagattccgaatac
cgcaagcgacaggccgatcatcgtcgcgctccagcgaaagcggtcctcgccgaaaatga
cccagagcgctgccggcacctgtcctacgagttgcatgataaagaagacagtcataagt
gcggcgacgatagtcatgccccgcgcccaccggaaggagctgactgggttgaaggctct
caagggcatcggtcgagatcccggtgcctaatgagtgagctaacttacattaattgcgt
tgcgctcactgcccgctttccagtcgggaaacctgtcgtgccagctgcattaatgaatc
ggccaacgcgcggggagaggcggtttgcgtattgggcgccagggtggtttttcttttca
ccagtgagacgggcaacagctgattgcccttcaccgcctggccctgagagagttgcagc
aagcggtccacgctggtttgccccagcaggcgaaaatcctgtttgatggtggttaacgg
cgggatataacatgagctgtcttcggtatcgtcgtatcccactaccgagatatccgcac
caacgcgcagcccggactcggtaatggcgcgcattgcgcccagcgccatctgatcgttg
gcaaccagcatcgcagtgggaacgatgccctcattcagcatttgcatggtttgttgaaa
accggacatggcactccagtcgccttcccgttccgctatcggctgaatttgattgcgag
tgagatatttatgccagccagccagacgcagacgcgccgagacagaacttaatgggccc
gctaacagcgcgatttgctggtgacccaatgcgaccagatgctccacgcccagtcgcgt
accgtcttcatgggagaaaataatactgttgatgggtgtctggtcagagacatcaagaa
ataacgccggaacattagtgcaggcagcttccacagcaatggcatcctggtcatccagc
ggatagttaatgatcagcccactgacgcgttgcgcgagaagattgtgcaccgccgcttt
acaggcttcgacgccgcttcgttctaccatcgacaccaccacgctggcacccagttgat
cggcgcgagatttaatcgccgcgacaatttgcgacggcgcgtgcagggccagactggag
gtggcaacgccaatcagcaacgactgtttgcccgccagttgttgtgccacgcggttggg
aatgtaattcagctccgccatcgccgcttccactttttcccgcgttttcgcagaaacgt
ggctggcctggttcaccacgcgggaaacggtctgataagagacaccggcatactctgcg
acatcgtataacgttactggtttcacattcaccaccctgaattgactctcttccgggcg
ctatcatgccataccgcgaaaggttttgcgccattcgatggtgtccgggatctcgacgc
tctccccttatgcgactcctgcattaggaagcagcccagtagtaggttgaggccgttgag Figure 22C (DNA sequence of pDu27)

caccgccgccgcaaggaatggtgcatgcaaggagatggcgcccaacagtcccccggcca
cggggcctgccaccatacccacgccgaaacaagcgctcatgagcccgaagtggcgagcc
cgatcttccccatcggtgatgtcggcgatataggcgccagcaaccgcacctgtggcgcc
ggtgatgccggccacgatgcgtccggcgtagaggatcgagatctcgatcccgcgaaatt
aatacgactcactataggggaattgtgagcggataacaattcccctctagaaataattt
tgtttaactttaagaaggagatatacatatgcggggttctcatcatcatcatcatcatg
gtatggctagcatgactggtggacagcaaatgggtcgggatctgtacgacgatgacgat
aaggatcatcccttcaccatgcgttgtagcgtgtccaccgaaaatgtgtctttcaccga
aactgaaaccgaagctcgtcgttctgcgaactacgaacctaacagctgggactatgatt
acctgctgtcctccgacacggacgagtccatcgaagtatacaaagacaaagcgaaaaag
ctggaagccgaagttcgtcgcgagattaataacgaaaaagcagaatttctgaccctgct
ggaactgattgacaacgtccagcgcctgggcctgggttaccgtttcgagtctgatatcc
gtggtgcgctggatcgcttcgtttcctccggcggcttcgatgcggtaaccaagacttcc
ctgcacggtacggcactgtctttccgtctgctgcgtcaacacggttttgaggtttctca
ggaagcgttcagcggcttcaaagaccaaaacggcaacttcctggagaacctgaaggaag
atatcaaagctatcctgagcctgtacgaggccagcttcctggctctggaaggcgaaaac
atcctggacgaggcgaaggttttcgcaatctctcatctgaaagaactgtctgaagaaaa
gatcggtaaagagctggcagaacaggtgaaccatgcactggaactgccactgcatcgcc
gtactcagcgtctggaagcagtatggtctatcgaggcctaccgtaaaaaggaggacgcg
aatcaggttctgctggagctggcaattctggattacaacatgatccagtctgtatacca
gcgtgatctgcgtgaaacgtcccgttggtggcgtcgtgtgggtctggcgaccaaactgc
actttgctcgtgaccgcctgattgagagcttctactgggccgtgggtgtagcattcgaa
ccgcaatactccgactgccgtaactccgtcgcaaaaatgttttctttcgtaaccattat
cgacgatatctacgatgtatacggcaccctggacgaactggagctgtttactgatgcag
ttgagcgttgggacgtaaacgccatcaacgacctgccggattacatgaaactgtgcttt
ctggctctgtataacactattaacgaaatcgcctacgacaacctgaaagataaaggtga
gaacatcctgccgtatctgaccaaagcctgggctgacctgtgcaacgctttcctgcaag
aagccaagtggctgtacaacaaatctactccgacctttgacgactacttcggcaacgca
tggaaatcctcttctggcccgctgcaactggtgttcgcttacttcgctgtcgtgcagaa
cattaaaaaggaagagatcgaaaacctgcaaaaataccatgacaccatctctcgtcctt
cccatatcttccgtctgtgcaatgacctggctagcgcgtctgcggaaattgcgcgtggt
gaaaccgcaaatagcgtttcttgttacatgcgcactaaaggtatctccgaagaactggc
taccgaaagcgtgatgaatctgatcgatgaaacctggaaaaagatgaacaaggaaaaac
tgggtggtagcctgttcgcgaaaccgttcgtggaaaccgcgatcaacctggcacgtcaa
tctcactgcacttatcataacggcgacgcgcatacctctccggatgagctgacccgcaa
acgcgttctgtctgtaatcactgaaccgattctgccgtttgaacgctaa Figure 23 (Amino Acid Sequence of Full Length P. alba IspS (in P. alba pET24a))

MRCSVSTENVSFTETETEARRSANYEPNSWDYDYLLSSDTDESIEVYKDKAKKLEAEVR
REINNEKAEFLTLLELIDNVQRLGLGYRFESDIRGALDRFVSSGGFDAVTKTSLHGTAL
SFRLLRQHGFEVSQEAFSGFKDQNGNFLENLKEDIKAILSLYEASFLALEGENILDEAK
VFAISHLKELSEEKIGKELAEQVNHALELPLHRRTQRLEAVWSIEAYRKKEDANQVLLE
LAILDYNMIQSVYQRDLRETSRWWRRVGLATKLHFARDRLIESFYWAVGVAFEPQYSDC
RNSVAKMFSFVTIIDDIYDVYGTLDELELFTDAVERWDVNAINDLPDYMKLCFLALYNT
INEIAYDNLKDKGENILPYLTKAWADLCNAFLQEAKWLYNKSTPTFDDYFGNAWKSSSG
PLQLVFAYFAVVQNIKKEEIENLQKYHDTISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFER

Figure 24A (DNA sequence of P. alba pET24a)

tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctccctttt
agggttccgatttagtgctttacggcacctcgaccccaaaaaacttgattagggtgatg
gttcacgtagtgggccatcgccctgatagacggtttttcgccctttgacgttggagtcc
acgttctttaatagtggactcttgttccaaactggaacaacactcaaccctatctcggt
ctattcttttgatttataagggattttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatatttttgaaaaagccgtttctgtaa
tgaaggagaaaactcaccgaggcagttccataggatggcaagatcctggtatcggtctg
cgattccgactcgtccaacatcaatacaacctattaatttcccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttcccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacaccccttgtattactgtttatgtaagcagacagtttta
ttgttcatgaccaaaatcccttaacgtgagttttcgttccactgagcgtcagaccccgt
agaaaagatcaaaggatcttcttgagatcctttttttctgcgcgtaatctgctgcttgc
aaacaaaaaaaccaccgctaccagcggtggtttgtttgccggatcaagagctaccaact
ctttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccagggggaaacgcctggtatcttta
tagtcctgtcgggtttcgccacctctgacttgagcgtcgatttttgtgatgctcgtcag
gggggcggagcctatggaaaaacgccagcaacgcggcctttttacggttcctggcctttt
tgctggccttttgctcacatgttctttcctgcgttatcccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag
atgtctgcctgttcatccgcgtccagctcgttgagtttctccagaagcgttaatgtctg Figure 24B (DNA sequence of P. alba pET24a)

gcttctgataaagcgggccatgttaagggcggttttttcctgtttggtcactgatgcct
ccgtgtaaggggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgcccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggtttttcttttcaccagtgagacgggcaacagctgattgccctt
caccgcctggccctgagagagttgcagcaagcggtccacgctggtttgccccagcaggc
gaaaatcctgtttgatggtggttaacggcgggatataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
actttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctcccttatgcgactcctgcattaggaagc
agcccagtagtaggttgaggccgttgagcaccgccgccgcaaggaatggtgcatgcaag
gagatggcgcccaacagtcccccggccacggggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactataggggaattgtgagcg
gataacaattcccctctagaaataattttgtttaactttaagaaggagatatacatatg
cgttgtagcgtgtccaccgaaaatgtgtctttcaccgaaactgaaaccgaagctcgtcg
ttctgcgaactacgaacctaacagctgggactatgattacctgctgtcctccgacacgg
acgagtccatcgaagtatacaaagacaaagcgaaaaagctggaagccgaagttcgtcgc
gagattaataacgaaaaagcagaatttctgaccctgctggaactgattgacaacgtcca Figure 24C (<u>DNA sequence of P. alba pET24a)</u>

```
gcgcctgggcctgggttaccgtttcgagtctgatatccgtggtgcgctggatcgcttcg
tttcctccggcggcttcgatgcggtaaccaagacttccctgcacggtacggcactgtct
ttccgtctgctgcgtcaacacggttttgaggtttctcaggaagcgttcagcggcttcaa
agaccaaaacggcaacttcctggagaacctgaaggaagatatcaaagctatcctgagcc
tgtacgaggccagcttcctggctctggaaggcgaaaacatcctggacgaggcgaaggtt
ttcgcaatctctcatctgaaagaactgtctgaagaaaagatcggtaaagagctggcaga
acaggtgaaccatgcactggaactgccactgcatcgccgtactcagcgtctggaagcag
tatggtctatcgaggcctaccgtaaaaaggaggacgcgaatcaggttctgctggagctg
gcaattctggattacaacatgatccagtctgtataccagcgtgatctgcgtgaaacgtc
ccgttggtggcgtcgtgtgggtctggcgaccaaactgcactttgctcgtgaccgcctga
ttgagagcttctactgggccgtgggtgtagcattcgaaccgcaatactccgactgccgt
aactccgtcgcaaaaatgttttctttcgtaaccattatcgacgatatctacgatgtata
cggcaccctggacgaactggagctgtttactgatgcagttgagcgttgggacgtaaacg
ccatcaacgacctgccggattacatgaaactgtgctttctggctctgtataacactatt
aacgaaatcgcctacgacaacctgaaagataaaggtgagaacatcctgccgtatctgac
caaagcctgggctgacctgtgcaacgctttcctgcaagaagccaagtggctgtacaaca
aatctactccgacctttgacgactacttcggcaacgcatggaaatcctcttctggcccg
ctgcaactggtgttcgcttacttcgctgtcgtgcagaacattaaaaaggaagagatcga
aaacctgcaaaaataccatgacaccatctctcgtccttcccatatcttccgtctgtgca
atgacctggctagcgcgtctgcggaaattgcgcgtggtgaaaccgcaaatagcgtttct
tgttacatgcgcactaaaggtatctccgaagaactggctaccgaaagcgtgatgaatct
gatcgatgaaacctggaaaaagatgaacaaggaaaaactgggtggtagcctgttcgcga
aaccgttcgtggaaaccgcgatcaacctggcacgtcaatctcactgcacttatcataac
ggcgacgcgcatacctctccggatgagctgacccgcaaacgcgttctgtctgtaatcac
tgaaccgattctgccgtttgaacgctaaggatccgaattcgagctccgtcgacaagctt
gcggccgcactcgagcaccaccaccaccaccactgagatccggctgctaacaaagcccg
aaaggaagctgagttggctgctgccaccgctgagcaataactagcataaccccttgggg
cctctaaacgggtcttgaggggttttttgctgaaaggaggaactatatccggat
```

Figure 25
A.
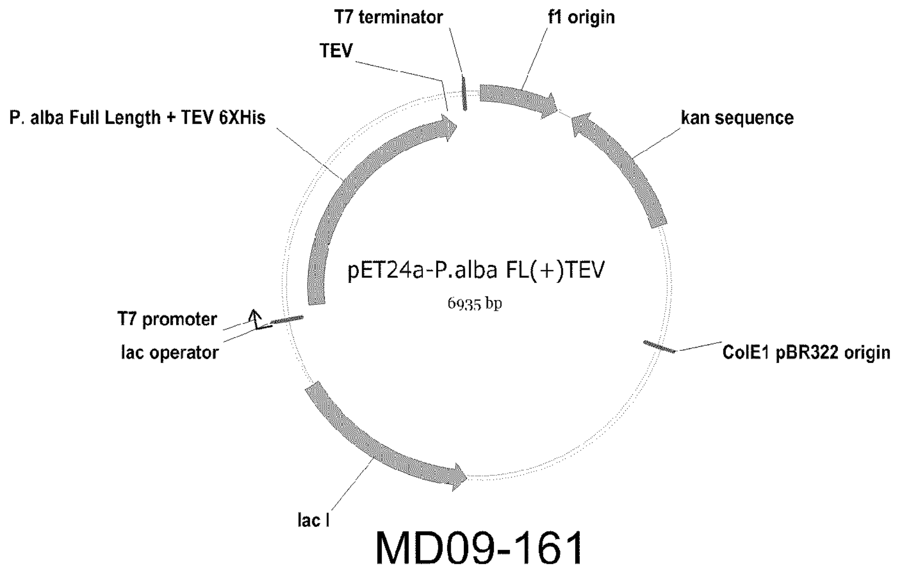
MD09-161
B.
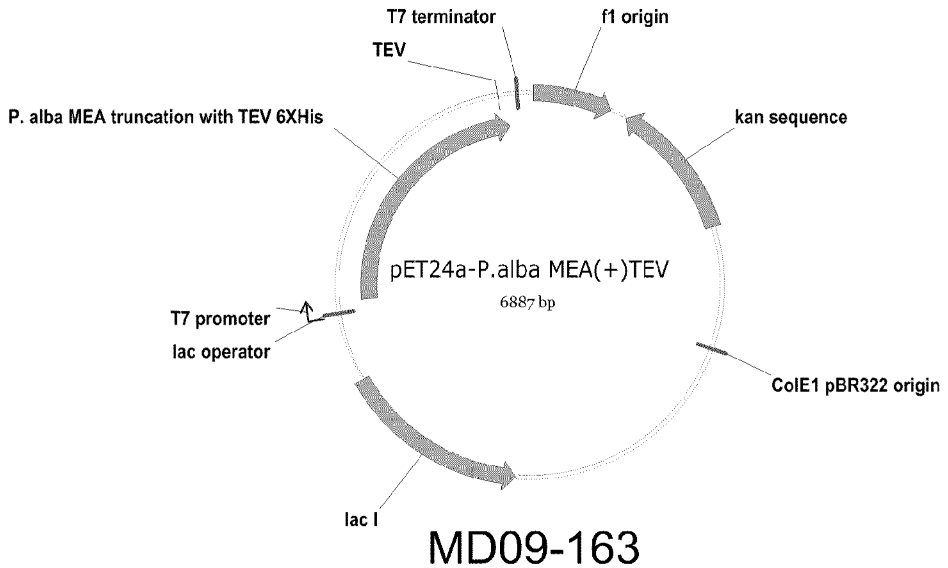
MD09-163

Figure 26 (Amino Acid Sequence of P. alba MEA(+)TEV (in MD09-163))

MEARRSANYEPNSWDYDYLLSSDTDESIEVYKDKAKKLEAEVRREINNEKAEFLTLLEL
IDNVQRLGLGYRFESDIRGALDRFVSSGGFDAVTKTSLHGTALSFRLLRQHGFEVSQEA
FSGFKDQNGNFLENLKEDIKAILSLYEASFLALEGENILDEAKVFAISHLKELSEEKIG
KELAEQVNHALELPLHRRTQRLEAVWSIEAYRKKEDANQVLLELAILDYNMIQSVYQRD
LRETSRWWRRVGLATKLHFARDRLIESFYWAVGVAFEPQYSDCRNSVAKMFSFVTIIDD
IYDVYGTLDELELFTDAVERWDVNAINDLPDYMKLCFLALYNTINEIAYDNLKDKGENI
LPYLTKAWADLCNAFLQEAKWLYNKSTPTFDDYFGNAWKSSSGPLQLVFAYFAVVQNIK
KEEIENLQKYHDTISRPSHIFRLCNDLASASAEIARGETANSVSCYMRTKGISEELATE
SVMNLIDETWKKMNKEKLGGSLFAKPFVETAINLARQSHCTYHNGDAHTSPDELTRKRV
LSVITEPILPFERENLYFQGLEHHHHHH

Figure 27A (DNA sequence of MD09-163 = pET24a-P. alba MEA(+)TEV)

(CDS is underlined, TEV protease site is bold) (Figure 6 shows plasmid map)

tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctcccttt
agggttccgatttagtgctttacggcacctcgaccccaaaaaacttgattagggtgatg
gttcacgtagtgggccatcgccctgatagacggtttttcgccctttgacgttggagtcc
acgttctttaatagtggactcttgttccaaactggaacaacactcaaccctatctcggt
ctattcttttgatttataagggattttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatatttttgaaaaagccgtttctgtaa
tgaaggagaaaactcaccgaggcagttccataggatggcaagatcctggtatcggtctg
cgattccgactcgtccaacatcaatacaacctattaatttcccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttcccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacaccccttgtattactgtttatgtaagcagacagtttta
ttgttcatgaccaaaatcccttaacgtgagttttcgttccactgagcgtcagaccccgt
agaaaagatcaaaggatcttcttgagatcctttttttctgcgcgtaatctgctgcttgc
aaacaaaaaaaccaccgctaccagcggtggtttgtttgccggatcaagagctaccaact
ctttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccagggggaaacgcctggtatcttta
tagtcctgtcgggtttcgccacctctgacttgagcgtcgatttttgtgatgctcgtcag
gggggcggagcctatggaaaaacgccagcaacgcggcctttttacggttcctggccttt
tgctggccttttgctcacatgttctttcctgcgttatcccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac Figure 27B (DNA sequence of MD09-163 = pET24a-P. alba MEA(+)TEV)

cgaaacgcgcgaggcagctgcggtaaagctcatcagcgtggtcgtgaagcgattcacag
atgtctgcctgttcatccgcgtccagctcgttgagtttctccagaagcgttaatgtctg
gcttctgataaagcgggccatgttaagggcggttttttcctgtttggtcactgatgcct
ccgtgtaagggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgcccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggtttttcttttcaccagtgagacgggcaacagctgattgccctt
caccgcctggccctgagagagttgcagcaagcggtccacgctggtttgccccagcaggc
gaaaatcctgtttgatggtggttaacggcgggatataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
actttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctcccttatgcgactcctgcattaggaagc
agcccagtagtaggttgaggccgttgagcaccgccgccgcaaggaatggtgcatgcaag
gagatggcgcccaacagtcccccggccacggggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactataggggaattgtgagcg
gataacaattcccctctagaaataattttgtttaactttaagaaggagatatacatatg
gaagctcgtcgttctgcgaactacgaacctaacagctgggactatgattacctgctgtc
ctccgacacggacgagtccatcgaagtatacaaagacaaagcgaaaaagctggaagccg Figure 27C (DNA sequence of MD09-163 = pET24a-P. alba MEA(+)TEV)

aagttcgtcgcgagattaataacgaaaaagcagaatttctgaccctgctggaactgatt
gacaacgtccagcgcctgggcctgggttaccgtttcgagtctgatatccgtggtgcgct
ggatcgcttcgtttcctccggcggcttcgatgcggtaaccaagacttccctgcacggta
cggcactgtctttccgtctgctgcgtcaacacggttttgaggtttctcaggaagcgttc
agcggcttcaaagaccaaaacggcaacttcctggagaacctgaaggaagatatcaaagc
tatcctgagcctgtacgaggccagcttcctggctctggaaggcgaaaacatcctggacg
aggcgaaggtttcgcaatctctcatctgaaagaactgtctgaagaaaagatcggtaaa
gagctggcagaacaggtgaaccatgcactggaactgccactgcatcgccgtactcagcg
tctggaagcagtatggtctatcgaggcctaccgtaaaaaggaggacgcgaatcaggttc
tgctggagctggcaattctggattacaacatgatccagtctgtataccagcgtgatctg
cgtgaaacgtcccgttggtggcgtcgtgtgggtctggcgaccaaactgcactttgctcg
tgaccgcctgattgagagcttctactgggccgtgggtgtagcattcgaaccgcaatact
ccgactgccgtaactccgtcgcaaaaatgtttctttcgtaaccattatcgacgatatc
tacgatgtatacggcaccctggacgaactggagctgtttactgatgcagttgagcgttg
ggacgtaaacgccatcaacgacctgccggattacatgaaactgtgctttctggctctgt
ataacactattaacgaaatcgcctacgacaacctgaaagataaaggtgagaacatcctg
ccgtatctgaccaaagcctgggctgacctgtgcaacgctttcctgcaagaagccaagtg
gctgtacaacaaatctactccgacctttgacgactacttcggcaacgcatggaaatcct
cttctggcccgctgcaactggtgttcgcttacttcgctgtcgtgcagaacattaaaaag
gaagagatcgaaaacctgcaaaaataccatgacaccatctctcgtccttcccatatctt
ccgtctgtgcaatgacctggctagcgcgtctgcggaaattgcgcgtggtgaaaccgcaa
atagcgtttcttgttacatgcgcactaaaggtatctccgaagaactggctaccgaaagc
gtgatgaatctgatcgatgaaacctggaaaaagatgaacaaggaaaaactgggtggtag
cctgttcgcgaaaccgttcgtggaaaccgcgatcaacctggcacgtcaatctcactgca
cttatcataacggcgacgcgcatacctctccggatgagctgacccgcaaacgcgttctg
tctgtaatcactgaaccgattctgccgtttgaacgcgaaaacctgtattttcagggcct
cgagcaccaccaccaccaccactgagatccggctgctaacaaagcccgaaaggaagctg
agttggctgctgccaccgctgagcaataactagcataaccccttggggcctctaaacgg
gtcttgaggggttttttgctgaaaggaggaactatatccggat Figure 28 (Amino Acid Sequence of P. alba FL (+) TEV (in MD09-161))

MRCSVSTENVSFTETETEARRSANYEPNSWDYDYLLSSDTDESIEVYKDKAKKLEAEVR
REINNEKAEFLTLLELIDNVQRLGLGYRFESDIRGALDRFVSSGGFDAVTKTSLHGTAL
SFRLLRQHGFEVSQEAFSGFKDQNGNFLENLKEDIKAILSLYEASFLALEGENILDEAK
VFAISHLKELSEEKIGKELAEQVNHALELPLHRRTQRLEAVWSIEAYRKKEDANQVLLE
LAILDYNMIQSVYQRDLRETSRWWRRVGLATKLHFARDRLIESFYWAVGVAFEPQYSDC
RNSVAKMFSFVTIIDDIYDVYGTLDELELFTDAVERWDVNAINDLPDYMKLCFLALYNT
INEIAYDNLKDKGENILPYLTKAWADLCNAFLQEAKWLYNKSTPTFDDYFGNAWKSSSG
PLQLVFAYFAVVQNIKKEEIENLQKYHDTISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFERENLYFQGLEHHHHHH

Figure 29A (DNA sequence of MD09-161 = pET24a-P. alba FL(+)TEV)

(CDS is underlined, TEV protease site is bold) (Figure 6 shows plasmid map)

tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctcccttt
agggttccgatttagtgctttacggcacctcgaccccaaaaaacttgattagggtgatg
gttcacgtagtgggccatcgccctgatagacggtttttcgccctttgacgttggagtcc
acgttctttaatagtggactcttgttccaaactggaacaacactcaaccctatctcggt
ctattcttttgatttataagggattttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatatttttgaaaaagccgtttctgtaa
tgaaggagaaaactcaccgaggcagttccataggatggcaagatcctggtatcggtctg
cgattccgactcgtccaacatcaatacaacctattaatttcccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttcccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacaccccttgtattactgtttatgtaagcagacagtttta
ttgttcatgaccaaaatcccttaacgtgagttttcgttccactgagcgtcagaccccgt
agaaaagatcaaaggatcttcttgagatcctttttttctgcgcgtaatctgctgcttgc
aaacaaaaaaaccaccgctaccagcggtggtttgtttgccggatcaagagctaccaact
ctttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccagggggaaacgcctggtatcttta
tagtcctgtcgggtttcgccacctctgacttgagcgtcgatttttgtgatgctcgtcag
gggggcggagcctatggaaaaacgccagcaacgcggcctttttacggttcctggccttt
tgctggccttttgctcacatgttctttcctgcgttatcccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac Figure 29B <u>(DNA sequence of MD09-161 = pET24a-P. alba FL(+)TEV)</u> cgaaacgcgcgaggcagctgcggtaaagctcatcagcgtggtcgtgaagcgattcacag
atgtctgcctgttcatccgcgtccagctcgttgagtttctccagaagcgttaatgtctg
gcttctgataaagcgggccatgttaagggcggttttttcctgtttggtcactgatgcct
ccgtgtaagggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgcccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggtttttcttttcaccagtgagacgggcaacagctgattgccctt
caccgcctggccctgagagagttgcagcaagcggtccacgctggtttgccccagcaggc
gaaaatcctgtttgatggtggttaacggcgggatataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
actttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctcccttatgcgactcctgcattaggaagc
agcccagtagtaggttgaggccgttgagcaccgccgccgcaaggaatggtgcatgcaag
gagatggcgcccaacagtcccccggccacggggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactataggggaattgtgagcg
gataacaattcccctctagaaataattttgtttaactttaagaaggagatatacat<u>atg</u>
<u>cgttgtagcgtgtccaccgaaaatgtgtctttcaccgaaactgaaaccgaagctcgtcg</u>
<u>ttctgcgaactacgaacctaacagctgggactatgattacctgctgtcctccgacacgg</u>

Figure 29C (DNA sequence of MD09-161 = pET24a-P. alba FL(+)TEV)

acgagtccatcgaagtatacaaagacaaagcgaaaaagctggaagccgaagttcgtcgc
gagattaataacgaaaaagcagaatttctgaccctgctggaactgattgacaacgtcca
gcgcctgggcctgggttaccgtttcgagtctgatatccgtggtgcgctggatcgcttcg
tttcctccggcggcttcgatgcggtaaccaagacttccctgcacggtacggcactgtct
ttccgtctgctgcgtcaacacggttttgaggtttctcaggaagcgttcagcggcttcaa
agaccaaaacggcaacttcctggagaacctgaaggaagatatcaaagctatcctgagcc
tgtacgaggccagcttcctggctctggaaggcgaaaacatcctggacgaggcgaaggtt
ttcgcaatctctcatctgaaagaactgtctgaagaaaagatcggtaaagagctggcaga
acaggtgaaccatgcactggaactgccactgcatcgccgtactcagcgtctggaagcag
tatggtctatcgaggcctaccgtaaaaaggaggacgcgaatcaggttctgctggagctg
gcaattctggattacaacatgatccagtctgtataccagcgtgatctgcgtgaaacgtc
ccgttggtggcgtcgtgtgggtctggcgaccaaactgcactttgctcgtgaccgcctga
ttgagagcttctactgggccgtgggtgtagcattcgaaccgcaatactccgactgccgt
aactccgtcgcaaaaatgtttctttcgtaaccattatcgacgatatctacgatgtata
cggcaccctggacgaactggagctgtttactgatgcagttgagcgttgggacgtaaacg
ccatcaacgacctgccggattacatgaaactgtgctttctggctctgtataacactatt
aacgaaatcgcctacgacaacctgaaagataaaggtgagaacatcctgccgtatctgac
caaagcctgggctgacctgtgcaacgctttcctgcaagaagccaagtggctgtacaaca
aatctactccgacctttgacgactacttcggcaacgcatggaaatcctcttctggcccg
ctgcaactggtgttcgcttacttcgctgtcgtgcagaacattaaaaaggaagagatcga
aaacctgcaaaaataccatgacaccatctctcgtccttcccatatcttccgtctgtgca
atgacctggctagcgcgtctgcggaaattgcgcgtggtgaaaccgcaaatagcgtttct
tgttacatgcgcactaaaggtatctccgaagaactggctaccgaaagcgtgatgaatct
gatcgatgaaacctggaaaaagatgaacaaggaaaaactgggtggtagcctgttcgcga
aaccgttcgtggaaaccgcgatcaacctggcacgtcaatctcactgcacttatcataac
ggcgacgcgcatacctctccggatgagctgacccgcaaacgcgttctgtctgtaatcac
tgaaccgattctgccgtttgaacgcgaaaacctgtattttcagggcctcgagcaccacc
accaccaccactgagatccggctgctaacaaagcccgaaaggaagctgagttggctgct
gccaccgctgagcaataactagcataaccccttggggcctctaaacgggtcttgagggg
tttttgctgaaaggaggaactatatccggat

Figure 37

Kudzu IspS protein (SEQ ID NO:42)

MCATSSQFTQITEHNSRRSANYQPNLWNFEFLQSLENDLKVEKLEEKATK
LEEEVRCMINRVDTQPLSLLELIDDVQRLGLTYKFEKDIIKALENIVLLD
ENKKNKSDLHATALSFRLLRQHGFEVSQDVFERFKDKEGGFSGELKGDVQ
GLLSLYEASYLGFEGENLLEEARTFSITHLKNNLKEGINTKVAEQVSHAL
ELPYHQRLHRLEARWFLDKYEPKEPHHQLLLELAKLDFNMVQTLHQKELQ
DLSRWWTEMGLASKLDFVRDRLMEVYFWALGMAPDPQFGECRKAVTKMFG
LVTIIDDVYDVYGTLDELQLFTDAVERWDVNAINTLPDYMKLCFLALYNT
VNDTSYSILKEKGHNNLSYLTKSWRELCKAFLQEAKWSNNKIIPAFSKYL
ENASVSSSGVALLAPSYFSVCQQQEDISDHALRSLTDFHGLVRSSCVIFR
LCNDLATSAAELERGETTNSIISYMHENDGTSEEQAREELRKLIDAEWKK
MNRERVSDSTLLPKAFMEIAVNMARVSHCTYQYGDGLGRPDYATENRIKL
LLIDPFPINQLMYV

Figure 38

*Populus [alba v tremuloides]* IspS protein (SEQ ID NO:43)

MCSVSTENVSFTETETEARRSANYEPNSWDYDFLLSSDTDESIEVYKDKAKKLEAEVRRE
INNEKAEFLTLLELIDNVQRLGLGYRFESDIRRALDRFVSSGGFDGVTKTSLHATALSFR
LLRQHGFEVSQEAFSGFKDQNGNFLENLKEDTKAILSLYEASFLALEGENILDEARVFAI
SHLKELSEEKIGKELAEQVNHALELPLHRRTQRLEAVWSIEAYRKKEDANQVLLELAILD
YNMIQSVYQRDLRETSRWWRRVGLATKLHFAKDRLIESFYWAVGVAFEPQYSDCRNSVAK
MFSFVTIIDDIYDVYGTLDELELFTDAVERWDVNAINDLPDYMKLCFLALYNTINEIAYD
NLKDKGENILPYLTKAWADLCNAFLQEAKWLYNKSTPTFDDYFGNAWKSSSGPLQLIFAY
FAVVQNIKKEEIENLQKYHDIISRPSHIFRLCNDLASASAEIARGETANSVSCYMRTKGI
SEELATESVMNLIDETCKKMNKEKLGGSLFAKPFVETAINLARQSHCTYHNGDAHTSPDE
LTRKRVLSVITEPILPFER

Figure 40A DNA sequence of pCL201 (IspS CDS is underlined):

tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctccctttt
agggttccgatttagtgctttacggcacctcgaccccaaaaaacttgattagggtgatg
gttcacgtagtgggccatcgccctgatagacggtttttcgccctttgacgttggagtcc
acgttctttaatagtggactcttgttccaaactggaacaacactcaaccctatctcggt
ctattcttttgatttataagggattttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatatttttgaaaaagccgtttctgtaa
tgaaggagaaaactcaccgaggcagttccataggatggcaagatcctggtatcggtctg
cgattccgactcgtccaacatcaatacaacctattaatttcccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttcccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacaccccttgtattactgtttatgtaagcagacagtttta
ttgttcatgaccaaaatcccttaacgtgagttttcgttccactgagcgtcagaccccgt
agaaaagatcaaaggatcttcttgagatcctttttttctgcgcgtaatctgctgcttgc
aaacaaaaaaaccaccgctaccagcggtggtttgtttgccggatcaagagctaccaact
ctttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccagggggaaacgcctggtatcttta
tagtcctgtcgggtttcgccacctctgacttgagcgtcgatttttgtgatgctcgtcag
gggggcggagcctatggaaaaacgccagcaacgcggcctttttacggttcctggccttt
tgctggccttttgctcacatgttctttcctgcgttatcccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag

Figure 40B atgtctgcctgttcatccgcgtccagctcgttgagtttctccagaagcgttaatgtctg
gcttctgataaagcgggccatgttaagggcggtttttcctgtttggtcactgatgcct
ccgtgtaagggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgcccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggtttttcttttcaccagtgagacgggcaacagctgattgccctt
caccgcctggccctgagagagttgcagcaagcggtccacgctggtttgccccagcaggc
gaaaatcctgtttgatggtggttaacggcgggatataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
actttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctcccttatgcgactcctgcattaggaagc
agcccagtagtaggttgaggccgttgagcaccgccgccgcaaggaatggtgcatgcaag
gagatggcgcccaacagtcccccggccacggggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactataggggaattgtgagcg
gataacaattcccctctagaaataattttgtttaactttaagaaggagatatacatatg
gaagcacgtcgctctgcgaactacgaacctaacagctgggactatgattacctgctgtc
ctccgacacggacgagtccatcgaagtatacaaagacaaagcgaaaaagctggaagccg
aagttcgtcgcgagattaataacgaaaaagcagaatttctgaccctgctggaactgatt

Figure 40C

```
gacaacgtccagcgcctgggcctgggttaccgtttcgagtctgatatccgtggtgcgct
ggatcgcttcgtttcctccggcggcttcgatgcggtaaccaagacttccctgcacggta
cggcactgtctttccgtctgctgcgtcaacacggttttgaggtttctcaggaagcgttc
agcggcttcaaagaccaaaacggcaacttcctggagaacctgaaggaagatatcaaagc
tatcctgagcctgtacgaggccagcttcctggctctggaaggcgaaaacatcctggacg
aggcgaaggttttcgcaatctctcatctgaaagaactgtctgaagaaagatcggtaaa
gagctggcagaacaggtgaaccatgcactggaactgccactgcatcgccgtactcagcg
tctggaagcagtatggtctatcgaggcctaccgtaaaaaggaggacgcgaatcaggttc
tgctggagctggcaattctggattacaacatgatccagtctgtataccagcgtgatctg
cgtgaaacgtcccgttggtggcgtcgtgtgggtctggcgaccaaactgcactttgctcg
tgaccgcctgattgagagcttctactgggccgtgggtgtagcattcgaaccgcaatact
ccgactgccgtaactccgtcgcaaaaatgttttctttcgtaaccattatcgacgatatc
tacgatgtatacggcaccctggacgaactggagctgtttactgatgcagttgagcgttg
ggacgtaaacgccatcaacgacctgccggattacatgaaactgtgctttctggctctgt
ataacactattaacgaaatcgcctacgacaacctgaaagataaaggtgagaacatcctg
ccgtatctgaccaaagcctgggctgacctgtgcaacgctttcctgcaagaagccaagtg
gctgtacaacaaatctactccgacctttgacgactacttcggcaacgcatggaaatcct
cttctggcccgctgcaactggtgttcgcttacttcgctgtcgtgcagaacattaaaaag
gaagagatcgaaaacctgcaaaaataccatgacaccatctctcgtccttcccatatctt
ccgtctgtgcaatgacctggctagcgcgtctgcggaaattgcgcgtggtgaaaccgcaa
atagcgtttcttgttacatgcgcactaaaggtatctccgaagaactggctaccgaaagc
gtgatgaatctgatcgatgaaacctggaaaaagatgaacaaggaaaaactgggtggtag
cctgttcgcgaaaccgttcgtggaaaccgcgatcaacctggcacgtcaatctcactgca
cttatcataacggcgacgcgcatacctctccggatgagctgacccgcaaacgcgttctg
tctgtaatcactgaaccgattctgccgtttgaacgctaaggatccgaattcgagctccg
tcgacaagcttgcggccgcactcgagcaccaccaccaccaccactgagatccggctgct
aacaaagcccgaaaggaagctgagttggctgctgccaccgctgagcaataactagcata
accccttggggcctctaaacgggtcttgaggggttttttgctgaaaggaggaactatat
ccggat
```

Figure 41. Amino Acid Sequence of P. alba IspS (residues 1 through 544):

MEARRSANYEPNSWDYDYLLSSDTDESIEVYKDKAKKLEAEVRREINNEKAEFLTLLELI
DNVQRLGLGYRFESDIRGALDRFVSSGGFDAVTKTSLHGTALSFRLLRQHGFEVSQEAFS
GFKDQNGNFLENLKEDIKAILSLYEASFLALEGENILDEAKVFAISHLKELSEEKIGKEL
AEQVNHALELPLHRRTQRLEAVWSIEAYRKKEDANQVLLELAILDYNMIQSVYQRDLRET
SRWWRRVGLATKLHFARDRLIESFYWAVGVAFEPQYSDCRNSVAKMFSFVTIIDDIYDVY
GTLDELELFTDAVERWDVNAINDLPDYMKLCFLALYNTINEIAYDNLKDKGENILPYLTK
AWADLCNAFLQEAKWLYNKSTPTFDDYFGNAWKSSSGPLQLVFAYFAVVQNIKKEEIENL
QKYHDTISRPSHIFRLCNDLASASAEIARGETANSVSCYMRTKGISEELATESVMNLIDE
TWKKMNKEKLGGSLFAKPFVETAINLARQSHCTYHNGDAHTSPDELTRKRVLSVITEPIL
PFER

Figure 45

| | | 1 | 2 | 3 | 4 | 5 | 6 | 7 | 8 | 9 | 10 | 11 | 12 |
|---|---|---|---|---|---|---|---|---|---|---|---|---|---|
| Position 1 | A | A | C | D | E | F | G | H | I | K | L | 1 wt | Vector only |
| | B | M | N | P | Q | R | S | T | V | W | Y | 1 wt | Vector only |
| Position 2 | C | A | C | D | E | F | G | H | I | K | L | 2 wt | Vector only |
| | D | M | N | P | Q | R | S | T | V | W | Y | 2 wt | Vector only |
| Position 3 | E | A | C | D | E | F | G | H | I | K | L | 3 wt | Vector only |
| | F | M | N | P | Q | R | S | T | V | W | Y | 3 wt | Vector only |
| Position 4 | G | A | C | D | E | F | G | H | I | K | L | 4 wt | Vector only |
| | H | M | N | P | Q | R | S | T | V | W | Y | 4 wt | Vector only |

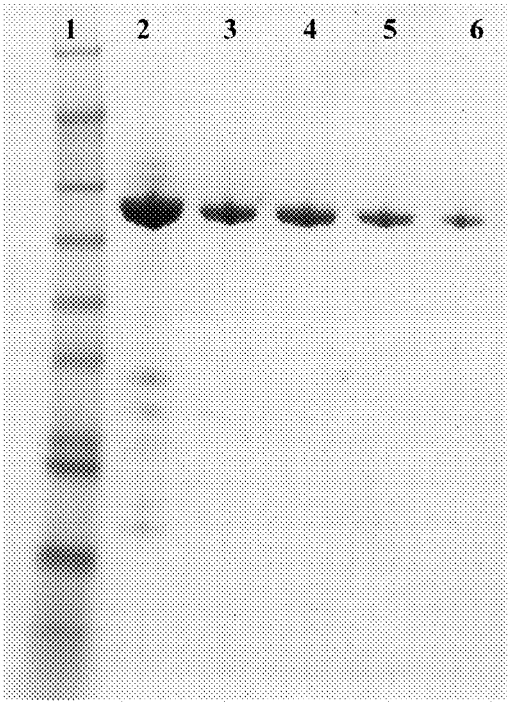
Figure 51. SDS-PAGE gel showing IspS-L494P at different stages of the purification. Lane 1- molecular weight standard; Lane 2- IspS-L494P prior to treatment with TurboTEV; Lane 3- IspS-L494P treated with TurboTEV; Lanes 4-6- IspS-L494P after final buffer exchange at different dilution levels.

Figure 52: $2F_O$-$2F_C$ electron density map at residue 494 contoured at 1-sigma. Panel A shows 494L, Panel B shows 494P.
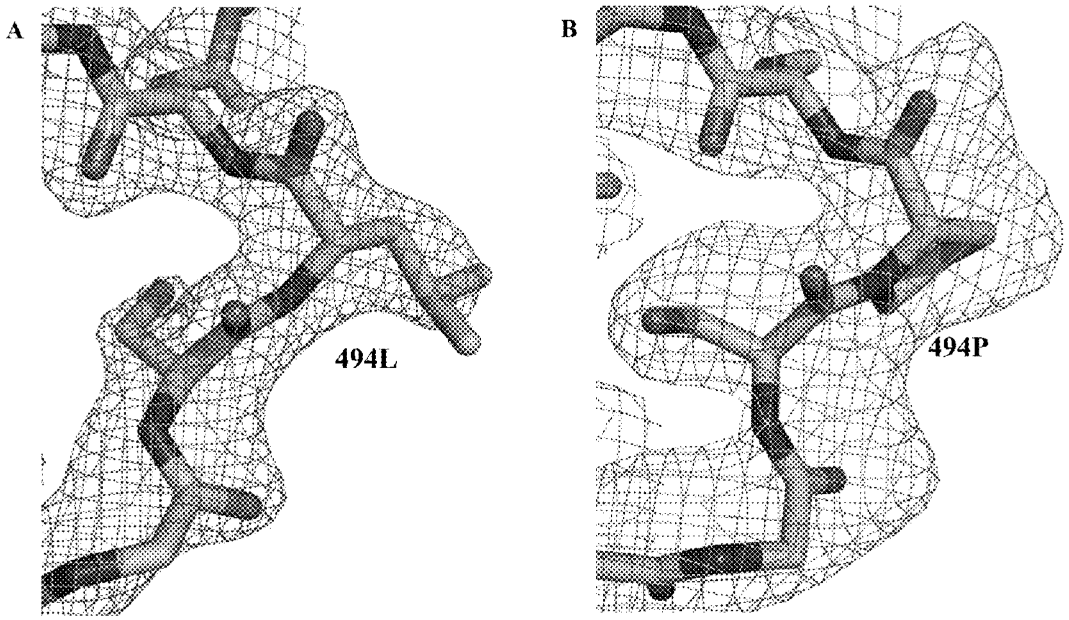

Figure 53: Alignment of the loop containing residue 494. Wild type IspS is light grey and IspS-L494P is dark grey. The L494P mutation results in an alternate loop structure.
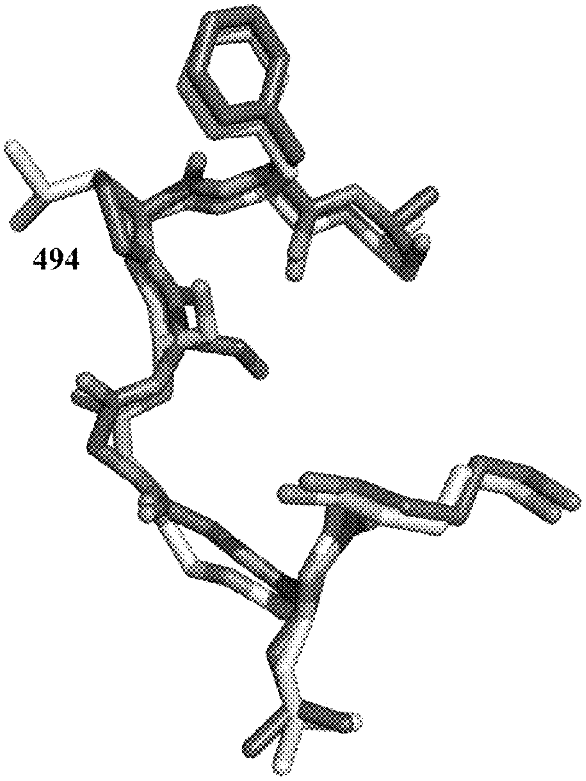

Figure 54: SDS-PAGE gel showing purified IspS-T536F at different dilutions (lanes 2-4) and molecular weight standard (lane 1).
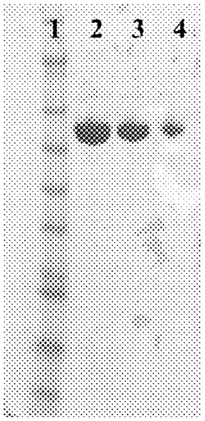
Figure 55: SDS-PAGE gel showing total cell lysate (lanes 2, 5, 8), supernatant (lanes 3, 6, 9), and purified protein (lanes 4, 7, 10) for wild type IspS, IspS-L494P and IspS-T536F, respectively. A molecular weight marker is in lane 1.
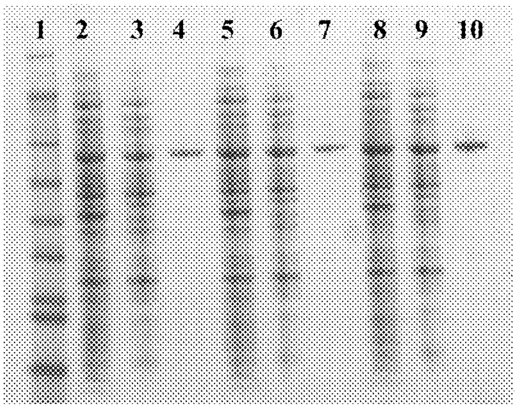

Figure 56: Thermal unfolding curves for wild type IspS, IspS-L494P, and IspS-T536F incubated with buffer only. $T_M$ values are indicated for each variant.
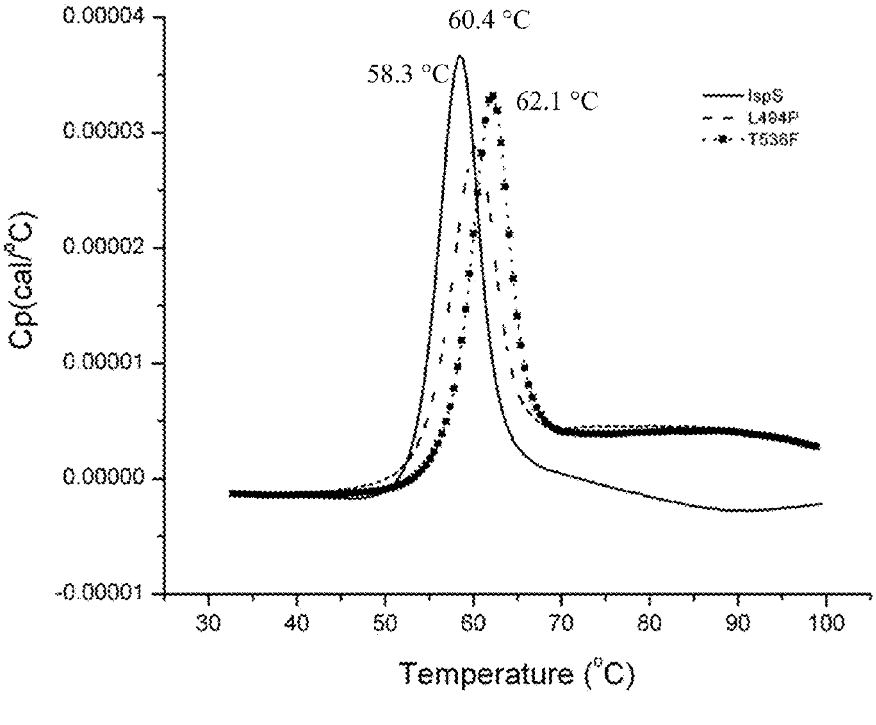

Figure 57: Thermal unfolding curves for wild type IspS, IspS-L494P, and IspS-T536F incubated with 5 mM sodium pyrophosphate. $T_M$ values are indicated for each variant.
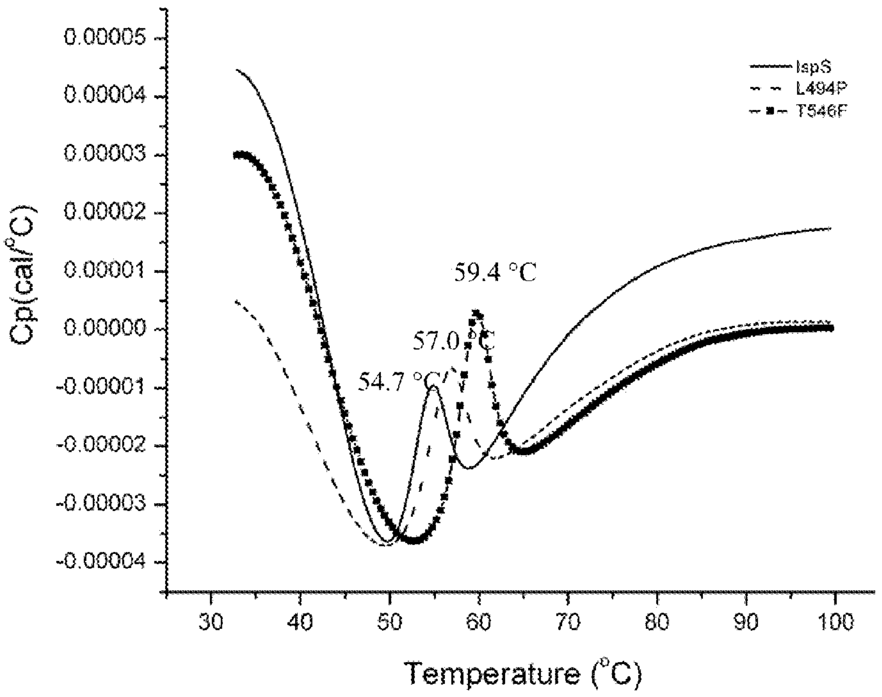

Figure 58: Temperature activity ration curves for wild type IspS (WT), IspS-L494P (LP), and IspS-T536F (TF). Data are plotted as a ratio of the specific activity (nmol/mg/min) of the protein at a given temperature divided by the specific activity at 35 °C.
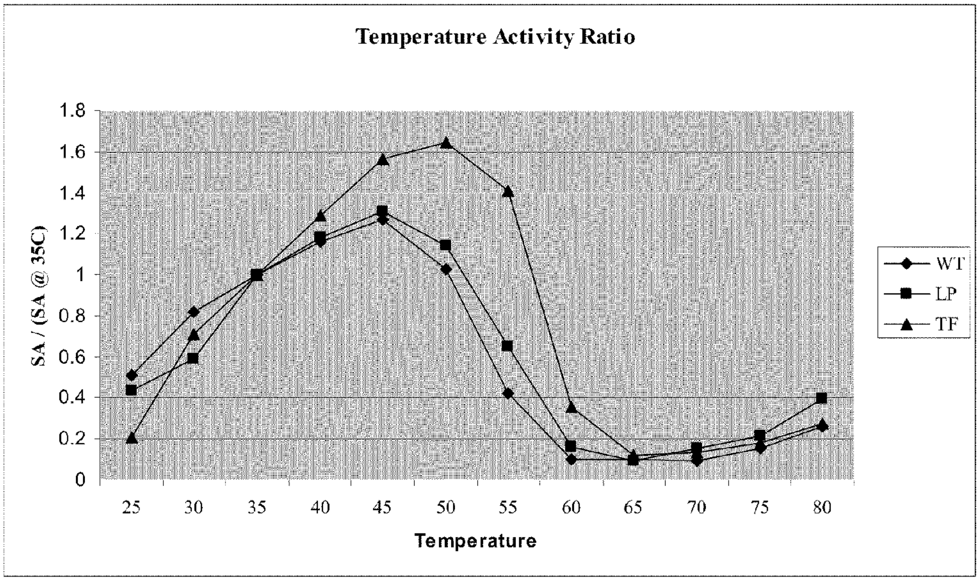

Figure 59: Local alignment of *P. alba* isoprene synthase and related terpene synthase enzymes

```
                                                                       L494                                              T536
                                                                         ↓                                                 ↓
SEQ ID NO: 99  P. alba IspS                          ANSVSCYMRT-KGISEELATESVMNLIDETWKKMN--KEKLGGSLFAKPFVETAINLARQSHCTYHN-GDAHTSPDELTRKRVLSVITEPILP
SEQ ID NO: 100 P. nigra IspS                         ANSVSCYMRT-KGISEELATESVMNLIDETWKKMN--KEKLGGSLFAKPFVETAINLARQSHCTYHN-GDAHTSPDELTRKRVLSVITEPILP
SEQ ID NO: 101 P. tremuloides IspS                   ANSVSCYMRT-KGISEELATESVMNLIDETWKKMN--KEKLGGSLFAKPFVETAINLARQSHCTYHN-GDAHTSPDELTRKRVLSVITEPILP
SEQ ID NO: 102 P. trichocarpa IspS                   ANSVSCYMRT-KGISEELATESVMNLIDETWKKMN--KEKLGGSLFAKPFVETAINLARQSHCIYHN-GDAHTSPDELTRKRVLSVITEPILP
SEQ ID NO: 103 P. alba x P. tremula IspS             ANSVSCYMRT-KGISEELATESVMNLIDETCKKMN--KEKLGGSLFAKPFVETAINLARQSHCTYHN-GDAHTSPDELTRKRVLSVITEPILP
SEQ ID NO: 104 P. montana IspS                       TNSIISYMHENDGISEEQAREELRKLIDAEWKKMNR-ERVSDSTLLPKAFMEIAVNMARVSHCTYQY-GDGLGRPDYATENRIKILLIDFFPI
SEQ ID NO: 105 M. spicata 4S-limonene synthase       PKSLQCYMSD-YNASEAEARKHVKWLIAEVWKKMNA-ERVSKDSPFGKDFIGCAVDLGRMAQLMYHN-GDGHGTQHPIIHQQMTRTLFFPFA-
SEQ ID NO: 106 S. officinalis bornyl diphosphate synthase PKTIQCYMKE-TNASEEEAVEHVKFLIREAWKIDMN--TAIAAGYPFPDGMVAGAANIGRVAQFIYLH-GDGFGVQHSKTYEHIAGLLFPYA-
SEQ ID NO: 107 Q. ilex pinene synthase               PKAIQCYMNE-TGASEEDAREYIKYLISAIWKKMN--EDRVASSPFSHIFIEIALNLARMAQCMYQH-GDGHGHGNHETKDRILSLLIQPIPL
SEQ ID NO: 108 N. tabacum epi-aristolochene synthase ATGIECCMRD-YGISTKEAMAKFQNMAETAWKDIN--EGLLRFTPVSTEFLTPILNLARIVEVTYIHNLDGYTHPEKVLKPHIINLLVDSIKI
SEQ ID NO: 109 E. globulus                           TNSIRCFMOE-KGISELEARECVKEEIDTAWKKMN--KYMVDRSTFNOSFVRMTYNLARMAHCVYOD-GDAIGSPDDLSWNRVHSLIIRPISP
SEQ ID NO: 110 M. alternifolia                       TNSILCYMRE-KGFSESEARKQVIEQIDTAWRQMN--KYMVDHSTFNRSFMOMTYNLARMAHCVYQD-GDAIGAPDDQSWNRVHSLIIKPVSL
SEQ ID NO: 111 V. vinifera                           ANSISCYMGQ-TGVSEEDAREHMKILIDESWKKMNKVREMDSDSPFAKPFVETAINLARIAQCTYQT-GDSHGAPDARSKKRVLSLIVEPIPX
SEQ ID NO: 112 M. truncatula                         ANSILCYMNE-NGVSEEVAYKHIQNLLDQIWKKMN--KDRVLNSPSSKYFSETIINLARLSHCIYQY-GDGHGAPDILAKNRLKALILEPLN-
```

Figure 60: Map of plasmid MD09-163 with A453N, G491S, L494P, and T536C/F Mutations
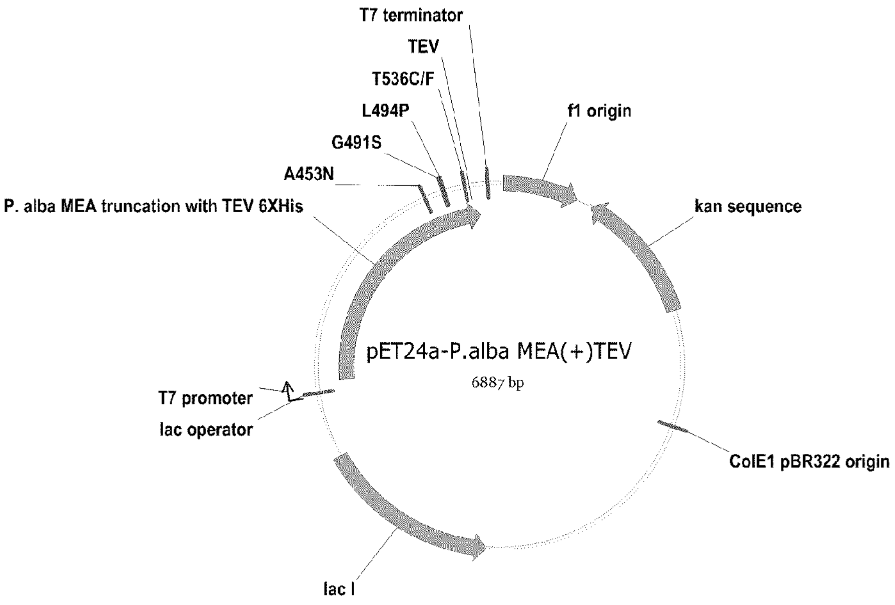

Figure 61: Dilution Series of Isoprene Synthases Assayed for Rate vs. [DMAPP]
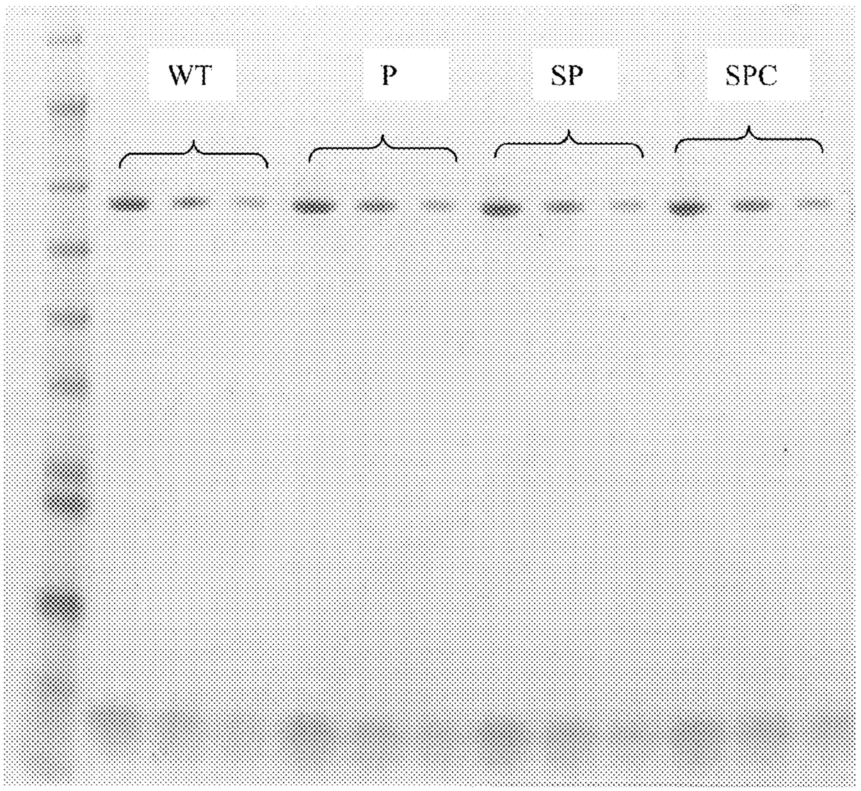

Figure 62: Specific activity of each variant with 4 mM DMAPP assayed at 30°C. The black bar indicates the specific activity of the WT isoprene synthase.
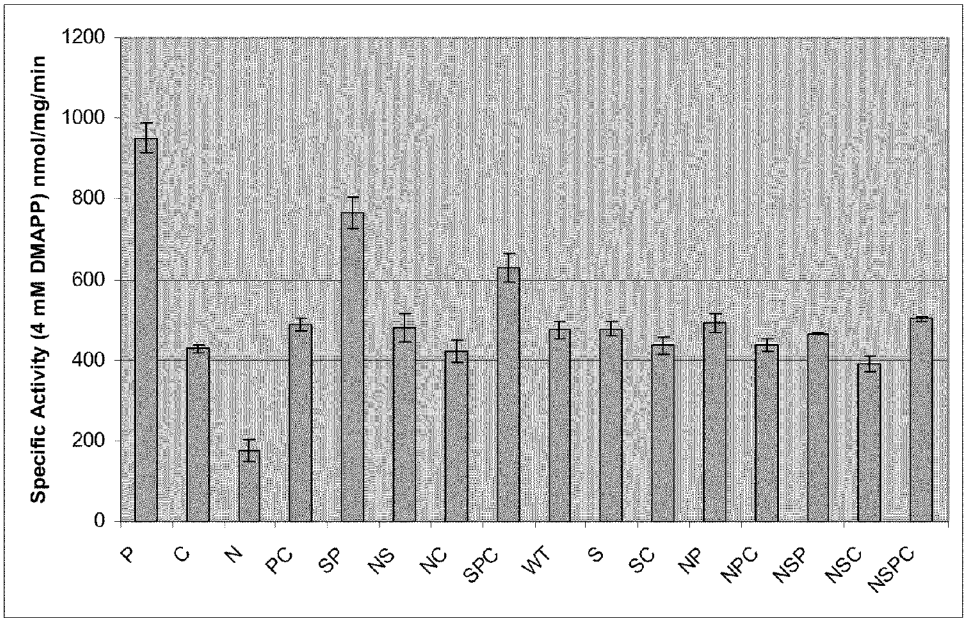

Figure 63: Rate vs. [DMAPP] for the P, SP and SPC variants of isoprene synthase and WT isoprene synthase. Each data point on the graph is the average of three independently performed kinetic assays. Error bars are reported as one standard deviation above and below the data point.
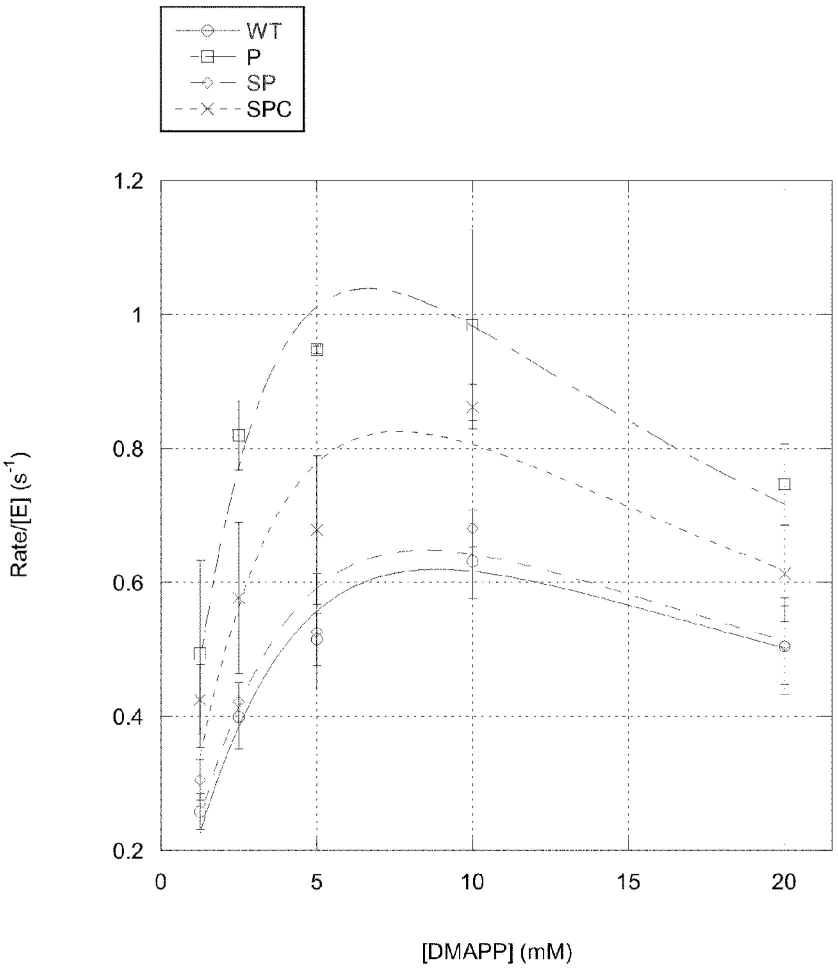

Figure 64: Alignment of the *P. tremuloides* (black) and *P. alba* structures (grey) showing high level of structural homology.
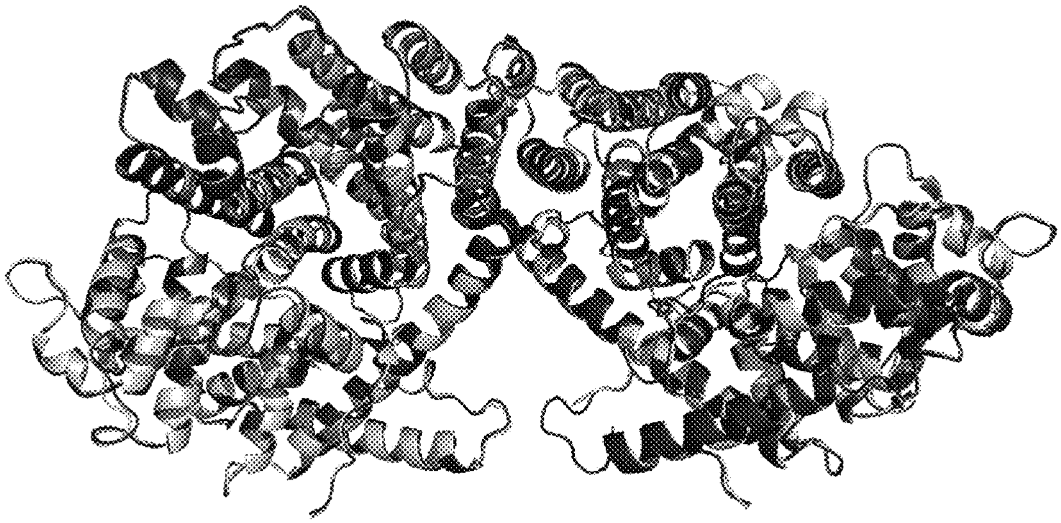

THREE-DIMENSIONAL STRUCTURE OF ISOPRENE SYNTHASE AND ITS USE THEREOF FOR GENERATING VARIANTS

CROSS-REFERENCE TO RELATED APPLICATIONS

This applications claims the benefit of U.S. Provisional patent application 61/172,199, filed on Apr. 23, 2009, and U.S. Provisional patent application 61/255,831, filed on Oct. 28, 2009, the contents of both are hereby incorporated by reference in its entirety.

FIELD OF INVENTION

The present invention is related to the crystallization and three-dimensional structure determination of *Populus tremuloides* isoprene synthase and *Populus alba* isoprene synthase. The invention also provides methods of producing variants of isoprene synthase for increased isoprene production in microbial host cells.

BACKGROUND OF THE INVENTION

Isoprenoids are isoprene polymers that find use in pharmaceuticals, neutraceuticals, flavors, fragrances, and rubber products. Natural isoprenoid supplies, however, are limited due to ecological concerns. For this reason, and to provide isoprenoid compositions having fewer impurities and greater uniformity, isoprenoids such as rubber are often produced synthetically.

Isoprene (2-methyl-1,3-butadiene) is a volatile hydrocarbon that is insoluble in water and soluble in alcohol. Commercially viable quantities of isoprene can be obtained by direct isolation from petroleum C5 cracking fractions or by dehydration of C5 isoalkanes or isoalkenes (Weissermel and Arpe, Industrial Organic Chemistry, 4th ed., Wiley-VCH, pp. 117-122, 2003). The C5 skeleton can also be synthesized from smaller subunits. It would be desirable, however, to have a commercially viable method of producing isoprene that was independent of nonrenewable resources.

Biosynthetic production of isoprene occurs by two distinct metabolic pathways (Julsing et al., Appl Microbiol Biotechnol, 75:1377-1384, 2007). In eukaryotes and archae, isoprene is formed via the mevalonate (MVA) pathway, while some eubacteria and higher plants produce isoprene via the methylerythritol phosphate (MEP) pathway. Isoprene emissions from plants are light and temperature-dependent with increases linked to leaf development. An isoprene-producing enzyme, isoprene synthase, has been identified in Aspen trees (Silver and Fall, Plant Physiol, 97:1588-1591, 1991; and Silver and Fall, J Biol Chem, 270:13010-13016, 1995) and is believed to be responsible for the in vivo production of isoprene from whole leaves. Bacterial production of isoprene has also been described (Kuzma et al., Curr Microbiol, 30:97-103, 1995; and Wilkins, Chemosphere, 32:1427-1434, 1996), and varies in amount with the phase of bacterial growth and the nutrient content of the culture medium (U.S. Pat. No. 5,849,970 to Fall et al.; and Wagner et al., J Bacteriol, 181: 4700-4703, 1999, both herein incorporated by reference in their entirety). The levels of isoprene obtainable through bacterial systems of the prior art, however, are insufficient for commercial uses.

Polypeptides, e.g. isoprene synthase, have a three-dimensional structure determined by the primary amino acid sequence and the environment surrounding the polypeptide. This three-dimensional structure establishes the polypeptide's activity, stability, binding affinity, binding specificity, and other biochemical attributes. Thus, knowledge of a protein's three-dimensional structure can provide much guidance in designing improvements to its biological activity, for example, greater catalytic activity, dimerization and/or solubility.

The three-dimensional structure of a polypeptide can be determined in a number of ways. Many of the most precise methods employ X-ray crystallography (See, e.g., Van Holde, (1971) Physical Biochemistry, Prentice-Hall, New Jersey, pp. 221-39). This technique relies on the ability of crystalline lattices to diffract X-rays or other forms of radiation. Diffraction experiments suitable for determining the three-dimensional structure of macromolecules typically require high-quality crystals. The crystallization properties of a polypeptide vary greatly (Dale, et al., J. Struct. Biol. 142:88-97, 2003; MacPherson, A., Methods 34:254-265, 2004; and Slabinski, L et al., Protein Science 16:2472-2482, 2007). In some cases polypeptides crystallize readily whereas in other cases polypeptides have proven extremely difficult to obtain. There is no comprehensive theory to guide efforts to crystallize macromolecules and as a result, most efforts macromolecular crystal growth is empirical in nature (MacPherson, 2004).

Previous efforts to utilize the structure of isoprene synthase in order to improve production of isoprene have relied on the structures of other terpene synthases in which three-dimensional structures are available including bornyl diphosphate synthase and 5-epi-aristolochene synthase (See e.g., U.S. patent application Ser. No. 12/429,143 and WO 2008/137092). What is needed is a three-dimensional structure of isoprene synthase to aid in the design of variants of isoprene synthase to allow commercial scale biological production of isoprenoids.

A three-dimensional structure of isoprene synthase is found to have a structurally homologous fold with previously determined synthetases, e.g. bornyl diphosphate synthase and limonene synthase, including conservation in the region involved with the coordinates of required metal ion cofactors, the active and substrate binding sites. The structure has provided insight in the conformational changes that are necessary for these enzyme to bind substrate and catalyze a coordinated series of reactions. Specifically the structure has identified flexible regions that are likely to be shared by all structurally homologous synthetase and that modification of the amino acids found in these regions and the neighboring regions would be expected to effect improved performance of these enzymes. A three-dimensional structure of isoprene synthase may provide a three-dimensional configuration of points, or reaction coordinates, representing the active site of isoprene synthase for the conversion of dimethylallyl diphosphate (DMAPP) into isoprene. Such a configuration of points can aid in the design of synthetic agents for the conversion of DMAPP into isoprene.

BRIEF SUMMARY OF THE INVENTION

The invention provides methods and compositions for generating variants of isoprene synthase with improved activity, expression or stability by utilizing three dimensional structure of isoprene synthase. In one aspect, the invention provides a) using a three dimensional structure of isoprene synthase to identify at least one location in the isoprene synthase for amino acid substitutions that is capable of increasing the activity, expression or stability of isoprene synthase; and b) modifying the isoprene synthase at the location(s) to generate an isoprene synthase variant with improved activity, expression or stability. In one embodiment, the location is selected from the group consisting of: flexible loop, disphosphate/metal binding site, active site, isoprenyl binding site, surface region, negatively charged region, hinge region, and electrostatic patch region.

In another aspect, the invention provides for methods of generating a variant of an isoprene synthase with improved activity, expression or stability; the method comprising; a) identifying hydrophobic amino acid residues on the surface of isoprene synthase based on the three dimensional structure of *P. alba* isoprene synthase; b) introducing one or more amino acid substitutions in the surface amino acids of isoprene synthase; c) identifying variants with substitutions that improve activity, expression or stability of the isoprene synthase compared to the *P. alba* isoprene synthase amino acid sequence of SEQ ID NO:45. In some embodiments, the hydrophobic surface amino acid is selected from the group consisting of I28, V30, L130, G153, L303, L469 and L494.

In other aspects, the invention provides for an isoprene synthase variant produced any of the methods disclosed herein. In some aspects, the isoprene synthase variant is isolated.

In other aspects, the isoprene synthase variant comprises one or more substitution(s) selected from the group consisting of I28W, I28T, I28R, I28Y, V30K, L130W, L130K, L1305, L130Y, L130R, L130V, L130I, L130E, L130D, G153K, G153H, G153L, G153W, L3031, L469A, L469Q, L494P, L494C, L494I, L494V, L494S, L494G, and L494D.

In other aspects, the invention provides for isoprene synthase variant, wherein the variant comprises one or more substitution(s) of a hydrophobic surface amino acid selected from the group consisting of I28, V30, L130, G153, L303, L469 and L494. In some aspects, the mutation is selected from the group consisting of I28W, I28T, I28R, I28Y, V30K, L130W, L130K, L1305, L130Y, L130R, L130V, L130I, L130E, L130D, G153K, G153H, G153L, G153W, L3031, L469A, L469Q, L494P, L494C, L494I, L494V, L494S, L494G, and L494D.

In other aspects, the invention provides for any host cell comprising the nucleic acid encoding for any of the isoprene synthase variants disclosed herein. The invention also provides for host cells that express or are capable of expressing any of the isoprene synthase variants disclosed herein.

In other aspects, the invention provides for methods of generating a variant of an isoprene synthase with improved activity, expression or stability; the method comprising; a) identifying residues in the hinge region of isoprene synthase based on the three dimensional structure of *P. alba* isoprene synthase; b) introducing one or more amino acid substitutions in the hinge region amino acids of isoprene synthase; c) identifying variants with substitutions that improve activity, expression or stability of the isoprene synthase compared to the *P. alba* isoprene synthase amino acid sequence of SEQ ID NO:45. In some embodiments, the hinge region amino acid is selected from the group consisting of R198, I229 and L260.

In other aspects, the invention provides for an isolated isoprene synthase variant, wherein the variant comprises one or more substitution(s) in a hinge region amino acid selected from the group consisting of R198, I229 and L260. In other aspects, the invention provides for variants comprising one or more substitution(s) selected from the group consisting of I229V, I229L, I229C, I229T, I229P, I229N, L260N, L260M, and L260I.

In other aspects, the invention provides for methods of generating a variant of an isoprene synthase with improved activity, expression or stability; the method comprising; a) identifying amino acid residues in the negatively charged area of isoprene synthase based on the three dimensional structure of *P. alba* isoprene synthase; b) introducing one or more amino acid substitutions in the negatively charged area amino acids of isoprene synthase; c) identifying variants with substitutions that improve activity, expression or stability of the isoprene synthase compared to the *P. alba* isoprene synthase amino acid sequence of SEQ ID NO:45. In some embodiments, the negatively charged area amino acid is selected from the group consisting of D311 and D323. In some embodiments, the variant comprises one or more substitution(s) selected from the group consisting of D311M, D311F, D311L, D311G, D311I, D311A, D311T, D311R, D311V, D311E, D323M, D323W, D323Y, D323F, D323I, D323S, D323V, D323A, D323G, and D323Q.

In other aspects, the invention provides for an isoprene synthase variant, wherein the wherein the variant comprises one or more substitution(s) in a negatively charged area amino acid selected from the group consisting of D311 and D323.

In other aspects, the invention provides for methods of generating a variant of an isoprene synthase with improved activity, expression or stability; the method comprising; a) identifying amino acid residues in the flexible loops of isoprene synthase based on the three dimensional structure of *P. alba* isoprene synthase; b) introducing one or more amino acid substitutions in the flexible loop amino acids of isoprene synthase; and c) identifying variants with substitutions that improve activity, expression or stability of the isoprene synthase compared to the *P. alba* isoprene synthase amino acid sequence of SEQ ID NO:45. In some embodiments, the flexible loop amino acid is selected from the group consisting of A443, A453, N454, H515 and A519. In other embodiments, the variant comprises one or more substitution(s) selected from the group consisting of A443S, A443G, A443R, A443Q, A453L, A453N, A453I, A453V, H515M, H515Q, A519H, A519S, A519G, A519W and A519T.

In other aspects, the invention provides for an isoprene synthase variant, wherein the variant comprises one or more substitution(s) in a flexible loop amino acid selected from the group consisting of A443, A453, N454, H515 and A519. In some embodiments, the variant is substituted at amino acid T536. In other embodiments, the variant comprises one or more substitution(s) selected from the group consisting of T536F, T536Y, T536V, T536I, T536M, T536H, T536C, T536L, T536K, T536A, T536S and T536G.

In other aspects, the invention provides for methods of generating a variant of an isoprene synthase with improved activity, expression or stability; the method comprising; a) identifying amino acid residues in the diphosphate/metal binding site of isoprene synthase based on the three dimensional structure of *P. alba* isoprene synthase; b) introducing one or more amino acid substitutions in the diphosphate/metal binding site amino acids of isoprene synthase; and c) identifying variants with substitutions that improve activity, expression or stability of the isoprene synthase compared to the *P. alba* isoprene synthase amino acid sequence of SEQ ID NO:45.

In other aspects, the invention provides for isoprene synthase variants, wherein the variant comprises one or more substitution(s) in a diphosphate/metal binding site amino acid.

In other aspects, the invention provides for methods of generating a variant of an isoprene synthase with improved activity, expression or stability; the method comprising; a) identifying amino acid residues in the isoprenyl binding site of isoprene synthase based on the three dimensional structure of *P. alba* isoprene synthase; b) introducing one or more amino acid substitutions in the isoprenyl binding site amino acids of isoprene synthase; and c) identifying variants with substitutions that improve activity, expression or stability of the isoprene synthase compared to the *P. alba* isoprene synthase amino acid sequence of SEQ ID NO:45).

In other aspects, the invention provides for isoprene synthase variants, wherein the variant comprises one or more substitution(s) in a isoprenyl binding site amino acid.

In other aspects, the invention provides for methods of producing isoprene, comprising: (a) providing a host cell of any one of claims 9, 15, 21, 27, 30, 34, and 38; and (b) culturing the host cell under conditions suitable for producing isoprene.

The invention provides methods of generating a variant of an isoprene synthase with improved activity, expression or stability comprising; a) identifying amino acid residues on the surface of isoprene synthase based on the three dimensional structure of *P. alba* isoprene synthase; b) introducing one or more amino acid substitutions in the surface amino acids of isoprene synthase; c) identifying mutations that improve activity, expression or stability of the isoprene synthase compared to the *P. alba* isoprene synthase comprising the amino acid sequence of SEQ ID NO: 18. In some embodiments, the amino acid substitutions include one or more of the following: hydrophobic to positively charged, positively charged to hydrophobic, hydrophobic to negatively charged, negatively charged to hydrophobic, hydrophobic to neutral polar, neutral polar to hydrophobic, neutral polar to positively charged, positively charged to neutral polar, neutral polar to negatively charged, negatively charged to neutral polar, positively charged to negatively charged, and negatively charged to positively charged.

The invention provides methods for generating a variant of an isoprene synthase with improved activity comprising a) identifying amino acid residues in or near the diphosphate/metal binding site in the three dimensional structure of *P. tremuloides* isoprene synthase; b) introducing one or more amino acid substitutions in or near the diphosphate/metal binding site of isoprene synthase; c) identifying mutations that improve the activity of the isoprene synthase compared to the *P. tremuloides* isoprene synthase comprising the amino acid sequence of SEQ ID NO:11. In some embodiments the invention provides an isolated isoprene synthase variant produced by these methods. In some embodiments, the amino acids in the diphosphate/metal binding site are selected from the group consisting of D293, Y385, S392 and D437.

The invention provides methods of generating a variant of an isoprene synthase with improved activity comprising a) identifying amino acid residues in the isoprenyl binding site in the three dimensional structure of *P. tremuloides* isoprene synthase; b) introducing one or more amino acid substitutions in the isoprenyl binding site of isoprene synthase; c) identifying mutations that improve the activity of the isoprene synthase compared to the *P. tremuloides* isoprene synthase comprising the amino acid sequence of SEQ ID NO:11. In some embodiments the invention provides an isolated isoprene synthase variant produced by this method. In some embodiments, the amino acids in the isoprenyl binding site are selected from the group consisting of S261, W264, F285, T289, S393, S394, F432 and Y512.

The invention provides methods of generating a variant of an isoprene synthase with improved activity comprising a) identifying amino acid residues in the substrate access loop in the three dimensional structure of *P. tremuloides* isoprene synthase; b) introducing one or more amino acid substitutions in the substrate access loop of isoprene synthase; c) identifying mutations that improve the activity of the isoprene synthase compared to the *P. tremuloides* isoprene synthase comprising the amino acid sequence of SEQ ID NO:11. In some embodiments the invention provides an isolated isoprene synthase variant produced by these methods. In some embodiments the amino acids in the substrate access loop are selected from the group consisting of S440, A441, S442, A443, E444, I445, A446, R447, G448, E449, T450, A451, N452, S453, Y512, H513, N514, G515, D516, A517, H518, T519, S520, P521, D522, E523, and L524.

The invention provides a variant of a parent synthase that is structurally homologous to isoprene synthase and having modified residues corresponding to or analogous to the following residues of the flexible N-terminus and/or adjacent residues; 1-28, 239, 243, 253-257, 259, 260, 293, 295-300, 303, 325, 374 of an isoprene synthase. In some embodiments, the synthase is an isoprene synthase. In some embodiments, the invention provides a variant of a parent synthase that is structurally homologous to isoprene synthase and having modified residues corresponding to or analogous to the following residues of the flexible loop I and/or adjacent residues; 438-453, 293, 295, 297, 370, 371, 373, 374, 378-380, 382, 385, 386, 433-437, 454-458, 469, 472, 476, 512 of isoprene synthase. In some embodiments, the synthase is an isoprene synthase. In some embodiments, the invention provides a variant of a parent synthase that is structurally homologous to isoprene synthase and having modified residues corresponding to or analogous to the following residues of the flexible loop II and/or adjacent residues; 512-526, 187, 188, 255, 257, 270, 271, 273, 274, 285, 288, 439, 440, 442, 508-512, and 528-532 of isoprene synthase the synthase is an isoprene synthase.

The invention provides methods of generating a variant of a parent terpene synthase or terpene synthase structural homolog with improved activity comprising a) identifying amino acid residues in or near one or more substrate access loops in the three dimensional structure of the terpene synthase or terpene synthase structural homolog, b) introducing one or more amino acid substitutions in or near the one or more substrate access loops of the terpene synthase or terpene synthase structural homolog, c) identifying substitutions that improve the activity of the terpene synthase or terpene synthase structural homolog variant compared to the parent terpene synthase or terpene synthase structural homolog. In some embodiments, the terpene synthase or terpene synthase structural homolog is an isoprene synthase. In some embodiments, the isoprene synthase is *P. tremuloides* isoprene synthase comprising SEQ ID NO:11. In some embodiments, the isoprene synthase is *P. alba* isoprene synthase comprising SEQ ID NO: 18. In some embodiments, the variant comprises a substitution of one or more of the following amino acid residues L17, L18, S19, S20, S239, R243, F253, A254, R255, D256, R257, I259, E260, D293, Y295, D296, V297, Y298, G299, T300, E303, Y325, L374, Y375, V529, L530, T534, D293, Y295, V297, E370, A371, W373, L374, S378, T379, P380, F382, Y385, F386, R433, L434 C435, N436, D437, V454, S455, C456, Y457, M458, T469, V472, I476, Y512, E187, L188, R255, R257, F270, E271, Q273, Y274, F285, V288, A439, S440, S442, S508, H509, C510, T511, Y512, R528, V529, L530, S531, and V532.

The invention provides methods of generating a variant of isoprene synthase by a) obtaining a crystal comprising an isoprene synthase; b) obtaining the atomic coordinates of the crystal; c) correlating the atomic coordinate data with one or more molecular modeling techniques; d) identifying at least one modification predicted to effect the activity, expression or stability of isoprene synthase; and e) modifying the isoprene synthase based on the prediction. In some embodiments, the isoprene synthase is *P. tremuloides* isoprene synthase. In some embodiments, the isoprene synthase is a *P. alba* isoprene synthase.

In some aspects, the invention provides methods of generating a variant of an isoprene synthase comprising a) correlating the atomic coordinate data for *P. tremuloides* isoprene synthesis of Table 3-7 with one of more molecular modeling techniques b) identifying at least one modification predicted to effect the activity, expression or stability of isoprene synthase; and c) modifying the isoprene synthase based on the prediction obtained in b).

In some aspects, the invention provides methods of generating a variant of an isoprene synthase comprising a) correlating the atomic coordinate data for *P. alba* isoprene synthesis of Table 4-2 with one of more molecular modeling techniques b) identifying at least one modification predicted to effect the activity, expression or stability of isoprene synthase; and c) modifying the isoprene synthase based on the prediction obtained in b).

In other aspects, the invention provides methods of identifying a candidate variant of an isoprene synthase comprising: a) comparing the atomic structure of the isoprene synthase without a bound ligand to the atomic structure of the isoprene synthase with a bound ligand, and b) computationally identifying candidate variants of the isoprene synthesis for the ability to bind the ligand.

The invention provides methods of generating a variant of an isoprene synthase with improved activity, expression or stability comprising; a) identifying amino acid residues on the surface of isoprene synthase based on the three dimensional structure of *P. tremuloides* isoprene synthase; b) introducing one or more amino acid substitutions in the surface amino acids of isoprene synthase; c) identifying mutations that improve activity, expression or stability of the isoprene synthase compared to the *P. tremuloides* isoprene synthase comprising the amino acid sequence of SEQ ID NO: 11. In some embodiments, the amino acid substitutions include one or more of the following: hydrophobic to positively charged, positively charged to hydrophobic, hydrophobic to negatively charged, negatively charged to hydrophobic, hydrophobic to neutral polar, neutral polar to hydrophobic, neutral polar to positively charged, positively charged to neutral polar, neutral polar to negatively charged, negatively charged to neutral polar, positively charged to negatively charged, and negatively charged to positively charged.

The invention provides methods of generating variants of an isoprene synthase with improved activity, expression or stability by a) identifying hydrophobic amino acid residues on the surface of isoprene synthase based on the three dimensional structure of *P. alba* isoprene synthase; b) introducing one or more amino acid substitutions in the surface amino acids of isoprene synthase; c) identifying mutations that improve activity, expression or stability of the isoprene synthase compared to the parent *P. alba* isoprene synthase.

The invention provides isolated *P. alba* isoprene synthase variants comprising a mutation of a hydrophobic surface amino acid at one or more of the following residues: I28, V30, L130, G153, L303, L469 and L494. In some embodiments, the variant comprises one or more of the following mutations: I28W, I28T, I28R, I28Y, V30K, L130W, L130K, L1305, L130Y, L130R, L130V, L1301, L130E, L130D, G153K, G153H, G153L, G153W, L3031, L469A, L469Q, L494P, L494C, L494I, L494V, L494S, L494G, and L494D.

The invention provides methods of generating variants of a parent isoprene synthase with improved activity, expression or stability by a) identifying residues in the hinge region of isoprene synthase based on the three dimensional structure of *P. alba* isoprene synthase; b) introducing one or more amino acid substitutions in the hinge region amino acids of isoprene synthase; c) identifying mutations that improve activity, expression or stability of the isoprene synthase compared to the parent *P. alba* isoprene synthase.

In some aspects, the invention provides isolated *P. alba* isoprene synthase variants comprising a mutation in or near a hinge region wherein the variant comprises a mutation at one or more of the following residues R198, I229 and L260. In some embodiments, the variant comprises one or more of the following mutations: I229V, I229L, I229C, I229T, I229P, I229N, L260N, L260M, and L260I.

The invention provides methods of generating variants of an isoprene synthase with improved activity, expression or stability by a) identifying amino acid residues in the electrostatic patch of isoprene synthase based on the three dimensional structure of *P. alba* isoprene synthase; b) introducing one or more amino acid substitutions in the electrostatic patch amino acids of isoprene synthase; c) identifying mutations that improve activity, expression or stability of the isoprene synthase compared to the parent *P. alba* isoprene synthase.

In some aspects, the invention provides isolated *P. alba* isoprene synthase variants, wherein the wherein the variant comprises a mutation in an electrostatic patch amino acid including, but not limited to residues D311 and D323. In some embodiments, the variant comprises one or more of the following mutations: D311M, D311F, D311L, D311G, D311I, D311A, D311T, D311R, D311V, D311E, D323M, D323W, D323Y, D323F, D323I, D323S, D323V, D323A, D323G, and D323Q.

The invention provides methods of generating variants of an isoprene synthase with improved activity, expression or stability by a) identifying amino acid residues in the flexible loops of isoprene synthase based on the three dimensional structure of *P. alba* isoprene synthase; b) introducing one or more amino acid substitutions in the flexible loop amino acids of isoprene synthase; c) identifying mutations that improve activity, expression or stability of the isoprene synthase compared to the parent *P. alba* isoprene synthase.

The invention provides isolated *P. alba* isoprene synthase variants comprises a mutation in a flexible loop at one or more of the following residues: A443, A453, N454, H515, A519 and E525. In some embodiments, the variant comprises one or more of the following mutations: A443S, A443G, A443R, A443Q, A453L, A453N, A453I, A453V, H515M, H515Q, A519H, A519S, A519G, A519W and A519T.

In some aspects, the invention provides isolated *P. alba* isoprene synthase variants mutated at amino acid T536. In some embodiments, the variant comprises one of the following mutations: T536F, T536Y, T536V, T536I, T536M, T536H, T536C, T536L, T536K, T536A, T536S and T536G.

The invention provides methods of generating variants of an isoprene synthase with improved activity, expression or stability; the method comprising; a) identifying amino acid residues in the diphosphate/metal binding site of isoprene synthase based on the three dimensional structure of *P. alba* isoprene synthase; b) introducing one or more amino acid substitutions in the diphosphate/metal binding site amino acids of isoprene synthase; c) identifying mutations that improve activity, expression or stability of the isoprene synthase compared to the parent *P. alba* isoprene synthase. In some aspects, the invention provides isolated isoprene synthase variants, comprising a mutation in a diphosphate/metal binding site residue of *P. alba* isoprene synthase.

The invention provides methods of generating variants of an isoprene synthase with improved activity, expression or stability; the method comprising a) identifying amino acid residues in the isoprenyl binding site of isoprene synthase based on the three dimensional structure of *P. alba* isoprene synthase; b) introducing one or more amino acid substitutions in the isoprenyl binding site amino acids of isoprene synthase; c) identifying mutations that improve activity, expression or stability of the isoprene synthase compared to the parent *P. alba* isoprene synthase. In some aspects, the invention provides isolated *P. alba* isoprene synthase variants comprises a mutation in a isoprenyl binding site amino acid.

In another aspect, the invention provides a crystalline form of an isoprene synthase. In particular, the invention provides methods of improving the activity of a terpene synthase based on the crystalline form of isoprene synthase. In some embodiments, the crystalline form of the isoprene synthase further comprises a ligand, for example dimethylallyl pyrophosphate (DMAPP).

In some aspects, a crystalline form of *P. tremuloides* isoprene synthase comprises a structure characterized by tetragonal space group symmetry $P4_32_12$ and unit cell dimensions of a=154.2 angstroms, b=154.2 angstroms and c=142.7 angstroms and wherein the alpha=beta=gamma=90 degrees. In some embodiments, the unit cell dimensions are a=146.5 to 161.9 angstroms, b=146.5 to 161.9 angstroms and c=135.6 to 149.8 angstroms and wherein the alpha=beta=gamma=90 degrees.

In some aspects, a crystalline form of *P. alba* isoprene synthase comprises a structure characterized by tetragonal space group symmetry $P4_32_12$ and unit cell dimensions of a=156.8 angstroms, b=156.8 angstroms and c=142.5 angstroms and wherein the alpha=beta=gamma=90 degrees. In some embodiments, the unit cell dimensions are a=148.96 to 164.6 angstroms, b=148.96 to 164.6 angstroms and c=135.4 to 149.6 angstroms and wherein alpha=beta=gamma=90 degrees.

The invention provides a crystalline form of a polypeptide comprising a structure defined by one or more structure coordinates of *P. tremuloides* isoprene synthase amino acids Arg 255, Asp 292, Asp 296, Glu 370, Arg 433 and Asn436, Ser261, Trp264, Phe285, Thr289, Ser393, Phe432 and Tyr512 according to Table 3-7, or similar structural coordinates for said residues comprising a root mean square deviation of less than about 1.5 Å when superimposed on the non-hydrogen atom positions of the corresponding atomic coordinates of Table 3-7. In some embodiments, the root mean square deviation is less than about 0.75 Å when superimposed on the non-hydrogen atom positions of the corresponding atomic coordinates of Table 3-7. In some embodiments, the root mean square deviation is less than about 0.35 Å when superimposed on the non-hydrogen atom positions of the corresponding atomic coordinates of Table 3-7.

In some embodiments of the invention, the invention provides a crystalline form of a *P. tremuloides* isoprene synthase wherein amino acid residues Arg 255, Asp 292, Asp 296, Glu 370, Arg 433 and Asn 436 comprise the diphosphate/metal binding sites of the isoprene synthase. In some embodiments, amino acid residues Ser 261, Trp 264, Phe 285, Thr 289, Ser 393, Ser 394, Phe 432, and Try 512 comprise the isoprenyl binding site of the isoprene synthase. In some embodiments, amino acid residues 438-453 having the sequence SASAEIARGETANS (SEQ ID NO:40) and residues 512-526 having the sequence YHNGDAHTSPDEL (SEQ ID NO:41) comprise the substrate access loops of the isoprene synthase. In some embodiments, amino acids 1-16 and 17-28 comprise N-terminal loops designated N-terminal loop I and N-terminal loop II.

The invention provides a crystalline form of a polypeptide that comprises an amino acid sequence having at least 75% identity to SEQ ID NO:11. In some embodiments, the polypeptide comprises an amino acid sequence having at least 85% identity to SEQ ID NO:11. In other embodiments, the polypeptide comprises an amino acid sequence having at least 90% identity to SEQ ID NO:11.

The invention provides a crystalline form of a polypeptide that comprises an amino acid sequence having at least 75% identity to SEQ ID NO:18. In some embodiments, the polypeptide comprises an amino acid sequence having at least 85% identity to SEQ ID NO:18. In other embodiments, the polypeptide comprises an amino acid sequence having at least 90% identity to SEQ ID NO:11.

The invention provides a scalable three-dimensional configuration of points, at least a portion of said points derived from structure coordinates of at least a portion of a *P. tremuloides* isoprene synthase molecule or molecular complex listed in Table 3-7 and having a root mean square deviation of less than about 1.5 Å from said structure coordinates. In some embodiments, at least a portion of the points derived from the *P. tremuloides* isoprene synthase structure coordinates are derived from structure coordinates representing the locations of at least the backbone atoms of a plurality of the amino acids defining at least one *P. tremuloides* isoprene synthase or *P. tremuloides* isoprene synthase-like diphosphate/metal binding site comprising amino acids Arg 255, Asp 292, Asp 296, Glu 370, Arg 433 and Asn436. In some embodiments, at least a portion of the points derived from the *P. tremuloides* isoprene synthase structure coordinates are derived from structure coordinates representing the locations of at least the backbone atoms of a plurality of the amino acids defining at least one *P. tremuloides* isoprene synthase or *P. tremuloides* isoprene synthase-like isoprenyl binding site, the isoprenyl binding site comprising amino acids Ser 261, Trp 264, Phe 285, Thr 289, Ser 393, Ser 394, Phe 432, and Tyr 512. In other embodiments, at least a portion of the points derived from structure coordinates representing the locations of at least the backbone atoms of a plurality of the amino acids defining at least one *P. tremuloides* isoprene synthase or *P. tremuloides* isoprene synthase-like flexible loop including but not limited to Loop I amino acid residues 438-453 including the sequence SASAEIARGETANS (SEQ ID NO:40), residues 512-526 having the sequence YHNGDAHTSPDEL (SEQ ID NO:41), amino acids 1-16 forming N-terminal loop I amino acids 17-28 forming N-terminal loop II. In some embodiments, at least a portion of the points derived from the *P. tremuloides* isoprene synthase structure coordinates are derived from structure coordinates representing the locations of at least the backbone atoms of a plurality of the amino acids defining at least one *P. tremuloides* isoprene synthase or *P. tremuloides* isoprene synthase-like diphosphate/metal binding site, the diphosphate/metal binding site comprising amino acids Arg 255, Asp 292, Asp 296, Glu 370, Arg 433 and Asn436; and at least a portion of the points derived from the *P. tremuloides* isoprene synthase structure coordinates are derived from structure coordinates representing the locations of at least the backbone atoms of a plurality of the amino acids defining at least one *P. tremuloides* isoprene synthase or *P. tremuloides* isoprene synthase-like isoprenyl binding site, the isoprenyl binding site comprising amino acids Ser 261, Trp 264, Phe 285, Thr 289, Ser 393, Ser 394, Phe 432, and Try 512.

The invention provides a machine-readable medium embedded with information that corresponds to a three-dimensional structural representation of a crystalline form of a *P. tremuloides* isoprene synthase or of a *P. alba* isoprene synthase. Additionally, the invention provides a computer system comprising a database containing information on the three dimensional structure of a crystalline form of a *P. tremuloides* isoprene synthase or a *P. alba* isoprene synthase and a user interface to view the information. A figure showing the high structural homology between the two coordinate sets included is shown as a stereodisgram in FIG. 64.

The invention provides agents characterized by a three-dimensional configuration of points derived from structure coordinates of at least a portion of a *P. tremuloides* isoprene synthase molecule or molecular complex listed in Table 3-7 and having a root mean square deviation of less than about 1.5 Å from said structure coordinates. In some embodiments, agents are characterized by a three-dimensional configuration of points derived from structure coordinates representing the locations of at least the backbone atoms of a plurality of the amino acids defining at least one *P. tremuloides* isoprene synthase or *P. tremuloides* isoprene synthase-like diphosphate/metal binding site comprising amino acids Arg 255, Asp 292, Asp 296, Glu 370, Arg 433 and Asn436. In some embodiments, agents are characterized by at least a portion of the points derived from the *P. tremuloides* isoprene synthase structure coordinates are derived from structure coordinates representing the locations of at least the backbone atoms of a plurality of the amino acids defining at least one *P. tremuloides* isoprene synthase or *P. tremuloides* isoprene synthase-like isoprenyl binding site, the isoprenyl binding site comprising amino acids Ser 261, Trp 264, Phe 285, Thr 289, Ser 393, Ser 394, Phe 432, and Try 512. In other embodiments, agents are characterized by at least a portion of the points derived from structure coordinates representing the locations of at least the backbone atoms of a plurality of the amino acids defining at least one *P. tremuloides* isoprene synthase or *P. tremuloides* isoprene synthase-like flexible loop including but not limited to Loop I amino acid residues 438-453 including the sequence SASAEIARGETANS (SEQ ID NO:40), residues 512-526 having the sequence YHNGDAHTSPDEL (SEQ ID NO:41), amino acids 1-16 forming N-terminal loop I amino acids 17-28 forming N-terminal loop II.

The invention provides a scalable three-dimensional configuration of points, at least a portion of the points derived from structure coordinates of a *P. alba* isoprene synthase molecule or a molecular complex listed in Table 4-2 and having a root mean square deviation of less than about 1.5 Å from said structure coordinates. In some embodiments, at lease a portion of the points derived from the *P. alba* isoprene synthase structure coordinates are derived from structure coordinates representing the locations of at least the backbone atoms of a plurality of the amino acids defining at least one *P. alba* isoprene synthase or *P. alba* isoprene synthase-like sites, including but not limited to, a diphosphate/metal binding site, a isoprenyl binding site, a flexible loop, an electrostatic patch and a hinge region.

The invention provides agents characterized by a three-dimensional configuration of points derived from the structure coordinates of at lease a portion of a *P. alba* isoprene synthase molecule or molecular complex listed in Table 4-2 and having a root mean square deviation of less than about 1.5 Å from said structure coordinates. In some embodiments, agents are characterized by a three-dimensional configuration of points derived from the structural reaction coordinates representing the locations of at least the backbone atoms of a plurality of the amino acids defining at least one *P. alba* isoprene synthase or *P. alba* isoprene synthase-like of diphosphate/metal binding site, a flexible loop, an electrostatic patch and a hinge region.

The invention provides methods of producing isoprene by (a) providing a host cell comprising a *P. alba* isoprene synthase variant and (b) culturing the host cell under conditions suitable for producing isoprene.

BRIEF DESCRIPTION OF THE DRAWINGS

FIG. 3 (3A, B) provides the nucleotide sequence (SEQ ID NO:1) of plasmid p9795.

FIG. 5 (5A, B, C) provides the nucleotide sequence (SEQ ID NO:2) of plasmid pTrcKudzu.

FIG. 7 (7A, B, C) provides the nucleotide sequence (SEQ ID NO:3) of plasmid pMAL-C4X.

FIG. 9 (9A, B, C, D) provide the nucleotide sequence (SEQ ID NO:4) of pMAL-C4X-Kudzu.

FIG. 10 provides maps of pET24 *P. tremuloides* and pET24 *P. trichocarpa.*

FIG. 11 provides the amino acid Sequence (SEQ ID NO:5) of *P. tremuloides* IspS in *P. tremuloides* pET24a.

FIG. 12 (12A, B, C) provides the nucleotide sequence (SEQ ID NO:6) of plasmid *P. tremuloides* pET24.

FIG. 13 provides the amino acid sequence (SEQ ID NO:7) of *P. trichocarpa* IspS in *P. trichocarpa* pET24a.

FIG. 14 (14A, B, C) provides the nucleotide sequence (SEQ ID NO:8) of plasmid *P. trichocarpa* pET24.

FIG. 15A provides the map of plasmids pDu30.

FIG. 15B provides the map of plasmids pDu31.

FIG. 16 provides the amino acid sequence (SEQ ID NO:9) of the *P. alba* IspS variant in pDu30.

FIG. 17 (17A, B, C) provides the nucleotide sequence (SEQ ID NO:10) of plasmid pDu30.

FIG. 18 provides the amino acid sequence (SEQ ID NO:11) of the *P. tremuloides* IspS variant in pDu31. The numbering convention for purposes of describing the three-dimensional structure of isoprene synthase is such that the first number of the complete sequence containing the tag is −35, with the first three residues of IspS being MRR (underlined).

FIG. 19 (19A, B, C) provides the nucleotide sequence (SEQ ID NO:12) of plasmid pDu31.

FIG. 20 provides the amino acid sequence (SEQ ID NO:13) of the *P. trichocarpa* IspS variant in pDu32.

FIG. 21 (21A, B, C) provides the nucleotide sequence (SEQ ID NO:14) of plasmid pDu32.

FIG. 22 (22A, B, C) provides the nucleotide sequence (SEQ ID NO:15) of plasmid pDu27.

FIG. 23 provides the amino acid sequence (SEQ ID NO:16) of full length *P. alba* IspS in *P. alba* pET24a.

FIG. 24 (24A, B, C) provides the nucleotide sequence of sequence (SEQ ID NO:17) of *P. alba* pET24a.

FIG. 25 provides the maps of plasmids MD09-161 and MD09-163.

FIG. 26 provides amino acid sequence (SEQ ID NO:18) of *P. alba* MEA(+)TEV in MD09-163.

FIG. 27 (A, B, C) provides the nucleotide sequence (SEQ ID NO:19) of plasmid MD09-163. The CDS is underlined and the TEV protease site is bold.

FIG. 28 provides the amino acid sequence (SEQ ID NO:20) of *P. alba* FL (+) TEV in MD09-161.

FIG. 29 (29A, B, C) provides the nucleotide sequence (SEQ ID NO:21) of MD09-161. The CDS is underlined and the TEV protease site is bold.

FIG. 37 provides the amino acid sequence (SEQ ID NO:42) of a kudzu isoprene synthase.

FIG. 38 provides the amino acid sequence of a *Populus [alba×tremuloides]* isoprene synthase (SEQ ID NO:43).

FIG. 40 (40A, B, C) provides the nucleotide sequence (SEQ ID NO:44) of pCL201. The IspS CDS is underlined.

FIG. 41 provides the amino acid sequence of *P. alba* IspS residues 1 through 544 (SEQ ID NO:45).

FIG. 45 shows the layout of a typical 96-well plate containing four complete libraries to be screened for isoprene production and protein concentration.

FIG. 51 shows an SDS-PAGE gel showing IspS-L494P at different stages of the purification. Lane 1—molecular weight standard; Lane 2—IspS-L494P prior to treatment with TurboTEV; Lane 3—IspS-L494P treated with TurboTEV; Lanes 4-6—IspS-L494P after final buffer exchange at different dilution levels.

FIG. 52 shows $2F_O$-$2F_c$ electron density map at residue 494 contoured at 1-sigma. Panel A shows 494L, Panel B shows 494P.

FIG. 53 depicts the alignment of the loop containing residue 494. Wild type IspS is light grey and IspS-L494P is dark grey. The L494P mutation results in an alternate loop structure.

FIG. 54 depicts a SDS-PAGE gel showing purified IspS-T536F at different dilutions (lanes 2-4) and molecular weight standard (lane 1).

FIG. 55 depicts a SDS-PAGE gel showing total cell lysate (lanes 2, 5, 8), supernatant (lanes 3, 6, 9), and purified protein (lanes 4, 7, 10) for wild type IspS, IspS-L494P and IspS-T536F, respectively. A molecular weight marker is in lane 1.

FIG. 56 depicts thermal unfolding curves for wild type IspS, IspS-L494P, and IspS-T536F incubated with buffer only. $T_M$ values are indicated for each variant.

FIG. 57 depicts thermal unfolding curves for wild type IspS, IspS-L494P, and IspS-T536F incubated with 5 mM sodium pyrophosphate. $T_M$ values are indicated for each variant.

FIG. 58 depicts temperature activity ration curves for wild type IspS (WT), IspS-L494P (LP), and IspS-T536F (TF). Data are plotted as a ratio of the specific activity (nmol/mg/min) of the protein at a given temperature divided by the specific activity at 35° C.

FIG. 59 depicts local alignment of *P. alba* isoprene synthase and related terpene synthase enzymes (SEQ IDS NOs: 99-112).

FIG. 60 depicts a map of plasmid MD09-163 with A453N, G491S, L494P, and T536C/F mutations.

FIG. 61 depicts a gel showing a dilution series of Isoprene Synthases assayed for rate vs. [DMAPP].

FIG. 62 depicts a graph showing the specific activity of each variant with 4 mM DMAPP assayed at 30° C. The black bar indicates the specific activity of the WT isoprene synthase.

FIG. 63 depicts a graph showing rate vs. [DMAPP] for the P, SP and SPC variants of isoprene synthase and WT isoprene synthase. Each data point on the graph is the average of three independently performed kinetic assays. Error bars are reported as one standard deviation above and below the data point.

FIG. 64 depicts an alignment of the *P. tremuloides* (black) and *P. alba* structures (grey) showing high level of structural homology.

DETAILED DESCRIPTION OF THE INVENTION

Figure 1:
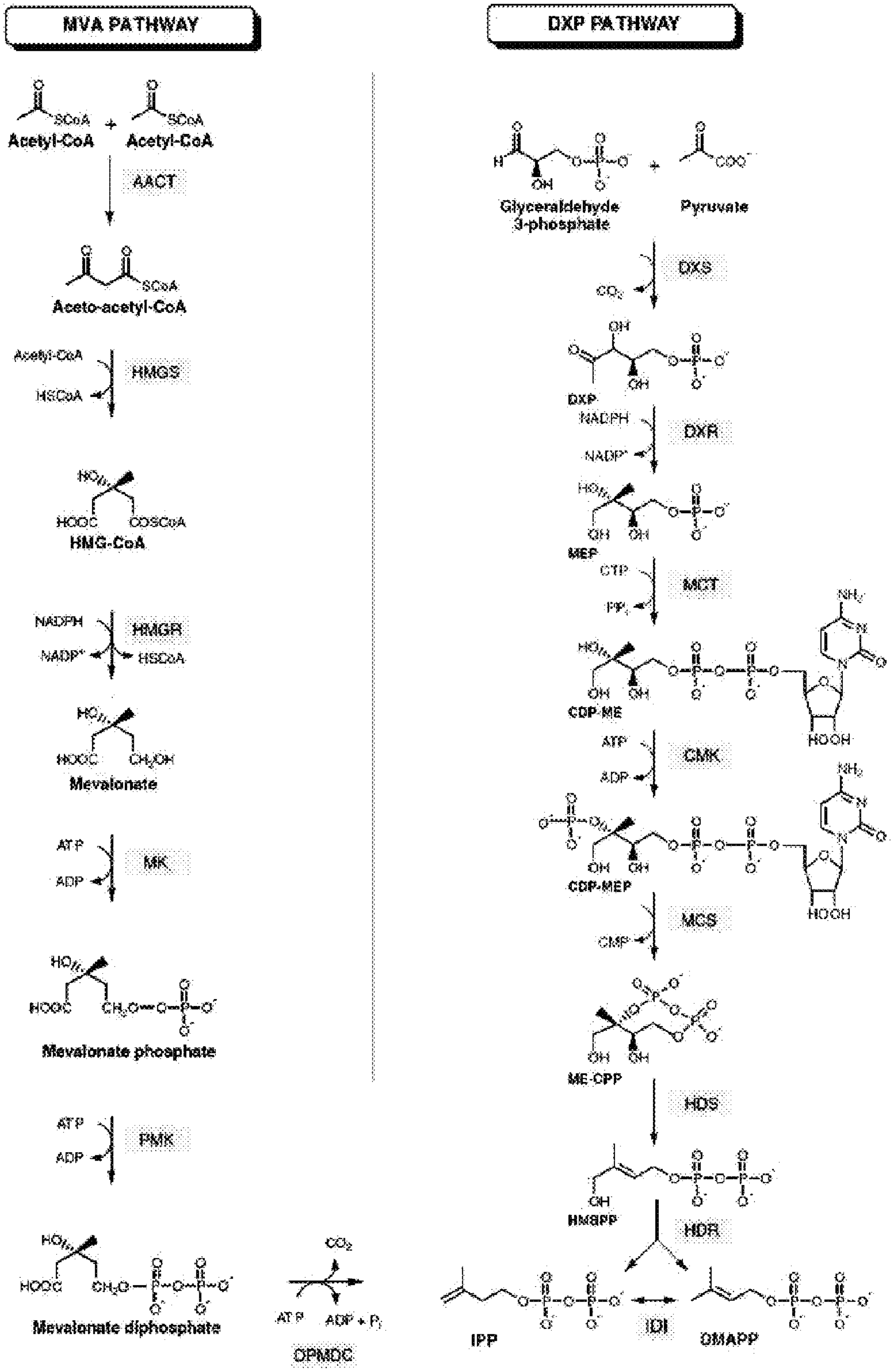
FIG. 1 shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet. 19:9-14, 1991. PMK; Phosphomevalonate kinase, ERGS, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

The present invention provides methods and compositions comprising at least one synthase enzyme with improved activity (e.g., catalytic activity) and/or solubility, variants of synthase and agents characterized by modifications of the amino acid residues in two flexible loops and/or N-terminus and/or their adjacent regions. In particular, the present invention provides for the selective modification of these segments in a three-dimensional structure of an isoprene synthase. Isoprene synthase contemplated by the invention include, but are not limited to plant isoprene synthases; e.g., poplar isoprene synthase, kudzu isoprene synthase, oak isoprene synthase and the like. Poplar isoprene synthase include, but are not limited to, isoprene synthases from *P. tremuloides, P. alba, P. alba v. tremuloides, P. trichocharpa*, and the like. Variant isoprene synthases for increased isoprene production in microbial host cells are derived based on the three-dimensional structure. Agents which can increase isoprene production can also be modeled using the three-dimensional structure of an isoprene synthase provided herein. Biosynthetically produced isoprene of the present invention finds use in the manufacture of rubber and elastomers.

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual," Third Edition, Cold Spring Harbor, 2001; and Ausubel et al., "Current Protocols in Molecular Biology," 1987). All patents, patent applications, articles and publications mentioned herein, both supra and infra, are hereby expressly incorporated herein by reference.

DEFINITIONS

As used herein, the term isoprene refers to 2-methyl-1,3-butadiene (CAS#78-79-5). Isoprene can be produced as the direct and final volatile C5 hydrocarbon product from the elimination of pyrophosphate from 3,3-dimethylallyl pyrophosphate (DMAPP), and does not involve the linking or polymerization of (an) IPP molecule(s) to (a) DMAPP molecule(s).

As used herein, the terms "isoprene synthase," and "IspS," refer to the enzymes that catalyze the elimination or pyrophosphate from diemethylallyl diphosphate (DMAPP) to form isoprene. In some preferred embodiments, the IspS is an enzyme obtained from plants such as kudzu, poplar or red oak. In some embodiments, the term "IspS" refers to a naturally occurring mature enzyme or portion thereof.

As used herein, the term "variant proteins" refers to proteins that differ from a parent protein (e.g., kudzu IspS set forth as SEQ ID NO:42 and *P. alba* IspS set forth in SEQ ID NO:16 or FIG. 23) and from one another by a small number of amino acid residues. The number of differing amino acid residues may be one or more, preferably 1, 2, 3, 4, 5, 6, 7, 8, 9, 10, 11, 12, 13, 14, 15, 20, 30, 40, 50, or more amino acid residues. In some preferred embodiments, the number of different amino acids between variants is between 1 and 10. In some particularly preferred embodiments, related proteins and particularly variant proteins have at least 35%, 40%, 45%, 50%, 55%, 60%, 65%, 70%, 75%, 80%, 85%, 90%, 95%, 97%, 98%, or 99% amino acid sequence identity. Related (and derivative) proteins can comprise "variant proteins." Additionally, a related protein or a variant protein as used herein refers to a protein that differs from another related protein or a parent protein in the number of prominent regions. For example, in some embodiments, variant proteins have 1, 2, 3, 4, 5, or 10 corresponding prominent regions that differ from the parent protein.

As discussed in greater detail herein, several methods are known in the art that are suitable for generating variants of the enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

As used herein, the singular form "a", "an", and "the" includes plural references unless indicated otherwise.

As used herein, the term "agent" can refer to any type of composition of matter, including but not limited to, polypeptides, nucleotides, small molecules, and synthetic compounds.

As used herein, the term "gene" refers to a polynucleotide (e.g., a DNA segment) that encodes a polypeptide and includes regions preceding and following the coding regions as well as intervening sequences (introns) between individual coding segments (exons).

As used herein, the terms "starting gene" and "parent gene" refer to a gene of interest that encodes a protein of interest that is to be improved and/or changed using the present invention. Likewise, the terms "starting protein" and "parent protein" refer to a protein of interest that is to be improved and/or changed using the present invention.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one.

As used herein, "homology" refers to sequence similarity or identity, with identity being preferred. This homology is determined using standard techniques known in the art (See e.g., Smith and Waterman, Adv Appl Math, 2:482, 1981; Needleman and Wunsch, J Mol Biol, 48:443, 1970; Pearson and Lipman, Proc Natl Acad Sci USA, 85:2444, 1988; programs such as GAP, BESTFIT, FASTA, and TFASTA in the Wisconsin Genetics Software Package, Genetics Computer Group, Madison, Wis.; and Devereux et al., Nucl Acid Res, 12:387-395, 1984).

As used herein, an "analogous sequence" on an isoprene synthase is one wherein the function of the gene is essentially the same as the gene based on the kudzu isoprene synthase. Additionally, analogous genes include at least 45%, 50%, 55%, 60%, 65%, 70%, 75%, 80%, 85%, 90%, 95%, 97%, 98%, 99% or 100% sequence identity with the sequence of the kudzu isoprene synthase. In additional embodiments more than one of the above properties applies to the sequence. Analogous sequences are determined by known methods of sequence alignment. A commonly used alignment method is BLAST, although as indicated above and below, there are other methods that also find use in aligning sequences.

"Percent sequence identity," "percent amino acid sequence identity," "percent gene sequence identity," and/or "percent nucleic acid/polynucleotide sequence identity," with respect to two amino acids, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, preferably at least 75%, preferably at least 80%, preferably at least 85%, preferably at least 90%, preferably at least 95%, preferably at least 97%, preferably at least 98% and preferably at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "crystal lattice" means the array of points defined by the vertices of packed unit cells.

As used herein, the term "unit cell" means a basic parallelipiped shaped block. The entire volume of a crystal can be constructed by regular assembly of such blocks. Each unit cell comprises a complete representation of the unit of pattern, the repetition of which builds up the crystal. Thus, the term "unit cell" means the fundamental portion of a crystal structure that is repeated infinitely by translation in three dimensions. A unit cell is characterized by three vectors a, b, and c, not located in one plane, which form the edges of a parallelepiped. Angles $\alpha$, $\beta$, and $\gamma$ define the angles between the vectors: angle $\alpha$ is the angle between vectors b and c; angle $\beta$ is the angle between vectors a and c; and angle $\gamma$ is the angle between vectors a and b. The entire volume of a crystal can be constructed by regular assembly of unit cells; each unit cell comprises a complete representation of the unit of pattern, the repetition of which builds up the crystal.

The term "structure coordinates" refers to Cartesian coordinates derived from mathematical equations related to the patterns obtained on diffraction of a monochromatic beam of x-rays by the atoms (scattering centers) of an isoprene synthase complex in crystal form. The diffraction data are used to calculate an electron density map of the repeating unit of the crystal. The electron density maps are then used to establish the positions of the individual atoms of the isoprene synthase protein or protein/ligand complex.

As used herein, the terms "active site," "binding site" or "binding pocket" refer to a region of a polypeptide or a molecular complex comprising the polypeptide that, as a result of the primary amino acid sequence of the polypeptide and/or its three-dimensional shape, favorably associates with another chemical entity or compound including ligands or inhibitors. Thus, an active site may include or consist of features such as interfaces between domains. Chemical entities or compounds that may associate with an active site include, but are not limited to, compounds, ligands, cofactors, substrates, inhibitors, agonists, antagonists, etc.

"Structural reaction residues" refers to a three-dimensional collection of atoms involved in an enzymatic reaction. For example, these would include those forming the active site, those coordinating metal ions and those forming the substrate bind region. In particular, those forming the flexible loops and N-terminus and the adjacent residues that stabilize the flexible segments when substrate is bound.

Structurally equivalent synthases refer to those synthases for which a crystallographic structure has been determined, whose atomic coordinates can be aligned by a publically available software package, such as PYMOL (DeLano Scientific LLC) such that a preponderance of the main chain alpha carbon atoms can be aligned within a rms deviation of 0.2 nm. For this purpose, a preponderance would be defined as either 50%, 60% or 70% of the total alpha carbons of the isoprene synthase structure.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of a *P. tremuloides* isoprene synthase, a *P. alba* isoprene synthase, or an active site portion thereof, as defined by the structure coordinates described herein.

"Having substantially the same three-dimensional structure" refers to a polypeptide that is characterized by a set of atomic structure coordinates that have a root mean square deviation (r.m.s.d.) of less than or equal to about 1.5 Å when superimposed onto the atomic structure coordinates of an isoprene synthase, e.g. the atomic structure coordinates of Table 3-7 or Table 4-2 when at least about 50% to 100% of the C$\alpha$ atoms of the coordinates are included in the superposition.

As used herein, "homologous segment" refers to a segment of an enzyme having a root mean square deviation of less than about 1.5 Å in models of related enzymes. For example the model of the *P. tremuloides* isoprene synthase molecule or molecular complex listed in Table 3-7 can be used to identify homologous segments having a root mean square deviation of less than about 1.5 Å in models of related isoprene synthases.

Slight variations in structure coordinates can be generated by mathematically manipulating the isoprene synthase structure coordinates provided herein. For example, the structure coordinates set forth in Table 3-7 or Table 4-2 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Thus, for the purpose of the structures provided herein, any active site, binding site or binding pocket defined by a set of structure coordinates for a polypeptide or for a homolog of a polypeptide from any source having a root mean square deviation of non-hydrogen atoms of less than about 1.5 Å when superimposed on the non-hydrogen atom positions of the corresponding atomic coordinates of Table 3-7 or Table 4-2, are considered substantially identical or homologous.

As used herein, "equivalent or homologous residues" refers to proteins that share particular amino acid residues. Equivalent residues may be identified by determining homology at the level of tertiary structure for a terpene synthase (e.g., isoprene synthase) whose tertiary structure has been determined by x-ray crystallography. Equivalent residues are defined as those for which the atomic coordinates of two (2) or more of the main chain atoms of a particular amino acid residue of the terpene synthase having putative equivalent residues and the substrate of interest (e.g., N on N, CA on CA, C on C and O on O) are within 0.2 nm and preferably 0.15 nm after alignment. Alignment is achieved after the best model has been oriented and positioned to give the maximum overlap of atomic coordinates of non-hydrogen protein atoms of the terpene synthases and substrates analyzed. The preferred model is the crystallographic model giving the lowest R factor for experimental diffraction data at the highest resolution available, determined using methods known to those skilled in the art of crystallography and protein characterization/analysis. For example, equivalent residues which are functionally analogous to a specific residue of isoprene synthase are defined as those amino acids at a structurally homologous synthase which may adopt a conformation such that they either alter, modify, or contribute to protein structure, substrate binding or catalysis in a manner defined or attributed to a specific residue of isoprene synthase.

Isoprene Synthase

Isoprene monomer is employed in the manufacture of polyisoprene and various copolymers (with isobutylene, butadiene, styrene, or other monomers). To build a strain (prokaryotic or eukaryotic) capable of producing commercially viable levels of isoprene requires optimization of the entire pathway, either MVA to isoprene or DXP to isoprene. A key enzyme in the pathway is isoprene synthase (IspS), which converts the precursor DMAPP to isoprene. The only isoprene synthases (IspS) identified to date are those from plants such as poplar, English oak and kudzu vine. Although some bacteria, such as *Bacillus subtilis*, also produce isoprene, a prokaryotic IspS has yet to be identified and the native IspS activity in *Bacillus* is not sufficient for a commercial process. The plant IspS enzymes identified to date have been partially characterized in part by expression in *E. coli* and some of the kinetic parameters of these enzymes have been determined in vitro with purified protein. However, the kinetic parameters ($K_m$, rate, etc.) of the native IspS enzymes are insufficient for commercial production of isoprene in a biological host.

To solve this problem as described herein, an isoprene synthase is expressed in a bacterial host. In addition, the isoprene synthase is engineered for a change in a property of interest. The invention provides a three-dimensional structure which can aid in the design of variants of isoprene synthase and agents with similar three-dimensional structure and/or reaction coordinates to the three-dimensional structure provided herein. These variants and agents are useful for the commercial production of isoprene in a biological host.

Characterization of wild-type and mutant isoprene synthase is accomplished via any means or "test" suitable and is preferably based on the assessment of properties of interest. Properties of interest include but are not limited to: pH optima, temperature stability (e.g., $T_m$ value), intracellular and extracellular solubility, $K_m$ value, $k_{cat}$ value, or specific activity, as well as sensitivity to potential inhibitors including substrate or product inhibition. Oxidative and proteolytic stability are also of interest. Furthermore, activation or inhibition due to metal ion effects and ionic strength is of interest. These properties and parameters can be assessed by the conversion of DMAPP to isoprene in vitro with purified or partially purified isoprene synthase or in vivo in the context of a host organism such as *E. coli* expressing the DXP pathway, the MVA pathway, or both. It is contemplated that enzymes having various degrees of stability, solubility, activity, and/or expression level in one or more of test conditions will find use in the present invention for the production of isoprene in a diversity of hosts.

The invention features compositions and methods for the production of increased amounts of isoprene. In particular, these compositions and methods increase the rate of isoprene production and increase the total amount of isoprene that is produced. The biosynthetic processes for isoprene production described herein are a desirable alternative to using natural rubber. As discussed further below, the amount of isoprene produced by cells can be greatly increased by introducing a heterologous nucleic acid encoding an isoprene synthase (IspS) polypeptide into the cells. Isoprene synthase polypeptides convert dimethylallyl diphosphate (DMAPP) into isoprene.

Additionally isoprene production by cells containing a heterologous isoprene synthase nucleic acid can be enhanced by increasing the amount of a 1-deoxy-D-xylulose-5-phosphate synthase (DXS) polypeptide, and/or an isopentenyl diphosphate isomerase (IDI) polypeptide, expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

The encoded DXS and IDI polypeptides are part of the DXP pathway for the biosynthesis of isoprene (FIG. 1). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount of IPP that is converted into DMAPP, which in turn is converted into isoprene.

In some embodiments, the production of isoprene by cells containing a heterologous isoprene synthase nucleic acid can be augmented by increasing expression of one or more MVA polypeptide(s) in the cells (FIG. 1). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain the entire MVA pathway, which includes AA-CoA thiolase, HMG-CoA synthase, HMG-CoA reductase, MVK, PMK, MVD, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity.

In one embodiment, DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 μl of 1M $MgCl_2$, 1 mM (250 μg/ml) DMAPP, 65 μl of Plant Extract Buffer (PEB) (50 mM Tris-HCl, pH 8.0, 20 mM $MgCl_2$, 5% glycerol, and 2 mM DTT) is added to 25 μl of cell extract in a 20 ml Headspace vial with a metal screw cap and teflon coated silicon septum (Agilent Technologies) and cultured at 37° C. for 15 minutes with shaking. The reaction is quenched by adding 200 μl of 250 mM EDTA or by heat inactivation, and isoprene is quantified by GC/MS.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as variant polypeptides and nucleic acids derived from any of the source organisms described herein.

In some embodiments, the isoprene synthase polypeptide or nucleic acid is from the family Fabaceae, the family Salicaceae, or the family Fagaceae. In some embodiments, the isoprene synthase polypeptide or nucleic acid is a naturally-occurring polypeptide or nucleic acid from *Pueraria montana* (kudzu) (Sharkey et al., Plant Physiology 137: 700-712, 2005), poplar (such as *Populus alba×tremula* CAC35696, Miller et al., Planta 213: 483-487, 2001) or *Populus alba*, aspen (such as *Populus tremuloides*) Silver et al., JBC 270 (22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by GenBank Accession Nos. AY341431, AY316691, AB198180, AJ294819.1, EU693027.1, EF638224.1, AM410988.1, EF147555.1, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is not a naturally-occurring polypeptide or nucleic acid from poplar (such as *Populus alba×tremula* CAC35696).

Three Dimensional Structure and/or Crystallization

Polypeptides, e.g. isoprene synthase, have a three-dimensional structure determined by the primary amino acid sequence and the environment surrounding the polypeptide. This three-dimensional structure establishes the polypeptide's activity, stability, binding affinity, binding specificity, and other biochemical attributes. Thus, knowledge of a protein's three-dimensional structure can provide much guidance in designing improvements to its biological activity; for example, greater catalytic activity and/or solubility.

The three-dimensional structure of a polypeptide can be determined in a number of ways. Many of the most precise methods employ X-ray crystallography (See, e.g., Van Holde, (1971) Physical Biochemistry, Prentice-Hall, New Jersey, pp. 221-39). This technique relies on the ability of crystalline lattices to diffract X-rays or other forms of radiation. Diffraction experiments suitable for determining the three-dimensional structure of macromolecules typically require high-quality crystals. The crystallization properties of a polypeptide vary greatly (Dale, et al., *J. Struct. Biol.* 142:88-97, 2003; MacPherson, A., *Methods* 34:254-265, 2004; and Slabinski, L et al., *Protein Science* 16:2472-2482, 2007). In some cases, polypeptides crystallize readily whereas in other cases, polypeptides have proven extremely difficult to obtain. There is no comprehensive theory to guide efforts to crystallize macromolecules and as a result, most efforts macromolecular crystal growth is empirical in nature (MacPherson, 2004). Factors which can influence the production of crystals including physical, chemical and biochemical factors. These factors include purity of the polypeptide, pH, salt, and concentrations of other precipitants.

Another key variable in the generation of crystals of a polypeptide is the polypeptide itself. Some polypeptides crystallize rather easily while homologous proteins prove to be very difficult to crystallize (Dale et al. 2003). It is generally recognized that rigid, stable proteins are much more likely to crystallize than proteins that are internally flexible or have dynamic surfaces. Solubility is another factor that impacts macromolecular crystallization. Insoluble polypeptides do not readily form crystals because they tend to aggregate. Highly soluble polypeptides, on the other hand, do not readily form crystals because of difficulties in obtaining a supersaturated state. Glycoslyated polypeptides also do not readily form crystals because they tend to be highly soluble. As such, posttranslational modifications can have a large impact on the crystallization of a polypeptide.

Another hurdle in the development of a three-dimensional structure of a polypeptide is the "phase problem." A crystal behaves like a three-dimensional diffraction grating, which gives rise to both constructive and destructive interference effects in the diffraction pattern, such that it appears on the detector as a series of discrete spots which are known as reflections. Each reflection contains information on all atoms in the structure and conversely each atom contributes to the intensity of each reflection. As with all forms of electromagnetic radiation, X-rays have wave properties, in other words, they have both an amplitude and a phase. In order to recombine a diffraction pattern, both of these parameters are required for each reflection. Unfortunately, only the amplitudes can be recorded experimentally and as such, all phase information is lost. One method to solve the "phase problem" is to compare the molecular coordinates with the coordinates of a similar protein by a process called Molecular Replacement.

"Molecular Replacement" refers to the method of calculating initial phases for a new crystal of a polypeptide whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the polypeptides comprising the new crystal (Jones et al., 1991, Acta Crystallogr. 47:753-70; Brunger et al., 1998, Acta Crystallogr. D. Biol. Crystallogr. 54:905-21).

The isoprene synthases of plants are expected to be homologous to terpene synthases. Previous efforts to utilize the structure of isoprene synthase in order to improve production of isoprene have relied on the structures of other terpene synthases in which three-dimensional structures are available including bornyl diphosphate synthase and 5-epi-aristolochene synthase (see e.g., U.S. Provisional patent application Ser. No. 12/429,143 and WO 2008/137092).

A set of coordinates determined by X-ray crystallography is not without standard error. In general, the error in the coordinates tends to be reduced as the resolution is increased, since more experimental diffraction data is available for the model fitting and refinement. Thus, for example, more diffraction data can be collected from a crystal that diffracts to a resolution of 3.0 angstroms than from a crystal that diffracts to a lower resolution, such as 3.5 angstroms. Consequently, the refined structural coordinates will usually be more accurate when fitted and refined using data from a crystal that diffracts to higher resolution. If the coordinates are not sufficiently accurate, then the design process will be ineffective. In most cases, it is very difficult or impossible to collect sufficient diffraction data to define atomic coordinates precisely when the crystals diffract to a resolution of only 3.5 angstroms or poorer. Thus, in most cases, it is difficult to use X-ray structures in structure-based ligand design when the X-ray structures are based on crystals that diffract to a resolution of only 3.5 angstroms or poorer. However, common experience has shown that crystals diffracting to 3.0 angstroms or better can yield X-ray structures with sufficient accuracy to greatly facilitate structure-based drug design. Further improvement in the resolution can further facilitate structure-based design, but the coordinates obtained at 3.0 angstroms resolution are generally adequate for most purposes. The three-dimensional structure of isoprene synthase provided by the present invention was resolved to 3.05 angstroms (see Example 3).

Three Dimensional Structure and/or Crystallization of IspS

A number of different constructs expressing different isoprene synthases were generated in order to obtain a three-dimensional structure of the enzyme. One construct contained the kudzu isoprene synthase linked to a fragment of the maltose binding protein (MBP) to facilitate purification. The purified MBD-Kudzu isoprene synthase was subjected to commercially available crystallization screens including Crystal Screen (Hampton Research) and JCSG+ Suite (Qiagen). No fewer than 1536 different conditions were surveyed, including ranges of pH, protein concentration and crystallization reagents. In the majority of cases, the MBP-Kudzu isoprene synthase fusion protein precipitated out of solution and no crystals were obtained.

A second attempt to crystallize isoprene synthase focused on isoprene synthase from *P. alba*. Here the protein was linked to a histidine tag for ease of purification. Over 288 conditions were screened and the nine best crystals were prepared for data collection but the crystals either did not defract or were salt crystals. Likewise, crystals derived from a full-length, untagged *P. alba* isoprene synthase and an N-terminally truncated *P. trichocharpa* isoprene synthase did not diffract.

Crystals were obtained from a construct containing a 19 residue N-terminal truncation of *P. alba* isoprene synthase and linked to a histidine tag. Resolution of the crystal structure was improved from 16 Å to 5 Å. As discussed above, it is preferred that three-dimensional structures are determined in cases where crystal resolution is 3.5 Å or finer. Crystals were obtained from a second N-terminally truncated *P. alba* isoprene synthase following a screen of 528 variations of pH, precipitating agents, concentrations and inhibitors. In order to improve diffraction, various crystal freezing conditions were tested but the diffraction limits only improved from 10 Å to 6.5 Å. Crystallization conditions were further optimized and a crystal resolution of 2.7 Å was obtained.

An isoprene synthase from *P. tremuloides* was generated with an N-terminal truncation and a histidine tag and used in commercially available screens. Rod and plate-like crystals were observed and an additional 120 experiments were performed by varying pH, concentration and crystallization reagents. Here, the best crystal has a resolution of 5 Å. Modification of the freezing conditions resulted in a crystal that diffracted at 3.3 Å and ultimately to 3.05 Å using beamline 11-1 of the Stanford Synchroton Radiation Laboratory.

The phasing problem was resolved by molecular replacement using a monomer of limonene synthase as the starting model. Like isoprene synthase, limonene synthase is terpene synthase which has 41.4% sequence identity to *P. tremuloides* isoprene synthase.

The invention provides a crystalline form of isoprene synthase. In some aspects, the invention provides a crystalline from of *P. tremuloides* isoprene synthase. The crystals belong to the tetragonal space group $P4_32_12$, and have unit cell dimensions a is about 154.2 Å, b is about 154.2 Å, c is about 142.7 Å where $\alpha=\beta=\gamma=90°$. Unit cells dimensions may vary; for example, by 5%. In some aspects, the invention provides a crystalline from of *P. alba* isoprene synthase. The crystals belong to the tetragonal space group $P4_32_12$, and have unit cell dimensions a is about 156.8 Å, b is about 156.8 Å, c is about 142.5 Å where $\alpha=\beta=\gamma=90°$.

The structure is found to be structurally homologous to other known synthase structures specifically bornyl diphosphate synthase, 5-epi-aritolochene synthase and 4S-limonene synthase. All share a common overall tertiary fold, as measured by a lower than 2.0 Angstrom (0.2 nm) standard deviation for a preponderance of the main chain alpha carbon atoms following alignment. Isoprene synthase has 541 amino acid residues, each with one alpha carbon atom: 433 of these can be aligned with those of limonene synthase with a root mean squared deviation (rms) of 0.12 nm; 418 of these can be aligned with those of bornyl diphosphate synthase with an rms of 0.12 nm; and 395 of these can be aligned with those of 5-epi-aristolochene synthase with an rms of 0.14 nm.

The invention provides the three-dimensional structure of the active site of isoprene synthase. The metal ion and phosphate recognition region comprises amino acid residues Arg 255, Asp 292, Asp 296, Glu 370, Arg 433 and Asn436 of the *P. tremuloides* isoprene synthase. As such, the invention provides the site where dimethylallyl pyrophosphate may bind and react with the isoprene synthase to produce isoprene. Side chains of amino acid residues in the *P. tremuloides* IspS that are found in proximity to the metal and diphosphate binding side chains include Asp 293, Tyr 385, Ser 392, and Asp 437.

The invention provides the substrate access loops of isoprene synthase. The substrate access loops of *P. tremuloides* IspS are in regions that deviate from the bornyl diphosphate synthase (BdpS) structure. In the BdpS structure, the residues create a cover over the active site. Upon substrate binding, the structure of *P. tremuloides* IspS may form a similar structure. In the *P. tremuloides* IspS enzyme, residues 440-453, which have the sequence SASAEIARGETANS (SEQ ID NO:40), and residues 512-526, which have the sequence YHNGDAHTSPDEL (SEQ ID NO:41), form the substrate access loops.

The invention provides the three-dimensional structure of the isoprenyl binding site of isoprene synthase. These are residues in the *P. tremuloides* IspS structure that may bind to the product, isoprene. These residues include Ser 261, Trp 264, Phe 285, Thr 289, Ser 393, Ser 394, Phe 432, and Tyr 512.

In some aspects the invention provides the three-dimensional structure of isoprene synthase which further comprises a ligand; for example, dimethylallyl pyrophosphate. In some cases, the three-dimensional structure of isoprene synthase without a ligand is compared to the three-dimensional structure of isoprene synthase with bound ligand. Such comparisons in the three-dimensional structures of isoprene synthase with or without a ligand may reveal structural perturbations in the enzyme following substrate binding. Molecular modeling may provide clues for designing variants of isoprene synthase for improved activity.

The invention provides structurally equivalent agents that mimic the structure of isoprene synthase or a portion thereof. A structurally equivalent agent is related in terms of its three-dimensional structure. In some cases, the structurally equivalent agent mimics the activity (e.g. catalytic activity) of the isoprene synthase or a structurally equivalent portion of the isoprene synthase. For example, a structurally equivalent agent may be structurally analogous to the active site of an isoprene synthase.

Use of Three-Dimensional Structure of Isoprene Synthase

Structure information, typically in the form of the atomic structure coordinates, can be used in a variety of computational or computer-based methods to, for example, design, screen for and/or identify variants of isoprene synthase for improved activity, expression or stability. Three-dimensional modeling may be performed using the experimentally determined coordinates derived from X-ray diffraction patterns, such as those in Table 3-7 and Table 4-2, for example, wherein such modeling includes, but is not limited to, drawing pictures of the actual structures, building physical models of the actual structures, and determining the structures of related subunits and /ligand and subunit/ligand complexes using the coordinates. Such molecular modeling can utilize known X-ray diffraction molecular modeling algorithms or molecular modeling software to generate atomic coordinates corresponding to the three-dimensional structure of an isoprene synthase.

The structure coordinates generated for *P. tremuloides* isoprene synthase or one of its active sites shown in Table 3-7, *P. alba* isoprene synthase or one of its active sites shown in Table 4-2 or the structure coordinates generated by *P. tremuloides* or *P. alba* isoprene synthase/ligand complex define a unique configuration of points in space. Those of skill in the art understand that a set of structure coordinates for protein or an protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a scalable configuration of points can be defined by increasing or decreasing the distances between coordinates by a scalar factor while keeping the angles essentially the same.

The invention provides methods for increasing the production of isoprene in a host cell by increasing the activity, expression or stability of an isoprene synthase in the host cell. Based on the three-dimensional structure of isoprene synthase, one of skill in the art can use computational methods to modify properties of the isoprene synthase including but not limited to pH optima, $K_M$ value, $k_{cat}$ value, and specific activity of the enzyme. In other aspects of the invention, the three-dimensional structure of isoprene synthase or agents with similar three-dimensional structures may be used as a guide to improve oxidative and/or proteolytic stability of isoprene synthase. The three-dimensional structure of isoprene synthase may be used to evaluate inhibitors of its enzymatic activity including, but not limited to, substrate and product inhibition. In other aspects of the invention, the three dimensional structure may be used to design isoprene synthase variants agents with similar three-dimensional structures for increased expression; for example, by making amino acid substitutions in the isoprene synthase protein which do not alter the three dimensional structure of the protein but allow more favorable expression for a given host cell.

In some aspects of the invention, a portion of the three dimensional structure of isoprene synthase may be used as a guide to design isoprene synthase variants or to design agents that mimic at least a portion of the isoprene synthase. As such, the invention provides a three dimensional configuration of points of a portion of the points shown in Table 3-7 or Table 4-2 or Table 8-2. Examples of portions of isoprene synthase include, but are not limited to, an active site, a diphosphate/metal binding site, an isoprenyl binding site, a flexible loop, a hinge region, and an electrostatic patch region.

In some aspects, the invention provides a three dimensional configuration of points that are analogous to the three dimensional configuration of points shown in Table 3-7 or Table 4-2 or Table 8-2 or a portion thereof. Analogous three dimensional configuration of points are at least 50%, 55%, 60%, 65%, 70%, 75%, 80%, 85%, 90%, 95%, or 100% identical to the three dimensional configuration of points shown in Table 3-7 or Table 4-2 or a portion thereof, such as an active site, a diphosphate/metal binding site, an isoprenyl binding site, a flexible loop, a hinge region or an electrostatic patch region.

The three-dimensional structures of *P. tremuloides* IspS provide the identification of sites in the *P. tremuloides* IspS and other poplar isoprene synthases (e.g. *P. alba* IspS) that are candidates for mutagenesis to produce variant isoprene synthase enzymes with improved performance. The present invention provides sites isoprene synthase that might alter the interaction of the metal binding, diphosphate recognition, DMAPP chain binding, isoprenyl binding and/or the approach to the active site. Variants of isoprene synthase are designed for greater production of isoprene in host cells.

In some aspects, the invention provides methods of developing variants of isoprene synthase with improved enzyme kinetics. Improved enzyme kinetics can be determined by enzymatic assays. An increase in $k_{cat}$ and/or a decrease in $K_i$ or $K_M$ compared to wild type isoprene synthase indicated an increase in the specific activity of the variant.

It is to be understood the disclosure herein for generating variants using three dimensional structure of isoprene synthase are equally applicable to other enzymes having substantially the same three-dimensional structure. This can refers to a polypeptide that is characterized by a set of atomic structure coordinates that have a root mean square deviation (r.m.s.d.) of less than or equal to about 1.5 Å when superimposed onto the atomic structure coordinates of an isoprene synthase, e.g. the atomic structure coordinates of Table 3-7 or Table 4-2 or Table 8-2 when at least about 50% to 100% of the Cα atoms of the coordinates are included in the superposition.

The invention also contemplates generating variants using homologous segments to the three dimensional structure of the isoprene synthases disclosed herein. This can refer to a segment of an enzyme having a root mean square deviation of less than about 1.5 Å in models of related enzymes. For example the model of the *P. tremuloides* isoprene synthase molecule or molecular complex listed in Table 3-7, Table 4-2 or Table 8-2 can be used to identify homologous segments having a root mean square deviation of less than about 1.5 Å in models of related isoprene synthases.

Slight variations in structure coordinates can be generated by mathematically manipulating the isoprene synthase structure coordinates provided herein. For example, the structure coordinates set forth in Table 3-7 or Table 4-2 or Table 8-2 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Thus, for the purpose of the structures provided herein, any active site, binding site or binding pocket defined by a set of structure coordinates for a polypeptide or for a homolog of a polypeptide from any source having a root mean square deviation of non-hydrogen atoms of less than about 1.5 Å when superimposed on the non-hydrogen atom positions of the corresponding atomic coordinates of Table 3-7 or Table 4-2 or Table 8-2, are considered substantially identical or homologous. As such, all variants with equivalent or homologous residues are contemplated within the scope of this invention, regardless if it is has the same amino acid(s) or a different amino acid(s).

As described above, the present invention provides the three-dimensional structure of the active site (diphosphate/metal binding site) of isoprene synthase. The active site includes amino acid residues Arg 255, Asp 292, Asp 296, Glu 370, Arg 433 and Asn436 if *P. tremuloides* isoprene synthase. In addition, based on the three-dimensional structure of *P. tremuloides* isoprene synthase, the side chains of amino acid residues found in proximity to the diphosphate/metal binding site were identified. These residues include, but are not limited to, Asp 293, Tyr 385, Ser 392, and Asp 437 of *P. tremuloides* isoprene synthase. Engineering of these sites may result in increased enzyme activity. In some cases, mutation in an active site residue may decrease or completely abolish the activity of the isoprene synthase.

The three-dimensional structure of isoprene synthase may also be used to identify residues that bind the substrate of isoprene synthase, e.g. DMAPP. The residues may be used as a basis to generate isoprene synthase variants that may be used modulate substrate specificity and/or reaction rates (altered on and off rates of substrate and product). These residues include, but are not limited to, Ser 261, Trp 264, Phe 285, Thr 289, Ser 393, Ser 394, Phe 432, and Try 512 of *P. tremuloides* isoprene synthase.

The three dimensional structure of isoprene synthase has revealed that several loops forming the active site are flexible. One may exploit the flexibility to enhance enzyme performance by making substitutions in the amino aids forming these segments to facilitate the transitions the enzyme must undergo in the steps of binding substrate and allowing rearrangement of substrate in different kinetic steps that are postulated to occur during enzymatic de-phosphorylation and for electron transfer to convert DMAPP to isoprene. Three segments have been identified that form a considerable portion of the substrate binding pocket, notably the truncated N-terminus, along with two loops comprised of residues 438-453 (Loop I) and residues 512-527 (Loop II) (FIGS. 33-36). These loops may be present in at least two conformations: the "open" form in the absence of substrate and a "closed," or active form when the substrate is bound. These residues provide targets for the generation of isoprene synthase variants with improved activity. For example, the residues in these loops of *P. tremuloides* isoprene synthase, including residues 440-453 (SASAEIARGETANS (SEQ ID NO:40)) and 512-524 (YHNGDAHTSPDEL (SEQ ID NO:41)), may be in a position to alter the activity of the isoprene synthase.

The flexible loop residues of isoprene synthase can be targets for Site Evaluation Library analysis. A library can be generated such that a particular amino acid residue(s) are mutated to different amino acid substitutions and then tested for activity (e.g. DMAPP activity) in an appropriate host cell. As exemplified in Example 5 below, residues A443, A453, N545, H515, A519 and E525 of the *P. alba* IspS (SEQ ID NO:41) were mutated and analyzed for DMAPP activity. *P. alba* IspS variants with improved activity identified by this analysis include, but are not limited to, A453N, H515M, A453I and A443S. Thus, other mutations in the flexible loop or mutations that affect the flexible loop can be found that increase isoprene synthase activity in the manner described herein. For example, conservative substitutions can be made that result in an increase in isoprene synthase activity.

The three-dimensional structure of isoprene synthase has revealed amino acids on the surface of the enzyme. For example, surface hydrophobic residues may affect protein folding, solubility or activity. In order to enhance the solubility of isoprene synthase, hydrophobic surface residues may be mutated to reduce the tendency of the enzyme to aggregate. In some cases, hydrophobic surface residues may be mutated to neutral of hydrophilic residues to increase the solubility and/or decrease the aggregation of isoprene synthase molecules. One skilled in the art would recognize hydrophobic residues, neutral residues and hydrophilic residues. Examples of surface hydrophobic residues include but are not limited to I28, V30, L130, G153, V299, L303, L469 and L494 of the *P. alba* IspS (SEQ ID NO:41). *P. alba* IspS variants with improved activity include, but are not limited to, L494P, L494C, L494V, L494G, L494I and L469A. Thus, other mutations in the surface hydrophobic residues can be found that increase isoprene synthase activity in the manner described herein. For example, conservative substitutions can be made that result in an increase in isoprene synthase activity. It is to be understood that all descriptions of mutations and/or substitutions herein refer to one mutation by itself or a combination (e.g., 2, 3, 4, 5, or more) of mutations. For example, an isoprene synthase variant with L494P is contemplated as well as an isoprene synthase variant with L494P and T536F.

The three dimensional structure of isoprene synthase has a "hinge region" located in a helix that spans the N-terminus and the C-terminus. In one aspect, the three dimensional structure of isoprene synthase has a "hinge region" located in a helix that spans the N-terminus and the C-terminus of the protein monomer. Without being bound by theory, the hinge region may dictate how these two halves of the enzyme may interact with each other. The hinge region includes residues 216-244. Examples of amino acid residues in the hinge region or that may interact with the hinge region include, but are not limited to, R198, I229 and L260 of the *P. alba* IspS (SEQ ID NO:41). Variants in the hinge region with improved activity include, but are not limited to, I229C, I229T, I229P, I229N, L260N, L260M, and L260I. Thus, other mutations in the hinge residues can be found that increase isoprene synthase activity in the manner described herein. For example, conservative substitutions can be made that result in an increase in isoprene synthase activity.

An electrostatic patch was identified by the three dimensional structure of isoprene synthase by the presence of a high density of acidic residues. Residues in the electrostatic patch include D304, E307, D311, E314 and D323. Without being bound by theory, this region may regulate activity of isoprene synthase. Examples of amino acid residues in the electrostatic patch include but are not limited to D311 and D323 of the *P. alba* IspS (SEQ ID NO:41). Variants with improved activity include, but are not limited to, D311M, D311F, D311L, D311G, D311I, D311A, D311T, D311R, D311V, D311E, D323W, D323Y, D323F, D323I, D323S, D323V, D323A, D323G, and D323Q. Thus, other mutations in the electrostatic patch residues or that affect the electrostatic patch can be found that increase isoprene synthase activity in the manner described herein. For example, conservative substitutions can be made that result in an increase in isoprene synthase activity.

Analysis of the three dimensional structure of isoprene synthase revealed other regions for targeting variants. For example, variants may be targeted to loop regions of the protein which can absorb structural perturbations to a greater extent than helices. As described in Example 5, residues D345, R528 and T536 of *P. alba* IspS (SEQ ID NO:41) were targets for SEL analysis. Without being bound by theory, D345 may be involved in dimerization of isoprene synthase. R528 adjacent to the flexible loop described above. Residue T536 is located at the C-terminal residue of the last helix on the C-terminal end of isoprene synthase. Variants with improved isoprene synthase activity include, but are not limited to, T536C, T536I, T536F, T536Y, T536A, T536K, T536L, T536R, T536V and T536M.

In some aspects of the invention, the variant isoprene synthase does not contain mutations at homologous residues corresponding to one or more of the following residues in kudzu isoprene synthase: A20, N21, Y22, Q23, P24, N25, L26, E30, F31, Q33, L35, E36, N37, L39, K40, V41, K43, L44, C57, R61, V62, D63, Q65, K87, E94, N95, L99, D100, N105, K137, E138, G143, E144, N182, L184, K185, G187, N189, T190, P225, H226, K247, T257, E258, M259, D266, R271, W278, C291, F299, V302, Y309, D310, N334, D353, S357, I358I, E361, L377, F381, E384, N389, I392, I393, K398, Y399, E401, N402, A403, S406, S407, S408, G409, A411, L413, C421, Q423, Q424, E425, D426, H430, L432, R433, S434, D437, R443, C446, F449, A456, T457, S458, A459, A460, E461, L462, E463, R464, G465, E466, T467, T468, N469, H476, N478, D479, Q485, D508, P513, A515, M523, S527, Y531, Q532, Y533, L537, G538, R539, Y542, A543, and P557 (based on FIG. 37; SEQ ID NO:42).

In other aspects of the invention, the variant isoprene synthase does not contain mutations at homologous residues corresponding to one or more of the following residues in *P. alba* v *tremuloides* isoprene synthase: K272, R274, W281, F302, V305, Y312, D313, L380, F384, E387, Y402, N404, A406, S409, S410, S411, G412, L414, Q415, L416, F449, N453, L454, A455, S456, A457, S4548, A459, E460, I461, A462, R463, G464, E465, T466, N469, C497, L521, S525, S537, E540, and residues 22 to 27 (based on FIG. 38; SEQ ID NO:43).

In other aspects of the invention, the variant isoprene synthase does not contain mutations at homologous residues corresponding to one or more of the following mutations in *P. alba* isoprene synthase: V10M, F125, T15A, E18G, V58I, V58F, L70Q, L70V, L70T, T71P, V79L, E89D, G94A, S119F, F120L, G127R, E175V, T212I, S257A, R262G, A266G, F280L, N297K, F305L, L319M, E323K, A328T, D342E, A359T, K366N, E368D, L374M, S396T, V4185, K438N, H440R, T442I, T442A, I449V, A469S, K500R, K505Q, G5075, 5509N, F511Y, and N532K (based on SEQ ID NO:16).

In some aspects of the invention, the variant isoprene synthase does not contain combinations of mutations at homologous residues corresponding to one or more of the following combination mutations in a single *P. alba* isoprene synthase: G127R/F511Y, L70Q/G94A/R262G/F305L, F12S/T15A/E18G/N297K, S396T/T442I, V10M/E323K, F120L/A266G, K438N/K500R, V79L/S509N, E175V/S257A/E368D/A469S, T71P/L374M, F280L/H440R, E89D/H440R, V58F/A328T/N532K, S119F/D342E/I449V, and K366N/G507S (based on SEQ ID NO:16).

It has been shown that mutating amino-acid residues on the surface of protease enzymes can improve their activity, expression, and stability (WO2008/153925, WO2008/153934, WO2008/153935). Surprisingly, we have found that mutating amino-acid residues on the surface of a completely different enzyme, isoprene synthase, can enhance its expression, solubility, and activity. L70R is an example of such a beneficial surface mutation.

Elucidation of the three-dimensional structure of an enzyme is essential for accurately identifying amino-acid residues on its surface. Homology modeling using structures with sequences approximately 40% identical to isoprene synthase (e.g., bornyl synthase and limonene synthase, the enzymes of known structure with closest identity to isoprene synthase) can reveal gross aspects of the modeled enzyme structure, but is insufficient to precisely identify surface-exposed residues and quantify their degree of surface exposure. Surface exposure of an amino-acid residue is quantified by the percentage of solvent-accessible surface area of its side chain.

The following classes of mutations in isoprene synthase may improve solubility of the enzyme by targeting amino-acid residues that are about >50% solvent-exposed, in some cases about >65% solvent-exposed, and in other cases >85% solvent-exposed:

Hydrophobic→positively charged, and vice versa
Hydrophobic→negatively charged, and vice versa
Hydrophobic→neutral polar, and vice versa
Neutral polar→positively charged, and vice versa
Neutral polar→negatively charged, and vice versa
Positively charged→negatively charged, and vice versa These classes of mutations may also be used to improve the activity, substrate stability, dimerization of isoprene synthase.

The three-dimensional structure of isoprene synthase reveals the structural reaction coordinates of isoprene synthesis. As such, the invention provides a three-dimensional configuration of atoms involved in the catalytic conversion of DMAPP to isoprene. In some aspects, the invention provides an agent comprising a three-dimensional configuration of atoms for the catalytic conversion of DMAPP to isoprene. Example of agents include, but are not limited to, synthetic molecules including synthetic polypeptides as well as re-engineered polypeptides. For example, other members of the terpene synthase family may be altered to comprise the three-dimensional configuration of atoms for the catalytic conversion of DMAPP to isoprene.

Machine Readable Storage Media

Transformation of the structure coordinates for all or a portion of *P. tremuloides* isoprene synthase or an isoprene synthase/ligand complex or one of its active sites, for structurally homologous molecules, or for the structural equivalents of any of these molecules or molecular complexes as defined above, into three-dimensional graphical representations of the molecule or complex can be conveniently achieved through the use of commercially-available software.

The invention thus further provides a machine-readable storage medium including a data storage material encoded with machine readable data which, when using a machine programmed with instructions for using said data, displays a graphical three-dimensional representation of any of the molecule or molecular complexes of this invention that have been described above. In a preferred embodiment, the machine-readable data storage medium includes a data storage material encoded with machine readable data which, when using a machine programmed with instructions for using said data, displays a graphical three-dimensional representation of a molecule or molecular complex including all or any parts of a *P. tremuloides* isoprene synthase active site or a *P. tremuloides*-like active site; for example from a poplar isoprene synthase including but not limited to *P. alba* isoprene synthase, as defined above. In another aspect, the machine-readable data storage medium displays a graphical three-dimensional representation of a molecule or molecular complex defined by the structure coordinates of all of the amino acids in Table 3-7, ±a root mean square deviation from the backbone atoms of said amino acids of not more than 1.5 Å. In another aspect, the machine-readable data storage medium displays a graphical three-dimensional representation of a molecule or molecular complex defined by the structure coordinates of all of the amino acids in Table 4-2, ±a root mean square deviation from the backbone atoms of said amino acids of not more than 1.5 Å.

In an alternative aspect of the invention, the machine-readable data storage medium includes a data storage material encoded with a first set of machine readable data which includes the Fourier transform of the structure coordinates set forth in Table 3-7 or 4-2, and which, when using a machine programmed with instructions for using said data, can be combined with a second set of machine readable data including the x-ray diffraction pattern of a molecule or molecular complex to determine at least a portion of the structure coordinates corresponding to the second set of machine readable data.

For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of this invention using a program such as QUANTA. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

Isoprene Synthase Variants, Agents with Similar 3-D Structures, and their Use

Compositions and methods to make and use variants derived from the three-dimensional structure of isoprene synthase and agents with similar three-dimensional structure to isoprene synthase are provided herein.

The invention provides methods to generate and test candidate variants of isoprene synthesis based on an evaluation of the three-dimensional structure of the protein. Candidate residues for alteration are derived by a computational analysis of the three-dimensional structure with regard to one or more desired characteristics of the variant; for example, increased specific activity, increased stability, increased expression and the like. Candidate variants may then be generated using standard molecular biology techniques. Variants can be assessed based on the desired outcome. For example, a variant isoprene synthase engineered for increased specific activity can be tested for the conversion of DMAPP to isoprene in vitro with purified or partially purified variant isoprene synthase or in vivo in the context of a host organism such as *E. coli*. In some cases, the *E. coli* may also express the DXP pathway, the MVA pathway, or both. Improved activity is assessed in comparison with other isoprene synthases; for example, a wild type isoprene synthase. It is contemplated that enzymes having various degrees of stability, solubility, activity, and/or expression level in one or more of test conditions will find use in the present invention for the production of isoprene in a diversity of hosts. High throughput methods may provide an investigation of these properties in an economical manner.

The invention provides compositions and methods for the production of increased amounts of isoprene. In particular, these compositions and methods increase the rate of isoprene production and increase the total amount of isoprene that is produced. In some aspects of the invention, the amount of isoprene produced by cells may be increased by introducing a heterologous nucleic acid encoding a variant isoprene synthase polypeptide into the cells.

Exemplary Polypeptides and Nucleic Acids

Various isoprene synthase polypeptides and nucleic acids can be used in the compositions and methods of the invention. As used herein, "polypeptides" includes polypeptides, proteins, peptides, fragments of polypeptides, and fusion polypeptides that include part or all of a first polypeptide (e.g., an isoprene synthase) and part or all of a second polypeptide (e.g., a peptide that facilitates purification or detection of the fusion polypeptide, such as a His-tag). In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, 100% or greater than 100% of an activity of a corresponding full-length polypeptide. In particular embodiments, the polypeptide includes a segment of or the entire amino acid sequence of any naturally-occurring isoprene synthase. In some embodiments, the polypeptide has one or more mutations compared to the sequence of a wild-type (i.e., a sequence occurring in nature) isoprene synthase.

In some embodiments, the polypeptide is a heterologous polypeptide. By "heterologous polypeptide" is meant a polypeptide whose amino acid sequence is not identical to that of another polypeptide naturally expressed in the same host cell.

In various embodiments, the nucleic acid is a recombinant nucleic acid. For instance, in some embodiments, an isoprene synthase nucleic acid is operably linked to another nucleic acid encoding all or a portion of another polypeptide such that the recombinant nucleic acid encodes a fusion polypeptide that includes an isoprene synthase and all or part of another polypeptide (e.g., a peptide that facilitates purification or detection of the fusion polypeptide, such as a His-tag). In some embodiments, part or all of a recombinant nucleic acid is chemically synthesized. In some aspects, the nucleic acid is a heterologous nucleic acid. By "heterologous nucleic acid" is meant a nucleic acid whose nucleic acid sequence is not identical to that of another nucleic acid naturally found in the same host cell.

In particular embodiments the nucleic acid includes a segment of or the entire nucleic acid sequence of any naturally-occurring isoprene synthase nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid. In some aspects, the nucleic acid has one or more mutations compared to the sequence of a wild-type (i.e., a sequence occurring in nature) isoprene synthase nucleic acid. In some embodiments, the nucleic acid has one or more mutations (e.g., a silent mutation) that increase the transcription or translation of isoprene synthase nucleic acid. In some embodiments, the nucleic acid is a degenerate variant of any nucleic acid encoding an isoprene synthase polypeptide.

An isoprene synthase nucleic acid can be incorporated into a vector, such as an expression vector, using standard techniques (Sambrook et al., Molecular Cloning: A Laboratory Manual, Cold Spring Harbor, 2001, which is hereby incorporated by reference in its entirety, particularly with respect to the screening of appropriate DNA sequences and the construction of vectors). Methods used to ligate the DNA construct comprising a nucleic acid of interest such as isoprene synthase, a promoter, a terminator, and other sequences and to insert them into a suitable vector are well known in the art. Additionally, vectors can be constructed using known recombination techniques (e.g., Invitrogen Life Technologies, Gateway Technology).

In some embodiments, it may be desirable to over-express isoprene synthase nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, 2nd ed., Cold Spring Harbor, 2001, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990; and Ausubel et al., Eds. Current Protocols in Molecular Biology, 1994, which are each hereby incorporated by reference in their entireties, particularly with respect to molecular biology and cloning techniques.

Exemplary Host Cells

A variety of host cells can be used to express isoprene synthase and to produce isoprene in the methods of the claimed invention. The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Other exemplary host cells that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Transformation Methods

Isoprene synthase, DXS, IDI, and/or MVA pathway nucleic acids or vectors containing them can be inserted into a host cell (e.g., a bacterial cell) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, 3rd ed., Cold Spring Harbor, 2001; and Campbell et al., Curr Genet, 16:53-56, 1989, which are each hereby incorporated by reference in their entireties, particularly with respect to transformation methods). The introduced nucleic acids may be integrated into chromosomal DNA or maintained as extrachromosomal replicating sequences.

Other exemplary transformation methods that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Cell Culture Media

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharides), invert sugar (e.g., enzymatically treated sucrose syrup), glycerol, glycerine (e.g., a glycerine byproduct of a biodiesel or soap-making process), dihydroxyacetone, one-carbon source, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source; beet sugar or cane sugar molasses), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

Exemplary lipids are any substance containing one or more fatty acids that are C4 and above fatty acids that are saturated, unsaturated, or branched.

Exemplary fatty acids include compounds of the formula R—COOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more C12-C22 fatty acids, such as a C12 saturated fatty acid, a C14 saturated fatty acid, a C16 saturated fatty acid, a C18 saturated fatty acid, a C20 saturated fatty acid, or a C22 saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, fatty acid, monoglyceride, diglyceride, or triglyceride that is added before and/or during the culturing of the host cells. In some embodiments, the carbon source includes both (i) a lipid, fatty acid, monoglyceride, diglyceride, or triglyceride and (ii) a carbohydrate, such as glucose. In some embodiments, the ratio of the lipid, fatty acid, monoglyceride, diglyceride, or triglyceride to the carbohydrate is about 1:1 on a carbon basis (i.e., one carbon in the lipid, fatty acid, monoglyceride, diglyceride, or triglyceride per carbohydrate carbon). In particular embodiments, the amount of the lipid, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassaya, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., Bioresource Technology 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., Bioresource Technology 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry-to-dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., Agric. Biol. Chem., 53(2) 541-543, 1989, which is hereby incorporated by reference in its entirety, particularly with respect to carbon sources) and in bacteria (Hunter et. al., Biochemistry, 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, Bacterial Metabolism, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylene-tetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth Cl Compd., Int. Symp., 7th ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., Arch. Microbiol. 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988; and Ilmen et al., Appl. Environ. Microbiol. 63:1298-1306, 1997, hereby incorporated by reference, particularly with respect to cell media). Exemplary growth media are common commercially prepared media such as Luria Bertani (LB) broth, Sabouraud Dextrose (SD) broth, or Yeast medium (YM) broth. One skilled in the art of microbiology or fermentation science would know other defined or synthetic growth media that may also be used, and the appropriate medium for growth of particular host cells.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect to cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Other exemplary cell culture media that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Production of Isoprene

In some embodiments, the cells are cultured in a culture medium under conditions permitting the production of isoprene by the cells. In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/gwcm/hr). In some embodiments, the amount of isoprene is between about 2 to about 5,000 nmole/gwcm/hr, such as between about 2 to about 100 nmole/gwcm/hr, about 100 to about 500 nmole/gwcm/hr, about 150 to about 500 nmole/gwcm/hr, about 500 to about 1,000 nmole/gwcm/hr, about 1,000 to about 2,000 nmole/gwcm/hr, or about 2,000 to about 5,000 nmole/gwcm/hr. The amount of isoprene in units of nmole/gwcm/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, e.g., Greenberg et al, Atmos. Environ. 27A: 2689-2692, 1993; Silver et al., Plant Physiol. 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/gwcm/h). In some embodiments, the amount of isoprene is between about 2 to about 5,000 ng/gwcm/h, such as between about 2 to about 100 ng/gwcm/h, about 100 to about 500 ng/gwcm/h, about 500 to about 1,000 ng/gwcm/h, about 1,000 to about 2,000 ng/gwcm/h, or about 2,000 to about 5,000 ng/gwcm/h. The amount of isoprene in ng/gwcm/h can be calculated by multiplying the value for isoprene production in the units of nmole/gwcm/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/L broth, wherein the volume of broth includes the volume of the cells and the cell medium). In some embodiments, the amount of isoprene is between about 2 to about 5,000 mg/L broth, such as between about 2 to about 100 mg/L broth, about 100 to about 500 mg/L broth, about 500 to about 1,000 mg/L broth, about 1,000 to about 2,000 mg/L broth, or about 2,000 to about 5,000 mg/L broth. The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace. If the $OD_{600}$ value is not 1.0, then the measurement can be normalized to an $OD_{600}$ value of 1.0 by dividing by the $OD_{600}$ value. The value of mg isoprene/L headspace can be converted to mg/Lbroth/hr/$OD_{600}$ of culture broth by multiplying by a factor of 38. The value in units of mg/Lbroth/hr/$OD_{600}$ can be multiplied by the number of hours and the $OD_{600}$ value to obtain the cumulative titer in units of mg of isoprene/L of broth.

The instantaneous isoprene production rate in mg/L broth/hr in a fermentor can be measured by taking a sample of the fermentor off-gas, analyzing it for the amount of isoprene (in units such as mg of isoprene per L of gas), and multiplying this value by the rate at which off-gas is passed though each liter of broth (e.g., at 1 vvm (volume of air/volume of broth/minute) this is 60 Lgas per hour). Thus, an off-gas level of 1 mg/Lgas corresponds to an instantaneous production rate of 60 mg/Lbroth/hr at air flow of 1 vvm. If desired, the value in the units mg/Lbroth/hr can be divided by the $OD_{600}$ value to obtain the specific rate in units of mg/Lbroth/hr/OD. The average value of mg isoprene/Lgas can be converted to the total product productivity (grams of isoprene per liter of fermentation broth, mg/Lbroth) by multiplying this average off-gas isoprene concentration by the total amount of off-gas sparged per liter of fermentation broth during the fermentation. Thus, an average off-gas isoprene concentration of 0.5 mg/Lbroth/hr over 10 hours at 1 vvm corresponds to a total product concentration of 300 mg isoprene/Lbroth.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, or 1.6% of the carbon in the cell culture medium into isoprene. In some embodiments, the percent conversion of carbon into isoprene is between about 0.002 to about 1.6%, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

% Carbon Yield=(moles carbon in isoprene produced)/(moles carbon in carbon source)*100 Equation 1

For this calculation, yeast extract can be assumed to contain 50% w/w carbon.

% Carbon Yield=(39.1 g isoprene*1/68.1 mol/g*5 C/mol)/[(181221 g glucose*1/180 mol/g*6 C/mol)+(17780 g yeast extract*0.5*1/12 mol/g)]*100=0.042% Equation 2

One skilled in the art can readily convert the rates of isoprene production or amount of isoprene produced into any other units. Exemplary equations are listed below for interconverting between units.

Units for Rate of Isoprene Production (Total and Specific)

1 g isoprene/$L_{broth}$/hr=14.7 mmol isoprene/$L_{broth}$/hr (total volumetric rate) Equation 3

1 nmol isoprene/$g_{wcm}$/hr=1 nmol isoprene/$L_{broth}$/hr/$OD_{600}$ (This conversion assumes that one liter of broth with an $OD_{600}$ value of 1 has a wet cell weight of 1 gram.) Equation 4

1 nmol isoprene/$g_{wcm}$/hr=68.1 ng isoprene/$g_{wcm}$/hr (given the molecular weight of isoprene) Equation 5

1 nmol isoprene/$L_{gas}$ $O_2$/hr=90 nmol isoprene/$L_{broth}$/hr (at an $O_2$ flow rate of 90 L/hr per L of culture broth) Equation 6

1 μg isoprene/$L_{gas}$ isoprene in off-gas=60 μg isoprene/$L_{broth}$/hr at a flow rate of 60 $L_{gas}$ per $L_{broth}$ (1 vvm) Equation 7

Units for Titer (total and specific)

1 nmol isoprene/mg cell protein=150 nmol isoprene/$L_{broth}$/$OD_{600}$ (This conversion assumes that one liter of broth with an $OD_{600}$ value of 1 has a total cell protein of approximately 150 mg) (specific productivity) Equation 8

1 g isoprene/$L_{broth}$=14.7 mmol isoprene/$L_{broth}$ (total titer) Equation 9

If desired, Equation 10 can be used to convert any of the units that include the wet weight of the cells into the corresponding units that include the dry weight of the cells.

Dry weight of cells=(wet weight of cells)/3.3 Equation 10

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

Exemplary Isoprene Purification Methods

In some embodiments, any of the methods described herein further include recovering the isoprene. For example, the isoprene produced using the compositions and methods of the invention can be recovered using standard techniques. such as gas stripping, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. See, e.g. U.S. Patent Application Publication No. 2009/0203102, PCT publication WO 2009/076676 and U.S. patent application Ser. No. 12/496,573. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. It is also to be understood that one, some, or all of the properties of the various embodiments described herein may be combined to form other embodiments of the present invention. These and other aspects of the invention will become apparent to one of skill in the art.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Construction of MBD Kudzu IspS

This example describes construction of a vector expressing a maltose-binding protein-kudzu isoprene synthase fusion molecule.

I. Construction of pTrcKudzu

Figure 2:
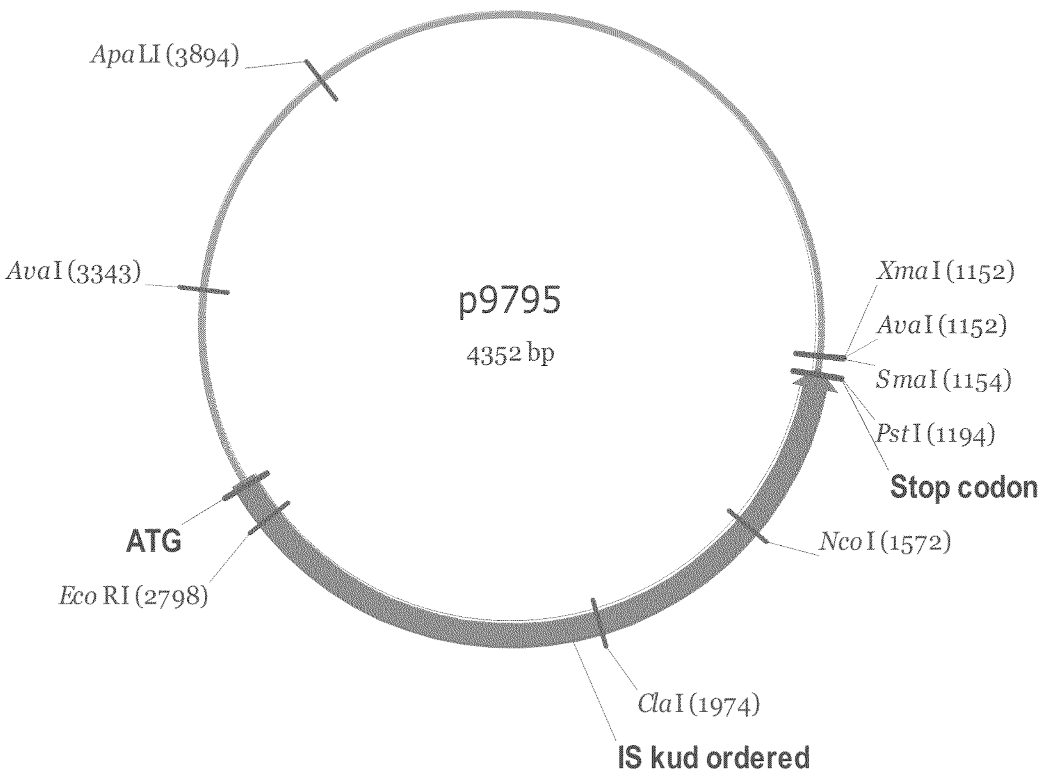
FIG. 2 provides a map of plasmid p9795.
Figure 4:
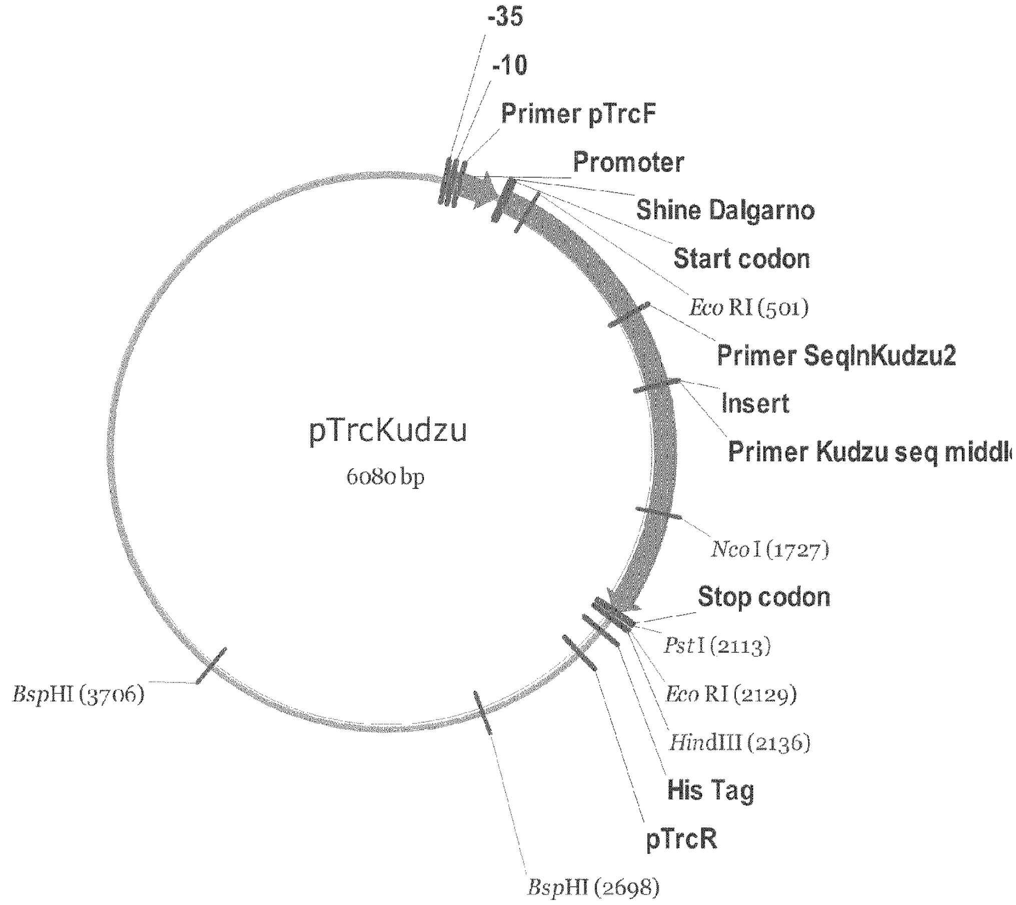
FIG. 4 provides a map of plasmid pTrcKudzu.

A synthetic gene, coding for isoprene synthase (IspS) of the kudzu vine (*Pueraria lobata*) and codon-optimized for *E. coli*, was purchased from DNA2.0 (Menlo Park, Calif.) and provided as plasmid p9795 (FIGS. 2 and 3). The Insert was been removed by digestion with BspLU11I/PstI, gel-purified, and religated into NcoI/PstI-digested pTrcHis2B (Invitrogen, Carlsbad, Calif.). The resulting plasmid was named pTrcKudzu (FIGS. 4 and 5). The stop codon in the insert is before the PstI site, which results in a construct in which the His-Tag is not attached to the IspS protein.

II. Construction of Plasmid pMAL-C4X Kudzu

A PCR reaction was performed to amplify the *E. coli* codon-optimized kudzu gene using plasmid pTrcKudzu as the DNA template, primers EL-959 and EL-960 Table 1-1, 10 mM dNTP (Roche, Indianapolis, Ind.), and Pfu Ultra II Fusion DNA polymerase (Stratagene, La Jolla, Calif.) according to manufacturer's protocol. PCR conditions were as follows: 95° C. for 2 min (first cycle only), 95° C. for 25 sec, 60° C. for 25 sec, 72° C. for 30 sec, and repeat for 28 cycles, with final extension at 72° C. for 1 min. The PCR product was then purified using the QIAquick PCR Purification Kit (Qiagen Inc, Valencia, Calif.).

Figure 6:
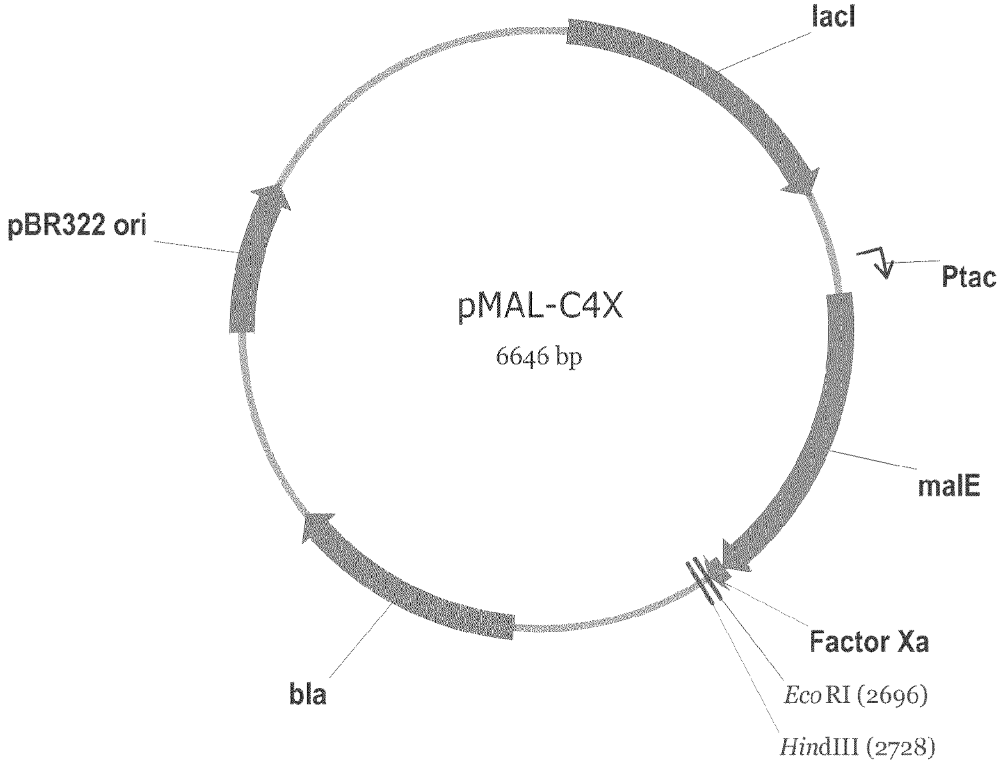
FIG. 6 provides a map of plasmid pMAL-C4X.

The kudzu PCR product (1 μg) was digested using EcoRI and HindIII restriction endonucleases (Roche) according to manufacturer's protocol. The digest was incubated 37° C. for 30 minutes to minimize digestion of the internal EcoRI site that is present in the kudzu gene. The digested PCR fragment was then purified using the QIAquick PCR Purification Kit. The vector pMAL-C4X (0.5 μg) (New England Biolabs, Ipswich, Mass.; FIGS. 6 and 7) was digested using EcoRI and HindIII restriction endonucleases (Roche) according to manufacturer's protocol. The digested vector was then gel purified using the QIAquick Gel Extraction Kit (Qiagen Inc). A DNA ligation reaction was performed using T4 DNA ligase (New England Biolabs) with a 5:1 ratio of digested kudzu PCR product to digested pMAL-C4X vector according to manufacturer's protocol. An aliquot of the ligation reaction was then transformed into TOP10 chemically competent cells (Invitrogen Corp). Transformants were selected on LA+50 μg/μl carbenicillin plates.

Figure 8:
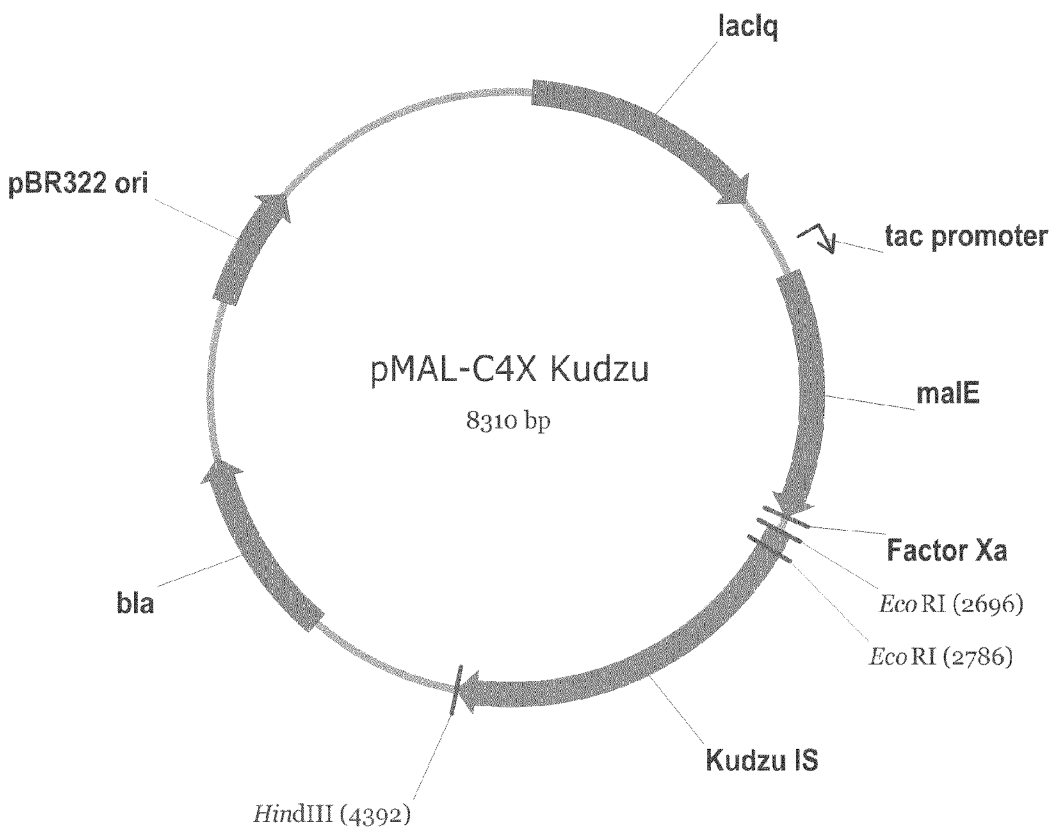
FIG. 8 provides a map of plasmid pMAL-C4X-Kudzu.
Figure 15C:
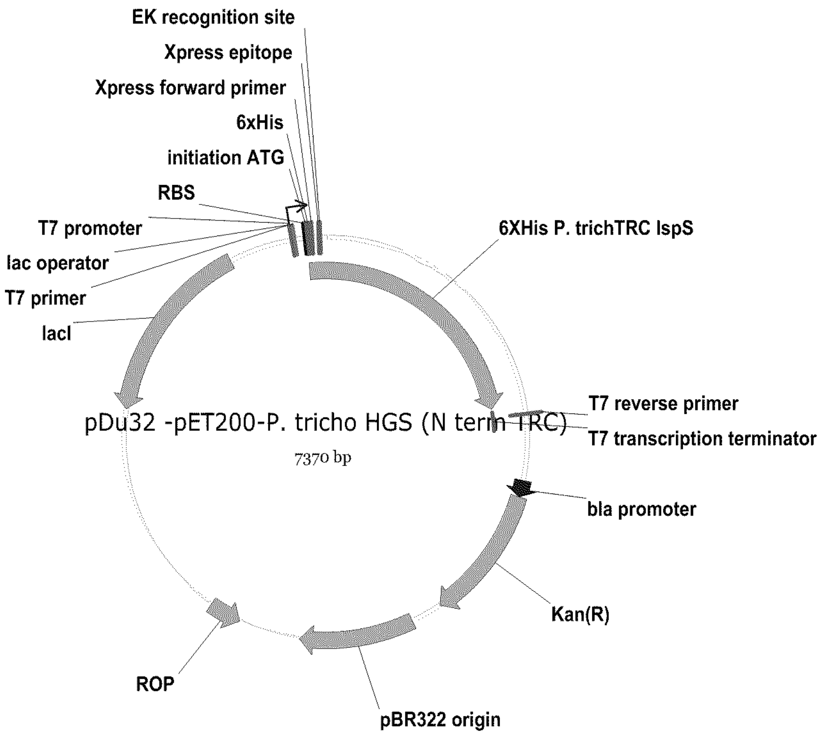
FIG. 15C provides the map of plasmids pDu32.

Screening of transformants containing the kudzu gene was performed by picking colonies and performing PCR with primers EL-957 and EL-966 using PuReTaq Ready-To-Go PCR beads (GE Healthcare, Piscataway, N.J.) according to manufacturer's protocol. PCR conditions were as follows: 95° C. for 2 min (first cycle only), 95° C. for 30 sec, 50° C. for 30 sec, 72° C. for 40 sec, and repeat for 28 cycles, with final extension at 72° C. for 1 min. PCR products were analyzed on a 2% E-gel (Invitrogen Corp) looking for a 600 by fragment. Colonies containing the correct sized PCR product insert were submitted for DNA sequencing using primers EL-950, EL-951, EL-953, and EL-957. DNA sequencing confirmed the construction of plasmid pMAL-C4X Kudzu (FIGS. 8 and 9).

TABLE 1-1

Primer sequences

| Primer name | Primer sequence |
|---|---|
| EL-950 | CGGTGAACTGAAAGGTGACGTCC (SEQ ID NO: 22) |
| EL-951 | GGACGTTAACGCTATTAACACCCTG (SEQ ID NO: 23) |
| EL-953 | CACATCGTCGATCAGCTCCAGC (SEQ ID NO: 24) |
| EL-957 | GGTCGTCAGACTGTCGATGAAGCC (SEQ ID NO: 25) |
| EL-959 | GCTTATGAATTCTGTGCGACCTCTTCTCAATTTACTCAG (SEQ ID NO: 26) |
| EL-960 | GCTTATAAGCTTAGACATACATCAGCTGGTTAATCGGG (SEQ ID NO: 27) |
| EL-966 | CTCCTCCAGCAGGTTCTCACC (SEQ ID NO: 28) |

III. Expression Strain MBP-Kudzu

Plasmid pMAL-C4X Kudzu was transformed into One-Shot BL21(λDE3) chemically competent cells (Invitrogen Corp). Expression strain transformants were selected on LA+50 mg/ml carbenicillin plates.

Example 2

IspS Variants for Crystal Structure Trials

This example describes methods to generate affinity tagged isoprene synthase (IspS) enzymes for expression, purification and crystallization.

I. Strain Construction

For constructs in the pET200D-TOPO vector (Invitrogen), PCR products of the IspS enzymes from *P. alba, P. tremuloides*, and *P. trichocharpa* were gel extracted and purified (Qiagen), using 0.8% E-gel (Invitrogen), according to the manufacturer's recommended protocol. PCR reactions for pET200 constructs are as follows: Reaction mixture was 1 μl (Templates)-pET24a-*P. alba,* 5 μl 10×PfuUltraII Fusion buffer, 1 μl dNTP's (10 mM), 1 μl primer (50 uM) primer F-(MCM219 or 218), 1 μl primer (50 uM) primer R-(MCM182), 41 μl di$H_2$O and 1 μl of PfuUltra II Fusion DNA Polymerase from Stratagene; Cycle Parameter were 95° C. 1 min., 95° C. 1 min, 55° C. 20 sec., 72° C. 27 sec. for 29 cycles followed by 72° C. for 3 min and then 4° C. until cool, using an Eppendorf Mastercycler. Similar reactions were performed for *P. tremuloides, P. trichocarpa*, and kudzu. 3 μl of purified product was then ligated to the pET200D/TOPO vector (Invitrogen), according to the manufacturer's protocol. The reaction was incubated for 5 minutes at room temperature, and the 6 μl topoisomerase mixture was then transformed into *E. coli* Top10 chemically competent cells (Invitrogen) according to the manufacturer's protocol. Transformants were selected for on LB Kan50, and incubated at 37° C. overnight. Five colonies per construct were chosen and screened using PuReTaq Ready-To-Go PCR Beads (Amersham) using the T7 Forward and MCM182 primers (Table 2-1). Clones harboring inserts of the correct size were further verified by plasmid miniprep using the QIAPrep Spin Miniprep kit (Qiagen) followed by sequencing using the T7 Forward and T7 Reverse primers (Quintara Biosciences). One fully sequenced construct for each IspS variant (FIGS. 10-14), was chosen for further study. 1 μl of each plasmid was transformed into BL21(λDE3) pLysS (Invitrogen) according to the manufacturer's protocol. Transformants were selected for on LB medium with Kan50+Cm35 and incubated at 37° C. overnight. The resulting strains were used for expression and purification of various IspS enzymes for crystallography studies.

Construction of an N-terminally 6×His-tagged IspS (in pDu27, see FIG. 22) for protein purification was prepared as follows. The following PCR Reaction mixture was used: 1 μl (Template)-*P. alba* pET24a, 5 μl 10×PfuUltraII Fusion buffer, 1 μl dNTP's (10 mM), 1 μl primer (50 uM) primer F-(MCM219), 1 μl primer (50 uM) primer R-(MCM182) (Table 2-1), 41 μl di$H_2$O and 1 μl of PfuUltra II Fusion DNA Polymerase (Stratagene). PCR Cycling Parameters were as follows: 95° C. 1 min., 95° C. 1 min, 55° C. 20 sec., 72° C. 27 sec. for 29 cycles followed by 72° C. for 3 min and 4° C. until cool, using an Eppendorf Mastercycler. The PCR product of the full length *P. alba* IspS (from the template *P. alba* pET24a, FIG. 24) was gel extracted and purified, using 0.8% E-gel (Invitrogen) and Qiagen QIAquick Gel Extraction and QIAprep Spin Miniprep kits, according to the manufacturer's recommended protocol. A 3 μl aliquot of purified product was ligated to the pET200D/TOPO vector (Invitrogen), according to the manufacturer's protocol. The reaction was incubated for 5 minutes at room temperature, and the 6 μl topoisomerase mixture was then transformed into *E. coli* Top10 chemically competent cells (Invitrogen) according to the manufacturer's protocol. Transformants were selected for on LB plates containing kanamycin (50 ug/ml) (Kan50), and incubated at 37° C. overnight. Five colonies were picked and screened using PuReTaq Ready-To-Go PCR Beads (Amersham) using the T7 Forward and MCM182 primers (Table 2-1). Clones harboring inserts of the correct size were further verified by sequencing using the T7 Forward and T7 Reverse primers (Quintara Biosciences). One construct, pDu27 (see FIG. 22), was chosen for further study. A 1 μl aliquot of the plasmid preparation was transformed into BL21(λDE3)pLysS (Invitrogen) according to the manufacturer's protocol. Transformants were selected for on LB plates containing Kan50+ and chloramphenicol (35 μg/ml) (Cm35) and incubated at 37° C. overnight. The resulting strain was used for expression and purification of N-terminally 6×His-tagged *P. alba* IspS.

Constructs with affinity (6×His) and proteolysis (TEV, Tobacco Etch Virus) tags were generated using *P. alba* pET24a as a template for PCR reactions. PCR reaction mixtures were prepared as follows: 1 ul (*P. alba* pET24a), 5 ul 10× PfuUltraII Fusion buffer, 1 ul dNTP's (10 mM), 1 ul primer (50 uM) Alba FL-NdeI-For or Alba TRC (MEA)-NdeI-F, 1 ul primer (50 uM) Alba FLTRC (+) TEV-R, 41 ul diH2O and 1 ul of PfuUltra II Fusion DNA Polymerase from Stratagene. PCR cycling parameters were as follows: 95° C. 1 min., 95° C. 30 sec., 55° C. 20 sec., 72° C. 25 sec. for one cycle and then repeating 95° C. 30 sec., 55° C. 20 sec., 72° C. 25 sec. for an additional 28 cycles, followed by 72° C. 3 min and then 4° C. After amplification and verification of the correct molecular weight of the product by visualization on 0.8% E-gel (Invitrogen), PCR products were digested with restriction enzymes NdeI and XhoI (Roche) for 2 hours at 37° C., and then gel purified using the Qiaquick Gel Purification system (Qiagen) according to the manufacturer's recommended protocol. 3 ul of purified product was ligated to pET-24a (Invitrogen) that was digested with NdeI and XhoI (Roche), gel purified and dephosphorylated (using SAP, shrimp alkaline phosphatase) (Promega) according to the manufacturer's recommended protocols. T4 ligase (NEB) was used for the ligation reaction, which was incubated overnight at 16° C. The ligation reaction was dialyzed into water for 30 min., and 2 μl of the reaction was used to electroporate MCM331 (see below) competent cells. Cells were allowed to recover at 30° C. for 2 hours, and then selected on Kan50 with 5 mM (R)-(−)-Mevalonolactone (MVA) (Sigma) spread onto the plate. Positive transformants were inoculated into 3 ml of liquid LB Kan50, and plasmids were isolated using the QIAPrep Spin miniprep kit (Qiagen). Inserts were verified by restriction digestion using NdeI and XhoI (Roche) and positive clones were sequenced (Quintara Biosciences) with T7 promoter and T7 terminator sequencing primers. 1 μl of each plasmid (see Table 2-3 for plasmid description; FIGS. 15-29) was transformed into chemically competent *E. coli* BL21(λDE3) pLysS (Invitrogen) according to the manufacturer's recommended protocol. Transformants were selected on LB Kan50+Cm35 (Chloramphenicol 35 ug/ml) plates and incubated at 37° C. See Table 2-4 for a description of all expression strains.

Preparation of strain MCM331

Strain MCM331 was prepared as follows. A synthetic operon containing mevalonate kinase, mevalonate phosphate kinase, mevalonate pyrophosphate decarboxylase, and the IPP isomerase was integrated into the chromosome of *E. coli*. If desired, expression may be altered by integrating different promoters 5' of the operon.

i) Target Vector Construction

The attTn7 site was selected for integration. Regions of homology upstream (attTn7 up) (primers MCM78 and MCM79; Table 2-2) and downstream (attTn7 down) (primers MCM88 and MCM89) were amplified by PCR from MG1655 cells. A 50 μL reaction with 1 μL 10 μM primers, 3 μL ddH2O, 45 μL Invitrogen Platinum PCR Supermix High Fidelity, and a scraped colony of MG1655 was denatured for 2:00 at 94° C., cycled 25 times (2:00 at 94° C., 0:30 at 50° C., and 1:00 at 68° C.), extended for 7:00 at 72° C., and cooled to 4° C. This resulting DNA was cloned into pCR2.1 (Invitrogen) according to the manufacturer's instructions, resulting in plasmids MCM278 (attTn7 up) and MCM252 (attTn7 down). The 832 by ApaI-PvuI fragment digested and gel purified from MCM252 was cloned into ApaI-PvuI digested and gel purified plasmid pR6K, creating plasmid MCM276. The 825 bp PstI-NotI fragment digested and gel purified from MCM278 was cloned into PstI-NotI digested and gel purified MCM276, creating plasmid MCM281.

ii) Cloning of Lower Pathway and Promoter

MVK-PMK-MVD-IDI genes were amplified from pTrcK-KDyIkIS with primers MCM104 and MCM105 using Roche Expand Long PCR System according to the manufacturer's instructions. This product was digested with NotI and ApaI and cloned into MCM281 which had been digested with NotI and ApaI and gel purified. Primers MCM120 and MCM127 were used to amplify CMR cassette from the GeneBridges FRT-gb2-Cm-FRT template DNA using Stratagene Pfu Ultra II. A PCR program of denaturing at 95° C. for 4:00, 5 cycles of 95° C. for 0:20, 55° C. for 0:20, 72° C. for 2:00, 25 cycles of 95° C. for 0:20, 58° C. for 0:20, 72° C. for 2:00, 72° C. for 10:00, and then cooling to 4° C. was used with four 50 μL PCR reactions containing 1 uL~10 ng/μL template, 1 μL each primer, 1.25 μL 10 mM dNTPs, 5 μL 10× buffer, 1 μL enzyme, and 39.75 μL ddH20. Reactions were pooled, purified on a Qiagen PCR cleanup column, and used to electroporate water-washed Pir1 cells containing plasmid MCM296. Electroporation was carried out in 2 mM cuvettes at 2.5V and 200 ohms. Electroporation reactions were recovered in LB for 3 hr at 30° C. Transformant MCM330 was selected on LA with CMP5, Kan50.

iii) Integration into *E. coli* Chromosome

Miniprepped DNA (Qiaquick Spin kit) from MCM330 was digested with SnaBI and used to electroporate BL21(DE3) (Novagen) or MG1655 containing GeneBridges plasmid pRedET Carb. Cells were grown at 30° C. to ~OD1 then induced with 0.4% L-arabinose at 37° C. for 1.5 hours. These cells were washed three times in 4 C ddH2O before electroporation with 2 μL of DNA. Integrants were selected on L agar with containing chloramphenicol (5 μg/ml) and subsequently confirmed not to grow on L agar+Kanamycin (50 μg/ml). BL21 integrant MCM331 and MG1655 integrant MCM333 were frozen.

TABLE 2-1

| Primers | |
|---|---|
| MCM219 | caccatgcgttgtagcgtgtcca (SEQ ID NO: 29) |
| MCM182 | gggcccgtttaaactttaactagactctgcagttagcgttcaaacggcagaa (SEQ ID NO: 30) |
| MCM218 | caccatgcgtcgttctgcgaactac (SEQ ID NO:31) |

TABLE 2-2

| Primers of construction of MCM331 | | |
|---|---|---|
| MCM78 | attTn7 up rev for integration construct | gcatgctcgagcggccgcTTTTAATCAAACATCCTGCCAACTC (SEQ ID NO: 32) |
| MCM79 | attTn7 down rev for integration construct | gatcgaagggcgatcgTGTCACAGTCTGGCGAAACCG (SEQ ID NO: 33) |
| MCM88 | attTn7 up forw for integration construct | ctgaattctgcagatatcTGTTTTTCCACTCTTCGTTCACTTT (SEQ ID NO: 34) |

TABLE 2-2-continued

| Primers of construction of MCM331 | | |
|---|---|---|
| MCM89 | attTn7 down forw for integration construct | tctagagggcccAAGAAAAATGCCCCGCTTACG (SEQ ID NO: 35) |
| MCM104 | GI1.2 promoter-MVK | Gatcgcggccgcgcccttgacgatgccacatcctgagcaa Ataattcaaccactaattgtgagcggataacacaaggagg Aaacagctatgtcattaccgttcttaacttc (SEQ ID NO: 36) |
| MCM105 | aspA terminator-yIDI | Gatcgggccccaagaaaaaaggcacgtcatctgacgtgcc Tttttatttgtagacgcgttgttatagcattcta (SEQ ID NO: 37) |
| MCM120 | Forward of attTn7: attTn7 homology, GB marker homology | aaagtagccgaagatgacggtttgtcacatggagtt ggcaggatgtttgattaaaagcAATTAACCCTCACTA AAGGGCGG (SEQ ID NO: 38) |
| MCM127 | Rev complement of 1.2 GI: GB marker homology(extra long), promoter, RBS, ATG | AGAGTGTTCACCAAAAATAATAACCTTTCCCGGTGCAgaa Gttaagaacggtaatgacatagctgtttcctccttgtgtt Atccgctcacaattagtggttgaattatttgctcaggatg tggcatcgtcaagggcTAATACGACTCACTATAGGGCTCG (SEQ ID NO: 39) |

TABLE 2-3

| Plasmids | |
|---|---|
| *P. alba* pET24a | pET24a with "full length" IspS from *P. alba* |
| *P. trichocharpa* pET24a | pET24a with "full length" IspS from *P. trichocharpa* |
| *P. tremuloides* pET24a | pET24a with "full length" IspS from *P. tremuloides* |
| MBP-Kudzu | |
| pDu27 | *P. alba* FL-pET200/Top 10 |
| pDu30 | *P. alba* TRC-pET200/Top10 |
| pDu31 | *P. trem* TRC-pET200/Top 10 |
| pDu32 | *P. trich* TRC-pET200/Top10 |
| MD09-161 | pET24a-*P.alba* FL C-Term (+) TEV, His tag/MCM331 |
| MD09-163 | pET24a-*P.alba* TRC (MEA) C-Term (+) TEV, His tag/MCM331 |

TABLE 2-4

| Strains | |
|---|---|
| MBP-Kudzu | |
| MD08-99 | BL21 DE3 pLys + pDu27 |
| MD08-100 | BL21 DE3 pLys + pDu30 |
| MD08-102 | BL21 DE3 pLys + pDu31 |
| MD08-104 | BL21 DE3 pLys + pDu32 |
| MD09-165 | BL21(DE3)pLysS, pET24a-*P.alba* FL C-Term (+) TEV, His tag |
| MD09-167 | BL21(DE3) pLysS, pET24a-*P.alba* TRC (MEA) C-Term (+) TEV, His tag |

II. Purification of 6×His-Tagged IspS

Expression of 6×His-Tagged IspS

N-terminally 6×His-tagged IspS was expressed and purified from strain MD08-99. The growth procedure is suitable for histidine tagged enzymes expressed in BL21(λDE3) pLysS cells. A 10 ml of overnight culture was prepared for each 1 L of planned growth. The appropriate antibiotics (50 mg/ml kanamycin, 50 mg/ml chloramphenicol, and/or 50 mg/ml Carbenecillin) was added to 10 ml of LB medium in a 25 ml flask and was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1 L Day culture was inoculated with 10 ml of overnight culture and grown at 30-37° C. with shaking at ~220 rpm until the $OD_{600}$ reached ~0.4-0.6. Day cultures were then induced with 400 μM IPTG and allowed to continue growing at 30° C. with shaking at 220 rpm for ~5-6 hours. Cells were then harvested by centrifugation at 10,000×g for 10 min, 4° C. Following Harvest, cells were used directly or stored at −80° C. until ready to process.

Purification of 6×His-Tagged IspS

For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 40-50 ml of lysis buffer was used per 1 L of cell pellet. Cells were then incubated on ice for approximately 30 min. The cell suspension was then lysed fully by passing 2-3 times through a french pressure cell (large french press cell at 1200 psi/High setting) until lysate started to look clear. A sample of the lysate was saved for activity assay and gel analysis (~100 μl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 μl).

The clarified lysate was run over HisTrap HP columns (GE Healthcare) using a gradient from 0-100% Ni buffer B. Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a HiPrep 26/10 Desalting column (GE healthcare) packed with Sephadex G25 resin. The G-25 buffer consisted of 50 mM HEPES, 50 mM NaCl, and 1 mM DTT, pH 7.4. The desired sample was then purified over a HiTrap Q HP column (GE) using a gradient elution from 0% Q seph buffer A to 100% Q seph buffer B (Q seph buffer A: 50 mM Tris, 0.05 M NaCl, 1 mM DTT, pH 7.6 and Q seph buffer B: 50 mM Tris, 1.0 M NaCl, 1 mM DTT, pH 7.6). Fractions containing the desired protein were analyzed and concentrated. Sample buffer was then exchanged into 50 mM HEPES, 50 mM NaCL, pH 7.4 with 1 mM DTT by passing the sample over a Hi Prep 26/10 Desalting column (GE healthcare) packed with Sephadex G25 resin. A final polishing step of Gel filtration was used when necessary. The sample was passed through a Hi Load 26/60 Superdex 200 prep grade (GE) in gel filtration buffer: (50 mM HEPES, 150 mM NaCl, 1 mM DTT, pH 7.4). Fractions were then analyzed and concentrated. The samples were then stored at −80° C. For preparation for analysis of the band, the sample is run on an SDS-PAGE gel (4-12% NUPAGE gel, Invitrogen), stained and the desired band excised and processed as described below.

III. Digestion of TEV (Tobacco Etch Virus) or EK (Enterokinase)-Tagged Enzymes

TEV Cleavage (IspS from Strains MD09-165 and MD09-167)

For digestion, enzymes were purified through a Ni charged sepharose (GE Healthcare) and desalted into 50 mM HEPES, 50 mM NaCl pH 7.4 buffer containing 1 mM DTT. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (that is also tagged) and impurities. The Ni column pass though and washes were analyzed using SDS-PAGE gel (NUPAGE, Invitrogen) and DMAPP activity assays. Samples containing pure enzyme were pooled and desalted into 50 mM NaCl pH 7.4 buffer containing 1 mM DTT and stored at −80° C.

EK Cleavage (IspS from Strains MD08-102 and MD08-104)

For digestion enzymes were purified through a Ni charges sepharose (GE Healthcare) and desalted into 50 mM HEPES, 50 mM NaCl pH 7.4 buffer containing 1 mM DTT.

Digestion was performed with EKMax (E180-02) (Invitrogen) using 1 unit of EKMax per 20 ug of purified protein at 4° C. overnight. Samples were passed over EK Away resin (Invitrogen) to remove excess enterokinase. Samples were batched onto Ni charged sepharose resin (equilibrated in the Ni was buffer) and incubated for 30 min at 4° C., with occasional inverting. This removed uncleaved enzyme, tag, and impurities. The Ni column pass though and washes were analyzed using SDS-PAGE gel (4-12% NUPAGE, Invitrogen) and DMAPP activity assays. Samples containing pure enzyme were pooled and desalted into 50 mM NaCl pH 7.4 buffer containing 1 mM DTT. Stored at −80° C.

IV. Purification of MBP-IspS

Construction of pMAL-C4X Kudzu for the expression of MBP-Kudzu isoprene synthase is described in Example 1. MBP-Kudzu isoprene synthase production from *E. coli* grown in batch culture at the 15-L scale.

Medium Recipe (Per Liter Fermentation Medium):

$K_2HPO_4$ 7.5 g, $MgSO_4$*$7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

Citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, ZnSO*$7H_2O$ 1 g, $CuSO_4$*$5H_2O$ 100 mg, $H_3BO_3$ 100 mg, $NaMoO_4$*$2H_2O$ 100 mg. Each component is dissolved one at a time in $diH_2O$, pH to 3.0 with HCl/NaOH, then q.s. to volume and filter sterilized with 0.22 micron filter.

Fermentation was performed in a 15-L bioreactor with BL21 (DE3) *E. coli* cells containing the pMAL-C4X plasmid expressing a maltose binding protein (MBP)-Kudzu isoprene synthase fusion molecule. This experiment was carried out to produce isoprene synthase at the desired fermentation pH 7.0 and temperature 30° C. A frozen vial of the *E. coli* strain was thawed and inoculated into tryptone-yeast extract medium. After the inoculum grew to OD 1.0, measured at 550 nm ($OD_{550}$), 120 mL was used to inoculate a 15-L bioreactor bringing the initial volume to 9-L.

Expression of the desired molecule was achieved by adding isopropyl-beta-D-1-thiogalactopyranoside (IPTG). The IPTG concentration was brought to 1 mM when the $OD_{550}$ reached a value of 10. Cells containing the desired product were harvested 3 hrs after IPTG addition.

MBP-IspS Purification

The broth was centrifuged for 15 min at 10000×g. The pellet was collected and frozen at −80° C. until further purification. Cells were resuspended in MBP-Bind Buffer (5% glycerol, 20 mM Tris pH 7.4, 200 mM NaCl, 2 mM DTT, 1 mg/ml lysozyme) and passed through the french press three times at 20000 psi. The lysate was then ultracentrifuged at 100000×g for 1 hour to yield a relatively clear solution. The supernatant was pipetted from the top of the tube without disturbing the gelatinous material on the bottom of the centrifuge tube. Gel filtration was performed on the supernatant using a Superdex-200 26/60 column (GE healthcare). The column was developed using MBP-Bind buffer at a flow rate of 3 mL/min at 23° C. Fractions were tested for DMAPP activity as described below. Active fractions were pooled and loaded onto 25 mL amylose resin (New England Biolabs). The column was washed with 10 column volumes MBP-Bind buffer and the protein was then eluted with 2 column volumes of MBP-Bind buffer containing 10 mM maltose to yield >90% pure MBP-IspS.

V. DMAPP Assay

The following reaction mixture was used for the DMAPP assay: 25 μL lysate mixture, 5 μL MgCl2 (1 M), 5 μL DMAPP (100 mM), and 65 μL 100 mM Tris pH 8, 100 mM NaCl for a total volume of 100 μL. The reaction is performed at 30° C. for 15 minutes in a gas tight 1.8 mL GC tube. Reactions are terminated by the addition of 100 μL 500 mM EDTA (pH 8). The amount of isoprene produced was measured by GC/MS.

The analysis was performed (for the 2 mL and 96-well plate methods) using an Agilent 6890 GC/MS system interfaced with a 5973 MS Leap CTC CombiPAL autosampler operating in headspace mode. An Agilent HP-5 (5% Phenyl Methyl Siloxane (15 m×0.25 mm×0.25 uM)) column was used for separation of analytes. The sampler was set up to inject 100 μL of headspace gas. The GC/MS method utilized helium as the carrier gas at a flow of 1 ml/min. The injection port was held at 250° C. with a split ratio of 50:1. The oven temperature was held at 37° C. for the 2 min duration of the analysis. The Agilent 5793N mass selective detector was run in single ion monitoring (SIM) mode on mass 67. The detector was switched off from 0.00 to 0.44 minutes to allow the elution of permanent gases and on 0.44 mins to 0.60 mins. Under these conditions isoprene (2-methyl-1,3-butadiene) was observed to elute at 0.49 minutes. A calibration table was used to quantify the absolute amount of isoprene and was found to be linear from 0 μg/L to 5600 mg/L (using calibration gas).

Example 3

Three-Dimensional Structure of IspS

Seven constructs of plant isoprene synthase (IspS) were prepared in the hope that one or more would yield crystals suitable for x-ray diffraction. These were: a construct containing N-terminal histidine-tagged maltose binding protein and kudzu IspS (MBP-kudzu), full-length *P. alba* IspS with N-terminal histidine-tag (MD08-99), *P. alba* IspS with the first nineteen N-terminal residues removed (MD08-100), this construct also had the N-terminal his-tag removed after purification. Full-length, untagged *P. alba* IspS (strain RM11608-2). A truncated *P. alba* IspS construct featuring two additional residues before the twin-arginine motif was generated (MD09-167). *P. tricharpa* IspS was generated, which contains both an N-terminal his-tag and N-terminal truncation (MD08-104), and another construct composed of IspS from *P. tremuloides* was generated with an N-terminal his-tag and N-terminal truncation (MD08-102). Construction of strains expressing various isoprene synthases are described above.

Protein from each construct was purified and a concentrated protein solution was then prepared for surveying possible crystallization conditions. Each protein was purified independently and surveyed as described below. All in-house crystallization screens were set up using the hanging drop vapor diffusion method. At a minimum, each protein was surveyed using the following commercial screens: the Crystal Screen from Hampton Research (Aliso Viejo, Calif.) and the JCSG+Suite from Qiagen (Valencia, Calif.).

Purified MBP-kudzu using was set up using the following commercial screens: the Crystal Screen from Hampton Research and the JCSG+Suite from. Additionally, purified MBP-kudzu was sent to the Hauptman-Woodward Institute (Buffalo, N.Y.) for high-throughput screening, where no fewer than 1536 conditions were surveyed. The purified MBP-kudzu fusion precipitated out of solution in the majority of conditions, and no protein crystals were observed.

The next construct used for crystallization screening was MD08-99 (full-length *P. alba* IspS with N-terminal histidine-tag). MD08-99 was purified and the histidine-tag was removed. The same three initial crystallization screens were performed as for MBP-kudzu. The Hampton Research Crystal Screen and Qiagen JCSG+Suite were each performed at multiple protein concentrations. Small needle-like crystals were observed in some Hampton Research Crystal Screen conditions. Further attempts to improve the crystals involved co-crystallization with the IspS inhibitor sodium ibandronate (Sigma-Aldrich, St Louis, Mo.). Taken together, an additional 288 crystallization conditions were attempted with variations of pH, concentration, and crystallization reagents. The nine best crystals were then prepared for data collection and tested in-house on a Rigaku RU200 rotating anode generator and R-AXIS IV++, and they either did not diffract x-rays or were salt crystals.

The first nineteen N-terminal residues of *P. alba* IspS were removed to produce construct MD08-100. This construct had the N-terminal histidine-tag removed after purification. In house crystallization screens were performed using the Hampton Research Crystal Screen and Qiagen JCS G+Suite, each with multiple protein concentrations. Initial crystal hits included hexagonal plates that diffracted to 16 Å resolution, and small rods that diffracted to 5 Å resolution using the in-house x-ray generator. In an attempt to improve the crystals, MD08-100 was co-crystallized with either sodium ibandronate or sodium pyrophosphate (Sigma-Aldrich, St Louis, Mo.), both of which are inhibitors of the IspS activity. Neither inhibitor resulted in improved crystals or improved diffraction. An additional 168 crystallization conditions were attempted with variations of pH, concentration, and crystallization reagents. The twenty-one most promising MD08-100 crystals were screened for diffraction, with the best resolution obtained being 5 Å.

Full-length, untagged *P. alba* IspS (strain RM11608-2) from a fermentation run was purified. An initial screen was set up using the Hampton Research Crystal Screen, and crystals were observed in four different conditions. All four crystals were tested for diffraction in-house, with three being salt crystals and one not diffracting.

A truncated *P. alba* IspS construct featuring two additional residues before the twin-arginine motif was generated (MD09-167). This construct contains a C-terminal histidine-tag, and crystallization experiments were set up with the tag either cleaved or not cleaved, at varying protein concentrations, and with or without sodium pyrophosphate. Initial crystallization screens were done as per MBP-kudzu. Crystals from this construct were observed in numerous conditions; optimization included 528 variations of pH, precipitating agents, concentrations, and inhibitors. From the optimization experiments, fifteen different MD09-167 crystals were screened in-house for diffraction. In an effort to improve the resolution, various crystal freezing conditions were tested, with the effect of improving the diffraction limits from 10 Å to 6.5 Å.

A new construct containing *P. tricharpa* IspS was generated, which contains both an N-terminal histidine-tag and an N-terminal truncation (MD08-104). Purified MD08-104 with cleaved histidine-tag was surveyed using the Hampton Research Crystal Screen and the Qiagen JCSG+suite. This construct generated heavier precipitate than the *P. alba* IspS constructs. Very small needles were observed, with none of the crystals being suitable for diffraction.

Another construct composed of IspS from *P. tremuloides* was generated with an N-terminal histidine-tag and an N-terminal truncation (MD08-102; SEQ ID NO:11). Purified MD08-102 with and without cleaved histidine-tag was set up using the Hampton Research Crystal Screen and the Qiagen JCSG+Suite at varying protein concentrations. Rod and plate-like crystals were observed in some conditions and an additional 120 experiments were performed to improve the crystals by varying pH, concentration, and crystallization reagents. From the optimization experiments, ten crystals were tested in-house, with the initial best diffraction reaching 5 Å. Upon further modification of the freezing conditions of the crystals, a crystal was found that diffracted to 3.3 Å from the uncleaved histidine-tagged protein. This crystal was grown by mixing 2 μL of protein (10 mg/ml, with 30 mM $MgCl_2$) with 2 μL of precipitant solution [10% (wt/vol) polyethylene glycol 8000, 0.1 M HEPES, pH 7.5, 8% ethylene glycol] and equilibrated against 500 μL of precipitant. A cluster of rod-shaped crystals appeared after three weeks. The crystals belong to the tetragonal space group P43212, and have unit cell dimensions a=154.2, b=154.2, c=142.7.

In-house x-ray diffraction data were collected under a nitrogen stream at 100 K using a Rigaku RU200 generator and R-AXIS IV++ detector. Before flash-freezing the crystal in liquid nitrogen, it was cryoprotected by swiping it through a solution containing 10% (wt/vol) polyethylene glycol 8000, 0.1 M HEPES, pH 7.5, and 25% ethylene glycol. Data were integrated using Mosflm (Leslie, A. (1998) J. of Appl. Crystallography 30, 1036-1040) and scaled using SCALA (Collaborative Computational Project, N. (1994) Acta Crystallographica Section D 50, 760-763). The data were then phased by molecular replacement using MrBUMP (Keegan, R. M., and Winn, M. D. (2007) Acta Crystallographica Section D 63, 447-457; Vagin, A., and Teplyakov, A. (1997) J. of Appl. Crystallography 30, 1022-1025), with a monomer of limonene synthase (Protein Data Bank ID 2ONH) (Berman, H., et al. (2007) Nucl. Acids Res. 35, D301-303) as the starting model. The crystal contains one dimer in the asymmetric unit with a solvent content of 66%.

A 3.05 Å data set from the same crystal was then collected using beamline 11-1 of the Stanford Synchrotron Radiation Laboratory. These data were also processed using Mosflm and SCALA. Data collection and refinement statistics are given in Table 3-1.

Refinement with Refmac5 (Collaborative Computational Project, N. (1994) Acta Crystallographica Section D 50, 760-763) was used with iterative manual rebuilding steps using the visualization program Coot (Emsley, P., and Cowtan, K. (2004) Acta Crystallographica Section D 60, 2126-2132). During refinement, the geometry of the protein was checked using Molprobity (Davis, I. W., et al. (2007) Nucl. Acids Res., gkm216).

Figure 30:
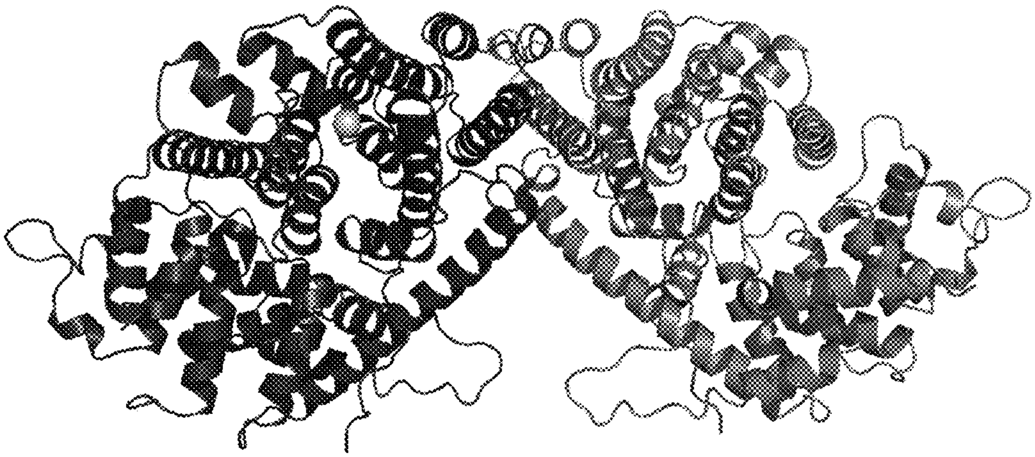
FIG. 30 provides the three-dimensional structure of *P. tremuloides* IspS shown as a dimer. Chain A is in dark gray, chain B is in medium gray and the single magnesium ion found in each active site is light gray.
Figure 31:
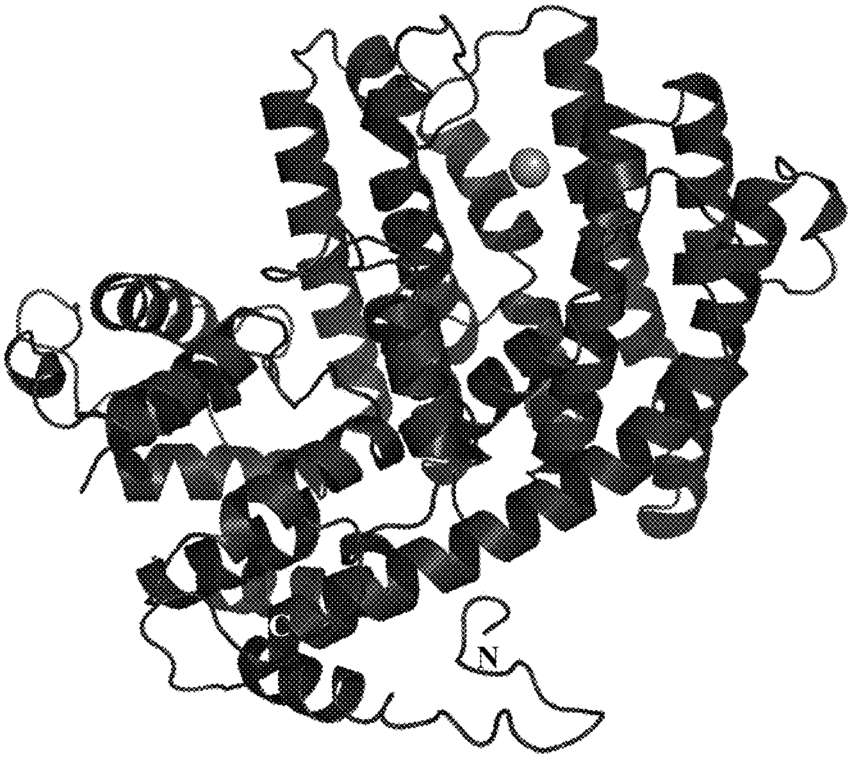
FIG. 31 provides a monomer view of the structure of *P. tremuloides* IspS. The magnesium is shown as a light gray sphere and the N- and C-terminals are indicated.

The fold of *P. tremuloides* IspS is similar to bornyl diphosphate synthase (Whittington, D. A., et al. (2002) Proc. Natl. Acad. Sci. USA 99, 15375-15380), limonene synthase (Hyatt, D. C., et al. (2007) Proc. Natl. Acad. Sci. USA 104, 5360-5365), and tobacco 5-epi-aristolochene synthase (Starks, C. M., et al. (1997) Science 277, 1815-1820). The structure consists of two helical domains, a C-terminal domain containing the active site and N-terminal domain with unknown function (FIGS. 30 and 31). Coordinates are provided in Table 3-7.

TABLE 3-1

Data Collection and Refinement Statistics

| | |
|---|---|
| Data Collection | |
| Space Group | $P4_32_12$ |
| Cell dimensions | |
| A, b, c (Å) | 154.2, 154.2, 142.7 |
| α, β, γ, (°) | 90.0, 90.0, 90.0 |
| Resolution (Å) | 37.8-3.05 |
| $R_{merge}$ | 16.4 (72.9)[a] |
| <I/σI> | 10.3 (2.6) |
| Completeness (%) | 99.8 (100) |
| Redundancy | 7.3 (7.4) |
| Refinement | |
| Resolution (Å) | 37.8-3.05 |
| No. measured reflections | 248741 |
| No. Unique reflections | 34201 |
| $R_{work}$ | 21.1 |
| $R_{free}$ | 27.1 |
| rmsd bonds, (Å) | 0.011 |
| rmsd angles, (°) | 1.28 |
| No. of Atoms | |
| Protein, ions[b] | 8331 |
| Water | 18 |

Flexible Loops

Figure 32:
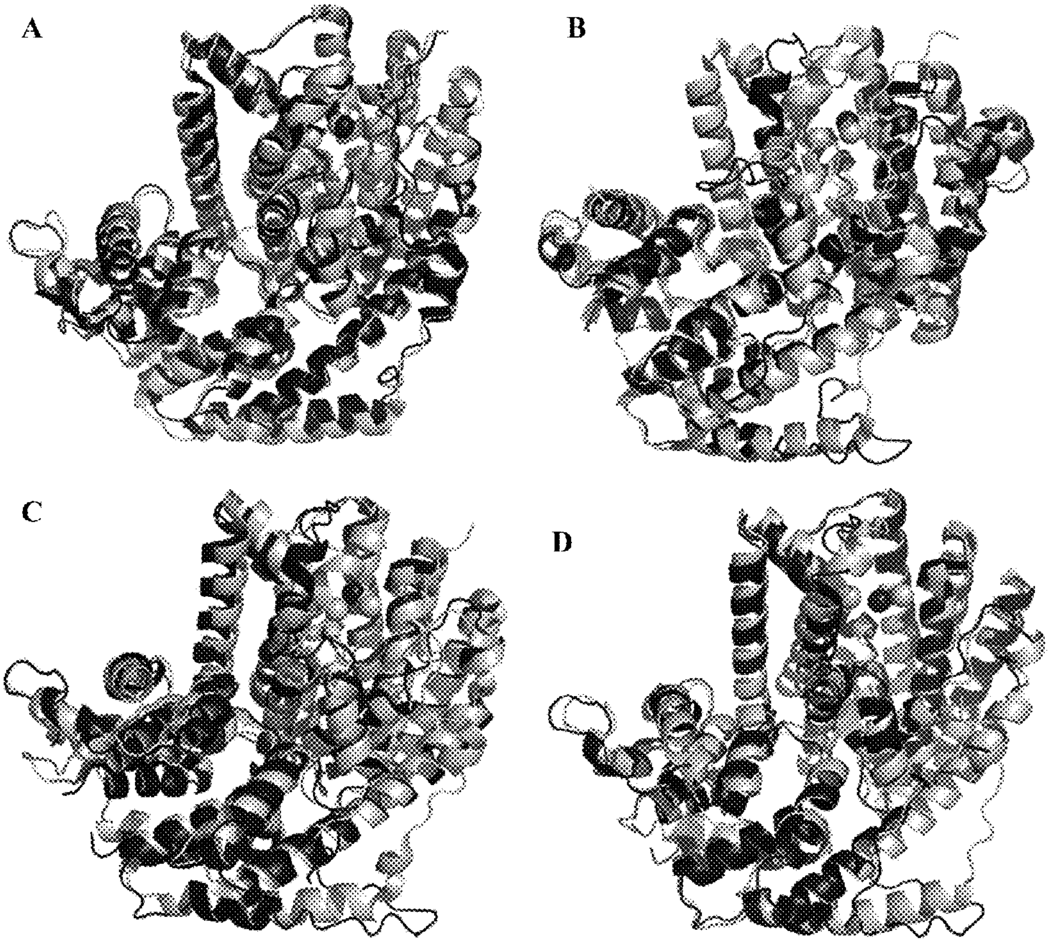
FIG. 32 shows the structural alignments between (A) BdpS and LS, (B) BdpS and *P. tremuloides* IspS, (C) LS and *P. tremuloides* IspS, and (D) TEAS and *P. tremuloides* IspS. In each case the first structure is in light gray and the second is in dark gray. Divalent cations are shown as spheres.
Figure 33:
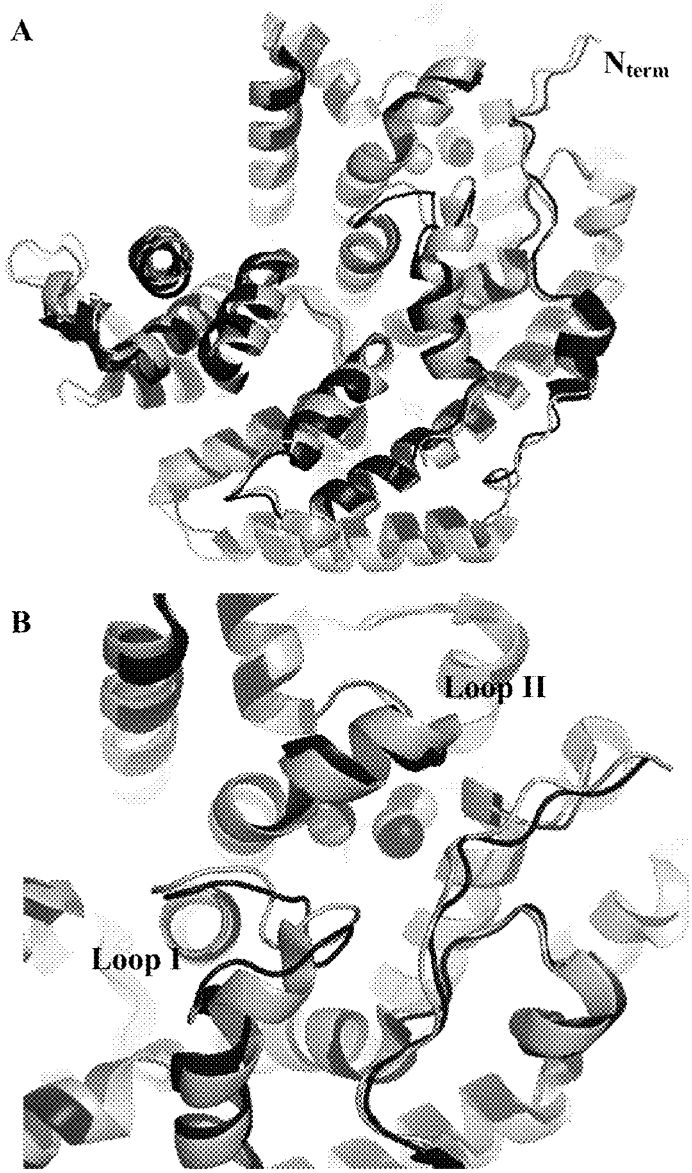
FIG. 33 shows the three dimensional structure of loops in BdpS and LS. Panel A shows the N-terminal loop of Ls in light gray and the N-terminal loop of BdpS in dark gray. Panel B shows that Loop I and Loop II are structurally homologous.
Figure 34:
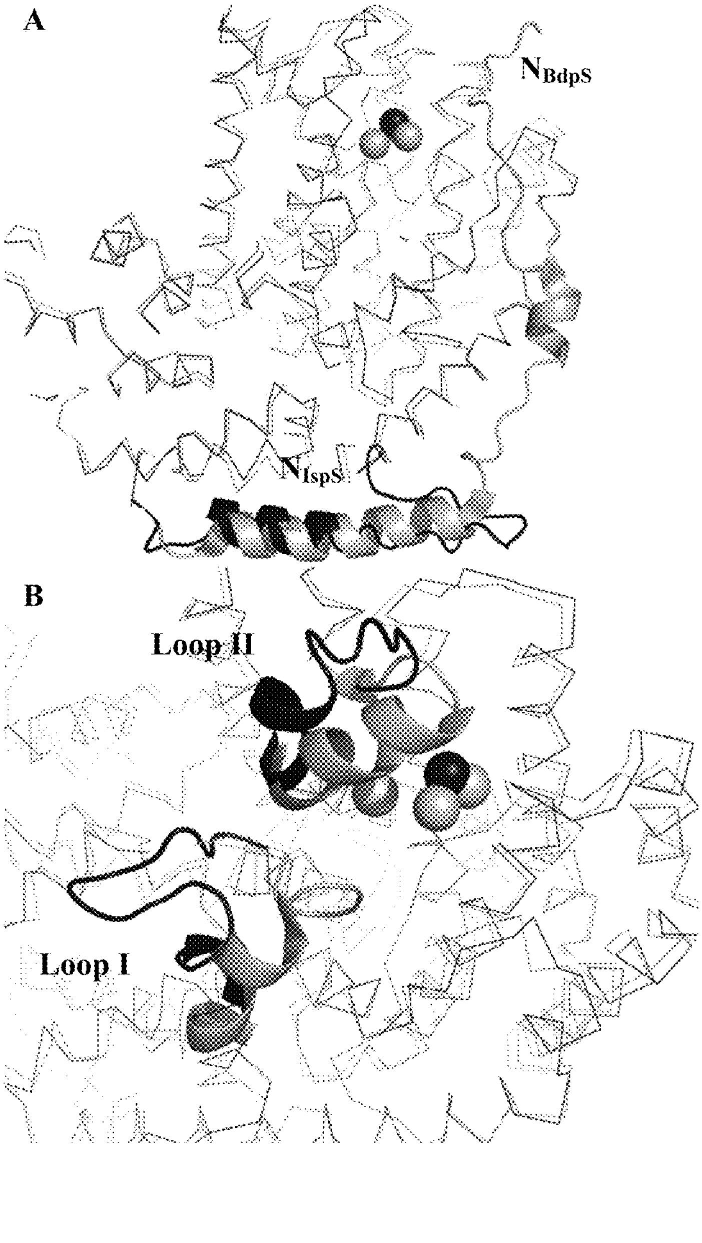
FIG. 34 shows the N-terminal loop of BdpS (dark gray) and *P. tremuloides* IspS (light gray) are structurally divergent. Panel A shows the N-terminal loop and panel B shows Loop I and Loop II.
Figure 35:
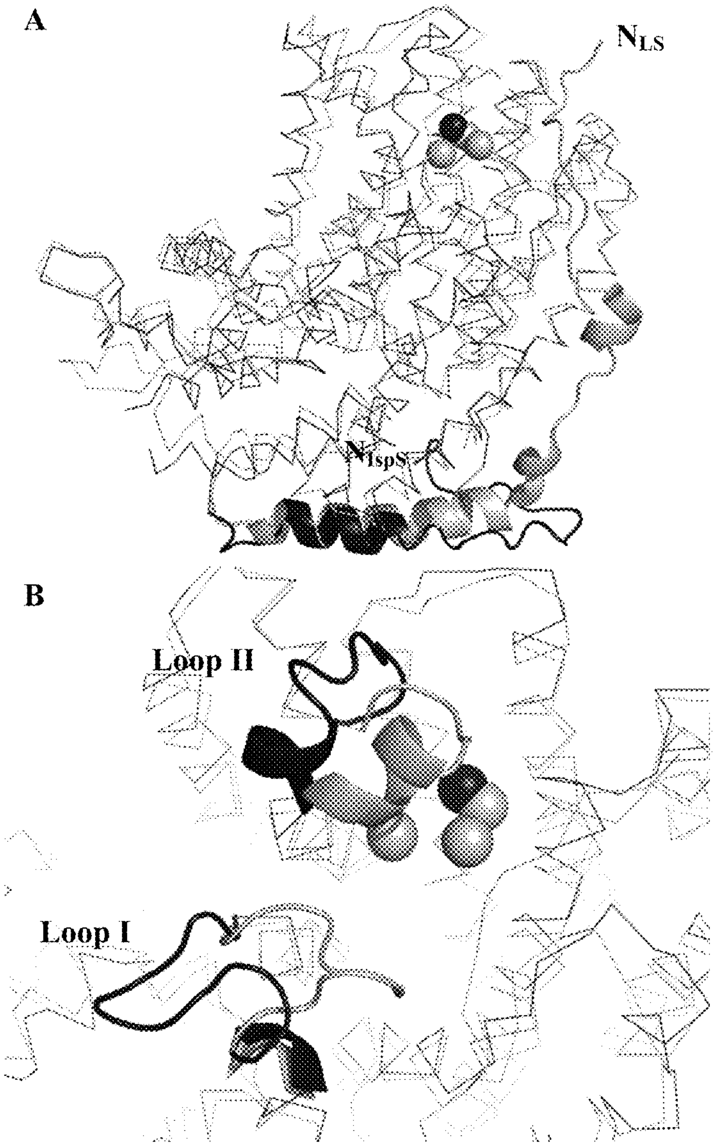
FIG. 35 shows the N-terminal loop of LS (light gray) and *P. tremuloides* IspS (dark gray) are structurally divergent. Panel A shows the N-terminal loop and panel B shows Loop I and Loop II.
Figure 36:
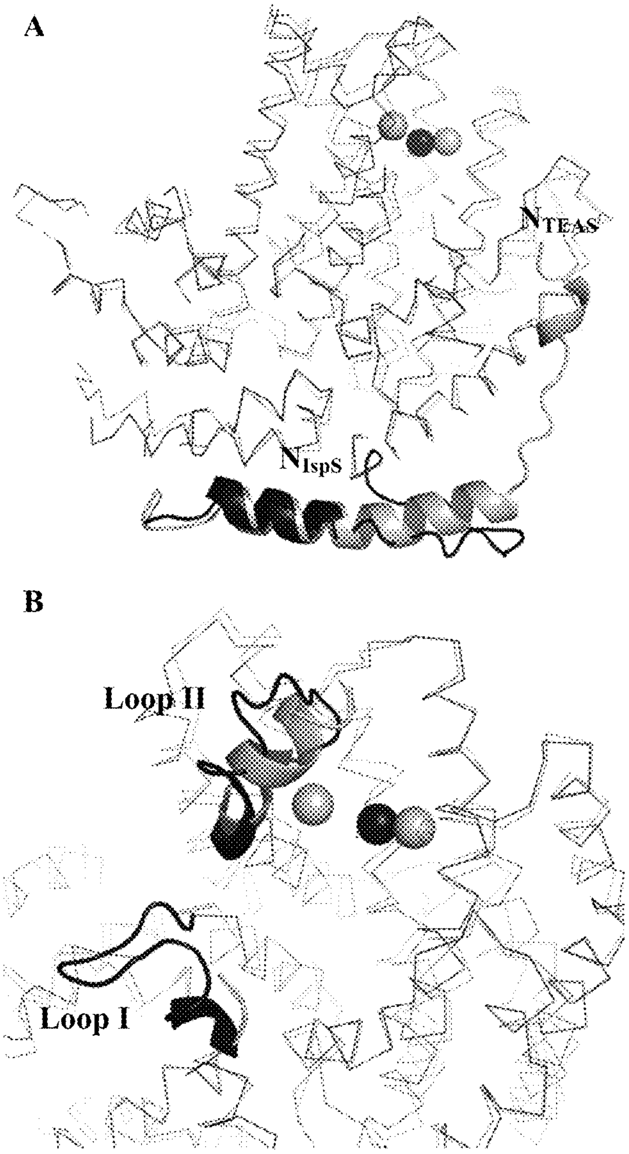
FIG. 36 shows the N-terminal loop of TEAS (light gray) and *P. tremuloides* IspS (dark gray) are structurally divergent. Panel A shows the N-terminal loop and panel B shows Loop I and Loop II. Loop I is disordered in TEAS.

The unique and unexpected discovery coming from the determination of the three-dimensional structure of isoprene synthase is that several crucial loops forming the active site are flexible. The discovery can be immediately seen when the known structure of other terpene synthases are compared with the structure of isoprene synthase (FIG. 32). Overall, the structures are highly conserved in the conformation of secondary structure and connectivity loops. (In this example of the *P. tremuloides* IspS from construct P.tremTRC-pET200, the numbering convention is such that the first number of the complete sequence containing the tag is −35, with the first residue of IspS being 1.) However, three segments, forming a considerable portion of the substrate binding pocket, notably the truncated N-terminus, along with two loops comprised of residues 438-453 (Loop I) and residues 512-527 (Loop II) are seen to diverge (FIGS. 33 to 36). This has been attributed to the absence of substrate complexed with the enzyme in our structure determination.

In comparing the enzyme with BdpS, for example, we find that the loops corresponding to residues 498-513 and 573-587 are composed of the same number of residues and have a homologous, but not identical amino sequence in these regions. We expect that the related terpene synthases will be found to display similar flexibility in the segments as these structures become more thoroughly studied. The residues in terpene synthases corresponding to these variable loop regions are enumerated in Table 3-2.

TABLE 3-2

Residues corresponding to variable loops in terpene synthases.

| | *P. tremuloides* IspS | LS | BdpS | TEAS |
|---|---|---|---|---|
| N-term I | Met 1 | Met 57 | Ile 54 | Val 14 |
| | Arg 2 | Arg 58 | Arg 55 | Arg 15 |
| | Arg 3 | Arg 59 | Arg 56 | Pro 16 |
| | Ser 4 | Ser 60 | Ser 57 | Val 17 |
| | Ala 5 | Gly 61 | Gly 58 | Ala 18 |
| | Asn 6 | Asn 62 | Asn 59 | Asp 19 |
| | Tyr 7 | Tyr 63 | Tyr 60 | Phe 20 |
| | Glu 8 | Asn 64 | Gln 61 | Ser 21 |
| | Pro 9 | Pro 65 | Pro 62 | Pro 22 |
| | Asn 10 | Ser 66 | Ala 63 | Ser 23 |
| | Ser 11 | Arg 67 | Leu 64 | Leu 24 |
| | Trp 12 | Trp 68 | Trp 65 | Trp 25 |
| | Asp 13 | Asp 69 | Asp 66 | Gly 26 |
| | Tyr 14 | Val 70 | Ser 67 | Asp 27 |
| | Asp 15 | Asn 71 | Asn 68 | Gln 28 |
| | Tyr 16 | Phe 72 | Tyr 69 | Phe 29 |
| N-term II | Leu 17 | Ile 73 | Ile 70 | Leu 30 |
| | Leu 18 | Gln 74 | Gln 71 | Ser 31 |
| | Ser 19 | Ser 75 | Ser 72 | Phe 32 |
| | Ser 20 | Leu 76 | Leu 73 | Ser 34 |
| | Asp 21 | Leu 77 | Asn 74 | Ile 35 |
| | Thr 22 | Ser 78 | Thr 75 | Asp 36 |
| | Asp 23 | Asp 79 | Pro 76 | Asn 37 |
| | Glu 24 | Tyr 80 | Tyr 77 | Gln 38 |
| | Ser 25 | Lys 81 | Thr 78 | Val 39 |
| | Ile 26 | Glu 82 | Glu 79 | Ala 40 |
| | Glu 27 | Asp 83 | Glu 80 | Glu 41 |
| | Val 28 | Lys 84 | Arg 81 | Lys 42 |
| Loop I | Leu 438 | Leu 498 | Leu 498 | Thr 446 |
| | Ala 439 | Gly 499 | Gly 499 | Ala 447 |
| | Ser 440 | Thr 500 | Thr 500 | The 448 |
| | Ala 441 | Ser 501 | Ser 502 | Tyr 449 |
| | Ser 442 | Val 502 | Tyr 503 | Glu 450 |
| | Ala 443 | Glu 503 | Phe 504 | Val 451 |
| | Glu 444 | Glu 504 | Glu 505 | Glu 452 |
| | Ile 445 | Val 505 | Leu 506 | Lys 453 |
| | Ala 446 | Ser 506 | Ala 507 | Ser 454 |
| | Arg 447 | Arg 507 | Arg 508 | Arg 455 |
| | Gly 448 | Gly 508 | Gly 509 | Gly 456 |
| | Glu 449 | Asp 509 | Asp 510 | Gln 457 |
| | Thr 450 | Val 510 | Val 511 | Ile 458 |
| | Ala 451 | Pro 511 | Pro 512 | Ala 459 |
| | Asn 452 | Lys 512 | Lys 513 | Thr 460 |
| | Ser 453 | Ser 513 | Thr 514 | Gly 461 |
| Loop II | Tyr 512 | Tyr 576 | Tyr 573 | Tyr 520 |
| | | | | Ile 521 |
| | His 513 | His 577 | Leu 574 | His 522 |
| | Asn 514 | Asn 578 | His 575 | Asn 523 |
| | Gly 515 | Gly 579 | Gly 576 | Leu 524 |
| | Asp 516 | Asp 580 | Asp 577 | Asp 525 |
| | Ala 517 | Gly 581 | Gly 578 | Gly 526 |
| | His 518 | His 582 | Phe 579 | Tyr 527 |
| | Thr 519 | Gly 583 | Gly 580 | The 528 |
| | Ser 520 | Thr 584 | Val 581 | His 529 |
| | Pro 521 | Gln 585 | Gln 582 | Pro 530 |
| | Asp 522 | His 585 | His 583 | Glu 531 |
| | Glu 523 | Pro 586 | Ser 584 | Lys 532 |
| | Leu 524 | Ile 587 | Lys 585 | Val 533 |
| | Thr 525 | Ile 588 | Thr 586 | Lue 534 |
| | Arg 526 | His 589 | Tyr 587 | Lys 535 |

This important finding can be exploited for the engineering of improved isoprene synthase in a straightforward manner. It would be desirable to exploit the flexibility to enhance enzyme performance by making substitutions in the amino aids forming these segments to facilitate the transitions the enzyme must undergo in the steps of binding substrate and allowing rearrangement of substrate in different kinetic steps that are postulated to occur during enzymatic de-phosphorylation and for electron transfer to convert DMAPP to isoprene.

The structure provides the new insight that these loops can be present in at least two conformations: the "open" form in the absence of substrate, as we have see in the uncomplexed structure of the isoprene synthase, and a "closed," or active form when the substrate is bound. It would therefore also be beneficial to modify residues coming in contact with the loops in the active form as described in Table 3-3.

TABLE 3-3

Residues coming within 5 angstroms of flexible elements

| | *P trem* IspS | 1N1B | 2ONG | 5EAS[e] |
|---|---|---|---|---|
| N-term neighbors | L17, L18, S19, S20, S239, R243, F253, A254, R255, D256, R257, I259, E260, D293, Y295, D296, V297, Y298, G299, T300, E303, Y325, L374, Y375, elements of loop I, elements of loop II, V529, L530, T534 | 70I, 71Q, 72S, 73L, 298S, 302S, 312F, 313V, 314R, 315D, 316R, 318V, 319E, 352D, 354Y, 355D, 356V, 357Y, 358G, 359T, 362E, 384Y, 433Y, 434H, elements of loop I, elements of loop II, 589I, 590A, 594F | I73, Q74, S75, L76, F299, R303, F313, A314, R315, A316, R317, V319, E320, D353, Y355, D356, V357, Y358, G359, T360, E363, Y385, F434, Y435, elements of loop I, elements of loop II, M590, T591, F595 | L30, S31, F32, S33, S248, K252, Y262, A263, R264, D265, R266, V268, E269, D302, F304, D305, A306, Y307, G308, T309, E312, Y334, F383, I384, elements of loop I, elements of loop II, I538, I538, V543 |
| Loop I neighbors | Elements of N-term, D293, Y295, V297, E370, A371, W373, L374, S378, T379, P380, F382, Y385, F386, R433, L434 C435, N436, D437, V454, S455, C456, Y457, M458, T469, V472, I476, Y512, elements of loop II | Elements of N-term, 352D, 354Y, 356V, 429E, 430A, 432W, 433Y, 437Y, 438T, 439P, 441L, 444Y, 445L, 493R, 494L, 495P, 496D, 497D, 514I, 515Q, 516C, 517Y, 518M, 529V, 532V, 536I, 572Y, elements of loop II | Elements of N-term, D353, Y355, V357, E430, A431, W433, F434, H438, K439, P440, L442, Y445, L446, R493, L494, A495, D496, D497, L514, Q515, C516, Y517, M518, R529, V532, I536, Y573, elements of loop II | Elements of N-term, D304, F304, A306, E379, S380, W382, F383, Y387, T388, P389, V391, Y394, L395, R441, V442, I443, D444, D445, I462, E463, C464, C465, M466, M477, F480, A484, Y520, elements of loop II |
| Loop II neighbors | Elements of N-terminus, E187, L188, R255, R257, F270, E271, Q273, Y274, F285, V288, A439, S440, S442, S508, H509, C510, T511, Y512, R528, V529, L530, S531, V532 | Elements of N-terminus, 246D, 247L, 314R, 316R, 329E, 330S, 332F, 333W, 344I, 348I, 499G, 500T, 503Y, 568A, 569Q, 570F, 571I, 572Y, 588H, 589I, 590A, 591G, 592L | Elements of N-terminus, D247, I248, R315, R317, E330, P331, Q333, H334, N345, I347, G499, T500, V502, A569, Q570, L571, M572, Y573, Q589, M590, T591, R592, T593 | Elements of N-terminus, E195, Q196, R264, R266, F279, E280, Q282, Y283, I294, I297, A447, T448, E450, V516, E517, V518, T519, Y520, H537, I538, I539, N540, L541 |

TABLE 3-4

Percent Identity of Terpene Cyclases.

| | *P trem* IspS | 1N1B | 2ONG | 5EAS[e] |
|---|---|---|---|---|
| *P alba* IspS[a] | 98.6 | 40.7 | 41.3 | 33.2 |
| *P trem* IspS[b] | | 41.0 | 41.4 | 33.2 |
| 1N1B[c] | | | 51.4 | 33.8 |
| 2ONG[d] | | | | 33.3 |

[a]*Polar alba* isoprene synthase
[b]*Polar tremuloides* isoprene synthase
[c]bornyl diphosphate synthase
[d]limonene synthase
[e]5-epi-aristolochene synthase Selection of Sites for Improvement of Plant Isoprene Synthase The isoprene synthases of plants were expected to be homologous to the terpene synthases. The three-dimensional structures of three homologous terpene synthases have been determined: *Salvia officinalis* bornyl diphosphate synthase (BdpS; pdb entry 1N1B), *Mentha spicata* limonene synthase (LS; pdb entry 2ONG), and tobacco 5-epi-aristolochene synthase (TEAS; pdb entry SEAS). These enzymes share only 33% homology but their tertiary structure is conserved. Sequence identity is shown in Table 3-4, and structural homology between the structures is shown in Table 3-5. In addition, the structures of intermediate complexes with all three related enzymes have shown that not only tertiary folding, but also detailed interactions in the active sites of these enzymes are highly conserved.

TABLE 3-5

Structural Alignment of Terpene Synthases.

| | 1N1B[b] | 2ONG[c] | 5EAS[d] |
|---|---|---|---|
| *P trem* IspS[a] | 1.40 (465)[e] | 1.29 (468) | 1.62 (458) |
| 1N1B | | 1.27 (520) | 1.97 (476) |
| 2ONG | | | 1.83 (477) |

[a]*Polar tremuloides* isoprene synthase
[b]bornyl diphosphate synthase
[c]limonene synthase
[d]5-epi-aristolochene synthase
[e]Root mean square deviation in Å for Cα atoms, with the number of aligned residues in parenthesis In this example of the *P. tremuloides* IspS from construct P.tremTRC-pET200, the numbering convention is such that the first number of the complete sequence containing the tag is −35, with the first residue of IspS being 1.

A comparison of the active site from the structure of BdpS and the structure of IspS indicates that the active site involved in metal ion binding and phosphate recognition is conserved. In particular, Arg 255, Asp 292, Asp 296, Glu 370, Arg 433 and Asn 436 of *P. tremuloides* IspS were observed to overlap equivalent residues in BdpS. The positioning of an intermediate of the BdpS was also compared with the IspS structure. Based on this it was possible to identify the analogous binding region and the approach direction that dimethylallyl pyrophosphate would require in order to bind and react with the IspS enzyme.

Based on the structure of IspS, sites in the IspS were identified as candidates for mutagenesis to produce variant IspS enzymes with improved performance. Briefly, sites were selected in the IspS that might alter the interaction of the metal binding, diphosphate recognition, DMAPP chain binding and/or the approach to the active site.

I. Diphosphate/Metal Binding Sites

The side chains of amino acid residues in the IspS that are found in proximity to the metal and diphosphate binding side chains were identified. These residues include Asp 293, Tyr 385, Ser 392, and Asp 437 of *P. tremuloides* IspS. Engineering of these sites may result in increased enzyme activity.

II. Substrate Access Loops

The substrate access loops of IspS are in regions that deviate from the BdpS structure. In the BdpS structure the residues create a cover over the active site. It is likely that upon substrate binding the structure of IspS will form a similar structure. As such the residues in these loops, including residues 440-453 and 512-524, may be in a position to alter the activity of the IspS. In the *P. tremuloides* IspS enzyme, residues 440-453 have the sequence SASAEIARGETANS (SEQ ID NO:40) and residues 512-526 have the sequence YHNGDAHTSPDEL (SEQ ID NO:41).

III. Isoprenyl Binding Site

The complex of BdpS and the product of the reaction, bornyl diphosphate (PDB entry 1N24), was used to identify residues in the IspS structure that with protein engineering may be used modulate substrate specificity and/or reaction rate (altered on and off rates of substrate and product). These residues include Ser 261, Trp 264, Phe 285, Thr 289, Ser 393, Ser 394, Phe 432, and Try 512 *P. tremuloides* IspS.

TABLE 3-6

Candidate Mutagenesis Sites

| | *P. tremuloides* IspS |
|---|---|
| DPP/Metal Binding Sites | Asp 293 |
| | Tyr 385 |
| | Ser 392 |
| | Asp 437 |
| Substrate Access Loop I | Ser 440 |
| | Ala 441 |
| | Ser 442 |
| | Ala 443 |
| | Glu 444 |
| | Ile 445 |
| | Ala 446 |
| | Arg 447 |
| | Gly 448 |
| | Glu 449 |
| | Thr 450 |
| | Ala 451 |
| | Asn 452 |
| | Ser 453 |
| Substate Access Loop II | Tyr 512 |
| | His 513 |
| | Asn 514 |
| | Gly 515 |
| | Asp 516 |
| | Ala 517 |
| | His 518 |
| | Thr 519 |
| | Ser 520 |
| | Pro 521 |
| | Asp 522 |
| | Glu 523 |
| | Leu 524 |
| Isoprenyl Binding Site | Ser 261 |
| | Trp 264 |
| | Phe 285 |
| | Thr 289 |
| | Ser 393 |
| | Ser 394 |
| | Phe 432 |
| | Tyr 512 |

TABLE 3-7

Coordinates of *P. tremuloides IspS*

| | | |
|---|---|---|
| HEADER | --- XX-XXX-XX xxxx | |
| COMPND | — | |
| REMARK | 3 | |
| REMARK | 3 | REFINEMENT. |
| REMARK | 3 | PROGRAM : REFMAC 5.5.0088 |
| REMARK | 3 | AUTHORS : MURSHUDOV, VAGIN, DODSON |
| REMARK | 3 | |
| REMARK | 3 | REFINEMENT TARGET: MAXIMUM LIKELIHOOD |
| REMARK | 3 | |
| REMARK | 3 | DATA USED IN REFINEMENT. |
| REMARK | 3 | RESOLUTION RANGE HIGH (ANGSTROMS): 3.05 |
| REMARK | 3 | RESOLUTION RANGE LOW (ANGSTROMS): 110.17 |
| REMARK | 3 | DATA CUTOFF (SIGMA(F)): NONE |
| REMARK | 3 | COMPLETENESS FOR RANGE (%): 99.67 |
| REMARK | 3 | NUMBER OF REFLECTIONS : 32446 |
| REMARK | 3 | |
| REMARK | 3 | FIT TO DATA USED IN REFINEMENT. |
| REMARK | 3 | CROSS-VALIDATION METHOD: THROUGHOUT |
| REMARK | 3 | FREE R VALUE TEST SET SELECTION: RANDOM |
| REMARK | 3 | R VALUE (WORKING + TEST SET): .21396 |
| REMARK | 3 | R VALUE (WORKING SET) : .21092 |
| REMARK | 3 | FREE R VALUE: .27112 |
| REMARK | 3 | FREE R VALUE TEST SET SIZE (%): 5.1 |

TABLE 3-7-continued

| Coordinates of *P. tremuloides IspS* | | |
|---|---|---|
| REMARK | 3 | FREE R VALUE TEST SET COUNT : 1727 |
| REMARK | 3 | |
| REMARK | 3 | FIT IN THE HIGHEST RESOLUTION BIN. |
| REMARK | 3 | TOTAL NUMBER OF BINS USED : 20 |
| REMARK | 3 | BIN RESOLUTION RANGE HIGH : 3.050 |
| REMARK | 3 | BIN RESOLUTION RANGE LOW : 3.129 |
| REMARK | 3 | REFLECTION IN BIN (WORKING SET): 2359 |
| REMARK | 3 | BIN COMPLETENESS (WORKING + TEST) (%): 100.00 |
| REMARK | 3 | BIN R VALUE (WORKING SET): .288 |
| REMARK | 3 | BIN FREE R VALUE SET COUNT : 127 |
| REMARK | 3 | BIN FREE R VALUE : .352 |
| REMARK | 3 | |
| REMARK | 3 | NUMBER OF NON-HYDROGEN ATOMS USED IN REFINEMENT. |
| REMARK | 3 | ALL ATOMS : 8349 |
| REMARK | 3 | |
| REMARK | 3 | B VALUES. |
| REMARK | 3 | FROM WILSON PLOT (A**2): NULL |
| REMARK | 3 | MEAN B VALUE (OVERALL, A**2): 24.592 |
| REMARK | 3 | OVERALL ANISOTROPIC B VALUE. |
| REMARK | 3 | B11 (A**2): .41 |
| REMARK | 3 | B22 (A**2): .41 |
| REMARK | 3 | B33 (A**2): −.81 |
| REMARK | 3 | B12 (A**2): .00 |
| REMARK | 3 | B13 (A**2): .00 |
| REMARK | 3 | B23 (A**2): .00 |
| REMARK | 3 | |
| REMARK | 3 | ESTIMATED OVERALL COORDINATE ERROR. |
| REMARK | 3 | ESU BASED ON R VALUE (A): NULL |
| REMARK | 3 | ESU BASED ON FREE R VALUE (A): .427 |
| REMARK | 3 | ESU BASED ON MAXIMUM LIKELIHOOD (A): .327 |
| REMARK | 3 | ESU FOR B VALUES BASED ON MAXIMUM LIKELIHOOD (A**2): 39.836 |
| REMARK | 3 | |
| REMARK | 3 | CORRELATION COEFFICIENTS. |
| REMARK | 3 | CORRELATION COEFFICIENT FO-FC : .916 |
| REMARK | 3 | CORRELATION COEFFICIENT FO-FC FREE : .868 |
| REMARK | 3 | |
| REMARK | 3 | RMS DEVIATIONS FROM IDEAL VALUES COUNT RMS WEIGHT |
| REMARK | 3 | BOND LENGTHS REFINED ATOMS (A): 8495; .011;.022 |
| REMARK | 3 | BOND LENGTHS OTHERS (A): 5804; .001; .020 |
| REMARK | 3 | BOND ANGLES REFINED ATOMS (DEGREES): 11476; 1.279; 1.953 |
| REMARK | 3 | BOND ANGLES OTHERS (DEGREES): 14093; .882; 3.000 |
| REMARK | 3 | TORSION ANGLES, PERIOD 1 (DEGREES): 1020; 7.002; 5.000 |
| REMARK | 3 | TORSION ANGLES, PERIOD 2 (DEGREES): 435; 35.412; 24.299 |
| REMARK | 3 | TORSION ANGLES, PERIOD 3 (DEGREES): 1525; 18.250; 15.000 |
| REMARK | 3 | TORSION ANGLES, PERIOD 4 (DEGREES): 58; 16.811; 15.000 |
| REMARK | 3 | CHIRAL-CENTER RESTRAINTS (A**3): 1266; .070; .200 |
| REMARK | 3 | GENERAL PLANES REFINED ATOMS (A): 9416; .005; .020 |
| REMARK | 3 | GENERAL PLANES OTHERS (A): 1780; .001; .020 |
| REMARK | 3 | |
| REMARK | 3 | ISOTROPIC THERMAL FACTOR RESTRAINTS. COUNT RMS WEIGHT |
| REMARK | 3 | MAIN-CHAIN BOND REFINED ATOMS (A**2): 5104; .514; 1.500 |
| REMARK | 3 | MAIN-CHAIN BOND OTHER ATOMS (A**2): 2068; .059; 1.500 |
| REMARK | 3 | MAIN-CHAIN ANGLE REFINED ATOMS (A**2): 8204; 1.000; 2.000 |
| REMARK | 3 | SIDE-CHAIN BOND REFINED ATOMS (A**2): 3391; 1.218; 3.000 |
| REMARK | 3 | SIDE-CHAIN ANGLE REFINED ATOMS (A**2): 3272; 2.157; 4.500 |
| REMARK | 3 | |
| REMARK | 3 | NCS RESTRAINTS STATISTICS |
| REMARK | 3 | NUMBER OF DIFFERENT NCS GROUPS: 1 |
| REMARK | 3 | |
| REMARK | 3 | NCS GROUP NUMBER : 1 |
| REMARK | 3 | CHAIN NAMES: A B |
| REMARK | 3 | NUMBER OF COMPONENTS NCS GROUP: 1 |
| REMARK | 3 | COMPONENT C SSSEQI TO C SSSEQI CODE |
| REMARK | 3 | 1 A 17 A 541 6 |
| REMARK | 3 | 1 B 17 B 541 6 |
| REMARK | 3 | GROUP CHAIN COUNT RMS WEIGHT |
| REMARK | 3 | LOOSE POSITIONAL 1 1 (A): 7038; .37; 5.00 |
| REMARK | 3 | LOOSE THERMAL 1 1 (A**2): 7038; 1.09; 10.00 |
| REMARK | 3 | |
| REMARK | 3 | TWIN DETAILS |
| REMARK | 3 | NUMBER OF TWIN DOMAINS: NULL |
| REMARK | 3 | |
| REMARK | 3 | |
| REMARK | 3 | TLS DETAILS |
| REMARK | 3 | NUMBER OF TLS GROUPS : 8 |

TABLE 3-7-continued

Coordinates of *P. tremuloides IspS*

| | | |
|---|---|---|
| REMARK | 3 | ATOM RECORD CONTAINS RESIDUAL B FACTORS ONLY |
| REMARK | 3 | |
| REMARK | 3 | TLS GROUP: 1 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: A 17 A 219 |
| REMARK | 3 | ORIGIN FOR THE GROUP (A): −64.7667 37.6643 −.0896 |
| REMARK | 3 | T TENSOR |
| REMARK | 3 | T11: .0648 T22: .0357 |
| REMARK | 3 | T33: .0787 T12: .0200 |
| REMARK | 3 | T13: .0129 T23: −.0089 |
| REMARK | 3 | L TENSOR |
| REMARK | 3 | L11: 3.7204 L22: 1.5111 |
| REMARK | 3 | L33: 2.6701 L12: .5715 |
| REMARK | 3 | L13: .6692 L23: −.9699 |
| REMARK | 3 | S TENSOR |
| REMARK | 3 | S11: .0562 S12: .0478 S13: −.1976 |
| REMARK | 3 | S21: −.1702 S22: −.0055 S23: .1376 |
| REMARK | 3 | S31: .0900 S32: −.2188 S33: −.0507 |
| REMARK | 3 | |
| REMARK | 3 | TLS GROUP: 2 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: A 220 A 287 |
| REMARK | 3 | ORIGIN FOR THE GROUP (A): −59.5787 8.4529 −.7693 |
| REMARK | 3 | T TENSOR |
| REMARK | 3 | T11: .1615 T22: .0645 |
| REMARK | 3 | T33: .1539 T12: −.0314 |
| REMARK | 3 | T13: −.0461 T23: .0198 |
| REMARK | 3 | L TENSOR |
| REMARK | 3 | L11: 2.4192 L22: 4.6709 |
| REMARK | 3 | L33: .7709 L12: −3.2943 |
| REMARK | 3 | L13: −.1814 L23: −.0705 |
| REMARK | 3 | S TENSOR |
| REMARK | 3 | S11: .0055 S12: −.0699 S13: −.2073 |
| REMARK | 3 | S21: −.1805 S22: .0996 S23: .3781 |
| REMARK | 3 | S31: .2596 S32: .0887 S33: −.1051 |
| REMARK | 3 | |
| REMARK | 3 | TLS GROUP: 3 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: A 288 A 374 |
| REMARK | 3 | ORIGIN FOR THE GROUP (A): −40.1866 1.6932 .5805 |
| REMARK | 3 | T TENSOR |
| REMARK | 3 | T11: .1149 T22: .1003 |
| REMARK | 3 | T33: .1629 T12: .0153 |
| REMARK | 3 | T13: .0224 T23: .0164 |
| REMARK | 3 | L TENSOR |
| REMARK | 3 | L11: .2271 L22: .7399 |
| REMARK | 3 | L33: 4.8529 L12: .3413 |
| REMARK | 3 | L13: .4755 L23: −.1746 |
| REMARK | 3 | S TENSOR |
| REMARK | 3 | S11: −.0449 S12: −.0288 S13: −.1131 |
| REMARK | 3 | S21: −.1346 S22: −.0665 S23: −.2749 |
| REMARK | 3 | S31: −.0040 S32: .1558 S33: 1114 |
| REMARK | 3 | |
| REMARK | 3 | TLS GROUP: 4 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: A 375 A 541 |
| REMARK | 3 | ORIGIN FOR THE GROUP (A): −47.2220 21.5399 6.9217 |
| REMARK | 3 | T TENSOR |
| REMARK | 3 | T11: .1551 T22: .1194 |
| REMARK | 3 | T33: .1485 T12: −.0666 |
| REMARK | 3 | T13: .0275 T23: .0272 |
| REMARK | 3 | L TENSOR |
| REMARK | 3 | L11: 2.2352 L22: 2.1698 |
| REMARK | 3 | L33: 2.3370 L12: −.4501 |
| REMARK | 3 | L13: 2.2662 L23: −.1852 |
| REMARK | 3 | S TENSOR |
| REMARK | 3 | S11: .0233 S12: −.3041 S13: −.0323 |
| REMARK | 3 | S21: .3375 S22: .0236 S23: .0121 |
| REMARK | 3 | S31: .0592 S32: −.2979 S33: −.0469 |
| REMARK | 3 | |
| REMARK | 3 | TLS GROUP: 5 |
| REMARK | 3 | NUMBER OF COMPONENTS GROUP: 1 |
| REMARK | 3 | COMPONENTS C SSSEQI TO C SSSEQI |

TABLE 3-7-continued

Coordinates of *P. tremuloides IspS*

| | | |
|---|---|---|
| REMARK | 3 | RESIDUE RANGE: B 17 B 219 |
| REMARK | 3 | ORIGIN FOR THE GROUP (A): −73.9834 −39.9016 −18.5783 |
| REMARK | 3 | T TENSOR |
| REMARK | 3 | T11: .0658 T22: .1153 |
| REMARK | 3 | T33: .1251 T12: −.0621 |
| REMARK | 3 | T13: −.0164 T23: −.0098 |
| REMARK | 3 | L TENSOR |
| REMARK | 3 | L11: 4.6230 L22: 1.7260 |
| REMARK | 3 | L33: 3.8816 L12: −.4202 |
| REMARK | 3 | L13: −1.8646 L23: −.9046 |
| REMARK | 3 | S TENSOR |
| REMARK | 3 | S11: −.0685 S12: .0375 S13: −.0003 |
| REMARK | 3 | S21: .1931 S22: .0510 S23: −.0097 |
| REMARK | 3 | S31: .0317 S32: −.2047 S33: .0175 |
| REMARK | 3 | |
| REMARK | 3 | TLS GROUP: 6 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: B 220 B 287 |
| REMARK | 3 | ORIGIN FOR THE GROUP (A): −62.1586 −12.7634 −18.1912 |
| REMARK | 3 | T TENSOR |
| REMARK | 3 | T11: .1825 T22: .0804 |
| REMARK | 3 | T33: .1512 T12: .0549 |
| REMARK | 3 | T13: .0773 T23: .0208 |
| REMARK | 3 | L TENSOR |
| REMARK | 3 | L11: 5.4421 L22: 4.0606 |
| REMARK | 3 | L33: 1.5369 L12: 4.6706 |
| REMARK | 3 | L13: −2.0058 L23: −1.5537 |
| REMARK | 3 | S TENSOR |
| REMARK | 3 | S11: .1622 S12: .0431 S13: .3257 |
| REMARK | 3 | S21: .1755 S22: .0292 S23: .2977 |
| REMARK | 3 | S31: −.1910 S32: −.0506 S33: −.1914 |
| REMARK | 3 | |
| REMARK | 3 | TLS GROUP: 7 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: B 288 B 374 |
| REMARK | 3 | ORIGIN FOR THE GROUP (A): −41.6930 −10.8250 −19.6636 |
| REMARK | 3 | T TENSOR |
| REMARK | 3 | T11: .1424 T22: .0604 |
| REMARK | 3 | T33: .1153 T12: .0184 |
| REMARK | 3 | T13: .0146 T23: .0276 |
| REMARK | 3 | L TENSOR |
| REMARK | 3 | L11: .6426 L22: .8163 |
| REMARK | 3 | L33: 2.3437 L12: −.1831 |
| REMARK | 3 | L13: −.5246 L23: .4917 |
| REMARK | 3 | S TENSOR |
| REMARK | 3 | S11: .0592 S12: −.0206 S13: .0071 |
| REMARK | 3 | S21: .0906 S22: −.0229 S23: −.1585 |
| REMARK | 3 | S31: −.0355 S32 .0262 S33: −.0363 |
| REMARK | 3 | |
| REMARK | 3 | TLS GROUP: 8 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: B 375 B 541 |
| REMARK | 3 | ORIGIN FOR THE GROUP (A): −53.4886 −28.3212 −26.0670 |
| REMARK | 3 | T TENSOR |
| REMARK | 3 | T11:.1107 T22: .1220 |
| REMARK | 3 | T33: .1514 T12 .0692 |
| REMARK | 3 | T13: −.0073 T23: .0518 |
| REMARK | 3 | L TENSOR |
| REMARK | 3 | L11: 2.6766 L22: 1.8433 |
| REMARK | 3 | L33: 2.6389 L12: .1130 |
| REMARK | 3 | L13: −2.4696 L23: .6986 |
| REMARK | 3 | S TENSOR |
| REMARK | 3 | S11: .1115 S12: .3882 S13: .0569 |
| REMARK | 3 | S21: −.0725 S22: −.0724 S23: .1450 |
| REMARK | 3 | S31: −.1453 S32: −.4044 S33: −.0392 |
| REMARK | 3 | |
| REMARK | 3 | |
| REMARK | 3 | BULK SOLVENT MODELLING. |
| REMARK | 3 | METHOD USED: MASK |
| REMARK | 3 | PARAMETERS FOR MASK CALCULATION |
| REMARK | 3 | VDW PROBE RADIUS: 1.40 |
| REMARK | 3 | ION PROBE RADIUS: .80 |
| REMARK | 3 | SHRINKAGE RADIUS: .80 |
| REMARK | 3 | |
| REMARK | 3 | OTHER REFINEMENT REMARKS: |

TABLE 3-7-continued

Coordinates of *P. tremuloides IspS*

REMARK 3 HYDROGENS HAVE BEEN ADDED IN THE RIDING POSITIONS
REMARK 3 U VALUES: RESIDUAL ONLY
REMARK 3
CISPEP 1 ALA A 446 ARG A 447 .00
CISPEP 2 GLY A 515 ASP A 516 .00
CISPEP 3 THR B 22 ASP B 23 .00
CISPEP 4 ALA B 446 ARG B 447 .00
CISPEP 5 GLY B 515 ASP B 516 .00
CRYST1 155.800 155.800 143.690 90.00 90.00 90.00 P 43 21 2
SCALE1 .006418 .000000 .000000 .00000
SCALE2 .000000 .006418 .000000 .00000
SCALE3 .000000 .000000 .006959 .00000

| | | | | | | | | | | | |
|---|---|---|---|---|---|---|---|---|---|---|---|
| ATOM | 1 | N | LEU | A | 17 | −63.930 | 24.416 | −19.202 | 1.00 | 30.90 | N |
| ATOM | 2 | CA | LEU | A | 17 | −64.132 | 23.019 | −19.731 | 1.00 | 31.43 | C |
| ATOM | 4 | CB | LEU | A | 17 | −63.308 | 22.800 | −21.021 | 1.00 | 31.35 | C |
| ATOM | 7 | CG | LEU | A | 17 | −64.002 | 23.016 | −22.386 | 1.00 | 31.95 | C |
| ATOM | 9 | CD1 | LEU | A | 17 | −62.989 | 23.068 | −23.550 | 1.00 | 31.88 | C |
| ATOM | 13 | CD2 | LEU | A | 17 | −65.052 | 21.915 | −22.676 | 1.00 | 31.95 | C |
| ATOM | 17 | C | LEU | A | 17 | −63.783 | 21.952 | −18.660 | 1.00 | 31.39 | C |
| ATOM | 18 | O | LEU | A | 17 | −63.142 | 22.291 | −17.651 | 1.00 | 31.61 | O |
| ATOM | 22 | N | LEU | A | 18 | −64.216 | 20.693 | −18.877 | 1.00 | 31.11 | N |
| ATOM | 23 | CA | LEU | A | 18 | −63.986 | 19.529 | −17.957 | 1.00 | 30.78 | C |
| ATOM | 25 | CB | LEU | A | 18 | −62.503 | 19.072 | −17.935 | 1.00 | 30.97 | C |
| ATOM | 28 | CG | LEU | A | 18 | −61.303 | 19.949 | −17.496 | 1.00 | 31.10 | C |
| ATOM | 30 | CD1 | LEU | A | 18 | −61.406 | 20.430 | −16.064 | 1.00 | 30.71 | C |
| ATOM | 34 | CD2 | LEU | A | 18 | −59.977 | 19.173 | −17.703 | 1.00 | 31.87 | C |
| ATOM | 38 | C | LEU | A | 18 | −64.531 | 19.665 | −16.522 | 1.00 | 30.38 | C |
| ATOM | 39 | O | LEU | A | 18 | −64.837 | 18.667 | −15.883 | 1.00 | 29.86 | O |
| ATOM | 41 | N | SER | A | 19 | −64.587 | 20.900 | −16.023 | 1.00 | 30.45 | N |
| ATOM | 42 | CA | SER | A | 19 | −65.335 | 21.276 | −14.815 | 1.00 | 30.37 | C |
| ATOM | 44 | CB | SER | A | 19 | −64.604 | 22.417 | −14.026 | 1.00 | 30.02 | C |
| ATOM | 47 | OG | SER | A | 19 | −64.881 | 23.741 | −14.489 | 1.00 | 28.00 | O |
| ATOM | 49 | C | SER | A | 19 | −66.784 | 21.654 | −15.218 | 1.00 | 31.03 | C |
| ATOM | 50 | O | SER | A | 19 | −67.666 | 21.711 | −14.367 | 1.00 | 30.95 | O |
| ATOM | 52 | N | SER | A | 20 | −67.023 | 21.880 | −16.519 | 1.00 | 31.85 | N |
| ATOM | 53 | CA | SER | A | 20 | −68.355 | 22.247 | −17.051 | 1.00 | 32.37 | C |
| ATOM | 55 | CB | SER | A | 20 | −68.291 | 22.507 | −18.579 | 1.00 | 32.39 | C |
| ATOM | 58 | OG | SER | A | 20 | −67.387 | 23.542 | −18.931 | 1.00 | 31.77 | O |
| ATOM | 60 | C | SER | A | 20 | −69.357 | 21.124 | −16.744 | 1.00 | 33.04 | C |
| ATOM | 61 | O | SER | A | 20 | −69.076 | 20.254 | −15.922 | 1.00 | 33.08 | O |
| ATOM | 63 | N | ASP | A | 21 | −70.522 | 21.136 | −17.393 | 1.00 | 33.88 | N |
| ATOM | 64 | CA | ASP | A | 21 | −71.512 | 20.069 | −17.206 | 1.00 | 34.48 | C |
| ATOM | 66 | CB | ASP | A | 21 | −72.907 | 20.655 | −17.127 | 1.00 | 34.59 | C |
| ATOM | 69 | CG | ASP | A | 21 | −73.022 | 21.661 | −16.006 | 1.00 | 35.54 | C |
| ATOM | 70 | OD1 | ASP | A | 21 | −72.041 | 21.836 | −15.251 | 1.00 | 35.31 | O |
| ATOM | 71 | OD2 | ASP | A | 21 | −74.082 | 22.289 | −15.870 | 1.00 | 38.72 | O |
| ATOM | 72 | C | ASP | A | 21 | −71.409 | 18.975 | −18.260 | 1.00 | 34.94 | C |
| ATOM | 73 | O | ASP | A | 21 | −72.134 | 18.947 | −19.269 | 1.00 | 34.58 | O |
| ATOM | 75 | N | THR | A | 22 | −70.457 | 18.086 | −17.989 | 1.00 | 35.66 | N |
| ATOM | 76 | CA | THR | A | 22 | −70.340 | 16.799 | −18.657 | 1.00 | 36.27 | C |
| ATOM | 78 | CB | THR | A | 22 | −68.895 | 16.576 | −19.168 | 1.00 | 36.30 | C |
| ATOM | 80 | OG1 | THR | A | 22 | −67.968 | 17.278 | −18.322 | 1.00 | 36.04 | O |
| ATOM | 82 | CG2 | THR | A | 22 | −68.755 | 17.088 | −20.604 | 1.00 | 36.11 | C |
| ATOM | 86 | C | THR | A | 22 | −70.792 | 15.714 | −17.648 | 1.00 | 36.83 | C |
| ATOM | 87 | O | THR | A | 22 | −69.968 | 15.022 | −17.035 | 1.00 | 37.05 | O |
| ATOM | 89 | N | ASP | A | 23 | −72.121 | 15.599 | −17.494 | 1.00 | 37.27 | N |
| ATOM | 90 | CA | ASP | A | 23 | −72.790 | 14.802 | −16.441 | 1.00 | 37.25 | C |
| ATOM | 92 | CB | ASP | A | 23 | −72.962 | 15.659 | −15.167 | 1.00 | 37.17 | C |
| ATOM | 95 | CG | ASP | A | 23 | −71.625 | 16.081 | −14.549 | 1.00 | 37.74 | C |
| ATOM | 96 | OD1 | ASP | A | 23 | −70.714 | 15.241 | −14.436 | 1.00 | 38.88 | O |
| ATOM | 97 | OD2 | ASP | A | 23 | −71.472 | 17.256 | −14.164 | 1.00 | 38.91 | O |
| ATOM | 98 | C | ASP | A | 23 | −74.172 | 14.351 | −16.956 | 1.00 | 37.18 | C |
| ATOM | 99 | O | ASP | A | 23 | −75.137 | 15.112 | −16.846 | 1.00 | 37.10 | O |
| ATOM | 101 | N | GLU | A | 24 | −74.280 | 13.134 | −17.501 | 1.00 | 37.23 | N |
| ATOM | 102 | CA | GLU | A | 24 | −75.406 | 12.815 | −18.410 | 1.00 | 37.58 | C |
| ATOM | 104 | CB | GLU | A | 24 | −74.941 | 13.007 | −19.865 | 1.00 | 37.77 | C |
| ATOM | 107 | CG | GLU | A | 24 | −74.424 | 14.417 | −20.239 | 1.00 | 37.98 | C |
| ATOM | 110 | CD | GLU | A | 24 | −74.121 | 14.556 | −21.746 | 1.00 | 38.35 | C |
| ATOM | 111 | OE1 | GLU | A | 24 | −74.284 | 13.564 | −22.503 | 1.00 | 38.12 | O |
| ATOM | 112 | OE2 | GLU | A | 24 | −73.721 | 15.661 | −22.174 | 1.00 | 38.18 | O |
| ATOM | 113 | C | GLU | A | 24 | −76.139 | 11.440 | −18.323 | 1.00 | 37.79 | C |
| ATOM | 114 | O | GLU | A | 24 | −77.323 | 11.397 | −17.960 | 1.00 | 37.90 | O |
| ATOM | 116 | N | SER | A | 25 | −75.462 | 10.345 | −18.696 | 1.00 | 37.92 | N |
| ATOM | 117 | CA | SER | A | 25 | −76.140 | 9.070 | −19.048 | 1.00 | 38.09 | C |
| ATOM | 119 | CB | SER | A | 25 | −75.167 | 8.076 | −19.723 | 1.00 | 38.11 | C |
| ATOM | 122 | OG | SER | A | 25 | −74.503 | 7.239 | −18.787 | 1.00 | 38.02 | O |
| ATOM | 124 | C | SER | A | 25 | −76.917 | 8.374 | −17.907 | 1.00 | 38.42 | C |

TABLE 3-7-continued

Coordinates of *P. tremuloides IspS*

| | | | | | | | | | | | |
|---|---|---|---|---|---|---|---|---|---|---|---|
| ATOM | 125 | O | SER | A | 25 | −76.635 | 8.581 | −16.724 | 1.00 | 38.15 | O |
| ATOM | 127 | N | ILE | A | 26 | −77.861 | 7.511 | −18.312 | 1.00 | 39.00 | N |
| ATOM | 128 | CA | ILE | A | 26 | −78.993 | 7.042 | −17.476 | 1.00 | 39.30 | C |
| ATOM | 130 | CB | ILE | A | 26 | −78.594 | 5.965 | −16.429 | 1.00 | 39.34 | C |
| ATOM | 132 | CG1 | ILE | A | 26 | −77.892 | 4.791 | −17.120 | 1.00 | 39.37 | C |
| ATOM | 135 | CD1 | ILE | A | 26 | −77.766 | 3.531 | −16.253 | 1.00 | 39.46 | C |
| ATOM | 139 | CG2 | ILE | A | 26 | −79.836 | 5.423 | −15.714 | 1.00 | 39.29 | C |
| ATOM | 143 | C | ILE | A | 26 | −79.716 | 8.260 | −16.852 | 1.00 | 39.66 | C |
| ATOM | 144 | O | ILE | A | 26 | −79.274 | 8.831 | −15.838 | 1.00 | 39.49 | O |
| ATOM | 146 | N | GLU | A | 27 | −80.837 | 8.623 | −17.486 | 1.00 | 39.99 | N |
| ATOM | 147 | CA | GLU | A | 27 | −81.450 | 9.965 | −17.383 | 1.00 | 40.11 | C |
| ATOM | 149 | CB | GLU | A | 27 | −82.395 | 10.183 | −18.587 | 1.00 | 40.19 | C |
| ATOM | 152 | CG | GLU | A | 27 | −81.632 | 10.311 | −19.904 | 1.00 | 40.60 | C |
| ATOM | 155 | CD | GLU | A | 27 | −82.528 | 10.434 | −21.116 | 1.00 | 41.06 | C |
| ATOM | 156 | OE1 | GLU | A | 27 | −83.328 | 9.502 | −21.367 | 1.00 | 41.10 | O |
| ATOM | 157 | OE2 | GLU | A | 27 | −82.409 | 11.458 | −21.830 | 1.00 | 41.36 | O |
| ATOM | 158 | C | GLU | A | 27 | −82.144 | 10.264 | −16.042 | 1.00 | 40.02 | C |
| ATOM | 159 | O | GLU | A | 27 | −81.977 | 9.518 | −15.071 | 1.00 | 40.01 | O |
| ATOM | 161 | N | VAL | A | 28 | −82.899 | 11.370 | −16.005 | 1.00 | 39.84 | N |
| ATOM | 162 | CA | VAL | A | 28 | −83.463 | 11.960 | −14.779 | 1.00 | 39.65 | C |
| ATOM | 164 | CB | VAL | A | 28 | −83.884 | 10.905 | −13.694 | 1.00 | 39.78 | C |
| ATOM | 166 | CG1 | VAL | A | 28 | −84.472 | 11.596 | −12.456 | 1.00 | 39.87 | C |
| ATOM | 170 | CG2 | VAL | A | 28 | −84.887 | 9.880 | −14.274 | 1.00 | 39.49 | C |
| ATOM | 174 | C | VAL | A | 28 | −82.469 | 12.980 | −14.206 | 1.00 | 39.46 | C |
| ATOM | 175 | O | VAL | A | 28 | −82.798 | 13.717 | −13.270 | 1.00 | 39.38 | O |
| ATOM | 177 | N | HIS | A | 29 | −81.264 | 13.025 | −14.786 | 1.00 | 39.30 | N |
| ATOM | 178 | CA | HIS | A | 29 | −80.236 | 14.006 | −14.412 | 1.00 | 39.23 | C |
| ATOM | 180 | CB | HIS | A | 29 | −78.866 | 13.344 | −14.186 | 1.00 | 39.45 | C |
| ATOM | 183 | CG | HIS | A | 29 | −78.910 | 12.139 | −13.296 | 1.00 | 41.29 | C |
| ATOM | 184 | ND1 | HIS | A | 29 | −78.407 | 12.140 | −12.007 | 1.00 | 42.51 | N |
| ATOM | 186 | CE1 | HIS | A | 29 | −78.585 | 10.942 | −11.472 | 1.00 | 43.37 | C |
| ATOM | 188 | NE2 | HIS | A | 29 | −79.181 | 10.164 | −12.365 | 1.00 | 43.18 | N |
| ATOM | 190 | CD2 | HIS | A | 29 | −79.393 | 10.888 | −13.515 | 1.00 | 42.55 | C |
| ATOM | 192 | C | HIS | A | 29 | −80.090 | 15.110 | −15.464 | 1.00 | 38.60 | C |
| ATOM | 193 | O | HIS | A | 29 | −79.049 | 15.774 | −15.499 | 1.00 | 38.61 | O |
| ATOM | 195 | N | LYS | A | 30 | −81.110 | 15.320 | −16.311 | 1.00 | 37.87 | N |
| ATOM | 196 | CA | LYS | A | 30 | −81.265 | 16.610 | −17.001 | 1.00 | 37.22 | C |
| ATOM | 198 | CB | LYS | A | 30 | −82.283 | 16.542 | −18.140 | 1.00 | 37.09 | C |
| ATOM | 201 | CG | LYS | A | 30 | −81.764 | 15.794 | −19.360 | 1.00 | 37.00 | C |
| ATOM | 204 | CD | LYS | A | 30 | −82.831 | 15.653 | −20.457 | 1.00 | 36.89 | C |
| ATOM | 207 | CE | LYS | A | 30 | −82.413 | 14.637 | −21.531 | 1.00 | 36.48 | C |
| ATOM | 210 | NZ | LYS | A | 30 | −83.422 | 14.458 | −22.611 | 1.00 | 35.46 | N |
| ATOM | 214 | C | LYS | A | 30 | −81.648 | 17.649 | −15.938 | 1.00 | 36.88 | C |
| ATOM | 215 | O | LYS | A | 30 | −82.516 | 18.499 | −16.136 | 1.00 | 36.71 | O |
| ATOM | 217 | N | ASP | A | 31 | −80.982 | 17.506 | −14.788 | 1.00 | 36.58 | N |
| ATOM | 218 | CA | ASP | A | 31 | −80.895 | 18.476 | −13.720 | 1.00 | 36.18 | C |
| ATOM | 220 | CB | ASP | A | 31 | −80.518 | 17.751 | −12.396 | 1.00 | 36.20 | C |
| ATOM | 223 | CG | ASP | A | 31 | −79.863 | 18.669 | −11.342 | 1.00 | 36.65 | C |
| ATOM | 224 | OD1 | ASP | A | 31 | −80.055 | 19.901 | −11.390 | 1.00 | 38.17 | O |
| ATOM | 225 | OD2 | ASP | A | 31 | −79.147 | 18.150 | −10.449 | 1.00 | 35.46 | O |
| ATOM | 226 | C | ASP | A | 31 | −79.811 | 19.426 | −14.226 | 1.00 | 35.74 | C |
| ATOM | 227 | O | ASP | A | 31 | −78.628 | 19.279 | −13.918 | 1.00 | 35.44 | O |
| ATOM | 229 | N | LYS | A | 32 | −80.220 | 20.343 | −15.096 | 1.00 | 35.30 | N |
| ATOM | 230 | CA | LYS | A | 32 | −79.360 | 21.449 | −15.507 | 1.00 | 34.69 | C |
| ATOM | 232 | CB | LYS | A | 32 | −78.698 | 21.188 | −16.849 | 1.00 | 34.63 | C |
| ATOM | 235 | CG | LYS | A | 32 | −77.699 | 20.042 | −16.765 | 1.00 | 34.51 | C |
| ATOM | 238 | CD | LYS | A | 32 | −76.953 | 19.853 | −18.078 | 1.00 | 34.48 | C |
| ATOM | 241 | CE | LYS | A | 32 | −76.859 | 18.387 | −18.503 | 1.00 | 33.77 | C |
| ATOM | 244 | NZ | LYS | A | 32 | −77.002 | 18.244 | −19.985 | 1.00 | 32.92 | N |
| ATOM | 248 | C | LYS | A | 32 | −80.162 | 22.745 | −15.459 | 1.00 | 34.01 | C |
| ATOM | 249 | O | LYS | A | 32 | −80.468 | 23.380 | −16.473 | 1.00 | 33.41 | O |
| ATOM | 251 | N | ALA | A | 33 | −80.540 | 23.051 | −14.219 | 1.00 | 33.21 | N |
| ATOM | 252 | CA | ALA | A | 33 | −80.785 | 24.381 | −13.766 | 1.00 | 32.60 | C |
| ATOM | 254 | CB | ALA | A | 33 | −81.619 | 24.347 | −12.484 | 1.00 | 32.28 | C |
| ATOM | 258 | C | ALA | A | 33 | −79.411 | 25.031 | −13.524 | 1.00 | 32.31 | C |
| ATOM | 259 | O | ALA | A | 33 | −79.335 | 26.081 | −12.901 | 1.00 | 32.80 | O |
| ATOM | 261 | N | LYS | A | 34 | −78.323 | 24.389 | −13.968 | 1.00 | 31.70 | N |
| ATOM | 262 | CA | LYS | A | 34 | −77.035 | 25.071 | −14.186 | 1.00 | 31.12 | C |
| ATOM | 264 | CB | LYS | A | 34 | −75.863 | 24.089 | −14.128 | 1.00 | 31.23 | C |
| ATOM | 267 | CG | LYS | A | 34 | −75.118 | 24.077 | −12.791 | 1.00 | 31.76 | C |
| ATOM | 270 | CD | LYS | A | 34 | −73.584 | 24.412 | −12.921 | 1.00 | 31.49 | C |
| ATOM | 273 | CE | LYS | A | 34 | −72.685 | 23.269 | −12.506 | 1.00 | 30.50 | C |
| ATOM | 276 | NZ | LYS | A | 34 | −72.951 | 22.090 | −13.348 | 1.00 | 29.53 | N |
| ATOM | 280 | C | LYS | A | 34 | −77.024 | 25.884 | −15.518 | 1.00 | 30.50 | C |
| ATOM | 281 | O | LYS | A | 34 | −76.977 | 25.353 | −16.625 | 1.00 | 29.82 | O |
| ATOM | 283 | N | LYS | A | 35 | −76.927 | 27.191 | −15.337 | 1.00 | 29.97 | N |
| ATOM | 284 | CA | LYS | A | 35 | −77.632 | 28.233 | −16.098 | 1.00 | 29.41 | C |
| ATOM | 286 | CB | LYS | A | 35 | −78.852 | 27.704 | −16.867 | 1.00 | 29.53 | C |

TABLE 3-7-continued

Coordinates of *P. tremuloides IspS*

| | | | | | | | | | | | |
|---|---|---|---|---|---|---|---|---|---|---|---|
| ATOM | 289 | CG | LYS | A | 35 | −80.166 | 27.594 | −16.077 | 1.00 | 30.18 | C |
| ATOM | 292 | CD | LYS | A | 35 | −81.030 | 28.858 | −16.203 | 1.00 | 31.25 | C |
| ATOM | 295 | CE | LYS | A | 35 | −82.375 | 28.721 | −15.486 | 1.00 | 31.85 | C |
| ATOM | 298 | NZ | LYS | A | 35 | −83.298 | 29.865 | −15.783 | 1.00 | 31.73 | N |
| ATOM | 302 | C | LYS | A | 35 | −78.053 | 29.277 | −15.026 | 1.00 | 28.53 | C |
| ATOM | 303 | O | LYS | A | 35 | −78.246 | 30.460 | −15.307 | 1.00 | 28.53 | O |
| ATOM | 305 | N | LEU | A | 36 | −78.225 | 28.791 | −13.796 | 1.00 | 27.29 | N |
| ATOM | 306 | CA | LEU | A | 36 | −77.998 | 29.576 | −12.594 | 1.00 | 26.21 | C |
| ATOM | 308 | CB | LEU | A | 36 | −78.088 | 28.679 | −11.364 | 1.00 | 25.76 | C |
| ATOM | 311 | CG | LEU | A | 36 | −79.468 | 28.350 | −10.832 | 1.00 | 24.08 | C |
| ATOM | 313 | CD1 | LEU | A | 36 | −79.376 | 27.233 | −9.836 | 1.00 | 22.16 | C |
| ATOM | 317 | CD2 | LEU | A | 36 | −80.051 | 29.586 | −10.213 | 1.00 | 23.45 | C |
| ATOM | 321 | C | LEU | A | 36 | −76.587 | 30.137 | −12.665 | 1.00 | 25.93 | C |
| ATOM | 322 | O | LEU | A | 36 | −76.290 | 31.221 | −12.137 | 1.00 | 26.11 | O |
| ATOM | 324 | N | GLU | A | 37 | −75.714 | 29.332 | −13.260 | 1.00 | 25.24 | N |
| ATOM | 325 | CA | GLU | A | 37 | −74.381 | 29.739 | −13.650 | 1.00 | 24.85 | C |
| ATOM | 327 | CB | GLU | A | 37 | −73.678 | 28.566 | −14.313 | 1.00 | 24.74 | C |
| ATOM | 330 | CG | GLU | A | 37 | −72.182 | 28.667 | −14.285 | 1.00 | 23.93 | C |
| ATOM | 333 | CD | GLU | A | 37 | −71.519 | 27.490 | −14.937 | 1.00 | 22.32 | C |
| ATOM | 334 | OE1 | GLU | A | 37 | −72.203 | 26.738 | −15.657 | 1.00 | 20.57 | O |
| ATOM | 335 | OE2 | GLU | A | 37 | −70.303 | 27.322 | −14.728 | 1.00 | 22.27 | O |
| ATOM | 336 | C | GLU | A | 37 | −74.391 | 30.927 | −14.600 | 1.00 | 24.69 | C |
| ATOM | 337 | O | GLU | A | 37 | −73.666 | 31.891 | −14.389 | 1.00 | 24.49 | O |
| ATOM | 339 | N | ALA | A | 38 | −75.203 | 30.850 | −15.650 | 1.00 | 24.68 | N |
| ATOM | 340 | CA | ALA | A | 38 | −75.352 | 31.960 | −16.599 | 1.00 | 24.87 | C |
| ATOM | 342 | CB | ALA | A | 38 | −76.453 | 31.656 | −17.609 | 1.00 | 24.53 | C |
| ATOM | 346 | C | ALA | A | 38 | −75.643 | 33.278 | −15.880 | 1.00 | 25.08 | C |
| ATOM | 347 | O | ALA | A | 38 | −75.009 | 34.295 | −16.135 | 1.00 | 25.21 | O |
| ATOM | 349 | N | GLU | A | 39 | −76.591 | 33.228 | −14.956 | 1.00 | 25.35 | N |
| ATOM | 350 | CA | GLU | A | 39 | −77.050 | 34.400 | −14.219 | 1.00 | 25.51 | C |
| ATOM | 352 | CB | GLU | A | 39 | −78.283 | 34.014 | −13.396 | 1.00 | 25.95 | C |
| ATOM | 355 | CG | GLU | A | 39 | −79.302 | 35.119 | −13.136 | 1.00 | 27.03 | C |
| ATOM | 358 | CD | GLU | A | 39 | −80.715 | 34.557 | −12.906 | 1.00 | 28.70 | C |
| ATOM | 359 | OE1 | GLU | A | 39 | −81.006 | 33.416 | −13.346 | 1.00 | 27.40 | O |
| ATOM | 360 | OE2 | GLU | A | 39 | −81.540 | 35.266 | −12.289 | 1.00 | 31.12 | O |
| ATOM | 361 | C | GLU | A | 39 | −75.970 | 34.966 | −13.306 | 1.00 | 25.11 | C |
| ATOM | 362 | O | GLU | A | 39 | −75.870 | 36.167 | −13.164 | 1.00 | 25.28 | O |
| ATOM | 364 | N | VAL | A | 40 | −75.182 | 34.107 | −12.672 | 1.00 | 24.86 | N |
| ATOM | 365 | CA | VAL | A | 40 | −74.079 | 34.568 | −11.824 | 1.00 | 24.69 | C |
| ATOM | 367 | CB | VAL | A | 40 | −73.511 | 33.420 | −10.952 | 1.00 | 24.56 | C |
| ATOM | 369 | CG1 | VAL | A | 40 | −72.239 | 33.857 | −10.240 | 1.00 | 23.69 | C |
| ATOM | 373 | CG2 | VAL | A | 40 | −74.553 | 32.955 | −9.955 | 1.00 | 24.68 | C |
| ATOM | 377 | C | VAL | A | 40 | −72.971 | 35.148 | −12.698 | 1.00 | 24.76 | C |
| ATOM | 378 | O | VAL | A | 40 | −72.337 | 36.139 | −12.362 | 1.00 | 24.16 | O |
| ATOM | 380 | N | ARG | A | 41 | −72.744 | 34.506 | −13.831 | 1.00 | 25.25 | N |
| ATOM | 381 | CA | ARG | A | 41 | −71.727 | 34.948 | −14.769 | 1.00 | 25.66 | C |
| ATOM | 383 | CB | ARG | A | 41 | −71.576 | 33.927 | −15.896 | 1.00 | 25.88 | C |
| ATOM | 386 | CG | ARG | A | 41 | −70.726 | 34.385 | −17.062 | 1.00 | 27.04 | C |
| ATOM | 389 | CD | ARG | A | 41 | −71.519 | 35.178 | −18.095 | 1.00 | 27.90 | C |
| ATOM | 392 | NE | ARG | A | 41 | −70.653 | 35.635 | −19.180 | 1.00 | 29.20 | N |
| ATOM | 394 | CZ | ARG | A | 41 | −70.946 | 36.615 | −20.034 | 1.00 | 29.94 | C |
| ATOM | 395 | NH1 | ARG | A | 41 | −70.077 | 36.945 | −20.980 | 1.00 | 29.86 | N |
| ATOM | 398 | NH2 | ARG | A | 41 | −72.096 | 37.273 | −19.957 | 1.00 | 30.54 | N |
| ATOM | 401 | C | ARG | A | 41 | −72.104 | 36.301 | −15.335 | 1.00 | 25.60 | C |
| ATOM | 402 | O | ARG | A | 41 | −71.237 | 37.113 | −15.612 | 1.00 | 25.77 | O |
| ATOM | 404 | N | ARG | A | 42 | −73.400 | 36.521 | −15.537 | 1.00 | 25.50 | N |
| ATOM | 405 | CA | ARG | A | 42 | −73.900 | 37.810 | −15.979 | 1.00 | 25.39 | C |
| ATOM | 407 | CB | ARG | A | 42 | −75.389 | 37.723 | −16.313 | 1.00 | 25.09 | C |
| ATOM | 410 | CG | ARG | A | 42 | −76.077 | 39.062 | −16.445 | 1.00 | 23.84 | C |
| ATOM | 413 | CD | ARG | A | 42 | −77.459 | 38.906 | −16.980 | 1.00 | 22.37 | C |
| ATOM | 416 | NE | ARG | A | 42 | −78.448 | 38.554 | −15.965 | 1.00 | 21.69 | N |
| ATOM | 418 | CZ | ARG | A | 42 | −79.705 | 38.206 | −16.248 | 1.00 | 22.99 | C |
| ATOM | 419 | NH1 | ARG | A | 42 | −80.122 | 38.146 | −17.517 | 1.00 | 24.16 | N |
| ATOM | 422 | NH2 | ARG | A | 42 | −80.557 | 37.900 | −15.275 | 1.00 | 22.94 | N |
| ATOM | 425 | C | ARG | A | 42 | −73.666 | 38.889 | −14.925 | 1.00 | 26.00 | C |
| ATOM | 426 | O | ARG | A | 42 | −73.173 | 39.959 | −15.244 | 1.00 | 26.17 | O |
| ATOM | 428 | N | GLU | A | 43 | −74.014 | 38.621 | −13.673 | 1.00 | 26.66 | N |
| ATOM | 429 | CA | GLU | A | 43 | −73.930 | 39.662 | −12.650 | 1.00 | 27.47 | C |
| ATOM | 431 | CB | GLU | A | 43 | −74.749 | 39.304 | −11.401 | 1.00 | 27.97 | C |
| ATOM | 434 | CG | GLU | A | 43 | −76.274 | 39.266 | −11.661 | 1.00 | 31.05 | C |
| ATOM | 437 | CD | GLU | A | 43 | −76.869 | 40.636 | −12.063 | 1.00 | 34.68 | C |
| ATOM | 438 | OE1 | GLU | A | 43 | −76.804 | 41.571 | −11.222 | 1.00 | 37.63 | O |
| ATOM | 439 | OE2 | GLU | A | 43 | −77.398 | 40.773 | −13.205 | 1.00 | 34.52 | O |
| ATOM | 440 | C | GLU | A | 43 | −72.494 | 40.035 | −12.275 | 1.00 | 27.15 | C |
| ATOM | 441 | O | GLU | A | 43 | −72.292 | 41.118 | −11.716 | 1.00 | 27.49 | O |
| ATOM | 443 | N | ILE | A | 44 | −71.517 | 39.166 | −12.588 | 1.00 | 26.57 | N |
| ATOM | 444 | CA | ILE | A | 44 | −70.090 | 39.456 | −12.334 | 1.00 | 25.80 | C |
| ATOM | 446 | CB | ILE | A | 44 | −69.206 | 38.187 | −12.187 | 1.00 | 25.52 | C |

TABLE 3-7-continued

| Coordinates of *P. tremuloides IspS* | | | | | | | | | | |
|---|---|---|---|---|---|---|---|---|---|---|
| ATOM | 448 | CG1 | ILE | A | 44 | −69.624 | 37.320 | −11.010 | 1.00 | 24.69 C |
| ATOM | 451 | CD1 | ILE | A | 44 | −68.828 | 36.061 | −10.899 | 1.00 | 23.08 C |
| ATOM | 455 | CG2 | ILE | A | 44 | −67.790 | 38.581 | −11.916 | 1.00 | 25.73 C |
| ATOM | 459 | C | ILE | A | 44 | −69.522 | 40.286 | −13.472 | 1.00 | 25.40 C |
| ATOM | 460 | O | ILE | A | 44 | −68.745 | 41.211 | −13.236 | 1.00 | 25.26 O |
| ATOM | 462 | N | ASN | A | 45 | −69.912 | 39.945 | −14.700 | 1.00 | 25.14 N |
| ATOM | 463 | CA | ASN | A | 45 | −69.480 | 40.669 | −15.906 | 1.00 | 25.02 C |
| ATOM | 465 | CB | ASN | A | 45 | −69.696 | 39.813 | −17.151 | 1.00 | 24.69 C |
| ATOM | 468 | CG | ASN | A | 45 | −68.662 | 38.735 | −17.302 | 1.00 | 24.01 C |
| ATOM | 469 | OD1 | ASN | A | 45 | −67.470 | 39.013 | −17.395 | 1.00 | 23.81 O |
| ATOM | 470 | ND2 | ASN | A | 45 | −69.111 | 37.490 | −17.344 | 1.00 | 23.28 N |
| ATOM | 473 | C | ASN | A | 45 | −70.177 | 42.014 | −16.114 | 1.00 | 25.52 C |
| ATOM | 474 | O | ASN | A | 45 | −69.704 | 42.836 | −16.890 | 1.00 | 25.40 O |
| ATOM | 476 | N | ASN | A | 46 | −71.308 | 42.210 | −15.437 | 1.00 | 26.33 N |
| ATOM | 477 | CA | ASN | A | 46 | −72.085 | 43.453 | −15.468 | 1.00 | 26.72 C |
| ATOM | 479 | CB | ASN | A | 46 | −73.102 | 43.404 | −14.322 | 1.00 | 26.31 C |
| ATOM | 482 | CG | ASN | A | 46 | −73.935 | 44.641 | −14.209 | 1.00 | 24.24 C |
| ATOM | 483 | OD1 | ASN | A | 46 | −73.948 | 45.472 | −15.091 | 1.00 | 22.38 O |
| ATOM | 484 | ND2 | ASN | A | 46 | −74.645 | 44.766 | −13.106 | 1.00 | 21.64 N |
| ATOM | 487 | C | ASN | A | 46 | −71.185 | 44.680 | −15.349 | 1.00 | 28.11 C |
| ATOM | 488 | O | ASN | A | 46 | −70.603 | 44.933 | −14.304 | 1.00 | 28.16 O |
| ATOM | 490 | N | GLU | A | 47 | −71.084 | 45.441 | −16.433 | 1.00 | 29.93 N |
| ATOM | 491 | CA | GLU | A | 47 | −70.128 | 46.558 | −16.544 | 1.00 | 31.30 C |
| ATOM | 493 | CB | GLU | A | 47 | −69.933 | 46.969 | −18.013 | 1.00 | 31.28 C |
| ATOM | 496 | CG | GLU | A | 47 | −69.737 | 45.795 | −19.020 | 1.00 | 32.37 C |
| ATOM | 499 | CD | GLU | A | 47 | −71.060 | 45.127 | −19.545 | 1.00 | 32.69 C |
| ATOM | 500 | OE1 | GLU | A | 47 | −72.055 | 45.833 | −19.816 | 1.00 | 32.16 O |
| ATOM | 501 | OE2 | GLU | A | 47 | −71.087 | 43.880 | −19.699 | 1.00 | 32.41 O |
| ATOM | 502 | C | GLU | A | 47 | −70.582 | 47.774 | −15.729 | 1.00 | 32.47 C |
| ATOM | 503 | O | GLU | A | 47 | −69.760 | 48.525 | −15.230 | 1.00 | 32.86 O |
| ATOM | 505 | N | LYS | A | 48 | −71.898 | 47.945 | −15.585 | 1.00 | 33.93 N |
| ATOM | 506 | CA | LYS | A | 48 | −72.491 | 49.075 | −14.861 | 1.00 | 34.85 C |
| ATOM | 508 | CB | LYS | A | 48 | −73.660 | 49.672 | −15.684 | 1.00 | 35.08 C |
| ATOM | 511 | CG | LYS | A | 48 | −73.221 | 50.119 | −17.126 | 1.00 | 36.58 C |
| ATOM | 514 | CD | LYS | A | 48 | −74.035 | 51.277 | −17.751 | 1.00 | 37.93 C |
| ATOM | 517 | CE | LYS | A | 48 | −75.353 | 50.799 | −18.415 | 1.00 | 39.02 C |
| ATOM | 520 | NZ | LYS | A | 48 | −75.159 | 49.990 | −19.669 | 1.00 | 39.11 N |
| ATOM | 524 | C | LYS | A | 48 | −72.926 | 48.632 | −13.465 | 1.00 | 35.26 C |
| ATOM | 525 | O | LYS | A | 48 | −74.011 | 48.954 | −13.015 | 1.00 | 35.04 O |
| ATOM | 527 | N | ALA | A | 49 | −72.051 | 47.890 | −12.790 | 1.00 | 36.29 N |
| ATOM | 528 | CA | ALA | A | 49 | −72.321 | 47.348 | −11.456 | 1.00 | 37.18 C |
| ATOM | 530 | CB | ALA | A | 49 | −71.828 | 45.923 | −11.353 | 1.00 | 37.20 C |
| ATOM | 534 | C | ALA | A | 49 | −71.618 | 48.191 | −10.418 | 1.00 | 37.88 C |
| ATOM | 535 | O | ALA | A | 49 | −70.480 | 48.610 | −10.638 | 1.00 | 38.17 O |
| ATOM | 537 | N | GLU | A | 50 | −72.278 | 48.404 | −9.280 | 1.00 | 38.53 N |
| ATOM | 538 | CA | GLU | A | 50 | −71.730 | 49.242 | −8.213 | 1.00 | 39.08 C |
| ATOM | 540 | CB | GLU | A | 50 | −72.790 | 49.545 | −7.146 | 1.00 | 39.43 C |
| ATOM | 543 | CG | GLU | A | 50 | −72.708 | 50.953 | −6.600 | 1.00 | 40.86 C |
| ATOM | 546 | CD | GLU | A | 50 | −73.089 | 52.010 | −7.639 | 1.00 | 42.77 C |
| ATOM | 547 | OE1 | GLU | A | 50 | −74.225 | 52.530 | −7.570 | 1.00 | 45.07 O |
| ATOM | 548 | OE2 | GLU | A | 50 | −72.265 | 52.320 | −8.530 | 1.00 | 43.35 O |
| ATOM | 549 | C | GLU | A | 50 | −70.560 | 48.521 | −7.600 | 1.00 | 38.89 C |
| ATOM | 550 | O | GLU | A | 50 | −70.699 | 47.378 | −7.201 | 1.00 | 39.05 O |
| ATOM | 552 | N | PHE | A | 51 | −69.411 | 49.181 | −7.536 | 1.00 | 38.99 N |
| ATOM | 553 | CA | PHE | A | 51 | −68.161 | 48.502 | −7.196 | 1.00 | 39.52 C |
| ATOM | 555 | CB | PHE | A | 51 | −67.000 | 49.494 | −7.098 | 1.00 | 40.05 C |
| ATOM | 558 | CG | PHE | A | 51 | −66.460 | 49.948 | −8.431 | 1.00 | 42.80 C |
| ATOM | 559 | CD1 | PHE | A | 51 | −66.135 | 49.014 | −9.435 | 1.00 | 45.21 C |
| ATOM | 561 | CE1 | PHE | A | 51 | −65.612 | 49.425 | −10.675 | 1.00 | 46.12 C |
| ATOM | 563 | CZ | PHE | A | 51 | −65.403 | 50.790 | −10.917 | 1.00 | 47.21 C |
| ATOM | 565 | CE2 | PHE | A | 51 | −65.726 | 51.741 | −9.913 | 1.00 | 46.72 C |
| ATOM | 567 | CD2 | PHE | A | 51 | −66.247 | 51.310 | −8.679 | 1.00 | 45.05 C |
| ATOM | 569 | C | PHE | A | 51 | −68.223 | 47.687 | −5.905 | 1.00 | 39.05 C |
| ATOM | 570 | O | PHE | A | 51 | −67.897 | 46.506 | −5.900 | 1.00 | 39.28 O |
| ATOM | 572 | N | LEU | A | 52 | −68.648 | 48.307 | −4.813 | 1.00 | 38.42 N |
| ATOM | 573 | CA | LEU | A | 52 | −68.709 | 47.610 | −3.528 | 1.00 | 37.94 C |
| ATOM | 575 | CB | LEU | A | 52 | −69.084 | 48.594 | −2.413 | 1.00 | 38.53 C |
| ATOM | 578 | CG | LEU | A | 52 | −68.057 | 49.726 | −2.181 | 1.00 | 40.46 C |
| ATOM | 580 | CD1 | LEU | A | 52 | −68.691 | 51.101 | −1.787 | 1.00 | 41.88 C |
| ATOM | 584 | CD2 | LEU | A | 52 | −67.020 | 49.274 | −1.141 | 1.00 | 41.83 C |
| ATOM | 588 | C | LEU | A | 52 | −69.667 | 46.406 | −3.532 | 1.00 | 36.72 C |
| ATOM | 589 | O | LEU | A | 52 | −69.517 | 45.494 | −2.724 | 1.00 | 36.84 O |
| ATOM | 591 | N | THR | A | 53 | −70.649 | 46.398 | −4.431 | 1.00 | 35.37 N |
| ATOM | 592 | CA | THR | A | 53 | −71.545 | 45.247 | −4.569 | 1.00 | 34.11 C |
| ATOM | 594 | CB | THR | A | 53 | −72.867 | 45.594 | −5.277 | 1.00 | 33.87 C |
| ATOM | 596 | OG1 | THR | A | 53 | −73.339 | 46.863 | −4.828 | 1.00 | 33.49 O |
| ATOM | 598 | CG2 | THR | A | 53 | −73.917 | 44.535 | −4.983 | 1.00 | 33.70 C |
| ATOM | 602 | C | THR | A | 53 | −70.853 | 44.148 | −5.359 | 1.00 | 33.04 C |

TABLE 3-7-continued

Coordinates of *P. tremuloides IspS*

| | | | | | | | | | | | |
|---|---|---|---|---|---|---|---|---|---|---|---|
| ATOM | 603 | O | THR | A | 53 | −70.893 | 42.977 | −4.973 | 1.00 | 32.90 | O |
| ATOM | 605 | N | LEU | A | 54 | −70.228 | 44.528 | −6.467 | 1.00 | 31.76 | N |
| ATOM | 606 | CA | LEU | A | 54 | −69.469 | 43.578 | −7.286 | 1.00 | 31.13 | C |
| ATOM | 608 | CB | LEU | A | 54 | −68.721 | 44.308 | −8.392 | 1.00 | 30.92 | C |
| ATOM | 611 | CG | LEU | A | 54 | −68.028 | 43.437 | −9.424 | 1.00 | 30.27 | C |
| ATOM | 613 | CD1 | LEU | A | 54 | −69.034 | 42.769 | −10.310 | 1.00 | 29.56 | C |
| ATOM | 617 | CD2 | LEU | A | 54 | −67.108 | 44.306 | −10.242 | 1.00 | 31.15 | C |
| ATOM | 621 | C | LEU | A | 54 | −68.466 | 42.808 | −6.443 | 1.00 | 30.60 | C |
| ATOM | 622 | O | LEU | A | 54 | −68.378 | 41.587 | −6.543 | 1.00 | 30.30 | O |
| ATOM | 624 | N | LEU | A | 55 | −67.725 | 43.551 | −5.618 | 1.00 | 30.09 | N |
| ATOM | 625 | CA | LEU | A | 55 | −66.730 | 43.000 | −4.695 | 1.00 | 29.47 | C |
| ATOM | 627 | CB | LEU | A | 55 | −66.006 | 44.126 | −3.944 | 1.00 | 29.44 | C |
| ATOM | 630 | CG | LEU | A | 55 | −65.069 | 45.017 | −4.781 | 1.00 | 29.74 | C |
| ATOM | 632 | CD1 | LEU | A | 55 | −64.609 | 46.255 | −4.003 | 1.00 | 29.43 | C |
| ATOM | 636 | CD2 | LEU | A | 55 | −63.859 | 44.234 | −5.286 | 1.00 | 29.64 | C |
| ATOM | 640 | C | LEU | A | 55 | −67.340 | 42.024 | −3.696 | 1.00 | 28.87 | C |
| ATOM | 641 | O | LEU | A | 55 | −66.746 | 40.991 | −3.383 | 1.00 | 28.98 | O |
| ATOM | 643 | N | GLU | A | 56 | −68.525 | 42.330 | −3.198 | 1.00 | 28.01 | N |
| ATOM | 644 | CA | GLU | A | 56 | −69.160 | 41.419 | −2.256 | 1.00 | 27.64 | C |
| ATOM | 646 | CB | GLU | A | 56 | −70.172 | 42.173 | −1.395 | 1.00 | 28.19 | C |
| ATOM | 649 | CG | GLU | A | 56 | −69.497 | 43.167 | −.459 | 1.00 | 29.75 | C |
| ATOM | 652 | CD | GLU | A | 56 | −70.457 | 43.858 | .478 | 1.00 | 33.04 | C |
| ATOM | 653 | OE1 | GLU | A | 56 | −71.667 | 43.538 | .481 | 1.00 | 34.46 | O |
| ATOM | 654 | OE2 | GLU | A | 56 | −69.988 | 44.737 | 1.226 | 1.00 | 36.78 | O |
| ATOM | 655 | C | GLU | A | 56 | −69.776 | 40.200 | −2.945 | 1.00 | 26.37 | C |
| ATOM | 656 | O | GLU | A | 56 | −69.914 | 39.146 | −2.333 | 1.00 | 26.02 | O |
| ATOM | 658 | N | LEU | A | 57 | −70.134 | 40.347 | −4.218 | 1.00 | 25.30 | N |
| ATOM | 659 | CA | LEU | A | 57 | −70.569 | 39.212 | −5.036 | 1.00 | 24.17 | C |
| ATOM | 661 | CB | LEU | A | 57 | −71.125 | 39.680 | −6.382 | 1.00 | 23.71 | C |
| ATOM | 664 | CG | LEU | A | 57 | −71.417 | 38.568 | −7.390 | 1.00 | 22.27 | C |
| ATOM | 666 | CD1 | LEU | A | 57 | −72.515 | 37.675 | −6.858 | 1.00 | 19.31 | C |
| ATOM | 670 | CD2 | LEU | A | 57 | −71.752 | 39.167 | −8.768 | 1.00 | 20.30 | C |
| ATOM | 674 | C | LEU | A | 57 | −69.404 | 38.267 | −5.284 | 1.00 | 23.69 | C |
| ATOM | 675 | O | LEU | A | 57 | −69.547 | 37.051 | −5.136 | 1.00 | 23.83 | O |
| ATOM | 677 | N | ILE | A | 58 | −68.261 | 38.822 | −5.682 | 1.00 | 22.82 | N |
| ATOM | 678 | CA | ILE | A | 58 | −67.070 | 38.019 | −5.925 | 1.00 | 22.39 | C |
| ATOM | 680 | CB | ILE | A | 58 | −65.884 | 38.899 | −6.355 | 1.00 | 22.21 | C |
| ATOM | 682 | CG1 | ILE | A | 58 | −66.088 | 39.386 | −7.792 | 1.00 | 21.83 | C |
| ATOM | 685 | CD1 | ILE | A | 58 | −65.002 | 40.314 | −8.320 | 1.00 | 20.43 | C |
| ATOM | 689 | CG2 | ILE | A | 58 | −64.565 | 38.131 | −6.245 | 1.00 | 22.64 | C |
| ATOM | 693 | C | ILE | A | 58 | −66.719 | 37.227 | −4.662 | 1.00 | 22.35 | C |
| ATOM | 694 | O | ILE | A | 58 | −66.520 | 36.002 | −4.706 | 1.00 | 21.95 | O |
| ATOM | 696 | N | ASP | A | 59 | −66.676 | 37.951 | −3.543 | 1.00 | 22.32 | N |
| ATOM | 697 | CA | ASP | A | 59 | −66.396 | 37.396 | −2.215 | 1.00 | 22.26 | C |
| ATOM | 699 | CB | ASP | A | 59 | −66.570 | 38.500 | −1.171 | 1.00 | 22.67 | C |
| ATOM | 702 | CG | ASP | A | 59 | −66.126 | 38.092 | .213 | 1.00 | 23.91 | C |
| ATOM | 703 | OD1 | ASP | A | 59 | −65.271 | 37.182 | .338 | 1.00 | 23.77 | O |
| ATOM | 704 | OD2 | ASP | A | 59 | −66.641 | 38.718 | 1.178 | 1.00 | 27.12 | O |
| ATOM | 705 | C | ASP | A | 59 | −67.304 | 36.216 | −1.901 | 1.00 | 21.79 | C |
| ATOM | 706 | O | ASP | A | 59 | −66.828 | 35.102 | −1.668 | 1.00 | 21.71 | O |
| ATOM | 708 | N | ASN | A | 60 | −68.610 | 36.466 | −1.926 | 1.00 | 21.51 | N |
| ATOM | 709 | CA | ASN | A | 60 | −69.619 | 35.418 | −1.759 | 1.00 | 21.28 | C |
| ATOM | 711 | CB | ASN | A | 60 | −71.012 | 36.006 | −1.958 | 1.00 | 21.25 | C |
| ATOM | 714 | CG | ASN | A | 60 | −71.476 | 36.827 | −.776 | 1.00 | 21.82 | C |
| ATOM | 715 | OD1 | ASN | A | 60 | −71.067 | 36.598 | .364 | 1.00 | 20.81 | O |
| ATOM | 716 | ND2 | ASN | A | 60 | −72.361 | 37.783 | −1.043 | 1.00 | 23.63 | N |
| ATOM | 719 | C | ASN | A | 60 | −69.445 | 34.240 | −2.725 | 1.00 | 21.22 | C |
| ATOM | 720 | O | ASN | A | 60 | −69.444 | 33.053 | −2.303 | 1.00 | 20.95 | O |
| ATOM | 722 | N | VAL | A | 61 | −69.308 | 34.566 | −4.018 | 1.00 | 20.83 | N |
| ATOM | 723 | CA | VAL | A | 61 | −69.147 | 33.536 | −5.043 | 1.00 | 20.57 | C |
| ATOM | 725 | CB | VAL | A | 61 | −68.915 | 34.122 | −6.466 | 1.00 | 20.53 | C |
| ATOM | 727 | CG1 | VAL | A | 61 | −68.382 | 33.042 | −7.430 | 1.00 | 19.44 | C |
| ATOM | 731 | CG2 | VAL | A | 61 | −70.190 | 34.758 | −7.006 | 1.00 | 19.75 | C |
| ATOM | 735 | C | VAL | A | 61 | −67.981 | 32.646 | −4.644 | 1.00 | 20.62 | C |
| ATOM | 736 | O | VAL | A | 61 | −68.080 | 31.431 | −4.699 | 1.00 | 20.56 | O |
| ATOM | 738 | N | GLN | A | 62 | −66.888 | 33.255 | −4.209 | 1.00 | 20.76 | N |
| ATOM | 739 | CA | GLN | A | 62 | −65.703 | 32.481 | −3.898 | 1.00 | 21.18 | C |
| ATOM | 741 | CB | GLN | A | 62 | −64.461 | 33.379 | −3.824 | 1.00 | 21.39 | C |
| ATOM | 744 | CG | GLN | A | 62 | −64.007 | 33.920 | −5.165 | 1.00 | 21.64 | C |
| ATOM | 747 | CD | GLN | A | 62 | −62.608 | 34.512 | −5.135 | 1.00 | 22.04 | C |
| ATOM | 748 | OE1 | GLN | A | 62 | −61.890 | 34.483 | −6.145 | 1.00 | 23.18 | O |
| ATOM | 749 | NE2 | GLN | A | 62 | −62.217 | 35.062 | −3.989 | 1.00 | 20.39 | N |
| ATOM | 752 | C | GLN | A | 62 | −65.891 | 31.681 | −2.607 | 1.00 | 21.09 | C |
| ATOM | 753 | O | GLN | A | 62 | −65.544 | 30.485 | −2.554 | 1.00 | 21.30 | O |
| ATOM | 755 | N | ARG | A | 63 | −66.448 | 32.325 | −1.583 | 1.00 | 20.63 | N |
| ATOM | 756 | CA | ARG | A | 63 | −66.590 | 31.677 | −.273 | 1.00 | 20.54 | C |
| ATOM | 758 | CB | ARG | A | 63 | −67.025 | 32.686 | .786 | 1.00 | 20.57 | C |
| ATOM | 761 | CG | ARG | A | 63 | −66.031 | 33.823 | .930 | 1.00 | 22.55 | C |

TABLE 3-7-continued

Coordinates of *P. tremuloides IspS*

| | | | | | | | | | | | |
|---|---|---|---|---|---|---|---|---|---|---|---|
| ATOM | 764 | CD | ARG | A | 63 | −66.214 | 34.632 | 2.179 | 1.00 | 24.93 | C |
| ATOM | 767 | NE | ARG | A | 63 | −66.123 | 33.781 | 3.355 | 1.00 | 27.75 | N |
| ATOM | 769 | CZ | ARG | A | 63 | −66.496 | 34.151 | 4.573 | 1.00 | 30.24 | C |
| ATOM | 770 | NH1 | ARG | A | 63 | −66.971 | 35.385 | 4.782 | 1.00 | 31.79 | N |
| ATOM | 773 | NH2 | ARG | A | 63 | −66.399 | 33.285 | 5.581 | 1.00 | 30.07 | N |
| ATOM | 776 | C | ARG | A | 63 | −67.557 | 30.499 | −.338 | 1.00 | 19.81 | C |
| ATOM | 777 | O | ARG | A | 63 | −67.283 | 29.431 | .209 | 1.00 | 19.67 | O |
| ATOM | 779 | N | LEU | A | 64 | −68.661 | 30.684 | −1.057 | 1.00 | 19.04 | N |
| ATOM | 780 | CA | LEU | A | 64 | −69.636 | 29.617 | −1.246 | 1.00 | 18.44 | C |
| ATOM | 782 | CB | LEU | A | 64 | −70.865 | 30.167 | −1.954 | 1.00 | 18.59 | C |
| ATOM | 785 | CG | LEU | A | 64 | −71.662 | 31.170 | −1.140 | 1.00 | 18.32 | C |
| ATOM | 787 | CD1 | LEU | A | 64 | −72.669 | 31.852 | −2.034 | 1.00 | 18.10 | C |
| ATOM | 791 | CD2 | LEU | A | 64 | −72.334 | 30.444 | .004 | 1.00 | 18.29 | C |
| ATOM | 795 | C | LEU | A | 64 | −69.089 | 28.436 | −2.037 | 1.00 | 17.80 | C |
| ATOM | 796 | O | LEU | A | 64 | −69.802 | 27.453 | −2.252 | 1.00 | 17.79 | O |
| ATOM | 798 | N | GLY | A | 65 | −67.850 | 28.573 | −2.515 | 1.00 | 17.07 | N |
| ATOM | 799 | CA | GLY | A | 65 | −67.084 | 27.480 | −3.081 | 1.00 | 16.27 | C |
| ATOM | 802 | C | GLY | A | 65 | −67.137 | 27.406 | −4.588 | 1.00 | 15.77 | C |
| ATOM | 803 | O | GLY | A | 65 | −66.893 | 26.347 | −5.154 | 1.00 | 15.78 | O |
| ATOM | 805 | N | LEU | A | 66 | −67.439 | 28.521 | −5.246 | 1.00 | 15.24 | N |
| ATOM | 806 | CA | LEU | A | 66 | −67.621 | 28.537 | −6.701 | 1.00 | 14.93 | C |
| ATOM | 808 | CB | LEU | A | 66 | −68.977 | 29.146 | −7.021 | 1.00 | 14.84 | C |
| ATOM | 811 | CG | LEU | A | 66 | −70.204 | 28.334 | −6.619 | 1.00 | 13.97 | C |
| ATOM | 813 | CD1 | LEU | A | 66 | −71.391 | 29.260 | −6.650 | 1.00 | 13.74 | C |
| ATOM | 817 | CD2 | LEU | A | 66 | −70.415 | 27.125 | −7.534 | 1.00 | 11.22 | C |
| ATOM | 821 | C | LEU | A | 66 | −66.533 | 29.314 | −7.454 | 1.00 | 15.09 | C |
| ATOM | 822 | O | LEU | A | 66 | −66.621 | 29.497 | −8.678 | 1.00 | 14.81 | O |
| ATOM | 824 | N | GLY | A | 67 | −65.510 | 29.758 | −6.720 | 1.00 | 15.21 | N |
| ATOM | 825 | CA | GLY | A | 67 | −64.404 | 30.526 | −7.280 | 1.00 | 14.98 | C |
| ATOM | 828 | C | GLY | A | 67 | −63.873 | 29.952 | −8.569 | 1.00 | 14.60 | C |
| ATOM | 829 | O | GLY | A | 67 | −63.891 | 30.619 | −9.579 | 1.00 | 14.63 | O |
| ATOM | 831 | N | TYR | A | 68 | −63.419 | 28.706 | −8.523 | 1.00 | 14.57 | N |
| ATOM | 832 | CA | TYR | A | 68 | −62.831 | 28.029 | −9.688 | 1.00 | 14.72 | C |
| ATOM | 834 | CB | TYR | A | 68 | −62.608 | 26.539 | −9.372 | 1.00 | 14.73 | C |
| ATOM | 837 | CG | TYR | A | 68 | −63.858 | 25.689 | −9.330 | 1.00 | 12.47 | C |
| ATOM | 838 | CD1 | TYR | A | 68 | −64.163 | 24.826 | −10.366 | 1.00 | 10.68 | C |
| ATOM | 840 | CE1 | TYR | A | 68 | −65.310 | 24.043 | −10.340 | 1.00 | 10.55 | C |
| ATOM | 842 | CZ | TYR | A | 68 | −66.163 | 24.119 | −9.258 | 1.00 | 10.41 | C |
| ATOM | 843 | OH | TYR | A | 68 | −67.311 | 23.349 | −9.212 | 1.00 | 6.97 | O |
| ATOM | 845 | CE2 | TYR | A | 68 | −65.864 | 24.979 | −8.210 | 1.00 | 11.44 | C |
| ATOM | 847 | CD2 | TYR | A | 68 | −64.722 | 25.750 | −8.252 | 1.00 | 11.29 | C |
| ATOM | 849 | C | TYR | A | 68 | −63.648 | 28.141 | −10.980 | 1.00 | 15.31 | C |
| ATOM | 850 | O | TYR | A | 68 | −63.106 | 28.230 | −12.083 | 1.00 | 15.01 | O |
| ATOM | 852 | N | ARG | A | 69 | −64.959 | 28.136 | −10.816 | 1.00 | 16.03 | N |
| ATOM | 853 | CA | ARG | A | 69 | −65.884 | 28.083 | −11.922 | 1.00 | 16.67 | C |
| ATOM | 855 | CB | ARG | A | 69 | −67.224 | 27.649 | −11.348 | 1.00 | 16.58 | C |
| ATOM | 858 | CG | ARG | A | 69 | −68.332 | 27.445 | −12.335 | 1.00 | 16.07 | C |
| ATOM | 861 | CD | ARG | A | 69 | −69.378 | 26.578 | −11.701 | 1.00 | 14.26 | C |
| ATOM | 864 | NE | ARG | A | 69 | −68.915 | 25.205 | −11.677 | 1.00 | 12.82 | N |
| ATOM | 866 | CZ | ARG | A | 69 | −69.063 | 24.346 | −12.676 | 1.00 | 12.42 | C |
| ATOM | 867 | NH1 | ARG | A | 69 | −69.676 | 24.694 | −13.792 | 1.00 | 12.27 | N |
| ATOM | 870 | NH2 | ARG | A | 69 | −68.601 | 23.119 | −12.553 | 1.00 | 13.23 | N |
| ATOM | 873 | C | ARG | A | 69 | −66.010 | 29.409 | −12.692 | 1.00 | 17.62 | C |
| ATOM | 874 | O | ARG | A | 69 | −66.281 | 29.401 | −13.892 | 1.00 | 17.10 | O |
| ATOM | 876 | N | PHE | A | 70 | −65.811 | 30.529 | −11.985 | 1.00 | 19.11 | N |
| ATOM | 877 | CA | PHE | A | 70 | −65.936 | 31.891 | −12.530 | 1.00 | 19.96 | C |
| ATOM | 879 | CB | PHE | A | 70 | −67.024 | 32.666 | −11.763 | 1.00 | 19.89 | C |
| ATOM | 882 | CG | PHE | A | 70 | −68.365 | 32.010 | −11.784 | 1.00 | 18.68 | C |
| ATOM | 883 | CD1 | PHE | A | 70 | −69.158 | 32.082 | −12.903 | 1.00 | 18.05 | C |
| ATOM | 885 | CE1 | PHE | A | 70 | −70.376 | 31.452 | −12.938 | 1.00 | 18.03 | C |
| ATOM | 887 | CZ | PHE | A | 70 | −70.825 | 30.754 | −11.851 | 1.00 | 17.26 | C |
| ATOM | 889 | CE2 | PHE | A | 70 | −70.051 | 30.672 | −10.736 | 1.00 | 17.60 | C |
| ATOM | 891 | CD2 | PHE | A | 70 | −68.822 | 31.300 | −10.700 | 1.00 | 17.86 | C |
| ATOM | 893 | C | PHE | A | 70 | −64.627 | 32.661 | −12.400 | 1.00 | 21.34 | C |
| ATOM | 894 | O | PHE | A | 70 | −64.629 | 33.862 | −12.171 | 1.00 | 21.25 | O |
| ATOM | 896 | N | GLU | A | 71 | −63.501 | 31.977 | −12.541 | 1.00 | 23.19 | N |
| ATOM | 897 | CA | GLU | A | 71 | −62.211 | 32.591 | −12.214 | 1.00 | 24.60 | C |
| ATOM | 899 | CB | GLU | A | 71 | −61.127 | 31.524 | −12.073 | 1.00 | 25.03 | C |
| ATOM | 902 | CG | GLU | A | 71 | −59.717 | 32.059 | −11.861 | 1.00 | 27.10 | C |
| ATOM | 905 | CD | GLU | A | 71 | −58.712 | 30.949 | −11.549 | 1.00 | 30.10 | C |
| ATOM | 906 | OE1 | GLU | A | 71 | −59.084 | 30.007 | −10.796 | 1.00 | 32.05 | O |
| ATOM | 907 | OE2 | GLU | A | 71 | −57.558 | 31.027 | −12.051 | 1.00 | 30.50 | O |
| ATOM | 908 | C | GLU | A | 71 | −61.809 | 33.644 | −13.241 | 1.00 | 25.23 | C |
| ATOM | 909 | O | GLU | A | 71 | −61.362 | 34.717 | −12.862 | 1.00 | 25.54 | O |
| ATOM | 911 | N | SER | A | 72 | −61.979 | 33.345 | −14.530 | 1.00 | 25.91 | N |
| ATOM | 912 | CA | SER | A | 72 | −61.641 | 34.294 | −15.588 | 1.00 | 26.37 | C |
| ATOM | 914 | CB | SER | A | 72 | −61.656 | 33.606 | −16.941 | 1.00 | 26.32 | C |
| ATOM | 917 | OG | SER | A | 72 | −62.985 | 33.278 | −17.291 | 1.00 | 27.28 | O |

TABLE 3-7-continued

Coordinates of *P. tremuloides IspS*

| | | | | | | | | | | | |
|---|---|---|---|---|---|---|---|---|---|---|---|
| ATOM | 919 | C | SER | A | 72 | −62.609 | 35.476 | −15.608 | 1.00 | 26.84 | C |
| ATOM | 920 | O | SER | A | 72 | −62.197 | 36.601 | −15.852 | 1.00 | 27.02 | O |
| ATOM | 922 | N | ASP | A | 73 | −63.893 | 35.214 | −15.361 | 1.00 | 27.45 | N |
| ATOM | 923 | CA | ASP | A | 73 | −64.895 | 36.277 | −15.246 | 1.00 | 27.87 | C |
| ATOM | 925 | CB | ASP | A | 73 | −66.289 | 35.705 | −14.968 | 1.00 | 27.99 | C |
| ATOM | 928 | CG | ASP | A | 73 | −66.842 | 34.913 | −16.140 | 1.00 | 29.49 | C |
| ATOM | 929 | OD1 | ASP | A | 73 | −67.215 | 35.530 | −17.155 | 1.00 | 30.90 | O |
| ATOM | 930 | OD2 | ASP | A | 73 | −66.916 | 33.667 | −16.054 | 1.00 | 31.85 | O |
| ATOM | 931 | C | ASP | A | 73 | −64.518 | 37.221 | −14.121 | 1.00 | 27.86 | C |
| ATOM | 932 | O | ASP | A | 73 | −64.598 | 38.435 | −14.286 | 1.00 | 28.05 | O |
| ATOM | 934 | N | ILE | A | 74 | −64.118 | 36.652 | −12.985 | 1.00 | 27.88 | N |
| ATOM | 935 | CA | ILE | A | 74 | −63.698 | 37.422 | −11.821 | 1.00 | 27.98 | C |
| ATOM | 937 | CB | ILE | A | 74 | −63.348 | 36.521 | −10.637 | 1.00 | 27.71 | C |
| ATOM | 939 | CG1 | ILE | A | 74 | −64.607 | 36.007 | −9.960 | 1.00 | 27.60 | C |
| ATOM | 942 | CD1 | ILE | A | 74 | −64.355 | 34.846 | −9.023 | 1.00 | 27.67 | C |
| ATOM | 946 | CG2 | ILE | A | 74 | −62.551 | 37.272 | −9.621 | 1.00 | 26.82 | C |
| ATOM | 950 | C | ILE | A | 74 | −62.472 | 38.252 | −12.133 | 1.00 | 28.80 | C |
| ATOM | 951 | O | ILE | A | 74 | −62.475 | 39.453 | −11.917 | 1.00 | 29.00 | O |
| ATOM | 953 | N | ARG | A | 75 | −61.415 | 37.616 | −12.628 | 1.00 | 29.80 | N |
| ATOM | 954 | CA | ARG | A | 75 | −60.197 | 38.341 | −12.968 | 1.00 | 30.79 | C |
| ATOM | 956 | CB | ARG | A | 75 | −59.286 | 37.507 | −13.841 | 1.00 | 31.33 | C |
| ATOM | 959 | CG | ARG | A | 75 | −58.506 | 36.441 | −13.115 | 1.00 | 34.25 | C |
| ATOM | 962 | CD | ARG | A | 75 | −57.286 | 36.009 | −13.929 | 1.00 | 37.53 | C |
| ATOM | 965 | NE | ARG | A | 75 | −56.238 | 37.019 | −13.799 | 1.00 | 40.89 | N |
| ATOM | 967 | CZ | ARG | A | 75 | −54.934 | 36.807 | −13.967 | 1.00 | 44.24 | C |
| ATOM | 968 | NH1 | ARG | A | 75 | −54.459 | 35.602 | −14.294 | 1.00 | 45.02 | N |
| ATOM | 971 | NH2 | ARG | A | 75 | −54.089 | 37.821 | −13.796 | 1.00 | 45.88 | N |
| ATOM | 974 | C | ARG | A | 75 | −60.548 | 39.596 | −13.727 | 1.00 | 30.95 | C |
| ATOM | 975 | O | ARG | A | 75 | −60.163 | 40.685 | −13.336 | 1.00 | 31.27 | O |
| ATOM | 977 | N | ARG | A | 76 | −61.293 | 39.435 | −14.815 | 1.00 | 31.31 | N |
| ATOM | 978 | CA | ARG | A | 76 | −61.712 | 40.567 | −15.638 | 1.00 | 31.62 | C |
| ATOM | 980 | CB | ARG | A | 76 | −62.593 | 40.106 | −16.794 | 1.00 | 31.97 | C |
| ATOM | 983 | CG | ARG | A | 76 | −61.833 | 39.392 | −17.895 | 1.00 | 32.91 | C |
| ATOM | 986 | CD | ARG | A | 76 | −62.615 | 39.453 | −19.205 | 1.00 | 34.43 | C |
| ATOM | 989 | NE | ARG | A | 76 | −63.925 | 38.803 | −19.128 | 1.00 | 35.66 | N |
| ATOM | 991 | CZ | ARG | A | 76 | −64.115 | 37.480 | −19.106 | 1.00 | 37.15 | C |
| ATOM | 992 | NH1 | ARG | A | 76 | −63.085 | 36.632 | −19.129 | 1.00 | 37.93 | N |
| ATOM | 995 | NH2 | ARG | A | 76 | −65.347 | 36.992 | −19.048 | 1.00 | 37.64 | N |
| ATOM | 998 | C | ARG | A | 76 | −62.453 | 41.629 | −14.849 | 1.00 | 31.41 | C |
| ATOM | 999 | O | ARG | A | 76 | −62.144 | 42.798 | −14.966 | 1.00 | 31.35 | O |
| ATOM | 1001 | N | ALA | A | 77 | −63.437 | 41.230 | −14.058 | 1.00 | 31.53 | N |
| ATOM | 1002 | CA | ALA | A | 77 | −64.136 | 42.177 | −13.211 | 1.00 | 31.73 | C |
| ATOM | 1004 | CB | ALA | A | 77 | −65.074 | 41.468 | −12.275 | 1.00 | 31.69 | C |
| ATOM | 1008 | C | ALA | A | 77 | −63.107 | 42.950 | −12.423 | 1.00 | 32.23 | C |
| ATOM | 1009 | O | ALA | A | 77 | −63.116 | 44.176 | −12.411 | 1.00 | 32.42 | O |
| ATOM | 1011 | N | LEU | A | 78 | −62.198 | 42.223 | −11.786 | 1.00 | 32.95 | N |
| ATOM | 1012 | CA | LEU | A | 78 | −61.168 | 42.838 | −10.963 | 1.00 | 33.51 | C |
| ATOM | 1014 | CB | LEU | A | 78 | −60.319 | 41.775 | −10.265 | 1.00 | 33.10 | C |
| ATOM | 1017 | CG | LEU | A | 78 | −60.959 | 41.077 | −9.081 | 1.00 | 32.30 | C |
| ATOM | 1019 | CD1 | LEU | A | 78 | −59.960 | 40.104 | −8.472 | 1.00 | 30.80 | C |
| ATOM | 1023 | CD2 | LEU | A | 78 | −61.438 | 42.117 | −8.056 | 1.00 | 31.89 | C |
| ATOM | 1027 | C | LEU | A | 78 | −60.249 | 43.752 | −11.753 | 1.00 | 34.70 | C |
| ATOM | 1028 | O | LEU | A | 78 | −59.790 | 44.753 | −11.214 | 1.00 | 35.18 | O |
| ATOM | 1030 | N | ASP | A | 79 | −59.955 | 43.404 | −13.007 | 1.00 | 35.91 | N |
| ATOM | 1031 | CA | ASP | A | 79 | −59.054 | 44.205 | −13.828 | 1.00 | 36.89 | C |
| ATOM | 1033 | CB | ASP | A | 79 | −58.637 | 43.452 | −15.083 | 1.00 | 37.06 | C |
| ATOM | 1036 | CG | ASP | A | 79 | −57.518 | 44.150 | −15.821 | 1.00 | 38.41 | C |
| ATOM | 1037 | OD1 | ASP | A | 79 | −57.800 | 45.080 | −16.615 | 1.00 | 39.85 | O |
| ATOM | 1038 | OD2 | ASP | A | 79 | −56.347 | 43.775 | −15.592 | 1.00 | 40.78 | O |
| ATOM | 1039 | C | ASP | A | 79 | −59.721 | 45.505 | −14.220 | 1.00 | 37.75 | C |
| ATOM | 1040 | O | ASP | A | 79 | −59.105 | 46.568 | −14.177 | 1.00 | 37.82 | O |
| ATOM | 1042 | N | ARG | A | 80 | −60.984 | 45.401 | −14.615 | 1.00 | 38.99 | N |
| ATOM | 1043 | CA | ARG | A | 80 | −61.814 | 46.558 | −14.923 | 1.00 | 39.88 | C |
| ATOM | 1045 | CB | ARG | A | 80 | −63.191 | 46.106 | −15.427 | 1.00 | 40.41 | C |
| ATOM | 1048 | CG | ARG | A | 80 | −64.025 | 47.183 | −16.122 | 1.00 | 42.77 | C |
| ATOM | 1051 | CD | ARG | A | 80 | −65.347 | 46.624 | −16.718 | 1.00 | 45.79 | C |
| ATOM | 1054 | NE | ARG | A | 80 | −66.107 | 45.799 | −15.765 | 1.00 | 48.55 | N |
| ATOM | 1056 | CZ | ARG | A | 80 | −66.136 | 44.457 | −15.742 | 1.00 | 50.37 | C |
| ATOM | 1057 | NH1 | ARG | A | 80 | −65.450 | 43.724 | −16.636 | 1.00 | 49.78 | N |
| ATOM | 1060 | NH2 | ARG | A | 80 | −66.868 | 43.835 | −14.805 | 1.00 | 50.77 | N |
| ATOM | 1063 | C | ARG | A | 80 | −61.946 | 47.409 | −13.668 | 1.00 | 39.80 | C |
| ATOM | 1064 | O | ARG | A | 80 | −61.840 | 48.630 | −13.742 | 1.00 | 40.37 | O |
| ATOM | 1066 | N | PHE | A | 81 | −62.136 | 46.771 | −12.516 | 1.00 | 39.62 | N |
| ATOM | 1067 | CA | PHE | A | 81 | −62.216 | 47.505 | −11.245 | 1.00 | 39.61 | C |
| ATOM | 1069 | CB | PHE | A | 81 | −62.392 | 46.561 | −10.053 | 1.00 | 39.74 | C |
| ATOM | 1072 | CG | PHE | A | 81 | −62.282 | 47.247 | −8.712 | 1.00 | 38.81 | C |
| ATOM | 1073 | CD1 | PHE | A | 81 | −63.238 | 48.153 | −8.315 | 1.00 | 39.03 | C |
| ATOM | 1075 | CE1 | PHE | A | 81 | −63.153 | 48.787 | −7.100 | 1.00 | 39.69 | C |

TABLE 3-7-continued

Coordinates of *P. tremuloides IspS*

| | | | | | | | | | | |
|---|---|---|---|---|---|---|---|---|---|---|
| ATOM | 1077 | CZ | PHE | A | 81 | −62.095 | 48.515 | −6.261 | 1.00 | 39.54 C |
| ATOM | 1079 | CE2 | PHE | A | 81 | −61.134 | 47.608 | −6.647 | 1.00 | 38.66 C |
| ATOM | 1081 | CD2 | PHE | A | 81 | −61.228 | 46.986 | −7.865 | 1.00 | 38.27 C |
| ATOM | 1083 | C | PHE | A | 81 | −61.006 | 48.378 | −10.970 | 1.00 | 39.58 C |
| ATOM | 1084 | O | PHE | A | 81 | −61.165 | 49.535 | −10.581 | 1.00 | 39.76 O |
| ATOM | 1086 | N | VAL | A | 82 | −59.810 | 47.817 | −11.142 | 1.00 | 39.50 N |
| ATOM | 1087 | CA | VAL | A | 82 | −58.575 | 48.562 | −10.892 | 1.00 | 39.47 C |
| ATOM | 1089 | CB | VAL | A | 82 | −57.314 | 47.659 | −10.977 | 1.00 | 39.37 C |
| ATOM | 1091 | CG1 | VAL | A | 82 | −56.108 | 48.426 | −11.521 | 1.00 | 39.06 C |
| ATOM | 1095 | CG2 | VAL | A | 82 | −57.009 | 47.079 | −9.614 | 1.00 | 39.23 C |
| ATOM | 1099 | C | VAL | A | 82 | −58.457 | 49.755 | −11.833 | 1.00 | 39.54 C |
| ATOM | 1100 | O | VAL | A | 82 | −58.222 | 50.884 | −11.378 | 1.00 | 39.45 O |
| ATOM | 1102 | N | SER | A | 83 | −58.678 | 49.513 | −13.126 | 1.00 | 39.65 N |
| ATOM | 1103 | CA | SER | A | 83 | −58.469 | 50.535 | −14.157 | 1.00 | 39.82 C |
| ATOM | 1105 | CB | SER | A | 83 | −58.196 | 49.880 | −15.526 | 1.00 | 39.84 C |
| ATOM | 1108 | OG | SER | A | 83 | −59.138 | 48.870 | −15.829 | 1.00 | 40.00 O |
| ATOM | 1110 | C | SER | A | 83 | −59.617 | 51.561 | −14.219 | 1.00 | 39.62 C |
| ATOM | 1111 | O | SER | A | 83 | −60.149 | 51.853 | −15.286 | 1.00 | 39.59 O |
| ATOM | 1113 | N | SER | A | 84 | −59.957 | 52.108 | −13.052 | 1.00 | 39.44 N |
| ATOM | 1114 | CA | SER | A | 84 | −60.926 | 53.197 | −12.910 | 1.00 | 39.13 C |
| ATOM | 1116 | CB | SER | A | 84 | −62.238 | 52.834 | −13.618 | 1.00 | 39.03 C |
| ATOM | 1119 | OG | SER | A | 84 | −62.620 | 51.505 | −13.325 | 1.00 | 37.97 O |
| ATOM | 1121 | C | SER | A | 84 | −61.243 | 53.580 | −11.446 | 1.00 | 39.17 C |
| ATOM | 1122 | O | SER | A | 84 | −62.189 | 54.341 | −11.230 | 1.00 | 39.58 O |
| ATOM | 1124 | N | GLY | A | 85 | −60.482 | 53.077 | −10.457 | 1.00 | 38.74 N |
| ATOM | 1125 | CA | GLY | A | 85 | −60.795 | 53.282 | −9.024 | 1.00 | 38.26 C |
| ATOM | 1128 | C | GLY | A | 85 | −61.724 | 52.238 | −8.413 | 1.00 | 37.79 C |
| ATOM | 1129 | O | GLY | A | 85 | −61.529 | 51.799 | −7.273 | 1.00 | 36.84 O |
| ATOM | 1131 | N | SER | A | 94 | −63.557 | 54.187 | 1.994 | 1.00 | 28.27 N |
| ATOM | 1132 | CA | SER | A | 94 | −64.069 | 52.892 | 2.476 | 1.00 | 28.03 C |
| ATOM | 1134 | CB | SER | A | 94 | −64.856 | 52.225 | 1.359 | 1.00 | 27.84 C |
| ATOM | 1137 | OG | SER | A | 94 | −65.234 | 50.921 | 1.743 | 1.00 | 28.20 O |
| ATOM | 1139 | C | SER | A | 94 | −62.992 | 51.910 | 2.934 | 1.00 | 27.83 C |
| ATOM | 1140 | O | SER | A | 94 | −62.339 | 51.325 | 2.090 | 1.00 | 28.15 O |
| ATOM | 1142 | N | LEU | A | 95 | −62.815 | 51.705 | 4.245 | 1.00 | 27.70 N |
| ATOM | 1143 | CA | LEU | A | 95 | −61.813 | 50.728 | 4.751 | 1.00 | 27.59 C |
| ATOM | 1145 | CB | LEU | A | 95 | −61.692 | 50.747 | 6.282 | 1.00 | 27.49 C |
| ATOM | 1148 | CG | LEU | A | 95 | −60.871 | 49.596 | 6.909 | 1.00 | 27.47 C |
| ATOM | 1150 | CD1 | LEU | A | 95 | −59.400 | 49.900 | 6.902 | 1.00 | 27.70 C |
| ATOM | 1154 | CD2 | LEU | A | 95 | −61.292 | 49.274 | 8.329 | 1.00 | 27.50 C |
| ATOM | 1158 | C | LEU | A | 95 | −62.173 | 49.314 | 4.318 | 1.00 | 27.71 C |
| ATOM | 1159 | O | LEU | A | 95 | −61.303 | 48.537 | 3.914 | 1.00 | 27.73 O |
| ATOM | 1161 | N | HIS | A | 96 | −63.461 | 48.989 | 4.437 | 1.00 | 27.74 N |
| ATOM | 1162 | CA | HIS | A | 96 | −64.003 | 47.715 | 3.977 | 1.00 | 27.54 C |
| ATOM | 1164 | CB | HIS | A | 96 | −65.497 | 47.680 | 4.230 | 1.00 | 27.57 C |
| ATOM | 1167 | CG | HIS | A | 96 | −66.161 | 46.482 | 3.654 | 1.00 | 28.65 C |
| ATOM | 1168 | ND1 | HIS | A | 96 | −65.790 | 45.201 | 3.988 | 1.00 | 30.59 N |
| ATOM | 1170 | CE1 | HIS | A | 96 | −66.540 | 44.341 | 3.325 | 1.00 | 31.88 C |
| ATOM | 1172 | NE2 | HIS | A | 96 | −67.384 | 45.021 | 2.570 | 1.00 | 32.06 N |
| ATOM | 1174 | CD2 | HIS | A | 96 | −67.166 | 46.364 | 2.758 | 1.00 | 30.47 C |
| ATOM | 1176 | C | HIS | A | 96 | −63.705 | 47.450 | 2.492 | 1.00 | 27.09 C |
| ATOM | 1177 | O | HIS | A | 96 | −63.128 | 46.425 | 2.150 | 1.00 | 27.18 O |
| ATOM | 1179 | N | GLY | A | 97 | −64.079 | 48.386 | 1.625 | 1.00 | 26.55 N |
| ATOM | 1180 | CA | GLY | A | 97 | −63.760 | 48.300 | .205 | 1.00 | 26.26 C |
| ATOM | 1183 | C | GLY | A | 97 | −62.277 | 48.112 | −.088 | 1.00 | 26.23 C |
| ATOM | 1184 | O | GLY | A | 97 | −61.918 | 47.334 | −.974 | 1.00 | 26.39 O |
| ATOM | 1186 | N | THR | A | 98 | −61.415 | 48.815 | .653 | 1.00 | 25.83 N |
| ATOM | 1187 | CA | THR | A | 98 | −59.967 | 48.755 | .435 | 1.00 | 25.36 C |
| ATOM | 1189 | CB | THR | A | 98 | −59.204 | 49.847 | 1.215 | 1.00 | 25.07 C |
| ATOM | 1191 | OG1 | THR | A | 98 | −59.796 | 51.123 | .980 | 1.00 | 23.62 O |
| ATOM | 1193 | CG2 | THR | A | 98 | −57.755 | 49.905 | .780 | 1.00 | 24.88 C |
| ATOM | 1197 | C | THR | A | 98 | −59.416 | 47.389 | .845 | 1.00 | 25.69 C |
| ATOM | 1198 | O | THR | A | 98 | −58.622 | 46.802 | .111 | 1.00 | 25.66 O |
| ATOM | 1200 | N | ALA | A | 99 | −59.847 | 46.890 | 2.008 | 1.00 | 25.95 N |
| ATOM | 1201 | CA | ALA | A | 99 | −59.468 | 45.540 | 2.495 | 1.00 | 25.93 C |
| ATOM | 1203 | CB | ALA | A | 99 | −59.945 | 45.330 | 3.929 | 1.00 | 25.82 C |
| ATOM | 1207 | C | ALA | A | 99 | −59.984 | 44.404 | 1.595 | 1.00 | 25.64 C |
| ATOM | 1208 | O | ALA | A | 99 | −59.204 | 43.599 | 1.102 | 1.00 | 25.38 O |
| ATOM | 1210 | N | LEU | A | 100 | −61.290 | 44.348 | 1.371 | 1.00 | 25.46 N |
| ATOM | 1211 | CA | LEU | A | 100 | −61.856 | 43.335 | .474 | 1.00 | 25.55 C |
| ATOM | 1213 | CB | LEU | A | 100 | −63.361 | 43.540 | .326 | 1.00 | 25.37 C |
| ATOM | 1216 | CG | LEU | A | 100 | −64.118 | 42.464 | −.443 | 1.00 | 25.41 C |
| ATOM | 1218 | CD1 | LEU | A | 100 | −64.038 | 41.115 | .281 | 1.00 | 26.01 C |
| ATOM | 1222 | CD2 | LEU | A | 100 | −65.555 | 42.893 | −.639 | 1.00 | 25.19 C |
| ATOM | 1226 | C | LEU | A | 100 | −61.196 | 43.353 | −.919 | 1.00 | 25.70 C |
| ATOM | 1227 | O | LEU | A | 100 | −60.819 | 42.301 | −1.469 | 1.00 | 25.36 O |
| ATOM | 1229 | N | SER | A | 101 | −61.064 | 44.550 | −1.489 | 1.00 | 25.77 N |
| ATOM | 1230 | CA | SER | A | 101 | −60.434 | 44.688 | −2.805 | 1.00 | 25.67 C |

TABLE 3-7-continued

Coordinates of *P. tremuloides IspS*

| | | | | | | | | | | | |
|---|---|---|---|---|---|---|---|---|---|---|---|
| ATOM | 1232 | CB | SER | A | 101 | −60.629 | 46.098 | −3.375 | 1.00 | 25.83 | C |
| ATOM | 1235 | OG | SER | A | 101 | −59.840 | 47.064 | −2.688 | 1.00 | 26.98 | O |
| ATOM | 1237 | C | SER | A | 101 | −58.947 | 44.336 | −2.756 | 1.00 | 25.01 | C |
| ATOM | 1238 | O | SER | A | 101 | −58.427 | 43.705 | −3.672 | 1.00 | 24.94 | O |
| ATOM | 1240 | N | PHE | A | 102 | −58.270 | 44.737 | −1.687 | 1.00 | 24.30 | N |
| ATOM | 1241 | CA | PHE | A | 102 | −56.852 | 44.436 | −1.560 | 1.00 | 23.99 | C |
| ATOM | 1243 | CB | PHE | A | 102 | −56.295 | 44.963 | −.229 | 1.00 | 23.84 | C |
| ATOM | 1246 | CG | PHE | A | 102 | −54.860 | 44.606 | .027 | 1.00 | 23.24 | C |
| ATOM | 1247 | CD1 | PHE | A | 102 | −53.849 | 45.504 | −.259 | 1.00 | 23.56 | C |
| ATOM | 1249 | CE1 | PHE | A | 102 | −52.507 | 45.182 | −.007 | 1.00 | 24.50 | C |
| ATOM | 1251 | CZ | PHE | A | 102 | −52.175 | 43.941 | .540 | 1.00 | 24.27 | C |
| ATOM | 1253 | CE2 | PHE | A | 102 | −53.180 | 43.042 | .834 | 1.00 | 23.95 | C |
| ATOM | 1255 | CD2 | PHE | A | 102 | −54.520 | 43.376 | .576 | 1.00 | 23.45 | C |
| ATOM | 1257 | C | PHE | A | 102 | −56.673 | 42.928 | −1.679 | 1.00 | 23.65 | C |
| ATOM | 1258 | O | PHE | A | 102 | −55.890 | 42.442 | −2.501 | 1.00 | 23.55 | O |
| ATOM | 1260 | N | ARG | A | 103 | −57.443 | 42.202 | −.880 | 1.00 | 23.20 | N |
| ATOM | 1261 | CA | ARG | A | 103 | −57.298 | 40.765 | −.764 | 1.00 | 22.84 | C |
| ATOM | 1263 | CB | ARG | A | 103 | −58.250 | 40.231 | .291 | 1.00 | 23.01 | C |
| ATOM | 1266 | CG | ARG | A | 103 | −58.054 | 38.774 | .597 | 1.00 | 23.93 | C |
| ATOM | 1269 | CD | ARG | A | 103 | −58.703 | 38.376 | 1.937 | 1.00 | 23.84 | C |
| ATOM | 1272 | NE | ARG | A | 103 | −60.150 | 38.538 | 1.919 | 1.00 | 22.36 | N |
| ATOM | 1274 | CZ | ARG | A | 103 | −60.982 | 37.763 | 1.240 | 1.00 | 20.62 | C |
| ATOM | 1275 | NH1 | ARG | A | 103 | −60.512 | 36.773 | .490 | 1.00 | 20.19 | N |
| ATOM | 1278 | NH2 | ARG | A | 103 | −62.288 | 38.003 | 1.293 | 1.00 | 20.32 | N |
| ATOM | 1281 | C | ARG | A | 103 | −57.602 | 40.117 | −2.082 | 1.00 | 22.34 | C |
| ATOM | 1282 | O | ARG | A | 103 | −56.826 | 39.303 | −2.576 | 1.00 | 22.37 | O |
| ATOM | 1284 | N | LEU | A | 104 | −58.729 | 40.496 | −2.667 | 1.00 | 21.98 | N |
| ATOM | 1285 | CA | LEU | A | 104 | −59.129 | 39.926 | −3.951 | 1.00 | 21.60 | C |
| ATOM | 1287 | CB | LEU | A | 104 | −60.503 | 40.442 | −4.378 | 1.00 | 21.23 | C |
| ATOM | 1290 | CG | LEU | A | 104 | −61.590 | 39.832 | −3.522 | 1.00 | 20.30 | C |
| ATOM | 1292 | CD1 | LEU | A | 104 | −62.949 | 40.401 | −3.856 | 1.00 | 19.53 | C |
| ATOM | 1296 | CD2 | LEU | A | 104 | −61.554 | 38.344 | −3.725 | 1.00 | 19.71 | C |
| ATOM | 1300 | C | LEU | A | 104 | −58.101 | 40.198 | −5.040 | 1.00 | 21.48 | C |
| ATOM | 1301 | O | LEU | A | 104 | −57.743 | 39.294 | −5.780 | 1.00 | 21.62 | O |
| ATOM | 1303 | N | LEU | A | 105 | −57.623 | 41.432 | −5.139 | 1.00 | 21.14 | N |
| ATOM | 1304 | CA | LEU | A | 105 | −56.655 | 41.747 | −6.173 | 1.00 | 21.05 | C |
| ATOM | 1306 | CB | LEU | A | 105 | −56.352 | 43.248 | −6.205 | 1.00 | 20.94 | C |
| ATOM | 1309 | CG | LEU | A | 105 | −57.465 | 44.165 | −6.732 | 1.00 | 20.06 | C |
| ATOM | 1311 | CD1 | LEU | A | 105 | −57.060 | 45.617 | −6.580 | 1.00 | 17.92 | C |
| ATOM | 1315 | CD2 | LEU | A | 105 | −57.804 | 43.857 | −8.174 | 1.00 | 19.18 | C |
| ATOM | 1319 | C | LEU | A | 105 | −55.372 | 40.908 | −5.997 | 1.00 | 21.32 | C |
| ATOM | 1320 | O | LEU | A | 105 | −54.840 | 40.357 | −6.976 | 1.00 | 21.37 | O |
| ATOM | 1322 | N | ARG | A | 106 | −54.893 | 40.777 | −4.763 | 1.00 | 21.25 | N |
| ATOM | 1323 | CA | ARG | A | 106 | −53.678 | 40.003 | −4.528 | 1.00 | 21.33 | C |
| ATOM | 1325 | CB | ARG | A | 106 | −53.151 | 40.211 | −3.117 | 1.00 | 21.53 | C |
| ATOM | 1328 | CG | ARG | A | 106 | −51.772 | 39.588 | −2.917 | 1.00 | 22.60 | C |
| ATOM | 1331 | CD | ARG | A | 106 | −51.098 | 40.091 | −1.666 | 1.00 | 23.60 | C |
| ATOM | 1334 | NE | ARG | A | 106 | −50.374 | 41.330 | −1.897 | 1.00 | 24.60 | N |
| ATOM | 1336 | CZ | ARG | A | 106 | −49.606 | 41.916 | −.989 | 1.00 | 26.54 | C |
| ATOM | 1337 | NH1 | ARG | A | 106 | −49.469 | 41.380 | .225 | 1.00 | 26.98 | N |
| ATOM | 1340 | NH2 | ARG | A | 106 | −48.967 | 43.041 | −1.295 | 1.00 | 27.19 | N |
| ATOM | 1343 | C | ARG | A | 106 | −53.888 | 38.517 | −4.767 | 1.00 | 21.19 | C |
| ATOM | 1344 | O | ARG | A | 106 | −52.998 | 37.821 | −5.278 | 1.00 | 21.18 | O |
| ATOM | 1346 | N | GLN | A | 107 | −55.061 | 38.028 | −4.378 | 1.00 | 21.09 | N |
| ATOM | 1347 | CA | GLN | A | 107 | −55.425 | 36.635 | −4.618 | 1.00 | 20.76 | C |
| ATOM | 1349 | CB | GLN | A | 107 | −56.861 | 36.378 | −4.168 | 1.00 | 20.51 | C |
| ATOM | 1352 | CG | GLN | A | 107 | −57.329 | 34.941 | −4.327 | 1.00 | 19.68 | C |
| ATOM | 1355 | CD | GLN | A | 107 | −58.790 | 34.772 | −4.010 | 1.00 | 18.26 | C |
| ATOM | 1356 | OE1 | GLN | A | 107 | −59.395 | 35.591 | −3.334 | 1.00 | 17.44 | O |
| ATOM | 1357 | NE2 | GLN | A | 107 | −59.366 | 33.698 | −4.497 | 1.00 | 18.48 | N |
| ATOM | 1360 | C | GLN | A | 107 | −55.304 | 36.306 | −6.094 | 1.00 | 20.93 | C |
| ATOM | 1361 | O | GLN | A | 107 | −54.917 | 35.212 | −6.447 | 1.00 | 21.45 | O |
| ATOM | 1363 | N | HIS | A | 108 | −55.642 | 37.260 | −6.951 | 1.00 | 21.09 | N |
| ATOM | 1364 | CA | HIS | A | 108 | −55.686 | 37.030 | −8.379 | 1.00 | 21.28 | C |
| ATOM | 1366 | CB | HIS | A | 108 | −57.024 | 37.541 | −8.913 | 1.00 | 21.02 | C |
| ATOM | 1369 | CG | HIS | A | 108 | −58.182 | 36.706 | −8.478 | 1.00 | 19.70 | C |
| ATOM | 1370 | ND1 | HIS | A | 108 | −58.637 | 35.632 | −9.210 | 1.00 | 19.91 | N |
| ATOM | 1372 | CE1 | HIS | A | 108 | −59.641 | 35.060 | −8.571 | 1.00 | 19.27 | C |
| ATOM | 1374 | NE2 | HIS | A | 108 | −59.851 | 35.720 | −7.449 | 1.00 | 18.10 | N |
| ATOM | 1376 | CD2 | HIS | A | 108 | −58.950 | 36.753 | −7.367 | 1.00 | 18.98 | C |
| ATOM | 1378 | C | HIS | A | 108 | −54.456 | 37.621 | −9.108 | 1.00 | 22.21 | C |
| ATOM | 1379 | O | HIS | A | 108 | −54.505 | 37.980 | −10.304 | 1.00 | 21.80 | O |
| ATOM | 1381 | N | GLY | A | 109 | −53.345 | 37.686 | −8.375 | 1.00 | 23.19 | N |
| ATOM | 1382 | CA | GLY | A | 109 | −52.055 | 38.007 | −8.956 | 1.00 | 24.17 | C |
| ATOM | 1385 | C | GLY | A | 109 | −51.813 | 39.470 | −9.275 | 1.00 | 25.25 | C |
| ATOM | 1386 | O | GLY | A | 109 | −50.767 | 39.802 | −9.845 | 1.00 | 25.26 | O |
| ATOM | 1388 | N | PHE | A | 110 | −52.755 | 40.349 | −8.917 | 1.00 | 26.42 | N |
| ATOM | 1389 | CA | PHE | A | 110 | −52.575 | 41.783 | −9.154 | 1.00 | 27.33 | C |

TABLE 3-7-continued

Coordinates of *P. tremuloides IspS*

| | | | | | | | | | | | |
|---|---|---|---|---|---|---|---|---|---|---|---|
| ATOM | 1391 | CB | PHE | A | 110 | −53.895 | 42.546 | −9.067 | 1.00 | 27.36 | C |
| ATOM | 1394 | CG | PHE | A | 110 | −54.838 | 42.250 | −10.193 | 1.00 | 27.83 | C |
| ATOM | 1395 | CD1 | PHE | A | 110 | −54.633 | 42.801 | −11.439 | 1.00 | 28.69 | C |
| ATOM | 1397 | CE1 | PHE | A | 110 | −55.490 | 42.529 | −12.488 | 1.00 | 28.91 | C |
| ATOM | 1399 | CZ | PHE | A | 110 | −56.568 | 41.702 | −12.295 | 1.00 | 28.85 | C |
| ATOM | 1401 | CE2 | PHE | A | 110 | −56.787 | 41.146 | −11.060 | 1.00 | 28.67 | C |
| ATOM | 1403 | CD2 | PHE | A | 110 | −55.923 | 41.418 | −10.013 | 1.00 | 28.39 | C |
| ATOM | 1405 | C | PHE | A | 110 | −51.582 | 42.369 | −8.163 | 1.00 | 28.25 | C |
| ATOM | 1406 | O | PHE | A | 110 | −51.449 | 41.890 | −7.024 | 1.00 | 28.71 | O |
| ATOM | 1408 | N | GLU | A | 111 | −50.886 | 43.411 | −8.607 | 1.00 | 29.05 | N |
| ATOM | 1409 | CA | GLU | A | 111 | −49.951 | 44.142 | −7.760 | 1.00 | 29.66 | C |
| ATOM | 1411 | CB | GLU | A | 111 | −48.902 | 44.803 | −8.648 | 1.00 | 30.37 | C |
| ATOM | 1414 | CG | GLU | A | 111 | −47.750 | 45.509 | −7.947 | 1.00 | 33.30 | C |
| ATOM | 1417 | CD | GLU | A | 111 | −46.916 | 46.342 | −8.946 | 1.00 | 38.00 | C |
| ATOM | 1418 | OE1 | GLU | A | 111 | −46.312 | 45.750 | −9.885 | 1.00 | 39.60 | O |
| ATOM | 1419 | OE2 | GLU | A | 111 | −46.886 | 47.594 | −8.802 | 1.00 | 40.87 | O |
| ATOM | 1420 | C | GLU | A | 111 | −50.724 | 45.184 | −6.935 | 1.00 | 28.98 | C |
| ATOM | 1421 | O | GLU | A | 111 | −51.293 | 46.123 | −7.495 | 1.00 | 28.45 | O |
| ATOM | 1423 | N | VAL | A | 112 | −50.787 | 44.961 | −5.618 | 1.00 | 28.47 | N |
| ATOM | 1424 | CA | VAL | A | 112 | −51.284 | 45.950 | −4.655 | 1.00 | 28.09 | C |
| ATOM | 1426 | CB | VAL | A | 112 | −52.564 | 45.501 | −3.908 | 1.00 | 27.76 | C |
| ATOM | 1428 | CG1 | VAL | A | 112 | −53.745 | 45.466 | −4.836 | 1.00 | 27.38 | C |
| ATOM | 1432 | CG2 | VAL | A | 112 | −52.360 | 44.167 | −3.252 | 1.00 | 27.80 | C |
| ATOM | 1436 | C | VAL | A | 112 | −50.193 | 46.199 | −3.631 | 1.00 | 28.15 | C |
| ATOM | 1437 | O | VAL | A | 112 | −49.339 | 45.354 | −3.436 | 1.00 | 27.90 | O |
| ATOM | 1439 | N | SER | A | 113 | −50.241 | 47.354 | −2.974 | 1.00 | 28.54 | N |
| ATOM | 1440 | CA | SER | A | 113 | −49.194 | 47.782 | −2.047 | 1.00 | 28.93 | C |
| ATOM | 1442 | CB | SER | A | 113 | −48.563 | 49.064 | −2.564 | 1.00 | 29.12 | C |
| ATOM | 1445 | OG | SER | A | 113 | −47.692 | 49.644 | −1.619 | 1.00 | 29.57 | O |
| ATOM | 1447 | C | SER | A | 113 | −49.780 | 48.041 | −.685 | 1.00 | 29.13 | C |
| ATOM | 1448 | O | SER | A | 113 | −50.937 | 48.426 | −.581 | 1.00 | 28.90 | O |
| ATOM | 1450 | N | GLN | A | 114 | −48.985 | 47.857 | .367 | 1.00 | 29.84 | N |
| ATOM | 1451 | CA | GLN | A | 114 | −49.524 | 48.019 | 1.736 | 1.00 | 30.40 | C |
| ATOM | 1453 | CB | GLN | A | 114 | −48.568 | 47.507 | 2.830 | 1.00 | 30.34 | C |
| ATOM | 1456 | CG | GLN | A | 114 | −47.199 | 48.159 | 2.844 | 1.00 | 30.61 | C |
| ATOM | 1459 | CD | GLN | A | 114 | −46.456 | 47.928 | 4.147 | 1.00 | 30.77 | C |
| ATOM | 1460 | OE1 | GLN | A | 114 | −46.876 | 47.129 | 4.982 | 1.00 | 31.92 | O |
| ATOM | 1461 | NE2 | GLN | A | 114 | −45.341 | 48.624 | 4.324 | 1.00 | 30.02 | N |
| ATOM | 1464 | C | GLN | A | 114 | −49.939 | 49.440 | 2.068 | 1.00 | 30.62 | C |
| ATOM | 1465 | O | GLN | A | 114 | −50.573 | 49.644 | 3.094 | 1.00 | 30.73 | O |
| ATOM | 1467 | N | GLU | A | 115 | −49.592 | 50.407 | 1.216 | 1.00 | 30.94 | N |
| ATOM | 1468 | CA | GLU | A | 115 | −49.963 | 51.794 | 1.458 | 1.00 | 31.45 | C |
| ATOM | 1470 | CB | GLU | A | 115 | −48.881 | 52.777 | .975 | 1.00 | 31.86 | C |
| ATOM | 1473 | CG | GLU | A | 115 | −48.489 | 52.723 | −.509 | 1.00 | 33.48 | C |
| ATOM | 1476 | CD | GLU | A | 115 | −47.006 | 53.100 | −.759 | 1.00 | 36.13 | C |
| ATOM | 1477 | OE1 | GLU | A | 115 | −46.106 | 52.668 | .022 | 1.00 | 38.72 | O |
| ATOM | 1478 | OE2 | GLU | A | 115 | −46.741 | 53.811 | −1.754 | 1.00 | 35.70 | O |
| ATOM | 1479 | C | GLU | A | 115 | −51.338 | 52.125 | .895 | 1.00 | 31.45 | C |
| ATOM | 1480 | O | GLU | A | 115 | −51.716 | 53.283 | .808 | 1.00 | 31.80 | O |
| ATOM | 1482 | N | ALA | A | 116 | −52.108 | 51.105 | .549 | 1.00 | 31.58 | N |
| ATOM | 1483 | CA | ALA | A | 116 | −53.524 | 51.286 | .284 | 1.00 | 31.67 | C |
| ATOM | 1485 | CB | ALA | A | 116 | −54.071 | 50.092 | −.461 | 1.00 | 31.62 | C |
| ATOM | 1489 | C | ALA | A | 116 | −54.273 | 51.473 | 1.596 | 1.00 | 31.88 | C |
| ATOM | 1490 | O | ALA | A | 116 | −55.428 | 51.874 | 1.604 | 1.00 | 31.82 | O |
| ATOM | 1492 | N | PHE | A | 117 | −53.608 | 51.161 | 2.702 | 1.00 | 32.39 | N |
| ATOM | 1493 | CA | PHE | A | 117 | −54.193 | 51.271 | 4.030 | 1.00 | 32.87 | C |
| ATOM | 1495 | CB | PHE | A | 117 | −53.884 | 50.003 | 4.856 | 1.00 | 32.79 | C |
| ATOM | 1498 | CG | PHE | A | 117 | −54.539 | 48.758 | 4.323 | 1.00 | 31.03 | C |
| ATOM | 1499 | CD1 | PHE | A | 117 | −53.782 | 47.749 | 3.760 | 1.00 | 28.79 | C |
| ATOM | 1501 | CE1 | PHE | A | 117 | −54.379 | 46.620 | 3.265 | 1.00 | 28.36 | C |
| ATOM | 1503 | CZ | PHE | A | 117 | −55.754 | 46.489 | 3.316 | 1.00 | 29.50 | C |
| ATOM | 1505 | CE2 | PHE | A | 117 | −56.527 | 47.493 | 3.872 | 1.00 | 29.91 | C |
| ATOM | 1507 | CD2 | PHE | A | 117 | −55.917 | 48.613 | 4.375 | 1.00 | 30.09 | C |
| ATOM | 1509 | C | PHE | A | 117 | −53.683 | 52.493 | 4.773 | 1.00 | 33.71 | C |
| ATOM | 1510 | O | PHE | A | 117 | −54.012 | 52.678 | 5.937 | 1.00 | 33.61 | O |
| ATOM | 1512 | N | SER | A | 118 | −52.886 | 53.325 | 4.107 | 1.00 | 35.09 | N |
| ATOM | 1513 | CA | SER | A | 118 | −52.186 | 54.429 | 4.779 | 1.00 | 36.12 | C |
| ATOM | 1515 | CB | SER | A | 118 | −51.073 | 54.990 | 3.895 | 1.00 | 36.09 | C |
| ATOM | 1518 | OG | SER | A | 118 | −51.607 | 55.747 | 2.820 | 1.00 | 35.96 | O |
| ATOM | 1520 | C | SER | A | 118 | −53.134 | 55.552 | 5.184 | 1.00 | 37.17 | C |
| ATOM | 1521 | O | SER | A | 118 | −52.873 | 56.255 | 6.166 | 1.00 | 37.22 | O |
| ATOM | 1523 | N | GLY | A | 119 | −54.231 | 55.705 | 4.436 | 1.00 | 38.40 | N |
| ATOM | 1524 | CA | GLY | A | 119 | −55.227 | 56.735 | 4.708 | 1.00 | 39.47 | C |
| ATOM | 1527 | C | GLY | A | 119 | −56.255 | 56.398 | 5.778 | 1.00 | 40.62 | C |
| ATOM | 1528 | O | GLY | A | 119 | −57.259 | 57.086 | 5.877 | 1.00 | 40.74 | O |
| ATOM | 1530 | N | PHE | A | 120 | −56.024 | 55.344 | 6.563 | 1.00 | 42.13 | N |
| ATOM | 1531 | CA | PHE | A | 120 | −56.906 | 54.971 | 7.684 | 1.00 | 43.27 | C |
| ATOM | 1533 | CB | PHE | A | 120 | −57.510 | 53.586 | 7.455 | 1.00 | 43.21 | C |

TABLE 3-7-continued

Coordinates of *P. tremuloides IspS*

| | | | | | | | | | | | |
|---|---|---|---|---|---|---|---|---|---|---|---|
| ATOM | 1536 | CG | PHE | A | 120 | −58.176 | 53.439 | 6.134 | 1.00 | 42.36 | C |
| ATOM | 1537 | CD1 | PHE | A | 120 | −59.418 | 54.006 | 5.911 | 1.00 | 41.23 | C |
| ATOM | 1539 | CE1 | PHE | A | 120 | −60.035 | 53.880 | 4.691 | 1.00 | 40.87 | C |
| ATOM | 1541 | CZ | PHE | A | 120 | −59.414 | 53.182 | 3.675 | 1.00 | 41.03 | C |
| ATOM | 1543 | CE2 | PHE | A | 120 | −58.167 | 52.618 | 3.883 | 1.00 | 40.92 | C |
| ATOM | 1545 | CD2 | PHE | A | 120 | −57.556 | 52.746 | 5.106 | 1.00 | 41.30 | C |
| ATOM | 1547 | C | PHE | A | 120 | −56.179 | 54.952 | 9.019 | 1.00 | 44.71 | C |
| ATOM | 1548 | O | PHE | A | 120 | −56.732 | 54.489 | 10.025 | 1.00 | 44.80 | O |
| ATOM | 1550 | N | LYS | A | 121 | −54.939 | 55.430 | 9.021 | 1.00 | 46.38 | N |
| ATOM | 1551 | CA | LYS | A | 121 | −54.153 | 55.519 | 10.235 | 1.00 | 47.81 | C |
| ATOM | 1553 | CB | LYS | A | 121 | −52.722 | 55.050 | 9.957 | 1.00 | 47.86 | C |
| ATOM | 1556 | CG | LYS | A | 121 | −52.648 | 53.537 | 9.648 | 1.00 | 48.24 | C |
| ATOM | 1559 | CD | LYS | A | 121 | −51.417 | 53.119 | 8.823 | 1.00 | 49.41 | C |
| ATOM | 1562 | CE | LYS | A | 121 | −50.095 | 53.142 | 9.621 | 1.00 | 49.88 | C |
| ATOM | 1565 | NZ | LYS | A | 121 | −49.944 | 52.005 | 10.584 | 1.00 | 49.89 | N |
| ATOM | 1569 | C | LYS | A | 121 | −54.257 | 56.964 | 10.735 | 1.00 | 49.00 | C |
| ATOM | 1570 | O | LYS | A | 121 | −54.712 | 57.839 | 10.000 | 1.00 | 49.11 | O |
| ATOM | 1572 | N | ASP | A | 122 | −53.899 | 57.206 | 11.995 | 1.00 | 50.51 | N |
| ATOM | 1573 | CA | ASP | A | 122 | −54.078 | 58.537 | 12.596 | 1.00 | 51.46 | C |
| ATOM | 1575 | CB | ASP | A | 122 | −54.604 | 58.443 | 14.050 | 1.00 | 51.29 | C |
| ATOM | 1578 | CG | ASP | A | 122 | −53.570 | 57.919 | 15.036 | 1.00 | 50.73 | C |
| ATOM | 1579 | OD1 | ASP | A | 122 | −52.353 | 58.025 | 14.777 | 1.00 | 49.90 | O |
| ATOM | 1580 | OD2 | ASP | A | 122 | −53.988 | 57.398 | 16.088 | 1.00 | 49.66 | O |
| ATOM | 1581 | C | ASP | A | 122 | −52.792 | 59.358 | 12.502 | 1.00 | 52.60 | C |
| ATOM | 1582 | O | ASP | A | 122 | −51.830 | 58.953 | 11.835 | 1.00 | 52.65 | O |
| ATOM | 1584 | N | GLN | A | 123 | −52.802 | 60.512 | 13.172 | 1.00 | 53.88 | N |
| ATOM | 1585 | CA | GLN | A | 123 | −51.680 | 61.456 | 13.195 | 1.00 | 54.66 | C |
| ATOM | 1587 | CB | GLN | A | 123 | −51.993 | 62.594 | 14.178 | 1.00 | 55.01 | C |
| ATOM | 1590 | CG | GLN | A | 123 | −53.249 | 63.442 | 13.831 | 1.00 | 56.15 | C |
| ATOM | 1593 | CD | GLN | A | 123 | −52.943 | 64.736 | 13.064 | 1.00 | 57.64 | C |
| ATOM | 1594 | OE1 | GLN | A | 123 | −51.779 | 65.102 | 12.859 | 1.00 | 59.10 | O |
| ATOM | 1595 | NE2 | GLN | A | 123 | −54.001 | 65.438 | 12.652 | 1.00 | 57.63 | N |
| ATOM | 1598 | C | GLN | A | 123 | −50.365 | 60.772 | 13.591 | 1.00 | 54.87 | C |
| ATOM | 1599 | O | GLN | A | 123 | −49.309 | 61.078 | 13.034 | 1.00 | 54.67 | O |
| ATOM | 1601 | N | ASN | A | 124 | −50.458 | 59.834 | 14.538 | 1.00 | 55.21 | N |
| ATOM | 1602 | CA | ASN | A | 124 | −49.300 | 59.137 | 15.109 | 1.00 | 55.39 | C |
| ATOM | 1604 | CB | ASN | A | 124 | −49.421 | 59.122 | 16.637 | 1.00 | 55.52 | C |
| ATOM | 1607 | CG | ASN | A | 124 | −49.833 | 60.478 | 17.202 | 1.00 | 55.98 | C |
| ATOM | 1608 | OD1 | ASN | A | 124 | −49.093 | 61.460 | 17.091 | 1.00 | 56.93 | O |
| ATOM | 1609 | ND2 | ASN | A | 124 | −51.026 | 60.540 | 17.797 | 1.00 | 55.99 | N |
| ATOM | 1612 | C | ASN | A | 124 | −49.116 | 57.705 | 14.589 | 1.00 | 55.27 | C |
| ATOM | 1613 | O | ASN | A | 124 | −48.530 | 56.864 | 15.271 | 1.00 | 55.18 | O |
| ATOM | 1615 | N | GLY | A | 125 | −49.626 | 57.430 | 13.391 | 1.00 | 55.18 | N |
| ATOM | 1616 | CA | GLY | A | 125 | −49.311 | 56.190 | 12.672 | 1.00 | 55.08 | C |
| ATOM | 1619 | C | GLY | A | 125 | −49.994 | 54.897 | 13.119 | 1.00 | 54.90 | C |
| ATOM | 1620 | O | GLY | A | 125 | −49.543 | 53.806 | 12.750 | 1.00 | 55.24 | O |
| ATOM | 1622 | N | ASN | A | 126 | −51.072 | 55.008 | 13.900 | 1.00 | 54.23 | N |
| ATOM | 1623 | CA | ASN | A | 126 | −51.871 | 53.853 | 14.329 | 1.00 | 53.39 | C |
| ATOM | 1625 | CB | ASN | A | 126 | −51.927 | 53.782 | 15.852 | 1.00 | 53.27 | C |
| ATOM | 1628 | CG | ASN | A | 126 | −50.596 | 53.425 | 16.466 | 1.00 | 52.81 | C |
| ATOM | 1629 | OD1 | ASN | A | 126 | −49.636 | 53.113 | 15.764 | 1.00 | 52.29 | O |
| ATOM | 1630 | ND2 | ASN | A | 126 | −50.532 | 53.460 | 17.789 | 1.00 | 52.53 | N |
| ATOM | 1633 | C | ASN | A | 126 | −53.274 | 53.978 | 13.771 | 1.00 | 52.82 | C |
| ATOM | 1634 | O | ASN | A | 126 | −53.724 | 55.081 | 13.494 | 1.00 | 52.69 | O |
| ATOM | 1636 | N | PHE | A | 127 | −53.968 | 52.857 | 13.607 | 1.00 | 52.17 | N |
| ATOM | 1637 | CA | PHE | A | 127 | −55.287 | 52.875 | 12.962 | 1.00 | 51.56 | C |
| ATOM | 1639 | CB | PHE | A | 127 | −55.805 | 51.451 | 12.721 | 1.00 | 51.35 | C |
| ATOM | 1642 | CG | PHE | A | 127 | −55.119 | 50.730 | 11.587 | 1.00 | 50.06 | C |
| ATOM | 1643 | CD1 | PHE | A | 127 | −54.068 | 49.856 | 11.831 | 1.00 | 48.90 | C |
| ATOM | 1645 | CE1 | PHE | A | 127 | −53.437 | 49.187 | 10.789 | 1.00 | 47.59 | C |
| ATOM | 1647 | CZ | PHE | A | 127 | −53.857 | 49.383 | 9.495 | 1.00 | 47.40 | C |
| ATOM | 1649 | CE2 | PHE | A | 127 | −54.906 | 50.244 | 9.234 | 1.00 | 47.96 | C |
| ATOM | 1651 | CD2 | PHE | A | 127 | −55.533 | 50.915 | 10.276 | 1.00 | 48.85 | C |
| ATOM | 1653 | C | PHE | A | 127 | −56.303 | 53.690 | 13.776 | 1.00 | 51.35 | C |
| ATOM | 1654 | O | PHE | A | 127 | −56.347 | 53.594 | 15.002 | 1.00 | 51.09 | O |
| ATOM | 1656 | N | LEU | A | 128 | −57.100 | 54.500 | 13.083 | 1.00 | 51.15 | N |
| ATOM | 1657 | CA | LEU | A | 128 | −58.143 | 55.280 | 13.727 | 1.00 | 51.09 | C |
| ATOM | 1659 | CB | LEU | A | 128 | −59.039 | 55.979 | 12.694 | 1.00 | 51.17 | C |
| ATOM | 1662 | CG | LEU | A | 128 | −58.463 | 57.046 | 11.746 | 1.00 | 51.31 | C |
| ATOM | 1664 | CD1 | LEU | A | 128 | −59.571 | 57.628 | 10.855 | 1.00 | 50.76 | C |
| ATOM | 1668 | CD2 | LEU | A | 128 | −57.762 | 58.157 | 12.508 | 1.00 | 50.98 | C |
| ATOM | 1672 | C | LEU | A | 128 | −58.996 | 54.353 | 14.581 | 1.00 | 51.06 | C |
| ATOM | 1673 | O | LEU | A | 128 | −59.573 | 53.393 | 14.078 | 1.00 | 50.94 | O |
| ATOM | 1675 | N | GLU | A | 129 | −59.053 | 54.637 | 15.879 | 1.00 | 51.12 | N |
| ATOM | 1676 | CA | GLU | A | 129 | −59.916 | 53.913 | 16.808 | 1.00 | 50.99 | C |
| ATOM | 1678 | CB | GLU | A | 129 | −60.019 | 54.665 | 18.132 | 1.00 | 51.14 | C |
| ATOM | 1681 | CG | GLU | A | 129 | −58.850 | 54.431 | 19.049 | 1.00 | 52.04 | C |
| ATOM | 1684 | CD | GLU | A | 129 | −58.903 | 53.069 | 19.697 | 1.00 | 53.22 | C |

TABLE 3-7-continued

| Coordinates of *P. tremuloides IspS* | | | | | | | | | | | |
|---|---|---|---|---|---|---|---|---|---|---|---|
| ATOM | 1685 | OE1 | GLU | A | 129 | −58.040 | 52.219 | 19.376 | 1.00 | 54.19 | O |
| ATOM | 1686 | OE2 | GLU | A | 129 | −59.823 | 52.848 | 20.516 | 1.00 | 53.51 | O |
| ATOM | 1687 | C | GLU | A | 129 | −61.314 | 53.712 | 16.260 | 1.00 | 50.66 | C |
| ATOM | 1688 | O | GLU | A | 129 | −61.791 | 52.587 | 16.200 | 1.00 | 50.83 | O |
| ATOM | 1690 | N | ASN | A | 130 | −61.960 | 54.799 | 15.839 | 1.00 | 50.28 | N |
| ATOM | 1691 | CA | ASN | A | 130 | −63.389 | 54.765 | 15.486 | 1.00 | 50.03 | C |
| ATOM | 1693 | CB | ASN | A | 130 | −63.910 | 56.182 | 15.193 | 1.00 | 50.09 | C |
| ATOM | 1696 | CG | ASN | A | 130 | −63.286 | 56.805 | 13.960 | 1.00 | 50.37 | C |
| ATOM | 1697 | OD1 | ASN | A | 130 | −62.504 | 56.177 | 13.249 | 1.00 | 51.44 | O |
| ATOM | 1698 | ND2 | ASN | A | 130 | −63.634 | 58.056 | 13.701 | 1.00 | 50.27 | N |
| ATOM | 1701 | C | ASN | A | 130 | −63.804 | 53.782 | 14.369 | 1.00 | 49.56 | C |
| ATOM | 1702 | O | ASN | A | 130 | −64.993 | 53.581 | 14.131 | 1.00 | 49.44 | O |
| ATOM | 1704 | N | LEU | A | 131 | −62.828 | 53.175 | 13.699 | 1.00 | 49.21 | N |
| ATOM | 1705 | CA | LEU | A | 131 | −63.087 | 52.103 | 12.729 | 1.00 | 48.78 | C |
| ATOM | 1707 | CB | LEU | A | 131 | −61.846 | 51.832 | 11.875 | 1.00 | 48.64 | C |
| ATOM | 1710 | CG | LEU | A | 131 | −61.445 | 52.939 | 10.898 | 1.00 | 48.26 | C |
| ATOM | 1712 | CD1 | LEU | A | 131 | −60.029 | 52.709 | 10.375 | 1.00 | 47.76 | C |
| ATOM | 1716 | CD2 | LEU | A | 131 | −62.441 | 53.039 | 9.754 | 1.00 | 47.32 | C |
| ATOM | 1720 | C | LEU | A | 131 | −63.516 | 50.798 | 13.394 | 1.00 | 48.58 | C |
| ATOM | 1721 | O | LEU | A | 131 | −64.093 | 49.939 | 12.731 | 1.00 | 48.64 | O |
| ATOM | 1723 | N | LYS | A | 132 | −63.225 | 50.645 | 14.689 | 1.00 | 48.23 | N |
| ATOM | 1724 | CA | LYS | A | 132 | −63.650 | 49.474 | 15.465 | 1.00 | 47.80 | C |
| ATOM | 1726 | CB | LYS | A | 132 | −63.156 | 49.587 | 16.913 | 1.00 | 47.71 | C |
| ATOM | 1729 | CG | LYS | A | 132 | −63.930 | 50.615 | 17.728 | 1.00 | 47.80 | C |
| ATOM | 1732 | CD | LYS | A | 132 | −63.430 | 50.779 | 19.153 | 1.00 | 47.75 | C |
| ATOM | 1735 | CE | LYS | A | 132 | −64.438 | 51.577 | 19.982 | 1.00 | 47.22 | C |
| ATOM | 1738 | NZ | LYS | A | 132 | −63.769 | 52.364 | 21.033 | 1.00 | 46.65 | N |
| ATOM | 1742 | C | LYS | A | 132 | −65.182 | 49.308 | 15.446 | 1.00 | 47.56 | C |
| ATOM | 1743 | O | LYS | A | 132 | −65.696 | 48.204 | 15.616 | 1.00 | 47.76 | O |
| ATOM | 1745 | N | GLU | A | 133 | −65.901 | 50.413 | 15.249 | 1.00 | 47.18 | N |
| ATOM | 1746 | CA | GLU | A | 133 | −67.371 | 50.412 | 15.191 | 1.00 | 46.79 | C |
| ATOM | 1748 | CB | GLU | A | 133 | −67.898 | 51.850 | 15.337 | 1.00 | 46.95 | C |
| ATOM | 1751 | CG | GLU | A | 133 | −67.840 | 52.376 | 16.776 | 1.00 | 47.56 | C |
| ATOM | 1754 | CD | GLU | A | 133 | −67.613 | 53.886 | 16.863 | 1.00 | 48.41 | C |
| ATOM | 1755 | OE1 | GLU | A | 133 | −68.247 | 54.648 | 16.093 | 1.00 | 47.67 | O |
| ATOM | 1756 | OE2 | GLU | A | 133 | −66.798 | 54.304 | 17.721 | 1.00 | 48.92 | O |
| ATOM | 1757 | C | GLU | A | 133 | −67.949 | 49.770 | 13.918 | 1.00 | 46.10 | C |
| ATOM | 1758 | O | GLU | A | 133 | −69.140 | 49.446 | 13.874 | 1.00 | 46.11 | O |
| ATOM | 1760 | N | ASP | A | 134 | −67.103 | 49.601 | 12.896 | 1.00 | 45.11 | N |
| ATOM | 1761 | CA | ASP | A | 134 | −67.477 | 48.995 | 11.608 | 1.00 | 44.06 | C |
| ATOM | 1763 | CB | ASP | A | 134 | −66.934 | 49.868 | 10.474 | 1.00 | 43.97 | C |
| ATOM | 1766 | CG | ASP | A | 134 | −67.380 | 49.411 | 9.104 | 1.00 | 44.08 | C |
| ATOM | 1767 | OD1 | ASP | A | 134 | −68.072 | 48.373 | 8.972 | 1.00 | 43.42 | O |
| ATOM | 1768 | OD2 | ASP | A | 134 | −67.020 | 50.116 | 8.141 | 1.00 | 44.84 | O |
| ATOM | 1769 | C | ASP | A | 134 | −66.910 | 47.570 | 11.526 | 1.00 | 43.12 | C |
| ATOM | 1770 | O | ASP | A | 134 | −65.788 | 47.357 | 11.080 | 1.00 | 43.19 | O |
| ATOM | 1772 | N | ILE | A | 135 | −67.708 | 46.594 | 11.944 | 1.00 | 41.85 | N |
| ATOM | 1773 | CA | ILE | A | 135 | −67.216 | 45.247 | 12.216 | 1.00 | 40.75 | C |
| ATOM | 1775 | CB | ILE | A | 135 | −68.183 | 44.507 | 13.170 | 1.00 | 40.80 | C |
| ATOM | 1777 | CG1 | ILE | A | 135 | −68.227 | 45.226 | 14.524 | 1.00 | 41.21 | C |
| ATOM | 1780 | CD1 | ILE | A | 135 | −69.353 | 46.283 | 14.633 | 1.00 | 42.86 | C |
| ATOM | 1784 | CG2 | ILE | A | 135 | −67.776 | 43.063 | 13.373 | 1.00 | 40.88 | C |
| ATOM | 1788 | C | ILE | A | 135 | −66.980 | 44.457 | 10.933 | 1.00 | 39.67 | C |
| ATOM | 1789 | O | ILE | A | 135 | −66.166 | 43.537 | 10.901 | 1.00 | 39.37 | O |
| ATOM | 1791 | N | LYS | A | 136 | −67.690 | 44.828 | 9.877 | 1.00 | 38.62 | N |
| ATOM | 1792 | CA | LYS | A | 136 | −67.465 | 44.256 | 8.554 | 1.00 | 37.88 | C |
| ATOM | 1794 | CB | LYS | A | 136 | −68.525 | 44.749 | 7.561 | 1.00 | 38.33 | C |
| ATOM | 1797 | CG | LYS | A | 136 | −69.955 | 44.342 | 7.879 | 1.00 | 40.17 | C |
| ATOM | 1800 | CD | LYS | A | 136 | −70.486 | 43.262 | 6.911 | 1.00 | 42.97 | C |
| ATOM | 1803 | CE | LYS | A | 136 | −71.624 | 42.389 | 7.536 | 1.00 | 44.00 | C |
| ATOM | 1806 | NZ | LYS | A | 136 | −72.950 | 43.086 | 7.726 | 1.00 | 43.82 | N |
| ATOM | 1810 | C | LYS | A | 136 | −66.097 | 44.687 | 8.047 | 1.00 | 36.38 | C |
| ATOM | 1811 | O | LYS | A | 136 | −65.399 | 43.914 | 7.388 | 1.00 | 36.24 | O |
| ATOM | 1813 | N | ALA | A | 137 | −65.728 | 45.931 | 8.341 | 1.00 | 34.51 | N |
| ATOM | 1814 | CA | ALA | A | 137 | −64.463 | 46.474 | 7.876 | 1.00 | 33.41 | C |
| ATOM | 1816 | CB | ALA | A | 137 | −64.432 | 47.981 | 8.058 | 1.00 | 33.43 | C |
| ATOM | 1820 | C | ALA | A | 137 | −63.291 | 45.827 | 8.600 | 1.00 | 32.30 | C |
| ATOM | 1821 | O | ALA | A | 137 | −62.288 | 45.481 | 7.995 | 1.00 | 31.89 | O |
| ATOM | 1823 | N | ILE | A | 138 | −63.437 | 45.662 | 9.905 | 1.00 | 31.41 | N |
| ATOM | 1824 | CA | ILE | A | 138 | −62.395 | 45.074 | 10.737 | 1.00 | 30.60 | C |
| ATOM | 1826 | CB | ILE | A | 138 | −62.770 | 45.131 | 12.238 | 1.00 | 30.20 | C |
| ATOM | 1828 | CG1 | ILE | A | 138 | −62.914 | 46.576 | 12.689 | 1.00 | 29.92 | C |
| ATOM | 1831 | CD1 | ILE | A | 138 | −61.681 | 47.414 | 12.417 | 1.00 | 30.50 | C |
| ATOM | 1835 | CG2 | ILE | A | 138 | −61.706 | 44.470 | 13.085 | 1.00 | 29.73 | C |
| ATOM | 1839 | C | ILE | A | 138 | −62.140 | 43.631 | 10.320 | 1.00 | 30.34 | C |
| ATOM | 1840 | O | ILE | A | 138 | −60.972 | 43.203 | 10.212 | 1.00 | 30.65 | O |
| ATOM | 1842 | N | LEU | A | 139 | −63.227 | 42.884 | 10.098 | 1.00 | 29.69 | N |
| ATOM | 1843 | CA | LEU | A | 139 | −63.134 | 41.523 | 9.562 | 1.00 | 29.23 | C |

TABLE 3-7-continued

Coordinates of *P. tremuloides IspS*

| | | | | | | | | | | | |
|---|---|---|---|---|---|---|---|---|---|---|---|
| ATOM | 1845 | CB | LEU | A | 139 | −64.517 | 40.917 | 9.332 | 1.00 | 28.92 | C |
| ATOM | 1848 | CG | LEU | A | 139 | −65.066 | 40.185 | 10.545 | 1.00 | 29.06 | C |
| ATOM | 1850 | CD1 | LEU | A | 139 | −66.541 | 39.875 | 10.352 | 1.00 | 28.20 | C |
| ATOM | 1854 | CD2 | LEU | A | 139 | −64.250 | 38.922 | 10.813 | 1.00 | 28.59 | C |
| ATOM | 1858 | C | LEU | A | 139 | −62.382 | 41.546 | 8.247 | 1.00 | 29.00 | C |
| ATOM | 1859 | O | LEU | A | 139 | −61.444 | 40.773 | 8.035 | 1.00 | 29.50 | O |
| ATOM | 1861 | N | SER | A | 140 | −62.790 | 42.458 | 7.372 | 1.00 | 28.14 | N |
| ATOM | 1862 | CA | SER | A | 140 | −62.222 | 42.526 | 6.054 | 1.00 | 27.40 | C |
| ATOM | 1864 | CB | SER | A | 140 | −62.912 | 43.619 | 5.260 | 1.00 | 27.35 | C |
| ATOM | 1867 | OG | SER | A | 140 | −63.310 | 43.103 | 4.015 | 1.00 | 28.43 | O |
| ATOM | 1869 | C | SER | A | 140 | −60.720 | 42.777 | 6.123 | 1.00 | 26.77 | C |
| ATOM | 1870 | O | SER | A | 140 | −59.975 | 42.269 | 5.298 | 1.00 | 27.29 | O |
| ATOM | 1872 | N | LEU | A | 141 | −60.285 | 43.563 | 7.105 | 1.00 | 25.89 | N |
| ATOM | 1873 | CA | LEU | A | 141 | −58.872 | 43.897 | 7.283 | 1.00 | 25.20 | C |
| ATOM | 1875 | CB | LEU | A | 141 | −58.717 | 45.164 | 8.155 | 1.00 | 25.00 | C |
| ATOM | 1878 | CG | LEU | A | 141 | −57.298 | 45.670 | 8.489 | 1.00 | 24.35 | C |
| ATOM | 1880 | CD1 | LEU | A | 141 | −56.497 | 45.974 | 7.232 | 1.00 | 22.75 | C |
| ATOM | 1884 | CD2 | LEU | A | 141 | −57.329 | 46.893 | 9.385 | 1.00 | 22.81 | C |
| ATOM | 1888 | C | LEU | A | 141 | −58.140 | 42.721 | 7.920 | 1.00 | 24.92 | C |
| ATOM | 1889 | O | LEU | A | 141 | −57.034 | 42.380 | 7.521 | 1.00 | 24.77 | O |
| ATOM | 1891 | N | TYR | A | 142 | −58.751 | 42.101 | 8.921 | 1.00 | 24.51 | N |
| ATOM | 1892 | CA | TYR | A | 142 | −58.163 | 40.913 | 9.514 | 1.00 | 24.36 | C |
| ATOM | 1894 | CB | TYR | A | 142 | −59.120 | 40.325 | 10.538 | 1.00 | 24.18 | C |
| ATOM | 1897 | CG | TYR | A | 142 | −58.774 | 38.941 | 11.046 | 1.00 | 23.72 | C |
| ATOM | 1898 | CD1 | TYR | A | 142 | −57.878 | 38.763 | 12.091 | 1.00 | 22.97 | C |
| ATOM | 1900 | CE1 | TYR | A | 142 | −57.593 | 37.500 | 12.582 | 1.00 | 24.25 | C |
| ATOM | 1902 | CZ | TYR | A | 142 | −58.229 | 36.386 | 12.030 | 1.00 | 25.75 | C |
| ATOM | 1903 | OH | TYR | A | 142 | −57.967 | 35.100 | 12.500 | 1.00 | 26.97 | O |
| ATOM | 1905 | CE2 | TYR | A | 142 | −59.120 | 36.551 | 10.988 | 1.00 | 25.02 | C |
| ATOM | 1907 | CD2 | TYR | A | 142 | −59.390 | 37.820 | 10.511 | 1.00 | 24.01 | C |
| ATOM | 1909 | C | TYR | A | 142 | −57.877 | 39.896 | 8.423 | 1.00 | 24.39 | C |
| ATOM | 1910 | O | TYR | A | 142 | −56.822 | 39.276 | 8.380 | 1.00 | 24.19 | O |
| ATOM | 1912 | N | GLU | A | 143 | −58.841 | 39.760 | 7.527 | 1.00 | 24.59 | N |
| ATOM | 1913 | CA | GLU | A | 143 | −58.820 | 38.728 | 6.521 | 1.00 | 24.70 | C |
| ATOM | 1915 | CB | GLU | A | 143 | −60.194 | 38.636 | 5.853 | 1.00 | 24.69 | C |
| ATOM | 1918 | CG | GLU | A | 143 | −60.651 | 37.219 | 5.547 | 1.00 | 27.21 | C |
| ATOM | 1921 | CD | GLU | A | 143 | −61.127 | 36.426 | 6.774 | 1.00 | 30.20 | C |
| ATOM | 1922 | OE1 | GLU | A | 143 | −60.261 | 35.776 | 7.393 | 1.00 | 33.40 | O |
| ATOM | 1923 | OE2 | GLU | A | 143 | −62.351 | 36.421 | 7.097 | 1.00 | 30.50 | O |
| ATOM | 1924 | C | GLU | A | 143 | −57.701 | 39.010 | 5.518 | 1.00 | 24.08 | C |
| ATOM | 1925 | O | GLU | A | 143 | −56.984 | 38.090 | 5.126 | 1.00 | 24.53 | O |
| ATOM | 1927 | N | ALA | A | 144 | −57.537 | 40.281 | 5.147 | 1.00 | 23.30 | N |
| ATOM | 1928 | CA | ALA | A | 144 | −56.515 | 40.715 | 4.173 | 1.00 | 22.79 | C |
| ATOM | 1930 | CB | ALA | A | 144 | −56.787 | 42.154 | 3.740 | 1.00 | 22.49 | C |
| ATOM | 1934 | C | ALA | A | 144 | −55.073 | 40.598 | 4.701 | 1.00 | 22.42 | C |
| ATOM | 1935 | O | ALA | A | 144 | −54.128 | 40.380 | 3.935 | 1.00 | 22.36 | O |
| ATOM | 1937 | N | SER | A | 145 | −54.909 | 40.713 | 6.012 | 1.00 | 21.80 | N |
| ATOM | 1938 | CA | SER | A | 145 | −53.593 | 40.822 | 6.600 | 1.00 | 21.36 | C |
| ATOM | 1940 | CB | SER | A | 145 | −53.726 | 41.170 | 8.066 | 1.00 | 21.21 | C |
| ATOM | 1943 | OG | SER | A | 145 | −54.337 | 40.100 | 8.753 | 1.00 | 21.59 | O |
| ATOM | 1945 | C | SER | A | 145 | −52.797 | 39.537 | 6.476 | 1.00 | 21.30 | C |
| ATOM | 1946 | O | SER | A | 145 | −51.571 | 39.533 | 6.701 | 1.00 | 21.50 | O |
| ATOM | 1948 | N | PHE | A | 146 | −53.488 | 38.439 | 6.154 | 1.00 | 21.00 | N |
| ATOM | 1949 | CA | PHE | A | 146 | −52.827 | 37.127 | 6.030 | 1.00 | 20.41 | C |
| ATOM | 1951 | CB | PHE | A | 146 | −53.796 | 35.979 | 6.338 | 1.00 | 20.20 | C |
| ATOM | 1954 | CG | PHE | A | 146 | −54.130 | 35.873 | 7.798 | 1.00 | 19.91 | C |
| ATOM | 1955 | CD1 | PHE | A | 146 | −53.382 | 35.087 | 8.637 | 1.00 | 20.48 | C |
| ATOM | 1957 | CE1 | PHE | A | 146 | −53.679 | 35.012 | 9.992 | 1.00 | 20.59 | C |
| ATOM | 1959 | CZ | PHE | A | 146 | −54.731 | 35.740 | 10.508 | 1.00 | 19.15 | C |
| ATOM | 1961 | CE2 | PHE | A | 146 | −55.464 | 36.536 | 9.691 | 1.00 | 19.10 | C |
| ATOM | 1963 | CD2 | PHE | A | 146 | −55.155 | 36.615 | 8.343 | 1.00 | 20.16 | C |
| ATOM | 1965 | C | PHE | A | 146 | −52.174 | 36.964 | 4.680 | 1.00 | 19.76 | C |
| ATOM | 1966 | O | PHE | A | 146 | −51.305 | 36.116 | 4.523 | 1.00 | 19.46 | O |
| ATOM | 1968 | N | LEU | A | 147 | −52.550 | 37.819 | 3.729 | 1.00 | 19.34 | N |
| ATOM | 1969 | CA | LEU | A | 147 | −51.933 | 37.804 | 2.402 | 1.00 | 19.13 | C |
| ATOM | 1971 | CB | LEU | A | 147 | −52.905 | 38.367 | 1.347 | 1.00 | 18.67 | C |
| ATOM | 1974 | CG | LEU | A | 147 | −53.964 | 37.334 | .919 | 1.00 | 18.11 | C |
| ATOM | 1976 | CD1 | LEU | A | 147 | −55.090 | 37.248 | 1.961 | 1.00 | 15.10 | C |
| ATOM | 1980 | CD2 | LEU | A | 147 | −54.494 | 37.609 | −.499 | 1.00 | 16.50 | C |
| ATOM | 1984 | C | LEU | A | 147 | −50.582 | 38.525 | 2.369 | 1.00 | 19.10 | C |
| ATOM | 1985 | O | LEU | A | 147 | −49.992 | 38.715 | 1.311 | 1.00 | 19.44 | O |
| ATOM | 1987 | N | ALA | A | 148 | −50.075 | 38.882 | 3.542 | 1.00 | 19.13 | N |
| ATOM | 1988 | CA | ALA | A | 148 | −48.967 | 39.806 | 3.664 | 1.00 | 18.84 | C |
| ATOM | 1990 | CB | ALA | A | 148 | −48.762 | 40.167 | 5.117 | 1.00 | 18.78 | C |
| ATOM | 1994 | C | ALA | A | 148 | −47.723 | 39.184 | 3.113 | 1.00 | 18.85 | C |
| ATOM | 1995 | O | ALA | A | 148 | −47.548 | 37.975 | 3.206 | 1.00 | 18.80 | O |
| ATOM | 1997 | N | LEU | A | 149 | −46.869 | 40.013 | 2.523 | 1.00 | 19.08 | N |
| ATOM | 1998 | CA | LEU | A | 149 | −45.507 | 39.601 | 2.215 | 1.00 | 19.32 | C |

TABLE 3-7-continued

Coordinates of *P. tremuloides IspS*

| | | | | | | | | | | | |
|---|---|---|---|---|---|---|---|---|---|---|---|
| ATOM | 2000 | CB | LEU | A | 149 | −45.056 | 40.145 | .863 | 1.00 | 19.14 | C |
| ATOM | 2003 | CG | LEU | A | 149 | −45.819 | 39.650 | −.364 | 1.00 | 19.16 | C |
| ATOM | 2005 | CD1 | LEU | A | 149 | −45.036 | 39.929 | −1.645 | 1.00 | 18.43 | C |
| ATOM | 2009 | CD2 | LEU | A | 149 | −46.089 | 38.175 | −.259 | 1.00 | 20.09 | C |
| ATOM | 2013 | C | LEU | A | 149 | −44.527 | 40.029 | 3.304 | 1.00 | 19.60 | C |
| ATOM | 2014 | O | LEU | A | 149 | −44.797 | 40.916 | 4.113 | 1.00 | 19.20 | O |
| ATOM | 2016 | N | GLU | A | 150 | −43.384 | 39.361 | 3.309 | 1.00 | 20.42 | N |
| ATOM | 2017 | CA | GLU | A | 150 | −42.286 | 39.674 | 4.215 | 1.00 | 21.03 | C |
| ATOM | 2019 | CB | GLU | A | 150 | −41.098 | 38.741 | 3.948 | 1.00 | 21.03 | C |
| ATOM | 2022 | CG | GLU | A | 150 | −40.491 | 38.176 | 5.205 | 1.00 | 22.23 | C |
| ATOM | 2025 | CD | GLU | A | 150 | −39.433 | 37.117 | 4.941 | 1.00 | 24.34 | C |
| ATOM | 2026 | OE1 | GLU | A | 150 | −39.189 | 36.786 | 3.753 | 1.00 | 24.53 | O |
| ATOM | 2027 | OE2 | GLU | A | 150 | −38.843 | 36.625 | 5.940 | 1.00 | 25.82 | O |
| ATOM | 2028 | C | GLU | A | 150 | −41.887 | 41.130 | 4.011 | 1.00 | 21.29 | C |
| ATOM | 2029 | O | GLU | A | 150 | −41.619 | 41.544 | 2.885 | 1.00 | 21.13 | O |
| ATOM | 2031 | N | GLY | A | 151 | −41.893 | 41.903 | 5.094 | 1.00 | 21.89 | N |
| ATOM | 2032 | CA | GLY | A | 151 | −41.636 | 43.341 | 5.030 | 1.00 | 22.25 | C |
| ATOM | 2035 | C | GLY | A | 151 | −42.871 | 44.221 | 5.152 | 1.00 | 22.67 | C |
| ATOM | 2036 | O | GLY | A | 151 | −42.757 | 45.397 | 5.462 | 1.00 | 22.84 | O |
| ATOM | 2038 | N | GLU | A | 152 | −44.055 | 43.669 | 4.918 | 1.00 | 23.19 | N |
| ATOM | 2039 | CA | GLU | A | 152 | −45.263 | 44.474 | 4.937 | 1.00 | 23.76 | C |
| ATOM | 2041 | CB | GLU | A | 152 | −46.350 | 43.813 | 4.100 | 1.00 | 23.79 | C |
| ATOM | 2044 | CG | GLU | A | 152 | −46.037 | 43.890 | 2.615 | 1.00 | 23.98 | C |
| ATOM | 2047 | CD | GLU | A | 152 | −47.147 | 43.368 | 1.749 | 1.00 | 23.72 | C |
| ATOM | 2048 | OE1 | GLU | A | 152 | −47.226 | 43.771 | .574 | 1.00 | 22.11 | O |
| ATOM | 2049 | OE2 | GLU | A | 152 | −47.939 | 42.542 | 2.241 | 1.00 | 25.41 | O |
| ATOM | 2050 | C | GLU | A | 152 | −45.722 | 44.719 | 6.365 | 1.00 | 24.47 | C |
| ATOM | 2051 | O | GLU | A | 152 | −46.586 | 44.006 | 6.906 | 1.00 | 24.70 | O |
| ATOM | 2053 | N | ASN | A | 153 | −45.134 | 45.744 | 6.969 | 1.00 | 25.00 | N |
| ATOM | 2054 | CA | ASN | A | 153 | −45.287 | 45.978 | 8.404 | 1.00 | 25.59 | C |
| ATOM | 2056 | CB | ASN | A | 153 | −44.221 | 46.957 | 8.902 | 1.00 | 25.55 | C |
| ATOM | 2059 | CG | ASN | A | 153 | −44.386 | 48.331 | 8.308 | 1.00 | 25.57 | C |
| ATOM | 2060 | OD1 | ASN | A | 153 | −44.114 | 48.557 | 7.128 | 1.00 | 24.52 | O |
| ATOM | 2061 | ND2 | ASN | A | 153 | −44.867 | 49.256 | 9.117 | 1.00 | 27.05 | N |
| ATOM | 2064 | C | ASN | A | 153 | −46.679 | 46.486 | 8.772 | 1.00 | 25.92 | C |
| ATOM | 2065 | O | ASN | A | 153 | −47.172 | 46.238 | 9.872 | 1.00 | 26.02 | O |
| ATOM | 2067 | N | ILE | A | 154 | −47.310 | 47.197 | 7.847 | 1.00 | 26.35 | N |
| ATOM | 2068 | CA | ILE | A | 154 | −48.638 | 47.751 | 8.082 | 1.00 | 26.57 | C |
| ATOM | 2070 | CB | ILE | A | 154 | −49.013 | 48.779 | 7.007 | 1.00 | 26.45 | C |
| ATOM | 2072 | CG1 | ILE | A | 154 | −48.159 | 50.023 | 7.164 | 1.00 | 26.36 | C |
| ATOM | 2075 | CD1 | ILE | A | 154 | −48.060 | 50.790 | 5.883 | 1.00 | 27.92 | C |
| ATOM | 2079 | CG2 | ILE | A | 154 | −50.467 | 49.152 | 7.089 | 1.00 | 26.25 | C |
| ATOM | 2083 | C | ILE | A | 154 | −49.674 | 46.643 | 8.111 | 1.00 | 26.96 | C |
| ATOM | 2084 | O | ILE | A | 154 | −50.650 | 46.741 | 8.851 | 1.00 | 27.12 | O |
| ATOM | 2086 | N | LEU | A | 155 | −49.467 | 45.588 | 7.320 | 1.00 | 27.35 | N |
| ATOM | 2087 | CA | LEU | A | 155 | −50.422 | 44.475 | 7.304 | 1.00 | 27.76 | C |
| ATOM | 2089 | CB | LEU | A | 155 | −50.238 | 43.594 | 6.067 | 1.00 | 27.73 | C |
| ATOM | 2092 | CG | LEU | A | 155 | −51.090 | 43.990 | 4.875 | 1.00 | 27.31 | C |
| ATOM | 2094 | CD1 | LEU | A | 155 | −50.980 | 45.456 | 4.683 | 1.00 | 28.13 | C |
| ATOM | 2098 | CD2 | LEU | A | 155 | −50.633 | 43.262 | 3.623 | 1.00 | 27.79 | C |
| ATOM | 2102 | C | LEU | A | 155 | −50.340 | 43.642 | 8.582 | 1.00 | 28.22 | C |
| ATOM | 2103 | O | LEU | A | 155 | −51.361 | 43.237 | 9.112 | 1.00 | 27.95 | O |
| ATOM | 2105 | N | ASP | A | 156 | −49.128 | 43.395 | 9.068 | 1.00 | 28.95 | N |
| ATOM | 2106 | CA | ASP | A | 156 | −48.944 | 42.723 | 10.348 | 1.00 | 29.71 | C |
| ATOM | 2108 | CB | ASP | A | 156 | −47.450 | 42.461 | 10.639 | 1.00 | 30.23 | C |
| ATOM | 2111 | CG | ASP | A | 156 | −46.938 | 41.125 | 10.027 | 1.00 | 32.82 | C |
| ATOM | 2112 | OD1 | ASP | A | 156 | −47.765 | 40.240 | 9.658 | 1.00 | 36.27 | O |
| ATOM | 2113 | OD2 | ASP | A | 156 | −45.700 | 40.961 | 9.923 | 1.00 | 34.48 | O |
| ATOM | 2114 | C | ASP | A | 156 | −49.570 | 43.539 | 11.469 | 1.00 | 29.66 | C |
| ATOM | 2115 | O | ASP | A | 156 | −50.109 | 42.969 | 12.425 | 1.00 | 29.81 | O |
| ATOM | 2117 | N | GLU | A | 157 | −49.514 | 44.866 | 11.345 | 1.00 | 29.69 | N |
| ATOM | 2118 | CA | GLU | A | 157 | −50.129 | 45.768 | 12.329 | 1.00 | 29.57 | C |
| ATOM | 2120 | CB | GLU | A | 157 | −49.581 | 47.186 | 12.178 | 1.00 | 29.71 | C |
| ATOM | 2123 | CG | GLU | A | 157 | −48.164 | 47.326 | 12.712 | 1.00 | 30.53 | C |
| ATOM | 2126 | CD | GLU | A | 157 | −47.455 | 48.544 | 12.169 | 1.00 | 31.96 | C |
| ATOM | 2127 | OE1 | GLU | A | 157 | −48.167 | 49.491 | 11.741 | 1.00 | 33.56 | O |
| ATOM | 2128 | OE2 | GLU | A | 157 | −46.195 | 48.546 | 12.166 | 1.00 | 31.54 | O |
| ATOM | 2129 | C | GLU | A | 157 | −51.649 | 45.771 | 12.230 | 1.00 | 29.16 | C |
| ATOM | 2130 | O | GLU | A | 157 | −52.330 | 45.819 | 13.241 | 1.00 | 29.00 | O |
| ATOM | 2132 | N | ALA | A | 158 | −52.172 | 45.716 | 11.010 | 1.00 | 28.86 | N |
| ATOM | 2133 | CA | ALA | A | 158 | −53.606 | 45.570 | 10.792 | 1.00 | 28.79 | C |
| ATOM | 2135 | CB | ALA | A | 158 | −53.893 | 45.456 | 9.301 | 1.00 | 28.44 | C |
| ATOM | 2139 | C | ALA | A | 158 | −54.171 | 44.352 | 11.536 | 1.00 | 28.93 | C |
| ATOM | 2140 | O | ALA | A | 158 | −55.265 | 44.402 | 12.098 | 1.00 | 28.77 | O |
| ATOM | 2142 | N | LYS | A | 159 | −53.416 | 43.260 | 11.528 | 1.00 | 29.19 | N |
| ATOM | 2143 | CA | LYS | A | 159 | −53.849 | 42.022 | 12.143 | 1.00 | 29.57 | C |
| ATOM | 2145 | CB | LYS | A | 159 | −52.929 | 40.880 | 11.710 | 1.00 | 29.62 | C |
| ATOM | 2148 | CG | LYS | A | 159 | −53.297 | 39.513 | 12.258 | 1.00 | 30.27 | C |

TABLE 3-7-continued

Coordinates of *P. tremuloides IspS*

| | | | | | | | | | | | |
|---|---|---|---|---|---|---|---|---|---|---|---|
| ATOM | 2151 | CD | LYS | A | 159 | −52.765 | 38.365 | 11.387 | 1.00 | 31.78 | C |
| ATOM | 2154 | CE | LYS | A | 159 | −51.259 | 38.132 | 11.525 | 1.00 | 33.15 | C |
| ATOM | 2157 | NZ | LYS | A | 159 | −50.911 | 36.696 | 11.248 | 1.00 | 33.88 | N |
| ATOM | 2161 | C | LYS | A | 159 | −53.866 | 42.160 | 13.670 | 1.00 | 29.99 | C |
| ATOM | 2162 | O | LYS | A | 159 | −54.767 | 41.642 | 14.332 | 1.00 | 30.29 | O |
| ATOM | 2164 | N | VAL | A | 160 | −52.886 | 42.862 | 14.236 | 1.00 | 30.07 | N |
| ATOM | 2165 | CA | VAL | A | 160 | −52.840 | 43.047 | 15.696 | 1.00 | 30.03 | C |
| ATOM | 2167 | CB | VAL | A | 160 | −51.520 | 43.691 | 16.162 | 1.00 | 29.88 | C |
| ATOM | 2169 | CG1 | VAL | A | 160 | −51.515 | 43.863 | 17.671 | 1.00 | 28.94 | C |
| ATOM | 2173 | CG2 | VAL | A | 160 | −50.341 | 42.848 | 15.707 | 1.00 | 30.23 | C |
| ATOM | 2177 | C | VAL | A | 160 | −53.996 | 43.925 | 16.149 | 1.00 | 30.05 | C |
| ATOM | 2178 | O | VAL | A | 160 | −54.544 | 43.752 | 17.234 | 1.00 | 30.31 | O |
| ATOM | 2180 | N | PHE | A | 161 | −54.355 | 44.862 | 15.290 | 1.00 | 30.08 | N |
| ATOM | 2181 | CA | PHE | A | 161 | −55.407 | 45.808 | 15.558 | 1.00 | 30.09 | C |
| ATOM | 2183 | CB | PHE | A | 161 | −55.255 | 46.993 | 14.598 | 1.00 | 29.92 | C |
| ATOM | 2186 | CG | PHE | A | 161 | −56.370 | 47.974 | 14.654 | 1.00 | 28.52 | C |
| ATOM | 2187 | CD1 | PHE | A | 161 | −56.347 | 49.005 | 15.554 | 1.00 | 27.92 | C |
| ATOM | 2189 | CE1 | PHE | A | 161 | −57.361 | 49.903 | 15.600 | 1.00 | 28.06 | C |
| ATOM | 2191 | CZ | PHE | A | 161 | −58.411 | 49.783 | 14.733 | 1.00 | 28.76 | C |
| ATOM | 2193 | CE2 | PHE | A | 161 | −58.441 | 48.757 | 13.826 | 1.00 | 28.31 | C |
| ATOM | 2195 | CD2 | PHE | A | 161 | −57.429 | 47.869 | 13.789 | 1.00 | 28.16 | C |
| ATOM | 2197 | C | PHE | A | 161 | −56.746 | 45.123 | 15.388 | 1.00 | 30.55 | C |
| ATOM | 2198 | O | PHE | A | 161 | −57.598 | 45.203 | 16.258 | 1.00 | 30.53 | O |
| ATOM | 2200 | N | ALA | A | 162 | −56.930 | 44.438 | 14.271 | 1.00 | 31.34 | N |
| ATOM | 2201 | CA | ALA | A | 162 | −58.193 | 43.770 | 14.023 | 1.00 | 32.26 | C |
| ATOM | 2203 | CB | ALA | A | 162 | −58.217 | 43.139 | 12.643 | 1.00 | 32.31 | C |
| ATOM | 2207 | C | ALA | A | 162 | −58.500 | 42.734 | 15.118 | 1.00 | 33.09 | C |
| ATOM | 2208 | O | ALA | A | 162 | −59.557 | 42.814 | 15.735 | 1.00 | 33.83 | O |
| ATOM | 2210 | N | ILE | A | 163 | −57.587 | 41.799 | 15.393 | 1.00 | 33.59 | N |
| ATOM | 2211 | CA | ILE | A | 163 | −57.826 | 40.799 | 16.438 | 1.00 | 34.02 | C |
| ATOM | 2213 | CB | ILE | A | 163 | −56.597 | 39.907 | 16.745 | 1.00 | 33.98 | C |
| ATOM | 2215 | CG1 | ILE | A | 163 | −56.235 | 39.008 | 15.566 | 1.00 | 34.37 | C |
| ATOM | 2218 | CD1 | ILE | A | 163 | −54.878 | 38.317 | 15.722 | 1.00 | 34.38 | C |
| ATOM | 2222 | CG2 | ILE | A | 163 | −56.883 | 38.995 | 17.919 | 1.00 | 33.38 | C |
| ATOM | 2226 | C | ILE | A | 163 | −58.225 | 41.472 | 17.744 | 1.00 | 34.75 | C |
| ATOM | 2227 | O | ILE | A | 163 | −59.189 | 41.064 | 18.373 | 1.00 | 35.03 | O |
| ATOM | 2229 | N | SER | A | 164 | −57.501 | 42.504 | 18.156 | 1.00 | 35.76 | N |
| ATOM | 2230 | CA | SER | A | 164 | −57.763 | 43.117 | 19.463 | 1.00 | 36.59 | C |
| ATOM | 2232 | CB | SER | A | 164 | −56.828 | 44.293 | 19.735 | 1.00 | 36.59 | C |
| ATOM | 2235 | OG | SER | A | 164 | −57.350 | 45.485 | 19.164 | 1.00 | 36.46 | O |
| ATOM | 2237 | C | SER | A | 164 | −59.196 | 43.611 | 19.556 | 1.00 | 37.42 | C |
| ATOM | 2238 | O | SER | A | 164 | −59.860 | 43.420 | 20.571 | 1.00 | 37.38 | O |
| ATOM | 2240 | N | HIS | A | 165 | −59.661 | 44.251 | 18.486 | 1.00 | 38.51 | N |
| ATOM | 2241 | CA | HIS | A | 165 | −60.990 | 44.851 | 18.467 | 1.00 | 39.40 | C |
| ATOM | 2243 | CB | HIS | A | 165 | −61.008 | 46.097 | 17.574 | 1.00 | 39.76 | C |
| ATOM | 2246 | CG | HIS | A | 165 | −60.467 | 47.323 | 18.251 | 1.00 | 42.06 | C |
| ATOM | 2247 | ND1 | HIS | A | 165 | −59.205 | 47.821 | 18.000 | 1.00 | 44.21 | N |
| ATOM | 2249 | CE1 | HIS | A | 165 | −58.998 | 48.893 | 18.748 | 1.00 | 45.04 | C |
| ATOM | 2251 | NE2 | HIS | A | 165 | −60.080 | 49.106 | 19.478 | 1.00 | 44.99 | N |
| ATOM | 2253 | CD2 | HIS | A | 165 | −61.011 | 48.135 | 19.192 | 1.00 | 43.76 | C |
| ATOM | 2255 | C | HIS | A | 165 | −62.078 | 43.872 | 18.060 | 1.00 | 39.38 | C |
| ATOM | 2256 | O | HIS | A | 165 | −63.248 | 44.244 | 18.067 | 1.00 | 39.43 | O |
| ATOM | 2258 | N | LEU | A | 166 | −61.683 | 42.632 | 17.745 | 1.00 | 39.54 | N |
| ATOM | 2259 | CA | LEU | A | 166 | −62.589 | 41.550 | 17.326 | 1.00 | 39.55 | C |
| ATOM | 2261 | CB | LEU | A | 166 | −62.001 | 40.766 | 16.154 | 1.00 | 39.28 | C |
| ATOM | 2264 | CG | LEU | A | 166 | −62.156 | 41.339 | 14.752 | 1.00 | 38.23 | C |
| ATOM | 2266 | CD1 | LEU | A | 166 | −61.361 | 40.501 | 13.805 | 1.00 | 37.53 | C |
| ATOM | 2270 | CD2 | LEU | A | 166 | −63.594 | 41.367 | 14.332 | 1.00 | 37.21 | C |
| ATOM | 2274 | C | LEU | A | 166 | −62.842 | 40.555 | 18.438 | 1.00 | 40.08 | C |
| ATOM | 2275 | O | LEU | A | 166 | −63.991 | 40.220 | 18.733 | 1.00 | 40.42 | O |
| ATOM | 2277 | N | LYS | A | 167 | −61.766 | 40.074 | 19.052 | 1.00 | 40.58 | N |
| ATOM | 2278 | CA | LYS | A | 167 | −61.875 | 39.090 | 20.133 | 1.00 | 41.09 | C |
| ATOM | 2280 | CB | LYS | A | 167 | −60.491 | 38.632 | 20.595 | 1.00 | 41.13 | C |
| ATOM | 2283 | CG | LYS | A | 167 | −59.897 | 39.399 | 21.768 | 1.00 | 42.16 | C |
| ATOM | 2286 | CD | LYS | A | 167 | −58.421 | 39.035 | 22.013 | 1.00 | 44.45 | C |
| ATOM | 2289 | CE | LYS | A | 167 | −58.070 | 37.561 | 21.654 | 1.00 | 45.56 | C |
| ATOM | 2292 | NZ | LYS | A | 167 | −56.610 | 37.237 | 21.798 | 1.00 | 46.20 | N |
| ATOM | 2296 | C | LYS | A | 167 | −62.678 | 39.584 | 21.337 | 1.00 | 41.23 | C |
| ATOM | 2297 | O | LYS | A | 167 | −62.994 | 38.793 | 22.215 | 1.00 | 41.47 | O |
| ATOM | 2299 | N | GLU | A | 168 | −62.995 | 40.884 | 21.352 | 1.00 | 41.49 | N |
| ATOM | 2300 | CA | GLU | A | 168 | −63.704 | 41.583 | 22.437 | 1.00 | 41.42 | C |
| ATOM | 2302 | CB | GLU | A | 168 | −65.201 | 41.730 | 22.100 | 1.00 | 41.27 | C |
| ATOM | 2305 | CG | GLU | A | 168 | −65.995 | 40.424 | 22.016 | 1.00 | 41.01 | C |
| ATOM | 2308 | CD | GLU | A | 168 | −66.928 | 40.328 | 20.787 | 1.00 | 40.84 | C |
| ATOM | 2309 | OE1 | GLU | A | 168 | −66.701 | 41.040 | 19.770 | 1.00 | 39.82 | O |
| ATOM | 2310 | OE2 | GLU | A | 168 | −67.884 | 39.509 | 20.845 | 1.00 | 39.04 | O |
| ATOM | 2311 | C | GLU | A | 168 | −63.484 | 41.004 | 23.843 | 1.00 | 41.66 | C |
| ATOM | 2312 | O | GLU | A | 168 | −62.435 | 41.231 | 24.469 | 1.00 | 41.46 | O |

TABLE 3-7-continued

Coordinates of *P. tremuloides IspS*

| | | | | | | | | | | | |
|---|---|---|---|---|---|---|---|---|---|---|---|
| ATOM | 2314 | N | GLU | A | 172 | −71.668 | 38.961 | 21.192 | 1.00 | 55.65 | N |
| ATOM | 2315 | CA | GLU | A | 172 | −73.052 | 39.153 | 20.721 | 1.00 | 56.00 | C |
| ATOM | 2317 | CB | GLU | A | 172 | −73.876 | 37.880 | 20.937 | 1.00 | 56.27 | C |
| ATOM | 2320 | CG | GLU | A | 172 | −73.198 | 36.620 | 20.390 | 1.00 | 57.12 | C |
| ATOM | 2323 | CD | GLU | A | 172 | −74.056 | 35.363 | 20.516 | 1.00 | 58.18 | C |
| ATOM | 2324 | OE1 | GLU | A | 172 | −75.300 | 35.480 | 20.622 | 1.00 | 58.84 | O |
| ATOM | 2325 | OE2 | GLU | A | 172 | −73.480 | 34.249 | 20.498 | 1.00 | 58.98 | O |
| ATOM | 2326 | C | GLU | A | 172 | −73.766 | 40.386 | 21.334 | 1.00 | 55.70 | C |
| ATOM | 2327 | O | GLU | A | 172 | −74.956 | 40.347 | 21.688 | 1.00 | 54.95 | O |
| ATOM | 2329 | N | LYS | A | 173 | −72.987 | 41.458 | 21.486 | 1.00 | 55.58 | N |
| ATOM | 2330 | CA | LYS | A | 173 | −73.496 | 42.831 | 21.466 | 1.00 | 55.43 | C |
| ATOM | 2332 | CB | LYS | A | 173 | −72.649 | 43.741 | 22.357 | 1.00 | 55.51 | C |
| ATOM | 2335 | CG | LYS | A | 173 | −72.527 | 43.223 | 23.793 | 1.00 | 56.07 | C |
| ATOM | 2338 | CD | LYS | A | 173 | −72.803 | 44.291 | 24.868 | 1.00 | 55.87 | C |
| ATOM | 2341 | CE | LYS | A | 173 | −73.111 | 43.642 | 26.221 | 1.00 | 55.20 | C |
| ATOM | 2344 | NZ | LYS | A | 173 | −72.893 | 44.576 | 27.348 | 1.00 | 54.63 | N |
| ATOM | 2348 | C | LYS | A | 173 | −73.449 | 43.297 | 20.009 | 1.00 | 55.01 | C |
| ATOM | 2349 | O | LYS | A | 173 | −74.091 | 44.274 | 19.625 | 1.00 | 54.97 | O |
| ATOM | 2351 | N | ILE | A | 174 | −72.647 | 42.581 | 19.223 | 1.00 | 54.57 | N |
| ATOM | 2352 | CA | ILE | A | 174 | −72.713 | 42.550 | 17.767 | 1.00 | 54.22 | C |
| ATOM | 2354 | CB | ILE | A | 174 | −71.429 | 41.845 | 17.227 | 1.00 | 54.21 | C |
| ATOM | 2356 | CG1 | ILE | A | 174 | −70.196 | 42.724 | 17.474 | 1.00 | 54.73 | C |
| ATOM | 2359 | CD1 | ILE | A | 174 | −68.858 | 41.949 | 17.553 | 1.00 | 55.78 | C |
| ATOM | 2363 | CG2 | ILE | A | 174 | −71.532 | 41.504 | 15.759 | 1.00 | 54.06 | C |
| ATOM | 2367 | C | ILE | A | 174 | −73.957 | 41.744 | 17.384 | 1.00 | 53.88 | C |
| ATOM | 2368 | O | ILE | A | 174 | −74.587 | 41.134 | 18.250 | 1.00 | 53.83 | O |
| ATOM | 2370 | N | GLY | A | 175 | −74.332 | 41.747 | 16.107 | 1.00 | 53.59 | N |
| ATOM | 2371 | CA | GLY | A | 175 | −75.351 | 40.817 | 15.613 | 1.00 | 53.51 | C |
| ATOM | 2374 | C | GLY | A | 175 | −75.130 | 39.395 | 16.126 | 1.00 | 53.43 | C |
| ATOM | 2375 | O | GLY | A | 175 | −74.119 | 39.105 | 16.760 | 1.00 | 53.80 | O |
| ATOM | 2377 | N | LYS | A | 176 | −76.070 | 38.495 | 15.861 | 1.00 | 53.10 | N |
| ATOM | 2378 | CA | LYS | A | 176 | −75.926 | 37.098 | 16.286 | 1.00 | 52.68 | C |
| ATOM | 2380 | CB | LYS | A | 176 | −77.291 | 36.522 | 16.677 | 1.00 | 52.99 | C |
| ATOM | 2383 | CG | LYS | A | 176 | −78.003 | 37.387 | 17.746 | 1.00 | 54.12 | C |
| ATOM | 2386 | CD | LYS | A | 176 | −79.201 | 36.697 | 18.436 | 1.00 | 54.57 | C |
| ATOM | 2389 | CE | LYS | A | 176 | −79.503 | 37.369 | 19.792 | 1.00 | 54.79 | C |
| ATOM | 2392 | NZ | LYS | A | 176 | −80.458 | 36.598 | 20.653 | 1.00 | 55.20 | N |
| ATOM | 2396 | C | LYS | A | 176 | −75.246 | 36.267 | 15.196 | 1.00 | 51.83 | C |
| ATOM | 2397 | O | LYS | A | 176 | −74.393 | 35.433 | 15.486 | 1.00 | 51.69 | O |
| ATOM | 2399 | N | GLU | A | 177 | −75.609 | 36.520 | 13.940 | 1.00 | 50.90 | N |
| ATOM | 2400 | CA | GLU | A | 177 | −74.975 | 35.854 | 12.800 | 1.00 | 50.19 | C |
| ATOM | 2402 | CB | GLU | A | 177 | −75.792 | 36.062 | 11.507 | 1.00 | 50.41 | C |
| ATOM | 2405 | CG | GLU | A | 177 | −75.506 | 37.368 | 10.735 | 1.00 | 51.03 | C |
| ATOM | 2408 | CD | GLU | A | 177 | −76.403 | 37.572 | 9.507 | 1.00 | 52.17 | C |
| ATOM | 2409 | OE1 | GLU | A | 177 | −75.955 | 38.276 | 8.569 | 1.00 | 52.63 | O |
| ATOM | 2410 | OE2 | GLU | A | 177 | −77.546 | 37.048 | 9.479 | 1.00 | 52.03 | O |
| ATOM | 2411 | C | GLU | A | 177 | −73.549 | 36.369 | 12.607 | 1.00 | 49.10 | C |
| ATOM | 2412 | O | GLU | A | 177 | −72.626 | 35.597 | 12.321 | 1.00 | 49.53 | O |
| ATOM | 2414 | N | LEU | A | 178 | −73.388 | 37.681 | 12.770 | 1.00 | 47.39 | N |
| ATOM | 2415 | CA | LEU | A | 178 | −72.110 | 38.371 | 12.575 | 1.00 | 45.63 | C |
| ATOM | 2417 | CB | LEU | A | 178 | −72.352 | 39.877 | 12.615 | 1.00 | 45.59 | C |
| ATOM | 2420 | CG | LEU | A | 178 | −71.280 | 40.809 | 12.085 | 1.00 | 45.45 | C |
| ATOM | 2422 | CD1 | LEU | A | 178 | −70.969 | 40.515 | 10.620 | 1.00 | 45.45 | C |
| ATOM | 2426 | CD2 | LEU | A | 178 | −71.765 | 42.233 | 12.279 | 1.00 | 44.63 | C |
| ATOM | 2430 | C | LEU | A | 178 | −71.095 | 37.979 | 13.634 | 1.00 | 44.06 | C |
| ATOM | 2431 | O | LEU | A | 178 | −69.902 | 38.012 | 13.387 | 1.00 | 43.70 | O |
| ATOM | 2433 | N | ALA | A | 179 | −71.586 | 37.611 | 14.810 | 1.00 | 42.54 | N |
| ATOM | 2434 | CA | ALA | A | 179 | −70.753 | 37.041 | 15.847 | 1.00 | 41.66 | C |
| ATOM | 2436 | CB | ALA | A | 179 | −71.545 | 36.884 | 17.122 | 1.00 | 41.69 | C |
| ATOM | 2440 | C | ALA | A | 179 | −70.193 | 35.695 | 15.416 | 1.00 | 40.75 | C |
| ATOM | 2441 | O | ALA | A | 179 | −69.078 | 35.351 | 15.769 | 1.00 | 40.61 | O |
| ATOM | 2443 | N | GLU | A | 180 | −70.974 | 34.931 | 14.664 | 1.00 | 39.88 | N |
| ATOM | 2444 | CA | GLU | A | 180 | −70.518 | 33.639 | 14.143 | 1.00 | 39.40 | C |
| ATOM | 2446 | CB | GLU | A | 180 | −71.710 | 32.781 | 13.718 | 1.00 | 39.74 | C |
| ATOM | 2449 | CG | GLU | A | 180 | −72.650 | 32.415 | 14.865 | 1.00 | 40.88 | C |
| ATOM | 2452 | CD | GLU | A | 180 | −73.913 | 31.710 | 14.398 | 1.00 | 42.02 | C |
| ATOM | 2453 | OE1 | GLU | A | 180 | −74.380 | 32.022 | 13.271 | 1.00 | 43.05 | O |
| ATOM | 2454 | OE2 | GLU | A | 180 | −74.437 | 30.857 | 15.166 | 1.00 | 41.93 | O |
| ATOM | 2455 | C | GLU | A | 180 | −69.565 | 33.805 | 12.960 | 1.00 | 38.29 | C |
| ATOM | 2456 | O | GLU | A | 180 | −68.739 | 32.940 | 12.699 | 1.00 | 38.23 | O |
| ATOM | 2458 | N | GLN | A | 181 | −69.704 | 34.911 | 12.240 | 1.00 | 36.92 | N |
| ATOM | 2459 | CA | GLN | A | 181 | −68.748 | 35.299 | 11.223 | 1.00 | 35.74 | C |
| ATOM | 2461 | CB | GLN | A | 181 | −69.272 | 36.516 | 10.463 | 1.00 | 35.94 | C |
| ATOM | 2464 | CG | GLN | A | 181 | −68.931 | 36.537 | 8.975 | 1.00 | 36.93 | C |
| ATOM | 2467 | CD | GLN | A | 181 | −69.693 | 35.492 | 8.176 | 1.00 | 37.72 | C |
| ATOM | 2468 | OE1 | GLN | A | 181 | −70.769 | 35.067 | 8.567 | 1.00 | 38.78 | O |
| ATOM | 2469 | NE2 | GLN | A | 181 | −69.139 | 35.083 | 7.050 | 1.00 | 38.11 | N |
| ATOM | 2472 | C | GLN | A | 181 | −67.406 | 35.632 | 11.881 | 1.00 | 34.64 | C |

TABLE 3-7-continued

Coordinates of *P. tremuloides IspS*

| | | | | | | | | | | | |
|---|---|---|---|---|---|---|---|---|---|---|---|
| ATOM | 2473 | O | GLN | A | 181 | −66.348 | 35.411 | 11.294 | 1.00 | 34.73 | O |
| ATOM | 2475 | N | VAL | A | 182 | −67.448 | 36.158 | 13.102 | 1.00 | 33.29 | N |
| ATOM | 2476 | CA | VAL | A | 182 | −66.224 | 36.488 | 13.842 | 1.00 | 32.28 | C |
| ATOM | 2478 | CB | VAL | A | 182 | −66.433 | 37.653 | 14.855 | 1.00 | 32.10 | C |
| ATOM | 2480 | CG1 | VAL | A | 182 | −66.328 | 38.991 | 14.166 | 1.00 | 31.51 | C |
| ATOM | 2484 | CG2 | VAL | A | 182 | −65.420 | 37.594 | 15.957 | 1.00 | 31.69 | C |
| ATOM | 2488 | C | VAL | A | 182 | −65.613 | 35.298 | 14.575 | 1.00 | 31.49 | C |
| ATOM | 2489 | O | VAL | A | 182 | −64.396 | 35.230 | 14.668 | 1.00 | 31.43 | O |
| ATOM | 2491 | N | SER | A | 183 | −66.422 | 34.378 | 15.106 | 1.00 | 30.56 | N |
| ATOM | 2492 | CA | SER | A | 183 | −65.860 | 33.174 | 15.744 | 1.00 | 30.16 | C |
| ATOM | 2494 | CB | SER | A | 183 | −66.926 | 32.253 | 16.327 | 1.00 | 30.29 | C |
| ATOM | 2497 | OG | SER | A | 183 | −67.796 | 32.934 | 17.214 | 1.00 | 32.35 | O |
| ATOM | 2499 | C | SER | A | 183 | −65.111 | 32.403 | 14.692 | 1.00 | 29.30 | C |
| ATOM | 2500 | O | SER | A | 183 | −63.974 | 31.981 | 14.903 | 1.00 | 29.32 | O |
| ATOM | 2502 | N | HIS | A | 184 | −65.768 | 32.252 | 13.546 | 1.00 | 28.24 | N |
| ATOM | 2503 | CA | HIS | A | 184 | −65.215 | 31.578 | 12.379 | 1.00 | 27.36 | C |
| ATOM | 2505 | CB | HIS | A | 184 | −66.245 | 31.653 | 11.254 | 1.00 | 27.41 | C |
| ATOM | 2508 | CG | HIS | A | 184 | −65.930 | 30.807 | 10.064 | 1.00 | 26.90 | C |
| ATOM | 2509 | ND1 | HIS | A | 184 | −65.484 | 29.511 | 10.166 | 1.00 | 27.76 | N |
| ATOM | 2511 | CE1 | HIS | A | 184 | −65.321 | 29.009 | 8.955 | 1.00 | 27.47 | C |
| ATOM | 2513 | NE2 | HIS | A | 184 | −65.661 | 29.929 | 8.075 | 1.00 | 26.52 | N |
| ATOM | 2515 | CD2 | HIS | A | 184 | −66.059 | 31.058 | 8.742 | 1.00 | 26.61 | C |
| ATOM | 2517 | C | HIS | A | 184 | −63.898 | 32.200 | 11.940 | 1.00 | 26.69 | C |
| ATOM | 2518 | O | HIS | A | 184 | −62.881 | 31.525 | 11.862 | 1.00 | 26.44 | O |
| ATOM | 2520 | N | ALA | A | 185 | −63.909 | 33.498 | 11.675 | 1.00 | 26.11 | N |
| ATOM | 2521 | CA | ALA | A | 185 | −62.711 | 34.176 | 11.205 | 1.00 | 25.63 | C |
| ATOM | 2523 | CB | ALA | A | 185 | −62.970 | 35.627 | 11.109 | 1.00 | 25.74 | C |
| ATOM | 2527 | C | ALA | A | 185 | −61.552 | 33.917 | 12.153 | 1.00 | 25.33 | C |
| ATOM | 2528 | O | ALA | A | 185 | −60.451 | 33.572 | 11.725 | 1.00 | 25.79 | O |
| ATOM | 2530 | N | LEU | A | 186 | −61.814 | 34.066 | 13.450 | 1.00 | 24.77 | N |
| ATOM | 2531 | CA | LEU | A | 186 | −60.776 | 33.940 | 14.470 | 1.00 | 24.05 | C |
| ATOM | 2533 | CB | LEU | A | 186 | −61.256 | 34.498 | 15.814 | 1.00 | 23.63 | C |
| ATOM | 2536 | CG | LEU | A | 186 | −61.516 | 36.012 | 15.903 | 1.00 | 22.51 | C |
| ATOM | 2538 | CD1 | LEU | A | 186 | −62.057 | 36.399 | 17.266 | 1.00 | 20.79 | C |
| ATOM | 2542 | CD2 | LEU | A | 186 | −60.273 | 36.793 | 15.613 | 1.00 | 21.13 | C |
| ATOM | 2546 | C | LEU | A | 186 | −60.316 | 32.497 | 14.613 | 1.00 | 24.02 | C |
| ATOM | 2547 | O | LEU | A | 186 | −59.169 | 32.250 | 14.943 | 1.00 | 24.27 | O |
| ATOM | 2549 | N | GLU | A | 187 | −61.201 | 31.543 | 14.347 | 1.00 | 23.88 | N |
| ATOM | 2550 | CA | GLU | A | 187 | −60.836 | 30.117 | 14.348 | 1.00 | 23.53 | C |
| ATOM | 2552 | CB | GLU | A | 187 | −62.029 | 29.270 | 13.919 | 1.00 | 23.66 | C |
| ATOM | 2555 | CG | GLU | A | 187 | −61.945 | 27.828 | 14.316 | 1.00 | 25.26 | C |
| ATOM | 2558 | CD | GLU | A | 187 | −63.049 | 26.971 | 13.693 | 1.00 | 28.04 | C |
| ATOM | 2559 | OE1 | GLU | A | 187 | −63.672 | 27.393 | 12.681 | 1.00 | 28.67 | O |
| ATOM | 2560 | OE2 | GLU | A | 187 | −63.288 | 25.858 | 14.225 | 1.00 | 29.72 | O |
| ATOM | 2561 | C | GLU | A | 187 | −59.686 | 29.838 | 13.395 | 1.00 | 22.92 | C |
| ATOM | 2562 | O | GLU | A | 187 | −58.765 | 29.091 | 13.729 | 1.00 | 22.53 | O |
| ATOM | 2564 | N | LEU | A | 188 | −59.763 | 30.446 | 12.209 | 1.00 | 22.46 | N |
| ATOM | 2565 | CA | LEU | A | 188 | −58.799 | 30.246 | 11.121 | 1.00 | 22.07 | C |
| ATOM | 2567 | CB | LEU | A | 188 | −58.802 | 28.794 | 10.635 | 1.00 | 22.11 | C |
| ATOM | 2570 | CG | LEU | A | 188 | −57.876 | 28.362 | 9.493 | 1.00 | 22.17 | C |
| ATOM | 2572 | CD1 | LEU | A | 188 | −56.456 | 28.051 | 9.961 | 1.00 | 21.62 | C |
| ATOM | 2576 | CD2 | LEU | A | 188 | −58.464 | 27.134 | 8.822 | 1.00 | 22.40 | C |
| ATOM | 2580 | C | LEU | A | 188 | −59.237 | 31.137 | 9.985 | 1.00 | 21.69 | C |
| ATOM | 2581 | O | LEU | A | 188 | −60.380 | 31.075 | 9.563 | 1.00 | 21.53 | O |
| ATOM | 2583 | N | PRO | A | 189 | −58.333 | 31.973 | 9.474 | 1.00 | 21.46 | N |
| ATOM | 2584 | CA | PRO | A | 189 | −58.745 | 32.935 | 8.472 | 1.00 | 21.18 | C |
| ATOM | 2586 | CB | PRO | A | 189 | −57.592 | 33.936 | 8.486 | 1.00 | 21.03 | C |
| ATOM | 2589 | CG | PRO | A | 189 | −56.423 | 33.118 | 8.757 | 1.00 | 21.21 | C |
| ATOM | 2592 | CD | PRO | A | 189 | −56.873 | 31.992 | 9.668 | 1.00 | 21.61 | C |
| ATOM | 2595 | C | PRO | A | 189 | −58.946 | 32.314 | 7.076 | 1.00 | 20.96 | C |
| ATOM | 2596 | O | PRO | A | 189 | −58.418 | 31.247 | 6.793 | 1.00 | 21.02 | O |
| ATOM | 2597 | N | LEU | A | 190 | −59.714 | 32.994 | 6.226 | 1.00 | 20.89 | N |
| ATOM | 2598 | CA | LEU | A | 190 | −60.018 | 32.533 | 4.867 | 1.00 | 20.74 | C |
| ATOM | 2600 | CB | LEU | A | 190 | −60.597 | 33.690 | 4.053 | 1.00 | 20.76 | C |
| ATOM | 2603 | CG | LEU | A | 190 | −62.090 | 33.924 | 4.259 | 1.00 | 21.35 | C |
| ATOM | 2605 | CD1 | LEU | A | 190 | −62.537 | 35.196 | 3.578 | 1.00 | 20.54 | C |
| ATOM | 2609 | CD2 | LEU | A | 190 | −62.889 | 32.712 | 3.720 | 1.00 | 23.39 | C |
| ATOM | 2613 | C | LEU | A | 190 | −58.814 | 31.971 | 4.112 | 1.00 | 20.35 | C |
| ATOM | 2614 | O | LEU | A | 190 | −58.859 | 30.871 | 3.546 | 1.00 | 20.08 | O |
| ATOM | 2616 | N | HIS | A | 191 | −57.734 | 32.746 | 4.132 | 1.00 | 19.81 | N |
| ATOM | 2617 | CA | HIS | A | 191 | −56.537 | 32.448 | 3.364 | 1.00 | 18.89 | C |
| ATOM | 2619 | CB | HIS | A | 191 | −55.548 | 33.592 | 3.536 | 1.00 | 18.92 | C |
| ATOM | 2622 | CG | HIS | A | 191 | −54.372 | 33.520 | 2.623 | 1.00 | 18.51 | C |
| ATOM | 2623 | ND1 | HIS | A | 191 | −54.482 | 33.647 | 1.258 | 1.00 | 18.08 | N |
| ATOM | 2625 | CE1 | HIS | A | 191 | −53.281 | 33.544 | .718 | 1.00 | 18.96 | C |
| ATOM | 2627 | NE2 | HIS | A | 191 | −52.397 | 33.371 | 1.684 | 1.00 | 17.01 | N |
| ATOM | 2629 | CD2 | HIS | A | 191 | −53.054 | 33.355 | 2.884 | 1.00 | 17.94 | C |
| ATOM | 2631 | C | HIS | A | 191 | −55.889 | 31.142 | 3.759 | 1.00 | 18.32 | C |

TABLE 3-7-continued

Coordinates of *P. tremuloides IspS*

| | | | | | | | | | | |
|---|---|---|---|---|---|---|---|---|---|---|
| ATOM | 2632 | O | HIS | A | 191 | −55.217 | 30.531 | 2.942 | 1.00 | 17.98 O |
| ATOM | 2634 | N | ARG | A | 192 | −56.093 | 30.719 | 5.006 | 1.00 | 18.06 N |
| ATOM | 2635 | CA | ARG | A | 192 | −55.502 | 29.480 | 5.523 | 1.00 | 17.99 C |
| ATOM | 2637 | CB | ARG | A | 192 | −54.940 | 29.722 | 6.909 | 1.00 | 17.77 C |
| ATOM | 2640 | CG | ARG | A | 192 | −53.822 | 30.683 | 6.881 | 1.00 | 18.47 C |
| ATOM | 2643 | CD | ARG | A | 192 | −53.082 | 30.748 | 8.196 | 1.00 | 19.80 C |
| ATOM | 2646 | NE | ARG | A | 192 | −52.174 | 31.900 | 8.224 | 1.00 | 20.33 N |
| ATOM | 2648 | CZ | ARG | A | 192 | −51.176 | 32.048 | 9.077 | 1.00 | 20.10 C |
| ATOM | 2649 | NH1 | ARG | A | 192 | −50.928 | 31.113 | 9.972 | 1.00 | 21.72 N |
| ATOM | 2652 | NH2 | ARG | A | 192 | −50.407 | 33.119 | 9.019 | 1.00 | 20.79 N |
| ATOM | 2655 | C | ARG | A | 192 | −56.477 | 28.311 | 5.590 | 1.00 | 18.00 C |
| ATOM | 2656 | O | ARG | A | 192 | −56.067 | 27.170 | 5.871 | 1.00 | 18.21 O |
| ATOM | 2658 | N | ARG | A | 193 | −57.758 | 28.588 | 5.335 | 1.00 | 17.59 N |
| ATOM | 2659 | CA | ARG | A | 193 | −58.779 | 27.563 | 5.382 | 1.00 | 17.16 C |
| ATOM | 2661 | CB | ARG | A | 193 | −60.141 | 28.164 | 5.741 | 1.00 | 17.45 C |
| ATOM | 2664 | CG | ARG | A | 193 | −61.109 | 27.132 | 6.322 | 1.00 | 18.70 C |
| ATOM | 2667 | CD | ARG | A | 193 | −62.479 | 27.682 | 6.686 | 1.00 | 20.20 C |
| ATOM | 2670 | NE | ARG | A | 193 | −62.423 | 28.682 | 7.751 | 1.00 | 22.59 N |
| ATOM | 2672 | CZ | ARG | A | 193 | −62.386 | 28.435 | 9.067 | 1.00 | 24.12 C |
| ATOM | 2673 | NH1 | ARG | A | 193 | −62.395 | 27.198 | 9.575 | 1.00 | 22.66 N |
| ATOM | 2676 | NH2 | ARG | A | 193 | −62.348 | 29.469 | 9.898 | 1.00 | 26.36 N |
| ATOM | 2679 | C | ARG | A | 193 | −58.871 | 26.842 | 4.058 | 1.00 | 16.63 C |
| ATOM | 2680 | O | ARG | A | 193 | −58.861 | 27.461 | 3.005 | 1.00 | 15.93 O |
| ATOM | 2682 | N | THR | A | 194 | −58.955 | 25.518 | 4.149 | 1.00 | 16.72 N |
| ATOM | 2683 | CA | THR | A | 194 | −59.332 | 24.638 | 3.051 | 1.00 | 16.88 C |
| ATOM | 2685 | CB | THR | A | 194 | −59.520 | 23.250 | 3.592 | 1.00 | 16.43 C |
| ATOM | 2687 | OG1 | THR | A | 194 | −58.252 | 22.605 | 3.583 | 1.00 | 17.74 O |
| ATOM | 2689 | CG2 | THR | A | 194 | −60.454 | 22.441 | 2.754 | 1.00 | 18.43 C |
| ATOM | 2693 | C | THR | A | 194 | −60.607 | 25.112 | 2.384 | 1.00 | 17.28 C |
| ATOM | 2694 | O | THR | A | 194 | −61.441 | 25.734 | 3.022 | 1.00 | 17.44 O |
| ATOM | 2696 | N | GLN | A | 195 | −60.765 | 24.855 | 1.091 | 1.00 | 18.05 N |
| ATOM | 2697 | CA | GLN | A | 195 | −61.925 | 25.402 | .397 | 1.00 | 18.76 C |
| ATOM | 2699 | CB | GLN | A | 195 | −61.768 | 25.381 | −1.114 | 1.00 | 18.87 C |
| ATOM | 2702 | CG | GLN | A | 195 | −63.145 | 25.523 | −1.761 | 1.00 | 20.75 C |
| ATOM | 2705 | CD | GLN | A | 195 | −63.095 | 25.922 | −3.179 | 1.00 | 23.41 C |
| ATOM | 2706 | OE1 | GLN | A | 195 | −62.031 | 26.088 | −3.733 | 1.00 | 27.07 O |
| ATOM | 2707 | NE2 | GLN | A | 195 | −64.248 | 26.090 | −3.791 | 1.00 | 25.02 N |
| ATOM | 2710 | C | GLN | A | 195 | −63.243 | 24.704 | .765 | 1.00 | 18.93 C |
| ATOM | 2711 | O | GLN | A | 195 | −64.169 | 25.333 | 1.291 | 1.00 | 19.42 O |
| ATOM | 2713 | N | ARG | A | 196 | −63.345 | 23.418 | .443 | 1.00 | 18.90 N |
| ATOM | 2714 | CA | ARG | A | 196 | −64.577 | 22.685 | .663 | 1.00 | 18.68 C |
| ATOM | 2716 | CB | ARG | A | 196 | −64.356 | 21.186 | .454 | 1.00 | 18.53 C |
| ATOM | 2719 | CG | ARG | A | 196 | −64.851 | 20.644 | −.888 | 1.00 | 18.31 C |
| ATOM | 2722 | CD | ARG | A | 196 | −64.705 | 21.622 | −2.037 | 1.00 | 17.93 C |
| ATOM | 2725 | NE | ARG | A | 196 | −65.930 | 21.720 | −2.834 | 1.00 | 18.52 N |
| ATOM | 2727 | CZ | ARG | A | 196 | −66.480 | 22.857 | −3.256 | 1.00 | 18.63 C |
| ATOM | 2728 | NH1 | ARG | A | 196 | −65.938 | 24.014 | −2.937 | 1.00 | 19.84 N |
| ATOM | 2731 | NH2 | ARG | A | 196 | −67.582 | 22.844 | −3.999 | 1.00 | 18.53 N |
| ATOM | 2734 | C | ARG | A | 196 | −65.070 | 22.982 | 2.061 | 1.00 | 19.02 C |
| ATOM | 2735 | O | ARG | A | 196 | −66.276 | 23.085 | 2.284 | 1.00 | 19.30 O |
| ATOM | 2737 | N | LEU | A | 197 | −64.127 | 23.152 | 2.990 | 1.00 | 19.09 N |
| ATOM | 2738 | CA | LEU | A | 197 | −64.444 | 23.432 | 4.379 | 1.00 | 19.19 C |
| ATOM | 2740 | CB | LEU | A | 197 | −63.203 | 23.346 | 5.262 | 1.00 | 19.14 C |
| ATOM | 2743 | CG | LEU | A | 197 | −63.135 | 22.097 | 6.130 | 1.00 | 19.99 C |
| ATOM | 2745 | CD1 | LEU | A | 197 | −64.476 | 21.899 | 6.811 | 1.00 | 21.56 C |
| ATOM | 2749 | CD2 | LEU | A | 197 | −62.016 | 22.198 | 7.161 | 1.00 | 20.06 C |
| ATOM | 2753 | C | LEU | A | 197 | −65.071 | 24.781 | 4.553 | 1.00 | 19.52 C |
| ATOM | 2754 | O | LEU | A | 197 | −66.052 | 24.902 | 5.252 | 1.00 | 19.85 O |
| ATOM | 2756 | N | GLU | A | 198 | −64.488 | 25.803 | 3.941 | 1.00 | 20.11 N |
| ATOM | 2757 | CA | GLU | A | 198 | −65.051 | 27.147 | 3.986 | 1.00 | 20.47 C |
| ATOM | 2759 | CB | GLU | A | 198 | −64.079 | 28.156 | 3.385 | 1.00 | 20.84 C |
| ATOM | 2762 | CG | GLU | A | 198 | −64.659 | 29.539 | 3.069 | 1.00 | 22.30 C |
| ATOM | 2765 | CD | GLU | A | 198 | −65.206 | 30.260 | 4.283 | 1.00 | 24.40 C |
| ATOM | 2766 | OE1 | GLU | A | 198 | −64.852 | 29.894 | 5.418 | 1.00 | 25.34 O |
| ATOM | 2767 | OE2 | GLU | A | 198 | −65.991 | 31.217 | 4.106 | 1.00 | 26.83 O |
| ATOM | 2768 | C | GLU | A | 198 | −66.360 | 27.186 | 3.226 | 1.00 | 20.57 C |
| ATOM | 2769 | O | GLU | A | 198 | −67.212 | 28.009 | 3.529 | 1.00 | 20.65 O |
| ATOM | 2771 | N | ALA | A | 199 | −66.519 | 26.298 | 2.240 | 1.00 | 20.76 N |
| ATOM | 2772 | CA | ALA | A | 199 | −67.751 | 26.229 | 1.452 | 1.00 | 20.52 C |
| ATOM | 2774 | CB | ALA | A | 199 | −67.521 | 25.492 | .166 | 1.00 | 20.44 C |
| ATOM | 2778 | C | ALA | A | 199 | −68.907 | 25.611 | 2.232 | 1.00 | 20.55 C |
| ATOM | 2779 | O | ALA | A | 199 | −69.988 | 26.158 | 2.202 | 1.00 | 20.17 O |
| ATOM | 2781 | N | VAL | A | 200 | −68.701 | 24.493 | 2.933 | 1.00 | 21.10 N |
| ATOM | 2782 | CA | VAL | A | 200 | −69.791 | 23.935 | 3.774 | 1.00 | 21.51 C |
| ATOM | 2784 | CB | VAL | A | 200 | −69.509 | 22.576 | 4.485 | 1.00 | 21.18 C |
| ATOM | 2786 | CG1 | VAL | A | 200 | −69.618 | 21.460 | 3.525 | 1.00 | 21.27 C |
| ATOM | 2790 | CG2 | VAL | A | 200 | −68.161 | 22.569 | 5.200 | 1.00 | 21.23 C |
| ATOM | 2794 | C | VAL | A | 200 | −70.170 | 24.905 | 4.860 | 1.00 | 21.99 C |

TABLE 3-7-continued

Coordinates of *P. tremuloides IspS*

| | | | | | | | | | | | |
|---|---|---|---|---|---|---|---|---|---|---|---|
| ATOM | 2795 | O | VAL | A | 200 | −71.338 | 25.022 | 5.186 | 1.00 | 22.99 | O |
| ATOM | 2797 | N | TRP | A | 201 | −69.204 | 25.590 | 5.440 | 1.00 | 22.10 | N |
| ATOM | 2798 | CA | TRP | A | 201 | −69.551 | 26.565 | 6.433 | 1.00 | 22.58 | C |
| ATOM | 2800 | CB | TRP | A | 201 | −68.315 | 27.144 | 7.121 | 1.00 | 22.92 | C |
| ATOM | 2803 | CG | TRP | A | 201 | −68.667 | 27.957 | 8.310 | 1.00 | 23.65 | C |
| ATOM | 2804 | CD1 | TRP | A | 201 | −68.758 | 27.520 | 9.588 | 1.00 | 25.08 | C |
| ATOM | 2806 | NE1 | TRP | A | 201 | −69.127 | 28.549 | 10.417 | 1.00 | 26.35 | N |
| ATOM | 2808 | CE2 | TRP | A | 201 | −69.290 | 29.683 | 9.669 | 1.00 | 25.48 | C |
| ATOM | 2809 | CD2 | TRP | A | 201 | −69.010 | 29.344 | 8.332 | 1.00 | 24.77 | C |
| ATOM | 2810 | CE3 | TRP | A | 201 | −69.095 | 30.336 | 7.355 | 1.00 | 24.92 | C |
| ATOM | 2812 | CZ3 | TRP | A | 201 | −69.450 | 31.616 | 7.739 | 1.00 | 24.96 | C |
| ATOM | 2814 | CH2 | TRP | A | 201 | −69.720 | 31.918 | 9.078 | 1.00 | 25.08 | C |
| ATOM | 2816 | CZ2 | TRP | A | 201 | −69.648 | 30.968 | 10.056 | 1.00 | 24.68 | C |
| ATOM | 2818 | C | TRP | A | 201 | −70.351 | 27.662 | 5.758 | 1.00 | 22.71 | C |
| ATOM | 2819 | O | TRP | A | 201 | −71.482 | 27.921 | 6.140 | 1.00 | 22.76 | O |
| ATOM | 2821 | N | SER | A | 202 | −69.776 | 28.272 | 4.727 | 1.00 | 23.04 | N |
| ATOM | 2822 | CA | SER | A | 202 | −70.335 | 29.500 | 4.165 | 1.00 | 23.29 | C |
| ATOM | 2824 | CB | SER | A | 202 | −69.304 | 30.205 | 3.290 | 1.00 | 23.20 | C |
| ATOM | 2827 | OG | SER | A | 202 | −68.306 | 30.807 | 4.111 | 1.00 | 23.07 | O |
| ATOM | 2829 | C | SER | A | 202 | −71.666 | 29.341 | 3.432 | 1.00 | 23.66 | C |
| ATOM | 2830 | O | SER | A | 202 | −72.392 | 30.310 | 3.265 | 1.00 | 23.38 | O |
| ATOM | 2832 | N | ILE | A | 203 | −71.996 | 28.124 | 3.016 | 1.00 | 24.49 | N |
| ATOM | 2833 | CA | ILE | A | 203 | −73.321 | 27.859 | 2.460 | 1.00 | 25.07 | C |
| ATOM | 2835 | CB | ILE | A | 203 | −73.391 | 26.530 | 1.653 | 1.00 | 24.74 | C |
| ATOM | 2837 | CG1 | ILE | A | 203 | −72.494 | 26.587 | .423 | 1.00 | 24.36 | C |
| ATOM | 2840 | CD1 | ILE | A | 203 | −72.344 | 25.255 | −.281 | 1.00 | 23.81 | C |
| ATOM | 2844 | CG2 | ILE | A | 203 | −74.795 | 26.292 | 1.156 | 1.00 | 24.45 | C |
| ATOM | 2848 | C | ILE | A | 203 | −74.338 | 27.858 | 3.607 | 1.00 | 25.91 | C |
| ATOM | 2849 | O | ILE | A | 203 | −75.350 | 28.554 | 3.546 | 1.00 | 26.26 | O |
| ATOM | 2851 | N | GLU | A | 204 | −74.051 | 27.104 | 4.662 | 1.00 | 26.69 | N |
| ATOM | 2852 | CA | GLU | A | 204 | −74.929 | 27.053 | 5.824 | 1.00 | 27.40 | C |
| ATOM | 2854 | CB | GLU | A | 204 | −74.286 | 26.217 | 6.931 | 1.00 | 27.65 | C |
| ATOM | 2857 | CG | GLU | A | 204 | −75.132 | 26.032 | 8.183 | 1.00 | 29.02 | C |
| ATOM | 2860 | CD | GLU | A | 204 | −76.530 | 25.491 | 7.903 | 1.00 | 30.44 | C |
| ATOM | 2861 | OE1 | GLU | A | 204 | −76.746 | 24.858 | 6.844 | 1.00 | 31.22 | O |
| ATOM | 2862 | OE2 | GLU | A | 204 | −77.417 | 25.703 | 8.753 | 1.00 | 31.96 | O |
| ATOM | 2863 | C | GLU | A | 204 | −75.258 | 28.451 | 6.342 | 1.00 | 27.61 | C |
| ATOM | 2864 | O | GLU | A | 204 | −76.409 | 28.778 | 6.526 | 1.00 | 27.78 | O |
| ATOM | 2866 | N | ALA | A | 205 | −74.240 | 29.274 | 6.547 | 1.00 | 28.15 | N |
| ATOM | 2867 | CA | ALA | A | 205 | −74.416 | 30.637 | 7.050 | 1.00 | 28.41 | C |
| ATOM | 2869 | CB | ALA | A | 205 | −73.062 | 31.285 | 7.274 | 1.00 | 28.41 | C |
| ATOM | 2873 | C | ALA | A | 205 | −75.234 | 31.520 | 6.136 | 1.00 | 28.84 | C |
| ATOM | 2874 | O | ALA | A | 205 | −76.050 | 32.302 | 6.610 | 1.00 | 28.54 | O |
| ATOM | 2876 | N | TYR | A | 206 | −74.978 | 31.408 | 4.832 | 1.00 | 29.84 | N |
| ATOM | 2877 | CA | TYR | A | 206 | −75.581 | 32.281 | 3.805 | 1.00 | 30.41 | C |
| ATOM | 2879 | CB | TYR | A | 206 | −74.801 | 32.170 | 2.493 | 1.00 | 30.20 | C |
| ATOM | 2882 | CG | TYR | A | 206 | −75.180 | 33.173 | 1.425 | 1.00 | 29.62 | C |
| ATOM | 2883 | CD1 | TYR | A | 206 | −74.721 | 34.482 | 1.484 | 1.00 | 30.32 | C |
| ATOM | 2885 | CE1 | TYR | A | 206 | −75.047 | 35.412 | .489 | 1.00 | 29.70 | C |
| ATOM | 2887 | CZ | TYR | A | 206 | −75.830 | 35.028 | −.578 | 1.00 | 28.41 | C |
| ATOM | 2888 | OH | TYR | A | 206 | −76.155 | 35.956 | −1.548 | 1.00 | 26.74 | O |
| ATOM | 2890 | CE2 | TYR | A | 206 | −76.291 | 33.724 | −.659 | 1.00 | 28.16 | C |
| ATOM | 2892 | CD2 | TYR | A | 206 | −75.958 | 32.806 | .335 | 1.00 | 28.39 | C |
| ATOM | 2894 | C | TYR | A | 206 | −77.038 | 31.918 | 3.561 | 1.00 | 31.15 | C |
| ATOM | 2895 | O | TYR | A | 206 | −77.858 | 32.781 | 3.268 | 1.00 | 31.30 | O |
| ATOM | 2897 | N | ARG | A | 207 | −77.341 | 30.631 | 3.676 | 1.00 | 32.05 | N |
| ATOM | 2898 | CA | ARG | A | 207 | −78.691 | 30.128 | 3.555 | 1.00 | 32.81 | C |
| ATOM | 2900 | CB | ARG | A | 207 | −78.684 | 28.623 | 3.813 | 1.00 | 32.86 | C |
| ATOM | 2903 | CG | ARG | A | 207 | −80.028 | 27.941 | 3.673 | 1.00 | 34.01 | C |
| ATOM | 2906 | CD | ARG | A | 207 | −80.066 | 26.632 | 4.450 | 1.00 | 35.11 | C |
| ATOM | 2909 | NE | ARG | A | 207 | −79.096 | 25.669 | 3.939 | 1.00 | 35.35 | N |
| ATOM | 2911 | CZ | ARG | A | 207 | −79.353 | 24.737 | 3.022 | 1.00 | 36.00 | C |
| ATOM | 2912 | NH1 | ARG | A | 207 | −80.562 | 24.611 | 2.478 | 1.00 | 35.55 | N |
| ATOM | 2915 | NH2 | ARG | A | 207 | −78.381 | 23.918 | 2.640 | 1.00 | 37.05 | N |
| ATOM | 2918 | C | ARG | A | 207 | −79.609 | 30.826 | 4.550 | 1.00 | 33.57 | C |
| ATOM | 2919 | O | ARG | A | 207 | −80.783 | 31.003 | 4.263 | 1.00 | 33.82 | O |
| ATOM | 2921 | N | LYS | A | 208 | −79.064 | 31.223 | 5.707 | 1.00 | 34.58 | N |
| ATOM | 2922 | CA | LYS | A | 208 | −79.835 | 31.830 | 6.812 | 1.00 | 35.21 | C |
| ATOM | 2924 | CB | LYS | A | 208 | −79.137 | 31.599 | 8.159 | 1.00 | 35.05 | C |
| ATOM | 2927 | CG | LYS | A | 208 | −78.847 | 30.147 | 8.496 | 1.00 | 34.78 | C |
| ATOM | 2930 | CD | LYS | A | 208 | −78.583 | 29.974 | 9.980 | 1.00 | 34.44 | C |
| ATOM | 2933 | CE | LYS | A | 208 | −77.992 | 28.619 | 10.309 | 1.00 | 34.16 | C |
| ATOM | 2936 | NZ | LYS | A | 208 | −76.540 | 28.693 | 10.572 | 1.00 | 33.81 | N |
| ATOM | 2940 | C | LYS | A | 208 | −80.075 | 33.333 | 6.663 | 1.00 | 36.06 | C |
| ATOM | 2941 | O | LYS | A | 208 | −81.032 | 33.857 | 7.226 | 1.00 | 36.19 | O |
| ATOM | 2943 | N | LYS | A | 209 | −79.197 | 34.032 | 5.946 | 1.00 | 36.93 | N |
| ATOM | 2944 | CA | LYS | A | 209 | −79.412 | 35.445 | 5.652 | 1.00 | 37.77 | C |
| ATOM | 2946 | CB | LYS | A | 209 | −78.284 | 35.998 | 4.779 | 1.00 | 38.18 | C |

TABLE 3-7-continued

Coordinates of *P. tremuloides IspS*

| | | | | | | | | | | | |
|---|---|---|---|---|---|---|---|---|---|---|---|
| ATOM | 2949 | CG | LYS | A | 209 | −76.928 | 36.134 | 5.458 | 1.00 | 39.90 | C |
| ATOM | 2952 | CD | LYS | A | 209 | −75.982 | 37.023 | 4.621 | 1.00 | 42.39 | C |
| ATOM | 2955 | CE | LYS | A | 209 | −74.531 | 37.016 | 5.169 | 1.00 | 44.21 | C |
| ATOM | 2958 | NZ | LYS | A | 209 | −74.350 | 37.688 | 6.509 | 1.00 | 44.75 | N |
| ATOM | 2962 | C | LYS | A | 209 | −80.738 | 35.600 | 4.911 | 1.00 | 37.89 | C |
| ATOM | 2963 | O | LYS | A | 209 | −81.049 | 34.785 | 4.036 | 1.00 | 38.20 | O |
| ATOM | 2965 | N | GLU | A | 210 | −81.518 | 36.632 | 5.243 | 1.00 | 37.87 | N |
| ATOM | 2966 | CA | GLU | A | 210 | −82.847 | 36.797 | 4.630 | 1.00 | 37.72 | C |
| ATOM | 2968 | CB | GLU | A | 210 | −83.821 | 37.578 | 5.549 | 1.00 | 38.19 | C |
| ATOM | 2971 | CG | GLU | A | 210 | −83.850 | 39.130 | 5.404 | 1.00 | 39.68 | C |
| ATOM | 2974 | CD | GLU | A | 210 | −85.270 | 39.736 | 5.534 | 1.00 | 41.27 | C |
| ATOM | 2975 | OE1 | GLU | A | 210 | −86.172 | 39.100 | 6.136 | 1.00 | 41.67 | O |
| ATOM | 2976 | OE2 | GLU | A | 210 | −85.482 | 40.859 | 5.019 | 1.00 | 42.17 | O |
| ATOM | 2977 | C | GLU | A | 210 | −82.760 | 37.394 | 3.219 | 1.00 | 36.68 | C |
| ATOM | 2978 | O | GLU | A | 210 | −83.605 | 37.103 | 2.371 | 1.00 | 36.39 | O |
| ATOM | 2980 | N | ASP | A | 211 | −81.725 | 38.198 | 2.969 | 1.00 | 35.65 | N |
| ATOM | 2981 | CA | ASP | A | 211 | −81.481 | 38.777 | 1.632 | 1.00 | 34.94 | C |
| ATOM | 2983 | CB | ASP | A | 211 | −81.064 | 40.257 | 1.740 | 1.00 | 35.22 | C |
| ATOM | 2986 | CG | ASP | A | 211 | −79.811 | 40.477 | 2.599 | 1.00 | 35.84 | C |
| ATOM | 2987 | OD1 | ASP | A | 211 | −79.379 | 39.557 | 3.341 | 1.00 | 35.60 | O |
| ATOM | 2988 | OD2 | ASP | A | 211 | −79.276 | 41.606 | 2.536 | 1.00 | 36.73 | O |
| ATOM | 2989 | C | ASP | A | 211 | −80.451 | 37.989 | .811 | 1.00 | 33.73 | C |
| ATOM | 2990 | O | ASP | A | 211 | −79.753 | 38.556 | −.021 | 1.00 | 33.40 | O |
| ATOM | 2992 | N | ALA | A | 212 | −80.366 | 36.682 | 1.057 | 1.00 | 32.53 | N |
| ATOM | 2993 | CA | ALA | A | 212 | −79.506 | 35.783 | .293 | 1.00 | 31.40 | C |
| ATOM | 2995 | CB | ALA | A | 212 | −79.569 | 34.382 | .889 | 1.00 | 30.79 | C |
| ATOM | 2999 | C | ALA | A | 212 | −79.940 | 35.762 | −1.176 | 1.00 | 30.60 | C |
| ATOM | 3000 | O | ALA | A | 212 | −81.124 | 35.594 | −1.467 | 1.00 | 30.37 | O |
| ATOM | 3002 | N | ASN | A | 213 | −79.000 | 35.967 | −2.097 | 1.00 | 29.71 | N |
| ATOM | 3003 | CA | ASN | A | 213 | −79.304 | 35.809 | −3.520 | 1.00 | 29.27 | C |
| ATOM | 3005 | CB | ASN | A | 213 | −78.144 | 36.315 | −4.402 | 1.00 | 29.30 | C |
| ATOM | 3008 | CG | ASN | A | 213 | −78.442 | 36.217 | −5.911 | 1.00 | 29.07 | C |
| ATOM | 3009 | OD1 | ASN | A | 213 | −78.437 | 37.215 | −6.624 | 1.00 | 29.38 | O |
| ATOM | 3010 | ND2 | ASN | A | 213 | −78.691 | 35.015 | −6.389 | 1.00 | 28.37 | N |
| ATOM | 3013 | C | ASN | A | 213 | −79.634 | 34.328 | −3.785 | 1.00 | 28.81 | C |
| ATOM | 3014 | O | ASN | A | 213 | −78.784 | 33.455 | −3.658 | 1.00 | 29.04 | O |
| ATOM | 3016 | N | GLN | A | 214 | −80.880 | 34.053 | −4.145 | 1.00 | 28.04 | N |
| ATOM | 3017 | CA | GLN | A | 214 | −81.376 | 32.692 | −4.191 | 1.00 | 27.32 | C |
| ATOM | 3019 | CB | GLN | A | 214 | −82.906 | 32.700 | −4.178 | 1.00 | 27.47 | C |
| ATOM | 3022 | CG | GLN | A | 214 | −83.505 | 33.269 | −2.889 | 1.00 | 27.68 | C |
| ATOM | 3025 | CD | GLN | A | 214 | −83.294 | 32.359 | −1.688 | 1.00 | 27.54 | C |
| ATOM | 3026 | OE1 | GLN | A | 214 | −83.940 | 31.320 | −1.571 | 1.00 | 28.19 | O |
| ATOM | 3027 | NE2 | GLN | A | 214 | −82.392 | 32.748 | −.790 | 1.00 | 26.90 | N |
| ATOM | 3030 | C | GLN | A | 214 | −80.858 | 31.902 | −5.385 | 1.00 | 26.71 | C |
| ATOM | 3031 | O | GLN | A | 214 | −80.863 | 30.668 | −5.355 | 1.00 | 26.91 | O |
| ATOM | 3033 | N | VAL | A | 215 | −80.439 | 32.600 | −6.442 | 1.00 | 25.81 | N |
| ATOM | 3034 | CA | VAL | A | 215 | −79.789 | 31.947 | −7.588 | 1.00 | 24.88 | C |
| ATOM | 3036 | CB | VAL | A | 215 | −79.651 | 32.894 | −8.808 | 1.00 | 24.81 | C |
| ATOM | 3038 | CG1 | VAL | A | 215 | −78.459 | 32.483 | −9.680 | 1.00 | 24.94 | C |
| ATOM | 3042 | CG2 | VAL | A | 215 | −80.935 | 32.907 | −9.620 | 1.00 | 23.74 | C |
| ATOM | 3046 | C | VAL | A | 215 | −78.415 | 31.427 | −7.176 | 1.00 | 24.18 | C |
| ATOM | 3047 | O | VAL | A | 215 | −78.073 | 30.282 | −7.430 | 1.00 | 23.74 | O |
| ATOM | 3049 | N | LEU | A | 216 | −77.650 | 32.283 | −6.510 | 1.00 | 23.78 | N |
| ATOM | 3050 | CA | LEU | A | 216 | −76.299 | 31.961 | −6.036 | 1.00 | 23.33 | C |
| ATOM | 3052 | CB | LEU | A | 216 | −75.680 | 33.195 | −5.373 | 1.00 | 23.10 | C |
| ATOM | 3055 | CG | LEU | A | 216 | −74.194 | 33.192 | −5.059 | 1.00 | 22.91 | C |
| ATOM | 3057 | CD1 | LEU | A | 216 | −73.383 | 32.962 | −6.312 | 1.00 | 22.88 | C |
| ATOM | 3061 | CD2 | LEU | A | 216 | −73.826 | 34.518 | −4.424 | 1.00 | 22.03 | C |
| ATOM | 3065 | C | LEU | A | 216 | −76.333 | 30.797 | −5.050 | 1.00 | 22.92 | C |
| ATOM | 3066 | O | LEU | A | 216 | −75.598 | 29.826 | −5.201 | 1.00 | 23.38 | O |
| ATOM | 3068 | N | LEU | A | 217 | −77.214 | 30.890 | −4.060 | 1.00 | 22.09 | N |
| ATOM | 3069 | CA | LEU | A | 217 | −77.367 | 29.851 | −3.054 | 1.00 | 21.14 | C |
| ATOM | 3071 | CB | LEU | A | 217 | −78.488 | 30.225 | −2.090 | 1.00 | 21.11 | C |
| ATOM | 3074 | CG | LEU | A | 217 | −78.782 | 29.236 | −.961 | 1.00 | 21.08 | C |
| ATOM | 3076 | CD1 | LEU | A | 217 | −77.703 | 29.267 | .101 | 1.00 | 19.87 | C |
| ATOM | 3080 | CD2 | LEU | A | 217 | −80.146 | 29.535 | −.360 | 1.00 | 21.46 | C |
| ATOM | 3084 | C | LEU | A | 217 | −77.682 | 28.517 | −3.685 | 1.00 | 20.38 | C |
| ATOM | 3085 | O | LEU | A | 217 | −77.133 | 27.508 | −3.286 | 1.00 | 20.04 | O |
| ATOM | 3087 | N | GLU | A | 218 | −78.579 | 28.512 | −4.661 | 1.00 | 19.97 | N |
| ATOM | 3088 | CA | GLU | A | 218 | −79.027 | 27.260 | −5.273 | 1.00 | 19.72 | C |
| ATOM | 3090 | CB | GLU | A | 218 | −80.220 | 27.499 | −6.212 | 1.00 | 19.87 | C |
| ATOM | 3093 | CG | GLU | A | 218 | −81.005 | 26.228 | −6.627 | 1.00 | 21.03 | C |
| ATOM | 3096 | CD | GLU | A | 218 | −82.303 | 26.535 | −7.424 | 1.00 | 22.59 | C |
| ATOM | 3097 | OE1 | GLU | A | 218 | −82.643 | 27.730 | −7.619 | 1.00 | 23.61 | O |
| ATOM | 3098 | OE2 | GLU | A | 218 | −82.983 | 25.578 | −7.863 | 1.00 | 22.31 | O |
| ATOM | 3099 | C | GLU | A | 218 | −77.854 | 26.613 | −6.009 | 1.00 | 19.03 | C |
| ATOM | 3100 | O | GLU | A | 218 | −77.522 | 25.452 | −5.764 | 1.00 | 18.97 | O |
| ATOM | 3102 | N | LEU | A | 219 | −77.203 | 27.381 | −6.878 | 1.00 | 18.06 | N |

TABLE 3-7-continued

Coordinates of *P. tremuloides IspS*

| | | | | | | | | | | | |
|---|---|---|---|---|---|---|---|---|---|---|---|
| ATOM | 3103 | CA | LEU | A | 219 | −76.012 | 26.907 | −7.573 | 1.00 | 17.15 | C |
| ATOM | 3105 | CB | LEU | A | 219 | −75.439 | 28.029 | −8.418 | 1.00 | 16.75 | C |
| ATOM | 3108 | CG | LEU | A | 219 | −74.196 | 27.717 | −9.231 | 1.00 | 16.01 | C |
| ATOM | 3110 | CD1 | LEU | A | 219 | −74.511 | 26.832 | −10.404 | 1.00 | 12.99 | C |
| ATOM | 3114 | CD2 | LEU | A | 219 | −73.577 | 29.028 | −9.675 | 1.00 | 16.20 | C |
| ATOM | 3118 | C | LEU | A | 219 | −74.973 | 26.409 | −6.570 | 1.00 | 16.75 | C |
| ATOM | 3119 | O | LEU | A | 219 | −74.377 | 25.355 | −6.757 | 1.00 | 16.47 | O |
| ATOM | 3121 | N | ALA | A | 220 | −74.786 | 27.169 | −5.496 | 1.00 | 16.40 | N |
| ATOM | 3122 | CA | ALA | A | 220 | −73.858 | 26.808 | −4.422 | 1.00 | 16.15 | C |
| ATOM | 3124 | CB | ALA | A | 220 | −73.906 | 27.830 | −3.302 | 1.00 | 16.13 | C |
| ATOM | 3128 | C | ALA | A | 220 | −74.137 | 25.436 | −3.862 | 1.00 | 16.03 | C |
| ATOM | 3129 | O | ALA | A | 220 | −73.253 | 24.603 | −3.799 | 1.00 | 16.30 | O |
| ATOM | 3131 | N | ILE | A | 221 | −75.371 | 25.201 | −3.447 | 1.00 | 16.24 | N |
| ATOM | 3132 | CA | ILE | A | 221 | −75.731 | 23.916 | −2.857 | 1.00 | 16.33 | C |
| ATOM | 3134 | CB | ILE | A | 221 | −77.203 | 23.895 | −2.352 | 1.00 | 15.94 | C |
| ATOM | 3136 | CG1 | ILE | A | 221 | −77.410 | 24.879 | −1.203 | 1.00 | 15.36 | C |
| ATOM | 3139 | CD1 | ILE | A | 221 | −78.842 | 25.234 | −.962 | 1.00 | 14.49 | C |
| ATOM | 3143 | CG2 | ILE | A | 221 | −77.571 | 22.537 | −1.836 | 1.00 | 15.18 | C |
| ATOM | 3147 | C | ILE | A | 221 | −75.509 | 22.841 | −3.911 | 1.00 | 17.06 | C |
| ATOM | 3148 | O | ILE | A | 221 | −74.899 | 21.819 | −3.653 | 1.00 | 16.51 | O |
| ATOM | 3150 | N | LEU | A | 222 | −75.981 | 23.138 | −5.117 | 1.00 | 18.53 | N |
| ATOM | 3151 | CA | LEU | A | 222 | −76.006 | 22.207 | −6.243 | 1.00 | 19.25 | C |
| ATOM | 3153 | CB | LEU | A | 222 | −76.657 | 22.891 | −7.445 | 1.00 | 19.18 | C |
| ATOM | 3156 | CG | LEU | A | 222 | −77.037 | 21.972 | −8.597 | 1.00 | 19.65 | C |
| ATOM | 3158 | CD1 | LEU | A | 222 | −78.318 | 22.489 | −9.268 | 1.00 | 19.24 | C |
| ATOM | 3162 | CD2 | LEU | A | 222 | −75.869 | 21.788 | −9.597 | 1.00 | 18.75 | C |
| ATOM | 3166 | C | LEU | A | 222 | −74.618 | 21.751 | −6.630 | 1.00 | 20.07 | C |
| ATOM | 3167 | O | LEU | A | 222 | −74.381 | 20.558 | −6.778 | 1.00 | 20.55 | O |
| ATOM | 3169 | N | ASP | A | 223 | −73.710 | 22.711 | −6.797 | 1.00 | 20.92 | N |
| ATOM | 3170 | CA | ASP | A | 223 | −72.330 | 22.427 | −7.189 | 1.00 | 21.43 | C |
| ATOM | 3172 | CB | ASP | A | 223 | −71.621 | 23.723 | −7.585 | 1.00 | 21.63 | C |
| ATOM | 3175 | CG | ASP | A | 223 | −70.202 | 23.495 | −8.070 | 1.00 | 22.51 | C |
| ATOM | 3176 | OD1 | ASP | A | 223 | −69.296 | 23.282 | −7.225 | 1.00 | 24.67 | O |
| ATOM | 3177 | OD2 | ASP | A | 223 | −69.990 | 23.544 | −9.296 | 1.00 | 22.73 | O |
| ATOM | 3178 | C | ASP | A | 223 | −71.573 | 21.722 | −6.060 | 1.00 | 21.79 | C |
| ATOM | 3179 | O | ASP | A | 223 | −70.843 | 20.764 | −6.313 | 1.00 | 21.73 | O |
| ATOM | 3181 | N | TYR | A | 224 | −71.755 | 22.182 | −4.820 | 1.00 | 22.14 | N |
| ATOM | 3182 | CA | TYR | A | 224 | −71.120 | 21.529 | −3.686 | 1.00 | 22.22 | C |
| ATOM | 3184 | CB | TYR | A | 224 | −71.462 | 22.190 | −2.355 | 1.00 | 22.38 | C |
| ATOM | 3187 | CG | TYR | A | 224 | −70.673 | 21.542 | −1.249 | 1.00 | 22.65 | C |
| ATOM | 3188 | CD1 | TYR | A | 224 | −69.356 | 21.864 | −1.053 | 1.00 | 22.59 | C |
| ATOM | 3190 | CE1 | TYR | A | 224 | −68.622 | 21.258 | −.098 | 1.00 | 23.38 | C |
| ATOM | 3192 | CZ | TYR | A | 224 | −69.177 | 20.288 | .670 | 1.00 | 23.22 | C |
| ATOM | 3193 | OH | TYR | A | 224 | −68.402 | 19.684 | 1.620 | 1.00 | 23.93 | O |
| ATOM | 3195 | CE2 | TYR | A | 224 | −70.483 | 19.931 | .500 | 1.00 | 23.36 | C |
| ATOM | 3197 | CD2 | TYR | A | 224 | −71.221 | 20.547 | −.464 | 1.00 | 23.41 | C |
| ATOM | 3199 | C | TYR | A | 224 | −71.485 | 20.065 | −3.605 | 1.00 | 22.52 | C |
| ATOM | 3200 | O | TYR | A | 224 | −70.641 | 19.233 | −3.311 | 1.00 | 22.93 | O |
| ATOM | 3202 | N | ASN | A | 225 | −72.742 | 19.749 | −3.856 | 1.00 | 22.94 | N |
| ATOM | 3203 | CA | ASN | A | 225 | −73.187 | 18.374 | −3.801 | 1.00 | 23.44 | C |
| ATOM | 3205 | CB | ASN | A | 225 | −74.706 | 18.310 | −3.729 | 1.00 | 23.34 | C |
| ATOM | 3208 | CG | ASN | A | 225 | −75.210 | 18.579 | −2.352 | 1.00 | 22.62 | C |
| ATOM | 3209 | OD1 | ASN | A | 225 | −74.749 | 17.977 | −1.407 | 1.00 | 23.33 | O |
| ATOM | 3210 | ND2 | ASN | A | 225 | −76.146 | 19.494 | −2.223 | 1.00 | 22.52 | N |
| ATOM | 3213 | C | ASN | A | 225 | −72.694 | 17.523 | −4.959 | 1.00 | 24.26 | C |
| ATOM | 3214 | O | ASN | A | 225 | −72.408 | 16.328 | −4.767 | 1.00 | 24.88 | O |
| ATOM | 3216 | N | MET | A | 226 | −72.607 | 18.119 | −6.150 | 1.00 | 24.67 | N |
| ATOM | 3217 | CA | MET | A | 226 | −72.167 | 17.395 | −7.349 | 1.00 | 24.95 | C |
| ATOM | 3219 | CB | MET | A | 226 | −72.421 | 18.237 | −8.594 | 1.00 | 25.37 | C |
| ATOM | 3222 | CG | MET | A | 226 | −71.785 | 17.713 | −9.873 | 1.00 | 27.23 | C |
| ATOM | 3225 | SD | MET | A | 226 | −70.837 | 19.010 | −10.708 | 1.00 | 31.73 | S |
| ATOM | 3226 | CE | MET | A | 226 | −72.185 | 20.000 | −11.367 | 1.00 | 31.30 | C |
| ATOM | 3230 | C | MET | A | 226 | −70.688 | 17.045 | −7.247 | 1.00 | 24.70 | C |
| ATOM | 3231 | O | MET | A | 226 | −70.291 | 15.929 | −7.568 | 1.00 | 24.91 | O |
| ATOM | 3233 | N | ILE | A | 227 | −69.873 | 17.995 | −6.799 | 1.00 | 24.43 | N |
| ATOM | 3234 | CA | ILE | A | 227 | −68.456 | 17.726 | −6.598 | 1.00 | 24.18 | C |
| ATOM | 3236 | CB | ILE | A | 227 | −67.656 | 18.971 | −6.154 | 1.00 | 24.15 | C |
| ATOM | 3238 | CG1 | ILE | A | 227 | −67.628 | 20.021 | −7.253 | 1.00 | 23.64 | C |
| ATOM | 3241 | CD1 | ILE | A | 227 | −66.853 | 21.246 | −6.880 | 1.00 | 23.11 | C |
| ATOM | 3245 | CG2 | ILE | A | 227 | −66.229 | 18.603 | −5.827 | 1.00 | 24.36 | C |
| ATOM | 3249 | C | ILE | A | 227 | −68.329 | 16.645 | −5.546 | 1.00 | 23.98 | C |
| ATOM | 3250 | O | ILE | A | 227 | −67.609 | 15.689 | −5.747 | 1.00 | 24.35 | O |
| ATOM | 3252 | N | GLN | A | 228 | −69.048 | 16.779 | −4.439 | 1.00 | 23.79 | N |
| ATOM | 3253 | CA | GLN | A | 228 | −69.020 | 15.754 | −3.382 | 1.00 | 23.66 | C |
| ATOM | 3255 | CB | GLN | A | 228 | −70.077 | 16.010 | −2.305 | 1.00 | 23.64 | C |
| ATOM | 3258 | CG | GLN | A | 228 | −69.972 | 15.049 | −1.145 | 1.00 | 22.91 | C |
| ATOM | 3261 | CD | GLN | A | 228 | −70.891 | 15.417 | −.033 | 1.00 | 23.26 | C |
| ATOM | 3262 | OE1 | GLN | A | 228 | −72.082 | 15.098 | −.069 | 1.00 | 25.64 | O |

TABLE 3-7-continued

Coordinates of *P. tremuloides IspS*

| | | | | | | | | | | | |
|---|---|---|---|---|---|---|---|---|---|---|---|
| ATOM | 3263 | NE2 | GLN | A | 228 | −70.357 | 16.083 | .978 | 1.00 | 21.77 | N |
| ATOM | 3266 | C | GLN | A | 228 | −69.243 | 14.349 | −3.893 | 1.00 | 23.54 | C |
| ATOM | 3267 | O | GLN | A | 228 | −68.664 | 13.412 | −3.357 | 1.00 | 23.59 | O |
| ATOM | 3269 | N | SER | A | 229 | −70.105 | 14.194 | −4.893 | 1.00 | 23.27 | N |
| ATOM | 3270 | CA | SER | A | 229 | −70.394 | 12.868 | −5.406 | 1.00 | 23.35 | C |
| ATOM | 3272 | CB | SER | A | 229 | −71.753 | 12.812 | −6.095 | 1.00 | 23.31 | C |
| ATOM | 3275 | OG | SER | A | 229 | −71.836 | 13.823 | −7.060 | 1.00 | 24.31 | O |
| ATOM | 3277 | C | SER | A | 229 | −69.287 | 12.394 | −6.331 | 1.00 | 23.19 | C |
| ATOM | 3278 | O | SER | A | 229 | −69.130 | 11.194 | −6.512 | 1.00 | 23.44 | O |
| ATOM | 3280 | N | VAL | A | 230 | −68.512 | 13.306 | −6.914 | 1.00 | 23.14 | N |
| ATOM | 3281 | CA | VAL | A | 230 | −67.269 | 12.874 | −7.552 | 1.00 | 23.00 | C |
| ATOM | 3283 | CB | VAL | A | 230 | −66.469 | 13.998 | −8.253 | 1.00 | 22.75 | C |
| ATOM | 3285 | CG1 | VAL | A | 230 | −65.091 | 13.470 | −8.667 | 1.00 | 21.87 | C |
| ATOM | 3289 | CG2 | VAL | A | 230 | −67.222 | 14.539 | −9.459 | 1.00 | 21.74 | C |
| ATOM | 3293 | C | VAL | A | 230 | −66.417 | 12.268 | −6.452 | 1.00 | 23.35 | C |
| ATOM | 3294 | O | VAL | A | 230 | −65.917 | 11.173 | −6.589 | 1.00 | 23.68 | O |
| ATOM | 3296 | N | TYR | A | 231 | −66.284 | 12.968 | −5.340 | 1.00 | 23.96 | N |
| ATOM | 3297 | CA | TYR | A | 231 | −65.414 | 12.509 | −4.274 | 1.00 | 24.60 | C |
| ATOM | 3299 | CB | TYR | A | 231 | −65.486 | 13.426 | −3.051 | 1.00 | 24.69 | C |
| ATOM | 3302 | CG | TYR | A | 231 | −64.963 | 14.837 | −3.211 | 1.00 | 24.11 | C |
| ATOM | 3303 | CD1 | TYR | A | 231 | −64.071 | 15.190 | −4.214 | 1.00 | 24.31 | C |
| ATOM | 3305 | CE1 | TYR | A | 231 | −63.592 | 16.491 | −4.322 | 1.00 | 24.63 | C |
| ATOM | 3307 | CZ | TYR | A | 231 | −63.994 | 17.441 | −3.406 | 1.00 | 25.13 | C |
| ATOM | 3308 | OH | TYR | A | 231 | −63.554 | 18.754 | −3.456 | 1.00 | 24.64 | O |
| ATOM | 3310 | CE2 | TYR | A | 231 | −64.863 | 17.086 | −2.402 | 1.00 | 25.76 | C |
| ATOM | 3312 | CD2 | TYR | A | 231 | −65.329 | 15.800 | −2.308 | 1.00 | 24.28 | C |
| ATOM | 3314 | C | TYR | A | 231 | −65.785 | 11.111 | −3.833 | 1.00 | 25.26 | C |
| ATOM | 3315 | O | TYR | A | 231 | −64.917 | 10.315 | −3.488 | 1.00 | 25.44 | O |
| ATOM | 3317 | N | GLN | A | 232 | −67.079 | 10.819 | −3.833 | 1.00 | 26.04 | N |
| ATOM | 3318 | CA | GLN | A | 232 | −67.566 | 9.532 | −3.362 | 1.00 | 26.57 | C |
| ATOM | 3320 | CB | GLN | A | 232 | −69.060 | 9.621 | −3.057 | 1.00 | 26.44 | C |
| ATOM | 3323 | CG | GLN | A | 232 | −69.339 | 10.397 | −1.778 | 1.00 | 26.25 | C |
| ATOM | 3326 | CD | GLN | A | 232 | −70.786 | 10.819 | −1.630 | 1.00 | 26.53 | C |
| ATOM | 3327 | OE1 | GLN | A | 232 | −71.667 | 10.305 | −2.318 | 1.00 | 27.77 | O |
| ATOM | 3328 | NE2 | GLN | A | 232 | −71.040 | 11.759 | −.723 | 1.00 | 25.51 | N |
| ATOM | 3331 | C | GLN | A | 232 | −67.238 | 8.414 | −4.351 | 1.00 | 27.44 | C |
| ATOM | 3332 | O | GLN | A | 232 | −66.852 | 7.319 | −3.935 | 1.00 | 27.33 | O |
| ATOM | 3334 | N | ARG | A | 233 | −67.373 | 8.691 | −5.649 | 1.00 | 28.66 | N |
| ATOM | 3335 | CA | ARG | A | 233 | −66.905 | 7.768 | −6.685 | 1.00 | 29.86 | C |
| ATOM | 3337 | CB | ARG | A | 233 | −67.212 | 8.292 | −8.090 | 1.00 | 30.08 | C |
| ATOM | 3340 | CG | ARG | A | 233 | −66.378 | 7.634 | −9.179 | 1.00 | 32.80 | C |
| ATOM | 3343 | CD | ARG | A | 233 | −66.913 | 7.923 | −10.572 | 1.00 | 36.74 | C |
| ATOM | 3346 | NE | ARG | A | 233 | −66.962 | 9.363 | −10.860 | 1.00 | 40.33 | N |
| ATOM | 3348 | CZ | ARG | A | 233 | −68.069 | 10.119 | −10.891 | 1.00 | 43.12 | C |
| ATOM | 3349 | NH1 | ARG | A | 233 | −69.276 | 9.600 | −10.655 | 1.00 | 44.55 | N |
| ATOM | 3352 | NH2 | ARG | A | 233 | −67.971 | 11.418 | −11.169 | 1.00 | 43.38 | N |
| ATOM | 3355 | C | ARG | A | 233 | −65.401 | 7.518 | −6.514 | 1.00 | 30.34 | C |
| ATOM | 3356 | O | ARG | A | 233 | −64.962 | 6.374 | −6.412 | 1.00 | 30.55 | O |
| ATOM | 3358 | N | ASP | A | 234 | −64.621 | 8.591 | −6.461 | 1.00 | 31.00 | N |
| ATOM | 3359 | CA | ASP | A | 234 | −63.187 | 8.487 | −6.205 | 1.00 | 31.48 | C |
| ATOM | 3361 | CB | ASP | A | 234 | −62.594 | 9.870 | −5.942 | 1.00 | 31.56 | C |
| ATOM | 3364 | CG | ASP | A | 234 | −62.573 | 10.741 | −7.167 | 1.00 | 32.78 | C |
| ATOM | 3365 | OD1 | ASP | A | 234 | −62.911 | 10.249 | −8.276 | 1.00 | 34.25 | O |
| ATOM | 3366 | OD2 | ASP | A | 234 | −62.215 | 11.930 | −7.011 | 1.00 | 34.81 | O |
| ATOM | 3367 | C | ASP | A | 234 | −62.885 | 7.596 | −5.010 | 1.00 | 31.70 | C |
| ATOM | 3368 | O | ASP | A | 234 | −61.985 | 6.780 | −5.053 | 1.00 | 31.56 | O |
| ATOM | 3370 | N | LEU | A | 235 | −63.647 | 7.766 | −3.943 | 1.00 | 32.43 | N |
| ATOM | 3371 | CA | LEU | A | 235 | −63.366 | 7.102 | −2.685 | 1.00 | 33.04 | C |
| ATOM | 3373 | CB | LEU | A | 235 | −64.072 | 7.833 | −1.553 | 1.00 | 32.57 | C |
| ATOM | 3376 | CG | LEU | A | 235 | −63.884 | 7.252 | −.167 | 1.00 | 30.85 | C |
| ATOM | 3378 | CD1 | LEU | A | 235 | −62.428 | 7.261 | .174 | 1.00 | 28.78 | C |
| ATOM | 3382 | CD2 | LEU | A | 235 | −64.703 | 8.050 | .823 | 1.00 | 29.93 | C |
| ATOM | 3386 | C | LEU | A | 235 | −63.789 | 5.637 | −2.686 | 1.00 | 34.69 | C |
| ATOM | 3387 | O | LEU | A | 235 | −63.123 | 4.812 | −2.065 | 1.00 | 35.29 | O |
| ATOM | 3389 | N | ARG | A | 236 | −64.893 | 5.299 | −3.354 | 1.00 | 36.09 | N |
| ATOM | 3390 | CA | ARG | A | 236 | −65.290 | 3.893 | −3.458 | 1.00 | 37.26 | C |
| ATOM | 3392 | CB | ARG | A | 236 | −66.672 | 3.736 | −4.103 | 1.00 | 37.64 | C |
| ATOM | 3395 | CG | ARG | A | 236 | −67.839 | 4.000 | −3.157 | 1.00 | 39.15 | C |
| ATOM | 3398 | CD | ARG | A | 236 | −69.162 | 3.528 | −3.741 | 1.00 | 40.25 | C |
| ATOM | 3401 | NE | ARG | A | 236 | −69.385 | 4.046 | −5.095 | 1.00 | 41.64 | N |
| ATOM | 3403 | CZ | ARG | A | 236 | −69.837 | 5.269 | −5.392 | 1.00 | 42.54 | C |
| ATOM | 3404 | NH1 | ARG | A | 236 | −70.115 | 6.147 | −4.430 | 1.00 | 42.18 | N |
| ATOM | 3407 | NH2 | ARG | A | 236 | −70.012 | 5.621 | −6.668 | 1.00 | 43.04 | N |
| ATOM | 3410 | C | ARG | A | 236 | −64.266 | 3.108 | −4.262 | 1.00 | 37.81 | C |
| ATOM | 3411 | O | ARG | A | 236 | −64.104 | 1.912 | −4.060 | 1.00 | 38.07 | O |
| ATOM | 3413 | N | GLU | A | 237 | −63.584 | 3.801 | −5.168 | 1.00 | 38.69 | N |
| ATOM | 3414 | CA | GLU | A | 237 | −62.639 | 3.189 | −6.102 | 1.00 | 39.45 | C |
| ATOM | 3416 | CB | GLU | A | 237 | −62.452 | 4.108 | −7.338 | 1.00 | 40.25 | C |

TABLE 3-7-continued

Coordinates of *P. tremuloides IspS*

| | | | | | | | | | | | |
|---|---|---|---|---|---|---|---|---|---|---|---|
| ATOM | 3419 | CG | GLU | A | 237 | −62.268 | 3.387 | −8.710 | 1.00 | 43.02 | C |
| ATOM | 3422 | CD | GLU | A | 237 | −60.835 | 3.458 | −9.287 | 1.00 | 46.64 | C |
| ATOM | 3423 | OE1 | GLU | A | 237 | −60.093 | 4.440 | −8.997 | 1.00 | 48.03 | O |
| ATOM | 3424 | OE2 | GLU | A | 237 | −60.466 | 2.519 | −10.047 | 1.00 | 48.35 | O |
| ATOM | 3425 | C | GLU | A | 237 | −61.310 | 2.905 | −5.408 | 1.00 | 38.70 | C |
| ATOM | 3426 | O | GLU | A | 237 | −60.832 | 1.782 | −5.440 | 1.00 | 38.33 | O |
| ATOM | 3428 | N | THR | A | 238 | −60.726 | 3.908 | −4.764 | 1.00 | 38.40 | N |
| ATOM | 3429 | CA | THR | A | 238 | −59.504 | 3.669 | −4.009 | 1.00 | 38.74 | C |
| ATOM | 3431 | CB | THR | A | 238 | −58.710 | 4.965 | −3.593 | 1.00 | 38.78 | C |
| ATOM | 3433 | OG1 | THR | A | 238 | −59.294 | 5.583 | −2.444 | 1.00 | 38.38 | O |
| ATOM | 3435 | CG2 | THR | A | 238 | −58.612 | 5.963 | −4.743 | 1.00 | 38.94 | C |
| ATOM | 3439 | C | THR | A | 238 | −59.802 | 2.834 | −2.773 | 1.00 | 39.05 | C |
| ATOM | 3440 | O | THR | A | 238 | −58.886 | 2.294 | −2.153 | 1.00 | 39.17 | O |
| ATOM | 3442 | N | SER | A | 239 | −61.076 | 2.717 | −2.408 | 1.00 | 39.34 | N |
| ATOM | 3443 | CA | SER | A | 239 | −61.443 | 1.841 | −1.304 | 1.00 | 39.47 | C |
| ATOM | 3445 | CB | SER | A | 239 | −62.844 | 2.149 | −.792 | 1.00 | 39.34 | C |
| ATOM | 3448 | OG | SER | A | 239 | −63.087 | 1.428 | .396 | 1.00 | 39.94 | O |
| ATOM | 3450 | C | SER | A | 239 | −61.313 | .367 | −1.699 | 1.00 | 39.53 | C |
| ATOM | 3451 | O | SER | A | 239 | −60.834 | −.439 | −.900 | 1.00 | 39.53 | O |
| ATOM | 3453 | N | ARG | A | 240 | −61.728 | .021 | −2.921 | 1.00 | 39.69 | N |
| ATOM | 3454 | CA | ARG | A | 240 | −61.559 | −1.341 | −3.439 | 1.00 | 39.79 | C |
| ATOM | 3456 | CB | ARG | A | 240 | −62.105 | −1.492 | −4.867 | 1.00 | 40.34 | C |
| ATOM | 3459 | CG | ARG | A | 240 | −63.624 | −1.715 | −4.947 | 1.00 | 43.03 | C |
| ATOM | 3462 | CD | ARG | A | 240 | −64.104 | −2.125 | −6.364 | 1.00 | 46.66 | C |
| ATOM | 3465 | NE | ARG | A | 240 | −63.780 | −1.136 | −7.416 | 1.00 | 50.46 | N |
| ATOM | 3467 | CZ | ARG | A | 240 | −64.535 | −.082 | −7.775 | 1.00 | 53.13 | C |
| ATOM | 3468 | NH1 | ARG | A | 240 | −64.112 | .732 | −8.749 | 1.00 | 53.13 | N |
| ATOM | 3471 | NH2 | ARG | A | 240 | −65.707 | .178 | −7.178 | 1.00 | 54.02 | N |
| ATOM | 3474 | C | ARG | A | 240 | −60.089 | −1.704 | −3.414 | 1.00 | 38.94 | C |
| ATOM | 3475 | O | ARG | A | 240 | −59.732 | −2.795 | −2.978 | 1.00 | 39.09 | O |
| ATOM | 3477 | N | TRP | A | 241 | −59.246 | −.775 | −3.862 | 1.00 | 37.92 | N |
| ATOM | 3478 | CA | TRP | A | 241 | −57.787 | −.947 | −3.842 | 1.00 | 36.93 | C |
| ATOM | 3480 | CB | TRP | A | 241 | −57.099 | .318 | −4.388 | 1.00 | 36.57 | C |
| ATOM | 3483 | CG | TRP | A | 241 | −55.624 | .333 | −4.209 | 1.00 | 34.71 | C |
| ATOM | 3484 | CD1 | TRP | A | 241 | −54.702 | −.312 | −4.969 | 1.00 | 33.50 | C |
| ATOM | 3486 | NE1 | TRP | A | 241 | −53.441 | −.068 | −4.482 | 1.00 | 32.62 | N |
| ATOM | 3488 | CE2 | TRP | A | 241 | −53.538 | .747 | −3.392 | 1.00 | 31.16 | C |
| ATOM | 3489 | CD2 | TRP | A | 241 | −54.896 | 1.022 | −3.191 | 1.00 | 32.61 | C |
| ATOM | 3490 | CE3 | TRP | A | 241 | −55.268 | 1.837 | −2.117 | 1.00 | 32.63 | C |
| ATOM | 3492 | CZ3 | TRP | A | 241 | −54.293 | 2.345 | −1.307 | 1.00 | 31.31 | C |
| ATOM | 3494 | CH2 | TRP | A | 241 | −52.956 | 2.053 | −1.537 | 1.00 | 31.81 | C |
| ATOM | 3496 | CZ2 | TRP | A | 241 | −52.560 | 1.252 | −2.577 | 1.00 | 31.18 | C |
| ATOM | 3498 | C | TRP | A | 241 | −57.263 | −1.274 | −2.444 | 1.00 | 36.67 | C |
| ATOM | 3499 | O | TRP | A | 241 | −56.540 | −2.247 | −2.252 | 1.00 | 36.32 | O |
| ATOM | 3501 | N | TRP | A | 242 | −57.647 | −.460 | −1.471 | 1.00 | 36.59 | N |
| ATOM | 3502 | CA | TRP | A | 242 | −57.150 | −.593 | −.100 | 1.00 | 36.80 | C |
| ATOM | 3504 | CB | TRP | A | 242 | −57.694 | .582 | .734 | 1.00 | 36.47 | C |
| ATOM | 3507 | CG | TRP | A | 242 | −57.113 | .754 | 2.107 | 1.00 | 35.59 | C |
| ATOM | 3508 | CD1 | TRP | A | 242 | −57.806 | .831 | 3.270 | 1.00 | 35.14 | C |
| ATOM | 3510 | NE1 | TRP | A | 242 | −56.950 | .999 | 4.328 | 1.00 | 34.47 | N |
| ATOM | 3512 | CE2 | TRP | A | 242 | −55.667 | 1.032 | 3.859 | 1.00 | 34.64 | C |
| ATOM | 3513 | CD2 | TRP | A | 242 | −55.728 | .884 | 2.461 | 1.00 | 35.26 | C |
| ATOM | 3514 | CE3 | TRP | A | 242 | −54.531 | .882 | 1.732 | 1.00 | 35.22 | C |
| ATOM | 3516 | CZ3 | TRP | A | 242 | −53.342 | 1.024 | 2.409 | 1.00 | 34.30 | C |
| ATOM | 3518 | CH2 | TRP | A | 242 | −53.318 | 1.169 | 3.799 | 1.00 | 34.70 | C |
| ATOM | 3520 | CZ2 | TRP | A | 242 | −54.467 | 1.173 | 4.542 | 1.00 | 34.63 | C |
| ATOM | 3522 | C | TRP | A | 242 | −57.482 | −1.975 | .524 | 1.00 | 37.34 | C |
| ATOM | 3523 | O | TRP | A | 242 | −56.628 | −2.623 | 1.126 | 1.00 | 36.53 | O |
| ATOM | 3525 | N | ARG | A | 243 | −58.720 | −2.421 | .348 | 1.00 | 38.54 | N |
| ATOM | 3526 | CA | ARG | A | 243 | −59.149 | −3.734 | .822 | 1.00 | 39.71 | C |
| ATOM | 3528 | CB | ARG | A | 243 | −60.669 | −3.896 | .687 | 1.00 | 40.10 | C |
| ATOM | 3531 | CG | ARG | A | 243 | −61.495 | −3.134 | 1.747 | 1.00 | 42.18 | C |
| ATOM | 3534 | CD | ARG | A | 243 | −62.826 | −2.623 | 1.169 | 1.00 | 45.18 | C |
| ATOM | 3537 | NE | ARG | A | 243 | −63.506 | −3.656 | .369 | 1.00 | 48.22 | N |
| ATOM | 3539 | CZ | ARG | A | 243 | −64.374 | −3.431 | −.629 | 1.00 | 49.95 | C |
| ATOM | 3540 | NH1 | ARG | A | 243 | −64.717 | −2.182 | −.991 | 1.00 | 50.13 | N |
| ATOM | 3543 | NH2 | ARG | A | 243 | −64.911 | −4.477 | −1.273 | 1.00 | 49.77 | N |
| ATOM | 3546 | C | ARG | A | 243 | −58.438 | −4.852 | .068 | 1.00 | 40.08 | C |
| ATOM | 3547 | O | ARG | A | 243 | −58.084 | −5.870 | .665 | 1.00 | 40.45 | O |
| ATOM | 3549 | N | ARG | A | 244 | −58.236 | −4.663 | −1.236 | 1.00 | 40.42 | N |
| ATOM | 3550 | CA | ARG | A | 244 | −57.499 | −5.621 | −2.063 | 1.00 | 40.65 | C |
| ATOM | 3552 | CB | ARG | A | 244 | −57.370 | −5.100 | −3.503 | 1.00 | 41.29 | C |
| ATOM | 3555 | CG | ARG | A | 244 | −56.939 | −6.126 | −4.560 | 1.00 | 43.27 | C |
| ATOM | 3558 | CD | ARG | A | 244 | −58.090 | −7.062 | −4.952 | 1.00 | 46.01 | C |
| ATOM | 3561 | NE | ARG | A | 244 | −57.595 | −8.337 | −5.485 | 1.00 | 48.77 | N |
| ATOM | 3563 | CZ | ARG | A | 244 | −57.075 | −9.332 | −4.752 | 1.00 | 51.17 | C |
| ATOM | 3564 | NH1 | ARG | A | 244 | −56.968 | −9.234 | −3.422 | 1.00 | 51.63 | N |
| ATOM | 3567 | NH2 | ARG | A | 244 | −56.656 | −10.448 | −5.353 | 1.00 | 52.11 | N |

TABLE 3-7-continued

| Coordinates of *P. tremuloides IspS* | | | | | | | | | | | |
|---|---|---|---|---|---|---|---|---|---|---|---|
| ATOM | 3570 | C | ARG | A | 244 | −56.120 | −5.861 | −1.465 | 1.00 | 40.12 | C |
| ATOM | 3571 | O | ARG | A | 244 | −55.728 | −7.000 | −1.235 | 1.00 | 39.96 | O |
| ATOM | 3573 | N | VAL | A | 245 | −55.399 | −4.778 | −1.201 | 1.00 | 39.78 | N |
| ATOM | 3574 | CA | VAL | A | 245 | −54.099 | −4.858 | −.543 | 1.00 | 39.68 | C |
| ATOM | 3576 | CB | VAL | A | 245 | −53.430 | −3.458 | −.437 | 1.00 | 39.70 | C |
| ATOM | 3578 | CG1 | VAL | A | 245 | −53.133 | −2.914 | −1.824 | 1.00 | 39.54 | C |
| ATOM | 3582 | CG2 | VAL | A | 245 | −52.145 | −3.507 | .395 | 1.00 | 39.41 | C |
| ATOM | 3586 | C | VAL | A | 245 | −54.262 | −5.472 | .841 | 1.00 | 39.73 | C |
| ATOM | 3587 | O | VAL | A | 245 | −53.455 | −6.291 | 1.253 | 1.00 | 39.53 | O |
| ATOM | 3589 | N | GLY | A | 246 | −55.312 | −5.051 | 1.544 | 1.00 | 40.11 | N |
| ATOM | 3590 | CA | GLY | A | 246 | −55.705 | −5.617 | 2.839 | 1.00 | 40.35 | C |
| ATOM | 3593 | C | GLY | A | 246 | −54.621 | −5.648 | 3.894 | 1.00 | 40.58 | C |
| ATOM | 3594 | O | GLY | A | 246 | −54.396 | −6.676 | 4.510 | 1.00 | 40.68 | O |
| ATOM | 3596 | N | LEU | A | 247 | −53.963 | −4.522 | 4.129 | 1.00 | 41.15 | N |
| ATOM | 3597 | CA | LEU | A | 247 | −52.778 | −4.519 | 4.982 | 1.00 | 41.71 | C |
| ATOM | 3599 | CB | LEU | A | 247 | −51.808 | −3.422 | 4.537 | 1.00 | 41.60 | C |
| ATOM | 3602 | CG | LEU | A | 247 | −50.334 | −3.815 | 4.441 | 1.00 | 40.83 | C |
| ATOM | 3604 | CD1 | LEU | A | 247 | −50.158 | −5.014 | 3.539 | 1.00 | 40.54 | C |
| ATOM | 3608 | CD2 | LEU | A | 247 | −49.534 | −2.644 | 3.918 | 1.00 | 39.92 | C |
| ATOM | 3612 | C | LEU | A | 247 | −53.136 | −4.385 | 6.471 | 1.00 | 42.60 | C |
| ATOM | 3613 | O | LEU | A | 247 | −52.588 | −5.111 | 7.313 | 1.00 | 42.06 | O |
| ATOM | 3615 | N | ALA | A | 248 | −54.064 | −3.475 | 6.788 | 1.00 | 43.75 | N |
| ATOM | 3616 | CA | ALA | A | 248 | −54.603 | −3.352 | 8.162 | 1.00 | 44.52 | C |
| ATOM | 3618 | CB | ALA | A | 248 | −55.712 | −2.296 | 8.210 | 1.00 | 44.31 | C |
| ATOM | 3622 | C | ALA | A | 248 | −55.129 | −4.706 | 8.695 | 1.00 | 45.10 | C |
| ATOM | 3623 | O | ALA | A | 248 | −54.969 | −5.041 | 9.875 | 1.00 | 44.96 | O |
| ATOM | 3625 | N | THR | A | 249 | −55.742 | −5.477 | 7.802 | 1.00 | 45.91 | N |
| ATOM | 3626 | CA | THR | A | 249 | −56.328 | −6.768 | 8.154 | 1.00 | 46.50 | C |
| ATOM | 3628 | CB | THR | A | 249 | −57.303 | −7.277 | 7.041 | 1.00 | 46.48 | C |
| ATOM | 3630 | OG1 | THR | A | 249 | −56.583 | −8.039 | 6.063 | 1.00 | 46.20 | O |
| ATOM | 3632 | CG2 | THR | A | 249 | −58.033 | −6.102 | 6.350 | 1.00 | 46.70 | C |
| ATOM | 3636 | C | THR | A | 249 | −55.257 | −7.840 | 8.447 | 1.00 | 47.06 | C |
| ATOM | 3637 | O | THR | A | 249 | −55.531 | −8.813 | 9.159 | 1.00 | 47.22 | O |
| ATOM | 3639 | N | LYS | A | 250 | −54.049 | −7.661 | 7.905 | 1.00 | 47.52 | N |
| ATOM | 3640 | CA | LYS | A | 250 | −52.952 | −8.620 | 8.096 | 1.00 | 47.91 | C |
| ATOM | 3642 | CB | LYS | A | 250 | −52.319 | −8.976 | 6.744 | 1.00 | 48.09 | C |
| ATOM | 3645 | CG | LYS | A | 250 | −52.911 | −10.229 | 6.088 | 1.00 | 48.91 | C |
| ATOM | 3648 | CD | LYS | A | 250 | −52.210 | −11.510 | 6.585 | 1.00 | 49.88 | C |
| ATOM | 3651 | CE | LYS | A | 250 | −53.066 | −12.760 | 6.349 | 1.00 | 50.12 | C |
| ATOM | 3654 | NZ | LYS | A | 250 | −52.385 | −14.011 | 6.791 | 1.00 | 49.99 | N |
| ATOM | 3658 | C | LYS | A | 250 | −51.880 | −8.129 | 9.078 | 1.00 | 48.13 | C |
| ATOM | 3659 | O | LYS | A | 250 | −51.252 | −8.939 | 9.759 | 1.00 | 47.89 | O |
| ATOM | 3661 | N | LEU | A | 251 | −51.667 | −6.812 | 9.134 | 1.00 | 48.63 | N |
| ATOM | 3662 | CA | LEU | A | 251 | −50.758 | −6.187 | 10.114 | 1.00 | 48.83 | C |
| ATOM | 3664 | CB | LEU | A | 251 | −49.981 | −5.020 | 9.485 | 1.00 | 48.74 | C |
| ATOM | 3667 | CG | LEU | A | 251 | −48.569 | −5.296 | 8.960 | 1.00 | 48.51 | C |
| ATOM | 3669 | CD1 | LEU | A | 251 | −48.472 | −6.594 | 8.174 | 1.00 | 47.96 | C |
| ATOM | 3673 | CD2 | LEU | A | 251 | −48.102 | −4.115 | 8.116 | 1.00 | 48.76 | C |
| ATOM | 3677 | C | LEU | A | 251 | −51.559 | −5.703 | 11.324 | 1.00 | 49.17 | C |
| ATOM | 3678 | O | LEU | A | 251 | −52.176 | −4.632 | 11.304 | 1.00 | 49.28 | O |
| ATOM | 3680 | N | HIS | A | 252 | −51.521 | −6.486 | 12.393 | 1.00 | 49.53 | N |
| ATOM | 3681 | CA | HIS | A | 252 | −52.470 | −6.322 | 13.494 | 1.00 | 50.02 | C |
| ATOM | 3683 | CB | HIS | A | 252 | −52.598 | −7.647 | 14.266 | 1.00 | 50.42 | C |
| ATOM | 3686 | CG | HIS | A | 252 | −52.860 | −8.834 | 13.380 | 1.00 | 52.23 | C |
| ATOM | 3687 | ND1 | HIS | A | 252 | −54.032 | −8.989 | 12.667 | 1.00 | 53.75 | N |
| ATOM | 3689 | CE1 | HIS | A | 252 | −53.978 | −10.113 | 11.973 | 1.00 | 54.43 | C |
| ATOM | 3691 | NE2 | HIS | A | 252 | −52.810 | −10.689 | 12.201 | 1.00 | 54.52 | N |
| ATOM | 3693 | CD2 | HIS | A | 252 | −52.090 | −9.910 | 13.077 | 1.00 | 53.70 | C |
| ATOM | 3695 | C | HIS | A | 252 | −52.161 | −5.147 | 14.441 | 1.00 | 49.64 | C |
| ATOM | 3696 | O | HIS | A | 252 | −52.951 | −4.849 | 15.336 | 1.00 | 49.61 | O |
| ATOM | 3698 | N | PHE | A | 253 | −51.027 | −4.483 | 14.229 | 1.00 | 49.37 | N |
| ATOM | 3699 | CA | PHE | A | 253 | −50.652 | −3.273 | 14.973 | 1.00 | 49.15 | C |
| ATOM | 3701 | CB | PHE | A | 253 | −49.144 | −3.273 | 15.260 | 1.00 | 49.07 | C |
| ATOM | 3704 | CG | PHE | A | 253 | −48.307 | −3.112 | 14.025 | 1.00 | 48.30 | C |
| ATOM | 3705 | CD1 | PHE | A | 253 | −48.028 | −1.851 | 13.518 | 1.00 | 48.10 | C |
| ATOM | 3707 | CE1 | PHE | A | 253 | −47.290 | −1.702 | 12.349 | 1.00 | 48.21 | C |
| ATOM | 3709 | CZ | PHE | A | 253 | −46.825 | −2.825 | 11.675 | 1.00 | 47.88 | C |
| ATOM | 3711 | CE2 | PHE | A | 253 | −47.101 | −4.090 | 12.175 | 1.00 | 47.66 | C |
| ATOM | 3713 | CD2 | PHE | A | 253 | −47.842 | −4.226 | 13.338 | 1.00 | 47.74 | C |
| ATOM | 3715 | C | PHE | A | 253 | −50.974 | −2.006 | 14.176 | 1.00 | 49.31 | C |
| ATOM | 3716 | O | PHE | A | 253 | −50.846 | −.893 | 14.702 | 1.00 | 49.01 | O |
| ATOM | 3718 | N | ALA | A | 254 | −51.365 | −2.185 | 12.910 | 1.00 | 49.48 | N |
| ATOM | 3719 | CA | ALA | A | 254 | −51.412 | −1.095 | 11.931 | 1.00 | 49.63 | C |
| ATOM | 3721 | CB | ALA | A | 254 | −51.344 | −1.663 | 10.524 | 1.00 | 49.64 | C |
| ATOM | 3725 | C | ALA | A | 254 | −52.650 | −.224 | 12.061 | 1.00 | 49.77 | C |
| ATOM | 3726 | O | ALA | A | 254 | −53.761 | −.735 | 12.219 | 1.00 | 49.86 | O |
| ATOM | 3728 | N | ARG | A | 255 | −52.452 | 1.090 | 11.975 | 1.00 | 49.93 | N |
| ATOM | 3729 | CA | ARG | A | 255 | −53.562 | 2.042 | 11.908 | 1.00 | 50.27 | C |

TABLE 3-7-continued

Coordinates of *P. tremuloides IspS*

| | | | | | | | | | | | |
|---|---|---|---|---|---|---|---|---|---|---|---|
| ATOM | 3731 | CB | ARG | A | 255 | −53.094 | 3.468 | 12.237 | 1.00 | 50.43 | C |
| ATOM | 3734 | CG | ARG | A | 255 | −52.678 | 3.736 | 13.696 | 1.00 | 50.82 | C |
| ATOM | 3737 | CD | ARG | A | 255 | −52.242 | 5.211 | 13.887 | 1.00 | 51.32 | C |
| ATOM | 3740 | NE | ARG | A | 255 | −51.003 | 5.522 | 13.155 | 1.00 | 51.81 | N |
| ATOM | 3742 | CZ | ARG | A | 255 | −50.571 | 6.746 | 12.829 | 1.00 | 51.67 | C |
| ATOM | 3743 | NH1 | ARG | A | 255 | −51.264 | 7.839 | 13.146 | 1.00 | 51.63 | N |
| ATOM | 3746 | NH2 | ARG | A | 255 | −49.427 | 6.877 | 12.162 | 1.00 | 51.52 | N |
| ATOM | 3749 | C | ARG | A | 255 | −54.160 | 2.040 | 10.497 | 1.00 | 50.32 | C |
| ATOM | 3750 | O | ARG | A | 255 | −53.416 | 2.081 | 9.504 | 1.00 | 50.35 | O |
| ATOM | 3752 | N | ASP | A | 256 | −55.492 | 2.005 | 10.412 | 1.00 | 50.17 | N |
| ATOM | 3753 | CA | ASP | A | 256 | −56.190 | 2.090 | 9.128 | 1.00 | 50.18 | C |
| ATOM | 3755 | CB | ASP | A | 256 | −57.259 | 1.009 | 9.037 | 1.00 | 50.37 | C |
| ATOM | 3758 | CG | ASP | A | 256 | −58.095 | 1.130 | 7.780 | 1.00 | 50.96 | C |
| ATOM | 3759 | OD1 | ASP | A | 256 | −59.252 | 1.601 | 7.881 | 1.00 | 52.00 | O |
| ATOM | 3760 | OD2 | ASP | A | 256 | −57.581 | .787 | 6.693 | 1.00 | 50.94 | O |
| ATOM | 3761 | C | ASP | A | 256 | −56.838 | 3.470 | 8.945 | 1.00 | 49.85 | C |
| ATOM | 3762 | O | ASP | A | 256 | −57.812 | 3.804 | 9.624 | 1.00 | 50.13 | O |
| ATOM | 3764 | N | ARG | A | 257 | −56.315 | 4.263 | 8.013 | 1.00 | 49.11 | N |
| ATOM | 3765 | CA | ARG | A | 257 | −56.712 | 5.665 | 7.913 | 1.00 | 48.59 | C |
| ATOM | 3767 | CB | ARG | A | 257 | −55.622 | 6.553 | 8.529 | 1.00 | 48.79 | C |
| ATOM | 3770 | CG | ARG | A | 257 | −55.318 | 6.275 | 10.006 | 1.00 | 49.85 | C |
| ATOM | 3773 | CD | ARG | A | 257 | −56.538 | 6.480 | 10.908 | 1.00 | 51.01 | C |
| ATOM | 3776 | NE | ARG | A | 257 | −56.198 | 7.274 | 12.089 | 1.00 | 51.80 | N |
| ATOM | 3778 | CZ | ARG | A | 257 | −55.779 | 6.791 | 13.260 | 1.00 | 52.00 | C |
| ATOM | 3779 | NH1 | ARG | A | 257 | −55.643 | 5.486 | 13.468 | 1.00 | 51.64 | N |
| ATOM | 3782 | NH2 | ARG | A | 257 | −55.501 | 7.638 | 14.245 | 1.00 | 52.62 | N |
| ATOM | 3785 | C | ARG | A | 257 | −56.988 | 6.112 | 6.477 | 1.00 | 47.58 | C |
| ATOM | 3786 | O | ARG | A | 257 | −56.476 | 7.144 | 6.031 | 1.00 | 47.40 | O |
| ATOM | 3788 | N | LEU | A | 258 | −57.814 | 5.352 | 5.761 | 1.00 | 46.18 | N |
| ATOM | 3789 | CA | LEU | A | 258 | −58.094 | 5.672 | 4.358 | 1.00 | 44.78 | C |
| ATOM | 3791 | CB | LEU | A | 258 | −58.777 | 4.508 | 3.629 | 1.00 | 44.57 | C |
| ATOM | 3794 | CG | LEU | A | 258 | −58.917 | 4.731 | 2.121 | 1.00 | 43.79 | C |
| ATOM | 3796 | CD1 | LEU | A | 258 | −57.557 | 4.661 | 1.478 | 1.00 | 43.89 | C |
| ATOM | 3800 | CD2 | LEU | A | 258 | −59.850 | 3.733 | 1.492 | 1.00 | 42.88 | C |
| ATOM | 3804 | C | LEU | A | 258 | −58.970 | 6.907 | 4.259 | 1.00 | 43.52 | C |
| ATOM | 3805 | O | LEU | A | 258 | −58.643 | 7.849 | 3.545 | 1.00 | 43.42 | O |
| ATOM | 3807 | N | ILE | A | 259 | −60.080 | 6.895 | 4.983 | 1.00 | 41.98 | N |
| ATOM | 3808 | CA | ILE | A | 259 | −61.072 | 7.948 | 4.843 | 1.00 | 40.89 | C |
| ATOM | 3810 | CB | ILE | A | 259 | −62.349 | 7.703 | 5.693 | 1.00 | 41.02 | C |
| ATOM | 3812 | CG1 | ILE | A | 259 | −62.846 | 6.248 | 5.570 | 1.00 | 41.82 | C |
| ATOM | 3815 | CD1 | ILE | A | 259 | −64.029 | 5.872 | 6.508 | 1.00 | 42.29 | C |
| ATOM | 3819 | CG2 | ILE | A | 259 | −63.446 | 8.662 | 5.262 | 1.00 | 40.47 | C |
| ATOM | 3823 | C | ILE | A | 259 | −60.424 | 9.253 | 5.273 | 1.00 | 39.74 | C |
| ATOM | 3824 | O | ILE | A | 259 | −60.607 | 10.291 | 4.635 | 1.00 | 39.25 | O |
| ATOM | 3826 | N | GLU | A | 260 | −59.650 | 9.191 | 6.355 | 1.00 | 38.46 | N |
| ATOM | 3827 | CA | GLU | A | 260 | −58.951 | 10.366 | 6.846 | 1.00 | 37.44 | C |
| ATOM | 3829 | CB | GLU | A | 260 | −58.183 | 10.072 | 8.140 | 1.00 | 37.74 | C |
| ATOM | 3832 | CG | GLU | A | 260 | −59.041 | 9.934 | 9.393 | 1.00 | 38.71 | C |
| ATOM | 3835 | CD | GLU | A | 260 | −59.469 | 8.501 | 9.693 | 1.00 | 41.00 | C |
| ATOM | 3836 | OE1 | GLU | A | 260 | −59.273 | 7.594 | 8.842 | 1.00 | 42.70 | O |
| ATOM | 3837 | OE2 | GLU | A | 260 | −60.012 | 8.281 | 10.800 | 1.00 | 42.43 | O |
| ATOM | 3838 | C | GLU | A | 260 | −57.995 | 10.841 | 5.764 | 1.00 | 35.94 | C |
| ATOM | 3839 | O | GLU | A | 260 | −57.981 | 12.020 | 5.418 | 1.00 | 36.10 | O |
| ATOM | 3841 | N | SER | A | 261 | −57.222 | 9.908 | 5.212 | 1.00 | 34.02 | N |
| ATOM | 3842 | CA | SER | A | 261 | −56.263 | 10.229 | 4.152 | 1.00 | 32.47 | C |
| ATOM | 3844 | CB | SER | A | 261 | −55.407 | 9.015 | 3.774 | 1.00 | 32.51 | C |
| ATOM | 3847 | OG | SER | A | 261 | −54.253 | 8.940 | 4.584 | 1.00 | 33.14 | O |
| ATOM | 3849 | C | SER | A | 261 | −56.894 | 10.764 | 2.889 | 1.00 | 30.82 | C |
| ATOM | 3850 | O | SER | A | 261 | −56.199 | 11.306 | 2.062 | 1.00 | 30.79 | O |
| ATOM | 3852 | N | PHE | A | 262 | −58.194 | 10.589 | 2.713 | 1.00 | 29.25 | N |
| ATOM | 3853 | CA | PHE | A | 262 | −58.861 | 11.091 | 1.514 | 1.00 | 27.98 | C |
| ATOM | 3855 | CB | PHE | A | 262 | −60.011 | 10.185 | 1.119 | 1.00 | 27.57 | C |
| ATOM | 3858 | CG | PHE | A | 262 | −60.473 | 10.423 | −.251 | 1.00 | 26.11 | C |
| ATOM | 3859 | CD1 | PHE | A | 262 | −59.763 | 9.914 | −1.318 | 1.00 | 25.14 | C |
| ATOM | 3861 | CE1 | PHE | A | 262 | −60.169 | 10.147 | −2.605 | 1.00 | 24.32 | C |
| ATOM | 3863 | CZ | PHE | A | 262 | −61.284 | 10.917 | −2.840 | 1.00 | 24.36 | C |
| ATOM | 3865 | CE2 | PHE | A | 262 | −61.987 | 11.445 | −1.785 | 1.00 | 25.23 | C |
| ATOM | 3867 | CD2 | PHE | A | 262 | −61.575 | 11.201 | −.492 | 1.00 | 25.61 | C |
| ATOM | 3869 | C | PHE | A | 262 | −59.394 | 12.507 | 1.707 | 1.00 | 27.29 | C |
| ATOM | 3870 | O | PHE | A | 262 | −59.275 | 13.359 | .821 | 1.00 | 27.39 | O |
| ATOM | 3872 | N | TYR | A | 263 | −60.025 | 12.723 | 2.856 | 1.00 | 26.19 | N |
| ATOM | 3873 | CA | TYR | A | 263 | −60.415 | 14.052 | 3.310 | 1.00 | 25.22 | C |
| ATOM | 3875 | CB | TYR | A | 263 | −60.975 | 13.942 | 4.735 | 1.00 | 25.21 | C |
| ATOM | 3878 | CG | TYR | A | 263 | −61.037 | 15.199 | 5.578 | 1.00 | 25.37 | C |
| ATOM | 3879 | CD1 | TYR | A | 263 | −62.020 | 16.152 | 5.385 | 1.00 | 24.95 | C |
| ATOM | 3881 | CE1 | TYR | A | 263 | −62.084 | 17.282 | 6.197 | 1.00 | 26.54 | C |
| ATOM | 3883 | CZ | TYR | A | 263 | −61.158 | 17.455 | 7.229 | 1.00 | 27.44 | C |
| ATOM | 3884 | OH | TYR | A | 263 | −61.186 | 18.567 | 8.059 | 1.00 | 28.97 | O |

TABLE 3-7-continued

Coordinates of *P. tremuloides IspS*

| | | | | | | | | | | | |
|---|---|---|---|---|---|---|---|---|---|---|---|
| ATOM | 3886 | CE2 | TYR | A | 263 | −60.185 | 16.512 | 7.438 | 1.00 | 27.10 | C |
| ATOM | 3888 | CD2 | TYR | A | 263 | −60.136 | 15.390 | 6.626 | 1.00 | 26.91 | C |
| ATOM | 3890 | C | TYR | A | 263 | −59.190 | 14.946 | 3.238 | 1.00 | 24.29 | C |
| ATOM | 3891 | O | TYR | A | 263 | −59.267 | 16.077 | 2.757 | 1.00 | 24.13 | O |
| ATOM | 3893 | N | TRP | A | 264 | −58.055 | 14.415 | 3.682 | 1.00 | 23.01 | N |
| ATOM | 3894 | CA | TRP | A | 264 | −56.789 | 15.121 | 3.567 | 1.00 | 22.32 | C |
| ATOM | 3896 | CB | TRP | A | 264 | −55.642 | 14.261 | 4.119 | 1.00 | 22.26 | C |
| ATOM | 3899 | CG | TRP | A | 264 | −54.326 | 14.874 | 3.860 | 1.00 | 22.16 | C |
| ATOM | 3900 | CD1 | TRP | A | 264 | −53.614 | 14.821 | 2.699 | 1.00 | 22.68 | C |
| ATOM | 3902 | NE1 | TRP | A | 264 | −52.456 | 15.538 | 2.818 | 1.00 | 23.08 | N |
| ATOM | 3904 | CE2 | TRP | A | 264 | −52.407 | 16.083 | 4.072 | 1.00 | 23.07 | C |
| ATOM | 3905 | CD2 | TRP | A | 264 | −53.579 | 15.686 | 4.753 | 1.00 | 22.18 | C |
| ATOM | 3906 | CE3 | TRP | A | 264 | −53.782 | 16.119 | 6.066 | 1.00 | 22.57 | C |
| ATOM | 3908 | CZ3 | TRP | A | 264 | −52.824 | 16.925 | 6.657 | 1.00 | 23.43 | C |
| ATOM | 3910 | CH2 | TRP | A | 264 | −51.656 | 17.297 | 5.955 | 1.00 | 24.14 | C |
| ATOM | 3912 | CZ2 | TRP | A | 264 | −51.433 | 16.886 | 4.663 | 1.00 | 23.64 | C |
| ATOM | 3914 | C | TRP | A | 264 | −56.485 | 15.523 | 2.112 | 1.00 | 21.50 | C |
| ATOM | 3915 | O | TRP | A | 264 | −56.179 | 16.682 | 1.820 | 1.00 | 21.29 | O |
| ATOM | 3917 | N | ALA | A | 265 | −56.561 | 14.547 | 1.213 | 1.00 | 20.41 | N |
| ATOM | 3918 | CA | ALA | A | 265 | −56.242 | 14.760 | −.187 | 1.00 | 19.63 | C |
| ATOM | 3920 | CB | ALA | A | 265 | −56.298 | 13.437 | −.953 | 1.00 | 19.39 | C |
| ATOM | 3924 | C | ALA | A | 265 | −57.176 | 15.792 | −.798 | 1.00 | 19.07 | C |
| ATOM | 3925 | O | ALA | A | 265 | −56.760 | 16.573 | −1.633 | 1.00 | 18.99 | O |
| ATOM | 3927 | N | VAL | A | 266 | −58.431 | 15.814 | −.359 | 1.00 | 18.78 | N |
| ATOM | 3928 | CA | VAL | A | 266 | −59.396 | 16.828 | −.818 | 1.00 | 18.56 | C |
| ATOM | 3930 | CB | VAL | A | 266 | −60.839 | 16.541 | −.278 | 1.00 | 18.41 | C |
| ATOM | 3932 | CG1 | VAL | A | 266 | −61.405 | 15.298 | −.935 | 1.00 | 18.88 | C |
| ATOM | 3936 | CG2 | VAL | A | 266 | −61.780 | 17.709 | −.505 | 1.00 | 17.21 | C |
| ATOM | 3940 | C | VAL | A | 266 | −58.947 | 18.257 | −.450 | 1.00 | 18.43 | C |
| ATOM | 3941 | O | VAL | A | 266 | −59.250 | 19.200 | −1.171 | 1.00 | 18.83 | O |
| ATOM | 3943 | N | GLY | A | 267 | −58.230 | 18.411 | .663 | 1.00 | 17.96 | N |
| ATOM | 3944 | CA | GLY | A | 267 | −57.714 | 19.712 | 1.067 | 1.00 | 17.45 | C |
| ATOM | 3947 | C | GLY | A | 267 | −56.687 | 20.180 | .070 | 1.00 | 17.20 | C |
| ATOM | 3948 | O | GLY | A | 267 | −56.574 | 21.365 | −.215 | 1.00 | 17.41 | O |
| ATOM | 3950 | N | VAL | A | 268 | −55.959 | 19.219 | −.480 | 1.00 | 16.88 | N |
| ATOM | 3951 | CA | VAL | A | 268 | −54.822 | 19.487 | −1.319 | 1.00 | 16.62 | C |
| ATOM | 3953 | CB | VAL | A | 268 | −53.833 | 18.300 | −1.290 | 1.00 | 16.19 | C |
| ATOM | 3955 | CG1 | VAL | A | 268 | −52.691 | 18.536 | −2.240 | 1.00 | 15.50 | C |
| ATOM | 3959 | CG2 | VAL | A | 268 | −53.310 | 18.121 | .103 | 1.00 | 15.30 | C |
| ATOM | 3963 | C | VAL | A | 268 | −55.262 | 19.788 | −2.736 | 1.00 | 17.15 | C |
| ATOM | 3964 | O | VAL | A | 268 | −54.748 | 20.710 | −3.350 | 1.00 | 17.12 | O |
| ATOM | 3966 | N | ALA | A | 269 | −56.217 | 19.014 | −3.243 | 1.00 | 17.99 | N |
| ATOM | 3967 | CA | ALA | A | 269 | −56.688 | 19.158 | −4.622 | 1.00 | 18.79 | C |
| ATOM | 3969 | CB | ALA | A | 269 | −55.958 | 18.183 | −5.551 | 1.00 | 18.26 | C |
| ATOM | 3973 | C | ALA | A | 269 | −58.196 | 18.938 | −4.672 | 1.00 | 19.70 | C |
| ATOM | 3974 | O | ALA | A | 269 | −58.665 | 17.834 | −4.958 | 1.00 | 19.50 | O |
| ATOM | 3976 | N | PHE | A | 270 | −58.945 | 20.011 | −4.417 | 1.00 | 21.09 | N |
| ATOM | 3977 | CA | PHE | A | 270 | −60.393 | 19.910 | −4.211 | 1.00 | 22.32 | C |
| ATOM | 3979 | CB | PHE | A | 270 | −60.925 | 21.108 | −3.404 | 1.00 | 22.49 | C |
| ATOM | 3982 | CG | PHE | A | 270 | −61.193 | 22.321 | −4.246 | 1.00 | 23.31 | C |
| ATOM | 3983 | CD1 | PHE | A | 270 | −62.423 | 22.483 | −4.883 | 1.00 | 24.16 | C |
| ATOM | 3985 | CE1 | PHE | A | 270 | −62.662 | 23.569 | −5.683 | 1.00 | 23.84 | C |
| ATOM | 3987 | CZ | PHE | A | 270 | −61.675 | 24.497 | −5.871 | 1.00 | 23.93 | C |
| ATOM | 3989 | CE2 | PHE | A | 270 | −60.448 | 24.349 | −5.242 | 1.00 | 23.33 | C |
| ATOM | 3991 | CD2 | PHE | A | 270 | −60.213 | 23.268 | −4.443 | 1.00 | 23.11 | C |
| ATOM | 3993 | C | PHE | A | 270 | −61.173 | 19.820 | −5.515 | 1.00 | 23.21 | C |
| ATOM | 3994 | O | PHE | A | 270 | −62.142 | 19.069 | −5.599 | 1.00 | 23.48 | O |
| ATOM | 3996 | N | GLU | A | 271 | −60.771 | 20.599 | −6.522 | 1.00 | 24.16 | N |
| ATOM | 3997 | CA | GLU | A | 271 | −61.595 | 20.744 | −7.741 | 1.00 | 25.01 | C |
| ATOM | 3999 | CB | GLU | A | 271 | −61.065 | 21.863 | −8.655 | 1.00 | 25.19 | C |
| ATOM | 4002 | CG | GLU | A | 271 | −59.563 | 21.909 | −8.794 | 1.00 | 27.45 | C |
| ATOM | 4005 | CD | GLU | A | 271 | −58.857 | 22.910 | −7.857 | 1.00 | 30.03 | C |
| ATOM | 4006 | OE1 | GLU | A | 271 | −58.905 | 24.145 | −8.147 | 1.00 | 29.41 | O |
| ATOM | 4007 | OE2 | GLU | A | 271 | −58.227 | 22.431 | −6.865 | 1.00 | 30.71 | O |
| ATOM | 4008 | C | GLU | A | 271 | −61.799 | 19.391 | −8.484 | 1.00 | 24.95 | C |
| ATOM | 4009 | O | GLU | A | 271 | −60.972 | 18.480 | −8.352 | 1.00 | 25.70 | O |
| ATOM | 4011 | N | PRO | A | 272 | −62.918 | 19.242 | −9.224 | 1.00 | 24.59 | N |
| ATOM | 4012 | CA | PRO | A | 272 | −63.399 | 17.915 | −9.656 | 1.00 | 24.38 | C |
| ATOM | 4014 | CB | PRO | A | 272 | −64.675 | 18.243 | −10.430 | 1.00 | 24.25 | C |
| ATOM | 4017 | CG | PRO | A | 272 | −65.105 | 19.536 | −9.869 | 1.00 | 24.53 | C |
| ATOM | 4020 | CD | PRO | A | 272 | −63.855 | 20.295 | −9.639 | 1.00 | 24.42 | C |
| ATOM | 4023 | C | PRO | A | 272 | −62.475 | 17.111 | −10.549 | 1.00 | 24.29 | C |
| ATOM | 4024 | O | PRO | A | 272 | −62.406 | 15.886 | −10.410 | 1.00 | 24.45 | O |
| ATOM | 4025 | N | GLN | A | 273 | −61.777 | 17.781 | −11.462 | 1.00 | 24.13 | N |
| ATOM | 4026 | CA | GLN | A | 273 | −60.998 | 17.064 | −12.461 | 1.00 | 24.13 | C |
| ATOM | 4028 | CB | GLN | A | 273 | −60.523 | 17.983 | −13.567 | 1.00 | 23.84 | C |
| ATOM | 4031 | CG | GLN | A | 273 | −59.556 | 19.041 | −13.117 | 1.00 | 24.37 | C |
| ATOM | 4034 | CD | GLN | A | 273 | −60.222 | 20.360 | −12.775 | 1.00 | 25.22 | C |

TABLE 3-7-continued

| Coordinates of *P. tremuloides IspS* | | | | | | | | | | | |
|---|---|---|---|---|---|---|---|---|---|---|---|
| ATOM | 4035 | OE1 | GLN | A | 273 | −61.392 | 20.412 | −12.367 | 1.00 | 25.71 | O |
| ATOM | 4036 | NE2 | GLN | A | 273 | −59.468 | 21.441 | −12.932 | 1.00 | 24.95 | N |
| ATOM | 4039 | C | GLN | A | 273 | −59.808 | 16.327 | −11.877 | 1.00 | 24.33 | C |
| ATOM | 4040 | O | GLN | A | 273 | −59.224 | 15.486 | −12.555 | 1.00 | 24.91 | O |
| ATOM | 4042 | N | TYR | A | 274 | −59.462 | 16.607 | −10.626 | 1.00 | 24.27 | N |
| ATOM | 4043 | CA | TYR | A | 274 | −58.211 | 16.119 | −10.067 | 1.00 | 24.38 | C |
| ATOM | 4045 | CB | TYR | A | 274 | −57.639 | 17.180 | −9.138 | 1.00 | 24.36 | C |
| ATOM | 4048 | CG | TYR | A | 274 | −57.066 | 18.398 | −9.819 | 1.00 | 24.35 | C |
| ATOM | 4049 | CD1 | TYR | A | 274 | −56.249 | 18.291 | −10.935 | 1.00 | 24.13 | C |
| ATOM | 4051 | CE1 | TYR | A | 274 | −55.716 | 19.409 | −11.542 | 1.00 | 23.75 | C |
| ATOM | 4053 | CZ | TYR | A | 274 | −55.968 | 20.646 | −11.019 | 1.00 | 24.14 | C |
| ATOM | 4054 | OH | TYR | A | 274 | −55.431 | 21.762 | −11.597 | 1.00 | 24.45 | O |
| ATOM | 4056 | CE2 | TYR | A | 274 | −56.755 | 20.780 | −9.903 | 1.00 | 24.92 | C |
| ATOM | 4058 | CD2 | TYR | A | 274 | −57.297 | 19.658 | −9.308 | 1.00 | 24.74 | C |
| ATOM | 4060 | C | TYR | A | 274 | −58.319 | 14.796 | −9.310 | 1.00 | 24.63 | C |
| ATOM | 4061 | O | TYR | A | 274 | −57.681 | 14.613 | −8.276 | 1.00 | 24.47 | O |
| ATOM | 4063 | N | SER | A | 275 | −59.097 | 13.852 | −9.821 | 1.00 | 25.00 | N |
| ATOM | 4064 | CA | SER | A | 275 | −59.254 | 12.575 | −9.116 | 1.00 | 25.11 | C |
| ATOM | 4066 | CB | SER | A | 275 | −60.244 | 11.664 | −9.842 | 1.00 | 25.14 | C |
| ATOM | 4069 | OG | SER | A | 275 | −61.537 | 12.252 | −9.852 | 1.00 | 25.96 | O |
| ATOM | 4071 | C | SER | A | 275 | −57.907 | 11.885 | −8.963 | 1.00 | 24.94 | C |
| ATOM | 4072 | O | SER | A | 275 | −57.544 | 11.439 | −7.877 | 1.00 | 24.57 | O |
| ATOM | 4074 | N | ASP | A | 276 | −57.149 | 11.822 | −10.052 | 1.00 | 25.01 | N |
| ATOM | 4075 | CA | ASP | A | 276 | −55.840 | 11.187 | −9.990 | 1.00 | 24.92 | C |
| ATOM | 4077 | CB | ASP | A | 276 | −55.102 | 11.257 | −11.324 | 1.00 | 25.02 | C |
| ATOM | 4080 | CG | ASP | A | 276 | −55.827 | 10.495 | −12.407 | 1.00 | 26.27 | C |
| ATOM | 4081 | OD1 | ASP | A | 276 | −56.372 | 9.411 | −12.080 | 1.00 | 26.65 | O |
| ATOM | 4082 | OD2 | ASP | A | 276 | −55.880 | 10.991 | −13.563 | 1.00 | 28.21 | O |
| ATOM | 4083 | C | ASP | A | 276 | −55.026 | 11.798 | −8.881 | 1.00 | 24.30 | C |
| ATOM | 4084 | O | ASP | A | 276 | −54.454 | 11.064 | −8.099 | 1.00 | 24.64 | O |
| ATOM | 4086 | N | CYS | A | 277 | −55.005 | 13.124 | −8.772 | 1.00 | 23.61 | N |
| ATOM | 4087 | CA | CYS | A | 277 | −54.210 | 13.746 | −7.715 | 1.00 | 22.91 | C |
| ATOM | 4089 | CB | CYS | A | 277 | −54.262 | 15.268 | −7.748 | 1.00 | 22.83 | C |
| ATOM | 4092 | SG | CYS | A | 277 | −53.048 | 15.994 | −6.615 | 1.00 | 22.43 | S |
| ATOM | 4094 | C | CYS | A | 277 | −54.653 | 13.251 | −6.357 | 1.00 | 22.39 | C |
| ATOM | 4095 | O | CYS | A | 277 | −53.822 | 12.833 | −5.559 | 1.00 | 22.23 | O |
| ATOM | 4097 | N | ARG | A | 278 | −55.962 | 13.262 | −6.115 | 1.00 | 22.01 | N |
| ATOM | 4098 | CA | ARG | A | 278 | −56.519 | 12.813 | −4.829 | 1.00 | 21.40 | C |
| ATOM | 4100 | CB | ARG | A | 278 | −58.021 | 13.053 | −4.753 | 1.00 | 21.07 | C |
| ATOM | 4103 | CG | ARG | A | 278 | −58.382 | 14.509 | −4.754 | 1.00 | 20.39 | C |
| ATOM | 4106 | CD | ARG | A | 278 | −59.852 | 14.698 | −4.527 | 1.00 | 20.05 | C |
| ATOM | 4109 | NE | ARG | A | 278 | −60.683 | 14.331 | −5.675 | 1.00 | 18.86 | N |
| ATOM | 4111 | CZ | ARG | A | 278 | −60.993 | 15.144 | −6.679 | 1.00 | 18.58 | C |
| ATOM | 4112 | NH1 | ARG | A | 278 | −60.530 | 16.391 | −6.730 | 1.00 | 18.45 | N |
| ATOM | 4115 | NH2 | ARG | A | 278 | −61.775 | 14.702 | −7.647 | 1.00 | 19.04 | N |
| ATOM | 4118 | C | ARG | A | 278 | −56.224 | 11.358 | −4.530 | 1.00 | 21.12 | C |
| ATOM | 4119 | O | ARG | A | 278 | −55.804 | 11.050 | −3.434 | 1.00 | 21.59 | O |
| ATOM | 4121 | N | ASN | A | 279 | −56.412 | 10.467 | −5.493 | 1.00 | 20.94 | N |
| ATOM | 4122 | CA | ASN | A | 279 | −56.168 | 9.044 | −5.243 | 1.00 | 21.08 | C |
| ATOM | 4124 | CB | ASN | A | 279 | −56.672 | 8.182 | −6.401 | 1.00 | 21.54 | C |
| ATOM | 4127 | CG | ASN | A | 279 | −58.199 | 8.346 | −6.642 | 1.00 | 23.94 | C |
| ATOM | 4128 | OD1 | ASN | A | 279 | −58.920 | 8.941 | −5.823 | 1.00 | 26.47 | O |
| ATOM | 4129 | ND2 | ASN | A | 279 | −58.685 | 7.825 | −7.769 | 1.00 | 25.52 | N |
| ATOM | 4132 | C | ASN | A | 279 | −54.699 | 8.798 | −4.972 | 1.00 | 20.30 | C |
| ATOM | 4133 | O | ASN | A | 279 | −54.337 | 8.200 | −3.977 | 1.00 | 19.95 | O |
| ATOM | 4135 | N | SER | A | 280 | −53.851 | 9.297 | −5.856 | 1.00 | 20.02 | N |
| ATOM | 4136 | CA | SER | A | 280 | −52.409 | 9.335 | −5.612 | 1.00 | 19.32 | C |
| ATOM | 4138 | CB | SER | A | 280 | −51.725 | 10.304 | −6.580 | 1.00 | 19.35 | C |
| ATOM | 4141 | OG | SER | A | 280 | −50.624 | 9.705 | −7.212 | 1.00 | 19.77 | O |
| ATOM | 4143 | C | SER | A | 280 | −52.122 | 9.745 | −4.166 | 1.00 | 18.55 | C |
| ATOM | 4144 | O | SER | A | 280 | −51.514 | 8.976 | −3.436 | 1.00 | 18.98 | O |
| ATOM | 4146 | N | VAL | A | 281 | −52.580 | 10.923 | −3.743 | 1.00 | 17.45 | N |
| ATOM | 4147 | CA | VAL | A | 281 | −52.235 | 11.444 | −2.416 | 1.00 | 17.01 | C |
| ATOM | 4149 | CB | VAL | A | 281 | −52.650 | 12.934 | −2.235 | 1.00 | 17.20 | C |
| ATOM | 4151 | CG1 | VAL | A | 281 | −52.492 | 13.376 | −.787 | 1.00 | 16.76 | C |
| ATOM | 4155 | CG2 | VAL | A | 281 | −51.826 | 13.847 | −3.128 | 1.00 | 17.13 | C |
| ATOM | 4159 | C | VAL | A | 281 | −52.861 | 10.607 | −1.301 | 1.00 | 16.82 | C |
| ATOM | 4160 | O | VAL | A | 281 | −52.217 | 10.314 | −.289 | 1.00 | 16.81 | O |
| ATOM | 4162 | N | ALA | A | 282 | −54.118 | 10.225 | −1.481 | 1.00 | 16.55 | N |
| ATOM | 4163 | CA | ALA | A | 282 | −54.774 | 9.304 | −.559 | 1.00 | 16.31 | C |
| ATOM | 4165 | CB | ALA | A | 282 | −56.174 | 8.951 | −1.060 | 1.00 | 16.08 | C |
| ATOM | 4169 | C | ALA | A | 282 | −53.946 | 8.036 | −.355 | 1.00 | 16.31 | C |
| ATOM | 4170 | O | ALA | A | 282 | −53.671 | 7.653 | .762 | 1.00 | 16.16 | O |
| ATOM | 4172 | N | LYS | A | 283 | −53.539 | 7.395 | −1.443 | 1.00 | 16.92 | N |
| ATOM | 4173 | CA | LYS | A | 283 | −52.773 | 6.139 | −1.368 | 1.00 | 17.39 | C |
| ATOM | 4175 | CB | LYS | A | 283 | −52.454 | 5.596 | −2.773 | 1.00 | 17.31 | C |
| ATOM | 4178 | CG | LYS | A | 283 | −53.680 | 5.066 | −3.519 | 1.00 | 17.85 | C |
| ATOM | 4181 | CD | LYS | A | 283 | −53.389 | 4.527 | −4.941 | 1.00 | 18.98 | C |

TABLE 3-7-continued

Coordinates of *P. tremuloides IspS*

| | | | | | | | | | | | |
|---|---|---|---|---|---|---|---|---|---|---|---|
| ATOM | 4184 | CE | LYS | A | 283 | −54.709 | 4.275 | −5.718 | 1.00 | 19.79 | C |
| ATOM | 4187 | NZ | LYS | A | 283 | −54.695 | 3.091 | −6.625 | 1.00 | 20.11 | N |
| ATOM | 4191 | C | LYS | A | 283 | −51.483 | 6.338 | −.591 | 1.00 | 17.82 | C |
| ATOM | 4192 | O | LYS | A | 283 | −51.170 | 5.577 | .331 | 1.00 | 17.37 | O |
| ATOM | 4194 | N | MET | A | 284 | −50.744 | 7.381 | −.964 | 1.00 | 18.49 | N |
| ATOM | 4195 | CA | MET | A | 284 | −49.434 | 7.622 | −.373 | 1.00 | 18.82 | C |
| ATOM | 4197 | CB | MET | A | 284 | −48.688 | 8.795 | −1.047 | 1.00 | 18.84 | C |
| ATOM | 4200 | CG | MET | A | 284 | −48.118 | 8.506 | −2.444 | 1.00 | 18.47 | C |
| ATOM | 4203 | SD | MET | A | 284 | −47.540 | 6.819 | −2.718 | 1.00 | 19.50 | S |
| ATOM | 4204 | CE | MET | A | 284 | −49.088 | 5.982 | −3.094 | 1.00 | 19.36 | C |
| ATOM | 4208 | C | MET | A | 284 | −49.575 | 7.848 | 1.115 | 1.00 | 18.95 | C |
| ATOM | 4209 | O | MET | A | 284 | −48.901 | 7.166 | 1.892 | 1.00 | 19.29 | O |
| ATOM | 4211 | N | PHE | A | 285 | −50.465 | 8.762 | 1.507 | 1.00 | 18.94 | N |
| ATOM | 4212 | CA | PHE | A | 285 | −50.671 | 9.082 | 2.930 | 1.00 | 19.26 | C |
| ATOM | 4214 | CB | PHE | A | 285 | −51.714 | 10.185 | 3.073 | 1.00 | 19.72 | C |
| ATOM | 4217 | CG | PHE | A | 285 | −51.575 | 11.016 | 4.328 | 1.00 | 21.97 | C |
| ATOM | 4218 | CD1 | PHE | A | 285 | −50.335 | 11.202 | 4.954 | 1.00 | 24.49 | C |
| ATOM | 4220 | CE1 | PHE | A | 285 | −50.209 | 11.996 | 6.086 | 1.00 | 25.11 | C |
| ATOM | 4222 | CZ | PHE | A | 285 | −51.321 | 12.634 | 6.597 | 1.00 | 26.40 | C |
| ATOM | 4224 | CE2 | PHE | A | 285 | −52.566 | 12.470 | 5.977 | 1.00 | 26.44 | C |
| ATOM | 4226 | CD2 | PHE | A | 285 | −52.678 | 11.670 | 4.846 | 1.00 | 24.55 | C |
| ATOM | 4228 | C | PHE | A | 285 | −51.097 | 7.879 | 3.770 | 1.00 | 18.74 | C |
| ATOM | 4229 | O | PHE | A | 285 | −50.700 | 7.729 | 4.924 | 1.00 | 18.31 | O |
| ATOM | 4231 | N | SER | A | 286 | −51.903 | 7.019 | 3.169 | 1.00 | 18.49 | N |
| ATOM | 4232 | CA | SER | A | 286 | −52.281 | 5.772 | 3.791 | 1.00 | 18.38 | C |
| ATOM | 4234 | CB | SER | A | 286 | −53.302 | 5.065 | 2.926 | 1.00 | 18.45 | C |
| ATOM | 4237 | OG | SER | A | 286 | −54.389 | 5.949 | 2.687 | 1.00 | 19.82 | O |
| ATOM | 4239 | C | SER | A | 286 | −51.070 | 4.888 | 4.048 | 1.00 | 18.08 | C |
| ATOM | 4240 | O | SER | A | 286 | −50.931 | 4.376 | 5.146 | 1.00 | 18.18 | O |
| ATOM | 4242 | N | PHE | A | 287 | −50.195 | 4.714 | 3.054 | 1.00 | 17.72 | N |
| ATOM | 4243 | CA | PHE | A | 287 | −48.911 | 4.024 | 3.279 | 1.00 | 17.23 | C |
| ATOM | 4245 | CB | PHE | A | 287 | −48.133 | 3.801 | 1.977 | 1.00 | 17.09 | C |
| ATOM | 4248 | CG | PHE | A | 287 | −48.513 | 2.555 | 1.258 | 1.00 | 17.26 | C |
| ATOM | 4249 | CD1 | PHE | A | 287 | −48.220 | 1.315 | 1.802 | 1.00 | 18.31 | C |
| ATOM | 4251 | CE1 | PHE | A | 287 | −48.583 | .129 | 1.131 | 1.00 | 18.47 | C |
| ATOM | 4253 | CZ | PHE | A | 287 | −49.237 | .198 | −.091 | 1.00 | 17.88 | C |
| ATOM | 4255 | CE2 | PHE | A | 287 | −49.530 | 1.441 | −.642 | 1.00 | 17.57 | C |
| ATOM | 4257 | CD2 | PHE | A | 287 | −49.168 | 2.608 | .031 | 1.00 | 17.79 | C |
| ATOM | 4259 | C | PHE | A | 287 | −48.022 | 4.787 | 4.277 | 1.00 | 16.92 | C |
| ATOM | 4260 | O | PHE | A | 287 | −47.369 | 4.173 | 5.143 | 1.00 | 17.18 | O |
| ATOM | 4262 | N | VAL | A | 288 | −47.989 | 6.113 | 4.174 | 1.00 | 16.00 | N |
| ATOM | 4263 | CA | VAL | A | 288 | −47.148 | 6.883 | 5.080 | 1.00 | 15.45 | C |
| ATOM | 4265 | CB | VAL | A | 288 | −47.289 | 8.399 | 4.863 | 1.00 | 15.21 | C |
| ATOM | 4267 | CG1 | VAL | A | 288 | −46.433 | 9.162 | 5.852 | 1.00 | 14.24 | C |
| ATOM | 4271 | CG2 | VAL | A | 288 | −46.898 | 8.757 | 3.450 | 1.00 | 14.46 | C |
| ATOM | 4275 | C | VAL | A | 288 | −47.479 | 6.499 | 6.527 | 1.00 | 15.46 | C |
| ATOM | 4276 | O | VAL | A | 288 | −46.590 | 6.160 | 7.299 | 1.00 | 14.79 | O |
| ATOM | 4278 | N | THR | A | 289 | −48.759 | 6.494 | 6.880 | 1.00 | 15.62 | N |
| ATOM | 4279 | CA | THR | A | 289 | −49.110 | 6.272 | 8.274 | 1.00 | 16.09 | C |
| ATOM | 4281 | CB | THR | A | 289 | −50.602 | 6.557 | 8.588 | 1.00 | 15.72 | C |
| ATOM | 4283 | OG1 | THR | A | 289 | −51.422 | 5.827 | 7.708 | 1.00 | 16.52 | O |
| ATOM | 4285 | CG2 | THR | A | 289 | −50.927 | 8.007 | 8.371 | 1.00 | 16.56 | C |
| ATOM | 4289 | C | THR | A | 289 | −48.677 | 4.879 | 8.727 | 1.00 | 16.34 | C |
| ATOM | 4290 | O | THR | A | 289 | −48.234 | 4.707 | 9.881 | 1.00 | 16.68 | O |
| ATOM | 4292 | N | ILE | A | 290 | −48.737 | 3.904 | 7.820 | 1.00 | 16.29 | N |
| ATOM | 4293 | CA | ILE | A | 290 | −48.347 | 2.538 | 8.166 | 1.00 | 16.56 | C |
| ATOM | 4295 | CB | ILE | A | 290 | −48.734 | 1.516 | 7.096 | 1.00 | 16.48 | C |
| ATOM | 4297 | CG1 | ILE | A | 290 | −50.247 | 1.440 | 6.944 | 1.00 | 16.91 | C |
| ATOM | 4300 | CD1 | ILE | A | 290 | −50.677 | .564 | 5.811 | 1.00 | 16.52 | C |
| ATOM | 4304 | CG2 | ILE | A | 290 | −48.262 | .145 | 7.488 | 1.00 | 16.52 | C |
| ATOM | 4308 | C | ILE | A | 290 | −46.842 | 2.456 | 8.402 | 1.00 | 16.94 | C |
| ATOM | 4309 | O | ILE | A | 290 | −46.404 | 1.968 | 9.443 | 1.00 | 17.06 | O |
| ATOM | 4311 | N | ILE | A | 291 | −46.048 | 2.942 | 7.451 | 1.00 | 17.22 | N |
| ATOM | 4312 | CA | ILE | A | 291 | −44.595 | 2.969 | 7.640 | 1.00 | 17.20 | C |
| ATOM | 4314 | CB | ILE | A | 291 | −43.842 | 3.534 | 6.405 | 1.00 | 17.32 | C |
| ATOM | 4316 | CG1 | ILE | A | 291 | −44.172 | 2.744 | 5.125 | 1.00 | 17.61 | C |
| ATOM | 4319 | CD1 | ILE | A | 291 | −44.004 | 1.265 | 5.250 | 1.00 | 18.21 | C |
| ATOM | 4323 | CG2 | ILE | A | 291 | −42.336 | 3.550 | 6.637 | 1.00 | 16.64 | C |
| ATOM | 4327 | C | ILE | A | 291 | −44.262 | 3.794 | 8.886 | 1.00 | 17.36 | C |
| ATOM | 4328 | O | ILE | A | 291 | −43.420 | 3.413 | 9.670 | 1.00 | 17.06 | O |
| ATOM | 4330 | N | ASP | A | 292 | −44.950 | 4.906 | 9.093 | 1.00 | 18.12 | N |
| ATOM | 4331 | CA | ASP | A | 292 | −44.627 | 5.755 | 10.227 | 1.00 | 18.83 | C |
| ATOM | 4333 | CB | ASP | A | 292 | −45.511 | 7.017 | 10.285 | 1.00 | 19.22 | C |
| ATOM | 4336 | CG | ASP | A | 292 | −45.185 | 7.920 | 11.485 | 1.00 | 19.93 | C |
| ATOM | 4337 | OD1 | ASP | A | 292 | −44.062 | 8.460 | 11.544 | 1.00 | 21.80 | O |
| ATOM | 4338 | OD2 | ASP | A | 292 | −46.048 | 8.080 | 12.375 | 1.00 | 20.46 | O |
| ATOM | 4339 | C | ASP | A | 292 | −44.745 | 4.947 | 11.509 | 1.00 | 18.96 | C |
| ATOM | 4340 | O | ASP | A | 292 | −43.902 | 5.094 | 12.394 | 1.00 | 19.05 | O |

TABLE 3-7-continued

Coordinates of *P. tremuloides IspS*

| | | | | | | | | | | | |
|---|---|---|---|---|---|---|---|---|---|---|---|
| ATOM | 4342 | N | ASP | A | 293 | −45.774 | 4.097 | 11.610 | 1.00 | 19.05 | N |
| ATOM | 4343 | CA | ASP | A | 293 | −45.951 | 3.273 | 12.817 | 1.00 | 18.99 | C |
| ATOM | 4345 | CB | ASP | A | 293 | −47.237 | 2.443 | 12.790 | 1.00 | 18.95 | C |
| ATOM | 4348 | CG | ASP | A | 293 | −48.496 | 3.272 | 12.921 | 1.00 | 19.27 | C |
| ATOM | 4349 | OD1 | ASP | A | 293 | −48.483 | 4.361 | 13.523 | 1.00 | 21.51 | O |
| ATOM | 4350 | OD2 | ASP | A | 293 | −49.536 | 2.812 | 12.421 | 1.00 | 19.61 | O |
| ATOM | 4351 | C | ASP | A | 293 | −44.783 | 2.322 | 12.935 | 1.00 | 19.07 | C |
| ATOM | 4352 | O | ASP | A | 293 | −44.244 | 2.135 | 14.024 | 1.00 | 19.35 | O |
| ATOM | 4354 | N | ILE | A | 294 | −44.390 | 1.730 | 11.805 | 1.00 | 19.10 | N |
| ATOM | 4355 | CA | ILE | A | 294 | −43.320 | .727 | 11.786 | 1.00 | 19.04 | C |
| ATOM | 4357 | CB | ILE | A | 294 | −43.137 | .109 | 10.386 | 1.00 | 18.49 | C |
| ATOM | 4359 | CG1 | ILE | A | 294 | −44.343 | −.754 | 10.038 | 1.00 | 17.60 | C |
| ATOM | 4362 | CD1 | ILE | A | 294 | −44.204 | −1.504 | 8.752 | 1.00 | 16.77 | C |
| ATOM | 4366 | CG2 | ILE | A | 294 | −41.895 | −.745 | 10.348 | 1.00 | 18.77 | C |
| ATOM | 4370 | C | ILE | A | 294 | −41.974 | 1.273 | 12.298 | 1.00 | 19.55 | C |
| ATOM | 4371 | O | ILE | A | 294 | −41.234 | .550 | 12.974 | 1.00 | 19.75 | O |
| ATOM | 4373 | N | TYR | A | 295 | −41.649 | 2.525 | 11.983 | 1.00 | 19.75 | N |
| ATOM | 4374 | CA | TYR | A | 295 | −40.411 | 3.103 | 12.476 | 1.00 | 19.91 | C |
| ATOM | 4376 | CB | TYR | A | 295 | −39.856 | 4.178 | 11.542 | 1.00 | 19.66 | C |
| ATOM | 4379 | CG | TYR | A | 295 | −39.206 | 3.695 | 10.245 | 1.00 | 18.19 | C |
| ATOM | 4380 | CD1 | TYR | A | 295 | −37.821 | 3.727 | 10.075 | 1.00 | 16.19 | C |
| ATOM | 4382 | CE1 | TYR | A | 295 | −37.222 | 3.331 | 8.882 | 1.00 | 14.68 | C |
| ATOM | 4384 | CZ | TYR | A | 295 | −38.004 | 2.906 | 7.828 | 1.00 | 15.04 | C |
| ATOM | 4385 | OH | TYR | A | 295 | −37.428 | 2.485 | 6.631 | 1.00 | 12.25 | O |
| ATOM | 4387 | CE2 | TYR | A | 295 | −39.383 | 2.871 | 7.975 | 1.00 | 16.48 | C |
| ATOM | 4389 | CD2 | TYR | A | 295 | −39.975 | 3.271 | 9.172 | 1.00 | 17.01 | C |
| ATOM | 4391 | C | TYR | A | 295 | −40.647 | 3.677 | 13.858 | 1.00 | 20.73 | C |
| ATOM | 4392 | O | TYR | A | 295 | −39.749 | 3.635 | 14.717 | 1.00 | 21.64 | O |
| ATOM | 4394 | N | ASP | A | 296 | −41.843 | 4.200 | 14.103 | 1.00 | 21.38 | N |
| ATOM | 4395 | CA | ASP | A | 296 | −42.100 | 4.865 | 15.391 | 1.00 | 22.20 | C |
| ATOM | 4397 | CB | ASP | A | 296 | −43.421 | 5.644 | 15.391 | 1.00 | 22.69 | C |
| ATOM | 4400 | CG | ASP | A | 296 | −43.567 | 6.548 | 16.607 | 1.00 | 23.85 | C |
| ATOM | 4401 | OD1 | ASP | A | 296 | −42.568 | 7.179 | 17.014 | 1.00 | 25.49 | O |
| ATOM | 4402 | OD2 | ASP | A | 296 | −44.689 | 6.648 | 17.145 | 1.00 | 26.12 | O |
| ATOM | 4403 | C | ASP | A | 296 | −42.106 | 3.890 | 16.549 | 1.00 | 22.10 | C |
| ATOM | 4404 | O | ASP | A | 296 | −41.376 | 4.082 | 17.506 | 1.00 | 22.14 | O |
| ATOM | 4406 | N | VAL | A | 297 | −42.900 | 2.828 | 16.435 | 1.00 | 22.25 | N |
| ATOM | 4407 | CA | VAL | A | 297 | −43.163 | 1.937 | 17.570 | 1.00 | 22.22 | C |
| ATOM | 4409 | CB | VAL | A | 297 | −44.635 | 2.116 | 18.057 | 1.00 | 22.07 | C |
| ATOM | 4411 | CG1 | VAL | A | 297 | −44.958 | 3.587 | 18.215 | 1.00 | 21.63 | C |
| ATOM | 4415 | CG2 | VAL | A | 297 | −45.618 | 1.459 | 17.099 | 1.00 | 20.76 | C |
| ATOM | 4419 | C | VAL | A | 297 | −42.861 | .422 | 17.373 | 1.00 | 22.49 | C |
| ATOM | 4420 | O | VAL | A | 297 | −42.517 | −.255 | 18.343 | 1.00 | 22.40 | O |
| ATOM | 4422 | N | TYR | A | 298 | −42.990 | −.117 | 16.157 | 1.00 | 22.69 | N |
| ATOM | 4423 | CA | TYR | A | 298 | −43.065 | −1.579 | 15.993 | 1.00 | 22.90 | C |
| ATOM | 4425 | CB | TYR | A | 298 | −44.089 | −1.974 | 14.934 | 1.00 | 22.77 | C |
| ATOM | 4428 | CG | TYR | A | 298 | −44.341 | −3.469 | 14.932 | 1.00 | 23.74 | C |
| ATOM | 4429 | CD1 | TYR | A | 298 | −45.249 | −4.043 | 15.819 | 1.00 | 25.72 | C |
| ATOM | 4431 | CE1 | TYR | A | 298 | −45.484 | −5.435 | 15.833 | 1.00 | 26.12 | C |
| ATOM | 4433 | CZ | TYR | A | 298 | −44.798 | −6.247 | 14.954 | 1.00 | 25.59 | C |
| ATOM | 4434 | OH | TYR | A | 298 | −45.027 | −7.593 | 14.970 | 1.00 | 25.33 | O |
| ATOM | 4436 | CE2 | TYR | A | 298 | −43.890 | −5.702 | 14.062 | 1.00 | 24.79 | C |
| ATOM | 4438 | CD2 | TYR | A | 298 | −43.661 | −4.317 | 14.061 | 1.00 | 24.20 | C |
| ATOM | 4440 | C | TYR | A | 298 | −41.750 | −2.258 | 15.649 | 1.00 | 23.02 | C |
| ATOM | 4441 | O | TYR | A | 298 | −41.387 | −3.257 | 16.256 | 1.00 | 22.80 | O |
| ATOM | 4443 | N | GLY | A | 299 | −41.069 | −1.747 | 14.634 | 1.00 | 23.47 | N |
| ATOM | 4444 | CA | GLY | A | 299 | −39.839 | −2.361 | 14.149 | 1.00 | 23.36 | C |
| ATOM | 4447 | C | GLY | A | 299 | −38.631 | −1.978 | 14.984 | 1.00 | 23.27 | C |
| ATOM | 4448 | O | GLY | A | 299 | −38.532 | −.858 | 15.501 | 1.00 | 23.35 | O |
| ATOM | 4450 | N | THR | A | 300 | −37.702 | −2.918 | 15.098 | 1.00 | 23.11 | N |
| ATOM | 4451 | CA | THR | A | 300 | −36.459 | −2.682 | 15.797 | 1.00 | 22.90 | C |
| ATOM | 4453 | CB | THR | A | 300 | −35.869 | −3.957 | 16.386 | 1.00 | 22.83 | C |
| ATOM | 4455 | OG1 | THR | A | 300 | −35.328 | −4.756 | 15.328 | 1.00 | 22.61 | O |
| ATOM | 4457 | CG2 | THR | A | 300 | −36.928 | −4.732 | 17.162 | 1.00 | 22.18 | C |
| ATOM | 4461 | C | THR | A | 300 | −35.482 | −2.120 | 14.796 | 1.00 | 23.00 | C |
| ATOM | 4462 | O | THR | A | 300 | −35.606 | −2.364 | 13.602 | 1.00 | 23.13 | O |
| ATOM | 4464 | N | LEU | A | 301 | −34.496 | −1.394 | 15.309 | 1.00 | 23.07 | N |
| ATOM | 4465 | CA | LEU | A | 301 | −33.596 | −.572 | 14.498 | 1.00 | 22.84 | C |
| ATOM | 4467 | CB | LEU | A | 301 | −32.515 | .007 | 15.403 | 1.00 | 22.80 | C |
| ATOM | 4470 | CG | LEU | A | 301 | −31.965 | 1.412 | 15.182 | 1.00 | 22.39 | C |
| ATOM | 4472 | CD1 | LEU | A | 301 | −32.983 | 2.365 | 14.587 | 1.00 | 22.44 | C |
| ATOM | 4476 | CD2 | LEU | A | 301 | −31.482 | 1.919 | 16.536 | 1.00 | 22.19 | C |
| ATOM | 4480 | C | LEU | A | 301 | −32.964 | −1.358 | 13.361 | 1.00 | 22.95 | C |
| ATOM | 4481 | O | LEU | A | 301 | −32.910 | −.888 | 12.232 | 1.00 | 22.50 | O |
| ATOM | 4483 | N | ASP | A | 302 | −32.511 | −2.569 | 13.673 | 1.00 | 23.35 | N |
| ATOM | 4484 | CA | ASP | A | 302 | −31.929 | −3.469 | 12.670 | 1.00 | 23.65 | C |
| ATOM | 4486 | CB | ASP | A | 302 | −31.332 | −4.747 | 13.328 | 1.00 | 24.12 | C |
| ATOM | 4489 | CG | ASP | A | 302 | −29.984 | −4.498 | 14.057 | 1.00 | 25.23 | C |

TABLE 3-7-continued

Coordinates of *P. tremuloides IspS*

| | | | | | | | | | | | |
|---|---|---|---|---|---|---|---|---|---|---|---|
| ATOM | 4490 | OD1 | ASP | A | 302 | −29.003 | −4.051 | 13.409 | 1.00 | 26.43 | O |
| ATOM | 4491 | OD2 | ASP | A | 302 | −29.896 | −4.780 | 15.277 | 1.00 | 26.92 | O |
| ATOM | 4492 | C | ASP | A | 302 | −32.945 | −3.859 | 11.581 | 1.00 | 23.11 | C |
| ATOM | 4493 | O | ASP | A | 302 | −32.544 | −4.086 | 10.445 | 1.00 | 23.05 | O |
| ATOM | 4495 | N | GLU | A | 303 | −34.235 | −3.965 | 11.927 | 1.00 | 22.63 | N |
| ATOM | 4496 | CA | GLU | A | 303 | −35.295 | −4.248 | 10.931 | 1.00 | 22.40 | C |
| ATOM | 4498 | CB | GLU | A | 303 | −36.625 | −4.675 | 11.589 | 1.00 | 22.20 | C |
| ATOM | 4501 | CG | GLU | A | 303 | −36.537 | −5.956 | 12.426 | 1.00 | 22.66 | C |
| ATOM | 4504 | CD | GLU | A | 303 | −37.832 | −6.341 | 13.159 | 1.00 | 22.69 | C |
| ATOM | 4505 | OE1 | GLU | A | 303 | −38.614 | −5.449 | 13.568 | 1.00 | 22.23 | O |
| ATOM | 4506 | OE2 | GLU | A | 303 | −38.051 | −7.558 | 13.338 | 1.00 | 21.64 | O |
| ATOM | 4507 | C | GLU | A | 303 | −35.533 | −3.017 | 10.067 | 1.00 | 22.35 | C |
| ATOM | 4508 | O | GLU | A | 303 | −35.658 | −3.105 | 8.841 | 1.00 | 22.27 | O |
| ATOM | 4510 | N | LEU | A | 304 | −35.597 | −1.866 | 10.724 | 1.00 | 22.34 | N |
| ATOM | 4511 | CA | LEU | A | 304 | −35.776 | −.607 | 10.040 | 1.00 | 22.26 | C |
| ATOM | 4513 | CB | LEU | A | 304 | −35.861 | .537 | 11.052 | 1.00 | 22.49 | C |
| ATOM | 4516 | CG | LEU | A | 304 | −37.089 | .517 | 11.973 | 1.00 | 23.05 | C |
| ATOM | 4518 | CD1 | LEU | A | 304 | −37.109 | 1.708 | 12.932 | 1.00 | 23.46 | C |
| ATOM | 4522 | CD2 | LEU | A | 304 | −38.353 | .511 | 11.142 | 1.00 | 23.96 | C |
| ATOM | 4526 | C | LEU | A | 304 | −34.634 | −.383 | 9.063 | 1.00 | 22.09 | C |
| ATOM | 4527 | O | LEU | A | 304 | −34.873 | .094 | 7.969 | 1.00 | 22.32 | O |
| ATOM | 4529 | N | GLU | A | 305 | −33.408 | −.740 | 9.450 | 1.00 | 21.91 | N |
| ATOM | 4530 | CA | GLU | A | 305 | −32.259 | −.685 | 8.541 | 1.00 | 21.93 | C |
| ATOM | 4532 | CB | GLU | A | 305 | −30.988 | −1.194 | 9.219 | 1.00 | 22.35 | C |
| ATOM | 4535 | CG | GLU | A | 305 | −30.363 | −.258 | 10.249 | 1.00 | 24.12 | C |
| ATOM | 4538 | CD | GLU | A | 305 | −29.751 | 1.002 | 9.649 | 1.00 | 26.11 | C |
| ATOM | 4539 | OE1 | GLU | A | 305 | −29.275 | 1.846 | 10.454 | 1.00 | 25.68 | O |
| ATOM | 4540 | OE2 | GLU | A | 305 | −29.756 | 1.146 | 8.391 | 1.00 | 27.67 | O |
| ATOM | 4541 | C | GLU | A | 305 | −32.475 | −1.524 | 7.295 | 1.00 | 21.54 | C |
| ATOM | 4542 | O | GLU | A | 305 | −32.010 | −1.162 | 6.220 | 1.00 | 21.75 | O |
| ATOM | 4544 | N | LEU | A | 306 | −33.155 | −2.660 | 7.448 | 1.00 | 21.21 | N |
| ATOM | 4545 | CA | LEU | A | 306 | −33.459 | −3.557 | 6.316 | 1.00 | 20.66 | C |
| ATOM | 4547 | CB | LEU | A | 306 | −33.880 | −4.956 | 6.795 | 1.00 | 20.26 | C |
| ATOM | 4550 | CG | LEU | A | 306 | −32.725 | −5.854 | 7.220 | 1.00 | 19.57 | C |
| ATOM | 4552 | CD1 | LEU | A | 306 | −33.261 | −7.150 | 7.777 | 1.00 | 20.18 | C |
| ATOM | 4556 | CD2 | LEU | A | 306 | −31.791 | −6.120 | 6.061 | 1.00 | 18.29 | C |
| ATOM | 4560 | C | LEU | A | 306 | −34.535 | −2.967 | 5.416 | 1.00 | 20.23 | C |
| ATOM | 4561 | O | LEU | A | 306 | −34.412 | −2.966 | 4.197 | 1.00 | 19.97 | O |
| ATOM | 4563 | N | PHE | A | 307 | −35.588 | −2.457 | 6.023 | 1.00 | 19.99 | N |
| ATOM | 4564 | CA | PHE | A | 307 | −36.635 | −1.861 | 5.237 | 1.00 | 20.00 | C |
| ATOM | 4566 | CB | PHE | A | 307 | −37.771 | −1.388 | 6.118 | 1.00 | 20.08 | C |
| ATOM | 4569 | CG | PHE | A | 307 | −39.011 | −1.115 | 5.370 | 1.00 | 19.05 | C |
| ATOM | 4570 | CD1 | PHE | A | 307 | −39.895 | −2.118 | 5.119 | 1.00 | 18.77 | C |
| ATOM | 4572 | CE1 | PHE | A | 307 | −41.037 | −1.873 | 4.421 | 1.00 | 20.07 | C |
| ATOM | 4574 | CZ | PHE | A | 307 | −41.296 | −.621 | 3.959 | 1.00 | 19.63 | C |
| ATOM | 4576 | CE2 | PHE | A | 307 | −40.411 | .391 | 4.199 | 1.00 | 19.27 | C |
| ATOM | 4578 | CD2 | PHE | A | 307 | −39.278 | .142 | 4.900 | 1.00 | 19.17 | C |
| ATOM | 4580 | C | PHE | A | 307 | −36.087 | −.695 | 4.447 | 1.00 | 20.25 | C |
| ATOM | 4581 | O | PHE | A | 307 | −36.356 | −.589 | 3.242 | 1.00 | 20.08 | O |
| ATOM | 4583 | N | THR | A | 308 | −35.325 | .167 | 5.137 | 1.00 | 20.51 | N |
| ATOM | 4584 | CA | THR | A | 308 | −34.737 | 1.379 | 4.538 | 1.00 | 20.60 | C |
| ATOM | 4586 | CB | THR | A | 308 | −33.860 | 2.177 | 5.541 | 1.00 | 20.41 | C |
| ATOM | 4588 | OG1 | THR | A | 308 | −34.672 | 2.661 | 6.611 | 1.00 | 20.05 | O |
| ATOM | 4590 | CG2 | THR | A | 308 | −33.198 | 3.376 | 4.864 | 1.00 | 20.38 | C |
| ATOM | 4594 | C | THR | A | 308 | −33.895 | 1.009 | 3.331 | 1.00 | 20.82 | C |
| ATOM | 4595 | O | THR | A | 308 | −34.057 | 1.571 | 2.243 | 1.00 | 20.45 | O |
| ATOM | 4597 | N | ASP | A | 309 | −33.020 | .031 | 3.522 | 1.00 | 21.32 | N |
| ATOM | 4598 | CA | ASP | A | 309 | −32.138 | −.399 | 2.449 | 1.00 | 21.88 | C |
| ATOM | 4600 | CB | ASP | A | 309 | −31.042 | −1.324 | 2.971 | 1.00 | 22.44 | C |
| ATOM | 4603 | CG | ASP | A | 309 | −30.164 | −1.847 | 1.857 | 1.00 | 25.69 | C |
| ATOM | 4604 | OD1 | ASP | A | 309 | −29.599 | −1.010 | 1.089 | 1.00 | 28.02 | O |
| ATOM | 4605 | OD2 | ASP | A | 309 | −30.076 | −3.100 | 1.730 | 1.00 | 30.59 | O |
| ATOM | 4606 | C | ASP | A | 309 | −32.928 | −1.085 | 1.357 | 1.00 | 21.17 | C |
| ATOM | 4607 | O | ASP | A | 309 | −32.601 | −.948 | .188 | 1.00 | 20.95 | O |
| ATOM | 4609 | N | ALA | A | 310 | −33.965 | −1.818 | 1.757 | 1.00 | 20.99 | N |
| ATOM | 4610 | CA | ALA | A | 310 | −34.885 | −2.474 | .828 | 1.00 | 20.91 | C |
| ATOM | 4612 | CB | ALA | A | 310 | −35.931 | −3.244 | 1.591 | 1.00 | 20.77 | C |
| ATOM | 4616 | C | ALA | A | 310 | −35.567 | −1.501 | −.123 | 1.00 | 21.08 | C |
| ATOM | 4617 | O | ALA | A | 310 | −35.745 | −1.816 | −1.305 | 1.00 | 20.76 | O |
| ATOM | 4619 | N | VAL | A | 311 | −35.958 | −.334 | .402 | 1.00 | 21.51 | N |
| ATOM | 4620 | CA | VAL | A | 311 | −36.594 | .719 | −.396 | 1.00 | 21.50 | C |
| ATOM | 4622 | CB | VAL | A | 311 | −37.424 | 1.715 | .477 | 1.00 | 21.73 | C |
| ATOM | 4624 | CG1 | VAL | A | 311 | −38.724 | 1.076 | .941 | 1.00 | 21.01 | C |
| ATOM | 4628 | CG2 | VAL | A | 311 | −37.765 | 2.993 | −.292 | 1.00 | 21.88 | C |
| ATOM | 4632 | C | VAL | A | 311 | −35.553 | 1.445 | −1.230 | 1.00 | 21.67 | C |
| ATOM | 4633 | O | VAL | A | 311 | −35.811 | 1.728 | −2.389 | 1.00 | 21.71 | O |
| ATOM | 4635 | N | GLU | A | 312 | −34.381 | 1.724 | −.663 | 1.00 | 22.25 | N |
| ATOM | 4636 | CA | GLU | A | 312 | −33.248 | 2.284 | −1.443 | 1.00 | 23.00 | C |

TABLE 3-7-continued

Coordinates of *P. tremuloides IspS*

| | | | | | | | | | | | |
|---|---|---|---|---|---|---|---|---|---|---|---|
| ATOM | 4638 | CB | GLU | A | 312 | −31.951 | 2.331 | −.608 | 1.00 | 23.36 | C |
| ATOM | 4641 | CG | GLU | A | 312 | −31.897 | 3.383 | .511 | 1.00 | 24.72 | C |
| ATOM | 4644 | CD | GLU | A | 312 | −30.526 | 3.469 | 1.189 | 1.00 | 27.09 | C |
| ATOM | 4645 | OE1 | GLU | A | 312 | −30.083 | 4.608 | 1.458 | 1.00 | 30.07 | O |
| ATOM | 4646 | OE2 | GLU | A | 312 | −29.885 | 2.418 | 1.454 | 1.00 | 27.86 | O |
| ATOM | 4647 | C | GLU | A | 312 | −32.954 | 1.498 | −2.731 | 1.00 | 23.13 | C |
| ATOM | 4648 | O | GLU | A | 312 | −32.851 | 2.064 | −3.803 | 1.00 | 22.88 | O |
| ATOM | 4650 | N | ARG | A | 313 | −32.819 | .188 | −2.615 | 1.00 | 23.74 | N |
| ATOM | 4651 | CA | ARG | A | 313 | −32.400 | −.628 | −3.743 | 1.00 | 24.46 | C |
| ATOM | 4653 | CB | ARG | A | 313 | −31.758 | −1.916 | −3.232 | 1.00 | 25.01 | C |
| ATOM | 4656 | CG | ARG | A | 313 | −30.421 | −1.667 | −2.481 | 1.00 | 27.74 | C |
| ATOM | 4659 | CD | ARG | A | 313 | −29.715 | −2.963 | −2.072 | 1.00 | 31.41 | C |
| ATOM | 4662 | NE | ARG | A | 313 | −30.675 | −3.921 | −1.499 | 1.00 | 34.94 | N |
| ATOM | 4664 | CZ | ARG | A | 313 | −31.203 | −4.974 | −2.138 | 1.00 | 37.87 | C |
| ATOM | 4665 | NH1 | ARG | A | 313 | −30.861 | −5.282 | −3.402 | 1.00 | 38.35 | N |
| ATOM | 4668 | NH2 | ARG | A | 313 | −32.079 | −5.746 | −1.495 | 1.00 | 38.82 | N |
| ATOM | 4671 | C | ARG | A | 313 | −33.523 | −.914 | −4.739 | 1.00 | 24.27 | C |
| ATOM | 4672 | O | ARG | A | 313 | −33.257 | −1.178 | −5.898 | 1.00 | 24.17 | O |
| ATOM | 4674 | N | TRP | A | 314 | −34.770 | −.873 | −4.282 | 1.00 | 24.59 | N |
| ATOM | 4675 | CA | TRP | A | 314 | −35.939 | −1.042 | −5.142 | 1.00 | 24.66 | C |
| ATOM | 4677 | CB | TRP | A | 314 | −36.175 | .234 | −5.961 | 1.00 | 24.39 | C |
| ATOM | 4680 | CG | TRP | A | 314 | −37.575 | .382 | −6.386 | 1.00 | 22.61 | C |
| ATOM | 4681 | CD1 | TRP | A | 314 | −38.073 | .204 | −7.635 | 1.00 | 21.66 | C |
| ATOM | 4683 | NE1 | TRP | A | 314 | −39.429 | .403 | −7.634 | 1.00 | 21.42 | N |
| ATOM | 4685 | CE2 | TRP | A | 314 | −39.829 | .707 | −6.360 | 1.00 | 20.99 | C |
| ATOM | 4686 | CD2 | TRP | A | 314 | −38.683 | .701 | −5.550 | 1.00 | 21.41 | C |
| ATOM | 4687 | CE3 | TRP | A | 314 | −38.817 | .991 | −4.191 | 1.00 | 21.48 | C |
| ATOM | 4689 | CZ3 | TRP | A | 314 | −40.080 | 1.277 | −3.693 | 1.00 | 21.38 | C |
| ATOM | 4691 | CH2 | TRP | A | 314 | −41.204 | 1.269 | −4.523 | 1.00 | 20.84 | C |
| ATOM | 4693 | CZ2 | TRP | A | 314 | −41.099 | .985 | −5.857 | 1.00 | 20.87 | C |
| ATOM | 4695 | C | TRP | A | 314 | −35.831 | −2.286 | −6.038 | 1.00 | 25.65 | C |
| ATOM | 4696 | O | TRP | A | 314 | −36.069 | −2.238 | −7.259 | 1.00 | 25.69 | O |
| ATOM | 4698 | N | ASP | A | 315 | −35.480 | −3.400 | −5.404 | 1.00 | 26.79 | N |
| ATOM | 4699 | CA | ASP | A | 315 | −35.253 | −4.667 | −6.087 | 1.00 | 28.01 | C |
| ATOM | 4701 | CB | ASP | A | 315 | −33.801 | −5.097 | −5.890 | 1.00 | 28.07 | C |
| ATOM | 4704 | CG | ASP | A | 315 | −33.553 | −6.536 | −6.296 | 1.00 | 29.92 | C |
| ATOM | 4705 | OD1 | ASP | A | 315 | −34.262 | −7.026 | −7.197 | 1.00 | 32.58 | O |
| ATOM | 4706 | OD2 | ASP | A | 315 | −32.648 | −7.194 | −5.722 | 1.00 | 32.73 | O |
| ATOM | 4707 | C | ASP | A | 315 | −36.202 | −5.710 | −5.518 | 1.00 | 28.91 | C |
| ATOM | 4708 | O | ASP | A | 315 | −36.019 | −6.163 | −4.399 | 1.00 | 29.17 | O |
| ATOM | 4710 | N | VAL | A | 316 | −37.218 | −6.091 | −6.283 | 1.00 | 30.25 | N |
| ATOM | 4711 | CA | VAL | A | 316 | −38.233 | −7.012 | −5.778 | 1.00 | 31.47 | C |
| ATOM | 4713 | CB | VAL | A | 316 | −39.396 | −7.156 | −6.755 | 1.00 | 31.56 | C |
| ATOM | 4715 | CG1 | VAL | A | 316 | −40.668 | −7.590 | −6.027 | 1.00 | 30.99 | C |
| ATOM | 4719 | CG2 | VAL | A | 316 | −39.033 | −8.141 | −7.862 | 1.00 | 31.84 | C |
| ATOM | 4723 | C | VAL | A | 316 | −37.663 | −8.405 | −5.540 | 1.00 | 32.86 | C |
| ATOM | 4724 | O | VAL | A | 316 | −38.170 | −9.153 | −4.708 | 1.00 | 32.99 | O |
| ATOM | 4726 | N | ASN | A | 317 | −36.607 | −8.750 | −6.278 | 1.00 | 34.55 | N |
| ATOM | 4727 | CA | ASN | A | 317 | −35.940 | −10.060 | −6.160 | 1.00 | 35.53 | C |
| ATOM | 4729 | CB | ASN | A | 317 | −35.013 | −10.298 | −7.367 | 1.00 | 35.68 | C |
| ATOM | 4732 | CG | ASN | A | 317 | −35.752 | −10.264 | −8.713 | 1.00 | 35.92 | C |
| ATOM | 4733 | OD1 | ASN | A | 317 | −36.634 | −11.092 | −8.971 | 1.00 | 36.95 | O |
| ATOM | 4734 | ND2 | ASN | A | 317 | −35.368 | −9.323 | −9.585 | 1.00 | 34.17 | N |
| ATOM | 4737 | C | ASN | A | 317 | −35.126 | −10.225 | −4.871 | 1.00 | 36.40 | C |
| ATOM | 4738 | O | ASN | A | 317 | −34.385 | −11.195 | −4.747 | 1.00 | 36.47 | O |
| ATOM | 4740 | N | ALA | A | 318 | −35.239 | −9.265 | −3.944 | 1.00 | 37.52 | N |
| ATOM | 4741 | CA | ALA | A | 318 | −34.614 | −9.335 | −2.613 | 1.00 | 38.45 | C |
| ATOM | 4743 | CB | ALA | A | 318 | −33.371 | −8.465 | −2.557 | 1.00 | 38.43 | C |
| ATOM | 4747 | C | ALA | A | 318 | −35.631 | −8.902 | −1.554 | 1.00 | 39.28 | C |
| ATOM | 4748 | O | ALA | A | 318 | −35.361 | −8.094 | −.662 | 1.00 | 39.55 | O |
| ATOM | 4750 | N | ILE | A | 319 | −36.823 | −9.456 | −1.698 | 1.00 | 40.17 | N |
| ATOM | 4751 | CA | ILE | A | 319 | −37.905 | −9.310 | −.740 | 1.00 | 40.49 | C |
| ATOM | 4753 | CB | ILE | A | 319 | −39.275 | −9.588 | −1.469 | 1.00 | 40.64 | C |
| ATOM | 4755 | CG1 | ILE | A | 319 | −40.473 | −9.078 | −.683 | 1.00 | 40.88 | C |
| ATOM | 4758 | CD1 | ILE | A | 319 | −41.799 | −9.535 | −1.280 | 1.00 | 40.86 | C |
| ATOM | 4762 | CG2 | ILE | A | 319 | −39.460 | −11.082 | −1.801 | 1.00 | 40.50 | C |
| ATOM | 4766 | C | ILE | A | 319 | −37.656 | −10.319 | .393 | 1.00 | 40.69 | C |
| ATOM | 4767 | O | ILE | A | 319 | −38.136 | −10.138 | 1.504 | 1.00 | 40.88 | O |
| ATOM | 4769 | N | ASN | A | 320 | −36.886 | −11.374 | .104 | 1.00 | 40.79 | N |
| ATOM | 4770 | CA | ASN | A | 320 | −36.689 | −12.483 | 1.049 | 1.00 | 40.64 | C |
| ATOM | 4772 | CB | ASN | A | 320 | −36.240 | −13.761 | .314 | 1.00 | 40.73 | C |
| ATOM | 4775 | CG | ASN | A | 320 | −37.370 | −14.422 | −.468 | 1.00 | 40.98 | C |
| ATOM | 4776 | OD1 | ASN | A | 320 | −38.556 | −14.309 | −.119 | 1.00 | 40.77 | O |
| ATOM | 4777 | ND2 | ASN | A | 320 | −37.001 | −15.131 | −1.529 | 1.00 | 41.31 | N |
| ATOM | 4780 | C | ASN | A | 320 | −35.711 | −12.175 | 2.169 | 1.00 | 40.16 | C |
| ATOM | 4781 | O | ASN | A | 320 | −35.546 | −12.978 | 3.077 | 1.00 | 40.15 | O |
| ATOM | 4783 | N | ASP | A | 321 | −35.067 | −11.017 | 2.101 | 1.00 | 39.66 | N |
| ATOM | 4784 | CA | ASP | A | 321 | −34.111 | −10.615 | 3.126 | 1.00 | 39.51 | C |

TABLE 3-7-continued

Coordinates of *P. tremuloides IspS*

| | | | | | | | | | | | |
|---|---|---|---|---|---|---|---|---|---|---|---|
| ATOM | 4786 | CB | ASP | A | 321 | −33.114 | −9.571 | 2.575 | 1.00 | 40.17 | C |
| ATOM | 4789 | CG | ASP | A | 321 | −32.595 | −9.904 | 1.152 | 1.00 | 42.12 | C |
| ATOM | 4790 | OD1 | ASP | A | 321 | −32.425 | −11.115 | .820 | 1.00 | 44.15 | O |
| ATOM | 4791 | OD2 | ASP | A | 321 | −32.354 | −8.934 | .375 | 1.00 | 43.28 | O |
| ATOM | 4792 | C | ASP | A | 321 | −34.851 | −10.030 | 4.337 | 1.00 | 38.27 | C |
| ATOM | 4793 | O | ASP | A | 321 | −34.304 | −9.987 | 5.443 | 1.00 | 38.15 | O |
| ATOM | 4795 | N | LEU | A | 322 | −36.089 | −9.583 | 4.108 | 1.00 | 36.72 | N |
| ATOM | 4796 | CA | LEU | A | 322 | −36.887 | −8.875 | 5.104 | 1.00 | 35.38 | C |
| ATOM | 4798 | CB | LEU | A | 322 | −37.894 | −7.942 | 4.422 | 1.00 | 35.15 | C |
| ATOM | 4801 | CG | LEU | A | 322 | −37.370 | −6.840 | 3.503 | 1.00 | 34.83 | C |
| ATOM | 4803 | CD1 | LEU | A | 322 | −38.479 | −6.286 | 2.626 | 1.00 | 34.45 | C |
| ATOM | 4807 | CD2 | LEU | A | 322 | −36.742 | −5.740 | 4.316 | 1.00 | 34.89 | C |
| ATOM | 4811 | C | LEU | A | 322 | −37.683 | −9.834 | 5.963 | 1.00 | 34.57 | C |
| ATOM | 4812 | O | LEU | A | 322 | −37.975 | −10.933 | 5.527 | 1.00 | 34.27 | O |
| ATOM | 4814 | N | PRO | A | 323 | −38.039 | −9.402 | 7.189 | 1.00 | 33.93 | N |
| ATOM | 4815 | CA | PRO | A | 323 | −39.070 | −9.917 | 8.067 | 1.00 | 33.49 | C |
| ATOM | 4817 | CB | PRO | A | 323 | −39.151 | −8.840 | 9.141 | 1.00 | 33.31 | C |
| ATOM | 4820 | CG | PRO | A | 323 | −37.791 | −8.419 | 9.311 | 1.00 | 33.67 | C |
| ATOM | 4823 | CD | PRO | A | 323 | −37.154 | −8.496 | 7.941 | 1.00 | 34.20 | C |
| ATOM | 4826 | C | PRO | A | 323 | −40.429 | −10.036 | 7.425 | 1.00 | 33.33 | C |
| ATOM | 4827 | O | PRO | A | 323 | −40.776 | −9.232 | 6.579 | 1.00 | 33.35 | O |
| ATOM | 4828 | N | ASP | A | 324 | −41.209 | −11.005 | 7.891 | 1.00 | 33.37 | N |
| ATOM | 4829 | CA | ASP | A | 324 | −42.511 | −11.329 | 7.313 | 1.00 | 33.36 | C |
| ATOM | 4831 | CB | ASP | A | 324 | −43.137 | −12.542 | 8.037 | 1.00 | 33.59 | C |
| ATOM | 4834 | CG | ASP | A | 324 | −42.496 | −13.881 | 7.619 | 1.00 | 34.18 | C |
| ATOM | 4835 | OD1 | ASP | A | 324 | −41.885 | −13.915 | 6.518 | 1.00 | 36.44 | O |
| ATOM | 4836 | OD2 | ASP | A | 324 | −42.607 | −14.887 | 8.371 | 1.00 | 32.19 | O |
| ATOM | 4837 | C | ASP | A | 324 | −43.484 | −10.149 | 7.289 | 1.00 | 32.90 | C |
| ATOM | 4838 | O | ASP | A | 324 | −44.108 | −9.885 | 6.255 | 1.00 | 33.36 | O |
| ATOM | 4840 | N | TYR | A | 325 | −43.606 | −9.423 | 8.392 | 1.00 | 32.10 | N |
| ATOM | 4841 | CA | TYR | A | 325 | −44.515 | −8.279 | 8.400 | 1.00 | 31.65 | C |
| ATOM | 4843 | CB | TYR | A | 325 | −44.718 | −7.726 | 9.815 | 1.00 | 31.68 | C |
| ATOM | 4846 | CG | TYR | A | 325 | −43.618 | −6.846 | 10.352 | 1.00 | 31.35 | C |
| ATOM | 4847 | CD1 | TYR | A | 325 | −42.507 | −7.389 | 10.992 | 1.00 | 31.31 | C |
| ATOM | 4849 | CE1 | TYR | A | 325 | −41.497 | −6.574 | 11.504 | 1.00 | 31.46 | C |
| ATOM | 4851 | CZ | TYR | A | 325 | −41.613 | −5.192 | 11.392 | 1.00 | 32.41 | C |
| ATOM | 4852 | OH | TYR | A | 325 | −40.637 | −4.336 | 11.893 | 1.00 | 32.78 | O |
| ATOM | 4854 | CE2 | TYR | A | 325 | −42.723 | −4.644 | 10.769 | 1.00 | 32.17 | C |
| ATOM | 4856 | CD2 | TYR | A | 325 | −43.713 | −5.470 | 10.261 | 1.00 | 31.47 | C |
| ATOM | 4858 | C | TYR | A | 325 | −44.094 | −7.179 | 7.424 | 1.00 | 31.17 | C |
| ATOM | 4859 | O | TYR | A | 325 | −44.947 | −6.458 | 6.920 | 1.00 | 31.09 | O |
| ATOM | 4861 | N | MET | A | 326 | −42.796 | −7.068 | 7.145 | 1.00 | 30.73 | N |
| ATOM | 4862 | CA | MET | A | 326 | −42.277 | −6.036 | 6.225 | 1.00 | 30.49 | C |
| ATOM | 4864 | CB | MET | A | 326 | −40.832 | −5.702 | 6.565 | 1.00 | 30.16 | C |
| ATOM | 4867 | CG | MET | A | 326 | −40.725 | −4.918 | 7.830 | 1.00 | 29.57 | C |
| ATOM | 4870 | SD | MET | A | 326 | −39.057 | −4.376 | 8.166 | 1.00 | 28.39 | S |
| ATOM | 4871 | CE | MET | A | 326 | −39.407 | −2.787 | 8.933 | 1.00 | 26.18 | C |
| ATOM | 4875 | C | MET | A | 326 | −42.371 | −6.418 | 4.748 | 1.00 | 30.59 | C |
| ATOM | 4876 | O | MET | A | 326 | −42.786 | −5.603 | 3.920 | 1.00 | 30.48 | O |
| ATOM | 4878 | N | LYS | A | 327 | −41.936 | −7.643 | 4.438 | 1.00 | 30.68 | N |
| ATOM | 4879 | CA | LYS | A | 327 | −42.170 | −8.299 | 3.143 | 1.00 | 30.56 | C |
| ATOM | 4881 | CB | LYS | A | 327 | −42.267 | −9.830 | 3.326 | 1.00 | 30.84 | C |
| ATOM | 4884 | CG | LYS | A | 327 | −41.052 | −10.607 | 2.844 | 1.00 | 32.35 | C |
| ATOM | 4887 | CD | LYS | A | 327 | −40.990 | −12.019 | 3.412 | 1.00 | 34.43 | C |
| ATOM | 4890 | CE | LYS | A | 327 | −40.221 | −12.941 | 2.462 | 1.00 | 35.77 | C |
| ATOM | 4893 | NZ | LYS | A | 327 | −39.691 | −14.162 | 3.150 | 1.00 | 37.20 | N |
| ATOM | 4897 | C | LYS | A | 327 | −43.453 | −7.811 | 2.515 | 1.00 | 29.89 | C |
| ATOM | 4898 | O | LYS | A | 327 | −43.447 | −7.220 | 1.436 | 1.00 | 29.85 | O |
| ATOM | 4900 | N | LEU | A | 328 | −44.544 | −8.046 | 3.230 | 1.00 | 29.10 | N |
| ATOM | 4901 | CA | LEU | A | 328 | −45.871 | −7.781 | 2.730 | 1.00 | 28.77 | C |
| ATOM | 4903 | CB | LEU | A | 328 | −46.899 | −8.336 | 3.709 | 1.00 | 28.81 | C |
| ATOM | 4906 | CG | LEU | A | 328 | −48.349 | −8.364 | 3.257 | 1.00 | 28.82 | C |
| ATOM | 4908 | CD1 | LEU | A | 328 | −48.519 | −9.260 | 2.046 | 1.00 | 29.09 | C |
| ATOM | 4912 | CD2 | LEU | A | 328 | −49.202 | −8.845 | 4.411 | 1.00 | 29.16 | C |
| ATOM | 4916 | C | LEU | A | 328 | −46.057 | −6.291 | 2.564 | 1.00 | 28.61 | C |
| ATOM | 4917 | O | LEU | A | 328 | −46.582 | −5.828 | 1.554 | 1.00 | 29.00 | O |
| ATOM | 4919 | N | CYS | A | 329 | −45.612 | −5.532 | 3.557 | 1.00 | 28.24 | N |
| ATOM | 4920 | CA | CYS | A | 329 | −45.737 | −4.086 | 3.504 | 1.00 | 27.95 | C |
| ATOM | 4922 | CB | CYS | A | 329 | −45.311 | −3.459 | 4.834 | 1.00 | 28.21 | C |
| ATOM | 4925 | SG | CYS | A | 329 | −45.280 | −1.630 | 4.817 | 1.00 | 32.39 | S |
| ATOM | 4927 | C | CYS | A | 329 | −44.921 | −3.541 | 2.327 | 1.00 | 26.34 | C |
| ATOM | 4928 | O | CYS | A | 329 | −45.459 | −2.853 | 1.475 | 1.00 | 26.23 | O |
| ATOM | 4930 | N | PHE | A | 330 | −43.642 | −3.882 | 2.269 | 1.00 | 24.82 | N |
| ATOM | 4931 | CA | PHE | A | 330 | −42.790 | −3.514 | 1.130 | 1.00 | 23.82 | C |
| ATOM | 4933 | CB | PHE | A | 330 | −41.397 | −4.137 | 1.283 | 1.00 | 23.64 | C |
| ATOM | 4936 | CG | PHE | A | 330 | −40.492 | −3.873 | .117 | 1.00 | 22.63 | C |
| ATOM | 4937 | CD1 | PHE | A | 330 | −39.845 | −2.658 | −.008 | 1.00 | 21.68 | C |
| ATOM | 4939 | CE1 | PHE | A | 330 | −39.020 | −2.393 | −1.082 | 1.00 | 21.07 | C |

TABLE 3-7-continued

| Coordinates of *P. tremuloides IspS* | | | | | | | | | | | |
|---|---|---|---|---|---|---|---|---|---|---|---|
| ATOM | 4941 | CZ | PHE | A | 330 | −38.829 | −3.343 | −2.046 | 1.00 | 22.00 | C |
| ATOM | 4943 | CE2 | PHE | A | 330 | −39.474 | −4.568 | −1.944 | 1.00 | 22.60 | C |
| ATOM | 4945 | CD2 | PHE | A | 330 | −40.309 | −4.824 | −.865 | 1.00 | 22.36 | C |
| ATOM | 4947 | C | PHE | A | 330 | −43.348 | −3.863 | −.281 | 1.00 | 22.99 | C |
| ATOM | 4948 | O | PHE | A | 330 | −43.350 | −3.012 | −1.182 | 1.00 | 22.98 | O |
| ATOM | 4950 | N | LEU | A | 331 | −43.789 | −5.101 | −.492 | 1.00 | 21.65 | N |
| ATOM | 4951 | CA | LEU | A | 331 | −44.306 | −5.484 | −1.816 | 1.00 | 20.74 | C |
| ATOM | 4953 | CB | LEU | A | 331 | −44.573 | −6.990 | −1.912 | 1.00 | 20.57 | C |
| ATOM | 4956 | CG | LEU | A | 331 | −44.959 | −7.575 | −3.277 | 1.00 | 19.82 | C |
| ATOM | 4958 | CD1 | LEU | A | 331 | −43.936 | −7.246 | −4.329 | 1.00 | 19.00 | C |
| ATOM | 4962 | CD2 | LEU | A | 331 | −45.128 | −9.092 | −3.165 | 1.00 | 19.11 | C |
| ATOM | 4966 | C | LEU | A | 331 | −45.568 | −4.710 | −2.159 | 1.00 | 19.98 | C |
| ATOM | 4967 | O | LEU | A | 331 | −45.753 | −4.324 | −3.300 | 1.00 | 20.15 | O |
| ATOM | 4969 | N | ALA | A | 332 | −46.431 | −4.495 | −1.172 | 1.00 | 19.09 | N |
| ATOM | 4970 | CA | ALA | A | 332 | −47.619 | −3.675 | −1.353 | 1.00 | 18.46 | C |
| ATOM | 4972 | CB | ALA | A | 332 | −48.406 | −3.587 | −.045 | 1.00 | 18.20 | C |
| ATOM | 4976 | C | ALA | A | 332 | −47.248 | −2.279 | −1.856 | 1.00 | 17.91 | C |
| ATOM | 4977 | O | ALA | A | 332 | −47.890 | −1.745 | −2.744 | 1.00 | 17.98 | O |
| ATOM | 4979 | N | LEU | A | 333 | −46.197 | −1.706 | −1.295 | 1.00 | 17.62 | N |
| ATOM | 4980 | CA | LEU | A | 333 | −45.753 | −.353 | −1.637 | 1.00 | 17.60 | C |
| ATOM | 4982 | CB | LEU | A | 333 | −44.725 | .132 | −.598 | 1.00 | 17.59 | C |
| ATOM | 4985 | CG | LEU | A | 333 | −44.122 | 1.533 | −.761 | 1.00 | 17.16 | C |
| ATOM | 4987 | CD1 | LEU | A | 333 | −45.166 | 2.629 | −.554 | 1.00 | 16.99 | C |
| ATOM | 4991 | CD2 | LEU | A | 333 | −42.979 | 1.704 | .200 | 1.00 | 15.89 | C |
| ATOM | 4995 | C | LEU | A | 333 | −45.100 | −.320 | −3.005 | 1.00 | 17.70 | C |
| ATOM | 4996 | O | LEU | A | 333 | −45.321 | .603 | −3.795 | 1.00 | 17.86 | O |
| ATOM | 4998 | N | TYR | A | 334 | −44.248 | −1.319 | −3.234 | 1.00 | 17.63 | N |
| ATOM | 4999 | CA | TYR | A | 334 | −43.542 | −1.531 | −4.489 | 1.00 | 17.44 | C |
| ATOM | 5001 | CB | TYR | A | 334 | −42.893 | −2.908 | −4.444 | 1.00 | 17.50 | C |
| ATOM | 5004 | CG | TYR | A | 334 | −41.897 | −3.169 | −5.523 | 1.00 | 18.03 | C |
| ATOM | 5005 | CD1 | TYR | A | 334 | −40.698 | −2.473 | −5.569 | 1.00 | 18.83 | C |
| ATOM | 5007 | CE1 | TYR | A | 334 | −39.764 | −2.725 | −6.542 | 1.00 | 18.13 | C |
| ATOM | 5009 | CZ | TYR | A | 334 | −40.016 | −3.678 | −7.478 | 1.00 | 18.78 | C |
| ATOM | 5010 | OH | TYR | A | 334 | −39.096 | −3.929 | −8.439 | 1.00 | 21.71 | O |
| ATOM | 5012 | CE2 | TYR | A | 334 | −41.180 | −4.391 | −7.462 | 1.00 | 19.74 | C |
| ATOM | 5014 | CD2 | TYR | A | 334 | −42.118 | −4.139 | −6.472 | 1.00 | 19.59 | C |
| ATOM | 5016 | C | TYR | A | 334 | −44.500 | −1.497 | −5.649 | 1.00 | 17.43 | C |
| ATOM | 5017 | O | TYR | A | 334 | −44.264 | −.803 | −6.636 | 1.00 | 17.64 | O |
| ATOM | 5019 | N | ASN | A | 335 | −45.589 | −2.253 | −5.504 | 1.00 | 17.30 | N |
| ATOM | 5020 | CA | ASN | A | 335 | −46.574 | −2.448 | −6.553 | 1.00 | 17.23 | C |
| ATOM | 5022 | CB | ASN | A | 335 | −47.544 | −3.551 | −6.166 | 1.00 | 17.32 | C |
| ATOM | 5025 | CG | ASN | A | 335 | −46.952 | −4.920 | −6.332 | 1.00 | 18.16 | C |
| ATOM | 5026 | OD1 | ASN | A | 335 | −45.913 | −5.090 | −6.989 | 1.00 | 18.99 | O |
| ATOM | 5027 | ND2 | ASN | A | 335 | −47.616 | −5.921 | −5.749 | 1.00 | 18.49 | N |
| ATOM | 5030 | C | ASN | A | 335 | −47.365 | −1.218 | −6.812 | 1.00 | 17.12 | C |
| ATOM | 5031 | O | ASN | A | 335 | −47.613 | −.852 | −7.965 | 1.00 | 17.36 | O |
| ATOM | 5033 | N | THR | A | 336 | −47.789 | −.602 | −5.722 | 1.00 | 17.20 | N |
| ATOM | 5034 | CA | THR | A | 336 | −48.601 | .593 | −5.779 | 1.00 | 17.36 | C |
| ATOM | 5036 | CB | THR | A | 336 | −48.888 | 1.104 | −4.381 | 1.00 | 17.20 | C |
| ATOM | 5038 | OG1 | THR | A | 336 | −49.611 | .103 | −3.657 | 1.00 | 16.26 | O |
| ATOM | 5040 | CG2 | THR | A | 336 | −49.688 | 2.384 | −4.452 | 1.00 | 17.18 | C |
| ATOM | 5044 | C | THR | A | 336 | −47.893 | 1.691 | −6.550 | 1.00 | 17.84 | C |
| ATOM | 5045 | O | THR | A | 336 | −48.511 | 2.388 | −7.360 | 1.00 | 18.07 | O |
| ATOM | 5047 | N | ILE | A | 337 | −46.595 | 1.831 | −6.298 | 1.00 | 18.14 | N |
| ATOM | 5048 | CA | ILE | A | 337 | −45.817 | 2.904 | −6.895 | 1.00 | 18.50 | C |
| ATOM | 5050 | CB | ILE | A | 337 | −44.584 | 3.209 | −6.066 | 1.00 | 18.31 | C |
| ATOM | 5052 | CG1 | ILE | A | 337 | −45.014 | 3.997 | −4.837 | 1.00 | 18.58 | C |
| ATOM | 5055 | CD1 | ILE | A | 337 | −44.043 | 3.866 | −3.735 | 1.00 | 20.66 | C |
| ATOM | 5059 | CG2 | ILE | A | 337 | −43.570 | 3.988 | −6.867 | 1.00 | 16.98 | C |
| ATOM | 5063 | C | ILE | A | 337 | −45.447 | 2.548 | −8.314 | 1.00 | 19.29 | C |
| ATOM | 5064 | O | ILE | A | 337 | −45.556 | 3.387 | −9.214 | 1.00 | 19.17 | O |
| ATOM | 5066 | N | ASN | A | 338 | −45.033 | 1.299 | −8.513 | 1.00 | 20.16 | N |
| ATOM | 5067 | CA | ASN | A | 338 | −44.861 | .767 | −9.864 | 1.00 | 20.93 | C |
| ATOM | 5069 | CB | ASN | A | 338 | −44.409 | −.695 | −9.830 | 1.00 | 21.07 | C |
| ATOM | 5072 | CG | ASN | A | 338 | −42.953 | −.845 | −9.439 | 1.00 | 21.61 | C |
| ATOM | 5073 | OD1 | ASN | A | 338 | −42.232 | .143 | −9.308 | 1.00 | 22.40 | O |
| ATOM | 5074 | ND2 | ASN | A | 338 | −42.509 | −2.086 | −9.260 | 1.00 | 21.92 | N |
| ATOM | 5077 | C | ASN | A | 338 | −46.123 | .914 | −10.719 | 1.00 | 21.44 | C |
| ATOM | 5078 | O | ASN | A | 338 | −46.022 | 1.202 | −11.904 | 1.00 | 21.25 | O |
| ATOM | 5080 | N | GLU | A | 339 | −47.303 | .747 | −10.128 | 1.00 | 22.21 | N |
| ATOM | 5081 | CA | GLU | A | 339 | −48.532 | 1.000 | −10.880 | 1.00 | 23.31 | C |
| ATOM | 5083 | CB | GLU | A | 339 | −49.768 | .464 | −10.164 | 1.00 | 24.13 | C |
| ATOM | 5086 | CG | GLU | A | 339 | −50.146 | −.936 | −10.660 | 1.00 | 28.69 | C |
| ATOM | 5089 | CD | GLU | A | 339 | −50.939 | −1.740 | −9.638 | 1.00 | 35.06 | C |
| ATOM | 5090 | OE1 | GLU | A | 339 | −51.899 | −1.136 | −9.067 | 1.00 | 39.51 | O |
| ATOM | 5091 | OE2 | GLU | A | 339 | −50.596 | −2.952 | −9.414 | 1.00 | 36.64 | O |
| ATOM | 5092 | C | GLU | A | 339 | −48.725 | 2.463 | −11.269 | 1.00 | 22.71 | C |
| ATOM | 5093 | O | GLU | A | 339 | −49.215 | 2.743 | −12.372 | 1.00 | 22.48 | O |

TABLE 3-7-continued

Coordinates of *P. tremuloides IspS*

| | | | | | | | | | | | |
|---|---|---|---|---|---|---|---|---|---|---|---|
| ATOM | 5095 | N | ILE | A | 340 | −48.339 | 3.390 | −10.390 | 1.00 | 22.19 | N |
| ATOM | 5096 | CA | ILE | A | 340 | −48.406 | 4.813 | −10.734 | 1.00 | 21.64 | C |
| ATOM | 5098 | CB | ILE | A | 340 | −48.135 | 5.739 | −9.538 | 1.00 | 21.33 | C |
| ATOM | 5100 | CG1 | ILE | A | 340 | −49.229 | 5.596 | −8.482 | 1.00 | 21.29 | C |
| ATOM | 5103 | CD1 | ILE | A | 340 | −48.925 | 6.306 | −7.150 | 1.00 | 20.00 | C |
| ATOM | 5107 | CG2 | ILE | A | 340 | −48.091 | 7.177 | −9.982 | 1.00 | 20.28 | C |
| ATOM | 5111 | C | ILE | A | 340 | −47.414 | 5.128 | −11.861 | 1.00 | 21.78 | C |
| ATOM | 5112 | O | ILE | A | 340 | −47.786 | 5.826 | −12.818 | 1.00 | 22.13 | O |
| ATOM | 5114 | N | ALA | A | 341 | −46.179 | 4.609 | −11.771 | 1.00 | 21.34 | N |
| ATOM | 5115 | CA | ALA | A | 341 | −45.147 | 4.892 | −12.787 | 1.00 | 21.03 | C |
| ATOM | 5117 | CB | ALA | A | 341 | −43.837 | 4.268 | −12.406 | 1.00 | 20.55 | C |
| ATOM | 5121 | C | ALA | A | 341 | −45.592 | 4.426 | −14.183 | 1.00 | 21.32 | C |
| ATOM | 5122 | O | ALA | A | 341 | −45.228 | 5.036 | −15.217 | 1.00 | 21.11 | O |
| ATOM | 5124 | N | TYR | A | 342 | −46.393 | 3.355 | −14.196 | 1.00 | 21.45 | N |
| ATOM | 5125 | CA | TYR | A | 342 | −47.008 | 2.861 | −15.414 | 1.00 | 21.41 | C |
| ATOM | 5127 | CB | TYR | A | 342 | −47.627 | 1.468 | −15.208 | 1.00 | 21.31 | C |
| ATOM | 5130 | CG | TYR | A | 342 | −48.336 | .957 | −16.450 | 1.00 | 19.60 | C |
| ATOM | 5131 | CD1 | TYR | A | 342 | −47.613 | .463 | −17.521 | 1.00 | 16.69 | C |
| ATOM | 5133 | CE1 | TYR | A | 342 | −48.231 | .032 | −18.643 | 1.00 | 15.50 | C |
| ATOM | 5135 | CZ | TYR | A | 342 | −49.595 | .085 | −18.728 | 1.00 | 15.88 | C |
| ATOM | 5136 | OH | TYR | A | 342 | −50.196 | −.352 | −19.877 | 1.00 | 16.46 | O |
| ATOM | 5138 | CE2 | TYR | A | 342 | −50.352 | .558 | −17.681 | 1.00 | 16.50 | C |
| ATOM | 5140 | CD2 | TYR | A | 342 | −49.725 | .997 | −16.556 | 1.00 | 18.17 | C |
| ATOM | 5142 | C | TYR | A | 342 | −48.064 | 3.830 | −15.899 | 1.00 | 22.08 | C |
| ATOM | 5143 | O | TYR | A | 342 | −48.094 | 4.169 | −17.048 | 1.00 | 22.07 | O |
| ATOM | 5145 | N | ASP | A | 343 | −48.942 | 4.283 | −15.032 | 1.00 | 23.41 | N |
| ATOM | 5146 | CA | ASP | A | 343 | −49.970 | 5.211 | −15.481 | 1.00 | 24.66 | C |
| ATOM | 5148 | CB | ASP | A | 343 | −50.851 | 5.674 | −14.318 | 1.00 | 25.10 | C |
| ATOM | 5151 | CG | ASP | A | 343 | −51.720 | 4.552 | −13.732 | 1.00 | 26.06 | C |
| ATOM | 5152 | OD1 | ASP | A | 343 | −52.107 | 3.613 | −14.477 | 1.00 | 26.39 | O |
| ATOM | 5153 | OD2 | ASP | A | 343 | −52.032 | 4.642 | −12.516 | 1.00 | 27.29 | O |
| ATOM | 5154 | C | ASP | A | 343 | −49.316 | 6.420 | −16.142 | 1.00 | 25.22 | C |
| ATOM | 5155 | O | ASP | A | 343 | −49.755 | 6.874 | −17.192 | 1.00 | 25.47 | O |
| ATOM | 5157 | N | ASN | A | 344 | −48.260 | 6.936 | −15.528 | 1.00 | 25.87 | N |
| ATOM | 5158 | CA | ASN | A | 344 | −47.508 | 8.042 | −16.127 | 1.00 | 26.41 | C |
| ATOM | 5160 | CB | ASN | A | 344 | −46.498 | 8.605 | −15.134 | 1.00 | 26.56 | C |
| ATOM | 5163 | CG | ASN | A | 344 | −47.152 | 9.407 | −14.073 | 1.00 | 26.95 | C |
| ATOM | 5164 | OD1 | ASN | A | 344 | −47.495 | 10.568 | −14.296 | 1.00 | 29.13 | O |
| ATOM | 5165 | ND2 | ASN | A | 344 | −47.367 | 8.799 | −12.916 | 1.00 | 26.36 | N |
| ATOM | 5168 | C | ASN | A | 344 | −46.785 | 7.674 | −17.416 | 1.00 | 26.53 | C |
| ATOM | 5169 | O | ASN | A | 344 | −46.658 | 8.508 | −18.304 | 1.00 | 26.74 | O |
| ATOM | 5171 | N | LEU | A | 345 | −46.280 | 6.448 | −17.510 | 1.00 | 26.56 | N |
| ATOM | 5172 | CA | LEU | A | 345 | −45.634 | 6.019 | −18.739 | 1.00 | 26.37 | C |
| ATOM | 5174 | CB | LEU | A | 345 | −44.890 | 4.693 | −18.550 | 1.00 | 26.32 | C |
| ATOM | 5177 | CG | LEU | A | 345 | −43.995 | 4.339 | −19.750 | 1.00 | 25.96 | C |
| ATOM | 5179 | CD1 | LEU | A | 345 | −42.706 | 5.133 | −19.665 | 1.00 | 25.07 | C |
| ATOM | 5183 | CD2 | LEU | A | 345 | −43.724 | 2.835 | −19.874 | 1.00 | 24.75 | C |
| ATOM | 5187 | C | LEU | A | 345 | −46.679 | 5.908 | −19.856 | 1.00 | 26.38 | C |
| ATOM | 5188 | O | LEU | A | 345 | −46.435 | 6.335 | −20.966 | 1.00 | 26.52 | O |
| ATOM | 5190 | N | LYS | A | 346 | −47.839 | 5.340 | −19.563 | 1.00 | 26.59 | N |
| ATOM | 5191 | CA | LYS | A | 346 | −48.880 | 5.176 | −20.572 | 1.00 | 26.89 | C |
| ATOM | 5193 | CB | LYS | A | 346 | −50.065 | 4.367 | −20.011 | 1.00 | 26.80 | C |
| ATOM | 5196 | CG | LYS | A | 346 | −51.073 | 3.931 | −21.062 | 1.00 | 26.26 | C |
| ATOM | 5199 | CD | LYS | A | 346 | −52.210 | 3.080 | −20.517 | 1.00 | 26.15 | C |
| ATOM | 5202 | CE | LYS | A | 346 | −53.227 | 3.849 | −19.689 | 1.00 | 26.40 | C |
| ATOM | 5205 | NZ | LYS | A | 346 | −53.136 | 3.506 | −18.223 | 1.00 | 27.67 | N |
| ATOM | 5209 | C | LYS | A | 346 | −49.372 | 6.537 | −21.071 | 1.00 | 27.52 | C |
| ATOM | 5210 | O | LYS | A | 346 | −49.562 | 6.742 | −22.272 | 1.00 | 27.57 | O |
| ATOM | 5212 | N | ASP | A | 347 | −49.567 | 7.472 | −20.148 | 1.00 | 28.10 | N |
| ATOM | 5213 | CA | ASP | A | 347 | −50.309 | 8.689 | −20.465 | 1.00 | 28.58 | C |
| ATOM | 5215 | CB | ASP | A | 347 | −51.305 | 9.017 | −19.329 | 1.00 | 28.85 | C |
| ATOM | 5218 | CG | ASP | A | 347 | −52.426 | 7.950 | −19.197 | 1.00 | 30.01 | C |
| ATOM | 5219 | OD1 | ASP | A | 347 | −52.827 | 7.349 | −20.223 | 1.00 | 30.51 | O |
| ATOM | 5220 | OD2 | ASP | A | 347 | −52.910 | 7.704 | −18.069 | 1.00 | 32.61 | O |
| ATOM | 5221 | C | ASP | A | 347 | −49.407 | 9.871 | −20.804 | 1.00 | 28.22 | C |
| ATOM | 5222 | O | ASP | A | 347 | −49.778 | 10.710 | −21.611 | 1.00 | 28.39 | O |
| ATOM | 5224 | N | LYS | A | 348 | −48.228 | 9.930 | −20.206 | 1.00 | 28.03 | N |
| ATOM | 5225 | CA | LYS | A | 348 | −47.301 | 11.021 | −20.467 | 1.00 | 28.01 | C |
| ATOM | 5227 | CB | LYS | A | 348 | −46.785 | 11.648 | −19.164 | 1.00 | 28.39 | C |
| ATOM | 5230 | CG | LYS | A | 348 | −47.834 | 12.305 | −18.257 | 1.00 | 30.18 | C |
| ATOM | 5233 | CD | LYS | A | 348 | −47.143 | 12.898 | −17.003 | 1.00 | 32.40 | C |
| ATOM | 5236 | CE | LYS | A | 348 | −48.124 | 13.121 | −15.874 | 1.00 | 33.59 | C |
| ATOM | 5239 | NZ | LYS | A | 348 | −49.319 | 13.878 | −16.341 | 1.00 | 35.48 | N |
| ATOM | 5243 | C | LYS | A | 348 | −46.107 | 10.551 | −21.260 | 1.00 | 27.25 | C |
| ATOM | 5244 | O | LYS | A | 348 | −45.241 | 11.345 | −21.566 | 1.00 | 27.60 | O |
| ATOM | 5246 | N | GLY | A | 349 | −46.036 | 9.271 | −21.583 | 1.00 | 26.47 | N |
| ATOM | 5247 | CA | GLY | A | 349 | −44.863 | 8.742 | −22.261 | 1.00 | 26.01 | C |
| ATOM | 5250 | C | GLY | A | 349 | −43.559 | 9.109 | −21.587 | 1.00 | 25.67 | C |

TABLE 3-7-continued

Coordinates of *P. tremuloides IspS*

| | | | | | | | | | | | |
|---|---|---|---|---|---|---|---|---|---|---|---|
| ATOM | 5251 | O | GLY | A | 349 | −42.613 | 9.472 | −22.250 | 1.00 | 25.85 | O |
| ATOM | 5253 | N | GLU | A | 350 | −43.498 | 9.032 | −20.269 | 1.00 | 25.55 | N |
| ATOM | 5254 | CA | GLU | A | 350 | −42.272 | 9.374 | −19.555 | 1.00 | 25.76 | C |
| ATOM | 5256 | CB | GLU | A | 350 | −42.332 | 10.814 | −19.021 | 1.00 | 26.34 | C |
| ATOM | 5259 | CG | GLU | A | 350 | −42.179 | 11.928 | −20.106 | 1.00 | 29.04 | C |
| ATOM | 5262 | CD | GLU | A | 350 | −40.745 | 12.101 | −20.598 | 1.00 | 32.08 | C |
| ATOM | 5263 | OE1 | GLU | A | 350 | −39.853 | 12.170 | −19.716 | 1.00 | 35.46 | O |
| ATOM | 5264 | OE2 | GLU | A | 350 | −40.516 | 12.174 | −21.839 | 1.00 | 31.64 | O |
| ATOM | 5265 | C | GLU | A | 350 | −42.084 | 8.414 | −18.400 | 1.00 | 24.87 | C |
| ATOM | 5266 | O | GLU | A | 350 | −43.067 | 8.046 | −17.760 | 1.00 | 25.16 | O |
| ATOM | 5268 | N | ASN | A | 351 | −40.833 | 8.009 | −18.145 | 1.00 | 23.71 | N |
| ATOM | 5269 | CA | ASN | A | 351 | −40.494 | 7.189 | −16.980 | 1.00 | 22.88 | C |
| ATOM | 5271 | CB | ASN | A | 351 | −39.351 | 6.229 | −17.287 | 1.00 | 22.88 | C |
| ATOM | 5274 | CG | ASN | A | 351 | −39.141 | 5.215 | −16.184 | 1.00 | 22.98 | C |
| ATOM | 5275 | OD1 | ASN | A | 351 | −39.006 | 5.584 | −15.035 | 1.00 | 22.68 | O |
| ATOM | 5276 | ND2 | ASN | A | 351 | −39.139 | 3.924 | −16.529 | 1.00 | 24.38 | N |
| ATOM | 5279 | C | ASN | A | 351 | −40.126 | 8.058 | −15.786 | 1.00 | 22.40 | C |
| ATOM | 5280 | O | ASN | A | 351 | −39.097 | 8.741 | −15.785 | 1.00 | 22.66 | O |
| ATOM | 5282 | N | ILE | A | 352 | −40.965 | 8.021 | −14.760 | 1.00 | 21.55 | N |
| ATOM | 5283 | CA | ILE | A | 352 | −40.770 | 8.860 | −13.591 | 1.00 | 20.75 | C |
| ATOM | 5285 | CB | ILE | A | 352 | −42.002 | 9.788 | −13.360 | 1.00 | 20.95 | C |
| ATOM | 5287 | CG1 | ILE | A | 352 | −43.263 | 8.970 | −13.022 | 1.00 | 20.82 | C |
| ATOM | 5290 | CD1 | ILE | A | 352 | −44.237 | 9.698 | −12.122 | 1.00 | 20.21 | C |
| ATOM | 5294 | CG2 | ILE | A | 352 | −42.266 | 10.669 | −14.582 | 1.00 | 19.85 | C |
| ATOM | 5298 | C | ILE | A | 352 | −40.516 | 8.016 | −12.339 | 1.00 | 20.37 | C |
| ATOM | 5299 | O | ILE | A | 352 | −40.574 | 8.513 | −11.224 | 1.00 | 20.55 | O |
| ATOM | 5301 | N | LEU | A | 353 | −40.236 | 6.733 | −12.519 | 1.00 | 19.98 | N |
| ATOM | 5302 | CA | LEU | A | 353 | −40.061 | 5.828 | −11.387 | 1.00 | 19.42 | C |
| ATOM | 5304 | CB | LEU | A | 353 | −39.894 | 4.392 | −11.870 | 1.00 | 19.27 | C |
| ATOM | 5307 | CG | LEU | A | 353 | −39.989 | 3.318 | −10.799 | 1.00 | 19.01 | C |
| ATOM | 5309 | CD1 | LEU | A | 353 | −41.164 | 3.574 | −9.867 | 1.00 | 18.35 | C |
| ATOM | 5313 | CD2 | LEU | A | 353 | −40.085 | 1.938 | −11.468 | 1.00 | 18.74 | C |
| ATOM | 5317 | C | LEU | A | 353 | −38.890 | 6.240 | −10.523 | 1.00 | 19.11 | C |
| ATOM | 5318 | O | LEU | A | 353 | −39.022 | 6.319 | −9.314 | 1.00 | 18.96 | O |
| ATOM | 5320 | N | PRO | A | 354 | −37.746 | 6.549 | −11.142 | 1.00 | 19.06 | N |
| ATOM | 5321 | CA | PRO | A | 354 | −36.631 | 7.069 | −10.367 | 1.00 | 19.29 | C |
| ATOM | 5323 | CB | PRO | A | 354 | −35.749 | 7.717 | −11.438 | 1.00 | 19.25 | C |
| ATOM | 5326 | CG | PRO | A | 354 | −35.997 | 6.942 | −12.638 | 1.00 | 19.08 | C |
| ATOM | 5329 | CD | PRO | A | 354 | −37.409 | 6.472 | −12.572 | 1.00 | 19.00 | C |
| ATOM | 5332 | C | PRO | A | 354 | −37.024 | 8.122 | −9.328 | 1.00 | 19.33 | C |
| ATOM | 5333 | O | PRO | A | 354 | −36.534 | 8.057 | −8.193 | 1.00 | 19.73 | O |
| ATOM | 5334 | N | TYR | A | 355 | −37.891 | 9.063 | −9.721 | 1.00 | 18.83 | N |
| ATOM | 5335 | CA | TYR | A | 355 | −38.206 | 10.221 | −8.898 | 1.00 | 18.79 | C |
| ATOM | 5337 | CB | TYR | A | 355 | −38.836 | 11.359 | −9.707 | 1.00 | 19.10 | C |
| ATOM | 5340 | CG | TYR | A | 355 | −38.142 | 11.708 | −11.009 | 1.00 | 20.15 | C |
| ATOM | 5341 | CD1 | TYR | A | 355 | −36.940 | 12.403 | −11.027 | 1.00 | 20.78 | C |
| ATOM | 5343 | CE1 | TYR | A | 355 | −36.321 | 12.719 | −12.232 | 1.00 | 22.19 | C |
| ATOM | 5345 | CZ | TYR | A | 355 | −36.918 | 12.347 | −13.438 | 1.00 | 22.19 | C |
| ATOM | 5346 | OH | TYR | A | 355 | −36.341 | 12.660 | −14.657 | 1.00 | 23.29 | O |
| ATOM | 5348 | CE2 | TYR | A | 355 | −38.113 | 11.677 | −13.430 | 1.00 | 21.62 | C |
| ATOM | 5350 | CD2 | TYR | A | 355 | −38.720 | 11.371 | −12.227 | 1.00 | 21.05 | C |
| ATOM | 5352 | C | TYR | A | 355 | −39.155 | 9.864 | −7.777 | 1.00 | 18.43 | C |
| ATOM | 5353 | O | TYR | A | 355 | −39.081 | 10.460 | −6.709 | 1.00 | 18.61 | O |
| ATOM | 5355 | N | LEU | A | 356 | −40.058 | 8.917 | −8.023 | 1.00 | 17.92 | N |
| ATOM | 5356 | CA | LEU | A | 356 | −40.993 | 8.467 | −6.994 | 1.00 | 17.38 | C |
| ATOM | 5358 | CB | LEU | A | 356 | −42.136 | 7.658 | −7.597 | 1.00 | 17.17 | C |
| ATOM | 5361 | CG | LEU | A | 356 | −42.956 | 8.366 | −8.682 | 1.00 | 17.56 | C |
| ATOM | 5363 | CD1 | LEU | A | 356 | −43.933 | 7.419 | −9.371 | 1.00 | 17.47 | C |
| ATOM | 5367 | CD2 | LEU | A | 356 | −43.698 | 9.548 | −8.112 | 1.00 | 18.08 | C |
| ATOM | 5371 | C | LEU | A | 356 | −40.241 | 7.623 | −5.978 | 1.00 | 17.10 | C |
| ATOM | 5372 | O | LEU | A | 356 | −40.332 | 7.859 | −4.783 | 1.00 | 17.62 | O |
| ATOM | 5374 | N | THR | A | 357 | −39.464 | 6.656 | −6.442 | 1.00 | 16.64 | N |
| ATOM | 5375 | CA | THR | A | 357 | −38.775 | 5.769 | −5.513 | 1.00 | 16.18 | C |
| ATOM | 5377 | CB | THR | A | 357 | −38.104 | 4.554 | −6.213 | 1.00 | 16.04 | C |
| ATOM | 5379 | OG1 | THR | A | 357 | −37.092 | 4.996 | −7.123 | 1.00 | 15.93 | O |
| ATOM | 5381 | CG2 | THR | A | 357 | −39.142 | 3.732 | −6.962 | 1.00 | 14.99 | C |
| ATOM | 5385 | C | THR | A | 357 | −37.764 | 6.544 | −4.686 | 1.00 | 16.16 | C |
| ATOM | 5386 | O | THR | A | 357 | −37.599 | 6.278 | −3.506 | 1.00 | 16.07 | O |
| ATOM | 5388 | N | LYS | A | 358 | −37.107 | 7.524 | −5.291 | 1.00 | 16.20 | N |
| ATOM | 5389 | CA | LYS | A | 358 | −36.186 | 8.365 | −4.543 | 1.00 | 16.46 | C |
| ATOM | 5391 | CB | LYS | A | 358 | −35.518 | 9.386 | −5.453 | 1.00 | 16.80 | C |
| ATOM | 5394 | CG | LYS | A | 358 | −34.612 | 10.388 | −4.741 | 1.00 | 18.30 | C |
| ATOM | 5397 | CD | LYS | A | 358 | −33.352 | 9.738 | −4.168 | 1.00 | 20.21 | C |
| ATOM | 5400 | CE | LYS | A | 358 | −32.335 | 10.811 | −3.768 | 1.00 | 21.96 | C |
| ATOM | 5403 | NZ | LYS | A | 358 | −31.163 | 10.275 | −3.019 | 1.00 | 22.95 | N |
| ATOM | 5407 | C | LYS | A | 358 | −36.936 | 9.083 | −3.440 | 1.00 | 16.26 | C |
| ATOM | 5408 | O | LYS | A | 358 | −36.448 | 9.161 | −2.320 | 1.00 | 16.15 | O |
| ATOM | 5410 | N | ALA | A | 359 | −38.126 | 9.593 | −3.763 | 1.00 | 16.11 | N |

TABLE 3-7-continued

Coordinates of *P. tremuloides IspS*

| | | | | | | | | | | | |
|---|---|---|---|---|---|---|---|---|---|---|---|
| ATOM | 5411 | CA | ALA | A | 359 | −38.937 | 10.332 | −2.798 | 1.00 | 16.10 | C |
| ATOM | 5413 | CB | ALA | A | 359 | −40.221 | 10.768 | −3.406 | 1.00 | 15.71 | C |
| ATOM | 5417 | C | ALA | A | 359 | −39.215 | 9.476 | −1.588 | 1.00 | 16.52 | C |
| ATOM | 5418 | O | ALA | A | 359 | −39.247 | 9.970 | −.442 | 1.00 | 16.82 | O |
| ATOM | 5420 | N | TRP | A | 360 | −39.398 | 8.187 | −1.843 | 1.00 | 16.79 | N |
| ATOM | 5421 | CA | TRP | A | 360 | −39.704 | 7.247 | −.780 | 1.00 | 17.25 | C |
| ATOM | 5423 | CB | TRP | A | 360 | −40.390 | 6.006 | −1.352 | 1.00 | 17.41 | C |
| ATOM | 5426 | CG | TRP | A | 360 | −41.852 | 6.129 | −1.318 | 1.00 | 17.06 | C |
| ATOM | 5427 | CD1 | TRP | A | 360 | −42.664 | 6.451 | −2.346 | 1.00 | 17.94 | C |
| ATOM | 5429 | NE1 | TRP | A | 360 | −43.967 | 6.489 | −1.926 | 1.00 | 18.03 | N |
| ATOM | 5431 | CE2 | TRP | A | 360 | −44.002 | 6.193 | −.592 | 1.00 | 17.72 | C |
| ATOM | 5432 | CD2 | TRP | A | 360 | −42.684 | 5.965 | −.179 | 1.00 | 16.60 | C |
| ATOM | 5433 | CE3 | TRP | A | 360 | −42.441 | 5.654 | 1.155 | 1.00 | 16.65 | C |
| ATOM | 5435 | CZ3 | TRP | A | 360 | −43.508 | 5.573 | 2.022 | 1.00 | 16.91 | C |
| ATOM | 5437 | CH2 | TRP | A | 360 | −44.811 | 5.807 | 1.586 | 1.00 | 17.82 | C |
| ATOM | 5439 | CZ2 | TRP | A | 360 | −45.080 | 6.114 | .282 | 1.00 | 18.49 | C |
| ATOM | 5441 | C | TRP | A | 360 | −38.490 | 6.865 | .073 | 1.00 | 17.52 | C |
| ATOM | 5442 | O | TRP | A | 360 | −38.603 | 6.767 | 1.297 | 1.00 | 17.38 | O |
| ATOM | 5444 | N | ALA | A | 361 | −37.344 | 6.651 | −.568 | 1.00 | 17.82 | N |
| ATOM | 5445 | CA | ALA | A | 361 | −36.122 | 6.336 | .157 | 1.00 | 18.11 | C |
| ATOM | 5447 | CB | ALA | A | 361 | −34.982 | 6.050 | −.805 | 1.00 | 17.92 | C |
| ATOM | 5451 | C | ALA | A | 361 | −35.781 | 7.507 | 1.063 | 1.00 | 18.52 | C |
| ATOM | 5452 | O | ALA | A | 361 | −35.434 | 7.327 | 2.229 | 1.00 | 18.48 | O |
| ATOM | 5454 | N | ASP | A | 362 | −35.911 | 8.711 | .521 | 1.00 | 19.16 | N |
| ATOM | 5455 | CA | ASP | A | 362 | −35.627 | 9.925 | 1.276 | 1.00 | 19.90 | C |
| ATOM | 5457 | CB | ASP | A | 362 | −35.797 | 11.167 | .387 | 1.00 | 20.39 | C |
| ATOM | 5460 | CG | ASP | A | 362 | −34.596 | 11.424 | −.530 | 1.00 | 21.84 | C |
| ATOM | 5461 | OD1 | ASP | A | 362 | −33.630 | 10.625 | −.561 | 1.00 | 22.88 | O |
| ATOM | 5462 | OD2 | ASP | A | 362 | −34.630 | 12.453 | −1.231 | 1.00 | 24.83 | O |
| ATOM | 5463 | C | ASP | A | 362 | −36.532 | 10.039 | 2.510 | 1.00 | 19.91 | C |
| ATOM | 5464 | O | ASP | A | 362 | −36.074 | 10.427 | 3.591 | 1.00 | 19.76 | O |
| ATOM | 5466 | N | LEU | A | 363 | −37.813 | 9.707 | 2.346 | 1.00 | 19.95 | N |
| ATOM | 5467 | CA | LEU | A | 363 | −38.747 | 9.688 | 3.478 | 1.00 | 19.85 | C |
| ATOM | 5469 | CB | LEU | A | 363 | −40.175 | 9.415 | 3.006 | 1.00 | 19.70 | C |
| ATOM | 5472 | CG | LEU | A | 363 | −41.219 | 9.293 | 4.123 | 1.00 | 18.58 | C |
| ATOM | 5474 | CD1 | LEU | A | 363 | −41.189 | 10.551 | 4.965 | 1.00 | 18.37 | C |
| ATOM | 5478 | CD2 | LEU | A | 363 | −42.597 | 9.073 | 3.551 | 1.00 | 16.43 | C |
| ATOM | 5482 | C | LEU | A | 363 | −38.368 | 8.613 | 4.488 | 1.00 | 20.24 | C |
| ATOM | 5483 | O | LEU | A | 363 | −38.314 | 8.875 | 5.691 | 1.00 | 20.52 | O |
| ATOM | 5485 | N | CYS | A | 364 | −38.129 | 7.397 | 3.997 | 1.00 | 20.29 | N |
| ATOM | 5486 | CA | CYS | A | 364 | −37.741 | 6.308 | 4.874 | 1.00 | 20.39 | C |
| ATOM | 5488 | CB | CYS | A | 364 | −37.595 | 4.985 | 4.111 | 1.00 | 20.37 | C |
| ATOM | 5491 | SG | CYS | A | 364 | −39.208 | 4.201 | 3.666 | 1.00 | 20.69 | S |
| ATOM | 5493 | C | CYS | A | 364 | −36.467 | 6.683 | 5.646 | 1.00 | 20.59 | C |
| ATOM | 5494 | O | CYS | A | 364 | −36.386 | 6.445 | 6.863 | 1.00 | 20.82 | O |
| ATOM | 5496 | N | ASN | A | 365 | −35.495 | 7.314 | 4.980 | 1.00 | 20.35 | N |
| ATOM | 5497 | CA | ASN | A | 365 | −34.282 | 7.716 | 5.697 | 1.00 | 20.14 | C |
| ATOM | 5499 | CB | ASN | A | 365 | −33.188 | 8.203 | 4.754 | 1.00 | 20.18 | C |
| ATOM | 5502 | CG | ASN | A | 365 | −32.359 | 7.064 | 4.184 | 1.00 | 20.55 | C |
| ATOM | 5503 | OD1 | ASN | A | 365 | −31.706 | 6.316 | 4.925 | 1.00 | 20.40 | O |
| ATOM | 5504 | ND2 | ASN | A | 365 | −32.365 | 6.938 | 2.854 | 1.00 | 21.25 | N |
| ATOM | 5507 | C | ASN | A | 365 | −34.590 | 8.746 | 6.779 | 1.00 | 19.92 | C |
| ATOM | 5508 | O | ASN | A | 365 | −33.997 | 8.685 | 7.857 | 1.00 | 19.94 | O |
| ATOM | 5510 | N | ALA | A | 366 | −35.531 | 9.658 | 6.507 | 1.00 | 19.58 | N |
| ATOM | 5511 | CA | ALA | A | 366 | −36.036 | 10.578 | 7.537 | 1.00 | 19.39 | C |
| ATOM | 5513 | CB | ALA | A | 366 | −37.083 | 11.507 | 6.971 | 1.00 | 18.79 | C |
| ATOM | 5517 | C | ALA | A | 366 | −36.597 | 9.784 | 8.730 | 1.00 | 19.75 | C |
| ATOM | 5518 | O | ALA | A | 366 | −36.215 | 10.049 | 9.891 | 1.00 | 19.53 | O |
| ATOM | 5520 | N | PHE | A | 367 | −37.460 | 8.797 | 8.447 | 1.00 | 19.69 | N |
| ATOM | 5521 | CA | PHE | A | 367 | −37.985 | 7.925 | 9.502 | 1.00 | 20.11 | C |
| ATOM | 5523 | CB | PHE | A | 367 | −38.952 | 6.857 | 8.967 | 1.00 | 20.47 | C |
| ATOM | 5526 | CG | PHE | A | 367 | −40.293 | 7.370 | 8.494 | 1.00 | 21.35 | C |
| ATOM | 5527 | CD1 | PHE | A | 367 | −40.985 | 8.347 | 9.180 | 1.00 | 21.54 | C |
| ATOM | 5529 | CE1 | PHE | A | 367 | −42.224 | 8.775 | 8.732 | 1.00 | 21.47 | C |
| ATOM | 5531 | CZ | PHE | A | 367 | −42.798 | 8.213 | 7.612 | 1.00 | 21.87 | C |
| ATOM | 5533 | CE2 | PHE | A | 367 | −42.135 | 7.230 | 6.924 | 1.00 | 22.60 | C |
| ATOM | 5535 | CD2 | PHE | A | 367 | −40.894 | 6.798 | 7.373 | 1.00 | 22.90 | C |
| ATOM | 5537 | C | PHE | A | 367 | −36.871 | 7.179 | 10.252 | 1.00 | 20.12 | C |
| ATOM | 5538 | O | PHE | A | 367 | −36.940 | 7.009 | 11.476 | 1.00 | 19.88 | O |
| ATOM | 5540 | N | LEU | A | 368 | −35.868 | 6.696 | 9.516 | 1.00 | 20.30 | N |
| ATOM | 5541 | CA | LEU | A | 368 | −34.775 | 5.931 | 10.133 | 1.00 | 20.19 | C |
| ATOM | 5543 | CB | LEU | A | 368 | −33.783 | 5.413 | 9.085 | 1.00 | 20.08 | C |
| ATOM | 5546 | CG | LEU | A | 368 | −32.743 | 4.363 | 9.514 | 1.00 | 19.30 | C |
| ATOM | 5548 | CD1 | LEU | A | 368 | −33.384 | 3.227 | 10.260 | 1.00 | 18.66 | C |
| ATOM | 5552 | CD2 | LEU | A | 368 | −31.968 | 3.807 | 8.319 | 1.00 | 18.16 | C |
| ATOM | 5556 | C | LEU | A | 368 | −34.063 | 6.812 | 11.128 | 1.00 | 20.41 | C |
| ATOM | 5557 | O | LEU | A | 368 | −33.842 | 6.407 | 12.257 | 1.00 | 20.01 | O |
| ATOM | 5559 | N | GLN | A | 369 | −33.751 | 8.036 | 10.711 | 1.00 | 20.89 | N |

TABLE 3-7-continued

Coordinates of *P. tremuloides IspS*

| | | | | | | | | | | | |
|---|---|---|---|---|---|---|---|---|---|---|---|
| ATOM | 5560 | CA | GLN | A | 369 | −33.037 | 8.970 | 11.564 | 1.00 | 21.49 | C |
| ATOM | 5562 | CB | GLN | A | 369 | −32.782 | 10.280 | 10.832 | 1.00 | 21.58 | C |
| ATOM | 5565 | CG | GLN | A | 369 | −32.071 | 11.359 | 11.677 | 1.00 | 21.20 | C |
| ATOM | 5568 | CD | GLN | A | 369 | −30.639 | 11.006 | 11.976 | 1.00 | 20.04 | C |
| ATOM | 5569 | OE1 | GLN | A | 369 | −30.282 | 10.650 | 13.108 | 1.00 | 19.10 | O |
| ATOM | 5570 | NE2 | GLN | A | 369 | −29.803 | 11.095 | 10.956 | 1.00 | 18.75 | N |
| ATOM | 5573 | C | GLN | A | 369 | −33.763 | 9.265 | 12.870 | 1.00 | 22.21 | C |
| ATOM | 5574 | O | GLN | A | 369 | −33.122 | 9.343 | 13.909 | 1.00 | 22.41 | O |
| ATOM | 5576 | N | GLU | A | 370 | −35.080 | 9.455 | 12.822 | 1.00 | 23.05 | N |
| ATOM | 5577 | CA | GLU | A | 370 | −35.856 | 9.718 | 14.046 | 1.00 | 23.71 | C |
| ATOM | 5579 | CB | GLU | A | 370 | −37.329 | 10.041 | 13.726 | 1.00 | 24.04 | C |
| ATOM | 5582 | CG | GLU | A | 370 | −37.484 | 11.293 | 12.862 | 1.00 | 26.84 | C |
| ATOM | 5585 | CD | GLU | A | 370 | −38.897 | 11.910 | 12.834 | 1.00 | 30.36 | C |
| ATOM | 5586 | OE1 | GLU | A | 370 | −39.886 | 11.161 | 12.586 | 1.00 | 31.90 | O |
| ATOM | 5587 | OE2 | GLU | A | 370 | −38.992 | 13.164 | 13.014 | 1.00 | 31.62 | O |
| ATOM | 5588 | C | GLU | A | 370 | −35.755 | 8.523 | 14.994 | 1.00 | 23.60 | C |
| ATOM | 5589 | O | GLU | A | 370 | −35.534 | 8.689 | 16.199 | 1.00 | 23.33 | O |
| ATOM | 5591 | N | ALA | A | 371 | −35.904 | 7.322 | 14.435 | 1.00 | 23.72 | N |
| ATOM | 5592 | CA | ALA | A | 371 | −35.771 | 6.091 | 15.201 | 1.00 | 23.91 | C |
| ATOM | 5594 | CB | ALA | A | 371 | −35.991 | 4.868 | 14.312 | 1.00 | 23.76 | C |
| ATOM | 5598 | C | ALA | A | 371 | −34.392 | 6.051 | 15.840 | 1.00 | 24.20 | C |
| ATOM | 5599 | O | ALA | A | 371 | −34.277 | 5.804 | 17.035 | 1.00 | 24.54 | O |
| ATOM | 5601 | N | LYS | A | 372 | −33.355 | 6.333 | 15.049 | 1.00 | 24.38 | N |
| ATOM | 5602 | CA | LYS | A | 372 | −31.979 | 6.273 | 15.530 | 1.00 | 24.39 | C |
| ATOM | 5604 | CB | LYS | A | 372 | −30.970 | 6.466 | 14.393 | 1.00 | 24.43 | C |
| ATOM | 5607 | CG | LYS | A | 372 | −30.623 | 5.164 | 13.645 | 1.00 | 25.20 | C |
| ATOM | 5610 | CD | LYS | A | 372 | −29.188 | 5.149 | 13.069 | 1.00 | 26.09 | C |
| ATOM | 5613 | CE | LYS | A | 372 | −29.114 | 5.437 | 11.557 | 1.00 | 27.01 | C |
| ATOM | 5616 | NZ | LYS | A | 372 | −29.002 | 4.200 | 10.709 | 1.00 | 26.82 | N |
| ATOM | 5620 | C | LYS | A | 372 | −31.717 | 7.268 | 16.645 | 1.00 | 24.59 | C |
| ATOM | 5621 | O | LYS | A | 372 | −31.096 | 6.908 | 17.627 | 1.00 | 25.13 | O |
| ATOM | 5623 | N | TRP | A | 373 | −32.181 | 8.507 | 16.520 | 1.00 | 24.78 | N |
| ATOM | 5624 | CA | TRP | A | 373 | −32.006 | 9.473 | 17.610 | 1.00 | 24.90 | C |
| ATOM | 5626 | CB | TRP | A | 373 | −32.565 | 10.863 | 17.266 | 1.00 | 24.75 | C |
| ATOM | 5629 | CG | TRP | A | 373 | −31.701 | 11.677 | 16.338 | 1.00 | 23.59 | C |
| ATOM | 5630 | CD1 | TRP | A | 373 | −30.344 | 11.663 | 16.259 | 1.00 | 22.38 | C |
| ATOM | 5632 | NE1 | TRP | A | 373 | −29.915 | 12.539 | 15.298 | 1.00 | 21.59 | N |
| ATOM | 5634 | CE2 | TRP | A | 373 | −30.999 | 13.162 | 14.744 | 1.00 | 21.69 | C |
| ATOM | 5635 | CD2 | TRP | A | 373 | −32.147 | 12.644 | 15.376 | 1.00 | 22.41 | C |
| ATOM | 5636 | CE3 | TRP | A | 373 | −33.409 | 13.110 | 14.976 | 1.00 | 21.98 | C |
| ATOM | 5638 | CZ3 | TRP | A | 373 | −33.480 | 14.072 | 13.979 | 1.00 | 22.08 | C |
| ATOM | 5640 | CH2 | TRP | A | 373 | −32.313 | 14.567 | 13.366 | 1.00 | 22.31 | C |
| ATOM | 5642 | CZ2 | TRP | A | 373 | −31.067 | 14.124 | 13.736 | 1.00 | 21.87 | C |
| ATOM | 5644 | C | TRP | A | 373 | −32.678 | 8.970 | 18.881 | 1.00 | 25.53 | C |
| ATOM | 5645 | O | TRP | A | 373 | −32.101 | 9.072 | 19.972 | 1.00 | 25.99 | O |
| ATOM | 5647 | N | LEU | A | 374 | −33.881 | 8.420 | 18.739 | 1.00 | 25.84 | N |
| ATOM | 5648 | CA | LEU | A | 374 | −34.667 | 7.980 | 19.893 | 1.00 | 26.29 | C |
| ATOM | 5650 | CB | LEU | A | 374 | −36.070 | 7.562 | 19.443 | 1.00 | 26.32 | C |
| ATOM | 5653 | CG | LEU | A | 374 | −37.227 | 7.646 | 20.444 | 1.00 | 26.39 | C |
| ATOM | 5655 | CD1 | LEU | A | 374 | −38.456 | 8.286 | 19.761 | 1.00 | 26.95 | C |
| ATOM | 5659 | CD2 | LEU | A | 374 | −37.583 | 6.281 | 21.050 | 1.00 | 26.24 | C |
| ATOM | 5663 | C | LEU | A | 374 | −33.982 | 6.824 | 20.623 | 1.00 | 26.77 | C |
| ATOM | 5664 | O | LEU | A | 374 | −33.995 | 6.758 | 21.860 | 1.00 | 26.95 | O |
| ATOM | 5666 | N | TYR | A | 375 | −33.383 | 5.919 | 19.854 | 1.00 | 27.23 | N |
| ATOM | 5667 | CA | TYR | A | 375 | −32.706 | 4.761 | 20.425 | 1.00 | 27.74 | C |
| ATOM | 5669 | CB | TYR | A | 375 | −32.195 | 3.814 | 19.328 | 1.00 | 27.78 | C |
| ATOM | 5672 | CG | TYR | A | 375 | −31.526 | 2.556 | 19.848 | 1.00 | 28.74 | C |
| ATOM | 5673 | CD1 | TYR | A | 375 | −32.264 | 1.394 | 20.090 | 1.00 | 29.61 | C |
| ATOM | 5675 | CE1 | TYR | A | 375 | −31.652 | .232 | 20.573 | 1.00 | 29.89 | C |
| ATOM | 5677 | CZ | TYR | A | 375 | −30.287 | .226 | 20.817 | 1.00 | 30.15 | C |
| ATOM | 5678 | OH | TYR | A | 375 | −29.676 | −.917 | 21.286 | 1.00 | 30.57 | O |
| ATOM | 5680 | CE2 | TYR | A | 375 | −29.530 | 1.367 | 20.579 | 1.00 | 30.05 | C |
| ATOM | 5682 | CD2 | TYR | A | 375 | −30.152 | 2.522 | 20.096 | 1.00 | 29.74 | C |
| ATOM | 5684 | C | TYR | A | 375 | −31.553 | 5.248 | 21.275 | 1.00 | 27.97 | C |
| ATOM | 5685 | O | TYR | A | 375 | −31.404 | 4.837 | 22.422 | 1.00 | 28.00 | O |
| ATOM | 5687 | N | ASN | A | 376 | −30.763 | 6.158 | 20.719 | 1.00 | 28.32 | N |
| ATOM | 5688 | CA | ASN | A | 376 | −29.531 | 6.590 | 21.368 | 1.00 | 28.71 | C |
| ATOM | 5690 | CB | ASN | A | 376 | −28.569 | 7.161 | 20.329 | 1.00 | 28.60 | C |
| ATOM | 5693 | CG | ASN | A | 376 | −28.215 | 6.159 | 19.255 | 1.00 | 28.32 | C |
| ATOM | 5694 | OD1 | ASN | A | 376 | −27.961 | 4.977 | 19.527 | 1.00 | 25.72 | O |
| ATOM | 5695 | ND2 | ASN | A | 376 | −28.195 | 6.631 | 18.015 | 1.00 | 29.29 | N |
| ATOM | 5698 | C | ASN | A | 376 | −29.728 | 7.617 | 22.484 | 1.00 | 29.05 | C |
| ATOM | 5699 | O | ASN | A | 376 | −28.752 | 8.021 | 23.136 | 1.00 | 29.03 | O |
| ATOM | 5701 | N | LYS | A | 377 | −30.977 | 8.021 | 22.716 | 1.00 | 29.16 | N |
| ATOM | 5702 | CA | LYS | A | 377 | −31.254 | 9.178 | 23.549 | 1.00 | 29.27 | C |
| ATOM | 5704 | CB | LYS | A | 377 | −31.051 | 8.879 | 25.050 | 1.00 | 29.52 | C |
| ATOM | 5707 | CG | LYS | A | 377 | −32.202 | 8.112 | 25.723 | 1.00 | 30.36 | C |
| ATOM | 5710 | CD | LYS | A | 377 | −32.202 | 6.638 | 25.340 | 1.00 | 31.54 | C |

TABLE 3-7-continued

Coordinates of *P. tremuloides IspS*

| | | | | | | | | | | | |
|---|---|---|---|---|---|---|---|---|---|---|---|
| ATOM | 5713 | CE | LYS | A | 377 | −33.322 | 5.862 | 26.031 | 1.00 | 32.30 | C |
| ATOM | 5716 | NZ | LYS | A | 377 | −33.559 | 4.509 | 25.411 | 1.00 | 32.13 | N |
| ATOM | 5720 | C | LYS | A | 377 | −30.337 | 10.299 | 23.080 | 1.00 | 28.92 | C |
| ATOM | 5721 | O | LYS | A | 377 | −29.590 | 10.867 | 23.875 | 1.00 | 28.94 | O |
| ATOM | 5723 | N | SER | A | 378 | −30.377 | 10.575 | 21.776 | 1.00 | 28.52 | N |
| ATOM | 5724 | CA | SER | A | 378 | −29.652 | 11.700 | 21.201 | 1.00 | 28.30 | C |
| ATOM | 5726 | CB | SER | A | 378 | −29.623 | 11.620 | 19.678 | 1.00 | 28.33 | C |
| ATOM | 5729 | OG | SER | A | 378 | −28.919 | 10.482 | 19.237 | 1.00 | 29.36 | O |
| ATOM | 5731 | C | SER | A | 378 | −30.355 | 12.977 | 21.594 | 1.00 | 27.97 | C |
| ATOM | 5732 | O | SER | A | 378 | −31.483 | 12.947 | 22.108 | 1.00 | 27.91 | O |
| ATOM | 5734 | N | THR | A | 379 | −29.684 | 14.098 | 21.344 | 1.00 | 27.60 | N |
| ATOM | 5735 | CA | THR | A | 379 | −30.257 | 15.422 | 21.581 | 1.00 | 27.24 | C |
| ATOM | 5737 | CB | THR | A | 379 | −29.929 | 15.950 | 23.002 | 1.00 | 27.23 | C |
| ATOM | 5739 | OG1 | THR | A | 379 | −28.512 | 16.102 | 23.158 | 1.00 | 26.85 | O |
| ATOM | 5741 | CG2 | THR | A | 379 | −30.467 | 15.007 | 24.067 | 1.00 | 27.48 | C |
| ATOM | 5745 | C | THR | A | 379 | −29.738 | 16.414 | 20.548 | 1.00 | 26.83 | C |
| ATOM | 5746 | O | THR | A | 379 | −28.834 | 17.190 | 20.844 | 1.00 | 26.69 | O |
| ATOM | 5748 | N | PRO | A | 380 | −30.305 | 16.390 | 19.331 | 1.00 | 26.56 | N |
| ATOM | 5749 | CA | PRO | A | 380 | −29.884 | 17.315 | 18.278 | 1.00 | 26.52 | C |
| ATOM | 5751 | CB | PRO | A | 380 | −30.380 | 16.648 | 16.992 | 1.00 | 26.46 | C |
| ATOM | 5754 | CG | PRO | A | 380 | −31.281 | 15.533 | 17.408 | 1.00 | 26.41 | C |
| ATOM | 5757 | CD | PRO | A | 380 | −31.395 | 15.508 | 18.887 | 1.00 | 26.53 | C |
| ATOM | 5760 | C | PRO | A | 380 | −30.469 | 18.728 | 18.386 | 1.00 | 26.55 | C |
| ATOM | 5761 | O | PRO | A | 380 | −31.472 | 18.966 | 19.063 | 1.00 | 26.69 | O |
| ATOM | 5762 | N | THR | A | 381 | −29.840 | 19.661 | 17.692 | 1.00 | 26.51 | N |
| ATOM | 5763 | CA | THR | A | 381 | −30.299 | 21.034 | 17.699 | 1.00 | 26.51 | C |
| ATOM | 5765 | CB | THR | A | 381 | −29.261 | 21.955 | 17.033 | 1.00 | 26.99 | C |
| ATOM | 5767 | OG1 | THR | A | 381 | −28.919 | 21.431 | 15.732 | 1.00 | 27.65 | O |
| ATOM | 5769 | CG2 | THR | A | 381 | −28.003 | 22.082 | 17.930 | 1.00 | 26.41 | C |
| ATOM | 5773 | C | THR | A | 381 | −31.635 | 21.167 | 16.970 | 1.00 | 26.06 | C |
| ATOM | 5774 | O | THR | A | 381 | −31.972 | 20.347 | 16.112 | 1.00 | 26.03 | O |
| ATOM | 5776 | N | PHE | A | 382 | −32.386 | 22.218 | 17.294 | 1.00 | 25.52 | N |
| ATOM | 5777 | CA | PHE | A | 382 | −33.681 | 22.436 | 16.654 | 1.00 | 24.83 | C |
| ATOM | 5779 | CB | PHE | A | 382 | −34.284 | 23.793 | 17.011 | 1.00 | 24.53 | C |
| ATOM | 5782 | CG | PHE | A | 382 | −35.495 | 24.113 | 16.211 | 1.00 | 23.77 | C |
| ATOM | 5783 | CD1 | PHE | A | 382 | −36.745 | 23.715 | 16.637 | 1.00 | 24.50 | C |
| ATOM | 5785 | CE1 | PHE | A | 382 | −37.873 | 23.977 | 15.878 | 1.00 | 24.49 | C |
| ATOM | 5787 | CZ | PHE | A | 382 | −37.744 | 24.630 | 14.673 | 1.00 | 24.41 | C |
| ATOM | 5789 | CE2 | PHE | A | 382 | −36.490 | 25.014 | 14.235 | 1.00 | 23.88 | C |
| ATOM | 5791 | CD2 | PHE | A | 382 | −35.381 | 24.752 | 14.999 | 1.00 | 23.29 | C |
| ATOM | 5793 | C | PHE | A | 382 | −33.542 | 22.342 | 15.150 | 1.00 | 24.49 | C |
| ATOM | 5794 | O | PHE | A | 382 | −34.361 | 21.731 | 14.485 | 1.00 | 24.32 | O |
| ATOM | 5796 | N | ASP | A | 383 | −32.498 | 22.969 | 14.627 | 1.00 | 24.42 | N |
| ATOM | 5797 | CA | ASP | A | 383 | −32.257 | 23.005 | 13.190 | 1.00 | 24.19 | C |
| ATOM | 5799 | CB | ASP | A | 383 | −31.101 | 23.966 | 12.867 | 1.00 | 24.21 | C |
| ATOM | 5802 | CG | ASP | A | 383 | −31.473 | 25.423 | 13.050 | 1.00 | 23.72 | C |
| ATOM | 5803 | OD1 | ASP | A | 383 | −32.634 | 25.794 | 12.837 | 1.00 | 25.60 | O |
| ATOM | 5804 | OD2 | ASP | A | 383 | −30.594 | 26.220 | 13.383 | 1.00 | 24.03 | O |
| ATOM | 5805 | C | ASP | A | 383 | −31.982 | 21.612 | 12.599 | 1.00 | 24.06 | C |
| ATOM | 5806 | O | ASP | A | 383 | −32.393 | 21.342 | 11.473 | 1.00 | 24.00 | O |
| ATOM | 5808 | N | ASP | A | 384 | −31.298 | 20.739 | 13.336 | 1.00 | 23.78 | N |
| ATOM | 5809 | CA | ASP | A | 384 | −31.078 | 19.379 | 12.848 | 1.00 | 24.11 | C |
| ATOM | 5811 | CB | ASP | A | 384 | −29.981 | 18.651 | 13.632 | 1.00 | 24.54 | C |
| ATOM | 5814 | CG | ASP | A | 384 | −28.573 | 19.009 | 13.159 | 1.00 | 26.32 | C |
| ATOM | 5815 | OD1 | ASP | A | 384 | −28.441 | 19.852 | 12.232 | 1.00 | 28.55 | O |
| ATOM | 5816 | OD2 | ASP | A | 384 | −27.599 | 18.451 | 13.728 | 1.00 | 27.18 | O |
| ATOM | 5817 | C | ASP | A | 384 | −32.351 | 18.550 | 12.905 | 1.00 | 23.83 | C |
| ATOM | 5818 | O | ASP | A | 384 | −32.670 | 17.825 | 11.955 | 1.00 | 24.24 | O |
| ATOM | 5820 | N | TYR | A | 385 | −33.070 | 18.637 | 14.017 | 1.00 | 23.31 | N |
| ATOM | 5821 | CA | TYR | A | 385 | −34.294 | 17.861 | 14.179 | 1.00 | 22.89 | C |
| ATOM | 5823 | CB | TYR | A | 385 | −34.833 | 17.979 | 15.608 | 1.00 | 22.86 | C |
| ATOM | 5826 | CG | TYR | A | 385 | −36.144 | 17.245 | 15.807 | 1.00 | 22.65 | C |
| ATOM | 5827 | CD1 | TYR | A | 385 | −36.163 | 15.868 | 16.030 | 1.00 | 22.36 | C |
| ATOM | 5829 | CE1 | TYR | A | 385 | −37.351 | 15.189 | 16.206 | 1.00 | 22.77 | C |
| ATOM | 5831 | CZ | TYR | A | 385 | −38.545 | 15.887 | 16.146 | 1.00 | 23.54 | C |
| ATOM | 5832 | OH | TYR | A | 385 | −39.733 | 15.212 | 16.309 | 1.00 | 24.38 | O |
| ATOM | 5834 | CE2 | TYR | A | 385 | −38.554 | 17.258 | 15.913 | 1.00 | 22.76 | C |
| ATOM | 5836 | CD2 | TYR | A | 385 | −37.360 | 17.923 | 15.744 | 1.00 | 22.12 | C |
| ATOM | 5838 | C | TYR | A | 385 | −35.375 | 18.299 | 13.190 | 1.00 | 22.55 | C |
| ATOM | 5839 | O | TYR | A | 385 | −36.050 | 17.467 | 12.584 | 1.00 | 22.85 | O |
| ATOM | 5841 | N | PHE | A | 386 | −35.537 | 19.609 | 13.042 | 1.00 | 22.08 | N |
| ATOM | 5842 | CA | PHE | A | 386 | −36.626 | 20.155 | 12.248 | 1.00 | 21.62 | C |
| ATOM | 5844 | CB | PHE | A | 386 | −36.857 | 21.628 | 12.568 | 1.00 | 21.73 | C |
| ATOM | 5847 | CG | PHE | A | 386 | −38.033 | 22.209 | 11.851 | 1.00 | 21.54 | C |
| ATOM | 5848 | CD1 | PHE | A | 386 | −39.311 | 21.933 | 12.273 | 1.00 | 21.29 | C |
| ATOM | 5850 | CE1 | PHE | A | 386 | −40.380 | 22.444 | 11.623 | 1.00 | 22.11 | C |
| ATOM | 5852 | CZ | PHE | A | 386 | −40.193 | 23.240 | 10.517 | 1.00 | 23.28 | C |
| ATOM | 5854 | CE2 | PHE | A | 386 | −38.920 | 23.502 | 10.069 | 1.00 | 23.10 | C |

TABLE 3-7-continued

Coordinates of *P. tremuloides IspS*

| | | | | | | | | | | | |
|---|---|---|---|---|---|---|---|---|---|---|---|
| ATOM | 5856 | CD2 | PHE | A | 386 | −37.853 | 22.989 | 10.737 | 1.00 | 22.15 | C |
| ATOM | 5858 | C | PHE | A | 386 | −36.369 | 19.987 | 10.769 | 1.00 | 21.09 | C |
| ATOM | 5859 | O | PHE | A | 386 | −37.278 | 19.700 | 10.006 | 1.00 | 20.91 | O |
| ATOM | 5861 | N | GLY | A | 387 | −35.127 | 20.177 | 10.362 | 1.00 | 20.68 | N |
| ATOM | 5862 | CA | GLY | A | 387 | −34.747 | 19.917 | 8.985 | 1.00 | 20.43 | C |
| ATOM | 5865 | C | GLY | A | 387 | −35.151 | 18.521 | 8.544 | 1.00 | 19.95 | C |
| ATOM | 5866 | O | GLY | A | 387 | −35.553 | 18.327 | 7.398 | 1.00 | 20.24 | O |
| ATOM | 5868 | N | ASN | A | 388 | −35.032 | 17.554 | 9.451 | 1.00 | 19.12 | N |
| ATOM | 5869 | CA | ASN | A | 388 | −35.451 | 16.182 | 9.202 | 1.00 | 18.73 | C |
| ATOM | 5871 | CB | ASN | A | 388 | −34.744 | 15.272 | 10.205 | 1.00 | 18.90 | C |
| ATOM | 5874 | CG | ASN | A | 388 | −34.863 | 13.795 | 9.871 | 1.00 | 18.35 | C |
| ATOM | 5875 | OD1 | ASN | A | 388 | −34.163 | 13.284 | 8.993 | 1.00 | 17.24 | O |
| ATOM | 5876 | ND2 | ASN | A | 388 | −35.714 | 13.092 | 10.614 | 1.00 | 17.01 | N |
| ATOM | 5879 | C | ASN | A | 388 | −36.968 | 16.033 | 9.350 | 1.00 | 18.65 | C |
| ATOM | 5880 | O | ASN | A | 388 | −37.624 | 15.370 | 8.551 | 1.00 | 18.82 | O |
| ATOM | 5882 | N | ALA | A | 389 | −37.527 | 16.670 | 10.371 | 1.00 | 18.38 | N |
| ATOM | 5883 | CA | ALA | A | 389 | −38.926 | 16.477 | 10.728 | 1.00 | 18.02 | C |
| ATOM | 5885 | CB | ALA | A | 389 | −39.203 | 17.107 | 12.084 | 1.00 | 17.83 | C |
| ATOM | 5889 | C | ALA | A | 389 | −39.949 | 16.966 | 9.700 | 1.00 | 17.90 | C |
| ATOM | 5890 | O | ALA | A | 389 | −41.095 | 16.544 | 9.760 | 1.00 | 17.74 | O |
| ATOM | 5892 | N | TRP | A | 390 | −39.585 | 17.860 | 8.783 | 1.00 | 18.11 | N |
| ATOM | 5893 | CA | TRP | A | 390 | −40.543 | 18.254 | 7.731 | 1.00 | 18.46 | C |
| ATOM | 5895 | CB | TRP | A | 390 | −40.459 | 19.737 | 7.329 | 1.00 | 18.59 | C |
| ATOM | 5898 | CG | TRP | A | 390 | −39.143 | 20.224 | 6.821 | 1.00 | 19.26 | C |
| ATOM | 5899 | CD1 | TRP | A | 390 | −38.224 | 20.947 | 7.519 | 1.00 | 20.64 | C |
| ATOM | 5901 | NE1 | TRP | A | 390 | −37.138 | 21.224 | 6.729 | 1.00 | 20.62 | N |
| ATOM | 5903 | CE2 | TRP | A | 390 | −37.352 | 20.694 | 5.485 | 1.00 | 19.57 | C |
| ATOM | 5904 | CD2 | TRP | A | 390 | −38.607 | 20.066 | 5.504 | 1.00 | 19.15 | C |
| ATOM | 5905 | CE3 | TRP | A | 390 | −39.060 | 19.448 | 4.344 | 1.00 | 20.13 | C |
| ATOM | 5907 | CZ3 | TRP | A | 390 | −38.254 | 19.477 | 3.224 | 1.00 | 20.27 | C |
| ATOM | 5909 | CH2 | TRP | A | 390 | −37.017 | 20.110 | 3.239 | 1.00 | 19.38 | C |
| ATOM | 5911 | CZ2 | TRP | A | 390 | −36.549 | 20.724 | 4.356 | 1.00 | 19.49 | C |
| ATOM | 5913 | C | TRP | A | 390 | −40.407 | 17.343 | 6.527 | 1.00 | 18.73 | C |
| ATOM | 5914 | O | TRP | A | 390 | −41.369 | 17.143 | 5.788 | 1.00 | 18.32 | O |
| ATOM | 5916 | N | LYS | A | 391 | −39.200 | 16.806 | 6.336 | 1.00 | 19.30 | N |
| ATOM | 5917 | CA | LYS | A | 391 | −38.969 | 15.692 | 5.404 | 1.00 | 19.70 | C |
| ATOM | 5919 | CB | LYS | A | 391 | −37.459 | 15.392 | 5.244 | 1.00 | 19.92 | C |
| ATOM | 5922 | CG | LYS | A | 391 | −36.812 | 15.953 | 3.935 | 1.00 | 22.08 | C |
| ATOM | 5925 | CD | LYS | A | 391 | −35.257 | 16.217 | 4.040 | 1.00 | 23.92 | C |
| ATOM | 5928 | CE | LYS | A | 391 | −34.918 | 17.698 | 4.426 | 1.00 | 24.43 | C |
| ATOM | 5931 | NZ | LYS | A | 391 | −33.699 | 17.901 | 5.307 | 1.00 | 23.23 | N |
| ATOM | 5935 | C | LYS | A | 391 | −39.731 | 14.441 | 5.861 | 1.00 | 19.46 | C |
| ATOM | 5936 | O | LYS | A | 391 | −40.284 | 13.709 | 5.032 | 1.00 | 20.07 | O |
| ATOM | 5938 | N | SER | A | 392 | −39.793 | 14.202 | 7.170 | 1.00 | 18.95 | N |
| ATOM | 5939 | CA | SER | A | 392 | −40.455 | 12.998 | 7.666 | 1.00 | 18.63 | C |
| ATOM | 5941 | CB | SER | A | 392 | −39.850 | 12.508 | 9.000 | 1.00 | 18.75 | C |
| ATOM | 5944 | OG | SER | A | 392 | −40.314 | 13.230 | 10.126 | 1.00 | 18.94 | O |
| ATOM | 5946 | C | SER | A | 392 | −41.964 | 13.152 | 7.771 | 1.00 | 18.20 | C |
| ATOM | 5947 | O | SER | A | 392 | −42.654 | 12.182 | 8.031 | 1.00 | 18.12 | O |
| ATOM | 5949 | N | SER | A | 393 | −42.477 | 14.360 | 7.567 | 1.00 | 18.07 | N |
| ATOM | 5950 | CA | SER | A | 393 | −43.929 | 14.591 | 7.556 | 1.00 | 18.02 | C |
| ATOM | 5952 | CB | SER | A | 393 | −44.229 | 16.078 | 7.504 | 1.00 | 18.08 | C |
| ATOM | 5955 | OG | SER | A | 393 | −43.995 | 16.558 | 6.192 | 1.00 | 18.01 | O |
| ATOM | 5957 | C | SER | A | 393 | −44.594 | 13.971 | 6.340 | 1.00 | 17.87 | C |
| ATOM | 5958 | O | SER | A | 393 | −45.778 | 13.661 | 6.372 | 1.00 | 18.03 | O |
| ATOM | 5960 | N | SER | A | 394 | −43.823 | 13.841 | 5.264 | 1.00 | 17.69 | N |
| ATOM | 5961 | CA | SER | A | 394 | −44.284 | 13.306 | 3.989 | 1.00 | 17.59 | C |
| ATOM | 5963 | CB | SER | A | 394 | −45.329 | 12.180 | 4.149 | 1.00 | 17.61 | C |
| ATOM | 5966 | OG | SER | A | 394 | −46.648 | 12.681 | 4.294 | 1.00 | 17.18 | O |
| ATOM | 5968 | C | SER | A | 394 | −44.828 | 14.415 | 3.115 | 1.00 | 17.42 | C |
| ATOM | 5969 | O | SER | A | 394 | −45.345 | 14.146 | 2.024 | 1.00 | 17.31 | O |
| ATOM | 5971 | N | GLY | A | 395 | −44.711 | 15.654 | 3.592 | 1.00 | 17.23 | N |
| ATOM | 5972 | CA | GLY | A | 395 | −45.088 | 16.827 | 2.807 | 1.00 | 17.26 | C |
| ATOM | 5975 | C | GLY | A | 395 | −44.478 | 16.749 | 1.415 | 1.00 | 17.29 | C |
| ATOM | 5976 | O | GLY | A | 395 | −45.203 | 16.653 | .413 | 1.00 | 18.06 | O |
| ATOM | 5978 | N | PRO | A | 396 | −43.145 | 16.754 | 1.331 | 1.00 | 16.72 | N |
| ATOM | 5979 | CA | PRO | A | 396 | −42.582 | 16.610 | .006 | 1.00 | 16.40 | C |
| ATOM | 5981 | CB | PRO | A | 396 | −41.080 | 16.549 | .259 | 1.00 | 16.62 | C |
| ATOM | 5984 | CG | PRO | A | 396 | −40.903 | 16.749 | 1.775 | 1.00 | 17.11 | C |
| ATOM | 5987 | CD | PRO | A | 396 | −42.157 | 17.252 | 2.296 | 1.00 | 16.87 | C |
| ATOM | 5990 | C | PRO | A | 396 | −43.053 | 15.374 | −.748 | 1.00 | 15.89 | C |
| ATOM | 5991 | O | PRO | A | 396 | −43.501 | 15.498 | −1.894 | 1.00 | 15.90 | O |
| ATOM | 5992 | N | LEU | A | 397 | −42.973 | 14.197 | −.135 | 1.00 | 15.27 | N |
| ATOM | 5993 | CA | LEU | A | 397 | −43.287 | 12.976 | −.886 | 1.00 | 14.57 | C |
| ATOM | 5995 | CB | LEU | A | 397 | −43.332 | 11.733 | −.008 | 1.00 | 14.36 | C |
| ATOM | 5998 | CG | LEU | A | 397 | −43.541 | 10.431 | −.781 | 1.00 | 14.02 | C |
| ATOM | 6000 | CD1 | LEU | A | 397 | −42.690 | 9.348 | −.206 | 1.00 | 15.04 | C |
| ATOM | 6004 | CD2 | LEU | A | 397 | −44.985 | 9.976 | −.805 | 1.00 | 13.75 | C |

TABLE 3-7-continued

| Coordinates of *P. tremuloides IspS* | | | | | | | | | | | |
|---|---|---|---|---|---|---|---|---|---|---|---|
| ATOM | 6008 | C | LEU | A | 397 | −44.618 | 13.182 | −1.542 | 1.00 | 14.39 | C |
| ATOM | 6009 | O | LEU | A | 397 | −44.736 | 12.999 | −2.745 | 1.00 | 14.57 | O |
| ATOM | 6011 | N | GLN | A | 398 | −45.604 | 13.607 | −.751 | 1.00 | 14.08 | N |
| ATOM | 6012 | CA | GLN | A | 398 | −46.962 | 13.828 | −1.245 | 1.00 | 13.91 | C |
| ATOM | 6014 | CB | GLN | A | 398 | −47.860 | 14.363 | −.136 | 1.00 | 13.99 | C |
| ATOM | 6017 | CG | GLN | A | 398 | −48.274 | 13.321 | .909 | 1.00 | 14.01 | C |
| ATOM | 6020 | CD | GLN | A | 398 | −49.189 | 13.902 | 1.983 | 1.00 | 13.41 | C |
| ATOM | 6021 | OE1 | GLN | A | 398 | −49.941 | 14.847 | 1.740 | 1.00 | 14.65 | O |
| ATOM | 6022 | NE2 | GLN | A | 398 | −49.122 | 13.344 | 3.168 | 1.00 | 12.17 | N |
| ATOM | 6025 | C | GLN | A | 398 | −47.015 | 14.800 | −2.403 | 1.00 | 13.84 | C |
| ATOM | 6026 | O | GLN | A | 398 | −47.677 | 14.547 | −3.396 | 1.00 | 13.46 | O |
| ATOM | 6028 | N | LEU | A | 399 | −46.319 | 15.922 | −2.272 | 1.00 | 14.11 | N |
| ATOM | 6029 | CA | LEU | A | 399 | −46.359 | 16.942 | −3.315 | 1.00 | 14.37 | C |
| ATOM | 6031 | CB | LEU | A | 399 | −45.900 | 18.282 | −2.756 | 1.00 | 14.26 | C |
| ATOM | 6034 | CG | LEU | A | 399 | −46.882 | 18.830 | −1.704 | 1.00 | 14.44 | C |
| ATOM | 6036 | CD1 | LEU | A | 399 | −46.250 | 19.960 | −.919 | 1.00 | 16.43 | C |
| ATOM | 6040 | CD2 | LEU | A | 399 | −48.191 | 19.304 | −2.317 | 1.00 | 12.20 | C |
| ATOM | 6044 | C | LEU | A | 399 | −45.582 | 16.525 | −4.578 | 1.00 | 14.68 | C |
| ATOM | 6045 | O | LEU | A | 399 | −46.043 | 16.784 | −5.687 | 1.00 | 14.70 | O |
| ATOM | 6047 | N | ILE | A | 400 | −44.443 | 15.844 | −4.419 | 1.00 | 14.92 | N |
| ATOM | 6048 | CA | ILE | A | 400 | −43.748 | 15.221 | −5.564 | 1.00 | 15.08 | C |
| ATOM | 6050 | CB | ILE | A | 400 | −42.549 | 14.355 | −5.129 | 1.00 | 15.35 | C |
| ATOM | 6052 | CG1 | ILE | A | 400 | −41.406 | 15.254 | −4.611 | 1.00 | 16.83 | C |
| ATOM | 6055 | CD1 | ILE | A | 400 | −40.234 | 14.490 | −3.958 | 1.00 | 17.18 | C |
| ATOM | 6059 | CG2 | ILE | A | 400 | −42.060 | 13.486 | −6.292 | 1.00 | 14.03 | C |
| ATOM | 6063 | C | ILE | A | 400 | −44.682 | 14.329 | −6.358 | 1.00 | 15.08 | C |
| ATOM | 6064 | O | ILE | A | 400 | −44.672 | 14.362 | −7.574 | 1.00 | 15.18 | O |
| ATOM | 6066 | N | PHE | A | 401 | −45.474 | 13.524 | −5.650 | 1.00 | 15.16 | N |
| ATOM | 6067 | CA | PHE | A | 401 | −46.501 | 12.674 | −6.258 | 1.00 | 14.90 | C |
| ATOM | 6069 | CB | PHE | A | 401 | −47.052 | 11.663 | −5.240 | 1.00 | 14.51 | C |
| ATOM | 6072 | CG | PHE | A | 401 | −46.294 | 10.378 | −5.201 | 1.00 | 12.92 | C |
| ATOM | 6073 | CD1 | PHE | A | 401 | −46.727 | 9.282 | −5.931 | 1.00 | 11.98 | C |
| ATOM | 6075 | CE1 | PHE | A | 401 | −46.032 | 8.093 | −5.917 | 1.00 | 11.20 | C |
| ATOM | 6077 | CZ | PHE | A | 401 | −44.881 | 7.985 | −5.165 | 1.00 | 12.03 | C |
| ATOM | 6079 | CE2 | PHE | A | 401 | −44.431 | 9.078 | −4.428 | 1.00 | 11.98 | C |
| ATOM | 6081 | CD2 | PHE | A | 401 | −45.143 | 10.263 | −4.453 | 1.00 | 12.09 | C |
| ATOM | 6083 | C | PHE | A | 401 | −47.641 | 13.509 | −6.806 | 1.00 | 15.39 | C |
| ATOM | 6084 | O | PHE | A | 401 | −48.183 | 13.215 | −7.858 | 1.00 | 15.51 | O |
| ATOM | 6086 | N | ALA | A | 402 | −48.022 | 14.545 | −6.080 | 1.00 | 16.15 | N |
| ATOM | 6087 | CA | ALA | A | 402 | −49.110 | 15.393 | −6.525 | 1.00 | 16.90 | C |
| ATOM | 6089 | CB | ALA | A | 402 | −49.391 | 16.473 | −5.505 | 1.00 | 16.99 | C |
| ATOM | 6093 | C | ALA | A | 402 | −48.722 | 16.003 | −7.856 | 1.00 | 17.50 | C |
| ATOM | 6094 | O | ALA | A | 402 | −49.549 | 16.100 | −8.770 | 1.00 | 17.48 | O |
| ATOM | 6096 | N | TYR | A | 403 | −47.444 | 16.367 | −7.963 | 1.00 | 18.28 | N |
| ATOM | 6097 | CA | TYR | A | 403 | −46.916 | 17.046 | −9.142 | 1.00 | 18.94 | C |
| ATOM | 6099 | CB | TYR | A | 403 | −45.412 | 17.252 | −9.043 | 1.00 | 19.03 | C |
| ATOM | 6102 | CG | TYR | A | 403 | −44.823 | 17.801 | −10.314 | 1.00 | 19.79 | C |
| ATOM | 6103 | CD1 | TYR | A | 403 | −44.973 | 19.138 | −10.652 | 1.00 | 20.80 | C |
| ATOM | 6105 | CE1 | TYR | A | 403 | −44.436 | 19.643 | −11.827 | 1.00 | 20.73 | C |
| ATOM | 6107 | CZ | TYR | A | 403 | −43.759 | 18.804 | −12.674 | 1.00 | 21.16 | C |
| ATOM | 6108 | OH | TYR | A | 403 | −43.231 | 19.283 | −13.836 | 1.00 | 22.98 | O |
| ATOM | 6110 | CE2 | TYR | A | 403 | −43.608 | 17.476 | −12.370 | 1.00 | 21.23 | C |
| ATOM | 6112 | CD2 | TYR | A | 403 | −44.137 | 16.980 | −11.195 | 1.00 | 20.93 | C |
| ATOM | 6114 | C | TYR | A | 403 | −47.198 | 16.293 | −10.413 | 1.00 | 19.39 | C |
| ATOM | 6115 | O | TYR | A | 403 | −47.567 | 16.904 | −11.422 | 1.00 | 19.57 | O |
| ATOM | 6117 | N | PHE | A | 404 | −47.023 | 14.976 | −10.376 | 1.00 | 19.74 | N |
| ATOM | 6118 | CA | PHE | A | 404 | −47.239 | 14.177 | −11.573 | 1.00 | 20.35 | C |
| ATOM | 6120 | CB | PHE | A | 404 | −46.533 | 12.841 | −11.466 | 1.00 | 19.96 | C |
| ATOM | 6123 | CG | PHE | A | 404 | −45.048 | 12.971 | −11.387 | 1.00 | 18.81 | C |
| ATOM | 6124 | CD1 | PHE | A | 404 | −44.292 | 13.115 | −12.528 | 1.00 | 17.42 | C |
| ATOM | 6126 | CE1 | PHE | A | 404 | −42.935 | 13.239 | −12.457 | 1.00 | 17.24 | C |
| ATOM | 6128 | CZ | PHE | A | 404 | −42.312 | 13.237 | −11.237 | 1.00 | 17.40 | C |
| ATOM | 6130 | CE2 | PHE | A | 404 | −43.056 | 13.106 | −10.093 | 1.00 | 17.72 | C |
| ATOM | 6132 | CD2 | PHE | A | 404 | −44.413 | 12.975 | −10.170 | 1.00 | 17.93 | C |
| ATOM | 6134 | C | PHE | A | 404 | −48.713 | 13.994 | −11.894 | 1.00 | 21.59 | C |
| ATOM | 6135 | O | PHE | A | 404 | −49.072 | 13.717 | −13.046 | 1.00 | 21.71 | O |
| ATOM | 6137 | N | ALA | A | 405 | −49.572 | 14.169 | −10.896 | 1.00 | 22.87 | N |
| ATOM | 6138 | CA | ALA | A | 405 | −50.990 | 13.939 | −11.099 | 1.00 | 24.06 | C |
| ATOM | 6140 | CB | ALA | A | 405 | −51.604 | 13.408 | −9.833 | 1.00 | 24.15 | C |
| ATOM | 6144 | C | ALA | A | 405 | −51.724 | 15.192 | −11.556 | 1.00 | 25.21 | C |
| ATOM | 6145 | O | ALA | A | 405 | −52.876 | 15.114 | −11.939 | 1.00 | 25.51 | O |
| ATOM | 6147 | N | VAL | A | 406 | −51.056 | 16.336 | −11.530 | 1.00 | 26.52 | N |
| ATOM | 6148 | CA | VAL | A | 406 | −51.713 | 17.617 | −11.759 | 1.00 | 27.68 | C |
| ATOM | 6150 | CB | VAL | A | 406 | −51.694 | 18.406 | −10.434 | 1.00 | 27.60 | C |
| ATOM | 6152 | CG1 | VAL | A | 406 | −51.654 | 19.913 | −10.663 | 1.00 | 28.07 | C |
| ATOM | 6156 | CG2 | VAL | A | 406 | −52.883 | 18.009 | −9.596 | 1.00 | 27.41 | C |
| ATOM | 6160 | C | VAL | A | 406 | −51.097 | 18.429 | −12.925 | 1.00 | 29.10 | C |
| ATOM | 6161 | O | VAL | A | 406 | −51.810 | 19.104 | −13.678 | 1.00 | 28.53 | O |

TABLE 3-7-continued

Coordinates of *P. tremuloides IspS*

| | | | | | | | | | | | |
|---|---|---|---|---|---|---|---|---|---|---|---|
| ATOM | 6163 | N | VAL | A | 407 | −49.772 | 18.356 | −13.059 | 1.00 | 30.90 | N |
| ATOM | 6164 | CA | VAL | A | 407 | −49.052 | 19.003 | −14.151 | 1.00 | 32.15 | C |
| ATOM | 6166 | CB | VAL | A | 407 | −47.574 | 19.228 | −13.777 | 1.00 | 32.25 | C |
| ATOM | 6168 | CG1 | VAL | A | 407 | −46.770 | 19.780 | −14.964 | 1.00 | 32.22 | C |
| ATOM | 6172 | CG2 | VAL | A | 407 | −47.490 | 20.154 | −12.583 | 1.00 | 32.25 | C |
| ATOM | 6176 | C | VAL | A | 407 | −49.134 | 18.160 | −15.421 | 1.00 | 33.36 | C |
| ATOM | 6177 | O | VAL | A | 407 | −48.688 | 17.009 | −15.454 | 1.00 | 33.40 | O |
| ATOM | 6179 | N | GLN | A | 408 | −49.693 | 18.767 | −16.463 | 1.00 | 34.93 | N |
| ATOM | 6180 | CA | GLN | A | 408 | −49.930 | 18.102 | −17.749 | 1.00 | 36.16 | C |
| ATOM | 6182 | CB | GLN | A | 408 | −50.779 | 19.016 | −18.638 | 1.00 | 36.63 | C |
| ATOM | 6185 | CG | GLN | A | 408 | −51.625 | 18.270 | −19.672 | 1.00 | 38.95 | C |
| ATOM | 6188 | CD | GLN | A | 408 | −52.991 | 18.930 | −19.887 | 1.00 | 41.80 | C |
| ATOM | 6189 | OE1 | GLN | A | 408 | −53.739 | 19.150 | −18.921 | 1.00 | 43.40 | O |
| ATOM | 6190 | NE2 | GLN | A | 408 | −53.323 | 19.244 | −21.151 | 1.00 | 41.68 | N |
| ATOM | 6193 | C | GLN | A | 408 | −48.630 | 17.725 | −18.470 | 1.00 | 36.22 | C |
| ATOM | 6194 | O | GLN | A | 408 | −48.456 | 16.588 | −18.920 | 1.00 | 35.86 | O |
| ATOM | 6196 | N | ASN | A | 409 | −47.726 | 18.694 | −18.578 | 1.00 | 36.64 | N |
| ATOM | 6197 | CA | ASN | A | 409 | −46.400 | 18.441 | −19.136 | 1.00 | 36.85 | C |
| ATOM | 6199 | CB | ASN | A | 409 | −46.134 | 19.306 | −20.373 | 1.00 | 36.73 | C |
| ATOM | 6202 | CG | ASN | A | 409 | −46.808 | 18.752 | −21.604 | 1.00 | 36.19 | C |
| ATOM | 6203 | OD1 | ASN | A | 409 | −46.178 | 18.072 | −22.420 | 1.00 | 35.00 | O |
| ATOM | 6204 | ND2 | ASN | A | 409 | −48.110 | 18.994 | −21.720 | 1.00 | 34.99 | N |
| ATOM | 6207 | C | ASN | A | 409 | −45.312 | 18.613 | −18.095 | 1.00 | 36.96 | C |
| ATOM | 6208 | O | ASN | A | 409 | −45.032 | 19.720 | −17.618 | 1.00 | 36.81 | O |
| ATOM | 6210 | N | ILE | A | 410 | −44.713 | 17.488 | −17.734 | 1.00 | 37.10 | N |
| ATOM | 6211 | CA | ILE | A | 410 | −43.625 | 17.508 | −16.792 | 1.00 | 37.27 | C |
| ATOM | 6213 | CB | ILE | A | 410 | −43.265 | 16.092 | −16.295 | 1.00 | 37.38 | C |
| ATOM | 6215 | CG1 | ILE | A | 410 | −42.745 | 15.209 | −17.426 | 1.00 | 37.84 | C |
| ATOM | 6218 | CD1 | ILE | A | 410 | −42.416 | 13.824 | −16.985 | 1.00 | 38.96 | C |
| ATOM | 6222 | CG2 | ILE | A | 410 | −44.491 | 15.437 | −15.676 | 1.00 | 37.67 | C |
| ATOM | 6226 | C | ILE | A | 410 | −42.467 | 18.179 | −17.492 | 1.00 | 37.12 | C |
| ATOM | 6227 | O | ILE | A | 410 | −42.150 | 17.839 | −18.617 | 1.00 | 36.87 | O |
| ATOM | 6229 | N | LYS | A | 411 | −41.896 | 19.187 | −16.851 | 1.00 | 37.38 | N |
| ATOM | 6230 | CA | LYS | A | 411 | −40.680 | 19.813 | −17.332 | 1.00 | 37.73 | C |
| ATOM | 6232 | CB | LYS | A | 411 | −40.756 | 21.332 | −17.171 | 1.00 | 38.15 | C |
| ATOM | 6235 | CG | LYS | A | 411 | −41.979 | 21.962 | −17.837 | 1.00 | 39.89 | C |
| ATOM | 6238 | CD | LYS | A | 411 | −41.797 | 23.463 | −18.080 | 1.00 | 42.48 | C |
| ATOM | 6241 | CE | LYS | A | 411 | −43.029 | 24.069 | −18.795 | 1.00 | 44.22 | C |
| ATOM | 6244 | NZ | LYS | A | 411 | −42.977 | 25.576 | −18.904 | 1.00 | 45.31 | N |
| ATOM | 6248 | C | LYS | A | 411 | −39.562 | 19.244 | −16.489 | 1.00 | 37.38 | C |
| ATOM | 6249 | O | LYS | A | 411 | −39.721 | 19.112 | −15.281 | 1.00 | 37.28 | O |
| ATOM | 6251 | N | LYS | A | 412 | −38.445 | 18.886 | −17.122 | 1.00 | 37.24 | N |
| ATOM | 6252 | CA | LYS | A | 412 | −37.333 | 18.243 | −16.413 | 1.00 | 36.95 | C |
| ATOM | 6254 | CB | LYS | A | 412 | −36.286 | 17.701 | −17.384 | 1.00 | 37.14 | C |
| ATOM | 6257 | CG | LYS | A | 412 | −35.233 | 16.818 | −16.720 | 1.00 | 37.89 | C |
| ATOM | 6260 | CD | LYS | A | 412 | −34.334 | 16.125 | −17.757 | 1.00 | 39.54 | C |
| ATOM | 6263 | CE | LYS | A | 412 | −33.263 | 17.068 | −18.348 | 1.00 | 40.08 | C |
| ATOM | 6266 | NZ | LYS | A | 412 | −32.161 | 17.399 | −17.376 | 1.00 | 40.16 | N |
| ATOM | 6270 | C | LYS | A | 412 | −36.664 | 19.177 | −15.419 | 1.00 | 36.42 | C |
| ATOM | 6271 | O | LYS | A | 412 | −36.246 | 18.728 | −14.357 | 1.00 | 36.56 | O |
| ATOM | 6273 | N | GLU | A | 413 | −36.570 | 20.466 | −15.744 | 1.00 | 35.77 | N |
| ATOM | 6274 | CA | GLU | A | 413 | −35.948 | 21.423 | −14.820 | 1.00 | 35.38 | C |
| ATOM | 6276 | CB | GLU | A | 413 | −35.688 | 22.792 | −15.489 | 1.00 | 35.73 | C |
| ATOM | 6279 | CG | GLU | A | 413 | −36.510 | 24.013 | −14.973 | 1.00 | 37.10 | C |
| ATOM | 6282 | CD | GLU | A | 413 | −35.621 | 25.235 | −14.633 | 1.00 | 38.51 | C |
| ATOM | 6283 | OE1 | GLU | A | 413 | −34.778 | 25.125 | −13.714 | 1.00 | 39.24 | O |
| ATOM | 6284 | OE2 | GLU | A | 413 | −35.768 | 26.306 | −15.266 | 1.00 | 39.04 | O |
| ATOM | 6285 | C | GLU | A | 413 | −36.760 | 21.551 | −13.522 | 1.00 | 34.43 | C |
| ATOM | 6286 | O | GLU | A | 413 | −36.196 | 21.801 | −12.460 | 1.00 | 34.34 | O |
| ATOM | 6288 | N | GLU | A | 414 | −38.074 | 21.360 | −13.616 | 1.00 | 33.45 | N |
| ATOM | 6289 | CA | GLU | A | 414 | −38.956 | 21.407 | −12.452 | 1.00 | 32.80 | C |
| ATOM | 6291 | CB | GLU | A | 414 | −40.435 | 21.425 | −12.864 | 1.00 | 32.83 | C |
| ATOM | 6294 | CG | GLU | A | 414 | −40.923 | 22.736 | −13.478 | 1.00 | 33.15 | C |
| ATOM | 6297 | CD | GLU | A | 414 | −42.360 | 22.668 | −14.003 | 1.00 | 33.82 | C |
| ATOM | 6298 | OE1 | GLU | A | 414 | −42.876 | 21.560 | −14.231 | 1.00 | 35.31 | O |
| ATOM | 6299 | OE2 | GLU | A | 414 | −42.985 | 23.727 | −14.204 | 1.00 | 33.98 | O |
| ATOM | 6300 | C | GLU | A | 414 | −38.715 | 20.222 | −11.536 | 1.00 | 32.18 | C |
| ATOM | 6301 | O | GLU | A | 414 | −38.407 | 20.409 | −10.372 | 1.00 | 32.25 | O |
| ATOM | 6303 | N | ILE | A | 415 | −38.863 | 19.002 | −12.044 | 1.00 | 31.63 | N |
| ATOM | 6304 | CA | ILE | A | 415 | −38.725 | 17.819 | −11.181 | 1.00 | 31.28 | C |
| ATOM | 6306 | CB | ILE | A | 415 | −39.131 | 16.472 | −11.852 | 1.00 | 31.14 | C |
| ATOM | 6308 | CG1 | ILE | A | 415 | −38.349 | 16.204 | −13.133 | 1.00 | 31.13 | C |
| ATOM | 6311 | CD1 | ILE | A | 415 | −38.786 | 14.926 | −13.836 | 1.00 | 30.72 | C |
| ATOM | 6315 | CG2 | ILE | A | 415 | −40.611 | 16.454 | −12.160 | 1.00 | 31.12 | C |
| ATOM | 6319 | C | ILE | A | 415 | −37.316 | 17.705 | −10.636 | 1.00 | 31.08 | C |
| ATOM | 6320 | O | ILE | A | 415 | −37.105 | 17.188 | −9.539 | 1.00 | 31.22 | O |
| ATOM | 6322 | N | GLU | A | 416 | −36.345 | 18.208 | −11.381 | 1.00 | 30.67 | N |
| ATOM | 6323 | CA | GLU | A | 416 | −34.998 | 18.270 | −10.850 | 1.00 | 30.55 | C |

TABLE 3-7-continued

Coordinates of *P. tremuloides IspS*

| | | | | | | | | | | |
|---|---|---|---|---|---|---|---|---|---|---|
| ATOM | 6325 | CB | GLU | A | 416 | −34.011 | 18.654 | −11.955 | 1.00 | 30.91 C |
| ATOM | 6328 | CG | GLU | A | 416 | −32.654 | 17.967 | −11.845 | 1.00 | 32.55 C |
| ATOM | 6331 | CD | GLU | A | 416 | −31.802 | 18.130 | −13.109 | 1.00 | 34.91 C |
| ATOM | 6332 | OE1 | GLU | A | 416 | −32.337 | 18.563 | −14.161 | 1.00 | 35.53 O |
| ATOM | 6333 | OE2 | GLU | A | 416 | −30.590 | 17.816 | −13.052 | 1.00 | 36.45 O |
| ATOM | 6334 | C | GLU | A | 416 | −34.962 | 19.249 | −9.650 | 1.00 | 29.74 C |
| ATOM | 6335 | O | GLU | A | 416 | −34.143 | 19.097 | −8.738 | 1.00 | 29.73 O |
| ATOM | 6337 | N | ASN | A | 417 | −35.864 | 20.234 | −9.652 | 1.00 | 28.69 N |
| ATOM | 6338 | CA | ASN | A | 417 | −36.060 | 21.134 | −8.503 | 1.00 | 27.92 C |
| ATOM | 6340 | CB | ASN | A | 417 | −36.632 | 22.477 | −8.963 | 1.00 | 27.75 C |
| ATOM | 6343 | CG | ASN | A | 417 | −35.572 | 23.532 | −9.095 | 1.00 | 26.84 C |
| ATOM | 6344 | OD1 | ASN | A | 417 | −35.160 | 24.132 | −8.105 | 1.00 | 24.88 O |
| ATOM | 6345 | ND2 | ASN | A | 417 | −35.117 | 23.765 | −10.318 | 1.00 | 26.28 N |
| ATOM | 6348 | C | ASN | A | 417 | −36.917 | 20.580 | −7.356 | 1.00 | 27.41 C |
| ATOM | 6349 | O | ASN | A | 417 | −36.650 | 20.838 | −6.187 | 1.00 | 27.15 O |
| ATOM | 6351 | N | LEU | A | 418 | −37.955 | 19.834 | −7.675 | 1.00 | 27.09 N |
| ATOM | 6352 | CA | LEU | A | 418 | −38.694 | 19.156 | −6.628 | 1.00 | 27.02 C |
| ATOM | 6354 | CB | LEU | A | 418 | −39.921 | 18.423 | −7.200 | 1.00 | 26.95 C |
| ATOM | 6357 | CG | LEU | A | 418 | −41.030 | 19.284 | −7.826 | 1.00 | 25.97 C |
| ATOM | 6359 | CD1 | LEU | A | 418 | −42.127 | 18.429 | −8.447 | 1.00 | 24.88 C |
| ATOM | 6363 | CD2 | LEU | A | 418 | −41.623 | 20.226 | −6.803 | 1.00 | 24.50 C |
| ATOM | 6367 | C | LEU | A | 418 | −37.763 | 18.196 | −5.860 | 1.00 | 27.26 C |
| ATOM | 6368 | O | LEU | A | 418 | −37.834 | 18.123 | −4.644 | 1.00 | 27.07 O |
| ATOM | 6370 | N | GLN | A | 419 | −36.873 | 17.494 | −6.561 | 1.00 | 27.67 N |
| ATOM | 6371 | CA | GLN | A | 419 | −35.924 | 16.575 | −5.909 | 1.00 | 28.28 C |
| ATOM | 6373 | CB | GLN | A | 419 | −35.155 | 15.758 | −6.945 | 1.00 | 28.36 C |
| ATOM | 6376 | CG | GLN | A | 419 | −35.747 | 14.375 | −7.146 | 1.00 | 29.43 C |
| ATOM | 6379 | CD | GLN | A | 419 | −35.052 | 13.573 | −8.215 | 1.00 | 29.76 C |
| ATOM | 6380 | OE1 | GLN | A | 419 | −34.355 | 14.112 | −9.066 | 1.00 | 29.93 O |
| ATOM | 6381 | NE2 | GLN | A | 419 | −35.252 | 12.270 | −8.184 | 1.00 | 31.33 N |
| ATOM | 6384 | C | GLN | A | 419 | −34.922 | 17.219 | −4.947 | 1.00 | 28.73 C |
| ATOM | 6385 | O | GLN | A | 419 | −34.540 | 16.608 | −3.952 | 1.00 | 28.90 O |
| ATOM | 6387 | N | LYS | A | 420 | −34.490 | 18.440 | −5.240 | 1.00 | 29.27 N |
| ATOM | 6388 | CA | LYS | A | 420 | −33.608 | 19.166 | −4.335 | 1.00 | 29.81 C |
| ATOM | 6390 | CB | LYS | A | 420 | −32.758 | 20.163 | −5.129 | 1.00 | 30.24 C |
| ATOM | 6393 | CG | LYS | A | 420 | −31.592 | 19.513 | −5.867 | 1.00 | 31.75 C |
| ATOM | 6396 | CD | LYS | A | 420 | −31.259 | 20.217 | −7.183 | 1.00 | 34.14 C |
| ATOM | 6399 | CE | LYS | A | 420 | −30.140 | 19.463 | −7.953 | 1.00 | 36.21 C |
| ATOM | 6402 | NZ | LYS | A | 420 | −30.073 | 19.759 | −9.439 | 1.00 | 36.76 N |
| ATOM | 6406 | C | LYS | A | 420 | −34.375 | 19.872 | −3.204 | 1.00 | 29.98 C |
| ATOM | 6407 | O | LYS | A | 420 | −33.759 | 20.547 | −2.384 | 1.00 | 30.44 O |
| ATOM | 6409 | N | TYR | A | 421 | −35.706 | 19.694 | −3.162 | 1.00 | 30.07 N |
| ATOM | 6410 | CA | TYR | A | 421 | −36.646 | 20.309 | −2.171 | 1.00 | 29.73 C |
| ATOM | 6412 | CB | TYR | A | 421 | −36.298 | 19.949 | −.712 | 1.00 | 29.59 C |
| ATOM | 6415 | CG | TYR | A | 421 | −36.386 | 18.468 | −.470 | 1.00 | 30.57 C |
| ATOM | 6416 | CD1 | TYR | A | 421 | −37.582 | 17.785 | −.643 | 1.00 | 30.87 C |
| ATOM | 6418 | CE1 | TYR | A | 421 | −37.665 | 16.414 | −.448 | 1.00 | 31.28 C |
| ATOM | 6420 | CZ | TYR | A | 421 | −36.549 | 15.705 | −.068 | 1.00 | 31.90 C |
| ATOM | 6421 | OH | TYR | A | 421 | −36.620 | 14.347 | .124 | 1.00 | 32.43 O |
| ATOM | 6423 | CE2 | TYR | A | 421 | −35.355 | 16.354 | .119 | 1.00 | 32.68 C |
| ATOM | 6425 | CD2 | TYR | A | 421 | −35.274 | 17.736 | −.095 | 1.00 | 32.42 C |
| ATOM | 6427 | C | TYR | A | 421 | −36.850 | 21.816 | −2.347 | 1.00 | 29.24 C |
| ATOM | 6428 | O | TYR | A | 421 | −36.709 | 22.590 | −1.401 | 1.00 | 29.26 O |
| ATOM | 6430 | N | HIS | A | 422 | −37.219 | 22.214 | −3.563 | 1.00 | 28.65 N |
| ATOM | 6431 | CA | HIS | A | 422 | −37.540 | 23.604 | −3.859 | 1.00 | 28.26 C |
| ATOM | 6433 | CB | HIS | A | 422 | −38.150 | 23.715 | −5.256 | 1.00 | 28.33 C |
| ATOM | 6436 | CG | HIS | A | 422 | −38.299 | 25.124 | −5.748 | 1.00 | 28.44 C |
| ATOM | 6437 | ND1 | HIS | A | 422 | −37.225 | 25.904 | −6.106 | 1.00 | 28.97 N |
| ATOM | 6439 | CE1 | HIS | A | 422 | −37.660 | 27.082 | −6.520 | 1.00 | 29.40 C |
| ATOM | 6441 | NE2 | HIS | A | 422 | −38.977 | 27.090 | −6.443 | 1.00 | 28.14 N |
| ATOM | 6443 | CD2 | HIS | A | 422 | −39.399 | 25.879 | −5.965 | 1.00 | 27.76 C |
| ATOM | 6445 | C | HIS | A | 422 | −38.511 | 24.147 | −2.816 | 1.00 | 27.74 C |
| ATOM | 6446 | O | HIS | A | 422 | −39.357 | 23.408 | −2.310 | 1.00 | 27.53 O |
| ATOM | 6448 | N | ASP | A | 423 | −38.384 | 25.437 | −2.505 | 1.00 | 27.12 N |
| ATOM | 6449 | CA | ASP | A | 423 | −39.186 | 26.072 | −1.454 | 1.00 | 26.63 C |
| ATOM | 6451 | CB | ASP | A | 423 | −38.877 | 27.575 | −1.349 | 1.00 | 27.05 C |
| ATOM | 6454 | CG | ASP | A | 423 | −37.456 | 27.875 | −.851 | 1.00 | 28.35 C |
| ATOM | 6455 | OD1 | ASP | A | 423 | −36.951 | 27.121 | .018 | 1.00 | 30.99 O |
| ATOM | 6456 | OD2 | ASP | A | 423 | −36.860 | 28.884 | −1.322 | 1.00 | 27.89 O |
| ATOM | 6457 | C | ASP | A | 423 | −40.689 | 25.883 | −1.698 | 1.00 | 25.71 C |
| ATOM | 6458 | O | ASP | A | 423 | −41.487 | 25.831 | −.749 | 1.00 | 26.26 O |
| ATOM | 6460 | N | ILE | A | 424 | −41.075 | 25.781 | −2.966 | 1.00 | 24.01 N |
| ATOM | 6461 | CA | ILE | A | 424 | −42.479 | 25.596 | −3.327 | 1.00 | 22.72 C |
| ATOM | 6463 | CB | ILE | A | 424 | −42.639 | 25.391 | −4.843 | 1.00 | 22.40 C |
| ATOM | 6465 | CG1 | ILE | A | 424 | −44.029 | 25.668 | −5.318 | 1.00 | 21.78 C |
| ATOM | 6468 | CD1 | ILE | A | 424 | −44.086 | 25.499 | −6.793 | 1.00 | 22.22 C |
| ATOM | 6472 | CG2 | ILE | A | 424 | −42.340 | 23.985 | −5.255 | 1.00 | 22.87 C |
| ATOM | 6476 | C | ILE | A | 424 | −43.103 | 24.442 | −2.562 | 1.00 | 21.91 C |

TABLE 3-7-continued

Coordinates of *P. tremuloides IspS*

| | | | | | | | | | | | |
|---|---|---|---|---|---|---|---|---|---|---|---|
| ATOM | 6477 | O | ILE | A | 424 | −44.238 | 24.574 | −2.115 | 1.00 | 21.73 | O |
| ATOM | 6479 | N | ILE | A | 425 | −42.365 | 23.334 | −2.399 | 1.00 | 21.23 | N |
| ATOM | 6480 | CA | ILE | A | 425 | −42.853 | 22.173 | −1.634 | 1.00 | 20.73 | C |
| ATOM | 6482 | CB | ILE | A | 425 | −42.622 | 20.820 | −2.330 | 1.00 | 20.10 | C |
| ATOM | 6484 | CG1 | ILE | A | 425 | −41.158 | 20.409 | −2.290 | 1.00 | 18.72 | C |
| ATOM | 6487 | CD1 | ILE | A | 425 | −40.923 | 19.075 | −2.948 | 1.00 | 18.27 | C |
| ATOM | 6491 | CG2 | ILE | A | 425 | −43.146 | 20.840 | −3.741 | 1.00 | 19.57 | C |
| ATOM | 6495 | C | ILE | A | 425 | −42.252 | 22.060 | −.242 | 1.00 | 21.21 | C |
| ATOM | 6496 | O | ILE | A | 425 | −42.810 | 21.370 | .613 | 1.00 | 21.30 | O |
| ATOM | 6498 | N | SER | A | 426 | −41.129 | 22.721 | −.002 | 1.00 | 21.56 | N |
| ATOM | 6499 | CA | SER | A | 426 | −40.492 | 22.620 | 1.299 | 1.00 | 22.23 | C |
| ATOM | 6501 | CB | SER | A | 426 | −39.043 | 23.082 | 1.234 | 1.00 | 22.36 | C |
| ATOM | 6504 | OG | SER | A | 426 | −38.977 | 24.501 | 1.342 | 1.00 | 24.09 | O |
| ATOM | 6506 | C | SER | A | 426 | −41.242 | 23.460 | 2.334 | 1.00 | 22.39 | C |
| ATOM | 6507 | O | SER | A | 426 | −41.390 | 23.051 | 3.491 | 1.00 | 22.95 | O |
| ATOM | 6509 | N | ARG | A | 427 | −41.701 | 24.643 | 1.937 | 1.00 | 22.08 | N |
| ATOM | 6510 | CA | ARG | A | 427 | −42.332 | 25.541 | 2.905 | 1.00 | 21.87 | C |
| ATOM | 6512 | CB | ARG | A | 427 | −42.466 | 26.955 | 2.345 | 1.00 | 21.99 | C |
| ATOM | 6515 | CG | ARG | A | 427 | −41.170 | 27.696 | 2.493 | 1.00 | 23.36 | C |
| ATOM | 6518 | CD | ARG | A | 427 | −40.954 | 28.727 | 1.433 | 1.00 | 26.07 | C |
| ATOM | 6521 | NE | ARG | A | 427 | −39.680 | 29.407 | 1.667 | 1.00 | 28.18 | N |
| ATOM | 6523 | CZ | ARG | A | 427 | −39.127 | 30.298 | .844 | 1.00 | 29.21 | C |
| ATOM | 6524 | NH1 | ARG | A | 427 | −39.723 | 30.633 | −.298 | 1.00 | 28.60 | N |
| ATOM | 6527 | NH2 | ARG | A | 427 | −37.962 | 30.854 | 1.173 | 1.00 | 30.48 | N |
| ATOM | 6530 | C | ARG | A | 427 | −43.651 | 25.003 | 3.434 | 1.00 | 21.21 | C |
| ATOM | 6531 | O | ARG | A | 427 | −43.817 | 24.891 | 4.645 | 1.00 | 21.11 | O |
| ATOM | 6533 | N | PRO | A | 428 | −44.573 | 24.622 | 2.541 | 1.00 | 20.52 | N |
| ATOM | 6534 | CA | PRO | A | 428 | −45.789 | 23.999 | 3.040 | 1.00 | 20.27 | C |
| ATOM | 6536 | CB | PRO | A | 428 | −46.410 | 23.369 | 1.791 | 1.00 | 20.44 | C |
| ATOM | 6539 | CG | PRO | A | 428 | −45.864 | 24.119 | .666 | 1.00 | 20.63 | C |
| ATOM | 6542 | CD | PRO | A | 428 | −44.521 | 24.644 | 1.074 | 1.00 | 20.54 | C |
| ATOM | 6545 | C | PRO | A | 428 | −45.450 | 22.917 | 4.050 | 1.00 | 19.75 | C |
| ATOM | 6546 | O | PRO | A | 428 | −46.089 | 22.834 | 5.095 | 1.00 | 19.77 | O |
| ATOM | 6547 | N | SER | A | 429 | −44.424 | 22.123 | 3.747 | 1.00 | 18.97 | N |
| ATOM | 6548 | CA | SER | A | 429 | −44.008 | 21.045 | 4.636 | 1.00 | 18.45 | C |
| ATOM | 6550 | CB | SER | A | 429 | −42.954 | 20.180 | 3.972 | 1.00 | 18.35 | C |
| ATOM | 6553 | OG | SER | A | 429 | −43.452 | 19.716 | 2.733 | 1.00 | 19.12 | O |
| ATOM | 6555 | C | SER | A | 429 | −43.519 | 21.525 | 5.985 | 1.00 | 17.97 | C |
| ATOM | 6556 | O | SER | A | 429 | −43.733 | 20.846 | 6.968 | 1.00 | 17.88 | O |
| ATOM | 6558 | N | HIS | A | 430 | −42.879 | 22.689 | 6.053 | 1.00 | 17.73 | N |
| ATOM | 6559 | CA | HIS | A | 430 | −42.593 | 23.289 | 7.359 | 1.00 | 17.71 | C |
| ATOM | 6561 | CB | HIS | A | 430 | −41.937 | 24.668 | 7.241 | 1.00 | 17.97 | C |
| ATOM | 6564 | CG | HIS | A | 430 | −40.558 | 24.663 | 6.651 | 1.00 | 18.87 | C |
| ATOM | 6565 | ND1 | HIS | A | 430 | −39.940 | 23.524 | 6.186 | 1.00 | 19.85 | N |
| ATOM | 6567 | CE1 | HIS | A | 430 | −38.746 | 23.836 | 5.709 | 1.00 | 19.43 | C |
| ATOM | 6569 | NE2 | HIS | A | 430 | −38.573 | 25.137 | 5.838 | 1.00 | 19.06 | N |
| ATOM | 6571 | CD2 | HIS | A | 430 | −39.693 | 25.681 | 6.418 | 1.00 | 19.32 | C |
| ATOM | 6573 | C | HIS | A | 430 | −43.914 | 23.444 | 8.131 | 1.00 | 17.31 | C |
| ATOM | 6574 | O | HIS | A | 430 | −44.023 | 23.013 | 9.287 | 1.00 | 17.06 | O |
| ATOM | 6576 | N | ILE | A | 431 | −44.913 | 24.050 | 7.475 | 1.00 | 16.74 | N |
| ATOM | 6577 | CA | ILE | A | 431 | −46.218 | 24.304 | 8.091 | 1.00 | 16.15 | C |
| ATOM | 6579 | CB | ILE | A | 431 | −47.174 | 25.057 | 7.174 | 1.00 | 16.18 | C |
| ATOM | 6581 | CG1 | ILE | A | 431 | −46.613 | 26.428 | 6.801 | 1.00 | 17.05 | C |
| ATOM | 6584 | CD1 | ILE | A | 431 | −46.441 | 27.352 | 7.994 | 1.00 | 18.34 | C |
| ATOM | 6588 | CG2 | ILE | A | 431 | −48.496 | 25.263 | 7.860 | 1.00 | 15.28 | C |
| ATOM | 6592 | C | ILE | A | 431 | −46.899 | 23.021 | 8.476 | 1.00 | 15.75 | C |
| ATOM | 6593 | O | ILE | A | 431 | −47.624 | 22.980 | 9.445 | 1.00 | 15.95 | O |
| ATOM | 6595 | N | PHE | A | 432 | −46.663 | 21.969 | 7.714 | 1.00 | 15.59 | N |
| ATOM | 6596 | CA | PHE | A | 432 | −47.192 | 20.652 | 8.041 | 1.00 | 15.52 | C |
| ATOM | 6598 | CB | PHE | A | 432 | −46.837 | 19.683 | 6.913 | 1.00 | 15.23 | C |
| ATOM | 6601 | CG | PHE | A | 432 | −47.451 | 18.318 | 7.031 | 1.00 | 15.98 | C |
| ATOM | 6602 | CD1 | PHE | A | 432 | −48.324 | 17.972 | 8.052 | 1.00 | 16.55 | C |
| ATOM | 6604 | CE1 | PHE | A | 432 | −48.867 | 16.700 | 8.102 | 1.00 | 16.04 | C |
| ATOM | 6606 | CZ | PHE | A | 432 | −48.559 | 15.774 | 7.130 | 1.00 | 15.29 | C |
| ATOM | 6608 | CE2 | PHE | A | 432 | −47.718 | 16.107 | 6.114 | 1.00 | 15.37 | C |
| ATOM | 6610 | CD2 | PHE | A | 432 | −47.172 | 17.364 | 6.061 | 1.00 | 16.74 | C |
| ATOM | 6612 | C | PHE | A | 432 | −46.640 | 20.191 | 9.392 | 1.00 | 15.54 | C |
| ATOM | 6613 | O | PHE | A | 432 | −47.383 | 20.006 | 10.343 | 1.00 | 15.37 | O |
| ATOM | 6615 | N | ARG | A | 433 | −45.328 | 20.041 | 9.483 | 1.00 | 15.98 | N |
| ATOM | 6616 | CA | ARG | A | 433 | −44.695 | 19.542 | 10.709 | 1.00 | 16.20 | C |
| ATOM | 6618 | CB | ARG | A | 433 | −43.176 | 19.476 | 10.526 | 1.00 | 15.85 | C |
| ATOM | 6621 | CG | ARG | A | 433 | −42.411 | 19.183 | 11.804 | 1.00 | 16.11 | C |
| ATOM | 6624 | CD | ARG | A | 433 | −42.848 | 17.890 | 12.489 | 1.00 | 15.70 | C |
| ATOM | 6627 | NE | ARG | A | 433 | −42.811 | 16.747 | 11.588 | 1.00 | 15.64 | N |
| ATOM | 6629 | CZ | ARG | A | 433 | −43.377 | 15.571 | 11.838 | 1.00 | 16.27 | C |
| ATOM | 6630 | NH1 | ARG | A | 433 | −44.029 | 15.359 | 12.965 | 1.00 | 16.82 | N |
| ATOM | 6633 | NH2 | ARG | A | 433 | −43.302 | 14.598 | 10.948 | 1.00 | 16.96 | N |
| ATOM | 6636 | C | ARG | A | 433 | −45.029 | 20.411 | 11.935 | 1.00 | 16.46 | C |

TABLE 3-7-continued

Coordinates of *P. tremuloides IspS*

| | | | | | | | | | | | |
|---|---|---|---|---|---|---|---|---|---|---|---|
| ATOM | 6637 | O | ARG | A | 433 | −45.296 | 19.890 | 13.031 | 1.00 | 16.31 | O |
| ATOM | 6639 | N | LEU | A | 434 | −45.006 | 21.731 | 11.724 | 1.00 | 16.47 | N |
| ATOM | 6640 | CA | LEU | A | 434 | −45.123 | 22.701 | 12.800 | 1.00 | 15.98 | C |
| ATOM | 6642 | CB | LEU | A | 434 | −44.771 | 24.114 | 12.303 | 1.00 | 15.83 | C |
| ATOM | 6645 | CG | LEU | A | 434 | −43.287 | 24.486 | 12.218 | 1.00 | 14.95 | C |
| ATOM | 6647 | CD1 | LEU | A | 434 | −43.130 | 25.918 | 11.826 | 1.00 | 15.09 | C |
| ATOM | 6651 | CD2 | LEU | A | 434 | −42.600 | 24.281 | 13.536 | 1.00 | 14.37 | C |
| ATOM | 6655 | C | LEU | A | 434 | −46.517 | 22.660 | 13.387 | 1.00 | 16.19 | C |
| ATOM | 6656 | O | LEU | A | 434 | −46.669 | 22.564 | 14.604 | 1.00 | 15.92 | O |
| ATOM | 6658 | N | CYS | A | 435 | −47.529 | 22.715 | 12.520 | 1.00 | 16.78 | N |
| ATOM | 6659 | CA | CYS | A | 435 | −48.936 | 22.591 | 12.940 | 1.00 | 17.48 | C |
| ATOM | 6661 | CB | CYS | A | 435 | −49.870 | 22.617 | 11.726 | 1.00 | 17.54 | C |
| ATOM | 6664 | SG | CYS | A | 435 | −50.110 | 24.233 | 10.985 | 1.00 | 18.80 | S |
| ATOM | 6666 | C | CYS | A | 435 | −49.192 | 21.296 | 13.708 | 1.00 | 17.84 | C |
| ATOM | 6667 | O | CYS | A | 435 | −50.043 | 21.250 | 14.597 | 1.00 | 17.92 | O |
| ATOM | 6669 | N | ASN | A | 436 | −48.446 | 20.257 | 13.333 | 1.00 | 18.24 | N |
| ATOM | 6670 | CA | ASN | A | 436 | −48.603 | 18.913 | 13.846 | 1.00 | 18.50 | C |
| ATOM | 6672 | CB | ASN | A | 436 | −47.936 | 17.949 | 12.867 | 1.00 | 18.63 | C |
| ATOM | 6675 | CG | ASN | A | 436 | −48.156 | 16.487 | 13.213 | 1.00 | 18.58 | C |
| ATOM | 6676 | OD1 | ASN | A | 436 | −48.810 | 16.129 | 14.185 | 1.00 | 18.80 | O |
| ATOM | 6677 | ND2 | ASN | A | 436 | −47.588 | 15.633 | 12.398 | 1.00 | 19.29 | N |
| ATOM | 6680 | C | ASN | A | 436 | −47.975 | 18.755 | 15.210 | 1.00 | 18.83 | C |
| ATOM | 6681 | O | ASN | A | 436 | −48.551 | 18.153 | 16.115 | 1.00 | 19.00 | O |
| ATOM | 6683 | N | ASP | A | 437 | −46.763 | 19.255 | 15.351 | 1.00 | 19.29 | N |
| ATOM | 6684 | CA | ASP | A | 437 | −46.097 | 19.179 | 16.634 | 1.00 | 19.62 | C |
| ATOM | 6686 | CB | ASP | A | 437 | −44.615 | 19.522 | 16.510 | 1.00 | 19.45 | C |
| ATOM | 6689 | CG | ASP | A | 437 | −43.849 | 18.480 | 15.734 | 1.00 | 19.36 | C |
| ATOM | 6690 | OD1 | ASP | A | 437 | −44.491 | 17.586 | 15.158 | 1.00 | 19.89 | O |
| ATOM | 6691 | OD2 | ASP | A | 437 | −42.608 | 18.543 | 15.699 | 1.00 | 19.86 | O |
| ATOM | 6692 | C | ASP | A | 437 | −46.799 | 20.106 | 17.597 | 1.00 | 20.01 | C |
| ATOM | 6693 | O | ASP | A | 437 | −46.916 | 19.790 | 18.779 | 1.00 | 20.30 | O |
| ATOM | 6695 | N | LEU | A | 438 | −47.288 | 21.233 | 17.092 | 1.00 | 20.40 | N |
| ATOM | 6696 | CA | LEU | A | 438 | −47.996 | 22.174 | 17.940 | 1.00 | 21.03 | C |
| ATOM | 6698 | CB | LEU | A | 438 | −48.510 | 23.363 | 17.126 | 1.00 | 21.01 | C |
| ATOM | 6701 | CG | LEU | A | 438 | −47.575 | 24.565 | 17.078 | 1.00 | 20.32 | C |
| ATOM | 6703 | CD1 | LEU | A | 438 | −47.938 | 25.524 | 15.952 | 1.00 | 19.14 | C |
| ATOM | 6707 | CD2 | LEU | A | 438 | −47.611 | 25.263 | 18.415 | 1.00 | 19.73 | C |
| ATOM | 6711 | C | LEU | A | 438 | −49.153 | 21.496 | 18.679 | 1.00 | 21.81 | C |
| ATOM | 6712 | O | LEU | A | 438 | −49.277 | 21.633 | 19.902 | 1.00 | 21.55 | O |
| ATOM | 6714 | N | ALA | A | 439 | −49.973 | 20.754 | 17.932 | 1.00 | 22.76 | N |
| ATOM | 6715 | CA | ALA | A | 439 | −51.138 | 20.055 | 18.486 | 1.00 | 23.58 | C |
| ATOM | 6717 | CB | ALA | A | 439 | −51.905 | 19.360 | 17.386 | 1.00 | 23.57 | C |
| ATOM | 6721 | C | ALA | A | 439 | −50.746 | 19.042 | 19.542 | 1.00 | 24.47 | C |
| ATOM | 6722 | O | ALA | A | 439 | −51.386 | 18.951 | 20.575 | 1.00 | 24.63 | O |
| ATOM | 6724 | N | SER | A | 440 | −49.685 | 18.291 | 19.276 | 1.00 | 25.78 | N |
| ATOM | 6725 | CA | SER | A | 440 | −49.242 | 17.227 | 20.168 | 1.00 | 26.84 | C |
| ATOM | 6727 | CB | SER | A | 440 | −48.566 | 16.130 | 19.353 | 1.00 | 26.92 | C |
| ATOM | 6730 | OG | SER | A | 440 | −47.321 | 16.582 | 18.859 | 1.00 | 27.46 | O |
| ATOM | 6732 | C | SER | A | 440 | −48.270 | 17.691 | 21.244 | 1.00 | 27.68 | C |
| ATOM | 6733 | O | SER | A | 440 | −47.934 | 16.923 | 22.132 | 1.00 | 28.00 | O |
| ATOM | 6735 | N | ALA | A | 441 | −47.822 | 18.935 | 21.174 | 1.00 | 28.83 | N |
| ATOM | 6736 | CA | ALA | A | 441 | −46.760 | 19.419 | 22.056 | 1.00 | 29.73 | C |
| ATOM | 6738 | CB | ALA | A | 441 | −46.529 | 20.910 | 21.841 | 1.00 | 29.84 | C |
| ATOM | 6742 | C | ALA | A | 441 | −46.982 | 19.132 | 23.539 | 1.00 | 30.57 | C |
| ATOM | 6743 | O | ALA | A | 441 | −46.306 | 18.274 | 24.093 | 1.00 | 30.50 | O |
| ATOM | 6745 | N | SER | A | 442 | −47.929 | 19.827 | 24.172 | 1.00 | 31.90 | N |
| ATOM | 6746 | CA | SER | A | 442 | −47.999 | 19.862 | 25.654 | 1.00 | 32.95 | C |
| ATOM | 6748 | CB | SER | A | 442 | −49.043 | 20.870 | 26.169 | 1.00 | 32.91 | C |
| ATOM | 6751 | OG | SER | A | 442 | −50.331 | 20.614 | 25.650 | 1.00 | 33.50 | O |
| ATOM | 6753 | C | SER | A | 442 | −48.219 | 18.497 | 26.289 | 1.00 | 33.69 | C |
| ATOM | 6754 | O | SER | A | 442 | −47.754 | 18.246 | 27.397 | 1.00 | 33.59 | O |
| ATOM | 6756 | N | ALA | A | 443 | −48.922 | 17.623 | 25.578 | 1.00 | 34.93 | N |
| ATOM | 6757 | CA | ALA | A | 443 | −49.050 | 16.231 | 25.980 | 1.00 | 35.81 | C |
| ATOM | 6759 | CB | ALA | A | 443 | −49.981 | 15.488 | 25.030 | 1.00 | 35.72 | C |
| ATOM | 6763 | C | ALA | A | 443 | −47.663 | 15.580 | 25.996 | 1.00 | 36.71 | C |
| ATOM | 6764 | O | ALA | A | 443 | −47.198 | 15.115 | 27.047 | 1.00 | 36.94 | O |
| ATOM | 6766 | N | GLU | A | 444 | −46.999 | 15.567 | 24.838 | 1.00 | 37.47 | N |
| ATOM | 6767 | CA | GLU | A | 444 | −45.688 | 14.930 | 24.718 | 1.00 | 37.93 | C |
| ATOM | 6769 | CB | GLU | A | 444 | −45.164 | 14.996 | 23.277 | 1.00 | 37.99 | C |
| ATOM | 6772 | CG | GLU | A | 444 | −45.952 | 14.100 | 22.326 | 1.00 | 39.24 | C |
| ATOM | 6775 | CD | GLU | A | 444 | −45.419 | 14.080 | 20.886 | 1.00 | 41.03 | C |
| ATOM | 6776 | OE1 | GLU | A | 444 | −44.612 | 14.958 | 20.510 | 1.00 | 42.16 | O |
| ATOM | 6777 | OE2 | GLU | A | 444 | −45.827 | 13.178 | 20.119 | 1.00 | 42.36 | O |
| ATOM | 6778 | C | GLU | A | 444 | −44.694 | 15.534 | 25.708 | 1.00 | 38.09 | C |
| ATOM | 6779 | O | GLU | A | 444 | −43.924 | 14.803 | 26.324 | 1.00 | 38.17 | O |
| ATOM | 6781 | N | ILE | A | 445 | −44.739 | 16.851 | 25.889 | 1.00 | 38.41 | N |
| ATOM | 6782 | CA | ILE | A | 445 | −43.829 | 17.530 | 26.814 | 1.00 | 38.75 | C |
| ATOM | 6784 | CB | ILE | A | 445 | −43.802 | 19.065 | 26.587 | 1.00 | 38.69 | C |

TABLE 3-7-continued

Coordinates of *P. tremuloides IspS*

| | | | | | | | | | | |
|---|---|---|---|---|---|---|---|---|---|---|
| ATOM | 6786 | CG1 | ILE | A | 445 | −43.314 | 19.396 | 25.170 | 1.00 | 38.18 C |
| ATOM | 6789 | CD1 | ILE | A | 445 | −43.702 | 20.775 | 24.712 | 1.00 | 37.58 C |
| ATOM | 6793 | CG2 | ILE | A | 445 | −42.909 | 19.753 | 27.617 | 1.00 | 38.26 C |
| ATOM | 6797 | C | ILE | A | 445 | −44.243 | 17.194 | 28.246 | 1.00 | 39.35 C |
| ATOM | 6798 | O | ILE | A | 445 | −45.039 | 17.901 | 28.870 | 1.00 | 39.44 O |
| ATOM | 6800 | N | ALA | A | 446 | −43.696 | 16.092 | 28.750 | 1.00 | 40.02 N |
| ATOM | 6801 | CA | ALA | A | 446 | −44.082 | 15.540 | 30.045 | 1.00 | 40.51 C |
| ATOM | 6803 | CB | ALA | A | 446 | −43.815 | 16.552 | 31.170 | 1.00 | 40.55 C |
| ATOM | 6807 | C | ALA | A | 446 | −45.559 | 15.130 | 30.029 | 1.00 | 40.86 C |
| ATOM | 6808 | O | ALA | A | 446 | −46.407 | 16.021 | 30.121 | 1.00 | 40.77 O |
| ATOM | 6810 | N | ARG | A | 447 | −45.925 | 13.842 | 29.899 | 1.00 | 41.31 N |
| ATOM | 6811 | CA | ARG | A | 447 | −45.072 | 12.633 | 29.691 | 1.00 | 41.58 C |
| ATOM | 6813 | CB | ARG | A | 447 | −45.272 | 12.092 | 28.258 | 1.00 | 41.84 C |
| ATOM | 6816 | CG | ARG | A | 447 | −46.667 | 11.495 | 27.991 | 1.00 | 42.69 C |
| ATOM | 6819 | CD | ARG | A | 447 | −46.778 | 10.901 | 26.582 | 1.00 | 43.92 C |
| ATOM | 6822 | NE | ARG | A | 447 | −47.764 | 11.589 | 25.744 | 1.00 | 45.34 N |
| ATOM | 6824 | CZ | ARG | A | 447 | −47.887 | 11.435 | 24.420 | 1.00 | 46.56 C |
| ATOM | 6825 | NH1 | ARG | A | 447 | −47.077 | 10.623 | 23.742 | 1.00 | 46.71 N |
| ATOM | 6828 | NH2 | ARG | A | 447 | −48.828 | 12.107 | 23.757 | 1.00 | 46.97 N |
| ATOM | 6831 | C | ARG | A | 447 | −43.581 | 12.728 | 30.054 | 1.00 | 41.38 C |
| ATOM | 6832 | O | ARG | A | 447 | −43.231 | 12.747 | 31.238 | 1.00 | 41.92 O |
| ATOM | 6834 | N | GLY | A | 448 | −42.710 | 12.736 | 29.051 | 1.00 | 40.88 N |
| ATOM | 6835 | CA | GLY | A | 448 | −41.312 | 13.128 | 29.234 | 1.00 | 40.44 C |
| ATOM | 6838 | C | GLY | A | 448 | −40.579 | 13.316 | 27.915 | 1.00 | 40.08 C |
| ATOM | 6839 | O | GLY | A | 448 | −39.364 | 13.488 | 27.901 | 1.00 | 40.05 O |
| ATOM | 6841 | N | GLU | A | 449 | −41.323 | 13.332 | 26.809 | 1.00 | 39.56 N |
| ATOM | 6842 | CA | GLU | A | 449 | −40.750 | 13.132 | 25.486 | 1.00 | 39.19 C |
| ATOM | 6844 | CB | GLU | A | 449 | −41.827 | 12.668 | 24.502 | 1.00 | 39.52 C |
| ATOM | 6847 | CG | GLU | A | 449 | −42.403 | 11.290 | 24.810 | 1.00 | 40.61 C |
| ATOM | 6850 | CD | GLU | A | 449 | −43.348 | 10.782 | 23.715 | 1.00 | 42.21 C |
| ATOM | 6851 | OE1 | GLU | A | 449 | −43.068 | 11.019 | 22.503 | 1.00 | 41.83 O |
| ATOM | 6852 | OE2 | GLU | A | 449 | −44.368 | 10.141 | 24.082 | 1.00 | 42.41 O |
| ATOM | 6853 | C | GLU | A | 449 | −40.037 | 14.365 | 24.921 | 1.00 | 38.34 C |
| ATOM | 6854 | O | GLU | A | 449 | −40.511 | 15.497 | 25.031 | 1.00 | 38.01 O |
| ATOM | 6856 | N | THR | A | 450 | −38.904 | 14.106 | 24.279 | 1.00 | 37.37 N |
| ATOM | 6857 | CA | THR | A | 450 | −38.047 | 15.138 | 23.726 | 1.00 | 36.37 C |
| ATOM | 6859 | CB | THR | A | 450 | −36.607 | 14.985 | 24.285 | 1.00 | 36.39 C |
| ATOM | 6861 | OG1 | THR | A | 450 | −35.846 | 16.153 | 23.982 | 1.00 | 36.63 O |
| ATOM | 6863 | CG2 | THR | A | 450 | −35.888 | 13.749 | 23.706 | 1.00 | 36.52 C |
| ATOM | 6867 | C | THR | A | 450 | −38.013 | 15.100 | 22.190 | 1.00 | 35.36 C |
| ATOM | 6868 | O | THR | A | 450 | −37.175 | 15.764 | 21.583 | 1.00 | 35.43 O |
| ATOM | 6870 | N | ALA | A | 451 | −38.917 | 14.338 | 21.563 | 1.00 | 33.98 N |
| ATOM | 6871 | CA | ALA | A | 451 | −38.920 | 14.182 | 20.096 | 1.00 | 32.81 C |
| ATOM | 6873 | CB | ALA | A | 451 | −39.030 | 12.708 | 19.708 | 1.00 | 32.99 C |
| ATOM | 6877 | C | ALA | A | 451 | −40.043 | 14.987 | 19.459 | 1.00 | 31.46 C |
| ATOM | 6878 | O | ALA | A | 451 | −41.050 | 14.432 | 18.996 | 1.00 | 31.06 O |
| ATOM | 6880 | N | ASN | A | 452 | −39.848 | 16.302 | 19.432 | 1.00 | 29.88 N |
| ATOM | 6881 | CA | ASN | A | 452 | −40.881 | 17.225 | 18.973 | 1.00 | 28.81 C |
| ATOM | 6883 | CB | ASN | A | 452 | −41.957 | 17.329 | 20.051 | 1.00 | 28.57 C |
| ATOM | 6886 | CG | ASN | A | 452 | −42.969 | 18.380 | 19.757 | 1.00 | 28.30 C |
| ATOM | 6887 | OD1 | ASN | A | 452 | −42.622 | 19.517 | 19.468 | 1.00 | 29.35 O |
| ATOM | 6888 | ND2 | ASN | A | 452 | −44.236 | 18.018 | 19.836 | 1.00 | 28.36 N |
| ATOM | 6891 | C | ASN | A | 452 | −40.285 | 18.590 | 18.641 | 1.00 | 27.76 C |
| ATOM | 6892 | O | ASN | A | 452 | −39.365 | 19.018 | 19.296 | 1.00 | 28.04 O |
| ATOM | 6894 | N | SER | A | 453 | −40.807 | 19.269 | 17.630 | 1.00 | 26.77 N |
| ATOM | 6895 | CA | SER | A | 453 | −40.226 | 20.533 | 17.182 | 1.00 | 26.38 C |
| ATOM | 6897 | CB | SER | A | 453 | −40.912 | 21.015 | 15.903 | 1.00 | 26.40 C |
| ATOM | 6900 | OG | SER | A | 453 | −40.796 | 20.044 | 14.876 | 1.00 | 25.79 O |
| ATOM | 6902 | C | SER | A | 453 | −40.253 | 21.643 | 18.233 | 1.00 | 26.12 C |
| ATOM | 6903 | O | SER | A | 453 | −39.280 | 22.361 | 18.385 | 1.00 | 25.97 O |
| ATOM | 6905 | N | VAL | A | 454 | −41.368 | 21.784 | 18.942 | 1.00 | 26.15 N |
| ATOM | 6906 | CA | VAL | A | 454 | −41.518 | 22.780 | 20.022 | 1.00 | 26.21 C |
| ATOM | 6908 | CB | VAL | A | 454 | −42.975 | 22.818 | 20.532 | 1.00 | 26.04 C |
| ATOM | 6910 | CG1 | VAL | A | 454 | −43.122 | 23.787 | 21.694 | 1.00 | 25.24 C |
| ATOM | 6914 | CG2 | VAL | A | 454 | −43.913 | 23.190 | 19.401 | 1.00 | 26.32 C |
| ATOM | 6918 | C | VAL | A | 454 | −40.617 | 22.451 | 21.211 | 1.00 | 26.63 C |
| ATOM | 6919 | O | VAL | A | 454 | −40.173 | 23.328 | 21.959 | 1.00 | 26.53 O |
| ATOM | 6921 | N | SER | A | 455 | −40.374 | 21.160 | 21.380 | 1.00 | 27.21 N |
| ATOM | 6922 | CA | SER | A | 455 | −39.541 | 20.651 | 22.437 | 1.00 | 27.60 C |
| ATOM | 6924 | CB | SER | A | 455 | −39.677 | 19.141 | 22.490 | 1.00 | 27.31 C |
| ATOM | 6927 | OG | SER | A | 455 | −38.922 | 18.625 | 23.545 | 1.00 | 28.13 O |
| ATOM | 6929 | C | SER | A | 455 | −38.096 | 21.045 | 22.181 | 1.00 | 28.29 C |
| ATOM | 6930 | O | SER | A | 455 | −37.445 | 21.628 | 23.043 | 1.00 | 28.63 O |
| ATOM | 6932 | N | CYS | A | 456 | −37.599 | 20.748 | 20.988 | 1.00 | 29.04 N |
| ATOM | 6933 | CA | CYS | A | 456 | −36.219 | 21.082 | 20.640 | 1.00 | 29.65 C |
| ATOM | 6935 | CB | CYS | A | 456 | −35.868 | 20.535 | 19.256 | 1.00 | 29.52 C |
| ATOM | 6938 | SG | CYS | A | 456 | −35.959 | 18.734 | 19.163 | 1.00 | 29.71 S |
| ATOM | 6940 | C | CYS | A | 456 | −35.955 | 22.589 | 20.710 | 1.00 | 30.26 C |

TABLE 3-7-continued

Coordinates of *P. tremuloides IspS*

| | | | | | | | | | | | |
|---|---|---|---|---|---|---|---|---|---|---|---|
| ATOM | 6941 | O | CYS | A | 456 | −34.887 | 23.007 | 21.162 | 1.00 | 30.49 | O |
| ATOM | 6943 | N | TYR | A | 457 | −36.924 | 23.399 | 20.283 | 1.00 | 30.88 | N |
| ATOM | 6944 | CA | TYR | A | 457 | −36.767 | 24.850 | 20.308 | 1.00 | 31.45 | C |
| ATOM | 6946 | CB | TYR | A | 457 | −37.967 | 25.557 | 19.648 | 1.00 | 31.55 | C |
| ATOM | 6949 | CG | TYR | A | 457 | −37.691 | 26.991 | 19.178 | 1.00 | 32.09 | C |
| ATOM | 6950 | CD1 | TYR | A | 457 | −37.378 | 27.269 | 17.843 | 1.00 | 31.69 | C |
| ATOM | 6952 | CE1 | TYR | A | 457 | −37.128 | 28.569 | 17.418 | 1.00 | 31.73 | C |
| ATOM | 6954 | CZ | TYR | A | 457 | −37.186 | 29.613 | 18.328 | 1.00 | 32.84 | C |
| ATOM | 6955 | OH | TYR | A | 457 | −36.945 | 30.917 | 17.927 | 1.00 | 33.81 | O |
| ATOM | 6957 | CE2 | TYR | A | 457 | −37.492 | 29.364 | 19.658 | 1.00 | 32.72 | C |
| ATOM | 6959 | CD2 | TYR | A | 457 | −37.746 | 28.064 | 20.074 | 1.00 | 32.44 | C |
| ATOM | 6961 | C | TYR | A | 457 | −36.571 | 25.295 | 21.758 | 1.00 | 31.99 | C |
| ATOM | 6962 | O | TYR | A | 457 | −35.648 | 26.053 | 22.052 | 1.00 | 31.98 | O |
| ATOM | 6964 | N | MET | A | 458 | −37.419 | 24.799 | 22.661 | 1.00 | 32.76 | N |
| ATOM | 6965 | CA | MET | A | 458 | −37.211 | 24.987 | 24.105 | 1.00 | 33.37 | C |
| ATOM | 6967 | CB | MET | A | 458 | −38.151 | 24.097 | 24.921 | 1.00 | 33.43 | C |
| ATOM | 6970 | CG | MET | A | 458 | −39.570 | 24.593 | 25.059 | 1.00 | 33.70 | C |
| ATOM | 6973 | SD | MET | A | 458 | −40.641 | 23.312 | 25.737 | 1.00 | 34.59 | S |
| ATOM | 6974 | CE | MET | A | 458 | −39.709 | 22.763 | 27.179 | 1.00 | 34.71 | C |
| ATOM | 6978 | C | MET | A | 458 | −35.784 | 24.641 | 24.517 | 1.00 | 33.78 | C |
| ATOM | 6979 | O | MET | A | 458 | −35.101 | 25.437 | 25.151 | 1.00 | 33.73 | O |
| ATOM | 6981 | N | ARG | A | 459 | −35.347 | 23.445 | 24.145 | 1.00 | 34.46 | N |
| ATOM | 6982 | CA | ARG | A | 459 | −34.051 | 22.926 | 24.581 | 1.00 | 35.15 | C |
| ATOM | 6984 | CB | ARG | A | 459 | −33.876 | 21.447 | 24.171 | 1.00 | 35.68 | C |
| ATOM | 6987 | CG | ARG | A | 459 | −32.494 | 20.864 | 24.500 | 1.00 | 37.23 | C |
| ATOM | 6990 | CD | ARG | A | 459 | −32.491 | 19.345 | 24.752 | 1.00 | 39.80 | C |
| ATOM | 6993 | NE | ARG | A | 459 | −33.140 | 18.538 | 23.711 | 1.00 | 42.88 | N |
| ATOM | 6995 | CZ | ARG | A | 459 | −32.704 | 18.407 | 22.453 | 1.00 | 45.43 | C |
| ATOM | 6996 | NH1 | ARG | A | 459 | −31.615 | 19.062 | 22.035 | 1.00 | 47.50 | N |
| ATOM | 6999 | NH2 | ARG | A | 459 | −33.366 | 17.629 | 21.595 | 1.00 | 44.77 | N |
| ATOM | 7002 | C | ARG | A | 459 | −32.878 | 23.749 | 24.072 | 1.00 | 34.92 | C |
| ATOM | 7003 | O | ARG | A | 459 | −32.007 | 24.109 | 24.849 | 1.00 | 35.06 | O |
| ATOM | 7005 | N | THR | A | 460 | −32.854 | 24.047 | 22.778 | 1.00 | 34.96 | N |
| ATOM | 7006 | CA | THR | A | 460 | −31.674 | 24.678 | 22.163 | 1.00 | 34.91 | C |
| ATOM | 7008 | CB | THR | A | 460 | −31.494 | 24.263 | 20.680 | 1.00 | 34.88 | C |
| ATOM | 7010 | OG1 | THR | A | 460 | −32.330 | 25.067 | 19.841 | 1.00 | 34.39 | O |
| ATOM | 7012 | CG2 | THR | A | 460 | −31.825 | 22.776 | 20.488 | 1.00 | 35.44 | C |
| ATOM | 7016 | C | THR | A | 460 | −31.672 | 26.210 | 22.258 | 1.00 | 34.78 | C |
| ATOM | 7017 | O | THR | A | 460 | −30.673 | 26.837 | 21.911 | 1.00 | 34.92 | O |
| ATOM | 7019 | N | LYS | A | 461 | −32.781 | 26.806 | 22.701 | 1.00 | 34.41 | N |
| ATOM | 7020 | CA | LYS | A | 461 | −32.811 | 28.231 | 23.039 | 1.00 | 34.25 | C |
| ATOM | 7022 | CB | LYS | A | 461 | −33.921 | 28.947 | 22.265 | 1.00 | 34.56 | C |
| ATOM | 7025 | CG | LYS | A | 461 | −33.717 | 28.986 | 20.750 | 1.00 | 35.84 | C |
| ATOM | 7028 | CD | LYS | A | 461 | −32.519 | 29.859 | 20.347 | 1.00 | 37.64 | C |
| ATOM | 7031 | CE | LYS | A | 461 | −32.232 | 29.804 | 18.838 | 1.00 | 38.44 | C |
| ATOM | 7034 | NZ | LYS | A | 461 | −33.141 | 30.671 | 18.027 | 1.00 | 38.31 | N |
| ATOM | 7038 | C | LYS | A | 461 | −32.974 | 28.476 | 24.544 | 1.00 | 33.73 | C |
| ATOM | 7039 | O | LYS | A | 461 | −32.994 | 29.626 | 24.983 | 1.00 | 33.23 | O |
| ATOM | 7041 | N | GLY | A | 462 | −33.078 | 27.395 | 25.321 | 1.00 | 33.48 | N |
| ATOM | 7042 | CA | GLY | A | 462 | −33.173 | 27.464 | 26.784 | 1.00 | 33.23 | C |
| ATOM | 7045 | C | GLY | A | 462 | −34.332 | 28.320 | 27.239 | 1.00 | 32.95 | C |
| ATOM | 7046 | O | GLY | A | 462 | −34.144 | 29.258 | 28.004 | 1.00 | 33.17 | O |
| ATOM | 7048 | N | ILE | A | 463 | −35.528 | 28.000 | 26.757 | 1.00 | 32.52 | N |
| ATOM | 7049 | CA | ILE | A | 463 | −36.694 | 28.843 | 26.971 | 1.00 | 32.32 | C |
| ATOM | 7051 | CB | ILE | A | 463 | −37.006 | 29.724 | 25.734 | 1.00 | 32.47 | C |
| ATOM | 7053 | CG1 | ILE | A | 463 | −37.152 | 28.866 | 24.463 | 1.00 | 32.41 | C |
| ATOM | 7056 | CD1 | ILE | A | 463 | −37.359 | 29.675 | 23.191 | 1.00 | 32.02 | C |
| ATOM | 7060 | CG2 | ILE | A | 463 | −35.937 | 30.810 | 25.571 | 1.00 | 32.44 | C |
| ATOM | 7064 | C | ILE | A | 463 | −37.902 | 28.006 | 27.309 | 1.00 | 32.15 | C |
| ATOM | 7065 | O | ILE | A | 463 | −37.886 | 26.799 | 27.145 | 1.00 | 32.01 | O |
| ATOM | 7067 | N | SER | A | 464 | −38.950 | 28.670 | 27.780 | 1.00 | 32.27 | N |
| ATOM | 7068 | CA | SER | A | 464 | −40.163 | 28.006 | 28.239 | 1.00 | 32.52 | C |
| ATOM | 7070 | CB | SER | A | 464 | −40.964 | 28.974 | 29.110 | 1.00 | 32.65 | C |
| ATOM | 7073 | OG | SER | A | 464 | −41.112 | 30.224 | 28.457 | 1.00 | 32.69 | O |
| ATOM | 7075 | C | SER | A | 464 | −41.036 | 27.522 | 27.079 | 1.00 | 32.53 | C |
| ATOM | 7076 | O | SER | A | 464 | −40.968 | 28.069 | 25.986 | 1.00 | 32.62 | O |
| ATOM | 7078 | N | GLU | A | 465 | −41.857 | 26.500 | 27.332 | 1.00 | 32.47 | N |
| ATOM | 7079 | CA | GLU | A | 465 | −42.836 | 26.010 | 26.353 | 1.00 | 32.33 | C |
| ATOM | 7081 | CB | GLU | A | 465 | −43.689 | 24.868 | 26.935 | 1.00 | 32.34 | C |
| ATOM | 7084 | CG | GLU | A | 465 | −44.756 | 24.312 | 25.974 | 1.00 | 32.37 | C |
| ATOM | 7087 | CD | GLU | A | 465 | −45.675 | 23.279 | 26.611 | 1.00 | 32.47 | C |
| ATOM | 7088 | OE1 | GLU | A | 465 | −45.297 | 22.659 | 27.630 | 1.00 | 31.63 | O |
| ATOM | 7089 | OE2 | GLU | A | 465 | −46.785 | 23.086 | 26.074 | 1.00 | 32.77 | O |
| ATOM | 7090 | C | GLU | A | 465 | −43.758 | 27.124 | 25.864 | 1.00 | 32.33 | C |
| ATOM | 7091 | O | GLU | A | 465 | −44.078 | 27.183 | 24.676 | 1.00 | 32.60 | O |
| ATOM | 7093 | N | GLU | A | 466 | −44.196 | 28.001 | 26.767 | 1.00 | 32.08 | N |
| ATOM | 7094 | CA | GLU | A | 466 | −45.085 | 29.097 | 26.380 | 1.00 | 31.79 | C |
| ATOM | 7096 | CB | GLU | A | 466 | −45.606 | 29.832 | 27.624 | 1.00 | 31.91 | C |

TABLE 3-7-continued

Coordinates of *P. tremuloides IspS*

| | | | | | | | | | | | |
|---|---|---|---|---|---|---|---|---|---|---|---|
| ATOM | 7099 | CG | GLU | A | 466 | −46.503 | 31.041 | 27.304 | 1.00 | 32.82 | C |
| ATOM | 7102 | CD | GLU | A | 466 | −47.426 | 31.472 | 28.452 | 1.00 | 33.67 | C |
| ATOM | 7103 | OE1 | GLU | A | 466 | −47.519 | 30.756 | 29.478 | 1.00 | 35.09 | O |
| ATOM | 7104 | OE2 | GLU | A | 466 | −48.077 | 32.533 | 28.312 | 1.00 | 33.12 | O |
| ATOM | 7105 | C | GLU | A | 466 | −44.392 | 30.052 | 25.386 | 1.00 | 31.13 | C |
| ATOM | 7106 | O | GLU | A | 466 | −45.032 | 30.603 | 24.492 | 1.00 | 30.87 | O |
| ATOM | 7108 | N | LEU | A | 467 | −43.077 | 30.194 | 25.531 | 1.00 | 30.57 | N |
| ATOM | 7109 | CA | LEU | A | 467 | −42.265 | 31.102 | 24.708 | 1.00 | 30.18 | C |
| ATOM | 7111 | CB | LEU | A | 467 | −41.055 | 31.604 | 25.524 | 1.00 | 30.38 | C |
| ATOM | 7114 | CG | LEU | A | 467 | −40.674 | 33.087 | 25.463 | 1.00 | 30.39 | C |
| ATOM | 7116 | CD1 | LEU | A | 467 | −41.608 | 33.900 | 26.362 | 1.00 | 30.23 | C |
| ATOM | 7120 | CD2 | LEU | A | 467 | −39.214 | 33.308 | 25.872 | 1.00 | 30.31 | C |
| ATOM | 7124 | C | LEU | A | 467 | −41.773 | 30.401 | 23.439 | 1.00 | 29.47 | C |
| ATOM | 7125 | O | LEU | A | 467 | −41.660 | 31.010 | 22.382 | 1.00 | 29.17 | O |
| ATOM | 7127 | N | ALA | A | 468 | −41.445 | 29.121 | 23.562 | 1.00 | 28.93 | N |
| ATOM | 7128 | CA | ALA | A | 468 | −41.095 | 28.310 | 22.404 | 1.00 | 28.45 | C |
| ATOM | 7130 | CB | ALA | A | 468 | −40.613 | 26.935 | 22.830 | 1.00 | 28.10 | C |
| ATOM | 7134 | C | ALA | A | 468 | −42.306 | 28.193 | 21.494 | 1.00 | 28.08 | C |
| ATOM | 7135 | O | ALA | A | 468 | −42.179 | 28.321 | 20.285 | 1.00 | 28.24 | O |
| ATOM | 7137 | N | THR | A | 469 | −43.479 | 27.964 | 22.080 | 1.00 | 27.58 | N |
| ATOM | 7138 | CA | THR | A | 469 | −44.719 | 27.870 | 21.322 | 1.00 | 27.26 | C |
| ATOM | 7140 | CB | THR | A | 469 | −45.928 | 27.710 | 22.261 | 1.00 | 27.28 | C |
| ATOM | 7142 | OG1 | THR | A | 469 | −46.063 | 26.330 | 22.627 | 1.00 | 27.55 | O |
| ATOM | 7144 | CG2 | THR | A | 469 | −47.222 | 28.185 | 21.597 | 1.00 | 27.34 | C |
| ATOM | 7148 | C | THR | A | 469 | −44.916 | 29.099 | 20.449 | 1.00 | 27.10 | C |
| ATOM | 7149 | O | THR | A | 469 | −45.176 | 28.989 | 19.250 | 1.00 | 27.11 | O |
| ATOM | 7151 | N | GLU | A | 470 | −44.774 | 30.267 | 21.061 | 1.00 | 26.88 | N |
| ATOM | 7152 | CA | GLU | A | 470 | −44.944 | 31.542 | 20.376 | 1.00 | 26.84 | C |
| ATOM | 7154 | CB | GLU | A | 470 | −44.832 | 32.663 | 21.400 | 1.00 | 27.07 | C |
| ATOM | 7157 | CG | GLU | A | 470 | −45.357 | 34.003 | 20.958 | 1.00 | 28.47 | C |
| ATOM | 7160 | CD | GLU | A | 470 | −45.140 | 35.087 | 22.008 | 1.00 | 30.51 | C |
| ATOM | 7161 | OE1 | GLU | A | 470 | −45.029 | 34.775 | 23.221 | 1.00 | 31.53 | O |
| ATOM | 7162 | OE2 | GLU | A | 470 | −45.083 | 36.269 | 21.608 | 1.00 | 32.59 | O |
| ATOM | 7163 | C | GLU | A | 470 | −43.926 | 31.750 | 19.239 | 1.00 | 26.48 | C |
| ATOM | 7164 | O | GLU | A | 470 | −44.261 | 32.296 | 18.184 | 1.00 | 26.29 | O |
| ATOM | 7166 | N | SER | A | 471 | −42.686 | 31.316 | 19.452 | 1.00 | 26.12 | N |
| ATOM | 7167 | CA | SER | A | 471 | −41.660 | 31.386 | 18.408 | 1.00 | 25.85 | C |
| ATOM | 7169 | CB | SER | A | 471 | −40.296 | 30.933 | 18.941 | 1.00 | 25.96 | C |
| ATOM | 7172 | OG | SER | A | 471 | −39.656 | 31.939 | 19.711 | 1.00 | 26.53 | O |
| ATOM | 7174 | C | SER | A | 471 | −42.036 | 30.529 | 17.208 | 1.00 | 25.35 | C |
| ATOM | 7175 | O | SER | A | 471 | −41.761 | 30.899 | 16.067 | 1.00 | 25.43 | O |
| ATOM | 7177 | N | VAL | A | 472 | −42.653 | 29.381 | 17.482 | 1.00 | 24.95 | N |
| ATOM | 7178 | CA | VAL | A | 472 | −43.097 | 28.451 | 16.438 | 1.00 | 24.65 | C |
| ATOM | 7180 | CB | VAL | A | 472 | −43.485 | 27.055 | 17.024 | 1.00 | 24.57 | C |
| ATOM | 7182 | CG1 | VAL | A | 472 | −44.257 | 26.222 | 16.016 | 1.00 | 23.23 | C |
| ATOM | 7186 | CG2 | VAL | A | 472 | −42.232 | 26.309 | 17.494 | 1.00 | 23.83 | C |
| ATOM | 7190 | C | VAL | A | 472 | −44.252 | 29.039 | 15.631 | 1.00 | 24.71 | C |
| ATOM | 7191 | O | VAL | A | 472 | −44.369 | 28.776 | 14.440 | 1.00 | 24.63 | O |
| ATOM | 7193 | N | MET | A | 473 | −45.073 | 29.866 | 16.269 | 1.00 | 24.79 | N |
| ATOM | 7194 | CA | MET | A | 473 | −46.143 | 30.591 | 15.565 | 1.00 | 24.94 | C |
| ATOM | 7196 | CB | MET | A | 473 | −47.059 | 31.266 | 16.576 | 1.00 | 25.11 | C |
| ATOM | 7199 | CG | MET | A | 473 | −47.683 | 30.335 | 17.560 | 1.00 | 25.11 | C |
| ATOM | 7202 | SD | MET | A | 473 | −48.967 | 29.391 | 16.780 | 1.00 | 25.35 | S |
| ATOM | 7203 | CE | MET | A | 473 | −50.064 | 29.163 | 18.189 | 1.00 | 26.11 | C |
| ATOM | 7207 | C | MET | A | 473 | −45.613 | 31.672 | 14.605 | 1.00 | 24.86 | C |
| ATOM | 7208 | O | MET | A | 473 | −46.132 | 31.849 | 13.513 | 1.00 | 24.57 | O |
| ATOM | 7210 | N | ASN | A | 474 | −44.589 | 32.405 | 15.032 | 1.00 | 24.89 | N |
| ATOM | 7211 | CA | ASN | A | 474 | −43.951 | 33.383 | 14.166 | 1.00 | 25.00 | C |
| ATOM | 7213 | CB | ASN | A | 474 | −43.009 | 34.278 | 14.966 | 1.00 | 25.12 | C |
| ATOM | 7216 | CG | ASN | A | 474 | −43.700 | 34.966 | 16.127 | 1.00 | 25.77 | C |
| ATOM | 7217 | OD1 | ASN | A | 474 | −43.058 | 35.312 | 17.114 | 1.00 | 26.96 | O |
| ATOM | 7218 | ND2 | ASN | A | 474 | −45.015 | 35.163 | 16.021 | 1.00 | 26.31 | N |
| ATOM | 7221 | C | ASN | A | 474 | −43.195 | 32.707 | 13.024 | 1.00 | 24.84 | C |
| ATOM | 7222 | O | ASN | A | 474 | −42.979 | 33.313 | 11.973 | 1.00 | 25.07 | O |
| ATOM | 7224 | N | LEU | A | 475 | −42.792 | 31.455 | 13.227 | 1.00 | 24.46 | N |
| ATOM | 7225 | CA | LEU | A | 475 | −42.218 | 30.671 | 12.142 | 1.00 | 24.06 | C |
| ATOM | 7227 | CB | LEU | A | 475 | −41.596 | 29.367 | 12.653 | 1.00 | 24.27 | C |
| ATOM | 7230 | CG | LEU | A | 475 | −40.307 | 29.072 | 11.886 | 1.00 | 25.08 | C |
| ATOM | 7232 | CD1 | LEU | A | 475 | −39.207 | 30.000 | 12.419 | 1.00 | 25.89 | C |
| ATOM | 7236 | CD2 | LEU | A | 475 | −39.887 | 27.622 | 11.985 | 1.00 | 25.33 | C |
| ATOM | 7240 | C | LEU | A | 475 | −43.278 | 30.365 | 11.085 | 1.00 | 23.26 | C |
| ATOM | 7241 | O | LEU | A | 475 | −43.018 | 30.479 | 9.884 | 1.00 | 22.90 | O |
| ATOM | 7243 | N | ILE | A | 476 | −44.471 | 29.978 | 11.534 | 1.00 | 22.53 | N |
| ATOM | 7244 | CA | ILE | A | 476 | −45.544 | 29.632 | 10.606 | 1.00 | 21.93 | C |
| ATOM | 7246 | CB | ILE | A | 476 | −46.773 | 29.017 | 11.308 | 1.00 | 21.58 | C |
| ATOM | 7248 | CG1 | ILE | A | 476 | −46.499 | 27.550 | 11.664 | 1.00 | 21.32 | C |
| ATOM | 7251 | CD1 | ILE | A | 476 | −47.552 | 26.902 | 12.598 | 1.00 | 20.33 | C |
| ATOM | 7255 | CG2 | ILE | A | 476 | −47.994 | 29.104 | 10.428 | 1.00 | 20.46 | C |

TABLE 3-7-continued

Coordinates of *P. tremuloides IspS*

| | | | | | | | | | | | |
|---|---|---|---|---|---|---|---|---|---|---|---|
| ATOM | 7259 | C | ILE | A | 476 | −45.926 | 30.887 | 9.853 | 1.00 | 22.07 | C |
| ATOM | 7260 | O | ILE | A | 476 | −46.007 | 30.869 | 8.626 | 1.00 | 22.47 | O |
| ATOM | 7262 | N | ASP | A | 477 | −46.122 | 31.982 | 10.584 | 1.00 | 21.81 | N |
| ATOM | 7263 | CA | ASP | A | 477 | −46.483 | 33.245 | 9.970 | 1.00 | 21.56 | C |
| ATOM | 7265 | CB | ASP | A | 477 | −46.643 | 34.337 | 11.032 | 1.00 | 21.89 | C |
| ATOM | 7268 | CG | ASP | A | 477 | −47.962 | 34.217 | 11.817 | 1.00 | 23.39 | C |
| ATOM | 7269 | OD1 | ASP | A | 477 | −48.854 | 33.441 | 11.375 | 1.00 | 24.41 | O |
| ATOM | 7270 | OD2 | ASP | A | 477 | −48.103 | 34.902 | 12.875 | 1.00 | 23.80 | O |
| ATOM | 7271 | C | ASP | A | 477 | −45.425 | 33.626 | 8.947 | 1.00 | 21.06 | C |
| ATOM | 7272 | O | ASP | A | 477 | −45.759 | 33.913 | 7.795 | 1.00 | 20.78 | O |
| ATOM | 7274 | N | GLU | A | 478 | −44.156 | 33.591 | 9.361 | 1.00 | 20.63 | N |
| ATOM | 7275 | CA | GLU | A | 478 | −43.027 | 33.919 | 8.467 | 1.00 | 20.45 | C |
| ATOM | 7277 | CB | GLU | A | 478 | −41.680 | 33.793 | 9.200 | 1.00 | 20.66 | C |
| ATOM | 7280 | CG | GLU | A | 478 | −40.422 | 34.044 | 8.339 | 1.00 | 22.27 | C |
| ATOM | 7283 | CD | GLU | A | 478 | −39.107 | 33.579 | 9.018 | 1.00 | 24.72 | C |
| ATOM | 7284 | OE1 | GLU | A | 478 | −38.553 | 34.367 | 9.817 | 1.00 | 26.19 | O |
| ATOM | 7285 | OE2 | GLU | A | 478 | −38.619 | 32.442 | 8.745 | 1.00 | 25.66 | O |
| ATOM | 7286 | C | GLU | A | 478 | −43.041 | 33.042 | 7.217 | 1.00 | 19.54 | C |
| ATOM | 7287 | O | GLU | A | 478 | −42.879 | 33.544 | 6.102 | 1.00 | 19.02 | O |
| ATOM | 7289 | N | THR | A | 479 | −43.250 | 31.743 | 7.413 | 1.00 | 18.76 | N |
| ATOM | 7290 | CA | THR | A | 479 | −43.358 | 30.808 | 6.294 | 1.00 | 18.45 | C |
| ATOM | 7292 | CB | THR | A | 479 | −43.503 | 29.339 | 6.774 | 1.00 | 18.26 | C |
| ATOM | 7294 | OG1 | THR | A | 479 | −42.334 | 28.955 | 7.494 | 1.00 | 17.30 | O |
| ATOM | 7296 | CG2 | THR | A | 479 | −43.669 | 28.394 | 5.592 | 1.00 | 17.93 | C |
| ATOM | 7300 | C | THR | A | 479 | −44.504 | 31.173 | 5.314 | 1.00 | 18.39 | C |
| ATOM | 7301 | O | THR | A | 479 | −44.280 | 31.200 | 4.103 | 1.00 | 18.58 | O |
| ATOM | 7303 | N | TRP | A | 480 | −45.709 | 31.457 | 5.818 | 1.00 | 17.85 | N |
| ATOM | 7304 | CA | TRP | A | 480 | −46.801 | 31.909 | 4.942 | 1.00 | 17.44 | C |
| ATOM | 7306 | CB | TRP | A | 480 | −48.086 | 32.225 | 5.728 | 1.00 | 17.67 | C |
| ATOM | 7309 | CG | TRP | A | 480 | −48.969 | 31.042 | 5.888 | 1.00 | 17.09 | C |
| ATOM | 7310 | CD1 | TRP | A | 480 | −48.996 | 30.195 | 6.936 | 1.00 | 16.76 | C |
| ATOM | 7312 | NE1 | TRP | A | 480 | −49.914 | 29.216 | 6.724 | 1.00 | 17.08 | N |
| ATOM | 7314 | CE2 | TRP | A | 480 | −50.501 | 29.410 | 5.507 | 1.00 | 17.86 | C |
| ATOM | 7315 | CD2 | TRP | A | 480 | −49.930 | 30.559 | 4.954 | 1.00 | 17.15 | C |
| ATOM | 7316 | CE3 | TRP | A | 480 | −50.356 | 30.980 | 3.696 | 1.00 | 18.31 | C |
| ATOM | 7318 | CZ3 | TRP | A | 480 | −51.337 | 30.244 | 3.039 | 1.00 | 19.10 | C |
| ATOM | 7320 | CH2 | TRP | A | 480 | −51.897 | 29.107 | 3.622 | 1.00 | 18.83 | C |
| ATOM | 7322 | CZ2 | TRP | A | 480 | −51.493 | 28.673 | 4.855 | 1.00 | 18.86 | C |
| ATOM | 7324 | C | TRP | A | 480 | −46.426 | 33.124 | 4.097 | 1.00 | 17.10 | C |
| ATOM | 7325 | O | TRP | A | 480 | −46.824 | 33.215 | 2.943 | 1.00 | 17.22 | O |
| ATOM | 7327 | N | LYS | A | 481 | −45.675 | 34.062 | 4.659 | 1.00 | 16.60 | N |
| ATOM | 7328 | CA | LYS | A | 481 | −45.275 | 35.215 | 3.886 | 1.00 | 16.23 | C |
| ATOM | 7330 | CB | LYS | A | 481 | −44.566 | 36.243 | 4.747 | 1.00 | 16.42 | C |
| ATOM | 7333 | CG | LYS | A | 481 | −45.417 | 36.954 | 5.769 | 1.00 | 16.42 | C |
| ATOM | 7336 | CD | LYS | A | 481 | −44.555 | 37.979 | 6.505 | 1.00 | 16.40 | C |
| ATOM | 7339 | CE | LYS | A | 481 | −45.199 | 38.504 | 7.782 | 1.00 | 16.66 | C |
| ATOM | 7342 | NZ | LYS | A | 481 | −44.184 | 38.717 | 8.846 | 1.00 | 16.72 | N |
| ATOM | 7346 | C | LYS | A | 481 | −44.357 | 34.782 | 2.767 | 1.00 | 15.94 | C |
| ATOM | 7347 | O | LYS | A | 481 | −44.451 | 35.291 | 1.674 | 1.00 | 16.09 | O |
| ATOM | 7349 | N | LYS | A | 482 | −43.461 | 33.849 | 3.034 | 1.00 | 15.98 | N |
| ATOM | 7350 | CA | LYS | A | 482 | −42.559 | 33.369 | 1.996 | 1.00 | 16.30 | C |
| ATOM | 7352 | CB | LYS | A | 482 | −41.409 | 32.563 | 2.594 | 1.00 | 16.51 | C |
| ATOM | 7355 | CG | LYS | A | 482 | −40.354 | 33.445 | 3.286 | 1.00 | 17.46 | C |
| ATOM | 7358 | CD | LYS | A | 482 | −39.486 | 32.647 | 4.241 | 1.00 | 18.48 | C |
| ATOM | 7361 | CE | LYS | A | 482 | −38.625 | 33.548 | 5.096 | 1.00 | 18.94 | C |
| ATOM | 7364 | NZ | LYS | A | 482 | −37.865 | 32.773 | 6.129 | 1.00 | 20.40 | N |
| ATOM | 7368 | C | LYS | A | 482 | −43.296 | 32.561 | .938 | 1.00 | 16.40 | C |
| ATOM | 7369 | O | LYS | A | 482 | −42.941 | 32.614 | −.229 | 1.00 | 16.85 | O |
| ATOM | 7371 | N | MET | A | 483 | −44.328 | 31.824 | 1.332 | 1.00 | 16.57 | N |
| ATOM | 7372 | CA | MET | A | 483 | −45.149 | 31.100 | .366 | 1.00 | 16.67 | C |
| ATOM | 7374 | CB | MET | A | 483 | −46.128 | 30.156 | 1.057 | 1.00 | 16.55 | C |
| ATOM | 7377 | CG | MET | A | 483 | −45.496 | 28.923 | 1.675 | 1.00 | 16.50 | C |
| ATOM | 7380 | SD | MET | A | 483 | −46.715 | 27.684 | 2.194 | 1.00 | 17.39 | S |
| ATOM | 7381 | CE | MET | A | 483 | −47.937 | 28.704 | 3.025 | 1.00 | 17.27 | C |
| ATOM | 7385 | C | MET | A | 483 | −45.928 | 32.069 | −.495 | 1.00 | 17.06 | C |
| ATOM | 7386 | O | MET | A | 483 | −46.027 | 31.867 | −1.688 | 1.00 | 17.17 | O |
| ATOM | 7388 | N | ASN | A | 484 | −46.483 | 33.110 | .118 | 1.00 | 17.72 | N |
| ATOM | 7389 | CA | ASN | A | 484 | −47.305 | 34.093 | −.587 | 1.00 | 18.35 | C |
| ATOM | 7391 | CB | ASN | A | 484 | −47.861 | 35.129 | .397 | 1.00 | 18.26 | C |
| ATOM | 7394 | CG | ASN | A | 484 | −48.994 | 34.601 | 1.248 | 1.00 | 17.35 | C |
| ATOM | 7395 | OD1 | ASN | A | 484 | −49.597 | 33.577 | .934 | 1.00 | 17.54 | O |
| ATOM | 7396 | ND2 | ASN | A | 484 | −49.304 | 35.317 | 2.331 | 1.00 | 14.10 | N |
| ATOM | 7399 | C | ASN | A | 484 | −46.541 | 34.839 | −1.677 | 1.00 | 19.51 | C |
| ATOM | 7400 | O | ASN | A | 484 | −47.123 | 35.250 | −2.685 | 1.00 | 19.49 | O |
| ATOM | 7402 | N | LYS | A | 485 | −45.243 | 35.035 | −1.463 | 1.00 | 20.86 | N |
| ATOM | 7403 | CA | LYS | A | 485 | −44.394 | 35.681 | −2.456 | 1.00 | 22.12 | C |
| ATOM | 7405 | CB | LYS | A | 485 | −43.070 | 36.092 | −1.823 | 1.00 | 22.08 | C |
| ATOM | 7408 | CG | LYS | A | 485 | −42.229 | 37.060 | −2.641 | 1.00 | 23.09 | C |

TABLE 3-7-continued

Coordinates of *P. tremuloides IspS*

| | | | | | | | | | | |
|---|---|---|---|---|---|---|---|---|---|---|
| ATOM | 7411 | CD | LYS | A | 485 | −40.783 | 37.072 | −2.109 | 1.00 | 25.38 C |
| ATOM | 7414 | CE | LYS | A | 485 | −40.098 | 38.460 | −2.135 | 1.00 | 26.12 C |
| ATOM | 7417 | NZ | LYS | A | 485 | −38.943 | 38.555 | −3.086 | 1.00 | 26.61 N |
| ATOM | 7421 | C | LYS | A | 485 | −44.164 | 34.743 | −3.656 | 1.00 | 23.36 C |
| ATOM | 7422 | O | LYS | A | 485 | −44.120 | 35.191 | −4.802 | 1.00 | 23.00 O |
| ATOM | 7424 | N | GLU | A | 486 | −44.027 | 33.442 | −3.400 | 1.00 | 24.99 N |
| ATOM | 7425 | CA | GLU | A | 486 | −43.902 | 32.479 | −4.491 | 1.00 | 26.35 C |
| ATOM | 7427 | CB | GLU | A | 486 | −43.627 | 31.061 | −3.978 | 1.00 | 26.55 C |
| ATOM | 7430 | CG | GLU | A | 486 | −42.985 | 30.130 | −5.033 | 1.00 | 28.29 C |
| ATOM | 7433 | CD | GLU | A | 486 | −41.466 | 30.324 | −5.191 | 1.00 | 31.11 C |
| ATOM | 7434 | OE1 | GLU | A | 486 | −40.981 | 30.466 | −6.341 | 1.00 | 32.07 O |
| ATOM | 7435 | OE2 | GLU | A | 486 | −40.744 | 30.335 | −4.159 | 1.00 | 33.04 O |
| ATOM | 7436 | C | GLU | A | 486 | −45.157 | 32.501 | −5.362 | 1.00 | 27.13 C |
| ATOM | 7437 | O | GLU | A | 486 | −45.064 | 32.618 | −6.583 | 1.00 | 27.57 O |
| ATOM | 7439 | N | LYS | A | 487 | −46.325 | 32.422 | −4.739 | 1.00 | 28.12 N |
| ATOM | 7440 | CA | LYS | A | 487 | −47.582 | 32.378 | −5.485 | 1.00 | 29.12 C |
| ATOM | 7442 | CB | LYS | A | 487 | −48.788 | 32.260 | −4.542 | 1.00 | 29.21 C |
| ATOM | 7445 | CG | LYS | A | 487 | −50.167 | 32.296 | −5.235 | 1.00 | 28.57 C |
| ATOM | 7448 | CD | LYS | A | 487 | −50.403 | 31.040 | −6.036 | 1.00 | 27.91 C |
| ATOM | 7451 | CE | LYS | A | 487 | −51.615 | 31.141 | −6.936 | 1.00 | 28.38 C |
| ATOM | 7454 | NZ | LYS | A | 487 | −52.874 | 31.460 | −6.211 | 1.00 | 28.03 N |
| ATOM | 7458 | C | LYS | A | 487 | −47.756 | 33.603 | −6.352 | 1.00 | 30.18 C |
| ATOM | 7459 | O | LYS | A | 487 | −48.308 | 33.514 | −7.446 | 1.00 | 30.21 O |
| ATOM | 7461 | N | LEU | A | 488 | −47.295 | 34.743 | −5.844 | 1.00 | 31.64 N |
| ATOM | 7462 | CA | LEU | A | 488 | −47.422 | 36.026 | −6.532 | 1.00 | 32.65 C |
| ATOM | 7464 | CB | LEU | A | 488 | −47.426 | 37.144 | −5.494 | 1.00 | 32.43 C |
| ATOM | 7467 | CG | LEU | A | 488 | −48.091 | 38.446 | −5.907 | 1.00 | 32.50 C |
| ATOM | 7469 | CD1 | LEU | A | 488 | −49.593 | 38.288 | −5.943 | 1.00 | 32.66 C |
| ATOM | 7473 | CD2 | LEU | A | 488 | −47.707 | 39.554 | −4.943 | 1.00 | 33.38 C |
| ATOM | 7477 | C | LEU | A | 488 | −46.286 | 36.242 | −7.542 | 1.00 | 33.99 C |
| ATOM | 7478 | O | LEU | A | 488 | −46.536 | 36.539 | −8.705 | 1.00 | 33.72 O |
| ATOM | 7480 | N | GLY | A | 489 | −45.046 | 36.045 | −7.091 | 1.00 | 35.85 N |
| ATOM | 7481 | CA | GLY | A | 489 | −43.845 | 36.361 | −7.874 | 1.00 | 37.37 C |
| ATOM | 7484 | C | GLY | A | 489 | −43.278 | 35.221 | −8.709 | 1.00 | 38.76 C |
| ATOM | 7485 | O | GLY | A | 489 | −42.414 | 34.467 | −8.250 | 1.00 | 39.06 O |
| ATOM | 7487 | N | GLY | A | 490 | −43.760 | 35.119 | −9.947 | 1.00 | 40.26 N |
| ATOM | 7488 | CA | GLY | A | 490 | −43.285 | 34.130 | −10.927 | 1.00 | 41.03 C |
| ATOM | 7491 | C | GLY | A | 490 | −42.193 | 33.194 | −10.436 | 1.00 | 41.61 C |
| ATOM | 7492 | O | GLY | A | 490 | −41.010 | 33.547 | −10.423 | 1.00 | 41.62 O |
| ATOM | 7494 | N | SER | A | 491 | −42.590 | 31.996 | −10.023 | 1.00 | 42.17 N |
| ATOM | 7495 | CA | SER | A | 491 | −41.619 | 30.962 | −9.662 | 1.00 | 42.54 C |
| ATOM | 7497 | CB | SER | A | 491 | −42.279 | 29.909 | −8.741 | 1.00 | 42.63 C |
| ATOM | 7500 | OG | SER | A | 491 | −43.451 | 29.345 | −9.294 | 1.00 | 42.44 O |
| ATOM | 7502 | C | SER | A | 491 | −41.032 | 30.349 | −10.952 | 1.00 | 42.50 C |
| ATOM | 7503 | O | SER | A | 491 | −41.117 | 30.961 | −12.030 | 1.00 | 42.57 O |
| ATOM | 7505 | N | LEU | A | 492 | −40.405 | 29.177 | −10.843 | 1.00 | 42.18 N |
| ATOM | 7506 | CA | LEU | A | 492 | −40.185 | 28.333 | −12.021 | 1.00 | 41.96 C |
| ATOM | 7508 | CB | LEU | A | 492 | −39.110 | 27.270 | −11.782 | 1.00 | 42.39 C |
| ATOM | 7511 | CG | LEU | A | 492 | −37.695 | 27.671 | −11.353 | 1.00 | 44.21 C |
| ATOM | 7513 | CD1 | LEU | A | 492 | −36.783 | 26.438 | −11.498 | 1.00 | 45.26 C |
| ATOM | 7517 | CD2 | LEU | A | 492 | −37.120 | 28.896 | −12.129 | 1.00 | 45.51 C |
| ATOM | 7521 | C | LEU | A | 492 | −41.479 | 27.610 | −12.356 | 1.00 | 40.88 C |
| ATOM | 7522 | O | LEU | A | 492 | −41.713 | 27.244 | −13.504 | 1.00 | 40.78 O |
| ATOM | 7524 | N | PHE | A | 493 | −42.308 | 27.409 | −11.339 | 1.00 | 39.61 N |
| ATOM | 7525 | CA | PHE | A | 493 | −43.500 | 26.595 | −11.460 | 1.00 | 38.85 C |
| ATOM | 7527 | CB | PHE | A | 493 | −43.783 | 25.911 | −10.124 | 1.00 | 38.62 C |
| ATOM | 7530 | CG | PHE | A | 493 | −42.725 | 24.937 | −9.713 | 1.00 | 37.16 C |
| ATOM | 7531 | CD1 | PHE | A | 493 | −42.901 | 23.587 | −9.916 | 1.00 | 35.26 C |
| ATOM | 7533 | CE1 | PHE | A | 493 | −41.934 | 22.698 | −9.546 | 1.00 | 34.86 C |
| ATOM | 7535 | CZ | PHE | A | 493 | −40.769 | 23.143 | −8.966 | 1.00 | 35.09 C |
| ATOM | 7537 | CE2 | PHE | A | 493 | −40.574 | 24.482 | −8.759 | 1.00 | 35.45 C |
| ATOM | 7539 | CD2 | PHE | A | 493 | −41.549 | 25.374 | −9.130 | 1.00 | 36.36 C |
| ATOM | 7541 | C | PHE | A | 493 | −44.714 | 27.412 | −11.890 | 1.00 | 38.62 C |
| ATOM | 7542 | O | PHE | A | 493 | −44.756 | 28.621 | −11.702 | 1.00 | 38.86 O |
| ATOM | 7544 | N | ALA | A | 494 | −45.698 | 26.731 | −12.469 | 1.00 | 38.32 N |
| ATOM | 7545 | CA | ALA | A | 494 | −46.977 | 27.337 | −12.843 | 1.00 | 38.09 C |
| ATOM | 7547 | CB | ALA | A | 494 | −47.658 | 26.486 | −13.906 | 1.00 | 38.17 C |
| ATOM | 7551 | C | ALA | A | 494 | −47.891 | 27.479 | −11.623 | 1.00 | 37.76 C |
| ATOM | 7552 | O | ALA | A | 494 | −48.039 | 26.541 | −10.845 | 1.00 | 38.15 O |
| ATOM | 7554 | N | LYS | A | 495 | −48.541 | 28.629 | −11.484 | 1.00 | 37.15 N |
| ATOM | 7555 | CA | LYS | A | 495 | −49.321 | 28.947 | −10.270 | 1.00 | 36.53 C |
| ATOM | 7557 | CB | LYS | A | 495 | −50.116 | 30.258 | −10.477 | 1.00 | 36.90 C |
| ATOM | 7560 | CG | LYS | A | 495 | −49.235 | 31.524 | −10.582 | 1.00 | 37.72 C |
| ATOM | 7563 | CD | LYS | A | 495 | −50.061 | 32.826 | −10.585 | 1.00 | 38.87 C |
| ATOM | 7566 | CE | LYS | A | 495 | −49.140 | 34.065 | −10.665 | 1.00 | 39.78 C |
| ATOM | 7569 | NZ | LYS | A | 495 | −49.786 | 35.369 | −10.282 | 1.00 | 39.78 N |
| ATOM | 7573 | C | LYS | A | 495 | −50.238 | 27.809 | −9.724 | 1.00 | 35.25 C |
| ATOM | 7574 | O | LYS | A | 495 | −50.261 | 27.563 | −8.523 | 1.00 | 34.91 O |

TABLE 3-7-continued

Coordinates of *P. tremuloides IspS*

| | | | | | | | | | | | |
|---|---|---|---|---|---|---|---|---|---|---|---|
| ATOM | 7576 | N | PRO | A | 496 | −50.978 | 27.107 | −10.599 | 1.00 | 33.76 | N |
| ATOM | 7577 | CA | PRO | A | 496 | −51.846 | 26.015 | −10.162 | 1.00 | 32.74 | C |
| ATOM | 7579 | CB | PRO | A | 496 | −52.222 | 25.340 | −11.474 | 1.00 | 32.99 | C |
| ATOM | 7582 | CG | PRO | A | 496 | −52.337 | 26.470 | −12.385 | 1.00 | 33.75 | C |
| ATOM | 7585 | CD | PRO | A | 496 | −51.196 | 27.400 | −12.022 | 1.00 | 33.83 | C |
| ATOM | 7588 | C | PRO | A | 496 | −51.194 | 24.998 | −9.267 | 1.00 | 31.24 | C |
| ATOM | 7589 | O | PRO | A | 496 | −51.822 | 24.522 | −8.331 | 1.00 | 31.54 | O |
| ATOM | 7590 | N | PHE | A | 497 | −49.954 | 24.642 | −9.566 | 1.00 | 29.40 | N |
| ATOM | 7591 | CA | PHE | A | 497 | −49.229 | 23.726 | −8.708 | 1.00 | 27.76 | C |
| ATOM | 7593 | CB | PHE | A | 497 | −48.162 | 22.948 | −9.474 | 1.00 | 27.62 | C |
| ATOM | 7596 | CG | PHE | A | 497 | −47.351 | 22.040 | −8.597 | 1.00 | 26.33 | C |
| ATOM | 7597 | CD1 | PHE | A | 497 | −47.944 | 20.969 | −7.974 | 1.00 | 24.96 | C |
| ATOM | 7599 | CE1 | PHE | A | 497 | −47.218 | 20.151 | −7.156 | 1.00 | 25.04 | C |
| ATOM | 7601 | CZ | PHE | A | 497 | −45.875 | 20.396 | −6.940 | 1.00 | 24.79 | C |
| ATOM | 7603 | CE2 | PHE | A | 497 | −45.274 | 21.457 | −7.549 | 1.00 | 24.73 | C |
| ATOM | 7605 | CD2 | PHE | A | 497 | −46.010 | 22.282 | −8.366 | 1.00 | 25.48 | C |
| ATOM | 7607 | C | PHE | A | 497 | −48.592 | 24.407 | −7.494 | 1.00 | 26.59 | C |
| ATOM | 7608 | O | PHE | A | 497 | −48.361 | 23.738 | −6.500 | 1.00 | 26.77 | O |
| ATOM | 7610 | N | VAL | A | 498 | −48.291 | 25.704 | −7.535 | 1.00 | 24.83 | N |
| ATOM | 7611 | CA | VAL | A | 498 | −47.869 | 26.338 | −6.289 | 1.00 | 23.86 | C |
| ATOM | 7613 | CB | VAL | A | 498 | −47.181 | 27.722 | −6.455 | 1.00 | 23.47 | C |
| ATOM | 7615 | CG1 | VAL | A | 498 | −48.163 | 28.755 | −6.759 | 1.00 | 24.57 | C |
| ATOM | 7619 | CG2 | VAL | A | 498 | −46.151 | 27.690 | −7.551 | 1.00 | 23.54 | C |
| ATOM | 7623 | C | VAL | A | 498 | −49.094 | 26.396 | −5.355 | 1.00 | 22.97 | C |
| ATOM | 7624 | O | VAL | A | 498 | −48.978 | 26.130 | −4.161 | 1.00 | 23.39 | O |
| ATOM | 7626 | N | GLU | A | 499 | −50.268 | 26.687 | −5.903 | 1.00 | 21.68 | N |
| ATOM | 7627 | CA | GLU | A | 499 | −51.473 | 26.719 | −5.106 | 1.00 | 20.84 | C |
| ATOM | 7629 | CB | GLU | A | 499 | −52.677 | 27.136 | −5.930 | 1.00 | 20.99 | C |
| ATOM | 7632 | CG | GLU | A | 499 | −53.957 | 27.352 | −5.099 | 1.00 | 21.25 | C |
| ATOM | 7635 | CD | GLU | A | 499 | −53.930 | 28.630 | −4.265 | 1.00 | 21.77 | C |
| ATOM | 7636 | OE1 | GLU | A | 499 | −52.982 | 29.448 | −4.383 | 1.00 | 20.74 | O |
| ATOM | 7637 | OE2 | GLU | A | 499 | −54.876 | 28.812 | −3.476 | 1.00 | 22.76 | O |
| ATOM | 7638 | C | GLU | A | 499 | −51.766 | 25.371 | −4.497 | 1.00 | 20.35 | C |
| ATOM | 7639 | O | GLU | A | 499 | −52.137 | 25.308 | −3.318 | 1.00 | 20.78 | O |
| ATOM | 7641 | N | THR | A | 500 | −51.629 | 24.286 | −5.264 | 1.00 | 19.40 | N |
| ATOM | 7642 | CA | THR | A | 500 | −51.894 | 22.970 | −4.667 | 1.00 | 18.94 | C |
| ATOM | 7644 | CB | THR | A | 500 | −51.993 | 21.782 | −5.683 | 1.00 | 18.96 | C |
| ATOM | 7646 | OG1 | THR | A | 500 | −50.708 | 21.475 | −6.202 | 1.00 | 19.44 | O |
| ATOM | 7648 | CG2 | THR | A | 500 | −52.991 | 22.071 | −6.835 | 1.00 | 18.75 | C |
| ATOM | 7652 | C | THR | A | 500 | −50.895 | 22.674 | −3.526 | 1.00 | 18.20 | C |
| ATOM | 7653 | O | THR | A | 500 | −51.280 | 22.100 | −2.519 | 1.00 | 17.68 | O |
| ATOM | 7655 | N | ALA | A | 501 | −49.646 | 23.119 | −3.666 | 1.00 | 17.49 | N |
| ATOM | 7656 | CA | ALA | A | 501 | −48.663 | 23.021 | −2.593 | 1.00 | 17.18 | C |
| ATOM | 7658 | CB | ALA | A | 501 | −47.348 | 23.563 | −3.051 | 1.00 | 16.98 | C |
| ATOM | 7662 | C | ALA | A | 501 | −49.120 | 23.770 | −1.338 | 1.00 | 17.38 | C |
| ATOM | 7663 | O | ALA | A | 501 | −49.098 | 23.219 | −.230 | 1.00 | 17.45 | O |
| ATOM | 7665 | N | ILE | A | 502 | −49.517 | 25.031 | −1.508 | 1.00 | 17.29 | N |
| ATOM | 7666 | CA | ILE | A | 502 | −49.971 | 25.857 | −.386 | 1.00 | 17.07 | C |
| ATOM | 7668 | CB | ILE | A | 502 | −50.353 | 27.304 | −.846 | 1.00 | 17.09 | C |
| ATOM | 7670 | CG1 | ILE | A | 502 | −49.092 | 28.069 | −1.286 | 1.00 | 17.17 | C |
| ATOM | 7673 | CD1 | ILE | A | 502 | −49.345 | 29.345 | −2.116 | 1.00 | 16.25 | C |
| ATOM | 7677 | CG2 | ILE | A | 502 | −51.110 | 28.076 | .265 | 1.00 | 16.14 | C |
| ATOM | 7681 | C | ILE | A | 502 | −51.155 | 25.168 | .285 | 1.00 | 17.24 | C |
| ATOM | 7682 | O | ILE | A | 502 | −51.265 | 25.163 | 1.516 | 1.00 | 17.03 | O |
| ATOM | 7684 | N | ASN | A | 503 | −52.022 | 24.559 | −.522 | 1.00 | 17.32 | N |
| ATOM | 7685 | CA | ASN | A | 503 | −53.167 | 23.823 | .022 | 1.00 | 17.75 | C |
| ATOM | 7687 | CB | ASN | A | 503 | −53.986 | 23.221 | −1.121 | 1.00 | 17.70 | C |
| ATOM | 7690 | CG | ASN | A | 503 | −54.760 | 24.261 | −1.888 | 1.00 | 18.41 | C |
| ATOM | 7691 | OD1 | ASN | A | 503 | −55.058 | 25.334 | −1.382 | 1.00 | 18.94 | O |
| ATOM | 7692 | ND2 | ASN | A | 503 | −55.107 | 23.939 | −3.119 | 1.00 | 20.42 | N |
| ATOM | 7695 | C | ASN | A | 503 | −52.803 | 22.727 | 1.075 | 1.00 | 17.74 | C |
| ATOM | 7696 | O | ASN | A | 503 | −53.619 | 22.387 | 1.949 | 1.00 | 17.96 | O |
| ATOM | 7698 | N | LEU | A | 504 | −51.589 | 22.185 | .993 | 1.00 | 17.23 | N |
| ATOM | 7699 | CA | LEU | A | 504 | −51.105 | 21.249 | 1.994 | 1.00 | 17.10 | C |
| ATOM | 7701 | CB | LEU | A | 504 | −49.745 | 20.686 | 1.583 | 1.00 | 17.28 | C |
| ATOM | 7704 | CG | LEU | A | 504 | −49.213 | 19.528 | 2.426 | 1.00 | 17.29 | C |
| ATOM | 7706 | CD1 | LEU | A | 504 | −49.570 | 18.196 | 1.762 | 1.00 | 17.22 | C |
| ATOM | 7710 | CD2 | LEU | A | 504 | −47.708 | 19.686 | 2.616 | 1.00 | 16.83 | C |
| ATOM | 7714 | C | LEU | A | 504 | −50.971 | 21.939 | 3.347 | 1.00 | 16.97 | C |
| ATOM | 7715 | O | LEU | A | 504 | −51.237 | 21.330 | 4.379 | 1.00 | 16.84 | O |
| ATOM | 7717 | N | ALA | A | 505 | −50.535 | 23.201 | 3.330 | 1.00 | 16.90 | N |
| ATOM | 7718 | CA | ALA | A | 505 | −50.433 | 24.015 | 4.540 | 1.00 | 16.68 | C |
| ATOM | 7720 | CB | ALA | A | 505 | −49.739 | 25.309 | 4.243 | 1.00 | 16.54 | C |
| ATOM | 7724 | C | ALA | A | 505 | −51.826 | 24.281 | 5.074 | 1.00 | 16.77 | C |
| ATOM | 7725 | O | ALA | A | 505 | −52.087 | 24.123 | 6.266 | 1.00 | 16.80 | O |
| ATOM | 7727 | N | ARG | A | 506 | −52.726 | 24.664 | 4.172 | 1.00 | 16.82 | N |
| ATOM | 7728 | CA | ARG | A | 506 | −54.128 | 24.875 | 4.521 | 1.00 | 16.84 | C |
| ATOM | 7730 | CB | ARG | A | 506 | −54.944 | 25.274 | 3.286 | 1.00 | 16.86 | C |

TABLE 3-7-continued

| Coordinates of *P. tremuloides IspS* | | | | | | | | | | | |
|---|---|---|---|---|---|---|---|---|---|---|---|
| ATOM | 7733 | CG | ARG | A | 506 | −54.649 | 26.661 | 2.795 | 1.00 | 16.27 | C |
| ATOM | 7736 | CD | ARG | A | 506 | −55.586 | 27.090 | 1.726 | 1.00 | 15.26 | C |
| ATOM | 7739 | NE | ARG | A | 506 | −55.240 | 28.436 | 1.273 | 1.00 | 15.31 | N |
| ATOM | 7741 | CZ | ARG | A | 506 | −54.744 | 28.758 | .082 | 1.00 | 14.28 | C |
| ATOM | 7742 | NH1 | ARG | A | 506 | −54.519 | 27.856 | −.856 | 1.00 | 14.12 | N |
| ATOM | 7745 | NH2 | ARG | A | 506 | −54.471 | 30.018 | −.176 | 1.00 | 15.94 | N |
| ATOM | 7748 | C | ARG | A | 506 | −54.732 | 23.631 | 5.122 | 1.00 | 16.96 | C |
| ATOM | 7749 | O | ARG | A | 506 | −55.480 | 23.707 | 6.089 | 1.00 | 16.71 | O |
| ATOM | 7751 | N | GLN | A | 507 | −54.415 | 22.481 | 4.542 | 1.00 | 17.37 | N |
| ATOM | 7752 | CA | GLN | A | 507 | −54.962 | 21.233 | 5.048 | 1.00 | 17.87 | C |
| ATOM | 7754 | CB | GLN | A | 507 | −54.712 | 20.075 | 4.087 | 1.00 | 17.80 | C |
| ATOM | 7757 | CG | GLN | A | 507 | −55.293 | 18.740 | 4.571 | 1.00 | 17.24 | C |
| ATOM | 7760 | CD | GLN | A | 507 | −56.777 | 18.805 | 4.860 | 1.00 | 16.23 | C |
| ATOM | 7761 | OE1 | GLN | A | 507 | −57.506 | 19.585 | 4.250 | 1.00 | 16.66 | O |
| ATOM | 7762 | NE2 | GLN | A | 507 | −57.233 | 17.980 | 5.790 | 1.00 | 14.96 | N |
| ATOM | 7765 | C | GLN | A | 507 | −54.401 | 20.890 | 6.423 | 1.00 | 18.28 | C |
| ATOM | 7766 | O | GLN | A | 507 | −55.148 | 20.419 | 7.287 | 1.00 | 18.53 | O |
| ATOM | 7768 | N | SER | A | 508 | −53.096 | 21.113 | 6.609 | 1.00 | 18.50 | N |
| ATOM | 7769 | CA | SER | A | 508 | −52.435 | 20.924 | 7.908 | 1.00 | 18.54 | C |
| ATOM | 7771 | CB | SER | A | 508 | −50.979 | 21.385 | 7.856 | 1.00 | 18.40 | C |
| ATOM | 7774 | OG | SER | A | 508 | −50.259 | 20.694 | 6.857 | 1.00 | 18.51 | O |
| ATOM | 7776 | C | SER | A | 508 | −53.147 | 21.752 | 8.942 | 1.00 | 18.78 | C |
| ATOM | 7777 | O | SER | A | 508 | −53.535 | 21.278 | 10.006 | 1.00 | 18.33 | O |
| ATOM | 7779 | N | HIS | A | 509 | −53.324 | 23.014 | 8.599 | 1.00 | 19.37 | N |
| ATOM | 7780 | CA | HIS | A | 509 | −54.014 | 23.922 | 9.466 | 1.00 | 19.92 | C |
| ATOM | 7782 | CB | HIS | A | 509 | −54.126 | 25.295 | 8.818 | 1.00 | 20.07 | C |
| ATOM | 7785 | CG | HIS | A | 509 | −53.000 | 26.188 | 9.174 | 1.00 | 19.82 | C |
| ATOM | 7786 | ND1 | HIS | A | 509 | −52.079 | 26.631 | 8.255 | 1.00 | 19.73 | N |
| ATOM | 7788 | CE1 | HIS | A | 509 | −51.187 | 27.383 | 8.866 | 1.00 | 20.25 | C |
| ATOM | 7790 | NE2 | HIS | A | 509 | −51.485 | 27.426 | 10.149 | 1.00 | 21.66 | N |
| ATOM | 7792 | CD2 | HIS | A | 509 | −52.615 | 26.682 | 10.368 | 1.00 | 20.98 | C |
| ATOM | 7794 | C | HIS | A | 509 | −55.389 | 23.448 | 9.839 | 1.00 | 20.41 | C |
| ATOM | 7795 | O | HIS | A | 509 | −55.821 | 23.694 | 10.934 | 1.00 | 20.22 | O |
| ATOM | 7797 | N | CYS | A | 510 | −56.093 | 22.808 | 8.918 | 1.00 | 21.33 | N |
| ATOM | 7798 | CA | CYS | A | 510 | −57.470 | 22.396 | 9.189 | 1.00 | 22.03 | C |
| ATOM | 7800 | CB | CYS | A | 510 | −58.278 | 22.383 | 7.894 | 1.00 | 21.90 | C |
| ATOM | 7803 | SG | CYS | A | 510 | −58.522 | 24.055 | 7.270 | 1.00 | 21.93 | S |
| ATOM | 7805 | C | CYS | A | 510 | −57.527 | 21.054 | 9.908 | 1.00 | 22.60 | C |
| ATOM | 7806 | O | CYS | A | 510 | −58.423 | 20.822 | 10.706 | 1.00 | 22.23 | O |
| ATOM | 7808 | N | THR | A | 511 | −56.553 | 20.194 | 9.627 | 1.00 | 23.67 | N |
| ATOM | 7809 | CA | THR | A | 511 | −56.421 | 18.920 | 10.305 | 1.00 | 24.81 | C |
| ATOM | 7811 | CB | THR | A | 511 | −55.437 | 18.000 | 9.565 | 1.00 | 24.70 | C |
| ATOM | 7813 | OG1 | THR | A | 511 | −56.071 | 17.485 | 8.394 | 1.00 | 24.45 | O |
| ATOM | 7815 | CG2 | THR | A | 511 | −55.003 | 16.844 | 10.448 | 1.00 | 24.23 | C |
| ATOM | 7819 | C | THR | A | 511 | −55.965 | 19.086 | 11.756 | 1.00 | 26.22 | C |
| ATOM | 7820 | O | THR | A | 511 | −56.685 | 18.717 | 12.679 | 1.00 | 26.12 | O |
| ATOM | 7822 | N | TYR | A | 512 | −54.775 | 19.643 | 11.959 | 1.00 | 28.08 | N |
| ATOM | 7823 | CA | TYR | A | 512 | −54.177 | 19.657 | 13.298 | 1.00 | 29.63 | C |
| ATOM | 7825 | CB | TYR | A | 512 | −52.663 | 19.783 | 13.238 | 1.00 | 29.67 | C |
| ATOM | 7828 | CG | TYR | A | 512 | −52.117 | 18.579 | 12.560 | 1.00 | 29.56 | C |
| ATOM | 7829 | CD1 | TYR | A | 512 | −51.965 | 17.395 | 13.246 | 1.00 | 29.66 | C |
| ATOM | 7831 | CE1 | TYR | A | 512 | −51.507 | 16.273 | 12.614 | 1.00 | 30.94 | C |
| ATOM | 7833 | CZ | TYR | A | 512 | −51.217 | 16.326 | 11.263 | 1.00 | 32.04 | C |
| ATOM | 7834 | OH | TYR | A | 512 | −50.757 | 15.209 | 10.608 | 1.00 | 33.78 | O |
| ATOM | 7836 | CE2 | TYR | A | 512 | −51.390 | 17.492 | 10.557 | 1.00 | 31.29 | C |
| ATOM | 7838 | CD2 | TYR | A | 512 | −51.847 | 18.600 | 11.205 | 1.00 | 30.53 | C |
| ATOM | 7840 | C | TYR | A | 512 | −54.812 | 20.676 | 14.206 | 1.00 | 31.11 | C |
| ATOM | 7841 | O | TYR | A | 512 | −55.494 | 20.277 | 15.139 | 1.00 | 31.34 | O |
| ATOM | 7843 | N | HIS | A | 513 | −54.583 | 21.969 | 13.966 | 1.00 | 32.89 | N |
| ATOM | 7844 | CA | HIS | A | 513 | −55.505 | 23.023 | 14.442 | 1.00 | 34.48 | C |
| ATOM | 7846 | CB | HIS | A | 513 | −56.372 | 23.461 | 13.225 | 1.00 | 35.13 | C |
| ATOM | 7849 | CG | HIS | A | 513 | −57.704 | 24.108 | 13.529 | 1.00 | 37.10 | C |
| ATOM | 7850 | ND1 | HIS | A | 513 | −58.265 | 25.040 | 12.678 | 1.00 | 38.69 | N |
| ATOM | 7852 | CE1 | HIS | A | 513 | −59.442 | 25.416 | 13.151 | 1.00 | 39.23 | C |
| ATOM | 7854 | NE2 | HIS | A | 513 | −59.678 | 24.751 | 14.268 | 1.00 | 38.18 | N |
| ATOM | 7856 | CD2 | HIS | A | 513 | −58.615 | 23.915 | 14.519 | 1.00 | 38.17 | C |
| ATOM | 7858 | C | HIS | A | 513 | −56.337 | 22.503 | 15.610 | 1.00 | 35.00 | C |
| ATOM | 7859 | O | HIS | A | 513 | −56.302 | 23.074 | 16.712 | 1.00 | 35.48 | O |
| ATOM | 7861 | N | ASN | A | 514 | −57.079 | 21.419 | 15.351 | 1.00 | 35.23 | N |
| ATOM | 7862 | CA | ASN | A | 514 | −57.934 | 20.768 | 16.347 | 1.00 | 35.46 | C |
| ATOM | 7864 | CB | ASN | A | 514 | −58.342 | 19.343 | 15.903 | 1.00 | 35.39 | C |
| ATOM | 7867 | CG | ASN | A | 514 | −59.383 | 19.345 | 14.786 | 1.00 | 34.01 | C |
| ATOM | 7868 | OD1 | ASN | A | 514 | −59.336 | 20.185 | 13.896 | 1.00 | 33.36 | O |
| ATOM | 7869 | ND2 | ASN | A | 514 | −60.315 | 18.406 | 14.833 | 1.00 | 31.13 | N |
| ATOM | 7872 | C | ASN | A | 514 | −57.464 | 20.751 | 17.818 | 1.00 | 36.15 | C |
| ATOM | 7873 | O | ASN | A | 514 | −56.397 | 20.211 | 18.153 | 1.00 | 36.13 | O |
| ATOM | 7875 | N | GLY | A | 515 | −58.277 | 21.430 | 18.640 | 1.00 | 36.95 | N |
| ATOM | 7876 | CA | GLY | A | 515 | −58.427 | 21.235 | 20.079 | 1.00 | 37.43 | C |

TABLE 3-7-continued

Coordinates of *P. tremuloides IspS*

| | | | | | | | | | | | |
|---|---|---|---|---|---|---|---|---|---|---|---|
| ATOM | 7879 | C | GLY | A | 515 | −59.724 | 20.470 | 20.381 | 1.00 | 38.18 | C |
| ATOM | 7880 | O | GLY | A | 515 | −59.636 | 19.418 | 21.021 | 1.00 | 38.57 | O |
| ATOM | 7882 | N | ASP | A | 516 | −60.930 | 20.921 | 19.969 | 1.00 | 38.73 | N |
| ATOM | 7883 | CA | ASP | A | 516 | −61.249 | 22.194 | 19.293 | 1.00 | 39.26 | C |
| ATOM | 7885 | CB | ASP | A | 516 | −61.607 | 21.904 | 17.845 | 1.00 | 39.51 | C |
| ATOM | 7888 | CG | ASP | A | 516 | −60.523 | 22.291 | 16.894 | 1.00 | 42.32 | C |
| ATOM | 7889 | OD1 | ASP | A | 516 | −59.613 | 23.084 | 17.286 | 1.00 | 45.56 | O |
| ATOM | 7890 | OD2 | ASP | A | 516 | −60.578 | 21.797 | 15.740 | 1.00 | 45.52 | O |
| ATOM | 7891 | C | ASP | A | 516 | −62.466 | 22.913 | 19.884 | 1.00 | 39.38 | C |
| ATOM | 7892 | O | ASP | A | 516 | −63.032 | 22.454 | 20.880 | 1.00 | 39.74 | O |
| ATOM | 7894 | N | ALA | A | 517 | −62.850 | 24.038 | 19.259 | 1.00 | 39.40 | N |
| ATOM | 7895 | CA | ALA | A | 517 | −64.140 | 24.752 | 19.481 | 1.00 | 39.50 | C |
| ATOM | 7897 | CB | ALA | A | 517 | −65.117 | 24.403 | 18.333 | 1.00 | 39.27 | C |
| ATOM | 7901 | C | ALA | A | 517 | −64.837 | 24.566 | 20.863 | 1.00 | 39.90 | C |
| ATOM | 7902 | O | ALA | A | 517 | −64.173 | 24.428 | 21.899 | 1.00 | 39.89 | O |
| ATOM | 7904 | N | HIS | A | 518 | −66.175 | 24.617 | 20.876 | 1.00 | 40.33 | N |
| ATOM | 7905 | CA | HIS | A | 518 | −66.973 | 24.112 | 22.016 | 1.00 | 40.73 | C |
| ATOM | 7907 | CB | HIS | A | 518 | −68.091 | 25.092 | 22.396 | 1.00 | 41.22 | C |
| ATOM | 7910 | CG | HIS | A | 518 | −67.578 | 26.419 | 22.866 | 1.00 | 43.58 | C |
| ATOM | 7911 | ND1 | HIS | A | 518 | −67.426 | 26.725 | 24.207 | 1.00 | 45.88 | N |
| ATOM | 7913 | CE1 | HIS | A | 518 | −66.938 | 27.950 | 24.320 | 1.00 | 46.42 | C |
| ATOM | 7915 | NE2 | HIS | A | 518 | −66.760 | 28.446 | 23.102 | 1.00 | 46.25 | N |
| ATOM | 7917 | CD2 | HIS | A | 518 | −67.145 | 27.506 | 22.174 | 1.00 | 45.24 | C |
| ATOM | 7919 | C | HIS | A | 518 | −67.526 | 22.725 | 21.655 | 1.00 | 40.17 | C |
| ATOM | 7920 | O | HIS | A | 518 | −68.738 | 22.501 | 21.571 | 1.00 | 40.02 | O |
| ATOM | 7922 | N | THR | A | 519 | −66.581 | 21.812 | 21.448 | 1.00 | 39.64 | N |
| ATOM | 7923 | CA | THR | A | 519 | −66.808 | 20.466 | 20.918 | 1.00 | 39.16 | C |
| ATOM | 7925 | CB | THR | A | 519 | −67.414 | 20.469 | 19.453 | 1.00 | 39.16 | C |
| ATOM | 7927 | OG1 | THR | A | 519 | −66.847 | 21.529 | 18.665 | 1.00 | 39.04 | O |
| ATOM | 7929 | CG2 | THR | A | 519 | −68.942 | 20.633 | 19.480 | 1.00 | 38.82 | C |
| ATOM | 7933 | C | THR | A | 519 | −65.428 | 19.771 | 20.978 | 1.00 | 38.85 | C |
| ATOM | 7934 | O | THR | A | 519 | −64.391 | 20.433 | 20.878 | 1.00 | 38.66 | O |
| ATOM | 7936 | N | SER | A | 520 | −65.407 | 18.455 | 21.170 | 1.00 | 38.37 | N |
| ATOM | 7937 | CA | SER | A | 520 | −64.160 | 17.745 | 21.500 | 1.00 | 38.08 | C |
| ATOM | 7939 | CB | SER | A | 520 | −64.514 | 16.320 | 21.931 | 1.00 | 38.06 | C |
| ATOM | 7942 | OG | SER | A | 520 | −64.560 | 15.475 | 20.805 | 1.00 | 38.66 | O |
| ATOM | 7944 | C | SER | A | 520 | −63.136 | 17.771 | 20.327 | 1.00 | 37.86 | C |
| ATOM | 7945 | O | SER | A | 520 | −63.420 | 18.369 | 19.289 | 1.00 | 37.50 | O |
| ATOM | 7947 | N | PRO | A | 521 | −61.948 | 17.122 | 20.482 | 1.00 | 37.98 | N |
| ATOM | 7948 | CA | PRO | A | 521 | −60.944 | 17.170 | 19.379 | 1.00 | 37.92 | C |
| ATOM | 7950 | CB | PRO | A | 521 | −59.674 | 16.527 | 19.987 | 1.00 | 37.87 | C |
| ATOM | 7953 | CG | PRO | A | 521 | −60.091 | 15.919 | 21.330 | 1.00 | 38.28 | C |
| ATOM | 7956 | CD | PRO | A | 521 | −61.577 | 16.137 | 21.526 | 1.00 | 38.13 | C |
| ATOM | 7959 | C | PRO | A | 521 | −61.432 | 16.446 | 18.110 | 1.00 | 37.96 | C |
| ATOM | 7960 | O | PRO | A | 521 | −61.769 | 17.118 | 17.140 | 1.00 | 38.09 | O |
| ATOM | 7961 | N | ASP | A | 522 | −61.483 | 15.108 | 18.107 | 1.00 | 38.07 | N |
| ATOM | 7962 | CA | ASP | A | 522 | −62.351 | 14.393 | 17.161 | 1.00 | 38.14 | C |
| ATOM | 7964 | CB | ASP | A | 522 | −62.132 | 12.877 | 17.204 | 1.00 | 38.31 | C |
| ATOM | 7967 | CG | ASP | A | 522 | −60.769 | 12.456 | 16.640 | 1.00 | 39.45 | C |
| ATOM | 7968 | OD1 | ASP | A | 522 | −60.160 | 13.200 | 15.827 | 1.00 | 39.72 | O |
| ATOM | 7969 | OD2 | ASP | A | 522 | −60.302 | 11.361 | 17.025 | 1.00 | 41.59 | O |
| ATOM | 7970 | C | ASP | A | 522 | −63.760 | 14.780 | 17.591 | 1.00 | 37.92 | C |
| ATOM | 7971 | O | ASP | A | 522 | −63.908 | 15.608 | 18.474 | 1.00 | 38.01 | O |
| ATOM | 7973 | N | GLU | A | 523 | −64.799 | 14.239 | 16.974 | 1.00 | 37.79 | N |
| ATOM | 7974 | CA | GLU | A | 523 | −66.150 | 14.818 | 17.121 | 1.00 | 37.83 | C |
| ATOM | 7976 | CB | GLU | A | 523 | −66.618 | 14.919 | 18.591 | 1.00 | 37.85 | C |
| ATOM | 7979 | CG | GLU | A | 523 | −66.346 | 13.678 | 19.483 | 1.00 | 39.40 | C |
| ATOM | 7982 | CD | GLU | A | 523 | −66.916 | 13.802 | 20.931 | 1.00 | 41.49 | C |
| ATOM | 7983 | OE1 | GLU | A | 523 | −67.714 | 14.737 | 21.207 | 1.00 | 42.81 | O |
| ATOM | 7984 | OE2 | GLU | A | 523 | −66.566 | 12.957 | 21.800 | 1.00 | 42.04 | O |
| ATOM | 7985 | C | GLU | A | 523 | −66.242 | 16.203 | 16.430 | 1.00 | 37.51 | C |
| ATOM | 7986 | O | GLU | A | 523 | −67.338 | 16.751 | 16.283 | 1.00 | 37.70 | O |
| ATOM | 7988 | N | LEU | A | 524 | −65.097 | 16.775 | 16.043 | 1.00 | 37.03 | N |
| ATOM | 7989 | CA | LEU | A | 524 | −65.044 | 17.863 | 15.067 | 1.00 | 36.58 | C |
| ATOM | 7991 | CB | LEU | A | 524 | −64.174 | 19.022 | 15.559 | 1.00 | 36.56 | C |
| ATOM | 7994 | CG | LEU | A | 524 | −63.963 | 20.225 | 14.624 | 1.00 | 36.35 | C |
| ATOM | 7996 | CD1 | LEU | A | 524 | −63.400 | 21.376 | 15.418 | 1.00 | 35.74 | C |
| ATOM | 8000 | CD2 | LEU | A | 524 | −65.242 | 20.681 | 13.910 | 1.00 | 36.53 | C |
| ATOM | 8004 | C | LEU | A | 524 | −64.478 | 17.287 | 13.782 | 1.00 | 36.20 | C |
| ATOM | 8005 | O | LEU | A | 524 | −65.106 | 17.363 | 12.733 | 1.00 | 36.14 | O |
| ATOM | 8007 | N | THR | A | 525 | −63.298 | 16.686 | 13.869 | 1.00 | 35.83 | N |
| ATOM | 8008 | CA | THR | A | 525 | −62.756 | 15.935 | 12.748 | 1.00 | 35.66 | C |
| ATOM | 8010 | CB | THR | A | 525 | −61.585 | 15.015 | 13.173 | 1.00 | 35.48 | C |
| ATOM | 8012 | OG1 | THR | A | 525 | −60.776 | 15.678 | 14.152 | 1.00 | 35.55 | O |
| ATOM | 8014 | CG2 | THR | A | 525 | −60.720 | 14.641 | 11.978 | 1.00 | 34.73 | C |
| ATOM | 8018 | C | THR | A | 525 | −63.875 | 15.098 | 12.123 | 1.00 | 35.89 | C |
| ATOM | 8019 | O | THR | A | 525 | −64.040 | 15.095 | 10.909 | 1.00 | 35.98 | O |
| ATOM | 8021 | N | ARG | A | 526 | −64.667 | 14.420 | 12.954 | 1.00 | 36.06 | N |

TABLE 3-7-continued

Coordinates of *P. tremuloides IspS*

| | | | | | | | | | | | |
|---|---|---|---|---|---|---|---|---|---|---|---|
| ATOM | 8022 | CA | ARG | A | 526 | −65.739 | 13.574 | 12.448 | 1.00 | 36.18 | C |
| ATOM | 8024 | CB | ARG | A | 526 | −66.340 | 12.718 | 13.555 | 1.00 | 36.56 | C |
| ATOM | 8027 | CG | ARG | A | 526 | −67.416 | 11.754 | 13.054 | 1.00 | 38.35 | C |
| ATOM | 8030 | CD | ARG | A | 526 | −67.781 | 10.702 | 14.092 | 1.00 | 41.00 | C |
| ATOM | 8033 | NE | ARG | A | 526 | −67.740 | 11.207 | 15.470 | 1.00 | 43.08 | N |
| ATOM | 8035 | CZ | ARG | A | 526 | −68.637 | 12.033 | 16.024 | 1.00 | 44.51 | C |
| ATOM | 8036 | NH1 | ARG | A | 526 | −69.681 | 12.500 | 15.336 | 1.00 | 44.46 | N |
| ATOM | 8039 | NH2 | ARG | A | 526 | −68.476 | 12.406 | 17.288 | 1.00 | 45.02 | N |
| ATOM | 8042 | C | ARG | A | 526 | −66.834 | 14.384 | 11.774 | 1.00 | 35.68 | C |
| ATOM | 8043 | O | ARG | A | 526 | −67.253 | 14.035 | 10.675 | 1.00 | 35.84 | O |
| ATOM | 8045 | N | LYS | A | 527 | −67.309 | 15.447 | 12.424 | 1.00 | 35.06 | N |
| ATOM | 8046 | CA | LYS | A | 527 | −68.285 | 16.343 | 11.780 | 1.00 | 34.61 | C |
| ATOM | 8048 | CB | LYS | A | 527 | −68.680 | 17.528 | 12.683 | 1.00 | 34.74 | C |
| ATOM | 8051 | CG | LYS | A | 527 | −69.818 | 17.225 | 13.651 | 1.00 | 35.40 | C |
| ATOM | 8054 | CD | LYS | A | 527 | −70.301 | 18.452 | 14.441 | 1.00 | 35.99 | C |
| ATOM | 8057 | CE | LYS | A | 527 | −71.280 | 18.021 | 15.556 | 1.00 | 36.42 | C |
| ATOM | 8060 | NZ | LYS | A | 527 | −71.652 | 19.095 | 16.530 | 1.00 | 36.31 | N |
| ATOM | 8064 | C | LYS | A | 527 | −67.723 | 16.860 | 10.457 | 1.00 | 33.77 | C |
| ATOM | 8065 | O | LYS | A | 527 | −68.377 | 16.763 | 9.423 | 1.00 | 33.75 | O |
| ATOM | 8067 | N | ARG | A | 528 | −66.501 | 17.388 | 10.499 | 1.00 | 32.71 | N |
| ATOM | 8068 | CA | ARG | A | 528 | −65.840 | 17.929 | 9.310 | 1.00 | 31.79 | C |
| ATOM | 8070 | CB | ARG | A | 528 | −64.425 | 18.464 | 9.644 | 1.00 | 31.74 | C |
| ATOM | 8073 | CG | ARG | A | 528 | −64.419 | 19.844 | 10.330 | 1.00 | 30.90 | C |
| ATOM | 8076 | CD | ARG | A | 528 | −63.021 | 20.439 | 10.527 | 1.00 | 29.75 | C |
| ATOM | 8079 | NE | ARG | A | 528 | −63.098 | 21.745 | 11.190 | 1.00 | 29.55 | N |
| ATOM | 8081 | CZ | ARG | A | 528 | −62.056 | 22.513 | 11.528 | 1.00 | 29.96 | C |
| ATOM | 8082 | NH1 | ARG | A | 528 | −60.801 | 22.145 | 11.284 | 1.00 | 29.74 | N |
| ATOM | 8085 | NH2 | ARG | A | 528 | −62.269 | 23.677 | 12.130 | 1.00 | 30.71 | N |
| ATOM | 8088 | C | ARG | A | 528 | −65.796 | 16.904 | 8.172 | 1.00 | 30.99 | C |
| ATOM | 8089 | O | ARG | A | 528 | −66.226 | 17.206 | 7.068 | 1.00 | 30.97 | O |
| ATOM | 8091 | N | VAL | A | 529 | −65.313 | 15.694 | 8.450 | 1.00 | 30.12 | N |
| ATOM | 8092 | CA | VAL | A | 529 | −65.239 | 14.631 | 7.438 | 1.00 | 29.43 | C |
| ATOM | 8094 | CB | VAL | A | 529 | −64.557 | 13.354 | 7.972 | 1.00 | 29.39 | C |
| ATOM | 8096 | CG1 | VAL | A | 529 | −64.785 | 12.187 | 7.023 | 1.00 | 28.89 | C |
| ATOM | 8100 | CG2 | VAL | A | 529 | −63.062 | 13.589 | 8.186 | 1.00 | 29.44 | C |
| ATOM | 8104 | C | VAL | A | 529 | −66.609 | 14.243 | 6.887 | 1.00 | 28.95 | C |
| ATOM | 8105 | O | VAL | A | 529 | −66.755 | 14.016 | 5.690 | 1.00 | 29.09 | O |
| ATOM | 8107 | N | LEU | A | 530 | −67.615 | 14.153 | 7.744 | 1.00 | 28.18 | N |
| ATOM | 8108 | CA | LEU | A | 530 | −68.956 | 13.874 | 7.246 | 1.00 | 27.72 | C |
| ATOM | 8110 | CB | LEU | A | 530 | −69.971 | 13.715 | 8.395 | 1.00 | 27.75 | C |
| ATOM | 8113 | CG | LEU | A | 530 | −70.334 | 12.274 | 8.775 | 1.00 | 27.36 | C |
| ATOM | 8115 | CD1 | LEU | A | 530 | −69.096 | 11.415 | 9.050 | 1.00 | 26.86 | C |
| ATOM | 8119 | CD2 | LEU | A | 530 | −71.273 | 12.279 | 9.968 | 1.00 | 27.14 | C |
| ATOM | 8123 | C | LEU | A | 530 | −69.401 | 14.963 | 6.256 | 1.00 | 27.16 | C |
| ATOM | 8124 | O | LEU | A | 530 | −69.861 | 14.652 | 5.161 | 1.00 | 27.42 | O |
| ATOM | 8126 | N | SER | A | 531 | −69.230 | 16.229 | 6.635 | 1.00 | 26.21 | N |
| ATOM | 8127 | CA | SER | A | 531 | −69.730 | 17.359 | 5.853 | 1.00 | 25.12 | C |
| ATOM | 8129 | CB | SER | A | 531 | −69.519 | 18.657 | 6.618 | 1.00 | 25.01 | C |
| ATOM | 8132 | OG | SER | A | 531 | −68.167 | 18.791 | 6.985 | 1.00 | 23.94 | O |
| ATOM | 8134 | C | SER | A | 531 | −69.055 | 17.476 | 4.507 | 1.00 | 24.48 | C |
| ATOM | 8135 | O | SER | A | 531 | −69.687 | 17.886 | 3.538 | 1.00 | 24.14 | O |
| ATOM | 8137 | N | VAL | A | 532 | −67.774 | 17.115 | 4.461 | 1.00 | 23.89 | N |
| ATOM | 8138 | CA | VAL | A | 532 | −66.962 | 17.226 | 3.246 | 1.00 | 23.53 | C |
| ATOM | 8140 | CB | VAL | A | 532 | −65.470 | 17.437 | 3.575 | 1.00 | 23.09 | C |
| ATOM | 8142 | CG1 | VAL | A | 532 | −64.633 | 17.355 | 2.348 | 1.00 | 22.32 | C |
| ATOM | 8146 | CG2 | VAL | A | 532 | −65.268 | 18.773 | 4.198 | 1.00 | 23.07 | C |
| ATOM | 8150 | C | VAL | A | 532 | −67.100 | 16.028 | 2.316 | 1.00 | 23.67 | C |
| ATOM | 8151 | O | VAL | A | 532 | −67.137 | 16.209 | 1.099 | 1.00 | 23.58 | O |
| ATOM | 8153 | N | ILE | A | 533 | −67.187 | 14.824 | 2.886 | 1.00 | 23.85 | N |
| ATOM | 8154 | CA | ILE | A | 533 | −67.172 | 13.578 | 2.107 | 1.00 | 24.08 | C |
| ATOM | 8156 | CB | ILE | A | 533 | −66.172 | 12.555 | 2.691 | 1.00 | 24.10 | C |
| ATOM | 8158 | CG1 | ILE | A | 533 | −64.745 | 13.079 | 2.631 | 1.00 | 23.47 | C |
| ATOM | 8161 | CD1 | ILE | A | 533 | −64.178 | 13.083 | 1.255 | 1.00 | 23.42 | C |
| ATOM | 8165 | CG2 | ILE | A | 533 | −66.254 | 11.231 | 1.932 | 1.00 | 24.56 | C |
| ATOM | 8169 | C | ILE | A | 533 | −68.522 | 12.859 | 1.990 | 1.00 | 24.27 | C |
| ATOM | 8170 | O | ILE | A | 533 | −68.991 | 12.620 | .887 | 1.00 | 24.34 | O |
| ATOM | 8172 | N | THR | A | 534 | −69.133 | 12.487 | 3.111 | 1.00 | 24.57 | N |
| ATOM | 8173 | CA | THR | A | 534 | −70.279 | 11.564 | 3.072 | 1.00 | 24.92 | C |
| ATOM | 8175 | CB | THR | A | 534 | −70.200 | 10.522 | 4.207 | 1.00 | 24.93 | C |
| ATOM | 8177 | OG1 | THR | A | 534 | −70.491 | 11.149 | 5.458 | 1.00 | 25.28 | O |
| ATOM | 8179 | CG2 | THR | A | 534 | −68.804 | 9.885 | 4.257 | 1.00 | 24.75 | C |
| ATOM | 8183 | C | THR | A | 534 | −71.673 | 12.209 | 3.083 | 1.00 | 25.00 | C |
| ATOM | 8184 | O | THR | A | 534 | −72.601 | 11.646 | 2.522 | 1.00 | 24.94 | O |
| ATOM | 8186 | N | GLU | A | 535 | −71.821 | 13.374 | 3.708 | 1.00 | 25.26 | N |
| ATOM | 8187 | CA | GLU | A | 535 | −73.132 | 14.024 | 3.833 | 1.00 | 25.34 | C |
| ATOM | 8189 | CB | GLU | A | 535 | −73.333 | 14.523 | 5.255 | 1.00 | 25.44 | C |
| ATOM | 8192 | CG | GLU | A | 535 | −73.753 | 13.424 | 6.196 | 1.00 | 25.80 | C |
| ATOM | 8195 | CD | GLU | A | 535 | −74.307 | 13.963 | 7.468 | 1.00 | 25.72 | C |

TABLE 3-7-continued

Coordinates of *P. tremuloides IspS*

| | | | | | | | | | | | |
|---|---|---|---|---|---|---|---|---|---|---|---|
| ATOM | 8196 | OE1 | GLU | A | 535 | −75.375 | 13.487 | 7.881 | 1.00 | 24.50 | O |
| ATOM | 8197 | OE2 | GLU | A | 535 | −73.678 | 14.877 | 8.039 | 1.00 | 27.03 | O |
| ATOM | 8198 | C | GLU | A | 535 | −73.363 | 15.179 | 2.859 | 1.00 | 25.26 | C |
| ATOM | 8199 | O | GLU | A | 535 | −72.686 | 16.206 | 2.939 | 1.00 | 25.02 | O |
| ATOM | 8201 | N | PRO | A | 536 | −74.351 | 15.030 | 1.959 | 1.00 | 25.25 | N |
| ATOM | 8202 | CA | PRO | A | 536 | −74.655 | 16.111 | 1.050 | 1.00 | 25.18 | C |
| ATOM | 8204 | CB | PRO | A | 536 | −75.661 | 15.484 | .076 | 1.00 | 25.15 | C |
| ATOM | 8207 | CG | PRO | A | 536 | −75.825 | 14.077 | .476 | 1.00 | 24.98 | C |
| ATOM | 8210 | CD | PRO | A | 536 | −75.363 | 13.965 | 1.868 | 1.00 | 25.26 | C |
| ATOM | 8213 | C | PRO | A | 536 | −75.289 | 17.265 | 1.801 | 1.00 | 25.30 | C |
| ATOM | 8214 | O | PRO | A | 536 | −75.826 | 17.070 | 2.883 | 1.00 | 25.57 | O |
| ATOM | 8215 | N | ILE | A | 537 | −75.213 | 18.458 | 1.230 | 1.00 | 25.36 | N |
| ATOM | 8216 | CA | ILE | A | 537 | −75.807 | 19.638 | 1.827 | 1.00 | 25.34 | C |
| ATOM | 8218 | CB | ILE | A | 537 | −75.201 | 20.918 | 1.221 | 1.00 | 25.14 | C |
| ATOM | 8220 | CG1 | ILE | A | 537 | −73.787 | 21.131 | 1.744 | 1.00 | 24.32 | C |
| ATOM | 8223 | CD1 | ILE | A | 537 | −73.228 | 22.472 | 1.406 | 1.00 | 23.22 | C |
| ATOM | 8227 | CG2 | ILE | A | 537 | −76.030 | 22.131 | 1.569 | 1.00 | 25.54 | C |
| ATOM | 8231 | C | ILE | A | 537 | −77.313 | 19.603 | 1.611 | 1.00 | 25.67 | C |
| ATOM | 8232 | O | ILE | A | 537 | −77.786 | 19.132 | .579 | 1.00 | 25.47 | O |
| ATOM | 8234 | N | LEU | A | 538 | −78.071 | 20.088 | 2.586 | 1.00 | 26.22 | N |
| ATOM | 8235 | CA | LEU | A | 538 | −79.514 | 20.051 | 2.467 | 1.00 | 26.65 | C |
| ATOM | 8237 | CB | LEU | A | 538 | −80.213 | 20.525 | 3.749 | 1.00 | 26.78 | C |
| ATOM | 8240 | CG | LEU | A | 538 | −80.162 | 19.609 | 4.989 | 1.00 | 26.64 | C |
| ATOM | 8242 | CD1 | LEU | A | 538 | −81.218 | 20.033 | 6.007 | 1.00 | 26.16 | C |
| ATOM | 8246 | CD2 | LEU | A | 538 | −80.346 | 18.138 | 4.633 | 1.00 | 26.12 | C |
| ATOM | 8250 | C | LEU | A | 538 | −79.925 | 20.881 | 1.262 | 1.00 | 27.08 | C |
| ATOM | 8253 | N | PRO | A | 539 | −80.786 | 20.306 | .414 | 1.00 | 28.03 | N |
| ATOM | 8254 | CA | PRO | A | 539 | −81.117 | 20.855 | −.888 | 1.00 | 28.44 | C |
| ATOM | 8256 | CB | PRO | A | 539 | −82.093 | 19.828 | −1.449 | 1.00 | 28.40 | C |
| ATOM | 8259 | CG | PRO | A | 539 | −82.793 | 19.328 | −.253 | 1.00 | 28.30 | C |
| ATOM | 8262 | CD | PRO | A | 539 | −81.720 | 19.228 | .787 | 1.00 | 28.11 | C |
| ATOM | 8265 | C | PRO | A | 539 | −81.813 | 22.194 | −.804 | 1.00 | 28.89 | C |
| ATOM | 8266 | O | PRO | A | 539 | −82.396 | 22.535 | .226 | 1.00 | 28.97 | O |
| ATOM | 8267 | N | PHE | A | 540 | −81.774 | 22.932 | −1.906 | 1.00 | 29.32 | N |
| ATOM | 8268 | CA | PHE | A | 540 | −82.380 | 24.245 | −1.962 | 1.00 | 29.50 | C |
| ATOM | 8270 | CB | PHE | A | 540 | −82.146 | 24.874 | −3.326 | 1.00 | 29.56 | C |
| ATOM | 8273 | CG | PHE | A | 540 | −82.757 | 26.227 | −3.463 | 1.00 | 29.75 | C |
| ATOM | 8274 | CD1 | PHE | A | 540 | −83.874 | 26.429 | −4.255 | 1.00 | 29.47 | C |
| ATOM | 8276 | CE1 | PHE | A | 540 | −84.441 | 27.681 | −4.364 | 1.00 | 29.46 | C |
| ATOM | 8278 | CZ | PHE | A | 540 | −83.901 | 28.743 | −3.674 | 1.00 | 29.81 | C |
| ATOM | 8280 | CE2 | PHE | A | 540 | −82.791 | 28.553 | −2.877 | 1.00 | 30.21 | C |
| ATOM | 8282 | CD2 | PHE | A | 540 | −82.229 | 27.300 | −2.770 | 1.00 | 30.17 | C |
| ATOM | 8284 | C | PHE | A | 540 | −83.865 | 24.129 | −1.722 | 1.00 | 29.66 | C |
| ATOM | 8285 | O | PHE | A | 540 | −84.568 | 23.551 | −2.545 | 1.00 | 29.66 | O |
| ATOM | 8287 | N | GLU | A | 541 | −84.337 | 24.673 | −.601 | 1.00 | 29.90 | N |
| ATOM | 8288 | CA | GLU | A | 541 | −85.761 | 24.605 | −.233 | 1.00 | 30.06 | C |
| ATOM | 8290 | CB | GLU | A | 541 | −85.951 | 23.724 | 1.017 | 1.00 | 30.15 | C |
| ATOM | 8293 | CG | GLU | A | 541 | −87.411 | 23.361 | 1.367 | 1.00 | 30.64 | C |
| ATOM | 8296 | CD | GLU | A | 541 | −88.091 | 24.351 | 2.322 | 1.00 | 31.35 | C |
| ATOM | 8297 | OE1 | GLU | A | 541 | −87.468 | 25.370 | 2.680 | 1.00 | 32.67 | O |
| ATOM | 8298 | OE2 | GLU | A | 541 | −89.254 | 24.114 | 2.719 | 1.00 | 30.48 | O |
| ATOM | 8299 | C | GLU | A | 541 | −86.315 | 26.011 | −.010 | 1.00 | 29.89 | C |
| ATOM | 8300 | O | GLU | A | 541 | −86.835 | 26.636 | −.936 | 1.00 | 29.71 | O |
| ATOM | 8302 | N | LEU | B | 17 | −69.666 | −25.325 | 2.227 | 1.00 | 33.20 | N |
| ATOM | 8303 | CA | LEU | B | 17 | −69.356 | −25.417 | .755 | 1.00 | 33.49 | C |
| ATOM | 8305 | CB | LEU | B | 17 | −70.240 | −26.475 | .048 | 1.00 | 33.44 | C |
| ATOM | 8308 | CG | LEU | B | 17 | −70.077 | −27.986 | .328 | 1.00 | 33.60 | C |
| ATOM | 8310 | CD1 | LEU | B | 17 | −71.285 | −28.778 | −.217 | 1.00 | 32.76 | C |
| ATOM | 8314 | CD2 | LEU | B | 17 | −68.763 | −28.553 | −.230 | 1.00 | 33.21 | C |
| ATOM | 8318 | C | LEU | B | 17 | −69.513 | −24.044 | .055 | 1.00 | 33.54 | C |
| ATOM | 8319 | O | LEU | B | 17 | −70.550 | −23.380 | .195 | 1.00 | 33.77 | O |
| ATOM | 8323 | N | LEU | B | 18 | −68.481 | −23.637 | −.696 | 1.00 | 33.44 | N |
| ATOM | 8324 | CA | LEU | B | 18 | −68.476 | −22.362 | −1.454 | 1.00 | 33.07 | C |
| ATOM | 8326 | CB | LEU | B | 18 | −67.029 | −21.960 | −1.840 | 1.00 | 33.21 | C |
| ATOM | 8329 | CG | LEU | B | 18 | −66.065 | −21.488 | −.721 | 1.00 | 34.06 | C |
| ATOM | 8331 | CD1 | LEU | B | 18 | −64.607 | −21.351 | −1.235 | 1.00 | 34.51 | C |
| ATOM | 8335 | CD2 | LEU | B | 18 | −66.516 | −20.164 | −.061 | 1.00 | 33.43 | C |
| ATOM | 8339 | C | LEU | B | 18 | −69.379 | −22.400 | −2.714 | 1.00 | 32.37 | C |
| ATOM | 8340 | O | LEU | B | 18 | −69.710 | −21.355 | −3.274 | 1.00 | 32.29 | O |
| ATOM | 8342 | N | SER | B | 19 | −69.765 | −23.597 | −3.153 | 1.00 | 31.62 | N |
| ATOM | 8343 | CA | SER | B | 19 | −70.711 | −23.749 | −4.253 | 1.00 | 31.16 | C |
| ATOM | 8345 | CB | SER | B | 19 | −70.443 | −25.067 | −5.033 | 1.00 | 31.09 | C |
| ATOM | 8348 | OG | SER | B | 19 | −70.977 | −26.243 | −4.421 | 1.00 | 29.36 | O |
| ATOM | 8350 | C | SER | B | 19 | −72.168 | −23.663 | −3.759 | 1.00 | 31.45 | C |
| ATOM | 8351 | O | SER | B | 19 | −73.076 | −23.432 | −4.551 | 1.00 | 31.13 | O |
| ATOM | 8353 | N | SER | B | 20 | −72.386 | −23.824 | −2.451 | 1.00 | 31.91 | N |
| ATOM | 8354 | CA | SER | B | 20 | −73.749 | −23.900 | −1.879 | 1.00 | 32.34 | C |
| ATOM | 8356 | CB | SER | B | 20 | −73.706 | −24.122 | −.357 | 1.00 | 32.35 | C |

TABLE 3-7-continued

Coordinates of *P. tremuloides IspS*

| | | | | | | | | | | | |
|---|---|---|---|---|---|---|---|---|---|---|---|
| ATOM | 8359 | OG | SER | B | 20 | −73.393 | −25.473 | −.055 | 1.00 | 32.34 | O |
| ATOM | 8361 | C | SER | B | 20 | −74.601 | −22.670 | −2.204 | 1.00 | 32.69 | C |
| ATOM | 8362 | O | SER | B | 20 | −74.072 | −21.600 | −2.487 | 1.00 | 32.89 | O |
| ATOM | 8364 | N | ASP | B | 21 | −75.921 | −22.831 | −2.119 | 1.00 | 33.13 | N |
| ATOM | 8365 | CA | ASP | B | 21 | −76.874 | −21.901 | −2.745 | 1.00 | 33.40 | C |
| ATOM | 8367 | CB | ASP | B | 21 | −78.179 | −22.628 | −3.045 | 1.00 | 33.64 | C |
| ATOM | 8370 | CG | ASP | B | 21 | −77.943 | −23.883 | −3.828 | 1.00 | 35.35 | C |
| ATOM | 8371 | OD1 | ASP | B | 21 | −77.031 | −23.866 | −4.684 | 1.00 | 38.26 | O |
| ATOM | 8372 | OD2 | ASP | B | 21 | −78.631 | −24.890 | −3.590 | 1.00 | 37.55 | O |
| ATOM | 8373 | C | ASP | B | 21 | −77.141 | −20.649 | −1.940 | 1.00 | 33.23 | C |
| ATOM | 8374 | O | ASP | B | 21 | −78.039 | −20.616 | −1.106 | 1.00 | 32.91 | O |
| ATOM | 8376 | N | THR | B | 22 | −76.348 | −19.621 | −2.229 | 1.00 | 33.46 | N |
| ATOM | 8377 | CA | THR | B | 22 | −76.443 | −18.307 | −1.593 | 1.00 | 33.79 | C |
| ATOM | 8379 | CB | THR | B | 22 | −76.460 | −18.378 | −.016 | 1.00 | 33.74 | C |
| ATOM | 8381 | OG1 | THR | B | 22 | −75.426 | −19.250 | .460 | 1.00 | 32.97 | O |
| ATOM | 8383 | CG2 | THR | B | 22 | −77.805 | −18.838 | .535 | 1.00 | 33.55 | C |
| ATOM | 8387 | C | THR | B | 22 | −75.217 | −17.479 | −2.018 | 1.00 | 34.24 | C |
| ATOM | 8388 | O | THR | B | 22 | −74.102 | −17.988 | −1.892 | 1.00 | 33.95 | O |
| ATOM | 8390 | N | ASP | B | 23 | −75.361 | −16.248 | −2.543 | 1.00 | 34.99 | N |
| ATOM | 8391 | CA | ASP | B | 23 | −76.603 | −15.620 | −3.103 | 1.00 | 35.61 | C |
| ATOM | 8393 | CB | ASP | B | 23 | −77.242 | −16.538 | −4.170 | 1.00 | 35.51 | C |
| ATOM | 8396 | CG | ASP | B | 23 | −76.196 | −17.236 | −5.034 | 1.00 | 36.08 | C |
| ATOM | 8397 | OD1 | ASP | B | 23 | −75.084 | −16.685 | −5.194 | 1.00 | 35.58 | O |
| ATOM | 8398 | OD2 | ASP | B | 23 | −76.473 | −18.344 | −5.541 | 1.00 | 37.65 | O |
| ATOM | 8399 | C | ASP | B | 23 | −77.662 | −15.083 | −2.097 | 1.00 | 36.10 | C |
| ATOM | 8400 | O | ASP | B | 23 | −78.644 | −15.770 | −1.799 | 1.00 | 36.13 | O |
| ATOM | 8402 | N | GLU | B | 24 | −77.487 | −13.845 | −1.616 | 1.00 | 36.74 | N |
| ATOM | 8403 | CA | GLU | B | 24 | −78.358 | −13.316 | −.543 | 1.00 | 37.59 | C |
| ATOM | 8405 | CB | GLU | B | 24 | −77.765 | −13.666 | .838 | 1.00 | 37.88 | C |
| ATOM | 8408 | CG | GLU | B | 24 | −77.624 | −15.173 | 1.120 | 1.00 | 38.51 | C |
| ATOM | 8411 | CD | GLU | B | 24 | −77.314 | −15.510 | 2.588 | 1.00 | 39.48 | C |
| ATOM | 8412 | OE1 | GLU | B | 24 | −77.171 | −14.581 | 3.434 | 1.00 | 39.60 | O |
| ATOM | 8413 | OE2 | GLU | B | 24 | −77.221 | −16.725 | 2.884 | 1.00 | 39.51 | O |
| ATOM | 8414 | C | GLU | B | 24 | −78.730 | −11.809 | −.559 | 1.00 | 38.11 | C |
| ATOM | 8415 | O | GLU | B | 24 | −79.840 | −11.453 | −.972 | 1.00 | 38.20 | O |
| ATOM | 8417 | N | SER | B | 25 | −77.825 | −10.941 | −.089 | 1.00 | 38.70 | N |
| ATOM | 8418 | CA | SER | B | 25 | −78.192 | −9.560 | .312 | 1.00 | 39.21 | C |
| ATOM | 8420 | CB | SER | B | 25 | −76.995 | −8.783 | .916 | 1.00 | 39.29 | C |
| ATOM | 8423 | OG | SER | B | 25 | −76.267 | −8.037 | −.056 | 1.00 | 39.40 | O |
| ATOM | 8425 | C | SER | B | 25 | −78.853 | −8.738 | −.802 | 1.00 | 39.69 | C |
| ATOM | 8426 | O | SER | B | 25 | −78.707 | −9.050 | −1.995 | 1.00 | 39.75 | O |
| ATOM | 8428 | N | ILE | B | 26 | −79.544 | −7.670 | −.378 | 1.00 | 40.21 | N |
| ATOM | 8429 | CA | ILE | B | 26 | −80.554 | −6.962 | −1.189 | 1.00 | 40.55 | C |
| ATOM | 8431 | CB | ILE | B | 26 | −79.925 | −6.082 | −2.319 | 1.00 | 40.66 | C |
| ATOM | 8433 | CG1 | ILE | B | 26 | −79.083 | −4.951 | −1.700 | 1.00 | 40.73 | C |
| ATOM | 8436 | CD1 | ILE | B | 26 | −78.596 | −3.877 | −2.698 | 1.00 | 40.68 | C |
| ATOM | 8440 | CG2 | ILE | B | 26 | −81.018 | −5.475 | −3.203 | 1.00 | 40.88 | C |
| ATOM | 8444 | C | ILE | B | 26 | −81.575 | −7.999 | −1.714 | 1.00 | 40.72 | C |
| ATOM | 8445 | O | ILE | B | 26 | −81.311 | −8.710 | −2.690 | 1.00 | 40.80 | O |
| ATOM | 8447 | N | GLU | B | 27 | −82.729 | −8.070 | −1.037 | 1.00 | 40.86 | N |
| ATOM | 8448 | CA | GLU | B | 27 | −83.694 | −9.190 | −1.160 | 1.00 | 40.88 | C |
| ATOM | 8450 | CB | GLU | B | 27 | −84.782 | −9.060 | −.061 | 1.00 | 40.95 | C |
| ATOM | 8453 | CG | GLU | B | 27 | −84.235 | −9.257 | 1.379 | 1.00 | 41.28 | C |
| ATOM | 8456 | CD | GLU | B | 27 | −85.123 | −8.657 | 2.484 | 1.00 | 41.74 | C |
| ATOM | 8457 | OE1 | GLU | B | 27 | −85.593 | −7.504 | 2.344 | 1.00 | 41.14 | O |
| ATOM | 8458 | OE2 | GLU | B | 27 | −85.332 | −9.337 | 3.514 | 1.00 | 42.36 | O |
| ATOM | 8459 | C | GLU | B | 27 | −84.290 | −9.355 | −2.587 | 1.00 | 40.75 | C |
| ATOM | 8460 | O | GLU | B | 27 | −83.664 | −8.936 | −3.569 | 1.00 | 40.88 | O |
| ATOM | 8462 | N | VAL | B | 28 | −85.461 | −9.994 | −2.712 | 1.00 | 40.40 | N |
| ATOM | 8463 | CA | VAL | B | 28 | −86.033 | −10.361 | −4.027 | 1.00 | 39.97 | C |
| ATOM | 8465 | CB | VAL | B | 28 | −86.034 | −9.157 | −5.053 | 1.00 | 40.03 | C |
| ATOM | 8467 | CG1 | VAL | B | 28 | −86.494 | −9.600 | −6.444 | 1.00 | 39.63 | C |
| ATOM | 8471 | CG2 | VAL | B | 28 | −86.900 | −7.994 | −4.525 | 1.00 | 39.86 | C |
| ATOM | 8475 | C | VAL | B | 28 | −85.335 | −11.600 | −4.625 | 1.00 | 39.63 | C |
| ATOM | 8476 | O | VAL | B | 28 | −85.858 | −12.204 | −5.567 | 1.00 | 39.63 | O |
| ATOM | 8478 | N | HIS | B | 29 | −84.175 | −11.980 | −4.069 | 1.00 | 39.21 | N |
| ATOM | 8479 | CA | HIS | B | 29 | −83.431 | −13.177 | −4.504 | 1.00 | 38.81 | C |
| ATOM | 8481 | CB | HIS | B | 29 | −81.914 | −12.913 | −4.665 | 1.00 | 38.97 | C |
| ATOM | 8484 | CG | HIS | B | 29 | −81.571 | −11.721 | −5.512 | 1.00 | 39.99 | C |
| ATOM | 8485 | ND1 | HIS | B | 29 | −81.181 | −11.825 | −6.834 | 1.00 | 40.79 | N |
| ATOM | 8487 | CE1 | HIS | B | 29 | −80.931 | −10.615 | −7.312 | 1.00 | 40.76 | C |
| ATOM | 8489 | NE2 | HIS | B | 29 | −81.134 | −9.734 | −6.346 | 1.00 | 40.27 | N |
| ATOM | 8491 | CD2 | HIS | B | 29 | −81.525 | −10.400 | −5.209 | 1.00 | 40.17 | C |
| ATOM | 8493 | C | HIS | B | 29 | −83.611 | −14.340 | −3.523 | 1.00 | 38.05 | C |
| ATOM | 8494 | O | HIS | B | 29 | −82.782 | −15.259 | −3.526 | 1.00 | 38.02 | O |
| ATOM | 8496 | N | LYS | B | 30 | −84.667 | −14.321 | −2.694 | 1.00 | 37.06 | N |
| ATOM | 8497 | CA | LYS | B | 30 | −85.107 | −15.559 | −2.022 | 1.00 | 36.33 | C |
| ATOM | 8499 | CB | LYS | B | 30 | −86.056 | −15.286 | −.836 | 1.00 | 36.27 | C |

TABLE 3-7-continued

Coordinates of *P. tremuloides IspS*

| | | | | | | | | | | | |
|---|---|---|---|---|---|---|---|---|---|---|---|
| ATOM | 8502 | CG | LYS | B | 30 | −85.352 | −14.818 | .461 | 1.00 | 36.09 | C |
| ATOM | 8505 | CD | LYS | B | 30 | −86.355 | −14.599 | 1.612 | 1.00 | 36.03 | C |
| ATOM | 8508 | CE | LYS | B | 30 | −85.811 | −13.659 | 2.701 | 1.00 | 36.24 | C |
| ATOM | 8511 | NZ | LYS | B | 30 | −86.802 | −13.356 | 3.789 | 1.00 | 35.65 | N |
| ATOM | 8515 | C | LYS | B | 30 | −85.710 | −16.510 | −3.094 | 1.00 | 35.69 | C |
| ATOM | 8516 | O | LYS | B | 30 | −86.706 | −17.205 | −2.879 | 1.00 | 35.35 | O |
| ATOM | 8518 | N | ASP | B | 31 | −85.075 | −16.484 | −4.268 | 1.00 | 35.13 | N |
| ATOM | 8519 | CA | ASP | B | 31 | −85.145 | −17.519 | −5.282 | 1.00 | 34.64 | C |
| ATOM | 8521 | CB | ASP | B | 31 | −84.592 | −16.962 | −6.623 | 1.00 | 34.60 | C |
| ATOM | 8524 | CG | ASP | B | 31 | −84.419 | −18.032 | −7.725 | 1.00 | 34.24 | C |
| ATOM | 8525 | OD1 | ASP | B | 31 | −84.914 | −19.165 | −7.570 | 1.00 | 34.58 | O |
| ATOM | 8526 | OD2 | ASP | B | 31 | −83.776 | −17.732 | −8.761 | 1.00 | 31.56 | O |
| ATOM | 8527 | C | ASP | B | 31 | −84.304 | −18.675 | −4.721 | 1.00 | 34.31 | C |
| ATOM | 8528 | O | ASP | B | 31 | −83.122 | −18.838 | −5.038 | 1.00 | 34.03 | O |
| ATOM | 8530 | N | LYS | B | 32 | −84.917 | −19.429 | −3.813 | 1.00 | 33.94 | N |
| ATOM | 8531 | CA | LYS | B | 32 | −84.380 | −20.710 | −3.369 | 1.00 | 33.36 | C |
| ATOM | 8533 | CB | LYS | B | 32 | −83.772 | −20.607 | −1.973 | 1.00 | 33.45 | C |
| ATOM | 8536 | CG | LYS | B | 32 | −82.540 | −19.693 | −1.951 | 1.00 | 33.56 | C |
| ATOM | 8539 | CD | LYS | B | 32 | −82.025 | −19.455 | −.532 | 1.00 | 34.17 | C |
| ATOM | 8542 | CE | LYS | B | 32 | −81.671 | −17.987 | −.283 | 1.00 | 34.16 | C |
| ATOM | 8545 | NZ | LYS | B | 32 | −80.746 | −17.437 | −1.311 | 1.00 | 34.07 | N |
| ATOM | 8549 | C | LYS | B | 32 | −85.490 | −21.764 | −3.499 | 1.00 | 32.57 | C |
| ATOM | 8550 | O | LYS | B | 32 | −85.908 | −22.412 | −2.538 | 1.00 | 32.10 | O |
| ATOM | 8552 | N | ALA | B | 33 | −85.976 | −21.859 | −4.738 | 1.00 | 31.66 | N |
| ATOM | 8553 | CA | ALA | B | 33 | −86.576 | −23.055 | −5.259 | 1.00 | 30.94 | C |
| ATOM | 8555 | CB | ALA | B | 33 | −87.247 | −22.773 | −6.597 | 1.00 | 30.47 | C |
| ATOM | 8559 | C | ALA | B | 33 | −85.442 | −24.081 | −5.403 | 1.00 | 30.55 | C |
| ATOM | 8560 | O | ALA | B | 33 | −85.684 | −25.230 | −5.751 | 1.00 | 31.12 | O |
| ATOM | 8562 | N | LYS | B | 34 | −84.200 | −23.660 | −5.161 | 1.00 | 29.73 | N |
| ATOM | 8563 | CA | LYS | B | 34 | −83.107 | −24.585 | −4.839 | 1.00 | 29.09 | C |
| ATOM | 8565 | CB | LYS | B | 34 | −81.776 | −23.817 | −4.865 | 1.00 | 29.30 | C |
| ATOM | 8568 | CG | LYS | B | 34 | −80.678 | −24.474 | −5.726 | 1.00 | 29.76 | C |
| ATOM | 8571 | CD | LYS | B | 34 | −79.633 | −23.458 | −6.283 | 1.00 | 28.74 | C |
| ATOM | 8574 | CE | LYS | B | 34 | −78.417 | −24.186 | −6.890 | 1.00 | 27.56 | C |
| ATOM | 8577 | NZ | LYS | B | 34 | −78.745 | −25.174 | −7.935 | 1.00 | 26.16 | N |
| ATOM | 8581 | C | LYS | B | 34 | −83.376 | −25.320 | −3.472 | 1.00 | 28.37 | C |
| ATOM | 8582 | O | LYS | B | 34 | −83.254 | −24.755 | −2.374 | 1.00 | 27.82 | O |
| ATOM | 8584 | N | LYS | B | 35 | −83.635 | −26.620 | −3.604 | 1.00 | 27.53 | N |
| ATOM | 8585 | CA | LYS | B | 35 | −84.629 | −27.429 | −2.851 | 1.00 | 26.77 | C |
| ATOM | 8587 | CB | LYS | B | 35 | −85.729 | −26.602 | −2.170 | 1.00 | 26.81 | C |
| ATOM | 8590 | CG | LYS | B | 35 | −87.089 | −26.520 | −2.907 | 1.00 | 27.05 | C |
| ATOM | 8593 | CD | LYS | B | 35 | −88.096 | −27.604 | −2.452 | 1.00 | 27.41 | C |
| ATOM | 8596 | CE | LYS | B | 35 | −89.394 | −27.636 | −3.300 | 1.00 | 27.21 | C |
| ATOM | 8599 | NZ | LYS | B | 35 | −90.501 | −26.792 | −2.762 | 1.00 | 26.28 | N |
| ATOM | 8603 | C | LYS | B | 35 | −85.257 | −28.357 | −3.920 | 1.00 | 26.03 | C |
| ATOM | 8604 | O | LYS | B | 35 | −85.853 | −29.386 | −3.626 | 1.00 | 26.00 | O |
| ATOM | 8606 | N | LEU | B | 36 | −85.171 | −27.909 | −5.168 | 1.00 | 24.98 | N |
| ATOM | 8607 | CA | LEU | B | 36 | −85.095 | −28.783 | −6.319 | 1.00 | 24.02 | C |
| ATOM | 8609 | CB | LEU | B | 36 | −85.004 | −27.930 | −7.594 | 1.00 | 23.83 | C |
| ATOM | 8612 | CG | LEU | B | 36 | −86.208 | −27.103 | −8.062 | 1.00 | 22.23 | C |
| ATOM | 8614 | CD1 | LEU | B | 36 | −85.762 | −25.873 | −8.802 | 1.00 | 19.93 | C |
| ATOM | 8618 | CD2 | LEU | B | 36 | −87.092 | −27.930 | −8.951 | 1.00 | 22.11 | C |
| ATOM | 8622 | C | LEU | B | 36 | −83.834 | −29.659 | −6.185 | 1.00 | 23.58 | C |
| ATOM | 8623 | O | LEU | B | 36 | −83.840 | −30.842 | −6.508 | 1.00 | 23.38 | O |
| ATOM | 8625 | N | GLU | B | 37 | −82.742 | −29.046 | −5.739 | 1.00 | 23.18 | N |
| ATOM | 8626 | CA | GLU | B | 37 | −81.510 | −29.753 | −5.396 | 1.00 | 22.88 | C |
| ATOM | 8628 | CB | GLU | B | 37 | −80.466 | −28.766 | −4.855 | 1.00 | 22.76 | C |
| ATOM | 8631 | CG | GLU | B | 37 | −79.038 | −29.297 | −4.874 | 1.00 | 22.24 | C |
| ATOM | 8634 | CD | GLU | B | 37 | −78.085 | −28.505 | −4.009 | 1.00 | 21.06 | C |
| ATOM | 8635 | OE1 | GLU | B | 37 | −78.368 | −27.331 | −3.737 | 1.00 | 19.65 | O |
| ATOM | 8636 | OE2 | GLU | B | 37 | −77.037 | −29.059 | −3.615 | 1.00 | 20.62 | O |
| ATOM | 8637 | C | GLU | B | 37 | −81.748 | −30.856 | −4.364 | 1.00 | 22.95 | C |
| ATOM | 8638 | O | GLU | B | 37 | −81.164 | −31.933 | −4.458 | 1.00 | 22.99 | O |
| ATOM | 8640 | N | ALA | B | 38 | −82.591 | −30.575 | −3.372 | 1.00 | 23.02 | N |
| ATOM | 8641 | CA | ALA | B | 38 | −82.973 | −31.565 | −2.364 | 1.00 | 22.93 | C |
| ATOM | 8643 | CB | ALA | B | 38 | −83.966 | −30.959 | −1.374 | 1.00 | 22.73 | C |
| ATOM | 8647 | C | ALA | B | 38 | −83.580 | −32.778 | −3.044 | 1.00 | 23.05 | C |
| ATOM | 8648 | O | ALA | B | 38 | −83.170 | −33.909 | −2.813 | 1.00 | 22.52 | O |
| ATOM | 8650 | N | GLU | B | 39 | −84.546 | −32.506 | −3.912 | 1.00 | 23.66 | N |
| ATOM | 8651 | CA | GLU | B | 39 | −85.273 | −33.534 | −4.642 | 1.00 | 24.08 | C |
| ATOM | 8653 | CB | GLU | B | 39 | −86.403 | −32.891 | −5.453 | 1.00 | 24.28 | C |
| ATOM | 8656 | CG | GLU | B | 39 | −87.405 | −33.869 | −6.075 | 1.00 | 25.14 | C |
| ATOM | 8659 | CD | GLU | B | 39 | −88.773 | −33.227 | −6.341 | 1.00 | 26.43 | C |
| ATOM | 8660 | OE1 | GLU | B | 39 | −89.232 | −32.381 | −5.519 | 1.00 | 25.90 | O |
| ATOM | 8661 | OE2 | GLU | B | 39 | −89.387 | −33.584 | −7.375 | 1.00 | 26.99 | O |
| ATOM | 8662 | C | GLU | B | 39 | −84.362 | −34.359 | −5.545 | 1.00 | 24.18 | C |
| ATOM | 8663 | O | GLU | B | 39 | −84.483 | −35.579 | −5.575 | 1.00 | 24.32 | O |
| ATOM | 8665 | N | VAL | B | 40 | −83.450 | −33.710 | −6.269 | 1.00 | 24.43 | N |

TABLE 3-7-continued

Coordinates of *P. tremuloides IspS*

| | | | | | | | | | | | |
|---|---|---|---|---|---|---|---|---|---|---|---|
| ATOM | 8666 | CA | VAL | B | 40 | −82.533 | −34.437 | −7.153 | 1.00 | 24.59 | C |
| ATOM | 8668 | CB | VAL | B | 40 | −81.734 | −33.496 | −8.087 | 1.00 | 24.65 | C |
| ATOM | 8670 | CG1 | VAL | B | 40 | −80.611 | −34.258 | −8.792 | 1.00 | 24.14 | C |
| ATOM | 8674 | CG2 | VAL | B | 40 | −82.662 | −32.852 | −9.106 | 1.00 | 23.89 | C |
| ATOM | 8678 | C | VAL | B | 40 | −81.592 | −35.304 | −6.328 | 1.00 | 24.99 | C |
| ATOM | 8679 | O | VAL | B | 40 | −81.265 | −36.407 | −6.717 | 1.00 | 24.77 | O |
| ATOM | 8681 | N | ARG | B | 41 | −81.184 | −34.811 | −5.171 | 1.00 | 25.79 | N |
| ATOM | 8682 | CA | ARG | B | 41 | −80.387 | −35.613 | −4.248 | 1.00 | 26.75 | C |
| ATOM | 8684 | CB | ARG | B | 41 | −80.032 | −34.823 | −2.998 | 1.00 | 27.38 | C |
| ATOM | 8687 | CG | ARG | B | 41 | −78.568 | −34.777 | −2.757 | 1.00 | 30.18 | C |
| ATOM | 8690 | CD | ARG | B | 41 | −78.281 | −34.610 | −1.273 | 1.00 | 34.43 | C |
| ATOM | 8693 | NE | ARG | B | 41 | −76.896 | −34.198 | −1.016 | 1.00 | 37.07 | N |
| ATOM | 8695 | CZ | ARG | B | 41 | −76.350 | −33.045 | −1.416 | 1.00 | 38.54 | C |
| ATOM | 8696 | NH1 | ARG | B | 41 | −75.083 | −32.797 | −1.112 | 1.00 | 40.04 | N |
| ATOM | 8699 | NH2 | ARG | B | 41 | −77.037 | −32.145 | −2.128 | 1.00 | 38.45 | N |
| ATOM | 8702 | C | ARG | B | 41 | −81.081 | −36.860 | −3.762 | 1.00 | 26.60 | C |
| ATOM | 8703 | O | ARG | B | 41 | −80.446 | −37.894 | −3.627 | 1.00 | 26.89 | O |
| ATOM | 8705 | N | ARG | B | 42 | −82.363 | −36.733 | −3.423 | 1.00 | 26.41 | N |
| ATOM | 8706 | CA | ARG | B | 42 | −83.159 | −37.870 | −3.002 | 1.00 | 26.09 | C |
| ATOM | 8708 | CB | ARG | B | 42 | −84.588 | −37.452 | −2.674 | 1.00 | 25.99 | C |
| ATOM | 8711 | CG | ARG | B | 42 | −85.426 | −38.562 | −2.049 | 1.00 | 25.45 | C |
| ATOM | 8714 | CD | ARG | B | 42 | −86.783 | −38.078 | −1.645 | 1.00 | 24.26 | C |
| ATOM | 8717 | NE | ARG | B | 42 | −87.549 | −37.602 | −2.794 | 1.00 | 23.73 | N |
| ATOM | 8719 | CZ | ARG | B | 42 | −88.547 | −36.722 | −2.717 | 1.00 | 24.51 | C |
| ATOM | 8720 | NH1 | ARG | B | 42 | −88.912 | −36.195 | −1.545 | 1.00 | 24.99 | N |
| ATOM | 8723 | NH2 | ARG | B | 42 | −89.185 | −36.354 | −3.816 | 1.00 | 24.46 | N |
| ATOM | 8726 | C | ARG | B | 42 | −83.167 | −38.894 | −4.118 | 1.00 | 26.28 | C |
| ATOM | 8727 | O | ARG | B | 42 | −82.864 | −40.054 | −3.888 | 1.00 | 26.39 | O |
| ATOM | 8729 | N | GLU | B | 43 | −83.476 | −38.460 | −5.334 | 1.00 | 26.52 | N |
| ATOM | 8730 | CA | GLU | B | 43 | −83.476 | −39.370 | −6.479 | 1.00 | 27.00 | C |
| ATOM | 8732 | CB | GLU | B | 43 | −83.982 | −38.676 | −7.753 | 1.00 | 27.50 | C |
| ATOM | 8735 | CG | GLU | B | 43 | −85.469 | −38.275 | −7.699 | 1.00 | 29.78 | C |
| ATOM | 8738 | CD | GLU | B | 43 | −86.342 | −39.301 | −6.974 | 1.00 | 32.52 | C |
| ATOM | 8739 | OE1 | GLU | B | 43 | −86.388 | −40.455 | −7.445 | 1.00 | 35.06 | O |
| ATOM | 8740 | OE2 | GLU | B | 43 | −86.966 | −38.963 | −5.936 | 1.00 | 33.80 | O |
| ATOM | 8741 | C | GLU | B | 43 | −82.147 | −40.059 | −6.769 | 1.00 | 26.37 | C |
| ATOM | 8742 | O | GLU | B | 43 | −82.162 | −41.126 | −7.355 | 1.00 | 26.63 | O |
| ATOM | 8744 | N | ILE | B | 44 | −81.018 | −39.472 | −6.373 | 1.00 | 25.85 | N |
| ATOM | 8745 | CA | ILE | B | 44 | −79.717 | −40.126 | −6.555 | 1.00 | 25.55 | C |
| ATOM | 8747 | CB | ILE | B | 44 | −78.547 | −39.121 | −6.692 | 1.00 | 25.26 | C |
| ATOM | 8749 | CG1 | ILE | B | 44 | −78.706 | −38.273 | −7.953 | 1.00 | 24.47 | C |
| ATOM | 8752 | CD1 | ILE | B | 44 | −77.690 | −37.163 | −8.114 | 1.00 | 23.21 | C |
| ATOM | 8756 | CG2 | ILE | B | 44 | −77.207 | −39.863 | −6.778 | 1.00 | 25.35 | C |
| ATOM | 8760 | C | ILE | B | 44 | −79.404 | −41.109 | −5.428 | 1.00 | 25.84 | C |
| ATOM | 8761 | O | ILE | B | 44 | −78.925 | −42.208 | −5.698 | 1.00 | 25.97 | O |
| ATOM | 8763 | N | ASN | B | 45 | −79.663 | −40.708 | −4.177 | 1.00 | 26.25 | N |
| ATOM | 8764 | CA | ASN | B | 45 | −79.403 | −41.542 | −2.983 | 1.00 | 26.34 | C |
| ATOM | 8766 | CB | ASN | B | 45 | −79.284 | −40.681 | −1.719 | 1.00 | 26.01 | C |
| ATOM | 8769 | CG | ASN | B | 45 | −78.072 | −39.789 | −1.723 | 1.00 | 24.65 | C |
| ATOM | 8770 | OD1 | ASN | B | 45 | −76.957 | −40.226 | −1.434 | 1.00 | 22.47 | O |
| ATOM | 8771 | ND2 | ASN | B | 45 | −78.288 | −38.516 | −2.009 | 1.00 | 23.36 | N |
| ATOM | 8774 | C | ASN | B | 45 | −80.488 | −42.586 | −2.731 | 1.00 | 27.18 | C |
| ATOM | 8775 | O | ASN | B | 45 | −80.374 | −43.390 | −1.806 | 1.00 | 27.30 | O |
| ATOM | 8777 | N | ASN | B | 46 | −81.553 | −42.541 | −3.527 | 1.00 | 28.17 | N |
| ATOM | 8778 | CA | ASN | B | 46 | −82.619 | −43.536 | −3.489 | 1.00 | 29.02 | C |
| ATOM | 8780 | CB | ASN | B | 46 | −83.558 | −43.289 | −4.665 | 1.00 | 29.05 | C |
| ATOM | 8783 | CG | ASN | B | 46 | −84.615 | −44.345 | −4.806 | 1.00 | 28.82 | C |
| ATOM | 8784 | OD1 | ASN | B | 46 | −84.861 | −45.132 | −3.895 | 1.00 | 28.14 | O |
| ATOM | 8785 | ND2 | ASN | B | 46 | −85.255 | −44.369 | −5.968 | 1.00 | 29.67 | N |
| ATOM | 8788 | C | ASN | B | 46 | −82.076 | −44.958 | −3.549 | 1.00 | 30.14 | C |
| ATOM | 8789 | O | ASN | B | 46 | −81.566 | −45.408 | −4.581 | 1.00 | 30.30 | O |
| ATOM | 8791 | N | GLU | B | 47 | −82.218 | −45.674 | −2.446 | 1.00 | 31.36 | N |
| ATOM | 8792 | CA | GLU | B | 47 | −81.575 | −46.968 | −2.295 | 1.00 | 32.61 | C |
| ATOM | 8794 | CB | GLU | B | 47 | −81.617 | −47.430 | −.823 | 1.00 | 33.09 | C |
| ATOM | 8797 | CG | GLU | B | 47 | −80.974 | −46.466 | .218 | 1.00 | 34.19 | C |
| ATOM | 8800 | CD | GLU | B | 47 | −81.919 | −45.337 | .721 | 1.00 | 34.57 | C |
| ATOM | 8801 | OE1 | GLU | B | 47 | −82.911 | −45.012 | .029 | 1.00 | 34.53 | O |
| ATOM | 8802 | OE2 | GLU | B | 47 | −81.652 | −44.762 | 1.805 | 1.00 | 34.30 | O |
| ATOM | 8803 | C | GLU | B | 47 | −82.205 | −48.046 | −3.172 | 1.00 | 33.18 | C |
| ATOM | 8804 | O | GLU | B | 47 | −81.604 | −49.088 | −3.370 | 1.00 | 33.44 | O |
| ATOM | 8806 | N | LYS | B | 48 | −83.408 | −47.808 | −3.692 | 1.00 | 34.11 | N |
| ATOM | 8807 | CA | LYS | B | 48 | −84.164 | −48.853 | −4.396 | 1.00 | 34.85 | C |
| ATOM | 8809 | CB | LYS | B | 48 | −85.379 | −49.254 | −3.542 | 1.00 | 35.09 | C |
| ATOM | 8812 | CG | LYS | B | 48 | −85.003 | −49.723 | −2.127 | 1.00 | 36.00 | C |
| ATOM | 8815 | CD | LYS | B | 48 | −86.174 | −50.338 | −1.350 | 1.00 | 37.13 | C |
| ATOM | 8818 | CE | LYS | B | 48 | −87.312 | −49.340 | −1.094 | 1.00 | 37.90 | C |
| ATOM | 8821 | NZ | LYS | B | 48 | −86.908 | −48.161 | −.272 | 1.00 | 38.31 | N |
| ATOM | 8825 | C | LYS | B | 48 | −84.586 | −48.487 | −5.835 | 1.00 | 35.13 | C |

TABLE 3-7-continued

Coordinates of *P. tremuloides IspS*

| | | | | | | | | | | | |
|---|---|---|---|---|---|---|---|---|---|---|---|
| ATOM | 8826 | O | LYS | B | 48 | −85.544 | −49.030 | −6.361 | 1.00 | 34.60 | O |
| ATOM | 8828 | N | ALA | B | 49 | −83.858 | −47.576 | −6.474 | 1.00 | 36.09 | N |
| ATOM | 8829 | CA | ALA | B | 49 | −84.093 | −47.261 | −7.886 | 1.00 | 36.87 | C |
| ATOM | 8831 | CB | ALA | B | 49 | −83.550 | −45.880 | −8.238 | 1.00 | 36.73 | C |
| ATOM | 8835 | C | ALA | B | 49 | −83.406 | −48.325 | −8.714 | 1.00 | 37.56 | C |
| ATOM | 8836 | O | ALA | B | 49 | −82.315 | −48.761 | −8.363 | 1.00 | 37.62 | O |
| ATOM | 8838 | N | GLU | B | 50 | −84.028 | −48.754 | −9.807 | 1.00 | 38.54 | N |
| ATOM | 8839 | CA | GLU | B | 50 | −83.399 | −49.772 | −10.652 | 1.00 | 39.40 | C |
| ATOM | 8841 | CB | GLU | B | 50 | −84.380 | −50.384 | −11.673 | 1.00 | 39.71 | C |
| ATOM | 8844 | CG | GLU | B | 50 | −83.959 | −51.808 | −12.179 | 1.00 | 41.33 | C |
| ATOM | 8847 | CD | GLU | B | 50 | −83.733 | −52.860 | −11.039 | 1.00 | 42.88 | C |
| ATOM | 8848 | OE1 | GLU | B | 50 | −84.683 | −53.628 | −10.718 | 1.00 | 42.94 | O |
| ATOM | 8849 | OE2 | GLU | B | 50 | −82.603 | −52.921 | −10.472 | 1.00 | 42.96 | O |
| ATOM | 8850 | C | GLU | B | 50 | −82.171 | −49.163 | −11.330 | 1.00 | 39.43 | C |
| ATOM | 8851 | O | GLU | B | 50 | −82.211 | −48.017 | −11.791 | 1.00 | 39.66 | O |
| ATOM | 8853 | N | PHE | B | 51 | −81.084 | −49.929 | −11.376 | 1.00 | 39.32 | N |
| ATOM | 8854 | CA | PHE | B | 51 | −79.763 | −49.360 | −11.636 | 1.00 | 39.32 | C |
| ATOM | 8856 | CB | PHE | B | 51 | −78.675 | −50.429 | −11.476 | 1.00 | 39.62 | C |
| ATOM | 8859 | CG | PHE | B | 51 | −78.470 | −50.889 | −10.032 | 1.00 | 41.82 | C |
| ATOM | 8860 | CD1 | PHE | B | 51 | −78.093 | −49.978 | −9.032 | 1.00 | 42.93 | C |
| ATOM | 8862 | CE1 | PHE | B | 51 | −77.892 | −50.391 | −7.705 | 1.00 | 43.30 | C |
| ATOM | 8864 | CZ | PHE | B | 51 | −78.059 | −51.729 | −7.359 | 1.00 | 44.33 | C |
| ATOM | 8866 | CE2 | PHE | B | 51 | −78.430 | −52.659 | −8.341 | 1.00 | 44.75 | C |
| ATOM | 8868 | CD2 | PHE | B | 51 | −78.633 | −52.234 | −9.677 | 1.00 | 44.06 | C |
| ATOM | 8870 | C | PHE | B | 51 | −79.646 | −48.625 | −12.976 | 1.00 | 38.57 | C |
| ATOM | 8871 | O | PHE | B | 51 | −79.045 | −47.564 | −13.046 | 1.00 | 38.50 | O |
| ATOM | 8873 | N | LEU | B | 52 | −80.262 | −49.155 | −14.024 | 1.00 | 37.99 | N |
| ATOM | 8874 | CA | LEU | B | 52 | −80.176 | −48.539 | −15.351 | 1.00 | 37.42 | C |
| ATOM | 8876 | CB | LEU | B | 52 | −80.774 | −49.476 | −16.399 | 1.00 | 37.66 | C |
| ATOM | 8879 | CG | LEU | B | 52 | −80.502 | −49.168 | −17.876 | 1.00 | 38.39 | C |
| ATOM | 8881 | CD1 | LEU | B | 52 | −80.171 | −50.452 | −18.652 | 1.00 | 38.46 | C |
| ATOM | 8885 | CD2 | LEU | B | 52 | −81.703 | −48.432 | −18.500 | 1.00 | 39.23 | C |
| ATOM | 8889 | C | LEU | B | 52 | −80.824 | −47.143 | −15.431 | 1.00 | 36.69 | C |
| ATOM | 8890 | O | LEU | B | 52 | −80.383 | −46.312 | −16.224 | 1.00 | 36.59 | O |
| ATOM | 8892 | N | THR | B | 53 | −81.859 | −46.879 | −14.625 | 1.00 | 35.87 | N |
| ATOM | 8893 | CA | THR | B | 53 | −82.409 | −45.510 | −14.513 | 1.00 | 34.91 | C |
| ATOM | 8895 | CB | THR | B | 53 | −83.784 | −45.421 | −13.805 | 1.00 | 34.72 | C |
| ATOM | 8897 | OG1 | THR | B | 53 | −84.724 | −46.269 | −14.455 | 1.00 | 34.04 | O |
| ATOM | 8899 | CG2 | THR | B | 53 | −84.316 | −43.981 | −13.855 | 1.00 | 34.81 | C |
| ATOM | 8903 | C | THR | B | 53 | −81.454 | −44.642 | −13.722 | 1.00 | 34.05 | C |
| ATOM | 8904 | O | THR | B | 53 | −81.170 | −43.513 | −14.121 | 1.00 | 34.16 | O |
| ATOM | 8906 | N | LEU | B | 54 | −80.987 | −45.167 | −12.593 | 1.00 | 32.84 | N |
| ATOM | 8907 | CA | LEU | B | 54 | −80.027 | −44.461 | −11.772 | 1.00 | 32.16 | C |
| ATOM | 8909 | CB | LEU | B | 54 | −79.506 | −45.354 | −10.662 | 1.00 | 32.27 | C |
| ATOM | 8912 | CG | LEU | B | 54 | −78.521 | −44.702 | −9.698 | 1.00 | 32.56 | C |
| ATOM | 8914 | CD1 | LEU | B | 54 | −79.275 | −43.760 | −8.769 | 1.00 | 32.38 | C |
| ATOM | 8918 | CD2 | LEU | B | 54 | −77.755 | −45.789 | −8.917 | 1.00 | 33.29 | C |
| ATOM | 8922 | C | LEU | B | 54 | −78.870 | −44.006 | −12.634 | 1.00 | 31.50 | C |
| ATOM | 8923 | O | LEU | B | 54 | −78.509 | −42.840 | −12.607 | 1.00 | 31.98 | O |
| ATOM | 8925 | N | LEU | B | 55 | −78.297 | −44.914 | −13.418 | 1.00 | 30.43 | N |
| ATOM | 8926 | CA | LEU | B | 55 | −77.220 | −44.540 | −14.333 | 1.00 | 29.36 | C |
| ATOM | 8928 | CB | LEU | B | 55 | −76.765 | −45.733 | −15.173 | 1.00 | 29.23 | C |
| ATOM | 8931 | CG | LEU | B | 55 | −76.157 | −46.902 | −14.391 | 1.00 | 28.60 | C |
| ATOM | 8933 | CD1 | LEU | B | 55 | −75.697 | −48.004 | −15.348 | 1.00 | 27.60 | C |
| ATOM | 8937 | CD2 | LEU | B | 55 | −75.020 | −46.440 | −13.469 | 1.00 | 27.20 | C |
| ATOM | 8941 | C | LEU | B | 55 | −77.678 | −43.406 | −15.230 | 1.00 | 28.60 | C |
| ATOM | 8942 | O | LEU | B | 55 | −77.063 | −42.365 | −15.267 | 1.00 | 28.17 | O |
| ATOM | 8944 | N | GLU | B | 56 | −78.786 | −43.594 | −15.919 | 1.00 | 28.23 | N |
| ATOM | 8945 | CA | GLU | B | 56 | −79.326 | −42.530 | −16.759 | 1.00 | 28.64 | C |
| ATOM | 8947 | CB | GLU | B | 56 | −80.567 | −43.031 | −17.524 | 1.00 | 29.27 | C |
| ATOM | 8950 | CG | GLU | B | 56 | −80.229 | −43.783 | −18.829 | 1.00 | 31.73 | C |
| ATOM | 8953 | CD | GLU | B | 56 | −81.265 | −44.860 | −19.206 | 1.00 | 35.52 | C |
| ATOM | 8954 | OE1 | GLU | B | 56 | −82.474 | −44.693 | −18.889 | 1.00 | 36.97 | O |
| ATOM | 8955 | OE2 | GLU | B | 56 | −80.856 | −45.877 | −19.825 | 1.00 | 37.55 | O |
| ATOM | 8956 | C | GLU | B | 56 | −79.632 | −41.203 | −15.995 | 1.00 | 27.77 | C |
| ATOM | 8957 | O | GLU | B | 56 | −79.561 | −40.103 | −16.582 | 1.00 | 27.84 | O |
| ATOM | 8959 | N | LEU | B | 57 | −79.976 | −41.303 | −14.710 | 1.00 | 26.29 | N |
| ATOM | 8960 | CA | LEU | B | 57 | −80.158 | −40.120 | −13.895 | 1.00 | 25.06 | C |
| ATOM | 8962 | CB | LEU | B | 57 | −80.724 | −40.462 | −12.514 | 1.00 | 24.83 | C |
| ATOM | 8965 | CG | LEU | B | 57 | −80.952 | −39.298 | −11.544 | 1.00 | 23.72 | C |
| ATOM | 8967 | CD1 | LEU | B | 57 | −81.909 | −38.278 | −12.117 | 1.00 | 21.43 | C |
| ATOM | 8971 | CD2 | LEU | B | 57 | −81.477 | −39.830 | −10.227 | 1.00 | 22.41 | C |
| ATOM | 8975 | C | LEU | B | 57 | −78.801 | −39.459 | −13.780 | 1.00 | 24.40 | C |
| ATOM | 8976 | O | LEU | B | 57 | −78.591 | −38.373 | −14.306 | 1.00 | 24.70 | O |
| ATOM | 8978 | N | ILE | B | 58 | −77.855 | −40.133 | −13.144 | 1.00 | 23.56 | N |
| ATOM | 8979 | CA | ILE | B | 58 | −76.509 | −39.574 | −12.991 | 1.00 | 22.91 | C |
| ATOM | 8981 | CB | ILE | B | 58 | −75.454 | −40.635 | −12.599 | 1.00 | 22.49 | C |
| ATOM | 8983 | CG1 | ILE | B | 58 | −75.753 | −41.251 | −11.235 | 1.00 | 22.09 | C |

TABLE 3-7-continued

Coordinates of *P. tremuloides IspS*

| | | | | | | | | | | | |
|---|---|---|---|---|---|---|---|---|---|---|---|
| ATOM | 8986 | CD1 | ILE | B | 58 | −74.936 | −42.464 | −10.926 | 1.00 | 20.88 | C |
| ATOM | 8990 | CG2 | ILE | B | 58 | −74.103 | −39.992 | −12.534 | 1.00 | 22.63 | C |
| ATOM | 8994 | C | ILE | B | 58 | −76.062 | −38.927 | −14.302 | 1.00 | 22.64 | C |
| ATOM | 8995 | O | ILE | B | 58 | −75.603 | −37.796 | −14.315 | 1.00 | 22.38 | O |
| ATOM | 8997 | N | ASP | B | 59 | −76.228 | −39.646 | −15.404 | 1.00 | 22.56 | N |
| ATOM | 8998 | CA | ASP | B | 59 | −75.715 | −39.196 | −16.684 | 1.00 | 22.76 | C |
| ATOM | 9000 | CB | ASP | B | 59 | −75.926 | −40.269 | −17.757 | 1.00 | 22.93 | C |
| ATOM | 9003 | CG | ASP | B | 59 | −75.274 | −39.904 | −19.088 | 1.00 | 24.58 | C |
| ATOM | 9004 | OD1 | ASP | B | 59 | −74.157 | −39.322 | −19.081 | 1.00 | 25.70 | O |
| ATOM | 9005 | OD2 | ASP | B | 59 | −75.897 | −40.186 | −20.142 | 1.00 | 27.51 | O |
| ATOM | 9006 | C | ASP | B | 59 | −76.343 | −37.863 | −17.104 | 1.00 | 22.40 | C |
| ATOM | 9007 | O | ASP | B | 59 | −75.634 | −36.939 | −17.520 | 1.00 | 22.40 | O |
| ATOM | 9009 | N | ASN | B | 60 | −77.662 | −37.767 | −16.991 | 1.00 | 21.91 | N |
| ATOM | 9010 | CA | ASN | B | 60 | −78.349 | −36.500 | −17.217 | 1.00 | 21.70 | C |
| ATOM | 9012 | CB | ASN | B | 60 | −79.867 | −36.674 | −17.088 | 1.00 | 22.12 | C |
| ATOM | 9015 | CG | ASN | B | 60 | −80.477 | −37.390 | −18.268 | 1.00 | 22.76 | C |
| ATOM | 9016 | OD1 | ASN | B | 60 | −80.027 | −37.233 | −19.393 | 1.00 | 24.28 | O |
| ATOM | 9017 | ND2 | ASN | B | 60 | −81.515 | −38.172 | −18.017 | 1.00 | 24.36 | N |
| ATOM | 9020 | C | ASN | B | 60 | −77.898 | −35.427 | −16.234 | 1.00 | 21.17 | C |
| ATOM | 9021 | O | ASN | B | 60 | −77.700 | −34.273 | −16.614 | 1.00 | 20.85 | O |
| ATOM | 9023 | N | VAL | B | 61 | −77.745 | −35.805 | −14.968 | 1.00 | 20.60 | N |
| ATOM | 9024 | CA | VAL | B | 61 | −77.382 | −34.841 | −13.942 | 1.00 | 20.48 | C |
| ATOM | 9026 | CB | VAL | B | 61 | −77.277 | −35.490 | −12.551 | 1.00 | 20.26 | C |
| ATOM | 9028 | CG1 | VAL | B | 61 | −76.585 | −34.562 | −11.565 | 1.00 | 19.92 | C |
| ATOM | 9032 | CG2 | VAL | B | 61 | −78.668 | −35.857 | −12.049 | 1.00 | 20.66 | C |
| ATOM | 9036 | C | VAL | B | 61 | −76.068 | −34.208 | −14.335 | 1.00 | 20.66 | C |
| ATOM | 9037 | O | VAL | B | 61 | −75.871 | −32.998 | −14.182 | 1.00 | 20.74 | O |
| ATOM | 9039 | N | GLN | B | 62 | −75.187 | −35.048 | −14.875 | 1.00 | 20.92 | N |
| ATOM | 9040 | CA | GLN | B | 62 | −73.854 | −34.636 | −15.285 | 1.00 | 20.69 | C |
| ATOM | 9042 | CB | GLN | B | 62 | −72.917 | −35.847 | −15.404 | 1.00 | 20.77 | C |
| ATOM | 9045 | CG | GLN | B | 62 | −72.456 | −36.369 | −14.035 | 1.00 | 20.91 | C |
| ATOM | 9048 | CD | GLN | B | 62 | −71.328 | −37.383 | −14.112 | 1.00 | 20.75 | C |
| ATOM | 9049 | OE1 | GLN | B | 62 | −70.512 | −37.498 | −13.192 | 1.00 | 20.93 | O |
| ATOM | 9050 | NE2 | GLN | B | 62 | −71.291 | −38.135 | −15.195 | 1.00 | 20.39 | N |
| ATOM | 9053 | C | GLN | B | 62 | −73.900 | −33.834 | −16.567 | 1.00 | 20.32 | C |
| ATOM | 9054 | O | GLN | B | 62 | −73.410 | −32.712 | −16.569 | 1.00 | 20.79 | O |
| ATOM | 9056 | N | ARG | B | 63 | −74.512 | −34.373 | −17.625 | 1.00 | 19.87 | N |
| ATOM | 9057 | CA | ARG | B | 63 | −74.520 | −33.696 | −18.940 | 1.00 | 19.81 | C |
| ATOM | 9059 | CB | ARG | B | 63 | −75.240 | −34.536 | −20.013 | 1.00 | 19.75 | C |
| ATOM | 9062 | CG | ARG | B | 63 | −74.492 | −35.846 | −20.345 | 1.00 | 21.69 | C |
| ATOM | 9065 | CD | ARG | B | 63 | −75.158 | −36.786 | −21.368 | 1.00 | 24.89 | C |
| ATOM | 9068 | NE | ARG | B | 63 | −74.674 | −36.558 | −22.741 | 1.00 | 29.32 | N |
| ATOM | 9070 | CZ | ARG | B | 63 | −75.323 | −35.878 | −23.702 | 1.00 | 33.71 | C |
| ATOM | 9071 | NH1 | ARG | B | 63 | −76.537 | −35.345 | −23.510 | 1.00 | 36.67 | N |
| ATOM | 9074 | NH2 | ARG | B | 63 | −74.761 | −35.736 | −24.894 | 1.00 | 34.58 | N |
| ATOM | 9077 | C | ARG | B | 63 | −75.099 | −32.276 | −18.822 | 1.00 | 19.39 | C |
| ATOM | 9078 | O | ARG | B | 63 | −74.553 | −31.310 | −19.395 | 1.00 | 19.63 | O |
| ATOM | 9080 | N | LEU | B | 64 | −76.155 | −32.148 | −18.017 | 1.00 | 18.62 | N |
| ATOM | 9081 | CA | LEU | B | 64 | −76.811 | −30.856 | −17.753 | 1.00 | 17.96 | C |
| ATOM | 9083 | CB | LEU | B | 64 | −78.136 | −31.077 | −17.008 | 1.00 | 17.97 | C |
| ATOM | 9086 | CG | LEU | B | 64 | −79.264 | −31.737 | −17.809 | 1.00 | 17.08 | C |
| ATOM | 9088 | CD1 | LEU | B | 64 | −80.276 | −32.354 | −16.879 | 1.00 | 15.15 | C |
| ATOM | 9092 | CD2 | LEU | B | 64 | −79.904 | −30.734 | −18.737 | 1.00 | 15.30 | C |
| ATOM | 9096 | C | LEU | B | 64 | −75.975 | −29.847 | −16.966 | 1.00 | 17.39 | C |
| ATOM | 9097 | O | LEU | B | 64 | −76.370 | −28.685 | −16.825 | 1.00 | 17.38 | O |
| ATOM | 9099 | N | GLY | B | 65 | −74.848 | −30.286 | −16.432 | 1.00 | 16.73 | N |
| ATOM | 9100 | CA | GLY | B | 65 | −73.917 | −29.374 | −15.818 | 1.00 | 16.65 | C |
| ATOM | 9103 | C | GLY | B | 65 | −74.077 | −29.249 | −14.319 | 1.00 | 16.68 | C |
| ATOM | 9104 | O | GLY | B | 65 | −73.565 | −28.302 | −13.718 | 1.00 | 16.79 | O |
| ATOM | 9106 | N | LEU | B | 66 | −74.758 | −30.209 | −13.702 | 1.00 | 16.60 | N |
| ATOM | 9107 | CA | LEU | B | 66 | −74.978 | −30.177 | −12.264 | 1.00 | 16.58 | C |
| ATOM | 9109 | CB | LEU | B | 66 | −76.465 | −30.389 | −11.957 | 1.00 | 16.35 | C |
| ATOM | 9112 | CG | LEU | B | 66 | −77.363 | −29.187 | −12.234 | 1.00 | 15.57 | C |
| ATOM | 9114 | CD1 | LEU | B | 66 | −78.828 | −29.602 | −12.163 | 1.00 | 15.26 | C |
| ATOM | 9118 | CD2 | LEU | B | 66 | −77.063 | −28.051 | −11.270 | 1.00 | 13.66 | C |
| ATOM | 9122 | C | LEU | B | 66 | −74.129 | −31.203 | −11.513 | 1.00 | 16.94 | C |
| ATOM | 9123 | O | LEU | B | 66 | −74.152 | −31.251 | −10.279 | 1.00 | 17.50 | O |
| ATOM | 9125 | N | GLY | B | 67 | −73.373 | −32.017 | −12.236 | 1.00 | 17.03 | N |
| ATOM | 9126 | CA | GLY | B | 67 | −72.541 | −33.036 | −11.602 | 1.00 | 17.13 | C |
| ATOM | 9129 | C | GLY | B | 67 | −71.642 | −32.557 | −10.461 | 1.00 | 17.08 | C |
| ATOM | 9130 | O | GLY | B | 67 | −71.378 | −33.317 | −9.522 | 1.00 | 17.33 | O |
| ATOM | 9132 | N | TYR | B | 68 | −71.159 | −31.316 | −10.541 | 1.00 | 16.83 | N |
| ATOM | 9133 | CA | TYR | B | 68 | −70.217 | −30.804 | −9.552 | 1.00 | 16.64 | C |
| ATOM | 9135 | CB | TYR | B | 68 | −69.654 | −29.437 | −9.951 | 1.00 | 16.25 | C |
| ATOM | 9138 | CG | TYR | B | 68 | −70.609 | −28.273 | −9.802 | 1.00 | 13.51 | C |
| ATOM | 9139 | CD1 | TYR | B | 68 | −70.521 | −27.411 | −8.738 | 1.00 | 10.49 | C |
| ATOM | 9141 | CE1 | TYR | B | 68 | −71.407 | −26.342 | −8.608 | 1.00 | 10.25 | C |
| ATOM | 9143 | CZ | TYR | B | 68 | −72.382 | −26.135 | −9.555 | 1.00 | 9.74 | C |

TABLE 3-7-continued

Coordinates of *P. tremuloides IspS*

| | | | | | | | | | | | |
|---|---|---|---|---|---|---|---|---|---|---|---|
| ATOM | 9144 | OH | TYR | B | 68 | −73.253 | −25.086 | −9.450 | 1.00 | 7.62 | O |
| ATOM | 9146 | CE2 | TYR | B | 68 | −72.484 | −26.978 | −10.625 | 1.00 | 11.14 | C |
| ATOM | 9148 | CD2 | TYR | B | 68 | −71.603 | −28.037 | −10.748 | 1.00 | 12.56 | C |
| ATOM | 9150 | C | TYR | B | 68 | −70.828 | −30.700 | −8.172 | 1.00 | 17.79 | C |
| ATOM | 9151 | O | TYR | B | 68 | −70.107 | −30.811 | −7.182 | 1.00 | 18.00 | O |
| ATOM | 9153 | N | ARG | B | 69 | −72.146 | −30.485 | −8.090 | 1.00 | 18.85 | N |
| ATOM | 9154 | CA | ARG | B | 69 | −72.784 | −30.269 | −6.789 | 1.00 | 19.46 | C |
| ATOM | 9156 | CB | ARG | B | 69 | −73.708 | −29.047 | −6.819 | 1.00 | 19.23 | C |
| ATOM | 9159 | CG | ARG | B | 69 | −75.030 | −29.219 | −7.509 | 1.00 | 18.83 | C |
| ATOM | 9162 | CD | ARG | B | 69 | −76.053 | −28.192 | −6.985 | 1.00 | 17.73 | C |
| ATOM | 9165 | NE | ARG | B | 69 | −75.642 | −26.830 | −7.297 | 1.00 | 16.01 | N |
| ATOM | 9167 | CZ | ARG | B | 69 | −75.330 | −25.889 | −6.417 | 1.00 | 14.68 | C |
| ATOM | 9168 | NH1 | ARG | B | 69 | −75.400 | −26.093 | −5.112 | 1.00 | 14.99 | N |
| ATOM | 9171 | NH2 | ARG | B | 69 | −74.959 | −24.707 | −6.861 | 1.00 | 15.04 | N |
| ATOM | 9174 | C | ARG | B | 69 | −73.490 | −31.489 | −6.234 | 1.00 | 20.50 | C |
| ATOM | 9175 | O | ARG | B | 69 | −74.084 | −31.418 | −5.163 | 1.00 | 20.67 | O |
| ATOM | 9177 | N | PHE | B | 70 | −73.416 | −32.607 | −6.959 | 1.00 | 22.04 | N |
| ATOM | 9178 | CA | PHE | B | 70 | −73.853 | −33.917 | −6.450 | 1.00 | 23.03 | C |
| ATOM | 9180 | CB | PHE | B | 70 | −75.081 | −34.428 | −7.211 | 1.00 | 22.94 | C |
| ATOM | 9183 | CG | PHE | B | 70 | −76.236 | −33.503 | −7.157 | 1.00 | 21.78 | C |
| ATOM | 9184 | CD1 | PHE | B | 70 | −77.024 | −33.441 | −6.028 | 1.00 | 20.54 | C |
| ATOM | 9186 | CE1 | PHE | B | 70 | −78.076 | −32.571 | −5.959 | 1.00 | 20.32 | C |
| ATOM | 9188 | CZ | PHE | B | 70 | −78.353 | −31.752 | −7.025 | 1.00 | 20.73 | C |
| ATOM | 9190 | CE2 | PHE | B | 70 | −77.564 | −31.796 | −8.160 | 1.00 | 21.24 | C |
| ATOM | 9192 | CD2 | PHE | B | 70 | −76.511 | −32.665 | −8.220 | 1.00 | 21.22 | C |
| ATOM | 9194 | C | PHE | B | 70 | −72.765 | −34.962 | −6.570 | 1.00 | 24.33 | C |
| ATOM | 9195 | O | PHE | B | 70 | −73.069 | −36.142 | −6.614 | 1.00 | 24.56 | O |
| ATOM | 9197 | N | GLU | B | 71 | −71.500 | −34.547 | −6.624 | 1.00 | 26.01 | N |
| ATOM | 9198 | CA | GLU | B | 71 | −70.413 | −35.506 | −6.804 | 1.00 | 27.04 | C |
| ATOM | 9200 | CB | GLU | B | 71 | −69.042 | −34.824 | −6.885 | 1.00 | 27.48 | C |
| ATOM | 9203 | CG | GLU | B | 71 | −67.851 | −35.816 | −6.794 | 1.00 | 28.94 | C |
| ATOM | 9206 | CD | GLU | B | 71 | −66.491 | −35.192 | −7.081 | 1.00 | 30.38 | C |
| ATOM | 9207 | OE1 | GLU | B | 71 | −66.398 | −34.192 | −7.835 | 1.00 | 30.52 | O |
| ATOM | 9208 | OE2 | GLU | B | 71 | −65.501 | −35.730 | −6.544 | 1.00 | 32.16 | O |
| ATOM | 9209 | C | GLU | B | 71 | −70.436 | −36.531 | −5.680 | 1.00 | 27.46 | C |
| ATOM | 9210 | O | GLU | B | 71 | −70.449 | −37.723 | −5.937 | 1.00 | 27.67 | O |
| ATOM | 9212 | N | SER | B | 72 | −70.464 | −36.087 | −4.435 | 1.00 | 28.04 | N |
| ATOM | 9213 | CA | SER | B | 72 | −70.381 | −37.044 | −3.348 | 1.00 | 28.86 | C |
| ATOM | 9215 | CB | SER | B | 72 | −70.388 | −36.340 | −1.983 | 1.00 | 29.09 | C |
| ATOM | 9218 | OG | SER | B | 72 | −71.649 | −35.751 | −1.687 | 1.00 | 30.21 | O |
| ATOM | 9220 | C | SER | B | 72 | −71.519 | −38.058 | −3.481 | 1.00 | 29.30 | C |
| ATOM | 9221 | O | SER | B | 72 | −71.304 | −39.265 | −3.384 | 1.00 | 29.24 | O |
| ATOM | 9223 | N | ASP | B | 73 | −72.719 | −37.560 | −3.756 | 1.00 | 30.03 | N |
| ATOM | 9224 | CA | ASP | B | 73 | −73.897 | −38.417 | −3.874 | 1.00 | 30.63 | C |
| ATOM | 9226 | CB | ASP | B | 73 | −75.184 | −37.598 | −4.116 | 1.00 | 30.74 | C |
| ATOM | 9229 | CG | ASP | B | 73 | −75.419 | −36.509 | −3.052 | 1.00 | 31.84 | C |
| ATOM | 9230 | OD1 | ASP | B | 73 | −75.562 | −36.830 | −1.841 | 1.00 | 31.70 | O |
| ATOM | 9231 | OD2 | ASP | B | 73 | −75.473 | −35.317 | −3.443 | 1.00 | 33.81 | O |
| ATOM | 9232 | C | ASP | B | 73 | −73.722 | −39.443 | −4.994 | 1.00 | 30.81 | C |
| ATOM | 9233 | O | ASP | B | 73 | −74.130 | −40.590 | −4.835 | 1.00 | 31.39 | O |
| ATOM | 9235 | N | ILE | B | 74 | −73.122 | −39.031 | −6.112 | 1.00 | 30.96 | N |
| ATOM | 9236 | CA | ILE | B | 74 | −72.917 | −39.912 | −7.282 | 1.00 | 31.04 | C |
| ATOM | 9238 | CB | ILE | B | 74 | −72.461 | −39.114 | −8.524 | 1.00 | 30.88 | C |
| ATOM | 9240 | CG1 | ILE | B | 74 | −73.585 | −38.213 | −9.018 | 1.00 | 30.99 | C |
| ATOM | 9243 | CD1 | ILE | B | 74 | −73.105 | −37.120 | −9.923 | 1.00 | 31.54 | C |
| ATOM | 9247 | CG2 | ILE | B | 74 | −72.052 | −40.035 | −9.642 | 1.00 | 29.85 | C |
| ATOM | 9251 | C | ILE | B | 74 | −71.885 | −41.005 | −6.999 | 1.00 | 31.45 | C |
| ATOM | 9252 | O | ILE | B | 74 | −72.098 | −42.165 | −7.347 | 1.00 | 31.31 | O |
| ATOM | 9254 | N | ARG | B | 75 | −70.768 | −40.628 | −6.380 | 1.00 | 31.93 | N |
| ATOM | 9255 | CA | ARG | B | 75 | −69.778 | −41.601 | −5.947 | 1.00 | 32.38 | C |
| ATOM | 9257 | CB | ARG | B | 75 | −68.629 | −40.959 | −5.137 | 1.00 | 32.87 | C |
| ATOM | 9260 | CG | ARG | B | 75 | −67.310 | −40.751 | −5.915 | 1.00 | 35.01 | C |
| ATOM | 9263 | CD | ARG | B | 75 | −66.089 | −40.489 | −5.003 | 1.00 | 37.62 | C |
| ATOM | 9266 | NE | ARG | B | 75 | −65.260 | −41.687 | −4.783 | 1.00 | 41.03 | N |
| ATOM | 9268 | CZ | ARG | B | 75 | −64.461 | −42.253 | −5.700 | 1.00 | 44.29 | C |
| ATOM | 9269 | NH1 | ARG | B | 75 | −64.385 | −41.751 | −6.931 | 1.00 | 46.22 | N |
| ATOM | 9272 | NH2 | ARG | B | 75 | −63.741 | −43.341 | −5.404 | 1.00 | 44.30 | N |
| ATOM | 9275 | C | ARG | B | 75 | −70.478 | −42.673 | −5.126 | 1.00 | 32.18 | C |
| ATOM | 9276 | O | ARG | B | 75 | −70.307 | −43.849 | −5.398 | 1.00 | 32.19 | O |
| ATOM | 9278 | N | ARG | B | 76 | −71.280 | −42.275 | −4.143 | 1.00 | 32.21 | N |
| ATOM | 9279 | CA | ARG | B | 76 | −71.975 | −43.256 | −3.307 | 1.00 | 32.61 | C |
| ATOM | 9281 | CB | ARG | B | 76 | −72.737 | −42.582 | −2.162 | 1.00 | 32.75 | C |
| ATOM | 9284 | CG | ARG | B | 76 | −71.880 | −42.320 | −.929 | 1.00 | 33.44 | C |
| ATOM | 9287 | CD | ARG | B | 76 | −72.720 | −42.046 | .334 | 1.00 | 34.16 | C |
| ATOM | 9290 | NE | ARG | B | 76 | −73.797 | −41.074 | .124 | 1.00 | 34.53 | N |
| ATOM | 9292 | CZ | ARG | B | 76 | −73.627 | −39.765 | −.063 | 1.00 | 34.38 | C |
| ATOM | 9293 | NH1 | ARG | B | 76 | −72.414 | −39.219 | −.092 | 1.00 | 34.34 | N |
| ATOM | 9296 | NH2 | ARG | B | 76 | −74.689 | −38.993 | −.241 | 1.00 | 34.71 | N |

TABLE 3-7-continued

| Coordinates of *P. tremuloides IspS* | | | | | | | | | | | |
|---|---|---|---|---|---|---|---|---|---|---|---|
| ATOM | 9299 | C | ARG | B | 76 | −72.918 | −44.159 | −4.112 | 1.00 | 32.81 | C |
| ATOM | 9300 | O | ARG | B | 76 | −72.863 | −45.379 | −3.995 | 1.00 | 32.86 | O |
| ATOM | 9302 | N | ALA | B | 77 | −73.780 | −43.559 | −4.923 | 1.00 | 33.10 | N |
| ATOM | 9303 | CA | ALA | B | 77 | −74.655 | −44.307 | −5.813 | 1.00 | 33.27 | C |
| ATOM | 9305 | CB | ALA | B | 77 | −75.321 | −43.366 | −6.770 | 1.00 | 33.26 | C |
| ATOM | 9309 | C | ALA | B | 77 | −73.884 | −45.370 | −6.578 | 1.00 | 33.80 | C |
| ATOM | 9310 | O | ALA | B | 77 | −74.235 | −46.542 | −6.559 | 1.00 | 33.75 | O |
| ATOM | 9312 | N | LEU | B | 78 | −72.816 | −44.952 | −7.242 | 1.00 | 34.77 | N |
| ATOM | 9313 | CA | LEU | B | 78 | −71.987 | −45.868 | −8.019 | 1.00 | 35.41 | C |
| ATOM | 9315 | CB | LEU | B | 78 | −70.845 | −45.109 | −8.702 | 1.00 | 35.01 | C |
| ATOM | 9318 | CG | LEU | B | 78 | −71.220 | −44.092 | −9.782 | 1.00 | 34.37 | C |
| ATOM | 9320 | CD1 | LEU | B | 78 | −69.945 | −43.502 | −10.381 | 1.00 | 33.93 | C |
| ATOM | 9324 | CD2 | LEU | B | 78 | −72.109 | −44.692 | −10.873 | 1.00 | 32.94 | C |
| ATOM | 9328 | C | LEU | B | 78 | −71.409 | −46.974 | −7.142 | 1.00 | 36.50 | C |
| ATOM | 9329 | O | LEU | B | 78 | −71.336 | −48.124 | −7.552 | 1.00 | 36.87 | O |
| ATOM | 9331 | N | ASP | B | 79 | −71.005 | −46.619 | −5.931 | 1.00 | 37.74 | N |
| ATOM | 9332 | CA | ASP | B | 79 | −70.308 | −47.545 | −5.056 | 1.00 | 38.74 | C |
| ATOM | 9334 | CB | ASP | B | 79 | −69.787 | −46.810 | −3.819 | 1.00 | 38.99 | C |
| ATOM | 9337 | CG | ASP | B | 79 | −68.499 | −47.386 | −3.313 | 1.00 | 40.08 | C |
| ATOM | 9338 | OD1 | ASP | B | 79 | −68.494 | −48.591 | −2.976 | 1.00 | 42.32 | O |
| ATOM | 9339 | OD2 | ASP | B | 79 | −67.494 | −46.638 | −3.261 | 1.00 | 41.24 | O |
| ATOM | 9340 | C | ASP | B | 79 | −71.207 | −48.705 | −4.645 | 1.00 | 39.42 | C |
| ATOM | 9341 | O | ASP | B | 79 | −70.736 | −49.835 | −4.505 | 1.00 | 39.58 | O |
| ATOM | 9343 | N | ARG | B | 80 | −72.495 | −48.424 | −4.450 | 1.00 | 40.26 | N |
| ATOM | 9344 | CA | ARG | B | 80 | −73.471 | −49.470 | −4.143 | 1.00 | 40.92 | C |
| ATOM | 9346 | CB | ARG | B | 80 | −74.823 | −48.881 | −3.716 | 1.00 | 41.46 | C |
| ATOM | 9349 | CG | ARG | B | 80 | −74.871 | −48.247 | −2.308 | 1.00 | 42.87 | C |
| ATOM | 9352 | CD | ARG | B | 80 | −76.316 | −47.826 | −1.936 | 1.00 | 44.62 | C |
| ATOM | 9355 | NE | ARG | B | 80 | −76.946 | −46.968 | −2.949 | 1.00 | 45.87 | N |
| ATOM | 9357 | CZ | ARG | B | 80 | −76.741 | −45.651 | −3.089 | 1.00 | 46.82 | C |
| ATOM | 9358 | NH1 | ARG | B | 80 | −75.905 | −44.989 | −2.282 | 1.00 | 46.27 | N |
| ATOM | 9361 | NH2 | ARG | B | 80 | −77.378 | −44.988 | −4.059 | 1.00 | 47.22 | N |
| ATOM | 9364 | C | ARG | B | 80 | −73.667 | −50.341 | −5.371 | 1.00 | 40.77 | C |
| ATOM | 9365 | O | ARG | B | 80 | −73.642 | −51.563 | −5.275 | 1.00 | 41.06 | O |
| ATOM | 9367 | N | PHE | B | 81 | −73.863 | −49.705 | −6.520 | 1.00 | 40.56 | N |
| ATOM | 9368 | CA | PHE | B | 81 | −73.986 | −50.418 | −7.787 | 1.00 | 40.59 | C |
| ATOM | 9370 | CB | PHE | B | 81 | −73.984 | −49.426 | −8.956 | 1.00 | 40.73 | C |
| ATOM | 9373 | CG | PHE | B | 81 | −73.898 | −50.063 | −10.323 | 1.00 | 40.84 | C |
| ATOM | 9374 | CD1 | PHE | B | 81 | −75.000 | −50.668 | −10.893 | 1.00 | 41.39 | C |
| ATOM | 9376 | CE1 | PHE | B | 81 | −74.925 | −51.236 | −12.167 | 1.00 | 41.67 | C |
| ATOM | 9378 | CZ | PHE | B | 81 | −73.741 | −51.191 | −12.877 | 1.00 | 41.33 | C |
| ATOM | 9380 | CE2 | PHE | B | 81 | −72.638 | −50.580 | −12.326 | 1.00 | 41.19 | C |
| ATOM | 9382 | CD2 | PHE | B | 81 | −72.720 | −50.012 | −11.057 | 1.00 | 41.39 | C |
| ATOM | 9384 | C | PHE | B | 81 | −72.871 | −51.441 | −7.953 | 1.00 | 40.47 | C |
| ATOM | 9385 | O | PHE | B | 81 | −73.134 | −52.583 | −8.311 | 1.00 | 40.85 | O |
| ATOM | 9387 | N | VAL | B | 82 | −71.633 | −51.051 | −7.683 | 1.00 | 40.26 | N |
| ATOM | 9388 | CA | VAL | B | 82 | −70.522 | −51.986 | −7.821 | 1.00 | 40.24 | C |
| ATOM | 9390 | CB | VAL | B | 82 | −69.173 | −51.386 | −7.379 | 1.00 | 40.28 | C |
| ATOM | 9392 | CG1 | VAL | B | 82 | −68.164 | −52.493 | −7.063 | 1.00 | 39.98 | C |
| ATOM | 9396 | CG2 | VAL | B | 82 | −68.644 | −50.462 | −8.451 | 1.00 | 40.09 | C |
| ATOM | 9400 | C | VAL | B | 82 | −70.788 | −53.230 | −7.005 | 1.00 | 40.16 | C |
| ATOM | 9401 | O | VAL | B | 82 | −70.880 | −54.313 | −7.559 | 1.00 | 40.13 | O |
| ATOM | 9403 | N | SER | B | 83 | −70.953 | −53.056 | −5.698 | 1.00 | 40.26 | N |
| ATOM | 9404 | CA | SER | B | 83 | −71.070 | −54.174 | −4.749 | 1.00 | 40.43 | C |
| ATOM | 9406 | CB | SER | B | 83 | −70.797 | −53.666 | −3.331 | 1.00 | 40.54 | C |
| ATOM | 9409 | OG | SER | B | 83 | −71.256 | −52.330 | −3.191 | 1.00 | 40.89 | O |
| ATOM | 9411 | C | SER | B | 83 | −72.415 | −54.912 | −4.831 | 1.00 | 40.34 | C |
| ATOM | 9412 | O | SER | B | 83 | −73.137 | −55.046 | −3.845 | 1.00 | 39.99 | O |
| ATOM | 9414 | N | SER | B | 84 | −72.698 | −55.400 | −6.038 | 1.00 | 40.57 | N |
| ATOM | 9415 | CA | SER | B | 84 | −73.902 | −56.154 | −6.411 | 1.00 | 40.63 | C |
| ATOM | 9417 | CB | SER | B | 84 | −75.154 | −55.679 | −5.651 | 1.00 | 40.56 | C |
| ATOM | 9420 | OG | SER | B | 84 | −75.292 | −54.268 | −5.663 | 1.00 | 39.82 | O |
| ATOM | 9422 | C | SER | B | 84 | −74.104 | −56.026 | −7.940 | 1.00 | 40.85 | C |
| ATOM | 9423 | O | SER | B | 84 | −75.104 | −55.462 | −8.395 | 1.00 | 41.24 | O |
| ATOM | 9425 | N | GLY | B | 85 | −73.136 | −56.524 | −8.720 | 1.00 | 40.75 | N |
| ATOM | 9426 | CA | GLY | B | 85 | −73.201 | −56.506 | −10.191 | 1.00 | 40.64 | C |
| ATOM | 9429 | C | GLY | B | 85 | −73.225 | −55.120 | −10.815 | 1.00 | 40.64 | C |
| ATOM | 9430 | O | GLY | B | 85 | −74.133 | −54.794 | −11.590 | 1.00 | 40.32 | O |
| ATOM | 9432 | N | THR | B | 93 | −74.847 | −57.360 | −18.759 | 1.00 | 36.30 | N |
| ATOM | 9433 | CA | THR | B | 93 | −75.593 | −58.129 | −19.774 | 1.00 | 35.99 | C |
| ATOM | 9435 | CB | THR | B | 93 | −76.251 | −59.379 | −19.152 | 1.00 | 35.87 | C |
| ATOM | 9437 | OG1 | THR | B | 93 | −76.347 | −60.389 | −20.158 | 1.00 | 35.64 | O |
| ATOM | 9439 | CG2 | THR | B | 93 | −77.646 | −59.062 | −18.548 | 1.00 | 34.95 | C |
| ATOM | 9443 | C | THR | B | 93 | −76.625 | −57.274 | −20.583 | 1.00 | 35.90 | C |
| ATOM | 9444 | O | THR | B | 93 | −77.764 | −57.688 | −20.843 | 1.00 | 35.74 | O |
| ATOM | 9446 | N | SER | B | 94 | −76.175 | −56.076 | −20.963 | 1.00 | 35.58 | N |
| ATOM | 9447 | CA | SER | B | 94 | −76.874 | −55.150 | −21.866 | 1.00 | 34.97 | C |
| ATOM | 9449 | CB | SER | B | 94 | −78.074 | −54.472 | −21.190 | 1.00 | 35.06 | C |

TABLE 3-7-continued

Coordinates of *P. tremuloides IspS*

| | | | | | | | | | | | |
|---|---|---|---|---|---|---|---|---|---|---|---|
| ATOM | 9452 | OG | SER | B | 94 | −77.702 | −53.260 | −20.541 | 1.00 | 34.37 | O |
| ATOM | 9454 | C | SER | B | 94 | −75.831 | −54.097 | −22.232 | 1.00 | 34.39 | C |
| ATOM | 9455 | O | SER | B | 94 | −75.212 | −53.518 | −21.341 | 1.00 | 34.11 | O |
| ATOM | 9457 | N | LEU | B | 95 | −75.619 | −53.864 | −23.522 | 1.00 | 33.77 | N |
| ATOM | 9458 | CA | LEU | B | 95 | −74.490 | −53.045 | −23.952 | 1.00 | 33.33 | C |
| ATOM | 9460 | CB | LEU | B | 95 | −74.373 | −53.010 | −25.475 | 1.00 | 33.30 | C |
| ATOM | 9463 | CG | LEU | B | 95 | −73.154 | −52.246 | −26.006 | 1.00 | 33.27 | C |
| ATOM | 9465 | CD1 | LEU | B | 95 | −71.909 | −52.455 | −25.137 | 1.00 | 32.89 | C |
| ATOM | 9469 | CD2 | LEU | B | 95 | −72.864 | −52.649 | −27.438 | 1.00 | 33.19 | C |
| ATOM | 9473 | C | LEU | B | 95 | −74.551 | −51.623 | −23.413 | 1.00 | 33.00 | C |
| ATOM | 9474 | O | LEU | B | 95 | −73.588 | −51.151 | −22.809 | 1.00 | 32.83 | O |
| ATOM | 9476 | N | HIS | B | 96 | −75.678 | −50.949 | −23.633 | 1.00 | 32.64 | N |
| ATOM | 9477 | CA | HIS | B | 96 | −75.853 | −49.576 | −23.171 | 1.00 | 32.39 | C |
| ATOM | 9479 | CB | HIS | B | 96 | −77.246 | −49.069 | −23.527 | 1.00 | 32.64 | C |
| ATOM | 9482 | CG | HIS | B | 96 | −77.528 | −47.689 | −23.025 | 1.00 | 34.16 | C |
| ATOM | 9483 | ND1 | HIS | B | 96 | −76.565 | −46.703 | −22.981 | 1.00 | 36.21 | N |
| ATOM | 9485 | CE1 | HIS | B | 96 | −77.096 | −45.594 | −22.496 | 1.00 | 36.92 | C |
| ATOM | 9487 | NE2 | HIS | B | 96 | −78.371 | −45.827 | −22.227 | 1.00 | 37.06 | N |
| ATOM | 9489 | CD2 | HIS | B | 96 | −78.664 | −47.130 | −22.548 | 1.00 | 35.43 | C |
| ATOM | 9491 | C | HIS | B | 96 | −75.612 | −49.445 | −21.665 | 1.00 | 31.78 | C |
| ATOM | 9492 | O | HIS | B | 96 | −74.936 | −48.523 | −21.215 | 1.00 | 31.95 | O |
| ATOM | 9494 | N | GLY | B | 97 | −76.156 | −50.372 | −20.887 | 1.00 | 31.10 | N |
| ATOM | 9495 | CA | GLY | B | 97 | −75.907 | −50.396 | −19.446 | 1.00 | 30.52 | C |
| ATOM | 9498 | C | GLY | B | 97 | −74.434 | −50.532 | −19.085 | 1.00 | 29.95 | C |
| ATOM | 9499 | O | GLY | B | 97 | −73.936 | −49.797 | −18.241 | 1.00 | 30.21 | O |
| ATOM | 9501 | N | THR | B | 98 | −73.740 | −51.470 | −19.726 | 1.00 | 29.15 | N |
| ATOM | 9502 | CA | THR | B | 98 | −72.314 | −51.690 | −19.490 | 1.00 | 28.55 | C |
| ATOM | 9504 | CB | THR | B | 98 | −71.803 | −52.955 | −20.248 | 1.00 | 28.48 | C |
| ATOM | 9506 | OG1 | THR | B | 98 | −72.678 | −54.066 | −19.997 | 1.00 | 28.41 | O |
| ATOM | 9508 | CG2 | THR | B | 98 | −70.405 | −53.331 | −19.816 | 1.00 | 27.74 | C |
| ATOM | 9512 | C | THR | B | 98 | −71.492 | −50.452 | −19.894 | 1.00 | 28.31 | C |
| ATOM | 9513 | O | THR | B | 98 | −70.658 | −49.979 | −19.127 | 1.00 | 28.13 | O |
| ATOM | 9515 | N | ALA | B | 99 | −71.750 | −49.910 | −21.080 | 1.00 | 28.04 | N |
| ATOM | 9516 | CA | ALA | B | 99 | −70.984 | −48.758 | −21.578 | 1.00 | 27.88 | C |
| ATOM | 9518 | CB | ALA | B | 99 | −71.387 | −48.406 | −23.014 | 1.00 | 27.78 | C |
| ATOM | 9522 | C | ALA | B | 99 | −71.127 | −47.538 | −20.684 | 1.00 | 27.62 | C |
| ATOM | 9523 | O | ALA | B | 99 | −70.135 | −46.885 | −20.361 | 1.00 | 27.84 | O |
| ATOM | 9525 | N | LEU | B | 100 | −72.357 | −47.233 | −20.290 | 1.00 | 27.20 | N |
| ATOM | 9526 | CA | LEU | B | 100 | −72.613 | −46.088 | −19.422 | 1.00 | 27.08 | C |
| ATOM | 9528 | CB | LEU | B | 100 | −74.122 | −45.900 | −19.230 | 1.00 | 26.95 | C |
| ATOM | 9531 | CG | LEU | B | 100 | −74.560 | −44.715 | −18.367 | 1.00 | 26.27 | C |
| ATOM | 9533 | CD1 | LEU | B | 100 | −73.753 | −43.478 | −18.734 | 1.00 | 26.19 | C |
| ATOM | 9537 | CD2 | LEU | B | 100 | −76.052 | −44.445 | −18.504 | 1.00 | 25.20 | C |
| ATOM | 9541 | C | LEU | B | 100 | −71.928 | −46.221 | −18.046 | 1.00 | 27.23 | C |
| ATOM | 9542 | O | LEU | B | 100 | −71.368 | −45.243 | −17.523 | 1.00 | 27.16 | O |
| ATOM | 9544 | N | SER | B | 101 | −71.980 | −47.429 | −17.472 | 1.00 | 27.00 | N |
| ATOM | 9545 | CA | SER | B | 101 | −71.475 | −47.682 | −16.117 | 1.00 | 26.63 | C |
| ATOM | 9547 | CB | SER | B | 101 | −72.039 | −48.992 | −15.568 | 1.00 | 26.49 | C |
| ATOM | 9550 | OG | SER | B | 101 | −71.758 | −50.063 | −16.442 | 1.00 | 26.38 | O |
| ATOM | 9552 | C | SER | B | 101 | −69.956 | −47.740 | −16.090 | 1.00 | 26.47 | C |
| ATOM | 9553 | O | SER | B | 101 | −69.326 | −47.324 | −15.121 | 1.00 | 26.35 | O |
| ATOM | 9555 | N | PHE | B | 102 | −69.381 | −48.288 | −17.154 | 1.00 | 26.29 | N |
| ATOM | 9556 | CA | PHE | B | 102 | −67.934 | −48.332 | −17.322 | 1.00 | 25.91 | C |
| ATOM | 9558 | CB | PHE | B | 102 | −67.588 | −49.005 | −18.652 | 1.00 | 25.96 | C |
| ATOM | 9561 | CG | PHE | B | 102 | −66.133 | −49.020 | −18.958 | 1.00 | 25.81 | C |
| ATOM | 9562 | CD1 | PHE | B | 102 | −65.360 | −50.115 | −18.633 | 1.00 | 25.96 | C |
| ATOM | 9564 | CE1 | PHE | B | 102 | −63.999 | −50.122 | −18.909 | 1.00 | 26.94 | C |
| ATOM | 9566 | CZ | PHE | B | 102 | −63.403 | −49.026 | −19.519 | 1.00 | 26.27 | C |
| ATOM | 9568 | CE2 | PHE | B | 102 | −64.174 | −47.930 | −19.848 | 1.00 | 26.19 | C |
| ATOM | 9570 | CD2 | PHE | B | 102 | −65.531 | −47.933 | −19.573 | 1.00 | 26.04 | C |
| ATOM | 9572 | C | PHE | B | 102 | −67.416 | −46.911 | −17.315 | 1.00 | 25.56 | C |
| ATOM | 9573 | O | PHE | B | 102 | −66.486 | −46.564 | −16.568 | 1.00 | 25.37 | O |
| ATOM | 9575 | N | ARG | B | 103 | −68.050 | −46.095 | −18.152 | 1.00 | 25.20 | N |
| ATOM | 9576 | CA | ARG | B | 103 | −67.663 | −44.696 | −18.322 | 1.00 | 25.09 | C |
| ATOM | 9578 | CB | ARG | B | 103 | −68.510 | −44.026 | −19.400 | 1.00 | 25.12 | C |
| ATOM | 9581 | CG | ARG | B | 103 | −68.194 | −42.561 | −19.572 | 1.00 | 25.41 | C |
| ATOM | 9584 | CD | ARG | B | 103 | −68.744 | −42.035 | −20.889 | 1.00 | 26.68 | C |
| ATOM | 9587 | NE | ARG | B | 103 | −70.197 | −41.843 | −20.877 | 1.00 | 27.49 | N |
| ATOM | 9589 | CZ | ARG | B | 103 | −70.826 | −40.851 | −20.246 | 1.00 | 26.56 | C |
| ATOM | 9590 | NH1 | ARG | B | 103 | −70.139 | −39.963 | −19.531 | 1.00 | 27.11 | N |
| ATOM | 9593 | NH2 | ARG | B | 103 | −72.148 | −40.759 | −20.310 | 1.00 | 25.20 | N |
| ATOM | 9596 | C | ARG | B | 103 | −67.785 | −43.898 | −17.033 | 1.00 | 24.61 | C |
| ATOM | 9597 | O | ARG | B | 103 | −66.865 | −43.168 | −16.659 | 1.00 | 24.67 | O |
| ATOM | 9599 | N | LEU | B | 104 | −68.927 | −44.013 | −16.371 | 1.00 | 23.79 | N |
| ATOM | 9600 | CA | LEU | B | 104 | −69.125 | −43.263 | −15.148 | 1.00 | 23.23 | C |
| ATOM | 9602 | CB | LEU | B | 104 | −70.591 | −43.342 | −14.693 | 1.00 | 23.01 | C |
| ATOM | 9605 | CG | LEU | B | 104 | −71.607 | −42.620 | −15.584 | 1.00 | 21.36 | C |
| ATOM | 9607 | CD1 | LEU | B | 104 | −73.002 | −42.860 | −15.067 | 1.00 | 19.31 | C |

TABLE 3-7-continued

Coordinates of *P. tremuloides IspS*

| | | | | | | | | | | | |
|---|---|---|---|---|---|---|---|---|---|---|---|
| ATOM | 9611 | CD2 | LEU | B | 104 | −71.310 | −41.157 | −15.633 | 1.00 | 19.57 | C |
| ATOM | 9615 | C | LEU | B | 104 | −68.156 | −43.781 | −14.071 | 1.00 | 23.15 | C |
| ATOM | 9616 | O | LEU | B | 104 | −67.445 | −43.007 | −13.423 | 1.00 | 23.40 | O |
| ATOM | 9618 | N | LEU | B | 105 | −68.106 | −45.091 | −13.894 | 1.00 | 22.79 | N |
| ATOM | 9619 | CA | LEU | B | 105 | −67.203 | −45.659 | −12.916 | 1.00 | 22.40 | C |
| ATOM | 9621 | CB | LEU | B | 105 | −67.303 | −47.178 | −12.912 | 1.00 | 22.42 | C |
| ATOM | 9624 | CG | LEU | B | 105 | −68.505 | −47.709 | −12.163 | 1.00 | 21.82 | C |
| ATOM | 9626 | CD1 | LEU | B | 105 | −68.810 | −49.120 | −12.591 | 1.00 | 21.95 | C |
| ATOM | 9630 | CD2 | LEU | B | 105 | −68.201 | −47.648 | −10.692 | 1.00 | 22.14 | C |
| ATOM | 9634 | C | LEU | B | 105 | −65.767 | −45.239 | −13.196 | 1.00 | 22.33 | C |
| ATOM | 9635 | O | LEU | B | 105 | −65.049 | −44.823 | −12.275 | 1.00 | 22.13 | O |
| ATOM | 9637 | N | ARG | B | 106 | −65.331 | −45.342 | −14.451 | 1.00 | 22.08 | N |
| ATOM | 9638 | CA | ARG | B | 106 | −63.953 | −44.973 | −14.730 | 1.00 | 22.20 | C |
| ATOM | 9640 | CB | ARG | B | 106 | −63.521 | −45.266 | −16.151 | 1.00 | 22.33 | C |
| ATOM | 9643 | CG | ARG | B | 106 | −62.075 | −44.827 | −16.329 | 1.00 | 23.60 | C |
| ATOM | 9646 | CD | ARG | B | 106 | −61.383 | −45.445 | −17.513 | 1.00 | 24.71 | C |
| ATOM | 9649 | NE | ARG | B | 106 | −61.078 | −46.852 | −17.319 | 1.00 | 24.66 | N |
| ATOM | 9651 | CZ | ARG | B | 106 | −60.418 | −47.582 | −18.206 | 1.00 | 25.75 | C |
| ATOM | 9652 | NH1 | ARG | B | 106 | −59.995 | −47.028 | −19.337 | 1.00 | 26.41 | N |
| ATOM | 9655 | NH2 | ARG | B | 106 | −60.182 | −48.866 | −17.971 | 1.00 | 26.54 | N |
| ATOM | 9658 | C | ARG | B | 106 | −63.732 | −43.504 | −14.438 | 1.00 | 21.75 | C |
| ATOM | 9659 | O | ARG | B | 106 | −62.801 | −43.145 | −13.725 | 1.00 | 21.50 | O |
| ATOM | 9661 | N | GLN | B | 107 | −64.609 | −42.680 | −15.003 | 1.00 | 21.69 | N |
| ATOM | 9662 | CA | GLN | B | 107 | −64.630 | −41.239 | −14.794 | 1.00 | 21.64 | C |
| ATOM | 9664 | CB | GLN | B | 107 | −65.964 | −40.664 | −15.261 | 1.00 | 21.71 | C |
| ATOM | 9667 | CG | GLN | B | 107 | −66.169 | −39.178 | −14.929 | 1.00 | 21.97 | C |
| ATOM | 9670 | CD | GLN | B | 107 | −67.588 | −38.723 | −15.172 | 1.00 | 21.54 | C |
| ATOM | 9671 | OE1 | GLN | B | 107 | −68.355 | −39.365 | −15.906 | 1.00 | 20.08 | O |
| ATOM | 9672 | NE2 | GLN | B | 107 | −67.948 | −37.600 | −14.556 | 1.00 | 21.45 | N |
| ATOM | 9675 | C | GLN | B | 107 | −64.454 | −40.850 | −13.352 | 1.00 | 21.70 | C |
| ATOM | 9676 | O | GLN | B | 107 | −63.776 | −39.865 | −13.078 | 1.00 | 22.14 | O |
| ATOM | 9678 | N | HIS | B | 108 | −65.091 | −41.599 | −12.450 | 1.00 | 21.53 | N |
| ATOM | 9679 | CA | HIS | B | 108 | −65.049 | −41.326 | −11.019 | 1.00 | 21.63 | C |
| ATOM | 9681 | CB | HIS | B | 108 | −66.447 | −41.535 | −10.429 | 1.00 | 21.47 | C |
| ATOM | 9684 | CG | HIS | B | 108 | −67.416 | −40.445 | −10.752 | 1.00 | 20.91 | C |
| ATOM | 9685 | ND1 | HIS | B | 108 | −67.541 | −39.315 | −9.976 | 1.00 | 20.66 | N |
| ATOM | 9687 | CE1 | HIS | B | 108 | −68.476 | −38.535 | −10.490 | 1.00 | 20.90 | C |
| ATOM | 9689 | NE2 | HIS | B | 108 | −68.966 | −39.118 | −11.567 | 1.00 | 19.67 | N |
| ATOM | 9691 | CD2 | HIS | B | 108 | −68.326 | −40.320 | −11.747 | 1.00 | 20.76 | C |
| ATOM | 9693 | C | HIS | B | 108 | −64.024 | −42.209 | −10.269 | 1.00 | 22.22 | C |
| ATOM | 9694 | O | HIS | B | 108 | −64.220 | −42.553 | −9.104 | 1.00 | 22.17 | O |
| ATOM | 9696 | N | GLY | B | 109 | −62.950 | −42.613 | −10.933 | 1.00 | 22.91 | N |
| ATOM | 9697 | CA | GLY | B | 109 | −61.846 | −43.288 | −10.245 | 1.00 | 23.85 | C |
| ATOM | 9700 | C | GLY | B | 109 | −61.986 | −44.748 | −9.800 | 1.00 | 24.50 | C |
| ATOM | 9701 | O | GLY | B | 109 | −61.053 | −45.306 | −9.189 | 1.00 | 24.12 | O |
| ATOM | 9703 | N | PHE | B | 110 | −63.128 | −45.371 | −10.094 | 1.00 | 25.16 | N |
| ATOM | 9704 | CA | PHE | B | 110 | −63.309 | −46.791 | −9.800 | 1.00 | 25.67 | C |
| ATOM | 9706 | CB | PHE | B | 110 | −64.782 | −47.187 | −9.891 | 1.00 | 25.80 | C |
| ATOM | 9709 | CG | PHE | B | 110 | −65.625 | −46.656 | −8.772 | 1.00 | 26.12 | C |
| ATOM | 9710 | CD1 | PHE | B | 110 | −65.564 | −47.230 | −7.510 | 1.00 | 27.13 | C |
| ATOM | 9712 | CE1 | PHE | B | 110 | −66.353 | −46.751 | −6.468 | 1.00 | 27.42 | C |
| ATOM | 9714 | CZ | PHE | B | 110 | −67.215 | −45.691 | −6.692 | 1.00 | 26.93 | C |
| ATOM | 9716 | CE2 | PHE | B | 110 | −67.284 | −45.119 | −7.954 | 1.00 | 26.49 | C |
| ATOM | 9718 | CD2 | PHE | B | 110 | −66.494 | −45.601 | −8.981 | 1.00 | 25.96 | C |
| ATOM | 9720 | C | PHE | B | 110 | −62.505 | −47.615 | −10.793 | 1.00 | 25.92 | C |
| ATOM | 9721 | O | PHE | B | 110 | −62.232 | −47.157 | −11.898 | 1.00 | 26.41 | O |
| ATOM | 9723 | N | GLU | B | 111 | −62.134 | −48.832 | −10.406 | 1.00 | 26.06 | N |
| ATOM | 9724 | CA | GLU | B | 111 | −61.403 | −49.724 | −11.304 | 1.00 | 26.17 | C |
| ATOM | 9726 | CB | GLU | B | 111 | −60.444 | −50.609 | −10.511 | 1.00 | 26.50 | C |
| ATOM | 9729 | CG | GLU | B | 111 | −59.372 | −51.272 | −11.374 | 1.00 | 28.11 | C |
| ATOM | 9732 | CD | GLU | B | 111 | −58.607 | −52.377 | −10.646 | 1.00 | 30.70 | C |
| ATOM | 9733 | OE1 | GLU | B | 111 | −58.660 | −52.436 | −9.390 | 1.00 | 31.99 | O |
| ATOM | 9734 | OE2 | GLU | B | 111 | −57.948 | −53.190 | −11.338 | 1.00 | 32.09 | O |
| ATOM | 9735 | C | GLU | B | 111 | −62.355 | −50.598 | −12.130 | 1.00 | 25.60 | C |
| ATOM | 9736 | O | GLU | B | 111 | −63.116 | −51.388 | −11.585 | 1.00 | 25.48 | O |
| ATOM | 9738 | N | VAL | B | 112 | −62.314 | −50.439 | −13.447 | 1.00 | 25.24 | N |
| ATOM | 9739 | CA | VAL | B | 112 | −63.026 | −51.331 | −14.357 | 1.00 | 24.90 | C |
| ATOM | 9741 | CB | VAL | B | 112 | −64.308 | −50.712 | −14.908 | 1.00 | 24.92 | C |
| ATOM | 9743 | CG1 | VAL | B | 112 | −65.268 | −50.437 | −13.771 | 1.00 | 25.26 | C |
| ATOM | 9747 | CG2 | VAL | B | 112 | −63.999 | −49.450 | −15.706 | 1.00 | 24.77 | C |
| ATOM | 9751 | C | VAL | B | 112 | −62.144 | −51.701 | −15.522 | 1.00 | 24.66 | C |
| ATOM | 9752 | O | VAL | B | 112 | −61.217 | −50.964 | −15.862 | 1.00 | 23.80 | O |
| ATOM | 9754 | N | SER | B | 113 | −62.467 | −52.842 | −16.132 | 1.00 | 24.88 | N |
| ATOM | 9755 | CA | SER | B | 113 | −61.604 | −53.494 | −17.109 | 1.00 | 25.21 | C |
| ATOM | 9757 | CB | SER | B | 113 | −61.286 | −54.913 | −16.654 | 1.00 | 24.94 | C |
| ATOM | 9760 | OG | SER | B | 113 | −60.357 | −55.523 | −17.528 | 1.00 | 24.31 | O |
| ATOM | 9762 | C | SER | B | 113 | −62.233 | −53.532 | −18.492 | 1.00 | 25.88 | C |
| ATOM | 9763 | O | SER | B | 113 | −63.446 | −53.651 | −18.630 | 1.00 | 25.86 | O |

TABLE 3-7-continued

Coordinates of *P. tremuloides IspS*

| | | | | | | | | | | | |
|---|---|---|---|---|---|---|---|---|---|---|---|
| ATOM | 9765 | N | GLN | B | 114 | −61.406 | −53.438 | −19.526 | 1.00 | 26.92 | N |
| ATOM | 9766 | CA | GLN | B | 114 | −61.928 | −53.491 | −20.880 | 1.00 | 27.83 | C |
| ATOM | 9768 | CB | GLN | B | 114 | −60.846 | −53.194 | −21.917 | 1.00 | 27.75 | C |
| ATOM | 9771 | CG | GLN | B | 114 | −59.559 | −53.952 | −21.726 | 1.00 | 28.05 | C |
| ATOM | 9774 | CD | GLN | B | 114 | −58.739 | −54.077 | −23.007 | 1.00 | 28.39 | C |
| ATOM | 9775 | OE1 | GLN | B | 114 | −59.086 | −53.515 | −24.051 | 1.00 | 29.05 | O |
| ATOM | 9776 | NE2 | GLN | B | 114 | −57.637 | −54.808 | −22.925 | 1.00 | 27.62 | N |
| ATOM | 9779 | C | GLN | B | 114 | −62.615 | −54.827 | −21.158 | 1.00 | 28.78 | C |
| ATOM | 9780 | O | GLN | B | 114 | −63.484 | −54.905 | −22.022 | 1.00 | 29.10 | O |
| ATOM | 9782 | N | GLU | B | 115 | −62.248 | −55.861 | −20.401 | 1.00 | 29.99 | N |
| ATOM | 9783 | CA | GLU | B | 115 | −62.888 | −57.181 | −20.505 | 1.00 | 30.89 | C |
| ATOM | 9785 | CB | GLU | B | 115 | −62.252 | −58.202 | −19.549 | 1.00 | 31.10 | C |
| ATOM | 9788 | CG | GLU | B | 115 | −60.740 | −58.394 | −19.697 | 1.00 | 32.35 | C |
| ATOM | 9791 | CD | GLU | B | 115 | −60.320 | −58.796 | −21.106 | 1.00 | 34.20 | C |
| ATOM | 9792 | OE1 | GLU | B | 115 | −60.965 | −59.699 | −21.688 | 1.00 | 34.94 | O |
| ATOM | 9793 | OE2 | GLU | B | 115 | −59.348 | −58.201 | −21.634 | 1.00 | 35.60 | O |
| ATOM | 9794 | C | GLU | B | 115 | −64.380 | −57.120 | −20.224 | 1.00 | 31.26 | C |
| ATOM | 9795 | O | GLU | B | 115 | −65.125 | −57.971 | −20.691 | 1.00 | 31.54 | O |
| ATOM | 9797 | N | ALA | B | 116 | −64.825 | −56.127 | −19.465 | 1.00 | 31.91 | N |
| ATOM | 9798 | CA | ALA | B | 116 | −66.255 | −55.937 | −19.259 | 1.00 | 32.69 | C |
| ATOM | 9800 | CB | ALA | B | 116 | −66.521 | −54.648 | −18.513 | 1.00 | 32.62 | C |
| ATOM | 9804 | C | ALA | B | 116 | −66.999 | −55.950 | −20.597 | 1.00 | 33.33 | C |
| ATOM | 9805 | O | ALA | B | 116 | −68.156 | −56.364 | −20.668 | 1.00 | 33.26 | O |
| ATOM | 9807 | N | PHE | B | 117 | −66.316 | −55.521 | −21.655 | 1.00 | 34.16 | N |
| ATOM | 9808 | CA | PHE | B | 117 | −66.889 | −55.498 | −22.996 | 1.00 | 34.98 | C |
| ATOM | 9810 | CB | PHE | B | 117 | −66.310 | −54.314 | −23.766 | 1.00 | 35.02 | C |
| ATOM | 9813 | CG | PHE | B | 117 | −66.868 | −52.997 | −23.345 | 1.00 | 35.06 | C |
| ATOM | 9814 | CD1 | PHE | B | 117 | −66.061 | −52.046 | −22.729 | 1.00 | 35.33 | C |
| ATOM | 9816 | CE1 | PHE | B | 117 | −66.576 | −50.825 | −22.342 | 1.00 | 35.16 | C |
| ATOM | 9818 | CZ | PHE | B | 117 | −67.907 | −50.544 | −22.570 | 1.00 | 35.37 | C |
| ATOM | 9820 | CE2 | PHE | B | 117 | −68.723 | −51.488 | −23.187 | 1.00 | 35.28 | C |
| ATOM | 9822 | CD2 | PHE | B | 117 | −68.201 | −52.701 | −23.571 | 1.00 | 34.68 | C |
| ATOM | 9824 | C | PHE | B | 117 | −66.676 | −56.766 | −23.830 | 1.00 | 35.86 | C |
| ATOM | 9825 | O | PHE | B | 117 | −66.934 | −56.755 | −25.037 | 1.00 | 35.91 | O |
| ATOM | 9827 | N | SER | B | 118 | −66.215 | −57.853 | −23.212 | 1.00 | 36.98 | N |
| ATOM | 9828 | CA | SER | B | 118 | −65.924 | −59.086 | −23.960 | 1.00 | 37.76 | C |
| ATOM | 9830 | CB | SER | B | 118 | −64.836 | −59.907 | −23.262 | 1.00 | 37.73 | C |
| ATOM | 9833 | OG | SER | B | 118 | −65.272 | −60.346 | −21.987 | 1.00 | 37.77 | O |
| ATOM | 9835 | C | SER | B | 118 | −67.178 | −59.939 | −24.215 | 1.00 | 38.48 | C |
| ATOM | 9836 | O | SER | B | 118 | −67.207 | −60.724 | −25.157 | 1.00 | 38.42 | O |
| ATOM | 9838 | N | GLY | B | 119 | −68.221 | −59.765 | −23.407 | 1.00 | 39.51 | N |
| ATOM | 9839 | CA | GLY | B | 119 | −69.481 | −60.473 | −23.629 | 1.00 | 40.51 | C |
| ATOM | 9842 | C | GLY | B | 119 | −70.287 | −60.034 | −24.848 | 1.00 | 41.51 | C |
| ATOM | 9843 | O | GLY | B | 119 | −71.444 | −60.433 | −25.002 | 1.00 | 41.53 | O |
| ATOM | 9845 | N | PHE | B | 120 | −69.688 | −59.210 | −25.709 | 1.00 | 42.79 | N |
| ATOM | 9846 | CA | PHE | B | 120 | −70.382 | −58.621 | −26.864 | 1.00 | 43.81 | C |
| ATOM | 9848 | CB | PHE | B | 120 | −70.643 | −57.121 | −26.601 | 1.00 | 43.76 | C |
| ATOM | 9851 | CG | PHE | B | 120 | −71.367 | −56.853 | −25.293 | 1.00 | 43.65 | C |
| ATOM | 9852 | CD1 | PHE | B | 120 | −72.762 | −56.874 | −25.230 | 1.00 | 43.48 | C |
| ATOM | 9854 | CE1 | PHE | B | 120 | −73.437 | −56.650 | −24.023 | 1.00 | 43.03 | C |
| ATOM | 9856 | CZ | PHE | B | 120 | −72.717 | −56.413 | −22.865 | 1.00 | 43.09 | C |
| ATOM | 9858 | CE2 | PHE | B | 120 | −71.323 | −56.397 | −22.909 | 1.00 | 43.38 | C |
| ATOM | 9860 | CD2 | PHE | B | 120 | −70.655 | −56.619 | −24.120 | 1.00 | 43.41 | C |
| ATOM | 9862 | C | PHE | B | 120 | −69.607 | −58.832 | −28.175 | 1.00 | 44.81 | C |
| ATOM | 9863 | O | PHE | B | 120 | −69.930 | −58.238 | −29.205 | 1.00 | 44.65 | O |
| ATOM | 9865 | N | LYS | B | 121 | −68.602 | −59.705 | −28.126 | 1.00 | 46.19 | N |
| ATOM | 9866 | CA | LYS | B | 121 | −67.757 | −60.004 | −29.272 | 1.00 | 47.31 | C |
| ATOM | 9868 | CB | LYS | B | 121 | −66.275 | −59.928 | −28.870 | 1.00 | 47.47 | C |
| ATOM | 9871 | CG | LYS | B | 121 | −65.743 | −58.495 | −28.637 | 1.00 | 48.13 | C |
| ATOM | 9874 | CD | LYS | B | 121 | −64.532 | −58.439 | −27.675 | 1.00 | 48.89 | C |
| ATOM | 9877 | CE | LYS | B | 121 | −63.261 | −59.094 | −28.241 | 1.00 | 49.20 | C |
| ATOM | 9880 | NZ | LYS | B | 121 | −62.541 | −58.232 | −29.218 | 1.00 | 49.04 | N |
| ATOM | 9884 | C | LYS | B | 121 | −68.096 | −61.400 | −29.810 | 1.00 | 48.15 | C |
| ATOM | 9885 | O | LYS | B | 121 | −68.199 | −62.361 | −29.043 | 1.00 | 48.36 | O |
| ATOM | 9887 | N | ASP | B | 122 | −68.270 | −61.510 | −31.126 | 1.00 | 49.04 | N |
| ATOM | 9888 | CA | ASP | B | 122 | −68.611 | −62.788 | −31.754 | 1.00 | 49.60 | C |
| ATOM | 9890 | CB | ASP | B | 122 | −69.070 | −62.596 | −33.217 | 1.00 | 49.52 | C |
| ATOM | 9893 | CG | ASP | B | 122 | −67.989 | −62.015 | −34.126 | 1.00 | 49.18 | C |
| ATOM | 9894 | OD1 | ASP | B | 122 | −66.792 | −62.306 | −33.938 | 1.00 | 48.96 | O |
| ATOM | 9895 | OD2 | ASP | B | 122 | −68.351 | −61.268 | −35.057 | 1.00 | 48.82 | O |
| ATOM | 9896 | C | ASP | B | 122 | −67.455 | −63.785 | −31.651 | 1.00 | 50.31 | C |
| ATOM | 9897 | O | ASP | B | 122 | −66.369 | −63.441 | −31.171 | 1.00 | 50.33 | O |
| ATOM | 9899 | N | GLN | B | 123 | −67.705 | −65.014 | −32.098 | 1.00 | 51.05 | N |
| ATOM | 9900 | CA | GLN | B | 123 | −66.716 | −66.095 | −32.057 | 1.00 | 51.61 | C |
| ATOM | 9902 | CB | GLN | B | 123 | −67.263 | −67.330 | −32.785 | 1.00 | 51.82 | C |
| ATOM | 9905 | CG | GLN | B | 123 | −68.483 | −67.986 | −32.117 | 1.00 | 52.32 | C |
| ATOM | 9908 | CD | GLN | B | 123 | −68.117 | −69.137 | −31.184 | 1.00 | 52.64 | C |
| ATOM | 9909 | OE1 | GLN | B | 123 | −67.146 | −69.062 | −30.432 | 1.00 | 53.02 | O |

TABLE 3-7-continued

Coordinates of *P. tremuloides IspS*

| | | | | | | | | | | | |
|---|---|---|---|---|---|---|---|---|---|---|---|
| ATOM | 9910 | NE2 | GLN | B | 123 | −68.904 | −70.207 | −31.230 | 1.00 | 52.04 | N |
| ATOM | 9913 | C | GLN | B | 123 | −65.358 | −65.694 | −32.659 | 1.00 | 51.78 | C |
| ATOM | 9914 | O | GLN | B | 123 | −64.309 | −66.000 | −32.090 | 1.00 | 51.67 | O |
| ATOM | 9916 | N | ASN | B | 124 | −65.388 | −65.004 | −33.799 | 1.00 | 52.05 | N |
| ATOM | 9917 | CA | ASN | B | 124 | −64.166 | −64.547 | −34.473 | 1.00 | 52.25 | C |
| ATOM | 9919 | CB | ASN | B | 124 | −64.486 | −64.042 | −35.884 | 1.00 | 52.25 | C |
| ATOM | 9922 | CG | ASN | B | 124 | −64.911 | −65.158 | −36.819 | 1.00 | 51.88 | C |
| ATOM | 9923 | OD1 | ASN | B | 124 | −65.918 | −65.825 | −36.592 | 1.00 | 51.43 | O |
| ATOM | 9924 | ND2 | ASN | B | 124 | −64.144 | −65.364 | −37.880 | 1.00 | 51.23 | N |
| ATOM | 9927 | C | ASN | B | 124 | −63.382 | −63.466 | −33.716 | 1.00 | 52.43 | C |
| ATOM | 9928 | O | ASN | B | 124 | −62.189 | −63.287 | −33.959 | 1.00 | 52.33 | O |
| ATOM | 9930 | N | GLY | B | 125 | −64.051 | −62.747 | −32.815 | 1.00 | 52.66 | N |
| ATOM | 9931 | CA | GLY | B | 125 | −63.396 | −61.745 | −31.968 | 1.00 | 52.68 | C |
| ATOM | 9934 | C | GLY | B | 125 | −63.916 | −60.329 | −32.135 | 1.00 | 52.63 | C |
| ATOM | 9935 | O | GLY | B | 125 | −63.539 | −59.447 | −31.367 | 1.00 | 52.57 | O |
| ATOM | 9937 | N | ASN | B | 126 | −64.782 | −60.117 | −33.129 | 1.00 | 52.54 | N |
| ATOM | 9938 | CA | ASN | B | 126 | −65.343 | −58.793 | −33.443 | 1.00 | 52.41 | C |
| ATOM | 9940 | CB | ASN | B | 126 | −65.575 | −58.671 | −34.949 | 1.00 | 52.40 | C |
| ATOM | 9943 | CG | ASN | B | 126 | −64.322 | −58.951 | −35.751 | 1.00 | 52.64 | C |
| ATOM | 9944 | OD1 | ASN | B | 126 | −63.426 | −59.665 | −35.297 | 1.00 | 52.77 | O |
| ATOM | 9945 | ND2 | ASN | B | 126 | −64.249 | −58.390 | −36.952 | 1.00 | 53.00 | N |
| ATOM | 9948 | C | ASN | B | 126 | −66.656 | −58.524 | −32.712 | 1.00 | 52.10 | C |
| ATOM | 9949 | O | ASN | B | 126 | −67.253 | −59.432 | −32.153 | 1.00 | 52.27 | O |
| ATOM | 9951 | N | PHE | B | 127 | −67.111 | −57.279 | −32.724 | 1.00 | 51.61 | N |
| ATOM | 9952 | CA | PHE | B | 127 | −68.362 | −56.936 | −32.055 | 1.00 | 51.23 | C |
| ATOM | 9954 | CB | PHE | B | 127 | −68.506 | −55.416 | −31.905 | 1.00 | 51.21 | C |
| ATOM | 9957 | CG | PHE | B | 127 | −67.702 | −54.848 | −30.770 | 1.00 | 50.58 | C |
| ATOM | 9958 | CD1 | PHE | B | 127 | −66.513 | −54.192 | −31.003 | 1.00 | 50.15 | C |
| ATOM | 9960 | CE1 | PHE | B | 127 | −65.777 | −53.686 | −29.948 | 1.00 | 50.15 | C |
| ATOM | 9962 | CZ | PHE | B | 127 | −66.225 | −53.839 | −28.647 | 1.00 | 49.71 | C |
| ATOM | 9964 | CE2 | PHE | B | 127 | −67.399 | −54.496 | −28.405 | 1.00 | 49.50 | C |
| ATOM | 9966 | CD2 | PHE | B | 127 | −68.132 | −54.999 | −29.459 | 1.00 | 49.99 | C |
| ATOM | 9968 | C | PHE | B | 127 | −69.537 | −57.505 | −32.821 | 1.00 | 50.99 | C |
| ATOM | 9969 | O | PHE | B | 127 | −69.468 | −57.641 | −34.040 | 1.00 | 50.92 | O |
| ATOM | 9971 | N | LEU | B | 128 | −70.609 | −57.840 | −32.106 | 1.00 | 50.83 | N |
| ATOM | 9972 | CA | LEU | B | 128 | −71.799 | −58.422 | −32.731 | 1.00 | 50.76 | C |
| ATOM | 9974 | CB | LEU | B | 128 | −72.780 | −58.953 | −31.669 | 1.00 | 50.80 | C |
| ATOM | 9977 | CG | LEU | B | 128 | −72.341 | −60.098 | −30.734 | 1.00 | 50.91 | C |
| ATOM | 9979 | CD1 | LEU | B | 128 | −73.483 | −60.532 | −29.813 | 1.00 | 50.61 | C |
| ATOM | 9983 | CD2 | LEU | B | 128 | −71.818 | −61.303 | −31.497 | 1.00 | 50.79 | C |
| ATOM | 9987 | C | LEU | B | 128 | −72.500 | −57.407 | −33.646 | 1.00 | 50.55 | C |
| ATOM | 9988 | O | LEU | B | 128 | −73.105 | −56.455 | −33.171 | 1.00 | 50.34 | O |
| ATOM | 9990 | N | GLU | B | 129 | −72.402 | −57.628 | −34.957 | 1.00 | 50.50 | N |
| ATOM | 9991 | CA | GLU | B | 129 | −73.038 | −56.783 | −35.982 | 1.00 | 50.48 | C |
| ATOM | 9993 | CB | GLU | B | 129 | −73.150 | −57.551 | −37.310 | 1.00 | 50.68 | C |
| ATOM | 9996 | CG | GLU | B | 129 | −72.262 | −57.024 | −38.434 | 1.00 | 51.36 | C |
| ATOM | 9999 | CD | GLU | B | 129 | −72.799 | −55.745 | −39.060 | 1.00 | 51.88 | C |
| ATOM | 10000 | OE1 | GLU | B | 129 | −72.110 | −54.707 | −38.961 | 1.00 | 52.72 | O |
| ATOM | 10001 | OE2 | GLU | B | 129 | −73.906 | −55.773 | −39.643 | 1.00 | 51.58 | O |
| ATOM | 10002 | C | GLU | B | 129 | −74.428 | −56.264 | −35.629 | 1.00 | 50.25 | C |
| ATOM | 10003 | O | GLU | B | 129 | −74.737 | −55.110 | −35.899 | 1.00 | 50.18 | O |
| ATOM | 10005 | N | ASN | B | 130 | −75.263 | −57.125 | −35.047 | 1.00 | 50.06 | N |
| ATOM | 10006 | CA | ASN | B | 130 | −76.678 | −56.806 | −34.785 | 1.00 | 49.71 | C |
| ATOM | 10008 | CB | ASN | B | 130 | −77.477 | −58.100 | −34.550 | 1.00 | 49.69 | C |
| ATOM | 10011 | CG | ASN | B | 130 | −77.053 | −58.837 | −33.291 | 1.00 | 49.39 | C |
| ATOM | 10012 | OD1 | ASN | B | 130 | −76.357 | −59.848 | −33.361 | 1.00 | 48.74 | O |
| ATOM | 10013 | ND2 | ASN | B | 130 | −77.468 | −58.329 | −32.134 | 1.00 | 48.99 | N |
| ATOM | 10016 | C | ASN | B | 130 | −76.934 | −55.800 | −33.646 | 1.00 | 49.37 | C |
| ATOM | 10017 | O | ASN | B | 130 | −78.083 | −55.456 | −33.366 | 1.00 | 49.29 | O |
| ATOM | 10019 | N | LEU | B | 131 | −75.868 | −55.336 | −32.996 | 1.00 | 48.98 | N |
| ATOM | 10020 | CA | LEU | B | 131 | −75.957 | −54.279 | −31.988 | 1.00 | 48.56 | C |
| ATOM | 10022 | CB | LEU | B | 131 | −74.797 | −54.392 | −30.991 | 1.00 | 48.44 | C |
| ATOM | 10025 | CG | LEU | B | 131 | −74.759 | −55.671 | −30.148 | 1.00 | 48.19 | C |
| ATOM | 10027 | CD1 | LEU | B | 131 | −73.382 | −55.852 | −29.523 | 1.00 | 47.23 | C |
| ATOM | 10031 | CD2 | LEU | B | 131 | −75.861 | −55.670 | −29.083 | 1.00 | 47.77 | C |
| ATOM | 10035 | C | LEU | B | 131 | −75.968 | −52.875 | −32.604 | 1.00 | 48.29 | C |
| ATOM | 10036 | O | LEU | B | 131 | −76.022 | −51.895 | −31.874 | 1.00 | 48.44 | O |
| ATOM | 10038 | N | LYS | B | 132 | −75.927 | −52.771 | −33.934 | 1.00 | 47.95 | N |
| ATOM | 10039 | CA | LYS | B | 132 | −76.020 | −51.471 | −34.621 | 1.00 | 47.64 | C |
| ATOM | 10041 | CB | LYS | B | 132 | −75.548 | −51.590 | −36.080 | 1.00 | 47.63 | C |
| ATOM | 10044 | CG | LYS | B | 132 | −76.595 | −52.235 | −36.998 | 1.00 | 48.19 | C |
| ATOM | 10047 | CD | LYS | B | 132 | −76.111 | −52.483 | −38.429 | 1.00 | 48.16 | C |
| ATOM | 10050 | CE | LYS | B | 132 | −77.239 | −53.040 | −39.290 | 1.00 | 47.23 | C |
| ATOM | 10053 | NZ | LYS | B | 132 | −76.725 | −53.936 | −40.331 | 1.00 | 47.01 | N |
| ATOM | 10057 | C | LYS | B | 132 | −77.449 | −50.907 | −34.597 | 1.00 | 47.13 | C |
| ATOM | 10058 | O | LYS | B | 132 | −77.683 | −49.772 | −35.005 | 1.00 | 46.87 | O |
| ATOM | 10060 | N | GLU | B | 133 | −78.403 | −51.716 | −34.149 | 1.00 | 46.77 | N |
| ATOM | 10061 | CA | GLU | B | 133 | −79.806 | −51.315 | −34.107 | 1.00 | 46.49 | C |

TABLE 3-7-continued

Coordinates of *P. tremuloides IspS*

| | | | | | | | | | | | |
|---|---|---|---|---|---|---|---|---|---|---|---|
| ATOM | 10063 | CB | GLU | B | 133 | −80.691 | −52.458 | −34.622 | 1.00 | 46.56 | C |
| ATOM | 10066 | CG | GLU | B | 133 | −80.732 | −52.515 | −36.155 | 1.00 | 47.01 | C |
| ATOM | 10069 | CD | GLU | B | 133 | −80.737 | −53.926 | −36.715 | 1.00 | 47.40 | C |
| ATOM | 10070 | OE1 | GLU | B | 133 | −81.500 | −54.775 | −36.206 | 1.00 | 47.97 | O |
| ATOM | 10071 | OE2 | GLU | B | 133 | −79.983 | −54.177 | −37.679 | 1.00 | 47.22 | O |
| ATOM | 10072 | C | GLU | B | 133 | −80.260 | −50.830 | −32.723 | 1.00 | 45.92 | C |
| ATOM | 10073 | O | GLU | B | 133 | −81.369 | −50.308 | −32.600 | 1.00 | 46.14 | O |
| ATOM | 10075 | N | ASP | B | 134 | −79.424 | −51.002 | −31.691 | 1.00 | 44.98 | N |
| ATOM | 10076 | CA | ASP | B | 134 | −79.611 | −50.277 | −30.428 | 1.00 | 44.14 | C |
| ATOM | 10078 | CB | ASP | B | 134 | −79.375 | −51.162 | −29.197 | 1.00 | 43.95 | C |
| ATOM | 10081 | CG | ASP | B | 134 | −79.646 | −50.419 | −27.883 | 1.00 | 43.57 | C |
| ATOM | 10082 | OD1 | ASP | B | 134 | −80.014 | −49.230 | −27.919 | 1.00 | 42.21 | O |
| ATOM | 10083 | OD2 | ASP | B | 134 | −79.488 | −51.011 | −26.802 | 1.00 | 43.69 | O |
| ATOM | 10084 | C | ASP | B | 134 | −78.662 | −49.073 | −30.426 | 1.00 | 43.47 | C |
| ATOM | 10085 | O | ASP | B | 134 | −77.478 | −49.196 | −30.104 | 1.00 | 43.55 | O |
| ATOM | 10087 | N | ILE | B | 135 | −79.198 | −47.908 | −30.776 | 1.00 | 42.47 | N |
| ATOM | 10088 | CA | ILE | B | 135 | −78.375 | −46.739 | −31.033 | 1.00 | 41.65 | C |
| ATOM | 10090 | CB | ILE | B | 135 | −79.080 | −45.783 | −32.012 | 1.00 | 41.45 | C |
| ATOM | 10092 | CG1 | ILE | B | 135 | −78.877 | −46.313 | −33.434 | 1.00 | 41.74 | C |
| ATOM | 10095 | CD1 | ILE | B | 135 | −79.174 | −45.331 | −34.540 | 1.00 | 42.77 | C |
| ATOM | 10099 | CG2 | ILE | B | 135 | −78.533 | −44.391 | −31.905 | 1.00 | 41.68 | C |
| ATOM | 10103 | C | ILE | B | 135 | −77.901 | −46.059 | −29.746 | 1.00 | 41.14 | C |
| ATOM | 10104 | O | ILE | B | 135 | −76.752 | −45.624 | −29.676 | 1.00 | 41.11 | O |
| ATOM | 10106 | N | LYS | B | 136 | −78.742 | −45.998 | −28.714 | 1.00 | 40.53 | N |
| ATOM | 10107 | CA | LYS | B | 136 | −78.281 | −45.480 | −27.409 | 1.00 | 40.10 | C |
| ATOM | 10109 | CB | LYS | B | 136 | −79.431 | −45.361 | −26.375 | 1.00 | 40.40 | C |
| ATOM | 10112 | CG | LYS | B | 136 | −79.910 | −46.697 | −25.786 | 1.00 | 42.49 | C |
| ATOM | 10115 | CD | LYS | B | 136 | −81.002 | −46.574 | −24.698 | 1.00 | 44.79 | C |
| ATOM | 10118 | CE | LYS | B | 136 | −81.599 | −47.994 | −24.363 | 1.00 | 46.03 | C |
| ATOM | 10121 | NZ | LYS | B | 136 | −82.231 | −48.149 | −22.994 | 1.00 | 46.23 | N |
| ATOM | 10125 | C | LYS | B | 136 | −77.104 | −46.327 | −26.863 | 1.00 | 38.85 | C |
| ATOM | 10126 | O | LYS | B | 136 | −76.246 | −45.806 | −26.143 | 1.00 | 38.91 | O |
| ATOM | 10128 | N | ALA | B | 137 | −77.062 | −47.617 | −27.219 | 1.00 | 37.27 | N |
| ATOM | 10129 | CA | ALA | B | 137 | −75.935 | −48.486 | −26.864 | 1.00 | 35.88 | C |
| ATOM | 10131 | CB | ALA | B | 137 | −76.255 | −49.952 | −27.116 | 1.00 | 35.69 | C |
| ATOM | 10135 | C | ALA | B | 137 | −74.708 | −48.085 | −27.645 | 1.00 | 34.63 | C |
| ATOM | 10136 | O | ALA | B | 137 | −73.647 | −47.894 | −27.055 | 1.00 | 34.70 | O |
| ATOM | 10138 | N | ILE | B | 138 | −74.845 | −47.946 | −28.965 | 1.00 | 33.12 | N |
| ATOM | 10139 | CA | ILE | B | 138 | −73.693 | −47.597 | −29.805 | 1.00 | 31.97 | C |
| ATOM | 10141 | CB | ILE | B | 138 | −74.020 | −47.572 | −31.296 | 1.00 | 31.50 | C |
| ATOM | 10143 | CG1 | ILE | B | 138 | −74.433 | −48.955 | −31.774 | 1.00 | 31.28 | C |
| ATOM | 10146 | CD1 | ILE | B | 138 | −73.460 | −50.052 | −31.417 | 1.00 | 30.86 | C |
| ATOM | 10150 | CG2 | ILE | B | 138 | −72.819 | −47.138 | −32.073 | 1.00 | 30.61 | C |
| ATOM | 10154 | C | ILE | B | 138 | −73.124 | −46.245 | −29.413 | 1.00 | 31.57 | C |
| ATOM | 10155 | O | ILE | B | 138 | −71.909 | −46.090 | −29.305 | 1.00 | 31.77 | O |
| ATOM | 10157 | N | LEU | B | 139 | −73.997 | −45.268 | −29.192 | 1.00 | 30.92 | N |
| ATOM | 10158 | CA | LEU | B | 139 | −73.555 | −43.962 | −28.713 | 1.00 | 30.29 | C |
| ATOM | 10160 | CB | LEU | B | 139 | −74.732 | −43.000 | −28.530 | 1.00 | 30.13 | C |
| ATOM | 10163 | CG | LEU | B | 139 | −74.778 | −41.890 | −29.574 | 1.00 | 29.96 | C |
| ATOM | 10165 | CD1 | LEU | B | 139 | −73.496 | −41.060 | −29.508 | 1.00 | 28.26 | C |
| ATOM | 10169 | CD2 | LEU | B | 139 | −76.022 | −41.019 | −29.397 | 1.00 | 29.48 | C |
| ATOM | 10173 | C | LEU | B | 139 | −72.835 | −44.136 | −27.397 | 1.00 | 29.95 | C |
| ATOM | 10174 | O | LEU | B | 139 | −71.709 | −43.687 | −27.232 | 1.00 | 30.45 | O |
| ATOM | 10176 | N | SER | B | 140 | −73.492 | −44.807 | −26.463 | 1.00 | 29.33 | N |
| ATOM | 10177 | CA | SER | B | 140 | −72.916 | −45.061 | −25.150 | 1.00 | 28.84 | C |
| ATOM | 10179 | CB | SER | B | 140 | −73.900 | −45.878 | −24.298 | 1.00 | 28.93 | C |
| ATOM | 10182 | OG | SER | B | 140 | −73.527 | −45.870 | −22.930 | 1.00 | 30.33 | O |
| ATOM | 10184 | C | SER | B | 140 | −71.555 | −45.770 | −25.243 | 1.00 | 27.78 | C |
| ATOM | 10185 | O | SER | B | 140 | −70.637 | −45.454 | −24.489 | 1.00 | 27.46 | O |
| ATOM | 10187 | N | LEU | B | 141 | −71.432 | −46.719 | −26.167 | 1.00 | 26.82 | N |
| ATOM | 10188 | CA | LEU | B | 141 | −70.178 | −47.433 | −26.348 | 1.00 | 26.34 | C |
| ATOM | 10190 | CB | LEU | B | 141 | −70.366 | −48.658 | −27.256 | 1.00 | 26.16 | C |
| ATOM | 10193 | CG | LEU | B | 141 | −69.098 | −49.472 | −27.584 | 1.00 | 26.09 | C |
| ATOM | 10195 | CD1 | LEU | B | 141 | −68.355 | −49.960 | −26.330 | 1.00 | 24.64 | C |
| ATOM | 10199 | CD2 | LEU | B | 141 | −69.455 | −50.643 | −28.481 | 1.00 | 25.94 | C |
| ATOM | 10203 | C | LEU | B | 141 | −69.124 | −46.476 | −26.914 | 1.00 | 25.89 | C |
| ATOM | 10204 | O | LEU | B | 141 | −68.025 | −46.346 | −26.366 | 1.00 | 25.77 | O |
| ATOM | 10206 | N | TYR | B | 142 | −69.471 | −45.809 | −28.008 | 1.00 | 25.41 | N |
| ATOM | 10207 | CA | TYR | B | 142 | −68.609 | −44.804 | −28.610 | 1.00 | 25.03 | C |
| ATOM | 10209 | CB | TYR | B | 142 | −69.399 | −43.982 | −29.617 | 1.00 | 24.80 | C |
| ATOM | 10212 | CG | TYR | B | 142 | −68.736 | −42.695 | −30.043 | 1.00 | 24.47 | C |
| ATOM | 10213 | CD1 | TYR | B | 142 | −67.761 | −42.686 | −31.029 | 1.00 | 24.18 | C |
| ATOM | 10215 | CE1 | TYR | B | 142 | −67.166 | −41.516 | −31.438 | 1.00 | 24.70 | C |
| ATOM | 10217 | CZ | TYR | B | 142 | −67.548 | −40.315 | −30.871 | 1.00 | 25.80 | C |
| ATOM | 10218 | OH | TYR | B | 142 | −66.940 | −39.129 | −31.279 | 1.00 | 27.63 | O |
| ATOM | 10220 | CE2 | TYR | B | 142 | −68.522 | −40.299 | −29.890 | 1.00 | 25.57 | C |
| ATOM | 10222 | CD2 | TYR | B | 142 | −69.110 | −41.485 | −29.485 | 1.00 | 24.73 | C |
| ATOM | 10224 | C | TYR | B | 142 | −68.095 | −43.883 | −27.537 | 1.00 | 25.17 | C |

TABLE 3-7-continued

Coordinates of *P. tremuloides* IspS

| | | | | | | | | | | | |
|---|---|---|---|---|---|---|---|---|---|---|---|
| ATOM | 10225 | O | TYR | B | 142 | −66.886 | −43.732 | −27.360 | 1.00 | 25.40 | O |
| ATOM | 10227 | N | GLU | B | 143 | −69.038 | −43.293 | −26.807 | 1.00 | 25.12 | N |
| ATOM | 10228 | CA | GLU | B | 143 | −68.744 | −42.256 | −25.828 | 1.00 | 25.10 | C |
| ATOM | 10230 | CB | GLU | B | 143 | −70.046 | −41.726 | −25.226 | 1.00 | 25.33 | C |
| ATOM | 10233 | CG | GLU | B | 143 | −70.006 | −40.244 | −24.849 | 1.00 | 27.57 | C |
| ATOM | 10236 | CD | GLU | B | 143 | −70.321 | −39.313 | −26.023 | 1.00 | 30.43 | C |
| ATOM | 10237 | OE1 | GLU | B | 143 | −69.343 | −38.764 | −26.583 | 1.00 | 32.89 | O |
| ATOM | 10238 | OE2 | GLU | B | 143 | −71.526 | −39.130 | −26.377 | 1.00 | 30.86 | O |
| ATOM | 10239 | C | GLU | B | 143 | −67.794 | −42.746 | −24.729 | 1.00 | 24.43 | C |
| ATOM | 10240 | O | GLU | B | 143 | −67.026 | −41.959 | −24.179 | 1.00 | 24.06 | O |
| ATOM | 10242 | N | ALA | B | 144 | −67.840 | −44.050 | −24.449 | 1.00 | 24.01 | N |
| ATOM | 10243 | CA | ALA | B | 144 | −67.033 | −44.681 | −23.399 | 1.00 | 23.74 | C |
| ATOM | 10245 | CB | ALA | B | 144 | −67.726 | −45.943 | −22.883 | 1.00 | 23.48 | C |
| ATOM | 10249 | C | ALA | B | 144 | −65.631 | −45.025 | −23.864 | 1.00 | 23.57 | C |
| ATOM | 10250 | O | ALA | B | 144 | −64.720 | −45.171 | −23.060 | 1.00 | 23.69 | O |
| ATOM | 10252 | N | SER | B | 145 | −65.455 | −45.168 | −25.165 | 1.00 | 23.45 | N |
| ATOM | 10253 | CA | SER | B | 145 | −64.168 | −45.568 | −25.701 | 1.00 | 23.44 | C |
| ATOM | 10255 | CB | SER | B | 145 | −64.300 | −45.856 | −27.214 | 1.00 | 23.63 | C |
| ATOM | 10258 | OG | SER | B | 145 | −64.822 | −44.748 | −27.952 | 1.00 | 24.24 | O |
| ATOM | 10260 | C | SER | B | 145 | −63.065 | −44.520 | −25.416 | 1.00 | 23.24 | C |
| ATOM | 10261 | O | SER | B | 145 | −61.877 | −44.848 | −25.288 | 1.00 | 23.25 | O |
| ATOM | 10263 | N | PHE | B | 146 | −63.454 | −43.257 | −25.285 | 1.00 | 22.92 | N |
| ATOM | 10264 | CA | PHE | B | 146 | −62.464 | −42.189 | −25.170 | 1.00 | 22.35 | C |
| ATOM | 10266 | CB | PHE | B | 146 | −63.090 | −40.837 | −25.478 | 1.00 | 22.09 | C |
| ATOM | 10269 | CG | PHE | B | 146 | −63.505 | −40.717 | −26.911 | 1.00 | 22.40 | C |
| ATOM | 10270 | CD1 | PHE | B | 146 | −62.619 | −40.229 | −27.868 | 1.00 | 21.98 | C |
| ATOM | 10272 | CE1 | PHE | B | 146 | −62.985 | −40.156 | −29.201 | 1.00 | 21.80 | C |
| ATOM | 10274 | CZ | PHE | B | 146 | −64.241 | −40.579 | −29.594 | 1.00 | 21.91 | C |
| ATOM | 10276 | CE2 | PHE | B | 146 | −65.123 | −41.098 | −28.649 | 1.00 | 22.29 | C |
| ATOM | 10278 | CD2 | PHE | B | 146 | −64.751 | −41.170 | −27.323 | 1.00 | 22.34 | C |
| ATOM | 10280 | C | PHE | B | 146 | −61.762 | −42.208 | −23.837 | 1.00 | 21.91 | C |
| ATOM | 10281 | O | PHE | B | 146 | −60.669 | −41.683 | −23.733 | 1.00 | 22.30 | O |
| ATOM | 10283 | N | LEU | B | 147 | −62.361 | −42.864 | −22.841 | 1.00 | 21.27 | N |
| ATOM | 10284 | CA | LEU | B | 147 | −61.727 | −43.050 | −21.535 | 1.00 | 20.49 | C |
| ATOM | 10286 | CB | LEU | B | 147 | −62.791 | −43.333 | −20.478 | 1.00 | 20.14 | C |
| ATOM | 10289 | CG | LEU | B | 147 | −63.609 | −42.109 | −20.102 | 1.00 | 18.87 | C |
| ATOM | 10291 | CD1 | LEU | B | 147 | −64.813 | −42.020 | −20.959 | 1.00 | 15.94 | C |
| ATOM | 10295 | CD2 | LEU | B | 147 | −63.988 | −42.189 | −18.642 | 1.00 | 18.62 | C |
| ATOM | 10299 | C | LEU | B | 147 | −60.678 | −44.163 | −21.498 | 1.00 | 20.41 | C |
| ATOM | 10300 | O | LEU | B | 147 | −60.243 | −44.552 | −20.415 | 1.00 | 20.44 | O |
| ATOM | 10302 | N | ALA | B | 148 | −60.268 | −44.664 | −22.662 | 1.00 | 20.28 | N |
| ATOM | 10303 | CA | ALA | B | 148 | −59.330 | −45.784 | −22.745 | 1.00 | 20.33 | C |
| ATOM | 10305 | CB | ALA | B | 148 | −59.188 | −46.231 | −24.194 | 1.00 | 20.15 | C |
| ATOM | 10309 | C | ALA | B | 148 | −57.952 | −45.462 | −22.170 | 1.00 | 20.54 | C |
| ATOM | 10310 | O | ALA | B | 148 | −57.435 | −44.366 | −22.341 | 1.00 | 20.23 | O |
| ATOM | 10312 | N | LEU | B | 149 | −57.366 | −46.435 | −21.486 | 1.00 | 21.19 | N |
| ATOM | 10313 | CA | LEU | B | 149 | −55.969 | −46.354 | −21.067 | 1.00 | 22.02 | C |
| ATOM | 10315 | CB | LEU | B | 149 | −55.768 | −47.073 | −19.725 | 1.00 | 21.90 | C |
| ATOM | 10318 | CG | LEU | B | 149 | −56.541 | −46.496 | −18.523 | 1.00 | 21.50 | C |
| ATOM | 10320 | CD1 | LEU | B | 149 | −55.979 | −47.006 | −17.223 | 1.00 | 20.96 | C |
| ATOM | 10324 | CD2 | LEU | B | 149 | −56.520 | −44.974 | −18.505 | 1.00 | 20.95 | C |
| ATOM | 10328 | C | LEU | B | 149 | −55.054 | −46.930 | −22.159 | 1.00 | 22.84 | C |
| ATOM | 10329 | O | LEU | B | 149 | −55.507 | −47.678 | −23.017 | 1.00 | 22.91 | O |
| ATOM | 10331 | N | GLU | B | 150 | −53.781 | −46.550 | −22.163 | 1.00 | 23.93 | N |
| ATOM | 10332 | CA | GLU | B | 150 | −52.858 | −47.071 | −23.174 | 1.00 | 25.03 | C |
| ATOM | 10334 | CB | GLU | B | 150 | −51.472 | −46.431 | −23.012 | 1.00 | 25.41 | C |
| ATOM | 10337 | CG | GLU | B | 150 | −50.530 | −46.608 | −24.213 | 1.00 | 27.44 | C |
| ATOM | 10340 | CD | GLU | B | 150 | −49.132 | −45.987 | −23.992 | 1.00 | 30.04 | C |
| ATOM | 10341 | OE1 | GLU | B | 150 | −48.925 | −45.330 | −22.943 | 1.00 | 31.41 | O |
| ATOM | 10342 | OE2 | GLU | B | 150 | −48.242 | −46.161 | −24.867 | 1.00 | 30.34 | O |
| ATOM | 10343 | C | GLU | B | 150 | −52.787 | −48.600 | −23.024 | 1.00 | 25.36 | C |
| ATOM | 10344 | O | GLU | B | 150 | −52.613 | −49.098 | −21.911 | 1.00 | 25.58 | O |
| ATOM | 10346 | N | GLY | B | 151 | −52.968 | −49.337 | −24.122 | 1.00 | 25.79 | N |
| ATOM | 10347 | CA | GLY | B | 151 | −52.959 | −50.816 | −24.086 | 1.00 | 26.11 | C |
| ATOM | 10350 | C | GLY | B | 151 | −54.323 | −51.522 | −24.047 | 1.00 | 26.44 | C |
| ATOM | 10351 | O | GLY | B | 151 | −54.393 | −52.747 | −24.135 | 1.00 | 26.91 | O |
| ATOM | 10353 | N | GLU | B | 152 | −55.407 | −50.768 | −23.899 | 1.00 | 26.58 | N |
| ATOM | 10354 | CA | GLU | B | 152 | −56.757 | −51.319 | −23.971 | 1.00 | 26.57 | C |
| ATOM | 10356 | CB | GLU | B | 152 | −57.697 | −50.531 | −23.065 | 1.00 | 26.74 | C |
| ATOM | 10359 | CG | GLU | B | 152 | −57.291 | −50.595 | −21.596 | 1.00 | 27.63 | C |
| ATOM | 10362 | CD | GLU | B | 152 | −58.271 | −49.893 | −20.668 | 1.00 | 28.86 | C |
| ATOM | 10363 | OE1 | GLU | B | 152 | −58.239 | −50.192 | −19.449 | 1.00 | 28.80 | O |
| ATOM | 10364 | OE2 | GLU | B | 152 | −59.066 | −49.044 | −21.154 | 1.00 | 29.26 | O |
| ATOM | 10365 | C | GLU | B | 152 | −57.254 | −51.303 | −25.415 | 1.00 | 26.53 | C |
| ATOM | 10366 | O | GLU | B | 152 | −57.937 | −50.381 | −25.869 | 1.00 | 26.00 | O |
| ATOM | 10368 | N | ASN | B | 153 | −56.888 | −52.354 | −26.127 | 1.00 | 26.77 | N |
| ATOM | 10369 | CA | ASN | B | 153 | −57.189 | −52.498 | −27.545 | 1.00 | 27.05 | C |
| ATOM | 10371 | CB | ASN | B | 153 | −56.345 | −53.640 | −28.104 | 1.00 | 27.12 | C |

TABLE 3-7-continued

Coordinates of *P. tremuloides IspS*

| | | | | | | | | | | | |
|---|---|---|---|---|---|---|---|---|---|---|---|
| ATOM | 10374 | CG | ASN | B | 153 | −56.770 | −54.992 | −27.549 | 1.00 | 27.81 | C |
| ATOM | 10375 | OD1 | ASN | B | 153 | −56.540 | −55.307 | −26.379 | 1.00 | 27.65 | O |
| ATOM | 10376 | ND2 | ASN | B | 153 | −57.426 | −55.782 | −28.382 | 1.00 | 29.43 | N |
| ATOM | 10379 | C | ASN | B | 153 | −58.659 | −52.788 | −27.873 | 1.00 | 27.09 | C |
| ATOM | 10380 | O | ASN | B | 153 | −59.053 | −52.658 | −29.029 | 1.00 | 27.11 | O |
| ATOM | 10382 | N | ILE | B | 154 | −59.448 | −53.223 | −26.884 | 1.00 | 27.17 | N |
| ATOM | 10383 | CA | ILE | B | 154 | −60.865 | −53.544 | −27.100 | 1.00 | 27.11 | C |
| ATOM | 10385 | CB | ILE | B | 154 | −61.454 | −54.369 | −25.956 | 1.00 | 26.99 | C |
| ATOM | 10387 | CG1 | ILE | B | 154 | −60.811 | −55.750 | −25.907 | 1.00 | 27.16 | C |
| ATOM | 10390 | CD1 | ILE | B | 154 | −61.309 | −56.622 | −24.746 | 1.00 | 27.41 | C |
| ATOM | 10394 | CG2 | ILE | B | 154 | −62.953 | −54.519 | −26.124 | 1.00 | 26.65 | C |
| ATOM | 10398 | C | ILE | B | 154 | −61.704 | −52.284 | −27.229 | 1.00 | 27.43 | C |
| ATOM | 10399 | O | ILE | B | 154 | −62.718 | −52.279 | −27.939 | 1.00 | 27.39 | O |
| ATOM | 10401 | N | LEU | B | 155 | −61.296 | −51.226 | −26.522 | 1.00 | 27.76 | N |
| ATOM | 10402 | CA | LEU | B | 155 | −61.964 | −49.918 | −26.609 | 1.00 | 27.75 | C |
| ATOM | 10404 | CB | LEU | B | 155 | −61.578 | −49.024 | −25.430 | 1.00 | 27.31 | C |
| ATOM | 10407 | CG | LEU | B | 155 | −61.968 | −49.544 | −24.052 | 1.00 | 26.64 | C |
| ATOM | 10409 | CD1 | LEU | B | 155 | −61.444 | −48.631 | −22.981 | 1.00 | 25.82 | C |
| ATOM | 10413 | CD2 | LEU | B | 155 | −63.465 | −49.674 | −23.944 | 1.00 | 26.45 | C |
| ATOM | 10417 | C | LEU | B | 155 | −61.620 | −49.226 | −27.924 | 1.00 | 28.32 | C |
| ATOM | 10418 | O | LEU | B | 155 | −62.499 | −48.672 | −28.583 | 1.00 | 28.72 | O |
| ATOM | 10420 | N | ASP | B | 156 | −60.348 | −49.264 | −28.309 | 1.00 | 28.84 | N |
| ATOM | 10421 | CA | ASP | B | 156 | −59.934 | −48.737 | −29.601 | 1.00 | 29.43 | C |
| ATOM | 10423 | CB | ASP | B | 156 | −58.423 | −48.928 | −29.823 | 1.00 | 29.92 | C |
| ATOM | 10426 | CG | ASP | B | 156 | −57.566 | −47.912 | −29.045 | 1.00 | 31.35 | C |
| ATOM | 10427 | OD1 | ASP | B | 156 | −57.803 | −46.680 | −29.162 | 1.00 | 33.23 | O |
| ATOM | 10428 | OD2 | ASP | B | 156 | −56.640 | −48.351 | −28.324 | 1.00 | 33.08 | O |
| ATOM | 10429 | C | ASP | B | 156 | −60.719 | −49.411 | −30.717 | 1.00 | 29.36 | C |
| ATOM | 10430 | O | ASP | B | 156 | −61.075 | −48.768 | −31.697 | 1.00 | 29.33 | O |
| ATOM | 10432 | N | GLU | B | 157 | −60.981 | −50.705 | −30.558 | 1.00 | 29.63 | N |
| ATOM | 10433 | CA | GLU | B | 157 | −61.845 | −51.457 | −31.479 | 1.00 | 29.98 | C |
| ATOM | 10435 | CB | GLU | B | 157 | −61.729 | −52.971 | −31.234 | 1.00 | 30.30 | C |
| ATOM | 10438 | CG | GLU | B | 157 | −60.664 | −53.647 | −32.087 | 1.00 | 31.79 | C |
| ATOM | 10441 | CD | GLU | B | 157 | −60.075 | −54.901 | −31.439 | 1.00 | 33.87 | C |
| ATOM | 10442 | OE1 | GLU | B | 157 | −60.793 | −55.560 | −30.640 | 1.00 | 35.07 | O |
| ATOM | 10443 | OE2 | GLU | B | 157 | −58.894 | −55.223 | −31.743 | 1.00 | 33.70 | O |
| ATOM | 10444 | C | GLU | B | 157 | −63.304 | −51.030 | −31.349 | 1.00 | 29.53 | C |
| ATOM | 10445 | O | GLU | B | 157 | −63.999 | −50.878 | −32.351 | 1.00 | 29.53 | O |
| ATOM | 10447 | N | ALA | B | 158 | −63.758 | −50.853 | −30.112 | 1.00 | 29.11 | N |
| ATOM | 10448 | CA | ALA | B | 158 | −65.104 | −50.370 | −29.840 | 1.00 | 28.87 | C |
| ATOM | 10450 | CB | ALA | B | 158 | −65.307 | −50.195 | −28.351 | 1.00 | 28.82 | C |
| ATOM | 10454 | C | ALA | B | 158 | −65.383 | −49.065 | −30.567 | 1.00 | 28.73 | C |
| ATOM | 10455 | O | ALA | B | 158 | −66.485 | −48.857 | −31.065 | 1.00 | 28.80 | O |
| ATOM | 10457 | N | LYS | B | 159 | −64.385 | −48.197 | −30.642 | 1.00 | 28.65 | N |
| ATOM | 10458 | CA | LYS | B | 159 | −64.553 | −46.910 | −31.296 | 1.00 | 28.98 | C |
| ATOM | 10460 | CB | LYS | B | 159 | −63.439 | −45.950 | −30.857 | 1.00 | 29.16 | C |
| ATOM | 10463 | CG | LYS | B | 159 | −63.558 | −44.536 | −31.426 | 1.00 | 29.82 | C |
| ATOM | 10466 | CD | LYS | B | 159 | −62.812 | −43.493 | −30.592 | 1.00 | 30.96 | C |
| ATOM | 10469 | CE | LYS | B | 159 | −61.295 | −43.610 | −30.691 | 1.00 | 31.57 | C |
| ATOM | 10472 | NZ | LYS | B | 159 | −60.630 | −42.426 | −30.079 | 1.00 | 31.49 | N |
| ATOM | 10476 | C | LYS | B | 159 | −64.594 | −47.041 | −32.826 | 1.00 | 29.08 | C |
| ATOM | 10477 | O | LYS | B | 159 | −65.385 | −46.372 | −33.486 | 1.00 | 28.73 | O |
| ATOM | 10479 | N | VAL | B | 160 | −63.736 | −47.891 | −33.386 | 1.00 | 29.53 | N |
| ATOM | 10480 | CA | VAL | B | 160 | −63.686 | −48.087 | −34.836 | 1.00 | 29.89 | C |
| ATOM | 10482 | CB | VAL | B | 160 | −62.466 | −48.971 | −35.282 | 1.00 | 29.93 | C |
| ATOM | 10484 | CG1 | VAL | B | 160 | −62.576 | −49.375 | −36.756 | 1.00 | 29.58 | C |
| ATOM | 10488 | CG2 | VAL | B | 160 | −61.152 | −48.244 | −35.040 | 1.00 | 29.41 | C |
| ATOM | 10492 | C | VAL | B | 160 | −65.001 | −48.723 | −35.263 | 1.00 | 30.32 | C |
| ATOM | 10493 | O | VAL | B | 160 | −65.507 | −48.459 | −36.362 | 1.00 | 30.41 | O |
| ATOM | 10495 | N | PHE | B | 161 | −65.558 | −49.540 | −34.371 | 1.00 | 30.83 | N |
| ATOM | 10496 | CA | PHE | B | 161 | −66.854 | −50.178 | −34.599 | 1.00 | 31.34 | C |
| ATOM | 10498 | CB | PHE | B | 161 | −67.090 | −51.321 | −33.599 | 1.00 | 31.34 | C |
| ATOM | 10501 | CG | PHE | B | 161 | −68.492 | −51.834 | −33.603 | 1.00 | 31.09 | C |
| ATOM | 10502 | CD1 | PHE | B | 161 | −68.940 | −52.636 | −34.633 | 1.00 | 31.61 | C |
| ATOM | 10504 | CE1 | PHE | B | 161 | −70.249 | −53.098 | −34.649 | 1.00 | 31.48 | C |
| ATOM | 10506 | CZ | PHE | B | 161 | −71.114 | −52.748 | −33.628 | 1.00 | 30.76 | C |
| ATOM | 10508 | CE2 | PHE | B | 161 | −70.677 | −51.944 | −32.606 | 1.00 | 30.19 | C |
| ATOM | 10510 | CD2 | PHE | B | 161 | −69.378 | −51.486 | −32.597 | 1.00 | 30.70 | C |
| ATOM | 10512 | C | PHE | B | 161 | −67.992 | −49.173 | −34.504 | 1.00 | 31.65 | C |
| ATOM | 10513 | O | PHE | B | 161 | −68.785 | −49.038 | −35.432 | 1.00 | 31.62 | O |
| ATOM | 10515 | N | ALA | B | 162 | −68.068 | −48.483 | −33.373 | 1.00 | 32.26 | N |
| ATOM | 10516 | CA | ALA | B | 162 | −69.135 | −47.519 | −33.129 | 1.00 | 32.84 | C |
| ATOM | 10518 | CB | ALA | B | 162 | −68.948 | −46.854 | −31.778 | 1.00 | 32.66 | C |
| ATOM | 10522 | C | ALA | B | 162 | −69.224 | −46.474 | −34.245 | 1.00 | 33.40 | C |
| ATOM | 10523 | O | ALA | B | 162 | −70.229 | −46.408 | −34.937 | 1.00 | 33.45 | O |
| ATOM | 10525 | N | ILE | B | 163 | −68.164 | −45.697 | −34.444 | 1.00 | 34.38 | N |
| ATOM | 10526 | CA | ILE | B | 163 | −68.166 | −44.610 | −35.439 | 1.00 | 35.23 | C |
| ATOM | 10528 | CB | ILE | B | 163 | −66.734 | −44.062 | −35.733 | 1.00 | 35.18 | C |

TABLE 3-7-continued

Coordinates of *P. tremuloides IspS*

| | | | | | | | | | | | |
|---|---|---|---|---|---|---|---|---|---|---|---|
| ATOM | 10530 | CG1 | ILE | B | 163 | −66.092 | −43.457 | −34.488 | 1.00 | 35.21 | C |
| ATOM | 10533 | CD1 | ILE | B | 163 | −64.620 | −43.171 | −34.663 | 1.00 | 35.96 | C |
| ATOM | 10537 | CG2 | ILE | B | 163 | −66.778 | −42.977 | −36.799 | 1.00 | 34.72 | C |
| ATOM | 10541 | C | ILE | B | 163 | −68.778 | −45.052 | −36.766 | 1.00 | 36.18 | C |
| ATOM | 10542 | O | ILE | B | 163 | −69.588 | −44.335 | −37.360 | 1.00 | 35.87 | O |
| ATOM | 10544 | N | SER | B | 164 | −68.379 | −46.240 | −37.217 | 1.00 | 37.67 | N |
| ATOM | 10545 | CA | SER | B | 164 | −68.761 | −46.752 | −38.539 | 1.00 | 38.74 | C |
| ATOM | 10547 | CB | SER | B | 164 | −68.104 | −48.117 | −38.815 | 1.00 | 38.80 | C |
| ATOM | 10550 | OG | SER | B | 164 | −68.733 | −49.158 | −38.077 | 1.00 | 39.07 | O |
| ATOM | 10552 | C | SER | B | 164 | −70.277 | −46.861 | −38.699 | 1.00 | 39.51 | C |
| ATOM | 10553 | O | SER | B | 164 | −70.820 | −46.494 | −39.737 | 1.00 | 39.96 | O |
| ATOM | 10555 | N | HIS | B | 165 | −70.962 | −47.363 | −37.680 | 1.00 | 40.28 | N |
| ATOM | 10556 | CA | HIS | B | 165 | −72.410 | −47.485 | −37.767 | 1.00 | 41.07 | C |
| ATOM | 10558 | CB | HIS | B | 165 | −72.911 | −48.686 | −36.957 | 1.00 | 41.38 | C |
| ATOM | 10561 | CG | HIS | B | 165 | −72.571 | −50.005 | −37.587 | 1.00 | 42.65 | C |
| ATOM | 10562 | ND1 | HIS | B | 165 | −71.647 | −50.875 | −37.046 | 1.00 | 43.54 | N |
| ATOM | 10564 | CE1 | HIS | B | 165 | −71.535 | −51.938 | −37.825 | 1.00 | 43.54 | C |
| ATOM | 10566 | NE2 | HIS | B | 165 | −72.346 | −51.785 | −38.858 | 1.00 | 43.25 | N |
| ATOM | 10568 | CD2 | HIS | B | 165 | −73.001 | −50.582 | −38.737 | 1.00 | 43.31 | C |
| ATOM | 10570 | C | HIS | B | 165 | −73.125 | −46.193 | −37.380 | 1.00 | 41.21 | C |
| ATOM | 10571 | O | HIS | B | 165 | −74.257 | −45.980 | −37.805 | 1.00 | 41.53 | O |
| ATOM | 10573 | N | LEU | B | 166 | −72.459 | −45.326 | −36.614 | 1.00 | 41.32 | N |
| ATOM | 10574 | CA | LEU | B | 166 | −73.042 | −44.039 | −36.201 | 1.00 | 41.31 | C |
| ATOM | 10576 | CB | LEU | B | 166 | −72.317 | −43.460 | −34.973 | 1.00 | 41.14 | C |
| ATOM | 10579 | CG | LEU | B | 166 | −72.732 | −43.975 | −33.589 | 1.00 | 40.03 | C |
| ATOM | 10581 | CD1 | LEU | B | 166 | −71.673 | −43.634 | −32.579 | 1.00 | 38.86 | C |
| ATOM | 10585 | CD2 | LEU | B | 166 | −74.077 | −43.421 | −33.151 | 1.00 | 38.52 | C |
| ATOM | 10589 | C | LEU | B | 166 | −73.045 | −42.992 | −37.313 | 1.00 | 41.80 | C |
| ATOM | 10590 | O | LEU | B | 166 | −74.006 | −42.230 | −37.442 | 1.00 | 41.73 | O |
| ATOM | 10592 | N | LYS | B | 167 | −71.982 | −42.947 | −38.116 | 1.00 | 42.47 | N |
| ATOM | 10593 | CA | LYS | B | 167 | −71.847 | −41.891 | −39.137 | 1.00 | 43.00 | C |
| ATOM | 10595 | CB | LYS | B | 167 | −70.416 | −41.822 | −39.702 | 1.00 | 43.12 | C |
| ATOM | 10598 | CG | LYS | B | 167 | −69.937 | −43.068 | −40.450 | 1.00 | 44.12 | C |
| ATOM | 10601 | CD | LYS | B | 167 | −69.138 | −42.725 | −41.736 | 1.00 | 45.36 | C |
| ATOM | 10604 | CE | LYS | B | 167 | −67.898 | −41.842 | −41.483 | 1.00 | 45.65 | C |
| ATOM | 10607 | NZ | LYS | B | 167 | −67.267 | −41.400 | −42.762 | 1.00 | 44.94 | N |
| ATOM | 10611 | C | LYS | B | 167 | −72.873 | −41.950 | −40.283 | 1.00 | 42.99 | C |
| ATOM | 10612 | O | LYS | B | 167 | −72.826 | −41.124 | −41.182 | 1.00 | 42.95 | O |
| ATOM | 10614 | N | GLU | B | 168 | −73.791 | −42.912 | −40.244 | 1.00 | 43.23 | N |
| ATOM | 10615 | CA | GLU | B | 168 | −74.928 | −42.940 | −41.167 | 1.00 | 43.44 | C |
| ATOM | 10617 | CB | GLU | B | 168 | −74.652 | −43.969 | −42.272 | 1.00 | 43.58 | C |
| ATOM | 10620 | CG | GLU | B | 168 | −73.918 | −43.363 | −43.501 | 1.00 | 44.36 | C |
| ATOM | 10623 | CD | GLU | B | 168 | −72.618 | −44.082 | −43.895 | 1.00 | 44.53 | C |
| ATOM | 10624 | OE1 | GLU | B | 168 | −71.853 | −44.494 | −42.992 | 1.00 | 44.71 | O |
| ATOM | 10625 | OE2 | GLU | B | 168 | −72.351 | −44.197 | −45.115 | 1.00 | 43.31 | O |
| ATOM | 10626 | C | GLU | B | 168 | −76.263 | −43.214 | −40.442 | 1.00 | 43.24 | C |
| ATOM | 10627 | O | GLU | B | 168 | −76.932 | −42.291 | −39.942 | 1.00 | 42.54 | O |
| ATOM | 10629 | N | GLY | B | 175 | −83.548 | −42.037 | −36.239 | 1.00 | 49.43 | N |
| ATOM | 10630 | CA | GLY | B | 175 | −84.473 | −41.266 | −35.416 | 1.00 | 49.54 | C |
| ATOM | 10633 | C | GLY | B | 175 | −84.709 | −39.884 | −36.001 | 1.00 | 49.76 | C |
| ATOM | 10634 | O | GLY | B | 175 | −84.828 | −39.741 | −37.220 | 1.00 | 49.70 | O |
| ATOM | 10636 | N | LYS | B | 176 | −84.766 | −38.870 | −35.131 | 1.00 | 49.95 | N |
| ATOM | 10637 | CA | LYS | B | 176 | −85.014 | −37.468 | −35.534 | 1.00 | 50.05 | C |
| ATOM | 10639 | CB | LYS | B | 176 | −86.522 | −37.225 | −35.730 | 1.00 | 50.27 | C |
| ATOM | 10642 | CG | LYS | B | 176 | −87.301 | −36.813 | −34.460 | 1.00 | 51.33 | C |
| ATOM | 10645 | CD | LYS | B | 176 | −88.553 | −37.658 | −34.202 | 1.00 | 52.21 | C |
| ATOM | 10648 | CE | LYS | B | 176 | −88.841 | −37.754 | −32.695 | 1.00 | 52.36 | C |
| ATOM | 10651 | NZ | LYS | B | 176 | −90.029 | −38.607 | −32.422 | 1.00 | 52.15 | N |
| ATOM | 10655 | C | LYS | B | 176 | −84.427 | −36.432 | −34.554 | 1.00 | 49.75 | C |
| ATOM | 10656 | O | LYS | B | 176 | −83.990 | −35.370 | −34.972 | 1.00 | 49.88 | O |
| ATOM | 10658 | N | GLU | B | 177 | −84.473 | −36.729 | −33.254 | 1.00 | 49.46 | N |
| ATOM | 10659 | CA | GLU | B | 177 | −83.769 | −35.959 | −32.221 | 1.00 | 48.92 | C |
| ATOM | 10661 | CB | GLU | B | 177 | −84.628 | −35.813 | −30.946 | 1.00 | 49.03 | C |
| ATOM | 10664 | CG | GLU | B | 177 | −84.196 | −36.691 | −29.732 | 1.00 | 49.60 | C |
| ATOM | 10667 | CD | GLU | B | 177 | −85.278 | −36.871 | −28.662 | 1.00 | 50.10 | C |
| ATOM | 10668 | OE1 | GLU | B | 177 | −84.998 | −37.576 | −27.670 | 1.00 | 49.78 | O |
| ATOM | 10669 | OE2 | GLU | B | 177 | −86.401 | −36.336 | −28.808 | 1.00 | 50.78 | O |
| ATOM | 10670 | C | GLU | B | 177 | −82.469 | −36.703 | −31.924 | 1.00 | 48.19 | C |
| ATOM | 10671 | O | GLU | B | 177 | −81.421 | −36.085 | −31.721 | 1.00 | 48.68 | O |
| ATOM | 10673 | N | LEU | B | 178 | −82.557 | −38.037 | −31.900 | 1.00 | 46.98 | N |
| ATOM | 10674 | CA | LEU | B | 178 | −81.398 | −38.924 | −31.817 | 1.00 | 45.91 | C |
| ATOM | 10676 | CB | LEU | B | 178 | −81.838 | −40.387 | −31.945 | 1.00 | 45.70 | C |
| ATOM | 10679 | CG | LEU | B | 178 | −81.111 | −41.408 | −31.074 | 1.00 | 45.24 | C |
| ATOM | 10681 | CD1 | LEU | B | 178 | −81.498 | −41.225 | −29.609 | 1.00 | 44.88 | C |
| ATOM | 10685 | CD2 | LEU | B | 178 | −81.413 | −42.826 | −31.539 | 1.00 | 44.19 | C |
| ATOM | 10689 | C | LEU | B | 178 | −80.423 | −38.571 | −32.934 | 1.00 | 45.27 | C |
| ATOM | 10690 | O | LEU | B | 178 | −79.211 | −38.624 | −32.759 | 1.00 | 44.99 | O |
| ATOM | 10692 | N | ALA | B | 179 | −80.970 | −38.203 | −34.088 | 1.00 | 44.75 | N |

TABLE 3-7-continued

| Coordinates of *P. tremuloides IspS* | | | | | | | | | | |
|---|---|---|---|---|---|---|---|---|---|---|
| ATOM | 10693 | CA | ALA | B | 179 | −80.174 | −37.661 | −35.181 | 1.00 | 44.24 C |
| ATOM | 10695 | CB | ALA | B | 179 | −81.088 | −37.069 | −36.231 | 1.00 | 44.30 C |
| ATOM | 10699 | C | ALA | B | 179 | −79.192 | −36.602 | −34.683 | 1.00 | 43.65 C |
| ATOM | 10700 | O | ALA | B | 179 | −78.028 | −36.604 | −35.061 | 1.00 | 43.56 O |
| ATOM | 10702 | N | GLU | B | 180 | −79.675 | −35.707 | −33.827 | 1.00 | 43.01 N |
| ATOM | 10703 | CA | GLU | B | 180 | −78.863 | −34.610 | −33.311 | 1.00 | 42.49 C |
| ATOM | 10705 | CB | GLU | B | 180 | −79.749 | −33.477 | −32.789 | 1.00 | 42.85 C |
| ATOM | 10708 | CG | GLU | B | 180 | −80.574 | −32.800 | −33.881 | 1.00 | 44.23 C |
| ATOM | 10711 | CD | GLU | B | 180 | −80.991 | −31.382 | −33.519 | 1.00 | 45.80 C |
| ATOM | 10712 | OE1 | GLU | B | 180 | −80.098 | −30.580 | −33.156 | 1.00 | 46.69 O |
| ATOM | 10713 | OE2 | GLU | B | 180 | −82.203 | −31.065 | −33.610 | 1.00 | 46.71 O |
| ATOM | 10714 | C | GLU | B | 180 | −77.944 | −35.075 | −32.210 | 1.00 | 41.39 C |
| ATOM | 10715 | O | GLU | B | 180 | −76.843 | −34.562 | −32.071 | 1.00 | 41.27 O |
| ATOM | 10717 | N | GLN | B | 181 | −78.404 | −36.035 | −31.419 | 1.00 | 40.20 N |
| ATOM | 10718 | CA | GLN | B | 181 | −77.570 | −36.632 | −30.394 | 1.00 | 39.45 C |
| ATOM | 10720 | CB | GLN | B | 181 | −78.280 | −37.809 | −29.736 | 1.00 | 39.88 C |
| ATOM | 10723 | CG | GLN | B | 181 | −78.005 | −37.959 | −28.249 | 1.00 | 41.64 C |
| ATOM | 10726 | CD | GLN | B | 181 | −78.873 | −37.036 | −27.404 | 1.00 | 44.00 C |
| ATOM | 10727 | OE1 | GLN | B | 181 | −80.109 | −36.992 | −27.581 | 1.00 | 45.65 O |
| ATOM | 10728 | NE2 | GLN | B | 181 | −78.235 | −36.291 | −26.474 | 1.00 | 43.41 N |
| ATOM | 10731 | C | GLN | B | 181 | −76.270 | −37.120 | −31.003 | 1.00 | 38.28 C |
| ATOM | 10732 | O | GLN | B | 181 | −75.203 | −36.767 | −30.523 | 1.00 | 38.27 O |
| ATOM | 10734 | N | VAL | B | 182 | −76.358 | −37.911 | −32.072 | 1.00 | 37.05 N |
| ATOM | 10735 | CA | VAL | B | 182 | −75.160 | −38.515 | −32.675 | 1.00 | 36.20 C |
| ATOM | 10737 | CB | VAL | B | 182 | −75.486 | −39.661 | −33.681 | 1.00 | 36.11 C |
| ATOM | 10739 | CG1 | VAL | B | 182 | −76.493 | −40.641 | −33.080 | 1.00 | 36.13 C |
| ATOM | 10743 | CG2 | VAL | B | 182 | −75.977 | −39.106 | −35.004 | 1.00 | 36.06 C |
| ATOM | 10747 | C | VAL | B | 182 | −74.238 | −37.495 | −33.364 | 1.00 | 35.44 C |
| ATOM | 10748 | O | VAL | B | 182 | −73.012 | −37.682 | −33.375 | 1.00 | 35.19 O |
| ATOM | 10750 | N | SER | B | 183 | −74.811 | −36.432 | −33.936 | 1.00 | 34.41 N |
| ATOM | 10751 | CA | SER | B | 183 | −73.998 | −35.416 | −34.630 | 1.00 | 33.74 C |
| ATOM | 10753 | CB | SER | B | 183 | −74.858 | −34.438 | −35.422 | 1.00 | 33.58 C |
| ATOM | 10756 | OG | SER | B | 183 | −76.003 | −35.085 | −35.925 | 1.00 | 34.52 O |
| ATOM | 10758 | C | SER | B | 183 | −73.184 | −34.644 | −33.625 | 1.00 | 32.88 C |
| ATOM | 10759 | O | SER | B | 183 | −72.055 | −34.251 | −33.906 | 1.00 | 33.25 O |
| ATOM | 10761 | N | HIS | B | 184 | −73.788 | −34.427 | −32.461 | 1.00 | 31.83 N |
| ATOM | 10762 | CA | HIS | B | 184 | −73.150 | −33.787 | −31.326 | 1.00 | 30.98 C |
| ATOM | 10764 | CB | HIS | B | 184 | −74.188 | −33.627 | −30.212 | 1.00 | 31.14 C |
| ATOM | 10767 | CG | HIS | B | 184 | −73.710 | −32.849 | −29.030 | 1.00 | 31.91 C |
| ATOM | 10768 | ND1 | HIS | B | 184 | −73.326 | −31.527 | −29.114 | 1.00 | 33.18 N |
| ATOM | 10770 | CE1 | HIS | B | 184 | −72.960 | −31.107 | −27.914 | 1.00 | 33.10 C |
| ATOM | 10772 | NE2 | HIS | B | 184 | −73.106 | −32.102 | −27.056 | 1.00 | 31.85 N |
| ATOM | 10774 | CD2 | HIS | B | 184 | −73.583 | −33.200 | −27.727 | 1.00 | 31.86 C |
| ATOM | 10776 | C | HIS | B | 184 | −71.968 | −34.632 | −30.865 | 1.00 | 30.13 C |
| ATOM | 10777 | O | HIS | B | 184 | −70.863 | −34.122 | −30.709 | 1.00 | 29.95 O |
| ATOM | 10779 | N | ALA | B | 185 | −72.194 | −35.931 | −30.683 | 1.00 | 29.27 N |
| ATOM | 10780 | CA | ALA | B | 185 | −71.123 | −36.856 | −30.281 | 1.00 | 28.64 C |
| ATOM | 10782 | CB | ALA | B | 185 | −71.689 | −38.233 | −29.986 | 1.00 | 28.44 C |
| ATOM | 10786 | C | ALA | B | 185 | −70.017 | −36.965 | −31.330 | 1.00 | 28.08 C |
| ATOM | 10787 | O | ALA | B | 185 | −68.839 | −37.043 | −30.992 | 1.00 | 28.26 O |
| ATOM | 10789 | N | LEU | B | 186 | −70.394 | −36.984 | −32.602 | 1.00 | 27.40 N |
| ATOM | 10790 | CA | LEU | B | 186 | −69.412 | −37.101 | −33.674 | 1.00 | 26.84 C |
| ATOM | 10792 | CB | LEU | B | 186 | −70.088 | −37.481 | −35.000 | 1.00 | 26.75 C |
| ATOM | 10795 | CG | LEU | B | 186 | −70.085 | −38.983 | −35.320 | 1.00 | 26.70 C |
| ATOM | 10797 | CD1 | LEU | B | 186 | −70.214 | −39.868 | −34.075 | 1.00 | 27.07 C |
| ATOM | 10801 | CD2 | LEU | B | 186 | −71.179 | −39.306 | −36.303 | 1.00 | 26.29 C |
| ATOM | 10805 | C | LEU | B | 186 | −68.594 | −35.822 | −33.815 | 1.00 | 26.45 C |
| ATOM | 10806 | O | LEU | B | 186 | −67.449 | −35.875 | −34.237 | 1.00 | 26.48 O |
| ATOM | 10808 | N | GLU | B | 187 | −69.186 | −34.685 | −33.454 | 1.00 | 25.93 N |
| ATOM | 10809 | CA | GLU | B | 187 | −68.479 | −33.406 | −33.403 | 1.00 | 25.57 C |
| ATOM | 10811 | CB | GLU | B | 187 | −69.447 | −32.310 | −32.962 | 1.00 | 25.61 C |
| ATOM | 10814 | CG | GLU | B | 187 | −69.035 | −30.899 | −33.325 | 1.00 | 26.29 C |
| ATOM | 10817 | CD | GLU | B | 187 | −69.930 | −29.857 | −32.671 | 1.00 | 27.10 C |
| ATOM | 10818 | OE1 | GLU | B | 187 | −70.312 | −30.057 | −31.487 | 1.00 | 26.51 O |
| ATOM | 10819 | OE2 | GLU | B | 187 | −70.251 | −28.846 | −33.344 | 1.00 | 27.54 O |
| ATOM | 10820 | C | GLU | B | 187 | −67.307 | −33.490 | −32.418 | 1.00 | 25.13 C |
| ATOM | 10821 | O | GLU | B | 187 | −66.155 | −33.165 | −32.749 | 1.00 | 24.85 O |
| ATOM | 10823 | N | LEU | B | 188 | −67.625 | −33.938 | −31.204 | 1.00 | 24.58 N |
| ATOM | 10824 | CA | LEU | B | 188 | −66.644 | −34.137 | −30.148 | 1.00 | 24.06 C |
| ATOM | 10826 | CB | LEU | B | 188 | −66.343 | −32.817 | −29.451 | 1.00 | 24.12 C |
| ATOM | 10829 | CG | LEU | B | 188 | −65.042 | −32.714 | −28.670 | 1.00 | 23.61 C |
| ATOM | 10831 | CD1 | LEU | B | 188 | −63.895 | −32.872 | −29.629 | 1.00 | 23.12 C |
| ATOM | 10835 | CD2 | LEU | B | 188 | −64.976 | −31.368 | −27.964 | 1.00 | 23.18 C |
| ATOM | 10839 | C | LEU | B | 188 | −67.248 | −35.087 | −29.140 | 1.00 | 23.70 C |
| ATOM | 10840 | O | LEU | B | 188 | −68.392 | −34.901 | −28.743 | 1.00 | 23.68 O |
| ATOM | 10842 | N | PRO | B | 189 | −66.493 | −36.106 | −28.713 | 1.00 | 23.34 N |
| ATOM | 10843 | CA | PRO | B | 189 | −67.031 | −36.983 | −27.692 | 1.00 | 23.08 C |
| ATOM | 10845 | CB | PRO | B | 189 | −66.018 | −38.115 | −27.638 | 1.00 | 22.96 C |

TABLE 3-7-continued

Coordinates of *P. tremuloides IspS*

| | | | | | | | | | | | |
|---|---|---|---|---|---|---|---|---|---|---|---|
| ATOM | 10848 | CG | PRO | B | 189 | −64.743 | −37.452 | −27.940 | 1.00 | 23.22 | C |
| ATOM | 10851 | CD | PRO | B | 189 | −65.059 | −36.350 | −28.929 | 1.00 | 23.54 | C |
| ATOM | 10854 | C | PRO | B | 189 | −67.053 | −36.229 | −26.387 | 1.00 | 22.86 | C |
| ATOM | 10855 | O | PRO | B | 189 | −66.284 | −35.285 | −26.215 | 1.00 | 23.03 | O |
| ATOM | 10856 | N | LEU | B | 190 | −67.912 | −36.628 | −25.465 | 1.00 | 22.56 | N |
| ATOM | 10857 | CA | LEU | B | 190 | −68.152 | −35.773 | −24.323 | 1.00 | 22.41 | C |
| ATOM | 10859 | CB | LEU | B | 190 | −69.567 | −35.970 | −23.766 | 1.00 | 23.04 | C |
| ATOM | 10862 | CG | LEU | B | 190 | −69.853 | −37.136 | −22.848 | 1.00 | 23.41 | C |
| ATOM | 10864 | CD1 | LEU | B | 190 | −69.303 | −36.733 | −21.481 | 1.00 | 25.02 | C |
| ATOM | 10868 | CD2 | LEU | B | 190 | −71.342 | −37.411 | −22.820 | 1.00 | 21.69 | C |
| ATOM | 10872 | C | LEU | B | 190 | −67.065 | −35.899 | −23.266 | 1.00 | 21.56 | C |
| ATOM | 10873 | O | LEU | B | 190 | −66.860 | −34.976 | −22.477 | 1.00 | 21.67 | O |
| ATOM | 10875 | N | HIS | B | 191 | −66.320 | −36.998 | −23.283 | 1.00 | 20.39 | N |
| ATOM | 10876 | CA | HIS | B | 191 | −65.089 | −37.037 | −22.490 | 1.00 | 19.40 | C |
| ATOM | 10878 | CB | HIS | B | 191 | −64.399 | −38.393 | −22.597 | 1.00 | 19.19 | C |
| ATOM | 10881 | CG | HIS | B | 191 | −63.222 | −38.530 | −21.689 | 1.00 | 19.32 | C |
| ATOM | 10882 | ND1 | HIS | B | 191 | −63.347 | −38.562 | −20.317 | 1.00 | 20.95 | N |
| ATOM | 10884 | CE1 | HIS | B | 191 | −62.145 | −38.659 | −19.771 | 1.00 | 21.15 | C |
| ATOM | 10886 | NE2 | HIS | B | 191 | −61.245 | −38.689 | −20.741 | 1.00 | 19.36 | N |
| ATOM | 10888 | CD2 | HIS | B | 191 | −61.893 | −38.604 | −21.948 | 1.00 | 19.49 | C |
| ATOM | 10890 | C | HIS | B | 191 | −64.094 | −35.913 | −22.841 | 1.00 | 18.62 | C |
| ATOM | 10891 | O | HIS | B | 191 | −63.150 | −35.677 | −22.085 | 1.00 | 18.59 | O |
| ATOM | 10893 | N | ARG | B | 192 | −64.307 | −35.216 | −23.957 | 1.00 | 17.72 | N |
| ATOM | 10894 | CA | ARG | B | 192 | −63.394 | −34.150 | −24.394 | 1.00 | 17.57 | C |
| ATOM | 10896 | CB | ARG | B | 192 | −62.838 | −34.504 | −25.773 | 1.00 | 17.81 | C |
| ATOM | 10899 | CG | ARG | B | 192 | −61.971 | −35.736 | −25.781 | 1.00 | 18.59 | C |
| ATOM | 10902 | CD | ARG | B | 192 | −61.484 | −36.067 | −27.181 | 1.00 | 20.10 | C |
| ATOM | 10905 | NE | ARG | B | 192 | −60.462 | −37.116 | −27.165 | 1.00 | 21.62 | N |
| ATOM | 10907 | CZ | ARG | B | 192 | −59.919 | −37.648 | −28.254 | 1.00 | 22.77 | C |
| ATOM | 10908 | NH1 | ARG | B | 192 | −60.304 | −37.248 | −29.454 | 1.00 | 24.20 | N |
| ATOM | 10911 | NH2 | ARG | B | 192 | −58.987 | −38.581 | −28.149 | 1.00 | 23.37 | N |
| ATOM | 10914 | C | ARG | B | 192 | −63.983 | −32.726 | −24.440 | 1.00 | 17.01 | C |
| ATOM | 10915 | O | ARG | B | 192 | −63.242 | −31.739 | −24.526 | 1.00 | 15.78 | O |
| ATOM | 10917 | N | ARG | B | 193 | −65.309 | −32.634 | −24.392 | 1.00 | 17.01 | N |
| ATOM | 10918 | CA | ARG | B | 193 | −66.015 | −31.350 | −24.453 | 1.00 | 16.99 | C |
| ATOM | 10920 | CB | ARG | B | 193 | −67.476 | −31.582 | −24.892 | 1.00 | 17.29 | C |
| ATOM | 10923 | CG | ARG | B | 193 | −68.192 | −30.318 | −25.377 | 1.00 | 18.42 | C |
| ATOM | 10926 | CD | ARG | B | 193 | −69.664 | −30.559 | −25.646 | 1.00 | 19.63 | C |
| ATOM | 10929 | NE | ARG | B | 193 | −69.912 | −31.592 | −26.648 | 1.00 | 21.16 | N |
| ATOM | 10931 | CZ | ARG | B | 193 | −69.868 | −31.398 | −27.971 | 1.00 | 23.56 | C |
| ATOM | 10932 | NH1 | ARG | B | 193 | −69.575 | −30.210 | −28.496 | 1.00 | 23.37 | N |
| ATOM | 10935 | NH2 | ARG | B | 193 | −70.112 | −32.413 | −28.789 | 1.00 | 25.37 | N |
| ATOM | 10938 | C | ARG | B | 193 | −65.974 | −30.658 | −23.087 | 1.00 | 16.46 | C |
| ATOM | 10939 | O | ARG | B | 193 | −66.040 | −31.323 | −22.034 | 1.00 | 16.47 | O |
| ATOM | 10941 | N | THR | B | 194 | −65.864 | −29.335 | −23.078 | 1.00 | 15.84 | N |
| ATOM | 10942 | CA | THR | B | 194 | −65.886 | −28.629 | −21.799 | 1.00 | 15.67 | C |
| ATOM | 10944 | CB | THR | B | 194 | −65.354 | −27.199 | −21.884 | 1.00 | 15.48 | C |
| ATOM | 10946 | OG1 | THR | B | 194 | −66.077 | −26.478 | −22.882 | 1.00 | 15.55 | O |
| ATOM | 10948 | CG2 | THR | B | 194 | −63.877 | −27.189 | −22.211 | 1.00 | 14.65 | C |
| ATOM | 10952 | C | THR | B | 194 | −67.310 | −28.613 | −21.270 | 1.00 | 15.79 | C |
| ATOM | 10953 | O | THR | B | 194 | −68.264 | −28.652 | −22.030 | 1.00 | 15.73 | O |
| ATOM | 10955 | N | GLN | B | 195 | −67.444 | −28.557 | −19.957 | 1.00 | 16.20 | N |
| ATOM | 10956 | CA | GLN | B | 195 | −68.737 | −28.711 | −19.328 | 1.00 | 16.84 | C |
| ATOM | 10958 | CB | GLN | B | 195 | −68.601 | −28.781 | −17.816 | 1.00 | 17.07 | C |
| ATOM | 10961 | CG | GLN | B | 195 | −69.921 | −28.440 | −17.153 | 1.00 | 18.86 | C |
| ATOM | 10964 | CD | GLN | B | 195 | −69.999 | −28.875 | −15.746 | 1.00 | 20.95 | C |
| ATOM | 10965 | OE1 | GLN | B | 195 | −69.099 | −29.511 | −15.245 | 1.00 | 24.63 | O |
| ATOM | 10966 | NE2 | GLN | B | 195 | −71.071 | −28.529 | −15.082 | 1.00 | 22.36 | N |
| ATOM | 10969 | C | GLN | B | 195 | −69.757 | −27.623 | −19.669 | 1.00 | 16.93 | C |
| ATOM | 10970 | O | GLN | B | 195 | −70.858 | −27.931 | −20.136 | 1.00 | 16.98 | O |
| ATOM | 10972 | N | ARG | B | 196 | −69.430 | −26.366 | −19.386 | 1.00 | 16.92 | N |
| ATOM | 10973 | CA | ARG | B | 196 | −70.358 | −25.301 | −19.685 | 1.00 | 17.06 | C |
| ATOM | 10975 | CB | ARG | B | 196 | −69.719 | −23.932 | −19.459 | 1.00 | 17.00 | C |
| ATOM | 10978 | CG | ARG | B | 196 | −70.095 | −23.289 | −18.120 | 1.00 | 17.09 | C |
| ATOM | 10981 | CD | ARG | B | 196 | −70.283 | −24.320 | −16.995 | 1.00 | 17.56 | C |
| ATOM | 10984 | NE | ARG | B | 196 | −71.452 | −24.043 | −16.146 | 1.00 | 17.64 | N |
| ATOM | 10986 | CZ | ARG | B | 196 | −72.289 | −24.965 | −15.664 | 1.00 | 17.93 | C |
| ATOM | 10987 | NH1 | ARG | B | 196 | −72.136 | −26.244 | −15.966 | 1.00 | 17.72 | N |
| ATOM | 10990 | NH2 | ARG | B | 196 | −73.305 | −24.611 | −14.878 | 1.00 | 18.27 | N |
| ATOM | 10993 | C | ARG | B | 196 | −70.881 | −25.481 | −21.098 | 1.00 | 17.42 | C |
| ATOM | 10994 | O | ARG | B | 196 | −72.079 | −25.519 | −21.317 | 1.00 | 17.66 | O |
| ATOM | 10996 | N | LEU | B | 197 | −69.984 | −25.676 | −22.044 | 1.00 | 18.04 | N |
| ATOM | 10997 | CA | LEU | B | 197 | −70.379 | −25.925 | −23.425 | 1.00 | 18.51 | C |
| ATOM | 10999 | CB | LEU | B | 197 | −69.133 | −26.085 | −24.289 | 1.00 | 18.52 | C |
| ATOM | 11002 | CG | LEU | B | 197 | −68.998 | −25.185 | −25.508 | 1.00 | 18.06 | C |
| ATOM | 11004 | CD1 | LEU | B | 197 | −68.209 | −23.932 | −25.205 | 1.00 | 15.52 | C |
| ATOM | 11008 | CD2 | LEU | B | 197 | −68.293 | −26.002 | −26.574 | 1.00 | 20.21 | C |
| ATOM | 11012 | C | LEU | B | 197 | −71.290 | −27.163 | −23.580 | 1.00 | 19.14 | C |

TABLE 3-7-continued

Coordinates of *P. tremuloides IspS*

| | | | | | | | | | | | |
|---|---|---|---|---|---|---|---|---|---|---|---|
| ATOM | 11013 | O | LEU | B | 197 | −72.226 | −27.150 | −24.372 | 1.00 | 19.52 | O |
| ATOM | 11015 | N | GLU | B | 198 | −71.030 | −28.235 | −22.842 | 1.00 | 19.72 | N |
| ATOM | 11016 | CA | GLU | B | 198 | −71.918 | −29.396 | −22.909 | 1.00 | 20.43 | C |
| ATOM | 11018 | CB | GLU | B | 198 | −71.272 | −30.631 | −22.270 | 1.00 | 20.65 | C |
| ATOM | 11021 | CG | GLU | B | 198 | −72.176 | −31.880 | −22.172 | 1.00 | 22.51 | C |
| ATOM | 11024 | CD | GLU | B | 198 | −72.635 | −32.460 | −23.522 | 1.00 | 25.57 | C |
| ATOM | 11025 | OE1 | GLU | B | 198 | −72.315 | −31.896 | −24.581 | 1.00 | 28.90 | O |
| ATOM | 11026 | OE2 | GLU | B | 198 | −73.326 | −33.506 | −23.540 | 1.00 | 28.09 | O |
| ATOM | 11027 | C | GLU | B | 198 | −73.271 | −29.101 | −22.259 | 1.00 | 20.72 | C |
| ATOM | 11028 | O | GLU | B | 198 | −74.281 | −29.693 | −22.644 | 1.00 | 20.82 | O |
| ATOM | 11030 | N | ALA | B | 199 | −73.282 | −28.199 | −21.270 | 1.00 | 20.86 | N |
| ATOM | 11031 | CA | ALA | B | 199 | −74.508 | −27.814 | −20.565 | 1.00 | 20.66 | C |
| ATOM | 11033 | CB | ALA | B | 199 | −74.176 | −27.013 | −19.326 | 1.00 | 20.36 | C |
| ATOM | 11037 | C | ALA | B | 199 | −75.472 | −27.033 | −21.461 | 1.00 | 20.84 | C |
| ATOM | 11038 | O | ALA | B | 199 | −76.644 | −27.404 | −21.590 | 1.00 | 20.84 | O |
| ATOM | 11040 | N | VAL | B | 200 | −75.002 | −25.961 | −22.092 | 1.00 | 21.12 | N |
| ATOM | 11041 | CA | VAL | B | 200 | −75.903 | −25.177 | −22.942 | 1.00 | 21.60 | C |
| ATOM | 11043 | CB | VAL | B | 200 | −75.215 | −24.042 | −23.701 | 1.00 | 21.30 | C |
| ATOM | 11045 | CG1 | VAL | B | 200 | −74.660 | −23.055 | −22.738 | 1.00 | 21.26 | C |
| ATOM | 11049 | CG2 | VAL | B | 200 | −74.135 | −24.575 | −24.626 | 1.00 | 21.28 | C |
| ATOM | 11053 | C | VAL | B | 200 | −76.603 | −26.077 | −23.944 | 1.00 | 22.32 | C |
| ATOM | 11054 | O | VAL | B | 200 | −77.791 | −25.908 | −24.218 | 1.00 | 22.32 | O |
| ATOM | 11056 | N | TRP | B | 201 | −75.872 | −27.047 | −24.472 | 1.00 | 23.16 | N |
| ATOM | 11057 | CA | TRP | B | 201 | −76.441 | −27.946 | −25.454 | 1.00 | 24.02 | C |
| ATOM | 11059 | CB | TRP | B | 201 | −75.348 | −28.718 | −26.195 | 1.00 | 24.36 | C |
| ATOM | 11062 | CG | TRP | B | 201 | −75.898 | −29.510 | −27.331 | 1.00 | 24.84 | C |
| ATOM | 11063 | CD1 | TRP | B | 201 | −76.060 | −29.092 | −28.613 | 1.00 | 25.41 | C |
| ATOM | 11065 | NE1 | TRP | B | 201 | −76.599 | −30.094 | −29.374 | 1.00 | 25.61 | N |
| ATOM | 11067 | CE2 | TRP | B | 201 | −76.807 | −31.184 | −28.579 | 1.00 | 25.34 | C |
| ATOM | 11068 | CD2 | TRP | B | 201 | −76.374 | −30.847 | −27.279 | 1.00 | 25.56 | C |
| ATOM | 11069 | CE3 | TRP | B | 201 | −76.466 | −31.800 | −26.264 | 1.00 | 27.13 | C |
| ATOM | 11071 | CZ3 | TRP | B | 201 | −76.989 | −33.046 | −26.574 | 1.00 | 28.66 | C |
| ATOM | 11073 | CH2 | TRP | B | 201 | −77.419 | −33.347 | −27.885 | 1.00 | 28.01 | C |
| ATOM | 11075 | CZ2 | TRP | B | 201 | −77.332 | −32.425 | −28.894 | 1.00 | 26.09 | C |
| ATOM | 11077 | C | TRP | B | 201 | −77.411 | −28.938 | −24.833 | 1.00 | 24.22 | C |
| ATOM | 11078 | O | TRP | B | 201 | −78.473 | −29.172 | −25.383 | 1.00 | 24.83 | O |
| ATOM | 11080 | N | SER | B | 202 | −77.034 | −29.541 | −23.715 | 1.00 | 24.39 | N |
| ATOM | 11081 | CA | SER | B | 202 | −77.818 | −30.626 | −23.144 | 1.00 | 24.50 | C |
| ATOM | 11083 | CB | SER | B | 202 | −76.968 | −31.455 | −22.184 | 1.00 | 24.42 | C |
| ATOM | 11086 | OG | SER | B | 202 | −75.848 | −32.021 | −22.848 | 1.00 | 23.80 | O |
| ATOM | 11088 | C | SER | B | 202 | −79.067 | −30.099 | −22.441 | 1.00 | 24.98 | C |
| ATOM | 11089 | O | SER | B | 202 | −80.057 | −30.816 | −22.324 | 1.00 | 24.73 | O |
| ATOM | 11091 | N | ILE | B | 203 | −79.032 | −28.849 | −21.982 | 1.00 | 25.60 | N |
| ATOM | 11092 | CA | ILE | B | 203 | −80.219 | −28.255 | −21.372 | 1.00 | 25.98 | C |
| ATOM | 11094 | CB | ILE | B | 203 | −79.908 | −26.967 | −20.591 | 1.00 | 25.85 | C |
| ATOM | 11096 | CG1 | ILE | B | 203 | −79.086 | −27.326 | −19.348 | 1.00 | 25.76 | C |
| ATOM | 11099 | CD1 | ILE | B | 203 | −78.779 | −26.159 | −18.431 | 1.00 | 26.28 | C |
| ATOM | 11103 | CG2 | ILE | B | 203 | −81.212 | −26.253 | −20.206 | 1.00 | 24.51 | C |
| ATOM | 11107 | C | ILE | B | 203 | −81.280 | −28.016 | −22.443 | 1.00 | 26.67 | C |
| ATOM | 11108 | O | ILE | B | 203 | −82.428 | −28.398 | −22.260 | 1.00 | 26.96 | O |
| ATOM | 11110 | N | GLU | B | 204 | −80.879 | −27.412 | −23.563 | 1.00 | 27.30 | N |
| ATOM | 11111 | CA | GLU | B | 204 | −81.758 | −27.205 | −24.720 | 1.00 | 27.49 | C |
| ATOM | 11113 | CB | GLU | B | 204 | −81.036 | −26.384 | −25.804 | 1.00 | 27.67 | C |
| ATOM | 11116 | CG | GLU | B | 204 | −81.849 | −26.077 | −27.073 | 1.00 | 28.50 | C |
| ATOM | 11119 | CD | GLU | B | 204 | −82.987 | −25.072 | −26.855 | 1.00 | 29.81 | C |
| ATOM | 11120 | OE1 | GLU | B | 204 | −83.158 | −24.600 | −25.711 | 1.00 | 31.40 | O |
| ATOM | 11121 | OE2 | GLU | B | 204 | −83.710 | −24.750 | −27.832 | 1.00 | 29.57 | O |
| ATOM | 11122 | C | GLU | B | 204 | −82.201 | −28.542 | −25.287 | 1.00 | 27.52 | C |
| ATOM | 11123 | O | GLU | B | 204 | −83.321 | −28.667 | −25.738 | 1.00 | 27.67 | O |
| ATOM | 11125 | N | ALA | B | 205 | −81.326 | −29.539 | −25.266 | 1.00 | 27.74 | N |
| ATOM | 11126 | CA | ALA | B | 205 | −81.684 | −30.872 | −25.728 | 1.00 | 28.09 | C |
| ATOM | 11128 | CB | ALA | B | 205 | −80.472 | −31.789 | −25.726 | 1.00 | 27.75 | C |
| ATOM | 11132 | C | ALA | B | 205 | −82.771 | −31.448 | −24.839 | 1.00 | 28.81 | C |
| ATOM | 11133 | O | ALA | B | 205 | −83.811 | −31.877 | −25.325 | 1.00 | 28.90 | O |
| ATOM | 11135 | N | TYR | B | 206 | −82.517 | −31.433 | −23.531 | 1.00 | 29.72 | N |
| ATOM | 11136 | CA | TYR | B | 206 | −83.408 | −32.020 | −22.527 | 1.00 | 30.30 | C |
| ATOM | 11138 | CB | TYR | B | 206 | −82.760 | −31.915 | −21.149 | 1.00 | 30.24 | C |
| ATOM | 11141 | CG | TYR | B | 206 | −83.276 | −32.889 | −20.127 | 1.00 | 29.79 | C |
| ATOM | 11142 | CD1 | TYR | B | 206 | −83.055 | −34.245 | −20.286 | 1.00 | 30.71 | C |
| ATOM | 11144 | CE1 | TYR | B | 206 | −83.498 | −35.161 | −19.360 | 1.00 | 30.78 | C |
| ATOM | 11146 | CZ | TYR | B | 206 | −84.159 | −34.731 | −18.238 | 1.00 | 30.03 | C |
| ATOM | 11147 | OH | TYR | B | 206 | −84.582 | −35.684 | −17.343 | 1.00 | 30.51 | O |
| ATOM | 11149 | CE2 | TYR | B | 206 | −84.394 | −33.379 | −18.042 | 1.00 | 29.42 | C |
| ATOM | 11151 | CD2 | TYR | B | 206 | −83.945 | −32.463 | −18.989 | 1.00 | 29.05 | C |
| ATOM | 11153 | C | TYR | B | 206 | −84.744 | −31.308 | −22.467 | 1.00 | 31.19 | C |
| ATOM | 11154 | O | TYR | B | 206 | −85.790 | −31.930 | −22.311 | 1.00 | 31.44 | O |
| ATOM | 11156 | N | ARG | B | 207 | −84.683 | −29.988 | −22.558 | 1.00 | 32.21 | N |
| ATOM | 11157 | CA | ARG | B | 207 | −85.853 | −29.128 | −22.521 | 1.00 | 33.04 | C |

TABLE 3-7-continued

Coordinates of *P. tremuloides IspS*

| | | | | | | | | | | | |
|---|---|---|---|---|---|---|---|---|---|---|---|
| ATOM | 11159 | CB | ARG | B | 207 | −85.394 | −27.700 | −22.843 | 1.00 | 32.86 | C |
| ATOM | 11162 | CG | ARG | B | 207 | −86.441 | −26.637 | −22.846 | 1.00 | 32.82 | C |
| ATOM | 11165 | CD | ARG | B | 207 | −85.905 | −25.360 | −23.462 | 1.00 | 32.76 | C |
| ATOM | 11168 | NE | ARG | B | 207 | −85.148 | −24.561 | −22.504 | 1.00 | 32.80 | N |
| ATOM | 11170 | CZ | ARG | B | 207 | −85.676 | −23.709 | −21.628 | 1.00 | 33.40 | C |
| ATOM | 11171 | NH1 | ARG | B | 207 | −86.989 | −23.526 | −21.555 | 1.00 | 34.29 | N |
| ATOM | 11174 | NH2 | ARG | B | 207 | −84.884 | −23.030 | −20.808 | 1.00 | 33.89 | N |
| ATOM | 11177 | C | ARG | B | 207 | −86.971 | −29.606 | −23.478 | 1.00 | 34.14 | C |
| ATOM | 11178 | O | ARG | B | 207 | −88.144 | −29.521 | −23.128 | 1.00 | 34.34 | O |
| ATOM | 11180 | N | LYS | B | 208 | −86.607 | −30.137 | −24.652 | 1.00 | 35.32 | N |
| ATOM | 11181 | CA | LYS | B | 208 | −87.581 | −30.535 | −25.688 | 1.00 | 36.16 | C |
| ATOM | 11183 | CB | LYS | B | 208 | −86.960 | −30.468 | −27.090 | 1.00 | 36.01 | C |
| ATOM | 11186 | CG | LYS | B | 208 | −86.126 | −29.234 | −27.368 | 1.00 | 35.85 | C |
| ATOM | 11189 | CD | LYS | B | 208 | −85.934 | −29.023 | −28.861 | 1.00 | 35.98 | C |
| ATOM | 11192 | CE | LYS | B | 208 | −84.774 | −28.086 | −29.186 | 1.00 | 35.63 | C |
| ATOM | 11195 | NZ | LYS | B | 208 | −83.566 | −28.843 | −29.596 | 1.00 | 35.17 | N |
| ATOM | 11199 | C | LYS | B | 208 | −88.166 | −31.937 | −25.490 | 1.00 | 37.25 | C |
| ATOM | 11200 | O | LYS | B | 208 | −89.212 | −32.250 | −26.054 | 1.00 | 37.50 | O |
| ATOM | 11202 | N | LYS | B | 209 | −87.484 | −32.788 | −24.730 | 1.00 | 38.58 | N |
| ATOM | 11203 | CA | LYS | B | 209 | −88.026 | −34.106 | −24.383 | 1.00 | 39.89 | C |
| ATOM | 11205 | CB | LYS | B | 209 | −87.013 | −34.923 | −23.578 | 1.00 | 40.23 | C |
| ATOM | 11208 | CG | LYS | B | 209 | −85.914 | −35.604 | −24.373 | 1.00 | 41.47 | C |
| ATOM | 11211 | CD | LYS | B | 209 | −84.858 | −36.178 | −23.417 | 1.00 | 43.71 | C |
| ATOM | 11214 | CE | LYS | B | 209 | −84.448 | −37.612 | −23.764 | 1.00 | 45.15 | C |
| ATOM | 11217 | NZ | LYS | B | 209 | −85.390 | −38.621 | −23.163 | 1.00 | 45.73 | N |
| ATOM | 11221 | C | LYS | B | 209 | −89.288 | −33.950 | −23.530 | 1.00 | 40.51 | C |
| ATOM | 11222 | O | LYS | B | 209 | −89.230 | −33.367 | −22.441 | 1.00 | 40.84 | O |
| ATOM | 11224 | N | GLU | B | 210 | −90.418 | −34.477 | −24.000 | 1.00 | 40.92 | N |
| ATOM | 11225 | CA | GLU | B | 210 | −91.652 | −34.386 | −23.223 | 1.00 | 41.27 | C |
| ATOM | 11227 | CB | GLU | B | 210 | −92.855 | −34.935 | −23.998 | 1.00 | 41.77 | C |
| ATOM | 11230 | CG | GLU | B | 210 | −92.822 | −36.446 | −24.265 | 1.00 | 43.47 | C |
| ATOM | 11233 | CD | GLU | B | 210 | −94.049 | −36.922 | −25.032 | 1.00 | 45.23 | C |
| ATOM | 11234 | OE1 | GLU | B | 210 | −95.188 | −36.590 | −24.612 | 1.00 | 45.02 | O |
| ATOM | 11235 | OE2 | GLU | B | 210 | −93.863 | −37.629 | −26.053 | 1.00 | 46.74 | O |
| ATOM | 11236 | C | GLU | B | 210 | −91.494 | −35.121 | −21.895 | 1.00 | 40.71 | C |
| ATOM | 11237 | O | GLU | B | 210 | −91.996 | −34.667 | −20.864 | 1.00 | 40.99 | O |
| ATOM | 11239 | N | ASP | B | 211 | −90.773 | −36.240 | −21.924 | 1.00 | 39.76 | N |
| ATOM | 11240 | CA | ASP | B | 211 | −90.533 | −37.050 | −20.721 | 1.00 | 38.96 | C |
| ATOM | 11242 | CB | ASP | B | 211 | −90.151 | −38.476 | −21.123 | 1.00 | 39.10 | C |
| ATOM | 11245 | CG | ASP | B | 211 | −89.101 | −38.499 | −22.212 | 1.00 | 40.26 | C |
| ATOM | 11246 | OD1 | ASP | B | 211 | −89.327 | −37.827 | −23.254 | 1.00 | 41.25 | O |
| ATOM | 11247 | OD2 | ASP | B | 211 | −88.055 | −39.160 | −22.020 | 1.00 | 41.66 | O |
| ATOM | 11248 | C | ASP | B | 211 | −89.440 | −36.468 | −19.826 | 1.00 | 37.75 | C |
| ATOM | 11249 | O | ASP | B | 211 | −89.009 | −37.131 | −18.892 | 1.00 | 37.62 | O |
| ATOM | 11251 | N | ALA | B | 212 | −88.989 | −35.245 | −20.115 | 1.00 | 36.47 | N |
| ATOM | 11252 | CA | ALA | B | 212 | −87.941 | −34.587 | −19.335 | 1.00 | 35.36 | C |
| ATOM | 11254 | CB | ALA | B | 212 | −87.516 | −33.294 | −20.011 | 1.00 | 35.23 | C |
| ATOM | 11258 | C | ALA | B | 212 | −88.423 | −34.307 | −17.920 | 1.00 | 34.40 | C |
| ATOM | 11259 | O | ALA | B | 212 | −89.559 | −33.870 | −17.728 | 1.00 | 34.42 | O |
| ATOM | 11261 | N | ASN | B | 213 | −87.565 | −34.574 | −16.937 | 1.00 | 33.24 | N |
| ATOM | 11262 | CA | ASN | B | 213 | −87.890 | −34.333 | −15.533 | 1.00 | 32.67 | C |
| ATOM | 11264 | CB | ASN | B | 213 | −86.840 | −34.986 | −14.623 | 1.00 | 32.58 | C |
| ATOM | 11267 | CG | ASN | B | 213 | −87.204 | −34.912 | −13.152 | 1.00 | 32.67 | C |
| ATOM | 11268 | OD1 | ASN | B | 213 | −87.891 | −33.994 | −12.722 | 1.00 | 32.62 | O |
| ATOM | 11269 | ND2 | ASN | B | 213 | −86.734 | −35.882 | −12.371 | 1.00 | 33.18 | N |
| ATOM | 11272 | C | ASN | B | 213 | −87.990 | −32.825 | −15.266 | 1.00 | 32.19 | C |
| ATOM | 11273 | O | ASN | B | 213 | −87.010 | −32.092 | −15.376 | 1.00 | 32.38 | O |
| ATOM | 11275 | N | GLN | B | 214 | −89.182 | −32.356 | −14.923 | 1.00 | 31.48 | N |
| ATOM | 11276 | CA | GLN | B | 214 | −89.389 | −30.924 | −14.756 | 1.00 | 30.85 | C |
| ATOM | 11278 | CB | GLN | B | 214 | −90.889 | −30.581 | −14.693 | 1.00 | 30.82 | C |
| ATOM | 11281 | CG | GLN | B | 214 | −91.684 | −30.869 | −16.002 | 1.00 | 30.80 | C |
| ATOM | 11284 | CD | GLN | B | 214 | −90.990 | −30.378 | −17.291 | 1.00 | 29.69 | C |
| ATOM | 11285 | OE1 | GLN | B | 214 | −90.893 | −29.174 | −17.543 | 1.00 | 29.07 | O |
| ATOM | 11286 | NE2 | GLN | B | 214 | −90.526 | −31.321 | −18.113 | 1.00 | 27.71 | N |
| ATOM | 11289 | C | GLN | B | 214 | −88.638 | −30.369 | −13.543 | 1.00 | 30.37 | C |
| ATOM | 11290 | O | GLN | B | 214 | −88.263 | −29.200 | −13.533 | 1.00 | 30.80 | O |
| ATOM | 11292 | N | VAL | B | 215 | −88.393 | −31.200 | −12.532 | 1.00 | 29.54 | N |
| ATOM | 11293 | CA | VAL | B | 215 | −87.566 | −30.779 | −11.395 | 1.00 | 28.56 | C |
| ATOM | 11295 | CB | VAL | B | 215 | −87.564 | −31.818 | −10.260 | 1.00 | 28.64 | C |
| ATOM | 11297 | CG1 | VAL | B | 215 | −86.758 | −31.299 | −9.075 | 1.00 | 27.94 | C |
| ATOM | 11301 | CG2 | VAL | B | 215 | −88.999 | −32.167 | −9.856 | 1.00 | 28.26 | C |
| ATOM | 11305 | C | VAL | B | 215 | −86.124 | −30.545 | −11.845 | 1.00 | 27.63 | C |
| ATOM | 11306 | O | VAL | B | 215 | −85.566 | −29.472 | −11.615 | 1.00 | 27.58 | O |
| ATOM | 11308 | N | LEU | B | 216 | −85.546 | −31.548 | −12.504 | 1.00 | 26.37 | N |
| ATOM | 11309 | CA | LEU | B | 216 | −84.143 | −31.509 | −12.930 | 1.00 | 25.47 | C |
| ATOM | 11311 | CB | LEU | B | 216 | −83.714 | −32.866 | −13.490 | 1.00 | 25.46 | C |
| ATOM | 11314 | CG | LEU | B | 216 | −82.274 | −32.995 | −13.979 | 1.00 | 24.97 | C |
| ATOM | 11316 | CD1 | LEU | B | 216 | −81.289 | −32.640 | −12.883 | 1.00 | 24.62 | C |

TABLE 3-7-continued

Coordinates of *P. tremuloides IspS*

| | | | | | | | | | | | |
|---|---|---|---|---|---|---|---|---|---|---|---|
| ATOM | 11320 | CD2 | LEU | B | 216 | −82.042 | −34.407 | −14.472 | 1.00 | 24.55 | C |
| ATOM | 11324 | C | LEU | B | 216 | −83.861 | −30.447 | −13.972 | 1.00 | 24.68 | C |
| ATOM | 11325 | O | LEU | B | 216 | −82.819 | −29.820 | −13.929 | 1.00 | 24.91 | O |
| ATOM | 11327 | N | LEU | B | 217 | −84.776 | −30.269 | −14.916 | 1.00 | 23.79 | N |
| ATOM | 11328 | CA | LEU | B | 217 | −84.625 | −29.260 | −15.960 | 1.00 | 23.13 | C |
| ATOM | 11330 | CB | LEU | B | 217 | −85.765 | −29.384 | −16.972 | 1.00 | 23.36 | C |
| ATOM | 11333 | CG | LEU | B | 217 | −85.808 | −28.374 | −18.123 | 1.00 | 23.18 | C |
| ATOM | 11335 | CD1 | LEU | B | 217 | −84.462 | −28.268 | −18.796 | 1.00 | 22.69 | C |
| ATOM | 11339 | CD2 | LEU | B | 217 | −86.861 | −28.786 | −19.126 | 1.00 | 23.38 | C |
| ATOM | 11343 | C | LEU | B | 217 | −84.631 | −27.853 | −15.383 | 1.00 | 22.51 | C |
| ATOM | 11344 | O | LEU | B | 217 | −83.903 | −26.973 | −15.855 | 1.00 | 22.08 | O |
| ATOM | 11346 | N | GLU | B | 218 | −85.481 | −27.647 | −14.375 | 1.00 | 21.84 | N |
| ATOM | 11347 | CA | GLU | B | 218 | −85.619 | −26.339 | −13.725 | 1.00 | 21.26 | C |
| ATOM | 11349 | CB | GLU | B | 218 | −86.813 | −26.341 | −12.768 | 1.00 | 21.27 | C |
| ATOM | 11352 | CG | GLU | B | 218 | −87.206 | −24.956 | −12.246 | 1.00 | 21.35 | C |
| ATOM | 11355 | CD | GLU | B | 218 | −88.501 | −24.964 | −11.441 | 1.00 | 20.89 | C |
| ATOM | 11356 | OE1 | GLU | B | 218 | −89.097 | −26.052 | −11.263 | 1.00 | 20.47 | O |
| ATOM | 11357 | OE2 | GLU | B | 218 | −88.915 | −23.874 | −10.986 | 1.00 | 20.15 | O |
| ATOM | 11358 | C | GLU | B | 218 | −84.348 | −26.001 | −12.969 | 1.00 | 20.58 | C |
| ATOM | 11359 | O | GLU | B | 218 | −83.877 | −24.865 | −12.982 | 1.00 | 20.31 | O |
| ATOM | 11361 | N | LEU | B | 219 | −83.802 | −27.015 | −12.312 | 1.00 | 19.87 | N |
| ATOM | 11362 | CA | LEU | B | 219 | −82.559 | −26.885 | −11.592 | 1.00 | 19.12 | C |
| ATOM | 11364 | CB | LEU | B | 219 | −82.310 | −28.132 | −10.746 | 1.00 | 18.58 | C |
| ATOM | 11367 | CG | LEU | B | 219 | −81.159 | −28.054 | −9.762 | 1.00 | 17.07 | C |
| ATOM | 11369 | CD1 | LEU | B | 219 | −81.321 | −26.847 | −8.872 | 1.00 | 16.10 | C |
| ATOM | 11373 | CD2 | LEU | B | 219 | −81.107 | −29.311 | −8.954 | 1.00 | 15.22 | C |
| ATOM | 11377 | C | LEU | B | 219 | −81.443 | −26.675 | −12.599 | 1.00 | 19.16 | C |
| ATOM | 11378 | O | LEU | B | 219 | −80.684 | −25.721 | −12.478 | 1.00 | 19.42 | O |
| ATOM | 11380 | N | ALA | B | 220 | −81.368 | −27.546 | −13.606 | 1.00 | 19.04 | N |
| ATOM | 11381 | CA | ALA | B | 220 | −80.356 | −27.431 | −14.669 | 1.00 | 19.04 | C |
| ATOM | 11383 | CB | ALA | B | 220 | −80.648 | −28.398 | −15.817 | 1.00 | 18.64 | C |
| ATOM | 11387 | C | ALA | B | 220 | −80.257 | −26.004 | −15.196 | 1.00 | 19.06 | C |
| ATOM | 11388 | O | ALA | B | 220 | −79.159 | −25.472 | −15.321 | 1.00 | 19.08 | O |
| ATOM | 11390 | N | ILE | B | 221 | −81.410 | −25.393 | −15.475 | 1.00 | 19.19 | N |
| ATOM | 11391 | CA | ILE | B | 221 | −81.473 | −24.016 | −15.963 | 1.00 | 19.22 | C |
| ATOM | 11393 | CB | ILE | B | 221 | −82.898 | −23.638 | −16.423 | 1.00 | 19.03 | C |
| ATOM | 11395 | CG1 | ILE | B | 221 | −83.229 | −24.323 | −17.755 | 1.00 | 18.52 | C |
| ATOM | 11398 | CD1 | ILE | B | 221 | −84.687 | −24.645 | −17.928 | 1.00 | 17.52 | C |
| ATOM | 11402 | CG2 | ILE | B | 221 | −83.024 | −22.121 | −16.564 | 1.00 | 18.03 | C |
| ATOM | 11406 | C | ILE | B | 221 | −81.030 | −23.013 | −14.906 | 1.00 | 19.62 | C |
| ATOM | 11407 | O | ILE | B | 221 | −80.137 | −22.190 | −15.136 | 1.00 | 19.53 | O |
| ATOM | 11409 | N | LEU | B | 222 | −81.666 | −23.096 | −13.745 | 1.00 | 20.27 | N |
| ATOM | 11410 | CA | LEU | B | 222 | −81.412 | −22.161 | −12.654 | 1.00 | 20.63 | C |
| ATOM | 11412 | CB | LEU | B | 222 | −82.203 | −22.561 | −11.412 | 1.00 | 20.50 | C |
| ATOM | 11415 | CG | LEU | B | 222 | −82.195 | −21.523 | −10.296 | 1.00 | 20.76 | C |
| ATOM | 11417 | CD1 | LEU | B | 222 | −83.439 | −21.675 | −9.431 | 1.00 | 21.02 | C |
| ATOM | 11421 | CD2 | LEU | B | 222 | −80.924 | −21.625 | −9.453 | 1.00 | 20.21 | C |
| ATOM | 11425 | C | LEU | B | 222 | −79.925 | −22.089 | −12.341 | 1.00 | 20.98 | C |
| ATOM | 11426 | O | LEU | B | 222 | −79.337 | −21.011 | −12.381 | 1.00 | 21.40 | O |
| ATOM | 11428 | N | ASP | B | 223 | −79.319 | −23.240 | −12.064 | 1.00 | 21.24 | N |
| ATOM | 11429 | CA | ASP | B | 223 | −77.907 | −23.298 | −11.709 | 1.00 | 21.48 | C |
| ATOM | 11431 | CB | ASP | B | 223 | −77.509 | −24.724 | −11.314 | 1.00 | 21.66 | C |
| ATOM | 11434 | CG | ASP | B | 223 | −76.168 | −24.792 | −10.589 | 1.00 | 22.70 | C |
| ATOM | 11435 | OD1 | ASP | B | 223 | −75.095 | −24.775 | −11.244 | 1.00 | 24.25 | O |
| ATOM | 11436 | OD2 | ASP | B | 223 | −76.190 | −24.893 | −9.349 | 1.00 | 24.85 | O |
| ATOM | 11437 | C | ASP | B | 223 | −77.017 | −22.768 | −12.835 | 1.00 | 21.64 | C |
| ATOM | 11438 | O | ASP | B | 223 | −76.035 | −22.104 | −12.548 | 1.00 | 21.66 | O |
| ATOM | 11440 | N | TYR | B | 224 | −77.361 | −23.023 | −14.100 | 1.00 | 22.07 | N |
| ATOM | 11441 | CA | TYR | B | 224 | −76.517 | −22.561 | −15.218 | 1.00 | 22.47 | C |
| ATOM | 11443 | CB | TYR | B | 224 | −76.980 | −23.111 | −16.589 | 1.00 | 22.35 | C |
| ATOM | 11446 | CG | TYR | B | 224 | −76.032 | −22.733 | −17.724 | 1.00 | 22.25 | C |
| ATOM | 11447 | CD1 | TYR | B | 224 | −75.002 | −23.576 | −18.116 | 1.00 | 21.46 | C |
| ATOM | 11449 | CE1 | TYR | B | 224 | −74.126 | −23.216 | −19.135 | 1.00 | 21.43 | C |
| ATOM | 11451 | CZ | TYR | B | 224 | −74.260 | −21.991 | −19.761 | 1.00 | 21.62 | C |
| ATOM | 11452 | OH | TYR | B | 224 | −73.387 | −21.618 | −20.760 | 1.00 | 20.46 | O |
| ATOM | 11454 | CE2 | TYR | B | 224 | −75.270 | −21.132 | −19.387 | 1.00 | 22.04 | C |
| ATOM | 11456 | CD2 | TYR | B | 224 | −76.144 | −21.500 | −18.373 | 1.00 | 22.73 | C |
| ATOM | 11458 | C | TYR | B | 224 | −76.414 | −21.023 | −15.262 | 1.00 | 23.06 | C |
| ATOM | 11459 | O | TYR | B | 224 | −75.323 | −20.467 | −15.507 | 1.00 | 22.89 | O |
| ATOM | 11461 | N | ASN | B | 225 | −77.543 | −20.350 | −15.027 | 1.00 | 23.66 | N |
| ATOM | 11462 | CA | ASN | B | 225 | −77.593 | −18.884 | −15.072 | 1.00 | 24.16 | C |
| ATOM | 11464 | CB | ASN | B | 225 | −79.040 | −18.367 | −15.107 | 1.00 | 24.12 | C |
| ATOM | 11467 | CG | ASN | B | 225 | −79.778 | −18.761 | −16.365 | 1.00 | 23.89 | C |
| ATOM | 11468 | OD1 | ASN | B | 225 | −79.182 | −18.877 | −17.437 | 1.00 | 24.33 | O |
| ATOM | 11469 | ND2 | ASN | B | 225 | −81.088 | −18.965 | −16.244 | 1.00 | 22.05 | N |
| ATOM | 11472 | C | ASN | B | 225 | −76.880 | −18.265 | −13.881 | 1.00 | 24.73 | C |
| ATOM | 11473 | O | ASN | B | 225 | −76.195 | −17.247 | −14.027 | 1.00 | 25.09 | O |
| ATOM | 11475 | N | MET | B | 226 | −77.067 | −18.864 | −12.703 | 1.00 | 25.15 | N |

TABLE 3-7-continued

Coordinates of *P. tremuloides IspS*

| | | | | | | | | | | | |
|---|---|---|---|---|---|---|---|---|---|---|---|
| ATOM | 11476 | CA | MET | B | 226 | −76.423 | −18.390 | −11.479 | 1.00 | 25.53 | C |
| ATOM | 11478 | CB | MET | B | 226 | −76.806 | −19.278 | −10.282 | 1.00 | 26.11 | C |
| ATOM | 11481 | CG | MET | B | 226 | −75.905 | −19.169 | −9.023 | 1.00 | 27.59 | C |
| ATOM | 11484 | SD | MET | B | 226 | −75.676 | −20.788 | −8.214 | 1.00 | 30.67 | S |
| ATOM | 11485 | CE | MET | B | 226 | −77.308 | −21.005 | −7.476 | 1.00 | 29.78 | C |
| ATOM | 11489 | C | MET | B | 226 | −74.920 | −18.380 | −11.692 | 1.00 | 25.16 | C |
| ATOM | 11490 | O | MET | B | 226 | −74.258 | −17.387 | −11.391 | 1.00 | 25.10 | O |
| ATOM | 11492 | N | ILE | B | 227 | −74.388 | −19.473 | −12.239 | 1.00 | 24.88 | N |
| ATOM | 11493 | CA | ILE | B | 227 | −72.944 | −19.564 | −12.501 | 1.00 | 24.70 | C |
| ATOM | 11495 | CB | ILE | B | 227 | −72.476 | −20.994 | −12.882 | 1.00 | 24.45 | C |
| ATOM | 11497 | CG1 | ILE | B | 227 | −72.656 | −21.947 | −11.695 | 1.00 | 23.80 | C |
| ATOM | 11500 | CD1 | ILE | B | 227 | −72.094 | −23.332 | −11.885 | 1.00 | 21.97 | C |
| ATOM | 11504 | CG2 | ILE | B | 227 | −71.030 | −20.969 | −13.266 | 1.00 | 24.90 | C |
| ATOM | 11508 | C | ILE | B | 227 | −72.529 | −18.550 | −13.566 | 1.00 | 24.45 | C |
| ATOM | 11509 | O | ILE | B | 227 | −71.578 | −17.810 | −13.373 | 1.00 | 24.42 | O |
| ATOM | 11511 | N | GLN | B | 228 | −73.264 | −18.484 | −14.668 | 1.00 | 24.31 | N |
| ATOM | 11512 | CA | GLN | B | 228 | −73.038 | −17.414 | −15.639 | 1.00 | 24.19 | C |
| ATOM | 11514 | CB | GLN | B | 228 | −74.143 | −17.363 | −16.688 | 1.00 | 24.02 | C |
| ATOM | 11517 | CG | GLN | B | 228 | −73.788 | −16.488 | −17.864 | 1.00 | 23.42 | C |
| ATOM | 11520 | CD | GLN | B | 228 | −74.807 | −16.567 | −18.983 | 1.00 | 23.70 | C |
| ATOM | 11521 | OE1 | GLN | B | 228 | −75.790 | −15.813 | −19.015 | 1.00 | 24.07 | O |
| ATOM | 11522 | NE2 | GLN | B | 228 | −74.564 | −17.465 | −19.927 | 1.00 | 23.49 | N |
| ATOM | 11525 | C | GLN | B | 228 | −72.913 | −16.037 | −14.987 | 1.00 | 24.37 | C |
| ATOM | 11526 | O | GLN | B | 228 | −72.145 | −15.210 | −15.470 | 1.00 | 24.45 | O |
| ATOM | 11528 | N | SER | B | 229 | −73.653 | −15.776 | −13.909 | 1.00 | 24.45 | N |
| ATOM | 11529 | CA | SER | B | 229 | −73.578 | −14.459 | −13.264 | 1.00 | 24.76 | C |
| ATOM | 11531 | CB | SER | B | 229 | −74.815 | −14.163 | −12.397 | 1.00 | 24.84 | C |
| ATOM | 11534 | OG | SER | B | 229 | −74.711 | −14.718 | −11.096 | 1.00 | 25.81 | O |
| ATOM | 11536 | C | SER | B | 229 | −72.270 | −14.279 | −12.469 | 1.00 | 24.64 | C |
| ATOM | 11537 | O | SER | B | 229 | −71.726 | −13.172 | −12.408 | 1.00 | 24.95 | O |
| ATOM | 11539 | N | VAL | B | 230 | −71.751 | −15.350 | −11.878 | 1.00 | 24.20 | N |
| ATOM | 11540 | CA | VAL | B | 230 | −70.415 | −15.277 | −11.299 | 1.00 | 23.99 | C |
| ATOM | 11542 | CB | VAL | B | 230 | −70.006 | −16.581 | −10.574 | 1.00 | 23.92 | C |
| ATOM | 11544 | CG1 | VAL | B | 230 | −68.546 | −16.510 | −10.105 | 1.00 | 23.71 | C |
| ATOM | 11548 | CG2 | VAL | B | 230 | −70.923 | −16.853 | −9.409 | 1.00 | 23.52 | C |
| ATOM | 11552 | C | VAL | B | 230 | −69.386 | −14.966 | −12.400 | 1.00 | 24.12 | C |
| ATOM | 11553 | O | VAL | B | 230 | −68.397 | −14.291 | −12.136 | 1.00 | 24.01 | O |
| ATOM | 11555 | N | TYR | B | 231 | −69.612 | −15.461 | −13.621 | 1.00 | 24.30 | N |
| ATOM | 11556 | CA | TYR | B | 231 | −68.672 | −15.235 | −14.728 | 1.00 | 24.53 | C |
| ATOM | 11558 | CB | TYR | B | 231 | −68.997 | −16.104 | −15.946 | 1.00 | 24.08 | C |
| ATOM | 11561 | CG | TYR | B | 231 | −68.892 | −17.605 | −15.754 | 1.00 | 23.29 | C |
| ATOM | 11562 | CD1 | TYR | B | 231 | −68.173 | −18.168 | −14.706 | 1.00 | 23.08 | C |
| ATOM | 11564 | CE1 | TYR | B | 231 | −68.073 | −19.547 | −14.565 | 1.00 | 22.01 | C |
| ATOM | 11566 | CZ | TYR | B | 231 | −68.685 | −20.369 | −15.479 | 1.00 | 21.16 | C |
| ATOM | 11567 | OH | TYR | B | 231 | −68.607 | −21.746 | −15.353 | 1.00 | 20.18 | O |
| ATOM | 11569 | CE2 | TYR | B | 231 | −69.387 | −19.825 | −16.523 | 1.00 | 21.64 | C |
| ATOM | 11571 | CD2 | TYR | B | 231 | −69.476 | −18.464 | −16.662 | 1.00 | 22.15 | C |
| ATOM | 11573 | C | TYR | B | 231 | −68.658 | −13.772 | −15.166 | 1.00 | 25.37 | C |
| ATOM | 11574 | O | TYR | B | 231 | −67.602 | −13.221 | −15.528 | 1.00 | 25.25 | O |
| ATOM | 11576 | N | GLN | B | 232 | −69.832 | −13.148 | −15.129 | 1.00 | 26.11 | N |
| ATOM | 11577 | CA | GLN | B | 232 | −69.978 | −11.797 | −15.622 | 1.00 | 26.68 | C |
| ATOM | 11579 | CB | GLN | B | 232 | −71.430 | −11.541 | −15.995 | 1.00 | 26.45 | C |
| ATOM | 11582 | CG | GLN | B | 232 | −71.883 | −12.385 | −17.176 | 1.00 | 25.67 | C |
| ATOM | 11585 | CD | GLN | B | 232 | −73.388 | −12.394 | −17.381 | 1.00 | 24.91 | C |
| ATOM | 11586 | OE1 | GLN | B | 232 | −74.140 | −11.761 | −16.637 | 1.00 | 24.81 | O |
| ATOM | 11587 | NE2 | GLN | B | 232 | −73.834 | −13.113 | −18.407 | 1.00 | 23.39 | N |
| ATOM | 11590 | C | GLN | B | 232 | −69.445 | −10.802 | −14.593 | 1.00 | 27.90 | C |
| ATOM | 11591 | O | GLN | B | 232 | −68.909 | −9.752 | −14.958 | 1.00 | 27.96 | O |
| ATOM | 11593 | N | ARG | B | 233 | −69.572 | −11.145 | −13.312 | 1.00 | 29.35 | N |
| ATOM | 11594 | CA | ARG | B | 233 | −68.908 | −10.396 | −12.241 | 1.00 | 30.59 | C |
| ATOM | 11596 | CB | ARG | B | 233 | −69.490 | −10.775 | −10.867 | 1.00 | 30.99 | C |
| ATOM | 11599 | CG | ARG | B | 233 | −68.824 | −10.114 | −9.661 | 1.00 | 32.72 | C |
| ATOM | 11602 | CD | ARG | B | 233 | −69.695 | −10.210 | −8.391 | 1.00 | 35.70 | C |
| ATOM | 11605 | NE | ARG | B | 233 | −70.162 | −11.578 | −8.086 | 1.00 | 38.29 | N |
| ATOM | 11607 | CZ | ARG | B | 233 | −71.403 | −12.053 | −8.276 | 1.00 | 39.65 | C |
| ATOM | 11608 | NH1 | ARG | B | 233 | −72.367 | −11.287 | −8.787 | 1.00 | 40.23 | N |
| ATOM | 11611 | NH2 | ARG | B | 233 | −71.687 | −13.320 | −7.949 | 1.00 | 39.61 | N |
| ATOM | 11614 | C | ARG | B | 233 | −67.390 | −10.632 | −12.303 | 1.00 | 31.10 | C |
| ATOM | 11615 | O | ARG | B | 233 | −66.615 | −9.693 | −12.181 | 1.00 | 31.19 | O |
| ATOM | 11617 | N | ASP | B | 234 | −66.954 | −11.868 | −12.517 | 1.00 | 31.91 | N |
| ATOM | 11618 | CA | ASP | B | 234 | −65.530 | −12.102 | −12.750 | 1.00 | 32.63 | C |
| ATOM | 11620 | CB | ASP | B | 234 | −65.220 | −13.566 | −13.090 | 1.00 | 32.53 | C |
| ATOM | 11623 | CG | ASP | B | 234 | −65.336 | −14.493 | −11.894 | 1.00 | 32.90 | C |
| ATOM | 11624 | OD1 | ASP | B | 234 | −65.477 | −14.028 | −10.746 | 1.00 | 33.06 | O |
| ATOM | 11625 | OD2 | ASP | B | 234 | −65.293 | −15.713 | −12.107 | 1.00 | 34.22 | O |
| ATOM | 11626 | C | ASP | B | 234 | −65.058 | −11.206 | −13.886 | 1.00 | 33.10 | C |
| ATOM | 11627 | O | ASP | B | 234 | −64.097 | −10.458 | −13.723 | 1.00 | 33.55 | O |
| ATOM | 11629 | N | LEU | B | 235 | −65.753 | −11.256 | −15.017 | 1.00 | 33.49 | N |

TABLE 3-7-continued

Coordinates of *P. tremuloides IspS*

| | | | | | | | | | | | |
|---|---|---|---|---|---|---|---|---|---|---|---|
| ATOM | 11630 | CA | LEU | B | 235 | −65.311 | −10.550 | −16.216 | 1.00 | 34.06 | C |
| ATOM | 11632 | CB | LEU | B | 235 | −66.139 | −10.996 | −17.422 | 1.00 | 33.80 | C |
| ATOM | 11635 | CG | LEU | B | 235 | −65.769 | −10.403 | −18.775 | 1.00 | 32.13 | C |
| ATOM | 11637 | CD1 | LEU | B | 235 | −64.303 | −10.679 | −19.050 | 1.00 | 30.94 | C |
| ATOM | 11641 | CD2 | LEU | B | 235 | −66.670 | −10.959 | −19.870 | 1.00 | 29.93 | C |
| ATOM | 11645 | C | LEU | B | 235 | −65.345 | −9.023 | −16.103 | 1.00 | 35.40 | C |
| ATOM | 11646 | O | LEU | B | 235 | −64.500 | −8.352 | −16.682 | 1.00 | 35.61 | O |
| ATOM | 11648 | N | ARG | B | 236 | −66.327 | −8.473 | −15.386 | 1.00 | 36.92 | N |
| ATOM | 11649 | CA | ARG | B | 236 | −66.380 | −7.019 | −15.137 | 1.00 | 38.06 | C |
| ATOM | 11651 | CB | ARG | B | 236 | −67.650 | −6.607 | −14.367 | 1.00 | 38.43 | C |
| ATOM | 11654 | CG | ARG | B | 236 | −68.882 | −6.321 | −15.230 | 1.00 | 39.58 | C |
| ATOM | 11657 | CD | ARG | B | 236 | −69.958 | −5.520 | −14.459 | 1.00 | 40.93 | C |
| ATOM | 11660 | NE | ARG | B | 236 | −70.383 | −6.149 | −13.199 | 1.00 | 41.74 | N |
| ATOM | 11662 | CZ | ARG | B | 236 | −71.208 | −7.195 | −13.095 | 1.00 | 42.20 | C |
| ATOM | 11663 | NH1 | ARG | B | 236 | −71.719 | −7.784 | −14.175 | 1.00 | 41.61 | N |
| ATOM | 11666 | NH2 | ARG | B | 236 | −71.517 | −7.672 | −11.892 | 1.00 | 42.99 | N |
| ATOM | 11669 | C | ARG | B | 236 | −65.170 | −6.550 | −14.343 | 1.00 | 38.57 | C |
| ATOM | 11670 | O | ARG | B | 236 | −64.593 | −5.524 | −14.665 | 1.00 | 38.61 | O |
| ATOM | 11672 | N | GLU | B | 237 | −64.822 | −7.292 | −13.291 | 1.00 | 39.42 | N |
| ATOM | 11673 | CA | GLU | B | 237 | −63.625 | −7.017 | −12.480 | 1.00 | 40.18 | C |
| ATOM | 11675 | CB | GLU | B | 237 | −63.471 | −8.033 | −11.317 | 1.00 | 40.67 | C |
| ATOM | 11678 | CG | GLU | B | 237 | −64.336 | −7.750 | −10.057 | 1.00 | 42.61 | C |
| ATOM | 11681 | CD | GLU | B | 237 | −64.258 | −8.858 | −8.961 | 1.00 | 45.07 | C |
| ATOM | 11682 | OE1 | GLU | B | 237 | −64.051 | −10.066 | −9.282 | 1.00 | 46.74 | O |
| ATOM | 11683 | OE2 | GLU | B | 237 | −64.436 | −8.511 | −7.764 | 1.00 | 45.87 | O |
| ATOM | 11684 | C | GLU | B | 237 | −62.352 | −7.024 | −13.344 | 1.00 | 39.93 | C |
| ATOM | 11685 | O | GLU | B | 237 | −61.593 | −6.050 | −13.332 | 1.00 | 39.96 | O |
| ATOM | 11687 | N | THR | B | 238 | −62.123 | −8.104 | −14.095 | 1.00 | 39.56 | N |
| ATOM | 11688 | CA | THR | B | 238 | −60.900 | −8.200 | −14.895 | 1.00 | 39.42 | C |
| ATOM | 11690 | CB | THR | B | 238 | −60.492 | −9.666 | −15.268 | 1.00 | 39.39 | C |
| ATOM | 11692 | OG1 | THR | B | 238 | −61.222 | −10.123 | −16.413 | 1.00 | 39.37 | O |
| ATOM | 11694 | CG2 | THR | B | 238 | −60.683 | −10.612 | −14.095 | 1.00 | 38.73 | C |
| ATOM | 11698 | C | THR | B | 238 | −60.961 | −7.326 | −16.156 | 1.00 | 39.48 | C |
| ATOM | 11699 | O | THR | B | 238 | −59.930 | −7.062 | −16.761 | 1.00 | 39.48 | O |
| ATOM | 11701 | N | SER | B | 239 | −62.149 | −6.871 | −16.549 | 1.00 | 39.62 | N |
| ATOM | 11702 | CA | SER | B | 239 | −62.264 | −5.882 | −17.631 | 1.00 | 39.63 | C |
| ATOM | 11704 | CB | SER | B | 239 | −63.689 | −5.810 | −18.172 | 1.00 | 39.56 | C |
| ATOM | 11707 | OG | SER | B | 239 | −63.945 | −6.917 | −19.010 | 1.00 | 38.96 | O |
| ATOM | 11709 | C | SER | B | 239 | −61.796 | −4.496 | −17.181 | 1.00 | 39.99 | C |
| ATOM | 11710 | O | SER | B | 239 | −61.108 | −3.807 | −17.933 | 1.00 | 40.10 | O |
| ATOM | 11712 | N | ARG | B | 240 | −62.168 | −4.088 | −15.965 | 1.00 | 40.35 | N |
| ATOM | 11713 | CA | ARG | B | 240 | −61.624 | −2.864 | −15.363 | 1.00 | 40.68 | C |
| ATOM | 11715 | CB | ARG | B | 240 | −62.025 | −2.712 | −13.881 | 1.00 | 41.26 | C |
| ATOM | 11718 | CG | ARG | B | 240 | −63.231 | −1.782 | −13.621 | 1.00 | 43.86 | C |
| ATOM | 11721 | CD | ARG | B | 240 | −63.334 | −1.375 | −12.130 | 1.00 | 47.07 | C |
| ATOM | 11724 | NE | ARG | B | 240 | −63.365 | −2.537 | −11.222 | 1.00 | 50.14 | N |
| ATOM | 11726 | CZ | ARG | B | 240 | −64.462 | −3.077 | −10.671 | 1.00 | 52.32 | C |
| ATOM | 11727 | NH1 | ARG | B | 240 | −64.342 | −4.141 | −9.875 | 1.00 | 53.16 | N |
| ATOM | 11730 | NH2 | ARG | B | 240 | −65.677 | −2.577 | −10.899 | 1.00 | 53.18 | N |
| ATOM | 11733 | C | ARG | B | 240 | −60.113 | −2.914 | −15.464 | 1.00 | 39.91 | C |
| ATOM | 11734 | O | ARG | B | 240 | −59.490 | −2.000 | −15.988 | 1.00 | 39.86 | O |
| ATOM | 11736 | N | TRP | B | 241 | −59.541 | −4.002 | −14.962 | 1.00 | 39.14 | N |
| ATOM | 11737 | CA | TRP | B | 241 | −58.105 | −4.217 | −15.004 | 1.00 | 38.37 | C |
| ATOM | 11739 | CB | TRP | B | 241 | −57.773 | −5.635 | −14.521 | 1.00 | 38.17 | C |
| ATOM | 11742 | CG | TRP | B | 241 | −56.373 | −6.005 | −14.773 | 1.00 | 36.58 | C |
| ATOM | 11743 | CD1 | TRP | B | 241 | −55.290 | −5.668 | −14.022 | 1.00 | 36.32 | C |
| ATOM | 11745 | NE1 | TRP | B | 241 | −54.152 | −6.176 | −14.587 | 1.00 | 35.63 | N |
| ATOM | 11747 | CE2 | TRP | B | 241 | −54.494 | −6.846 | −15.731 | 1.00 | 34.31 | C |
| ATOM | 11748 | CD2 | TRP | B | 241 | −55.883 | −6.757 | −15.874 | 1.00 | 33.99 | C |
| ATOM | 11749 | CE3 | TRP | B | 241 | −56.484 | −7.357 | −16.977 | 1.00 | 33.28 | C |
| ATOM | 11751 | CZ3 | TRP | B | 241 | −55.691 | −8.034 | −17.883 | 1.00 | 32.79 | C |
| ATOM | 11753 | CH2 | TRP | B | 241 | −54.313 | −8.101 | −17.720 | 1.00 | 33.06 | C |
| ATOM | 11755 | CZ2 | TRP | B | 241 | −53.697 | −7.515 | −16.648 | 1.00 | 34.16 | C |
| ATOM | 11757 | C | TRP | B | 241 | −57.561 | −3.999 | −16.409 | 1.00 | 38.25 | C |
| ATOM | 11758 | O | TRP | B | 241 | −56.607 | −3.252 | −16.603 | 1.00 | 38.13 | O |
| ATOM | 11760 | N | TRP | B | 242 | −58.186 | −4.644 | −17.386 | 1.00 | 38.21 | N |
| ATOM | 11761 | CA | TRP | B | 242 | −57.695 | −4.628 | −18.765 | 1.00 | 38.27 | C |
| ATOM | 11763 | CB | TRP | B | 242 | −58.479 | −5.640 | −19.609 | 1.00 | 38.31 | C |
| ATOM | 11766 | CG | TRP | B | 242 | −57.948 | −5.872 | −20.990 | 1.00 | 38.61 | C |
| ATOM | 11767 | CD1 | TRP | B | 242 | −58.642 | −5.754 | −22.156 | 1.00 | 39.11 | C |
| ATOM | 11769 | NE1 | TRP | B | 242 | −57.828 | −6.046 | −23.224 | 1.00 | 39.31 | N |
| ATOM | 11771 | CE2 | TRP | B | 242 | −56.582 | −6.363 | −22.759 | 1.00 | 38.95 | C |
| ATOM | 11772 | CD2 | TRP | B | 242 | −56.617 | −6.263 | −21.356 | 1.00 | 38.66 | C |
| ATOM | 11773 | CE3 | TRP | B | 242 | −55.454 | −6.528 | −20.637 | 1.00 | 38.98 | C |
| ATOM | 11775 | CZ3 | TRP | B | 242 | −54.314 | −6.886 | −21.326 | 1.00 | 39.20 | C |
| ATOM | 11777 | CH2 | TRP | B | 242 | −54.313 | −6.985 | −22.716 | 1.00 | 39.12 | C |
| ATOM | 11779 | CZ2 | TRP | B | 242 | −55.434 | −6.724 | −23.451 | 1.00 | 39.22 | C |
| ATOM | 11781 | C | TRP | B | 242 | −57.739 | −3.241 | −19.400 | 1.00 | 38.27 | C |

TABLE 3-7-continued

Coordinates of *P. tremuloides IspS*

| | | | | | | | | | | | |
|---|---|---|---|---|---|---|---|---|---|---|---|
| ATOM | 11782 | O | TRP | B | 242 | −56.814 | −2.873 | −20.108 | 1.00 | 37.81 | O |
| ATOM | 11784 | N | ARG | B | 243 | −58.809 | −2.489 | −19.140 | 1.00 | 38.79 | N |
| ATOM | 11785 | CA | ARG | B | 243 | −58.936 | −1.097 | −19.607 | 1.00 | 39.37 | C |
| ATOM | 11787 | CB | ARG | B | 243 | −60.351 | −.552 | −19.346 | 1.00 | 39.66 | C |
| ATOM | 11790 | CG | ARG | B | 243 | −61.324 | −.792 | −20.520 | 1.00 | 41.96 | C |
| ATOM | 11793 | CD | ARG | B | 243 | −62.687 | −1.338 | −20.085 | 1.00 | 44.82 | C |
| ATOM | 11796 | NE | ARG | B | 243 | −63.461 | −.380 | −19.296 | 1.00 | 47.15 | N |
| ATOM | 11798 | CZ | ARG | B | 243 | −64.389 | −.704 | −18.386 | 1.00 | 49.26 | C |
| ATOM | 11799 | NH1 | ARG | B | 243 | −64.685 | −1.976 | −18.109 | 1.00 | 49.18 | N |
| ATOM | 11802 | NH2 | ARG | B | 243 | −65.028 | .262 | −17.729 | 1.00 | 50.40 | N |
| ATOM | 11805 | C | ARG | B | 243 | −57.890 | −.183 | −18.980 | 1.00 | 39.28 | C |
| ATOM | 11806 | O | ARG | B | 243 | −57.246 | .577 | −19.681 | 1.00 | 39.40 | O |
| ATOM | 11808 | N | ARG | B | 244 | −57.724 | −.282 | −17.665 | 1.00 | 39.52 | N |
| ATOM | 11809 | CA | ARG | B | 244 | −56.734 | .489 | −16.888 | 1.00 | 39.61 | C |
| ATOM | 11811 | CB | ARG | B | 244 | −56.774 | .041 | −15.409 | 1.00 | 40.25 | C |
| ATOM | 11814 | CG | ARG | B | 244 | −56.115 | .971 | −14.383 | 1.00 | 42.01 | C |
| ATOM | 11817 | CD | ARG | B | 244 | −57.029 | 2.154 | −14.017 | 1.00 | 44.39 | C |
| ATOM | 11820 | NE | ARG | B | 244 | −56.391 | 3.115 | −13.103 | 1.00 | 46.36 | N |
| ATOM | 11822 | CZ | ARG | B | 244 | −55.434 | 3.984 | −13.441 | 1.00 | 48.06 | C |
| ATOM | 11823 | NH1 | ARG | B | 244 | −54.951 | 4.043 | −14.686 | 1.00 | 48.90 | N |
| ATOM | 11826 | NH2 | ARG | B | 244 | −54.947 | 4.805 | −12.519 | 1.00 | 48.82 | N |
| ATOM | 11829 | C | ARG | B | 244 | −55.323 | .322 | −17.437 | 1.00 | 38.83 | C |
| ATOM | 11830 | O | ARG | B | 244 | −54.594 | 1.300 | −17.567 | 1.00 | 38.39 | O |
| ATOM | 11832 | N | VAL | B | 245 | −54.953 | −.922 | −17.738 | 1.00 | 38.52 | N |
| ATOM | 11833 | CA | VAL | B | 245 | −53.694 | −1.241 | −18.437 | 1.00 | 38.43 | C |
| ATOM | 11835 | CB | VAL | B | 245 | −53.491 | −2.760 | −18.614 | 1.00 | 38.31 | C |
| ATOM | 11837 | CG1 | VAL | B | 245 | −53.247 | −3.426 | −17.283 | 1.00 | 37.77 | C |
| ATOM | 11841 | CG2 | VAL | B | 245 | −52.344 | −3.036 | −19.561 | 1.00 | 37.66 | C |
| ATOM | 11845 | C | VAL | B | 245 | −53.650 | −.638 | −19.832 | 1.00 | 38.68 | C |
| ATOM | 11846 | O | VAL | B | 245 | −52.615 | −.153 | −20.247 | 1.00 | 38.57 | O |
| ATOM | 11848 | N | GLY | B | 246 | −54.765 | −.724 | −20.559 | 1.00 | 39.26 | N |
| ATOM | 11849 | CA | GLY | B | 246 | −54.974 | −.012 | −21.834 | 1.00 | 39.62 | C |
| ATOM | 11852 | C | GLY | B | 246 | −53.962 | −.262 | −22.942 | 1.00 | 40.08 | C |
| ATOM | 11853 | O | GLY | B | 246 | −53.617 | .650 | −23.700 | 1.00 | 39.89 | O |
| ATOM | 11855 | N | LEU | B | 247 | −53.502 | −1.500 | −23.062 | 1.00 | 40.75 | N |
| ATOM | 11856 | CA | LEU | B | 247 | −52.347 | −1.778 | −23.905 | 1.00 | 41.34 | C |
| ATOM | 11858 | CB | LEU | B | 247 | −51.655 | −3.065 | −23.459 | 1.00 | 41.15 | C |
| ATOM | 11861 | CG | LEU | B | 247 | −50.132 | −3.026 | −23.298 | 1.00 | 40.49 | C |
| ATOM | 11863 | CD1 | LEU | B | 247 | −49.622 | −1.769 | −22.605 | 1.00 | 39.50 | C |
| ATOM | 11867 | CD2 | LEU | B | 247 | −49.695 | −4.242 | −22.526 | 1.00 | 39.98 | C |
| ATOM | 11871 | C | LEU | B | 247 | −52.744 | −1.836 | −25.370 | 1.00 | 42.50 | C |
| ATOM | 11872 | O | LEU | B | 247 | −52.005 | −1.358 | −26.225 | 1.00 | 42.33 | O |
| ATOM | 11874 | N | ALA | B | 248 | −53.925 | −2.390 | −25.654 | 1.00 | 44.14 | N |
| ATOM | 11875 | CA | ALA | B | 248 | −54.439 | −2.494 | −27.041 | 1.00 | 45.16 | C |
| ATOM | 11877 | CB | ALA | B | 248 | −55.705 | −3.347 | −27.087 | 1.00 | 45.15 | C |
| ATOM | 11881 | C | ALA | B | 248 | −54.692 | −1.140 | −27.739 | 1.00 | 45.98 | C |
| ATOM | 11882 | O | ALA | B | 248 | −54.604 | −1.053 | −28.971 | 1.00 | 46.37 | O |
| ATOM | 11884 | N | THR | B | 249 | −55.004 | −.095 | −26.975 | 1.00 | 46.64 | N |
| ATOM | 11885 | CA | THR | B | 249 | −55.142 | 1.234 | −27.570 | 1.00 | 47.25 | C |
| ATOM | 11887 | CB | THR | B | 249 | −55.905 | 2.253 | −26.655 | 1.00 | 47.44 | C |
| ATOM | 11889 | OG1 | THR | B | 249 | −55.001 | 2.845 | −25.706 | 1.00 | 47.52 | O |
| ATOM | 11891 | CG2 | THR | B | 249 | −57.104 | 1.592 | −25.928 | 1.00 | 47.44 | C |
| ATOM | 11895 | C | THR | B | 249 | −53.756 | 1.793 | −27.931 | 1.00 | 47.59 | C |
| ATOM | 11896 | O | THR | B | 249 | −53.553 | 2.279 | −29.049 | 1.00 | 48.07 | O |
| ATOM | 11898 | N | LYS | B | 250 | −52.808 | 1.710 | −26.995 | 1.00 | 47.67 | N |
| ATOM | 11899 | CA | LYS | B | 250 | −51.469 | 2.299 | −27.185 | 1.00 | 47.68 | C |
| ATOM | 11901 | CB | LYS | B | 250 | −50.793 | 2.553 | −25.833 | 1.00 | 47.68 | C |
| ATOM | 11904 | CG | LYS | B | 250 | −51.428 | 3.673 | −24.999 | 1.00 | 47.77 | C |
| ATOM | 11907 | CD | LYS | B | 250 | −51.142 | 5.086 | −25.552 | 1.00 | 47.59 | C |
| ATOM | 11910 | CE | LYS | B | 250 | −49.676 | 5.496 | −25.441 | 1.00 | 46.75 | C |
| ATOM | 11913 | NZ | LYS | B | 250 | −49.479 | 6.878 | −25.948 | 1.00 | 46.49 | N |
| ATOM | 11917 | C | LYS | B | 250 | −50.541 | 1.465 | −28.082 | 1.00 | 47.72 | C |
| ATOM | 11918 | O | LYS | B | 250 | −49.591 | 1.988 | −28.663 | 1.00 | 47.54 | O |
| ATOM | 11920 | N | LEU | B | 251 | −50.804 | .169 | −28.184 | 1.00 | 47.82 | N |
| ATOM | 11921 | CA | LEU | B | 251 | −50.072 | −.675 | −29.118 | 1.00 | 47.96 | C |
| ATOM | 11923 | CB | LEU | B | 251 | −49.584 | −1.970 | −28.447 | 1.00 | 48.04 | C |
| ATOM | 11926 | CG | LEU | B | 251 | −48.109 | −2.064 | −28.033 | 1.00 | 47.39 | C |
| ATOM | 11928 | CD1 | LEU | B | 251 | −47.659 | −.881 | −27.186 | 1.00 | 46.47 | C |
| ATOM | 11932 | CD2 | LEU | B | 251 | −47.894 | −3.376 | −27.304 | 1.00 | 46.78 | C |
| ATOM | 11936 | C | LEU | B | 251 | −50.985 | −.964 | −30.306 | 1.00 | 48.19 | C |
| ATOM | 11937 | O | LEU | B | 251 | −51.975 | −1.693 | −30.194 | 1.00 | 48.38 | O |
| ATOM | 11939 | N | HIS | B | 252 | −50.627 | −.396 | −31.449 | 1.00 | 48.42 | N |
| ATOM | 11940 | CA | HIS | B | 252 | −51.521 | −.329 | −32.601 | 1.00 | 48.62 | C |
| ATOM | 11942 | CB | HIS | B | 252 | −51.110 | .850 | −33.492 | 1.00 | 48.99 | C |
| ATOM | 11945 | CG | HIS | B | 252 | −51.000 | 2.145 | −32.742 | 1.00 | 50.56 | C |
| ATOM | 11946 | ND1 | HIS | B | 252 | −52.095 | 2.935 | −32.453 | 1.00 | 52.11 | N |
| ATOM | 11948 | CE1 | HIS | B | 252 | −51.704 | 3.993 | −31.766 | 1.00 | 52.68 | C |
| ATOM | 11950 | NE2 | HIS | B | 252 | −50.397 | 3.912 | −31.585 | 1.00 | 52.86 | N |

TABLE 3-7-continued

Coordinates of *P. tremuloides IspS*

| | | | | | | | | | | | |
|---|---|---|---|---|---|---|---|---|---|---|---|
| ATOM | 11952 | CD2 | HIS | B | 252 | −49.932 | 2.764 | −32.181 | 1.00 | 51.68 | C |
| ATOM | 11954 | C | HIS | B | 252 | −51.582 | −1.636 | −33.383 | 1.00 | 48.14 | C |
| ATOM | 11955 | O | HIS | B | 252 | −52.615 | −1.975 | −33.935 | 1.00 | 48.02 | O |
| ATOM | 11957 | N | PHE | B | 253 | −50.481 | −2.372 | −33.405 | 1.00 | 48.10 | N |
| ATOM | 11958 | CA | PHE | B | 253 | −50.422 | −3.702 | −34.044 | 1.00 | 48.18 | C |
| ATOM | 11960 | CB | PHE | B | 253 | −48.965 | −4.070 | −34.375 | 1.00 | 48.16 | C |
| ATOM | 11963 | CG | PHE | B | 253 | −48.119 | −4.311 | −33.163 | 1.00 | 47.85 | C |
| ATOM | 11964 | CD1 | PHE | B | 253 | −47.900 | −5.596 | −32.702 | 1.00 | 48.56 | C |
| ATOM | 11966 | CE1 | PHE | B | 253 | −47.140 | −5.812 | −31.576 | 1.00 | 48.98 | C |
| ATOM | 11968 | CZ | PHE | B | 253 | −46.602 | −4.729 | −30.895 | 1.00 | 48.50 | C |
| ATOM | 11970 | CE2 | PHE | B | 253 | −46.817 | −3.454 | −31.349 | 1.00 | 47.40 | C |
| ATOM | 11972 | CD2 | PHE | B | 253 | −47.569 | −3.249 | −32.465 | 1.00 | 47.22 | C |
| ATOM | 11974 | C | PHE | B | 253 | −51.038 | −4.819 | −33.185 | 1.00 | 48.30 | C |
| ATOM | 11975 | O | PHE | B | 253 | −51.344 | −5.903 | −33.691 | 1.00 | 47.63 | O |
| ATOM | 11977 | N | ALA | B | 254 | −51.204 | −4.541 | −31.888 | 1.00 | 48.86 | N |
| ATOM | 11978 | CA | ALA | B | 254 | −51.653 | −5.531 | −30.903 | 1.00 | 49.13 | C |
| ATOM | 11980 | CB | ALA | B | 254 | −51.290 | −5.071 | −29.494 | 1.00 | 49.02 | C |
| ATOM | 11984 | C | ALA | B | 254 | −53.153 | −5.806 | −30.982 | 1.00 | 49.46 | C |
| ATOM | 11985 | O | ALA | B | 254 | −53.967 | −4.870 | −31.011 | 1.00 | 49.50 | O |
| ATOM | 11987 | N | ARG | B | 255 | −53.501 | −7.097 | −31.006 | 1.00 | 49.75 | N |
| ATOM | 11988 | CA | ARG | B | 255 | −54.896 | −7.549 | −30.918 | 1.00 | 49.89 | C |
| ATOM | 11990 | CB | ARG | B | 255 | −55.028 | −9.051 | −31.245 | 1.00 | 49.94 | C |
| ATOM | 11993 | CG | ARG | B | 255 | −54.839 | −9.439 | −32.724 | 1.00 | 49.93 | C |
| ATOM | 11996 | CD | ARG | B | 255 | −54.709 | −10.967 | −32.904 | 1.00 | 49.79 | C |
| ATOM | 11999 | NE | ARG | B | 255 | −53.527 | −11.505 | −32.219 | 1.00 | 50.11 | N |
| ATOM | 12001 | CZ | ARG | B | 255 | −53.276 | −12.801 | −32.010 | 1.00 | 50.54 | C |
| ATOM | 12002 | NH1 | ARG | B | 255 | −54.117 | −13.736 | −32.439 | 1.00 | 51.36 | N |
| ATOM | 12005 | NH2 | ARG | B | 255 | −52.175 | −13.172 | −31.360 | 1.00 | 50.21 | N |
| ATOM | 12008 | C | ARG | B | 255 | −55.425 | −7.308 | −29.511 | 1.00 | 49.83 | C |
| ATOM | 12009 | O | ARG | B | 255 | −54.666 | −6.975 | −28.599 | 1.00 | 49.95 | O |
| ATOM | 12011 | N | ASP | B | 256 | −56.736 | −7.463 | −29.350 | 1.00 | 49.72 | N |
| ATOM | 12012 | CA | ASP | B | 256 | −57.360 | −7.483 | −28.034 | 1.00 | 49.55 | C |
| ATOM | 12014 | CB | ASP | B | 256 | −58.183 | −6.222 | −27.812 | 1.00 | 49.52 | C |
| ATOM | 12017 | CG | ASP | B | 256 | −59.134 | −6.362 | −26.654 | 1.00 | 50.30 | C |
| ATOM | 12018 | OD1 | ASP | B | 256 | −60.310 | −5.944 | −26.780 | 1.00 | 50.45 | O |
| ATOM | 12019 | OD2 | ASP | B | 256 | −58.702 | −6.926 | −25.622 | 1.00 | 51.68 | O |
| ATOM | 12020 | C | ASP | B | 256 | −58.254 | −8.721 | −27.931 | 1.00 | 49.15 | C |
| ATOM | 12021 | O | ASP | B | 256 | −59.159 | −8.901 | −28.737 | 1.00 | 49.28 | O |
| ATOM | 12023 | N | ARG | B | 257 | −57.998 | −9.565 | −26.937 | 1.00 | 48.61 | N |
| ATOM | 12024 | CA | ARG | B | 257 | −58.743 | −10.809 | −26.765 | 1.00 | 48.20 | C |
| ATOM | 12026 | CB | ARG | B | 257 | −57.949 | −11.984 | −27.373 | 1.00 | 48.41 | C |
| ATOM | 12029 | CG | ARG | B | 257 | −57.505 | −11.799 | −28.821 | 1.00 | 49.37 | C |
| ATOM | 12032 | CD | ARG | B | 257 | −58.693 | −11.636 | −29.784 | 1.00 | 50.80 | C |
| ATOM | 12035 | NE | ARG | B | 257 | −58.908 | −12.814 | −30.627 | 1.00 | 52.11 | N |
| ATOM | 12037 | CZ | ARG | B | 257 | −58.678 | −12.876 | −31.944 | 1.00 | 52.99 | C |
| ATOM | 12038 | NH1 | ARG | B | 257 | −58.214 | −11.820 | −32.623 | 1.00 | 52.37 | N |
| ATOM | 12041 | NH2 | ARG | B | 257 | −58.918 | −14.016 | −32.596 | 1.00 | 52.97 | N |
| ATOM | 12044 | C | ARG | B | 257 | −59.032 | −11.089 | −25.280 | 1.00 | 47.32 | C |
| ATOM | 12045 | O | ARG | B | 257 | −58.579 | −12.101 | −24.735 | 1.00 | 47.46 | O |
| ATOM | 12047 | N | LEU | B | 258 | −59.770 | −10.201 | −24.616 | 1.00 | 45.94 | N |
| ATOM | 12048 | CA | LEU | B | 258 | −60.108 | −10.430 | −23.205 | 1.00 | 44.67 | C |
| ATOM | 12050 | CB | LEU | B | 258 | −60.332 | −9.130 | −22.438 | 1.00 | 44.61 | C |
| ATOM | 12053 | CG | LEU | B | 258 | −60.422 | −9.323 | −20.920 | 1.00 | 43.83 | C |
| ATOM | 12055 | CD1 | LEU | B | 258 | −59.045 | −9.552 | −20.339 | 1.00 | 43.48 | C |
| ATOM | 12059 | CD2 | LEU | B | 258 | −61.073 | −8.139 | −20.262 | 1.00 | 43.85 | C |
| ATOM | 12063 | C | LEU | B | 258 | −61.347 | −11.286 | −23.090 | 1.00 | 43.49 | C |
| ATOM | 12064 | O | LEU | B | 258 | −61.375 | −12.220 | −22.295 | 1.00 | 43.84 | O |
| ATOM | 12066 | N | ILE | B | 259 | −62.364 | −10.968 | −23.883 | 1.00 | 41.92 | N |
| ATOM | 12067 | CA | ILE | B | 259 | −63.617 | −11.711 | −23.841 | 1.00 | 40.80 | C |
| ATOM | 12069 | CB | ILE | B | 259 | −64.718 | −11.132 | −24.783 | 1.00 | 41.05 | C |
| ATOM | 12071 | CG1 | ILE | B | 259 | −64.852 | −9.598 | −24.653 | 1.00 | 41.61 | C |
| ATOM | 12074 | CD1 | ILE | B | 259 | −65.200 | −8.874 | −25.985 | 1.00 | 42.16 | C |
| ATOM | 12078 | CG2 | ILE | B | 259 | −66.065 | −11.816 | −24.496 | 1.00 | 40.46 | C |
| ATOM | 12082 | C | ILE | B | 259 | −63.319 | −13.151 | −24.250 | 1.00 | 39.50 | C |
| ATOM | 12083 | O | ILE | B | 259 | −63.782 | −14.082 | −23.598 | 1.00 | 39.30 | O |
| ATOM | 12085 | N | GLU | B | 260 | −62.524 | −13.318 | −25.316 | 1.00 | 37.99 | N |
| ATOM | 12086 | CA | GLU | B | 260 | −62.120 | −14.652 | −25.812 | 1.00 | 36.60 | C |
| ATOM | 12088 | CB | GLU | B | 260 | −61.329 | −14.574 | −27.142 | 1.00 | 36.75 | C |
| ATOM | 12091 | CG | GLU | B | 260 | −62.167 | −14.319 | −28.425 | 1.00 | 37.79 | C |
| ATOM | 12094 | CD | GLU | B | 260 | −62.134 | −12.851 | −28.905 | 1.00 | 39.47 | C |
| ATOM | 12095 | OE1 | GLU | B | 260 | −62.207 | −11.923 | −28.055 | 1.00 | 39.97 | O |
| ATOM | 12096 | OE2 | GLU | B | 260 | −62.033 | −12.628 | −30.139 | 1.00 | 40.31 | O |
| ATOM | 12097 | C | GLU | B | 260 | −61.282 | −15.381 | −24.770 | 1.00 | 34.83 | C |
| ATOM | 12098 | O | GLU | B | 260 | −61.465 | −16.568 | −24.544 | 1.00 | 34.69 | O |
| ATOM | 12100 | N | SER | B | 261 | −60.365 | −14.669 | −24.131 | 1.00 | 32.89 | N |
| ATOM | 12101 | CA | SER | B | 261 | −59.508 | −15.292 | −23.139 | 1.00 | 31.48 | C |
| ATOM | 12103 | CB | SER | B | 261 | −58.341 | −14.376 | −22.768 | 1.00 | 31.55 | C |
| ATOM | 12106 | OG | SER | B | 261 | −57.298 | −14.493 | −23.728 | 1.00 | 31.75 | O |

TABLE 3-7-continued

Coordinates of *P. tremuloides IspS*

| | | | | | | | | | | | |
|---|---|---|---|---|---|---|---|---|---|---|---|
| ATOM | 12108 | C | SER | B | 261 | −60.294 | −15.716 | −21.900 | 1.00 | 30.04 | C |
| ATOM | 12109 | O | SER | B | 261 | −59.921 | −16.674 | −21.208 | 1.00 | 29.70 | O |
| ATOM | 12111 | N | PHE | B | 262 | −61.389 | −15.021 | −21.618 | 1.00 | 28.25 | N |
| ATOM | 12112 | CA | PHE | B | 262 | −62.203 | −15.404 | −20.480 | 1.00 | 26.75 | C |
| ATOM | 12114 | CB | PHE | B | 262 | −63.111 | −14.278 | −20.009 | 1.00 | 26.36 | C |
| ATOM | 12117 | CG | PHE | B | 262 | −63.532 | −14.453 | −18.603 | 1.00 | 24.33 | C |
| ATOM | 12118 | CD1 | PHE | B | 262 | −62.697 | −14.092 | −17.584 | 1.00 | 22.66 | C |
| ATOM | 12120 | CE1 | PHE | B | 262 | −63.047 | −14.283 | −16.301 | 1.00 | 22.65 | C |
| ATOM | 12122 | CZ | PHE | B | 262 | −64.245 | −14.873 | −16.007 | 1.00 | 23.93 | C |
| ATOM | 12124 | CE2 | PHE | B | 262 | −65.076 | −15.267 | −17.010 | 1.00 | 24.08 | C |
| ATOM | 12126 | CD2 | PHE | B | 262 | −64.711 | −15.067 | −18.304 | 1.00 | 23.96 | C |
| ATOM | 12128 | C | PHE | B | 262 | −63.017 | −16.660 | −20.751 | 1.00 | 26.02 | C |
| ATOM | 12129 | O | PHE | B | 262 | −63.074 | −17.546 | −19.909 | 1.00 | 26.32 | O |
| ATOM | 12131 | N | TYR | B | 263 | −63.652 | −16.732 | −21.915 | 1.00 | 24.98 | N |
| ATOM | 12132 | CA | TYR | B | 263 | −64.299 | −17.969 | −22.396 | 1.00 | 24.14 | C |
| ATOM | 12134 | CB | TYR | B | 263 | −64.701 | −17.756 | −23.853 | 1.00 | 24.00 | C |
| ATOM | 12137 | CG | TYR | B | 263 | −65.080 | −18.961 | −24.667 | 1.00 | 24.32 | C |
| ATOM | 12138 | CD1 | TYR | B | 263 | −66.302 | −19.604 | −24.489 | 1.00 | 25.03 | C |
| ATOM | 12140 | CE1 | TYR | B | 263 | −66.666 | −20.694 | −25.285 | 1.00 | 25.81 | C |
| ATOM | 12142 | CZ | TYR | B | 263 | −65.798 | −21.132 | −26.287 | 1.00 | 27.06 | C |
| ATOM | 12143 | OH | TYR | B | 263 | −66.106 | −22.191 | −27.123 | 1.00 | 27.14 | O |
| ATOM | 12145 | CE2 | TYR | B | 263 | −64.590 | −20.489 | −26.479 | 1.00 | 26.80 | C |
| ATOM | 12147 | CD2 | TYR | B | 263 | −64.250 | −19.404 | −25.680 | 1.00 | 25.65 | C |
| ATOM | 12149 | C | TYR | B | 263 | −63.351 | −19.162 | −22.256 | 1.00 | 23.35 | C |
| ATOM | 12150 | O | TYR | B | 263 | −63.712 | −20.219 | −21.740 | 1.00 | 22.80 | O |
| ATOM | 12152 | N | TRP | B | 264 | −62.119 | −18.955 | −22.702 | 1.00 | 22.64 | N |
| ATOM | 12153 | CA | TRP | B | 264 | −61.047 | −19.918 | −22.523 | 1.00 | 21.95 | C |
| ATOM | 12155 | CB | TRP | B | 264 | −59.737 | −19.334 | −23.061 | 1.00 | 21.84 | C |
| ATOM | 12158 | CG | TRP | B | 264 | −58.603 | −20.278 | −22.964 | 1.00 | 22.90 | C |
| ATOM | 12159 | CD1 | TRP | B | 264 | −57.700 | −20.387 | −21.943 | 1.00 | 23.98 | C |
| ATOM | 12161 | NE1 | TRP | B | 264 | −56.800 | −21.386 | −22.214 | 1.00 | 23.95 | N |
| ATOM | 12163 | CE2 | TRP | B | 264 | −57.124 | −21.949 | −23.417 | 1.00 | 23.51 | C |
| ATOM | 12164 | CD2 | TRP | B | 264 | −58.252 | −21.273 | −23.915 | 1.00 | 23.40 | C |
| ATOM | 12165 | CE3 | TRP | B | 264 | −58.776 | −21.652 | −25.147 | 1.00 | 23.68 | C |
| ATOM | 12167 | CZ3 | TRP | B | 264 | −58.178 | −22.669 | −25.826 | 1.00 | 24.44 | C |
| ATOM | 12169 | CH2 | TRP | B | 264 | −57.060 | −23.324 | −25.310 | 1.00 | 24.97 | C |
| ATOM | 12171 | CZ2 | TRP | B | 264 | −56.521 | −22.978 | −24.103 | 1.00 | 24.44 | C |
| ATOM | 12173 | C | TRP | B | 264 | −60.897 | −20.326 | −21.050 | 1.00 | 21.11 | C |
| ATOM | 12174 | O | TRP | B | 264 | −60.768 | −21.511 | −20.748 | 1.00 | 20.98 | O |
| ATOM | 12176 | N | ALA | B | 265 | −60.916 | −19.344 | −20.147 | 1.00 | 20.17 | N |
| ATOM | 12177 | CA | ALA | B | 265 | −60.774 | −19.602 | −18.712 | 1.00 | 19.36 | C |
| ATOM | 12179 | CB | ALA | B | 265 | −60.621 | −18.305 | −17.944 | 1.00 | 19.30 | C |
| ATOM | 12183 | C | ALA | B | 265 | −61.947 | −20.397 | −18.171 | 1.00 | 18.63 | C |
| ATOM | 12184 | O | ALA | B | 265 | −61.763 | −21.349 | −17.434 | 1.00 | 18.64 | O |
| ATOM | 12186 | N | VAL | B | 266 | −63.159 | −20.034 | −18.557 | 1.00 | 18.11 | N |
| ATOM | 12187 | CA | VAL | B | 266 | −64.335 | −20.758 | −18.075 | 1.00 | 17.60 | C |
| ATOM | 12189 | CB | VAL | B | 266 | −65.652 | −20.221 | −18.675 | 1.00 | 17.38 | C |
| ATOM | 12191 | CG1 | VAL | B | 266 | −65.902 | −18.803 | −18.199 | 1.00 | 17.09 | C |
| ATOM | 12195 | CG2 | VAL | B | 266 | −66.817 | −21.120 | −18.312 | 1.00 | 15.40 | C |
| ATOM | 12199 | C | VAL | B | 266 | −64.221 | −22.246 | −18.376 | 1.00 | 17.67 | C |
| ATOM | 12200 | O | VAL | B | 266 | −64.766 | −23.058 | −17.647 | 1.00 | 18.27 | O |
| ATOM | 12202 | N | GLY | B | 267 | −63.516 | −22.607 | −19.444 | 1.00 | 17.43 | N |
| ATOM | 12203 | CA | GLY | B | 267 | −63.316 | −24.013 | −19.789 | 1.00 | 16.98 | C |
| ATOM | 12206 | C | GLY | B | 267 | −62.253 | −24.683 | −18.947 | 1.00 | 16.55 | C |
| ATOM | 12207 | O | GLY | B | 267 | −62.360 | −25.859 | −18.609 | 1.00 | 16.37 | O |
| ATOM | 12209 | N | VAL | B | 268 | −61.215 | −23.939 | −18.608 | 1.00 | 16.30 | N |
| ATOM | 12210 | CA | VAL | B | 268 | −60.160 | −24.500 | −17.794 | 1.00 | 16.23 | C |
| ATOM | 12212 | CB | VAL | B | 268 | −58.893 | −23.651 | −17.840 | 1.00 | 15.68 | C |
| ATOM | 12214 | CG1 | VAL | B | 268 | −57.857 | −24.194 | −16.894 | 1.00 | 15.01 | C |
| ATOM | 12218 | CG2 | VAL | B | 268 | −58.361 | −23.674 | −19.235 | 1.00 | 15.01 | C |
| ATOM | 12222 | C | VAL | B | 268 | −60.654 | −24.718 | −16.374 | 1.00 | 16.86 | C |
| ATOM | 12223 | O | VAL | B | 268 | −60.421 | −25.784 | −15.813 | 1.00 | 16.93 | O |
| ATOM | 12225 | N | ALA | B | 269 | −61.362 | −23.733 | −15.817 | 1.00 | 17.64 | N |
| ATOM | 12226 | CA | ALA | B | 269 | −61.911 | −23.838 | −14.461 | 1.00 | 18.46 | C |
| ATOM | 12228 | CB | ALA | B | 269 | −60.958 | −23.215 | −13.472 | 1.00 | 18.15 | C |
| ATOM | 12232 | C | ALA | B | 269 | −63.312 | −23.213 | −14.340 | 1.00 | 19.34 | C |
| ATOM | 12233 | O | ALA | B | 269 | −63.448 | −22.030 | −14.047 | 1.00 | 19.78 | O |
| ATOM | 12235 | N | PHE | B | 270 | −64.347 | −24.028 | −14.529 | 1.00 | 20.34 | N |
| ATOM | 12236 | CA | PHE | B | 270 | −65.724 | −23.535 | −14.631 | 1.00 | 21.21 | C |
| ATOM | 12238 | CB | PHE | B | 270 | −66.564 | −24.483 | −15.482 | 1.00 | 21.34 | C |
| ATOM | 12241 | CG | PHE | B | 270 | −67.083 | −25.667 | −14.718 | 1.00 | 22.46 | C |
| ATOM | 12242 | CD1 | PHE | B | 270 | −68.294 | −25.596 | −14.039 | 1.00 | 23.19 | C |
| ATOM | 12244 | CE1 | PHE | B | 270 | −68.756 | −26.672 | −13.315 | 1.00 | 23.27 | C |
| ATOM | 12246 | CZ | PHE | B | 270 | −68.003 | −27.836 | −13.258 | 1.00 | 23.35 | C |
| ATOM | 12248 | CE2 | PHE | B | 270 | −66.794 | −27.918 | −13.932 | 1.00 | 22.73 | C |
| ATOM | 12250 | CD2 | PHE | B | 270 | −66.340 | −26.843 | −14.646 | 1.00 | 22.88 | C |
| ATOM | 12252 | C | PHE | B | 270 | −66.464 | −23.366 | −13.316 | 1.00 | 21.98 | C |
| ATOM | 12253 | O | PHE | B | 270 | −67.408 | −22.583 | −13.268 | 1.00 | 21.93 | O |

TABLE 3-7-continued

Coordinates of *P. tremuloides IspS*

| | | | | | | | | | | | |
|---|---|---|---|---|---|---|---|---|---|---|---|
| ATOM | 12255 | N | GLU | B | 271 | −66.102 | −24.126 | −12.275 | 1.00 | 23.01 | N |
| ATOM | 12256 | CA | GLU | B | 271 | −66.929 | −24.142 | −11.037 | 1.00 | 23.99 | C |
| ATOM | 12258 | CB | GLU | B | 271 | −66.679 | −25.353 | −10.113 | 1.00 | 24.25 | C |
| ATOM | 12261 | CG | GLU | B | 271 | −65.286 | −25.877 | −10.092 | 1.00 | 26.22 | C |
| ATOM | 12264 | CD | GLU | B | 271 | −65.013 | −26.914 | −11.183 | 1.00 | 29.01 | C |
| ATOM | 12265 | OE1 | GLU | B | 271 | −65.563 | −28.032 | −11.090 | 1.00 | 31.36 | O |
| ATOM | 12266 | OE2 | GLU | B | 271 | −64.232 | −26.622 | −12.121 | 1.00 | 30.98 | O |
| ATOM | 12267 | C | GLU | B | 271 | −66.795 | −22.831 | −10.281 | 1.00 | 23.90 | C |
| ATOM | 12268 | O | GLU | B | 271 | −65.702 | −22.296 | −10.181 | 1.00 | 24.29 | O |
| ATOM | 12270 | N | PRO | B | 272 | −67.913 | −22.316 | −9.745 | 1.00 | 24.09 | N |
| ATOM | 12271 | CA | PRO | B | 272 | −68.005 | −20.885 | −9.428 | 1.00 | 24.11 | C |
| ATOM | 12273 | CB | PRO | B | 272 | −69.380 | −20.751 | −8.751 | 1.00 | 24.03 | C |
| ATOM | 12276 | CG | PRO | B | 272 | −70.083 | −22.069 | −8.997 | 1.00 | 24.12 | C |
| ATOM | 12279 | CD | PRO | B | 272 | −69.013 | −23.083 | −9.132 | 1.00 | 23.99 | C |
| ATOM | 12282 | C | PRO | B | 272 | −66.900 | −20.386 | −8.501 | 1.00 | 24.28 | C |
| ATOM | 12283 | O | PRO | B | 272 | −66.421 | −19.261 | −8.676 | 1.00 | 24.40 | O |
| ATOM | 12284 | N | GLN | B | 273 | −66.480 | −21.222 | −7.547 | 1.00 | 24.20 | N |
| ATOM | 12285 | CA | GLN | B | 273 | −65.500 | −20.809 | −6.551 | 1.00 | 24.20 | C |
| ATOM | 12287 | CB | GLN | B | 273 | −65.437 | −21.840 | −5.426 | 1.00 | 24.42 | C |
| ATOM | 12290 | CG | GLN | B | 273 | −64.750 | −23.176 | −5.775 | 1.00 | 25.17 | C |
| ATOM | 12293 | CD | GLN | B | 273 | −65.717 | −24.334 | −6.007 | 1.00 | 26.13 | C |
| ATOM | 12294 | OE1 | GLN | B | 273 | −66.857 | −24.141 | −6.453 | 1.00 | 27.46 | O |
| ATOM | 12295 | NE2 | GLN | B | 273 | −65.251 | −25.554 | −5.721 | 1.00 | 25.05 | N |
| ATOM | 12298 | C | GLN | B | 273 | −64.086 | −20.546 | −7.088 | 1.00 | 24.27 | C |
| ATOM | 12299 | O | GLN | B | 273 | −63.221 | −20.151 | −6.329 | 1.00 | 24.32 | O |
| ATOM | 12301 | N | TYR | B | 274 | −63.842 | −20.759 | −8.380 | 1.00 | 24.59 | N |
| ATOM | 12302 | CA | TYR | B | 274 | −62.509 | −20.551 | −8.962 | 1.00 | 24.85 | C |
| ATOM | 12304 | CB | TYR | B | 274 | −62.129 | −21.724 | −9.880 | 1.00 | 24.62 | C |
| ATOM | 12307 | CG | TYR | B | 274 | −62.009 | −23.054 | −9.184 | 1.00 | 24.35 | C |
| ATOM | 12308 | CD1 | TYR | B | 274 | −61.395 | −23.169 | −7.946 | 1.00 | 24.62 | C |
| ATOM | 12310 | CE1 | TYR | B | 274 | −61.280 | −24.391 | −7.314 | 1.00 | 25.10 | C |
| ATOM | 12312 | CZ | TYR | B | 274 | −61.771 | −25.525 | −7.920 | 1.00 | 24.92 | C |
| ATOM | 12313 | OH | TYR | B | 274 | −61.661 | −26.748 | −7.299 | 1.00 | 24.73 | O |
| ATOM | 12315 | CE2 | TYR | B | 274 | −62.366 | −25.437 | −9.150 | 1.00 | 24.76 | C |
| ATOM | 12317 | CD2 | TYR | B | 274 | −62.477 | −24.203 | −9.779 | 1.00 | 24.70 | C |
| ATOM | 12319 | C | TYR | B | 274 | −62.409 | −19.235 | −9.745 | 1.00 | 25.27 | C |
| ATOM | 12320 | O | TYR | B | 274 | −61.956 | −19.210 | −10.895 | 1.00 | 25.42 | O |
| ATOM | 12322 | N | SER | B | 275 | −62.808 | −18.134 | −9.121 | 1.00 | 25.40 | N |
| ATOM | 12323 | CA | SER | B | 275 | −62.755 | −16.849 | −9.802 | 1.00 | 25.43 | C |
| ATOM | 12325 | CB | SER | B | 275 | −63.615 | −15.814 | −9.071 | 1.00 | 25.53 | C |
| ATOM | 12328 | OG | SER | B | 275 | −65.006 | −16.068 | −9.291 | 1.00 | 25.52 | O |
| ATOM | 12330 | C | SER | B | 275 | −61.300 | −16.403 | −9.948 | 1.00 | 25.36 | C |
| ATOM | 12331 | O | SER | B | 275 | −60.885 | −15.903 | −10.996 | 1.00 | 25.17 | O |
| ATOM | 12333 | N | ASP | B | 276 | −60.517 | −16.617 | −8.901 | 1.00 | 25.41 | N |
| ATOM | 12334 | CA | ASP | B | 276 | −59.095 | −16.353 | −8.979 | 1.00 | 25.42 | C |
| ATOM | 12336 | CB | ASP | B | 276 | −58.390 | −16.794 | −7.712 | 1.00 | 25.44 | C |
| ATOM | 12339 | CG | ASP | B | 276 | −58.728 | −15.925 | −6.558 | 1.00 | 26.32 | C |
| ATOM | 12340 | OD1 | ASP | B | 276 | −59.302 | −14.857 | −6.818 | 1.00 | 27.50 | O |
| ATOM | 12341 | OD2 | ASP | B | 276 | −58.442 | −16.299 | −5.398 | 1.00 | 30.16 | O |
| ATOM | 12342 | C | ASP | B | 276 | −58.495 | −17.069 | −10.157 | 1.00 | 25.20 | C |
| ATOM | 12343 | O | ASP | B | 276 | −57.745 | −16.461 | −10.929 | 1.00 | 25.66 | O |
| ATOM | 12345 | N | CYS | B | 277 | −58.814 | −18.353 | −10.305 | 1.00 | 24.60 | N |
| ATOM | 12346 | CA | CYS | B | 277 | −58.228 | −19.110 | −11.391 | 1.00 | 24.30 | C |
| ATOM | 12348 | CB | CYS | B | 277 | −58.684 | −20.561 | −11.392 | 1.00 | 24.28 | C |
| ATOM | 12351 | SG | CYS | B | 277 | −57.737 | −21.574 | −12.569 | 1.00 | 23.82 | S |
| ATOM | 12353 | C | CYS | B | 277 | −58.593 | −18.448 | −12.698 | 1.00 | 24.09 | C |
| ATOM | 12354 | O | CYS | B | 277 | −57.727 | −18.013 | −13.450 | 1.00 | 23.87 | O |
| ATOM | 12356 | N | ARG | B | 278 | −59.893 | −18.329 | −12.933 | 1.00 | 24.22 | N |
| ATOM | 12357 | CA | ARG | B | 278 | −60.400 | −17.746 | −14.171 | 1.00 | 23.98 | C |
| ATOM | 12359 | CB | ARG | B | 278 | −61.917 | −17.556 | −14.123 | 1.00 | 23.93 | C |
| ATOM | 12362 | CG | ARG | B | 278 | −62.662 | −18.871 | −14.283 | 1.00 | 24.07 | C |
| ATOM | 12365 | CD | ARG | B | 278 | −64.132 | −18.670 | −14.607 | 1.00 | 24.48 | C |
| ATOM | 12368 | NE | ARG | B | 278 | −64.874 | −18.141 | −13.472 | 1.00 | 23.75 | N |
| ATOM | 12370 | CZ | ARG | B | 278 | −65.254 | −18.856 | −12.419 | 1.00 | 23.72 | C |
| ATOM | 12371 | NH1 | ARG | B | 278 | −64.973 | −20.149 | −12.326 | 1.00 | 22.86 | N |
| ATOM | 12374 | NH2 | ARG | B | 278 | −65.927 | −18.262 | −11.443 | 1.00 | 25.08 | N |
| ATOM | 12377 | C | ARG | B | 278 | −59.701 | −16.453 | −14.491 | 1.00 | 23.56 | C |
| ATOM | 12378 | O | ARG | B | 278 | −59.296 | −16.265 | −15.628 | 1.00 | 23.87 | O |
| ATOM | 12380 | N | ASN | B | 279 | −59.512 | −15.593 | −13.495 | 1.00 | 23.24 | N |
| ATOM | 12381 | CA | ASN | B | 279 | −58.854 | −14.301 | −13.734 | 1.00 | 23.48 | C |
| ATOM | 12383 | CB | ASN | B | 279 | −59.055 | −13.340 | −12.574 | 1.00 | 24.05 | C |
| ATOM | 12386 | CG | ASN | B | 279 | −60.510 | −13.017 | −12.346 | 1.00 | 26.58 | C |
| ATOM | 12387 | OD1 | ASN | B | 279 | −61.378 | −13.310 | −13.189 | 1.00 | 28.96 | O |
| ATOM | 12388 | ND2 | ASN | B | 279 | −60.799 | −12.416 | −11.194 | 1.00 | 30.30 | N |
| ATOM | 12391 | C | ASN | B | 279 | −57.376 | −14.404 | −14.027 | 1.00 | 22.58 | C |
| ATOM | 12392 | O | ASN | B | 279 | −56.903 | −13.749 | −14.941 | 1.00 | 22.73 | O |
| ATOM | 12394 | N | SER | B | 280 | −56.648 | −15.205 | −13.251 | 1.00 | 21.62 | N |
| ATOM | 12395 | CA | SER | B | 280 | −55.243 | −15.483 | −13.550 | 1.00 | 20.73 | C |

TABLE 3-7-continued

Coordinates of *P. tremuloides IspS*

| | | | | | | | | | | | |
|---|---|---|---|---|---|---|---|---|---|---|---|
| ATOM | 12397 | CB | SER | B | 280 | −54.696 | −16.597 | −12.659 | 1.00 | 20.85 | C |
| ATOM | 12400 | OG | SER | B | 280 | −53.805 | −16.099 | −11.683 | 1.00 | 21.55 | O |
| ATOM | 12402 | C | SER | B | 280 | −55.091 | −15.896 | −15.004 | 1.00 | 20.04 | C |
| ATOM | 12403 | O | SER | B | 280 | −54.293 | −15.312 | −15.738 | 1.00 | 19.87 | O |
| ATOM | 12405 | N | VAL | B | 281 | −55.875 | −16.893 | −15.413 | 1.00 | 19.24 | N |
| ATOM | 12406 | CA | VAL | B | 281 | −55.720 | −17.491 | −16.720 | 1.00 | 18.77 | C |
| ATOM | 12408 | CB | VAL | B | 281 | −56.482 | −18.834 | −16.815 | 1.00 | 18.74 | C |
| ATOM | 12410 | CG1 | VAL | B | 281 | −56.467 | −19.404 | −18.251 | 1.00 | 18.34 | C |
| ATOM | 12414 | CG2 | VAL | B | 281 | −55.863 | −19.844 | −15.848 | 1.00 | 18.13 | C |
| ATOM | 12418 | C | VAL | B | 281 | −56.142 | −16.486 | −17.787 | 1.00 | 18.89 | C |
| ATOM | 12419 | O | VAL | B | 281 | −55.483 | −16.364 | −18.832 | 1.00 | 18.75 | O |
| ATOM | 12421 | N | ALA | B | 282 | −57.210 | −15.739 | −17.505 | 1.00 | 18.85 | N |
| ATOM | 12422 | CA | ALA | B | 282 | −57.709 | −14.723 | −18.439 | 1.00 | 18.80 | C |
| ATOM | 12424 | CB | ALA | B | 282 | −59.051 | −14.191 | −17.991 | 1.00 | 18.32 | C |
| ATOM | 12428 | C | ALA | B | 282 | −56.718 | −13.576 | −18.615 | 1.00 | 18.94 | C |
| ATOM | 12429 | O | ALA | B | 282 | −56.582 | −13.021 | −19.700 | 1.00 | 19.16 | O |
| ATOM | 12431 | N | LYS | B | 283 | −56.022 | −13.211 | −17.553 | 1.00 | 19.24 | N |
| ATOM | 12432 | CA | LYS | B | 283 | −55.037 | −12.145 | −17.658 | 1.00 | 19.62 | C |
| ATOM | 12434 | CB | LYS | B | 283 | −54.649 | −11.615 | −16.276 | 1.00 | 19.68 | C |
| ATOM | 12437 | CG | LYS | B | 283 | −55.779 | −10.923 | −15.518 | 1.00 | 19.95 | C |
| ATOM | 12440 | CD | LYS | B | 283 | −55.265 | −10.398 | −14.196 | 1.00 | 21.72 | C |
| ATOM | 12443 | CE | LYS | B | 283 | −56.364 | −10.236 | −13.164 | 1.00 | 23.83 | C |
| ATOM | 12446 | NZ | LYS | B | 283 | −56.129 | −9.003 | −12.351 | 1.00 | 24.72 | N |
| ATOM | 12450 | C | LYS | B | 283 | −53.802 | −12.643 | −18.396 | 1.00 | 19.77 | C |
| ATOM | 12451 | O | LYS | B | 283 | −53.237 | −11.929 | −19.208 | 1.00 | 20.05 | O |
| ATOM | 12453 | N | MET | B | 284 | −53.387 | −13.871 | −18.117 | 1.00 | 19.88 | N |
| ATOM | 12454 | CA | MET | B | 284 | −52.136 | −14.367 | −18.652 | 1.00 | 19.90 | C |
| ATOM | 12456 | CB | MET | B | 284 | −51.719 | −15.676 | −17.960 | 1.00 | 20.08 | C |
| ATOM | 12459 | CG | MET | B | 284 | −51.125 | −15.505 | −16.560 | 1.00 | 20.62 | C |
| ATOM | 12462 | SD | MET | B | 284 | −49.782 | −14.295 | −16.485 | 1.00 | 23.69 | S |
| ATOM | 12463 | CE | MET | B | 284 | −50.600 | −12.872 | −15.754 | 1.00 | 23.82 | C |
| ATOM | 12467 | C | MET | B | 284 | −52.257 | −14.572 | −20.145 | 1.00 | 19.82 | C |
| ATOM | 12468 | O | MET | B | 284 | −51.326 | −14.269 | −20.889 | 1.00 | 20.21 | O |
| ATOM | 12470 | N | PHE | B | 285 | −53.401 | −15.088 | −20.579 | 1.00 | 19.72 | N |
| ATOM | 12471 | CA | PHE | B | 285 | −53.620 | −15.428 | −21.986 | 1.00 | 19.66 | C |
| ATOM | 12473 | CB | PHE | B | 285 | −54.863 | −16.324 | −22.114 | 1.00 | 20.09 | C |
| ATOM | 12476 | CG | PHE | B | 285 | −54.986 | −17.077 | −23.427 | 1.00 | 21.18 | C |
| ATOM | 12477 | CD1 | PHE | B | 285 | −53.877 | −17.362 | −24.232 | 1.00 | 22.86 | C |
| ATOM | 12479 | CE1 | PHE | B | 285 | −54.013 | −18.070 | −25.424 | 1.00 | 22.58 | C |
| ATOM | 12481 | CZ | PHE | B | 285 | −55.254 | −18.518 | −25.806 | 1.00 | 23.49 | C |
| ATOM | 12483 | CE2 | PHE | B | 285 | −56.365 | −18.254 | −25.002 | 1.00 | 23.36 | C |
| ATOM | 12485 | CD2 | PHE | B | 285 | −56.222 | −17.551 | −23.823 | 1.00 | 21.76 | C |
| ATOM | 12487 | C | PHE | B | 285 | −53.781 | −14.148 | −22.781 | 1.00 | 19.18 | C |
| ATOM | 12488 | O | PHE | B | 285 | −53.333 | −14.046 | −23.914 | 1.00 | 18.98 | O |
| ATOM | 12490 | N | SER | B | 286 | −54.410 | −13.161 | −22.164 | 1.00 | 18.92 | N |
| ATOM | 12491 | CA | SER | B | 286 | −54.488 | −11.843 | −22.753 | 1.00 | 19.15 | C |
| ATOM | 12493 | CB | SER | B | 286 | −55.292 | −10.894 | −21.863 | 1.00 | 19.38 | C |
| ATOM | 12496 | OG | SER | B | 286 | −56.684 | −11.180 | −21.957 | 1.00 | 20.24 | O |
| ATOM | 12498 | C | SER | B | 286 | −53.106 | −11.267 | −23.032 | 1.00 | 18.91 | C |
| ATOM | 12499 | O | SER | B | 286 | −52.894 | −10.668 | −24.087 | 1.00 | 19.48 | O |
| ATOM | 12501 | N | PHE | B | 287 | −52.172 | −11.446 | −22.102 | 1.00 | 18.48 | N |
| ATOM | 12502 | CA | PHE | B | 287 | −50.768 | −11.065 | −22.339 | 1.00 | 18.30 | C |
| ATOM | 12504 | CB | PHE | B | 287 | −49.958 | −11.035 | −21.044 | 1.00 | 18.27 | C |
| ATOM | 12507 | CG | PHE | B | 287 | −50.040 | −9.740 | −20.324 | 1.00 | 18.59 | C |
| ATOM | 12508 | CD1 | PHE | B | 287 | −49.375 | −8.624 | −20.813 | 1.00 | 20.02 | C |
| ATOM | 12510 | CE1 | PHE | B | 287 | −49.456 | −7.410 | −20.152 | 1.00 | 20.57 | C |
| ATOM | 12512 | CZ | PHE | B | 287 | −50.208 | −7.308 | −18.985 | 1.00 | 20.02 | C |
| ATOM | 12514 | CE2 | PHE | B | 287 | −50.869 | −8.417 | −18.503 | 1.00 | 19.78 | C |
| ATOM | 12516 | CD2 | PHE | B | 287 | −50.781 | −9.623 | −19.164 | 1.00 | 19.05 | C |
| ATOM | 12518 | C | PHE | B | 287 | −50.067 | −11.978 | −23.339 | 1.00 | 18.01 | C |
| ATOM | 12519 | O | PHE | B | 287 | −49.374 | −11.498 | −24.229 | 1.00 | 18.00 | O |
| ATOM | 12521 | N | VAL | B | 288 | −50.236 | −13.286 | −23.194 | 1.00 | 17.69 | N |
| ATOM | 12522 | CA | VAL | B | 288 | −49.720 | −14.206 | −24.197 | 1.00 | 17.66 | C |
| ATOM | 12524 | CB | VAL | B | 288 | −50.168 | −15.649 | −23.930 | 1.00 | 17.37 | C |
| ATOM | 12526 | CG1 | VAL | B | 288 | −49.937 | −16.529 | −25.134 | 1.00 | 16.24 | C |
| ATOM | 12530 | CG2 | VAL | B | 288 | −49.414 | −16.185 | −22.758 | 1.00 | 17.21 | C |
| ATOM | 12534 | C | VAL | B | 288 | −50.081 | −13.761 | −25.633 | 1.00 | 18.08 | C |
| ATOM | 12535 | O | VAL | B | 288 | −49.207 | −13.710 | −26.492 | 1.00 | 18.08 | O |
| ATOM | 12537 | N | THR | B | 289 | −51.327 | −13.396 | −25.895 | 1.00 | 18.42 | N |
| ATOM | 12538 | CA | THR | B | 289 | −51.683 | −13.001 | −27.256 | 1.00 | 19.33 | C |
| ATOM | 12540 | CB | THR | B | 289 | −53.171 | −12.736 | −27.401 | 1.00 | 19.35 | C |
| ATOM | 12542 | OG1 | THR | B | 289 | −53.573 | −11.895 | −26.321 | 1.00 | 21.59 | O |
| ATOM | 12544 | CG2 | THR | B | 289 | −53.973 | −14.046 | −27.350 | 1.00 | 19.09 | C |
| ATOM | 12548 | C | THR | B | 289 | −50.901 | −11.766 | −27.723 | 1.00 | 19.71 | C |
| ATOM | 12549 | O | THR | B | 289 | −50.469 | −11.707 | −28.891 | 1.00 | 19.88 | O |
| ATOM | 12551 | N | ILE | B | 290 | −50.689 | −10.796 | −26.829 | 1.00 | 19.94 | N |
| ATOM | 12552 | CA | ILE | B | 290 | −49.943 | −9.585 | −27.225 | 1.00 | 20.39 | C |
| ATOM | 12554 | CB | ILE | B | 290 | −50.069 | −8.410 | −26.221 | 1.00 | 20.50 | C |

TABLE 3-7-continued

| Coordinates of *P. tremuloides IspS* | | | | | | | | | | | |
|---|---|---|---|---|---|---|---|---|---|---|---|
| ATOM | 12556 | CG1 | ILE | B | 290 | −51.510 | −8.137 | −25.823 | 1.00 | 21.25 | C |
| ATOM | 12559 | CD1 | ILE | B | 290 | −51.650 | −6.854 | −25.002 | 1.00 | 21.58 | C |
| ATOM | 12563 | CG2 | ILE | B | 290 | −49.546 | −7.134 | −26.853 | 1.00 | 20.39 | C |
| ATOM | 12567 | C | ILE | B | 290 | −48.434 | −9.840 | −27.438 | 1.00 | 20.45 | C |
| ATOM | 12568 | O | ILE | B | 290 | −47.853 | −9.317 | −28.393 | 1.00 | 20.76 | O |
| ATOM | 12570 | N | ILE | B | 291 | −47.808 | −10.616 | −26.546 | 1.00 | 20.21 | N |
| ATOM | 12571 | CA | ILE | B | 291 | −46.375 | −10.869 | −26.618 | 1.00 | 19.87 | C |
| ATOM | 12573 | CB | ILE | B | 291 | −45.840 | −11.603 | −25.407 | 1.00 | 19.79 | C |
| ATOM | 12575 | CG1 | ILE | B | 291 | −46.205 | −10.879 | −24.102 | 1.00 | 19.71 | C |
| ATOM | 12578 | CD1 | ILE | B | 291 | −45.326 | −9.734 | −23.748 | 1.00 | 19.77 | C |
| ATOM | 12582 | CG2 | ILE | B | 291 | −44.336 | −11.747 | −25.516 | 1.00 | 18.91 | C |
| ATOM | 12586 | C | ILE | B | 291 | −46.134 | −11.735 | −27.825 | 1.00 | 20.44 | C |
| ATOM | 12587 | O | ILE | B | 291 | −45.233 | −11.481 | −28.600 | 1.00 | 20.35 | O |
| ATOM | 12589 | N | ASP | B | 292 | −46.965 | −12.751 | −28.005 | 1.00 | 21.33 | N |
| ATOM | 12590 | CA | ASP | B | 292 | −46.915 | −13.563 | −29.228 | 1.00 | 22.13 | C |
| ATOM | 12592 | CB | ASP | B | 292 | −48.120 | −14.508 | −29.316 | 1.00 | 22.40 | C |
| ATOM | 12595 | CG | ASP | B | 292 | −47.847 | −15.741 | −30.160 | 1.00 | 23.47 | C |
| ATOM | 12596 | OD1 | ASP | B | 292 | −46.852 | −15.765 | −30.923 | 1.00 | 24.83 | O |
| ATOM | 12597 | OD2 | ASP | B | 292 | −48.637 | −16.707 | −30.038 | 1.00 | 25.22 | O |
| ATOM | 12598 | C | ASP | B | 292 | −46.856 | −12.716 | −30.507 | 1.00 | 22.28 | C |
| ATOM | 12599 | O | ASP | B | 292 | −46.088 | −13.033 | −31.399 | 1.00 | 22.73 | O |
| ATOM | 12601 | N | ASP | B | 293 | −47.656 | −11.658 | −30.611 | 1.00 | 22.22 | N |
| ATOM | 12602 | CA | ASP | B | 293 | −47.630 | −10.828 | −31.822 | 1.00 | 22.43 | C |
| ATOM | 12604 | CB | ASP | B | 293 | −48.840 | −9.894 | −31.885 | 1.00 | 23.03 | C |
| ATOM | 12607 | CG | ASP | B | 293 | −50.157 | −10.644 | −31.959 | 1.00 | 24.69 | C |
| ATOM | 12608 | OD1 | ASP | B | 293 | −50.113 | −11.900 | −32.025 | 1.00 | 28.66 | O |
| ATOM | 12609 | OD2 | ASP | B | 293 | −51.231 | −9.986 | −31.930 | 1.00 | 23.57 | O |
| ATOM | 12610 | C | ASP | B | 293 | −46.354 | −9.997 | −31.921 | 1.00 | 21.94 | C |
| ATOM | 12611 | O | ASP | B | 293 | −45.898 | −9.674 | −33.019 | 1.00 | 22.31 | O |
| ATOM | 12613 | N | ILE | B | 294 | −45.783 | −9.643 | −30.780 | 1.00 | 21.05 | N |
| ATOM | 12614 | CA | ILE | B | 294 | −44.513 | −8.941 | −30.770 | 1.00 | 20.53 | C |
| ATOM | 12616 | CB | ILE | B | 294 | −44.166 | −8.448 | −29.344 | 1.00 | 20.42 | C |
| ATOM | 12618 | CG1 | ILE | B | 294 | −45.150 | −7.349 | −28.945 | 1.00 | 19.66 | C |
| ATOM | 12621 | CD1 | ILE | B | 294 | −45.057 | −6.956 | −27.536 | 1.00 | 18.81 | C |
| ATOM | 12625 | CG2 | ILE | B | 294 | −42.726 | −7.924 | −29.253 | 1.00 | 19.99 | C |
| ATOM | 12629 | C | ILE | B | 294 | −43.416 | −9.845 | −31.343 | 1.00 | 20.44 | C |
| ATOM | 12630 | O | ILE | B | 294 | −42.650 | −9.431 | −32.205 | 1.00 | 20.17 | O |
| ATOM | 12632 | N | TYR | B | 295 | −43.355 | −11.088 | −30.886 | 1.00 | 20.65 | N |
| ATOM | 12633 | CA | TYR | B | 295 | −42.313 | −12.008 | −31.353 | 1.00 | 20.76 | C |
| ATOM | 12635 | CB | TYR | B | 295 | −42.145 | −13.198 | −30.412 | 1.00 | 20.29 | C |
| ATOM | 12638 | CG | TYR | B | 295 | −41.393 | −12.926 | −29.129 | 1.00 | 17.92 | C |
| ATOM | 12639 | CD1 | TYR | B | 295 | −40.117 | −13.409 | −28.936 | 1.00 | 17.62 | C |
| ATOM | 12641 | CE1 | TYR | B | 295 | −39.427 | −13.195 | −27.747 | 1.00 | 17.12 | C |
| ATOM | 12643 | CZ | TYR | B | 295 | −40.022 | −12.493 | −26.730 | 1.00 | 16.61 | C |
| ATOM | 12644 | OH | TYR | B | 295 | −39.357 | −12.281 | −25.528 | 1.00 | 14.46 | O |
| ATOM | 12646 | CE2 | TYR | B | 295 | −41.296 | −12.008 | −26.911 | 1.00 | 16.82 | C |
| ATOM | 12648 | CD2 | TYR | B | 295 | −41.972 | −12.235 | −28.102 | 1.00 | 16.39 | C |
| ATOM | 12650 | C | TYR | B | 295 | −42.619 | −12.519 | −32.749 | 1.00 | 21.65 | C |
| ATOM | 12651 | O | TYR | B | 295 | −41.698 | −12.751 | −33.540 | 1.00 | 22.13 | O |
| ATOM | 12653 | N | ASP | B | 296 | −43.905 | −12.677 | −33.049 | 1.00 | 22.47 | N |
| ATOM | 12654 | CA | ASP | B | 296 | −44.327 | −13.316 | −34.285 | 1.00 | 23.52 | C |
| ATOM | 12656 | CB | ASP | B | 296 | −45.761 | −13.851 | −34.185 | 1.00 | 23.99 | C |
| ATOM | 12659 | CG | ASP | B | 296 | −46.134 | −14.744 | −35.369 | 1.00 | 26.22 | C |
| ATOM | 12660 | OD1 | ASP | B | 296 | −45.508 | −15.832 | −35.538 | 1.00 | 27.70 | O |
| ATOM | 12661 | OD2 | ASP | B | 296 | −47.052 | −14.348 | −36.128 | 1.00 | 28.78 | O |
| ATOM | 12662 | C | ASP | B | 296 | −44.228 | −12.392 | −35.478 | 1.00 | 23.68 | C |
| ATOM | 12663 | O | ASP | B | 296 | −43.673 | −12.784 | −36.502 | 1.00 | 24.01 | O |
| ATOM | 12665 | N | VAL | B | 297 | −44.765 | −11.178 | −35.364 | 1.00 | 23.90 | N |
| ATOM | 12666 | CA | VAL | B | 297 | −44.801 | −10.273 | −36.524 | 1.00 | 23.99 | C |
| ATOM | 12668 | CB | VAL | B | 297 | −46.251 | −10.003 | −36.973 | 1.00 | 23.87 | C |
| ATOM | 12670 | CG1 | VAL | B | 297 | −46.949 | −11.310 | −37.197 | 1.00 | 23.75 | C |
| ATOM | 12674 | CG2 | VAL | B | 297 | −47.002 | −9.136 | −35.966 | 1.00 | 23.05 | C |
| ATOM | 12678 | C | VAL | B | 297 | −44.060 | −8.940 | −36.383 | 1.00 | 24.27 | C |
| ATOM | 12679 | O | VAL | B | 297 | −43.485 | −8.465 | −37.342 | 1.00 | 23.84 | O |
| ATOM | 12681 | N | TYR | B | 298 | −44.058 | −8.347 | −35.199 | 1.00 | 24.87 | N |
| ATOM | 12682 | CA | TYR | B | 298 | −43.760 | −6.926 | −35.078 | 1.00 | 25.67 | C |
| ATOM | 12684 | CB | TYR | B | 298 | −44.656 | −6.294 | −34.010 | 1.00 | 26.06 | C |
| ATOM | 12687 | CG | TYR | B | 298 | −44.520 | −4.789 | −33.932 | 1.00 | 27.95 | C |
| ATOM | 12688 | CD1 | TYR | B | 298 | −45.097 | −3.968 | −34.901 | 1.00 | 29.74 | C |
| ATOM | 12690 | CE1 | TYR | B | 298 | −44.982 | −2.574 | −34.843 | 1.00 | 29.93 | C |
| ATOM | 12692 | CZ | TYR | B | 298 | −44.282 | −1.991 | −33.806 | 1.00 | 29.96 | C |
| ATOM | 12693 | OH | TYR | B | 298 | −44.165 | −.631 | −33.746 | 1.00 | 30.01 | O |
| ATOM | 12695 | CE2 | TYR | B | 298 | −43.697 | −2.777 | −32.829 | 1.00 | 30.39 | C |
| ATOM | 12697 | CD2 | TYR | B | 298 | −43.811 | −4.181 | −32.899 | 1.00 | 29.96 | C |
| ATOM | 12699 | C | TYR | B | 298 | −42.318 | −6.592 | −34.755 | 1.00 | 25.76 | C |
| ATOM | 12700 | O | TYR | B | 298 | −41.696 | −5.830 | −35.470 | 1.00 | 26.54 | O |
| ATOM | 12702 | N | GLY | B | 299 | −41.798 | −7.111 | −33.653 | 1.00 | 25.89 | N |
| ATOM | 12703 | CA | GLY | B | 299 | −40.473 | −6.706 | −33.167 | 1.00 | 25.78 | C |

TABLE 3-7-continued

Coordinates of *P. tremuloides IspS*

| | | | | | | | | | | | |
|---|---|---|---|---|---|---|---|---|---|---|---|
| ATOM | 12706 | C | GLY | B | 299 | −39.346 | −7.341 | −33.951 | 1.00 | 25.52 | C |
| ATOM | 12707 | O | GLY | B | 299 | −39.513 | −8.410 | −34.525 | 1.00 | 26.04 | O |
| ATOM | 12709 | N | THR | B | 300 | −38.196 | −6.685 | −33.990 | 1.00 | 25.32 | N |
| ATOM | 12710 | CA | THR | B | 300 | −37.063 | −7.237 | −34.716 | 1.00 | 25.16 | C |
| ATOM | 12712 | CB | THR | B | 300 | −36.088 | −6.164 | −35.295 | 1.00 | 25.08 | C |
| ATOM | 12714 | OG1 | THR | B | 300 | −35.191 | −5.710 | −34.281 | 1.00 | 25.07 | O |
| ATOM | 12716 | CG2 | THR | B | 300 | −36.833 | −4.978 | −35.875 | 1.00 | 25.08 | C |
| ATOM | 12720 | C | THR | B | 300 | −36.324 | −8.139 | −33.771 | 1.00 | 25.13 | C |
| ATOM | 12721 | O | THR | B | 300 | −36.335 | −7.950 | −32.570 | 1.00 | 25.28 | O |
| ATOM | 12723 | N | LEU | B | 301 | −35.662 | −9.129 | −34.332 | 1.00 | 25.50 | N |
| ATOM | 12724 | CA | LEU | B | 301 | −34.918 | −10.093 | −33.538 | 1.00 | 25.42 | C |
| ATOM | 12726 | CB | LEU | B | 301 | −34.148 | −11.020 | −34.479 | 1.00 | 25.17 | C |
| ATOM | 12729 | CG | LEU | B | 301 | −33.624 | −12.338 | −33.941 | 1.00 | 24.95 | C |
| ATOM | 12731 | CD1 | LEU | B | 301 | −34.715 | −13.233 | −33.437 | 1.00 | 24.42 | C |
| ATOM | 12735 | CD2 | LEU | B | 301 | −32.900 | −12.998 | −35.080 | 1.00 | 26.50 | C |
| ATOM | 12739 | C | LEU | B | 301 | −33.995 | −9.425 | −32.485 | 1.00 | 25.54 | C |
| ATOM | 12740 | O | LEU | B | 301 | −33.843 | −9.959 | −31.394 | 1.00 | 25.35 | O |
| ATOM | 12742 | N | ASP | B | 302 | −33.417 | −8.257 | −32.782 | 1.00 | 25.68 | N |
| ATOM | 12743 | CA | ASP | B | 302 | −32.598 | −7.550 | −31.774 | 1.00 | 26.02 | C |
| ATOM | 12745 | CB | ASP | B | 302 | −31.800 | −6.377 | −32.378 | 1.00 | 26.37 | C |
| ATOM | 12748 | CG | ASP | B | 302 | −30.563 | −6.833 | −33.167 | 1.00 | 28.27 | C |
| ATOM | 12749 | OD1 | ASP | B | 302 | −29.508 | −6.156 | −33.048 | 1.00 | 29.05 | O |
| ATOM | 12750 | OD2 | ASP | B | 302 | −30.652 | −7.852 | −33.910 | 1.00 | 31.04 | O |
| ATOM | 12751 | C | ASP | B | 302 | −33.472 | −7.037 | −30.630 | 1.00 | 25.69 | C |
| ATOM | 12752 | O | ASP | B | 302 | −33.110 | −7.142 | −29.447 | 1.00 | 25.90 | O |
| ATOM | 12754 | N | GLU | B | 303 | −34.622 | −6.473 | −30.993 | 1.00 | 25.04 | N |
| ATOM | 12755 | CA | GLU | B | 303 | −35.600 | −6.029 | −30.011 | 1.00 | 24.33 | C |
| ATOM | 12757 | CB | GLU | B | 303 | −36.783 | −5.346 | −30.697 | 1.00 | 24.20 | C |
| ATOM | 12760 | CG | GLU | B | 303 | −36.399 | −4.109 | −31.466 | 1.00 | 24.23 | C |
| ATOM | 12763 | CD | GLU | B | 303 | −37.589 | −3.382 | −32.063 | 1.00 | 24.23 | C |
| ATOM | 12764 | OE1 | GLU | B | 303 | −38.496 | −4.065 | −32.604 | 1.00 | 22.66 | O |
| ATOM | 12765 | OE2 | GLU | B | 303 | −37.592 | −2.121 | −31.995 | 1.00 | 23.93 | O |
| ATOM | 12766 | C | GLU | B | 303 | −36.103 | −7.212 | −29.193 | 1.00 | 23.87 | C |
| ATOM | 12767 | O | GLU | B | 303 | −36.396 | −7.058 | −28.011 | 1.00 | 23.59 | O |
| ATOM | 12769 | N | LEU | B | 304 | −36.204 | −8.383 | −29.825 | 1.00 | 23.39 | N |
| ATOM | 12770 | CA | LEU | B | 304 | −36.766 | −9.570 | −29.166 | 1.00 | 23.23 | C |
| ATOM | 12772 | CB | LEU | B | 304 | −37.180 | −10.624 | −30.208 | 1.00 | 22.83 | C |
| ATOM | 12775 | CG | LEU | B | 304 | −38.381 | −10.217 | −31.074 | 1.00 | 22.06 | C |
| ATOM | 12777 | CD1 | LEU | B | 304 | −38.822 | −11.321 | −32.037 | 1.00 | 20.11 | C |
| ATOM | 12781 | CD2 | LEU | B | 304 | −39.551 | −9.800 | −30.163 | 1.00 | 21.94 | C |
| ATOM | 12785 | C | LEU | B | 304 | −35.810 | −10.147 | −28.106 | 1.00 | 23.37 | C |
| ATOM | 12786 | O | LEU | B | 304 | −36.248 | −10.785 | −27.141 | 1.00 | 23.22 | O |
| ATOM | 12788 | N | GLU | B | 305 | −34.514 | −9.892 | −28.283 | 1.00 | 23.30 | N |
| ATOM | 12789 | CA | GLU | B | 305 | −33.512 | −10.308 | −27.324 | 1.00 | 23.18 | C |
| ATOM | 12791 | CB | GLU | B | 305 | −32.114 | −10.176 | −27.899 | 1.00 | 23.58 | C |
| ATOM | 12794 | CG | GLU | B | 305 | −31.832 | −11.142 | −29.047 | 1.00 | 25.27 | C |
| ATOM | 12797 | CD | GLU | B | 305 | −31.306 | −12.488 | −28.585 | 1.00 | 27.91 | C |
| ATOM | 12798 | OE1 | GLU | B | 305 | −30.946 | −13.303 | −29.470 | 1.00 | 29.87 | O |
| ATOM | 12799 | OE2 | GLU | B | 305 | −31.244 | −12.728 | −27.351 | 1.00 | 29.28 | O |
| ATOM | 12800 | C | GLU | B | 305 | −33.633 | −9.440 | −26.104 | 1.00 | 22.52 | C |
| ATOM | 12801 | O | GLU | B | 305 | −33.793 | −9.956 | −25.005 | 1.00 | 23.39 | O |
| ATOM | 12803 | N | LEU | B | 306 | −33.576 | −8.124 | −26.274 | 1.00 | 21.51 | N |
| ATOM | 12804 | CA | LEU | B | 306 | −33.715 | −7.224 | −25.114 | 1.00 | 20.70 | C |
| ATOM | 12806 | CB | LEU | B | 306 | −33.899 | −5.764 | −25.544 | 1.00 | 20.59 | C |
| ATOM | 12809 | CG | LEU | B | 306 | −32.769 | −5.065 | −26.293 | 1.00 | 20.12 | C |
| ATOM | 12811 | CD1 | LEU | B | 306 | −32.992 | −3.576 | −26.203 | 1.00 | 19.89 | C |
| ATOM | 12815 | CD2 | LEU | B | 306 | −31.402 | −5.437 | −25.739 | 1.00 | 19.81 | C |
| ATOM | 12819 | C | LEU | B | 306 | −34.896 | −7.645 | −24.237 | 1.00 | 19.91 | C |
| ATOM | 12820 | O | LEU | B | 306 | −34.771 | −7.778 | −23.031 | 1.00 | 19.53 | O |
| ATOM | 12822 | N | PHE | B | 307 | −36.030 | −7.883 | −24.872 | 1.00 | 19.48 | N |
| ATOM | 12823 | CA | PHE | B | 307 | −37.231 | −8.267 | −24.170 | 1.00 | 19.36 | C |
| ATOM | 12825 | CB | PHE | B | 307 | −38.400 | −8.406 | −25.138 | 1.00 | 19.54 | C |
| ATOM | 12828 | CG | PHE | B | 307 | −39.729 | −8.296 | −24.482 | 1.00 | 19.66 | C |
| ATOM | 12829 | CD1 | PHE | B | 307 | −40.365 | −7.079 | −24.400 | 1.00 | 21.03 | C |
| ATOM | 12831 | CE1 | PHE | B | 307 | −41.590 | −6.968 | −23.787 | 1.00 | 21.62 | C |
| ATOM | 12833 | CZ | PHE | B | 307 | −42.182 | −8.072 | −23.248 | 1.00 | 20.25 | C |
| ATOM | 12835 | CE2 | PHE | B | 307 | −41.553 | −9.292 | −23.329 | 1.00 | 20.07 | C |
| ATOM | 12837 | CD2 | PHE | B | 307 | −40.338 | −9.400 | −23.939 | 1.00 | 19.62 | C |
| ATOM | 12839 | C | PHE | B | 307 | −37.039 | −9.577 | −23.443 | 1.00 | 19.22 | C |
| ATOM | 12840 | O | PHE | B | 307 | −37.354 | −9.684 | −22.260 | 1.00 | 19.50 | O |
| ATOM | 12842 | N | THR | B | 308 | −36.532 | −10.583 | −24.143 | 1.00 | 18.96 | N |
| ATOM | 12843 | CA | THR | B | 308 | −36.321 | −11.874 | −23.511 | 1.00 | 18.84 | C |
| ATOM | 12845 | CB | THR | B | 308 | −35.774 | −12.879 | −24.490 | 1.00 | 18.62 | C |
| ATOM | 12847 | OG1 | THR | B | 308 | −36.687 | −12.988 | −25.579 | 1.00 | 18.88 | O |
| ATOM | 12849 | CG2 | THR | B | 308 | −35.626 | −14.228 | −23.833 | 1.00 | 18.74 | C |
| ATOM | 12853 | C | THR | B | 308 | −35.384 | −11.737 | −22.317 | 1.00 | 19.04 | C |
| ATOM | 12854 | O | THR | B | 308 | −35.686 | −12.244 | −21.233 | 1.00 | 18.69 | O |
| ATOM | 12856 | N | ASP | B | 309 | −34.264 | −11.031 | −22.511 | 1.00 | 19.36 | N |

TABLE 3-7-continued

Coordinates of *P. tremuloides IspS*

| | | | | | | | | | | | |
|---|---|---|---|---|---|---|---|---|---|---|---|
| ATOM | 12857 | CA | ASP | B | 309 | −33.335 | −10.751 | −21.421 | 1.00 | 19.65 | C |
| ATOM | 12859 | CB | ASP | B | 309 | −32.121 | −9.983 | −21.942 | 1.00 | 19.92 | C |
| ATOM | 12862 | CG | ASP | B | 309 | −31.171 | −9.536 | −20.814 | 1.00 | 23.51 | C |
| ATOM | 12863 | OD1 | ASP | B | 309 | −30.520 | −10.412 | −20.175 | 1.00 | 27.27 | O |
| ATOM | 12864 | OD2 | ASP | B | 309 | −31.076 | −8.299 | −20.561 | 1.00 | 27.40 | O |
| ATOM | 12865 | C | ASP | B | 309 | −34.048 | −9.977 | −20.295 | 1.00 | 19.08 | C |
| ATOM | 12866 | O | ASP | B | 309 | −33.912 | −10.308 | −19.124 | 1.00 | 18.55 | O |
| ATOM | 12868 | N | ALA | B | 310 | −34.836 | −8.975 | −20.665 | 1.00 | 18.93 | N |
| ATOM | 12869 | CA | ALA | B | 310 | −35.546 | −8.151 | −19.688 | 1.00 | 19.12 | C |
| ATOM | 12871 | CB | ALA | B | 310 | −36.346 | −7.062 | −20.380 | 1.00 | 18.79 | C |
| ATOM | 12875 | C | ALA | B | 310 | −36.462 | −8.965 | −18.784 | 1.00 | 19.36 | C |
| ATOM | 12876 | O | ALA | B | 310 | −36.560 | −8.696 | −17.577 | 1.00 | 19.58 | O |
| ATOM | 12878 | N | VAL | B | 311 | −37.143 | −9.942 | −19.370 | 1.00 | 19.61 | N |
| ATOM | 12879 | CA | VAL | B | 311 | −37.996 | −10.845 | −18.611 | 1.00 | 19.68 | C |
| ATOM | 12881 | CB | VAL | B | 311 | −38.867 | −11.682 | −19.555 | 1.00 | 19.46 | C |
| ATOM | 12883 | CG1 | VAL | B | 311 | −39.948 | −10.825 | −20.123 | 1.00 | 18.49 | C |
| ATOM | 12887 | CG2 | VAL | B | 311 | −39.469 | −12.863 | −18.843 | 1.00 | 19.31 | C |
| ATOM | 12891 | C | VAL | B | 311 | −37.161 | −11.726 | −17.673 | 1.00 | 20.46 | C |
| ATOM | 12892 | O | VAL | B | 311 | −37.479 | −11.843 | −16.494 | 1.00 | 20.25 | O |
| ATOM | 12894 | N | GLU | B | 312 | −36.085 | −12.317 | −18.189 | 1.00 | 21.67 | N |
| ATOM | 12895 | CA | GLU | B | 312 | −35.198 | −13.168 | −17.384 | 1.00 | 22.65 | C |
| ATOM | 12897 | CB | GLU | B | 312 | −34.056 | −13.708 | −18.239 | 1.00 | 23.03 | C |
| ATOM | 12900 | CG | GLU | B | 312 | −34.454 | −14.764 | −19.261 | 1.00 | 24.88 | C |
| ATOM | 12903 | CD | GLU | B | 312 | −33.335 | −15.077 | −20.267 | 1.00 | 27.34 | C |
| ATOM | 12904 | OE1 | GLU | B | 312 | −33.485 | −16.057 | −21.028 | 1.00 | 29.07 | O |
| ATOM | 12905 | OE2 | GLU | B | 312 | −32.316 | −14.342 | −20.313 | 1.00 | 28.63 | O |
| ATOM | 12906 | C | GLU | B | 312 | −34.598 | −12.443 | −16.167 | 1.00 | 23.09 | C |
| ATOM | 12907 | O | GLU | B | 312 | −34.506 | −13.007 | −15.082 | 1.00 | 23.04 | O |
| ATOM | 12909 | N | ARG | B | 313 | −34.186 | −11.199 | −16.335 | 1.00 | 23.67 | N |
| ATOM | 12910 | CA | ARG | B | 313 | −33.590 | −10.486 | −15.222 | 1.00 | 24.60 | C |
| ATOM | 12912 | CB | ARG | B | 313 | −32.609 | −9.436 | −15.735 | 1.00 | 25.26 | C |
| ATOM | 12915 | CG | ARG | B | 313 | −31.333 | −10.030 | −16.398 | 1.00 | 27.83 | C |
| ATOM | 12918 | CD | ARG | B | 313 | −30.289 | −8.943 | −16.754 | 1.00 | 31.87 | C |
| ATOM | 12921 | NE | ARG | B | 313 | −30.922 | −7.793 | −17.430 | 1.00 | 35.71 | N |
| ATOM | 12923 | CZ | ARG | B | 313 | −31.341 | −6.661 | −16.837 | 1.00 | 38.42 | C |
| ATOM | 12924 | NH1 | ARG | B | 313 | −31.189 | −6.452 | −15.522 | 1.00 | 39.15 | N |
| ATOM | 12927 | NH2 | ARG | B | 313 | −31.919 | −5.711 | −17.576 | 1.00 | 39.25 | N |
| ATOM | 12930 | C | ARG | B | 313 | −34.638 | −9.879 | −14.280 | 1.00 | 24.67 | C |
| ATOM | 12931 | O | ARG | B | 313 | −34.359 | −9.645 | −13.117 | 1.00 | 24.09 | O |
| ATOM | 12933 | N | TRP | B | 314 | −35.843 | −9.635 | −14.781 | 1.00 | 25.60 | N |
| ATOM | 12934 | CA | TRP | B | 314 | −36.971 | −9.180 | −13.951 | 1.00 | 26.20 | C |
| ATOM | 12936 | CB | TRP | B | 314 | −37.488 | −10.339 | −13.097 | 1.00 | 25.90 | C |
| ATOM | 12939 | CG | TRP | B | 314 | −38.912 | −10.184 | −12.662 | 1.00 | 23.93 | C |
| ATOM | 12940 | CD1 | TRP | B | 314 | −39.355 | −9.854 | −11.424 | 1.00 | 22.76 | C |
| ATOM | 12942 | NE1 | TRP | B | 314 | −40.727 | −9.804 | −11.412 | 1.00 | 21.93 | N |
| ATOM | 12944 | CE2 | TRP | B | 314 | −41.189 | −10.107 | −12.659 | 1.00 | 20.38 | C |
| ATOM | 12945 | CD2 | TRP | B | 314 | −40.074 | −10.352 | −13.473 | 1.00 | 21.17 | C |
| ATOM | 12946 | CE3 | TRP | B | 314 | −40.277 | −10.684 | −14.811 | 1.00 | 20.19 | C |
| ATOM | 12948 | CZ3 | TRP | B | 314 | −41.549 | −10.766 | −15.280 | 1.00 | 19.79 | C |
| ATOM | 12950 | CH2 | TRP | B | 314 | −42.640 | −10.512 | −14.445 | 1.00 | 21.00 | C |
| ATOM | 12952 | CZ2 | TRP | B | 314 | −42.474 | −10.179 | −13.130 | 1.00 | 20.60 | C |
| ATOM | 12954 | C | TRP | B | 314 | −36.620 | −7.966 | −13.076 | 1.00 | 27.57 | C |
| ATOM | 12955 | O | TRP | B | 314 | −36.890 | −7.935 | −11.870 | 1.00 | 27.56 | O |
| ATOM | 12957 | N | ASP | B | 315 | −36.039 | −6.959 | −13.718 | 1.00 | 29.12 | N |
| ATOM | 12958 | CA | ASP | B | 315 | −35.452 | −5.822 | −13.027 | 1.00 | 30.46 | C |
| ATOM | 12960 | CB | ASP | B | 315 | −33.935 | −5.796 | −13.315 | 1.00 | 30.84 | C |
| ATOM | 12963 | CG | ASP | B | 315 | −33.227 | −4.551 | −12.772 | 1.00 | 32.75 | C |
| ATOM | 12964 | OD1 | ASP | B | 315 | −33.747 | −3.904 | −11.830 | 1.00 | 35.67 | O |
| ATOM | 12965 | OD2 | ASP | B | 315 | −32.128 | −4.222 | −13.295 | 1.00 | 34.91 | O |
| ATOM | 12966 | C | ASP | B | 315 | −36.157 | −4.592 | −13.557 | 1.00 | 31.10 | C |
| ATOM | 12967 | O | ASP | B | 315 | −35.888 | −4.157 | −14.674 | 1.00 | 31.35 | O |
| ATOM | 12969 | N | VAL | B | 316 | −37.088 | −4.044 | −12.781 | 1.00 | 32.06 | N |
| ATOM | 12970 | CA | VAL | B | 316 | −37.864 | −2.896 | −13.262 | 1.00 | 32.65 | C |
| ATOM | 12972 | CB | VAL | B | 316 | −39.016 | −2.510 | −12.334 | 1.00 | 32.45 | C |
| ATOM | 12974 | CG1 | VAL | B | 316 | −39.911 | −1.499 | −13.012 | 1.00 | 32.15 | C |
| ATOM | 12978 | CG2 | VAL | B | 316 | −38.490 | −1.960 | −11.040 | 1.00 | 32.91 | C |
| ATOM | 12982 | C | VAL | B | 316 | −36.964 | −1.692 | −13.442 | 1.00 | 33.43 | C |
| ATOM | 12983 | O | VAL | B | 316 | −37.228 | −.854 | −14.294 | 1.00 | 33.74 | O |
| ATOM | 12985 | N | ASN | B | 317 | −35.881 | −1.628 | −12.663 | 1.00 | 34.29 | N |
| ATOM | 12986 | CA | ASN | B | 317 | −34.937 | −.510 | −12.730 | 1.00 | 34.63 | C |
| ATOM | 12988 | CB | ASN | B | 317 | −33.995 | −.526 | −11.505 | 1.00 | 34.50 | C |
| ATOM | 12991 | CG | ASN | B | 317 | −34.692 | −.084 | −10.201 | 1.00 | 34.08 | C |
| ATOM | 12992 | OD1 | ASN | B | 317 | −35.198 | 1.042 | −10.104 | 1.00 | 33.72 | O |
| ATOM | 12993 | ND2 | ASN | B | 317 | −34.690 | −.961 | −9.193 | 1.00 | 31.22 | N |
| ATOM | 12996 | C | ASN | B | 317 | −34.124 | −.481 | −14.029 | 1.00 | 35.21 | C |
| ATOM | 12997 | O | ASN | B | 317 | −33.196 | .296 | −14.127 | 1.00 | 35.52 | O |
| ATOM | 12999 | N | ALA | B | 318 | −34.470 | −1.318 | −15.013 | 1.00 | 35.89 | N |
| ATOM | 13000 | CA | ALA | B | 318 | −33.757 | −1.382 | −16.299 | 1.00 | 36.48 | C |

TABLE 3-7-continued

| Coordinates of *P. tremuloides IspS* | | | | | | | | | | |
|---|---|---|---|---|---|---|---|---|---|---|
| ATOM | 13002 | CB | ALA | B | 318 | −32.727 | −2.508 | −16.253 | 1.00 | 36.49 C |
| ATOM | 13006 | C | ALA | B | 318 | −34.695 | −1.525 | −17.534 | 1.00 | 37.02 C |
| ATOM | 13007 | O | ALA | B | 318 | −34.297 | −1.984 | −18.616 | 1.00 | 36.52 O |
| ATOM | 13009 | N | ILE | B | 319 | −35.952 | −1.137 | −17.339 | 1.00 | 37.76 N |
| ATOM | 13010 | CA | ILE | B | 319 | −36.848 | −.733 | −18.424 | 1.00 | 38.08 C |
| ATOM | 13012 | CB | ILE | B | 319 | −37.926 | .247 | −17.893 | 1.00 | 38.11 C |
| ATOM | 13014 | CG1 | ILE | B | 319 | −39.110 | −.495 | −17.293 | 1.00 | 38.08 C |
| ATOM | 13017 | CD1 | ILE | B | 319 | −40.068 | .451 | −16.596 | 1.00 | 38.27 C |
| ATOM | 13021 | CG2 | ILE | B | 319 | −38.408 | 1.189 | −18.996 | 1.00 | 37.84 C |
| ATOM | 13025 | C | ILE | B | 319 | −36.134 | .053 | −19.516 | 1.00 | 38.29 C |
| ATOM | 13026 | O | ILE | B | 319 | −36.192 | −.324 | −20.677 | 1.00 | 38.68 O |
| ATOM | 13028 | N | ASN | B | 320 | −35.460 | 1.141 | −19.125 | 1.00 | 38.36 N |
| ATOM | 13029 | CA | ASN | B | 320 | −34.977 | 2.168 | −20.074 | 1.00 | 38.17 C |
| ATOM | 13031 | CB | ASN | B | 320 | −34.278 | 3.331 | −19.331 | 1.00 | 38.16 C |
| ATOM | 13034 | CG | ASN | B | 320 | −35.258 | 4.207 | −18.514 | 1.00 | 37.87 C |
| ATOM | 13035 | OD1 | ASN | B | 320 | −36.366 | 4.542 | −18.955 | 1.00 | 36.50 O |
| ATOM | 13036 | ND2 | ASN | B | 320 | −34.827 | 4.589 | −17.322 | 1.00 | 38.12 N |
| ATOM | 13039 | C | ASN | B | 320 | −34.082 | 1.643 | −21.206 | 1.00 | 37.78 C |
| ATOM | 13040 | O | ASN | B | 320 | −33.856 | 2.332 | −22.181 | 1.00 | 37.76 O |
| ATOM | 13042 | N | ASP | B | 321 | −33.600 | .416 | −21.083 | 1.00 | 37.46 N |
| ATOM | 13043 | CA | ASP | B | 321 | −32.852 | −.224 | −22.162 | 1.00 | 37.25 C |
| ATOM | 13045 | CB | ASP | B | 321 | −32.091 | −1.467 | −21.629 | 1.00 | 37.83 C |
| ATOM | 13048 | CG | ASP | B | 321 | −31.351 | −1.207 | −20.285 | 1.00 | 39.33 C |
| ATOM | 13049 | OD1 | ASP | B | 321 | −31.247 | −.021 | −19.871 | 1.00 | 40.72 O |
| ATOM | 13050 | OD2 | ASP | B | 321 | −30.887 | −2.199 | −19.648 | 1.00 | 39.62 O |
| ATOM | 13051 | C | ASP | B | 321 | −33.764 | −.636 | −23.339 | 1.00 | 35.99 C |
| ATOM | 13052 | O | ASP | B | 321 | −33.273 | −.904 | −24.436 | 1.00 | 35.87 O |
| ATOM | 13054 | N | LEU | B | 322 | −35.076 | −.674 | −23.111 | 1.00 | 34.66 N |
| ATOM | 13055 | CA | LEU | B | 322 | −36.024 | −1.263 | −24.061 | 1.00 | 33.77 C |
| ATOM | 13057 | CB | LEU | B | 322 | −37.180 | −1.961 | −23.327 | 1.00 | 33.65 C |
| ATOM | 13060 | CG | LEU | B | 322 | −36.994 | −3.260 | −22.544 | 1.00 | 32.41 C |
| ATOM | 13062 | CD1 | LEU | B | 322 | −38.223 | −3.482 | −21.693 | 1.00 | 31.54 C |
| ATOM | 13066 | CD2 | LEU | B | 322 | −36.769 | −4.432 | −23.460 | 1.00 | 30.73 C |
| ATOM | 13070 | C | LEU | B | 322 | −36.670 | −.243 | −24.982 | 1.00 | 33.32 C |
| ATOM | 13071 | O | LEU | B | 322 | −36.910 | .893 | −24.570 | 1.00 | 33.37 O |
| ATOM | 13073 | N | PRO | B | 323 | −37.005 | −.667 | −26.218 | 1.00 | 32.72 N |
| ATOM | 13074 | CA | PRO | B | 323 | −37.856 | .068 | −27.126 | 1.00 | 32.42 C |
| ATOM | 13076 | CB | PRO | B | 323 | −38.239 | −.985 | −28.158 | 1.00 | 32.28 C |
| ATOM | 13079 | CG | PRO | B | 323 | −37.098 | −1.849 | −28.231 | 1.00 | 32.46 C |
| ATOM | 13082 | CD | PRO | B | 323 | −36.498 | −1.891 | −26.857 | 1.00 | 32.79 C |
| ATOM | 13085 | C | PRO | B | 323 | −39.115 | .576 | −26.453 | 1.00 | 32.50 C |
| ATOM | 13086 | O | PRO | B | 323 | −39.655 | −.083 | −25.550 | 1.00 | 32.46 O |
| ATOM | 13087 | N | ASP | B | 324 | −39.590 | 1.725 | −26.923 | 1.00 | 32.44 N |
| ATOM | 13088 | CA | ASP | B | 324 | −40.729 | 2.387 | −26.318 | 1.00 | 32.44 C |
| ATOM | 13090 | CB | ASP | B | 324 | −41.059 | 3.678 | −27.071 | 1.00 | 32.91 C |
| ATOM | 13093 | CG | ASP | B | 324 | −40.241 | 4.873 | −26.576 | 1.00 | 34.17 C |
| ATOM | 13094 | OD1 | ASP | B | 324 | −39.507 | 4.728 | −25.562 | 1.00 | 35.83 O |
| ATOM | 13095 | OD2 | ASP | B | 324 | −40.351 | 5.960 | −27.196 | 1.00 | 35.42 O |
| ATOM | 13096 | C | ASP | B | 324 | −41.967 | 1.504 | −26.186 | 1.00 | 31.78 C |
| ATOM | 13097 | O | ASP | B | 324 | −42.546 | 1.440 | −25.102 | 1.00 | 31.77 O |
| ATOM | 13099 | N | TYR | B | 325 | −42.368 | .821 | −27.258 | 1.00 | 30.99 N |
| ATOM | 13100 | CA | TYR | B | 325 | −43.519 | −.086 | −27.167 | 1.00 | 30.49 C |
| ATOM | 13102 | CB | TYR | B | 325 | −43.941 | −.640 | −28.536 | 1.00 | 30.28 C |
| ATOM | 13105 | CG | TYR | B | 325 | −43.027 | −1.688 | −29.134 | 1.00 | 30.25 C |
| ATOM | 13106 | CD1 | TYR | B | 325 | −41.917 | −1.332 | −29.893 | 1.00 | 29.81 C |
| ATOM | 13108 | CE1 | TYR | B | 325 | −41.089 | −2.300 | −30.449 | 1.00 | 29.74 C |
| ATOM | 13110 | CZ | TYR | B | 325 | −41.371 | −3.643 | −30.258 | 1.00 | 30.22 C |
| ATOM | 13111 | OH | TYR | B | 325 | −40.565 | −4.625 | −30.805 | 1.00 | 31.28 O |
| ATOM | 13113 | CE2 | TYR | B | 325 | −42.466 | −4.015 | −29.519 | 1.00 | 30.23 C |
| ATOM | 13115 | CD2 | TYR | B | 325 | −43.288 | −3.038 | −28.963 | 1.00 | 30.49 C |
| ATOM | 13117 | C | TYR | B | 325 | −43.284 | −1.221 | −26.168 | 1.00 | 30.14 C |
| ATOM | 13118 | O | TYR | B | 325 | −44.219 | −1.638 | −25.483 | 1.00 | 30.19 O |
| ATOM | 13120 | N | MET | B | 326 | −42.048 | −1.700 | −26.060 | 1.00 | 29.74 N |
| ATOM | 13121 | CA | MET | B | 326 | −41.755 | −2.820 | −25.155 | 1.00 | 29.82 C |
| ATOM | 13123 | CB | MET | B | 326 | −40.461 | −3.541 | −25.549 | 1.00 | 29.69 C |
| ATOM | 13126 | CG | MET | B | 326 | −40.650 | −4.510 | −26.686 | 1.00 | 28.83 C |
| ATOM | 13129 | SD | MET | B | 326 | −39.123 | −5.272 | −27.204 | 1.00 | 26.99 S |
| ATOM | 13130 | CE | MET | B | 326 | −39.761 | −6.499 | −28.328 | 1.00 | 29.13 C |
| ATOM | 13134 | C | MET | B | 326 | −41.696 | −2.402 | −23.683 | 1.00 | 29.92 C |
| ATOM | 13135 | O | MET | B | 326 | −42.032 | −3.204 | −22.801 | 1.00 | 29.75 O |
| ATOM | 13137 | N | LYS | B | 327 | −41.251 | −1.166 | −23.429 | 1.00 | 29.68 N |
| ATOM | 13138 | CA | LYS | B | 327 | −41.318 | −.578 | −22.088 | 1.00 | 29.46 C |
| ATOM | 13140 | CB | LYS | B | 327 | −41.016 | .921 | −22.114 | 1.00 | 29.93 C |
| ATOM | 13143 | CG | LYS | B | 327 | −39.572 | 1.305 | −21.951 | 1.00 | 31.63 C |
| ATOM | 13146 | CD | LYS | B | 327 | −39.410 | 2.803 | −22.249 | 1.00 | 34.93 C |
| ATOM | 13149 | CE | LYS | B | 327 | −37.986 | 3.291 | −22.021 | 1.00 | 36.86 C |
| ATOM | 13152 | NZ | LYS | B | 327 | −37.642 | 4.436 | −22.917 | 1.00 | 37.83 N |
| ATOM | 13156 | C | LYS | B | 327 | −42.708 | −.752 | −21.531 | 1.00 | 28.46 C |

TABLE 3-7-continued

Coordinates of *P. tremuloides IspS*

| | | | | | | | | | | | |
|---|---|---|---|---|---|---|---|---|---|---|---|
| ATOM | 13157 | O | LYS | B | 327 | −42.879 | −1.314 | −20.461 | 1.00 | 28.54 | O |
| ATOM | 13159 | N | LEU | B | 328 | −43.696 | −.258 | −22.268 | 1.00 | 27.39 | N |
| ATOM | 13160 | CA | LEU | B | 328 | −45.056 | −.216 | −21.785 | 1.00 | 26.79 | C |
| ATOM | 13162 | CB | LEU | B | 328 | −45.946 | .519 | −22.773 | 1.00 | 26.68 | C |
| ATOM | 13165 | CG | LEU | B | 328 | −47.265 | 1.034 | −22.212 | 1.00 | 26.00 | C |
| ATOM | 13167 | CD1 | LEU | B | 328 | −47.010 | 1.964 | −21.036 | 1.00 | 24.88 | C |
| ATOM | 13171 | CD2 | LEU | B | 328 | −48.051 | 1.740 | −23.308 | 1.00 | 24.55 | C |
| ATOM | 13175 | C | LEU | B | 328 | −45.560 | −1.628 | −21.587 | 1.00 | 26.70 | C |
| ATOM | 13176 | O | LEU | B | 328 | −46.110 | −1.983 | −20.543 | 1.00 | 27.03 | O |
| ATOM | 13178 | N | CYS | B | 329 | −45.341 | −2.453 | −22.591 | 1.00 | 26.39 | N |
| ATOM | 13179 | CA | CYS | B | 329 | −45.750 | −3.843 | −22.524 | 1.00 | 26.12 | C |
| ATOM | 13181 | CB | CYS | B | 329 | −45.382 | −4.526 | −23.838 | 1.00 | 26.47 | C |
| ATOM | 13184 | SG | CYS | B | 329 | −45.857 | −6.236 | −23.880 | 1.00 | 30.60 | S |
| ATOM | 13186 | C | CYS | B | 329 | −45.124 | −4.568 | −21.319 | 1.00 | 24.45 | C |
| ATOM | 13187 | O | CYS | B | 329 | −45.829 | −5.105 | −20.486 | 1.00 | 23.93 | O |
| ATOM | 13189 | N | PHE | B | 330 | −43.801 | −4.553 | −21.228 | 1.00 | 23.30 | N |
| ATOM | 13190 | CA | PHE | B | 330 | −43.087 | −5.220 | −20.141 | 1.00 | 22.47 | C |
| ATOM | 13192 | CB | PHE | B | 330 | −41.575 | −5.019 | −20.267 | 1.00 | 22.42 | C |
| ATOM | 13195 | CG | PHE | B | 330 | −40.800 | −5.518 | −19.076 | 1.00 | 22.37 | C |
| ATOM | 13196 | CD1 | PHE | B | 330 | −40.502 | −6.864 | −18.940 | 1.00 | 22.47 | C |
| ATOM | 13198 | CE1 | PHE | B | 330 | −39.799 | −7.339 | −17.836 | 1.00 | 21.64 | C |
| ATOM | 13200 | CZ | PHE | B | 330 | −39.379 | −6.472 | −16.866 | 1.00 | 21.50 | C |
| ATOM | 13202 | CE2 | PHE | B | 330 | −39.659 | −5.122 | −16.983 | 1.00 | 21.92 | C |
| ATOM | 13204 | CD2 | PHE | B | 330 | −40.374 | −4.648 | −18.084 | 1.00 | 22.29 | C |
| ATOM | 13206 | C | PHE | B | 330 | −43.524 | −4.739 | −18.765 | 1.00 | 21.87 | C |
| ATOM | 13207 | O | PHE | B | 330 | −43.779 | −5.552 | −17.875 | 1.00 | 21.98 | O |
| ATOM | 13209 | N | LEU | B | 331 | −43.594 | −3.427 | −18.573 | 1.00 | 20.88 | N |
| ATOM | 13210 | CA | LEU | B | 331 | −43.997 | −2.894 | −17.276 | 1.00 | 20.25 | C |
| ATOM | 13212 | CB | LEU | B | 331 | −43.927 | −1.354 | −17.257 | 1.00 | 20.06 | C |
| ATOM | 13215 | CG | LEU | B | 331 | −44.124 | −.628 | −15.912 | 1.00 | 19.21 | C |
| ATOM | 13217 | CD1 | LEU | B | 331 | −43.542 | −1.408 | −14.737 | 1.00 | 18.78 | C |
| ATOM | 13221 | CD2 | LEU | B | 331 | −43.555 | .770 | −15.957 | 1.00 | 15.75 | C |
| ATOM | 13225 | C | LEU | B | 331 | −45.398 | −3.408 | −16.902 | 1.00 | 19.99 | C |
| ATOM | 13226 | O | LEU | B | 331 | −45.606 | −3.860 | −15.771 | 1.00 | 19.67 | O |
| ATOM | 13228 | N | ALA | B | 332 | −46.336 | −3.373 | −17.860 | 1.00 | 19.56 | N |
| ATOM | 13229 | CA | ALA | B | 332 | −47.695 | −3.882 | −17.629 | 1.00 | 19.24 | C |
| ATOM | 13231 | CB | ALA | B | 332 | −48.528 | −3.802 | −18.891 | 1.00 | 18.58 | C |
| ATOM | 13235 | C | ALA | B | 332 | −47.637 | −5.321 | −17.108 | 1.00 | 19.23 | C |
| ATOM | 13236 | O | ALA | B | 332 | −48.235 | −5.650 | −16.079 | 1.00 | 19.18 | O |
| ATOM | 13238 | N | LEU | B | 333 | −46.891 | −6.162 | −17.816 | 1.00 | 19.16 | N |
| ATOM | 13239 | CA | LEU | B | 333 | −46.727 | −7.554 | −17.438 | 1.00 | 19.08 | C |
| ATOM | 13241 | CB | LEU | B | 333 | −45.830 | −8.260 | −18.462 | 1.00 | 18.97 | C |
| ATOM | 13244 | CG | LEU | B | 333 | −45.511 | −9.758 | −18.307 | 1.00 | 19.18 | C |
| ATOM | 13246 | CD1 | LEU | B | 333 | −46.779 | −10.611 | −18.121 | 1.00 | 18.09 | C |
| ATOM | 13250 | CD2 | LEU | B | 333 | −44.676 | −10.262 | −19.499 | 1.00 | 17.17 | C |
| ATOM | 13254 | C | LEU | B | 333 | −46.111 | −7.616 | −16.042 | 1.00 | 19.16 | C |
| ATOM | 13255 | O | LEU | B | 333 | −46.629 | −8.279 | −15.137 | 1.00 | 18.97 | O |
| ATOM | 13257 | N | TYR | B | 334 | −45.013 | −6.887 | −15.884 | 1.00 | 19.23 | N |
| ATOM | 13258 | CA | TYR | B | 334 | −44.212 | −6.906 | −14.664 | 1.00 | 19.33 | C |
| ATOM | 13260 | CB | TYR | B | 334 | −43.092 | −5.873 | −14.785 | 1.00 | 19.43 | C |
| ATOM | 13263 | CG | TYR | B | 334 | −42.190 | −5.748 | −13.596 | 1.00 | 19.44 | C |
| ATOM | 13264 | CD1 | TYR | B | 334 | −41.006 | −6.464 | −13.524 | 1.00 | 20.60 | C |
| ATOM | 13266 | CE1 | TYR | B | 334 | −40.148 | −6.347 | −12.442 | 1.00 | 20.77 | C |
| ATOM | 13268 | CZ | TYR | B | 334 | −40.474 | −5.503 | −11.417 | 1.00 | 21.51 | C |
| ATOM | 13269 | OH | TYR | B | 334 | −39.628 | −5.387 | −10.353 | 1.00 | 21.42 | O |
| ATOM | 13271 | CE2 | TYR | B | 334 | −41.646 | −4.768 | −11.466 | 1.00 | 22.15 | C |
| ATOM | 13273 | CD2 | TYR | B | 334 | −42.495 | −4.892 | −12.565 | 1.00 | 20.55 | C |
| ATOM | 13275 | C | TYR | B | 334 | −45.065 | −6.614 | −13.443 | 1.00 | 19.37 | C |
| ATOM | 13276 | O | TYR | B | 334 | −44.980 | −7.337 | −12.441 | 1.00 | 19.94 | O |
| ATOM | 13278 | N | ASN | B | 335 | −45.888 | −5.565 | −13.527 | 1.00 | 18.83 | N |
| ATOM | 13279 | CA | ASN | B | 335 | −46.784 | −5.236 | −12.443 | 1.00 | 18.37 | C |
| ATOM | 13281 | CB | ASN | B | 335 | −47.452 | −3.896 | −12.675 | 1.00 | 18.52 | C |
| ATOM | 13284 | CG | ASN | B | 335 | −46.493 | −2.742 | −12.518 | 1.00 | 19.27 | C |
| ATOM | 13285 | OD1 | ASN | B | 335 | −45.421 | −2.906 | −11.953 | 1.00 | 21.25 | O |
| ATOM | 13286 | ND2 | ASN | B | 335 | −46.872 | −1.566 | −13.022 | 1.00 | 19.24 | N |
| ATOM | 13289 | C | ASN | B | 335 | −47.812 | −6.333 | −12.291 | 1.00 | 18.22 | C |
| ATOM | 13290 | O | ASN | B | 335 | −47.966 | −6.891 | −11.207 | 1.00 | 18.53 | O |
| ATOM | 13292 | N | THR | B | 336 | −48.481 | −6.697 | −13.379 | 1.00 | 17.95 | N |
| ATOM | 13293 | CA | THR | B | 336 | −49.525 | −7.728 | −13.301 | 1.00 | 17.61 | C |
| ATOM | 13295 | CB | THR | B | 336 | −49.980 | −8.204 | −14.676 | 1.00 | 17.36 | C |
| ATOM | 13297 | OG1 | THR | B | 336 | −50.249 | −7.065 | −15.500 | 1.00 | 17.02 | O |
| ATOM | 13299 | CG2 | THR | B | 336 | −51.228 | −9.044 | −14.551 | 1.00 | 16.07 | C |
| ATOM | 13303 | C | THR | B | 336 | −49.065 | −8.941 | −12.501 | 1.00 | 17.75 | C |
| ATOM | 13304 | O | THR | B | 336 | −49.788 | −9.429 | −11.621 | 1.00 | 18.09 | O |
| ATOM | 13306 | N | ILE | B | 337 | −47.859 | −9.411 | −12.785 | 1.00 | 17.69 | N |
| ATOM | 13307 | CA | ILE | B | 337 | −47.384 | −10.630 | −12.165 | 1.00 | 17.74 | C |
| ATOM | 13309 | CB | ILE | B | 337 | −46.228 | −11.245 | −12.949 | 1.00 | 17.40 | C |
| ATOM | 13311 | CG1 | ILE | B | 337 | −46.795 | −11.865 | −14.227 | 1.00 | 18.44 | C |

TABLE 3-7-continued

Coordinates of *P. tremuloides IspS*

| | | | | | | | | | | | |
|---|---|---|---|---|---|---|---|---|---|---|---|
| ATOM | 13314 | CD1 | ILE | B | 337 | −45.767 | −12.192 | −15.300 | 1.00 | 19.26 | C |
| ATOM | 13318 | CG2 | ILE | B | 337 | −45.568 | −12.320 | −12.152 | 1.00 | 16.25 | C |
| ATOM | 13322 | C | ILE | B | 337 | −47.053 | −10.395 | −10.699 | 1.00 | 18.32 | C |
| ATOM | 13323 | O | ILE | B | 337 | −47.497 | −11.175 | −9.838 | 1.00 | 18.06 | O |
| ATOM | 13325 | N | ASN | B | 338 | −46.321 | −9.311 | −10.404 | 1.00 | 18.89 | N |
| ATOM | 13326 | CA | ASN | B | 338 | −45.985 | −8.978 | −9.007 | 1.00 | 19.49 | C |
| ATOM | 13328 | CB | ASN | B | 338 | −45.189 | −7.690 | −8.917 | 1.00 | 19.43 | C |
| ATOM | 13331 | CG | ASN | B | 338 | −43.789 | −7.836 | −9.444 | 1.00 | 20.83 | C |
| ATOM | 13332 | OD1 | ASN | B | 338 | −43.292 | −8.954 | −9.634 | 1.00 | 21.52 | O |
| ATOM | 13333 | ND2 | ASN | B | 338 | −43.124 | −6.697 | −9.676 | 1.00 | 22.32 | N |
| ATOM | 13336 | C | ASN | B | 338 | −47.229 | −8.835 | −8.146 | 1.00 | 20.05 | C |
| ATOM | 13337 | O | ASN | B | 338 | −47.182 | −9.055 | −6.953 | 1.00 | 19.81 | O |
| ATOM | 13339 | N | GLU | B | 339 | −48.337 | −8.459 | −8.770 | 1.00 | 20.81 | N |
| ATOM | 13340 | CA | GLU | B | 339 | −49.589 | −8.347 | −8.086 | 1.00 | 21.81 | C |
| ATOM | 13342 | CB | GLU | B | 339 | −50.563 | −7.544 | −8.933 | 1.00 | 22.69 | C |
| ATOM | 13345 | CG | GLU | B | 339 | −51.240 | −6.422 | −8.148 | 1.00 | 27.28 | C |
| ATOM | 13348 | CD | GLU | B | 339 | −52.571 | −5.959 | −8.768 | 1.00 | 32.79 | C |
| ATOM | 13349 | OE1 | GLU | B | 339 | −52.761 | −4.713 | −8.897 | 1.00 | 36.20 | O |
| ATOM | 13350 | OE2 | GLU | B | 339 | −53.416 | −6.837 | −9.114 | 1.00 | 34.35 | O |
| ATOM | 13351 | C | GLU | B | 339 | −50.170 | −9.732 | −7.762 | 1.00 | 21.59 | C |
| ATOM | 13352 | O | GLU | B | 339 | −50.690 | −9.946 | −6.666 | 1.00 | 21.38 | O |
| ATOM | 13354 | N | ILE | B | 340 | −50.094 | −10.676 | −8.700 | 1.00 | 21.48 | N |
| ATOM | 13355 | CA | ILE | B | 340 | −50.486 | −12.049 | −8.384 | 1.00 | 21.27 | C |
| ATOM | 13357 | CB | ILE | B | 340 | −50.437 | −12.990 | −9.603 | 1.00 | 21.17 | C |
| ATOM | 13359 | CG1 | ILE | B | 340 | −51.478 | −12.589 | −10.643 | 1.00 | 20.99 | C |
| ATOM | 13362 | CD1 | ILE | B | 340 | −51.245 | −13.202 | −12.017 | 1.00 | 19.72 | C |
| ATOM | 13366 | CG2 | ILE | B | 340 | −50.702 | −14.444 | −9.177 | 1.00 | 21.09 | C |
| ATOM | 13370 | C | ILE | B | 340 | −49.557 | −12.585 | −7.278 | 1.00 | 21.40 | C |
| ATOM | 13371 | O | ILE | B | 340 | −50.023 | −13.238 | −6.334 | 1.00 | 21.74 | O |
| ATOM | 13373 | N | ALA | B | 341 | −48.256 | −12.301 | −7.380 | 1.00 | 20.90 | N |
| ATOM | 13374 | CA | ALA | B | 341 | −47.312 | −12.721 | −6.349 | 1.00 | 20.62 | C |
| ATOM | 13376 | CB | ALA | B | 341 | −45.922 | −12.260 | −6.694 | 1.00 | 20.53 | C |
| ATOM | 13380 | C | ALA | B | 341 | −47.720 | −12.195 | −4.969 | 1.00 | 20.59 | C |
| ATOM | 13381 | O | ALA | B | 341 | −47.606 | −12.901 | −3.950 | 1.00 | 20.57 | O |
| ATOM | 13383 | N | TYR | B | 342 | −48.208 | −10.958 | −4.949 | 1.00 | 20.62 | N |
| ATOM | 13384 | CA | TYR | B | 342 | −48.600 | −10.303 | −3.707 | 1.00 | 20.59 | C |
| ATOM | 13386 | CB | TYR | B | 342 | −48.790 | −8.792 | −3.907 | 1.00 | 20.05 | C |
| ATOM | 13389 | CG | TYR | B | 342 | −49.309 | −8.143 | −2.674 | 1.00 | 18.29 | C |
| ATOM | 13390 | CD1 | TYR | B | 342 | −48.443 | −7.683 | −1.698 | 1.00 | 17.62 | C |
| ATOM | 13392 | CE1 | TYR | B | 342 | −48.914 | −7.111 | −.518 | 1.00 | 17.91 | C |
| ATOM | 13394 | CZ | TYR | B | 342 | −50.285 | −7.005 | −.298 | 1.00 | 18.18 | C |
| ATOM | 13395 | OH | TYR | B | 342 | −50.763 | −6.433 | .877 | 1.00 | 16.00 | O |
| ATOM | 13397 | CE2 | TYR | B | 342 | −51.169 | −7.467 | −1.275 | 1.00 | 18.10 | C |
| ATOM | 13399 | CD2 | TYR | B | 342 | −50.670 | −8.037 | −2.450 | 1.00 | 17.67 | C |
| ATOM | 13401 | C | TYR | B | 342 | −49.863 | −10.928 | −3.118 | 1.00 | 21.48 | C |
| ATOM | 13402 | O | TYR | B | 342 | −49.960 | −11.089 | −1.913 | 1.00 | 20.91 | O |
| ATOM | 13404 | N | ASP | B | 343 | −50.832 | −11.273 | −3.959 | 1.00 | 22.93 | N |
| ATOM | 13405 | CA | ASP | B | 343 | −52.048 | −11.925 | −3.470 | 1.00 | 24.30 | C |
| ATOM | 13407 | CB | ASP | B | 343 | −53.010 | −12.282 | −4.608 | 1.00 | 24.59 | C |
| ATOM | 13410 | CG | ASP | B | 343 | −53.577 | −11.060 | −5.334 | 1.00 | 26.66 | C |
| ATOM | 13411 | OD1 | ASP | B | 343 | −53.619 | −9.936 | −4.756 | 1.00 | 28.24 | O |
| ATOM | 13412 | OD2 | ASP | B | 343 | −54.004 | −11.247 | −6.506 | 1.00 | 29.56 | O |
| ATOM | 13413 | C | ASP | B | 343 | −51.660 | −13.208 | −2.761 | 1.00 | 24.97 | C |
| ATOM | 13414 | O | ASP | B | 343 | −52.128 | −13.495 | −1.658 | 1.00 | 24.95 | O |
| ATOM | 13416 | N | ASN | B | 344 | −50.792 | −13.973 | −3.413 | 1.00 | 25.90 | N |
| ATOM | 13417 | CA | ASN | B | 344 | −50.322 | −15.252 | −2.884 | 1.00 | 26.59 | C |
| ATOM | 13419 | CB | ASN | B | 344 | −49.623 | −16.043 | −3.978 | 1.00 | 26.74 | C |
| ATOM | 13422 | CG | ASN | B | 344 | −50.594 | −16.639 | −4.933 | 1.00 | 28.21 | C |
| ATOM | 13423 | OD1 | ASN | B | 344 | −51.080 | −17.737 | −4.688 | 1.00 | 32.10 | O |
| ATOM | 13424 | ND2 | ASN | B | 344 | −50.923 | −15.916 | −6.016 | 1.00 | 28.40 | N |
| ATOM | 13427 | C | ASN | B | 344 | −49.421 | −15.146 | −1.655 | 1.00 | 26.78 | C |
| ATOM | 13428 | O | ASN | B | 344 | −49.424 | −16.053 | −.821 | 1.00 | 27.06 | O |
| ATOM | 13430 | N | LEU | B | 345 | −48.647 | −14.067 | −1.533 | 1.00 | 26.74 | N |
| ATOM | 13431 | CA | LEU | B | 345 | −47.970 | −13.793 | −.261 | 1.00 | 26.59 | C |
| ATOM | 13433 | CB | LEU | B | 345 | −47.005 | −12.618 | −.396 | 1.00 | 26.25 | C |
| ATOM | 13436 | CG | LEU | B | 345 | −46.046 | −12.376 | .764 | 1.00 | 24.65 | C |
| ATOM | 13438 | CD1 | LEU | B | 345 | −45.258 | −13.621 | 1.115 | 1.00 | 22.50 | C |
| ATOM | 13442 | CD2 | LEU | B | 345 | −45.119 | −11.251 | .387 | 1.00 | 23.54 | C |
| ATOM | 13446 | C | LEU | B | 345 | −49.004 | −13.503 | .840 | 1.00 | 27.00 | C |
| ATOM | 13447 | O | LEU | B | 345 | −48.903 | −14.014 | 1.947 | 1.00 | 26.93 | O |
| ATOM | 13449 | N | LYS | B | 346 | −50.008 | −12.697 | .518 | 1.00 | 27.54 | N |
| ATOM | 13450 | CA | LYS | B | 346 | −51.012 | −12.300 | 1.491 | 1.00 | 27.96 | C |
| ATOM | 13452 | CB | LYS | B | 346 | −51.998 | −11.288 | .889 | 1.00 | 28.13 | C |
| ATOM | 13455 | CG | LYS | B | 346 | −52.822 | −10.527 | 1.926 | 1.00 | 28.70 | C |
| ATOM | 13458 | CD | LYS | B | 346 | −53.781 | −9.526 | 1.281 | 1.00 | 29.73 | C |
| ATOM | 13461 | CE | LYS | B | 346 | −55.205 | −10.063 | 1.133 | 1.00 | 31.17 | C |
| ATOM | 13464 | NZ | LYS | B | 346 | −55.839 | −9.661 | −.171 | 1.00 | 32.83 | N |
| ATOM | 13468 | C | LYS | B | 346 | −51.788 | −13.498 | 1.984 | 1.00 | 28.31 | C |

TABLE 3-7-continued

Coordinates of *P. tremuloides IspS*

| | | | | | | | | | | | |
|---|---|---|---|---|---|---|---|---|---|---|---|
| ATOM | 13469 | O | LYS | B | 346 | −52.074 | −13.600 | 3.177 | 1.00 | 28.52 | O |
| ATOM | 13471 | N | ASP | B | 347 | −52.149 | −14.396 | 1.075 | 1.00 | 28.56 | N |
| ATOM | 13472 | CA | ASP | B | 347 | −53.102 | −15.441 | 1.427 | 1.00 | 29.11 | C |
| ATOM | 13474 | CB | ASP | B | 347 | −54.068 | −15.736 | .268 | 1.00 | 29.50 | C |
| ATOM | 13477 | CG | ASP | B | 347 | −54.902 | −14.500 | −.150 | 1.00 | 31.04 | C |
| ATOM | 13478 | OD1 | ASP | B | 347 | −54.961 | −13.500 | .616 | 1.00 | 31.35 | O |
| ATOM | 13479 | OD2 | ASP | B | 347 | −55.496 | −14.534 | −1.261 | 1.00 | 33.39 | O |
| ATOM | 13480 | C | ASP | B | 347 | −52.403 | −16.699 | 1.891 | 1.00 | 28.79 | C |
| ATOM | 13481 | O | ASP | B | 347 | −52.824 | −17.321 | 2.854 | 1.00 | 29.02 | O |
| ATOM | 13483 | N | LYS | B | 348 | −51.326 | −17.068 | 1.222 | 1.00 | 28.74 | N |
| ATOM | 13484 | CA | LYS | B | 348 | −50.612 | −18.293 | 1.564 | 1.00 | 28.84 | C |
| ATOM | 13486 | CB | LYS | B | 348 | −50.290 | −19.101 | .299 | 1.00 | 29.24 | C |
| ATOM | 13489 | CG | LYS | B | 348 | −51.513 | −19.470 | −.576 | 1.00 | 30.97 | C |
| ATOM | 13492 | CD | LYS | B | 348 | −51.051 | −20.300 | −1.803 | 1.00 | 33.66 | C |
| ATOM | 13495 | CE | LYS | B | 348 | −52.033 | −20.244 | −2.989 | 1.00 | 34.52 | C |
| ATOM | 13498 | NZ | LYS | B | 348 | −53.445 | −20.542 | −2.607 | 1.00 | 35.61 | N |
| ATOM | 13502 | C | LYS | B | 348 | −49.330 | −18.029 | 2.358 | 1.00 | 27.97 | C |
| ATOM | 13503 | O | LYS | B | 348 | −48.763 | −18.948 | 2.925 | 1.00 | 27.88 | O |
| ATOM | 13505 | N | GLY | B | 349 | −48.874 | −16.785 | 2.403 | 1.00 | 27.21 | N |
| ATOM | 13506 | CA | GLY | B | 349 | −47.625 | −16.473 | 3.075 | 1.00 | 26.87 | C |
| ATOM | 13509 | C | GLY | B | 349 | −46.437 | −17.227 | 2.514 | 1.00 | 26.71 | C |
| ATOM | 13510 | O | GLY | B | 349 | −45.576 | −17.669 | 3.271 | 1.00 | 26.65 | O |
| ATOM | 13512 | N | GLU | B | 350 | −46.409 | −17.390 | 1.191 | 1.00 | 26.61 | N |
| ATOM | 13513 | CA | GLU | B | 350 | −45.263 | −17.953 | .470 | 1.00 | 26.43 | C |
| ATOM | 13515 | CB | GLU | B | 350 | −45.624 | −19.310 | −.128 | 1.00 | 26.85 | C |
| ATOM | 13518 | CG | GLU | B | 350 | −45.685 | −20.453 | .888 | 1.00 | 29.63 | C |
| ATOM | 13521 | CD | GLU | B | 350 | −44.304 | −21.036 | 1.227 | 1.00 | 34.21 | C |
| ATOM | 13522 | OE1 | GLU | B | 350 | −43.417 | −21.045 | .328 | 1.00 | 36.93 | O |
| ATOM | 13523 | OE2 | GLU | B | 350 | −44.106 | −21.498 | 2.384 | 1.00 | 35.89 | O |
| ATOM | 13524 | C | GLU | B | 350 | −44.900 | −16.981 | −.637 | 1.00 | 25.49 | C |
| ATOM | 13525 | O | GLU | B | 350 | −45.774 | −16.312 | −1.181 | 1.00 | 25.35 | O |
| ATOM | 13527 | N | ASN | B | 351 | −43.616 | −16.866 | −.955 | 1.00 | 24.74 | N |
| ATOM | 13528 | CA | ASN | B | 351 | −43.206 | −16.046 | −2.090 | 1.00 | 24.47 | C |
| ATOM | 13530 | CB | ASN | B | 351 | −41.851 | −15.369 | −1.867 | 1.00 | 24.94 | C |
| ATOM | 13533 | CG | ASN | B | 351 | −41.428 | −14.489 | −3.062 | 1.00 | 26.98 | C |
| ATOM | 13534 | OD1 | ASN | B | 351 | −41.976 | −14.605 | −4.170 | 1.00 | 28.96 | O |
| ATOM | 13535 | ND2 | ASN | B | 351 | −40.457 | −13.601 | −2.834 | 1.00 | 29.55 | N |
| ATOM | 13538 | C | ASN | B | 351 | −43.095 | −16.918 | −3.303 | 1.00 | 23.33 | C |
| ATOM | 13539 | O | ASN | B | 351 | −42.120 | −17.641 | −3.429 | 1.00 | 23.47 | O |
| ATOM | 13541 | N | ILE | B | 352 | −44.060 | −16.823 | −4.208 | 1.00 | 22.09 | N |
| ATOM | 13542 | CA | ILE | B | 352 | −44.048 | −17.644 | −5.410 | 1.00 | 21.22 | C |
| ATOM | 13544 | CB | ILE | B | 352 | −45.452 | −18.213 | −5.675 | 1.00 | 21.23 | C |
| ATOM | 13546 | CG1 | ILE | B | 352 | −46.464 | −17.080 | −5.913 | 1.00 | 21.11 | C |
| ATOM | 13549 | CD1 | ILE | B | 352 | −47.346 | −17.305 | −7.126 | 1.00 | 20.33 | C |
| ATOM | 13553 | CG2 | ILE | B | 352 | −45.875 | −19.116 | −4.519 | 1.00 | 19.79 | C |
| ATOM | 13557 | C | ILE | B | 352 | −43.508 | −16.947 | −6.689 | 1.00 | 20.88 | C |
| ATOM | 13558 | O | ILE | B | 352 | −43.486 | −17.553 | −7.758 | 1.00 | 20.76 | O |
| ATOM | 13560 | N | LEU | B | 353 | −43.030 | −15.705 | −6.574 | 1.00 | 20.44 | N |
| ATOM | 13561 | CA | LEU | B | 353 | −42.603 | −14.907 | −7.750 | 1.00 | 19.84 | C |
| ATOM | 13563 | CB | LEU | B | 353 | −42.055 | −13.527 | −7.325 | 1.00 | 19.67 | C |
| ATOM | 13566 | CG | LEU | B | 353 | −42.003 | −12.339 | −8.311 | 1.00 | 18.47 | C |
| ATOM | 13568 | CD1 | LEU | B | 353 | −43.306 | −12.083 | −9.008 | 1.00 | 17.03 | C |
| ATOM | 13572 | CD2 | LEU | B | 353 | −41.604 | −11.064 | −7.597 | 1.00 | 17.08 | C |
| ATOM | 13576 | C | LEU | B | 353 | −41.587 | −15.628 | −8.633 | 1.00 | 19.81 | C |
| ATOM | 13577 | O | LEU | B | 353 | −41.720 | −15.596 | −9.851 | 1.00 | 19.55 | O |
| ATOM | 13579 | N | PRO | B | 354 | −40.578 | −16.299 | −8.024 | 1.00 | 20.01 | N |
| ATOM | 13580 | CA | PRO | B | 354 | −39.571 | −17.010 | −8.822 | 1.00 | 19.73 | C |
| ATOM | 13582 | CB | PRO | B | 354 | −38.781 | −17.796 | −7.779 | 1.00 | 19.55 | C |
| ATOM | 13585 | CG | PRO | B | 354 | −38.928 | −17.037 | −6.542 | 1.00 | 19.61 | C |
| ATOM | 13588 | CD | PRO | B | 354 | −40.289 | −16.413 | −6.578 | 1.00 | 19.90 | C |
| ATOM | 13591 | C | PRO | B | 354 | −40.187 | −17.971 | −9.804 | 1.00 | 19.87 | C |
| ATOM | 13592 | O | PRO | B | 354 | −39.693 | −18.103 | −10.918 | 1.00 | 20.08 | O |
| ATOM | 13593 | N | TYR | B | 355 | −41.264 | −18.636 | −9.387 | 1.00 | 20.14 | N |
| ATOM | 13594 | CA | TYR | B | 355 | −41.909 | −19.665 | −10.216 | 1.00 | 20.24 | C |
| ATOM | 13596 | CB | TYR | B | 355 | −42.878 | −20.520 | −9.394 | 1.00 | 20.40 | C |
| ATOM | 13599 | CG | TYR | B | 355 | −42.189 | −21.153 | −8.214 | 1.00 | 21.82 | C |
| ATOM | 13600 | CD1 | TYR | B | 355 | −41.119 | −21.999 | −8.412 | 1.00 | 22.86 | C |
| ATOM | 13602 | CE1 | TYR | B | 355 | −40.457 | −22.564 | −7.353 | 1.00 | 25.07 | C |
| ATOM | 13604 | CZ | TYR | B | 355 | −40.850 | −22.285 | −6.053 | 1.00 | 25.58 | C |
| ATOM | 13605 | OH | TYR | B | 355 | −40.153 | −22.887 | −5.020 | 1.00 | 27.33 | O |
| ATOM | 13607 | CE2 | TYR | B | 355 | −41.918 | −21.433 | −5.815 | 1.00 | 23.93 | C |
| ATOM | 13609 | CD2 | TYR | B | 355 | −42.577 | −20.867 | −6.900 | 1.00 | 23.10 | C |
| ATOM | 13611 | C | TYR | B | 355 | −42.625 | −19.001 | −11.361 | 1.00 | 19.67 | C |
| ATOM | 13612 | O | TYR | B | 355 | −42.455 | −19.405 | −12.510 | 1.00 | 19.75 | O |
| ATOM | 13614 | N | LEU | B | 356 | −43.385 | −17.954 | −11.030 | 1.00 | 18.97 | N |
| ATOM | 13615 | CA | LEU | B | 356 | −44.180 | −17.205 | −12.004 | 1.00 | 18.26 | C |
| ATOM | 13617 | CB | LEU | B | 356 | −45.039 | −16.157 | −11.293 | 1.00 | 18.03 | C |
| ATOM | 13620 | CG | LEU | B | 356 | −46.056 | −16.727 | −10.312 | 1.00 | 18.13 | C |

TABLE 3-7-continued

Coordinates of *P. tremuloides IspS*

| | | | | | | | | | | | |
|---|---|---|---|---|---|---|---|---|---|---|---|
| ATOM | 13622 | CD1 | LEU | B | 356 | −46.691 | −15.613 | −9.500 | 1.00 | 19.37 | C |
| ATOM | 13626 | CD2 | LEU | B | 356 | −47.106 | −17.521 | −11.046 | 1.00 | 17.93 | C |
| ATOM | 13630 | C | LEU | B | 356 | −43.298 | −16.536 | −13.056 | 1.00 | 17.76 | C |
| ATOM | 13631 | O | LEU | B | 356 | −43.598 | −16.567 | −14.259 | 1.00 | 16.93 | O |
| ATOM | 13633 | N | THR | B | 357 | −42.201 | −15.949 | −12.600 | 1.00 | 17.56 | N |
| ATOM | 13634 | CA | THR | B | 357 | −41.335 | −15.215 | −13.501 | 1.00 | 17.63 | C |
| ATOM | 13636 | CB | THR | B | 357 | −40.438 | −14.236 | −12.759 | 1.00 | 17.69 | C |
| ATOM | 13638 | OG1 | THR | B | 357 | −39.530 | −14.974 | −11.934 | 1.00 | 18.39 | O |
| ATOM | 13640 | CG2 | THR | B | 357 | −41.288 | −13.242 | −11.927 | 1.00 | 16.47 | C |
| ATOM | 13644 | C | THR | B | 357 | −40.477 | −16.145 | −14.356 | 1.00 | 17.55 | C |
| ATOM | 13645 | O | THR | B | 357 | −40.154 | −15.793 | −15.498 | 1.00 | 17.17 | O |
| ATOM | 13647 | N | LYS | B | 358 | −40.127 | −17.321 | −13.824 | 1.00 | 17.37 | N |
| ATOM | 13648 | CA | LYS | B | 358 | −39.462 | −18.337 | −14.649 | 1.00 | 17.55 | C |
| ATOM | 13650 | CB | LYS | B | 358 | −39.030 | −19.542 | −13.827 | 1.00 | 17.87 | C |
| ATOM | 13653 | CG | LYS | B | 358 | −38.450 | −20.718 | −14.640 | 1.00 | 18.75 | C |
| ATOM | 13656 | CD | LYS | B | 358 | −37.013 | −20.497 | −15.112 | 1.00 | 20.18 | C |
| ATOM | 13659 | CE | LYS | B | 358 | −36.361 | −21.843 | −15.457 | 1.00 | 21.49 | C |
| ATOM | 13662 | NZ | LYS | B | 358 | −35.189 | −21.702 | −16.361 | 1.00 | 22.89 | N |
| ATOM | 13666 | C | LYS | B | 358 | −40.403 | −18.777 | −15.754 | 1.00 | 17.43 | C |
| ATOM | 13667 | O | LYS | B | 358 | −40.031 | −18.775 | −16.926 | 1.00 | 17.52 | O |
| ATOM | 13669 | N | ALA | B | 359 | −41.633 | −19.120 | −15.384 | 1.00 | 17.42 | N |
| ATOM | 13670 | CA | ALA | B | 359 | −42.654 | −19.471 | −16.359 | 1.00 | 17.52 | C |
| ATOM | 13672 | CB | ALA | B | 359 | −44.011 | −19.434 | −15.738 | 1.00 | 17.16 | C |
| ATOM | 13676 | C | ALA | B | 359 | −42.585 | −18.521 | −17.531 | 1.00 | 18.18 | C |
| ATOM | 13677 | O | ALA | B | 359 | −42.513 | −18.956 | −18.675 | 1.00 | 18.50 | O |
| ATOM | 13679 | N | TRP | B | 360 | −42.556 | −17.223 | −17.245 | 1.00 | 19.14 | N |
| ATOM | 13680 | CA | TRP | B | 360 | −42.526 | −16.206 | −18.301 | 1.00 | 19.77 | C |
| ATOM | 13682 | CB | TRP | B | 360 | −42.922 | −14.837 | −17.746 | 1.00 | 20.15 | C |
| ATOM | 13685 | CG | TRP | B | 360 | −44.377 | −14.653 | −17.813 | 1.00 | 20.50 | C |
| ATOM | 13686 | CD1 | TRP | B | 360 | −45.259 | −14.729 | −16.788 | 1.00 | 22.15 | C |
| ATOM | 13688 | NE1 | TRP | B | 360 | −46.536 | −14.533 | −17.248 | 1.00 | 22.84 | N |
| ATOM | 13690 | CE2 | TRP | B | 360 | −46.487 | −14.348 | −18.603 | 1.00 | 21.68 | C |
| ATOM | 13691 | CD2 | TRP | B | 360 | −45.134 | −14.418 | −18.987 | 1.00 | 20.85 | C |
| ATOM | 13692 | CE3 | TRP | B | 360 | −44.802 | −14.253 | −20.334 | 1.00 | 21.21 | C |
| ATOM | 13694 | CZ3 | TRP | B | 360 | −45.821 | −14.025 | −21.245 | 1.00 | 20.75 | C |
| ATOM | 13696 | CH2 | TRP | B | 360 | −47.166 | −13.961 | −20.827 | 1.00 | 21.21 | C |
| ATOM | 13698 | CZ2 | TRP | B | 360 | −47.515 | −14.123 | −19.516 | 1.00 | 20.97 | C |
| ATOM | 13700 | C | TRP | B | 360 | −41.215 | −16.110 | −19.081 | 1.00 | 19.96 | C |
| ATOM | 13701 | O | TRP | B | 360 | −41.242 | −15.791 | −20.271 | 1.00 | 19.94 | O |
| ATOM | 13703 | N | ALA | B | 361 | −40.089 | −16.368 | −18.420 | 1.00 | 20.14 | N |
| ATOM | 13704 | CA | ALA | B | 361 | −38.790 | −16.437 | −19.102 | 1.00 | 20.41 | C |
| ATOM | 13706 | CB | ALA | B | 361 | −37.676 | −16.581 | −18.102 | 1.00 | 20.67 | C |
| ATOM | 13710 | C | ALA | B | 361 | −38.763 | −17.618 | −20.041 | 1.00 | 20.55 | C |
| ATOM | 13711 | O | ALA | B | 361 | −38.330 | −17.510 | −21.187 | 1.00 | 20.76 | O |
| ATOM | 13713 | N | ASP | B | 362 | −39.230 | −18.749 | −19.534 | 1.00 | 20.57 | N |
| ATOM | 13714 | CA | ASP | B | 362 | −39.360 | −19.965 | −20.326 | 1.00 | 20.97 | C |
| ATOM | 13716 | CB | ASP | B | 362 | −39.984 | −21.082 | −19.470 | 1.00 | 21.39 | C |
| ATOM | 13719 | CG | ASP | B | 362 | −38.938 | −21.902 | −18.693 | 1.00 | 22.80 | C |
| ATOM | 13720 | OD1 | ASP | B | 362 | −38.836 | −23.109 | −18.970 | 1.00 | 28.57 | O |
| ATOM | 13721 | OD2 | ASP | B | 362 | −38.210 | −21.384 | −17.825 | 1.00 | 22.78 | O |
| ATOM | 13722 | C | ASP | B | 362 | −40.179 | −19.748 | −21.618 | 1.00 | 20.66 | C |
| ATOM | 13723 | O | ASP | B | 362 | −39.740 | −20.141 | −22.701 | 1.00 | 20.69 | O |
| ATOM | 13725 | N | LEU | B | 363 | −41.346 | −19.110 | −21.501 | 1.00 | 20.22 | N |
| ATOM | 13726 | CA | LEU | B | 363 | −42.245 | −18.885 | −22.648 | 1.00 | 19.82 | C |
| ATOM | 13728 | CB | LEU | B | 363 | −43.592 | −18.327 | −22.164 | 1.00 | 19.11 | C |
| ATOM | 13731 | CG | LEU | B | 363 | −44.644 | −17.945 | −23.209 | 1.00 | 17.02 | C |
| ATOM | 13733 | CD1 | LEU | B | 363 | −44.829 | −19.033 | −24.214 | 1.00 | 16.20 | C |
| ATOM | 13737 | CD2 | LEU | B | 363 | −45.979 | −17.618 | −22.586 | 1.00 | 14.21 | C |
| ATOM | 13741 | C | LEU | B | 363 | −41.633 | −17.950 | −23.706 | 1.00 | 20.76 | C |
| ATOM | 13742 | O | LEU | B | 363 | −41.656 | −18.235 | −24.910 | 1.00 | 21.00 | O |
| ATOM | 13744 | N | CYS | B | 364 | −41.088 | −16.826 | −23.253 | 1.00 | 21.42 | N |
| ATOM | 13745 | CA | CYS | B | 364 | −40.427 | −15.884 | −24.147 | 1.00 | 21.67 | C |
| ATOM | 13747 | CB | CYS | B | 364 | −39.969 | −14.639 | −23.376 | 1.00 | 21.86 | C |
| ATOM | 13750 | SG | CYS | B | 364 | −41.327 | −13.638 | −22.722 | 1.00 | 23.36 | S |
| ATOM | 13752 | C | CYS | B | 364 | −39.229 | −16.547 | −24.835 | 1.00 | 21.52 | C |
| ATOM | 13753 | O | CYS | B | 364 | −39.010 | −16.323 | −26.037 | 1.00 | 21.67 | O |
| ATOM | 13755 | N | ASN | B | 365 | −38.454 | −17.352 | −24.095 | 1.00 | 20.83 | N |
| ATOM | 13756 | CA | ASN | B | 365 | −37.306 | −18.025 | −24.713 | 1.00 | 20.65 | C |
| ATOM | 13758 | CB | ASN | B | 365 | −36.425 | −18.756 | −23.691 | 1.00 | 20.74 | C |
| ATOM | 13761 | CG | ASN | B | 365 | −35.330 | −17.865 | −23.100 | 1.00 | 20.53 | C |
| ATOM | 13762 | OD1 | ASN | B | 365 | −34.553 | −17.229 | −23.830 | 1.00 | 18.26 | O |
| ATOM | 13763 | ND2 | ASN | B | 365 | −35.252 | −17.841 | −21.763 | 1.00 | 20.69 | N |
| ATOM | 13766 | C | ASN | B | 365 | −37.756 | −18.987 | −25.811 | 1.00 | 20.43 | C |
| ATOM | 13767 | O | ASN | B | 365 | −36.998 | −19.253 | −26.759 | 1.00 | 20.11 | O |
| ATOM | 13769 | N | ALA | B | 366 | −38.987 | −19.492 | −25.667 | 1.00 | 20.01 | N |
| ATOM | 13770 | CA | ALA | B | 366 | −39.618 | −20.340 | −26.665 | 1.00 | 19.70 | C |
| ATOM | 13772 | CB | ALA | B | 366 | −40.766 | −21.113 | −26.045 | 1.00 | 19.53 | C |
| ATOM | 13776 | C | ALA | B | 366 | −40.099 | −19.494 | −27.838 | 1.00 | 19.74 | C |

TABLE 3-7-continued

Coordinates of *P. tremuloides IspS*

| | | | | | | | | | | | |
|---|---|---|---|---|---|---|---|---|---|---|---|
| ATOM | 13777 | O | ALA | B | 366 | −39.846 | −19.824 | −28.989 | 1.00 | 19.61 | O |
| ATOM | 13779 | N | PHE | B | 367 | −40.791 | −18.399 | −27.553 | 1.00 | 19.99 | N |
| ATOM | 13780 | CA | PHE | B | 367 | −41.138 | −17.446 | −28.606 | 1.00 | 20.36 | C |
| ATOM | 13782 | CB | PHE | B | 367 | −41.805 | −16.194 | −28.026 | 1.00 | 20.62 | C |
| ATOM | 13785 | CG | PHE | B | 367 | −43.200 | −16.403 | −27.537 | 1.00 | 21.75 | C |
| ATOM | 13786 | CD1 | PHE | B | 367 | −44.136 | −17.071 | −28.315 | 1.00 | 23.00 | C |
| ATOM | 13788 | CE1 | PHE | B | 367 | −45.435 | −17.242 | −27.874 | 1.00 | 23.60 | C |
| ATOM | 13790 | CZ | PHE | B | 367 | −45.819 | −16.731 | −26.648 | 1.00 | 23.64 | C |
| ATOM | 13792 | CE2 | PHE | B | 367 | −44.901 | −16.049 | −25.871 | 1.00 | 23.56 | C |
| ATOM | 13794 | CD2 | PHE | B | 367 | −43.599 | −15.883 | −26.316 | 1.00 | 22.91 | C |
| ATOM | 13796 | C | PHE | B | 367 | −39.906 | −16.986 | −29.393 | 1.00 | 20.19 | C |
| ATOM | 13797 | O | PHE | B | 367 | −39.934 | −16.903 | −30.615 | 1.00 | 19.98 | O |
| ATOM | 13799 | N | LEU | B | 368 | −38.839 | −16.659 | −28.675 | 1.00 | 20.24 | N |
| ATOM | 13800 | CA | LEU | B | 368 | −37.629 | −16.161 | −29.298 | 1.00 | 20.31 | C |
| ATOM | 13802 | CB | LEU | B | 368 | −36.569 | −15.900 | −28.232 | 1.00 | 20.27 | C |
| ATOM | 13805 | CG | LEU | B | 368 | −35.235 | −15.313 | −28.694 | 1.00 | 20.12 | C |
| ATOM | 13807 | CD1 | LEU | B | 368 | −35.417 | −14.069 | −29.592 | 1.00 | 20.05 | C |
| ATOM | 13811 | CD2 | LEU | B | 368 | −34.409 | −14.987 | −27.465 | 1.00 | 18.60 | C |
| ATOM | 13815 | C | LEU | B | 368 | −37.122 | −17.179 | −30.295 | 1.00 | 20.53 | C |
| ATOM | 13816 | O | LEU | B | 368 | −36.844 | −16.844 | −31.446 | 1.00 | 20.49 | O |
| ATOM | 13818 | N | GLN | B | 369 | −37.032 | −18.426 | −29.832 | 1.00 | 20.80 | N |
| ATOM | 13819 | CA | GLN | B | 369 | −36.565 | −19.557 | −30.638 | 1.00 | 20.90 | C |
| ATOM | 13821 | CB | GLN | B | 369 | −36.614 | −20.857 | −29.815 | 1.00 | 20.98 | C |
| ATOM | 13824 | CG | GLN | B | 369 | −36.343 | −22.159 | −30.576 | 1.00 | 20.75 | C |
| ATOM | 13827 | CD | GLN | B | 369 | −34.946 | −22.238 | −31.126 | 1.00 | 20.29 | C |
| ATOM | 13828 | OE1 | GLN | B | 369 | −34.718 | −21.984 | −32.305 | 1.00 | 20.17 | O |
| ATOM | 13829 | NE2 | GLN | B | 369 | −33.996 | −22.581 | −30.272 | 1.00 | 20.33 | N |
| ATOM | 13832 | C | GLN | B | 369 | −37.365 | −19.718 | −31.910 | 1.00 | 21.04 | C |
| ATOM | 13833 | O | GLN | B | 369 | −36.803 | −20.097 | −32.929 | 1.00 | 20.82 | O |
| ATOM | 13835 | N | GLU | B | 370 | −38.668 | −19.453 | −31.863 | 1.00 | 21.80 | N |
| ATOM | 13836 | CA | GLU | B | 370 | −39.480 | −19.512 | −33.087 | 1.00 | 22.73 | C |
| ATOM | 13838 | CB | GLU | B | 370 | −40.996 | −19.518 | −32.801 | 1.00 | 23.18 | C |
| ATOM | 13841 | CG | GLU | B | 370 | −41.449 | −20.608 | −31.809 | 1.00 | 25.92 | C |
| ATOM | 13844 | CD | GLU | B | 370 | −42.927 | −21.064 | −31.957 | 1.00 | 29.74 | C |
| ATOM | 13845 | OE1 | GLU | B | 370 | −43.840 | −20.191 | −32.101 | 1.00 | 30.13 | O |
| ATOM | 13846 | OE2 | GLU | B | 370 | −43.156 | −22.316 | −31.892 | 1.00 | 31.94 | O |
| ATOM | 13847 | C | GLU | B | 370 | −39.079 | −18.358 | −34.016 | 1.00 | 22.62 | C |
| ATOM | 13848 | O | GLU | B | 370 | −38.933 | −18.565 | −35.221 | 1.00 | 22.53 | O |
| ATOM | 13850 | N | ALA | B | 371 | −38.864 | −17.166 | −33.456 | 1.00 | 22.65 | N |
| ATOM | 13851 | CA | ALA | B | 371 | −38.427 | −16.023 | −34.254 | 1.00 | 22.95 | C |
| ATOM | 13853 | CB | ALA | B | 371 | −38.375 | −14.753 | −33.424 | 1.00 | 22.97 | C |
| ATOM | 13857 | C | ALA | B | 371 | −37.070 | −16.296 | −34.891 | 1.00 | 23.13 | C |
| ATOM | 13858 | O | ALA | B | 371 | −36.900 | −16.063 | −36.091 | 1.00 | 23.38 | O |
| ATOM | 13860 | N | LYS | B | 372 | −36.113 | −16.804 | −34.107 | 1.00 | 23.15 | N |
| ATOM | 13861 | CA | LYS | B | 372 | −34.776 | −17.102 | −34.640 | 1.00 | 23.10 | C |
| ATOM | 13863 | CB | LYS | B | 372 | −33.808 | −17.633 | −33.575 | 1.00 | 22.85 | C |
| ATOM | 13866 | CG | LYS | B | 372 | −33.414 | −16.616 | −32.514 | 1.00 | 24.28 | C |
| ATOM | 13869 | CD | LYS | B | 372 | −31.973 | −16.806 | −31.969 | 1.00 | 26.34 | C |
| ATOM | 13872 | CE | LYS | B | 372 | −31.919 | −17.407 | −30.544 | 1.00 | 27.84 | C |
| ATOM | 13875 | NZ | LYS | B | 372 | −31.673 | −16.405 | −29.458 | 1.00 | 27.93 | N |
| ATOM | 13879 | C | LYS | B | 372 | −34.887 | −18.093 | −35.790 | 1.00 | 23.16 | C |
| ATOM | 13880 | O | LYS | B | 372 | −34.231 | −17.920 | −36.804 | 1.00 | 23.73 | O |
| ATOM | 13882 | N | TRP | B | 373 | −35.720 | −19.122 | −35.658 | 1.00 | 23.11 | N |
| ATOM | 13883 | CA | TRP | B | 373 | −35.844 | −20.094 | −36.742 | 1.00 | 22.99 | C |
| ATOM | 13885 | CB | TRP | B | 373 | −36.746 | −21.274 | −36.370 | 1.00 | 22.71 | C |
| ATOM | 13888 | CG | TRP | B | 373 | −36.081 | −22.343 | −35.562 | 1.00 | 20.71 | C |
| ATOM | 13889 | CD1 | TRP | B | 373 | −34.770 | −22.740 | −35.623 | 1.00 | 19.89 | C |
| ATOM | 13891 | NE1 | TRP | B | 373 | −34.540 | −23.757 | −34.734 | 1.00 | 19.05 | N |
| ATOM | 13893 | CE2 | TRP | B | 373 | −35.715 | −24.050 | −34.090 | 1.00 | 18.91 | C |
| ATOM | 13894 | CD2 | TRP | B | 373 | −36.707 | −23.184 | −34.599 | 1.00 | 18.41 | C |
| ATOM | 13895 | CE3 | TRP | B | 373 | −38.007 | −23.288 | −34.105 | 1.00 | 15.66 | C |
| ATOM | 13897 | CZ3 | TRP | B | 373 | −38.271 | −24.216 | −33.130 | 1.00 | 15.41 | C |
| ATOM | 13899 | CH2 | TRP | B | 373 | −37.276 | −25.069 | −32.647 | 1.00 | 16.33 | C |
| ATOM | 13901 | CZ2 | TRP | B | 373 | −35.994 | −25.005 | −33.112 | 1.00 | 17.53 | C |
| ATOM | 13903 | C | TRP | B | 373 | −36.374 | −19.416 | −37.991 | 1.00 | 23.59 | C |
| ATOM | 13904 | O | TRP | B | 373 | −35.878 | −19.653 | −39.096 | 1.00 | 23.60 | O |
| ATOM | 13906 | N | LEU | B | 374 | −37.374 | −18.559 | −37.801 | 1.00 | 24.32 | N |
| ATOM | 13907 | CA | LEU | B | 374 | −38.008 | −17.859 | −38.915 | 1.00 | 24.66 | C |
| ATOM | 13909 | CB | LEU | B | 374 | −39.181 | −17.019 | −38.428 | 1.00 | 24.85 | C |
| ATOM | 13912 | CG | LEU | B | 374 | −40.112 | −16.449 | −39.496 | 1.00 | 25.45 | C |
| ATOM | 13914 | CD1 | LEU | B | 374 | −41.002 | −17.535 | −40.070 | 1.00 | 24.83 | C |
| ATOM | 13918 | CD2 | LEU | B | 374 | −40.959 | −15.293 | −38.885 | 1.00 | 26.92 | C |
| ATOM | 13922 | C | LEU | B | 374 | −37.009 | −16.975 | −39.618 | 1.00 | 24.64 | C |
| ATOM | 13923 | O | LEU | B | 374 | −36.934 | −16.992 | −40.830 | 1.00 | 24.33 | O |
| ATOM | 13925 | N | TYR | B | 375 | −36.232 | −16.220 | −38.850 | 1.00 | 25.09 | N |
| ATOM | 13926 | CA | TYR | B | 375 | −35.283 | −15.274 | −39.433 | 1.00 | 25.71 | C |
| ATOM | 13928 | CB | TYR | B | 375 | −34.534 | −14.479 | −38.349 | 1.00 | 25.91 | C |
| ATOM | 13931 | CG | TYR | B | 375 | −33.536 | −13.468 | −38.892 | 1.00 | 27.11 | C |

TABLE 3-7-continued

Coordinates of *P. tremuloides IspS*

| | | | | | | | | | | | |
|---|---|---|---|---|---|---|---|---|---|---|---|
| ATOM | 13932 | CD1 | TYR | B | 375 | −33.950 | −12.200 | −39.305 | 1.00 | 27.98 | C |
| ATOM | 13934 | CE1 | TYR | B | 375 | −33.039 | −11.271 | −39.811 | 1.00 | 28.61 | C |
| ATOM | 13936 | CZ | TYR | B | 375 | −31.693 | −11.605 | −39.904 | 1.00 | 29.13 | C |
| ATOM | 13937 | OH | TYR | B | 375 | −30.790 | −10.685 | −40.397 | 1.00 | 29.83 | O |
| ATOM | 13939 | CE2 | TYR | B | 375 | −31.256 | −12.863 | −39.501 | 1.00 | 28.79 | C |
| ATOM | 13941 | CD2 | TYR | B | 375 | −32.177 | −13.783 | −38.995 | 1.00 | 28.03 | C |
| ATOM | 13943 | C | TYR | B | 375 | −34.305 | −16.036 | −40.301 | 1.00 | 25.64 | C |
| ATOM | 13944 | O | TYR | B | 375 | −34.201 | −15.788 | −41.503 | 1.00 | 25.74 | O |
| ATOM | 13946 | N | ASN | B | 376 | −33.635 | −17.000 | −39.685 | 1.00 | 25.73 | N |
| ATOM | 13947 | CA | ASN | B | 376 | −32.599 | −17.777 | −40.346 | 1.00 | 25.78 | C |
| ATOM | 13949 | CB | ASN | B | 376 | −31.739 | −18.497 | −39.303 | 1.00 | 25.73 | C |
| ATOM | 13952 | CG | ASN | B | 376 | −31.155 | −17.565 | −38.273 | 1.00 | 25.13 | C |
| ATOM | 13953 | OD1 | ASN | B | 376 | −30.491 | −16.590 | −38.601 | 1.00 | 25.53 | O |
| ATOM | 13954 | ND2 | ASN | B | 376 | −31.389 | −17.874 | −37.013 | 1.00 | 24.64 | N |
| ATOM | 13957 | C | ASN | B | 376 | −33.126 | −18.824 | −41.332 | 1.00 | 26.04 | C |
| ATOM | 13958 | O | ASN | B | 376 | −32.343 | −19.644 | −41.807 | 1.00 | 26.36 | O |
| ATOM | 13960 | N | LYS | B | 377 | −34.428 | −18.824 | −41.632 | 1.00 | 26.16 | N |
| ATOM | 13961 | CA | LYS | B | 377 | −35.012 | −19.811 | −42.552 | 1.00 | 26.27 | C |
| ATOM | 13963 | CB | LYS | B | 377 | −34.575 | −19.538 | −44.010 | 1.00 | 26.51 | C |
| ATOM | 13966 | CG | LYS | B | 377 | −35.470 | −18.561 | −44.802 | 1.00 | 28.01 | C |
| ATOM | 13969 | CD | LYS | B | 377 | −34.629 | −17.592 | −45.667 | 1.00 | 29.99 | C |
| ATOM | 13972 | CE | LYS | B | 377 | −35.493 | −16.605 | −46.465 | 1.00 | 31.02 | C |
| ATOM | 13975 | NZ | LYS | B | 377 | −36.420 | −15.819 | −45.589 | 1.00 | 32.17 | N |
| ATOM | 13979 | C | LYS | B | 377 | −34.647 | −21.243 | −42.150 | 1.00 | 25.93 | C |
| ATOM | 13980 | O | LYS | B | 377 | −34.380 | −22.084 | −43.003 | 1.00 | 25.82 | O |
| ATOM | 13982 | N | SER | B | 378 | −34.637 | −21.522 | −40.852 | 1.00 | 25.65 | N |
| ATOM | 13983 | CA | SER | B | 378 | −34.324 | −22.860 | −40.385 | 1.00 | 25.54 | C |
| ATOM | 13985 | CB | SER | B | 378 | −34.132 | −22.877 | −38.882 | 1.00 | 25.41 | C |
| ATOM | 13988 | OG | SER | B | 378 | −32.905 | −22.269 | −38.570 | 1.00 | 25.67 | O |
| ATOM | 13990 | C | SER | B | 378 | −35.412 | −23.838 | −40.790 | 1.00 | 25.62 | C |
| ATOM | 13991 | O | SER | B | 378 | −36.495 | −23.435 | −41.199 | 1.00 | 25.70 | O |
| ATOM | 13993 | N | THR | B | 379 | −35.108 | −25.129 | −40.690 | 1.00 | 25.66 | N |
| ATOM | 13994 | CA | THR | B | 379 | −36.038 | −26.175 | −41.097 | 1.00 | 25.55 | C |
| ATOM | 13996 | CB | THR | B | 379 | −35.788 | −26.635 | −42.546 | 1.00 | 25.59 | C |
| ATOM | 13998 | OG1 | THR | B | 379 | −34.391 | −26.899 | −42.736 | 1.00 | 25.46 | O |
| ATOM | 14000 | CG2 | THR | B | 379 | −36.255 | −25.574 | −43.528 | 1.00 | 25.88 | C |
| ATOM | 14004 | C | THR | B | 379 | −35.886 | −27.348 | −40.160 | 1.00 | 25.45 | C |
| ATOM | 14005 | O | THR | B | 379 | −35.372 | −28.393 | −40.548 | 1.00 | 25.70 | O |
| ATOM | 14007 | N | PRO | B | 380 | −36.335 | −27.179 | −38.915 | 1.00 | 25.37 | N |
| ATOM | 14008 | CA | PRO | B | 380 | −36.144 | −28.182 | −37.876 | 1.00 | 25.22 | C |
| ATOM | 14010 | CB | PRO | B | 380 | −36.500 | −27.437 | −36.583 | 1.00 | 25.19 | C |
| ATOM | 14013 | CG | PRO | B | 380 | −36.643 | −26.021 | −36.955 | 1.00 | 25.83 | C |
| ATOM | 14016 | CD | PRO | B | 380 | −37.025 | −25.998 | −38.390 | 1.00 | 25.71 | C |
| ATOM | 14019 | C | PRO | B | 380 | −37.052 | −29.379 | −38.009 | 1.00 | 24.82 | C |
| ATOM | 14020 | O | PRO | B | 380 | −38.143 | −29.280 | −38.575 | 1.00 | 24.84 | O |
| ATOM | 14021 | N | THR | B | 381 | −36.607 | −30.493 | −37.436 | 1.00 | 24.42 | N |
| ATOM | 14022 | CA | THR | B | 381 | −37.386 | −31.712 | −37.429 | 1.00 | 23.99 | C |
| ATOM | 14024 | CB | THR | B | 381 | −36.614 | −32.873 | −36.789 | 1.00 | 23.99 | C |
| ATOM | 14026 | OG1 | THR | B | 381 | −36.339 | −32.575 | −35.418 | 1.00 | 24.02 | O |
| ATOM | 14028 | CG2 | THR | B | 381 | −35.302 | −33.117 | −37.524 | 1.00 | 23.76 | C |
| ATOM | 14032 | C | THR | B | 381 | −38.649 | −31.461 | −36.636 | 1.00 | 23.78 | C |
| ATOM | 14033 | O | THR | B | 381 | −38.700 | −30.548 | −35.813 | 1.00 | 23.89 | O |
| ATOM | 14035 | N | PHE | B | 382 | −39.672 | −32.267 | −36.889 | 1.00 | 23.53 | N |
| ATOM | 14036 | CA | PHE | B | 382 | −40.905 | −32.204 | −36.105 | 1.00 | 22.97 | C |
| ATOM | 14038 | CB | PHE | B | 382 | −41.870 | −33.305 | −36.527 | 1.00 | 22.89 | C |
| ATOM | 14041 | CG | PHE | B | 382 | −43.079 | −33.394 | −35.655 | 1.00 | 22.26 | C |
| ATOM | 14042 | CD1 | PHE | B | 382 | −44.189 | −32.601 | −35.910 | 1.00 | 21.65 | C |
| ATOM | 14044 | CE1 | PHE | B | 382 | −45.300 | −32.672 | −35.099 | 1.00 | 20.87 | C |
| ATOM | 14046 | CZ | PHE | B | 382 | −45.310 | −33.534 | −34.016 | 1.00 | 20.36 | C |
| ATOM | 14048 | CE2 | PHE | B | 382 | −44.204 | −34.317 | −33.744 | 1.00 | 20.52 | C |
| ATOM | 14050 | CD2 | PHE | B | 382 | −43.098 | −34.243 | −34.556 | 1.00 | 21.17 | C |
| ATOM | 14052 | C | PHE | B | 382 | −40.677 | −32.329 | −34.605 | 1.00 | 22.69 | C |
| ATOM | 14053 | O | PHE | B | 382 | −41.341 | −31.657 | −33.834 | 1.00 | 22.44 | O |
| ATOM | 14055 | N | ASP | B | 383 | −39.764 | −33.205 | −34.191 | 1.00 | 22.52 | N |
| ATOM | 14056 | CA | ASP | B | 383 | −39.491 | −33.375 | −32.765 | 1.00 | 22.50 | C |
| ATOM | 14058 | CB | ASP | B | 383 | −38.531 | −34.525 | −32.527 | 1.00 | 22.43 | C |
| ATOM | 14061 | CG | ASP | B | 383 | −39.174 | −35.863 | −32.711 | 1.00 | 22.71 | C |
| ATOM | 14062 | OD1 | ASP | B | 383 | −40.359 | −35.945 | −33.074 | 1.00 | 22.89 | O |
| ATOM | 14063 | OD2 | ASP | B | 383 | −38.470 | −36.856 | −32.492 | 1.00 | 25.17 | O |
| ATOM | 14064 | C | ASP | B | 383 | −38.954 | −32.116 | −32.091 | 1.00 | 22.43 | C |
| ATOM | 14065 | O | ASP | B | 383 | −39.438 | −31.758 | −31.014 | 1.00 | 22.40 | O |
| ATOM | 14067 | N | ASP | B | 384 | −37.966 | −31.464 | −32.713 | 1.00 | 22.37 | N |
| ATOM | 14068 | CA | ASP | B | 384 | −37.422 | −30.191 | −32.213 | 1.00 | 22.61 | C |
| ATOM | 14070 | CB | ASP | B | 384 | −36.317 | −29.648 | −33.124 | 1.00 | 22.82 | C |
| ATOM | 14073 | CG | ASP | B | 384 | −34.963 | −30.208 | −32.807 | 1.00 | 23.40 | C |
| ATOM | 14074 | OD1 | ASP | B | 384 | −34.847 | −30.973 | −31.832 | 1.00 | 25.33 | O |
| ATOM | 14075 | OD2 | ASP | B | 384 | −34.009 | −29.891 | −33.545 | 1.00 | 24.26 | O |
| ATOM | 14076 | C | ASP | B | 384 | −38.482 | −29.113 | −32.130 | 1.00 | 22.56 | C |

TABLE 3-7-continued

Coordinates of *P. tremuloides IspS*

| | | | | | | | | | | | |
|---|---|---|---|---|---|---|---|---|---|---|---|
| ATOM | 14077 | O | ASP | B | 384 | −38.598 | −28.429 | −31.108 | 1.00 | 22.48 | O |
| ATOM | 14079 | N | TYR | B | 385 | −39.227 | −28.963 | −33.227 | 1.00 | 22.36 | N |
| ATOM | 14080 | CA | TYR | B | 385 | −40.170 | −27.870 | −33.402 | 1.00 | 22.18 | C |
| ATOM | 14082 | CB | TYR | B | 385 | −40.738 | −27.867 | −34.812 | 1.00 | 22.05 | C |
| ATOM | 14085 | CG | TYR | B | 385 | −41.818 | −26.834 | −35.019 | 1.00 | 22.60 | C |
| ATOM | 14086 | CD1 | TYR | B | 385 | −41.493 | −25.553 | −35.437 | 1.00 | 23.64 | C |
| ATOM | 14088 | CE1 | TYR | B | 385 | −42.462 | −24.580 | −35.630 | 1.00 | 25.00 | C |
| ATOM | 14090 | CZ | TYR | B | 385 | −43.788 | −24.882 | −35.410 | 1.00 | 26.86 | C |
| ATOM | 14091 | OH | TYR | B | 385 | −44.734 | −23.883 | −35.622 | 1.00 | 28.48 | O |
| ATOM | 14093 | CE2 | TYR | B | 385 | −44.149 | −26.171 | −34.980 | 1.00 | 25.95 | C |
| ATOM | 14095 | CD2 | TYR | B | 385 | −43.158 | −27.133 | −34.790 | 1.00 | 23.94 | C |
| ATOM | 14097 | C | TYR | B | 385 | −41.319 | −27.986 | −32.446 | 1.00 | 22.13 | C |
| ATOM | 14098 | O | TYR | B | 385 | −41.703 | −27.017 | −31.808 | 1.00 | 22.95 | O |
| ATOM | 14100 | N | PHE | B | 386 | −41.899 | −29.169 | −32.380 | 1.00 | 21.80 | N |
| ATOM | 14101 | CA | PHE | B | 386 | −43.048 | −29.394 | −31.525 | 1.00 | 21.62 | C |
| ATOM | 14103 | CB | PHE | B | 386 | −43.624 | −30.795 | −31.768 | 1.00 | 21.73 | C |
| ATOM | 14106 | CG | PHE | B | 386 | −44.834 | −31.104 | −30.952 | 1.00 | 21.27 | C |
| ATOM | 14107 | CD1 | PHE | B | 386 | −46.034 | −30.447 | −31.196 | 1.00 | 22.55 | C |
| ATOM | 14109 | CE1 | PHE | B | 386 | −47.164 | −30.732 | −30.448 | 1.00 | 23.14 | C |
| ATOM | 14111 | CZ | PHE | B | 386 | −47.095 | −31.699 | −29.446 | 1.00 | 23.20 | C |
| ATOM | 14113 | CE2 | PHE | B | 386 | −45.896 | −32.358 | −29.208 | 1.00 | 21.57 | C |
| ATOM | 14115 | CD2 | PHE | B | 386 | −44.781 | −32.057 | −29.959 | 1.00 | 20.29 | C |
| ATOM | 14117 | C | PHE | B | 386 | −42.630 | −29.226 | −30.073 | 1.00 | 21.34 | C |
| ATOM | 14118 | O | PHE | B | 386 | −43.353 | −28.639 | −29.284 | 1.00 | 21.44 | O |
| ATOM | 14120 | N | GLY | B | 387 | −41.447 | −29.725 | −29.736 | 1.00 | 20.84 | N |
| ATOM | 14121 | CA | GLY | B | 387 | −40.935 | −29.618 | −28.387 | 1.00 | 20.57 | C |
| ATOM | 14124 | C | GLY | B | 387 | −40.854 | −28.186 | −27.916 | 1.00 | 20.26 | C |
| ATOM | 14125 | O | GLY | B | 387 | −40.930 | −27.908 | −26.724 | 1.00 | 20.86 | O |
| ATOM | 14127 | N | ASN | B | 388 | −40.691 | −27.268 | −28.852 | 1.00 | 19.81 | N |
| ATOM | 14128 | CA | ASN | B | 388 | −40.758 | −25.853 | −28.536 | 1.00 | 19.51 | C |
| ATOM | 14130 | CB | ASN | B | 388 | −39.877 | −25.086 | −29.508 | 1.00 | 19.42 | C |
| ATOM | 14133 | CG | ASN | B | 388 | −39.593 | −23.700 | −29.045 | 1.00 | 19.26 | C |
| ATOM | 14134 | OD1 | ASN | B | 388 | −38.916 | −23.513 | −28.038 | 1.00 | 18.93 | O |
| ATOM | 14135 | ND2 | ASN | B | 388 | −40.105 | −22.709 | −29.774 | 1.00 | 17.99 | N |
| ATOM | 14138 | C | ASN | B | 388 | −42.200 | −25.320 | −28.604 | 1.00 | 19.41 | C |
| ATOM | 14139 | O | ASN | B | 388 | −42.591 | −24.447 | −27.833 | 1.00 | 19.58 | O |
| ATOM | 14141 | N | ALA | B | 389 | −42.989 | −25.848 | −29.532 | 1.00 | 19.11 | N |
| ATOM | 14142 | CA | ALA | B | 389 | −44.313 | −25.307 | −29.808 | 1.00 | 18.87 | C |
| ATOM | 14144 | CB | ALA | B | 389 | −44.897 | −25.949 | −31.060 | 1.00 | 18.87 | C |
| ATOM | 14148 | C | ALA | B | 389 | −45.264 | −25.460 | −28.634 | 1.00 | 18.51 | C |
| ATOM | 14149 | O | ALA | B | 389 | −45.916 | −24.511 | −28.262 | 1.00 | 18.33 | O |
| ATOM | 14151 | N | TRP | B | 390 | −45.344 | −26.652 | −28.054 | 1.00 | 18.73 | N |
| ATOM | 14152 | CA | TRP | B | 390 | −46.258 | −26.887 | −26.935 | 1.00 | 18.74 | C |
| ATOM | 14154 | CB | TRP | B | 390 | −46.389 | −28.377 | −26.569 | 1.00 | 18.75 | C |
| ATOM | 14157 | CG | TRP | B | 390 | −45.166 | −29.122 | −26.019 | 1.00 | 18.46 | C |
| ATOM | 14158 | CD1 | TRP | B | 390 | −44.390 | −30.001 | −26.705 | 1.00 | 18.75 | C |
| ATOM | 14160 | NE1 | TRP | B | 390 | −43.417 | −30.519 | −25.897 | 1.00 | 17.56 | N |
| ATOM | 14162 | CE2 | TRP | B | 390 | −43.559 | −30.005 | −24.642 | 1.00 | 16.67 | C |
| ATOM | 14163 | CD2 | TRP | B | 390 | −44.661 | −29.124 | −24.674 | 1.00 | 17.50 | C |
| ATOM | 14164 | CE3 | TRP | B | 390 | −45.008 | −28.448 | −23.505 | 1.00 | 18.38 | C |
| ATOM | 14166 | CZ3 | TRP | B | 390 | −44.251 | −28.685 | −22.347 | 1.00 | 18.34 | C |
| ATOM | 14168 | CH2 | TRP | B | 390 | −43.164 | −29.573 | −22.361 | 1.00 | 16.75 | C |
| ATOM | 14170 | CZ2 | TRP | B | 390 | −42.805 | −30.234 | −23.495 | 1.00 | 15.75 | C |
| ATOM | 14172 | C | TRP | B | 390 | −45.861 | −26.066 | −25.727 | 1.00 | 18.91 | C |
| ATOM | 14173 | O | TRP | B | 390 | −46.707 | −25.691 | −24.919 | 1.00 | 19.02 | O |
| ATOM | 14175 | N | LYS | B | 391 | −44.570 | −25.787 | −25.612 | 1.00 | 18.95 | N |
| ATOM | 14176 | CA | LYS | B | 391 | −44.085 | −24.810 | −24.643 | 1.00 | 18.85 | C |
| ATOM | 14178 | CB | LYS | B | 391 | −42.544 | −24.888 | −24.508 | 1.00 | 19.52 | C |
| ATOM | 14181 | CG | LYS | B | 391 | −42.023 | −25.373 | −23.143 | 1.00 | 21.17 | C |
| ATOM | 14184 | CD | LYS | B | 391 | −40.516 | −25.689 | −23.191 | 1.00 | 22.87 | C |
| ATOM | 14187 | CE | LYS | B | 391 | −40.251 | −27.159 | −23.508 | 1.00 | 23.91 | C |
| ATOM | 14190 | NZ | LYS | B | 391 | −38.938 | −27.354 | −24.191 | 1.00 | 25.44 | N |
| ATOM | 14194 | C | LYS | B | 391 | −44.537 | −23.400 | −25.032 | 1.00 | 17.57 | C |
| ATOM | 14195 | O | LYS | B | 391 | −44.937 | −22.629 | −24.180 | 1.00 | 17.66 | O |
| ATOM | 14197 | N | SER | B | 392 | −44.490 | −23.068 | −26.314 | 1.00 | 16.65 | N |
| ATOM | 14198 | CA | SER | B | 392 | −44.879 | −21.718 | −26.764 | 1.00 | 16.27 | C |
| ATOM | 14200 | CB | SER | B | 392 | −44.241 | −21.375 | −28.119 | 1.00 | 16.22 | C |
| ATOM | 14203 | OG | SER | B | 392 | −44.937 | −21.969 | −29.207 | 1.00 | 15.94 | O |
| ATOM | 14205 | C | SER | B | 392 | −46.384 | −21.504 | −26.866 | 1.00 | 15.87 | C |
| ATOM | 14206 | O | SER | B | 392 | −46.825 | −20.395 | −27.093 | 1.00 | 15.56 | O |
| ATOM | 14208 | N | SER | B | 393 | −47.167 | −22.568 | −26.724 | 1.00 | 15.92 | N |
| ATOM | 14209 | CA | SER | B | 393 | −48.629 | −22.474 | −26.718 | 1.00 | 15.80 | C |
| ATOM | 14211 | CB | SER | B | 393 | −49.240 | −23.867 | −26.630 | 1.00 | 15.78 | C |
| ATOM | 14214 | OG | SER | B | 393 | −49.025 | −24.426 | −25.348 | 1.00 | 15.00 | O |
| ATOM | 14216 | C | SER | B | 393 | −49.097 | −21.646 | −25.533 | 1.00 | 15.94 | C |
| ATOM | 14217 | O | SER | B | 393 | −50.115 | −20.948 | −25.599 | 1.00 | 15.60 | O |
| ATOM | 14219 | N | SER | B | 394 | −48.296 | −21.740 | −24.471 | 1.00 | 16.14 | N |
| ATOM | 14220 | CA | SER | B | 394 | −48.487 | −21.091 | −23.177 | 1.00 | 16.31 | C |

TABLE 3-7-continued

| Coordinates of *P. tremuloides IspS* | | | | | | | | | | | |
|---|---|---|---|---|---|---|---|---|---|---|---|
| ATOM | 14222 | CB | SER | B | 394 | −49.062 | −19.662 | −23.271 | 1.00 | 16.18 | C |
| ATOM | 14225 | OG | SER | B | 394 | −50.472 | −19.649 | −23.358 | 1.00 | 16.57 | O |
| ATOM | 14227 | C | SER | B | 394 | −49.316 | −22.006 | −22.297 | 1.00 | 16.34 | C |
| ATOM | 14228 | O | SER | B | 394 | −49.822 | −21.595 | −21.261 | 1.00 | 16.47 | O |
| ATOM | 14230 | N | GLY | B | 395 | −49.403 | −23.268 | −22.702 | 1.00 | 16.55 | N |
| ATOM | 14231 | CA | GLY | B | 395 | −50.103 | −24.282 | −21.927 | 1.00 | 16.79 | C |
| ATOM | 14234 | C | GLY | B | 395 | −49.543 | −24.391 | −20.534 | 1.00 | 16.80 | C |
| ATOM | 14235 | O | GLY | B | 395 | −50.222 | −24.083 | −19.556 | 1.00 | 16.74 | O |
| ATOM | 14237 | N | PRO | B | 396 | −48.291 | −24.824 | −20.430 | 1.00 | 17.07 | N |
| ATOM | 14238 | CA | PRO | B | 396 | −47.698 | −24.930 | −19.103 | 1.00 | 17.18 | C |
| ATOM | 14240 | CB | PRO | B | 396 | −46.273 | −25.399 | −19.386 | 1.00 | 17.09 | C |
| ATOM | 14243 | CG | PRO | B | 396 | −46.087 | −25.237 | −20.874 | 1.00 | 17.77 | C |
| ATOM | 14246 | CD | PRO | B | 396 | −47.424 | −25.390 | −21.470 | 1.00 | 17.20 | C |
| ATOM | 14249 | C | PRO | B | 396 | −47.707 | −23.615 | −18.313 | 1.00 | 17.17 | C |
| ATOM | 14250 | O | PRO | B | 396 | −47.921 | −23.644 | −17.089 | 1.00 | 17.10 | O |
| ATOM | 14251 | N | LEU | B | 397 | −47.499 | −22.475 | −18.983 | 1.00 | 17.04 | N |
| ATOM | 14252 | CA | LEU | B | 397 | −47.513 | −21.183 | −18.261 | 1.00 | 16.77 | C |
| ATOM | 14254 | CB | LEU | B | 397 | −47.116 | −19.969 | −19.135 | 1.00 | 16.84 | C |
| ATOM | 14257 | CG | LEU | B | 397 | −47.145 | −18.576 | −18.458 | 1.00 | 16.91 | C |
| ATOM | 14259 | CD1 | LEU | B | 397 | −46.577 | −18.641 | −17.096 | 1.00 | 18.36 | C |
| ATOM | 14263 | CD2 | LEU | B | 397 | −46.373 | −17.515 | −19.196 | 1.00 | 16.88 | C |
| ATOM | 14267 | C | LEU | B | 397 | −48.894 | −20.988 | −17.682 | 1.00 | 16.24 | C |
| ATOM | 14268 | O | LEU | B | 397 | −49.051 | −20.710 | −16.494 | 1.00 | 16.09 | O |
| ATOM | 14270 | N | GLN | B | 398 | −49.902 | −21.173 | −18.515 | 1.00 | 15.72 | N |
| ATOM | 14271 | CA | GLN | B | 398 | −51.262 | −21.093 | −18.024 | 1.00 | 15.49 | C |
| ATOM | 14273 | CB | GLN | B | 398 | −52.267 | −21.387 | −19.120 | 1.00 | 15.51 | C |
| ATOM | 14276 | CG | GLN | B | 398 | −52.371 | −20.275 | −20.118 | 1.00 | 16.12 | C |
| ATOM | 14279 | CD | GLN | B | 398 | −53.436 | −20.545 | −21.114 | 1.00 | 17.86 | C |
| ATOM | 14280 | OE1 | GLN | B | 398 | −54.509 | −21.028 | −20.757 | 1.00 | 20.99 | O |
| ATOM | 14281 | NE2 | GLN | B | 398 | −53.170 | −20.239 | −22.374 | 1.00 | 18.31 | N |
| ATOM | 14284 | C | GLN | B | 398 | −51.471 | −22.040 | −16.873 | 1.00 | 15.03 | C |
| ATOM | 14285 | O | GLN | B | 398 | −51.974 | −21.638 | −15.843 | 1.00 | 15.21 | O |
| ATOM | 14287 | N | LEU | B | 399 | −51.065 | −23.291 | −17.022 | 1.00 | 14.72 | N |
| ATOM | 14288 | CA | LEU | B | 399 | −51.361 | −24.254 | −15.978 | 1.00 | 14.65 | C |
| ATOM | 14290 | CB | LEU | B | 399 | −51.201 | −25.688 | −16.475 | 1.00 | 14.44 | C |
| ATOM | 14293 | CG | LEU | B | 399 | −52.250 | −26.191 | −17.478 | 1.00 | 14.28 | C |
| ATOM | 14295 | CD1 | LEU | B | 399 | −51.907 | −27.633 | −17.846 | 1.00 | 15.50 | C |
| ATOM | 14299 | CD2 | LEU | B | 399 | −53.713 | −26.077 | −16.986 | 1.00 | 10.96 | C |
| ATOM | 14303 | C | LEU | B | 399 | −50.554 | −23.995 | −14.704 | 1.00 | 14.88 | C |
| ATOM | 14304 | O | LEU | B | 399 | −51.100 | −24.161 | −13.618 | 1.00 | 15.21 | O |
| ATOM | 14306 | N | ILE | B | 400 | −49.291 | −23.562 | −14.810 | 1.00 | 14.91 | N |
| ATOM | 14307 | CA | ILE | B | 400 | −48.532 | −23.174 | −13.607 | 1.00 | 14.89 | C |
| ATOM | 14309 | CB | ILE | B | 400 | −47.158 | −22.574 | −13.907 | 1.00 | 15.19 | C |
| ATOM | 14311 | CG1 | ILE | B | 400 | −46.189 | −23.674 | −14.353 | 1.00 | 16.76 | C |
| ATOM | 14314 | CD1 | ILE | B | 400 | −44.777 | −23.162 | −14.716 | 1.00 | 18.19 | C |
| ATOM | 14318 | CG2 | ILE | B | 400 | −46.603 | −21.906 | −12.665 | 1.00 | 13.65 | C |
| ATOM | 14322 | C | ILE | B | 400 | −49.288 | −22.137 | −12.819 | 1.00 | 14.77 | C |
| ATOM | 14323 | O | ILE | B | 400 | −49.485 | −22.302 | −11.632 | 1.00 | 15.36 | O |
| ATOM | 14325 | N | PHE | B | 401 | −49.717 | −21.071 | −13.486 | 1.00 | 14.59 | N |
| ATOM | 14326 | CA | PHE | B | 401 | −50.491 | −20.001 | −12.844 | 1.00 | 14.22 | C |
| ATOM | 14328 | CB | PHE | B | 401 | −50.825 | −18.900 | −13.845 | 1.00 | 14.12 | C |
| ATOM | 14331 | CG | PHE | B | 401 | −49.803 | −17.790 | −13.872 | 1.00 | 13.83 | C |
| ATOM | 14332 | CD1 | PHE | B | 401 | −50.012 | −16.623 | −13.173 | 1.00 | 12.77 | C |
| ATOM | 14334 | CE1 | PHE | B | 401 | −49.074 | −15.629 | −13.189 | 1.00 | 13.09 | C |
| ATOM | 14336 | CZ | PHE | B | 401 | −47.906 | −15.781 | −13.902 | 1.00 | 12.96 | C |
| ATOM | 14338 | CE2 | PHE | B | 401 | −47.684 | −16.928 | −14.592 | 1.00 | 12.86 | C |
| ATOM | 14340 | CD2 | PHE | B | 401 | −48.622 | −17.932 | −14.574 | 1.00 | 13.30 | C |
| ATOM | 14342 | C | PHE | B | 401 | −51.765 | −20.478 | −12.212 | 1.00 | 14.26 | C |
| ATOM | 14343 | O | PHE | B | 401 | −52.184 | −19.944 | −11.207 | 1.00 | 13.90 | O |
| ATOM | 14345 | N | ALA | B | 402 | −52.377 | −21.480 | −12.828 | 1.00 | 15.09 | N |
| ATOM | 14346 | CA | ALA | B | 402 | −53.641 | −22.054 | −12.364 | 1.00 | 15.76 | C |
| ATOM | 14348 | CB | ALA | B | 402 | −54.264 | −22.899 | −13.454 | 1.00 | 15.57 | C |
| ATOM | 14352 | C | ALA | B | 402 | −53.417 | −22.896 | −11.129 | 1.00 | 16.63 | C |
| ATOM | 14353 | O | ALA | B | 402 | −54.284 | −22.970 | −10.259 | 1.00 | 17.00 | O |
| ATOM | 14355 | N | TYR | B | 403 | −52.253 | −23.544 | −11.060 | 1.00 | 17.50 | N |
| ATOM | 14356 | CA | TYR | B | 403 | −51.885 | −24.317 | −9.894 | 1.00 | 17.86 | C |
| ATOM | 14358 | CB | TYR | B | 403 | −50.486 | −24.911 | −10.038 | 1.00 | 17.73 | C |
| ATOM | 14361 | CG | TYR | B | 403 | −50.006 | −25.576 | −8.764 | 1.00 | 18.24 | C |
| ATOM | 14362 | CD1 | TYR | B | 403 | −50.401 | −26.867 | −8.436 | 1.00 | 18.12 | C |
| ATOM | 14364 | CE1 | TYR | B | 403 | −49.971 | −27.476 | −7.273 | 1.00 | 18.07 | C |
| ATOM | 14366 | CZ | TYR | B | 403 | −49.145 | −26.790 | −6.409 | 1.00 | 18.62 | C |
| ATOM | 14367 | OH | TYR | B | 403 | −48.727 | −27.383 | −5.244 | 1.00 | 17.70 | O |
| ATOM | 14369 | CE2 | TYR | B | 403 | −48.748 | −25.499 | −6.703 | 1.00 | 18.93 | C |
| ATOM | 14371 | CD2 | TYR | B | 403 | −49.177 | −24.901 | −7.876 | 1.00 | 18.88 | C |
| ATOM | 14373 | C | TYR | B | 403 | −51.966 | −23.461 | −8.630 | 1.00 | 18.48 | C |
| ATOM | 14374 | O | TYR | B | 403 | −52.494 | −23.908 | −7.616 | 1.00 | 18.66 | O |
| ATOM | 14376 | N | PHE | B | 404 | −51.468 | −22.232 | −8.682 | 1.00 | 18.91 | N |
| ATOM | 14377 | CA | PHE | B | 404 | −51.400 | −21.430 | −7.468 | 1.00 | 19.53 | C |

TABLE 3-7-continued

Coordinates of *P. tremuloides IspS*

| | | | | | | | | | | | |
|---|---|---|---|---|---|---|---|---|---|---|---|
| ATOM | 14379 | CB | PHE | B | 404 | −50.395 | −20.325 | −7.644 | 1.00 | 19.35 | C |
| ATOM | 14382 | CG | PHE | B | 404 | −49.014 | −20.808 | −7.799 | 1.00 | 18.79 | C |
| ATOM | 14383 | CD1 | PHE | B | 404 | −48.311 | −21.246 | −6.701 | 1.00 | 17.67 | C |
| ATOM | 14385 | CE1 | PHE | B | 404 | −47.001 | −21.683 | −6.832 | 1.00 | 18.44 | C |
| ATOM | 14387 | CZ | PHE | B | 404 | −46.384 | −21.688 | −8.078 | 1.00 | 18.44 | C |
| ATOM | 14389 | CE2 | PHE | B | 404 | −47.083 | −21.245 | −9.190 | 1.00 | 18.79 | C |
| ATOM | 14391 | CD2 | PHE | B | 404 | −48.396 | −20.805 | −9.047 | 1.00 | 18.90 | C |
| ATOM | 14393 | C | PHE | B | 404 | −52.733 | −20.817 | −7.072 | 1.00 | 20.49 | C |
| ATOM | 14394 | O | PHE | B | 404 | −52.925 | −20.389 | −5.924 | 1.00 | 19.95 | O |
| ATOM | 14396 | N | ALA | B | 405 | −53.636 | −20.756 | −8.043 | 1.00 | 21.92 | N |
| ATOM | 14397 | CA | ALA | B | 405 | −54.918 | −20.106 | −7.872 | 1.00 | 23.09 | C |
| ATOM | 14399 | CB | ALA | B | 405 | −55.333 | −19.426 | −9.167 | 1.00 | 23.15 | C |
| ATOM | 14403 | C | ALA | B | 405 | −55.959 | −21.113 | −7.446 | 1.00 | 24.23 | C |
| ATOM | 14404 | O | ALA | B | 405 | −57.003 | −20.726 | −6.925 | 1.00 | 24.33 | O |
| ATOM | 14406 | N | VAL | B | 406 | −55.657 | −22.399 | −7.662 | 1.00 | 25.80 | N |
| ATOM | 14407 | CA | VAL | B | 406 | −56.569 | −23.511 | −7.355 | 1.00 | 26.88 | C |
| ATOM | 14409 | CB | VAL | B | 406 | −56.640 | −24.514 | −8.512 | 1.00 | 26.64 | C |
| ATOM | 14411 | CG1 | VAL | B | 406 | −57.132 | −25.854 | −8.012 | 1.00 | 27.24 | C |
| ATOM | 14415 | CG2 | VAL | B | 406 | −57.547 | −23.986 | −9.593 | 1.00 | 26.45 | C |
| ATOM | 14419 | C | VAL | B | 406 | −56.161 | −24.266 | −6.094 | 1.00 | 27.91 | C |
| ATOM | 14420 | O | VAL | B | 406 | −56.932 | −24.345 | −5.155 | 1.00 | 28.28 | O |
| ATOM | 14422 | N | VAL | B | 407 | −54.954 | −24.825 | −6.087 | 1.00 | 29.25 | N |
| ATOM | 14423 | CA | VAL | B | 407 | −54.443 | −25.573 | −4.941 | 1.00 | 30.16 | C |
| ATOM | 14425 | CB | VAL | B | 407 | −53.128 | −26.276 | −5.279 | 1.00 | 30.04 | C |
| ATOM | 14427 | CG1 | VAL | B | 407 | −52.482 | −26.831 | −4.032 | 1.00 | 30.42 | C |
| ATOM | 14431 | CG2 | VAL | B | 407 | −53.378 | −27.376 | −6.280 | 1.00 | 30.14 | C |
| ATOM | 14435 | C | VAL | B | 407 | −54.208 | −24.646 | −3.755 | 1.00 | 31.34 | C |
| ATOM | 14436 | O | VAL | B | 407 | −53.535 | −23.618 | −3.876 | 1.00 | 31.46 | O |
| ATOM | 14438 | N | GLN | B | 408 | −54.753 | −25.032 | −2.604 | 1.00 | 32.63 | N |
| ATOM | 14439 | CA | GLN | B | 408 | −54.727 | −24.191 | −1.417 | 1.00 | 33.51 | C |
| ATOM | 14441 | CB | GLN | B | 408 | −55.891 | −24.572 | −.514 | 1.00 | 33.84 | C |
| ATOM | 14444 | CG | GLN | B | 408 | −56.161 | −23.548 | .577 | 1.00 | 35.49 | C |
| ATOM | 14447 | CD | GLN | B | 408 | −57.623 | −23.161 | .656 | 1.00 | 37.61 | C |
| ATOM | 14448 | OE1 | GLN | B | 408 | −58.519 | −24.006 | .501 | 1.00 | 38.23 | O |
| ATOM | 14449 | NE2 | GLN | B | 408 | −57.876 | −21.874 | .893 | 1.00 | 38.64 | N |
| ATOM | 14452 | C | GLN | B | 408 | −53.399 | −24.274 | −.647 | 1.00 | 33.72 | C |
| ATOM | 14453 | O | GLN | B | 408 | −52.852 | −23.253 | −.204 | 1.00 | 33.52 | O |
| ATOM | 14455 | N | ASN | B | 409 | −52.889 | −25.491 | −.490 | 1.00 | 33.95 | N |
| ATOM | 14456 | CA | ASN | B | 409 | −51.642 | −25.707 | .226 | 1.00 | 34.16 | C |
| ATOM | 14458 | CB | ASN | B | 409 | −51.865 | −26.665 | 1.391 | 1.00 | 34.25 | C |
| ATOM | 14461 | CG | ASN | B | 409 | −52.756 | −26.069 | 2.459 | 1.00 | 34.39 | C |
| ATOM | 14462 | OD1 | ASN | B | 409 | −52.269 | −25.577 | 3.480 | 1.00 | 34.40 | O |
| ATOM | 14463 | ND2 | ASN | B | 409 | −54.070 | −26.089 | 2.222 | 1.00 | 34.12 | N |
| ATOM | 14466 | C | ASN | B | 409 | −50.582 | −26.244 | −.709 | 1.00 | 34.12 | C |
| ATOM | 14467 | O | ASN | B | 409 | −50.578 | −27.422 | −1.046 | 1.00 | 34.41 | O |
| ATOM | 14469 | N | ILE | B | 410 | −49.681 | −25.369 | −1.127 | 1.00 | 34.07 | N |
| ATOM | 14470 | CA | ILE | B | 410 | −48.699 | −25.718 | −2.138 | 1.00 | 34.08 | C |
| ATOM | 14472 | CB | ILE | B | 410 | −48.138 | −24.455 | −2.840 | 1.00 | 34.15 | C |
| ATOM | 14474 | CG1 | ILE | B | 410 | −47.274 | −23.610 | −1.891 | 1.00 | 34.26 | C |
| ATOM | 14477 | CD1 | ILE | B | 410 | −47.216 | −22.139 | −2.249 | 1.00 | 34.10 | C |
| ATOM | 14481 | CG2 | ILE | B | 410 | −49.290 | −23.634 | −3.404 | 1.00 | 34.49 | C |
| ATOM | 14485 | C | ILE | B | 410 | −47.586 | −26.553 | −1.533 | 1.00 | 33.93 | C |
| ATOM | 14486 | O | ILE | B | 410 | −47.181 | −26.317 | −.405 | 1.00 | 33.80 | O |
| ATOM | 14488 | N | LYS | B | 411 | −47.123 | −27.546 | −2.285 | 1.00 | 34.12 | N |
| ATOM | 14489 | CA | LYS | B | 411 | −46.012 | −28.395 | −1.874 | 1.00 | 34.45 | C |
| ATOM | 14491 | CB | LYS | B | 411 | −46.414 | −29.873 | −1.907 | 1.00 | 34.67 | C |
| ATOM | 14494 | CG | LYS | B | 411 | −47.850 | −30.130 | −1.460 | 1.00 | 35.79 | C |
| ATOM | 14497 | CD | LYS | B | 411 | −48.102 | −31.586 | −1.052 | 1.00 | 37.60 | C |
| ATOM | 14500 | CE | LYS | B | 411 | −49.450 | −31.728 | −.309 | 1.00 | 38.80 | C |
| ATOM | 14503 | NZ | LYS | B | 411 | −49.568 | −32.992 | .488 | 1.00 | 39.20 | N |
| ATOM | 14507 | C | LYS | B | 411 | −44.843 | −28.132 | −2.810 | 1.00 | 34.33 | C |
| ATOM | 14508 | O | LYS | B | 411 | −45.038 | −27.956 | −4.006 | 1.00 | 34.14 | O |
| ATOM | 14510 | N | LYS | B | 412 | −43.631 | −28.102 | −2.265 | 1.00 | 34.50 | N |
| ATOM | 14511 | CA | LYS | B | 412 | −42.460 | −27.688 | −3.042 | 1.00 | 34.69 | C |
| ATOM | 14513 | CB | LYS | B | 412 | −41.242 | −27.398 | −2.154 | 1.00 | 35.13 | C |
| ATOM | 14516 | CG | LYS | B | 412 | −41.205 | −25.960 | −1.613 | 1.00 | 36.90 | C |
| ATOM | 14519 | CD | LYS | B | 412 | −40.079 | −25.749 | −.588 | 1.00 | 38.57 | C |
| ATOM | 14522 | CE | LYS | B | 412 | −40.546 | −24.852 | .555 | 1.00 | 39.55 | C |
| ATOM | 14525 | NZ | LYS | B | 412 | −39.491 | −24.644 | 1.587 | 1.00 | 40.83 | N |
| ATOM | 14529 | C | LYS | B | 412 | −42.075 | −28.687 | −4.103 | 1.00 | 34.13 | C |
| ATOM | 14530 | O | LYS | B | 412 | −41.468 | −28.308 | −5.093 | 1.00 | 34.21 | O |
| ATOM | 14532 | N | GLU | B | 413 | −42.408 | −29.958 | −3.910 | 1.00 | 33.54 | N |
| ATOM | 14533 | CA | GLU | B | 413 | −42.095 | −30.949 | −4.933 | 1.00 | 33.19 | C |
| ATOM | 14535 | CB | GLU | B | 413 | −41.886 | −32.335 | −4.330 | 1.00 | 33.44 | C |
| ATOM | 14538 | CG | GLU | B | 413 | −43.127 | −33.037 | −3.807 | 1.00 | 34.37 | C |
| ATOM | 14541 | CD | GLU | B | 413 | −42.834 | −34.490 | −3.499 | 1.00 | 35.56 | C |
| ATOM | 14542 | OE1 | GLU | B | 413 | −42.662 | −35.264 | −4.471 | 1.00 | 35.30 | O |
| ATOM | 14543 | OE2 | GLU | B | 413 | −42.751 | −34.847 | −2.297 | 1.00 | 36.69 | O |

TABLE 3-7-continued

Coordinates of *P. tremuloides IspS*

| | | | | | | | | | | | |
|---|---|---|---|---|---|---|---|---|---|---|---|
| ATOM | 14544 | C | GLU | B | 413 | −43.157 | −30.965 | −6.029 | 1.00 | 32.47 | C |
| ATOM | 14545 | O | GLU | B | 413 | −42.846 | −31.232 | −7.193 | 1.00 | 32.28 | O |
| ATOM | 14547 | N | GLU | B | 414 | −44.403 | −30.676 | −5.652 | 1.00 | 31.58 | N |
| ATOM | 14548 | CA | GLU | B | 414 | −45.482 | −30.512 | −6.614 | 1.00 | 30.99 | C |
| ATOM | 14550 | CB | GLU | B | 414 | −46.781 | −30.101 | −5.927 | 1.00 | 30.98 | C |
| ATOM | 14553 | CG | GLU | B | 414 | −47.732 | −31.245 | −5.642 | 1.00 | 31.82 | C |
| ATOM | 14556 | CD | GLU | B | 414 | −49.100 | −30.774 | −5.138 | 1.00 | 34.29 | C |
| ATOM | 14557 | OE1 | GLU | B | 414 | −49.258 | −29.581 | −4.777 | 1.00 | 35.53 | O |
| ATOM | 14558 | OE2 | GLU | B | 414 | −50.036 | −31.603 | −5.101 | 1.00 | 36.44 | O |
| ATOM | 14559 | C | GLU | B | 414 | −45.104 | −29.455 | −7.628 | 1.00 | 30.59 | C |
| ATOM | 14560 | O | GLU | B | 414 | −45.169 | −29.687 | −8.828 | 1.00 | 30.37 | O |
| ATOM | 14562 | N | ILE | B | 415 | −44.684 | −28.295 | −7.140 | 1.00 | 30.49 | N |
| ATOM | 14563 | CA | ILE | B | 415 | −44.367 | −27.177 | −8.028 | 1.00 | 30.40 | C |
| ATOM | 14565 | CB | ILE | B | 415 | −44.412 | −25.797 | −7.320 | 1.00 | 30.40 | C |
| ATOM | 14567 | CG1 | ILE | B | 415 | −43.235 | −25.589 | −6.388 | 1.00 | 30.36 | C |
| ATOM | 14570 | CD1 | ILE | B | 415 | −43.373 | −24.313 | −5.611 | 1.00 | 31.01 | C |
| ATOM | 14574 | CG2 | ILE | B | 415 | −45.686 | −25.644 | −6.523 | 1.00 | 30.85 | C |
| ATOM | 14578 | C | ILE | B | 415 | −43.037 | −27.347 | −8.730 | 1.00 | 30.12 | C |
| ATOM | 14579 | O | ILE | B | 415 | −42.870 | −26.865 | −9.840 | 1.00 | 30.42 | O |
| ATOM | 14581 | N | GLU | B | 416 | −42.095 | −28.030 | −8.099 | 1.00 | 29.75 | N |
| ATOM | 14582 | CA | GLU | B | 416 | −40.799 | −28.249 | −8.719 | 1.00 | 29.70 | C |
| ATOM | 14584 | CB | GLU | B | 416 | −39.825 | −28.777 | −7.690 | 1.00 | 30.02 | C |
| ATOM | 14587 | CG | GLU | B | 416 | −38.386 | −28.426 | −7.948 | 1.00 | 31.20 | C |
| ATOM | 14590 | CD | GLU | B | 416 | −37.523 | −28.839 | −6.776 | 1.00 | 32.91 | C |
| ATOM | 14591 | OE1 | GLU | B | 416 | −38.008 | −28.723 | −5.632 | 1.00 | 32.37 | O |
| ATOM | 14592 | OE2 | GLU | B | 416 | −36.377 | −29.294 | −6.994 | 1.00 | 35.31 | O |
| ATOM | 14593 | C | GLU | B | 416 | −40.917 | −29.222 | −9.890 | 1.00 | 29.24 | C |
| ATOM | 14594 | O | GLU | B | 416 | −40.121 | −29.177 | −10.835 | 1.00 | 28.86 | O |
| ATOM | 14596 | N | ASN | B | 417 | −41.915 | −30.097 | −9.819 | 1.00 | 28.81 | N |
| ATOM | 14597 | CA | ASN | B | 417 | −42.252 | −30.960 | −10.941 | 1.00 | 28.66 | C |
| ATOM | 14599 | CB | ASN | B | 417 | −43.165 | −32.105 | −10.503 | 1.00 | 28.72 | C |
| ATOM | 14602 | CG | ASN | B | 417 | −42.379 | −33.285 | −9.973 | 1.00 | 29.78 | C |
| ATOM | 14603 | OD1 | ASN | B | 417 | −41.887 | −34.108 | −10.744 | 1.00 | 30.39 | O |
| ATOM | 14604 | ND2 | ASN | B | 417 | −42.223 | −33.358 | −8.653 | 1.00 | 31.45 | N |
| ATOM | 14607 | C | ASN | B | 417 | −42.888 | −30.183 | −12.067 | 1.00 | 28.32 | C |
| ATOM | 14608 | O | ASN | B | 417 | −42.611 | −30.456 | −13.232 | 1.00 | 27.95 | O |
| ATOM | 14610 | N | LEU | B | 418 | −43.740 | −29.217 | −11.713 | 1.00 | 28.23 | N |
| ATOM | 14611 | CA | LEU | B | 418 | −44.349 | −28.313 | −12.697 | 1.00 | 27.92 | C |
| ATOM | 14613 | CB | LEU | B | 418 | −45.298 | −27.320 | −12.023 | 1.00 | 27.48 | C |
| ATOM | 14616 | CG | LEU | B | 418 | −46.636 | −27.896 | −11.553 | 1.00 | 27.02 | C |
| ATOM | 14618 | CD1 | LEU | B | 418 | −47.393 | −26.882 | −10.691 | 1.00 | 26.70 | C |
| ATOM | 14622 | CD2 | LEU | B | 418 | −47.499 | −28.355 | −12.720 | 1.00 | 25.90 | C |
| ATOM | 14626 | C | LEU | B | 418 | −43.275 | −27.567 | −13.491 | 1.00 | 28.20 | C |
| ATOM | 14627 | O | LEU | B | 418 | −43.310 | −27.541 | −14.733 | 1.00 | 27.90 | O |
| ATOM | 14629 | N | GLN | B | 419 | −42.308 | −26.995 | −12.770 | 1.00 | 28.43 | N |
| ATOM | 14630 | CA | GLN | B | 419 | −41.170 | −26.315 | −13.395 | 1.00 | 28.72 | C |
| ATOM | 14632 | CB | GLN | B | 419 | −40.223 | −25.746 | −12.347 | 1.00 | 28.81 | C |
| ATOM | 14635 | CG | GLN | B | 419 | −40.592 | −24.332 | −11.946 | 1.00 | 30.14 | C |
| ATOM | 14638 | CD | GLN | B | 419 | −39.535 | −23.671 | −11.092 | 1.00 | 32.05 | C |
| ATOM | 14639 | OE1 | GLN | B | 419 | −39.246 | −22.477 | −11.257 | 1.00 | 33.88 | O |
| ATOM | 14640 | NE2 | GLN | B | 419 | −38.948 | −24.437 | −10.170 | 1.00 | 31.84 | N |
| ATOM | 14643 | C | GLN | B | 419 | −40.390 | −27.179 | −14.370 | 1.00 | 28.83 | C |
| ATOM | 14644 | O | GLN | B | 419 | −39.922 | −26.668 | −15.386 | 1.00 | 28.72 | O |
| ATOM | 14646 | N | LYS | B | 420 | −40.265 | −28.475 | −14.067 | 1.00 | 29.21 | N |
| ATOM | 14647 | CA | LYS | B | 420 | −39.613 | −29.451 | −14.968 | 1.00 | 29.26 | C |
| ATOM | 14649 | CB | LYS | B | 420 | −38.924 | −30.555 | −14.143 | 1.00 | 29.42 | C |
| ATOM | 14652 | CG | LYS | B | 420 | −37.800 | −30.052 | −13.207 | 1.00 | 30.58 | C |
| ATOM | 14655 | CD | LYS | B | 420 | −37.373 | −31.113 | −12.151 | 1.00 | 32.35 | C |
| ATOM | 14658 | CE | LYS | B | 420 | −36.572 | −30.506 | −10.955 | 1.00 | 33.05 | C |
| ATOM | 14661 | NZ | LYS | B | 420 | −36.520 | −31.368 | −9.702 | 1.00 | 32.62 | N |
| ATOM | 14665 | C | LYS | B | 420 | −40.579 | −30.057 | −16.021 | 1.00 | 28.96 | C |
| ATOM | 14666 | O | LYS | B | 420 | −40.216 | −30.965 | −16.753 | 1.00 | 28.66 | O |
| ATOM | 14668 | N | TYR | B | 421 | −41.804 | −29.543 | −16.088 | 1.00 | 29.01 | N |
| ATOM | 14669 | CA | TYR | B | 421 | −42.777 | −29.893 | −17.134 | 1.00 | 29.16 | C |
| ATOM | 14671 | CB | TYR | B | 421 | −42.209 | −29.602 | −18.534 | 1.00 | 29.48 | C |
| ATOM | 14674 | CG | TYR | B | 421 | −41.968 | −28.127 | −18.773 | 1.00 | 31.04 | C |
| ATOM | 14675 | CD1 | TYR | B | 421 | −43.018 | −27.219 | −18.716 | 1.00 | 32.54 | C |
| ATOM | 14677 | CE1 | TYR | B | 421 | −42.815 | −25.878 | −18.914 | 1.00 | 33.35 | C |
| ATOM | 14679 | CZ | TYR | B | 421 | −41.556 | −25.413 | −19.193 | 1.00 | 34.56 | C |
| ATOM | 14680 | OH | TYR | B | 421 | −41.377 | −24.066 | −19.384 | 1.00 | 37.99 | O |
| ATOM | 14838 | CB | ILE | B | 431 | −54.400 | −31.738 | −26.375 | 1.00 | 16.53 | C |
| ATOM | 14840 | CG1 | ILE | B | 431 | −54.225 | −33.123 | −25.728 | 1.00 | 16.06 | C |
| ATOM | 14843 | CD1 | ILE | B | 431 | −54.069 | −34.212 | −26.698 | 1.00 | 16.05 | C |
| ATOM | 14847 | CG2 | ILE | B | 431 | −55.701 | −31.666 | −27.149 | 1.00 | 15.49 | C |
| ATOM | 14851 | C | ILE | B | 431 | −53.431 | −29.949 | −27.748 | 1.00 | 16.35 | C |
| ATOM | 14852 | O | ILE | B | 431 | −53.856 | −29.712 | −28.860 | 1.00 | 16.74 | O |
| ATOM | 14854 | N | PHE | B | 432 | −53.110 | −29.003 | −26.881 | 1.00 | 16.15 | N |
| ATOM | 14855 | CA | PHE | B | 432 | −53.353 | −27.577 | −27.145 | 1.00 | 16.19 | C |

TABLE 3-7-continued

Coordinates of *P. tremuloides IspS*

| | | | | | | | | | | | |
|---|---|---|---|---|---|---|---|---|---|---|---|
| ATOM | 14857 | CB | PHE | B | 432 | −52.811 | −26.776 | −25.956 | 1.00 | 16.36 | C |
| ATOM | 14860 | CG | PHE | B | 432 | −53.007 | −25.295 | −26.043 | 1.00 | 16.54 | C |
| ATOM | 14861 | CD1 | PHE | B | 432 | −53.869 | −24.708 | −26.946 | 1.00 | 16.55 | C |
| ATOM | 14863 | CE1 | PHE | B | 432 | −54.007 | −23.334 | −26.974 | 1.00 | 17.89 | C |
| ATOM | 14865 | CZ | PHE | B | 432 | −53.305 | −22.538 | −26.080 | 1.00 | 17.96 | C |
| ATOM | 14867 | CE2 | PHE | B | 432 | −52.461 | −23.114 | −25.169 | 1.00 | 17.30 | C |
| ATOM | 14869 | CD2 | PHE | B | 432 | −52.323 | −24.482 | −25.151 | 1.00 | 17.54 | C |
| ATOM | 14871 | C | PHE | B | 432 | −52.726 | −27.104 | −28.452 | 1.00 | 15.93 | C |
| ATOM | 14872 | O | PHE | B | 432 | −53.398 | −26.525 | −29.303 | 1.00 | 15.63 | O |
| ATOM | 14874 | N | ARG | B | 433 | −51.438 | −27.387 | −28.594 | 1.00 | 15.79 | N |
| ATOM | 14875 | CA | ARG | B | 433 | −50.674 | −27.044 | −29.778 | 1.00 | 15.74 | C |
| ATOM | 14877 | CB | ARG | B | 433 | −49.196 | −27.279 | −29.470 | 1.00 | 15.68 | C |
| ATOM | 14880 | CG | ARG | B | 433 | −48.259 | −27.218 | −30.665 | 1.00 | 16.39 | C |
| ATOM | 14883 | CD | ARG | B | 433 | −48.348 | −25.919 | −31.388 | 1.00 | 16.27 | C |
| ATOM | 14886 | NE | ARG | B | 433 | −47.969 | −24.850 | −30.492 | 1.00 | 17.34 | N |
| ATOM | 14888 | CZ | ARG | B | 433 | −48.210 | −23.565 | −30.703 | 1.00 | 17.89 | C |
| ATOM | 14889 | NH1 | ARG | B | 433 | −48.834 | −23.142 | −31.803 | 1.00 | 16.79 | N |
| ATOM | 14892 | NH2 | ARG | B | 433 | −47.805 | −22.701 | −29.792 | 1.00 | 18.53 | N |
| ATOM | 14895 | C | ARG | B | 433 | −51.114 | −27.852 | −31.011 | 1.00 | 15.85 | C |
| ATOM | 14896 | O | ARG | B | 433 | −51.197 | −27.328 | −32.120 | 1.00 | 15.40 | O |
| ATOM | 14898 | N | LEU | B | 434 | −51.381 | −29.134 | −30.813 | 1.00 | 16.18 | N |
| ATOM | 14899 | CA | LEU | B | 434 | −51.794 | −29.986 | −31.902 | 1.00 | 16.58 | C |
| ATOM | 14901 | CB | LEU | B | 434 | −51.802 | −31.453 | −31.468 | 1.00 | 16.79 | C |
| ATOM | 14904 | CG | LEU | B | 434 | −50.408 | −32.055 | −31.232 | 1.00 | 17.49 | C |
| ATOM | 14906 | CD1 | LEU | B | 434 | −50.486 | −33.548 | −30.864 | 1.00 | 16.63 | C |
| ATOM | 14910 | CD2 | LEU | B | 434 | −49.511 | −31.836 | −32.467 | 1.00 | 18.00 | C |
| ATOM | 14914 | C | LEU | B | 434 | −53.158 | −29.559 | −32.423 | 1.00 | 17.07 | C |
| ATOM | 14915 | O | LEU | B | 434 | −53.333 | −29.442 | −33.633 | 1.00 | 17.44 | O |
| ATOM | 14917 | N | CYS | B | 435 | −54.118 | −29.308 | −31.532 | 1.00 | 17.23 | N |
| ATOM | 14918 | CA | CYS | B | 435 | −55.419 | −28.778 | −31.947 | 1.00 | 17.44 | C |
| ATOM | 14920 | CB | CYS | B | 435 | −56.301 | −28.529 | −30.746 | 1.00 | 17.38 | C |
| ATOM | 14923 | SG | CYS | B | 435 | −56.825 | −29.993 | −29.971 | 1.00 | 17.90 | S |
| ATOM | 14925 | C | CYS | B | 435 | −55.295 | −27.460 | −32.696 | 1.00 | 17.78 | C |
| ATOM | 14926 | O | CYS | B | 435 | −55.978 | −27.232 | −33.701 | 1.00 | 17.44 | O |
| ATOM | 14928 | N | ASN | B | 436 | −54.442 | −26.585 | −32.178 | 1.00 | 18.31 | N |
| ATOM | 14929 | CA | ASN | B | 436 | −54.248 | −25.267 | −32.769 | 1.00 | 19.14 | C |
| ATOM | 14931 | CB | ASN | B | 436 | −53.392 | −24.394 | −31.844 | 1.00 | 19.31 | C |
| ATOM | 14934 | CG | ASN | B | 436 | −52.984 | −23.068 | −32.478 | 1.00 | 20.07 | C |
| ATOM | 14935 | OD1 | ASN | B | 436 | −53.456 | −22.686 | −33.555 | 1.00 | 22.72 | O |
| ATOM | 14936 | ND2 | ASN | B | 436 | −52.099 | −22.356 | −31.800 | 1.00 | 20.90 | N |
| ATOM | 14939 | C | ASN | B | 436 | −53.615 | −25.345 | −34.157 | 1.00 | 19.51 | C |
| ATOM | 14940 | O | ASN | B | 436 | −54.173 | −24.840 | −35.131 | 1.00 | 19.79 | O |
| ATOM | 14942 | N | ASP | B | 437 | −52.446 | −25.965 | −34.245 | 1.00 | 19.85 | N |
| ATOM | 14943 | CA | ASP | B | 437 | −51.754 | −26.058 | −35.517 | 1.00 | 20.01 | C |
| ATOM | 14945 | CB | ASP | B | 437 | −50.340 | −26.638 | −35.331 | 1.00 | 20.00 | C |
| ATOM | 14948 | CG | ASP | B | 437 | −49.397 | −25.675 | −34.557 | 1.00 | 21.23 | C |
| ATOM | 14949 | OD1 | ASP | B | 437 | −49.902 | −24.749 | −33.877 | 1.00 | 22.90 | O |
| ATOM | 14950 | OD2 | ASP | B | 437 | −48.149 | −25.821 | −34.632 | 1.00 | 22.18 | O |
| ATOM | 14951 | C | ASP | B | 437 | −52.629 | −26.838 | −36.512 | 1.00 | 20.00 | C |
| ATOM | 14952 | O | ASP | B | 437 | −52.678 | −26.491 | −37.695 | 1.00 | 20.02 | O |
| ATOM | 14954 | N | LEU | B | 438 | −53.372 | −27.836 | −36.021 | 1.00 | 20.02 | N |
| ATOM | 14955 | CA | LEU | B | 438 | −54.352 | −28.558 | −36.858 | 1.00 | 20.18 | C |
| ATOM | 14957 | CB | LEU | B | 438 | −55.144 | −29.593 | −36.049 | 1.00 | 19.88 | C |
| ATOM | 14960 | CG | LEU | B | 438 | −54.699 | −31.050 | −36.142 | 1.00 | 18.97 | C |
| ATOM | 14962 | CD1 | LEU | B | 438 | −55.537 | −31.869 | −35.200 | 1.00 | 18.86 | C |
| ATOM | 14966 | CD2 | LEU | B | 438 | −54.818 | −31.585 | −37.550 | 1.00 | 16.23 | C |
| ATOM | 14970 | C | LEU | B | 438 | −55.358 | −27.644 | −37.564 | 1.00 | 20.60 | C |
| ATOM | 14971 | O | LEU | B | 438 | −55.717 | −27.889 | −38.712 | 1.00 | 20.30 | O |
| ATOM | 14973 | N | ALA | B | 439 | −55.825 | −26.620 | −36.853 | 1.00 | 21.39 | N |
| ATOM | 14974 | CA | ALA | B | 439 | −56.802 | −25.654 | −37.377 | 1.00 | 21.96 | C |
| ATOM | 14976 | CB | ALA | B | 439 | −57.306 | −24.741 | −36.242 | 1.00 | 21.77 | C |
| ATOM | 14980 | C | ALA | B | 439 | −56.214 | −24.805 | −38.494 | 1.00 | 22.47 | C |
| ATOM | 14981 | O | ALA | B | 439 | −56.850 | −24.559 | −39.517 | 1.00 | 22.13 | O |
| ATOM | 14983 | N | SER | B | 440 | −54.983 | −24.370 | −38.282 | 1.00 | 23.40 | N |
| ATOM | 14984 | CA | SER | B | 440 | −54.337 | −23.428 | −39.169 | 1.00 | 24.40 | C |
| ATOM | 14986 | CB | SER | B | 440 | −53.423 | −22.529 | −38.342 | 1.00 | 24.44 | C |
| ATOM | 14989 | OG | SER | B | 440 | −52.994 | −23.206 | −37.166 | 1.00 | 25.19 | O |
| ATOM | 14991 | C | SER | B | 440 | −53.544 | −24.103 | −40.289 | 1.00 | 25.15 | C |
| ATOM | 14992 | O | SER | B | 440 | −53.093 | −23.424 | −41.210 | 1.00 | 25.24 | O |
| ATOM | 14994 | N | ALA | B | 441 | −53.392 | −25.428 | −40.222 | 1.00 | 25.99 | N |
| ATOM | 14995 | CA | ALA | B | 441 | −52.488 | −26.160 | −41.119 | 1.00 | 26.53 | C |
| ATOM | 14997 | CB | ALA | B | 441 | −52.532 | −27.655 | −40.830 | 1.00 | 26.26 | C |
| ATOM | 15001 | C | ALA | B | 441 | −52.726 | −25.903 | −42.608 | 1.00 | 27.31 | C |
| ATOM | 15002 | O | ALA | B | 441 | −51.811 | −25.489 | −43.310 | 1.00 | 27.26 | O |
| ATOM | 15004 | N | SER | B | 442 | −53.940 | −26.134 | −43.098 | 1.00 | 28.45 | N |
| ATOM | 15005 | CA | SER | B | 442 | −54.138 | −26.138 | −44.545 | 1.00 | 29.47 | C |
| ATOM | 15007 | CB | SER | B | 442 | −55.477 | −26.769 | −44.936 | 1.00 | 29.40 | C |
| ATOM | 15010 | OG | SER | B | 442 | −56.454 | −25.784 | −45.181 | 1.00 | 30.36 | O |

TABLE 3-7-continued

Coordinates of *P. tremuloides IspS*

| | | | | | | | | | | | |
|---|---|---|---|---|---|---|---|---|---|---|---|
| ATOM | 15012 | C | SER | B | 442 | −53.966 | −24.731 | −45.125 | 1.00 | 30.22 | C |
| ATOM | 15013 | O | SER | B | 442 | −53.304 | −24.562 | −46.139 | 1.00 | 30.26 | O |
| ATOM | 15015 | N | ALA | B | 443 | −54.537 | −23.729 | −44.467 | 1.00 | 31.38 | N |
| ATOM | 15016 | CA | ALA | B | 443 | −54.308 | −22.333 | −44.835 | 1.00 | 32.22 | C |
| ATOM | 15018 | CB | ALA | B | 443 | −55.057 | −21.410 | −43.893 | 1.00 | 32.28 | C |
| ATOM | 15022 | C | ALA | B | 443 | −52.820 | −21.992 | −44.818 | 1.00 | 33.12 | C |
| ATOM | 15023 | O | ALA | B | 443 | −52.302 | −21.419 | −45.766 | 1.00 | 33.24 | O |
| ATOM | 15025 | N | GLU | B | 444 | −52.136 | −22.351 | −43.736 | 1.00 | 34.43 | N |
| ATOM | 15026 | CA | GLU | B | 444 | −50.711 | −22.033 | −43.582 | 1.00 | 35.35 | C |
| ATOM | 15028 | CB | GLU | B | 444 | −50.237 | −22.271 | −42.134 | 1.00 | 35.46 | C |
| ATOM | 15031 | CG | GLU | B | 444 | −50.757 | −21.227 | −41.126 | 1.00 | 36.42 | C |
| ATOM | 15034 | CD | GLU | B | 444 | −50.178 | −21.376 | −39.708 | 1.00 | 37.82 | C |
| ATOM | 15035 | OE1 | GLU | B | 444 | −49.965 | −22.506 | −39.224 | 1.00 | 37.92 | O |
| ATOM | 15036 | OE2 | GLU | B | 444 | −49.955 | −20.344 | −39.049 | 1.00 | 40.09 | O |
| ATOM | 15037 | C | GLU | B | 444 | −49.840 | −22.794 | −44.594 | 1.00 | 35.87 | C |
| ATOM | 15038 | O | GLU | B | 444 | −48.870 | −22.239 | −45.107 | 1.00 | 35.85 | O |
| ATOM | 15040 | N | ILE | B | 445 | −50.193 | −24.048 | −44.883 | 1.00 | 36.63 | N |
| ATOM | 15041 | CA | ILE | B | 445 | −49.517 | −24.837 | −45.928 | 1.00 | 37.21 | C |
| ATOM | 15043 | CB | ILE | B | 445 | −49.854 | −26.366 | −45.832 | 1.00 | 37.15 | C |
| ATOM | 15045 | CG1 | ILE | B | 445 | −49.181 | −26.991 | −44.609 | 1.00 | 36.85 | C |
| ATOM | 15048 | CD1 | ILE | B | 445 | −49.867 | −28.244 | −44.102 | 1.00 | 36.62 | C |
| ATOM | 15052 | CG2 | ILE | B | 445 | −49.416 | −27.120 | −47.093 | 1.00 | 36.66 | C |
| ATOM | 15056 | C | ILE | B | 445 | −49.933 | −24.289 | −47.290 | 1.00 | 37.88 | C |
| ATOM | 15057 | O | ILE | B | 445 | −50.926 | −24.733 | −47.874 | 1.00 | 38.20 | O |
| ATOM | 15059 | N | ALA | B | 446 | −49.175 | −23.314 | −47.785 | 1.00 | 38.56 | N |
| ATOM | 15060 | CA | ALA | B | 446 | −49.544 | −22.575 | −48.992 | 1.00 | 39.03 | C |
| ATOM | 15062 | CB | ALA | B | 446 | −49.833 | −23.522 | −50.169 | 1.00 | 39.19 | C |
| ATOM | 15066 | C | ALA | B | 446 | −50.768 | −21.740 | −48.685 | 1.00 | 39.42 | C |
| ATOM | 15067 | O | ALA | B | 446 | −51.866 | −22.288 | −48.742 | 1.00 | 39.26 | O |
| ATOM | 15069 | N | ARG | B | 447 | −50.650 | −20.443 | −48.361 | 1.00 | 40.06 | N |
| ATOM | 15070 | CA | ARG | B | 447 | −49.426 | −19.589 | −48.361 | 1.00 | 40.54 | C |
| ATOM | 15072 | CB | ARG | B | 447 | −49.276 | −18.901 | −46.986 | 1.00 | 40.70 | C |
| ATOM | 15075 | CG | ARG | B | 447 | −50.121 | −17.634 | −46.836 | 1.00 | 41.82 | C |
| ATOM | 15078 | CD | ARG | B | 447 | −50.292 | −17.234 | −45.377 | 1.00 | 42.99 | C |
| ATOM | 15081 | NE | ARG | B | 447 | −51.628 | −17.546 | −44.864 | 1.00 | 44.22 | N |
| ATOM | 15083 | CZ | ARG | B | 447 | −51.924 | −17.766 | −43.580 | 1.00 | 46.00 | C |
| ATOM | 15084 | NH1 | ARG | B | 447 | −50.977 | −17.730 | −42.633 | 1.00 | 46.34 | N |
| ATOM | 15087 | NH2 | ARG | B | 447 | −53.184 | −18.039 | −43.236 | 1.00 | 46.39 | N |
| ATOM | 15090 | C | ARG | B | 447 | −48.095 | −20.208 | −48.837 | 1.00 | 40.35 | C |
| ATOM | 15091 | O | ARG | B | 447 | −47.897 | −20.403 | −50.038 | 1.00 | 40.95 | O |
| ATOM | 15093 | N | GLY | B | 448 | −47.170 | −20.442 | −47.918 | 1.00 | 39.87 | N |
| ATOM | 15094 | CA | GLY | B | 448 | −46.020 | −21.306 | −48.162 | 1.00 | 39.52 | C |
| ATOM | 15097 | C | GLY | B | 448 | −45.258 | −21.517 | −46.865 | 1.00 | 39.26 | C |
| ATOM | 15098 | O | GLY | B | 448 | −44.071 | −21.842 | −46.885 | 1.00 | 39.15 | O |
| ATOM | 15100 | N | GLU | B | 449 | −45.966 | −21.344 | −45.742 | 1.00 | 38.85 | N |
| ATOM | 15101 | CA | GLU | B | 449 | −45.365 | −21.215 | −44.426 | 1.00 | 38.45 | C |
| ATOM | 15103 | CB | GLU | B | 449 | −46.288 | −20.472 | −43.444 | 1.00 | 38.76 | C |
| ATOM | 15106 | CG | GLU | B | 449 | −46.346 | −18.943 | −43.636 | 1.00 | 40.34 | C |
| ATOM | 15109 | CD | GLU | B | 449 | −47.486 | −18.257 | −42.839 | 1.00 | 42.09 | C |
| ATOM | 15110 | OE1 | GLU | B | 449 | −47.897 | −18.787 | −41.780 | 1.00 | 43.23 | O |
| ATOM | 15111 | OE2 | GLU | B | 449 | −47.972 | −17.184 | −43.274 | 1.00 | 42.13 | O |
| ATOM | 15112 | C | GLU | B | 449 | −45.073 | −22.600 | −43.906 | 1.00 | 37.54 | C |
| ATOM | 15113 | O | GLU | B | 449 | −45.810 | −23.553 | −44.167 | 1.00 | 37.34 | O |
| ATOM | 15115 | N | THR | B | 450 | −43.986 | −22.688 | −43.159 | 1.00 | 36.47 | N |
| ATOM | 15116 | CA | THR | B | 450 | −43.459 | −23.950 | −42.702 | 1.00 | 35.65 | C |
| ATOM | 15118 | CB | THR | B | 450 | −42.017 | −24.105 | −43.245 | 1.00 | 35.81 | C |
| ATOM | 15120 | OG1 | THR | B | 450 | −41.593 | −25.465 | −43.109 | 1.00 | 37.67 | O |
| ATOM | 15122 | CG2 | THR | B | 450 | −41.029 | −23.152 | −42.538 | 1.00 | 36.21 | C |
| ATOM | 15126 | C | THR | B | 450 | −43.528 | −24.084 | −41.166 | 1.00 | 34.22 | C |
| ATOM | 15127 | O | THR | B | 450 | −43.165 | −25.127 | −40.619 | 1.00 | 34.00 | O |
| ATOM | 15129 | N | ALA | B | 451 | −44.024 | −23.034 | −40.495 | 1.00 | 32.69 | N |
| ATOM | 15130 | CA | ALA | B | 451 | −44.144 | −22.974 | −39.026 | 1.00 | 31.28 | C |
| ATOM | 15132 | CB | ALA | B | 451 | −43.952 | −21.546 | −38.545 | 1.00 | 31.06 | C |
| ATOM | 15136 | C | ALA | B | 451 | −45.495 | −23.500 | −38.547 | 1.00 | 29.97 | C |
| ATOM | 15137 | O | ALA | B | 451 | −46.337 | −22.735 | −38.082 | 1.00 | 30.08 | O |
| ATOM | 15139 | N | ASN | B | 452 | −45.690 | −24.809 | −38.656 | 1.00 | 28.19 | N |
| ATOM | 15140 | CA | ASN | B | 452 | −46.935 | −25.444 | −38.272 | 1.00 | 26.73 | C |
| ATOM | 15142 | CB | ASN | B | 452 | −47.929 | −25.339 | −39.422 | 1.00 | 26.45 | C |
| ATOM | 15145 | CG | ASN | B | 452 | −49.311 | −25.832 | −39.057 | 1.00 | 25.38 | C |
| ATOM | 15146 | OD1 | ASN | B | 452 | −49.608 | −27.004 | −39.195 | 1.00 | 24.57 | O |
| ATOM | 15147 | ND2 | ASN | B | 452 | −50.171 | −24.928 | −38.618 | 1.00 | 24.44 | N |
| ATOM | 15150 | C | ASN | B | 452 | −46.631 | −26.889 | −37.952 | 1.00 | 26.05 | C |
| ATOM | 15151 | O | ASN | B | 452 | −45.930 | −27.544 | −38.695 | 1.00 | 26.21 | O |
| ATOM | 15153 | N | SER | B | 453 | −47.131 | −27.388 | −36.834 | 1.00 | 25.30 | N |
| ATOM | 15154 | CA | SER | B | 453 | −46.843 | −28.760 | −36.432 | 1.00 | 24.72 | C |
| ATOM | 15156 | CB | SER | B | 453 | −47.638 | −29.139 | −35.174 | 1.00 | 24.81 | C |
| ATOM | 15159 | OG | SER | B | 453 | −47.143 | −28.455 | −34.031 | 1.00 | 24.36 | O |
| ATOM | 15161 | C | SER | B | 453 | −47.111 | −29.770 | −37.543 | 1.00 | 24.12 | C |

TABLE 3-7-continued

Coordinates of *P. tremuloides IspS*

| | | | | | | | | | | | |
|---|---|---|---|---|---|---|---|---|---|---|---|
| ATOM | 15162 | O | SER | B | 453 | −46.325 | −30.679 | −37.743 | 1.00 | 24.33 | O |
| ATOM | 15164 | N | VAL | B | 454 | −48.202 | −29.606 | −38.272 | 1.00 | 23.57 | N |
| ATOM | 15165 | CA | VAL | B | 454 | −48.546 | −30.541 | −39.328 | 1.00 | 23.27 | C |
| ATOM | 15167 | CB | VAL | B | 454 | −50.001 | −30.361 | −39.795 | 1.00 | 23.06 | C |
| ATOM | 15169 | CG1 | VAL | B | 454 | −50.363 | −31.385 | −40.829 | 1.00 | 22.41 | C |
| ATOM | 15173 | CG2 | VAL | B | 454 | −50.946 | −30.489 | −38.622 | 1.00 | 22.80 | C |
| ATOM | 15177 | C | VAL | B | 454 | −47.581 | −30.473 | −40.521 | 1.00 | 23.83 | C |
| ATOM | 15178 | O | VAL | B | 454 | −47.370 | −31.493 | −41.175 | 1.00 | 24.48 | O |
| ATOM | 15180 | N | SER | B | 455 | −46.981 | −29.309 | −40.803 | 1.00 | 23.99 | N |
| ATOM | 15181 | CA | SER | B | 455 | −45.978 | −29.198 | −41.881 | 1.00 | 24.22 | C |
| ATOM | 15183 | CB | SER | B | 455 | −45.577 | −27.767 | −42.111 | 1.00 | 24.02 | C |
| ATOM | 15186 | OG | SER | B | 455 | −46.655 | −27.098 | −42.689 | 1.00 | 25.57 | O |
| ATOM | 15188 | C | SER | B | 455 | −44.708 | −29.949 | −41.582 | 1.00 | 24.65 | C |
| ATOM | 15189 | O | SER | B | 455 | −44.211 | −30.700 | −42.417 | 1.00 | 25.23 | O |
| ATOM | 15191 | N | CYS | B | 456 | −44.151 | −29.700 | −40.405 | 1.00 | 24.82 | N |
| ATOM | 15192 | CA | CYS | B | 456 | −43.024 | −30.462 | −39.935 | 1.00 | 24.81 | C |
| ATOM | 15194 | CB | CYS | B | 456 | −42.765 | −30.170 | −38.470 | 1.00 | 24.92 | C |
| ATOM | 15197 | SG | CYS | B | 456 | −42.139 | −28.541 | −38.190 | 1.00 | 25.18 | S |
| ATOM | 15199 | C | CYS | B | 456 | −43.304 | −31.938 | −40.124 | 1.00 | 24.84 | C |
| ATOM | 15200 | O | CYS | B | 456 | −42.507 | −32.634 | −40.728 | 1.00 | 25.34 | O |
| ATOM | 15202 | N | TYR | B | 457 | −44.442 | −32.421 | −39.644 | 1.00 | 24.75 | N |
| ATOM | 15203 | CA | TYR | B | 457 | −44.735 | −33.838 | −39.778 | 1.00 | 24.85 | C |
| ATOM | 15205 | CB | TYR | B | 457 | −46.069 | −34.197 | −39.142 | 1.00 | 24.64 | C |
| ATOM | 15208 | CG | TYR | B | 457 | −46.057 | −35.537 | −38.451 | 1.00 | 24.00 | C |
| ATOM | 15209 | CD1 | TYR | B | 457 | −45.846 | −35.635 | −37.083 | 1.00 | 24.19 | C |
| ATOM | 15211 | CE1 | TYR | B | 457 | −45.848 | −36.873 | −36.436 | 1.00 | 23.72 | C |
| ATOM | 15213 | CZ | TYR | B | 457 | −46.059 | −38.025 | −37.170 | 1.00 | 23.27 | C |
| ATOM | 15214 | OH | TYR | B | 457 | −46.063 | −39.244 | −36.554 | 1.00 | 22.94 | O |
| ATOM | 15216 | CE2 | TYR | B | 457 | −46.268 | −37.961 | −38.528 | 1.00 | 23.68 | C |
| ATOM | 15218 | CD2 | TYR | B | 457 | −46.265 | −36.711 | −39.163 | 1.00 | 24.16 | C |
| ATOM | 15220 | C | TYR | B | 457 | −44.676 | −34.267 | −41.251 | 1.00 | 25.30 | C |
| ATOM | 15221 | O | TYR | B | 457 | −43.965 | −35.208 | −41.584 | 1.00 | 24.94 | O |
| ATOM | 15223 | N | MET | B | 458 | −45.388 | −33.569 | −42.134 | 1.00 | 26.02 | N |
| ATOM | 15224 | CA | MET | B | 458 | −45.207 | −33.775 | −43.585 | 1.00 | 26.76 | C |
| ATOM | 15226 | CB | MET | B | 458 | −45.913 | −32.685 | −44.407 | 1.00 | 26.84 | C |
| ATOM | 15229 | CG | MET | B | 458 | −47.419 | −32.720 | −44.429 | 1.00 | 27.32 | C |
| ATOM | 15232 | SD | MET | B | 458 | −48.092 | −31.238 | −45.229 | 1.00 | 27.76 | S |
| ATOM | 15233 | CE | MET | B | 458 | −47.283 | −31.311 | −46.830 | 1.00 | 26.95 | C |
| ATOM | 15237 | C | MET | B | 458 | −43.723 | −33.759 | −43.996 | 1.00 | 27.06 | C |
| ATOM | 15238 | O | MET | B | 458 | −43.192 | −34.746 | −44.485 | 1.00 | 26.94 | O |
| ATOM | 15240 | N | ARG | B | 459 | −43.069 | −32.624 | −43.800 | 1.00 | 27.58 | N |
| ATOM | 15241 | CA | ARG | B | 459 | −41.720 | −32.419 | −44.289 | 1.00 | 28.38 | C |
| ATOM | 15243 | CB | ARG | B | 459 | −41.313 | −30.965 | −44.041 | 1.00 | 28.96 | C |
| ATOM | 15246 | CG | ARG | B | 459 | −39.862 | −30.642 | −44.328 | 1.00 | 31.93 | C |
| ATOM | 15249 | CD | ARG | B | 459 | −39.656 | −29.139 | −44.480 | 1.00 | 36.88 | C |
| ATOM | 15252 | NE | ARG | B | 459 | −40.318 | −28.349 | −43.427 | 1.00 | 41.70 | N |
| ATOM | 15254 | CZ | ARG | B | 459 | −39.890 | −28.241 | −42.161 | 1.00 | 45.68 | C |
| ATOM | 15255 | NH1 | ARG | B | 459 | −38.795 | −28.899 | −41.751 | 1.00 | 48.08 | N |
| ATOM | 15258 | NH2 | ARG | B | 459 | −40.566 | −27.489 | −41.284 | 1.00 | 45.92 | N |
| ATOM | 15261 | C | ARG | B | 459 | −40.717 | −33.401 | −43.672 | 1.00 | 28.03 | C |
| ATOM | 15262 | O | ARG | B | 459 | −39.829 | −33.881 | −44.356 | 1.00 | 28.13 | O |
| ATOM | 15264 | N | THR | B | 460 | −40.882 | −33.711 | −42.393 | 1.00 | 27.88 | N |
| ATOM | 15265 | CA | THR | B | 460 | −40.002 | −34.635 | −41.664 | 1.00 | 27.75 | C |
| ATOM | 15267 | CB | THR | B | 460 | −40.240 | −34.502 | −40.134 | 1.00 | 27.79 | C |
| ATOM | 15269 | OG1 | THR | B | 460 | −39.805 | −33.209 | −39.689 | 1.00 | 27.98 | O |
| ATOM | 15271 | CG2 | THR | B | 460 | −39.519 | −35.589 | −39.356 | 1.00 | 27.46 | C |
| ATOM | 15275 | C | THR | B | 460 | −40.171 | −36.114 | −42.045 | 1.00 | 27.72 | C |
| ATOM | 15276 | O | THR | B | 460 | −39.211 | −36.857 | −42.069 | 1.00 | 27.60 | O |
| ATOM | 15278 | N | LYS | B | 461 | −41.398 | −36.538 | −42.313 | 1.00 | 28.05 | N |
| ATOM | 15279 | CA | LYS | B | 461 | −41.701 | −37.929 | −42.649 | 1.00 | 28.25 | C |
| ATOM | 15281 | CB | LYS | B | 461 | −42.972 | −38.381 | −41.914 | 1.00 | 28.32 | C |
| ATOM | 15284 | CG | LYS | B | 461 | −42.767 | −38.763 | −40.453 | 1.00 | 28.57 | C |
| ATOM | 15287 | CD | LYS | B | 461 | −42.569 | −40.271 | −40.299 | 1.00 | 29.79 | C |
| ATOM | 15290 | CE | LYS | B | 461 | −41.913 | −40.651 | −38.970 | 1.00 | 30.32 | C |
| ATOM | 15293 | NZ | LYS | B | 461 | −42.651 | −40.184 | −37.749 | 1.00 | 30.60 | N |
| ATOM | 15297 | C | LYS | B | 461 | −41.876 | −38.139 | −44.155 | 1.00 | 28.50 | C |
| ATOM | 15298 | O | LYS | B | 461 | −42.071 | −39.269 | −44.598 | 1.00 | 28.58 | O |
| ATOM | 15300 | N | GLY | B | 462 | −41.818 | −37.057 | −44.933 | 1.00 | 28.79 | N |
| ATOM | 15301 | CA | GLY | B | 462 | −41.978 | −37.114 | −46.385 | 1.00 | 29.04 | C |
| ATOM | 15304 | C | GLY | B | 462 | −43.333 | −37.610 | −46.853 | 1.00 | 29.39 | C |
| ATOM | 15305 | O | GLY | B | 462 | −43.410 | −38.452 | −47.738 | 1.00 | 29.53 | O |
| ATOM | 15307 | N | ILE | B | 463 | −44.406 | −37.081 | −46.270 | 1.00 | 29.91 | N |
| ATOM | 15308 | CA | ILE | B | 463 | −45.764 | −37.552 | −46.572 | 1.00 | 30.27 | C |
| ATOM | 15310 | CB | ILE | B | 463 | −46.333 | −38.444 | −45.433 | 1.00 | 30.13 | C |
| ATOM | 15312 | CG1 | ILE | B | 463 | −46.308 | −37.706 | −44.092 | 1.00 | 30.22 | C |
| ATOM | 15315 | CD1 | ILE | B | 463 | −46.983 | −38.462 | −42.965 | 1.00 | 30.14 | C |
| ATOM | 15319 | CG2 | ILE | B | 463 | −45.558 | −39.740 | −45.340 | 1.00 | 29.85 | C |
| ATOM | 15323 | C | ILE | B | 463 | −46.775 | −36.429 | −46.881 | 1.00 | 30.75 | C |

TABLE 3-7-continued

Coordinates of *P. tremuloides IspS*

| | | | | | | | | | | | |
|---|---|---|---|---|---|---|---|---|---|---|---|
| ATOM | 15324 | O | ILE | B | 463 | −46.595 | −35.270 | −46.495 | 1.00 | 30.52 | O |
| ATOM | 15326 | N | SER | B | 464 | −47.842 | −36.822 | −47.581 | 1.00 | 31.33 | N |
| ATOM | 15327 | CA | SER | B | 464 | −48.951 | −35.944 | −47.952 | 1.00 | 31.68 | C |
| ATOM | 15329 | CB | SER | B | 464 | −49.948 | −36.709 | −48.830 | 1.00 | 32.02 | C |
| ATOM | 15332 | OG | SER | B | 464 | −50.547 | −37.793 | −48.123 | 1.00 | 32.84 | O |
| ATOM | 15334 | C | SER | B | 464 | −49.705 | −35.396 | −46.747 | 1.00 | 31.62 | C |
| ATOM | 15335 | O | SER | B | 464 | −49.897 | −36.097 | −45.747 | 1.00 | 31.69 | O |
| ATOM | 15337 | N | GLU | B | 465 | −50.165 | −34.153 | −46.874 | 1.00 | 31.42 | N |
| ATOM | 15338 | CA | GLU | B | 465 | −50.881 | −33.466 | −45.803 | 1.00 | 31.20 | C |
| ATOM | 15340 | CB | GLU | B | 465 | −51.465 | −32.141 | −46.324 | 1.00 | 31.33 | C |
| ATOM | 15343 | CG | GLU | B | 465 | −52.441 | −31.455 | −45.359 | 1.00 | 31.42 | C |
| ATOM | 15346 | CD | GLU | B | 465 | −52.768 | −30.006 | −45.712 | 1.00 | 31.30 | C |
| ATOM | 15347 | OE1 | GLU | B | 465 | −52.325 | −29.490 | −46.765 | 1.00 | 30.56 | O |
| ATOM | 15348 | OE2 | GLU | B | 465 | −53.487 | −29.380 | −44.906 | 1.00 | 31.84 | O |
| ATOM | 15349 | C | GLU | B | 465 | −51.985 | −34.325 | −45.202 | 1.00 | 30.97 | C |
| ATOM | 15350 | O | GLU | B | 465 | −52.175 | −34.327 | −43.992 | 1.00 | 30.72 | O |
| ATOM | 15352 | N | GLU | B | 466 | −52.709 | −35.052 | −46.055 | 1.00 | 30.98 | N |
| ATOM | 15353 | CA | GLU | B | 466 | −53.865 | −35.833 | −45.618 | 1.00 | 30.65 | C |
| ATOM | 15355 | CB | GLU | B | 466 | −54.553 | −36.541 | −46.788 | 1.00 | 30.62 | C |
| ATOM | 15358 | CG | GLU | B | 466 | −55.733 | −37.401 | −46.336 | 1.00 | 31.50 | C |
| ATOM | 15361 | CD | GLU | B | 466 | −56.353 | −38.240 | −47.446 | 1.00 | 33.14 | C |
| ATOM | 15362 | OE1 | GLU | B | 466 | −56.512 | −37.736 | −48.581 | 1.00 | 34.40 | O |
| ATOM | 15363 | OE2 | GLU | B | 466 | −56.699 | −39.413 | −47.173 | 1.00 | 33.21 | O |
| ATOM | 15364 | C | GLU | B | 466 | −53.477 | −36.851 | −44.564 | 1.00 | 30.17 | C |
| ATOM | 15365 | O | GLU | B | 466 | −54.215 | −37.049 | −43.606 | 1.00 | 30.46 | O |
| ATOM | 15367 | N | LEU | B | 467 | −52.333 | −37.506 | −44.726 | 1.00 | 29.59 | N |
| ATOM | 15368 | CA | LEU | B | 467 | −51.953 | −38.540 | −43.769 | 1.00 | 29.19 | C |
| ATOM | 15370 | CB | LEU | B | 467 | −51.640 | −39.869 | −44.476 | 1.00 | 29.27 | C |
| ATOM | 15373 | CG | LEU | B | 467 | −50.356 | −40.081 | −45.268 | 1.00 | 29.84 | C |
| ATOM | 15375 | CD1 | LEU | B | 467 | −49.341 | −40.761 | −44.357 | 1.00 | 31.06 | C |
| ATOM | 15379 | CD2 | LEU | B | 467 | −50.589 | −40.920 | −46.523 | 1.00 | 29.47 | C |
| ATOM | 15383 | C | LEU | B | 467 | −50.865 | −38.092 | −42.794 | 1.00 | 28.54 | C |
| ATOM | 15384 | O | LEU | B | 467 | −50.490 | −38.834 | −41.894 | 1.00 | 28.28 | O |
| ATOM | 15386 | N | ALA | B | 468 | −50.388 | −36.862 | −42.962 | 1.00 | 28.04 | N |
| ATOM | 15387 | CA | ALA | B | 468 | −49.682 | −36.158 | −41.893 | 1.00 | 27.54 | C |
| ATOM | 15389 | CB | ALA | B | 468 | −48.922 | −34.970 | −42.435 | 1.00 | 27.34 | C |
| ATOM | 15393 | C | ALA | B | 468 | −50.711 | −35.698 | −40.865 | 1.00 | 27.17 | C |
| ATOM | 15394 | O | ALA | B | 468 | −50.482 | −35.801 | −39.662 | 1.00 | 27.40 | O |
| ATOM | 15396 | N | THR | B | 469 | −51.841 | −35.182 | −41.349 | 1.00 | 26.57 | N |
| ATOM | 15397 | CA | THR | B | 469 | −52.957 | −34.795 | −40.490 | 1.00 | 25.87 | C |
| ATOM | 15399 | CB | THR | B | 469 | −54.130 | −34.297 | −41.328 | 1.00 | 25.53 | C |
| ATOM | 15401 | OG1 | THR | B | 469 | −53.737 | −33.111 | −42.025 | 1.00 | 24.99 | O |
| ATOM | 15403 | CG2 | THR | B | 469 | −55.316 | −33.993 | −40.453 | 1.00 | 24.62 | C |
| ATOM | 15407 | C | THR | B | 469 | −53.412 | −35.988 | −39.669 | 1.00 | 25.95 | C |
| ATOM | 15408 | O | THR | B | 469 | −53.551 | −35.925 | −38.450 | 1.00 | 25.80 | O |
| ATOM | 15410 | N | GLU | B | 470 | −53.618 | −37.091 | −40.367 | 1.00 | 26.06 | N |
| ATOM | 15411 | CA | GLU | B | 470 | −54.043 | −38.344 | −39.756 | 1.00 | 26.10 | C |
| ATOM | 15413 | CB | GLU | B | 470 | −54.057 | −39.436 | −40.848 | 1.00 | 26.60 | C |
| ATOM | 15416 | CG | GLU | B | 470 | −55.038 | −40.587 | −40.646 | 1.00 | 28.01 | C |
| ATOM | 15419 | CD | GLU | B | 470 | −54.553 | −41.897 | −41.286 | 1.00 | 29.05 | C |
| ATOM | 15420 | OE1 | GLU | B | 470 | −54.298 | −41.930 | −42.515 | 1.00 | 27.96 | O |
| ATOM | 15421 | OE2 | GLU | B | 470 | −54.435 | −42.892 | −40.536 | 1.00 | 30.42 | O |
| ATOM | 15422 | C | GLU | B | 470 | −53.148 | −38.746 | −38.557 | 1.00 | 25.28 | C |
| ATOM | 15423 | O | GLU | B | 470 | −53.629 | −39.266 | −37.556 | 1.00 | 25.08 | O |
| ATOM | 15425 | N | SER | B | 471 | −51.850 | −38.497 | −38.654 | 1.00 | 24.70 | N |
| ATOM | 15426 | CA | SER | B | 471 | −50.930 | −38.906 | −37.599 | 1.00 | 24.26 | C |
| ATOM | 15428 | CB | SER | B | 471 | −49.494 | −38.842 | −38.085 | 1.00 | 24.11 | C |
| ATOM | 15431 | OG | SER | B | 471 | −49.315 | −39.693 | −39.186 | 1.00 | 23.98 | O |
| ATOM | 15433 | C | SER | B | 471 | −51.085 | −38.029 | −36.377 | 1.00 | 23.92 | C |
| ATOM | 15434 | O | SER | B | 471 | −51.240 | −38.530 | −35.270 | 1.00 | 24.09 | O |
| ATOM | 15436 | N | VAL | B | 472 | −51.032 | −36.719 | −36.582 | 1.00 | 23.48 | N |
| ATOM | 15437 | CA | VAL | B | 472 | −51.279 | −35.774 | −35.510 | 1.00 | 23.15 | C |
| ATOM | 15439 | CB | VAL | B | 472 | −51.377 | −34.332 | −36.045 | 1.00 | 23.03 | C |
| ATOM | 15441 | CG1 | VAL | B | 472 | −51.739 | −33.347 | −34.929 | 1.00 | 21.74 | C |
| ATOM | 15445 | CG2 | VAL | B | 472 | −50.067 | −33.945 | −36.728 | 1.00 | 22.27 | C |
| ATOM | 15449 | C | VAL | B | 472 | −52.572 | −36.192 | −34.830 | 1.00 | 23.49 | C |
| ATOM | 15450 | O | VAL | B | 472 | −52.663 | −36.276 | −33.614 | 1.00 | 23.29 | O |
| ATOM | 15452 | N | MET | B | 473 | −53.573 | −36.508 | −35.626 | 1.00 | 24.34 | N |
| ATOM | 15453 | CA | MET | B | 473 | −54.850 | −36.901 | −35.070 | 1.00 | 24.93 | C |
| ATOM | 15455 | CB | MET | B | 473 | −55.816 | −37.266 | −36.190 | 1.00 | 25.09 | C |
| ATOM | 15458 | CG | MET | B | 473 | −57.191 | −36.788 | −35.912 | 1.00 | 26.94 | C |
| ATOM | 15461 | SD | MET | B | 473 | −57.328 | −35.035 | −36.251 | 1.00 | 29.69 | S |
| ATOM | 15462 | CE | MET | B | 473 | −58.316 | −35.080 | −37.775 | 1.00 | 29.12 | C |
| ATOM | 15466 | C | MET | B | 473 | −54.668 | −38.072 | −34.100 | 1.00 | 25.00 | C |
| ATOM | 15467 | O | MET | B | 473 | −55.135 | −38.018 | −32.963 | 1.00 | 24.78 | O |
| ATOM | 15469 | N | ASN | B | 474 | −53.965 | −39.110 | −34.556 | 1.00 | 25.30 | N |
| ATOM | 15470 | CA | ASN | B | 474 | −53.681 | −40.293 | −33.738 | 1.00 | 25.55 | C |
| ATOM | 15472 | CB | ASN | B | 474 | −53.143 | −41.439 | −34.601 | 1.00 | 25.82 | C |

TABLE 3-7-continued

Coordinates of *P. tremuloides IspS*

| | | | | | | | | | | | |
|---|---|---|---|---|---|---|---|---|---|---|---|
| ATOM | 15475 | CG | ASN | B | 474 | −54.243 | −42.137 | −35.402 | 1.00 | 27.62 | C |
| ATOM | 15476 | OD1 | ASN | B | 474 | −54.238 | −42.102 | −36.638 | 1.00 | 29.33 | O |
| ATOM | 15477 | ND2 | ASN | B | 474 | −55.196 | −42.780 | −34.697 | 1.00 | 28.58 | N |
| ATOM | 15480 | C | ASN | B | 474 | −52.711 | −40.034 | −32.592 | 1.00 | 25.20 | C |
| ATOM | 15481 | O | ASN | B | 474 | −52.711 | −40.773 | −31.621 | 1.00 | 25.71 | O |
| ATOM | 15483 | N | LEU | B | 475 | −51.883 | −38.999 | −32.704 | 1.00 | 24.65 | N |
| ATOM | 15484 | CA | LEU | B | 475 | −50.987 | −38.595 | −31.614 | 1.00 | 24.04 | C |
| ATOM | 15486 | CB | LEU | B | 475 | −49.939 | −37.626 | −32.142 | 1.00 | 23.88 | C |
| ATOM | 15489 | CG | LEU | B | 475 | −48.837 | −37.285 | −31.164 | 1.00 | 23.70 | C |
| ATOM | 15491 | CD1 | LEU | B | 475 | −47.936 | −38.471 | −31.004 | 1.00 | 23.97 | C |
| ATOM | 15495 | CD2 | LEU | B | 475 | −48.088 | −36.104 | −31.679 | 1.00 | 23.99 | C |
| ATOM | 15499 | C | LEU | B | 475 | −51.747 | −37.940 | −30.453 | 1.00 | 23.65 | C |
| ATOM | 15500 | O | LEU | B | 475 | −51.323 | −38.014 | −29.299 | 1.00 | 23.74 | O |
| ATOM | 15502 | N | ILE | B | 476 | −52.858 | −37.282 | −30.766 | 1.00 | 23.15 | N |
| ATOM | 15503 | CA | ILE | B | 476 | −53.728 | −36.711 | −29.742 | 1.00 | 22.50 | C |
| ATOM | 15505 | CB | ILE | B | 476 | −54.779 | −35.755 | −30.359 | 1.00 | 22.27 | C |
| ATOM | 15507 | CG1 | ILE | B | 476 | −54.099 | −34.508 | −30.910 | 1.00 | 20.55 | C |
| ATOM | 15510 | CD1 | ILE | B | 476 | −55.000 | −33.671 | −31.693 | 1.00 | 19.19 | C |
| ATOM | 15514 | CG2 | ILE | B | 476 | −55.817 | −35.363 | −29.336 | 1.00 | 22.15 | C |
| ATOM | 15518 | C | ILE | B | 476 | −54.398 | −37.849 | −28.985 | 1.00 | 22.40 | C |
| ATOM | 15519 | O | ILE | B | 476 | −54.316 | −37.900 | −27.767 | 1.00 | 22.32 | O |
| ATOM | 15521 | N | ASP | B | 477 | −55.023 | −38.777 | −29.708 | 1.00 | 22.37 | N |
| ATOM | 15522 | CA | ASP | B | 477 | −55.616 | −39.975 | −29.090 | 1.00 | 22.55 | C |
| ATOM | 15524 | CB | ASP | B | 477 | −55.996 | −41.007 | −30.151 | 1.00 | 22.67 | C |
| ATOM | 15527 | CG | ASP | B | 477 | −57.262 | −40.636 | −30.892 | 1.00 | 24.93 | C |
| ATOM | 15528 | OD1 | ASP | B | 477 | −57.690 | −39.458 | −30.818 | 1.00 | 28.87 | O |
| ATOM | 15529 | OD2 | ASP | B | 477 | −57.847 | −41.523 | −31.549 | 1.00 | 27.92 | O |
| ATOM | 15530 | C | ASP | B | 477 | −54.675 | −40.622 | −28.083 | 1.00 | 22.10 | C |
| ATOM | 15531 | O | ASP | B | 477 | −55.048 | −40.877 | −26.938 | 1.00 | 21.83 | O |
| ATOM | 15533 | N | GLU | B | 478 | −53.444 | −40.867 | −28.510 | 1.00 | 21.73 | N |
| ATOM | 15534 | CA | GLU | B | 478 | −52.472 | −41.506 | −27.645 | 1.00 | 21.69 | C |
| ATOM | 15536 | CB | GLU | B | 478 | −51.233 | −41.920 | −28.437 | 1.00 | 21.97 | C |
| ATOM | 15539 | CG | GLU | B | 478 | −50.786 | −43.360 | −28.150 | 1.00 | 24.18 | C |
| ATOM | 15542 | CD | GLU | B | 478 | −51.793 | −44.429 | −28.618 | 1.00 | 27.03 | C |
| ATOM | 15543 | OE1 | GLU | B | 478 | −51.599 | −45.627 | −28.285 | 1.00 | 29.15 | O |
| ATOM | 15544 | OE2 | GLU | B | 478 | −52.770 | −44.080 | −29.323 | 1.00 | 28.37 | O |
| ATOM | 15545 | C | GLU | B | 478 | −52.107 | −40.608 | −26.449 | 1.00 | 20.97 | C |
| ATOM | 15546 | O | GLU | B | 478 | −51.928 | −41.110 | −25.316 | 1.00 | 21.15 | O |
| ATOM | 15548 | N | THR | B | 479 | −52.031 | −39.291 | −26.687 | 1.00 | 19.82 | N |
| ATOM | 15549 | CA | THR | B | 479 | −51.787 | −38.319 | −25.604 | 1.00 | 18.59 | C |
| ATOM | 15551 | CB | THR | B | 479 | −51.587 | −36.897 | −26.129 | 1.00 | 17.95 | C |
| ATOM | 15553 | OG1 | THR | B | 479 | −50.291 | −36.779 | −26.712 | 1.00 | 17.43 | O |
| ATOM | 15555 | CG2 | THR | B | 479 | −51.654 | −35.938 | −25.009 | 1.00 | 17.90 | C |
| ATOM | 15559 | C | THR | B | 479 | −52.927 | −38.342 | −24.580 | 1.00 | 18.16 | C |
| ATOM | 15560 | O | THR | B | 479 | −52.695 | −38.339 | −23.383 | 1.00 | 18.06 | O |
| ATOM | 15562 | N | TRP | B | 480 | −54.160 | −38.390 | −25.057 | 1.00 | 17.77 | N |
| ATOM | 15563 | CA | TRP | B | 480 | −55.301 | −38.493 | −24.169 | 1.00 | 17.54 | C |
| ATOM | 15565 | CB | TRP | B | 480 | −56.605 | −38.464 | −24.970 | 1.00 | 17.49 | C |
| ATOM | 15568 | CG | TRP | B | 480 | −57.239 | −37.099 | −25.028 | 1.00 | 17.53 | C |
| ATOM | 15569 | CD1 | TRP | B | 480 | −57.150 | −36.186 | −26.041 | 1.00 | 17.04 | C |
| ATOM | 15571 | NE1 | TRP | B | 480 | −57.857 | −35.067 | −25.721 | 1.00 | 16.57 | N |
| ATOM | 15573 | CE2 | TRP | B | 480 | −58.423 | −35.236 | −24.484 | 1.00 | 16.41 | C |
| ATOM | 15574 | CD2 | TRP | B | 480 | −58.055 | −36.498 | −24.020 | 1.00 | 16.68 | C |
| ATOM | 15575 | CE3 | TRP | B | 480 | −58.507 | −36.914 | −22.765 | 1.00 | 16.92 | C |
| ATOM | 15577 | CZ3 | TRP | B | 480 | −59.300 | −36.076 | −22.039 | 1.00 | 16.97 | C |
| ATOM | 15579 | CH2 | TRP | B | 480 | −59.654 | −34.823 | −22.524 | 1.00 | 16.91 | C |
| ATOM | 15581 | CZ2 | TRP | B | 480 | −59.223 | −34.383 | −23.742 | 1.00 | 16.89 | C |
| ATOM | 15583 | C | TRP | B | 480 | −55.232 | −39.760 | −23.334 | 1.00 | 17.75 | C |
| ATOM | 15584 | O | TRP | B | 480 | −55.582 | −39.747 | −22.164 | 1.00 | 17.74 | O |
| ATOM | 15586 | N | LYS | B | 481 | −54.784 | −40.861 | −23.933 | 1.00 | 18.09 | N |
| ATOM | 15587 | CA | LYS | B | 481 | −54.721 | −42.124 | −23.210 | 1.00 | 18.10 | C |
| ATOM | 15589 | CB | LYS | B | 481 | −54.277 | −43.282 | −24.115 | 1.00 | 18.01 | C |
| ATOM | 15592 | CG | LYS | B | 481 | −55.311 | −43.803 | −25.114 | 1.00 | 16.89 | C |
| ATOM | 15595 | CD | LYS | B | 481 | −54.613 | −44.663 | −26.199 | 1.00 | 15.83 | C |
| ATOM | 15598 | CE | LYS | B | 481 | −55.587 | −45.500 | −27.025 | 1.00 | 14.74 | C |
| ATOM | 15601 | NZ | LYS | B | 481 | −55.119 | −45.725 | −28.413 | 1.00 | 12.34 | N |
| ATOM | 15605 | C | LYS | B | 481 | −53.750 | −41.970 | −22.054 | 1.00 | 18.46 | C |
| ATOM | 15606 | O | LYS | B | 481 | −53.976 | −42.494 | −20.969 | 1.00 | 18.44 | O |
| ATOM | 15608 | N | LYS | B | 482 | −52.662 | −41.252 | −22.279 | 1.00 | 18.80 | N |
| ATOM | 15609 | CA | LYS | B | 482 | −51.727 | −41.019 | −21.192 | 1.00 | 19.58 | C |
| ATOM | 15611 | CB | LYS | B | 482 | −50.425 | −40.424 | −21.727 | 1.00 | 20.03 | C |
| ATOM | 15614 | CG | LYS | B | 482 | −49.499 | −41.500 | −22.277 | 1.00 | 22.03 | C |
| ATOM | 15617 | CD | LYS | B | 482 | −48.706 | −41.063 | −23.506 | 1.00 | 24.87 | C |
| ATOM | 15620 | CE | LYS | B | 482 | −47.908 | −42.268 | −24.066 | 1.00 | 26.65 | C |
| ATOM | 15623 | NZ | LYS | B | 482 | −47.287 | −41.996 | −25.408 | 1.00 | 28.80 | N |
| ATOM | 15627 | C | LYS | B | 482 | −52.363 | −40.156 | −20.096 | 1.00 | 19.56 | C |
| ATOM | 15628 | O | LYS | B | 482 | −52.367 | −40.537 | −18.926 | 1.00 | 19.19 | O |
| ATOM | 15630 | N | MET | B | 483 | −52.922 | −39.013 | −20.483 | 1.00 | 20.00 | N |

TABLE 3-7-continued

Coordinates of *P. tremuloides IspS*

| | | | | | | | | | | | |
|---|---|---|---|---|---|---|---|---|---|---|---|
| ATOM | 15631 | CA | MET | B | 483 | −53.677 | −38.165 | −19.552 | 1.00 | 20.37 | C |
| ATOM | 15633 | CB | MET | B | 483 | −54.426 | −37.057 | −20.295 | 1.00 | 20.25 | C |
| ATOM | 15636 | CG | MET | B | 483 | −53.529 | −35.951 | −20.807 | 1.00 | 20.52 | C |
| ATOM | 15639 | SD | MET | B | 483 | −54.461 | −34.483 | −21.225 | 1.00 | 20.47 | S |
| ATOM | 15640 | CE | MET | B | 483 | −55.361 | −35.084 | −22.649 | 1.00 | 22.07 | C |
| ATOM | 15644 | C | MET | B | 483 | −54.668 | −38.981 | −18.741 | 1.00 | 20.72 | C |
| ATOM | 15645 | O | MET | B | 483 | −54.809 | −38.779 | −17.543 | 1.00 | 20.37 | O |
| ATOM | 15647 | N | ASN | B | 484 | −55.345 | −39.910 | −19.403 | 1.00 | 21.57 | N |
| ATOM | 15648 | CA | ASN | B | 484 | −56.339 | −40.731 | −18.744 | 1.00 | 22.46 | C |
| ATOM | 15650 | CB | ASN | B | 484 | −57.042 | −41.631 | −19.765 | 1.00 | 22.23 | C |
| ATOM | 15653 | CG | ASN | B | 484 | −58.118 | −40.900 | −20.576 | 1.00 | 21.61 | C |
| ATOM | 15654 | OD1 | ASN | B | 484 | −58.412 | −39.722 | −20.362 | 1.00 | 20.25 | O |
| ATOM | 15655 | ND2 | ASN | B | 484 | −58.720 | −41.622 | −21.510 | 1.00 | 20.80 | N |
| ATOM | 15658 | C | ASN | B | 484 | −55.723 | −41.555 | −17.598 | 1.00 | 23.83 | C |
| ATOM | 15659 | O | ASN | B | 484 | −56.262 | −41.591 | −16.484 | 1.00 | 23.76 | O |
| ATOM | 15661 | N | LYS | B | 485 | −54.585 | −42.190 | −17.868 | 1.00 | 25.69 | N |
| ATOM | 15662 | CA | LYS | B | 485 | −53.854 | −42.937 | −16.843 | 1.00 | 27.11 | C |
| ATOM | 15664 | CB | LYS | B | 485 | −52.679 | −43.712 | −17.447 | 1.00 | 27.13 | C |
| ATOM | 15667 | CG | LYS | B | 485 | −52.073 | −44.755 | −16.489 | 1.00 | 28.85 | C |
| ATOM | 15670 | CD | LYS | B | 485 | −51.643 | −46.082 | −17.187 | 1.00 | 31.17 | C |
| ATOM | 15673 | CE | LYS | B | 485 | −50.150 | −46.132 | −17.555 | 1.00 | 32.11 | C |
| ATOM | 15676 | NZ | LYS | B | 485 | −49.291 | −46.282 | −16.344 | 1.00 | 33.08 | N |
| ATOM | 15680 | C | LYS | B | 485 | −53.370 | −42.035 | −15.701 | 1.00 | 28.37 | C |
| ATOM | 15681 | O | LYS | B | 485 | −53.288 | −42.481 | −14.563 | 1.00 | 28.59 | O |
| ATOM | 15683 | N | GLU | B | 486 | −53.083 | −40.766 | −15.980 | 1.00 | 29.89 | N |
| ATOM | 15684 | CA | GLU | B | 486 | −52.683 | −39.849 | −14.910 | 1.00 | 31.09 | C |
| ATOM | 15686 | CB | GLU | B | 486 | −52.174 | −38.511 | −15.470 | 1.00 | 31.55 | C |
| ATOM | 15689 | CG | GLU | B | 486 | −51.059 | −37.851 | −14.643 | 1.00 | 32.69 | C |
| ATOM | 15692 | CD | GLU | B | 486 | −49.785 | −38.689 | −14.605 | 1.00 | 34.51 | C |
| ATOM | 15693 | OE1 | GLU | B | 486 | −49.104 | −38.682 | −13.557 | 1.00 | 36.35 | O |
| ATOM | 15694 | OE2 | GLU | B | 486 | −49.476 | −39.368 | −15.611 | 1.00 | 34.55 | O |
| ATOM | 15695 | C | GLU | B | 486 | −53.836 | −39.615 | −13.939 | 1.00 | 31.70 | C |
| ATOM | 15696 | O | GLU | B | 486 | −53.684 | −39.868 | −12.750 | 1.00 | 31.90 | O |
| ATOM | 15698 | N | LYS | B | 487 | −54.983 | −39.164 | −14.453 | 1.00 | 32.71 | N |
| ATOM | 15699 | CA | LYS | B | 487 | −56.177 | −38.856 | −13.629 | 1.00 | 33.57 | C |
| ATOM | 15701 | CB | LYS | B | 487 | −57.343 | −38.402 | −14.519 | 1.00 | 33.54 | C |
| ATOM | 15704 | CG | LYS | B | 487 | −58.703 | −38.196 | −13.823 | 1.00 | 33.45 | C |
| ATOM | 15707 | CD | LYS | B | 487 | −58.686 | −37.024 | −12.866 | 1.00 | 33.71 | C |
| ATOM | 15710 | CE | LYS | B | 487 | −59.906 | −36.996 | −11.931 | 1.00 | 34.48 | C |
| ATOM | 15713 | NZ | LYS | B | 487 | −61.123 | −36.378 | −12.526 | 1.00 | 35.03 | N |
| ATOM | 15717 | C | LYS | B | 487 | −56.626 | −40.046 | −12.802 | 1.00 | 34.60 | C |
| ATOM | 15718 | O | LYS | B | 487 | −57.126 | −39.892 | −11.681 | 1.00 | 34.55 | O |
| ATOM | 15720 | N | LEU | B | 488 | −56.453 | −41.233 | −13.371 | 1.00 | 35.94 | N |
| ATOM | 15721 | CA | LEU | B | 488 | −56.878 | −42.451 | −12.723 | 1.00 | 37.00 | C |
| ATOM | 15723 | CB | LEU | B | 488 | −57.280 | −43.489 | −13.778 | 1.00 | 36.90 | C |
| ATOM | 15726 | CG | LEU | B | 488 | −58.081 | −44.714 | −13.312 | 1.00 | 37.52 | C |
| ATOM | 15728 | CD1 | LEU | B | 488 | −58.758 | −44.536 | −11.946 | 1.00 | 38.76 | C |
| ATOM | 15732 | CD2 | LEU | B | 488 | −59.121 | −45.084 | −14.346 | 1.00 | 38.42 | C |
| ATOM | 15736 | C | LEU | B | 488 | −55.786 | −42.980 | −11.803 | 1.00 | 38.02 | C |
| ATOM | 15737 | O | LEU | B | 488 | −56.063 | −43.315 | −10.653 | 1.00 | 38.19 | O |
| ATOM | 15739 | N | GLY | B | 489 | −54.550 | −43.016 | −12.298 | 1.00 | 39.44 | N |
| ATOM | 15740 | CA | GLY | B | 489 | −53.441 | −43.710 | −11.621 | 1.00 | 40.62 | C |
| ATOM | 15743 | C | GLY | B | 489 | −52.563 | −42.837 | −10.740 | 1.00 | 41.76 | C |
| ATOM | 15744 | O | GLY | B | 489 | −51.357 | −42.703 | −10.988 | 1.00 | 41.83 | O |
| ATOM | 15746 | N | GLY | B | 490 | −53.183 | −42.230 | −9.726 | 1.00 | 43.10 | N |
| ATOM | 15747 | CA | GLY | B | 490 | −52.481 | −41.538 | −8.636 | 1.00 | 43.82 | C |
| ATOM | 15750 | C | GLY | B | 490 | −51.131 | −40.924 | −8.967 | 1.00 | 44.31 | C |
| ATOM | 15751 | O | GLY | B | 490 | −50.084 | −41.560 | −8.831 | 1.00 | 44.25 | O |
| ATOM | 15753 | N | SER | B | 491 | −51.161 | −39.672 | −9.396 | 1.00 | 44.87 | N |
| ATOM | 15754 | CA | SER | B | 491 | −49.939 | −38.892 | −9.575 | 1.00 | 45.22 | C |
| ATOM | 15756 | CB | SER | B | 491 | −50.224 | −37.723 | −10.537 | 1.00 | 45.34 | C |
| ATOM | 15759 | OG | SER | B | 491 | −51.411 | −37.032 | −10.166 | 1.00 | 45.38 | O |
| ATOM | 15761 | C | SER | B | 491 | −49.419 | −38.389 | −8.203 | 1.00 | 45.14 | C |
| ATOM | 15762 | O | SER | B | 491 | −49.896 | −38.824 | −7.140 | 1.00 | 45.11 | O |
| ATOM | 15764 | N | LEU | B | 492 | −48.429 | −37.491 | −8.227 | 1.00 | 44.77 | N |
| ATOM | 15765 | CA | LEU | B | 492 | −48.046 | −36.752 | −7.018 | 1.00 | 44.31 | C |
| ATOM | 15767 | CB | LEU | B | 492 | −46.726 | −35.971 | −7.188 | 1.00 | 44.55 | C |
| ATOM | 15770 | CG | LEU | B | 492 | −45.530 | −36.546 | −7.972 | 1.00 | 45.73 | C |
| ATOM | 15772 | CD1 | LEU | B | 492 | −44.373 | −35.556 | −7.859 | 1.00 | 46.25 | C |
| ATOM | 15776 | CD2 | LEU | B | 492 | −45.084 | −37.972 | −7.530 | 1.00 | 46.14 | C |
| ATOM | 15780 | C | LEU | B | 492 | −49.151 | −35.760 | −6.703 | 1.00 | 43.30 | C |
| ATOM | 15781 | O | LEU | B | 492 | −49.315 | −35.370 | −5.555 | 1.00 | 43.49 | O |
| ATOM | 15783 | N | PHE | B | 493 | −49.903 | −35.367 | −7.735 | 1.00 | 42.05 | N |
| ATOM | 15784 | CA | PHE | B | 493 | −50.822 | −34.239 | −7.668 | 1.00 | 41.03 | C |
| ATOM | 15786 | CB | PHE | B | 493 | −50.913 | −33.549 | −9.028 | 1.00 | 40.81 | C |
| ATOM | 15789 | CG | PHE | B | 493 | −49.696 | −32.771 | −9.408 | 1.00 | 38.96 | C |
| ATOM | 15790 | CD1 | PHE | B | 493 | −49.651 | −31.408 | −9.233 | 1.00 | 37.06 | C |
| ATOM | 15792 | CE1 | PHE | B | 493 | −48.543 | −30.697 | −9.603 | 1.00 | 36.41 | C |

TABLE 3-7-continued

Coordinates of *P. tremuloides IspS*

| | | | | | | | | | | | |
|---|---|---|---|---|---|---|---|---|---|---|---|
| ATOM | 15794 | CZ | PHE | B | 493 | −47.471 | −31.341 | −10.158 | 1.00 | 35.87 | C |
| ATOM | 15796 | CE2 | PHE | B | 493 | −47.507 | −32.690 | −10.343 | 1.00 | 36.39 | C |
| ATOM | 15798 | CD2 | PHE | B | 493 | −48.612 | −33.400 | −9.977 | 1.00 | 37.36 | C |
| ATOM | 15800 | C | PHE | B | 493 | −52.240 | −34.603 | −7.268 | 1.00 | 40.76 | C |
| ATOM | 15801 | O | PHE | B | 493 | −52.686 | −35.733 | −7.419 | 1.00 | 40.35 | O |
| ATOM | 15803 | N | ALA | B | 494 | −52.943 | −33.584 | −6.790 | 1.00 | 40.72 | N |
| ATOM | 15804 | CA | ALA | B | 494 | −54.355 | −33.658 | −6.471 | 1.00 | 40.68 | C |
| ATOM | 15806 | CB | ALA | B | 494 | −54.786 | −32.362 | −5.770 | 1.00 | 40.70 | C |
| ATOM | 15810 | C | ALA | B | 494 | −55.175 | −33.851 | −7.744 | 1.00 | 40.59 | C |
| ATOM | 15811 | O | ALA | B | 494 | −55.013 | −33.099 | −8.716 | 1.00 | 40.95 | O |
| ATOM | 15813 | N | LYS | B | 495 | −56.071 | −34.835 | −7.733 | 1.00 | 40.12 | N |
| ATOM | 15814 | CA | LYS | B | 495 | −57.000 | −35.047 | −8.854 | 1.00 | 39.67 | C |
| ATOM | 15816 | CB | LYS | B | 495 | −58.008 | −36.166 | −8.520 | 1.00 | 39.98 | C |
| ATOM | 15819 | CG | LYS | B | 495 | −57.388 | −37.590 | −8.496 | 1.00 | 40.57 | C |
| ATOM | 15822 | CD | LYS | B | 495 | −58.468 | −38.688 | −8.419 | 1.00 | 41.18 | C |
| ATOM | 15825 | CE | LYS | B | 495 | −57.878 | −40.065 | −8.132 | 1.00 | 41.28 | C |
| ATOM | 15828 | NZ | LYS | B | 495 | −58.736 | −41.159 | −8.671 | 1.00 | 41.39 | N |
| ATOM | 15832 | C | LYS | B | 495 | −57.717 | −33.752 | −9.333 | 1.00 | 38.82 | C |
| ATOM | 15833 | O | LYS | B | 495 | −57.847 | −33.535 | −10.537 | 1.00 | 38.70 | O |
| ATOM | 15835 | N | PRO | B | 496 | −58.169 | −32.890 | −8.397 | 1.00 | 37.71 | N |
| ATOM | 15836 | CA | PRO | B | 496 | −58.701 | −31.551 | −8.687 | 1.00 | 36.80 | C |
| ATOM | 15838 | CB | PRO | B | 496 | −58.820 | −30.937 | −7.304 | 1.00 | 36.94 | C |
| ATOM | 15841 | CG | PRO | B | 496 | −59.255 | −32.073 | −6.483 | 1.00 | 37.90 | C |
| ATOM | 15844 | CD | PRO | B | 496 | −58.534 | −33.294 | −7.030 | 1.00 | 37.86 | C |
| ATOM | 15847 | C | PRO | B | 496 | −57.845 | −30.625 | −9.536 | 1.00 | 35.57 | C |
| ATOM | 15848 | O | PRO | B | 496 | −58.389 | −29.693 | −10.139 | 1.00 | 35.93 | O |
| ATOM | 15849 | N | PHE | B | 497 | −56.527 | −30.836 | −9.546 | 1.00 | 33.52 | N |
| ATOM | 15850 | CA | PHE | B | 497 | −55.654 | −30.083 | −10.439 | 1.00 | 31.34 | C |
| ATOM | 15852 | CB | PHE | B | 497 | −54.355 | −29.710 | −9.750 | 1.00 | 30.86 | C |
| ATOM | 15855 | CG | PHE | B | 497 | −53.394 | −28.989 | −10.634 | 1.00 | 29.04 | C |
| ATOM | 15856 | CD1 | PHE | B | 497 | −53.639 | −27.700 | −11.022 | 1.00 | 27.89 | C |
| ATOM | 15858 | CE1 | PHE | B | 497 | −52.752 | −27.028 | −11.834 | 1.00 | 27.39 | C |
| ATOM | 15860 | CZ | PHE | B | 497 | −51.599 | −27.653 | −12.259 | 1.00 | 27.40 | C |
| ATOM | 15862 | CE2 | PHE | B | 497 | −51.341 | −28.941 | −11.877 | 1.00 | 27.44 | C |
| ATOM | 15864 | CD2 | PHE | B | 497 | −52.236 | −29.604 | −11.074 | 1.00 | 28.18 | C |
| ATOM | 15866 | C | PHE | B | 497 | −55.390 | −30.870 | −11.714 | 1.00 | 30.24 | C |
| ATOM | 15867 | O | PHE | B | 497 | −55.301 | −30.266 | −12.786 | 1.00 | 30.39 | O |
| ATOM | 15869 | N | VAL | B | 498 | −55.295 | −32.200 | −11.630 | 1.00 | 28.50 | N |
| ATOM | 15870 | CA | VAL | B | 498 | −55.076 | −32.983 | −12.854 | 1.00 | 27.54 | C |
| ATOM | 15872 | CB | VAL | B | 498 | −54.778 | −34.472 | −12.611 | 1.00 | 27.34 | C |
| ATOM | 15874 | CG1 | VAL | B | 498 | −56.027 | −35.194 | −12.262 | 1.00 | 28.14 | C |
| ATOM | 15878 | CG2 | VAL | B | 498 | −53.731 | −34.649 | −11.530 | 1.00 | 27.04 | C |
| ATOM | 15882 | C | VAL | B | 498 | −56.277 | −32.857 | −13.784 | 1.00 | 26.60 | C |
| ATOM | 15883 | O | VAL | B | 498 | −56.129 | −32.864 | −14.995 | 1.00 | 26.33 | O |
| ATOM | 15885 | N | GLU | B | 499 | −57.468 | −32.731 | −13.214 | 1.00 | 25.87 | N |
| ATOM | 15886 | CA | GLU | B | 499 | −58.662 | −32.484 | −14.022 | 1.00 | 25.20 | C |
| ATOM | 15888 | CB | GLU | B | 499 | −59.975 | −32.639 | −13.206 | 1.00 | 25.26 | C |
| ATOM | 15891 | CG | GLU | B | 499 | −61.287 | −32.694 | −14.028 | 1.00 | 25.16 | C |
| ATOM | 15894 | CD | GLU | B | 499 | −61.422 | −33.922 | −14.973 | 1.00 | 26.79 | C |
| ATOM | 15895 | OE1 | GLU | B | 499 | −60.607 | −34.880 | −14.928 | 1.00 | 26.39 | O |
| ATOM | 15896 | OE2 | GLU | B | 499 | −62.379 | −33.926 | −15.785 | 1.00 | 27.83 | O |
| ATOM | 15897 | C | GLU | B | 499 | −58.542 | −31.097 | −14.641 | 1.00 | 24.27 | C |
| ATOM | 15898 | O | GLU | B | 499 | −58.819 | −30.948 | −15.832 | 1.00 | 24.32 | O |
| ATOM | 15900 | N | THR | B | 500 | −58.098 | −30.093 | −13.882 | 1.00 | 22.90 | N |
| ATOM | 15901 | CA | THR | B | 500 | −58.027 | −28.764 | −14.487 | 1.00 | 22.29 | C |
| ATOM | 15903 | CB | THR | B | 500 | −57.908 | −27.592 | −13.488 | 1.00 | 22.43 | C |
| ATOM | 15905 | OG1 | THR | B | 500 | −56.536 | −27.259 | −13.274 | 1.00 | 22.65 | O |
| ATOM | 15907 | CG2 | THR | B | 500 | −58.614 | −27.899 | −12.183 | 1.00 | 22.84 | C |
| ATOM | 15911 | C | THR | B | 500 | −56.940 | −28.671 | −15.565 | 1.00 | 21.20 | C |
| ATOM | 15912 | O | THR | B | 500 | −57.120 | −27.939 | −16.536 | 1.00 | 21.06 | O |
| ATOM | 15914 | N | ALA | B | 501 | −55.845 | −29.414 | −15.422 | 1.00 | 19.88 | N |
| ATOM | 15915 | CA | ALA | B | 501 | −54.906 | −29.574 | −16.537 | 1.00 | 19.24 | C |
| ATOM | 15917 | CB | ALA | B | 501 | −53.704 | −30.393 | −16.115 | 1.00 | 19.22 | C |
| ATOM | 15921 | C | ALA | B | 501 | −55.581 | −30.226 | −17.757 | 1.00 | 18.68 | C |
| ATOM | 15922 | O | ALA | B | 501 | −55.427 | −29.768 | −18.881 | 1.00 | 18.32 | O |
| ATOM | 15924 | N | ILE | B | 502 | −56.324 | −31.300 | −17.523 | 1.00 | 18.11 | N |
| ATOM | 15925 | CA | ILE | B | 502 | −57.023 | −31.988 | −18.591 | 1.00 | 17.68 | C |
| ATOM | 15927 | CB | ILE | B | 502 | −57.750 | −33.251 | −18.059 | 1.00 | 17.63 | C |
| ATOM | 15929 | CG1 | ILE | B | 502 | −56.713 | −34.350 | −17.769 | 1.00 | 18.16 | C |
| ATOM | 15932 | CD1 | ILE | B | 502 | −57.253 | −35.645 | −17.115 | 1.00 | 17.02 | C |
| ATOM | 15936 | CG2 | ILE | B | 502 | −58.756 | −33.762 | −19.063 | 1.00 | 16.93 | C |
| ATOM | 15940 | C | ILE | B | 502 | −57.990 | −31.030 | −19.289 | 1.00 | 17.50 | C |
| ATOM | 15941 | O | ILE | B | 502 | −58.153 | −31.071 | −20.512 | 1.00 | 17.62 | O |
| ATOM | 15943 | N | ASN | B | 503 | −58.604 | −30.139 | −18.524 | 1.00 | 17.23 | N |
| ATOM | 15944 | CA | ASN | B | 503 | −59.545 | −29.184 | −19.102 | 1.00 | 17.07 | C |
| ATOM | 15946 | CB | ASN | B | 503 | −60.184 | −28.327 | −18.016 | 1.00 | 17.21 | C |
| ATOM | 15949 | CG | ASN | B | 503 | −61.155 | −29.094 | −17.176 | 1.00 | 17.29 | C |
| ATOM | 15950 | OD1 | ASN | B | 503 | −61.721 | −30.097 | −17.609 | 1.00 | 16.66 | O |

TABLE 3-7-continued

Coordinates of *P. tremuloides IspS*

| | | | | | | | | | | | |
|---|---|---|---|---|---|---|---|---|---|---|---|
| ATOM | 15951 | ND2 | ASN | B | 503 | −61.365 | −28.621 | −15.958 | 1.00 | 19.16 | N |
| ATOM | 15954 | C | ASN | B | 503 | −58.920 | −28.270 | −20.149 | 1.00 | 16.59 | C |
| ATOM | 15955 | O | ASN | B | 503 | −59.611 | −27.811 | −21.071 | 1.00 | 16.67 | O |
| ATOM | 15957 | N | LEU | B | 504 | −57.629 | −27.992 | −20.014 | 1.00 | 15.79 | N |
| ATOM | 15958 | CA | LEU | B | 504 | −56.948 | −27.204 | −21.031 | 1.00 | 15.44 | C |
| ATOM | 15960 | CB | LEU | B | 504 | −55.530 | −26.865 | −20.609 | 1.00 | 15.07 | C |
| ATOM | 15963 | CG | LEU | B | 504 | −54.933 | −25.837 | −21.552 | 1.00 | 14.21 | C |
| ATOM | 15965 | CD1 | LEU | B | 504 | −54.246 | −24.726 | −20.800 | 1.00 | 14.21 | C |
| ATOM | 15969 | CD2 | LEU | B | 504 | −54.000 | −26.538 | −22.462 | 1.00 | 14.27 | C |
| ATOM | 15973 | C | LEU | B | 504 | −56.954 | −27.933 | −22.375 | 1.00 | 15.59 | C |
| ATOM | 15974 | O | LEU | B | 504 | −57.177 | −27.323 | −23.414 | 1.00 | 15.30 | O |
| ATOM | 15976 | N | ALA | B | 505 | −56.732 | −29.242 | −22.341 | 1.00 | 15.89 | N |
| ATOM | 15977 | CA | ALA | B | 505 | −56.914 | −30.073 | −23.514 | 1.00 | 16.23 | C |
| ATOM | 15979 | CB | ALA | B | 505 | −56.608 | −31.483 | −23.188 | 1.00 | 16.05 | C |
| ATOM | 15983 | C | ALA | B | 505 | −58.352 | −29.955 | −24.010 | 1.00 | 16.69 | C |
| ATOM | 15984 | O | ALA | B | 505 | −58.598 | −29.738 | −25.204 | 1.00 | 16.88 | O |
| ATOM | 15986 | N | ARG | B | 506 | −59.300 | −30.071 | −23.090 | 1.00 | 16.88 | N |
| ATOM | 15987 | CA | ARG | B | 506 | −60.709 | −29.972 | −23.457 | 1.00 | 17.20 | C |
| ATOM | 15989 | CB | ARG | B | 506 | −61.630 | −30.170 | −22.248 | 1.00 | 17.34 | C |
| ATOM | 15992 | CG | ARG | B | 506 | −61.549 | −31.537 | −21.614 | 1.00 | 17.46 | C |
| ATOM | 15995 | CD | ARG | B | 506 | −62.837 | −31.917 | −20.962 | 1.00 | 17.48 | C |
| ATOM | 15998 | NE | ARG | B | 506 | −62.783 | −33.280 | −20.435 | 1.00 | 18.37 | N |
| ATOM | 16000 | CZ | ARG | B | 506 | −62.404 | −33.613 | −19.201 | 1.00 | 19.03 | C |
| ATOM | 16001 | NH1 | ARG | B | 506 | −62.008 | −32.690 | −18.324 | 1.00 | 18.83 | N |
| ATOM | 16004 | NH2 | ARG | B | 506 | −62.415 | −34.892 | −18.841 | 1.00 | 19.72 | N |
| ATOM | 16007 | C | ARG | B | 506 | −61.038 | −28.646 | −24.114 | 1.00 | 17.32 | C |
| ATOM | 16008 | O | ARG | B | 506 | −61.754 | −28.622 | −25.111 | 1.00 | 17.41 | O |
| ATOM | 16010 | N | GLN | B | 507 | −60.540 | −27.543 | −23.564 | 1.00 | 17.59 | N |
| ATOM | 16011 | CA | GLN | B | 507 | −60.864 | −26.233 | −24.139 | 1.00 | 18.05 | C |
| ATOM | 16013 | CB | GLN | B | 507 | −60.382 | −25.090 | −23.258 | 1.00 | 18.16 | C |
| ATOM | 16016 | CG | GLN | B | 507 | −60.798 | −23.709 | −23.764 | 1.00 | 17.57 | C |
| ATOM | 16019 | CD | GLN | B | 507 | −62.291 | −23.508 | −23.723 | 1.00 | 17.42 | C |
| ATOM | 16020 | OE1 | GLN | B | 507 | −62.953 | −23.959 | −22.800 | 1.00 | 17.55 | O |
| ATOM | 16021 | NE2 | GLN | B | 507 | −62.832 | −22.823 | −24.722 | 1.00 | 17.56 | N |
| ATOM | 16024 | C | GLN | B | 507 | −60.258 | −26.060 | −25.521 | 1.00 | 18.49 | C |
| ATOM | 16025 | O | GLN | B | 507 | −60.855 | −25.413 | −26.380 | 1.00 | 18.73 | O |
| ATOM | 16027 | N | SER | B | 508 | −59.066 | −26.619 | −25.724 | 1.00 | 18.85 | N |
| ATOM | 16028 | CA | SER | B | 508 | −58.427 | −26.621 | −27.037 | 1.00 | 19.07 | C |
| ATOM | 16030 | CB | SER | B | 508 | −57.108 | −27.364 | −26.969 | 1.00 | 19.04 | C |
| ATOM | 16033 | OG | SER | B | 508 | −56.304 | −26.772 | −25.979 | 1.00 | 20.10 | O |
| ATOM | 16035 | C | SER | B | 508 | −59.305 | −27.296 | −28.065 | 1.00 | 19.12 | C |
| ATOM | 16036 | O | SER | B | 508 | −59.438 | −26.827 | −29.187 | 1.00 | 19.00 | O |
| ATOM | 16038 | N | HIS | B | 509 | −59.905 | −28.409 | −27.674 | 1.00 | 19.26 | N |
| ATOM | 16039 | CA | HIS | B | 509 | −60.814 | −29.095 | −28.559 | 1.00 | 19.33 | C |
| ATOM | 16041 | CB | HIS | B | 509 | −61.275 | −30.412 | −27.959 | 1.00 | 19.30 | C |
| ATOM | 16044 | CG | HIS | B | 509 | −60.263 | −31.501 | −28.067 | 1.00 | 18.71 | C |
| ATOM | 16045 | ND1 | HIS | B | 509 | −59.941 | −32.089 | −29.267 | 1.00 | 18.57 | N |
| ATOM | 16047 | CE1 | HIS | B | 509 | −59.020 | −33.012 | −29.064 | 1.00 | 19.07 | C |
| ATOM | 16049 | NE2 | HIS | B | 509 | −58.738 | −33.044 | −27.774 | 1.00 | 18.52 | N |
| ATOM | 16051 | CD2 | HIS | B | 509 | −59.499 | −32.105 | −27.129 | 1.00 | 18.43 | C |
| ATOM | 16053 | C | HIS | B | 509 | −62.017 | −28.251 | −28.878 | 1.00 | 19.60 | C |
| ATOM | 16054 | O | HIS | B | 509 | −62.491 | −28.286 | −29.969 | 1.00 | 19.68 | O |
| ATOM | 16056 | N | CYS | B | 510 | −62.540 | −27.502 | −27.932 | 1.00 | 20.12 | N |
| ATOM | 16057 | CA | CYS | B | 510 | −63.748 | −26.738 | −28.216 | 1.00 | 20.63 | C |
| ATOM | 16059 | CB | CYS | B | 510 | −64.493 | −26.492 | −26.915 | 1.00 | 20.70 | C |
| ATOM | 16062 | SG | CYS | B | 510 | −64.856 | −28.020 | −26.065 | 1.00 | 22.93 | S |
| ATOM | 16064 | C | CYS | B | 510 | −63.465 | −25.422 | −28.950 | 1.00 | 20.55 | C |
| ATOM | 16065 | O | CYS | B | 510 | −64.338 | −24.881 | −29.622 | 1.00 | 20.16 | O |
| ATOM | 16067 | N | THR | B | 511 | −62.236 | −24.933 | −28.827 | 1.00 | 20.89 | N |
| ATOM | 16068 | CA | THR | B | 511 | −61.833 | −23.654 | −29.378 | 1.00 | 21.32 | C |
| ATOM | 16070 | CB | THR | B | 511 | −60.682 | −23.107 | −28.550 | 1.00 | 20.76 | C |
| ATOM | 16072 | OG1 | THR | B | 511 | −61.208 | −22.619 | −27.324 | 1.00 | 19.50 | O |
| ATOM | 16074 | CG2 | THR | B | 511 | −59.961 | −21.994 | −29.253 | 1.00 | 19.79 | C |
| ATOM | 16078 | C | THR | B | 511 | −61.417 | −23.735 | −30.851 | 1.00 | 23.11 | C |
| ATOM | 16079 | O | THR | B | 511 | −61.910 | −22.992 | −31.694 | 1.00 | 22.75 | O |
| ATOM | 16081 | N | TYR | B | 512 | −60.501 | −24.646 | −31.152 | 1.00 | 25.46 | N |
| ATOM | 16082 | CA | TYR | B | 512 | −59.867 | −24.704 | −32.462 | 1.00 | 27.09 | C |
| ATOM | 16084 | CB | TYR | B | 512 | −58.397 | −25.107 | −32.327 | 1.00 | 27.16 | C |
| ATOM | 16087 | CG | TYR | B | 512 | −57.598 | −24.056 | −31.582 | 1.00 | 27.26 | C |
| ATOM | 16088 | CD1 | TYR | B | 512 | −57.300 | −22.834 | −32.182 | 1.00 | 28.18 | C |
| ATOM | 16090 | CE1 | TYR | B | 512 | −56.583 | −21.844 | −31.511 | 1.00 | 27.98 | C |
| ATOM | 16092 | CZ | TYR | B | 512 | −56.164 | −22.068 | −30.226 | 1.00 | 27.72 | C |
| ATOM | 16093 | OH | TYR | B | 512 | −55.462 | −21.072 | −29.584 | 1.00 | 27.09 | O |
| ATOM | 16095 | CE2 | TYR | B | 512 | −56.453 | −23.281 | −29.602 | 1.00 | 27.52 | C |
| ATOM | 16097 | CD2 | TYR | B | 512 | −57.171 | −24.262 | −30.278 | 1.00 | 26.68 | C |
| ATOM | 16099 | C | TYR | B | 512 | −60.633 | −25.623 | −33.382 | 1.00 | 28.79 | C |
| ATOM | 16100 | O | TYR | B | 512 | −61.050 | −25.179 | −34.444 | 1.00 | 28.98 | O |
| ATOM | 16102 | N | HIS | B | 513 | −60.789 | −26.893 | −32.991 | 1.00 | 31.06 | N |

TABLE 3-7-continued

| Coordinates of *P. tremuloides IspS* | | | | | | | | | | | |
|---|---|---|---|---|---|---|---|---|---|---|---|
| ATOM | 16103 | CA | HIS | B | 513 | −61.865 | −27.800 | −33.492 | 1.00 | 33.07 | C |
| ATOM | 16105 | CB | HIS | B | 513 | −62.740 | −28.208 | −32.265 | 1.00 | 33.66 | C |
| ATOM | 16108 | CG | HIS | B | 513 | −64.181 | −28.602 | −32.535 | 1.00 | 34.73 | C |
| ATOM | 16109 | ND1 | HIS | B | 513 | −65.035 | −27.903 | −33.367 | 1.00 | 35.70 | N |
| ATOM | 16111 | CE1 | HIS | B | 513 | −66.234 | −28.464 | −33.343 | 1.00 | 35.40 | C |
| ATOM | 16113 | NE2 | HIS | B | 513 | −66.206 | −29.469 | −32.491 | 1.00 | 35.10 | N |
| ATOM | 16115 | CD2 | HIS | B | 513 | −64.943 | −29.565 | −31.956 | 1.00 | 35.07 | C |
| ATOM | 16117 | C | HIS | B | 513 | −62.692 | −27.179 | −34.623 | 1.00 | 34.03 | C |
| ATOM | 16118 | O | HIS | B | 513 | −63.003 | −27.848 | −35.627 | 1.00 | 34.55 | O |
| ATOM | 16120 | N | ASN | B | 514 | −63.047 | −25.906 | −34.444 | 1.00 | 34.65 | N |
| ATOM | 16121 | CA | ASN | B | 514 | −63.713 | −25.123 | −35.483 | 1.00 | 35.15 | C |
| ATOM | 16123 | CB | ASN | B | 514 | −63.845 | −23.643 | −35.070 | 1.00 | 35.01 | C |
| ATOM | 16126 | CG | ASN | B | 514 | −64.704 | −23.456 | −33.820 | 1.00 | 33.48 | C |
| ATOM | 16127 | OD1 | ASN | B | 514 | −64.787 | −24.343 | −32.968 | 1.00 | 30.92 | O |
| ATOM | 16128 | ND2 | ASN | B | 514 | −65.327 | −22.295 | −33.703 | 1.00 | 32.16 | N |
| ATOM | 16131 | C | ASN | B | 514 | −63.192 | −25.274 | −36.942 | 1.00 | 36.08 | C |
| ATOM | 16132 | O | ASN | B | 514 | −62.010 | −25.051 | −37.254 | 1.00 | 35.69 | O |
| ATOM | 16134 | N | GLY | B | 515 | −64.119 | −25.765 | −37.772 | 1.00 | 37.15 | N |
| ATOM | 16135 | CA | GLY | B | 515 | −64.224 | −25.493 | −39.177 | 1.00 | 37.94 | C |
| ATOM | 16138 | C | GLY | B | 515 | −65.269 | −24.384 | −39.284 | 1.00 | 39.01 | C |
| ATOM | 16139 | O | GLY | B | 515 | −64.904 | −23.286 | −39.702 | 1.00 | 39.58 | O |
| ATOM | 16141 | N | ASP | B | 516 | −66.550 | −24.585 | −38.909 | 1.00 | 39.95 | N |
| ATOM | 16142 | CA | ASP | B | 516 | −67.167 | −25.810 | −38.349 | 1.00 | 40.65 | C |
| ATOM | 16144 | CB | ASP | B | 516 | −67.296 | −25.652 | −36.836 | 1.00 | 41.09 | C |
| ATOM | 16147 | CG | ASP | B | 516 | −66.318 | −26.511 | −36.063 | 1.00 | 43.63 | C |
| ATOM | 16148 | OD1 | ASP | B | 516 | −65.697 | −27.434 | −36.662 | 1.00 | 45.83 | O |
| ATOM | 16149 | OD2 | ASP | B | 516 | −66.152 | −26.246 | −34.843 | 1.00 | 47.12 | O |
| ATOM | 16150 | C | ASP | B | 516 | −68.603 | −26.067 | −38.853 | 1.00 | 40.78 | C |
| ATOM | 16151 | O | ASP | B | 516 | −69.134 | −25.301 | −39.660 | 1.00 | 41.28 | O |
| ATOM | 16153 | N | ALA | B | 517 | −69.222 | −27.141 | −38.349 | 1.00 | 40.66 | N |
| ATOM | 16154 | CA | ALA | B | 517 | −70.675 | −27.396 | −38.468 | 1.00 | 40.60 | C |
| ATOM | 16156 | CB | ALA | B | 517 | −71.422 | −26.622 | −37.359 | 1.00 | 40.27 | C |
| ATOM | 16160 | C | ALA | B | 517 | −71.295 | −27.106 | −39.862 | 1.00 | 40.79 | C |
| ATOM | 16161 | O | ALA | B | 517 | −70.654 | −27.296 | −40.899 | 1.00 | 40.67 | O |
| ATOM | 16163 | N | HIS | B | 518 | −72.562 | −26.696 | −39.874 | 1.00 | 41.13 | N |
| ATOM | 16164 | CA | HIS | B | 518 | −73.162 | −26.033 | −41.039 | 1.00 | 41.60 | C |
| ATOM | 16166 | CB | HIS | B | 518 | −74.446 | −26.756 | −41.480 | 1.00 | 42.24 | C |
| ATOM | 16169 | CG | HIS | B | 518 | −74.207 | −28.179 | −41.910 | 1.00 | 45.54 | C |
| ATOM | 16170 | ND1 | HIS | B | 518 | −73.441 | −28.509 | −43.012 | 1.00 | 48.51 | N |
| ATOM | 16172 | CE1 | HIS | B | 518 | −73.392 | −29.825 | −43.140 | 1.00 | 48.79 | C |
| ATOM | 16174 | NE2 | HIS | B | 518 | −74.092 | −30.364 | −42.156 | 1.00 | 49.12 | N |
| ATOM | 16176 | CD2 | HIS | B | 518 | −74.608 | −29.357 | −41.369 | 1.00 | 48.28 | C |
| ATOM | 16178 | C | HIS | B | 518 | −73.377 | −24.545 | −40.686 | 1.00 | 40.84 | C |
| ATOM | 16179 | O | HIS | B | 518 | −74.487 | −23.997 | −40.769 | 1.00 | 40.60 | O |
| ATOM | 16181 | N | THR | B | 519 | −72.261 | −23.932 | −40.275 | 1.00 | 40.10 | N |
| ATOM | 16182 | CA | THR | B | 519 | −72.143 | −22.521 | −39.878 | 1.00 | 39.39 | C |
| ATOM | 16184 | CB | THR | B | 519 | −72.561 | −22.263 | −38.393 | 1.00 | 39.40 | C |
| ATOM | 16186 | OG1 | THR | B | 519 | −71.823 | −23.131 | −37.517 | 1.00 | 39.55 | O |
| ATOM | 16188 | CG2 | THR | B | 519 | −74.074 | −22.460 | −38.178 | 1.00 | 38.98 | C |
| ATOM | 16192 | C | THR | B | 519 | −70.654 | −22.164 | −40.059 | 1.00 | 38.81 | C |
| ATOM | 16193 | O | THR | B | 519 | −69.800 | −23.050 | −40.067 | 1.00 | 38.48 | O |
| ATOM | 16195 | N | SER | B | 520 | −70.338 | −20.881 | −40.199 | 1.00 | 38.19 | N |
| ATOM | 16196 | CA | SER | B | 520 | −68.959 | −20.453 | −40.521 | 1.00 | 37.77 | C |
| ATOM | 16198 | CB | SER | B | 520 | −68.983 | −18.976 | −40.960 | 1.00 | 37.76 | C |
| ATOM | 16201 | OG | SER | B | 520 | −68.760 | −18.106 | −39.870 | 1.00 | 38.49 | O |
| ATOM | 16203 | C | SER | B | 520 | −67.974 | −20.724 | −39.340 | 1.00 | 37.24 | C |
| ATOM | 16204 | O | SER | B | 520 | −68.394 | −21.267 | −38.320 | 1.00 | 36.89 | O |
| ATOM | 16206 | N | PRO | B | 521 | −66.671 | −20.350 | −39.472 | 1.00 | 36.96 | N |
| ATOM | 16207 | CA | PRO | B | 521 | −65.692 | −20.638 | −38.396 | 1.00 | 36.80 | C |
| ATOM | 16209 | CB | PRO | B | 521 | −64.320 | −20.354 | −39.041 | 1.00 | 36.68 | C |
| ATOM | 16212 | CG | PRO | B | 521 | −64.599 | −19.593 | −40.309 | 1.00 | 37.19 | C |
| ATOM | 16215 | CD | PRO | B | 521 | −66.091 | −19.469 | −40.507 | 1.00 | 37.10 | C |
| ATOM | 16218 | C | PRO | B | 521 | −65.915 | −19.763 | −37.168 | 1.00 | 36.68 | C |
| ATOM | 16219 | O | PRO | B | 521 | −66.233 | −20.289 | −36.105 | 1.00 | 36.90 | O |
| ATOM | 16220 | N | ASP | B | 522 | −65.744 | −18.445 | −37.298 | 1.00 | 36.61 | N |
| ATOM | 16221 | CA | ASP | B | 522 | −66.373 | −17.528 | −36.347 | 1.00 | 36.58 | C |
| ATOM | 16223 | CB | ASP | B | 522 | −65.938 | −16.070 | −36.543 | 1.00 | 36.82 | C |
| ATOM | 16226 | CG | ASP | B | 522 | −64.456 | −15.846 | −36.243 | 1.00 | 37.94 | C |
| ATOM | 16227 | OD1 | ASP | B | 522 | −63.848 | −16.627 | −35.473 | 1.00 | 39.62 | O |
| ATOM | 16228 | OD2 | ASP | B | 522 | −63.891 | −14.876 | −36.790 | 1.00 | 39.40 | O |
| ATOM | 16229 | C | ASP | B | 522 | −67.836 | −17.718 | −36.681 | 1.00 | 36.12 | C |
| ATOM | 16230 | O | ASP | B | 522 | −68.150 | −18.306 | −37.702 | 1.00 | 35.98 | O |
| ATOM | 16232 | N | GLU | B | 523 | −68.732 | −17.249 | −35.830 | 1.00 | 35.69 | N |
| ATOM | 16233 | CA | GLU | B | 523 | −70.152 | −17.605 | −35.927 | 1.00 | 35.46 | C |
| ATOM | 16235 | CB | GLU | B | 523 | −70.703 | −17.560 | −37.379 | 1.00 | 35.51 | C |
| ATOM | 16238 | CG | GLU | B | 523 | −70.535 | −16.175 | −38.061 | 1.00 | 36.11 | C |
| ATOM | 16241 | CD | GLU | B | 523 | −70.854 | −16.136 | −39.572 | 1.00 | 36.72 | C |
| ATOM | 16242 | OE1 | GLU | B | 523 | −71.848 | −16.767 | −40.013 | 1.00 | 37.20 | O |

TABLE 3-7-continued

Coordinates of *P. tremuloides IspS*

| | | | | | | | | | | | |
|---|---|---|---|---|---|---|---|---|---|---|---|
| ATOM | 16243 | OE2 | GLU | B | 523 | −70.101 | −15.452 | −40.314 | 1.00 | 35.53 | O |
| ATOM | 16244 | C | GLU | B | 523 | −70.440 | −18.943 | −35.216 | 1.00 | 34.97 | C |
| ATOM | 16245 | O | GLU | B | 523 | −71.557 | −19.148 | −34.765 | 1.00 | 35.02 | O |
| ATOM | 16247 | N | LEU | B | 524 | −69.462 | −19.846 | −35.099 | 1.00 | 34.59 | N |
| ATOM | 16248 | CA | LEU | B | 524 | −69.503 | −20.832 | −34.004 | 1.00 | 34.45 | C |
| ATOM | 16250 | CB | LEU | B | 524 | −68.735 | −22.136 | −34.286 | 1.00 | 34.21 | C |
| ATOM | 16253 | CG | LEU | B | 524 | −69.530 | −23.434 | −34.508 | 1.00 | 33.92 | C |
| ATOM | 16255 | CD1 | LEU | B | 524 | −68.657 | −24.627 | −34.227 | 1.00 | 32.21 | C |
| ATOM | 16259 | CD2 | LEU | B | 524 | −70.794 | −23.520 | −33.641 | 1.00 | 34.06 | C |
| ATOM | 16263 | C | LEU | B | 524 | −68.901 | −20.162 | −32.791 | 1.00 | 34.38 | C |
| ATOM | 16264 | O | LEU | B | 524 | −69.535 | −20.067 | −31.741 | 1.00 | 34.49 | O |
| ATOM | 16266 | N | THR | B | 525 | −67.670 | −19.688 | −32.958 | 1.00 | 34.30 | N |
| ATOM | 16267 | CA | THR | B | 525 | −66.913 | −19.073 | −31.874 | 1.00 | 34.23 | C |
| ATOM | 16269 | CB | THR | B | 525 | −65.570 | −18.524 | −32.380 | 1.00 | 34.04 | C |
| ATOM | 16271 | OG1 | THR | B | 525 | −64.894 | −19.549 | −33.112 | 1.00 | 33.83 | O |
| ATOM | 16273 | CG2 | THR | B | 525 | −64.689 | −18.087 | −31.227 | 1.00 | 33.37 | C |
| ATOM | 16277 | C | THR | B | 525 | −67.702 | −17.960 | −31.184 | 1.00 | 34.46 | C |
| ATOM | 16278 | O | THR | B | 525 | −67.684 | −17.858 | −29.955 | 1.00 | 34.57 | O |
| ATOM | 16280 | N | ARG | B | 526 | −68.401 | −17.144 | −31.969 | 1.00 | 34.54 | N |
| ATOM | 16281 | CA | ARG | B | 526 | −69.200 | −16.056 | −31.418 | 1.00 | 34.60 | C |
| ATOM | 16283 | CB | ARG | B | 526 | −69.571 | −15.059 | −32.513 | 1.00 | 35.04 | C |
| ATOM | 16286 | CG | ARG | B | 526 | −70.256 | −13.800 | −32.013 | 1.00 | 37.13 | C |
| ATOM | 16289 | CD | ARG | B | 526 | −70.143 | −12.656 | −33.026 | 1.00 | 39.87 | C |
| ATOM | 16292 | NE | ARG | B | 526 | −70.353 | −13.075 | −34.420 | 1.00 | 42.28 | N |
| ATOM | 16294 | CZ | ARG | B | 526 | −71.543 | −13.292 | −35.000 | 1.00 | 44.26 | C |
| ATOM | 16295 | NH1 | ARG | B | 526 | −72.685 | −13.159 | −34.320 | 1.00 | 44.66 | N |
| ATOM | 16298 | NH2 | ARG | B | 526 | −71.593 | −13.658 | −36.279 | 1.00 | 44.49 | N |
| ATOM | 16301 | C | ARG | B | 526 | −70.448 | −16.593 | −30.735 | 1.00 | 33.91 | C |
| ATOM | 16302 | O | ARG | B | 526 | −70.848 | −16.074 | −29.704 | 1.00 | 33.74 | O |
| ATOM | 16304 | N | LYS | B | 527 | −71.048 | −17.637 | −31.306 | 1.00 | 33.39 | N |
| ATOM | 16305 | CA | LYS | B | 527 | −72.240 | −18.252 | −30.722 | 1.00 | 33.15 | C |
| ATOM | 16307 | CB | LYS | B | 527 | −72.837 | −19.332 | −31.639 | 1.00 | 33.42 | C |
| ATOM | 16310 | CG | LYS | B | 527 | −73.898 | −18.804 | −32.609 | 1.00 | 34.55 | C |
| ATOM | 16313 | CD | LYS | B | 527 | −74.643 | −19.919 | −33.358 | 1.00 | 35.43 | C |
| ATOM | 16316 | CE | LYS | B | 527 | −75.230 | −19.383 | −34.667 | 1.00 | 36.11 | C |
| ATOM | 16319 | NZ | LYS | B | 527 | −76.076 | −20.372 | −35.384 | 1.00 | 37.04 | N |
| ATOM | 16323 | C | LYS | B | 527 | −71.925 | −18.865 | −29.378 | 1.00 | 32.36 | C |
| ATOM | 16324 | O | LYS | B | 527 | −72.589 | −18.584 | −28.387 | 1.00 | 32.56 | O |
| ATOM | 16326 | N | ARG | B | 528 | −70.909 | −19.713 | −29.358 | 1.00 | 31.53 | N |
| ATOM | 16327 | CA | ARG | B | 528 | −70.502 | −20.401 | −28.138 | 1.00 | 30.77 | C |
| ATOM | 16329 | CB | ARG | B | 528 | −69.283 | −21.286 | −28.414 | 1.00 | 30.55 | C |
| ATOM | 16332 | CG | ARG | B | 528 | −69.624 | −22.519 | −29.252 | 1.00 | 29.48 | C |
| ATOM | 16335 | CD | ARG | B | 528 | −68.418 | −23.417 | −29.493 | 1.00 | 28.05 | C |
| ATOM | 16338 | NE | ARG | B | 528 | −68.811 | −24.774 | −29.880 | 1.00 | 26.55 | N |
| ATOM | 16340 | CZ | ARG | B | 528 | −67.968 | −25.719 | −30.288 | 1.00 | 25.87 | C |
| ATOM | 16341 | NH1 | ARG | B | 528 | −66.668 | −25.472 | −30.385 | 1.00 | 26.33 | N |
| ATOM | 16344 | NH2 | ARG | B | 528 | −68.424 | −26.920 | −30.615 | 1.00 | 25.49 | N |
| ATOM | 16347 | C | ARG | B | 528 | −70.225 | −19.415 | −27.004 | 1.00 | 30.42 | C |
| ATOM | 16348 | O | ARG | B | 528 | −70.721 | −19.582 | −25.885 | 1.00 | 30.30 | O |
| ATOM | 16350 | N | VAL | B | 529 | −69.455 | −18.376 | −27.307 | 1.00 | 29.96 | N |
| ATOM | 16351 | CA | VAL | B | 529 | −69.194 | −17.312 | −26.342 | 1.00 | 29.47 | C |
| ATOM | 16353 | CB | VAL | B | 529 | −68.261 | −16.227 | −26.932 | 1.00 | 29.40 | C |
| ATOM | 16355 | CG1 | VAL | B | 529 | −68.269 | −14.968 | −26.081 | 1.00 | 29.18 | C |
| ATOM | 16359 | CG2 | VAL | B | 529 | −66.845 | −16.782 | −27.062 | 1.00 | 28.90 | C |
| ATOM | 16363 | C | VAL | B | 529 | −70.516 | −16.723 | −25.841 | 1.00 | 28.98 | C |
| ATOM | 16364 | O | VAL | B | 529 | −70.759 | −16.682 | −24.641 | 1.00 | 28.97 | O |
| ATOM | 16366 | N | LEU | B | 530 | −71.384 | −16.308 | −26.752 | 1.00 | 28.54 | N |
| ATOM | 16367 | CA | LEU | B | 530 | −72.709 | −15.824 | −26.353 | 1.00 | 28.23 | C |
| ATOM | 16369 | CB | LEU | B | 530 | −73.631 | −15.604 | −27.559 | 1.00 | 28.09 | C |
| ATOM | 16372 | CG | LEU | B | 530 | −73.767 | −14.150 | −28.007 | 1.00 | 28.15 | C |
| ATOM | 16374 | CD1 | LEU | B | 530 | −72.412 | −13.570 | −28.406 | 1.00 | 27.99 | C |
| ATOM | 16378 | CD2 | LEU | B | 530 | −74.784 | −14.034 | −29.150 | 1.00 | 28.85 | C |
| ATOM | 16382 | C | LEU | B | 530 | −73.389 | −16.767 | −25.367 | 1.00 | 27.88 | C |
| ATOM | 16383 | O | LEU | B | 530 | −73.932 | −16.319 | −24.363 | 1.00 | 28.11 | O |
| ATOM | 16385 | N | SER | B | 531 | −73.352 | −18.066 | −25.652 | 1.00 | 27.28 | N |
| ATOM | 16386 | CA | SER | B | 531 | −74.081 | −19.049 | −24.849 | 1.00 | 26.68 | C |
| ATOM | 16388 | CB | SER | B | 531 | −74.209 | −20.363 | −25.612 | 1.00 | 26.68 | C |
| ATOM | 16391 | OG | SER | B | 531 | −72.970 | −21.033 | −25.681 | 1.00 | 26.67 | O |
| ATOM | 16393 | C | SER | B | 531 | −73.410 | −19.312 | −23.514 | 1.00 | 26.20 | C |
| ATOM | 16394 | O | SER | B | 531 | −74.076 | −19.550 | −22.511 | 1.00 | 25.86 | O |
| ATOM | 16396 | N | VAL | B | 532 | −72.085 | −19.281 | −23.512 | 1.00 | 25.86 | N |
| ATOM | 16397 | CA | VAL | B | 532 | −71.320 | −19.562 | −22.306 | 1.00 | 25.51 | C |
| ATOM | 16399 | CB | VAL | B | 532 | −69.891 | −20.055 | −22.651 | 1.00 | 25.34 | C |
| ATOM | 16401 | CG1 | VAL | B | 532 | −68.955 | −19.932 | −21.460 | 1.00 | 24.01 | C |
| ATOM | 16405 | CG2 | VAL | B | 532 | −69.950 | −21.484 | −23.158 | 1.00 | 24.95 | C |
| ATOM | 16409 | C | VAL | B | 532 | −71.271 | −18.357 | −21.373 | 1.00 | 25.52 | C |
| ATOM | 16410 | O | VAL | B | 532 | −71.377 | −18.523 | −20.164 | 1.00 | 25.82 | O |
| ATOM | 16412 | N | ILE | B | 533 | −71.137 | −17.158 | −21.935 | 1.00 | 25.39 | N |

TABLE 3-7-continued

Coordinates of *P. tremuloides IspS*

| | | | | | | | | | | | |
|---|---|---|---|---|---|---|---|---|---|---|---|
| ATOM | 16413 | CA | ILE | B | 533 | −70.875 | −15.954 | −21.151 | 1.00 | 25.48 | C |
| ATOM | 16415 | CB | ILE | B | 533 | −69.666 | −15.185 | −21.732 | 1.00 | 25.30 | C |
| ATOM | 16417 | CG1 | ILE | B | 533 | −68.375 | −15.928 | −21.451 | 1.00 | 24.91 | C |
| ATOM | 16420 | CD1 | ILE | B | 533 | −68.118 | −16.120 | −19.989 | 1.00 | 25.00 | C |
| ATOM | 16424 | CG2 | ILE | B | 533 | −69.553 | −13.797 | −21.130 | 1.00 | 25.81 | C |
| ATOM | 16428 | C | ILE | B | 533 | −72.065 | −14.983 | −21.030 | 1.00 | 25.77 | C |
| ATOM | 16429 | O | ILE | B | 533 | −72.537 | −14.707 | −19.928 | 1.00 | 25.77 | O |
| ATOM | 16431 | N | THR | B | 534 | −72.541 | −14.442 | −22.142 | 1.00 | 25.98 | N |
| ATOM | 16432 | CA | THR | B | 534 | −73.446 | −13.295 | −22.064 | 1.00 | 26.31 | C |
| ATOM | 16434 | CB | THR | B | 534 | −73.094 | −12.253 | −23.143 | 1.00 | 26.21 | C |
| ATOM | 16436 | OG1 | THR | B | 534 | −72.914 | −12.909 | −24.397 | 1.00 | 26.72 | O |
| ATOM | 16438 | CG2 | THR | B | 534 | −71.795 | −11.535 | −22.781 | 1.00 | 25.97 | C |
| ATOM | 16442 | C | THR | B | 534 | −74.961 | −13.621 | −22.064 | 1.00 | 26.50 | C |
| ATOM | 16443 | O | THR | B | 534 | −75.713 | −12.974 | −21.344 | 1.00 | 26.67 | O |
| ATOM | 16445 | N | GLU | B | 535 | −75.410 | −14.616 | −22.829 | 1.00 | 26.55 | N |
| ATOM | 16446 | CA | GLU | B | 535 | −76.851 | −14.892 | −22.961 | 1.00 | 26.50 | C |
| ATOM | 16448 | CB | GLU | B | 535 | −77.197 | −15.197 | −24.426 | 1.00 | 26.68 | C |
| ATOM | 16451 | CG | GLU | B | 535 | −77.226 | −13.936 | −25.296 | 1.00 | 27.68 | C |
| ATOM | 16454 | CD | GLU | B | 535 | −78.193 | −14.014 | −26.475 | 1.00 | 28.75 | C |
| ATOM | 16455 | OE1 | GLU | B | 535 | −79.370 | −13.588 | −26.330 | 1.00 | 27.72 | O |
| ATOM | 16456 | OE2 | GLU | B | 535 | −77.762 | −14.492 | −27.549 | 1.00 | 30.06 | O |
| ATOM | 16457 | C | GLU | B | 535 | −77.355 | −16.019 | −22.056 | 1.00 | 26.19 | C |
| ATOM | 16458 | O | GLU | B | 535 | −77.021 | −17.171 | −22.279 | 1.00 | 26.15 | O |
| ATOM | 16460 | N | PRO | B | 536 | −78.186 | −15.697 | −21.047 | 1.00 | 26.05 | N |
| ATOM | 16461 | CA | PRO | B | 536 | −78.692 | −16.763 | −20.196 | 1.00 | 26.05 | C |
| ATOM | 16463 | CB | PRO | B | 536 | −79.495 | −16.018 | −19.118 | 1.00 | 25.87 | C |
| ATOM | 16466 | CG | PRO | B | 536 | −79.140 | −14.621 | −19.239 | 1.00 | 25.88 | C |
| ATOM | 16469 | CD | PRO | B | 536 | −78.760 | −14.402 | −20.660 | 1.00 | 26.21 | C |
| ATOM | 16472 | C | PRO | B | 536 | −79.608 | −17.717 | −20.943 | 1.00 | 26.14 | C |
| ATOM | 16473 | O | PRO | B | 536 | −80.173 | −17.359 | −21.973 | 1.00 | 25.99 | O |
| ATOM | 16474 | N | ILE | B | 537 | −79.746 | −18.924 | −20.411 | 1.00 | 26.38 | N |
| ATOM | 16475 | CA | ILE | B | 537 | −80.662 | −19.905 | −20.960 | 1.00 | 26.58 | C |
| ATOM | 16477 | CB | ILE | B | 537 | −80.443 | −21.292 | −20.333 | 1.00 | 26.47 | C |
| ATOM | 16479 | CG1 | ILE | B | 537 | −79.023 | −21.789 | −20.600 | 1.00 | 26.38 | C |
| ATOM | 16482 | CD1 | ILE | B | 537 | −78.709 | −23.102 | −19.907 | 1.00 | 26.40 | C |
| ATOM | 16486 | CG2 | ILE | B | 537 | −81.430 | −22.300 | −20.890 | 1.00 | 26.71 | C |
| ATOM | 16490 | C | ILE | B | 537 | −82.072 | −19.420 | −20.657 | 1.00 | 26.93 | C |
| ATOM | 16491 | O | ILE | B | 537 | −82.347 | −18.965 | −19.545 | 1.00 | 26.81 | O |
| ATOM | 16493 | N | LEU | B | 538 | −82.963 | −19.491 | −21.641 | 1.00 | 27.36 | N |
| ATOM | 16494 | CA | LEU | B | 538 | −84.309 | −18.984 | −21.439 | 1.00 | 27.68 | C |
| ATOM | 16496 | CB | LEU | B | 538 | −85.181 | −19.094 | −22.698 | 1.00 | 27.75 | C |
| ATOM | 16499 | CG | LEU | B | 538 | −84.782 | −18.291 | −23.949 | 1.00 | 27.47 | C |
| ATOM | 16501 | CD1 | LEU | B | 538 | −85.992 | −18.109 | −24.844 | 1.00 | 27.11 | C |
| ATOM | 16505 | CD2 | LEU | B | 538 | −84.164 | −16.933 | −23.621 | 1.00 | 26.99 | C |
| ATOM | 16509 | C | LEU | B | 538 | −84.919 | −19.752 | −20.288 | 1.00 | 28.01 | C |
| ATOM | 16512 | N | PRO | B | 539 | −85.645 | −19.046 | −19.421 | 1.00 | 28.69 | N |
| ATOM | 16513 | CA | PRO | B | 539 | −86.028 | −19.631 | −18.152 | 1.00 | 29.05 | C |
| ATOM | 16515 | CB | PRO | B | 539 | −86.640 | −18.452 | −17.397 | 1.00 | 29.08 | C |
| ATOM | 16518 | CG | PRO | B | 539 | −87.144 | −17.548 | −18.447 | 1.00 | 28.86 | C |
| ATOM | 16521 | CD | PRO | B | 539 | −86.298 | −17.748 | −19.660 | 1.00 | 28.62 | C |
| ATOM | 16524 | C | PRO | B | 539 | −87.035 | −20.767 | −18.259 | 1.00 | 29.51 | C |
| ATOM | 16525 | O | PRO | B | 539 | −87.665 | −20.970 | −19.297 | 1.00 | 29.23 | O |
| ATOM | 16526 | N | PHE | B | 540 | −87.164 | −21.500 | −17.159 | 1.00 | 30.25 | N |
| ATOM | 16527 | CA | PHE | B | 540 | −88.089 | −22.613 | −17.070 | 1.00 | 30.56 | C |
| ATOM | 16529 | CB | PHE | B | 540 | −87.971 | −23.297 | −15.708 | 1.00 | 30.73 | C |
| ATOM | 16532 | CG | PHE | B | 540 | −88.848 | −24.499 | −15.567 | 1.00 | 30.49 | C |
| ATOM | 16533 | CD1 | PHE | B | 540 | −89.910 | −24.505 | −14.683 | 1.00 | 30.32 | C |
| ATOM | 16535 | CE1 | PHE | B | 540 | −90.718 | −25.614 | −14.568 | 1.00 | 30.59 | C |
| ATOM | 16537 | CZ | PHE | B | 540 | −90.475 | −26.722 | −15.346 | 1.00 | 30.55 | C |
| ATOM | 16539 | CE2 | PHE | B | 540 | −89.420 | −26.720 | −16.234 | 1.00 | 30.68 | C |
| ATOM | 16541 | CD2 | PHE | B | 540 | −88.619 | −25.617 | −16.342 | 1.00 | 30.43 | C |
| ATOM | 16543 | C | PHE | B | 540 | −89.507 | −22.120 | −17.257 | 1.00 | 30.76 | C |
| ATOM | 16544 | O | PHE | B | 540 | −89.967 | −21.257 | −16.508 | 1.00 | 30.59 | O |
| ATOM | 16546 | N | GLU | B | 541 | −90.184 | −22.677 | −18.259 | 1.00 | 31.13 | N |
| ATOM | 16547 | CA | GLU | B | 541 | −91.553 | −22.289 | −18.608 | 1.00 | 31.45 | C |
| ATOM | 16549 | CB | GLU | B | 541 | −91.525 | −21.186 | −19.680 | 1.00 | 31.60 | C |
| ATOM | 16552 | CG | GLU | B | 541 | −92.860 | −20.454 | −19.911 | 1.00 | 32.56 | C |
| ATOM | 16555 | CD | GLU | B | 541 | −93.773 | −21.133 | −20.935 | 1.00 | 33.64 | C |
| ATOM | 16556 | OE1 | GLU | B | 541 | −93.261 | −21.922 | −21.771 | 1.00 | 35.06 | O |
| ATOM | 16557 | OE2 | GLU | B | 541 | −95.002 | −20.868 | −20.901 | 1.00 | 32.44 | O |
| ATOM | 16558 | C | GLU | B | 541 | −92.326 | −23.510 | −19.105 | 1.00 | 31.31 | C |
| ATOM | 16559 | O | GLU | B | 541 | −92.860 | −24.286 | −18.310 | 1.00 | 31.30 | O |
| ATOM | 16562 | MG | MG | C | 1 | −42.844 | 11.427 | 13.309 | 1.00 | 46.29 | MG |
| ATOM | 16561 | MG | MG | C | 2 | −46.615 | −18.454 | −33.231 | 1.00 | 48.45 | MG |
| ATOM | 16563 | O | HOH | E | 1 | −50.507 | −5.408 | −4.491 | 1.00 | 17.42 | O |
| ATOM | 16566 | O | HOH | E | 2 | −64.748 | −36.007 | −11.725 | 1.00 | 2.00 | O |
| ATOM | 16569 | O | HOH | E | 3 | −40.643 | −2.220 | −34.996 | 1.00 | 2.00 | O |
| ATOM | 16572 | O | HOH | E | 4 | −36.090 | −9.757 | −37.074 | 1.00 | 17.20 | O |

TABLE 3-7-continued

| Coordinates of *P. tremuloides IspS* | | | | | | | | | | |
|---|---|---|---|---|---|---|---|---|---|---|
| ATOM | 16575 | O | HOH | E | 5 | −46.117 | −37.662 | −22.916 | 1.00 | 17.03 O |
| ATOM | 16578 | O | HOH | E | 6 | −49.541 | 35.476 | 6.921 | 1.00 | 14.03 O |
| ATOM | 16581 | O | HOH | E | 7 | −32.288 | 27.572 | 16.443 | 1.00 | 13.16 O |
| ATOM | 16584 | O | HOH | E | 8 | −50.706 | 10.207 | −15.061 | 1.00 | 18.73 O |
| ATOM | 16587 | O | HOH | E | 9 | −77.188 | 36.767 | −9.218 | 1.00 | 8.05 O |
| ATOM | 16590 | O | HOH | E | 10 | −90.260 | −31.248 | −21.071 | 1.00 | 2.00 O |
| ATOM | 16593 | O | HOH | E | 11 | −70.920 | −33.414 | −3.884 | 1.00 | 9.35 O |
| ATOM | 16596 | O | HOH | E | 12 | −37.761 | −21.294 | −9.249 | 1.00 | 25.78 O |
| ATOM | 16599 | O | HOH | E | 13 | −76.050 | 23.855 | −18.293 | 1.00 | 2.00 O |
| ATOM | 16602 | O | HOH | E | 14 | −76.876 | −19.575 | −22.856 | 1.00 | 19.25 O |
| ATOM | 16605 | O | HOH | E | 15 | −40.936 | 11.629 | −24.832 | 1.00 | 22.29 O |
| ATOM | 16608 | O | HOH | E | 16 | −85.551 | 34.832 | 3.260 | 1.00 | 25.14 O |
| ATOM | 16611 | O | HOH | E | 17 | −56.825 | 31.771 | −7.464 | 1.00 | 17.27 O |
| ATOM | 16614 | O | HOH | E | 18 | −76.222 | 39.261 | −.613 | 1.00 | 25.47 O |

Example 4

Three-Dimensional Structure of *P. alba* IspS

I. Expression of 6×His-Tagged IspS

N-terminally 6×His-tagged IspS was expressed and purified from strain MD09-167. Construction of MD09-167 is described in Example 2. The growth procedure is suitable for histidine tagged enzymes expressed in BL21(λDE3)pLysS cells. A 10 ml of overnight culture was prepared for each 1 L of planned growth. The appropriate antibiotics (50 mg/ml kanamycin, 50 mg/ml chloramphenicol, and/or 50 mg/ml Carbenecillin) was added to 10 ml of LB medium in a 25 ml flask and was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1 L day culture was inoculated with 10 ml of overnight culture and grown at 30-37° C. with shaking at ~220 rpm until the $OD_{600}$ reached ~0.4-0.6. Day cultures were then induced with 400 μM IPTG and allowed to continue growing at 30° C. with shaking at 220 rpm for ~5-6 hours. Cells were then harvested by centrifugation at 10,000×g for 10 min, 4° C. Following Harvest, cells were used directly or stored at −80° C. until ready to process II. Purification of 6×His-Tagged IspS For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 40-50 ml of lysis buffer was used per 1 L of cell pellet. Cells were then incubated on ice for approximately 30 min. The cell suspension was then lysed fully by passing 2-3 times through a french pressure cell (large french press cell at 1200 psi/High setting) until lysate started to look clear. A sample of the lysate was saved for activity assay and gel analysis (~100 μl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 μl).

The clarified lysate was run over HisTrap HP columns (GE healthcare) using a gradient from 0-100% Ni buffer B. Following loading of the lysate on the column, the column was washed with Ni wash buffer (50 mM $NaH_2PO_4$, 300 mm NaCl, 20 mM imidazole, ph 8.0). The his-tagged IspS was then eluted from the column using a gradient from 0-100% Ni elution buffer (50 mM $NaH_2PO_4$, 300 mM NaCl, 500 mM imidazole, ph 8.0) and fractions containing the his-tagged IspS were collected. The column was then washed with Ni stripping buffer (20 mM $NaH_2PO_4$, 0.5 m NaCl, 50 mM EDTA, ph 7.4). Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a Hi Prep 26/10 Desalting column (GE healthcare) packed with Sephadex G25 resin. The G-25 buffer consisted of 50 mM HEPES, 50 mM NaCl, and 1 mM DTT, pH 7.4. The desired sample was then chromatographed on Hi Trap Q HP column (GE) (Q seph buffer A was 50 mM Tris, 0.05 M NaCl, 1 mM DTT, pH 7.6. Q seph buffer B was 50 mM Tris, 1.0 M NaCl, 1 mM DTT, pH 7.6) and concentrated if necessary. Sample buffer was then exchanged by passing sample over a Hi Prep 26/10 Desalting column (GE healthcare) packed with Sephadex G25 resin. A final polishing step of Gel filtration is used as necessary. Pass the sample over a Hi Load 26/60 Superdex 200 prep grade (GE) in gel filtration buffer: (50 mM HEPES, 150 mM NaCl, 1 mM DTT, pH 7.4). Fractions were then analyzed and concentrated. The samples were then stored at −80° C.

TEV Cleavage (IspS from Strains MD09-165 and MD09-167)

For digestion, enzymes were purified through a Ni charged sepharose (GE Healthcare) and desalted into 50 mM HEPES, 50 mM NaCl pH 7.4 buffer containing 1 mM DTT. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (which is also tagged), and impurities. The Ni column pass though and washes were analyzed using SDS-PAGE gel (NUPAGE, Invitrogen) and DMAPP activity assays. Samples containing pure enzyme were pooled and desalted into 50 mM NaCl pH 7.4 buffer containing 1 mM DTT and stored at −80° C.

III. Crystal Structure Determination

The enzyme expressed from MD09-167 was purified and a concentrated protein solution was then prepared for surveying possible crystallization conditions. The protein was purified independently and surveyed as described below. All in-house crystallization screens were set up using the hanging drop vapor diffusion method. At a minimum, the protein was surveyed using the following commercial screens: the Crystal Screen from Hampton Research (Aliso Viejo, Calif.) and the JCSG+Suite from Qiagen (Valencia, Calif.).

A truncated *P. alba* IspS construct featuring two additional residues before the twin-arginine motif was generated (MD09-167). This construct contains a C-terminal histidine-tag, and crystallization experiments were set up with the tag either cleaved or not cleaved, at varying protein concentrations, and with or without sodium pyrophosphate. Initial crystallization screens were setup using the Crystal Screen from Hampton Research and the JCSG+Suite from Qiagen. Crystals of protein derived from MD09-167 were observed in numerous conditions; optimization included 528 variations of pH, precipitating agents, concentrations, and inhibitors. From the optimization experiments, twenty different MD09-167 crystals were screened in-house for diffraction. In an effort to improve the resolution, various crystal freezing conditions were tested, with the effect of improving the diffraction limits from 10 Å to 6.5 Å. Upon further optimization of both crystallization and freezing conditions, a crystal composed of non-cleaved histidine-tagged protein was obtained that diffracted to 2.7 Å in house. The large, rod-shaped crystals belong to the tetragonal space group $P4_32_12$, and have unit cell dimensions a=156.8, b=156.8, c=142.5. The crystals were grown by mixing 2 μL of protein (9 mg/ml protein) with 2 μL of precipitant solution (0.2 M NaMalonate, pH 7.0 and 18% (wt/vol) polyethylene glycol 3350) and equilibrated against 500 μL of precipitant. Prior to flash-freezing the crystal in liquid nitrogen, the crystals were cryoprotected by swishing through 0.2 M NaMalonate, pH 7.0, 18% (wt/vol) polyethylene glycol 3350, and 25% (wt/vol) ethylene glycol.

An identical crystal was prepared and sent to Stanford Synchrotron Radiation Laboratory, and data were collected at Beamline 11-1. Data were integrated using Mosflm (Leslie, A. (1998) J. of Appl. Crystallography 30, 1036-1040) and scaled using SCALA (Collaborative Computational Project, N. (1994) Acta Crystallographica Section D 50, 760-763). The data were phased with MOLREP (Vagin, A., and Teplyakov, A. (1997) J. of Appl. Crystallography 30, 1022-1025), using the IspS from *P. tremuloides* (Example 3) as the starting model. The crystal contains one dimer in the asymmetric unit with a solvent content of 64%. Data collection and refinement statistics are given in Table 4-1.

Refinement with Refmac5 (Collaborative Computational Project, N. (1994) Acta Crystallographica Section D 50, 760-763) was used with iterative manual rebuilding steps using the visualization program Coot (Emsley, P., and Cowtan, K. (2004) Acta Crystallographica Section D 60, 2126-2132). During refinement, the geometry of the protein was checked using Molprobity (Davis, I. W., et al. (2007) Nucl. Acids Res., 35:W375-W383). The coordinates are provided in Table 4-2.

TABLE 4-1

Data Collection and Refinement Statistics

| | |
|---|---|
| Data Collection | |
| Space Group | $P4_32_12$ |
| Cell dimensions | |
| A, b, c (Å) | 156.8, 156.8, 142.5 |
| α, β, γ, (°) | 90.0, 90.0, 90.0 |
| Resolution (Å) | 45.5-2.30 |
| $R_{merge}$ | 8.2 (60.6)[a] |
| <I/σI> | 10.0 (2.2) |
| Completeness (%) | 99.1 (96.2) |
| Redundancy | 4.7 (4.3) |
| Refinement | |
| Resolution (Å) | 38.0-2.30 |
| No. measured reflections | 366320 |
| No. Unique reflections | 74242 |
| $R_{work}$ | 20.7 |
| $R_{free}$ | 24.2 |
| rmsd bonds, (Å) | 0.012 |
| rmsd angles, (°) | 1.206 |
| No. of Atoms | |
| Protein | 8689 |
| Water | 205 |

[a]Values in parenthesis refer to highest resolution shell.

TABLE 4-2

Coordinates of *P. alba* IspS

```
HEADER   ----  XX-XXX-9- xxxx
COMPND   ---
REMARK   3
REMARK   3  REFINEMENT.
REMARK   3  PROGRAM     : REFMAC 5.5.0088
REMARK   3  AUTHORS     : MURSHUDOV, VAGIN, DODSON
REMARK   3
REMARK   3  REFINEMENT TARGET: MAXIMUM LIKELIHOOD
REMARK   3
REMARK   3  DATA USED IN REFINEMENT.
REMARK   3  RESOLUTION RANGE HIGH (ANGSTROMS): 2.30
REMARK   3  RESOLUTION RANGE LOW (ANGSTROMS): 43.66
REMARK   3  DATA CUTOFF (SIGMA(F)): NONE
REMARK   3  COMPLETENESS FOR RANGE  (%): 98.90
REMARK   3  NUMBER OF REFLECTIONS    : 74242
REMARK   3
REMARK   3  FIT TO DATA USED IN REFINEMENT.
REMARK   3  CROSS-VALIDATION METHOD  : THROUGHOUT
REMARK   3  FREE R VALUE TEST SET SELECTION : RANDOM    p
REMARK   3  R VALUE (WORKING + TEST SET): 0.20949
REMARK   3  R VALUE (WORKING SET): 0.20777
REMARK   3  FREE R VALUE : 0.24192
REMARK   3  FREE R VALUE TEST SET SIZE (%): 5.1
REMARK   3  FREE R VALUE TEST SET COUNT : 3968
REMARK   3
REMARK   3  FIT IN THE HIGHEST RESOLUTION BIN.
REMARK   3  TOTAL NUMBER OF BINS USED   : 20
REMARK   3  BIN RESOLUTION RANGE HIGH    : 2.300
REMARK   3  BIN RESOLUTION RANGE LOW  : 2.360
REMARK   3  REFLECTION IN BIN (WORKING SET): 5205
REMARK   3  BIN COMPLETENESS (WORKING + TEST) (%): 95.11
```

TABLE 4-2-continued

| Coordinates of *P. alba* IspS | | |
|---|---|---|
| REMARK | 3 | BIN R VALUE (WORKING SET): 0.350 |
| REMARK | 3 | BIN FREE R VALUE SET COUNT : 257 |
| REMARK | 3 | BIN FREE R VALUE : 0.364 |
| REMARK | 3 | |
| REMARK | 3 | NUMBER OF NON-HYDROGEN ATOMS USED IN REFINEMENT. |
| REMARK | 3 | ALL ATOMS : 8894 |
| REMARK | 3 | |
| REMARK | 3 | B VALUES. |
| REMARK | 3 | FROM WILSON PLOT (A**2): NULL |
| REMARK | 3 | MEAN B VALUE (OVERALL, A**2): 28.532 |
| REMARK | 3 | OVERALL ANISOTROPIC B VALUE. |
| REMARK | 3 | B11 (A**2): 0.19 |
| REMARK | 3 | B22 (A**2): 0.19 |
| REMARK | 3 | B33 (A**2): −0.39 |
| REMARK | 3 | B12 (A**2): −0.00 |
| REMARK | 3 | B13 (A**2): −0.00 |
| REMARK | 3 | B23 (A**2): 0.00 |
| REMARK | 3 | |
| REMARK | 3 | ESTIMATED OVERALL COORDINATE ERROR. |
| REMARK | 3 | ESU BASED ON R VALUE (A): 0.234 |
| REMARK | 3 | ESU BASED ON FREE R VALUE (A): 0.197 |
| REMARK | 3 | ESU BASED ON MAXIMUM LIKELIHOOD (A): 0.132 |
| REMARK | 3 | ESU FOR B VALUES BASED ON MAXIMUM LIKELIHOOD (A**2): 12.016 |
| REMARK | 3 | |
| REMARK | 3 | CORRELATION COEFFICIENTS. |
| REMARK | 3 | CORRELATION COEFFICIENT FO-FC : 0.949 |
| REMARK | 3 | CORRELATION COEFFICIENT FO-FC FREE: 0.932 |
| REMARK | 3 | |
| REMARK | 3 | RMS DEVIATIONS FROM IDEAL VALUES COUNT RMS WEIGHT |
| REMARK | 3 | BOND LENGTHS REFINED ATOMS (A): 8874 ; 0.012; 0.022 |
| REMARK | 3 | BOND LENGTHS OTHERS (A): 6064 ; 0.001 ;0.020 |
| REMARK | 3 | BOND ANGLES REFINED ATOMS (DEGREES): 12007 ; 1.206 ; 1.952 |
| REMARK | 3 | BOND ANGLES OTHERS (DEGREES): 14720 ; 0.851 ; 3.000 |
| REMARK | 3 | TORSION ANGLES, PERIOD 1 (DEGREES): 1070 ; 5.228; 5.000 |
| REMARK | 3 | TORSION ANGLES, PERIOD 2 (DEGREES): 460 ;35.290 ;24.304 |
| REMARK | 3 | TORSION ANGLES, PERIOD 3 (DEGREES): 1582 ;14.921 ;15.000 |
| REMARK | 3 | TORSION ANGLES, PERIOD 4 (DEGREES): 61 ;16.584 ;15.000 |
| REMARK | 3 | CHIRAL-CENTER RESTRAINTS (A**3): 1314 ; 0.072 ; 0.200 |
| REMARK | 3 | GENERAL PLANES REFINED ATOMS (A): 9879 ; 0.005 ; 0.020 |
| REMARK | 3 | GENERAL PLANES OTHERS (A): 1878 ; 0.001 ;0.020 |
| REMARK | 3 | |
| REMARK | 3 | ISOTROPIC THERMAL FACTOR RESTRAINTS. COUNT RMS WEIGHT |
| REMARK | 3 | MAIN-CHAIN BOND REFINED ATOMS (A**2): 5310; 1.592; 3.000 |
| REMARK | 3 | MAIN-CHAIN BOND OTHER ATOMS (A**2): 2148 ; 0.457 ; 3.000 |
| REMARK | 3 | MAIN-CHAIN ANGLE REFINED ATOMS (A**2): 8546 ; 3.009 ; 5.000 |
| REMARK | 3 | SIDE-CHAIN BOND REFINED ATOMS (A**2): 3564 ;4.694 ; 8.000 |
| REMARK | 3 | SIDE-CHAIN ANGLE REFINED ATOMS (A**2): 3455; 7.036 ;11.000 |
| REMARK | 3 | |
| REMARK | 3 | NCS RESTRAINTS STATISTICS |
| REMARK | 3 | NUMBER OF DIFFERENT NCS GROUPS : 1 |
| REMARK | 3 | |
| REMARK | 3 | NCS GROUP NUMBER : 1 |
| REMARK | 3 | CHAIN NAMES : A B |
| REMARK | 3 | NUMBER OF COMPONENTS NCS GROUP: 1 |
| REMARK | 3 | COMPONENT C SSSEQI TO C SSSEQI CODE |
| REMARK | 3 | 1 A 1 A 560 4 |
| REMARK | 3 | 1 B 1 B 560 4 |
| REMARK | 3 | GROUP CHAIN COUNT RMS WEIGHT |
| REMARK | 3 | MEDIUM POSITIONAL 1 1 (A): 7275 ; 0.30 ; 0.50 |
| REMARK | 3 | MEDIUM THERMAL 1 1 (A**2): 7275 ; 0.78 ; 2.00 |
| REMARK | 3 | |

TABLE 4-2-continued

Coordinates of *P. alba* IspS

| | | |
|---|---|---|
| REMARK | 3 | TWIN DETAILS |
| REMARK | 3 | NUMBER OF TWIN DOMAINS : NULL |
| REMARK | 3 | |
| REMARK | 3 | |
| REMARK | 3 | TLS DETAILS |
| REMARK | 3 | NUMBER OF TLS GROUPS : 2 |
| REMARK | 3 | ATOM RECORD CONTAINS RESIDUAL B FACTORS ONLY |
| REMARK | 3 | |
| REMARK | 3 | TLS GROUP : 1 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: A −10 A 9999 |
| REMARK | 3 | ORIGIN FOR THE GROUP (A): 55.1340 −22.7990 1.5640 |
| REMARK | 3 | T TENSOR |
| REMARK | 3 | T11: 0.1012 T22: 0.0842 |
| REMARK | 3 | T33: 0.0487 T12: −0.0797 |
| REMARK | 3 | T13: −0.0129 T23: −0.0050 |
| REMARK | 3 | L TENSOR |
| REMARK | 3 | L11: 0.4547 L22: 1.7223 |
| REMARK | 3 | L33: 0.4716 L12: −0.3910 |
| REMARK | 3 | L13: 0.0096 L23: 0.1512 |
| REMARK | 3 | S TENSOR |
| REMARK | 3 | S11: 0.0834 S12: −0.1118 S13: 0.0428 |
| REMARK | 3 | S21: −0.0018 S22: −0.0458 S23: −0.0748 |
| REMARK | 3 | S31: −0.0352 S32: 0.0105 S33: −0.0376 |
| REMARK | 3 | |
| REMARK | 3 | TLS GROUP : 2 |
| REMARK | 3 | NUMBER OF COMPONENTS GROUP : 1 |
| REMARK | 3 | COMPONENTS C SSSEQI TO C SSSEQI |
| REMARK | 3 | RESIDUE RANGE: B −10 B 9999 |
| REMARK | 3 | ORIGIN FOR THE GROUP (A): 61.5680 28.1500 −20.5740 |
| REMARK | 3 | T TENSOR |
| REMARK | 3 | T11: 0.1284 T22: 0.1262 |
| REMARK | 3 | T33: 0.1080 T12: 0.0397 |
| REMARK | 3 | T13: −0.0366 T23: 0.0120 |
| REMARK | 3 | L TENSOR |
| REMARK | 3 | L11: 1.1443 L22: 0.6715 |
| REMARK | 3 | L33: 0.8680 L12: 0.4490 |
| REMARK | 3 | L13: 0.6089 L23: 0.2346 |
| REMARK | 3 | S TENSOR |
| REMARK | 3 | S11: 0.0652 S12: 0.1638 S13: 0.0430 |
| REMARK | 3 | S21: 0.0628 S22: −0.0956 S23: −0.0492 |
| REMARK | 3 | S31: −0.0269 S32: 0.2044 S33: 0.0305 |
| REMARK | 3 | |
| REMARK | 3 | |
| REMARK | 3 | BULK SOLVENT MODELLING. |
| REMARK | 3 | METHOD USED: MASK |
| REMARK | 3 | PARAMETERS FOR MASK CALCULATION |
| REMARK | 3 | VDW PROBE RADIUS : 1.40 |
| REMARK | 3 | ION PROBE RADIUS : 0.80 |
| REMARK | 3 | SHRINKAGE RADIUS : 0.80 |
| REMARK | 3 | |
| REMARK | 3 | OTHER REFINEMENT REMARKS: |
| REMARK | 3 | HYDROGENS HAVE BEEN ADDED IN THE RIDING POSITIONS |
| REMARK | 3 | U VALUES: RESIDUAL ONLY |
| REMARK | 3 | |
| REMARK | 3 | OTHER REFINEMENT REMARKS: 1. RESIDUES A39, A539, A541 ARE |
| REMARK | 3 | RAMACHANDRAN OUTLIERS AND ARE LOCATED IN POOR DENSITY. |

LINKR ASN A 512 THR A 517 gap
LINKR SER B 18 ILE B 24 gap
LINKR ASN B 512 THR B 517 gap

| | |
|---|---|
| CRYST1 | 156.800 156.800 142.480 90.00 90.00 90.00 P 43 21 2 |
| SCALE1 | 0.006378 0.000000 0.000000 0.00000 |
| SCALE2 | −0.000000 0.006378 0.000000 0.00000 |
| SCALE3 | 0.000000 −0.000000 0.007019 0.00000 |

| | | | | | | | | | | | | |
|---|---|---|---|---|---|---|---|---|---|---|---|---|
| ATOM | 1 | N | ALA | A | 23 | 59.766 | −33.590 | −29.936 | 1.00 | 64.60 | A | N |
| ATOM | 2 | CA | ALA | A | 23 | 60.006 | −32.892 | −28.637 | 1.00 | 65.14 | A | C |
| ATOM | 4 | CB | ALA | A | 23 | 60.361 | −33.912 | −27.536 | 1.00 | 65.26 | A | C |
| ATOM | 8 | C | ALA | A | 23 | 61.108 | −31.833 | −28.796 | 1.00 | 64.48 | A | C |
| ATOM | 9 | O | ALA | A | 23 | 62.101 | −32.081 | −29.489 | 1.00 | 64.58 | A | O |
| ATOM | 13 | N | ASN | A | 24 | 60.937 | −30.692 | −28.111 | 1.00 | 63.60 | A | N |
| ATOM | 14 | CA | ASN | A | 24 | 61.661 | −29.425 | −28.393 | 1.00 | 63.75 | A | C |
| ATOM | 16 | CB | ASN | A | 24 | 60.620 | −28.275 | −28.535 | 1.00 | 65.26 | A | C |
| ATOM | 19 | CG | ASN | A | 24 | 61.091 | −27.095 | −29.448 | 1.00 | 66.51 | A | C |
| ATOM | 20 | OD1 | ASN | A | 24 | 62.282 | −26.926 | −29.744 | 1.00 | 66.15 | A | O |

TABLE 4-2-continued

| Coordinates of *P. alba* IspS | | | | | | | | | | | | |
|---|---|---|---|---|---|---|---|---|---|---|---|---|
| ATOM | 21 | ND2 | ASN | A | 24 | 60.132 | −26.265 | −29.865 | 1.00 | 65.85 | A | N |
| ATOM | 24 | C | ASN | A | 24 | 62.780 | −29.018 | −27.379 | 1.00 | 61.71 | A | C |
| ATOM | 25 | O | ASN | A | 24 | 62.970 | −29.635 | −26.325 | 1.00 | 60.31 | A | O |
| ATOM | 27 | N | TYR | A | 25 | 63.472 | −27.935 | −27.748 | 1.00 | 59.76 | A | N |
| ATOM | 28 | CA | TYR | A | 25 | 64.743 | −27.478 | −27.188 | 1.00 | 57.41 | A | C |
| ATOM | 30 | CB | TYR | A | 25 | 65.795 | −27.490 | −28.311 | 1.00 | 56.05 | A | C |
| ATOM | 33 | CG | TYR | A | 25 | 65.932 | −28.808 | −29.027 | 1.00 | 47.11 | A | C |
| ATOM | 34 | CD1 | TYR | A | 25 | 66.574 | −29.878 | −28.415 | 1.00 | 37.57 | A | C |
| ATOM | 36 | CE1 | TYR | A | 25 | 66.711 | −31.092 | −29.059 | 1.00 | 36.77 | A | C |
| ATOM | 38 | CZ | TYR | A | 25 | 66.203 | −31.268 | −30.344 | 1.00 | 28.44 | A | C |
| ATOM | 39 | OH | TYR | A | 25 | 66.356 | −32.509 | −30.967 | 1.00 | 27.40 | A | O |
| ATOM | 41 | CE2 | TYR | A | 25 | 65.558 | −30.217 | −30.979 | 1.00 | 25.06 | A | C |
| ATOM | 43 | CD2 | TYR | A | 25 | 65.426 | −28.988 | −30.317 | 1.00 | 37.00 | A | C |
| ATOM | 45 | C | TYR | A | 25 | 64.687 | −26.036 | −26.661 | 1.00 | 57.89 | A | C |
| ATOM | 46 | O | TYR | A | 25 | 65.729 | −25.384 | −26.543 | 1.00 | 56.82 | A | O |
| ATOM | 48 | N | GLU | A | 26 | 63.490 | −25.529 | −26.363 | 1.00 | 59.48 | A | N |
| ATOM | 49 | CA | GLU | A | 26 | 63.341 | −24.135 | −25.907 | 1.00 | 60.53 | A | C |
| ATOM | 51 | CB | GLU | A | 26 | 61.868 | −23.677 | −25.947 | 1.00 | 61.98 | A | C |
| ATOM | 54 | CG | GLU | A | 26 | 61.348 | −23.344 | −27.364 | 1.00 | 67.81 | A | C |
| ATOM | 57 | CD | GLU | A | 26 | 61.904 | −22.027 | −27.939 | 1.00 | 76.35 | A | C |
| ATOM | 58 | OE1 | GLU | A | 26 | 61.559 | −20.940 | −27.414 | 1.00 | 79.99 | A | O |
| ATOM | 59 | OE2 | GLU | A | 26 | 62.671 | −22.083 | −28.931 | 1.00 | 78.41 | A | O |
| ATOM | 60 | C | GLU | A | 26 | 63.936 | −23.968 | −24.504 | 1.00 | 57.46 | A | C |
| ATOM | 61 | O | GLU | A | 26 | 63.895 | −24.895 | −23.710 | 1.00 | 55.07 | A | O |
| ATOM | 63 | N | PRO | A | 27 | 64.507 | −22.787 | −24.210 | 1.00 | 56.78 | A | N |
| ATOM | 64 | CA | PRO | A | 27 | 65.154 | −22.598 | −22.915 | 1.00 | 56.84 | A | C |
| ATOM | 66 | CB | PRO | A | 27 | 65.814 | −21.217 | −23.045 | 1.00 | 57.69 | A | C |
| ATOM | 69 | CG | PRO | A | 27 | 65.016 | −20.504 | −24.075 | 1.00 | 58.63 | A | C |
| ATOM | 72 | CD | PRO | A | 27 | 64.502 | −21.552 | −25.017 | 1.00 | 57.02 | A | C |
| ATOM | 75 | C | PRO | A | 27 | 64.169 | −22.625 | −21.736 | 1.00 | 55.20 | A | C |
| ATOM | 76 | O | PRO | A | 27 | 62.977 | −22.370 | −21.913 | 1.00 | 54.56 | A | O |
| ATOM | 77 | N | ASN | A | 28 | 64.673 | −22.977 | −20.560 | 1.00 | 53.26 | A | N |
| ATOM | 78 | CA | ASN | A | 28 | 63.936 | −22.792 | −19.328 | 1.00 | 53.80 | A | C |
| ATOM | 80 | CB | ASN | A | 28 | 64.226 | −23.922 | −18.345 | 1.00 | 55.37 | A | C |
| ATOM | 83 | CG | ASN | A | 28 | 63.955 | −25.285 | −18.938 | 1.00 | 57.15 | A | C |
| ATOM | 84 | OD1 | ASN | A | 28 | 62.803 | −25.708 | −19.041 | 1.00 | 59.44 | A | O |
| ATOM | 85 | ND2 | ASN | A | 28 | 65.019 | −25.984 | −19.329 | 1.00 | 56.57 | A | N |
| ATOM | 88 | C | ASN | A | 28 | 64.302 | −21.453 | −18.702 | 1.00 | 52.53 | A | C |
| ATOM | 89 | O | ASN | A | 28 | 65.445 | −20.999 | −18.790 | 1.00 | 51.17 | A | O |
| ATOM | 91 | N | SER | A | 29 | 63.318 | −20.836 | −18.057 | 1.00 | 52.53 | A | N |
| ATOM | 92 | CA | SER | A | 29 | 63.497 | −19.563 | −17.340 | 1.00 | 52.63 | A | C |
| ATOM | 94 | CB | SER | A | 29 | 62.153 | −19.136 | −16.735 | 1.00 | 53.29 | A | C |
| ATOM | 97 | OG | SER | A | 29 | 61.572 | −20.222 | −16.014 | 1.00 | 52.43 | A | O |
| ATOM | 99 | C | SER | A | 29 | 64.545 | −19.616 | −16.215 | 1.00 | 51.47 | A | C |
| ATOM | 100 | O | SER | A | 29 | 64.999 | −18.576 | −15.746 | 1.00 | 51.59 | A | O |
| ATOM | 102 | N | TRP | A | 30 | 64.891 | −20.826 | −15.774 | 1.00 | 50.43 | A | N |
| ATOM | 103 | CA | TRP | A | 30 | 65.901 | −21.041 | −14.731 | 1.00 | 50.20 | A | C |
| ATOM | 105 | CB | TRP | A | 30 | 65.343 | −21.978 | −13.637 | 1.00 | 50.36 | A | C |
| ATOM | 108 | CG | TRP | A | 30 | 64.573 | −23.177 | −14.155 | 1.00 | 51.86 | A | C |
| ATOM | 109 | CD1 | TRP | A | 30 | 63.214 | −23.313 | −14.211 | 1.00 | 56.08 | A | C |
| ATOM | 111 | NE1 | TRP | A | 30 | 62.880 | −24.533 | −14.750 | 1.00 | 60.74 | A | N |
| ATOM | 113 | CE2 | TRP | A | 30 | 64.029 | −25.215 | −15.051 | 1.00 | 54.80 | A | C |
| ATOM | 114 | CD2 | TRP | A | 30 | 65.119 | −24.392 | −14.688 | 1.00 | 51.20 | A | C |
| ATOM | 115 | CE3 | TRP | A | 30 | 66.419 | −24.862 | −14.894 | 1.00 | 57.41 | A | C |
| ATOM | 117 | CZ3 | TRP | A | 30 | 66.591 | −26.131 | −15.460 | 1.00 | 60.80 | A | C |
| ATOM | 119 | CH2 | TRP | A | 30 | 65.483 | −26.925 | −15.807 | 1.00 | 61.30 | A | C |
| ATOM | 121 | CZ2 | TRP | A | 30 | 64.199 | −26.484 | −15.611 | 1.00 | 60.79 | A | C |
| ATOM | 123 | C | TRP | A | 30 | 67.266 | −21.562 | −15.250 | 1.00 | 49.62 | A | C |
| ATOM | 124 | O | TRP | A | 30 | 68.187 | −21.761 | −14.454 | 1.00 | 48.73 | A | O |
| ATOM | 126 | N | ASP | A | 31 | 67.411 | −21.778 | −16.561 | 1.00 | 49.12 | A | N |
| ATOM | 127 | CA | ASP | A | 31 | 68.692 | −22.273 | −17.113 | 1.00 | 48.38 | A | C |
| ATOM | 129 | CB | ASP | A | 31 | 68.649 | −22.407 | −18.638 | 1.00 | 48.56 | A | C |
| ATOM | 132 | CG | ASP | A | 31 | 67.723 | −23.505 | −19.108 | 1.00 | 47.65 | A | C |
| ATOM | 133 | OD1 | ASP | A | 31 | 67.602 | −24.547 | −18.429 | 1.00 | 50.40 | A | O |
| ATOM | 134 | OD2 | ASP | A | 31 | 67.117 | −23.313 | −20.175 | 1.00 | 49.25 | A | O |
| ATOM | 135 | C | ASP | A | 31 | 69.801 | −21.307 | −16.760 | 1.00 | 47.85 | A | C |
| ATOM | 136 | O | ASP | A | 31 | 69.563 | −20.102 | −16.691 | 1.00 | 47.37 | A | O |
| ATOM | 138 | N | TYR | A | 32 | 71.010 | −21.821 | −16.546 | 1.00 | 46.83 | A | N |
| ATOM | 139 | CA | TYR | A | 32 | 72.126 | −20.945 | −16.201 | 1.00 | 47.06 | A | C |
| ATOM | 141 | CB | TYR | A | 32 | 73.335 | −21.742 | −15.707 | 1.00 | 44.99 | A | C |
| ATOM | 144 | CG | TYR | A | 32 | 73.105 | −22.461 | −14.388 | 1.00 | 41.43 | A | C |
| ATOM | 145 | CD1 | TYR | A | 32 | 72.786 | −21.755 | −13.213 | 1.00 | 36.43 | A | C |
| ATOM | 147 | CE1 | TYR | A | 32 | 72.587 | −22.428 | −12.008 | 1.00 | 26.59 | A | C |
| ATOM | 149 | CZ | TYR | A | 32 | 72.708 | −23.786 | −11.980 | 1.00 | 28.34 | A | C |
| ATOM | 150 | OH | TYR | A | 32 | 72.521 | −24.456 | −10.829 | 1.00 | 27.28 | A | O |
| ATOM | 152 | CE2 | TYR | A | 32 | 73.043 | −24.506 | −13.113 | 1.00 | 33.62 | A | C |
| ATOM | 154 | CD2 | TYR | A | 32 | 73.241 | −23.843 | −14.302 | 1.00 | 36.99 | A | C |
| ATOM | 156 | C | TYR | A | 32 | 72.520 | −19.999 | −17.343 | 1.00 | 49.23 | A | C |

TABLE 4-2-continued

| Coordinates of *P. alba* IspS | | | | | | | | | | | | |
|---|---|---|---|---|---|---|---|---|---|---|---|---|
| ATOM | 157 | O | TYR | A | 32 | 73.087 | −18.945 | −17.081 | 1.00 | 46.64 | A | O |
| ATOM | 159 | N | ASP | A | 33 | 72.229 | −20.380 | −18.591 | 1.00 | 53.18 | A | N |
| ATOM | 160 | CA | ASP | A | 33 | 72.441 | −19.503 | −19.758 | 1.00 | 56.33 | A | C |
| ATOM | 162 | CB | ASP | A | 33 | 72.191 | −20.264 | −21.080 | 1.00 | 56.22 | A | C |
| ATOM | 165 | CG | ASP | A | 33 | 73.311 | −21.266 | −21.435 | 1.00 | 55.52 | A | C |
| ATOM | 166 | OD1 | ASP | A | 33 | 74.495 | −21.027 | −21.103 | 1.00 | 50.09 | A | O |
| ATOM | 167 | OD2 | ASP | A | 33 | 73.004 | −22.293 | −22.087 | 1.00 | 54.49 | A | O |
| ATOM | 168 | C | ASP | A | 33 | 71.539 | −18.250 | −19.701 | 1.00 | 60.14 | A | C |
| ATOM | 169 | O | ASP | A | 33 | 71.973 | −17.150 | −20.064 | 1.00 | 59.09 | A | O |
| ATOM | 171 | N | TYR | A | 34 | 70.298 | −18.429 | −19.241 | 1.00 | 64.30 | A | N |
| ATOM | 172 | CA | TYR | A | 34 | 69.300 | −17.346 | −19.158 | 1.00 | 68.93 | A | C |
| ATOM | 174 | CB | TYR | A | 34 | 67.880 | −17.942 | −19.169 | 1.00 | 69.88 | A | C |
| ATOM | 177 | CG | TYR | A | 34 | 66.754 | −16.929 | −19.206 | 1.00 | 79.07 | A | C |
| ATOM | 178 | CD1 | TYR | A | 34 | 66.346 | −16.345 | −20.411 | 1.00 | 87.57 | A | C |
| ATOM | 180 | CE1 | TYR | A | 34 | 65.300 | −15.405 | −20.444 | 1.00 | 90.15 | A | C |
| ATOM | 182 | CZ | TYR | A | 34 | 64.653 | −15.057 | −19.261 | 1.00 | 92.74 | A | C |
| ATOM | 183 | OH | TYR | A | 34 | 63.620 | −14.141 | −19.270 | 1.00 | 95.62 | A | O |
| ATOM | 185 | CE2 | TYR | A | 34 | 65.041 | −15.631 | −18.056 | 1.00 | 89.91 | A | C |
| ATOM | 187 | CD2 | TYR | A | 34 | 66.084 | −16.561 | −18.034 | 1.00 | 85.72 | A | C |
| ATOM | 189 | C | TYR | A | 34 | 69.529 | −16.449 | −17.926 | 1.00 | 70.23 | A | C |
| ATOM | 190 | O | TYR | A | 34 | 69.797 | −15.260 | −18.063 | 1.00 | 70.32 | A | O |
| ATOM | 192 | N | LEU | A | 35 | 69.427 | −17.020 | −16.727 | 1.00 | 73.06 | A | N |
| ATOM | 193 | CA | LEU | A | 35 | 69.867 | −16.341 | −15.501 | 1.00 | 75.25 | A | C |
| ATOM | 195 | CB | LEU | A | 35 | 69.506 | −17.156 | −14.250 | 1.00 | 74.64 | A | C |
| ATOM | 198 | CG | LEU | A | 35 | 68.069 | −17.615 | −13.995 | 1.00 | 71.74 | A | C |
| ATOM | 200 | CD1 | LEU | A | 35 | 68.046 | −18.584 | −12.822 | 1.00 | 67.99 | A | C |
| ATOM | 204 | CD2 | LEU | A | 35 | 67.150 | −16.432 | −13.741 | 1.00 | 67.75 | A | C |
| ATOM | 208 | C | LEU | A | 35 | 71.379 | −16.252 | −15.592 | 1.00 | 78.42 | A | C |
| ATOM | 209 | O | LEU | A | 35 | 71.962 | −16.873 | −16.472 | 1.00 | 80.06 | A | O |
| ATOM | 211 | N | LEU | A | 36 | 72.028 | −15.505 | −14.705 | 1.00 | 81.43 | A | N |
| ATOM | 212 | CA | LEU | A | 36 | 73.494 | −15.583 | −14.598 | 1.00 | 84.46 | A | C |
| ATOM | 214 | CB | LEU | A | 36 | 73.881 | −16.978 | −14.068 | 1.00 | 84.18 | A | C |
| ATOM | 217 | CG | LEU | A | 36 | 75.259 | −17.216 | −13.442 | 1.00 | 84.76 | A | C |
| ATOM | 219 | CD1 | LEU | A | 36 | 75.421 | −16.414 | −12.157 | 1.00 | 87.18 | A | C |
| ATOM | 223 | CD2 | LEU | A | 36 | 75.470 | −18.700 | −13.189 | 1.00 | 83.02 | A | C |
| ATOM | 227 | C | LEU | A | 36 | 74.237 | −15.311 | −15.928 | 1.00 | 86.75 | A | C |
| ATOM | 228 | O | LEU | A | 36 | 75.330 | −15.834 | −16.156 | 1.00 | 86.15 | A | O |
| ATOM | 230 | N | SER | A | 37 | 73.644 | −14.503 | −16.805 | 1.00 | 90.20 | A | N |
| ATOM | 231 | CA | SER | A | 37 | 74.279 | −14.168 | −18.080 | 1.00 | 92.56 | A | C |
| ATOM | 233 | CB | SER | A | 37 | 73.237 | −14.010 | −19.189 | 1.00 | 92.69 | A | C |
| ATOM | 236 | OG | SER | A | 37 | 73.808 | −14.292 | −20.454 | 1.00 | 92.23 | A | O |
| ATOM | 238 | C | SER | A | 37 | 75.107 | −12.893 | −17.907 | 1.00 | 94.60 | A | C |
| ATOM | 239 | O | SER | A | 37 | 74.881 | −12.121 | −16.964 | 1.00 | 94.48 | A | O |
| ATOM | 241 | N | SER | A | 38 | 76.056 | −12.684 | −18.822 | 1.00 | 96.76 | A | N |
| ATOM | 242 | CA | SER | A | 38 | 77.120 | −11.683 | −18.643 | 1.00 | 98.37 | A | C |
| ATOM | 244 | CB | SER | A | 38 | 78.236 | −11.866 | −19.687 | 1.00 | 98.25 | A | C |
| ATOM | 247 | OG | SER | A | 38 | 77.731 | −11.924 | −21.008 | 1.00 | 97.84 | A | O |
| ATOM | 249 | C | SER | A | 38 | 76.642 | −10.232 | −18.666 | 1.00 | 99.95 | A | C |
| ATOM | 250 | O | SER | A | 38 | 76.185 | −9.731 | −19.698 | 1.00 | 100.18 | A | O |
| ATOM | 252 | N | ASP | A | 39 | 76.771 | −9.569 | −17.517 | 1.00 | 101.78 | A | N |
| ATOM | 253 | CA | ASP | A | 39 | 76.622 | −8.115 | −17.417 | 1.00 | 103.16 | A | C |
| ATOM | 255 | CB | ASP | A | 39 | 76.312 | −7.727 | −15.956 | 1.00 | 103.31 | A | C |
| ATOM | 258 | CG | ASP | A | 39 | 75.475 | −6.452 | −15.835 | 1.00 | 103.40 | A | C |
| ATOM | 259 | OD1 | ASP | A | 39 | 75.487 | −5.615 | −16.765 | 1.00 | 100.38 | A | O |
| ATOM | 260 | OD2 | ASP | A | 39 | 74.804 | −6.290 | −14.792 | 1.00 | 103.82 | A | O |
| ATOM | 261 | C | ASP | A | 39 | 77.945 | −7.505 | −17.942 | 1.00 | 104.15 | A | C |
| ATOM | 262 | O | ASP | A | 39 | 78.518 | −8.032 | −18.904 | 1.00 | 104.67 | A | O |
| ATOM | 264 | N | THR | A | 40 | 78.436 | −6.414 | −17.343 | 1.00 | 104.86 | A | N |
| ATOM | 265 | CA | THR | A | 40 | 79.818 | −5.955 | −17.599 | 1.00 | 105.03 | A | C |
| ATOM | 267 | CB | THR | A | 40 | 79.942 | −4.397 | −17.544 | 1.00 | 105.17 | A | C |
| ATOM | 269 | OG1 | THR | A | 40 | 78.774 | −3.789 | −18.111 | 1.00 | 104.08 | A | O |
| ATOM | 271 | CG2 | THR | A | 40 | 81.187 | −3.917 | −18.306 | 1.00 | 103.97 | A | C |
| ATOM | 275 | C | THR | A | 40 | 80.802 | −6.605 | −16.594 | 1.00 | 105.16 | A | C |
| ATOM | 276 | O | THR | A | 40 | 81.804 | −5.992 | −16.206 | 1.00 | 105.14 | A | O |
| ATOM | 278 | N | ASP | A | 41 | 80.509 | −7.851 | −16.198 | 1.00 | 104.87 | A | N |
| ATOM | 279 | CA | ASP | A | 41 | 81.285 | −8.600 | −15.198 | 1.00 | 104.03 | A | C |
| ATOM | 281 | CB | ASP | A | 41 | 80.400 | −8.951 | −13.991 | 1.00 | 103.68 | A | C |
| ATOM | 284 | CG | ASP | A | 41 | 80.063 | −7.737 | −13.126 | 1.00 | 103.58 | A | C |
| ATOM | 285 | OD1 | ASP | A | 41 | 80.402 | −6.594 | −13.506 | 1.00 | 101.01 | A | O |
| ATOM | 286 | OD2 | ASP | A | 41 | 79.455 | −7.929 | −12.053 | 1.00 | 103.04 | A | O |
| ATOM | 287 | C | ASP | A | 41 | 81.884 | −9.883 | −15.807 | 1.00 | 103.35 | A | C |
| ATOM | 288 | O | ASP | A | 41 | 81.159 | −10.738 | −16.329 | 1.00 | 102.89 | A | O |
| ATOM | 290 | N | GLU | A | 42 | 83.210 | −10.005 | −15.715 | 1.00 | 102.70 | A | N |
| ATOM | 291 | CA | GLU | A | 42 | 83.965 | −11.067 | −16.392 | 1.00 | 102.05 | A | C |
| ATOM | 293 | CB | GLU | A | 42 | 85.477 | −10.775 | −16.342 | 1.00 | 101.98 | A | C |
| ATOM | 296 | CG | GLU | A | 42 | 85.924 | −9.517 | −17.102 | 1.00 | 101.14 | A | C |
| ATOM | 299 | CD | GLU | A | 42 | 87.445 | −9.357 | −17.170 | 1.00 | 99.92 | A | C |
| ATOM | 300 | OE1 | GLU | A | 42 | 88.174 | −10.198 | −16.603 | 1.00 | 99.06 | A | O |

TABLE 4-2-continued

Coordinates of *P. alba* IspS

| | | | | | | | | | | | | |
|---|---|---|---|---|---|---|---|---|---|---|---|---|
| ATOM | 301 | OE2 | GLU | A | 42 | 87.916 | −8.384 | −17.797 | 1.00 | 96.85 | A | O |
| ATOM | 302 | C | GLU | A | 42 | 83.700 | −12.466 | −15.820 | 1.00 | 101.77 | A | C |
| ATOM | 303 | O | GLU | A | 42 | 83.463 | −13.410 | −16.582 | 1.00 | 102.06 | A | O |
| ATOM | 305 | N | SER | A | 43 | 83.748 | −12.599 | −14.491 | 1.00 | 100.69 | A | N |
| ATOM | 306 | CA | SER | A | 43 | 83.632 | −13.915 | −13.829 | 1.00 | 99.39 | A | C |
| ATOM | 308 | CB | SER | A | 43 | 84.695 | −14.072 | −12.721 | 1.00 | 99.42 | A | C |
| ATOM | 311 | OG | SER | A | 43 | 84.503 | −13.160 | −11.657 | 1.00 | 98.04 | A | O |
| ATOM | 313 | C | SER | A | 43 | 82.213 | −14.252 | −13.308 | 1.00 | 97.81 | A | C |
| ATOM | 314 | O | SER | A | 43 | 82.054 | −15.108 | −12.424 | 1.00 | 96.95 | A | O |
| ATOM | 316 | N | ILE | A | 44 | 81.195 | −13.579 | −13.859 | 1.00 | 95.85 | A | N |
| ATOM | 317 | CA | ILE | A | 44 | 79.816 | −14.092 | −13.827 | 1.00 | 94.49 | A | C |
| ATOM | 319 | CB | ILE | A | 44 | 78.734 | −12.989 | −14.132 | 1.00 | 94.92 | A | C |
| ATOM | 321 | CG1 | ILE | A | 44 | 78.344 | −12.217 | −12.858 | 1.00 | 95.86 | A | C |
| ATOM | 324 | CD1 | ILE | A | 44 | 77.084 | −11.338 | −13.006 | 1.00 | 93.80 | A | C |
| ATOM | 328 | CG2 | ILE | A | 44 | 77.467 | −13.603 | −14.731 | 1.00 | 94.41 | A | C |
| ATOM | 332 | C | ILE | A | 44 | 79.704 | −15.251 | −14.832 | 1.00 | 92.51 | A | C |
| ATOM | 333 | O | ILE | A | 44 | 78.815 | −16.099 | −14.698 | 1.00 | 91.97 | A | O |
| ATOM | 335 | N | GLU | A | 45 | 80.615 | −15.284 | −15.817 | 1.00 | 90.17 | A | N |
| ATOM | 336 | CA | GLU | A | 45 | 80.662 | −16.342 | −16.845 | 1.00 | 88.08 | A | C |
| ATOM | 338 | CB | GLU | A | 45 | 81.071 | −15.768 | −18.205 | 1.00 | 88.74 | A | C |
| ATOM | 341 | CG | GLU | A | 45 | 79.979 | −14.922 | −18.864 | 1.00 | 91.64 | A | C |
| ATOM | 344 | CD | GLU | A | 45 | 79.561 | −15.416 | −20.250 | 1.00 | 94.30 | A | C |
| ATOM | 345 | OE1 | GLU | A | 45 | 80.265 | −16.268 | −20.839 | 1.00 | 95.27 | A | O |
| ATOM | 346 | OE2 | GLU | A | 45 | 78.513 | −14.946 | −20.746 | 1.00 | 92.80 | A | O |
| ATOM | 347 | C | GLU | A | 45 | 81.570 | −17.536 | −16.521 | 1.00 | 85.08 | A | C |
| ATOM | 348 | O | GLU | A | 45 | 81.331 | −18.638 | −17.021 | 1.00 | 84.95 | A | O |
| ATOM | 350 | N | VAL | A | 46 | 82.620 | −17.323 | −15.727 | 1.00 | 81.35 | A | N |
| ATOM | 351 | CA | VAL | A | 46 | 83.420 | −18.442 | −15.202 | 1.00 | 78.09 | A | C |
| ATOM | 353 | CB | VAL | A | 46 | 84.741 | −17.959 | −14.548 | 1.00 | 78.08 | A | C |
| ATOM | 355 | CG1 | VAL | A | 46 | 85.516 | −19.136 | −13.944 | 1.00 | 78.15 | A | C |
| ATOM | 359 | CG2 | VAL | A | 46 | 85.603 | −17.213 | −15.570 | 1.00 | 79.62 | A | C |
| ATOM | 363 | C | VAL | A | 46 | 82.583 | −19.247 | −14.187 | 1.00 | 74.06 | A | C |
| ATOM | 364 | O | VAL | A | 46 | 82.718 | −20.472 | −14.090 | 1.00 | 73.88 | A | O |
| ATOM | 366 | N | TYR | A | 47 | 81.728 | −18.528 | −13.451 | 1.00 | 68.93 | A | N |
| ATOM | 367 | CA | TYR | A | 47 | 80.741 | −19.086 | −12.512 | 1.00 | 65.54 | A | C |
| ATOM | 369 | CB | TYR | A | 47 | 80.142 | −17.905 | −11.718 | 1.00 | 65.84 | A | C |
| ATOM | 372 | CG | TYR | A | 47 | 79.247 | −18.192 | −10.516 | 1.00 | 68.89 | A | C |
| ATOM | 373 | CD1 | TYR | A | 47 | 79.776 | −18.352 | −9.229 | 1.00 | 72.76 | A | C |
| ATOM | 375 | CE1 | TYR | A | 47 | 78.930 | −18.585 | −8.113 | 1.00 | 72.95 | A | C |
| ATOM | 377 | CZ | TYR | A | 47 | 77.542 | −18.631 | −8.291 | 1.00 | 72.91 | A | C |
| ATOM | 378 | OH | TYR | A | 47 | 76.679 | −18.853 | −7.222 | 1.00 | 53.89 | A | O |
| ATOM | 380 | CE2 | TYR | A | 47 | 77.008 | −18.448 | −9.560 | 1.00 | 71.64 | A | C |
| ATOM | 382 | CD2 | TYR | A | 47 | 77.859 | −18.216 | −10.655 | 1.00 | 72.02 | A | C |
| ATOM | 384 | C | TYR | A | 47 | 79.658 | −19.899 | −13.280 | 1.00 | 61.30 | A | C |
| ATOM | 385 | O | TYR | A | 47 | 79.353 | −21.044 | −12.929 | 1.00 | 59.34 | A | O |
| ATOM | 387 | N | LYS | A | 48 | 79.109 | −19.287 | −14.333 | 1.00 | 56.43 | A | N |
| ATOM | 388 | CA | LYS | A | 48 | 78.171 | −19.918 | −15.284 | 1.00 | 52.55 | A | C |
| ATOM | 390 | CB | LYS | A | 48 | 77.920 | −18.945 | −16.451 | 1.00 | 53.28 | A | C |
| ATOM | 393 | CG | LYS | A | 48 | 76.989 | −19.391 | −17.592 | 1.00 | 55.50 | A | C |
| ATOM | 396 | CD | LYS | A | 48 | 77.428 | −18.712 | −18.913 | 1.00 | 61.02 | A | C |
| ATOM | 399 | CE | LYS | A | 48 | 76.323 | −18.612 | −19.970 | 1.00 | 65.42 | A | C |
| ATOM | 402 | NZ | LYS | A | 48 | 75.608 | −17.279 | −19.985 | 1.00 | 66.42 | A | N |
| ATOM | 406 | C | LYS | A | 48 | 78.673 | −21.255 | −15.828 | 1.00 | 47.94 | A | C |
| ATOM | 407 | O | LYS | A | 48 | 78.023 | −22.273 | −15.643 | 1.00 | 47.33 | A | O |
| ATOM | 409 | N | ASP | A | 49 | 79.822 | −21.250 | −16.496 | 1.00 | 44.41 | A | N |
| ATOM | 410 | CA | ASP | A | 49 | 80.382 | −22.471 | −17.087 | 1.00 | 43.52 | A | C |
| ATOM | 412 | CB | ASP | A | 49 | 81.659 | −22.188 | −17.915 | 1.00 | 44.86 | A | C |
| ATOM | 415 | CG | ASP | A | 49 | 81.387 | −21.342 | −19.179 | 1.00 | 48.93 | A | C |
| ATOM | 416 | OD1 | ASP | A | 49 | 80.230 | −21.330 | −19.679 | 1.00 | 53.55 | A | O |
| ATOM | 417 | OD2 | ASP | A | 49 | 82.339 | −20.689 | −19.670 | 1.00 | 47.52 | A | O |
| ATOM | 418 | C | ASP | A | 49 | 80.680 | −23.512 | −16.011 | 1.00 | 41.34 | A | C |
| ATOM | 419 | O | ASP | A | 49 | 80.564 | −24.715 | −16.263 | 1.00 | 39.75 | A | O |
| ATOM | 421 | N | LYS | A | 50 | 81.052 | −23.055 | −14.813 | 1.00 | 39.19 | A | N |
| ATOM | 422 | CA | LYS | A | 50 | 81.252 | −23.967 | −13.693 | 1.00 | 37.19 | A | C |
| ATOM | 424 | CB | LYS | A | 50 | 81.870 | −23.260 | −12.480 | 1.00 | 39.17 | A | C |
| ATOM | 427 | CG | LYS | A | 50 | 82.291 | −24.204 | −11.330 | 1.00 | 44.35 | A | C |
| ATOM | 430 | CD | LYS | A | 50 | 82.896 | −23.401 | −10.166 | 1.00 | 55.34 | A | C |
| ATOM | 433 | CE | LYS | A | 50 | 84.411 | −23.260 | −10.273 | 1.00 | 59.44 | A | C |
| ATOM | 436 | NZ | LYS | A | 50 | 84.866 | −21.942 | −9.757 | 1.00 | 57.35 | A | N |
| ATOM | 440 | C | LYS | A | 50 | 79.920 | −24.617 | −13.344 | 1.00 | 33.13 | A | C |
| ATOM | 441 | O | LYS | A | 50 | 79.846 | −25.845 | −13.254 | 1.00 | 31.70 | A | O |
| ATOM | 443 | N | ALA | A | 51 | 78.862 | −23.813 | −13.195 | 1.00 | 28.95 | A | N |
| ATOM | 444 | CA | ALA | A | 51 | 77.540 | −24.361 | −12.872 | 1.00 | 27.76 | A | C |
| ATOM | 446 | CB | ALA | A | 51 | 76.523 | −23.233 | −12.640 | 1.00 | 27.51 | A | C |
| ATOM | 450 | C | ALA | A | 51 | 77.030 | −25.359 | −13.942 | 1.00 | 26.48 | A | C |
| ATOM | 451 | O | ALA | A | 51 | 76.596 | −26.462 | −13.615 | 1.00 | 28.45 | A | O |
| ATOM | 453 | N | LYS | A | 52 | 77.104 | −24.980 | −15.212 | 1.00 | 25.84 | A | N |
| ATOM | 454 | CA | LYS | A | 52 | 76.704 | −25.867 | −16.319 | 1.00 | 25.55 | A | C |

TABLE 4-2-continued

Coordinates of *P. alba* IspS

| | | | | | | | | | | | | |
|---|---|---|---|---|---|---|---|---|---|---|---|---|
| ATOM | 456 | CB | LYS | A | 52 | 77.062 | −25.228 | −17.679 | 1.00 | 25.87 | A | C |
| ATOM | 459 | CG | LYS | A | 52 | 76.061 | −24.158 | −18.106 | 1.00 | 30.35 | A | C |
| ATOM | 462 | CD | LYS | A | 52 | 76.635 | −23.079 | −19.007 | 1.00 | 29.72 | A | C |
| ATOM | 465 | CE | LYS | A | 52 | 76.636 | −23.486 | −20.493 | 1.00 | 39.59 | A | C |
| ATOM | 468 | NZ | LYS | A | 52 | 77.217 | −22.424 | −21.416 | 1.00 | 37.70 | A | N |
| ATOM | 472 | C | LYS | A | 52 | 77.345 | −27.247 | −16.217 | 1.00 | 25.06 | A | C |
| ATOM | 473 | O | LYS | A | 52 | 76.678 | −28.266 | −16.388 | 1.00 | 24.13 | A | O |
| ATOM | 475 | N | LYS | A | 53 | 78.647 | −27.270 | −15.941 | 1.00 | 25.32 | A | N |
| ATOM | 476 | CA | LYS | A | 53 | 79.407 | −28.529 | −15.862 | 1.00 | 26.67 | A | C |
| ATOM | 478 | CB | LYS | A | 53 | 80.915 | −28.230 | −15.729 | 1.00 | 28.91 | A | C |
| ATOM | 481 | CG | LYS | A | 53 | 81.781 | −29.479 | −15.584 | 1.00 | 38.89 | A | C |
| ATOM | 484 | CD | LYS | A | 53 | 83.274 | −29.214 | −15.866 | 1.00 | 51.52 | A | C |
| ATOM | 487 | CE | LYS | A | 53 | 84.101 | −30.510 | −15.696 | 1.00 | 55.41 | A | C |
| ATOM | 490 | NZ | LYS | A | 53 | 85.467 | −30.399 | −16.280 | 1.00 | 56.50 | A | N |
| ATOM | 494 | C | LYS | A | 53 | 78.940 | −29.439 | −14.705 | 1.00 | 23.90 | A | C |
| ATOM | 495 | O | LYS | A | 53 | 78.751 | −30.648 | −14.893 | 1.00 | 21.50 | A | O |
| ATOM | 497 | N | LEU | A | 54 | 78.770 | −28.847 | −13.523 | 1.00 | 20.73 | A | N |
| ATOM | 498 | CA | LEU | A | 54 | 78.317 | −29.568 | −12.343 | 1.00 | 21.72 | A | C |
| ATOM | 500 | CB | LEU | A | 54 | 78.280 | −28.637 | −11.120 | 1.00 | 21.06 | A | C |
| ATOM | 503 | CG | LEU | A | 54 | 79.601 | −27.919 | −10.778 | 1.00 | 26.70 | A | C |
| ATOM | 505 | CD1 | LEU | A | 54 | 79.389 | −26.832 | −9.753 | 1.00 | 21.18 | A | C |
| ATOM | 509 | CD2 | LEU | A | 54 | 80.674 | −28.909 | −10.299 | 1.00 | 27.08 | A | C |
| ATOM | 513 | C | LEU | A | 54 | 76.927 | −30.132 | −12.611 | 1.00 | 21.21 | A | C |
| ATOM | 514 | O | LEU | A | 54 | 76.642 | −31.304 | −12.353 | 1.00 | 21.09 | A | O |
| ATOM | 516 | N | GLU | A | 55 | 76.073 | −29.270 | −13.144 | 1.00 | 21.62 | A | N |
| ATOM | 517 | CA | GLU | A | 55 | 74.692 | −29.602 | −13.409 | 1.00 | 20.09 | A | C |
| ATOM | 519 | CB | GLU | A | 55 | 73.961 | −28.375 | −13.955 | 1.00 | 20.04 | A | C |
| ATOM | 522 | CG | GLU | A | 55 | 72.497 | −28.639 | −14.395 | 1.00 | 25.33 | A | C |
| ATOM | 525 | CD | GLU | A | 55 | 71.880 | −27.437 | −15.100 | 1.00 | 25.76 | A | C |
| ATOM | 526 | OE1 | GLU | A | 55 | 72.558 | −26.836 | −15.953 | 1.00 | 27.45 | A | O |
| ATOM | 527 | OE2 | GLU | A | 55 | 70.731 | −27.095 | −14.790 | 1.00 | 28.92 | A | O |
| ATOM | 528 | C | GLU | A | 55 | 74.614 | −30.736 | −14.410 | 1.00 | 19.08 | A | C |
| ATOM | 529 | O | GLU | A | 55 | 73.764 | −31.614 | −14.286 | 1.00 | 17.95 | A | O |
| ATOM | 531 | N | ALA | A | 56 | 75.505 | −30.721 | −15.396 | 1.00 | 18.58 | A | N |
| ATOM | 532 | CA | ALA | A | 56 | 75.516 | −31.770 | −16.419 | 1.00 | 18.68 | A | C |
| ATOM | 534 | CB | ALA | A | 56 | 76.589 | −31.476 | −17.477 | 1.00 | 17.67 | A | C |
| ATOM | 538 | C | ALA | A | 56 | 75.782 | −33.105 | −15.784 | 1.00 | 18.70 | A | C |
| ATOM | 539 | O | ALA | A | 56 | 75.164 | −34.107 | −16.140 | 1.00 | 21.50 | A | O |
| ATOM | 541 | N | GLU | A | 57 | 76.717 | −33.118 | −14.840 | 1.00 | 19.66 | A | N |
| ATOM | 542 | CA | GLU | A | 57 | 77.138 | −34.352 | −14.191 | 1.00 | 19.60 | A | C |
| ATOM | 544 | CB | GLU | A | 57 | 78.451 | −34.147 | −13.404 | 1.00 | 21.64 | A | C |
| ATOM | 547 | CG | GLU | A | 57 | 78.990 | −35.425 | −12.709 | 1.00 | 27.13 | A | C |
| ATOM | 550 | CD | GLU | A | 57 | 80.415 | −35.275 | −12.139 | 1.00 | 28.89 | A | C |
| ATOM | 551 | OE1 | GLU | A | 57 | 81.165 | −34.363 | −12.546 | 1.00 | 30.32 | A | O |
| ATOM | 552 | OE2 | GLU | A | 57 | 80.781 | −36.104 | −11.276 | 1.00 | 36.69 | A | O |
| ATOM | 553 | C | GLU | A | 57 | 76.009 | −34.867 | −13.316 | 1.00 | 18.61 | A | C |
| ATOM | 554 | O | GLU | A | 57 | 75.731 | −36.037 | −13.348 | 1.00 | 19.99 | A | O |
| ATOM | 556 | N | VAL | A | 58 | 75.313 | −33.996 | −12.580 | 1.00 | 19.50 | A | N |
| ATOM | 557 | CA | VAL | A | 58 | 74.171 | −34.452 | −11.772 | 1.00 | 18.20 | A | C |
| ATOM | 559 | CB | VAL | A | 58 | 73.603 | −33.329 | −10.893 | 1.00 | 21.45 | A | C |
| ATOM | 561 | CG1 | VAL | A | 58 | 72.374 | −33.841 | −10.141 | 1.00 | 16.09 | A | C |
| ATOM | 565 | CG2 | VAL | A | 58 | 74.659 | −32.800 | −9.918 | 1.00 | 17.59 | A | C |
| ATOM | 569 | C | VAL | A | 58 | 73.062 | −35.007 | −12.676 | 1.00 | 18.18 | A | C |
| ATOM | 570 | O | VAL | A | 58 | 72.461 | −36.063 | −12.402 | 1.00 | 17.53 | A | O |
| ATOM | 572 | N | ARG | A | 59 | 72.841 | −34.337 | −13.802 | 1.00 | 20.36 | A | N |
| ATOM | 573 | CA | ARG | A | 59 | 71.896 | −34.833 | −14.819 | 1.00 | 19.83 | A | C |
| ATOM | 575 | CB | ARG | A | 59 | 71.891 | −33.923 | −16.049 | 1.00 | 20.72 | A | C |
| ATOM | 578 | CG | ARG | A | 59 | 70.959 | −34.357 | −17.180 | 1.00 | 21.44 | A | C |
| ATOM | 581 | CD | ARG | A | 59 | 71.656 | −35.311 | −18.172 | 1.00 | 26.88 | A | C |
| ATOM | 584 | NE | ARG | A | 59 | 70.756 | −35.765 | −19.235 | 1.00 | 26.75 | A | N |
| ATOM | 586 | CZ | ARG | A | 59 | 70.980 | −36.808 | −20.035 | 1.00 | 27.29 | A | C |
| ATOM | 587 | NH1 | ARG | A | 59 | 70.079 | −37.128 | −20.948 | 1.00 | 26.52 | A | N |
| ATOM | 590 | NH2 | ARG | A | 59 | 72.106 | −37.527 | −19.954 | 1.00 | 26.33 | A | N |
| ATOM | 593 | C | ARG | A | 59 | 72.271 | −36.239 | −15.210 | 1.00 | 20.53 | A | C |
| ATOM | 594 | O | ARG | A | 59 | 71.435 | −37.137 | −15.233 | 1.00 | 21.41 | A | O |
| ATOM | 596 | N | ARG | A | 60 | 73.546 | −36.445 | −15.495 | 1.00 | 21.14 | A | N |
| ATOM | 597 | CA | ARG | A | 60 | 73.988 | −37.755 | −15.936 | 1.00 | 19.56 | A | C |
| ATOM | 599 | CB | ARG | A | 60 | 75.477 | −37.765 | −16.209 | 1.00 | 19.04 | A | C |
| ATOM | 602 | CG | ARG | A | 60 | 75.986 | −39.109 | −16.690 | 1.00 | 21.95 | A | C |
| ATOM | 605 | CD | ARG | A | 60 | 77.465 | −39.067 | −16.905 | 1.00 | 21.61 | A | C |
| ATOM | 608 | NE | ARG | A | 60 | 78.162 | −38.960 | −15.637 | 1.00 | 25.86 | A | N |
| ATOM | 610 | CZ | ARG | A | 60 | 79.450 | −38.659 | −15.502 | 1.00 | 27.72 | A | C |
| ATOM | 611 | NH1 | ARG | A | 60 | 79.957 | −38.595 | −14.288 | 1.00 | 27.66 | A | N |
| ATOM | 614 | NH2 | ARG | A | 60 | 80.239 | −38.429 | −16.561 | 1.00 | 24.85 | A | N |
| ATOM | 617 | C | ARG | A | 60 | 73.680 | −38.834 | −14.910 | 1.00 | 20.09 | A | C |
| ATOM | 618 | O | ARG | A | 60 | 73.184 | −39.907 | −15.260 | 1.00 | 19.04 | A | O |
| ATOM | 620 | N | GLU | A | 61 | 73.987 | −38.556 | −13.652 | 1.00 | 21.36 | A | N |
| ATOM | 621 | CA | GLU | A | 61 | 73.834 | −39.565 | −12.586 | 1.00 | 21.08 | A | C |

TABLE 4-2-continued

Coordinates of *P. alba* IspS

| | | | | | | | | | | | | |
|---|---|---|---|---|---|---|---|---|---|---|---|---|
| ATOM | 623 | CB | GLU | A | 61 | 74.503 | −39.095 | −11.291 | 1.00 | 20.78 | A | C |
| ATOM | 626 | CG | GLU | A | 61 | 76.019 | −38.914 | −11.424 | 1.00 | 29.32 | A | C |
| ATOM | 629 | CD | GLU | A | 61 | 76.700 | −40.205 | −11.825 | 1.00 | 33.44 | A | C |
| ATOM | 630 | OE1 | GLU | A | 61 | 76.614 | −41.174 | −11.038 | 1.00 | 32.69 | A | O |
| ATOM | 631 | OE2 | GLU | A | 61 | 77.297 | −40.251 | −12.930 | 1.00 | 36.93 | A | O |
| ATOM | 632 | C | GLU | A | 61 | 72.376 | −39.954 | −12.308 | 1.00 | 19.59 | A | C |
| ATOM | 633 | O | GLU | A | 61 | 72.124 | −41.076 | −11.938 | 1.00 | 21.54 | A | O |
| ATOM | 635 | N | ILE | A | 62 | 71.443 | −39.024 | −12.485 | 1.00 | 20.46 | A | N |
| ATOM | 636 | CA | ILE | A | 62 | 70.019 | −39.298 | −12.290 | 1.00 | 20.63 | A | C |
| ATOM | 638 | CB | ILE | A | 62 | 69.195 | −38.010 | −12.148 | 1.00 | 20.75 | A | C |
| ATOM | 640 | CG1 | ILE | A | 62 | 69.651 | −37.184 | −10.937 | 1.00 | 20.34 | A | C |
| ATOM | 643 | CD1 | ILE | A | 62 | 69.052 | −35.781 | −10.885 | 1.00 | 17.82 | A | C |
| ATOM | 647 | CG2 | ILE | A | 62 | 67.708 | −38.363 | −12.000 | 1.00 | 21.70 | A | C |
| ATOM | 651 | C | ILE | A | 62 | 69.462 | −40.108 | −13.462 | 1.00 | 22.58 | A | C |
| ATOM | 652 | O | ILE | A | 62 | 68.548 | −40.895 | −13.298 | 1.00 | 23.12 | A | O |
| ATOM | 654 | N | ASN | A | 63 | 70.008 | −39.899 | −14.656 | 1.00 | 24.14 | A | N |
| ATOM | 655 | CA | ASN | A | 63 | 69.567 | −40.628 | −15.840 | 1.00 | 22.08 | A | C |
| ATOM | 657 | CB | ASN | A | 63 | 69.839 | −39.776 | −17.071 | 1.00 | 20.09 | A | C |
| ATOM | 660 | CG | ASN | A | 63 | 68.812 | −38.693 | −17.256 | 1.00 | 24.05 | A | C |
| ATOM | 661 | OD1 | ASN | A | 63 | 67.809 | −38.925 | −17.893 | 1.00 | 28.24 | A | O |
| ATOM | 662 | ND2 | ASN | A | 63 | 69.063 | −37.493 | −16.717 | 1.00 | 22.91 | A | N |
| ATOM | 665 | C | ASN | A | 63 | 70.232 | −41.999 | −15.980 | 1.00 | 23.43 | A | C |
| ATOM | 666 | O | ASN | A | 63 | 69.809 | −42.829 | −16.783 | 1.00 | 25.36 | A | O |
| ATOM | 668 | N | ASN | A | 64 | 71.277 | −42.226 | −15.194 | 1.00 | 25.57 | A | N |
| ATOM | 669 | CA | ASN | A | 64 | 72.064 | −43.451 | −15.242 | 1.00 | 27.94 | A | C |
| ATOM | 671 | CB | ASN | A | 64 | 73.151 | −43.357 | −14.165 | 1.00 | 27.54 | A | C |
| ATOM | 674 | CG | ASN | A | 64 | 74.104 | −44.557 | −14.138 | 1.00 | 30.25 | A | C |
| ATOM | 675 | OD1 | ASN | A | 64 | 74.164 | −45.350 | −15.074 | 1.00 | 24.98 | A | O |
| ATOM | 676 | ND2 | ASN | A | 64 | 74.876 | −44.666 | −13.054 | 1.00 | 20.45 | A | N |
| ATOM | 679 | C | ASN | A | 64 | 71.185 | −44.656 | −14.992 | 1.00 | 30.41 | A | C |
| ATOM | 680 | O | ASN | A | 64 | 70.691 | −44.821 | −13.892 | 1.00 | 32.21 | A | O |
| ATOM | 682 | N | GLU | A | 65 | 71.004 | −45.516 | −15.989 | 1.00 | 33.50 | A | N |
| ATOM | 683 | CA | GLU | A | 65 | 70.150 | −46.701 | −15.800 | 1.00 | 35.73 | A | C |
| ATOM | 685 | CB | GLU | A | 65 | 69.578 | −47.175 | −17.129 | 1.00 | 36.73 | A | C |
| ATOM | 688 | CG | GLU | A | 65 | 68.675 | −46.102 | −17.762 | 1.00 | 41.17 | A | C |
| ATOM | 691 | CD | GLU | A | 65 | 67.803 | −46.596 | −18.908 | 1.00 | 48.22 | A | C |
| ATOM | 692 | OE1 | GLU | A | 65 | 67.712 | −47.831 | −19.150 | 1.00 | 47.55 | A | O |
| ATOM | 693 | OE2 | GLU | A | 65 | 67.194 | −45.716 | −19.562 | 1.00 | 48.75 | A | O |
| ATOM | 694 | C | GLU | A | 65 | 70.871 | −47.836 | −15.094 | 1.00 | 36.68 | A | C |
| ATOM | 695 | O | GLU | A | 65 | 70.240 | −48.776 | −14.634 | 1.00 | 37.20 | A | O |
| ATOM | 697 | N | LYS | A | 66 | 72.189 | −47.730 | −14.984 | 1.00 | 36.43 | A | N |
| ATOM | 698 | CA | LYS | A | 66 | 72.999 | −48.790 | −14.404 | 1.00 | 37.11 | A | C |
| ATOM | 700 | CB | LYS | A | 66 | 74.383 | −48.828 | −15.084 | 1.00 | 38.18 | A | C |
| ATOM | 703 | CG | LYS | A | 66 | 74.340 | −48.999 | −16.621 | 1.00 | 41.19 | A | C |
| ATOM | 706 | CD | LYS | A | 66 | 75.757 | −48.982 | −17.252 | 1.00 | 47.45 | A | C |
| ATOM | 709 | CE | LYS | A | 66 | 75.731 | −49.109 | −18.801 | 1.00 | 47.41 | A | C |
| ATOM | 712 | NZ | LYS | A | 66 | 74.829 | −50.210 | −19.287 | 1.00 | 47.24 | A | N |
| ATOM | 716 | C | LYS | A | 66 | 73.166 | −48.635 | −12.890 | 1.00 | 35.98 | A | C |
| ATOM | 717 | O | LYS | A | 66 | 73.803 | −49.470 | −12.252 | 1.00 | 36.59 | A | O |
| ATOM | 719 | N | ALA | A | 67 | 72.594 | −47.585 | −12.309 | 1.00 | 35.32 | A | N |
| ATOM | 720 | CA | ALA | A | 67 | 72.761 | −47.334 | −10.869 | 1.00 | 35.29 | A | C |
| ATOM | 722 | CB | ALA | A | 67 | 72.338 | −45.929 | −10.522 | 1.00 | 34.33 | A | C |
| ATOM | 726 | C | ALA | A | 67 | 71.970 | −48.331 | −10.027 | 1.00 | 35.67 | A | C |
| ATOM | 727 | O | ALA | A | 67 | 70.907 | −48.823 | −10.436 | 1.00 | 34.29 | A | O |
| ATOM | 729 | N | GLU | A | 68 | 72.502 | −48.627 | −8.850 | 1.00 | 36.18 | A | N |
| ATOM | 730 | CA | GLU | A | 68 | 71.759 | −49.403 | −7.869 | 1.00 | 38.84 | A | C |
| ATOM | 732 | CB | GLU | A | 68 | 72.619 | −49.725 | −6.645 | 1.00 | 40.31 | A | C |
| ATOM | 735 | CG | GLU | A | 68 | 72.545 | −51.178 | −6.224 | 1.00 | 51.58 | A | C |
| ATOM | 738 | CD | GLU | A | 68 | 73.198 | −52.108 | −7.240 | 1.00 | 62.21 | A | C |
| ATOM | 739 | OE1 | GLU | A | 68 | 74.352 | −51.827 | −7.646 | 1.00 | 67.12 | A | O |
| ATOM | 740 | OE2 | GLU | A | 68 | 72.558 | −53.114 | −7.632 | 1.00 | 64.39 | A | O |
| ATOM | 741 | C | GLU | A | 68 | 70.558 | −48.554 | −7.476 | 1.00 | 38.64 | A | C |
| ATOM | 742 | O | GLU | A | 68 | 70.672 | −47.332 | −7.342 | 1.00 | 37.36 | A | O |
| ATOM | 744 | N | PHE | A | 69 | 69.407 | −49.194 | −7.315 | 1.00 | 39.25 | A | N |
| ATOM | 745 | CA | PHE | A | 69 | 68.163 | −48.453 | −7.180 | 1.00 | 41.61 | A | C |
| ATOM | 747 | CB | PHE | A | 69 | 66.925 | −49.361 | −7.351 | 1.00 | 43.96 | A | C |
| ATOM | 750 | CG | PHE | A | 69 | 66.460 | −49.487 | −8.795 | 1.00 | 54.44 | A | C |
| ATOM | 751 | CD1 | PHE | A | 69 | 66.310 | −48.336 | −9.610 | 1.00 | 61.05 | A | C |
| ATOM | 753 | CE1 | PHE | A | 69 | 65.882 | −48.429 | −10.943 | 1.00 | 61.96 | A | C |
| ATOM | 755 | CZ | PHE | A | 69 | 65.586 | −49.684 | −11.483 | 1.00 | 65.52 | A | C |
| ATOM | 757 | CE2 | PHE | A | 69 | 65.728 | −50.846 | −10.681 | 1.00 | 65.07 | A | C |
| ATOM | 759 | CD2 | PHE | A | 69 | 66.161 | −50.739 | −9.344 | 1.00 | 62.25 | A | C |
| ATOM | 761 | C | PHE | A | 69 | 68.094 | −47.639 | −5.889 | 1.00 | 39.35 | A | C |
| ATOM | 762 | O | PHE | A | 69 | 67.620 | −46.506 | −5.906 | 1.00 | 34.88 | A | O |
| ATOM | 764 | N | LEU | A | 70 | 68.605 | −48.185 | −4.793 | 1.00 | 38.05 | A | N |
| ATOM | 765 | CA | LEU | A | 70 | 68.642 | −47.417 | −3.547 | 1.00 | 37.39 | A | C |
| ATOM | 767 | CB | LEU | A | 70 | 68.989 | −48.320 | −2.367 | 1.00 | 38.91 | A | C |
| ATOM | 770 | CG | LEU | A | 70 | 68.749 | −47.727 | −0.970 | 1.00 | 45.09 | A | C |

TABLE 4-2-continued

Coordinates of *P. alba* IspS

| | | | | | | | | | | | | |
|---|---|---|---|---|---|---|---|---|---|---|---|---|
| ATOM | 772 | CD1 | LEU | A | 70 | 67.365 | −47.093 | −0.854 | 1.00 | 42.32 | A | C |
| ATOM | 776 | CD2 | LEU | A | 70 | 68.950 | −48.819 | 0.092 | 1.00 | 48.11 | A | C |
| ATOM | 780 | C | LEU | A | 70 | 69.585 | −46.208 | −3.616 | 1.00 | 35.24 | A | C |
| ATOM | 781 | O | LEU | A | 70 | 69.273 | −45.134 | −3.076 | 1.00 | 33.59 | A | O |
| ATOM | 783 | N | THR | A | 71 | 70.715 | −46.351 | −4.308 | 1.00 | 32.18 | A | N |
| ATOM | 784 | CA | THR | A | 71 | 71.664 | −45.232 | −4.462 | 1.00 | 30.26 | A | C |
| ATOM | 786 | CB | THR | A | 71 | 72.975 | −45.686 | −5.151 | 1.00 | 31.18 | A | C |
| ATOM | 788 | OG1 | THR | A | 71 | 73.583 | −46.737 | −4.380 | 1.00 | 35.88 | A | O |
| ATOM | 790 | CG2 | THR | A | 71 | 73.957 | −44.539 | −5.269 | 1.00 | 32.21 | A | C |
| ATOM | 794 | C | THR | A | 71 | 71.023 | −44.120 | −5.277 | 1.00 | 27.98 | A | C |
| ATOM | 795 | O | THR | A | 71 | 71.215 | −42.940 | −5.011 | 1.00 | 29.70 | A | O |
| ATOM | 797 | N | LEU | A | 72 | 70.235 | −44.508 | −6.258 | 1.00 | 25.13 | A | N |
| ATOM | 798 | CA | LEU | A | 72 | 69.560 | −43.566 | −7.120 | 1.00 | 25.64 | A | C |
| ATOM | 800 | CB | LEU | A | 72 | 68.879 | −44.315 | −8.262 | 1.00 | 24.76 | A | C |
| ATOM | 803 | CG | LEU | A | 72 | 68.348 | −43.417 | −9.367 | 1.00 | 33.13 | A | C |
| ATOM | 805 | CD1 | LEU | A | 72 | 69.500 | −42.625 | −9.999 | 1.00 | 34.90 | A | C |
| ATOM | 809 | CD2 | LEU | A | 72 | 67.635 | −44.244 | −10.419 | 1.00 | 33.87 | A | C |
| ATOM | 813 | C | LEU | A | 72 | 68.515 | −42.792 | −6.344 | 1.00 | 25.13 | A | C |
| ATOM | 814 | O | LEU | A | 72 | 68.442 | −41.559 | −6.423 | 1.00 | 24.06 | A | O |
| ATOM | 816 | N | LEU | A | 73 | 67.705 | −43.530 | −5.593 | 1.00 | 24.72 | A | N |
| ATOM | 817 | CA | LEU | A | 73 | 66.685 | −42.926 | −4.767 | 1.00 | 24.94 | A | C |
| ATOM | 819 | CB | LEU | A | 73 | 65.863 | −43.986 | −4.053 | 1.00 | 25.13 | A | C |
| ATOM | 822 | CG | LEU | A | 73 | 65.002 | −44.831 | −4.983 | 1.00 | 24.35 | A | C |
| ATOM | 824 | CD1 | LEU | A | 73 | 64.535 | −46.087 | −4.255 | 1.00 | 25.41 | A | C |
| ATOM | 828 | CD2 | LEU | A | 73 | 63.853 | −44.027 | −5.559 | 1.00 | 20.54 | A | C |
| ATOM | 832 | C | LEU | A | 73 | 67.279 | −41.941 | −3.776 | 1.00 | 24.82 | A | C |
| ATOM | 833 | O | LEU | A | 73 | 66.697 | −40.868 | −3.534 | 1.00 | 24.80 | A | O |
| ATOM | 835 | N | GLU | A | 74 | 68.432 | −42.287 | −3.213 | 1.00 | 23.25 | A | N |
| ATOM | 836 | CA | GLU | A | 74 | 69.094 | −41.412 | −2.258 | 1.00 | 23.34 | A | C |
| ATOM | 838 | CB | GLU | A | 74 | 70.095 | −42.214 | −1.406 | 1.00 | 24.35 | A | C |
| ATOM | 841 | CG | GLU | A | 74 | 69.391 | −43.188 | −0.427 | 1.00 | 32.72 | A | C |
| ATOM | 844 | CD | GLU | A | 74 | 70.321 | −43.919 | 0.537 | 1.00 | 43.15 | A | C |
| ATOM | 845 | OE1 | GLU | A | 74 | 71.558 | −43.826 | 0.407 | 1.00 | 44.90 | A | O |
| ATOM | 846 | OE2 | GLU | A | 74 | 69.799 | −44.603 | 1.438 | 1.00 | 48.93 | A | O |
| ATOM | 847 | C | GLU | A | 74 | 69.729 | −40.186 | −2.941 | 1.00 | 22.43 | A | C |
| ATOM | 848 | O | GLU | A | 74 | 69.785 | −39.096 | −2.362 | 1.00 | 24.16 | A | O |
| ATOM | 850 | N | LEU | A | 75 | 70.183 | −40.335 | −4.177 | 1.00 | 22.16 | A | N |
| ATOM | 851 | CA | LEU | A | 75 | 70.613 | −39.180 | −4.959 | 1.00 | 20.37 | A | C |
| ATOM | 853 | CB | LEU | A | 75 | 71.150 | −39.622 | −6.304 | 1.00 | 22.89 | A | C |
| ATOM | 856 | CG | LEU | A | 75 | 71.569 | −38.495 | −7.268 | 1.00 | 22.68 | A | C |
| ATOM | 858 | CD1 | LEU | A | 75 | 72.741 | −37.711 | −6.687 | 1.00 | 15.06 | A | C |
| ATOM | 862 | CD2 | LEU | A | 75 | 71.934 | −39.153 | −8.602 | 1.00 | 25.81 | A | C |
| ATOM | 866 | C | LEU | A | 75 | 69.465 | −38.220 | −5.224 | 1.00 | 20.23 | A | C |
| ATOM | 867 | O | LEU | A | 75 | 69.629 | −37.017 | −5.137 | 1.00 | 23.40 | A | O |
| ATOM | 869 | N | ILE | A | 76 | 68.307 | −38.754 | −5.582 | 1.00 | 21.55 | A | N |
| ATOM | 870 | CA | ILE | A | 76 | 67.174 | −37.912 | −5.923 | 1.00 | 23.06 | A | C |
| ATOM | 872 | CB | ILE | A | 76 | 65.974 | −38.746 | −6.401 | 1.00 | 22.62 | A | C |
| ATOM | 874 | CG1 | ILE | A | 76 | 66.259 | −39.323 | −7.790 | 1.00 | 24.94 | A | C |
| ATOM | 877 | CD1 | ILE | A | 76 | 65.388 | −40.527 | −8.171 | 1.00 | 19.96 | A | C |
| ATOM | 881 | CG2 | ILE | A | 76 | 64.717 | −37.881 | −6.400 | 1.00 | 19.22 | A | C |
| ATOM | 885 | C | ILE | A | 76 | 66.755 | −37.093 | −4.711 | 1.00 | 24.28 | A | C |
| ATOM | 886 | O | ILE | A | 76 | 66.472 | −35.896 | −4.821 | 1.00 | 26.54 | A | O |
| ATOM | 888 | N | ASP | A | 77 | 66.717 | −37.761 | −3.563 | 1.00 | 23.78 | A | N |
| ATOM | 889 | CA | ASP | A | 77 | 66.327 | −37.154 | −2.298 | 1.00 | 24.77 | A | C |
| ATOM | 891 | CB | ASP | A | 77 | 66.306 | −38.227 | −1.200 | 1.00 | 23.52 | A | C |
| ATOM | 894 | CG | ASP | A | 77 | 65.627 | −37.769 | 0.071 | 1.00 | 30.63 | A | C |
| ATOM | 895 | OD1 | ASP | A | 77 | 64.773 | −36.826 | 0.038 | 1.00 | 30.60 | A | O |
| ATOM | 896 | OD2 | ASP | A | 77 | 65.941 | −38.387 | 1.119 | 1.00 | 33.55 | A | O |
| ATOM | 897 | C | ASP | A | 77 | 67.308 | −36.068 | −1.909 | 1.00 | 25.16 | A | C |
| ATOM | 898 | O | ASP | A | 77 | 66.907 | −34.999 | −1.440 | 1.00 | 24.30 | A | O |
| ATOM | 900 | N | ASN | A | 78 | 68.602 | −36.348 | −2.093 | 1.00 | 25.18 | A | N |
| ATOM | 901 | CA | ASN | A | 78 | 69.643 | −35.372 | −1.765 | 1.00 | 23.87 | A | C |
| ATOM | 903 | CB | ASN | A | 78 | 71.032 | −36.003 | −1.918 | 1.00 | 27.24 | A | C |
| ATOM | 906 | CG | ASN | A | 78 | 71.448 | −36.844 | −0.701 | 1.00 | 29.01 | A | C |
| ATOM | 907 | OD1 | ASN | A | 78 | 71.108 | −36.503 | 0.421 | 1.00 | 29.64 | A | O |
| ATOM | 908 | ND2 | ASN | A | 78 | 72.208 | −37.933 | −0.928 | 1.00 | 22.29 | A | N |
| ATOM | 911 | C | ASN | A | 78 | 69.482 | −34.154 | −2.679 | 1.00 | 23.28 | A | C |
| ATOM | 912 | O | ASN | A | 78 | 69.488 | −32.988 | −2.235 | 1.00 | 22.07 | A | O |
| ATOM | 914 | N | VAL | A | 79 | 69.293 | −34.431 | −3.962 | 1.00 | 21.38 | A | N |
| ATOM | 915 | CA | VAL | A | 79 | 69.097 | −33.364 | −4.947 | 1.00 | 22.16 | A | C |
| ATOM | 917 | CB | VAL | A | 79 | 68.883 | −33.961 | −6.357 | 1.00 | 23.08 | A | C |
| ATOM | 919 | CG1 | VAL | A | 79 | 68.336 | −32.907 | −7.305 | 1.00 | 19.92 | A | C |
| ATOM | 923 | CG2 | VAL | A | 79 | 70.195 | −34.593 | −6.876 | 1.00 | 18.18 | A | C |
| ATOM | 927 | C | VAL | A | 79 | 67.892 | −32.487 | −4.573 | 1.00 | 21.06 | A | C |
| ATOM | 928 | O | VAL | A | 79 | 67.950 | −31.257 | −4.642 | 1.00 | 22.39 | A | O |
| ATOM | 930 | N | GLN | A | 80 | 66.805 | −33.109 | −4.155 | 1.00 | 20.41 | A | N |
| ATOM | 931 | CA | GLN | A | 80 | 65.613 | −32.315 | −3.760 | 1.00 | 21.13 | A | C |
| ATOM | 933 | CB | GLN | A | 80 | 64.376 | −33.203 | −3.656 | 1.00 | 19.81 | A | C |

TABLE 4-2-continued

Coordinates of *P. alba* IspS

| | | | | | | | | | | | | |
|---|---|---|---|---|---|---|---|---|---|---|---|---|
| ATOM | 936 | CG | GLN | A | 80 | 64.025 | −33.857 | −5.004 | 1.00 | 16.22 | A | C |
| ATOM | 939 | CD | GLN | A | 80 | 62.628 | −34.460 | −5.034 | 1.00 | 23.03 | A | C |
| ATOM | 940 | OE1 | GLN | A | 80 | 61.984 | −34.492 | −6.087 | 1.00 | 19.49 | A | O |
| ATOM | 941 | NE2 | GLN | A | 80 | 62.146 | −34.930 | −3.873 | 1.00 | 19.16 | A | N |
| ATOM | 944 | C | GLN | A | 80 | 65.829 | −31.542 | −2.465 | 1.00 | 22.00 | A | C |
| ATOM | 945 | O | GLN | A | 80 | 65.497 | −30.360 | −2.366 | 1.00 | 25.58 | A | O |
| ATOM | 947 | N | ARG | A | 81 | 66.399 | −32.200 | −1.475 | 1.00 | 20.76 | A | N |
| ATOM | 948 | CA | ARG | A | 81 | 66.557 | −31.579 | −0.171 | 1.00 | 22.60 | A | C |
| ATOM | 950 | CB | ARG | A | 81 | 67.004 | −32.619 | 0.840 | 1.00 | 22.73 | A | C |
| ATOM | 953 | CG | ARG | A | 81 | 65.896 | −33.644 | 1.107 | 1.00 | 27.58 | A | C |
| ATOM | 956 | CD | ARG | A | 81 | 66.200 | −34.449 | 2.360 | 1.00 | 26.39 | A | C |
| ATOM | 959 | NE | ARG | A | 81 | 66.352 | −33.563 | 3.508 | 1.00 | 33.93 | A | N |
| ATOM | 961 | CZ | ARG | A | 81 | 66.523 | −33.991 | 4.754 | 1.00 | 44.75 | A | C |
| ATOM | 962 | NH1 | ARG | A | 81 | 66.529 | −35.296 | 5.011 | 1.00 | 46.21 | A | N |
| ATOM | 965 | NH2 | ARG | A | 81 | 66.665 | −33.114 | 5.747 | 1.00 | 38.64 | A | N |
| ATOM | 968 | C | ARG | A | 81 | 67.534 | −30.418 | −0.225 | 1.00 | 21.64 | A | C |
| ATOM | 969 | O | ARG | A | 81 | 67.329 | −29.389 | 0.424 | 1.00 | 22.17 | A | O |
| ATOM | 971 | N | LEU | A | 82 | 68.575 | −30.578 | −1.032 | 1.00 | 18.90 | A | N |
| ATOM | 972 | CA | LEU | A | 82 | 69.556 | −29.522 | −1.230 | 1.00 | 16.62 | A | C |
| ATOM | 974 | CB | LEU | A | 82 | 70.796 | −30.076 | −1.937 | 1.00 | 15.07 | A | C |
| ATOM | 977 | CG | LEU | A | 82 | 71.610 | −31.097 | −1.137 | 1.00 | 19.59 | A | C |
| ATOM | 979 | CD1 | LEU | A | 82 | 72.585 | −31.806 | −2.061 | 1.00 | 19.94 | A | C |
| ATOM | 983 | CD2 | LEU | A | 82 | 72.325 | −30.424 | 0.043 | 1.00 | 16.09 | A | C |
| ATOM | 987 | C | LEU | A | 82 | 68.998 | −28.356 | −2.013 | 1.00 | 17.05 | A | C |
| ATOM | 988 | O | LEU | A | 82 | 69.691 | −27.374 | −2.197 | 1.00 | 18.11 | A | O |
| ATOM | 990 | N | GLY | A | 83 | 67.759 | −28.470 | −2.490 | 1.00 | 19.79 | A | N |
| ATOM | 991 | CA | GLY | A | 83 | 67.064 | −27.359 | −3.130 | 1.00 | 20.72 | A | C |
| ATOM | 994 | C | GLY | A | 83 | 67.100 | −27.353 | −4.651 | 1.00 | 21.28 | A | C |
| ATOM | 995 | O | GLY | A | 83 | 66.622 | −26.412 | −5.277 | 1.00 | 21.81 | A | O |
| ATOM | 997 | N | LEU | A | 84 | 67.620 | −28.418 | −5.254 | 1.00 | 22.14 | A | N |
| ATOM | 998 | CA | LEU | A | 84 | 67.836 | −28.450 | −6.704 | 1.00 | 22.65 | A | C |
| ATOM | 1000 | CB | LEU | A | 84 | 69.193 | −29.092 | −6.998 | 1.00 | 20.71 | A | C |
| ATOM | 1003 | CG | LEU | A | 84 | 70.398 | −28.272 | −6.564 | 1.00 | 21.65 | A | C |
| ATOM | 1005 | CD1 | LEU | A | 84 | 71.625 | −29.158 | −6.493 | 1.00 | 18.26 | A | C |
| ATOM | 1009 | CD2 | LEU | A | 84 | 70.634 | −27.090 | −7.483 | 1.00 | 14.55 | A | C |
| ATOM | 1013 | C | LEU | A | 84 | 66.744 | −29.200 | −7.505 | 1.00 | 24.69 | A | C |
| ATOM | 1014 | O | LEU | A | 84 | 66.853 | −29.305 | −8.734 | 1.00 | 24.25 | A | O |
| ATOM | 1016 | N | GLY | A | 85 | 65.718 | −29.718 | −6.826 | 1.00 | 23.20 | A | N |
| ATOM | 1017 | CA | GLY | A | 85 | 64.646 | −30.512 | −7.476 | 1.00 | 24.92 | A | C |
| ATOM | 1020 | C | GLY | A | 85 | 63.962 | −29.846 | −8.659 | 1.00 | 24.61 | A | C |
| ATOM | 1021 | O | GLY | A | 85 | 63.792 | −30.465 | −9.714 | 1.00 | 26.70 | A | O |
| ATOM | 1023 | N | TYR | A | 86 | 63.625 | −28.570 | −8.511 | 1.00 | 26.13 | A | N |
| ATOM | 1024 | CA | TYR | A | 86 | 63.032 | −27.765 | −9.616 | 1.00 | 27.13 | A | C |
| ATOM | 1026 | CB | TYR | A | 86 | 62.880 | −26.295 | −9.195 | 1.00 | 25.38 | A | C |
| ATOM | 1029 | CG | TYR | A | 86 | 64.180 | −25.458 | −9.276 | 1.00 | 21.72 | A | C |
| ATOM | 1030 | CD1 | TYR | A | 86 | 64.428 | −24.637 | −10.362 | 1.00 | 19.43 | A | C |
| ATOM | 1032 | CE1 | TYR | A | 86 | 65.582 | −23.874 | −10.435 | 1.00 | 24.50 | A | C |
| ATOM | 1034 | CZ | TYR | A | 86 | 66.513 | −23.916 | −9.398 | 1.00 | 20.21 | A | C |
| ATOM | 1035 | OH | TYR | A | 86 | 67.655 | −23.164 | −9.489 | 1.00 | 16.34 | A | O |
| ATOM | 1037 | CE2 | TYR | A | 86 | 66.287 | −24.695 | −8.297 | 1.00 | 15.09 | A | C |
| ATOM | 1039 | CD2 | TYR | A | 86 | 65.123 | −25.470 | −8.235 | 1.00 | 20.89 | A | C |
| ATOM | 1041 | C | TYR | A | 86 | 63.861 | −27.803 | −10.904 | 1.00 | 28.47 | A | C |
| ATOM | 1042 | O | TYR | A | 86 | 63.369 | −27.573 | −12.003 | 1.00 | 33.02 | A | O |
| ATOM | 1044 | N | ARG | A | 87 | 65.140 | −28.075 | −10.752 | 1.00 | 28.58 | A | N |
| ATOM | 1045 | CA | ARG | A | 87 | 66.067 | −28.023 | −11.854 | 1.00 | 28.18 | A | C |
| ATOM | 1047 | CB | ARG | A | 87 | 67.395 | −27.694 | −11.215 | 1.00 | 29.83 | A | C |
| ATOM | 1050 | CG | ARG | A | 87 | 68.405 | −27.210 | −12.098 | 1.00 | 31.31 | A | C |
| ATOM | 1053 | CD | ARG | A | 87 | 69.334 | −26.189 | −11.405 | 1.00 | 29.77 | A | C |
| ATOM | 1056 | NE | ARG | A | 87 | 69.857 | −25.501 | −12.548 | 1.00 | 28.60 | A | N |
| ATOM | 1058 | CZ | ARG | A | 87 | 69.522 | −24.301 | −12.934 | 1.00 | 21.90 | A | C |
| ATOM | 1059 | NH1 | ARG | A | 87 | 70.033 | −23.874 | −14.064 | 1.00 | 36.21 | A | N |
| ATOM | 1062 | NH2 | ARG | A | 87 | 68.772 | −23.510 | −12.182 | 1.00 | 22.93 | A | N |
| ATOM | 1065 | C | ARG | A | 87 | 66.115 | −29.349 | −12.639 | 1.00 | 27.31 | A | C |
| ATOM | 1066 | O | ARG | A | 87 | 66.425 | −29.375 | −13.824 | 1.00 | 27.32 | A | O |
| ATOM | 1068 | N | PHE | A | 88 | 65.773 | −30.448 | −11.982 | 1.00 | 26.33 | A | N |
| ATOM | 1069 | CA | PHE | A | 88 | 65.973 | −31.773 | −12.557 | 1.00 | 26.77 | A | C |
| ATOM | 1071 | CB | PHE | A | 88 | 66.993 | −32.547 | −11.717 | 1.00 | 24.89 | A | C |
| ATOM | 1074 | CG | PHE | A | 88 | 68.349 | −31.933 | −11.722 | 1.00 | 24.57 | A | C |
| ATOM | 1075 | CD1 | PHE | A | 88 | 69.151 | −32.027 | −12.851 | 1.00 | 22.34 | A | C |
| ATOM | 1077 | CE1 | PHE | A | 88 | 70.407 | −31.449 | −12.879 | 1.00 | 24.25 | A | C |
| ATOM | 1079 | CZ | PHE | A | 88 | 70.870 | −30.733 | −11.773 | 1.00 | 24.17 | A | C |
| ATOM | 1081 | CE2 | PHE | A | 88 | 70.069 | −30.614 | −10.653 | 1.00 | 22.88 | A | C |
| ATOM | 1083 | CD2 | PHE | A | 88 | 68.808 | −31.217 | −10.629 | 1.00 | 21.57 | A | C |
| ATOM | 1085 | C | PHE | A | 88 | 64.687 | −32.558 | −12.629 | 1.00 | 27.69 | A | C |
| ATOM | 1086 | O | PHE | A | 88 | 64.708 | −33.773 | −12.532 | 1.00 | 28.94 | A | O |
| ATOM | 1088 | N | GLU | A | 89 | 63.571 | −31.870 | −12.834 | 1.00 | 29.75 | A | N |
| ATOM | 1089 | CA | GLU | A | 89 | 62.274 | −32.508 | −12.692 | 1.00 | 32.99 | A | C |
| ATOM | 1091 | CB | GLU | A | 89 | 61.102 | −31.513 | −12.765 | 1.00 | 33.37 | A | C |

TABLE 4-2-continued

Coordinates of *P. alba* IspS

| | | | | | | | | | | | | |
|---|---|---|---|---|---|---|---|---|---|---|---|---|
| ATOM | 1094 | CG | GLU | A | 89 | 59.763 | −32.231 | −12.470 | 1.00 | 46.55 | A | C |
| ATOM | 1097 | CD | GLU | A | 89 | 58.580 | −31.316 | −12.217 | 1.00 | 57.05 | A | C |
| ATOM | 1098 | OE1 | GLU | A | 89 | 58.729 | −30.328 | −11.448 | 1.00 | 60.68 | A | O |
| ATOM | 1099 | OE2 | GLU | A | 89 | 57.496 | −31.622 | −12.775 | 1.00 | 57.95 | A | O |
| ATOM | 1100 | C | GLU | A | 89 | 62.042 | −33.637 | −13.678 | 1.00 | 32.53 | A | C |
| ATOM | 1101 | O | GLU | A | 89 | 61.662 | −34.736 | −13.269 | 1.00 | 32.44 | A | O |
| ATOM | 1103 | N | SER | A | 90 | 62.244 | −33.379 | −14.965 | 1.00 | 31.61 | A | N |
| ATOM | 1104 | CA | SER | A | 90 | 62.011 | −34.420 | −15.965 | 1.00 | 32.03 | A | C |
| ATOM | 1106 | CB | SER | A | 90 | 62.136 | −33.884 | −17.397 | 1.00 | 32.86 | A | C |
| ATOM | 1109 | OG | SER | A | 90 | 63.207 | −32.968 | −17.531 | 1.00 | 41.77 | A | O |
| ATOM | 1111 | C | SER | A | 90 | 62.947 | −35.591 | −15.756 | 1.00 | 29.81 | A | C |
| ATOM | 1112 | O | SER | A | 90 | 62.586 | −36.718 | −16.032 | 1.00 | 31.36 | A | O |
| ATOM | 1114 | N | ASP | A | 91 | 64.154 | −35.326 | −15.256 | 1.00 | 28.19 | A | N |
| ATOM | 1115 | CA | ASP | A | 91 | 65.126 | −36.396 | −15.014 | 1.00 | 24.23 | A | C |
| ATOM | 1117 | CB | ASP | A | 91 | 66.521 | −35.807 | −14.750 | 1.00 | 23.78 | A | C |
| ATOM | 1120 | CG | ASP | A | 91 | 66.966 | −34.819 | −15.851 | 1.00 | 27.08 | A | C |
| ATOM | 1121 | OD1 | ASP | A | 91 | 67.311 | −35.261 | −16.954 | 1.00 | 33.39 | A | O |
| ATOM | 1122 | OD2 | ASP | A | 91 | 66.968 | −33.601 | −15.619 | 1.00 | 36.51 | A | O |
| ATOM | 1123 | C | ASP | A | 91 | 64.657 | −37.237 | −13.820 | 1.00 | 25.06 | A | C |
| ATOM | 1124 | O | ASP | A | 91 | 64.691 | −38.467 | −13.864 | 1.00 | 22.54 | A | O |
| ATOM | 1126 | N | ILE | A | 92 | 64.213 | −36.573 | −12.749 | 1.00 | 22.98 | A | N |
| ATOM | 1127 | CA | ILE | A | 92 | 63.739 | −37.290 | −11.568 | 1.00 | 23.78 | A | C |
| ATOM | 1129 | CB | ILE | A | 92 | 63.401 | −36.337 | −10.446 | 1.00 | 22.94 | A | C |
| ATOM | 1131 | CG1 | ILE | A | 92 | 64.687 | −35.861 | −9.804 | 1.00 | 19.21 | A | C |
| ATOM | 1134 | CD1 | ILE | A | 92 | 64.563 | −34.555 | −9.062 | 1.00 | 17.83 | A | C |
| ATOM | 1138 | CG2 | ILE | A | 92 | 62.526 | −37.040 | −9.414 | 1.00 | 23.71 | A | C |
| ATOM | 1142 | C | ILE | A | 92 | 62.509 | −38.135 | −11.919 | 1.00 | 24.89 | A | C |
| ATOM | 1143 | O | ILE | A | 92 | 62.486 | −39.327 | −11.669 | 1.00 | 23.25 | A | O |
| ATOM | 1145 | N | ARG | A | 93 | 61.513 | −37.524 | −12.542 | 1.00 | 26.25 | A | N |
| ATOM | 1146 | CA | ARG | A | 93 | 60.331 | −38.275 | −12.964 | 1.00 | 28.67 | A | C |
| ATOM | 1148 | CB | ARG | A | 93 | 59.345 | −37.394 | −13.747 | 1.00 | 30.12 | A | C |
| ATOM | 1151 | CG | ARG | A | 93 | 58.786 | −36.167 | −13.040 | 1.00 | 34.31 | A | C |
| ATOM | 1154 | CD | ARG | A | 93 | 57.781 | −35.434 | −14.024 | 1.00 | 38.26 | A | C |
| ATOM | 1157 | NE | ARG | A | 93 | 56.850 | −36.429 | −14.548 | 1.00 | 40.69 | A | N |
| ATOM | 1159 | CZ | ARG | A | 93 | 55.847 | −36.955 | −13.847 | 1.00 | 45.91 | A | C |
| ATOM | 1160 | NH1 | ARG | A | 93 | 55.602 | −36.551 | −12.602 | 1.00 | 47.58 | A | N |
| ATOM | 1163 | NH2 | ARG | A | 93 | 55.059 | −37.874 | −14.392 | 1.00 | 49.96 | A | N |
| ATOM | 1166 | C | ARG | A | 93 | 60.712 | −39.443 | −13.877 | 1.00 | 28.48 | A | C |
| ATOM | 1167 | O | ARG | A | 93 | 60.134 | −40.512 | −13.783 | 1.00 | 28.33 | A | O |
| ATOM | 1169 | N | GLY | A | 94 | 61.655 | −39.219 | −14.790 | 1.00 | 27.77 | A | N |
| ATOM | 1170 | CA | GLY | A | 94 | 62.097 | −40.281 | −15.692 | 1.00 | 26.95 | A | C |
| ATOM | 1173 | C | GLY | A | 94 | 62.607 | −41.477 | −14.914 | 1.00 | 28.30 | A | C |
| ATOM | 1174 | O | GLY | A | 94 | 62.298 | −42.631 | −15.231 | 1.00 | 30.24 | A | O |
| ATOM | 1176 | N | ALA | A | 95 | 63.390 | −41.203 | −13.882 | 1.00 | 25.47 | A | N |
| ATOM | 1177 | CA | ALA | A | 95 | 64.045 | −42.254 | −13.123 | 1.00 | 25.65 | A | C |
| ATOM | 1179 | CB | ALA | A | 95 | 65.183 | −41.658 | −12.263 | 1.00 | 23.46 | A | C |
| ATOM | 1183 | C | ALA | A | 95 | 63.044 | −42.991 | −12.250 | 1.00 | 25.68 | A | C |
| ATOM | 1184 | O | ALA | A | 95 | 63.149 | −44.208 | −12.070 | 1.00 | 27.08 | A | O |
| ATOM | 1186 | N | LEU | A | 96 | 62.073 | −42.266 | −11.711 | 1.00 | 24.42 | A | N |
| ATOM | 1187 | CA | LEU | A | 96 | 61.032 | −42.899 | −10.893 | 1.00 | 25.56 | A | C |
| ATOM | 1189 | CB | LEU | A | 96 | 60.201 | −41.851 | −10.150 | 1.00 | 24.25 | A | C |
| ATOM | 1192 | CG | LEU | A | 96 | 60.979 | −41.085 | −9.090 | 1.00 | 26.81 | A | C |
| ATOM | 1194 | CD1 | LEU | A | 96 | 60.175 | −39.926 | −8.563 | 1.00 | 21.85 | A | C |
| ATOM | 1198 | CD2 | LEU | A | 96 | 61.365 | −42.017 | −7.974 | 1.00 | 23.10 | A | C |
| ATOM | 1202 | C | LEU | A | 96 | 60.121 | −43.764 | −11.755 | 1.00 | 27.28 | A | C |
| ATOM | 1203 | O | LEU | A | 96 | 59.707 | −44.848 | −11.352 | 1.00 | 24.29 | A | O |
| ATOM | 1205 | N | ASP | A | 97 | 59.805 | −43.278 | −12.952 | 1.00 | 31.37 | A | N |
| ATOM | 1206 | CA | ASP | A | 97 | 59.040 | −44.080 | −13.895 | 1.00 | 34.30 | A | C |
| ATOM | 1208 | CB | ASP | A | 97 | 58.875 | −43.351 | −15.205 | 1.00 | 34.30 | A | C |
| ATOM | 1211 | CG | ASP | A | 97 | 57.901 | −44.050 | −16.125 | 1.00 | 47.50 | A | C |
| ATOM | 1212 | OD1 | ASP | A | 97 | 58.360 | −44.783 | −17.041 | 1.00 | 55.79 | A | O |
| ATOM | 1213 | OD2 | ASP | A | 97 | 56.676 | −43.884 | −15.908 | 1.00 | 54.69 | A | O |
| ATOM | 1214 | C | ASP | A | 97 | 59.735 | −45.428 | −14.131 | 1.00 | 35.14 | A | C |
| ATOM | 1215 | O | ASP | A | 97 | 59.110 | −46.485 | −14.136 | 1.00 | 34.56 | A | O |
| ATOM | 1217 | N | ARG | A | 98 | 61.043 | −45.376 | −14.299 | 1.00 | 36.78 | A | N |
| ATOM | 1218 | CA | ARG | A | 98 | 61.813 | −46.568 | −14.600 | 1.00 | 38.34 | A | C |
| ATOM | 1220 | CB | ARG | A | 98 | 63.232 | −46.187 | −15.013 | 1.00 | 38.88 | A | C |
| ATOM | 1223 | CG | ARG | A | 98 | 63.620 | −46.641 | −16.400 | 1.00 | 43.64 | A | C |
| ATOM | 1226 | CD | ARG | A | 98 | 64.485 | −45.611 | −17.145 | 1.00 | 43.57 | A | C |
| ATOM | 1229 | NE | ARG | A | 98 | 65.396 | −44.847 | −16.278 | 1.00 | 39.48 | A | N |
| ATOM | 1231 | CZ | ARG | A | 98 | 65.577 | −43.522 | −16.340 | 1.00 | 34.93 | A | C |
| ATOM | 1232 | NH1 | ARG | A | 98 | 64.927 | −42.778 | −17.238 | 1.00 | 36.94 | A | N |
| ATOM | 1235 | NH2 | ARG | A | 98 | 66.431 | −42.932 | −15.512 | 1.00 | 36.51 | A | N |
| ATOM | 1238 | C | ARG | A | 98 | 61.842 | −47.475 | −13.379 | 1.00 | 37.58 | A | C |
| ATOM | 1239 | O | ARG | A | 98 | 61.787 | −48.692 | −13.519 | 1.00 | 38.96 | A | O |
| ATOM | 1241 | N | PHE | A | 99 | 61.928 | −46.879 | −12.192 | 1.00 | 35.87 | A | N |
| ATOM | 1242 | CA | PHE | A | 99 | 61.924 | −47.629 | −10.948 | 1.00 | 36.10 | A | C |
| ATOM | 1244 | CB | PHE | A | 99 | 62.170 | −46.693 | −9.756 | 1.00 | 37.12 | A | C |

TABLE 4-2-continued

Coordinates of *P. alba* IspS

| | | | | | | | | | | | | |
|---|---|---|---|---|---|---|---|---|---|---|---|---|
| ATOM | 1247 | CG | PHE | A | 99 | 62.224 | −47.401 | −8.427 | 1.00 | 34.31 | A | C |
| ATOM | 1248 | CD1 | PHE | A | 99 | 63.223 | −48.307 | −8.162 | 1.00 | 37.07 | A | C |
| ATOM | 1250 | CE1 | PHE | A | 99 | 63.275 | −48.973 | −6.943 | 1.00 | 37.15 | A | C |
| ATOM | 1252 | CZ | PHE | A | 99 | 62.322 | −48.714 | −5.970 | 1.00 | 35.62 | A | C |
| ATOM | 1254 | CE2 | PHE | A | 99 | 61.329 | −47.799 | −6.221 | 1.00 | 30.23 | A | C |
| ATOM | 1256 | CD2 | PHE | A | 99 | 61.271 | −47.153 | −7.444 | 1.00 | 34.40 | A | C |
| ATOM | 1258 | C | PHE | A | 99 | 60.614 | −48.406 | −10.759 | 1.00 | 36.72 | A | C |
| ATOM | 1259 | O | PHE | A | 99 | 60.617 | −49.513 | −10.213 | 1.00 | 37.39 | A | O |
| ATOM | 1261 | N | VAL | A | 100 | 59.502 | −47.838 | −11.202 | 1.00 | 35.36 | A | N |
| ATOM | 1262 | CA | VAL | A | 100 | 58.258 | −48.570 | −11.191 | 1.00 | 38.56 | A | C |
| ATOM | 1264 | CB | VAL | A | 100 | 57.054 | −47.635 | −11.263 | 1.00 | 40.72 | A | C |
| ATOM | 1266 | CG1 | VAL | A | 100 | 55.755 | −48.457 | −11.465 | 1.00 | 37.62 | A | C |
| ATOM | 1270 | CG2 | VAL | A | 100 | 56.985 | −46.787 | −9.999 | 1.00 | 33.69 | A | C |
| ATOM | 1274 | C | VAL | A | 100 | 58.202 | −49.563 | −12.367 | 1.00 | 41.18 | A | C |
| ATOM | 1275 | O | VAL | A | 100 | 57.974 | −50.760 | −12.164 | 1.00 | 40.05 | A | O |
| ATOM | 1277 | N | SER | A | 101 | 58.437 | −49.072 | −13.585 | 1.00 | 42.95 | A | N |
| ATOM | 1278 | CA | SER | A | 101 | 58.207 | −49.880 | −14.799 | 1.00 | 45.08 | A | C |
| ATOM | 1280 | CB | SER | A | 101 | 58.507 | −49.087 | −16.079 | 1.00 | 46.29 | A | C |
| ATOM | 1283 | OG | SER | A | 101 | 59.856 | −49.282 | −16.492 | 1.00 | 50.51 | A | O |
| ATOM | 1285 | C | SER | A | 101 | 59.010 | −51.169 | −14.802 | 1.00 | 44.71 | A | C |
| ATOM | 1286 | O | SER | A | 101 | 58.550 | −52.167 | −15.313 | 1.00 | 46.34 | A | O |
| ATOM | 1288 | N | SER | A | 102 | 60.200 | −51.136 | −14.218 | 1.00 | 44.39 | A | N |
| ATOM | 1289 | CA | SER | A | 102 | 61.053 | −52.306 | −14.113 | 1.00 | 45.16 | A | C |
| ATOM | 1291 | CB | SER | A | 102 | 62.506 | −51.847 | −13.944 | 1.00 | 46.36 | A | C |
| ATOM | 1294 | OG | SER | A | 102 | 62.747 | −51.406 | −12.615 | 1.00 | 47.55 | A | O |
| ATOM | 1296 | C | SER | A | 102 | 60.712 | −53.225 | −12.925 | 1.00 | 45.37 | A | C |
| ATOM | 1297 | O | SER | A | 102 | 61.418 | −54.185 | −12.672 | 1.00 | 44.04 | A | O |
| ATOM | 1299 | N | GLY | A | 103 | 59.669 | −52.904 | −12.167 | 1.00 | 46.21 | A | N |
| ATOM | 1300 | CA | GLY | A | 103 | 59.343 | −53.663 | −10.955 | 1.00 | 46.61 | A | C |
| ATOM | 1303 | C | GLY | A | 103 | 60.241 | −53.437 | −9.745 | 1.00 | 45.81 | A | C |
| ATOM | 1304 | O | GLY | A | 103 | 60.133 | −54.155 | −8.747 | 1.00 | 46.61 | A | O |
| ATOM | 1306 | N | GLY | A | 104 | 61.123 | −52.444 | −9.817 | 1.00 | 45.47 | A | N |
| ATOM | 1307 | CA | GLY | A | 104 | 62.011 | −52.136 | −8.702 | 1.00 | 44.33 | A | C |
| ATOM | 1310 | C | GLY | A | 104 | 61.271 | −51.766 | −7.434 | 1.00 | 42.90 | A | C |
| ATOM | 1311 | O | GLY | A | 104 | 61.640 | −52.210 | −6.339 | 1.00 | 43.32 | A | O |
| ATOM | 1313 | N | PHE | A | 105 | 60.228 | −50.955 | −7.574 | 1.00 | 41.44 | A | N |
| ATOM | 1314 | CA | PHE | A | 105 | 59.401 | −50.578 | −6.426 | 1.00 | 42.25 | A | C |
| ATOM | 1316 | CB | PHE | A | 105 | 58.309 | −49.569 | −6.800 | 1.00 | 40.65 | A | C |
| ATOM | 1319 | CG | PHE | A | 105 | 57.434 | −49.159 | −5.634 | 1.00 | 39.69 | A | C |
| ATOM | 1320 | CD1 | PHE | A | 105 | 57.991 | −48.615 | −4.485 | 1.00 | 35.48 | A | C |
| ATOM | 1322 | CE1 | PHE | A | 105 | 57.189 | −48.232 | −3.411 | 1.00 | 38.34 | A | C |
| ATOM | 1324 | CZ | PHE | A | 105 | 55.816 | −48.397 | −3.486 | 1.00 | 41.55 | A | C |
| ATOM | 1326 | CE2 | PHE | A | 105 | 55.253 | −48.938 | −4.612 | 1.00 | 38.70 | A | C |
| ATOM | 1328 | CD2 | PHE | A | 105 | 56.058 | −49.308 | −5.687 | 1.00 | 42.66 | A | C |
| ATOM | 1330 | C | PHE | A | 105 | 58.765 | −51.800 | −5.799 | 1.00 | 43.53 | A | C |
| ATOM | 1331 | O | PHE | A | 105 | 58.700 | −51.904 | −4.584 | 1.00 | 42.87 | A | O |
| ATOM | 1333 | N | ASP | A | 106 | 58.297 | −52.729 | −6.623 | 1.00 | 46.74 | A | N |
| ATOM | 1334 | CA | ASP | A | 106 | 57.714 | −53.948 | −6.093 | 1.00 | 49.25 | A | C |
| ATOM | 1336 | CB | ASP | A | 106 | 57.058 | −54.776 | −7.199 | 1.00 | 52.47 | A | C |
| ATOM | 1339 | CG | ASP | A | 106 | 55.671 | −55.256 | −6.807 | 1.00 | 60.96 | A | C |
| ATOM | 1340 | OD1 | ASP | A | 106 | 54.826 | −54.386 | −6.468 | 1.00 | 69.59 | A | O |
| ATOM | 1341 | OD2 | ASP | A | 106 | 55.436 | −56.486 | −6.828 | 1.00 | 66.22 | A | O |
| ATOM | 1342 | C | ASP | A | 106 | 58.775 | −54.756 | −5.354 | 1.00 | 48.33 | A | C |
| ATOM | 1343 | O | ASP | A | 106 | 58.521 | −55.290 | −4.271 | 1.00 | 48.27 | A | O |
| ATOM | 1345 | N | ALA | A | 107 | 59.971 | −54.821 | −5.927 | 1.00 | 46.84 | A | N |
| ATOM | 1346 | CA | ALA | A | 107 | 61.096 | −55.440 | −5.246 | 1.00 | 45.49 | A | C |
| ATOM | 1348 | CB | ALA | A | 107 | 62.380 | −55.283 | −6.070 | 1.00 | 46.29 | A | C |
| ATOM | 1352 | C | ALA | A | 107 | 61.285 | −54.846 | −3.853 | 1.00 | 44.32 | A | C |
| ATOM | 1353 | O | ALA | A | 107 | 61.248 | −55.581 | −2.861 | 1.00 | 45.24 | A | O |
| ATOM | 1355 | N | VAL | A | 108 | 61.468 | −53.527 | −3.752 | 1.00 | 42.93 | A | N |
| ATOM | 1356 | CA | VAL | A | 108 | 61.877 | −52.954 | −2.458 | 1.00 | 40.66 | A | C |
| ATOM | 1358 | CB | VAL | A | 108 | 62.288 | −51.469 | −2.511 | 1.00 | 41.66 | A | C |
| ATOM | 1360 | CG1 | VAL | A | 108 | 63.411 | −51.263 | −3.531 | 1.00 | 48.84 | A | C |
| ATOM | 1364 | CG2 | VAL | A | 108 | 61.078 | −50.566 | −2.778 | 1.00 | 34.77 | A | C |
| ATOM | 1368 | C | VAL | A | 108 | 60.835 | −53.130 | −1.373 | 1.00 | 39.03 | A | C |
| ATOM | 1369 | O | VAL | A | 108 | 61.198 | −53.207 | −0.210 | 1.00 | 38.61 | A | O |
| ATOM | 1371 | N | THR | A | 109 | 59.558 | −53.220 | −1.739 | 1.00 | 39.24 | A | N |
| ATOM | 1372 | CA | THR | A | 109 | 58.504 | −53.460 | −0.747 | 1.00 | 40.61 | A | C |
| ATOM | 1374 | CB | THR | A | 109 | 57.078 | −53.384 | −1.330 | 1.00 | 40.51 | A | C |
| ATOM | 1376 | OG1 | THR | A | 109 | 56.840 | −54.523 | −2.162 | 1.00 | 40.09 | A | O |
| ATOM | 1378 | CG2 | THR | A | 109 | 56.853 | −52.075 | −2.115 | 1.00 | 38.58 | A | C |
| ATOM | 1382 | C | THR | A | 109 | 58.656 | −54.815 | −0.042 | 1.00 | 42.53 | A | C |
| ATOM | 1383 | O | THR | A | 109 | 58.130 | −54.999 | 1.061 | 1.00 | 42.34 | A | O |
| ATOM | 1385 | N | LYS | A | 110 | 59.365 | −55.751 | −0.673 | 1.00 | 44.78 | A | N |
| ATOM | 1386 | CA | LYS | A | 110 | 59.616 | −57.080 | −0.082 | 1.00 | 47.15 | A | C |
| ATOM | 1388 | CB | LYS | A | 110 | 59.788 | −58.164 | −1.164 | 1.00 | 48.00 | A | C |
| ATOM | 1391 | CG | LYS | A | 110 | 58.761 | −58.189 | −2.295 | 1.00 | 52.11 | A | C |
| ATOM | 1394 | CD | LYS | A | 110 | 57.351 | −58.484 | −1.819 | 1.00 | 60.28 | A | C |

TABLE 4-2-continued

Coordinates of *P. alba* IspS

| | | | | | | | | | | | | |
|---|---|---|---|---|---|---|---|---|---|---|---|---|
| ATOM | 1397 | CE | LYS | A | 110 | 56.382 | −58.578 | −3.010 | 1.00 | 65.15 | A | C |
| ATOM | 1400 | NZ | LYS | A | 110 | 55.021 | −58.046 | −2.683 | 1.00 | 64.69 | A | N |
| ATOM | 1404 | C | LYS | A | 110 | 60.873 | −57.096 | 0.778 | 1.00 | 46.28 | A | C |
| ATOM | 1405 | O | LYS | A | 110 | 61.028 | −57.984 | 1.603 | 1.00 | 47.54 | A | O |
| ATOM | 1407 | N | THR | A | 111 | 61.770 | −56.131 | 0.570 | 1.00 | 46.36 | A | N |
| ATOM | 1408 | CA | THR | A | 111 | 63.123 | −56.191 | 1.133 | 1.00 | 45.50 | A | C |
| ATOM | 1410 | CB | THR | A | 111 | 64.197 | −56.315 | 0.003 | 1.00 | 47.36 | A | C |
| ATOM | 1412 | OG1 | THR | A | 111 | 64.312 | −55.076 | −0.711 | 1.00 | 50.35 | A | O |
| ATOM | 1414 | CG2 | THR | A | 111 | 63.837 | −57.451 | −1.000 | 1.00 | 47.26 | A | C |
| ATOM | 1418 | C | THR | A | 111 | 63.530 | −55.041 | 2.061 | 1.00 | 44.00 | A | C |
| ATOM | 1419 | O | THR | A | 111 | 64.272 | −55.284 | 3.019 | 1.00 | 44.86 | A | O |
| ATOM | 1421 | N | SER | A | 112 | 63.078 | −53.806 | 1.798 | 1.00 | 40.92 | A | N |
| ATOM | 1422 | CA | SER | A | 112 | 63.645 | −52.611 | 2.480 | 1.00 | 37.38 | A | C |
| ATOM | 1424 | CB | SER | A | 112 | 64.723 | −51.988 | 1.578 | 1.00 | 38.61 | A | C |
| ATOM | 1427 | OG | SER | A | 112 | 65.350 | −50.861 | 2.173 | 1.00 | 42.50 | A | O |
| ATOM | 1429 | C | SER | A | 112 | 62.600 | −51.542 | 2.889 | 1.00 | 33.43 | A | C |
| ATOM | 1430 | O | SER | A | 112 | 61.986 | −50.896 | 2.037 | 1.00 | 31.07 | A | O |
| ATOM | 1432 | N | LEU | A | 113 | 62.399 | −51.372 | 4.194 | 1.00 | 29.38 | A | N |
| ATOM | 1433 | CA | LEU | A | 113 | 61.529 | −50.323 | 4.709 | 1.00 | 29.45 | A | C |
| ATOM | 1435 | CB | LEU | A | 113 | 61.443 | −50.353 | 6.241 | 1.00 | 29.86 | A | C |
| ATOM | 1438 | CG | LEU | A | 113 | 60.553 | −49.263 | 6.868 | 1.00 | 31.38 | A | C |
| ATOM | 1440 | CD1 | LEU | A | 113 | 59.109 | −49.437 | 6.427 | 1.00 | 29.65 | A | C |
| ATOM | 1444 | CD2 | LEU | A | 113 | 60.631 | −49.299 | 8.378 | 1.00 | 33.60 | A | C |
| ATOM | 1448 | C | LEU | A | 113 | 62.017 | −48.954 | 4.268 | 1.00 | 28.16 | A | C |
| ATOM | 1449 | O | LEU | A | 113 | 61.237 | −48.138 | 3.810 | 1.00 | 29.40 | A | O |
| ATOM | 1451 | N | HIS | A | 114 | 63.308 | −48.706 | 4.417 | 1.00 | 27.25 | A | N |
| ATOM | 1452 | CA | HIS | A | 114 | 63.902 | −47.461 | 3.960 | 1.00 | 28.38 | A | C |
| ATOM | 1454 | CB | HIS | A | 114 | 65.418 | −47.448 | 4.175 | 1.00 | 29.85 | A | C |
| ATOM | 1457 | CG | HIS | A | 114 | 66.073 | −46.214 | 3.663 | 1.00 | 29.52 | A | C |
| ATOM | 1458 | ND1 | HIS | A | 114 | 65.529 | −44.961 | 3.846 | 1.00 | 36.46 | A | N |
| ATOM | 1460 | CE1 | HIS | A | 114 | 66.310 | −44.057 | 3.281 | 1.00 | 35.11 | A | C |
| ATOM | 1462 | NE2 | HIS | A | 114 | 67.322 | −44.682 | 2.711 | 1.00 | 36.38 | A | N |
| ATOM | 1464 | CD2 | HIS | A | 114 | 67.197 | −46.033 | 2.937 | 1.00 | 36.40 | A | C |
| ATOM | 1466 | C | HIS | A | 114 | 63.595 | −47.220 | 2.493 | 1.00 | 27.08 | A | C |
| ATOM | 1467 | O | HIS | A | 114 | 63.089 | −46.166 | 2.127 | 1.00 | 25.36 | A | O |
| ATOM | 1469 | N | GLY | A | 115 | 63.884 | −48.214 | 1.665 | 1.00 | 27.32 | A | N |
| ATOM | 1470 | CA | GLY | A | 115 | 63.647 | −48.120 | 0.234 | 1.00 | 25.75 | A | C |
| ATOM | 1473 | C | GLY | A | 115 | 62.184 | −47.904 | −0.102 | 1.00 | 26.39 | A | C |
| ATOM | 1474 | O | GLY | A | 115 | 61.858 | −47.150 | −1.041 | 1.00 | 26.71 | A | O |
| ATOM | 1476 | N | THR | A | 116 | 61.306 | −48.567 | 0.657 | 1.00 | 24.29 | A | N |
| ATOM | 1477 | CA | THR | A | 116 | 59.865 | −48.470 | 0.431 | 1.00 | 24.57 | A | C |
| ATOM | 1479 | CB | THR | A | 116 | 59.111 | −49.555 | 1.168 | 1.00 | 25.44 | A | C |
| ATOM | 1481 | OG1 | THR | A | 116 | 59.620 | −50.825 | 0.738 | 1.00 | 27.83 | A | O |
| ATOM | 1483 | CG2 | THR | A | 116 | 57.589 | −49.476 | 0.868 | 1.00 | 20.09 | A | C |
| ATOM | 1487 | C | THR | A | 116 | 59.307 | −47.113 | 0.832 | 1.00 | 25.48 | A | C |
| ATOM | 1488 | O | THR | A | 116 | 58.594 | −46.491 | 0.046 | 1.00 | 25.53 | A | O |
| ATOM | 1490 | N | ALA | A | 117 | 59.659 | −46.647 | 2.028 | 1.00 | 23.44 | A | N |
| ATOM | 1491 | CA | ALA | A | 117 | 59.194 | −45.356 | 2.505 | 1.00 | 24.19 | A | C |
| ATOM | 1493 | CB | ALA | A | 117 | 59.478 | −45.193 | 4.016 | 1.00 | 23.46 | A | C |
| ATOM | 1497 | C | ALA | A | 117 | 59.791 | −44.201 | 1.699 | 1.00 | 24.21 | A | C |
| ATOM | 1498 | O | ALA | A | 117 | 59.112 | −43.225 | 1.436 | 1.00 | 23.16 | A | O |
| ATOM | 1500 | N | LEU | A | 118 | 61.048 | −44.301 | 1.286 | 1.00 | 24.65 | A | N |
| ATOM | 1501 | CA | LEU | A | 118 | 61.631 | −43.222 | 0.443 | 1.00 | 25.43 | A | C |
| ATOM | 1503 | CB | LEU | A | 118 | 63.157 | −43.356 | 0.339 | 1.00 | 24.64 | A | C |
| ATOM | 1506 | CG | LEU | A | 118 | 63.924 | −42.343 | −0.519 | 1.00 | 29.58 | A | C |
| ATOM | 1508 | CD1 | LEU | A | 118 | 63.697 | −40.923 | −0.069 | 1.00 | 22.30 | A | C |
| ATOM | 1512 | CD2 | LEU | A | 118 | 65.403 | −42.690 | −0.477 | 1.00 | 24.34 | A | C |
| ATOM | 1516 | C | LEU | A | 118 | 60.986 | −43.203 | −0.936 | 1.00 | 24.40 | A | C |
| ATOM | 1517 | O | LEU | A | 118 | 60.497 | −42.172 | −1.409 | 1.00 | 24.21 | A | O |
| ATOM | 1519 | N | SER | A | 119 | 60.943 | −44.362 | −1.580 | 1.00 | 25.13 | A | N |
| ATOM | 1520 | CA | SER | A | 119 | 60.368 | −44.416 | −2.916 | 1.00 | 23.95 | A | C |
| ATOM | 1522 | CB | SER | A | 119 | 60.589 | −45.779 | −3.563 | 1.00 | 25.32 | A | C |
| ATOM | 1525 | OG | SER | A | 119 | 59.934 | −46.812 | −2.867 | 1.00 | 26.72 | A | O |
| ATOM | 1527 | C | SER | A | 119 | 58.892 | −44.054 | −2.902 | 1.00 | 23.29 | A | C |
| ATOM | 1528 | O | SER | A | 119 | 58.429 | −43.326 | −3.770 | 1.00 | 23.89 | A | O |
| ATOM | 1530 | N | PHE | A | 120 | 58.162 | −44.537 | −1.903 | 1.00 | 22.65 | A | N |
| ATOM | 1531 | CA | PHE | A | 120 | 56.760 | −44.152 | −1.715 | 1.00 | 22.34 | A | C |
| ATOM | 1533 | CB | PHE | A | 120 | 56.202 | −44.766 | −0.422 | 1.00 | 22.44 | A | C |
| ATOM | 1536 | CG | PHE | A | 120 | 54.758 | −44.427 | −0.154 | 1.00 | 23.67 | A | C |
| ATOM | 1537 | CD1 | PHE | A | 120 | 53.752 | −45.312 | −0.480 | 1.00 | 26.16 | A | C |
| ATOM | 1539 | CE1 | PHE | A | 120 | 52.413 | −45.001 | −0.220 | 1.00 | 26.81 | A | C |
| ATOM | 1541 | CZ | PHE | A | 120 | 52.092 | −43.791 | 0.378 | 1.00 | 23.94 | A | C |
| ATOM | 1543 | CE2 | PHE | A | 120 | 53.089 | −42.932 | 0.722 | 1.00 | 23.73 | A | C |
| ATOM | 1545 | CD2 | PHE | A | 120 | 54.414 | −43.240 | 0.454 | 1.00 | 25.92 | A | C |
| ATOM | 1547 | C | PHE | A | 120 | 56.606 | −42.630 | −1.669 | 1.00 | 20.61 | A | C |
| ATOM | 1548 | O | PHE | A | 120 | 55.759 | −42.066 | −2.345 | 1.00 | 19.01 | A | O |
| ATOM | 1550 | N | ARG | A | 121 | 57.410 | −41.966 | −0.850 | 1.00 | 19.18 | A | N |
| ATOM | 1551 | CA | ARG | A | 121 | 57.326 | −40.506 | −0.775 | 1.00 | 20.59 | A | C |

TABLE 4-2-continued

Coordinates of *P. alba* IspS

| | | | | | | | | | | | | |
|---|---|---|---|---|---|---|---|---|---|---|---|---|
| ATOM | 1553 | CB | ARG | A | 121 | 58.263 | −39.962 | 0.293 | 1.00 | 20.27 | A | C |
| ATOM | 1556 | CG | ARG | A | 121 | 58.293 | −38.443 | 0.373 | 1.00 | 20.89 | A | C |
| ATOM | 1559 | CD | ARG | A | 121 | 58.902 | −37.979 | 1.690 | 1.00 | 25.20 | A | C |
| ATOM | 1562 | NE | ARG | A | 121 | 60.315 | −38.344 | 1.819 | 1.00 | 23.57 | A | N |
| ATOM | 1564 | CZ | ARG | A | 121 | 61.313 | −37.708 | 1.209 | 1.00 | 23.54 | A | C |
| ATOM | 1565 | NH1 | ARG | A | 121 | 61.068 | −36.674 | 0.414 | 1.00 | 25.58 | A | N |
| ATOM | 1568 | NH2 | ARG | A | 121 | 62.566 | −38.101 | 1.399 | 1.00 | 26.88 | A | N |
| ATOM | 1571 | C | ARG | A | 121 | 57.648 | −39.851 | −2.127 | 1.00 | 19.48 | A | C |
| ATOM | 1572 | O | ARG | A | 121 | 56.909 | −38.997 | −2.609 | 1.00 | 19.29 | A | O |
| ATOM | 1574 | N | LEU | A | 122 | 58.759 | −40.238 | −2.730 | 1.00 | 18.56 | A | N |
| ATOM | 1575 | CA | LEU | A | 122 | 59.159 | −39.613 | −4.017 | 1.00 | 20.57 | A | C |
| ATOM | 1577 | CB | LEU | A | 122 | 60.537 | −40.098 | −4.452 | 1.00 | 18.26 | A | C |
| ATOM | 1580 | CG | LEU | A | 122 | 61.666 | −39.788 | −3.466 | 1.00 | 21.60 | A | C |
| ATOM | 1582 | CD1 | LEU | A | 122 | 62.946 | −40.470 | −3.896 | 1.00 | 21.70 | A | C |
| ATOM | 1586 | CD2 | LEU | A | 122 | 61.855 | −38.314 | −3.393 | 1.00 | 16.48 | A | C |
| ATOM | 1590 | C | LEU | A | 122 | 58.121 | −39.881 | −5.129 | 1.00 | 20.63 | A | C |
| ATOM | 1591 | O | LEU | A | 122 | 57.780 | −39.002 | −5.914 | 1.00 | 21.52 | A | O |
| ATOM | 1593 | N | LEU | A | 123 | 57.594 | −41.088 | −5.167 | 1.00 | 20.62 | A | N |
| ATOM | 1594 | CA | LEU | A | 123 | 56.623 | −41.439 | −6.195 | 1.00 | 20.75 | A | C |
| ATOM | 1596 | CB | LEU | A | 123 | 56.330 | −42.919 | −6.128 | 1.00 | 20.28 | A | C |
| ATOM | 1599 | CG | LEU | A | 123 | 57.412 | −43.829 | −6.735 | 1.00 | 22.58 | A | C |
| ATOM | 1601 | CD1 | LEU | A | 123 | 57.134 | −45.289 | −6.354 | 1.00 | 20.41 | A | C |
| ATOM | 1605 | CD2 | LEU | A | 123 | 57.468 | −43.716 | −8.242 | 1.00 | 19.56 | A | C |
| ATOM | 1609 | C | LEU | A | 123 | 55.345 | −40.604 | −6.046 | 1.00 | 21.54 | A | C |
| ATOM | 1610 | O | LEU | A | 123 | 54.858 | −39.995 | −7.011 | 1.00 | 20.27 | A | O |
| ATOM | 1612 | N | ARG | A | 124 | 54.820 | −40.534 | −4.829 | 1.00 | 22.21 | A | N |
| ATOM | 1613 | CA | ARG | A | 124 | 53.585 | −39.797 | −4.615 | 1.00 | 20.97 | A | C |
| ATOM | 1615 | CB | ARG | A | 124 | 52.987 | −40.096 | −3.246 | 1.00 | 19.35 | A | C |
| ATOM | 1618 | CG | ARG | A | 124 | 51.792 | −39.228 | −2.932 | 1.00 | 23.37 | A | C |
| ATOM | 1621 | CD | ARG | A | 124 | 51.015 | −39.762 | −1.753 | 1.00 | 23.81 | A | C |
| ATOM | 1624 | NE | ARG | A | 124 | 50.298 | −41.008 | −2.048 | 1.00 | 20.90 | A | N |
| ATOM | 1626 | CZ | ARG | A | 124 | 49.550 | −41.652 | −1.158 | 1.00 | 23.68 | A | C |
| ATOM | 1627 | NH1 | ARG | A | 124 | 49.450 | −41.192 | 0.085 | 1.00 | 19.23 | A | N |
| ATOM | 1630 | NH2 | ARG | A | 124 | 48.900 | −42.746 | −1.502 | 1.00 | 20.41 | A | N |
| ATOM | 1633 | C | ARG | A | 124 | 53.831 | −38.321 | −4.814 | 1.00 | 18.12 | A | C |
| ATOM | 1634 | O | ARG | A | 124 | 53.021 | −37.627 | −5.402 | 1.00 | 21.48 | A | O |
| ATOM | 1636 | N | GLN | A | 125 | 54.959 | −37.831 | −4.343 | 1.00 | 20.20 | A | N |
| ATOM | 1637 | CA | GLN | A | 125 | 55.321 | −36.430 | −4.584 | 1.00 | 21.03 | A | C |
| ATOM | 1639 | CB | GLN | A | 125 | 56.744 | −36.147 | −4.080 | 1.00 | 21.65 | A | C |
| ATOM | 1642 | CG | GLN | A | 125 | 57.280 | −34.765 | −4.498 | 1.00 | 20.36 | A | C |
| ATOM | 1645 | CD | GLN | A | 125 | 58.726 | −34.527 | −4.121 | 1.00 | 26.60 | A | C |
| ATOM | 1646 | OE1 | GLN | A | 125 | 59.381 | −35.390 | −3.526 | 1.00 | 21.64 | A | O |
| ATOM | 1647 | NE2 | GLN | A | 125 | 59.247 | −33.352 | −4.492 | 1.00 | 18.29 | A | N |
| ATOM | 1650 | C | GLN | A | 125 | 55.266 | −36.089 | −6.080 | 1.00 | 21.86 | A | C |
| ATOM | 1651 | O | GLN | A | 125 | 54.826 | −34.999 | −6.477 | 1.00 | 23.50 | A | O |
| ATOM | 1653 | N | HIS | A | 126 | 55.739 | −37.011 | −6.912 | 1.00 | 22.17 | A | N |
| ATOM | 1654 | CA | HIS | A | 126 | 55.787 | −36.760 | −8.350 | 1.00 | 23.23 | A | C |
| ATOM | 1656 | CB | HIS | A | 126 | 57.100 | −37.293 | −8.904 | 1.00 | 23.41 | A | C |
| ATOM | 1659 | CG | HIS | A | 126 | 58.250 | −36.415 | −8.563 | 1.00 | 20.04 | A | C |
| ATOM | 1660 | ND1 | HIS | A | 126 | 58.516 | −35.260 | −9.256 | 1.00 | 26.32 | A | N |
| ATOM | 1662 | CE1 | HIS | A | 126 | 59.541 | −34.646 | −8.700 | 1.00 | 22.03 | A | C |
| ATOM | 1664 | NE2 | HIS | A | 126 | 59.942 | −35.359 | −7.667 | 1.00 | 19.54 | A | N |
| ATOM | 1666 | CD2 | HIS | A | 126 | 59.139 | −36.463 | −7.548 | 1.00 | 18.20 | A | C |
| ATOM | 1668 | C | HIS | A | 126 | 54.568 | −37.274 | −9.096 | 1.00 | 25.26 | A | C |
| ATOM | 1669 | O | HIS | A | 126 | 54.602 | −37.438 | −10.311 | 1.00 | 26.07 | A | O |
| ATOM | 1671 | N | GLY | A | 127 | 53.479 | −37.528 | −8.371 | 1.00 | 25.78 | A | N |
| ATOM | 1672 | CA | GLY | A | 127 | 52.198 | −37.783 | −9.033 | 1.00 | 24.01 | A | C |
| ATOM | 1675 | C | GLY | A | 127 | 51.898 | −39.232 | −9.348 | 1.00 | 23.73 | A | C |
| ATOM | 1676 | O | GLY | A | 127 | 50.879 | −39.513 | −9.937 | 1.00 | 28.90 | A | O |
| ATOM | 1678 | N | PHE | A | 128 | 52.763 | −40.163 | −8.977 | 1.00 | 23.33 | A | N |
| ATOM | 1679 | CA | PHE | A | 128 | 52.490 | −41.563 | −9.251 | 1.00 | 25.32 | A | C |
| ATOM | 1681 | CB | PHE | A | 128 | 53.775 | −42.381 | −9.271 | 1.00 | 23.93 | A | C |
| ATOM | 1684 | CG | PHE | A | 128 | 54.725 | −42.003 | −10.366 | 1.00 | 26.62 | A | C |
| ATOM | 1685 | CD1 | PHE | A | 128 | 54.739 | −42.698 | −11.555 | 1.00 | 27.05 | A | C |
| ATOM | 1687 | CE1 | PHE | A | 128 | 55.633 | −42.369 | −12.551 | 1.00 | 30.59 | A | C |
| ATOM | 1689 | CZ | PHE | A | 128 | 56.513 | −41.321 | −12.368 | 1.00 | 33.45 | A | C |
| ATOM | 1691 | CE2 | PHE | A | 128 | 56.500 | −40.627 | −11.187 | 1.00 | 30.11 | A | C |
| ATOM | 1693 | CD2 | PHE | A | 128 | 55.629 | −40.979 | −10.194 | 1.00 | 25.68 | A | C |
| ATOM | 1695 | C | PHE | A | 128 | 51.535 | −42.136 | −8.193 | 1.00 | 28.35 | A | C |
| ATOM | 1696 | O | PHE | A | 128 | 51.473 | −41.657 | −7.062 | 1.00 | 28.35 | A | O |
| ATOM | 1698 | N | GLU | A | 129 | 50.828 | −43.178 | −8.584 | 1.00 | 30.58 | A | N |
| ATOM | 1699 | CA | GLU | A | 129 | 49.896 | −43.880 | −7.739 | 1.00 | 33.23 | A | C |
| ATOM | 1701 | CB | GLU | A | 129 | 48.816 | −44.578 | −8.589 | 1.00 | 34.45 | A | C |
| ATOM | 1704 | CG | GLU | A | 129 | 47.751 | −43.588 | −9.137 | 1.00 | 47.35 | A | C |
| ATOM | 1707 | CD | GLU | A | 129 | 46.460 | −44.250 | −9.690 | 1.00 | 59.81 | A | C |
| ATOM | 1708 | OE1 | GLU | A | 129 | 45.701 | −43.545 | −10.403 | 1.00 | 60.68 | A | O |
| ATOM | 1709 | OE2 | GLU | A | 129 | 46.191 | −45.448 | −9.409 | 1.00 | 66.05 | A | O |
| ATOM | 1710 | C | GLU | A | 129 | 50.630 | −44.910 | −6.913 | 1.00 | 30.73 | A | C |

TABLE 4-2-continued

Coordinates of *P. alba* IspS

| | | | | | | | | | | | | |
|---|---|---|---|---|---|---|---|---|---|---|---|---|
| ATOM | 1711 | O | GLU | A | 129 | 51.213 | −45.846 | −7.455 | 1.00 | 30.68 | A | O |
| ATOM | 1713 | N | VAL | A | 130 | 50.610 | −44.735 | −5.601 | 1.00 | 27.24 | A | N |
| ATOM | 1714 | CA | VAL | A | 130 | 51.116 | −45.775 | −4.718 | 1.00 | 26.66 | A | C |
| ATOM | 1716 | CB | VAL | A | 130 | 52.486 | −45.414 | −4.131 | 1.00 | 26.82 | A | C |
| ATOM | 1718 | CG1 | VAL | A | 130 | 53.534 | −45.415 | −5.233 | 1.00 | 26.47 | A | C |
| ATOM | 1722 | CG2 | VAL | A | 130 | 52.439 | −44.045 | −3.428 | 1.00 | 22.87 | A | C |
| ATOM | 1726 | C | VAL | A | 130 | 50.101 | −45.976 | −3.618 | 1.00 | 25.49 | A | C |
| ATOM | 1727 | O | VAL | A | 130 | 49.328 | −45.069 | −3.314 | 1.00 | 23.94 | A | O |
| ATOM | 1729 | N | SER | A | 131 | 50.094 | −47.168 | −3.035 | 1.00 | 25.58 | A | N |
| ATOM | 1730 | CA | SER | A | 131 | 49.112 | −47.518 | −2.021 | 1.00 | 25.94 | A | C |
| ATOM | 1732 | CB | SER | A | 131 | 48.356 | −48.780 | −2.443 | 1.00 | 29.50 | A | C |
| ATOM | 1735 | OG | SER | A | 131 | 47.847 | −49.475 | −1.304 | 1.00 | 28.83 | A | O |
| ATOM | 1737 | C | SER | A | 131 | 49.764 | −47.783 | −0.707 | 1.00 | 23.83 | A | C |
| ATOM | 1738 | O | SER | A | 131 | 50.909 | −48.214 | −0.668 | 1.00 | 24.97 | A | O |
| ATOM | 1740 | N | GLN | A | 132 | 49.015 | −47.581 | 0.375 | 1.00 | 24.32 | A | N |
| ATOM | 1741 | CA | GLN | A | 132 | 49.526 | −47.858 | 1.733 | 1.00 | 25.61 | A | C |
| ATOM | 1743 | CB | GLN | A | 132 | 48.516 | −47.393 | 2.800 | 1.00 | 24.08 | A | C |
| ATOM | 1746 | CG | GLN | A | 132 | 47.161 | −48.125 | 2.806 | 1.00 | 27.85 | A | C |
| ATOM | 1749 | CD | GLN | A | 132 | 46.283 | −47.760 | 4.011 | 1.00 | 25.79 | A | C |
| ATOM | 1750 | OE1 | GLN | A | 132 | 46.644 | −46.918 | 4.824 | 1.00 | 26.01 | A | O |
| ATOM | 1751 | NE2 | GLN | A | 132 | 45.129 | −48.398 | 4.118 | 1.00 | 27.24 | A | N |
| ATOM | 1754 | C | GLN | A | 132 | 49.904 | −49.353 | 1.924 | 1.00 | 26.55 | A | C |
| ATOM | 1755 | O | GLN | A | 132 | 50.751 | −49.702 | 2.742 | 1.00 | 23.45 | A | O |
| ATOM | 1757 | N | GLU | A | 133 | 49.299 | −50.236 | 1.147 | 1.00 | 26.74 | A | N |
| ATOM | 1758 | CA | GLU | A | 133 | 49.661 | −51.643 | 1.243 | 1.00 | 30.43 | A | C |
| ATOM | 1760 | CB | GLU | A | 133 | 48.627 | −52.582 | 0.584 | 1.00 | 31.92 | A | C |
| ATOM | 1763 | CG | GLU | A | 133 | 48.242 | −52.326 | −0.834 | 1.00 | 41.00 | A | C |
| ATOM | 1766 | CD | GLU | A | 133 | 46.890 | −52.992 | −1.251 | 1.00 | 47.38 | A | C |
| ATOM | 1767 | OE1 | GLU | A | 133 | 45.793 | −52.388 | −1.115 | 1.00 | 48.99 | A | O |
| ATOM | 1768 | OE2 | GLU | A | 133 | 46.944 | −54.114 | −1.767 | 1.00 | 48.11 | A | O |
| ATOM | 1769 | C | GLU | A | 133 | 51.104 | −51.920 | 0.816 | 1.00 | 30.03 | A | C |
| ATOM | 1770 | O | GLU | A | 133 | 51.634 | −52.980 | 1.099 | 1.00 | 30.56 | A | O |
| ATOM | 1772 | N | ALA | A | 134 | 51.779 | −50.944 | 0.220 | 1.00 | 30.33 | A | N |
| ATOM | 1773 | CA | ALA | A | 134 | 53.229 | −51.050 | 0.026 | 1.00 | 29.74 | A | C |
| ATOM | 1775 | CB | ALA | A | 134 | 53.759 | −49.793 | −0.603 | 1.00 | 28.04 | A | C |
| ATOM | 1779 | C | ALA | A | 134 | 53.976 | −51.319 | 1.333 | 1.00 | 30.69 | A | C |
| ATOM | 1780 | O | ALA | A | 134 | 55.073 | −51.845 | 1.323 | 1.00 | 31.48 | A | O |
| ATOM | 1782 | N | PHE | A | 135 | 53.377 | −50.946 | 2.454 | 1.00 | 31.85 | A | N |
| ATOM | 1783 | CA | PHE | A | 135 | 53.987 | −51.134 | 3.762 | 1.00 | 31.97 | A | C |
| ATOM | 1785 | CB | PHE | A | 135 | 53.673 | −49.906 | 4.633 | 1.00 | 29.56 | A | C |
| ATOM | 1788 | CG | PHE | A | 135 | 54.296 | −48.619 | 4.122 | 1.00 | 28.98 | A | C |
| ATOM | 1789 | CD1 | PHE | A | 135 | 53.549 | −47.697 | 3.402 | 1.00 | 24.38 | A | C |
| ATOM | 1791 | CE1 | PHE | A | 135 | 54.120 | −46.519 | 2.916 | 1.00 | 21.90 | A | C |
| ATOM | 1793 | CZ | PHE | A | 135 | 55.450 | −46.254 | 3.153 | 1.00 | 24.74 | A | C |
| ATOM | 1795 | CE2 | PHE | A | 135 | 56.215 | −47.169 | 3.850 | 1.00 | 26.09 | A | C |
| ATOM | 1797 | CD2 | PHE | A | 135 | 55.635 | −48.350 | 4.336 | 1.00 | 28.54 | A | C |
| ATOM | 1799 | C | PHE | A | 135 | 53.522 | −52.442 | 4.470 | 1.00 | 34.24 | A | C |
| ATOM | 1800 | O | PHE | A | 135 | 53.953 | −52.727 | 5.590 | 1.00 | 33.24 | A | O |
| ATOM | 1802 | N | SER | A | 136 | 52.667 | −53.235 | 3.825 | 1.00 | 35.02 | A | N |
| ATOM | 1803 | CA | SER | A | 136 | 52.050 | −54.394 | 4.506 | 1.00 | 37.80 | A | C |
| ATOM | 1805 | CB | SER | A | 136 | 50.943 | −55.039 | 3.654 | 1.00 | 37.47 | A | C |
| ATOM | 1808 | OG | SER | A | 136 | 51.480 | −55.711 | 2.531 | 1.00 | 37.80 | A | O |
| ATOM | 1810 | C | SER | A | 136 | 53.065 | −55.448 | 4.966 | 1.00 | 38.21 | A | C |
| ATOM | 1811 | O | SER | A | 136 | 52.917 | −56.015 | 6.045 | 1.00 | 40.62 | A | O |
| ATOM | 1813 | N | GLY | A | 137 | 54.120 | −55.662 | 4.188 | 1.00 | 38.95 | A | N |
| ATOM | 1814 | CA | GLY | A | 137 | 55.167 | −56.606 | 4.562 | 1.00 | 38.95 | A | C |
| ATOM | 1817 | C | GLY | A | 137 | 56.057 | −56.211 | 5.738 | 1.00 | 39.26 | A | C |
| ATOM | 1818 | O | GLY | A | 137 | 57.001 | −56.924 | 6.045 | 1.00 | 39.28 | A | O |
| ATOM | 1820 | N | PHE | A | 138 | 55.770 | −55.096 | 6.405 | 1.00 | 39.21 | A | N |
| ATOM | 1821 | CA | PHE | A | 138 | 56.593 | −54.643 | 7.532 | 1.00 | 40.53 | A | C |
| ATOM | 1823 | CB | PHE | A | 138 | 57.131 | −53.223 | 7.260 | 1.00 | 38.00 | A | C |
| ATOM | 1826 | CG | PHE | A | 138 | 57.991 | −53.154 | 6.039 | 1.00 | 34.18 | A | C |
| ATOM | 1827 | CD1 | PHE | A | 138 | 59.251 | −53.731 | 6.040 | 1.00 | 34.73 | A | C |
| ATOM | 1829 | CE1 | PHE | A | 138 | 60.049 | −53.705 | 4.893 | 1.00 | 34.21 | A | C |
| ATOM | 1831 | CZ | PHE | A | 138 | 59.572 | −53.132 | 3.736 | 1.00 | 30.84 | A | C |
| ATOM | 1833 | CE2 | PHE | A | 138 | 58.307 | −52.565 | 3.720 | 1.00 | 32.61 | A | C |
| ATOM | 1835 | CD2 | PHE | A | 138 | 57.522 | −52.590 | 4.867 | 1.00 | 33.77 | A | C |
| ATOM | 1837 | C | PHE | A | 138 | 55.837 | −54.727 | 8.856 | 1.00 | 43.36 | A | C |
| ATOM | 1838 | O | PHE | A | 138 | 56.261 | −54.163 | 9.862 | 1.00 | 43.05 | A | O |
| ATOM | 1840 | N | LYS | A | 139 | 54.727 | −55.455 | 8.852 | 1.00 | 47.23 | A | N |
| ATOM | 1841 | CA | LYS | A | 139 | 53.884 | −55.562 | 10.029 | 1.00 | 51.13 | A | C |
| ATOM | 1843 | CB | LYS | A | 139 | 52.457 | −55.086 | 9.696 | 1.00 | 51.78 | A | C |
| ATOM | 1846 | CG | LYS | A | 139 | 52.392 | −53.546 | 9.534 | 1.00 | 54.28 | A | C |
| ATOM | 1849 | CD | LYS | A | 139 | 51.184 | −53.029 | 8.748 | 1.00 | 61.08 | A | C |
| ATOM | 1852 | CE | LYS | A | 139 | 49.951 | −52.824 | 9.631 | 1.00 | 64.23 | A | C |
| ATOM | 1855 | NZ | LYS | A | 139 | 50.121 | −51.700 | 10.603 | 1.00 | 59.56 | A | N |
| ATOM | 1859 | C | LYS | A | 139 | 53.964 | −56.984 | 10.582 | 1.00 | 53.19 | A | C |
| ATOM | 1860 | O | LYS | A | 139 | 54.306 | −57.915 | 9.856 | 1.00 | 54.52 | A | O |

TABLE 4-2-continued

Coordinates of *P. alba* IspS

| | | | | | | | | | | | | |
|---|---|---|---|---|---|---|---|---|---|---|---|---|
| ATOM | 1862 | N | ASP | A | 140 | 53.715 | −57.124 | 11.886 | 1.00 | 55.49 | A | N |
| ATOM | 1863 | CA | ASP | A | 140 | 53.821 | −58.410 | 12.591 | 1.00 | 56.32 | A | C |
| ATOM | 1865 | CB | ASP | A | 140 | 54.282 | −58.194 | 14.050 | 1.00 | 56.20 | A | C |
| ATOM | 1868 | CG | ASP | A | 140 | 53.262 | −57.437 | 14.902 | 1.00 | 53.48 | A | C |
| ATOM | 1869 | OD1 | ASP | A | 140 | 52.109 | −57.244 | 14.468 | 1.00 | 47.36 | A | O |
| ATOM | 1870 | OD2 | ASP | A | 140 | 53.627 | −57.019 | 16.016 | 1.00 | 50.19 | A | O |
| ATOM | 1871 | C | ASP | A | 140 | 52.503 | −59.184 | 12.535 | 1.00 | 58.61 | A | C |
| ATOM | 1872 | O | ASP | A | 140 | 51.591 | −58.814 | 11.787 | 1.00 | 57.83 | A | O |
| ATOM | 1874 | N | GLN | A | 141 | 52.409 | −60.260 | 13.321 | 1.00 | 61.75 | A | N |
| ATOM | 1875 | CA | GLN | A | 141 | 51.191 | −61.083 | 13.382 | 1.00 | 63.46 | A | C |
| ATOM | 1877 | CB | GLN | A | 141 | 51.350 | −62.206 | 14.419 | 1.00 | 64.54 | A | C |
| ATOM | 1880 | CG | GLN | A | 141 | 52.401 | −63.260 | 14.080 | 1.00 | 67.62 | A | C |
| ATOM | 1883 | CD | GLN | A | 141 | 52.236 | −64.534 | 14.912 | 1.00 | 71.72 | A | C |
| ATOM | 1884 | OE1 | GLN | A | 141 | 51.201 | −65.200 | 14.845 | 1.00 | 71.94 | A | O |
| ATOM | 1885 | NE2 | GLN | A | 141 | 53.256 | −64.873 | 15.698 | 1.00 | 69.09 | A | N |
| ATOM | 1888 | C | GLN | A | 141 | 49.927 | −60.264 | 13.708 | 1.00 | 63.18 | A | C |
| ATOM | 1889 | O | GLN | A | 141 | 48.854 | −60.539 | 13.161 | 1.00 | 63.42 | A | O |
| ATOM | 1891 | N | ASN | A | 142 | 50.071 | −59.265 | 14.585 | 1.00 | 62.04 | A | N |
| ATOM | 1892 | CA | ASN | A | 142 | 48.948 | −58.447 | 15.067 | 1.00 | 61.76 | A | C |
| ATOM | 1894 | CB | ASN | A | 142 | 49.211 | −58.041 | 16.521 | 1.00 | 62.74 | A | C |
| ATOM | 1897 | CG | ASN | A | 142 | 49.124 | −59.216 | 17.476 | 1.00 | 64.28 | A | C |
| ATOM | 1898 | OD1 | ASN | A | 142 | 48.147 | −59.967 | 17.461 | 1.00 | 65.28 | A | O |
| ATOM | 1899 | ND2 | ASN | A | 142 | 50.143 | −59.379 | 18.314 | 1.00 | 61.18 | A | N |
| ATOM | 1902 | C | ASN | A | 142 | 48.609 | −57.182 | 14.259 | 1.00 | 60.73 | A | C |
| ATOM | 1903 | O | ASN | A | 142 | 47.790 | −56.374 | 14.696 | 1.00 | 60.76 | A | O |
| ATOM | 1905 | N | GLY | A | 143 | 49.223 | −57.006 | 13.094 | 1.00 | 58.94 | A | N |
| ATOM | 1906 | CA | GLY | A | 143 | 48.969 | −55.823 | 12.273 | 1.00 | 58.11 | A | C |
| ATOM | 1909 | C | GLY | A | 143 | 49.577 | −54.533 | 12.818 | 1.00 | 56.81 | A | C |
| ATOM | 1910 | O | GLY | A | 143 | 49.040 | −53.451 | 12.596 | 1.00 | 56.75 | A | O |
| ATOM | 1912 | N | ASN | A | 144 | 50.684 | −54.658 | 13.551 | 1.00 | 54.34 | A | N |
| ATOM | 1913 | CA | ASN | A | 144 | 51.452 | −53.517 | 14.036 | 1.00 | 51.31 | A | C |
| ATOM | 1915 | CB | ASN | A | 144 | 51.523 | −53.532 | 15.561 | 1.00 | 50.99 | A | C |
| ATOM | 1918 | CG | ASN | A | 144 | 50.156 | −53.394 | 16.203 | 1.00 | 54.98 | A | C |
| ATOM | 1919 | OD1 | ASN | A | 144 | 49.390 | −52.496 | 15.861 | 1.00 | 57.50 | A | O |
| ATOM | 1920 | ND2 | ASN | A | 144 | 49.836 | −54.291 | 17.129 | 1.00 | 54.41 | A | N |
| ATOM | 1923 | C | ASN | A | 144 | 52.842 | −53.594 | 13.421 | 1.00 | 47.91 | A | C |
| ATOM | 1924 | O | ASN | A | 144 | 53.314 | −54.678 | 13.096 | 1.00 | 45.74 | A | O |
| ATOM | 1926 | N | PHE | A | 145 | 53.487 | −52.450 | 13.225 | 1.00 | 45.60 | A | N |
| ATOM | 1927 | CA | PHE | A | 145 | 54.827 | −52.432 | 12.636 | 1.00 | 42.79 | A | C |
| ATOM | 1929 | CB | PHE | A | 145 | 55.315 | −50.995 | 12.429 | 1.00 | 41.21 | A | C |
| ATOM | 1932 | CG | PHE | A | 145 | 54.767 | −50.342 | 11.190 | 1.00 | 34.59 | A | C |
| ATOM | 1933 | CD1 | PHE | A | 145 | 53.612 | −49.583 | 11.241 | 1.00 | 28.50 | A | C |
| ATOM | 1935 | CE1 | PHE | A | 145 | 53.097 | −48.999 | 10.107 | 1.00 | 33.37 | A | C |
| ATOM | 1937 | CZ | PHE | A | 145 | 53.749 | −49.159 | 8.890 | 1.00 | 34.40 | A | C |
| ATOM | 1939 | CE2 | PHE | A | 145 | 54.909 | −49.912 | 8.827 | 1.00 | 36.36 | A | C |
| ATOM | 1941 | CD2 | PHE | A | 145 | 55.403 | −50.508 | 9.971 | 1.00 | 33.35 | A | C |
| ATOM | 1943 | C | PHE | A | 145 | 55.811 | −53.220 | 13.509 | 1.00 | 43.43 | A | C |
| ATOM | 1944 | O | PHE | A | 145 | 55.739 | −53.168 | 14.740 | 1.00 | 39.77 | A | O |
| ATOM | 1946 | N | LEU | A | 146 | 56.719 | −53.949 | 12.862 | 1.00 | 45.03 | A | N |
| ATOM | 1947 | CA | LEU | A | 146 | 57.658 | −54.811 | 13.574 | 1.00 | 47.52 | A | C |
| ATOM | 1949 | CB | LEU | A | 146 | 58.571 | −55.562 | 12.600 | 1.00 | 48.77 | A | C |
| ATOM | 1952 | CG | LEU | A | 146 | 57.939 | −56.744 | 11.854 | 1.00 | 51.30 | A | C |
| ATOM | 1954 | CD1 | LEU | A | 146 | 58.802 | −57.157 | 10.656 | 1.00 | 53.93 | A | C |
| ATOM | 1958 | CD2 | LEU | A | 146 | 57.724 | −57.920 | 12.803 | 1.00 | 50.78 | A | C |
| ATOM | 1962 | C | LEU | A | 146 | 58.503 | −53.994 | 14.521 | 1.00 | 47.29 | A | C |
| ATOM | 1963 | O | LEU | A | 146 | 59.085 | −53.004 | 14.122 | 1.00 | 46.58 | A | O |
| ATOM | 1965 | N | GLU | A | 147 | 58.546 | −54.418 | 15.778 | 1.00 | 48.15 | A | N |
| ATOM | 1966 | CA | GLU | A | 147 | 59.333 | −53.766 | 16.818 | 1.00 | 49.25 | A | C |
| ATOM | 1968 | CB | GLU | A | 147 | 59.243 | −54.591 | 18.121 | 1.00 | 51.28 | A | C |
| ATOM | 1971 | CG | GLU | A | 147 | 59.923 | −53.979 | 19.359 | 1.00 | 56.00 | A | C |
| ATOM | 1974 | CD | GLU | A | 147 | 59.228 | −52.725 | 19.877 | 1.00 | 63.07 | A | C |
| ATOM | 1975 | OE1 | GLU | A | 147 | 58.125 | −52.395 | 19.387 | 1.00 | 66.00 | A | O |
| ATOM | 1976 | OE2 | GLU | A | 147 | 59.788 | −52.068 | 20.785 | 1.00 | 66.72 | A | O |
| ATOM | 1977 | C | GLU | A | 147 | 60.791 | −53.608 | 16.404 | 1.00 | 47.26 | A | C |
| ATOM | 1978 | O | GLU | A | 147 | 61.365 | −52.554 | 16.584 | 1.00 | 46.13 | A | O |
| ATOM | 1980 | N | ASN | A | 148 | 61.383 | −54.649 | 15.830 | 1.00 | 47.30 | A | N |
| ATOM | 1981 | CA | ASN | A | 148 | 62.824 | −54.639 | 15.564 | 1.00 | 48.47 | A | C |
| ATOM | 1983 | CB | ASN | A | 148 | 63.333 | −56.046 | 15.259 | 1.00 | 49.35 | A | C |
| ATOM | 1986 | CG | ASN | A | 148 | 62.710 | −56.636 | 14.014 | 1.00 | 55.86 | A | C |
| ATOM | 1987 | OD1 | ASN | A | 148 | 62.358 | −55.913 | 13.075 | 1.00 | 62.15 | A | O |
| ATOM | 1988 | ND2 | ASN | A | 148 | 62.566 | −57.959 | 13.994 | 1.00 | 57.68 | A | N |
| ATOM | 1991 | C | ASN | A | 148 | 63.268 | −53.665 | 14.470 | 1.00 | 48.40 | A | C |
| ATOM | 1992 | O | ASN | A | 148 | 64.470 | −53.493 | 14.255 | 1.00 | 48.76 | A | O |
| ATOM | 1994 | N | LEU | A | 149 | 62.308 | −53.037 | 13.781 | 1.00 | 47.17 | A | N |
| ATOM | 1995 | CA | LEU | A | 149 | 62.612 | −52.012 | 12.775 | 1.00 | 45.22 | A | C |
| ATOM | 1997 | CB | LEU | A | 149 | 61.391 | −51.719 | 11.883 | 1.00 | 44.21 | A | C |
| ATOM | 2000 | CG | LEU | A | 149 | 60.901 | −52.874 | 10.985 | 1.00 | 45.00 | A | C |
| ATOM | 2002 | CD1 | LEU | A | 149 | 59.457 | −52.641 | 10.487 | 1.00 | 35.64 | A | C |

TABLE 4-2-continued

Coordinates of *P. alba* IspS

| | | | | | | | | | | | | |
|---|---|---|---|---|---|---|---|---|---|---|---|---|
| ATOM | 2006 | CD2 | LEU | A | 149 | 61.859 | −53.134 | 9.818 | 1.00 | 40.71 | A | C |
| ATOM | 2010 | C | LEU | A | 149 | 63.119 | −50.719 | 13.427 | 1.00 | 44.14 | A | C |
| ATOM | 2011 | O | LEU | A | 149 | 63.767 | −49.915 | 12.767 | 1.00 | 43.38 | A | O |
| ATOM | 2013 | N | LYS | A | 150 | 62.848 | −50.535 | 14.723 | 1.00 | 43.89 | A | N |
| ATOM | 2014 | CA | LYS | A | 150 | 63.299 | −49.345 | 15.459 | 1.00 | 43.64 | A | C |
| ATOM | 2016 | CB | LYS | A | 150 | 62.834 | −49.395 | 16.921 | 1.00 | 44.18 | A | C |
| ATOM | 2019 | CG | LYS | A | 150 | 63.567 | −50.438 | 17.776 | 1.00 | 45.80 | A | C |
| ATOM | 2022 | CD | LYS | A | 150 | 62.990 | −50.566 | 19.179 | 1.00 | 46.45 | A | C |
| ATOM | 2025 | CE | LYS | A | 150 | 63.602 | −51.772 | 19.932 | 1.00 | 46.45 | A | C |
| ATOM | 2028 | NZ | LYS | A | 150 | 63.600 | −51.578 | 21.410 | 1.00 | 44.46 | A | N |
| ATOM | 2032 | C | LYS | A | 150 | 64.816 | −49.166 | 15.418 | 1.00 | 43.28 | A | C |
| ATOM | 2033 | O | LYS | A | 150 | 65.307 | −48.058 | 15.547 | 1.00 | 43.46 | A | O |
| ATOM | 2035 | N | GLU | A | 151 | 65.548 | −50.262 | 15.231 | 1.00 | 43.96 | A | N |
| ATOM | 2036 | CA | GLU | A | 151 | 67.016 | −50.229 | 15.193 | 1.00 | 44.86 | A | C |
| ATOM | 2038 | CB | GLU | A | 151 | 67.590 | −51.660 | 15.231 | 1.00 | 46.17 | A | C |
| ATOM | 2041 | CG | GLU | A | 151 | 67.109 | −52.575 | 16.391 | 1.00 | 48.12 | A | C |
| ATOM | 2044 | CD | GLU | A | 151 | 67.468 | −52.062 | 17.783 | 1.00 | 57.25 | A | C |
| ATOM | 2045 | OE1 | GLU | A | 151 | 68.205 | −51.057 | 17.895 | 1.00 | 58.32 | A | O |
| ATOM | 2046 | OE2 | GLU | A | 151 | 67.010 | −52.679 | 18.776 | 1.00 | 64.54 | A | O |
| ATOM | 2047 | C | GLU | A | 151 | 67.568 | −49.510 | 13.960 | 1.00 | 44.01 | A | C |
| ATOM | 2048 | O | GLU | A | 151 | 68.687 | −49.009 | 13.987 | 1.00 | 45.27 | A | O |
| ATOM | 2050 | N | ASP | A | 152 | 66.778 | −49.481 | 12.887 | 1.00 | 43.54 | A | N |
| ATOM | 2051 | CA | ASP | A | 152 | 67.182 | −48.939 | 11.586 | 1.00 | 42.81 | A | C |
| ATOM | 2053 | CB | ASP | A | 152 | 66.628 | −49.846 | 10.469 | 1.00 | 42.48 | A | C |
| ATOM | 2056 | CG | ASP | A | 152 | 67.076 | −49.431 | 9.065 | 1.00 | 44.12 | A | C |
| ATOM | 2057 | OD1 | ASP | A | 152 | 67.707 | −48.356 | 8.890 | 1.00 | 44.74 | A | O |
| ATOM | 2058 | OD2 | ASP | A | 152 | 66.785 | −50.208 | 8.122 | 1.00 | 43.55 | A | O |
| ATOM | 2059 | C | ASP | A | 152 | 66.619 | −47.524 | 11.481 | 1.00 | 41.46 | A | C |
| ATOM | 2060 | O | ASP | A | 152 | 65.557 | −47.307 | 10.902 | 1.00 | 41.35 | A | O |
| ATOM | 2062 | N | ILE | A | 153 | 67.345 | −46.569 | 12.045 | 1.00 | 39.78 | A | N |
| ATOM | 2063 | CA | ILE | A | 153 | 66.816 | −45.228 | 12.270 | 1.00 | 39.72 | A | C |
| ATOM | 2065 | CB | ILE | A | 153 | 67.695 | −44.468 | 13.244 | 1.00 | 40.91 | A | C |
| ATOM | 2067 | CG1 | ILE | A | 153 | 67.578 | −45.131 | 14.627 | 1.00 | 43.16 | A | C |
| ATOM | 2070 | CD1 | ILE | A | 153 | 68.849 | −45.081 | 15.411 | 1.00 | 50.21 | A | C |
| ATOM | 2074 | CG2 | ILE | A | 153 | 67.288 | −42.997 | 13.309 | 1.00 | 36.49 | A | C |
| ATOM | 2078 | C | ILE | A | 153 | 66.625 | −44.422 | 10.992 | 1.00 | 39.38 | A | C |
| ATOM | 2079 | O | ILE | A | 153 | 65.718 | −43.606 | 10.902 | 1.00 | 38.41 | A | O |
| ATOM | 2081 | N | LYS | A | 154 | 67.483 | −44.667 | 10.011 | 1.00 | 38.77 | A | N |
| ATOM | 2082 | CA | LYS | A | 154 | 67.316 | −44.131 | 8.675 | 1.00 | 38.08 | A | C |
| ATOM | 2084 | CB | LYS | A | 154 | 68.439 | −44.657 | 7.771 | 1.00 | 39.94 | A | C |
| ATOM | 2087 | CG | LYS | A | 154 | 69.030 | −43.679 | 6.791 | 1.00 | 46.34 | A | C |
| ATOM | 2090 | CD | LYS | A | 154 | 69.998 | −44.418 | 5.833 | 1.00 | 57.75 | A | C |
| ATOM | 2093 | CE | LYS | A | 154 | 71.163 | −43.526 | 5.362 | 1.00 | 63.86 | A | C |
| ATOM | 2096 | NZ | LYS | A | 154 | 72.090 | −43.113 | 6.477 | 1.00 | 66.28 | A | N |
| ATOM | 2100 | C | LYS | A | 154 | 65.966 | −44.582 | 8.123 | 1.00 | 34.45 | A | C |
| ATOM | 2101 | O | LYS | A | 154 | 65.265 | −43.806 | 7.491 | 1.00 | 34.91 | A | O |
| ATOM | 2103 | N | ALA | A | 155 | 65.602 | −45.841 | 8.360 | 1.00 | 31.65 | A | N |
| ATOM | 2104 | CA | ALA | A | 155 | 64.367 | −46.382 | 7.796 | 1.00 | 29.70 | A | C |
| ATOM | 2106 | CB | ALA | A | 155 | 64.349 | −47.881 | 7.905 | 1.00 | 28.03 | A | C |
| ATOM | 2110 | C | ALA | A | 155 | 63.147 | −45.772 | 8.484 | 1.00 | 29.53 | A | C |
| ATOM | 2111 | O | ALA | A | 155 | 62.118 | −45.546 | 7.862 | 1.00 | 28.76 | A | O |
| ATOM | 2113 | N | ILE | A | 156 | 63.291 | −45.483 | 9.769 | 1.00 | 28.30 | A | N |
| ATOM | 2114 | CA | ILE | A | 156 | 62.218 | −44.941 | 10.574 | 1.00 | 29.28 | A | C |
| ATOM | 2116 | CB | ILE | A | 156 | 62.573 | −45.035 | 12.062 | 1.00 | 30.53 | A | C |
| ATOM | 2118 | CG1 | ILE | A | 156 | 62.606 | −46.500 | 12.498 | 1.00 | 32.30 | A | C |
| ATOM | 2121 | CD1 | ILE | A | 156 | 61.294 | −47.182 | 12.411 | 1.00 | 34.89 | A | C |
| ATOM | 2125 | CG2 | ILE | A | 156 | 61.599 | −44.209 | 12.894 | 1.00 | 35.42 | A | C |
| ATOM | 2129 | C | ILE | A | 156 | 61.957 | −43.486 | 10.232 | 1.00 | 26.18 | A | C |
| ATOM | 2130 | O | ILE | A | 156 | 60.816 | −43.061 | 10.146 | 1.00 | 25.91 | A | O |
| ATOM | 2132 | N | LEU | A | 157 | 63.026 | −42.738 | 10.049 | 1.00 | 25.45 | A | N |
| ATOM | 2133 | CA | LEU | A | 157 | 62.941 | −41.363 | 9.595 | 1.00 | 27.66 | A | C |
| ATOM | 2135 | CB | LEU | A | 157 | 64.320 | −40.773 | 9.381 | 1.00 | 28.15 | A | C |
| ATOM | 2138 | CG | LEU | A | 157 | 64.937 | −39.982 | 10.520 | 1.00 | 34.36 | A | C |
| ATOM | 2140 | CD1 | LEU | A | 157 | 66.210 | −39.356 | 9.983 | 1.00 | 31.72 | A | C |
| ATOM | 2144 | CD2 | LEU | A | 157 | 63.996 | −38.917 | 11.050 | 1.00 | 32.16 | A | C |
| ATOM | 2148 | C | LEU | A | 157 | 62.215 | −41.330 | 8.271 | 1.00 | 27.68 | A | C |
| ATOM | 2149 | O | LEU | A | 157 | 61.279 | −40.551 | 8.073 | 1.00 | 26.10 | A | O |
| ATOM | 2151 | N | SER | A | 158 | 62.658 | −42.199 | 7.371 | 1.00 | 26.74 | A | N |
| ATOM | 2152 | CA | SER | A | 158 | 62.074 | −42.255 | 6.064 | 1.00 | 27.94 | A | C |
| ATOM | 2154 | CB | SER | A | 158 | 62.861 | −43.219 | 5.198 | 1.00 | 27.98 | A | C |
| ATOM | 2157 | OG | SER | A | 158 | 62.518 | −43.042 | 3.845 | 1.00 | 44.57 | A | O |
| ATOM | 2159 | C | SER | A | 158 | 60.573 | −42.600 | 6.186 | 1.00 | 25.94 | A | C |
| ATOM | 2160 | O | SER | A | 158 | 59.730 | −41.938 | 5.574 | 1.00 | 23.44 | A | O |
| ATOM | 2162 | N | LEU | A | 159 | 60.227 | −43.568 | 7.034 | 1.00 | 24.38 | A | N |
| ATOM | 2163 | CA | LEU | A | 159 | 58.807 | −43.865 | 7.292 | 1.00 | 23.67 | A | C |
| ATOM | 2165 | CB | LEU | A | 159 | 58.667 | −45.082 | 8.206 | 1.00 | 23.04 | A | C |
| ATOM | 2168 | CG | LEU | A | 159 | 57.261 | −45.601 | 8.496 | 1.00 | 23.72 | A | C |
| ATOM | 2170 | CD1 | LEU | A | 159 | 56.577 | −46.056 | 7.202 | 1.00 | 19.76 | A | C |

TABLE 4-2-continued

| Coordinates of *P. alba* IspS | | | | | | | | | | | | |
|---|---|---|---|---|---|---|---|---|---|---|---|---|
| ATOM | 2174 | CD2 | LEU | A | 159 | 57.295 | −46.735 | 9.527 | 1.00 | 24.23 | A | C |
| ATOM | 2178 | C | LEU | A | 159 | 58.065 | −42.651 | 7.881 | 1.00 | 22.73 | A | C |
| ATOM | 2179 | O | LEU | A | 159 | 56.955 | −42.353 | 7.468 | 1.00 | 25.33 | A | O |
| ATOM | 2181 | N | TYR | A | 160 | 58.676 | −41.950 | 8.834 | 1.00 | 21.28 | A | N |
| ATOM | 2182 | CA | TYR | A | 160 | 58.069 | −40.740 | 9.406 | 1.00 | 19.99 | A | C |
| ATOM | 2184 | CB | TYR | A | 160 | 58.966 | −40.158 | 10.499 | 1.00 | 16.21 | A | C |
| ATOM | 2187 | CG | TYR | A | 160 | 58.612 | −38.765 | 11.028 | 1.00 | 15.97 | A | C |
| ATOM | 2188 | CD1 | TYR | A | 160 | 57.726 | −38.581 | 12.074 | 1.00 | 20.63 | A | C |
| ATOM | 2190 | CE1 | TYR | A | 160 | 57.431 | −37.309 | 12.550 | 1.00 | 23.21 | A | C |
| ATOM | 2192 | CZ | TYR | A | 160 | 58.069 | −36.229 | 12.008 | 1.00 | 24.75 | A | C |
| ATOM | 2193 | OH | TYR | A | 160 | 57.813 | −34.949 | 12.441 | 1.00 | 37.71 | A | O |
| ATOM | 2195 | CE2 | TYR | A | 160 | 58.962 | −36.401 | 10.988 | 1.00 | 27.54 | A | C |
| ATOM | 2197 | CD2 | TYR | A | 160 | 59.228 | −37.648 | 10.513 | 1.00 | 27.04 | A | C |
| ATOM | 2199 | C | TYR | A | 160 | 57.758 | −39.715 | 8.301 | 1.00 | 20.86 | A | C |
| ATOM | 2200 | O | TYR | A | 160 | 56.670 | −39.148 | 8.261 | 1.00 | 19.44 | A | O |
| ATOM | 2202 | N | GLU | A | 161 | 58.691 | −39.529 | 7.376 | 1.00 | 22.74 | A | N |
| ATOM | 2203 | CA | GLU | A | 161 | 58.562 | −38.479 | 6.366 | 1.00 | 22.29 | A | C |
| ATOM | 2205 | CB | GLU | A | 161 | 59.869 | −38.239 | 5.586 | 1.00 | 22.32 | A | C |
| ATOM | 2208 | CG | GLU | A | 161 | 61.065 | −37.781 | 6.403 | 1.00 | 25.25 | A | C |
| ATOM | 2211 | CD | GLU | A | 161 | 60.985 | −36.329 | 6.883 | 1.00 | 29.78 | A | C |
| ATOM | 2212 | OE1 | GLU | A | 161 | 59.985 | −35.612 | 6.600 | 1.00 | 30.17 | A | O |
| ATOM | 2213 | OE2 | GLU | A | 161 | 61.934 | −35.925 | 7.588 | 1.00 | 23.68 | A | O |
| ATOM | 2214 | C | GLU | A | 161 | 57.477 | −38.855 | 5.384 | 1.00 | 23.03 | A | C |
| ATOM | 2215 | O | GLU | A | 161 | 56.726 | −37.983 | 4.954 | 1.00 | 23.28 | A | O |
| ATOM | 2217 | N | ALA | A | 162 | 57.404 | −40.139 | 5.031 | 1.00 | 19.57 | A | N |
| ATOM | 2218 | CA | ALA | A | 162 | 56.377 | −40.621 | 4.113 | 1.00 | 20.19 | A | C |
| ATOM | 2220 | CB | ALA | A | 162 | 56.619 | −42.067 | 3.743 | 1.00 | 17.81 | A | C |
| ATOM | 2224 | C | ALA | A | 162 | 54.968 | −40.459 | 4.674 | 1.00 | 20.85 | A | C |
| ATOM | 2225 | O | ALA | A | 162 | 54.042 | −40.179 | 3.921 | 1.00 | 20.56 | A | O |
| ATOM | 2227 | N | SER | A | 163 | 54.795 | −40.651 | 5.983 | 1.00 | 21.00 | A | N |
| ATOM | 2228 | CA | SER | A | 163 | 53.453 | −40.617 | 6.584 | 1.00 | 20.15 | A | C |
| ATOM | 2230 | CB | SER | A | 163 | 53.512 | −40.917 | 8.077 | 1.00 | 20.26 | A | C |
| ATOM | 2233 | OG | SER | A | 163 | 54.223 | −39.914 | 8.772 | 1.00 | 22.70 | A | O |
| ATOM | 2235 | C | SER | A | 163 | 52.758 | −39.276 | 6.398 | 1.00 | 20.14 | A | C |
| ATOM | 2236 | O | SER | A | 163 | 51.553 | −39.212 | 6.412 | 1.00 | 21.29 | A | O |
| ATOM | 2238 | N | PHE | A | 164 | 53.505 | −38.194 | 6.207 | 1.00 | 21.91 | A | N |
| ATOM | 2239 | CA | PHE | A | 164 | 52.852 | −36.893 | 6.012 | 1.00 | 21.51 | A | C |
| ATOM | 2241 | CB | PHE | A | 164 | 53.783 | −35.742 | 6.353 | 1.00 | 21.26 | A | C |
| ATOM | 2244 | CG | PHE | A | 164 | 54.107 | −35.680 | 7.823 | 1.00 | 20.56 | A | C |
| ATOM | 2245 | CD1 | PHE | A | 164 | 53.300 | −34.984 | 8.692 | 1.00 | 19.82 | A | C |
| ATOM | 2247 | CE1 | PHE | A | 164 | 53.593 | −34.950 | 10.044 | 1.00 | 20.99 | A | C |
| ATOM | 2249 | CZ | PHE | A | 164 | 54.694 | −35.621 | 10.537 | 1.00 | 19.87 | A | C |
| ATOM | 2251 | CE2 | PHE | A | 164 | 55.491 | −36.343 | 9.683 | 1.00 | 22.05 | A | C |
| ATOM | 2253 | CD2 | PHE | A | 164 | 55.178 | −36.390 | 8.335 | 1.00 | 19.04 | A | C |
| ATOM | 2255 | C | PHE | A | 164 | 52.235 | −36.724 | 4.651 | 1.00 | 20.83 | A | C |
| ATOM | 2256 | O | PHE | A | 164 | 51.564 | −35.732 | 4.420 | 1.00 | 20.53 | A | O |
| ATOM | 2258 | N | LEU | A | 165 | 52.434 | −37.694 | 3.759 | 1.00 | 21.43 | A | N |
| ATOM | 2259 | CA | LEU | A | 165 | 51.817 | −37.634 | 2.443 | 1.00 | 21.34 | A | C |
| ATOM | 2261 | CB | LEU | A | 165 | 52.808 | −38.064 | 1.356 | 1.00 | 21.77 | A | C |
| ATOM | 2264 | CG | LEU | A | 165 | 53.927 | −37.066 | 0.985 | 1.00 | 24.00 | A | C |
| ATOM | 2266 | CD1 | LEU | A | 165 | 55.125 | −37.119 | 1.950 | 1.00 | 24.11 | A | C |
| ATOM | 2270 | CD2 | LEU | A | 165 | 54.414 | −37.300 | −0.424 | 1.00 | 21.22 | A | C |
| ATOM | 2274 | C | LEU | A | 165 | 50.496 | −38.420 | 2.372 | 1.00 | 21.79 | A | C |
| ATOM | 2275 | O | LEU | A | 165 | 49.967 | −38.657 | 1.306 | 1.00 | 24.21 | A | O |
| ATOM | 2277 | N | ALA | A | 166 | 49.957 | −38.775 | 3.523 | 1.00 | 21.05 | A | N |
| ATOM | 2278 | CA | ALA | A | 166 | 48.760 | −39.562 | 3.627 | 1.00 | 21.13 | A | C |
| ATOM | 2280 | CB | ALA | A | 166 | 48.449 | −39.848 | 5.112 | 1.00 | 16.14 | A | C |
| ATOM | 2284 | C | ALA | A | 166 | 47.564 | −38.887 | 2.998 | 1.00 | 22.34 | A | C |
| ATOM | 2285 | O | ALA | A | 166 | 47.448 | −37.664 | 3.031 | 1.00 | 23.04 | A | O |
| ATOM | 2287 | N | LEU | A | 167 | 46.670 | −39.710 | 2.446 | 1.00 | 22.65 | A | N |
| ATOM | 2288 | CA | LEU | A | 167 | 45.315 | −39.299 | 2.123 | 1.00 | 22.73 | A | C |
| ATOM | 2290 | CB | LEU | A | 167 | 44.903 | −39.929 | 0.805 | 1.00 | 22.79 | A | C |
| ATOM | 2293 | CG | LEU | A | 167 | 45.870 | −39.733 | −0.367 | 1.00 | 29.42 | A | C |
| ATOM | 2295 | CD1 | LEU | A | 167 | 45.269 | −40.327 | −1.669 | 1.00 | 17.64 | A | C |
| ATOM | 2299 | CD2 | LEU | A | 167 | 46.250 | −38.249 | −0.540 | 1.00 | 18.14 | A | C |
| ATOM | 2303 | C | LEU | A | 167 | 44.351 | −39.758 | 3.235 | 1.00 | 23.82 | A | C |
| ATOM | 2304 | O | LEU | A | 167 | 44.694 | −40.592 | 4.059 | 1.00 | 22.47 | A | O |
| ATOM | 2306 | N | GLU | A | 168 | 43.139 | −39.228 | 3.239 | 1.00 | 24.07 | A | N |
| ATOM | 2307 | CA | GLU | A | 168 | 42.132 | −39.692 | 4.157 | 1.00 | 25.29 | A | C |
| ATOM | 2309 | CB | GLU | A | 168 | 40.818 | −38.931 | 3.943 | 1.00 | 27.27 | A | C |
| ATOM | 2312 | CG | GLU | A | 168 | 40.738 | −37.525 | 4.576 | 1.00 | 30.92 | A | C |
| ATOM | 2315 | CD | GLU | A | 168 | 39.356 | −36.894 | 4.371 | 1.00 | 38.89 | A | C |
| ATOM | 2316 | OE1 | GLU | A | 168 | 38.996 | −36.617 | 3.199 | 1.00 | 36.18 | A | O |
| ATOM | 2317 | OE2 | GLU | A | 168 | 38.626 | −36.700 | 5.379 | 1.00 | 42.80 | A | O |
| ATOM | 2318 | C | GLU | A | 168 | 41.902 | −41.186 | 3.935 | 1.00 | 25.25 | A | C |
| ATOM | 2319 | O | GLU | A | 168 | 41.855 | −41.652 | 2.798 | 1.00 | 22.24 | A | O |
| ATOM | 2321 | N | GLY | A | 169 | 41.748 | −41.928 | 5.034 | 1.00 | 24.73 | A | N |
| ATOM | 2322 | CA | GLY | A | 169 | 41.540 | −43.370 | 4.977 | 1.00 | 21.86 | A | C |

TABLE 4-2-continued

Coordinates of *P. alba* IspS

| | | | | | | | | | | | | |
|---|---|---|---|---|---|---|---|---|---|---|---|---|
| ATOM | 2325 | C | GLY | A | 169 | 42.785 | −44.213 | 5.048 | 1.00 | 21.58 | A | C |
| ATOM | 2326 | O | GLY | A | 169 | 42.692 | −45.426 | 5.190 | 1.00 | 24.46 | A | O |
| ATOM | 2328 | N | GLU | A | 170 | 43.956 | −43.598 | 4.967 | 1.00 | 20.95 | A | N |
| ATOM | 2329 | CA | GLU | A | 170 | 45.179 | −44.378 | 4.872 | 1.00 | 21.33 | A | C |
| ATOM | 2331 | CB | GLU | A | 170 | 46.219 | −43.717 | 3.960 | 1.00 | 16.76 | A | C |
| ATOM | 2334 | CG | GLU | A | 170 | 45.778 | −43.588 | 2.518 | 1.00 | 22.22 | A | C |
| ATOM | 2337 | CD | GLU | A | 170 | 46.915 | −43.209 | 1.542 | 1.00 | 28.05 | A | C |
| ATOM | 2338 | OE1 | GLU | A | 170 | 47.070 | −43.885 | 0.497 | 1.00 | 32.07 | A | O |
| ATOM | 2339 | OE2 | GLU | A | 170 | 47.654 | −42.242 | 1.822 | 1.00 | 24.57 | A | O |
| ATOM | 2340 | C | GLU | A | 170 | 45.699 | −44.577 | 6.271 | 1.00 | 21.42 | A | C |
| ATOM | 2341 | O | GLU | A | 170 | 46.699 | −43.979 | 6.686 | 1.00 | 21.14 | A | O |
| ATOM | 2343 | N | ASN | A | 171 | 45.000 | −45.435 | 6.992 | 1.00 | 21.46 | A | N |
| ATOM | 2344 | CA | ASN | A | 171 | 45.247 | −45.636 | 8.406 | 1.00 | 23.53 | A | C |
| ATOM | 2346 | CB | ASN | A | 171 | 44.197 | −46.587 | 8.999 | 1.00 | 24.69 | A | C |
| ATOM | 2349 | CG | ASN | A | 171 | 44.256 | −47.982 | 8.375 | 1.00 | 28.66 | A | C |
| ATOM | 2350 | OD1 | ASN | A | 171 | 43.992 | −48.155 | 7.177 | 1.00 | 21.35 | A | O |
| ATOM | 2351 | ND2 | ASN | A | 171 | 44.645 | −48.972 | 9.178 | 1.00 | 19.68 | A | N |
| ATOM | 2354 | C | ASN | A | 171 | 46.648 | −46.164 | 8.692 | 1.00 | 24.20 | A | C |
| ATOM | 2355 | O | ASN | A | 171 | 47.193 | −45.894 | 9.753 | 1.00 | 24.52 | A | O |
| ATOM | 2357 | N | ILE | A | 172 | 47.217 | −46.909 | 7.745 | 1.00 | 25.20 | A | N |
| ATOM | 2358 | CA | ILE | A | 172 | 48.549 | −47.478 | 7.893 | 1.00 | 27.16 | A | C |
| ATOM | 2360 | CB | ILE | A | 172 | 48.898 | −48.455 | 6.738 | 1.00 | 27.07 | A | C |
| ATOM | 2362 | CG1 | ILE | A | 172 | 47.981 | −49.677 | 6.764 | 1.00 | 30.96 | A | C |
| ATOM | 2365 | CD1 | ILE | A | 172 | 48.252 | −50.653 | 5.616 | 1.00 | 34.90 | A | C |
| ATOM | 2369 | CG2 | ILE | A | 172 | 50.354 | −48.935 | 6.825 | 1.00 | 23.91 | A | C |
| ATOM | 2373 | C | ILE | A | 172 | 49.595 | −46.348 | 8.004 | 1.00 | 28.36 | A | C |
| ATOM | 2374 | O | ILE | A | 172 | 50.534 | −46.443 | 8.787 | 1.00 | 29.81 | A | O |
| ATOM | 2376 | N | LEU | A | 173 | 49.393 | −45.268 | 7.264 | 1.00 | 27.42 | A | N |
| ATOM | 2377 | CA | LEU | A | 173 | 50.326 | −44.141 | 7.300 | 1.00 | 27.76 | A | C |
| ATOM | 2379 | CB | LEU | A | 173 | 50.138 | −43.217 | 6.096 | 1.00 | 27.01 | A | C |
| ATOM | 2382 | CG | LEU | A | 173 | 50.933 | −43.554 | 4.842 | 1.00 | 27.25 | A | C |
| ATOM | 2384 | CD1 | LEU | A | 173 | 50.747 | −44.951 | 4.446 | 1.00 | 27.88 | A | C |
| ATOM | 2388 | CD2 | LEU | A | 173 | 50.482 | −42.633 | 3.687 | 1.00 | 29.35 | A | C |
| ATOM | 2392 | C | LEU | A | 173 | 50.197 | −43.362 | 8.605 | 1.00 | 26.43 | A | C |
| ATOM | 2393 | O | LEU | A | 173 | 51.201 | −42.925 | 9.141 | 1.00 | 25.15 | A | O |
| ATOM | 2395 | N | ASP | A | 174 | 48.981 | −43.205 | 9.121 | 1.00 | 24.34 | A | N |
| ATOM | 2396 | CA | ASP | A | 174 | 48.792 | −42.610 | 10.443 | 1.00 | 26.66 | A | C |
| ATOM | 2398 | CB | ASP | A | 174 | 47.310 | −42.444 | 10.771 | 1.00 | 27.51 | A | C |
| ATOM | 2401 | CG | ASP | A | 174 | 46.649 | −41.327 | 9.959 | 1.00 | 34.04 | A | C |
| ATOM | 2402 | OD1 | ASP | A | 174 | 47.363 | −40.551 | 9.305 | 1.00 | 40.90 | A | O |
| ATOM | 2403 | OD2 | ASP | A | 174 | 45.406 | −41.228 | 9.980 | 1.00 | 42.95 | A | O |
| ATOM | 2404 | C | ASP | A | 174 | 49.438 | −43.451 | 11.539 | 1.00 | 27.18 | A | C |
| ATOM | 2405 | O | ASP | A | 174 | 50.099 | −42.926 | 12.432 | 1.00 | 28.53 | A | O |
| ATOM | 2407 | N | GLU | A | 175 | 49.228 | −44.756 | 11.480 | 1.00 | 28.79 | A | N |
| ATOM | 2408 | CA | GLU | A | 175 | 49.843 | −45.659 | 12.431 | 1.00 | 29.42 | A | C |
| ATOM | 2410 | CB | GLU | A | 175 | 49.321 | −47.083 | 12.237 | 1.00 | 29.10 | A | C |
| ATOM | 2413 | CG | GLU | A | 175 | 47.835 | −47.244 | 12.560 | 1.00 | 36.91 | A | C |
| ATOM | 2416 | CD | GLU | A | 175 | 47.189 | −48.421 | 11.819 | 1.00 | 41.63 | A | C |
| ATOM | 2417 | OE1 | GLU | A | 175 | 47.928 | −49.311 | 11.327 | 1.00 | 42.73 | A | O |
| ATOM | 2418 | OE2 | GLU | A | 175 | 45.946 | −48.436 | 11.719 | 1.00 | 39.01 | A | O |
| ATOM | 2419 | C | GLU | A | 175 | 51.356 | −45.616 | 12.230 | 1.00 | 27.89 | A | C |
| ATOM | 2420 | O | GLU | A | 175 | 52.100 | −45.726 | 13.180 | 1.00 | 27.43 | A | O |
| ATOM | 2422 | N | ALA | A | 176 | 51.797 | −45.473 | 10.982 | 1.00 | 27.66 | A | N |
| ATOM | 2423 | CA | ALA | A | 176 | 53.225 | −45.370 | 10.668 | 1.00 | 28.24 | A | C |
| ATOM | 2425 | CB | ALA | A | 176 | 53.428 | −45.280 | 9.153 | 1.00 | 26.14 | A | C |
| ATOM | 2429 | C | ALA | A | 176 | 53.872 | −44.173 | 11.387 | 1.00 | 27.46 | A | C |
| ATOM | 2430 | O | ALA | A | 176 | 54.970 | −44.276 | 11.929 | 1.00 | 27.53 | A | O |
| ATOM | 2432 | N | LYS | A | 177 | 53.155 | −43.055 | 11.418 | 1.00 | 26.90 | A | N |
| ATOM | 2433 | CA | LYS | A | 177 | 53.626 | −41.840 | 12.060 | 1.00 | 27.36 | A | C |
| ATOM | 2435 | CB | LYS | A | 177 | 52.670 | −40.666 | 11.775 | 1.00 | 26.52 | A | C |
| ATOM | 2438 | CG | LYS | A | 177 | 53.138 | −39.310 | 12.294 | 1.00 | 26.21 | A | C |
| ATOM | 2441 | CD | LYS | A | 177 | 52.073 | −38.200 | 12.199 | 1.00 | 27.44 | A | C |
| ATOM | 2444 | CE | LYS | A | 177 | 51.689 | −37.893 | 10.754 | 1.00 | 28.20 | A | C |
| ATOM | 2447 | NZ | LYS | A | 177 | 50.565 | −36.898 | 10.663 | 1.00 | 27.57 | A | N |
| ATOM | 2451 | C | LYS | A | 177 | 53.783 | −42.067 | 13.558 | 1.00 | 28.77 | A | C |
| ATOM | 2452 | O | LYS | A | 177 | 54.830 | −41.743 | 14.117 | 1.00 | 28.26 | A | O |
| ATOM | 2454 | N | VAL | A | 178 | 52.749 | −42.617 | 14.196 | 1.00 | 29.28 | A | N |
| ATOM | 2455 | CA | VAL | A | 178 | 52.737 | −42.855 | 15.654 | 1.00 | 27.74 | A | C |
| ATOM | 2457 | CB | VAL | A | 178 | 51.409 | −43.524 | 16.103 | 1.00 | 28.79 | A | C |
| ATOM | 2459 | CG1 | VAL | A | 178 | 51.481 | −44.089 | 17.585 | 1.00 | 22.40 | A | C |
| ATOM | 2463 | CG2 | VAL | A | 178 | 50.228 | −42.565 | 15.919 | 1.00 | 23.47 | A | C |
| ATOM | 2467 | C | VAL | A | 178 | 53.907 | −43.758 | 16.025 | 1.00 | 29.18 | A | C |
| ATOM | 2468 | O | VAL | A | 178 | 54.651 | −43.485 | 16.955 | 1.00 | 30.11 | A | O |
| ATOM | 2470 | N | PHE | A | 179 | 54.058 | −44.838 | 15.273 | 1.00 | 28.49 | A | N |
| ATOM | 2471 | CA | PHE | A | 179 | 55.168 | −45.759 | 15.448 | 1.00 | 28.24 | A | C |
| ATOM | 2473 | CB | PHE | A | 179 | 54.990 | −46.915 | 14.466 | 1.00 | 28.43 | A | C |
| ATOM | 2476 | CG | PHE | A | 179 | 56.115 | −47.880 | 14.457 | 1.00 | 29.30 | A | C |
| ATOM | 2477 | CD1 | PHE | A | 179 | 56.233 | −48.824 | 15.453 | 1.00 | 30.81 | A | C |

TABLE 4-2-continued

| Coordinates of *P. alba* IspS | | | | | | | | | | | |
|---|---|---|---|---|---|---|---|---|---|---|---|
| ATOM | 2479 | CE1 | PHE | A | 179 | 57.278 | −49.725 | 15.441 | 1.00 | 28.19 | A | C |
| ATOM | 2481 | CZ | PHE | A | 179 | 58.208 | −49.687 | 14.431 | 1.00 | 30.08 | A | C |
| ATOM | 2483 | CE2 | PHE | A | 179 | 58.089 | −48.755 | 13.424 | 1.00 | 30.12 | A | C |
| ATOM | 2485 | CD2 | PHE | A | 179 | 57.051 | −47.860 | 13.444 | 1.00 | 29.06 | A | C |
| ATOM | 2487 | C | PHE | A | 179 | 56.555 | −45.097 | 15.276 | 1.00 | 28.33 | A | C |
| ATOM | 2488 | O | PHE | A | 179 | 57.435 | −45.283 | 16.104 | 1.00 | 25.10 | A | O |
| ATOM | 2490 | N | ALA | A | 180 | 56.757 | −44.332 | 14.204 | 1.00 | 28.10 | A | N |
| ATOM | 2491 | CA | ALA | A | 180 | 58.054 | −43.728 | 13.971 | 1.00 | 26.76 | A | C |
| ATOM | 2493 | CB | ALA | A | 180 | 58.150 | −43.168 | 12.577 | 1.00 | 24.69 | A | C |
| ATOM | 2497 | C | ALA | A | 180 | 58.382 | −42.652 | 15.034 | 1.00 | 29.09 | A | C |
| ATOM | 2498 | O | ALA | A | 180 | 59.485 | −42.646 | 15.586 | 1.00 | 27.52 | A | O |
| ATOM | 2500 | N | ILE | A | 181 | 57.420 | −41.775 | 15.319 | 1.00 | 28.79 | A | N |
| ATOM | 2501 | CA | ILE | A | 181 | 57.591 | −40.717 | 16.285 | 1.00 | 30.81 | A | C |
| ATOM | 2503 | CB | ILE | A | 181 | 56.310 | −39.865 | 16.483 | 1.00 | 31.36 | A | C |
| ATOM | 2505 | CG1 | ILE | A | 181 | 56.105 | −38.909 | 15.302 | 1.00 | 38.18 | A | C |
| ATOM | 2508 | CD1 | ILE | A | 181 | 54.765 | −38.081 | 15.352 | 1.00 | 37.32 | A | C |
| ATOM | 2512 | CG2 | ILE | A | 181 | 56.415 | −39.000 | 17.738 | 1.00 | 34.50 | A | C |
| ATOM | 2516 | C | ILE | A | 181 | 58.002 | −41.293 | 17.629 | 1.00 | 33.92 | A | C |
| ATOM | 2517 | O | ILE | A | 181 | 58.908 | −40.757 | 18.270 | 1.00 | 32.34 | A | O |
| ATOM | 2519 | N | SER | A | 182 | 57.359 | −42.383 | 18.045 | 1.00 | 34.21 | A | N |
| ATOM | 2520 | CA | SER | A | 182 | 57.608 | −42.923 | 19.361 | 1.00 | 37.21 | A | C |
| ATOM | 2522 | CB | SER | A | 182 | 56.573 | −43.991 | 19.721 | 1.00 | 37.94 | A | C |
| ATOM | 2525 | OG | SER | A | 182 | 56.744 | −45.180 | 18.958 | 1.00 | 41.64 | A | O |
| ATOM | 2527 | C | SER | A | 182 | 59.030 | −43.474 | 19.473 | 1.00 | 38.60 | A | C |
| ATOM | 2528 | O | SER | A | 182 | 59.618 | −43.437 | 20.553 | 1.00 | 40.23 | A | O |
| ATOM | 2530 | N | HIS | A | 183 | 59.570 | −43.982 | 18.366 | 1.00 | 38.90 | A | N |
| ATOM | 2531 | CA | HIS | A | 183 | 60.933 | −44.519 | 18.342 | 1.00 | 40.39 | A | C |
| ATOM | 2533 | CB | HIS | A | 183 | 61.054 | −45.715 | 17.401 | 1.00 | 39.71 | A | C |
| ATOM | 2536 | CG | HIS | A | 183 | 60.270 | −46.913 | 17.839 | 1.00 | 46.09 | A | C |
| ATOM | 2537 | ND1 | HIS | A | 183 | 60.409 | −47.479 | 19.089 | 1.00 | 52.45 | A | N |
| ATOM | 2539 | CE1 | HIS | A | 183 | 59.597 | −48.516 | 19.192 | 1.00 | 55.12 | A | C |
| ATOM | 2541 | NE2 | HIS | A | 183 | 58.945 | −48.648 | 18.051 | 1.00 | 54.77 | A | N |
| ATOM | 2543 | CD2 | HIS | A | 183 | 59.349 | −47.660 | 17.188 | 1.00 | 47.51 | A | C |
| ATOM | 2545 | C | HIS | A | 183 | 61.972 | −43.469 | 17.945 | 1.00 | 41.16 | A | C |
| ATOM | 2546 | O | HIS | A | 183 | 63.162 | −43.724 | 18.087 | 1.00 | 44.04 | A | O |
| ATOM | 2548 | N | LEU | A | 184 | 61.536 | −42.314 | 17.439 | 1.00 | 38.00 | A | N |
| ATOM | 2549 | CA | LEU | A | 184 | 62.448 | −41.207 | 17.193 | 1.00 | 37.65 | A | C |
| ATOM | 2551 | CB | LEU | A | 184 | 62.018 | −40.400 | 15.968 | 1.00 | 34.76 | A | C |
| ATOM | 2554 | CG | LEU | A | 184 | 62.130 | −41.133 | 14.624 | 1.00 | 35.32 | A | C |
| ATOM | 2556 | CD1 | LEU | A | 184 | 61.311 | −40.390 | 13.576 | 1.00 | 22.44 | A | C |
| ATOM | 2560 | CD2 | LEU | A | 184 | 63.579 | −41.297 | 14.167 | 1.00 | 24.78 | A | C |
| ATOM | 2564 | C | LEU | A | 184 | 62.591 | −40.267 | 18.400 | 1.00 | 37.45 | A | C |
| ATOM | 2565 | O | LEU | A | 184 | 63.620 | −39.647 | 18.551 | 1.00 | 33.63 | A | O |
| ATOM | 2567 | N | LYS | A | 185 | 61.558 | −40.165 | 19.231 | 1.00 | 40.96 | A | N |
| ATOM | 2568 | CA | LYS | A | 185 | 61.490 | −39.158 | 20.286 | 1.00 | 46.25 | A | C |
| ATOM | 2570 | CB | LYS | A | 185 | 60.062 | −39.043 | 20.825 | 1.00 | 47.18 | A | C |
| ATOM | 2573 | CG | LYS | A | 185 | 59.568 | −37.619 | 20.940 | 1.00 | 54.79 | A | C |
| ATOM | 2576 | CD | LYS | A | 185 | 58.037 | −37.534 | 21.071 | 1.00 | 62.29 | A | C |
| ATOM | 2579 | CE | LYS | A | 185 | 57.489 | −36.307 | 20.328 | 1.00 | 65.20 | A | C |
| ATOM | 2582 | NZ | LYS | A | 185 | 56.019 | −36.110 | 20.508 | 1.00 | 64.22 | A | N |
| ATOM | 2586 | C | LYS | A | 185 | 62.412 | −39.502 | 21.447 | 1.00 | 50.17 | A | C |
| ATOM | 2587 | O | LYS | A | 185 | 62.835 | −38.626 | 22.190 | 1.00 | 50.48 | A | O |
| ATOM | 2589 | N | GLU | A | 186 | 62.695 | −40.786 | 21.608 | 1.00 | 54.79 | A | N |
| ATOM | 2590 | CA | GLU | A | 186 | 63.492 | −41.268 | 22.714 | 1.00 | 59.57 | A | C |
| ATOM | 2592 | CB | GLU | A | 186 | 62.748 | −42.417 | 23.422 | 1.00 | 61.31 | A | C |
| ATOM | 2595 | CG | GLU | A | 186 | 61.324 | −42.053 | 23.918 | 1.00 | 65.37 | A | C |
| ATOM | 2598 | CD | GLU | A | 186 | 61.289 | −40.817 | 24.837 | 1.00 | 71.20 | A | C |
| ATOM | 2599 | OE1 | GLU | A | 186 | 62.279 | −40.570 | 25.570 | 1.00 | 72.40 | A | O |
| ATOM | 2600 | OE2 | GLU | A | 186 | 60.266 | −40.090 | 24.826 | 1.00 | 69.58 | A | O |
| ATOM | 2601 | C | GLU | A | 186 | 64.859 | −41.715 | 22.199 | 1.00 | 61.26 | A | C |
| ATOM | 2602 | O | GLU | A | 186 | 65.344 | −42.800 | 22.545 | 1.00 | 61.31 | A | O |
| ATOM | 2604 | N | LEU | A | 187 | 65.474 | −40.871 | 21.368 | 1.00 | 61.95 | A | N |
| ATOM | 2605 | CA | LEU | A | 187 | 66.803 | −41.144 | 20.832 | 1.00 | 62.48 | A | C |
| ATOM | 2607 | CB | LEU | A | 187 | 66.795 | −41.069 | 19.309 | 1.00 | 61.46 | A | C |
| ATOM | 2610 | CG | LEU | A | 187 | 66.046 | −42.207 | 18.622 | 1.00 | 60.67 | A | C |
| ATOM | 2612 | CD1 | LEU | A | 187 | 66.159 | −42.112 | 17.107 | 1.00 | 54.64 | A | C |
| ATOM | 2616 | CD2 | LEU | A | 187 | 66.571 | −43.549 | 19.105 | 1.00 | 60.19 | A | C |
| ATOM | 2620 | C | LEU | A | 187 | 67.848 | −40.185 | 21.403 | 1.00 | 64.11 | A | C |
| ATOM | 2621 | O | LEU | A | 187 | 67.646 | −38.964 | 21.436 | 1.00 | 63.36 | A | O |
| ATOM | 2623 | N | SER | A | 188 | 68.968 | −40.764 | 21.842 | 1.00 | 66.14 | A | N |
| ATOM | 2624 | CA | SER | A | 188 | 70.064 | −40.014 | 22.460 | 1.00 | 66.96 | A | C |
| ATOM | 2626 | CB | SER | A | 188 | 70.591 | −40.762 | 23.685 | 1.00 | 67.57 | A | C |
| ATOM | 2629 | OG | SER | A | 188 | 69.575 | −40.923 | 24.660 | 1.00 | 70.39 | A | O |
| ATOM | 2631 | C | SER | A | 188 | 71.203 | −39.809 | 21.472 | 1.00 | 66.59 | A | C |
| ATOM | 2632 | O | SER | A | 188 | 71.607 | −40.744 | 20.766 | 1.00 | 64.52 | A | O |
| ATOM | 2634 | N | GLU | A | 189 | 71.720 | −38.583 | 21.438 | 1.00 | 67.77 | A | N |
| ATOM | 2635 | CA | GLU | A | 189 | 72.847 | −38.231 | 20.578 | 1.00 | 69.56 | A | C |
| ATOM | 2637 | CB | GLU | A | 189 | 73.248 | −36.765 | 20.791 | 1.00 | 70.17 | A | C |

TABLE 4-2-continued

Coordinates of *P. alba* IspS

| | | | | | | | | | | | | |
|---|---|---|---|---|---|---|---|---|---|---|---|---|
| ATOM | 2640 | CG | GLU | A | 189 | 74.339 | −36.266 | 19.841 | 1.00 | 73.91 | A | C |
| ATOM | 2643 | CD | GLU | A | 189 | 74.480 | −34.742 | 19.820 | 1.00 | 79.04 | A | C |
| ATOM | 2644 | OE1 | GLU | A | 189 | 73.752 | −34.043 | 20.565 | 1.00 | 78.69 | A | O |
| ATOM | 2645 | OE2 | GLU | A | 189 | 75.329 | −34.244 | 19.044 | 1.00 | 81.94 | A | O |
| ATOM | 2646 | C | GLU | A | 189 | 74.039 | −39.156 | 20.818 | 1.00 | 70.07 | A | C |
| ATOM | 2647 | O | GLU | A | 189 | 74.733 | −39.517 | 19.875 | 1.00 | 68.55 | A | O |
| ATOM | 2649 | N | GLU | A | 190 | 74.260 | −39.536 | 22.078 | 1.00 | 71.69 | A | N |
| ATOM | 2650 | CA | GLU | A | 190 | 75.327 | −40.477 | 22.448 | 1.00 | 72.75 | A | C |
| ATOM | 2652 | CB | GLU | A | 190 | 75.285 | −40.796 | 23.952 | 1.00 | 73.95 | A | C |
| ATOM | 2655 | CG | GLU | A | 190 | 76.108 | −39.856 | 24.832 | 1.00 | 77.12 | A | C |
| ATOM | 2658 | CD | GLU | A | 190 | 75.626 | −38.415 | 24.801 | 1.00 | 81.42 | A | C |
| ATOM | 2659 | OE1 | GLU | A | 190 | 74.514 | −38.146 | 24.284 | 1.00 | 82.03 | A | O |
| ATOM | 2660 | OE2 | GLU | A | 190 | 76.372 | −37.546 | 25.303 | 1.00 | 83.94 | A | O |
| ATOM | 2661 | C | GLU | A | 190 | 75.242 | −41.777 | 21.654 | 1.00 | 72.09 | A | C |
| ATOM | 2662 | O | GLU | A | 190 | 76.225 | −42.207 | 21.051 | 1.00 | 72.00 | A | O |
| ATOM | 2664 | N | LYS | A | 191 | 74.058 | −42.384 | 21.648 | 1.00 | 71.50 | A | N |
| ATOM | 2665 | CA | LYS | A | 191 | 73.837 | −43.669 | 20.977 | 1.00 | 71.87 | A | C |
| ATOM | 2667 | CB | LYS | A | 191 | 72.406 | −44.167 | 21.222 | 1.00 | 72.85 | A | C |
| ATOM | 2670 | CG | LYS | A | 191 | 71.999 | −44.262 | 22.685 | 1.00 | 77.73 | A | C |
| ATOM | 2673 | CD | LYS | A | 191 | 72.705 | −45.417 | 23.395 | 1.00 | 84.01 | A | C |
| ATOM | 2676 | CE | LYS | A | 191 | 72.961 | −45.117 | 24.873 | 1.00 | 85.51 | A | C |
| ATOM | 2679 | NZ | LYS | A | 191 | 74.197 | −45.799 | 25.352 | 1.00 | 86.45 | A | N |
| ATOM | 2683 | C | LYS | A | 191 | 74.081 | −43.581 | 19.467 | 1.00 | 70.30 | A | C |
| ATOM | 2684 | O | LYS | A | 191 | 74.929 | −44.293 | 18.923 | 1.00 | 70.06 | A | O |
| ATOM | 2686 | N | ILE | A | 192 | 73.337 | −42.700 | 18.803 | 1.00 | 68.27 | A | N |
| ATOM | 2687 | CA | ILE | A | 192 | 73.412 | −42.559 | 17.344 | 1.00 | 67.41 | A | C |
| ATOM | 2689 | CB | ILE | A | 192 | 72.021 | −42.259 | 16.721 | 1.00 | 66.84 | A | C |
| ATOM | 2691 | CG1 | ILE | A | 192 | 71.413 | −40.959 | 17.266 | 1.00 | 66.08 | A | C |
| ATOM | 2694 | CD1 | ILE | A | 192 | 70.180 | −40.498 | 16.516 | 1.00 | 61.79 | A | C |
| ATOM | 2698 | CG2 | ILE | A | 192 | 71.079 | −43.397 | 17.011 | 1.00 | 66.67 | A | C |
| ATOM | 2702 | C | ILE | A | 192 | 74.418 | −41.476 | 16.984 | 1.00 | 66.49 | A | C |
| ATOM | 2703 | O | ILE | A | 192 | 75.005 | −40.860 | 17.864 | 1.00 | 65.60 | A | O |
| ATOM | 2705 | N | GLY | A | 193 | 74.623 | −41.241 | 15.694 | 1.00 | 66.38 | A | N |
| ATOM | 2706 | CA | GLY | A | 193 | 75.553 | −40.195 | 15.259 | 1.00 | 66.52 | A | C |
| ATOM | 2709 | C | GLY | A | 193 | 75.264 | −38.810 | 15.831 | 1.00 | 65.05 | A | C |
| ATOM | 2710 | O | GLY | A | 193 | 74.192 | −38.557 | 16.396 | 1.00 | 64.86 | A | O |
| ATOM | 2712 | N | LYS | A | 194 | 76.235 | −37.910 | 15.701 | 1.00 | 62.68 | A | N |
| ATOM | 2713 | CA | LYS | A | 194 | 75.958 | −36.492 | 15.879 | 1.00 | 61.11 | A | C |
| ATOM | 2715 | CB | LYS | A | 194 | 77.243 | −35.657 | 15.953 | 1.00 | 62.09 | A | C |
| ATOM | 2718 | CG | LYS | A | 194 | 78.355 | −36.254 | 16.839 | 1.00 | 69.49 | A | C |
| ATOM | 2721 | CD | LYS | A | 194 | 79.386 | −35.198 | 17.291 | 1.00 | 73.25 | A | C |
| ATOM | 2724 | CE | LYS | A | 194 | 80.488 | −35.828 | 18.136 | 1.00 | 73.20 | A | C |
| ATOM | 2727 | NZ | LYS | A | 194 | 81.352 | −34.809 | 18.783 | 1.00 | 72.29 | A | N |
| ATOM | 2731 | C | LYS | A | 194 | 75.096 | −36.058 | 14.680 | 1.00 | 58.07 | A | C |
| ATOM | 2732 | O | LYS | A | 194 | 74.119 | −35.337 | 14.842 | 1.00 | 56.95 | A | O |
| ATOM | 2734 | N | GLU | A | 195 | 75.447 | −36.528 | 13.484 | 1.00 | 54.22 | A | N |
| ATOM | 2735 | CA | GLU | A | 195 | 74.722 | −36.140 | 12.287 | 1.00 | 53.49 | A | C |
| ATOM | 2737 | CB | GLU | A | 195 | 75.507 | −36.489 | 11.005 | 1.00 | 53.97 | A | C |
| ATOM | 2740 | CG | GLU | A | 195 | 75.487 | −37.950 | 10.549 | 1.00 | 60.23 | A | C |
| ATOM | 2743 | CD | GLU | A | 195 | 76.394 | −38.208 | 9.329 | 1.00 | 66.28 | A | C |
| ATOM | 2744 | OE1 | GLU | A | 195 | 76.046 | −39.079 | 8.500 | 1.00 | 68.96 | A | O |
| ATOM | 2745 | OE2 | GLU | A | 195 | 77.450 | −37.544 | 9.194 | 1.00 | 62.48 | A | O |
| ATOM | 2746 | C | GLU | A | 195 | 73.296 | −36.714 | 12.261 | 1.00 | 50.83 | A | C |
| ATOM | 2747 | O | GLU | A | 195 | 72.363 | −36.050 | 11.773 | 1.00 | 48.97 | A | O |
| ATOM | 2749 | N | LEU | A | 196 | 73.125 | −37.925 | 12.792 | 1.00 | 46.53 | A | N |
| ATOM | 2750 | CA | LEU | A | 196 | 71.808 | −38.556 | 12.821 | 1.00 | 43.53 | A | C |
| ATOM | 2752 | CB | LEU | A | 196 | 71.892 | −40.048 | 13.130 | 1.00 | 43.43 | A | C |
| ATOM | 2755 | CG | LEU | A | 196 | 71.893 | −40.894 | 11.870 | 1.00 | 43.50 | A | C |
| ATOM | 2757 | CD1 | LEU | A | 196 | 72.472 | −42.286 | 12.143 | 1.00 | 46.58 | A | C |
| ATOM | 2761 | CD2 | LEU | A | 196 | 70.472 | −40.959 | 11.279 | 1.00 | 43.97 | A | C |
| ATOM | 2765 | C | LEU | A | 196 | 70.881 | −37.857 | 13.799 | 1.00 | 40.68 | A | C |
| ATOM | 2766 | O | LEU | A | 196 | 69.731 | −37.587 | 13.461 | 1.00 | 40.50 | A | O |
| ATOM | 2768 | N | ALA | A | 197 | 71.383 | −37.531 | 14.983 | 1.00 | 36.99 | A | N |
| ATOM | 2769 | CA | ALA | A | 197 | 70.584 | −36.804 | 15.961 | 1.00 | 35.57 | A | C |
| ATOM | 2771 | CB | ALA | A | 197 | 71.364 | −36.595 | 17.246 | 1.00 | 33.51 | A | C |
| ATOM | 2775 | C | ALA | A | 197 | 70.119 | −35.460 | 15.406 | 1.00 | 35.11 | A | C |
| ATOM | 2776 | O | ALA | A | 197 | 68.995 | −35.042 | 15.677 | 1.00 | 35.72 | A | O |
| ATOM | 2778 | N | GLU | A | 198 | 70.986 | −34.778 | 14.653 | 1.00 | 33.60 | A | N |
| ATOM | 2779 | CA | GLU | A | 198 | 70.605 | −33.513 | 14.002 | 1.00 | 35.29 | A | C |
| ATOM | 2781 | CB | GLU | A | 198 | 71.836 | −32.795 | 13.432 | 1.00 | 36.22 | A | C |
| ATOM | 2784 | CG | GLU | A | 198 | 72.762 | −32.235 | 14.540 | 1.00 | 50.06 | A | C |
| ATOM | 2787 | CD | GLU | A | 198 | 74.148 | −31.764 | 14.057 | 1.00 | 60.04 | A | C |
| ATOM | 2788 | OE1 | GLU | A | 198 | 74.806 | −32.492 | 13.272 | 1.00 | 66.90 | A | O |
| ATOM | 2789 | OE2 | GLU | A | 198 | 74.585 | −30.667 | 14.491 | 1.00 | 63.26 | A | O |
| ATOM | 2790 | C | GLU | A | 198 | 69.534 | −33.754 | 12.916 | 1.00 | 31.70 | A | C |
| ATOM | 2791 | O | GLU | A | 198 | 68.608 | −32.969 | 12.768 | 1.00 | 33.74 | A | O |
| ATOM | 2793 | N | GLN | A | 199 | 69.647 | −34.857 | 12.201 | 1.00 | 28.08 | A | N |
| ATOM | 2794 | CA | GLN | A | 199 | 68.694 | −35.215 | 11.158 | 1.00 | 29.52 | A | C |

TABLE 4-2-continued

| Coordinates of *P. alba* IspS | | | | | | | | | | | | |
|---|---|---|---|---|---|---|---|---|---|---|---|---|
| ATOM | 2796 | CB | GLN | A | 199 | 69.315 | −36.342 | 10.323 | 1.00 | 30.33 | A | C |
| ATOM | 2799 | CG | GLN | A | 199 | 68.764 | −36.594 | 8.954 | 1.00 | 42.18 | A | C |
| ATOM | 2802 | CD | GLN | A | 199 | 69.077 | −35.489 | 7.927 | 1.00 | 53.91 | A | C |
| ATOM | 2803 | OE1 | GLN | A | 199 | 68.161 | −34.927 | 7.316 | 1.00 | 54.02 | A | O |
| ATOM | 2804 | NE2 | GLN | A | 199 | 70.359 | −35.211 | 7.705 | 1.00 | 47.12 | A | N |
| ATOM | 2807 | C | GLN | A | 199 | 67.326 | −35.566 | 11.828 | 1.00 | 27.82 | A | C |
| ATOM | 2808 | O | GLN | A | 199 | 66.277 | −35.071 | 11.419 | 1.00 | 24.92 | A | O |
| ATOM | 2810 | N | VAL | A | 200 | 67.361 | −36.329 | 12.922 | 1.00 | 27.96 | A | N |
| ATOM | 2811 | CA | VAL | A | 200 | 66.162 | −36.642 | 13.712 | 1.00 | 26.88 | A | C |
| ATOM | 2813 | CB | VAL | A | 200 | 66.485 | −37.637 | 14.821 | 1.00 | 28.23 | A | C |
| ATOM | 2815 | CG1 | VAL | A | 200 | 66.795 | −39.011 | 14.204 | 1.00 | 29.92 | A | C |
| ATOM | 2819 | CG2 | VAL | A | 200 | 65.342 | −37.736 | 15.839 | 1.00 | 23.69 | A | C |
| ATOM | 2823 | C | VAL | A | 200 | 65.496 | −35.422 | 14.336 | 1.00 | 27.44 | A | C |
| ATOM | 2824 | O | VAL | A | 200 | 64.277 | −35.274 | 14.235 | 1.00 | 26.51 | A | O |
| ATOM | 2826 | N | ASN | A | 201 | 66.288 | −34.536 | 14.946 | 1.00 | 27.44 | A | N |
| ATOM | 2827 | CA | ASN | A | 201 | 65.754 | −33.319 | 15.554 | 1.00 | 29.08 | A | C |
| ATOM | 2829 | CB | ASN | A | 201 | 66.835 | −32.603 | 16.398 | 1.00 | 30.46 | A | C |
| ATOM | 2832 | CG | ASN | A | 201 | 67.362 | −33.468 | 17.575 | 1.00 | 34.58 | A | C |
| ATOM | 2833 | OD1 | ASN | A | 201 | 66.665 | −34.330 | 18.124 | 1.00 | 43.42 | A | O |
| ATOM | 2834 | ND2 | ASN | A | 201 | 68.604 | −33.231 | 17.947 | 1.00 | 39.12 | A | N |
| ATOM | 2837 | C | ASN | A | 201 | 65.140 | −32.337 | 14.530 | 1.00 | 28.73 | A | C |
| ATOM | 2838 | O | ASN | A | 201 | 64.107 | −31.710 | 14.783 | 1.00 | 27.87 | A | O |
| ATOM | 2840 | N | HIS | A | 202 | 65.784 | −32.192 | 13.382 | 1.00 | 27.02 | A | N |
| ATOM | 2841 | CA | HIS | A | 202 | 65.237 | −31.386 | 12.299 | 1.00 | 26.81 | A | C |
| ATOM | 2843 | CB | HIS | A | 202 | 66.303 | −31.281 | 11.211 | 1.00 | 27.94 | A | C |
| ATOM | 2846 | CG | HIS | A | 202 | 65.862 | −30.625 | 9.942 | 1.00 | 26.52 | A | C |
| ATOM | 2847 | ND1 | HIS | A | 202 | 65.804 | −29.258 | 9.788 | 1.00 | 29.59 | A | N |
| ATOM | 2849 | CE1 | HIS | A | 202 | 65.435 | −28.970 | 8.554 | 1.00 | 28.13 | A | C |
| ATOM | 2851 | NE2 | HIS | A | 202 | 65.288 | −30.102 | 7.890 | 1.00 | 26.07 | A | N |
| ATOM | 2853 | CD2 | HIS | A | 202 | 65.564 | −31.150 | 8.733 | 1.00 | 26.24 | A | C |
| ATOM | 2855 | C | HIS | A | 202 | 63.901 | −32.018 | 11.785 | 1.00 | 25.69 | A | C |
| ATOM | 2856 | O | HIS | A | 202 | 62.890 | −31.339 | 11.667 | 1.00 | 21.65 | A | O |
| ATOM | 2858 | N | ALA | A | 203 | 63.867 | −33.315 | 11.553 | 1.00 | 25.23 | A | N |
| ATOM | 2859 | CA | ALA | A | 203 | 62.598 | −33.931 | 11.112 | 1.00 | 25.49 | A | C |
| ATOM | 2861 | CB | ALA | A | 203 | 62.812 | −35.337 | 10.748 | 1.00 | 24.59 | A | C |
| ATOM | 2865 | C | ALA | A | 203 | 61.489 | −33.824 | 12.173 | 1.00 | 27.25 | A | C |
| ATOM | 2866 | O | ALA | A | 203 | 60.321 | −33.627 | 11.837 | 1.00 | 29.18 | A | O |
| ATOM | 2868 | N | LEU | A | 204 | 61.839 | −33.928 | 13.451 | 1.00 | 26.81 | A | N |
| ATOM | 2869 | CA | LEU | A | 204 | 60.807 | −33.831 | 14.517 | 1.00 | 26.42 | A | C |
| ATOM | 2871 | CB | LEU | A | 204 | 61.317 | −34.405 | 15.850 | 1.00 | 24.88 | A | C |
| ATOM | 2874 | CG | LEU | A | 204 | 61.517 | −35.936 | 15.832 | 1.00 | 26.48 | A | C |
| ATOM | 2876 | CD1 | LEU | A | 204 | 62.119 | −36.465 | 17.114 | 1.00 | 26.30 | A | C |
| ATOM | 2880 | CD2 | LEU | A | 204 | 60.203 | −36.639 | 15.557 | 1.00 | 23.97 | A | C |
| ATOM | 2884 | C | LEU | A | 204 | 60.305 | −32.392 | 14.672 | 1.00 | 27.71 | A | C |
| ATOM | 2885 | O | LEU | A | 204 | 59.148 | −32.160 | 15.001 | 1.00 | 27.30 | A | O |
| ATOM | 2887 | N | GLU | A | 205 | 61.183 | −31.430 | 14.415 | 1.00 | 27.31 | A | N |
| ATOM | 2888 | CA | GLU | A | 205 | 60.805 | −30.037 | 14.394 | 1.00 | 27.78 | A | C |
| ATOM | 2890 | CB | GLU | A | 205 | 62.015 | −29.143 | 14.068 | 1.00 | 27.71 | A | C |
| ATOM | 2893 | CG | GLU | A | 205 | 61.697 | −27.658 | 14.056 | 1.00 | 29.29 | A | C |
| ATOM | 2896 | CD | GLU | A | 205 | 62.860 | −26.816 | 13.541 | 1.00 | 37.90 | A | C |
| ATOM | 2897 | OE1 | GLU | A | 205 | 63.289 | −27.047 | 12.395 | 1.00 | 32.00 | A | O |
| ATOM | 2898 | OE2 | GLU | A | 205 | 63.349 | −25.930 | 14.288 | 1.00 | 44.77 | A | O |
| ATOM | 2899 | C | GLU | A | 205 | 59.729 | −29.859 | 13.348 | 1.00 | 27.03 | A | C |
| ATOM | 2900 | O | GLU | A | 205 | 58.699 | −29.270 | 13.627 | 1.00 | 27.56 | A | O |
| ATOM | 2902 | N | LEU | A | 206 | 59.982 | −30.359 | 12.144 | 1.00 | 25.59 | A | N |
| ATOM | 2903 | CA | LEU | A | 206 | 59.004 | −30.289 | 11.062 | 1.00 | 25.22 | A | C |
| ATOM | 2905 | CB | LEU | A | 206 | 58.886 | −28.840 | 10.561 | 1.00 | 24.64 | A | C |
| ATOM | 2908 | CG | LEU | A | 206 | 57.694 | −28.433 | 9.711 | 1.00 | 24.27 | A | C |
| ATOM | 2910 | CD1 | LEU | A | 206 | 56.411 | −28.371 | 10.529 | 1.00 | 17.46 | A | C |
| ATOM | 2914 | CD2 | LEU | A | 206 | 57.955 | −27.063 | 9.063 | 1.00 | 21.01 | A | C |
| ATOM | 2918 | C | LEU | A | 206 | 59.416 | −31.196 | 9.917 | 1.00 | 24.56 | A | C |
| ATOM | 2919 | O | LEU | A | 206 | 60.540 | −31.118 | 9.444 | 1.00 | 25.68 | A | O |
| ATOM | 2921 | N | PRO | A | 207 | 58.492 | −32.045 | 9.437 | 1.00 | 24.29 | A | N |
| ATOM | 2922 | CA | PRO | A | 207 | 58.784 | −32.963 | 8.354 | 1.00 | 23.07 | A | C |
| ATOM | 2924 | CB | PRO | A | 207 | 57.522 | −33.795 | 8.289 | 1.00 | 25.30 | A | C |
| ATOM | 2927 | CG | PRO | A | 207 | 56.469 | −32.830 | 8.679 | 1.00 | 25.11 | A | C |
| ATOM | 2930 | CD | PRO | A | 207 | 57.058 | −32.039 | 9.765 | 1.00 | 23.79 | A | C |
| ATOM | 2933 | C | PRO | A | 207 | 59.003 | −32.256 | 7.014 | 1.00 | 21.55 | A | C |
| ATOM | 2934 | O | PRO | A | 207 | 58.522 | −31.166 | 6.819 | 1.00 | 22.11 | A | O |
| ATOM | 2935 | N | LEU | A | 208 | 59.694 | −32.924 | 6.102 | 1.00 | 22.41 | A | N |
| ATOM | 2936 | CA | LEU | A | 208 | 60.022 | −32.401 | 4.805 | 1.00 | 22.23 | A | C |
| ATOM | 2938 | CB | LEU | A | 208 | 60.690 | −33.496 | 3.997 | 1.00 | 26.10 | A | C |
| ATOM | 2941 | CG | LEU | A | 208 | 62.061 | −33.942 | 4.475 | 1.00 | 32.53 | A | C |
| ATOM | 2943 | CD1 | LEU | A | 208 | 62.395 | −35.348 | 3.945 | 1.00 | 35.78 | A | C |
| ATOM | 2947 | CD2 | LEU | A | 208 | 63.091 | −32.897 | 4.009 | 1.00 | 35.33 | A | C |
| ATOM | 2951 | C | LEU | A | 208 | 58.814 | −31.930 | 4.019 | 1.00 | 23.30 | A | C |
| ATOM | 2952 | O | LEU | A | 208 | 58.865 | −30.914 | 3.333 | 1.00 | 27.80 | A | O |
| ATOM | 2954 | N | HIS | A | 209 | 57.733 | −32.688 | 4.081 | 1.00 | 21.48 | A | N |

TABLE 4-2-continued

| Coordinates of *P. alba* IspS | | | | | | | | | | | | |
|---|---|---|---|---|---|---|---|---|---|---|---|---|
| ATOM | 2955 | CA | HIS | A | 209 | 56.531 | −32.356 | 3.333 | 1.00 | 20.94 | A | C |
| ATOM | 2957 | CB | HIS | A | 209 | 55.497 | −33.453 | 3.521 | 1.00 | 20.23 | A | C |
| ATOM | 2960 | CG | HIS | A | 209 | 54.347 | −33.380 | 2.571 | 1.00 | 21.97 | A | C |
| ATOM | 2961 | ND1 | HIS | A | 209 | 54.509 | −33.408 | 1.200 | 1.00 | 19.00 | A | N |
| ATOM | 2963 | CE1 | HIS | A | 209 | 53.316 | −33.366 | 0.621 | 1.00 | 17.86 | A | C |
| ATOM | 2965 | NE2 | HIS | A | 209 | 52.392 | −33.319 | 1.568 | 1.00 | 20.62 | A | N |
| ATOM | 2967 | CD2 | HIS | A | 209 | 53.011 | −33.333 | 2.797 | 1.00 | 17.40 | A | C |
| ATOM | 2969 | C | HIS | A | 209 | 55.890 | −31.039 | 3.769 | 1.00 | 20.60 | A | C |
| ATOM | 2970 | O | HIS | A | 209 | 55.095 | −30.479 | 3.030 | 1.00 | 22.10 | A | O |
| ATOM | 2972 | N | ARG | A | 210 | 56.182 | −30.578 | 4.970 | 1.00 | 19.06 | A | N |
| ATOM | 2973 | CA | ARG | A | 210 | 55.590 | −29.330 | 5.442 | 1.00 | 21.68 | A | C |
| ATOM | 2975 | CB | ARG | A | 210 | 54.984 | −29.513 | 6.825 | 1.00 | 21.62 | A | C |
| ATOM | 2978 | CG | ARG | A | 210 | 53.868 | −30.527 | 6.845 | 1.00 | 21.69 | A | C |
| ATOM | 2981 | CD | ARG | A | 210 | 53.157 | −30.548 | 8.198 | 1.00 | 21.87 | A | C |
| ATOM | 2984 | NE | ARG | A | 210 | 52.032 | −31.469 | 8.145 | 1.00 | 28.50 | A | N |
| ATOM | 2986 | CZ | ARG | A | 210 | 51.306 | −31.867 | 9.185 | 1.00 | 27.73 | A | C |
| ATOM | 2987 | NH1 | ARG | A | 210 | 51.565 | −31.422 | 10.396 | 1.00 | 25.20 | A | N |
| ATOM | 2990 | NH2 | ARG | A | 210 | 50.306 | −32.732 | 9.001 | 1.00 | 22.65 | A | N |
| ATOM | 2993 | C | ARG | A | 210 | 56.554 | −28.162 | 5.510 | 1.00 | 23.56 | A | C |
| ATOM | 2994 | O | ARG | A | 210 | 56.098 | −27.052 | 5.712 | 1.00 | 25.20 | A | O |
| ATOM | 2996 | N | ARG | A | 211 | 57.861 | −28.390 | 5.317 | 1.00 | 22.15 | A | N |
| ATOM | 2997 | CA | ARG | A | 211 | 58.824 | −27.328 | 5.454 | 1.00 | 22.08 | A | C |
| ATOM | 2999 | CB | ARG | A | 211 | 60.164 | −27.898 | 5.911 | 1.00 | 21.53 | A | C |
| ATOM | 3002 | CG | ARG | A | 211 | 61.184 | −26.803 | 6.252 | 1.00 | 25.30 | A | C |
| ATOM | 3005 | CD | ARG | A | 211 | 62.498 | −27.377 | 6.683 | 1.00 | 23.90 | A | C |
| ATOM | 3008 | NE | ARG | A | 211 | 62.394 | −28.298 | 7.815 | 1.00 | 20.68 | A | N |
| ATOM | 3010 | CZ | ARG | A | 211 | 62.577 | −27.968 | 9.097 | 1.00 | 29.21 | A | C |
| ATOM | 3011 | NH1 | ARG | A | 211 | 62.842 | −26.723 | 9.458 | 1.00 | 31.64 | A | N |
| ATOM | 3014 | NH2 | ARG | A | 211 | 62.482 | −28.895 | 10.040 | 1.00 | 33.26 | A | N |
| ATOM | 3017 | C | ARG | A | 211 | 58.995 | −26.636 | 4.124 | 1.00 | 22.87 | A | C |
| ATOM | 3018 | O | ARG | A | 211 | 58.943 | −27.308 | 3.080 | 1.00 | 23.69 | A | O |
| ATOM | 3020 | N | THR | A | 212 | 59.225 | −25.313 | 4.131 | 1.00 | 21.93 | A | N |
| ATOM | 3021 | CA | THR | A | 212 | 59.457 | −24.587 | 2.846 | 1.00 | 22.40 | A | C |
| ATOM | 3023 | CB | THR | A | 212 | 59.553 | −23.073 | 3.006 | 1.00 | 21.65 | A | C |
| ATOM | 3025 | OG1 | THR | A | 212 | 60.391 | −22.782 | 4.111 | 1.00 | 28.79 | A | O |
| ATOM | 3027 | CG2 | THR | A | 212 | 58.204 | −22.457 | 3.215 | 1.00 | 21.41 | A | C |
| ATOM | 3031 | C | THR | A | 212 | 60.748 | −25.035 | 2.161 | 1.00 | 24.44 | A | C |
| ATOM | 3032 | O | THR | A | 212 | 61.667 | −25.593 | 2.790 | 1.00 | 22.73 | A | O |
| ATOM | 3034 | N | GLN | A | 213 | 60.831 | −24.769 | 0.862 | 1.00 | 24.88 | A | N |
| ATOM | 3035 | CA | GLN | A | 213 | 61.890 | −25.361 | 0.042 | 1.00 | 23.30 | A | C |
| ATOM | 3037 | CB | GLN | A | 213 | 61.510 | −25.230 | −1.431 | 1.00 | 22.38 | A | C |
| ATOM | 3040 | CG | GLN | A | 213 | 62.232 | −26.167 | −2.392 | 1.00 | 26.87 | A | C |
| ATOM | 3043 | CD | GLN | A | 213 | 63.551 | −25.606 | −2.913 | 1.00 | 30.03 | A | C |
| ATOM | 3044 | OE1 | GLN | A | 213 | 64.199 | −24.764 | −2.277 | 1.00 | 31.33 | A | O |
| ATOM | 3045 | NE2 | GLN | A | 213 | 63.969 | −26.095 | −4.062 | 1.00 | 27.33 | A | N |
| ATOM | 3048 | C | GLN | A | 213 | 63.238 | −24.674 | 0.385 | 1.00 | 23.77 | A | C |
| ATOM | 3049 | O | GLN | A | 213 | 64.269 | −25.339 | 0.641 | 1.00 | 23.11 | A | O |
| ATOM | 3051 | N | ARG | A | 214 | 63.242 | −23.348 | 0.444 | 1.00 | 22.75 | A | N |
| ATOM | 3052 | CA | ARG | A | 214 | 64.496 | −22.646 | 0.771 | 1.00 | 22.94 | A | C |
| ATOM | 3054 | CB | ARG | A | 214 | 64.351 | −21.150 | 0.591 | 1.00 | 21.67 | A | C |
| ATOM | 3057 | CG | ARG | A | 214 | 64.105 | −20.728 | −0.863 | 1.00 | 25.36 | A | C |
| ATOM | 3060 | CD | ARG | A | 214 | 65.370 | −20.851 | −1.745 | 1.00 | 25.37 | A | C |
| ATOM | 3063 | NE | ARG | A | 214 | 65.517 | −22.198 | −2.265 | 1.00 | 19.85 | A | N |
| ATOM | 3065 | CZ | ARG | A | 214 | 66.500 | −22.609 | −3.067 | 1.00 | 22.24 | A | C |
| ATOM | 3066 | NH1 | ARG | A | 214 | 67.440 | −21.780 | −3.482 | 1.00 | 23.25 | A | N |
| ATOM | 3069 | NH2 | ARG | A | 214 | 66.530 | −23.870 | −3.478 | 1.00 | 21.78 | A | N |
| ATOM | 3072 | C | ARG | A | 214 | 65.045 | −22.987 | 2.163 | 1.00 | 22.57 | A | C |
| ATOM | 3073 | O | ARG | A | 214 | 66.276 | −23.153 | 2.325 | 1.00 | 22.67 | A | O |
| ATOM | 3075 | N | LEU | A | 215 | 64.168 | −23.142 | 3.156 | 1.00 | 21.88 | A | N |
| ATOM | 3076 | CA | LEU | A | 215 | 64.640 | −23.425 | 4.534 | 1.00 | 22.10 | A | C |
| ATOM | 3078 | CB | LEU | A | 215 | 63.530 | −23.342 | 5.574 | 1.00 | 23.69 | A | C |
| ATOM | 3081 | CG | LEU | A | 215 | 63.166 | −22.064 | 6.320 | 1.00 | 34.74 | A | C |
| ATOM | 3083 | CD1 | LEU | A | 215 | 64.377 | −21.478 | 7.038 | 1.00 | 30.99 | A | C |
| ATOM | 3087 | CD2 | LEU | A | 215 | 62.022 | −22.394 | 7.334 | 1.00 | 34.69 | A | C |
| ATOM | 3091 | C | LEU | A | 215 | 65.225 | −24.807 | 4.601 | 1.00 | 21.97 | A | C |
| ATOM | 3092 | O | LEU | A | 215 | 66.251 | −25.033 | 5.243 | 1.00 | 23.04 | A | O |
| ATOM | 3094 | N | GLU | A | 216 | 64.563 | −25.759 | 3.964 | 1.00 | 22.38 | A | N |
| ATOM | 3095 | CA | GLU | A | 216 | 65.143 | −27.091 | 3.849 | 1.00 | 23.79 | A | C |
| ATOM | 3097 | CB | GLU | A | 216 | 64.203 | −28.054 | 3.092 | 1.00 | 24.11 | A | C |
| ATOM | 3100 | CG | GLU | A | 216 | 64.735 | −29.469 | 3.009 | 1.00 | 23.98 | A | C |
| ATOM | 3103 | CD | GLU | A | 216 | 65.092 | −30.054 | 4.372 | 1.00 | 30.09 | A | C |
| ATOM | 3104 | OE1 | GLU | A | 216 | 64.489 | −29.635 | 5.368 | 1.00 | 38.31 | A | O |
| ATOM | 3105 | OE2 | GLU | A | 216 | 65.963 | −30.950 | 4.462 | 1.00 | 31.71 | A | O |
| ATOM | 3106 | C | GLU | A | 216 | 66.495 | −27.043 | 3.151 | 1.00 | 22.00 | A | C |
| ATOM | 3107 | O | GLU | A | 216 | 67.417 | −27.725 | 3.566 | 1.00 | 25.42 | A | O |
| ATOM | 3109 | N | ALA | A | 217 | 66.609 | −26.265 | 2.075 | 1.00 | 21.69 | A | N |
| ATOM | 3110 | CA | ALA | A | 217 | 67.860 | −26.207 | 1.307 | 1.00 | 21.04 | A | C |
| ATOM | 3112 | CB | ALA | A | 217 | 67.713 | −25.322 | 0.057 | 1.00 | 16.62 | A | C |

TABLE 4-2-continued

Coordinates of *P. alba* IspS

| | | | | | | | | | | | | |
|---|---|---|---|---|---|---|---|---|---|---|---|---|
| ATOM | 3116 | C | ALA | A | 217 | 68.997 | −25.695 | 2.170 | 1.00 | 22.50 | A | C |
| ATOM | 3117 | O | ALA | A | 217 | 70.086 | −26.294 | 2.207 | 1.00 | 24.32 | A | O |
| ATOM | 3119 | N | VAL | A | 218 | 68.754 | −24.598 | 2.880 | 1.00 | 22.51 | A | N |
| ATOM | 3120 | CA | VAL | A | 218 | 69.841 | −23.970 | 3.638 | 1.00 | 23.74 | A | C |
| ATOM | 3122 | CB | VAL | A | 218 | 69.501 | −22.546 | 4.127 | 1.00 | 24.58 | A | C |
| ATOM | 3124 | CG1 | VAL | A | 218 | 68.630 | −22.593 | 5.350 | 1.00 | 23.58 | A | C |
| ATOM | 3128 | CG2 | VAL | A | 218 | 70.816 | −21.738 | 4.397 | 1.00 | 28.37 | A | C |
| ATOM | 3132 | C | VAL | A | 218 | 70.244 | −24.871 | 4.785 | 1.00 | 23.83 | A | C |
| ATOM | 3133 | O | VAL | A | 218 | 71.408 | −24.959 | 5.120 | 1.00 | 28.06 | A | O |
| ATOM | 3135 | N | TRP | A | 219 | 69.292 | −25.582 | 5.366 | 1.00 | 25.17 | A | N |
| ATOM | 3136 | CA | TRP | A | 219 | 69.614 | −26.553 | 6.384 | 1.00 | 24.87 | A | C |
| ATOM | 3138 | CB | TRP | A | 219 | 68.353 | −27.038 | 7.105 | 1.00 | 25.79 | A | C |
| ATOM | 3141 | CG | TRP | A | 219 | 68.684 | −27.877 | 8.273 | 1.00 | 25.24 | A | C |
| ATOM | 3142 | CD1 | TRP | A | 219 | 68.904 | −27.444 | 9.559 | 1.00 | 26.80 | A | C |
| ATOM | 3144 | NE1 | TRP | A | 219 | 69.218 | −28.508 | 10.361 | 1.00 | 24.26 | A | N |
| ATOM | 3146 | CE2 | TRP | A | 219 | 69.240 | −29.648 | 9.604 | 1.00 | 28.74 | A | C |
| ATOM | 3147 | CD2 | TRP | A | 219 | 68.921 | −29.281 | 8.274 | 1.00 | 20.92 | A | C |
| ATOM | 3148 | CE3 | TRP | A | 219 | 68.869 | −30.273 | 7.291 | 1.00 | 28.67 | A | C |
| ATOM | 3150 | CZ3 | TRP | A | 219 | 69.133 | −31.587 | 7.659 | 1.00 | 31.01 | A | C |
| ATOM | 3152 | CH2 | TRP | A | 219 | 69.464 | −31.920 | 8.991 | 1.00 | 31.59 | A | C |
| ATOM | 3154 | CZ2 | TRP | A | 219 | 69.524 | −30.968 | 9.974 | 1.00 | 31.18 | A | C |
| ATOM | 3156 | C | TRP | A | 219 | 70.368 | −27.756 | 5.817 | 1.00 | 23.79 | A | C |
| ATOM | 3157 | O | TRP | A | 219 | 71.341 | −28.186 | 6.403 | 1.00 | 26.06 | A | O |
| ATOM | 3159 | N | SER | A | 220 | 69.912 | −28.314 | 4.700 | 1.00 | 23.59 | A | N |
| ATOM | 3160 | CA | SER | A | 220 | 70.515 | −29.556 | 4.168 | 1.00 | 23.50 | A | C |
| ATOM | 3162 | CB | SER | A | 220 | 69.604 | −30.197 | 3.104 | 1.00 | 23.55 | A | C |
| ATOM | 3165 | OG | SER | A | 220 | 68.632 | −31.034 | 3.711 | 1.00 | 29.70 | A | O |
| ATOM | 3167 | C | SER | A | 220 | 71.909 | −29.365 | 3.572 | 1.00 | 23.39 | A | C |
| ATOM | 3168 | O | SER | A | 220 | 72.739 | −30.270 | 3.630 | 1.00 | 25.12 | A | O |
| ATOM | 3170 | N | ILE | A | 221 | 72.141 | −28.206 | 2.976 | 1.00 | 23.77 | A | N |
| ATOM | 3171 | CA | ILE | A | 221 | 73.448 | −27.844 | 2.429 | 1.00 | 27.11 | A | C |
| ATOM | 3173 | CB | ILE | A | 221 | 73.397 | −26.472 | 1.704 | 1.00 | 26.36 | A | C |
| ATOM | 3175 | CG1 | ILE | A | 221 | 72.680 | −26.608 | 0.360 | 1.00 | 22.83 | A | C |
| ATOM | 3178 | CD1 | ILE | A | 221 | 72.358 | −25.299 | −0.336 | 1.00 | 15.93 | A | C |
| ATOM | 3182 | CG2 | ILE | A | 221 | 74.804 | −25.940 | 1.473 | 1.00 | 28.45 | A | C |
| ATOM | 3186 | C | ILE | A | 221 | 74.509 | −27.769 | 3.525 | 1.00 | 28.33 | A | C |
| ATOM | 3187 | O | ILE | A | 221 | 75.621 | −28.265 | 3.366 | 1.00 | 28.37 | A | O |
| ATOM | 3189 | N | GLU | A | 222 | 74.165 | −27.148 | 4.640 | 1.00 | 29.36 | A | N |
| ATOM | 3190 | CA | GLU | A | 222 | 75.089 | −27.078 | 5.770 | 1.00 | 29.36 | A | C |
| ATOM | 3192 | CB | GLU | A | 222 | 74.540 | −26.124 | 6.842 | 1.00 | 29.54 | A | C |
| ATOM | 3195 | CG | GLU | A | 222 | 75.301 | −26.042 | 8.170 | 1.00 | 37.23 | A | C |
| ATOM | 3198 | CD | GLU | A | 222 | 76.756 | −25.564 | 8.041 | 1.00 | 40.53 | A | C |
| ATOM | 3199 | OE1 | GLU | A | 222 | 77.153 | −25.010 | 6.984 | 1.00 | 44.11 | A | O |
| ATOM | 3200 | OE2 | GLU | A | 222 | 77.499 | −25.737 | 9.030 | 1.00 | 46.46 | A | O |
| ATOM | 3201 | C | GLU | A | 222 | 75.311 | −28.503 | 6.286 | 1.00 | 29.13 | A | C |
| ATOM | 3202 | O | GLU | A | 222 | 76.438 | −28.891 | 6.532 | 1.00 | 28.56 | A | O |
| ATOM | 3204 | N | ALA | A | 223 | 74.246 | −29.305 | 6.379 | 1.00 | 28.23 | A | N |
| ATOM | 3205 | CA | ALA | A | 223 | 74.377 | −30.670 | 6.882 | 1.00 | 27.59 | A | C |
| ATOM | 3207 | CB | ALA | A | 223 | 73.003 | −31.344 | 7.026 | 1.00 | 29.69 | A | C |
| ATOM | 3211 | C | ALA | A | 223 | 75.255 | −31.497 | 5.959 | 1.00 | 28.61 | A | C |
| ATOM | 3212 | O | ALA | A | 223 | 76.131 | −32.225 | 6.420 | 1.00 | 28.90 | A | O |
| ATOM | 3214 | N | TYR | A | 224 | 74.995 | −31.386 | 4.657 | 1.00 | 27.73 | A | N |
| ATOM | 3215 | CA | TYR | A | 224 | 75.677 | −32.186 | 3.652 | 1.00 | 28.06 | A | C |
| ATOM | 3217 | CB | TYR | A | 224 | 75.020 | −31.964 | 2.284 | 1.00 | 26.68 | A | C |
| ATOM | 3220 | CG | TYR | A | 224 | 75.272 | −33.036 | 1.247 | 1.00 | 23.01 | A | C |
| ATOM | 3221 | CD1 | TYR | A | 224 | 74.715 | −34.296 | 1.372 | 1.00 | 24.54 | A | C |
| ATOM | 3223 | CE1 | TYR | A | 224 | 74.929 | −35.278 | 0.410 | 1.00 | 28.25 | A | C |
| ATOM | 3225 | CZ | TYR | A | 224 | 75.687 | −34.995 | −0.710 | 1.00 | 26.14 | A | C |
| ATOM | 3226 | OH | TYR | A | 224 | 75.902 | −35.965 | −1.669 | 1.00 | 30.14 | A | O |
| ATOM | 3228 | CE2 | TYR | A | 224 | 76.244 | −33.755 | −0.859 | 1.00 | 24.49 | A | C |
| ATOM | 3230 | CD2 | TYR | A | 224 | 76.030 | −32.772 | 0.112 | 1.00 | 25.46 | A | C |
| ATOM | 3232 | C | TYR | A | 224 | 77.166 | −31.809 | 3.607 | 1.00 | 28.75 | A | C |
| ATOM | 3233 | O | TYR | A | 224 | 78.029 | −32.671 | 3.448 | 1.00 | 27.95 | A | O |
| ATOM | 3235 | N | ARG | A | 225 | 77.452 | −30.525 | 3.769 | 1.00 | 29.70 | A | N |
| ATOM | 3236 | CA | ARG | A | 225 | 78.833 | −30.042 | 3.733 | 1.00 | 34.37 | A | C |
| ATOM | 3238 | CB | ARG | A | 225 | 78.874 | −28.525 | 3.945 | 1.00 | 34.39 | A | C |
| ATOM | 3241 | CG | ARG | A | 225 | 80.182 | −27.914 | 3.518 | 1.00 | 42.08 | A | C |
| ATOM | 3244 | CD | ARG | A | 225 | 80.440 | −26.599 | 4.201 | 1.00 | 44.17 | A | C |
| ATOM | 3247 | NE | ARG | A | 225 | 79.492 | −25.587 | 3.768 | 1.00 | 33.41 | A | N |
| ATOM | 3249 | CZ | ARG | A | 225 | 79.757 | −24.598 | 2.921 | 1.00 | 31.84 | A | C |
| ATOM | 3250 | NH1 | ARG | A | 225 | 80.969 | −24.440 | 2.360 | 1.00 | 26.16 | A | N |
| ATOM | 3253 | NH2 | ARG | A | 225 | 78.789 | −23.732 | 2.647 | 1.00 | 28.39 | A | N |
| ATOM | 3256 | C | ARG | A | 225 | 79.731 | −30.720 | 4.782 | 1.00 | 34.95 | A | C |
| ATOM | 3257 | O | ARG | A | 225 | 80.924 | −30.847 | 4.571 | 1.00 | 33.72 | A | O |
| ATOM | 3259 | N | LYS | A | 226 | 79.148 | −31.153 | 5.897 | 1.00 | 38.87 | A | N |
| ATOM | 3260 | CA | LYS | A | 226 | 79.895 | −31.805 | 6.980 | 1.00 | 41.98 | A | C |
| ATOM | 3262 | CB | LYS | A | 226 | 79.195 | −31.585 | 8.323 | 1.00 | 41.81 | A | C |
| ATOM | 3265 | CG | LYS | A | 226 | 79.118 | −30.139 | 8.760 | 1.00 | 43.92 | A | C |

TABLE 4-2-continued

Coordinates of *P. alba* IspS

| | | | | | | | | | | | | |
|---|---|---|---|---|---|---|---|---|---|---|---|---|
| ATOM | 3268 | CD | LYS | A | 226 | 78.200 | −30.008 | 9.967 | 1.00 | 48.86 | A | C |
| ATOM | 3271 | CE | LYS | A | 226 | 77.814 | −28.571 | 10.214 | 1.00 | 50.51 | A | C |
| ATOM | 3274 | NZ | LYS | A | 226 | 76.638 | −28.436 | 11.125 | 1.00 | 50.92 | A | N |
| ATOM | 3278 | C | LYS | A | 226 | 80.099 | −33.305 | 6.780 | 1.00 | 43.06 | A | C |
| ATOM | 3279 | O | LYS | A | 226 | 80.952 | −33.885 | 7.435 | 1.00 | 43.06 | A | O |
| ATOM | 3281 | N | LYS | A | 227 | 79.322 | −33.938 | 5.905 | 1.00 | 44.99 | A | N |
| ATOM | 3282 | CA | LYS | A | 227 | 79.499 | −35.372 | 5.641 | 1.00 | 46.76 | A | C |
| ATOM | 3284 | CB | LYS | A | 227 | 78.334 | −35.933 | 4.840 | 1.00 | 46.98 | A | C |
| ATOM | 3287 | CG | LYS | A | 227 | 76.994 | −35.858 | 5.523 | 1.00 | 51.16 | A | C |
| ATOM | 3290 | CD | LYS | A | 227 | 76.018 | −36.864 | 4.900 | 1.00 | 58.14 | A | C |
| ATOM | 3293 | CE | LYS | A | 227 | 74.634 | −36.793 | 5.566 | 1.00 | 65.96 | A | C |
| ATOM | 3296 | NZ | LYS | A | 227 | 74.529 | −37.575 | 6.846 | 1.00 | 67.08 | A | N |
| ATOM | 3300 | C | LYS | A | 227 | 80.786 | −35.607 | 4.854 | 1.00 | 48.34 | A | C |
| ATOM | 3301 | O | LYS | A | 227 | 80.992 | −34.995 | 3.799 | 1.00 | 48.62 | A | O |
| ATOM | 3303 | N | GLU | A | 228 | 81.638 | −36.503 | 5.359 | 1.00 | 49.33 | A | N |
| ATOM | 3304 | CA | GLU | A | 228 | 82.956 | −36.761 | 4.757 | 1.00 | 49.51 | A | C |
| ATOM | 3306 | CB | GLU | A | 228 | 83.814 | −37.641 | 5.689 | 1.00 | 50.88 | A | C |
| ATOM | 3309 | CG | GLU | A | 228 | 85.196 | −38.038 | 5.113 | 1.00 | 58.59 | A | C |
| ATOM | 3312 | CD | GLU | A | 228 | 86.120 | −38.742 | 6.127 | 1.00 | 63.27 | A | C |
| ATOM | 3313 | OE1 | GLU | A | 228 | 86.715 | −38.048 | 6.986 | 1.00 | 63.25 | A | O |
| ATOM | 3314 | OE2 | GLU | A | 228 | 86.269 | −39.985 | 6.040 | 1.00 | 60.49 | A | O |
| ATOM | 3315 | C | GLU | A | 228 | 82.839 | −37.401 | 3.370 | 1.00 | 47.39 | A | C |
| ATOM | 3316 | O | GLU | A | 228 | 83.681 | −37.153 | 2.503 | 1.00 | 48.29 | A | O |
| ATOM | 3318 | N | ASP | A | 229 | 81.792 | −38.204 | 3.173 | 1.00 | 43.95 | A | N |
| ATOM | 3319 | CA | ASP | A | 229 | 81.528 | −38.887 | 1.903 | 1.00 | 42.40 | A | C |
| ATOM | 3321 | CB | ASP | A | 229 | 81.004 | −40.301 | 2.198 | 1.00 | 44.51 | A | C |
| ATOM | 3324 | CG | ASP | A | 229 | 79.635 | −40.288 | 2.889 | 1.00 | 48.08 | A | C |
| ATOM | 3325 | OD1 | ASP | A | 229 | 79.412 | −39.414 | 3.764 | 1.00 | 52.32 | A | O |
| ATOM | 3326 | OD2 | ASP | A | 229 | 78.791 | −41.154 | 2.563 | 1.00 | 55.55 | A | O |
| ATOM | 3327 | C | ASP | A | 229 | 80.505 | −38.161 | 1.001 | 1.00 | 39.47 | A | C |
| ATOM | 3328 | O | ASP | A | 229 | 79.905 | −38.774 | 0.111 | 1.00 | 38.26 | A | O |
| ATOM | 3330 | N | ALA | A | 230 | 80.287 | −36.871 | 1.232 | 1.00 | 35.85 | A | N |
| ATOM | 3331 | CA | ALA | A | 230 | 79.406 | −36.089 | 0.360 | 1.00 | 34.54 | A | C |
| ATOM | 3333 | CB | ALA | A | 230 | 79.252 | −34.654 | 0.911 | 1.00 | 34.43 | A | C |
| ATOM | 3337 | C | ALA | A | 230 | 79.943 | −36.039 | −1.075 | 1.00 | 31.71 | A | C |
| ATOM | 3338 | O | ALA | A | 230 | 81.139 | −35.893 | −1.293 | 1.00 | 31.71 | A | O |
| ATOM | 3340 | N | ASN | A | 231 | 79.052 | −36.149 | −2.048 | 1.00 | 30.30 | A | N |
| ATOM | 3341 | CA | ASN | A | 231 | 79.405 | −35.899 | −3.445 | 1.00 | 29.41 | A | C |
| ATOM | 3343 | CB | ASN | A | 231 | 78.209 | −36.246 | −4.341 | 1.00 | 28.84 | A | C |
| ATOM | 3346 | CG | ASN | A | 231 | 78.477 | −36.010 | −5.831 | 1.00 | 33.88 | A | C |
| ATOM | 3347 | OD1 | ASN | A | 231 | 79.040 | −34.979 | −6.245 | 1.00 | 29.21 | A | O |
| ATOM | 3348 | ND2 | ASN | A | 231 | 78.034 | −36.955 | −6.647 | 1.00 | 39.93 | A | N |
| ATOM | 3351 | C | ASN | A | 231 | 79.790 | −34.424 | −3.610 | 1.00 | 28.30 | A | C |
| ATOM | 3352 | O | ASN | A | 231 | 78.954 | −33.553 | −3.407 | 1.00 | 29.80 | A | O |
| ATOM | 3354 | N | GLN | A | 232 | 81.032 | −34.144 | −3.987 | 1.00 | 26.07 | A | N |
| ATOM | 3355 | CA | GLN | A | 232 | 81.501 | −32.758 | −4.080 | 1.00 | 26.86 | A | C |
| ATOM | 3357 | CB | GLN | A | 232 | 83.033 | −32.713 | −4.132 | 1.00 | 28.05 | A | C |
| ATOM | 3360 | CG | GLN | A | 232 | 83.748 | −33.343 | −2.907 | 1.00 | 32.80 | A | C |
| ATOM | 3363 | CD | GLN | A | 232 | 83.312 | −32.742 | −1.576 | 1.00 | 33.27 | A | C |
| ATOM | 3364 | OE1 | GLN | A | 232 | 83.561 | −31.573 | −1.287 | 1.00 | 32.93 | A | O |
| ATOM | 3365 | NE2 | GLN | A | 232 | 82.657 | −33.550 | −0.762 | 1.00 | 34.64 | A | N |
| ATOM | 3368 | C | GLN | A | 232 | 80.914 | −31.962 | −5.265 | 1.00 | 26.08 | A | C |
| ATOM | 3369 | O | GLN | A | 232 | 80.757 | −30.731 | −5.179 | 1.00 | 26.37 | A | O |
| ATOM | 3371 | N | VAL | A | 233 | 80.598 | −32.647 | −6.363 | 1.00 | 23.92 | A | N |
| ATOM | 3372 | CA | VAL | A | 233 | 79.939 | −32.005 | −7.513 | 1.00 | 23.21 | A | C |
| ATOM | 3374 | CB | VAL | A | 233 | 79.852 | −32.957 | −8.737 | 1.00 | 24.28 | A | C |
| ATOM | 3376 | CG1 | VAL | A | 233 | 78.831 | −32.450 | −9.732 | 1.00 | 19.74 | A | C |
| ATOM | 3380 | CG2 | VAL | A | 233 | 81.256 | −33.115 | −9.399 | 1.00 | 23.81 | A | C |
| ATOM | 3384 | C | VAL | A | 233 | 78.535 | −31.501 | −7.127 | 1.00 | 23.21 | A | C |
| ATOM | 3385 | O | VAL | A | 233 | 78.180 | −30.351 | −7.391 | 1.00 | 21.93 | A | O |
| ATOM | 3387 | N | LEU | A | 234 | 77.774 | −32.344 | −6.435 | 1.00 | 22.20 | A | N |
| ATOM | 3388 | CA | LEU | A | 234 | 76.438 | −31.982 | −5.981 | 1.00 | 22.67 | A | C |
| ATOM | 3390 | CB | LEU | A | 234 | 75.746 | −33.221 | −5.425 | 1.00 | 24.22 | A | C |
| ATOM | 3393 | CG | LEU | A | 234 | 74.276 | −33.151 | −4.995 | 1.00 | 25.50 | A | C |
| ATOM | 3395 | CD1 | LEU | A | 234 | 73.370 | −32.553 | −6.102 | 1.00 | 18.15 | A | C |
| ATOM | 3399 | CD2 | LEU | A | 234 | 73.833 | −34.547 | −4.622 | 1.00 | 18.42 | A | C |
| ATOM | 3403 | C | LEU | A | 234 | 76.469 | −30.846 | −4.941 | 1.00 | 23.82 | A | C |
| ATOM | 3404 | O | LEU | A | 234 | 75.701 | −29.896 | −5.041 | 1.00 | 24.91 | A | O |
| ATOM | 3406 | N | LEU | A | 235 | 77.374 | −30.930 | −3.966 | 1.00 | 23.57 | A | N |
| ATOM | 3407 | CA | LEU | A | 235 | 77.510 | −29.892 | −2.946 | 1.00 | 22.98 | A | C |
| ATOM | 3409 | CB | LEU | A | 235 | 78.597 | −30.259 | −1.944 | 1.00 | 24.41 | A | C |
| ATOM | 3412 | CG | LEU | A | 235 | 78.878 | −29.265 | −0.815 | 1.00 | 26.92 | A | C |
| ATOM | 3414 | CD1 | LEU | A | 235 | 77.604 | −29.078 | 0.019 | 1.00 | 15.89 | A | C |
| ATOM | 3418 | CD2 | LEU | A | 235 | 80.061 | −29.754 | 0.038 | 1.00 | 18.04 | A | C |
| ATOM | 3422 | C | LEU | A | 235 | 77.842 | −28.566 | −3.580 | 1.00 | 20.58 | A | C |
| ATOM | 3423 | O | LEU | A | 235 | 77.236 | −27.545 | −3.277 | 1.00 | 19.83 | A | O |
| ATOM | 3425 | N | GLU | A | 236 | 78.801 | −28.572 | −4.482 | 1.00 | 22.61 | A | N |
| ATOM | 3426 | CA | GLU | A | 236 | 79.170 | −27.327 | −5.122 | 1.00 | 22.75 | A | C |

TABLE 4-2-continued

| Coordinates of *P. alba* IspS | | | | | | | | | | | |
|---|---|---|---|---|---|---|---|---|---|---|---|
| ATOM | 3428 | CB | GLU | A | 236 | 80.383 | −27.502 | −6.026 | 1.00 | 22.70 | A | C |
| ATOM | 3431 | CG | GLU | A | 236 | 80.871 | −26.189 | −6.606 | 1.00 | 23.04 | A | C |
| ATOM | 3434 | CD | GLU | A | 236 | 82.258 | −26.245 | −7.215 | 1.00 | 27.07 | A | C |
| ATOM | 3435 | OE1 | GLU | A | 236 | 82.771 | −27.340 | −7.541 | 1.00 | 33.98 | A | O |
| ATOM | 3436 | OE2 | GLU | A | 236 | 82.838 | −25.154 | −7.363 | 1.00 | 30.70 | A | O |
| ATOM | 3437 | C | GLU | A | 236 | 77.973 | −26.757 | −5.875 | 1.00 | 21.06 | A | C |
| ATOM | 3438 | O | GLU | A | 236 | 77.621 | −25.602 | −5.693 | 1.00 | 23.31 | A | O |
| ATOM | 3440 | N | LEU | A | 237 | 77.318 | −27.567 | −6.691 | 1.00 | 22.06 | A | N |
| ATOM | 3441 | CA | LEU | A | 237 | 76.183 | −27.054 | −7.480 | 1.00 | 19.57 | A | C |
| ATOM | 3443 | CB | LEU | A | 237 | 75.566 | −28.155 | −8.336 | 1.00 | 15.98 | A | C |
| ATOM | 3446 | CG | LEU | A | 237 | 74.366 | −27.737 | −9.187 | 1.00 | 15.57 | A | C |
| ATOM | 3448 | CD1 | LEU | A | 237 | 74.786 | −26.710 | −10.243 | 1.00 | 14.06 | A | C |
| ATOM | 3452 | CD2 | LEU | A | 237 | 73.740 | −28.975 | −9.837 | 1.00 | 15.04 | A | C |
| ATOM | 3456 | C | LEU | A | 237 | 75.133 | −26.460 | −6.562 | 1.00 | 19.31 | A | C |
| ATOM | 3457 | O | LEU | A | 237 | 74.608 | −25.393 | −6.820 | 1.00 | 20.86 | A | O |
| ATOM | 3459 | N | ALA | A | 238 | 74.846 | −27.161 | −5.474 | 1.00 | 19.04 | A | N |
| ATOM | 3460 | CA | ALA | A | 238 | 73.834 | −26.739 | −4.531 | 1.00 | 18.52 | A | C |
| ATOM | 3462 | CB | ALA | A | 238 | 73.675 | −27.811 | −3.413 | 1.00 | 18.25 | A | C |
| ATOM | 3466 | C | ALA | A | 238 | 74.193 | −25.392 | −3.927 | 1.00 | 19.60 | A | C |
| ATOM | 3467 | O | ALA | A | 238 | 73.350 | −24.489 | −3.794 | 1.00 | 21.50 | A | O |
| ATOM | 3469 | N | ILE | A | 239 | 75.448 | −25.233 | −3.539 | 1.00 | 19.28 | A | N |
| ATOM | 3470 | CA | ILE | A | 239 | 75.849 | −23.943 | −2.994 | 1.00 | 19.80 | A | C |
| ATOM | 3472 | CB | ILE | A | 239 | 77.274 | −23.988 | −2.476 | 1.00 | 20.00 | A | C |
| ATOM | 3474 | CG1 | ILE | A | 239 | 77.319 | −24.875 | −1.218 | 1.00 | 17.31 | A | C |
| ATOM | 3477 | CD1 | ILE | A | 239 | 78.704 | −25.050 | −0.668 | 1.00 | 21.36 | A | C |
| ATOM | 3481 | CG2 | ILE | A | 239 | 77.786 | −22.592 | −2.202 | 1.00 | 17.51 | A | C |
| ATOM | 3485 | C | ILE | A | 239 | 75.665 | −22.871 | −4.062 | 1.00 | 20.41 | A | C |
| ATOM | 3486 | O | ILE | A | 239 | 75.042 | −21.848 | −3.806 | 1.00 | 19.36 | A | O |
| ATOM | 3488 | N | LEU | A | 240 | 76.198 | −23.118 | −5.258 | 1.00 | 21.30 | A | N |
| ATOM | 3489 | CA | LEU | A | 240 | 76.149 | −22.135 | −6.356 | 1.00 | 21.36 | A | C |
| ATOM | 3491 | CB | LEU | A | 240 | 76.776 | −22.696 | −7.645 | 1.00 | 22.81 | A | C |
| ATOM | 3494 | CG | LEU | A | 240 | 78.227 | −22.426 | −7.967 | 1.00 | 30.14 | A | C |
| ATOM | 3496 | CD1 | LEU | A | 240 | 78.568 | −23.128 | −9.255 | 1.00 | 32.64 | A | C |
| ATOM | 3500 | CD2 | LEU | A | 240 | 79.131 | −22.906 | −6.840 | 1.00 | 37.35 | A | C |
| ATOM | 3504 | C | LEU | A | 240 | 74.719 | −21.794 | −6.687 | 1.00 | 20.26 | A | C |
| ATOM | 3505 | O | LEU | A | 240 | 74.394 | −20.648 | −6.875 | 1.00 | 21.20 | A | O |
| ATOM | 3507 | N | ASP | A | 241 | 73.864 | −22.806 | −6.784 | 1.00 | 19.89 | A | N |
| ATOM | 3508 | CA | ASP | A | 241 | 72.482 | −22.569 | −7.156 | 1.00 | 20.98 | A | C |
| ATOM | 3510 | CB | ASP | A | 241 | 71.727 | −23.866 | −7.456 | 1.00 | 20.86 | A | C |
| ATOM | 3513 | CG | ASP | A | 241 | 70.487 | −23.614 | −8.317 | 1.00 | 26.59 | A | C |
| ATOM | 3514 | OD1 | ASP | A | 241 | 69.370 | −23.431 | −7.778 | 1.00 | 23.99 | A | O |
| ATOM | 3515 | OD2 | ASP | A | 241 | 70.638 | −23.525 | −9.538 | 1.00 | 24.62 | A | O |
| ATOM | 3516 | C | ASP | A | 241 | 71.741 | −21.775 | −6.091 | 1.00 | 21.28 | A | C |
| ATOM | 3517 | O | ASP | A | 241 | 70.980 | −20.872 | −6.411 | 1.00 | 22.40 | A | O |
| ATOM | 3519 | N | TYR | A | 242 | 71.967 | −22.089 | −4.828 | 1.00 | 20.15 | A | N |
| ATOM | 3520 | CA | TYR | A | 242 | 71.259 | −21.393 | −3.771 | 1.00 | 20.85 | A | C |
| ATOM | 3522 | CB | TYR | A | 242 | 71.568 | −22.050 | −2.438 | 1.00 | 22.45 | A | C |
| ATOM | 3525 | CG | TYR | A | 242 | 70.857 | −21.437 | −1.265 | 1.00 | 23.33 | A | C |
| ATOM | 3526 | CD1 | TYR | A | 242 | 69.691 | −21.998 | −0.761 | 1.00 | 18.55 | A | C |
| ATOM | 3528 | CE1 | TYR | A | 242 | 69.041 | −21.418 | 0.330 | 1.00 | 24.47 | A | C |
| ATOM | 3530 | CZ | TYR | A | 242 | 69.569 | −20.276 | 0.908 | 1.00 | 18.54 | A | C |
| ATOM | 3531 | OH | TYR | A | 242 | 68.956 | −19.675 | 1.972 | 1.00 | 25.94 | A | O |
| ATOM | 3533 | CE2 | TYR | A | 242 | 70.713 | −19.709 | 0.406 | 1.00 | 21.27 | A | C |
| ATOM | 3535 | CD2 | TYR | A | 242 | 71.346 | −20.283 | −0.666 | 1.00 | 19.29 | A | C |
| ATOM | 3537 | C | TYR | A | 242 | 71.620 | −19.907 | −3.718 | 1.00 | 22.79 | A | C |
| ATOM | 3538 | O | TYR | A | 242 | 70.727 | −19.047 | −3.526 | 1.00 | 22.49 | A | O |
| ATOM | 3540 | N | ASN | A | 243 | 72.912 | −19.603 | −3.864 | 1.00 | 20.76 | A | N |
| ATOM | 3541 | CA | ASN | A | 243 | 73.375 | −18.205 | −3.845 | 1.00 | 22.06 | A | C |
| ATOM | 3543 | CB | ASN | A | 243 | 74.906 | −18.124 | −3.672 | 1.00 | 20.78 | A | C |
| ATOM | 3546 | CG | ASN | A | 243 | 75.349 | −18.533 | −2.275 | 1.00 | 25.87 | A | C |
| ATOM | 3547 | OD1 | ASN | A | 243 | 74.529 | −18.590 | −1.347 | 1.00 | 27.54 | A | O |
| ATOM | 3548 | ND2 | ASN | A | 243 | 76.639 | −18.815 | −2.110 | 1.00 | 19.91 | A | N |
| ATOM | 3551 | C | ASN | A | 243 | 72.933 | −17.409 | −5.066 | 1.00 | 21.72 | A | C |
| ATOM | 3552 | O | ASN | A | 243 | 72.662 | −16.203 | −4.983 | 1.00 | 22.95 | A | O |
| ATOM | 3554 | N | MET | A | 244 | 72.846 | −18.070 | −6.205 | 1.00 | 21.84 | A | N |
| ATOM | 3555 | CA | MET | A | 244 | 72.301 | −17.412 | −7.384 | 1.00 | 23.63 | A | C |
| ATOM | 3557 | CB | MET | A | 244 | 72.478 | −18.316 | −8.582 | 1.00 | 23.14 | A | C |
| ATOM | 3560 | CG | MET | A | 244 | 71.729 | −17.885 | −9.801 | 1.00 | 25.17 | A | C |
| ATOM | 3563 | SD | MET | A | 244 | 71.520 | −19.311 | −10.849 | 1.00 | 37.78 | A | S |
| ATOM | 3564 | CE | MET | A | 244 | 70.066 | −20.130 | −10.156 | 1.00 | 36.34 | A | C |
| ATOM | 3568 | C | MET | A | 244 | 70.810 | −17.060 | −7.194 | 1.00 | 24.55 | A | C |
| ATOM | 3569 | O | MET | A | 244 | 70.367 | −15.958 | −7.524 | 1.00 | 27.20 | A | O |
| ATOM | 3571 | N | ILE | A | 245 | 70.029 | −17.988 | −6.665 | 1.00 | 23.34 | A | N |
| ATOM | 3572 | CA | ILE | A | 245 | 68.612 | −17.708 | −6.487 | 1.00 | 23.03 | A | C |
| ATOM | 3574 | CB | ILE | A | 245 | 67.828 | −18.961 | −6.067 | 1.00 | 23.79 | A | C |
| ATOM | 3576 | CG1 | ILE | A | 245 | 67.753 | −19.935 | −7.251 | 1.00 | 24.90 | A | C |
| ATOM | 3579 | CD1 | ILE | A | 245 | 67.053 | −21.262 | −6.934 | 1.00 | 20.17 | A | C |
| ATOM | 3583 | CG2 | ILE | A | 245 | 66.428 | −18.579 | −5.537 | 1.00 | 18.88 | A | C |

TABLE 4-2-continued

| Coordinates of *P. alba* IspS | | | | | | | | | | | | |
|---|---|---|---|---|---|---|---|---|---|---|---|---|
| ATOM | 3587 | C | ILE | A | 245 | 68.452 | −16.565 | −5.475 | 1.00 | 22.27 | A | C |
| ATOM | 3588 | O | ILE | A | 245 | 67.673 | −15.646 | −5.689 | 1.00 | 23.18 | A | O |
| ATOM | 3590 | N | GLN | A | 246 | 69.222 | −16.618 | −4.400 | 1.00 | 21.78 | A | N |
| ATOM | 3591 | CA | GLN | A | 246 | 69.201 | −15.585 | −3.385 | 1.00 | 22.32 | A | C |
| ATOM | 3593 | CB | GLN | A | 246 | 70.192 | −15.913 | −2.267 | 1.00 | 22.29 | A | C |
| ATOM | 3596 | CG | GLN | A | 246 | 70.105 | −14.977 | −1.079 | 1.00 | 22.47 | A | C |
| ATOM | 3599 | CD | GLN | A | 246 | 71.193 | −15.238 | −0.086 | 1.00 | 23.64 | A | C |
| ATOM | 3600 | OE1 | GLN | A | 246 | 72.333 | −14.876 | −0.330 | 1.00 | 30.86 | A | O |
| ATOM | 3601 | NE2 | GLN | A | 246 | 70.855 | −15.897 | 1.046 | 1.00 | 27.00 | A | N |
| ATOM | 3604 | C | GLN | A | 246 | 69.519 | −14.220 | −3.969 | 1.00 | 25.79 | A | C |
| ATOM | 3605 | O | GLN | A | 246 | 68.906 | −13.227 | −3.574 | 1.00 | 28.66 | A | O |
| ATOM | 3607 | N | SER | A | 247 | 70.448 | −14.156 | −4.918 | 1.00 | 24.24 | A | N |
| ATOM | 3608 | CA | SER | A | 247 | 70.741 | −12.881 | −5.566 | 1.00 | 25.76 | A | C |
| ATOM | 3610 | CB | SER | A | 247 | 71.984 | −12.957 | −6.460 | 1.00 | 25.65 | A | C |
| ATOM | 3613 | OG | SER | A | 247 | 71.670 | −13.655 | −7.661 | 1.00 | 32.02 | A | O |
| ATOM | 3615 | C | SER | A | 247 | 69.557 | −12.390 | −6.377 | 1.00 | 24.68 | A | C |
| ATOM | 3616 | O | SER | A | 247 | 69.434 | −11.184 | −6.615 | 1.00 | 26.69 | A | O |
| ATOM | 3618 | N | VAL | A | 248 | 68.700 | −13.295 | −6.833 | 1.00 | 23.54 | A | N |
| ATOM | 3619 | CA | VAL | A | 248 | 67.456 | −12.855 | −7.466 | 1.00 | 23.71 | A | C |
| ATOM | 3621 | CB | VAL | A | 248 | 66.766 | −13.966 | −8.265 | 1.00 | 26.06 | A | C |
| ATOM | 3623 | CG1 | VAL | A | 248 | 65.435 | −13.455 | −8.867 | 1.00 | 19.39 | A | C |
| ATOM | 3627 | CG2 | VAL | A | 248 | 67.716 | −14.472 | −9.386 | 1.00 | 23.18 | A | C |
| ATOM | 3631 | C | VAL | A | 248 | 66.521 | −12.281 | −6.398 | 1.00 | 25.20 | A | C |
| ATOM | 3632 | O | VAL | A | 248 | 65.871 | −11.268 | −6.617 | 1.00 | 28.02 | A | O |
| ATOM | 3634 | N | TYR | A | 249 | 66.482 | −12.898 | −5.231 | 1.00 | 23.81 | A | N |
| ATOM | 3635 | CA | TYR | A | 249 | 65.652 | −12.372 | −4.165 | 1.00 | 27.09 | A | C |
| ATOM | 3637 | CB | TYR | A | 249 | 65.642 | −13.297 | −2.919 | 1.00 | 27.78 | A | C |
| ATOM | 3640 | CG | TYR | A | 249 | 65.127 | −14.716 | −3.122 | 1.00 | 22.87 | A | C |
| ATOM | 3641 | CD1 | TYR | A | 249 | 64.358 | −15.066 | −4.225 | 1.00 | 20.29 | A | C |
| ATOM | 3643 | CE1 | TYR | A | 249 | 63.892 | −16.351 | −4.383 | 1.00 | 20.19 | A | C |
| ATOM | 3645 | CZ | TYR | A | 249 | 64.185 | −17.292 | −3.431 | 1.00 | 24.01 | A | C |
| ATOM | 3646 | OH | TYR | A | 249 | 63.731 | −18.576 | −3.586 | 1.00 | 21.28 | A | O |
| ATOM | 3648 | CE2 | TYR | A | 249 | 64.938 | −16.969 | −2.329 | 1.00 | 17.32 | A | C |
| ATOM | 3650 | CD2 | TYR | A | 249 | 65.402 | −15.698 | −2.185 | 1.00 | 22.81 | A | C |
| ATOM | 3652 | C | TYR | A | 249 | 66.152 | −10.995 | −3.752 | 1.00 | 28.26 | A | C |
| ATOM | 3653 | O | TYR | A | 249 | 65.361 | −10.086 | −3.502 | 1.00 | 28.96 | A | O |
| ATOM | 3655 | N | GLN | A | 250 | 67.470 | −10.835 | −3.655 | 1.00 | 30.13 | A | N |
| ATOM | 3656 | CA | GLN | A | 250 | 68.017 | −9.558 | −3.209 | 1.00 | 29.19 | A | C |
| ATOM | 3658 | CB | GLN | A | 250 | 69.523 | −9.646 | −2.980 | 1.00 | 29.25 | A | C |
| ATOM | 3661 | CG | GLN | A | 250 | 69.842 | −10.420 | −1.714 | 1.00 | 27.79 | A | C |
| ATOM | 3664 | CD | GLN | A | 250 | 71.234 | −11.016 | −1.662 | 1.00 | 32.54 | A | C |
| ATOM | 3665 | OE1 | GLN | A | 250 | 72.048 | −10.868 | −2.584 | 1.00 | 30.29 | A | O |
| ATOM | 3666 | NE2 | GLN | A | 250 | 71.510 | −11.717 | −0.573 | 1.00 | 28.97 | A | N |
| ATOM | 3669 | C | GLN | A | 250 | 67.616 | −8.450 | −4.174 | 1.00 | 29.47 | A | C |
| ATOM | 3670 | O | GLN | A | 250 | 67.253 | −7.356 | −3.727 | 1.00 | 30.74 | A | O |
| ATOM | 3672 | N | ARG | A | 251 | 67.600 | −8.748 | −5.471 | 1.00 | 29.60 | A | N |
| ATOM | 3673 | CA | ARG | A | 251 | 67.112 | −7.789 | −6.465 | 1.00 | 30.89 | A | C |
| ATOM | 3675 | CB | ARG | A | 251 | 67.463 | −8.185 | −7.905 | 1.00 | 32.50 | A | C |
| ATOM | 3678 | CG | ARG | A | 251 | 67.113 | −7.073 | −8.936 | 1.00 | 40.34 | A | C |
| ATOM | 3681 | CD | ARG | A | 251 | 67.748 | −7.272 | −10.319 | 1.00 | 50.67 | A | C |
| ATOM | 3684 | NE | ARG | A | 251 | 67.564 | −8.647 | −10.781 | 1.00 | 60.70 | A | N |
| ATOM | 3686 | CZ | ARG | A | 251 | 68.526 | −9.565 | −10.909 | 1.00 | 68.22 | A | C |
| ATOM | 3687 | NH1 | ARG | A | 251 | 69.808 | −9.281 | −10.650 | 1.00 | 66.48 | A | N |
| ATOM | 3690 | NH2 | ARG | A | 251 | 68.200 | −10.793 | −11.318 | 1.00 | 67.68 | A | N |
| ATOM | 3693 | C | ARG | A | 251 | 65.621 | −7.568 | −6.373 | 1.00 | 30.00 | A | C |
| ATOM | 3694 | O | ARG | A | 251 | 65.156 | −6.438 | −6.483 | 1.00 | 31.03 | A | O |
| ATOM | 3696 | N | ASP | A | 252 | 64.855 | −8.637 | −6.197 | 1.00 | 29.66 | A | N |
| ATOM | 3697 | CA | ASP | A | 252 | 63.422 | −8.487 | −6.004 | 1.00 | 27.76 | A | C |
| ATOM | 3699 | CB | ASP | A | 252 | 62.766 | −9.838 | −5.688 | 1.00 | 28.05 | A | C |
| ATOM | 3702 | CG | ASP | A | 252 | 62.734 | −10.802 | −6.881 | 1.00 | 31.72 | A | C |
| ATOM | 3703 | OD1 | ASP | A | 252 | 62.980 | −10.396 | −8.039 | 1.00 | 32.65 | A | O |
| ATOM | 3704 | OD2 | ASP | A | 252 | 62.453 | −11.998 | −6.635 | 1.00 | 31.73 | A | O |
| ATOM | 3705 | C | ASP | A | 252 | 63.149 | −7.507 | −4.849 | 1.00 | 27.28 | A | C |
| ATOM | 3706 | O | ASP | A | 252 | 62.343 | −6.590 | −4.965 | 1.00 | 28.15 | A | O |
| ATOM | 3708 | N | LEU | A | 253 | 63.831 | −7.709 | −3.738 | 1.00 | 28.14 | A | N |
| ATOM | 3709 | CA | LEU | A | 253 | 63.621 | −6.912 | −2.539 | 1.00 | 29.87 | A | C |
| ATOM | 3711 | CB | LEU | A | 253 | 64.347 | −7.566 | −1.372 | 1.00 | 29.41 | A | C |
| ATOM | 3714 | CG | LEU | A | 253 | 64.118 | −6.971 | −0.001 | 1.00 | 34.75 | A | C |
| ATOM | 3716 | CD1 | LEU | A | 253 | 62.630 | −6.934 | 0.321 | 1.00 | 26.24 | A | C |
| ATOM | 3720 | CD2 | LEU | A | 253 | 64.893 | −7.766 | 1.038 | 1.00 | 36.83 | A | C |
| ATOM | 3724 | C | LEU | A | 253 | 64.071 | −5.451 | −2.681 | 1.00 | 31.45 | A | C |
| ATOM | 3725 | O | LEU | A | 253 | 63.406 | −4.547 | −2.168 | 1.00 | 32.50 | A | O |
| ATOM | 3727 | N | ARG | A | 254 | 65.180 | −5.203 | −3.364 | 1.00 | 33.17 | A | N |
| ATOM | 3728 | CA | ARG | A | 254 | 65.632 | −3.810 | −3.557 | 1.00 | 34.97 | A | C |
| ATOM | 3730 | CB | ARG | A | 254 | 66.973 | −3.726 | −4.297 | 1.00 | 35.48 | A | C |
| ATOM | 3733 | CG | ARG | A | 254 | 68.190 | −3.919 | −3.399 | 1.00 | 40.57 | A | C |
| ATOM | 3736 | CD | ARG | A | 254 | 69.493 | −3.551 | −4.113 | 1.00 | 42.70 | A | C |
| ATOM | 3739 | NE | ARG | A | 254 | 69.666 | −4.290 | −5.366 | 1.00 | 42.33 | A | N |

TABLE 4-2-continued

| Coordinates of *P. alba* IspS | | | | | | | | | | | |
|---|---|---|---|---|---|---|---|---|---|---|---|
| ATOM | 3741 | CZ | ARG | A | 254 | 70.190 | −5.516 | −5.483 | 1.00 | 43.80 | A | C |
| ATOM | 3742 | NH1 | ARG | A | 254 | 70.619 | −6.197 | −4.422 | 1.00 | 40.69 | A | N |
| ATOM | 3745 | NH2 | ARG | A | 254 | 70.293 | −6.067 | −6.689 | 1.00 | 45.83 | A | N |
| ATOM | 3748 | C | ARG | A | 254 | 64.563 | −3.054 | −4.316 | 1.00 | 34.14 | A | C |
| ATOM | 3749 | O | ARG | A | 254 | 64.154 | −1.977 | −3.915 | 1.00 | 35.76 | A | O |
| ATOM | 3751 | N | GLU | A | 255 | 64.096 | −3.667 | −5.390 | 1.00 | 34.42 | A | N |
| ATOM | 3752 | CA | GLU | A | 255 | 63.024 | −3.139 | −6.221 | 1.00 | 36.63 | A | C |
| ATOM | 3754 | CB | GLU | A | 255 | 62.724 | −4.179 | −7.296 | 1.00 | 38.74 | A | C |
| ATOM | 3757 | CG | GLU | A | 255 | 61.825 | −3.773 | −8.455 | 1.00 | 50.85 | A | C |
| ATOM | 3760 | CD | GLU | A | 255 | 61.681 | −4.909 | −9.497 | 1.00 | 60.07 | A | C |
| ATOM | 3761 | OE1 | GLU | A | 255 | 62.720 | −5.463 | −9.957 | 1.00 | 60.17 | A | O |
| ATOM | 3762 | OE2 | GLU | A | 255 | 60.523 | −5.246 | −9.844 | 1.00 | 63.55 | A | O |
| ATOM | 3763 | C | GLU | A | 255 | 61.756 | −2.831 | −5.420 | 1.00 | 36.27 | A | C |
| ATOM | 3764 | O | GLU | A | 255 | 61.129 | −1.794 | −5.593 | 1.00 | 39.35 | A | O |
| ATOM | 3766 | N | THR | A | 256 | 61.383 | −3.739 | −4.539 | 1.00 | 33.73 | A | N |
| ATOM | 3767 | CA | THR | A | 256 | 60.151 | −3.622 | −3.790 | 1.00 | 31.80 | A | C |
| ATOM | 3769 | CB | THR | A | 256 | 59.703 | −5.018 | −3.323 | 1.00 | 30.64 | A | C |
| ATOM | 3771 | OG1 | THR | A | 256 | 59.309 | −5.757 | −4.469 | 1.00 | 33.76 | A | O |
| ATOM | 3773 | CG2 | THR | A | 256 | 58.537 | −4.966 | −2.325 | 1.00 | 32.44 | A | C |
| ATOM | 3777 | C | THR | A | 256 | 60.360 | −2.667 | −2.618 | 1.00 | 30.31 | A | C |
| ATOM | 3778 | O | THR | A | 256 | 59.460 | −1.916 | −2.260 | 1.00 | 29.39 | A | O |
| ATOM | 3780 | N | SER | A | 257 | 61.544 | −2.705 | −2.022 | 1.00 | 30.11 | A | N |
| ATOM | 3781 | CA | SER | A | 257 | 61.920 | −1.693 | −1.036 | 1.00 | 33.18 | A | C |
| ATOM | 3783 | CB | SER | A | 257 | 63.327 | −1.943 | −0.475 | 1.00 | 32.22 | A | C |
| ATOM | 3786 | OG | SER | A | 257 | 63.336 | −3.128 | 0.297 | 1.00 | 33.34 | A | O |
| ATOM | 3788 | C | SER | A | 257 | 61.834 | −0.281 | −1.621 | 1.00 | 33.22 | A | C |
| ATOM | 3789 | O | SER | A | 257 | 61.449 | 0.638 | −0.907 | 1.00 | 33.37 | A | O |
| ATOM | 3791 | N | ARG | A | 258 | 62.173 | −0.111 | −2.901 | 1.00 | 32.43 | A | N |
| ATOM | 3792 | CA | ARG | A | 258 | 62.019 | 1.204 | −3.565 | 1.00 | 35.63 | A | C |
| ATOM | 3794 | CB | ARG | A | 258 | 62.525 | 1.207 | −5.024 | 1.00 | 38.19 | A | C |
| ATOM | 3797 | CG | ARG | A | 258 | 63.974 | 1.629 | −5.235 | 1.00 | 43.51 | A | C |
| ATOM | 3800 | CD | ARG | A | 258 | 64.204 | 2.128 | −6.670 | 1.00 | 49.21 | A | C |
| ATOM | 3803 | NE | ARG | A | 258 | 63.874 | 1.127 | −7.692 | 1.00 | 50.92 | A | N |
| ATOM | 3805 | CZ | ARG | A | 258 | 64.697 | 0.173 | −8.133 | 1.00 | 57.27 | A | C |
| ATOM | 3806 | NH1 | ARG | A | 258 | 64.275 | −0.679 | −9.060 | 1.00 | 57.78 | A | N |
| ATOM | 3809 | NH2 | ARG | A | 258 | 65.935 | 0.050 | −7.653 | 1.00 | 60.74 | A | N |
| ATOM | 3812 | C | ARG | A | 258 | 60.571 | 1.623 | −3.602 | 1.00 | 33.91 | A | C |
| ATOM | 3813 | O | ARG | A | 258 | 60.254 | 2.753 | −3.318 | 1.00 | 33.23 | A | O |
| ATOM | 3815 | N | TRP | A | 259 | 59.697 | 0.714 | −4.015 | 1.00 | 33.11 | A | N |
| ATOM | 3816 | CA | TRP | A | 259 | 58.266 | 1.003 | −4.026 | 1.00 | 32.00 | A | C |
| ATOM | 3818 | CB | TRP | A | 259 | 57.487 | −0.183 | −4.587 | 1.00 | 31.64 | A | C |
| ATOM | 3821 | CG | TRP | A | 259 | 56.053 | −0.155 | −4.267 | 1.00 | 27.92 | A | C |
| ATOM | 3822 | CD1 | TRP | A | 259 | 55.084 | 0.569 | −4.900 | 1.00 | 32.00 | A | C |
| ATOM | 3824 | NE1 | TRP | A | 259 | 53.861 | 0.357 | −4.299 | 1.00 | 30.37 | A | N |
| ATOM | 3826 | CE2 | TRP | A | 259 | 54.033 | −0.523 | −3.264 | 1.00 | 26.02 | A | C |
| ATOM | 3827 | CD2 | TRP | A | 259 | 55.400 | −0.861 | −3.211 | 1.00 | 28.92 | A | C |
| ATOM | 3828 | CE3 | TRP | A | 259 | 55.839 | −1.732 | −2.212 | 1.00 | 24.22 | A | C |
| ATOM | 3830 | CZ3 | TRP | A | 259 | 54.932 | −2.229 | −1.337 | 1.00 | 28.49 | A | C |
| ATOM | 3832 | CH2 | TRP | A | 259 | 53.584 | −1.882 | −1.425 | 1.00 | 32.67 | A | C |
| ATOM | 3834 | CZ2 | TRP | A | 259 | 53.125 | −1.025 | −2.382 | 1.00 | 22.99 | A | C |
| ATOM | 3836 | C | TRP | A | 259 | 57.753 | 1.358 | −2.623 | 1.00 | 31.98 | A | C |
| ATOM | 3837 | O | TRP | A | 259 | 56.957 | 2.274 | −2.465 | 1.00 | 34.30 | A | O |
| ATOM | 3839 | N | TRP | A | 260 | 58.224 | 0.639 | −1.611 | 1.00 | 30.69 | A | N |
| ATOM | 3840 | CA | TRP | A | 260 | 57.676 | 0.755 | −0.270 | 1.00 | 29.45 | A | C |
| ATOM | 3842 | CB | TRP | A | 260 | 58.190 | −0.399 | 0.578 | 1.00 | 29.19 | A | C |
| ATOM | 3845 | CG | TRP | A | 260 | 57.621 | −0.512 | 1.985 | 1.00 | 32.70 | A | C |
| ATOM | 3846 | CD1 | TRP | A | 260 | 58.333 | −0.569 | 3.137 | 1.00 | 31.86 | A | C |
| ATOM | 3848 | NE1 | TRP | A | 260 | 57.489 | −0.698 | 4.209 | 1.00 | 33.52 | A | N |
| ATOM | 3850 | CE2 | TRP | A | 260 | 56.202 | −0.741 | 3.762 | 1.00 | 27.99 | A | C |
| ATOM | 3851 | CD2 | TRP | A | 260 | 56.240 | −0.627 | 2.364 | 1.00 | 25.33 | A | C |
| ATOM | 3852 | CE3 | TRP | A | 260 | 55.038 | −0.632 | 1.658 | 1.00 | 28.45 | A | C |
| ATOM | 3854 | CZ3 | TRP | A | 260 | 53.863 | −0.755 | 2.356 | 1.00 | 24.24 | A | C |
| ATOM | 3856 | CH2 | TRP | A | 260 | 53.859 | −0.875 | 3.741 | 1.00 | 29.24 | A | C |
| ATOM | 3858 | CZ2 | TRP | A | 260 | 55.017 | −0.858 | 4.466 | 1.00 | 31.81 | A | C |
| ATOM | 3860 | C | TRP | A | 260 | 58.052 | 2.102 | 0.332 | 1.00 | 29.67 | A | C |
| ATOM | 3861 | O | TRP | A | 260 | 57.218 | 2.763 | 0.934 | 1.00 | 26.76 | A | O |
| ATOM | 3863 | N | ARG | A | 261 | 59.288 | 2.528 | 0.111 | 1.00 | 32.87 | A | N |
| ATOM | 3864 | CA | AARG | A | 261 | 59.778 | 3.810 | 0.630 | 0.50 | 35.92 | A | C |
| ATOM | 3865 | CA | BARG | A | 261 | 59.768 | 3.809 | 0.649 | 0.50 | 35.98 | A | C |
| ATOM | 3868 | CB | AARG | A | 261 | 61.299 | 3.917 | 0.447 | 0.50 | 36.14 | A | C |
| ATOM | 3869 | CB | BARG | A | 261 | 61.293 | 3.938 | 0.514 | 0.50 | 36.20 | A | C |
| ATOM | 3874 | CG | AARG | A | 261 | 62.081 | 3.255 | 1.576 | 0.50 | 40.00 | A | C |
| ATOM | 3875 | CG | BARG | A | 261 | 61.962 | 4.656 | 1.691 | 0.50 | 40.66 | A | C |
| ATOM | 3880 | CD | AARG | A | 261 | 63.347 | 2.553 | 1.086 | 0.50 | 45.53 | A | C |
| ATOM | 3881 | CD | BARG | A | 261 | 61.787 | 3.877 | 3.002 | 0.50 | 44.00 | A | C |
| ATOM | 3886 | NE | AARG | A | 261 | 63.970 | 3.229 | −0.049 | 0.50 | 45.59 | A | N |
| ATOM | 3887 | NE | BARG | A | 261 | 62.789 | 4.234 | 4.005 | 0.50 | 45.46 | A | N |
| ATOM | 3890 | CZ | AARG | A | 261 | 64.845 | 2.643 | −0.856 | 0.50 | 42.15 | A | C |

TABLE 4-2-continued

Coordinates of *P. alba* IspS

| | | | | | | | | | | | | |
|---|---|---|---|---|---|---|---|---|---|---|---|---|
| ATOM | 3891 | CZ | BARG | A | 261 | 62.660 | 5.236 | 4.869 | 0.50 | 50.02 | A | C |
| ATOM | 3892 | NH1 | AARG | A | 261 | 65.188 | 1.382 | −0.637 | 0.50 | 33.28 | A | N |
| ATOM | 3893 | NH1 | BARG | A | 261 | 61.567 | 5.987 | 4.861 | 0.50 | 49.40 | A | N |
| ATOM | 3898 | NH2 | AARG | A | 261 | 65.370 | 3.311 | −1.874 | 0.50 | 42.47 | A | N |
| ATOM | 3899 | NH2 | BARG | A | 261 | 63.625 | 5.484 | 5.745 | 0.50 | 49.02 | A | N |
| ATOM | 3904 | C | ARG | A | 261 | 59.061 | 4.997 | −0.024 | 1.00 | 37.61 | A | C |
| ATOM | 3905 | O | ARG | A | 261 | 58.729 | 5.981 | 0.642 | 1.00 | 38.28 | A | O |
| ATOM | 3907 | N | ARG | A | 262 | 58.808 | 4.897 | −1.327 | 1.00 | 38.01 | A | N |
| ATOM | 3908 | CA | ARG | A | 262 | 58.026 | 5.922 | −2.019 | 1.00 | 39.29 | A | C |
| ATOM | 3910 | CB | ARG | A | 262 | 57.878 | 5.607 | −3.516 | 1.00 | 42.22 | A | C |
| ATOM | 3913 | CG | ARG | A | 262 | 59.136 | 5.898 | −4.350 | 1.00 | 52.27 | A | C |
| ATOM | 3916 | CD | ARG | A | 262 | 58.787 | 6.242 | −5.811 | 1.00 | 62.63 | A | C |
| ATOM | 3919 | NE | ARG | A | 262 | 57.884 | 5.261 | −6.428 | 1.00 | 67.61 | A | N |
| ATOM | 3921 | CZ | ARG | A | 262 | 58.273 | 4.146 | −7.054 | 1.00 | 71.86 | A | C |
| ATOM | 3922 | NH1 | ARG | A | 262 | 59.567 | 3.837 | −7.171 | 1.00 | 69.63 | A | N |
| ATOM | 3925 | NH2 | ARG | A | 262 | 57.354 | 3.328 | −7.566 | 1.00 | 71.10 | A | N |
| ATOM | 3928 | C | ARG | A | 262 | 56.646 | 6.038 | −1.398 | 1.00 | 35.13 | A | C |
| ATOM | 3929 | O | ARG | A | 262 | 56.192 | 7.127 | −1.072 | 1.00 | 39.41 | A | O |
| ATOM | 3931 | N | VAL | A | 263 | 55.978 | 4.913 | −1.229 | 1.00 | 31.29 | A | N |
| ATOM | 3932 | CA | VAL | A | 263 | 54.684 | 4.899 | −0.577 | 1.00 | 28.48 | A | C |
| ATOM | 3934 | CB | VAL | A | 263 | 54.116 | 3.501 | −0.518 | 1.00 | 26.56 | A | C |
| ATOM | 3936 | CG1 | VAL | A | 263 | 53.801 | 3.029 | −1.925 | 1.00 | 30.17 | A | C |
| ATOM | 3940 | CG2 | VAL | A | 263 | 52.879 | 3.480 | 0.354 | 1.00 | 27.85 | A | C |
| ATOM | 3944 | C | VAL | A | 263 | 54.745 | 5.479 | 0.844 | 1.00 | 28.20 | A | C |
| ATOM | 3945 | O | VAL | A | 263 | 53.801 | 6.150 | 1.259 | 1.00 | 26.93 | A | O |
| ATOM | 3947 | N | GLY | A | 264 | 55.847 | 5.199 | 1.559 | 1.00 | 28.31 | A | N |
| ATOM | 3948 | CA | GLY | A | 264 | 56.160 | 5.750 | 2.871 | 1.00 | 27.54 | A | C |
| ATOM | 3951 | C | GLY | A | 264 | 55.063 | 5.691 | 3.909 | 1.00 | 29.80 | A | C |
| ATOM | 3952 | O | GLY | A | 264 | 54.978 | 6.560 | 4.760 | 1.00 | 32.57 | A | O |
| ATOM | 3954 | N | LEU | A | 265 | 54.219 | 4.673 | 3.842 | 1.00 | 32.96 | A | N |
| ATOM | 3955 | CA | LEU | A | 265 | 53.026 | 4.593 | 4.679 | 1.00 | 36.19 | A | C |
| ATOM | 3957 | CB | LEU | A | 265 | 52.050 | 3.553 | 4.111 | 1.00 | 34.50 | A | C |
| ATOM | 3960 | CG | LEU | A | 265 | 50.568 | 3.516 | 4.505 | 1.00 | 36.39 | A | C |
| ATOM | 3962 | CD1 | LEU | A | 265 | 49.833 | 4.834 | 4.299 | 1.00 | 27.01 | A | C |
| ATOM | 3966 | CD2 | LEU | A | 265 | 49.858 | 2.406 | 3.721 | 1.00 | 31.32 | A | C |
| ATOM | 3970 | C | LEU | A | 265 | 53.376 | 4.316 | 6.151 | 1.00 | 40.47 | A | C |
| ATOM | 3971 | O | LEU | A | 265 | 52.828 | 4.964 | 7.046 | 1.00 | 41.90 | A | O |
| ATOM | 3973 | N | ALA | A | 266 | 54.306 | 3.402 | 6.413 | 1.00 | 45.05 | A | N |
| ATOM | 3974 | CA | ALA | A | 266 | 54.692 | 3.097 | 7.803 | 1.00 | 48.60 | A | C |
| ATOM | 3976 | CB | ALA | A | 266 | 55.536 | 1.834 | 7.871 | 1.00 | 49.61 | A | C |
| ATOM | 3980 | C | ALA | A | 266 | 55.414 | 4.263 | 8.486 | 1.00 | 50.25 | A | C |
| ATOM | 3981 | O | ALA | A | 266 | 55.437 | 4.354 | 9.709 | 1.00 | 53.50 | A | O |
| ATOM | 3983 | N | THR | A | 267 | 55.989 | 5.161 | 7.693 | 1.00 | 51.71 | A | N |
| ATOM | 3984 | CA | THR | A | 267 | 56.599 | 6.383 | 8.220 | 1.00 | 50.87 | A | C |
| ATOM | 3986 | CB | THR | A | 267 | 57.494 | 7.042 | 7.158 | 1.00 | 50.67 | A | C |
| ATOM | 3988 | OG1 | THR | A | 267 | 58.268 | 6.030 | 6.501 | 1.00 | 54.33 | A | O |
| ATOM | 3990 | CG2 | THR | A | 267 | 58.420 | 8.057 | 7.783 | 1.00 | 53.96 | A | C |
| ATOM | 3994 | C | THR | A | 267 | 55.537 | 7.383 | 8.678 | 1.00 | 49.72 | A | C |
| ATOM | 3995 | O | THR | A | 267 | 55.657 | 7.966 | 9.753 | 1.00 | 51.35 | A | O |
| ATOM | 3997 | N | LYS | A | 268 | 54.494 | 7.567 | 7.870 | 1.00 | 47.73 | A | N |
| ATOM | 3998 | CA | LYS | A | 268 | 53.515 | 8.655 | 8.074 | 1.00 | 45.94 | A | C |
| ATOM | 4000 | CB | LYS | A | 268 | 52.935 | 9.113 | 6.720 | 1.00 | 46.30 | A | C |
| ATOM | 4003 | CG | LYS | A | 268 | 53.986 | 9.658 | 5.725 | 1.00 | 47.05 | A | C |
| ATOM | 4006 | CD | LYS | A | 268 | 54.376 | 11.104 | 6.011 | 1.00 | 49.29 | A | C |
| ATOM | 4009 | CE | LYS | A | 268 | 55.573 | 11.543 | 5.161 | 1.00 | 52.85 | A | C |
| ATOM | 4012 | NZ | LYS | A | 268 | 55.780 | 13.020 | 5.207 | 1.00 | 54.81 | A | N |
| ATOM | 4016 | C | LYS | A | 268 | 52.378 | 8.275 | 9.024 | 1.00 | 44.32 | A | C |
| ATOM | 4017 | O | LYS | A | 268 | 51.749 | 9.148 | 9.610 | 1.00 | 44.98 | A | O |
| ATOM | 4019 | N | LEU | A | 269 | 52.095 | 6.980 | 9.138 | 1.00 | 43.49 | A | N |
| ATOM | 4020 | CA | LEU | A | 269 | 51.151 | 6.457 | 10.122 | 1.00 | 43.04 | A | C |
| ATOM | 4022 | CB | LEU | A | 269 | 50.429 | 5.222 | 9.561 | 1.00 | 42.92 | A | C |
| ATOM | 4025 | CG | LEU | A | 269 | 49.100 | 5.381 | 8.814 | 1.00 | 42.16 | A | C |
| ATOM | 4027 | CD1 | LEU | A | 269 | 49.147 | 6.491 | 7.813 | 1.00 | 38.88 | A | C |
| ATOM | 4031 | CD2 | LEU | A | 269 | 48.721 | 4.062 | 8.144 | 1.00 | 40.39 | A | C |
| ATOM | 4035 | C | LEU | A | 269 | 51.943 | 6.068 | 11.380 | 1.00 | 43.46 | A | C |
| ATOM | 4036 | O | LEU | A | 269 | 52.741 | 5.132 | 11.344 | 1.00 | 45.75 | A | O |
| ATOM | 4038 | N | HIS | A | 270 | 51.718 | 6.762 | 12.489 | 1.00 | 42.57 | A | N |
| ATOM | 4039 | CA | HIS | A | 270 | 52.559 | 6.585 | 13.689 | 1.00 | 42.20 | A | C |
| ATOM | 4041 | CB | HIS | A | 270 | 52.334 | 7.730 | 14.706 | 1.00 | 43.68 | A | C |
| ATOM | 4044 | CG | HIS | A | 270 | 52.315 | 9.101 | 14.088 | 1.00 | 55.54 | A | C |
| ATOM | 4045 | ND1 | HIS | A | 270 | 53.195 | 9.489 | 13.097 | 1.00 | 59.69 | A | N |
| ATOM | 4047 | CE1 | HIS | A | 270 | 52.936 | 10.737 | 12.746 | 1.00 | 62.20 | A | C |
| ATOM | 4049 | NE2 | HIS | A | 270 | 51.925 | 11.177 | 13.475 | 1.00 | 61.94 | A | N |
| ATOM | 4051 | CD2 | HIS | A | 270 | 51.515 | 10.173 | 14.321 | 1.00 | 61.38 | A | C |
| ATOM | 4053 | C | HIS | A | 270 | 52.340 | 5.224 | 14.372 | 1.00 | 37.82 | A | C |
| ATOM | 4054 | O | HIS | A | 270 | 53.221 | 4.720 | 15.063 | 1.00 | 35.89 | A | O |
| ATOM | 4056 | N | PHE | A | 271 | 51.160 | 4.649 | 14.178 | 1.00 | 34.74 | A | N |
| ATOM | 4057 | CA | PHE | A | 271 | 50.818 | 3.349 | 14.756 | 1.00 | 35.98 | A | C |

TABLE 4-2-continued

| Coordinates of *P. alba* IspS | | | | | | | | | | | | |
|---|---|---|---|---|---|---|---|---|---|---|---|---|
| ATOM | 4059 | CB | PHE | A | 271 | 49.297 | 3.246 | 14.975 | 1.00 | 36.24 | A | C |
| ATOM | 4062 | CG | PHE | A | 271 | 48.513 | 3.176 | 13.700 | 1.00 | 32.72 | A | C |
| ATOM | 4063 | CD1 | PHE | A | 271 | 48.245 | 1.962 | 13.107 | 1.00 | 36.61 | A | C |
| ATOM | 4065 | CE1 | PHE | A | 271 | 47.542 | 1.895 | 11.905 | 1.00 | 41.78 | A | C |
| ATOM | 4067 | CZ | PHE | A | 271 | 47.106 | 3.050 | 11.293 | 1.00 | 39.23 | A | C |
| ATOM | 4069 | CE2 | PHE | A | 271 | 47.370 | 4.267 | 11.868 | 1.00 | 40.49 | A | C |
| ATOM | 4071 | CD2 | PHE | A | 271 | 48.081 | 4.330 | 13.072 | 1.00 | 36.58 | A | C |
| ATOM | 4073 | C | PHE | A | 271 | 51.277 | 2.144 | 13.928 | 1.00 | 36.24 | A | C |
| ATOM | 4074 | O | PHE | A | 271 | 51.232 | 1.028 | 14.425 | 1.00 | 36.55 | A | O |
| ATOM | 4076 | N | ALA | A | 272 | 51.705 | 2.352 | 12.681 | 1.00 | 36.36 | A | N |
| ATOM | 4077 | CA | ALA | A | 272 | 51.905 | 1.217 | 11.753 | 1.00 | 38.44 | A | C |
| ATOM | 4079 | CB | ALA | A | 272 | 51.767 | 1.683 | 10.299 | 1.00 | 37.11 | A | C |
| ATOM | 4083 | C | ALA | A | 272 | 53.235 | 0.493 | 11.939 | 1.00 | 37.87 | A | C |
| ATOM | 4084 | O | ALA | A | 272 | 54.260 | 1.128 | 12.126 | 1.00 | 38.46 | A | O |
| ATOM | 4086 | N | ARG | A | 273 | 53.199 | −0.838 | 11.895 | 1.00 | 39.95 | A | N |
| ATOM | 4087 | CA | ARG | A | 273 | 54.415 | −1.651 | 11.843 | 1.00 | 42.71 | A | C |
| ATOM | 4089 | CB | ARG | A | 273 | 54.161 | −3.077 | 12.354 | 1.00 | 44.71 | A | C |
| ATOM | 4092 | CG | ARG | A | 273 | 53.612 | −3.232 | 13.785 | 1.00 | 52.26 | A | C |
| ATOM | 4095 | CD | ARG | A | 273 | 53.137 | −4.699 | 14.060 | 1.00 | 58.75 | A | C |
| ATOM | 4098 | NE | ARG | A | 273 | 51.872 | −5.018 | 13.384 | 1.00 | 59.61 | A | N |
| ATOM | 4100 | CZ | ARG | A | 273 | 51.440 | −6.241 | 13.062 | 1.00 | 65.74 | A | C |
| ATOM | 4101 | NH1 | ARG | A | 273 | 52.168 | −7.320 | 13.327 | 1.00 | 72.19 | A | N |
| ATOM | 4104 | NH2 | ARG | A | 273 | 50.268 | −6.390 | 12.441 | 1.00 | 62.91 | A | N |
| ATOM | 4107 | C | ARG | A | 273 | 54.886 | −1.731 | 10.387 | 1.00 | 41.28 | A | C |
| ATOM | 4108 | O | ARG | A | 273 | 54.067 | −1.896 | 9.486 | 1.00 | 42.18 | A | O |
| ATOM | 4110 | N | ASP | A | 274 | 56.195 | −1.605 | 10.171 | 1.00 | 40.00 | A | N |
| ATOM | 4111 | CA | ASP | A | 274 | 56.819 | −1.798 | 8.854 | 1.00 | 38.76 | A | C |
| ATOM | 4113 | CB | ASP | A | 274 | 57.983 | −0.808 | 8.684 | 1.00 | 38.55 | A | C |
| ATOM | 4116 | CG | ASP | A | 274 | 58.733 | −0.993 | 7.370 | 1.00 | 42.03 | A | C |
| ATOM | 4117 | OD1 | ASP | A | 274 | 58.666 | −2.086 | 6.781 | 1.00 | 39.25 | A | O |
| ATOM | 4118 | OD2 | ASP | A | 274 | 59.404 | −0.044 | 6.918 | 1.00 | 46.81 | A | O |
| ATOM | 4119 | C | ASP | A | 274 | 57.306 | −3.260 | 8.725 | 1.00 | 37.31 | A | C |
| ATOM | 4120 | O | ASP | A | 274 | 58.281 | −3.644 | 9.349 | 1.00 | 36.99 | A | O |
| ATOM | 4122 | N | ARG | A | 275 | 56.612 | −4.069 | 7.925 | 1.00 | 37.37 | A | N |
| ATOM | 4123 | CA | ARG | A | 275 | 56.889 | −5.498 | 7.826 | 1.00 | 37.69 | A | C |
| ATOM | 4125 | CB | ARG | A | 275 | 55.702 | −6.299 | 8.391 | 1.00 | 39.25 | A | C |
| ATOM | 4128 | CG | ARG | A | 275 | 55.490 | −6.180 | 9.913 | 1.00 | 47.84 | A | C |
| ATOM | 4131 | CD | ARG | A | 275 | 56.044 | −7.381 | 10.697 | 1.00 | 59.27 | A | C |
| ATOM | 4134 | NE | ARG | A | 275 | 55.924 | −7.187 | 12.150 | 1.00 | 68.25 | A | N |
| ATOM | 4136 | CZ | ARG | A | 275 | 56.679 | −6.355 | 12.886 | 1.00 | 74.47 | A | C |
| ATOM | 4137 | NH1 | ARG | A | 275 | 57.641 | −5.618 | 12.324 | 1.00 | 74.61 | A | N |
| ATOM | 4140 | NH2 | ARG | A | 275 | 56.473 | −6.252 | 14.204 | 1.00 | 72.98 | A | N |
| ATOM | 4143 | C | ARG | A | 275 | 57.168 | −5.943 | 6.388 | 1.00 | 36.06 | A | C |
| ATOM | 4144 | O | ARG | A | 275 | 56.729 | −7.017 | 5.973 | 1.00 | 35.65 | A | O |
| ATOM | 4146 | N | LEU | A | 276 | 57.898 | −5.137 | 5.623 | 1.00 | 35.38 | A | N |
| ATOM | 4147 | CA | LEU | A | 276 | 58.209 | −5.505 | 4.231 | 1.00 | 34.05 | A | C |
| ATOM | 4149 | CB | LEU | A | 276 | 58.824 | −4.340 | 3.438 | 1.00 | 35.05 | A | C |
| ATOM | 4152 | CG | LEU | A | 276 | 59.320 | −4.741 | 2.049 | 1.00 | 34.24 | A | C |
| ATOM | 4154 | CD1 | LEU | A | 276 | 58.157 | −5.203 | 1.208 | 1.00 | 37.51 | A | C |
| ATOM | 4158 | CD2 | LEU | A | 276 | 60.030 | −3.629 | 1.374 | 1.00 | 37.66 | A | C |
| ATOM | 4162 | C | LEU | A | 276 | 59.147 | −6.698 | 4.170 | 1.00 | 31.37 | A | C |
| ATOM | 4163 | O | LEU | A | 276 | 58.890 | −7.636 | 3.443 | 1.00 | 30.37 | A | O |
| ATOM | 4165 | N | ILE | A | 277 | 60.221 | −6.664 | 4.950 | 1.00 | 30.01 | A | N |
| ATOM | 4166 | CA | ILE | A | 277 | 61.242 | −7.701 | 4.870 | 1.00 | 29.44 | A | C |
| ATOM | 4168 | CB | ILE | A | 277 | 62.459 | −7.360 | 5.755 | 1.00 | 30.70 | A | C |
| ATOM | 4170 | CG1 | ILE | A | 277 | 63.124 | −6.061 | 5.253 | 1.00 | 35.07 | A | C |
| ATOM | 4173 | CD1 | ILE | A | 277 | 64.038 | −5.345 | 6.291 | 1.00 | 36.73 | A | C |
| ATOM | 4177 | CG2 | ILE | A | 277 | 63.463 | −8.487 | 5.705 | 1.00 | 27.89 | A | C |
| ATOM | 4181 | C | ILE | A | 277 | 60.654 | −9.045 | 5.267 | 1.00 | 28.92 | A | C |
| ATOM | 4182 | O | ILE | A | 277 | 60.847 | −10.054 | 4.583 | 1.00 | 28.83 | A | O |
| ATOM | 4184 | N | GLU | A | 278 | 59.905 | −9.048 | 6.359 | 1.00 | 27.84 | A | N |
| ATOM | 4185 | CA | GLU | A | 278 | 59.220 | −10.244 | 6.818 | 1.00 | 29.71 | A | C |
| ATOM | 4187 | CB | GLU | A | 278 | 58.538 | −9.966 | 8.161 | 1.00 | 30.64 | A | C |
| ATOM | 4190 | CG | GLU | A | 278 | 59.515 | −9.600 | 9.291 | 1.00 | 41.88 | A | C |
| ATOM | 4193 | CD | GLU | A | 278 | 59.736 | −8.097 | 9.493 | 1.00 | 50.18 | A | C |
| ATOM | 4194 | OE1 | GLU | A | 278 | 59.920 | −7.333 | 8.508 | 1.00 | 48.05 | A | O |
| ATOM | 4195 | OE2 | GLU | A | 278 | 59.742 | −7.686 | 10.673 | 1.00 | 59.82 | A | O |
| ATOM | 4196 | C | GLU | A | 278 | 58.197 | −10.733 | 5.761 | 1.00 | 28.62 | A | C |
| ATOM | 4197 | O | GLU | A | 278 | 58.066 | −11.929 | 5.519 | 1.00 | 28.77 | A | O |
| ATOM | 4199 | N | SER | A | 279 | 57.509 | −9.791 | 5.114 | 1.00 | 25.67 | A | N |
| ATOM | 4200 | CA | SER | A | 279 | 56.510 | −10.111 | 4.115 | 1.00 | 25.01 | A | C |
| ATOM | 4202 | CB | SER | A | 279 | 55.694 | −8.869 | 3.762 | 1.00 | 26.35 | A | C |
| ATOM | 4205 | OG | SER | A | 279 | 54.839 | −8.541 | 4.839 | 1.00 | 32.90 | A | O |
| ATOM | 4207 | C | SER | A | 279 | 57.152 | −10.682 | 2.875 | 1.00 | 24.05 | A | C |
| ATOM | 4208 | O | SER | A | 279 | 56.560 | −11.514 | 2.223 | 1.00 | 23.50 | A | O |
| ATOM | 4210 | N | PHE | A | 280 | 58.365 | −10.237 | 2.551 | 1.00 | 21.71 | A | N |
| ATOM | 4211 | CA | PHE | A | 280 | 59.091 | −10.801 | 1.419 | 1.00 | 23.37 | A | C |
| ATOM | 4213 | CB | PHE | A | 280 | 60.266 | −9.902 | 1.017 | 1.00 | 25.01 | A | C |

TABLE 4-2-continued

| Coordinates of *P. alba* IspS | | | | | | | | | | | | |
|---|---|---|---|---|---|---|---|---|---|---|---|---|
| ATOM | 4216 | CG | PHE | A | 280 | 60.841 | −10.261 | −0.298 | 1.00 | 22.72 | A | C |
| ATOM | 4217 | CD1 | PHE | A | 280 | 60.259 | −9.812 | −1.466 | 1.00 | 26.45 | A | C |
| ATOM | 4219 | CE1 | PHE | A | 280 | 60.747 | −10.180 | −2.677 | 1.00 | 25.95 | A | C |
| ATOM | 4221 | CZ | PHE | A | 280 | 61.836 | −11.022 | −2.737 | 1.00 | 25.35 | A | C |
| ATOM | 4223 | CE2 | PHE | A | 280 | 62.415 | −11.486 | −1.584 | 1.00 | 24.77 | A | C |
| ATOM | 4225 | CD2 | PHE | A | 280 | 61.917 | −11.108 | −0.370 | 1.00 | 26.82 | A | C |
| ATOM | 4227 | C | PHE | A | 280 | 59.599 | −12.226 | 1.709 | 1.00 | 23.03 | A | C |
| ATOM | 4228 | O | PHE | A | 280 | 59.491 | −13.103 | 0.863 | 1.00 | 25.85 | A | O |
| ATOM | 4230 | N | TYR | A | 281 | 60.156 | −12.429 | 2.896 | 1.00 | 23.11 | A | N |
| ATOM | 4231 | CA | TYR | A | 281 | 60.546 | −13.751 | 3.392 | 1.00 | 24.07 | A | C |
| ATOM | 4233 | CB | TYR | A | 281 | 61.140 | −13.640 | 4.806 | 1.00 | 24.19 | A | C |
| ATOM | 4236 | CG | TYR | A | 281 | 61.313 | −14.958 | 5.545 | 1.00 | 26.46 | A | C |
| ATOM | 4237 | CD1 | TYR | A | 281 | 62.469 | −15.728 | 5.401 | 1.00 | 28.95 | A | C |
| ATOM | 4239 | CE1 | TYR | A | 281 | 62.607 | −16.960 | 6.070 | 1.00 | 32.82 | A | C |
| ATOM | 4241 | CZ | TYR | A | 281 | 61.584 | −17.403 | 6.899 | 1.00 | 23.73 | A | C |
| ATOM | 4242 | OH | TYR | A | 281 | 61.699 | −18.572 | 7.602 | 1.00 | 37.06 | A | O |
| ATOM | 4244 | CE2 | TYR | A | 281 | 60.463 | −16.627 | 7.091 | 1.00 | 27.38 | A | C |
| ATOM | 4246 | CD2 | TYR | A | 281 | 60.336 | −15.409 | 6.424 | 1.00 | 28.38 | A | C |
| ATOM | 4248 | C | TYR | A | 281 | 59.327 | −14.681 | 3.339 | 1.00 | 23.90 | A | C |
| ATOM | 4249 | O | TYR | A | 281 | 59.407 | −15.778 | 2.841 | 1.00 | 22.03 | A | O |
| ATOM | 4251 | N | TRP | A | 282 | 58.178 | −14.190 | 3.769 | 1.00 | 24.19 | A | N |
| ATOM | 4252 | CA | TRP | A | 282 | 56.946 | −14.940 | 3.645 | 1.00 | 23.89 | A | C |
| ATOM | 4254 | CB | TRP | A | 282 | 55.772 | −14.098 | 4.127 | 1.00 | 24.11 | A | C |
| ATOM | 4257 | CG | TRP | A | 282 | 54.466 | −14.809 | 4.037 | 1.00 | 24.19 | A | C |
| ATOM | 4258 | CD1 | TRP | A | 282 | 53.597 | −14.786 | 2.998 | 1.00 | 22.17 | A | C |
| ATOM | 4260 | NE1 | TRP | A | 282 | 52.491 | −15.562 | 3.279 | 1.00 | 24.03 | A | N |
| ATOM | 4262 | CE2 | TRP | A | 282 | 52.657 | −16.120 | 4.518 | 1.00 | 27.44 | A | C |
| ATOM | 4263 | CD2 | TRP | A | 282 | 53.888 | −15.656 | 5.029 | 1.00 | 23.48 | A | C |
| ATOM | 4264 | CE3 | TRP | A | 282 | 54.291 | −16.075 | 6.296 | 1.00 | 29.21 | A | C |
| ATOM | 4266 | CZ3 | TRP | A | 282 | 53.470 | −16.930 | 7.001 | 1.00 | 30.47 | A | C |
| ATOM | 4268 | CH2 | TRP | A | 282 | 52.255 | −17.363 | 6.468 | 1.00 | 29.72 | A | C |
| ATOM | 4270 | CZ2 | TRP | A | 282 | 51.830 | −16.962 | 5.233 | 1.00 | 25.51 | A | C |
| ATOM | 4272 | C | TRP | A | 282 | 56.717 | −15.400 | 2.195 | 1.00 | 24.21 | A | C |
| ATOM | 4273 | O | TRP | A | 282 | 56.504 | −16.587 | 1.947 | 1.00 | 22.03 | A | O |
| ATOM | 4275 | N | ALA | A | 283 | 56.806 | −14.455 | 1.259 | 1.00 | 22.23 | A | N |
| ATOM | 4276 | CA | ALA | A | 283 | 56.573 | −14.706 | −0.165 | 1.00 | 20.96 | A | C |
| ATOM | 4278 | CB | ALA | A | 283 | 56.663 | −13.402 | −0.961 | 1.00 | 18.60 | A | C |
| ATOM | 4282 | C | ALA | A | 283 | 57.522 | −15.728 | −0.781 | 1.00 | 21.39 | A | C |
| ATOM | 4283 | O | ALA | A | 283 | 57.118 | −16.474 | −1.679 | 1.00 | 20.52 | A | O |
| ATOM | 4285 | N | VAL | A | 284 | 58.769 | −15.754 | −0.318 | 1.00 | 22.30 | A | N |
| ATOM | 4286 | CA | VAL | A | 284 | 59.758 | −16.758 | −0.764 | 1.00 | 23.58 | A | C |
| ATOM | 4288 | CB | VAL | A | 284 | 61.144 | −16.478 | −0.111 | 1.00 | 24.57 | A | C |
| ATOM | 4290 | CG1 | VAL | A | 284 | 61.727 | −15.180 | −0.672 | 1.00 | 19.22 | A | C |
| ATOM | 4294 | CG2 | VAL | A | 284 | 62.095 | −17.641 | −0.320 | 1.00 | 19.35 | A | C |
| ATOM | 4298 | C | VAL | A | 284 | 59.302 | −18.202 | −0.456 | 1.00 | 24.32 | A | C |
| ATOM | 4299 | O | VAL | A | 284 | 59.566 | −19.151 | −1.208 | 1.00 | 23.82 | A | O |
| ATOM | 4301 | N | GLY | A | 285 | 58.599 | −18.369 | 0.649 | 1.00 | 24.47 | A | N |
| ATOM | 4302 | CA | GLY | A | 285 | 57.973 | −19.648 | 0.958 | 1.00 | 21.25 | A | C |
| ATOM | 4305 | C | GLY | A | 285 | 56.907 | −20.048 | −0.031 | 1.00 | 20.54 | A | C |
| ATOM | 4306 | O | GLY | A | 285 | 56.745 | −21.226 | −0.300 | 1.00 | 22.10 | A | O |
| ATOM | 4308 | N | VAL | A | 286 | 56.162 | −19.078 | −0.547 | 1.00 | 22.33 | A | N |
| ATOM | 4309 | CA | VAL | A | 286 | 55.029 | −19.347 | −1.441 | 1.00 | 20.31 | A | C |
| ATOM | 4311 | CB | VAL | A | 286 | 54.045 | −18.169 | −1.463 | 1.00 | 23.35 | A | C |
| ATOM | 4313 | CG1 | VAL | A | 286 | 52.961 | −18.408 | −2.468 | 1.00 | 22.65 | A | C |
| ATOM | 4317 | CG2 | VAL | A | 286 | 53.388 | −17.973 | −0.051 | 1.00 | 22.60 | A | C |
| ATOM | 4321 | C | VAL | A | 286 | 55.529 | −19.659 | −2.834 | 1.00 | 22.01 | A | C |
| ATOM | 4322 | O | VAL | A | 286 | 55.056 | −20.605 | −3.472 | 1.00 | 22.74 | A | O |
| ATOM | 4324 | N | ALA | A | 287 | 56.540 | −18.915 | −3.279 | 1.00 | 21.32 | A | N |
| ATOM | 4325 | CA | ALA | A | 287 | 57.034 | −19.003 | −4.629 | 1.00 | 20.30 | A | C |
| ATOM | 4327 | CB | ALA | A | 287 | 56.297 | −17.991 | −5.503 | 1.00 | 21.67 | A | C |
| ATOM | 4331 | C | ALA | A | 287 | 58.540 | −18.779 | −4.678 | 1.00 | 23.56 | A | C |
| ATOM | 4332 | O | ALA | A | 287 | 59.038 | −17.632 | −4.868 | 1.00 | 25.80 | A | O |
| ATOM | 4334 | N | PHE | A | 288 | 59.286 | −19.860 | −4.502 | 1.00 | 21.24 | A | N |
| ATOM | 4335 | CA | PHE | A | 288 | 60.720 | −19.748 | −4.348 | 1.00 | 22.02 | A | C |
| ATOM | 4337 | CB | PHE | A | 288 | 61.254 | −20.872 | −3.493 | 1.00 | 22.68 | A | C |
| ATOM | 4340 | CG | PHE | A | 288 | 61.372 | −22.180 | −4.225 | 1.00 | 26.97 | A | C |
| ATOM | 4341 | CD1 | PHE | A | 288 | 62.541 | −22.512 | −4.885 | 1.00 | 31.37 | A | C |
| ATOM | 4343 | CE1 | PHE | A | 288 | 62.649 | −23.713 | −5.570 | 1.00 | 35.11 | A | C |
| ATOM | 4345 | CZ | PHE | A | 288 | 61.587 | −24.584 | −5.596 | 1.00 | 29.46 | A | C |
| ATOM | 4347 | CE2 | PHE | A | 288 | 60.415 | −24.273 | −4.937 | 1.00 | 33.40 | A | C |
| ATOM | 4349 | CD2 | PHE | A | 288 | 60.310 | −23.067 | −4.255 | 1.00 | 33.76 | A | C |
| ATOM | 4351 | C | PHE | A | 288 | 61.451 | −19.743 | −5.697 | 1.00 | 26.03 | A | C |
| ATOM | 4352 | O | PHE | A | 288 | 62.568 | −19.226 | −5.784 | 1.00 | 25.19 | A | O |
| ATOM | 4354 | N | GLU | A | 289 | 60.836 | −20.322 | −6.734 | 1.00 | 27.65 | A | N |
| ATOM | 4355 | CA | GLU | A | 289 | 61.515 | −20.489 | −8.023 | 1.00 | 30.57 | A | C |
| ATOM | 4357 | CB | GLU | A | 289 | 60.643 | −21.265 | −9.023 | 1.00 | 32.76 | A | C |
| ATOM | 4360 | CG | GLU | A | 289 | 60.270 | −22.716 | −8.620 | 1.00 | 35.64 | A | C |
| ATOM | 4363 | CD | GLU | A | 289 | 58.926 | −22.861 | −7.872 | 1.00 | 42.73 | A | C |

TABLE 4-2-continued

Coordinates of *P. alba* IspS

| | | | | | | | | | | | | |
|---|---|---|---|---|---|---|---|---|---|---|---|---|
| ATOM | 4364 | OE1 | GLU | A | 289 | 58.488 | −21.920 | −7.160 | 1.00 | 37.11 | A | O |
| ATOM | 4365 | OE2 | GLU | A | 289 | 58.306 | −23.949 | −8.008 | 1.00 | 42.82 | A | O |
| ATOM | 4366 | C | GLU | A | 289 | 61.916 | −19.123 | −8.599 | 1.00 | 30.30 | A | C |
| ATOM | 4367 | O | GLU | A | 289 | 61.153 | −18.141 | −8.491 | 1.00 | 29.03 | A | O |
| ATOM | 4369 | N | PRO | A | 290 | 63.115 | −19.049 | −9.204 | 1.00 | 28.09 | A | N |
| ATOM | 4370 | CA | PRO | A | 290 | 63.664 | −17.754 | −9.554 | 1.00 | 29.01 | A | C |
| ATOM | 4372 | CB | PRO | A | 290 | 65.013 | −18.089 | −10.205 | 1.00 | 29.11 | A | C |
| ATOM | 4375 | CG | PRO | A | 290 | 64.972 | −19.515 | −10.485 | 1.00 | 29.92 | A | C |
| ATOM | 4378 | CD | PRO | A | 290 | 64.059 | −20.129 | −9.491 | 1.00 | 29.29 | A | C |
| ATOM | 4381 | C | PRO | A | 290 | 62.789 | −16.958 | −10.500 | 1.00 | 28.51 | A | C |
| ATOM | 4382 | O | PRO | A | 290 | 62.732 | −15.737 | −10.385 | 1.00 | 28.65 | A | O |
| ATOM | 4383 | N | GLN | A | 291 | 62.099 | −17.650 | −11.397 | 1.00 | 27.75 | A | N |
| ATOM | 4384 | CA | GLN | A | 291 | 61.250 | −16.998 | −12.382 | 1.00 | 28.53 | A | C |
| ATOM | 4386 | CB | GLN | A | 291 | 60.845 | −17.961 | −13.519 | 1.00 | 27.02 | A | C |
| ATOM | 4389 | CG | GLN | A | 291 | 59.893 | −19.074 | −13.155 | 1.00 | 31.90 | A | C |
| ATOM | 4392 | CD | GLN | A | 291 | 60.583 | −20.284 | −12.532 | 1.00 | 38.40 | A | C |
| ATOM | 4393 | OE1 | GLN | A | 291 | 61.709 | −20.183 | −12.037 | 1.00 | 39.73 | A | O |
| ATOM | 4394 | NE2 | GLN | A | 291 | 59.911 | −21.449 | −12.576 | 1.00 | 32.16 | A | N |
| ATOM | 4397 | C | GLN | A | 291 | 59.993 | −16.369 | −11.795 | 1.00 | 29.44 | A | C |
| ATOM | 4398 | O | GLN | A | 291 | 59.343 | −15.592 | −12.496 | 1.00 | 31.07 | A | O |
| ATOM | 4400 | N | TYR | A | 292 | 59.633 | −16.690 | −10.547 | 1.00 | 28.42 | A | N |
| ATOM | 4401 | CA | TYR | A | 292 | 58.398 | −16.147 | −9.951 | 1.00 | 27.91 | A | C |
| ATOM | 4403 | CB | TYR | A | 292 | 57.733 | −17.182 | −9.046 | 1.00 | 30.21 | A | C |
| ATOM | 4406 | CG | TYR | A | 292 | 57.131 | −18.402 | −9.740 | 1.00 | 31.70 | A | C |
| ATOM | 4407 | CD1 | TYR | A | 292 | 56.502 | −18.299 | −10.975 | 1.00 | 31.99 | A | C |
| ATOM | 4409 | CE1 | TYR | A | 292 | 55.951 | −19.407 | −11.591 | 1.00 | 39.31 | A | C |
| ATOM | 4411 | CZ | TYR | A | 292 | 55.999 | −20.641 | −10.970 | 1.00 | 38.20 | A | C |
| ATOM | 4412 | OH | TYR | A | 292 | 55.441 | −21.716 | −11.596 | 1.00 | 45.03 | A | O |
| ATOM | 4414 | CE2 | TYR | A | 292 | 56.601 | −20.781 | −9.735 | 1.00 | 42.05 | A | C |
| ATOM | 4416 | CD2 | TYR | A | 292 | 57.166 | −19.663 | −9.126 | 1.00 | 39.69 | A | C |
| ATOM | 4418 | C | TYR | A | 292 | 58.594 | −14.816 | −9.182 | 1.00 | 28.53 | A | C |
| ATOM | 4419 | O | TYR | A | 292 | 57.989 | −14.590 | −8.118 | 1.00 | 25.90 | A | O |
| ATOM | 4421 | N | SER | A | 293 | 59.398 | −13.916 | −9.747 | 1.00 | 28.30 | A | N |
| ATOM | 4422 | CA | SER | A | 293 | 59.641 | −12.601 | −9.135 | 1.00 | 28.09 | A | C |
| ATOM | 4424 | CB | SER | A | 293 | 60.602 | −11.763 | −10.009 | 1.00 | 29.47 | A | C |
| ATOM | 4427 | OG | SER | A | 293 | 61.965 | −11.924 | −9.592 | 1.00 | 29.79 | A | O |
| ATOM | 4429 | C | SER | A | 293 | 58.352 | −11.808 | −8.874 | 1.00 | 28.45 | A | C |
| ATOM | 4430 | O | SER | A | 293 | 58.189 | −11.199 | −7.805 | 1.00 | 28.09 | A | O |
| ATOM | 4432 | N | ASP | A | 294 | 57.449 | −11.808 | −9.855 | 1.00 | 26.88 | A | N |
| ATOM | 4433 | CA | ASP | A | 294 | 56.223 | −11.048 | −9.784 | 1.00 | 25.77 | A | C |
| ATOM | 4435 | CB | ASP | A | 294 | 55.461 | −11.124 | −11.117 | 1.00 | 28.17 | A | C |
| ATOM | 4438 | CG | ASP | A | 294 | 56.157 | −10.395 | −12.248 | 1.00 | 34.74 | A | C |
| ATOM | 4439 | OD1 | ASP | A | 294 | 56.956 | −9.462 | −12.000 | 1.00 | 36.83 | A | O |
| ATOM | 4440 | OD2 | ASP | A | 294 | 55.888 | −10.765 | −13.412 | 1.00 | 45.26 | A | O |
| ATOM | 4441 | C | ASP | A | 294 | 55.313 | −11.591 | −8.684 | 1.00 | 28.84 | A | C |
| ATOM | 4442 | O | ASP | A | 294 | 54.585 | −10.823 | −8.009 | 1.00 | 29.14 | A | O |
| ATOM | 4444 | N | CYS | A | 295 | 55.322 | −12.912 | −8.517 | 1.00 | 26.55 | A | N |
| ATOM | 4445 | CA | CYS | A | 295 | 54.540 | −13.511 | −7.464 | 1.00 | 27.07 | A | C |
| ATOM | 4447 | CB | CYS | A | 295 | 54.524 | −15.043 | −7.567 | 1.00 | 28.06 | A | C |
| ATOM | 4450 | SG | CYS | A | 295 | 53.328 | −15.810 | −6.436 | 1.00 | 26.81 | A | S |
| ATOM | 4452 | C | CYS | A | 295 | 55.044 | −13.060 | −6.100 | 1.00 | 25.39 | A | C |
| ATOM | 4453 | O | CYS | A | 295 | 54.254 | −12.597 | −5.284 | 1.00 | 26.37 | A | O |
| ATOM | 4455 | N | ARG | A | 296 | 56.345 | −13.169 | −5.861 | 1.00 | 24.67 | A | N |
| ATOM | 4456 | CA | ARG | A | 296 | 56.923 | −12.732 | −4.592 | 1.00 | 24.65 | A | C |
| ATOM | 4458 | CB | ARG | A | 296 | 58.437 | −12.963 | −4.543 | 1.00 | 25.23 | A | C |
| ATOM | 4461 | CG | ARG | A | 296 | 58.835 | −14.418 | −4.502 | 1.00 | 22.91 | A | C |
| ATOM | 4464 | CD | ARG | A | 296 | 60.318 | −14.618 | −4.304 | 1.00 | 19.82 | A | C |
| ATOM | 4467 | NE | ARG | A | 296 | 61.076 | −14.305 | −5.507 | 1.00 | 19.18 | A | N |
| ATOM | 4469 | CZ | ARG | A | 296 | 61.223 | −15.096 | −6.561 | 1.00 | 22.17 | A | C |
| ATOM | 4470 | NH1 | ARG | A | 296 | 60.647 | −16.274 | −6.620 | 1.00 | 26.97 | A | N |
| ATOM | 4473 | NH2 | ARG | A | 296 | 61.933 | −14.676 | −7.592 | 1.00 | 26.83 | A | N |
| ATOM | 4476 | C | ARG | A | 296 | 56.651 | −11.249 | −4.321 | 1.00 | 24.07 | A | C |
| ATOM | 4477 | O | ARG | A | 296 | 56.264 | −10.893 | −3.221 | 1.00 | 24.88 | A | O |
| ATOM | 4479 | N | ASN | A | 297 | 56.849 | −10.408 | −5.325 | 1.00 | 23.19 | A | N |
| ATOM | 4480 | CA | ASN | A | 297 | 56.624 | −8.982 | −5.192 | 1.00 | 24.62 | A | C |
| ATOM | 4482 | CB | ASN | A | 297 | 57.063 | −8.215 | −6.463 | 1.00 | 25.20 | A | C |
| ATOM | 4485 | CG | ASN | A | 297 | 58.598 | −8.235 | −6.676 | 1.00 | 30.05 | A | C |
| ATOM | 4486 | OD1 | ASN | A | 297 | 59.359 | −8.502 | −5.753 | 1.00 | 36.93 | A | O |
| ATOM | 4487 | ND2 | ASN | A | 297 | 59.039 | −7.959 | −7.903 | 1.00 | 25.92 | A | N |
| ATOM | 4490 | C | ASN | A | 297 | 55.152 | −8.696 | −4.866 | 1.00 | 24.78 | A | C |
| ATOM | 4491 | O | ASN | A | 297 | 54.871 | −7.960 | −3.926 | 1.00 | 22.91 | A | O |
| ATOM | 4493 | N | SER | A | 298 | 54.236 | −9.305 | −5.613 | 1.00 | 23.57 | A | N |
| ATOM | 4494 | CA | SER | A | 298 | 52.813 | −9.173 | −5.338 | 1.00 | 25.11 | A | C |
| ATOM | 4496 | CB | SER | A | 298 | 51.968 | −10.060 | −6.272 | 1.00 | 24.10 | A | C |
| ATOM | 4499 | OG | SER | A | 298 | 51.678 | −9.429 | −7.493 | 1.00 | 32.64 | A | O |
| ATOM | 4501 | C | SER | A | 298 | 52.475 | −9.579 | −3.916 | 1.00 | 22.38 | A | C |
| ATOM | 4502 | O | SER | A | 298 | 51.809 | −8.846 | −3.192 | 1.00 | 24.02 | A | O |
| ATOM | 4504 | N | VAL | A | 299 | 52.857 | −10.791 | −3.552 | 1.00 | 21.05 | A | N |

TABLE 4-2-continued

Coordinates of *P. alba* IspS

| | | | | | | | | | | | | |
|---|---|---|---|---|---|---|---|---|---|---|---|---|
| ATOM | 4505 | CA | VAL | A | 299 | 52.520 | −11.321 | −2.237 | 1.00 | 20.22 | A | C |
| ATOM | 4507 | CB | VAL | A | 299 | 52.949 | −12.794 | −2.091 | 1.00 | 20.34 | A | C |
| ATOM | 4509 | CG1 | VAL | A | 299 | 52.838 | −13.258 | −0.650 | 1.00 | 22.69 | A | C |
| ATOM | 4513 | CG2 | VAL | A | 299 | 52.089 | −13.647 | −2.954 | 1.00 | 18.14 | A | C |
| ATOM | 4517 | C | VAL | A | 299 | 53.124 | −10.468 | −1.133 | 1.00 | 19.72 | A | C |
| ATOM | 4518 | O | VAL | A | 299 | 52.466 | −10.220 | −0.122 | 1.00 | 21.66 | A | O |
| ATOM | 4520 | N | ALA | A | 300 | 54.342 | −9.970 | −1.342 | 1.00 | 19.58 | A | N |
| ATOM | 4521 | CA | ALA | A | 300 | 55.011 | −9.150 | −0.320 | 1.00 | 21.43 | A | C |
| ATOM | 4523 | CB | ALA | A | 300 | 56.486 | −8.987 | −0.667 | 1.00 | 19.80 | A | C |
| ATOM | 4527 | C | ALA | A | 300 | 54.339 | −7.779 | −0.181 | 1.00 | 21.64 | A | C |
| ATOM | 4528 | O | ALA | A | 300 | 54.232 | −7.202 | 0.922 | 1.00 | 21.71 | A | O |
| ATOM | 4530 | N | LYS | A | 301 | 53.872 | −7.255 | −1.303 | 1.00 | 22.14 | A | N |
| ATOM | 4531 | CA | LYS | A | 301 | 53.204 | −5.964 | −1.281 | 1.00 | 21.36 | A | C |
| ATOM | 4533 | CB | LYS | A | 301 | 52.984 | −5.439 | −2.690 | 1.00 | 20.86 | A | C |
| ATOM | 4536 | CG | LYS | A | 301 | 54.236 | −4.921 | −3.366 | 1.00 | 19.27 | A | C |
| ATOM | 4539 | CD | LYS | A | 301 | 53.965 | −4.388 | −4.792 | 1.00 | 19.50 | A | C |
| ATOM | 4542 | CE | LYS | A | 301 | 55.276 | −3.879 | −5.400 | 1.00 | 29.29 | A | C |
| ATOM | 4545 | NZ | LYS | A | 301 | 55.116 | −3.235 | −6.741 | 1.00 | 34.09 | A | N |
| ATOM | 4549 | C | LYS | A | 301 | 51.879 | −6.131 | −0.548 | 1.00 | 21.48 | A | C |
| ATOM | 4550 | O | LYS | A | 301 | 51.540 | −5.352 | 0.338 | 1.00 | 22.68 | A | O |
| ATOM | 4552 | N | MET | A | 302 | 51.160 | −7.192 | −0.878 | 1.00 | 20.39 | A | N |
| ATOM | 4553 | CA | MET | A | 302 | 49.849 | −7.409 | −0.282 | 1.00 | 20.92 | A | C |
| ATOM | 4555 | CB | MET | A | 302 | 49.133 | −8.583 | −0.969 | 1.00 | 20.09 | A | C |
| ATOM | 4558 | CG | MET | A | 302 | 48.712 | −8.266 | −2.405 | 1.00 | 19.65 | A | C |
| ATOM | 4561 | SD | MET | A | 302 | 47.843 | −6.709 | −2.587 | 1.00 | 28.88 | A | S |
| ATOM | 4562 | CE | MET | A | 302 | 49.185 | −5.629 | −3.034 | 1.00 | 23.45 | A | C |
| ATOM | 4566 | C | MET | A | 302 | 49.937 | −7.677 | 1.199 | 1.00 | 22.54 | A | C |
| ATOM | 4567 | O | MET | A | 302 | 49.185 | −7.097 | 1.998 | 1.00 | 24.84 | A | O |
| ATOM | 4569 | N | PHE | A | 303 | 50.861 | −8.551 | 1.579 | 1.00 | 22.29 | A | N |
| ATOM | 4570 | CA | PHE | A | 303 | 51.019 | −8.862 | 2.982 | 1.00 | 22.99 | A | C |
| ATOM | 4572 | CB | PHE | A | 303 | 51.984 | −10.050 | 3.159 | 1.00 | 25.28 | A | C |
| ATOM | 4575 | CG | PHE | A | 303 | 51.716 | −10.891 | 4.387 | 1.00 | 30.30 | A | C |
| ATOM | 4576 | CD1 | PHE | A | 303 | 50.589 | −10.683 | 5.192 | 1.00 | 34.42 | A | C |
| ATOM | 4578 | CE1 | PHE | A | 303 | 50.371 | −11.460 | 6.324 | 1.00 | 42.97 | A | C |
| ATOM | 4580 | CZ | PHE | A | 303 | 51.274 | −12.459 | 6.657 | 1.00 | 41.14 | A | C |
| ATOM | 4582 | CE2 | PHE | A | 303 | 52.381 | −12.678 | 5.871 | 1.00 | 34.43 | A | C |
| ATOM | 4584 | CD2 | PHE | A | 303 | 52.599 | −11.899 | 4.741 | 1.00 | 36.11 | A | C |
| ATOM | 4586 | C | PHE | A | 303 | 51.455 | −7.625 | 3.816 | 1.00 | 21.77 | A | C |
| ATOM | 4587 | O | PHE | A | 303 | 51.033 | −7.464 | 4.938 | 1.00 | 23.38 | A | O |
| ATOM | 4589 | N | SER | A | 304 | 52.270 | −6.755 | 3.244 | 1.00 | 20.77 | A | N |
| ATOM | 4590 | CA | SER | A | 304 | 52.648 | −5.517 | 3.876 | 1.00 | 21.72 | A | C |
| ATOM | 4592 | CB | SER | A | 304 | 53.638 | −4.750 | 2.997 | 1.00 | 24.31 | A | C |
| ATOM | 4595 | OG | SER | A | 304 | 54.847 | −5.480 | 2.795 | 1.00 | 28.25 | A | O |
| ATOM | 4597 | C | SER | A | 304 | 51.440 | −4.622 | 4.150 | 1.00 | 23.63 | A | C |
| ATOM | 4598 | O | SER | A | 304 | 51.387 | −4.005 | 5.212 | 1.00 | 24.50 | A | O |
| ATOM | 4600 | N | PHE | A | 305 | 50.497 | −4.541 | 3.205 | 1.00 | 23.27 | A | N |
| ATOM | 4601 | CA | PHE | A | 305 | 49.230 | −3.804 | 3.424 | 1.00 | 21.89 | A | C |
| ATOM | 4603 | CB | PHE | A | 305 | 48.466 | −3.560 | 2.113 | 1.00 | 22.71 | A | C |
| ATOM | 4606 | CG | PHE | A | 305 | 48.938 | −2.345 | 1.368 | 1.00 | 20.52 | A | C |
| ATOM | 4607 | CD1 | PHE | A | 305 | 48.659 | −1.073 | 1.850 | 1.00 | 24.16 | A | C |
| ATOM | 4609 | CE1 | PHE | A | 305 | 49.097 | 0.050 | 1.181 | 1.00 | 23.31 | A | C |
| ATOM | 4611 | CZ | PHE | A | 305 | 49.826 | −0.078 | 0.013 | 1.00 | 23.43 | A | C |
| ATOM | 4613 | CE2 | PHE | A | 305 | 50.120 | −1.337 | −0.478 | 1.00 | 29.03 | A | C |
| ATOM | 4615 | CD2 | PHE | A | 305 | 49.682 | −2.469 | 0.219 | 1.00 | 22.45 | A | C |
| ATOM | 4617 | C | PHE | A | 305 | 48.313 | −4.499 | 4.393 | 1.00 | 20.95 | A | C |
| ATOM | 4618 | O | PHE | A | 305 | 47.674 | −3.849 | 5.226 | 1.00 | 20.99 | A | O |
| ATOM | 4620 | N | VAL | A | 306 | 48.255 | −5.821 | 4.309 | 1.00 | 20.76 | A | N |
| ATOM | 4621 | CA | VAL | A | 306 | 47.434 | −6.575 | 5.229 | 1.00 | 19.75 | A | C |
| ATOM | 4623 | CB | VAL | A | 306 | 47.506 | −8.080 | 4.963 | 1.00 | 22.66 | A | C |
| ATOM | 4625 | CG1 | VAL | A | 306 | 46.885 | −8.886 | 6.091 | 1.00 | 16.37 | A | C |
| ATOM | 4629 | CG2 | VAL | A | 306 | 46.790 | −8.388 | 3.645 | 1.00 | 21.60 | A | C |
| ATOM | 4633 | C | VAL | A | 306 | 47.823 | −6.224 | 6.636 | 1.00 | 22.33 | A | C |
| ATOM | 4634 | O | VAL | A | 306 | 46.962 | −5.861 | 7.435 | 1.00 | 24.20 | A | O |
| ATOM | 4636 | N | THR | A | 307 | 49.108 | −6.225 | 6.945 | 1.00 | 24.63 | A | N |
| ATOM | 4637 | CA | THR | A | 307 | 49.502 | −6.040 | 8.344 | 1.00 | 26.20 | A | C |
| ATOM | 4639 | CB | THR | A | 307 | 51.009 | −6.313 | 8.570 | 1.00 | 26.67 | A | C |
| ATOM | 4641 | OG1 | THR | A | 307 | 51.771 | −5.398 | 7.828 | 1.00 | 36.85 | A | O |
| ATOM | 4643 | CG2 | THR | A | 307 | 51.386 | −7.698 | 8.106 | 1.00 | 31.58 | A | C |
| ATOM | 4647 | C | THR | A | 307 | 49.092 | −4.669 | 8.895 | 1.00 | 25.04 | A | C |
| ATOM | 4648 | O | THR | A | 307 | 48.668 | −4.547 | 10.049 | 1.00 | 26.45 | A | O |
| ATOM | 4650 | N | ILE | A | 308 | 49.172 | −3.647 | 8.060 | 1.00 | 23.77 | A | N |
| ATOM | 4651 | CA | ILE | A | 308 | 48.761 | −2.299 | 8.445 | 1.00 | 23.18 | A | C |
| ATOM | 4653 | CB | ILE | A | 308 | 49.219 | −1.270 | 7.409 | 1.00 | 24.44 | A | C |
| ATOM | 4655 | CG1 | ILE | A | 308 | 50.742 | −1.206 | 7.371 | 1.00 | 29.53 | A | C |
| ATOM | 4658 | CD1 | ILE | A | 308 | 51.267 | −0.355 | 6.265 | 1.00 | 30.91 | A | C |
| ATOM | 4662 | CG2 | ILE | A | 308 | 48.639 | 0.078 | 7.714 | 1.00 | 23.42 | A | C |
| ATOM | 4666 | C | ILE | A | 308 | 47.252 | −2.223 | 8.554 | 1.00 | 20.59 | A | C |
| ATOM | 4667 | O | ILE | A | 308 | 46.723 | −1.650 | 9.506 | 1.00 | 20.09 | A | O |

TABLE 4-2-continued

Coordinates of *P. alba* IspS

| | | | | | | | | | | | | |
|---|---|---|---|---|---|---|---|---|---|---|---|---|
| ATOM | 4669 | N | ILE | A | 309 | 46.551 | −2.802 | 7.585 | 1.00 | 20.24 | A | N |
| ATOM | 4670 | CA | ILE | A | 309 | 45.093 | −2.712 | 7.594 | 1.00 | 22.80 | A | C |
| ATOM | 4672 | CB | ILE | A | 309 | 44.466 | −3.173 | 6.284 | 1.00 | 24.10 | A | C |
| ATOM | 4674 | CG1 | ILE | A | 309 | 44.927 | −2.279 | 5.128 | 1.00 | 25.79 | A | C |
| ATOM | 4677 | CD1 | ILE | A | 309 | 44.234 | −1.018 | 5.079 | 1.00 | 37.61 | A | C |
| ATOM | 4681 | CG2 | ILE | A | 309 | 42.941 | −3.162 | 6.360 | 1.00 | 17.79 | A | C |
| ATOM | 4685 | C | ILE | A | 309 | 44.584 | −3.521 | 8.777 | 1.00 | 23.44 | A | C |
| ATOM | 4686 | O | ILE | A | 309 | 43.626 | −3.118 | 9.447 | 1.00 | 23.95 | A | O |
| ATOM | 4688 | N | ASP | A | 310 | 45.278 | −4.617 | 9.076 | 1.00 | 24.85 | A | N |
| ATOM | 4689 | CA | ASP | A | 310 | 44.942 | −5.453 | 10.226 | 1.00 | 25.67 | A | C |
| ATOM | 4691 | CB | ASP | A | 310 | 45.823 | −6.716 | 10.278 | 1.00 | 29.93 | A | C |
| ATOM | 4694 | CG | ASP | A | 310 | 45.316 | −7.775 | 11.294 | 1.00 | 34.30 | A | C |
| ATOM | 4695 | OD1 | ASP | A | 310 | 44.106 | −7.830 | 11.573 | 1.00 | 46.69 | A | O |
| ATOM | 4696 | OD2 | ASP | A | 310 | 46.139 | −8.566 | 11.790 | 1.00 | 50.27 | A | O |
| ATOM | 4697 | C | ASP | A | 310 | 45.084 | −4.658 | 11.501 | 1.00 | 23.92 | A | C |
| ATOM | 4698 | O | ASP | A | 310 | 44.202 | −4.696 | 12.344 | 1.00 | 23.74 | A | O |
| ATOM | 4700 | N | ASP | A | 311 | 46.167 | −3.903 | 11.648 | 1.00 | 23.61 | A | N |
| ATOM | 4701 | CA | ASP | A | 311 | 46.302 | −3.063 | 12.840 | 1.00 | 24.15 | A | C |
| ATOM | 4703 | CB | ASP | A | 311 | 47.653 | −2.346 | 12.864 | 1.00 | 25.79 | A | C |
| ATOM | 4706 | CG | ASP | A | 311 | 48.811 | −3.283 | 13.157 | 1.00 | 33.35 | A | C |
| ATOM | 4707 | OD1 | ASP | A | 311 | 48.578 | −4.327 | 13.802 | 1.00 | 37.00 | A | O |
| ATOM | 4708 | OD2 | ASP | A | 311 | 49.951 | −2.976 | 12.720 | 1.00 | 42.12 | A | O |
| ATOM | 4709 | C | ASP | A | 311 | 45.185 | −2.013 | 12.963 | 1.00 | 22.01 | A | C |
| ATOM | 4710 | O | ASP | A | 311 | 44.750 | −1.689 | 14.066 | 1.00 | 20.06 | A | O |
| ATOM | 4712 | N | ILE | A | 312 | 44.738 | −1.486 | 11.827 | 1.00 | 20.61 | A | N |
| ATOM | 4713 | CA | ILE | A | 312 | 43.693 | −0.467 | 11.814 | 1.00 | 20.98 | A | C |
| ATOM | 4715 | CB | ILE | A | 312 | 43.462 | 0.111 | 10.392 | 1.00 | 20.72 | A | C |
| ATOM | 4717 | CG1 | ILE | A | 312 | 44.605 | 1.043 | 10.000 | 1.00 | 19.24 | A | C |
| ATOM | 4720 | CD1 | ILE | A | 312 | 44.576 | 1.481 | 8.508 | 1.00 | 18.67 | A | C |
| ATOM | 4724 | CG2 | ILE | A | 312 | 42.163 | 0.844 | 10.337 | 1.00 | 17.52 | A | C |
| ATOM | 4728 | C | ILE | A | 312 | 42.403 | −1.049 | 12.373 | 1.00 | 21.29 | A | C |
| ATOM | 4729 | O | ILE | A | 312 | 41.781 | −0.462 | 13.259 | 1.00 | 22.89 | A | O |
| ATOM | 4731 | N | TYR | A | 313 | 42.036 | −2.232 | 11.905 | 1.00 | 21.99 | A | N |
| ATOM | 4732 | CA | TYR | A | 313 | 40.816 | −2.852 | 12.362 | 1.00 | 22.07 | A | C |
| ATOM | 4734 | CB | TYR | A | 313 | 40.395 | −3.962 | 11.408 | 1.00 | 21.44 | A | C |
| ATOM | 4737 | CG | TYR | A | 313 | 39.668 | −3.483 | 10.187 | 1.00 | 17.68 | A | C |
| ATOM | 4738 | CD1 | TYR | A | 313 | 38.273 | −3.567 | 10.095 | 1.00 | 17.60 | A | C |
| ATOM | 4740 | CE1 | TYR | A | 313 | 37.601 | −3.157 | 8.927 | 1.00 | 18.93 | A | C |
| ATOM | 4742 | CZ | TYR | A | 313 | 38.333 | −2.642 | 7.866 | 1.00 | 20.93 | A | C |
| ATOM | 4743 | OH | TYR | A | 313 | 37.713 | −2.225 | 6.703 | 1.00 | 21.19 | A | O |
| ATOM | 4745 | CE2 | TYR | A | 313 | 39.705 | −2.556 | 7.953 | 1.00 | 21.64 | A | C |
| ATOM | 4747 | CD2 | TYR | A | 313 | 40.361 | −2.958 | 9.111 | 1.00 | 20.65 | A | C |
| ATOM | 4749 | C | TYR | A | 313 | 40.929 | −3.399 | 13.761 | 1.00 | 24.20 | A | C |
| ATOM | 4750 | O | TYR | A | 313 | 39.957 | −3.362 | 14.526 | 1.00 | 25.90 | A | O |
| ATOM | 4752 | N | ASP | A | 314 | 42.119 | −3.872 | 14.108 | 1.00 | 26.32 | A | N |
| ATOM | 4753 | CA | ASP | A | 314 | 42.339 | −4.552 | 15.395 | 1.00 | 27.33 | A | C |
| ATOM | 4755 | CB | ASP | A | 314 | 43.622 | −5.398 | 15.321 | 1.00 | 29.31 | A | C |
| ATOM | 4758 | CG | ASP | A | 314 | 43.891 | −6.217 | 16.598 | 1.00 | 33.13 | A | C |
| ATOM | 4759 | OD1 | ASP | A | 314 | 42.985 | −6.889 | 17.107 | 1.00 | 38.25 | A | O |
| ATOM | 4760 | OD2 | ASP | A | 314 | 45.038 | −6.219 | 17.065 | 1.00 | 42.87 | A | O |
| ATOM | 4761 | C | ASP | A | 314 | 42.415 | −3.565 | 16.560 | 1.00 | 25.83 | A | C |
| ATOM | 4762 | O | ASP | A | 314 | 41.786 | −3.798 | 17.589 | 1.00 | 24.11 | A | O |
| ATOM | 4764 | N | VAL | A | 315 | 43.168 | −2.469 | 16.419 | 1.00 | 25.13 | A | N |
| ATOM | 4765 | CA | VAL | A | 315 | 43.388 | −1.571 | 17.581 | 1.00 | 23.81 | A | C |
| ATOM | 4767 | CB | VAL | A | 315 | 44.803 | −1.707 | 18.175 | 1.00 | 24.08 | A | C |
| ATOM | 4769 | CG1 | VAL | A | 315 | 44.920 | −3.047 | 18.917 | 1.00 | 27.01 | A | C |
| ATOM | 4773 | CG2 | VAL | A | 315 | 45.876 | −1.542 | 17.111 | 1.00 | 18.89 | A | C |
| ATOM | 4777 | C | VAL | A | 315 | 43.121 | −0.091 | 17.390 | 1.00 | 24.28 | A | C |
| ATOM | 4778 | O | VAL | A | 315 | 42.626 | 0.550 | 18.316 | 1.00 | 25.60 | A | O |
| ATOM | 4780 | N | TYR | A | 316 | 43.452 | 0.454 | 16.218 | 1.00 | 23.17 | A | N |
| ATOM | 4781 | CA | TYR | A | 316 | 43.463 | 1.888 | 16.012 | 1.00 | 22.03 | A | C |
| ATOM | 4783 | CB | TYR | A | 316 | 44.468 | 2.250 | 14.921 | 1.00 | 24.42 | A | C |
| ATOM | 4786 | CG | TYR | A | 316 | 44.780 | 3.741 | 14.847 | 1.00 | 24.19 | A | C |
| ATOM | 4787 | CD1 | TYR | A | 316 | 45.669 | 4.330 | 15.734 | 1.00 | 22.67 | A | C |
| ATOM | 4789 | CE1 | TYR | A | 316 | 45.956 | 5.710 | 15.664 | 1.00 | 26.80 | A | C |
| ATOM | 4791 | CZ | TYR | A | 316 | 45.343 | 6.487 | 14.689 | 1.00 | 23.98 | A | C |
| ATOM | 4792 | OH | TYR | A | 316 | 45.616 | 7.825 | 14.594 | 1.00 | 23.58 | A | O |
| ATOM | 4794 | CE2 | TYR | A | 316 | 44.462 | 5.915 | 13.802 | 1.00 | 27.54 | A | C |
| ATOM | 4796 | CD2 | TYR | A | 316 | 44.188 | 4.553 | 13.880 | 1.00 | 23.46 | A | C |
| ATOM | 4798 | C | TYR | A | 316 | 42.109 | 2.489 | 15.659 | 1.00 | 21.60 | A | C |
| ATOM | 4799 | O | TYR | A | 316 | 41.709 | 3.471 | 16.256 | 1.00 | 21.67 | A | O |
| ATOM | 4801 | N | GLY | A | 317 | 41.407 | 1.917 | 14.684 | 1.00 | 22.29 | A | N |
| ATOM | 4802 | CA | GLY | A | 317 | 40.150 | 2.510 | 14.186 | 1.00 | 21.66 | A | C |
| ATOM | 4805 | C | GLY | A | 317 | 38.877 | 2.302 | 15.016 | 1.00 | 22.48 | A | C |
| ATOM | 4806 | O | GLY | A | 317 | 38.613 | 1.212 | 15.566 | 1.00 | 20.21 | A | O |
| ATOM | 4808 | N | THR | A | 318 | 38.050 | 3.335 | 15.090 | 1.00 | 21.00 | A | N |
| ATOM | 4809 | CA | THR | A | 318 | 36.756 | 3.163 | 15.737 | 1.00 | 22.14 | A | C |
| ATOM | 4811 | CB | THR | A | 318 | 36.126 | 4.472 | 16.125 | 1.00 | 20.46 | A | C |

TABLE 4-2-continued

| Coordinates of *P. alba* IspS | | | | | | | | | | | |
|---|---|---|---|---|---|---|---|---|---|---|---|
| ATOM | 4813 | OG1 | THR | A | 318 | 35.835 | 5.197 | 14.935 | 1.00 | 20.90 | A | O |
| ATOM | 4815 | CG2 | THR | A | 318 | 37.073 | 5.280 | 17.008 | 1.00 | 21.19 | A | C |
| ATOM | 4819 | C | THR | A | 318 | 35.844 | 2.436 | 14.759 | 1.00 | 21.63 | A | C |
| ATOM | 4820 | O | THR | A | 318 | 36.110 | 2.395 | 13.550 | 1.00 | 21.76 | A | O |
| ATOM | 4822 | N | LEU | A | 319 | 34.777 | 1.864 | 15.297 | 1.00 | 20.18 | A | N |
| ATOM | 4823 | CA | LEU | A | 319 | 33.830 | 1.067 | 14.514 | 1.00 | 22.24 | A | C |
| ATOM | 4825 | CB | LEU | A | 319 | 32.701 | 0.551 | 15.416 | 1.00 | 22.04 | A | C |
| ATOM | 4828 | CG | LEU | A | 319 | 32.239 | −0.897 | 15.249 | 1.00 | 31.30 | A | C |
| ATOM | 4830 | CD1 | LEU | A | 319 | 33.410 | −1.842 | 15.024 | 1.00 | 25.53 | A | C |
| ATOM | 4834 | CD2 | LEU | A | 319 | 31.421 | −1.339 | 16.464 | 1.00 | 34.06 | A | C |
| ATOM | 4838 | C | LEU | A | 319 | 33.258 | 1.867 | 13.347 | 1.00 | 23.17 | A | C |
| ATOM | 4839 | O | LEU | A | 319 | 33.195 | 1.361 | 12.226 | 1.00 | 23.56 | A | O |
| ATOM | 4841 | N | ASP | A | 320 | 32.877 | 3.118 | 13.610 | 1.00 | 23.84 | A | N |
| ATOM | 4842 | CA | ASP | A | 320 | 32.388 | 4.035 | 12.580 | 1.00 | 26.41 | A | C |
| ATOM | 4844 | CB | ASP | A | 320 | 31.999 | 5.411 | 13.174 | 1.00 | 28.62 | A | C |
| ATOM | 4847 | CG | ASP | A | 320 | 30.753 | 5.370 | 14.089 | 1.00 | 34.92 | A | C |
| ATOM | 4848 | OD1 | ASP | A | 320 | 29.889 | 4.480 | 13.934 | 1.00 | 40.85 | A | O |
| ATOM | 4849 | OD2 | ASP | A | 320 | 30.633 | 6.273 | 14.960 | 1.00 | 45.71 | A | O |
| ATOM | 4850 | C | ASP | A | 320 | 33.454 | 4.260 | 11.490 | 1.00 | 25.67 | A | C |
| ATOM | 4851 | O | ASP | A | 320 | 33.133 | 4.313 | 10.319 | 1.00 | 26.46 | A | O |
| ATOM | 4853 | N | GLU | A | 321 | 34.713 | 4.420 | 11.879 | 1.00 | 24.15 | A | N |
| ATOM | 4854 | CA | GLU | A | 321 | 35.787 | 4.613 | 10.895 | 1.00 | 22.51 | A | C |
| ATOM | 4856 | CB | GLU | A | 321 | 37.102 | 4.984 | 11.579 | 1.00 | 21.98 | A | C |
| ATOM | 4859 | CG | GLU | A | 321 | 37.114 | 6.354 | 12.250 | 1.00 | 22.24 | A | C |
| ATOM | 4862 | CD | GLU | A | 321 | 38.425 | 6.622 | 13.009 | 1.00 | 26.20 | A | C |
| ATOM | 4863 | OE1 | GLU | A | 321 | 39.060 | 5.664 | 13.490 | 1.00 | 22.42 | A | O |
| ATOM | 4864 | OE2 | GLU | A | 321 | 38.823 | 7.795 | 13.126 | 1.00 | 26.34 | A | O |
| ATOM | 4865 | C | GLU | A | 321 | 35.997 | 3.346 | 10.075 | 1.00 | 22.83 | A | C |
| ATOM | 4866 | O | GLU | A | 321 | 36.239 | 3.410 | 8.869 | 1.00 | 20.72 | A | O |
| ATOM | 4868 | N | LEU | A | 322 | 35.902 | 2.191 | 10.735 | 1.00 | 21.58 | A | N |
| ATOM | 4869 | CA | LEU | A | 322 | 36.126 | 0.944 | 10.053 | 1.00 | 21.00 | A | C |
| ATOM | 4871 | CB | LEU | A | 322 | 36.303 | −0.196 | 11.051 | 1.00 | 20.31 | A | C |
| ATOM | 4874 | CG | LEU | A | 322 | 37.454 | −0.038 | 12.044 | 1.00 | 21.17 | A | C |
| ATOM | 4876 | CD1 | LEU | A | 322 | 37.523 | −1.242 | 12.977 | 1.00 | 21.39 | A | C |
| ATOM | 4880 | CD2 | LEU | A | 322 | 38.778 | 0.167 | 11.355 | 1.00 | 21.53 | A | C |
| ATOM | 4884 | C | LEU | A | 322 | 34.998 | 0.636 | 9.065 | 1.00 | 22.33 | A | C |
| ATOM | 4885 | O | LEU | A | 322 | 35.233 | −0.029 | 8.055 | 1.00 | 23.58 | A | O |
| ATOM | 4887 | N | GLU | A | 323 | 33.784 | 1.099 | 9.351 | 1.00 | 23.50 | A | N |
| ATOM | 4888 | CA | GLU | A | 323 | 32.687 | 0.991 | 8.396 | 1.00 | 23.70 | A | C |
| ATOM | 4890 | CB | GLU | A | 323 | 31.342 | 1.418 | 9.002 | 1.00 | 25.90 | A | C |
| ATOM | 4893 | CG | GLU | A | 323 | 30.728 | 0.464 | 10.031 | 1.00 | 31.83 | A | C |
| ATOM | 4896 | CD | GLU | A | 323 | 29.981 | −0.734 | 9.421 | 1.00 | 38.05 | A | C |
| ATOM | 4897 | OE1 | GLU | A | 323 | 29.503 | −1.575 | 10.218 | 1.00 | 40.48 | A | O |
| ATOM | 4898 | OE2 | GLU | A | 323 | 29.875 | −0.839 | 8.170 | 1.00 | 39.62 | A | O |
| ATOM | 4899 | C | GLU | A | 323 | 32.991 | 1.873 | 7.193 | 1.00 | 23.25 | A | C |
| ATOM | 4900 | O | GLU | A | 323 | 32.756 | 1.466 | 6.043 | 1.00 | 20.74 | A | O |
| ATOM | 4902 | N | LEU | A | 324 | 33.507 | 3.082 | 7.434 | 1.00 | 22.29 | A | N |
| ATOM | 4903 | CA | LEU | A | 324 | 33.832 | 3.961 | 6.302 | 1.00 | 23.80 | A | C |
| ATOM | 4905 | CB | LEU | A | 324 | 34.286 | 5.340 | 6.768 | 1.00 | 25.06 | A | C |
| ATOM | 4908 | CG | LEU | A | 324 | 33.225 | 6.246 | 7.386 | 1.00 | 30.71 | A | C |
| ATOM | 4910 | CD1 | LEU | A | 324 | 33.874 | 7.501 | 8.031 | 1.00 | 27.53 | A | C |
| ATOM | 4914 | CD2 | LEU | A | 324 | 32.178 | 6.642 | 6.330 | 1.00 | 32.67 | A | C |
| ATOM | 4918 | C | LEU | A | 324 | 34.888 | 3.306 | 5.399 | 1.00 | 22.01 | A | C |
| ATOM | 4919 | O | LEU | A | 324 | 34.739 | 3.259 | 4.180 | 1.00 | 23.37 | A | O |
| ATOM | 4921 | N | PHE | A | 325 | 35.916 | 2.736 | 6.003 | 1.00 | 21.76 | A | N |
| ATOM | 4922 | CA | PHE | A | 325 | 36.998 | 2.111 | 5.239 | 1.00 | 21.09 | A | C |
| ATOM | 4924 | CB | PHE | A | 325 | 38.125 | 1.683 | 6.176 | 1.00 | 20.33 | A | C |
| ATOM | 4927 | CG | PHE | A | 325 | 39.389 | 1.362 | 5.465 | 1.00 | 18.41 | A | C |
| ATOM | 4928 | CD1 | PHE | A | 325 | 40.259 | 2.364 | 5.107 | 1.00 | 19.45 | A | C |
| ATOM | 4930 | CE1 | PHE | A | 325 | 41.431 | 2.078 | 4.437 | 1.00 | 17.94 | A | C |
| ATOM | 4932 | CZ | PHE | A | 325 | 41.746 | 0.809 | 4.112 | 1.00 | 18.28 | A | C |
| ATOM | 4934 | CE2 | PHE | A | 325 | 40.879 | −0.223 | 4.450 | 1.00 | 27.60 | A | C |
| ATOM | 4936 | CD2 | PHE | A | 325 | 39.702 | 0.070 | 5.143 | 1.00 | 19.26 | A | C |
| ATOM | 4938 | C | PHE | A | 325 | 36.516 | 0.919 | 4.430 | 1.00 | 19.97 | A | C |
| ATOM | 4939 | O | PHE | A | 325 | 36.797 | 0.802 | 3.238 | 1.00 | 19.86 | A | O |
| ATOM | 4941 | N | THR | A | 326 | 35.785 | 0.036 | 5.094 | 1.00 | 21.26 | A | N |
| ATOM | 4942 | CA | THR | A | 326 | 35.189 | −1.144 | 4.453 | 1.00 | 20.87 | A | C |
| ATOM | 4944 | CB | THR | A | 326 | 34.294 | −1.897 | 5.435 | 1.00 | 21.86 | A | C |
| ATOM | 4946 | OG1 | THR | A | 326 | 35.065 | −2.222 | 6.594 | 1.00 | 24.18 | A | O |
| ATOM | 4948 | CG2 | THR | A | 326 | 33.754 | −3.180 | 4.828 | 1.00 | 15.64 | A | C |
| ATOM | 4952 | C | THR | A | 326 | 34.364 | −0.770 | 3.234 | 1.00 | 21.47 | A | C |
| ATOM | 4953 | O | THR | A | 326 | 34.581 | −1.306 | 2.146 | 1.00 | 20.27 | A | O |
| ATOM | 4955 | N | ASP | A | 327 | 33.454 | 0.183 | 3.422 | 1.00 | 23.46 | A | N |
| ATOM | 4956 | CA | ASP | A | 327 | 32.624 | 0.717 | 2.342 | 1.00 | 24.01 | A | C |
| ATOM | 4958 | CB | ASP | A | 327 | 31.644 | 1.747 | 2.914 | 1.00 | 24.35 | A | C |
| ATOM | 4961 | CG | ASP | A | 327 | 30.821 | 2.461 | 1.837 | 1.00 | 33.07 | A | C |
| ATOM | 4962 | OD1 | ASP | A | 327 | 29.907 | 1.827 | 1.249 | 1.00 | 35.22 | A | O |
| ATOM | 4963 | OD2 | ASP | A | 327 | 31.080 | 3.674 | 1.594 | 1.00 | 39.61 | A | O |

TABLE 4-2-continued

| Coordinates of *P. alba* IspS | | | | | | | | | | | | |
|---|---|---|---|---|---|---|---|---|---|---|---|---|
| ATOM | 4964 | C | ASP | A | 327 | 33.486 | 1.322 | 1.210 | 1.00 | 24.37 | A | C |
| ATOM | 4965 | O | ASP | A | 327 | 33.203 | 1.124 | 0.026 | 1.00 | 24.49 | A | O |
| ATOM | 4967 | N | ALA | A | 328 | 34.547 | 2.038 | 1.568 | 1.00 | 23.77 | A | N |
| ATOM | 4968 | CA | ALA | A | 328 | 35.410 | 2.652 | 0.559 | 1.00 | 21.98 | A | C |
| ATOM | 4970 | CB | ALA | A | 328 | 36.444 | 3.553 | 1.211 | 1.00 | 20.52 | A | C |
| ATOM | 4974 | C | ALA | A | 328 | 36.101 | 1.571 | −0.290 | 1.00 | 20.95 | A | C |
| ATOM | 4975 | O | ALA | A | 328 | 36.252 | 1.727 | −1.498 | 1.00 | 19.89 | A | O |
| ATOM | 4977 | N | VAL | A | 329 | 36.504 | 0.475 | 0.341 | 1.00 | 19.74 | A | N |
| ATOM | 4978 | CA | VAL | A | 329 | 37.136 | −0.623 | −0.385 | 1.00 | 18.98 | A | C |
| ATOM | 4980 | CB | VAL | A | 329 | 37.802 | −1.638 | 0.563 | 1.00 | 18.57 | A | C |
| ATOM | 4982 | CG1 | VAL | A | 329 | 38.961 | −0.957 | 1.330 | 1.00 | 15.41 | A | C |
| ATOM | 4986 | CG2 | VAL | A | 329 | 38.301 | −2.860 | −0.184 | 1.00 | 19.70 | A | C |
| ATOM | 4990 | C | VAL | A | 329 | 36.100 | −1.269 | −1.289 | 1.00 | 21.12 | A | C |
| ATOM | 4991 | O | VAL | A | 329 | 36.383 | −1.524 | −2.448 | 1.00 | 23.23 | A | O |
| ATOM | 4993 | N | GLU | A | 330 | 34.882 | −1.455 | −0.799 | 1.00 | 22.69 | A | N |
| ATOM | 4994 | CA | GLU | A | 330 | 33.828 | −2.078 | −1.610 | 1.00 | 24.26 | A | C |
| ATOM | 4996 | CB | GLU | A | 330 | 32.564 | −2.299 | −0.789 | 1.00 | 24.45 | A | C |
| ATOM | 4999 | CG | GLU | A | 330 | 32.659 | −3.424 | 0.254 | 1.00 | 32.15 | A | C |
| ATOM | 5002 | CD | GLU | A | 330 | 31.415 | −3.522 | 1.181 | 1.00 | 37.11 | A | C |
| ATOM | 5003 | OE1 | GLU | A | 330 | 31.335 | −4.497 | 1.946 | 1.00 | 41.56 | A | O |
| ATOM | 5004 | OE2 | GLU | A | 330 | 30.536 | −2.629 | 1.162 | 1.00 | 37.97 | A | O |
| ATOM | 5005 | C | GLU | A | 330 | 33.484 | −1.252 | −2.842 | 1.00 | 24.43 | A | C |
| ATOM | 5006 | O | GLU | A | 330 | 33.372 | −1.785 | −3.931 | 1.00 | 23.22 | A | O |
| ATOM | 5008 | N | ARG | A | 331 | 33.305 | 0.048 | −2.659 | 1.00 | 24.59 | A | N |
| ATOM | 5009 | CA | AARG | A | 331 | 32.926 | 0.933 | −3.762 | 0.50 | 25.42 | A | C |
| ATOM | 5010 | CA | BARG | A | 331 | 32.924 | 0.934 | −3.762 | 0.50 | 25.53 | A | C |
| ATOM | 5013 | CB | AARG | A | 331 | 32.331 | 2.240 | −3.217 | 0.50 | 25.39 | A | C |
| ATOM | 5014 | CB | BARG | A | 331 | 32.311 | 2.238 | −3.215 | 0.50 | 25.60 | A | C |
| ATOM | 5019 | CG | AARG | A | 331 | 30.912 | 2.068 | −2.616 | 0.50 | 29.35 | A | C |
| ATOM | 5020 | CG | BARG | A | 331 | 31.013 | 1.984 | −2.402 | 0.50 | 30.09 | A | C |
| ATOM | 5025 | CD | AARG | A | 331 | 30.467 | 3.348 | −1.936 | 0.50 | 31.41 | A | C |
| ATOM | 5026 | CD | BARG | A | 331 | 30.354 | 3.255 | −1.877 | 0.50 | 32.13 | A | C |
| ATOM | 5031 | NE | AARG | A | 331 | 31.254 | 4.455 | −2.460 | 0.50 | 36.48 | A | N |
| ATOM | 5032 | NE | BARG | A | 331 | 29.105 | 3.539 | −2.578 | 0.50 | 39.36 | A | N |
| ATOM | 5035 | CZ | AARG | A | 331 | 32.146 | 5.140 | −1.754 | 0.50 | 36.08 | A | C |
| ATOM | 5036 | CZ | BARG | A | 331 | 27.909 | 3.144 | −2.156 | 0.50 | 40.76 | A | C |
| ATOM | 5037 | NH1 | AARG | A | 331 | 32.820 | 6.106 | −2.332 | 0.50 | 37.83 | A | N |
| ATOM | 5038 | NH1 | BARG | A | 331 | 27.798 | 2.459 | −1.027 | 0.50 | 40.70 | A | N |
| ATOM | 5043 | NH2 | AARG | A | 331 | 32.348 | 4.880 | −0.471 | 0.50 | 33.30 | A | N |
| ATOM | 5044 | NH2 | BARG | A | 331 | 26.824 | 3.439 | −2.854 | 0.50 | 39.88 | A | N |
| ATOM | 5049 | C | ARG | A | 331 | 34.092 | 1.210 | −4.719 | 1.00 | 24.63 | A | C |
| ATOM | 5050 | O | ARG | A | 331 | 33.886 | 1.403 | −5.905 | 1.00 | 25.83 | A | O |
| ATOM | 5052 | N | TRP | A | 332 | 35.315 | 1.224 | −4.198 | 1.00 | 23.38 | A | N |
| ATOM | 5053 | CA | TRP | A | 332 | 36.540 | 1.354 | −5.008 | 1.00 | 22.12 | A | C |
| ATOM | 5055 | CB | TRP | A | 332 | 36.827 | 0.035 | −5.797 | 1.00 | 22.05 | A | C |
| ATOM | 5058 | CG | TRP | A | 332 | 38.233 | −0.101 | −6.263 | 1.00 | 19.00 | A | C |
| ATOM | 5059 | CD1 | TRP | A | 332 | 38.704 | 0.112 | −7.524 | 1.00 | 20.39 | A | C |
| ATOM | 5061 | NE1 | TRP | A | 332 | 40.077 | −0.096 | −7.562 | 1.00 | 21.23 | A | N |
| ATOM | 5063 | CE2 | TRP | A | 332 | 40.509 | −0.451 | −6.312 | 1.00 | 14.45 | A | C |
| ATOM | 5064 | CD2 | TRP | A | 332 | 39.381 | −0.461 | −5.462 | 1.00 | 22.97 | A | C |
| ATOM | 5065 | CE3 | TRP | A | 332 | 39.558 | −0.801 | −4.120 | 1.00 | 19.44 | A | C |
| ATOM | 5067 | CZ3 | TRP | A | 332 | 40.841 | −1.098 | −3.666 | 1.00 | 21.88 | A | C |
| ATOM | 5069 | CH2 | TRP | A | 332 | 41.936 | −1.073 | −4.536 | 1.00 | 23.07 | A | C |
| ATOM | 5071 | CZ2 | TRP | A | 332 | 41.787 | −0.751 | −5.859 | 1.00 | 27.36 | A | C |
| ATOM | 5073 | C | TRP | A | 332 | 36.468 | 2.569 | −5.923 | 1.00 | 21.31 | A | C |
| ATOM | 5074 | O | TRP | A | 332 | 36.673 | 2.481 | −7.133 | 1.00 | 21.30 | A | O |
| ATOM | 5076 | N | ASP | A | 333 | 36.203 | 3.715 | −5.311 | 1.00 | 23.84 | A | N |
| ATOM | 5077 | CA | ASP | A | 333 | 35.996 | 4.962 | −6.028 | 1.00 | 25.51 | A | C |
| ATOM | 5079 | CB | ASP | A | 333 | 34.525 | 5.365 | −5.884 | 1.00 | 28.49 | A | C |
| ATOM | 5082 | CG | ASP | A | 333 | 34.207 | 6.764 | −6.429 | 1.00 | 31.34 | A | C |
| ATOM | 5083 | OD1 | ASP | A | 333 | 35.061 | 7.438 | −7.055 | 1.00 | 37.88 | A | O |
| ATOM | 5084 | OD2 | ASP | A | 333 | 33.054 | 7.180 | −6.224 | 1.00 | 35.04 | A | O |
| ATOM | 5085 | C | ASP | A | 333 | 36.901 | 6.000 | −5.408 | 1.00 | 25.74 | A | C |
| ATOM | 5086 | O | ASP | A | 333 | 36.638 | 6.473 | −4.315 | 1.00 | 27.33 | A | O |
| ATOM | 5088 | N | VAL | A | 334 | 37.950 | 6.377 | −6.131 | 1.00 | 25.22 | A | N |
| ATOM | 5089 | CA | VAL | A | 334 | 38.913 | 7.315 | −5.629 | 1.00 | 24.40 | A | C |
| ATOM | 5091 | CB | VAL | A | 334 | 40.154 | 7.336 | −6.508 | 1.00 | 23.40 | A | C |
| ATOM | 5093 | CG1 | VAL | A | 334 | 41.277 | 8.090 | −5.851 | 1.00 | 22.78 | A | C |
| ATOM | 5097 | CG2 | VAL | A | 334 | 39.839 | 7.911 | −7.873 | 1.00 | 22.06 | A | C |
| ATOM | 5101 | C | VAL | A | 334 | 38.336 | 8.721 | −5.512 | 1.00 | 28.91 | A | C |
| ATOM | 5102 | O | VAL | A | 334 | 38.857 | 9.535 | −4.750 | 1.00 | 29.34 | A | O |
| ATOM | 5104 | N | ASN | A | 335 | 37.261 | 9.015 | −6.246 | 1.00 | 30.93 | A | N |
| ATOM | 5105 | CA | ASN | A | 335 | 36.668 | 10.356 | −6.204 | 1.00 | 32.90 | A | C |
| ATOM | 5107 | CB | ASN | A | 335 | 35.767 | 10.617 | −7.430 | 1.00 | 33.01 | A | C |
| ATOM | 5110 | CG | ASN | A | 335 | 36.539 | 10.559 | −8.768 | 1.00 | 35.09 | A | C |
| ATOM | 5111 | OD1 | ASN | A | 335 | 37.513 | 11.293 | −8.972 | 1.00 | 31.46 | A | O |
| ATOM | 5112 | ND2 | ASN | A | 335 | 36.080 | 9.693 | −9.690 | 1.00 | 29.46 | A | N |
| ATOM | 5115 | C | ASN | A | 335 | 35.889 | 10.616 | −4.916 | 1.00 | 35.23 | A | C |

TABLE 4-2-continued

| Coordinates of *P. alba* IspS | | | | | | | | | | | |
|---|---|---|---|---|---|---|---|---|---|---|---|
| ATOM | 5116 | O | ASN | A | 335 | 35.438 | 11.744 | −4.718 | 1.00 | 37.55 | A | O |
| ATOM | 5118 | N | ALA | A | 336 | 35.737 | 9.588 | −4.062 | 1.00 | 36.18 | A | N |
| ATOM | 5119 | CA | ALA | A | 336 | 35.107 | 9.702 | −2.717 | 1.00 | 38.28 | A | C |
| ATOM | 5121 | CB | ALA | A | 336 | 33.972 | 8.678 | −2.600 | 1.00 | 37.37 | A | O |
| ATOM | 5125 | C | ALA | A | 336 | 36.067 | 9.540 | −1.501 | 1.00 | 38.39 | A | C |
| ATOM | 5126 | O | ALA | A | 336 | 35.632 | 9.516 | −0.357 | 1.00 | 40.53 | A | O |
| ATOM | 5128 | N | ILE | A | 337 | 37.357 | 9.392 | −1.766 | 1.00 | 39.34 | A | N |
| ATOM | 5129 | CA | ILE | A | 337 | 38.442 | 9.438 | −0.767 | 1.00 | 39.49 | A | C |
| ATOM | 5131 | CB | ILE | A | 337 | 39.770 | 9.736 | −1.552 | 1.00 | 41.71 | A | C |
| ATOM | 5133 | CG1 | ILE | A | 337 | 41.026 | 9.661 | −0.714 | 1.00 | 45.87 | A | C |
| ATOM | 5136 | CD1 | ILE | A | 337 | 42.218 | 10.171 | −1.518 | 1.00 | 45.13 | A | C |
| ATOM | 5140 | CG2 | ILE | A | 337 | 39.745 | 11.124 | −2.199 | 1.00 | 40.01 | A | C |
| ATOM | 5144 | C | ILE | A | 337 | 38.231 | 10.470 | 0.388 | 1.00 | 41.00 | A | C |
| ATOM | 5145 | O | ILE | A | 337 | 38.497 | 10.165 | 1.550 | 1.00 | 41.18 | A | O |
| ATOM | 5147 | N | ASN | A | 338 | 37.726 | 11.667 | 0.070 | 1.00 | 39.57 | A | N |
| ATOM | 5148 | CA | ASN | A | 338 | 37.503 | 12.723 | 1.064 | 1.00 | 39.05 | A | C |
| ATOM | 5150 | CB | ASN | A | 338 | 37.154 | 14.057 | 0.369 | 1.00 | 38.88 | A | C |
| ATOM | 5153 | CG | ASN | A | 338 | 38.379 | 14.735 | −0.240 | 1.00 | 38.68 | A | C |
| ATOM | 5154 | OD1 | ASN | A | 338 | 39.518 | 14.355 | 0.056 | 1.00 | 37.66 | A | O |
| ATOM | 5155 | ND2 | ASN | A | 338 | 38.154 | 15.740 | −1.091 | 1.00 | 32.26 | A | N |
| ATOM | 5158 | C | ASN | A | 338 | 36.484 | 12.420 | 2.180 | 1.00 | 38.52 | A | C |
| ATOM | 5159 | O | ASN | A | 338 | 36.443 | 13.142 | 3.179 | 1.00 | 36.24 | A | O |
| ATOM | 5161 | N | ASP | A | 339 | 35.695 | 11.360 | 2.017 | 1.00 | 37.68 | A | N |
| ATOM | 5162 | CA | ASP | A | 339 | 34.804 | 10.866 | 3.080 | 1.00 | 38.81 | A | C |
| ATOM | 5164 | CB | ASP | A | 339 | 33.943 | 9.699 | 2.546 | 1.00 | 41.47 | A | C |
| ATOM | 5167 | CG | ASP | A | 339 | 32.967 | 10.110 | 1.435 | 1.00 | 45.43 | A | C |
| ATOM | 5168 | OD1 | ASP | A | 339 | 32.684 | 11.323 | 1.284 | 1.00 | 49.71 | A | O |
| ATOM | 5169 | OD2 | ASP | A | 339 | 32.466 | 9.191 | 0.738 | 1.00 | 42.53 | A | O |
| ATOM | 5170 | C | ASP | A | 339 | 35.566 | 10.336 | 4.319 | 1.00 | 36.47 | A | C |
| ATOM | 5171 | O | ASP | A | 339 | 35.045 | 10.344 | 5.440 | 1.00 | 37.33 | A | O |
| ATOM | 5173 | N | LEU | A | 340 | 36.777 | 9.835 | 4.088 | 1.00 | 31.99 | A | N |
| ATOM | 5174 | CA | LEU | A | 340 | 37.551 | 9.126 | 5.099 | 1.00 | 28.85 | A | C |
| ATOM | 5176 | CB | LEU | A | 340 | 38.562 | 8.206 | 4.419 | 1.00 | 26.83 | A | C |
| ATOM | 5179 | CG | LEU | A | 340 | 38.040 | 7.105 | 3.512 | 1.00 | 26.05 | A | C |
| ATOM | 5181 | CD1 | LEU | A | 340 | 39.177 | 6.481 | 2.697 | 1.00 | 19.73 | A | C |
| ATOM | 5185 | CD2 | LEU | A | 340 | 37.335 | 6.075 | 4.347 | 1.00 | 28.12 | A | C |
| ATOM | 5189 | C | LEU | A | 340 | 38.342 | 10.102 | 5.973 | 1.00 | 27.33 | A | C |
| ATOM | 5190 | O | LEU | A | 340 | 38.664 | 11.198 | 5.525 | 1.00 | 28.68 | A | O |
| ATOM | 5192 | N | PRO | A | 341 | 38.698 | 9.681 | 7.199 | 1.00 | 24.34 | A | N |
| ATOM | 5193 | CA | PRO | A | 341 | 39.596 | 10.458 | 8.061 | 1.00 | 24.84 | A | C |
| ATOM | 5195 | CB | PRO | A | 341 | 39.422 | 9.801 | 9.439 | 1.00 | 26.28 | A | C |
| ATOM | 5198 | CG | PRO | A | 341 | 38.974 | 8.411 | 9.152 | 1.00 | 25.66 | A | C |
| ATOM | 5201 | CD | PRO | A | 341 | 38.256 | 8.427 | 7.838 | 1.00 | 23.02 | A | C |
| ATOM | 5204 | C | PRO | A | 341 | 41.037 | 10.361 | 7.585 | 1.00 | 23.92 | A | C |
| ATOM | 5205 | O | PRO | A | 341 | 41.409 | 9.379 | 6.966 | 1.00 | 23.65 | A | O |
| ATOM | 5206 | N | ASP | A | 342 | 41.835 | 11.381 | 7.878 | 1.00 | 24.01 | A | N |
| ATOM | 5207 | CA | ASP | A | 342 | 43.159 | 11.568 | 7.257 | 1.00 | 24.20 | A | C |
| ATOM | 5209 | CB | ASP | A | 342 | 43.956 | 12.647 | 8.021 | 1.00 | 24.30 | A | C |
| ATOM | 5212 | CG | ASP | A | 342 | 43.410 | 14.066 | 7.807 | 1.00 | 32.75 | A | C |
| ATOM | 5213 | OD1 | ASP | A | 342 | 42.564 | 14.253 | 6.896 | 1.00 | 33.36 | A | O |
| ATOM | 5214 | OD2 | ASP | A | 342 | 43.842 | 14.998 | 8.548 | 1.00 | 38.90 | A | O |
| ATOM | 5215 | C | ASP | A | 342 | 44.009 | 10.276 | 7.125 | 1.00 | 23.76 | A | C |
| ATOM | 5216 | O | ASP | A | 342 | 44.523 | 9.958 | 6.030 | 1.00 | 23.73 | A | O |
| ATOM | 5218 | N | TYR | A | 343 | 44.148 | 9.524 | 8.216 | 1.00 | 21.13 | A | N |
| ATOM | 5219 | CA | TYR | A | 343 | 45.020 | 8.355 | 8.192 | 1.00 | 20.93 | A | C |
| ATOM | 5221 | CB | TYR | A | 343 | 45.222 | 7.786 | 9.584 | 1.00 | 20.26 | A | C |
| ATOM | 5224 | CG | TYR | A | 343 | 44.066 | 7.002 | 10.157 | 1.00 | 23.08 | A | C |
| ATOM | 5225 | CD1 | TYR | A | 343 | 43.048 | 7.626 | 10.855 | 1.00 | 18.13 | A | C |
| ATOM | 5227 | CE1 | TYR | A | 343 | 42.009 | 6.903 | 11.384 | 1.00 | 27.05 | A | C |
| ATOM | 5229 | CZ | TYR | A | 343 | 41.994 | 5.521 | 11.239 | 1.00 | 24.51 | A | C |
| ATOM | 5230 | OH | TYR | A | 343 | 40.978 | 4.744 | 11.763 | 1.00 | 27.02 | A | O |
| ATOM | 5232 | CE2 | TYR | A | 343 | 43.012 | 4.892 | 10.571 | 1.00 | 23.11 | A | C |
| ATOM | 5234 | CD2 | TYR | A | 343 | 44.034 | 5.625 | 10.048 | 1.00 | 21.57 | A | C |
| ATOM | 5236 | C | TYR | A | 343 | 44.515 | 7.299 | 7.210 | 1.00 | 21.42 | A | C |
| ATOM | 5237 | O | TYR | A | 343 | 45.303 | 6.590 | 6.572 | 1.00 | 20.42 | A | O |
| ATOM | 5239 | N | MET | A | 344 | 43.204 | 7.235 | 7.053 | 1.00 | 20.78 | A | N |
| ATOM | 5240 | CA | MET | A | 344 | 42.599 | 6.275 | 6.146 | 1.00 | 22.17 | A | C |
| ATOM | 5242 | CB | MET | A | 344 | 41.151 | 5.989 | 6.556 | 1.00 | 21.39 | A | C |
| ATOM | 5245 | CG | MET | A | 344 | 41.055 | 5.081 | 7.781 | 1.00 | 19.99 | A | C |
| ATOM | 5248 | SD | MET | A | 344 | 39.358 | 4.723 | 8.256 | 1.00 | 25.10 | A | S |
| ATOM | 5249 | CE | MET | A | 344 | 39.531 | 3.255 | 9.301 | 1.00 | 20.13 | A | C |
| ATOM | 5253 | C | MET | A | 344 | 42.676 | 6.742 | 4.696 | 1.00 | 22.77 | A | C |
| ATOM | 5254 | O | MET | A | 344 | 42.854 | 5.928 | 3.799 | 1.00 | 23.66 | A | O |
| ATOM | 5256 | N | LYS | A | 345 | 42.553 | 8.045 | 4.454 | 1.00 | 24.61 | A | N |
| ATOM | 5257 | CA | LYS | A | 345 | 42.676 | 8.561 | 3.080 | 1.00 | 23.37 | A | C |
| ATOM | 5259 | CB | LYS | A | 345 | 42.640 | 10.084 | 3.016 | 1.00 | 26.29 | A | C |
| ATOM | 5262 | CG | LYS | A | 345 | 41.362 | 10.721 | 3.574 | 1.00 | 35.34 | A | C |
| ATOM | 5265 | CD | LYS | A | 345 | 41.422 | 12.243 | 3.653 | 1.00 | 37.03 | A | C |

TABLE 4-2-continued

| Coordinates of *P. alba* IspS | | | | | | | | | | | |
|---|---|---|---|---|---|---|---|---|---|---|---|
| ATOM | 5268 | CE | LYS | A | 345 | 41.242 | 12.907 | 2.298 | 1.00 | 40.90 | A | C |
| ATOM | 5271 | NZ | LYS | A | 345 | 40.766 | 14.317 | 2.466 | 1.00 | 40.33 | A | N |
| ATOM | 5275 | C | LYS | A | 345 | 43.996 | 8.084 | 2.536 | 1.00 | 20.93 | A | C |
| ATOM | 5276 | O | LYS | A | 345 | 44.055 | 7.542 | 1.448 | 1.00 | 20.13 | A | O |
| ATOM | 5278 | N | LEU | A | 346 | 45.051 | 8.262 | 3.317 | 1.00 | 19.43 | A | N |
| ATOM | 5279 | CA | LEU | A | 346 | 46.392 | 7.947 | 2.861 | 1.00 | 19.97 | A | C |
| ATOM | 5281 | CB | LEU | A | 346 | 47.424 | 8.456 | 3.868 | 1.00 | 20.42 | A | C |
| ATOM | 5284 | CG | LEU | A | 346 | 48.885 | 8.424 | 3.430 | 1.00 | 24.60 | A | C |
| ATOM | 5286 | CD1 | LEU | A | 346 | 49.118 | 9.356 | 2.220 | 1.00 | 17.76 | A | C |
| ATOM | 5290 | CD2 | LEU | A | 346 | 49.789 | 8.796 | 4.594 | 1.00 | 27.43 | A | C |
| ATOM | 5294 | C | LEU | A | 346 | 46.534 | 6.470 | 2.661 | 1.00 | 21.21 | A | C |
| ATOM | 5295 | O | LEU | A | 346 | 47.029 | 6.024 | 1.655 | 1.00 | 21.29 | A | O |
| ATOM | 5297 | N | CYS | A | 347 | 46.051 | 5.698 | 3.624 | 1.00 | 23.15 | A | N |
| ATOM | 5298 | CA | CYS | A | 347 | 46.178 | 4.259 | 3.575 | 1.00 | 23.21 | A | C |
| ATOM | 5300 | CB | CYS | A | 347 | 45.760 | 3.653 | 4.943 | 1.00 | 25.14 | A | C |
| ATOM | 5303 | SG | CYS | A | 347 | 45.888 | 1.868 | 4.961 | 1.00 | 38.60 | A | S |
| ATOM | 5305 | C | CYS | A | 347 | 45.353 | 3.712 | 2.408 | 1.00 | 20.58 | A | C |
| ATOM | 5306 | O | CYS | A | 347 | 45.825 | 2.883 | 1.599 | 1.00 | 19.70 | A | O |
| ATOM | 5308 | N | PHE | A | 348 | 44.134 | 4.214 | 2.287 | 1.00 | 19.65 | A | N |
| ATOM | 5309 | CA | PHE | A | 348 | 43.299 | 3.863 | 1.155 | 1.00 | 19.61 | A | C |
| ATOM | 5311 | CB | PHE | A | 348 | 41.965 | 4.567 | 1.206 | 1.00 | 19.08 | A | C |
| ATOM | 5314 | CG | PHE | A | 348 | 41.070 | 4.192 | 0.080 | 1.00 | 18.31 | A | C |
| ATOM | 5315 | CD1 | PHE | A | 348 | 40.420 | 2.990 | 0.083 | 1.00 | 22.66 | A | C |
| ATOM | 5317 | CE1 | PHE | A | 348 | 39.594 | 2.623 | −0.973 | 1.00 | 23.56 | A | C |
| ATOM | 5319 | CZ | PHE | A | 348 | 39.444 | 3.455 | −2.043 | 1.00 | 21.10 | A | C |
| ATOM | 5321 | CE2 | PHE | A | 348 | 40.096 | 4.662 | −2.069 | 1.00 | 20.44 | A | C |
| ATOM | 5323 | CD2 | PHE | A | 348 | 40.907 | 5.031 | −1.011 | 1.00 | 24.44 | A | C |
| ATOM | 5325 | C | PHE | A | 348 | 43.951 | 4.141 | −0.197 | 1.00 | 19.37 | A | C |
| ATOM | 5326 | O | PHE | A | 348 | 44.056 | 3.244 | −1.037 | 1.00 | 17.63 | A | O |
| ATOM | 5328 | N | LEU | A | 349 | 44.408 | 5.367 | −0.413 | 1.00 | 16.49 | A | N |
| ATOM | 5329 | CA | LEU | A | 349 | 44.896 | 5.727 | −1.740 | 1.00 | 17.38 | A | C |
| ATOM | 5331 | CB | LEU | A | 349 | 45.157 | 7.229 | −1.849 | 1.00 | 18.66 | A | C |
| ATOM | 5334 | CG | LEU | A | 349 | 45.633 | 7.793 | −3.200 | 1.00 | 18.16 | A | C |
| ATOM | 5336 | CD1 | LEU | A | 349 | 44.756 | 7.364 | −4.359 | 1.00 | 16.21 | A | C |
| ATOM | 5340 | CD2 | LEU | A | 349 | 45.700 | 9.321 | −3.091 | 1.00 | 13.49 | A | C |
| ATOM | 5344 | C | LEU | A | 349 | 46.147 | 4.936 | −2.076 | 1.00 | 18.98 | A | C |
| ATOM | 5345 | O | LEU | A | 349 | 46.338 | 4.550 | −3.229 | 1.00 | 18.83 | A | O |
| ATOM | 5347 | N | ALA | A | 350 | 46.988 | 4.663 | −1.078 | 1.00 | 19.12 | A | N |
| ATOM | 5348 | CA | ALA | A | 350 | 48.147 | 3.791 | −1.316 | 1.00 | 20.75 | A | C |
| ATOM | 5350 | CB | ALA | A | 350 | 49.056 | 3.651 | −0.061 | 1.00 | 19.54 | A | C |
| ATOM | 5354 | C | ALA | A | 350 | 47.716 | 2.426 | −1.805 | 1.00 | 18.92 | A | C |
| ATOM | 5355 | O | ALA | A | 350 | 48.254 | 1.953 | −2.787 | 1.00 | 24.29 | A | O |
| ATOM | 5357 | N | LEU | A | 351 | 46.776 | 1.795 | −1.118 | 1.00 | 19.04 | A | N |
| ATOM | 5358 | CA | LEU | A | 351 | 46.259 | 0.458 | −1.506 | 1.00 | 19.56 | A | C |
| ATOM | 5360 | CB | LEU | A | 351 | 45.172 | −0.018 | −0.503 | 1.00 | 20.96 | A | C |
| ATOM | 5363 | CG | LEU | A | 351 | 44.558 | −1.412 | −0.691 | 1.00 | 24.54 | A | C |
| ATOM | 5365 | CD1 | LEU | A | 351 | 45.630 | −2.485 | −0.530 | 1.00 | 21.96 | A | C |
| ATOM | 5369 | CD2 | LEU | A | 351 | 43.419 | −1.645 | 0.287 | 1.00 | 20.98 | A | C |
| ATOM | 5373 | C | LEU | A | 351 | 45.637 | 0.519 | −2.884 | 1.00 | 19.78 | A | C |
| ATOM | 5374 | O | LEU | A | 351 | 45.941 | −0.293 | −3.762 | 1.00 | 20.30 | A | O |
| ATOM | 5376 | N | TYR | A | 352 | 44.744 | 1.496 | −3.056 | 1.00 | 19.85 | A | N |
| ATOM | 5377 | CA | TYR | A | 352 | 44.057 | 1.755 | −4.316 | 1.00 | 17.66 | A | C |
| ATOM | 5379 | CB | TYR | A | 352 | 43.296 | 3.075 | −4.210 | 1.00 | 20.69 | A | C |
| ATOM | 5382 | CG | TYR | A | 352 | 42.369 | 3.409 | −5.357 | 1.00 | 16.64 | A | C |
| ATOM | 5383 | CD1 | TYR | A | 352 | 41.126 | 2.831 | −5.453 | 1.00 | 21.99 | A | C |
| ATOM | 5385 | CE1 | TYR | A | 352 | 40.246 | 3.146 | −6.517 | 1.00 | 23.38 | A | C |
| ATOM | 5387 | CZ | TYR | A | 352 | 40.618 | 4.062 | −7.458 | 1.00 | 18.80 | A | C |
| ATOM | 5388 | OH | TYR | A | 352 | 39.759 | 4.352 | −8.509 | 1.00 | 23.84 | A | O |
| ATOM | 5390 | CE2 | TYR | A | 352 | 41.867 | 4.678 | −7.364 | 1.00 | 18.76 | A | C |
| ATOM | 5392 | CD2 | TYR | A | 352 | 42.727 | 4.353 | −6.316 | 1.00 | 18.81 | A | C |
| ATOM | 5394 | C | TYR | A | 352 | 45.036 | 1.781 | −5.468 | 1.00 | 17.34 | A | C |
| ATOM | 5395 | O | TYR | A | 352 | 44.892 | 1.025 | −6.435 | 1.00 | 17.23 | A | O |
| ATOM | 5397 | N | ASN | A | 353 | 46.046 | 2.633 | −5.374 | 1.00 | 17.53 | A | N |
| ATOM | 5398 | CA | ASN | A | 353 | 47.037 | 2.724 | −6.448 | 1.00 | 18.17 | A | C |
| ATOM | 5400 | CB | ASN | A | 353 | 48.000 | 3.874 | −6.213 | 1.00 | 18.33 | A | C |
| ATOM | 5403 | CG | ASN | A | 353 | 47.348 | 5.216 | −6.429 | 1.00 | 21.12 | A | C |
| ATOM | 5404 | OD1 | ASN | A | 353 | 46.297 | 5.299 | −7.068 | 1.00 | 16.85 | A | O |
| ATOM | 5405 | ND2 | ASN | A | 353 | 47.972 | 6.277 | −5.919 | 1.00 | 12.84 | A | N |
| ATOM | 5408 | C | ASN | A | 353 | 47.819 | 1.441 | −6.640 | 1.00 | 20.04 | A | C |
| ATOM | 5409 | O | ASN | A | 353 | 48.074 | 1.037 | −7.770 | 1.00 | 19.38 | A | O |
| ATOM | 5411 | N | THR | A | 354 | 48.201 | 0.790 | −5.542 | 1.00 | 19.93 | A | N |
| ATOM | 5412 | CA | THR | A | 354 | 48.989 | −0.408 | −5.668 | 1.00 | 19.28 | A | C |
| ATOM | 5414 | CB | THR | A | 354 | 49.441 | −0.944 | −4.307 | 1.00 | 21.85 | A | C |
| ATOM | 5416 | OG1 | THR | A | 354 | 50.234 | 0.055 | −3.636 | 1.00 | 18.52 | A | O |
| ATOM | 5418 | CG2 | THR | A | 354 | 50.267 | −2.217 | −4.509 | 1.00 | 20.83 | A | C |
| ATOM | 5422 | C | THR | A | 354 | 48.210 | −1.475 | −6.410 | 1.00 | 19.60 | A | C |
| ATOM | 5423 | O | THR | A | 354 | 48.749 | −2.127 | −7.287 | 1.00 | 21.37 | A | O |
| ATOM | 5425 | N | ILE | A | 355 | 46.939 | −1.651 | −6.065 | 1.00 | 19.20 | A | N |

TABLE 4-2-continued

Coordinates of *P. alba* IspS

| | | | | | | | | | | | | |
|---|---|---|---|---|---|---|---|---|---|---|---|---|
| ATOM | 5426 | CA | ILE | A | 355 | 46.126 | −2.677 | −6.694 | 1.00 | 18.48 | A | C |
| ATOM | 5428 | CB | ILE | A | 355 | 44.795 | −2.901 | −5.921 | 1.00 | 18.37 | A | C |
| ATOM | 5430 | CG1 | ILE | A | 355 | 45.061 | −3.350 | −4.483 | 1.00 | 20.38 | A | C |
| ATOM | 5433 | CD1 | ILE | A | 355 | 46.192 | −4.335 | −4.324 | 1.00 | 29.16 | A | C |
| ATOM | 5437 | CG2 | ILE | A | 355 | 43.883 | −3.902 | −6.618 | 1.00 | 18.31 | A | C |
| ATOM | 5441 | C | ILE | A | 355 | 45.879 | −2.313 | −8.176 | 1.00 | 19.56 | A | C |
| ATOM | 5442 | O | ILE | A | 355 | 45.989 | −3.176 | −9.061 | 1.00 | 18.02 | A | O |
| ATOM | 5444 | N | ASN | A | 356 | 45.581 | −1.042 | −8.450 | 1.00 | 18.36 | A | N |
| ATOM | 5445 | CA | ASN | A | 356 | 45.340 | −0.616 | −9.819 | 1.00 | 18.34 | A | C |
| ATOM | 5447 | CB | ASN | A | 356 | 44.863 | 0.832 | −9.900 | 1.00 | 17.65 | A | C |
| ATOM | 5450 | CG | ASN | A | 356 | 43.476 | 1.028 | −9.334 | 1.00 | 16.23 | A | C |
| ATOM | 5451 | OD1 | ASN | A | 356 | 42.725 | 0.075 | −9.138 | 1.00 | 19.91 | A | O |
| ATOM | 5452 | ND2 | ASN | A | 356 | 43.116 | 2.290 | −9.083 | 1.00 | 20.98 | A | N |
| ATOM | 5455 | C | ASN | A | 356 | 46.564 | −0.825 | −10.703 | 1.00 | 19.43 | A | C |
| ATOM | 5456 | O | ASN | A | 356 | 46.422 | −1.142 | −11.887 | 1.00 | 20.70 | A | O |
| ATOM | 5458 | N | GLU | A | 357 | 47.753 | −0.671 | −10.132 | 1.00 | 20.68 | A | N |
| ATOM | 5459 | CA | AGLU | A | 357 | 48.994 | −0.866 | −10.888 | 0.50 | 21.52 | A | C |
| ATOM | 5460 | CA | BGLU | A | 357 | 49.010 | −0.884 | −10.874 | 0.50 | 20.35 | A | C |
| ATOM | 5463 | CB | AGLU | A | 357 | 50.194 | −0.231 | −10.148 | 0.50 | 22.00 | A | C |
| ATOM | 5464 | CB | BGLU | A | 357 | 50.217 | −0.366 | −10.079 | 0.50 | 20.11 | A | C |
| ATOM | 5469 | CG | AGLU | A | 357 | 50.380 | 1.275 | −10.466 | 0.50 | 28.65 | A | C |
| ATOM | 5470 | CG | BGLU | A | 357 | 51.579 | −0.813 | −10.618 | 0.50 | 19.78 | A | C |
| ATOM | 5475 | CD | AGLU | A | 357 | 50.846 | 2.136 | −9.291 | 0.50 | 33.37 | A | C |
| ATOM | 5476 | CD | BGLU | A | 357 | 52.743 | −0.147 | −9.918 | 0.50 | 23.84 | A | C |
| ATOM | 5477 | OE1 | AGLU | A | 357 | 51.301 | 1.583 | −8.270 | 0.50 | 33.65 | A | O |
| ATOM | 5478 | OE1 | BGLU | A | 357 | 52.594 | 0.268 | −8.744 | 0.50 | 29.12 | A | O |
| ATOM | 5479 | OE2 | AGLU | A | 357 | 50.754 | 3.387 | −9.402 | 0.50 | 37.95 | A | O |
| ATOM | 5480 | OE2 | BGLU | A | 357 | 53.816 | −0.051 | −10.544 | 0.50 | 25.37 | A | O |
| ATOM | 5481 | C | GLU | A | 357 | 49.201 | −2.360 | −11.206 | 1.00 | 19.73 | A | C |
| ATOM | 5482 | O | GLU | A | 357 | 49.669 | −2.716 | −12.285 | 1.00 | 18.33 | A | O |
| ATOM | 5484 | N | ILE | A | 358 | 48.822 | −3.231 | −10.280 | 1.00 | 20.56 | A | N |
| ATOM | 5485 | CA | ILE | A | 358 | 48.876 | −4.659 | −10.536 | 1.00 | 20.75 | A | C |
| ATOM | 5487 | CB | ILE | A | 358 | 48.706 | −5.508 | −9.260 | 1.00 | 22.24 | A | C |
| ATOM | 5489 | CG1 | ILE | A | 358 | 49.953 | −5.357 | −8.385 | 1.00 | 23.28 | A | C |
| ATOM | 5492 | CD1 | ILE | A | 358 | 49.763 | −5.808 | −6.885 | 1.00 | 20.16 | A | C |
| ATOM | 5496 | CG2 | ILE | A | 358 | 48.505 | −7.015 | −9.623 | 1.00 | 19.35 | A | C |
| ATOM | 5500 | C | ILE | A | 358 | 47.841 | −5.018 | −11.601 | 1.00 | 21.23 | A | C |
| ATOM | 5501 | O | ILE | A | 358 | 48.119 | −5.810 | −12.489 | 1.00 | 22.96 | A | O |
| ATOM | 5503 | N | ALA | A | 359 | 46.665 | −4.418 | −11.544 | 1.00 | 21.80 | A | N |
| ATOM | 5504 | CA | ALA | A | 359 | 45.693 | −4.608 | −12.625 | 1.00 | 20.99 | A | C |
| ATOM | 5506 | CB | ALA | A | 359 | 44.394 | −3.864 | −12.316 | 1.00 | 19.18 | A | C |
| ATOM | 5510 | C | ALA | A | 359 | 46.272 | −4.131 | −13.952 | 1.00 | 20.71 | A | C |
| ATOM | 5511 | O | ALA | A | 359 | 46.094 | −4.789 | −14.991 | 1.00 | 19.81 | A | O |
| ATOM | 5513 | N | TYR | A | 360 | 46.943 | −2.972 | −13.948 | 1.00 | 20.31 | A | N |
| ATOM | 5514 | CA | TYR | A | 360 | 47.532 | −2.470 | −15.209 | 1.00 | 18.47 | A | C |
| ATOM | 5516 | CB | TYR | A | 360 | 48.199 | −1.099 | −15.038 | 1.00 | 18.10 | A | C |
| ATOM | 5519 | CG | TYR | A | 360 | 48.851 | −0.625 | −16.318 | 1.00 | 15.44 | A | C |
| ATOM | 5520 | CD1 | TYR | A | 360 | 48.097 | −0.026 | −17.321 | 1.00 | 12.29 | A | C |
| ATOM | 5522 | CE1 | TYR | A | 360 | 48.666 | 0.360 | −18.518 | 1.00 | 9.88 | A | C |
| ATOM | 5524 | CZ | TYR | A | 360 | 50.010 | 0.118 | −18.751 | 1.00 | 13.42 | A | C |
| ATOM | 5525 | OH | TYR | A | 360 | 50.565 | 0.520 | −19.932 | 1.00 | 16.96 | A | O |
| ATOM | 5527 | CE2 | TYR | A | 360 | 50.790 | −0.485 | −17.786 | 1.00 | 8.89 | A | C |
| ATOM | 5529 | CD2 | TYR | A | 360 | 50.203 | −0.861 | −16.568 | 1.00 | 13.09 | A | C |
| ATOM | 5531 | C | TYR | A | 360 | 48.519 | −3.512 | −15.761 | 1.00 | 19.61 | A | C |
| ATOM | 5532 | O | TYR | A | 360 | 48.396 | −3.939 | −16.901 | 1.00 | 21.66 | A | O |
| ATOM | 5534 | N | ASP | A | 361 | 49.453 | −3.976 | −14.931 | 1.00 | 20.81 | A | N |
| ATOM | 5535 | CA | ASP | A | 361 | 50.465 | −4.969 | −15.377 | 1.00 | 22.44 | A | C |
| ATOM | 5537 | CB | ASP | A | 361 | 51.307 | −5.501 | −14.218 | 1.00 | 23.16 | A | C |
| ATOM | 5540 | CG | ASP | A | 361 | 52.175 | −4.431 | −13.551 | 1.00 | 29.65 | A | C |
| ATOM | 5541 | OD1 | ASP | A | 361 | 52.375 | −3.309 | −14.095 | 1.00 | 30.92 | A | O |
| ATOM | 5542 | OD2 | ASP | A | 361 | 52.684 | −4.754 | −12.462 | 1.00 | 39.54 | A | O |
| ATOM | 5543 | C | ASP | A | 361 | 49.828 | −6.163 | −16.063 | 1.00 | 21.86 | A | C |
| ATOM | 5544 | O | ASP | A | 361 | 50.296 | −6.612 | −17.095 | 1.00 | 20.13 | A | O |
| ATOM | 5546 | N | ASN | A | 362 | 48.751 | −6.668 | −15.482 | 1.00 | 22.54 | A | N |
| ATOM | 5547 | CA | ASN | A | 362 | 48.066 | −7.813 | −16.036 | 1.00 | 23.29 | A | C |
| ATOM | 5549 | CB | ASN | A | 362 | 47.121 | −8.407 | −15.005 | 1.00 | 26.74 | A | C |
| ATOM | 5552 | CG | ASN | A | 362 | 47.831 | −9.340 | −14.072 | 1.00 | 27.43 | A | C |
| ATOM | 5553 | OD1 | ASN | A | 362 | 47.917 | −10.526 | −14.337 | 1.00 | 26.92 | A | O |
| ATOM | 5554 | ND2 | ASN | A | 362 | 48.403 | −8.797 | −13.004 | 1.00 | 30.27 | A | N |
| ATOM | 5557 | C | ASN | A | 362 | 47.324 | −7.491 | −17.322 | 1.00 | 24.48 | A | C |
| ATOM | 5558 | O | ASN | A | 362 | 47.420 | −8.243 | −18.278 | 1.00 | 23.43 | A | O |
| ATOM | 5560 | N | LEU | A | 363 | 46.628 | −6.354 | −17.362 | 1.00 | 23.94 | A | N |
| ATOM | 5561 | CA | LEU | A | 363 | 45.966 | −5.918 | −18.581 | 1.00 | 22.60 | A | C |
| ATOM | 5563 | CB | LEU | A | 363 | 45.287 | −4.570 | −18.389 | 1.00 | 20.18 | A | C |
| ATOM | 5566 | CG | LEU | A | 363 | 44.590 | −3.967 | −19.601 | 1.00 | 23.96 | A | C |
| ATOM | 5568 | CD1 | LEU | A | 363 | 43.503 | −4.907 | −20.108 | 1.00 | 14.88 | A | C |
| ATOM | 5572 | CD2 | LEU | A | 363 | 44.030 | −2.552 | −19.279 | 1.00 | 17.49 | A | C |
| ATOM | 5576 | C | LEU | A | 363 | 46.985 | −5.838 | −19.707 | 1.00 | 23.16 | A | C |

TABLE 4-2-continued

Coordinates of *P. alba* IspS

| | | | | | | | | | | | | |
|---|---|---|---|---|---|---|---|---|---|---|---|---|
| ATOM | 5577 | O | LEU | A | 363 | 46.734 | −6.307 | −20.800 | 1.00 | 24.96 | A | O |
| ATOM | 5579 | N | LYS | A | 364 | 48.143 | −5.263 | −19.432 | 1.00 | 24.48 | A | N |
| ATOM | 5580 | CA | LYS | A | 364 | 49.149 | −5.054 | −20.469 | 1.00 | 23.95 | A | C |
| ATOM | 5582 | CB | LYS | A | 364 | 50.288 | −4.165 | −19.964 | 1.00 | 23.52 | A | C |
| ATOM | 5585 | CG | LYS | A | 364 | 51.326 | −3.846 | −21.033 | 1.00 | 28.36 | A | C |
| ATOM | 5588 | CD | LYS | A | 364 | 52.416 | −2.904 | −20.568 | 1.00 | 33.18 | A | C |
| ATOM | 5591 | CE | LYS | A | 364 | 53.575 | −3.616 | −19.903 | 1.00 | 29.42 | A | C |
| ATOM | 5594 | NZ | LYS | A | 364 | 53.277 | −3.791 | −18.504 | 1.00 | 34.02 | A | N |
| ATOM | 5598 | C | LYS | A | 364 | 49.752 | −6.361 | −20.967 | 1.00 | 25.61 | A | C |
| ATOM | 5599 | O | LYS | A | 364 | 50.000 | −6.488 | −22.163 | 1.00 | 24.47 | A | O |
| ATOM | 5601 | N | ASP | A | 365 | 50.020 | −7.304 | −20.053 | 1.00 | 26.63 | A | N |
| ATOM | 5602 | CA | ASP | A | 365 | 50.760 | −8.530 | −20.395 | 1.00 | 29.60 | A | C |
| ATOM | 5604 | CB | ASP | A | 365 | 51.663 | −8.970 | −19.235 | 1.00 | 28.67 | A | C |
| ATOM | 5607 | CG | ASP | A | 365 | 52.733 | −7.936 | −18.896 | 1.00 | 38.74 | A | C |
| ATOM | 5608 | OD1 | ASP | A | 365 | 52.986 | −7.008 | −19.711 | 1.00 | 45.92 | A | O |
| ATOM | 5609 | OD2 | ASP | A | 365 | 53.314 | −8.040 | −17.799 | 1.00 | 47.56 | A | O |
| ATOM | 5610 | C | ASP | A | 365 | 49.867 | −9.705 | −20.793 | 1.00 | 30.41 | A | C |
| ATOM | 5611 | O | ASP | A | 365 | 50.295 | −10.549 | −21.574 | 1.00 | 30.84 | A | O |
| ATOM | 5613 | N | LYS | A | 366 | 48.655 | −9.775 | −20.238 | 1.00 | 29.91 | A | N |
| ATOM | 5614 | CA | LYS | A | 366 | 47.732 | −10.890 | −20.515 | 1.00 | 31.66 | A | C |
| ATOM | 5616 | CB | LYS | A | 366 | 47.282 | −11.573 | −19.222 | 1.00 | 31.27 | A | C |
| ATOM | 5619 | CG | LYS | A | 366 | 48.393 | −12.030 | −18.325 | 1.00 | 37.24 | A | C |
| ATOM | 5622 | CD | LYS | A | 366 | 47.831 | −12.620 | −17.023 | 1.00 | 51.74 | A | C |
| ATOM | 5625 | CE | LYS | A | 366 | 48.938 | −13.013 | −16.050 | 1.00 | 58.01 | A | C |
| ATOM | 5628 | NZ | LYS | A | 366 | 49.938 | −13.909 | −16.721 | 1.00 | 65.78 | A | N |
| ATOM | 5632 | C | LYS | A | 366 | 46.493 | −10.433 | −21.260 | 1.00 | 31.36 | A | C |
| ATOM | 5633 | O | LYS | A | 366 | 45.638 | −11.244 | −21.579 | 1.00 | 34.55 | A | O |
| ATOM | 5635 | N | GLY | A | 367 | 46.372 | −9.139 | −21.516 | 1.00 | 29.56 | A | N |
| ATOM | 5636 | CA | GLY | A | 367 | 45.215 | −8.637 | −22.233 | 1.00 | 28.57 | A | C |
| ATOM | 5639 | C | GLY | A | 367 | 43.893 | −8.799 | −21.503 | 1.00 | 28.83 | A | C |
| ATOM | 5640 | O | GLY | A | 367 | 42.846 | −8.755 | −22.145 | 1.00 | 29.71 | A | O |
| ATOM | 5642 | N | GLU | A | 368 | 43.921 | −8.940 | −20.174 | 1.00 | 27.22 | A | N |
| ATOM | 5643 | CA | GLU | A | 368 | 42.685 | −9.147 | −19.396 | 1.00 | 27.74 | A | C |
| ATOM | 5645 | CB | GLU | A | 368 | 42.648 | −10.563 | −18.784 | 1.00 | 28.93 | A | C |
| ATOM | 5648 | CG | GLU | A | 368 | 42.646 | −11.732 | −19.784 | 1.00 | 38.81 | A | C |
| ATOM | 5651 | CD | GLU | A | 368 | 41.343 | −11.888 | −20.567 | 1.00 | 47.54 | A | C |
| ATOM | 5652 | OE1 | GLU | A | 368 | 40.389 | −11.104 | −20.360 | 1.00 | 49.64 | A | O |
| ATOM | 5653 | OE2 | GLU | A | 368 | 41.284 | −12.808 | −21.410 | 1.00 | 54.32 | A | O |
| ATOM | 5654 | C | GLU | A | 368 | 42.543 | −8.135 | −18.268 | 1.00 | 24.49 | A | C |
| ATOM | 5655 | O | GLU | A | 368 | 43.499 | −7.861 | −17.565 | 1.00 | 25.04 | A | O |
| ATOM | 5657 | N | ASN | A | 369 | 41.345 | −7.610 | −18.068 | 1.00 | 23.64 | A | N |
| ATOM | 5658 | CA | ASN | A | 369 | 41.070 | −6.743 | −16.922 | 1.00 | 23.23 | A | C |
| ATOM | 5660 | CB | ASN | A | 369 | 39.965 | −5.744 | −17.246 | 1.00 | 23.47 | A | C |
| ATOM | 5663 | CG | ASN | A | 369 | 39.625 | −4.846 | −16.059 | 1.00 | 26.64 | A | C |
| ATOM | 5664 | OD1 | ASN | A | 369 | 40.103 | −5.046 | −14.935 | 1.00 | 27.47 | A | O |
| ATOM | 5665 | ND2 | ASN | A | 369 | 38.801 | −3.848 | −16.310 | 1.00 | 21.10 | A | N |
| ATOM | 5668 | C | ASN | A | 369 | 40.646 | −7.564 | −15.716 | 1.00 | 22.50 | A | C |
| ATOM | 5669 | O | ASN | A | 369 | 39.515 | −8.037 | −15.662 | 1.00 | 23.28 | A | O |
| ATOM | 5671 | N | ILE | A | 370 | 41.548 | −7.697 | −14.749 | 1.00 | 20.03 | A | N |
| ATOM | 5672 | CA | ILE | A | 370 | 41.339 | −8.531 | −13.587 | 1.00 | 20.96 | A | C |
| ATOM | 5674 | CB | ILE | A | 370 | 42.596 | −9.422 | −13.301 | 1.00 | 22.00 | A | C |
| ATOM | 5676 | CG1 | ILE | A | 370 | 43.822 | −8.555 | −12.918 | 1.00 | 22.25 | A | C |
| ATOM | 5679 | CD1 | ILE | A | 370 | 44.991 | −9.307 | −12.305 | 1.00 | 24.22 | A | C |
| ATOM | 5683 | CG2 | ILE | A | 370 | 42.925 | −10.275 | −14.521 | 1.00 | 22.49 | A | C |
| ATOM | 5687 | C | ILE | A | 370 | 41.038 | −7.700 | −12.345 | 1.00 | 22.36 | A | C |
| ATOM | 5688 | O | ILE | A | 370 | 40.934 | −8.245 | −11.246 | 1.00 | 23.94 | A | O |
| ATOM | 5690 | N | LEU | A | 371 | 40.927 | −6.388 | −12.500 | 1.00 | 21.80 | A | N |
| ATOM | 5691 | CA | LEU | A | 371 | 40.640 | −5.508 | −11.350 | 1.00 | 22.30 | A | C |
| ATOM | 5693 | CB | LEU | A | 371 | 40.420 | −4.071 | −11.808 | 1.00 | 20.64 | A | C |
| ATOM | 5696 | CG | LEU | A | 371 | 40.364 | −3.036 | −10.684 | 1.00 | 22.73 | A | C |
| ATOM | 5698 | CD1 | LEU | A | 371 | 41.588 | −3.133 | −9.844 | 1.00 | 17.10 | A | C |
| ATOM | 5702 | CD2 | LEU | A | 371 | 40.230 | −1.641 | −11.247 | 1.00 | 17.41 | A | C |
| ATOM | 5706 | C | LEU | A | 371 | 39.477 | −5.941 | −10.442 | 1.00 | 22.81 | A | C |
| ATOM | 5707 | O | LEU | A | 371 | 39.636 | −5.947 | −9.221 | 1.00 | 25.48 | A | O |
| ATOM | 5709 | N | PRO | A | 372 | 38.323 | −6.322 | −11.018 | 1.00 | 24.23 | A | N |
| ATOM | 5710 | CA | PRO | A | 372 | 37.194 | −6.750 | −10.172 | 1.00 | 24.59 | A | C |
| ATOM | 5712 | CB | PRO | A | 372 | 36.136 | −7.207 | −11.186 | 1.00 | 25.42 | A | C |
| ATOM | 5715 | CG | PRO | A | 372 | 36.502 | −6.557 | −12.470 | 1.00 | 27.16 | A | C |
| ATOM | 5718 | CD | PRO | A | 372 | 37.991 | −6.388 | −12.457 | 1.00 | 26.65 | A | C |
| ATOM | 5721 | C | PRO | A | 372 | 37.520 | −7.921 | −9.235 | 1.00 | 24.27 | A | C |
| ATOM | 5722 | O | PRO | A | 372 | 36.936 | −8.036 | −8.165 | 1.00 | 24.63 | A | O |
| ATOM | 5723 | N | TYR | A | 373 | 38.444 | −8.778 | −9.629 | 1.00 | 22.56 | A | N |
| ATOM | 5724 | CA | TYR | A | 373 | 38.785 | −9.923 | −8.804 | 1.00 | 23.41 | A | C |
| ATOM | 5726 | CB | TYR | A | 373 | 39.355 | −11.030 | −9.678 | 1.00 | 25.44 | A | C |
| ATOM | 5729 | CG | TYR | A | 373 | 38.520 | −11.288 | −10.950 | 1.00 | 28.81 | A | C |
| ATOM | 5730 | CD1 | TYR | A | 373 | 37.220 | −11.783 | −10.877 | 1.00 | 39.04 | A | C |
| ATOM | 5732 | CE1 | TYR | A | 373 | 36.452 | −12.013 | −12.040 | 1.00 | 38.13 | A | C |
| ATOM | 5734 | CZ | TYR | A | 373 | 36.999 | −11.743 | −13.272 | 1.00 | 39.16 | A | C |

TABLE 4-2-continued

Coordinates of *P. alba* IspS

| | | | | | | | | | | | | |
|---|---|---|---|---|---|---|---|---|---|---|---|---|
| ATOM | 5735 | OH | TYR | A | 373 | 36.279 | −11.950 | −14.425 | 1.00 | 47.13 | A | O |
| ATOM | 5737 | CE2 | TYR | A | 373 | 38.284 | −11.243 | −13.361 | 1.00 | 40.64 | A | C |
| ATOM | 5739 | CD2 | TYR | A | 373 | 39.037 | −11.025 | −12.208 | 1.00 | 30.70 | A | C |
| ATOM | 5741 | C | TYR | A | 373 | 39.750 | −9.516 | −7.676 | 1.00 | 24.07 | A | C |
| ATOM | 5742 | O | TYR | A | 373 | 39.657 | −10.021 | −6.574 | 1.00 | 24.75 | A | O |
| ATOM | 5744 | N | LEU | A | 374 | 40.640 | −8.562 | −7.935 | 1.00 | 21.92 | A | N |
| ATOM | 5745 | CA | LEU | A | 374 | 41.543 | −8.065 | −6.904 | 1.00 | 20.05 | A | C |
| ATOM | 5747 | CB | LEU | A | 374 | 42.697 | −7.268 | −7.533 | 1.00 | 18.59 | A | C |
| ATOM | 5750 | CG | LEU | A | 374 | 43.440 | −7.920 | −8.708 | 1.00 | 21.18 | A | C |
| ATOM | 5752 | CD1 | LEU | A | 374 | 44.568 | −7.012 | −9.281 | 1.00 | 15.63 | A | C |
| ATOM | 5756 | CD2 | LEU | A | 374 | 44.002 | −9.288 | −8.329 | 1.00 | 21.62 | A | C |
| ATOM | 5760 | C | LEU | A | 374 | 40.748 | −7.194 | −5.916 | 1.00 | 19.90 | A | C |
| ATOM | 5761 | O | LEU | A | 374 | 40.908 | −7.312 | −4.711 | 1.00 | 21.65 | A | O |
| ATOM | 5763 | N | THR | A | 375 | 39.875 | −6.324 | −6.403 | 1.00 | 19.48 | A | N |
| ATOM | 5764 | CA | THR | A | 375 | 39.118 | −5.465 | −5.482 | 1.00 | 20.29 | A | C |
| ATOM | 5766 | CB | THR | A | 375 | 38.419 | −4.297 | −6.219 | 1.00 | 21.53 | A | C |
| ATOM | 5768 | OG1 | THR | A | 375 | 37.533 | −4.818 | −7.222 | 1.00 | 23.71 | A | O |
| ATOM | 5770 | CG2 | THR | A | 375 | 39.458 | −3.379 | −6.875 | 1.00 | 17.49 | A | C |
| ATOM | 5774 | C | THR | A | 375 | 38.093 | −6.269 | −4.665 | 1.00 | 20.82 | A | C |
| ATOM | 5775 | O | THR | A | 375 | 37.854 | −5.989 | −3.499 | 1.00 | 23.34 | A | O |
| ATOM | 5777 | N | LYS | A | 376 | 37.510 | −7.299 | −5.243 | 1.00 | 21.46 | A | N |
| ATOM | 5778 | CA | LYS | A | 376 | 36.592 | −8.149 | −4.476 | 1.00 | 22.11 | A | C |
| ATOM | 5780 | CB | LYS | A | 376 | 35.915 | −9.162 | −5.411 | 1.00 | 24.77 | A | C |
| ATOM | 5783 | CG | LYS | A | 376 | 35.075 | −10.225 | −4.732 | 1.00 | 30.99 | A | C |
| ATOM | 5786 | CD | LYS | A | 376 | 33.828 | −9.640 | −4.119 | 1.00 | 37.68 | A | C |
| ATOM | 5789 | CE | LYS | A | 376 | 32.933 | −10.753 | −3.552 | 1.00 | 43.15 | A | C |
| ATOM | 5792 | NZ | LYS | A | 376 | 32.101 | −10.264 | −2.422 | 1.00 | 47.30 | A | N |
| ATOM | 5796 | C | LYS | A | 376 | 37.324 | −8.858 | −3.345 | 1.00 | 20.58 | A | C |
| ATOM | 5797 | O | LYS | A | 376 | 36.805 | −8.964 | −2.259 | 1.00 | 22.25 | A | O |
| ATOM | 5799 | N | ALA | A | 377 | 38.522 | −9.369 | −3.612 | 1.00 | 20.81 | A | N |
| ATOM | 5800 | CA | ALA | A | 377 | 39.307 | −10.072 | −2.597 | 1.00 | 19.65 | A | C |
| ATOM | 5802 | CB | ALA | A | 377 | 40.581 | −10.615 | −3.187 | 1.00 | 20.54 | A | C |
| ATOM | 5806 | C | ALA | A | 377 | 39.635 | −9.157 | −1.438 | 1.00 | 22.21 | A | C |
| ATOM | 5807 | O | ALA | A | 377 | 39.599 | −9.577 | −0.265 | 1.00 | 24.06 | A | O |
| ATOM | 5809 | N | TRP | A | 378 | 39.918 | −7.892 | −1.748 | 1.00 | 20.95 | A | N |
| ATOM | 5810 | CA | TRP | A | 378 | 40.154 | −6.899 | −0.686 | 1.00 | 19.91 | A | C |
| ATOM | 5812 | CB | TRP | A | 378 | 40.823 | −5.645 | −1.240 | 1.00 | 19.12 | A | C |
| ATOM | 5815 | CG | TRP | A | 378 | 42.266 | −5.807 | −1.234 | 1.00 | 18.82 | A | C |
| ATOM | 5816 | CD1 | TRP | A | 378 | 43.045 | −6.192 | −2.261 | 1.00 | 17.16 | A | C |
| ATOM | 5818 | NE1 | TRP | A | 378 | 44.343 | −6.281 | −1.858 | 1.00 | 20.04 | A | N |
| ATOM | 5820 | CE2 | TRP | A | 378 | 44.416 | −5.964 | −0.528 | 1.00 | 15.91 | A | C |
| ATOM | 5821 | CD2 | TRP | A | 378 | 43.115 | −5.692 | −0.098 | 1.00 | 19.67 | A | C |
| ATOM | 5822 | CE3 | TRP | A | 378 | 42.903 | −5.345 | 1.237 | 1.00 | 17.94 | A | C |
| ATOM | 5824 | CZ3 | TRP | A | 378 | 43.989 | −5.290 | 2.080 | 1.00 | 22.51 | A | C |
| ATOM | 5826 | CH2 | TRP | A | 378 | 45.271 | −5.571 | 1.624 | 1.00 | 15.95 | A | C |
| ATOM | 5828 | CZ2 | TRP | A | 378 | 45.510 | −5.902 | 0.324 | 1.00 | 15.79 | A | C |
| ATOM | 5830 | C | TRP | A | 378 | 38.908 | −6.516 | 0.109 | 1.00 | 19.57 | A | C |
| ATOM | 5831 | O | TRP | A | 378 | 38.994 | −6.297 | 1.313 | 1.00 | 19.10 | A | O |
| ATOM | 5833 | N | ALA | A | 379 | 37.779 | −6.386 | −0.577 | 1.00 | 17.51 | A | N |
| ATOM | 5834 | CA | ALA | A | 379 | 36.511 | −6.130 | 0.083 | 1.00 | 18.56 | A | C |
| ATOM | 5836 | CB | ALA | A | 379 | 35.377 | −5.971 | −0.957 | 1.00 | 19.21 | A | C |
| ATOM | 5840 | C | ALA | A | 379 | 36.179 | −7.267 | 1.040 | 1.00 | 20.27 | A | C |
| ATOM | 5841 | O | ALA | A | 379 | 35.706 | −7.046 | 2.155 | 1.00 | 22.16 | A | O |
| ATOM | 5843 | N | ASP | A | 380 | 36.405 | −8.495 | 0.601 | 1.00 | 20.50 | A | N |
| ATOM | 5844 | CA | ASP | A | 380 | 36.081 | −9.638 | 1.448 | 1.00 | 21.17 | A | C |
| ATOM | 5846 | CB | ASP | A | 380 | 36.238 | −10.964 | 0.695 | 1.00 | 21.00 | A | C |
| ATOM | 5849 | CG | ASP | A | 380 | 35.187 | −11.187 | −0.412 | 1.00 | 21.43 | A | C |
| ATOM | 5850 | OD1 | ASP | A | 380 | 34.167 | −10.468 | −0.515 | 1.00 | 25.52 | A | O |
| ATOM | 5851 | OD2 | ASP | A | 380 | 35.379 | −12.153 | −1.177 | 1.00 | 29.89 | A | O |
| ATOM | 5852 | C | ASP | A | 380 | 37.009 | −9.625 | 2.662 | 1.00 | 21.11 | A | C |
| ATOM | 5853 | O | ASP | A | 380 | 36.589 | −9.925 | 3.778 | 1.00 | 25.31 | A | O |
| ATOM | 5855 | N | LEU | A | 381 | 38.273 | −9.283 | 2.456 | 1.00 | 21.14 | A | N |
| ATOM | 5856 | CA | LEU | A | 381 | 39.216 | −9.230 | 3.581 | 1.00 | 20.85 | A | C |
| ATOM | 5858 | CB | LEU | A | 381 | 40.641 | −8.952 | 3.113 | 1.00 | 19.68 | A | C |
| ATOM | 5861 | CG | LEU | A | 381 | 41.690 | −8.904 | 4.212 | 1.00 | 22.69 | A | C |
| ATOM | 5863 | CD1 | LEU | A | 381 | 41.645 | −10.153 | 5.076 | 1.00 | 17.32 | A | C |
| ATOM | 5867 | CD2 | LEU | A | 381 | 43.038 | −8.730 | 3.552 | 1.00 | 20.69 | A | C |
| ATOM | 5871 | C | LEU | A | 381 | 38.781 | −8.183 | 4.584 | 1.00 | 18.62 | A | C |
| ATOM | 5872 | O | LEU | A | 381 | 38.690 | −8.459 | 5.778 | 1.00 | 20.47 | A | O |
| ATOM | 5874 | N | CYS | A | 382 | 38.457 | −6.990 | 4.102 | 1.00 | 21.03 | A | N |
| ATOM | 5875 | CA | CYS | A | 382 | 38.090 | −5.891 | 5.023 | 1.00 | 20.56 | A | C |
| ATOM | 5877 | CB | CYS | A | 382 | 38.032 | −4.551 | 4.283 | 1.00 | 21.31 | A | C |
| ATOM | 5880 | SG | CYS | A | 382 | 39.664 | −3.962 | 3.712 | 1.00 | 24.85 | A | S |
| ATOM | 5882 | C | CYS | A | 382 | 36.799 | −6.217 | 5.764 | 1.00 | 19.73 | A | C |
| ATOM | 5883 | O | CYS | A | 382 | 36.676 | −5.968 | 6.959 | 1.00 | 23.50 | A | O |
| ATOM | 5885 | N | ASN | A | 383 | 35.850 | −6.829 | 5.080 | 1.00 | 21.14 | A | N |
| ATOM | 5886 | CA | ASN | A | 383 | 34.646 | −7.367 | 5.742 | 1.00 | 21.35 | A | C |
| ATOM | 5888 | CB | ASN | A | 383 | 33.630 | −7.901 | 4.721 | 1.00 | 21.45 | A | C |

TABLE 4-2-continued

Coordinates of *P. alba* IspS

| | | | | | | | | | | | | |
|---|---|---|---|---|---|---|---|---|---|---|---|---|
| ATOM | 5891 | CG | ASN | A | 383 | 32.701 | −6.810 | 4.213 | 1.00 | 26.00 | A | C |
| ATOM | 5892 | OD1 | ASN | A | 383 | 31.849 | −6.300 | 4.960 | 1.00 | 32.37 | A | O |
| ATOM | 5893 | ND2 | ASN | A | 383 | 32.875 | −6.426 | 2.948 | 1.00 | 24.66 | A | N |
| ATOM | 5896 | C | ASN | A | 383 | 34.936 | −8.458 | 6.753 | 1.00 | 21.61 | A | C |
| ATOM | 5897 | O | ASN | A | 383 | 34.282 | −8.523 | 7.780 | 1.00 | 22.90 | A | O |
| ATOM | 5899 | N | ALA | A | 384 | 35.900 | −9.328 | 6.486 | 1.00 | 21.49 | A | N |
| ATOM | 5900 | CA | ALA | A | 384 | 36.234 | −10.330 | 7.505 | 1.00 | 19.41 | A | C |
| ATOM | 5902 | CB | ALA | A | 384 | 37.163 | −11.414 | 6.934 | 1.00 | 15.55 | A | C |
| ATOM | 5906 | C | ALA | A | 384 | 36.851 | −9.602 | 8.744 | 1.00 | 18.65 | A | C |
| ATOM | 5907 | O | ALA | A | 384 | 36.449 | −9.851 | 9.886 | 1.00 | 18.75 | A | O |
| ATOM | 5909 | N | PHE | A | 385 | 37.785 | −8.682 | 8.517 | 1.00 | 18.91 | A | N |
| ATOM | 5910 | CA | PHE | A | 385 | 38.319 | −7.831 | 9.626 | 1.00 | 20.64 | A | C |
| ATOM | 5912 | CB | PHE | A | 385 | 39.311 | −6.773 | 9.127 | 1.00 | 21.86 | A | C |
| ATOM | 5915 | CG | PHE | A | 385 | 40.647 | −7.296 | 8.653 | 1.00 | 18.71 | A | C |
| ATOM | 5916 | CD1 | PHE | A | 385 | 41.305 | −8.317 | 9.312 | 1.00 | 27.92 | A | C |
| ATOM | 5918 | CE1 | PHE | A | 385 | 42.566 | −8.754 | 8.889 | 1.00 | 23.74 | A | C |
| ATOM | 5920 | CZ | PHE | A | 385 | 43.190 | −8.126 | 7.810 | 1.00 | 25.70 | A | C |
| ATOM | 5922 | CE2 | PHE | A | 385 | 42.544 | −7.058 | 7.171 | 1.00 | 24.54 | A | C |
| ATOM | 5924 | CD2 | PHE | A | 385 | 41.296 | −6.652 | 7.608 | 1.00 | 22.39 | A | C |
| ATOM | 5926 | C | PHE | A | 385 | 37.199 | −7.059 | 10.362 | 1.00 | 21.40 | A | C |
| ATOM | 5927 | O | PHE | A | 385 | 37.158 | −7.013 | 11.590 | 1.00 | 24.82 | A | O |
| ATOM | 5929 | N | LEU | A | 386 | 36.293 | −6.439 | 9.621 | 1.00 | 21.38 | A | N |
| ATOM | 5930 | CA | LEU | A | 386 | 35.174 | −5.721 | 10.254 | 1.00 | 20.88 | A | C |
| ATOM | 5932 | CB | LEU | A | 386 | 34.226 | −5.138 | 9.186 | 1.00 | 20.67 | A | C |
| ATOM | 5935 | CG | LEU | A | 386 | 33.068 | −4.256 | 9.667 | 1.00 | 24.05 | A | C |
| ATOM | 5937 | CD1 | LEU | A | 386 | 33.624 | −2.975 | 10.307 | 1.00 | 17.84 | A | C |
| ATOM | 5941 | CD2 | LEU | A | 386 | 32.096 | −3.922 | 8.539 | 1.00 | 14.02 | A | C |
| ATOM | 5945 | C | LEU | A | 386 | 34.390 | −6.629 | 11.200 | 1.00 | 20.84 | A | C |
| ATOM | 5946 | O | LEU | A | 386 | 34.093 | −6.263 | 12.350 | 1.00 | 22.03 | A | O |
| ATOM | 5948 | N | GLN | A | 387 | 34.050 | −7.816 | 10.725 | 1.00 | 21.21 | A | N |
| ATOM | 5949 | CA | GLN | A | 387 | 33.315 | −8.754 | 11.561 | 1.00 | 22.62 | A | C |
| ATOM | 5951 | CB | GLN | A | 387 | 33.016 | −10.052 | 10.816 | 1.00 | 23.54 | A | C |
| ATOM | 5954 | CG | GLN | A | 387 | 32.222 | −11.067 | 11.634 | 1.00 | 23.83 | A | C |
| ATOM | 5957 | CD | GLN | A | 387 | 30.830 | −10.587 | 11.951 | 1.00 | 23.98 | A | C |
| ATOM | 5958 | OE1 | GLN | A | 387 | 30.560 | −10.108 | 13.050 | 1.00 | 26.91 | A | O |
| ATOM | 5959 | NE2 | GLN | A | 387 | 29.933 | −10.715 | 10.987 | 1.00 | 30.18 | A | N |
| ATOM | 5962 | C | GLN | A | 387 | 34.082 | −9.045 | 12.847 | 1.00 | 23.68 | A | C |
| ATOM | 5963 | O | GLN | A | 387 | 33.491 | −9.080 | 13.933 | 1.00 | 21.96 | A | O |
| ATOM | 5965 | N | GLU | A | 388 | 35.393 | −9.237 | 12.738 | 1.00 | 24.58 | A | N |
| ATOM | 5966 | CA | GLU | A | 388 | 36.209 | −9.469 | 13.935 | 1.00 | 24.13 | A | C |
| ATOM | 5968 | CB | GLU | A | 388 | 37.684 | −9.705 | 13.601 | 1.00 | 23.71 | A | C |
| ATOM | 5971 | CG | GLU | A | 388 | 37.932 | −11.099 | 13.059 | 1.00 | 31.30 | A | C |
| ATOM | 5974 | CD | GLU | A | 388 | 39.385 | −11.373 | 12.675 | 1.00 | 36.02 | A | C |
| ATOM | 5975 | OE1 | GLU | A | 388 | 40.209 | −10.407 | 12.511 | 1.00 | 32.55 | A | O |
| ATOM | 5976 | OE2 | GLU | A | 388 | 39.674 | −12.582 | 12.531 | 1.00 | 30.48 | A | O |
| ATOM | 5977 | C | GLU | A | 388 | 36.108 | −8.308 | 14.885 | 1.00 | 21.29 | A | C |
| ATOM | 5978 | O | GLU | A | 388 | 35.996 | −8.503 | 16.091 | 1.00 | 19.35 | A | O |
| ATOM | 5980 | N | ALA | A | 389 | 36.164 | −7.098 | 14.343 | 1.00 | 20.43 | A | N |
| ATOM | 5981 | CA | ALA | A | 389 | 36.155 | −5.918 | 15.196 | 1.00 | 19.95 | A | C |
| ATOM | 5983 | CB | ALA | A | 389 | 36.443 | −4.670 | 14.404 | 1.00 | 17.61 | A | C |
| ATOM | 5987 | C | ALA | A | 389 | 34.797 | −5.816 | 15.883 | 1.00 | 20.79 | A | C |
| ATOM | 5988 | O | ALA | A | 389 | 34.724 | −5.453 | 17.045 | 1.00 | 22.39 | A | O |
| ATOM | 5990 | N | LYS | A | 390 | 33.729 | −6.150 | 15.162 | 1.00 | 21.47 | A | N |
| ATOM | 5991 | CA | LYS | A | 390 | 32.387 | −6.056 | 15.711 | 1.00 | 22.95 | A | C |
| ATOM | 5993 | CB | LYS | A | 390 | 31.347 | −6.272 | 14.611 | 1.00 | 22.84 | A | C |
| ATOM | 5996 | CG | LYS | A | 390 | 31.150 | −5.048 | 13.739 | 1.00 | 25.85 | A | C |
| ATOM | 5999 | CD | LYS | A | 390 | 30.033 | −5.259 | 12.719 | 1.00 | 33.32 | A | C |
| ATOM | 6002 | CE | LYS | A | 390 | 29.796 | −4.002 | 11.896 | 1.00 | 31.02 | A | C |
| ATOM | 6005 | NZ | LYS | A | 390 | 28.888 | −4.249 | 10.737 | 1.00 | 29.50 | A | N |
| ATOM | 6009 | C | LYS | A | 390 | 32.187 | −7.065 | 16.837 | 1.00 | 24.05 | A | C |
| ATOM | 6010 | O | LYS | A | 390 | 31.632 | −6.753 | 17.885 | 1.00 | 24.65 | A | O |
| ATOM | 6012 | N | TRP | A | 391 | 32.641 | −8.283 | 16.616 | 1.00 | 24.13 | A | N |
| ATOM | 6013 | CA | TRP | A | 391 | 32.563 | −9.303 | 17.650 | 1.00 | 24.58 | A | C |
| ATOM | 6015 | CB | TRP | A | 391 | 33.143 | −10.619 | 17.154 | 1.00 | 23.28 | A | C |
| ATOM | 6018 | CG | TRP | A | 391 | 32.225 | −11.389 | 16.264 | 1.00 | 23.35 | A | C |
| ATOM | 6019 | CD1 | TRP | A | 391 | 30.864 | −11.354 | 16.250 | 1.00 | 21.14 | A | C |
| ATOM | 6021 | NE1 | TRP | A | 391 | 30.373 | −12.235 | 15.311 | 1.00 | 24.01 | A | N |
| ATOM | 6023 | CE2 | TRP | A | 391 | 31.428 | −12.876 | 14.721 | 1.00 | 24.82 | A | C |
| ATOM | 6024 | CD2 | TRP | A | 391 | 32.610 | −12.365 | 15.298 | 1.00 | 19.00 | A | C |
| ATOM | 6025 | CE3 | TRP | A | 391 | 33.838 | −12.866 | 14.868 | 1.00 | 23.69 | A | C |
| ATOM | 6027 | CZ3 | TRP | A | 391 | 33.850 | −13.832 | 13.882 | 1.00 | 17.43 | A | C |
| ATOM | 6029 | CH2 | TRP | A | 391 | 32.657 | −14.317 | 13.325 | 1.00 | 20.76 | A | C |
| ATOM | 6031 | CZ2 | TRP | A | 391 | 31.444 | −13.852 | 13.722 | 1.00 | 22.46 | A | C |
| ATOM | 6033 | C | TRP | A | 391 | 33.288 | −8.885 | 18.920 | 1.00 | 25.69 | A | C |
| ATOM | 6034 | O | TRP | A | 391 | 32.775 | −9.100 | 20.029 | 1.00 | 25.53 | A | O |
| ATOM | 6036 | N | LEU | A | 392 | 34.463 | −8.286 | 18.764 | 1.00 | 25.73 | A | N |
| ATOM | 6037 | CA | LEU | A | 392 | 35.227 | −7.805 | 19.918 | 1.00 | 28.86 | A | C |
| ATOM | 6039 | CB | LEU | A | 392 | 36.604 | −7.319 | 19.470 | 1.00 | 30.60 | A | C |

TABLE 4-2-continued

Coordinates of *P. alba* IspS

| | | | | | | | | | | | | |
|---|---|---|---|---|---|---|---|---|---|---|---|---|
| ATOM | 6042 | CG | LEU | A | 392 | 37.653 | −7.119 | 20.559 | 1.00 | 36.67 | A | C |
| ATOM | 6044 | CD1 | LEU | A | 392 | 39.053 | −7.245 | 19.946 | 1.00 | 40.63 | A | C |
| ATOM | 6048 | CD2 | LEU | A | 392 | 37.478 | −5.762 | 21.262 | 1.00 | 44.84 | A | C |
| ATOM | 6052 | C | LEU | A | 392 | 34.491 | −6.698 | 20.687 | 1.00 | 28.06 | A | C |
| ATOM | 6053 | O | LEU | A | 392 | 34.347 | −6.775 | 21.910 | 1.00 | 28.35 | A | O |
| ATOM | 6055 | N | TYR | A | 393 | 34.014 | −5.684 | 19.972 | 1.00 | 26.84 | A | N |
| ATOM | 6056 | CA | TYR | A | 393 | 33.328 | −4.551 | 20.604 | 1.00 | 27.94 | A | C |
| ATOM | 6058 | CB | TYR | A | 393 | 32.933 | −3.512 | 19.543 | 1.00 | 29.05 | A | C |
| ATOM | 6061 | CG | TYR | A | 393 | 32.189 | −2.306 | 20.078 | 1.00 | 33.13 | A | C |
| ATOM | 6062 | CD1 | TYR | A | 393 | 32.877 | −1.226 | 20.635 | 1.00 | 38.76 | A | C |
| ATOM | 6064 | CE1 | TYR | A | 393 | 32.198 | −0.112 | 21.146 | 1.00 | 40.86 | A | C |
| ATOM | 6066 | CZ | TYR | A | 393 | 30.817 | −0.066 | 21.085 | 1.00 | 42.91 | A | C |
| ATOM | 6067 | OH | TYR | A | 393 | 30.143 | 1.030 | 21.583 | 1.00 | 50.26 | A | O |
| ATOM | 6069 | CE2 | TYR | A | 393 | 30.107 | −1.123 | 20.526 | 1.00 | 40.58 | A | C |
| ATOM | 6071 | CD2 | TYR | A | 393 | 30.801 | −2.236 | 20.021 | 1.00 | 39.09 | A | C |
| ATOM | 6073 | C | TYR | A | 393 | 32.079 | −4.996 | 21.374 | 1.00 | 27.58 | A | C |
| ATOM | 6074 | O | TYR | A | 393 | 31.853 | −4.573 | 22.506 | 1.00 | 26.98 | A | O |
| ATOM | 6076 | N | ASN | A | 394 | 31.282 | −5.851 | 20.738 | 1.00 | 27.69 | A | N |
| ATOM | 6077 | CA | ASN | A | 394 | 30.010 | −6.312 | 21.272 | 1.00 | 27.80 | A | C |
| ATOM | 6079 | CB | ASN | A | 394 | 29.091 | −6.716 | 20.120 | 1.00 | 26.84 | A | C |
| ATOM | 6082 | CG | ASN | A | 394 | 28.616 | −5.521 | 19.324 | 1.00 | 28.06 | A | C |
| ATOM | 6083 | OD1 | ASN | A | 394 | 28.225 | −4.498 | 19.890 | 1.00 | 31.10 | A | O |
| ATOM | 6084 | ND2 | ASN | A | 394 | 28.644 | −5.636 | 18.010 | 1.00 | 32.05 | A | N |
| ATOM | 6087 | C | ASN | A | 394 | 30.156 | −7.458 | 22.261 | 1.00 | 29.31 | A | C |
| ATOM | 6088 | O | ASN | A | 394 | 29.158 | −7.944 | 22.801 | 1.00 | 29.60 | A | O |
| ATOM | 6090 | N | LYS | A | 395 | 31.402 | −7.865 | 22.511 | 1.00 | 30.96 | A | N |
| ATOM | 6091 | CA | LYS | A | 395 | 31.706 | −9.034 | 23.329 | 1.00 | 32.88 | A | C |
| ATOM | 6093 | CB | LYS | A | 395 | 31.443 | −8.749 | 24.815 | 1.00 | 34.38 | A | C |
| ATOM | 6096 | CG | LYS | A | 395 | 32.374 | −7.690 | 25.445 | 1.00 | 42.56 | A | C |
| ATOM | 6099 | CD | LYS | A | 395 | 31.603 | −6.475 | 25.978 | 1.00 | 50.78 | A | C |
| ATOM | 6102 | CE | LYS | A | 395 | 32.434 | −5.652 | 26.968 | 1.00 | 54.57 | A | C |
| ATOM | 6105 | NZ | LYS | A | 395 | 31.610 | −4.582 | 27.621 | 1.00 | 55.82 | A | N |
| ATOM | 6109 | C | LYS | A | 395 | 30.923 | −10.279 | 22.863 | 1.00 | 32.85 | A | C |
| ATOM | 6110 | O | LYS | A | 395 | 30.490 | −11.090 | 23.686 | 1.00 | 34.23 | A | O |
| ATOM | 6112 | N | SER | A | 396 | 30.765 | −10.431 | 21.546 | 1.00 | 31.79 | A | N |
| ATOM | 6113 | CA | SER | A | 396 | 30.034 | −11.571 | 20.970 | 1.00 | 30.45 | A | C |
| ATOM | 6115 | CB | SER | A | 396 | 29.868 | −11.402 | 19.464 | 1.00 | 29.95 | A | C |
| ATOM | 6118 | OG | SER | A | 396 | 29.007 | −10.318 | 19.148 | 1.00 | 31.64 | A | O |
| ATOM | 6120 | C | SER | A | 396 | 30.730 | −12.899 | 21.259 | 1.00 | 29.40 | A | C |
| ATOM | 6121 | O | SER | A | 396 | 31.933 | −12.948 | 21.512 | 1.00 | 31.77 | A | O |
| ATOM | 6123 | N | THR | A | 397 | 29.948 | −13.971 | 21.222 | 1.00 | 28.99 | A | N |
| ATOM | 6124 | CA | THR | A | 397 | 30.423 | −15.315 | 21.529 | 1.00 | 27.69 | A | C |
| ATOM | 6126 | CB | THR | A | 397 | 29.822 | −15.821 | 22.880 | 1.00 | 28.85 | A | C |
| ATOM | 6128 | OG1 | THR | A | 397 | 28.392 | −15.908 | 22.774 | 1.00 | 29.53 | A | O |
| ATOM | 6130 | CG2 | THR | A | 397 | 30.183 | −14.877 | 24.028 | 1.00 | 27.66 | A | C |
| ATOM | 6134 | C | THR | A | 397 | 30.017 | −16.273 | 20.407 | 1.00 | 26.90 | A | C |
| ATOM | 6135 | O | THR | A | 397 | 29.316 | −17.266 | 20.658 | 1.00 | 29.05 | A | O |
| ATOM | 6137 | N | PRO | A | 398 | 30.466 | −16.003 | 19.168 | 1.00 | 23.74 | A | N |
| ATOM | 6138 | CA | PRO | A | 398 | 30.051 | −16.849 | 18.046 | 1.00 | 23.94 | A | C |
| ATOM | 6140 | CB | PRO | A | 398 | 30.741 | −16.196 | 16.855 | 1.00 | 23.33 | A | C |
| ATOM | 6143 | CG | PRO | A | 398 | 32.020 | −15.684 | 17.456 | 1.00 | 24.23 | A | C |
| ATOM | 6146 | CD | PRO | A | 398 | 31.632 | −15.176 | 18.816 | 1.00 | 23.86 | A | C |
| ATOM | 6149 | C | PRO | A | 398 | 30.558 | −18.274 | 18.192 | 1.00 | 22.60 | A | C |
| ATOM | 6150 | O | PRO | A | 398 | 31.522 | −18.516 | 18.905 | 1.00 | 23.64 | A | O |
| ATOM | 6151 | N | THR | A | 399 | 29.918 | −19.210 | 17.511 | 1.00 | 22.40 | A | N |
| ATOM | 6152 | CA | THR | A | 399 | 30.354 | −20.602 | 17.542 | 1.00 | 21.81 | A | C |
| ATOM | 6154 | CB | THR | A | 399 | 29.367 | −21.499 | 16.770 | 1.00 | 23.98 | A | C |
| ATOM | 6156 | OG1 | THR | A | 399 | 29.377 | −21.129 | 15.376 | 1.00 | 24.75 | A | O |
| ATOM | 6158 | CG2 | THR | A | 399 | 27.909 | −21.381 | 17.366 | 1.00 | 14.91 | A | C |
| ATOM | 6162 | C | THR | A | 399 | 31.716 | −20.718 | 16.882 | 1.00 | 22.61 | A | C |
| ATOM | 6163 | O | THR | A | 399 | 32.127 | −19.807 | 16.181 | 1.00 | 26.36 | A | O |
| ATOM | 6165 | N | PHE | A | 400 | 32.411 | −21.839 | 17.094 | 1.00 | 23.40 | A | N |
| ATOM | 6166 | CA | PHE | A | 400 | 33.704 | −22.095 | 16.443 | 1.00 | 22.11 | A | C |
| ATOM | 6168 | CB | PHE | A | 400 | 34.252 | −23.474 | 16.814 | 1.00 | 22.13 | A | C |
| ATOM | 6171 | CG | PHE | A | 400 | 35.471 | −23.874 | 16.008 | 1.00 | 24.27 | A | C |
| ATOM | 6172 | CD1 | PHE | A | 400 | 36.709 | −23.344 | 16.297 | 1.00 | 25.15 | A | C |
| ATOM | 6174 | CE1 | PHE | A | 400 | 37.825 | −23.700 | 15.562 | 1.00 | 27.59 | A | C |
| ATOM | 6176 | CZ | PHE | A | 400 | 37.706 | −24.594 | 14.508 | 1.00 | 24.77 | A | C |
| ATOM | 6178 | CE2 | PHE | A | 400 | 36.485 | −25.112 | 14.212 | 1.00 | 26.28 | A | C |
| ATOM | 6180 | CD2 | PHE | A | 400 | 35.370 | −24.765 | 14.961 | 1.00 | 27.15 | A | C |
| ATOM | 6182 | C | PHE | A | 400 | 33.607 | −22.031 | 14.942 | 1.00 | 22.50 | A | C |
| ATOM | 6183 | O | PHE | A | 400 | 34.444 | −21.431 | 14.291 | 1.00 | 24.88 | A | O |
| ATOM | 6185 | N | ASP | A | 401 | 32.592 | −22.671 | 14.386 | 1.00 | 23.39 | A | N |
| ATOM | 6186 | CA | ASP | A | 401 | 32.403 | −22.692 | 12.937 | 1.00 | 24.28 | A | C |
| ATOM | 6188 | CB | ASP | A | 401 | 31.188 | −23.522 | 12.564 | 1.00 | 23.91 | A | C |
| ATOM | 6191 | CG | ASP | A | 401 | 31.358 | −24.979 | 12.941 | 1.00 | 28.76 | A | C |
| ATOM | 6192 | OD1 | ASP | A | 401 | 32.437 | −25.532 | 12.673 | 1.00 | 27.85 | A | O |
| ATOM | 6193 | OD2 | ASP | A | 401 | 30.423 | −25.559 | 13.533 | 1.00 | 36.29 | A | O |

TABLE 4-2-continued

Coordinates of *P. alba* IspS

| | | | | | | | | | | | | |
|---|---|---|---|---|---|---|---|---|---|---|---|---|
| ATOM | 6194 | C | ASP | A | 401 | 32.284 | −21.294 | 12.338 | 1.00 | 25.29 | A | C |
| ATOM | 6195 | O | ASP | A | 401 | 32.891 | −21.033 | 11.298 | 1.00 | 24.72 | A | O |
| ATOM | 6197 | N | ASP | A | 402 | 31.512 | −20.417 | 12.991 | 1.00 | 25.45 | A | N |
| ATOM | 6198 | CA | ASP | A | 402 | 31.359 | −19.016 | 12.557 | 1.00 | 25.75 | A | C |
| ATOM | 6200 | CB | ASP | A | 402 | 30.248 | −18.298 | 13.337 | 1.00 | 24.45 | A | C |
| ATOM | 6203 | CG | ASP | A | 402 | 28.864 | −18.808 | 13.005 | 1.00 | 31.45 | A | C |
| ATOM | 6204 | OD1 | ASP | A | 402 | 28.671 | −19.403 | 11.913 | 1.00 | 37.61 | A | O |
| ATOM | 6205 | OD2 | ASP | A | 402 | 27.959 | −18.589 | 13.847 | 1.00 | 37.38 | A | O |
| ATOM | 6206 | C | ASP | A | 402 | 32.664 | −18.196 | 12.708 | 1.00 | 25.83 | A | C |
| ATOM | 6207 | O | ASP | A | 402 | 33.042 | −17.481 | 11.782 | 1.00 | 26.75 | A | O |
| ATOM | 6209 | N | TYR | A | 403 | 33.329 | −18.301 | 13.861 | 1.00 | 23.13 | A | N |
| ATOM | 6210 | CA | TYR | A | 403 | 34.579 | −17.565 | 14.082 | 1.00 | 24.59 | A | C |
| ATOM | 6212 | CB | TYR | A | 403 | 35.098 | −17.728 | 15.511 | 1.00 | 24.61 | A | C |
| ATOM | 6215 | CG | TYR | A | 403 | 36.334 | −16.894 | 15.730 | 1.00 | 28.40 | A | C |
| ATOM | 6216 | CD1 | TYR | A | 403 | 36.236 | −15.532 | 15.998 | 1.00 | 32.59 | A | C |
| ATOM | 6218 | CE1 | TYR | A | 403 | 37.367 | −14.758 | 16.178 | 1.00 | 34.56 | A | C |
| ATOM | 6220 | CZ | TYR | A | 403 | 38.607 | −15.340 | 16.074 | 1.00 | 33.11 | A | C |
| ATOM | 6221 | OH | TYR | A | 403 | 39.730 | −14.586 | 16.261 | 1.00 | 39.07 | A | O |
| ATOM | 6223 | CE2 | TYR | A | 403 | 38.730 | −16.683 | 15.799 | 1.00 | 36.49 | A | C |
| ATOM | 6225 | CD2 | TYR | A | 403 | 37.598 | −17.450 | 15.621 | 1.00 | 29.76 | A | C |
| ATOM | 6227 | C | TYR | A | 403 | 35.694 | −17.999 | 13.161 | 1.00 | 24.10 | A | C |
| ATOM | 6228 | O | TYR | A | 403 | 36.406 | −17.162 | 12.585 | 1.00 | 24.93 | A | O |
| ATOM | 6230 | N | PHE | A | 404 | 35.873 | −19.315 | 13.073 | 1.00 | 23.56 | A | N |
| ATOM | 6231 | CA | PHE | A | 404 | 36.904 | −19.899 | 12.235 | 1.00 | 22.27 | A | C |
| ATOM | 6233 | CB | PHE | A | 404 | 37.024 | −21.394 | 12.494 | 1.00 | 21.27 | A | C |
| ATOM | 6236 | CG | PHE | A | 404 | 38.023 | −22.073 | 11.628 | 1.00 | 21.41 | A | C |
| ATOM | 6237 | CD1 | PHE | A | 404 | 39.364 | −21.747 | 11.713 | 1.00 | 23.52 | A | C |
| ATOM | 6239 | CE1 | PHE | A | 404 | 40.280 | −22.365 | 10.908 | 1.00 | 20.75 | A | C |
| ATOM | 6241 | CZ | PHE | A | 404 | 39.877 | −23.310 | 10.012 | 1.00 | 19.51 | A | C |
| ATOM | 6243 | CE2 | PHE | A | 404 | 38.550 | −23.641 | 9.903 | 1.00 | 24.73 | A | C |
| ATOM | 6245 | CD2 | PHE | A | 404 | 37.627 | −23.022 | 10.701 | 1.00 | 25.71 | A | C |
| ATOM | 6247 | C | PHE | A | 404 | 36.611 | −19.655 | 10.769 | 1.00 | 23.34 | A | C |
| ATOM | 6248 | O | PHE | A | 404 | 37.539 | −19.400 | 9.990 | 1.00 | 24.39 | A | O |
| ATOM | 6250 | N | GLY | A | 405 | 35.338 | −19.738 | 10.387 | 1.00 | 23.21 | A | N |
| ATOM | 6251 | CA | GLY | A | 405 | 34.937 | −19.437 | 9.004 | 1.00 | 24.54 | A | C |
| ATOM | 6254 | C | GLY | A | 405 | 35.401 | −18.050 | 8.580 | 1.00 | 24.99 | A | C |
| ATOM | 6255 | O | GLY | A | 405 | 35.994 | −17.879 | 7.533 | 1.00 | 28.71 | A | O |
| ATOM | 6257 | N | ASN | A | 406 | 35.145 | −17.062 | 9.423 | 1.00 | 24.64 | A | N |
| ATOM | 6258 | CA | ASN | A | 406 | 35.613 | −15.697 | 9.202 | 1.00 | 23.03 | A | C |
| ATOM | 6260 | CB | ASN | A | 406 | 34.943 | −14.761 | 10.193 | 1.00 | 22.91 | A | C |
| ATOM | 6263 | CG | ASN | A | 406 | 35.200 | −13.294 | 9.881 | 1.00 | 22.65 | A | C |
| ATOM | 6264 | OD1 | ASN | A | 406 | 34.666 | −12.755 | 8.927 | 1.00 | 21.35 | A | O |
| ATOM | 6265 | ND2 | ASN | A | 406 | 35.999 | −12.646 | 10.709 | 1.00 | 10.69 | A | N |
| ATOM | 6268 | C | ASN | A | 406 | 37.137 | −15.589 | 9.322 | 1.00 | 22.38 | A | C |
| ATOM | 6269 | O | ASN | A | 406 | 37.770 | −14.927 | 8.512 | 1.00 | 22.73 | A | O |
| ATOM | 6271 | N | ALA | A | 407 | 37.717 | −16.273 | 10.311 | 1.00 | 21.38 | A | N |
| ATOM | 6272 | CA | ALA | A | 407 | 39.138 | −16.136 | 10.630 | 1.00 | 19.47 | A | C |
| ATOM | 6274 | CB | ALA | A | 407 | 39.437 | −16.829 | 11.920 | 1.00 | 18.28 | A | C |
| ATOM | 6278 | C | ALA | A | 407 | 40.118 | −16.626 | 9.546 | 1.00 | 21.80 | A | C |
| ATOM | 6279 | O | ALA | A | 407 | 41.210 | −16.042 | 9.394 | 1.00 | 20.64 | A | O |
| ATOM | 6281 | N | TRP | A | 408 | 39.767 | −17.691 | 8.817 | 1.00 | 20.25 | A | N |
| ATOM | 6282 | CA | TRP | A | 408 | 40.648 | −18.153 | 7.738 | 1.00 | 21.62 | A | C |
| ATOM | 6284 | CB | TRP | A | 408 | 40.410 | −19.619 | 7.303 | 1.00 | 20.05 | A | C |
| ATOM | 6287 | CG | TRP | A | 408 | 39.101 | −20.016 | 6.707 | 1.00 | 20.37 | A | C |
| ATOM | 6288 | CD1 | TRP | A | 408 | 38.120 | −20.717 | 7.331 | 1.00 | 22.39 | A | C |
| ATOM | 6290 | NE1 | TRP | A | 408 | 37.081 | −20.959 | 6.468 | 1.00 | 22.00 | A | N |
| ATOM | 6292 | CE2 | TRP | A | 408 | 37.389 | −20.445 | 5.242 | 1.00 | 25.44 | A | C |
| ATOM | 6293 | CD2 | TRP | A | 408 | 38.661 | −19.852 | 5.342 | 1.00 | 24.30 | A | C |
| ATOM | 6294 | CE3 | TRP | A | 408 | 39.204 | −19.239 | 4.215 | 1.00 | 21.11 | A | C |
| ATOM | 6296 | CZ3 | TRP | A | 408 | 38.484 | −19.231 | 3.054 | 1.00 | 23.35 | A | C |
| ATOM | 6298 | CH2 | TRP | A | 408 | 37.218 | −19.843 | 2.972 | 1.00 | 25.47 | A | C |
| ATOM | 6300 | CZ2 | TRP | A | 408 | 36.656 | −20.454 | 4.058 | 1.00 | 28.32 | A | C |
| ATOM | 6302 | C | TRP | A | 408 | 40.645 | −17.193 | 6.560 | 1.00 | 21.64 | A | C |
| ATOM | 6303 | O | TRP | A | 408 | 41.626 | −17.105 | 5.835 | 1.00 | 25.03 | A | O |
| ATOM | 6305 | N | LYS | A | 409 | 39.555 | −16.457 | 6.393 | 1.00 | 21.99 | A | N |
| ATOM | 6306 | CA | LYS | A | 409 | 39.512 | −15.343 | 5.452 | 1.00 | 20.54 | A | C |
| ATOM | 6308 | CB | LYS | A | 409 | 38.064 | −14.918 | 5.204 | 1.00 | 21.65 | A | C |
| ATOM | 6311 | CG | LYS | A | 409 | 37.258 | −15.966 | 4.401 | 1.00 | 26.50 | A | C |
| ATOM | 6314 | CD | LYS | A | 409 | 35.889 | −15.427 | 3.920 | 1.00 | 37.40 | A | C |
| ATOM | 6317 | CE | LYS | A | 409 | 34.998 | −16.525 | 3.284 | 1.00 | 37.80 | A | C |
| ATOM | 6320 | NZ | LYS | A | 409 | 34.458 | −17.478 | 4.334 | 1.00 | 45.51 | A | N |
| ATOM | 6324 | C | LYS | A | 409 | 40.336 | −14.142 | 5.947 | 1.00 | 20.29 | A | C |
| ATOM | 6325 | O | LYS | A | 409 | 41.041 | −13.522 | 5.166 | 1.00 | 19.77 | A | O |
| ATOM | 6327 | N | SER | A | 410 | 40.238 | −13.822 | 7.240 | 1.00 | 20.14 | A | N |
| ATOM | 6328 | CA | SER | A | 410 | 40.942 | −12.689 | 7.809 | 1.00 | 20.34 | A | C |
| ATOM | 6330 | CB | SER | A | 410 | 40.355 | −12.306 | 9.171 | 1.00 | 21.88 | A | C |
| ATOM | 6333 | OG | SER | A | 410 | 40.776 | −13.162 | 10.222 | 1.00 | 22.69 | A | O |
| ATOM | 6335 | C | SER | A | 410 | 42.444 | −12.915 | 7.940 | 1.00 | 21.36 | A | C |

TABLE 4-2-continued

Coordinates of *P. alba* IspS

| | | | | | | | | | | | | |
|---|---|---|---|---|---|---|---|---|---|---|---|---|
| ATOM | 6336 | O | SER | A | 410 | 43.181 | −11.974 | 8.121 | 1.00 | 25.27 | A | O |
| ATOM | 6338 | N | SER | A | 411 | 42.894 | −14.159 | 7.853 | 1.00 | 21.66 | A | N |
| ATOM | 6339 | CA | SER | A | 411 | 44.323 | −14.472 | 7.749 | 1.00 | 19.61 | A | C |
| ATOM | 6341 | CB | SER | A | 411 | 44.498 | −15.982 | 7.515 | 1.00 | 20.08 | A | C |
| ATOM | 6344 | OG | SER | A | 411 | 44.053 | −16.360 | 6.210 | 1.00 | 16.88 | A | O |
| ATOM | 6346 | C | SER | A | 411 | 44.978 | −13.744 | 6.578 | 1.00 | 19.91 | A | C |
| ATOM | 6347 | O | SER | A | 411 | 46.162 | −13.450 | 6.635 | 1.00 | 21.95 | A | O |
| ATOM | 6349 | N | SER | A | 412 | 44.191 | −13.545 | 5.514 | 1.00 | 21.23 | A | N |
| ATOM | 6350 | CA | SER | A | 412 | 44.583 | −13.016 | 4.210 | 1.00 | 22.76 | A | C |
| ATOM | 6352 | CB | SER | A | 412 | 45.556 | −11.838 | 4.292 | 1.00 | 23.35 | A | C |
| ATOM | 6355 | OG | SER | A | 412 | 46.887 | −12.243 | 4.513 | 1.00 | 23.24 | A | O |
| ATOM | 6357 | C | SER | A | 412 | 45.145 | −14.076 | 3.279 | 1.00 | 24.50 | A | C |
| ATOM | 6358 | O | SER | A | 412 | 45.498 | −13.765 | 2.140 | 1.00 | 25.91 | A | O |
| ATOM | 6360 | N | GLY | A | 413 | 45.193 | −15.324 | 3.726 | 1.00 | 21.84 | A | N |
| ATOM | 6361 | CA | GLY | A | 413 | 45.631 | −16.399 | 2.840 | 1.00 | 21.18 | A | C |
| ATOM | 6364 | C | GLY | A | 413 | 44.883 | −16.434 | 1.512 | 1.00 | 21.67 | A | C |
| ATOM | 6365 | O | GLY | A | 413 | 45.486 | −16.563 | 0.421 | 1.00 | 23.81 | A | O |
| ATOM | 6367 | N | PRO | A | 414 | 43.563 | −16.338 | 1.573 | 1.00 | 19.53 | A | N |
| ATOM | 6368 | CA | PRO | A | 414 | 42.874 | −16.401 | 0.317 | 1.00 | 20.30 | A | C |
| ATOM | 6370 | CB | PRO | A | 414 | 41.403 | −16.323 | 0.743 | 1.00 | 21.26 | A | C |
| ATOM | 6373 | CG | PRO | A | 414 | 41.405 | −16.957 | 2.086 | 1.00 | 19.47 | A | C |
| ATOM | 6376 | CD | PRO | A | 414 | 42.621 | −16.372 | 2.708 | 1.00 | 18.13 | A | C |
| ATOM | 6379 | C | PRO | A | 414 | 43.244 | −15.251 | −0.621 | 1.00 | 20.27 | A | C |
| ATOM | 6380 | O | PRO | A | 414 | 43.472 | −15.460 | −1.813 | 1.00 | 21.85 | A | O |
| ATOM | 6381 | N | LEU | A | 415 | 43.319 | −14.047 | −0.088 | 1.00 | 22.69 | A | N |
| ATOM | 6382 | CA | LEU | A | 415 | 43.651 | −12.894 | −0.914 | 1.00 | 21.21 | A | C |
| ATOM | 6384 | CB | LEU | A | 415 | 43.542 | −11.617 | −0.091 | 1.00 | 23.62 | A | C |
| ATOM | 6387 | CG | LEU | A | 415 | 44.014 | −10.325 | −0.761 | 1.00 | 25.57 | A | C |
| ATOM | 6389 | CD1 | LEU | A | 415 | 43.140 | −9.131 | −0.331 | 1.00 | 24.96 | A | C |
| ATOM | 6393 | CD2 | LEU | A | 415 | 45.473 | −10.080 | −0.413 | 1.00 | 23.56 | A | C |
| ATOM | 6397 | C | LEU | A | 415 | 45.037 | −13.046 | −1.495 | 1.00 | 20.90 | A | C |
| ATOM | 6398 | O | LEU | A | 415 | 45.251 | −12.774 | −2.673 | 1.00 | 20.89 | A | O |
| ATOM | 6400 | N | GLN | A | 416 | 45.991 | −13.480 | −0.682 | 1.00 | 20.64 | A | N |
| ATOM | 6401 | CA | GLN | A | 416 | 47.343 | −13.694 | −1.193 | 1.00 | 21.69 | A | C |
| ATOM | 6403 | CB | GLN | A | 416 | 48.251 | −14.217 | −0.111 | 1.00 | 22.06 | A | C |
| ATOM | 6406 | CG | GLN | A | 416 | 48.534 | −13.218 | 0.973 | 1.00 | 22.59 | A | C |
| ATOM | 6409 | CD | GLN | A | 416 | 49.502 | −13.765 | 1.993 | 1.00 | 26.11 | A | C |
| ATOM | 6410 | OE1 | GLN | A | 416 | 50.390 | −14.547 | 1.671 | 1.00 | 29.66 | A | O |
| ATOM | 6411 | NE2 | GLN | A | 416 | 49.336 | −13.354 | 3.230 | 1.00 | 25.39 | A | N |
| ATOM | 6414 | C | GLN | A | 416 | 47.377 | −14.662 | −2.355 | 1.00 | 22.17 | A | C |
| ATOM | 6415 | O | GLN | A | 416 | 48.115 | −14.479 | −3.326 | 1.00 | 23.08 | A | O |
| ATOM | 6417 | N | LEU | A | 417 | 46.557 | −15.693 | −2.258 | 1.00 | 22.31 | A | N |
| ATOM | 6418 | CA | LEU | A | 417 | 46.551 | −16.738 | −3.261 | 1.00 | 21.08 | A | C |
| ATOM | 6420 | CB | LEU | A | 417 | 45.990 | −18.030 | −2.654 | 1.00 | 21.91 | A | C |
| ATOM | 6423 | CG | LEU | A | 417 | 46.945 | −18.669 | −1.639 | 1.00 | 19.81 | A | C |
| ATOM | 6425 | CD1 | LEU | A | 417 | 46.344 | −19.945 | −1.113 | 1.00 | 14.21 | A | C |
| ATOM | 6429 | CD2 | LEU | A | 417 | 48.346 | −18.927 | −2.256 | 1.00 | 18.26 | A | C |
| ATOM | 6433 | C | LEU | A | 417 | 45.790 | −16.309 | −4.513 | 1.00 | 20.42 | A | C |
| ATOM | 6434 | O | LEU | A | 417 | 46.103 | −16.788 | −5.593 | 1.00 | 22.88 | A | O |
| ATOM | 6436 | N | VAL | A | 418 | 44.810 | −15.411 | −4.392 | 1.00 | 19.02 | A | N |
| ATOM | 6437 | CA | VAL | A | 418 | 44.225 | −14.779 | −5.577 | 1.00 | 18.67 | A | C |
| ATOM | 6439 | CB | VAL | A | 418 | 42.998 | −13.900 | −5.236 | 1.00 | 20.97 | A | C |
| ATOM | 6441 | CG1 | VAL | A | 418 | 41.818 | −14.753 | −4.788 | 1.00 | 18.15 | A | C |
| ATOM | 6445 | CG2 | VAL | A | 418 | 42.578 | −13.054 | −6.466 | 1.00 | 20.23 | A | C |
| ATOM | 6449 | C | VAL | A | 418 | 45.294 | −13.951 | −6.316 | 1.00 | 21.16 | A | C |
| ATOM | 6450 | O | VAL | A | 418 | 45.461 | −14.083 | −7.528 | 1.00 | 22.26 | A | O |
| ATOM | 6452 | N | PHE | A | 419 | 46.042 | −13.109 | −5.596 | 1.00 | 21.17 | A | N |
| ATOM | 6453 | CA | PHE | A | 419 | 47.119 | −12.364 | −6.258 | 1.00 | 21.54 | A | C |
| ATOM | 6455 | CB | PHE | A | 419 | 47.765 | −11.331 | −5.319 | 1.00 | 23.17 | A | C |
| ATOM | 6458 | CG | PHE | A | 419 | 46.958 | −10.072 | −5.184 | 1.00 | 21.42 | A | C |
| ATOM | 6459 | CD1 | PHE | A | 419 | 47.326 | −8.931 | −5.865 | 1.00 | 22.64 | A | C |
| ATOM | 6461 | CE1 | PHE | A | 419 | 46.556 | −7.776 | −5.772 | 1.00 | 25.28 | A | C |
| ATOM | 6463 | CZ | PHE | A | 419 | 45.400 | −7.762 | −5.000 | 1.00 | 19.63 | A | C |
| ATOM | 6465 | CE2 | PHE | A | 419 | 45.006 | −8.907 | −4.339 | 1.00 | 19.52 | A | C |
| ATOM | 6467 | CD2 | PHE | A | 419 | 45.780 | −10.056 | −4.431 | 1.00 | 16.56 | A | C |
| ATOM | 6469 | C | PHE | A | 419 | 48.170 | −13.309 | −6.836 | 1.00 | 23.38 | A | C |
| ATOM | 6470 | O | PHE | A | 419 | 48.675 | −13.070 | −7.931 | 1.00 | 25.01 | A | O |
| ATOM | 6472 | N | ALA | A | 420 | 48.485 | −14.385 | −6.112 | 1.00 | 23.32 | A | N |
| ATOM | 6473 | CA | ALA | A | 420 | 49.475 | −15.361 | −6.567 | 1.00 | 23.26 | A | C |
| ATOM | 6475 | CB | ALA | A | 420 | 49.690 | −16.442 | −5.494 | 1.00 | 23.21 | A | C |
| ATOM | 6479 | C | ALA | A | 420 | 49.055 | −15.988 | −7.887 | 1.00 | 23.77 | A | C |
| ATOM | 6480 | O | ALA | A | 420 | 49.844 | −16.087 | −8.828 | 1.00 | 25.95 | A | O |
| ATOM | 6482 | N | TYR | A | 421 | 47.794 | −16.363 | −7.978 | 1.00 | 23.54 | A | N |
| ATOM | 6483 | CA | TYR | A | 421 | 47.263 | −16.960 | −9.198 | 1.00 | 23.07 | A | C |
| ATOM | 6485 | CB | TYR | A | 421 | 45.749 | −17.152 | −9.089 | 1.00 | 21.91 | A | C |
| ATOM | 6488 | CG | TYR | A | 421 | 45.100 | −17.619 | −10.361 | 1.00 | 27.04 | A | C |
| ATOM | 6489 | CD1 | TYR | A | 421 | 44.986 | −18.967 | −10.667 | 1.00 | 27.50 | A | C |
| ATOM | 6491 | CE1 | TYR | A | 421 | 44.387 | −19.382 | −11.857 | 1.00 | 24.79 | A | C |

TABLE 4-2-continued

Coordinates of *P. alba* IspS

| | | | | | | | | | | | | |
|---|---|---|---|---|---|---|---|---|---|---|---|---|
| ATOM | 6493 | CZ | TYR | A | 421 | 43.913 | −18.448 | −12.741 | 1.00 | 29.31 | A | C |
| ATOM | 6494 | OH | TYR | A | 421 | 43.313 | −18.816 | −13.933 | 1.00 | 31.42 | A | O |
| ATOM | 6496 | CE2 | TYR | A | 421 | 44.033 | −17.116 | −12.450 | 1.00 | 27.45 | A | C |
| ATOM | 6498 | CD2 | TYR | A | 421 | 44.619 | −16.714 | −11.274 | 1.00 | 28.49 | A | C |
| ATOM | 6500 | C | TYR | A | 421 | 47.595 | −16.104 | −10.417 | 1.00 | 24.43 | A | C |
| ATOM | 6501 | O | TYR | A | 421 | 48.121 | −16.591 | −11.394 | 1.00 | 24.22 | A | O |
| ATOM | 6503 | N | PHE | A | 422 | 47.276 | −14.823 | −10.369 | 1.00 | 26.68 | A | N |
| ATOM | 6504 | CA | PHE | A | 422 | 47.503 | −13.956 | −11.530 | 1.00 | 25.20 | A | C |
| ATOM | 6506 | CB | PHE | A | 422 | 46.767 | −12.615 | −11.366 | 1.00 | 24.18 | A | C |
| ATOM | 6509 | CG | PHE | A | 422 | 45.256 | −12.751 | −11.365 | 1.00 | 22.43 | A | C |
| ATOM | 6510 | CD1 | PHE | A | 422 | 44.575 | −13.050 | −12.530 | 1.00 | 24.26 | A | C |
| ATOM | 6512 | CE1 | PHE | A | 422 | 43.211 | −13.195 | −12.532 | 1.00 | 19.71 | A | C |
| ATOM | 6514 | CZ | PHE | A | 422 | 42.501 | −13.018 | −11.375 | 1.00 | 23.62 | A | C |
| ATOM | 6516 | CE2 | PHE | A | 422 | 43.173 | −12.692 | −10.206 | 1.00 | 23.66 | A | C |
| ATOM | 6518 | CD2 | PHE | A | 422 | 44.528 | −12.584 | −10.209 | 1.00 | 23.28 | A | C |
| ATOM | 6520 | C | PHE | A | 422 | 48.995 | −13.758 | −11.820 | 1.00 | 25.13 | A | C |
| ATOM | 6521 | O | PHE | A | 422 | 49.373 | −13.524 | −12.938 | 1.00 | 26.88 | A | O |
| ATOM | 6523 | N | ALA | A | 423 | 49.848 | −13.890 | −10.816 | 1.00 | 26.63 | A | N |
| ATOM | 6524 | CA | ALA | A | 423 | 51.276 | −13.786 | −11.044 | 1.00 | 25.44 | A | C |
| ATOM | 6526 | CB | ALA | A | 423 | 51.948 | −13.230 | −9.802 | 1.00 | 23.79 | A | C |
| ATOM | 6530 | C | ALA | A | 423 | 51.971 | −15.094 | −11.494 | 1.00 | 26.97 | A | C |
| ATOM | 6531 | O | ALA | A | 423 | 53.081 | −15.036 | −12.004 | 1.00 | 27.50 | A | O |
| ATOM | 6533 | N | VAL | A | 424 | 51.374 | −16.264 | −11.299 | 1.00 | 28.07 | A | N |
| ATOM | 6534 | CA | VAL | A | 424 | 52.066 | −17.507 | −11.685 | 1.00 | 29.42 | A | C |
| ATOM | 6536 | CB | VAL | A | 424 | 52.283 | −18.495 | −10.493 | 1.00 | 29.38 | A | C |
| ATOM | 6538 | CG1 | VAL | A | 424 | 52.977 | −17.799 | −9.333 | 1.00 | 25.33 | A | C |
| ATOM | 6542 | CG2 | VAL | A | 424 | 50.996 | −19.113 | −10.041 | 1.00 | 22.76 | A | C |
| ATOM | 6546 | C | VAL | A | 424 | 51.408 | −18.251 | −12.844 | 1.00 | 33.66 | A | C |
| ATOM | 6547 | O | VAL | A | 424 | 52.053 | −19.079 | −13.490 | 1.00 | 35.50 | A | O |
| ATOM | 6549 | N | VAL | A | 425 | 50.146 | −17.965 | −13.127 | 1.00 | 35.54 | A | N |
| ATOM | 6550 | CA | VAL | A | 425 | 49.462 | −18.645 | −14.216 | 1.00 | 39.97 | A | C |
| ATOM | 6552 | CB | VAL | A | 425 | 47.958 | −18.802 | −13.917 | 1.00 | 41.70 | A | C |
| ATOM | 6554 | CG1 | VAL | A | 425 | 47.191 | −19.173 | −15.166 | 1.00 | 40.48 | A | C |
| ATOM | 6558 | CG2 | VAL | A | 425 | 47.747 | −19.848 | −12.808 | 1.00 | 38.62 | A | C |
| ATOM | 6562 | C | VAL | A | 425 | 49.640 | −17.919 | −15.547 | 1.00 | 43.30 | A | C |
| ATOM | 6563 | O | VAL | A | 425 | 49.391 | −16.728 | −15.649 | 1.00 | 45.08 | A | O |
| ATOM | 6565 | N | GLN | A | 426 | 50.020 | −18.681 | −16.567 | 1.00 | 47.38 | A | N |
| ATOM | 6566 | CA | GLN | A | 426 | 50.299 | −18.169 | −17.911 | 1.00 | 50.63 | A | C |
| ATOM | 6568 | CB | GLN | A | 426 | 50.890 | −19.311 | −18.767 | 1.00 | 52.86 | A | C |
| ATOM | 6571 | CG | GLN | A | 426 | 51.846 | −18.861 | −19.889 | 1.00 | 62.22 | A | C |
| ATOM | 6574 | CD | GLN | A | 426 | 52.389 | −20.034 | −20.719 | 1.00 | 68.68 | A | C |
| ATOM | 6575 | OE1 | GLN | A | 426 | 52.756 | −21.079 | −20.174 | 1.00 | 74.04 | A | O |
| ATOM | 6576 | NE2 | GLN | A | 426 | 52.439 | −19.857 | −22.039 | 1.00 | 69.99 | A | N |
| ATOM | 6579 | C | GLN | A | 426 | 49.041 | −17.602 | −18.573 | 1.00 | 48.57 | A | C |
| ATOM | 6580 | O | GLN | A | 426 | 49.002 | −16.441 | −18.976 | 1.00 | 49.10 | A | O |
| ATOM | 6582 | N | ASN | A | 427 | 48.014 | −18.437 | −18.675 | 1.00 | 46.60 | A | N |
| ATOM | 6583 | CA | ASN | A | 427 | 46.748 | −18.043 | −19.265 | 1.00 | 44.60 | A | C |
| ATOM | 6585 | CB | ASN | A | 427 | 46.429 | −18.906 | −20.487 | 1.00 | 44.23 | A | C |
| ATOM | 6588 | CG | ASN | A | 427 | 47.362 | −18.637 | −21.657 | 1.00 | 46.94 | A | C |
| ATOM | 6589 | OD1 | ASN | A | 427 | 47.181 | −17.674 | −22.416 | 1.00 | 45.67 | A | O |
| ATOM | 6590 | ND2 | ASN | A | 427 | 48.363 | −19.501 | −21.818 | 1.00 | 41.48 | A | N |
| ATOM | 6593 | C | ASN | A | 427 | 45.649 | −18.200 | −18.231 | 1.00 | 42.84 | A | C |
| ATOM | 6594 | O | ASN | A | 427 | 45.421 | −19.292 | −17.709 | 1.00 | 42.87 | A | O |
| ATOM | 6596 | N | ILE | A | 428 | 44.957 | −17.105 | −17.973 | 1.00 | 40.25 | A | N |
| ATOM | 6597 | CA | ILE | A | 428 | 43.853 | −17.067 | −17.038 | 1.00 | 40.59 | A | C |
| ATOM | 6599 | CB | ILE | A | 428 | 43.459 | −15.599 | −16.777 | 1.00 | 41.62 | A | C |
| ATOM | 6601 | CG1 | ILE | A | 428 | 44.629 | −14.848 | −16.128 | 1.00 | 40.01 | A | C |
| ATOM | 6604 | CD1 | ILE | A | 428 | 44.658 | −13.322 | −16.465 | 1.00 | 35.27 | A | C |
| ATOM | 6608 | CG2 | ILE | A | 428 | 42.222 | −15.507 | −15.910 | 1.00 | 44.80 | A | C |
| ATOM | 6612 | C | ILE | A | 428 | 42.693 | −17.839 | −17.658 | 1.00 | 41.08 | A | C |
| ATOM | 6613 | O | ILE | A | 428 | 42.553 | −17.846 | −18.880 | 1.00 | 42.37 | A | O |
| ATOM | 6615 | N | LYS | A | 429 | 41.896 | −18.518 | −16.832 | 1.00 | 40.25 | A | N |
| ATOM | 6616 | CA | LYS | A | 429 | 40.658 | −19.174 | −17.289 | 1.00 | 39.88 | A | C |
| ATOM | 6618 | CB | LYS | A | 429 | 40.765 | −20.701 | −17.218 | 1.00 | 40.54 | A | C |
| ATOM | 6621 | CG | LYS | A | 429 | 41.990 | −21.287 | −17.914 | 1.00 | 44.77 | A | C |
| ATOM | 6624 | CD | LYS | A | 429 | 42.057 | −22.807 | −17.758 | 1.00 | 51.10 | A | C |
| ATOM | 6627 | CE | LYS | A | 429 | 43.171 | −23.422 | −18.624 | 1.00 | 55.81 | A | C |
| ATOM | 6630 | NZ | LYS | A | 429 | 43.150 | −24.926 | −18.619 | 1.00 | 55.50 | A | N |
| ATOM | 6634 | C | LYS | A | 429 | 39.503 | −18.725 | −16.422 | 1.00 | 38.57 | A | C |
| ATOM | 6635 | O | LYS | A | 429 | 39.622 | −18.686 | −15.203 | 1.00 | 37.64 | A | O |
| ATOM | 6637 | N | LYS | A | 430 | 38.387 | −18.402 | −17.057 | 1.00 | 39.36 | A | N |
| ATOM | 6638 | CA | LYS | A | 430 | 37.202 | −17.914 | −16.377 | 1.00 | 41.11 | A | C |
| ATOM | 6640 | CB | LYS | A | 430 | 36.047 | −17.755 | −17.374 | 1.00 | 42.76 | A | C |
| ATOM | 6643 | CG | LYS | A | 430 | 34.811 | −17.033 | −16.805 | 1.00 | 52.15 | A | C |
| ATOM | 6646 | CD | LYS | A | 430 | 33.595 | −17.025 | −17.779 | 1.00 | 62.30 | A | C |
| ATOM | 6649 | CE | LYS | A | 430 | 33.214 | −18.434 | −18.289 | 1.00 | 67.69 | A | C |
| ATOM | 6652 | NZ | LYS | A | 430 | 33.285 | −19.518 | −17.240 | 1.00 | 70.45 | A | N |
| ATOM | 6656 | C | LYS | A | 430 | 36.760 | −18.829 | −15.242 | 1.00 | 39.57 | A | C |

TABLE 4-2-continued

| Coordinates of *P. alba* IspS | | | | | | | | | | | |
|---|---|---|---|---|---|---|---|---|---|---|---|
| ATOM | 6657 | O | LYS | A | 430 | 36.417 | −18.359 | −14.164 | 1.00 | 40.96 | A | O |
| ATOM | 6659 | N | GLU | A | 431 | 36.750 | −20.128 | −15.481 | 1.00 | 38.13 | A | N |
| ATOM | 6660 | CA | GLU | A | 431 | 36.268 | −21.066 | −14.481 | 1.00 | 38.67 | A | C |
| ATOM | 6662 | CB | GLU | A | 431 | 36.170 | −22.473 | −15.077 | 1.00 | 40.19 | A | C |
| ATOM | 6665 | CG | GLU | A | 431 | 35.497 | −23.511 | −14.161 | 1.00 | 48.81 | A | C |
| ATOM | 6668 | CD | GLU | A | 431 | 35.757 | −24.965 | −14.584 | 1.00 | 61.18 | A | C |
| ATOM | 6669 | OE1 | GLU | A | 431 | 36.689 | −25.202 | −15.394 | 1.00 | 63.32 | A | O |
| ATOM | 6670 | OE2 | GLU | A | 431 | 35.035 | −25.871 | −14.094 | 1.00 | 62.58 | A | O |
| ATOM | 6671 | C | GLU | A | 431 | 37.190 | −21.073 | −13.259 | 1.00 | 36.48 | A | C |
| ATOM | 6672 | O | GLU | A | 431 | 36.734 | −21.199 | −12.129 | 1.00 | 36.23 | A | O |
| ATOM | 6674 | N | GLU | A | 432 | 38.488 | −20.954 | −13.497 | 1.00 | 33.62 | A | N |
| ATOM | 6675 | CA | GLU | A | 432 | 39.445 | −20.894 | −12.420 | 1.00 | 32.85 | A | C |
| ATOM | 6677 | CB | GLU | A | 432 | 40.866 | −20.914 | −12.983 | 1.00 | 33.14 | A | C |
| ATOM | 6680 | CG | GLU | A | 432 | 41.222 | −22.249 | −13.661 | 1.00 | 32.44 | A | C |
| ATOM | 6683 | CD | GLU | A | 432 | 42.707 | −22.372 | −14.031 | 1.00 | 39.53 | A | C |
| ATOM | 6684 | OE1 | GLU | A | 432 | 43.375 | −21.332 | −14.238 | 1.00 | 36.98 | A | O |
| ATOM | 6685 | OE2 | GLU | A | 432 | 43.201 | −23.522 | −14.119 | 1.00 | 43.09 | A | O |
| ATOM | 6686 | C | GLU | A | 432 | 39.184 | −19.665 | −11.532 | 1.00 | 32.20 | A | C |
| ATOM | 6687 | O | GLU | A | 432 | 39.045 | −19.781 | −10.320 | 1.00 | 30.88 | A | O |
| ATOM | 6689 | N | ILE | A | 433 | 39.068 | −18.493 | −12.134 | 1.00 | 32.33 | A | N |
| ATOM | 6690 | CA | ILE | A | 433 | 38.908 | −17.281 | −11.335 | 1.00 | 34.37 | A | C |
| ATOM | 6692 | CB | ILE | A | 433 | 39.317 | −15.983 | −12.109 | 1.00 | 33.78 | A | C |
| ATOM | 6694 | CG1 | ILE | A | 433 | 38.480 | −15.704 | −13.327 | 1.00 | 38.66 | A | C |
| ATOM | 6697 | CD1 | ILE | A | 433 | 39.103 | −14.565 | −14.169 | 1.00 | 38.73 | A | C |
| ATOM | 6701 | CG2 | ILE | A | 433 | 40.739 | −16.106 | −12.614 | 1.00 | 35.34 | A | C |
| ATOM | 6705 | C | ILE | A | 433 | 37.524 | −17.235 | −10.645 | 1.00 | 33.31 | A | C |
| ATOM | 6706 | O | ILE | A | 433 | 37.414 | −16.838 | −9.485 | 1.00 | 33.97 | A | O |
| ATOM | 6708 | N | GLU | A | 434 | 36.501 | −17.744 | −11.305 | 1.00 | 30.95 | A | N |
| ATOM | 6709 | CA | GLU | A | 434 | 35.221 | −17.944 | −10.643 | 1.00 | 32.93 | A | C |
| ATOM | 6711 | CB | GLU | A | 434 | 34.242 | −18.683 | −11.551 | 1.00 | 33.75 | A | C |
| ATOM | 6714 | CG | GLU | A | 434 | 32.961 | −17.939 | −11.781 | 1.00 | 46.39 | A | C |
| ATOM | 6717 | CD | GLU | A | 434 | 33.044 | −17.044 | −12.995 | 1.00 | 58.82 | A | C |
| ATOM | 6718 | OE1 | GLU | A | 434 | 32.768 | −17.555 | −14.111 | 1.00 | 63.42 | A | O |
| ATOM | 6719 | OE2 | GLU | A | 434 | 33.383 | −15.842 | −12.828 | 1.00 | 62.69 | A | O |
| ATOM | 6720 | C | GLU | A | 434 | 35.349 | −18.777 | −9.367 | 1.00 | 31.62 | A | C |
| ATOM | 6721 | O | GLU | A | 434 | 34.681 | −18.501 | −8.378 | 1.00 | 30.48 | A | O |
| ATOM | 6723 | N | ASN | A | 435 | 36.149 | −19.844 | −9.428 | 1.00 | 29.51 | A | N |
| ATOM | 6724 | CA | ASN | A | 435 | 36.342 | −20.710 | −8.285 | 1.00 | 27.90 | A | C |
| ATOM | 6726 | CB | ASN | A | 435 | 36.878 | −22.070 | −8.714 | 1.00 | 28.27 | A | C |
| ATOM | 6729 | CG | ASN | A | 435 | 35.756 | −23.015 | −9.168 | 1.00 | 33.33 | A | C |
| ATOM | 6730 | OD1 | ASN | A | 435 | 35.103 | −23.671 | −8.354 | 1.00 | 37.87 | A | O |
| ATOM | 6731 | ND2 | ASN | A | 435 | 35.524 | −23.063 | −10.466 | 1.00 | 29.41 | A | N |
| ATOM | 6734 | C | ASN | A | 435 | 37.212 | −20.060 | −7.199 | 1.00 | 25.58 | A | C |
| ATOM | 6735 | O | ASN | A | 435 | 36.985 | −20.285 | −6.037 | 1.00 | 23.42 | A | O |
| ATOM | 6737 | N | LEU | A | 436 | 38.163 | −19.221 | −7.582 | 1.00 | 25.17 | A | N |
| ATOM | 6738 | CA | LEU | A | 436 | 38.861 | −18.411 | −6.597 | 1.00 | 27.41 | A | C |
| ATOM | 6740 | CB | LEU | A | 436 | 39.909 | −17.535 | −7.240 | 1.00 | 26.64 | A | C |
| ATOM | 6743 | CG | LEU | A | 436 | 41.090 | −18.252 | −7.868 | 1.00 | 26.99 | A | C |
| ATOM | 6745 | CD1 | LEU | A | 436 | 42.017 | −17.177 | −8.425 | 1.00 | 26.84 | A | C |
| ATOM | 6749 | CD2 | LEU | A | 436 | 41.819 | −19.140 | −6.861 | 1.00 | 23.22 | A | C |
| ATOM | 6753 | C | LEU | A | 436 | 37.892 | −17.536 | −5.800 | 1.00 | 28.45 | A | C |
| ATOM | 6754 | O | LEU | A | 436 | 37.991 | −17.504 | −4.587 | 1.00 | 29.36 | A | O |
| ATOM | 6756 | N | GLN | A | 437 | 36.936 | −16.891 | −6.465 | 1.00 | 30.08 | A | N |
| ATOM | 6757 | CA | GLN | A | 437 | 35.973 | −16.014 | −5.778 | 1.00 | 32.71 | A | C |
| ATOM | 6759 | CB | GLN | A | 437 | 35.120 | −15.210 | −6.760 | 1.00 | 34.60 | A | C |
| ATOM | 6762 | CG | GLN | A | 437 | 35.934 | −14.322 | −7.670 | 1.00 | 40.35 | A | C |
| ATOM | 6765 | CD | GLN | A | 437 | 35.165 | −13.112 | −8.186 | 1.00 | 41.37 | A | C |
| ATOM | 6766 | OE1 | GLN | A | 437 | 34.156 | −13.238 | −8.889 | 1.00 | 39.37 | A | O |
| ATOM | 6767 | NE2 | GLN | A | 437 | 35.667 | −11.931 | −7.865 | 1.00 | 36.34 | A | N |
| ATOM | 6770 | C | GLN | A | 437 | 35.034 | −16.781 | −4.887 | 1.00 | 32.09 | A | C |
| ATOM | 6771 | O | GLN | A | 437 | 34.485 | −16.215 | −3.930 | 1.00 | 31.31 | A | O |
| ATOM | 6773 | N | LYS | A | 438 | 34.824 | −18.058 | −5.192 | 1.00 | 31.99 | A | N |
| ATOM | 6774 | CA | LYS | A | 438 | 34.012 | −18.893 | −4.314 | 1.00 | 33.99 | A | C |
| ATOM | 6776 | CB | LYS | A | 438 | 33.202 | −19.913 | −5.124 | 1.00 | 35.73 | A | C |
| ATOM | 6779 | CG | LYS | A | 438 | 32.247 | −19.275 | −6.153 | 1.00 | 45.89 | A | C |
| ATOM | 6782 | CD | LYS | A | 438 | 31.513 | −20.316 | −7.024 | 1.00 | 55.14 | A | C |
| ATOM | 6785 | CE | LYS | A | 438 | 30.386 | −19.644 | −7.869 | 1.00 | 63.38 | A | C |
| ATOM | 6788 | NZ | LYS | A | 438 | 29.546 | −20.589 | −8.694 | 1.00 | 60.75 | A | N |
| ATOM | 6792 | C | LYS | A | 438 | 34.865 | −19.586 | −3.236 | 1.00 | 31.23 | A | C |
| ATOM | 6793 | O | LYS | A | 438 | 34.392 | −20.495 | −2.582 | 1.00 | 32.53 | A | O |
| ATOM | 6795 | N | TYR | A | 439 | 36.106 | −19.154 | −3.025 | 1.00 | 29.33 | A | N |
| ATOM | 6796 | CA | TYR | A | 439 | 36.987 | −19.827 | −2.037 | 1.00 | 30.37 | A | C |
| ATOM | 6798 | CB | TYR | A | 439 | 36.580 | −19.469 | −0.619 | 1.00 | 30.63 | A | C |
| ATOM | 6801 | CG | TYR | A | 439 | 36.618 | −18.009 | −0.425 | 1.00 | 34.45 | A | C |
| ATOM | 6802 | CD1 | TYR | A | 439 | 37.797 | −17.379 | −0.140 | 1.00 | 34.10 | A | C |
| ATOM | 6804 | CE1 | TYR | A | 439 | 37.843 | −16.017 | 0.018 | 1.00 | 46.73 | A | C |
| ATOM | 6806 | CZ | TYR | A | 439 | 36.696 | −15.271 | −0.125 | 1.00 | 42.16 | A | C |
| ATOM | 6807 | OH | TYR | A | 439 | 36.764 | −13.915 | 0.022 | 1.00 | 47.04 | A | O |

TABLE 4-2-continued

Coordinates of *P. alba* IspS

| | | | | | | | | | | | | |
|---|---|---|---|---|---|---|---|---|---|---|---|---|
| ATOM | 6809 | CE2 | TYR | A | 439 | 35.511 | −15.873 | −0.425 | 1.00 | 40.10 | A | C |
| ATOM | 6811 | CD2 | TYR | A | 439 | 35.471 | −17.237 | −0.574 | 1.00 | 40.92 | A | C |
| ATOM | 6813 | C | TYR | A | 439 | 37.069 | −21.348 | −2.189 | 1.00 | 28.38 | A | C |
| ATOM | 6814 | O | TYR | A | 439 | 36.845 | −22.103 | −1.260 | 1.00 | 29.86 | A | O |
| ATOM | 6816 | N | HIS | A | 440 | 37.398 | −21.772 | −3.393 | 1.00 | 28.22 | A | N |
| ATOM | 6817 | CA | HIS | A | 440 | 37.588 | −23.162 | −3.706 | 1.00 | 27.43 | A | C |
| ATOM | 6819 | CB | HIS | A | 440 | 38.015 | −23.245 | −5.154 | 1.00 | 27.12 | A | C |
| ATOM | 6822 | CG | HIS | A | 440 | 38.138 | −24.635 | −5.681 | 1.00 | 32.93 | A | C |
| ATOM | 6823 | ND1 | HIS | A | 440 | 39.347 | −25.286 | −5.776 | 1.00 | 33.95 | A | N |
| ATOM | 6825 | CE1 | HIS | A | 440 | 39.159 | −26.476 | −6.317 | 1.00 | 37.85 | A | C |
| ATOM | 6827 | NE2 | HIS | A | 440 | 37.873 | −26.615 | −6.576 | 1.00 | 39.10 | A | N |
| ATOM | 6829 | CD2 | HIS | A | 440 | 37.213 | −25.475 | −6.197 | 1.00 | 32.98 | A | C |
| ATOM | 6831 | C | HIS | A | 440 | 38.672 | −23.786 | −2.837 | 1.00 | 28.12 | A | C |
| ATOM | 6832 | O | HIS | A | 440 | 39.654 | −23.120 | −2.456 | 1.00 | 28.00 | A | O |
| ATOM | 6834 | N | ASP | A | 441 | 38.503 | −25.080 | −2.588 | 1.00 | 26.13 | A | N |
| ATOM | 6835 | CA | ASP | A | 441 | 39.400 | −25.896 | −1.767 | 1.00 | 26.61 | A | C |
| ATOM | 6837 | CB | ASP | A | 441 | 39.147 | −27.387 | −2.031 | 1.00 | 27.37 | A | C |
| ATOM | 6840 | CG | ASP | A | 441 | 37.763 | −27.853 | −1.564 | 1.00 | 29.75 | A | C |
| ATOM | 6841 | OD1 | ASP | A | 441 | 37.167 | −27.195 | −0.690 | 1.00 | 33.53 | A | O |
| ATOM | 6842 | OD2 | ASP | A | 441 | 37.280 | −28.881 | −2.096 | 1.00 | 42.48 | A | O |
| ATOM | 6843 | C | ASP | A | 441 | 40.881 | −25.637 | −1.966 | 1.00 | 25.58 | A | C |
| ATOM | 6844 | O | ASP | A | 441 | 41.660 | −25.729 | −1.031 | 1.00 | 24.77 | A | O |
| ATOM | 6846 | N | THR | A | 442 | 41.277 | −25.366 | −3.193 | 1.00 | 24.56 | A | N |
| ATOM | 6847 | CA | THR | A | 442 | 42.673 | −25.189 | −3.491 | 1.00 | 25.67 | A | C |
| ATOM | 6849 | CB | THR | A | 442 | 42.868 | −24.892 | −4.992 | 1.00 | 27.90 | A | C |
| ATOM | 6851 | OG1 | THR | A | 442 | 42.233 | −25.923 | −5.760 | 1.00 | 35.85 | A | O |
| ATOM | 6853 | CG2 | THR | A | 442 | 44.321 | −24.853 | −5.349 | 1.00 | 30.00 | A | C |
| ATOM | 6857 | C | THR | A | 442 | 43.224 | −24.046 | −2.635 | 1.00 | 24.91 | A | C |
| ATOM | 6858 | O | THR | A | 442 | 44.337 | −24.143 | −2.151 | 1.00 | 25.25 | A | O |
| ATOM | 6860 | N | ILE | A | 443 | 42.444 | −22.980 | −2.426 | 1.00 | 22.84 | A | N |
| ATOM | 6861 | CA | ILE | A | 443 | 42.947 | −21.824 | −1.701 | 1.00 | 22.34 | A | C |
| ATOM | 6863 | CB | ILE | A | 443 | 42.756 | −20.489 | −2.471 | 1.00 | 22.85 | A | C |
| ATOM | 6865 | CG1 | ILE | A | 443 | 41.323 | −20.006 | −2.467 | 1.00 | 21.22 | A | C |
| ATOM | 6868 | CD1 | ILE | A | 443 | 41.213 | −18.584 | −3.057 | 1.00 | 21.90 | A | C |
| ATOM | 6872 | CG2 | ILE | A | 443 | 43.241 | −20.606 | −3.900 | 1.00 | 18.47 | A | C |
| ATOM | 6876 | C | ILE | A | 443 | 42.392 | −21.728 | −0.294 | 1.00 | 23.52 | A | C |
| ATOM | 6877 | O | ILE | A | 443 | 43.045 | −21.179 | 0.600 | 1.00 | 24.12 | A | O |
| ATOM | 6879 | N | SER | A | 444 | 41.229 | −22.322 | −0.060 | 1.00 | 24.10 | A | N |
| ATOM | 6880 | CA | SER | A | 444 | 40.649 | −22.275 | 1.259 | 1.00 | 23.55 | A | C |
| ATOM | 6882 | CB | SER | A | 444 | 39.190 | −22.705 | 1.213 | 1.00 | 25.69 | A | C |
| ATOM | 6885 | OG | SER | A | 444 | 39.087 | −24.090 | 0.993 | 1.00 | 26.17 | A | O |
| ATOM | 6887 | C | SER | A | 444 | 41.453 | −23.163 | 2.210 | 1.00 | 24.88 | A | C |
| ATOM | 6888 | O | SER | A | 444 | 41.745 | −22.766 | 3.322 | 1.00 | 26.85 | A | O |
| ATOM | 6890 | N | ARG | A | 445 | 41.866 | −24.344 | 1.776 | 1.00 | 22.69 | A | N |
| ATOM | 6891 | CA | ARG | A | 445 | 42.481 | −25.273 | 2.732 | 1.00 | 23.70 | A | C |
| ATOM | 6893 | CB | ARG | A | 445 | 42.542 | −26.686 | 2.164 | 1.00 | 24.49 | A | C |
| ATOM | 6896 | CG | ARG | A | 445 | 41.178 | −27.309 | 2.168 | 1.00 | 24.68 | A | C |
| ATOM | 6899 | CD | ARG | A | 445 | 41.233 | −28.614 | 1.536 | 1.00 | 35.00 | A | C |
| ATOM | 6902 | NE | ARG | A | 445 | 39.915 | −29.227 | 1.462 | 1.00 | 41.73 | A | N |
| ATOM | 6904 | CZ | ARG | A | 445 | 39.533 | −30.015 | 0.465 | 1.00 | 40.99 | A | C |
| ATOM | 6905 | NH1 | ARG | A | 445 | 40.365 | −30.263 | −0.544 | 1.00 | 41.35 | A | N |
| ATOM | 6908 | NH2 | ARG | A | 445 | 38.333 | −30.562 | 0.478 | 1.00 | 38.98 | A | N |
| ATOM | 6911 | C | ARG | A | 445 | 43.820 | −24.835 | 3.305 | 1.00 | 23.32 | A | C |
| ATOM | 6912 | O | ARG | A | 445 | 44.022 | −24.930 | 4.514 | 1.00 | 23.11 | A | O |
| ATOM | 6914 | N | PRO | A | 446 | 44.722 | −24.325 | 2.458 | 1.00 | 23.47 | A | N |
| ATOM | 6915 | CA | PRO | A | 446 | 45.955 | −23.766 | 2.988 | 1.00 | 21.78 | A | C |
| ATOM | 6917 | CB | PRO | A | 446 | 46.703 | −23.284 | 1.751 | 1.00 | 21.26 | A | C |
| ATOM | 6920 | CG | PRO | A | 446 | 46.082 | −23.962 | 0.618 | 1.00 | 26.11 | A | C |
| ATOM | 6923 | CD | PRO | A | 446 | 44.688 | −24.299 | 0.985 | 1.00 | 25.66 | A | C |
| ATOM | 6926 | C | PRO | A | 446 | 45.677 | −22.599 | 3.903 | 1.00 | 20.98 | A | C |
| ATOM | 6927 | O | PRO | A | 446 | 46.397 | −22.418 | 4.875 | 1.00 | 22.87 | A | O |
| ATOM | 6928 | N | SER | A | 447 | 44.620 | −21.845 | 3.619 | 1.00 | 21.42 | A | N |
| ATOM | 6929 | CA | SER | A | 447 | 44.230 | −20.731 | 4.469 | 1.00 | 20.70 | A | C |
| ATOM | 6931 | CB | SER | A | 447 | 43.183 | −19.827 | 3.806 | 1.00 | 21.82 | A | C |
| ATOM | 6934 | OG | SER | A | 447 | 43.690 | −19.313 | 2.556 | 1.00 | 20.36 | A | O |
| ATOM | 6936 | C | SER | A | 447 | 43.777 | −21.209 | 5.822 | 1.00 | 22.31 | A | C |
| ATOM | 6937 | O | SER | A | 447 | 44.075 | −20.554 | 6.820 | 1.00 | 23.84 | A | O |
| ATOM | 6939 | N | HIS | A | 448 | 43.104 | −22.358 | 5.876 | 1.00 | 21.04 | A | N |
| ATOM | 6940 | CA | HIS | A | 448 | 42.712 | −22.952 | 7.144 | 1.00 | 20.19 | A | C |
| ATOM | 6942 | CB | HIS | A | 448 | 42.004 | −24.317 | 6.968 | 1.00 | 21.41 | A | C |
| ATOM | 6945 | CG | HIS | A | 448 | 40.675 | −24.253 | 6.277 | 1.00 | 21.38 | A | C |
| ATOM | 6946 | ND1 | HIS | A | 448 | 39.944 | −25.382 | 5.969 | 1.00 | 29.82 | A | N |
| ATOM | 6948 | CE1 | HIS | A | 448 | 38.812 | −25.025 | 5.382 | 1.00 | 29.77 | A | C |
| ATOM | 6950 | NE2 | HIS | A | 448 | 38.790 | −23.705 | 5.289 | 1.00 | 24.12 | A | N |
| ATOM | 6952 | CD2 | HIS | A | 448 | 39.939 | −23.202 | 5.844 | 1.00 | 24.45 | A | C |
| ATOM | 6954 | C | HIS | A | 448 | 43.959 | −23.180 | 7.969 | 1.00 | 20.74 | A | C |
| ATOM | 6955 | O | HIS | A | 448 | 44.002 | −22.864 | 9.156 | 1.00 | 21.08 | A | O |
| ATOM | 6957 | N | ILE | A | 449 | 44.979 | −23.756 | 7.340 | 1.00 | 23.35 | A | N |

TABLE 4-2-continued

| Coordinates of *P. alba* IspS | | | | | | | | | | | | |
|---|---|---|---|---|---|---|---|---|---|---|---|---|
| ATOM | 6958 | CA | ILE | A | 449 | 46.212 | −24.095 | 8.052 | 1.00 | 23.10 | A | C |
| ATOM | 6960 | CB | ILE | A | 449 | 47.188 | −24.850 | 7.162 | 1.00 | 24.84 | A | C |
| ATOM | 6962 | CG1 | ILE | A | 449 | 46.563 | −26.145 | 6.663 | 1.00 | 26.29 | A | C |
| ATOM | 6965 | CD1 | ILE | A | 449 | 46.302 | −27.059 | 7.721 | 1.00 | 29.80 | A | C |
| ATOM | 6969 | CG2 | ILE | A | 449 | 48.490 | −25.168 | 7.926 | 1.00 | 20.98 | A | C |
| ATOM | 6973 | C | ILE | A | 449 | 46.928 | −22.848 | 8.571 | 1.00 | 22.77 | A | C |
| ATOM | 6974 | O | ILE | A | 449 | 47.479 | −22.863 | 9.658 | 1.00 | 23.35 | A | O |
| ATOM | 6976 | N | PHE | A | 450 | 46.918 | −21.796 | 7.764 | 1.00 | 22.40 | A | N |
| ATOM | 6977 | CA | PHE | A | 450 | 47.527 | −20.514 | 8.097 | 1.00 | 23.32 | A | C |
| ATOM | 6979 | CB | PHE | A | 450 | 47.411 | −19.599 | 6.857 | 1.00 | 25.81 | A | C |
| ATOM | 6982 | CG | PHE | A | 450 | 47.936 | −18.168 | 7.029 | 1.00 | 26.15 | A | C |
| ATOM | 6983 | CD1 | PHE | A | 450 | 48.744 | −17.792 | 8.083 | 1.00 | 29.10 | A | C |
| ATOM | 6985 | CE1 | PHE | A | 450 | 49.178 | −16.483 | 8.205 | 1.00 | 27.29 | A | C |
| ATOM | 6987 | CZ | PHE | A | 450 | 48.850 | −15.548 | 7.238 | 1.00 | 27.02 | A | C |
| ATOM | 6989 | CE2 | PHE | A | 450 | 48.056 | −15.914 | 6.167 | 1.00 | 30.51 | A | C |
| ATOM | 6991 | CD2 | PHE | A | 450 | 47.625 | −17.214 | 6.062 | 1.00 | 23.58 | A | C |
| ATOM | 6993 | C | PHE | A | 450 | 46.854 | −19.966 | 9.342 | 1.00 | 22.59 | A | C |
| ATOM | 6994 | O | PHE | A | 450 | 47.505 | −19.733 | 10.370 | 1.00 | 23.10 | A | O |
| ATOM | 6996 | N | ARG | A | 451 | 45.538 | −19.856 | 9.327 | 1.00 | 22.00 | A | N |
| ATOM | 6997 | CA | ARG | A | 451 | 44.884 | −19.370 | 10.531 | 1.00 | 22.22 | A | C |
| ATOM | 6999 | CB | ARG | A | 451 | 43.396 | −19.215 | 10.307 | 1.00 | 20.08 | A | C |
| ATOM | 7002 | CG | ARG | A | 451 | 42.583 | −18.918 | 11.559 | 1.00 | 20.62 | A | C |
| ATOM | 7005 | CD | ARG | A | 451 | 43.123 | −17.713 | 12.310 | 1.00 | 20.48 | A | C |
| ATOM | 7008 | NE | ARG | A | 451 | 43.009 | −16.489 | 11.536 | 1.00 | 22.29 | A | N |
| ATOM | 7010 | CZ | ARG | A | 451 | 43.506 | −15.318 | 11.908 | 1.00 | 22.48 | A | C |
| ATOM | 7011 | NH1 | ARG | A | 451 | 44.207 | −15.207 | 13.027 | 1.00 | 20.34 | A | N |
| ATOM | 7014 | NH2 | ARG | A | 451 | 43.317 | −14.259 | 11.149 | 1.00 | 22.06 | A | N |
| ATOM | 7017 | C | ARG | A | 451 | 45.183 | −20.281 | 11.740 | 1.00 | 22.94 | A | C |
| ATOM | 7018 | O | ARG | A | 451 | 45.522 | −19.806 | 12.825 | 1.00 | 22.52 | A | O |
| ATOM | 7020 | N | LEU | A | 452 | 45.044 | −21.587 | 11.561 | 1.00 | 23.09 | A | N |
| ATOM | 7021 | CA | LEU | A | 452 | 45.208 | −22.500 | 12.700 | 1.00 | 22.53 | A | C |
| ATOM | 7023 | CB | LEU | A | 452 | 44.799 | −23.931 | 12.332 | 1.00 | 19.50 | A | C |
| ATOM | 7026 | CG | LEU | A | 452 | 43.313 | −24.152 | 12.034 | 1.00 | 22.38 | A | C |
| ATOM | 7028 | CD1 | LEU | A | 452 | 43.089 | −25.564 | 11.548 | 1.00 | 17.99 | A | C |
| ATOM | 7032 | CD2 | LEU | A | 452 | 42.403 | −23.854 | 13.257 | 1.00 | 20.44 | A | C |
| ATOM | 7036 | C | LEU | A | 452 | 46.632 | −22.453 | 13.278 | 1.00 | 22.42 | A | C |
| ATOM | 7037 | O | LEU | A | 452 | 46.793 | −22.522 | 14.485 | 1.00 | 24.48 | A | O |
| ATOM | 7039 | N | CYS | A | 453 | 47.656 | −22.340 | 12.433 | 1.00 | 22.44 | A | N |
| ATOM | 7040 | CA | CYS | A | 453 | 49.031 | −22.312 | 12.933 | 1.00 | 24.59 | A | C |
| ATOM | 7042 | CB | CYS | A | 453 | 50.051 | −22.425 | 11.804 | 1.00 | 26.01 | A | C |
| ATOM | 7045 | SG | CYS | A | 453 | 50.255 | −24.066 | 11.075 | 1.00 | 27.17 | A | S |
| ATOM | 7047 | C | CYS | A | 453 | 49.283 | −21.015 | 13.709 | 1.00 | 28.20 | A | C |
| ATOM | 7048 | O | CYS | A | 453 | 49.935 | −21.023 | 14.753 | 1.00 | 31.95 | A | O |
| ATOM | 7050 | N | ASN | A | 454 | 48.768 | −19.901 | 13.184 | 1.00 | 28.25 | A | N |
| ATOM | 7051 | CA | ASN | A | 454 | 48.874 | −18.600 | 13.832 | 1.00 | 25.74 | A | C |
| ATOM | 7053 | CB | ASN | A | 454 | 48.292 | −17.509 | 12.914 | 1.00 | 25.90 | A | C |
| ATOM | 7056 | CG | ASN | A | 454 | 48.465 | −16.083 | 13.470 | 1.00 | 26.47 | A | C |
| ATOM | 7057 | OD1 | ASN | A | 454 | 48.991 | −15.875 | 14.552 | 1.00 | 40.48 | A | O |
| ATOM | 7058 | ND2 | ASN | A | 454 | 48.002 | −15.108 | 12.715 | 1.00 | 31.43 | A | N |
| ATOM | 7061 | C | ASN | A | 454 | 48.183 | −18.595 | 15.180 | 1.00 | 26.43 | A | C |
| ATOM | 7062 | O | ASN | A | 454 | 48.774 | −18.191 | 16.180 | 1.00 | 28.40 | A | O |
| ATOM | 7064 | N | ASP | A | 455 | 46.927 | −19.024 | 15.205 | 1.00 | 26.39 | A | N |
| ATOM | 7065 | CA | ASP | A | 455 | 46.154 | −19.022 | 16.434 | 1.00 | 25.96 | A | C |
| ATOM | 7067 | CB | ASP | A | 455 | 44.695 | −19.399 | 16.185 | 1.00 | 26.38 | A | C |
| ATOM | 7070 | CG | ASP | A | 455 | 43.848 | −18.229 | 15.635 | 1.00 | 30.58 | A | C |
| ATOM | 7071 | OD1 | ASP | A | 455 | 44.407 | −17.210 | 15.161 | 1.00 | 23.66 | A | O |
| ATOM | 7072 | OD2 | ASP | A | 455 | 42.597 | −18.359 | 15.672 | 1.00 | 27.94 | A | O |
| ATOM | 7073 | C | ASP | A | 455 | 46.775 | −19.977 | 17.451 | 1.00 | 28.81 | A | C |
| ATOM | 7074 | O | ASP | A | 455 | 46.716 | −19.705 | 18.659 | 1.00 | 29.70 | A | O |
| ATOM | 7076 | N | LEU | A | 456 | 47.368 | −21.081 | 16.982 | 1.00 | 28.29 | A | N |
| ATOM | 7077 | CA | LEU | A | 456 | 48.072 | −21.997 | 17.886 | 1.00 | 29.09 | A | C |
| ATOM | 7079 | CB | LEU | A | 456 | 48.609 | −23.237 | 17.180 | 1.00 | 28.53 | A | C |
| ATOM | 7082 | CG | LEU | A | 456 | 47.613 | −24.345 | 16.893 | 1.00 | 30.92 | A | C |
| ATOM | 7084 | CD1 | LEU | A | 456 | 48.213 | −25.380 | 15.920 | 1.00 | 27.62 | A | C |
| ATOM | 7088 | CD2 | LEU | A | 456 | 47.182 | −24.972 | 18.197 | 1.00 | 26.10 | A | C |
| ATOM | 7092 | C | LEU | A | 456 | 49.240 | −21.292 | 18.552 | 1.00 | 30.48 | A | C |
| ATOM | 7093 | O | LEU | A | 456 | 49.465 | −21.492 | 19.733 | 1.00 | 30.20 | A | O |
| ATOM | 7095 | N | ALA | A | 457 | 49.965 | −20.458 | 17.807 | 1.00 | 30.94 | A | N |
| ATOM | 7096 | CA | ALA | A | 457 | 51.170 | −19.838 | 18.350 | 1.00 | 30.89 | A | C |
| ATOM | 7098 | CB | ALA | A | 457 | 51.906 | −19.078 | 17.293 | 1.00 | 28.28 | A | C |
| ATOM | 7102 | C | ALA | A | 457 | 50.847 | −18.917 | 19.515 | 1.00 | 32.02 | A | C |
| ATOM | 7103 | O | ALA | A | 457 | 51.601 | −18.841 | 20.466 | 1.00 | 34.01 | A | O |
| ATOM | 7105 | N | SER | A | 458 | 49.728 | −18.222 | 19.441 | 1.00 | 34.20 | A | N |
| ATOM | 7106 | CA | SER | A | 458 | 49.383 | −17.264 | 20.468 | 1.00 | 35.38 | A | C |
| ATOM | 7108 | CB | SER | A | 458 | 48.963 | −15.943 | 19.823 | 1.00 | 36.92 | A | C |
| ATOM | 7111 | OG | SER | A | 458 | 47.792 | −16.106 | 19.042 | 1.00 | 42.95 | A | O |
| ATOM | 7113 | C | SER | A | 458 | 48.282 | −17.746 | 21.385 | 1.00 | 34.92 | A | C |
| ATOM | 7114 | O | SER | A | 458 | 47.901 | −17.026 | 22.295 | 1.00 | 37.00 | A | O |

TABLE 4-2-continued

Coordinates of *P. alba* IspS

| | | | | | | | | | | | | |
|---|---|---|---|---|---|---|---|---|---|---|---|---|
| ATOM | 7116 | N | ALA | A | 459 | 47.772 | −18.955 | 21.178 | 1.00 | 34.97 | A | N |
| ATOM | 7117 | CA | ALA | A | 459 | 46.608 | −19.381 | 21.934 | 1.00 | 34.82 | A | C |
| ATOM | 7119 | CB | ALA | A | 459 | 46.246 | −20.833 | 21.642 | 1.00 | 33.75 | A | C |
| ATOM | 7123 | C | ALA | A | 459 | 46.827 | −19.195 | 23.424 | 1.00 | 36.34 | A | C |
| ATOM | 7124 | O | ALA | A | 459 | 46.042 | −18.506 | 24.078 | 1.00 | 34.86 | A | O |
| ATOM | 7126 | N | SER | A | 460 | 47.892 | −19.805 | 23.948 | 1.00 | 39.24 | A | N |
| ATOM | 7127 | CA | SER | A | 460 | 48.081 | −19.909 | 25.403 | 1.00 | 42.73 | A | C |
| ATOM | 7129 | CB | SER | A | 460 | 49.266 | −20.832 | 25.765 | 1.00 | 43.60 | A | C |
| ATOM | 7132 | OG | SER | A | 460 | 50.520 | −20.221 | 25.514 | 1.00 | 50.63 | A | O |
| ATOM | 7134 | C | SER | A | 460 | 48.188 | −18.543 | 26.093 | 1.00 | 42.82 | A | C |
| ATOM | 7135 | O | SER | A | 460 | 47.591 | −18.342 | 27.150 | 1.00 | 45.33 | A | O |
| ATOM | 7137 | N | ALA | A | 461 | 48.894 | −17.598 | 25.482 | 1.00 | 43.05 | A | N |
| ATOM | 7138 | CA | ALA | A | 461 | 49.000 | −16.245 | 26.037 | 1.00 | 43.65 | A | C |
| ATOM | 7140 | CB | ALA | A | 461 | 50.032 | −15.414 | 25.263 | 1.00 | 42.89 | A | C |
| ATOM | 7144 | C | ALA | A | 461 | 47.647 | −15.539 | 26.035 | 1.00 | 44.95 | A | C |
| ATOM | 7145 | O | ALA | A | 461 | 47.237 | −14.969 | 27.045 | 1.00 | 46.39 | A | O |
| ATOM | 7147 | N | GLU | A | 462 | 46.947 | −15.588 | 24.905 | 1.00 | 45.01 | A | N |
| ATOM | 7148 | CA | GLU | A | 462 | 45.666 | −14.906 | 24.787 | 1.00 | 43.89 | A | C |
| ATOM | 7150 | CB | GLU | A | 462 | 45.159 | −14.966 | 23.346 | 1.00 | 44.36 | A | C |
| ATOM | 7153 | CG | GLU | A | 462 | 46.045 | −14.140 | 22.394 | 1.00 | 46.73 | A | C |
| ATOM | 7156 | CD | GLU | A | 462 | 45.617 | −14.211 | 20.936 | 1.00 | 48.39 | A | C |
| ATOM | 7157 | OE1 | GLU | A | 462 | 44.548 | −14.792 | 20.655 | 1.00 | 52.33 | A | O |
| ATOM | 7158 | OE2 | GLU | A | 462 | 46.361 | −13.686 | 20.071 | 1.00 | 51.40 | A | O |
| ATOM | 7159 | C | GLU | A | 462 | 44.653 | −15.472 | 25.763 | 1.00 | 42.95 | A | C |
| ATOM | 7160 | O | GLU | A | 462 | 43.856 | −14.731 | 26.336 | 1.00 | 43.58 | A | O |
| ATOM | 7162 | N | ILE | A | 463 | 44.710 | −16.776 | 25.985 | 1.00 | 42.70 | A | N |
| ATOM | 7163 | CA | ILE | A | 463 | 43.782 | −17.436 | 26.897 | 1.00 | 44.06 | A | C |
| ATOM | 7165 | CB | ILE | A | 463 | 43.862 | −18.971 | 26.773 | 1.00 | 43.11 | A | C |
| ATOM | 7167 | CG1 | ILE | A | 463 | 43.216 | −19.427 | 25.461 | 1.00 | 43.65 | A | C |
| ATOM | 7170 | CD1 | ILE | A | 463 | 43.585 | −20.854 | 25.026 | 1.00 | 35.99 | A | C |
| ATOM | 7174 | CG2 | ILE | A | 463 | 43.180 | −19.641 | 27.948 | 1.00 | 43.57 | A | C |
| ATOM | 7178 | C | ILE | A | 463 | 44.055 | −17.028 | 28.344 | 1.00 | 46.68 | A | C |
| ATOM | 7179 | O | ILE | A | 463 | 43.119 | −16.877 | 29.134 | 1.00 | 47.89 | A | O |
| ATOM | 7181 | N | ALA | A | 464 | 45.334 | −16.854 | 28.678 | 1.00 | 47.67 | A | N |
| ATOM | 7182 | CA | ALA | A | 464 | 45.744 | −16.469 | 30.028 | 1.00 | 48.52 | A | C |
| ATOM | 7184 | CB | ALA | A | 464 | 47.240 | −16.690 | 30.214 | 1.00 | 47.57 | A | C |
| ATOM | 7188 | C | ALA | A | 464 | 45.365 | −15.013 | 30.335 | 1.00 | 49.52 | A | C |
| ATOM | 7189 | O | ALA | A | 464 | 45.060 | −14.690 | 31.477 | 1.00 | 49.39 | A | O |
| ATOM | 7191 | N | ARG | A | 465 | 45.362 | −14.153 | 29.311 | 1.00 | 50.44 | A | N |
| ATOM | 7192 | CA | ARG | A | 465 | 44.869 | −12.768 | 29.442 | 1.00 | 51.06 | A | C |
| ATOM | 7194 | CB | ARG | A | 465 | 45.373 | −11.889 | 28.285 | 1.00 | 51.52 | A | C |
| ATOM | 7197 | CG | ARG | A | 465 | 46.878 | −11.770 | 28.142 | 1.00 | 55.59 | A | C |
| ATOM | 7200 | CD | ARG | A | 465 | 47.250 | −10.670 | 27.135 | 1.00 | 58.49 | A | C |
| ATOM | 7203 | NE | ARG | A | 465 | 48.351 | −11.095 | 26.268 | 1.00 | 64.38 | A | N |
| ATOM | 7205 | CZ | ARG | A | 465 | 48.272 | −11.296 | 24.947 | 1.00 | 68.81 | A | C |
| ATOM | 7206 | NH1 | ARG | A | 465 | 47.138 | −11.087 | 24.269 | 1.00 | 68.12 | A | N |
| ATOM | 7209 | NH2 | ARG | A | 465 | 49.356 | −11.696 | 24.282 | 1.00 | 69.02 | A | N |
| ATOM | 7212 | C | ARG | A | 465 | 43.330 | −12.663 | 29.474 | 1.00 | 50.68 | A | C |
| ATOM | 7213 | O | ARG | A | 465 | 42.785 | −11.559 | 29.542 | 1.00 | 50.12 | A | O |
| ATOM | 7215 | N | GLY | A | 466 | 42.635 | −13.795 | 29.397 | 1.00 | 51.02 | A | N |
| ATOM | 7216 | CA | GLY | A | 466 | 41.175 | −13.811 | 29.340 | 1.00 | 50.69 | A | C |
| ATOM | 7219 | C | GLY | A | 466 | 40.582 | −13.347 | 28.015 | 1.00 | 49.88 | A | C |
| ATOM | 7220 | O | GLY | A | 466 | 39.478 | −12.817 | 27.989 | 1.00 | 50.15 | A | O |
| ATOM | 7222 | N | GLU | A | 467 | 41.304 | −13.545 | 26.914 | 1.00 | 49.42 | A | N |
| ATOM | 7223 | CA | GLU | A | 467 | 40.783 | −13.204 | 25.591 | 1.00 | 48.91 | A | C |
| ATOM | 7225 | CB | GLU | A | 467 | 41.897 | −12.706 | 24.677 | 1.00 | 49.79 | A | C |
| ATOM | 7228 | CG | GLU | A | 467 | 42.400 | −11.308 | 25.017 | 1.00 | 54.31 | A | C |
| ATOM | 7231 | CD | GLU | A | 467 | 43.488 | −10.836 | 24.059 | 1.00 | 62.07 | A | C |
| ATOM | 7232 | OE1 | GLU | A | 467 | 43.370 | −11.106 | 22.831 | 1.00 | 58.12 | A | O |
| ATOM | 7233 | OE2 | GLU | A | 467 | 44.457 | −10.198 | 24.543 | 1.00 | 65.78 | A | O |
| ATOM | 7234 | C | GLU | A | 467 | 40.046 | −14.372 | 24.923 | 1.00 | 46.84 | A | C |
| ATOM | 7235 | O | GLU | A | 467 | 40.258 | −15.543 | 25.245 | 1.00 | 46.20 | A | O |
| ATOM | 7237 | N | THR | A | 468 | 39.182 | −14.009 | 23.983 | 1.00 | 44.02 | A | N |
| ATOM | 7238 | CA | THR | A | 468 | 38.326 | −14.934 | 23.255 | 1.00 | 41.85 | A | C |
| ATOM | 7240 | CB | THR | A | 468 | 36.893 | −14.390 | 23.234 | 1.00 | 41.87 | A | C |
| ATOM | 7242 | OG1 | THR | A | 468 | 36.268 | −14.693 | 24.475 | 1.00 | 44.70 | A | O |
| ATOM | 7244 | CG2 | THR | A | 468 | 36.079 | −14.983 | 22.064 | 1.00 | 43.08 | A | C |
| ATOM | 7248 | C | THR | A | 468 | 38.732 | −15.112 | 21.793 | 1.00 | 39.84 | A | C |
| ATOM | 7249 | O | THR | A | 468 | 38.459 | −16.149 | 21.206 | 1.00 | 40.48 | A | O |
| ATOM | 7251 | N | ALA | A | 469 | 39.366 | −14.098 | 21.210 | 1.00 | 36.45 | A | N |
| ATOM | 7252 | CA | ALA | A | 469 | 39.501 | −14.004 | 19.772 | 1.00 | 35.32 | A | C |
| ATOM | 7254 | CB | ALA | A | 469 | 39.721 | −12.524 | 19.353 | 1.00 | 34.04 | A | C |
| ATOM | 7258 | C | ALA | A | 469 | 40.636 | −14.890 | 19.278 | 1.00 | 32.68 | A | C |
| ATOM | 7259 | O | ALA | A | 469 | 41.677 | −14.392 | 18.837 | 1.00 | 33.79 | A | O |
| ATOM | 7261 | N | ASN | A | 470 | 40.399 | −16.201 | 19.338 | 1.00 | 29.47 | A | N |
| ATOM | 7262 | CA | ASN | A | 470 | 41.373 | −17.233 | 18.951 | 1.00 | 27.64 | A | C |
| ATOM | 7264 | CB | ASN | A | 470 | 42.374 | −17.461 | 20.088 | 1.00 | 27.10 | A | C |
| ATOM | 7267 | CG | ASN | A | 470 | 43.550 | −18.304 | 19.660 | 1.00 | 28.28 | A | C |

TABLE 4-2-continued

Coordinates of *P. alba* IspS

| | | | | | | | | | | | | |
|---|---|---|---|---|---|---|---|---|---|---|---|---|
| ATOM | 7268 | OD1 | ASN | A | 470 | 43.450 | −19.524 | 19.605 | 1.00 | 34.80 | A | O |
| ATOM | 7269 | ND2 | ASN | A | 470 | 44.676 | −17.657 | 19.346 | 1.00 | 30.77 | A | N |
| ATOM | 7272 | C | ASN | A | 470 | 40.651 | −18.546 | 18.607 | 1.00 | 27.38 | A | C |
| ATOM | 7273 | O | ASN | A | 470 | 39.675 | −18.909 | 19.274 | 1.00 | 28.84 | A | O |
| ATOM | 7275 | N | SER | A | 471 | 41.115 | −19.259 | 17.580 | 1.00 | 25.73 | A | N |
| ATOM | 7276 | CA | SER | A | 471 | 40.413 | −20.476 | 17.127 | 1.00 | 25.56 | A | C |
| ATOM | 7278 | CB | SER | A | 471 | 41.033 | −21.026 | 15.831 | 1.00 | 24.86 | A | C |
| ATOM | 7281 | OG | SER | A | 471 | 40.941 | −20.066 | 14.773 | 1.00 | 24.10 | A | O |
| ATOM | 7283 | C | SER | A | 471 | 40.387 | −21.555 | 18.208 | 1.00 | 25.57 | A | C |
| ATOM | 7284 | O | SER | A | 471 | 39.370 | −22.234 | 18.392 | 1.00 | 28.49 | A | O |
| ATOM | 7286 | N | VAL | A | 472 | 41.487 | −21.689 | 18.940 | 1.00 | 24.63 | A | N |
| ATOM | 7287 | CA | VAL | A | 472 | 41.573 | −22.638 | 20.058 | 1.00 | 24.83 | A | C |
| ATOM | 7289 | CB | VAL | A | 472 | 42.976 | −22.647 | 20.681 | 1.00 | 24.78 | A | C |
| ATOM | 7291 | CG1 | VAL | A | 472 | 43.062 | −23.699 | 21.804 | 1.00 | 24.97 | A | C |
| ATOM | 7295 | CG2 | VAL | A | 472 | 44.025 | −22.919 | 19.612 | 1.00 | 24.81 | A | C |
| ATOM | 7299 | C | VAL | A | 472 | 40.585 | −22.302 | 21.161 | 1.00 | 25.99 | A | C |
| ATOM | 7300 | O | VAL | A | 472 | 39.878 | −23.166 | 21.682 | 1.00 | 27.14 | A | O |
| ATOM | 7302 | N | SER | A | 473 | 40.548 | −21.027 | 21.517 | 1.00 | 28.17 | A | N |
| ATOM | 7303 | CA | SER | A | 473 | 39.639 | −20.538 | 22.539 | 1.00 | 27.38 | A | C |
| ATOM | 7305 | CB | SER | A | 473 | 39.877 | −19.048 | 22.775 | 1.00 | 28.17 | A | C |
| ATOM | 7308 | OG | SER | A | 473 | 38.904 | −18.546 | 23.666 | 1.00 | 36.50 | A | O |
| ATOM | 7310 | C | SER | A | 473 | 38.199 | −20.785 | 22.134 | 1.00 | 26.74 | A | C |
| ATOM | 7311 | O | SER | A | 473 | 37.391 | −21.244 | 22.942 | 1.00 | 26.77 | A | O |
| ATOM | 7313 | N | CYS | A | 474 | 37.872 | −20.526 | 20.874 | 1.00 | 26.84 | A | N |
| ATOM | 7314 | CA | CYS | A | 474 | 36.513 | −20.796 | 20.410 | 1.00 | 27.97 | A | C |
| ATOM | 7316 | CB | CYS | A | 474 | 36.248 | −20.181 | 19.037 | 1.00 | 28.57 | A | C |
| ATOM | 7319 | SG | CYS | A | 474 | 36.094 | −18.392 | 19.116 | 1.00 | 37.03 | A | S |
| ATOM | 7321 | C | CYS | A | 474 | 36.219 | −22.290 | 20.396 | 1.00 | 27.00 | A | C |
| ATOM | 7322 | O | CYS | A | 474 | 35.094 | −22.698 | 20.680 | 1.00 | 27.66 | A | O |
| ATOM | 7324 | N | TYR | A | 475 | 37.221 | −23.106 | 20.076 | 1.00 | 26.04 | A | N |
| ATOM | 7325 | CA | TYR | A | 475 | 37.015 | −24.547 | 20.082 | 1.00 | 25.17 | A | C |
| ATOM | 7327 | CB | TYR | A | 475 | 38.209 | −25.290 | 19.486 | 1.00 | 24.75 | A | C |
| ATOM | 7330 | CG | TYR | A | 475 | 37.853 | −26.656 | 18.929 | 1.00 | 28.24 | A | C |
| ATOM | 7331 | CD1 | TYR | A | 475 | 37.516 | −26.821 | 17.587 | 1.00 | 32.56 | A | C |
| ATOM | 7333 | CE1 | TYR | A | 475 | 37.192 | −28.071 | 17.081 | 1.00 | 36.43 | A | C |
| ATOM | 7335 | CZ | TYR | A | 475 | 37.199 | −29.178 | 17.923 | 1.00 | 34.35 | A | C |
| ATOM | 7336 | OH | TYR | A | 475 | 36.886 | −30.419 | 17.441 | 1.00 | 43.05 | A | O |
| ATOM | 7338 | CE2 | TYR | A | 475 | 37.533 | −29.045 | 19.246 | 1.00 | 34.85 | A | C |
| ATOM | 7340 | CD2 | TYR | A | 475 | 37.858 | −27.783 | 19.747 | 1.00 | 34.43 | A | C |
| ATOM | 7342 | C | TYR | A | 475 | 36.749 | −25.003 | 21.518 | 1.00 | 26.37 | A | C |
| ATOM | 7343 | O | TYR | A | 475 | 35.869 | −25.833 | 21.752 | 1.00 | 27.21 | A | O |
| ATOM | 7345 | N | MET | A | 476 | 37.481 | −24.438 | 22.479 | 1.00 | 26.99 | A | N |
| ATOM | 7346 | CA | MET | A | 476 | 37.252 | −24.759 | 23.901 | 1.00 | 26.98 | A | C |
| ATOM | 7348 | CB | MET | A | 476 | 38.202 | −23.971 | 24.789 | 1.00 | 26.60 | A | C |
| ATOM | 7351 | CG | MET | A | 476 | 39.652 | −24.384 | 24.656 | 1.00 | 30.73 | A | C |
| ATOM | 7354 | SD | MET | A | 476 | 40.740 | −23.174 | 25.392 | 1.00 | 36.77 | A | S |
| ATOM | 7355 | CE | MET | A | 476 | 39.937 | −22.903 | 26.995 | 1.00 | 30.88 | A | C |
| ATOM | 7359 | C | MET | A | 476 | 35.826 | −24.444 | 24.319 | 1.00 | 26.91 | A | C |
| ATOM | 7360 | O | MET | A | 476 | 35.137 | −25.270 | 24.911 | 1.00 | 28.08 | A | O |
| ATOM | 7362 | N | ARG | A | 477 | 35.386 | −23.237 | 24.009 | 1.00 | 28.18 | A | N |
| ATOM | 7363 | CA | ARG | A | 477 | 34.058 | −22.797 | 24.398 | 1.00 | 29.26 | A | C |
| ATOM | 7365 | CB | ARG | A | 477 | 33.880 | −21.314 | 24.079 | 1.00 | 28.98 | A | C |
| ATOM | 7368 | CG | ARG | A | 477 | 32.520 | −20.733 | 24.449 | 1.00 | 32.12 | A | C |
| ATOM | 7371 | CD | ARG | A | 477 | 32.537 | −19.223 | 24.275 | 1.00 | 40.29 | A | C |
| ATOM | 7374 | NE | ARG | A | 477 | 32.786 | −18.815 | 22.888 | 1.00 | 44.21 | A | N |
| ATOM | 7376 | CZ | ARG | A | 477 | 33.290 | −17.637 | 22.514 | 1.00 | 46.88 | A | C |
| ATOM | 7377 | NH1 | ARG | A | 477 | 33.619 | −16.721 | 23.420 | 1.00 | 48.90 | A | N |
| ATOM | 7380 | NH2 | ARG | A | 477 | 33.469 | −17.371 | 21.222 | 1.00 | 45.48 | A | N |
| ATOM | 7383 | C | ARG | A | 477 | 32.971 | −23.620 | 23.702 | 1.00 | 29.87 | A | C |
| ATOM | 7384 | O | ARG | A | 477 | 32.006 | −24.035 | 24.352 | 1.00 | 31.04 | A | O |
| ATOM | 7386 | N | THR | A | 478 | 33.110 | −23.852 | 22.397 | 1.00 | 28.61 | A | N |
| ATOM | 7387 | CA | THR | A | 478 | 32.044 | −24.539 | 21.657 | 1.00 | 28.83 | A | C |
| ATOM | 7389 | CB | THR | A | 478 | 32.216 | −24.430 | 20.131 | 1.00 | 28.55 | A | C |
| ATOM | 7391 | OG1 | THR | A | 478 | 32.238 | −23.056 | 19.746 | 1.00 | 26.42 | A | O |
| ATOM | 7393 | CG2 | THR | A | 478 | 31.034 | −25.107 | 19.407 | 1.00 | 30.41 | A | C |
| ATOM | 7397 | C | THR | A | 478 | 31.911 | −26.014 | 22.075 | 1.00 | 28.98 | A | C |
| ATOM | 7398 | O | THR | A | 478 | 30.822 | −26.467 | 22.400 | 1.00 | 28.85 | A | O |
| ATOM | 7400 | N | LYS | A | 479 | 33.013 | −26.758 | 22.074 | 1.00 | 29.87 | A | N |
| ATOM | 7401 | CA | LYS | A | 479 | 32.969 | −28.157 | 22.516 | 1.00 | 30.10 | A | C |
| ATOM | 7403 | CB | LYS | A | 479 | 34.143 | −28.960 | 21.938 | 1.00 | 30.29 | A | C |
| ATOM | 7406 | CG | LYS | A | 479 | 34.249 | −28.964 | 20.406 | 1.00 | 33.64 | A | C |
| ATOM | 7409 | CD | LYS | A | 479 | 33.118 | −29.688 | 19.695 | 1.00 | 42.31 | A | C |
| ATOM | 7412 | CE | LYS | A | 479 | 33.306 | −29.581 | 18.174 | 1.00 | 47.79 | A | C |
| ATOM | 7415 | NZ | LYS | A | 479 | 32.463 | −30.535 | 17.381 | 1.00 | 47.97 | A | N |
| ATOM | 7419 | C | LYS | A | 479 | 32.936 | −28.290 | 24.057 | 1.00 | 30.88 | A | C |
| ATOM | 7420 | O | LYS | A | 479 | 32.660 | −29.360 | 24.576 | 1.00 | 30.47 | A | O |
| ATOM | 7422 | N | GLY | A | 480 | 33.223 | −27.207 | 24.781 | 1.00 | 31.72 | A | N |
| ATOM | 7423 | CA | GLY | A | 480 | 33.206 | −27.231 | 26.248 | 1.00 | 31.97 | A | C |

TABLE 4-2-continued

Coordinates of *P. alba* IspS

| | | | | | | | | | | | | |
|---|---|---|---|---|---|---|---|---|---|---|---|---|
| ATOM | 7426 | C | GLY | A | 480 | 34.311 | −28.088 | 26.843 | 1.00 | 31.96 | A | C |
| ATOM | 7427 | O | GLY | A | 480 | 34.044 | −28.932 | 27.722 | 1.00 | 31.49 | A | O |
| ATOM | 7429 | N | ILE | A | 481 | 35.544 | −27.847 | 26.382 | 1.00 | 29.64 | A | N |
| ATOM | 7430 | CA | ILE | A | 481 | 36.702 | −28.660 | 26.747 | 1.00 | 29.31 | A | C |
| ATOM | 7432 | CB | ILE | A | 481 | 37.044 | −29.668 | 25.621 | 1.00 | 29.72 | A | C |
| ATOM | 7434 | CG1 | ILE | A | 481 | 37.398 | −28.940 | 24.302 | 1.00 | 30.04 | A | C |
| ATOM | 7437 | CD1 | ILE | A | 481 | 37.581 | −29.865 | 23.094 | 1.00 | 25.37 | A | C |
| ATOM | 7441 | CG2 | ILE | A | 481 | 35.865 | −30.602 | 25.391 | 1.00 | 29.26 | A | C |
| ATOM | 7445 | C | ILE | A | 481 | 37.926 | −27.807 | 27.052 | 1.00 | 31.21 | A | C |
| ATOM | 7446 | O | ILE | A | 481 | 37.964 | −26.613 | 26.746 | 1.00 | 32.82 | A | O |
| ATOM | 7448 | N | SER | A | 482 | 38.939 | −28.439 | 27.634 | 1.00 | 32.10 | A | N |
| ATOM | 7449 | CA | SER | A | 482 | 40.162 | −27.756 | 28.052 | 1.00 | 31.77 | A | C |
| ATOM | 7451 | CB | SER | A | 482 | 41.010 | −28.718 | 28.874 | 1.00 | 32.78 | A | C |
| ATOM | 7454 | OG | SER | A | 482 | 41.130 | −29.963 | 28.191 | 1.00 | 34.52 | A | O |
| ATOM | 7456 | C | SER | A | 482 | 41.000 | −27.281 | 26.883 | 1.00 | 32.56 | A | C |
| ATOM | 7457 | O | SER | A | 482 | 40.839 | −27.765 | 25.763 | 1.00 | 35.17 | A | O |
| ATOM | 7459 | N | GLU | A | 483 | 41.931 | −26.369 | 27.161 | 1.00 | 32.02 | A | N |
| ATOM | 7460 | CA | GLU | A | 483 | 42.928 | −25.941 | 26.186 | 1.00 | 33.48 | A | C |
| ATOM | 7462 | CB | GLU | A | 483 | 43.916 | −24.948 | 26.815 | 1.00 | 33.20 | A | C |
| ATOM | 7465 | CG | GLU | A | 483 | 45.047 | −24.524 | 25.877 | 1.00 | 33.67 | A | C |
| ATOM | 7468 | CD | GLU | A | 483 | 45.858 | −23.351 | 26.389 | 1.00 | 40.22 | A | C |
| ATOM | 7469 | OE1 | GLU | A | 483 | 45.594 | −22.861 | 27.519 | 1.00 | 43.03 | A | O |
| ATOM | 7470 | OE2 | GLU | A | 483 | 46.774 | −22.916 | 25.657 | 1.00 | 38.81 | A | O |
| ATOM | 7471 | C | GLU | A | 483 | 43.714 | −27.102 | 25.558 | 1.00 | 35.98 | A | C |
| ATOM | 7472 | O | GLU | A | 483 | 43.954 | −27.120 | 24.335 | 1.00 | 37.13 | A | O |
| ATOM | 7474 | N | GLU | A | 484 | 44.134 | −28.045 | 26.393 | 1.00 | 36.43 | A | N |
| ATOM | 7475 | CA | GLU | A | 484 | 44.980 | −29.149 | 25.948 | 1.00 | 37.19 | A | C |
| ATOM | 7477 | CB | GLU | A | 484 | 45.523 | −29.932 | 27.153 | 1.00 | 39.57 | A | C |
| ATOM | 7480 | CG | GLU | A | 484 | 46.686 | −30.866 | 26.813 | 1.00 | 49.47 | A | C |
| ATOM | 7483 | CD | GLU | A | 484 | 47.292 | −31.543 | 28.041 | 1.00 | 62.43 | A | C |
| ATOM | 7484 | OE1 | GLU | A | 484 | 47.606 | −30.824 | 29.026 | 1.00 | 66.87 | A | O |
| ATOM | 7485 | OE2 | GLU | A | 484 | 47.459 | −32.791 | 28.014 | 1.00 | 63.06 | A | O |
| ATOM | 7486 | C | GLU | A | 484 | 44.226 | −30.084 | 25.005 | 1.00 | 35.28 | A | C |
| ATOM | 7487 | O | GLU | A | 484 | 44.768 | −30.493 | 23.976 | 1.00 | 33.82 | A | O |
| ATOM | 7489 | N | LEU | A | 485 | 42.989 | −30.433 | 25.351 | 1.00 | 33.95 | A | N |
| ATOM | 7490 | CA | LEU | A | 485 | 42.175 | −31.227 | 24.425 | 1.00 | 33.76 | A | C |
| ATOM | 7492 | CB | LEU | A | 485 | 40.886 | −31.745 | 25.069 | 1.00 | 34.55 | A | C |
| ATOM | 7495 | CG | LEU | A | 485 | 40.968 | −33.207 | 25.551 | 1.00 | 39.74 | A | C |
| ATOM | 7497 | CD1 | LEU | A | 485 | 42.126 | −33.394 | 26.541 | 1.00 | 40.89 | A | C |
| ATOM | 7501 | CD2 | LEU | A | 485 | 39.647 | −33.669 | 26.180 | 1.00 | 42.87 | A | C |
| ATOM | 7505 | C | LEU | A | 485 | 41.870 | −30.436 | 23.155 | 1.00 | 32.05 | A | C |
| ATOM | 7506 | O | LEU | A | 485 | 41.963 | −30.972 | 22.062 | 1.00 | 30.76 | A | O |
| ATOM | 7508 | N | ALA | A | 486 | 41.522 | −29.164 | 23.308 | 1.00 | 30.65 | A | N |
| ATOM | 7509 | CA | ALA | A | 486 | 41.225 | −28.305 | 22.164 | 1.00 | 29.72 | A | C |
| ATOM | 7511 | CB | ALA | A | 486 | 40.771 | −26.933 | 22.648 | 1.00 | 28.94 | A | C |
| ATOM | 7515 | C | ALA | A | 486 | 42.435 | −28.176 | 21.228 | 1.00 | 30.16 | A | C |
| ATOM | 7516 | O | ALA | A | 486 | 42.310 | −28.256 | 19.998 | 1.00 | 32.78 | A | O |
| ATOM | 7518 | N | THR | A | 487 | 43.607 | −27.990 | 21.816 | 1.00 | 29.51 | A | N |
| ATOM | 7519 | CA | THR | A | 487 | 44.836 | −27.889 | 21.068 | 1.00 | 29.35 | A | C |
| ATOM | 7521 | CB | THR | A | 487 | 46.016 | −27.585 | 22.018 | 1.00 | 31.65 | A | C |
| ATOM | 7523 | OG1 | THR | A | 487 | 45.866 | −26.262 | 22.551 | 1.00 | 34.58 | A | O |
| ATOM | 7525 | CG2 | THR | A | 487 | 47.356 | −27.676 | 21.303 | 1.00 | 29.45 | A | C |
| ATOM | 7529 | C | THR | A | 487 | 45.083 | −29.179 | 20.293 | 1.00 | 30.58 | A | C |
| ATOM | 7530 | O | THR | A | 487 | 45.510 | −29.148 | 19.136 | 1.00 | 30.56 | A | O |
| ATOM | 7532 | N | GLU | A | 488 | 44.778 | −30.311 | 20.912 | 1.00 | 30.73 | A | N |
| ATOM | 7533 | CA | GLU | A | 488 | 44.909 | −31.596 | 20.251 | 1.00 | 31.69 | A | C |
| ATOM | 7535 | CB | GLU | A | 488 | 44.559 | −32.726 | 21.226 | 1.00 | 34.61 | A | C |
| ATOM | 7538 | CG | GLU | A | 488 | 44.929 | −34.158 | 20.782 | 1.00 | 42.91 | A | C |
| ATOM | 7541 | CD | GLU | A | 488 | 44.468 | −35.230 | 21.805 | 1.00 | 51.83 | A | C |
| ATOM | 7542 | OE1 | GLU | A | 488 | 45.312 | −36.038 | 22.257 | 1.00 | 53.97 | A | O |
| ATOM | 7543 | OE2 | GLU | A | 488 | 43.263 | −35.252 | 22.169 | 1.00 | 57.42 | A | O |
| ATOM | 7544 | C | GLU | A | 488 | 43.990 | −31.653 | 19.039 | 1.00 | 30.86 | A | C |
| ATOM | 7545 | O | GLU | A | 488 | 44.406 | −32.077 | 17.959 | 1.00 | 30.25 | A | O |
| ATOM | 7547 | N | SER | A | 489 | 42.742 | −31.226 | 19.216 | 1.00 | 28.77 | A | N |
| ATOM | 7548 | CA | SER | A | 489 | 41.759 | −31.338 | 18.153 | 1.00 | 29.03 | A | C |
| ATOM | 7550 | CB | SER | A | 489 | 40.361 | −31.004 | 18.646 | 1.00 | 28.33 | A | C |
| ATOM | 7553 | OG | SER | A | 489 | 40.002 | −31.853 | 19.725 | 1.00 | 37.93 | A | O |
| ATOM | 7555 | C | SER | A | 489 | 42.124 | −30.416 | 17.000 | 1.00 | 28.35 | A | C |
| ATOM | 7556 | O | SER | A | 489 | 41.905 | −30.761 | 15.842 | 1.00 | 29.09 | A | O |
| ATOM | 7558 | N | VAL | A | 490 | 42.683 | −29.257 | 17.327 | 1.00 | 27.58 | A | N |
| ATOM | 7559 | CA | VAL | A | 490 | 43.156 | −28.332 | 16.308 | 1.00 | 27.37 | A | C |
| ATOM | 7561 | CB | VAL | A | 490 | 43.492 | −26.971 | 16.899 | 1.00 | 27.54 | A | C |
| ATOM | 7563 | CG1 | VAL | A | 490 | 44.224 | −26.084 | 15.887 | 1.00 | 23.38 | A | C |
| ATOM | 7567 | CG2 | VAL | A | 490 | 42.186 | −26.322 | 17.351 | 1.00 | 26.23 | A | C |
| ATOM | 7571 | C | VAL | A | 490 | 44.308 | −28.940 | 15.538 | 1.00 | 27.62 | A | C |
| ATOM | 7572 | O | VAL | A | 490 | 44.316 | −28.869 | 14.319 | 1.00 | 28.81 | A | O |
| ATOM | 7574 | N | MET | A | 491 | 45.242 | −29.589 | 16.225 | 1.00 | 29.11 | A | N |
| ATOM | 7575 | CA | MET | A | 491 | 46.328 | −30.317 | 15.530 | 1.00 | 28.74 | A | C |

TABLE 4-2-continued

| Coordinates of *P. alba* IspS | | | | | | | | | | | |
|---|---|---|---|---|---|---|---|---|---|---|---|
| ATOM | 7577 | CB | MET | A | 491 | 47.254 | −31.019 | 16.529 | 1.00 | 32.05 | A | C |
| ATOM | 7580 | CG | MET | A | 491 | 48.053 | −30.105 | 17.437 | 1.00 | 34.71 | A | C |
| ATOM | 7583 | SD | MET | A | 491 | 49.345 | −29.289 | 16.533 | 1.00 | 54.88 | A | S |
| ATOM | 7584 | CE | MET | A | 491 | 50.240 | −28.583 | 17.932 | 1.00 | 61.26 | A | C |
| ATOM | 7588 | C | MET | A | 491 | 45.764 | −31.376 | 14.592 | 1.00 | 27.27 | A | C |
| ATOM | 7589 | O | MET | A | 491 | 46.251 | −31.544 | 13.480 | 1.00 | 29.18 | A | O |
| ATOM | 7591 | N | ASN | A | 492 | 44.742 | −32.102 | 15.042 | 1.00 | 24.90 | A | N |
| ATOM | 7592 | CA | ASN | A | 492 | 44.112 | −33.108 | 14.194 | 1.00 | 24.42 | A | C |
| ATOM | 7594 | CB | ASN | A | 492 | 43.117 | −33.973 | 14.976 | 1.00 | 27.09 | A | C |
| ATOM | 7597 | CG | ASN | A | 492 | 43.790 | −34.834 | 16.076 | 1.00 | 32.10 | A | C |
| ATOM | 7598 | OD1 | ASN | A | 492 | 45.011 | −35.022 | 16.111 | 1.00 | 36.38 | A | O |
| ATOM | 7599 | ND2 | ASN | A | 492 | 42.971 | −35.342 | 16.983 | 1.00 | 29.67 | A | N |
| ATOM | 7602 | C | ASN | A | 492 | 43.416 | −32.509 | 12.971 | 1.00 | 21.31 | A | C |
| ATOM | 7603 | O | ASN | A | 492 | 43.365 | −33.141 | 11.924 | 1.00 | 19.60 | A | O |
| ATOM | 7605 | N | LEU | A | 493 | 42.864 | −31.312 | 13.119 | 1.00 | 19.85 | A | N |
| ATOM | 7606 | CA | LEU | A | 493 | 42.208 | −30.609 | 12.026 | 1.00 | 21.49 | A | C |
| ATOM | 7608 | CB | LEU | A | 493 | 41.438 | −29.402 | 12.570 | 1.00 | 22.55 | A | C |
| ATOM | 7611 | CG | LEU | A | 493 | 40.562 | −28.537 | 11.637 | 1.00 | 30.39 | A | C |
| ATOM | 7613 | CD1 | LEU | A | 493 | 39.640 | −29.355 | 10.718 | 1.00 | 30.23 | A | C |
| ATOM | 7617 | CD2 | LEU | A | 493 | 39.693 | −27.559 | 12.479 | 1.00 | 23.06 | A | C |
| ATOM | 7621 | C | LEU | A | 493 | 43.253 | −30.196 | 10.988 | 1.00 | 20.61 | A | C |
| ATOM | 7622 | O | LEU | A | 493 | 43.024 | −30.298 | 9.781 | 1.00 | 21.55 | A | O |
| ATOM | 7624 | N | ILE | A | 494 | 44.427 | −29.800 | 11.463 | 1.00 | 19.95 | A | N |
| ATOM | 7625 | CA | ILE | A | 494 | 45.529 | −29.519 | 10.574 | 1.00 | 21.52 | A | C |
| ATOM | 7627 | CB | ILE | A | 494 | 46.739 | −28.978 | 11.329 | 1.00 | 20.44 | A | C |
| ATOM | 7629 | CG1 | ILE | A | 494 | 46.492 | −27.511 | 11.724 | 1.00 | 22.83 | A | C |
| ATOM | 7632 | CD1 | ILE | A | 494 | 47.454 | −27.023 | 12.815 | 1.00 | 19.27 | A | C |
| ATOM | 7636 | CG2 | ILE | A | 494 | 47.989 | −29.041 | 10.489 | 1.00 | 18.64 | A | C |
| ATOM | 7640 | C | ILE | A | 494 | 45.898 | −30.764 | 9.762 | 1.00 | 22.01 | A | C |
| ATOM | 7641 | O | ILE | A | 494 | 46.021 | −30.688 | 8.539 | 1.00 | 25.12 | A | O |
| ATOM | 7643 | N | ASP | A | 495 | 46.087 | −31.885 | 10.437 | 1.00 | 20.80 | A | N |
| ATOM | 7644 | CA | ASP | A | 495 | 46.397 | −33.138 | 9.773 | 1.00 | 21.60 | A | C |
| ATOM | 7646 | CB | ASP | A | 495 | 46.473 | −34.281 | 10.791 | 1.00 | 22.75 | A | C |
| ATOM | 7649 | CG | ASP | A | 495 | 47.682 | −34.161 | 11.731 | 1.00 | 24.78 | A | C |
| ATOM | 7650 | OD1 | ASP | A | 495 | 48.662 | −33.458 | 11.379 | 1.00 | 31.93 | A | O |
| ATOM | 7651 | OD2 | ASP | A | 495 | 47.641 | −34.762 | 12.831 | 1.00 | 35.25 | A | O |
| ATOM | 7652 | C | ASP | A | 495 | 45.346 | −33.462 | 8.740 | 1.00 | 22.09 | A | C |
| ATOM | 7653 | O | ASP | A | 495 | 45.666 | −33.770 | 7.596 | 1.00 | 22.13 | A | O |
| ATOM | 7655 | N | GLU | A | 496 | 44.087 | −33.342 | 9.134 | 1.00 | 23.17 | A | N |
| ATOM | 7656 | CA | GLU | A | 496 | 42.972 | −33.693 | 8.258 | 1.00 | 25.14 | A | C |
| ATOM | 7658 | CB | GLU | A | 496 | 41.643 | −33.501 | 8.984 | 1.00 | 26.79 | A | C |
| ATOM | 7661 | CG | GLU | A | 496 | 40.397 | −33.761 | 8.177 | 1.00 | 35.71 | A | C |
| ATOM | 7664 | CD | GLU | A | 496 | 39.117 | −33.280 | 8.886 | 1.00 | 44.71 | A | C |
| ATOM | 7665 | OE1 | GLU | A | 496 | 38.810 | −33.788 | 9.987 | 1.00 | 47.95 | A | O |
| ATOM | 7666 | OE2 | GLU | A | 496 | 38.416 | −32.402 | 8.328 | 1.00 | 50.58 | A | O |
| ATOM | 7667 | C | GLU | A | 496 | 43.032 | −32.834 | 7.024 | 1.00 | 24.17 | A | C |
| ATOM | 7668 | O | GLU | A | 496 | 42.890 | −33.344 | 5.909 | 1.00 | 23.57 | A | O |
| ATOM | 7670 | N | THR | A | 497 | 43.271 | −31.535 | 7.232 | 1.00 | 23.07 | A | N |
| ATOM | 7671 | CA | THR | A | 497 | 43.327 | −30.575 | 6.143 | 1.00 | 21.41 | A | C |
| ATOM | 7673 | CB | THR | A | 497 | 43.465 | −29.157 | 6.674 | 1.00 | 22.58 | A | C |
| ATOM | 7675 | OG1 | THR | A | 497 | 42.381 | −28.887 | 7.575 | 1.00 | 25.05 | A | O |
| ATOM | 7677 | CG2 | THR | A | 497 | 43.436 | −28.162 | 5.551 | 1.00 | 17.59 | A | C |
| ATOM | 7681 | C | THR | A | 497 | 44.481 | −30.901 | 5.175 | 1.00 | 22.39 | A | C |
| ATOM | 7682 | O | THR | A | 497 | 44.304 | −30.840 | 3.961 | 1.00 | 20.87 | A | O |
| ATOM | 7684 | N | TRP | A | 498 | 45.641 | −31.275 | 5.718 | 1.00 | 20.20 | A | N |
| ATOM | 7685 | CA | TRP | A | 498 | 46.743 | −31.748 | 4.888 | 1.00 | 21.37 | A | C |
| ATOM | 7687 | CB | TRP | A | 498 | 47.973 | −32.065 | 5.760 | 1.00 | 18.97 | A | C |
| ATOM | 7690 | CG | TRP | A | 498 | 48.874 | −30.887 | 5.894 | 1.00 | 21.52 | A | C |
| ATOM | 7691 | CD1 | TRP | A | 498 | 48.969 | −30.038 | 6.953 | 1.00 | 13.13 | A | C |
| ATOM | 7693 | NE1 | TRP | A | 498 | 49.885 | −29.084 | 6.704 | 1.00 | 21.91 | A | N |
| ATOM | 7695 | CE2 | TRP | A | 498 | 50.399 | −29.277 | 5.454 | 1.00 | 19.92 | A | C |
| ATOM | 7696 | CD2 | TRP | A | 498 | 49.780 | −30.409 | 4.920 | 1.00 | 17.93 | A | C |
| ATOM | 7697 | CE3 | TRP | A | 498 | 50.135 | −30.832 | 3.646 | 1.00 | 23.82 | A | C |
| ATOM | 7699 | CZ3 | TRP | A | 498 | 51.097 | −30.125 | 2.961 | 1.00 | 24.54 | A | C |
| ATOM | 7701 | CH2 | TRP | A | 498 | 51.705 | −29.007 | 3.526 | 1.00 | 25.21 | A | C |
| ATOM | 7703 | CZ2 | TRP | A | 498 | 51.375 | −28.572 | 4.775 | 1.00 | 24.04 | A | C |
| ATOM | 7705 | C | TRP | A | 498 | 46.387 | −32.963 | 4.013 | 1.00 | 19.42 | A | C |
| ATOM | 7706 | O | TRP | A | 498 | 46.715 | −33.008 | 2.836 | 1.00 | 20.26 | A | O |
| ATOM | 7708 | N | LYS | A | 499 | 45.727 | −33.944 | 4.588 | 1.00 | 19.66 | A | N |
| ATOM | 7709 | CA | LYS | A | 499 | 45.320 | −35.113 | 3.824 | 1.00 | 21.18 | A | C |
| ATOM | 7711 | CB | LYS | A | 499 | 44.554 | −36.105 | 4.701 | 1.00 | 20.73 | A | C |
| ATOM | 7714 | CG | LYS | A | 499 | 45.406 | −36.825 | 5.766 | 1.00 | 20.29 | A | C |
| ATOM | 7717 | CD | LYS | A | 499 | 44.547 | −37.888 | 6.525 | 1.00 | 21.48 | A | C |
| ATOM | 7720 | CE | LYS | A | 499 | 45.126 | −38.323 | 7.841 | 1.00 | 21.99 | A | C |
| ATOM | 7723 | NZ | LYS | A | 499 | 44.166 | −39.231 | 8.565 | 1.00 | 24.95 | A | N |
| ATOM | 7727 | C | LYS | A | 499 | 44.451 | −34.701 | 2.655 | 1.00 | 20.41 | A | C |
| ATOM | 7728 | O | LYS | A | 499 | 44.532 | −35.278 | 1.598 | 1.00 | 23.27 | A | O |
| ATOM | 7730 | N | LYS | A | 500 | 43.628 | −33.688 | 2.842 | 1.00 | 20.82 | A | N |

TABLE 4-2-continued

| Coordinates of *P. alba* IspS | | | | | | | | | | | | |
|---|---|---|---|---|---|---|---|---|---|---|---|---|
| ATOM | 7731 | CA | LYS | A | 500 | 42.761 | −33.233 | 1.779 | 1.00 | 23.10 | A | C |
| ATOM | 7733 | CB | LYS | A | 500 | 41.613 | −32.392 | 2.351 | 1.00 | 24.87 | A | C |
| ATOM | 7736 | CG | LYS | A | 500 | 40.575 | −33.199 | 3.110 | 1.00 | 24.42 | A | C |
| ATOM | 7739 | CD | LYS | A | 500 | 39.505 | −32.282 | 3.741 | 1.00 | 34.06 | A | C |
| ATOM | 7742 | CE | LYS | A | 500 | 38.487 | −33.073 | 4.598 | 1.00 | 33.59 | A | C |
| ATOM | 7745 | NZ | LYS | A | 500 | 37.318 | −32.261 | 5.058 | 1.00 | 39.36 | A | N |
| ATOM | 7749 | C | LYS | A | 500 | 43.529 | −32.461 | 0.703 | 1.00 | 22.13 | A | C |
| ATOM | 7750 | O | LYS | A | 500 | 43.233 | −32.586 | −0.469 | 1.00 | 23.08 | A | O |
| ATOM | 7752 | N | MET | A | 501 | 44.516 | −31.665 | 1.088 | 1.00 | 22.16 | A | N |
| ATOM | 7753 | CA | MET | A | 501 | 45.324 | −30.960 | 0.101 | 1.00 | 19.81 | A | C |
| ATOM | 7755 | CB | MET | A | 501 | 46.228 | −29.944 | 0.770 | 1.00 | 19.32 | A | C |
| ATOM | 7758 | CG | MET | A | 501 | 45.516 | −28.822 | 1.490 | 1.00 | 21.43 | A | C |
| ATOM | 7761 | SD | MET | A | 501 | 46.681 | −27.490 | 1.974 | 1.00 | 27.05 | A | S |
| ATOM | 7762 | CE | MET | A | 501 | 47.856 | −28.310 | 3.053 | 1.00 | 23.38 | A | C |
| ATOM | 7766 | C | MET | A | 501 | 46.176 | −31.946 | −0.698 | 1.00 | 18.61 | A | C |
| ATOM | 7767 | O | MET | A | 501 | 46.410 | −31.758 | −1.888 | 1.00 | 18.54 | A | O |
| ATOM | 7769 | N | ASN | A | 502 | 46.658 | −32.991 | −0.037 | 1.00 | 19.21 | A | N |
| ATOM | 7770 | CA | ASN | A | 502 | 47.440 | −34.013 | −0.717 | 1.00 | 18.62 | A | C |
| ATOM | 7772 | CB | ASN | A | 502 | 47.922 | −35.069 | 0.277 | 1.00 | 18.18 | A | C |
| ATOM | 7775 | CG | ASN | A | 502 | 48.980 | −34.544 | 1.216 | 1.00 | 20.41 | A | C |
| ATOM | 7776 | OD1 | ASN | A | 502 | 49.635 | −33.522 | 0.933 | 1.00 | 20.85 | A | O |
| ATOM | 7777 | ND2 | ASN | A | 502 | 49.167 | −35.244 | 2.353 | 1.00 | 14.88 | A | N |
| ATOM | 7780 | C | ASN | A | 502 | 46.629 | −34.674 | −1.815 | 1.00 | 20.92 | A | C |
| ATOM | 7781 | O | ASN | A | 502 | 47.140 | −34.963 | −2.889 | 1.00 | 21.10 | A | O |
| ATOM | 7783 | N | LYS | A | 503 | 45.361 | −34.902 | −1.548 | 1.00 | 21.59 | A | N |
| ATOM | 7784 | CA | LYS | A | 503 | 44.492 | −35.487 | −2.543 | 1.00 | 26.84 | A | C |
| ATOM | 7786 | CB | LYS | A | 503 | 43.158 | −35.894 | −1.907 | 1.00 | 25.07 | A | C |
| ATOM | 7789 | CG | LYS | A | 503 | 42.272 | −36.688 | −2.832 | 1.00 | 31.50 | A | C |
| ATOM | 7792 | CD | LYS | A | 503 | 41.048 | −37.279 | −2.122 | 1.00 | 37.63 | A | C |
| ATOM | 7795 | CE | LYS | A | 503 | 40.180 | −38.027 | −3.135 | 1.00 | 42.50 | A | C |
| ATOM | 7798 | NZ | LYS | A | 503 | 38.799 | −38.319 | −2.637 | 1.00 | 39.80 | A | N |
| ATOM | 7802 | C | LYS | A | 503 | 44.265 | −34.554 | −3.751 | 1.00 | 26.24 | A | C |
| ATOM | 7803 | O | LYS | A | 503 | 44.388 | −34.969 | −4.896 | 1.00 | 24.15 | A | O |
| ATOM | 7805 | N | GLU | A | 504 | 43.937 | −33.301 | −3.477 | 1.00 | 28.57 | A | N |
| ATOM | 7806 | CA | GLU | A | 504 | 43.681 | −32.298 | −4.520 | 1.00 | 28.52 | A | C |
| ATOM | 7808 | CB | GLU | A | 504 | 43.343 | −30.946 | −3.865 | 1.00 | 30.61 | A | C |
| ATOM | 7811 | CG | GLU | A | 504 | 42.958 | −29.790 | −4.821 | 1.00 | 38.94 | A | C |
| ATOM | 7814 | CD | GLU | A | 504 | 41.566 | −29.921 | −5.427 | 1.00 | 46.58 | A | C |
| ATOM | 7815 | OE1 | GLU | A | 504 | 41.310 | −29.262 | −6.453 | 1.00 | 52.18 | A | O |
| ATOM | 7816 | OE2 | GLU | A | 504 | 40.723 | −30.683 | −4.896 | 1.00 | 53.41 | A | O |
| ATOM | 7817 | C | GLU | A | 504 | 44.920 | −32.185 | −5.412 | 1.00 | 27.76 | A | C |
| ATOM | 7818 | O | GLU | A | 504 | 44.814 | −32.059 | −6.628 | 1.00 | 26.82 | A | O |
| ATOM | 7820 | N | LYS | A | 505 | 46.101 | −32.268 | −4.805 | 1.00 | 25.80 | A | N |
| ATOM | 7821 | CA | LYS | A | 505 | 47.338 | −32.166 | −5.559 | 1.00 | 26.51 | A | C |
| ATOM | 7823 | CB | LYS | A | 505 | 48.533 | −32.046 | −4.617 | 1.00 | 23.37 | A | C |
| ATOM | 7826 | CG | LYS | A | 505 | 49.916 | −32.048 | −5.295 | 1.00 | 23.18 | A | C |
| ATOM | 7829 | CD | LYS | A | 505 | 50.165 | −30.869 | −6.209 | 1.00 | 27.18 | A | C |
| ATOM | 7832 | CE | LYS | A | 505 | 51.471 | −31.033 | −7.011 | 1.00 | 21.66 | A | C |
| ATOM | 7835 | NZ | LYS | A | 505 | 52.684 | −30.936 | −6.205 | 1.00 | 31.62 | A | N |
| ATOM | 7839 | C | LYS | A | 505 | 47.531 | −33.360 | −6.491 | 1.00 | 28.51 | A | C |
| ATOM | 7840 | O | LYS | A | 505 | 48.058 | −33.230 | −7.598 | 1.00 | 28.28 | A | O |
| ATOM | 7842 | N | LEU | A | 506 | 47.137 | −34.520 | −6.011 | 1.00 | 31.86 | A | N |
| ATOM | 7843 | CA | LEU | A | 506 | 47.448 | −35.765 | −6.663 | 1.00 | 36.04 | A | C |
| ATOM | 7845 | CB | LEU | A | 506 | 47.288 | −36.918 | −5.682 | 1.00 | 37.63 | A | C |
| ATOM | 7848 | CG | LEU | A | 506 | 48.038 | −38.207 | −5.980 | 1.00 | 42.29 | A | C |
| ATOM | 7850 | CD1 | LEU | A | 506 | 49.507 | −37.926 | −6.154 | 1.00 | 35.85 | A | C |
| ATOM | 7854 | CD2 | LEU | A | 506 | 47.800 | −39.204 | −4.820 | 1.00 | 46.05 | A | C |
| ATOM | 7858 | C | LEU | A | 506 | 46.558 | −35.972 | −7.872 | 1.00 | 37.67 | A | C |
| ATOM | 7859 | O | LEU | A | 506 | 47.003 | −36.495 | −8.875 | 1.00 | 38.71 | A | O |
| ATOM | 7861 | N | GLY | A | 507 | 45.309 | −35.552 | −7.797 | 1.00 | 39.52 | A | N |
| ATOM | 7862 | CA | GLY | A | 507 | 44.443 | −35.753 | −8.922 | 1.00 | 43.92 | A | C |
| ATOM | 7865 | C | GLY | A | 507 | 43.260 | −34.842 | −8.940 | 1.00 | 46.84 | A | C |
| ATOM | 7866 | O | GLY | A | 507 | 42.912 | −34.221 | −7.932 | 1.00 | 49.96 | A | O |
| ATOM | 7868 | N | GLY | A | 508 | 42.676 | −34.743 | −10.122 | 1.00 | 49.06 | A | N |
| ATOM | 7869 | CA | GLY | A | 508 | 41.363 | −34.150 | −10.302 | 1.00 | 50.99 | A | C |
| ATOM | 7872 | C | GLY | A | 508 | 41.194 | −32.736 | −9.777 | 1.00 | 50.71 | A | C |
| ATOM | 7873 | O | GLY | A | 508 | 40.122 | −32.409 | −9.241 | 1.00 | 52.36 | A | O |
| ATOM | 7875 | N | SER | A | 509 | 42.203 | −31.880 | −9.918 | 1.00 | 47.13 | A | N |
| ATOM | 7876 | CA | SER | A | 509 | 41.952 | −30.484 | −9.528 | 1.00 | 47.06 | A | C |
| ATOM | 7878 | CB | SER | A | 509 | 43.191 | −29.736 | −8.981 | 1.00 | 45.68 | A | C |
| ATOM | 7881 | OG | SER | A | 509 | 42.806 | −28.477 | −8.381 | 1.00 | 42.36 | A | O |
| ATOM | 7883 | C | SER | A | 509 | 41.382 | −29.749 | −10.715 | 1.00 | 44.82 | A | C |
| ATOM | 7884 | O | SER | A | 509 | 41.689 | −30.070 | −11.852 | 1.00 | 42.86 | A | O |
| ATOM | 7886 | N | LEU | A | 510 | 40.554 | −28.756 | −10.416 | 1.00 | 45.06 | A | N |
| ATOM | 7887 | CA | LEU | A | 510 | 40.113 | −27.777 | −11.399 | 1.00 | 45.40 | A | C |
| ATOM | 7889 | CB | LEU | A | 510 | 38.958 | −26.930 | −10.832 | 1.00 | 47.41 | A | C |
| ATOM | 7892 | CG | LEU | A | 510 | 37.786 | −27.690 | −10.165 | 1.00 | 55.26 | A | C |
| ATOM | 7894 | CD1 | LEU | A | 510 | 36.624 | −26.741 | −9.788 | 1.00 | 57.58 | A | C |

TABLE 4-2-continued

| Coordinates of *P. alba* IspS | | | | | | | | | | | |
|---|---|---|---|---|---|---|---|---|---|---|---|
| ATOM | 7898 | CD2 | LEU | A | 510 | 37.270 | −28.882 | −11.042 | 1.00 | 61.12 | A | C |
| ATOM | 7902 | C | LEU | A | 510 | 41.286 | −26.872 | −11.801 | 1.00 | 42.51 | A | C |
| ATOM | 7903 | O | LEU | A | 510 | 41.294 | −26.326 | −12.901 | 1.00 | 44.42 | A | O |
| ATOM | 7905 | N | PHE | A | 511 | 42.267 | −26.730 | −10.908 | 1.00 | 37.23 | A | N |
| ATOM | 7906 | CA | PHE | A | 511 | 43.472 | −25.953 | −11.166 | 1.00 | 34.84 | A | C |
| ATOM | 7908 | CB | PHE | A | 511 | 43.886 | −25.210 | −9.902 | 1.00 | 34.34 | A | C |
| ATOM | 7911 | CG | PHE | A | 511 | 42.953 | −24.144 | −9.522 | 1.00 | 28.92 | A | C |
| ATOM | 7912 | CD1 | PHE | A | 511 | 43.120 | −22.857 | −10.008 | 1.00 | 29.05 | A | C |
| ATOM | 7914 | CE1 | PHE | A | 511 | 42.239 | −21.868 | −9.667 | 1.00 | 31.91 | A | C |
| ATOM | 7916 | CZ | PHE | A | 511 | 41.166 | −22.149 | −8.835 | 1.00 | 34.31 | A | C |
| ATOM | 7918 | CE2 | PHE | A | 511 | 40.987 | −23.436 | −8.353 | 1.00 | 31.94 | A | C |
| ATOM | 7920 | CD2 | PHE | A | 511 | 41.879 | −24.420 | −8.705 | 1.00 | 28.15 | A | C |
| ATOM | 7922 | C | PHE | A | 511 | 44.646 | −26.806 | −11.627 | 1.00 | 33.67 | A | C |
| ATOM | 7923 | O | PHE | A | 511 | 44.729 | −27.979 | −11.330 | 1.00 | 32.95 | A | O |
| ATOM | 7925 | N | ALA | A | 512 | 45.581 | −26.186 | −12.334 | 1.00 | 35.25 | A | N |
| ATOM | 7926 | CA | ALA | A | 512 | 46.800 | −26.873 | −12.750 | 1.00 | 35.70 | A | C |
| ATOM | 7928 | CB | ALA | A | 512 | 47.539 | −26.051 | −13.813 | 1.00 | 34.66 | A | C |
| ATOM | 7932 | C | ALA | A | 512 | 47.707 | −27.148 | −11.529 | 1.00 | 36.10 | A | C |
| ATOM | 7933 | O | ALA | A | 512 | 47.699 | −26.406 | −10.547 | 1.00 | 36.63 | A | O |
| ATOM | 7935 | N | LYS | A | 513 | 48.475 | −28.225 | −11.603 | 1.00 | 36.02 | A | N |
| ATOM | 7936 | CA | LYS | A | 513 | 49.284 | −28.673 | −10.484 | 1.00 | 37.34 | A | C |
| ATOM | 7938 | CB | LYS | A | 513 | 50.063 | −29.942 | −10.849 | 1.00 | 37.46 | A | C |
| ATOM | 7941 | CG | LYS | A | 513 | 49.162 | −31.182 | −10.883 | 1.00 | 43.80 | A | C |
| ATOM | 7944 | CD | LYS | A | 513 | 49.963 | −32.482 | −10.925 | 1.00 | 50.12 | A | C |
| ATOM | 7947 | CE | LYS | A | 513 | 49.023 | −33.696 | −10.922 | 1.00 | 56.16 | A | C |
| ATOM | 7950 | NZ | LYS | A | 513 | 49.717 | −34.969 | −10.585 | 1.00 | 55.05 | A | N |
| ATOM | 7954 | C | LYS | A | 513 | 50.214 | −27.622 | −9.884 | 1.00 | 35.55 | A | C |
| ATOM | 7955 | O | LYS | A | 513 | 50.337 | −27.571 | −8.679 | 1.00 | 34.97 | A | O |
| ATOM | 7957 | N | PRO | A | 514 | 50.850 | −26.775 | −10.715 | 1.00 | 33.86 | A | N |
| ATOM | 7958 | CA | PRO | A | 514 | 51.776 | −25.809 | −10.137 | 1.00 | 30.23 | A | C |
| ATOM | 7960 | CB | PRO | A | 514 | 52.402 | −25.116 | −11.359 | 1.00 | 30.51 | A | C |
| ATOM | 7963 | CG | PRO | A | 514 | 52.125 | −26.036 | −12.529 | 1.00 | 34.84 | A | C |
| ATOM | 7966 | CD | PRO | A | 514 | 50.855 | −26.753 | −12.197 | 1.00 | 35.73 | A | C |
| ATOM | 7969 | C | PRO | A | 514 | 51.082 | −24.796 | −9.233 | 1.00 | 27.77 | A | C |
| ATOM | 7970 | O | PRO | A | 514 | 51.627 | −24.406 | −8.205 | 1.00 | 30.05 | A | O |
| ATOM | 7971 | N | PHE | A | 515 | 49.886 | −24.373 | −9.587 | 1.00 | 25.77 | A | N |
| ATOM | 7972 | CA | PHE | A | 515 | 49.195 | −23.428 | −8.732 | 1.00 | 24.83 | A | C |
| ATOM | 7974 | CB | PHE | A | 515 | 48.074 | −22.699 | −9.462 | 1.00 | 23.92 | A | C |
| ATOM | 7977 | CG | PHE | A | 515 | 47.262 | −21.818 | −8.557 | 1.00 | 26.15 | A | C |
| ATOM | 7978 | CD1 | PHE | A | 515 | 47.779 | −20.626 | −8.087 | 1.00 | 25.26 | A | C |
| ATOM | 7980 | CE1 | PHE | A | 515 | 47.041 | −19.832 | −7.203 | 1.00 | 25.88 | A | C |
| ATOM | 7982 | CZ | PHE | A | 515 | 45.780 | −20.227 | −6.804 | 1.00 | 22.17 | A | C |
| ATOM | 7984 | CE2 | PHE | A | 515 | 45.266 | −21.432 | −7.253 | 1.00 | 23.27 | A | C |
| ATOM | 7986 | CD2 | PHE | A | 515 | 46.011 | −22.225 | −8.108 | 1.00 | 26.63 | A | C |
| ATOM | 7988 | C | PHE | A | 515 | 48.675 | −24.143 | −7.460 | 1.00 | 24.34 | A | C |
| ATOM | 7989 | O | PHE | A | 515 | 48.794 | −23.599 | −6.371 | 1.00 | 23.33 | A | O |
| ATOM | 7991 | N | VAL | A | 516 | 48.156 | −25.369 | −7.588 | 1.00 | 22.98 | A | N |
| ATOM | 7992 | CA | VAL | A | 516 | 47.815 | −26.159 | −6.401 | 1.00 | 22.66 | A | C |
| ATOM | 7994 | CB | VAL | A | 516 | 47.387 | −27.605 | −6.706 | 1.00 | 24.87 | A | C |
| ATOM | 7996 | CG1 | VAL | A | 516 | 46.149 | −27.671 | −7.666 | 1.00 | 22.01 | A | C |
| ATOM | 8000 | CG2 | VAL | A | 516 | 47.109 | −28.387 | −5.377 | 1.00 | 17.25 | A | C |
| ATOM | 8004 | C | VAL | A | 516 | 49.022 | −26.187 | −5.432 | 1.00 | 22.26 | A | C |
| ATOM | 8005 | O | VAL | A | 516 | 48.861 | −25.964 | −4.228 | 1.00 | 21.22 | A | O |
| ATOM | 8007 | N | GLU | A | 517 | 50.213 | −26.411 | −5.976 | 1.00 | 21.70 | A | N |
| ATOM | 8008 | CA | GLU | A | 517 | 51.456 | −26.510 | −5.188 | 1.00 | 22.29 | A | C |
| ATOM | 8010 | CB | GLU | A | 517 | 52.584 | −27.047 | −6.072 | 1.00 | 22.50 | A | C |
| ATOM | 8013 | CG | GLU | A | 517 | 53.939 | −27.283 | −5.376 | 1.00 | 19.35 | A | C |
| ATOM | 8016 | CD | GLU | A | 517 | 53.941 | −28.451 | −4.347 | 1.00 | 27.61 | A | C |
| ATOM | 8017 | OE1 | GLU | A | 517 | 52.962 | −29.218 | −4.228 | 1.00 | 23.47 | A | O |
| ATOM | 8018 | OE2 | GLU | A | 517 | 54.940 | −28.605 | −3.631 | 1.00 | 30.16 | A | O |
| ATOM | 8019 | C | GLU | A | 517 | 51.847 | −25.157 | −4.576 | 1.00 | 22.35 | A | C |
| ATOM | 8020 | O | GLU | A | 517 | 52.253 | −25.096 | −3.404 | 1.00 | 26.83 | A | O |
| ATOM | 8022 | N | THR | A | 518 | 51.709 | −24.082 | −5.354 | 1.00 | 21.58 | A | N |
| ATOM | 8023 | CA | THR | A | 518 | 51.902 | −22.731 | −4.836 | 1.00 | 24.40 | A | C |
| ATOM | 8025 | CB | THR | A | 518 | 51.689 | −21.634 | −5.925 | 1.00 | 26.67 | A | C |
| ATOM | 8027 | OG1 | THR | A | 518 | 52.642 | −21.808 | −6.973 | 1.00 | 23.81 | A | O |
| ATOM | 8029 | CG2 | THR | A | 518 | 51.876 | −20.228 | −5.351 | 1.00 | 24.26 | A | C |
| ATOM | 8033 | C | THR | A | 518 | 50.969 | −22.518 | −3.644 | 1.00 | 25.98 | A | C |
| ATOM | 8034 | O | THR | A | 518 | 51.400 | −22.003 | −2.596 | 1.00 | 25.54 | A | O |
| ATOM | 8036 | N | ALA | A | 519 | 49.717 | −22.968 | −3.774 | 1.00 | 23.55 | A | N |
| ATOM | 8037 | CA | ALA | A | 519 | 48.772 | −22.859 | −2.676 | 1.00 | 23.19 | A | C |
| ATOM | 8039 | CB | ALA | A | 519 | 47.375 | −23.219 | −3.096 | 1.00 | 20.70 | A | C |
| ATOM | 8043 | C | ALA | A | 519 | 49.182 | −23.644 | −1.436 | 1.00 | 23.29 | A | C |
| ATOM | 8044 | O | ALA | A | 519 | 49.096 | −23.125 | −0.286 | 1.00 | 24.26 | A | O |
| ATOM | 8046 | N | ILE | A | 520 | 49.673 | −24.853 | −1.639 | 1.00 | 21.17 | A | N |
| ATOM | 8047 | CA | ILE | A | 520 | 50.097 | −25.677 | −0.500 | 1.00 | 19.87 | A | C |
| ATOM | 8049 | CB | ILE | A | 520 | 50.425 | −27.126 | −0.957 | 1.00 | 20.77 | A | C |
| ATOM | 8051 | CG1 | ILE | A | 520 | 49.146 | −27.857 | −1.421 | 1.00 | 20.74 | A | C |

TABLE 4-2-continued

Coordinates of *P. alba* IspS

| | | | | | | | | | | | | |
|---|---|---|---|---|---|---|---|---|---|---|---|---|
| ATOM | 8054 | CD1 | ILE | A | 520 | 49.421 | −29.223 | −2.184 | 1.00 | 19.45 | A | C |
| ATOM | 8058 | CG2 | ILE | A | 520 | 51.083 | −27.909 | 0.152 | 1.00 | 16.11 | A | C |
| ATOM | 8062 | C | ILE | A | 520 | 51.288 | −25.003 | 0.202 | 1.00 | 20.17 | A | C |
| ATOM | 8063 | O | ILE | A | 520 | 51.384 | −25.018 | 1.437 | 1.00 | 19.37 | A | O |
| ATOM | 8065 | N | ASN | A | 521 | 52.166 | −24.366 | −0.574 | 1.00 | 21.54 | A | N |
| ATOM | 8066 | CA | ASN | A | 521 | 53.299 | −23.620 | 0.014 | 1.00 | 20.54 | A | C |
| ATOM | 8068 | CB | ASN | A | 521 | 54.188 | −22.992 | −1.066 | 1.00 | 21.56 | A | C |
| ATOM | 8071 | CG | ASN | A | 521 | 54.966 | −24.024 | −1.867 | 1.00 | 24.44 | A | C |
| ATOM | 8072 | OD1 | ASN | A | 521 | 55.198 | −25.124 | −1.399 | 1.00 | 19.38 | A | O |
| ATOM | 8073 | ND2 | ASN | A | 521 | 55.365 | −23.666 | −3.084 | 1.00 | 18.91 | A | N |
| ATOM | 8076 | C | ASN | A | 521 | 52.892 | −22.559 | 1.017 | 1.00 | 19.40 | A | C |
| ATOM | 8077 | O | ASN | A | 521 | 53.621 | −22.274 | 1.946 | 1.00 | 20.79 | A | O |
| ATOM | 8079 | N | LEU | A | 522 | 51.724 | −21.961 | 0.870 | 1.00 | 22.97 | A | N |
| ATOM | 8080 | CA | LEU | A | 522 | 51.287 | −21.020 | 1.894 | 1.00 | 22.18 | A | C |
| ATOM | 8082 | CB | LEU | A | 522 | 49.999 | −20.375 | 1.480 | 1.00 | 21.54 | A | C |
| ATOM | 8085 | CG | LEU | A | 522 | 49.371 | −19.451 | 2.528 | 1.00 | 28.84 | A | C |
| ATOM | 8087 | CD1 | LEU | A | 522 | 49.451 | −18.040 | 2.067 | 1.00 | 28.12 | A | C |
| ATOM | 8091 | CD2 | LEU | A | 522 | 47.923 | −19.860 | 2.764 | 1.00 | 22.93 | A | C |
| ATOM | 8095 | C | LEU | A | 522 | 51.128 | −21.739 | 3.258 | 1.00 | 23.98 | A | C |
| ATOM | 8096 | O | LEU | A | 522 | 51.440 | −21.191 | 4.335 | 1.00 | 27.60 | A | O |
| ATOM | 8098 | N | ALA | A | 523 | 50.655 | −22.966 | 3.219 | 1.00 | 20.93 | A | N |
| ATOM | 8099 | CA | ALA | A | 523 | 50.483 | −23.745 | 4.435 | 1.00 | 20.65 | A | C |
| ATOM | 8101 | CB | ALA | A | 523 | 49.688 | −25.053 | 4.123 | 1.00 | 18.52 | A | C |
| ATOM | 8105 | C | ALA | A | 523 | 51.858 | −24.069 | 5.025 | 1.00 | 19.62 | A | C |
| ATOM | 8106 | O | ALA | A | 523 | 52.066 | −23.988 | 6.225 | 1.00 | 19.29 | A | O |
| ATOM | 8108 | N | ARG | A | 524 | 52.790 | −24.453 | 4.158 | 1.00 | 21.30 | A | N |
| ATOM | 8109 | CA | ARG | A | 524 | 54.160 | −24.730 | 4.566 | 1.00 | 19.62 | A | C |
| ATOM | 8111 | CB | ARG | A | 524 | 54.994 | −25.155 | 3.355 | 1.00 | 19.24 | A | C |
| ATOM | 8114 | CG | ARG | A | 524 | 54.604 | −26.493 | 2.752 | 1.00 | 20.08 | A | C |
| ATOM | 8117 | CD | ARG | A | 524 | 55.572 | −26.973 | 1.663 | 1.00 | 16.22 | A | C |
| ATOM | 8120 | NE | ARG | A | 524 | 55.254 | −28.341 | 1.267 | 1.00 | 17.63 | A | N |
| ATOM | 8122 | CZ | ARG | A | 524 | 54.851 | −28.736 | 0.065 | 1.00 | 22.37 | A | C |
| ATOM | 8123 | NH1 | ARG | A | 524 | 54.705 | −27.877 | −0.917 | 1.00 | 22.88 | A | N |
| ATOM | 8126 | NH2 | ARG | A | 524 | 54.577 | −30.020 | −0.153 | 1.00 | 22.48 | A | N |
| ATOM | 8129 | C | ARG | A | 524 | 54.783 | −23.497 | 5.211 | 1.00 | 18.86 | A | C |
| ATOM | 8130 | O | ARG | A | 524 | 55.416 | −23.587 | 6.243 | 1.00 | 20.03 | A | O |
| ATOM | 8132 | N | GLN | A | 525 | 54.627 | −22.344 | 4.577 | 1.00 | 21.45 | A | N |
| ATOM | 8133 | CA | GLN | A | 525 | 55.227 | −21.127 | 5.095 | 1.00 | 23.44 | A | C |
| ATOM | 8135 | CB | GLN | A | 525 | 55.050 | −19.940 | 4.126 | 1.00 | 24.10 | A | C |
| ATOM | 8138 | CG | GLN | A | 525 | 55.702 | −18.631 | 4.655 | 1.00 | 27.82 | A | C |
| ATOM | 8141 | CD | GLN | A | 525 | 57.200 | −18.783 | 4.854 | 1.00 | 31.75 | A | C |
| ATOM | 8142 | OE1 | GLN | A | 525 | 57.858 | −19.483 | 4.107 | 1.00 | 35.59 | A | O |
| ATOM | 8143 | NE2 | GLN | A | 525 | 57.741 | −18.116 | 5.854 | 1.00 | 35.48 | A | N |
| ATOM | 8146 | C | GLN | A | 525 | 54.618 | −20.823 | 6.442 | 1.00 | 21.93 | A | C |
| ATOM | 8147 | O | GLN | A | 525 | 55.301 | −20.367 | 7.349 | 1.00 | 24.82 | A | O |
| ATOM | 8149 | N | SER | A | 526 | 53.335 | −21.125 | 6.588 | 1.00 | 23.48 | A | N |
| ATOM | 8150 | CA | SER | A | 526 | 52.645 | −20.951 | 7.865 | 1.00 | 21.99 | A | C |
| ATOM | 8152 | CB | SER | A | 526 | 51.157 | −21.240 | 7.721 | 1.00 | 21.77 | A | C |
| ATOM | 8155 | OG | SER | A | 526 | 50.545 | −20.385 | 6.756 | 1.00 | 27.32 | A | O |
| ATOM | 8157 | C | SER | A | 526 | 53.245 | −21.829 | 8.945 | 1.00 | 24.68 | A | C |
| ATOM | 8158 | O | SER | A | 526 | 53.518 | −21.362 | 10.061 | 1.00 | 24.00 | A | O |
| ATOM | 8160 | N | HIS | A | 527 | 53.480 | −23.096 | 8.630 | 1.00 | 24.99 | A | N |
| ATOM | 8161 | CA | HIS | A | 527 | 54.171 | −23.962 | 9.610 | 1.00 | 28.16 | A | C |
| ATOM | 8163 | CB | HIS | A | 527 | 54.357 | −25.381 | 9.073 | 1.00 | 29.27 | A | C |
| ATOM | 8166 | CG | HIS | A | 527 | 53.101 | −26.172 | 9.090 | 1.00 | 25.87 | A | C |
| ATOM | 8167 | ND1 | HIS | A | 527 | 52.548 | −26.642 | 10.258 | 1.00 | 26.45 | A | N |
| ATOM | 8169 | CE1 | HIS | A | 527 | 51.424 | −27.278 | 9.982 | 1.00 | 25.98 | A | C |
| ATOM | 8171 | NE2 | HIS | A | 527 | 51.211 | −27.201 | 8.681 | 1.00 | 24.15 | A | N |
| ATOM | 8173 | CD2 | HIS | A | 527 | 52.241 | −26.501 | 8.102 | 1.00 | 26.74 | A | C |
| ATOM | 8175 | C | HIS | A | 527 | 55.523 | −23.428 | 10.010 | 1.00 | 28.59 | A | C |
| ATOM | 8176 | O | HIS | A | 527 | 55.911 | −23.545 | 11.155 | 1.00 | 29.28 | A | O |
| ATOM | 8178 | N | CYS | A | 528 | 56.233 | −22.863 | 9.042 | 1.00 | 29.41 | A | N |
| ATOM | 8179 | CA | CYS | A | 528 | 57.620 | −22.452 | 9.236 | 1.00 | 32.72 | A | C |
| ATOM | 8181 | CB | CYS | A | 528 | 58.325 | −22.320 | 7.884 | 1.00 | 30.69 | A | C |
| ATOM | 8184 | SG | CYS | A | 528 | 58.709 | −23.947 | 7.199 | 1.00 | 30.00 | A | S |
| ATOM | 8186 | C | CYS | A | 528 | 57.731 | −21.150 | 10.027 | 1.00 | 35.27 | A | C |
| ATOM | 8187 | O | CYS | A | 528 | 58.642 | −20.983 | 10.799 | 1.00 | 35.65 | A | O |
| ATOM | 8189 | N | THR | A | 529 | 56.784 | −20.249 | 9.814 | 1.00 | 39.06 | A | N |
| ATOM | 8190 | CA | THR | A | 529 | 56.751 | −18.951 | 10.470 | 1.00 | 40.10 | A | C |
| ATOM | 8192 | CB | THR | A | 529 | 55.848 | −18.006 | 9.689 | 1.00 | 40.17 | A | C |
| ATOM | 8194 | OG1 | THR | A | 529 | 56.529 | −17.624 | 8.491 | 1.00 | 38.25 | A | O |
| ATOM | 8196 | CG2 | THR | A | 529 | 55.488 | −16.770 | 10.521 | 1.00 | 39.82 | A | C |
| ATOM | 8200 | C | THR | A | 529 | 56.265 | −19.016 | 11.911 | 1.00 | 42.32 | A | C |
| ATOM | 8201 | O | THR | A | 529 | 56.803 | −18.308 | 12.775 | 1.00 | 43.34 | A | O |
| ATOM | 8203 | N | TYR | A | 530 | 55.263 | −19.854 | 12.173 | 1.00 | 44.35 | A | N |
| ATOM | 8204 | CA | TYR | A | 530 | 54.693 | −19.966 | 13.505 | 1.00 | 46.00 | A | C |
| ATOM | 8206 | CB | TYR | A | 530 | 53.166 | −20.032 | 13.439 | 1.00 | 44.27 | A | C |
| ATOM | 8209 | CG | TYR | A | 530 | 52.609 | −18.762 | 12.860 | 1.00 | 37.30 | A | C |

TABLE 4-2-continued

| Coordinates of *P. alba* IspS | | | | | | | | | | | | |
|---|---|---|---|---|---|---|---|---|---|---|---|---|
| ATOM | 8210 | CD1 | TYR | A | 530 | 52.537 | −17.608 | 13.623 | 1.00 | 41.32 | A | C |
| ATOM | 8212 | CE1 | TYR | A | 530 | 52.068 | −16.421 | 13.084 | 1.00 | 36.85 | A | C |
| ATOM | 8214 | CZ | TYR | A | 530 | 51.680 | −16.379 | 11.772 | 1.00 | 34.37 | A | C |
| ATOM | 8215 | OH | TYR | A | 530 | 51.224 | −15.203 | 11.239 | 1.00 | 42.34 | A | O |
| ATOM | 8217 | CE2 | TYR | A | 530 | 51.754 | −17.510 | 10.987 | 1.00 | 37.02 | A | C |
| ATOM | 8219 | CD2 | TYR | A | 530 | 52.225 | −18.687 | 11.535 | 1.00 | 33.51 | A | C |
| ATOM | 8221 | C | TYR | A | 530 | 55.343 | −21.106 | 14.288 | 1.00 | 51.39 | A | C |
| ATOM | 8222 | O | TYR | A | 530 | 54.775 | −22.175 | 14.481 | 1.00 | 52.31 | A | O |
| ATOM | 8224 | N | HIS | A | 531 | 56.561 | −20.811 | 14.740 | 1.00 | 58.00 | A | N |
| ATOM | 8225 | CA | HIS | A | 531 | 57.399 | −21.680 | 15.572 | 1.00 | 61.94 | A | C |
| ATOM | 8227 | CB | HIS | A | 531 | 58.753 | −21.900 | 14.875 | 1.00 | 62.85 | A | C |
| ATOM | 8230 | CG | HIS | A | 531 | 59.575 | −20.646 | 14.738 | 1.00 | 65.82 | A | C |
| ATOM | 8231 | ND1 | HIS | A | 531 | 59.608 | −19.895 | 13.579 | 1.00 | 70.80 | A | N |
| ATOM | 8233 | CE1 | HIS | A | 531 | 60.404 | −18.852 | 13.752 | 1.00 | 66.74 | A | C |
| ATOM | 8235 | NE2 | HIS | A | 531 | 60.883 | −18.894 | 14.982 | 1.00 | 63.48 | A | N |
| ATOM | 8237 | CD2 | HIS | A | 531 | 60.381 | −20.004 | 15.620 | 1.00 | 65.00 | A | C |
| ATOM | 8239 | C | HIS | A | 531 | 57.655 | −20.986 | 16.920 | 1.00 | 64.85 | A | C |
| ATOM | 8240 | O | HIS | A | 531 | 57.504 | −19.758 | 17.030 | 1.00 | 64.46 | A | O |
| ATOM | 8242 | N | ASN | A | 532 | 58.067 | −21.766 | 17.926 | 1.00 | 67.27 | A | N |
| ATOM | 8243 | CA | ASN | A | 532 | 58.496 | −21.224 | 19.224 | 1.00 | 68.94 | A | C |
| ATOM | 8245 | CB | ASN | A | 532 | 57.603 | −21.755 | 20.366 | 1.00 | 70.24 | A | C |
| ATOM | 8248 | CG | ASN | A | 532 | 56.240 | −21.039 | 20.445 | 1.00 | 75.92 | A | C |
| ATOM | 8249 | OD1 | ASN | A | 532 | 55.500 | −20.950 | 19.452 | 1.00 | 78.73 | A | O |
| ATOM | 8250 | ND2 | ASN | A | 532 | 55.906 | −20.536 | 21.638 | 1.00 | 74.91 | A | N |
| ATOM | 8253 | C | ASN | A | 532 | 59.981 | −21.534 | 19.481 | 1.00 | 68.89 | A | C |
| ATOM | 8254 | O | ASN | A | 532 | 60.352 | −22.156 | 20.484 | 1.00 | 68.53 | A | O |
| ATOM | 8256 | N | THR | A | 537 | 67.332 | −21.795 | 21.607 | 1.00 | 92.68 | A | N |
| ATOM | 8257 | CA | THR | A | 537 | 66.924 | −20.612 | 20.853 | 1.00 | 93.30 | A | C |
| ATOM | 8259 | CB | THR | A | 537 | 66.958 | −20.873 | 19.320 | 1.00 | 93.55 | A | C |
| ATOM | 8261 | OG1 | THR | A | 537 | 68.054 | −21.736 | 18.994 | 1.00 | 94.33 | A | O |
| ATOM | 8263 | CG2 | THR | A | 537 | 67.102 | −19.564 | 18.539 | 1.00 | 93.26 | A | C |
| ATOM | 8267 | C | THR | A | 537 | 65.513 | −20.160 | 21.260 | 1.00 | 93.42 | A | C |
| ATOM | 8268 | O | THR | A | 537 | 64.724 | −20.952 | 21.790 | 1.00 | 93.83 | A | O |
| ATOM | 8270 | N | SER | A | 538 | 65.215 | −18.883 | 21.009 | 1.00 | 92.90 | A | N |
| ATOM | 8271 | CA | SER | A | 538 | 63.908 | −18.278 | 21.299 | 1.00 | 92.33 | A | C |
| ATOM | 8273 | CB | SER | A | 538 | 64.113 | −17.011 | 22.137 | 1.00 | 92.35 | A | C |
| ATOM | 8276 | OG | SER | A | 538 | 64.875 | −16.046 | 21.429 | 1.00 | 90.48 | A | O |
| ATOM | 8278 | C | SER | A | 538 | 63.159 | −17.940 | 19.991 | 1.00 | 91.91 | A | C |
| ATOM | 8279 | O | SER | A | 538 | 63.751 | −18.023 | 18.918 | 1.00 | 90.87 | A | O |
| ATOM | 8281 | N | PRO | A | 539 | 61.852 | −17.583 | 20.077 | 1.00 | 92.14 | A | N |
| ATOM | 8282 | CA | PRO | A | 539 | 61.015 | −17.108 | 18.952 | 1.00 | 91.90 | A | C |
| ATOM | 8284 | CB | PRO | A | 539 | 59.778 | −16.550 | 19.670 | 1.00 | 92.24 | A | C |
| ATOM | 8287 | CG | PRO | A | 539 | 59.602 | −17.482 | 20.811 | 1.00 | 93.29 | A | C |
| ATOM | 8290 | CD | PRO | A | 539 | 61.005 | −17.907 | 21.244 | 1.00 | 92.54 | A | C |
| ATOM | 8293 | C | PRO | A | 539 | 61.663 | −16.079 | 17.996 | 1.00 | 90.64 | A | C |
| ATOM | 8294 | O | PRO | A | 539 | 62.570 | −16.453 | 17.254 | 1.00 | 90.97 | A | O |
| ATOM | 8295 | N | ASP | A | 540 | 61.200 | −14.823 | 17.973 | 1.00 | 88.91 | A | N |
| ATOM | 8296 | CA | ASP | A | 540 | 61.764 | −13.832 | 17.045 | 1.00 | 87.34 | A | C |
| ATOM | 8298 | CB | ASP | A | 540 | 60.995 | −12.501 | 17.090 | 1.00 | 88.16 | A | C |
| ATOM | 8301 | CG | ASP | A | 540 | 61.064 | −11.734 | 15.767 | 1.00 | 91.26 | A | C |
| ATOM | 8302 | OD1 | ASP | A | 540 | 62.082 | −11.847 | 15.046 | 1.00 | 92.68 | A | O |
| ATOM | 8303 | OD2 | ASP | A | 540 | 60.095 | −11.012 | 15.445 | 1.00 | 92.20 | A | O |
| ATOM | 8304 | C | ASP | A | 540 | 63.249 | −13.623 | 17.357 | 1.00 | 83.97 | A | C |
| ATOM | 8305 | O | ASP | A | 540 | 63.608 | −12.904 | 18.291 | 1.00 | 84.17 | A | O |
| ATOM | 8307 | N | GLU | A | 541 | 64.085 | −14.261 | 16.542 | 1.00 | 80.01 | A | N |
| ATOM | 8308 | CA | GLU | A | 541 | 65.522 | −14.464 | 16.780 | 1.00 | 77.67 | A | C |
| ATOM | 8310 | CB | GLU | A | 541 | 65.870 | −14.669 | 18.260 | 1.00 | 78.10 | A | C |
| ATOM | 8313 | CG | GLU | A | 541 | 67.352 | −14.486 | 18.565 | 1.00 | 81.78 | A | C |
| ATOM | 8316 | CD | GLU | A | 541 | 67.610 | −13.838 | 19.922 | 1.00 | 88.80 | A | C |
| ATOM | 8317 | OE1 | GLU | A | 541 | 67.125 | −12.702 | 20.144 | 1.00 | 90.81 | A | O |
| ATOM | 8318 | OE2 | GLU | A | 541 | 68.306 | −14.453 | 20.761 | 1.00 | 88.82 | A | O |
| ATOM | 8319 | C | GLU | A | 541 | 65.937 | −15.699 | 15.973 | 1.00 | 73.57 | A | C |
| ATOM | 8320 | O | GLU | A | 541 | 66.977 | −15.711 | 15.311 | 1.00 | 73.68 | A | O |
| ATOM | 8322 | N | LEU | A | 542 | 65.116 | −16.743 | 16.054 | 1.00 | 68.45 | A | N |
| ATOM | 8323 | CA | LEU | A | 542 | 65.113 | −17.805 | 15.051 | 1.00 | 64.32 | A | C |
| ATOM | 8325 | CB | LEU | A | 542 | 64.264 | −18.994 | 15.512 | 1.00 | 64.16 | A | C |
| ATOM | 8328 | CG | LEU | A | 542 | 64.082 | −20.157 | 14.527 | 1.00 | 66.34 | A | C |
| ATOM | 8330 | CD1 | LEU | A | 542 | 63.430 | −21.367 | 15.221 | 1.00 | 64.49 | A | C |
| ATOM | 8334 | CD2 | LEU | A | 542 | 65.418 | −20.547 | 13.870 | 1.00 | 67.67 | A | C |
| ATOM | 8338 | C | LEU | A | 542 | 64.583 | −17.236 | 13.731 | 1.00 | 59.26 | A | C |
| ATOM | 8339 | O | LEU | A | 542 | 65.135 | −17.512 | 12.679 | 1.00 | 56.08 | A | O |
| ATOM | 8341 | N | THR | A | 543 | 63.525 | −16.431 | 13.807 | 1.00 | 55.75 | A | N |
| ATOM | 8342 | CA | THR | A | 543 | 63.001 | −15.694 | 12.652 | 1.00 | 53.99 | A | C |
| ATOM | 8344 | CB | THR | A | 543 | 61.827 | −14.798 | 13.080 | 1.00 | 52.82 | A | C |
| ATOM | 8346 | OG1 | THR | A | 543 | 60.796 | −15.613 | 13.647 | 1.00 | 55.45 | A | O |
| ATOM | 8348 | CG2 | THR | A | 543 | 61.266 | −13.999 | 11.910 | 1.00 | 47.21 | A | C |
| ATOM | 8352 | C | THR | A | 543 | 64.055 | −14.811 | 11.984 | 1.00 | 53.90 | A | C |
| ATOM | 8353 | O | THR | A | 543 | 64.132 | −14.738 | 10.754 | 1.00 | 53.78 | A | O |

TABLE 4-2-continued

Coordinates of *P. alba* IspS

| | | | | | | | | | | | | |
|---|---|---|---|---|---|---|---|---|---|---|---|---|
| ATOM | 8355 | N | ARG | A | 544 | 64.861 | −14.141 | 12.807 | 1.00 | 53.78 | A | N |
| ATOM | 8356 | CA | ARG | A | 544 | 65.880 | −13.214 | 12.320 | 1.00 | 53.00 | A | C |
| ATOM | 8358 | CB | ARG | A | 544 | 66.482 | −12.402 | 13.487 | 1.00 | 54.30 | A | C |
| ATOM | 8361 | CG | ARG | A | 544 | 67.763 | −11.600 | 13.148 | 1.00 | 58.88 | A | C |
| ATOM | 8364 | CD | ARG | A | 544 | 68.416 | −10.977 | 14.395 | 1.00 | 68.64 | A | C |
| ATOM | 8367 | NE | ARG | A | 544 | 68.769 | −11.968 | 15.421 | 1.00 | 75.29 | A | N |
| ATOM | 8369 | CZ | ARG | A | 544 | 69.815 | −12.799 | 15.370 | 1.00 | 78.84 | A | C |
| ATOM | 8370 | NH1 | ARG | A | 544 | 70.654 | −12.793 | 14.334 | 1.00 | 78.60 | A | N |
| ATOM | 8373 | NH2 | ARG | A | 544 | 70.023 | −13.656 | 16.367 | 1.00 | 78.30 | A | N |
| ATOM | 8376 | C | ARG | A | 544 | 66.977 | −13.965 | 11.591 | 1.00 | 50.00 | A | C |
| ATOM | 8377 | O | ARG | A | 544 | 67.503 | −13.474 | 10.602 | 1.00 | 49.41 | A | O |
| ATOM | 8379 | N | LYS | A | 545 | 67.342 | −15.131 | 12.113 | 1.00 | 47.99 | A | N |
| ATOM | 8380 | CA | LYS | A | 545 | 68.378 | −15.955 | 11.497 | 1.00 | 48.74 | A | C |
| ATOM | 8382 | CB | LYS | A | 545 | 68.824 | −17.088 | 12.442 | 1.00 | 50.27 | A | C |
| ATOM | 8385 | CG | LYS | A | 545 | 69.814 | −16.611 | 13.534 | 1.00 | 59.32 | A | C |
| ATOM | 8388 | CD | LYS | A | 545 | 70.549 | −17.761 | 14.252 | 1.00 | 64.78 | A | C |
| ATOM | 8391 | CE | LYS | A | 545 | 71.708 | −17.208 | 15.089 | 1.00 | 70.21 | A | C |
| ATOM | 8394 | NZ | LYS | A | 545 | 72.591 | −18.251 | 15.680 | 1.00 | 71.30 | A | N |
| ATOM | 8398 | C | LYS | A | 545 | 67.892 | −16.520 | 10.167 | 1.00 | 44.99 | A | C |
| ATOM | 8399 | O | LYS | A | 545 | 68.642 | −16.585 | 9.194 | 1.00 | 42.74 | A | O |
| ATOM | 8401 | N | ARG | A | 546 | 66.624 | −16.911 | 10.141 | 1.00 | 43.75 | A | N |
| ATOM | 8402 | CA | ARG | A | 546 | 66.006 | −17.452 | 8.934 | 1.00 | 42.43 | A | C |
| ATOM | 8404 | CB | ARG | A | 546 | 64.624 | −18.006 | 9.244 | 1.00 | 41.43 | A | C |
| ATOM | 8407 | CG | ARG | A | 546 | 64.725 | −19.301 | 10.007 | 1.00 | 34.91 | A | C |
| ATOM | 8410 | CD | ARG | A | 546 | 63.396 | −19.926 | 10.297 | 1.00 | 35.83 | A | C |
| ATOM | 8413 | NE | ARG | A | 546 | 63.616 | −21.251 | 10.863 | 1.00 | 35.94 | A | N |
| ATOM | 8415 | CZ | ARG | A | 546 | 62.659 | −22.099 | 11.220 | 1.00 | 36.20 | A | C |
| ATOM | 8416 | NH1 | ARG | A | 546 | 61.380 | −21.769 | 11.093 | 1.00 | 37.38 | A | N |
| ATOM | 8419 | NH2 | ARG | A | 546 | 62.992 | −23.276 | 11.743 | 1.00 | 39.23 | A | N |
| ATOM | 8422 | C | ARG | A | 546 | 65.963 | −16.413 | 7.826 | 1.00 | 42.22 | A | C |
| ATOM | 8423 | O | ARG | A | 546 | 66.372 | −16.706 | 6.704 | 1.00 | 42.78 | A | O |
| ATOM | 8425 | N | VAL | A | 547 | 65.537 | −15.192 | 8.153 | 1.00 | 40.65 | A | N |
| ATOM | 8426 | CA | VAL | A | 547 | 65.599 | −14.085 | 7.193 | 1.00 | 40.43 | A | C |
| ATOM | 8428 | CB | VAL | A | 547 | 65.055 | −12.771 | 7.810 | 1.00 | 41.44 | A | C |
| ATOM | 8430 | CG1 | VAL | A | 547 | 65.454 | −11.568 | 6.974 | 1.00 | 43.77 | A | C |
| ATOM | 8434 | CG2 | VAL | A | 547 | 63.543 | −12.847 | 7.984 | 1.00 | 37.89 | A | C |
| ATOM | 8438 | C | VAL | A | 547 | 67.028 | −13.846 | 6.715 | 1.00 | 40.76 | A | C |
| ATOM | 8439 | O | VAL | A | 547 | 67.269 | −13.551 | 5.547 | 1.00 | 41.64 | A | O |
| ATOM | 8441 | N | LEU | A | 548 | 67.978 | −13.952 | 7.632 | 1.00 | 39.02 | A | N |
| ATOM | 8442 | CA | LEU | A | 548 | 69.369 | −13.763 | 7.283 | 1.00 | 37.94 | A | C |
| ATOM | 8444 | CB | LEU | A | 548 | 70.239 | −13.775 | 8.544 | 1.00 | 38.42 | A | C |
| ATOM | 8447 | CG | LEU | A | 548 | 71.184 | −12.599 | 8.823 | 1.00 | 45.83 | A | C |
| ATOM | 8449 | CD1 | LEU | A | 548 | 70.487 | −11.217 | 8.801 | 1.00 | 41.58 | A | C |
| ATOM | 8453 | CD2 | LEU | A | 548 | 71.866 | −12.861 | 10.179 | 1.00 | 43.53 | A | C |
| ATOM | 8457 | C | LEU | A | 548 | 69.805 | −14.866 | 6.305 | 1.00 | 36.31 | A | C |
| ATOM | 8458 | O | LEU | A | 548 | 70.419 | −14.589 | 5.281 | 1.00 | 37.41 | A | O |
| ATOM | 8460 | N | SER | A | 549 | 69.471 | −16.115 | 6.607 | 1.00 | 33.80 | A | N |
| ATOM | 8461 | CA | SER | A | 549 | 69.995 | −17.230 | 5.830 | 1.00 | 32.40 | A | C |
| ATOM | 8463 | CB | SER | A | 549 | 69.914 | −18.526 | 6.640 | 1.00 | 32.69 | A | C |
| ATOM | 8466 | OG | SER | A | 549 | 68.573 | −18.865 | 6.912 | 1.00 | 33.82 | A | O |
| ATOM | 8468 | C | SER | A | 549 | 69.258 | −17.374 | 4.497 | 1.00 | 29.96 | A | C |
| ATOM | 8469 | O | SER | A | 549 | 69.816 | −17.884 | 3.525 | 1.00 | 28.51 | A | O |
| ATOM | 8471 | N | VAL | A | 550 | 68.017 | −16.896 | 4.444 | 1.00 | 28.34 | A | N |
| ATOM | 8472 | CA | VAL | A | 550 | 67.218 | −16.982 | 3.232 | 1.00 | 26.12 | A | C |
| ATOM | 8474 | CB | VAL | A | 550 | 65.754 | −17.231 | 3.551 | 1.00 | 27.43 | A | C |
| ATOM | 8476 | CG1 | VAL | A | 550 | 64.912 | −17.149 | 2.274 | 1.00 | 22.74 | A | C |
| ATOM | 8480 | CG2 | VAL | A | 550 | 65.603 | −18.589 | 4.190 | 1.00 | 20.03 | A | C |
| ATOM | 8484 | C | VAL | A | 550 | 67.352 | −15.777 | 2.320 | 1.00 | 27.26 | A | C |
| ATOM | 8485 | O | VAL | A | 550 | 67.466 | −15.933 | 1.101 | 1.00 | 26.44 | A | O |
| ATOM | 8487 | N | ILE | A | 551 | 67.367 | −14.575 | 2.877 | 1.00 | 28.59 | A | N |
| ATOM | 8488 | CA | ILE | A | 551 | 67.457 | −13.380 | 2.037 | 1.00 | 30.46 | A | C |
| ATOM | 8490 | CB | ILE | A | 551 | 66.537 | −12.274 | 2.537 | 1.00 | 31.18 | A | C |
| ATOM | 8492 | CG1 | ILE | A | 551 | 65.093 | −12.747 | 2.553 | 1.00 | 29.53 | A | C |
| ATOM | 8495 | CD1 | ILE | A | 551 | 64.570 | −13.145 | 1.191 | 1.00 | 40.54 | A | C |
| ATOM | 8499 | CG2 | ILE | A | 551 | 66.697 | −11.023 | 1.653 | 1.00 | 29.98 | A | C |
| ATOM | 8503 | C | ILE | A | 551 | 68.841 | −12.746 | 1.941 | 1.00 | 31.12 | A | C |
| ATOM | 8504 | O | ILE | A | 551 | 69.329 | −12.460 | 0.843 | 1.00 | 30.57 | A | O |
| ATOM | 8506 | N | THR | A | 552 | 69.453 | −12.486 | 3.090 | 1.00 | 33.43 | A | N |
| ATOM | 8507 | CA | THR | A | 552 | 70.551 | −11.541 | 3.150 | 1.00 | 35.23 | A | C |
| ATOM | 8509 | CB | THR | A | 552 | 70.422 | −10.661 | 4.419 | 1.00 | 38.85 | A | C |
| ATOM | 8511 | OG1 | THR | A | 552 | 70.734 | −11.431 | 5.583 | 1.00 | 49.74 | A | O |
| ATOM | 8513 | CG2 | THR | A | 552 | 69.002 | −10.115 | 4.567 | 1.00 | 34.09 | A | C |
| ATOM | 8517 | C | THR | A | 552 | 71.979 | −12.148 | 3.020 | 1.00 | 35.34 | A | C |
| ATOM | 8518 | O | THR | A | 552 | 72.805 | −11.623 | 2.259 | 1.00 | 34.57 | A | O |
| ATOM | 8520 | N | GLU | A | 553 | 72.273 | −13.222 | 3.752 | 1.00 | 35.04 | A | N |
| ATOM | 8521 | CA | GLU | A | 553 | 73.628 | −13.801 | 3.777 | 1.00 | 36.99 | A | C |
| ATOM | 8523 | CB | GLU | A | 553 | 74.020 | −14.209 | 5.200 | 1.00 | 38.28 | A | C |
| ATOM | 8526 | CG | GLU | A | 553 | 74.412 | −13.034 | 6.080 | 1.00 | 46.45 | A | C |

TABLE 4-2-continued

| Coordinates of *P. alba* IspS | | | | | | | | | | | |
|---|---|---|---|---|---|---|---|---|---|---|---|
| ATOM | 8529 | CD | GLU | A | 553 | 75.002 | −13.456 | 7.418 | 1.00 | 57.04 | A | C |
| ATOM | 8530 | OE1 | GLU | A | 553 | 75.499 | −12.564 | 8.142 | 1.00 | 60.01 | A | O |
| ATOM | 8531 | OE2 | GLU | A | 553 | 74.972 | −14.667 | 7.750 | 1.00 | 60.27 | A | O |
| ATOM | 8532 | C | GLU | A | 553 | 73.756 | −15.027 | 2.879 | 1.00 | 35.15 | A | C |
| ATOM | 8533 | O | GLU | A | 553 | 73.085 | −16.016 | 3.094 | 1.00 | 33.64 | A | O |
| ATOM | 8535 | N | PRO | A | 554 | 74.649 | −14.979 | 1.890 | 1.00 | 35.47 | A | N |
| ATOM | 8536 | CA | PRO | A | 554 | 74.878 | −16.177 | 1.087 | 1.00 | 33.93 | A | C |
| ATOM | 8538 | CB | PRO | A | 554 | 75.924 | −15.722 | 0.056 | 1.00 | 35.05 | A | C |
| ATOM | 8541 | CG | PRO | A | 554 | 75.825 | −14.234 | 0.044 | 1.00 | 35.89 | A | C |
| ATOM | 8544 | CD | PRO | A | 554 | 75.486 | −13.854 | 1.441 | 1.00 | 36.23 | A | C |
| ATOM | 8547 | C | PRO | A | 554 | 75.426 | −17.330 | 1.903 | 1.00 | 31.36 | A | C |
| ATOM | 8548 | O | PRO | A | 554 | 75.880 | −17.153 | 3.018 | 1.00 | 31.42 | A | O |
| ATOM | 8549 | N | ILE | A | 555 | 75.349 | −18.518 | 1.342 | 1.00 | 30.82 | A | N |
| ATOM | 8550 | CA | ILE | A | 555 | 75.946 | −19.684 | 1.957 | 1.00 | 31.22 | A | C |
| ATOM | 8552 | CB | ILE | A | 555 | 75.349 | −20.985 | 1.366 | 1.00 | 30.17 | A | C |
| ATOM | 8554 | CG1 | ILE | A | 555 | 73.862 | −21.095 | 1.715 | 1.00 | 30.75 | A | C |
| ATOM | 8557 | CD1 | ILE | A | 555 | 73.166 | −22.359 | 1.159 | 1.00 | 26.65 | A | C |
| ATOM | 8561 | CG2 | ILE | A | 555 | 76.096 | −22.190 | 1.874 | 1.00 | 29.43 | A | C |
| ATOM | 8565 | C | ILE | A | 555 | 77.455 | −19.589 | 1.694 | 1.00 | 30.28 | A | C |
| ATOM | 8566 | O | ILE | A | 555 | 77.853 | −19.201 | 0.607 | 1.00 | 27.19 | A | O |
| ATOM | 8568 | N | LEU | A | 556 | 78.273 | −19.924 | 2.693 | 1.00 | 31.81 | A | N |
| ATOM | 8569 | CA | LEU | A | 556 | 79.736 | −19.843 | 2.571 | 1.00 | 33.19 | A | C |
| ATOM | 8571 | CB | LEU | A | 556 | 80.432 | −20.311 | 3.857 | 1.00 | 33.04 | A | C |
| ATOM | 8574 | CG | LEU | A | 556 | 80.327 | −19.370 | 5.071 | 1.00 | 40.15 | A | C |
| ATOM | 8576 | CD1 | LEU | A | 556 | 80.560 | −20.126 | 6.367 | 1.00 | 44.82 | A | C |
| ATOM | 8580 | CD2 | LEU | A | 556 | 81.297 | −18.182 | 4.960 | 1.00 | 40.79 | A | C |
| ATOM | 8584 | C | LEU | A | 556 | 80.195 | −20.687 | 1.391 | 1.00 | 33.20 | A | C |
| ATOM | 8585 | O | LEU | A | 556 | 79.754 | −21.814 | 1.234 | 1.00 | 34.64 | A | O |
| ATOM | 8587 | N | PRO | A | 557 | 81.093 | −20.150 | 0.560 | 1.00 | 34.80 | A | N |
| ATOM | 8588 | CA | PRO | A | 557 | 81.389 | −20.817 | −0.707 | 1.00 | 34.59 | A | C |
| ATOM | 8590 | CB | PRO | A | 557 | 82.379 | −19.878 | −1.402 | 1.00 | 35.42 | A | C |
| ATOM | 8593 | CG | PRO | A | 557 | 82.956 | −19.016 | −0.316 | 1.00 | 37.04 | A | C |
| ATOM | 8596 | CD | PRO | A | 557 | 82.005 | −19.023 | 0.846 | 1.00 | 35.67 | A | C |
| ATOM | 8599 | C | PRO | A | 557 | 82.003 | −22.187 | −0.532 | 1.00 | 34.31 | A | C |
| ATOM | 8600 | O | PRO | A | 557 | 82.598 | −22.485 | 0.497 | 1.00 | 34.81 | A | O |
| ATOM | 8601 | N | PHE | A | 558 | 81.824 | −23.015 | −1.548 | 1.00 | 34.16 | A | N |
| ATOM | 8602 | CA | PHE | A | 558 | 82.422 | −24.328 | −1.595 | 1.00 | 34.90 | A | C |
| ATOM | 8604 | CB | PHE | A | 558 | 82.071 | −24.950 | −2.929 | 1.00 | 32.02 | A | C |
| ATOM | 8607 | CG | PHE | A | 558 | 82.786 | −26.220 | −3.210 | 1.00 | 33.45 | A | C |
| ATOM | 8608 | CD1 | PHE | A | 558 | 83.795 | −26.268 | −4.157 | 1.00 | 35.45 | A | C |
| ATOM | 8610 | CE1 | PHE | A | 558 | 84.443 | −27.463 | −4.429 | 1.00 | 39.71 | A | C |
| ATOM | 8612 | CZ | PHE | A | 558 | 84.082 | −28.618 | −3.750 | 1.00 | 40.59 | A | C |
| ATOM | 8614 | CE2 | PHE | A | 558 | 83.074 | −28.575 | −2.805 | 1.00 | 37.21 | A | C |
| ATOM | 8616 | CD2 | PHE | A | 558 | 82.440 | −27.382 | −2.536 | 1.00 | 34.24 | A | C |
| ATOM | 8618 | C | PHE | A | 558 | 83.950 | −24.247 | −1.466 | 1.00 | 37.69 | A | C |
| ATOM | 8619 | O | PHE | A | 558 | 84.563 | −23.354 | −2.050 | 1.00 | 35.80 | A | O |
| ATOM | 8621 | N | GLU | A | 559 | 84.547 | −25.183 | −0.726 | 1.00 | 42.77 | A | N |
| ATOM | 8622 | CA | GLU | A | 559 | 86.019 | −25.260 | −0.597 | 1.00 | 49.59 | A | C |
| ATOM | 8624 | CB | GLU | A | 559 | 86.454 | −25.349 | 0.882 | 1.00 | 50.56 | A | C |
| ATOM | 8627 | CG | GLU | A | 559 | 86.515 | −23.989 | 1.607 | 1.00 | 54.49 | A | C |
| ATOM | 8630 | CD | GLU | A | 559 | 87.615 | −23.913 | 2.683 | 1.00 | 62.33 | A | C |
| ATOM | 8631 | OE1 | GLU | A | 559 | 88.034 | −24.964 | 3.225 | 1.00 | 60.02 | A | O |
| ATOM | 8632 | OE2 | GLU | A | 559 | 88.065 | −22.786 | 2.989 | 1.00 | 62.02 | A | O |
| ATOM | 8633 | C | GLU | A | 559 | 86.678 | −26.368 | −1.464 | 1.00 | 52.68 | A | C |
| ATOM | 8634 | O | GLU | A | 559 | 86.943 | −26.123 | −2.636 | 1.00 | 54.35 | A | O |
| ATOM | 8636 | N | ARG | A | 560 | 86.938 | −27.551 | −0.895 | 1.00 | 55.62 | A | N |
| ATOM | 8637 | CA | ARG | A | 560 | 87.722 | −28.662 | −1.529 | 1.00 | 58.23 | A | C |
| ATOM | 8639 | CB | ARG | A | 560 | 88.710 | −28.199 | −2.636 | 1.00 | 59.46 | A | C |
| ATOM | 8642 | CG | ARG | A | 560 | 88.211 | −28.475 | −4.084 | 1.00 | 65.26 | A | C |
| ATOM | 8645 | CD | ARG | A | 560 | 88.672 | −27.426 | −5.136 | 1.00 | 70.99 | A | C |
| ATOM | 8648 | NE | ARG | A | 560 | 87.572 | −27.065 | −6.051 | 1.00 | 76.26 | A | N |
| ATOM | 8650 | CZ | ARG | A | 560 | 87.471 | −25.927 | −6.754 | 1.00 | 78.60 | A | C |
| ATOM | 8651 | NH1 | ARG | A | 560 | 88.419 | −24.990 | −6.703 | 1.00 | 78.10 | A | N |
| ATOM | 8654 | NH2 | ARG | A | 560 | 86.402 | −25.724 | −7.529 | 1.00 | 77.34 | A | N |
| ATOM | 8657 | C | ARG | A | 560 | 88.497 | −29.449 | −0.470 | 1.00 | 57.56 | A | C |
| ATOM | 8658 | O | ARG | A | 560 | 89.485 | −28.950 | 0.077 | 1.00 | 57.69 | A | O |
| ATOM | 8660 | N | ALA | B | 23 | 68.865 | 37.021 | 10.784 | 1.00 | 63.55 | B | N |
| ATOM | 8661 | CA | ALA | B | 23 | 69.934 | 36.293 | 10.034 | 1.00 | 63.42 | B | C |
| ATOM | 8663 | CB | ALA | B | 23 | 71.193 | 36.204 | 10.865 | 1.00 | 63.20 | B | C |
| ATOM | 8667 | C | ALA | B | 23 | 69.468 | 34.898 | 9.638 | 1.00 | 63.10 | B | C |
| ATOM | 8668 | O | ALA | B | 23 | 68.478 | 34.404 | 10.177 | 1.00 | 63.23 | B | O |
| ATOM | 8672 | N | ASN | B | 24 | 70.182 | 34.274 | 8.698 | 1.00 | 62.83 | B | N |
| ATOM | 8673 | CA | ASN | B | 24 | 69.852 | 32.919 | 8.208 | 1.00 | 62.89 | B | C |
| ATOM | 8675 | CB | ASN | B | 24 | 68.986 | 33.004 | 6.939 | 1.00 | 64.13 | B | C |
| ATOM | 8678 | CG | ASN | B | 24 | 68.555 | 31.630 | 6.414 | 1.00 | 66.01 | B | C |
| ATOM | 8679 | OD1 | ASN | B | 24 | 67.998 | 30.809 | 7.149 | 1.00 | 66.06 | B | O |
| ATOM | 8680 | ND2 | ASN | B | 24 | 68.801 | 31.389 | 5.132 | 1.00 | 66.01 | B | N |
| ATOM | 8683 | C | ASN | B | 24 | 71.083 | 32.041 | 7.929 | 1.00 | 60.68 | B | C |

TABLE 4-2-continued

| Coordinates of *P. alba* IspS | | | | | | | | | | | |
|---|---|---|---|---|---|---|---|---|---|---|---|
| ATOM | 8684 | O | ASN | B | 24 | 71.878 | 32.334 | 7.029 | 1.00 | 60.33 | B | O |
| ATOM | 8686 | N | TYR | B | 25 | 71.215 | 30.959 | 8.699 | 1.00 | 58.42 | B | N |
| ATOM | 8687 | CA | TYR | B | 25 | 72.299 | 29.991 | 8.529 | 1.00 | 56.45 | B | C |
| ATOM | 8689 | CB | TYR | B | 25 | 73.034 | 29.771 | 9.854 | 1.00 | 54.20 | B | C |
| ATOM | 8692 | CG | TYR | B | 25 | 73.585 | 31.045 | 10.447 | 1.00 | 45.61 | B | C |
| ATOM | 8693 | CD1 | TYR | B | 25 | 74.573 | 31.785 | 9.789 | 1.00 | 37.42 | B | C |
| ATOM | 8695 | CE1 | TYR | B | 25 | 75.070 | 32.965 | 10.343 | 1.00 | 34.67 | B | C |
| ATOM | 8697 | CZ | TYR | B | 25 | 74.575 | 33.398 | 11.567 | 1.00 | 26.79 | B | C |
| ATOM | 8698 | OH | TYR | B | 25 | 75.031 | 34.555 | 12.166 | 1.00 | 22.69 | B | O |
| ATOM | 8700 | CE2 | TYR | B | 25 | 73.602 | 32.674 | 12.215 | 1.00 | 26.03 | B | C |
| ATOM | 8702 | CD2 | TYR | B | 25 | 73.112 | 31.521 | 11.660 | 1.00 | 34.02 | B | C |
| ATOM | 8704 | C | TYR | B | 25 | 71.835 | 28.640 | 7.990 | 1.00 | 57.64 | B | C |
| ATOM | 8705 | O | TYR | B | 25 | 72.641 | 27.717 | 7.901 | 1.00 | 57.97 | B | O |
| ATOM | 8707 | N | GLU | B | 26 | 70.560 | 28.511 | 7.620 | 1.00 | 59.08 | B | N |
| ATOM | 8708 | CA | GLU | B | 26 | 70.045 | 27.223 | 7.118 | 1.00 | 60.48 | B | C |
| ATOM | 8710 | CB | GLU | B | 26 | 68.510 | 27.159 | 7.198 | 1.00 | 61.50 | B | C |
| ATOM | 8713 | CG | GLU | B | 26 | 67.992 | 27.065 | 8.651 | 1.00 | 68.14 | B | C |
| ATOM | 8716 | CD | GLU | B | 26 | 66.579 | 26.483 | 8.775 | 1.00 | 76.80 | B | C |
| ATOM | 8717 | OE1 | GLU | B | 26 | 66.038 | 25.934 | 7.784 | 1.00 | 81.59 | B | O |
| ATOM | 8718 | OE2 | GLU | B | 26 | 66.008 | 26.568 | 9.885 | 1.00 | 80.08 | B | O |
| ATOM | 8719 | C | GLU | B | 26 | 70.551 | 26.918 | 5.694 | 1.00 | 58.35 | B | C |
| ATOM | 8720 | O | GLU | B | 26 | 70.748 | 27.837 | 4.898 | 1.00 | 55.74 | B | O |
| ATOM | 8722 | N | PRO | B | 27 | 70.785 | 25.623 | 5.389 | 1.00 | 58.14 | B | N |
| ATOM | 8723 | CA | PRO | B | 27 | 71.383 | 25.254 | 4.106 | 1.00 | 57.29 | B | C |
| ATOM | 8725 | CB | PRO | B | 27 | 71.677 | 23.759 | 4.265 | 1.00 | 58.74 | B | C |
| ATOM | 8728 | CG | PRO | B | 27 | 70.648 | 23.277 | 5.248 | 1.00 | 58.92 | B | C |
| ATOM | 8731 | CD | PRO | B | 27 | 70.460 | 24.434 | 6.207 | 1.00 | 58.03 | B | C |
| ATOM | 8734 | C | PRO | B | 27 | 70.427 | 25.464 | 2.951 | 1.00 | 56.06 | B | C |
| ATOM | 8735 | O | PRO | B | 27 | 69.206 | 25.463 | 3.137 | 1.00 | 56.00 | B | O |
| ATOM | 8736 | N | ASN | B | 28 | 70.993 | 25.657 | 1.768 | 1.00 | 54.96 | B | N |
| ATOM | 8737 | CA | ASN | B | 28 | 70.214 | 25.706 | 0.536 | 1.00 | 54.67 | B | C |
| ATOM | 8739 | CB | ASN | B | 28 | 70.821 | 26.721 | −0.448 | 1.00 | 55.69 | B | C |
| ATOM | 8742 | CG | ASN | B | 28 | 71.032 | 28.083 | 0.184 | 1.00 | 56.97 | B | C |
| ATOM | 8743 | OD1 | ASN | B | 28 | 70.102 | 28.660 | 0.744 | 1.00 | 59.86 | B | O |
| ATOM | 8744 | ND2 | ASN | B | 28 | 72.262 | 28.593 | 0.118 | 1.00 | 57.20 | B | N |
| ATOM | 8747 | C | ASN | B | 28 | 70.152 | 24.318 | −0.095 | 1.00 | 52.96 | B | C |
| ATOM | 8748 | O | ASN | B | 28 | 71.036 | 23.469 | 0.110 | 1.00 | 50.45 | B | O |
| ATOM | 8750 | N | SER | B | 29 | 69.092 | 24.090 | −0.858 | 1.00 | 52.74 | B | N |
| ATOM | 8751 | CA | SER | B | 29 | 68.943 | 22.848 | −1.620 | 1.00 | 53.12 | B | C |
| ATOM | 8753 | CB | SER | B | 29 | 67.530 | 22.783 | −2.229 | 1.00 | 53.87 | B | C |
| ATOM | 8756 | OG | SER | B | 29 | 67.129 | 24.045 | −2.769 | 1.00 | 50.23 | B | O |
| ATOM | 8758 | C | SER | B | 29 | 70.021 | 22.689 | −2.717 | 1.00 | 52.24 | B | C |
| ATOM | 8759 | O | SER | B | 29 | 70.258 | 21.579 | −3.202 | 1.00 | 53.74 | B | O |
| ATOM | 8761 | N | TRP | B | 30 | 70.662 | 23.796 | −3.095 | 1.00 | 50.38 | B | N |
| ATOM | 8762 | CA | TRP | B | 30 | 71.696 | 23.793 | −4.132 | 1.00 | 49.96 | B | C |
| ATOM | 8764 | CB | TRP | B | 30 | 71.494 | 24.969 | −5.109 | 1.00 | 49.93 | B | C |
| ATOM | 8767 | CG | TRP | B | 30 | 71.028 | 26.273 | −4.513 | 1.00 | 51.10 | B | C |
| ATOM | 8768 | CD1 | TRP | B | 30 | 69.736 | 26.720 | −4.435 | 1.00 | 57.17 | B | C |
| ATOM | 8770 | NE1 | TRP | B | 30 | 69.700 | 27.965 | −3.840 | 1.00 | 60.59 | B | N |
| ATOM | 8772 | CE2 | TRP | B | 30 | 70.981 | 28.348 | −3.534 | 1.00 | 55.40 | B | C |
| ATOM | 8773 | CD2 | TRP | B | 30 | 71.846 | 27.311 | −3.947 | 1.00 | 52.14 | B | C |
| ATOM | 8774 | CE3 | TRP | B | 30 | 73.224 | 27.459 | −3.736 | 1.00 | 57.76 | B | C |
| ATOM | 8776 | CZ3 | TRP | B | 30 | 73.692 | 28.628 | −3.134 | 1.00 | 59.65 | B | C |
| ATOM | 8778 | CH2 | TRP | B | 30 | 72.807 | 29.640 | −2.735 | 1.00 | 60.19 | B | C |
| ATOM | 8780 | CZ2 | TRP | B | 30 | 71.450 | 29.517 | −2.921 | 1.00 | 60.67 | B | C |
| ATOM | 8782 | C | TRP | B | 30 | 73.158 | 23.763 | −3.617 | 1.00 | 48.98 | B | C |
| ATOM | 8783 | O | TRP | B | 30 | 74.074 | 23.547 | −4.408 | 1.00 | 47.49 | B | O |
| ATOM | 8785 | N | ASP | B | 31 | 73.376 | 23.974 | −2.317 | 1.00 | 47.96 | B | N |
| ATOM | 8786 | CA | ASP | B | 31 | 74.734 | 23.951 | −1.732 | 1.00 | 47.91 | B | C |
| ATOM | 8788 | CB | ASP | B | 31 | 74.661 | 24.026 | −0.202 | 1.00 | 47.75 | B | C |
| ATOM | 8791 | CG | ASP | B | 31 | 74.301 | 25.413 | 0.310 | 1.00 | 50.81 | B | C |
| ATOM | 8792 | OD1 | ASP | B | 31 | 74.399 | 26.417 | −0.447 | 1.00 | 52.74 | B | O |
| ATOM | 8793 | OD2 | ASP | B | 31 | 73.939 | 25.489 | 1.505 | 1.00 | 54.84 | B | O |
| ATOM | 8794 | C | ASP | B | 31 | 75.545 | 22.705 | −2.113 | 1.00 | 47.82 | B | C |
| ATOM | 8795 | O | ASP | B | 31 | 74.989 | 21.614 | −2.241 | 1.00 | 46.75 | B | O |
| ATOM | 8797 | N | TYR | B | 32 | 76.861 | 22.863 | −2.267 | 1.00 | 47.95 | B | N |
| ATOM | 8798 | CA | TYR | B | 32 | 77.729 | 21.724 | −2.620 | 1.00 | 48.39 | B | C |
| ATOM | 8800 | CB | TYR | B | 32 | 79.107 | 22.187 | −3.111 | 1.00 | 46.33 | B | C |
| ATOM | 8803 | CG | TYR | B | 32 | 79.061 | 22.966 | −4.404 | 1.00 | 42.06 | B | C |
| ATOM | 8804 | CD1 | TYR | B | 32 | 78.597 | 22.375 | −5.600 | 1.00 | 32.87 | B | C |
| ATOM | 8806 | CE1 | TYR | B | 32 | 78.565 | 23.094 | −6.785 | 1.00 | 24.91 | B | C |
| ATOM | 8808 | CZ | TYR | B | 32 | 78.983 | 24.416 | −6.780 | 1.00 | 29.67 | B | C |
| ATOM | 8809 | OH | TYR | B | 32 | 78.959 | 25.162 | −7.917 | 1.00 | 28.02 | B | O |
| ATOM | 8811 | CE2 | TYR | B | 32 | 79.435 | 25.021 | −5.609 | 1.00 | 33.06 | B | C |
| ATOM | 8813 | CD2 | TYR | B | 32 | 79.481 | 24.295 | −4.442 | 1.00 | 38.13 | B | C |
| ATOM | 8815 | C | TYR | B | 32 | 77.912 | 20.694 | −1.496 | 1.00 | 50.79 | B | C |
| ATOM | 8816 | O | TYR | B | 32 | 78.332 | 19.566 | −1.774 | 1.00 | 49.23 | B | O |
| ATOM | 8818 | N | ASP | B | 33 | 77.621 | 21.082 | −0.247 | 1.00 | 54.28 | B | N |

TABLE 4-2-continued

Coordinates of *P. alba* IspS

| | | | | | | | | | | | | |
|---|---|---|---|---|---|---|---|---|---|---|---|---|
| ATOM | 8819 | CA | ASP | B | 33 | 77.619 | 20.140 | 0.897 | 1.00 | 56.96 | B | C |
| ATOM | 8821 | CB | ASP | B | 33 | 77.480 | 20.882 | 2.244 | 1.00 | 56.67 | B | C |
| ATOM | 8824 | CG | ASP | B | 33 | 78.786 | 21.540 | 2.715 | 1.00 | 54.94 | B | C |
| ATOM | 8825 | OD1 | ASP | B | 33 | 79.876 | 21.054 | 2.353 | 1.00 | 51.15 | B | O |
| ATOM | 8826 | OD2 | ASP | B | 33 | 78.720 | 22.540 | 3.471 | 1.00 | 53.38 | B | O |
| ATOM | 8827 | C | ASP | B | 33 | 76.479 | 19.130 | 0.751 | 1.00 | 60.30 | B | C |
| ATOM | 8828 | O | ASP | B | 33 | 76.675 | 17.922 | 0.940 | 1.00 | 59.85 | B | O |
| ATOM | 8830 | N | TYR | B | 34 | 75.299 | 19.650 | 0.402 | 1.00 | 64.90 | B | N |
| ATOM | 8831 | CA | TYR | B | 34 | 74.073 | 18.860 | 0.224 | 1.00 | 69.43 | B | C |
| ATOM | 8833 | CB | TYR | B | 34 | 72.841 | 19.789 | 0.239 | 1.00 | 70.86 | B | C |
| ATOM | 8836 | CG | TYR | B | 34 | 71.502 | 19.080 | 0.363 | 1.00 | 79.22 | B | C |
| ATOM | 8837 | CD1 | TYR | B | 34 | 70.964 | 18.781 | 1.617 | 1.00 | 87.20 | B | C |
| ATOM | 8839 | CE1 | TYR | B | 34 | 69.737 | 18.137 | 1.740 | 1.00 | 89.29 | B | C |
| ATOM | 8841 | CZ | TYR | B | 34 | 69.029 | 17.792 | 0.600 | 1.00 | 92.08 | B | C |
| ATOM | 8842 | OH | TYR | B | 34 | 67.812 | 17.157 | 0.722 | 1.00 | 95.47 | B | O |
| ATOM | 8844 | CE2 | TYR | B | 34 | 69.537 | 18.085 | −0.659 | 1.00 | 89.29 | B | C |
| ATOM | 8846 | CD2 | TYR | B | 34 | 70.767 | 18.728 | −0.770 | 1.00 | 85.21 | B | C |
| ATOM | 8848 | C | TYR | B | 34 | 74.118 | 18.028 | −1.070 | 1.00 | 70.87 | B | C |
| ATOM | 8849 | O | TYR | B | 34 | 73.976 | 16.808 | −1.022 | 1.00 | 71.02 | B | O |
| ATOM | 8851 | N | LEU | B | 35 | 74.306 | 18.686 | −2.217 | 1.00 | 73.23 | B | N |
| ATOM | 8852 | CA | LEU | B | 35 | 74.646 | 17.990 | −3.465 | 1.00 | 75.05 | B | C |
| ATOM | 8854 | CB | LEU | B | 35 | 74.518 | 18.928 | −4.672 | 1.00 | 73.87 | B | C |
| ATOM | 8857 | CG | LEU | B | 35 | 73.181 | 19.646 | −4.918 | 1.00 | 72.69 | B | C |
| ATOM | 8859 | CD1 | LEU | B | 35 | 73.321 | 20.646 | −6.063 | 1.00 | 69.30 | B | C |
| ATOM | 8863 | CD2 | LEU | B | 35 | 72.033 | 18.678 | −5.204 | 1.00 | 66.46 | B | C |
| ATOM | 8867 | C | LEU | B | 35 | 76.092 | 17.517 | −3.304 | 1.00 | 78.50 | B | C |
| ATOM | 8868 | O | LEU | B | 35 | 76.785 | 17.996 | −2.414 | 1.00 | 79.84 | B | O |
| ATOM | 8870 | N | LEU | B | 36 | 76.554 | 16.580 | −4.126 | 1.00 | 81.41 | B | N |
| ATOM | 8871 | CA | LEU | B | 36 | 77.964 | 16.142 | −4.067 | 1.00 | 84.34 | B | C |
| ATOM | 8873 | CB | LEU | B | 36 | 78.905 | 17.267 | −4.546 | 1.00 | 84.18 | B | C |
| ATOM | 8876 | CG | LEU | B | 36 | 79.015 | 17.545 | −6.043 | 1.00 | 85.03 | B | C |
| ATOM | 8878 | CD1 | LEU | B | 36 | 79.771 | 18.850 | −6.269 | 1.00 | 85.63 | B | C |
| ATOM | 8882 | CD2 | LEU | B | 36 | 79.688 | 16.379 | −6.768 | 1.00 | 84.74 | B | C |
| ATOM | 8886 | C | LEU | B | 36 | 78.429 | 15.663 | −2.676 | 1.00 | 86.98 | B | C |
| ATOM | 8887 | O | LEU | B | 36 | 79.490 | 16.072 | −2.193 | 1.00 | 87.19 | B | O |
| ATOM | 8889 | N | SER | B | 37 | 77.637 | 14.812 | −2.029 | 1.00 | 90.52 | B | N |
| ATOM | 8890 | CA | SER | B | 37 | 78.077 | 14.126 | −0.804 | 1.00 | 92.80 | B | C |
| ATOM | 8892 | CB | SER | B | 37 | 77.125 | 14.406 | 0.375 | 1.00 | 93.04 | B | C |
| ATOM | 8895 | OG | SER | B | 37 | 76.054 | 13.477 | 0.440 | 1.00 | 93.00 | B | O |
| ATOM | 8897 | C | SER | B | 37 | 78.202 | 12.623 | −1.103 | 1.00 | 94.93 | B | C |
| ATOM | 8898 | O | SER | B | 37 | 77.529 | 12.105 | −2.009 | 1.00 | 95.38 | B | O |
| ATOM | 8900 | N | SER | B | 38 | 79.068 | 11.936 | −0.353 | 1.00 | 96.53 | B | N |
| ATOM | 8901 | CA | SER | B | 38 | 79.407 | 10.533 | −0.635 | 1.00 | 97.64 | B | C |
| ATOM | 8903 | CB | SER | B | 38 | 80.710 | 10.135 | 0.070 | 1.00 | 97.75 | B | C |
| ATOM | 8906 | OG | SER | B | 38 | 80.469 | 9.681 | 1.391 | 1.00 | 98.14 | B | O |
| ATOM | 8908 | C | SER | B | 38 | 78.277 | 9.586 | −0.222 | 1.00 | 98.41 | B | C |
| ATOM | 8909 | O | SER | B | 38 | 78.104 | 8.514 | −0.802 | 1.00 | 98.59 | B | O |
| ATOM | 8911 | N | ILE | B | 44 | 83.839 | 12.635 | −5.393 | 1.00 | 94.49 | B | N |
| ATOM | 8912 | CA | ILE | B | 44 | 82.761 | 13.547 | −5.022 | 1.00 | 93.90 | B | C |
| ATOM | 8914 | CB | ILE | B | 44 | 81.411 | 12.780 | −4.783 | 1.00 | 94.49 | B | C |
| ATOM | 8916 | CG1 | ILE | B | 44 | 81.066 | 11.873 | −5.977 | 1.00 | 95.23 | B | C |
| ATOM | 8919 | CD1 | ILE | B | 44 | 79.671 | 11.239 | −5.902 | 1.00 | 93.84 | B | C |
| ATOM | 8923 | CG2 | ILE | B | 44 | 80.260 | 13.748 | −4.553 | 1.00 | 94.85 | B | C |
| ATOM | 8927 | C | ILE | B | 44 | 83.150 | 14.379 | −3.786 | 1.00 | 92.23 | B | C |
| ATOM | 8928 | O | ILE | B | 44 | 82.375 | 15.230 | −3.340 | 1.00 | 92.29 | B | O |
| ATOM | 8930 | N | GLU | B | 45 | 84.357 | 14.149 | −3.257 | 1.00 | 89.93 | B | N |
| ATOM | 8931 | CA | GLU | B | 45 | 84.858 | 14.871 | −2.079 | 1.00 | 88.17 | B | C |
| ATOM | 8933 | CB | GLU | B | 45 | 85.549 | 13.906 | −1.114 | 1.00 | 88.70 | B | C |
| ATOM | 8936 | CG | GLU | B | 45 | 84.632 | 12.834 | −0.533 | 1.00 | 91.80 | B | C |
| ATOM | 8939 | CD | GLU | B | 45 | 85.373 | 11.838 | 0.361 | 1.00 | 95.23 | B | C |
| ATOM | 8940 | OE1 | GLU | B | 45 | 86.408 | 12.215 | 0.962 | 1.00 | 95.84 | B | O |
| ATOM | 8941 | OE2 | GLU | B | 45 | 84.916 | 10.676 | 0.465 | 1.00 | 93.58 | B | O |
| ATOM | 8942 | C | GLU | B | 45 | 85.821 | 16.011 | −2.435 | 1.00 | 85.13 | B | C |
| ATOM | 8943 | O | GLU | B | 45 | 85.588 | 17.159 | −2.053 | 1.00 | 84.84 | B | O |
| ATOM | 8945 | N | VAL | B | 46 | 86.909 | 15.693 | −3.139 | 1.00 | 81.48 | B | N |
| ATOM | 8946 | CA | VAL | B | 46 | 87.890 | 16.710 | −3.562 | 1.00 | 78.17 | B | C |
| ATOM | 8948 | CB | VAL | B | 46 | 89.203 | 16.066 | −4.107 | 1.00 | 78.25 | B | C |
| ATOM | 8950 | CG1 | VAL | B | 46 | 90.111 | 17.117 | −4.756 | 1.00 | 77.80 | B | C |
| ATOM | 8954 | CG2 | VAL | B | 46 | 89.942 | 15.339 | −2.989 | 1.00 | 78.65 | B | C |
| ATOM | 8958 | C | VAL | B | 46 | 87.271 | 17.647 | −4.609 | 1.00 | 74.01 | B | C |
| ATOM | 8959 | O | VAL | B | 46 | 87.633 | 18.815 | −4.691 | 1.00 | 74.42 | B | O |
| ATOM | 8961 | N | TYR | B | 47 | 86.343 | 17.111 | −5.397 | 1.00 | 68.89 | B | N |
| ATOM | 8962 | CA | TYR | B | 47 | 85.530 | 17.877 | −6.341 | 1.00 | 65.57 | B | C |
| ATOM | 8964 | CB | TYR | B | 47 | 84.662 | 16.884 | −7.117 | 1.00 | 65.80 | B | C |
| ATOM | 8967 | CG | TYR | B | 47 | 83.812 | 17.399 | −8.261 | 1.00 | 68.62 | B | C |
| ATOM | 8968 | CD1 | TYR | B | 47 | 84.261 | 17.333 | −9.579 | 1.00 | 72.47 | B | C |
| ATOM | 8970 | CE1 | TYR | B | 47 | 83.452 | 17.766 | −10.647 | 1.00 | 72.49 | B | C |
| ATOM | 8972 | CZ | TYR | B | 47 | 82.165 | 18.246 | −10.397 | 1.00 | 73.07 | B | C |

TABLE 4-2-continued

Coordinates of *P. alba* IspS

| | | | | | | | | | | | | |
|---|---|---|---|---|---|---|---|---|---|---|---|---|
| ATOM | 8973 | OH | TYR | B | 47 | 81.346 | 18.679 | −11.437 | 1.00 | 56.23 | B | O |
| ATOM | 8975 | CE2 | TYR | B | 47 | 81.697 | 18.296 | −9.090 | 1.00 | 72.24 | B | C |
| ATOM | 8977 | CD2 | TYR | B | 47 | 82.516 | 17.861 | −8.036 | 1.00 | 72.42 | B | C |
| ATOM | 8979 | C | TYR | B | 47 | 84.670 | 18.905 | −5.585 | 1.00 | 61.56 | B | C |
| ATOM | 8980 | O | TYR | B | 47 | 84.605 | 20.068 | −5.981 | 1.00 | 60.03 | B | O |
| ATOM | 8982 | N | LYS | B | 48 | 84.041 | 18.471 | −4.488 | 1.00 | 57.03 | B | N |
| ATOM | 8983 | CA | LYS | B | 48 | 83.250 | 19.350 | −3.606 | 1.00 | 53.54 | B | C |
| ATOM | 8985 | CB | LYS | B | 48 | 82.637 | 18.549 | −2.448 | 1.00 | 53.56 | B | C |
| ATOM | 8988 | CG | LYS | B | 48 | 81.822 | 19.383 | −1.449 | 1.00 | 55.92 | B | C |
| ATOM | 8991 | CD | LYS | B | 48 | 81.250 | 18.518 | −0.323 | 1.00 | 61.31 | B | C |
| ATOM | 8994 | CE | LYS | B | 48 | 82.258 | 18.292 | 0.806 | 1.00 | 65.33 | B | C |
| ATOM | 8997 | NZ | LYS | B | 48 | 81.669 | 17.565 | 1.968 | 1.00 | 65.45 | B | N |
| ATOM | 9001 | C | LYS | B | 48 | 84.064 | 20.505 | −3.023 | 1.00 | 49.39 | B | C |
| ATOM | 9002 | O | LYS | B | 48 | 83.614 | 21.643 | −3.014 | 1.00 | 48.79 | B | O |
| ATOM | 9004 | N | ASP | B | 49 | 85.252 | 20.197 | −2.526 | 1.00 | 45.46 | B | N |
| ATOM | 9005 | CA | ASP | B | 49 | 86.102 | 21.189 | −1.878 | 1.00 | 44.14 | B | C |
| ATOM | 9007 | CB | ASP | B | 49 | 87.217 | 20.505 | −1.049 | 1.00 | 45.26 | B | C |
| ATOM | 9010 | CG | ASP | B | 49 | 86.675 | 19.718 | 0.166 | 1.00 | 48.58 | B | C |
| ATOM | 9011 | OD1 | ASP | B | 49 | 85.493 | 19.908 | 0.553 | 1.00 | 51.70 | B | O |
| ATOM | 9012 | OD2 | ASP | B | 49 | 87.447 | 18.916 | 0.745 | 1.00 | 47.26 | B | O |
| ATOM | 9013 | C | ASP | B | 49 | 86.707 | 22.135 | −2.910 | 1.00 | 40.94 | B | C |
| ATOM | 9014 | O | ASP | B | 49 | 87.065 | 23.274 | −2.581 | 1.00 | 38.32 | B | O |
| ATOM | 9016 | N | LYS | B | 50 | 86.830 | 21.655 | −4.151 | 1.00 | 38.29 | B | N |
| ATOM | 9017 | CA | LYS | B | 50 | 87.259 | 22.502 | −5.260 | 1.00 | 36.73 | B | C |
| ATOM | 9019 | CB | LYS | B | 50 | 87.580 | 21.669 | −6.500 | 1.00 | 38.18 | B | C |
| ATOM | 9022 | CG | LYS | B | 50 | 88.431 | 22.387 | −7.554 | 1.00 | 44.48 | B | C |
| ATOM | 9025 | CD | LYS | B | 50 | 89.936 | 22.153 | −7.346 | 1.00 | 56.72 | B | C |
| ATOM | 9028 | CE | LYS | B | 50 | 90.744 | 22.329 | −8.644 | 1.00 | 59.64 | B | C |
| ATOM | 9031 | NZ | LYS | B | 50 | 90.457 | 21.259 | −9.654 | 1.00 | 56.87 | B | N |
| ATOM | 9035 | C | LYS | B | 50 | 86.141 | 23.497 | −5.555 | 1.00 | 33.08 | B | C |
| ATOM | 9036 | O | LYS | B | 50 | 86.391 | 24.692 | −5.665 | 1.00 | 32.79 | B | O |
| ATOM | 9038 | N | ALA | B | 51 | 84.905 | 23.011 | −5.635 | 1.00 | 28.99 | B | N |
| ATOM | 9039 | CA | ALA | B | 51 | 83.779 | 23.878 | −5.971 | 1.00 | 28.45 | B | C |
| ATOM | 9041 | CB | ALA | B | 51 | 82.493 | 23.070 | −6.203 | 1.00 | 26.35 | B | C |
| ATOM | 9045 | C | ALA | B | 51 | 83.570 | 24.969 | −4.908 | 1.00 | 25.62 | B | C |
| ATOM | 9046 | O | ALA | B | 51 | 83.382 | 26.125 | −5.250 | 1.00 | 27.03 | B | O |
| ATOM | 9048 | N | LYS | B | 52 | 83.640 | 24.605 | −3.639 | 1.00 | 23.23 | B | N |
| ATOM | 9049 | CA | LYS | B | 52 | 83.402 | 25.549 | −2.558 | 1.00 | 25.12 | B | C |
| ATOM | 9051 | CB | LYS | B | 52 | 83.462 | 24.826 | −1.222 | 1.00 | 26.00 | B | C |
| ATOM | 9054 | CG | LYS | B | 52 | 82.247 | 23.917 | −0.950 | 1.00 | 32.90 | B | C |
| ATOM | 9057 | CD | LYS | B | 52 | 82.548 | 22.836 | 0.119 | 1.00 | 33.42 | B | C |
| ATOM | 9060 | CE | LYS | B | 52 | 82.519 | 23.382 | 1.545 | 1.00 | 38.08 | B | C |
| ATOM | 9063 | NZ | LYS | B | 52 | 83.221 | 22.478 | 2.543 | 1.00 | 41.70 | B | N |
| ATOM | 9067 | C | LYS | B | 52 | 84.382 | 26.734 | −2.559 | 1.00 | 25.93 | B | C |
| ATOM | 9068 | O | LYS | B | 52 | 83.977 | 27.889 | −2.356 | 1.00 | 25.95 | B | O |
| ATOM | 9070 | N | LYS | B | 53 | 85.659 | 26.441 | −2.800 | 1.00 | 24.65 | B | N |
| ATOM | 9071 | CA | LYS | B | 53 | 86.713 | 27.468 | −2.865 | 1.00 | 26.16 | B | C |
| ATOM | 9073 | CB | LYS | B | 53 | 88.072 | 26.795 | −3.053 | 1.00 | 28.69 | B | C |
| ATOM | 9076 | CG | LYS | B | 53 | 89.272 | 27.687 | −2.785 | 1.00 | 38.87 | B | C |
| ATOM | 9079 | CD | LYS | B | 53 | 90.559 | 26.848 | −2.633 | 1.00 | 49.83 | B | C |
| ATOM | 9082 | CE | LYS | B | 53 | 91.819 | 27.730 | −2.464 | 1.00 | 57.01 | B | C |
| ATOM | 9085 | NZ | LYS | B | 53 | 91.931 | 28.843 | −3.484 | 1.00 | 55.43 | B | N |
| ATOM | 9089 | C | LYS | B | 53 | 86.476 | 28.458 | −4.011 | 1.00 | 23.98 | B | C |
| ATOM | 9090 | O | LYS | B | 53 | 86.553 | 29.666 | −3.818 | 1.00 | 22.54 | B | O |
| ATOM | 9092 | N | LEU | B | 54 | 86.180 | 27.918 | −5.188 | 1.00 | 22.61 | B | N |
| ATOM | 9093 | CA | LEU | B | 54 | 85.881 | 28.705 | −6.377 | 1.00 | 23.43 | B | C |
| ATOM | 9095 | CB | LEU | B | 54 | 85.746 | 27.787 | −7.601 | 1.00 | 25.24 | B | C |
| ATOM | 9098 | CG | LEU | B | 54 | 86.885 | 26.810 | −7.946 | 1.00 | 24.59 | B | C |
| ATOM | 9100 | CD1 | LEU | B | 54 | 86.382 | 25.820 | −8.997 | 1.00 | 16.54 | B | C |
| ATOM | 9104 | CD2 | LEU | B | 54 | 88.140 | 27.524 | −8.433 | 1.00 | 26.50 | B | C |
| ATOM | 9108 | C | LEU | B | 54 | 84.602 | 29.524 | −6.185 | 1.00 | 22.18 | B | C |
| ATOM | 9109 | O | LEU | B | 54 | 84.580 | 30.696 | −6.496 | 1.00 | 20.99 | B | O |
| ATOM | 9111 | N | GLU | B | 55 | 83.544 | 28.909 | −5.656 | 1.00 | 21.18 | B | N |
| ATOM | 9112 | CA | GLU | B | 55 | 82.297 | 29.631 | −5.346 | 1.00 | 19.85 | B | C |
| ATOM | 9114 | CB | GLU | B | 55 | 81.221 | 28.667 | −4.811 | 1.00 | 19.93 | B | C |
| ATOM | 9117 | CG | GLU | B | 55 | 79.945 | 29.338 | −4.252 | 1.00 | 21.78 | B | C |
| ATOM | 9120 | CD | GLU | B | 55 | 78.928 | 28.318 | −3.683 | 1.00 | 25.47 | B | C |
| ATOM | 9121 | OE1 | GLU | B | 55 | 79.358 | 27.408 | −2.970 | 1.00 | 25.89 | B | O |
| ATOM | 9122 | OE2 | GLU | B | 55 | 77.712 | 28.432 | −3.943 | 1.00 | 30.12 | B | O |
| ATOM | 9123 | C | GLU | B | 55 | 82.507 | 30.751 | −4.333 | 1.00 | 16.88 | B | C |
| ATOM | 9124 | O | GLU | B | 55 | 81.902 | 31.810 | −4.444 | 1.00 | 18.42 | B | O |
| ATOM | 9126 | N | ALA | B | 56 | 83.331 | 30.498 | −3.332 | 1.00 | 17.01 | B | N |
| ATOM | 9127 | CA | ALA | B | 56 | 83.662 | 31.512 | −2.318 | 1.00 | 17.77 | B | C |
| ATOM | 9129 | CB | ALA | B | 56 | 84.639 | 30.933 | −1.285 | 1.00 | 14.61 | B | C |
| ATOM | 9133 | C | ALA | B | 56 | 84.260 | 32.750 | −2.974 | 1.00 | 16.65 | B | C |
| ATOM | 9134 | O | ALA | B | 56 | 83.866 | 33.892 | −2.698 | 1.00 | 17.77 | B | O |
| ATOM | 9136 | N | GLU | B | 57 | 85.192 | 32.504 | −3.881 | 1.00 | 17.66 | B | N |
| ATOM | 9137 | CA | GLU | B | 57 | 85.891 | 33.568 | −4.576 | 1.00 | 19.52 | B | C |

TABLE 4-2-continued

Coordinates of *P. alba* IspS

| | | | | | | | | | | | | |
|---|---|---|---|---|---|---|---|---|---|---|---|---|
| ATOM | 9139 | CB | GLU | B | 57 | 87.061 | 32.978 | −5.370 | 1.00 | 20.51 | B | C |
| ATOM | 9142 | CG | GLU | B | 57 | 87.856 | 34.013 | −6.123 | 1.00 | 28.03 | B | C |
| ATOM | 9145 | CD | GLU | B | 57 | 89.220 | 33.529 | −6.584 | 1.00 | 29.71 | B | C |
| ATOM | 9146 | OE1 | GLU | B | 57 | 89.788 | 32.582 | −5.980 | 1.00 | 32.81 | B | O |
| ATOM | 9147 | OE2 | GLU | B | 57 | 89.714 | 34.123 | −7.558 | 1.00 | 32.47 | B | O |
| ATOM | 9148 | C | GLU | B | 57 | 84.926 | 34.373 | −5.464 | 1.00 | 18.10 | B | C |
| ATOM | 9149 | O | GLU | B | 57 | 84.956 | 35.612 | −5.451 | 1.00 | 17.86 | B | O |
| ATOM | 9151 | N | VAL | B | 58 | 84.052 | 33.683 | −6.201 | 1.00 | 15.98 | B | N |
| ATOM | 9152 | CA | VAL | B | 58 | 83.038 | 34.371 | −6.998 | 1.00 | 15.98 | B | C |
| ATOM | 9154 | CB | VAL | B | 58 | 82.222 | 33.394 | −7.875 | 1.00 | 18.04 | B | C |
| ATOM | 9156 | CG1 | VAL | B | 58 | 81.131 | 34.128 | −8.663 | 1.00 | 15.64 | B | C |
| ATOM | 9160 | CG2 | VAL | B | 58 | 83.138 | 32.696 | −8.844 | 1.00 | 18.23 | B | C |
| ATOM | 9164 | C | VAL | B | 58 | 82.135 | 35.203 | −6.089 | 1.00 | 14.38 | B | C |
| ATOM | 9165 | O | VAL | B | 58 | 81.813 | 36.330 | −6.395 | 1.00 | 12.91 | B | O |
| ATOM | 9167 | N | ARG | B | 59 | 81.773 | 34.666 | −4.935 | 1.00 | 18.23 | B | N |
| ATOM | 9168 | CA | ARG | B | 59 | 80.953 | 35.412 | −3.976 | 1.00 | 19.65 | B | C |
| ATOM | 9170 | CB | ARG | B | 59 | 80.619 | 34.534 | −2.741 | 1.00 | 22.03 | B | C |
| ATOM | 9173 | CG | ARG | B | 59 | 79.877 | 35.245 | −1.579 | 1.00 | 22.47 | B | C |
| ATOM | 9176 | CD | ARG | B | 59 | 80.840 | 36.086 | −0.641 | 1.00 | 25.58 | B | C |
| ATOM | 9179 | NE | ARG | B | 59 | 80.117 | 36.788 | 0.431 | 1.00 | 24.31 | B | N |
| ATOM | 9181 | CZ | ARG | B | 59 | 80.644 | 37.698 | 1.250 | 1.00 | 27.67 | B | C |
| ATOM | 9182 | NH1 | ARG | B | 59 | 79.881 | 38.260 | 2.182 | 1.00 | 25.80 | B | N |
| ATOM | 9185 | NH2 | ARG | B | 59 | 81.926 | 38.056 | 1.146 | 1.00 | 25.89 | B | N |
| ATOM | 9188 | C | ARG | B | 59 | 81.673 | 36.705 | −3.578 | 1.00 | 19.80 | B | C |
| ATOM | 9189 | O | ARG | B | 59 | 81.077 | 37.780 | −3.578 | 1.00 | 21.68 | B | O |
| ATOM | 9191 | N | ARG | B | 60 | 82.953 | 36.603 | −3.241 | 1.00 | 20.03 | B | N |
| ATOM | 9192 | CA | ARG | B | 60 | 83.717 | 37.782 | −2.820 | 1.00 | 18.94 | B | C |
| ATOM | 9194 | CB | ARG | B | 60 | 85.145 | 37.411 | −2.468 | 1.00 | 19.04 | B | C |
| ATOM | 9197 | CG | ARG | B | 60 | 86.020 | 38.589 | −2.002 | 1.00 | 22.87 | B | C |
| ATOM | 9200 | CD | ARG | B | 60 | 87.442 | 38.164 | −1.777 | 1.00 | 19.95 | B | C |
| ATOM | 9203 | NE | ARG | B | 60 | 88.075 | 37.838 | −3.049 | 1.00 | 25.88 | B | N |
| ATOM | 9205 | CZ | ARG | B | 60 | 89.176 | 37.106 | −3.209 | 1.00 | 26.18 | B | C |
| ATOM | 9206 | NH1 | ARG | B | 60 | 89.836 | 36.578 | −2.176 | 1.00 | 24.93 | B | N |
| ATOM | 9209 | NH2 | ARG | B | 60 | 89.620 | 36.904 | −4.435 | 1.00 | 23.40 | B | N |
| ATOM | 9212 | C | ARG | B | 60 | 83.718 | 38.843 | −3.915 | 1.00 | 18.30 | B | C |
| ATOM | 9213 | O | ARG | B | 60 | 83.427 | 40.007 | −3.650 | 1.00 | 16.21 | B | O |
| ATOM | 9215 | N | GLU | B | 61 | 84.015 | 38.434 | −5.140 | 1.00 | 18.15 | B | N |
| ATOM | 9216 | CA | GLU | B | 61 | 84.066 | 39.367 | −6.264 | 1.00 | 18.45 | B | C |
| ATOM | 9218 | CB | GLU | B | 61 | 84.564 | 38.663 | −7.523 | 1.00 | 18.70 | B | C |
| ATOM | 9221 | CG | GLU | B | 61 | 86.037 | 38.270 | −7.425 | 1.00 | 25.62 | B | C |
| ATOM | 9224 | CD | GLU | B | 61 | 86.901 | 39.429 | −6.970 | 1.00 | 31.59 | B | C |
| ATOM | 9225 | OE1 | GLU | B | 61 | 86.893 | 40.488 | −7.648 | 1.00 | 33.81 | B | O |
| ATOM | 9226 | OE2 | GLU | B | 61 | 87.559 | 39.290 | −5.918 | 1.00 | 30.53 | B | O |
| ATOM | 9227 | C | GLU | B | 61 | 82.734 | 40.062 | −6.528 | 1.00 | 17.97 | B | C |
| ATOM | 9228 | O | GLU | B | 61 | 82.711 | 41.245 | −6.761 | 1.00 | 19.38 | B | O |
| ATOM | 9230 | N | ILE | B | 62 | 81.617 | 39.356 | −6.435 | 1.00 | 17.52 | B | N |
| ATOM | 9231 | CA | ILE | B | 62 | 80.341 | 40.023 | −6.594 | 1.00 | 18.58 | B | C |
| ATOM | 9233 | CB | ILE | B | 62 | 79.169 | 39.006 | −6.731 | 1.00 | 19.89 | B | C |
| ATOM | 9235 | CG1 | ILE | B | 62 | 79.343 | 38.137 | −7.974 | 1.00 | 21.73 | B | C |
| ATOM | 9238 | CD1 | ILE | B | 62 | 78.456 | 36.881 | −8.000 | 1.00 | 15.32 | B | C |
| ATOM | 9242 | CG2 | ILE | B | 62 | 77.810 | 39.738 | −6.823 | 1.00 | 21.38 | B | C |
| ATOM | 9246 | C | ILE | B | 62 | 80.071 | 41.005 | −5.433 | 1.00 | 19.09 | B | C |
| ATOM | 9247 | O | ILE | B | 62 | 79.379 | 41.984 | −5.615 | 1.00 | 20.23 | B | O |
| ATOM | 9249 | N | ASN | B | 63 | 80.606 | 40.732 | −4.244 | 1.00 | 20.89 | B | N |
| ATOM | 9250 | CA | ASN | B | 63 | 80.300 | 41.510 | −3.024 | 1.00 | 21.02 | B | C |
| ATOM | 9252 | CB | ASN | B | 63 | 80.355 | 40.597 | −1.783 | 1.00 | 20.11 | B | C |
| ATOM | 9255 | CG | ASN | B | 63 | 79.061 | 39.859 | −1.543 | 1.00 | 25.79 | B | C |
| ATOM | 9256 | OD1 | ASN | B | 63 | 78.128 | 40.417 | −0.976 | 1.00 | 29.46 | B | O |
| ATOM | 9257 | ND2 | ASN | B | 63 | 78.999 | 38.591 | −1.957 | 1.00 | 22.36 | B | N |
| ATOM | 9260 | C | ASN | B | 63 | 81.262 | 42.671 | −2.838 | 1.00 | 23.00 | B | C |
| ATOM | 9261 | O | ASN | B | 63 | 81.077 | 43.514 | −1.968 | 1.00 | 22.33 | B | O |
| ATOM | 9263 | N | ASN | B | 64 | 82.292 | 42.697 | −3.674 | 1.00 | 25.47 | B | N |
| ATOM | 9264 | CA | ASN | B | 64 | 83.322 | 43.708 | −3.630 | 1.00 | 27.17 | B | C |
| ATOM | 9266 | CB | ASN | B | 64 | 84.400 | 43.341 | −4.646 | 1.00 | 28.05 | B | C |
| ATOM | 9269 | CG | ASN | B | 64 | 85.562 | 44.319 | −4.642 | 1.00 | 28.60 | B | C |
| ATOM | 9270 | OD1 | ASN | B | 64 | 85.793 | 45.052 | −3.663 | 1.00 | 21.94 | B | O |
| ATOM | 9271 | ND2 | ASN | B | 64 | 86.299 | 44.331 | −5.732 | 1.00 | 18.57 | B | N |
| ATOM | 9274 | C | ASN | B | 64 | 82.840 | 45.121 | −3.922 | 1.00 | 29.58 | B | C |
| ATOM | 9275 | O | ASN | B | 64 | 82.518 | 45.441 | −5.073 | 1.00 | 30.80 | B | O |
| ATOM | 9277 | N | GLU | B | 65 | 82.848 | 45.977 | −2.901 | 1.00 | 31.46 | B | N |
| ATOM | 9278 | CA | GLU | B | 65 | 82.308 | 47.333 | −3.039 | 1.00 | 34.52 | B | C |
| ATOM | 9280 | CB | GLU | B | 65 | 81.787 | 47.849 | −1.680 | 1.00 | 36.07 | B | C |
| ATOM | 9283 | CG | GLU | B | 65 | 80.519 | 47.079 | −1.202 | 1.00 | 40.76 | B | C |
| ATOM | 9286 | CD | GLU | B | 65 | 79.853 | 47.631 | 0.070 | 1.00 | 46.69 | B | C |
| ATOM | 9287 | OE1 | GLU | B | 65 | 79.267 | 46.807 | 0.819 | 1.00 | 45.52 | B | O |
| ATOM | 9288 | OE2 | GLU | B | 65 | 79.891 | 48.862 | 0.314 | 1.00 | 44.38 | B | O |
| ATOM | 9289 | C | GLU | B | 65 | 83.299 | 48.314 | −3.700 | 1.00 | 34.91 | B | C |
| ATOM | 9290 | O | GLU | B | 65 | 82.903 | 49.396 | −4.110 | 1.00 | 35.59 | B | O |

TABLE 4-2-continued

| Coordinates of *P. alba* IspS | | | | | | | | | | | | |
|---|---|---|---|---|---|---|---|---|---|---|---|---|
| ATOM | 9292 | N | LYS | B | 66 | 84.561 | 47.909 | −3.843 | 1.00 | 34.28 | B | N |
| ATOM | 9293 | CA | LYS | B | 66 | 85.599 | 48.730 | −4.488 | 1.00 | 35.18 | B | C |
| ATOM | 9295 | CB | LYS | B | 66 | 86.982 | 48.469 | −3.863 | 1.00 | 35.99 | B | C |
| ATOM | 9298 | CG | LYS | B | 66 | 87.045 | 48.467 | −2.339 | 1.00 | 38.17 | B | C |
| ATOM | 9301 | CD | LYS | B | 66 | 88.463 | 48.112 | −1.873 | 1.00 | 44.44 | B | C |
| ATOM | 9304 | CE | LYS | B | 66 | 88.568 | 47.948 | −0.356 | 1.00 | 45.69 | B | C |
| ATOM | 9307 | NZ | LYS | B | 66 | 87.722 | 48.925 | 0.382 | 1.00 | 46.38 | B | N |
| ATOM | 9311 | C | LYS | B | 66 | 85.706 | 48.474 | −5.997 | 1.00 | 33.33 | B | C |
| ATOM | 9312 | O | LYS | B | 66 | 86.472 | 49.135 | −6.685 | 1.00 | 31.57 | B | O |
| ATOM | 9314 | N | ALA | B | 67 | 84.959 | 47.506 | −6.507 | 1.00 | 33.36 | B | N |
| ATOM | 9315 | CA | ALA | B | 67 | 85.026 | 47.165 | −7.925 | 1.00 | 34.20 | B | C |
| ATOM | 9317 | CB | ALA | B | 67 | 84.218 | 45.897 | −8.204 | 1.00 | 33.29 | B | C |
| ATOM | 9321 | C | ALA | B | 67 | 84.525 | 48.322 | −8.800 | 1.00 | 33.66 | B | C |
| ATOM | 9322 | O | ALA | B | 67 | 83.650 | 49.084 | −8.405 | 1.00 | 30.94 | B | O |
| ATOM | 9324 | N | GLU | B | 68 | 85.105 | 48.461 | −9.983 | 1.00 | 35.83 | B | N |
| ATOM | 9325 | CA | GLU | B | 68 | 84.593 | 49.428 | −10.952 | 1.00 | 38.70 | B | C |
| ATOM | 9327 | CB | GLU | B | 68 | 85.515 | 49.528 | −12.176 | 1.00 | 40.06 | B | C |
| ATOM | 9330 | CG | GLU | B | 68 | 85.648 | 50.931 | −12.771 | 1.00 | 49.30 | B | C |
| ATOM | 9333 | CD | GLU | B | 68 | 86.723 | 51.762 | −12.087 | 1.00 | 60.51 | B | C |
| ATOM | 9334 | OE1 | GLU | B | 68 | 86.676 | 51.895 | −10.839 | 1.00 | 64.15 | B | O |
| ATOM | 9335 | OE2 | GLU | B | 68 | 87.615 | 52.287 | −12.800 | 1.00 | 64.74 | B | O |
| ATOM | 9336 | C | GLU | B | 68 | 83.188 | 48.938 | −11.336 | 1.00 | 38.52 | B | C |
| ATOM | 9337 | O | GLU | B | 68 | 82.979 | 47.736 | −11.557 | 1.00 | 35.34 | B | O |
| ATOM | 9339 | N | PHE | B | 69 | 82.231 | 49.862 | −11.388 | 1.00 | 39.72 | B | N |
| ATOM | 9340 | CA | PHE | B | 69 | 80.824 | 49.499 | −11.583 | 1.00 | 40.88 | B | C |
| ATOM | 9342 | CB | PHE | B | 69 | 79.890 | 50.704 | −11.385 | 1.00 | 43.17 | B | C |
| ATOM | 9345 | CG | PHE | B | 69 | 79.457 | 50.916 | −9.936 | 1.00 | 53.21 | B | C |
| ATOM | 9346 | CD1 | PHE | B | 69 | 78.868 | 49.875 | −9.202 | 1.00 | 61.30 | B | C |
| ATOM | 9348 | CE1 | PHE | B | 69 | 78.463 | 50.062 | −7.870 | 1.00 | 62.25 | B | C |
| ATOM | 9350 | CZ | PHE | B | 69 | 78.638 | 51.301 | −7.260 | 1.00 | 64.99 | B | C |
| ATOM | 9352 | CE2 | PHE | B | 69 | 79.218 | 52.351 | −7.978 | 1.00 | 65.67 | B | C |
| ATOM | 9354 | CD2 | PHE | B | 69 | 79.621 | 52.156 | −9.312 | 1.00 | 63.60 | B | C |
| ATOM | 9356 | C | PHE | B | 69 | 80.540 | 48.786 | −12.914 | 1.00 | 38.20 | B | C |
| ATOM | 9357 | O | PHE | B | 69 | 79.713 | 47.862 | −12.946 | 1.00 | 35.79 | B | O |
| ATOM | 9359 | N | LEU | B | 70 | 81.237 | 49.159 | −13.983 | 1.00 | 34.86 | B | N |
| ATOM | 9360 | CA | LEU | B | 70 | 81.085 | 48.435 | −15.256 | 1.00 | 35.39 | B | C |
| ATOM | 9362 | CB | LEU | B | 70 | 81.786 | 49.157 | −16.411 | 1.00 | 35.66 | B | C |
| ATOM | 9365 | CG | LEU | B | 70 | 81.573 | 48.513 | −17.786 | 1.00 | 42.16 | B | C |
| ATOM | 9367 | CD1 | LEU | B | 70 | 80.104 | 48.554 | −18.171 | 1.00 | 42.12 | B | C |
| ATOM | 9371 | CD2 | LEU | B | 70 | 82.425 | 49.189 | −18.855 | 1.00 | 49.16 | B | C |
| ATOM | 9375 | C | LEU | B | 70 | 81.603 | 46.999 | −15.160 | 1.00 | 32.47 | B | C |
| ATOM | 9376 | O | LEU | B | 70 | 80.945 | 46.071 | −15.596 | 1.00 | 31.99 | B | O |
| ATOM | 9378 | N | THR | B | 71 | 82.790 | 46.834 | −14.592 | 1.00 | 31.77 | B | N |
| ATOM | 9379 | CA | THR | B | 71 | 83.396 | 45.516 | −14.366 | 1.00 | 30.39 | B | C |
| ATOM | 9381 | CB | THR | B | 71 | 84.794 | 45.678 | −13.756 | 1.00 | 31.06 | B | C |
| ATOM | 9383 | OG1 | THR | B | 71 | 85.585 | 46.494 | −14.633 | 1.00 | 34.93 | B | O |
| ATOM | 9385 | CG2 | THR | B | 71 | 85.476 | 44.322 | −13.563 | 1.00 | 31.45 | B | C |
| ATOM | 9389 | C | THR | B | 71 | 82.533 | 44.619 | −13.460 | 1.00 | 27.80 | B | C |
| ATOM | 9390 | O | THR | B | 71 | 82.450 | 43.412 | −13.675 | 1.00 | 27.97 | B | O |
| ATOM | 9392 | N | LEU | B | 72 | 81.878 | 45.215 | −12.467 | 1.00 | 25.13 | B | N |
| ATOM | 9393 | CA | LEU | B | 72 | 80.955 | 44.476 | −11.614 | 1.00 | 24.98 | B | C |
| ATOM | 9395 | CB | LEU | B | 72 | 80.511 | 45.327 | −10.443 | 1.00 | 24.24 | B | C |
| ATOM | 9398 | CG | LEU | B | 72 | 79.716 | 44.642 | −9.339 | 1.00 | 33.31 | B | C |
| ATOM | 9400 | CD1 | LEU | B | 72 | 80.492 | 43.465 | −8.715 | 1.00 | 32.42 | B | C |
| ATOM | 9404 | CD2 | LEU | B | 72 | 79.346 | 45.677 | −8.266 | 1.00 | 35.81 | B | C |
| ATOM | 9408 | C | LEU | B | 72 | 79.736 | 44.026 | −12.410 | 1.00 | 24.17 | B | C |
| ATOM | 9409 | O | LEU | B | 72 | 79.330 | 42.888 | −12.318 | 1.00 | 21.92 | B | O |
| ATOM | 9411 | N | LEU | B | 73 | 79.158 | 44.928 | −13.196 | 1.00 | 24.75 | B | N |
| ATOM | 9412 | CA | LEU | B | 73 | 78.018 | 44.568 | −14.012 | 1.00 | 25.30 | B | C |
| ATOM | 9414 | CB | LEU | B | 73 | 77.467 | 45.786 | −14.758 | 1.00 | 25.87 | B | C |
| ATOM | 9417 | CG | LEU | B | 73 | 76.666 | 46.820 | −13.948 | 1.00 | 26.49 | B | C |
| ATOM | 9419 | CD1 | LEU | B | 73 | 76.237 | 47.980 | −14.845 | 1.00 | 24.24 | B | C |
| ATOM | 9423 | CD2 | LEU | B | 73 | 75.462 | 46.210 | −13.265 | 1.00 | 20.11 | B | C |
| ATOM | 9427 | C | LEU | B | 73 | 78.383 | 43.437 | −14.996 | 1.00 | 24.80 | B | C |
| ATOM | 9428 | O | LEU | B | 73 | 77.630 | 42.492 | −15.150 | 1.00 | 24.71 | B | O |
| ATOM | 9430 | N | GLU | B | 74 | 79.530 | 43.526 | −15.650 | 1.00 | 23.04 | B | N |
| ATOM | 9431 | CA | GLU | B | 74 | 79.934 | 42.456 | −16.561 | 1.00 | 24.32 | B | C |
| ATOM | 9433 | CB | GLU | B | 74 | 81.164 | 42.873 | −17.383 | 1.00 | 24.31 | B | C |
| ATOM | 9436 | CG | GLU | B | 74 | 80.842 | 43.894 | −18.492 | 1.00 | 35.06 | B | C |
| ATOM | 9439 | CD | GLU | B | 74 | 82.069 | 44.669 | −19.044 | 1.00 | 42.57 | B | C |
| ATOM | 9440 | OE1 | GLU | B | 74 | 83.235 | 44.254 | −18.819 | 1.00 | 41.46 | B | O |
| ATOM | 9441 | OE2 | GLU | B | 74 | 81.844 | 45.714 | −19.713 | 1.00 | 49.19 | B | O |
| ATOM | 9442 | C | GLU | B | 74 | 80.187 | 41.124 | −15.811 | 1.00 | 23.65 | B | C |
| ATOM | 9443 | O | GLU | B | 74 | 79.951 | 40.034 | −16.343 | 1.00 | 24.23 | B | O |
| ATOM | 9445 | N | LEU | B | 75 | 80.667 | 41.208 | −14.579 | 1.00 | 22.21 | B | N |
| ATOM | 9446 | CA | LEU | B | 75 | 80.888 | 40.012 | −13.794 | 1.00 | 20.79 | B | C |
| ATOM | 9448 | CB | LEU | B | 75 | 81.548 | 40.334 | −12.445 | 1.00 | 19.72 | B | C |
| ATOM | 9451 | CG | LEU | B | 75 | 81.715 | 39.168 | −11.461 | 1.00 | 19.52 | B | C |

TABLE 4-2-continued

Coordinates of *P. alba* IspS

| | | | | | | | | | | | | |
|---|---|---|---|---|---|---|---|---|---|---|---|---|
| ATOM | 9453 | CD1 | LEU | B | 75 | 82.486 | 38.032 | −12.119 | 1.00 | 16.13 | B | C |
| ATOM | 9457 | CD2 | LEU | B | 75 | 82.437 | 39.647 | −10.211 | 1.00 | 21.45 | B | C |
| ATOM | 9461 | C | LEU | B | 75 | 79.553 | 39.335 | −13.576 | 1.00 | 19.44 | B | C |
| ATOM | 9462 | O | LEU | B | 75 | 79.445 | 38.130 | −13.753 | 1.00 | 21.48 | B | O |
| ATOM | 9464 | N | ILE | B | 76 | 78.543 | 40.115 | −13.197 | 1.00 | 19.42 | B | N |
| ATOM | 9465 | CA | ILE | B | 76 | 77.230 | 39.579 | −12.907 | 1.00 | 21.46 | B | C |
| ATOM | 9467 | CB | ILE | B | 76 | 76.256 | 40.654 | −12.379 | 1.00 | 23.58 | B | C |
| ATOM | 9469 | CG1 | ILE | B | 76 | 76.708 | 41.135 | −10.996 | 1.00 | 24.75 | B | C |
| ATOM | 9472 | CD1 | ILE | B | 76 | 75.987 | 42.362 | −10.509 | 1.00 | 22.54 | B | C |
| ATOM | 9476 | CG2 | ILE | B | 76 | 74.826 | 40.102 | −12.297 | 1.00 | 15.99 | B | C |
| ATOM | 9480 | C | ILE | B | 76 | 76.632 | 38.972 | −14.151 | 1.00 | 23.08 | B | C |
| ATOM | 9481 | O | ILE | B | 76 | 75.984 | 37.933 | −14.081 | 1.00 | 24.81 | B | O |
| ATOM | 9483 | N | ASP | B | 77 | 76.854 | 39.610 | −15.293 | 1.00 | 23.68 | B | N |
| ATOM | 9484 | CA | ASP | B | 77 | 76.279 | 39.122 | −16.545 | 1.00 | 23.98 | B | C |
| ATOM | 9486 | CB | ASP | B | 77 | 76.545 | 40.109 | −17.669 | 1.00 | 24.72 | B | C |
| ATOM | 9489 | CG | ASP | B | 77 | 75.708 | 39.838 | −18.906 | 1.00 | 28.60 | B | C |
| ATOM | 9490 | OD1 | ASP | B | 77 | 74.657 | 39.176 | −18.811 | 1.00 | 27.91 | B | O |
| ATOM | 9491 | OD2 | ASP | B | 77 | 76.095 | 40.332 | −19.984 | 1.00 | 33.20 | B | O |
| ATOM | 9492 | C | ASP | B | 77 | 76.900 | 37.791 | −16.896 | 1.00 | 22.93 | B | C |
| ATOM | 9493 | O | ASP | B | 77 | 76.206 | 36.855 | −17.301 | 1.00 | 21.74 | B | O |
| ATOM | 9495 | N | ASN | B | 78 | 78.211 | 37.703 | −16.733 | 1.00 | 21.06 | B | N |
| ATOM | 9496 | CA | ASN | B | 78 | 78.925 | 36.463 | −17.029 | 1.00 | 22.27 | B | C |
| ATOM | 9498 | CB | ASN | B | 78 | 80.438 | 36.637 | −16.866 | 1.00 | 25.30 | B | C |
| ATOM | 9501 | CG | ASN | B | 78 | 81.081 | 37.404 | −18.019 | 1.00 | 26.72 | B | C |
| ATOM | 9502 | OD1 | ASN | B | 78 | 80.708 | 37.233 | −19.156 | 1.00 | 23.36 | B | O |
| ATOM | 9503 | ND2 | ASN | B | 78 | 82.081 | 38.219 | −17.714 | 1.00 | 21.70 | B | N |
| ATOM | 9506 | C | ASN | B | 78 | 78.458 | 35.353 | −16.109 | 1.00 | 21.56 | B | C |
| ATOM | 9507 | O | ASN | B | 78 | 78.201 | 34.240 | −16.549 | 1.00 | 20.19 | B | O |
| ATOM | 9509 | N | VAL | B | 79 | 78.340 | 35.664 | −14.825 | 1.00 | 20.29 | B | N |
| ATOM | 9510 | CA | VAL | B | 79 | 77.917 | 34.672 | −13.843 | 1.00 | 21.77 | B | C |
| ATOM | 9512 | CB | VAL | B | 79 | 77.857 | 35.306 | −12.419 | 1.00 | 23.62 | B | C |
| ATOM | 9514 | CG1 | VAL | B | 79 | 77.001 | 34.467 | −11.466 | 1.00 | 19.36 | B | C |
| ATOM | 9518 | CG2 | VAL | B | 79 | 79.265 | 35.515 | −11.862 | 1.00 | 19.30 | B | C |
| ATOM | 9522 | C | VAL | B | 79 | 76.552 | 34.064 | −14.217 | 1.00 | 22.02 | B | C |
| ATOM | 9523 | O | VAL | B | 79 | 76.349 | 32.862 | −14.107 | 1.00 | 22.00 | B | O |
| ATOM | 9525 | N | GLN | B | 80 | 75.630 | 34.910 | −14.672 | 1.00 | 21.01 | B | N |
| ATOM | 9526 | CA | GLN | B | 80 | 74.265 | 34.482 | −15.024 | 1.00 | 19.29 | B | C |
| ATOM | 9528 | CB | GLN | B | 80 | 73.343 | 35.686 | −15.126 | 1.00 | 15.00 | B | C |
| ATOM | 9531 | CG | GLN | B | 80 | 73.128 | 36.374 | −13.771 | 1.00 | 17.76 | B | C |
| ATOM | 9534 | CD | GLN | B | 80 | 71.957 | 37.344 | −13.766 | 1.00 | 21.46 | B | C |
| ATOM | 9535 | OE1 | GLN | B | 80 | 71.283 | 37.519 | −12.744 | 1.00 | 24.61 | B | O |
| ATOM | 9536 | NE2 | GLN | B | 80 | 71.702 | 37.966 | −14.903 | 1.00 | 18.12 | B | N |
| ATOM | 9539 | C | GLN | B | 80 | 74.244 | 33.713 | −16.339 | 1.00 | 21.60 | B | C |
| ATOM | 9540 | O | GLN | B | 80 | 73.655 | 32.624 | −16.426 | 1.00 | 23.34 | B | O |
| ATOM | 9542 | N | ARG | B | 81 | 74.930 | 34.258 | −17.340 | 1.00 | 19.85 | B | N |
| ATOM | 9543 | CA | ARG | B | 81 | 75.018 | 33.618 | −18.651 | 1.00 | 21.31 | B | C |
| ATOM | 9545 | CB | ARG | B | 81 | 75.744 | 34.528 | −19.651 | 1.00 | 22.39 | B | C |
| ATOM | 9548 | CG | ARG | B | 81 | 74.902 | 35.779 | −19.950 | 1.00 | 24.93 | B | C |
| ATOM | 9551 | CD | ARG | B | 81 | 75.364 | 36.514 | −21.183 | 1.00 | 27.95 | B | C |
| ATOM | 9554 | NE | ARG | B | 81 | 75.370 | 35.628 | −22.346 | 1.00 | 33.40 | B | N |
| ATOM | 9556 | CZ | ARG | B | 81 | 75.597 | 36.035 | −23.594 | 1.00 | 44.92 | B | C |
| ATOM | 9557 | NH1 | ARG | B | 81 | 75.801 | 37.326 | −23.849 | 1.00 | 43.90 | B | N |
| ATOM | 9560 | NH2 | ARG | B | 81 | 75.593 | 35.149 | −24.597 | 1.00 | 41.12 | B | N |
| ATOM | 9563 | C | ARG | B | 81 | 75.669 | 32.256 | −18.590 | 1.00 | 20.24 | B | C |
| ATOM | 9564 | O | ARG | B | 81 | 75.228 | 31.322 | −19.268 | 1.00 | 23.90 | B | O |
| ATOM | 9566 | N | LEU | B | 82 | 76.683 | 32.119 | −17.747 | 1.00 | 18.56 | B | N |
| ATOM | 9567 | CA | LEU | B | 82 | 77.374 | 30.837 | −17.558 | 1.00 | 17.31 | B | C |
| ATOM | 9569 | CB | LEU | B | 82 | 78.723 | 31.056 | −16.857 | 1.00 | 17.11 | B | C |
| ATOM | 9572 | CG | LEU | B | 82 | 79.810 | 31.804 | −17.660 | 1.00 | 23.24 | B | C |
| ATOM | 9574 | CD1 | LEU | B | 82 | 80.870 | 32.349 | −16.695 | 1.00 | 14.65 | B | C |
| ATOM | 9578 | CD2 | LEU | B | 82 | 80.450 | 30.919 | −18.756 | 1.00 | 16.24 | B | C |
| ATOM | 9582 | C | LEU | B | 82 | 76.546 | 29.833 | −16.757 | 1.00 | 16.56 | B | C |
| ATOM | 9583 | O | LEU | B | 82 | 76.966 | 28.708 | −16.571 | 1.00 | 17.24 | B | O |
| ATOM | 9585 | N | GLY | B | 83 | 75.391 | 30.245 | −16.253 | 1.00 | 19.51 | B | N |
| ATOM | 9586 | CA | GLY | B | 83 | 74.459 | 29.326 | −15.600 | 1.00 | 20.32 | B | C |
| ATOM | 9589 | C | GLY | B | 83 | 74.479 | 29.334 | −14.085 | 1.00 | 21.68 | B | C |
| ATOM | 9590 | O | GLY | B | 83 | 73.823 | 28.495 | −13.459 | 1.00 | 24.50 | B | O |
| ATOM | 9592 | N | LEU | B | 84 | 75.188 | 30.288 | −13.480 | 1.00 | 21.90 | B | N |
| ATOM | 9593 | CA | LEU | B | 84 | 75.440 | 30.252 | −12.043 | 1.00 | 23.56 | B | C |
| ATOM | 9595 | CB | LEU | B | 84 | 76.918 | 30.462 | −11.762 | 1.00 | 21.53 | B | C |
| ATOM | 9598 | CG | LEU | B | 84 | 77.914 | 29.392 | −12.227 | 1.00 | 22.51 | B | C |
| ATOM | 9600 | CD1 | LEU | B | 84 | 79.332 | 30.012 | −12.350 | 1.00 | 17.35 | B | C |
| ATOM | 9604 | CD2 | LEU | B | 84 | 77.936 | 28.211 | −11.274 | 1.00 | 14.52 | B | C |
| ATOM | 9608 | C | LEU | B | 84 | 74.614 | 31.286 | −11.267 | 1.00 | 24.75 | B | C |
| ATOM | 9609 | O | LEU | B | 84 | 74.793 | 31.464 | −10.050 | 1.00 | 23.23 | B | O |
| ATOM | 9611 | N | GLY | B | 85 | 73.704 | 31.946 | −11.957 | 1.00 | 20.07 | B | N |
| ATOM | 9612 | CA | GLY | B | 85 | 72.905 | 32.986 | −11.331 | 1.00 | 23.42 | B | C |
| ATOM | 9615 | C | GLY | B | 85 | 72.103 | 32.548 | −10.128 | 1.00 | 23.55 | B | C |

TABLE 4-2-continued

Coordinates of *P. alba* IspS

| | | | | | | | | | | | | |
|---|---|---|---|---|---|---|---|---|---|---|---|---|
| ATOM | 9616 | O | GLY | B | 85 | 72.051 | 33.276 | −9.129 | 1.00 | 24.14 | B | O |
| ATOM | 9618 | N | TYR | B | 86 | 71.493 | 31.358 | −10.216 | 1.00 | 25.41 | B | N |
| ATOM | 9619 | CA | TYR | B | 86 | 70.653 | 30.780 | −9.138 | 1.00 | 24.89 | B | C |
| ATOM | 9621 | CB | TYR | B | 86 | 70.088 | 29.405 | −9.555 | 1.00 | 23.46 | B | C |
| ATOM | 9624 | CG | TYR | B | 86 | 71.098 | 28.272 | −9.477 | 1.00 | 20.27 | B | C |
| ATOM | 9625 | CD1 | TYR | B | 86 | 71.113 | 27.378 | −8.409 | 1.00 | 18.85 | B | C |
| ATOM | 9627 | CE1 | TYR | B | 86 | 72.051 | 26.334 | −8.361 | 1.00 | 21.28 | B | C |
| ATOM | 9629 | CZ | TYR | B | 86 | 72.972 | 26.173 | −9.391 | 1.00 | 21.08 | B | C |
| ATOM | 9630 | OH | TYR | B | 86 | 73.936 | 25.171 | −9.372 | 1.00 | 14.76 | B | O |
| ATOM | 9632 | CE2 | TYR | B | 86 | 72.949 | 27.035 | −10.447 | 1.00 | 15.78 | B | C |
| ATOM | 9634 | CD2 | TYR | B | 86 | 72.029 | 28.084 | −10.477 | 1.00 | 18.71 | B | C |
| ATOM | 9636 | C | TYR | B | 86 | 71.418 | 30.580 | −7.843 | 1.00 | 27.93 | B | C |
| ATOM | 9637 | O | TYR | B | 86 | 70.847 | 30.313 | −6.788 | 1.00 | 29.61 | B | O |
| ATOM | 9639 | N | ARG | B | 87 | 72.730 | 30.655 | −7.953 | 1.00 | 27.91 | B | N |
| ATOM | 9640 | CA | ARG | B | 87 | 73.620 | 30.275 | −6.899 | 1.00 | 27.88 | B | C |
| ATOM | 9642 | CB | ARG | B | 87 | 74.812 | 29.611 | −7.587 | 1.00 | 30.15 | B | C |
| ATOM | 9645 | CG | ARG | B | 87 | 75.709 | 28.864 | −6.734 | 1.00 | 30.85 | B | C |
| ATOM | 9648 | CD | ARG | B | 87 | 76.316 | 27.640 | −7.442 | 1.00 | 29.13 | B | C |
| ATOM | 9651 | NE | ARG | B | 87 | 76.612 | 26.804 | −6.332 | 1.00 | 26.20 | B | N |
| ATOM | 9653 | CZ | ARG | B | 87 | 75.932 | 25.744 | −5.944 | 1.00 | 24.61 | B | C |
| ATOM | 9654 | NH1 | ARG | B | 87 | 76.289 | 25.177 | −4.803 | 1.00 | 36.76 | B | N |
| ATOM | 9657 | NH2 | ARG | B | 87 | 74.970 | 25.210 | −6.680 | 1.00 | 26.43 | B | N |
| ATOM | 9660 | C | ARG | B | 87 | 74.038 | 31.512 | −6.147 | 1.00 | 27.03 | B | C |
| ATOM | 9661 | O | ARG | B | 87 | 74.506 | 31.421 | −5.028 | 1.00 | 25.59 | B | O |
| ATOM | 9663 | N | PHE | B | 88 | 73.855 | 32.679 | −6.776 | 1.00 | 28.24 | B | N |
| ATOM | 9664 | CA | PHE | B | 88 | 74.438 | 33.940 | −6.297 | 1.00 | 28.26 | B | C |
| ATOM | 9666 | CB | PHE | B | 88 | 75.605 | 34.341 | −7.210 | 1.00 | 25.39 | B | C |
| ATOM | 9669 | CG | PHE | B | 88 | 76.807 | 33.456 | −7.079 | 1.00 | 25.44 | B | C |
| ATOM | 9670 | CD1 | PHE | B | 88 | 77.569 | 33.468 | −5.924 | 1.00 | 18.49 | B | C |
| ATOM | 9672 | CE1 | PHE | B | 88 | 78.678 | 32.671 | −5.811 | 1.00 | 25.00 | B | C |
| ATOM | 9674 | CZ | PHE | B | 88 | 79.048 | 31.820 | −6.862 | 1.00 | 22.42 | B | C |
| ATOM | 9676 | CE2 | PHE | B | 88 | 78.292 | 31.788 | −8.000 | 1.00 | 19.97 | B | C |
| ATOM | 9678 | CD2 | PHE | B | 88 | 77.180 | 32.609 | −8.112 | 1.00 | 21.12 | B | C |
| ATOM | 9680 | C | PHE | B | 88 | 73.404 | 35.074 | −6.240 | 1.00 | 29.32 | B | C |
| ATOM | 9681 | O | PHE | B | 88 | 73.756 | 36.270 | −6.250 | 1.00 | 29.34 | B | O |
| ATOM | 9683 | N | GLU | B | 89 | 72.140 | 34.695 | −6.141 | 1.00 | 29.21 | B | N |
| ATOM | 9684 | CA | GLU | B | 89 | 71.049 | 35.650 | −6.224 | 1.00 | 32.70 | B | C |
| ATOM | 9686 | CB | GLU | B | 89 | 69.701 | 34.937 | −6.103 | 1.00 | 33.74 | B | C |
| ATOM | 9689 | CG | GLU | B | 89 | 68.512 | 35.887 | −6.195 | 1.00 | 45.69 | B | C |
| ATOM | 9692 | CD | GLU | B | 89 | 67.208 | 35.206 | −6.586 | 1.00 | 55.76 | B | C |
| ATOM | 9693 | OE1 | GLU | B | 89 | 67.250 | 34.124 | −7.225 | 1.00 | 57.29 | B | O |
| ATOM | 9694 | OE2 | GLU | B | 89 | 66.142 | 35.787 | −6.272 | 1.00 | 58.91 | B | O |
| ATOM | 9695 | C | GLU | B | 89 | 71.156 | 36.755 | −5.186 | 1.00 | 31.50 | B | C |
| ATOM | 9696 | O | GLU | B | 89 | 71.011 | 37.913 | −5.516 | 1.00 | 33.00 | B | O |
| ATOM | 9698 | N | SER | B | 90 | 71.421 | 36.425 | −3.935 | 1.00 | 31.61 | B | N |
| ATOM | 9699 | CA | SER | B | 90 | 71.404 | 37.470 | −2.907 | 1.00 | 31.80 | B | C |
| ATOM | 9701 | CB | SER | B | 90 | 71.315 | 36.860 | −1.490 | 1.00 | 32.58 | B | C |
| ATOM | 9704 | OG | SER | B | 90 | 72.570 | 36.431 | −0.986 | 1.00 | 41.51 | B | O |
| ATOM | 9706 | C | SER | B | 90 | 72.600 | 38.420 | −3.061 | 1.00 | 29.63 | B | C |
| ATOM | 9707 | O | SER | B | 90 | 72.524 | 39.599 | −2.730 | 1.00 | 30.79 | B | O |
| ATOM | 9709 | N | ASP | B | 91 | 73.707 | 37.902 | −3.576 | 1.00 | 26.77 | B | N |
| ATOM | 9710 | CA | ASP | B | 91 | 74.889 | 38.721 | −3.783 | 1.00 | 24.01 | B | C |
| ATOM | 9712 | CB | ASP | B | 91 | 76.103 | 37.821 | −4.010 | 1.00 | 25.50 | B | C |
| ATOM | 9715 | CG | ASP | B | 91 | 76.251 | 36.765 | −2.909 | 1.00 | 26.74 | B | C |
| ATOM | 9716 | OD1 | ASP | B | 91 | 76.655 | 37.118 | −1.779 | 1.00 | 29.64 | B | O |
| ATOM | 9717 | OD2 | ASP | B | 91 | 75.922 | 35.587 | −3.167 | 1.00 | 39.56 | B | O |
| ATOM | 9718 | C | ASP | B | 91 | 74.638 | 39.638 | −4.962 | 1.00 | 22.71 | B | C |
| ATOM | 9719 | O | ASP | B | 91 | 74.987 | 40.816 | −4.931 | 1.00 | 19.92 | B | O |
| ATOM | 9721 | N | ILE | B | 92 | 73.984 | 39.105 | −5.989 | 1.00 | 22.65 | B | N |
| ATOM | 9722 | CA | ILE | B | 92 | 73.661 | 39.888 | −7.185 | 1.00 | 22.89 | B | C |
| ATOM | 9724 | CB | ILE | B | 92 | 73.071 | 39.000 | −8.272 | 1.00 | 22.20 | B | C |
| ATOM | 9726 | CG1 | ILE | B | 92 | 74.203 | 38.179 | −8.899 | 1.00 | 22.79 | B | C |
| ATOM | 9729 | CD1 | ILE | B | 92 | 73.755 | 36.921 | −9.639 | 1.00 | 17.50 | B | C |
| ATOM | 9733 | CG2 | ILE | B | 92 | 72.332 | 39.853 | −9.316 | 1.00 | 20.85 | B | C |
| ATOM | 9737 | C | ILE | B | 92 | 72.710 | 41.049 | −6.869 | 1.00 | 24.13 | B | C |
| ATOM | 9738 | O | ILE | B | 92 | 72.974 | 42.200 | −7.246 | 1.00 | 22.72 | B | O |
| ATOM | 9740 | N | ARG | B | 93 | 71.624 | 40.744 | −6.167 | 1.00 | 24.93 | B | N |
| ATOM | 9741 | CA | ARG | B | 93 | 70.659 | 41.766 | −5.731 | 1.00 | 27.69 | B | C |
| ATOM | 9743 | CB | ARG | B | 93 | 69.522 | 41.150 | −4.895 | 1.00 | 29.92 | B | C |
| ATOM | 9746 | CG | ARG | B | 93 | 68.573 | 40.217 | −5.631 | 1.00 | 32.70 | B | C |
| ATOM | 9749 | CD | ARG | B | 93 | 67.427 | 39.746 | −4.685 | 1.00 | 39.32 | B | C |
| ATOM | 9752 | NE | ARG | B | 93 | 66.650 | 40.894 | −4.231 | 1.00 | 40.88 | B | N |
| ATOM | 9754 | CZ | ARG | B | 93 | 65.793 | 41.575 | −4.993 | 1.00 | 47.67 | B | C |
| ATOM | 9755 | NH1 | ARG | B | 93 | 65.565 | 41.216 | −6.262 | 1.00 | 47.75 | B | N |
| ATOM | 9758 | NH2 | ARG | B | 93 | 65.147 | 42.622 | −4.484 | 1.00 | 51.17 | B | N |
| ATOM | 9761 | C | ARG | B | 93 | 71.322 | 42.797 | −4.865 | 1.00 | 26.85 | B | C |
| ATOM | 9762 | O | ARG | B | 93 | 71.039 | 43.980 | −4.983 | 1.00 | 28.19 | B | O |
| ATOM | 9764 | N | GLY | B | 94 | 72.186 | 42.340 | −3.966 | 1.00 | 26.87 | B | N |

TABLE 4-2-continued

Coordinates of *P. alba* IspS

| | | | | | | | | | | | | |
|---|---|---|---|---|---|---|---|---|---|---|---|---|
| ATOM | 9765 | CA | GLY | B | 94 | 72.934 | 43.248 | −3.122 | 1.00 | 27.08 | B | C |
| ATOM | 9768 | C | GLY | B | 94 | 73.776 | 44.208 | −3.939 | 1.00 | 27.51 | B | C |
| ATOM | 9769 | O | GLY | B | 94 | 73.809 | 45.401 | −3.656 | 1.00 | 31.87 | B | O |
| ATOM | 9771 | N | ALA | B | 95 | 74.464 | 43.704 | −4.957 | 1.00 | 25.26 | B | N |
| ATOM | 9772 | CA | ALA | B | 95 | 75.283 | 44.564 | −5.793 | 1.00 | 23.60 | B | C |
| ATOM | 9774 | CB | ALA | B | 95 | 76.133 | 43.743 | −6.728 | 1.00 | 21.73 | B | C |
| ATOM | 9778 | C | ALA | B | 95 | 74.397 | 45.521 | −6.578 | 1.00 | 23.80 | B | C |
| ATOM | 9779 | O | ALA | B | 95 | 74.670 | 46.712 | −6.666 | 1.00 | 23.61 | B | O |
| ATOM | 9781 | N | LEU | B | 96 | 73.322 | 45.005 | −7.152 | 1.00 | 25.22 | B | N |
| ATOM | 9782 | CA | LEU | B | 96 | 72.452 | 45.858 | −7.955 | 1.00 | 26.19 | B | C |
| ATOM | 9784 | CB | LEU | B | 96 | 71.359 | 45.040 | −8.659 | 1.00 | 25.27 | B | C |
| ATOM | 9787 | CG | LEU | B | 96 | 71.931 | 44.096 | −9.719 | 1.00 | 26.21 | B | C |
| ATOM | 9789 | CD1 | LEU | B | 96 | 70.839 | 43.152 | −10.263 | 1.00 | 20.34 | B | C |
| ATOM | 9793 | CD2 | LEU | B | 96 | 72.591 | 44.898 | −10.840 | 1.00 | 19.97 | B | C |
| ATOM | 9797 | C | LEU | B | 96 | 71.855 | 46.943 | −7.070 | 1.00 | 27.60 | B | C |
| ATOM | 9798 | O | LEU | B | 96 | 71.741 | 48.080 | −7.486 | 1.00 | 25.32 | B | O |
| ATOM | 9800 | N | ASP | B | 97 | 71.510 | 46.589 | −5.834 | 1.00 | 30.71 | B | N |
| ATOM | 9801 | CA | ASP | B | 97 | 70.894 | 47.534 | −4.922 | 1.00 | 34.41 | B | C |
| ATOM | 9803 | CB | ASP | B | 97 | 70.407 | 46.810 | −3.668 | 1.00 | 36.18 | B | C |
| ATOM | 9806 | CG | ASP | B | 97 | 69.603 | 47.704 | −2.770 | 1.00 | 46.19 | B | C |
| ATOM | 9807 | OD1 | ASP | B | 97 | 70.026 | 47.902 | −1.611 | 1.00 | 56.68 | B | O |
| ATOM | 9808 | OD2 | ASP | B | 97 | 68.567 | 48.239 | −3.235 | 1.00 | 53.71 | B | O |
| ATOM | 9809 | C | ASP | B | 97 | 71.855 | 48.672 | −4.568 | 1.00 | 35.18 | B | C |
| ATOM | 9810 | O | ASP | B | 97 | 71.452 | 49.829 | −4.438 | 1.00 | 35.44 | B | O |
| ATOM | 9812 | N | ARG | B | 98 | 73.128 | 48.328 | −4.428 | 1.00 | 37.40 | B | N |
| ATOM | 9813 | CA | ARG | B | 98 | 74.183 | 49.305 | −4.148 | 1.00 | 38.06 | B | C |
| ATOM | 9815 | CB | ARG | B | 98 | 75.536 | 48.601 | −3.947 | 1.00 | 39.12 | B | C |
| ATOM | 9818 | CG | ARG | B | 98 | 76.260 | 48.876 | −2.626 | 1.00 | 41.93 | B | C |
| ATOM | 9821 | CD | ARG | B | 98 | 76.328 | 47.616 | −1.786 | 1.00 | 44.63 | B | C |
| ATOM | 9824 | NE | ARG | B | 98 | 77.027 | 46.541 | −2.495 | 1.00 | 40.39 | B | N |
| ATOM | 9826 | CZ | ARG | B | 98 | 76.878 | 45.243 | −2.248 | 1.00 | 33.84 | B | C |
| ATOM | 9827 | NH1 | ARG | B | 98 | 76.044 | 44.819 | −1.303 | 1.00 | 38.65 | B | N |
| ATOM | 9830 | NH2 | ARG | B | 98 | 77.564 | 44.360 | −2.963 | 1.00 | 35.04 | B | N |
| ATOM | 9833 | C | ARG | B | 98 | 74.298 | 50.240 | −5.337 | 1.00 | 37.03 | B | C |
| ATOM | 9834 | O | ARG | B | 98 | 74.388 | 51.452 | −5.189 | 1.00 | 35.80 | B | O |
| ATOM | 9836 | N | PHE | B | 99 | 74.289 | 49.641 | −6.522 | 1.00 | 36.87 | B | N |
| ATOM | 9837 | CA | PHE | B | 99 | 74.457 | 50.365 | −7.767 | 1.00 | 36.19 | B | C |
| ATOM | 9839 | CB | PHE | B | 99 | 74.402 | 49.380 | −8.927 | 1.00 | 36.62 | B | C |
| ATOM | 9842 | CG | PHE | B | 99 | 74.636 | 49.997 | −10.260 | 1.00 | 33.49 | B | C |
| ATOM | 9843 | CD1 | PHE | B | 99 | 75.826 | 50.641 | −10.534 | 1.00 | 38.87 | B | C |
| ATOM | 9845 | CE1 | PHE | B | 99 | 76.054 | 51.211 | −11.773 | 1.00 | 37.59 | B | C |
| ATOM | 9847 | CZ | PHE | B | 99 | 75.087 | 51.116 | −12.749 | 1.00 | 36.98 | B | C |
| ATOM | 9849 | CE2 | PHE | B | 99 | 73.901 | 50.457 | −12.486 | 1.00 | 29.58 | B | C |
| ATOM | 9851 | CD2 | PHE | B | 99 | 73.677 | 49.916 | −11.252 | 1.00 | 33.52 | B | C |
| ATOM | 9853 | C | PHE | B | 99 | 73.396 | 51.431 | −7.953 | 1.00 | 36.68 | B | C |
| ATOM | 9854 | O | PHE | B | 99 | 73.686 | 52.516 | −8.465 | 1.00 | 37.64 | B | O |
| ATOM | 9856 | N | VAL | B | 100 | 72.170 | 51.134 | −7.540 | 1.00 | 36.30 | B | N |
| ATOM | 9857 | CA | VAL | B | 100 | 71.102 | 52.123 | −7.615 | 1.00 | 38.42 | B | C |
| ATOM | 9859 | CB | VAL | B | 100 | 69.704 | 51.479 | −7.546 | 1.00 | 39.36 | B | C |
| ATOM | 9861 | CG1 | VAL | B | 100 | 68.625 | 52.555 | −7.520 | 1.00 | 38.06 | B | C |
| ATOM | 9865 | CG2 | VAL | B | 100 | 69.486 | 50.541 | −8.738 | 1.00 | 35.08 | B | C |
| ATOM | 9869 | C | VAL | B | 100 | 71.258 | 53.138 | −6.489 | 1.00 | 40.92 | B | C |
| ATOM | 9870 | O | VAL | B | 100 | 71.400 | 54.336 | −6.745 | 1.00 | 41.13 | B | O |
| ATOM | 9872 | N | SER | B | 101 | 71.261 | 52.643 | −5.251 | 1.00 | 42.85 | B | N |
| ATOM | 9873 | CA | SER | B | 101 | 71.290 | 53.499 | −4.056 | 1.00 | 44.85 | B | C |
| ATOM | 9875 | CB | SER | B | 101 | 71.364 | 52.641 | −2.783 | 1.00 | 45.99 | B | C |
| ATOM | 9878 | OG | SER | B | 101 | 72.670 | 52.116 | −2.592 | 1.00 | 48.88 | B | O |
| ATOM | 9880 | C | SER | B | 101 | 72.435 | 54.514 | −4.026 | 1.00 | 44.67 | B | C |
| ATOM | 9881 | O | SER | B | 101 | 72.314 | 55.554 | −3.390 | 1.00 | 45.09 | B | O |
| ATOM | 9883 | N | SER | B | 102 | 73.546 | 54.195 | −4.685 | 1.00 | 44.99 | B | N |
| ATOM | 9884 | CA | SER | B | 102 | 74.709 | 55.078 | −4.710 | 1.00 | 45.30 | B | C |
| ATOM | 9886 | CB | SER | B | 102 | 76.001 | 54.249 | −4.754 | 1.00 | 45.54 | B | C |
| ATOM | 9889 | OG | SER | B | 102 | 76.305 | 53.829 | −6.074 | 1.00 | 46.99 | B | O |
| ATOM | 9891 | C | SER | B | 102 | 74.680 | 56.051 | −5.892 | 1.00 | 44.38 | B | C |
| ATOM | 9892 | O | SER | B | 102 | 75.651 | 56.748 | −6.133 | 1.00 | 44.36 | B | O |
| ATOM | 9894 | N | GLY | B | 103 | 73.579 | 56.086 | −6.632 | 1.00 | 45.09 | B | N |
| ATOM | 9895 | CA | GLY | B | 103 | 73.474 | 56.931 | −7.820 | 1.00 | 46.00 | B | C |
| ATOM | 9898 | C | GLY | B | 103 | 74.299 | 56.453 | −9.007 | 1.00 | 45.92 | B | C |
| ATOM | 9899 | O | GLY | B | 103 | 74.416 | 57.159 | −10.016 | 1.00 | 45.89 | B | O |
| ATOM | 9901 | N | GLY | B | 104 | 74.861 | 55.251 | −8.900 | 1.00 | 45.67 | B | N |
| ATOM | 9902 | CA | GLY | B | 104 | 75.678 | 54.681 | −9.965 | 1.00 | 45.47 | B | C |
| ATOM | 9905 | C | GLY | B | 104 | 74.878 | 54.459 | −11.234 | 1.00 | 45.06 | B | C |
| ATOM | 9906 | O | GLY | B | 104 | 75.402 | 54.617 | −12.343 | 1.00 | 46.05 | B | O |
| ATOM | 9908 | N | PHE | B | 105 | 73.603 | 54.114 | −11.074 | 1.00 | 43.92 | B | N |
| ATOM | 9909 | CA | PHE | B | 105 | 72.735 | 53.885 | −12.220 | 1.00 | 44.36 | B | C |
| ATOM | 9911 | CB | PHE | B | 105 | 71.423 | 53.191 | −11.814 | 1.00 | 42.94 | B | C |
| ATOM | 9914 | CG | PHE | B | 105 | 70.454 | 53.021 | −12.957 | 1.00 | 42.37 | B | C |
| ATOM | 9915 | CD1 | PHE | B | 105 | 70.829 | 52.332 | −14.103 | 1.00 | 36.91 | B | C |

TABLE 4-2-continued

Coordinates of *P. alba* IspS

| | | | | | | | | | | | | |
|---|---|---|---|---|---|---|---|---|---|---|---|---|
| ATOM | 9917 | CE1 | PHE | B | 105 | 69.952 | 52.182 | −15.166 | 1.00 | 37.47 | B | C |
| ATOM | 9919 | CZ | PHE | B | 105 | 68.680 | 52.719 | −15.094 | 1.00 | 41.23 | B | C |
| ATOM | 9921 | CE2 | PHE | B | 105 | 68.291 | 53.412 | −13.959 | 1.00 | 42.58 | B | C |
| ATOM | 9923 | CD2 | PHE | B | 105 | 69.178 | 53.564 | −12.897 | 1.00 | 44.83 | B | C |
| ATOM | 9925 | C | PHE | B | 105 | 72.459 | 55.200 | −12.938 | 1.00 | 45.55 | B | C |
| ATOM | 9926 | O | PHE | B | 105 | 72.515 | 55.272 | −14.165 | 1.00 | 46.03 | B | O |
| ATOM | 9928 | N | ASP | B | 106 | 72.181 | 56.251 | −12.184 | 1.00 | 48.32 | B | N |
| ATOM | 9929 | CA | ASP | B | 106 | 71.949 | 57.544 | −12.816 | 1.00 | 50.02 | B | C |
| ATOM | 9931 | CB | ASP | B | 106 | 71.521 | 58.609 | −11.799 | 1.00 | 51.66 | B | C |
| ATOM | 9934 | CG | ASP | B | 106 | 70.532 | 59.608 | −12.389 | 1.00 | 59.23 | B | C |
| ATOM | 9935 | OD1 | ASP | B | 106 | 70.967 | 60.722 | −12.764 | 1.00 | 68.92 | B | O |
| ATOM | 9936 | OD2 | ASP | B | 106 | 69.329 | 59.265 | −12.503 | 1.00 | 64.95 | B | O |
| ATOM | 9937 | C | ASP | B | 106 | 73.202 | 57.974 | −13.594 | 1.00 | 48.61 | B | C |
| ATOM | 9938 | O | ASP | B | 106 | 73.086 | 58.477 | −14.710 | 1.00 | 49.31 | B | O |
| ATOM | 9940 | N | ALA | B | 107 | 74.384 | 57.740 | −13.017 | 1.00 | 46.79 | B | N |
| ATOM | 9941 | CA | ALA | B | 107 | 75.666 | 58.062 | −13.663 | 1.00 | 45.20 | B | C |
| ATOM | 9943 | CB | ALA | B | 107 | 76.843 | 57.556 | −12.813 | 1.00 | 45.79 | B | C |
| ATOM | 9947 | C | ALA | B | 107 | 75.773 | 57.487 | −15.070 | 1.00 | 44.20 | B | C |
| ATOM | 9948 | O | ALA | B | 107 | 76.122 | 58.209 | −16.012 | 1.00 | 43.29 | B | O |
| ATOM | 9950 | N | VAL | B | 108 | 75.468 | 56.193 | −15.214 | 1.00 | 42.78 | B | N |
| ATOM | 9951 | CA | VAL | B | 108 | 75.678 | 55.509 | −16.490 | 1.00 | 41.56 | B | C |
| ATOM | 9953 | CB | VAL | B | 108 | 75.580 | 53.961 | −16.398 | 1.00 | 42.67 | B | C |
| ATOM | 9955 | CG1 | VAL | B | 108 | 76.575 | 53.424 | −15.362 | 1.00 | 47.74 | B | C |
| ATOM | 9959 | CG2 | VAL | B | 108 | 74.146 | 53.506 | −16.103 | 1.00 | 37.79 | B | C |
| ATOM | 9963 | C | VAL | B | 108 | 74.736 | 56.019 | −17.565 | 1.00 | 40.56 | B | C |
| ATOM | 9964 | O | VAL | B | 108 | 75.140 | 56.108 | −18.716 | 1.00 | 41.01 | B | O |
| ATOM | 9966 | N | THR | B | 109 | 73.502 | 56.372 | −17.201 | 1.00 | 40.25 | B | N |
| ATOM | 9967 | CA | THR | B | 109 | 72.547 | 56.895 | −18.191 | 1.00 | 41.97 | B | C |
| ATOM | 9969 | CB | THR | B | 109 | 71.113 | 57.091 | −17.604 | 1.00 | 41.78 | B | C |
| ATOM | 9971 | OG1 | THR | B | 109 | 71.096 | 58.187 | −16.682 | 1.00 | 41.41 | B | O |
| ATOM | 9973 | CG2 | THR | B | 109 | 70.628 | 55.818 | −16.897 | 1.00 | 40.99 | B | C |
| ATOM | 9977 | C | THR | B | 109 | 73.024 | 58.197 | −18.874 | 1.00 | 43.11 | B | C |
| ATOM | 9978 | O | THR | B | 109 | 72.439 | 58.614 | −19.887 | 1.00 | 42.41 | B | O |
| ATOM | 9980 | N | LYS | B | 110 | 74.077 | 58.819 | −18.328 | 1.00 | 44.55 | B | N |
| ATOM | 9981 | CA | LYS | B | 110 | 74.712 | 60.008 | −18.934 | 1.00 | 46.75 | B | C |
| ATOM | 9983 | CB | LYS | B | 110 | 75.089 | 61.044 | −17.862 | 1.00 | 47.58 | B | C |
| ATOM | 9986 | CG | LYS | B | 110 | 74.109 | 61.209 | −16.687 | 1.00 | 52.76 | B | C |
| ATOM | 9989 | CD | LYS | B | 110 | 72.754 | 61.764 | −17.101 | 1.00 | 59.40 | B | C |
| ATOM | 9992 | CE | LYS | B | 110 | 71.958 | 62.222 | −15.878 | 1.00 | 63.05 | B | C |
| ATOM | 9995 | NZ | LYS | B | 110 | 70.552 | 62.553 | −16.225 | 1.00 | 62.78 | B | N |
| ATOM | 9999 | C | LYS | B | 110 | 75.976 | 59.657 | −19.743 | 1.00 | 46.76 | B | C |
| ATOM | 10000 | O | LYS | B | 110 | 76.282 | 60.317 | −20.748 | 1.00 | 47.35 | B | O |
| ATOM | 10002 | N | THR | B | 111 | 76.697 | 58.619 | −19.304 | 1.00 | 46.07 | B | N |
| ATOM | 10003 | CA | THR | B | 111 | 77.998 | 58.251 | −19.878 | 1.00 | 44.96 | B | C |
| ATOM | 10005 | CB | THR | B | 111 | 79.002 | 57.862 | −18.753 | 1.00 | 46.02 | B | C |
| ATOM | 10007 | OG1 | THR | B | 111 | 78.445 | 56.851 | −17.896 | 1.00 | 46.80 | B | O |
| ATOM | 10009 | CG2 | THR | B | 111 | 79.355 | 59.091 | −17.907 | 1.00 | 48.57 | B | C |
| ATOM | 10013 | C | THR | B | 111 | 77.980 | 57.145 | −20.961 | 1.00 | 43.55 | B | C |
| ATOM | 10014 | O | THR | B | 111 | 78.579 | 57.326 | −22.031 | 1.00 | 43.45 | B | O |
| ATOM | 10016 | N | SER | B | 112 | 77.288 | 56.026 | −20.695 | 1.00 | 40.85 | B | N |
| ATOM | 10017 | CA | SER | B | 112 | 77.475 | 54.771 | −21.460 | 1.00 | 38.21 | B | C |
| ATOM | 10019 | CB | SER | B | 112 | 78.367 | 53.817 | −20.654 | 1.00 | 38.70 | B | C |
| ATOM | 10022 | OG | SER | B | 112 | 78.963 | 52.840 | −21.489 | 1.00 | 42.04 | B | O |
| ATOM | 10024 | C | SER | B | 112 | 76.191 | 54.013 | −21.850 | 1.00 | 35.38 | B | C |
| ATOM | 10025 | O | SER | B | 112 | 75.380 | 53.635 | −20.990 | 1.00 | 33.95 | B | O |
| ATOM | 10027 | N | LEU | B | 113 | 76.039 | 53.751 | −23.146 | 1.00 | 32.47 | B | N |
| ATOM | 10028 | CA | LEU | B | 113 | 74.920 | 52.960 | −23.647 | 1.00 | 30.72 | B | C |
| ATOM | 10030 | CB | LEU | B | 113 | 74.878 | 52.958 | −25.174 | 1.00 | 30.16 | B | C |
| ATOM | 10033 | CG | LEU | B | 113 | 73.792 | 52.095 | −25.831 | 1.00 | 29.63 | B | C |
| ATOM | 10035 | CD1 | LEU | B | 113 | 72.399 | 52.493 | −25.368 | 1.00 | 27.97 | B | C |
| ATOM | 10039 | CD2 | LEU | B | 113 | 73.891 | 52.182 | −27.341 | 1.00 | 34.38 | B | C |
| ATOM | 10043 | C | LEU | B | 113 | 75.025 | 51.529 | −23.144 | 1.00 | 30.25 | B | C |
| ATOM | 10044 | O | LEU | B | 113 | 74.071 | 51.011 | −22.567 | 1.00 | 29.96 | B | O |
| ATOM | 10046 | N | HIS | B | 114 | 76.182 | 50.901 | −23.371 | 1.00 | 29.63 | B | N |
| ATOM | 10047 | CA | HIS | B | 114 | 76.423 | 49.536 | −22.917 | 1.00 | 29.61 | B | C |
| ATOM | 10049 | CB | HIS | B | 114 | 77.874 | 49.098 | −23.189 | 1.00 | 28.64 | B | C |
| ATOM | 10052 | CG | HIS | B | 114 | 78.237 | 47.786 | −22.557 | 1.00 | 30.75 | B | C |
| ATOM | 10053 | ND1 | HIS | B | 114 | 77.483 | 46.642 | −22.722 | 1.00 | 32.60 | B | N |
| ATOM | 10055 | CE1 | HIS | B | 114 | 78.039 | 45.648 | −22.048 | 1.00 | 36.57 | B | C |
| ATOM | 10057 | NE2 | HIS | B | 114 | 79.126 | 46.105 | −21.449 | 1.00 | 37.27 | B | N |
| ATOM | 10059 | CD2 | HIS | B | 114 | 79.271 | 47.439 | −21.750 | 1.00 | 36.73 | B | C |
| ATOM | 10061 | C | HIS | B | 114 | 76.095 | 49.445 | −21.426 | 1.00 | 28.21 | B | C |
| ATOM | 10062 | O | HIS | B | 114 | 75.330 | 48.587 | −21.002 | 1.00 | 24.16 | B | O |
| ATOM | 10064 | N | GLY | B | 115 | 76.666 | 50.363 | −20.651 | 1.00 | 26.67 | B | N |
| ATOM | 10065 | CA | GLY | B | 115 | 76.454 | 50.389 | −19.215 | 1.00 | 25.56 | B | C |
| ATOM | 10068 | C | GLY | B | 115 | 74.993 | 50.506 | −18.845 | 1.00 | 25.02 | B | C |
| ATOM | 10069 | O | GLY | B | 115 | 74.544 | 49.881 | −17.891 | 1.00 | 25.22 | B | O |
| ATOM | 10071 | N | THR | B | 116 | 74.255 | 51.327 | −19.585 | 1.00 | 24.92 | B | N |

TABLE 4-2-continued

Coordinates of *P. alba* IspS

| | | | | | | | | | | | | |
|---|---|---|---|---|---|---|---|---|---|---|---|---|
| ATOM | 10072 | CA | THR | B | 116 | 72.854 | 51.580 | −19.282 | 1.00 | 23.97 | B | C |
| ATOM | 10074 | CB | THR | B | 116 | 72.386 | 52.889 | −19.917 | 1.00 | 24.60 | B | C |
| ATOM | 10076 | OG1 | THR | B | 116 | 73.118 | 53.974 | −19.331 | 1.00 | 30.58 | B | O |
| ATOM | 10078 | CG2 | THR | B | 116 | 70.907 | 53.144 | −19.699 | 1.00 | 21.02 | B | C |
| ATOM | 10082 | C | THR | B | 116 | 72.002 | 50.387 | −19.711 | 1.00 | 26.00 | B | C |
| ATOM | 10083 | O | THR | B | 116 | 71.102 | 49.976 | −18.967 | 1.00 | 27.03 | B | O |
| ATOM | 10085 | N | ALA | B | 117 | 72.304 | 49.799 | −20.868 | 1.00 | 25.43 | B | N |
| ATOM | 10086 | CA | ALA | B | 117 | 71.505 | 48.662 | −21.378 | 1.00 | 25.89 | B | C |
| ATOM | 10088 | CB | ALA | B | 117 | 71.933 | 48.268 | −22.811 | 1.00 | 24.62 | B | C |
| ATOM | 10092 | C | ALA | B | 117 | 71.643 | 47.470 | −20.448 | 1.00 | 24.68 | B | C |
| ATOM | 10093 | O | ALA | B | 117 | 70.652 | 46.837 | −20.047 | 1.00 | 24.91 | B | O |
| ATOM | 10095 | N | LEU | B | 118 | 72.883 | 47.160 | −20.117 | 1.00 | 23.09 | B | N |
| ATOM | 10096 | CA | LEU | B | 118 | 73.178 | 46.044 | −19.230 | 1.00 | 23.36 | B | C |
| ATOM | 10098 | CB | LEU | B | 118 | 74.686 | 45.887 | −19.068 | 1.00 | 23.58 | B | C |
| ATOM | 10101 | CG | LEU | B | 118 | 75.181 | 44.714 | −18.231 | 1.00 | 26.99 | B | C |
| ATOM | 10103 | CD1 | LEU | B | 118 | 74.478 | 43.412 | −18.671 | 1.00 | 21.92 | B | C |
| ATOM | 10107 | CD2 | LEU | B | 118 | 76.708 | 44.613 | −18.322 | 1.00 | 19.81 | B | C |
| ATOM | 10111 | C | LEU | B | 118 | 72.521 | 46.257 | −17.880 | 1.00 | 22.07 | B | C |
| ATOM | 10112 | O | LEU | B | 118 | 71.777 | 45.405 | −17.412 | 1.00 | 21.86 | B | O |
| ATOM | 10114 | N | SER | B | 119 | 72.753 | 47.417 | −17.273 | 1.00 | 23.56 | B | N |
| ATOM | 10115 | CA | SER | B | 119 | 72.214 | 47.677 | −15.938 | 1.00 | 23.71 | B | C |
| ATOM | 10117 | CB | SER | B | 119 | 72.787 | 48.959 | −15.318 | 1.00 | 25.08 | B | C |
| ATOM | 10120 | OG | SER | B | 119 | 72.384 | 50.147 | −15.974 | 1.00 | 25.85 | B | O |
| ATOM | 10122 | C | SER | B | 119 | 70.697 | 47.691 | −15.957 | 1.00 | 22.91 | B | C |
| ATOM | 10123 | O | SER | B | 119 | 70.050 | 47.212 | −15.017 | 1.00 | 23.88 | B | O |
| ATOM | 10125 | N | PHE | B | 120 | 70.124 | 48.197 | −17.036 | 1.00 | 21.99 | B | N |
| ATOM | 10126 | CA | PHE | B | 120 | 68.674 | 48.240 | −17.144 | 1.00 | 22.07 | B | C |
| ATOM | 10128 | CB | PHE | B | 120 | 68.269 | 48.927 | −18.441 | 1.00 | 22.76 | B | C |
| ATOM | 10131 | CG | PHE | B | 120 | 66.792 | 48.936 | −18.703 | 1.00 | 23.93 | B | C |
| ATOM | 10132 | CD1 | PHE | B | 120 | 66.012 | 50.026 | −18.329 | 1.00 | 24.72 | B | C |
| ATOM | 10134 | CE1 | PHE | B | 120 | 64.651 | 50.041 | −18.588 | 1.00 | 21.87 | B | C |
| ATOM | 10136 | CZ | PHE | B | 120 | 64.064 | 48.965 | −19.235 | 1.00 | 25.59 | B | C |
| ATOM | 10138 | CE2 | PHE | B | 120 | 64.831 | 47.875 | −19.615 | 1.00 | 21.43 | B | C |
| ATOM | 10140 | CD2 | PHE | B | 120 | 66.187 | 47.870 | −19.355 | 1.00 | 26.77 | B | C |
| ATOM | 10142 | C | PHE | B | 120 | 68.138 | 46.820 | −17.108 | 1.00 | 22.44 | B | C |
| ATOM | 10143 | O | PHE | B | 120 | 67.232 | 46.510 | −16.330 | 1.00 | 23.78 | B | O |
| ATOM | 10145 | N | ARG | B | 121 | 68.708 | 45.967 | −17.954 | 1.00 | 20.63 | B | N |
| ATOM | 10146 | CA | ARG | B | 121 | 68.315 | 44.563 | −18.023 | 1.00 | 22.16 | B | C |
| ATOM | 10148 | CB | ARG | B | 121 | 69.116 | 43.838 | −19.109 | 1.00 | 20.34 | B | C |
| ATOM | 10151 | CG | ARG | B | 121 | 68.782 | 42.387 | −19.214 | 1.00 | 22.78 | B | C |
| ATOM | 10154 | CD | ARG | B | 121 | 69.278 | 41.785 | −20.511 | 1.00 | 23.57 | B | C |
| ATOM | 10157 | NE | ARG | B | 121 | 70.735 | 41.705 | −20.574 | 1.00 | 22.85 | B | N |
| ATOM | 10159 | CZ | ARG | B | 121 | 71.486 | 40.804 | −19.954 | 1.00 | 21.72 | B | C |
| ATOM | 10160 | NH1 | ARG | B | 121 | 70.943 | 39.879 | −19.173 | 1.00 | 27.91 | B | N |
| ATOM | 10163 | NH2 | ARG | B | 121 | 72.797 | 40.835 | −20.117 | 1.00 | 22.89 | B | N |
| ATOM | 10166 | C | ARG | B | 121 | 68.467 | 43.826 | −16.691 | 1.00 | 20.89 | B | C |
| ATOM | 10167 | O | ARG | B | 121 | 67.536 | 43.185 | −16.244 | 1.00 | 22.14 | B | O |
| ATOM | 10169 | N | LEU | B | 122 | 69.634 | 43.918 | −16.075 | 1.00 | 19.65 | B | N |
| ATOM | 10170 | CA | LEU | B | 122 | 69.877 | 43.198 | −14.829 | 1.00 | 21.62 | B | C |
| ATOM | 10172 | CB | LEU | B | 122 | 71.342 | 43.312 | −14.409 | 1.00 | 19.60 | B | C |
| ATOM | 10175 | CG | LEU | B | 122 | 72.377 | 42.726 | −15.362 | 1.00 | 20.38 | B | C |
| ATOM | 10177 | CD1 | LEU | B | 122 | 73.745 | 43.081 | −14.843 | 1.00 | 20.38 | B | C |
| ATOM | 10181 | CD2 | LEU | B | 122 | 72.217 | 41.193 | −15.508 | 1.00 | 15.76 | B | C |
| ATOM | 10185 | C | LEU | B | 122 | 68.947 | 43.705 | −13.710 | 1.00 | 22.20 | B | C |
| ATOM | 10186 | O | LEU | B | 122 | 68.419 | 42.921 | −12.921 | 1.00 | 22.69 | B | O |
| ATOM | 10188 | N | LEU | B | 123 | 68.712 | 45.009 | −13.681 | 1.00 | 23.60 | B | N |
| ATOM | 10189 | CA | LEU | B | 123 | 67.893 | 45.608 | −12.624 | 1.00 | 24.18 | B | C |
| ATOM | 10191 | CB | LEU | B | 123 | 67.931 | 47.130 | −12.701 | 1.00 | 21.92 | B | C |
| ATOM | 10194 | CG | LEU | B | 123 | 69.156 | 47.757 | −12.041 | 1.00 | 22.98 | B | C |
| ATOM | 10196 | CD1 | LEU | B | 123 | 69.363 | 49.223 | −12.487 | 1.00 | 19.39 | B | C |
| ATOM | 10200 | CD2 | LEU | B | 123 | 68.981 | 47.662 | −10.548 | 1.00 | 20.14 | B | C |
| ATOM | 10204 | C | LEU | B | 123 | 66.466 | 45.120 | −12.738 | 1.00 | 23.74 | B | C |
| ATOM | 10205 | O | LEU | B | 123 | 65.855 | 44.696 | −11.753 | 1.00 | 21.87 | B | O |
| ATOM | 10207 | N | ARG | B | 124 | 65.947 | 45.176 | −13.951 | 1.00 | 23.61 | B | N |
| ATOM | 10208 | CA | ARG | B | 124 | 64.580 | 44.747 | −14.194 | 1.00 | 22.51 | B | C |
| ATOM | 10210 | CB | ARG | B | 124 | 64.101 | 45.189 | −15.566 | 1.00 | 21.92 | B | C |
| ATOM | 10213 | CG | ARG | B | 124 | 62.624 | 44.861 | −15.768 | 1.00 | 23.90 | B | C |
| ATOM | 10216 | CD | ARG | B | 124 | 62.050 | 45.560 | −16.965 | 1.00 | 23.86 | B | C |
| ATOM | 10219 | NE | ARG | B | 124 | 61.591 | 46.926 | −16.676 | 1.00 | 24.72 | B | N |
| ATOM | 10221 | CZ | ARG | B | 124 | 61.083 | 47.743 | −17.601 | 1.00 | 24.21 | B | C |
| ATOM | 10222 | NH1 | ARG | B | 124 | 60.998 | 47.363 | −18.872 | 1.00 | 21.36 | B | N |
| ATOM | 10225 | NH2 | ARG | B | 124 | 60.671 | 48.955 | −17.265 | 1.00 | 25.66 | B | N |
| ATOM | 10228 | C | ARG | B | 124 | 64.420 | 43.247 | −14.052 | 1.00 | 22.28 | B | C |
| ATOM | 10229 | O | ARG | B | 124 | 63.435 | 42.768 | −13.479 | 1.00 | 23.53 | B | O |
| ATOM | 10231 | N | GLN | B | 125 | 65.389 | 42.490 | −14.549 | 1.00 | 23.20 | B | N |
| ATOM | 10232 | CA | GLN | B | 125 | 65.371 | 41.051 | −14.344 | 1.00 | 20.98 | B | C |
| ATOM | 10234 | CB | GLN | B | 125 | 66.693 | 40.426 | −14.832 | 1.00 | 22.19 | B | C |
| ATOM | 10237 | CG | GLN | B | 125 | 66.800 | 38.889 | −14.619 | 1.00 | 17.52 | B | C |

TABLE 4-2-continued

Coordinates of *P. alba* IspS

| | | | | | | | | | | | | |
|---|---|---|---|---|---|---|---|---|---|---|---|---|
| ATOM | 10240 | CD | GLN | B | 125 | 68.218 | 38.364 | −14.797 | 1.00 | 23.28 | B | C |
| ATOM | 10241 | OE1 | GLN | B | 125 | 69.105 | 39.069 | −15.273 | 1.00 | 19.79 | B | O |
| ATOM | 10242 | NE2 | GLN | B | 125 | 68.435 | 37.121 | −14.405 | 1.00 | 17.64 | B | N |
| ATOM | 10245 | C | GLN | B | 125 | 65.164 | 40.777 | −12.847 | 1.00 | 23.00 | B | C |
| ATOM | 10246 | O | GLN | B | 125 | 64.420 | 39.865 | −12.453 | 1.00 | 24.90 | B | O |
| ATOM | 10248 | N | HIS | B | 126 | 65.828 | 41.561 | −12.005 | 1.00 | 20.88 | B | N |
| ATOM | 10249 | CA | HIS | B | 126 | 65.780 | 41.310 | −10.576 | 1.00 | 22.19 | B | C |
| ATOM | 10251 | CB | HIS | B | 126 | 67.179 | 41.491 | −9.966 | 1.00 | 22.02 | B | C |
| ATOM | 10254 | CG | HIS | B | 126 | 68.109 | 40.381 | −10.310 | 1.00 | 21.58 | B | C |
| ATOM | 10255 | ND1 | HIS | B | 126 | 68.196 | 39.230 | −9.557 | 1.00 | 24.31 | B | N |
| ATOM | 10257 | CE1 | HIS | B | 126 | 69.090 | 38.425 | −10.103 | 1.00 | 23.72 | B | C |
| ATOM | 10259 | NE2 | HIS | B | 126 | 69.560 | 38.997 | −11.199 | 1.00 | 20.64 | B | N |
| ATOM | 10261 | CD2 | HIS | B | 126 | 68.960 | 40.218 | −11.353 | 1.00 | 17.59 | B | C |
| ATOM | 10263 | C | HIS | B | 126 | 64.742 | 42.137 | −9.829 | 1.00 | 23.10 | B | C |
| ATOM | 10264 | O | HIS | B | 126 | 64.850 | 42.311 | −8.624 | 1.00 | 23.65 | B | O |
| ATOM | 10266 | N | GLY | B | 127 | 63.739 | 42.655 | −10.529 | 1.00 | 25.00 | B | N |
| ATOM | 10267 | CA | GLY | B | 127 | 62.577 | 43.232 | −9.849 | 1.00 | 24.96 | B | C |
| ATOM | 10270 | C | GLY | B | 127 | 62.665 | 44.712 | −9.523 | 1.00 | 27.27 | B | C |
| ATOM | 10271 | O | GLY | B | 127 | 61.701 | 45.275 | −9.007 | 1.00 | 31.01 | B | O |
| ATOM | 10273 | N | PHE | B | 128 | 63.798 | 45.353 | −9.818 | 1.00 | 27.09 | B | N |
| ATOM | 10274 | CA | PHE | B | 128 | 63.946 | 46.787 | −9.589 | 1.00 | 27.86 | B | C |
| ATOM | 10276 | CB | PHE | B | 128 | 65.418 | 47.218 | −9.615 | 1.00 | 28.07 | B | C |
| ATOM | 10279 | CG | PHE | B | 128 | 66.208 | 46.655 | −8.482 | 1.00 | 28.18 | B | C |
| ATOM | 10280 | CD1 | PHE | B | 128 | 66.303 | 47.336 | −7.294 | 1.00 | 28.13 | B | C |
| ATOM | 10282 | CE1 | PHE | B | 128 | 67.003 | 46.811 | −6.249 | 1.00 | 33.20 | B | C |
| ATOM | 10284 | CZ | PHE | B | 128 | 67.592 | 45.571 | −6.362 | 1.00 | 34.73 | B | C |
| ATOM | 10286 | CE2 | PHE | B | 128 | 67.479 | 44.871 | −7.535 | 1.00 | 30.35 | B | C |
| ATOM | 10288 | CD2 | PHE | B | 128 | 66.785 | 45.409 | −8.580 | 1.00 | 26.88 | B | C |
| ATOM | 10290 | C | PHE | B | 128 | 63.150 | 47.567 | −10.605 | 1.00 | 30.22 | B | C |
| ATOM | 10291 | O | PHE | B | 128 | 62.932 | 47.122 | −11.725 | 1.00 | 30.38 | B | O |
| ATOM | 10293 | N | GLU | B | 129 | 62.703 | 48.739 | −10.185 | 1.00 | 31.72 | B | N |
| ATOM | 10294 | CA | GLU | B | 129 | 61.883 | 49.589 | −10.999 | 1.00 | 32.85 | B | C |
| ATOM | 10296 | CB | GLU | B | 129 | 60.995 | 50.460 | −10.091 | 1.00 | 35.17 | B | C |
| ATOM | 10299 | CG | GLU | B | 129 | 59.781 | 51.091 | −10.797 | 1.00 | 46.55 | B | C |
| ATOM | 10302 | CD | GLU | B | 129 | 59.293 | 52.392 | −10.153 | 1.00 | 59.19 | B | C |
| ATOM | 10303 | OE1 | GLU | B | 129 | 59.590 | 52.647 | −8.963 | 1.00 | 62.18 | B | O |
| ATOM | 10304 | OE2 | GLU | B | 129 | 58.598 | 53.169 | −10.850 | 1.00 | 66.91 | B | O |
| ATOM | 10305 | C | GLU | B | 129 | 62.833 | 50.455 | −11.828 | 1.00 | 30.85 | B | C |
| ATOM | 10306 | O | GLU | B | 129 | 63.634 | 51.200 | −11.283 | 1.00 | 34.34 | B | O |
| ATOM | 10308 | N | VAL | B | 130 | 62.773 | 50.339 | −13.140 | 1.00 | 28.74 | B | N |
| ATOM | 10309 | CA | VAL | B | 130 | 63.538 | 51.222 | −14.013 | 1.00 | 27.95 | B | C |
| ATOM | 10311 | CB | VAL | B | 130 | 64.783 | 50.533 | −14.591 | 1.00 | 28.89 | B | C |
| ATOM | 10313 | CG1 | VAL | B | 130 | 65.800 | 50.323 | −13.491 | 1.00 | 29.52 | B | C |
| ATOM | 10317 | CG2 | VAL | B | 130 | 64.422 | 49.201 | −15.242 | 1.00 | 25.33 | B | C |
| ATOM | 10321 | C | VAL | B | 130 | 62.647 | 51.707 | −15.142 | 1.00 | 27.27 | B | C |
| ATOM | 10322 | O | VAL | B | 130 | 61.695 | 51.033 | −15.506 | 1.00 | 26.56 | B | O |
| ATOM | 10324 | N | SER | B | 131 | 62.969 | 52.872 | −15.692 | 1.00 | 27.05 | B | N |
| ATOM | 10325 | CA | SER | B | 131 | 62.140 | 53.510 | −16.713 | 1.00 | 27.56 | B | C |
| ATOM | 10327 | CB | SER | B | 131 | 61.864 | 54.978 | −16.339 | 1.00 | 29.10 | B | C |
| ATOM | 10330 | OG | SER | B | 131 | 61.318 | 55.713 | −17.434 | 1.00 | 34.05 | B | O |
| ATOM | 10332 | C | SER | B | 131 | 62.871 | 53.470 | −18.031 | 1.00 | 26.59 | B | C |
| ATOM | 10333 | O | SER | B | 131 | 64.091 | 53.530 | −18.056 | 1.00 | 27.34 | B | O |
| ATOM | 10335 | N | GLN | B | 132 | 62.125 | 53.379 | −19.127 | 1.00 | 26.19 | B | N |
| ATOM | 10336 | CA | GLN | B | 132 | 62.718 | 53.487 | −20.450 | 1.00 | 26.48 | B | C |
| ATOM | 10338 | CB | GLN | B | 132 | 61.660 | 53.267 | −21.528 | 1.00 | 26.03 | B | C |
| ATOM | 10341 | CG | GLN | B | 132 | 60.477 | 54.223 | −21.463 | 1.00 | 26.99 | B | C |
| ATOM | 10344 | CD | GLN | B | 132 | 59.623 | 54.191 | −22.711 | 1.00 | 29.29 | B | C |
| ATOM | 10345 | OE1 | GLN | B | 132 | 59.822 | 53.355 | −23.602 | 1.00 | 27.92 | B | O |
| ATOM | 10346 | NE2 | GLN | B | 132 | 58.662 | 55.110 | −22.787 | 1.00 | 28.13 | B | N |
| ATOM | 10349 | C | GLN | B | 132 | 63.404 | 54.840 | −20.664 | 1.00 | 28.30 | B | C |
| ATOM | 10350 | O | GLN | B | 132 | 64.219 | 54.978 | −21.568 | 1.00 | 29.48 | B | O |
| ATOM | 10352 | N | GLU | B | 133 | 63.073 | 55.840 | −19.846 | 1.00 | 30.19 | B | N |
| ATOM | 10353 | CA | GLU | B | 133 | 63.686 | 57.179 | −19.974 | 1.00 | 32.53 | B | C |
| ATOM | 10355 | CB | GLU | B | 133 | 62.976 | 58.238 | −19.113 | 1.00 | 33.08 | B | C |
| ATOM | 10358 | CG | GLU | B | 133 | 61.500 | 58.466 | −19.448 | 1.00 | 38.45 | B | C |
| ATOM | 10361 | CD | GLU | B | 133 | 61.264 | 59.001 | −20.854 | 1.00 | 45.49 | B | C |
| ATOM | 10362 | OE1 | GLU | B | 133 | 62.178 | 59.632 | −21.439 | 1.00 | 49.73 | B | O |
| ATOM | 10363 | OE2 | GLU | B | 133 | 60.144 | 58.798 | −21.376 | 1.00 | 46.47 | B | O |
| ATOM | 10364 | C | GLU | B | 133 | 65.155 | 57.140 | −19.609 | 1.00 | 31.46 | B | C |
| ATOM | 10365 | O | GLU | B | 133 | 65.884 | 58.069 | −19.912 | 1.00 | 32.50 | B | O |
| ATOM | 10367 | N | ALA | B | 134 | 65.584 | 56.061 | −18.964 | 1.00 | 30.90 | B | N |
| ATOM | 10368 | CA | ALA | B | 134 | 67.002 | 55.760 | −18.824 | 1.00 | 30.86 | B | C |
| ATOM | 10370 | CB | ALA | B | 134 | 67.185 | 54.385 | −18.224 | 1.00 | 28.22 | B | C |
| ATOM | 10374 | C | ALA | B | 134 | 67.723 | 55.849 | −20.170 | 1.00 | 31.89 | B | C |
| ATOM | 10375 | O | ALA | B | 134 | 68.913 | 56.107 | −20.222 | 1.00 | 34.24 | B | O |
| ATOM | 10377 | N | PHE | B | 135 | 66.997 | 55.657 | −21.261 | 1.00 | 33.61 | B | N |
| ATOM | 10378 | CA | PHE | B | 135 | 67.597 | 55.727 | −22.588 | 1.00 | 34.02 | B | C |
| ATOM | 10380 | CB | PHE | B | 135 | 67.014 | 54.608 | −23.456 | 1.00 | 32.07 | B | C |

TABLE 4-2-continued

Coordinates of *P. alba* IspS

| | | | | | | | | | | | | |
|---|---|---|---|---|---|---|---|---|---|---|---|---|
| ATOM | 10383 | CG | PHE | B | 135 | 67.399 | 53.261 | −22.980 | 1.00 | 28.15 | B | C |
| ATOM | 10384 | CD1 | PHE | B | 135 | 66.564 | 52.535 | −22.159 | 1.00 | 26.04 | B | C |
| ATOM | 10386 | CE1 | PHE | B | 135 | 66.955 | 51.280 | −21.677 | 1.00 | 24.62 | B | C |
| ATOM | 10388 | CZ | PHE | B | 135 | 68.188 | 50.768 | −22.013 | 1.00 | 27.19 | B | C |
| ATOM | 10390 | CE2 | PHE | B | 135 | 69.039 | 51.497 | −22.821 | 1.00 | 28.77 | B | C |
| ATOM | 10392 | CD2 | PHE | B | 135 | 68.648 | 52.740 | −23.294 | 1.00 | 30.81 | B | C |
| ATOM | 10394 | C | PHE | B | 135 | 67.454 | 57.082 | −23.281 | 1.00 | 36.30 | B | C |
| ATOM | 10395 | O | PHE | B | 135 | 67.929 | 57.245 | −24.414 | 1.00 | 37.39 | B | O |
| ATOM | 10397 | N | SER | B | 136 | 66.840 | 58.058 | −22.611 | 1.00 | 37.55 | B | N |
| ATOM | 10398 | CA | SER | B | 136 | 66.566 | 59.356 | −23.244 | 1.00 | 38.94 | B | C |
| ATOM | 10400 | CB | SER | B | 136 | 65.767 | 60.282 | −22.305 | 1.00 | 39.41 | B | C |
| ATOM | 10403 | OG | SER | B | 136 | 66.461 | 60.527 | −21.086 | 1.00 | 40.01 | B | O |
| ATOM | 10405 | C | SER | B | 136 | 67.848 | 60.047 | −23.724 | 1.00 | 39.27 | B | C |
| ATOM | 10406 | O | SER | B | 136 | 67.839 | 60.721 | −24.753 | 1.00 | 41.19 | B | O |
| ATOM | 10408 | N | GLY | B | 137 | 68.949 | 59.847 | −23.010 | 1.00 | 38.96 | B | N |
| ATOM | 10409 | CA | GLY | B | 137 | 70.199 | 60.526 | −23.333 | 1.00 | 39.72 | B | C |
| ATOM | 10412 | C | GLY | B | 137 | 70.897 | 60.111 | −24.622 | 1.00 | 39.94 | B | C |
| ATOM | 10413 | O | GLY | B | 137 | 71.863 | 60.761 | −25.027 | 1.00 | 40.11 | B | O |
| ATOM | 10415 | N | PHE | B | 138 | 70.432 | 59.038 | −25.265 | 1.00 | 40.41 | B | N |
| ATOM | 10416 | CA | PHE | B | 138 | 71.074 | 58.516 | −26.490 | 1.00 | 41.42 | B | C |
| ATOM | 10418 | CB | PHE | B | 138 | 71.367 | 57.019 | −26.332 | 1.00 | 40.22 | B | C |
| ATOM | 10421 | CG | PHE | B | 138 | 72.080 | 56.695 | −25.064 | 1.00 | 37.60 | B | C |
| ATOM | 10422 | CD1 | PHE | B | 138 | 73.441 | 56.898 | −24.959 | 1.00 | 35.26 | B | C |
| ATOM | 10424 | CE1 | PHE | B | 138 | 74.103 | 56.628 | −23.776 | 1.00 | 35.62 | B | C |
| ATOM | 10426 | CZ | PHE | B | 138 | 73.400 | 56.170 | −22.682 | 1.00 | 34.61 | B | C |
| ATOM | 10428 | CE2 | PHE | B | 138 | 72.035 | 55.974 | −22.773 | 1.00 | 32.75 | B | C |
| ATOM | 10430 | CD2 | PHE | B | 138 | 71.383 | 56.235 | −23.955 | 1.00 | 35.81 | B | C |
| ATOM | 10432 | C | PHE | B | 138 | 70.254 | 58.760 | −27.758 | 1.00 | 43.98 | B | C |
| ATOM | 10433 | O | PHE | B | 138 | 70.642 | 58.317 | −28.843 | 1.00 | 43.19 | B | O |
| ATOM | 10435 | N | LYS | B | 139 | 69.128 | 59.460 | −27.609 | 1.00 | 47.54 | B | N |
| ATOM | 10436 | CA | LYS | B | 139 | 68.279 | 59.824 | −28.734 | 1.00 | 51.04 | B | C |
| ATOM | 10438 | CB | LYS | B | 139 | 66.799 | 59.812 | −28.322 | 1.00 | 51.46 | B | C |
| ATOM | 10441 | CG | LYS | B | 139 | 66.192 | 58.391 | −28.258 | 1.00 | 55.89 | B | C |
| ATOM | 10444 | CD | LYS | B | 139 | 64.883 | 58.314 | −27.450 | 1.00 | 59.90 | B | C |
| ATOM | 10447 | CE | LYS | B | 139 | 63.667 | 58.845 | −28.219 | 1.00 | 63.07 | B | C |
| ATOM | 10450 | NZ | LYS | B | 139 | 63.073 | 57.860 | −29.172 | 1.00 | 58.78 | B | N |
| ATOM | 10454 | C | LYS | B | 139 | 68.699 | 61.198 | −29.255 | 1.00 | 53.29 | B | C |
| ATOM | 10455 | O | LYS | B | 139 | 68.986 | 62.106 | −28.470 | 1.00 | 54.74 | B | O |
| ATOM | 10457 | N | ASP | B | 140 | 68.743 | 61.339 | −30.579 | 1.00 | 55.19 | B | N |
| ATOM | 10458 | CA | ASP | B | 140 | 69.183 | 62.580 | −31.216 | 1.00 | 56.63 | B | C |
| ATOM | 10460 | CB | ASP | B | 140 | 69.663 | 62.312 | −32.662 | 1.00 | 55.93 | B | C |
| ATOM | 10463 | CG | ASP | B | 140 | 68.528 | 61.932 | −33.627 | 1.00 | 54.78 | B | C |
| ATOM | 10464 | OD1 | ASP | B | 140 | 67.331 | 62.035 | −33.273 | 1.00 | 48.15 | B | O |
| ATOM | 10465 | OD2 | ASP | B | 140 | 68.847 | 61.518 | −34.763 | 1.00 | 51.45 | B | O |
| ATOM | 10466 | C | ASP | B | 140 | 68.090 | 63.656 | −31.172 | 1.00 | 59.23 | B | C |
| ATOM | 10467 | O | ASP | B | 140 | 67.021 | 63.456 | −30.576 | 1.00 | 59.10 | B | O |
| ATOM | 10469 | N | GLN | B | 141 | 68.385 | 64.794 | −31.803 | 1.00 | 62.19 | B | N |
| ATOM | 10470 | CA | GLN | B | 141 | 67.447 | 65.918 | −31.951 | 1.00 | 63.69 | B | C |
| ATOM | 10472 | CB | GLN | B | 141 | 67.947 | 66.889 | −33.034 | 1.00 | 64.14 | B | C |
| ATOM | 10475 | CG | GLN | B | 141 | 69.332 | 67.484 | −32.792 | 1.00 | 67.32 | B | C |
| ATOM | 10478 | CD | GLN | B | 141 | 69.331 | 68.608 | −31.775 | 1.00 | 70.44 | B | C |
| ATOM | 10479 | OE1 | GLN | B | 141 | 68.722 | 68.506 | −30.710 | 1.00 | 70.76 | B | O |
| ATOM | 10480 | NE2 | GLN | B | 141 | 70.032 | 69.686 | −32.097 | 1.00 | 68.92 | B | N |
| ATOM | 10483 | C | GLN | B | 141 | 66.032 | 65.451 | −32.314 | 1.00 | 63.72 | B | C |
| ATOM | 10484 | O | GLN | B | 141 | 65.086 | 65.649 | −31.544 | 1.00 | 63.99 | B | O |
| ATOM | 10486 | N | ASN | B | 142 | 65.912 | 64.804 | −33.473 | 1.00 | 63.20 | B | N |
| ATOM | 10487 | CA | ASN | B | 142 | 64.622 | 64.348 | −33.997 | 1.00 | 62.48 | B | C |
| ATOM | 10489 | CB | ASN | B | 142 | 64.795 | 63.752 | −35.399 | 1.00 | 62.80 | B | C |
| ATOM | 10492 | CG | ASN | B | 142 | 65.133 | 64.801 | −36.442 | 1.00 | 64.18 | B | C |
| ATOM | 10493 | OD1 | ASN | B | 142 | 64.277 | 65.195 | −37.234 | 1.00 | 64.38 | B | O |
| ATOM | 10494 | ND2 | ASN | B | 142 | 66.381 | 65.261 | −36.446 | 1.00 | 61.04 | B | N |
| ATOM | 10497 | C | ASN | B | 142 | 63.913 | 63.330 | −33.100 | 1.00 | 61.50 | B | C |
| ATOM | 10498 | O | ASN | B | 142 | 62.686 | 63.236 | −33.128 | 1.00 | 61.52 | B | O |
| ATOM | 10500 | N | GLY | B | 143 | 64.685 | 62.579 | −32.311 | 1.00 | 59.99 | B | N |
| ATOM | 10501 | CA | GLY | B | 143 | 64.141 | 61.554 | −31.415 | 1.00 | 58.60 | B | C |
| ATOM | 10504 | C | GLY | B | 143 | 64.432 | 60.122 | −31.846 | 1.00 | 57.01 | B | C |
| ATOM | 10505 | O | GLY | B | 143 | 63.800 | 59.186 | −31.353 | 1.00 | 57.12 | B | O |
| ATOM | 10507 | N | ASN | B | 144 | 65.374 | 59.963 | −32.778 | 1.00 | 54.93 | B | N |
| ATOM | 10508 | CA | ASN | B | 144 | 65.892 | 58.658 | −33.197 | 1.00 | 52.65 | B | C |
| ATOM | 10510 | CB | ASN | B | 144 | 66.171 | 58.636 | −34.709 | 1.00 | 52.20 | B | C |
| ATOM | 10513 | CG | ASN | B | 144 | 64.960 | 59.056 | −35.545 | 1.00 | 55.56 | B | C |
| ATOM | 10514 | OD1 | ASN | B | 144 | 64.720 | 60.251 | −35.772 | 1.00 | 57.00 | B | O |
| ATOM | 10515 | ND2 | ASN | B | 144 | 64.208 | 58.073 | −36.026 | 1.00 | 53.61 | B | N |
| ATOM | 10518 | C | ASN | B | 144 | 67.189 | 58.393 | −32.442 | 1.00 | 49.76 | B | C |
| ATOM | 10519 | O | ASN | B | 144 | 67.842 | 59.331 | −32.005 | 1.00 | 48.69 | B | O |
| ATOM | 10521 | N | PHE | B | 145 | 67.569 | 57.126 | −32.281 | 1.00 | 47.64 | B | N |
| ATOM | 10522 | CA | PHE | B | 145 | 68.855 | 56.807 | −31.638 | 1.00 | 44.61 | B | C |
| ATOM | 10524 | CB | PHE | B | 145 | 69.028 | 55.293 | −31.433 | 1.00 | 43.24 | B | C |

TABLE 4-2-continued

Coordinates of *P. alba* IspS

| | | | | | | | | | | | | |
|---|---|---|---|---|---|---|---|---|---|---|---|---|
| ATOM | 10527 | CG | PHE | B | 145 | 68.385 | 54.778 | −30.171 | 1.00 | 37.63 | B | C |
| ATOM | 10528 | CD1 | PHE | B | 145 | 67.113 | 54.240 | −30.192 | 1.00 | 30.84 | B | C |
| ATOM | 10530 | CE1 | PHE | B | 145 | 66.516 | 53.777 | −29.038 | 1.00 | 32.98 | B | C |
| ATOM | 10532 | CZ | PHE | B | 145 | 67.188 | 53.849 | −27.839 | 1.00 | 35.80 | B | C |
| ATOM | 10534 | CE2 | PHE | B | 145 | 68.462 | 54.383 | −27.796 | 1.00 | 36.24 | B | C |
| ATOM | 10536 | CD2 | PHE | B | 145 | 69.052 | 54.851 | −28.958 | 1.00 | 35.52 | B | C |
| ATOM | 10538 | C | PHE | B | 145 | 70.014 | 57.381 | −32.452 | 1.00 | 44.54 | B | C |
| ATOM | 10539 | O | PHE | B | 145 | 69.957 | 57.418 | −33.679 | 1.00 | 43.23 | B | O |
| ATOM | 10541 | N | LEU | B | 146 | 71.051 | 57.846 | −31.761 | 1.00 | 45.81 | B | N |
| ATOM | 10542 | CA | LEU | B | 146 | 72.210 | 58.429 | −32.429 | 1.00 | 47.80 | B | C |
| ATOM | 10544 | CB | LEU | B | 146 | 73.211 | 58.969 | −31.402 | 1.00 | 48.75 | B | C |
| ATOM | 10547 | CG | LEU | B | 146 | 72.777 | 60.256 | −30.682 | 1.00 | 50.65 | B | C |
| ATOM | 10549 | CD1 | LEU | B | 146 | 73.588 | 60.481 | −29.409 | 1.00 | 52.76 | B | C |
| ATOM | 10553 | CD2 | LEU | B | 146 | 72.894 | 61.455 | −31.605 | 1.00 | 50.35 | B | C |
| ATOM | 10557 | C | LEU | B | 146 | 72.860 | 57.390 | −33.344 | 1.00 | 48.09 | B | C |
| ATOM | 10558 | O | LEU | B | 146 | 73.014 | 56.241 | −32.960 | 1.00 | 47.53 | B | O |
| ATOM | 10560 | N | GLU | B | 147 | 73.217 | 57.803 | −34.559 | 1.00 | 49.06 | B | N |
| ATOM | 10561 | CA | GLU | B | 147 | 73.758 | 56.896 | −35.582 | 1.00 | 49.97 | B | C |
| ATOM | 10563 | CB | GLU | B | 147 | 73.868 | 57.627 | −36.934 | 1.00 | 51.58 | B | C |
| ATOM | 10566 | CG | GLU | B | 147 | 74.260 | 56.747 | −38.147 | 1.00 | 56.44 | B | C |
| ATOM | 10569 | CD | GLU | B | 147 | 73.083 | 55.980 | −38.761 | 1.00 | 62.69 | B | C |
| ATOM | 10570 | OE1 | GLU | B | 147 | 71.979 | 56.554 | −38.876 | 1.00 | 64.99 | B | O |
| ATOM | 10571 | OE2 | GLU | B | 147 | 73.267 | 54.806 | −39.153 | 1.00 | 66.36 | B | O |
| ATOM | 10572 | C | GLU | B | 147 | 75.132 | 56.348 | −35.201 | 1.00 | 49.04 | B | C |
| ATOM | 10573 | O | GLU | B | 147 | 75.434 | 55.185 | −35.479 | 1.00 | 47.66 | B | O |
| ATOM | 10575 | N | ASN | B | 148 | 75.961 | 57.187 | −34.579 | 1.00 | 48.87 | B | N |
| ATOM | 10576 | CA | ASN | B | 148 | 77.347 | 56.814 | −34.262 | 1.00 | 49.90 | B | C |
| ATOM | 10578 | CB | ASN | B | 148 | 78.202 | 58.067 | −33.992 | 1.00 | 51.02 | B | C |
| ATOM | 10581 | CG | ASN | B | 148 | 78.031 | 58.610 | −32.576 | 1.00 | 56.07 | B | C |
| ATOM | 10582 | OD1 | ASN | B | 148 | 78.936 | 58.492 | −31.742 | 1.00 | 61.26 | B | O |
| ATOM | 10583 | ND2 | ASN | B | 148 | 76.868 | 59.198 | −32.297 | 1.00 | 58.99 | B | N |
| ATOM | 10586 | C | ASN | B | 148 | 77.497 | 55.801 | −33.110 | 1.00 | 48.73 | B | C |
| ATOM | 10587 | O | ASN | B | 148 | 78.611 | 55.402 | −32.776 | 1.00 | 49.75 | B | O |
| ATOM | 10589 | N | LEU | B | 149 | 76.382 | 55.390 | −32.507 | 1.00 | 47.68 | B | N |
| ATOM | 10590 | CA | LEU | B | 149 | 76.389 | 54.305 | −31.515 | 1.00 | 46.24 | B | C |
| ATOM | 10592 | CB | LEU | B | 149 | 75.105 | 54.326 | −30.675 | 1.00 | 44.68 | B | C |
| ATOM | 10595 | CG | LEU | B | 149 | 74.933 | 55.554 | −29.764 | 1.00 | 43.56 | B | C |
| ATOM | 10597 | CD1 | LEU | B | 149 | 73.479 | 55.709 | −29.326 | 1.00 | 39.02 | B | C |
| ATOM | 10601 | CD2 | LEU | B | 149 | 75.853 | 55.508 | −28.553 | 1.00 | 40.99 | B | C |
| ATOM | 10605 | C | LEU | B | 149 | 76.588 | 52.934 | −32.184 | 1.00 | 45.14 | B | C |
| ATOM | 10606 | O | LEU | B | 149 | 77.087 | 52.003 | −31.546 | 1.00 | 44.56 | B | O |
| ATOM | 10608 | N | LYS | B | 150 | 76.239 | 52.828 | −33.470 | 1.00 | 43.79 | B | N |
| ATOM | 10609 | CA | LYS | B | 150 | 76.438 | 51.593 | −34.246 | 1.00 | 43.54 | B | C |
| ATOM | 10611 | CB | LYS | B | 150 | 75.933 | 51.764 | −35.682 | 1.00 | 43.61 | B | C |
| ATOM | 10614 | CG | LYS | B | 150 | 76.894 | 52.553 | −36.587 | 1.00 | 46.08 | B | C |
| ATOM | 10617 | CD | LYS | B | 150 | 76.268 | 52.898 | −37.924 | 1.00 | 46.55 | B | C |
| ATOM | 10620 | CE | LYS | B | 150 | 77.268 | 53.562 | −38.861 | 1.00 | 44.81 | B | C |
| ATOM | 10623 | NZ | LYS | B | 150 | 76.697 | 53.648 | −40.228 | 1.00 | 43.17 | B | N |
| ATOM | 10627 | C | LYS | B | 150 | 77.893 | 51.098 | −34.291 | 1.00 | 43.90 | B | C |
| ATOM | 10628 | O | LYS | B | 150 | 78.127 | 49.952 | −34.663 | 1.00 | 43.76 | B | O |
| ATOM | 10630 | N | GLU | B | 151 | 78.854 | 51.963 | −33.953 | 1.00 | 44.36 | B | N |
| ATOM | 10631 | CA | AGLU | B | 151 | 80.275 | 51.600 | −33.889 | 0.50 | 45.03 | B | C |
| ATOM | 10632 | CA | BGLU | B | 151 | 80.259 | 51.556 | −33.922 | 0.50 | 44.55 | B | C |
| ATOM | 10635 | CB | AGLU | B | 151 | 81.158 | 52.860 | −33.903 | 0.50 | 45.31 | B | C |
| ATOM | 10636 | CB | BGLU | B | 151 | 81.192 | 52.765 | −34.101 | 0.50 | 44.49 | B | C |
| ATOM | 10641 | CG | AGLU | B | 151 | 81.067 | 53.700 | −35.176 | 0.50 | 46.10 | B | C |
| ATOM | 10642 | CG | BGLU | B | 151 | 80.988 | 53.561 | −35.408 | 0.50 | 42.68 | B | C |
| ATOM | 10647 | CD | AGLU | B | 151 | 81.927 | 54.953 | −35.116 | 0.50 | 46.35 | B | C |
| ATOM | 10648 | CD | BGLU | B | 151 | 81.246 | 52.747 | −36.675 | 0.50 | 39.43 | B | C |
| ATOM | 10649 | OE1 | AGLU | B | 151 | 82.923 | 54.965 | −34.361 | 0.50 | 46.87 | B | O |
| ATOM | 10650 | OE1 | BGLU | B | 151 | 82.082 | 51.820 | −36.641 | 0.50 | 33.96 | B | O |
| ATOM | 10651 | OE2 | AGLU | B | 151 | 81.610 | 55.927 | −35.830 | 0.50 | 47.69 | B | O |
| ATOM | 10652 | OE2 | BGLU | B | 151 | 80.611 | 53.048 | −37.711 | 0.50 | 33.24 | B | O |
| ATOM | 10653 | C | GLU | B | 151 | 80.593 | 50.796 | −32.629 | 1.00 | 44.92 | B | C |
| ATOM | 10654 | O | GLU | B | 151 | 81.544 | 50.008 | −32.603 | 1.00 | 45.51 | B | O |
| ATOM | 10656 | N | ASP | B | 152 | 79.806 | 51.022 | −31.573 | 1.00 | 43.91 | B | N |
| ATOM | 10657 | CA | ASP | B | 152 | 79.998 | 50.341 | −30.286 | 1.00 | 43.25 | B | C |
| ATOM | 10659 | CB | ASP | B | 152 | 79.682 | 51.305 | −29.129 | 1.00 | 42.94 | B | C |
| ATOM | 10662 | CG | ASP | B | 152 | 80.049 | 50.733 | −27.762 | 1.00 | 45.23 | B | C |
| ATOM | 10663 | OD1 | ASP | B | 152 | 80.532 | 49.581 | −27.686 | 1.00 | 44.55 | B | O |
| ATOM | 10664 | OD2 | ASP | B | 152 | 79.861 | 51.449 | −26.754 | 1.00 | 46.70 | B | O |
| ATOM | 10665 | C | ASP | B | 152 | 79.118 | 49.076 | −30.217 | 1.00 | 42.56 | B | C |
| ATOM | 10666 | O | ASP | B | 152 | 78.040 | 49.079 | −29.619 | 1.00 | 42.14 | B | O |
| ATOM | 10668 | N | ILE | B | 153 | 79.596 | 47.994 | −30.826 | 1.00 | 41.74 | B | N |
| ATOM | 10669 | CA | ILE | B | 153 | 78.793 | 46.777 | −31.016 | 1.00 | 40.19 | B | C |
| ATOM | 10671 | CB | ILE | B | 153 | 79.541 | 45.753 | −31.887 | 1.00 | 41.10 | B | C |
| ATOM | 10673 | CG1 | ILE | B | 153 | 79.823 | 46.346 | −33.276 | 1.00 | 43.65 | B | C |
| ATOM | 10676 | CD1 | ILE | B | 153 | 81.312 | 46.361 | −33.649 | 1.00 | 51.03 | B | C |

TABLE 4-2-continued

| Coordinates of *P. alba* IspS | | | | | | | | | | | |
|---|---|---|---|---|---|---|---|---|---|---|---|
| ATOM | 10680 | CG2 | ILE | B | 153 | 78.717 | 44.468 | −32.025 | 1.00 | 37.99 | B | C |
| ATOM | 10684 | C | ILE | B | 153 | 78.407 | 46.112 | −29.702 | 1.00 | 39.38 | B | C |
| ATOM | 10685 | O | ILE | B | 153 | 77.333 | 45.532 | −29.578 | 1.00 | 39.13 | B | O |
| ATOM | 10687 | N | LYS | B | 154 | 79.306 | 46.185 | −28.732 | 1.00 | 38.79 | B | N |
| ATOM | 10688 | CA | LYS | B | 154 | 79.039 | 45.739 | −27.379 | 1.00 | 38.18 | B | C |
| ATOM | 10690 | CB | LYS | B | 154 | 80.232 | 46.100 | −26.488 | 1.00 | 40.20 | B | C |
| ATOM | 10693 | CG | LYS | B | 154 | 80.401 | 45.276 | −25.243 | 1.00 | 45.47 | B | C |
| ATOM | 10696 | CD | LYS | B | 154 | 81.444 | 45.920 | −24.337 | 1.00 | 55.39 | B | C |
| ATOM | 10699 | CE | LYS | B | 154 | 82.112 | 44.908 | −23.420 | 1.00 | 61.69 | B | C |
| ATOM | 10702 | NZ | LYS | B | 154 | 83.180 | 44.159 | −24.141 | 1.00 | 65.48 | B | N |
| ATOM | 10706 | C | LYS | B | 154 | 77.772 | 46.418 | −26.863 | 1.00 | 35.45 | B | C |
| ATOM | 10707 | O | LYS | B | 154 | 76.867 | 45.753 | −26.351 | 1.00 | 34.35 | B | O |
| ATOM | 10709 | N | ALA | B | 155 | 77.702 | 47.740 | −27.023 | 1.00 | 32.93 | B | N |
| ATOM | 10710 | CA | ALA | B | 155 | 76.556 | 48.512 | −26.536 | 1.00 | 30.98 | B | C |
| ATOM | 10712 | CB | ALA | B | 155 | 76.862 | 50.001 | −26.539 | 1.00 | 28.88 | B | C |
| ATOM | 10716 | C | ALA | B | 155 | 75.300 | 48.222 | −27.344 | 1.00 | 30.46 | B | C |
| ATOM | 10717 | O | ALA | B | 155 | 74.190 | 48.256 | −26.799 | 1.00 | 31.94 | B | O |
| ATOM | 10719 | N | ILE | B | 156 | 75.457 | 47.925 | −28.632 | 1.00 | 29.25 | B | N |
| ATOM | 10720 | CA | ILE | B | 156 | 74.293 | 47.587 | −29.471 | 1.00 | 29.09 | B | C |
| ATOM | 10722 | CB | ILE | B | 156 | 74.595 | 47.690 | −30.966 | 1.00 | 28.51 | B | C |
| ATOM | 10724 | CG1 | ILE | B | 156 | 75.094 | 49.091 | −31.310 | 1.00 | 31.99 | B | C |
| ATOM | 10727 | CD1 | ILE | B | 156 | 74.186 | 50.194 | −30.831 | 1.00 | 34.35 | B | C |
| ATOM | 10731 | CG2 | ILE | B | 156 | 73.331 | 47.424 | −31.791 | 1.00 | 32.40 | B | C |
| ATOM | 10735 | C | ILE | B | 156 | 73.710 | 46.207 | −29.149 | 1.00 | 27.53 | B | C |
| ATOM | 10736 | O | ILE | B | 156 | 72.504 | 46.040 | −29.207 | 1.00 | 26.96 | B | O |
| ATOM | 10738 | N | LEU | B | 157 | 74.557 | 45.234 | −28.806 | 1.00 | 26.87 | B | N |
| ATOM | 10739 | CA | LEU | B | 157 | 74.082 | 43.932 | −28.339 | 1.00 | 28.36 | B | C |
| ATOM | 10741 | CB | LEU | B | 157 | 75.228 | 42.972 | −28.089 | 1.00 | 29.14 | B | C |
| ATOM | 10744 | CG | LEU | B | 157 | 75.829 | 42.284 | −29.298 | 1.00 | 33.60 | B | C |
| ATOM | 10746 | CD1 | LEU | B | 157 | 77.039 | 41.499 | −28.814 | 1.00 | 34.46 | B | C |
| ATOM | 10750 | CD2 | LEU | B | 157 | 74.802 | 41.359 | −29.938 | 1.00 | 34.45 | B | C |
| ATOM | 10754 | C | LEU | B | 157 | 73.345 | 44.078 | −27.029 | 1.00 | 27.60 | B | C |
| ATOM | 10755 | O | LEU | B | 157 | 72.273 | 43.506 | −26.850 | 1.00 | 26.85 | B | O |
| ATOM | 10757 | N | SER | B | 158 | 73.944 | 44.835 | −26.114 | 1.00 | 27.41 | B | N |
| ATOM | 10758 | CA | SER | B | 158 | 73.348 | 45.048 | −24.804 | 1.00 | 28.54 | B | C |
| ATOM | 10760 | CB | SER | B | 158 | 74.277 | 45.838 | −23.896 | 1.00 | 27.73 | B | C |
| ATOM | 10763 | OG | SER | B | 158 | 75.455 | 45.098 | −23.664 | 1.00 | 38.76 | B | O |
| ATOM | 10765 | C | SER | B | 158 | 72.015 | 45.762 | −24.937 | 1.00 | 26.50 | B | C |
| ATOM | 10766 | O | SER | B | 158 | 71.080 | 45.412 | −24.253 | 1.00 | 24.81 | B | O |
| ATOM | 10768 | N | LEU | B | 159 | 71.927 | 46.739 | −25.835 | 1.00 | 25.52 | B | N |
| ATOM | 10769 | CA | LEU | B | 159 | 70.659 | 47.441 | −26.078 | 1.00 | 24.28 | B | C |
| ATOM | 10771 | CB | LEU | B | 159 | 70.858 | 48.603 | −27.043 | 1.00 | 24.65 | B | C |
| ATOM | 10774 | CG | LEU | B | 159 | 69.626 | 49.433 | −27.397 | 1.00 | 24.51 | B | C |
| ATOM | 10776 | CD1 | LEU | B | 159 | 68.956 | 49.970 | −26.131 | 1.00 | 18.59 | B | C |
| ATOM | 10780 | CD2 | LEU | B | 159 | 70.046 | 50.557 | −28.350 | 1.00 | 23.65 | B | C |
| ATOM | 10784 | C | LEU | B | 159 | 69.624 | 46.484 | −26.647 | 1.00 | 23.61 | B | C |
| ATOM | 10785 | O | LEU | B | 159 | 68.469 | 46.488 | −26.226 | 1.00 | 25.84 | B | O |
| ATOM | 10787 | N | TYR | B | 160 | 70.046 | 45.665 | −27.602 | 1.00 | 21.32 | B | N |
| ATOM | 10788 | CA | TYR | B | 160 | 69.176 | 44.661 | −28.182 | 1.00 | 19.66 | B | C |
| ATOM | 10790 | CB | TYR | B | 160 | 69.963 | 43.869 | −29.209 | 1.00 | 18.24 | B | C |
| ATOM | 10793 | CG | TYR | B | 160 | 69.268 | 42.660 | −29.777 | 1.00 | 17.21 | B | C |
| ATOM | 10794 | CD1 | TYR | B | 160 | 68.354 | 42.773 | −30.807 | 1.00 | 23.20 | B | C |
| ATOM | 10796 | CE1 | TYR | B | 160 | 67.735 | 41.642 | −31.345 | 1.00 | 27.22 | B | C |
| ATOM | 10798 | CZ | TYR | B | 160 | 68.049 | 40.398 | −30.847 | 1.00 | 27.43 | B | C |
| ATOM | 10799 | OH | TYR | B | 160 | 67.454 | 39.267 | −31.356 | 1.00 | 42.06 | B | O |
| ATOM | 10801 | CE2 | TYR | B | 160 | 68.952 | 40.273 | −29.823 | 1.00 | 29.75 | B | C |
| ATOM | 10803 | CD2 | TYR | B | 160 | 69.558 | 41.398 | −29.300 | 1.00 | 27.84 | B | C |
| ATOM | 10805 | C | TYR | B | 160 | 68.611 | 43.735 | −27.102 | 1.00 | 21.10 | B | C |
| ATOM | 10806 | O | TYR | B | 160 | 67.392 | 43.479 | −27.061 | 1.00 | 20.13 | B | O |
| ATOM | 10808 | N | GLU | B | 161 | 69.491 | 43.246 | −26.223 | 1.00 | 22.83 | B | N |
| ATOM | 10809 | CA | GLU | B | 161 | 69.086 | 42.289 | −25.195 | 1.00 | 22.44 | B | C |
| ATOM | 10811 | CB | GLU | B | 161 | 70.292 | 41.754 | −24.422 | 1.00 | 22.12 | B | C |
| ATOM | 10814 | CG | GLU | B | 161 | 71.263 | 40.919 | −25.261 | 1.00 | 25.71 | B | C |
| ATOM | 10817 | CD | GLU | B | 161 | 70.733 | 39.523 | −25.628 | 1.00 | 27.66 | B | C |
| ATOM | 10818 | OE1 | GLU | B | 161 | 69.565 | 39.178 | −25.328 | 1.00 | 34.19 | B | O |
| ATOM | 10819 | OE2 | GLU | B | 161 | 71.505 | 38.754 | −26.223 | 1.00 | 23.37 | B | O |
| ATOM | 10820 | C | GLU | B | 161 | 68.120 | 42.947 | −24.227 | 1.00 | 22.70 | B | C |
| ATOM | 10821 | O | GLU | B | 161 | 67.144 | 42.332 | −23.790 | 1.00 | 23.48 | B | O |
| ATOM | 10823 | N | ALA | B | 162 | 68.396 | 44.199 | −23.899 | 1.00 | 20.82 | B | N |
| ATOM | 10824 | CA | ALA | B | 162 | 67.568 | 44.936 | −22.974 | 1.00 | 21.15 | B | C |
| ATOM | 10826 | CB | ALA | B | 162 | 68.202 | 46.260 | −22.655 | 1.00 | 18.59 | B | C |
| ATOM | 10830 | C | ALA | B | 162 | 66.170 | 45.145 | −23.528 | 1.00 | 22.41 | B | C |
| ATOM | 10831 | O | ALA | B | 162 | 65.197 | 45.161 | −22.765 | 1.00 | 24.55 | B | O |
| ATOM | 10833 | N | SER | B | 163 | 66.063 | 45.300 | −24.845 | 1.00 | 21.15 | B | N |
| ATOM | 10834 | CA | SER | B | 163 | 64.781 | 45.630 | −25.451 | 1.00 | 22.45 | B | C |
| ATOM | 10836 | CB | SER | B | 163 | 64.925 | 45.885 | −26.971 | 1.00 | 22.21 | B | C |
| ATOM | 10839 | OG | SER | B | 163 | 65.265 | 44.708 | −27.695 | 1.00 | 22.00 | B | O |
| ATOM | 10841 | C | SER | B | 163 | 63.725 | 44.554 | −25.191 | 1.00 | 22.67 | B | C |

TABLE 4-2-continued

Coordinates of *P. alba* IspS

| | | | | | | | | | | | | |
|---|---|---|---|---|---|---|---|---|---|---|---|---|
| ATOM | 10842 | O | SER | B | 163 | 62.529 | 44.867 | −25.088 | 1.00 | 22.75 | B | O |
| ATOM | 10844 | N | PHE | B | 164 | 64.149 | 43.297 | −25.057 | 1.00 | 22.13 | B | N |
| ATOM | 10845 | CA | PHE | B | 164 | 63.175 | 42.225 | −24.898 | 1.00 | 22.96 | B | C |
| ATOM | 10847 | CB | PHE | B | 164 | 63.789 | 40.856 | −25.224 | 1.00 | 22.93 | B | C |
| ATOM | 10850 | CG | PHE | B | 164 | 64.027 | 40.683 | −26.692 | 1.00 | 22.93 | B | C |
| ATOM | 10851 | CD1 | PHE | B | 164 | 63.027 | 40.169 | −27.515 | 1.00 | 24.94 | B | C |
| ATOM | 10853 | CE1 | PHE | B | 164 | 63.205 | 40.072 | −28.886 | 1.00 | 20.58 | B | C |
| ATOM | 10855 | CZ | PHE | B | 164 | 64.377 | 40.516 | −29.455 | 1.00 | 20.41 | B | C |
| ATOM | 10857 | CE2 | PHE | B | 164 | 65.387 | 41.073 | −28.633 | 1.00 | 24.66 | B | C |
| ATOM | 10859 | CD2 | PHE | B | 164 | 65.186 | 41.171 | −27.271 | 1.00 | 19.04 | B | C |
| ATOM | 10861 | C | PHE | B | 164 | 62.492 | 42.257 | −23.547 | 1.00 | 22.65 | B | C |
| ATOM | 10862 | O | PHE | B | 164 | 61.512 | 41.539 | −23.338 | 1.00 | 23.15 | B | O |
| ATOM | 10864 | N | LEU | B | 165 | 62.952 | 43.122 | −22.642 | 1.00 | 22.52 | B | N |
| ATOM | 10865 | CA | LEU | B | 165 | 62.341 | 43.187 | −21.315 | 1.00 | 21.55 | B | C |
| ATOM | 10867 | CB | LEU | B | 165 | 63.392 | 43.432 | −20.237 | 1.00 | 23.26 | B | C |
| ATOM | 10870 | CG | LEU | B | 165 | 64.195 | 42.197 | −19.851 | 1.00 | 23.00 | B | C |
| ATOM | 10872 | CD1 | LEU | B | 165 | 65.339 | 41.953 | −20.829 | 1.00 | 20.20 | B | C |
| ATOM | 10876 | CD2 | LEU | B | 165 | 64.728 | 42.347 | −18.432 | 1.00 | 23.73 | B | C |
| ATOM | 10880 | C | LEU | B | 165 | 61.258 | 44.228 | −21.256 | 1.00 | 22.76 | B | C |
| ATOM | 10881 | O | LEU | B | 165 | 60.804 | 44.591 | −20.174 | 1.00 | 23.40 | B | O |
| ATOM | 10883 | N | ALA | B | 166 | 60.822 | 44.692 | −22.426 | 1.00 | 22.61 | B | N |
| ATOM | 10884 | CA | ALA | B | 166 | 59.900 | 45.804 | −22.517 | 1.00 | 23.27 | B | C |
| ATOM | 10886 | CB | ALA | B | 166 | 59.693 | 46.181 | −23.973 | 1.00 | 21.35 | B | C |
| ATOM | 10890 | C | ALA | B | 166 | 58.565 | 45.464 | −21.899 | 1.00 | 22.57 | B | C |
| ATOM | 10891 | O | ALA | B | 166 | 58.155 | 44.325 | −21.932 | 1.00 | 24.73 | B | O |
| ATOM | 10893 | N | LEU | B | 167 | 57.906 | 46.463 | −21.338 | 1.00 | 23.68 | B | N |
| ATOM | 10894 | CA | LEU | B | 167 | 56.489 | 46.397 | −21.010 | 1.00 | 25.21 | B | C |
| ATOM | 10896 | CB | LEU | B | 167 | 56.234 | 47.072 | −19.671 | 1.00 | 25.95 | B | C |
| ATOM | 10899 | CG | LEU | B | 167 | 57.098 | 46.586 | −18.506 | 1.00 | 29.63 | B | C |
| ATOM | 10901 | CD1 | LEU | B | 167 | 56.644 | 47.255 | −17.228 | 1.00 | 27.25 | B | C |
| ATOM | 10905 | CD2 | LEU | B | 167 | 57.012 | 45.081 | −18.375 | 1.00 | 25.26 | B | C |
| ATOM | 10909 | C | LEU | B | 167 | 55.663 | 47.096 | −22.097 | 1.00 | 26.22 | B | C |
| ATOM | 10910 | O | LEU | B | 167 | 56.203 | 47.772 | −22.981 | 1.00 | 28.50 | B | O |
| ATOM | 10912 | N | GLU | B | 168 | 54.352 | 46.917 | −22.039 | 1.00 | 26.78 | B | N |
| ATOM | 10913 | CA | GLU | B | 168 | 53.440 | 47.650 | −22.919 | 1.00 | 27.31 | B | C |
| ATOM | 10915 | CB | GLU | B | 168 | 52.004 | 47.290 | −22.578 | 1.00 | 28.21 | B | C |
| ATOM | 10918 | CG | GLU | B | 168 | 51.505 | 46.007 | −23.166 | 1.00 | 35.50 | B | C |
| ATOM | 10921 | CD | GLU | B | 168 | 49.971 | 45.971 | −23.198 | 1.00 | 43.15 | B | C |
| ATOM | 10922 | OE1 | GLU | B | 168 | 49.400 | 45.294 | −22.314 | 1.00 | 41.77 | B | O |
| ATOM | 10923 | OE2 | GLU | B | 168 | 49.352 | 46.633 | −24.084 | 1.00 | 44.65 | B | O |
| ATOM | 10924 | C | GLU | B | 168 | 53.584 | 49.172 | −22.760 | 1.00 | 25.57 | B | C |
| ATOM | 10925 | O | GLU | B | 168 | 53.595 | 49.675 | −21.638 | 1.00 | 25.79 | B | O |
| ATOM | 10927 | N | GLY | B | 169 | 53.657 | 49.887 | −23.880 | 1.00 | 25.49 | B | N |
| ATOM | 10928 | CA | GLY | B | 169 | 53.772 | 51.356 | −23.887 | 1.00 | 24.53 | B | C |
| ATOM | 10931 | C | GLY | B | 169 | 55.226 | 51.835 | −23.860 | 1.00 | 25.77 | B | C |
| ATOM | 10932 | O | GLY | B | 169 | 55.504 | 53.029 | −24.003 | 1.00 | 25.33 | B | O |
| ATOM | 10934 | N | GLU | B | 170 | 56.170 | 50.916 | −23.681 | 1.00 | 24.26 | B | N |
| ATOM | 10935 | CA | GLU | B | 170 | 57.563 | 51.316 | −23.691 | 1.00 | 24.47 | B | C |
| ATOM | 10937 | CB | GLU | B | 170 | 58.409 | 50.390 | −22.809 | 1.00 | 23.98 | B | C |
| ATOM | 10940 | CG | GLU | B | 170 | 58.085 | 50.601 | −21.322 | 1.00 | 27.09 | B | C |
| ATOM | 10943 | CD | GLU | B | 170 | 58.979 | 49.840 | −20.370 | 1.00 | 32.50 | B | C |
| ATOM | 10944 | OE1 | GLU | B | 170 | 59.047 | 50.248 | −19.187 | 1.00 | 33.97 | B | O |
| ATOM | 10945 | OE2 | GLU | B | 170 | 59.600 | 48.835 | −20.791 | 1.00 | 33.76 | B | O |
| ATOM | 10946 | C | GLU | B | 170 | 58.057 | 51.391 | −25.122 | 1.00 | 25.33 | B | C |
| ATOM | 10947 | O | GLU | B | 170 | 58.854 | 50.580 | −25.562 | 1.00 | 25.77 | B | O |
| ATOM | 10949 | N | ASN | B | 171 | 57.583 | 52.405 | −25.838 | 1.00 | 25.86 | B | N |
| ATOM | 10950 | CA | ASN | B | 171 | 57.942 | 52.584 | −27.238 | 1.00 | 26.42 | B | C |
| ATOM | 10952 | CB | ASN | B | 171 | 57.206 | 53.793 | −27.826 | 1.00 | 26.53 | B | C |
| ATOM | 10955 | CG | ASN | B | 171 | 57.401 | 55.060 | −26.997 | 1.00 | 32.07 | B | C |
| ATOM | 10956 | OD1 | ASN | B | 171 | 56.890 | 55.173 | −25.877 | 1.00 | 29.89 | B | O |
| ATOM | 10957 | ND2 | ASN | B | 171 | 58.153 | 56.012 | −27.539 | 1.00 | 28.86 | B | N |
| ATOM | 10960 | C | ASN | B | 171 | 59.449 | 52.727 | −27.472 | 1.00 | 27.85 | B | C |
| ATOM | 10961 | O | ASN | B | 171 | 59.962 | 52.316 | −28.511 | 1.00 | 29.62 | B | O |
| ATOM | 10963 | N | ILE | B | 172 | 60.163 | 53.299 | −26.512 | 1.00 | 28.75 | B | N |
| ATOM | 10964 | CA | ILE | B | 172 | 61.596 | 53.523 | −26.679 | 1.00 | 29.05 | B | C |
| ATOM | 10966 | CB | ILE | B | 172 | 62.175 | 54.382 | −25.549 | 1.00 | 29.12 | B | C |
| ATOM | 10968 | CG1 | ILE | B | 172 | 61.608 | 55.804 | −25.644 | 1.00 | 31.03 | B | C |
| ATOM | 10971 | CD1 | ILE | B | 172 | 61.983 | 56.695 | −24.488 | 1.00 | 32.54 | B | C |
| ATOM | 10975 | CG2 | ILE | B | 172 | 63.686 | 54.472 | −25.651 | 1.00 | 28.63 | B | C |
| ATOM | 10979 | C | ILE | B | 172 | 62.337 | 52.200 | −26.804 | 1.00 | 30.66 | B | C |
| ATOM | 10980 | O | ILE | B | 172 | 63.244 | 52.075 | −27.629 | 1.00 | 32.83 | B | O |
| ATOM | 10982 | N | LEU | B | 173 | 61.922 | 51.200 | −26.029 | 1.00 | 30.45 | B | N |
| ATOM | 10983 | CA | LEU | B | 173 | 62.542 | 49.875 | −26.103 | 1.00 | 28.89 | B | C |
| ATOM | 10985 | CB | LEU | B | 173 | 62.098 | 49.006 | −24.923 | 1.00 | 28.96 | B | C |
| ATOM | 10988 | CG | LEU | B | 173 | 62.869 | 49.210 | −23.615 | 1.00 | 28.06 | B | C |
| ATOM | 10990 | CD1 | LEU | B | 173 | 63.107 | 50.664 | −23.324 | 1.00 | 28.03 | B | C |
| ATOM | 10994 | CD2 | LEU | B | 173 | 62.101 | 48.562 | −22.474 | 1.00 | 28.74 | B | C |
| ATOM | 10998 | C | LEU | B | 173 | 62.221 | 49.191 | −27.433 | 1.00 | 28.15 | B | C |

TABLE 4-2-continued

| Coordinates of *P. alba* IspS | | | | | | | | | | | |
|---|---|---|---|---|---|---|---|---|---|---|---|
| ATOM | 10999 | O | LEU | B | 173 | 63.094 | 48.582 | −28.049 | 1.00 | 29.10 | B | O |
| ATOM | 11001 | N | ASP | B | 174 | 60.976 | 49.298 | −27.878 | 1.00 | 27.45 | B | N |
| ATOM | 11002 | CA | ASP | B | 174 | 60.586 | 48.825 | −29.222 | 1.00 | 28.78 | B | C |
| ATOM | 11004 | CB | ASP | B | 174 | 59.117 | 49.152 | −29.509 | 1.00 | 29.66 | B | C |
| ATOM | 11007 | CG | ASP | B | 174 | 58.140 | 48.181 | −28.843 | 1.00 | 36.16 | B | C |
| ATOM | 11008 | OD1 | ASP | B | 174 | 58.535 | 47.387 | −27.960 | 1.00 | 45.20 | B | O |
| ATOM | 11009 | OD2 | ASP | B | 174 | 56.954 | 48.219 | −29.219 | 1.00 | 44.48 | B | O |
| ATOM | 11010 | C | ASP | B | 174 | 61.439 | 49.465 | −30.314 | 1.00 | 28.84 | B | C |
| ATOM | 11011 | O | ASP | B | 174 | 61.879 | 48.805 | −31.254 | 1.00 | 30.79 | B | O |
| ATOM | 11013 | N | GLU | B | 175 | 61.660 | 50.760 | −30.193 | 1.00 | 29.80 | B | N |
| ATOM | 11014 | CA | GLU | B | 175 | 62.492 | 51.469 | −31.151 | 1.00 | 30.39 | B | C |
| ATOM | 11016 | CB | GLU | B | 175 | 62.349 | 52.977 | −30.949 | 1.00 | 30.54 | B | C |
| ATOM | 11019 | CG | GLU | B | 175 | 60.948 | 53.528 | −31.292 | 1.00 | 35.87 | B | C |
| ATOM | 11022 | CD | GLU | B | 175 | 60.612 | 54.872 | −30.601 | 1.00 | 42.68 | B | C |
| ATOM | 11023 | OE1 | GLU | B | 175 | 61.530 | 55.551 | −30.070 | 1.00 | 40.27 | B | O |
| ATOM | 11024 | OE2 | GLU | B | 175 | 59.413 | 55.246 | −30.602 | 1.00 | 43.14 | B | O |
| ATOM | 11025 | C | GLU | B | 175 | 63.944 | 51.005 | −30.982 | 1.00 | 30.18 | B | C |
| ATOM | 11026 | O | GLU | B | 175 | 64.660 | 50.798 | −31.969 | 1.00 | 30.45 | B | O |
| ATOM | 11028 | N | ALA | B | 176 | 64.359 | 50.807 | −29.732 | 1.00 | 28.90 | B | N |
| ATOM | 11029 | CA | ALA | B | 176 | 65.695 | 50.272 | −29.433 | 1.00 | 27.90 | B | C |
| ATOM | 11031 | CB | ALA | B | 176 | 65.829 | 49.984 | −27.974 | 1.00 | 26.60 | B | C |
| ATOM | 11035 | C | ALA | B | 176 | 65.973 | 49.011 | −30.228 | 1.00 | 27.63 | B | C |
| ATOM | 11036 | O | ALA | B | 176 | 67.037 | 48.867 | −30.823 | 1.00 | 27.16 | B | O |
| ATOM | 11038 | N | LYS | B | 177 | 64.992 | 48.118 | −30.253 | 1.00 | 27.87 | B | N |
| ATOM | 11039 | CA | LYS | B | 177 | 65.143 | 46.821 | −30.902 | 1.00 | 27.75 | B | C |
| ATOM | 11041 | CB | LYS | B | 177 | 63.983 | 45.879 | −30.524 | 1.00 | 25.44 | B | C |
| ATOM | 11044 | CG | LYS | B | 177 | 63.931 | 44.587 | −31.332 | 1.00 | 27.36 | B | C |
| ATOM | 11047 | CD | LYS | B | 177 | 63.211 | 43.426 | −30.638 | 1.00 | 31.71 | B | C |
| ATOM | 11050 | CE | LYS | B | 177 | 61.774 | 43.731 | −30.205 | 1.00 | 32.14 | B | C |
| ATOM | 11053 | NZ | LYS | B | 177 | 61.287 | 42.780 | −29.169 | 1.00 | 25.79 | B | N |
| ATOM | 11057 | C | LYS | B | 177 | 65.251 | 46.964 | −32.419 | 1.00 | 29.31 | B | C |
| ATOM | 11058 | O | LYS | B | 177 | 66.057 | 46.272 | −33.042 | 1.00 | 30.76 | B | O |
| ATOM | 11060 | N | VAL | B | 178 | 64.420 | 47.828 | −33.006 | 1.00 | 30.40 | B | N |
| ATOM | 11061 | CA | VAL | B | 178 | 64.425 | 48.056 | −34.460 | 1.00 | 29.52 | B | C |
| ATOM | 11063 | CB | VAL | B | 178 | 63.367 | 49.122 | −34.909 | 1.00 | 29.52 | B | C |
| ATOM | 11065 | CG1 | VAL | B | 178 | 63.644 | 49.609 | −36.351 | 1.00 | 27.87 | B | C |
| ATOM | 11069 | CG2 | VAL | B | 178 | 61.941 | 48.598 | −34.790 | 1.00 | 27.79 | B | C |
| ATOM | 11073 | C | VAL | B | 178 | 65.797 | 48.585 | −34.819 | 1.00 | 30.34 | B | C |
| ATOM | 11074 | O | VAL | B | 178 | 66.452 | 48.101 | −35.752 | 1.00 | 31.89 | B | O |
| ATOM | 11076 | N | PHE | B | 179 | 66.229 | 49.575 | −34.047 | 1.00 | 30.22 | B | N |
| ATOM | 11077 | CA | PHE | B | 179 | 67.516 | 50.223 | −34.258 | 1.00 | 29.99 | B | C |
| ATOM | 11079 | CB | PHE | B | 179 | 67.688 | 51.372 | −33.260 | 1.00 | 29.89 | B | C |
| ATOM | 11082 | CG | PHE | B | 179 | 69.056 | 51.967 | −33.262 | 1.00 | 29.85 | B | C |
| ATOM | 11083 | CD1 | PHE | B | 179 | 69.476 | 52.745 | −34.322 | 1.00 | 30.02 | B | C |
| ATOM | 11085 | CE1 | PHE | B | 179 | 70.743 | 53.287 | −34.335 | 1.00 | 30.08 | B | C |
| ATOM | 11087 | CZ | PHE | B | 179 | 71.607 | 53.063 | −33.276 | 1.00 | 31.16 | B | C |
| ATOM | 11089 | CE2 | PHE | B | 179 | 71.207 | 52.288 | −32.215 | 1.00 | 32.64 | B | C |
| ATOM | 11091 | CD2 | PHE | B | 179 | 69.929 | 51.735 | −32.213 | 1.00 | 31.27 | B | C |
| ATOM | 11093 | C | PHE | B | 179 | 68.694 | 49.251 | −34.147 | 1.00 | 30.91 | B | C |
| ATOM | 11094 | O | PHE | B | 179 | 69.531 | 49.183 | −35.054 | 1.00 | 33.53 | B | O |
| ATOM | 11096 | N | ALA | B | 180 | 68.763 | 48.502 | −33.049 | 1.00 | 29.27 | B | N |
| ATOM | 11097 | CA | ALA | B | 180 | 69.898 | 47.602 | −32.831 | 1.00 | 28.27 | B | C |
| ATOM | 11099 | CB | ALA | B | 180 | 69.951 | 47.121 | −31.393 | 1.00 | 26.03 | B | C |
| ATOM | 11103 | C | ALA | B | 180 | 69.886 | 46.429 | −33.794 | 1.00 | 28.76 | B | C |
| ATOM | 11104 | O | ALA | B | 180 | 70.928 | 46.013 | −34.264 | 1.00 | 30.14 | B | O |
| ATOM | 11106 | N | ILE | B | 181 | 68.713 | 45.903 | −34.105 | 1.00 | 30.72 | B | N |
| ATOM | 11107 | CA | ILE | B | 181 | 68.621 | 44.841 | −35.108 | 1.00 | 32.83 | B | C |
| ATOM | 11109 | CB | ILE | B | 181 | 67.160 | 44.382 | −35.331 | 1.00 | 32.27 | B | C |
| ATOM | 11111 | CG1 | ILE | B | 181 | 66.724 | 43.407 | −34.235 | 1.00 | 37.17 | B | C |
| ATOM | 11114 | CD1 | ILE | B | 181 | 65.238 | 42.897 | −34.385 | 1.00 | 36.59 | B | C |
| ATOM | 11118 | CG2 | ILE | B | 181 | 66.995 | 43.703 | −36.694 | 1.00 | 34.78 | B | C |
| ATOM | 11122 | C | ILE | B | 181 | 69.217 | 45.289 | −36.452 | 1.00 | 34.90 | B | C |
| ATOM | 11123 | O | ILE | B | 181 | 69.973 | 44.539 | −37.078 | 1.00 | 35.81 | B | O |
| ATOM | 11125 | N | SER | B | 182 | 68.885 | 46.501 | −36.893 | 1.00 | 36.36 | B | N |
| ATOM | 11126 | CA | SER | B | 182 | 69.314 | 46.952 | −38.229 | 1.00 | 38.78 | B | C |
| ATOM | 11128 | CB | SER | B | 182 | 68.701 | 48.315 | −38.607 | 1.00 | 38.10 | B | C |
| ATOM | 11131 | OG | SER | B | 182 | 69.333 | 49.382 | −37.919 | 1.00 | 41.06 | B | O |
| ATOM | 11133 | C | SER | B | 182 | 70.840 | 46.992 | −38.350 | 1.00 | 39.40 | B | C |
| ATOM | 11134 | O | SER | B | 182 | 71.385 | 46.696 | −39.407 | 1.00 | 40.69 | B | O |
| ATOM | 11136 | N | HIS | B | 183 | 71.532 | 47.334 | −37.269 | 1.00 | 40.96 | B | N |
| ATOM | 11137 | CA | HIS | B | 183 | 72.998 | 47.410 | −37.315 | 1.00 | 41.22 | B | C |
| ATOM | 11139 | CB | HIS | B | 183 | 73.503 | 48.563 | −36.448 | 1.00 | 40.88 | B | C |
| ATOM | 11142 | CG | HIS | B | 183 | 73.160 | 49.899 | −37.014 | 1.00 | 46.75 | B | C |
| ATOM | 11143 | ND1 | HIS | B | 183 | 72.264 | 50.757 | −36.415 | 1.00 | 50.90 | B | N |
| ATOM | 11145 | CE1 | HIS | B | 183 | 72.134 | 51.840 | −37.161 | 1.00 | 54.30 | B | C |
| ATOM | 11147 | NE2 | HIS | B | 183 | 72.896 | 51.704 | −38.231 | 1.00 | 53.96 | B | N |
| ATOM | 11149 | CD2 | HIS | B | 183 | 73.543 | 50.495 | −38.167 | 1.00 | 48.27 | B | C |
| ATOM | 11151 | C | HIS | B | 183 | 73.703 | 46.112 | −36.955 | 1.00 | 40.72 | B | C |

TABLE 4-2-continued

| Coordinates of *P. alba* IspS | | | | | | | | | | | | |
|---|---|---|---|---|---|---|---|---|---|---|---|---|
| ATOM | 11152 | O | HIS | B | 183 | 74.900 | 46.003 | −37.173 | 1.00 | 42.77 | B | O |
| ATOM | 11154 | N | LEU | B | 184 | 72.973 | 45.128 | −36.432 | 1.00 | 39.36 | B | N |
| ATOM | 11155 | CA | LEU | B | 184 | 73.590 | 43.855 | −36.043 | 1.00 | 38.20 | B | C |
| ATOM | 11157 | CB | LEU | B | 184 | 72.887 | 43.260 | −34.811 | 1.00 | 36.21 | B | C |
| ATOM | 11160 | CG | LEU | B | 184 | 73.193 | 43.912 | −33.457 | 1.00 | 33.67 | B | C |
| ATOM | 11162 | CD1 | LEU | B | 184 | 72.210 | 43.448 | −32.429 | 1.00 | 23.99 | B | C |
| ATOM | 11166 | CD2 | LEU | B | 184 | 74.618 | 43.608 | −33.002 | 1.00 | 27.65 | B | C |
| ATOM | 11170 | C | LEU | B | 184 | 73.628 | 42.823 | −37.179 | 1.00 | 40.01 | B | C |
| ATOM | 11171 | O | LEU | B | 184 | 74.596 | 42.065 | −37.301 | 1.00 | 37.78 | B | O |
| ATOM | 11173 | N | LYS | B | 185 | 72.590 | 42.763 | −38.006 | 1.00 | 43.51 | B | N |
| ATOM | 11174 | CA | LYS | B | 185 | 72.541 | 41.685 | −39.001 | 1.00 | 48.61 | B | C |
| ATOM | 11176 | CB | LYS | B | 185 | 71.099 | 41.321 | −39.391 | 1.00 | 49.10 | B | C |
| ATOM | 11179 | CG | LYS | B | 185 | 70.449 | 42.148 | −40.488 | 1.00 | 55.39 | B | C |
| ATOM | 11182 | CD | LYS | B | 185 | 68.962 | 41.760 | −40.670 | 1.00 | 62.71 | B | C |
| ATOM | 11185 | CE | LYS | B | 185 | 68.785 | 40.320 | −41.201 | 1.00 | 66.06 | B | C |
| ATOM | 11188 | NZ | LYS | B | 185 | 67.354 | 39.952 | −41.448 | 1.00 | 65.27 | B | N |
| ATOM | 11192 | C | LYS | B | 185 | 73.431 | 41.961 | −40.218 | 1.00 | 50.99 | B | C |
| ATOM | 11193 | O | LYS | B | 185 | 73.784 | 41.040 | −40.944 | 1.00 | 51.11 | B | O |
| ATOM | 11195 | N | GLU | B | 186 | 73.828 | 43.213 | −40.403 | 1.00 | 54.84 | B | N |
| ATOM | 11196 | CA | GLU | B | 186 | 74.706 | 43.569 | −41.513 | 1.00 | 59.61 | B | C |
| ATOM | 11198 | CB | GLU | B | 186 | 74.519 | 45.052 | −41.895 | 1.00 | 60.90 | B | C |
| ATOM | 11201 | CG | GLU | B | 186 | 73.110 | 45.425 | −42.369 | 1.00 | 64.87 | B | C |
| ATOM | 11204 | CD | GLU | B | 186 | 72.750 | 44.835 | −43.733 | 1.00 | 70.39 | B | C |
| ATOM | 11205 | OE1 | GLU | B | 186 | 73.310 | 45.292 | −44.758 | 1.00 | 71.34 | B | O |
| ATOM | 11206 | OE2 | GLU | B | 186 | 71.889 | 43.925 | −43.777 | 1.00 | 69.40 | B | O |
| ATOM | 11207 | C | GLU | B | 186 | 76.197 | 43.293 | −41.233 | 1.00 | 60.98 | B | C |
| ATOM | 11208 | O | GLU | B | 186 | 77.017 | 43.423 | −42.139 | 1.00 | 61.95 | B | O |
| ATOM | 11210 | N | LEU | B | 187 | 76.549 | 42.907 | −40.004 | 1.00 | 62.28 | B | N |
| ATOM | 11211 | CA | LEU | B | 187 | 77.964 | 42.855 | −39.581 | 1.00 | 62.62 | B | C |
| ATOM | 11213 | CB | LEU | B | 187 | 78.078 | 42.851 | −38.054 | 1.00 | 61.51 | B | C |
| ATOM | 11216 | CG | LEU | B | 187 | 77.507 | 44.076 | −37.343 | 1.00 | 60.53 | B | C |
| ATOM | 11218 | CD1 | LEU | B | 187 | 77.696 | 43.951 | −35.843 | 1.00 | 56.66 | B | C |
| ATOM | 11222 | CD2 | LEU | B | 187 | 78.131 | 45.375 | −37.861 | 1.00 | 60.27 | B | C |
| ATOM | 11226 | C | LEU | B | 187 | 78.736 | 41.662 | −40.143 | 1.00 | 64.20 | B | C |
| ATOM | 11227 | O | LEU | B | 187 | 78.216 | 40.546 | −40.198 | 1.00 | 64.08 | B | O |
| ATOM | 11229 | N | SER | B | 188 | 79.987 | 41.914 | −40.533 | 1.00 | 65.99 | B | N |
| ATOM | 11230 | CA | SER | B | 188 | 80.843 | 40.903 | −41.168 | 1.00 | 67.23 | B | C |
| ATOM | 11232 | CB | SER | B | 188 | 81.579 | 41.514 | −42.370 | 1.00 | 67.61 | B | C |
| ATOM | 11235 | OG | SER | B | 188 | 82.193 | 40.517 | −43.168 | 1.00 | 68.97 | B | O |
| ATOM | 11237 | C | SER | B | 188 | 81.862 | 40.357 | −40.172 | 1.00 | 67.24 | B | C |
| ATOM | 11238 | O | SER | B | 188 | 82.548 | 41.136 | −39.507 | 1.00 | 66.19 | B | O |
| ATOM | 11240 | N | GLU | B | 189 | 81.970 | 39.026 | −40.093 | 1.00 | 68.52 | B | N |
| ATOM | 11241 | CA | GLU | B | 189 | 82.944 | 38.357 | −39.206 | 1.00 | 70.09 | B | C |
| ATOM | 11243 | CB | GLU | B | 189 | 82.912 | 36.818 | −39.372 | 1.00 | 70.61 | B | C |
| ATOM | 11246 | CG | GLU | B | 189 | 84.084 | 36.079 | −38.655 | 1.00 | 74.42 | B | C |
| ATOM | 11249 | CD | GLU | B | 189 | 83.884 | 34.571 | −38.451 | 1.00 | 78.48 | B | C |
| ATOM | 11250 | OE1 | GLU | B | 189 | 82.846 | 34.014 | −38.868 | 1.00 | 78.02 | B | O |
| ATOM | 11251 | OE2 | GLU | B | 189 | 84.790 | 33.939 | −37.857 | 1.00 | 81.03 | B | O |
| ATOM | 11252 | C | GLU | B | 189 | 84.366 | 38.869 | −39.429 | 1.00 | 70.71 | B | C |
| ATOM | 11253 | O | GLU | B | 189 | 85.214 | 38.768 | −38.538 | 1.00 | 69.61 | B | O |
| ATOM | 11255 | N | GLU | B | 190 | 84.619 | 39.412 | −40.617 | 1.00 | 71.86 | B | N |
| ATOM | 11256 | CA | GLU | B | 190 | 85.936 | 39.921 | −40.967 | 1.00 | 73.09 | B | C |
| ATOM | 11258 | CB | GLU | B | 190 | 86.081 | 39.953 | −42.492 | 1.00 | 74.22 | B | C |
| ATOM | 11261 | CG | GLU | B | 190 | 85.947 | 38.559 | −43.117 | 1.00 | 77.50 | B | C |
| ATOM | 11264 | CD | GLU | B | 190 | 85.806 | 38.582 | −44.623 | 1.00 | 80.99 | B | C |
| ATOM | 11265 | OE1 | GLU | B | 190 | 86.833 | 38.752 | −45.309 | 1.00 | 81.25 | B | O |
| ATOM | 11266 | OE2 | GLU | B | 190 | 84.674 | 38.400 | −45.121 | 1.00 | 84.29 | B | O |
| ATOM | 11267 | C | GLU | B | 190 | 86.227 | 41.289 | −40.324 | 1.00 | 72.73 | B | C |
| ATOM | 11268 | O | GLU | B | 190 | 87.328 | 41.505 | −39.808 | 1.00 | 72.35 | B | O |
| ATOM | 11270 | N | LYS | B | 191 | 85.246 | 42.195 | −40.334 | 1.00 | 72.21 | B | N |
| ATOM | 11271 | CA | LYS | B | 191 | 85.414 | 43.512 | −39.697 | 1.00 | 72.24 | B | C |
| ATOM | 11273 | CB | LYS | B | 191 | 84.208 | 44.417 | −39.967 | 1.00 | 73.12 | B | C |
| ATOM | 11276 | CG | LYS | B | 191 | 84.121 | 44.922 | −41.378 | 1.00 | 78.07 | B | C |
| ATOM | 11279 | CD | LYS | B | 191 | 82.949 | 45.868 | −41.546 | 1.00 | 83.68 | B | C |
| ATOM | 11282 | CE | LYS | B | 191 | 82.589 | 46.014 | −43.012 | 1.00 | 85.64 | B | C |
| ATOM | 11285 | NZ | LYS | B | 191 | 81.322 | 46.764 | −43.228 | 1.00 | 85.74 | B | N |
| ATOM | 11289 | C | LYS | B | 191 | 85.587 | 43.362 | −38.192 | 1.00 | 70.52 | B | C |
| ATOM | 11290 | O | LYS | B | 191 | 86.656 | 43.635 | −37.640 | 1.00 | 69.35 | B | O |
| ATOM | 11292 | N | ILE | B | 192 | 84.515 | 42.917 | −37.546 | 1.00 | 68.76 | B | N |
| ATOM | 11293 | CA | ILE | B | 192 | 84.498 | 42.712 | −36.102 | 1.00 | 67.68 | B | C |
| ATOM | 11295 | CB | ILE | B | 192 | 83.059 | 42.833 | −35.544 | 1.00 | 67.45 | B | C |
| ATOM | 11297 | CG1 | ILE | B | 192 | 82.129 | 41.758 | −36.137 | 1.00 | 66.91 | B | C |
| ATOM | 11300 | CD1 | ILE | B | 192 | 80.731 | 41.750 | −35.544 | 1.00 | 62.95 | B | C |
| ATOM | 11304 | CG2 | ILE | B | 192 | 82.495 | 44.217 | −35.848 | 1.00 | 67.23 | B | C |
| ATOM | 11308 | C | ILE | B | 192 | 85.101 | 41.346 | −35.781 | 1.00 | 66.59 | B | C |
| ATOM | 11309 | O | ILE | B | 192 | 85.310 | 40.533 | −36.678 | 1.00 | 65.89 | B | O |
| ATOM | 11311 | N | GLY | B | 193 | 85.381 | 41.092 | −34.508 | 1.00 | 65.99 | B | N |
| ATOM | 11312 | CA | GLY | B | 193 | 85.987 | 39.820 | −34.095 | 1.00 | 66.09 | B | C |

TABLE 4-2-continued

Coordinates of *P. alba* IspS

| | | | | | | | | | | | | |
|---|---|---|---|---|---|---|---|---|---|---|---|---|
| ATOM | 11315 | C | GLY | B | 193 | 85.240 | 38.558 | −34.522 | 1.00 | 65.01 | B | C |
| ATOM | 11316 | O | GLY | B | 193 | 84.047 | 38.599 | −34.838 | 1.00 | 65.07 | B | O |
| ATOM | 11318 | N | LYS | B | 194 | 85.950 | 37.431 | −34.522 | 1.00 | 63.20 | B | N |
| ATOM | 11319 | CA | LYS | B | 194 | 85.349 | 36.125 | −34.810 | 1.00 | 61.59 | B | C |
| ATOM | 11321 | CB | LYS | B | 194 | 86.420 | 35.045 | −35.024 | 1.00 | 62.81 | B | C |
| ATOM | 11324 | CG | LYS | B | 194 | 87.707 | 35.553 | −35.719 | 1.00 | 69.11 | B | C |
| ATOM | 11327 | CD | LYS | B | 194 | 88.577 | 34.426 | −36.265 | 1.00 | 73.14 | B | C |
| ATOM | 11330 | CE | LYS | B | 194 | 89.964 | 34.937 | −36.630 | 1.00 | 73.97 | B | C |
| ATOM | 11333 | NZ | LYS | B | 194 | 90.701 | 33.974 | −37.486 | 1.00 | 72.97 | B | N |
| ATOM | 11337 | C | LYS | B | 194 | 84.449 | 35.739 | −33.642 | 1.00 | 58.97 | B | C |
| ATOM | 11338 | O | LYS | B | 194 | 83.352 | 35.227 | −33.848 | 1.00 | 58.12 | B | O |
| ATOM | 11340 | N | GLU | B | 195 | 84.916 | 36.004 | −32.419 | 1.00 | 56.35 | B | N |
| ATOM | 11341 | CA | GLU | B | 195 | 84.129 | 35.732 | −31.211 | 1.00 | 54.87 | B | C |
| ATOM | 11343 | CB | GLU | B | 195 | 84.997 | 35.779 | −29.942 | 1.00 | 55.37 | B | C |
| ATOM | 11346 | CG | GLU | B | 195 | 85.305 | 37.173 | −29.405 | 1.00 | 59.74 | B | C |
| ATOM | 11349 | CD | GLU | B | 195 | 86.263 | 37.147 | −28.214 | 1.00 | 65.81 | B | C |
| ATOM | 11350 | OE1 | GLU | B | 195 | 85.953 | 37.804 | −27.195 | 1.00 | 68.11 | B | O |
| ATOM | 11351 | OE2 | GLU | B | 195 | 87.321 | 36.478 | −28.292 | 1.00 | 62.87 | B | O |
| ATOM | 11352 | C | GLU | B | 195 | 82.938 | 36.687 | −31.088 | 1.00 | 52.05 | B | C |
| ATOM | 11353 | O | GLU | B | 195 | 81.881 | 36.302 | −30.569 | 1.00 | 51.42 | B | O |
| ATOM | 11355 | N | LEU | B | 196 | 83.104 | 37.917 | −31.575 | 1.00 | 48.06 | B | N |
| ATOM | 11356 | CA | LEU | B | 196 | 82.024 | 38.902 | −31.518 | 1.00 | 44.72 | B | C |
| ATOM | 11358 | CB | LEU | B | 196 | 82.556 | 40.327 | −31.685 | 1.00 | 44.61 | B | C |
| ATOM | 11361 | CG | LEU | B | 196 | 81.759 | 41.396 | −30.928 | 1.00 | 44.98 | B | C |
| ATOM | 11363 | CD1 | LEU | B | 196 | 81.934 | 41.257 | −29.418 | 1.00 | 47.04 | B | C |
| ATOM | 11367 | CD2 | LEU | B | 196 | 82.168 | 42.798 | −31.387 | 1.00 | 45.98 | B | C |
| ATOM | 11371 | C | LEU | B | 196 | 80.918 | 38.607 | −32.538 | 1.00 | 41.82 | B | C |
| ATOM | 11372 | O | LEU | B | 196 | 79.750 | 38.849 | −32.256 | 1.00 | 40.86 | B | O |
| ATOM | 11374 | N | ALA | B | 197 | 81.273 | 38.069 | −33.705 | 1.00 | 39.07 | B | N |
| ATOM | 11375 | CA | ALA | B | 197 | 80.260 | 37.639 | −34.679 | 1.00 | 37.43 | B | C |
| ATOM | 11377 | CB | ALA | B | 197 | 80.898 | 37.300 | −36.021 | 1.00 | 36.56 | B | C |
| ATOM | 11381 | C | ALA | B | 197 | 79.487 | 36.437 | −34.146 | 1.00 | 36.90 | B | C |
| ATOM | 11382 | O | ALA | B | 197 | 78.300 | 36.286 | −34.411 | 1.00 | 39.21 | B | O |
| ATOM | 11384 | N | GLU | B | 198 | 80.166 | 35.574 | −33.404 | 1.00 | 36.09 | B | N |
| ATOM | 11385 | CA | GLU | B | 198 | 79.496 | 34.465 | −32.744 | 1.00 | 36.69 | B | C |
| ATOM | 11387 | CB | GLU | B | 198 | 80.519 | 33.469 | −32.174 | 1.00 | 38.24 | B | C |
| ATOM | 11390 | CG | GLU | B | 198 | 81.044 | 32.504 | −33.263 | 1.00 | 49.87 | B | C |
| ATOM | 11393 | CD | GLU | B | 198 | 82.379 | 31.814 | −32.933 | 1.00 | 59.13 | B | C |
| ATOM | 11394 | OE1 | GLU | B | 198 | 82.981 | 32.093 | −31.870 | 1.00 | 66.73 | B | O |
| ATOM | 11395 | OE2 | GLU | B | 198 | 82.824 | 30.983 | −33.760 | 1.00 | 62.01 | B | O |
| ATOM | 11396 | C | GLU | B | 198 | 78.522 | 34.985 | −31.677 | 1.00 | 32.99 | B | C |
| ATOM | 11397 | O | GLU | B | 198 | 77.413 | 34.491 | −31.592 | 1.00 | 34.75 | B | O |
| ATOM | 11399 | N | GLN | B | 199 | 78.913 | 36.001 | −30.908 | 1.00 | 29.51 | B | N |
| ATOM | 11400 | CA | GLN | B | 199 | 77.997 | 36.612 | −29.945 | 1.00 | 29.35 | B | C |
| ATOM | 11402 | CB | GLN | B | 199 | 78.656 | 37.722 | −29.115 | 1.00 | 30.73 | B | C |
| ATOM | 11405 | CG | GLN | B | 199 | 79.775 | 37.269 | −28.142 | 1.00 | 39.02 | B | C |
| ATOM | 11408 | CD | GLN | B | 199 | 79.280 | 36.756 | −26.781 | 1.00 | 51.63 | B | C |
| ATOM | 11409 | OE1 | GLN | B | 199 | 78.074 | 36.694 | −26.513 | 1.00 | 54.70 | B | O |
| ATOM | 11410 | NE2 | GLN | B | 199 | 80.229 | 36.385 | −25.912 | 1.00 | 48.54 | B | N |
| ATOM | 11413 | C | GLN | B | 199 | 76.783 | 37.171 | −30.668 | 1.00 | 28.02 | B | C |
| ATOM | 11414 | O | GLN | B | 199 | 75.660 | 36.876 | −30.286 | 1.00 | 26.21 | B | O |
| ATOM | 11416 | N | VAL | B | 200 | 77.008 | 37.933 | −31.739 | 1.00 | 27.32 | B | N |
| ATOM | 11417 | CA | VAL | B | 200 | 75.911 | 38.572 | −32.485 | 1.00 | 27.54 | B | C |
| ATOM | 11419 | CB | VAL | B | 200 | 76.453 | 39.523 | −33.589 | 1.00 | 28.36 | B | C |
| ATOM | 11421 | CG1 | VAL | B | 200 | 77.351 | 40.596 | −32.963 | 1.00 | 29.95 | B | C |
| ATOM | 11425 | CG2 | VAL | B | 200 | 75.324 | 40.190 | −34.359 | 1.00 | 26.02 | B | C |
| ATOM | 11429 | C | VAL | B | 200 | 74.949 | 37.540 | −33.088 | 1.00 | 27.67 | B | C |
| ATOM | 11430 | O | VAL | B | 200 | 73.738 | 37.684 | −32.976 | 1.00 | 26.60 | B | O |
| ATOM | 11432 | N | ASN | B | 201 | 75.484 | 36.489 | −33.705 | 1.00 | 28.51 | B | N |
| ATOM | 11433 | CA | ASN | B | 201 | 74.636 | 35.429 | −34.266 | 1.00 | 29.14 | B | C |
| ATOM | 11435 | CB | ASN | B | 201 | 75.477 | 34.473 | −35.110 | 1.00 | 29.87 | B | C |
| ATOM | 11438 | CG | ASN | B | 201 | 76.085 | 35.156 | −36.340 | 1.00 | 35.29 | B | C |
| ATOM | 11439 | OD1 | ASN | B | 201 | 75.519 | 36.111 | −36.876 | 1.00 | 40.73 | B | O |
| ATOM | 11440 | ND2 | ASN | B | 201 | 77.240 | 34.666 | −36.786 | 1.00 | 36.68 | B | N |
| ATOM | 11443 | C | ASN | B | 201 | 73.866 | 34.654 | −33.186 | 1.00 | 28.87 | B | C |
| ATOM | 11444 | O | ASN | B | 201 | 72.728 | 34.266 | −33.380 | 1.00 | 30.14 | B | O |
| ATOM | 11446 | N | HIS | B | 202 | 74.488 | 34.432 | −32.039 | 1.00 | 28.36 | B | N |
| ATOM | 11447 | CA | HIS | B | 202 | 73.802 | 33.791 | −30.935 | 1.00 | 27.61 | B | C |
| ATOM | 11449 | CB | HIS | B | 202 | 74.777 | 33.640 | −29.779 | 1.00 | 28.85 | B | C |
| ATOM | 11452 | CG | HIS | B | 202 | 74.225 | 32.906 | −28.604 | 1.00 | 27.09 | B | C |
| ATOM | 11453 | ND1 | HIS | B | 202 | 73.851 | 31.583 | −28.665 | 1.00 | 23.27 | B | N |
| ATOM | 11455 | CE1 | HIS | B | 202 | 73.430 | 31.198 | −27.473 | 1.00 | 31.18 | B | C |
| ATOM | 11457 | NE2 | HIS | B | 202 | 73.510 | 32.228 | −26.646 | 1.00 | 29.63 | B | N |
| ATOM | 11459 | CD2 | HIS | B | 202 | 74.018 | 33.304 | −27.326 | 1.00 | 26.11 | B | C |
| ATOM | 11461 | C | HIS | B | 202 | 72.606 | 34.649 | −30.537 | 1.00 | 26.71 | B | C |
| ATOM | 11462 | O | HIS | B | 202 | 71.478 | 34.167 | −30.448 | 1.00 | 26.81 | B | O |
| ATOM | 11464 | N | ALA | B | 203 | 72.850 | 35.941 | −30.355 | 1.00 | 27.12 | B | N |
| ATOM | 11465 | CA | ALA | B | 203 | 71.799 | 36.880 | −29.978 | 1.00 | 26.93 | B | C |

TABLE 4-2-continued

Coordinates of *P. alba* IspS

| | | | | | | | | | | | | |
|---|---|---|---|---|---|---|---|---|---|---|---|---|
| ATOM | 11467 | CB | ALA | B | 203 | 72.402 | 38.252 | −29.671 | 1.00 | 25.40 | B | C |
| ATOM | 11471 | C | ALA | B | 203 | 70.689 | 37.000 | −31.026 | 1.00 | 28.19 | B | C |
| ATOM | 11472 | O | ALA | B | 203 | 69.521 | 37.124 | −30.667 | 1.00 | 32.01 | B | O |
| ATOM | 11474 | N | LEU | B | 204 | 71.041 | 36.991 | −32.309 | 1.00 | 27.53 | B | N |
| ATOM | 11475 | CA | LEU | B | 204 | 70.039 | 37.155 | −33.359 | 1.00 | 27.75 | B | C |
| ATOM | 11477 | CB | LEU | B | 204 | 70.657 | 37.643 | −34.688 | 1.00 | 28.47 | B | C |
| ATOM | 11480 | CG | LEU | B | 204 | 71.244 | 39.070 | −34.727 | 1.00 | 28.70 | B | C |
| ATOM | 11482 | CD1 | LEU | B | 204 | 71.765 | 39.386 | −36.107 | 1.00 | 29.73 | B | C |
| ATOM | 11486 | CD2 | LEU | B | 204 | 70.227 | 40.118 | −34.324 | 1.00 | 26.53 | B | C |
| ATOM | 11490 | C | LEU | B | 204 | 69.259 | 35.862 | −33.570 | 1.00 | 28.30 | B | C |
| ATOM | 11491 | O | LEU | B | 204 | 68.130 | 35.899 | −34.012 | 1.00 | 29.24 | B | O |
| ATOM | 11493 | N | GLU | B | 205 | 69.849 | 34.721 | −33.240 | 1.00 | 28.21 | B | N |
| ATOM | 11494 | CA | GLU | B | 205 | 69.089 | 33.481 | −33.215 | 1.00 | 27.87 | B | C |
| ATOM | 11496 | CB | GLU | B | 205 | 70.020 | 32.319 | −32.906 | 1.00 | 27.30 | B | C |
| ATOM | 11499 | CG | GLU | B | 205 | 69.340 | 30.975 | −32.757 | 1.00 | 31.98 | B | C |
| ATOM | 11502 | CD | GLU | B | 205 | 70.312 | 29.900 | −32.313 | 1.00 | 38.53 | B | C |
| ATOM | 11503 | OE1 | GLU | B | 205 | 70.900 | 30.036 | −31.211 | 1.00 | 37.57 | B | O |
| ATOM | 11504 | OE2 | GLU | B | 205 | 70.500 | 28.926 | −33.072 | 1.00 | 44.27 | B | O |
| ATOM | 11505 | C | GLU | B | 205 | 67.953 | 33.579 | −32.177 | 1.00 | 28.31 | B | C |
| ATOM | 11506 | O | GLU | B | 205 | 66.799 | 33.221 | −32.455 | 1.00 | 28.82 | B | O |
| ATOM | 11508 | N | LEU | B | 206 | 68.288 | 34.069 | −30.985 | 1.00 | 27.57 | B | N |
| ATOM | 11509 | CA | LEU | B | 206 | 67.320 | 34.184 | −29.894 | 1.00 | 26.20 | B | C |
| ATOM | 11511 | CB | LEU | B | 206 | 66.913 | 32.791 | −29.389 | 1.00 | 24.32 | B | C |
| ATOM | 11514 | CG | LEU | B | 206 | 65.658 | 32.728 | −28.529 | 1.00 | 26.26 | B | C |
| ATOM | 11516 | CD1 | LEU | B | 206 | 64.389 | 33.063 | −29.342 | 1.00 | 20.27 | B | C |
| ATOM | 11520 | CD2 | LEU | B | 206 | 65.519 | 31.347 | −27.850 | 1.00 | 22.33 | B | C |
| ATOM | 11524 | C | LEU | B | 206 | 67.953 | 34.958 | −28.753 | 1.00 | 24.67 | B | C |
| ATOM | 11525 | O | LEU | B | 206 | 69.042 | 34.609 | −28.322 | 1.00 | 25.77 | B | O |
| ATOM | 11527 | N | PRO | B | 207 | 67.274 | 35.992 | −28.247 | 1.00 | 22.87 | B | N |
| ATOM | 11528 | CA | PRO | B | 207 | 67.814 | 36.834 | −27.206 | 1.00 | 22.69 | B | C |
| ATOM | 11530 | CB | PRO | B | 207 | 66.802 | 37.980 | −27.138 | 1.00 | 24.47 | B | C |
| ATOM | 11533 | CG | PRO | B | 207 | 65.548 | 37.352 | −27.566 | 1.00 | 22.66 | B | C |
| ATOM | 11536 | CD | PRO | B | 207 | 65.953 | 36.470 | −28.679 | 1.00 | 24.94 | B | C |
| ATOM | 11539 | C | PRO | B | 207 | 67.835 | 36.135 | −25.879 | 1.00 | 22.68 | B | C |
| ATOM | 11540 | O | PRO | B | 207 | 67.086 | 35.181 | −25.683 | 1.00 | 21.77 | B | O |
| ATOM | 11541 | N | LEU | B | 208 | 68.661 | 36.645 | −24.967 | 1.00 | 23.36 | B | N |
| ATOM | 11542 | CA | LEU | B | 208 | 68.863 | 36.031 | −23.652 | 1.00 | 22.82 | B | C |
| ATOM | 11544 | CB | LEU | B | 208 | 69.783 | 36.906 | −22.799 | 1.00 | 26.09 | B | C |
| ATOM | 11547 | CG | LEU | B | 208 | 71.296 | 36.760 | −22.912 | 1.00 | 29.62 | B | C |
| ATOM | 11549 | CD1 | LEU | B | 208 | 71.965 | 37.877 | −22.134 | 1.00 | 35.38 | B | C |
| ATOM | 11553 | CD2 | LEU | B | 208 | 71.688 | 35.403 | −22.345 | 1.00 | 31.33 | B | C |
| ATOM | 11557 | C | LEU | B | 208 | 67.554 | 35.893 | −22.915 | 1.00 | 22.27 | B | C |
| ATOM | 11558 | O | LEU | B | 208 | 67.304 | 34.901 | −22.272 | 1.00 | 23.52 | B | O |
| ATOM | 11560 | N | HIS | B | 209 | 66.710 | 36.912 | −23.010 | 1.00 | 19.79 | B | N |
| ATOM | 11561 | CA | HIS | B | 209 | 65.496 | 36.918 | −22.232 | 1.00 | 19.81 | B | C |
| ATOM | 11563 | CB | HIS | B | 209 | 64.819 | 38.278 | −22.387 | 1.00 | 18.57 | B | C |
| ATOM | 11566 | CG | HIS | B | 209 | 63.665 | 38.491 | −21.464 | 1.00 | 20.89 | B | C |
| ATOM | 11567 | ND1 | HIS | B | 209 | 63.798 | 38.455 | −20.095 | 1.00 | 18.30 | B | N |
| ATOM | 11569 | CE1 | HIS | B | 209 | 62.624 | 38.687 | −19.537 | 1.00 | 19.90 | B | C |
| ATOM | 11571 | NE2 | HIS | B | 209 | 61.732 | 38.865 | −20.497 | 1.00 | 24.74 | B | N |
| ATOM | 11573 | CD2 | HIS | B | 209 | 62.357 | 38.745 | −21.713 | 1.00 | 19.23 | B | C |
| ATOM | 11575 | C | HIS | B | 209 | 64.550 | 35.775 | −22.659 | 1.00 | 18.96 | B | C |
| ATOM | 11576 | O | HIS | B | 209 | 63.638 | 35.417 | −21.928 | 1.00 | 20.40 | B | O |
| ATOM | 11578 | N | ARG | B | 210 | 64.771 | 35.214 | −23.838 | 1.00 | 17.53 | B | N |
| ATOM | 11579 | CA | ARG | B | 210 | 63.921 | 34.159 | −24.339 | 1.00 | 21.00 | B | C |
| ATOM | 11581 | CB | ARG | B | 210 | 63.417 | 34.519 | −25.736 | 1.00 | 21.58 | B | C |
| ATOM | 11584 | CG | ARG | B | 210 | 62.558 | 35.776 | −25.720 | 1.00 | 25.30 | B | C |
| ATOM | 11587 | CD | ARG | B | 210 | 61.972 | 36.079 | −27.098 | 1.00 | 26.92 | B | C |
| ATOM | 11590 | NE | ARG | B | 210 | 61.038 | 37.199 | −27.044 | 1.00 | 26.04 | B | N |
| ATOM | 11592 | CZ | ARG | B | 210 | 60.373 | 37.677 | −28.089 | 1.00 | 25.39 | B | C |
| ATOM | 11593 | NH1 | ARG | B | 210 | 60.529 | 37.128 | −29.286 | 1.00 | 28.28 | B | N |
| ATOM | 11596 | NH2 | ARG | B | 210 | 59.530 | 38.704 | −27.933 | 1.00 | 26.88 | B | N |
| ATOM | 11599 | C | ARG | B | 210 | 64.564 | 32.786 | −24.362 | 1.00 | 21.01 | B | C |
| ATOM | 11600 | O | ARG | B | 210 | 63.852 | 31.814 | −24.500 | 1.00 | 22.57 | B | O |
| ATOM | 11602 | N | ARG | B | 211 | 65.881 | 32.694 | −24.190 | 1.00 | 21.79 | B | N |
| ATOM | 11603 | CA | ARG | B | 211 | 66.560 | 31.387 | −24.219 | 1.00 | 21.96 | B | C |
| ATOM | 11605 | CB | ARG | B | 211 | 68.017 | 31.568 | −24.607 | 1.00 | 20.36 | B | C |
| ATOM | 11608 | CG | ARG | B | 211 | 68.659 | 30.320 | −25.118 | 1.00 | 25.64 | B | C |
| ATOM | 11611 | CD | ARG | B | 211 | 70.125 | 30.557 | −25.409 | 1.00 | 25.18 | B | C |
| ATOM | 11614 | NE | ARG | B | 211 | 70.339 | 31.518 | −26.488 | 1.00 | 22.19 | B | N |
| ATOM | 11616 | CZ | ARG | B | 211 | 70.325 | 31.219 | −27.789 | 1.00 | 31.36 | B | C |
| ATOM | 11617 | NH1 | ARG | B | 211 | 70.100 | 29.974 | −28.203 | 1.00 | 32.36 | B | N |
| ATOM | 11620 | NH2 | ARG | B | 211 | 70.545 | 32.174 | −28.692 | 1.00 | 31.10 | B | N |
| ATOM | 11623 | C | ARG | B | 211 | 66.482 | 30.715 | −22.858 | 1.00 | 21.08 | B | C |
| ATOM | 11624 | O | ARG | B | 211 | 66.562 | 31.380 | −21.829 | 1.00 | 23.84 | B | O |
| ATOM | 11626 | N | THR | B | 212 | 66.332 | 29.401 | −22.841 | 1.00 | 21.62 | B | N |
| ATOM | 11627 | CA | THR | B | 212 | 66.258 | 28.663 | −21.584 | 1.00 | 22.86 | B | C |
| ATOM | 11629 | CB | THR | B | 212 | 65.883 | 27.196 | −21.796 | 1.00 | 24.07 | B | C |

TABLE 4-2-continued

| Coordinates of *P. alba* IspS | | | | | | | | | | | | |
|---|---|---|---|---|---|---|---|---|---|---|---|---|
| ATOM | 11631 | OG1 | THR | B | 212 | 66.761 | 26.625 | −22.770 | 1.00 | 31.00 | B | O |
| ATOM | 11633 | CG2 | THR | B | 212 | 64.443 | 27.050 | −22.274 | 1.00 | 19.45 | B | C |
| ATOM | 11637 | C | THR | B | 212 | 67.628 | 28.725 | −20.923 | 1.00 | 23.79 | B | C |
| ATOM | 11638 | O | THR | B | 212 | 68.643 | 28.997 | −21.580 | 1.00 | 23.93 | B | O |
| ATOM | 11640 | N | GLN | B | 213 | 67.656 | 28.454 | −19.630 | 1.00 | 23.05 | B | N |
| ATOM | 11641 | CA | GLN | B | 213 | 68.850 | 28.713 | −18.832 | 1.00 | 21.92 | B | C |
| ATOM | 11643 | CB | GLN | B | 213 | 68.513 | 28.620 | −17.345 | 1.00 | 21.12 | B | C |
| ATOM | 11646 | CG | GLN | B | 213 | 69.466 | 29.407 | −16.398 | 1.00 | 26.64 | B | C |
| ATOM | 11649 | CD | GLN | B | 213 | 70.578 | 28.551 | −15.863 | 1.00 | 26.56 | B | C |
| ATOM | 11650 | OE1 | GLN | B | 213 | 70.991 | 27.565 | −16.490 | 1.00 | 26.61 | B | O |
| ATOM | 11651 | NE2 | GLN | B | 213 | 71.079 | 28.915 | −14.701 | 1.00 | 20.90 | B | N |
| ATOM | 11654 | C | GLN | B | 213 | 69.985 | 27.753 | −19.202 | 1.00 | 20.81 | B | C |
| ATOM | 11655 | O | GLN | B | 213 | 71.121 | 28.187 | −19.439 | 1.00 | 20.28 | B | O |
| ATOM | 11657 | N | ARG | B | 214 | 69.690 | 26.457 | −19.252 | 1.00 | 20.19 | B | N |
| ATOM | 11658 | CA | ARG | B | 214 | 70.746 | 25.484 | −19.544 | 1.00 | 21.47 | B | C |
| ATOM | 11660 | CB | ARG | B | 214 | 70.290 | 24.041 | −19.386 | 1.00 | 21.13 | B | C |
| ATOM | 11663 | CG | ARG | B | 214 | 69.953 | 23.656 | −17.970 | 1.00 | 21.84 | B | C |
| ATOM | 11666 | CD | ARG | B | 214 | 71.190 | 23.470 | −17.110 | 1.00 | 24.31 | B | C |
| ATOM | 11669 | NE | ARG | B | 214 | 71.582 | 24.706 | −16.457 | 1.00 | 25.78 | B | N |
| ATOM | 11671 | CZ | ARG | B | 214 | 72.655 | 24.854 | −15.693 | 1.00 | 23.08 | B | C |
| ATOM | 11672 | NH1 | ARG | B | 214 | 73.481 | 23.834 | −15.486 | 1.00 | 23.99 | B | N |
| ATOM | 11675 | NH2 | ARG | B | 214 | 72.915 | 26.046 | −15.155 | 1.00 | 19.12 | B | N |
| ATOM | 11678 | C | ARG | B | 214 | 71.327 | 25.675 | −20.919 | 1.00 | 20.24 | B | C |
| ATOM | 11679 | O | ARG | B | 214 | 72.531 | 25.534 | −21.070 | 1.00 | 20.21 | B | O |
| ATOM | 11681 | N | LEU | B | 215 | 70.506 | 26.014 | −21.910 | 1.00 | 19.38 | B | N |
| ATOM | 11682 | CA | LEU | B | 215 | 71.021 | 26.177 | −23.278 | 1.00 | 21.93 | B | C |
| ATOM | 11684 | CB | LEU | B | 215 | 69.896 | 26.332 | −24.294 | 1.00 | 23.52 | B | C |
| ATOM | 11687 | CG | LEU | B | 215 | 69.313 | 25.060 | −24.892 | 1.00 | 32.95 | B | C |
| ATOM | 11689 | CD1 | LEU | B | 215 | 70.415 | 24.335 | −25.695 | 1.00 | 29.05 | B | C |
| ATOM | 11693 | CD2 | LEU | B | 215 | 68.102 | 25.417 | −25.789 | 1.00 | 29.82 | B | C |
| ATOM | 11697 | C | LEU | B | 215 | 71.983 | 27.354 | −23.406 | 1.00 | 22.32 | B | C |
| ATOM | 11698 | O | LEU | B | 215 | 73.016 | 27.231 | −24.041 | 1.00 | 22.96 | B | O |
| ATOM | 11700 | N | GLU | B | 216 | 71.631 | 28.488 | −22.806 | 1.00 | 23.34 | B | N |
| ATOM | 11701 | CA | GLU | B | 216 | 72.543 | 29.621 | −22.693 | 1.00 | 23.77 | B | C |
| ATOM | 11703 | CB | GLU | B | 216 | 71.860 | 30.793 | −21.958 | 1.00 | 24.84 | B | C |
| ATOM | 11706 | CG | GLU | B | 216 | 72.711 | 32.044 | −21.844 | 1.00 | 26.26 | B | C |
| ATOM | 11709 | CD | GLU | B | 216 | 73.313 | 32.494 | −23.185 | 1.00 | 29.08 | B | C |
| ATOM | 11710 | OE1 | GLU | B | 216 | 72.657 | 32.349 | −24.232 | 1.00 | 30.45 | B | O |
| ATOM | 11711 | OE2 | GLU | B | 216 | 74.452 | 33.006 | −23.181 | 1.00 | 29.22 | B | O |
| ATOM | 11712 | C | GLU | B | 216 | 73.815 | 29.224 | −21.940 | 1.00 | 23.03 | B | C |
| ATOM | 11713 | O | GLU | B | 216 | 74.910 | 29.595 | −22.331 | 1.00 | 25.15 | B | O |
| ATOM | 11715 | N | ALA | B | 217 | 73.692 | 28.461 | −20.865 | 1.00 | 21.75 | B | N |
| ATOM | 11716 | CA | ALA | B | 217 | 74.889 | 28.141 | −20.110 | 1.00 | 21.54 | B | C |
| ATOM | 11718 | CB | ALA | B | 217 | 74.557 | 27.429 | −18.817 | 1.00 | 18.56 | B | C |
| ATOM | 11722 | C | ALA | B | 217 | 75.880 | 27.336 | −20.949 | 1.00 | 22.53 | B | C |
| ATOM | 11723 | O | ALA | B | 217 | 77.092 | 27.634 | −20.954 | 1.00 | 24.18 | B | O |
| ATOM | 11725 | N | VAL | B | 218 | 75.380 | 26.356 | −21.693 | 1.00 | 24.24 | B | N |
| ATOM | 11726 | CA | VAL | B | 218 | 76.264 | 25.447 | −22.423 | 1.00 | 24.89 | B | C |
| ATOM | 11728 | CB | VAL | B | 218 | 75.544 | 24.155 | −22.910 | 1.00 | 26.35 | B | C |
| ATOM | 11730 | CG1 | VAL | B | 218 | 74.605 | 24.436 | −24.089 | 1.00 | 24.54 | B | C |
| ATOM | 11734 | CG2 | VAL | B | 218 | 76.595 | 23.062 | −23.278 | 1.00 | 27.94 | B | C |
| ATOM | 11738 | C | VAL | B | 218 | 76.947 | 26.169 | −23.569 | 1.00 | 24.67 | B | C |
| ATOM | 11739 | O | VAL | B | 218 | 78.083 | 25.880 | −23.877 | 1.00 | 26.68 | B | O |
| ATOM | 11741 | N | TRP | B | 219 | 76.260 | 27.128 | −24.179 | 1.00 | 25.65 | B | N |
| ATOM | 11742 | CA | TRP | B | 219 | 76.875 | 27.976 | −25.199 | 1.00 | 24.72 | B | C |
| ATOM | 11744 | CB | TRP | B | 219 | 75.789 | 28.722 | −25.996 | 1.00 | 26.46 | B | C |
| ATOM | 11747 | CG | TRP | B | 219 | 76.344 | 29.516 | −27.131 | 1.00 | 27.34 | B | C |
| ATOM | 11748 | CD1 | TRP | B | 219 | 76.444 | 29.122 | −28.431 | 1.00 | 29.10 | B | C |
| ATOM | 11750 | NE1 | TRP | B | 219 | 77.032 | 30.117 | −29.184 | 1.00 | 26.04 | B | N |
| ATOM | 11752 | CE2 | TRP | B | 219 | 77.329 | 31.171 | −28.366 | 1.00 | 26.96 | B | C |
| ATOM | 11753 | CD2 | TRP | B | 219 | 76.916 | 30.826 | −27.063 | 1.00 | 22.98 | B | C |
| ATOM | 11754 | CE3 | TRP | B | 219 | 77.110 | 31.745 | −26.030 | 1.00 | 29.02 | B | C |
| ATOM | 11756 | CZ3 | TRP | B | 219 | 77.708 | 32.965 | −26.327 | 1.00 | 30.21 | B | C |
| ATOM | 11758 | CH2 | TRP | B | 219 | 78.117 | 33.273 | −27.620 | 1.00 | 28.87 | B | C |
| ATOM | 11760 | CZ2 | TRP | B | 219 | 77.937 | 32.390 | −28.657 | 1.00 | 32.64 | B | C |
| ATOM | 11762 | C | TRP | B | 219 | 77.855 | 28.978 | −24.584 | 1.00 | 23.76 | B | C |
| ATOM | 11763 | O | TRP | B | 219 | 78.924 | 29.224 | −25.124 | 1.00 | 27.15 | B | O |
| ATOM | 11765 | N | SER | B | 220 | 77.495 | 29.574 | −23.456 | 1.00 | 23.73 | B | N |
| ATOM | 11766 | CA | SER | B | 220 | 78.330 | 30.616 | −22.874 | 1.00 | 23.51 | B | C |
| ATOM | 11768 | CB | SER | B | 220 | 77.573 | 31.395 | −21.803 | 1.00 | 22.98 | B | C |
| ATOM | 11771 | OG | SER | B | 220 | 76.786 | 32.384 | −22.416 | 1.00 | 25.03 | B | O |
| ATOM | 11773 | C | SER | B | 220 | 79.606 | 30.054 | −22.286 | 1.00 | 24.58 | B | C |
| ATOM | 11774 | O | SER | B | 220 | 80.623 | 30.723 | −22.291 | 1.00 | 26.26 | B | O |
| ATOM | 11776 | N | ILE | B | 221 | 79.542 | 28.837 | −21.755 | 1.00 | 24.53 | B | N |
| ATOM | 11777 | CA | ILE | B | 221 | 80.726 | 28.191 | −21.221 | 1.00 | 25.43 | B | C |
| ATOM | 11779 | CB | ILE | B | 221 | 80.380 | 26.930 | −20.433 | 1.00 | 24.62 | B | C |
| ATOM | 11781 | CG1 | ILE | B | 221 | 79.697 | 27.327 | −19.128 | 1.00 | 21.02 | B | C |
| ATOM | 11784 | CD1 | ILE | B | 221 | 78.873 | 26.217 | −18.505 | 1.00 | 18.22 | B | C |

TABLE 4-2-continued

Coordinates of *P. alba* IspS

| | | | | | | | | | | | | |
|---|---|---|---|---|---|---|---|---|---|---|---|---|
| ATOM | 11788 | CG2 | ILE | B | 221 | 81.634 | 26.132 | −20.129 | 1.00 | 24.19 | B | C |
| ATOM | 11792 | C | ILE | B | 221 | 81.711 | 27.866 | −22.347 | 1.00 | 28.11 | B | C |
| ATOM | 11793 | O | ILE | B | 221 | 82.907 | 28.122 | −22.224 | 1.00 | 25.44 | B | O |
| ATOM | 11795 | N | GLU | B | 222 | 81.208 | 27.331 | −23.452 | 1.00 | 29.17 | B | N |
| ATOM | 11796 | CA | GLU | B | 222 | 82.064 | 27.117 | −24.612 | 1.00 | 30.37 | B | C |
| ATOM | 11798 | CB | GLU | B | 222 | 81.305 | 26.393 | −25.728 | 1.00 | 31.94 | B | C |
| ATOM | 11801 | CG | GLU | B | 222 | 82.195 | 25.909 | −26.897 | 1.00 | 37.68 | B | C |
| ATOM | 11804 | CD | GLU | B | 222 | 83.413 | 25.100 | −26.431 | 1.00 | 40.63 | B | C |
| ATOM | 11805 | OE1 | GLU | B | 222 | 83.347 | 24.445 | −25.362 | 1.00 | 46.08 | B | O |
| ATOM | 11806 | OE2 | GLU | B | 222 | 84.437 | 25.133 | −27.136 | 1.00 | 49.29 | B | O |
| ATOM | 11807 | C | GLU | B | 222 | 82.681 | 28.425 | −25.139 | 1.00 | 29.60 | B | C |
| ATOM | 11808 | O | GLU | B | 222 | 83.845 | 28.445 | −25.474 | 1.00 | 31.39 | B | O |
| ATOM | 11810 | N | ALA | B | 223 | 81.917 | 29.511 | −25.198 | 1.00 | 29.46 | B | N |
| ATOM | 11811 | CA | ALA | B | 223 | 82.460 | 30.794 | −25.669 | 1.00 | 27.98 | B | C |
| ATOM | 11813 | CB | ALA | B | 223 | 81.354 | 31.779 | −25.924 | 1.00 | 27.66 | B | C |
| ATOM | 11817 | C | ALA | B | 223 | 83.446 | 31.378 | −24.672 | 1.00 | 29.38 | B | C |
| ATOM | 11818 | O | ALA | B | 223 | 84.539 | 31.784 | −25.049 | 1.00 | 30.35 | B | O |
| ATOM | 11820 | N | TYR | B | 224 | 83.073 | 31.405 | −23.393 | 1.00 | 29.56 | B | N |
| ATOM | 11821 | CA | TYR | B | 224 | 83.948 | 31.970 | −22.364 | 1.00 | 28.89 | B | C |
| ATOM | 11823 | CB | TYR | B | 224 | 83.281 | 31.910 | −20.991 | 1.00 | 27.75 | B | C |
| ATOM | 11826 | CG | TYR | B | 224 | 83.845 | 32.869 | −19.962 | 1.00 | 21.93 | B | C |
| ATOM | 11827 | CD1 | TYR | B | 224 | 83.706 | 34.246 | −20.111 | 1.00 | 25.72 | B | C |
| ATOM | 11829 | CE1 | TYR | B | 224 | 84.200 | 35.134 | −19.150 | 1.00 | 28.65 | B | C |
| ATOM | 11831 | CZ | TYR | B | 224 | 84.823 | 34.646 | −18.019 | 1.00 | 26.53 | B | C |
| ATOM | 11832 | OH | TYR | B | 224 | 85.322 | 35.516 | −17.065 | 1.00 | 31.14 | B | O |
| ATOM | 11834 | CE2 | TYR | B | 224 | 84.959 | 33.293 | −17.849 | 1.00 | 24.43 | B | C |
| ATOM | 11836 | CD2 | TYR | B | 224 | 84.464 | 32.409 | −18.827 | 1.00 | 24.32 | B | C |
| ATOM | 11838 | C | TYR | B | 224 | 85.280 | 31.227 | −22.319 | 1.00 | 30.12 | B | C |
| ATOM | 11839 | O | TYR | B | 224 | 86.333 | 31.827 | −22.135 | 1.00 | 30.99 | B | O |
| ATOM | 11841 | N | ARG | B | 225 | 85.220 | 29.915 | −22.486 | 1.00 | 31.92 | B | N |
| ATOM | 11842 | CA | ARG | B | 225 | 86.409 | 29.069 | −22.478 | 1.00 | 34.85 | B | C |
| ATOM | 11844 | CB | ARG | B | 225 | 85.991 | 27.615 | −22.733 | 1.00 | 34.71 | B | C |
| ATOM | 11847 | CG | ARG | B | 225 | 87.030 | 26.604 | −22.328 | 1.00 | 41.35 | B | C |
| ATOM | 11850 | CD | ARG | B | 225 | 86.910 | 25.349 | −23.161 | 1.00 | 44.42 | B | C |
| ATOM | 11853 | NE | ARG | B | 225 | 85.793 | 24.534 | −22.728 | 1.00 | 29.27 | B | N |
| ATOM | 11855 | CZ | ARG | B | 225 | 85.866 | 23.584 | −21.803 | 1.00 | 26.94 | B | C |
| ATOM | 11856 | NH1 | ARG | B | 225 | 87.007 | 23.300 | −21.189 | 1.00 | 22.41 | B | N |
| ATOM | 11859 | NH2 | ARG | B | 225 | 84.776 | 22.892 | −21.496 | 1.00 | 24.98 | B | N |
| ATOM | 11862 | C | ARG | B | 225 | 87.452 | 29.515 | −23.529 | 1.00 | 36.03 | B | C |
| ATOM | 11863 | O | ARG | B | 225 | 88.644 | 29.365 | −23.320 | 1.00 | 34.54 | B | O |
| ATOM | 11865 | N | LYS | B | 226 | 86.986 | 30.054 | −24.655 | 1.00 | 39.58 | B | N |
| ATOM | 11866 | CA | LYS | B | 226 | 87.860 | 30.507 | −25.732 | 1.00 | 41.75 | B | C |
| ATOM | 11868 | CB | LYS | B | 226 | 87.114 | 30.457 | −27.069 | 1.00 | 41.97 | B | C |
| ATOM | 11871 | CG | LYS | B | 226 | 86.581 | 29.085 | −27.431 | 1.00 | 44.77 | B | C |
| ATOM | 11874 | CD | LYS | B | 226 | 86.073 | 29.053 | −28.870 | 1.00 | 49.54 | B | C |
| ATOM | 11877 | CE | LYS | B | 226 | 85.298 | 27.780 | −29.192 | 1.00 | 50.36 | B | C |
| ATOM | 11880 | NZ | LYS | B | 226 | 83.891 | 28.078 | −29.559 | 1.00 | 51.17 | B | N |
| ATOM | 11884 | C | LYS | B | 226 | 88.421 | 31.919 | −25.534 | 1.00 | 43.33 | B | C |
| ATOM | 11885 | O | LYS | B | 226 | 89.259 | 32.355 | −26.324 | 1.00 | 43.89 | B | O |
| ATOM | 11887 | N | LYS | B | 227 | 87.962 | 32.642 | −24.514 | 1.00 | 45.03 | B | N |
| ATOM | 11888 | CA | LYS | B | 227 | 88.498 | 33.981 | −24.226 | 1.00 | 47.42 | B | C |
| ATOM | 11890 | CB | LYS | B | 227 | 87.508 | 34.828 | −23.413 | 1.00 | 47.85 | B | C |
| ATOM | 11893 | CG | LYS | B | 227 | 86.288 | 35.318 | −24.172 | 1.00 | 50.13 | B | C |
| ATOM | 11896 | CD | LYS | B | 227 | 85.580 | 36.442 | −23.402 | 1.00 | 56.73 | B | C |
| ATOM | 11899 | CE | LYS | B | 227 | 84.102 | 36.545 | −23.774 | 1.00 | 64.18 | B | C |
| ATOM | 11902 | NZ | LYS | B | 227 | 83.858 | 36.666 | −25.249 | 1.00 | 66.49 | B | N |
| ATOM | 11906 | C | LYS | B | 227 | 89.814 | 33.870 | −23.453 | 1.00 | 48.79 | B | C |
| ATOM | 11907 | O | LYS | B | 227 | 89.862 | 33.243 | −22.382 | 1.00 | 49.31 | B | O |
| ATOM | 11909 | N | GLU | B | 228 | 90.873 | 34.484 | −23.987 | 1.00 | 48.99 | B | N |
| ATOM | 11910 | CA | GLU | B | 228 | 92.184 | 34.472 | −23.327 | 1.00 | 49.23 | B | C |
| ATOM | 11912 | CB | GLU | B | 228 | 93.265 | 35.098 | −24.220 | 1.00 | 50.17 | B | C |
| ATOM | 11915 | CG | GLU | B | 228 | 94.651 | 35.139 | −23.556 | 1.00 | 56.84 | B | C |
| ATOM | 11918 | CD | GLU | B | 228 | 95.805 | 35.113 | −24.551 | 1.00 | 62.65 | B | C |
| ATOM | 11919 | OE1 | GLU | B | 228 | 95.772 | 35.883 | −25.536 | 1.00 | 63.14 | B | O |
| ATOM | 11920 | OE2 | GLU | B | 228 | 96.753 | 34.324 | −24.336 | 1.00 | 62.24 | B | O |
| ATOM | 11921 | C | GLU | B | 228 | 92.150 | 35.184 | −21.972 | 1.00 | 46.82 | B | C |
| ATOM | 11922 | O | GLU | B | 228 | 92.875 | 34.808 | −21.048 | 1.00 | 47.31 | B | O |
| ATOM | 11924 | N | ASP | B | 229 | 91.304 | 36.202 | −21.859 | 1.00 | 43.57 | B | N |
| ATOM | 11925 | CA | ASP | B | 229 | 91.168 | 36.959 | −20.621 | 1.00 | 42.02 | B | C |
| ATOM | 11927 | CB | ASP | B | 229 | 90.946 | 38.439 | −20.943 | 1.00 | 43.47 | B | C |
| ATOM | 11930 | CG | ASP | B | 229 | 89.751 | 38.661 | −21.854 | 1.00 | 47.72 | B | C |
| ATOM | 11931 | OD1 | ASP | B | 229 | 89.491 | 37.784 | −22.704 | 1.00 | 51.55 | B | O |
| ATOM | 11932 | OD2 | ASP | B | 229 | 89.079 | 39.704 | −21.726 | 1.00 | 55.81 | B | O |
| ATOM | 11933 | C | ASP | B | 229 | 90.035 | 36.448 | −19.714 | 1.00 | 38.44 | B | C |
| ATOM | 11934 | O | ASP | B | 229 | 89.667 | 37.131 | −18.769 | 1.00 | 37.66 | B | O |
| ATOM | 11936 | N | ALA | B | 230 | 89.489 | 35.261 | −19.983 | 1.00 | 35.09 | B | N |
| ATOM | 11937 | CA | ALA | B | 230 | 88.432 | 34.696 | −19.131 | 1.00 | 33.38 | B | C |
| ATOM | 11939 | CB | ALA | B | 230 | 87.915 | 33.392 | −19.704 | 1.00 | 33.10 | B | C |

TABLE 4-2-continued

Coordinates of *P. alba* IspS

| | | | | | | | | | | | | |
|---|---|---|---|---|---|---|---|---|---|---|---|---|
| ATOM | 11943 | C | ALA | B | 230 | 88.934 | 34.465 | −17.711 | 1.00 | 32.12 | B | C |
| ATOM | 11944 | O | ALA | B | 230 | 90.070 | 34.048 | −17.495 | 1.00 | 30.75 | B | O |
| ATOM | 11946 | N | ASN | B | 231 | 88.080 | 34.738 | −16.736 | 1.00 | 30.68 | B | N |
| ATOM | 11947 | CA | ASN | B | 231 | 88.422 | 34.453 | −15.359 | 1.00 | 29.53 | B | C |
| ATOM | 11949 | CB | ASN | B | 231 | 87.456 | 35.129 | −14.388 | 1.00 | 29.88 | B | C |
| ATOM | 11952 | CG | ASN | B | 231 | 87.820 | 34.867 | −12.947 | 1.00 | 33.58 | B | C |
| ATOM | 11953 | OD1 | ASN | B | 231 | 87.935 | 33.714 | −12.520 | 1.00 | 31.88 | B | O |
| ATOM | 11954 | ND2 | ASN | B | 231 | 88.032 | 35.936 | −12.189 | 1.00 | 42.97 | B | N |
| ATOM | 11957 | C | ASN | B | 231 | 88.388 | 32.960 | −15.152 | 1.00 | 27.93 | B | C |
| ATOM | 11958 | O | ASN | B | 231 | 87.334 | 32.338 | −15.276 | 1.00 | 26.52 | B | O |
| ATOM | 11960 | N | GLN | B | 232 | 89.539 | 32.398 | −14.806 | 1.00 | 27.85 | B | N |
| ATOM | 11961 | CA | GLN | B | 232 | 89.696 | 30.945 | −14.719 | 1.00 | 28.06 | B | C |
| ATOM | 11963 | CB | GLN | B | 232 | 91.178 | 30.574 | −14.669 | 1.00 | 27.87 | B | C |
| ATOM | 11966 | CG | GLN | B | 232 | 91.958 | 30.978 | −15.931 | 1.00 | 33.14 | B | C |
| ATOM | 11969 | CD | GLN | B | 232 | 91.460 | 30.284 | −17.202 | 1.00 | 35.07 | B | C |
| ATOM | 11970 | OE1 | GLN | B | 232 | 91.496 | 29.059 | −17.301 | 1.00 | 37.93 | B | O |
| ATOM | 11971 | NE2 | GLN | B | 232 | 91.003 | 31.069 | −18.177 | 1.00 | 32.06 | B | N |
| ATOM | 11974 | C | GLN | B | 232 | 88.940 | 30.326 | −13.538 | 1.00 | 27.32 | B | C |
| ATOM | 11975 | O | GLN | B | 232 | 88.472 | 29.175 | −13.625 | 1.00 | 28.40 | B | O |
| ATOM | 11977 | N | VAL | B | 233 | 88.814 | 31.081 | −12.449 | 1.00 | 23.84 | B | N |
| ATOM | 11978 | CA | VAL | B | 233 | 88.047 | 30.625 | −11.305 | 1.00 | 23.03 | B | C |
| ATOM | 11980 | CB | VAL | B | 233 | 88.182 | 31.592 | −10.105 | 1.00 | 23.26 | B | C |
| ATOM | 11982 | CG1 | VAL | B | 233 | 87.102 | 31.342 | −9.096 | 1.00 | 19.84 | B | C |
| ATOM | 11986 | CG2 | VAL | B | 233 | 89.581 | 31.440 | −9.438 | 1.00 | 25.03 | B | C |
| ATOM | 11990 | C | VAL | B | 233 | 86.583 | 30.457 | −11.713 | 1.00 | 23.81 | B | C |
| ATOM | 11991 | O | VAL | B | 233 | 85.990 | 29.405 | −11.492 | 1.00 | 23.11 | B | O |
| ATOM | 11993 | N | LEU | B | 234 | 86.014 | 31.491 | −12.330 | 1.00 | 22.26 | B | N |
| ATOM | 11994 | CA | LEU | B | 234 | 84.630 | 31.454 | −12.733 | 1.00 | 22.19 | B | C |
| ATOM | 11996 | CB | LEU | B | 234 | 84.219 | 32.814 | −13.267 | 1.00 | 22.77 | B | C |
| ATOM | 11999 | CG | LEU | B | 234 | 82.774 | 33.046 | −13.690 | 1.00 | 21.02 | B | C |
| ATOM | 12001 | CD1 | LEU | B | 234 | 81.821 | 32.913 | −12.510 | 1.00 | 13.82 | B | C |
| ATOM | 12005 | CD2 | LEU | B | 234 | 82.673 | 34.433 | −14.302 | 1.00 | 18.88 | B | C |
| ATOM | 12009 | C | LEU | B | 234 | 84.402 | 30.345 | −13.776 | 1.00 | 22.30 | B | C |
| ATOM | 12010 | O | LEU | B | 234 | 83.411 | 29.637 | −13.717 | 1.00 | 20.57 | B | O |
| ATOM | 12012 | N | LEU | B | 235 | 85.344 | 30.188 | −14.702 | 1.00 | 22.73 | B | N |
| ATOM | 12013 | CA | LEU | B | 235 | 85.219 | 29.215 | −15.783 | 1.00 | 22.64 | B | C |
| ATOM | 12015 | CB | LEU | B | 235 | 86.431 | 29.277 | −16.707 | 1.00 | 23.38 | B | C |
| ATOM | 12018 | CG | LEU | B | 235 | 86.482 | 28.297 | −17.885 | 1.00 | 26.34 | B | C |
| ATOM | 12020 | CD1 | LEU | B | 235 | 85.223 | 28.417 | −18.756 | 1.00 | 16.79 | B | C |
| ATOM | 12024 | CD2 | LEU | B | 235 | 87.756 | 28.530 | −18.717 | 1.00 | 19.46 | B | C |
| ATOM | 12028 | C | LEU | B | 235 | 85.121 | 27.835 | −15.206 | 1.00 | 21.21 | B | C |
| ATOM | 12029 | O | LEU | B | 235 | 84.249 | 27.054 | −15.565 | 1.00 | 20.49 | B | O |
| ATOM | 12031 | N | GLU | B | 236 | 86.038 | 27.550 | −14.301 | 1.00 | 22.20 | B | N |
| ATOM | 12032 | CA | GLU | B | 236 | 86.112 | 26.249 | −13.692 | 1.00 | 22.88 | B | C |
| ATOM | 12034 | CB | GLU | B | 236 | 87.348 | 26.114 | −12.787 | 1.00 | 22.27 | B | C |
| ATOM | 12037 | CG | GLU | B | 236 | 87.471 | 24.721 | −12.224 | 1.00 | 25.07 | B | C |
| ATOM | 12040 | CD | GLU | B | 236 | 88.782 | 24.458 | −11.508 | 1.00 | 30.11 | B | C |
| ATOM | 12041 | OE1 | GLU | B | 236 | 89.489 | 25.432 | −11.145 | 1.00 | 32.54 | B | O |
| ATOM | 12042 | OE2 | GLU | B | 236 | 89.081 | 23.254 | −11.316 | 1.00 | 28.82 | B | O |
| ATOM | 12043 | C | GLU | B | 236 | 84.852 | 25.988 | −12.902 | 1.00 | 21.39 | B | C |
| ATOM | 12044 | O | GLU | B | 236 | 84.299 | 24.885 | −12.977 | 1.00 | 23.11 | B | O |
| ATOM | 12046 | N | LEU | B | 237 | 84.395 | 26.989 | −12.154 | 1.00 | 19.15 | B | N |
| ATOM | 12047 | CA | LEU | B | 237 | 83.205 | 26.805 | −11.340 | 1.00 | 17.76 | B | C |
| ATOM | 12049 | CB | LEU | B | 237 | 82.892 | 28.060 | −10.548 | 1.00 | 15.89 | B | C |
| ATOM | 12052 | CG | LEU | B | 237 | 81.682 | 27.946 | −9.637 | 1.00 | 14.28 | B | C |
| ATOM | 12054 | CD1 | LEU | B | 237 | 81.846 | 26.791 | −8.650 | 1.00 | 8.37 | B | C |
| ATOM | 12058 | CD2 | LEU | B | 237 | 81.476 | 29.262 | −8.914 | 1.00 | 13.97 | B | C |
| ATOM | 12062 | C | LEU | B | 237 | 82.035 | 26.434 | −12.255 | 1.00 | 18.88 | B | C |
| ATOM | 12063 | O | LEU | B | 237 | 81.303 | 25.467 | −11.980 | 1.00 | 21.48 | B | O |
| ATOM | 12065 | N | ALA | B | 238 | 81.911 | 27.163 | −13.362 | 1.00 | 16.52 | B | N |
| ATOM | 12066 | CA | ALA | B | 238 | 80.791 | 27.010 | −14.287 | 1.00 | 18.32 | B | C |
| ATOM | 12068 | CB | ALA | B | 238 | 80.871 | 28.022 | −15.404 | 1.00 | 16.15 | B | C |
| ATOM | 12072 | C | ALA | B | 238 | 80.759 | 25.621 | −14.881 | 1.00 | 20.18 | B | C |
| ATOM | 12073 | O | ALA | B | 238 | 79.683 | 25.009 | −14.973 | 1.00 | 22.18 | B | O |
| ATOM | 12075 | N | ILE | B | 239 | 81.932 | 25.132 | −15.293 | 1.00 | 19.80 | B | N |
| ATOM | 12076 | CA | ILE | B | 239 | 82.039 | 23.792 | −15.821 | 1.00 | 19.87 | B | C |
| ATOM | 12078 | CB | ILE | B | 239 | 83.461 | 23.458 | −16.279 | 1.00 | 20.01 | B | C |
| ATOM | 12080 | CG1 | ILE | B | 239 | 83.800 | 24.223 | −17.567 | 1.00 | 21.51 | B | C |
| ATOM | 12083 | CD1 | ILE | B | 239 | 85.250 | 23.962 | −18.074 | 1.00 | 19.39 | B | C |
| ATOM | 12087 | CG2 | ILE | B | 239 | 83.601 | 21.955 | −16.508 | 1.00 | 13.60 | B | C |
| ATOM | 12091 | C | ILE | B | 239 | 81.589 | 22.800 | −14.757 | 1.00 | 21.11 | B | C |
| ATOM | 12092 | O | ILE | B | 239 | 80.781 | 21.917 | −15.030 | 1.00 | 22.06 | B | O |
| ATOM | 12094 | N | LEU | B | 240 | 82.090 | 22.968 | −13.543 | 1.00 | 21.72 | B | N |
| ATOM | 12095 | CA | LEU | B | 240 | 81.820 | 22.022 | −12.474 | 1.00 | 23.21 | B | C |
| ATOM | 12097 | CB | LEU | B | 240 | 82.645 | 22.326 | −11.208 | 1.00 | 23.26 | B | C |
| ATOM | 12100 | CG | LEU | B | 240 | 83.815 | 21.443 | −10.789 | 1.00 | 32.42 | B | C |
| ATOM | 12102 | CD1 | LEU | B | 240 | 84.539 | 20.728 | −11.964 | 1.00 | 33.31 | B | C |
| ATOM | 12106 | CD2 | LEU | B | 240 | 84.799 | 22.287 | −9.940 | 1.00 | 30.31 | B | C |

TABLE 4-2-continued

| Coordinates of *P. alba* IspS | | | | | | | | | | | | |
|---|---|---|---|---|---|---|---|---|---|---|---|---|
| ATOM | 12110 | C | LEU | B | 240 | 80.353 | 22.027 | −12.106 | 1.00 | 21.05 | B | C |
| ATOM | 12111 | O | LEU | B | 240 | 79.753 | 20.969 | −11.972 | 1.00 | 23.99 | B | O |
| ATOM | 12113 | N | ASP | B | 241 | 79.800 | 23.205 | −11.876 | 1.00 | 20.47 | B | N |
| ATOM | 12114 | CA | ASP | B | 241 | 78.395 | 23.319 | −11.512 | 1.00 | 20.64 | B | C |
| ATOM | 12116 | CB | ASP | B | 241 | 78.004 | 24.779 | −11.273 | 1.00 | 21.72 | B | C |
| ATOM | 12119 | CG | ASP | B | 241 | 76.721 | 24.920 | −10.461 | 1.00 | 25.74 | B | C |
| ATOM | 12120 | OD1 | ASP | B | 241 | 75.606 | 24.991 | −11.048 | 1.00 | 24.61 | B | O |
| ATOM | 12121 | OD2 | ASP | B | 241 | 76.829 | 24.948 | −9.231 | 1.00 | 20.16 | B | O |
| ATOM | 12122 | C | ASP | B | 241 | 77.513 | 22.698 | −12.610 | 1.00 | 20.65 | B | C |
| ATOM | 12123 | O | ASP | B | 241 | 76.609 | 21.925 | −12.306 | 1.00 | 20.46 | B | O |
| ATOM | 12125 | N | TYR | B | 242 | 77.816 | 22.985 | −13.876 | 1.00 | 20.03 | B | N |
| ATOM | 12126 | CA | TYR | B | 242 | 76.993 | 22.490 | −14.981 | 1.00 | 21.97 | B | C |
| ATOM | 12128 | CB | TYR | B | 242 | 77.486 | 23.024 | −16.327 | 1.00 | 21.09 | B | C |
| ATOM | 12131 | CG | TYR | B | 242 | 76.593 | 22.662 | −17.515 | 1.00 | 21.48 | B | C |
| ATOM | 12132 | CD1 | TYR | B | 242 | 75.662 | 23.564 | −18.022 | 1.00 | 20.87 | B | C |
| ATOM | 12134 | CE1 | TYR | B | 242 | 74.844 | 23.217 | −19.112 | 1.00 | 23.37 | B | C |
| ATOM | 12136 | CZ | TYR | B | 242 | 74.986 | 21.976 | −19.706 | 1.00 | 19.51 | B | C |
| ATOM | 12137 | OH | TYR | B | 242 | 74.216 | 21.612 | −20.777 | 1.00 | 27.52 | B | O |
| ATOM | 12139 | CE2 | TYR | B | 242 | 75.914 | 21.084 | −19.226 | 1.00 | 19.92 | B | C |
| ATOM | 12141 | CD2 | TYR | B | 242 | 76.702 | 21.429 | −18.138 | 1.00 | 21.77 | B | C |
| ATOM | 12143 | C | TYR | B | 242 | 76.922 | 20.967 | −15.033 | 1.00 | 22.49 | B | C |
| ATOM | 12144 | O | TYR | B | 242 | 75.836 | 20.393 | −15.206 | 1.00 | 22.20 | B | O |
| ATOM | 12146 | N | ASN | B | 243 | 78.082 | 20.324 | −14.937 | 1.00 | 22.43 | B | N |
| ATOM | 12147 | CA | ASN | B | 243 | 78.157 | 18.857 | −14.990 | 1.00 | 22.60 | B | C |
| ATOM | 12149 | CB | ASN | B | 243 | 79.601 | 18.375 | −15.194 | 1.00 | 20.63 | B | C |
| ATOM | 12152 | CG | ASN | B | 243 | 80.153 | 18.766 | −16.560 | 1.00 | 25.15 | B | C |
| ATOM | 12153 | OD1 | ASN | B | 243 | 79.389 | 18.975 | −17.507 | 1.00 | 28.79 | B | O |
| ATOM | 12154 | ND2 | ASN | B | 243 | 81.478 | 18.871 | −16.670 | 1.00 | 18.72 | B | N |
| ATOM | 12157 | C | ASN | B | 243 | 77.546 | 18.240 | −13.741 | 1.00 | 20.99 | B | C |
| ATOM | 12158 | O | ASN | B | 243 | 76.966 | 17.154 | −13.795 | 1.00 | 22.45 | B | O |
| ATOM | 12160 | N | MET | B | 244 | 77.646 | 18.942 | −12.626 | 1.00 | 19.24 | B | N |
| ATOM | 12161 | CA | MET | B | 244 | 76.979 | 18.480 | −11.426 | 1.00 | 22.91 | B | C |
| ATOM | 12163 | CB | MET | B | 244 | 77.363 | 19.339 | −10.230 | 1.00 | 22.09 | B | C |
| ATOM | 12166 | CG | MET | B | 244 | 76.629 | 18.976 | −8.959 | 1.00 | 26.36 | B | C |
| ATOM | 12169 | SD | MET | B | 244 | 76.675 | 20.330 | −7.774 | 1.00 | 40.41 | B | S |
| ATOM | 12170 | CE | MET | B | 244 | 75.425 | 21.413 | −8.512 | 1.00 | 38.87 | B | C |
| ATOM | 12174 | C | MET | B | 244 | 75.449 | 18.467 | −11.621 | 1.00 | 23.24 | B | C |
| ATOM | 12175 | O | MET | B | 244 | 74.793 | 17.460 | −11.333 | 1.00 | 24.26 | B | O |
| ATOM | 12177 | N | ILE | B | 245 | 74.898 | 19.569 | −12.120 | 1.00 | 22.08 | B | N |
| ATOM | 12178 | CA | ILE | B | 245 | 73.457 | 19.669 | −12.309 | 1.00 | 21.64 | B | C |
| ATOM | 12180 | CB | ILE | B | 245 | 73.036 | 21.093 | −12.702 | 1.00 | 22.89 | B | C |
| ATOM | 12182 | CG1 | ILE | B | 245 | 73.240 | 22.044 | −11.518 | 1.00 | 22.42 | B | C |
| ATOM | 12185 | CD1 | ILE | B | 245 | 72.776 | 23.512 | −11.793 | 1.00 | 23.27 | B | C |
| ATOM | 12189 | CG2 | ILE | B | 245 | 71.558 | 21.129 | −13.161 | 1.00 | 20.97 | B | C |
| ATOM | 12193 | C | ILE | B | 245 | 73.037 | 18.640 | −13.356 | 1.00 | 21.34 | B | C |
| ATOM | 12194 | O | ILE | B | 245 | 72.069 | 17.912 | −13.180 | 1.00 | 21.20 | B | O |
| ATOM | 12196 | N | GLN | B | 246 | 73.803 | 18.526 | −14.423 | 1.00 | 21.82 | B | N |
| ATOM | 12197 | CA | GLN | B | 246 | 73.522 | 17.493 | −15.396 | 1.00 | 22.03 | B | C |
| ATOM | 12199 | CB | GLN | B | 246 | 74.574 | 17.464 | −16.484 | 1.00 | 22.15 | B | C |
| ATOM | 12202 | CG | GLN | B | 246 | 74.215 | 16.563 | −17.638 | 1.00 | 21.61 | B | C |
| ATOM | 12205 | CD | GLN | B | 246 | 75.271 | 16.560 | −18.695 | 1.00 | 21.70 | B | C |
| ATOM | 12206 | OE1 | GLN | B | 246 | 76.364 | 16.058 | −18.472 | 1.00 | 32.02 | B | O |
| ATOM | 12207 | NE2 | GLN | B | 246 | 74.962 | 17.133 | −19.861 | 1.00 | 24.97 | B | N |
| ATOM | 12210 | C | GLN | B | 246 | 73.417 | 16.121 | −14.743 | 1.00 | 24.58 | B | C |
| ATOM | 12211 | O | GLN | B | 246 | 72.529 | 15.355 | −15.097 | 1.00 | 24.66 | B | O |
| ATOM | 12213 | N | SER | B | 247 | 74.285 | 15.797 | −13.784 | 1.00 | 23.32 | B | N |
| ATOM | 12214 | CA | SER | B | 247 | 74.229 | 14.455 | −13.209 | 1.00 | 25.50 | B | C |
| ATOM | 12216 | CB | SER | B | 247 | 75.468 | 14.111 | −12.354 | 1.00 | 24.49 | B | C |
| ATOM | 12219 | OG | SER | B | 247 | 75.372 | 14.688 | −11.056 | 1.00 | 30.70 | B | O |
| ATOM | 12221 | C | SER | B | 247 | 72.932 | 14.269 | −12.417 | 1.00 | 25.70 | B | C |
| ATOM | 12222 | O | SER | B | 247 | 72.401 | 13.167 | −12.346 | 1.00 | 26.49 | B | O |
| ATOM | 12224 | N | VAL | B | 248 | 72.412 | 15.338 | −11.833 | 1.00 | 25.46 | B | N |
| ATOM | 12225 | CA | VAL | B | 248 | 71.079 | 15.268 | −11.244 | 1.00 | 25.37 | B | C |
| ATOM | 12227 | CB | VAL | B | 248 | 70.708 | 16.577 | −10.534 | 1.00 | 25.38 | B | C |
| ATOM | 12229 | CG1 | VAL | B | 248 | 69.289 | 16.493 | −9.982 | 1.00 | 21.73 | B | C |
| ATOM | 12233 | CG2 | VAL | B | 248 | 71.737 | 16.887 | −9.411 | 1.00 | 21.11 | B | C |
| ATOM | 12237 | C | VAL | B | 248 | 70.019 | 14.910 | −12.324 | 1.00 | 27.50 | B | C |
| ATOM | 12238 | O | VAL | B | 248 | 69.186 | 14.022 | −12.114 | 1.00 | 30.45 | B | O |
| ATOM | 12240 | N | TYR | B | 249 | 70.069 | 15.575 | −13.475 | 1.00 | 25.85 | B | N |
| ATOM | 12241 | CA | TYR | B | 249 | 69.129 | 15.288 | −14.571 | 1.00 | 26.78 | B | C |
| ATOM | 12243 | CB | TYR | B | 249 | 69.407 | 16.170 | −15.807 | 1.00 | 25.46 | B | C |
| ATOM | 12246 | CG | TYR | B | 249 | 69.297 | 17.684 | −15.619 | 1.00 | 24.49 | B | C |
| ATOM | 12247 | CD1 | TYR | B | 249 | 68.579 | 18.237 | −14.570 | 1.00 | 19.54 | B | C |
| ATOM | 12249 | CE1 | TYR | B | 249 | 68.456 | 19.592 | −14.429 | 1.00 | 21.35 | B | C |
| ATOM | 12251 | CZ | TYR | B | 249 | 69.059 | 20.421 | −15.335 | 1.00 | 23.71 | B | C |
| ATOM | 12252 | OH | TYR | B | 249 | 68.955 | 21.768 | −15.170 | 1.00 | 24.97 | B | O |
| ATOM | 12254 | CE2 | TYR | B | 249 | 69.757 | 19.909 | −16.406 | 1.00 | 21.28 | B | C |
| ATOM | 12256 | CD2 | TYR | B | 249 | 69.880 | 18.553 | −16.539 | 1.00 | 22.56 | B | C |

TABLE 4-2-continued

Coordinates of *P. alba* IspS

| | | | | | | | | | | | | |
|---|---|---|---|---|---|---|---|---|---|---|---|---|
| ATOM | 12258 | C | TYR | B | 249 | 69.190 | 13.819 | −15.025 | 1.00 | 28.33 | B | C |
| ATOM | 12259 | O | TYR | B | 249 | 68.153 | 13.182 | −15.264 | 1.00 | 27.41 | B | O |
| ATOM | 12261 | N | GLN | B | 250 | 70.411 | 13.317 | −15.184 | 1.00 | 27.94 | B | N |
| ATOM | 12262 | CA | GLN | B | 250 | 70.647 | 11.928 | −15.547 | 1.00 | 28.73 | B | C |
| ATOM | 12264 | CB | GLN | B | 250 | 72.140 | 11.676 | −15.770 | 1.00 | 28.24 | B | C |
| ATOM | 12267 | CG | GLN | B | 250 | 72.701 | 12.430 | −16.993 | 1.00 | 26.66 | B | C |
| ATOM | 12270 | CD | GLN | B | 250 | 74.230 | 12.432 | −17.049 | 1.00 | 30.68 | B | C |
| ATOM | 12271 | OE1 | GLN | B | 250 | 74.890 | 12.107 | −16.073 | 1.00 | 28.92 | B | O |
| ATOM | 12272 | NE2 | GLN | B | 250 | 74.792 | 12.819 | −18.196 | 1.00 | 27.40 | B | N |
| ATOM | 12275 | C | GLN | B | 250 | 70.044 | 10.973 | −14.505 | 1.00 | 29.66 | B | C |
| ATOM | 12276 | O | GLN | B | 250 | 69.393 | 10.007 | −14.868 | 1.00 | 30.79 | B | O |
| ATOM | 12278 | N | ARG | B | 251 | 70.179 | 11.263 | −13.219 | 1.00 | 30.47 | B | N |
| ATOM | 12279 | CA | ARG | B | 251 | 69.458 | 10.465 | −12.218 | 1.00 | 31.78 | B | C |
| ATOM | 12281 | CB | ARG | B | 251 | 69.915 | 10.799 | −10.792 | 1.00 | 32.21 | B | C |
| ATOM | 12284 | CG | ARG | B | 251 | 69.243 | 9.926 | −9.703 | 1.00 | 39.99 | B | C |
| ATOM | 12287 | CD | ARG | B | 251 | 69.850 | 10.113 | −8.314 | 1.00 | 51.23 | B | C |
| ATOM | 12290 | NE | ARG | B | 251 | 70.143 | 11.526 | −8.019 | 1.00 | 62.83 | B | N |
| ATOM | 12292 | CZ | ARG | B | 251 | 71.360 | 12.091 | −7.992 | 1.00 | 67.84 | B | C |
| ATOM | 12293 | NH1 | ARG | B | 251 | 72.469 | 11.384 | −8.228 | 1.00 | 66.43 | B | N |
| ATOM | 12296 | NH2 | ARG | B | 251 | 71.470 | 13.391 | −7.716 | 1.00 | 67.17 | B | N |
| ATOM | 12299 | C | ARG | B | 251 | 67.914 | 10.585 | −12.351 | 1.00 | 31.19 | B | C |
| ATOM | 12300 | O | ARG | B | 251 | 67.212 | 9.576 | −12.358 | 1.00 | 31.09 | B | O |
| ATOM | 12302 | N | ASP | B | 252 | 67.397 | 11.806 | −12.450 | 1.00 | 29.49 | B | N |
| ATOM | 12303 | CA | ASP | B | 252 | 65.973 | 12.026 | −12.633 | 1.00 | 27.24 | B | C |
| ATOM | 12305 | CB | ASP | B | 252 | 65.686 | 13.502 | −12.947 | 1.00 | 28.05 | B | C |
| ATOM | 12308 | CG | ASP | B | 252 | 66.003 | 14.474 | −11.791 | 1.00 | 30.79 | B | C |
| ATOM | 12309 | OD1 | ASP | B | 252 | 66.059 | 14.063 | −10.612 | 1.00 | 31.73 | B | O |
| ATOM | 12310 | OD2 | ASP | B | 252 | 66.155 | 15.691 | −12.096 | 1.00 | 28.66 | B | O |
| ATOM | 12311 | C | ASP | B | 252 | 65.474 | 11.193 | −13.831 | 1.00 | 28.33 | B | C |
| ATOM | 12312 | O | ASP | B | 252 | 64.457 | 10.512 | −13.754 | 1.00 | 28.67 | B | O |
| ATOM | 12314 | N | LEU | B | 253 | 66.203 | 11.267 | −14.940 | 1.00 | 28.59 | B | N |
| ATOM | 12315 | CA | LEU | B | 253 | 65.850 | 10.580 | −16.179 | 1.00 | 29.23 | B | C |
| ATOM | 12317 | CB | LEU | B | 253 | 66.735 | 11.070 | −17.332 | 1.00 | 26.17 | B | C |
| ATOM | 12320 | CG | LEU | B | 253 | 66.435 | 10.484 | −18.704 | 1.00 | 32.56 | B | C |
| ATOM | 12322 | CD1 | LEU | B | 253 | 64.988 | 10.790 | −19.120 | 1.00 | 22.29 | B | C |
| ATOM | 12326 | CD2 | LEU | B | 253 | 67.448 | 10.988 | −19.739 | 1.00 | 36.23 | B | C |
| ATOM | 12330 | C | LEU | B | 253 | 65.945 | 9.055 | −16.093 | 1.00 | 30.46 | B | C |
| ATOM | 12331 | O | LEU | B | 253 | 65.246 | 8.361 | −16.831 | 1.00 | 29.74 | B | O |
| ATOM | 12333 | N | ARG | B | 254 | 66.819 | 8.537 | −15.231 | 1.00 | 32.61 | B | N |
| ATOM | 12334 | CA | ARG | B | 254 | 66.942 | 7.083 | −15.057 | 1.00 | 35.04 | B | C |
| ATOM | 12336 | CB | ARG | B | 254 | 68.241 | 6.682 | −14.330 | 1.00 | 36.65 | B | C |
| ATOM | 12339 | CG | ARG | B | 254 | 69.522 | 6.685 | −15.202 | 1.00 | 39.59 | B | C |
| ATOM | 12342 | CD | ARG | B | 254 | 70.676 | 5.892 | −14.532 | 1.00 | 45.23 | B | C |
| ATOM | 12345 | NE | ARG | B | 254 | 71.001 | 6.378 | −13.184 | 1.00 | 43.70 | B | N |
| ATOM | 12347 | CZ | ARG | B | 254 | 71.747 | 7.452 | −12.921 | 1.00 | 44.00 | B | C |
| ATOM | 12348 | NH1 | ARG | B | 254 | 72.276 | 8.181 | −13.910 | 1.00 | 39.76 | B | N |
| ATOM | 12351 | NH2 | ARG | B | 254 | 71.961 | 7.807 | −11.659 | 1.00 | 43.71 | B | N |
| ATOM | 12354 | C | ARG | B | 254 | 65.720 | 6.574 | −14.306 | 1.00 | 34.86 | B | C |
| ATOM | 12355 | O | ARG | B | 254 | 65.111 | 5.593 | −14.712 | 1.00 | 35.53 | B | O |
| ATOM | 12357 | N | GLU | B | 255 | 65.346 | 7.291 | −13.251 | 1.00 | 34.73 | B | N |
| ATOM | 12358 | CA | GLU | B | 255 | 64.149 | 7.011 | −12.450 | 1.00 | 37.10 | B | C |
| ATOM | 12360 | CB | GLU | B | 255 | 64.060 | 8.073 | −11.345 | 1.00 | 39.63 | B | C |
| ATOM | 12363 | CG | GLU | B | 255 | 63.692 | 7.589 | −9.941 | 1.00 | 52.09 | B | C |
| ATOM | 12366 | CD | GLU | B | 255 | 64.217 | 8.541 | −8.844 | 1.00 | 59.96 | B | C |
| ATOM | 12367 | OE1 | GLU | B | 255 | 65.456 | 8.703 | −8.728 | 1.00 | 62.20 | B | O |
| ATOM | 12368 | OE2 | GLU | B | 255 | 63.393 | 9.120 | −8.103 | 1.00 | 63.44 | B | O |
| ATOM | 12369 | C | GLU | B | 255 | 62.851 | 7.043 | −13.298 | 1.00 | 37.49 | B | C |
| ATOM | 12370 | O | GLU | B | 255 | 61.983 | 6.172 | −13.179 | 1.00 | 38.24 | B | O |
| ATOM | 12372 | N | THR | B | 256 | 62.726 | 8.066 | −14.139 | 1.00 | 33.48 | B | N |
| ATOM | 12373 | CA | THR | B | 256 | 61.550 | 8.236 | −14.970 | 1.00 | 32.03 | B | C |
| ATOM | 12375 | CB | THR | B | 256 | 61.489 | 9.676 | −15.484 | 1.00 | 28.82 | B | C |
| ATOM | 12377 | OG1 | THR | B | 256 | 61.258 | 10.518 | −14.365 | 1.00 | 31.10 | B | O |
| ATOM | 12379 | CG2 | THR | B | 256 | 60.378 | 9.886 | −16.462 | 1.00 | 32.38 | B | C |
| ATOM | 12383 | C | THR | B | 256 | 61.529 | 7.209 | −16.104 | 1.00 | 31.37 | B | C |
| ATOM | 12384 | O | THR | B | 256 | 60.465 | 6.736 | −16.483 | 1.00 | 30.12 | B | O |
| ATOM | 12386 | N | SER | B | 257 | 62.704 | 6.859 | −16.632 | 1.00 | 32.20 | B | N |
| ATOM | 12387 | CA | SER | B | 257 | 62.816 | 5.812 | −17.662 | 1.00 | 32.63 | B | C |
| ATOM | 12389 | CB | SER | B | 257 | 64.257 | 5.674 | −18.156 | 1.00 | 32.05 | B | C |
| ATOM | 12392 | OG | SER | B | 257 | 64.640 | 6.805 | −18.913 | 1.00 | 35.00 | B | O |
| ATOM | 12394 | C | SER | B | 257 | 62.329 | 4.460 | −17.135 | 1.00 | 32.30 | B | C |
| ATOM | 12395 | O | SER | B | 257 | 61.626 | 3.731 | −17.836 | 1.00 | 32.52 | B | O |
| ATOM | 12397 | N | ARG | B | 258 | 62.687 | 4.150 | −15.893 | 1.00 | 31.83 | B | N |
| ATOM | 12398 | CA | ARG | B | 258 | 62.215 | 2.934 | −15.244 | 1.00 | 35.46 | B | C |
| ATOM | 12400 | CB | ARG | B | 258 | 62.737 | 2.777 | −13.798 | 1.00 | 37.72 | B | C |
| ATOM | 12403 | CG | ARG | B | 258 | 64.138 | 2.136 | −13.696 | 1.00 | 46.00 | B | C |
| ATOM | 12406 | CD | ARG | B | 258 | 64.423 | 1.530 | −12.295 | 1.00 | 51.03 | B | C |
| ATOM | 12409 | NE | ARG | B | 258 | 64.165 | 2.474 | −11.198 | 1.00 | 52.82 | B | N |
| ATOM | 12411 | CZ | ARG | B | 258 | 65.033 | 3.368 | −10.717 | 1.00 | 56.37 | B | C |

TABLE 4-2-continued

Coordinates of *P. alba* IspS

| | | | | | | | | | | | | |
|---|---|---|---|---|---|---|---|---|---|---|---|---|
| ATOM | 12412 | NH1 | ARG | B | 258 | 64.663 | 4.155 | −9.715 | 1.00 | 57.59 | B | N |
| ATOM | 12415 | NH2 | ARG | B | 258 | 66.261 | 3.492 | −11.219 | 1.00 | 58.73 | B | N |
| ATOM | 12418 | C | ARG | B | 258 | 60.715 | 2.938 | −15.235 | 1.00 | 33.44 | B | C |
| ATOM | 12419 | O | ARG | B | 258 | 60.098 | 1.963 | −15.640 | 1.00 | 34.72 | B | O |
| ATOM | 12421 | N | TRP | B | 259 | 60.132 | 4.032 | −14.773 | 1.00 | 31.58 | B | N |
| ATOM | 12422 | CA | TRP | B | 259 | 58.695 | 4.182 | −14.811 | 1.00 | 31.82 | B | C |
| ATOM | 12424 | CB | TRP | B | 259 | 58.281 | 5.561 | −14.324 | 1.00 | 32.08 | B | C |
| ATOM | 12427 | CG | TRP | B | 259 | 56.866 | 5.918 | −14.621 | 1.00 | 27.02 | B | C |
| ATOM | 12428 | CD1 | TRP | B | 259 | 55.764 | 5.504 | −13.935 | 1.00 | 30.20 | B | C |
| ATOM | 12430 | NE1 | TRP | B | 259 | 54.632 | 6.051 | −14.491 | 1.00 | 34.18 | B | N |
| ATOM | 12432 | CE2 | TRP | B | 259 | 54.991 | 6.832 | −15.558 | 1.00 | 25.57 | B | C |
| ATOM | 12433 | CD2 | TRP | B | 259 | 56.394 | 6.780 | −15.666 | 1.00 | 26.24 | B | C |
| ATOM | 12434 | CE3 | TRP | B | 259 | 57.015 | 7.473 | −16.706 | 1.00 | 21.19 | B | C |
| ATOM | 12436 | CZ3 | TRP | B | 259 | 56.238 | 8.204 | −17.569 | 1.00 | 25.68 | B | C |
| ATOM | 12438 | CH2 | TRP | B | 259 | 54.848 | 8.253 | −17.423 | 1.00 | 31.07 | B | C |
| ATOM | 12440 | CZ2 | TRP | B | 259 | 54.209 | 7.562 | −16.425 | 1.00 | 26.47 | B | C |
| ATOM | 12442 | C | TRP | B | 259 | 58.158 | 3.980 | −16.222 | 1.00 | 31.90 | B | C |
| ATOM | 12443 | O | TRP | B | 259 | 57.209 | 3.231 | −16.416 | 1.00 | 34.40 | B | O |
| ATOM | 12445 | N | TRP | B | 260 | 58.755 | 4.650 | −17.201 | 1.00 | 29.58 | B | N |
| ATOM | 12446 | CA | TRP | B | 260 | 58.219 | 4.623 | −18.564 | 1.00 | 29.21 | B | C |
| ATOM | 12448 | CB | TRP | B | 260 | 59.020 | 5.542 | −19.471 | 1.00 | 28.39 | B | C |
| ATOM | 12451 | CG | TRP | B | 260 | 58.463 | 5.760 | −20.832 | 1.00 | 31.21 | B | C |
| ATOM | 12452 | CD1 | TRP | B | 260 | 59.128 | 5.613 | −22.011 | 1.00 | 32.56 | B | C |
| ATOM | 12454 | NE1 | TRP | B | 260 | 58.305 | 5.952 | −23.056 | 1.00 | 35.69 | B | N |
| ATOM | 12456 | CE2 | TRP | B | 260 | 57.088 | 6.341 | −22.564 | 1.00 | 28.01 | B | C |
| ATOM | 12457 | CD2 | TRP | B | 260 | 57.140 | 6.220 | −21.171 | 1.00 | 26.28 | B | C |
| ATOM | 12458 | CE3 | TRP | B | 260 | 56.006 | 6.556 | −20.426 | 1.00 | 29.49 | B | C |
| ATOM | 12460 | CZ3 | TRP | B | 260 | 54.871 | 6.979 | −21.092 | 1.00 | 27.25 | B | C |
| ATOM | 12462 | CH2 | TRP | B | 260 | 54.851 | 7.081 | −22.477 | 1.00 | 26.73 | B | C |
| ATOM | 12464 | CZ2 | TRP | B | 260 | 55.947 | 6.764 | −23.232 | 1.00 | 32.88 | B | C |
| ATOM | 12466 | C | TRP | B | 260 | 58.244 | 3.226 | −19.150 | 1.00 | 27.50 | B | C |
| ATOM | 12467 | O | TRP | B | 260 | 57.308 | 2.844 | −19.832 | 1.00 | 23.27 | B | O |
| ATOM | 12469 | N | ARG | B | 261 | 59.324 | 2.503 | −18.865 | 1.00 | 29.60 | B | N |
| ATOM | 12470 | CA | ARG | B | 261 | 59.551 | 1.144 | −19.348 | 1.00 | 34.53 | B | C |
| ATOM | 12472 | CB | ARG | B | 261 | 60.971 | 0.697 | −18.977 | 1.00 | 35.16 | B | C |
| ATOM | 12475 | CG | ARG | B | 261 | 61.605 | −0.290 | −19.932 | 1.00 | 46.23 | B | C |
| ATOM | 12478 | CD | ARG | B | 261 | 63.068 | −0.626 | −19.554 | 1.00 | 55.36 | B | C |
| ATOM | 12481 | NE | ARG | B | 261 | 63.895 | 0.584 | −19.412 | 1.00 | 60.95 | B | N |
| ATOM | 12483 | CZ | ARG | B | 261 | 64.475 | 1.013 | −18.281 | 1.00 | 63.65 | B | C |
| ATOM | 12484 | NH1 | ARG | B | 261 | 65.189 | 2.134 | −18.300 | 1.00 | 57.86 | B | N |
| ATOM | 12487 | NH2 | ARG | B | 261 | 64.369 | 0.342 | −17.130 | 1.00 | 65.79 | B | N |
| ATOM | 12490 | C | ARG | B | 261 | 58.509 | 0.198 | −18.741 | 1.00 | 37.14 | B | C |
| ATOM | 12491 | O | ARG | B | 261 | 57.920 | −0.634 | −19.435 | 1.00 | 39.01 | B | O |
| ATOM | 12493 | N | ARG | B | 262 | 58.284 | 0.360 | −17.442 | 1.00 | 38.02 | B | N |
| ATOM | 12494 | CA | ARG | B | 262 | 57.177 | −0.268 | −16.716 | 1.00 | 39.33 | B | C |
| ATOM | 12496 | CB | ARG | B | 262 | 57.015 | 0.410 | −15.345 | 1.00 | 43.52 | B | C |
| ATOM | 12499 | CG | ARG | B | 262 | 56.465 | −0.472 | −14.256 | 1.00 | 52.63 | B | C |
| ATOM | 12502 | CD | ARG | B | 262 | 57.576 | −1.181 | −13.525 | 1.00 | 62.09 | B | C |
| ATOM | 12505 | NE | ARG | B | 262 | 57.050 | −2.325 | −12.786 | 1.00 | 69.73 | B | N |
| ATOM | 12507 | CZ | ARG | B | 262 | 56.722 | −3.494 | −13.333 | 1.00 | 71.95 | B | C |
| ATOM | 12508 | NH1 | ARG | B | 262 | 56.865 | −3.698 | −14.642 | 1.00 | 69.88 | B | N |
| ATOM | 12511 | NH2 | ARG | B | 262 | 56.243 | −4.462 | −12.561 | 1.00 | 73.11 | B | N |
| ATOM | 12514 | C | ARG | B | 262 | 55.852 | −0.134 | −17.434 | 1.00 | 34.28 | B | C |
| ATOM | 12515 | O | ARG | B | 262 | 55.161 | −1.109 | −17.686 | 1.00 | 36.30 | B | O |
| ATOM | 12517 | N | VAL | B | 263 | 55.504 | 1.100 | −17.747 | 1.00 | 30.95 | B | N |
| ATOM | 12518 | CA | VAL | B | 263 | 54.232 | 1.419 | −18.372 | 1.00 | 28.88 | B | C |
| ATOM | 12520 | CB | VAL | B | 263 | 53.991 | 2.937 | −18.339 | 1.00 | 29.02 | B | C |
| ATOM | 12522 | CG1 | VAL | B | 263 | 53.972 | 3.419 | −16.887 | 1.00 | 31.64 | B | C |
| ATOM | 12526 | CG2 | VAL | B | 263 | 52.725 | 3.282 | −19.018 | 1.00 | 23.71 | B | C |
| ATOM | 12530 | C | VAL | B | 263 | 54.178 | 0.879 | −19.806 | 1.00 | 28.33 | B | C |
| ATOM | 12531 | O | VAL | B | 263 | 53.120 | 0.527 | −20.282 | 1.00 | 28.41 | B | O |
| ATOM | 12533 | N | GLY | B | 264 | 55.328 | 0.793 | −20.473 | 1.00 | 28.72 | B | N |
| ATOM | 12534 | CA | GLY | B | 264 | 55.455 | 0.142 | −21.782 | 1.00 | 28.49 | B | C |
| ATOM | 12537 | C | GLY | B | 264 | 54.407 | 0.496 | −22.813 | 1.00 | 29.83 | B | C |
| ATOM | 12538 | O | GLY | B | 264 | 54.075 | −0.304 | −23.665 | 1.00 | 33.27 | B | O |
| ATOM | 12540 | N | LEU | B | 265 | 53.866 | 1.692 | −22.740 | 1.00 | 32.92 | B | N |
| ATOM | 12541 | CA | LEU | B | 265 | 52.709 | 2.035 | −23.561 | 1.00 | 36.59 | B | C |
| ATOM | 12543 | CB | LEU | B | 265 | 52.038 | 3.282 | −22.981 | 1.00 | 34.56 | B | C |
| ATOM | 12546 | CG | LEU | B | 265 | 50.645 | 3.685 | −23.411 | 1.00 | 34.01 | B | C |
| ATOM | 12548 | CD1 | LEU | B | 265 | 49.599 | 2.606 | −23.171 | 1.00 | 25.90 | B | C |
| ATOM | 12552 | CD2 | LEU | B | 265 | 50.267 | 4.994 | −22.672 | 1.00 | 34.22 | B | C |
| ATOM | 12556 | C | LEU | B | 265 | 53.113 | 2.229 | −25.033 | 1.00 | 41.17 | B | C |
| ATOM | 12557 | O | LEU | B | 265 | 52.405 | 1.785 | −25.947 | 1.00 | 40.79 | B | O |
| ATOM | 12559 | N | ALA | B | 266 | 54.263 | 2.867 | −25.250 | 1.00 | 45.34 | B | N |
| ATOM | 12560 | CA | ALA | B | 266 | 54.839 | 3.029 | −26.591 | 1.00 | 49.21 | B | C |
| ATOM | 12562 | CB | ALA | B | 266 | 56.169 | 3.765 | −26.497 | 1.00 | 51.02 | B | C |
| ATOM | 12566 | C | ALA | B | 266 | 55.042 | 1.697 | −27.325 | 1.00 | 51.05 | B | C |
| ATOM | 12567 | O | ALA | B | 266 | 54.816 | 1.605 | −28.525 | 1.00 | 54.29 | B | O |

TABLE 4-2-continued

Coordinates of *P. alba* IspS

| | | | | | | | | | | | | |
|---|---|---|---|---|---|---|---|---|---|---|---|---|
| ATOM | 12569 | N | THR | B | 267 | 55.487 | 0.674 | −26.602 | 1.00 | 51.62 | B | N |
| ATOM | 12570 | CA | THR | B | 267 | 55.674 | −0.659 | −27.166 | 1.00 | 50.64 | B | C |
| ATOM | 12572 | CB | THR | B | 267 | 56.249 | −1.603 | −26.109 | 1.00 | 50.95 | B | C |
| ATOM | 12574 | OG1 | THR | B | 267 | 57.237 | −0.904 | −25.348 | 1.00 | 53.05 | B | O |
| ATOM | 12576 | CG2 | THR | B | 267 | 56.856 | −2.837 | −26.747 | 1.00 | 53.61 | B | C |
| ATOM | 12580 | C | THR | B | 267 | 54.363 | −1.270 | −27.629 | 1.00 | 49.87 | B | C |
| ATOM | 12581 | O | THR | B | 267 | 54.276 | −1.822 | −28.729 | 1.00 | 52.54 | B | O |
| ATOM | 12583 | N | LYS | B | 268 | 53.345 | −1.168 | −26.781 | 1.00 | 47.07 | B | N |
| ATOM | 12584 | CA | LYS | B | 268 | 52.106 | −1.927 | −26.953 | 1.00 | 45.30 | B | C |
| ATOM | 12586 | CB | LYS | B | 268 | 51.514 | −2.270 | −25.578 | 1.00 | 45.48 | B | C |
| ATOM | 12589 | CG | LYS | B | 268 | 52.430 | −3.115 | −24.675 | 1.00 | 45.38 | B | C |
| ATOM | 12592 | CD | LYS | B | 268 | 52.465 | −4.594 | −25.090 | 1.00 | 49.05 | B | C |
| ATOM | 12595 | CE | LYS | B | 268 | 53.528 | −5.398 | −24.328 | 1.00 | 51.83 | B | C |
| ATOM | 12598 | NZ | LYS | B | 268 | 53.838 | −6.705 | −24.985 | 1.00 | 54.82 | B | N |
| ATOM | 12602 | C | LYS | B | 268 | 51.078 | −1.207 | −27.819 | 1.00 | 43.95 | B | C |
| ATOM | 12603 | O | LYS | B | 268 | 50.152 | −1.829 | −28.343 | 1.00 | 44.75 | B | O |
| ATOM | 12605 | N | LEU | B | 269 | 51.229 | 0.105 | −27.947 | 1.00 | 43.27 | B | N |
| ATOM | 12606 | CA | LEU | B | 269 | 50.456 | 0.896 | −28.900 | 1.00 | 42.83 | B | C |
| ATOM | 12608 | CB | LEU | B | 269 | 50.081 | 2.274 | −28.316 | 1.00 | 42.53 | B | C |
| ATOM | 12611 | CG | LEU | B | 269 | 48.694 | 2.512 | −27.709 | 1.00 | 42.48 | B | C |
| ATOM | 12613 | CD1 | LEU | B | 269 | 48.340 | 1.537 | −26.633 | 1.00 | 40.39 | B | C |
| ATOM | 12617 | CD2 | LEU | B | 269 | 48.603 | 3.935 | −27.181 | 1.00 | 43.69 | B | C |
| ATOM | 12621 | C | LEU | B | 269 | 51.341 | 1.081 | −30.134 | 1.00 | 43.67 | B | C |
| ATOM | 12622 | O | LEU | B | 269 | 52.298 | 1.875 | −30.115 | 1.00 | 44.75 | B | O |
| ATOM | 12624 | N | HIS | B | 270 | 51.014 | 0.353 | −31.200 | 1.00 | 42.52 | B | N |
| ATOM | 12625 | CA | HIS | B | 270 | 51.820 | 0.323 | −32.430 | 1.00 | 42.36 | B | C |
| ATOM | 12627 | CB | HIS | B | 270 | 51.297 | −0.765 | −33.406 | 1.00 | 44.29 | B | C |
| ATOM | 12630 | CG | HIS | B | 270 | 50.914 | −2.062 | −32.743 | 1.00 | 55.81 | B | C |
| ATOM | 12631 | ND1 | HIS | B | 270 | 51.604 | −2.596 | −31.670 | 1.00 | 59.93 | B | N |
| ATOM | 12633 | CE1 | HIS | B | 270 | 51.038 | −3.734 | −31.307 | 1.00 | 61.45 | B | C |
| ATOM | 12635 | NE2 | HIS | B | 270 | 50.011 | −3.964 | −32.106 | 1.00 | 62.50 | B | N |
| ATOM | 12637 | CD2 | HIS | B | 270 | 49.910 | −2.935 | −33.012 | 1.00 | 61.72 | B | C |
| ATOM | 12639 | C | HIS | B | 270 | 51.862 | 1.683 | −33.164 | 1.00 | 38.47 | B | C |
| ATOM | 12640 | O | HIS | B | 270 | 52.821 | 1.980 | −33.872 | 1.00 | 36.44 | B | O |
| ATOM | 12642 | N | PHE | B | 271 | 50.813 | 2.487 | −33.019 | 1.00 | 34.67 | B | N |
| ATOM | 12643 | CA | PHE | B | 271 | 50.782 | 3.831 | −33.616 | 1.00 | 35.53 | B | C |
| ATOM | 12645 | CB | PHE | B | 271 | 49.327 | 4.306 | −33.814 | 1.00 | 35.09 | B | C |
| ATOM | 12648 | CG | PHE | B | 271 | 48.598 | 4.542 | −32.527 | 1.00 | 32.41 | B | C |
| ATOM | 12649 | CD1 | PHE | B | 271 | 48.680 | 5.764 | −31.891 | 1.00 | 36.89 | B | C |
| ATOM | 12651 | CE1 | PHE | B | 271 | 48.031 | 5.986 | −30.662 | 1.00 | 42.82 | B | C |
| ATOM | 12653 | CZ | PHE | B | 271 | 47.311 | 4.955 | −30.061 | 1.00 | 41.42 | B | C |
| ATOM | 12655 | CE2 | PHE | B | 271 | 47.234 | 3.714 | −30.695 | 1.00 | 43.35 | B | C |
| ATOM | 12657 | CD2 | PHE | B | 271 | 47.881 | 3.516 | −31.920 | 1.00 | 37.61 | B | C |
| ATOM | 12659 | C | PHE | B | 271 | 51.570 | 4.893 | −32.797 | 1.00 | 37.13 | B | C |
| ATOM | 12660 | O | PHE | B | 271 | 51.846 | 5.976 | −33.321 | 1.00 | 37.34 | B | O |
| ATOM | 12662 | N | ALA | B | 272 | 51.940 | 4.589 | −31.543 | 1.00 | 37.26 | B | N |
| ATOM | 12663 | CA | ALA | B | 272 | 52.442 | 5.634 | −30.600 | 1.00 | 38.89 | B | C |
| ATOM | 12665 | CB | ALA | B | 272 | 52.094 | 5.270 | −29.140 | 1.00 | 36.66 | B | C |
| ATOM | 12669 | C | ALA | B | 272 | 53.938 | 5.971 | −30.703 | 1.00 | 39.07 | B | C |
| ATOM | 12670 | O | ALA | B | 272 | 54.797 | 5.092 | −30.725 | 1.00 | 39.92 | B | O |
| ATOM | 12672 | N | ARG | B | 273 | 54.230 | 7.265 | −30.746 | 1.00 | 41.88 | B | N |
| ATOM | 12673 | CA | ARG | B | 273 | 55.598 | 7.754 | −30.590 | 1.00 | 43.68 | B | C |
| ATOM | 12675 | CB | ARG | B | 273 | 55.688 | 9.247 | −30.928 | 1.00 | 45.24 | B | C |
| ATOM | 12678 | CG | ARG | B | 273 | 55.566 | 9.610 | −32.409 | 1.00 | 54.15 | B | C |
| ATOM | 12681 | CD | ARG | B | 273 | 55.488 | 11.141 | −32.589 | 1.00 | 58.80 | B | C |
| ATOM | 12684 | NE | ARG | B | 273 | 54.171 | 11.685 | −32.226 | 1.00 | 59.04 | B | N |
| ATOM | 12686 | CZ | ARG | B | 273 | 53.934 | 12.957 | −31.892 | 1.00 | 67.66 | B | C |
| ATOM | 12687 | NH1 | ARG | B | 273 | 54.925 | 13.849 | −31.851 | 1.00 | 73.10 | B | N |
| ATOM | 12690 | NH2 | ARG | B | 273 | 52.699 | 13.348 | −31.579 | 1.00 | 66.54 | B | N |
| ATOM | 12693 | C | ARG | B | 273 | 56.033 | 7.570 | −29.146 | 1.00 | 42.37 | B | C |
| ATOM | 12694 | O | ARG | B | 273 | 55.259 | 7.841 | −28.231 | 1.00 | 44.16 | B | O |
| ATOM | 12696 | N | ASP | B | 274 | 57.259 | 7.102 | −28.953 | 1.00 | 41.17 | B | N |
| ATOM | 12697 | CA | ASP | B | 274 | 57.943 | 7.200 | −27.663 | 1.00 | 39.65 | B | C |
| ATOM | 12699 | CB | ASP | B | 274 | 58.887 | 6.003 | −27.479 | 1.00 | 37.65 | B | C |
| ATOM | 12702 | CG | ASP | B | 274 | 59.781 | 6.132 | −26.246 | 1.00 | 41.72 | B | C |
| ATOM | 12703 | OD1 | ASP | B | 274 | 59.773 | 7.202 | −25.594 | 1.00 | 40.60 | B | O |
| ATOM | 12704 | OD2 | ASP | B | 274 | 60.514 | 5.165 | −25.926 | 1.00 | 46.31 | B | O |
| ATOM | 12705 | C | ASP | B | 274 | 58.730 | 8.542 | −27.618 | 1.00 | 39.30 | B | C |
| ATOM | 12706 | O | ASP | B | 274 | 59.720 | 8.711 | −28.349 | 1.00 | 38.18 | B | O |
| ATOM | 12708 | N | ARG | B | 275 | 58.307 | 9.459 | −26.744 | 1.00 | 38.02 | B | N |
| ATOM | 12709 | CA | ARG | B | 275 | 58.890 | 10.796 | −26.645 | 1.00 | 38.08 | B | C |
| ATOM | 12711 | CB | ARG | B | 275 | 57.833 | 11.834 | −27.058 | 1.00 | 39.92 | B | C |
| ATOM | 12714 | CG | ARG | B | 275 | 57.840 | 12.200 | −28.556 | 1.00 | 47.80 | B | C |
| ATOM | 12717 | CD | ARG | B | 275 | 58.691 | 13.450 | −28.835 | 1.00 | 61.16 | B | C |
| ATOM | 12720 | NE | ARG | B | 275 | 58.526 | 13.945 | −30.206 | 1.00 | 68.47 | B | N |
| ATOM | 12722 | CZ | ARG | B | 275 | 59.096 | 13.401 | −31.281 | 1.00 | 74.79 | B | C |
| ATOM | 12723 | NH1 | ARG | B | 275 | 59.875 | 12.326 | −31.169 | 1.00 | 76.37 | B | N |
| ATOM | 12726 | NH2 | ARG | B | 275 | 58.876 | 13.926 | −32.484 | 1.00 | 75.18 | B | N |

TABLE 4-2-continued

Coordinates of *P. alba* IspS

| | | | | | | | | | | | | |
|---|---|---|---|---|---|---|---|---|---|---|---|---|
| ATOM | 12729 | C | ARG | B | 275 | 59.425 | 11.147 | −25.254 | 1.00 | 37.19 | B | C |
| ATOM | 12730 | O | ARG | B | 275 | 59.433 | 12.316 | −24.879 | 1.00 | 36.87 | B | O |
| ATOM | 12732 | N | LEU | B | 276 | 59.886 | 10.160 | −24.485 | 1.00 | 37.00 | B | N |
| ATOM | 12733 | CA | LEU | B | 276 | 60.295 | 10.426 | −23.098 | 1.00 | 34.98 | B | C |
| ATOM | 12735 | CB | LEU | B | 276 | 60.573 | 9.134 | −22.292 | 1.00 | 36.67 | B | C |
| ATOM | 12738 | CG | LEU | B | 276 | 60.890 | 9.375 | −20.797 | 1.00 | 35.76 | B | C |
| ATOM | 12740 | CD1 | LEU | B | 276 | 59.754 | 10.147 | −20.115 | 1.00 | 33.92 | B | C |
| ATOM | 12744 | CD2 | LEU | B | 276 | 61.169 | 8.113 | −20.053 | 1.00 | 36.13 | B | C |
| ATOM | 12748 | C | LEU | B | 276 | 61.503 | 11.363 | −23.013 | 1.00 | 32.92 | B | C |
| ATOM | 12749 | O | LEU | B | 276 | 61.435 | 12.361 | −22.318 | 1.00 | 31.67 | B | O |
| ATOM | 12751 | N | ILE | B | 277 | 62.582 | 11.055 | −23.725 | 1.00 | 30.95 | B | N |
| ATOM | 12752 | CA | ILE | B | 277 | 63.822 | 11.841 | −23.617 | 1.00 | 29.96 | B | C |
| ATOM | 12754 | CB | ILE | B | 277 | 64.948 | 11.249 | −24.510 | 1.00 | 31.64 | B | C |
| ATOM | 12756 | CG1 | ILE | B | 277 | 65.404 | 9.882 | −23.979 | 1.00 | 34.19 | B | C |
| ATOM | 12759 | CD1 | ILE | B | 277 | 66.155 | 9.043 | −25.015 | 1.00 | 37.10 | B | C |
| ATOM | 12763 | CG2 | ILE | B | 277 | 66.155 | 12.185 | −24.569 | 1.00 | 30.97 | B | C |
| ATOM | 12767 | C | ILE | B | 277 | 63.591 | 13.296 | −24.024 | 1.00 | 29.71 | B | C |
| ATOM | 12768 | O | ILE | B | 277 | 64.075 | 14.213 | −23.367 | 1.00 | 29.06 | B | O |
| ATOM | 12770 | N | GLU | B | 278 | 62.851 | 13.492 | −25.113 | 1.00 | 28.47 | B | N |
| ATOM | 12771 | CA | GLU | B | 278 | 62.515 | 14.814 | −25.599 | 1.00 | 30.52 | B | C |
| ATOM | 12773 | CB | GLU | B | 278 | 61.773 | 14.746 | −26.949 | 1.00 | 32.74 | B | C |
| ATOM | 12776 | CG | GLU | B | 278 | 62.616 | 14.225 | −28.148 | 1.00 | 44.05 | B | C |
| ATOM | 12779 | CD | GLU | B | 278 | 62.477 | 12.706 | −28.437 | 1.00 | 50.83 | B | C |
| ATOM | 12780 | OE1 | GLU | B | 278 | 62.589 | 11.868 | −27.508 | 1.00 | 47.29 | B | O |
| ATOM | 12781 | OE2 | GLU | B | 278 | 62.263 | 12.357 | −29.624 | 1.00 | 59.50 | B | O |
| ATOM | 12782 | C | GLU | B | 278 | 61.650 | 15.529 | −24.554 | 1.00 | 29.96 | B | C |
| ATOM | 12783 | O | GLU | B | 278 | 61.811 | 16.720 | −24.328 | 1.00 | 29.51 | B | O |
| ATOM | 12785 | N | SER | B | 279 | 60.753 | 14.787 | −23.900 | 1.00 | 27.64 | B | N |
| ATOM | 12786 | CA | SER | B | 279 | 59.880 | 15.369 | −22.906 | 1.00 | 24.85 | B | C |
| ATOM | 12788 | CB | SER | B | 279 | 58.779 | 14.387 | −22.528 | 1.00 | 25.36 | B | C |
| ATOM | 12791 | OG | SER | B | 279 | 57.866 | 14.222 | −23.614 | 1.00 | 31.09 | B | O |
| ATOM | 12793 | C | SER | B | 279 | 60.692 | 15.817 | −21.689 | 1.00 | 24.19 | B | C |
| ATOM | 12794 | O | SER | B | 279 | 60.402 | 16.841 | −21.072 | 1.00 | 20.81 | B | O |
| ATOM | 12796 | N | PHE | B | 280 | 61.726 | 15.060 | −21.358 | 1.00 | 22.21 | B | N |
| ATOM | 12797 | CA | PHE | B | 280 | 62.538 | 15.405 | −20.233 | 1.00 | 22.68 | B | C |
| ATOM | 12799 | CB | PHE | B | 280 | 63.394 | 14.219 | −19.801 | 1.00 | 23.70 | B | C |
| ATOM | 12802 | CG | PHE | B | 280 | 63.993 | 14.420 | −18.458 | 1.00 | 22.17 | B | C |
| ATOM | 12803 | CD1 | PHE | B | 280 | 63.282 | 14.110 | −17.326 | 1.00 | 26.73 | B | C |
| ATOM | 12805 | CE1 | PHE | B | 280 | 63.815 | 14.336 | −16.082 | 1.00 | 28.79 | B | C |
| ATOM | 12807 | CZ | PHE | B | 280 | 65.071 | 14.912 | −15.977 | 1.00 | 26.30 | B | C |
| ATOM | 12809 | CE2 | PHE | B | 280 | 65.767 | 15.240 | −17.094 | 1.00 | 23.82 | B | C |
| ATOM | 12811 | CD2 | PHE | B | 280 | 65.224 | 15.010 | −18.332 | 1.00 | 25.89 | B | C |
| ATOM | 12813 | C | PHE | B | 280 | 63.421 | 16.639 | −20.521 | 1.00 | 23.35 | B | C |
| ATOM | 12814 | O | PHE | B | 280 | 63.538 | 17.546 | −19.684 | 1.00 | 22.15 | B | O |
| ATOM | 12816 | N | TYR | B | 281 | 64.035 | 16.663 | −21.702 | 1.00 | 22.05 | B | N |
| ATOM | 12817 | CA | TYR | B | 281 | 64.744 | 17.845 | −22.179 | 1.00 | 22.89 | B | C |
| ATOM | 12819 | CB | TYR | B | 281 | 65.243 | 17.599 | −23.613 | 1.00 | 24.85 | B | C |
| ATOM | 12822 | CG | TYR | B | 281 | 65.725 | 18.824 | −24.340 | 1.00 | 27.86 | B | C |
| ATOM | 12823 | CD1 | TYR | B | 281 | 67.038 | 19.263 | −24.199 | 1.00 | 29.60 | B | C |
| ATOM | 12825 | CE1 | TYR | B | 281 | 67.481 | 20.396 | −24.830 | 1.00 | 30.12 | B | C |
| ATOM | 12827 | CZ | TYR | B | 281 | 66.619 | 21.106 | −25.645 | 1.00 | 27.86 | B | C |
| ATOM | 12828 | OH | TYR | B | 281 | 67.094 | 22.218 | −26.293 | 1.00 | 40.12 | B | O |
| ATOM | 12830 | CE2 | TYR | B | 281 | 65.321 | 20.681 | −25.831 | 1.00 | 27.61 | B | C |
| ATOM | 12832 | CD2 | TYR | B | 281 | 64.880 | 19.541 | −25.164 | 1.00 | 26.08 | B | C |
| ATOM | 12834 | C | TYR | B | 281 | 63.774 | 19.033 | −22.107 | 1.00 | 23.97 | B | C |
| ATOM | 12835 | O | TYR | B | 281 | 64.114 | 20.107 | −21.638 | 1.00 | 23.50 | B | O |
| ATOM | 12837 | N | TRP | B | 282 | 62.535 | 18.821 | −22.522 | 1.00 | 23.00 | B | N |
| ATOM | 12838 | CA | TRP | B | 282 | 61.567 | 19.906 | −22.475 | 1.00 | 23.33 | B | C |
| ATOM | 12840 | CB | TRP | B | 282 | 60.235 | 19.447 | −23.059 | 1.00 | 22.37 | B | C |
| ATOM | 12843 | CG | TRP | B | 282 | 59.154 | 20.412 | −22.895 | 1.00 | 22.74 | B | C |
| ATOM | 12844 | CD1 | TRP | B | 282 | 58.337 | 20.555 | −21.821 | 1.00 | 22.39 | B | C |
| ATOM | 12846 | NE1 | TRP | B | 282 | 57.435 | 21.564 | −22.047 | 1.00 | 23.45 | B | N |
| ATOM | 12848 | CE2 | TRP | B | 282 | 57.667 | 22.082 | −23.291 | 1.00 | 23.69 | B | C |
| ATOM | 12849 | CD2 | TRP | B | 282 | 58.742 | 21.375 | −23.850 | 1.00 | 22.10 | B | C |
| ATOM | 12850 | CE3 | TRP | B | 282 | 59.184 | 21.712 | −25.131 | 1.00 | 26.55 | B | C |
| ATOM | 12852 | CZ3 | TRP | B | 282 | 58.546 | 22.733 | −25.798 | 1.00 | 28.88 | B | C |
| ATOM | 12854 | CH2 | TRP | B | 282 | 57.483 | 23.424 | −25.210 | 1.00 | 30.17 | B | C |
| ATOM | 12856 | CZ2 | TRP | B | 282 | 57.028 | 23.111 | −23.960 | 1.00 | 27.03 | B | C |
| ATOM | 12858 | C | TRP | B | 282 | 61.418 | 20.387 | −21.028 | 1.00 | 22.80 | B | C |
| ATOM | 12859 | O | TRP | B | 282 | 61.406 | 21.593 | −20.769 | 1.00 | 20.61 | B | O |
| ATOM | 12861 | N | ALA | B | 283 | 61.308 | 19.431 | −20.103 | 1.00 | 21.05 | B | N |
| ATOM | 12862 | CA | ALA | B | 283 | 61.084 | 19.723 | −18.692 | 1.00 | 20.62 | B | C |
| ATOM | 12864 | CB | ALA | B | 283 | 60.816 | 18.452 | −17.899 | 1.00 | 18.78 | B | C |
| ATOM | 12868 | C | ALA | B | 283 | 62.249 | 20.468 | −18.081 | 1.00 | 19.81 | B | C |
| ATOM | 12869 | O | ALA | B | 283 | 62.048 | 21.246 | −17.179 | 1.00 | 19.59 | B | O |
| ATOM | 12871 | N | VAL | B | 284 | 63.459 | 20.228 | −18.570 | 1.00 | 21.14 | B | N |
| ATOM | 12872 | CA | VAL | B | 284 | 64.621 | 20.924 | −18.054 | 1.00 | 22.45 | B | C |
| ATOM | 12874 | CB | VAL | B | 284 | 65.935 | 20.350 | −18.615 | 1.00 | 25.86 | B | C |

TABLE 4-2-continued

Coordinates of *P. alba* IspS

| | | | | | | | | | | | | |
|---|---|---|---|---|---|---|---|---|---|---|---|---|
| ATOM | 12876 | CG1 | VAL | B | 284 | 66.234 | 18.966 | −17.953 | 1.00 | 18.72 | B | C |
| ATOM | 12880 | CG2 | VAL | B | 284 | 67.075 | 21.325 | −18.378 | 1.00 | 20.18 | B | C |
| ATOM | 12884 | C | VAL | B | 284 | 64.537 | 22.416 | −18.333 | 1.00 | 23.71 | B | C |
| ATOM | 12885 | O | VAL | B | 284 | 64.993 | 23.221 | −17.526 | 1.00 | 22.26 | B | O |
| ATOM | 12887 | N | GLY | B | 285 | 63.948 | 22.793 | −19.464 | 1.00 | 21.46 | B | N |
| ATOM | 12888 | CA | GLY | B | 285 | 63.763 | 24.215 | −19.762 | 1.00 | 20.96 | B | C |
| ATOM | 12891 | C | GLY | B | 285 | 62.773 | 24.857 | −18.808 | 1.00 | 21.82 | B | C |
| ATOM | 12892 | O | GLY | B | 285 | 62.909 | 26.011 | −18.460 | 1.00 | 21.74 | B | O |
| ATOM | 12894 | N | VAL | B | 286 | 61.794 | 24.090 | −18.345 | 1.00 | 22.60 | B | N |
| ATOM | 12895 | CA | VAL | B | 286 | 60.781 | 24.620 | −17.450 | 1.00 | 20.48 | B | C |
| ATOM | 12897 | CB | VAL | B | 286 | 59.539 | 23.732 | −17.498 | 1.00 | 23.12 | B | C |
| ATOM | 12899 | CG1 | VAL | B | 286 | 58.485 | 24.177 | −16.490 | 1.00 | 20.49 | B | C |
| ATOM | 12903 | CG2 | VAL | B | 286 | 58.976 | 23.732 | −18.955 | 1.00 | 17.84 | B | C |
| ATOM | 12907 | C | VAL | B | 286 | 61.309 | 24.792 | −16.046 | 1.00 | 20.31 | B | C |
| ATOM | 12908 | O | VAL | B | 286 | 61.106 | 25.842 | −15.436 | 1.00 | 22.39 | B | O |
| ATOM | 12910 | N | ALA | B | 287 | 61.979 | 23.772 | −15.527 | 1.00 | 19.27 | B | N |
| ATOM | 12911 | CA | ALA | B | 287 | 62.563 | 23.827 | −14.186 | 1.00 | 20.62 | B | C |
| ATOM | 12913 | CB | ALA | B | 287 | 61.690 | 23.117 | −13.227 | 1.00 | 22.01 | B | C |
| ATOM | 12917 | C | ALA | B | 287 | 63.988 | 23.242 | −14.163 | 1.00 | 21.88 | B | C |
| ATOM | 12918 | O | ALA | B | 287 | 64.196 | 22.022 | −14.069 | 1.00 | 24.85 | B | O |
| ATOM | 12920 | N | PHE | B | 288 | 64.972 | 24.115 | −14.247 | 1.00 | 20.90 | B | N |
| ATOM | 12921 | CA | PHE | B | 288 | 66.345 | 23.674 | −14.426 | 1.00 | 21.67 | B | C |
| ATOM | 12923 | CB | PHE | B | 288 | 67.122 | 24.674 | −15.275 | 1.00 | 22.83 | B | C |
| ATOM | 12926 | CG | PHE | B | 288 | 67.541 | 25.900 | −14.520 | 1.00 | 23.91 | B | C |
| ATOM | 12927 | CD1 | PHE | B | 288 | 68.710 | 25.905 | −13.784 | 1.00 | 33.80 | B | C |
| ATOM | 12929 | CE1 | PHE | B | 288 | 69.088 | 27.037 | −13.074 | 1.00 | 37.48 | B | C |
| ATOM | 12931 | CZ | PHE | B | 288 | 68.287 | 28.167 | −13.095 | 1.00 | 31.38 | B | C |
| ATOM | 12933 | CE2 | PHE | B | 288 | 67.137 | 28.167 | −13.821 | 1.00 | 36.32 | B | C |
| ATOM | 12935 | CD2 | PHE | B | 288 | 66.761 | 27.029 | −14.529 | 1.00 | 34.62 | B | C |
| ATOM | 12937 | C | PHE | B | 288 | 67.047 | 23.497 | −13.099 | 1.00 | 24.48 | B | C |
| ATOM | 12938 | O | PHE | B | 288 | 68.005 | 22.741 | −13.031 | 1.00 | 23.65 | B | O |
| ATOM | 12940 | N | GLU | B | 289 | 66.587 | 24.190 | −12.057 | 1.00 | 26.02 | B | N |
| ATOM | 12941 | CA | GLU | B | 289 | 67.310 | 24.197 | −10.792 | 1.00 | 29.62 | B | C |
| ATOM | 12943 | CB | GLU | B | 289 | 66.689 | 25.166 | −9.776 | 1.00 | 31.32 | B | C |
| ATOM | 12946 | CG | GLU | B | 289 | 66.721 | 26.644 | −10.177 | 1.00 | 36.70 | B | C |
| ATOM | 12949 | CD | GLU | B | 289 | 65.440 | 27.118 | −10.890 | 1.00 | 45.07 | B | C |
| ATOM | 12950 | OE1 | GLU | B | 289 | 65.081 | 28.295 | −10.677 | 1.00 | 47.42 | B | O |
| ATOM | 12951 | OE2 | GLU | B | 289 | 64.793 | 26.352 | −11.659 | 1.00 | 39.96 | B | O |
| ATOM | 12952 | C | GLU | B | 289 | 67.350 | 22.795 | −10.180 | 1.00 | 29.55 | B | C |
| ATOM | 12953 | O | GLU | B | 289 | 66.350 | 22.084 | −10.180 | 1.00 | 30.10 | B | O |
| ATOM | 12955 | N | PRO | B | 290 | 68.495 | 22.419 | −9.606 | 1.00 | 29.22 | B | N |
| ATOM | 12956 | CA | PRO | B | 290 | 68.716 | 21.062 | −9.120 | 1.00 | 28.35 | B | C |
| ATOM | 12958 | CB | PRO | B | 290 | 69.998 | 21.185 | −8.304 | 1.00 | 29.34 | B | C |
| ATOM | 12961 | CG | PRO | B | 290 | 70.632 | 22.443 | −8.746 | 1.00 | 31.20 | B | C |
| ATOM | 12964 | CD | PRO | B | 290 | 69.568 | 23.338 | −9.199 | 1.00 | 29.41 | B | C |
| ATOM | 12967 | C | PRO | B | 290 | 67.597 | 20.503 | −8.245 | 1.00 | 27.13 | B | C |
| ATOM | 12968 | O | PRO | B | 290 | 67.211 | 19.356 | −8.429 | 1.00 | 26.99 | B | O |
| ATOM | 12969 | N | GLN | B | 291 | 67.073 | 21.317 | −7.333 | 1.00 | 26.56 | B | N |
| ATOM | 12970 | CA | GLN | B | 291 | 66.043 | 20.889 | −6.395 | 1.00 | 28.08 | B | C |
| ATOM | 12972 | CB | GLN | B | 291 | 65.903 | 21.923 | −5.273 | 1.00 | 28.20 | B | C |
| ATOM | 12975 | CG | GLN | B | 291 | 65.226 | 23.240 | −5.649 | 1.00 | 29.54 | B | C |
| ATOM | 12978 | CD | GLN | B | 291 | 66.216 | 24.301 | −6.116 | 1.00 | 39.09 | B | C |
| ATOM | 12979 | OE1 | GLN | B | 291 | 67.318 | 23.982 | −6.604 | 1.00 | 38.40 | B | O |
| ATOM | 12980 | NE2 | GLN | B | 291 | 65.835 | 25.579 | −5.957 | 1.00 | 34.88 | B | N |
| ATOM | 12983 | C | GLN | B | 291 | 64.631 | 20.595 | −6.967 | 1.00 | 28.38 | B | C |
| ATOM | 12984 | O | GLN | B | 291 | 63.778 | 20.058 | −6.256 | 1.00 | 28.46 | B | O |
| ATOM | 12986 | N | TYR | B | 292 | 64.375 | 20.955 | −8.219 | 1.00 | 28.39 | B | N |
| ATOM | 12987 | CA | TYR | B | 292 | 63.043 | 20.732 | −8.817 | 1.00 | 29.49 | B | C |
| ATOM | 12989 | CB | TYR | B | 292 | 62.665 | 21.897 | −9.751 | 1.00 | 29.50 | B | C |
| ATOM | 12992 | CG | TYR | B | 292 | 62.448 | 23.230 | −9.077 | 1.00 | 31.00 | B | C |
| ATOM | 12993 | CD1 | TYR | B | 292 | 61.801 | 23.327 | −7.844 | 1.00 | 32.31 | B | C |
| ATOM | 12995 | CE1 | TYR | B | 292 | 61.595 | 24.565 | −7.235 | 1.00 | 36.98 | B | C |
| ATOM | 12997 | CZ | TYR | B | 292 | 62.016 | 25.723 | −7.869 | 1.00 | 39.38 | B | C |
| ATOM | 12998 | OH | TYR | B | 292 | 61.804 | 26.951 | −7.281 | 1.00 | 45.92 | B | O |
| ATOM | 13000 | CE2 | TYR | B | 292 | 62.634 | 25.655 | −9.106 | 1.00 | 42.09 | B | C |
| ATOM | 13002 | CD2 | TYR | B | 292 | 62.849 | 24.413 | −9.701 | 1.00 | 39.44 | B | C |
| ATOM | 13004 | C | TYR | B | 292 | 62.942 | 19.410 | −9.590 | 1.00 | 28.42 | B | C |
| ATOM | 13005 | O | TYR | B | 292 | 62.355 | 19.362 | −10.659 | 1.00 | 27.22 | B | O |
| ATOM | 13007 | N | SER | B | 293 | 63.523 | 18.344 | −9.050 | 1.00 | 28.09 | B | N |
| ATOM | 13008 | CA | SER | B | 293 | 63.430 | 17.036 | −9.669 | 1.00 | 28.01 | B | C |
| ATOM | 13010 | CB | SER | B | 293 | 64.181 | 15.987 | −8.824 | 1.00 | 29.51 | B | C |
| ATOM | 13013 | OG | SER | B | 293 | 65.590 | 16.068 | −9.070 | 1.00 | 30.76 | B | O |
| ATOM | 13015 | C | SER | B | 293 | 61.973 | 16.635 | −9.898 | 1.00 | 26.55 | B | C |
| ATOM | 13016 | O | SER | B | 293 | 61.634 | 16.155 | −10.968 | 1.00 | 28.86 | B | O |
| ATOM | 13018 | N | ASP | B | 294 | 61.120 | 16.853 | −8.907 | 1.00 | 25.23 | B | N |
| ATOM | 13019 | CA | ASP | B | 294 | 59.721 | 16.469 | −9.000 | 1.00 | 28.08 | B | C |
| ATOM | 13021 | CB | ASP | B | 294 | 58.962 | 16.785 | −7.696 | 1.00 | 28.58 | B | C |
| ATOM | 13024 | CG | ASP | B | 294 | 59.432 | 15.942 | −6.522 | 1.00 | 37.32 | B | C |

TABLE 4-2-continued

Coordinates of *P. alba* IspS

| | | | | | | | | | | | | |
|---|---|---|---|---|---|---|---|---|---|---|---|---|
| ATOM | 13025 | OD1 | ASP | B | 294 | 60.154 | 14.943 | −6.741 | 1.00 | 36.71 | B | O |
| ATOM | 13026 | OD2 | ASP | B | 294 | 59.094 | 16.301 | −5.363 | 1.00 | 45.41 | B | O |
| ATOM | 13027 | C | ASP | B | 294 | 59.019 | 17.171 | −10.163 | 1.00 | 28.26 | B | C |
| ATOM | 13028 | O | ASP | B | 294 | 58.249 | 16.544 | −10.891 | 1.00 | 27.19 | B | O |
| ATOM | 13030 | N | CYS | B | 295 | 59.261 | 18.477 | −10.298 | 1.00 | 26.75 | B | N |
| ATOM | 13031 | CA | CYS | B | 295 | 58.687 | 19.249 | −11.376 | 1.00 | 24.72 | B | C |
| ATOM | 13033 | CB | CYS | B | 295 | 59.091 | 20.714 | −11.313 | 1.00 | 24.78 | B | C |
| ATOM | 13036 | SG | CYS | B | 295 | 58.157 | 21.730 | −12.489 | 1.00 | 24.85 | B | S |
| ATOM | 13038 | C | CYS | B | 295 | 59.090 | 18.651 | −12.702 | 1.00 | 25.01 | B | C |
| ATOM | 13039 | O | CYS | B | 295 | 58.222 | 18.397 | −13.539 | 1.00 | 23.90 | B | O |
| ATOM | 13041 | N | ARG | B | 296 | 60.386 | 18.396 | −12.893 | 1.00 | 24.46 | B | N |
| ATOM | 13042 | CA | ARG | B | 296 | 60.851 | 17.831 | −14.172 | 1.00 | 24.09 | B | C |
| ATOM | 13044 | CB | ARG | B | 296 | 62.369 | 17.647 | −14.205 | 1.00 | 24.77 | B | C |
| ATOM | 13047 | CG | ARG | B | 296 | 63.153 | 18.936 | −14.354 | 1.00 | 23.30 | B | C |
| ATOM | 13050 | CD | ARG | B | 296 | 64.643 | 18.682 | −14.514 | 1.00 | 19.69 | B | C |
| ATOM | 13053 | NE | ARG | B | 296 | 65.243 | 18.178 | −13.289 | 1.00 | 19.76 | B | N |
| ATOM | 13055 | CZ | ARG | B | 296 | 65.634 | 18.927 | −12.254 | 1.00 | 24.50 | B | C |
| ATOM | 13056 | NH1 | ARG | B | 296 | 65.496 | 20.255 | −12.255 | 1.00 | 25.75 | B | N |
| ATOM | 13059 | NH2 | ARG | B | 296 | 66.166 | 18.328 | −11.191 | 1.00 | 27.06 | B | N |
| ATOM | 13062 | C | ARG | B | 296 | 60.185 | 16.495 | −14.463 | 1.00 | 23.06 | B | C |
| ATOM | 13063 | O | ARG | B | 296 | 59.718 | 16.245 | −15.597 | 1.00 | 22.98 | B | O |
| ATOM | 13065 | N | ASN | B | 297 | 60.138 | 15.641 | −13.447 | 1.00 | 22.07 | B | N |
| ATOM | 13066 | CA | ASN | B | 297 | 59.565 | 14.316 | −13.609 | 1.00 | 24.36 | B | C |
| ATOM | 13068 | CB | ASN | B | 297 | 59.763 | 13.460 | −12.364 | 1.00 | 24.91 | B | C |
| ATOM | 13071 | CG | ASN | B | 297 | 61.206 | 13.110 | −12.150 | 1.00 | 31.79 | B | C |
| ATOM | 13072 | OD1 | ASN | B | 297 | 61.998 | 13.156 | −13.095 | 1.00 | 38.41 | B | O |
| ATOM | 13073 | ND2 | ASN | B | 297 | 61.570 | 12.757 | −10.911 | 1.00 | 29.95 | B | N |
| ATOM | 13076 | C | ASN | B | 297 | 58.095 | 14.399 | −13.952 | 1.00 | 24.42 | B | C |
| ATOM | 13077 | O | ASN | B | 297 | 57.622 | 13.726 | −14.876 | 1.00 | 23.19 | B | O |
| ATOM | 13079 | N | SER | B | 298 | 57.393 | 15.242 | −13.215 | 1.00 | 23.97 | B | N |
| ATOM | 13080 | CA | SER | B | 298 | 55.976 | 15.474 | −13.444 | 1.00 | 24.63 | B | C |
| ATOM | 13082 | CB | SER | B | 298 | 55.466 | 16.475 | −12.403 | 1.00 | 25.85 | B | C |
| ATOM | 13085 | OG | SER | B | 298 | 54.275 | 16.038 | −11.808 | 1.00 | 36.11 | B | O |
| ATOM | 13087 | C | SER | B | 298 | 55.694 | 16.009 | −14.851 | 1.00 | 23.06 | B | C |
| ATOM | 13088 | O | SER | B | 298 | 54.827 | 15.490 | −15.572 | 1.00 | 21.42 | B | O |
| ATOM | 13090 | N | VAL | B | 299 | 56.412 | 17.066 | −15.240 | 1.00 | 20.75 | B | N |
| ATOM | 13091 | CA | VAL | B | 299 | 56.238 | 17.639 | −16.554 | 1.00 | 18.08 | B | C |
| ATOM | 13093 | CB | VAL | B | 299 | 57.037 | 18.933 | −16.690 | 1.00 | 19.98 | B | C |
| ATOM | 13095 | CG1 | VAL | B | 299 | 57.029 | 19.453 | −18.146 | 1.00 | 20.35 | B | C |
| ATOM | 13099 | CG2 | VAL | B | 299 | 56.457 | 19.960 | −15.770 | 1.00 | 21.88 | B | C |
| ATOM | 13103 | C | VAL | B | 299 | 56.636 | 16.633 | −17.648 | 1.00 | 19.45 | B | C |
| ATOM | 13104 | O | VAL | B | 299 | 55.996 | 16.570 | −18.700 | 1.00 | 17.92 | B | O |
| ATOM | 13106 | N | ALA | B | 300 | 57.665 | 15.826 | −17.393 | 1.00 | 18.10 | B | N |
| ATOM | 13107 | CA | ALA | B | 300 | 58.147 | 14.869 | −18.404 | 1.00 | 19.47 | B | C |
| ATOM | 13109 | CB | ALA | B | 300 | 59.535 | 14.263 | −18.011 | 1.00 | 15.98 | B | C |
| ATOM | 13113 | C | ALA | B | 300 | 57.121 | 13.762 | −18.590 | 1.00 | 20.75 | B | C |
| ATOM | 13114 | O | ALA | B | 300 | 56.813 | 13.354 | −19.714 | 1.00 | 21.28 | B | O |
| ATOM | 13116 | N | LYS | B | 301 | 56.573 | 13.283 | −17.482 | 1.00 | 21.38 | B | N |
| ATOM | 13117 | CA | LYS | B | 301 | 55.560 | 12.239 | −17.553 | 1.00 | 20.81 | B | C |
| ATOM | 13119 | CB | LYS | B | 301 | 55.187 | 11.785 | −16.160 | 1.00 | 20.47 | B | C |
| ATOM | 13122 | CG | LYS | B | 301 | 56.259 | 10.978 | −15.481 | 1.00 | 20.34 | B | C |
| ATOM | 13125 | CD | LYS | B | 301 | 55.758 | 10.422 | −14.150 | 1.00 | 20.67 | B | C |
| ATOM | 13128 | CE | LYS | B | 301 | 56.846 | 9.711 | −13.349 | 1.00 | 28.61 | B | C |
| ATOM | 13131 | NZ | LYS | B | 301 | 56.310 | 9.346 | −11.992 | 1.00 | 31.10 | B | N |
| ATOM | 13135 | C | LYS | B | 301 | 54.313 | 12.719 | −18.283 | 1.00 | 19.17 | B | C |
| ATOM | 13136 | O | LYS | B | 301 | 53.752 | 11.998 | −19.088 | 1.00 | 19.72 | B | O |
| ATOM | 13138 | N | MET | B | 302 | 53.880 | 13.940 | −17.995 | 1.00 | 18.82 | B | N |
| ATOM | 13139 | CA | MET | B | 302 | 52.656 | 14.473 | −18.598 | 1.00 | 19.48 | B | C |
| ATOM | 13141 | CB | MET | B | 302 | 52.169 | 15.752 | −17.900 | 1.00 | 18.45 | B | C |
| ATOM | 13144 | CG | MET | B | 302 | 51.728 | 15.582 | −16.463 | 1.00 | 16.26 | B | C |
| ATOM | 13147 | SD | MET | B | 302 | 50.418 | 14.399 | −16.251 | 1.00 | 27.62 | B | S |
| ATOM | 13148 | CE | MET | B | 302 | 51.337 | 12.933 | −15.824 | 1.00 | 23.65 | B | C |
| ATOM | 13152 | C | MET | B | 302 | 52.860 | 14.765 | −20.067 | 1.00 | 21.47 | B | C |
| ATOM | 13153 | O | MET | B | 302 | 52.007 | 14.431 | −20.896 | 1.00 | 23.42 | B | O |
| ATOM | 13155 | N | PHE | B | 303 | 53.966 | 15.404 | −20.412 | 1.00 | 21.99 | B | N |
| ATOM | 13156 | CA | PHE | B | 303 | 54.225 | 15.621 | −21.834 | 1.00 | 22.67 | B | C |
| ATOM | 13158 | CB | PHE | B | 303 | 55.475 | 16.466 | −22.069 | 1.00 | 23.73 | B | C |
| ATOM | 13161 | CG | PHE | B | 303 | 55.398 | 17.344 | −23.304 | 1.00 | 31.04 | B | C |
| ATOM | 13162 | CD1 | PHE | B | 303 | 54.200 | 17.518 | −24.009 | 1.00 | 29.05 | B | C |
| ATOM | 13164 | CE1 | PHE | B | 303 | 54.144 | 18.322 | −25.144 | 1.00 | 42.79 | B | C |
| ATOM | 13166 | CZ | PHE | B | 303 | 55.280 | 18.986 | −25.577 | 1.00 | 41.71 | B | C |
| ATOM | 13168 | CE2 | PHE | B | 303 | 56.469 | 18.843 | −24.877 | 1.00 | 37.08 | B | C |
| ATOM | 13170 | CD2 | PHE | B | 303 | 56.525 | 18.023 | −23.742 | 1.00 | 37.60 | B | C |
| ATOM | 13172 | C | PHE | B | 303 | 54.312 | 14.315 | −22.621 | 1.00 | 21.08 | B | C |
| ATOM | 13173 | O | PHE | B | 303 | 53.799 | 14.238 | −23.733 | 1.00 | 21.61 | B | O |
| ATOM | 13175 | N | SER | B | 304 | 54.907 | 13.277 | −22.036 | 1.00 | 21.32 | B | N |
| ATOM | 13176 | CA | SER | B | 304 | 54.949 | 11.965 | −22.692 | 1.00 | 20.73 | B | C |
| ATOM | 13178 | CB | SER | B | 304 | 55.700 | 10.941 | −21.850 | 1.00 | 22.39 | B | C |

TABLE 4-2-continued

Coordinates of *P. alba* IspS

| | | | | | | | | | | | | |
|---|---|---|---|---|---|---|---|---|---|---|---|---|
| ATOM | 13181 | OG | SER | B | 304 | 57.032 | 11.374 | −21.573 | 1.00 | 24.34 | B | O |
| ATOM | 13183 | C | SER | B | 304 | 53.551 | 11.444 | −22.967 | 1.00 | 21.58 | B | C |
| ATOM | 13184 | O | SER | B | 304 | 53.296 | 10.929 | −24.034 | 1.00 | 23.78 | B | O |
| ATOM | 13186 | N | PHE | B | 305 | 52.639 | 11.591 | −22.011 | 1.00 | 21.21 | B | N |
| ATOM | 13187 | CA | PHE | B | 305 | 51.256 | 11.195 | −22.225 | 1.00 | 19.19 | B | C |
| ATOM | 13189 | CB | PHE | B | 305 | 50.487 | 11.141 | −20.903 | 1.00 | 21.39 | B | C |
| ATOM | 13192 | CG | PHE | B | 305 | 50.574 | 9.814 | −20.230 | 1.00 | 22.98 | B | C |
| ATOM | 13193 | CD1 | PHE | B | 305 | 49.894 | 8.742 | −20.738 | 1.00 | 22.59 | B | C |
| ATOM | 13195 | CE1 | PHE | B | 305 | 49.983 | 7.507 | −20.135 | 1.00 | 23.64 | B | C |
| ATOM | 13197 | CZ | PHE | B | 305 | 50.747 | 7.338 | −19.024 | 1.00 | 24.33 | B | C |
| ATOM | 13199 | CE2 | PHE | B | 305 | 51.435 | 8.406 | −18.505 | 1.00 | 27.51 | B | C |
| ATOM | 13201 | CD2 | PHE | B | 305 | 51.349 | 9.634 | −19.112 | 1.00 | 22.45 | B | C |
| ATOM | 13203 | C | PHE | B | 305 | 50.542 | 12.110 | −23.197 | 1.00 | 20.45 | B | C |
| ATOM | 13204 | O | PHE | B | 305 | 49.770 | 11.631 | −24.020 | 1.00 | 19.27 | B | O |
| ATOM | 13206 | N | VAL | B | 306 | 50.791 | 13.421 | −23.126 | 1.00 | 20.75 | B | N |
| ATOM | 13207 | CA | VAL | B | 306 | 50.184 | 14.351 | −24.081 | 1.00 | 19.25 | B | C |
| ATOM | 13209 | CB | VAL | B | 306 | 50.655 | 15.809 | −23.878 | 1.00 | 22.43 | B | C |
| ATOM | 13211 | CG1 | VAL | B | 306 | 50.202 | 16.687 | −25.012 | 1.00 | 14.46 | B | C |
| ATOM | 13215 | CG2 | VAL | B | 306 | 50.145 | 16.385 | −22.528 | 1.00 | 16.22 | B | C |
| ATOM | 13219 | C | VAL | B | 306 | 50.464 | 13.914 | −25.511 | 1.00 | 22.34 | B | C |
| ATOM | 13220 | O | VAL | B | 306 | 49.566 | 13.856 | −26.316 | 1.00 | 23.30 | B | O |
| ATOM | 13222 | N | THR | B | 307 | 51.696 | 13.555 | −25.830 | 1.00 | 25.01 | B | N |
| ATOM | 13223 | CA | THR | B | 307 | 52.025 | 13.284 | −27.227 | 1.00 | 26.57 | B | C |
| ATOM | 13225 | CB | THR | B | 307 | 53.520 | 13.087 | −27.435 | 1.00 | 26.12 | B | C |
| ATOM | 13227 | OG1 | THR | B | 307 | 53.909 | 11.896 | −26.774 | 1.00 | 40.17 | B | O |
| ATOM | 13229 | CG2 | THR | B | 307 | 54.339 | 14.252 | −26.872 | 1.00 | 33.09 | B | C |
| ATOM | 13233 | C | THR | B | 307 | 51.284 | 12.043 | −27.757 | 1.00 | 26.12 | B | C |
| ATOM | 13234 | O | THR | B | 307 | 50.866 | 12.016 | −28.903 | 1.00 | 25.66 | B | O |
| ATOM | 13236 | N | ILE | B | 308 | 51.139 | 11.031 | −26.908 | 1.00 | 24.81 | B | N |
| ATOM | 13237 | CA | ILE | B | 308 | 50.352 | 9.833 | −27.215 | 1.00 | 23.60 | B | C |
| ATOM | 13239 | CB | ILE | B | 308 | 50.545 | 8.768 | −26.118 | 1.00 | 25.72 | B | C |
| ATOM | 13241 | CG1 | ILE | B | 308 | 51.994 | 8.263 | −26.119 | 1.00 | 27.99 | B | C |
| ATOM | 13244 | CD1 | ILE | B | 308 | 52.272 | 7.297 | −24.983 | 1.00 | 28.28 | B | C |
| ATOM | 13248 | CG2 | ILE | B | 308 | 49.588 | 7.595 | −26.318 | 1.00 | 24.09 | B | C |
| ATOM | 13252 | C | ILE | B | 308 | 48.865 | 10.144 | −27.337 | 1.00 | 22.14 | B | C |
| ATOM | 13253 | O | ILE | B | 308 | 48.245 | 9.781 | −28.321 | 1.00 | 22.79 | B | O |
| ATOM | 13255 | N | ILE | B | 309 | 48.292 | 10.823 | −26.344 | 1.00 | 20.84 | B | N |
| ATOM | 13256 | CA | ILE | B | 309 | 46.882 | 11.147 | −26.371 | 1.00 | 21.20 | B | C |
| ATOM | 13258 | CB | ILE | B | 309 | 46.435 | 11.822 | −25.093 | 1.00 | 22.62 | B | C |
| ATOM | 13260 | CG1 | ILE | B | 309 | 46.643 | 10.910 | −23.874 | 1.00 | 26.22 | B | C |
| ATOM | 13263 | CD1 | ILE | B | 309 | 45.698 | 9.823 | −23.812 | 1.00 | 38.91 | B | C |
| ATOM | 13267 | CG2 | ILE | B | 309 | 44.993 | 12.206 | −25.188 | 1.00 | 18.44 | B | C |
| ATOM | 13271 | C | ILE | B | 309 | 46.612 | 12.069 | −27.563 | 1.00 | 22.75 | B | C |
| ATOM | 13272 | O | ILE | B | 309 | 45.645 | 11.896 | −28.307 | 1.00 | 23.59 | B | O |
| ATOM | 13274 | N | ASP | B | 310 | 47.506 | 13.010 | −27.796 | 1.00 | 22.88 | B | N |
| ATOM | 13275 | CA | ASP | B | 310 | 47.402 | 13.867 | −28.991 | 1.00 | 24.17 | B | C |
| ATOM | 13277 | CB | ASP | B | 310 | 48.606 | 14.828 | −29.062 | 1.00 | 25.25 | B | C |
| ATOM | 13280 | CG | ASP | B | 310 | 48.464 | 15.924 | −30.125 | 1.00 | 31.57 | B | C |
| ATOM | 13281 | OD1 | ASP | B | 310 | 47.362 | 16.203 | −30.614 | 1.00 | 41.50 | B | O |
| ATOM | 13282 | OD2 | ASP | B | 310 | 49.503 | 16.528 | −30.461 | 1.00 | 46.26 | B | O |
| ATOM | 13283 | C | ASP | B | 310 | 47.268 | 13.005 | −30.264 | 1.00 | 23.28 | B | C |
| ATOM | 13284 | O | ASP | B | 310 | 46.344 | 13.216 | −31.032 | 1.00 | 22.28 | B | O |
| ATOM | 13286 | N | ASP | B | 311 | 48.139 | 12.012 | −30.464 | 1.00 | 23.05 | B | N |
| ATOM | 13287 | CA | ASP | B | 311 | 48.040 | 11.175 | −31.666 | 1.00 | 25.68 | B | C |
| ATOM | 13289 | CB | ASP | B | 311 | 49.146 | 10.136 | −31.720 | 1.00 | 27.71 | B | C |
| ATOM | 13292 | CG | ASP | B | 311 | 50.509 | 10.741 | −31.947 | 1.00 | 35.42 | B | C |
| ATOM | 13293 | OD1 | ASP | B | 311 | 50.567 | 11.862 | −32.501 | 1.00 | 39.96 | B | O |
| ATOM | 13294 | OD2 | ASP | B | 311 | 51.516 | 10.092 | −31.558 | 1.00 | 44.33 | B | O |
| ATOM | 13295 | C | ASP | B | 311 | 46.703 | 10.442 | −31.770 | 1.00 | 24.73 | B | C |
| ATOM | 13296 | O | ASP | B | 311 | 46.168 | 10.275 | −32.866 | 1.00 | 25.59 | B | O |
| ATOM | 13298 | N | ILE | B | 312 | 46.169 | 9.998 | −30.640 | 1.00 | 21.14 | B | N |
| ATOM | 13299 | CA | ILE | B | 312 | 44.901 | 9.300 | −30.658 | 1.00 | 20.46 | B | C |
| ATOM | 13301 | CB | ILE | B | 312 | 44.558 | 8.792 | −29.225 | 1.00 | 21.25 | B | C |
| ATOM | 13303 | CG1 | ILE | B | 312 | 45.428 | 7.566 | −28.870 | 1.00 | 22.56 | B | C |
| ATOM | 13306 | CD1 | ILE | B | 312 | 45.327 | 7.127 | −27.386 | 1.00 | 15.81 | B | C |
| ATOM | 13310 | CG2 | ILE | B | 312 | 43.089 | 8.428 | −29.087 | 1.00 | 17.97 | B | C |
| ATOM | 13314 | C | ILE | B | 312 | 43.803 | 10.213 | −31.251 | 1.00 | 22.04 | B | C |
| ATOM | 13315 | O | ILE | B | 312 | 43.047 | 9.805 | −32.119 | 1.00 | 21.87 | B | O |
| ATOM | 13317 | N | TYR | B | 313 | 43.700 | 11.445 | −30.756 | 1.00 | 24.10 | B | N |
| ATOM | 13318 | CA | TYR | B | 313 | 42.717 | 12.413 | −31.269 | 1.00 | 22.33 | B | C |
| ATOM | 13320 | CB | TYR | B | 313 | 42.602 | 13.613 | −30.321 | 1.00 | 22.53 | B | C |
| ATOM | 13323 | CG | TYR | B | 313 | 41.860 | 13.350 | −29.049 | 1.00 | 18.01 | B | C |
| ATOM | 13324 | CD1 | TYR | B | 313 | 40.533 | 13.713 | −28.908 | 1.00 | 15.63 | B | C |
| ATOM | 13326 | CE1 | TYR | B | 313 | 39.838 | 13.478 | −27.730 | 1.00 | 18.26 | B | C |
| ATOM | 13328 | CZ | TYR | B | 313 | 40.489 | 12.864 | −26.664 | 1.00 | 22.61 | B | C |
| ATOM | 13329 | OH | TYR | B | 313 | 39.833 | 12.629 | −25.474 | 1.00 | 18.89 | B | O |
| ATOM | 13331 | CE2 | TYR | B | 313 | 41.811 | 12.496 | −26.785 | 1.00 | 23.65 | B | C |
| ATOM | 13333 | CD2 | TYR | B | 313 | 42.486 | 12.734 | −27.977 | 1.00 | 22.64 | B | C |

TABLE 4-2-continued

| Coordinates of *P. alba* IspS | | | | | | | | | | | | |
|---|---|---|---|---|---|---|---|---|---|---|---|---|
| ATOM | 13335 | C | TYR | B | 313 | 43.080 | 12.921 | −32.665 | 1.00 | 22.74 | B | C |
| ATOM | 13336 | O | TYR | B | 313 | 42.214 | 13.176 | −33.481 | 1.00 | 22.56 | B | O |
| ATOM | 13338 | N | ASP | B | 314 | 44.365 | 13.066 | −32.950 | 1.00 | 25.71 | B | N |
| ATOM | 13339 | CA | ASP | B | 314 | 44.768 | 13.652 | −34.221 | 1.00 | 26.66 | B | C |
| ATOM | 13341 | CB | ASP | B | 314 | 46.227 | 14.059 | −34.185 | 1.00 | 28.17 | B | C |
| ATOM | 13344 | CG | ASP | B | 314 | 46.668 | 14.758 | −35.459 | 1.00 | 34.44 | B | C |
| ATOM | 13345 | OD1 | ASP | B | 314 | 45.874 | 15.565 | −35.987 | 1.00 | 35.69 | B | O |
| ATOM | 13346 | OD2 | ASP | B | 314 | 47.809 | 14.501 | −35.924 | 1.00 | 42.75 | B | O |
| ATOM | 13347 | C | ASP | B | 314 | 44.529 | 12.699 | −35.409 | 1.00 | 26.37 | B | C |
| ATOM | 13348 | O | ASP | B | 314 | 43.935 | 13.112 | −36.405 | 1.00 | 24.33 | B | O |
| ATOM | 13350 | N | VAL | B | 315 | 44.949 | 11.441 | −35.282 | 1.00 | 24.78 | B | N |
| ATOM | 13351 | CA | VAL | B | 315 | 44.922 | 10.484 | −36.415 | 1.00 | 25.23 | B | C |
| ATOM | 13353 | CB | VAL | B | 315 | 46.340 | 10.251 | −36.987 | 1.00 | 23.87 | B | C |
| ATOM | 13355 | CG1 | VAL | B | 315 | 46.851 | 11.532 | −37.688 | 1.00 | 27.00 | B | C |
| ATOM | 13359 | CG2 | VAL | B | 315 | 47.289 | 9.792 | −35.902 | 1.00 | 22.09 | B | C |
| ATOM | 13363 | C | VAL | B | 315 | 44.305 | 9.096 | −36.185 | 1.00 | 25.17 | B | C |
| ATOM | 13364 | O | VAL | B | 315 | 43.729 | 8.544 | −37.109 | 1.00 | 27.94 | B | O |
| ATOM | 13366 | N | TYR | B | 316 | 44.426 | 8.520 | −34.993 | 1.00 | 24.11 | B | N |
| ATOM | 13367 | CA | TYR | B | 316 | 44.020 | 7.122 | −34.779 | 1.00 | 23.73 | B | C |
| ATOM | 13369 | CB | TYR | B | 316 | 44.867 | 6.522 | −33.672 | 1.00 | 25.65 | B | C |
| ATOM | 13372 | CG | TYR | B | 316 | 44.824 | 5.019 | −33.620 | 1.00 | 27.69 | B | C |
| ATOM | 13373 | CD1 | TYR | B | 316 | 45.597 | 4.235 | −34.499 | 1.00 | 25.15 | B | C |
| ATOM | 13375 | CE1 | TYR | B | 316 | 45.550 | 2.814 | −34.447 | 1.00 | 25.74 | B | C |
| ATOM | 13377 | CZ | TYR | B | 316 | 44.740 | 2.208 | −33.503 | 1.00 | 24.05 | B | C |
| ATOM | 13378 | OH | TYR | B | 316 | 44.669 | 0.862 | −33.392 | 1.00 | 25.86 | B | O |
| ATOM | 13380 | CE2 | TYR | B | 316 | 43.966 | 2.972 | −32.630 | 1.00 | 31.18 | B | C |
| ATOM | 13382 | CD2 | TYR | B | 316 | 44.012 | 4.368 | −32.692 | 1.00 | 27.68 | B | C |
| ATOM | 13384 | C | TYR | B | 316 | 42.540 | 6.883 | −34.427 | 1.00 | 23.79 | B | C |
| ATOM | 13385 | O | TYR | B | 316 | 41.897 | 5.976 | −34.977 | 1.00 | 23.24 | B | O |
| ATOM | 13387 | N | GLY | B | 317 | 41.999 | 7.665 | −33.502 | 1.00 | 21.86 | B | N |
| ATOM | 13388 | CA | GLY | B | 317 | 40.677 | 7.383 | −32.966 | 1.00 | 20.83 | B | C |
| ATOM | 13391 | C | GLY | B | 317 | 39.577 | 7.917 | −33.858 | 1.00 | 23.66 | B | C |
| ATOM | 13392 | O | GLY | B | 317 | 39.701 | 9.008 | −34.444 | 1.00 | 21.52 | B | O |
| ATOM | 13394 | N | THR | B | 318 | 38.490 | 7.152 | −33.975 | 1.00 | 22.28 | B | N |
| ATOM | 13395 | CA | THR | B | 318 | 37.315 | 7.674 | −34.607 | 1.00 | 22.27 | B | C |
| ATOM | 13397 | CB | THR | B | 318 | 36.314 | 6.564 | −34.989 | 1.00 | 23.50 | B | C |
| ATOM | 13399 | OG1 | THR | B | 318 | 35.746 | 6.006 | −33.803 | 1.00 | 25.49 | B | O |
| ATOM | 13401 | CG2 | THR | B | 318 | 37.006 | 5.456 | −35.807 | 1.00 | 21.97 | B | C |
| ATOM | 13405 | C | THR | B | 318 | 36.625 | 8.610 | −33.638 | 1.00 | 23.75 | B | C |
| ATOM | 13406 | O | THR | B | 318 | 36.823 | 8.542 | −32.412 | 1.00 | 23.62 | B | O |
| ATOM | 13408 | N | LEU | B | 319 | 35.757 | 9.446 | −34.189 | 1.00 | 22.45 | B | N |
| ATOM | 13409 | CA | LEU | B | 319 | 35.009 | 10.398 | −33.393 | 1.00 | 24.74 | B | C |
| ATOM | 13411 | CB | LEU | B | 319 | 34.040 | 11.176 | −34.274 | 1.00 | 24.05 | B | C |
| ATOM | 13414 | CG | LEU | B | 319 | 33.903 | 12.670 | −34.012 | 1.00 | 34.66 | B | C |
| ATOM | 13416 | CD1 | LEU | B | 319 | 35.268 | 13.345 | −33.825 | 1.00 | 22.94 | B | C |
| ATOM | 13420 | CD2 | LEU | B | 319 | 33.063 | 13.338 | −35.150 | 1.00 | 33.27 | B | C |
| ATOM | 13424 | C | LEU | B | 319 | 34.273 | 9.736 | −32.238 | 1.00 | 24.81 | B | C |
| ATOM | 13425 | O | LEU | B | 319 | 34.300 | 10.224 | −31.127 | 1.00 | 27.70 | B | O |
| ATOM | 13427 | N | ASP | B | 320 | 33.637 | 8.605 | −32.498 | 1.00 | 26.74 | B | N |
| ATOM | 13428 | CA | ASP | B | 320 | 32.910 | 7.881 | −31.469 | 1.00 | 26.27 | B | C |
| ATOM | 13430 | CB | ASP | B | 320 | 32.192 | 6.650 | −32.064 | 1.00 | 29.58 | B | C |
| ATOM | 13433 | CG | ASP | B | 320 | 30.855 | 6.977 | −32.760 | 1.00 | 35.82 | B | C |
| ATOM | 13434 | OD1 | ASP | B | 320 | 30.397 | 8.145 | −32.767 | 1.00 | 38.73 | B | O |
| ATOM | 13435 | OD2 | ASP | B | 320 | 30.261 | 6.018 | −33.315 | 1.00 | 45.55 | B | O |
| ATOM | 13436 | C | ASP | B | 320 | 33.857 | 7.413 | −30.361 | 1.00 | 23.93 | B | C |
| ATOM | 13437 | O | ASP | B | 320 | 33.509 | 7.435 | −29.199 | 1.00 | 23.76 | B | O |
| ATOM | 13439 | N | GLU | B | 321 | 35.044 | 6.951 | −30.724 | 1.00 | 23.54 | B | N |
| ATOM | 13440 | CA | GLU | B | 321 | 35.977 | 6.478 | −29.721 | 1.00 | 22.08 | B | C |
| ATOM | 13442 | CB | GLU | B | 321 | 37.129 | 5.748 | −30.378 | 1.00 | 21.78 | B | C |
| ATOM | 13445 | CG | GLU | B | 321 | 36.748 | 4.435 | −31.077 | 1.00 | 21.27 | B | C |
| ATOM | 13448 | CD | GLU | B | 321 | 37.959 | 3.809 | −31.762 | 1.00 | 25.99 | B | C |
| ATOM | 13449 | OE1 | GLU | B | 321 | 38.908 | 4.571 | −32.114 | 1.00 | 24.28 | B | O |
| ATOM | 13450 | OE2 | GLU | B | 321 | 37.983 | 2.569 | −31.922 | 1.00 | 26.77 | B | O |
| ATOM | 13451 | C | GLU | B | 321 | 36.506 | 7.668 | −28.909 | 1.00 | 22.57 | B | C |
| ATOM | 13452 | O | GLU | B | 321 | 36.761 | 7.548 | −27.714 | 1.00 | 21.71 | B | O |
| ATOM | 13454 | N | LEU | B | 322 | 36.665 | 8.813 | −29.569 | 1.00 | 21.65 | B | N |
| ATOM | 13455 | CA | LEU | B | 322 | 37.187 | 9.993 | −28.909 | 1.00 | 22.06 | B | C |
| ATOM | 13457 | CB | LEU | B | 322 | 37.611 | 11.059 | −29.909 | 1.00 | 20.94 | B | C |
| ATOM | 13460 | CG | LEU | B | 322 | 38.692 | 10.615 | −30.885 | 1.00 | 20.78 | B | C |
| ATOM | 13462 | CD1 | LEU | B | 322 | 38.999 | 11.683 | −31.924 | 1.00 | 17.20 | B | C |
| ATOM | 13466 | CD2 | LEU | B | 322 | 39.949 | 10.199 | −30.146 | 1.00 | 17.86 | B | C |
| ATOM | 13470 | C | LEU | B | 322 | 36.169 | 10.546 | −27.927 | 1.00 | 23.46 | B | C |
| ATOM | 13471 | O | LEU | B | 322 | 36.555 | 11.005 | −26.852 | 1.00 | 24.73 | B | O |
| ATOM | 13473 | N | GLU | B | 323 | 34.880 | 10.460 | −28.243 | 1.00 | 21.53 | B | N |
| ATOM | 13474 | CA | GLU | B | 323 | 33.875 | 10.850 | −27.261 | 1.00 | 23.97 | B | C |
| ATOM | 13476 | CB | GLU | B | 323 | 32.469 | 10.840 | −27.851 | 1.00 | 26.47 | B | C |
| ATOM | 13479 | CG | GLU | B | 323 | 32.292 | 11.810 | −29.011 | 1.00 | 31.79 | B | C |
| ATOM | 13482 | CD | GLU | B | 323 | 31.723 | 13.145 | −28.600 | 1.00 | 39.43 | B | C |

TABLE 4-2-continued

| Coordinates of *P. alba* IspS | | | | | | | | | | | |
|---|---|---|---|---|---|---|---|---|---|---|---|
| ATOM | 13483 | OE1 | GLU | B | 323 | 31.263 | 13.876 | −29.515 | 1.00 | 44.91 | B | O |
| ATOM | 13484 | OE2 | GLU | B | 323 | 31.713 | 13.459 | −27.383 | 1.00 | 40.00 | B | O |
| ATOM | 13485 | C | GLU | B | 323 | 33.930 | 9.940 | −26.030 | 1.00 | 24.87 | B | C |
| ATOM | 13486 | O | GLU | B | 323 | 33.810 | 10.409 | −24.899 | 1.00 | 23.87 | B | O |
| ATOM | 13488 | N | LEU | B | 324 | 34.129 | 8.643 | −26.238 | 1.00 | 24.68 | B | N |
| ATOM | 13489 | CA | LEU | B | 324 | 34.224 | 7.719 | −25.099 | 1.00 | 24.65 | B | C |
| ATOM | 13491 | CB | LEU | B | 324 | 34.330 | 6.249 | −25.566 | 1.00 | 25.50 | B | C |
| ATOM | 13494 | CG | LEU | B | 324 | 33.033 | 5.612 | −26.107 | 1.00 | 31.61 | B | C |
| ATOM | 13496 | CD1 | LEU | B | 324 | 33.328 | 4.286 | −26.843 | 1.00 | 26.20 | B | C |
| ATOM | 13500 | CD2 | LEU | B | 324 | 32.020 | 5.401 | −24.966 | 1.00 | 29.59 | B | C |
| ATOM | 13504 | C | LEU | B | 324 | 35.403 | 8.054 | −24.199 | 1.00 | 22.74 | B | C |
| ATOM | 13505 | O | LEU | B | 324 | 35.294 | 7.976 | −22.983 | 1.00 | 22.76 | B | O |
| ATOM | 13507 | N | PHE | B | 325 | 36.539 | 8.406 | −24.794 | 1.00 | 21.75 | B | N |
| ATOM | 13508 | CA | PHE | B | 325 | 37.765 | 8.651 | −24.017 | 1.00 | 19.99 | B | C |
| ATOM | 13510 | CB | PHE | B | 325 | 38.977 | 8.726 | −24.943 | 1.00 | 18.14 | B | C |
| ATOM | 13513 | CG | PHE | B | 325 | 40.293 | 8.727 | −24.222 | 1.00 | 20.43 | B | C |
| ATOM | 13514 | CD1 | PHE | B | 325 | 40.921 | 7.542 | −23.911 | 1.00 | 20.73 | B | C |
| ATOM | 13516 | CE1 | PHE | B | 325 | 42.133 | 7.529 | −23.250 | 1.00 | 18.54 | B | C |
| ATOM | 13518 | CZ | PHE | B | 325 | 42.741 | 8.712 | −22.890 | 1.00 | 18.75 | B | C |
| ATOM | 13520 | CE2 | PHE | B | 325 | 42.129 | 9.912 | −23.189 | 1.00 | 29.13 | B | C |
| ATOM | 13522 | CD2 | PHE | B | 325 | 40.901 | 9.918 | −23.855 | 1.00 | 20.29 | B | C |
| ATOM | 13524 | C | PHE | B | 325 | 37.660 | 9.930 | −23.215 | 1.00 | 19.39 | B | C |
| ATOM | 13525 | O | PHE | B | 325 | 38.067 | 9.999 | −22.050 | 1.00 | 21.89 | B | O |
| ATOM | 13527 | N | THR | B | 326 | 37.153 | 10.956 | −23.872 | 1.00 | 20.85 | B | N |
| ATOM | 13528 | CA | THR | B | 326 | 36.929 | 12.251 | −23.274 | 1.00 | 21.29 | B | C |
| ATOM | 13530 | CB | THR | B | 326 | 36.274 | 13.175 | −24.300 | 1.00 | 22.64 | B | C |
| ATOM | 13532 | OG1 | THR | B | 326 | 37.159 | 13.340 | −25.420 | 1.00 | 21.93 | B | O |
| ATOM | 13534 | CG2 | THR | B | 326 | 35.978 | 14.532 | −23.685 | 1.00 | 15.42 | B | C |
| ATOM | 13538 | C | THR | B | 326 | 36.034 | 12.107 | −22.056 | 1.00 | 21.59 | B | C |
| ATOM | 13539 | O | THR | B | 326 | 36.334 | 12.624 | −21.006 | 1.00 | 22.13 | B | O |
| ATOM | 13541 | N | ASP | B | 327 | 34.952 | 11.363 | −22.213 | 1.00 | 25.12 | B | N |
| ATOM | 13542 | CA | ASP | B | 327 | 33.991 | 11.091 | −21.144 | 1.00 | 24.52 | B | C |
| ATOM | 13544 | CB | ASP | B | 327 | 32.805 | 10.309 | −21.729 | 1.00 | 26.23 | B | C |
| ATOM | 13547 | CG | ASP | B | 327 | 31.880 | 9.726 | −20.654 | 1.00 | 35.17 | B | C |
| ATOM | 13548 | OD1 | ASP | B | 327 | 31.041 | 10.485 | −20.095 | 1.00 | 38.22 | B | O |
| ATOM | 13549 | OD2 | ASP | B | 327 | 31.994 | 8.499 | −20.370 | 1.00 | 41.20 | B | O |
| ATOM | 13550 | C | ASP | B | 327 | 34.635 | 10.320 | −20.002 | 1.00 | 24.61 | B | C |
| ATOM | 13551 | O | ASP | B | 327 | 34.422 | 10.642 | −18.824 | 1.00 | 25.19 | B | O |
| ATOM | 13553 | N | ALA | B | 328 | 35.440 | 9.313 | −20.339 | 1.00 | 22.67 | B | N |
| ATOM | 13554 | CA | ALA | B | 328 | 36.152 | 8.535 | −19.326 | 1.00 | 21.90 | B | C |
| ATOM | 13556 | CB | ALA | B | 328 | 36.923 | 7.388 | −19.966 | 1.00 | 21.68 | B | C |
| ATOM | 13560 | C | ALA | B | 328 | 37.102 | 9.399 | −18.487 | 1.00 | 21.10 | B | C |
| ATOM | 13561 | O | ALA | B | 328 | 37.245 | 9.183 | −17.287 | 1.00 | 20.62 | B | O |
| ATOM | 13563 | N | VAL | B | 329 | 37.762 | 10.356 | −19.118 | 1.00 | 18.66 | B | N |
| ATOM | 13564 | CA | VAL | B | 329 | 38.652 | 11.232 | −18.405 | 1.00 | 18.17 | B | C |
| ATOM | 13566 | CB | VAL | B | 329 | 39.547 | 12.030 | −19.362 | 1.00 | 18.54 | B | C |
| ATOM | 13568 | CG1 | VAL | B | 329 | 40.599 | 11.070 | −20.002 | 1.00 | 20.31 | B | C |
| ATOM | 13572 | CG2 | VAL | B | 329 | 40.267 | 13.148 | −18.630 | 1.00 | 16.84 | B | C |
| ATOM | 13576 | C | VAL | B | 329 | 37.841 | 12.144 | −17.498 | 1.00 | 22.27 | B | C |
| ATOM | 13577 | O | VAL | B | 329 | 38.210 | 12.343 | −16.342 | 1.00 | 24.05 | B | O |
| ATOM | 13579 | N | GLU | B | 330 | 36.725 | 12.664 | −17.999 | 1.00 | 22.49 | B | N |
| ATOM | 13580 | CA | GLU | B | 330 | 35.830 | 13.499 | −17.185 | 1.00 | 24.53 | B | C |
| ATOM | 13582 | CB | GLU | B | 330 | 34.638 | 14.006 | −18.032 | 1.00 | 23.64 | B | C |
| ATOM | 13585 | CG | GLU | B | 330 | 35.054 | 15.060 | −19.039 | 1.00 | 29.46 | B | C |
| ATOM | 13588 | CD | GLU | B | 330 | 33.972 | 15.467 | −20.043 | 1.00 | 36.72 | B | C |
| ATOM | 13589 | OE1 | GLU | B | 330 | 34.141 | 16.536 | −20.688 | 1.00 | 38.15 | B | O |
| ATOM | 13590 | OE2 | GLU | B | 330 | 32.969 | 14.739 | −20.205 | 1.00 | 39.50 | B | O |
| ATOM | 13591 | C | GLU | B | 330 | 35.321 | 12.765 | −15.952 | 1.00 | 25.12 | B | C |
| ATOM | 13592 | O | GLU | B | 330 | 35.371 | 13.295 | −14.850 | 1.00 | 24.76 | B | O |
| ATOM | 13594 | N | ARG | B | 331 | 34.843 | 11.537 | −16.129 | 1.00 | 26.13 | B | N |
| ATOM | 13595 | CA | AARG | B | 331 | 34.264 | 10.779 | −15.016 | 0.50 | 25.43 | B | C |
| ATOM | 13596 | CA | BARG | B | 331 | 34.261 | 10.787 | −15.019 | 0.50 | 25.52 | B | C |
| ATOM | 13599 | CB | AARG | B | 331 | 33.385 | 9.643 | −15.539 | 0.50 | 25.68 | B | C |
| ATOM | 13600 | CB | BARG | B | 331 | 33.350 | 9.683 | −15.563 | 0.50 | 25.87 | B | C |
| ATOM | 13605 | CG | AARG | B | 331 | 32.054 | 10.133 | −16.144 | 0.50 | 29.23 | B | C |
| ATOM | 13606 | CG | BARG | B | 331 | 32.115 | 10.255 | −16.312 | 0.50 | 29.59 | B | C |
| ATOM | 13611 | CD | AARG | B | 331 | 31.197 | 8.990 | −16.686 | 0.50 | 32.54 | B | C |
| ATOM | 13612 | CD | BARG | B | 331 | 31.212 | 9.190 | −16.943 | 0.50 | 32.56 | B | C |
| ATOM | 13617 | NE | AARG | B | 331 | 32.007 | 8.014 | −17.403 | 0.50 | 39.07 | B | N |
| ATOM | 13618 | NE | BARG | B | 331 | 30.097 | 9.778 | −17.691 | 0.50 | 37.34 | B | N |
| ATOM | 13621 | CZ | AARG | B | 331 | 32.223 | 6.766 | −17.000 | 0.50 | 36.77 | B | C |
| ATOM | 13622 | CZ | BARG | B | 331 | 28.967 | 10.208 | −17.135 | 0.50 | 40.94 | B | C |
| ATOM | 13623 | NH1 | AARG | B | 331 | 31.656 | 6.300 | −15.886 | 0.50 | 38.70 | B | N |
| ATOM | 13624 | NH1 | BARG | B | 331 | 28.782 | 10.113 | −15.825 | 0.50 | 38.56 | B | N |
| ATOM | 13629 | NH2 | AARG | B | 331 | 32.998 | 5.985 | −17.733 | 0.50 | 33.12 | B | N |
| ATOM | 13630 | NH2 | BARG | B | 331 | 28.016 | 10.734 | −17.891 | 0.50 | 39.98 | B | N |
| ATOM | 13635 | C | ARG | B | 331 | 35.327 | 10.245 | −14.044 | 1.00 | 25.39 | B | C |
| ATOM | 13636 | O | ARG | B | 331 | 35.081 | 10.116 | −12.841 | 1.00 | 23.54 | B | O |

TABLE 4-2-continued

Coordinates of *P. alba* IspS

| | | | | | | | | | | | | |
|---|---|---|---|---|---|---|---|---|---|---|---|---|
| ATOM | 13638 | N | TRP | B | 332 | 36.509 | 9.935 | −14.559 | 1.00 | 24.49 | B | N |
| ATOM | 13639 | CA | TRP | B | 332 | 37.622 | 9.451 | −13.737 | 1.00 | 22.84 | B | C |
| ATOM | 13641 | CB | TRP | B | 332 | 38.153 | 10.576 | −12.838 | 1.00 | 19.58 | B | C |
| ATOM | 13644 | CG | TRP | B | 332 | 39.557 | 10.379 | −12.453 | 1.00 | 19.36 | B | C |
| ATOM | 13645 | CD1 | TRP | B | 332 | 40.027 | 9.997 | −11.234 | 1.00 | 18.47 | B | C |
| ATOM | 13647 | NE1 | TRP | B | 332 | 41.393 | 9.903 | −11.264 | 1.00 | 21.06 | B | N |
| ATOM | 13649 | CE2 | TRP | B | 332 | 41.831 | 10.202 | −12.524 | 1.00 | 17.15 | B | C |
| ATOM | 13650 | CD2 | TRP | B | 332 | 40.701 | 10.503 | −13.302 | 1.00 | 20.00 | B | C |
| ATOM | 13651 | CE3 | TRP | B | 332 | 40.875 | 10.827 | −14.648 | 1.00 | 16.76 | B | C |
| ATOM | 13653 | CZ3 | TRP | B | 332 | 42.149 | 10.869 | −15.154 | 1.00 | 18.63 | B | C |
| ATOM | 13655 | CH2 | TRP | B | 332 | 43.257 | 10.567 | −14.354 | 1.00 | 21.96 | B | C |
| ATOM | 13657 | CZ2 | TRP | B | 332 | 43.115 | 10.241 | −13.033 | 1.00 | 23.99 | B | C |
| ATOM | 13659 | C | TRP | B | 332 | 37.252 | 8.223 | −12.919 | 1.00 | 21.89 | B | C |
| ATOM | 13660 | O | TRP | B | 332 | 37.517 | 8.160 | −11.715 | 1.00 | 21.86 | B | O |
| ATOM | 13662 | N | ASP | B | 333 | 36.660 | 7.240 | −13.591 | 1.00 | 22.25 | B | N |
| ATOM | 13663 | CA | ASP | B | 333 | 36.126 | 6.051 | −12.932 | 1.00 | 24.19 | B | C |
| ATOM | 13665 | CB | ASP | B | 333 | 34.598 | 5.972 | −13.154 | 1.00 | 24.72 | B | C |
| ATOM | 13668 | CG | ASP | B | 333 | 33.947 | 4.754 | −12.473 | 1.00 | 28.67 | B | C |
| ATOM | 13669 | OD1 | ASP | B | 333 | 34.580 | 4.096 | −11.612 | 1.00 | 32.90 | B | O |
| ATOM | 13670 | OD2 | ASP | B | 333 | 32.773 | 4.466 | −12.795 | 1.00 | 34.32 | B | O |
| ATOM | 13671 | C | ASP | B | 333 | 36.796 | 4.790 | −13.490 | 1.00 | 24.39 | B | C |
| ATOM | 13672 | O | ASP | B | 333 | 36.486 | 4.352 | −14.599 | 1.00 | 23.16 | B | O |
| ATOM | 13674 | N | VAL | B | 334 | 37.673 | 4.183 | −12.699 | 1.00 | 24.63 | B | N |
| ATOM | 13675 | CA | VAL | B | 334 | 38.392 | 3.011 | −13.157 | 1.00 | 25.01 | B | C |
| ATOM | 13677 | CB | VAL | B | 334 | 39.571 | 2.670 | −12.260 | 1.00 | 24.07 | B | C |
| ATOM | 13679 | CG1 | VAL | B | 334 | 40.484 | 1.692 | −12.972 | 1.00 | 22.74 | B | C |
| ATOM | 13683 | CG2 | VAL | B | 334 | 39.094 | 2.132 | −10.916 | 1.00 | 22.48 | B | C |
| ATOM | 13687 | C | VAL | B | 334 | 37.471 | 1.805 | −13.298 | 1.00 | 28.84 | B | C |
| ATOM | 13688 | O | VAL | B | 334 | 37.724 | 0.960 | −14.132 | 1.00 | 30.66 | B | O |
| ATOM | 13690 | N | ASN | B | 335 | 36.384 | 1.751 | −12.530 | 1.00 | 30.57 | B | N |
| ATOM | 13691 | CA | ASN | B | 335 | 35.396 | 0.670 | −12.667 | 1.00 | 32.76 | B | C |
| ATOM | 13693 | CB | ASN | B | 335 | 34.426 | 0.659 | −11.474 | 1.00 | 32.97 | B | C |
| ATOM | 13696 | CG | ASN | B | 335 | 35.150 | 0.526 | −10.136 | 1.00 | 36.11 | B | C |
| ATOM | 13697 | OD1 | ASN | B | 335 | 35.846 | −0.464 | −9.891 | 1.00 | 32.01 | B | O |
| ATOM | 13698 | ND2 | ASN | B | 335 | 35.002 | 1.537 | −9.272 | 1.00 | 31.45 | B | N |
| ATOM | 13701 | C | ASN | B | 335 | 34.595 | 0.714 | −13.973 | 1.00 | 33.61 | B | C |
| ATOM | 13702 | O | ASN | B | 335 | 33.783 | −0.158 | −14.187 | 1.00 | 32.20 | B | O |
| ATOM | 13704 | N | ALA | B | 336 | 34.819 | 1.725 | −14.821 | 1.00 | 35.40 | B | N |
| ATOM | 13705 | CA | ALA | B | 336 | 34.165 | 1.832 | −16.139 | 1.00 | 37.44 | B | C |
| ATOM | 13707 | CB | ALA | B | 336 | 33.391 | 3.153 | −16.239 | 1.00 | 36.12 | B | C |
| ATOM | 13711 | C | ALA | B | 336 | 35.147 | 1.708 | −17.306 | 1.00 | 37.97 | B | C |
| ATOM | 13712 | O | ALA | B | 336 | 34.797 | 1.970 | −18.451 | 1.00 | 40.52 | B | O |
| ATOM | 13714 | N | ILE | B | 337 | 36.371 | 1.291 | −17.006 | 1.00 | 39.74 | B | N |
| ATOM | 13715 | CA | ILE | B | 337 | 37.417 | 1.027 | −18.010 | 1.00 | 39.19 | B | C |
| ATOM | 13717 | CB | ILE | B | 337 | 38.706 | 0.448 | −17.308 | 1.00 | 40.69 | B | C |
| ATOM | 13719 | CG1 | ILE | B | 337 | 39.903 | 0.392 | −18.237 | 1.00 | 45.92 | B | C |
| ATOM | 13722 | CD1 | ILE | B | 337 | 41.134 | −0.183 | −17.566 | 1.00 | 45.35 | B | C |
| ATOM | 13726 | CG2 | ILE | B | 337 | 38.488 | −0.946 | −16.773 | 1.00 | 38.80 | B | C |
| ATOM | 13730 | C | ILE | B | 337 | 36.959 | 0.093 | −19.138 | 1.00 | 39.32 | B | C |
| ATOM | 13731 | O | ILE | B | 337 | 37.385 | 0.260 | −20.278 | 1.00 | 39.83 | B | O |
| ATOM | 13733 | N | ASN | B | 338 | 36.080 | −0.866 | −18.837 | 1.00 | 37.82 | B | N |
| ATOM | 13734 | CA | ASN | B | 338 | 35.609 | −1.831 | −19.854 | 1.00 | 38.11 | B | C |
| ATOM | 13736 | CB | ASN | B | 338 | 34.944 | −3.076 | −19.201 | 1.00 | 37.75 | B | C |
| ATOM | 13739 | CG | ASN | B | 338 | 35.970 | −4.092 | −18.627 | 1.00 | 38.84 | B | C |
| ATOM | 13740 | OD1 | ASN | B | 338 | 37.163 | −4.064 | −18.937 | 1.00 | 33.79 | B | O |
| ATOM | 13741 | ND2 | ASN | B | 338 | 35.479 | −5.010 | −17.801 | 1.00 | 36.06 | B | N |
| ATOM | 13744 | C | ASN | B | 338 | 34.705 | −1.253 | −20.973 | 1.00 | 36.95 | B | C |
| ATOM | 13745 | O | ASN | B | 338 | 34.464 | −1.915 | −21.965 | 1.00 | 36.60 | B | O |
| ATOM | 13747 | N | ASP | B | 339 | 34.243 | −0.019 | −20.839 | 1.00 | 37.98 | B | N |
| ATOM | 13748 | CA | ASP | B | 339 | 33.479 | 0.647 | −21.920 | 1.00 | 38.56 | B | C |
| ATOM | 13750 | CB | ASP | B | 339 | 32.804 | 1.938 | −21.394 | 1.00 | 40.02 | B | C |
| ATOM | 13753 | CG | ASP | B | 339 | 31.899 | 1.706 | −20.161 | 1.00 | 44.52 | B | C |
| ATOM | 13754 | OD1 | ASP | B | 339 | 31.430 | 0.568 | −19.940 | 1.00 | 49.31 | B | O |
| ATOM | 13755 | OD2 | ASP | B | 339 | 31.641 | 2.690 | −19.430 | 1.00 | 45.68 | B | O |
| ATOM | 13756 | C | ASP | B | 339 | 34.381 | 1.036 | −23.110 | 1.00 | 34.68 | B | C |
| ATOM | 13757 | O | ASP | B | 339 | 33.918 | 1.279 | −24.221 | 1.00 | 34.99 | B | O |
| ATOM | 13759 | N | LEU | B | 340 | 35.674 | 1.116 | −22.855 | 1.00 | 31.43 | B | N |
| ATOM | 13760 | CA | LEU | B | 340 | 36.619 | 1.597 | −23.846 | 1.00 | 29.09 | B | C |
| ATOM | 13762 | CB | LEU | B | 340 | 37.803 | 2.257 | −23.138 | 1.00 | 27.62 | B | C |
| ATOM | 13765 | CG | LEU | B | 340 | 37.483 | 3.472 | −22.279 | 1.00 | 26.44 | B | C |
| ATOM | 13767 | CD1 | LEU | B | 340 | 38.682 | 3.873 | −21.426 | 1.00 | 20.10 | B | C |
| ATOM | 13771 | CD2 | LEU | B | 340 | 37.050 | 4.595 | −23.174 | 1.00 | 24.57 | B | C |
| ATOM | 13775 | C | LEU | B | 340 | 37.145 | 0.464 | −24.725 | 1.00 | 25.95 | B | C |
| ATOM | 13776 | O | LEU | B | 340 | 37.281 | −0.666 | −24.260 | 1.00 | 26.50 | B | O |
| ATOM | 13778 | N | PRO | B | 341 | 37.472 | 0.773 | −25.984 | 1.00 | 24.08 | B | N |
| ATOM | 13779 | CA | PRO | B | 341 | 38.167 | −0.187 | −26.836 | 1.00 | 24.62 | B | C |
| ATOM | 13781 | CB | PRO | B | 341 | 38.191 | 0.493 | −28.218 | 1.00 | 24.85 | B | C |
| ATOM | 13784 | CG | PRO | B | 341 | 38.063 | 1.910 | −27.954 | 1.00 | 26.60 | B | C |

TABLE 4-2-continued

| Coordinates of *P. alba* IspS | | | | | | | | | | | | |
|---|---|---|---|---|---|---|---|---|---|---|---|---|
| ATOM | 13787 | CD | PRO | B | 341 | 37.281 | 2.065 | −26.661 | 1.00 | 25.30 | B | C |
| ATOM | 13790 | C | PRO | B | 341 | 39.564 | −0.443 | −26.320 | 1.00 | 23.26 | B | C |
| ATOM | 13791 | O | PRO | B | 341 | 40.103 | 0.360 | −25.544 | 1.00 | 21.32 | B | O |
| ATOM | 13792 | N | ASP | B | 342 | 40.134 | −1.571 | −26.725 | 1.00 | 23.87 | B | N |
| ATOM | 13793 | CA | ASP | B | 342 | 41.289 | −2.122 | −26.026 | 1.00 | 23.29 | B | C |
| ATOM | 13795 | CB | ASP | B | 342 | 41.767 | −3.425 | −26.696 | 1.00 | 25.56 | B | C |
| ATOM | 13798 | CG | ASP | B | 342 | 40.790 | −4.605 | −26.491 | 1.00 | 31.22 | B | C |
| ATOM | 13799 | OD1 | ASP | B | 342 | 39.943 | −4.549 | −25.566 | 1.00 | 32.95 | B | O |
| ATOM | 13800 | OD2 | ASP | B | 342 | 40.889 | −5.599 | −27.254 | 1.00 | 37.04 | B | O |
| ATOM | 13801 | C | ASP | B | 342 | 42.436 | −1.120 | −25.929 | 1.00 | 22.80 | B | C |
| ATOM | 13802 | O | ASP | B | 342 | 43.042 | −0.938 | −24.845 | 1.00 | 21.42 | B | O |
| ATOM | 13804 | N | TYR | B | 343 | 42.747 | −0.457 | −27.039 | 1.00 | 20.42 | B | N |
| ATOM | 13805 | CA | TYR | B | 343 | 43.912 | 0.428 | −27.038 | 1.00 | 20.57 | B | C |
| ATOM | 13807 | CB | TYR | B | 343 | 44.273 | 0.888 | −28.460 | 1.00 | 20.66 | B | C |
| ATOM | 13810 | CG | TYR | B | 343 | 43.398 | 1.977 | −29.041 | 1.00 | 23.23 | B | C |
| ATOM | 13811 | CD1 | TYR | B | 343 | 42.233 | 1.680 | −29.747 | 1.00 | 20.78 | B | C |
| ATOM | 13813 | CE1 | TYR | B | 343 | 41.441 | 2.700 | −30.274 | 1.00 | 26.89 | B | C |
| ATOM | 13815 | CZ | TYR | B | 343 | 41.836 | 4.026 | −30.103 | 1.00 | 23.64 | B | C |
| ATOM | 13816 | OH | TYR | B | 343 | 41.124 | 5.055 | −30.630 | 1.00 | 26.31 | B | O |
| ATOM | 13818 | CE2 | TYR | B | 343 | 42.993 | 4.332 | −29.437 | 1.00 | 22.44 | B | C |
| ATOM | 13820 | CD2 | TYR | B | 343 | 43.765 | 3.316 | −28.910 | 1.00 | 23.71 | B | C |
| ATOM | 13822 | C | TYR | B | 343 | 43.689 | 1.603 | −26.069 | 1.00 | 20.00 | B | C |
| ATOM | 13823 | O | TYR | B | 343 | 44.602 | 2.031 | −25.396 | 1.00 | 18.99 | B | O |
| ATOM | 13825 | N | MET | B | 344 | 42.459 | 2.080 | −25.966 | 1.00 | 20.82 | B | N |
| ATOM | 13826 | CA | MET | B | 344 | 42.145 | 3.158 | −25.030 | 1.00 | 20.77 | B | C |
| ATOM | 13828 | CB | MET | B | 344 | 40.819 | 3.806 | −25.392 | 1.00 | 20.51 | B | C |
| ATOM | 13831 | CG | MET | B | 344 | 40.953 | 4.773 | −26.564 | 1.00 | 21.38 | B | C |
| ATOM | 13834 | SD | MET | B | 344 | 39.418 | 5.528 | −27.088 | 1.00 | 22.33 | B | S |
| ATOM | 13835 | CE | MET | B | 344 | 40.022 | 6.860 | −28.132 | 1.00 | 16.19 | B | C |
| ATOM | 13839 | C | MET | B | 344 | 42.134 | 2.677 | −23.591 | 1.00 | 22.13 | B | C |
| ATOM | 13840 | O | MET | B | 344 | 42.497 | 3.420 | −22.682 | 1.00 | 20.90 | B | O |
| ATOM | 13842 | N | LYS | B | 345 | 41.731 | 1.427 | −23.402 | 1.00 | 23.38 | B | N |
| ATOM | 13843 | CA | LYS | B | 345 | 41.726 | 0.791 | −22.077 | 1.00 | 24.79 | B | C |
| ATOM | 13845 | CB | LYS | B | 345 | 41.476 | −0.712 | −22.211 | 1.00 | 27.00 | B | C |
| ATOM | 13848 | CG | LYS | B | 345 | 40.331 | −1.290 | −21.421 | 1.00 | 35.72 | B | C |
| ATOM | 13851 | CD | LYS | B | 345 | 39.732 | −2.426 | −22.257 | 1.00 | 37.84 | B | C |
| ATOM | 13854 | CE | LYS | B | 345 | 38.753 | −3.251 | −21.507 | 1.00 | 39.59 | B | C |
| ATOM | 13857 | NZ | LYS | B | 345 | 37.824 | −3.918 | −22.467 | 1.00 | 43.84 | B | N |
| ATOM | 13861 | C | LYS | B | 345 | 43.082 | 0.957 | −21.458 | 1.00 | 21.39 | B | C |
| ATOM | 13862 | O | LYS | B | 345 | 43.214 | 1.460 | −20.349 | 1.00 | 21.62 | B | O |
| ATOM | 13864 | N | LEU | B | 346 | 44.086 | 0.500 | −22.192 | 1.00 | 19.29 | B | N |
| ATOM | 13865 | CA | LEU | B | 346 | 45.449 | 0.496 | −21.723 | 1.00 | 20.97 | B | C |
| ATOM | 13867 | CB | LEU | B | 346 | 46.322 | −0.210 | −22.743 | 1.00 | 21.36 | B | C |
| ATOM | 13870 | CG | LEU | B | 346 | 47.675 | −0.639 | −22.223 | 1.00 | 23.78 | B | C |
| ATOM | 13872 | CD1 | LEU | B | 346 | 47.477 | −1.675 | −21.112 | 1.00 | 20.34 | B | C |
| ATOM | 13876 | CD2 | LEU | B | 346 | 48.444 | −1.253 | −23.370 | 1.00 | 27.71 | B | C |
| ATOM | 13880 | C | LEU | B | 346 | 45.958 | 1.908 | −21.486 | 1.00 | 21.00 | B | C |
| ATOM | 13881 | O | LEU | B | 346 | 46.523 | 2.225 | −20.433 | 1.00 | 21.92 | B | O |
| ATOM | 13883 | N | CYS | B | 347 | 45.753 | 2.763 | −22.469 | 1.00 | 19.96 | B | N |
| ATOM | 13884 | CA | CYS | B | 347 | 46.241 | 4.139 | −22.383 | 1.00 | 21.49 | B | C |
| ATOM | 13886 | CB | CYS | B | 347 | 45.945 | 4.847 | −23.725 | 1.00 | 23.29 | B | C |
| ATOM | 13889 | SG | CYS | B | 347 | 46.580 | 6.488 | −23.807 | 1.00 | 37.91 | B | S |
| ATOM | 13891 | C | CYS | B | 347 | 45.571 | 4.880 | −21.211 | 1.00 | 19.02 | B | C |
| ATOM | 13892 | O | CYS | B | 347 | 46.215 | 5.622 | −20.460 | 1.00 | 16.76 | B | O |
| ATOM | 13894 | N | PHE | B | 348 | 44.271 | 4.649 | −21.038 | 1.00 | 18.76 | B | N |
| ATOM | 13895 | CA | PHE | B | 348 | 43.529 | 5.306 | −19.983 | 1.00 | 18.67 | B | C |
| ATOM | 13897 | CB | PHE | B | 348 | 42.035 | 5.009 | −20.055 | 1.00 | 17.98 | B | C |
| ATOM | 13900 | CG | PHE | B | 348 | 41.269 | 5.635 | −18.939 | 1.00 | 17.07 | B | C |
| ATOM | 13901 | CD1 | PHE | B | 348 | 41.030 | 6.990 | −18.933 | 1.00 | 21.41 | B | C |
| ATOM | 13903 | CE1 | PHE | B | 348 | 40.352 | 7.592 | −17.885 | 1.00 | 23.96 | B | C |
| ATOM | 13905 | CZ | PHE | B | 348 | 39.939 | 6.844 | −16.815 | 1.00 | 21.12 | B | C |
| ATOM | 13907 | CE2 | PHE | B | 348 | 40.191 | 5.484 | −16.803 | 1.00 | 22.43 | B | C |
| ATOM | 13909 | CD2 | PHE | B | 348 | 40.867 | 4.894 | −17.855 | 1.00 | 21.94 | B | C |
| ATOM | 13911 | C | PHE | B | 348 | 44.032 | 4.868 | −18.616 | 1.00 | 18.84 | B | C |
| ATOM | 13912 | O | PHE | B | 348 | 44.286 | 5.700 | −17.738 | 1.00 | 17.72 | B | O |
| ATOM | 13914 | N | LEU | B | 349 | 44.174 | 3.562 | −18.429 | 1.00 | 17.46 | B | N |
| ATOM | 13915 | CA | LEU | B | 349 | 44.520 | 3.063 | −17.118 | 1.00 | 18.56 | B | C |
| ATOM | 13917 | CB | LEU | B | 349 | 44.388 | 1.545 | −17.053 | 1.00 | 19.12 | B | C |
| ATOM | 13920 | CG | LEU | B | 349 | 44.690 | 0.832 | −15.727 | 1.00 | 19.64 | B | C |
| ATOM | 13922 | CD1 | LEU | B | 349 | 44.000 | 1.519 | −14.535 | 1.00 | 13.56 | B | C |
| ATOM | 13926 | CD2 | LEU | B | 349 | 44.259 | −0.634 | −15.855 | 1.00 | 11.45 | B | C |
| ATOM | 13930 | C | LEU | B | 349 | 45.926 | 3.532 | −16.771 | 1.00 | 19.38 | B | C |
| ATOM | 13931 | O | LEU | B | 349 | 46.196 | 3.873 | −15.620 | 1.00 | 16.91 | B | O |
| ATOM | 13933 | N | ALA | B | 350 | 46.810 | 3.590 | −17.774 | 1.00 | 21.32 | B | N |
| ATOM | 13934 | CA | ALA | B | 350 | 48.189 | 4.094 | −17.560 | 1.00 | 20.38 | B | C |
| ATOM | 13936 | CB | ALA | B | 350 | 49.004 | 3.959 | −18.854 | 1.00 | 20.36 | B | C |
| ATOM | 13940 | C | ALA | B | 350 | 48.232 | 5.538 | −17.068 | 1.00 | 17.92 | B | C |
| ATOM | 13941 | O | ALA | B | 350 | 48.948 | 5.872 | −16.148 | 1.00 | 15.97 | B | O |

TABLE 4-2-continued

| Coordinates of *P. alba* IspS | | | | | | | | | | | | |
|---|---|---|---|---|---|---|---|---|---|---|---|---|
| ATOM | 13943 | N | LEU | B | 351 | 47.493 | 6.400 | −17.747 | 1.00 | 19.62 | B | N |
| ATOM | 13944 | CA | LEU | B | 351 | 47.334 | 7.796 | −17.357 | 1.00 | 18.33 | B | C |
| ATOM | 13946 | CB | LEU | B | 351 | 46.440 | 8.505 | −18.390 | 1.00 | 21.12 | B | C |
| ATOM | 13949 | CG | LEU | B | 351 | 46.123 | 9.988 | −18.131 | 1.00 | 23.41 | B | C |
| ATOM | 13951 | CD1 | LEU | B | 351 | 47.364 | 10.823 | −18.236 | 1.00 | 19.59 | B | C |
| ATOM | 13955 | CD2 | LEU | B | 351 | 45.052 | 10.462 | −19.098 | 1.00 | 22.85 | B | C |
| ATOM | 13959 | C | LEU | B | 351 | 46.694 | 7.924 | −15.972 | 1.00 | 18.87 | B | C |
| ATOM | 13960 | O | LEU | B | 351 | 47.165 | 8.709 | −15.117 | 1.00 | 19.16 | B | O |
| ATOM | 13962 | N | TYR | B | 352 | 45.604 | 7.176 | −15.780 | 1.00 | 16.72 | B | N |
| ATOM | 13963 | CA | TYR | B | 352 | 44.870 | 7.128 | −14.520 | 1.00 | 16.75 | B | C |
| ATOM | 13965 | CB | TYR | B | 352 | 43.799 | 6.040 | −14.614 | 1.00 | 18.50 | B | C |
| ATOM | 13968 | CG | TYR | B | 352 | 42.765 | 5.984 | −13.519 | 1.00 | 17.16 | B | C |
| ATOM | 13969 | CD1 | TYR | B | 352 | 41.688 | 6.868 | −13.514 | 1.00 | 22.74 | B | C |
| ATOM | 13971 | CE1 | TYR | B | 352 | 40.702 | 6.807 | −12.524 | 1.00 | 21.64 | B | C |
| ATOM | 13973 | CZ | TYR | B | 352 | 40.788 | 5.858 | −11.535 | 1.00 | 21.98 | B | C |
| ATOM | 13974 | OH | TYR | B | 352 | 39.800 | 5.795 | −10.560 | 1.00 | 25.58 | B | O |
| ATOM | 13976 | CE2 | TYR | B | 352 | 41.861 | 4.956 | −11.528 | 1.00 | 19.79 | B | C |
| ATOM | 13978 | CD2 | TYR | B | 352 | 42.828 | 5.022 | −12.524 | 1.00 | 17.06 | B | C |
| ATOM | 13980 | C | TYR | B | 352 | 45.801 | 6.835 | −13.363 | 1.00 | 16.79 | B | C |
| ATOM | 13981 | O | TYR | B | 352 | 45.874 | 7.601 | −12.384 | 1.00 | 17.65 | B | O |
| ATOM | 13983 | N | ASN | B | 353 | 46.534 | 5.734 | −13.460 | 1.00 | 16.33 | B | N |
| ATOM | 13984 | CA | ASN | B | 353 | 47.437 | 5.356 | −12.361 | 1.00 | 18.36 | B | C |
| ATOM | 13986 | CB | ASN | B | 353 | 48.058 | 3.995 | −12.629 | 1.00 | 15.27 | B | C |
| ATOM | 13989 | CG | ASN | B | 353 | 47.068 | 2.864 | −12.502 | 1.00 | 19.46 | B | C |
| ATOM | 13990 | OD1 | ASN | B | 353 | 45.965 | 3.037 | −11.982 | 1.00 | 17.65 | B | O |
| ATOM | 13991 | ND2 | ASN | B | 353 | 47.463 | 1.677 | −12.969 | 1.00 | 15.56 | B | N |
| ATOM | 13994 | C | ASN | B | 353 | 48.538 | 6.420 | −12.127 | 1.00 | 18.63 | B | C |
| ATOM | 13995 | O | ASN | B | 353 | 48.930 | 6.688 | −10.994 | 1.00 | 13.58 | B | O |
| ATOM | 13997 | N | THR | B | 354 | 49.012 | 7.047 | −13.210 | 1.00 | 19.49 | B | N |
| ATOM | 13998 | CA | THR | B | 354 | 50.102 | 7.999 | −13.110 | 1.00 | 17.67 | B | C |
| ATOM | 14000 | CB | THR | B | 354 | 50.610 | 8.406 | −14.501 | 1.00 | 20.08 | B | C |
| ATOM | 14002 | OG1 | THR | B | 354 | 51.004 | 7.243 | −15.238 | 1.00 | 18.36 | B | O |
| ATOM | 14004 | CG2 | THR | B | 354 | 51.789 | 9.381 | −14.389 | 1.00 | 17.15 | B | C |
| ATOM | 14008 | C | THR | B | 354 | 49.634 | 9.239 | −12.347 | 1.00 | 18.15 | B | C |
| ATOM | 14009 | O | THR | B | 354 | 50.316 | 9.713 | −11.462 | 1.00 | 18.88 | B | O |
| ATOM | 14011 | N | ILE | B | 355 | 48.454 | 9.728 | −12.694 | 1.00 | 16.69 | B | N |
| ATOM | 14012 | CA | ILE | B | 355 | 47.908 | 10.920 | −12.095 | 1.00 | 17.85 | B | C |
| ATOM | 14014 | CB | ILE | B | 355 | 46.657 | 11.416 | −12.875 | 1.00 | 18.34 | B | C |
| ATOM | 14016 | CG1 | ILE | B | 355 | 46.999 | 11.833 | −14.317 | 1.00 | 21.17 | B | C |
| ATOM | 14019 | CD1 | ILE | B | 355 | 48.356 | 12.354 | −14.519 | 1.00 | 25.46 | B | C |
| ATOM | 14023 | CG2 | ILE | B | 355 | 45.993 | 12.558 | −12.164 | 1.00 | 19.09 | B | C |
| ATOM | 14027 | C | ILE | B | 355 | 47.550 | 10.632 | −10.630 | 1.00 | 17.55 | B | C |
| ATOM | 14028 | O | ILE | B | 355 | 47.954 | 11.376 | −9.729 | 1.00 | 14.98 | B | O |
| ATOM | 14030 | N | ASN | B | 356 | 46.806 | 9.557 | −10.387 | 1.00 | 17.07 | B | N |
| ATOM | 14031 | CA | ASN | B | 356 | 46.532 | 9.152 | −9.008 | 1.00 | 18.16 | B | C |
| ATOM | 14033 | CB | ASN | B | 356 | 45.687 | 7.874 | −8.941 | 1.00 | 17.23 | B | C |
| ATOM | 14036 | CG | ASN | B | 356 | 44.314 | 8.080 | −9.531 | 1.00 | 17.52 | B | C |
| ATOM | 14037 | OD1 | ASN | B | 356 | 43.925 | 9.217 | −9.798 | 1.00 | 25.68 | B | O |
| ATOM | 14038 | ND2 | ASN | B | 356 | 43.592 | 7.004 | −9.782 | 1.00 | 19.09 | B | N |
| ATOM | 14041 | C | ASN | B | 356 | 47.783 | 9.003 | −8.161 | 1.00 | 19.24 | B | C |
| ATOM | 14042 | O | ASN | B | 356 | 47.765 | 9.283 | −6.975 | 1.00 | 22.07 | B | O |
| ATOM | 14044 | N | GLU | B | 357 | 48.885 | 8.596 | −8.752 | 1.00 | 21.23 | B | N |
| ATOM | 14045 | CA | GLU | B | 357 | 50.112 | 8.425 | −7.967 | 1.00 | 19.96 | B | C |
| ATOM | 14047 | CB | GLU | B | 357 | 51.064 | 7.495 | −8.708 | 1.00 | 18.90 | B | C |
| ATOM | 14050 | CG | GLU | B | 357 | 52.445 | 7.346 | −8.117 | 1.00 | 34.11 | B | C |
| ATOM | 14053 | CD | GLU | B | 357 | 53.308 | 6.403 | −8.934 | 1.00 | 49.89 | B | C |
| ATOM | 14054 | OE1 | GLU | B | 357 | 54.545 | 6.565 | −8.899 | 1.00 | 54.67 | B | O |
| ATOM | 14055 | OE2 | GLU | B | 357 | 52.742 | 5.520 | −9.630 | 1.00 | 62.79 | B | O |
| ATOM | 14056 | C | GLU | B | 357 | 50.738 | 9.782 | −7.660 | 1.00 | 18.63 | B | C |
| ATOM | 14057 | O | GLU | B | 357 | 51.308 | 9.983 | −6.589 | 1.00 | 17.61 | B | O |
| ATOM | 14059 | N | ILE | B | 358 | 50.625 | 10.741 | −8.571 | 1.00 | 20.13 | B | N |
| ATOM | 14060 | CA | ILE | B | 358 | 51.074 | 12.094 | −8.246 | 1.00 | 19.81 | B | C |
| ATOM | 14062 | CB | ILE | B | 358 | 51.160 | 12.978 | −9.495 | 1.00 | 23.03 | B | C |
| ATOM | 14064 | CG1 | ILE | B | 358 | 52.286 | 12.481 | −10.418 | 1.00 | 23.28 | B | C |
| ATOM | 14067 | CD1 | ILE | B | 358 | 52.104 | 12.900 | −11.898 | 1.00 | 17.88 | B | C |
| ATOM | 14071 | CG2 | ILE | B | 358 | 51.438 | 14.454 | −9.111 | 1.00 | 18.37 | B | C |
| ATOM | 14075 | C | ILE | B | 358 | 50.150 | 12.692 | −7.164 | 1.00 | 19.64 | B | C |
| ATOM | 14076 | O | ILE | B | 358 | 50.621 | 13.279 | −6.196 | 1.00 | 18.49 | B | O |
| ATOM | 14078 | N | ALA | B | 359 | 48.835 | 12.505 | −7.298 | 1.00 | 21.04 | B | N |
| ATOM | 14079 | CA | ALA | B | 359 | 47.910 | 12.942 | −6.247 | 1.00 | 19.40 | B | C |
| ATOM | 14081 | CB | ALA | B | 359 | 46.510 | 12.504 | −6.556 | 1.00 | 16.36 | B | C |
| ATOM | 14085 | C | ALA | B | 359 | 48.371 | 12.364 | −4.920 | 1.00 | 21.14 | B | C |
| ATOM | 14086 | O | ALA | B | 359 | 48.372 | 13.050 | −3.874 | 1.00 | 22.13 | B | O |
| ATOM | 14088 | N | TYR | B | 360 | 48.815 | 11.108 | −4.955 | 1.00 | 19.16 | B | N |
| ATOM | 14089 | CA | TYR | B | 360 | 49.215 | 10.452 | −3.712 | 1.00 | 18.42 | B | C |
| ATOM | 14091 | CB | TYR | B | 360 | 49.446 | 8.947 | −3.887 | 1.00 | 15.75 | B | C |
| ATOM | 14094 | CG | TYR | B | 360 | 49.888 | 8.307 | −2.601 | 1.00 | 12.33 | B | C |
| ATOM | 14095 | CD1 | TYR | B | 360 | 48.972 | 7.920 | −1.649 | 1.00 | 13.40 | B | C |

TABLE 4-2-continued

| Coordinates of *P. alba* IspS | | | | | | | | | | | | |
|---|---|---|---|---|---|---|---|---|---|---|---|---|
| ATOM | 14097 | CE1 | TYR | B | 360 | 49.371 | 7.368 | −0.458 | 1.00 | 9.59 | B | C |
| ATOM | 14099 | CZ | TYR | B | 360 | 50.716 | 7.214 | −0.194 | 1.00 | 15.43 | B | C |
| ATOM | 14100 | OH | TYR | B | 360 | 51.132 | 6.646 | 1.000 | 1.00 | 13.06 | B | O |
| ATOM | 14102 | CE2 | TYR | B | 360 | 51.646 | 7.606 | −1.132 | 1.00 | 12.26 | B | C |
| ATOM | 14104 | CD2 | TYR | B | 360 | 51.233 | 8.143 | −2.315 | 1.00 | 12.87 | B | C |
| ATOM | 14106 | C | TYR | B | 360 | 50.424 | 11.100 | −3.604 | 1.00 | 16.88 | B | C |
| ATOM | 14107 | O | TYR | B | 360 | 50.434 | 11.292 | −1.857 | 1.00 | 16.26 | B | O |
| ATOM | 14109 | N | ASP | B | 361 | 51.445 | 11.406 | −3.855 | 1.00 | 19.15 | B | N |
| ATOM | 14110 | CA | ASP | B | 361 | 52.668 | 12.027 | −3.354 | 1.00 | 20.70 | B | C |
| ATOM | 14112 | CB | ASP | B | 361 | 53.668 | 12.338 | −4.492 | 1.00 | 22.88 | B | C |
| ATOM | 14115 | CG | ASP | B | 361 | 54.242 | 11.079 | −5.177 | 1.00 | 30.52 | B | C |
| ATOM | 14116 | OD1 | ASP | B | 361 | 54.385 | 10.017 | −4.519 | 1.00 | 34.4 | B | O |
| ATOM | 14117 | OD2 | ASP | B | 361 | 54.556 | 11.171 | −6.382 | 1.00 | 37.22 | B | O |
| ATOM | 14118 | C | ASP | B | 361 | 52.319 | 13.350 | −2.676 | 1.00 | 22.70 | B | C |
| ATOM | 14119 | O | ASP | B | 361 | 52.856 | 13.697 | −1.635 | 1.00 | 21.32 | B | O |
| ATOM | 14121 | N | ASN | B | 362 | 51.427 | 14.097 | −3.308 | 1.00 | 22.85 | B | N |
| ATOM | 14122 | CA | ASN | B | 362 | 50.995 | 15.345 | −2.761 | 1.00 | 23.65 | B | C |
| ATOM | 14124 | CB | ASN | B | 3362 | 50.210 | 16.111 | −3.804 | 1.00 | 25.00 | B | C |
| ATOM | 14127 | CG | ASN | B | 362 | 51.100 | 16.886 | −4.672 | 1.00 | 30.68 | B | C |
| ATOM | 14128 | OD1 | ASN | B | 362 | 51.508 | 17.995 | −4.301 | 1.00 | 29.31 | B | O |
| ATOM | 14129 | ND2 | ASN | B | 362 | 51.492 | 16.295 | −5.823 | 1.00 | 34.07 | B | N |
| ATOM | 14132 | C | ASN | B | 362 | 50.178 | 15.225 | −1.495 | 1.00 | 22.70 | B | C |
| ATOM | 14133 | O | ASN | B | 362 | 50.337 | 16.038 | −0.590 | 1.00 | 22.27 | B | O |
| ATOM | 14135 | N | LEU | B | 363 | 49.292 | 14.249 | −1.438 | 1.00 | 20.22 | B | N |
| ATOM | 14136 | CA | LEU | B | 363 | 48.564 | 14.000 | −0.210 | 1.00 | 20.99 | B | C |
| ATOM | 14138 | CB | LEU | B | 363 | 47.544 | 12.874 | −0.388 | 1.00 | 19.03 | B | C |
| ATOM | 14141 | CG | LEU | B | 363 | 46.668 | 12.477 | 0.809 | 1.00 | 22.46 | B | C |
| ATOM | 14143 | CD1 | LEU | B | 363 | 45.834 | 13.657 | 1.352 | 1.00 | 16.50 | B | C |
| ATOM | 14147 | CD2 | LEU | B | 363 | 45.75 | 11.304 | 0.456 | 1.00 | 15.67 | B | C |
| ATOM | 14151 | C | LEU | B | 363 | 49.582 | 13.669 | 0.868 | 1.00 | 21.81 | B | C |
| ATOM | 14152 | O | LEU | B | 363 | 49.546 | 14.234 | 1.950 | 1.00 | 22.89 | B | O |
| ATOM | 14154 | N | LYS | B | 364 | 50.531 | 12.798 | 0.558 | 1.00 | 24.05 | B | N |
| ATOM | 14155 | CA | LYS | B | 364 | 51.494 | 12.362 | 1.566 | 1.00 | 24.81 | B | C |
| ATOM | 14157 | CB | LYS | B | 364 | 52.416 | 11.272 | 1.015 | 1.00 | 24.82 | B | C |
| ATOM | 14160 | CG | LYS | B | 364 | 53.281 | 10.584 | 2.058 | 1.00 | 27.90 | B | C |
| ATOM | 14163 | CD | LYS | B | 364 | 54.170 | 9.479 | 1.430 | 1.00 | 31.07 | B | C |
| ATOM | 14166 | CE | LYS | B | 364 | 55.496 | 9.983 | 0.869 | 1.00 | 27.35 | B | C |
| ATOM | 14169 | NZ | LYS | B | 364 | 55.461 | 10.244 | −0.578 | 1.00 | 39.19 | B | N |
| ATOM | 14173 | C | LYS | B | 364 | 52.340 | 13.526 | 2.066 | 1.00 | 26.11 | B | C |
| ATOM | 14174 | O | LYS | B | 364 | 52.554 | 13.650 | 3.281 | 1.00 | 23.11 | B | O |
| ATOM | 14176 | N | ASP | B | 365 | 52.838 | 14.349 | 1.133 | 1.00 | 25.89 | B | N |
| ATOM | 14177 | CA | ASP | B | 365 | 53.864 | 15.347 | 1.466 | 1.00 | 29.64 | B | C |
| ATOM | 14179 | CB | ASP | B | 365 | 54.815 | 15.590 | 0.286 | 1.00 | 31.01 | B | C |
| ATOM | 14182 | CG | ASP | B | 365 | 55.574 | 14.334 | −0.135 | 1.00 | 40.18 | B | C |
| ATOM | 14183 | OD1 | ASP | B | 365 | 55.800 | 13.438 | 0.719 | 1.00 | 43.63 | B | C |
| ATOM | 14184 | OD2 | ASP | B | 365 | 55.939 | 14.257 | −1.336 | 1.00 | 47.50 | B | O |
| ATOM | 14185 | C | ASP | B | 365 | 53.276 | 16.680 | 1.907 | 1.00 | 29.07 | B | C |
| ATOM | 14186 | O | ASP | B | 365 | 53.883 | 17.378 | 2.696 | 1.00 | 31.54 | B | O |
| ATOM | 14188 | N | LYS | B | 366 | 52.104 | 17.028 | 1.395 | 1.00 | 28.84 | B | N |
| ATOM | 14189 | CA | LYS | B | 366 | 51.490 | 18.322 | 1.681 | 1.00 | 31.06 | B | C |
| ATOM | 14191 | CB | LYS | B | 366 | 51.269 | 19.114 | 0.382 | 1.00 | 31.40 | B | C |
| ATOM | 14194 | CG | LYS | B | 366 | 52.545 | 19.404 | −0.401 | 1.00 | 37.02 | B | C |
| ATOM | 14197 | CD | LYS | B | 366 | 52.242 | 20.235 | −1.658 | 1.00 | 53.13 | B | C |
| ATOM | 14200 | CE | LYS | B | 366 | 53.336 | 20.108 | −2.732 | 1.00 | 53.38 | B | C |
| ATOM | 14203 | NZ | LYS | B | 366 | 54.714 | 20.334 | −2.185 | 1.00 | 64.76 | B | N |
| ATOM | 14207 | C | LYS | B | 366 | 50.172 | 18.210 | 2.446 | 1.00 | 31.50 | B | C |
| ATOM | 14208 | O | LYS | B | 366 | 49.653 | 19.220 | 2.915 | 1.00 | 33.61 | B | O |
| ATOM | 14210 | N | GLY | B | 367 | 49.631 | 17.002 | 2.579 | 1.00 | 28.68 | B | N |
| ATOM | 14211 | CA | GLY | B | 367 | 48.409 | 16.804 | 3.338 | 1.00 | 27.28 | B | C |
| ATOM | 14214 | C | GLY | B | 367 | 47.191 | 17.406 | 2.685 | 1.00 | 27.99 | B | C |
| ATOM | 14215 | O | GLY | B | 367 | 46.250 | 17.788 | 3.386 | 1.00 | 28.42 | B | O |
| ATOM | 14217 | N | GLU | B | 368 | 47.203 | 17.468 | 1.347 | 1.00 | 27.86 | B | N |
| ATOM | 14218 | CA | GLU | B | 368 | 46.081 | 17.979 | 0.547 | 1.00 | 27.52 | B | C |
| ATOM | 14220 | CB | GLU | B | 368 | 46.450 | 19.330 | −0.095 | 1.00 | 30.43 | B | C |
| ATOM | 14223 | CG | GLU | B | 368 | 46.948 | 20.426 | 0.862 | 1.00 | 39.15 | B | C |
| ATOM | 14226 | CD | GLU | B | 368 | 45.836 | 21.137 | 1.619 | 1.00 | 47.36 | B | C |
| ATOM | 14227 | OE1 | GLU | B | 368 | 44.658 | 20.703 | 1.548 | 1.00 | 49.41 | B | O |
| ATOM | 14228 | OE2 | GLU | B | 368 | 46.162 | 22.142 | 2.291 | 1.00 | 53.64 | B | O |
| ATOM | 14229 | C | GLU | B | 368 | 45.713 | 17.032 | −0.591 | 1.00 | 24.33 | B | C |
| ATOM | 14230 | O | GLU | B | 368 | 46.584 | 16.536 | −1.308 | 1.00 | 22.31 | B | O |
| ATOM | 14232 | N | ASN | B | 369 | 44.421 | 16.800 | −0.764 | 1.00 | 23.20 | B | N |
| ATOM | 14233 | CA | ASN | B | 369 | 43.909 | 16.123 | −1.947 | 1.00 | 23.98 | B | C |
| ATOM | 14235 | CB | ASN | B | 369 | 42.532 | 15.541 | −1.671 | 1.00 | 23.61 | B | C |
| ATOM | 14238 | CG | ASN | B | 369 | 42.019 | 14.665 | −2.820 | 1.00 | 28.43 | B | C |
| ATOM | 14239 | OD1 | ASN | B | 369 | 42.646 | 14.562 | −3.880 | 1.00 | 27.91 | B | O |
| ATOM | 14240 | ND2 | ASN | B | 369 | 40.871 | 14.015 | −2.597 | 1.00 | 22.66 | B | N |
| ATOM | 14243 | C | ASN | B | 369 | 43.806 | 17.093 | −3.129 | 1.00 | 23.36 | B | C |
| ATOM | 14244 | O | ASN | B | 369 | 42.863 | 17.874 | −3.200 | 1.00 | 24.65 | B | O |

TABLE 4-2-continued

| Coordinates of *P. alba* IspS | | | | | | | | | | | | |
|---|---|---|---|---|---|---|---|---|---|---|---|---|
| ATOM | 14246 | N | ILE | B | 370 | 44.751 | 17.015 | −4.059 | 1.00 | 21.14 | B | N |
| ATOM | 14247 | CA | ILE | B | 370 | 44.723 | 17.849 | −5.249 | 1.00 | 21.55 | B | C |
| ATOM | 14249 | CB | ILE | B | 370 | 46.137 | 18.417 | −5.572 | 1.00 | 22.76 | B | C |
| ATOM | 14251 | CG1 | ILE | B | 370 | 47.140 | 17.296 | −5.847 | 1.00 | 22.92 | B | C |
| ATOM | 14254 | CD1 | ILE | B | 370 | 48.345 | 17.766 | −6.586 | 1.00 | 25.13 | B | C |
| ATOM | 14258 | CG2 | ILE | B | 370 | 46.639 | 19.311 | −4.433 | 1.00 | 21.02 | B | C |
| ATOM | 14262 | C | ILE | B | 370 | 44.180 | 17.118 | −6.492 | 1.00 | 22.16 | B | C |
| ATOM | 14263 | O | ILE | B | 370 | 44.222 | 17.661 | −7.593 | 1.00 | 21.34 | B | O |
| ATOM | 14265 | N | LEU | B | 371 | 43.669 | 15.898 | −6.330 | 1.00 | 20.03 | B | N |
| ATOM | 14266 | CA | LEU | B | 371 | 43.260 | 15.105 | −7.485 | 1.00 | 20.80 | B | C |
| ATOM | 14268 | CB | LEU | B | 371 | 42.735 | 13.735 | −7.052 | 1.00 | 19.94 | B | C |
| ATOM | 14271 | CG | LEU | B | 371 | 42.452 | 12.746 | −8.191 | 1.00 | 22.27 | B | C |
| ATOM | 14273 | CD1 | LEU | B | 371 | 43.736 | 12.396 | −8.973 | 1.00 | 16.64 | B | C |
| ATOM | 14277 | CD2 | LEU | B | 371 | 41.792 | 11.477 | −7.642 | 1.00 | 18.00 | B | C |
| ATOM | 14281 | C | LEU | B | 371 | 42.219 | 15.800 | −8.387 | 1.00 | 22.85 | B | C |
| ATOM | 14282 | O | LEU | B | 371 | 42.340 | 15.738 | −9.623 | 1.00 | 24.00 | B | O |
| ATOM | 14284 | N | PRO | B | 372 | 41.201 | 16.468 | −7.787 | 1.00 | 23.30 | B | N |
| ATOM | 14285 | CA | PRO | B | 372 | 40.201 | 17.090 | −8.648 | 1.00 | 23.58 | B | C |
| ATOM | 14287 | CB | PRO | B | 372 | 39.225 | 17.761 | −7.670 | 1.00 | 24.01 | B | C |
| ATOM | 14290 | CG | PRO | B | 372 | 39.457 | 17.118 | −6.376 | 1.00 | 28.41 | B | C |
| ATOM | 14293 | CD | PRO | B | 372 | 40.897 | 16.685 | −6.359 | 1.00 | 25.80 | B | C |
| ATOM | 14296 | C | PRO | B | 372 | 40.804 | 18.105 | −9.604 | 1.00 | 22.18 | B | C |
| ATOM | 14297 | O | PRO | B | 372 | 40.310 | 18.227 | −10.701 | 1.00 | 23.54 | B | O |
| ATOM | 14298 | N | TYR | B | 373 | 41.867 | 18.790 | −9.195 | 1.00 | 21.49 | B | N |
| ATOM | 14299 | CA | TYR | B | 373 | 42.552 | 19.781 | −10.047 | 1.00 | 24.02 | B | C |
| ATOM | 14301 | CB | TYR | B | 373 | 43.456 | 20.714 | −9.213 | 1.00 | 25.06 | B | C |
| ATOM | 14304 | CG | TYR | B | 373 | 42.747 | 21.255 | −7.971 | 1.00 | 28.99 | B | C |
| ATOM | 14305 | CD1 | TYR | B | 373 | 41.617 | 22.058 | −8.083 | 1.00 | 37.98 | B | C |
| ATOM | 14307 | CE1 | TYR | B | 373 | 40.932 | 22.510 | −6.958 | 1.00 | 38.97 | B | C |
| ATOM | 14309 | CZ | TYR | B | 373 | 41.378 | 22.165 | −5.709 | 1.00 | 40.12 | B | C |
| ATOM | 14310 | OH | TYR | B | 373 | 40.713 | 22.610 | −4.589 | 1.00 | 48.27 | B | O |
| ATOM | 14312 | CE2 | TYR | B | 373 | 42.488 | 21.359 | −5.568 | 1.00 | 40.83 | B | C |
| ATOM | 14314 | CD2 | TYR | B | 373 | 43.160 | 20.898 | −6.702 | 1.00 | 33.96 | B | C |
| ATOM | 14316 | C | TYR | B | 373 | 43.366 | 19.107 | −11.147 | 1.00 | 25.44 | B | C |
| ATOM | 14317 | O | TYR | B | 373 | 43.388 | 19.591 | −12.283 | 1.00 | 26.29 | B | O |
| ATOM | 14319 | N | LEU | B | 374 | 44.013 | 17.980 | −10.834 | 1.00 | 24.17 | B | N |
| ATOM | 14320 | CA | LEU | B | 374 | 44.808 | 17.285 | −11.844 | 1.00 | 20.73 | B | C |
| ATOM | 14322 | CB | LEU | B | 374 | 45.721 | 16.236 | −11.224 | 1.00 | 20.86 | B | C |
| ATOM | 14325 | CG | LEU | B | 374 | 46.684 | 16.702 | −10.130 | 1.00 | 20.24 | B | C |
| ATOM | 14327 | CD1 | LEU | B | 374 | 47.543 | 15.508 | −9.612 | 1.00 | 16.80 | B | C |
| ATOM | 14331 | CD2 | LEU | B | 374 | 47.562 | 17.841 | −10.572 | 1.00 | 17.67 | B | C |
| ATOM | 14335 | C | LEU | B | 374 | 43.891 | 16.659 | −12.869 | 1.00 | 18.95 | B | C |
| ATOM | 14336 | O | LEU | B | 374 | 44.166 | 16.700 | −14.059 | 1.00 | 20.39 | B | O |
| ATOM | 14338 | N | THR | B | 375 | 42.772 | 16.107 | −12.439 | 1.00 | 20.66 | B | N |
| ATOM | 14339 | CA | THR | B | 375 | 41.896 | 15.466 | −13.399 | 1.00 | 19.66 | B | C |
| ATOM | 14341 | CB | THR | B | 375 | 40.958 | 14.480 | −12.726 | 1.00 | 21.51 | B | C |
| ATOM | 14343 | OG1 | THR | B | 375 | 40.128 | 15.161 | −11.787 | 1.00 | 22.47 | B | O |
| ATOM | 14345 | CG2 | THR | B | 375 | 41.788 | 13.374 | −12.020 | 1.00 | 15.76 | B | C |
| ATOM | 14349 | C | THR | B | 375 | 41.130 | 16.486 | −14.248 | 1.00 | 22.51 | B | C |
| ATOM | 14350 | O | THR | B | 375 | 40.859 | 16.249 | −15.429 | 1.00 | 23.67 | B | O |
| ATOM | 14352 | N | LYS | B | 376 | 40.798 | 17.631 | −13.670 | 1.00 | 23.19 | B | N |
| ATOM | 14353 | CA | LYS | B | 376 | 40.133 | 18.683 | −14.434 | 1.00 | 24.29 | B | C |
| ATOM | 14355 | CB | LYS | B | 376 | 39.727 | 19.837 | −13.517 | 1.00 | 25.69 | B | C |
| ATOM | 14358 | CG | LYS | B | 376 | 38.961 | 20.963 | −14.212 | 1.00 | 32.29 | B | C |
| ATOM | 14361 | CD | LYS | B | 376 | 37.580 | 20.536 | −14.716 | 1.00 | 36.20 | B | C |
| ATOM | 14364 | CE | LYS | B | 376 | 36.881 | 21.706 | −15.449 | 1.00 | 39.50 | B | C |
| ATOM | 14367 | NZ | LYS | B | 376 | 35.532 | 21.322 | −15.952 | 1.00 | 46.03 | B | N |
| ATOM | 14371 | C | LYS | B | 376 | 41.050 | 19.181 | −15.535 | 1.00 | 21.89 | B | C |
| ATOM | 14372 | O | LYS | B | 376 | 40.614 | 19.403 | −16.653 | 1.00 | 24.65 | B | O |
| ATOM | 14374 | N | ALA | B | 377 | 42.325 | 19.356 | −15.222 | 1.00 | 20.03 | B | N |
| ATOM | 14375 | CA | ALA | B | 377 | 43.294 | 19.765 | −16.228 | 1.00 | 18.15 | B | C |
| ATOM | 14377 | CB | ALA | B | 377 | 44.692 | 19.870 | −15.637 | 1.00 | 18.15 | B | C |
| ATOM | 14381 | C | ALA | B | 377 | 43.283 | 18.775 | −17.366 | 1.00 | 18.11 | B | C |
| ATOM | 14382 | O | ALA | B | 377 | 43.257 | 19.189 | −18.533 | 1.00 | 18.41 | B | O |
| ATOM | 14384 | N | TRP | B | 378 | 43.258 | 17.473 | −17.059 | 1.00 | 17.59 | B | N |
| ATOM | 14385 | CA | TRP | B | 378 | 43.221 | 16.492 | −18.146 | 1.00 | 19.76 | B | C |
| ATOM | 14387 | CB | TRP | B | 378 | 43.567 | 15.063 | −17.701 | 1.00 | 20.21 | B | C |
| ATOM | 14390 | CG | TRP | B | 378 | 45.032 | 14.853 | −17.733 | 1.00 | 19.57 | B | C |
| ATOM | 14391 | CD1 | TRP | B | 378 | 45.905 | 14.995 | −16.696 | 1.00 | 16.98 | B | C |
| ATOM | 14393 | NE1 | TRP | B | 378 | 47.183 | 14.779 | −17.128 | 1.00 | 19.55 | B | N |
| ATOM | 14395 | CE2 | TRP | B | 378 | 47.152 | 14.483 | −18.466 | 1.00 | 17.20 | B | C |
| ATOM | 14396 | CD2 | TRP | B | 378 | 45.816 | 14.528 | −18.878 | 1.00 | 17.73 | B | C |
| ATOM | 14397 | CE3 | TRP | B | 378 | 45.512 | 14.282 | −20.216 | 1.00 | 19.66 | B | C |
| ATOM | 14399 | CZ3 | TRP | B | 378 | 46.530 | 13.995 | −21.082 | 1.00 | 21.97 | B | C |
| ATOM | 14401 | CH2 | TRP | B | 378 | 47.851 | 13.935 | −20.644 | 1.00 | 21.81 | B | C |
| ATOM | 14403 | CZ2 | TRP | B | 378 | 48.188 | 14.197 | −19.340 | 1.00 | 20.44 | B | C |
| ATOM | 14405 | C | TRP | B | 378 | 41.919 | 16.552 | −18.924 | 1.00 | 19.35 | B | C |
| ATOM | 14406 | O | TRP | B | 378 | 41.929 | 16.331 | −20.136 | 1.00 | 20.96 | B | O |

TABLE 4-2-continued

| Coordinates of *P. alba* IspS | | | | | | | | | | | |
|---|---|---|---|---|---|---|---|---|---|---|---|
| ATOM | 14408 | N | ALA | B | 379 | 40.821 | 16.846 | −18.242 | 1.00 | 17.74 | B | N |
| ATOM | 14409 | CA | ALA | B | 379 | 39.499 | 16.867 | −18.893 | 1.00 | 20.62 | B | C |
| ATOM | 14411 | CB | ALA | B | 379 | 38.337 | 17.003 | −17.854 | 1.00 | 20.87 | B | C |
| ATOM | 14415 | C | ALA | B | 379 | 39.443 | 18.014 | −19.877 | 1.00 | 20.85 | B | C |
| ATOM | 14416 | O | ALA | B | 379 | 38.957 | 17.853 | −20.998 | 1.00 | 22.78 | B | O |
| ATOM | 14418 | N | ASP | B | 380 | 39.966 | 19.164 | −19.467 | 1.00 | 19.02 | B | N |
| ATOM | 14419 | CA | ASP | B | 380 | 40.048 | 20.318 | −20.354 | 1.00 | 20.32 | B | C |
| ATOM | 14421 | CB | ASP | B | 380 | 40.580 | 21.538 | −19.611 | 1.00 | 22.48 | B | C |
| ATOM | 14424 | CG | ASP | B | 380 | 39.628 | 22.029 | −18.535 | 1.00 | 22.07 | B | C |
| ATOM | 14425 | OD1 | ASP | B | 380 | 38.441 | 21.626 | −18.530 | 1.00 | 25.90 | B | O |
| ATOM | 14426 | OD2 | ASP | B | 380 | 40.081 | 22.808 | −17.697 | 1.00 | 25.80 | B | O |
| ATOM | 14427 | C | ASP | B | 380 | 40.920 | 20.075 | −21.561 | 1.00 | 20.78 | B | C |
| ATOM | 14428 | O | ASP | B | 380 | 40.604 | 20.529 | −22.650 | 1.00 | 24.69 | B | O |
| ATOM | 14430 | N | LEU | B | 381 | 42.016 | 19.361 | −21.385 | 1.00 | 20.48 | B | N |
| ATOM | 14431 | CA | LEU | B | 381 | 42.894 | 19.074 | −22.504 | 1.00 | 19.96 | B | C |
| ATOM | 14433 | CB | LEU | B | 381 | 44.226 | 18.505 | −22.047 | 1.00 | 18.35 | B | C |
| ATOM | 14436 | CG | LEU | B | 381 | 45.196 | 18.161 | −23.167 | 1.00 | 22.53 | B | C |
| ATOM | 14438 | CD1 | LEU | B | 381 | 45.503 | 19.376 | −24.030 | 1.00 | 16.10 | B | C |
| ATOM | 14442 | CD2 | LEU | B | 381 | 46.453 | 17.579 | −22.589 | 1.00 | 16.33 | B | C |
| ATOM | 14446 | C | LEU | B | 381 | 42.197 | 18.127 | −23.456 | 1.00 | 19.12 | B | C |
| ATOM | 14447 | O | LEU | B | 381 | 42.162 | 18.365 | −24.641 | 1.00 | 19.21 | B | O |
| ATOM | 14449 | N | CYS | B | 382 | 41.610 | 17.060 | −22.943 | 1.00 | 20.99 | B | N |
| ATOM | 14450 | CA | CYS | B | 382 | 40.929 | 16.115 | −23.842 | 1.00 | 19.91 | B | C |
| ATOM | 14452 | CB | CYS | B | 382 | 40.480 | 14.866 | −23.077 | 1.00 | 19.91 | B | C |
| ATOM | 14455 | SG | CYS | B | 382 | 41.915 | 13.875 | −22.517 | 1.00 | 24.88 | B | S |
| ATOM | 14457 | C | CYS | B | 382 | 39.775 | 16.780 | −24.594 | 1.00 | 19.49 | B | C |
| ATOM | 14458 | O | CYS | B | 382 | 39.598 | 16.514 | −25.774 | 1.00 | 22.41 | B | O |
| ATOM | 14460 | N | ASN | B | 383 | 39.013 | 17.660 | −23.938 | 1.00 | 19.54 | B | N |
| ATOM | 14461 | CA | ASN | B | 383 | 37.953 | 18.433 | −24.628 | 1.00 | 19.38 | B | C |
| ATOM | 14463 | CB | ASN | B | 383 | 37.078 | 19.250 | −23.644 | 1.00 | 17.80 | B | C |
| ATOM | 14466 | CG | ASN | B | 383 | 35.976 | 18.410 | −23.013 | 1.00 | 21.83 | B | C |
| ATOM | 14467 | OD1 | ASN | B | 383 | 35.030 | 18.011 | −23.692 | 1.00 | 28.68 | B | O |
| ATOM | 14468 | ND2 | ASN | B | 383 | 36.105 | 18.115 | −21.715 | 1.00 | 19.68 | B | N |
| ATOM | 14471 | C | ASN | B | 383 | 38.514 | 19.360 | −25.704 | 1.00 | 20.03 | B | C |
| ATOM | 14472 | O | ASN | B | 383 | 37.876 | 19.576 | −26.722 | 1.00 | 21.15 | B | O |
| ATOM | 14474 | N | ALA | B | 384 | 39.708 | 19.905 | −25.491 | 1.00 | 19.68 | B | N |
| ATOM | 14475 | CA | ALA | B | 384 | 40.312 | 20.759 | −26.500 | 1.00 | 18.25 | B | C |
| ATOM | 14477 | CB | ALA | B | 384 | 41.412 | 21.600 | −25.902 | 1.00 | 16.95 | B | C |
| ATOM | 14481 | C | ALA | B | 384 | 40.799 | 19.897 | −27.676 | 1.00 | 19.74 | B | C |
| ATOM | 14482 | O | ALA | B | 384 | 40.642 | 20.274 | −28.845 | 1.00 | 20.58 | B | O |
| ATOM | 14484 | N | PHE | B | 385 | 41.308 | 18.706 | −27.396 | 1.00 | 19.10 | B | N |
| ATOM | 14485 | CA | PHE | B | 385 | 41.644 | 17.783 | −28.492 | 1.00 | 19.23 | B | C |
| ATOM | 14487 | CB | PHE | B | 385 | 42.336 | 16.521 | −27.964 | 1.00 | 19.77 | B | C |
| ATOM | 14490 | CG | PHE | B | 385 | 43.757 | 16.714 | −27.473 | 1.00 | 20.37 | B | C |
| ATOM | 14491 | CD1 | PHE | B | 385 | 44.639 | 17.573 | −28.099 | 1.00 | 29.85 | B | C |
| ATOM | 14493 | CE1 | PHE | B | 385 | 45.940 | 17.681 | −27.665 | 1.00 | 22.48 | B | C |
| ATOM | 14495 | CZ | PHE | B | 385 | 46.382 | 16.924 | −26.617 | 1.00 | 24.37 | B | C |
| ATOM | 14497 | CE2 | PHE | B | 385 | 45.540 | 16.037 | −26.022 | 1.00 | 19.74 | B | C |
| ATOM | 14499 | CD2 | PHE | B | 385 | 44.238 | 15.934 | −26.441 | 1.00 | 22.30 | B | C |
| ATOM | 14501 | C | PHE | B | 385 | 40.375 | 17.371 | −29.231 | 1.00 | 19.10 | B | C |
| ATOM | 14502 | O | PHE | B | 385 | 40.352 | 17.236 | −30.447 | 1.00 | 20.62 | B | O |
| ATOM | 14504 | N | LEU | B | 386 | 39.293 | 17.190 | −28.487 | 1.00 | 20.82 | B | N |
| ATOM | 14505 | CA | LEU | B | 386 | 38.062 | 16.710 | −29.088 | 1.00 | 19.64 | B | C |
| ATOM | 14507 | CB | LEU | B | 386 | 37.033 | 16.356 | −28.010 | 1.00 | 17.81 | B | C |
| ATOM | 14510 | CG | LEU | B | 386 | 35.711 | 15.780 | −28.547 | 1.00 | 24.89 | B | C |
| ATOM | 14512 | CD1 | LEU | B | 386 | 35.866 | 14.382 | −29.197 | 1.00 | 17.85 | B | C |
| ATOM | 14516 | CD2 | LEU | B | 386 | 34.649 | 15.792 | −27.450 | 1.00 | 13.88 | B | C |
| ATOM | 14520 | C | LEU | B | 386 | 37.531 | 17.758 | −30.044 | 1.00 | 19.89 | B | C |
| ATOM | 14521 | O | LEU | B | 386 | 37.114 | 17.439 | −31.142 | 1.00 | 22.28 | B | O |
| ATOM | 14523 | N | GLN | B | 387 | 37.561 | 19.018 | −29.629 | 1.00 | 22.06 | B | N |
| ATOM | 14524 | CA | GLN | B | 387 | 37.101 | 20.123 | −30.479 | 1.00 | 21.92 | B | C |
| ATOM | 14526 | CB | GLN | B | 387 | 37.163 | 21.490 | −29.736 | 1.00 | 23.65 | B | C |
| ATOM | 14529 | CG | GLN | B | 387 | 36.756 | 22.718 | −30.578 | 1.00 | 24.14 | B | C |
| ATOM | 14532 | CD | GLN | B | 387 | 35.325 | 22.625 | −31.073 | 1.00 | 16.59 | B | C |
| ATOM | 14533 | OE1 | GLN | B | 387 | 35.071 | 22.082 | −32.132 | 1.00 | 26.49 | B | O |
| ATOM | 14534 | NE2 | GLN | B | 387 | 34.397 | 23.060 | −30.270 | 1.00 | 21.29 | B | N |
| ATOM | 14537 | C | GLN | B | 387 | 37.902 | 20.163 | −31.769 | 1.00 | 20.75 | B | C |
| ATOM | 14538 | O | GLN | B | 387 | 37.326 | 20.380 | −32.815 | 1.00 | 21.62 | B | O |
| ATOM | 14540 | N | GLU | B | 388 | 39.211 | 19.914 | −31.714 | 1.00 | 21.58 | B | N |
| ATOM | 14541 | CA | GLU | B | 388 | 40.045 | 19.919 | −32.920 | 1.00 | 22.44 | B | C |
| ATOM | 14543 | CB | GLU | B | 388 | 41.538 | 19.854 | −32.588 | 1.00 | 25.28 | B | C |
| ATOM | 14546 | CG | GLU | B | 388 | 42.068 | 21.146 | −31.939 | 1.00 | 32.65 | B | C |
| ATOM | 14549 | CD | GLU | B | 388 | 43.555 | 21.107 | −31.568 | 1.00 | 35.29 | B | C |
| ATOM | 14550 | OE1 | GLU | B | 388 | 44.121 | 20.004 | −31.343 | 1.00 | 36.54 | B | O |
| ATOM | 14551 | OE2 | GLU | B | 388 | 44.158 | 22.197 | −31.498 | 1.00 | 33.60 | B | O |
| ATOM | 14552 | C | GLU | B | 388 | 39.688 | 18.754 | −33.825 | 1.00 | 21.97 | B | C |
| ATOM | 14553 | O | GLU | B | 388 | 39.651 | 18.903 | −35.039 | 1.00 | 21.50 | B | O |
| ATOM | 14555 | N | ALA | B | 389 | 39.381 | 17.607 | −33.236 | 1.00 | 21.26 | B | N |

TABLE 4-2-continued

| Coordinates of *P. alba* IspS | | | | | | | | | | | |
|---|---|---|---|---|---|---|---|---|---|---|---|
| ATOM | 14556 | CA | ALA | B | 389 | 39.026 | 16.445 | −34.048 | 1.00 | 21.14 | B | C |
| ATOM | 14558 | CB | ALA | B | 389 | 38.959 | 15.156 | −33.221 | 1.00 | 20.09 | B | C |
| ATOM | 14562 | C | ALA | B | 389 | 37.707 | 16.691 | −34.731 | 1.00 | 19.85 | B | C |
| ATOM | 14563 | O | ALA | B | 389 | 37.538 | 16.311 | −35.875 | 1.00 | 20.01 | B | O |
| ATOM | 14565 | N | LYS | B | 390 | 36.771 | 17.324 | −34.040 | 1.00 | 19.84 | B | N |
| ATOM | 14566 | CA | LYS | B | 390 | 35.453 | 17.575 | −34.629 | 1.00 | 22.05 | B | C |
| ATOM | 14568 | CB | LYS | B | 390 | 34.455 | 18.051 | −33.572 | 1.00 | 24.20 | B | C |
| ATOM | 14571 | CG | LYS | B | 390 | 33.969 | 17.003 | −32.647 | 1.00 | 22.59 | B | C |
| ATOM | 14574 | CD | LYS | B | 390 | 32.947 | 17.600 | −31.704 | 1.00 | 34.38 | B | C |
| ATOM | 14577 | CE | LYS | B | 390 | 32.409 | 16.563 | −30.729 | 1.00 | 32.22 | B | C |
| ATOM | 14580 | NZ | LYS | B | 390 | 31.908 | 17.280 | −29.517 | 1.00 | 30.01 | B | N |
| ATOM | 14584 | C | LYS | B | 390 | 35.491 | 18.607 | −35.745 | 1.00 | 21.67 | B | C |
| ATOM | 14585 | O | LYS | B | 390 | 34.748 | 18.501 | −36.709 | 1.00 | 21.81 | B | O |
| ATOM | 14587 | N | TRP | B | 391 | 36.349 | 19.609 | −35.593 | 1.00 | 22.17 | B | N |
| ATOM | 14588 | CA | TRP | B | 391 | 36.538 | 20.662 | −36.605 | 1.00 | 22.08 | B | C |
| ATOM | 14590 | CB | TRP | B | 391 | 37.462 | 21.803 | −36.091 | 1.00 | 20.61 | B | C |
| ATOM | 14593 | CG | TRP | B | 391 | 36.758 | 22.833 | −35.264 | 1.00 | 21.47 | B | C |
| ATOM | 14594 | CD1 | TRP | B | 391 | 35.444 | 23.170 | −35.325 | 1.00 | 21.71 | B | C |
| ATOM | 14596 | NE1 | TRP | B | 391 | 35.169 | 24.177 | −34.438 | 1.00 | 25.90 | B | N |
| ATOM | 14598 | CE2 | TRP | B | 391 | 36.322 | 24.519 | −33.791 | 1.00 | 19.12 | B | C |
| ATOM | 14599 | CD2 | TRP | B | 391 | 37.345 | 23.702 | −34.295 | 1.00 | 20.50 | B | C |
| ATOM | 14600 | CE3 | TRP | B | 391 | 38.639 | 23.845 | −33.778 | 1.00 | 23.66 | B | C |
| ATOM | 14602 | CZ3 | TRP | B | 391 | 38.860 | 24.792 | −32.811 | 1.00 | 18.30 | B | C |
| ATOM | 14604 | CH2 | TRP | B | 391 | 37.825 | 25.605 | −32.338 | 1.00 | 18.94 | B | C |
| ATOM | 14606 | CZ2 | TRP | B | 391 | 36.546 | 25.480 | −32.804 | 1.00 | 20.38 | B | C |
| ATOM | 14608 | C | TRP | B | 391 | 37.132 | 20.090 | −37.860 | 1.00 | 22.57 | B | C |
| ATOM | 14609 | O | TRP | B | 391 | 36.765 | 20.495 | −38.976 | 1.00 | 18.85 | B | O |
| ATOM | 14611 | N | LEU | B | 392 | 38.089 | 19.189 | −37.676 | 1.00 | 23.55 | B | N |
| ATOM | 14612 | CA | LEU | B | 392 | 38.703 | 18.505 | −38.812 | 1.00 | 27.40 | B | C |
| ATOM | 14614 | CB | LEU | B | 392 | 39.929 | 17.704 | −38.359 | 1.00 | 28.77 | B | C |
| ATOM | 14617 | CG | LEU | B | 392 | 40.742 | 17.113 | −39.517 | 1.00 | 37.78 | B | C |
| ATOM | 14619 | CD1 | LEU | B | 392 | 41.420 | 18.237 | −40.349 | 1.00 | 40.60 | B | C |
| ATOM | 14623 | CD2 | LEU | B | 392 | 41.775 | 16.124 | −38.979 | 1.00 | 38.73 | B | C |
| ATOM | 14627 | C | LEU | B | 392 | 37.674 | 17.591 | −39.509 | 1.00 | 25.45 | B | C |
| ATOM | 14628 | O | LEU | B | 392 | 37.457 | 17.687 | −40.714 | 1.00 | 24.87 | B | O |
| ATOM | 14630 | N | TYR | B | 393 | 36.998 | 16.748 | −38.744 | 1.00 | 24.92 | B | N |
| ATOM | 14631 | CA | TYR | B | 393 | 35.977 | 15.878 | −39.329 | 1.00 | 27.07 | B | C |
| ATOM | 14633 | CB | TYR | B | 393 | 35.261 | 15.065 | −38.248 | 1.00 | 27.20 | B | C |
| ATOM | 14636 | CG | TYR | B | 393 | 34.250 | 14.084 | −38.801 | 1.00 | 32.35 | B | C |
| ATOM | 14637 | CD1 | TYR | B | 393 | 34.635 | 12.817 | −39.240 | 1.00 | 36.10 | B | C |
| ATOM | 14639 | CE1 | TYR | B | 393 | 33.685 | 11.915 | −39.762 | 1.00 | 41.26 | B | C |
| ATOM | 14641 | CZ | TYR | B | 393 | 32.347 | 12.292 | −39.829 | 1.00 | 42.05 | B | C |
| ATOM | 14642 | OH | TYR | B | 393 | 31.387 | 11.441 | −40.331 | 1.00 | 49.85 | B | O |
| ATOM | 14644 | CE2 | TYR | B | 393 | 31.959 | 13.542 | −39.397 | 1.00 | 40.87 | B | C |
| ATOM | 14646 | CD2 | TYR | B | 393 | 32.906 | 14.426 | −38.890 | 1.00 | 37.12 | B | C |
| ATOM | 14648 | C | TYR | B | 393 | 34.940 | 16.684 | −40.109 | 1.00 | 26.51 | B | C |
| ATOM | 14649 | O | TYR | B | 393 | 34.686 | 16.403 | −41.270 | 1.00 | 26.33 | B | O |
| ATOM | 14651 | N | ASN | B | 394 | 34.341 | 17.685 | −39.460 | 1.00 | 26.40 | B | N |
| ATOM | 14652 | CA | ASN | B | 394 | 33.277 | 18.486 | −40.081 | 1.00 | 27.32 | B | C |
| ATOM | 14654 | CB | ASN | B | 394 | 32.442 | 19.175 | −38.993 | 1.00 | 28.58 | B | C |
| ATOM | 14657 | CG | ASN | B | 394 | 31.679 | 18.176 | −38.123 | 1.00 | 28.94 | B | C |
| ATOM | 14658 | OD1 | ASN | B | 394 | 31.111 | 17.223 | −38.628 | 1.00 | 34.61 | B | O |
| ATOM | 14659 | ND2 | ASN | B | 394 | 31.632 | 18.420 | −36.833 | 1.00 | 30.26 | B | N |
| ATOM | 14662 | C | ASN | B | 394 | 33.781 | 19.513 | −41.110 | 1.00 | 27.48 | B | C |
| ATOM | 14663 | O | ASN | B | 394 | 32.997 | 20.225 | −41.670 | 1.00 | 27.41 | B | O |
| ATOM | 14665 | N | LYS | B | 395 | 35.089 | 19.562 | −41.372 | 1.00 | 29.77 | B | N |
| ATOM | 14666 | CA | LYS | B | 395 | 35.702 | 20.601 | −42.222 | 1.00 | 31.41 | B | C |
| ATOM | 14668 | CB | LYS | B | 395 | 35.413 | 20.316 | −43.699 | 1.00 | 33.28 | B | C |
| ATOM | 14671 | CG | LYS | B | 395 | 36.114 | 19.035 | −44.217 | 1.00 | 41.09 | B | C |
| ATOM | 14674 | CD | LYS | B | 395 | 35.295 | 18.354 | −45.321 | 1.00 | 50.28 | B | C |
| ATOM | 14677 | CE | LYS | B | 395 | 36.139 | 17.389 | −46.164 | 1.00 | 54.00 | B | C |
| ATOM | 14680 | NZ | LYS | B | 395 | 36.929 | 16.446 | −45.322 | 1.00 | 54.63 | B | N |
| ATOM | 14684 | C | LYS | B | 395 | 35.303 | 22.041 | −41.811 | 1.00 | 31.59 | B | C |
| ATOM | 14685 | O | LYS | B | 395 | 35.164 | 22.939 | −42.649 | 1.00 | 32.31 | B | O |
| ATOM | 14687 | N | SER | B | 396 | 35.137 | 22.249 | −40.504 | 1.00 | 30.78 | B | N |
| ATOM | 14688 | CA | SER | B | 396 | 34.832 | 23.558 | −39.971 | 1.00 | 29.21 | B | C |
| ATOM | 14690 | CB | SER | B | 396 | 34.656 | 23.475 | −38.479 | 1.00 | 29.18 | B | C |
| ATOM | 14693 | OG | SER | B | 396 | 33.613 | 22.573 | −38.184 | 1.00 | 28.88 | B | O |
| ATOM | 14695 | C | SER | B | 396 | 35.962 | 24.492 | −40.327 | 1.00 | 28.15 | B | C |
| ATOM | 14696 | O | SER | B | 396 | 37.054 | 24.038 | −40.604 | 1.00 | 30.53 | B | O |
| ATOM | 14698 | N | THR | B | 397 | 35.666 | 25.788 | −40.360 | 1.00 | 26.95 | B | N |
| ATOM | 14699 | CA | THR | B | 397 | 36.617 | 26.847 | −40.705 | 1.00 | 25.06 | B | C |
| ATOM | 14701 | CB | THR | B | 397 | 36.309 | 27.435 | −42.117 | 1.00 | 27.07 | B | C |
| ATOM | 14703 | OG1 | THR | B | 397 | 34.924 | 27.817 | −42.180 | 1.00 | 25.75 | B | O |
| ATOM | 14705 | CG2 | THR | B | 397 | 36.576 | 26.369 | −43.218 | 1.00 | 27.27 | B | C |
| ATOM | 14709 | C | THR | B | 397 | 36.509 | 27.959 | −39.641 | 1.00 | 24.96 | B | C |
| ATOM | 14710 | O | THR | B | 397 | 36.177 | 29.100 | −39.937 | 1.00 | 24.56 | B | O |
| ATOM | 14712 | N | PRO | B | 398 | 36.791 | 27.622 | −38.388 | 1.00 | 21.45 | B | N |

TABLE 4-2-continued

Coordinates of *P. alba* IspS

| | | | | | | | | | | | | |
|---|---|---|---|---|---|---|---|---|---|---|---|---|
| ATOM | 14713 | CA | PRO | B | 398 | 36.633 | 28.604 | −37.323 | 1.00 | 22.11 | B | C |
| ATOM | 14715 | CB | PRO | B | 398 | 37.058 | 27.831 | −36.068 | 1.00 | 22.56 | B | C |
| ATOM | 14718 | CG | PRO | B | 398 | 37.975 | 26.737 | −36.622 | 1.00 | 23.07 | B | C |
| ATOM | 14721 | CD | PRO | B | 398 | 37.438 | 26.379 | −37.933 | 1.00 | 20.76 | B | C |
| ATOM | 14724 | C | PRO | B | 398 | 37.525 | 29.813 | −37.478 | 1.00 | 19.82 | B | C |
| ATOM | 14725 | O | PRO | B | 398 | 38.602 | 29.720 | −38.032 | 1.00 | 22.01 | B | O |
| ATOM | 14726 | N | THR | B | 399 | 37.093 | 30.930 | −36.920 | 1.00 | 17.51 | B | N |
| ATOM | 14727 | CA | THR | B | 399 | 37.889 | 32.130 | −36.915 | 1.00 | 15.86 | B | C |
| ATOM | 14729 | CB | THR | B | 399 | 37.165 | 33.304 | −36.225 | 1.00 | 17.11 | B | C |
| ATOM | 14731 | OG1 | THR | B | 399 | 37.060 | 32.998 | −34.850 | 1.00 | 14.13 | B | O |
| ATOM | 14733 | CG2 | THR | B | 399 | 35.717 | 33.586 | −36.827 | 1.00 | 8.38 | B | C |
| ATOM | 14737 | C | THR | B | 399 | 39.152 | 31.912 | −36.130 | 1.00 | 16.82 | B | C |
| ATOM | 14738 | O | THR | B | 399 | 39.258 | 30.995 | −35.292 | 1.00 | 16.62 | B | O |
| ATOM | 14740 | N | PHE | B | 400 | 40.099 | 32.806 | −36.356 | 1.00 | 17.90 | B | N |
| ATOM | 14741 | CA | PHE | B | 400 | 41.335 | 32.771 | −35.628 | 1.00 | 20.04 | B | C |
| ATOM | 14743 | CB | PHE | B | 400 | 42.240 | 33.952 | −35.999 | 1.00 | 19.33 | B | C |
| ATOM | 14746 | CG | PHE | B | 400 | 43.454 | 34.023 | −35.144 | 1.00 | 22.23 | B | C |
| ATOM | 14747 | CD1 | PHE | B | 400 | 44.521 | 33.161 | −35.374 | 1.00 | 25.77 | B | C |
| ATOM | 14749 | CE1 | PHE | B | 400 | 45.663 | 33.194 | −34.559 | 1.00 | 23.21 | B | C |
| ATOM | 14751 | CZ | PHE | B | 400 | 45.721 | 34.093 | −33.485 | 1.00 | 22.27 | B | C |
| ATOM | 14753 | CE2 | PHE | B | 400 | 44.655 | 34.955 | −33.244 | 1.00 | 24.82 | B | C |
| ATOM | 14755 | CD2 | PHE | B | 400 | 43.524 | 34.914 | −34.075 | 1.00 | 25.67 | B | C |
| ATOM | 14757 | C | PHE | B | 400 | 41.113 | 32.770 | −34.120 | 1.00 | 20.59 | B | C |
| ATOM | 14758 | O | PHE | B | 400 | 41.692 | 31.965 | −33.427 | 1.00 | 19.12 | B | O |
| ATOM | 14760 | N | ASP | B | 401 | 40.339 | 33.726 | −33.612 | 1.00 | 19.68 | B | N |
| ATOM | 14761 | CA | ASP | B | 401 | 40.065 | 33.780 | −32.186 | 1.00 | 20.55 | B | C |
| ATOM | 14763 | CB | ASP | B | 401 | 39.100 | 34.942 | −31.855 | 1.00 | 19.50 | B | C |
| ATOM | 14766 | CG | ASP | B | 401 | 39.771 | 36.314 | −31.977 | 1.00 | 26.06 | B | C |
| ATOM | 14767 | OD1 | ASP | B | 401 | 41.024 | 36.425 | −31.871 | 1.00 | 27.25 | B | O |
| ATOM | 14768 | OD2 | ASP | B | 401 | 39.040 | 37.283 | −32.190 | 1.00 | 31.85 | B | O |
| ATOM | 14769 | C | ASP | B | 401 | 39.518 | 32.467 | −31.609 | 1.00 | 19.11 | B | C |
| ATOM | 14770 | O | ASP | B | 401 | 39.910 | 32.084 | −30.525 | 1.00 | 15.67 | B | O |
| ATOM | 14772 | N | ASP | B | 402 | 38.582 | 31.816 | −32.294 | 1.00 | 18.01 | B | N |
| ATOM | 14773 | CA | ASP | B | 402 | 38.058 | 30.539 | −31.800 | 1.00 | 20.72 | B | C |
| ATOM | 14775 | CB | ASP | B | 402 | 36.784 | 30.151 | −32.556 | 1.00 | 21.12 | B | C |
| ATOM | 14778 | CG | ASP | B | 402 | 35.608 | 31.018 | −32.192 | 1.00 | 24.45 | B | C |
| ATOM | 14779 | OD1 | ASP | B | 402 | 35.626 | 31.614 | −31.100 | 1.00 | 34.43 | B | O |
| ATOM | 14780 | OD2 | ASP | B | 402 | 34.655 | 31.099 | −32.986 | 1.00 | 33.91 | B | O |
| ATOM | 14781 | C | ASP | B | 402 | 39.102 | 29.413 | −31.902 | 1.00 | 20.64 | B | C |
| ATOM | 14782 | O | ASP | B | 402 | 39.301 | 28.658 | −30.946 | 1.00 | 20.80 | B | O |
| ATOM | 14784 | N | TYR | B | 403 | 39.796 | 29.322 | −33.037 | 1.00 | 17.89 | B | N |
| ATOM | 14785 | CA | TYR | B | 403 | 40.782 | 28.278 | −33.195 | 1.00 | 20.95 | B | C |
| ATOM | 14787 | CB | TYR | B | 403 | 41.398 | 28.285 | −34.593 | 1.00 | 24.16 | B | C |
| ATOM | 14790 | CG | TYR | B | 403 | 42.415 | 27.191 | −34.774 | 1.00 | 25.07 | B | C |
| ATOM | 14791 | CD1 | TYR | B | 403 | 41.994 | 25.920 | −35.085 | 1.00 | 33.87 | B | C |
| ATOM | 14793 | CE1 | TYR | B | 403 | 42.869 | 24.897 | −35.245 | 1.00 | 36.88 | B | C |
| ATOM | 14795 | CZ | TYR | B | 403 | 44.210 | 25.112 | −35.091 | 1.00 | 36.98 | B | C |
| ATOM | 14796 | OH | TYR | B | 403 | 45.014 | 24.010 | −35.296 | 1.00 | 43.37 | B | O |
| ATOM | 14798 | CE2 | TYR | B | 403 | 44.688 | 26.381 | −34.763 | 1.00 | 35.63 | B | C |
| ATOM | 14800 | CD2 | TYR | B | 403 | 43.772 | 27.416 | −34.602 | 1.00 | 28.89 | B | C |
| ATOM | 14802 | C | TYR | B | 403 | 41.897 | 28.421 | −32.195 | 1.00 | 20.62 | B | C |
| ATOM | 14803 | O | TYR | B | 403 | 42.306 | 27.462 | −31.567 | 1.00 | 21.48 | B | O |
| ATOM | 14805 | N | PHE | B | 404 | 42.401 | 29.633 | −32.053 | 1.00 | 21.49 | B | N |
| ATOM | 14806 | CA | PHE | B | 404 | 43.555 | 29.869 | −31.181 | 1.00 | 21.36 | B | C |
| ATOM | 14808 | CB | PHE | B | 404 | 44.194 | 31.232 | −31.479 | 1.00 | 20.72 | B | C |
| ATOM | 14811 | CG | PHE | B | 404 | 45.349 | 31.561 | −30.618 | 1.00 | 18.53 | B | C |
| ATOM | 14812 | CD1 | PHE | B | 404 | 46.497 | 30.774 | −30.637 | 1.00 | 24.02 | B | C |
| ATOM | 14814 | CE1 | PHE | B | 404 | 47.570 | 31.076 | −29.822 | 1.00 | 19.40 | B | C |
| ATOM | 14816 | CZ | PHE | B | 404 | 47.510 | 32.189 | −28.985 | 1.00 | 21.28 | B | C |
| ATOM | 14818 | CE2 | PHE | B | 404 | 46.382 | 32.969 | −28.957 | 1.00 | 24.12 | B | C |
| ATOM | 14820 | CD2 | PHE | B | 404 | 45.306 | 32.658 | −29.776 | 1.00 | 23.06 | B | C |
| ATOM | 14822 | C | PHE | B | 404 | 43.125 | 29.726 | −29.740 | 1.00 | 21.63 | B | C |
| ATOM | 14823 | O | PHE | B | 404 | 43.825 | 29.110 | −28.945 | 1.00 | 17.99 | B | O |
| ATOM | 14825 | N | GLY | B | 405 | 41.946 | 30.249 | −29.399 | 1.00 | 22.47 | B | N |
| ATOM | 14826 | CA | GLY | B | 405 | 41.436 | 30.071 | −28.039 | 1.00 | 22.00 | B | C |
| ATOM | 14829 | C | GLY | B | 405 | 41.509 | 28.604 | −27.605 | 1.00 | 23.01 | B | C |
| ATOM | 14830 | O | GLY | B | 405 | 41.945 | 28.286 | −26.503 | 1.00 | 25.26 | B | O |
| ATOM | 14832 | N | ASN | B | 406 | 41.049 | 27.711 | −28.474 | 1.00 | 21.92 | B | N |
| ATOM | 14833 | CA | ASN | B | 406 | 41.158 | 26.281 | −28.253 | 1.00 | 21.40 | B | C |
| ATOM | 14835 | CB | ASN | B | 406 | 40.293 | 25.515 | −29.253 | 1.00 | 21.75 | B | C |
| ATOM | 14838 | CG | ASN | B | 406 | 40.155 | 24.061 | −28.891 | 1.00 | 24.28 | B | C |
| ATOM | 14839 | OD1 | ASN | B | 406 | 39.504 | 23.735 | −27.911 | 1.00 | 22.62 | B | O |
| ATOM | 14840 | ND2 | ASN | B | 406 | 40.776 | 23.176 | −29.681 | 1.00 | 16.03 | B | N |
| ATOM | 14843 | C | ASN | B | 406 | 42.606 | 25.765 | −28.361 | 1.00 | 20.04 | B | C |
| ATOM | 14844 | O | ASN | B | 406 | 43.029 | 24.937 | −27.563 | 1.00 | 20.34 | B | O |
| ATOM | 14846 | N | ALA | B | 407 | 43.348 | 26.236 | −29.353 | 1.00 | 18.11 | B | N |
| ATOM | 14847 | CA | ALA | B | 407 | 44.675 | 25.668 | −29.610 | 1.00 | 19.56 | B | C |
| ATOM | 14849 | CB | ALA | B | 407 | 45.224 | 26.153 | −30.939 | 1.00 | 16.25 | B | C |

TABLE 4-2-continued

Coordinates of *P. alba* IspS

| | | | | | | | | | | | | |
|---|---|---|---|---|---|---|---|---|---|---|---|---|
| ATOM | 14853 | C | ALA | B | 407 | 45.701 | 25.884 | −28.493 | 1.00 | 20.02 | B | C |
| ATOM | 14854 | O | ALA | B | 407 | 46.604 | 25.031 | −28.294 | 1.00 | 20.33 | B | O |
| ATOM | 14856 | N | TRP | B | 408 | 45.611 | 27.007 | −27.782 | 1.00 | 18.45 | B | N |
| ATOM | 14857 | CA | TRP | B | 408 | 46.564 | 27.232 | −26.710 | 1.00 | 20.53 | B | C |
| ATOM | 14859 | CB | TRP | B | 408 | 46.737 | 28.706 | −26.290 | 1.00 | 19.32 | B | C |
| ATOM | 14862 | CG | TRP | B | 408 | 45.544 | 29.473 | −25.694 | 1.00 | 19.23 | B | C |
| ATOM | 14863 | CD1 | TRP | B | 408 | 44.789 | 30.419 | −26.330 | 1.00 | 22.29 | B | C |
| ATOM | 14865 | NE1 | TRP | B | 408 | 43.833 | 30.934 | −25.473 | 1.00 | 20.57 | B | N |
| ATOM | 14867 | CE2 | TRP | B | 408 | 43.966 | 30.336 | −24.257 | 1.00 | 21.54 | B | C |
| ATOM | 14868 | CD2 | TRP | B | 408 | 45.052 | 29.418 | −24.351 | 1.00 | 22.09 | B | C |
| ATOM | 14869 | CE3 | TRP | B | 408 | 45.409 | 28.682 | −23.214 | 1.00 | 22.59 | B | C |
| ATOM | 14871 | CZ3 | TRP | B | 408 | 44.687 | 28.893 | −22.028 | 1.00 | 23.88 | B | C |
| ATOM | 14873 | CH2 | TRP | B | 408 | 43.606 | 29.809 | −21.980 | 1.00 | 21.62 | B | C |
| ATOM | 14875 | CZ2 | TRP | B | 408 | 43.244 | 30.540 | −23.076 | 1.00 | 24.64 | B | C |
| ATOM | 14877 | C | TRP | B | 408 | 46.269 | 26.329 | −25.543 | 1.00 | 20.19 | B | C |
| ATOM | 14878 | O | TRP | B | 408 | 47.159 | 26.031 | −24.773 | 1.00 | 24.69 | B | O |
| ATOM | 14880 | N | LYS | B | 409 | 45.040 | 25.858 | −25.431 | 1.00 | 19.87 | B | N |
| ATOM | 14881 | CA | LYS | B | 409 | 44.720 | 24.842 | −24.443 | 1.00 | 20.66 | B | C |
| ATOM | 14883 | CB | LYS | B | 409 | 43.222 | 24.797 | −24.163 | 1.00 | 18.56 | B | C |
| ATOM | 14886 | CG | LYS | B | 409 | 42.667 | 26.085 | −23.503 | 1.00 | 25.88 | B | C |
| ATOM | 14889 | CD | LYS | B | 409 | 41.159 | 26.021 | −23.179 | 1.00 | 33.24 | B | C |
| ATOM | 14892 | CE | LYS | B | 409 | 40.581 | 27.370 | −22.701 | 1.00 | 37.85 | B | C |
| ATOM | 14895 | NZ | LYS | B | 409 | 40.211 | 28.350 | −23.840 | 1.00 | 45.13 | B | N |
| ATOM | 14899 | C | LYS | B | 409 | 45.248 | 23.476 | −24.902 | 1.00 | 20.55 | B | C |
| ATOM | 14900 | O | LYS | B | 409 | 45.859 | 22.746 | −24.116 | 1.00 | 18.30 | B | O |
| ATOM | 14902 | N | SER | B | 410 | 45.068 | 23.178 | −26.186 | 1.00 | 20.61 | B | N |
| ATOM | 14903 | CA | SER | B | 410 | 45.448 | 21.878 | −26.756 | 1.00 | 20.11 | B | C |
| ATOM | 14905 | CB | SER | B | 410 | 44.882 | 21.701 | −28.183 | 1.00 | 21.28 | B | C |
| ATOM | 14908 | OG | SER | B | 410 | 45.676 | 22.371 | −29.177 | 1.00 | 18.53 | B | O |
| ATOM | 14910 | C | SER | B | 410 | 46.943 | 21.693 | −26.827 | 1.00 | 21.39 | B | C |
| ATOM | 14911 | O | SER | B | 410 | 47.400 | 20.598 | −27.087 | 1.00 | 21.38 | B | O |
| ATOM | 14913 | N | SER | B | 411 | 47.703 | 22.775 | −26.667 | 1.00 | 22.35 | B | N |
| ATOM | 14914 | CA | SER | B | 411 | 49.155 | 22.694 | −26.608 | 1.00 | 20.21 | B | C |
| ATOM | 14916 | CB | SER | B | 411 | 49.790 | 24.084 | −26.486 | 1.00 | 21.74 | B | C |
| ATOM | 14919 | OG | SER | B | 411 | 49.520 | 24.719 | −25.216 | 1.00 | 20.26 | B | O |
| ATOM | 14921 | C | SER | B | 411 | 49.584 | 21.872 | −25.411 | 1.00 | 19.55 | B | C |
| ATOM | 14922 | O | SER | B | 411 | 50.645 | 21.322 | −25.433 | 1.00 | 19.31 | B | O |
| ATOM | 14924 | N | SER | B | 412 | 48.738 | 21.814 | −24.380 | 1.00 | 21.60 | B | N |
| ATOM | 14925 | CA | SER | B | 412 | 49.017 | 21.190 | −23.068 | 1.00 | 22.15 | B | C |
| ATOM | 14927 | CB | SER | B | 412 | 49.701 | 19.819 | −23.183 | 1.00 | 22.20 | B | C |
| ATOM | 14930 | OG | SER | B | 412 | 51.094 | 19.930 | −23.403 | 1.00 | 20.47 | B | O |
| ATOM | 14932 | C | SER | B | 412 | 49.810 | 22.101 | −22.119 | 1.00 | 21.31 | B | C |
| ATOM | 14933 | O | SER | B | 412 | 50.103 | 21.730 | −20.970 | 1.00 | 21.57 | B | O |
| ATOM | 14935 | N | GLY | B | 413 | 50.107 | 23.308 | −22.574 | 1.00 | 18.89 | B | N |
| ATOM | 14936 | CA | GLY | B | 413 | 50.807 | 24.295 | −21.751 | 1.00 | 19.18 | B | C |
| ATOM | 14939 | C | GLY | B | 413 | 50.152 | 24.531 | −20.408 | 1.00 | 19.27 | B | C |
| ATOM | 14940 | O | GLY | B | 413 | 50.809 | 24.440 | −19.363 | 1.00 | 20.22 | B | O |
| ATOM | 14942 | N | PRO | B | 414 | 48.851 | 24.815 | −20.412 | 1.00 | 17.74 | B | N |
| ATOM | 14943 | CA | PRO | B | 414 | 48.178 | 25.038 | −19.143 | 1.00 | 20.20 | B | C |
| ATOM | 14945 | CB | PRO | B | 414 | 46.720 | 25.297 | −19.567 | 1.00 | 20.76 | B | C |
| ATOM | 14948 | CG | PRO | B | 414 | 46.881 | 25.963 | −20.871 | 1.00 | 16.96 | B | C |
| ATOM | 14951 | CD | PRO | B | 414 | 47.965 | 25.139 | −21.537 | 1.00 | 18.57 | B | C |
| ATOM | 14954 | C | PRO | B | 414 | 48.247 | 23.840 | −18.218 | 1.00 | 20.58 | B | C |
| ATOM | 14955 | O | PRO | B | 414 | 48.536 | 23.995 | −17.047 | 1.00 | 20.97 | B | O |
| ATOM | 14956 | N | LEU | B | 415 | 48.005 | 22.654 | −18.768 | 1.00 | 22.11 | B | N |
| ATOM | 14957 | CA | LEU | B | 415 | 48.040 | 21.432 | −17.994 | 1.00 | 21.93 | B | C |
| ATOM | 14959 | CB | LEU | B | 415 | 47.677 | 20.224 | −18.870 | 1.00 | 22.71 | B | C |
| ATOM | 14962 | CG | LEU | B | 415 | 47.827 | 18.842 | −18.222 | 1.00 | 24.25 | B | C |
| ATOM | 14964 | CD1 | LEU | B | 415 | 46.773 | 17.860 | −18.751 | 1.00 | 21.18 | B | C |
| ATOM | 14968 | CD2 | LEU | B | 415 | 49.234 | 18.290 | −18.421 | 1.00 | 23.53 | B | C |
| ATOM | 14972 | C | LEU | B | 415 | 49.420 | 21.225 | −17.393 | 1.00 | 22.23 | B | C |
| ATOM | 14973 | O | LEU | B | 415 | 49.540 | 20.955 | −16.209 | 1.00 | 21.62 | B | O |
| ATOM | 14975 | N | GLN | B | 416 | 50.459 | 21.330 | −18.214 | 1.00 | 21.75 | B | N |
| ATOM | 14976 | CA | GLN | B | 416 | 51.824 | 21.221 | −17.701 | 1.00 | 20.58 | B | C |
| ATOM | 14978 | CB | GLN | B | 416 | 52.834 | 21.502 | −18.790 | 1.00 | 19.97 | B | C |
| ATOM | 14981 | CG | GLN | B | 416 | 52.840 | 20.447 | −19.842 | 1.00 | 19.48 | B | C |
| ATOM | 14984 | CD | GLN | B | 416 | 53.920 | 20.659 | −20.837 | 1.00 | 26.66 | B | C |
| ATOM | 14985 | OE1 | GLN | B | 416 | 55.002 | 21.132 | −20.494 | 1.00 | 29.08 | B | O |
| ATOM | 14986 | NE2 | GLN | B | 416 | 53.658 | 20.284 | −22.089 | 1.00 | 24.07 | B | N |
| ATOM | 14989 | C | GLN | B | 416 | 52.062 | 22.162 | −16.544 | 1.00 | 21.03 | B | C |
| ATOM | 14990 | O | GLN | B | 416 | 52.701 | 21.799 | −15.558 | 1.00 | 23.28 | B | O |
| ATOM | 14992 | N | LEU | B | 417 | 51.545 | 23.374 | −16.636 | 1.00 | 19.90 | B | N |
| ATOM | 14993 | CA | LEU | B | 417 | 51.878 | 24.340 | −15.611 | 1.00 | 20.19 | B | C |
| ATOM | 14995 | CB | LEU | B | 417 | 51.770 | 25.766 | −16.117 | 1.00 | 20.53 | B | C |
| ATOM | 14998 | CG | LEU | B | 417 | 52.799 | 26.171 | −17.174 | 1.00 | 17.82 | B | C |
| ATOM | 15000 | CD1 | LEU | B | 417 | 52.466 | 27.556 | −17.758 | 1.00 | 18.27 | B | C |
| ATOM | 15004 | CD2 | LEU | B | 417 | 54.219 | 26.142 | −16.607 | 1.00 | 18.14 | B | C |
| ATOM | 15008 | C | LEU | B | 417 | 51.034 | 24.114 | −14.371 | 1.00 | 20.73 | B | C |

TABLE 4-2-continued

Coordinates of *P. alba* IspS

| | | | | | | | | | | | | |
|---|---|---|---|---|---|---|---|---|---|---|---|---|
| ATOM | 15009 | O | LEU | B | 417 | 51.472 | 24.460 | −13.291 | 1.00 | 21.82 | B | O |
| ATOM | 15011 | N | VAL | B | 418 | 49.841 | 23.516 | −14.500 | 1.00 | 21.29 | B | N |
| ATOM | 15012 | CA | VAL | B | 418 | 49.081 | 23.104 | −13.310 | 1.00 | 20.26 | B | C |
| ATOM | 15014 | CB | VAL | B | 418 | 47.702 | 22.530 | −13.655 | 1.00 | 21.33 | B | C |
| ATOM | 15016 | CG1 | VAL | B | 418 | 46.715 | 23.671 | −14.083 | 1.00 | 17.04 | B | C |
| ATOM | 15020 | CG2 | VAL | B | 418 | 47.139 | 21.793 | −12.468 | 1.00 | 19.19 | B | C |
| ATOM | 15024 | C | VAL | B | 418 | 49.929 | 22.077 | −12.549 | 1.00 | 21.33 | B | C |
| ATOM | 15025 | O | VAL | B | 418 | 50.114 | 22.181 | −11.350 | 1.00 | 21.65 | B | O |
| ATOM | 15027 | N | PHE | B | 419 | 50.498 | 21.125 | −13.269 | 1.00 | 18.97 | B | N |
| ATOM | 15028 | CA | PHE | B | 419 | 51.345 | 20.140 | −12.648 | 1.00 | 19.89 | B | C |
| ATOM | 15030 | CB | PHE | B | 419 | 51.657 | 19.015 | −13.610 | 1.00 | 19.38 | B | C |
| ATOM | 15033 | CG | PHE | B | 419 | 50.563 | 17.967 | −13.689 | 1.00 | 19.90 | B | C |
| ATOM | 15034 | CD1 | PHE | B | 419 | 50.670 | 16.777 | −12.971 | 1.00 | 18.98 | B | C |
| ATOM | 15036 | CE1 | PHE | B | 419 | 49.668 | 15.827 | −13.011 | 1.00 | 19.09 | B | C |
| ATOM | 15038 | CZ | PHE | B | 419 | 48.533 | 16.046 | −13.802 | 1.00 | 20.18 | B | C |
| ATOM | 15040 | CE2 | PHE | B | 419 | 48.424 | 17.216 | −14.534 | 1.00 | 18.86 | B | C |
| ATOM | 15042 | CD2 | PHE | B | 419 | 49.436 | 18.178 | −14.460 | 1.00 | 17.01 | B | C |
| ATOM | 15044 | C | PHE | B | 419 | 52.620 | 20.762 | −12.087 | 1.00 | 20.16 | B | C |
| ATOM | 15045 | O | PHE | B | 419 | 53.021 | 20.417 | −10.991 | 1.00 | 20.38 | B | O |
| ATOM | 15047 | N | ALA | B | 420 | 53.239 | 21.684 | −12.812 | 1.00 | 20.42 | B | N |
| ATOM | 15048 | CA | ALA | B | 420 | 54.427 | 22.338 | −12.289 | 1.00 | 23.24 | B | C |
| ATOM | 15050 | CB | ALA | B | 420 | 55.062 | 23.322 | −13.324 | 1.00 | 21.28 | B | C |
| ATOM | 15054 | C | ALA | B | 420 | 54.061 | 23.045 | −10.988 | 1.00 | 24.47 | B | C |
| ATOM | 15055 | O | ALA | B | 420 | 54.800 | 22.943 | −10.007 | 1.00 | 25.28 | B | O |
| ATOM | 15057 | N | TYR | B | 421 | 52.889 | 23.683 | −10.947 | 1.00 | 24.54 | B | N |
| ATOM | 15058 | CA | TYR | B | 421 | 52.478 | 24.429 | −9.753 | 1.00 | 23.69 | B | C |
| ATOM | 15060 | CB | TYR | B | 421 | 51.039 | 24.958 | −9.879 | 1.00 | 23.32 | B | C |
| ATOM | 15063 | CG | TYR | B | 421 | 50.497 | 25.608 | −8.616 | 1.00 | 24.00 | B | C |
| ATOM | 15064 | CD1 | TYR | B | 421 | 50.904 | 26.885 | −8.220 | 1.00 | 27.39 | B | C |
| ATOM | 15066 | CE1 | TYR | B | 421 | 50.418 | 27.466 | −7.053 | 1.00 | 26.70 | B | C |
| ATOM | 15068 | CZ | TYR | B | 421 | 49.527 | 26.759 | −6.268 | 1.00 | 27.74 | B | C |
| ATOM | 15069 | OH | TYR | B | 421 | 49.003 | 27.300 | −5.109 | 1.00 | 29.86 | B | O |
| ATOM | 15071 | CE2 | TYR | B | 421 | 49.129 | 25.503 | −6.642 | 1.00 | 26.17 | B | C |
| ATOM | 15073 | CD2 | TYR | B | 421 | 49.616 | 24.931 | −7.797 | 1.00 | 28.12 | B | C |
| ATOM | 15075 | C | TYR | B | 421 | 52.618 | 23.546 | −8.524 | 1.00 | 25.70 | B | C |
| ATOM | 15076 | O | TYR | B | 421 | 53.296 | 23.894 | −7.553 | 1.00 | 25.07 | B | O |
| ATOM | 15078 | N | PHE | B | 422 | 52.001 | 22.374 | −8.560 | 1.00 | 26.45 | B | N |
| ATOM | 15079 | CA | PHE | B | 422 | 51.998 | 21.538 | −7.363 | 1.00 | 23.99 | B | C |
| ATOM | 15081 | CB | PHE | B | 422 | 50.959 | 20.448 | −7.476 | 1.00 | 23.45 | B | C |
| ATOM | 15084 | CG | PHE | B | 422 | 49.564 | 20.962 | −7.545 | 1.00 | 21.76 | B | C |
| ATOM | 15085 | CD1 | PHE | B | 422 | 48.963 | 21.499 | −6.425 | 1.00 | 22.67 | B | C |
| ATOM | 15087 | CE1 | PHE | B | 422 | 47.677 | 21.970 | −6.487 | 1.00 | 22.09 | B | C |
| ATOM | 15089 | CZ | PHE | B | 422 | 46.996 | 21.931 | −7.682 | 1.00 | 23.94 | B | C |
| ATOM | 15091 | CE2 | PHE | B | 422 | 47.594 | 21.400 | −8.798 | 1.00 | 24.20 | B | C |
| ATOM | 15093 | CD2 | PHE | B | 422 | 48.852 | 20.905 | −8.722 | 1.00 | 21.31 | B | C |
| ATOM | 15095 | C | PHE | B | 422 | 53.386 | 20.973 | −7.060 | 1.00 | 25.00 | B | C |
| ATOM | 15096 | O | PHE | B | 422 | 53.687 | 20.659 | −5.916 | 1.00 | 27.56 | B | O |
| ATOM | 15098 | N | ALA | B | 423 | 54.245 | 20.878 | −8.067 | 1.00 | 24.59 | B | N |
| ATOM | 15099 | CA | ALA | B | 423 | 55.591 | 20.352 | −7.857 | 1.00 | 24.37 | B | C |
| ATOM | 15101 | CB | ALA | B | 423 | 56.065 | 19.705 | −9.117 | 1.00 | 21.00 | B | C |
| ATOM | 15105 | C | ALA | B | 423 | 56.647 | 21.370 | −7.363 | 1.00 | 26.64 | B | C |
| ATOM | 15106 | O | ALA | B | 423 | 57.710 | 20.965 | −6.870 | 1.00 | 30.03 | B | O |
| ATOM | 15108 | N | VAL | B | 424 | 56.397 | 22.664 | −7.547 | 1.00 | 27.57 | B | N |
| ATOM | 15109 | CA | VAL | B | 424 | 57.351 | 23.700 | −7.160 | 1.00 | 29.54 | B | C |
| ATOM | 15111 | CB | VAL | B | 424 | 57.704 | 24.619 | −8.341 | 1.00 | 29.56 | B | C |
| ATOM | 15113 | CG1 | VAL | B | 424 | 58.149 | 23.780 | −9.552 | 1.00 | 26.25 | B | C |
| ATOM | 15117 | CG2 | VAL | B | 424 | 56.527 | 25.557 | −8.684 | 1.00 | 22.59 | B | C |
| ATOM | 15121 | C | VAL | B | 424 | 56.887 | 24.597 | −6.011 | 1.00 | 32.82 | B | C |
| ATOM | 15122 | O | VAL | B | 424 | 57.704 | 25.262 | −5.422 | 1.00 | 34.23 | B | O |
| ATOM | 15124 | N | VAL | B | 425 | 55.593 | 24.633 | −5.713 | 1.00 | 34.79 | B | N |
| ATOM | 15125 | CA | VAL | B | 425 | 55.076 | 25.505 | −4.675 | 1.00 | 38.89 | B | C |
| ATOM | 15127 | CB | VAL | B | 425 | 53.717 | 26.073 | −5.071 | 1.00 | 39.09 | B | C |
| ATOM | 15129 | CG1 | VAL | B | 425 | 53.005 | 26.649 | −3.867 | 1.00 | 38.93 | B | C |
| ATOM | 15133 | CG2 | VAL | B | 425 | 53.911 | 27.138 | −6.142 | 1.00 | 37.94 | B | C |
| ATOM | 15137 | C | VAL | B | 425 | 54.946 | 24.779 | −3.343 | 1.00 | 43.65 | B | C |
| ATOM | 15138 | O | VAL | B | 425 | 54.204 | 23.803 | −3.242 | 1.00 | 45.04 | B | O |
| ATOM | 15140 | N | GLN | B | 426 | 55.647 | 25.279 | −2.322 | 1.00 | 47.45 | B | N |
| ATOM | 15141 | CA | GLN | B | 426 | 55.676 | 24.630 | −1.008 | 1.00 | 50.46 | B | C |
| ATOM | 15143 | CB | GLN | B | 426 | 56.627 | 25.368 | −0.053 | 1.00 | 53.33 | B | C |
| ATOM | 15146 | CG | GLN | B | 426 | 58.129 | 25.084 | −0.275 | 1.00 | 61.88 | B | C |
| ATOM | 15149 | CD | GLN | B | 426 | 59.034 | 25.792 | 0.746 | 1.00 | 68.89 | B | C |
| ATOM | 15150 | OE1 | GLN | B | 426 | 59.973 | 26.503 | 0.376 | 1.00 | 73.47 | B | O |
| ATOM | 15151 | NE2 | GLN | B | 426 | 58.742 | 25.602 | 2.034 | 1.00 | 69.40 | B | N |
| ATOM | 15154 | C | GLN | B | 426 | 54.285 | 24.519 | −0.377 | 1.00 | 48.54 | B | C |
| ATOM | 15155 | O | GLN | B | 426 | 53.887 | 23.437 | 0.037 | 1.00 | 49.02 | B | O |
| ATOM | 15157 | N | ASN | B | 427 | 53.554 | 25.633 | −0.316 | 1.00 | 46.21 | B | N |
| ATOM | 15158 | CA | ASN | B | 427 | 52.232 | 25.673 | 0.318 | 1.00 | 44.18 | B | C |
| ATOM | 15160 | CB | ASN | B | 427 | 52.271 | 26.578 | 1.552 | 1.00 | 45.10 | B | C |

TABLE 4-2-continued

Coordinates of *P. alba* IspS

| | | | | | | | | | | | | |
|---|---|---|---|---|---|---|---|---|---|---|---|---|
| ATOM | 15163 | CG | ASN | B | 427 | 53.065 | 25.963 | 2.691 | 1.00 | 46.27 | B | C |
| ATOM | 15164 | OD1 | ASN | B | 427 | 52.520 | 25.213 | 3.510 | 1.00 | 43.08 | B | O |
| ATOM | 15165 | ND2 | ASN | B | 427 | 54.366 | 26.235 | 2.717 | 1.00 | 38.93 | B | N |
| ATOM | 15168 | C | ASN | B | 427 | 51.156 | 26.170 | −0.631 | 1.00 | 42.56 | B | C |
| ATOM | 15169 | O | ASN | B | 427 | 51.127 | 27.352 | −0.981 | 1.00 | 42.40 | B | O |
| ATOM | 15171 | N | ILE | B | 428 | 50.256 | 25.276 | −1.024 | 1.00 | 40.21 | B | N |
| ATOM | 15172 | CA | ILE | B | 428 | 49.250 | 25.617 | −2.008 | 1.00 | 40.37 | B | C |
| ATOM | 15174 | CB | ILE | B | 428 | 48.597 | 24.364 | −2.634 | 1.00 | 41.28 | B | C |
| ATOM | 15176 | CG1 | ILE | B | 428 | 47.742 | 23.600 | −1.630 | 1.00 | 40.63 | B | C |
| ATOM | 15179 | CD1 | ILE | B | 428 | 46.969 | 22.501 | −2.264 | 1.00 | 38.48 | B | C |
| ATOM | 15183 | CG2 | ILE | B | 428 | 49.675 | 23.424 | −3.196 | 1.00 | 43.55 | B | C |
| ATOM | 15187 | C | ILE | B | 428 | 48.200 | 26.516 | −1.391 | 1.00 | 40.76 | B | C |
| ATOM | 15188 | O | ILE | B | 428 | 47.902 | 26.395 | −0.201 | 1.00 | 41.46 | B | O |
| ATOM | 15190 | N | LYS | B | 429 | 47.657 | 27.422 | −2.198 | 1.00 | 39.80 | B | N |
| ATOM | 15191 | CA | LYS | B | 429 | 46.602 | 28.323 | −1.759 | 1.00 | 39.22 | B | C |
| ATOM | 15193 | CB | LYS | B | 429 | 47.071 | 29.776 | −1.808 | 1.00 | 39.67 | B | C |
| ATOM | 15196 | CG | LYS | B | 429 | 48.269 | 30.048 | −0.920 | 1.00 | 45.60 | B | C |
| ATOM | 15199 | CD | LYS | B | 429 | 48.879 | 31.429 | −1.157 | 1.00 | 50.03 | B | C |
| ATOM | 15202 | CE | LYS | B | 429 | 50.249 | 31.534 | −0.469 | 1.00 | 53.38 | B | C |
| ATOM | 15205 | NZ | LYS | B | 429 | 50.713 | 32.937 | −0.367 | 1.00 | 55.16 | B | N |
| ATOM | 15209 | C | LYS | B | 429 | 45.389 | 28.158 | −2.637 | 1.00 | 38.88 | B | C |
| ATOM | 15210 | O | LYS | B | 429 | 45.492 | 27.998 | −3.854 | 1.00 | 37.10 | B | O |
| ATOM | 15212 | N | LYS | B | 430 | 44.229 | 28.230 | −2.007 | 1.00 | 40.34 | B | N |
| ATOM | 15213 | CA | LYS | B | 430 | 42.985 | 27.967 | −2.682 | 1.00 | 41.57 | B | C |
| ATOM | 15215 | CB | LYS | B | 430 | 41.820 | 28.099 | −1.691 | 1.00 | 44.11 | B | C |
| ATOM | 15218 | CG | LYS | B | 430 | 40.448 | 27.690 | −2.234 | 1.00 | 52.05 | B | C |
| ATOM | 15221 | CD | LYS | B | 430 | 39.363 | 27.760 | −1.142 | 1.00 | 63.27 | B | C |
| ATOM | 15224 | CE | LYS | B | 430 | 38.943 | 29.200 | −0.822 | 1.00 | 67.72 | B | C |
| ATOM | 15227 | NZ | LYS | B | 430 | 38.124 | 29.784 | −1.928 | 1.00 | 71.21 | B | N |
| ATOM | 15231 | C | LYS | B | 430 | 42.802 | 28.927 | −3.843 | 1.00 | 39.97 | B | C |
| ATOM | 15232 | O | LYS | B | 430 | 42.358 | 28.523 | −4.913 | 1.00 | 39.98 | B | O |
| ATOM | 15234 | N | GLU | B | 431 | 43.130 | 30.198 | −3.639 | 1.00 | 39.37 | B | N |
| ATOM | 15235 | CA | GLU | B | 431 | 42.843 | 31.191 | −4.666 | 1.00 | 39.18 | B | C |
| ATOM | 15237 | CB | GLU | B | 431 | 42.743 | 32.612 | −4.088 | 1.00 | 40.15 | B | C |
| ATOM | 15240 | CG | GLU | B | 431 | 44.049 | 33.364 | −3.837 | 1.00 | 50.24 | B | C |
| ATOM | 15243 | CD | GLU | B | 431 | 43.829 | 34.872 | −3.580 | 1.00 | 60.38 | B | C |
| ATOM | 15244 | OE1 | GLU | B | 431 | 43.114 | 35.532 | −4.376 | 1.00 | 62.25 | B | O |
| ATOM | 15245 | OE2 | GLU | B | 431 | 44.376 | 35.396 | −2.582 | 1.00 | 62.66 | B | O |
| ATOM | 15246 | C | GLU | B | 431 | 43.813 | 31.070 | −5.848 | 1.00 | 35.93 | B | C |
| ATOM | 15247 | O | GLU | B | 431 | 43.442 | 31.367 | −6.982 | 1.00 | 34.81 | B | O |
| ATOM | 15249 | N | GLU | B | 432 | 45.034 | 30.618 | −5.585 | 1.00 | 33.41 | B | N |
| ATOM | 15250 | CA | GLU | B | 432 | 45.965 | 30.298 | −6.660 | 1.00 | 33.72 | B | C |
| ATOM | 15252 | CB | GLU | B | 432 | 47.353 | 29.955 | −6.109 | 1.00 | 33.21 | B | C |
| ATOM | 15255 | CG | GLU | B | 432 | 48.085 | 31.141 | −5.456 | 1.00 | 32.22 | B | C |
| ATOM | 15258 | CD | GLU | B | 432 | 49.493 | 30.803 | −4.956 | 1.00 | 37.75 | B | C |
| ATOM | 15259 | OE1 | GLU | B | 432 | 49.791 | 29.622 | −4.631 | 1.00 | 34.91 | B | O |
| ATOM | 15260 | OE2 | GLU | B | 432 | 50.317 | 31.745 | −4.883 | 1.00 | 45.57 | B | O |
| ATOM | 15261 | C | GLU | B | 432 | 45.406 | 29.146 | −7.507 | 1.00 | 33.26 | B | C |
| ATOM | 15262 | O | GLU | B | 432 | 45.304 | 29.260 | −8.728 | 1.00 | 34.10 | B | O |
| ATOM | 15264 | N | ILE | B | 433 | 44.992 | 28.056 | −6.873 | 1.00 | 33.07 | B | N |
| ATOM | 15265 | CA | ILE | B | 433 | 44.509 | 26.923 | −7.661 | 1.00 | 34.77 | B | C |
| ATOM | 15267 | CB | ILE | B | 433 | 44.529 | 25.571 | −6.921 | 1.00 | 33.31 | B | C |
| ATOM | 15269 | CG1 | ILE | B | 433 | 43.828 | 25.602 | −5.594 | 1.00 | 39.69 | B | C |
| ATOM | 15272 | CD1 | ILE | B | 433 | 44.565 | 24.744 | −4.570 | 1.00 | 40.72 | B | C |
| ATOM | 15276 | CG2 | ILE | B | 433 | 45.949 | 25.194 | −6.576 | 1.00 | 37.35 | B | C |
| ATOM | 15280 | C | ILE | B | 433 | 43.190 | 27.234 | −8.334 | 1.00 | 33.17 | B | C |
| ATOM | 15281 | O | ILE | B | 433 | 42.938 | 26.745 | −9.419 | 1.00 | 34.85 | B | O |
| ATOM | 15283 | N | GLU | B | 434 | 42.384 | 28.100 | −7.750 | 1.00 | 31.81 | B | N |
| ATOM | 15284 | CA | GLU | B | 434 | 41.167 | 28.532 | −8.428 | 1.00 | 33.28 | B | C |
| ATOM | 15286 | CB | GLU | B | 434 | 40.259 | 29.351 | −7.499 | 1.00 | 36.58 | B | C |
| ATOM | 15289 | CG | GLU | B | 434 | 39.295 | 28.482 | −6.669 | 1.00 | 45.80 | B | C |
| ATOM | 15292 | CD | GLU | B | 434 | 38.349 | 29.297 | −5.797 | 1.00 | 58.22 | B | C |
| ATOM | 15293 | OE1 | GLU | B | 434 | 38.744 | 30.392 | −5.318 | 1.00 | 61.60 | B | O |
| ATOM | 15294 | OE2 | GLU | B | 434 | 37.204 | 28.834 | −5.597 | 1.00 | 62.57 | B | O |
| ATOM | 15295 | C | GLU | B | 434 | 41.470 | 29.333 | −9.681 | 1.00 | 31.01 | B | C |
| ATOM | 15296 | O | GLU | B | 434 | 40.724 | 29.260 | −10.669 | 1.00 | 32.01 | B | O |
| ATOM | 15298 | N | ASN | B | 435 | 42.546 | 30.108 | −9.641 | 1.00 | 27.38 | B | N |
| ATOM | 15299 | CA | ASN | B | 435 | 42.931 | 30.894 | −10.794 | 1.00 | 28.08 | B | C |
| ATOM | 15301 | CB | ASN | B | 435 | 43.789 | 32.084 | −10.362 | 1.00 | 28.78 | B | C |
| ATOM | 15304 | CG | ASN | B | 435 | 42.934 | 33.315 | −10.028 | 1.00 | 32.39 | B | C |
| ATOM | 15305 | OD1 | ASN | B | 435 | 42.351 | 33.953 | −10.913 | 1.00 | 39.25 | B | O |
| ATOM | 15306 | ND2 | ASN | B | 435 | 42.835 | 33.621 | −8.761 | 1.00 | 27.21 | B | N |
| ATOM | 15309 | C | ASN | B | 435 | 43.603 | 30.038 | −11.878 | 1.00 | 27.27 | B | C |
| ATOM | 15310 | O | ASN | B | 435 | 43.453 | 30.315 | −13.060 | 1.00 | 28.23 | B | O |
| ATOM | 15312 | N | LEU | B | 436 | 44.310 | 28.984 | −11.483 | 1.00 | 27.03 | B | N |
| ATOM | 15313 | CA | LEU | B | 436 | 44.817 | 28.023 | −12.463 | 1.00 | 28.24 | B | C |
| ATOM | 15315 | CB | LEU | B | 436 | 45.623 | 26.891 | −11.820 | 1.00 | 27.45 | B | C |
| ATOM | 15318 | CG | LEU | B | 436 | 46.900 | 27.257 | −11.062 | 1.00 | 26.99 | B | C |

TABLE 4-2-continued

| Coordinates of *P. alba* IspS | | | | | | | | | | | | |
|---|---|---|---|---|---|---|---|---|---|---|---|---|
| ATOM | 15320 | CD1 | LEU | B | 436 | 47.517 | 26.029 | −10.392 | 1.00 | 25.59 | B | C |
| ATOM | 15324 | CD2 | LEU | B | 436 | 47.879 | 27.938 | −11.979 | 1.00 | 26.36 | B | C |
| ATOM | 15328 | C | LEU | B | 436 | 43.639 | 27.442 | −13.231 | 1.00 | 29.56 | B | C |
| ATOM | 15329 | O | LEU | B | 436 | 43.671 | 27.408 | −14.445 | 1.00 | 30.09 | B | O |
| ATOM | 15331 | N | GLN | B | 437 | 42.577 | 27.034 | −12.535 | 1.00 | 32.04 | B | N |
| ATOM | 15332 | CA | GLN | B | 437 | 41.444 | 26.395 | −13.212 | 1.00 | 33.09 | B | C |
| ATOM | 15334 | CB | GLN | B | 437 | 40.418 | 25.838 | −12.226 | 1.00 | 34.27 | B | C |
| ATOM | 15337 | CG | GLN | B | 437 | 40.927 | 24.764 | −11.314 | 1.00 | 38.74 | B | C |
| ATOM | 15340 | CD | GLN | B | 437 | 39.827 | 23.808 | −10.859 | 1.00 | 42.01 | B | C |
| ATOM | 15341 | OE1 | GLN | B | 437 | 39.776 | 22.664 | −11.304 | 1.00 | 38.35 | B | O |
| ATOM | 15342 | NE2 | GLN | B | 437 | 38.949 | 24.275 | −9.971 | 1.00 | 34.39 | B | N |
| ATOM | 15345 | C | GLN | B | 437 | 40.736 | 27.365 | −14.137 | 1.00 | 32.68 | B | C |
| ATOM | 15346 | O | GLN | B | 437 | 40.030 | 26.933 | −15.041 | 1.00 | 33.51 | B | O |
| ATOM | 15348 | N | LYS | B | 438 | 40.886 | 28.663 | −13.893 | 1.00 | 31.93 | B | N |
| ATOM | 15349 | CA | LYS | B | 438 | 40.284 | 29.683 | −14.765 | 1.00 | 34.40 | B | C |
| ATOM | 15351 | CB | LYS | B | 438 | 39.717 | 30.835 | −13.933 | 1.00 | 36.15 | B | C |
| ATOM | 15354 | CG | LYS | B | 438 | 38.461 | 30.443 | −13.155 | 1.00 | 46.92 | B | C |
| ATOM | 15357 | CD | LYS | B | 438 | 38.218 | 31.319 | −11.915 | 1.00 | 56.20 | B | C |
| ATOM | 15360 | CE | LYS | B | 438 | 36.928 | 30.868 | −11.170 | 1.00 | 62.26 | B | C |
| ATOM | 15363 | NZ | LYS | B | 438 | 36.666 | 31.585 | −9.878 | 1.00 | 59.98 | B | N |
| ATOM | 15367 | C | LYS | B | 438 | 41.268 | 30.207 | −15.810 | 1.00 | 31.95 | B | C |
| ATOM | 15368 | O | LYS | B | 438 | 40.973 | 31.152 | −16.523 | 1.00 | 34.95 | B | O |
| ATOM | 15370 | N | TYR | B | 439 | 42.429 | 29.584 | −15.901 | 1.00 | 30.59 | B | N |
| ATOM | 15371 | CA | TYR | B | 439 | 43.454 | 29.951 | −16.874 | 1.00 | 31.05 | B | C |
| ATOM | 15373 | CB | TYR | B | 439 | 42.995 | 29.728 | −18.308 | 1.00 | 31.76 | B | C |
| ATOM | 15376 | CG | TYR | B | 439 | 42.559 | 28.327 | −18.592 | 1.00 | 35.31 | B | C |
| ATOM | 15377 | CD1 | TYR | B | 439 | 43.486 | 27.367 | −18.911 | 1.00 | 31.89 | B | C |
| ATOM | 15379 | CE1 | TYR | B | 439 | 43.110 | 26.094 | −19.190 | 1.00 | 44.43 | B | C |
| ATOM | 15381 | CZ | TYR | B | 439 | 41.785 | 25.748 | −19.147 | 1.00 | 43.22 | B | C |
| ATOM | 15382 | OH | TYR | B | 439 | 41.462 | 24.467 | −19.437 | 1.00 | 43.75 | B | O |
| ATOM | 15384 | CE2 | TYR | B | 439 | 40.808 | 26.685 | −18.827 | 1.00 | 40.92 | B | C |
| ATOM | 15386 | CD2 | TYR | B | 439 | 41.202 | 27.970 | −18.554 | 1.00 | 39.09 | B | C |
| ATOM | 15388 | C | TYR | B | 439 | 43.888 | 31.383 | −16.714 | 1.00 | 29.52 | B | C |
| ATOM | 15389 | O | TYR | B | 439 | 43.889 | 32.157 | −17.664 | 1.00 | 29.95 | B | O |
| ATOM | 15391 | N | HIS | B | 440 | 44.266 | 31.718 | −15.493 | 1.00 | 29.00 | B | N |
| ATOM | 15392 | CA | HIS | B | 440 | 44.898 | 32.986 | −15.198 | 1.00 | 27.83 | B | C |
| ATOM | 15394 | CB | HIS | B | 440 | 45.457 | 32.918 | −13.782 | 1.00 | 27.70 | B | C |
| ATOM | 15397 | CG | HIS | B | 440 | 45.905 | 34.238 | −13.250 | 1.00 | 34.45 | B | C |
| ATOM | 15398 | ND1 | HIS | B | 440 | 47.203 | 34.688 | −13.373 | 1.00 | 33.50 | B | N |
| ATOM | 15400 | CE1 | HIS | B | 440 | 47.301 | 35.881 | −12.815 | 1.00 | 35.67 | B | C |
| ATOM | 15402 | NE2 | HIS | B | 440 | 46.117 | 36.217 | −12.336 | 1.00 | 38.29 | B | N |
| ATOM | 15404 | CD2 | HIS | B | 440 | 45.226 | 35.208 | −12.599 | 1.00 | 32.67 | B | C |
| ATOM | 15406 | C | HIS | B | 440 | 46.052 | 33.277 | −16.167 | 1.00 | 27.83 | B | C |
| ATOM | 15407 | O | HIS | B | 440 | 46.792 | 32.364 | −16.577 | 1.00 | 23.95 | B | O |
| ATOM | 15409 | N | ASP | B | 441 | 46.206 | 34.557 | −16.499 | 1.00 | 27.43 | B | N |
| ATOM | 15410 | CA | ASP | B | 441 | 47.296 | 35.072 | −17.343 | 1.00 | 25.55 | B | C |
| ATOM | 15412 | CB | ASP | B | 441 | 47.448 | 36.575 | −17.122 | 1.00 | 26.88 | B | C |
| ATOM | 15415 | CG | ASP | B | 441 | 46.214 | 37.382 | −17.555 | 1.00 | 32.29 | B | C |
| ATOM | 15416 | OD1 | ASP | B | 441 | 45.520 | 36.981 | −18.519 | 1.00 | 32.54 | B | O |
| ATOM | 15417 | OD2 | ASP | B | 441 | 45.947 | 38.424 | −16.910 | 1.00 | 38.34 | B | O |
| ATOM | 15418 | C | ASP | B | 441 | 48.665 | 34.427 | −17.077 | 1.00 | 25.73 | B | C |
| ATOM | 15419 | O | ASP | B | 441 | 49.455 | 34.247 | −18.009 | 1.00 | 26.54 | B | O |
| ATOM | 15421 | N | THR | B | 442 | 48.956 | 34.084 | −15.822 | 1.00 | 24.23 | B | N |
| ATOM | 15422 | CA | THR | B | 442 | 50.254 | 33.441 | −15.475 | 1.00 | 25.82 | B | C |
| ATOM | 15424 | CB | THR | B | 442 | 50.317 | 33.025 | −13.995 | 1.00 | 26.22 | B | C |
| ATOM | 15426 | OG1 | THR | B | 442 | 50.066 | 34.173 | −13.192 | 1.00 | 32.69 | B | O |
| ATOM | 15428 | CG2 | THR | B | 442 | 51.692 | 32.497 | −13.624 | 1.00 | 28.30 | B | C |
| ATOM | 15432 | C | THR | B | 442 | 50.562 | 32.211 | −16.317 | 1.00 | 22.08 | B | C |
| ATOM | 15433 | O | THR | B | 442 | 51.699 | 31.994 | −16.697 | 1.00 | 21.58 | B | O |
| ATOM | 15435 | N | ILE | B | 443 | 49.538 | 31.421 | −16.605 | 1.00 | 22.63 | B | N |
| ATOM | 15436 | CA | ILE | B | 443 | 49.703 | 30.173 | −17.329 | 1.00 | 21.27 | B | C |
| ATOM | 15438 | CB | ILE | B | 443 | 49.127 | 28.948 | −16.523 | 1.00 | 21.12 | B | C |
| ATOM | 15440 | CG1 | ILE | B | 443 | 47.612 | 28.928 | −16.433 | 1.00 | 22.72 | B | C |
| ATOM | 15443 | CD1 | ILE | B | 443 | 47.033 | 27.558 | −15.846 | 1.00 | 18.38 | B | C |
| ATOM | 15447 | CG2 | ILE | B | 443 | 49.685 | 28.915 | −15.113 | 1.00 | 22.19 | B | C |
| ATOM | 15451 | C | ILE | B | 443 | 49.151 | 30.266 | −18.751 | 1.00 | 21.71 | B | C |
| ATOM | 15452 | O | ILE | B | 443 | 49.603 | 29.544 | −19.632 | 1.00 | 22.40 | B | O |
| ATOM | 15454 | N | SER | B | 444 | 48.220 | 31.189 | −19.008 | 1.00 | 23.19 | B | N |
| ATOM | 15455 | CA | SER | B | 444 | 47.657 | 31.292 | −20.344 | 1.00 | 21.64 | B | C |
| ATOM | 15457 | CB | SER | B | 444 | 46.339 | 32.028 | −20.345 | 1.00 | 21.22 | B | C |
| ATOM | 15460 | OG | SER | B | 444 | 46.478 | 33.360 | −19.936 | 1.00 | 26.99 | B | O |
| ATOM | 15462 | C | SER | B | 444 | 48.652 | 31.930 | −21.295 | 1.00 | 22.27 | B | C |
| ATOM | 15463 | O | SER | B | 444 | 48.885 | 31.427 | −22.399 | 1.00 | 25.52 | B | O |
| ATOM | 15465 | N | ARG | B | 445 | 49.293 | 33.001 | −20.867 | 1.00 | 21.71 | B | N |
| ATOM | 15466 | CA | ARG | B | 445 | 50.158 | 33.724 | −21.788 | 1.00 | 21.57 | B | C |
| ATOM | 15468 | CB | ARG | B | 445 | 50.571 | 35.066 | −21.210 | 1.00 | 22.03 | B | C |
| ATOM | 15471 | CG | ARG | B | 445 | 49.356 | 35.981 | −21.031 | 1.00 | 23.51 | B | C |
| ATOM | 15474 | CD | ARG | B | 445 | 49.746 | 37.392 | −20.947 | 1.00 | 35.75 | B | C |

TABLE 4-2-continued

Coordinates of *P. alba* IspS

| | | | | | | | | | | | | |
|---|---|---|---|---|---|---|---|---|---|---|---|---|
| ATOM | 15477 | NE | ARG | B | 445 | 48.625 | 38.263 | −20.586 | 1.00 | 46.32 | B | N |
| ATOM | 15479 | CZ | ARG | B | 445 | 48.524 | 38.956 | −19.448 | 1.00 | 42.95 | B | C |
| ATOM | 15480 | NH1 | ARG | B | 445 | 49.463 | 38.885 | −18.497 | 1.00 | 41.13 | B | N |
| ATOM | 15483 | NH2 | ARG | B | 445 | 47.463 | 39.730 | −19.261 | 1.00 | 41.39 | B | N |
| ATOM | 15486 | C | ARG | B | 445 | 51.341 | 32.921 | −22.275 | 1.00 | 22.15 | B | C |
| ATOM | 15487 | O | ARG | B | 445 | 51.581 | 32.896 | −23.460 | 1.00 | 21.06 | B | O |
| ATOM | 15489 | N | PRO | B | 446 | 52.064 | 32.233 | −21.371 | 1.00 | 20.64 | B | N |
| ATOM | 15490 | CA | PRO | B | 446 | 53.093 | 31.345 | −21.884 | 1.00 | 20.55 | B | C |
| ATOM | 15492 | CB | PRO | B | 446 | 53.766 | 30.765 | −20.628 | 1.00 | 21.36 | B | C |
| ATOM | 15495 | CG | PRO | B | 446 | 53.127 | 31.394 | −19.456 | 1.00 | 26.98 | B | C |
| ATOM | 15498 | CD | PRO | B | 446 | 52.065 | 32.353 | −19.908 | 1.00 | 22.16 | B | C |
| ATOM | 15501 | C | PRO | B | 446 | 52.529 | 30.224 | −22.761 | 1.00 | 19.46 | B | C |
| ATOM | 15502 | O | PRO | B | 446 | 53.196 | 29.757 | −23.671 | 1.00 | 19.46 | B | O |
| ATOM | 15503 | N | SER | B | 447 | 51.316 | 29.781 | −22.494 | 1.00 | 21.05 | B | N |
| ATOM | 15504 | CA | SER | B | 447 | 50.692 | 28.808 | −23.397 | 1.00 | 21.90 | B | C |
| ATOM | 15506 | CB | SER | B | 447 | 49.439 | 28.196 | −22.759 | 1.00 | 22.29 | B | C |
| ATOM | 15509 | OG | SER | B | 447 | 49.766 | 27.644 | −21.480 | 1.00 | 23.50 | B | O |
| ATOM | 15511 | C | SER | B | 447 | 50.398 | 29.439 | −24.765 | 1.00 | 20.46 | B | C |
| ATOM | 15512 | O | SER | B | 447 | 50.526 | 28.757 | −25.772 | 1.00 | 18.99 | B | O |
| ATOM | 15514 | N | HIS | B | 448 | 50.065 | 30.736 | −24.809 | 1.00 | 18.56 | B | N |
| ATOM | 15515 | CA | HIS | B | 448 | 49.869 | 31.424 | −26.102 | 1.00 | 19.59 | B | C |
| ATOM | 15517 | CB | HIS | B | 448 | 49.575 | 32.940 | −25.943 | 1.00 | 20.25 | B | C |
| ATOM | 15520 | CG | HIS | B | 448 | 48.262 | 33.260 | −25.299 | 1.00 | 17.92 | B | C |
| ATOM | 15521 | ND1 | HIS | B | 448 | 47.442 | 32.305 | −24.739 | 1.00 | 28.87 | B | N |
| ATOM | 15523 | CE1 | HIS | B | 448 | 46.352 | 32.881 | −24.262 | 1.00 | 28.11 | B | C |
| ATOM | 15525 | NE2 | HIS | B | 448 | 46.445 | 34.180 | −24.475 | 1.00 | 27.76 | B | N |
| ATOM | 15527 | CD2 | HIS | B | 448 | 47.635 | 34.443 | −25.110 | 1.00 | 27.89 | B | C |
| ATOM | 15529 | C | HIS | B | 448 | 51.144 | 31.279 | −26.940 | 1.00 | 20.44 | B | C |
| ATOM | 15530 | O | HIS | B | 448 | 51.091 | 30.897 | −28.104 | 1.00 | 22.27 | B | O |
| ATOM | 15532 | N | ILE | B | 449 | 52.280 | 31.587 | −26.330 | 1.00 | 21.15 | B | N |
| ATOM | 15533 | CA | ILE | B | 449 | 53.582 | 31.551 | −26.989 | 1.00 | 22.39 | B | C |
| ATOM | 15535 | CB | ILE | B | 449 | 54.724 | 32.020 | −26.038 | 1.00 | 24.30 | B | C |
| ATOM | 15537 | CG1 | ILE | B | 449 | 54.491 | 33.446 | −25.519 | 1.00 | 23.85 | B | C |
| ATOM | 15540 | CD1 | ILE | B | 449 | 54.478 | 34.442 | −26.532 | 1.00 | 25.54 | B | C |
| ATOM | 15544 | CG2 | ILE | B | 449 | 56.112 | 31.942 | −26.722 | 1.00 | 18.30 | B | C |
| ATOM | 15548 | C | ILE | B | 449 | 53.927 | 30.142 | −27.449 | 1.00 | 22.56 | B | C |
| ATOM | 15549 | O | ILE | B | 449 | 54.427 | 29.944 | −28.551 | 1.00 | 24.34 | B | O |
| ATOM | 15551 | N | PHE | B | 450 | 53.688 | 29.163 | −26.586 | 1.00 | 23.02 | B | N |
| ATOM | 15552 | CA | PHE | B | 450 | 53.918 | 27.756 | −26.916 | 1.00 | 21.54 | B | C |
| ATOM | 15554 | CB | PHE | B | 450 | 53.473 | 26.918 | −25.716 | 1.00 | 23.75 | B | C |
| ATOM | 15557 | CG | PHE | B | 450 | 53.594 | 25.410 | −25.887 | 1.00 | 24.61 | B | C |
| ATOM | 15558 | CD1 | PHE | B | 450 | 54.374 | 24.827 | −26.878 | 1.00 | 26.66 | B | C |
| ATOM | 15560 | CE1 | PHE | B | 450 | 54.457 | 23.457 | −26.978 | 1.00 | 27.03 | B | C |
| ATOM | 15562 | CZ | PHE | B | 450 | 53.801 | 22.643 | −26.064 | 1.00 | 24.83 | B | C |
| ATOM | 15564 | CE2 | PHE | B | 450 | 53.052 | 23.206 | −25.056 | 1.00 | 28.16 | B | C |
| ATOM | 15566 | CD2 | PHE | B | 450 | 52.960 | 24.581 | −24.968 | 1.00 | 24.61 | B | C |
| ATOM | 15568 | C | PHE | B | 450 | 53.191 | 27.358 | −28.205 | 1.00 | 20.99 | B | C |
| ATOM | 15569 | O | PHE | B | 450 | 53.819 | 26.924 | −29.186 | 1.00 | 21.24 | B | O |
| ATOM | 15571 | N | ARG | B | 451 | 51.884 | 27.569 | −28.229 | 1.00 | 19.94 | B | N |
| ATOM | 15572 | CA | ARG | B | 451 | 51.098 | 27.288 | −29.420 | 1.00 | 20.74 | B | C |
| ATOM | 15574 | CB | ARG | B | 451 | 49.621 | 27.595 | −29.169 | 1.00 | 22.47 | B | C |
| ATOM | 15577 | CG | ARG | B | 451 | 48.730 | 27.505 | −30.419 | 1.00 | 25.35 | B | C |
| ATOM | 15580 | CD | ARG | B | 451 | 48.936 | 26.192 | −31.191 | 1.00 | 23.31 | B | C |
| ATOM | 15583 | NE | ARG | B | 451 | 48.475 | 25.041 | −30.448 | 1.00 | 19.56 | B | N |
| ATOM | 15585 | CZ | ARG | B | 451 | 48.731 | 23.772 | −30.790 | 1.00 | 23.42 | B | C |
| ATOM | 15586 | NH1 | ARG | B | 451 | 49.495 | 23.478 | −31.840 | 1.00 | 19.04 | B | N |
| ATOM | 15589 | NH2 | ARG | B | 451 | 48.232 | 22.788 | −30.062 | 1.00 | 18.74 | B | N |
| ATOM | 15592 | C | ARG | B | 451 | 51.588 | 28.065 | −30.632 | 1.00 | 19.72 | B | C |
| ATOM | 15593 | O | ARG | B | 451 | 51.806 | 27.489 | −31.685 | 1.00 | 19.96 | B | O |
| ATOM | 15595 | N | LEU | B | 452 | 51.786 | 29.369 | −30.495 | 1.00 | 21.57 | B | N |
| ATOM | 15596 | CA | LEU | B | 452 | 52.199 | 30.177 | −31.659 | 1.00 | 20.99 | B | C |
| ATOM | 15598 | CB | LEU | B | 452 | 52.191 | 31.663 | −31.330 | 1.00 | 18.72 | B | C |
| ATOM | 15601 | CG | LEU | B | 452 | 50.805 | 32.248 | −31.082 | 1.00 | 18.91 | B | C |
| ATOM | 15603 | CD1 | LEU | B | 452 | 50.863 | 33.633 | −30.405 | 1.00 | 15.37 | B | C |
| ATOM | 15607 | CD2 | LEU | B | 452 | 50.033 | 32.299 | −32.401 | 1.00 | 22.45 | B | C |
| ATOM | 15611 | C | LEU | B | 452 | 53.557 | 29.757 | −32.201 | 1.00 | 21.75 | B | C |
| ATOM | 15612 | O | LEU | B | 452 | 53.753 | 29.726 | −33.427 | 1.00 | 24.82 | B | O |
| ATOM | 15614 | N | CYS | B | 453 | 54.513 | 29.472 | −31.315 | 1.00 | 22.18 | B | N |
| ATOM | 15615 | CA | CYS | B | 453 | 55.844 | 29.031 | −31.758 | 1.00 | 22.41 | B | C |
| ATOM | 15617 | CB | CYS | B | 453 | 56.801 | 28.918 | −30.589 | 1.00 | 25.19 | B | C |
| ATOM | 15620 | SG | CYS | B | 453 | 57.373 | 30.478 | −29.922 | 1.00 | 28.92 | B | S |
| ATOM | 15622 | C | CYS | B | 453 | 55.744 | 27.682 | −32.476 | 1.00 | 23.45 | B | C |
| ATOM | 15623 | O | CYS | B | 453 | 56.283 | 27.514 | −33.545 | 1.00 | 25.24 | B | O |
| ATOM | 15625 | N | ASN | B | 454 | 55.004 | 26.743 | −31.901 | 1.00 | 23.96 | B | N |
| ATOM | 15626 | CA | ASN | B | 454 | 54.755 | 25.463 | −32.555 | 1.00 | 25.23 | B | C |
| ATOM | 15628 | CB | ASN | B | 454 | 53.889 | 24.583 | −31.643 | 1.00 | 25.52 | B | C |
| ATOM | 15631 | CG | ASN | B | 454 | 53.627 | 23.178 | −32.218 | 1.00 | 30.70 | B | C |
| ATOM | 15632 | OD1 | ASN | B | 454 | 54.124 | 22.811 | −33.295 | 1.00 | 41.50 | B | O |

TABLE 4-2-continued

Coordinates of *P. alba* IspS

| | | | | | | | | | | | | |
|---|---|---|---|---|---|---|---|---|---|---|---|---|
| ATOM | 15633 | ND2 | ASN | B | 454 | 52.848 | 22.382 | −31.480 | 1.00 | 30.45 | B | N |
| ATOM | 15636 | C | ASN | B | 454 | 54.103 | 25.614 | −33.935 | 1.00 | 26.69 | B | C |
| ATOM | 15637 | O | ASN | B | 454 | 54.551 | 25.039 | −34.924 | 1.00 | 25.94 | B | O |
| ATOM | 15639 | N | ASP | B | 455 | 53.039 | 26.393 | −34.006 | 1.00 | 25.79 | B | N |
| ATOM | 15640 | CA | ASP | B | 455 | 52.334 | 26.528 | −35.265 | 1.00 | 24.91 | B | C |
| ATOM | 15642 | CB | ASP | B | 455 | 50.983 | 27.213 | −35.077 | 1.00 | 24.32 | B | C |
| ATOM | 15645 | CG | ASP | B | 455 | 49.932 | 26.296 | −34.475 | 1.00 | 27.79 | B | C |
| ATOM | 15646 | OD1 | ASP | B | 455 | 50.267 | 25.171 | −34.053 | 1.00 | 23.64 | B | O |
| ATOM | 15647 | OD2 | ASP | B | 455 | 48.753 | 26.715 | −34.422 | 1.00 | 29.77 | B | O |
| ATOM | 15648 | C | ASP | B | 455 | 53.169 | 27.290 | −36.278 | 1.00 | 25.89 | B | C |
| ATOM | 15649 | O | ASP | B | 455 | 53.081 | 27.002 | −37.471 | 1.00 | 26.97 | B | O |
| ATOM | 15651 | N | LEU | B | 456 | 53.950 | 28.267 | −35.829 | 1.00 | 25.05 | B | N |
| ATOM | 15652 | CA | LEU | B | 456 | 54.864 | 28.975 | −36.734 | 1.00 | 27.30 | B | C |
| ATOM | 15654 | CB | LEU | B | 456 | 55.706 | 30.009 | −35.981 | 1.00 | 28.50 | B | C |
| ATOM | 15657 | CG | LEU | B | 456 | 55.165 | 31.412 | −35.754 | 1.00 | 31.82 | B | C |
| ATOM | 15659 | CD1 | LEU | B | 456 | 56.033 | 32.147 | −34.720 | 1.00 | 27.46 | B | C |
| ATOM | 15663 | CD2 | LEU | B | 456 | 55.143 | 32.136 | −37.066 | 1.00 | 27.67 | B | C |
| ATOM | 15667 | C | LEU | B | 456 | 55.831 | 27.999 | −37.417 | 1.00 | 29.38 | B | C |
| ATOM | 15668 | O | LEU | B | 456 | 56.116 | 28.138 | −38.610 | 1.00 | 27.77 | B | O |
| ATOM | 15670 | N | ALA | B | 457 | 56.332 | 27.022 | −36.653 | 1.00 | 29.83 | B | N |
| ATOM | 15671 | CA | ALA | B | 457 | 57.349 | 26.087 | −37.157 | 1.00 | 31.91 | B | C |
| ATOM | 15673 | CB | ALA | B | 457 | 58.006 | 25.277 | −35.983 | 1.00 | 28.83 | B | C |
| ATOM | 15677 | C | ALA | B | 457 | 56.801 | 25.140 | −38.232 | 1.00 | 32.51 | B | C |
| ATOM | 15678 | O | ALA | B | 457 | 57.519 | 24.802 | −39.166 | 1.00 | 34.24 | B | O |
| ATOM | 15680 | N | SER | B | 458 | 55.541 | 24.723 | −38.123 | 1.00 | 33.79 | B | N |
| ATOM | 15681 | CA | SER | B | 458 | 54.957 | 23.822 | −39.135 | 1.00 | 34.87 | B | C |
| ATOM | 15683 | CB | SER | B | 458 | 54.113 | 22.751 | −38.446 | 1.00 | 34.97 | B | C |
| ATOM | 15686 | OG | SER | B | 458 | 53.080 | 23.347 | −37.693 | 1.00 | 39.44 | B | O |
| ATOM | 15688 | C | SER | B | 458 | 54.094 | 24.531 | −40.189 | 1.00 | 33.97 | B | C |
| ATOM | 15689 | O | SER | B | 458 | 53.555 | 23.888 | −41.097 | 1.00 | 34.54 | B | O |
| ATOM | 15691 | N | ALA | B | 459 | 53.951 | 25.845 | −40.077 | 1.00 | 34.50 | B | N |
| ATOM | 15692 | CA | ALA | B | 459 | 52.971 | 26.580 | −40.907 | 1.00 | 33.99 | B | C |
| ATOM | 15694 | CB | ALA | B | 459 | 53.033 | 28.075 | −40.597 | 1.00 | 31.89 | B | C |
| ATOM | 15698 | C | ALA | B | 459 | 53.174 | 26.357 | −42.408 | 1.00 | 35.22 | B | C |
| ATOM | 15699 | O | ALA | B | 459 | 52.247 | 25.966 | −43.129 | 1.00 | 33.66 | B | O |
| ATOM | 15701 | N | SER | B | 460 | 54.386 | 26.616 | −42.878 | 1.00 | 37.80 | B | N |
| ATOM | 15702 | CA | SER | B | 460 | 54.671 | 26.532 | −44.308 | 1.00 | 42.19 | B | C |
| ATOM | 15704 | CB | SER | B | 460 | 56.131 | 26.863 | −44.593 | 1.00 | 41.81 | B | C |
| ATOM | 15707 | OG | SER | B | 460 | 56.959 | 25.873 | −44.007 | 1.00 | 52.01 | B | O |
| ATOM | 15709 | C | SER | B | 460 | 54.306 | 25.164 | −44.903 | 1.00 | 42.35 | B | C |
| ATOM | 15710 | O | SER | B | 460 | 53.632 | 25.107 | −45.925 | 1.00 | 43.43 | B | O |
| ATOM | 15712 | N | ALA | B | 461 | 54.718 | 24.073 | −44.264 | 1.00 | 42.83 | B | N |
| ATOM | 15713 | CA | ALA | B | 461 | 54.384 | 22.738 | −44.780 | 1.00 | 42.85 | B | C |
| ATOM | 15715 | CB | ALA | B | 461 | 55.110 | 21.645 | −44.000 | 1.00 | 42.43 | B | C |
| ATOM | 15719 | C | ALA | B | 461 | 52.881 | 22.504 | −44.737 | 1.00 | 43.66 | B | C |
| ATOM | 15720 | O | ALA | B | 461 | 52.300 | 22.003 | −45.696 | 1.00 | 44.63 | B | O |
| ATOM | 15722 | N | GLU | B | 462 | 52.253 | 22.884 | −43.627 | 1.00 | 43.99 | B | N |
| ATOM | 15723 | CA | GLU | B | 462 | 50.839 | 22.611 | −43.422 | 1.00 | 43.23 | B | C |
| ATOM | 15725 | CB | GLU | B | 462 | 50.439 | 22.868 | −41.960 | 1.00 | 43.40 | B | C |
| ATOM | 15728 | CG | GLU | B | 462 | 51.049 | 21.826 | −40.996 | 1.00 | 44.25 | B | C |
| ATOM | 15731 | CD | GLU | B | 462 | 50.581 | 21.932 | −39.541 | 1.00 | 47.19 | B | C |
| ATOM | 15732 | OE1 | GLU | B | 462 | 49.667 | 22.724 | −39.235 | 1.00 | 52.18 | B | O |
| ATOM | 15733 | OE2 | GLU | B | 462 | 51.140 | 21.208 | −38.685 | 1.00 | 50.84 | B | O |
| ATOM | 15734 | C | GLU | B | 462 | 49.979 | 23.397 | −44.405 | 1.00 | 43.66 | B | C |
| ATOM | 15735 | O | GLU | B | 462 | 48.979 | 22.885 | −44.919 | 1.00 | 43.54 | B | O |
| ATOM | 15737 | N | ILE | B | 463 | 50.388 | 24.624 | −44.701 | 1.00 | 43.85 | B | N |
| ATOM | 15738 | CA | ILE | B | 463 | 49.678 | 25.443 | −45.670 | 1.00 | 43.45 | B | C |
| ATOM | 15740 | CB | ILE | B | 463 | 50.147 | 26.910 | −45.599 | 1.00 | 42.49 | B | C |
| ATOM | 15742 | CG1 | ILE | B | 463 | 49.640 | 27.547 | −44.298 | 1.00 | 43.11 | B | C |
| ATOM | 15745 | CD1 | ILE | B | 463 | 50.272 | 28.903 | −43.970 | 1.00 | 34.75 | B | C |
| ATOM | 15749 | CG2 | ILE | B | 463 | 49.658 | 27.714 | −46.809 | 1.00 | 40.80 | B | C |
| ATOM | 15753 | C | ILE | B | 463 | 49.836 | 24.863 | −47.086 | 1.00 | 46.39 | B | C |
| ATOM | 15754 | O | ILE | B | 463 | 48.888 | 24.891 | −47.885 | 1.00 | 48.52 | B | O |
| ATOM | 15756 | N | ALA | B | 464 | 51.016 | 24.324 | −47.387 | 1.00 | 47.05 | B | N |
| ATOM | 15757 | CA | ALA | B | 464 | 51.302 | 23.784 | −48.719 | 1.00 | 48.40 | B | C |
| ATOM | 15759 | CB | ALA | B | 464 | 52.809 | 23.523 | −48.896 | 1.00 | 46.81 | B | C |
| ATOM | 15763 | C | ALA | B | 464 | 50.489 | 22.516 | −48.985 | 1.00 | 49.19 | B | C |
| ATOM | 15764 | O | ALA | B | 464 | 50.121 | 22.260 | −50.125 | 1.00 | 49.95 | B | O |
| ATOM | 15766 | N | ARG | B | 465 | 50.195 | 21.739 | −47.941 | 1.00 | 49.76 | B | N |
| ATOM | 15767 | CA | ARG | B | 465 | 49.306 | 20.569 | −48.075 | 1.00 | 51.15 | B | C |
| ATOM | 15769 | CB | ARG | B | 465 | 49.490 | 19.572 | −46.925 | 1.00 | 51.61 | B | C |
| ATOM | 15772 | CG | ARG | B | 465 | 50.880 | 18.967 | −46.767 | 1.00 | 55.53 | B | C |
| ATOM | 15775 | CD | ARG | B | 465 | 50.935 | 18.153 | −45.476 | 1.00 | 58.91 | B | C |
| ATOM | 15778 | NE | ARG | B | 465 | 52.181 | 18.367 | −44.734 | 1.00 | 65.49 | B | N |
| ATOM | 15780 | CZ | ARG | B | 465 | 52.308 | 18.305 | −43.404 | 1.00 | 67.24 | B | C |
| ATOM | 15781 | NH1 | ARG | B | 465 | 51.261 | 18.048 | −42.620 | 1.00 | 67.28 | B | N |
| ATOM | 15784 | NH2 | ARG | B | 465 | 53.500 | 18.517 | −42.849 | 1.00 | 67.61 | B | N |
| ATOM | 15787 | C | ARG | B | 465 | 47.831 | 20.956 | −48.095 | 1.00 | 51.06 | B | C |

TABLE 4-2-continued

Coordinates of *P. alba* IspS

| | | | | | | | | | | | | |
|---|---|---|---|---|---|---|---|---|---|---|---|---|
| ATOM | 15788 | O | ARG | B | 465 | 46.971 | 20.082 | −48.199 | 1.00 | 50.83 | B | O |
| ATOM | 15790 | N | GLY | B | 466 | 47.533 | 22.247 | −47.958 | 1.00 | 50.91 | B | N |
| ATOM | 15791 | CA | GLY | B | 466 | 46.152 | 22.716 | −47.896 | 1.00 | 50.39 | B | C |
| ATOM | 15794 | C | GLY | B | 466 | 45.486 | 22.489 | −46.547 | 1.00 | 49.96 | B | C |
| ATOM | 15795 | O | GLY | B | 466 | 44.259 | 22.509 | −46.466 | 1.00 | 48.27 | B | O |
| ATOM | 15797 | N | GLU | B | 467 | 46.279 | 22.272 | −45.492 | 1.00 | 48.91 | B | N |
| ATOM | 15798 | CA | GLU | B | 467 | 45.730 | 22.134 | −44.139 | 1.00 | 48.83 | B | C |
| ATOM | 15800 | CB | GLU | B | 467 | 46.683 | 21.365 | −43.215 | 1.00 | 50.22 | B | C |
| ATOM | 15803 | CG | GLU | B | 467 | 46.967 | 19.930 | −43.661 | 1.00 | 54.30 | B | C |
| ATOM | 15806 | CD | GLU | B | 467 | 47.790 | 19.116 | −42.653 | 1.00 | 62.14 | B | C |
| ATOM | 15807 | OE1 | GLU | B | 467 | 47.867 | 19.491 | −41.458 | 1.00 | 59.06 | B | O |
| ATOM | 15808 | OE2 | GLU | B | 467 | 48.354 | 18.078 | −43.069 | 1.00 | 67.03 | B | O |
| ATOM | 15809 | C | GLU | B | 467 | 45.424 | 23.515 | −43.548 | 1.00 | 47.13 | B | C |
| ATOM | 15810 | O | GLU | B | 467 | 46.114 | 24.497 | −43.847 | 1.00 | 47.48 | B | O |
| ATOM | 15812 | N | THR | B | 468 | 44.375 | 23.586 | −42.732 | 1.00 | 42.97 | B | N |
| ATOM | 15813 | CA | THR | B | 468 | 43.954 | 24.835 | −42.125 | 1.00 | 40.67 | B | C |
| ATOM | 15815 | CB | THR | B | 468 | 42.508 | 25.173 | −42.518 | 1.00 | 42.48 | B | C |
| ATOM | 15817 | OG1 | THR | B | 468 | 41.661 | 24.045 | −42.263 | 1.00 | 42.18 | B | O |
| ATOM | 15819 | CG2 | THR | B | 468 | 42.418 | 25.574 | −43.978 | 1.00 | 40.21 | B | C |
| ATOM | 15823 | C | THR | B | 468 | 44.074 | 24.847 | −40.585 | 1.00 | 38.82 | B | C |
| ATOM | 15824 | O | THR | B | 468 | 43.912 | 25.902 | −39.956 | 1.00 | 36.40 | B | O |
| ATOM | 15826 | N | ALA | B | 469 | 44.376 | 23.688 | −39.996 | 1.00 | 36.08 | B | N |
| ATOM | 15827 | CA | ALA | B | 469 | 44.455 | 23.532 | −38.542 | 1.00 | 35.79 | B | C |
| ATOM | 15829 | CB | ALA | B | 469 | 44.222 | 22.068 | −38.167 | 1.00 | 35.44 | B | C |
| ATOM | 15833 | C | ALA | B | 469 | 45.812 | 24.041 | −38.008 | 1.00 | 33.99 | B | C |
| ATOM | 15834 | O | ALA | B | 469 | 46.668 | 23.262 | −37.602 | 1.00 | 35.58 | B | O |
| ATOM | 15836 | N | ASN | B | 470 | 45.972 | 25.363 | −38.014 | 1.00 | 30.53 | B | N |
| ATOM | 15837 | CA | ASN | B | 470 | 47.231 | 26.025 | −37.741 | 1.00 | 25.50 | B | C |
| ATOM | 15839 | CB | ASN | B | 470 | 48.175 | 25.826 | −38.924 | 1.00 | 24.65 | B | C |
| ATOM | 15842 | CG | ASN | B | 470 | 49.538 | 26.437 | −38.688 | 1.00 | 24.87 | B | C |
| ATOM | 15843 | OD1 | ASN | B | 470 | 49.730 | 27.634 | −38.868 | 1.00 | 29.42 | B | O |
| ATOM | 15844 | ND2 | ASN | B | 470 | 50.501 | 25.609 | −38.281 | 1.00 | 29.64 | B | N |
| ATOM | 15847 | C | ASN | B | 470 | 46.974 | 27.515 | −37.559 | 1.00 | 24.47 | B | C |
| ATOM | 15848 | O | ASN | B | 470 | 46.291 | 28.128 | −38.365 | 1.00 | 25.58 | B | O |
| ATOM | 15850 | N | SER | B | 471 | 47.564 | 28.104 | −36.536 | 1.00 | 23.87 | B | N |
| ATOM | 15851 | CA | SER | B | 471 | 47.303 | 29.492 | −36.181 | 1.00 | 22.68 | B | C |
| ATOM | 15853 | CB | SER | B | 471 | 48.100 | 29.848 | −34.917 | 1.00 | 23.21 | B | C |
| ATOM | 15856 | OG | SER | B | 471 | 47.655 | 29.026 | −33.835 | 1.00 | 25.29 | B | O |
| ATOM | 15858 | C | SER | B | 471 | 47.606 | 30.484 | −37.296 | 1.00 | 22.53 | B | C |
| ATOM | 15859 | O | SER | B | 471 | 46.853 | 31.454 | −37.500 | 1.00 | 18.89 | B | O |
| ATOM | 15861 | N | VAL | B | 472 | 48.692 | 30.241 | −38.031 | 1.00 | 22.65 | B | N |
| ATOM | 15862 | CA | VAL | B | 472 | 49.105 | 31.147 | −39.088 | 1.00 | 21.42 | B | C |
| ATOM | 15864 | CB | VAL | B | 472 | 50.518 | 30.828 | −39.641 | 1.00 | 21.25 | B | C |
| ATOM | 15866 | CG1 | VAL | B | 472 | 50.905 | 31.826 | −40.704 | 1.00 | 17.98 | B | C |
| ATOM | 15870 | CG2 | VAL | B | 472 | 51.546 | 30.823 | −38.538 | 1.00 | 20.99 | B | C |
| ATOM | 15874 | C | VAL | B | 472 | 48.090 | 31.055 | −40.204 | 1.00 | 21.80 | B | C |
| ATOM | 15875 | O | VAL | B | 472 | 47.694 | 32.062 | −40.783 | 1.00 | 22.50 | B | O |
| ATOM | 15877 | N | SER | B | 473 | 47.659 | 29.841 | −40.498 | 1.00 | 24.12 | B | N |
| ATOM | 15878 | CA | SER | B | 473 | 46.680 | 29.630 | −41.544 | 1.00 | 25.40 | B | C |
| ATOM | 15880 | CB | SER | B | 473 | 46.400 | 28.146 | −41.745 | 1.00 | 26.05 | B | C |
| ATOM | 15883 | OG | SER | B | 473 | 45.232 | 27.940 | −42.515 | 1.00 | 32.34 | B | O |
| ATOM | 15885 | C | SER | B | 473 | 45.400 | 30.375 | −41.202 | 1.00 | 24.34 | B | C |
| ATOM | 15886 | O | SER | B | 473 | 44.847 | 31.051 | −42.064 | 1.00 | 23.63 | B | O |
| ATOM | 15888 | N | CYS | B | 474 | 44.921 | 30.280 | −39.960 | 1.00 | 23.27 | B | N |
| ATOM | 15889 | CA | CYS | B | 474 | 43.642 | 30.961 | −39.612 | 1.00 | 24.54 | B | C |
| ATOM | 15891 | CB | CYS | B | 474 | 43.162 | 30.643 | −38.196 | 1.00 | 26.93 | B | C |
| ATOM | 15894 | SG | CYS | B | 474 | 42.488 | 29.053 | −38.026 | 1.00 | 32.90 | B | S |
| ATOM | 15896 | C | CYS | B | 474 | 43.784 | 32.442 | −39.678 | 1.00 | 22.35 | B | C |
| ATOM | 15897 | O | CYS | B | 474 | 42.866 | 33.138 | −40.073 | 1.00 | 25.09 | B | O |
| ATOM | 15899 | N | TYR | B | 475 | 44.934 | 32.933 | −39.257 | 1.00 | 21.83 | B | N |
| ATOM | 15900 | CA | TYR | B | 475 | 45.190 | 34.340 | −39.332 | 1.00 | 22.48 | B | C |
| ATOM | 15902 | CB | TYR | B | 475 | 46.530 | 34.700 | −38.700 | 1.00 | 21.91 | B | C |
| ATOM | 15905 | CG | TYR | B | 475 | 46.519 | 36.065 | −38.080 | 1.00 | 23.95 | B | C |
| ATOM | 15906 | CD1 | TYR | B | 475 | 46.386 | 36.237 | −36.704 | 1.00 | 34.09 | B | C |
| ATOM | 15908 | CE1 | TYR | B | 475 | 46.373 | 37.512 | −36.136 | 1.00 | 35.55 | B | C |
| ATOM | 15910 | CZ | TYR | B | 475 | 46.497 | 38.611 | −36.954 | 1.00 | 34.14 | B | C |
| ATOM | 15911 | OH | TYR | B | 475 | 46.491 | 39.895 | −36.448 | 1.00 | 48.07 | B | O |
| ATOM | 15913 | CE2 | TYR | B | 475 | 46.635 | 38.456 | −38.307 | 1.00 | 35.92 | B | C |
| ATOM | 15915 | CD2 | TYR | B | 475 | 46.644 | 37.188 | −38.863 | 1.00 | 31.67 | B | C |
| ATOM | 15917 | C | TYR | B | 475 | 45.105 | 34.802 | −40.780 | 1.00 | 22.81 | B | C |
| ATOM | 15918 | O | TYR | B | 475 | 44.474 | 35.831 | −41.063 | 1.00 | 21.86 | B | O |
| ATOM | 15920 | N | MET | B | 476 | 45.690 | 34.038 | −41.702 | 1.00 | 23.95 | B | N |
| ATOM | 15921 | CA | MET | B | 476 | 45.575 | 34.362 | −43.138 | 1.00 | 23.98 | B | C |
| ATOM | 15923 | CB | MET | B | 476 | 46.227 | 33.304 | −44.022 | 1.00 | 23.03 | B | C |
| ATOM | 15926 | CG | MET | B | 476 | 47.734 | 33.236 | −43.917 | 1.00 | 31.57 | B | C |
| ATOM | 15929 | SD | MET | B | 476 | 48.370 | 31.791 | −44.783 | 1.00 | 35.82 | B | S |
| ATOM | 15930 | CE | MET | B | 476 | 47.693 | 31.997 | −46.420 | 1.00 | 24.22 | B | C |
| ATOM | 15934 | C | MET | B | 476 | 44.141 | 34.491 | −43.607 | 1.00 | 23.68 | B | C |

TABLE 4-2-continued

Coordinates of *P. alba* IspS

| | | | | | | | | | | | | |
|---|---|---|---|---|---|---|---|---|---|---|---|---|
| ATOM | 15935 | O | MET | B | 476 | 43.773 | 35.478 | −44.264 | 1.00 | 22.64 | B | O |
| ATOM | 15937 | N | ARG | B | 477 | 43.345 | 33.465 | −43.322 | 1.00 | 25.52 | B | N |
| ATOM | 15938 | CA | ARG | B | 477 | 41.970 | 33.395 | −43.827 | 1.00 | 25.98 | B | C |
| ATOM | 15940 | CB | ARG | B | 477 | 41.428 | 31.967 | −43.725 | 1.00 | 26.64 | B | C |
| ATOM | 15943 | CG | ARG | B | 477 | 42.138 | 31.022 | −44.683 | 1.00 | 33.11 | B | C |
| ATOM | 15946 | CD | ARG | B | 477 | 41.835 | 29.543 | −44.464 | 1.00 | 39.31 | B | C |
| ATOM | 15949 | NE | ARG | B | 477 | 42.179 | 29.067 | −43.121 | 1.00 | 44.33 | B | N |
| ATOM | 15951 | CZ | ARG | B | 477 | 41.305 | 28.880 | −42.129 | 1.00 | 46.94 | B | C |
| ATOM | 15952 | NH1 | ARG | B | 477 | 40.009 | 29.127 | −42.300 | 1.00 | 48.55 | B | N |
| ATOM | 15955 | NH2 | ARG | B | 477 | 41.736 | 28.447 | −40.947 | 1.00 | 49.68 | B | N |
| ATOM | 15958 | C | ARG | B | 477 | 41.058 | 34.367 | −43.100 | 1.00 | 25.86 | B | C |
| ATOM | 15959 | O | ARG | B | 477 | 40.157 | 34.945 | −43.720 | 1.00 | 28.90 | B | O |
| ATOM | 15961 | N | THR | B | 478 | 41.277 | 34.546 | −41.797 | 1.00 | 24.19 | B | N |
| ATOM | 15962 | CA | THR | B | 478 | 40.461 | 35.474 | −41.024 | 1.00 | 25.34 | B | C |
| ATOM | 15964 | CB | THR | B | 478 | 40.684 | 35.343 | −39.479 | 1.00 | 25.12 | B | C |
| ATOM | 15966 | OG1 | THR | B | 478 | 40.006 | 34.185 | −38.996 | 1.00 | 20.79 | B | O |
| ATOM | 15968 | CG2 | THR | B | 478 | 40.152 | 36.574 | −38.707 | 1.00 | 21.35 | B | C |
| ATOM | 15972 | C | THR | B | 478 | 40.692 | 36.916 | −41.477 | 1.00 | 25.19 | B | C |
| ATOM | 15973 | O | THR | B | 478 | 39.741 | 37.646 | −41.606 | 1.00 | 24.19 | B | O |
| ATOM | 15975 | N | LYS | B | 479 | 41.944 | 37.316 | −41.698 | 1.00 | 25.64 | B | N |
| ATOM | 15976 | CA | LYS | B | 479 | 42.261 | 38.694 | −42.081 | 1.00 | 27.05 | B | C |
| ATOM | 15978 | CB | LYS | B | 479 | 43.538 | 39.169 | −41.392 | 1.00 | 28.04 | B | C |
| ATOM | 15981 | CG | LYS | B | 479 | 43.434 | 39.286 | −39.858 | 1.00 | 32.43 | B | C |
| ATOM | 15984 | CD | LYS | B | 479 | 42.899 | 40.662 | −39.421 | 1.00 | 41.92 | B | C |
| ATOM | 15987 | CE | LYS | B | 479 | 42.652 | 40.733 | −37.915 | 1.00 | 48.99 | B | C |
| ATOM | 15990 | NZ | LYS | B | 479 | 42.370 | 42.129 | −37.475 | 1.00 | 48.92 | B | N |
| ATOM | 15994 | C | LYS | B | 479 | 42.368 | 38.915 | −43.593 | 1.00 | 28.30 | B | C |
| ATOM | 15995 | O | LYS | B | 479 | 42.444 | 40.064 | −44.042 | 1.00 | 30.46 | B | O |
| ATOM | 15997 | N | GLY | B | 480 | 42.335 | 37.844 | −44.384 | 1.00 | 27.75 | B | N |
| ATOM | 15998 | CA | GLY | B | 480 | 42.483 | 37.962 | −45.838 | 1.00 | 27.63 | B | C |
| ATOM | 16001 | C | GLY | B | 480 | 43.873 | 38.401 | −46.270 | 1.00 | 27.82 | B | C |
| ATOM | 16002 | O | GLY | B | 480 | 44.014 | 39.224 | −47.167 | 1.00 | 28.13 | B | O |
| ATOM | 16004 | N | ILE | B | 481 | 44.910 | 37.846 | −45.638 | 1.00 | 27.16 | B | N |
| ATOM | 16005 | CA | ILE | B | 481 | 46.294 | 38.221 | −45.964 | 1.00 | 27.84 | B | C |
| ATOM | 16007 | CB | ILE | B | 481 | 46.978 | 39.002 | −44.812 | 1.00 | 27.50 | B | C |
| ATOM | 16009 | CG1 | ILE | B | 481 | 47.018 | 38.173 | −43.515 | 1.00 | 26.34 | B | C |
| ATOM | 16012 | CD1 | ILE | B | 481 | 47.775 | 38.847 | −42.350 | 1.00 | 23.73 | B | C |
| ATOM | 16016 | CG2 | ILE | B | 481 | 46.260 | 40.328 | −44.607 | 1.00 | 27.59 | B | C |
| ATOM | 16020 | C | ILE | B | 481 | 47.138 | 37.024 | −46.393 | 1.00 | 28.16 | B | C |
| ATOM | 16021 | O | ILE | B | 481 | 46.725 | 35.888 | −46.255 | 1.00 | 30.84 | B | O |
| ATOM | 16023 | N | SER | B | 482 | 48.305 | 37.308 | −46.954 | 1.00 | 30.02 | B | N |
| ATOM | 16024 | CA | SER | B | 482 | 49.283 | 36.301 | −47.364 | 1.00 | 30.53 | B | C |
| ATOM | 16026 | CB | SER | B | 482 | 50.364 | 36.989 | −48.173 | 1.00 | 30.13 | B | C |
| ATOM | 16029 | OG | SER | B | 482 | 50.971 | 37.996 | −47.377 | 1.00 | 28.80 | B | O |
| ATOM | 16031 | C | SER | B | 482 | 49.968 | 35.638 | −46.164 | 1.00 | 31.57 | B | C |
| ATOM | 16032 | O | SER | B | 482 | 50.006 | 36.209 | −45.074 | 1.00 | 31.84 | B | O |
| ATOM | 16034 | N | GLU | B | 483 | 50.548 | 34.461 | −46.390 | 1.00 | 30.45 | B | N |
| ATOM | 16035 | CA | GLU | B | 483 | 51.308 | 33.774 | −45.371 | 1.00 | 31.95 | B | C |
| ATOM | 16037 | CB | GLU | B | 483 | 51.969 | 32.521 | −45.952 | 1.00 | 32.69 | B | C |
| ATOM | 16040 | CG | GLU | B | 483 | 52.874 | 31.797 | −44.939 | 1.00 | 35.01 | B | C |
| ATOM | 16043 | CD | GLU | B | 483 | 53.216 | 30.353 | −45.314 | 1.00 | 41.67 | B | C |
| ATOM | 16044 | OE1 | GLU | B | 483 | 52.776 | 29.875 | −46.389 | 1.00 | 39.44 | B | O |
| ATOM | 16045 | OE2 | GLU | B | 483 | 53.939 | 29.701 | −44.511 | 1.00 | 39.15 | B | O |
| ATOM | 16046 | C | GLU | B | 483 | 52.353 | 34.672 | −44.706 | 1.00 | 32.33 | B | C |
| ATOM | 16047 | O | GLU | B | 483 | 52.486 | 34.704 | −43.482 | 1.00 | 33.44 | B | O |
| ATOM | 16049 | N | GLU | B | 484 | 53.073 | 35.412 | −45.522 | 1.00 | 33.10 | B | N |
| ATOM | 16050 | CA | GLU | B | 484 | 54.133 | 36.271 | −45.054 | 1.00 | 35.44 | B | C |
| ATOM | 16052 | CB | GLU | B | 484 | 54.806 | 36.958 | −46.254 | 1.00 | 37.40 | B | C |
| ATOM | 16055 | CG | GLU | B | 484 | 56.049 | 37.754 | −45.888 | 1.00 | 47.37 | B | C |
| ATOM | 16058 | CD | GLU | B | 484 | 56.678 | 38.484 | −47.076 | 1.00 | 61.47 | B | C |
| ATOM | 16059 | OE1 | GLU | B | 484 | 56.049 | 38.576 | −48.162 | 1.00 | 64.59 | B | O |
| ATOM | 16060 | OE2 | GLU | B | 484 | 57.815 | 38.975 | −46.906 | 1.00 | 63.79 | B | O |
| ATOM | 16061 | C | GLU | B | 484 | 53.636 | 37.330 | −44.064 | 1.00 | 33.41 | B | C |
| ATOM | 16062 | O | GLU | B | 484 | 54.285 | 37.580 | −43.049 | 1.00 | 30.95 | B | O |
| ATOM | 16064 | N | LEU | B | 485 | 52.516 | 37.974 | −44.375 | 1.00 | 31.70 | B | N |
| ATOM | 16065 | CA | LEU | B | 485 | 51.982 | 39.005 | −43.489 | 1.00 | 31.52 | B | C |
| ATOM | 16067 | CB | LEU | B | 485 | 50.969 | 39.899 | −44.218 | 1.00 | 33.56 | B | C |
| ATOM | 16070 | CG | LEU | B | 485 | 51.561 | 40.942 | −45.174 | 1.00 | 37.32 | B | C |
| ATOM | 16072 | CD1 | LEU | B | 485 | 50.509 | 41.463 | −46.157 | 1.00 | 36.05 | B | C |
| ATOM | 16076 | CD2 | LEU | B | 485 | 52.180 | 42.087 | −44.377 | 1.00 | 42.57 | B | C |
| ATOM | 16080 | C | LEU | B | 485 | 51.360 | 38.383 | −42.229 | 1.00 | 28.30 | B | C |
| ATOM | 16081 | O | LEU | B | 485 | 51.426 | 38.957 | −41.157 | 1.00 | 25.25 | B | O |
| ATOM | 16083 | N | ALA | B | 486 | 50.782 | 37.201 | −42.367 | 1.00 | 26.73 | B | N |
| ATOM | 16084 | CA | ALA | B | 486 | 50.173 | 36.528 | −41.243 | 1.00 | 26.36 | B | C |
| ATOM | 16086 | CB | ALA | B | 486 | 49.358 | 35.304 | −41.718 | 1.00 | 23.95 | B | C |
| ATOM | 16090 | C | ALA | B | 486 | 51.281 | 36.134 | −40.269 | 1.00 | 24.95 | B | C |
| ATOM | 16091 | O | ALA | B | 486 | 51.141 | 36.267 | −39.048 | 1.00 | 22.96 | B | O |
| ATOM | 16093 | N | THR | B | 487 | 52.397 | 35.706 | −40.835 | 1.00 | 25.77 | B | N |

TABLE 4-2-continued

| Coordinates of *P. alba* IspS | | | | | | | | | | | |
|---|---|---|---|---|---|---|---|---|---|---|---|
| ATOM | 16094 | CA | THR | B | 487 | 53.581 | 35.312 | −40.069 | 1.00 | 27.48 | B | C |
| ATOM | 16096 | CB | THR | B | 487 | 54.654 | 34.714 | −41.004 | 1.00 | 29.14 | B | C |
| ATOM | 16098 | OG1 | THR | B | 487 | 54.120 | 33.537 | −41.647 | 1.00 | 29.56 | B | O |
| ATOM | 16100 | CG2 | THR | B | 487 | 55.884 | 34.343 | −40.234 | 1.00 | 24.58 | B | C |
| ATOM | 16104 | C | THR | B | 487 | 54.142 | 36.492 | −39.306 | 1.00 | 26.57 | B | C |
| ATOM | 16105 | O | THR | B | 487 | 54.450 | 36.400 | −38.119 | 1.00 | 22.40 | B | O |
| ATOM | 16107 | N | GLU | B | 488 | 54.225 | 37.624 | −39.977 | 1.00 | 28.65 | B | N |
| ATOM | 16108 | CA | GLU | B | 488 | 54.627 | 38.869 | −39.311 | 1.00 | 31.12 | B | C |
| ATOM | 16110 | CB | GLU | B | 488 | 54.701 | 40.012 | −40.336 | 1.00 | 33.28 | B | C |
| ATOM | 16113 | CG | GLU | B | 488 | 55.304 | 41.334 | −39.844 | 1.00 | 43.15 | B | C |
| ATOM | 16116 | CD | GLU | B | 488 | 55.275 | 42.458 | −40.908 | 1.00 | 50.77 | B | C |
| ATOM | 16117 | OE1 | GLU | B | 488 | 54.732 | 42.270 | −42.023 | 1.00 | 51.52 | B | O |
| ATOM | 16118 | OE2 | GLU | B | 488 | 55.802 | 43.548 | −40.611 | 1.00 | 57.46 | B | O |
| ATOM | 16119 | C | GLU | B | 488 | 53.669 | 39.187 | −38.131 | 1.00 | 28.39 | B | C |
| ATOM | 16120 | O | GLU | B | 488 | 54.129 | 39.472 | −37.027 | 1.00 | 25.62 | B | O |
| ATOM | 16122 | N | SER | B | 489 | 52.354 | 39.090 | −38.351 | 1.00 | 25.99 | B | N |
| ATOM | 16123 | CA | SER | B | 489 | 51.379 | 39.404 | −37.281 | 1.00 | 27.20 | B | C |
| ATOM | 16125 | CB | SER | B | 489 | 49.923 | 39.418 | −37.770 | 1.00 | 24.76 | B | C |
| ATOM | 16128 | OG | SER | B | 489 | 49.709 | 40.444 | −38.695 | 1.00 | 30.59 | B | O |
| ATOM | 16130 | C | SER | B | 489 | 51.473 | 38.435 | −36.118 | 1.00 | 25.26 | B | C |
| ATOM | 16131 | O | SER | B | 489 | 51.327 | 38.835 | −34.979 | 1.00 | 25.76 | B | O |
| ATOM | 16133 | N | VAL | B | 490 | 51.703 | 37.165 | −36.401 | 1.00 | 24.32 | B | N |
| ATOM | 16134 | CA | VAL | B | 490 | 51.890 | 36.201 | −35.318 | 1.00 | 24.64 | B | C |
| ATOM | 16136 | CB | VAL | B | 490 | 51.905 | 34.758 | −35.847 | 1.00 | 24.98 | B | C |
| ATOM | 16138 | CG1 | VAL | B | 490 | 52.313 | 33.755 | −34.747 | 1.00 | 24.04 | B | C |
| ATOM | 16142 | CG2 | VAL | B | 490 | 50.555 | 34.409 | −36.395 | 1.00 | 20.83 | B | C |
| ATOM | 16146 | C | VAL | B | 490 | 53.133 | 36.517 | −34.465 | 1.00 | 25.21 | B | C |
| ATOM | 16147 | O | VAL | B | 490 | 53.084 | 36.405 | −33.252 | 1.00 | 26.85 | B | O |
| ATOM | 16149 | N | MET | B | 491 | 54.221 | 36.962 | −35.085 | 1.00 | 27.17 | B | N |
| ATOM | 16150 | CA | MET | B | 491 | 55.441 | 37.314 | −34.345 | 1.00 | 27.17 | B | C |
| ATOM | 16152 | CB | MET | B | 491 | 56.619 | 37.595 | −35.286 | 1.00 | 29.59 | B | C |
| ATOM | 16155 | CG | MET | B | 491 | 56.984 | 36.475 | −36.254 | 1.00 | 32.48 | B | C |
| ATOM | 16158 | SD | MET | B | 491 | 58.082 | 35.259 | −35.532 | 1.00 | 54.54 | B | S |
| ATOM | 16159 | CE | MET | B | 491 | 58.676 | 34.476 | −37.042 | 1.00 | 58.30 | B | C |
| ATOM | 16163 | C | MET | B | 491 | 55.183 | 38.545 | −33.498 | 1.00 | 26.01 | B | C |
| ATOM | 16164 | O | MET | B | 491 | 55.677 | 38.646 | −32.387 | 1.00 | 27.29 | B | O |
| ATOM | 16166 | N | ASN | B | 492 | 54.414 | 39.494 | −34.024 | 1.00 | 25.33 | B | N |
| ATOM | 16167 | CA | ASN | B | 492 | 54.027 | 40.675 | −33.241 | 1.00 | 25.11 | B | C |
| ATOM | 16169 | CB | ASN | B | 492 | 53.294 | 41.713 | −34.100 | 1.00 | 26.44 | B | C |
| ATOM | 16172 | CG | ASN | B | 492 | 54.206 | 42.393 | −35.135 | 1.00 | 31.18 | B | C |
| ATOM | 16173 | OD1 | ASN | B | 492 | 55.413 | 42.496 | −34.944 | 1.00 | 41.61 | B | O |
| ATOM | 16174 | ND2 | ASN | B | 492 | 53.610 | 42.884 | −36.226 | 1.00 | 31.04 | B | N |
| ATOM | 16177 | C | ASN | B | 492 | 53.163 | 40.308 | −32.025 | 1.00 | 21.95 | B | C |
| ATOM | 16178 | O | ASN | B | 492 | 53.310 | 40.913 | −30.977 | 1.00 | 23.50 | B | O |
| ATOM | 16180 | N | LEU | B | 493 | 52.272 | 39.332 | −32.176 | 1.00 | 16.94 | B | N |
| ATOM | 16181 | CA | LEU | B | 493 | 51.452 | 38.837 | −31.078 | 1.00 | 19.50 | B | C |
| ATOM | 16183 | CB | LEU | B | 493 | 50.401 | 37.871 | −31.626 | 1.00 | 20.12 | B | C |
| ATOM | 16186 | CG | LEU | B | 493 | 49.330 | 37.252 | −30.730 | 1.00 | 29.36 | B | C |
| ATOM | 16188 | CD1 | LEU | B | 493 | 48.557 | 38.309 | −29.904 | 1.00 | 28.24 | B | C |
| ATOM | 16192 | CD2 | LEU | B | 493 | 48.355 | 36.399 | −31.599 | 1.00 | 21.19 | B | C |
| ATOM | 16196 | C | LEU | B | 493 | 52.359 | 38.162 | −30.021 | 1.00 | 19.84 | B | C |
| ATOM | 16197 | O | LEU | B | 493 | 52.219 | 38.393 | −28.819 | 1.00 | 19.40 | B | O |
| ATOM | 16199 | N | ILE | B | 494 | 53.326 | 37.380 | −30.477 | 1.00 | 20.01 | B | N |
| ATOM | 16200 | CA | ILE | B | 494 | 54.330 | 36.845 | −29.569 | 1.00 | 20.75 | B | C |
| ATOM | 16202 | CB | ILE | B | 494 | 55.346 | 35.966 | −30.315 | 1.00 | 20.42 | B | C |
| ATOM | 16204 | CG1 | ILE | B | 494 | 54.646 | 34.675 | −30.739 | 1.00 | 16.69 | B | C |
| ATOM | 16207 | CD1 | ILE | B | 494 | 55.474 | 33.814 | −31.610 | 1.00 | 19.06 | B | C |
| ATOM | 16211 | CG2 | ILE | B | 494 | 56.521 | 35.613 | −29.418 | 1.00 | 20.38 | B | C |
| ATOM | 16215 | C | ILE | B | 494 | 55.009 | 37.965 | −28.770 | 1.00 | 20.30 | B | C |
| ATOM | 16216 | O | ILE | B | 494 | 55.087 | 37.890 | −27.548 | 1.00 | 20.50 | B | O |
| ATOM | 16218 | N | ASP | B | 495 | 55.429 | 39.026 | −29.442 | 1.00 | 20.29 | B | N |
| ATOM | 16219 | CA | ASP | B | 495 | 56.042 | 40.169 | −28.763 | 1.00 | 20.00 | B | C |
| ATOM | 16221 | CB | ASP | B | 495 | 56.476 | 41.235 | −29.773 | 1.00 | 19.65 | B | C |
| ATOM | 16224 | CG | ASP | B | 495 | 57.672 | 40.795 | −30.609 | 1.00 | 22.70 | B | C |
| ATOM | 16225 | OD1 | ASP | B | 495 | 58.358 | 39.819 | −30.243 | 1.00 | 32.40 | B | O |
| ATOM | 16226 | OD2 | ASP | B | 495 | 57.943 | 41.429 | −31.644 | 1.00 | 33.90 | B | O |
| ATOM | 16227 | C | ASP | B | 495 | 55.140 | 40.800 | −27.717 | 1.00 | 22.04 | B | C |
| ATOM | 16228 | O | ASP | B | 495 | 55.567 | 41.053 | −26.588 | 1.00 | 23.10 | B | O |
| ATOM | 16230 | N | GLU | B | 496 | 53.897 | 41.061 | −28.088 | 1.00 | 23.21 | B | N |
| ATOM | 16231 | CA | GLU | B | 496 | 52.959 | 41.715 | −27.191 | 1.00 | 25.03 | B | C |
| ATOM | 16233 | CB | GLU | B | 496 | 51.643 | 42.007 | −27.902 | 1.00 | 24.60 | B | C |
| ATOM | 16236 | CG | GLU | B | 496 | 51.772 | 43.101 | −28.938 | 1.00 | 34.66 | B | C |
| ATOM | 16239 | CD | GLU | B | 496 | 52.250 | 44.433 | −28.354 | 1.00 | 43.94 | B | C |
| ATOM | 16240 | OE1 | GLU | B | 496 | 53.248 | 44.980 | −28.880 | 1.00 | 45.89 | B | O |
| ATOM | 16241 | OE2 | GLU | B | 496 | 51.633 | 44.926 | −27.377 | 1.00 | 48.24 | B | O |
| ATOM | 16242 | C | GLU | B | 496 | 52.693 | 40.840 | −26.003 | 1.00 | 23.68 | B | C |
| ATOM | 16243 | O | GLU | B | 496 | 52.579 | 41.339 | −24.882 | 1.00 | 23.34 | B | O |
| ATOM | 16245 | N | THR | B | 497 | 52.606 | 39.534 | −26.257 | 1.00 | 21.60 | B | N |

TABLE 4-2-continued

| Coordinates of *P. alba* IspS | | | | | | | | | | | | |
|---|---|---|---|---|---|---|---|---|---|---|---|---|
| ATOM | 16246 | CA | THR | B | 497 | 52.340 | 38.571 | −25.214 | 1.00 | 21.88 | B | C |
| ATOM | 16248 | CB | THR | B | 497 | 52.112 | 37.168 | −25.799 | 1.00 | 22.84 | B | C |
| ATOM | 16250 | OG1 | THR | B | 497 | 51.067 | 37.231 | −26.790 | 1.00 | 24.32 | B | O |
| ATOM | 16252 | CG2 | THR | B | 497 | 51.719 | 36.222 | −24.710 | 1.00 | 18.88 | B | C |
| ATOM | 16256 | C | THR | B | 497 | 53.510 | 38.565 | −24.217 | 1.00 | 21.49 | B | C |
| ATOM | 16257 | O | THR | B | 497 | 53.295 | 38.521 | −23.022 | 1.00 | 20.84 | B | O |
| ATOM | 16259 | N | TRP | B | 498 | 54.737 | 38.654 | −24.715 | 1.00 | 19.80 | B | N |
| ATOM | 16260 | CA | TRP | B | 498 | 55.892 | 38.786 | −23.847 | 1.00 | 21.21 | B | C |
| ATOM | 16262 | CB | TRP | B | 498 | 57.194 | 38.771 | −24.641 | 1.00 | 20.21 | B | C |
| ATOM | 16265 | CG | TRP | B | 498 | 57.821 | 37.406 | −24.729 | 1.00 | 22.28 | B | C |
| ATOM | 16266 | CD1 | TRP | B | 498 | 57.768 | 36.547 | −25.786 | 1.00 | 18.79 | B | C |
| ATOM | 16268 | NE1 | TRP | B | 498 | 58.454 | 35.404 | −25.497 | 1.00 | 23.07 | B | N |
| ATOM | 16270 | CE2 | TRP | B | 498 | 58.985 | 35.508 | −24.241 | 1.00 | 18.89 | B | C |
| ATOM | 16271 | CD2 | TRP | B | 498 | 58.603 | 36.756 | −23.726 | 1.00 | 23.52 | B | C |
| ATOM | 16272 | CE3 | TRP | B | 498 | 59.019 | 37.107 | −22.439 | 1.00 | 25.36 | B | C |
| ATOM | 16274 | CZ3 | TRP | B | 498 | 59.775 | 36.204 | −21.715 | 1.00 | 24.20 | B | C |
| ATOM | 16276 | CH2 | TRP | B | 498 | 60.147 | 34.974 | −22.259 | 1.00 | 20.69 | B | C |
| ATOM | 16278 | CZ2 | TRP | B | 498 | 59.759 | 34.607 | −23.516 | 1.00 | 25.94 | B | C |
| ATOM | 16280 | C | TRP | B | 498 | 55.844 | 40.048 | −22.992 | 1.00 | 21.86 | B | C |
| ATOM | 16281 | O | TRP | B | 498 | 56.199 | 40.028 | −21.809 | 1.00 | 22.63 | B | O |
| ATOM | 16283 | N | LYS | B | 499 | 55.404 | 41.147 | −23.576 | 1.00 | 22.03 | B | N |
| ATOM | 16284 | CA | LYS | B | 499 | 55.328 | 42.379 | −22.823 | 1.00 | 22.69 | B | C |
| ATOM | 16286 | CB | LYS | B | 499 | 54.851 | 43.541 | −23.692 | 1.00 | 23.12 | B | C |
| ATOM | 16289 | CG | LYS | B | 499 | 55.860 | 43.971 | −24.779 | 1.00 | 19.45 | B | C |
| ATOM | 16292 | CD | LYS | B | 499 | 55.348 | 45.181 | −25.597 | 1.00 | 20.45 | B | C |
| ATOM | 16295 | CE | LYS | B | 499 | 56.178 | 45.364 | −26.882 | 1.00 | 24.37 | B | C |
| ATOM | 16298 | NZ | LYS | B | 499 | 55.795 | 46.603 | −27.636 | 1.00 | 25.22 | B | N |
| ATOM | 16302 | C | LYS | B | 499 | 54.438 | 42.197 | −21.603 | 1.00 | 23.79 | B | C |
| ATOM | 16303 | O | LYS | B | 499 | 54.781 | 42.641 | −20.506 | 1.00 | 26.86 | B | O |
| ATOM | 16305 | N | LYS | B | 500 | 53.332 | 41.492 | −21.776 | 1.00 | 24.19 | B | N |
| ATOM | 16306 | CA | LYS | B | 500 | 52.421 | 41.226 | −20.670 | 1.00 | 24.67 | B | C |
| ATOM | 16308 | CB | LYS | B | 500 | 51.083 | 40.762 | −21.234 | 1.00 | 27.83 | B | C |
| ATOM | 16311 | CG | LYS | B | 500 | 50.405 | 41.905 | −21.987 | 1.00 | 27.12 | B | C |
| ATOM | 16314 | CD | LYS | B | 500 | 49.172 | 41.461 | −22.733 | 1.00 | 34.50 | B | C |
| ATOM | 16317 | CE | LYS | B | 500 | 48.524 | 42.638 | −23.450 | 1.00 | 34.28 | B | C |
| ATOM | 16320 | NZ | LYS | B | 500 | 47.799 | 42.149 | −24.632 | 1.00 | 42.60 | B | N |
| ATOM | 16324 | C | LYS | B | 500 | 52.951 | 40.237 | −19.628 | 1.00 | 23.00 | B | C |
| ATOM | 16325 | O | LYS | B | 500 | 52.735 | 40.416 | −18.443 | 1.00 | 24.58 | B | O |
| ATOM | 16327 | N | MET | B | 501 | 53.669 | 39.208 | −20.055 | 1.00 | 22.99 | B | N |
| ATOM | 16328 | CA | MET | B | 501 | 54.321 | 38.326 | −19.099 | 1.00 | 20.54 | B | C |
| ATOM | 16330 | CB | MET | B | 501 | 55.005 | 37.163 | −19.801 | 1.00 | 20.14 | B | C |
| ATOM | 16333 | CG | MET | B | 501 | 54.036 | 36.223 | −20.472 | 1.00 | 24.64 | B | C |
| ATOM | 16336 | SD | MET | B | 501 | 54.785 | 34.668 | −21.007 | 1.00 | 29.22 | B | S |
| ATOM | 16337 | CE | MET | B | 501 | 56.131 | 35.198 | −22.016 | 1.00 | 26.22 | B | C |
| ATOM | 16341 | C | MET | B | 501 | 55.330 | 39.112 | −18.278 | 1.00 | 19.87 | B | C |
| ATOM | 16342 | O | MET | B | 501 | 55.398 | 38.941 | −17.069 | 1.00 | 23.88 | B | O |
| ATOM | 16344 | N | ASN | B | 502 | 56.096 | 39.979 | −18.928 | 1.00 | 18.65 | B | N |
| ATOM | 16345 | CA | ASN | B | 502 | 57.129 | 40.749 | −18.260 | 1.00 | 19.97 | B | C |
| ATOM | 16347 | CB | ASN | B | 502 | 57.837 | 41.683 | −19.265 | 1.00 | 18.67 | B | C |
| ATOM | 16350 | CG | ASN | B | 502 | 58.811 | 40.958 | −20.196 | 1.00 | 22.60 | B | C |
| ATOM | 16351 | OD1 | ASN | B | 502 | 59.178 | 39.788 | −19.987 | 1.00 | 22.42 | B | O |
| ATOM | 16352 | ND2 | ASN | B | 502 | 59.273 | 41.685 | −21.224 | 1.00 | 16.81 | B | N |
| ATOM | 16355 | C | ASN | B | 502 | 56.523 | 41.576 | −17.119 | 1.00 | 22.98 | B | C |
| ATOM | 16356 | O | ASN | B | 502 | 57.114 | 41.713 | −16.027 | 1.00 | 24.16 | B | O |
| ATOM | 16358 | N | LYS | B | 503 | 55.342 | 42.136 | −17.376 | 1.00 | 24.97 | B | N |
| ATOM | 16359 | CA | LYS | B | 503 | 54.643 | 42.934 | −16.369 | 1.00 | 28.54 | B | C |
| ATOM | 16361 | CB | LYS | B | 503 | 53.493 | 43.719 | −17.003 | 1.00 | 27.67 | B | C |
| ATOM | 16364 | CG | LYS | B | 503 | 52.638 | 44.472 | −16.012 | 1.00 | 33.09 | B | C |
| ATOM | 16367 | CD | LYS | B | 503 | 51.658 | 45.394 | −16.757 | 1.00 | 41.49 | B | C |
| ATOM | 16370 | CE | LYS | B | 503 | 50.925 | 46.355 | −15.801 | 1.00 | 47.16 | B | C |
| ATOM | 16373 | NZ | LYS | B | 503 | 49.615 | 46.854 | −16.376 | 1.00 | 45.45 | B | N |
| ATOM | 16377 | C | LYS | B | 503 | 54.141 | 42.058 | −15.221 | 1.00 | 28.95 | B | C |
| ATOM | 16378 | O | LYS | B | 503 | 54.307 | 42.396 | −14.056 | 1.00 | 30.69 | B | O |
| ATOM | 16380 | N | GLU | B | 504 | 53.522 | 40.938 | −15.546 | 1.00 | 30.28 | B | N |
| ATOM | 16381 | CA | GLU | B | 504 | 53.101 | 39.983 | −14.508 | 1.00 | 31.89 | B | C |
| ATOM | 16383 | CB | GLU | B | 504 | 52.551 | 38.690 | −15.149 | 1.00 | 33.44 | B | C |
| ATOM | 16386 | CG | GLU | B | 504 | 51.701 | 37.808 | −14.225 | 1.00 | 38.98 | B | C |
| ATOM | 16389 | CD | GLU | B | 504 | 50.382 | 38.465 | −13.829 | 1.00 | 47.41 | B | C |
| ATOM | 16390 | OE1 | GLU | B | 504 | 49.897 | 38.183 | −12.715 | 1.00 | 52.15 | B | O |
| ATOM | 16391 | OE2 | GLU | B | 504 | 49.841 | 39.277 | −14.618 | 1.00 | 50.82 | B | O |
| ATOM | 16392 | C | GLU | B | 504 | 54.267 | 39.675 | −13.555 | 1.00 | 29.72 | B | C |
| ATOM | 16393 | O | GLU | B | 504 | 54.119 | 39.732 | −12.335 | 1.00 | 31.31 | B | O |
| ATOM | 16395 | N | LYS | B | 505 | 55.433 | 39.388 | −14.114 | 1.00 | 28.05 | B | N |
| ATOM | 16396 | CA | LYS | B | 505 | 56.601 | 38.981 | −13.323 | 1.00 | 27.17 | B | C |
| ATOM | 16398 | CB | LYS | B | 505 | 57.735 | 38.562 | −14.266 | 1.00 | 25.64 | B | C |
| ATOM | 16401 | CG | LYS | B | 505 | 59.066 | 38.259 | −13.594 | 1.00 | 26.00 | B | C |
| ATOM | 16404 | CD | LYS | B | 505 | 58.995 | 37.017 | −12.710 | 1.00 | 25.01 | B | C |
| ATOM | 16407 | CE | LYS | B | 505 | 60.305 | 36.802 | −11.941 | 1.00 | 22.47 | B | C |

TABLE 4-2-continued

Coordinates of *P. alba* IspS

| | | | | | | | | | | | | |
|---|---|---|---|---|---|---|---|---|---|---|---|---|
| ATOM | 16410 | NZ | LYS | B | 505 | 61.449 | 36.651 | −12.865 | 1.00 | 30.06 | B | N |
| ATOM | 16414 | C | LYS | B | 505 | 57.080 | 40.122 | −12.423 | 1.00 | 29.79 | B | C |
| ATOM | 16415 | O | LYS | B | 505 | 57.422 | 39.943 | −11.258 | 1.00 | 30.03 | B | O |
| ATOM | 16417 | N | LEU | B | 506 | 57.092 | 41.306 | −12.993 | 1.00 | 33.92 | B | N |
| ATOM | 16418 | CA | LEU | B | 506 | 57.667 | 42.466 | −12.352 | 1.00 | 37.31 | B | C |
| ATOM | 16420 | CB | LEU | B | 506 | 57.784 | 43.589 | −13.383 | 1.00 | 37.37 | B | C |
| ATOM | 16423 | CG | LEU | B | 506 | 58.791 | 44.692 | −13.143 | 1.00 | 42.52 | B | C |
| ATOM | 16425 | CD1 | LEU | B | 506 | 60.133 | 44.138 | −12.685 | 1.00 | 39.23 | B | C |
| ATOM | 16429 | CD2 | LEU | B | 506 | 58.933 | 45.485 | −14.443 | 1.00 | 47.19 | B | C |
| ATOM | 16433 | C | LEU | B | 506 | 56.838 | 42.932 | −11.174 | 1.00 | 39.52 | B | C |
| ATOM | 16434 | O | LEU | B | 506 | 57.386 | 43.311 | −10.144 | 1.00 | 40.98 | B | O |
| ATOM | 16436 | N | GLY | B | 507 | 55.521 | 42.894 | −11.319 | 1.00 | 42.30 | B | N |
| ATOM | 16437 | CA | GLY | B | 507 | 54.656 | 43.514 | −10.336 | 1.00 | 45.83 | B | C |
| ATOM | 16440 | C | GLY | B | 507 | 53.330 | 42.824 | −10.120 | 1.00 | 49.02 | B | C |
| ATOM | 16441 | O | GLY | B | 507 | 52.686 | 42.354 | −11.062 | 1.00 | 51.49 | B | O |
| ATOM | 16443 | N | GLY | B | 508 | 52.953 | 42.755 | −8.846 | 1.00 | 51.72 | B | N |
| ATOM | 16444 | CA | GLY | B | 508 | 51.591 | 42.445 | −8.415 | 1.00 | 52.78 | B | C |
| ATOM | 16447 | C | GLY | B | 508 | 50.900 | 41.218 | −8.984 | 1.00 | 51.93 | B | C |
| ATOM | 16448 | O | GLY | B | 508 | 49.723 | 41.287 | −9.375 | 1.00 | 54.01 | B | O |
| ATOM | 16450 | N | SER | B | 509 | 51.595 | 40.092 | −9.038 | 1.00 | 49.18 | B | N |
| ATOM | 16451 | CA | ASER | B | 509 | 50.977 | 38.831 | −9.421 | 0.50 | 48.36 | B | C |
| ATOM | 16452 | CA | BSER | B | 509 | 50.890 | 38.872 | −9.440 | 0.50 | 48.06 | B | C |
| ATOM | 16455 | CB | ASER | B | 509 | 52.060 | 37.834 | −9.871 | 0.50 | 48.19 | B | C |
| ATOM | 16456 | CB | BSER | B | 509 | 51.793 | 37.829 | −10.102 | 0.50 | 47.86 | B | C |
| ATOM | 16461 | OG | ASER | B | 509 | 53.237 | 37.924 | −9.070 | 0.50 | 46.36 | B | O |
| ATOM | 16462 | OG | BSER | B | 509 | 50.997 | 36.778 | −10.655 | 0.50 | 43.78 | B | O |
| ATOM | 16465 | C | SER | B | 509 | 50.184 | 38.268 | −8.237 | 1.00 | 47.03 | B | C |
| ATOM | 16466 | O | SER | B | 509 | 50.561 | 38.492 | −7.083 | 1.00 | 45.61 | B | O |
| ATOM | 16468 | N | LEU | B | 510 | 49.118 | 37.529 | −8.528 | 1.00 | 46.26 | B | N |
| ATOM | 16469 | CA | LEU | B | 510 | 48.442 | 36.736 | −7.513 | 1.00 | 45.94 | B | C |
| ATOM | 16471 | CB | LEU | B | 510 | 47.146 | 36.129 | −8.067 | 1.00 | 47.18 | B | C |
| ATOM | 16474 | CG | LEU | B | 510 | 46.198 | 37.118 | −8.781 | 1.00 | 53.98 | B | C |
| ATOM | 16476 | CD1 | LEU | B | 510 | 44.910 | 36.427 | −9.230 | 1.00 | 58.51 | B | C |
| ATOM | 16480 | CD2 | LEU | B | 510 | 45.873 | 38.358 | −7.911 | 1.00 | 59.66 | B | C |
| ATOM | 16484 | C | LEU | B | 510 | 49.432 | 35.643 | −7.040 | 1.00 | 43.67 | B | C |
| ATOM | 16485 | O | LEU | B | 510 | 49.486 | 35.316 | −5.843 | 1.00 | 45.41 | B | O |
| ATOM | 16487 | N | PHE | B | 511 | 50.262 | 35.156 | −7.969 | 1.00 | 37.67 | B | N |
| ATOM | 16488 | CA | PHE | B | 511 | 51.233 | 34.089 | −7.707 | 1.00 | 35.65 | B | C |
| ATOM | 16490 | CB | PHE | B | 511 | 51.418 | 33.218 | −8.967 | 1.00 | 34.37 | B | C |
| ATOM | 16493 | CG | PHE | B | 511 | 50.169 | 32.496 | −9.394 | 1.00 | 29.50 | B | C |
| ATOM | 16494 | CD1 | PHE | B | 511 | 49.935 | 31.208 | −8.981 | 1.00 | 27.92 | B | C |
| ATOM | 16496 | CE1 | PHE | B | 511 | 48.772 | 30.537 | −9.360 | 1.00 | 32.35 | B | C |
| ATOM | 16498 | CZ | PHE | B | 511 | 47.838 | 31.173 | −10.146 | 1.00 | 33.79 | B | C |
| ATOM | 16500 | CE2 | PHE | B | 511 | 48.062 | 32.483 | −10.557 | 1.00 | 31.04 | B | C |
| ATOM | 16502 | CD2 | PHE | B | 511 | 49.213 | 33.128 | −10.180 | 1.00 | 27.15 | B | C |
| ATOM | 16504 | C | PHE | B | 511 | 52.596 | 34.603 | −7.235 | 1.00 | 35.79 | B | C |
| ATOM | 16505 | O | PHE | B | 511 | 52.977 | 35.747 | −7.481 | 1.00 | 36.71 | B | O |
| ATOM | 16507 | N | ALA | B | 512 | 53.343 | 33.747 | −6.555 | 1.00 | 36.55 | B | N |
| ATOM | 16508 | CA | ALA | B | 512 | 54.681 | 34.127 | −6.137 | 1.00 | 37.34 | B | C |
| ATOM | 16510 | CB | ALA | B | 512 | 55.203 | 33.149 | −5.078 | 1.00 | 36.86 | B | C |
| ATOM | 16514 | C | ALA | B | 512 | 55.593 | 34.159 | −7.380 | 1.00 | 37.03 | B | C |
| ATOM | 16515 | O | ALA | B | 512 | 55.400 | 33.384 | −8.315 | 1.00 | 35.37 | B | O |
| ATOM | 16517 | N | LYS | B | 513 | 56.575 | 35.061 | −7.381 | 1.00 | 37.04 | B | N |
| ATOM | 16518 | CA | LYS | B | 513 | 57.500 | 35.233 | −8.519 | 1.00 | 36.97 | B | C |
| ATOM | 16520 | CB | LYS | B | 513 | 58.511 | 36.341 | −8.230 | 1.00 | 36.08 | B | C |
| ATOM | 16523 | CG | LYS | B | 513 | 57.877 | 37.716 | −8.124 | 1.00 | 43.23 | B | C |
| ATOM | 16526 | CD | LYS | B | 513 | 58.928 | 38.808 | −7.942 | 1.00 | 51.27 | B | C |
| ATOM | 16529 | CE | LYS | B | 513 | 58.301 | 40.198 | −7.948 | 1.00 | 56.81 | B | C |
| ATOM | 16532 | NZ | LYS | B | 513 | 59.264 | 41.260 | −8.368 | 1.00 | 56.22 | B | N |
| ATOM | 16536 | C | LYS | B | 513 | 58.236 | 33.964 | −9.006 | 1.00 | 34.73 | B | C |
| ATOM | 16537 | O | LYS | B | 513 | 58.529 | 33.847 | −10.184 | 1.00 | 35.14 | B | O |
| ATOM | 16539 | N | PRO | B | 514 | 58.539 | 33.019 | −8.111 | 1.00 | 33.75 | B | N |
| ATOM | 16540 | CA | PRO | B | 514 | 59.171 | 31.801 | −8.618 | 1.00 | 31.10 | B | C |
| ATOM | 16542 | CB | PRO | B | 514 | 59.475 | 30.993 | −7.350 | 1.00 | 31.76 | B | C |
| ATOM | 16545 | CG | PRO | B | 514 | 59.565 | 32.013 | −6.258 | 1.00 | 33.72 | B | C |
| ATOM | 16548 | CD | PRO | B | 514 | 58.575 | 33.088 | −6.636 | 1.00 | 34.82 | B | C |
| ATOM | 16551 | C | PRO | B | 514 | 58.274 | 30.994 | −9.531 | 1.00 | 29.47 | B | C |
| ATOM | 16552 | O | PRO | B | 514 | 58.761 | 30.432 | −10.505 | 1.00 | 31.73 | B | O |
| ATOM | 16553 | N | PHE | B | 515 | 56.980 | 30.921 | −9.229 | 1.00 | 27.01 | B | N |
| ATOM | 16554 | CA | PHE | B | 515 | 56.080 | 30.186 | −10.095 | 1.00 | 24.99 | B | C |
| ATOM | 16556 | CB | PHE | B | 515 | 54.791 | 29.771 | −9.412 | 1.00 | 22.89 | B | C |
| ATOM | 16559 | CG | PHE | B | 515 | 53.802 | 29.171 | −10.366 | 1.00 | 25.51 | B | C |
| ATOM | 16560 | CD1 | PHE | B | 515 | 54.021 | 27.920 | −10.902 | 1.00 | 26.17 | B | C |
| ATOM | 16562 | CE1 | PHE | B | 515 | 53.126 | 27.366 | −11.810 | 1.00 | 26.76 | B | C |
| ATOM | 16564 | CZ | PHE | B | 515 | 52.039 | 28.081 | −12.196 | 1.00 | 22.84 | B | C |
| ATOM | 16566 | CE2 | PHE | B | 515 | 51.816 | 29.356 | −11.661 | 1.00 | 20.66 | B | C |
| ATOM | 16568 | CD2 | PHE | B | 515 | 52.695 | 29.884 | −10.779 | 1.00 | 22.38 | B | C |
| ATOM | 16570 | C | PHE | B | 515 | 55.789 | 31.000 | −11.364 | 1.00 | 24.60 | B | C |

TABLE 4-2-continued

| Coordinates of *P. alba* IspS | | | | | | | | | | | | |
|---|---|---|---|---|---|---|---|---|---|---|---|---|
| ATOM | 16571 | O | PHE | B | 515 | 55.775 | 30.452 | −12.455 | 1.00 | 25.39 | B | O |
| ATOM | 16573 | N | VAL | B | 516 | 55.598 | 32.301 | −11.241 | 1.00 | 23.02 | B | N |
| ATOM | 16574 | CA | VAL | B | 516 | 55.459 | 33.127 | −12.435 | 1.00 | 22.33 | B | C |
| ATOM | 16576 | CB | VAL | B | 516 | 55.339 | 34.620 | −12.126 | 1.00 | 23.22 | B | C |
| ATOM | 16578 | CG1 | VAL | B | 516 | 54.200 | 34.904 | −11.108 | 1.00 | 23.93 | B | C |
| ATOM | 16582 | CG2 | VAL | B | 516 | 55.087 | 35.401 | −13.412 | 1.00 | 19.34 | B | C |
| ATOM | 16586 | C | VAL | B | 516 | 56.633 | 32.914 | −13.403 | 1.00 | 22.95 | B | C |
| ATOM | 16587 | O | VAL | B | 516 | 56.435 | 32.854 | −14.629 | 1.00 | 23.90 | B | O |
| ATOM | 16589 | N | GLU | B | 517 | 57.834 | 32.776 | −12.854 | 1.00 | 21.79 | B | N |
| ATOM | 16590 | CA | GLU | B | 517 | 59.049 | 32.572 | −13.651 | 1.00 | 22.46 | B | C |
| ATOM | 16592 | CB | GLU | B | 517 | 60.298 | 32.804 | −12.771 | 1.00 | 24.28 | B | C |
| ATOM | 16595 | CG | GLU | B | 517 | 61.663 | 32.717 | −13.489 | 1.00 | 22.17 | B | C |
| ATOM | 16598 | CD | GLU | B | 517 | 61.902 | 33.823 | −14.511 | 1.00 | 26.69 | B | C |
| ATOM | 16599 | OE1 | GLU | B | 517 | 61.121 | 34.806 | −14.594 | 1.00 | 26.06 | B | O |
| ATOM | 16600 | OE2 | GLU | B | 517 | 62.892 | 33.702 | −15.252 | 1.00 | 29.10 | B | O |
| ATOM | 16601 | C | GLU | B | 517 | 59.098 | 31.172 | −14.273 | 1.00 | 21.73 | B | C |
| ATOM | 16602 | O | GLU | B | 517 | 59.505 | 31.018 | −15.415 | 1.00 | 24.57 | B | O |
| ATOM | 16604 | N | THR | B | 518 | 58.717 | 30.151 | −13.512 | 1.00 | 23.11 | B | N |
| ATOM | 16605 | CA | THR | B | 518 | 58.574 | 28.798 | −14.050 | 1.00 | 22.81 | B | C |
| ATOM | 16607 | CB | THR | B | 518 | 58.094 | 27.811 | −12.963 | 1.00 | 24.80 | B | C |
| ATOM | 16609 | OG1 | THR | B | 518 | 59.091 | 27.713 | −11.936 | 1.00 | 21.57 | B | O |
| ATOM | 16611 | CG2 | THR | B | 518 | 57.851 | 26.398 | −13.562 | 1.00 | 21.21 | B | C |
| ATOM | 16615 | C | THR | B | 518 | 57.599 | 28.819 | −15.245 | 1.00 | 23.51 | B | C |
| ATOM | 16616 | O | THR | B | 518 | 57.850 | 28.237 | −16.297 | 1.00 | 22.08 | B | O |
| ATOM | 16618 | N | ALA | B | 519 | 56.515 | 29.554 | −15.105 | 1.00 | 21.37 | B | N |
| ATOM | 16619 | CA | ALA | B | 519 | 55.553 | 29.635 | −16.188 | 1.00 | 21.72 | B | C |
| ATOM | 16621 | CB | ALA | B | 519 | 54.308 | 30.395 | −15.737 | 1.00 | 20.07 | B | C |
| ATOM | 16625 | C | ALA | B | 519 | 56.190 | 30.272 | −17.429 | 1.00 | 20.28 | B | C |
| ATOM | 16626 | O | ALA | B | 519 | 56.043 | 29.775 | −18.555 | 1.00 | 19.22 | B | O |
| ATOM | 16628 | N | ILE | B | 520 | 56.935 | 31.350 | −17.227 | 1.00 | 19.49 | B | N |
| ATOM | 16629 | CA | ILE | B | 520 | 57.552 | 32.014 | −18.366 | 1.00 | 18.67 | B | C |
| ATOM | 16631 | CB | ILE | B | 520 | 58.218 | 33.311 | −17.947 | 1.00 | 19.91 | B | C |
| ATOM | 16633 | CG1 | ILE | B | 520 | 57.161 | 34.343 | −17.572 | 1.00 | 21.75 | B | C |
| ATOM | 16636 | CD1 | ILE | B | 520 | 57.701 | 35.559 | −16.769 | 1.00 | 20.13 | B | C |
| ATOM | 16640 | CG2 | ILE | B | 520 | 59.083 | 33.848 | −19.091 | 1.00 | 18.40 | B | C |
| ATOM | 16644 | C | ILE | B | 520 | 58.573 | 31.106 | −19.044 | 1.00 | 18.88 | B | C |
| ATOM | 16645 | O | ILE | B | 520 | 58.740 | 31.162 | −20.255 | 1.00 | 20.10 | B | O |
| ATOM | 16647 | N | ASN | B | 521 | 59.256 | 30.264 | −18.268 | 1.00 | 18.94 | B | N |
| ATOM | 16648 | CA | ASN | B | 521 | 60.166 | 29.282 | −18.848 | 1.00 | 21.21 | B | C |
| ATOM | 16650 | CB | ASN | B | 521 | 60.849 | 28.442 | −17.757 | 1.00 | 23.50 | B | C |
| ATOM | 16653 | CG | ASN | B | 521 | 61.829 | 29.269 | −16.895 | 1.00 | 26.39 | B | C |
| ATOM | 16654 | OD1 | ASN | B | 521 | 62.321 | 30.339 | −17.308 | 1.00 | 20.77 | B | O |
| ATOM | 16655 | ND2 | ASN | B | 521 | 62.126 | 28.755 | −15.700 | 1.00 | 21.46 | B | N |
| ATOM | 16658 | C | ASN | B | 521 | 59.486 | 28.367 | −19.862 | 1.00 | 19.68 | B | C |
| ATOM | 16659 | O | ASN | B | 521 | 60.113 | 27.923 | −20.824 | 1.00 | 22.84 | B | O |
| ATOM | 16661 | N | LEU | B | 522 | 58.208 | 28.091 | −19.692 | 1.00 | 20.02 | B | N |
| ATOM | 16662 | CA | LEU | B | 522 | 57.544 | 27.288 | −20.700 | 1.00 | 22.98 | B | C |
| ATOM | 16664 | CB | LEU | B | 522 | 56.093 | 27.008 | −20.356 | 1.00 | 23.26 | B | C |
| ATOM | 16667 | CG | LEU | B | 522 | 55.375 | 26.269 | −21.493 | 1.00 | 25.82 | B | C |
| ATOM | 16669 | CD1 | LEU | B | 522 | 55.246 | 24.827 | −21.145 | 1.00 | 31.80 | B | C |
| ATOM | 16673 | CD2 | LEU | B | 522 | 54.016 | 26.847 | −21.730 | 1.00 | 25.39 | B | C |
| ATOM | 16677 | C | LEU | B | 522 | 57.625 | 28.024 | −22.040 | 1.00 | 22.13 | B | C |
| ATOM | 16678 | O | LEU | B | 522 | 57.880 | 27.402 | −23.081 | 1.00 | 25.60 | B | O |
| ATOM | 16680 | N | ALA | B | 523 | 57.441 | 29.336 | −22.015 | 1.00 | 17.13 | B | N |
| ATOM | 16681 | CA | ALA | B | 523 | 57.550 | 30.111 | −23.240 | 1.00 | 19.20 | B | C |
| ATOM | 16683 | CB | ALA | B | 523 | 57.176 | 31.574 | −23.011 | 1.00 | 18.47 | B | C |
| ATOM | 16687 | C | ALA | B | 523 | 58.936 | 30.029 | −23.786 | 1.00 | 18.17 | B | C |
| ATOM | 16688 | O | ALA | B | 523 | 59.102 | 29.951 | −24.972 | 1.00 | 18.29 | B | O |
| ATOM | 16690 | N | ARG | B | 524 | 59.937 | 30.084 | −22.904 | 1.00 | 20.77 | B | N |
| ATOM | 16691 | CA | ARG | B | 524 | 61.325 | 30.052 | −23.343 | 1.00 | 20.63 | B | C |
| ATOM | 16693 | CB | ARG | B | 524 | 62.285 | 30.303 | −22.162 | 1.00 | 22.45 | B | C |
| ATOM | 16696 | CG | ARG | B | 524 | 62.178 | 31.723 | −21.612 | 1.00 | 20.20 | B | C |
| ATOM | 16699 | CD | ARG | B | 524 | 63.201 | 32.015 | −20.574 | 1.00 | 17.77 | B | C |
| ATOM | 16702 | NE | ARG | B | 524 | 63.198 | 33.425 | −20.165 | 1.00 | 17.96 | B | N |
| ATOM | 16704 | CZ | ARG | B | 524 | 62.938 | 33.867 | −18.944 | 1.00 | 20.16 | B | C |
| ATOM | 16705 | NH1 | ARG | B | 524 | 62.638 | 33.025 | −17.961 | 1.00 | 24.53 | B | N |
| ATOM | 16708 | NH2 | ARG | B | 524 | 63.015 | 35.165 | −18.692 | 1.00 | 19.14 | B | N |
| ATOM | 16711 | C | ARG | B | 524 | 61.643 | 28.717 | −23.998 | 1.00 | 19.90 | B | C |
| ATOM | 16712 | O | ARG | B | 524 | 62.287 | 28.679 | −25.017 | 1.00 | 19.59 | B | O |
| ATOM | 16714 | N | GLN | B | 525 | 61.179 | 27.632 | −23.398 | 1.00 | 21.47 | B | N |
| ATOM | 16715 | CA | GLN | B | 525 | 61.387 | 26.314 | −23.961 | 1.00 | 22.83 | B | C |
| ATOM | 16717 | CB | GLN | B | 525 | 60.887 | 25.221 | −23.002 | 1.00 | 21.14 | B | C |
| ATOM | 16720 | CG | GLN | B | 525 | 61.193 | 23.820 | −23.486 | 1.00 | 26.80 | B | C |
| ATOM | 16723 | CD | GLN | B | 525 | 62.683 | 23.560 | −23.672 | 1.00 | 31.34 | B | C |
| ATOM | 16724 | OE1 | GLN | B | 525 | 63.453 | 23.736 | −22.757 | 1.00 | 30.44 | B | O |
| ATOM | 16725 | NE2 | GLN | B | 525 | 63.075 | 23.120 | −24.851 | 1.00 | 33.52 | B | N |
| ATOM | 16728 | C | GLN | B | 525 | 60.721 | 26.191 | −25.332 | 1.00 | 23.13 | B | C |
| ATOM | 16729 | O | GLN | B | 525 | 61.251 | 25.517 | −26.226 | 1.00 | 24.85 | B | O |

TABLE 4-2-continued

| Coordinates of *P. alba* IspS | | | | | | | | | | | | |
|---|---|---|---|---|---|---|---|---|---|---|---|---|
| ATOM | 16731 | N | SER | B | 526 | 59.586 | 26.856 | −25.507 | 1.00 | 21.76 | B | N |
| ATOM | 16732 | CA | SER | B | 526 | 58.916 | 26.851 | −26.788 | 1.00 | 20.34 | B | C |
| ATOM | 16734 | CB | SER | B | 526 | 57.571 | 27.570 | −26.692 | 1.00 | 21.50 | B | C |
| ATOM | 16737 | OG | SER | B | 526 | 56.684 | 26.836 | −25.851 | 1.00 | 24.20 | B | O |
| ATOM | 16739 | C | SER | B | 526 | 59.779 | 27.479 | −27.833 | 1.00 | 21.36 | B | C |
| ATOM | 16740 | O | SER | B | 526 | 59.917 | 26.945 | −28.944 | 1.00 | 20.48 | B | O |
| ATOM | 16742 | N | HIS | B | 527 | 60.376 | 28.622 | −27.513 | 1.00 | 24.54 | B | N |
| ATOM | 16743 | CA | HIS | B | 527 | 61.245 | 29.288 | −28.500 | 1.00 | 26.44 | B | C |
| ATOM | 16745 | CB | HIS | B | 527 | 61.754 | 30.633 | −27.984 | 1.00 | 28.07 | B | C |
| ATOM | 16748 | CG | HIS | B | 527 | 60.721 | 31.719 | −27.999 | 1.00 | 25.63 | B | C |
| ATOM | 16749 | ND1 | HIS | B | 527 | 60.369 | 32.390 | −29.144 | 1.00 | 25.98 | B | N |
| ATOM | 16751 | CE1 | HIS | B | 527 | 59.433 | 33.278 | −28.867 | 1.00 | 25.15 | B | C |
| ATOM | 16753 | NE2 | HIS | B | 527 | 59.162 | 33.209 | −27.579 | 1.00 | 25.73 | B | N |
| ATOM | 16755 | CD2 | HIS | B | 527 | 59.961 | 32.245 | −27.009 | 1.00 | 29.05 | B | C |
| ATOM | 16757 | C | HIS | B | 527 | 62.431 | 28.401 | −28.858 | 1.00 | 28.50 | B | C |
| ATOM | 16758 | O | HIS | B | 527 | 62.881 | 28.401 | −29.992 | 1.00 | 29.68 | B | O |
| ATOM | 16760 | N | CYS | B | 528 | 62.930 | 27.631 | −27.893 | 1.00 | 28.29 | B | N |
| ATOM | 16761 | CA | CYS | B | 528 | 64.161 | 26.887 | −28.104 | 1.00 | 32.46 | B | C |
| ATOM | 16763 | CB | CYS | B | 528 | 64.855 | 26.629 | −26.769 | 1.00 | 32.27 | B | C |
| ATOM | 16766 | SG | CYS | B | 528 | 65.481 | 28.140 | −26.015 | 1.00 | 29.31 | B | S |
| ATOM | 16768 | C | CYS | B | 528 | 63.912 | 25.578 | −28.852 | 1.00 | 34.73 | B | C |
| ATOM | 16769 | O | CYS | B | 528 | 64.732 | 25.149 | −29.651 | 1.00 | 34.26 | B | O |
| ATOM | 16771 | N | THR | B | 529 | 62.760 | 24.979 | −28.597 | 1.00 | 37.83 | B | N |
| ATOM | 16772 | CA | THR | B | 529 | 62.332 | 23.742 | −29.230 | 1.00 | 39.52 | B | C |
| ATOM | 16774 | CB | THR | B | 529 | 61.225 | 23.101 | −28.376 | 1.00 | 39.20 | B | C |
| ATOM | 16776 | OG1 | THR | B | 529 | 61.806 | 22.677 | −27.142 | 1.00 | 39.54 | B | O |
| ATOM | 16778 | CG2 | THR | B | 529 | 60.595 | 21.913 | −29.067 | 1.00 | 38.45 | B | C |
| ATOM | 16782 | C | THR | B | 529 | 61.853 | 23.955 | −30.672 | 1.00 | 41.75 | B | C |
| ATOM | 16783 | O | THR | B | 529 | 62.213 | 23.186 | −31.559 | 1.00 | 41.23 | B | O |
| ATOM | 16785 | N | TYR | B | 530 | 61.062 | 25.001 | −30.908 | 1.00 | 44.34 | B | N |
| ATOM | 16786 | CA | TYR | B | 530 | 60.511 | 25.268 | −32.252 | 1.00 | 46.43 | B | C |
| ATOM | 16788 | CB | TYR | B | 530 | 59.041 | 25.705 | −32.158 | 1.00 | 44.01 | B | C |
| ATOM | 16791 | CG | TYR | B | 530 | 58.222 | 24.607 | −31.519 | 1.00 | 40.79 | B | C |
| ATOM | 16792 | CD1 | TYR | B | 530 | 57.972 | 23.409 | −32.208 | 1.00 | 40.31 | B | C |
| ATOM | 16794 | CE1 | TYR | B | 530 | 57.243 | 22.359 | −31.620 | 1.00 | 35.61 | B | C |
| ATOM | 16796 | CZ | TYR | B | 530 | 56.793 | 22.481 | −30.317 | 1.00 | 34.00 | B | C |
| ATOM | 16797 | OH | TYR | B | 530 | 56.080 | 21.443 | −29.749 | 1.00 | 38.96 | B | O |
| ATOM | 16799 | CE2 | TYR | B | 530 | 57.043 | 23.661 | −29.596 | 1.00 | 36.22 | B | C |
| ATOM | 16801 | CD2 | TYR | B | 530 | 57.760 | 24.716 | −30.202 | 1.00 | 32.71 | B | C |
| ATOM | 16803 | C | TYR | B | 530 | 61.389 | 26.233 | −33.046 | 1.00 | 51.24 | B | C |
| ATOM | 16804 | O | TYR | B | 530 | 61.027 | 27.367 | −33.322 | 1.00 | 52.48 | B | O |
| ATOM | 16806 | N | HIS | B | 531 | 62.574 | 25.735 | −33.384 | 1.00 | 57.86 | B | N |
| ATOM | 16807 | CA | HIS | B | 531 | 63.502 | 26.374 | −34.322 | 1.00 | 61.42 | B | C |
| ATOM | 16809 | CB | HIS | B | 531 | 64.946 | 26.178 | −33.832 | 1.00 | 61.98 | B | C |
| ATOM | 16812 | CG | HIS | B | 531 | 65.332 | 24.737 | −33.645 | 1.00 | 64.97 | B | C |
| ATOM | 16813 | ND1 | HIS | B | 531 | 65.394 | 24.135 | −32.404 | 1.00 | 69.47 | B | N |
| ATOM | 16815 | CE1 | HIS | B | 531 | 65.742 | 22.868 | −32.545 | 1.00 | 66.30 | B | C |
| ATOM | 16817 | NE2 | HIS | B | 531 | 65.906 | 22.625 | −33.833 | 1.00 | 67.05 | B | N |
| ATOM | 16819 | CD2 | HIS | B | 531 | 65.650 | 23.774 | −34.544 | 1.00 | 64.50 | B | C |
| ATOM | 16821 | C | HIS | B | 531 | 63.342 | 25.741 | −35.718 | 1.00 | 63.69 | B | C |
| ATOM | 16822 | O | HIS | B | 531 | 62.596 | 24.762 | −35.878 | 1.00 | 61.87 | B | O |
| ATOM | 16824 | N | ASN | B | 532 | 64.041 | 26.314 | −36.709 | 1.00 | 66.30 | B | N |
| ATOM | 16825 | CA | ASN | B | 532 | 64.175 | 25.735 | −38.056 | 1.00 | 68.40 | B | C |
| ATOM | 16827 | CB | ASN | B | 532 | 63.285 | 26.481 | −39.070 | 1.00 | 69.94 | B | C |
| ATOM | 16830 | CG | ASN | B | 532 | 61.830 | 25.955 | −39.112 | 1.00 | 74.76 | B | C |
| ATOM | 16831 | OD1 | ASN | B | 532 | 61.471 | 25.002 | −38.420 | 1.00 | 78.95 | B | O |
| ATOM | 16832 | ND2 | ASN | B | 532 | 60.999 | 26.584 | −39.941 | 1.00 | 74.30 | B | N |
| ATOM | 16835 | C | ASN | B | 532 | 65.637 | 25.768 | −38.523 | 1.00 | 67.88 | B | C |
| ATOM | 16836 | O | ASN | B | 532 | 66.527 | 25.213 | −37.869 | 1.00 | 66.63 | B | O |
| ATOM | 16838 | N | THR | B | 537 | 73.132 | 23.732 | −39.964 | 1.00 | 92.67 | B | N |
| ATOM | 16839 | CA | THR | B | 537 | 72.461 | 22.617 | −39.298 | 1.00 | 92.98 | B | C |
| ATOM | 16841 | CB | THR | B | 537 | 72.529 | 22.759 | −37.760 | 1.00 | 93.23 | B | C |
| ATOM | 16843 | OG1 | THR | B | 537 | 73.841 | 23.182 | −37.370 | 1.00 | 94.15 | B | O |
| ATOM | 16845 | CG2 | THR | B | 537 | 72.203 | 21.436 | −37.073 | 1.00 | 93.23 | B | C |
| ATOM | 16849 | C | THR | B | 537 | 70.993 | 22.511 | −39.725 | 1.00 | 92.54 | B | C |
| ATOM | 16850 | O | THR | B | 537 | 70.356 | 23.517 | −40.039 | 1.00 | 92.39 | B | O |
| ATOM | 16852 | N | SER | B | 538 | 70.470 | 21.286 | −39.728 | 1.00 | 92.35 | B | N |
| ATOM | 16853 | CA | SER | B | 538 | 69.082 | 21.011 | −40.126 | 1.00 | 92.17 | B | C |
| ATOM | 16855 | CB | SER | B | 538 | 68.996 | 19.620 | −40.773 | 1.00 | 92.20 | B | C |
| ATOM | 16858 | OG | SER | B | 538 | 69.869 | 18.702 | −40.139 | 1.00 | 90.38 | B | O |
| ATOM | 16860 | C | SER | B | 538 | 68.120 | 21.123 | −38.928 | 1.00 | 91.96 | B | C |
| ATOM | 16861 | O | SER | B | 538 | 68.571 | 21.300 | −37.795 | 1.00 | 91.29 | B | O |
| ATOM | 16863 | N | PRO | B | 539 | 66.793 | 21.049 | −39.177 | 1.00 | 92.14 | B | N |
| ATOM | 16864 | CA | PRO | B | 539 | 65.805 | 21.088 | −38.083 | 1.00 | 91.67 | B | C |
| ATOM | 16866 | CB | PRO | B | 539 | 64.457 | 20.853 | −38.796 | 1.00 | 92.19 | B | C |
| ATOM | 16869 | CG | PRO | B | 539 | 64.760 | 20.744 | −40.270 | 1.00 | 93.38 | B | C |
| ATOM | 16872 | CD | PRO | B | 539 | 66.147 | 21.257 | −40.486 | 1.00 | 92.84 | B | C |
| ATOM | 16875 | C | PRO | B | 539 | 66.045 | 20.051 | −36.975 | 1.00 | 90.54 | B | C |

TABLE 4-2-continued

Coordinates of *P. alba* IspS

| | | | | | | | | | | | | |
|---|---|---|---|---|---|---|---|---|---|---|---|---|
| ATOM | 16876 | O | PRO | B | 539 | 66.309 | 20.431 | −35.832 | 1.00 | 90.62 | B | O |
| ATOM | 16877 | N | ASP | B | 540 | 65.954 | 18.763 | −37.298 | 1.00 | 88.88 | B | N |
| ATOM | 16878 | CA | ASP | B | 540 | 66.455 | 17.730 | −36.392 | 1.00 | 87.42 | B | C |
| ATOM | 16880 | CB | ASP | B | 540 | 66.043 | 16.330 | −36.860 | 1.00 | 88.42 | B | C |
| ATOM | 16883 | CG | ASP | B | 540 | 64.596 | 15.999 | −36.524 | 1.00 | 91.80 | B | C |
| ATOM | 16884 | OD1 | ASP | B | 540 | 64.173 | 16.250 | −35.369 | 1.00 | 91.87 | B | O |
| ATOM | 16885 | OD2 | ASP | B | 540 | 63.893 | 15.468 | −37.417 | 1.00 | 93.61 | B | O |
| ATOM | 16886 | C | ASP | B | 540 | 67.972 | 17.858 | −36.375 | 1.00 | 84.38 | B | C |
| ATOM | 16887 | O | ASP | B | 540 | 68.541 | 18.552 | −37.212 | 1.00 | 84.49 | B | O |
| ATOM | 16889 | N | GLU | B | 541 | 68.626 | 17.214 | −35.416 | 1.00 | 80.82 | B | N |
| ATOM | 16890 | CA | GLU | B | 541 | 70.100 | 17.233 | −35.315 | 1.00 | 78.19 | B | C |
| ATOM | 16892 | CB | GLU | B | 541 | 70.777 | 16.841 | −36.642 | 1.00 | 79.32 | B | C |
| ATOM | 16895 | CG | GLU | B | 541 | 70.278 | 15.495 | −37.189 | 1.00 | 82.73 | B | C |
| ATOM | 16898 | CD | GLU | B | 541 | 71.283 | 14.798 | −38.084 | 1.00 | 87.94 | B | C |
| ATOM | 16899 | OE1 | GLU | B | 541 | 72.444 | 14.620 | −37.648 | 1.00 | 90.11 | B | O |
| ATOM | 16900 | OE2 | GLU | B | 541 | 70.904 | 14.416 | −39.216 | 1.00 | 88.49 | B | O |
| ATOM | 16901 | C | GLU | B | 541 | 70.682 | 18.540 | −34.751 | 1.00 | 73.56 | B | C |
| ATOM | 16902 | O | GLU | B | 541 | 71.815 | 18.556 | −34.273 | 1.00 | 73.40 | B | O |
| ATOM | 16904 | N | LEU | B | 542 | 69.927 | 19.632 | −34.816 | 1.00 | 68.80 | B | N |
| ATOM | 16905 | CA | LEU | B | 542 | 70.113 | 20.705 | −33.848 | 1.00 | 64.68 | B | C |
| ATOM | 16907 | CB | LEU | B | 542 | 69.553 | 22.044 | −34.340 | 1.00 | 64.53 | B | C |
| ATOM | 16910 | CG | LEU | B | 542 | 69.909 | 23.238 | −33.441 | 1.00 | 64.65 | B | C |
| ATOM | 16912 | CD1 | LEU | B | 542 | 69.389 | 24.543 | −34.021 | 1.00 | 63.68 | B | C |
| ATOM | 16916 | CD2 | LEU | B | 542 | 71.420 | 23.328 | −33.196 | 1.00 | 66.71 | B | C |
| ATOM | 16920 | C | LEU | B | 542 | 69.415 | 20.250 | −32.563 | 1.00 | 60.16 | B | C |
| ATOM | 16921 | O | LEU | B | 542 | 69.954 | 20.410 | −31.474 | 1.00 | 56.80 | B | O |
| ATOM | 16923 | N | THR | B | 543 | 68.239 | 19.641 | −32.702 | 1.00 | 56.33 | B | N |
| ATOM | 16924 | CA | THR | B | 543 | 67.526 | 19.101 | −31.546 | 1.00 | 54.58 | B | C |
| ATOM | 16926 | CB | THR | B | 543 | 66.124 | 18.577 | −31.927 | 1.00 | 52.91 | B | C |
| ATOM | 16928 | OG1 | THR | B | 543 | 65.436 | 19.560 | −32.707 | 1.00 | 55.01 | B | O |
| ATOM | 16930 | CG2 | THR | B | 543 | 65.311 | 18.285 | −30.686 | 1.00 | 50.48 | B | C |
| ATOM | 16934 | C | THR | B | 543 | 68.322 | 17.979 | −30.862 | 1.00 | 54.20 | B | C |
| ATOM | 16935 | O | THR | B | 543 | 68.443 | 17.967 | −29.631 | 1.00 | 53.54 | B | O |
| ATOM | 16937 | N | ARG | B | 544 | 68.859 | 17.042 | −31.650 | 1.00 | 53.07 | B | N |
| ATOM | 16938 | CA | ARG | B | 544 | 69.633 | 15.927 | −31.084 | 1.00 | 52.95 | B | C |
| ATOM | 16940 | CB | ARG | B | 544 | 69.966 | 14.867 | −32.153 | 1.00 | 53.76 | B | C |
| ATOM | 16943 | CG | ARG | B | 544 | 71.147 | 13.934 | −31.807 | 1.00 | 59.59 | B | C |
| ATOM | 16946 | CD | ARG | B | 544 | 71.594 | 13.065 | −32.998 | 1.00 | 69.45 | B | C |
| ATOM | 16949 | NE | ARG | B | 544 | 72.185 | 13.844 | −34.099 | 1.00 | 74.98 | B | N |
| ATOM | 16951 | CZ | ARG | B | 544 | 73.462 | 14.230 | −34.184 | 1.00 | 78.91 | B | C |
| ATOM | 16952 | NH1 | ARG | B | 544 | 74.342 | 13.930 | −33.226 | 1.00 | 79.02 | B | N |
| ATOM | 16955 | NH2 | ARG | B | 544 | 73.866 | 14.932 | −35.244 | 1.00 | 79.30 | B | N |
| ATOM | 16958 | C | ARG | B | 544 | 70.914 | 16.423 | −30.396 | 1.00 | 50.09 | B | C |
| ATOM | 16959 | O | ARG | B | 544 | 71.349 | 15.822 | −29.418 | 1.00 | 49.18 | B | O |
| ATOM | 16961 | N | LYS | B | 545 | 71.512 | 17.495 | −30.920 | 1.00 | 47.95 | B | N |
| ATOM | 16962 | CA | LYS | B | 545 | 72.733 | 18.060 | −30.332 | 1.00 | 49.20 | B | C |
| ATOM | 16964 | CB | LYS | B | 545 | 73.452 | 19.034 | −31.290 | 1.00 | 50.06 | B | C |
| ATOM | 16967 | CG | LYS | B | 545 | 74.568 | 18.354 | −32.088 | 1.00 | 58.27 | B | C |
| ATOM | 16970 | CD | LYS | B | 545 | 75.488 | 19.319 | −32.834 | 1.00 | 65.12 | B | C |
| ATOM | 16973 | CE | LYS | B | 545 | 76.657 | 18.535 | −33.467 | 1.00 | 70.31 | B | C |
| ATOM | 16976 | NZ | LYS | B | 545 | 77.822 | 19.378 | −33.889 | 1.00 | 72.09 | B | N |
| ATOM | 16980 | C | LYS | B | 545 | 72.446 | 18.743 | −29.008 | 1.00 | 46.91 | B | C |
| ATOM | 16981 | O | LYS | B | 545 | 73.292 | 18.769 | −28.115 | 1.00 | 48.01 | B | O |
| ATOM | 16983 | N | ARG | B | 546 | 71.248 | 19.288 | −28.873 | 1.00 | 44.64 | B | N |
| ATOM | 16984 | CA | ARG | B | 546 | 70.871 | 19.937 | −27.632 | 1.00 | 43.28 | B | C |
| ATOM | 16986 | CB | ARG | B | 546 | 69.730 | 20.917 | −27.871 | 1.00 | 43.53 | B | C |
| ATOM | 16989 | CG | ARG | B | 546 | 70.222 | 22.144 | −28.634 | 1.00 | 38.72 | B | C |
| ATOM | 16992 | CD | ARG | B | 546 | 69.107 | 23.107 | −28.977 | 1.00 | 38.25 | B | C |
| ATOM | 16995 | NE | ARG | B | 546 | 69.662 | 24.350 | −29.501 | 1.00 | 33.40 | B | N |
| ATOM | 16997 | CZ | ARG | B | 546 | 68.947 | 25.364 | −29.967 | 1.00 | 37.10 | B | C |
| ATOM | 16998 | NH1 | ARG | B | 546 | 67.619 | 25.316 | −29.984 | 1.00 | 37.22 | B | N |
| ATOM | 17001 | NH2 | ARG | B | 546 | 69.578 | 26.440 | −30.425 | 1.00 | 44.86 | B | N |
| ATOM | 17004 | C | ARG | B | 546 | 70.554 | 18.916 | −26.552 | 1.00 | 42.26 | B | C |
| ATOM | 17005 | O | ARG | B | 546 | 70.990 | 19.067 | −25.419 | 1.00 | 42.38 | B | O |
| ATOM | 17007 | N | VAL | B | 547 | 69.847 | 17.851 | −26.909 | 1.00 | 41.23 | B | N |
| ATOM | 17008 | CA | VAL | B | 547 | 69.610 | 16.766 | −25.965 | 1.00 | 40.03 | B | C |
| ATOM | 17010 | CB | VAL | B | 547 | 68.784 | 15.617 | −26.584 | 1.00 | 41.02 | B | C |
| ATOM | 17012 | CG1 | VAL | B | 547 | 68.755 | 14.403 | −25.652 | 1.00 | 42.61 | B | C |
| ATOM | 17016 | CG2 | VAL | B | 547 | 67.388 | 16.087 | −26.894 | 1.00 | 35.48 | B | C |
| ATOM | 17020 | C | VAL | B | 547 | 70.949 | 16.242 | −25.511 | 1.00 | 40.46 | B | C |
| ATOM | 17021 | O | VAL | B | 547 | 71.157 | 16.006 | −24.324 | 1.00 | 42.73 | B | O |
| ATOM | 17023 | N | LEU | B | 548 | 71.869 | 16.070 | −26.454 | 1.00 | 39.76 | B | N |
| ATOM | 17024 | CA | LEU | B | 548 | 73.210 | 15.609 | −26.116 | 1.00 | 39.29 | B | C |
| ATOM | 17026 | CB | LEU | B | 548 | 74.089 | 15.436 | −27.368 | 1.00 | 39.65 | B | C |
| ATOM | 17029 | CG | LEU | B | 548 | 74.394 | 13.996 | −27.805 | 1.00 | 45.33 | B | C |
| ATOM | 17031 | CD1 | LEU | B | 548 | 73.140 | 13.267 | −28.315 | 1.00 | 42.95 | B | C |
| ATOM | 17035 | CD2 | LEU | B | 548 | 75.493 | 13.998 | −28.880 | 1.00 | 46.14 | B | C |
| ATOM | 17039 | C | LEU | B | 548 | 73.895 | 16.545 | −25.107 | 1.00 | 37.32 | B | C |

TABLE 4-2-continued

Coordinates of *P. alba* IspS

| | | | | | | | | | | | | |
|---|---|---|---|---|---|---|---|---|---|---|---|---|
| ATOM | 17040 | O | LEU | B | 548 | 74.409 | 16.086 | −24.085 | 1.00 | 39.63 | B | O |
| ATOM | 17042 | N | SER | B | 549 | 73.895 | 17.844 | −25.389 | 1.00 | 33.98 | B | N |
| ATOM | 17043 | CA | SER | B | 549 | 74.656 | 18.804 | −24.587 | 1.00 | 32.24 | B | C |
| ATOM | 17045 | CB | SER | B | 549 | 74.859 | 20.074 | −25.377 | 1.00 | 32.05 | B | C |
| ATOM | 17048 | OG | SER | B | 549 | 73.605 | 20.666 | −25.577 | 1.00 | 34.09 | B | O |
| ATOM | 17050 | C | SER | B | 549 | 73.979 | 19.171 | −23.280 | 1.00 | 30.34 | B | C |
| ATOM | 17051 | O | SER | B | 549 | 74.643 | 19.569 | −22.328 | 1.00 | 32.04 | B | O |
| ATOM | 17053 | N | VAL | B | 550 | 72.658 | 19.064 | −23.232 | 1.00 | 28.62 | B | N |
| ATOM | 17054 | CA | VAL | B | 550 | 71.932 | 19.383 | −22.014 | 1.00 | 26.79 | B | C |
| ATOM | 17056 | CB | VAL | B | 550 | 70.551 | 19.991 | −22.299 | 1.00 | 26.82 | B | C |
| ATOM | 17058 | CG1 | VAL | B | 550 | 69.800 | 20.186 | −21.022 | 1.00 | 22.61 | B | C |
| ATOM | 17062 | CG2 | VAL | B | 550 | 70.688 | 21.353 | −23.017 | 1.00 | 18.25 | B | C |
| ATOM | 17066 | C | VAL | B | 550 | 71.828 | 18.162 | −21.097 | 1.00 | 29.02 | B | C |
| ATOM | 17067 | O | VAL | B | 550 | 72.112 | 18.264 | −19.906 | 1.00 | 28.22 | B | O |
| ATOM | 17069 | N | ILE | B | 551 | 71.481 | 16.999 | −21.652 | 1.00 | 30.73 | B | N |
| ATOM | 17070 | CA | ILE | B | 551 | 71.234 | 15.812 | −20.832 | 1.00 | 31.06 | B | C |
| ATOM | 17072 | CB | ILE | B | 551 | 70.034 | 14.999 | −21.334 | 1.00 | 31.51 | B | C |
| ATOM | 17074 | CG1 | ILE | B | 551 | 68.763 | 15.849 | −21.376 | 1.00 | 30.36 | B | C |
| ATOM | 17077 | CD1 | ILE | B | 551 | 68.327 | 16.382 | −20.035 | 1.00 | 37.56 | B | C |
| ATOM | 17081 | CG2 | ILE | B | 551 | 69.854 | 13.747 | −20.460 | 1.00 | 29.79 | B | C |
| ATOM | 17085 | C | ILE | B | 551 | 72.395 | 14.829 | −20.762 | 1.00 | 32.00 | B | C |
| ATOM | 17086 | O | ILE | B | 551 | 72.795 | 14.419 | −19.678 | 1.00 | 31.17 | B | O |
| ATOM | 17088 | N | THR | B | 552 | 72.903 | 14.418 | −21.917 | 1.00 | 34.78 | B | N |
| ATOM | 17089 | CA | THR | B | 552 | 73.696 | 13.200 | −21.985 | 1.00 | 35.86 | B | C |
| ATOM | 17091 | CB | THR | B | 552 | 73.372 | 12.395 | −23.266 | 1.00 | 38.74 | B | C |
| ATOM | 17093 | OG1 | THR | B | 552 | 73.836 | 13.097 | −24.419 | 1.00 | 47.68 | B | O |
| ATOM | 17095 | CG2 | THR | B | 552 | 71.879 | 12.179 | −23.414 | 1.00 | 30.46 | B | C |
| ATOM | 17099 | C | THR | B | 552 | 75.204 | 13.447 | −21.829 | 1.00 | 36.32 | B | C |
| ATOM | 17100 | O | THR | B | 552 | 75.870 | 12.723 | −21.082 | 1.00 | 37.04 | B | O |
| ATOM | 17102 | N | GLU | B | 553 | 75.753 | 14.469 | −22.483 | 1.00 | 36.21 | B | N |
| ATOM | 17103 | CA | GLU | B | 553 | 77.217 | 14.663 | −22.459 | 1.00 | 37.69 | B | C |
| ATOM | 17105 | CB | GLU | B | 553 | 77.744 | 14.854 | −23.887 | 1.00 | 40.39 | B | C |
| ATOM | 17108 | CG | GLU | B | 553 | 77.790 | 13.550 | −24.700 | 1.00 | 47.06 | B | C |
| ATOM | 17111 | CD | GLU | B | 553 | 78.488 | 13.705 | −26.052 | 1.00 | 57.90 | B | C |
| ATOM | 17112 | OE1 | GLU | B | 553 | 79.380 | 12.877 | −26.353 | 1.00 | 60.24 | B | O |
| ATOM | 17113 | OE2 | GLU | B | 553 | 78.145 | 14.649 | −26.810 | 1.00 | 60.91 | B | O |
| ATOM | 17114 | C | GLU | B | 553 | 77.701 | 15.811 | −21.563 | 1.00 | 35.39 | B | C |
| ATOM | 17115 | O | GLU | B | 553 | 77.311 | 16.947 | −21.751 | 1.00 | 34.26 | B | O |
| ATOM | 17117 | N | PRO | B | 554 | 78.574 | 15.515 | −20.589 | 1.00 | 36.02 | B | N |
| ATOM | 17118 | CA | PRO | B | 554 | 79.201 | 16.596 | −19.827 | 1.00 | 34.71 | B | C |
| ATOM | 17120 | CB | PRO | B | 554 | 80.207 | 15.875 | −18.918 | 1.00 | 34.87 | B | C |
| ATOM | 17123 | CG | PRO | B | 554 | 79.840 | 14.450 | −18.926 | 1.00 | 37.61 | B | C |
| ATOM | 17126 | CD | PRO | B | 554 | 79.055 | 14.183 | −20.176 | 1.00 | 37.77 | B | C |
| ATOM | 17129 | C | PRO | B | 554 | 79.954 | 17.593 | −20.699 | 1.00 | 33.50 | B | C |
| ATOM | 17130 | O | PRO | B | 554 | 80.283 | 17.322 | −21.858 | 1.00 | 34.84 | B | O |
| ATOM | 17131 | N | ILE | B | 555 | 80.209 | 18.757 | −20.132 | 1.00 | 32.88 | B | N |
| ATOM | 17132 | CA | ILE | B | 555 | 81.096 | 19.725 | −20.750 | 1.00 | 33.21 | B | C |
| ATOM | 17134 | CB | ILE | B | 555 | 80.876 | 21.140 | −20.138 | 1.00 | 32.95 | B | C |
| ATOM | 17136 | CG1 | ILE | B | 555 | 79.500 | 21.664 | −20.567 | 1.00 | 32.79 | B | C |
| ATOM | 17139 | CD1 | ILE | B | 555 | 79.137 | 23.039 | −20.029 | 1.00 | 29.41 | B | C |
| ATOM | 17143 | CG2 | ILE | B | 555 | 81.957 | 22.100 | −20.587 | 1.00 | 30.93 | B | C |
| ATOM | 17147 | C | ILE | B | 555 | 82.511 | 19.220 | −20.501 | 1.00 | 32.07 | B | C |
| ATOM | 17148 | O | ILE | B | 555 | 82.789 | 18.686 | −19.434 | 1.00 | 30.59 | B | O |
| ATOM | 17150 | N | LEU | B | 556 | 83.391 | 19.367 | −21.484 | 1.00 | 32.81 | B | N |
| ATOM | 17151 | CA | LEU | B | 556 | 84.761 | 18.848 | −21.362 | 1.00 | 34.73 | B | C |
| ATOM | 17153 | CB | LEU | B | 556 | 85.564 | 19.045 | −22.669 | 1.00 | 34.99 | B | C |
| ATOM | 17156 | CG | LEU | B | 556 | 85.005 | 18.383 | −23.948 | 1.00 | 39.49 | B | C |
| ATOM | 17158 | CD1 | LEU | B | 556 | 85.738 | 18.858 | −25.230 | 1.00 | 42.15 | B | C |
| ATOM | 17162 | CD2 | LEU | B | 556 | 85.067 | 16.866 | −23.827 | 1.00 | 40.24 | B | C |
| ATOM | 17166 | C | LEU | B | 556 | 85.454 | 19.540 | −20.179 | 1.00 | 34.19 | B | C |
| ATOM | 17167 | O | LEU | B | 556 | 85.268 | 20.731 | −19.971 | 1.00 | 35.29 | B | O |
| ATOM | 17169 | N | PRO | B | 557 | 86.252 | 18.795 | −19.401 | 1.00 | 34.37 | B | N |
| ATOM | 17170 | CA | PRO | B | 557 | 86.764 | 19.369 | −18.152 | 1.00 | 34.58 | B | C |
| ATOM | 17172 | CB | PRO | B | 557 | 87.532 | 18.209 | −17.506 | 1.00 | 34.08 | B | C |
| ATOM | 17175 | CG | PRO | B | 557 | 87.851 | 17.281 | −18.607 | 1.00 | 35.29 | B | C |
| ATOM | 17178 | CD | PRO | B | 557 | 86.815 | 17.462 | −19.685 | 1.00 | 34.74 | B | C |
| ATOM | 17181 | C | PRO | B | 557 | 87.672 | 20.587 | −18.327 | 1.00 | 34.93 | B | C |
| ATOM | 17182 | O | PRO | B | 557 | 88.198 | 20.847 | −19.407 | 1.00 | 35.00 | B | O |
| ATOM | 17183 | N | PHE | B | 558 | 87.827 | 21.332 | −17.245 | 1.00 | 35.20 | B | N |
| ATOM | 17184 | CA | PHE | B | 558 | 88.627 | 22.539 | −17.251 | 1.00 | 35.65 | B | C |
| ATOM | 17186 | CB | PHE | B | 558 | 88.342 | 23.308 | −15.962 | 1.00 | 32.90 | B | C |
| ATOM | 17189 | CG | PHE | B | 558 | 89.329 | 24.400 | −15.656 | 1.00 | 35.99 | B | C |
| ATOM | 17190 | CD1 | PHE | B | 558 | 90.270 | 24.248 | −14.636 | 1.00 | 38.91 | B | C |
| ATOM | 17192 | CE1 | PHE | B | 558 | 91.172 | 25.264 | −14.339 | 1.00 | 40.56 | B | C |
| ATOM | 17194 | CZ | PHE | B | 558 | 91.140 | 26.448 | −15.062 | 1.00 | 39.35 | B | C |
| ATOM | 17196 | CE2 | PHE | B | 558 | 90.208 | 26.608 | −16.074 | 1.00 | 38.08 | B | C |
| ATOM | 17198 | CD2 | PHE | B | 558 | 89.311 | 25.589 | −16.367 | 1.00 | 36.76 | B | C |
| ATOM | 17200 | C | PHE | B | 558 | 90.119 | 22.174 | −17.388 | 1.00 | 38.66 | B | C |

TABLE 4-2-continued

Coordinates of *P. alba* IspS

| | | | | | | | | | | | | |
|---|---|---|---|---|---|---|---|---|---|---|---|---|
| ATOM | 17201 | O | PHE | B | 558 | 90.588 | 21.221 | −16.768 | 1.00 | 35.43 | B | O |
| ATOM | 17203 | N | GLU | B | 559 | 90.841 | 22.934 | −18.210 | 1.00 | 43.59 | B | N |
| ATOM | 17204 | CA | GLU | B | 559 | 92.278 | 22.725 | −18.437 | 1.00 | 49.37 | B | C |
| ATOM | 17206 | CB | GLU | B | 559 | 92.527 | 22.302 | −19.886 | 1.00 | 50.25 | B | C |
| ATOM | 17209 | CG | GLU | B | 559 | 92.467 | 20.803 | −20.151 | 1.00 | 55.23 | B | C |
| ATOM | 17212 | CD | GLU | B | 559 | 92.918 | 20.460 | −21.569 | 1.00 | 62.27 | B | C |
| ATOM | 17213 | OE1 | GLU | B | 559 | 92.093 | 20.605 | −22.507 | 1.00 | 58.80 | B | O |
| ATOM | 17214 | OE2 | GLU | B | 559 | 94.100 | 20.059 | −21.736 | 1.00 | 59.57 | B | O |
| ATOM | 17215 | C | GLU | B | 559 | 93.083 | 24.001 | −18.161 | 1.00 | 52.39 | B | C |
| ATOM | 17216 | O | GLU | B | 559 | 92.772 | 25.061 | −18.707 | 1.00 | 52.68 | B | O |
| ATOM | 17218 | N | ARG | B | 560 | 94.128 | 23.886 | −17.343 | 1.00 | 55.22 | B | N |
| ATOM | 17219 | CA | ARG | B | 560 | 95.025 | 25.016 | −17.043 | 1.00 | 57.60 | B | C |
| ATOM | 17221 | CB | ARG | B | 560 | 95.966 | 24.658 | −15.890 | 1.00 | 58.83 | B | C |
| ATOM | 17224 | CG | ARG | B | 560 | 95.247 | 24.332 | −14.589 | 1.00 | 63.59 | B | C |
| ATOM | 17227 | CD | ARG | B | 560 | 95.488 | 25.362 | −13.492 | 1.00 | 69.13 | B | C |
| ATOM | 17230 | NE | ARG | B | 560 | 94.390 | 25.393 | −12.522 | 1.00 | 75.07 | B | N |
| ATOM | 17232 | CZ | ARG | B | 560 | 94.070 | 24.398 | −11.686 | 1.00 | 78.47 | B | C |
| ATOM | 17233 | NH1 | ARG | B | 560 | 94.752 | 23.252 | −11.675 | 1.00 | 78.68 | B | N |
| ATOM | 17236 | NH2 | ARG | B | 560 | 93.047 | 24.545 | −10.847 | 1.00 | 78.46 | B | N |
| ATOM | 17239 | C | ARG | B | 560 | 95.856 | 25.404 | −18.261 | 1.00 | 57.16 | B | C |
| ATOM | 17240 | O | ARG | B | 560 | 95.920 | 26.575 | −18.624 | 1.00 | 57.13 | B | O |
| ATOM | 17242 | O | HOH | W | 1 | 67.396 | 39.491 | −23.826 | 1.00 | 20.98 | W | O |
| ATOM | 17245 | O | HOH | W | 2 | 46.505 | 15.035 | −3.469 | 1.00 | 20.88 | W | O |
| ATOM | 17248 | O | HOH | W | 3 | 36.160 | 7.031 | −16.321 | 1.00 | 25.10 | W | O |
| ATOM | 17251 | O | HOH | W | 4 | 34.395 | 30.503 | −35.530 | 1.00 | 17.73 | W | O |
| ATOM | 17254 | O | HOH | W | 5 | 37.638 | 17.344 | −11.502 | 1.00 | 32.45 | W | O |
| ATOM | 17257 | O | HOH | W | 6 | 65.819 | −37.512 | 3.562 | 1.00 | 29.91 | W | O |
| ATOM | 17260 | O | HOH | W | 7 | 56.866 | −34.130 | −11.051 | 1.00 | 31.56 | W | O |
| ATOM | 17263 | O | HOH | W | 8 | 43.972 | −6.315 | −15.500 | 1.00 | 23.40 | W | O |
| ATOM | 17266 | O | HOH | W | 9 | 60.228 | −40.852 | 2.964 | 1.00 | 21.46 | W | O |
| ATOM | 17269 | O | HOH | W | 10 | 43.012 | 23.511 | −17.712 | 1.00 | 41.96 | W | O |
| ATOM | 17272 | O | HOH | W | 11 | 38.135 | 14.576 | −14.888 | 1.00 | 28.05 | W | O |
| ATOM | 17275 | O | HOH | W | 12 | 57.728 | −35.432 | 5.083 | 1.00 | 24.61 | W | O |
| ATOM | 17278 | O | HOH | W | 13 | 57.235 | −51.809 | −9.446 | 1.00 | 34.71 | W | O |
| ATOM | 17281 | O | HOH | W | 14 | 66.193 | 38.695 | −7.571 | 1.00 | 26.05 | W | O |
| ATOM | 17284 | O | HOH | W | 15 | 36.482 | −23.763 | 3.380 | 1.00 | 35.70 | W | O |
| ATOM | 17287 | O | HOH | W | 16 | 63.221 | −40.097 | 3.528 | 1.00 | 27.60 | W | O |
| ATOM | 17290 | O | HOH | W | 17 | 73.515 | 25.429 | 6.453 | 1.00 | 49.84 | W | O |
| ATOM | 17293 | O | HOH | W | 18 | 53.192 | 45.369 | −20.010 | 1.00 | 31.15 | W | O |
| ATOM | 17296 | O | HOH | W | 19 | 77.678 | 42.352 | 1.054 | 1.00 | 32.86 | W | O |
| ATOM | 17299 | O | HOH | W | 20 | 48.264 | −34.170 | 15.244 | 1.00 | 46.42 | W | O |
| ATOM | 17302 | O | HOH | W | 21 | 39.547 | 35.857 | −35.345 | 1.00 | 19.86 | W | O |
| ATOM | 17305 | O | HOH | W | 22 | 35.404 | −1.739 | −16.317 | 1.00 | 27.73 | W | O |
| ATOM | 17308 | O | HOH | W | 23 | 62.314 | 8.273 | −25.549 | 1.00 | 44.96 | W | O |
| ATOM | 17311 | O | HOH | W | 24 | 42.306 | 22.146 | −12.509 | 1.00 | 21.07 | W | O |
| ATOM | 17314 | O | HOH | W | 25 | 41.363 | 11.085 | −35.066 | 1.00 | 18.32 | W | O |
| ATOM | 17317 | O | HOH | W | 26 | 46.155 | −26.355 | −2.836 | 1.00 | 27.33 | W | O |
| ATOM | 17320 | O | HOH | W | 27 | 73.732 | 29.702 | −30.702 | 1.00 | 33.09 | W | O |
| ATOM | 17323 | O | HOH | W | 28 | 55.875 | −54.406 | 1.824 | 1.00 | 32.16 | W | O |
| ATOM | 17326 | O | HOH | W | 29 | 55.002 | 28.302 | −1.446 | 1.00 | 42.39 | W | O |
| ATOM | 17329 | O | HOH | W | 30 | 45.510 | −23.435 | −12.887 | 1.00 | 39.50 | W | O |
| ATOM | 17332 | O | HOH | W | 31 | 53.296 | 48.691 | −18.974 | 1.00 | 46.53 | W | O |
| ATOM | 17335 | O | HOH | W | 32 | 65.749 | −34.978 | 8.760 | 1.00 | 23.25 | W | O |
| ATOM | 17338 | O | HOH | W | 33 | 41.864 | −40.579 | 7.567 | 1.00 | 27.81 | W | O |
| ATOM | 17341 | O | HOH | W | 34 | 62.501 | 38.943 | −10.518 | 1.00 | 24.84 | W | O |
| ATOM | 17344 | O | HOH | W | 35 | 62.874 | −31.234 | 17.475 | 1.00 | 40.25 | W | O |
| ATOM | 17347 | O | HOH | W | 36 | 72.629 | −36.786 | 2.592 | 1.00 | 26.17 | W | O |
| ATOM | 17350 | O | HOH | W | 37 | 33.607 | 7.834 | −9.701 | 1.00 | 45.87 | W | O |
| ATOM | 17353 | O | HOH | W | 38 | 77.284 | −36.310 | −9.186 | 1.00 | 41.42 | W | O |
| ATOM | 17356 | O | HOH | W | 39 | 77.331 | 43.278 | −25.049 | 1.00 | 30.11 | W | O |
| ATOM | 17359 | O | HOH | W | 40 | 39.966 | −6.135 | −21.236 | 1.00 | 39.64 | W | O |
| ATOM | 17362 | O | HOH | W | 41 | 53.845 | −3.289 | 6.774 | 1.00 | 27.25 | W | O |
| ATOM | 17365 | O | HOH | W | 42 | 39.457 | 24.448 | −15.702 | 1.00 | 31.86 | W | O |
| ATOM | 17368 | O | HOH | W | 43 | 50.941 | −47.129 | 15.355 | 1.00 | 37.33 | W | O |
| ATOM | 17371 | O | HOH | W | 44 | 31.147 | 15.698 | −26.421 | 1.00 | 31.90 | W | O |
| ATOM | 17374 | O | HOH | W | 45 | 75.880 | 39.481 | −22.456 | 1.00 | 24.94 | W | O |
| ATOM | 17377 | O | HOH | W | 46 | 54.871 | 30.920 | −42.208 | 1.00 | 31.91 | W | O |
| ATOM | 17380 | O | HOH | W | 47 | 65.261 | −50.315 | 5.447 | 1.00 | 32.59 | W | O |
| ATOM | 17383 | O | HOH | W | 48 | 71.408 | −9.056 | −6.457 | 1.00 | 27.35 | W | O |
| ATOM | 17386 | O | HOH | W | 49 | 68.507 | −42.622 | −19.180 | 1.00 | 39.04 | W | O |
| ATOM | 17389 | O | HOH | W | 50 | 40.635 | −32.994 | −1.450 | 1.00 | 29.96 | W | O |
| ATOM | 17392 | O | HOH | W | 51 | 43.834 | 39.340 | −19.280 | 1.00 | 44.69 | W | O |
| ATOM | 17395 | O | HOH | W | 52 | 49.324 | −10.510 | −8.611 | 1.00 | 22.83 | W | O |
| ATOM | 17398 | O | HOH | W | 53 | 73.154 | −41.586 | −3.585 | 1.00 | 28.18 | W | O |
| ATOM | 17401 | O | HOH | W | 54 | 74.167 | −32.081 | 10.431 | 1.00 | 38.80 | W | O |
| ATOM | 17404 | O | HOH | W | 55 | 32.208 | −24.041 | 27.564 | 1.00 | 36.12 | W | O |
| ATOM | 17407 | O | HOH | W | 56 | 81.358 | 51.348 | −21.846 | 1.00 | 36.22 | W | O |
| ATOM | 17410 | O | HOH | W | 57 | 28.049 | −9.147 | 14.182 | 1.00 | 28.08 | W | O |

TABLE 4-2-continued

Coordinates of *P. alba* IspS

| | | | | | | | | | | | | |
|---|---|---|---|---|---|---|---|---|---|---|---|---|
| ATOM | 17413 | O | HOH | W | 58 | 53.295 | −33.548 | −8.420 | 1.00 | 32.02 | W | O |
| ATOM | 17416 | O | HOH | W | 59 | 33.141 | −27.930 | 14.065 | 1.00 | 49.40 | W | O |
| ATOM | 17419 | O | HOH | W | 60 | 73.963 | 42.850 | −22.320 | 1.00 | 27.05 | W | O |
| ATOM | 17422 | O | HOH | W | 61 | 57.737 | 18.482 | −4.811 | 1.00 | 40.88 | W | O |
| ATOM | 17425 | O | HOH | W | 62 | 41.825 | 42.820 | −42.173 | 1.00 | 33.38 | W | O |
| ATOM | 17428 | O | HOH | W | 63 | 32.765 | 16.578 | −23.918 | 1.00 | 31.22 | W | O |
| ATOM | 17431 | O | HOH | W | 64 | 37.857 | 13.924 | −10.555 | 1.00 | 34.26 | W | O |
| ATOM | 17434 | O | HOH | W | 65 | 89.849 | 19.986 | −14.523 | 1.00 | 30.80 | W | O |
| ATOM | 17437 | O | HOH | W | 66 | 28.309 | −3.232 | 7.889 | 1.00 | 33.97 | W | O |
| ATOM | 17440 | O | HOH | W | 67 | 81.027 | 23.484 | 4.883 | 1.00 | 29.67 | W | O |
| ATOM | 17443 | O | HOH | W | 68 | 92.000 | 34.104 | −14.235 | 1.00 | 25.36 | W | O |
| ATOM | 17446 | O | HOH | W | 69 | 33.611 | −22.981 | 9.544 | 1.00 | 26.38 | W | O |
| ATOM | 17449 | O | HOH | W | 70 | 69.544 | 29.746 | 3.258 | 1.00 | 45.00 | W | O |
| ATOM | 17452 | O | HOH | W | 71 | 33.580 | 19.200 | −28.527 | 1.00 | 28.54 | W | O |
| ATOM | 17455 | O | HOH | W | 72 | 60.973 | −6.895 | 13.133 | 1.00 | 51.02 | W | O |
| ATOM | 17458 | O | HOH | W | 73 | 63.662 | −53.195 | 6.160 | 1.00 | 31.10 | W | O |
| ATOM | 17461 | O | HOH | W | 74 | 40.501 | 13.400 | 9.740 | 1.00 | 29.39 | W | O |
| ATOM | 17464 | O | HOH | W | 75 | 31.268 | −0.700 | −16.248 | 1.00 | 38.68 | W | O |
| ATOM | 17467 | O | HOH | W | 76 | 64.405 | 12.253 | −9.311 | 1.00 | 32.15 | W | O |
| ATOM | 17470 | O | HOH | W | 77 | 51.823 | −41.573 | −13.076 | 1.00 | 38.60 | W | O |
| ATOM | 17473 | O | HOH | W | 78 | 52.094 | −48.948 | −6.963 | 1.00 | 36.07 | W | O |
| ATOM | 17476 | O | HOH | W | 79 | 65.280 | −37.041 | 19.710 | 1.00 | 36.79 | W | O |
| ATOM | 17479 | O | HOH | W | 80 | 73.752 | −42.738 | −1.116 | 1.00 | 42.80 | W | O |
| ATOM | 17482 | O | HOH | W | 81 | 33.127 | 5.296 | 2.323 | 1.00 | 34.50 | W | O |
| ATOM | 17485 | O | HOH | W | 82 | 52.917 | 19.244 | −39.930 | 1.00 | 38.53 | W | O |
| ATOM | 17488 | O | HOH | W | 83 | 31.947 | −16.214 | −2.242 | 1.00 | 42.38 | W | O |
| ATOM | 17491 | O | HOH | W | 84 | 44.466 | 34.961 | −48.175 | 1.00 | 39.18 | W | O |
| ATOM | 17494 | O | HOH | W | 85 | 73.801 | 10.513 | −12.397 | 1.00 | 34.17 | W | O |
| ATOM | 17497 | O | HOH | W | 86 | 56.162 | −30.900 | 13.891 | 1.00 | 36.49 | W | O |
| ATOM | 17500 | O | HOH | W | 87 | 58.302 | 40.830 | −34.099 | 1.00 | 38.00 | W | O |
| ATOM | 17503 | O | HOH | W | 88 | 67.361 | 57.337 | −12.595 | 1.00 | 35.90 | W | O |
| ATOM | 17506 | O | HOH | W | 89 | 36.407 | 16.844 | −14.535 | 1.00 | 34.76 | W | O |
| ATOM | 17509 | O | HOH | W | 90 | 36.526 | −2.835 | −11.577 | 1.00 | 29.09 | W | O |
| ATOM | 17512 | O | HOH | W | 91 | 63.568 | 38.471 | −8.120 | 1.00 | 33.00 | W | O |
| ATOM | 17515 | O | HOH | W | 92 | 31.876 | −24.706 | −14.685 | 1.00 | 47.13 | W | O |
| ATOM | 17518 | O | HOH | W | 93 | 57.122 | 46.180 | −41.231 | 1.00 | 38.56 | W | O |
| ATOM | 17521 | O | HOH | W | 94 | 40.989 | 25.119 | −38.866 | 1.00 | 34.26 | W | O |
| ATOM | 17524 | O | HOH | W | 95 | 70.573 | 35.539 | −11.174 | 1.00 | 34.26 | W | O |
| ATOM | 17527 | O | HOH | W | 96 | 67.166 | −18.296 | −0.056 | 1.00 | 21.97 | W | O |
| ATOM | 17530 | O | HOH | W | 97 | 68.329 | −19.165 | −2.481 | 1.00 | 27.46 | W | O |
| ATOM | 17533 | O | HOH | W | 98 | 46.453 | −46.459 | −0.096 | 1.00 | 23.67 | W | O |
| ATOM | 17536 | O | HOH | W | 99 | 64.859 | −27.821 | −0.476 | 1.00 | 23.74 | W | O |
| ATOM | 17539 | O | HOH | W | 100 | 49.889 | −41.983 | −4.752 | 1.00 | 19.81 | W | O |
| ATOM | 17542 | O | HOH | W | 101 | 63.104 | −35.094 | −0.981 | 1.00 | 21.48 | W | O |
| ATOM | 17545 | O | HOH | W | 102 | 46.208 | 22.160 | −21.251 | 1.00 | 17.27 | W | O |
| ATOM | 17548 | O | HOH | W | 103 | 44.240 | 21.517 | −19.373 | 1.00 | 18.97 | W | O |
| ATOM | 17551 | O | HOH | W | 104 | 60.940 | −21.568 | −0.115 | 1.00 | 20.52 | W | O |
| ATOM | 17554 | O | HOH | W | 105 | 58.540 | −23.194 | −0.426 | 1.00 | 28.03 | W | O |
| ATOM | 17557 | O | HOH | W | 106 | 52.842 | −31.073 | −2.319 | 1.00 | 18.19 | W | O |
| ATOM | 17560 | O | HOH | W | 107 | 50.708 | −32.784 | −1.585 | 1.00 | 21.26 | W | O |
| ATOM | 17563 | O | HOH | W | 108 | 42.573 | 24.337 | −31.730 | 1.00 | 23.68 | W | O |
| ATOM | 17566 | O | HOH | W | 109 | 41.632 | −13.280 | 2.319 | 1.00 | 19.40 | W | O |
| ATOM | 17569 | O | HOH | W | 110 | 40.075 | −12.128 | 0.609 | 1.00 | 22.13 | W | O |
| ATOM | 17572 | O | HOH | W | 111 | 61.623 | 26.993 | −12.882 | 1.00 | 31.00 | W | O |
| ATOM | 17575 | O | HOH | W | 112 | 53.819 | 33.804 | −16.115 | 1.00 | 25.71 | W | O |
| ATOM | 17578 | O | HOH | W | 113 | 45.232 | 4.296 | −9.419 | 1.00 | 19.63 | W | O |
| ATOM | 17581 | O | HOH | W | 114 | 67.086 | 25.456 | −18.731 | 1.00 | 20.32 | W | O |
| ATOM | 17584 | O | HOH | W | 115 | 69.127 | −23.507 | −5.191 | 1.00 | 19.05 | W | O |
| ATOM | 17587 | O | HOH | W | 116 | 40.100 | −27.766 | 7.117 | 1.00 | 26.86 | W | O |
| ATOM | 17590 | O | HOH | W | 117 | 41.450 | 14.502 | −35.661 | 1.00 | 21.87 | W | O |
| ATOM | 17593 | O | HOH | W | 118 | 39.215 | 14.175 | −36.764 | 1.00 | 21.90 | W | O |
| ATOM | 17596 | O | HOH | W | 119 | 61.445 | 47.858 | −13.974 | 1.00 | 30.41 | W | O |
| ATOM | 17599 | O | HOH | W | 120 | 42.487 | −37.324 | 1.207 | 1.00 | 19.42 | W | O |
| ATOM | 17602 | O | HOH | W | 121 | 41.098 | −41.117 | 0.324 | 1.00 | 20.14 | W | O |
| ATOM | 17605 | O | HOH | W | 122 | 58.612 | −35.406 | −0.839 | 1.00 | 24.21 | W | O |
| ATOM | 17608 | O | HOH | W | 123 | 50.164 | 1.626 | −14.069 | 1.00 | 17.73 | W | O |
| ATOM | 17611 | O | HOH | W | 124 | 50.992 | −34.804 | 12.341 | 1.00 | 30.50 | W | O |
| ATOM | 17614 | O | HOH | W | 125 | 70.666 | 34.211 | −26.020 | 1.00 | 27.41 | W | O |
| ATOM | 17617 | O | HOH | W | 126 | 57.737 | −13.710 | −12.328 | 1.00 | 35.35 | W | O |
| ATOM | 17620 | O | HOH | W | 127 | 75.308 | 25.160 | −13.718 | 1.00 | 16.25 | W | O |
| ATOM | 17623 | O | HOH | W | 128 | 60.917 | −29.336 | 2.205 | 1.00 | 27.11 | W | O |
| ATOM | 17626 | O | HOH | W | 129 | 37.974 | −12.318 | −6.397 | 1.00 | 29.33 | W | O |
| ATOM | 17629 | O | HOH | W | 130 | 63.665 | −29.882 | −4.118 | 1.00 | 31.17 | W | O |
| ATOM | 17632 | O | HOH | W | 131 | 61.715 | −32.330 | −8.029 | 1.00 | 41.88 | W | O |
| ATOM | 17635 | O | HOH | W | 132 | 72.648 | 30.403 | −18.375 | 1.00 | 23.01 | W | O |
| ATOM | 17638 | O | HOH | W | 133 | 53.042 | 17.634 | −10.102 | 1.00 | 23.18 | W | O |
| ATOM | 17641 | O | HOH | W | 134 | 60.025 | 38.653 | −17.369 | 1.00 | 20.09 | W | O |
| ATOM | 17644 | O | HOH | W | 135 | 61.712 | 36.617 | −16.767 | 1.00 | 26.79 | W | O |

TABLE 4-2-continued

Coordinates of *P. alba* IspS

| | | | | | | | | | | | | |
|---|---|---|---|---|---|---|---|---|---|---|---|---|
| ATOM | 17647 | O | HOH | W | 136 | 61.300 | 41.278 | −13.860 | 1.00 | 21.09 | W | O |
| ATOM | 17650 | O | HOH | W | 137 | 62.073 | −31.149 | 7.450 | 1.00 | 33.22 | W | O |
| ATOM | 17653 | O | HOH | W | 138 | 55.630 | −21.810 | −5.863 | 1.00 | 43.72 | W | O |
| ATOM | 17656 | O | HOH | W | 139 | 42.191 | 33.282 | −26.587 | 1.00 | 21.30 | W | O |
| ATOM | 17659 | O | HOH | W | 140 | 46.789 | 38.171 | −22.658 | 1.00 | 44.17 | W | O |
| ATOM | 17662 | O | HOH | W | 141 | 32.524 | 32.302 | −32.556 | 1.00 | 27.94 | W | O |
| ATOM | 17665 | O | HOH | W | 142 | 83.918 | 41.902 | −15.045 | 1.00 | 20.74 | W | O |
| ATOM | 17668 | O | HOH | W | 143 | 57.939 | −30.258 | 0.884 | 1.00 | 32.72 | W | O |
| ATOM | 17671 | O | HOH | W | 144 | 48.703 | −35.022 | 7.181 | 1.00 | 37.63 | W | O |
| ATOM | 17674 | O | HOH | W | 145 | 66.347 | 31.640 | −19.130 | 1.00 | 30.26 | W | O |
| ATOM | 17677 | O | HOH | W | 146 | 64.998 | 30.057 | −17.211 | 1.00 | 22.53 | W | O |
| ATOM | 17680 | O | HOH | W | 147 | 65.134 | 27.653 | −18.405 | 1.00 | 22.78 | W | O |
| ATOM | 17683 | O | HOH | W | 148 | 66.094 | 38.403 | −18.347 | 1.00 | 23.57 | W | O |
| ATOM | 17686 | O | HOH | W | 149 | 35.459 | 0.990 | 18.585 | 1.00 | 22.46 | W | O |
| ATOM | 17689 | O | HOH | W | 150 | 71.717 | −45.326 | −18.716 | 1.00 | 33.34 | W | O |
| ATOM | 17692 | O | HOH | W | 151 | 50.671 | 5.704 | −4.812 | 1.00 | 26.81 | W | O |
| ATOM | 17695 | O | HOH | W | 152 | 61.207 | −27.443 | −25.202 | 1.00 | 50.62 | W | O |
| ATOM | 17698 | O | HOH | W | 153 | 74.197 | −28.017 | −17.761 | 1.00 | 32.53 | W | O |
| ATOM | 17701 | O | HOH | W | 154 | 39.585 | −1.129 | 16.289 | 1.00 | 21.92 | W | O |
| ATOM | 17704 | O | HOH | W | 155 | 62.622 | −29.524 | −0.090 | 1.00 | 32.78 | W | O |
| ATOM | 17707 | O | HOH | W | 156 | 70.598 | −25.384 | −3.982 | 1.00 | 23.20 | W | O |
| ATOM | 17710 | O | HOH | W | 157 | 56.563 | −33.832 | −0.616 | 1.00 | 27.25 | W | O |
| ATOM | 17713 | O | HOH | W | 158 | 51.474 | −35.440 | −5.147 | 1.00 | 26.23 | W | O |
| ATOM | 17716 | O | HOH | W | 159 | 49.890 | −35.190 | −2.859 | 1.00 | 23.25 | W | O |
| ATOM | 17719 | O | HOH | W | 160 | 53.387 | −33.463 | −5.052 | 1.00 | 31.52 | W | O |
| ATOM | 17722 | O | HOH | W | 161 | 64.357 | −36.964 | 7.375 | 1.00 | 28.26 | W | O |
| ATOM | 17725 | O | HOH | W | 162 | 64.771 | −39.173 | 5.737 | 1.00 | 31.93 | W | O |
| ATOM | 17728 | O | HOH | W | 163 | 40.629 | −47.274 | 5.327 | 1.00 | 20.11 | W | O |
| ATOM | 17731 | O | HOH | W | 164 | 49.479 | −36.987 | 8.266 | 1.00 | 38.74 | W | O |
| ATOM | 17734 | O | HOH | W | 165 | 50.017 | −31.400 | 12.975 | 1.00 | 31.54 | W | O |
| ATOM | 17737 | O | HOH | W | 166 | 72.235 | −28.166 | 9.021 | 1.00 | 33.15 | W | O |
| ATOM | 17740 | O | HOH | W | 167 | 75.744 | −38.559 | −1.129 | 1.00 | 34.88 | W | O |
| ATOM | 17743 | O | HOH | W | 168 | 60.678 | −3.886 | 6.560 | 1.00 | 43.68 | W | O |
| ATOM | 17746 | O | HOH | W | 169 | 54.251 | −10.331 | 7.262 | 1.00 | 44.60 | W | O |
| ATOM | 17749 | O | HOH | W | 170 | 55.713 | −14.623 | −10.880 | 1.00 | 27.94 | W | O |
| ATOM | 17752 | O | HOH | W | 171 | 34.828 | 7.528 | 15.394 | 1.00 | 23.35 | W | O |
| ATOM | 17755 | O | HOH | W | 172 | 30.137 | −4.012 | 5.182 | 1.00 | 32.68 | W | O |
| ATOM | 17758 | O | HOH | W | 173 | 38.389 | −13.593 | −1.858 | 1.00 | 55.11 | W | O |
| ATOM | 17761 | O | HOH | W | 174 | 36.850 | −1.221 | 17.151 | 1.00 | 23.53 | W | O |
| ATOM | 17764 | O | HOH | W | 175 | 38.073 | −28.751 | 3.642 | 1.00 | 47.59 | W | O |
| ATOM | 17767 | O | HOH | W | 176 | 36.616 | −30.178 | 2.331 | 1.00 | 40.67 | W | O |
| ATOM | 17770 | O | HOH | W | 177 | 42.744 | −37.262 | 9.632 | 1.00 | 29.50 | W | O |
| ATOM | 17773 | O | HOH | W | 178 | 42.616 | −35.921 | 11.849 | 1.00 | 42.95 | W | O |
| ATOM | 17776 | O | HOH | W | 179 | 57.767 | −25.689 | −1.640 | 1.00 | 31.54 | W | O |
| ATOM | 17779 | O | HOH | W | 180 | 78.821 | 47.464 | −4.619 | 1.00 | 41.91 | W | O |
| ATOM | 17782 | O | HOH | W | 181 | 72.583 | 36.467 | −26.619 | 1.00 | 34.41 | W | O |
| ATOM | 17785 | O | HOH | W | 182 | 58.768 | 41.958 | −26.296 | 1.00 | 36.05 | W | O |
| ATOM | 17788 | O | HOH | W | 183 | 58.524 | 37.308 | −31.915 | 1.00 | 27.65 | W | O |
| ATOM | 17791 | O | HOH | W | 184 | 59.204 | 34.222 | −32.284 | 1.00 | 31.17 | W | O |
| ATOM | 17794 | O | HOH | W | 185 | 67.396 | 24.341 | −21.206 | 1.00 | 28.49 | W | O |
| ATOM | 17797 | O | HOH | W | 186 | 73.538 | 21.133 | −16.293 | 1.00 | 20.45 | W | O |
| ATOM | 17800 | O | HOH | W | 187 | 85.397 | 37.797 | −17.665 | 1.00 | 32.53 | W | O |
| ATOM | 17803 | O | HOH | W | 188 | 63.942 | 25.997 | −4.112 | 1.00 | 54.26 | W | O |
| ATOM | 17806 | O | HOH | W | 189 | 53.679 | 16.888 | −7.621 | 1.00 | 33.46 | W | O |
| ATOM | 17809 | O | HOH | W | 190 | 34.187 | 3.648 | −33.715 | 1.00 | 31.20 | W | O |
| ATOM | 17812 | O | HOH | W | 191 | 38.654 | −3.056 | −28.664 | 1.00 | 31.71 | W | O |
| ATOM | 17815 | O | HOH | W | 192 | 36.665 | 19.812 | −19.436 | 1.00 | 30.48 | W | O |
| ATOM | 17818 | O | HOH | W | 193 | 38.939 | 22.647 | −22.845 | 1.00 | 25.48 | W | O |
| ATOM | 17821 | O | HOH | W | 194 | 33.628 | 27.331 | −38.304 | 1.00 | 38.64 | W | O |
| ATOM | 17824 | O | HOH | W | 195 | 41.094 | 33.581 | −28.770 | 1.00 | 21.68 | W | O |
| ATOM | 17827 | O | HOH | W | 196 | 37.378 | 31.618 | −27.424 | 1.00 | 46.50 | W | O |
| ATOM | 17830 | O | HOH | W | 197 | 37.702 | 28.581 | −29.110 | 1.00 | 25.65 | W | O |
| ATOM | 17833 | O | HOH | W | 198 | 60.016 | 20.154 | −7.770 | 1.00 | 31.81 | W | O |
| ATOM | 17836 | O | HOH | W | 199 | 44.586 | 28.481 | 1.221 | 1.00 | 33.43 | W | O |
| ATOM | 17839 | O | HOH | W | 200 | 38.150 | 20.885 | −9.839 | 1.00 | 37.13 | W | O |
| ATOM | 17842 | O | HOH | W | 201 | 44.203 | 35.043 | −19.031 | 1.00 | 37.68 | W | O |
| ATOM | 17845 | O | HOH | W | 202 | 43.620 | 33.989 | −22.475 | 1.00 | 31.80 | W | O |
| ATOM | 17848 | O | HOH | W | 203 | 56.689 | 23.953 | −42.205 | 1.00 | 38.64 | W | O |
| ATOM | 17851 | O | HOH | W | 204 | 59.706 | 41.117 | −16.030 | 1.00 | 22.92 | W | O |
| ATOM | 17854 | O | HOH | W | 205 | 55.135 | 39.948 | −8.848 | 1.00 | 53.09 | W | O |
| END | | | | | | | | | | | | |

Example 5

Engineering *Populus alba* Isoprene Synthase for Improved Activity

This example described methods to identify *P. alba* isoprene synthase (IspS) variants with increased activity, sites for protein engineering studies were chosen based on the crystal structure of the enzyme. Twenty-five site evaluation libraries (SELs) were analyzed for specific activity, and subsequently ranked according to their performance relative to controls.

I. SEL Plasmid Backbone

Figure 39:
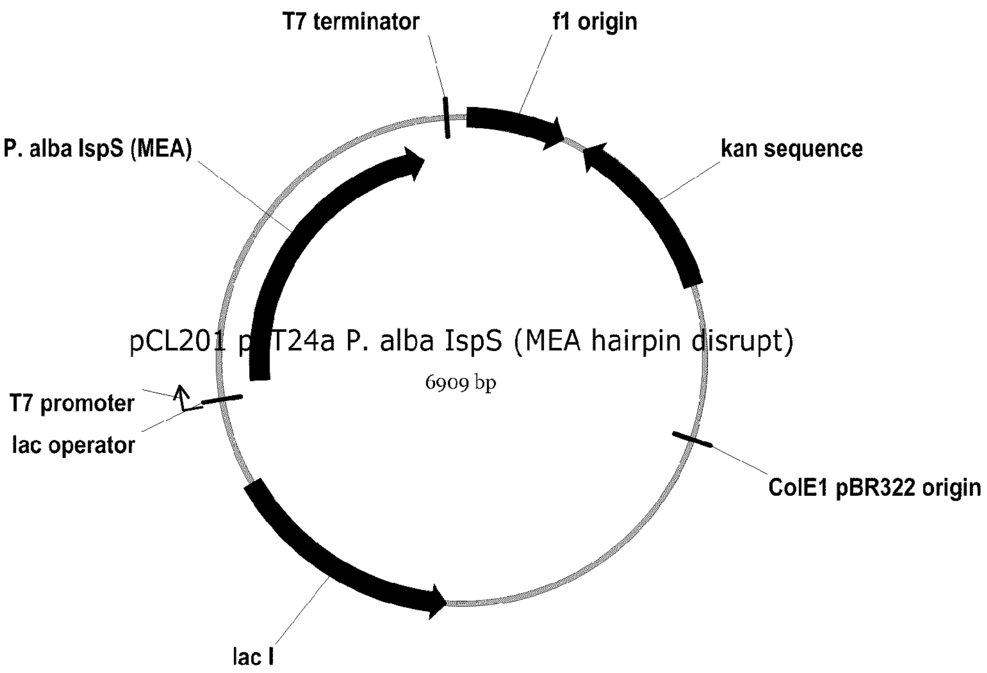
FIG. 39 provides a map of plasmid pCL201 (pET24a *P. alba* IspS (MEA hairpin disrupt)).

The plasmid backbone used to generate the 25 SELs was constructed by QuikChange (Stratagene) PCR on the template pDu39 (see U.S. patent application Ser. No. 12/429, 143). The PCR reaction mixtures were as follows: 1 μl pDu39, 5 μl 10× PfuUltra HF buffer, 1 μl dNTPs, 1 μl (50 μM) MEA Hairpin Disrupt (pET) F (Table 4-1), 1 μl (50 μM) MEA Hairpin Disrupt (pET) R (Table 5-1), 2 μl DMSO, 39 μl $diH_2O$, 1 μl PfuUltra HF Polymerase (Stratagene). The PCR Cycling Parameters for QuikChange were as follows: 1. 95° C. 1 min, 2. 95° C. 50 sec, 3. 60° C. 50 sec, 4. 68° C. 7 min, 5. Repeat steps 2-4 for 18 cycles, 6. 68° C. 7 min. The PCR product was treated with 1 μl DpnI (Roche) for 3 hours, and then 1 μl of the entire reaction was transformed into chemically competent *E. coli* Top10 cells (Invitrogen), recovered, and plated according to the manufacturer's recommendations. The next day, positive colonies were chosen for growth, plasmid purification (Qiagen) and sequencing (Quintara Biosciences). Plasmids which harbored the correct base changes introduced using the Quikchange Site-Directed Mutagenesis Kit (Stratagene) were selected for sequencing of the entire open reading frame to confirm the integrity of the coding sequence. One of these plasmids, pCL201 (see FIGS. 39-41), was selected as the backbone for construction of the 25 SELs (Verdezyne).

TABLE 5-1

| Primer sequences | |
|---|---|
| MEA Hairpin Disrupt (pET) F | ggagatatacatatggaagcacgtcgc tctgcgaactacgaacctaa (SEQ ID NO: 46) |
| MMEA Hairpin Disrupt (pET) R | ttaggttcgtagttcgcagagcgacgtg cttccatatgtatatctcc (SEQ ID NO: 47) |
| T7 Forward | taatacgactcactataggg (SEQ ID NO: 48) |
| T7 Reverse | gctagttattgctcagcgg (SEQ ID NO: 49) |
| 1000 | gcactgtctttccgtctgctgc (SEQ ID NO: 50) |
| QB1493 | cttcggcaacgcatggaaat (SEQ ID NO: 51) |
| A-rev | ctcgtacaggctcaggatag (SEQ ID NO: 52) |
| A-rev2 | ttacgtcccaacgctcaact (SEQ ID NO: 53) |

II. 25 Site Evaluation Libraries

Figure 42:
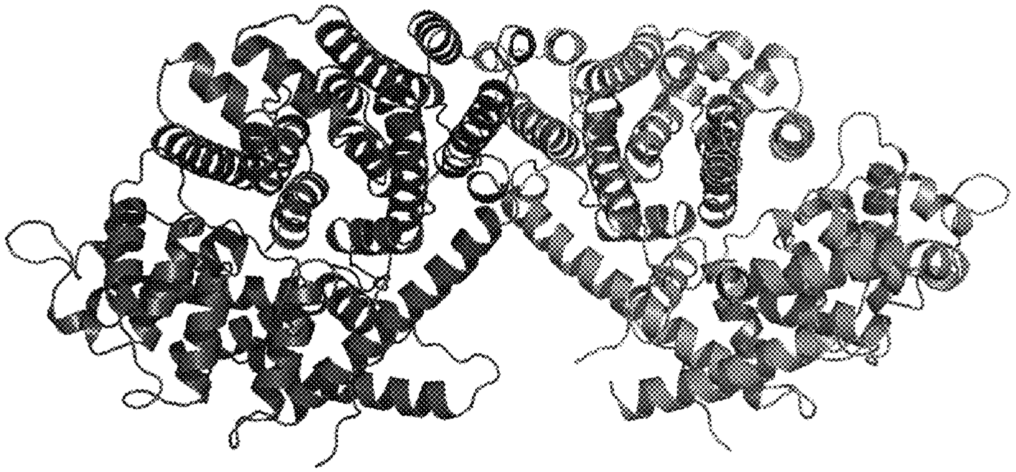
FIG. 42 provides the three-dimensional structure of *P. alba* IspS shown as a dimer. Chain A is in dark gray and chain B is in light gray.
Figure 43:
FIG. 43 provides a monomer view of the structure of *P. alba* IspS.
Figure 44:
FIG. 44 provides a view of the structure of 25 sites chosen for SEL in stick diagram on the ribbon diagram backbone of the *P. alba* IspS monomer.
Figure 46:
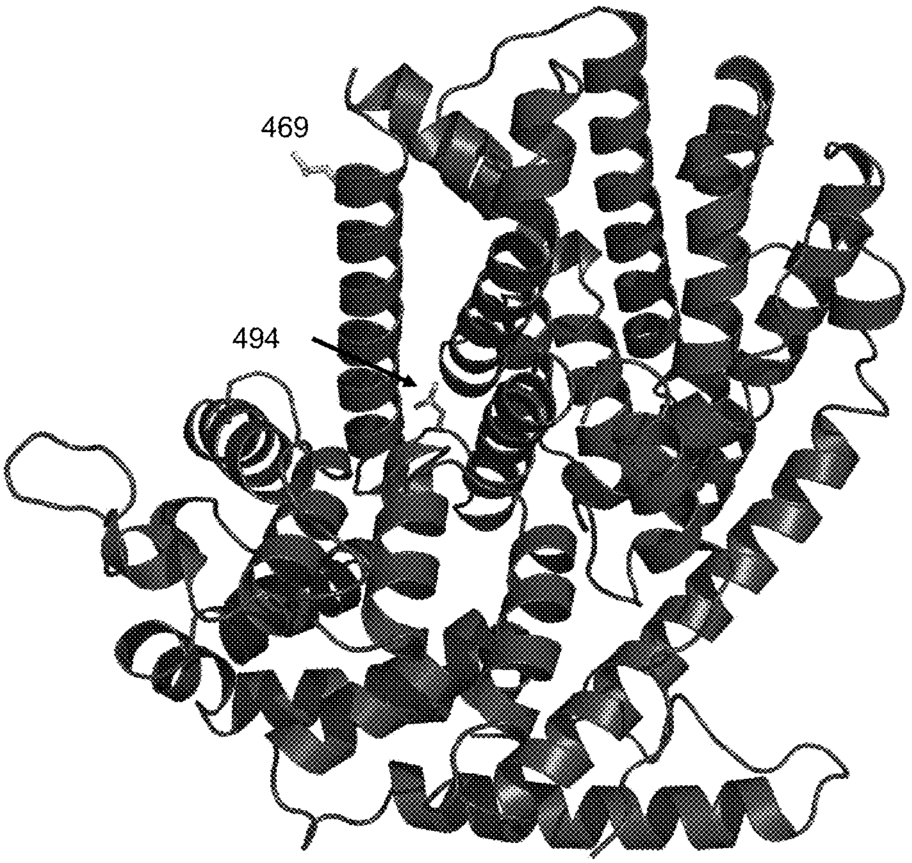
FIG. 46 provides the location of surface hydrophobic residue sites 469 and 494 of *P. alba* IspS.
Figure 47:
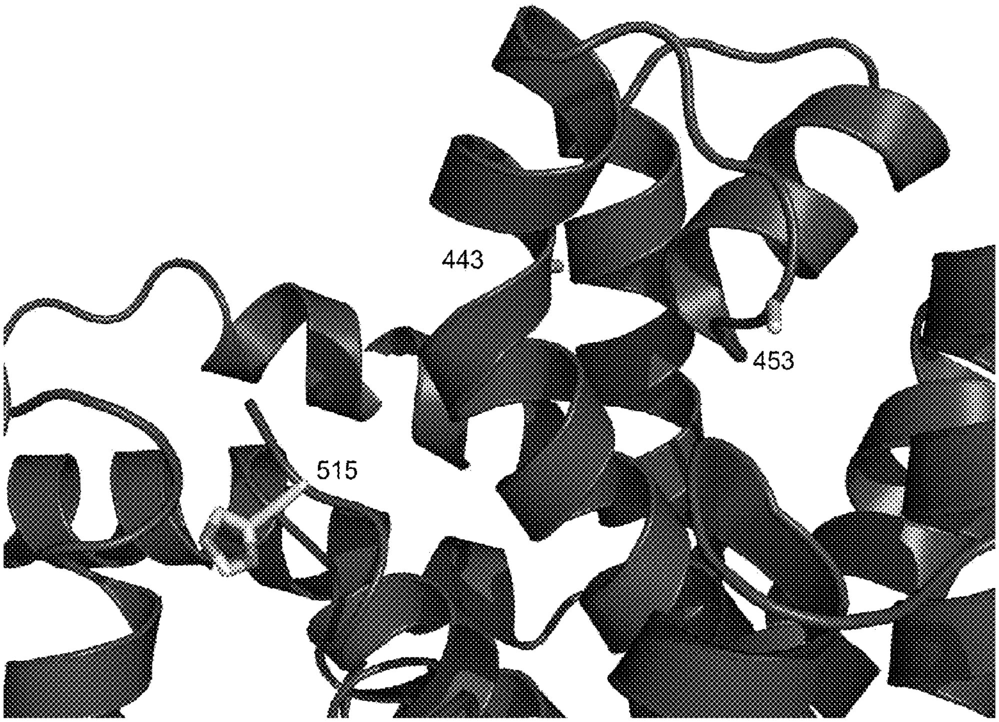
FIG. 47 provides the location of flexible loop residue sites 443, 453 and 515 of *P. alba* IspS.
Figure 48:
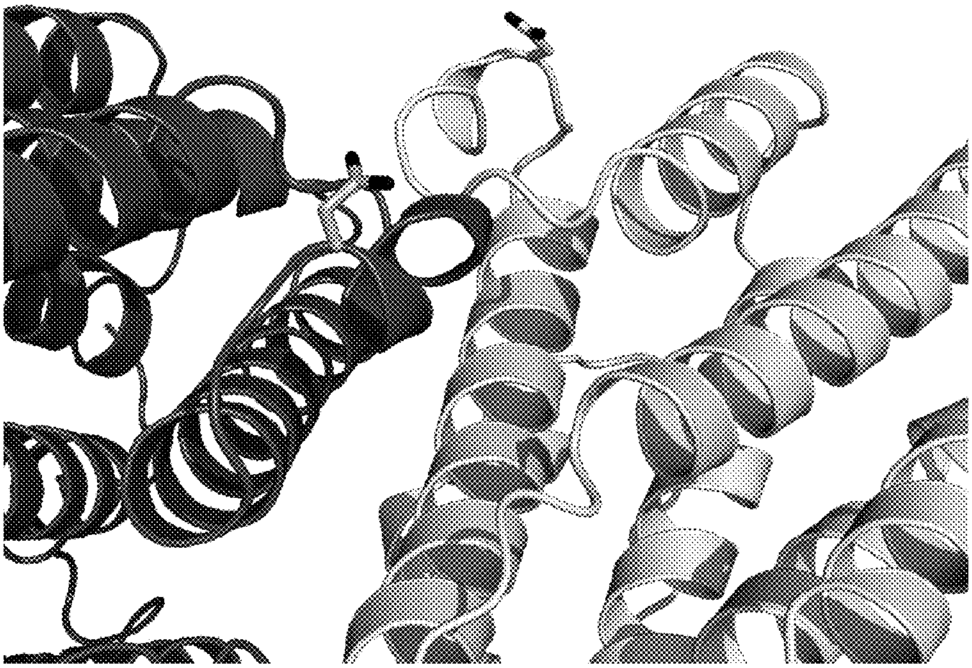
FIG. 48 provides the location of negatively charged residue site 323 of *P. alba* IspS dimer.
Figure 49:
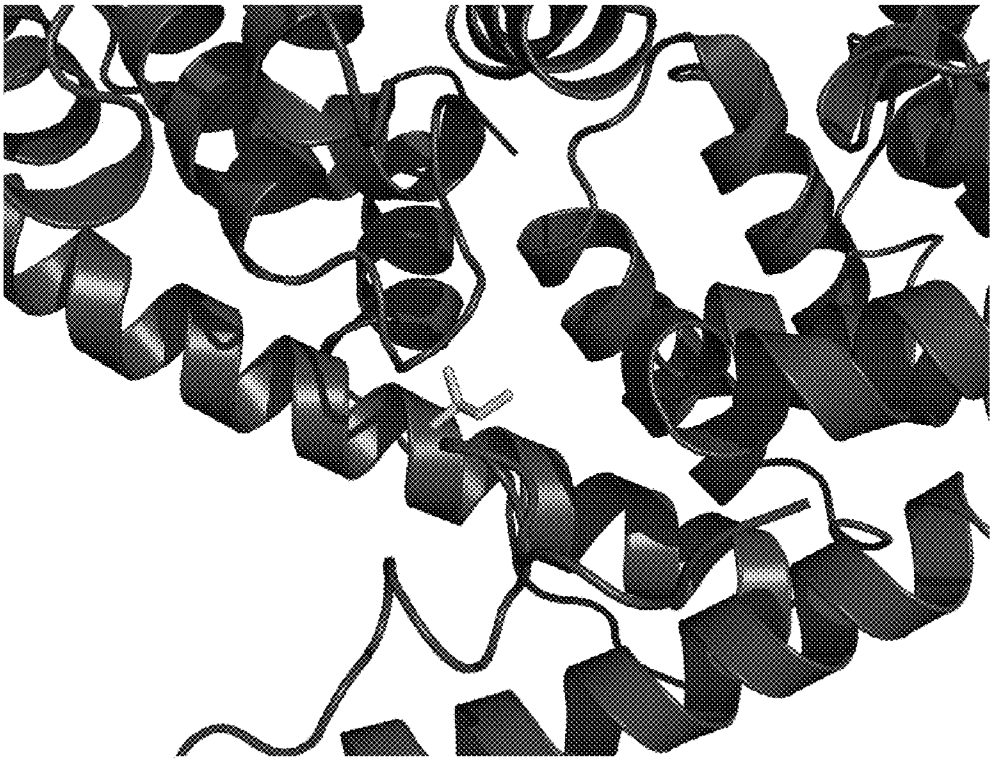
FIG. 49 provides the location of hinge residue site 229 of the *P. alba* IspS.
Figure 50:
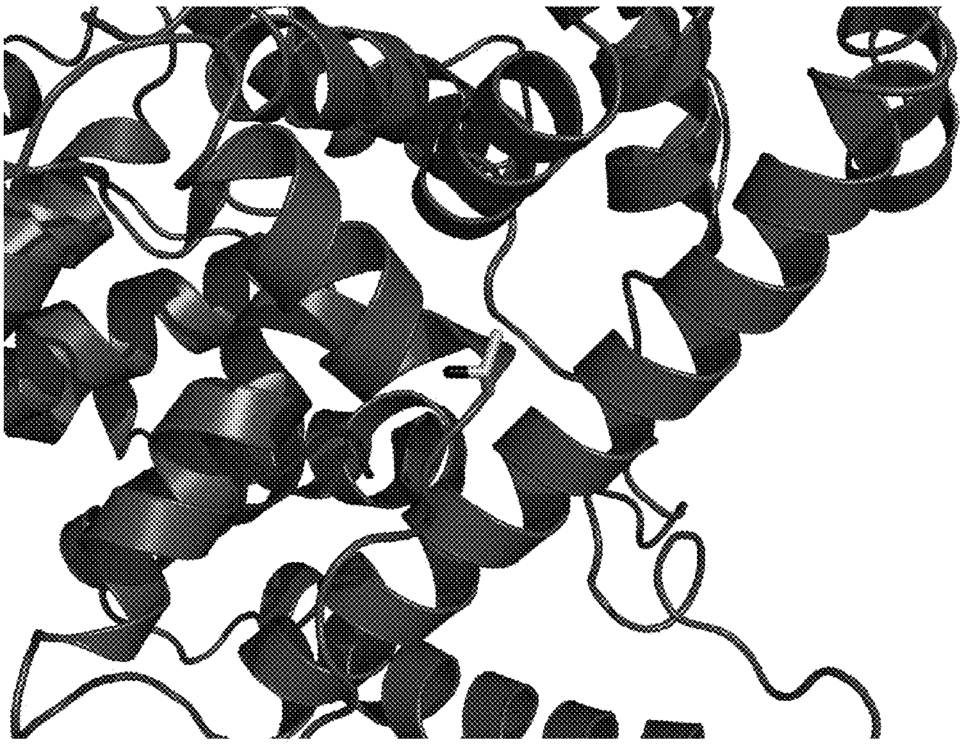
FIG. 50 provides the location of site 536 of *P. alba* IspS.

Sites for the 25 SELs were chosen based upon the crystal structure of *P. alba* IspS (Example 4). Table 5-2 lists all sites and a description of their putative role within the enzyme. Alterations in surface hydrophobic residues may affect protein folding, solubility or activity. Sites in the "hinge region" are located in a helix that spans the N-terminus and the C-terminus, and may dictate how those two halves of the enzyme interact with each other. Sites in the "negatively charged area" are in a region of the protein with a high density of acidic residues, which may somehow regulate activity. Sites within the "flexible loops" are proximal to the active site, and may affect substrate binding, as would sites that are directly within the active site (see Table 5-2). FIG. 42 shows the structure of an IspS dimer, and FIG. 43 shows a monomer. FIG. 44 shows all 25 sites chosen for SELs in stick diagram on the ribbon diagram backbone of the IspS monomer. SELs were generated in the pCL201 plasmid backbone. Plasmids harboring IspS variants were transformed into BL21 DE3 pLysS (Invitrogen) and delivered as glycerol stocks for subsequent growth and screening. FIG. 45 shows the layout of a typical 96-well plate containing 4 complete libraries to be screened for isoprene production and protein concentration. In some cases, where a specific substitution could not be isolated, a the wild type codon was substituted instead.

TABLE 5-2

| Sites for SEL | |
|---|---|
| Description | Sites for SEL |
| Surface hydrophobic residues | I28, V30, L130, G153, V299, L303, L469, L494 |
| Hinge region | R198, I229, L260 |
| Negatively charged area | D311, D323 |
| Flexible loops | A443, A453, N454, H515, A519, E525 |
| Active site | F388, N438, E451 |
| Miscellaneous | D345, R528, T536 |

III. DMAPP Assay

A) Growth and Induction

1. Prepared Patch Plates from Glycerol Stock Plates. Using a V&S 96 pin Replication Tool, cultures were patched onto a LB Agar 35 CMP/50 Kan large patch plates from overnight glycerol stock plates. Plates were incubated at 30° C. overnight for 20 to 24 hr. Cultures can be stored at 4° C. for up to a week.

2. Prepared Overnight Growth Plates. 500 mL of LB 35 CMP/50 Kan media were prepared. 300 μL/well of LB 35 CMP/50 Kan media were dispensed into deep 96 well plates (VWR). Using a V&S Replication Tool, the patch inoculum was transferred into deep 96 well plate by touching the tool pins to respective patch and using a circular motion to coat the pins with inoculum. The media was inoculated by dipping the tool then shaking the pin within the well. The overnight growth plates were sealed using a Breathe-Easier Sealing Membrane (Diversified Biotech). The plates were incubated in a Vertiga Shaking Incubator at 30° C. with shaking at 800 rpm overnight for 16 to 18 hr.

3. Prepared Day Growth Plate. Deep 96 well plates were prepared by dispensing 588 μL/well of LB 35 CMP/50 Kan media. Overnight growth plates were removed from the incubator. Overnight cultures were diluted 50-fold and 12 μL of overnight culture were transferred to day growth plates containing 588 μL/well of LB media containing antibiotics. Overnight growth plates were sealed with new Breathe-Easier Sealing Membranes. Cultures were incubated at 30° C. and 800 rpm for 2.5 hr. Frozen 12 mM IPTG (Sigma) vials were removed from −20° C. and placed in a hood to thaw.

4. $OD_{600}$ Plate Read of Overnight, Induction, and Harvest. 150 μL 1×PBS were dispensed into 96 well Costar Read Plates (#9017). 50 μL of culture samples were transferred to Read Plates. The $OD_{600}$ reading was recorded using a Spectramax Plate Reader (Molecular Devices).

5. Induction. Electronic multi-channel pipettors were prepared to dispense 4×20 μL/well of IPTG (if 4× replicates). The multi-dispense option in the electronic pipettor was adjusted if more replicates was necessary. Thawed 12 mM IPTG was poured into 50 mL or 100 mL sterile reservoirs. 20 μL/well of IPTG into each 600 μL/well culture. Overnight growth plates were resealed. Cultures were incubated at 30° C. and 800 rpm for 4 hr. $OD_{600}$ readings of plates were recorded according instructions above.

6. Harvest. 400 μL of induced culture were transferred to 800 μL Grenier storage plates. Plates were centrifuged at 3300 rpm for 20 min at 2° to 8° C. in a low speed benchtop centrifuge. Supernatants were discarded, pellets should stay in the conical bottom well. Residual supernatants were slapped out onto a paper towel on the benchtop. Plates were sealed with an aluminum foil membrane (Beckman-Coulter). Plates were covered with a plastic plate lid if available. Storage plates were labeled accordingly and stored frozen at −80° C.

B) DMAPP Assay

Plates containing induced cell pellets were removed from the −80° C. freezer and allowed to thaw on the benchtop for 30 minutes prior to lysis. 200 μl of lysis buffer (50 mM Tris pH 8, 25 mM $MgCl_2$, 74 μg/ml DNase I, 250 U/ml lysozyme, 0.1% Tween 20, 0.5 mM PMSF) was added to each pellet, and plates were incubated on an Eppendorf Thermomixer at 25° C. for 30 minutes at 1200 rpm. After lysis, plates were centrifuged at 3450 rpm for 15 minutes at 4° C. Supernatants were then removed and diluted 10-fold prior to DMAPP assay. 80 μl of the diluted supernatant was added to 20 μl of the DMAPP working stock (20 mM DMAPP in 0.1 M Phosphate Buffer pH 8.2, DMAPP triammonium salt, Cayman chemicals) in a Zinsser glass block. Blocks were then sealed with aluminum sealing membranes, and incubated in Thermomixers at 25° C. for 30 minutes at 450 rpm. Reactions were stopped by incubating blocks on Thermomixers at 70° C. for 12 minutes at 450 rpm. GC-MS was then used for headspace measurements to calculate the amount of isoprene produced by each lysates.

Headspace Assay. A sample of 200 μl of the desired culture is inoculated into 2 ml CTC headspace vials (Agilent vial Catalog No. 5188 2753, and cap Catalog No. 5188 2759). The cap was screwed on tightly and the vials were incubated at 37° C. with shaking at 250 rpm. After 30 minutes the vials were removed from the incubator and cooled briefly with ambient tap water. The vials were placed into the CombiPal Headspace auto sampler for analysis by GC-MS. The analysis was performed using an Agilent 6890 GC/MS system interfaced with a CTC Analytics CombiPAL autosampler operating in headspace mode. An Agilent HP-5MS GC/MS column (30 m×0.25 mm; 0.25 μm film thickness) was used for separation of analytes. The sampler was set up to inject 500 μL of headspace gas. The GC/MS method utilized helium as the carrier gas at a flow of 1 ml/min. The injection port was held at 250° C. with a split ratio of 50:1. The oven temperature was held at 37° C. for the 2 min duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 μg/L to 200 μg/L. The limit of detection was estimated to be 50-100 μg/L using this method.

IV. Rapid ELISA Protocol Using 96-Well PVDF Filter Plates:

Frozen liquid alkaline phosphatase substrate was removed from the freezer and allowed to come to room temperature. PVDF plates (Millipore, Whatman) are pre-wetted by adding 50 μl 50% MeOH per well. Calibration curve samples are prepared in blue PCR plates (Bio-Rad plates are good for low volumes). Normally, 10 μl of 100 ug/ml standard was added to 90 μl TBSD for 1:10 dilution, followed by 1:2 serial dilutions in TBSD. TBSD was 50 mM Tris pH 8, 150 mM NaCl, 0.1% Na deoxycholate (from a 10% w/v solution in 50% EtOH stock), 0.05% Na azide). Samples were prepared in one or more dilutions in blue PCR plate (or suitable low volume plate). 100 μl $H_2O$ was added to PVDF plate and removed by vacuum and washed with $H_2O$ (2×100 μl). A microtiter plate vacuum manifold, set for 10-15 in. Hg vacuum, was used. 50 μl TBSD was added to PVDF plate. Calibrators and samples were added to the PVDF plate, usually in duplicate, allowed to sit 5 min. or longer, and then removed by vacuum. 50 μl blocking buffer (TBST+1% BSA; TBST was 50 mM Tris pH 8, 150 mM NaCl, 0.1% Tween 80, 0.05% Na azide) was added to the PVDF plate and let sit 15 min. or longer. 1° antibody was prepared in blocking buffer (about 1:2000 dilution, depending on target). 2° antibody in blocking buffer (normally goat anti-rabbit alkaline phosphatase conjugate, 1:2000 dilution). PVDF plate was vacuumed and 50 μl 1° antibody was added. The plate was allowed to sit for 5 min. or longer and then vacuumed. The plate was washed 4 times with 200 μl TBST. The 2° antibody was added at a 1:2000 dilution and allowed to sit for 5 min. or longer and then the 2° antibody was removed by vacuum. The plate was washed 4 times with 200 μl TBST. 120 μl of Alkaline phosphatase substrate solution, p-nitrophenyl phosphate liquid substrate (Sigma #N7653), was added to the plate. Color development was monitored and stop reaction when appropriate, normally 10-30 min. The color reaction was stopped by transferring 80 μl to a clear microtiter plate, or by adding 50 μl 3N NaOH followed by transferring 130 μl to clear microtiter plate. The absorbance of each reaction was read in plate reader at 405 nm. Data was exported as a .txt file and imported into an Excel spreadsheet. The average of calibrator replicates was calculated and standard curves were plotted as $A_{405}$ (x-axis) and μg/ml (y-axis). Best curve fit were determined using linear, power, or exponential algorithms. For best results, only the calibrator range that corresponded to the sample range was used. Because Excel may have difficulty with the entire calibrator range, multiple smaller ranges may be used. Best curve fit equations were used to calculate concentrations of samples. Optimum antibody concentrations were determined empirically. Usual concentrations ran between 1:1000 and 1:8000, but results may vary with target immunogenicity, animal response, and assay concentration range.

V. Results

Site evaluation libraries were screened for specific activity. The performance of variant molecules was determined by activity on a substrate dimethylallyldiphosphate (DMAPP) per unit weight of the molecule (see above). Variant molecules were ranked relative to the parental molecule. The performance index was calculated as activity per unit weight relative the parental molecule. The parental molecule had a performance index of one, by definition. Activity of the parental molecule was calculated as the average of 22-24 assays of the parental molecule. A performance index greater than one indicates an improved molecule.

The positions of some high performing variants mapped onto the crystal structure of *P. alba* IspS are shown in FIGS. 46 through 50. These include but are not limited to sites 469 and 494 (surface hydrophobic, see Table 5-2 and FIGS. 46), 443, 453, and 515 (flexible loops, see Table 5-2 and FIG. 47), 323 (negatively charged area, see Table 5-2 and FIG. 48), 229 (hinge region, see Table 5-2 and FIGS. 49), and 536 (miscellaneous, see Table 5-2 and FIG. 50). The specific amino acid changes at these sites include but are not limited to I229V, I229L, D323M, A443S, A453I, A453L, A453N, L469A, L494C, L494G, L494I, L494P, L494V, H515M, T536F, T536Y, T536V, T536I, T536M, T536H, T536C, and T536L. Table 5-3 shows a list of variants at sites based on performance index.

Sites 198, 438, and 451 have a low tolerance for substitution as evidenced by all variants displaying reduced specific activity. Similarly, site 528 shows a low tolerance for substitution, with only a conservative variant lysine residue producing activity similar to the parental arginine.

TABLE 5-3

Performance indices of variants

| site | variant | performance index | site | variant | performance index |
|---|---|---|---|---|---|
| I28 | W | 1.53 | V30 | K | 1.06 |
| I28 | T | 1.25 | V30 | I | 0.90 |
| I28 | R | 1.05 | V30 | E | 0.86 |
| I28 | Y | 1.02 | V30 | W | 0.85 |
| I28 | G | 0.93 | V30 | Y | 0.81 |
| I28 | F | 0.84 | V30 | G | 0.80 |
| I28 | S | 0.75 | V30 | F | 0.76 |
| I28 | N | 0.73 | V30 | Q | 0.72 |
| I28 | V | 0.72 | V30 | C | 0.72 |
| I28 | M | 0.72 | V30 | P | 0.67 |
| I28 | P | 0.71 | V30 | R | 0.65 |
| I28 | A | 0.71 | V30 | L | 0.65 |
| I28 | L | 0.68 | V30 | D | 0.64 |
| I28 | E | 0.59 | V30 | T | 0.61 |
| I28 | D | 0.57 | V30 | A | 0.60 |
| I28 | C | 0.53 | V30 | S | 0.60 |
| | | | V30 | M | 0.57 |
| | | | V30 | N | 0.53 |

| site | variant | performance index | site | variant | performance index |
|---|---|---|---|---|---|
| L130 | W | 1.54 | G153 | K | 1.19 |
| L130 | K | 1.54 | G153 | H | 1.18 |
| L130 | S | 1.48 | G153 | L | 1.16 |
| L130 | Y | 1.37 | G153 | W | 1.08 |
| L130 | R | 1.30 | G153 | Y | 0.99 |
| L130 | V | 1.22 | G153 | N | 0.91 |
| L130 | I | 1.20 | G153 | R | 0.90 |
| L130 | E | 1.06 | G153 | S | 0.80 |
| L130 | D | 1.04 | G153 | Q | 0.79 |
| L130 | Q | 0.96 | G153 | A | 0.75 |
| L130 | G | 0.95 | G153 | T | 0.74 |
| L130 | A | 0.93 | G153 | P | 0.72 |
| L130 | M | 0.87 | G153 | D | 0.72 |
| L130 | C | 0.81 | G153 | C | 0.69 |
| L130 | P | 0.43 | G153 | M | 0.68 |
| | | | G153 | V | 0.64 |

| site | variant | performance index | site | variant | performance index |
|---|---|---|---|---|---|
| I229 | V | 4.41 | L260 | N | 1.12 |
| I229 | L | 3.77 | L260 | M | 1.10 |
| I229 | C | 1.35 | L260 | I | 1.04 |
| I229 | T | 1.33 | L260 | H | 0.93 |
| I229 | P | 1.22 | L260 | V | 0.67 |
| I229 | N | 1.04 | L260 | W | 0.40 |
| I229 | S | 0.92 | L260 | Q | 0.37 |
| I229 | W | 0.85 | L260 | A | 0.34 |
| I229 | Q | 0.69 | L260 | P | 0.32 |
| I229 | F | 0.60 | L260 | Y | 0.30 |
| I229 | M | 0.56 | L260 | G | 0.22 |
| I229 | E | 0.54 | L260 | K | 0.15 |
| I229 | A | 0.48 | L260 | S | 0.11 |

TABLE 5-3-continued

Performance indices of variants

| | | | | | |
|---|---|---|---|---|---|
| I229 | H | 0.47 | L260 | E | 0.07 |
| I229 | G | 0.45 | L260 | T | 0.05 |
| I229 | Y | 0.42 | L260 | R | 0.05 |
| I229 | K | 0.24 | L260 | D | 0.03 |
| I229 | D | 0.17 | | | |
| I229 | R | 0.07 | | | |

| site | variant | performance index | site | variant | performance index |
|---|---|---|---|---|---|
| R198 | D | 0.68 | V299 | L | 0.978 |
| R198 | G | 0.39 | V299 | A | 0.346 |
| R198 | V | 0.36 | V299 | T | 0.318 |
| R198 | T | 0.19 | V299 | S | 0.130 |
| R198 | S | 0.15 | V299 | M | 0.115 |
| R198 | H | 0.15 | V299 | N | 0.101 |
| R198 | A | 0.11 | V299 | K | 0.068 |
| R198 | C | 0.11 | V299 | R | 0.061 |
| R198 | I | 0.10 | V299 | W | 0.056 |
| R198 | M | 0.09 | V299 | G | 0.050 |
| R198 | N | 0.03 | V299 | H | 0.042 |
| R198 | F | 0.02 | V299 | E | 0.040 |
| R198 | Y | 0.02 | V299 | Y | 0.032 |
| R198 | H | 0.01 | V299 | D | 0.025 |
| R198 | L | 0.01 | V299 | P | 0.00 |

| site | variant | performance index | site | variant | performance index |
|---|---|---|---|---|---|
| D311 | M | 3.10 | D323 | M | 1.92 |
| D311 | F | 1.46 | D323 | W | 1.76 |
| D311 | L | 1.23 | D323 | Y | 1.38 |
| D311 | G | 1.22 | D323 | F | 1.33 |
| D311 | I | 1.21 | D323 | I | 1.27 |
| D311 | A | 1.12 | D323 | S | 1.22 |
| D311 | T | 1.10 | D323 | V | 1.10 |
| D311 | R | 1.08 | D323 | N | 1.07 |
| D311 | V | 1.06 | D323 | A | 1.03 |
| D311 | E | 1.02 | D323 | G | 1.03 |
| D311 | K | 0.95 | D323 | Q | 1.03 |
| D311 | S | 0.89 | D323 | K | 1.00 |
| D311 | W | 0.82 | D323 | T | 0.97 |
| D311 | Q | 0.67 | D323 | L | 0.93 |
| | | | D323 | C | 0.92 |
| | | | D323 | R | 0.90 |
| | | | D323 | E | 0.75 |

| site | variant | performance index | site | variant | performance index |
|---|---|---|---|---|---|
| D345 | Y | 0.84 | L303 | I | 1.11 |
| D345 | I | 0.73 | L303 | M | 1.07 |
| D345 | K | 0.69 | L303 | V | 0.93 |
| D345 | L | 0.65 | L303 | C | 0.85 |
| D345 | E | 0.61 | L303 | S | 0.78 |
| D345 | N | 0.58 | L303 | E | 0.77 |
| D345 | T | 0.56 | L303 | W | 0.74 |
| D345 | Q | 0.56 | L303 | T | 0.71 |
| D345 | G | 0.55 | L303 | P | 0.71 |
| D345 | V | 0.51 | L303 | H | 0.59 |
| D345 | A | 0.50 | L303 | Q | 0.58 |
| D345 | W | 0.46 | L303 | G | 0.55 |
| D345 | C | 0.43 | L303 | D | 0.54 |
| D345 | M | 0.43 | L303 | A | 0.52 |
| D345 | S | 0.41 | L303 | R | 0.49 |
| D345 | R | 0.40 | | | |
| D345 | P | 0.35 | | | |

| site | variant | performance index | site | variant | performance index |
|---|---|---|---|---|---|
| A443 | S | 1.79 | E451 | G | 0.16 |
| A443 | G | 1.28 | E451 | K | 0.15 |
| A443 | R | 1.19 | E451 | S | 0.14 |
| A443 | Q | 1.01 | E451 | I | 0.13 |
| A443 | H | 0.28 | E451 | H | 0.13 |
| A443 | L | 0.27 | E451 | Q | 0.13 |
| A443 | N | 0.24 | E451 | V | 0.12 |

TABLE 5-3-continued

Performance indices of variants

| | | | | | |
|---|---|---|---|---|---|
| A443 | F | 0.24 | E451 | L | 0.12 |
| A443 | I | 0.18 | E451 | F | 0.12 |
| A443 | V | 0.18 | E451 | Y | 0.12 |
| A443 | T | 0.12 | E451 | W | 0.12 |
| A443 | P | 0.10 | E451 | T | 0.12 |
| | | | E451 | D | 0.12 |
| | | | E451 | R | 0.11 |
| | | | E451 | N | 0.10 |
| | | | E451 | C | 0.09 |
| | | | E451 | A | 0.09 |
| | | | E451 | P | 0.08 |

| site | variant | performance index | site | variant | performance index |
|---|---|---|---|---|---|
| F388 | L | 1.06 | N438 | W | 1.02 |
| F388 | Y | 0.88 | N438 | K | 0.34 |
| F388 | H | 0.73 | N438 | P | 0.31 |
| F388 | P | 0.26 | N438 | I | 0.29 |
| F388 | K | 0.25 | N438 | R | 0.28 |
| F388 | S | 0.25 | N438 | V | 0.20 |
| F388 | T | 0.25 | N438 | Q | 0.20 |
| F388 | Q | 0.18 | N438 | L | 0.19 |
| F388 | V | 0.15 | N438 | M | 0.18 |
| F388 | G | 0.10 | N438 | S | 0.17 |
| F388 | R | 0.09 | N438 | H | 0.16 |
| F388 | C | 0.09 | N438 | Y | 0.15 |
| F388 | D | 0.09 | N438 | F | 0.14 |
| F388 | A | 0.08 | N438 | T | 0.13 |
| | | | N438 | C | 0.12 |
| | | | N438 | E | 0.12 |
| | | | N438 | G | 0.11 |
| | | | N438 | A | 0.11 |
| | | | N438 | D | 0.11 |

| site | variant | performance index | site | variant | performance index |
|---|---|---|---|---|---|
| N454 | S | 0.49 | L494 | P | 2.64 |
| N454 | G | 0.33 | L494 | C | 1.89 |
| N454 | H | 0.28 | L494 | I | 1.71 |
| N454 | T | 0.24 | L494 | V | 1.57 |
| N454 | D | 0.20 | L494 | S | 1.38 |
| N454 | A | 0.15 | L494 | G | 1.30 |
| N454 | E | 0.14 | L494 | D | 1.04 |
| N454 | Q | 0.11 | L494 | E | 0.87 |
| N454 | L | 0.05 | L494 | H | 0.70 |
| N454 | W | 0.05 | L494 | K | 0.68 |
| N454 | F | 0.03 | L494 | Y | 0.66 |
| N454 | I | 0.03 | L494 | Q | 0.63 |
| N454 | Y | 0.02 | L494 | N | 0.58 |
| N454 | V | 0.02 | L494 | R | 0.41 |
| N454 | R | 0.02 | L494 | A | 0.39 |
| N454 | C | 0.02 | L494 | W | 0.37 |
| N454 | P | 0.02 | L494 | T | 0.08 |
| N454 | M | 0.02 | | | |

| site | variant | performance index | site | variant | performance index |
|---|---|---|---|---|---|
| L469 | A | 1.45 | A453 | N | 2.99 |
| L469 | Q | 1.06 | A453 | I | 1.77 |
| L469 | S | 0.97 | A453 | V | 1.08 |
| L469 | L | 0.96 | A453 | T | 0.53 |
| L469 | R | 0.78 | A453 | Y | 0.43 |
| L469 | I | 0.75 | A453 | E | 0.39 |
| L469 | V | 0.74 | A453 | H | 0.37 |
| L469 | C | 0.71 | A453 | F | 0.35 |
| L469 | H | 0.66 | A453 | C | 0.35 |
| L469 | T | 0.63 | A453 | S | 0.34 |
| L469 | F | 0.60 | A453 | W | 0.22 |
| L469 | N | 0.57 | A453 | R | 0.21 |
| L469 | Y | 0.47 | A453 | D | 0.10 |
| L469 | W | 0.42 | A453 | K | 0.05 |
| L469 | P | 0.35 | A453 | P | 0.03 |
| L469 | G | 0.01 | A453 | G | 0.02 |

TABLE 5-3-continued

Performance indices of variants

| site | variant | performance index | site | variant | performance index |
|---|---|---|---|---|---|
| A519 | H | 1.41 | E525 | S | 1.62 |
| A519 | S | 1.27 | E525 | T | 1.25 |
| A519 | G | 1.21 | E525 | R | 1.24 |
| A519 | W | 1.17 | E525 | K | 1.22 |
| A519 | T | 1.12 | E525 | V | 1.17 |
| A519 | K | 0.93 | E525 | H | 1.09 |
| A519 | F | 0.78 | E525 | L | 1.07 |
| A519 | R | 0.61 | E525 | F | 1.05 |
| A519 | C | 0.60 | E525 | W | 1.05 |
| A519 | Q | 0.58 | E525 | Q | 1.05 |
| A519 | E | 0.44 | E525 | G | 1.00 |
| A519 | Y | 0.42 | E525 | M | 0.95 |
| A519 | V | 0.40 | E525 | C | 0.92 |
| A519 | L | 0.39 | E525 | A | 0.91 |
| A519 | D | 0.23 | E525 | P | 0.74 |
| A519 | P | 0.04 | E525 | N | 0.71 |
| | | | E525 | D | 0.68 |

| site | variant | performance index | site | variant | performance index |
|---|---|---|---|---|---|
| H515 | M | 2.00 | R528 | K | 1.00 |
| H515 | Q | 1.05 | R528 | F | 0.58 |
| H515 | N | 0.97 | R528 | H | 0.49 |
| H515 | R | 0.97 | R528 | M | 0.46 |
| H515 | G | 0.93 | R528 | V | 0.45 |
| H515 | H | 0.81 | R528 | L | 0.25 |
| H515 | Y | 0.75 | R528 | Y | 0.23 |
| H515 | I | 0.72 | R528 | T | 0.21 |
| H515 | A | 0.71 | R528 | C | 0.21 |
| H515 | E | 0.64 | R528 | E | 0.20 |
| H515 | F | 0.59 | R528 | S | 0.17 |
| H515 | D | 0.59 | R528 | A | 0.16 |
| H515 | L | 0.58 | R528 | N | 0.15 |
| H515 | V | 0.56 | R528 | G | 0.11 |
| H515 | C | 0.50 | R528 | W | 0.07 |
| H515 | T | 0.50 | R528 | D | 0.05 |
| H515 | W | 0.43 | R528 | P | 0.02 |
| H515 | S | 0.38 | | | |
| H515 | P | 0.03 | | | |

| site | variant | performance index |
|---|---|---|
| T536 | F | 3.60 |
| T536 | Y | 2.62 |
| T536 | V | 2.56 |
| T536 | I | 2.44 |
| T536 | M | 1.62 |
| T536 | H | 1.50 |
| T536 | C | 1.48 |
| T536 | L | 1.43 |
| T536 | K | 1.37 |
| T536 | A | 1.31 |
| T536 | S | 1.29 |
| T536 | G | 1.04 |
| T536 | R | 0.96 |
| T536 | N | 0.55 |
| T536 | E | 0.22 |
| T536 | D | 0.18 |
| T536 | P | 0.05 |

The entire library of T536, variants from all SELs which displayed the highest performance indices, and some control variants which displayed low performance indices were re-assayed for activity as described above. Table 5-4 shows the results from these assays. Results are presented as performance vs. wild-type (unmodified) molecule. Wild-type performance was determined as the average of 51 separate grown cultures. Results were variable between assays but results were in very good agreement with the primary screen results, indicating the assay is reliable. Beneficial sites for variation include but are not limited to flexible loop sites A453, H515, and A443; hydrophobic surface sites L494 and L469 and miscellaneous site T536. The highest performing variants, i.e. those that displayed a performance index greater than 1.5, were A453N, T536C, L494P, T5361, T536F, T536Y, and L494C.

TABLE 5-4

Performance indices of following retest.

| site | variant | performance index |
|---|---|---|
| A453 | N | 2.31 |
| T536 | C | 1.88 |
| L494 | P | 1.82 |
| T536 | I | 1.73 |
| T536 | F | 1.73 |
| T536 | Y | 1.73 |
| L494 | C | 1.56 |
| T536 | A | 1.48 |
| L494 | V | 1.48 |
| T536 | K | 1.46 |
| T536 | L | 1.46 |
| L494 | G | 1.39 |
| T536 | R | 1.36 |
| H515 | M | 1.34 |
| A453 | I | 1.31 |
| T536 | V | 1.27 |
| A443 | S | 1.16 |
| L494 | I | 1.10 |
| T536 | M | 1.09 |
| L469 | A | 1.09 |
| D323 | M | 0.95 |
| T536 | H | 0.94 |
| T536 | G | 0.90 |
| I229 | V | 0.89 |
| I229 | L | 0.89 |
| T536 | S | 0.72 |
| T536 | N | 0.49 |
| T536 | D | 0.17 |
| T536 | E | 0.16 |
| E451 | S | 0.14 |
| R528 | D | 0.11 |
| N438 | E | 0.10 |
| E451 | I | 0.08 |
| T536 | P | 0.08 |
| R528 | P | 0.05 |

Example 6

*P. alba* Isoprene Synthase Combinatorial Analysis, Expression, Crystallization, Activity, and Tm The *P. alba* isoprene synthase (IspS) SEL and enrichment studies identified several independent mutations displaying higher in vitro activity than the wild type (WT) enzyme. The experiments described below were aimed to determine if these mutations were mutually beneficial in combination with one another, and to determine if there were additional beneficial biochemical properties of any of the more active variants.

Methods

Three *P. alba* Isoprene Synthase (IspS) variants which demonstrated high performance index values relative to wild type in the SEL activity assay were chosen for further study. A fourth variant, previously isolated by a selection for randomly mutagenized IspS enzymes that tolerated protracted, high MVA pathway flux, was also included in the combinatorial analysis. These four variants harbored the mutations A453N, G491S (previously referred to as G507S), L494P, and T536C. In all possible combinations, these four mutations generated 16 possible variants of IspS. For ease of reference, the 16 variants to be assayed were annotated as containing the possible combinations of mutations N (A453 N), S (G491S), P (L494P), or C (T536C), or WT (no mutations) in a given IspS molecule.

The 16 variants were based upon the vector backbone MD09-163 (encoding the WT enzyme, see FIG. 60), which harbors a TEV protease site and 6×His tag at the C-terminal end of IspS. Variants were generated using the QuikChange Multi Site-Directed Mutagenesis Kit (Stratagene) according to the manufacturer's recommended protocol (see below for PCR reaction and cycling parameters). Since the mutations encoding G491S and L494P are within six nucleotides of each other, it was necessary to use an oligonucleotide harboring both mutations in addition to the single oligonucleotides for those mutations in the QuikChange Multi reaction in order to generate all 16 possible combinations of mutations. The QuikChange Multi reaction was transformed into chemically competent *E. coli* TOP10 cells (Invitrogen) according to the manufacturer's recommended protocol and plated onto LB Kan50 selective media plates. Colonies resistant to kanamycin were directly screened by PCR and verified by sequencing using the primers QB1493 and T7 Reverse (Quintara Biosciences). In some cases, if a certain variant was not isolated from the QuickChange Multi reaction, a modified version of QuikChange Mutagenesis (Stratagene) was employed to generate a given variant (see below for PCR reaction and cycling parameters). These two techniques yielded all 16 possible combinatorial variants of N, S, P, or C, which were subjected to complete sequencing using the primers T7 Forward, EL-1000, QB1493, A-rev, A-rev2, and T7 Reverse (see Table 6-1). TOP10 cells were grown in selective medium, and plasmids were purified (Qiagen) and then transformed into chemically competent BL21 DE3 pLysS (Invitrogen) according to the manufacturer's recommended protocol, prior to expression of the IspS variants. All variants of IspS were purified and analyzed for specific activity relative to WT (see FIG. 62).

In a separate set of constructs, the T536F mutation (shown to be a thermostable variant of IspS) was also introduced into both the MD09-163 and pDW101 backbones. This mutation was introduced by the QuikChange mutagenesis methodology described above (see below for PCR reaction and cycling parameters), and similarly transformed into BL21 DE3 pLysS (Invitrogen) for expression. These variants were assayed for their effect on IspS expression and melting point relative to WT.

QuikChange Multi Site-Directed Mutagenesis
9 μl $H_2O$
2.5 μl 10× QuikChange Multi reaction buffer
0.5 μl QuikSolution
1 μl DNA template (100 ng MD09-163)
2 μl each primer (200 ng each of N, S, P, C, SP)
1 μl dNTP mix
1 μl QuikChange Multi enzyme blend QuikChange Multi Site-Directed Mutagenesis—Cycling Parameters
1) 95° C.—4 min
2) 95° C.—1 min
3) 53° C.—1 min
4) 65° C.—14 min
5) goto Step 2—30×

6) 4° C.—for holding

QuikChange Mutagenesis (modified)

35 μl $H_2O$

5 μl 10×Pfu Ultra II rxn Buffer

6 μl 2.5 mM dNTPs (Roche)

1 μl 20 μM Primer 1 (e.g. G507S QC 2 For or alba T536F For)

1 μl 20 μM Primer 2 (e.g. G507S QC 2 Rev or alba T536F Rev)

1 μl Pfu Ultra II HS Polymerase (Stratagene)

1 μl DNA template (e.g. 100 ng MD09-163 or pDW101)

QuikChange Mutagenesis—Cycling Parameters 1) 95° C.—4 min
2) 95° C.—20 sec
3) 52° C.—20 sec
4) 68° C.—7 min
5) goto Step 2—5×
6) 95° C.—20 sec
7) 55° C.—20 sec
8) 68° C.—7 min
9) goto Step 2—20×
10) 68° C.—10 min
11) 4° C.—for holding

TABLE 6-1

| Primers | |
|---|---|
| alba A453N For (N) | gcgcgtggtgaaaccaacaatagcgtttcttgttac (SEQ ID NO: 54) |
| QC G507S For (S) | agatgaacaaggaaaaactgagtggtagcctgttcgcgaaa (SEQ ID NO: 55) |
| alba L494P For (P) | gaaaaactgggtggtagcccgttcgcgaaaccgttcg (SEQ ID NO: 56) |
| alba T536C For (C) | gttctgtctgtaatctgcgaaccgattctgccgtttg (SEQ ID NO: 57) |
| alba G491S L494P For (SP) | gaacaaggaaaaactgagtggtagcccgttcgcgaaaccgttcg (SEQ ID NO: 58) |
| G507S QC 2 For | gaaaaactgagtggtagcctgttcgcgaaac (SEQ ID NO: 59) |
| G507S QC 2 Rev | aggctaccactcagtttttccttgttcatct (SEQ ID NO: 60) |
| alba T536F For | gttctgtctgtaatctttgaaccgattctgccgtttg (SEQ ID NO: 61) |
| alba T536F Rev | cggttcaaagattacagacagaacgcgtt (SEQ ID NO: 62) |
| T7 Forward | taatacgactcactataggg (SEQ ID NO: 48) |
| T7 Reverse | gctagttattgctcagcgg (SEQ ID NO: 49) |
| EL-1000 | gcactgtctttccgtctgctgc (SEQ ID NO: 50) |
| A-rev | ctcgtacaggctcaggatag (SEQ ID NO: 52) |
| A-rev-2 | ttacgtcccaacgctcaact (SEQ ID NO: 53) |
| QB1493 | cttcggcaacgcatggaaat (SEQ ID NO: 51) |

TABLE 6-2

| Plasmids: | |
|---|---|
| MD09-163 | pET24a-*P. alba* TRC (MEA WT) C-Term (+) TEV, His tag |
| pDW87 | pET24a-*P. alba* TRC (MEA T536F) C-Term (+) TEV, His tag |
| pDW95 | pET24a-*P. alba* TRC (MEA L494P T536F) C-Term (+) TEV, His tag |
| pDW99 | pET24a-*P. alba* TRC (MEA A453N) C-Term (+) TEV, His tag |
| pDW100 | pET24a-*P. alba* TRC (MEA G491S) C-Term (+) TEV, His tag |
| pDW101 | pET24a-*P. alba* TRC (MEA L494P) C-Term (+) TEV, His tag |
| pDW102 | pET24a-*P. alba* TRC (MEA T536C) C-Term (+) TEV, His tag |
| pDW103 | pET24a-*P. alba* TRC (MEA A453N G491S) C-Term (+) TEV, His tag |
| pDW104 | pET24a-*P. alba* TRC (MEA A453N L494P) C-Term (+) TEV, His tag |
| pDW105 | pET24a-*P. alba* TRC (MEA A453N T536C) C-Term (+) TEV, His tag |
| pDW106 | pET24a-*P. alba* TRC (MEA A453N G491S L494P) C-Term (+) TEV, His tag |
| pDW107 | pET24a-*P. alba* TRC (MEA A453N G491S T536C) C-Term (+) TEV, His tag |
| pDW108 | pET24a-*P. alba* TRC (MEA A453N L494P T536C) C-Term (+) TEV, His tag |
| pDW109 | pET24a-*P. alba* TRC (MEA A453N G491S L494P T536C) C-Term (+) TEV, His tag |
| pDW110 | pET24a-*P. alba* TRC (MEA G491S L494P) C-Term (+) TEV, His tag |
| pDW111 | pET24a-*P. alba* TRC (MEA G491S T536C) C-Term (+) TEV, His tag |
| pDW112 | pET24a-*P. alba* TRC (MEA G491S L494P T536C) C-Term (+) TEV, His tag |
| pDW113 | pET24a-*P. alba* TRC (MEA L494P T536C) C-Term (+) TEV, His tag |

TABLE 6-3

| Strains: | |
|---|---|
| MD09-167 | BL21(DE3) pLysS, MD09-163 (WT) |
| DW363 | BL21(DE3) pLysS, pDW87 |
| DW381 | BL21(DE3) pLysS, pDW95 |
| DW397 | BL21(DE3) pLysS, pDW99 (N) |
| DW398 | BL21(DE3) pLysS, pDW100 (S) |
| DW399 | BL21(DE3) pLysS, pDW101 (P) |
| DW400 | BL21(DE3) pLysS, pDW102 (C) |
| DW401 | BL21(DE3) pLysS, pDW103 (NS) |
| DW402 | BL21(DE3) pLysS, pDW104 (NP) |
| DW403 | BL21(DE3) pLysS, pDW105 (NC) |
| DW404 | BL21(DE3) pLysS, pDW106 (NSP) |
| DW405 | BL21(DE3) pLysS, pDW107 (NSC) |
| DW406 | BL21(DE3) pLysS, pDW108 (NPC) |
| DW407 | BL21(DE3) pLysS, pDW109 (NSPC) |
| DW408 | BL21(DE3) pLysS, pDW110 (SP) |
| DW409 | BL21(DE3) pLysS, pDW111 (SC) |
| DW410 | BL21(DE3) pLysS, pDW112 (SPC) |
| DW411 | BL21(DE3) pLysS, pDW1113 (PC) |

1) Amino Acid Sequence of P. alba MEA(+)TEV - MD09-163 (WT) (SEQ ID NO: 63)

MEARRSANYEPNSWDYDYLLSSDTDESIEVYKDKAKKLEAEVRREINN

EKAEFLTLLELIDNVQRLGLGYRFESDIRGALDRFVSSGGFDAVTKTS

LHGTALSFRLLRQHGFEVSQEAFSGFKDQNGNFLENLKEDIKAILSLY

EASFLALEGENILDEAKVFAISHLKELSEEKIGKELAEQVNHALELPL

HRRTQRLEAVWSIEAYRKKEDANQVLLELAILDYNMIQSVYQRDLRET

SRWWRRVGLATKLHFARDRLIESFYWAVGVAFEPQYSDCRNSVAKMFS

FVTIIDDIYDVYGTLDELELFTDAVERWDVNAINDLPDYMKLCFLALY

NTINEIAYDNLKDKGENILPYLTKAWADLCNAFLQEAKWLYNKSTPTF

DDYFGNAWKSSSGPLQLVFAYFAVVQNIKKEEIENLQKYHDTISRPSH

IFRLCNDLASASAEIARGETANSVSCYMRTKGISEELATESVMNLIDE

TWKKMNKEKLGGSLFAKPFVETAINLARQSHCTYHNGDAHTSPDELTR

KRVLSVITEPILPFERENLYFQGLEHHHHHH

DNA sequence of MD09-163 (SEQ ID NO: 64)

tggcgaatgggacgcgccctgtagcggcgcattaagcgcggcgggtgt ggtggttacgcgcagcgtgaccgctacacttgccagcgccctagcgcc cgctcctttcgctttcttcccttcctttctcgccacgttcgccggctt tccccgtcaagctctaaatcgggggctccctttagggttccgatttag tgctttacggcacctcgaccccaaaaaacttgattagggtgatggttc acgtagtgggccatcgccctgatagacggtttttcgccctttgacgtt ggagtccacgttctttaatagtggactcttgttccaaactggaacaac actcaaccctatctcggtctattcttttgatttataagggattttgcc gatttcggcctattggttaaaaaatgagctgatttaacaaaaatttaa cgcgaattttaacaaaatattaacgtttacaatttcaggtggcacttt tcggggaaatgtgcgcggaacccctatttgtttatttttctaaataca ttcaaatatgtatccgctcatgaattaattcttagaaaaactcatcga gcatcaaatgaaactgcaatttattcatatcaggattatcaataccat -continued atttttgaaaaagccgtttctgtaatgaaggagaaaactcaccgaggc agttccataggatggcaagatcctggtatcggtctgcgattccgactc gtccaacatcaatacaacctattaatttcccctcgtcaaaaataaggt tatcaagtgagaaatcaccatgagtgacgactgaatccggtgagaatg gcaaaagtttatgcatttctttccagacttgttcaacaggccagccat tacgctcgtcatcaaaatcactcgcatcaaccaaaccgttattcattc gtgattgcgcctgagcgagacgaaatacgcgatcgctgttaaaaggac aattacaaacaggaatcgaatgcaaccggcgcaggaacactgccagcg catcaacaatattttcacctgaatcaggatattcttctaatacctgga atgctgttttcccggggatcgcagtggtgagtaaccatgcatcatcag gagtacggataaaatgcttgatggtcggaagaggcataaattccgtca gccagtttagtctgaccatctcatctgtaacatcattggcaacgctac ctttgccatgtttcagaaacaactctggcgcatcgggcttcccataca atcgatagattgtcgcacctgattgcccgacattatcgcgagcccatt tatacccatataaatcagcatccatgttggaatttaatcgcggcctag agcaagacgtttcccgttgaatatggctcataacaccccttgtattac tgtttatgtaagcagacagttttattgttcatgaccaaaatcccttaa cgtgagttttcgttccactgagcgtcagaccccgtagaaaagatcaaa ggatcttcttgagatcctttttttctgcgcgtaatctgctgcttgcaa acaaaaaaaccaccgctaccagcggtggtttgtttgccggatcaagag ctaccaactctttttccgaaggtaactggcttcagcagagcgcagata ccaaatactgtccttctagtgtagccgtagttaggccaccacttcaag aactctgtagcaccgcctacatacctcgctctgctaatcctgttacca gtggctgctgccagtggcgataagtcgtgtcttaccgggttggactca agacgatagttaccggataaggcgcagcggtcgggctgaacggggggt tcgtgcacacagcccagcttggagcgaacgacctacaccgaactgaga tacctacagcgtgagctatgagaaagcgccacgcttcccgaagggaga aaggcggacaggtatccggtaagcggcagggtcggaacaggagagcgc acgagggagcttccagggggaaacgcctggtatctttatagtcctgtc gggtttcgccacctctgacttgagcgtcgatttttgtgatgctcgtca ggggggcggagcctatggaaaaacgccagcaacgcggcctttttacgg ttcctggccttttgctggccttttgctcacatgttctttcctgcgtta tcccctgattctgtggataaccgtattaccgcctttgagtgagctgat accgctcgccgcagccgaacgaccgagcgcagcgagtcagtgagcgag gaagcggaagagcgcctgatgcggtattttctccttacgcatctgtgc ggtatttcacaccgcatatatggtgcactctcagtacaatctgctctg atgccgcatagttaagccagtatacactccgctatcgctacgtgactg ggtcatggctgcgccccgacacccgccaacacccgctgacgcgccctg acgggcttgtctgctcccggcatccgcttacagacaagctgtgaccgt ctccgggagctgcatgtgtcagaggttttcaccgtcatcaccgaaacg cgcgaggcagctgcggtaaagctcatcagcgtggtcgtgaagcgattc -continued acagatgtctgcctgttcatccgcgtccagctcgttgagtttctccag aagcgttaatgtctggcttctgataaagcgggccatgttaagggcggt tttttcctgtttggtcactgatgcctccgtgtaagggggatttctgtt catgggggtaatgataccgatgaaacgagagaggatgctcacgatacg ggttactgatgatgaacatgcccggttactggaacgttgtgagggtaa acaactggcggtatggatgcggcgggaccagagaaaaatcactcaggg tcaatgccagcgcttcgttaatacagatgtaggtgttccacagggtag ccagcagcatcctgcgatgcagatccggaacataatggtgcagggcgc tgacttccgcgtttccagactttacgaaacacggaaaccgaagaccat tcatgttgttgctcaggtcgcagacgttttgcagcagcagtcgcttca cgttcgctcgcgtatcggtgattcattctgctaaccagtaaggcaacc ccgccagcctagccgggtcctcaacgacaggagcacgatcatgcgcac ccgtggggccgccatgccggcgataatggcctgcttctcgccgaaacg tttggtggcgggaccagtgacgaaggcttgagcgagggcgtgcaagat tccgaataccgcaagcgacaggccgatcatcgtcgcgctccagcgaaa gcggtcctcgccgaaaatgacccagagcgctgccggcacctgtcctac gagttgcatgataaagaagacagtcataagtgcggcgacgatagtcat gccccgcgcccaccggaaggagctgactgggttgaaggctctcaaggg catcggtcgagatcccggtgcctaatgagtgagctaacttacattaat tgcgttgcgctcactgcccgctttccagtcgggaaacctgtcgtgcca gctgcattaatgaatcggccaacgcgcggggagaggcggtttgcgtat tgggcgccagggtggtttttcttttcaccagtgagacgggcaacagct gattgcccttcaccgcctggccctgagagagttgcagcaagcggtcca cgctggtttgccccagcaggcgaaaatcctgtttgatggtggttaacg gcgggatataacatgagctgtcttcggtatcgtcgtatcccactaccg agatatccgcaccaacgcgcagcccggactcggtaatggcgcgcattg cgcccagcgccatctgatcgttggcaaccagcatcgcagtgggaacga tgccctcattcagcatttgcatggtttgttgaaaaccggacatggcac tccagtcgccttcccgttccgctatcggctgaatttgattgcgagtga gatatttatgccagccagccagacgcagacgcgccgagacagaactta atgggcccgctaacagcgcgatttgctggtgacccaatgcgaccagat gctccacgcccagtcgcgtaccgtcttcatgggagaaaataatactgt tgatgggtgtctggtcagagacatcaagaaataacgccggaacattag tgcaggcagcttccacagcaatggcatcctggtcatccagcggatagt taatgatcagcccactgacgcgttgcgcgagaagattgtgcaccgccg ctttacaggcttcgacgccgcttcgttctaccatcgacaccaccacgc tggcacccagttgatcggcgcgagatttaatcgccgcgacaatttgcg acggcgcgtgcagggccagactggaggtggcaacgccaatcagcaacg actgtttgcccgccagttgttgtgccacgcggttgggaatgtaattca gctccgccatcgccgcttccacttttcccgcgttttcgcagaaacgt -continued ggctggcctggttcaccacgcgggaaacggtctgataagagacaccgg catactctgcgacatcgtataacgttactggtttcacattcaccaccc tgaattgactctcttccgggcgctatcatgccataccgcgaaaggttt tgcgccattcgatggtgtccgggatctcgacgctctcccttatgcgac tcctgcattaggaagcagcccagtagtaggttgaggccgttgagcacc gccgccgcaaggaatggtgcatgcaaggagatggcgcccaacagtccc ccggccacggggcctgccaccatacccacgccgaaacaagcgctcatg agcccgaagtggcgagcccgatcttccccatcggtgatgtcggcgata taggcgccagcaaccgcacctgtggcgccggtgatgccggccacgatg cgtccggcgtagaggatcgagatctcgatcccgcgaaattaatacgac tcactataggggaattgtgagcggataacaattcccctctagaaataa ttttgtttaactttaagaaggagatatacatatggaagctcgtcgttc tgcgaactacgaacctaacagctgggactatgattacctgctgtcctc cgacacggacgagtccatcgaagtatacaaagacaaagcgaaaaagct ggaagccgaagttcgtcgcgagattaataacgaaaaagcagaatttct gaccctgctggaactgattgacaacgtccagcgcctgggcctgggtta ccgtttcgagtctgatatccgtggtgcgctggatcgcttcgtttcctc cggcggcttcgatgcggtaaccaagacttccctgcacggtacggcact gtctttccgtctgctgcgtcaacacggttttgaggtttctcaggaagc gttcagcggcttcaaagaccaaaacggcaacttcctggagaacctgaa ggaagatatcaaagctatcctgagcctgtacgaggccagcttcctggc tctggaaggcgaaaacatcctggacgaggcgaaggttttcgcaatctc tcatctgaaagaactgtctgaagaaaagatcggtaaagagctggcaga acaggtgaaccatgcactggaactgccactgcatcgccgtactcagcg tctggaagcagtatggtctatcgaggcctaccgtaaaaaggaggacgc gaatcaggttctgctggagctggcaattctggattacaacatgatcca gtctgtataccagcgtgatctgcgtgaaacgtcccgttggtggcgtcg tgtgggtctggcgaccaaactgcactttgctcgtgaccgcctgattga gagcttctactgggccgtgggtgtagcattcgaaccgcaatactccga ctgccgtaactccgtcgcaaaaatgttttctttcgtaaccattatcga cgatatctacgatgtatacggcaccctggacgaactggagctgtttac tgatgcagttgagcgttgggacgtaaacgccatcaacgacctgccgga ttacatgaaactgtgctttctggctctgtataacactattaacgaaat cgcctacgacaacctgaaagataaaggtgagaacatcctgccgtatct gaccaaagcctgggctgacctgtgcaacgctttcctgcaagaagccaa gtggctgtacaacaaatctactccgacctttgacgactacttcggcaa cgcatggaaatcctcttctggcccgctgcaactggtgttcgcttactt cgctgtcgtgcagaacattaaaaaggaagagatcgaaaacctgcaaaa ataccatgacaccatctctcgtccttcccatatcttccgtctgtgcaa tgacctggctagcgcgtctgcggaaattgcgcgtggtgaaaccgcaaa tagcgtttcttgttacatgcgcactaaaggtatctccgaagaactggc -continued taccgaaagcgtgatgaatctgatcgatgaaacctggaaaaagatgaa caaggaaaaactgggtggtagcctgttcgcgaaaccgttcgtggaaac cgcgatcaacctggcacgtcaatctcactgcacttatcataacggcga cgcgcatacctctccggatgagctgacccgcaaacgcgttctgtctgt aatcactgaaccgattctgccgtttgaacgcgaaaacctgtattttca gggcctcgagcaccaccaccaccaccactgagatccggctgctaacaa agcccgaaaggaagctgagttggctgctgccaccgctgagcaataact agcataaccccttggggcctctaaacgggtcttgaggggttttttgct gaaaggaggaactatatccggat 2) Amino Acid Sequence of P. alba MEA A453N (+) TEV - pDW99 (N) (SEQ ID NO: 65)

MEARRSANYEPNSWDYDYLLSSDTDESIEVYKDKAKKLEAEVRREINN

EKAEFLTLLELIDNVQRLGLGYRFESDIRGALDRFVSSGGFDAVTKTS

LHGTALSFRLLRQHGFEVSQEAFSGFKDQNGNFLENLKEDIKAILSLY

EASFLALEGENILDEAKVFAISHLKELSEEKIGKELAEQVNHALELPL

HRRTQRLEAVWSIEAYRKKEDANQVLLELAILDYNMIQSVYQRDLRET

SRWWRRVGLATKLHFARDRLIESFYWAVGVAFEPQYSDCRNSVAKMFS

FVTIIDDIYDVYGTLDELELFTDAVERWDVNAINDLPDYMKLCFLALY

NTINEIAYDNLKDKGENILPYLTKAWADLCNAFLQEAKWLYNKSTPTF

DDYFGNAWKSSSGPLQLVFAYFAVVQNIKKEEIENLQKYHDTISRPSH

IFRLCNDLASASAEIARGETNNSVSCYMRTKGISEELATESVMNLIDE

TWKKMNKEKLGGSLFAKPFVETAINLARQSHCTYHNGDAHTSPDELTR

KRVLSITEPILPFERENLYFQGLEHHHHHH

DNA sequence of pDW99 (SEQ ID NO: 66)

tggcgaatgggacgcgccctgtagcggcgcattaagcgcggcgggtgt ggtggttacgcgcagcgtgaccgctacacttgccagcgccctagcgcc cgctcctttcgctttcttcccttcctttctcgccacgttcgccggctt tccccgtcaagctctaaatcgggggctccctttagggttccgatttag tgctttacggcacctcgaccccaaaaaacttgattagggtgatggttc acgtagtgggccatcgccctgatagacggtttttcgccctttgacgtt ggagtccacgttctttaatagtggactcttgttccaaactggaacaac actcaaccctatctcggtctattcttttgatttataagggattttgcc gatttcggcctattggttaaaaaatgagctgatttaacaaaaatttaa cgcgaattttaacaaaatattaacgtttacaatttcaggtggcacttt tcggggaaatgtgcgcggaacccctatttgtttatttttctaaataca ttcaaatatgtatccgctcatgaattaattcttagaaaaactcatcga gcatcaaatgaaactgcaatttattcatatcaggattatcaataccat atttttgaaaaagccgtttctgtaatgaaggagaaaactcaccgaggc agttccataggatggcaagatcctggtatcggtctgcgattccgactc -continued gtccaacatcaatacaacctattaatttcccctcgtcaaaaataaggt tatcaagtgagaaatcaccatgagtgacgactgaatccggtgagaatg gcaaaagtttatgcatttctttccagacttgttcaacaggccagccat tacgctcgtcatcaaaatcactcgcatcaaccaaaccgttattcattc gtgattgcgcctgagcgagacgaaatacgcgatcgctgttaaaaggac aattacaaacaggaatcgaatgcaaccggcgcaggaacactgccagcg catcaacaatattttcacctgaatcaggatattcttctaatacctgga atgctgttttcccggggatcgcagtggtgagtaaccatgcatcatcag gagtacggataaaatgcttgatggtcggaagaggcataaattccgtca gccagtttagtctgaccatctcatctgtaacatcattggcaacgctac ctttgccatgtttcagaaacaactctggcgcatcgggcttcccataca atcgatagattgtcgcacctgattgcccgacattatcgcgagcccatt tatacccatataaatcagcatccatgttggaatttaatcgcggcctag agcaagacgtttcccgttgaatatggctcataacaccccttgtattac tgtttatgtaagcagacagttttattgttcatgaccaaaatcccttaa cgtgagttttcgttccactgagcgtcagaccccgtagaaaagatcaaa ggatcttcttgagatcctttttttctgcgcgtaatctgctgcttgcaa acaaaaaaaccaccgctaccagcggtggtttgtttgccggatcaagag ctaccaactctttttccgaaggtaactggcttcagcagagcgcagata ccaaatactgtccttctagtgtagccgtagttaggccaccacttcaag aactctgtagcaccgcctacatacctcgctctgctaatcctgttacca gtggctgctgccagtggcgataagtcgtgtcttaccgggttggactca agacgatagttaccggataaggcgcagcggtcgggctgaacggggggt tcgtgcacacagcccagcttggagcgaacgacctacaccgaactgaga tacctacagcgtgagctatgagaaagcgccacgcttcccgaagggaga aaggcggacaggtatccggtaagcggcagggtcggaacaggagagcgc acgagggagcttccagggggaaacgcctggtatctttatagtcctgtc gggtttcgccacctctgacttgagcgtcgatttttgtgatgctcgtca ggggggcggagcctatggaaaaacgccagcaacgcggcctttttacgg ttcctggccttttgctggccttttgctcacatgttctttcctgcgtta tcccctgattctgtggataaccgtattaccgcctttgagtgagctgat accgctcgccgcagccgaacgaccgagcgcagcgagtcagtgagcgag gaagcggaagagcgcctgatgcggtattttctccttacgcatctgtgc ggtatttcacaccgcatatatggtgcactctcagtacaatctgctctg atgccgcatagttaagccagtatacactccgctatcgctacgtgactg ggtcatggctgcgccccgacacccgccaacacccgctgacgcgccctg acgggcttgtctgctcccggcatccgcttacagacaagctgtgaccgt ctccgggagctgcatgtgtcagaggttttcaccgtcatcaccgaaacg cgcgaggcagctgcggtaaagctcatcagcgtggtcgtgaagcgattc acagatgtctgcctgttcatccgcgtccagctcgttgagtttctccag aagcgttaatgtctggcttctgataaagcgggccatgttaagggcggt -continued tttttcctgtttggtcactgatgcctccgtgtaaggggggatttctgtt
catgggggtaatgataccgatgaaacgagagaggatgctcacgatacg
ggttactgatgatgaacatgcccggttactggaacgttgtgagggtaa
acaactggcggtatggatgcggcgggaccagagaaaaatcactcaggg
tcaatgccagcgcttcgttaatacagatgtaggtgttccacagggtag
ccagcagcatcctgcgatgcagatccggaacataatggtgcagggcgc
tgacttccgcgtttccagactttacgaaacacggaaaccgaagaccat
tcatgttgttgctcaggtcgcagacgttttgcagcagcagtcgcttca
cgttcgctcgcgtatcggtgattcattctgctaaccagtaaggcaacc
ccgccagcctagccgggtcctcaacgacaggagcacgatcatgcgcac
ccgtggggccgccatgccggcgataatggcctgcttctcgccgaaacg
tttggtggcgggaccagtgacgaaggcttgagcgagggcgtgcaagat
tccgaataccgcaagcgacaggccgatcatcgtcgcgctccagcgaaa
gcggtcctcgccgaaaatgacccagagcgctgccggcacctgtcctac
gagttgcatgataaagaagacagtcataagtgcggcgacgatagtcat
gccccgcgcccaccggaaggagctgactgggttgaaggctctcaaggg
catcggtcgagatcccggtgcctaatgagtgagctaacttacattaat
tgcgttgcgctcactgcccgctttccagtcgggaaacctgtcgtgcca
gctgcattaatgaatcggccaacgcgcggggagaggcggtttgcgtat
tgggcgccagggtggtttttcttttcaccagtgagacgggcaacagct
gattgcccttcaccgcctggccctgagagagttgcagcaagcggtcca
cgctggtttgccccagcaggcgaaaatcctgtttgatggtggttaacg
gcgggatataacatgagctgtcttcggtatcgtcgtatcccactaccg
agatatccgcaccaacgcgcagcccggactcggtaatggcgcgcattg
cgcccagcgccatctgatcgttggcaaccagcatcgcagtgggaacga
tgccctcattcagcatttgcatggtttgttgaaaaccggacatggcac
tccagtcgccttcccgttccgctatcggctgaatttgattgcgagtga
gatatttatgccagccagccagacgcagacgcgccgagacagaactta
atgggcccgctaacagcgcgatttgctggtgacccaatgcgaccagat
gctccacgcccagtcgcgtaccgtcttcatgggagaaaataatactgt
tgatgggtgtctggtcagagacatcaagaaataacgccggaacattag
tgcaggcagcttccacagcaatggcatcctggtcatccagcggatagt
taatgatcagcccactgacgcgttgcgcgagaagattgtgcaccgccg
ctttacaggcttcgacgccgcttcgttctaccatcgacaccaccacgc
tggcacccagttgatcggcgcgagatttaatcgccgcgacaatttgcg
acggcgcgtgcagggccagactggaggtggcaacgccaatcagcaacg
actgtttgcccgccagttgttgtgccacgcggttgggaatgtaattca
gctccgccatcgccgcttccactttttcccgcgttttcgcagaaacgt
ggctggcctggttcaccacgcgggaaacggtctgataagagacaccgg
catactctgcgacatcgtataacgttactggtttcacattcaccaccc
tgaattgactctcttccgggcgctatcatgccataccgcgaaaggttt
tgcgccattcgatggtgtccgggatctcgacgctctcccttatgcgac
tcctgcattaggaagcagcccagtagtaggttgaggccgttgagcacc
gccgccgcaaggaatggtgcatgcaaggagatggcgcccaacagtccc
ccggccacggggcctgccaccatacccacgccgaaacaagcgctcatg
agcccgaagtggcgagcccgatcttccccatcggtgatgtcggcgata
taggcgccagcaaccgcacctgtggcgccggtgatgccggccacgatg
cgtccggcgtagaggatcgagatctcgatcccgcgaaattaatacgac
tcactataggggaattgtgagcggataacaattcccctctagaaataa
ttttgtttaactttaagaaggagatatacatatggaagctcgtcgttc
tgcgaactacgaacctaacagctgggactatgattacctgctgtcctc
cgacacggacgagtccatcgaagtatacaaagacaaagcgaaaaagct
ggaagccgaagttcgtcgcgagattaataacgaaaaagcagaatttct
gaccctgctggaactgattgacaacgtccagcgcctgggcctgggtta
ccgtttcgagtctgatatccgtggtgcgctggatcgcttcgtttcctc
cggcggcttcgatgcggtaaccaagacttccctgcacggtacggcact
gtctttccgtctgctgcgtcaacacggttttgaggtttctcaggaagc
gttcagcggcttcaaagaccaaaacggcaacttcctggagaacctgaa
ggaagatatcaaagctatcctgagcctgtacgaggccagcttcctggc
tctggaaggcgaaaacatcctggacgaggcgaaggttttcgcaatctc
tcatctgaaagaactgtctgaagaaaagatcggtaaagagctggcaga
acaggtgaaccatgcactggaactgccactgcatcgccgtactcagcg
tctggaagcagtatggtctatcgaggcctaccgtaaaaaggaggacgc
gaatcaggttctgctggagctggcaattctggattacaacatgatcca
gtctgtataccagcgtgatctgcgtgaaacgtcccgttggtggcgtcg
tgtgggtctggcgaccaaactgcactttgctcgtgaccgcctgattga
gagcttctactgggccgtgggtgtagcattcgaaccgcaatactccga
ctgccgtaactccgtcgcaaaaatgttttctttcgtaaccattatcga
cgatatctacgatgtatacggcaccctggacgaactggagctgtttac
tgatgcagttgagcgttgggacgtaaacgccatcaacgacctgccgga
ttacatgaaactgtgctttctggctctgtataacactattaacgaaat
cgcctacgacaacctgaaagataaaggtgagaacatcctgccgtatct
gaccaaagcctgggctgacctgtgcaacgctttcctgcaagaagccaa
gtggctgtacaacaaatctactccgacctttgacgactacttcggcaa
cgcatggaaatcctcttctggcccgctgcaactggtgttcgcttactt
cgctgtcgtgcagaacattaaaaaggaagagatcgaaaacctgcaaaa
ataccatgacaccatctctcgtccttcccatatcttccgtctgtgcaa
tgacctggctagcgcgtctgcggaaattgcgcgtggtgaaaccAACaa
tagcgtttcttgttacatgcgcactaaaggtatctccgaagaactggc
taccgaaagcgtgatgaatctgatcgatgaaacctggaaaaagatgaa
caaggaaaaactgggtggtagcctgttcgcgaaaccgttcgtggaaac -continued cgcgatcaacctggcacgtcaatctcactgcacttatcataacggcga cgcgcatacctctccggatgagctgacccgcaaacgcgttctgtctgt aatcactgaaccgattctgccgtttgaacgcgaaaacctgtattttca gggcctcgagcaccaccaccaccaccactgagatccggctgctaacaa agcccgaaaggaagctgagttggctgctgccaccgctgagcaataact agcataaccccttggggcctctaaacgggtcttgaggggttttttgct gaaaggaggaactatatccggat 3) Amino Acid Sequence of P. alba MEA G491S (+) TEV - pDW100 (S) (SEQ ID NO: 67)

MEARRSANYEPNSWDYDYLLSSDTDESIEVYKDKAKKLEAEVRREINN

EKAEFLTLLELIDNVQRLGLGYRFESDIRGALDRFVSSGGFDAVTKTS

LHGTALSFRLLRQHGFEVSQEAFSGFKDQNGNFLENLKEDIKAILSLY

EASFLALEGENILDEAKVFAISHLKELSEEKIGKELAEQVNHALELPL

HRRTQRLEAVWSIEAYRKKEDANQVLLELAILDYNMIQSVYQRDLRET

SRWWRRVGLATKLHFARDRLIESFYWAVGVAFEPQYSDCRNSVAKMFS

FVTIIDDIYDVYGTLDELELFTDAVERWDVNAINDLPDYMKLCFLALY

NTINEIAYDNLKDKGENILPYLTKAWADLCNAFLQEAKWLYNKSTPTF

DDYFGNAWKSSSGPLQLVFAYFAVVQNIKKEEIENLQKYHDTISRPSH

IFRLCNDLASASAEIARGETANSVSCYMRTKGISEELATESVMNLIDE

TWKKMNKEKLSGSLFAKPFVETAINLARQSHCTYHNGDAHTSPDELTR

KRVLSVITEPILPFERENLYFQGLEHHHHHH

DNA sequence of pDW100 (SEQ ID NO: 68)

tggcgaatgggacgcgccctgtagcggcgcattaagcgcggcgggtgt ggtggttacgcgcagcgtgaccgctacacttgccagcgccctagcgcc cgctcctttcgctttcttcccttcctttctcgccacgttcgccggctt tccccgtcaagctctaaatcgggggctccctttagggttccgatttag tgctttacggcacctcgaccccaaaaaacttgattagggtgatggttc acgtagtgggccatcgccctgatagacggtttttcgccctttgacgtt ggagtccacgttctttaatagtggactcttgttccaaactggaacaac actcaaccctatctcggtctattcttttgatttataagggattttgcc gatttcggcctattggttaaaaaatgagctgatttaacaaaaatttaa cgcgaattttaacaaaatattaacgtttacaatttcaggtggcacttt tcggggaaatgtgcgcggaacccctatttgtttatttttctaaataca ttcaaatatgtatccgctcatgaattaattcttagaaaaactcatcga gcatcaaatgaaactgcaatttattcatatcaggattatcaataccat atttttgaaaaagccgtttctgtaatgaaggagaaaactcaccgaggc agttccataggatggcaagatcctggtatcggtctgcgattccgactc gtccaacatcaatacaacctattaatttcccctcgtcaaaaataaggt tatcaagtgagaaatcaccatgagtgacgactgaatccggtgagaatg -continued gcaaaagtttatgcatttctttccagacttgttcaacaggccagccat tacgctcgtcatcaaaatcactcgcatcaaccaaaccgttattcattc gtgattgcgcctgagcgagacgaaatacgcgatcgctgttaaaaggac aattacaaacaggaatcgaatgcaaccggcgcaggaacactgccagcg catcaacaatattttcacctgaatcaggatattcttctaatacctgga atgctgttttcccggggatcgcagtggtgagtaaccatgcatcatcag gagtacggataaaatgcttgatggtcggaagaggcataaattccgtca gccagtttagtctgaccatctcatctgtaacatcattggcaacgctac ctttgccatgtttcagaaacaactctggcgcatcgggcttcccataca atcgatagattgtcgcacctgattgcccgacattatcgcgagcccatt tatacccatataaatcagcatccatgttggaatttaatcgcggcctag agcaagacgtttcccgttgaatatggctcataacaccccttgtattac tgtttatgtaagcagacagttttattgttcatgaccaaaatcccttaa cgtgagttttcgttccactgagcgtcagaccccgtagaaaagatcaaa ggatcttcttgagatcctttttttctgcgcgtaatctgctgcttgcaa acaaaaaaaccaccgctaccagcggtggtttgtttgccggatcaagag ctaccaactctttttccgaaggtaactggcttcagcagagcgcagata ccaaatactgtccttctagtgtagccgtagttaggccaccacttcaag aactctgtagcaccgcctacatacctcgctctgctaatcctgttacca gtggctgctgccagtggcgataagtcgtgtcttaccgggttggactca agacgatagttaccggataaggcgcagcggtcgggctgaacggggggt tcgtgcacacagcccagcttggagcgaacgacctacaccgaactgaga tacctacagcgtgagctatgagaaagcgccacgcttcccgaagggaga aaggcggacaggtatccggtaagcggcagggtcggaacaggagagcgc acgagggagcttccagggggaaacgcctggtatctttatagtcctgtc gggtttcgccacctctgacttgagcgtcgatttttgtgatgctcgtca ggggggcggagcctatggaaaaacgccagcaacgcggcctttttacgg ttcctggccttttgctggccttttgctcacatgttctttcctgcgtta tcccctgattctgtggataaccgtattaccgcctttgagtgagctgat accgctcgccgcagccgaacgaccgagcgcagcgagtcagtgagcgag gaagcggaagagcgcctgatgcggtattttctccttacgcatctgtgc ggtatttcacaccgcatatatggtgcactctcagtacaatctgctctg atgccgcatagttaagccagtatacactccgctatcgctacgtgactg ggtcatggctgcgccccgacacccgccaacacccgctgacgcgccctg acgggcttgtctgctcccggcatccgcttacagacaagctgtgaccgt ctccgggagctgcatgtgtcagaggttttcaccgtcatcaccgaaacg cgcgaggcagctgcggtaaagctcatcagcgtggtcgtgaagcgattc acagatgtctgcctgttcatccgcgtccagctcgttgagtttctccag aagcgttaatgtctggcttctgataaagcgggccatgttaagggcggt tttttcctgtttggtcactgatgcctccgtgtaagggggatttctgtt catgggggtaatgataccgatgaaacgagagaggatgctcacgatacg -continued ggttactgatgatgaacatgcccggttactggaacgttgtgagggtaa
acaactggcggtatggatgcggcgggaccagagaaaaatcactcaggg
tcaatgccagcgcttcgttaatacagatgtaggtgttccacagggtag
ccagcagcatcctgcgatgcagatccggaacataatggtgcagggcgc
tgacttccgcgtttccagactttacgaaacacggaaaccgaagaccat
tcatgttgttgctcaggtcgcagacgttttgcagcagcagtcgcttca
cgttcgctcgcgtatcggtgattcattctgctaaccagtaaggcaacc
ccgccagcctagccgggtcctcaacgacaggagcacgatcatgcgcac
ccgtggggccgccatgccggcgataatggcctgcttctcgccgaaacg
tttggtggcgggaccagtgacgaaggcttgagcgagggcgtgcaagat
tccgaataccgcaagcgacaggccgatcatcgtcgcgctccagcgaaa
gcggtcctcgccgaaaatgacccagagcgctgccggcacctgtcctac
gagttgcatgataaagaagacagtcataagtgcggcgacgatagtcat
gccccgcgcccaccggaaggagctgactgggttgaaggctctcaaggg
catcggtcgagatcccggtgcctaatgagtgagctaacttacattaat
tgcgttgcgctcactgcccgctttccagtcgggaaacctgtcgtgcca
gctgcattaatgaatcggccaacgcgcggggagaggcggtttgcgtat
tgggcgccagggtggtttttcttttcaccagtgagacgggcaacagct
gattgcccttcaccgcctggccctgagagagttgcagcaagcggtcca
cgctggtttgccccagcaggcgaaaatcctgtttgatggtggttaacg
gcgggatataacatgagctgtcttcggtatcgtcgtatcccactaccg
agatatccgcaccaacgcgcagcccggactcggtaatggcgcgcattg
cgcccagcgccatctgatcgttggcaaccagcatcgcagtgggaacga
tgccctcattcagcatttgcatggtttgttgaaaaccggacatggcac
tccagtcgccttcccgttccgctatcggctgaatttgattgcgagtga
gatatttatgccagccagccagacgcagacgcgccgagacagaactta
atgggcccgctaacagcgcgatttgctggtgacccaatgcgaccagat
gctccacgcccagtcgcgtaccgtcttcatgggagaaaataatactgt
tgatgggtgtctggtcagagacatcaagaaataacgccggaacattag
tgcaggcagcttccacagcaatggcatcctggtcatccagcggatagt
taatgatcagcccactgacgcgttgcgcgagaagattgtgcaccgccg
ctttacaggcttcgacgccgcttcgttctaccatcgacaccaccacgc
tggcacccagttgatcggcgcgagatttaatcgccgcgacaatttgcg
acggcgcgtgcagggccagactggaggtggcaacgccaatcagcaacg
actgtttgcccgccagttgttgtgccacgcggttgggaatgtaattca
gctccgccatcgccgcttccactttttcccgcgttttcgcagaaacgt
ggctggcctggttcaccacgcgggaaacggtctgataagagacaccgg
catactctgcgacatcgtataacgttactggtttcacattcaccaccc
tgaattgactctcttccgggcgctatcatgccataccgcgaaaggttt
tgcgccattcgatggtgtccgggatctcgacgctctcccttatgcgac -continued tcctgcattaggaagcagcccagtagtaggttgaggccgttgagcacc
gccgccgcaaggaatggtgcatgcaaggagatggcgcccaacagtccc
ccggccacggggcctgccaccatacccacgccgaaacaagcgctcatg
agcccgaagtggcgagcccgatcttccccatcggtgatgtcggcgata
taggcgccagcaaccgcacctgtggcgccggtgatgccggccacgatg
cgtccggcgtagaggatcgagatctcgatcccgcgaaattaatacgac
tcactataggggaattgtgagcggataacaattcccctctagaaataa
ttttgtttaactttaagaaggagatatacatatggaagctcgtcgttc
tgcgaactacgaacctaacagctgggactatgattacctgctgtcctc
cgacacggacgagtccatcgaagtatacaaagacaaagcgaaaaagct
ggaagccgaagttcgtcgcgagattaataacgaaaaagcagaatttct
gaccctgctggaactgattgacaacgtccagcgcctgggcctgggtta
ccgtttcgagtctgatatccgtggtgcgctggatcgcttcgtttcctc
cggcggcttcgatgcggtaaccaagacttccctgcacggtacggcact
gtctttccgtctgctgcgtcaacacggttttgaggtttctcaggaagc
gttcagcggcttcaaagaccaaaacggcaacttcctggagaacctgaa
ggaagatatcaaagctatcctgagcctgtacgaggccagcttcctggc
tctggaaggcgaaaacatcctggacgaggcgaaggttttcgcaatctc
tcatctgaaagaactgtctgaagaaaagatcggtaaagagctggcaga
acaggtgaaccatgcactggaactgccactgcatcgccgtactcagcg
tctggaagcagtatggtctatcgaggcctaccgtaaaaaggaggacgc
gaatcaggttctgctggagctggcaattctggattacaacatgatcca
gtctgtataccagcgtgatctgcgtgaaacgtcccgttggtggcgtcg
tgtgggtctggcgaccaaactgcactttgctcgtgaccgcctgattga
gagcttctactgggccgtgggtgtagcattcgaaccgcaatactccga
ctgccgtaactccgtcgcaaaaatgttttctttcgtaaccattatcga
cgatatctacgatgtatacggcaccctggacgaactggagctgtttac
tgatgcagttgagcgttgggacgtaaacgccatcaacgacctgccgga
ttacatgaaactgtgctttctggctctgtataacactattaacgaaat
cgcctacgacaacctgaaagataaaggtgagaacatcctgccgtatct
gaccaaagcctgggctgacctgtgcaacgctttcctgcaagaagccaa
gtggctgtacaacaaatctactccgacctttgacgactacttcggcaa
cgcatggaaatcctcttctggcccgctgcaactggtgttcgcttactt
cgctgtcgtgcagaacattaaaaaggaagagatcgaaaacctgcaaaa
ataccatgacaccatctctcgtccttcccatatcttccgtctgtgcaa
tgacctggctagcgcgtctgcggaaattgcgcgtggtgaaaccgcaaa
tagcgtttcttgttacatgcgcactaaaggtatctccgaagaactggc
taccgaaagcgtgatgaatctgatcgatgaaacctggaaaaagatgaa
caaggaaaaactgAGTggtagcctgttcgcgaaaccgttcgtggaaac
cgcgatcaacctggcacgtcaatctcactgcacttatcataacggcga
cgcgcatacctctccggatgagctgacccgcaaacgcgttctgtctgt -continued aatcactgaaccgattctgccgtttgaacgcgaaaacctgtattttca gggcctcgagcaccaccaccaccaccactgagatccggctgctaacaa agcccgaaaggaagctgagttggctgctgccaccgctgagcaataact agcataaccccttggggcctctaaacgggtcttgaggggttttttgct gaaaggaggaactatatccggat 4) Amino Acid Sequence of P. alba MEA L494P (+) TEV - pDW101 (P) (SEQ ID NO: 69)

MEARRSANYEPNSWDYDYLLSSDTDESIEVYKDKAKKLEAEVRREINN

EKAEFLTLLELIDNVQRLGLGYRFESDIRGALDRFVSSGGFDAVTKTS

LHGTALSFRLLRQHGFEVSQEAFSGFKDQNGNFLENLKEDIKAILSLY

EASFLALEGENILDEAKVFAISHLKELSEEKIGKELAEQVNHALELPL

HRRTQRLEAVWSIEAYRKKEDANQVLLELAILDYNMIQSVYQRDLRET

SRWWRRVGLATKLHFARDRLIESFYWAVGVAFEPQYSDCRNSVAKMFS

FVTIIDDIYDVYGTLDELELFTDAVERWDVNAINDLPDYMKLCFLALY

NTINEIAYDNLKDKGENILPYLTKAWADLCNAFLQEAKWLYNKSTPTF

DDYFGNAWKSSSGPLQLVFAYFAVVQNIKKEEIENLQKYHDTISRPSH

IFRLCNDLASASAEIARGETANSVSCYMRTKGISEELATESVMNLIDE

TWKKMNKEKLGGSPFAKPFVETAINLARQSHCTYHNGDAHTSPDELTR

KRVLSVITEPILPFERENLYFQGLEHHHHHH

DNA sequence of pDW101 (SEQ ID NO: 70)

tggcgaatgggacgcgccctgtagcggcgcattaagcgcggcgggtgt ggtggttacgcgcagcgtgaccgctacacttgccagcgccctagcgcc cgctcctttcgctttcttcccttcctttctcgccacgttcgccggctt tccccgtcaagctctaaatcgggggctccctttagggttccgatttag tgctttacggcacctcgaccccaaaaaacttgattagggtgatggttc acgtagtgggccatcgccctgatagacggtttttcgccctttgacgtt ggagtccacgttctttaatagtggactcttgttccaaactggaacaac actcaaccctatctcggtctattcttttgatttataagggattttgcc gatttcggcctattggttaaaaaatgagctgatttaacaaaaatttaa cgcgaattttaacaaaatattaacgtttacaatttcaggtggcactt t tcggggaaatgtgcgcggaacccctatttgtttatttttctaaataca ttcaaatatgtatccgctcatgaattaattcttagaaaaactcatcga gcatcaaatgaaactgcaatttattcatatcaggattatcaataccat atttttgaaaaagccgtttctgtaatgaaggagaaaactcaccgaggc agttccataggatggcaagatcctggtatcggtctgcgattccgactc gtccaacatcaatacaacctattaatttcccctcgtcaaaaataaggt tatcaagtgagaaatcaccatgagtgacgactgaatccggtgagaatg gcaaaagtttatgcatttctttccagacttgttcaacaggccagccat tacgctcgtcatcaaaatcactcgcatcaaccaaaccgttattcattc gtgattgcgcctgagcgagacgaaatacgcgatcgctgttaaaaggac aattacaaacaggaatcgaatgcaaccggcgcaggaacactgccagcg catcaacaatattttcacctgaatcaggatattcttctaatacctgga atgctgttttcccggggatcgcagtggtgagtaaccatgcatcatcag gagtacggataaaatgcttgatggtcggaagaggcataaattccgtca gccagtttagtctgaccatctcatctgtaacatcattggcaacgctac ctttgccatgtttcagaaacaactctggcgcatcgggcttcccataca atcgatagattgtcgcacctgattgcccgacattatcgcgagcccatt tatacccatataaatcagcatccatgttggaatttaatcgcggcctag agcaagacgtttcccgttgaatatggctcataacaccccttgtattac tgtttatgtaagcagacagttttattgttcatgaccaaaatcccttaa cgtgagttttcgttccactgagcgtcagaccccgtagaaaagatcaaa ggatcttcttgagatcctttttttctgcgcgtaatctgctgcttgcaa acaaaaaaaccaccgctaccagcggtggtttgtttgccggatcaagag ctaccaactctttttccgaaggtaactggcttcagcagagcgcagata ccaaatactgtccttctagtgtagccgtagttaggccaccacttcaag aactctgtagcaccgcctacatacctcgctctgctaatcctgttacca gtggctgctgccagtggcgataagtcgtgtcttaccgggttggactca agacgatagttaccggataaggcgcagcggtcgggctgaacggggggt tcgtgcacacagcccagcttggagcgaacgacctacaccgaactgaga tacctacagcgtgagctatgagaaagcgccacgcttcccgaagggaga aaggcggacaggtatccggtaagcggcagggtcggaacaggagagcgc acgagggagcttccagggggaaacgcctggtatctttatagtcctgtc gggtttcgccacctctgacttgagcgtcgatttttgtgatgctcgtca ggggggcggagcctatggaaaaacgccagcaacgcggcctttttacgg ttcctggccttttgctggccttttgctcacatgttctttcctgcgtta tcccctgattctgtggataaccgtattaccgcctttgagtgagctgat accgctcgccgcagccgaacgaccgagcgcagcgagtcagtgagcgag gaagcggaagagcgcctgatgcggtattttctccttacgcatctgtgc ggtatttcacaccgcatatatggtgcactctcagtacaatctgctctg atgccgcatagttaagccagtatacactccgctatcgctacgtgactg ggtcatggctgcgccccgacacccgccaacacccgctgacgcgccctg acgggcttgtctgctcccggcatccgcttacagacaagctgtgaccgt ctccgggagctgcatgtgtcagaggttttcaccgtcatcaccgaaacg cgcgaggcagctgcggtaaagctcatcagcgtggtcgtgaagcgattc acagatgtctgcctgttcatccgcgtccagctcgttgagtttctccag aagcgttaatgtctggcttctgataaagcgggccatgttaagggcggt tttttcctgtttggtcactgatgcctccgtgtaagggggatttctgtt catgggggtaatgataccgatgaaacgagagaggatgctcacgatacg ggttactgatgatgaacatgcccggttactggaacgttgtgagggtaa acaactggcggtatggatgcggcgggaccagagaaaaatcactcaggg -continued tcaatgccagcgcttcgttaatacagatgtaggtgttccacagggtag ccagcagcatcctgcgatgcagatccggaacataatggtgcagggcgc tgacttccgcgtttccagactttacgaaacacggaaaccgaagaccat tcatgttgttgctcaggtcgcagacgttttgcagcagcagtcgcttca cgttcgctcgcgtatcggtgattcattctgctaaccagtaaggcaacc ccgccagcctagccgggtcctcaacgacaggagcacgatcatgcgcac ccgtggggccgccatgccggcgataatggcctgcttctcgccgaaacg tttggtggcgggaccagtgacgaaggcttgagcgagggcgtgcaagat tccgaataccgcaagcgacaggccgatcatcgtcgcgctccagcgaaa gcggtcctcgccgaaaatgacccagagcgctgccggcacctgtcctac gagttgcatgataaagaagacagtcataagtgcggcgacgatagtcat gccccgcgcccaccggaaggagctgactgggttgaaggctctcaaggg catcggtcgagatcccggtgcctaatgagtgagctaacttacattaat tgcgttgcgctcactgcccgctttccagtcgggaaacctgtcgtgcca gctgcattaatgaatcggccaacgcgcggggagaggcggtttgcgtat tgggcgccagggtggtttttcttttcaccagtgagacgggcaacagct gattgcccttcaccgcctggccctgagagagttgcagcaagcggtcca cgctggtttgccccagcaggcgaaaatcctgtttgatggtggttaacg gcgggatataacatgagctgtcttcggtatcgtcgtatcccactaccg agatatccgcaccaacgcgcagcccggactcggtaatggcgcgcattg cgcccagcgccatctgatcgttggcaaccagcatcgcagtgggaacga tgccctcattcagcatttgcatggtttgttgaaaaccggacatggcac tccagtcgccttcccgttccgctatcggctgaatttgattgcgagtga gatatttatgccagccagccagacgcagacgcgccgagacagaactta atgggcccgctaacagcgcgatttgctggtgacccaatgcgaccagat gctccacgcccagtcgcgtaccgtcttcatgggagaaaataatactgt tgatgggtgtctggtcagagacatcaagaaataacgccggaacattag tgcaggcagcttccacagcaatggcatcctggtcatccagcggatagt taatgatcagcccactgacgcgttgcgcgagaagattgtgcaccgccg ctttacaggcttcgacgccgcttcgttctaccatcgacaccaccacgc tggcacccagttgatcggcgcgagatttaatcgccgcgacaatttgcg acggcgcgtgcagggccagactggaggtggcaacgccaatcagcaacg actgtttgcccgccagttgttgtgccacgcggttgggaatgtaattca gctccgccatcgccgcttccactttttcccgcgttttcgcagaaacgt ggctggcctggttcaccacgcgggaaacggtctgataagagacaccgg catactctgcgacatcgtataacgttactggtttcacattcaccaccc tgaattgactctcttccgggcgctatcatgccataccgcgaaaggttt tgcgccattcgatggtgtccgggatctcgacgctctcccttatgcgac tcctgcattaggaagcagcccagtagtaggttgaggccgttgagcacc gccgccgcaaggaatggtgcatgcaaggagatggcgcccaacagtccc ccggccacggggcctgccaccatacccacgccgaaacaagcgctcatg agcccgaagtggcgagcccgatcttccccatcggtgatgtcggcgata taggcgccagcaaccgcacctgtggcgccggtgatgccggccacgatg cgtccggcgtagaggatcgagatctcgatcccgcgaaattaatacgac tcactataggggaattgtgagcggataacaattcccctctagaaataa ttttgtttaactttaagaaggagatatacatatggaagctcgtcgttc tgcgaactacgaacctaacagctgggactatgattacctgctgtcctc cgacacggacgagtccatcgaagtatacaaagacaaagcgaaaaagct ggaagccgaagttcgtcgcgagattaataacgaaaaagcagaatttct gaccctgctggaactgattgacaacgtccagcgcctgggcctgggtta ccgtttcgagtctgatatccgtggtgcgctggatcgcttcgtttcctc cggcggcttcgatgcggtaaccaagacttccctgcacggtacggcact gtctttccgtctgctgcgtcaacacggttttgaggtttctcaggaagc gttcagcggcttcaaagaccaaaacggcaacttcctggagaacctgaa ggaagatatcaaagctatcctgagcctgtacgaggccagcttcctggc tctggaaggcgaaaacatcctggacgaggcgaaggttttcgcaatctc tcatctgaaagaactgtctgaagaaaagatcggtaaagagctggcaga acaggtgaaccatgcactggaactgccactgcatcgccgtactcagcg tctggaagcagtatggtctatcgaggcctaccgtaaaaaggaggacgc gaatcaggttctgctggagctggcaattctggattacaacatgatcca gtctgtataccagcgtgatctgcgtgaaacgtcccgttggtggcgtcg tgtgggtctggcgaccaaactgcactttgctcgtgaccgcctgattga gagcttctactgggccgtgggtgtagcattcgaaccgcaatactccga ctgccgtaactccgtcgcaaaaatgtttctttcgtaaccattatcga cgatatctacgatgtatacggcaccctggacgaactggagctgtttac tgatgcagttgagcgttgggacgtaaacgccatcaacgacctgccgga ttacatgaaactgtgctttctggctctgtataacactattaacgaaat cgcctacgacaacctgaaagataaaggtgagaacatcctgccgtatct gaccaaagcctgggctgacctgtgcaacgctttcctgcaagaagccaa gtggctgtacaacaaatctactccgacctttgacgactacttcggcaa cgcatggaaatcctcttctggcccgctgcaactggtgttcgcttactt cgctgtcgtgcagaacattaaaaaggaagagatcgaaaacctgcaaaa ataccatgacaccatctctcgtccttcccatatcttccgtctgtgcaa tgacctggctagcgcgtctgcggaaattgcgcgtggtgaaaccgcaaa tagcgtttcttgttacatgcgcactaaaggtatctccgaagaactggc taccgaaagcgtgatgaatctgatcgatgaaacctggaaaaagatgaa caaggaaaaactgggtggtagcCCGttcgcgaaaccgttcgtggaaac cgcgatcaacctggcacgtcaatctcactgcacttatcataacggcga cgcgcatacctctccggatgagctgacccgcaaacgcgttctgtctgt aatcactgaaccgattctgccgtttgaacgcgaaaacctgtattttca gggcctcgagcaccaccaccaccaccactgagatccggctgctaacaa -continued agcccgaaaggaagctgagttggctgctgccaccgctgagcaataact agcataaccccttggggcctctaaacgggtcttgaggggttttttgct gaaaggaggaactatatccggat 5) Amino Acid Sequence of P. alba MEA T536C (+) TEV - pDW102 (C) (SEQ ID NO: 71)

MEARRSANYEPNSWDYDYLLSSDTDESIEVYKDKAKKLEAEVRREINN

EKAEFLTLLELIDNVQRLGLGYRFESDIRGALDRFVSSGGFDAVTKTS

LHGTALSFRLLRQHGFEVSQEAFSGFKDQNGNFLENLKEDIKAILSLY

EASFLALEGENILDEAKVFAISHLKELSEEKIGKELAEQVNHALELPL

HRRTQRLEAVWSIEAYRKKEDANQVLLELAILDYNMIQSVYQRDLRET

SRWWRRVGLATKLHFARDRLIESFYWAVGVAFEPQYSDCRNSVAKMFS

FVTIIDDIYDVYGTLDELELFTDAVERWDVNAINDLPDYMKLCFLALY

NTINEIAYDNLKDKGENILPYLTKAWADLCNAFLQEAKWLYNKSTPTF

DDYFGNAWKSSSGPLQLVFAYFAVVQNIKKEEIENLQKYHDTISRPSH

IFRLCNDLASASAEIARGETANSVSCYMRTKGISEELATESVMNLIDE

TWKKMNKEKLGGSLFAKPFVETAINLARQSHCTYHNGDAHTSPDELTR

KRVLSVICEPILPFERENLYFQGLEHHHHHH

DNA sequence of pDW102 (SEQ ID NO: 72)

tggcgaatgggacgcgccctgtagcggcgcattaagcgcggcgggtgt ggtggttacgcgcagcgtgaccgctacacttgccagcgccctagcgcc cgctcctttcgctttcttcccttcctttctcgccacgttcgccggctt tccccgtcaagctctaaatcgggggctccctttagggttccgatttag tgctttacggcacctcgaccccaaaaaacttgattagggtgatggttc acgtagtgggccatcgccctgatagacggtttttcgccctttgacgtt ggagtccacgttctttaatagtggactcttgttccaaactggaacaac actcaaccctatctcggtctattcttttgatttataagggattttgcc gatttcggcctattggttaaaaaatgagctgatttaacaaaaatttaa cgcgaattttaacaaaatattaacgtttacaatttcaggtggcacttt tcggggaaatgtgcgcggaacccctatttgtttatttttctaaataca ttcaaatatgtatccgctcatgaattaattcttagaaaaactcatcga gcatcaaatgaaactgcaatttattcatatcaggattatcaataccat atttttgaaaaagccgtttctgtaatgaaggagaaaactcaccgaggc agttccataggatggcaagatcctggtatcggtctgcgattccgactc gtccaacatcaatacaacctattaatttcccctcgtcaaaaataaggt tatcaagtgagaaatcaccatgagtgacgactgaatccggtgagaatg gcaaaagtttatgcatttctttccagacttgttcaacaggccagccat tacgctcgtcatcaaaatcactcgcatcaaccaaaccgttattcattc gtgattgcgcctgagcgagacgaaatacgcgatcgctgttaaaaggac aattacaaacaggaatcgaatgcaaccggcgcaggaacactgccagcg -continued catcaacaatattttcacctgaatcaggatattcttctaatacctgga atgctgttttcccggggatcgcagtggtgagtaaccatgcatcatcag gagtacggataaaatgcttgatggtcggaagaggcataaattccgtca gccagtttagtctgaccatctcatctgtaacatcattggcaacgctac ctttgccatgtttcagaaacaactctggcgcatcgggcttcccataca atcgatagattgtcgcacctgattgcccgacattatcgcgagcccatt tatacccatataaatcagcatccatgttggaatttaatcgcggcctag agcaagacgtttcccgttgaatatggctcataacaccccttgtattac tgtttatgtaagcagacagttttattgttcatgaccaaaatcccttaa cgtgagttttcgttccactgagcgtcagaccccgtagaaaagatcaaa ggatcttcttgagatcctttttttctgcgcgtaatctgctgcttgcaa acaaaaaaaccaccgctaccagcggtggtttgtttgccggatcaagag ctaccaactctttttccgaaggtaactggcttcagcagagcgcagata ccaaatactgtccttctagtgtagccgtagttaggccaccacttcaag aactctgtagcaccgcctacatacctcgctctgctaatcctgttacca gtggctgctgccagtggcgataagtcgtgtcttaccgggttggactca agacgatagttaccggataaggcgcagcggtcgggctgaacggggggt tcgtgcacacagcccagcttggagcgaacgacctacaccgaactgaga tacctacagcgtgagctatgagaaagcgccacgcttcccgaagggaga aaggcggacaggtatccggtaagcggcagggtcggaacaggagagcgc acgagggagcttccagggggaaacgcctggtatctttatagtcctgtc gggtttcgccacctctgacttgagcgtcgatttttgtgatgctcgtca ggggggcggagcctatggaaaaacgccagcaacgcggcctttttacgg ttcctggccttttgctggccttttgctcacatgttctttcctgcgtta tcccctgattctgtggataaccgtattaccgcctttgagtgagctgat accgctcgccgcagccgaacgaccgagcgcagcgagtcagtgagcgag gaagcggaagagcgcctgatgcggtattttctccttacgcatctgtgc ggtatttcacaccgcatatatggtgcactctcagtacaatctgctctg atgccgcatagttaagccagtatacactccgctatcgctacgtgactg ggtcatggctgcgccccgacacccgccaacacccgctgacgcgccctg acgggcttgtctgctcccggcatccgcttacagacaagctgtgaccgt ctccgggagctgcatgtgtcagaggttttcaccgtcatcaccgaaacg cgcgaggcagctgcggtaaagctcatcagcgtggtcgtgaagcgattc acagatgtctgcctgttcatccgcgtccagctcgttgagtttctccag aagcgttaatgtctggcttctgataaagcgggccatgttaagggcggt tttttcctgtttggtcactgatgcctccgtgtaagggggatttctgtt catgggggtaatgataccgatgaaacgagagaggatgctcacgatacg ggttactgatgatgaacatgcccggttactggaacgttgtgagggtaa acaactggcggtatggatgcggcgggaccagagaaaaatcactcaggg tcaatgccagcgcttcgttaatacagatgtaggtgttccacagggtag ccagcagcatcctgcgatgcagatccggaacataatggtgcagggcgc -continued

```
tgacttccgcgtttccagactttacgaaacacggaaaccgaagaccat
tcatgttgttgctcaggtcgcagacgttttgcagcagcagtcgcttca
cgttcgctcgcgtatcggtgattcattctgctaaccagtaaggcaacc
ccgccagcctagccgggtcctcaacgacaggagcacgatcatgcgcac
ccgtggggccgccatgccggcgataatggcctgcttctcgccgaaacg
tttggtggcgggaccagtgacgaaggcttgagcgagggcgtgcaagat
tccgaataccgcaagcgacaggccgatcatcgtcgcgctccagcgaaa
gcggtcctcgccgaaaatgacccagagcgctgccggcacctgtcctac
gagttgcatgataaagaagacagtcataagtgcggcgacgatagtcat
gccccgcgcccaccggaaggagctgactgggttgaaggctctcaaggg
catcggtcgagatcccggtgcctaatgagtgagctaacttacattaat
tgcgttgcgctcactgcccgctttccagtcgggaaacctgtcgtgcca
gctgcattaatgaatcggccaacgcgcggggagaggcggtttgcgtat
tgggcgccagggtggtttttcttttcaccagtgagacgggcaacagct
gattgcccttcaccgcctggccctgagagagttgcagcaagcggtcca
cgctggtttgccccagcaggcgaaaatcctgtttgatggtggttaacg
gcgggatataacatgagctgtcttcggtatcgtcgtatcccactaccg
agatatccgcaccaacgcgcagcccggactcggtaatggcgcgcattg
cgcccagcgccatctgatcgttggcaaccagcatcgcagtgggaacga
tgccctcattcagcatttgcatggtttgttgaaaaccggacatggcac
tccagtcgccttcccgttccgctatcggctgaatttgattgcgagtga
gatatttatgccagccagccagacgcagacgcgccgagacagaactta
atgggcccgctaacagcgcgatttgctggtgacccaatgcgaccagat
gctccacgcccagtcgcgtaccgtcttcatgggagaaaataatactgt
tgatgggtgtctggtcagagacatcaagaaataacgccggaacattag
tgcaggcagcttccacagcaatggcatcctggtcatccagcggatagt
taatgatcagcccactgacgcgttgcgcgagaagattgtgcaccgccg
ctttacaggcttcgacgccgcttcgttctaccatcgacaccaccacgc
tggcacccagttgatcggcgcgagatttaatcgccgcgacaatttgcg
acggcgcgtgcagggccagactggaggtggcaacgccaatcagcaacg
actgtttgcccgccagttgttgtgccacgcggttgggaatgtaattca
gctccgccatcgccgcttccactttttcccgcgttttcgcagaaacgt
ggctggcctggttcaccacgcgggaaacggtctgataagagacaccgg
catactctgcgacatcgtataacgttactggtttcacattcaccaccc
tgaattgactctcttccgggcgctatcatgccataccgcgaaaggttt
tgcgccattcgatggtgtccgggatctcgacgctctcccttatgcgac
tcctgcattaggaagcagcccagtagtaggttgaggccgttgagcacc
gccgccgcaaggaatggtgcatgcaaggagatggcgcccaacagtccc
ccggccacggggcctgccaccatacccacgccgaaacaagcgctcatg
agcccgaagtggcgagcccgatcttccccatcggtgatgtcggcgata
```

-continued

```
taggcgccagcaaccgcacctgtggcgccggtgatgccggccacgatg
cgtccggcgtagaggatcgagatctcgatcccgcgaaattaatacgac
tcactataggggaattgtgagcggataacaattcccctctagaaataa
ttttgtttaactttaagaaggagatatacatatggaagctcgtcgttc
tgcgaactacgaacctaacagctgggactatgattacctgctgtcctc
cgacacggacgagtccatcgaagtatacaaagacaaagcgaaaaagct
ggaagccgaagttcgtcgcgagattaataacgaaaaagcagaatttct
gaccctgctggaactgattgacaacgtccagcgcctgggcctgggtta
ccgtttcgagtctgatatccgtggtgcgctggatcgcttcgtttcctc
cggcggcttcgatgcggtaaccaagacttccctgcacggtacggcact
gtctttccgtctgctgcgtcaacacggttttgaggtttctcaggaagc
gttcagcggcttcaaagaccaaaacggcaacttcctggagaacctgaa
ggaagatatcaaagctatcctgagcctgtacgaggccagcttcctggc
tctggaaggcgaaaacatcctggacgaggcgaaggttttcgcaatctc
tcatctgaaagaactgtctgaagaaaagatcggtaaagagctggcaga
acaggtgaaccatgcactggaactgccactgcatcgccgtactcagcg
tctggaagcagtatggtctatcgaggcctaccgtaaaaaggaggacgc
gaatcaggttctgctggagctggcaattctggattacaacatgatcca
gtctgtataccagcgtgatctgcgtgaaacgtcccgttggtggcgtcg
tgtgggtctggcgaccaaactgcactttgctcgtgaccgcctgattga
gagcttctactgggccgtgggtgtagcattcgaaccgcaatactccga
ctgccgtaactccgtcgcaaaaatgtttctttcgtaaccattatcga
cgatatctacgatgtatacggcaccctggacgaactggagctgtttac
tgatgcagttgagcgttgggacgtaaacgccatcaacgacctgccgga
ttacatgaaactgtgctttctggctctgtataacactattaacgaaat
cgcctacgacaacctgaaagataaaggtgagaacatcctgccgtatct
gaccaaagcctgggctgacctgtgcaacgctttcctgcaagaagccaa
gtggctgtacaacaaatctactccgacctttgacgactacttcggcaa
cgcatggaaatcctcttctggcccgctgcaactggtgttcgcttactt
cgctgtcgtgcagaacattaaaaaggaagagatcgaaaacctgcaaaa
ataccatgacaccatctctcgtccttcccatatcttccgtctgtgcaa
tgacctggctagcgcgtctgcggaaattgcgcgtggtgaaaccgcaaa
tagcgtttcttgttacatgcgcactaaaggtatctccgaagaactggc
taccgaaagcgtgatgaatctgatcgatgaaacctggaaaaagatgaa
caaggaaaaactgggtggtagcctgttcgcgaaaccgttcgtggaaac
cgcgatcaacctggcacgtcaatctcactgcacttatcataacggcga
cgcgcatacctctccggatgagctgacccgcaaacgcgttctgtctgt
aatcTGCgaaccgattctgccgtttgaacgcgaaaacctgtattttca
gggcctcgagcaccaccaccaccaccactgagatccggctgctaacaa
agcccgaaaggaagctgagttggctgctgccaccgctgagcaataact
```

agcataaccccttggggcctctaaacgggtcttgaggggttttttgct gaaaggaggaactatatccggat

6) Amino Acid Sequence of P. alba MEA A453N G491S (+)TEV - pDW103 (NS) (SEQ ID NO: 73)

MEARRSANYEPNSWDYDYLLSSDTDESIEVYKDKAKKLEAEVRREINN

EKAEFLTLLELIDNVQRLGLGYRFESDIRGALDRFVSSGGFDAVTKTS

LHGTALSFRLLRQHGFEVSQEAFSGFKDQNGNFLENLKEDIKAILSLY

EASFLALEGENILDEAKVFAISHLKELSEEKIGKELAEQVNHALELPL

HRRTQRLEAVWSIEAYRKKEDANQVLLELAILDYNMIQSVYQRDLRET

SRWWRRVGLATKLHFARDRLIESFYWAVGVAFEPQYSDCRNSVAKMFS

FVTIIDDIYDVYGTLDELELFTDAVERWDVNAINDLPDYMKLCFLALY

NTINEIAYDNLKDKGENILPYLTKAWADLCNAFLQEAKWLYNKSTPTF

DDYFGNAWKSSSGPLQLVFAYFAVVQNIKKEEIENLQKYHDTISRPSH

IFRLCNDLASASAEIARGETNNSVSCYMRTKGISEELATESVMNLIDE

TWKKMNKEKLSGSLFAKPFVETAINLARQSHCTYHNGDAHTSPDELTR

KRVLSVITEPILPFERENLYFQGLEHHHHHH

DNA sequence of pDW103 (SEQ ID NO: 74)

tggcgaatgggacgcgccctgtagcggcgcattaagcgcggcgggtgt ggtggttacgcgcagcgtgaccgctacacttgccagcgccctagcgcc cgctcctttcgctttcttcccttcctttctcgccacgttcgccggctt tccccgtcaagctctaaatcgggggctccctttagggttccgatttag tgctttacggcacctcgaccccaaaaaacttgattagggtgatggttc acgtagtgggccatcgccctgatagacggtttttcgccctttgacgtt ggagtccacgttctttaatagtggactcttgttccaaactggaacaac actcaaccctatctcggtctattcttttgatttataagggattttgcc gatttcggcctattggttaaaaaatgagctgatttaacaaaaatttaa cgcgaattttaacaaaatattaacgtttacaatttcaggtggcacttt tcggggaaatgtgcgcggaacccctatttgtttatttttctaaataca ttcaaatatgtatccgctcatgaattaattcttagaaaaactcatcga gcatcaaatgaaactgcaatttattcatatcaggattatcaataccat atttttgaaaaagccgtttctgtaatgaaggagaaaactcaccgaggc agttccataggatggcaagatcctggtatcggtctgcgattccgactc gtccaacatcaatacaacctattaatttcccctcgtcaaaaataaggt tatcaagtgagaaatcaccatgagtgacgactgaatccggtgagaatg gcaaaagtttatgcatttctttccagacttgttcaacaggccagccat tacgctcgtcatcaaaatcactcgcatcaaccaaaccgttattcattc gtgattgcgcctgagcgagacgaaatacgcgatcgctgttaaaaggac aattacaaacaggaatcgaatgcaaccggcgcaggaacactgccagcg catcaacaatattttcacctgaatcaggatattcttctaatacctgga atgctgttttcccggggatcgcagtggtgagtaaccatgcatcatcag gagtacggataaaatgcttgatggtcggaagaggcataaattccgtca gccagtttagtctgaccatctcatctgtaacatcattggcaacgctac ctttgccatgtttcagaaacaactctggcgcatcgggcttcccataca atcgatagattgtcgcacctgattgcccgacattatcgcgagcccatt tatacccatataaatcagcatccatgttggaatttaatcgcggcctag agcaagacgtttcccgttgaatatggctcataacaccccttgtattac tgtttatgtaagcagacagttttattgttcatgaccaaaatcccttaa cgtgagttttcgttccactgagcgtcagaccccgtagaaaagatcaaa ggatcttcttgagatcctttttttctgcgcgtaatctgctgcttgcaa acaaaaaaaccaccgctaccagcggtggtttgtttgccggatcaagag ctaccaactctttttccgaaggtaactggcttcagcagagcgcagata ccaaatactgtccttctagtgtagccgtagttaggccaccacttcaag aactctgtagcaccgcctacatacctcgctctgctaatcctgttacca gtggctgctgccagtggcgataagtcgtgtcttaccgggttggactca agacgatagttaccggataaggcgcagcggtcgggctgaacggggggt tcgtgcacacagcccagcttggagcgaacgacctacaccgaactgaga tacctacagcgtgagctatgagaaagcgccacgcttcccgaagggaga aaggcggacaggtatccggtaagcggcagggtcggaacaggagagcgc acgagggagcttccagggggaaacgcctggtatctttatagtcctgtc gggtttcgccacctctgacttgagcgtcgatttttgtgatgctcgtca ggggggcggagcctatggaaaaacgccagcaacgcggcctttttacgg ttcctggccttttgctggccttttgctcacatgttctttcctgcgtta tcccctgattctgtggataaccgtattaccgcctttgagtgagctgat accgctcgccgcagccgaacgaccgagcgcagcgagtcagtgagcgag gaagcggaagagcgcctgatgcggtattttctccttacgcatctgtgc ggtatttcacaccgcatatatggtgcactctcagtacaatctgctctg atgccgcatagttaagccagtatacactccgctatcgctacgtgactg ggtcatggctgcgccccgacacccgccaacacccgctgacgcgccctg acgggcttgtctgctcccggcatccgcttacagacaagctgtgaccgt ctccgggagctgcatgtgtcagaggttttcaccgtcatcaccgaaacg cgcgaggcagctgcggtaaagctcatcagcgtggtcgtgaagcgattc acagatgtctgcctgttcatccgcgtccagctcgttgagtttctccag aagcgttaatgtctggcttctgataaagcgggccatgttaagggcggt ttttcctgtttggtcactgatgcctccgtgtaagggggatttctgtt catgggggtaatgataccgatgaaacgagagaggatgctcacgatacg ggttactgatgatgaacatgcccggttactggaacgttgtgagggtaa acaactggcggtatggatgcggcgggaccagagaaaaatcactcaggg tcaatgccagcgcttcgttaatacagatgtaggtgttccacagggtag ccagcagcatcctgcgatgcagatccggaacataatggtgcagggcgc tgacttccgcgtttccagactttacgaaacacggaaaccgaagaccat tcatgttgttgctcaggtcgcagacgttttgcagcagcagtcgcttca -continued cgttcgctcgcgtatcggtgattcattctgctaaccagtaaggcaacc ccgccagcctagccgggtcctcaacgacaggagcacgatcatgcgcac ccgtggggccgccatgccggcgataatggcctgcttctcgccgaaacg tttggtggcgggaccagtgacgaaggcttgagcgagggcgtgcaagat tccgaataccgcaagcgacaggccgatcatcgtcgcgctccagcgaaa gcggtcctcgccgaaaatgacccagagcgctgccggcacctgtcctac gagttgcatgataaagaagacagtcataagtgcggcgacgatagtcat gccccgcgcccaccggaaggagctgactgggttgaaggctctcaaggg catcggtcgagatcccggtgcctaatgagtgagctaacttacattaat tgcgttgcgctcactgcccgctttccagtcgggaaacctgtcgtgcca gctgcattaatgaatcggccaacgcgcggggagaggcggtttgcgtat tgggcgccagggtggtttttcttttcaccagtgagacgggcaacagct gattgcccttcaccgcctggccctgagagagttgcagcaagcggtcca cgctggtttgccccagcaggcgaaaatcctgtttgatggtggttaacg gcgggatataacatgagctgtcttcggtatcgtcgtatcccactaccg agatatccgcaccaacgcgcagcccggactcggtaatggcgcgcattg cgcccagcgccatctgatcgttggcaaccagcatcgcagtgggaacga tgccctcattcagcatttgcatggtttgttgaaaaccggacatggcac tccagtcgccttcccgttccgctatcggctgaatttgattgcgagtga gatatttatgccagccagccagacgcagacgcgccgagacagaactta atgggcccgctaacagcgcgatttgctggtgacccaatgcgaccagat gctccacgcccagtcgcgtaccgtcttcatgggagaaaataatactgt tgatgggtgtctggtcagagacatcaagaaataacgccggaacattag tgcaggcagcttccacagcaatggcatcctggtcatccagcggatagt taatgatcagcccactgacgcgttgcgcgagaagattgtgcaccgccg ctttacaggcttcgacgccgcttcgttctaccatcgacaccaccacgc tggcacccagttgatcggcgcgagatttaatcgccgcgacaatttgcg acggcgcgtgcagggccagactggaggtggcaacgccaatcagcaacg actgtttgcccgccagttgttgtgccacgcggttgggaatgtaattca gctccgccatcgccgcttccactttttcccgcgttttcgcagaaacgt ggctggcctggttcaccacgcgggaaacggtctgataagagacaccgg catactctgcgacatcgtataacgttactggtttcacattcaccaccc tgaattgactctcttccgggcgctatcatgccataccgcgaaaggttt tgcgccattcgatggtgtccgggatctcgacgctctcccttatgcgac tcctgcattaggaagcagcccagtagtaggttgaggccgttgagcacc gccgccgcaaggaatggtgcatgcaaggagatggcgcccaacagtccc ccggccacggggcctgccaccatacccacgccgaaacaagcgctcatg agcccgaagtggcgagcccgatcttccccatcggtgatgtcggcgata taggcgccagcaaccgcacctgtggcgccggtgatgccggccacgatg cgtccggcgtagaggatcgagatctcgatcccgcgaaattaatacgac -continued tcactataggggaattgtgagcggataacaattcccctctagaaataa ttttgtttaactttaagaaggagatatacatatggaagctcgtcgttc tgcgaactacgaacctaacagctgggactatgattacctgctgtcctc cgacacggacgagtccatcgaagtatacaaagacaaagcgaaaaagct ggaagccgaagttcgtcgcgagattaataacgaaaaagcagaatttct gaccctgctggaactgattgacaacgtccagcgcctgggcctgggtta ccgtttcgagtctgatatccgtggtgcgctggatcgcttcgtttcctc cggcggcttcgatgcggtaaccaagacttccctgcacggtacggcact gtctttccgtctgctgcgtcaacacggttttgaggtttctcaggaagc gttcagcggcttcaaagaccaaaacggcaacttcctggagaacctgaa ggaagatatcaaagctatcctgagcctgtacgaggccagcttcctggc tctggaaggcgaaaacatcctggacgaggcgaaggttttcgcaatctc tcatctgaaagaactgtctgaagaaaagatcggtaaagagctggcaga acaggtgaaccatgcactggaactgccactgcatcgccgtactcagcg tctggaagcagtatggtctatcgaggcctaccgtaaaaaggaggacgc gaatcaggttctgctggagctggcaattctggattacaacatgatcca gtctgtataccagcgtgatctgcgtgaaacgtcccgttggtggcgtcg tgtgggtctggcgaccaaactgcactttgctcgtgaccgcctgattga gagcttctactgggccgtgggtgtagcattcgaaccgcaatactccga ctgccgtaactccgtcgcaaaaatgtttttctttcgtaaccattatcg acgatatctacgatgtatacggcaccctggacgaactggagctgttta ctgatgcagttgagcgttgggacgtaaacgccatcaacgacctgccgg attacatgaaactgtgctttctggctctgtataacactattaacgaaa tcgcctacgacaacctgaaagataaaggtgagaacatcctgccgtatc tgaccaaagcctgggctgacctgtgcaacgctttcctgcaagaagcca agtggctgtacaacaaatctactccgacctttgacgactacttcggca acgcatggaaatcctcttctggcccgctgcaactggtgttcgcttact tcgctgtcgtgcagaacattaaaaaggaagagatcgaaaacctgcaaa aataccatgacaccatctctcgtccttcccatatcttccgtctgtgca atgacctggctagcgcgtctgcggaaattgcgcgtggtgaaaccaaca atagcgtttcttgttacatgcgcactaaaggtatctccgaagaactgg ctaccgaaagcgtgatgaatctgatcgatgaaacctggaaaaagatga acaaggaaaaactgAGTggtagcctgttcgcgaaaccgttcgtggaaa ccgcgatcaacctggcacgtcaatctcactgcactttatcataacggcg acgcgcatacctctccggatgagctgacccgcaaacgcgttctgtctg taatcactgaaccgattctgccgtttgaacgcgaaaacctgtattttc agggcctcgagcaccaccaccaccaccactgagatccggctgctaaca aagcccgaaaggaagctgagttggctgctgccaccgctgagcaataac tagcataaccccttggggcctctaaacgggtcttgaggggttttttgc tgaaaggaggaactatatccggat 7) Amino Acid Sequence of P. alba MEA A453N L494P (+)TEV - pDW104 (NP) (SEQ ID NO: 75)

MEARRSANYEPNSWDYDYLLSSDTDESIEVYKDKAKKLEAEVRREINN
EKAEFLTLLELIDNVQRLGLGYRFESDIRGALDRFVSSGGFDAVTKTS
LHGTALSFRLLRQHGFEVSQEAFSGFKDQNGNFLENLKEDIKAILSLY
EASFLALEGENILDEAKVFAISHLKELSEEKIGKELAEQVNHALELPL
HRRTQRLEAVWSIEAYRKKEDANQVLLELAILDYNMIQSVYQRDLRET
SRWWRRVGLATKLHFARDRLIESFYWAVGVAFEPQYSDCRNSVAKMFS
FVTIIDDIYDVYGTLDELELFTDAVERWDVNAINDLPDYMKLCFLALY
NTINEIAYDNLKDKGENILPYLTKAWADLCNAFLQEAKWLYNKSTPTF
DDYFGNAWKSSSGPLQLVFAYFAVVQNIKKEEIENLQKYHDTISRPSH
IFRLCNDLASASAEIARGETNNSVSCYMRTKGISEELATESVMNLIDE
TWKKMNKEKLGGSPFAKPFVETAINLARQSHCTYHNGDAHTSPDELTR
KRVLSVITEPILPFERENLYFQGLEHHHHHH

DNA sequence of pDW104 (SEQ ID NO: 76)

tggcgaatgggacgcgccctgtagcggcgcattaagcgcggcgggtgt
ggtggttacgcgcagcgtgaccgctacacttgccagcgccctagcgcc
cgctcctttcgctttcttcccttcctttctcgccacgttcgccggctt
tccccgtcaagctctaaatcgggggctccctttagggttccgatttag
tgctttacggcacctcgaccccaaaaaacttgattagggtgatggttc
acgtagtgggccatcgccctgatagacggtttttcgccctttgacgtt
ggagtccacgttctttaatagtggactcttgttccaaactggaacaac
actcaaccctatctcggtctattcttttgatttataagggattttgcc
gatttcggcctattggttaaaaaatgagctgatttaacaaaaatttaa
cgcgaattttaacaaaatattaacgtttacaatttcaggtggcacttt
tcggggaaatgtgcgcggaacccctatttgtttatttttctaaataca
ttcaaatatgtatccgctcatgaattaattcttagaaaaactcatcga
gcatcaaatgaaactgcaatttattcatatcaggattatcaataccat
atttttgaaaaagccgtttctgtaatgaaggagaaaactcaccgaggc
agttccataggatggcaagatcctggtatcggtctgcgattccgactc
gtccaacatcaatacaacctattaatttcccctcgtcaaaaataaggt
tatcaagtgagaaatcaccatgagtgacgactgaatccggtgagaatg
gcaaaagtttatgcatttctttccagacttgttcaacaggccagccat
tacgctcgtcatcaaaatcactcgcatcaaccaaaccgttattcattc
gtgattgcgcctgagcgagacgaaatacgcgatcgctgttaaaaggac
aattacaaacaggaatcgaatgcaaccggcgcaggaacactgccagcg
catcaacaatattttcacctgaatcaggatattcttctaatacctgga
atgctgttttcccggggatcgcagtggtgagtaaccatgcatcatcag
gagtacggataaaatgcttgatggtcggaagaggcataaattccgtca
gccagtttagtctgaccatctcatctgtaacatcattggcaacgctac
ctttgccatgtttcagaaacaactctggcgcatcgggcttcccataca -continued atcgatagattgtcgcacctgattgcccgacattatcgcgagcccatt
tatacccatataaatcagcatccatgttggaatttaatcgcggcctag
agcaagacgtttcccgttgaatatggctcataacaccccttgtattac
tgtttatgtaagcagacagttttattgttcatgaccaaaatcccttaa
cgtgagttttcgttccactgagcgtcagaccccgtagaaaagatcaaa
ggatcttcttgagatcctttttttctgcgcgtaatctgctgcttgcaa
acaaaaaaaccaccgctaccagcggtggtttgtttgccggatcaagag
ctaccaactctttttccgaaggtaactggcttcagcagagcgcagata
ccaaatactgtccttctagtgtagccgtagttaggccaccacttcaag
aactctgtagcaccgcctacatacctcgctctgctaatcctgttacca
gtggctgctgccagtggcgataagtcgtgtcttaccgggttggactca
agacgatagttaccggataaggcgcagcggtcgggctgaacggggggt
tcgtgcacacagcccagcttggagcgaacgacctacaccgaactgaga
tacctacagcgtgagctatgagaaagcgccacgcttcccgaagggaga
aaggcggacaggtatccggtaagcggcagggtcggaacaggagagcgc
acgagggagcttccagggggaaacgcctggtatctttatagtcctgtc
gggtttcgccacctctgacttgagcgtcgatttttgtgatgctcgtca
ggggggcggagcctatggaaaaacgccagcaacgcggcctttttacgg
ttcctggccttttgctggccttttgctcacatgttctttcctgcgtta
tcccctgattctgtggataaccgtattaccgcctttgagtgagctgat
accgctcgccgcagccgaacgaccgagcgcagcgagtcagtgagcgag
gaagcggaagagcgcctgatgcggtattttctccttacgcatctgtgc
ggtatttcacaccgcatatatggtgcactctcagtacaatctgctctg
atgccgcatagttaagccagtatacactccgctatcgctacgtgactg
ggtcatggctgcgccccgacacccgccaacacccgctgacgcgccctg
acgggcttgtctgctcccggcatccgcttacagacaagctgtgaccgt
ctccgggagctgcatgtgtcagaggttttcaccgtcatcaccgaaacg
cgcgaggcagctgcggtaaagctcatcagcgtggtcgtgaagcgattc
acagatgtctgcctgttcatccgcgtccagctcgttgagtttctccag
aagcgttaatgtctggcttctgataaagcgggccatgttaagggcggt
tttttcctgtttggtcactgatgcctccgtgtaagggggatttctgtt
catgggggtaatgataccgatgaaacgagagaggatgctcacgatacg
ggttactgatgatgaacatgcccggttactggaacgttgtgagggtaa
acaactggcggtatggatgcggcgggaccagagaaaaatcactcaggg
tcaatgccagcgcttcgttaatacagatgtaggtgttccacagggtag
ccagcagcatcctgcgatgcagatccggaacataatggtgcagggcgc
tgacttccgcgtttccagactttacgaaacacggaaaccgaagaccat
tcatgttgttgctcaggtcgcagacgttttgcagcagcagtcgcttca
cgttcgctcgcgtatcggtgattcattctgctaaccagtaaggcaacc
ccgccagcctagccgggtcctcaacgacaggagcacgatcatgcgcac -continued ccgtggggccgccatgccggcgataatggcctgcttctcgccgaaacg tttggtggcgggaccagtgacgaaggcttgagcgagggcgtgcaagat tccgaataccgcaagcgacaggccgatcatcgtcgcgctccagcgaaa gcggtcctcgccgaaaatgacccagagcgctgccggcacctgtcctac gagttgcatgataaagaagacagtcataagtgcggcgacgatagtcat gccccgcgcccaccggaaggagctgactgggttgaaggctctcaaggg catcggtcgagatcccggtgcctaatgagtgagctaacttacattaat tgcgttgcgctcactgcccgctttccagtcgggaaacctgtcgtgcca gctgcattaatgaatcggccaacgcgcggggagaggcggtttgcgtat tgggcgccagggtggtttttcttttcaccagtgagacgggcaacagct gattgcccttcaccgcctggccctgagagagttgcagcaagcggtcca cgctggtttgccccagcaggcgaaaatcctgtttgatggtggttaacg gcgggatataacatgagctgtcttcggtatcgtcgtatcccactaccg agatatccgcaccaacgcgcagcccggactcggtaatggcgcgcattg cgcccagcgccatctgatcgttggcaaccagcatcgcagtgggaacga tgccctcattcagcatttgcatggtttgttgaaaaccggacatggcac tccagtcgccttcccgttccgctatcggctgaatttgattgcgagtga gatatttatgccagccagccagacgcagacgcgccgagacagaactta atgggcccgctaacagcgcgatttgctggtgacccaatgcgaccagat gctccacgcccagtcgcgtaccgtcttcatgggagaaaataatactgt tgatgggtgtctggtcagagacatcaagaaataacgccggaacattag tgcaggcagcttccacagcaatggcatcctggtcatccagcggatagt taatgatcagcccactgacgcgttgcgcgagaagattgtgcaccgccg ctttacaggcttcgacgccgcttcgttctaccatcgacaccaccacgc tggcacccagttgatcggcgcgagatttaatcgccgcgacaatttgcg acggcgcgtgcagggccagactggaggtggcaacgccaatcagcaacg actgtttgcccgccagttgttgtgccacgcggttgggaatgtaattca gctccgccatcgccgcttccactttttcccgcgttttcgcagaaacgt ggctggcctggttcaccacgcgggaaacggtctgataagagacaccgg catactctgcgacatcgtataacgttactggtttcacattcaccaccc tgaattgactctcttccgggcgctatcatgccataccgcgaaaggttt tgcgccattcgatggtgtccgggatctcgacgctctcccttatgcgac tcctgcattaggaagcagcccagtagtaggttgaggccgttgagcacc gccgccgcaaggaatggtgcatgcaaggagatggcgcccaacagtccc ccggccacggggcctgccaccatacccacgccgaaacaagcgctcatg agcccgaagtggcgagcccgatcttccccatcggtgatgtcggcgata taggcgccagcaaccgcacctgtggcgccggtgatgccggccacgatg cgtccggcgtagaggatcgagatctcgatcccgcgaaattaatacgac tcactataggggaattgtgagcggataacaattcccctctagaaataa ttttgtttaactttaagaaggagatatacatatggaagctcgtcgttc tgcgaactacgaacctaacagctgggactatgattacctgctgtcctc -continued cgacacggacgagtccatcgaagtatacaaagacaaagcgaaaaagct ggaagccgaagttcgtcgcgagattaataacgaaaaagcagaatttct gaccctgctggaactgattgacaacgtccagcgcctgggcctgggtta ccgtttcgagtctgatatccgtggtgcgctggatcgcttcgtttcctc cggcggcttcgatgcggtaaccaagacttccctgcacggtacggcact gtctttccgtctgctgcgtcaacacggttttgaggtttctcaggaagc gttcagcggcttcaaagaccaaaacggcaacttcctggagaacctgaa ggaagatatcaaagctatcctgagcctgtacgaggccagcttcctggc tctggaaggcgaaaacatcctggacgaggcgaaggttttcgcaatctc tcatctgaaagaactgtctgaagaaaagatcggtaaagagctggcaga acaggtgaaccatgcactggaactgccactgcatcgccgtactcagcg tctggaagcagtatggtctatcgaggcctaccgtaaaaaggaggacgc gaatcaggttctgctggagctggcaattctggattacaacatgatcca gtctgtataccagcgtgatctgcgtgaaacgtcccgttggtggcgtcg tgtgggtctggcgaccaaactgcactttgctcgtgaccgcctgattga gagcttctactgggccgtgggtgtagcattcgaaccgcaatactccga ctgccgtaactccgtcgcaaaaatgttttctttcgtaaccattatcga cgatatctacgatgtatacggcaccctggacgaactggagctgtttac tgatgcagttgagcgttgggacgtaaacgccatcaacgacctgccgga ttacatgaaactgtgctttctggctctgtataacactattaacgaaat cgcctacgacaacctgaaagataaaggtgagaacatcctgccgtatct gaccaaagcctgggctgacctgtgcaacgctttcctgcaagaagccaa gtggctgtacaacaaatctactccgacctttgacgactacttcggcaa cgcatggaaatcctcttctggcccgctgcaactggtgttcgcttactt cgctgtcgtgcagaacattaaaaaggaagagatcgaaaacctgcaaaa ataccatgacaccatctctcgtccttcccatatcttccgtctgtgcaa tgacctggctagcgcgtctgcggaaattgcgcgtggtgaaaccaacaa tagcgtttcttgttacatgcgcactaaaggtatctccgaagaactggc taccgaaagcgtgatgaatctgatcgatgaaacctggaaaaagatgaa caaggaaaaactgggtggtagcccgttcgcgaaaccgttcgtggaaac cgcgatcaacctggcacgtcaatctcactgcacttatcataacggcga cgcgcatacctctccggatgagctgacccgcaaacgcgttctgtctgt aatcactgaaccgattctgccgtttgaacgcgaaaacctgtattttca gggcctcgagcaccaccaccaccaccactgagatccggctgctaacaa agcccgaaaggaagctgagttggctgctgccaccgctgagcaataact agcataaccccttggggcctctaaacgggtcttgaggggttttttgct gaaaggaggaactatatccggat 8) Amino Acid Sequence of P. alba MEA A453N T536C (+)TEV - pDW105 (NC) (SEQ ID NO: 77)
MEARRSANYEPNSWDYDYLLSSDTDESIEVYKDKAKKLEAEVRREINN
EKAEFLTLLELIDNVQRLGLGYRFESDIRGALDRFVSSGGFDAVTKTS
LHGTALSFRLLRQHGFEVSQEAFSGFKDQNGNFLENLKEDIKAILSLY
EASFLALEGENILDEAKVFAISHLKELSEEKIGKELAEQVNHALELPL
HRRTQRLEAVWSIEAYRKKEDANQVLLELAILDYNMIQSVYQRDLRET
SRWWRRVGLATKLHFARDRLIESFYWAVGVAFEPQYSDCRNSVAKMFS
FVTIIDDIYDVYGTLDELELFTDAVERWDVNAINDLPDYMKLCFLALY
NTINEIAYDNLKDKGENILPYLTKAWADLCNAFLQEAKWLYNKSTPTF
DDYFGNAWKSSSGPLQLVFAYFAVVQNIKKEEIENLQKYHDTISRPSH
IFRLCNDLASASAEIARGETNNSVSCYMRTKGISEELATESVMNLIDE
TWKKMNKEKLGGSLFAKPFVETAINLARQSHCTYHNGDAHTSPDELTR
KRVLSVICEPILPFERENLYFQGLEHHHHHH DNA sequence of pDW105 (SEQ ID NO: 78)
tggcgaatgggacgcgccctgtagcggcgcattaagcgcggcgggtgt
ggtggttacgcgcagcgtgaccgctacacttgccagcgccctagcgcc
cgctcctttcgctttcttcccttcctttctcgccacgttcgccggctt
tccccgtcaagctctaaatcgggggctccctttagggttccgatttag
tgctttacggcacctcgaccccaaaaaacttgattagggtgatggttc
acgtagtgggccatcgccctgatagacggtttttcgccctttgacgtt
ggagtccacgttctttaatagtggactcttgttccaaactggaacaac
actcaaccctatctcggtctattcttttgatttataagggattttgcc
gatttcggcctattggttaaaaaatgagctgatttaacaaaaatttaa
cgcgaattttaacaaaatattaacgtttacaatttcaggtggcacttt
tcggggaaatgtgcgcggaacccctatttgtttatttttctaaataca
ttcaaatatgtatccgctcatgaattaattcttagaaaaactcatcga
gcatcaaatgaaactgcaatttattcatatcaggattatcaataccat
atttttgaaaaagccgtttctgtaatgaaggagaaaactcaccgaggc
agttccataggatggcaagatcctggtatcggtctgcgattccgactc
gtccaacatcaatacaacctattaatttcccctcgtcaaaaataaggt
tatcaagtgagaaatcaccatgagtgacgactgaatccggtgagaatg
gcaaaagtttatgcatttctttccagacttgttcaacaggccagccat
tacgctcgtcatcaaaatcactcgcatcaaccaaaccgttattcattc
gtgattgcgcctgagcgagacgaaatacgcgatcgctgttaaaaggac
aattacaaacaggaatcgaatgcaaccggcgcaggaacactgccagcg
catcaacaatattttcacctgaatcaggatattcttctaatacctgga
atgctgttttcccggggatcgcagtggtgagtaaccatgcatcatcag
gagtacggataaaatgcttgatggtcggaagaggcataaattccgtca
gccagtttagtctgaccatctcatctgtaacatcattggcaacgctac
ctttgccatgtttcagaaacaactctggcgcatcgggcttcccataca -continued atcgatagattgtcgcacctgattgcccgacattatcgcgagcccatt
tatacccatataaatcagcatccatgttggaatttaatcgcggcctag
agcaagacgtttcccgttgaatatggctcataacaccccttgtattac
tgtttatgtaagcagacagttttattgttcatgaccaaaatcccttaa
cgtgagttttcgttccactgagcgtcagaccccgtagaaaagatcaaa
ggatcttcttgagatcctttttttctgcgcgtaatctgctgcttgcaa
acaaaaaaaccaccgctaccagcggtggtttgtttgccggatcaagag
ctaccaactctttttccgaaggtaactggcttcagcagagcgcagata
ccaaatactgtccttctagtgtagccgtagttaggccaccacttcaag
aactctgtagcaccgcctacatacctcgctctgctaatcctgttacca
gtggctgctgccagtggcgataagtcgtgtcttaccgggttggactca
agacgatagttaccggataaggcgcagcggtcgggctgaacggggggt
tcgtgcacacagcccagcttggagcgaacgacctacaccgaactgaga
tacctacagcgtgagctatgagaaagcgccacgcttcccgaagggaga
aaggcggacaggtatccggtaagcggcagggtcggaacaggagagcgc
acgagggagcttccagggggaaacgcctggtatctttatagtcctgtc
gggtttcgccacctctgacttgagcgtcgatttttgtgatgctcgtca
ggggggcggagcctatggaaaaacgccagcaacgcggcctttttacgg
ttcctggccttttgctggccttttgctcacatgttctttcctgcgtta
tcccctgattctgtggataaccgtattaccgcctttgagtgagctgat
accgctcgccgcagccgaacgaccgagcgcagcgagtcagtgagcgag
gaagcggaagagcgcctgatgcggtattttctccttacgcatctgtgc
ggtatttcacaccgcatatatggtgcactctcagtacaatctgctctg
atgccgcatagttaagccagtatacactccgctatcgctacgtgactg
ggtcatggctgcgccccgacacccgccaacacccgctgacgcgccctg
acgggcttgtctgctcccggcatccgcttacagacaagctgtgaccgt
ctccgggagctgcatgtgtcagaggttttcaccgtcatcaccgaaacg
cgcgaggcagctgcggtaaagctcatcagcgtggtcgtgaagcgattc
acagatgtctgcctgttcatccgcgtccagctcgttgagtttctccag
aagcgttaatgtctggcttctgataaagcgggccatgttaagggcggt
tttttcctgtttggtcactgatgcctccgtgtaagggggatttctgtt
catgggggtaatgataccgatgaaacgagagaggatgctcacgatacg
ggttactgatgatgaacatgcccggttactggaacgttgtgagggtaa
acaactggcggtatggatgcggcgggaccagagaaaaatcactcaggg
tcaatgccagcgcttcgttaatacagatgtaggtgttccacagggtag
ccagcagcatcctgcgatgcagatccggaacataatggtgcagggcgc
tgacttccgcgtttccagactttacgaaacacggaaaccgaagaccat
tcatgttgttgctcaggtcgcagacgttttgcagcagcagtcgcttca
cgttcgctcgcgtatcggtgattcattctgctaaccagtaaggcaacc
ccgccagcctagccgggtcctcaacgacaggagcacgatcatgcgcac -continued ccgtggggccgccatgccggcgataatggcctgcttctcgccgaaacg tttggtggcgggaccagtgacgaaggcttgagcgagggcgtgcaagat tccgaataccgcaagcgacaggccgatcatcgtcgcgctccagcgaaa gcggtcctcgccgaaaatgacccagagcgctgccggcacctgtcctac gagttgcatgataaagaagacagtcataagtgcggcgacgatagtcat gccccgcgcccaccggaaggagctgactgggttgaaggctctcaaggg catcggtcgagatcccggtgcctaatgagtgagctaacttacattaat tgcgttgcgctcactgcccgctttccagtcgggaaacctgtcgtgcca gctgcattaatgaatcggccaacgcgcggggagaggcggtttgcgtat tgggcgccagggtggtttttcttttcaccagtgagacgggcaacagct gattgcccttcaccgcctggccctgagagagttgcagcaagcggtcca cgctggtttgccccagcaggcgaaaatcctgtttgatggtggttaacg gcgggatataacatgagctgtcttcggtatcgtcgtatcccactaccg agatatccgcaccaacgcgcagcccggactcggtaatggcgcgcattg cgcccagcgccatctgatcgttggcaaccagcatcgcagtgggaacga tgccctcattcagcatttgcatggtttgttgaaaaccggacatggcac tccagtcgccttcccgttccgctatcggctgaatttgattgcgagtga gatatttatgccagccagccagacgcagacgcgccgagacagaactta atgggcccgctaacagcgcgatttgctggtgacccaatgcgaccagat gctccacgcccagtcgcgtaccgtcttcatgggagaaaataatactgt tgatgggtgtctggtcagagacatcaagaaataacgccggaacattag tgcaggcagcttccacagcaatggcatcctggtcatccagcggatagt taatgatcagcccactgacgcgttgcgcgagaagattgtgcaccgccg ctttacaggcttcgacgccgcttcgttctaccatcgacaccaccacgc tggcacccagttgatcggcgcgagatttaatcgccgcgacaatttgcg acggcgcgtgcagggccagactggaggtggcaacgccaatcagcaacg actgtttgcccgccagttgttgtgccacgcggttgggaatgtaattca gctccgccatcgccgcttccactttttcccgcgttttcgcagaaacgt ggctggcctggttcaccacgcgggaaacggtctgataagagacaccgg catactctgcgacatcgtataacgttactggtttcacattcaccaccc tgaattgactctcttccgggcgctatcatgccataccgcgaaaggttt tgcgccattcgatggtgtccgggatctcgacgctctcccttatgcgac tcctgcattaggaagcagcccagtagtaggttgaggccgttgagcacc gccgccgcaaggaatggtgcatgcaaggagatggcgcccaacagtccc ccggccacggggcctgccaccatacccacgccgaaacaagcgctcatg agcccgaagtggcgagcccgatcttccccatcggtgatgtcggcgata taggcgccagcaaccgcacctgtggcgccggtgatgccggccacgatg cgtccggcgtagaggatcgagatctcgatcccgcgaaattaatacgac tcactataggggaattgtgagcggataacaattcccctctagaaataa ttttgtttaactttaagaaggagatatacatatggaagctcgtcgttc tgcgaactacgaacctaacagctgggactatgattacctgctgtcctc -continued cgacacggacgagtccatcgaagtatacaaagacaaagcgaaaaagct ggaagccgaagttcgtcgcgagattaataacgaaaaagcagaatttct gaccctgctggaactgattgacaacgtccagcgcctgggcctgggtta ccgtttcgagtctgatatccgtggtgcgctggatcgcttcgtttcctc cggcggcttcgatgcggtaaccaagacttccctgcacggtacggcact gtctttccgtctgctgcgtcaacacggttttgaggtttctcaggaagc gttcagcggcttcaaagaccaaaacggcaacttcctggagaacctgaa ggaagatatcaaagctatcctgagcctgtacgaggccagcttcctggc tctggaaggcgaaaacatcctggacgaggcgaaggttttcgcaatctc tcatctgaaagaactgtctgaagaaaagatcggtaaagagctggcaga acaggtgaaccatgcactggaactgccactgcatcgccgtactcagcg tctggaagcagtatggtctatcgaggcctaccgtaaaaaggaggacgc gaatcaggttctgctggagctggcaattctggattacaacatgatcca gtctgtataccagcgtgatctgcgtgaaacgtcccgttggtggcgtcg tgtgggtctggcgaccaaactgcactttgctcgtgaccgcctgattga gagcttctactgggccgtgggtgtagcattcgaaccgcaatactccga ctgccgtaactccgtcgcaaaaatgttttctttcgtaaccattatcga cgatatctacgatgtatacggcaccctggacgaactggagctgtttac tgatgcagttgagcgttgggacgtaaacgccatcaacgacctgccgga ttacatgaaactgtgctttctggctctgtataacactattaacgaaat cgcctacgacaacctgaaagataaaggtgagaacatcctgccgtatct gaccaaagcctgggctgacctgtgcaacgctttcctgcaagaagccaa gtggctgtacaacaaatctactccgacctttgacgactacttcggcaa cgcatggaaatcctcttctggcccgctgcaactggtgttcgcttactt cgctgtcgtgcagaacattaaaaaggaagagatcgaaaacctgcaaaa ataccatgacaccatctctcgtccttcccatatcttccgtctgtgcaa tgacctggctagcgcgtctgcggaaattgcgcgtggtgaaaccaacaa tagcgtttcttgttacatgcgcactaaaggtatctccgaagaactggc taccgaaagcgtgatgaatctgatcgatgaaacctggaaaaagatgaa caaggaaaaactgggtggtagcctgttcgcgaaaccgttcgtggaaac cgcgatcaacctggcacgtcaatctcactgcacttatcataacggcga cgcgcatacctctccggatgagctgacccgcaaacgcgttctgtctgt aatctgcgaaccgattctgccgtttgaacgcgaaaacctgtattttca gggcctcgagcaccaccaccaccaccactgagatccggctgctaacaa agcccgaaaggaagctgagttggctgctgccaccgctgagcaataact agcataaccccttggggcctctaaacgggtcttgaggggttttttgct gaaaggaggaactatatccggat 9) Amino Acid Sequence of P. alba MEA A453N G491S L494P (+)TEV - pDW106 (NSP) (SEQ ID NO: 79)

MEARRSANYEPNSWDYDYLLSSDTDESIEVYKDKAKKLEAEVRREINN
EKAEFLTLLELIDNVQRLGLGYRFESDIRGALDRFVSSGGFDAVTKTS
LHGTALSFRLLRQHGFEVSQEAFSGFKDQNGNFLENLKEDIKAILSLY
EASFLALEGENILDEAKVFAISHLKELSEEKIGKELAEQVNHALELPL
HRRTQRLEAVWSIEAYRKKEDANQVLLELAILDYNMIQSVYQRDLRET
SRWWRRVGLATKLHFARDRLIESFYWAVGVAFEPQYSDCRNSVAKMFS
FVTIIDDIYDVYGTLDELELFTDAVERWDVNAINDLPDYMKLCFLALY
NTINEIAYDNLKDKGENILPYLTKAWADLCNAFLQEAKWLYNKSTPTF
DDYFGNAWKSSSGPLQLVFAYFAVVQNIKKEEIENLQKYHDTISRPSH
IFRLCNDLASASAEIARGETNNSVSCYMRTKGISEELATESVMNLIDE
TWKKMNKEKLSGSPFAKPFVETAINLARQSHCTYHNGDAHTSPDELTR
KRVLSVITEPILPFERENLYFQGLEHHHHHH

DNA sequence of pDW106 (SEQ ID NO: 80)

tggcgaatgggacgcgccctgtagcggcgcattaagcgcggcgggtgt
ggtggttacgcgcagcgtgaccgctacacttgccagcgccctagcgcc
cgctcctttcgctttcttcccttcctttctcgccacgttcgccggctt
tccccgtcaagctctaaatcgggggctccctttagggttccgatttag
tgctttacggcacctcgaccccaaaaaacttgattagggtgatggttc
acgtagtgggccatcgccctgatagacggtttttcgccctttgacgtt
ggagtccacgttctttaatagtggactcttgttccaaactggaacaac
actcaaccctatctcggtctattcttttgatttataagggattttgcc
gatttcggcctattggttaaaaaatgagctgatttaacaaaaatttaa
cgcgaattttaacaaaatattaacgtttacaatttcaggtggcacttt
tcggggaaatgtgcgcggaacccctatttgtttatttttctaaataca
ttcaaatatgtatccgctcatgaattaattcttagaaaaactcatcga
gcatcaaatgaaactgcaatttattcatatcaggattatcaataccat
atttttgaaaaagccgtttctgtaatgaaggagaaaactcaccgaggc
agttccataggatggcaagatcctggtatcggtctgcgattccgactc
gtccaacatcaatacaacctattaatttcccctcgtcaaaaataaggt
tatcaagtgagaaatcaccatgagtgacgactgaatccggtgagaatg
gcaaaagtttatgcatttctttccagacttgttcaacaggccagccat
tacgctcgtcatcaaaatcactcgcatcaaccaaaccgttattcattc
gtgattgcgcctgagcgagacgaaatacgcgatcgctgttaaaaggac
aattacaaacaggaatcgaatgcaaccggcgcaggaacactgccagcg
catcaacaatattttcacctgaatcaggatattcttctaatacctgga
atgctgttttcccggggatcgcagtggtgagtaaccatgcatcatcag
gagtacggataaaatgcttgatggtcggaagaggcataaattccgtca
gccagtttagtctgaccatctcatctgtaacatcattggcaacgctac -continued ctttgccatgtttcagaaacaactctggcgcatcgggcttcccataca
atcgatagattgtcgcacctgattgcccgacattatcgcgagcccatt
tatacccatataaatcagcatccatgttggaatttaatcgcggcctag
agcaagacgtttcccgttgaatatggctcataacaccccttgtattac
tgtttatgtaagcagacagttttattgttcatgaccaaaatcccttaa
cgtgagttttcgttccactgagcgtcagaccccgtagaaaagatcaaa
ggatcttcttgagatcctttttttctgcgcgtaatctgctgcttgcaa
acaaaaaaaccaccgctaccagcggtggtttgtttgccggatcaagag
ctaccaactctttttccgaaggtaactggcttcagcagagcgcagata
ccaaatactgtccttctagtgtagccgtagttaggccaccacttcaag
aactctgtagcaccgcctacatacctcgctctgctaatcctgttacca
gtggctgctgccagtggcgataagtcgtgtcttaccgggttggactca
agacgatagttaccggataaggcgcagcggtcgggctgaacggggggt
tcgtgcacacagcccagcttggagcgaacgacctacaccgaactgaga
tacctacagcgtgagctatgagaaagcgccacgcttcccgaagggaga
aaggcggacaggtatccggtaagcggcagggtcggaacaggagagcgc
acgagggagcttccagggggaaacgcctggtatctttatagtcctgtc
gggtttcgccacctctgacttgagcgtcgatttttgtgatgctcgtca
ggggggcggagcctatggaaaaacgccagcaacgcggcctttttacgg
ttcctggccttttgctggccttttgctcacatgttctttcctgcgtta
tcccctgattctgtggataaccgtattaccgcctttgagtgagctgat
accgctcgccgcagccgaacgaccgagcgcagcgagtcagtgagcgag
gaagcggaagagcgcctgatgcggtattttctccttacgcatctgtgc
ggtatttcacaccgcatatatggtgcactctcagtacaatctgctctg
atgccgcatagttaagccagtatacactccgctatcgctacgtgactg
ggtcatggctgcgccccgacacccgccaacacccgctgacgcgccctg
acgggcttgtctgctcccggcatccgcttacagacaagctgtgaccgt
ctccgggagctgcatgtgtcagaggttttcaccgtcatcaccgaaacg
cgcgaggcagctgcggtaaagctcatcagcgtggtcgtgaagcgattc
acagatgtctgcctgttcatccgcgtccagctcgttgagtttctccag
aagcgttaatgtctggcttctgataaagcgggccatgttaagggcggt
ttttcctgtttggtcactgatgcctccgtgtaagggggatttctgtt
catgggggtaatgataccgatgaaacgagagaggatgctcacgatacg
ggttactgatgatgaacatgcccggttactggaacgttgtgagggtaa
acaactggcggtatggatgcggcgggaccagagaaaaatcactcaggg
tcaatgccagcgcttcgttaatacagatgtaggtgttccacagggtag
ccagcagcatcctgcgatgcagatccggaacataatggtgcagggcgc
tgacttccgcgtttccagactttacgaaacacggaaaccgaagaccat
tcatgttgttgctcaggtcgcagacgttttgcagcagcagtcgcttca
cgttcgctcgcgtatcggtgattcattctgctaaccagtaaggcaacc
ccgccagcctagccgggtcctcaacgacaggagcacgatcatgcgcac -continued ccgtggggccgccatgccggcgataatggcctgcttctcgccgaaacg
tttggtggcgggaccagtgacgaaggcttgagcgagggcgtgcaagat
tccgaataccgcaagcgacaggccgatcatcgtcgcgctccagcgaaa
gcggtcctcgccgaaaatgacccagagcgctgccggcacctgtcctac
gagttgcatgataaagaagacagtcataagtgcggcgacgatagtcat
gccccgcgcccaccggaaggagctgactgggttgaaggctctcaaggg
catcggtcgagatcccggtgcctaatgagtgagctaacttacattaat
tgcgttgcgctcactgcccgctttccagtcgggaaacctgtcgtgcca
gctgcattaatgaatcggccaacgcgcggggagaggcggtttgcgtat
tgggcgccagggtggtttttcttttcaccagtgagacgggcaacagct
gattgcccttcaccgcctggccctgagagagttgcagcaagcggtcca
cgctggtttgccccagcaggcgaaaatcctgtttgatggtggttaacg
gcgggatataacatgagctgtcttcggtatcgtcgtatcccactaccg
agatatccgcaccaacgcgcagcccggactcggtaatggcgcgcattg
cgcccagcgccatctgatcgttggcaaccagcatcgcagtgggaacga
tgccctcattcagcatttgcatggtttgttgaaaaccggacatggcac
tccagtcgccttcccgttccgctatcggctgaatttgattgcgagtga
gatatttatgccagccagccagacgcagacgcgccgagacagaactta
atgggcccgctaacagcgcgatttgctggtgacccaatgcgaccagat
gctccacgcccagtcgcgtaccgtcttcatgggagaaaataatactgt
tgatgggtgtctggtcagagacatcaagaaataacgccggaacattag
tgcaggcagcttccacagcaatggcatcctggtcatccagcggatagt
taatgatcagcccactgacgcgttgcgcgagaagattgtgcaccgccg
ctttacaggcttcgacgccgcttcgttctaccatcgacaccaccacgc
tggcacccagttgatcggcgcgagatttaatcgccgcgacaatttgcg
acggcgcgtgcagggccagactggaggtggcaacgccaatcagcaacg
actgtttgcccgccagttgttgtgccacgcggttgggaatgtaattca
gctccgccatcgccgcttccacttttcccgcgttttcgcagaaacgt
ggctggcctggttcaccacgcgggaaacggtctgataagagacaccgg
catactctgcgacatcgtataacgttactggtttcacattcaccaccc
tgaattgactctcttccgggcgctatcatgccataccgcgaaaggttt
tgcgccattcgatggtgtccgggatctcgacgctctcccttatgcgac
tcctgcattaggaagcagcccagtagtaggttgaggccgttgagcacc
gccgccgcaaggaatggtgcatgcaaggagatggcgcccaacagtccc
ccggccacggggcctgccaccatacccacgccgaaacaagcgctcatg
agcccgaagtggcgagcccgatcttccccatcggtgatgtcggcgata
taggcgccagcaaccgcacctgtggcgccggtgatgccggccacgatg
cgtccggcgtagaggatcgagatctcgatcccgcgaaattaatacgac
tcactataggggaattgtgagcggataacaattcccctctagaaataa
ttttgtttaactttaagaaggagatatacatatggaagctcgtcgttc
tgcgaactacgaacctaacagctgggactatgattacctgctgtcctc
cgacacggacgagtccatcgaagtatacaaagacaaagcgaaaaagct
ggaagccgaagttcgtcgcgagattaataacgaaaaagcagaatttct
gaccctgctggaactgattgacaacgtccagcgcctgggcctgggtta
ccgtttcgagtctgatatccgtggtgcgctggatcgcttcgtttcctc
cggcggcttcgatgcggtaaccaagacttccctgcacggtacggcact
gtctttccgtctgctgcgtcaacacggttttgaggtttctcaggaagc
gttcagcggcttcaaagaccaaaacggcaacttcctggagaacctgaa
ggaagatatcaaagctatcctgagcctgtacgaggccagcttcctggc
tctggaaggcgaaaacatcctggacgaggcgaaggttttcgcaatctc
tcatctgaaagaactgtctgaagaaaagatcggtaaagagctggcaga
acaggtgaaccatgcactggaactgccactgcatcgccgtactcagcg
tctggaagcagtatggtctatcgaggcctaccgtaaaaaggaggacgc
gaatcaggttctgctggagctggcaattctggattacaacatgatcca
gtctgtataccagcgtgatctgcgtgaaacgtcccgttggtggcgtcg
tgtgggtctggcgaccaaactgcactttgctcgtgaccgcctgattga
gagcttctactgggccgtgggtgtagcattcgaaccgcaatactccga
ctgccgtaactccgtcgcaaaaatgttttctttcgtaaccattatcga
cgatatctacgatgtatacggcaccctggacgaactggagctgtttac
tgatgcagttgagcgttgggacgtaaacgccatcaacgacctgccgga
ttacatgaaactgtgctttctggctctgtataacactattaacgaaat
cgcctacgacaacctgaaagataaaggtgagaacatcctgccgtatct
gaccaaagcctgggctgacctgtgcaacgctttcctgcaagaagccaa
gtggctgtacaacaaatctactccgacctttgacgactacttcggcaa
cgcatggaaatcctcttctggcccgctgcaactggtgttcgcttactt
cgctgtcgtgcagaacattaaaaaggaagagatcgaaaacctgcaaaa
ataccatgacaccatctctcgtccttcccatatcttccgtctgtgcaa
tgacctggctagcgcgtctgcggaaattgcgcgtggtgaaaccaacaa
tagcgtttcttgttacatgcgcactaaaggtatctccgaagaactggc
taccgaaagcgtgatgaatctgatcgatgaaacctggaaaaagatgaa
caaggaaaaactgagtggtagcccgttcgcgaaaccgttcgtggaaac
cgcgatcaacctggcacgtcaatctcactgcacttatcataacggcga
cgcgcatacctctccggatgagctgacccgcaaacgcgttctgtctgt
aatcactgaaccgattctgccgtttgaacgcgaaaacctgtattttca
gggcctcgagcaccaccaccaccaccactgagatccggctgctaacaa
agcccgaaaggaagctgagttggctgctgccaccgctgagcaataact
agcataaccccttggggcctctaaacgggtcttgaggggttttttgct
gaaaggaggaactatatccggat 10) Amino Acid Sequence of P. alba MEA A453N G491S T536C (+)TEV - pDW107 (NSC) (SEQ ID NO: 81)

MEARRSANYEPNSWDYDYLLSSDTDESIEVYKDKAKKLEAEVRREINN
EKAEFLTLLELIDNVQRLGLGYRFESDIRGALDRFVSSGGFDAVTKTS
LHGTALSFRLLRQHGFEVSQEAFSGFKDQNGNFLENLKEDIKAILSLY
EASFLALEGENILDEAKVFAISHLKELSEEKIGKELAEQVNHALELPL
HRRTQRLEAVWSIEAYRKKEDANQVLLELAILDYNMIQSVYQRDLRET
SRWWRRVGLATKLHFARDRLIESFYWAVGVAFEPQYSDCRNSVAKMFS
FVTIIDDIYDVYGTLDELELFTDAVERWDVNAINDLPDYMKLCFLALY
NTINEIAYDNLKDKGENILPYLTKAWADLCNAFLQEAKWLYNKSTPTF
DDYFGNAWKSSSGPLQLVFAYFAVVQNIKKEEIENLQKYHDTISRPSH
IFRLCNDLASASAEIARGETNNSVSCYMRTKGISEELATESVMNLIDE
TWKKMNKEKLSGSLFAKPFVETAINLARQSHCTYHNGDAHTSPDELTR
KRVLSVICEPILPFERENLYFQGLEHHHHHH

DNA sequence of pDW107 (SEQ ID NO: 82)

tggcgaatgggacgcgccctgtagcggcgcattaagcgcggcgggtgt
ggtggttacgcgcagcgtgaccgctacacttgccagcgccctagcgcc
cgctcctttcgctttcttcccttcctttctcgccacgttcgccggctt
tccccgtcaagctctaaatcgggggctccctttagggttccgatttag
tgctttacggcacctcgaccccaaaaaacttgattagggtgatggttc
acgtagtgggccatcgccctgatagacggtttttcgccctttgacgtt
ggagtccacgttctttaatagtggactcttgttccaaactggaacaac
actcaaccctatctcggtctattcttttgatttataagggattttgcc
gatttcggcctattggttaaaaaatgagctgatttaacaaaaatttaa
cgcgaattttaacaaaatattaacgtttacaatttcaggtggcacttt
tcggggaaatgtgcgcggaacccctatttgtttatttttctaaataca
ttcaaatatgtatccgctcatgaattaattcttagaaaaactcatcga
gcatcaaatgaaactgcaatttattcatatcaggattatcaataccat
atttttgaaaaagccgtttctgtaatgaaggagaaaactcaccgaggc
agttccataggatggcaagatcctggtatcggtctgcgattccgactc
gtccaacatcaatacaacctattaatttcccctcgtcaaaaataaggt
tatcaagtgagaaatcaccatgagtgacgactgaatccggtgagaatg
gcaaaagtttatgcatttctttccagacttgttcaacaggccagccat
tacgctcgtcatcaaaatcactcgcatcaaccaaaccgttattcattc
gtgattgcgcctgagcgagacgaaatacgcgatcgctgttaaaaggac
aattacaaacaggaatcgaatgcaaccggcgcaggaacactgccagcg
catcaacaatattttcacctgaatcaggatattcttctaatacctgga
atgctgttttcccggggatcgcagtggtgagtaaccatgcatcatcag
gagtacggataaaatgcttgatggtcggaagaggcataaattccgtca
gccagtttagtctgaccatctcatctgtaacatcattggcaacgctac -continued ctttgccatgtttcagaaacaactctggcgcatcgggcttcccataca
atcgatagattgtcgcacctgattgcccgacattatcgcgagcccatt
tatacccatataaatcagcatccatgttggaatttaatcgcggcctag
agcaagacgtttcccgttgaatatggctcataacaccccttgtattac
tgtttatgtaagcagacagttttattgttcatgaccaaaatcccttaa
cgtgagttttcgttccactgagcgtcagaccccgtagaaaagatcaaa
ggatcttcttgagatcctttttttctgcgcgtaatctgctgcttgcaa
acaaaaaaaccaccgctaccagcggtggtttgtttgccggatcaagag
ctaccaactctttttccgaaggtaactggcttcagcagagcgcagata
ccaaatactgtccttctagtgtagccgtagttaggccaccacttcaag
aactctgtagcaccgcctacatacctcgctctgctaatcctgttacca
gtggctgctgccagtggcgataagtcgtgtcttaccgggttggactca
agacgatagttaccggataaggcgcagcggtcgggctgaacggggggt
tcgtgcacacagcccagcttggagcgaacgacctacaccgaactgaga
tacctacagcgtgagctatgagaaagcgccacgcttcccgaagggaga
aaggcggacaggtatccggtaagcggcagggtcggaacaggagagcgc
acgagggagcttccagggggaaacgcctggtatctttatagtcctgtc
gggtttcgccacctctgacttgagcgtcgatttttgtgatgctcgtca
ggggggcggagcctatggaaaaacgccagcaacgcggcctttttacgg
ttcctggccttttgctggccttttgctcacatgttctttcctgcgtta
tcccctgattctgtggataaccgtattaccgcctttgagtgagctgat
accgctcgccgcagccgaacgaccgagcgcagcgagtcagtgagcgag
gaagcggaagagcgcctgatgcggtattttctccttacgcatctgtgc
ggtatttcacaccgcatatatggtgcactctcagtacaatctgctctg
atgccgcatagttaagccagtatacactccgctatcgctacgtgactg
ggtcatggctgcgccccgacacccgccaacacccgctgacgcgccctg
acgggcttgtctgctcccggcatccgcttacagacaagctgtgaccgt
ctccgggagctgcatgtgtcagaggttttcaccgtcatcaccgaaacg
cgcgaggcagctgcggtaaagctcatcagcgtggtcgtgaagcgattc
acagatgtctgcctgttcatccgcgtccagctcgttgagtttctccag
aagcgttaatgtctggcttctgataaagcgggccatgttaagggcggt
tttttcctgtttggtcactgatgcctccgtgtaagggggatttctgtt
catgggggtaatgataccgatgaaacgagagaggatgctcacgatacg
ggttactgatgatgaacatgcccggttactggaacgttgtgagggtaa
acaactggcggtatggatgcggcgggaccagagaaaaatcactcaggg
tcaatgccagcgcttcgttaatacagatgtaggtgttccacagggtag
ccagcagcatcctgcgatgcagatccggaacataatggtgcagggcgc
tgacttccgcgtttccagactttacgaaacacggaaaccgaagaccat
tcatgttgttgctcaggtcgcagacgttttgcagcagcagtcgcttca
cgttcgctcgcgtatcggtgattcattctgctaaccagtaaggcaacc
ccgccagcctagccgggtcctcaacgacaggagcacgatcatgcgcac -continued ccgtggggccgccatgccggcgataatggcctgcttctcgccgaaacg
tttggtggcgggaccagtgacgaaggcttgagcgagggcgtgcaagat
tccgaataccgcaagcgacaggccgatcatcgtcgcgctccagcgaaa
gcggtcctcgccgaaaatgacccagagcgctgccggcacctgtcctac
gagttgcatgataaagaagacagtcataagtgcggcgacgatagtcat
gccccgcgcccaccggaaggagctgactgggttgaaggctctcaaggg
catcggtcgagatcccggtgcctaatgagtgagctaacttacattaat
tgcgttgcgctcactgcccgctttccagtcgggaaacctgtcgtgcca
gctgcattaatgaatcggccaacgcgcggggagaggcggtttgcgtat
tgggcgccagggtggtttttcttttcaccagtgagacgggcaacagct
gattgcccttcaccgcctggccctgagagagttgcagcaagcggtcca
cgctggtttgccccagcaggcgaaaatcctgtttgatggtggttaacg
gcgggatataacatgagctgtcttcggtatcgtcgtatcccactaccg
agatatccgcaccaacgcgcagcccggactcggtaatggcgcgcattg
cgcccagcgccatctgatcgttggcaaccagcatcgcagtgggaacga
tgccctcattcagcatttgcatggtttgttgaaaaccggacatggcac
tccagtcgccttcccgttccgctatcggctgaatttgattgcgagtga
gatatttatgccagccagccagacgcagacgcgccgagacagaactta
atgggcccgctaacagcgcgatttgctggtgacccaatgcgaccagat
gctccacgcccagtcgcgtaccgtcttcatgggagaaaataatactgt
tgatgggtgtctggtcagagacatcaagaaataacgccggaacattag
tgcaggcagcttccacagcaatggcatcctggtcatccagcggatagt
taatgatcagcccactgacgcgttgcgcgagaagattgtgcaccgccg
ctttacaggcttcgacgccgcttcgttctaccatcgacaccaccacgc
tggcacccagttgatcggcgcgagatttaatcgccgcgacaatttgcg
acggcgcgtgcagggccagactggaggtggcaacgccaatcagcaacg
actgtttgcccgccagttgttgtgccacgcggttgggaatgtaattca
gctccgccatcgccgcttccactttttcccgcgttttcgcagaaacgt
ggctggcctggttcaccacgcgggaaacggtctgataagagacaccgg
catactctgcgacatcgtataacgttactggtttcacattcaccaccc
tgaattgactctcttccgggcgctatcatgccataccgcgaaaggttt
tgcgccattcgatggtgtccgggatctcgacgctctcccttatgcgac
tcctgcattaggaagcagcccagtagtaggttgaggccgttgagcacc
gccgccgcaaggaatggtgcatgcaaggagatggcgcccaacagtccc
ccggccacggggcctgccaccatacccacgccgaaacaagcgctcatg
agcccgaagtggcgagcccgatcttccccatcggtgatgtcggcgata
taggcgccagcaaccgcacctgtggcgccggtgatgccggccacgatg
cgtccggcgtagaggatcgagatctcgatcccgcgaaattaatacgac
tcactataggggaattgtgagcggataacaattcccctctagaaataa
ttttgtttaactttaagaaggagatatacatatggaagctcgtcgttc -continued tgcgaactacgaacctaacagctgggactatgattacctgctgtcctc
cgacacggacgagtccatcgaagtatacaaagacaaagcgaaaaagct
ggaagccgaagttcgtcgcgagattaataacgaaaaagcagaatttct
gaccctgctggaactgattgacaacgtccagcgcctgggcctgggtta
ccgtttcgagtctgatatccgtggtgcgctggatcgcttcgtttcctc
cggcggcttcgatgcggtaaccaagacttccctgcacggtacggcact
gtctttccgtctgctgcgtcaacacggttttgaggtttctcaggaagc
gttcagcggcttcaaagaccaaaacggcaacttcctggagaacctgaa
ggaagatatcaaagctatcctgagcctgtacgaggccagcttcctggc
tctggaaggcgaaaacatcctggacgaggcgaaggttttcgcaatctc
tcatctgaaagaactgtctgaagaaaagatcggtaaagagctggcaga
acaggtgaaccatgcactggaactgccactgcatcgccgtactcagcg
tctggaagcagtatggtctatcgaggcctaccgtaaaaaggaggacgc
gaatcaggttctgctggagctggcaattctggattacaacatgatcca
gtctgtataccagcgtgatctgcgtgaaacgtcccgttggtggcgtcg
tgtgggtctggcgaccaaactgcactttgctcgtgaccgcctgattga
gagcttctactgggccgtgggtgtagcattcgaaccgcaatactccga
ctgccgtaactccgtcgcaaaaatgttttctttcgtaaccattatcga
cgatatctacgatgtatacggcaccctggacgaactggagctgtttac
tgatgcagttgagcgttgggacgtaaacgccatcaacgacctgccgga
ttacatgaaactgtgctttctggctctgtataacactattaacgaaat
cgcctacgacaacctgaaagataaaggtgagaacatcctgccgtatct
gaccaaagcctgggctgacctgtgcaacgctttcctgcaagaagccaa
gtggctgtacaacaaatctactccgacctttgacgactacttcggcaa
cgcatggaaatcctcttctggcccgctgcaactggtgttcgcttactt
cgctgtcgtgcagaacattaaaaaggaagagatcgaaaacctgcaaaa
ataccatgacaccatctctcgtccttcccatatcttccgtctgtgcaa
tgacctggctagcgcgtctgcggaaattgcgcgtggtgaaaccaacaa
tagcgtttcttgttacatgcgcactaaaggtatctccgaagaactggc
taccgaaagcgtgatgaatctgatcgatgaaacctggaaaaagatgaa
caaggaaaaactgagtggtagcctgttcgcgaaaccgttcgtggaaac
cgcgatcaacctggcacgtcaatctcactgcacttatcataacggcga
cgcgcatacctctccggatgagctgacccgcaaacgcgttctgtctgt
aatctgcgaaccgattctgccgtttgaacgcgaaaacctgtattttca
gggcctcgagcaccaccaccaccaccactgagatccggctgctaacaa
agcccgaaaggaagctgagttggctgctgccaccgctgagcaataact
agcataaccccttggggcctctaaacgggtcttgaggggttttttgct
gaaaggaggaactatatccggat 11) Amino Acid Sequence of P. alba MEA A453N L494P T536C (+)TEV - pDW108 (NPC) (SEQ ID NO: 83)

MEARRSANYEPNSWDYDYLLSSDTDESIEVYKDKAKKLEAEVRREINN

EKAEFLTLLELIDNVQRLGLGYRFESDIRGALDRFVSSGGFDAVTKTS

LHGTALSFRLLRQHGFEVSQEAFSGFKDQNGNFLENLKEDIKAILSLY

EASFLALEGENILDEAKVFAISHLKELSEEKIGKELAEQVNHALELPL

HRRTQRLEAVWSIEAYRKKEDANQVLLELAILDYNMIQSVYQRDLRET

SRWWRRVGLATKLHFARDRLIESFYWAVGVAFEPQYSDCRNSVAKMFS

FVTIIDDIYDVYGTLDELELFTDAVERWDVNAINDLPDYMKLCFLALY

NTINEIAYDNLKDKGENILPYLTKAWADLCNAFLQEAKWLYNKSTPTF

DDYFGNAWKSSSGPLQLVFAYFAVVQNIKKEEIENLQKYHDTISRPSH

IFRLCNDLASASAEIARGETNNSVSCYMRTKGISEELATESVMNLIDE

TWKKMNKEKLGGSPFAKPFVETAINLARQSHCTYHNGDAHTSPDELTR

KRVLSVICEPILPFERENLYFQGLEHHHHHH

DNA sequence of pDW108 (SEQ ID NO: 84)

tggcgaatgggacgcgccctgtagcggcgcattaagcgcggcgggtgt ggtggttacgcgcagcgtgaccgctacacttgccagcgccctagcgcc cgctcctttcgctttcttcccttcctttctcgccacgttcgccggctt tccccgtcaagctctaaatcgggggctccctttagggttccgatttag tgctttacggcacctcgaccccaaaaaacttgattagggtgatggttc acgtagtgggccatcgccctgatagacggtttttcgccctttgacgtt ggagtccacgttctttaatagtggactcttgttccaaactggaacaac actcaaccctatctcggtctattcttttgatttataagggattttgcc gatttcggcctattggttaaaaaatgagctgatttaacaaaaatttaa cgcgaattttaacaaaatattaacgtttacaatttcaggtggcacttt tcggggaaatgtgcgcggaacccctatttgtttatttttctaaataca ttcaaatatgtatccgctcatgaattaattcttagaaaaactcatcga gcatcaaatgaaactgcaatttattcatatcaggattatcaataccat atttttgaaaaagccgtttctgtaatgaaggagaaaactcaccgaggc agttccataggatggcaagatcctggtatcggtctgcgattccgactc gtccaacatcaatacaacctattaatttcccctcgtcaaaaataaggt tatcaagtgagaaatcaccatgagtgacgactgaatccggtgagaatg gcaaaagtttatgcatttctttccagacttgttcaacaggccagccat tacgctcgtcatcaaaatcactcgcatcaaccaaaccgttattcattc gtgattgcgcctgagcgagacgaaatacgcgatcgctgttaaaaggac aattacaaacaggaatcgaatgcaaccggcgcaggaacactgccagcg catcaacaatattttcacctgaatcaggatattcttctaatacctgga atgctgttttcccggggatcgcagtggtgagtaaccatgcatcatcag gagtacggataaaatgcttgatggtcggaagaggcataaattccgtca gccagtttagtctgaccatctcatctgtaacatcattggcaacgctac -continued ctttgccatgtttcagaaacaactctggcgcatcgggcttcccataca atcgatagattgtcgcacctgattgcccgacattatcgcgagcccatt tatacccatataaatcagcatccatgttggaatttaatcgcggcctag agcaagacgtttcccgttgaatatggctcataacaccccttgtattac tgtttatgtaagcagacagttttattgttcatgaccaaaatcccttaa cgtgagttttcgttccactgagcgtcagaccccgtagaaaagatcaaa ggatcttcttgagatcctttttttctgcgcgtaatctgctgcttgcaa acaaaaaaaccaccgctaccagcggtggtttgtttgccggatcaagag ctaccaactctttttccgaaggtaactggcttcagcagagcgcagata ccaaatactgtccttctagtgtagccgtagttaggccaccacttcaag aactctgtagcaccgcctacatacctcgctctgctaatcctgttacca gtggctgctgccagtggcgataagtcgtgtcttaccgggttggactca agacgatagttaccggataaggcgcagcggtcgggctgaacggggggt tcgtgcacacagcccagcttggagcgaacgacctacaccgaactgaga tacctacagcgtgagctatgagaaagcgccacgcttcccgaagggaga aaggcggacaggtatccggtaagcggcagggtcggaacaggagagcgc acgagggagcttccagggggaaacgcctggtatctttatagtcctgtc gggtttcgccacctctgacttgagcgtcgatttttgtgatgctcgtca ggggggcggagcctatggaaaaacgccagcaacgcggcctttttacgg ttcctggccttttgctggccttttgctcacatgttctttcctgcgtta tcccctgattctgtggataaccgtattaccgcctttgagtgagctgat accgctcgccgcagccgaacgaccgagcgcagcgagtcagtgagcgag gaagcggaagagcgcctgatgcggtattttctccttacgcatctgtgc ggtatttcacaccgcatatatggtgcactctcagtacaatctgctctg atgccgcatagttaagccagtatacactccgctatcgctacgtgactg ggtcatggctgcgccccgacacccgccaacacccgctgacgcgccctg acgggcttgtctgctcccggcatccgcttacagacaagctgtgaccgt ctccgggagctgcatgtgtcagaggttttcaccgtcatcaccgaaacg cgcgaggcagctgcggtaaagctcatcagcgtggtcgtgaagcgattc acagatgtctgcctgttcatccgcgtccagctcgttgagtttctccag aagcgttaatgtctggcttctgataaagcgggccatgttaagggcggt ttttcctgtttggtcactgatgcctccgtgtaagggggatttctgtt catgggggtaatgataccgatgaaacgagagaggatgctcacgatacg ggttactgatgatgaacatgcccggttactggaacgttgtgagggtaa acaactggcggtatggatgcggcgggaccagagaaaaatcactcaggg tcaatgccagcgcttcgttaatacagatgtaggtgttccacagggtag ccagcagcatcctgcgatgcagatccggaacataatggtgcagggcgc tgacttccgcgtttccagactttacgaaacacggaaaccgaagaccat tcatgttgttgctcaggtcgcagacgttttgcagcagcagtcgcttca cgttcgctcgcgtatcggtgattcattctgctaaccagtaaggcaacc ccgccagcctagccgggtcctcaacgacaggagcacgatcatgcgcac -continued ccgtggggccgccatgccggcgataatggcctgcttctcgccgaaacg tttggtggcgggaccagtgacgaaggcttgagcgagggcgtgcaagat tccgaataccgcaagcgacaggccgatcatcgtcgcgctccagcgaaa gcggtcctcgccgaaaatgacccagagcgctgccggcacctgtcctac gagttgcatgataaagaagacagtcataagtgcggcgacgatagtcat gccccgcgcccaccggaaggagctgactgggttgaaggctctcaaggg catcggtcgagatcccggtgcctaatgagtgagctaacttacattaat tgcgttgcgctcactgcccgctttccagtcgggaaacctgtcgtgcca gctgcattaatgaatcggccaacgcgcggggagaggcggtttgcgtat tgggcgccagggtggtttttcttttcaccagtgagacgggcaacagct gattgcccttcaccgcctggccctgagagagttgcagcaagcggtcca cgctggtttgccccagcaggcgaaaatcctgtttgatggtggttaacg gcgggatataacatgagctgtcttcggtatcgtcgtatcccactaccg agatatccgcaccaacgcgcagcccggactcggtaatggcgcgcattg cgcccagcgccatctgatcgttggcaaccagcatcgcagtgggaacga tgccctcattcagcatttgcatggtttgttgaaaaccggacatggcac tccagtcgccttcccgttccgctatcggctgaatttgattgcgagtga gatatttatgccagccagccagacgcagacgcgccgagacagaactta atgggcccgctaacagcgcgatttgctggtgacccaatgcgaccagat gctccacgcccagtcgcgtaccgtcttcatgggagaaaataatactgt tgatgggtgtctggtcagagacatcaagaaataacgccggaacattag tgcaggcagcttccacagcaatggcatcctggtcatccagcggatagt taatgatcagcccactgacgcgttgcgcgagaagattgtgcaccgccg ctttacaggcttcgacgccgcttcgttctaccatcgacaccaccacgc tggcacccagttgatcggcgcgagatttaatcgccgcgacaatttgcg acggcgcgtgcagggccagactggaggtggcaacgccaatcagcaacg actgtttgcccgccagttgttgtgccacgcggttgggaatgtaattca gctccgccatcgccgcttccactttttcccgcgttttcgcagaaacgt ggctggcctggttcaccacgcgggaaacggtctgataagagacaccgg catactctgcgacatcgtataacgttactggtttcacattcaccaccc tgaattgactctcttccgggcgctatcatgccataccgcgaaaggttt tgcgccattcgatggtgtccgggatctcgacgctctcccttatgcgac tcctgcattaggaagcagcccagtagtaggttgaggccgttgagcacc gccgccgcaaggaatggtgcatgcaaggagatggcgcccaacagtccc ccggccacggggcctgccaccatacccacgccgaaacaagcgctcatg agcccgaagtggcgagcccgatcttccccatcggtgatgtcggcgata taggcgccagcaaccgcacctgtggcgccggtgatgccggccacgatg cgtccggcgtagaggatcgagatctcgatcccgcgaaattaatacgac tcactataggggaattgtgagcggataacaattcccctctagaaataa ttttgtttaactttaagaaggagatatacatatggaagctcgtcgttc -continued tgcgaactacgaacctaacagctgggactatgattacctgctgtcctc cgacacggacgagtccatcgaagtatacaaagacaaagcgaaaaagct ggaagccgaagttcgtcgcgagattaataacgaaaaagcagaatttct gaccctgctggaactgattgacaacgtccagcgcctgggcctgggtta ccgtttcgagtctgatatccgtggtgcgctggatcgcttcgtttcctc cggcggcttcgatgcggtaaccaagacttccctgcacggtacggcact gtctttccgtctgctgcgtcaacacggttttgaggtttctcaggaagc gttcagcggcttcaaagaccaaaacggcaacttcctggagaacctgaa ggaagatatcaaagctatcctgagcctgtacgaggccagcttcctggc tctggaaggcgaaaacatcctggacgaggcgaaggttttcgcaatctc tcatctgaaagaactgtctgaagaaaagatcggtaaagagctggcaga acaggtgaaccatgcactggaactgccactgcatcgccgtactcagcg tctggaagcagtatggtctatcgaggcctaccgtaaaaaggaggacgc gaatcaggttctgctggagctggcaattctggattacaacatgatcca gtctgtataccagcgtgatctgcgtgaaacgtcccgttggtggcgtcg tgtgggtctggcgaccaaactgcactttgctcgtgaccgcctgattga gagcttctactgggccgtgggtgtagcattcgaaccgcaatactccga ctgccgtaactccgtcgcaaaaatgttttctttcgtaaccattatcga cgatatctacgatgtatacggcaccctggacgaactggagctgtttac tgatgcagttgagcgttgggacgtaaacgccatcaacgacctgccgga ttacatgaaactgtgctttctggctctgtataacactattaacgaaat cgcctacgacaacctgaaagataaaggtgagaacatcctgccgtatct gaccaaagcctgggctgacctgtgcaacgctttcctgcaagaagccaa gtggctgtacaacaaatctactccgacctttgacgactacttcggcaa cgcatggaaatcctcttctggcccgctgcaactggtgttcgcttactt cgctgtcgtgcagaacattaaaaaggaagagatcgaaaacctgcaaaa ataccatgacaccatctctcgtccttcccatatcttccgtctgtgcaa tgacctggctagcgcgtctgcggaaattgcgcgtggtgaaaccaacaa tagcgtttcttgttacatgcgcactaaaggtatctccgaagaactggc taccgaaagcgtgatgaatctgatcgatgaaacctggaaaaagatgaa caaggaaaaactgggtggtagcccgttcgcgaaaccgttcgtggaaac cgcgatcaacctggcacgtcaatctcactgcacttatcataacggcga cgcgcatacctctccggatgagctgacccgcaaacgcgttctgtctgt aatctgcgaaccgattctgccgtttgaacgcgaaaacctgtattttca gggcctcgagcaccaccaccaccaccactgagatccggctgctaacaa agcccgaaaggaagctgagttggctgctgccaccgctgagcaataact agcataaccccttggggcctctaaacgggtcttgaggggttttttgct gaaaggaggaactatatccggat 12) Amino Acid Sequence of P. alba MEA A453N G491S L494P T536C (+)TEV - pDW109 (NSPC) (SEQ ID NO: 85)

MEARRSANYEPNSWDYDYLLSSDTDESIEVYKDKAKKLEAEVRREINN

EKAEFLTLLELIDNVQRLGLGYRFESDIRGALDRFVSSGGFDAVTKTS

LHGTALSFRLLRQHGFEVSQEAFSGFKDQNGNFLENLKEDIKAILSLY

EASFLALEGENILDEAKVFAISHLKELSEEKIGKELAEQVNHALELPL

HRRTQRLEAVWSIEAYRKKEDANQVLLELAILDYNMIQSVYQRDLRET

SRWWRRVGLATKLHFARDRLIESFYWAVGVAFEPQYSDCRNSVAKMFS

FVTIIDDIYDVYGTLDELELFTDAVERWDVNAINDLPDYMKLCFLALY

NTINEIAYDNLKDKGENILPYLTKAWADLCNAFLQEAKWLYNKSTPTF

DDYFGNAWKSSSGPLQLVFAYFAVVQNIKKEEIENLQKYHDTISRPSH

IFRLCNDLASASAEIARGETNNSVSCYMRTKGISEELATESVMNLIDE

TWKKMNKEKLSGSPFAKPFVETAINLARQSHCTYHNGDAHTSPDELTR

KRVLSVICEPILPFERENLYFQGLEHHHHHH

DNA sequence of pDW109 (SEQ ID NO: 86)

tggcgaatgggacgcgccctgtagcggcgcattaagcgcggcgggtgt ggtggttacgcgcagcgtgaccgctacacttgccagcgccctagcgcc cgctcctttcgctttcttcccttcctttctcgccacgttcgccggctt tccccgtcaagctctaaatcgggggctccctttagggttccgatttag tgctttacggcacctcgaccccaaaaaacttgattagggtgatggttc acgtagtgggccatcgccctgatagacggtttttcgccctttgacgtt ggagtccacgttctttaatagtggactcttgttccaaactggaacaac actcaaccctatctcggtctattcttttgatttataagggattttgcc gatttcggcctattggttaaaaaatgagctgatttaacaaaaatttaa cgcgaattttaacaaaatattaacgtttacaatttcaggtggcacttt tcggggaaatgtgcgcggaacccctatttgtttatttttctaaataca ttcaaatatgtatccgctcatgaattaattcttagaaaaactcatcga gcatcaaatgaaactgcaatttattcatatcaggattatcaataccat atttttgaaaaagccgtttctgtaatgaaggagaaaactcaccgaggc agttccataggatggcaagatcctggtatcggtctgcgattccgactc gtccaacatcaatacaacctattaatttcccctcgtcaaaaataaggt tatcaagtgagaaatcaccatgagtgacgactgaatccggtgagaatg gcaaaagtttatgcatttctttccagacttgttcaacaggccagccat tacgctcgtcatcaaaatcactcgcatcaaccaaaccgttattcattc gtgattgcgcctgagcgagacgaaatacgcgatcgctgttaaaaggac aattacaaacaggaatcgaatgcaaccggcgcaggaacactgccagcg catcaacaatattttcacctgaatcaggatattcttctaatacctgga atgctgttttcccggggatcgcagtggtgagtaaccatgcatcatcag gagtacggataaaatgcttgatggtcggaagaggcataaattccgtca gccagtttagtctgaccatctcatctgtaacatcattggcaacgctac -continued ctttgccatgtttcagaaacaactctggcgcatcgggcttcccataca atcgatagattgtcgcacctgattgcccgacattatcgcgagcccatt tatacccatataaatcagcatccatgttggaatttaatcgcggcctag agcaagacgtttcccgttgaatatggctcataacaccccttgtattac tgtttatgtaagcagacagttttattgttcatgaccaaaatcccttaa cgtgagttttcgttccactgagcgtcagaccccgtagaaaagatcaaa ggatcttcttgagatcctttttttctgcgcgtaatctgctgcttgcaa acaaaaaaaccaccgctaccagcggtggtttgtttgccggatcaagag ctaccaactctttttccgaaggtaactggcttcagcagagcgcagata ccaaatactgtccttctagtgtagccgtagttaggccaccacttcaag aactctgtagcaccgcctacatacctcgctctgctaatcctgttacca gtggctgctgccagtggcgataagtcgtgtcttaccgggttggactca agacgatagttaccggataaggcgcagcggtcgggctgaacgggggt tcgtgcacacagcccagcttggagcgaacgacctacaccgaactgaga tacctacagcgtgagctatgagaaagcgccacgcttcccgaagggaga aaggcggacaggtatccggtaagcggcagggtcggaacaggagagcgc acgagggagcttccagggggaaacgcctggtatctttatagtcctgtc gggtttcgccacctctgacttgagcgtcgatttttgtgatgctcgtca ggggggcggagcctatggaaaaacgccagcaacgcggcctttttacgg ttcctggccttttgctggccttttgctcacatgttctttcctgcgtta tcccctgattctgtggataaccgtattaccgcctttgagtgagctgat accgctcgccgcagccgaacgaccgagcgcagcgagtcagtgagcgag gaagcggaagagcgcctgatgcggtattttctccttacgcatctgtgc ggtatttcacaccgcatatatggtgcactctcagtacaatctgctctg atgccgcatagttaagccagtatacactccgctatcgctacgtgactg ggtcatggctgcgccccgacacccgccaacacccgctgacgcgccctg acgggcttgtctgctcccggcatccgcttacagacaagctgtgaccgt ctccgggagctgcatgtgtcagaggttttcaccgtcatcaccgaaacg cgcgaggcagctgcggtaaagctcatcagcgtggtcgtgaagcgattc acagatgtctgcctgttcatccgcgtccagctcgttgagtttctccag aagcgttaatgtctggcttctgataaagcgggccatgttaagggcggt tttttcctgtttggtcactgatgcctccgtgtaagggggatttctgtt catgggggtaatgataccgatgaaacgagagaggatgctcacgatacg ggttactgatgatgaacatgcccggttactggaacgttgtgagggtaa acaactggcggtatggatgcggcgggaccagagaaaaatcactcaggg tcaatgccagcgcttcgttaatacagatgtaggtgttccacagggtag ccagcagcatcctgcgatgcagatccggaacataatggtgcagggcgc tgacttccgcgtttccagactttacgaaacacggaaaccgaagaccat tcatgttgttgctcaggtcgcagacgttttgcagcagcagtcgcttca cgttcgctcgcgtatcggtgattcattctgctaaccagtaaggcaacc ccgccagcctagccgggtcctcaacgacaggagcacgatcatgcgcac -continued ccgtggggccgccatgccggcgataatggcctgcttctcgccgaaacg tttggtggcgggaccagtgacgaaggcttgagcgagggcgtgcaagat tccgaataccgcaagcgacaggccgatcatcgtcgcgctccagcgaaa gcggtcctcgccgaaaatgacccagagcgctgccggcacctgtcctac gagttgcatgataaagaagacagtcataagtgcggcgacgatagtcat gccccgcgcccaccggaaggagctgactgggttgaaggctctcaaggg catcggtcgagatcccggtgcctaatgagtgagctaacttacattaat tgcgttgcgctcactgcccgctttccagtcgggaaacctgtcgtgcca gctgcattaatgaatcggccaacgcgcggggagaggcggtttgcgtat tgggcgccagggtggtttttcttttcaccagtgagacgggcaacagct gattgcccttcaccgcctggccctgagagagttgcagcaagcggtcca cgctggtttgccccagcaggcgaaaatcctgtttgatggtggttaacg gcgggatataacatgagctgtcttcggtatcgtcgtatcccactaccg agatatccgcaccaacgcgcagcccggactcggtaatggcgcgcattg cgcccagcgccatctgatcgttggcaaccagcatcgcagtgggaacga tgccctcattcagcatttgcatggtttgttgaaaaccggacatggcac tccagtcgccttcccgttccgctatcggctgaatttgattgcgagtga gatatttatgccagccagccagacgcagacgcgccgagacagaactta atgggcccgctaacagcgcgatttgctggtgacccaatgcgaccagat gctccacgcccagtcgcgtaccgtcttcatgggagaaaataatactgt tgatgggtgtctggtcagagacatcaagaaataacgccggaacattag tgcaggcagcttccacagcaatggcatcctggtcatccagcggatagt taatgatcagcccactgacgcgttgcgcgagaagattgtgcaccgccg ctttacaggcttcgacgccgcttcgttctaccatcgacaccaccacgc tggcacccagttgatcggcgcgagatttaatcgccgcgacaatttgcg acggcgcgtgcagggccagactggaggtggcaacgccaatcagcaacg actgtttgcccgccagttgttgtgccacgcggttgggaatgtaattca gctccgccatcgccgcttccacttttcccgcgttttcgcagaaacgt ggctggcctggttcaccacgcgggaaacggtctgataagagacaccgg catactctgcgacatcgtataacgttactggtttcacattcaccaccc tgaattgactctcttccgggcgctatcatgccataccgcgaaaggttt tgcgccattcgatggtgtccgggatctcgacgctctcccttatgcgac tcctgcattaggaagcagcccagtagtaggttgaggccgttgagcacc gccgccgcaaggaatggtgcatgcaaggagatggcgcccaacagtccc ccggccacggggcctgccaccatacccacgccgaaacaagcgctcatg agcccgaagtggcgagcccgatcttccccatcggtgatgtcggcgata taggcgccagcaaccgcacctgtggcgccggtgatgccggccacgatg cgtccggcgtagaggatcgagatctcgatcccgcgaaattaatacgac tcactataggggaattgtgagcggataacaattcccctctagaaataa ttttgtttaactttaagaaggagatatacatatggaagctcgtcgttc -continued tgcgaactacgaacctaacagctgggactatgattacctgctgtcctc cgacacggacgagtccatcgaagtatacaaagacaaagcgaaaaagct ggaagccgaagttcgtcgcgagattaataacgaaaaagcagaatttct gaccctgctggaactgattgacaacgtccagcgcctgggcctgggtta ccgtttcgagtctgatatccgtggtgcgctggatcgcttcgtttcctc cggcggcttcgatgcggtaaccaagacttccctgcacggtacggcact gtctttccgtctgctgcgtcaacacggttttgaggtttctcaggaagc gttcagcggcttcaaagaccaaaacggcaacttcctggagaacctgaa ggaagatatcaaagctatcctgagcctgtacgaggccagcttcctggc tctggaaggcgaaaacatcctggacgaggcgaaggttttcgcaatctc tcatctgaaagaactgtctgaagaaaagatcggtaaagagctggcaga acaggtgaaccatgcactggaactgccactgcatcgccgtactcagcg tctggaagcagtatggtctatcgaggcctaccgtaaaaaggaggacgc gaatcaggttctgctggagctggcaattctggattacaacatgatcca gtctgtataccagcgtgatctgcgtgaaacgtcccgttggtggcgtcg tgtgggtctggcgaccaaactgcactttgctcgtgaccgcctgattga gagcttctactgggccgtgggtgtagcattcgaaccgcaatactccga ctgccgtaactccgtcgcaaaaatgttttctttcgtaaccattatcga cgatatctacgatgtatacggcaccctggacgaactggagctgtttac tgatgcagttgagcgttgggacgtaaacgccatcaacgacctgccgga ttacatgaaactgtgctttctggctctgtataacactattaacgaaat cgcctacgacaacctgaaagataaaggtgagaacatcctgccgtatct gaccaaagcctgggctgacctgtgcaacgctttcctgcaagaagccaa gtggctgtacaacaaatctactccgacctttgacgactacttcggcaa cgcatggaaatcctcttctggcccgctgcaactggtgttcgcttactt cgctgtcgtgcagaacattaaaaaggaagagatcgaaaacctgcaaaa ataccatgacaccatctctcgtccttcccatatcttccgtctgtgcaa tgacctggctagcgcgtctgcggaaattgcgcgtggtgaaaccaacaa tagcgtttcttgttacatgcgcactaaaggtatctccgaagaactggc taccgaaagcgtgatgaatctgatcgatgaaacctggaaaaagatgaa caaggaaaaactgagtggtagcccgttcgcgaaaccgttcgtggaaac cgcgatcaacctggcacgtcaatctcactgcacttatcataacggcga cgcgcatacctctccggatgagctgacccgcaaacgcgttctgtctgt aatctgcgaaccgattctgccgtttgaacgcgaaaacctgtattttca gggcctcgagcaccaccaccaccaccactgagatccggctgctaacaa agcccgaaaggaagctgagttggctgctgccaccgctgagcaataact agcataaccccttggggcctctaaacgggtcttgaggggttttttgct gaaaggaggaactatatccggat 13) Amino Acid Sequence of P. alba MEA G491S L494P (+)TEV - pDW110 (SP) (SEQ ID NO: 87)

MEARRSANYEPNSWDYDYLLSSDTDESIEVYKDKAKKLEAEVRREINN
EKAEFLTLLELIDNVQRLGLGYRFESDIRGALDRFVSSGGFDAVTKTS
LHGTALSFRLLRQHGFEVSQEAFSGFKDQNGNFLENLKEDIKAILSLY
EASFLALEGENILDEAKVFAISHLKELSEEKIGKELAEQVNHALELPL
HRRTQRLEAVWSIEAYRKKEDANQVLLELAILDYNMIQSVYQRDLRET
SRWWRRVGLATKLHFARDRLIESFYWAVGVAFEPQYSDCRNSVAKMFS
FVTIIDDIYDVYGTLDELELFTDAVERWDVNAINDLPDYMKLCFLALY
NTINEIAYDNLKDKGENILPYLTKAWADLCNAFLQEAKWLYNKSTPTF
DDYFGNAWKSSSGPLQLVFAYFAVVQNIKKEEIENLQKYHDTISRPSH
IFRLCNDLASASAEIARGETANSVSCYMRTKGISEELATESVMNLIDE
TWKKMNKEKLSGSPFAKPFVETAINLARQSHCTYHNGDAHTSPDELTR
KRVLSVITEPILPFERENLYFQGLEHHHHHH

DNA sequence of pDW110 (SEQ ID NO: 88)

tggcgaatgggacgcgccctgtagcggcgcattaagcgcggcgggtgt
ggtggttacgcgcagcgtgaccgctacacttgccagcgccctagcgcc
cgctcctttcgctttcttcccttcctttctcgccacgttcgccggctt
tccccgtcaagctctaaatcgggggctccctttagggttccgatttag
tgctttacggcacctcgaccccaaaaaacttgattagggtgatggttc
acgtagtgggccatcgccctgatagacggtttttcgccctttgacgtt
ggagtccacgttctttaatagtggactcttgttccaaactggaacaac
actcaaccctatctcggtctattcttttgatttataagggattttgcc
gatttcggcctattggttaaaaaatgagctgatttaacaaaaatttaa
cgcgaattttaacaaaatattaacgtttacaatttcaggtggcacttt
tcggggaaatgtgcgcggaacccctatttgtttatttttctaaataca
ttcaaatatgtatccgctcatgaattaattcttagaaaaactcatcga
gcatcaaatgaaactgcaatttattcatatcaggattatcaataccat
atttttgaaaaagccgtttctgtaatgaaggagaaaactcaccgaggc
agttccataggatggcaagatcctggtatcggtctgcgattccgactc
gtccaacatcaatacaacctattaatttcccctcgtcaaaaataaggt
tatcaagtgagaaatcaccatgagtgacgactgaatccggtgagaatg
gcaaaagtttatgcatttctttccagacttgttcaacaggccagccat
tacgctcgtcatcaaaatcactcgcatcaaccaaaccgttattcattc
gtgattgcgcctgagcgagacgaaatacgcgatcgctgttaaaaggac
aattacaaacaggaatcgaatgcaaccggcgcaggaacactgccagcg
catcaacaatattttcacctgaatcaggatattcttctaatacctgga
atgctgttttcccggggatcgcagtggtgagtaaccatgcatcatcag
gagtacggataaaatgcttgatggtcggaagaggcataaattccgtca
gccagtttagtctgaccatctcatctgtaacatcattggcaacgctac -continued ctttgccatgtttcagaaacaactctggcgcatcgggcttcccataca
atcgatagattgtcgcacctgattgcccgacattatcgcgagcccatt
tatacccatataaatcagcatccatgttggaatttaatcgcggcctag
agcaagacgtttcccgttgaatatggctcataacaccccttgtattac
tgtttatgtaagcagacagttttattgttcatgaccaaaatcccttaa
cgtgagttttcgttccactgagcgtcagaccccgtagaaaagatcaaa
ggatcttcttgagatcctttttttctgcgcgtaatctgctgcttgcaa
acaaaaaaaccaccgctaccagcggtggtttgtttgccggatcaagag
ctaccaactctttttccgaaggtaactggcttcagcagagcgcagata
ccaaatactgtccttctagtgtagccgtagttaggccaccacttcaag
aactctgtagcaccgcctacatacctcgctctgctaatcctgttacca
gtggctgctgccagtggcgataagtcgtgtcttaccgggttggactca
agacgatagttaccggataaggcgcagcggtcgggctgaacggggggt
tcgtgcacacagcccagcttggagcgaacgacctacaccgaactgaga
tacctacagcgtgagctatgagaaagcgccacgcttcccgaagggaga
aaggcggacaggtatccggtaagcggcagggtcggaacaggagagcgc
acgagggagcttccagggggaaacgcctggtatctttatagtcctgtc
gggtttcgccacctctgacttgagcgtcgatttttgtgatgctcgtca
ggggggcggagcctatggaaaaacgccagcaacgcggcctttttacgg
ttcctggccttttgctggccttttgctcacatgttctttcctgcgtta
tcccctgattctgtggataaccgtattaccgcctttgagtgagctgat
accgctcgccgcagccgaacgaccgagcgcagcgagtcagtgagcgag
gaagcggaagagcgcctgatgcggtattttctccttacgcatctgtgc
ggtatttcacaccgcatatatggtgcactctcagtacaatctgctctg
atgccgcatagttaagccagtatacactccgctatcgctacgtgactg
ggtcatggctgcgccccgacacccgccaacacccgctgacgcgccctg
acgggcttgtctgctcccggcatccgcttacagacaagctgtgaccgt
ctccgggagctgcatgtgtcagaggttttcaccgtcatcaccgaaacg
cgcgaggcagctgcggtaaagctcatcagcgtggtcgtgaagcgattc
acagatgtctgcctgttcatccgcgtccagctcgttgagtttctccag
aagcgttaatgtctggcttctgataaagcgggccatgttaagggcggt
ttttcctgtttggtcactgatgcctccgtgtaagggggatttctgtt
catgggggtaatgataccgatgaaacgagagaggatgctcacgatacg
ggttactgatgatgaacatgcccggttactggaacgttgtgagggtaa
acaactggcggtatggatgcggcgggaccagagaaaaatcactcaggg
tcaatgccagcgcttcgttaatacagatgtaggtgttccacagggtag
ccagcagcatcctgcgatgcagatccggaacataatggtgcagggcgc
tgacttccgcgtttccagactttacgaaacacggaaaccgaagaccat
tcatgttgttgctcaggtcgcagacgttttgcagcagcagtcgcttca
cgttcgctcgcgtatcggtgattcattctgctaaccagtaaggcaacc
ccgccagcctagccgggtcctcaacgacaggagcacgatcatgcgcac -continued ccgtggggccgccatgccggcgataatggcctgcttctcgccgaaacg tttggtggcgggaccagtgacgaaggcttgagcgagggcgtgcaagat tccgaataccgcaagcgacaggccgatcatcgtcgcgctccagcgaaa gcggtcctcgccgaaaatgacccagagcgctgccggcacctgtcctac gagttgcatgataaagaagacagtcataagtgcggcgacgatagtcat gccccgcgcccaccggaaggagctgactgggttgaaggctctcaaggg catcggtcgagatcccggtgcctaatgagtgagctaacttacattaat tgcgttgcgctcactgcccgctttccagtcgggaaacctgtcgtgcca gctgcattaatgaatcggccaacgcgcggggagaggcggtttgcgtat tgggcgccagggtggtttttcttttcaccagtgagacgggcaacagct gattgcccttcaccgcctggccctgagagagttgcagcaagcggtcca cgctggtttgccccagcaggcgaaaatcctgtttgatggtggttaacg gcgggatataacatgagctgtcttcggtatcgtcgtatcccactaccg agatatccgcaccaacgcgcagcccggactcggtaatggcgcgcattg cgcccagcgccatctgatcgttggcaaccagcatcgcagtgggaacga tgccctcattcagcatttgcatggtttgttgaaaaccggacatggcac tccagtcgccttcccgttccgctatcggctgaatttgattgcgagtga gatatttatgccagccagccagacgcagacgcgccgagacagaactta atgggcccgctaacagcgcgatttgctggtgacccaatgcgaccagat gctccacgcccagtcgcgtaccgtcttcatgggagaaaataatactgt tgatgggtgtctggtcagagacatcaagaaataacgccggaacattag tgcaggcagcttccacagcaatggcatcctggtcatccagcggatagt taatgatcagcccactgacgcgttgcgcgagaagattgtgcaccgccg ctttacaggcttcgacgccgcttcgttctaccatcgacaccaccacgc tggcacccagttgatcggcgcgagatttaatcgccgcgacaatttgcg acggcgcgtgcagggccagactggaggtggcaacgccaatcagcaacg actgtttgcccgccagttgttgtgccacgcggttgggaatgtaattca gctccgccatcgccgcttccactttttcccgcgttttcgcagaaacgt ggctggcctggttcaccacgcgggaaacggtctgataagagacaccgg catactctgcgacatcgtataacgttactggtttcacattcaccaccc tgaattgactctcttccgggcgctatcatgccataccgcgaaaggttt tgcgccattcgatggtgtccgggatctcgacgctctcccttatgcgac tcctgcattaggaagcagcccagtagtaggttgaggccgttgagcacc gccgccgcaaggaatggtgcatgcaaggagatggcgcccaacagtccc ccggccacggggcctgccaccatacccacgccgaaacaagcgctcatg agcccgaagtggcgagcccgatcttccccatcggtgatgtcggcgata taggcgccagcaaccgcacctgtggcgccggtgatgccggccacgatg cgtccggcgtagaggatcgagatctcgatcccgcgaaattaatacgac tcactataggggaattgtgagcggataacaattcccctctagaaataa ttttgtttaactttaagaaggagatatacatatggaagctcgtcgttc -continued tgcgaactacgaacctaacagctgggactatgattacctgctgtcctc cgacacggacgagtccatcgaagtatacaaagacaaagcgaaaaagct ggaagccgaagttcgtcgcgagattaataacgaaaaagcagaatttct gaccctgctggaactgattgacaacgtccagcgcctgggcctgggtta ccgtttcgagtctgatatccgtggtgcgctggatcgcttcgtttcctc cggcggcttcgatgcggtaaccaagacttccctgcacggtacggcact gtctttccgtctgctgcgtcaacacggttttgaggtttctcaggaagc gttcagcggcttcaaagaccaaaacggcaacttcctggagaacctgaa ggaagatatcaaagctatcctgagcctgtacgaggccagcttcctggc tctggaaggcgaaaacatcctggacgaggcgaaggttttcgcaatctc tcatctgaaagaactgtctgaagaaaagatcggtaaagagctggcaga acaggtgaaccatgcactggaactgccactgcatcgccgtactcagcg tctggaagcagtatggtctatcgaggcctaccgtaaaaaggaggacgc gaatcaggttctgctggagctggcaattctggattacaacatgatcca gtctgtataccagcgtgatctgcgtgaaacgtcccgttggtggcgtcg tgtgggtctggcgaccaaactgcactttgctcgtgaccgcctgattga gagcttctactgggccgtgggtgtagcattcgaaccgcaatactccga ctgccgtaactccgtcgcaaaaatgttttctttcgtaaccattatcga cgatatctacgatgtatacggcaccctggacgaactggagctgtttac tgatgcagttgagcgttgggacgtaaacgccatcaacgacctgccgga ttacatgaaactgtgctttctggctctgtataacactattaacgaaat cgcctacgacaacctgaaagataaaggtgagaacatcctgccgtatct gaccaaagcctgggctgacctgtgcaacgctttcctgcaagaagccaa gtggctgtacaacaaatctactccgacctttgacgactacttcggcaa cgcatggaaatcctcttctggcccgctgcaactggtgttcgcttactt cgctgtcgtgcagaacattaaaaaggaagagatcgaaaacctgcaaaa ataccatgacaccatctctcgtccttcccatatcttccgtctgtgcaa tgacctggctagcgcgtctgcggaaattgcgcgtggtgaaaccgcaaa tagcgtttcttgttacatgcgcactaaaggtatctccgaagaactggc taccgaaagcgtgatgaatctgatcgatgaaacctggaaaaagatgaa caaggaaaaactgagtggtagcccgttcgcgaaaccgttcgtggaaac cgcgatcaacctggcacgtcaatctcactgcacttatcataacggcga cgcgcatacctctccggatgagctgacccgcaaacgcgttctgtctgt aatcactgaaccgattctgccgtttgaacgcgaaaacctgtattttca gggcctcgagcaccaccaccaccaccactgagatccggctgctaacaa agcccgaaaggaagctgagttggctgctgccaccgctgagcaataact agcataaccccttggggcctctaaacgggtcttgaggggttttttgct gaaaggaggaactatatccggat 14) Amino Acid Sequence of P. alba MEA G491S T536C (+)TEV - pDW111 (SC) (SEQ ID NO: 89)
MEARRSANYEPNSWDYDYLLSSDTDESIEVYKDKAKKLEAEVRREINN
EKAEFLTLLELIDNVQRLGLGYRFESDIRGALDRFVSSGGFDAVTKTS
LHGTALSFRLLRQHGFEVSQEAFSGFKDQNGNFLENLKEDIKAILSLY
EASFLALEGENILDEAKVFAISHLKELSEEKIGKELAEQVNHALELPL
HRRTQRLEAVWSIEAYRKKEDANQVLLELAILDYNMIQSVYQRDLRET
SRWWRRVGLATKLHFARDRLIESFYWAVGVAFEPQYSDCRNSVAKMFS
FVTIIDDIYDVYGTLDELELFTDAVERWDVNAINDLPDYMKLCFLALY
NTINEIAYDNLKDKGENILPYLTKAWADLCNAFLQEAKWLYNKSTPTF
DDYFGNAWKSSSGPLQLVFAYFAVVQNIKKEEIENLQKYHDTISRPSH
IFRLCNDLASASAEIARGETANSVSCYMRTKGISEELATESVMNLIDE
TWKKMNKEKLSGSLFAKPFVETAINLARQSHCTYHNGDAHTSPDELTR
KRVLSVICEPILPFERENLYFQGLEHHHHHH DNA sequence of pDW111 (SEQ ID NO: 90)
tggcgaatgggacgcgccctgtagcggcgcattaagcgcggcgggtgt
ggtggttacgcgcagcgtgaccgctacacttgccagcgccctagcgcc
cgctcctttcgctttcttcccttcctttctcgccacgttcgccggctt
tccccgtcaagctctaaatcgggggctccctttagggttccgatttag
tgctttacggcacctcgaccccaaaaaacttgattagggtgatggttc
acgtagtgggccatcgccctgatagacggtttttcgccctttgacgtt
ggagtccacgttctttaatagtggactcttgttccaaactggaacaac
actcaaccctatctcggtctattcttttgatttataagggattttgcc
gatttcggcctattggttaaaaaatgagctgatttaacaaaaatttaa
cgcgaattttaacaaaatattaacgtttacaatttcaggtggcacttt
tcggggaaatgtgcgcggaacccctatttgtttatttttctaaataca
ttcaaatatgtatccgctcatgaattaattcttagaaaaactcatcga
gcatcaaatgaaactgcaatttattcatatcaggattatcaataccat
atttttgaaaaagccgtttctgtaatgaaggagaaaactcaccgaggc
agttccataggatggcaagatcctggtatcggtctgcgattccgactc
gtccaacatcaatacaacctattaatttcccctcgtcaaaaataaggt
tatcaagtgagaaatcaccatgagtgacgactgaatccggtgagaatg
gcaaaagtttatgcatttctttccagacttgttcaacaggccagccat
tacgctcgtcatcaaaatcactcgcatcaaccaaaccgttattcattc
gtgattgcgcctgagcgagacgaaatacgcgatcgctgttaaaaggac
aattacaaacaggaatcgaatgcaaccggcgcaggaacactgccagcg
catcaacaatattttcacctgaatcaggatattcttctaatacctgga
atgctgttttcccggggatcgcagtggtgagtaaccatgcatcatcag
gagtacggataaaatgcttgatggtcggaagaggcataaattccgtca
gccagtttagtctgaccatctcatctgtaacatcattggcaacgctac
ctttgccatgtttcagaaacaactctggcgcatcgggcttcccataca -continued atcgatagattgtcgcacctgattgcccgacattatcgcgagcccatt
tatacccatataaatcagcatccatgttggaatttaatcgcggcctag
agcaagacgtttcccgttgaatatggctcataacaccccttgtattac
tgtttatgtaagcagacagttttattgttcatgaccaaaatcccttaa
cgtgagttttcgttccactgagcgtcagaccccgtagaaaagatcaaa
ggatcttcttgagatcctttttttctgcgcgtaatctgctgcttgcaa
acaaaaaaaccaccgctaccagcggtggtttgtttgccggatcaagag
ctaccaactctttttccgaaggtaactggcttcagcagagcgcagata
ccaaatactgtccttctagtgtagccgtagttaggccaccacttcaag
aactctgtagcaccgcctacatacctcgctctgctaatcctgttacca
gtggctgctgccagtggcgataagtcgtgtcttaccgggttggactca
agacgatagttaccggataaggcgcagcggtcgggctgaacggggggt
tcgtgcacacagcccagcttggagcgaacgacctacaccgaactgaga
tacctacagcgtgagctatgagaaagcgccacgcttcccgaagggaga
aaggcggacaggtatccggtaagcggcagggtcggaacaggagagcgc
acgagggagcttccagggggaaacgcctggtatctttatagtcctgtc
gggtttcgccacctctgacttgagcgtcgatttttgtgatgctcgtca
ggggggcggagcctatggaaaaacgccagcaacgcggcctttttacgg
ttcctggccttttgctggccttttgctcacatgttctttcctgcgtta
tcccctgattctgtggataaccgtattaccgcctttgagtgagctgat
accgctcgccgcagccgaacgaccgagcgcagcgagtcagtgagcgag
gaagcggaagagcgcctgatgcggtattttctccttacgcatctgtgc
ggtatttcacaccgcatatatggtgcactctcagtacaatctgctctg
atgccgcatagttaagccagtatacactccgctatcgctacgtgactg
ggtcatggctgcgccccgacacccgccaacacccgctgacgcgccctg
acgggcttgtctgctcccggcatccgcttacagacaagctgtgaccgt
ctccgggagctgcatgtgtcagaggttttcaccgtcatcaccgaaacg
cgcgaggcagctgcggtaaagctcatcagcgtggtcgtgaagcgattc
acagatgtctgcctgttcatccgcgtccagctcgttgagtttctccag
aagcgttaatgtctggcttctgataaagcgggccatgttaagggcggt
ttttcctgtttggtcactgatgcctccgtgtaagggggatttctgtt
catgggggtaatgataccgatgaaacgagagaggatgctcacgatacg
ggttactgatgatgaacatgcccggttactggaacgttgtgagggtaa
acaactggcggtatggatgcggcgggaccagagaaaaatcactcaggg
tcaatgccagcgcttcgttaatacagatgtaggtgttccacagggtag
ccagcagcatcctgcgatgcagatccggaacataatggtgcagggcgc
tgacttccgcgtttccagactttacgaaacacggaaaccgaagaccat
tcatgttgttgctcaggtcgcagacgttttgcagcagcagtcgcttca
cgttcgctcgcgtatcggtgattcattctgctaaccagtaaggcaacc
ccgccagcctagccgggtcctcaacgacaggagcacgatcatgcgcac -continued ccgtggggccgccatgccggcgataatggcctgcttctcgccgaaacg
tttggtggcgggaccagtgacgaaggcttgagcgagggcgtgcaagat
tccgaataccgcaagcgacaggccgatcatcgtcgcgctccagcgaaa
gcggtcctcgccgaaaatgacccagagcgctgccggcacctgtcctac
gagttgcatgataaagaagacagtcataagtgcggcgacgatagtcat
gccccgcgcccaccggaaggagctgactgggttgaaggctctcaaggg
catcggtcgagatcccggtgcctaatgagtgagctaacttacattaat
tgcgttgcgctcactgcccgctttccagtcgggaaacctgtcgtgcca
gctgcattaatgaatcggccaacgcgcggggagaggcggtttgcgtat
tgggcgccagggtggtttttcttttcaccagtgagacgggcaacagct
gattgcccttcaccgcctggccctgagagagttgcagcaagcggtcca
cgctggtttgccccagcaggcgaaaatcctgtttgatggtggttaacg
gcgggatataacatgagctgtcttcggtatcgtcgtatcccactaccg
agatatccgcaccaacgcgcagcccggactcggtaatggcgcgcattg
cgcccagcgccatctgatcgttggcaaccagcatcgcagtgggaacga
tgccctcattcagcatttgcatggtttgttgaaaaccggacatggcac
tccagtcgccttcccgttccgctatcggctgaatttgattgcgagtga
gatatttatgccagccagccagacgcagacgcgccgagacagaactta
atgggcccgctaacagcgcgatttgctggtgacccaatgcgaccagat
gctccacgcccagtcgcgtaccgtcttcatgggagaaaataatactgt
tgatgggtgtctggtcagagacatcaagaaataacgccggaacattag
tgcaggcagcttccacagcaatggcatcctggtcatccagcggatagt
taatgatcagcccactgacgcgttgcgcgagaagattgtgcaccgccg
ctttacaggcttcgacgccgcttcgttctaccatcgacaccaccacgc
tggcacccagttgatcggcgcgagatttaatcgccgcgacaatttgcg
acggcgcgtgcagggccagactggaggtggcaacgccaatcagcaacg
actgtttgcccgccagttgttgtgccacgcggttgggaatgtaattca
gctccgccatcgccgcttccactttttcccgcgttttcgcagaaacgt
ggctggcctggttcaccacgcgggaaacggtctgataagagacaccgg
catactctgcgacatcgtataacgttactggtttcacattcaccaccc
tgaattgactctcttccgggcgctatcatgccataccgcgaaaggttt
tgcgccattcgatggtgtccgggatctcgacgctctcccttatgcgac
tcctgcattaggaagcagcccagtagtaggttgaggccgttgagcacc
gccgccgcaaggaatggtgcatgcaaggagatggcgcccaacagtccc
ccggccacggggcctgccaccatacccacgccgaaacaagcgctcatg
agcccgaagtggcgagcccgatcttccccatcggtgatgtcggcgata
taggcgccagcaaccgcacctgtggcgccggtgatgccggccacgatg
cgtccggcgtagaggatcgagatctcgatcccgcgaaattaatacgac
tcactataggggaattgtgagcggataacaattcccctctagaaataa
ttttgtttaactttaagaaggagatatacatatggaagctcgtcgttc
tgcgaactacgaacctaacagctgggactatgattacctgctgtcctc -continued cgacacggacgagtccatcgaagtatacaaagacaaagcgaaaaagct
ggaagccgaagttcgtcgcgagattaataacgaaaaagcagaatttct
gaccctgctggaactgattgacaacgtccagcgcctgggcctgggtta
ccgtttcgagtctgatatccgtggtgcgctggatcgcttcgtttcctc
cggcggcttcgatgcggtaaccaagacttccctgcacggtacggcact
gtctttccgtctgctgcgtcaacacggttttgaggtttctcaggaagc
gttcagcggcttcaaagaccaaaacggcaacttcctggagaacctgaa
ggaagatatcaaagctatcctgagcctgtacgaggccagcttcctggc
tctggaaggcgaaaacatcctggacgaggcgaaggttttcgcaatctc
tcatctgaaagaactgtctgaagaaaagatcggtaaagagctggcaga
acaggtgaaccatgcactggaactgccactgcatcgccgtactcagcg
tctggaagcagtatggtctatcgaggcctaccgtaaaaaggaggacgc
gaatcaggttctgctggagctggcaattctggattacaacatgatcca
gtctgtataccagcgtgatctgcgtgaaacgtcccgttggtggcgtcg
tgtgggtctggcgaccaaactgcactttgctcgtgaccgcctgattga
gagcttctactgggccgtgggtgtagcattcgaaccgcaatactccga
ctgccgtaactccgtcgcaaaaatgttttctttcgtaaccattatcga
cgatatctacgatgtatacggcaccctggacgaactggagctgtttac
tgatgcagttgagcgttgggacgtaaacgccatcaacgacctgccgga
ttacatgaaactgtgctttctggctctgtataacactattaacgaaat
cgcctacgacaacctgaaagataaaggtgagaacatcctgccgtatct
gaccaaagcctgggctgacctgtgcaacgctttcctgcaagaagccaa
gtggctgtacaacaaatctactccgacctttgacgactacttcggcaa
cgcatggaaatcctcttctggcccgctgcaactggtgttcgcttactt
cgctgtcgtgcagaacattaaaaaggaagagatcgaaaacctgcaaaa
ataccatgacaccatctctcgtccttcccatatcttccgtctgtgcaa
tgacctggctagcgcgtctgcggaaattgcgcgtggtgaaaccgcaaa
tagcgtttcttgttacatgcgcactaaaggtatctccgaagaactggc
taccgaaagcgtgatgaatctgatcgatgaaacctggaaaaagatgaa
caaggaaaaactgagtggtagcctgttcgcgaaaccgttcgtggaaac
cgcgatcaacctggcacgtcaatctcactgcacttatcataacggcga
cgcgcatacctctccggatgagctgacccgcaaacgcgttctgtctgt
aatctgcgaaccgattctgccgtttgaacgcgaaaacctgtattttca
gggcctcgagcaccaccaccaccaccactgagatccggctgctaacaa
agcccgaaaggaagctgagttggctgctgccaccgctgagcaataact
agcataaccccttggggcctctaaacgggtcttgaggggttttttgct
gaaaggaggaactatatccggat 15) Amino Acid Sequence of P. alba MEA G491S L494P T536C (+)TEV - pDW112 (SPC) (SEQ ID NO: 91)

MEARRSANYEPNSWDYDYLLSSDTDESIEVYKDKAKKLEAEVRREINN
EKAEFLTLLELIDNVQRLGLGYRFESDIRGALDRFVSSGGFDAVTKTS
LHGTALSFRLLRQHGFEVSQEAFSGFKDQNGNFLENLKEDIKAILSLY
EASFLALEGENILDEAKVFAISHLKELSEEKIGKELAEQVNHALELPL
HRRTQRLEAVWSIEAYRKKEDANQVLLELAILDYNMIQSVYQRDLRET
SRWWRRVGLATKLHFARDRLIESFYWAVGVAFEPQYSDCRNSVAKMFS
FVTIIDDIYDVYGTLDELELFTDAVERWDVNAINDLPDYMKLCFLALY
NTINEIAYDNLKDKGENILPYLTKAWADLCNAFLQEAKWLYNKSTPTF
DDYFGNAWKSSSGPLQLVFAYFAVVQNIKKEEIENLQKYHDTISRPSH
IFRLCNDLASASAEIARGETANSVSCYMRTKGISEELATESVMNLIDE
TWKKMNKEKLSGSPFAKPFVETAINLARQSHCTYHNGDAHTSPDELTR
KRVLSVICEPILPFERENLYFQGLEHHHHHH

DNA sequence of pDW112 (SEQ ID NO: 92)

tggcgaatgggacgcgccctgtagcggcgcattaagcgcggcgggtgt
ggtggttacgcgcagcgtgaccgctacacttgccagcgccctagcgcc
cgctcctttcgctttcttcccttcctttctcgccacgttcgccggctt
tccccgtcaagctctaaatcgggggctccctttagggttccgatttag
tgctttacggcacctcgaccccaaaaaacttgattagggtgatggttc
acgtagtgggccatcgccctgatagacggtttttcgccctttgacgtt
ggagtccacgttctttaatagtggactcttgttccaaactggaacaac
actcaaccctatctcggtctattcttttgatttataagggattttgcc
gatttcggcctattggttaaaaaatgagctgatttaacaaaaatttaa
cgcgaattttaacaaaatattaacgtttacaatttcaggtggcacttt
tcggggaaatgtgcgcggaacccctatttgtttatttttctaaataca
ttcaaatatgtatccgctcatgaattaattcttagaaaaactcatcga
gcatcaaatgaaactgcaatttattcatatcaggattatcaataccat
atttttgaaaaagccgtttctgtaatgaaggagaaaactcaccgaggc
agttccataggatggcaagatcctggtatcggtctgcgattccgactc
gtccaacatcaatacaacctattaatttcccctcgtcaaaaataaggt
tatcaagtgagaaatcaccatgagtgacgactgaatccggtgagaatg
gcaaaagtttatgcatttctttccagacttgttcaacaggccagccat
tacgctcgtcatcaaaatcactcgcatcaaccaaaccgttattcattc
gtgattgcgcctgagcgagacgaaatacgcgatcgctgttaaaaggac
aattacaaacaggaatcgaatgcaaccggcgcaggaacactgccagcg
catcaacaatattttcacctgaatcaggatattcttctaatacctgga
atgctgttttcccggggatcgcagtggtgagtaaccatgcatcatcag
gagtacggataaaatgcttgatggtcggaagaggcataaattccgtca
gccagtttagtctgaccatctcatctgtaacatcattggcaacgctac -continued ctttgccatgtttcagaaacaactctggcgcatcgggcttcccataca
atcgatagattgtcgcacctgattgcccgacattatcgcgagcccatt
tatacccatataaatcagcatccatgttggaatttaatcgcggcctag
agcaagacgtttcccgttgaatatggctcataacaccccttgtattac
tgtttatgtaagcagacagttttattgttcatgaccaaaatcccttaa
cgtgagttttcgttccactgagcgtcagaccccgtagaaaagatcaaa
ggatcttcttgagatcctttttttctgcgcgtaatctgctgcttgcaa
acaaaaaaaccaccgctaccagcggtggtttgtttgccggatcaagag
ctaccaactctttttccgaaggtaactggcttcagcagagcgcagata
ccaaatactgtccttctagtgtagccgtagttaggccaccacttcaag
aactctgtagcaccgcctacatacctcgctctgctaatcctgttacca
gtggctgctgccagtggcgataagtcgtgtcttaccgggttggactca
agacgatagttaccggataaggcgcagcggtcgggctgaacggggggt
tcgtgcacacagcccagcttggagcgaacgacctacaccgaactgaga
tacctacagcgtgagctatgagaaagcgccacgcttcccgaagggaga
aaggcggacaggtatccggtaagcggcagggtcggaacaggagagcgc
acgagggagcttccagggggaaacgcctggtatctttatagtcctgtc
gggtttcgccacctctgacttgagcgtcgatttttgtgatgctcgtca
ggggggcggagcctatggaaaaacgccagcaacgcggcctttttacgg
ttcctggccttttgctggccttttgctcacatgttctttcctgcgtta
tcccctgattctgtggataaccgtattaccgcctttgagtgagctgat
accgctcgccgcagccgaacgaccgagcgcagcgagtcagtgagcgag
gaagcggaagagcgcctgatgcggtattttctccttacgcatctgtgc
ggtatttcacaccgcatatatggtgcactctcagtacaatctgctctg
atgccgcatagttaagccagtatacactccgctatcgctacgtgactg
ggtcatggctgcgccccgacacccgccaacacccgctgacgcgccctg
acgggcttgtctgctcccggcatccgcttacagacaagctgtgaccgt
ctccgggagctgcatgtgtcagaggttttcaccgtcatcaccgaaacg
cgcgaggcagctgcggtaaagctcatcagcgtggtcgtgaagcgattc
acagatgtctgcctgttcatccgcgtccagctcgttgagtttctccag
aagcgttaatgtctggcttctgataaagcgggccatgttaagggcggt
tttttcctgtttggtcactgatgcctccgtgtaagggggatttctgtt
catgggggtaatgataccgatgaaacgagagaggatgctcacgatacg
ggttactgatgatgaacatgcccggttactggaacgttgtgagggtaa
acaactggcggtatggatgcggcgggaccagagaaaaatcactcaggg
tcaatgccagcgcttcgttaatacagatgtaggtgttccacagggtag
ccagcagcatcctgcgatgcagatccggaacataatggtgcagggcgc
tgacttccgcgtttccagactttacgaaacacggaaaccgaagaccat
tcatgttgttgctcaggtcgcagacgttttgcagcagcagtcgcttca
cgttcgctcgcgtatcggtgattcattctgctaaccagtaaggcaacc
ccgccagcctagccgggtcctcaacgacaggagcacgatcatgcgcac -continued ccgtggggccgccatgccggcgataatggcctgcttctcgccgaaacg
tttggtggcgggaccagtgacgaaggcttgagcgagggcgtgcaagat
tccgaataccgcaagcgacaggccgatcatcgtcgcgctccagcgaaa
gcggtcctcgccgaaaatgacccagagcgctgccggcacctgtcctac
gagttgcatgataaagaagacagtcataagtgcggcgacgatagtcat
gccccgcgcccaccggaaggagctgactgggttgaaggctctcaaggg
catcggtcgagatcccggtgcctaatgagtgagctaacttacattaat
tgcgttgcgctcactgcccgctttccagtcgggaaacctgtcgtgcca
gctgcattaatgaatcggccaacgcgcggggagaggcggtttgcgtat
tgggcgccagggtggtttttcttttcaccagtgagacgggcaacagct
gattgcccttcaccgcctggccctgagagagttgcagcaagcggtcca
cgctggtttgccccagcaggcgaaaatcctgtttgatggtggttaacg
gcgggatataacatgagctgtcttcggtatcgtcgtatcccactaccg
agatatccgcaccaacgcgcagcccggactcggtaatggcgcgcattg
cgcccagcgccatctgatcgttggcaaccagcatcgcagtgggaacga
tgccctcattcagcatttgcatggtttgttgaaaaccggacatggcac
tccagtcgccttcccgttccgctatcggctgaatttgattgcgagtga
gatatttatgccagccagccagacgcagacgcgccgagacagaactta
aatgggcccgctaacagcgcgatttgctggtgacccaatgcgaccaga
tgctccacgcccagtcgcgtaccgtcttcatgggagaaaataatactg
ttgatgggtgtctggtcagagacatcaagaaataacgccggaacatta
gtgcaggcagcttccacagcaatggcatcctggtcatccagcggatag
ttaatgatcagcccactgacgcgttgcgcgagaagattgtgcaccgcc
gctttacaggcttcgacgccgcttcgttctaccatcgacaccaccacg
ctggcacccagttgatcggcgcgagatttaatcgccgcgacaatttgc
gacggcgcgtgcagggccagactggaggtggcaacgccaatcagcaac
gactgtttgcccgccagttgttgtgccacgcggttgggaatgtaattc
agctccgccatcgccgcttccacttttcccgcgttttcgcagaaacg
tggctggcctggttcaccacgcgggaaacggtctgataagagacaccg
gcatactctgcgacatcgtataacgttactggtttcacattcaccacc
ctgaattgactctcttccgggcgctatcatgccataccgcgaaaggtt
ttgcgccattcgatggtgtccgggatctcgacgctctcccttatgcga
ctcctgcattaggaagcagcccagtagtaggttgaggccgttgagcac
cgccgccgcaaggaatggtgcatgcaaggagatggcgcccaacagtcc
cccggccacggggcctgccaccatacccacgccgaaacaagcgctcat
gagcccgaagtggcgagcccgatcttccccatcggtgatgtcggcgat
ataggcgccagcaaccgcacctgtggcgccggtgatgccggccacgat
gcgtccggcgtagaggatcgagatctcgatcccgcgaaattaatacga
ctcactataggggaattgtgagcggataacaattcccctctagaaata
attttgtttaactttaagaaggagatatacatatggaagctcgtcgtt -continued ctgcgaactacgaacctaacagctgggactatgattacctgctgtcct
ccgacacggacgagtccatcgaagtatacaaagacaaagcgaaaaagc
tggaagccgaagttcgtcgcgagattaataacgaaaaagcagaatttc
tgaccctgctggaactgattgacaacgtccagcgcctgggcctgggtt
accgtttcgagtctgatatccgtggtgcgctggatcgcttcgtttcct
ccggcggcttcgatgcggtaaccaagacttccctgcacggtacggcac
tgtctttccgtctgctgcgtcaacacggttttgaggtttctcaggaag
cgttcagcggcttcaaagaccaaaacggcaacttcctggagaacctga
aggaagatatcaaagctatcctgagcctgtacgaggccagcttcctgg
ctctggaaggcgaaaacatcctggacgaggcgaaggttttcgcaatct
ctcatctgaaagaactgtctgaagaaaagatcggtaaagagctggcag
aacaggtgaaccatgcactggaactgccactgcatcgccgtactcagc
gtctggaagcagtatggtctatcgaggcctaccgtaaaaaggaggacg
cgaatcaggttctgctggagctggcaattctggattacaacatgatcc
agtctgtataccagcgtgatctgcgtgaaacgtcccgttggtggcgtc
gtgtgggtctggcgaccaaactgcactttgctcgtgaccgcctgattg
agagcttctactgggccgtgggtgtagcattcgaaccgcaatactccg
actgccgtaactccgtcgcaaaaatgttttctttcgtaaccattatcg
acgatatctacgatgtatacggcaccctggacgaactggagctgttta
ctgatgcagttgagcgttgggacgtaaacgccatcaacgacctgccgg
attacatgaaactgtgctttctggctctgtataacactattaacgaaa
tcgcctacgacaacctgaaagataaaggtgagaacatcctgccgtatc
tgaccaaagcctgggctgacctgtgcaacgctttcctgcaagaagcca
agtggctgtacaacaaatctactccgacctttgacgactacttcggca
acgcatggaaatcctcttctggcccgctgcaactggtgttcgcttact
tcgctgtcgtgcagaacattaaaaaggaagagatcgaaaacctgcaaa
aataccatgacaccatctctcgtccttcccatatcttccgtctgtgca
atgacctggctagcgcgtctgcggaaattgcgcgtggtgaaaccgcaa
atagcgtttcttgttacatgcgcactaaaggtatctccgaagaactgg
ctaccgaaagcgtgatgaatctgatcgatgaaacctggaaaaagatga
acaaggaaaaactgagtggtagcccgttcgcgaaaccgttcgtggaaa
ccgcgatcaacctggcacgtcaatctcactgcacttatcataacggcg
acgcgcatacctctccggatgagctgacccgcaaacgcgttctgtctg
taatctgcgaaccgattctgccgtttgaacgcgaaaacctgtattttc
agggcctcgagcaccaccaccaccaccactgagatccggctgctaaca
aagcccgaaaggaagctgagttggctgctgccaccgctgagcaataac
tagcataaccccttggggcctctaaacgggtcttgaggggttttttgc
tgaaaggaggaactatatccggat 16) Amino Acid Sequence of P. alba MEA L494P T536C (+)TEV - pDW113 (PC) (SEQ ID NO: 93)

MEARRSANYEPNSWDYDYLLSSDTDESIEVYKDKAKKLEAEVRREINN

EKAEFLTLLELIDNVQRLGLGYRFESDIRGALDRFVSSGGFDAVTKTS

LHGTALSFRLLRQHGFEVSQEAFSGFKDQNGNFLENLKEDIKAILSLY

EASFLALEGENILDEAKVFAISHLKELSEEKIGKELAEQVNHALELPL

HRRTQRLEAVWSIEAYRKKEDANQVLLELAILDYNMIQSVYQRDLRET

SRWWRRVGLATKLHFARDRLIESFYWAVGVAFEPQYSDCRNSVAKMFS

FVTIIDDIYDVYGTLDELELFTDAVERWDVNAINDLPDYMKLCFLALY

NTINEIAYDNLKDKGENILPYLTKAWADLCNAFLQEAKWLYNKSTPTF

DDYFGNAWKSSSGPLQLVFAYFAVVQNIKKEEIENLQKYHDTISRPSH

IFRLCNDLASASAEIARGETANSVSCYMRTKGISEELATESVMNLIDE

TWKKMNKEKLGGSPFAKPFVETAINLARQSHCTYHNGDAHTSPDELTR

KRVLSVICEPILPFERENLYFQGLEHHHHHH

DNA sequence of pDW113 (SEQ ID NO: 94)

tggcgaatgggacgcgccctgtagcggcgcattaagcgcggcgggtgt ggtggttacgcgcagcgtgaccgctacacttgccagcgccctagcgcc cgctcctttcgctttcttcccttcctttctcgccacgttcgccggctt tccccgtcaagctctaaatcgggggctccctttagggttccgatttag tgctttacggcacctcgaccccaaaaaacttgattagggtgatggttc acgtagtgggccatcgccctgatagacggtttttcgccctttgacgtt ggagtccacgttctttaatagtggactcttgttccaaactggaacaac actcaaccctatctcggtctattcttttgatttataagggattttgcc gatttcggcctattggttaaaaaatgagctgatttaacaaaaatttaa cgcgaattttaacaaaatattaacgtttacaatttcaggtggcacttt tcggggaaatgtgcgcggaacccctatttgtttatttttctaaataca ttcaaatatgtatccgctcatgaattaattcttagaaaaactcatcga gcatcaaatgaaactgcaatttattcatatcaggattatcaataccat atttttgaaaaagccgtttctgtaatgaaggagaaaactcaccgaggc agttccataggatggcaagatcctggtatcggtctgcgattccgactc gtccaacatcaatacaacctattaatttcccctcgtcaaaaataaggt tatcaagtgagaaatcaccatgagtgacgactgaatccggtgagaatg gcaaaagtttatgcatttctttccagacttgttcaacaggccagccat tacgctcgtcatcaaaatcactcgcatcaaccaaaccgttattcattc gtgattgcgcctgagcgagacgaaatacgcgatcgctgttaaaaggac aattacaaacaggaatcgaatgcaaccggcgcaggaacactgccagcg catcaacaatattttcacctgaatcaggatattcttctaatacctgga atgctgttttcccggggatcgcagtggtgagtaaccatgcatcatcag gagtacggataaaatgcttgatggtcggaagaggcataaattccgtca gccagtttagtctgaccatctcatctgtaacatcattggcaacgctac ctttgccatgtttcagaaacaactctggcgcatcgggcttcccataca -continued atcgatagattgtcgcacctgattgcccgacattatcgcgagcccatt tatacccatataaatcagcatccatgttggaatttaatcgcggcctag agcaagacgtttcccgttgaatatggctcataacaccccttgtattac tgtttatgtaagcagacagttttattgttcatgaccaaaatcccttaa cgtgagttttcgttccactgagcgtcagaccccgtagaaaagatcaaa ggatcttcttgagatcctttttttctgcgcgtaatctgctgcttgcaa acaaaaaaaccaccgctaccagcggtggtttgtttgccggatcaagag ctaccaactctttttccgaaggtaactggcttcagcagagcgcagata ccaaatactgtccttctagtgtagccgtagttaggccaccacttcaag aactctgtagcaccgcctacatacctcgctctgctaatcctgttacca gtggctgctgccagtggcgataagtcgtgtcttaccgggttggactca agacgatagttaccggataaggcgcagcggtcgggctgaacggggggt tcgtgcacacagcccagcttggagcgaacgacctacaccgaactgaga tacctacagcgtgagctatgagaaagcgccacgcttcccgaagggaga aaggcggacaggtatccggtaagcggcagggtcggaacaggagagcgc acgagggagcttccagggggaaacgcctggtatctttatagtcctgtc gggtttcgccacctctgacttgagcgtcgatttttgtgatgctcgtca ggggggcggagcctatggaaaaacgccagcaacgcggcctttttacgg ttcctggccttttgctggccttttgctcacatgttctttcctgcgtta tcccctgattctgtggataaccgtattaccgcctttgagtgagctgat accgctcgccgcagccgaacgaccgagcgcagcgagtcagtgagcgag gaagcggaagagcgcctgatgcggtattttctccttacgcatctgtgc ggtatttcacaccgcatatatggtgcactctcagtacaatctgctctg atgccgcatagttaagccagtatacactccgctatcgctacgtgactg ggtcatggctgcgccccgacacccgccaacacccgctgacgcgccctg acgggcttgtctgctcccggcatccgcttacagacaagctgtgaccgt ctccgggagctgcatgtgtcagaggttttcaccgtcatcaccgaaacg cgcgaggcagctgcggtaaagctcatcagcgtggtcgtgaagcgattc acagatgtctgcctgttcatccgcgtccagctcgttgagtttctccag aagcgttaatgtctggcttctgataaagcgggccatgttaagggcggt tttttcctgtttggtcactgatgcctccgtgtaagggggatttctgtt catgggggtaatgataccgatgaaacgagagaggatgctcacgatacg ggttactgatgatgaacatgcccggttactggaacgttgtgagggtaa acaactggcggtatggatgcggcgggaccagagaaaaatcactcaggg tcaatgccagcgcttcgttaatacagatgtaggtgttccacagggtag ccagcagcatcctgcgatgcagatccggaacataatggtgcagggcgc tgacttccgcgtttccagactttacgaaacacggaaaccgaagaccat tcatgttgttgctcaggtcgcagacgttttgcagcagcagtcgcttca cgttcgctcgcgtatcggtgattcattctgctaaccagtaaggcaacc ccgccagcctagccgggtcctcaacgacaggagcacgatcatgcgcac -continued ccgtggggccgccatgccggcgataatggcctgcttctcgccgaaacg
tttggtggcgggaccagtgacgaaggcttgagcgagggcgtgcaagat
tccgaataccgcaagcgacaggccgatcatcgtcgcgctccagcgaaa
gcggtcctcgccgaaaatgacccagagcgctgccggcacctgtcctac
gagttgcatgataaagaagacagtcataagtgcggcgacgatagtcat
gccccgcgcccaccggaaggagctgactgggttgaaggctctcaaggg
catcggtcgagatcccggtgcctaatgagtgagctaacttacattaat
tgcgttgcgctcactgcccgctttccagtcgggaaacctgtcgtgcca
gctgcattaatgaatcggccaacgcgcggggagaggcggtttgcgtat
tgggcgccagggtggtttttcttttcaccagtgagacgggcaacagct
gattgcccttcaccgcctggccctgagagagttgcagcaagcggtcca
cgctggtttgccccagcaggcgaaaatcctgtttgatggtggttaacg
gcgggatataacatgagctgtcttcggtatcgtcgtatcccactaccg
agatatccgcaccaacgcgcagcccggactcggtaatggcgcgcattg
cgcccagcgccatctgatcgttggcaaccagcatcgcagtgggaacga
tgccctcattcagcatttgcatggtttgttgaaaaccggacatggcac
tccagtcgccttcccgttccgctatcggctgaatttgattgcgagtga
gatatttatgccagccagccagacgcagacgcgccgagacagaactta
atgggcccgctaacagcgcgatttgctggtgacccaatgcgaccagat
gctccacgcccagtcgcgtaccgtcttcatgggagaaaataatactgt
tgatgggtgtctggtcagagacatcaagaaataacgccggaacattag
tgcaggcagcttccacagcaatggcatcctggtcatccagcggatagt
taatgatcagcccactgacgcgttgcgcgagaagattgtgcaccgccg
ctttacaggcttcgacgccgcttcgttctaccatcgacaccaccacgc
tggcacccagttgatcggcgcgagatttaatcgccgcgacaatttgcg
acggcgcgtgcagggccagactggaggtggcaacgccaatcagcaacg
actgtttgcccgccagttgttgtgccacgcggttgggaatgtaattca
gctccgccatcgccgcttccactttttcccgcgttttcgcagaaacgt
ggctggcctggttcaccacgcgggaaacggtctgataagagacaccgg
catactctgcgacatcgtataacgttactggtttcacattcaccaccc
tgaattgactctcttccgggcgctatcatgccataccgcgaaaggttt
tgcgccattcgatggtgtccgggatctcgacgctctcccttatgcgac
tcctgcattaggaagcagcccagtagtaggttgaggccgttgagcacc
gccgccgcaaggaatggtgcatgcaaggagatggcgcccaacagtccc
ccggccacggggcctgccaccatacccacgccgaaacaagcgctcatg
agcccgaagtggcgagcccgatcttccccatcggtgatgtcggcgata
taggcgccagcaaccgcacctgtggcgccggtgatgccggccacgatg
cgtccggcgtagaggatcgagatctcgatcccgcgaaattaatacgac
tcactataggggaattgtgagcggataacaattcccctctagaaataa
ttttgtttaactttaagaaggagatatacatatggaagctcgtcgttc
tgcgaactacgaacctaacagctgggactatgattacctgctgtcctc
cgacacggacgagtccatcgaagtatacaaagacaaagcgaaaaagct
ggaagccgaagttcgtcgcgagattaataacgaaaaagcagaatttct
gaccctgctggaactgattgacaacgtccagcgcctgggcctgggtta
ccgtttcgagtctgatatccgtggtgcgctggatcgcttcgtttcctc
cggcggcttcgatgcggtaaccaagacttccctgcacggtacggcact
gtctttccgtctgctgcgtcaacacggttttgaggtttctcaggaagc
gttcagcggcttcaaagaccaaaacggcaacttcctggagaacctgaa
ggaagatatcaaagctatcctgagcctgtacgaggccagcttcctggc
tctggaaggcgaaaacatcctggacgaggcgaaggttttcgcaatctc
tcatctgaaagaactgtctgaagaaaagatcggtaaagagctggcaga
acaggtgaaccatgcactggaactgccactgcatcgccgtactcagcg
tctggaagcagtatggtctatcgaggcctaccgtaaaaaggaggacgc
gaatcaggttctgctggagctggcaattctggattacaacatgatcca
gtctgtataccagcgtgatctgcgtgaaacgtcccgttggtggcgtcg
tgtgggtctggcgaccaaactgcactttgctcgtgaccgcctgattga
gagcttctactgggccgtgggtgtagcattcgaaccgcaatactccga
ctgccgtaactccgtcgcaaaaatgttttctttcgtaaccattatcga
cgatatctacgatgtatacggcaccctggacgaactggagctgtttac
tgatgcagttgagcgttgggacgtaaacgccatcaacgacctgccgga
ttacatgaaactgtgctttctggctctgtataacactattaacgaaat
cgcctacgacaacctgaaagataaaggtgagaacatcctgccgtatct
gaccaaagcctgggctgacctgtgcaacgctttcctgcaagaagccaa
gtggctgtacaacaaatctactccgacctttgacgactacttcggcaa
cgcatggaaatcctcttctggcccgctgcaactggtgttcgcttactt
cgctgtcgtgcagaacattaaaaaggaagagatcgaaaacctgcaaaa
ataccatgacaccatctctcgtccttcccatatcttccgtctgtgcaa
tgacctggctagcgcgtctgcggaaattgcgcgtggtgaaaccgcaaa
tagcgtttcttgttacatgcgcactaaaggtatctccgaagaactggc
taccgaaagcgtgatgaatctgatcgatgaaacctggaaaaagatgaa
caaggaaaaactgggtggtagcccgttcgcgaaaccgttcgtggaaac
cgcgatcaacctggcacgtcaatctcactgcacttatcataacggcga
cgcgcatacctctccggatgagctgacccgcaaacgcgttctgtctgt
aatctgcgaaccgattctgccgtttgaacgcgaaaacctgtattttca
gggcctcgagcaccaccaccaccaccactgagatccggctgctaacaa
agcccgaaaggaagctgagttggctgctgccaccgctgagcaataact
agcataaccccttggggcctctaaacgggtcttgaggggttttttgct
gaaaggaggaactatatccggat Amino Acid Sequence of P. alba MEA T536F (+)TEV - pDW87 (SEQ ID NO: 95)

MEARRSANYEPNSWDYDYLLSSDTDESIEVYKDKAKKLEAEVRREINN
EKAEFLTLLELIDNVQRLGLGYRFESDIRGALDRFVSSGGFDAVTKTS
LHGTALSFRLLRQHGFEVSQEAFSGFKDQNGNFLENLKEDIKAILSLY
EASFLALEGENILDEAKVFAISHLKELSEEKIGKELAEQVNHALELPL
HRRTQRLEAVWSIEAYRKKEDANQVLLELAILDYNMIQSVYQRDLRET
SRWWRRVGLATKLHFARDRLIESFYWAVGVAFEPQYSDCRNSVAKMFS
FVTIIDDIYDVYGTLDELELFTDAVERWDVNAINDLPDYMKLCFLALY
NTINEIAYDNLKDKGENILPYLTKAWADLCNAFLQEAKWLYNKSTPTF
DDYFGNAWKSSSGPLQLVFAYFAVVQNIKKEEIENLQKYHDTISRPSH
IFRLCNDLASASAEIARGETANSVSCYMRTKGISEELATESVMNLIDE
TWKKMNKEKLGGSLFAKPFVETAINLARQSHCTYHNGDAHTSPDELTR
KRVLSVIFEPILPFERENLYFQGLEHHHHHH

DNA sequence of pDW87 (SEQ ID NO: 96)

tggcgaatgggacgcgccctgtagcggcgcattaagcgcggcgggtgt
ggtggttacgcgcagcgtgaccgctacacttgccagcgccctagcgcc
cgctcctttcgctttcttcccttcctttctcgccacgttcgccggctt
tccccgtcaagctctaaatcgggggctccctttagggttccgatttag
tgctttacggcacctcgaccccaaaaaacttgattagggtgatggttc
acgtagtgggccatcgccctgatagacggtttttcgccctttgacgtt
ggagtccacgttctttaatagtggactcttgttccaaactggaacaac
actcaaccctatctcggtctattcttttgatttataagggattttgcc
gatttcggcctattggttaaaaaatgagctgatttaacaaaaatttaa
cgcgaattttaacaaaatattaacgtttacaatttcaggtggcacttt
tcggggaaatgtgcgcggaacccctatttgtttatttttctaaataca
ttcaaatatgtatccgctcatgaattaattcttagaaaaactcatcga
gcatcaaatgaaactgcaatttattcatatcaggattatcaataccat
atttttgaaaaagccgtttctgtaatgaaggagaaaactcaccgaggc
agttccataggatggcaagatcctggtatcggtctgcgattccgactc
gtccaacatcaatacaacctattaatttcccctcgtcaaaaataaggt
tatcaagtgagaaatcaccatgagtgacgactgaatccggtgagaatg
gcaaaagtttatgcatttctttccagacttgttcaacaggccagccat
tacgctcgtcatcaaaatcactcgcatcaaccaaaccgttattcattc
gtgattgcgcctgagcgagacgaaatacgcgatcgctgttaaaaggac
aattacaaacaggaatcgaatgcaaccggcgcaggaacactgccagcg
catcaacaatattttcacctgaatcaggatattcttctaatacctgga
atgctgttttcccggggatcgcagtggtgagtaaccatgcatcatcag
gagtacggataaaatgcttgatggtcggaagaggcataaattccgtca
gccagtttagtctgaccatctcatctgtaacatcattggcaacgctac
ctttgccatgtttcagaaacaactctggcgcatcgggcttcccataca -continued atcgatagattgtcgcacctgattgcccgacattatcgcgagcccatt
tatacccatataaatcagcatccatgttggaatttaatcgcggcctag
agcaagacgtttcccgttgaatatggctcataacaccccttgtattac
tgtttatgtaagcagacagttttattgttcatgaccaaaatcccttaa
cgtgagttttcgttccactgagcgtcagaccccgtagaaaagatcaaa
ggatcttcttgagatcctttttttctgcgcgtaatctgctgcttgcaa
acaaaaaaaccaccgctaccagcggtggtttgtttgccggatcaagag
ctaccaactctttttccgaaggtaactggcttcagcagagcgcagata
ccaaatactgtccttctagtgtagccgtagttaggccaccacttcaag
aactctgtagcaccgcctacatacctcgctctgctaatcctgttacca
gtggctgctgccagtggcgataagtcgtgtcttaccgggttggactca
agacgatagttaccggataaggcgcagcggtcgggctgaacggggggt
tcgtgcacacagcccagcttggagcgaacgacctacaccgaactgaga
tacctacagcgtgagctatgagaaagcgccacgcttcccgaagggaga
aaggcggacaggtatccggtaagcggcagggtcggaacaggagagcgc
acgagggagcttccagggggaaacgcctggtatctttatagtcctgtc
gggtttcgccacctctgacttgagcgtcgatttttgtgatgctcgtca
ggggggcggagcctatggaaaaacgccagcaacgcggcctttttacgg
ttcctggccttttgctggccttttgctcacatgttctttcctgcgtta
tcccctgattctgtggataaccgtattaccgcctttgagtgagctgat
accgctcgccgcagccgaacgaccgagcgcagcgagtcagtgagcgag
gaagcggaagagcgcctgatgcggtattttctccttacgcatctgtgc
ggtatttcacaccgcatatatggtgcactctcagtacaatctgctctg
atgccgcatagttaagccagtatacactccgctatcgctacgtgactg
ggtcatggctgcgccccgacacccgccaacacccgctgacgcgccctg
acgggcttgtctgctcccggcatccgcttacagacaagctgtgaccgt
ctccgggagctgcatgtgtcagaggttttcaccgtcatcaccgaaacg
cgcgaggcagctgcggtaaagctcatcagcgtggtcgtgaagcgattc
acagatgtctgcctgttcatccgcgtccagctcgttgagtttctccag
aagcgttaatgtctggcttctgataaagcgggccatgttaagggcggt
tttttcctgtttggtcactgatgcctccgtgtaagggggatttctgtt
catgggggtaatgataccgatgaaacgagagaggatgctcacgatacg
ggttactgatgatgaacatgcccggttactggaacgttgtgagggtaa
acaactggcggtatggatgcggcgggaccagagaaaaatcactcaggg
tcaatgccagcgcttcgttaatacagatgtaggtgttccacagggtag
ccagcagcatcctgcgatgcagatccggaacataatggtgcagggcgc
tgacttccgcgtttccagactttacgaaacacggaaaccgaagaccat
tcatgttgttgctcaggtcgcagacgttttgcagcagcagtcgcttca
cgttcgctcgcgtatcggtgattcattctgctaaccagtaaggcaacc
ccgccagcctagccgggtcctcaacgacaggagcacgatcatgcgcac -continued ccgtggggccgccatgccggcgataatggcctgcttctcgccgaaacg tttggtggcgggaccagtgacgaaggcttgagcgagggcgtgcaagat tccgaataccgcaagcgacaggccgatcatcgtcgcgctccagcgaaa gcggtcctcgccgaaaatgacccagagcgctgccggcacctgtcctac gagttgcatgataaagaagacagtcataagtgcggcgacgatagtcat gccccgcgcccaccggaaggagctgactgggttgaaggctctcaaggg catcggtcgagatcccggtgcctaatgagtgagctaacttacattaat tgcgttgcgctcactgcccgctttccagtcgggaaacctgtcgtgcca gctgcattaatgaatcggccaacgcgcggggagaggcggtttgcgtat tgggcgccagggtggtttttcttttcaccagtgagacgggcaacagct gattgcccttcaccgcctggccctgagagagttgcagcaagcggtcca cgctggtttgccccagcaggcgaaaatcctgtttgatggtggttaacg gcgggatataacatgagctgtcttcggtatcgtcgtatcccactaccg agatatccgcaccaacgcgcagcccggactcggtaatggcgcgcattg cgcccagcgccatctgatcgttggcaaccagcatcgcagtgggaacga tgccctcattcagcatttgcatggtttgttgaaaaccggacatggcac tccagtcgccttcccgttccgctatcggctgaatttgattgcgagtga gatatttatgccagccagccagacgcagacgcgccgagacagaactta atgggcccgctaacagcgcgatttgctggtgacccaatgcgaccagat gctccacgcccagtcgcgtaccgtcttcatgggagaaaataatactgt tgatgggtgtctggtcagagacatcaagaaataacgccggaacattag tgcaggcagcttccacagcaatggcatcctggtcatccagcggatagt taatgatcagcccactgacgcgttgcgcgagaagattgtgcaccgccg ctttacaggcttcgacgccgcttcgttctaccatcgacaccaccacgc tggcacccagttgatcggcgcgagatttaatcgccgcgacaatttgcg acggcgcgtgcagggccagactggaggtggcaacgccaatcagcaacg actgtttgcccgccagttgttgtgccacgcggttgggaatgtaattca gctccgccatcgccgcttccactttttcccgcgttttcgcagaaacgt ggctggcctggttcaccacgcgggaaacggtctgataagagacaccgg catactctgcgacatcgtataacgttactggtttcacattcaccaccc tgaattgactctcttccgggcgctatcatgccataccgcgaaaggttt tgcgccattcgatggtgtccgggatctcgacgctctcccttatgcgac tcctgcattaggaagcagcccagtagtaggttgaggccgttgagcacc gccgccgcaaggaatggtgcatgcaaggagatggcgcccaacagtccc ccggccacggggcctgccaccatacccacgccgaaacaagcgctcatg agcccgaagtggcgagcccgatcttccccatcggtgatgtcggcgata taggcgccagcaaccgcacctgtggcgccggtgatgccggccacgatg cgtccggcgtagaggatcgagatctcgatcccgcgaaattaatacgac tcactataggggaattgtgagcggataacaattcccctctagaaataa ttttgtttaactttaagaaggagatatacatatggaagctcgtcgttc tgcgaactacgaacctaacagctgggactatgattacctgctgtcctc -continued cgacacggacgagtccatcgaagtatacaaagacaaagcgaaaaagct ggaagccgaagttcgtcgcgagattaataacgaaaaagcagaatttct gaccctgctggaactgattgacaacgtccagcgcctgggcctgggtta ccgtttcgagtctgatatccgtggtgcgctggatcgcttcgtttcctc cggcggcttcgatgcggtaaccaagacttccctgcacggtacggcact gtctttccgtctgctgcgtcaacacggttttgaggtttctcaggaagc gttcagcggcttcaaagaccaaaacggcaacttcctggagaacctgaa ggaagatatcaaagctatcctgagcctgtacgaggccagcttcctggc tctggaaggcgaaaacatcctggacgaggcgaaggttttcgcaatctc tcatctgaaagaactgtctgaagaaaagatcggtaaagagctggcaga acaggtgaaccatgcactggaactgccactgcatcgccgtactcagcg tctggaagcagtatggtctatcgaggcctaccgtaaaaaggaggacgc gaatcaggttctgctggagctggcaattctggattacaacatgatcca gtctgtataccagcgtgatctgcgtgaaacgtcccgttggtggcgtcg tgtgggtctggcgaccaaactgcactttgctcgtgaccgcctgattga gagcttctactgggccgtgggtgtagcattcgaaccgcaatactccga ctgccgtaactccgtcgcaaaaatgttttctttcgtaaccattatcga cgatatctacgatgtatacggcaccctggacgaactggagctgtttac tgatgcagttgagcgttgggacgtaaacgccatcaacgacctgccgga ttacatgaaactgtgctttctggctctgtataacactattaacgaaat cgcctacgacaacctgaaagataaaggtgagaacatcctgccgtatct gaccaaagcctgggctgacctgtgcaacgctttcctgcaagaagccaa gtggctgtacaacaaatctactccgacctttgacgactacttcggcaa cgcatggaaatcctcttctggcccgctgcaactggtgttcgcttactt cgctgtcgtgcagaacattaaaaaggaagagatcgaaaacctgcaaaa ataccatgacaccatctctcgtccttcccatatcttccgtctgtgcaa tgacctggctagcgcgtctgcggaaattgcgcgtggtgaaaccgcaaa tagcgtttcttgttacatgcgcactaaaggtatctccgaagaactggc taccgaaagcgtgatgaatctgatcgatgaaacctggaaaaagatgaa caaggaaaaactgggtggtagcctgttcgcgaaaccgttcgtggaaac cgcgatcaacctggcacgtcaatctcactgcacttatcataacggcga cgcgcatacctctccggatgagctgacccgcaaacgcgttctgtctgt aatctttgaaccgattctgccgtttgaacgcgaaaacctgtattttca gggcctcgagcaccaccaccaccaccactgagatccggctgctaacaa agcccgaaaggaagctgagttggctgctgccaccgctgagcaataact agcataaccccttggggcctctaaacgggtcttgaggggttttttgct gaaaggaggaactatatccggat Amino Acid Sequence of P. alba MEA L494P T536F (+)TEV - pDW95 (SEQ ID NO: 97)

MEARRSANYEPNSWDYDYLLSSDTDESIEVYKDKAKKLEAEVRREINN

EKAEFLTLLELIDNVQRLGLGYRFESDIRGALDRFVSSGGFDAVTKTS

LHGTALSFRLLRQHGFEVSQEAFSGFKDQNGNFLENLKEDIKAILSLY

EASFLALEGENILDEAKVFAISHLKELSEEKIGKELAEQVNHALELPL

HRRTQRLEAVWSIEAYRKKEDANQVLLELAILDYNMIQSVYQRDLRET

SRWWRRVGLATKLHFARDRLIESFYWAVGVAFEPQYSDCRNSVAKMFS

FVTIIDDIYDVYGTLDELELFTDAVERWDVNAINDLPDYMKLCFLALY

NTINEIAYDNLKDKGENILPYLTKAWADLCNAFLQEAKWLYNKSTPTF

DDYFGNAWKSSSGPLQLVFAYFAVVQNIKKEEIENLQKYHDTISRPSH

IFRLCNDLASASAEIARGETANSVSCYMRTKGISEELATESVMNLIDE

TWKKMNKEKLGGSPFAKPFVETAINLARQSHCTYHNGDAHTSPDELTR

KRVLSVIFEPILPFERENLYFQGLEHHHHHH

DNA sequence of pDW95 (SEQ ID NO: 98)

tggcgaatgggacgcgccctgtagcggcgcattaagcgcggcgggtgt ggtggttacgcgcagcgtgaccgctacacttgccagcgccctagcgcc cgctcctttcgctttcttcccttcctttctcgccacgttcgccggctt tccccgtcaagctctaaatcgggggctccctttagggttccgatttag tgctttacggcacctcgaccccaaaaaacttgattagggtgatggttc acgtagtgggccatcgccctgatagacggtttttcgccctttgacgtt ggagtccacgttctttaatagtggactcttgttccaaactggaacaac actcaaccctatctcggtctattcttttgatttataagggattttgcc gatttcggcctattggttaaaaaatgagctgatttaacaaaaatttaa cgcgaattttaacaaaatattaacgtttacaatttcaggtggcacttt tcggggaaatgtgcgcggaacccctatttgtttatttttctaaataca ttcaaatatgtatccgctcatgaattaattcttagaaaaactcatcga gcatcaaatgaaactgcaatttattcatatcaggattatcaataccat atttttgaaaaagccgtttctgtaatgaaggagaaaactcaccgaggc agttccataggatggcaagatcctggtatcggtctgcgattccgactc gtccaacatcaatacaacctattaatttcccctcgtcaaaaataaggt tatcaagtgagaaatcaccatgagtgacgactgaatccggtgagaatg gcaaaagtttatgcatttctttccagacttgttcaacaggccagccat tacgctcgtcatcaaaatcactcgcatcaaccaaaccgttattcattc gtgattgcgcctgagcgagacgaaatacgcgatcgctgttaaaaggac aattacaaacaggaatcgaatgcaaccggcgcaggaacactgccagcg catcaacaatattttcacctgaatcaggatattcttctaatacctgga atgctgttttcccggggatcgcagtggtgagtaaccatgcatcatcag gagtacggataaaatgcttgatggtcggaagaggcataaattccgtca gccagtttagtctgaccatctcatctgtaacatcattggcaacgctac ctttgccatgtttcagaaacaactctggcgcatcgggcttcccataca -continued atcgatagattgtcgcacctgattgcccgacattatcgcgagcccatt tatacccatataaatcagcatccatgttggaatttaatcgcggcctag agcaagacgtttcccgttgaatatggctcataacaccccttgtattac tgtttatgtaagcagacagttttattgttcatgaccaaaatcccttaa cgtgagttttcgttccactgagcgtcagaccccgtagaaaagatcaaa ggatcttcttgagatcctttttttctgcgcgtaatctgctgcttgcaa acaaaaaaaccaccgctaccagcggtggtttgtttgccggatcaagag ctaccaactctttttccgaaggtaactggcttcagcagagcgcagata ccaaatactgtccttctagtgtagccgtagttaggccaccacttcaag aactctgtagcaccgcctacatacctcgctctgctaatcctgttacca gtggctgctgccagtggcgataagtcgtgtcttaccgggttggactca agacgatagttaccggataaggcgcagcggtcgggctgaacggggggt tcgtgcacacagcccagcttggagcgaacgacctacaccgaactgaga tacctacagcgtgagctatgagaaagcgccacgcttcccgaagggaga aaggcggacaggtatccggtaagcggcagggtcggaacaggagagcgc acgagggagcttccagggggaaacgcctggtatctttatagtcctgtc gggtttcgccacctctgacttgagcgtcgatttttgtgatgctcgtca ggggggcggagcctatggaaaaacgccagcaacgcggcctttttacgg ttcctggccttttgctggccttttgctcacatgttctttcctgcgtta tcccctgattctgtggataaccgtattaccgcctttgagtgagctgat accgctcgccgcagccgaacgaccgagcgcagcgagtcagtgagcgag gaagcggaagagcgcctgatgcggtattttctccttacgcatctgtgc ggtatttcacaccgcatatatggtgcactctcagtacaatctgctctg atgccgcatagttaagccagtatacactccgctatcgctacgtgactg ggtcatggctgcgccccgacacccgccaacacccgctgacgcgccctg acgggcttgtctgctcccggcatccgcttacagacaagctgtgaccgt ctccgggagctgcatgtgtcagaggttttcaccgtcatcaccgaaacg cgcgaggcagctgcggtaaagctcatcagcgtggtcgtgaagcgattc acagatgtctgcctgttcatccgcgtccagctcgttgagtttctccag aagcgttaatgtctggcttctgataaagcgggccatgttaagggcggt ttttcctgtttggtcactgatgcctccgtgtaagggggatttctgtt catgggggtaatgataccgatgaaacgagagaggatgctcacgatacg ggttactgatgatgaacatgcccggttactggaacgttgtgagggtaa acaactggcggtatggatgcggcgggaccagagaaaaatcactcaggg tcaatgccagcgcttcgttaatacagatgtaggtgttccacagggtag ccagcagcatcctgcgatgcagatccggaacataatggtgcagggcgc tgacttccgcgtttccagactttacgaaacacggaaaccgaagaccat tcatgttgttgctcaggtcgcagacgttttgcagcagcagtcgcttca cgttcgctcgcgtatcggtgattcattctgctaaccagtaaggcaacc ccgccagcctagccgggtcctcaacgacaggagcacgatcatgcgcac -continued ccgtggggccgccatgccggcgataatggcctgcttctcgccgaaacg tttggtggcgggaccagtgacgaaggcttgagcgagggcgtgcaagat tccgaataccgcaagcgacaggccgatcatcgtcgcgctccagcgaaa gcggtcctcgccgaaaatgacccagagcgctgccggcacctgtcctac gagttgcatgataaagaagacagtcataagtgcggcgacgatagtcat gccccgcgcccaccggaaggagctgactgggttgaaggctctcaaggg catcggtcgagatcccggtgcctaatgagtgagctaacttacattaat tgcgttgcgctcactgcccgctttccagtcgggaaacctgtcgtgcca gctgcattaatgaatcggccaacgcgcggggagaggcggtttgcgtat tgggcgccagggtggtttttcttttcaccagtgagacgggcaacagct gattgcccttcaccgcctggccctgagagagttgcagcaagcggtcca cgctggtttgccccagcaggcgaaaatcctgtttgatggtggttaacg gcgggatataacatgagctgtcttcggtatcgtcgtatcccactaccg agatatccgcaccaacgcgcagcccggactcggtaatggcgcgcattg cgcccagcgccatctgatcgttggcaaccagcatcgcagtgggaacga tgccctcattcagcatttgcatggtttgttgaaaaccggacatggcac tccagtcgccttcccgttccgctatcggctgaatttgattgcgagtga gatatttatgccagccagccagacgcagacgcgccgagacagaactta atgggcccgctaacagcgcgatttgctggtgacccaatgcgaccagat gctccacgcccagtcgcgtaccgtcttcatgggagaaaataatactgt tgatgggtgtctggtcagagacatcaagaaataacgccggaacattag tgcaggcagcttccacagcaatggcatcctggtcatccagcggatagt taatgatcagcccactgacgcgttgcgcgagaagattgtgcaccgccg ctttacaggcttcgacgccgcttcgttctaccatcgacaccaccacgc tggcacccagttgatcggcgcgagatttaatcgccgcgacaatttgcg acggcgcgtgcagggccagactggaggtggcaacgccaatcagcaacg actgtttgcccgccagttgttgtgccacgcggttgggaatgtaattca gctccgccatcgccgcttccactttttcccgcgttttcgcagaaacgt ggctggcctggttcaccacgcgggaaacggtctgataagagacaccgg catactctgcgacatcgtataacgttactggtttcacattcaccaccc tgaattgactctcttccgggcgctatcatgccataccgcgaaaggttt tgcgccattcgatggtgtccgggatctcgacgctctcccttatgcgac tcctgcattaggaagcagcccagtagtaggttgaggccgttgagcacc gccgccgcaaggaatggtgcatgcaaggagatggcgcccaacagtccc ccggccacggggcctgccaccatacccacgccgaaacaagcgctcatg agcccgaagtggcgagcccgatcttccccatcggtgatgtcggcgata taggcgccagcaaccgcacctgtggcgccggtgatgccggccacgatg cgtccggcgtagaggatcgagatctcgatcccgcgaaattaatacgac tcactataggggaattgtgagcggataacaattcccctctagaaataa ttttgtttaactttaagaaggagatatacatatggaagctcgtcgttc tgcgaactacgaacctaacagctgggactatgattacctgctgtcctc -continued cgacacggacgagtccatcgaagtatacaaagacaaagcgaaaaagct ggaagccgaagttcgtcgcgagattaataacgaaaaagcagaatttct gaccctgctggaactgattgacaacgtccagcgcctgggcctgggtta ccgtttcgagtctgatatccgtggtgcgctggatcgcttcgtttcctc cggcggcttcgatgcggtaaccaagacttccctgcacggtacggcact gtctttccgtctgctgcgtcaacacggttttgaggtttctcaggaagc gttcagcggcttcaaagaccaaaacggcaacttcctggagaacctgaa ggaagatatcaaagctatcctgagcctgtacgaggccagcttcctggc tctggaaggcgaaaacatcctggacgaggcgaaggttttcgcaatctc tcatctgaaagaactgtctgaagaaaagatcggtaaagagctggcaga acaggtgaaccatgcactggaactgccactgcatcgccgtactcagcg tctggaagcagtatggtctatcgaggcctaccgtaaaaaggaggacgc gaatcaggttctgctggagctggcaattctggattacaacatgatcca gtctgtataccagcgtgatctgcgtgaaacgtcccgttggtggcgtcg tgtgggtctggcgaccaaactgcactttgctcgtgaccgcctgattga gagcttctactgggccgtgggtgtagcattcgaaccgcaatactccga ctgccgtaactccgtcgcaaaaatgttttctttcgtaaccattatcga cgatatctacgatgtatacggcaccctggacgaactggagctgtttac tgatgcagttgagcgttgggacgtaaacgccatcaacgacctgccgga ttacatgaaactgtgctttctggctctgtataacactattaacgaaat cgcctacgacaacctgaaagataaaggtgagaacatcctgccgtatct gaccaaagcctgggctgacctgtgcaacgctttcctgcaagaagccaa gtggctgtacaacaaatctactccgacctttgacgactacttcggcaa cgcatggaaatcctcttctggcccgctgcaactggtgttcgcttactt cgctgtcgtgcagaacattaaaaaggaagagatcgaaaacctgcaaaa ataccatgacaccatctctcgtccttcccatatcttccgtctgtgcaa tgacctggctagcgcgtctgcggaaattgcgcgtggtgaaaccgcaaa tagcgtttcttgttacatgcgcactaaaggtatctccgaagaactggc taccgaaagcgtgatgaatctgatcgatgaaacctggaaaaagatgaa caaggaaaaactgggtggtagcccgttcgcgaaaccgttcgtggaaac cgcgatcaacctggcacgtcaatctcactgcacttatcataacggcga cgcgcatacctctccggatgagctgacccgcaaacgcgttctgtctgt aatctttgaaccgattctgccgtttgaacgcgaaaacctgtattttca gggcctcgagcaccaccaccaccaccactgagatccggctgctaacaa agcccgaaaggaagctgagttggctgctgccaccgctgagcaataact agcataaccccttggggcctctaaacgggtcttgaggggttttttgct gaaaggaggaactatatccggat Example 7

Biochemical Analysis of *P. alba* IspS Variants

As denoted in Example 8, P (L494P), SP (G491S, L494P) and SPC (G491S, L494P, T536C) isoprene synthase amino acid variants were determined to contain increased specific activity compared to WT isoprene synthase with the P variant containing the greatest specific activity (2.0 times greater than WT). The KMs of the P, SP, and SPC isoprene synthase amino acid variants were less than the KM of the WT isoprene synthase. In addition, the kcat of the β isoprene synthase amino acid variant was greater than the WT isoprene synthase. These results indicate that the P, SP and SPC amino acid variants of isoprene synthase may improve the efficiency (isoprene production rate/[Isoprene synthase]) of production of isoprene in vivo leading to an improved process for isoprene production.

Methods

Materials:

Lysis Buffer: Ni wash+0.5 mM PMST, 0.01% Tween-20, 1 mg/ml lysozyme, 0.2 mg/ml DNase Ni wash buffer: 50 mM NaH2PO4, 300 mM NaCl, 20 mM Imidazole, pH 8.0

Ni elution buffer: 50 mM NaH2PO4, 300 mM NaCl, 500 mM Imidazole, pH 8.0

PD-10 buffer: 50 mM Tris, 0.05 M NaCl, pH 8.0

Expression:

1. Overnight culture grown in 3 mL of LB broth at 30 C with $Kan_{50}$, $Chlor_{25}$
2. Transfer 50 uL of overnight culture into 100 mL of fresh LB with antibiotic
3. Grow at 37 C, 250 RPM for 3.5 hours
4. Induce with 400 uM IPTG at OD600~0.4
5. Reduce temp to 30 C and shake for 4 hours.
6. Transfer cells into 50 mL tubes and spin 25 min at 3800 RPM
7. Decant supernatant and repeat centrifugation step with remaining media
8. Decant supernatant
9. Store pellets at −80 C Purification:

1. Initial Purification—Resuspend the pellet in 3 ml of fresh lysis buffer. Break cells by passing them through the French Press using the small cylinder. Centrifuge samples for 1 hour at 30,000×G and collect the supernatant. Retain pellet in order to test for presence of insoluble protein. Pre equilibrate 0.5 mL Ni Sepharose 6 Fast Flow resin (Amersham) in a 20 ml disposable column with 10 mL of Ni wash buffer. Add protein to column and shake for 60 min at 4 C to bind protein. Elute protein with 2.5 mL Ni elution buffer.
2. Buffer Exchange—Equilibrate a PD-10 column (GE Healthcare) with 25 mL of PD-10 buffer. Load protein on to column and elute with 3.5 mL of PD-10 buffer.
3. Analyze samples using SDS-PAGE to determine relative purity of pellet (p), supernatant (s), and after both columns (ni).
4. Aliquot protein and store at −80 C.

Specific Activity Measurement—

10 uL of purified enzyme was incubated with 4 mM DMAPP, 50 mM MgCl2 in a buffer containing 50 mM Tris and 50 mM NaCl (pH=8) to a final volume of 100 uL for 15 min. at 30 C in gas tight 2 mL vials. Reactions were terminated with the addition of 100 uL of 250 uM EDTA, pH=8. Samples were analyzed by GC-MS to determine the concentration of isoprene in the headspace of the vials. All specific activity measurements were performed in triplicate.

$k_{cat}$ and $K_M$ Determination—

10 uL of purified enzyme was incubated with DMAPP at concentrations ranging from 1.25 to 20 mM DMAPP in a buffer containing 50 mM Tris, 50 mM MgCl2 and 50 mM NaCl (pH=8) to a final volume of 100 uL for 15 min. at 30 C in gas tight 2 mL vials. Reactions were terminated with the addition of 100 uL of 250 mM EDTA, pH=8. Samples were analyzed by GC-MS to determine the concentration of isoprene in the headspace of the vials. Data were analyzed using Kaleidagraph and fit to following equation for uncompetitive substrate inhibition: rate/E=kcat*S/(KM+S*(1+S/Ki)). All kinetic assays were performed in triplicate.

Protein Concentration Determination—

Protein concentration was determined by measuring the absorbance of each protein solution at 280 nm on a Helwlett Pachard 8453 UV-Vis spectrophotometer and converting the absorbance to protein concentration using the extinction coefficient as determined on the Expasy website (Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607). The protein concentrations of isoprene synthase variants assayed for $K_M$ and $k_{cat}$ determination were verified by comparative gel electrophoresis of a dilution series of each protein (FIG. 61).

Results/Discussion:

The specific activity of each protein was determined (FIG. 62 and Table 7-4). The specific activity of the β isoprene synthase amino acid variant was 2-fold greater than the specific activity of the WT isoprene synthase. The specific activities of the SP and SPC variants were greater than the WT isoprene synthase but less than the P isoprene synthase variant. All other isoprene synthases tested in this study displayed equal or decreased activity compared to the WT isoprene synthase.

The rate of conversion of DMAPP to isoprene was analyzed over a range of DMAPP concentrations in order to determine the kcat and KM parameters for WT, P, SP and SPC isoprene synthase amino acid variants (FIG. 63, Table 7-5). The enzymes all exhibited rate profiles consistent with uncompetitive substrate inhibition by DMAPP. The KMs of the P, SP, and SPC isoprene synthase variants were less than the KM of the WT isoprene synthase. In addition, the kcat of the β isoprene synthase variant was greater than the kcat of the WT isoprene synthase (Table 7-5)

The L494 residue was chosen for SEL studies because it is a hydrophobic residue within a surface-exposed loop of *P. alba* IspS. However, we observed that proline is conserved at this site in an alignment of other terpene synthase enzymes. Other *Populus* species isoprene synthases, along with IspS from *P. Montana* (Kudzu), and various other terpene synthase enzymes such as *M. spicata* limonene synthase, *S. officinalis* bornyl diphosphate synthase, *N. tabacum* epi-aristolochene synthase were aligned relative to *P. alba* IspS using the ClustalW algorithm in AlignX of the Vector NTI software (Invitrogen). FIG. 59 shows that at position 494, many other terpene synthase enzymes have a proline residue, suggesting that proline at that position not only is conserved, but that deviation from the consensus could lead to enzymes that are less efficient. Since position 494 is not near the active site of the enzyme, proline may provide stabilization to that specific loop of IspS and hence secondarily enhance the overall kinetic parameters of IspS.

TABLE 7-4

Specific activity of isoprene synthase amino acid variants. Reactions contained 4 mM DMAPP, 50 mM NaCl, 50 mM Tris pH = 8. Reactions were performed at 30° C.

| Variant | S.A. (nmol/mg/min) | Variant S.A./ WT S.A. |
|---|---|---|
| P | 950 ± 40 | 2.0 |
| C | 430 ± 10 | 0.9 |
| N | 170 ± 30 | 0.4 |
| PC | 490 ± 20 | 1.0 |
| SP | 770 ± 40 | 1.6 |
| NS | 480 ± 40 | 1.0 |
| NC | 420 ± 30 | 0.9 |
| SPC | 630 ± 40 | 1.3 |
| WT | 480 ± 20 | 1.0 |
| S | 480 ± 20 | 1.0 |
| SC | 440 ± 20 | 0.9 |
| NP | 490 ± 20 | 1.0 |
| NPC | 440 ± 20 | 0.9 |
| NSP | 465 ± 2 | 1.0 |
| NSC | 390 ± 20 | 0.8 |
| NSPC | 502 ± 6 | 1.1 |

TABLE 7-5 kcat, KM and Ki for WT, P, SP, and SPC amino acid variants of isoprene synthase. Kcat, KM and Ki were calculated for each trial and then averaged. The reported error is one standard deviation of the three trials that were performed.

| Variant | $k_{cat}$ | $K_M$ | $K_{iDMAPP}$ |
|---|---|---|---|
| WT | 1.5 ± 0.6 | 7 ± 4 | 16 ± 9 |
| P | 2.1 ± 0.1 | 3.6 ± 0.5 | 13 ± 1 |
| SP | 1.2 ± 0.1 | 4.4 ± 0.3 | 18 ± 1 |
| SPC | 1.5 ± 0.4 | 3.5 ± 0.8 | 25 ± 21 |

Example 8

Expression and Purification of IspS-L494P

Expression of 6×His-Tagged IspS-L494P

N-terminally 6×His-tagged IspS was expressed and purified from strain DW399. The growth procedure is suitable for histidine tagged enzymes expressed in BL21(λDE3)pLysS cells. 10 ml of overnight culture was prepared for each 1 L of planned growth. The appropriate antibiotics (50 ug/ml kanamycin, 50 ug/ml chloramphenicol) were added to 10 ml of LB medium in a 25 ml flask which was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1 L day culture was inoculated with 10 ml of overnight culture and grown at 30-37° C. with shaking at ~220 rpm until the $OD_{600}$ reached ~0.4-0.6. Day cultures were then induced with 400 μM IPTG and allowed to continue growing at 30° C. with shaking at 220 rpm for ~5-6 hours. Cells were then harvested by centrifugation at 10,000×g for 10 min, 4° C. Following harvest, cells were used directly or stored at −80° C. until ready to process.

Purification of 6×His-Tagged IspS

For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 40-50 ml of lysis buffer was used per 1 L of cell pellet. Cells were then incubated on ice for approximately 30 min. The cell suspension was then lysed fully by passing 2-3 times through a french pressure cell (large french press cell at 1200 psi/High setting) until lysate appeared clear. A sample of the lysate was saved for activity assay and gel analysis (~100 μl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 μl).

The clarified lysate was run over HisTrap HP columns (GE healthcare) using a gradient from 0-100% Ni buffer B. Following loading of the lysate on the column, the column was washed with Ni wash buffer (50 mM $NaH_2PO_4$, 300 mm NaCl, 20 mM imidazole, ph 8.0). The his-tagged IspS was then eluted from the column using a gradient from 0-100% Ni elution buffer (50 mM $NaH_2PO_4$, 300 mM NaCl, 500 mM imidazole, ph 8.0) and fractions containing the his-tagged IspS were collected. The column was then washed with Ni stripping buffer (20 mM NaH2PO4, 0.5 m NaCl, 50 mM EDTA, ph 7.4). Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a Hi Prep 26/10 Desalting column (GE healthcare) packed with Sephadex G25 resin. The G-25 buffer consisted of 50 mM HEPES, 50 mM NaCl, and 1 mM DTT, pH 7.4. Fractions were then analyzed and concentrated. The samples were then stored at −80° C.

TEV Cleavage (IspS-L494P from Strains DW399)

Strain DW399 is described in Example 6. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (which is also tagged), and impurities. The Ni column pass though and washes were analyzed using SDS-PAGE gel (NUPAGE, Invitrogen; FIG. 51) and DMAPP activity assays. Samples containing pure enzyme were pooled and desalted into 50 mM NaCl pH 7.4 buffer containing 1 mM DTT and stored at −80° C.

Crystal Structure Determination

The enzyme expressed from strain DW399 was purified as described and a concentrated protein solution was then prepared for surveying possible crystallization conditions. The enzyme was purified independently and surveyed as described below. All in-house crystallization screens were set up using the hanging drop vapor diffusion method. At a minimum, the protein was surveyed using the following commercial screens: the Crystal Screen from Hampton Research (Aliso Viejo, Calif.) and the JCSG+Suite from Qiagen (Valencia, Calif.).

Initial crystallization screens were setup using the Crystal Screen from Hampton Research and the JCSG+Suite from Qiagen. Crystals of the protein derived from DW399 were observed in numerous conditions; optimization included 200 variations of pH, precipitating agents, concentrations, and inhibitors. From the optimization experiments, ten different crystals derived from strain DW399 were screened in-house for diffraction. A crystal composed of IspS-L494P protein was obtained that diffracted to 3.2 Å in house. The large, rod-shaped crystals belong to the tetragonal space group $P4_32_12$, and have unit cell dimensions a=155.8, b=155.8, c=143.7. The crystals were grown by mixing 2 μL of protein (10 mg/ml protein) with 2 μL of precipitant solution [0.02 M $MgCl_2$, 0.1 M HEPES pH 7.5, 22% (wt/vol) Polyacrylic acid 5100 Na salt] and equilibrated against 500 μL of precipitant. Prior to flash-freezing the crystal in liquid nitrogen, the crystals were cryoprotected by swishing through 0.02 M $MgCl_2$, 0.1 M HEPES pH 7.5, 22% (wt/vol) Polyacrylic acid 5100 Na salt, and 25% (wt/vol) ethylene glycol.

Data were integrated using Mosflm (Leslie, A. (1998) J. of Appl. Crystallography 30, 1036-1040) and scaled using SCALA (Collaborative Computational Project, N. (1994) Acta Crystallographica Section D 50, 760-763). The data were phased with MOLREP (Vagin, A., and Teplyakov, A. (1997) J. of Appl. Crystallography 30, 1022-1025), using the previously determined structure of IspS from *P. alba* as the starting model. The crystal contains one dimer in the asymmetric unit with a solvent content of 63%. Data collection and refinement statistics are given in Table 8-1.

Refinement with Refmac5 (Collaborative Computational Project, N. (1994) Acta Crystallographica Section D 50, 760-763) was used with iterative manual rebuilding steps using the visualization program Coot (Emsley, P., and Cowtan, K. (2004) Acta Crystallographica Section D 60, 2126-2132). During refinement, the geometry of the protein was checked using Molprobity (Davis, I. W., et al. (2007) Nucl. Acids Res., 35:W375-W383).

The structure consists of two helical domains, a C-terminal domain containing the active site and N-terminal domain with unknown function. The electron density clearly supports the presence of a proline at position 494 in the enzyme derived from strain DW399 (FIG. 52). Structural alignment of the wild type IspS and IspS-L494P show that the overall fold is unchanged, however the conformation of the loop containing residues 490-497 does vary between the wild type and variant proteins (FIG. 53). Coordinates are provided in Table 8-2.

TABLE 8-1

| Data Collection and Refinement Statistics for IspS-L494P | |
|---|---|
| **Data Collection** | |
| Space Group | $P4_32_12$ |
| **Cell dimensions** | |
| A, b, c (Å) | 155.8, 155.8, 143.6 |
| α, β, γ, (°) | 90.0, 90.0, 90.0 |
| Resolution (Å) | 25.7-3.20 |
| $R_{merge}$ | 16.6 (40.5)[a] |
| <I/σI> | 5.7 (2.1) |
| Completeness (%) | 98.8 (95.1) |
| Redundancy | 3.4 (2.4) |
| **Refinement** | |
| Resolution (Å) | 25.7-3.20 |
| No. measured reflections | 99059 |
| No. Unique reflections | 27845 |
| $R_{work}$ | 23.5 |
| $R_{free}$ | 28.6 |
| rmsd bonds, (Å) | 0.005 |
| rmsd angles, (°) | 0.756 |
| **No. of Atoms** | |
| Protein | 8654 |
| Water | 4 |

[a]Values in parenthesis refer to highest resolution shell.

TABLE 8-2

Coordinates for L494P Structure

| | | | | | | | | | | | | |
|---|---|---|---|---|---|---|---|---|---|---|---|---|
| ATOM | 1 | N | ALA | A | 7 | 58.967 | −33.368 | −28.452 | 1.00 | 32.46 | A | N |
| ATOM | 2 | CA | ALA | A | 7 | 60.455 | −33.320 | −28.515 | 1.00 | 32.33 | A | C |
| ATOM | 4 | CB | ALA | A | 7 | 60.968 | −34.329 | −29.538 | 1.00 | 32.27 | A | C |
| ATOM | 8 | C | ALA | A | 7 | 60.928 | −31.913 | −28.869 | 1.00 | 32.20 | A | C |
| ATOM | 9 | O | ALA | A | 7 | 61.175 | −31.618 | −30.038 | 1.00 | 31.89 | A | O |
| ATOM | 13 | N | ASN | A | 8 | 61.056 | −31.054 | −27.855 | 1.00 | 32.28 | A | N |
| ATOM | 14 | CA | ASN | A | 8 | 61.414 | −29.646 | −28.067 | 1.00 | 32.54 | A | C |
| ATOM | 16 | CB | ASN | A | 8 | 60.171 | −28.754 | −27.938 | 1.00 | 32.84 | A | C |
| ATOM | 19 | CG | ASN | A | 8 | 60.193 | −27.562 | −28.897 | 1.00 | 33.76 | A | C |
| ATOM | 20 | OD1 | ASN | A | 8 | 61.242 | −26.964 | −29.150 | 1.00 | 34.16 | A | O |
| ATOM | 21 | ND2 | ASN | A | 8 | 59.027 | −27.215 | −29.432 | 1.00 | 34.29 | A | N |
| ATOM | 24 | C | ASN | A | 8 | 62.519 | −29.158 | −27.125 | 1.00 | 32.38 | A | C |
| ATOM | 25 | O | ASN | A | 8 | 62.774 | −29.764 | −26.081 | 1.00 | 31.88 | A | O |
| ATOM | 27 | N | TYR | A | 9 | 63.148 | −28.045 | −27.510 | 1.00 | 32.53 | A | N |
| ATOM | 28 | CA | TYR | A | 9 | 64.378 | −27.551 | −26.881 | 1.00 | 32.48 | A | C |
| ATOM | 30 | CB | TYR | A | 9 | 65.529 | −27.650 | −27.886 | 1.00 | 32.17 | A | C |
| ATOM | 33 | CG | TYR | A | 9 | 65.491 | −28.904 | −28.713 | 1.00 | 31.92 | A | C |
| ATOM | 34 | CD1 | TYR | A | 9 | 65.999 | −30.097 | −28.214 | 1.00 | 32.88 | A | C |
| ATOM | 36 | CE1 | TYR | A | 9 | 65.963 | −31.258 | −28.964 | 1.00 | 32.64 | A | C |
| ATOM | 38 | CZ | TYR | A | 9 | 65.409 | −31.241 | −30.230 | 1.00 | 32.19 | A | C |
| ATOM | 39 | OH | TYR | A | 9 | 65.370 | −32.394 | −30.978 | 1.00 | 31.19 | A | O |
| ATOM | 41 | CE2 | TYR | A | 9 | 64.892 | −30.067 | −30.748 | 1.00 | 31.99 | A | C |
| ATOM | 43 | CD2 | TYR | A | 9 | 64.933 | −28.906 | −29.987 | 1.00 | 31.30 | A | C |
| ATOM | 45 | C | TYR | A | 9 | 64.297 | −26.100 | −26.401 | 1.00 | 32.65 | A | C |
| ATOM | 46 | O | TYR | A | 9 | 65.333 | −25.490 | −26.119 | 1.00 | 32.90 | A | O |
| ATOM | 48 | N | GLU | A | 10 | 63.089 | −25.547 | −26.304 | 1.00 | 32.35 | A | N |
| ATOM | 49 | CA | GLU | A | 10 | 62.923 | −24.126 | −25.971 | 1.00 | 32.21 | A | C |
| ATOM | 51 | CB | GLU | A | 10 | 61.450 | −23.711 | −26.089 | 1.00 | 32.51 | A | C |
| ATOM | 54 | CG | GLU | A | 10 | 60.880 | −23.803 | −27.509 | 1.00 | 34.11 | A | C |
| ATOM | 57 | CD | GLU | A | 10 | 61.671 | −23.001 | −28.542 | 1.00 | 35.77 | A | C |
| ATOM | 58 | OE1 | GLU | A | 10 | 62.114 | −21.874 | −28.223 | 1.00 | 35.78 | A | O |
| ATOM | 59 | OE2 | GLU | A | 10 | 61.841 | −23.503 | −29.677 | 1.00 | 35.44 | A | O |
| ATOM | 60 | C | GLU | A | 10 | 63.473 | −23.814 | −24.572 | 1.00 | 31.42 | A | C |
| ATOM | 61 | O | GLU | A | 10 | 63.467 | −24.684 | −23.700 | 1.00 | 31.43 | A | O |
| ATOM | 63 | N | PRO | A | 11 | 63.953 | −22.572 | −24.359 | 1.00 | 30.52 | A | N |
| ATOM | 64 | CA | PRO | A | 11 | 64.709 | −22.252 | −23.148 | 1.00 | 30.13 | A | C |
| ATOM | 66 | CB | PRO | A | 11 | 65.263 | −20.857 | −23.449 | 1.00 | 30.16 | A | C |
| ATOM | 69 | CG | PRO | A | 11 | 64.250 | −20.247 | −24.336 | 1.00 | 30.10 | A | C |

TABLE 8-2-continued

Coordinates for L494P Structure

| | | | | | | | | | | | | |
|---|---|---|---|---|---|---|---|---|---|---|---|---|
| ATOM | 72 | CD | PRO | A | 11 | 63.722 | −21.372 | −25.186 | 1.00 | 30.45 | A | C |
| ATOM | 75 | C | PRO | A | 11 | 63.856 | −22.208 | −21.886 | 1.00 | 29.77 | A | C |
| ATOM | 76 | O | PRO | A | 11 | 62.763 | −21.645 | −21.902 | 1.00 | 30.21 | A | O |
| ATOM | 77 | N | ASN | A | 12 | 64.357 | −22.802 | −20.807 | 1.00 | 29.24 | A | N |
| ATOM | 78 | CA | ASN | A | 12 | 63.717 | −22.692 | −19.501 | 1.00 | 28.99 | A | C |
| ATOM | 80 | CB | ASN | A | 12 | 64.148 | −23.841 | −18.588 | 1.00 | 28.99 | A | C |
| ATOM | 83 | CG | ASN | A | 12 | 63.744 | −25.201 | −19.128 | 1.00 | 28.62 | A | C |
| ATOM | 84 | OD1 | ASN | A | 12 | 62.558 | −25.498 | −19.268 | 1.00 | 29.36 | A | O |
| ATOM | 85 | ND2 | ASN | A | 12 | 64.731 | −26.038 | −19.423 | 1.00 | 27.55 | A | N |
| ATOM | 88 | C | ASN | A | 12 | 64.083 | −21.348 | −18.872 | 1.00 | 28.99 | A | C |
| ATOM | 89 | O | ASN | A | 12 | 65.197 | −20.853 | −19.062 | 1.00 | 29.27 | A | O |
| ATOM | 91 | N | SER | A | 13 | 63.146 | −20.760 | −18.131 | 1.00 | 28.65 | A | N |
| ATOM | 92 | CA | SER | A | 13 | 63.365 | −19.461 | −17.482 | 1.00 | 28.22 | A | C |
| ATOM | 94 | CB | SER | A | 13 | 62.052 | −18.933 | −16.893 | 1.00 | 28.27 | A | C |
| ATOM | 97 | OG | SER | A | 13 | 61.433 | −19.905 | −16.067 | 1.00 | 27.86 | A | O |
| ATOM | 99 | C | SER | A | 13 | 64.437 | −19.531 | −16.388 | 1.00 | 27.86 | A | C |
| ATOM | 100 | O | SER | A | 13 | 65.127 | −18.545 | −16.117 | 1.00 | 27.35 | A | O |
| ATOM | 102 | N | TRP | A | 14 | 64.573 | −20.704 | −15.775 | 1.00 | 27.59 | A | N |
| ATOM | 103 | CA | TRP | A | 14 | 65.538 | −20.919 | −14.697 | 1.00 | 27.37 | A | C |
| ATOM | 105 | CB | TRP | A | 14 | 64.967 | −21.893 | −13.649 | 1.00 | 27.41 | A | C |
| ATOM | 108 | CG | TRP | A | 14 | 64.246 | −23.092 | −14.212 | 1.00 | 28.21 | A | C |
| ATOM | 109 | CD1 | TRP | A | 14 | 62.894 | −23.246 | −14.346 | 1.00 | 29.22 | A | C |
| ATOM | 111 | NE1 | TRP | A | 14 | 62.607 | −24.471 | −14.897 | 1.00 | 29.08 | A | N |
| ATOM | 113 | CE2 | TRP | A | 14 | 63.781 | −25.138 | −15.127 | 1.00 | 29.46 | A | C |
| ATOM | 114 | CD2 | TRP | A | 14 | 64.836 | −24.299 | −14.706 | 1.00 | 28.64 | A | C |
| ATOM | 115 | CE3 | TRP | A | 14 | 66.153 | −24.754 | −14.836 | 1.00 | 29.12 | A | C |
| ATOM | 117 | CZ3 | TRP | A | 14 | 66.373 | −26.014 | −15.377 | 1.00 | 30.29 | A | C |
| ATOM | 119 | CH2 | TRP | A | 14 | 65.303 | −26.825 | −15.788 | 1.00 | 30.52 | A | C |
| ATOM | 121 | CZ2 | TRP | A | 14 | 64.004 | −26.406 | −15.670 | 1.00 | 30.11 | A | C |
| ATOM | 123 | C | TRP | A | 14 | 66.912 | −21.401 | −15.189 | 1.00 | 27.25 | A | C |
| ATOM | 124 | O | TRP | A | 14 | 67.776 | −21.723 | −14.378 | 1.00 | 27.30 | A | O |
| ATOM | 126 | N | ASP | A | 15 | 67.127 | −21.435 | −16.503 | 1.00 | 27.11 | A | N |
| ATOM | 127 | CA | ASP | A | 15 | 68.419 | −21.859 | −17.055 | 1.00 | 27.19 | A | C |
| ATOM | 129 | CB | ASP | A | 15 | 68.371 | −21.911 | −18.587 | 1.00 | 27.21 | A | C |
| ATOM | 132 | CG | ASP | A | 15 | 67.685 | −23.157 | −19.117 | 1.00 | 27.43 | A | C |
| ATOM | 133 | OD1 | ASP | A | 15 | 67.686 | −24.200 | −18.426 | 1.00 | 26.27 | A | O |
| ATOM | 134 | OD2 | ASP | A | 15 | 67.154 | −23.094 | −20.246 | 1.00 | 29.06 | A | O |
| ATOM | 135 | C | ASP | A | 15 | 69.562 | −20.941 | −16.625 | 1.00 | 27.45 | A | C |
| ATOM | 136 | O | ASP | A | 15 | 69.347 | −19.773 | −16.302 | 1.00 | 27.69 | A | O |
| ATOM | 138 | N | TYR | A | 16 | 70.778 | −21.479 | −16.633 | 1.00 | 27.65 | A | N |
| ATOM | 139 | CA | TYR | A | 16 | 71.968 | −20.698 | −16.299 | 1.00 | 27.87 | A | C |
| ATOM | 141 | CB | TYR | A | 16 | 73.122 | −21.618 | −15.890 | 1.00 | 27.97 | A | C |
| ATOM | 144 | CG | TYR | A | 16 | 72.878 | −22.322 | −14.569 | 1.00 | 28.42 | A | C |
| ATOM | 145 | CD1 | TYR | A | 16 | 72.806 | −21.601 | −13.378 | 1.00 | 28.17 | A | C |
| ATOM | 147 | CE1 | TYR | A | 16 | 72.576 | −22.236 | −12.164 | 1.00 | 26.82 | A | C |
| ATOM | 149 | CZ | TYR | A | 16 | 72.417 | −23.606 | −12.130 | 1.00 | 26.17 | A | C |
| ATOM | 150 | OH | TYR | A | 16 | 72.191 | −24.230 | −10.929 | 1.00 | 25.22 | A | O |
| ATOM | 152 | CE2 | TYR | A | 16 | 72.485 | −24.348 | −13.296 | 1.00 | 26.88 | A | C |
| ATOM | 154 | CD2 | TYR | A | 16 | 72.715 | −23.704 | −14.509 | 1.00 | 27.97 | A | C |
| ATOM | 156 | C | TYR | A | 16 | 72.389 | −19.774 | −17.445 | 1.00 | 28.24 | A | C |
| ATOM | 157 | O | TYR | A | 16 | 73.125 | −18.814 | −17.225 | 1.00 | 28.23 | A | O |
| ATOM | 159 | N | ASP | A | 17 | 71.929 | −20.071 | −18.660 | 1.00 | 28.81 | A | N |
| ATOM | 160 | CA | ASP | A | 17 | 72.109 | −19.171 | −19.806 | 1.00 | 29.05 | A | C |
| ATOM | 162 | CB | ASP | A | 17 | 71.891 | −19.919 | −21.129 | 1.00 | 28.88 | A | C |
| ATOM | 165 | CG | ASP | A | 17 | 72.965 | −20.962 | −21.406 | 1.00 | 28.36 | A | C |
| ATOM | 166 | OD1 | ASP | A | 17 | 74.154 | −20.593 | −21.514 | 1.00 | 27.28 | A | O |
| ATOM | 167 | OD2 | ASP | A | 17 | 72.614 | −22.154 | −21.539 | 1.00 | 27.24 | A | O |
| ATOM | 168 | C | ASP | A | 17 | 71.140 | −17.987 | −19.726 | 1.00 | 29.57 | A | C |
| ATOM | 169 | O | ASP | A | 17 | 71.501 | −16.858 | −20.062 | 1.00 | 29.32 | A | O |
| ATOM | 171 | N | TYR | A | 18 | 69.916 | −18.260 | −19.274 | 1.00 | 30.37 | A | N |
| ATOM | 172 | CA | TYR | A | 18 | 68.828 | −17.278 | −19.250 | 1.00 | 31.29 | A | C |
| ATOM | 174 | CB | TYR | A | 18 | 67.495 | −18.008 | −19.056 | 1.00 | 31.77 | A | C |
| ATOM | 177 | CG | TYR | A | 18 | 66.249 | −17.171 | −19.266 | 1.00 | 35.14 | A | C |
| ATOM | 178 | CD1 | TYR | A | 18 | 65.523 | −17.255 | −20.456 | 1.00 | 37.79 | A | C |
| ATOM | 180 | CE1 | TYR | A | 18 | 64.370 | −16.503 | −20.650 | 1.00 | 38.22 | A | C |
| ATOM | 182 | CZ | TYR | A | 18 | 63.926 | −15.661 | −19.645 | 1.00 | 38.92 | A | C |
| ATOM | 183 | OH | TYR | A | 18 | 62.785 | −14.918 | −19.837 | 1.00 | 40.58 | A | O |
| ATOM | 185 | CE2 | TYR | A | 18 | 64.623 | −15.565 | −18.451 | 1.00 | 38.20 | A | C |
| ATOM | 187 | CD2 | TYR | A | 18 | 65.775 | −16.321 | −18.265 | 1.00 | 36.98 | A | C |
| ATOM | 189 | C | TYR | A | 18 | 69.043 | −16.237 | −18.149 | 1.00 | 31.48 | A | C |
| ATOM | 190 | O | TYR | A | 18 | 69.094 | −15.039 | −18.426 | 1.00 | 31.70 | A | O |
| ATOM | 192 | N | LEU | A | 19 | 69.156 | −16.699 | −16.905 | 1.00 | 31.72 | A | N |
| ATOM | 193 | CA | LEU | A | 19 | 69.585 | −15.852 | −15.792 | 1.00 | 31.90 | A | C |
| ATOM | 195 | CB | LEU | A | 19 | 69.089 | −16.416 | −14.455 | 1.00 | 31.77 | A | C |
| ATOM | 198 | CG | LEU | A | 19 | 67.574 | −16.531 | −14.261 | 1.00 | 32.74 | A | C |
| ATOM | 200 | CD1 | LEU | A | 19 | 67.248 | −17.518 | −13.141 | 1.00 | 32.00 | A | C |
| ATOM | 204 | CD2 | LEU | A | 19 | 66.943 | −15.164 | −13.989 | 1.00 | 31.72 | A | C |
| ATOM | 208 | C | LEU | A | 19 | 71.106 | −15.825 | −15.806 | 1.00 | 32.37 | A | C |

TABLE 8-2-continued

Coordinates for L494P Structure

| | | | | | | | | | | | | |
|---|---|---|---|---|---|---|---|---|---|---|---|---|
| ATOM | 209 | O | LEU | A | 19 | 71.727 | −16.380 | −16.712 | 1.00 | 32.67 | A | O |
| ATOM | 211 | N | LEU | A | 20 | 71.709 | −15.174 | −14.815 | 1.00 | 32.83 | A | N |
| ATOM | 212 | CA | LEU | A | 20 | 73.148 | −15.281 | −14.594 | 1.00 | 33.25 | A | C |
| ATOM | 214 | CB | LEU | A | 20 | 73.466 | −16.668 | −14.021 | 1.00 | 33.14 | A | C |
| ATOM | 217 | CG | LEU | A | 20 | 74.826 | −16.886 | −13.356 | 1.00 | 33.70 | A | C |
| ATOM | 219 | CD1 | LEU | A | 20 | 74.988 | −15.984 | −12.139 | 1.00 | 34.63 | A | C |
| ATOM | 223 | CD2 | LEU | A | 20 | 74.985 | −18.351 | −12.969 | 1.00 | 33.93 | A | C |
| ATOM | 227 | C | LEU | A | 20 | 73.947 | −15.025 | −15.880 | 1.00 | 33.88 | A | C |
| ATOM | 228 | O | LEU | A | 20 | 74.771 | −15.848 | −16.292 | 1.00 | 33.76 | A | O |
| ATOM | 230 | N | SER | A | 21 | 73.677 | −13.888 | −16.519 | 1.00 | 34.62 | A | N |
| ATOM | 231 | CA | SER | A | 21 | 74.409 | −13.467 | −17.718 | 1.00 | 35.00 | A | C |
| ATOM | 233 | CB | SER | A | 21 | 73.478 | −13.378 | −18.933 | 1.00 | 35.02 | A | C |
| ATOM | 236 | OG | SER | A | 21 | 73.457 | −14.605 | −19.644 | 1.00 | 34.89 | A | O |
| ATOM | 238 | C | SER | A | 21 | 75.117 | −12.136 | −17.488 | 1.00 | 35.34 | A | C |
| ATOM | 239 | O | SER | A | 21 | 74.711 | −11.334 | −16.639 | 1.00 | 34.98 | A | O |
| ATOM | 241 | N | SER | A | 22 | 76.173 | −11.913 | −18.266 | 1.00 | 35.95 | A | N |
| ATOM | 242 | CA | SER | A | 22 | 77.087 | −10.795 | −18.048 | 1.00 | 36.40 | A | C |
| ATOM | 244 | CB | SER | A | 22 | 78.430 | −11.076 | −18.732 | 1.00 | 36.31 | A | C |
| ATOM | 247 | OG | SER | A | 22 | 78.248 | −11.367 | −20.107 | 1.00 | 35.88 | A | O |
| ATOM | 249 | C | SER | A | 22 | 76.530 | −9.461 | −18.543 | 1.00 | 36.86 | A | C |
| ATOM | 250 | O | SER | A | 22 | 76.493 | −9.205 | −19.751 | 1.00 | 36.97 | A | O |
| ATOM | 252 | N | ASP | A | 23 | 76.099 | −8.619 | −17.603 | 1.00 | 37.22 | A | N |
| ATOM | 253 | CA | ASP | A | 23 | 75.752 | −7.232 | −17.906 | 1.00 | 37.43 | A | C |
| ATOM | 255 | CB | ASP | A | 23 | 75.077 | −6.567 | −16.694 | 1.00 | 37.44 | A | C |
| ATOM | 258 | CG | ASP | A | 23 | 74.428 | −5.228 | −17.030 | 1.00 | 37.60 | A | C |
| ATOM | 259 | OD1 | ASP | A | 23 | 74.332 | −4.869 | −18.223 | 1.00 | 37.88 | A | O |
| ATOM | 260 | OD2 | ASP | A | 23 | 74.003 | −4.531 | −16.084 | 1.00 | 37.64 | A | O |
| ATOM | 261 | C | ASP | A | 23 | 77.049 | −6.517 | −18.299 | 1.00 | 37.55 | A | C |
| ATOM | 262 | O | ASP | A | 23 | 77.168 | −5.993 | −19.410 | 1.00 | 37.66 | A | O |
| ATOM | 264 | N | THR | A | 24 | 78.015 | −6.509 | −17.380 | 1.00 | 37.50 | A | N |
| ATOM | 265 | CA | THR | A | 24 | 79.413 | −6.192 | −17.700 | 1.00 | 37.32 | A | C |
| ATOM | 267 | CB | THR | A | 24 | 79.691 | −4.665 | −17.661 | 1.00 | 37.41 | A | C |
| ATOM | 269 | OG1 | THR | A | 24 | 78.608 | −3.952 | −18.274 | 1.00 | 37.33 | A | O |
| ATOM | 271 | CG2 | THR | A | 24 | 80.991 | −4.330 | −18.392 | 1.00 | 36.82 | A | C |
| ATOM | 275 | C | THR | A | 24 | 80.360 | −6.925 | −16.730 | 1.00 | 37.05 | A | C |
| ATOM | 276 | O | THR | A | 24 | 81.444 | −6.430 | −16.407 | 1.00 | 37.13 | A | O |
| ATOM | 278 | N | ASP | A | 25 | 79.944 | −8.116 | −16.290 | 1.00 | 36.41 | A | N |
| ATOM | 279 | CA | ASP | A | 25 | 80.665 | −8.890 | −15.278 | 1.00 | 35.69 | A | C |
| ATOM | 281 | CB | ASP | A | 25 | 79.714 | −9.307 | −14.149 | 1.00 | 35.42 | A | C |
| ATOM | 284 | CG | ASP | A | 25 | 79.022 | −8.123 | −13.489 | 1.00 | 34.28 | A | C |
| ATOM | 285 | OD1 | ASP | A | 25 | 79.536 | −6.988 | −13.575 | 1.00 | 31.33 | A | O |
| ATOM | 286 | OD2 | ASP | A | 25 | 77.956 | −8.335 | −12.875 | 1.00 | 33.31 | A | O |
| ATOM | 287 | C | ASP | A | 25 | 81.298 | −10.136 | −15.899 | 1.00 | 35.33 | A | C |
| ATOM | 288 | O | ASP | A | 25 | 80.594 | −11.077 | −16.273 | 1.00 | 35.35 | A | O |
| ATOM | 290 | N | GLU | A | 26 | 82.625 | −10.134 | −16.002 | 1.00 | 34.79 | A | N |
| ATOM | 291 | CA | GLU | A | 26 | 83.372 | −11.273 | −16.546 | 1.00 | 34.55 | A | C |
| ATOM | 293 | CB | GLU | A | 26 | 84.858 | −10.920 | −16.690 | 1.00 | 34.43 | A | C |
| ATOM | 296 | CG | GLU | A | 26 | 85.159 | −9.814 | −17.695 | 1.00 | 33.53 | A | C |
| ATOM | 299 | CD | GLU | A | 26 | 86.645 | −9.516 | −17.821 | 1.00 | 31.34 | A | C |
| ATOM | 300 | OE1 | GLU | A | 26 | 87.432 | −9.968 | −16.962 | 1.00 | 30.11 | A | O |
| ATOM | 301 | OE2 | GLU | A | 26 | 87.026 | −8.822 | −18.785 | 1.00 | 29.48 | A | O |
| ATOM | 302 | C | GLU | A | 26 | 83.251 | −12.515 | −15.662 | 1.00 | 34.62 | A | C |
| ATOM | 303 | O | GLU | A | 26 | 83.213 | −13.644 | −16.159 | 1.00 | 34.51 | A | O |
| ATOM | 305 | N | SER | A | 27 | 83.197 | −12.292 | −14.351 | 1.00 | 34.63 | A | N |
| ATOM | 306 | CA | SER | A | 27 | 83.188 | −13.374 | −13.365 | 1.00 | 34.68 | A | C |
| ATOM | 308 | CB | SER | A | 27 | 83.367 | −12.794 | −11.957 | 1.00 | 34.79 | A | C |
| ATOM | 311 | OG | SER | A | 27 | 82.483 | −11.706 | −11.735 | 1.00 | 34.93 | A | O |
| ATOM | 313 | C | SER | A | 27 | 81.930 | −14.252 | −13.416 | 1.00 | 34.53 | A | C |
| ATOM | 314 | O | SER | A | 27 | 81.963 | −15.407 | −12.979 | 1.00 | 34.27 | A | O |
| ATOM | 316 | N | ILE | A | 28 | 80.831 | −13.709 | −13.942 | 1.00 | 34.31 | A | N |
| ATOM | 317 | CA | ILE | A | 28 | 79.602 | −14.484 | −14.119 | 1.00 | 34.09 | A | C |
| ATOM | 319 | CB | ILE | A | 28 | 78.412 | −13.598 | −14.561 | 1.00 | 34.14 | A | C |
| ATOM | 321 | CG1 | ILE | A | 28 | 78.065 | −12.575 | −13.476 | 1.00 | 34.77 | A | C |
| ATOM | 324 | CD1 | ILE | A | 28 | 76.877 | −11.689 | −13.824 | 1.00 | 35.54 | A | C |
| ATOM | 328 | CG2 | ILE | A | 28 | 77.190 | −14.457 | −14.860 | 1.00 | 33.66 | A | C |
| ATOM | 332 | C | ILE | A | 28 | 79.798 | −15.599 | −15.148 | 1.00 | 33.79 | A | C |
| ATOM | 333 | O | ILE | A | 28 | 79.289 | −16.700 | −14.968 | 1.00 | 33.59 | A | O |
| ATOM | 335 | N | GLU | A | 29 | 80.552 | −15.315 | −16.210 | 1.00 | 33.59 | A | N |
| ATOM | 336 | CA | GLU | A | 29 | 80.739 | −16.270 | −17.313 | 1.00 | 33.41 | A | C |
| ATOM | 338 | CB | GLU | A | 29 | 81.273 | −15.556 | −18.564 | 1.00 | 33.57 | A | C |
| ATOM | 341 | CG | GLU | A | 29 | 80.268 | −14.599 | −19.206 | 1.00 | 34.79 | A | C |
| ATOM | 344 | CD | GLU | A | 29 | 78.994 | −15.293 | −19.675 | 1.00 | 35.14 | A | C |
| ATOM | 345 | OE1 | GLU | A | 29 | 79.092 | −16.335 | −20.357 | 1.00 | 35.06 | A | O |
| ATOM | 346 | OE2 | GLU | A | 29 | 77.892 | −14.792 | −19.362 | 1.00 | 35.70 | A | O |
| ATOM | 347 | C | GLU | A | 29 | 81.627 | −17.476 | −16.984 | 1.00 | 32.74 | A | C |
| ATOM | 348 | O | GLU | A | 29 | 81.700 | −18.415 | −17.776 | 1.00 | 32.85 | A | O |
| ATOM | 350 | N | VAL | A | 30 | 82.309 | −17.449 | −15.840 | 1.00 | 31.82 | A | N |
| ATOM | 351 | CA | VAL | A | 30 | 82.990 | −18.640 | −15.320 | 1.00 | 30.90 | A | C |

TABLE 8-2-continued

Coordinates for L494P Structure

| | | | | | | | | | | | | |
|---|---|---|---|---|---|---|---|---|---|---|---|---|
| ATOM | 353 | CB | VAL | A | 30 | 84.379 | −18.305 | −14.736 | 1.00 | 30.95 | A | C |
| ATOM | 355 | CG1 | VAL | A | 30 | 85.158 | −19.583 | −14.445 | 1.00 | 30.39 | A | C |
| ATOM | 359 | CG2 | VAL | A | 30 | 85.160 | −17.412 | −15.693 | 1.00 | 30.85 | A | C |
| ATOM | 363 | C | VAL | A | 30 | 82.117 | −19.310 | −14.253 | 1.00 | 29.93 | A | C |
| ATOM | 364 | O | VAL | A | 30 | 82.088 | −20.533 | −14.149 | 1.00 | 29.30 | A | O |
| ATOM | 366 | N | TYR | A | 31 | 81.419 | −18.492 | −13.468 | 1.00 | 29.33 | A | N |
| ATOM | 367 | CA | TYR | A | 31 | 80.412 | −18.952 | −12.504 | 1.00 | 28.99 | A | C |
| ATOM | 369 | CB | TYR | A | 31 | 79.844 | −17.729 | −11.762 | 1.00 | 29.11 | A | C |
| ATOM | 372 | CG | TYR | A | 31 | 78.990 | −18.015 | −10.541 | 1.00 | 29.97 | A | C |
| ATOM | 373 | CD1 | TYR | A | 31 | 79.552 | −18.524 | −9.371 | 1.00 | 30.42 | A | C |
| ATOM | 375 | CE1 | TYR | A | 31 | 78.767 | −18.768 | −8.241 | 1.00 | 31.07 | A | C |
| ATOM | 377 | CZ | TYR | A | 31 | 77.406 | −18.490 | −8.274 | 1.00 | 31.23 | A | C |
| ATOM | 378 | OH | TYR | A | 31 | 76.621 | −18.728 | −7.165 | 1.00 | 30.48 | A | O |
| ATOM | 380 | CE2 | TYR | A | 31 | 76.829 | −17.972 | −9.420 | 1.00 | 30.59 | A | C |
| ATOM | 382 | CD2 | TYR | A | 31 | 77.623 | −17.731 | −10.542 | 1.00 | 31.01 | A | C |
| ATOM | 384 | C | TYR | A | 31 | 79.294 | −19.726 | −13.225 | 1.00 | 28.35 | A | C |
| ATOM | 385 | O | TYR | A | 31 | 78.896 | −20.815 | −12.802 | 1.00 | 28.24 | A | O |
| ATOM | 387 | N | LYS | A | 32 | 78.811 | −19.143 | −14.321 | 1.00 | 27.54 | A | N |
| ATOM | 388 | CA | LYS | A | 32 | 77.792 | −19.738 | −15.196 | 1.00 | 26.68 | A | C |
| ATOM | 390 | CB | LYS | A | 32 | 77.434 | −18.724 | −16.292 | 1.00 | 27.16 | A | C |
| ATOM | 393 | CG | LYS | A | 32 | 76.586 | −19.211 | −17.469 | 1.00 | 27.92 | A | C |
| ATOM | 396 | CD | LYS | A | 32 | 76.980 | −18.446 | −18.748 | 1.00 | 29.61 | A | C |
| ATOM | 399 | CE | LYS | A | 32 | 75.811 | −18.227 | −19.693 | 1.00 | 30.33 | A | C |
| ATOM | 402 | NZ | LYS | A | 32 | 74.948 | −17.083 | −19.266 | 1.00 | 30.04 | A | N |
| ATOM | 406 | C | LYS | A | 32 | 78.285 | −21.036 | −15.826 | 1.00 | 25.58 | A | C |
| ATOM | 407 | O | LYS | A | 32 | 77.620 | −22.067 | −15.728 | 1.00 | 25.63 | A | O |
| ATOM | 409 | N | ASP | A | 33 | 79.448 | −20.974 | −16.475 | 1.00 | 24.33 | A | N |
| ATOM | 410 | CA | ASP | A | 33 | 80.056 | −22.154 | −17.106 | 1.00 | 23.26 | A | C |
| ATOM | 412 | CB | ASP | A | 33 | 81.367 | −21.783 | −17.822 | 1.00 | 23.36 | A | C |
| ATOM | 415 | CG | ASP | A | 33 | 81.142 | −21.100 | −19.173 | 1.00 | 23.27 | A | C |
| ATOM | 416 | OD1 | ASP | A | 33 | 79.992 | −21.051 | −19.659 | 1.00 | 23.99 | A | O |
| ATOM | 417 | OD2 | ASP | A | 33 | 82.133 | −20.612 | −19.757 | 1.00 | 21.23 | A | O |
| ATOM | 418 | C | ASP | A | 33 | 80.313 | −23.278 | −16.099 | 1.00 | 22.17 | A | C |
| ATOM | 419 | O | ASP | A | 33 | 80.256 | −24.455 | −16.454 | 1.00 | 21.98 | A | O |
| ATOM | 421 | N | LYS | A | 34 | 80.592 | −22.910 | −14.849 | 1.00 | 21.18 | A | N |
| ATOM | 422 | CA | LYS | A | 34 | 80.789 | −23.885 | −13.774 | 1.00 | 20.15 | A | C |
| ATOM | 424 | CB | LYS | A | 34 | 81.420 | −23.221 | −12.541 | 1.00 | 19.97 | A | C |
| ATOM | 427 | CG | LYS | A | 34 | 82.264 | −24.155 | −11.679 | 1.00 | 19.67 | A | C |
| ATOM | 430 | CD | LYS | A | 34 | 83.466 | −23.426 | −11.061 | 1.00 | 20.43 | A | C |
| ATOM | 433 | CE | LYS | A | 34 | 84.646 | −24.371 | −10.818 | 1.00 | 20.70 | A | C |
| ATOM | 436 | NZ | LYS | A | 34 | 85.942 | −23.644 | −10.709 | 1.00 | 17.82 | A | N |
| ATOM | 440 | C | LYS | A | 34 | 79.457 | −24.534 | −13.409 | 1.00 | 19.43 | A | C |
| ATOM | 441 | O | LYS | A | 34 | 79.368 | −25.759 | −13.320 | 1.00 | 20.13 | A | O |
| ATOM | 443 | N | ALA | A | 35 | 78.427 | −23.712 | −13.209 | 1.00 | 17.92 | A | N |
| ATOM | 444 | CA | ALA | A | 35 | 77.080 | −24.211 | −12.927 | 1.00 | 16.84 | A | C |
| ATOM | 446 | CB | ALA | A | 35 | 76.086 | −23.063 | −12.871 | 1.00 | 16.71 | A | C |
| ATOM | 450 | C | ALA | A | 35 | 76.656 | −25.222 | −13.984 | 1.00 | 16.12 | A | C |
| ATOM | 451 | O | ALA | A | 35 | 76.317 | −26.360 | −13.663 | 1.00 | 15.55 | A | O |
| ATOM | 453 | N | LYS | A | 36 | 76.703 | −24.798 | −15.245 | 1.00 | 15.82 | A | N |
| ATOM | 454 | CA | LYS | A | 36 | 76.337 | −25.647 | −16.385 | 1.00 | 15.48 | A | C |
| ATOM | 456 | CB | LYS | A | 36 | 76.637 | −24.921 | −17.708 | 1.00 | 15.46 | A | C |
| ATOM | 459 | CG | LYS | A | 36 | 75.690 | −23.752 | −18.007 | 1.00 | 14.99 | A | C |
| ATOM | 462 | CD | LYS | A | 36 | 76.314 | −22.686 | −18.917 | 1.00 | 13.95 | A | C |
| ATOM | 465 | CE | LYS | A | 36 | 76.428 | −23.143 | −20.367 | 1.00 | 13.77 | A | C |
| ATOM | 468 | NZ | LYS | A | 36 | 76.844 | −22.031 | −21.277 | 1.00 | 12.18 | A | N |
| ATOM | 472 | C | LYS | A | 36 | 77.038 | −27.011 | −16.359 | 1.00 | 15.21 | A | C |
| ATOM | 473 | O | LYS | A | 36 | 76.413 | −28.030 | −16.650 | 1.00 | 15.02 | A | O |
| ATOM | 475 | N | LYS | A | 37 | 78.324 | −27.024 | −16.004 | 1.00 | 15.15 | A | N |
| ATOM | 476 | CA | LYS | A | 37 | 79.104 | −28.267 | −15.941 | 1.00 | 15.11 | A | C |
| ATOM | 478 | CB | LYS | A | 37 | 80.602 | −27.970 | −15.781 | 1.00 | 15.02 | A | C |
| ATOM | 481 | CG | LYS | A | 37 | 81.457 | −29.221 | −15.544 | 1.00 | 16.38 | A | C |
| ATOM | 484 | CD | LYS | A | 37 | 82.922 | −29.033 | −15.934 | 1.00 | 16.66 | A | C |
| ATOM | 487 | CE | LYS | A | 37 | 83.714 | −30.321 | −15.703 | 1.00 | 15.63 | A | C |
| ATOM | 490 | NZ | LYS | A | 37 | 85.058 | −30.304 | −16.342 | 1.00 | 14.75 | A | N |
| ATOM | 494 | C | LYS | A | 37 | 78.626 | −29.187 | −14.813 | 1.00 | 15.19 | A | C |
| ATOM | 495 | O | LYS | A | 37 | 78.467 | −30.397 | −15.011 | 1.00 | 15.35 | A | O |
| ATOM | 497 | N | LEU | A | 38 | 78.405 | −28.612 | −13.633 | 1.00 | 14.82 | A | N |
| ATOM | 498 | CA | LEU | A | 38 | 77.904 | −29.372 | −12.488 | 1.00 | 14.29 | A | C |
| ATOM | 500 | CB | LEU | A | 38 | 77.978 | −28.533 | −11.208 | 1.00 | 14.07 | A | C |
| ATOM | 503 | CG | LEU | A | 38 | 79.356 | −28.035 | −10.767 | 1.00 | 13.08 | A | C |
| ATOM | 505 | CD1 | LEU | A | 38 | 79.227 | −27.212 | −9.494 | 1.00 | 10.42 | A | C |
| ATOM | 509 | CD2 | LEU | A | 38 | 80.325 | −29.193 | −10.568 | 1.00 | 12.91 | A | C |
| ATOM | 513 | C | LEU | A | 38 | 76.463 | −29.837 | −12.717 | 1.00 | 14.27 | A | C |
| ATOM | 514 | O | LEU | A | 38 | 76.094 | −30.948 | −12.336 | 1.00 | 14.74 | A | O |
| ATOM | 516 | N | GLU | A | 39 | 75.656 | −28.979 | −13.339 | 1.00 | 13.96 | A | N |
| ATOM | 517 | CA | GLU | A | 39 | 74.263 | −29.296 | −13.651 | 1.00 | 13.65 | A | C |
| ATOM | 519 | CB | GLU | A | 39 | 73.599 | −28.108 | −14.354 | 1.00 | 13.97 | A | C |
| ATOM | 522 | CG | GLU | A | 39 | 72.085 | −28.233 | −14.528 | 1.00 | 14.95 | A | C |

TABLE 8-2-continued

Coordinates for L494P Structure

| | | | | | | | | | | | | |
|---|---|---|---|---|---|---|---|---|---|---|---|---|
| ATOM | 525 | CD | GLU | A | 39 | 71.485 | −27.097 | −15.345 | 1.00 | 16.13 | A | C |
| ATOM | 526 | OE1 | GLU | A | 39 | 72.200 | −26.522 | −16.200 | 1.00 | 15.33 | A | O |
| ATOM | 527 | OE2 | GLU | A | 39 | 70.291 | −26.787 | −15.136 | 1.00 | 15.50 | A | O |
| ATOM | 528 | C | GLU | A | 39 | 74.160 | −30.536 | −14.534 | 1.00 | 13.24 | A | C |
| ATOM | 529 | O | GLU | A | 39 | 73.290 | −31.379 | −14.327 | 1.00 | 13.19 | A | O |
| ATOM | 531 | N | ALA | A | 40 | 75.050 | −30.635 | −15.517 | 1.00 | 13.18 | A | N |
| ATOM | 532 | CA | ALA | A | 40 | 75.078 | −31.773 | −16.434 | 1.00 | 13.27 | A | C |
| ATOM | 534 | CB | ALA | A | 40 | 76.121 | −31.545 | −17.518 | 1.00 | 13.09 | A | C |
| ATOM | 538 | C | ALA | A | 40 | 75.372 | −33.075 | −15.694 | 1.00 | 13.60 | A | C |
| ATOM | 539 | O | ALA | A | 40 | 74.631 | −34.052 | −15.815 | 1.00 | 13.20 | A | O |
| ATOM | 541 | N | GLU | A | 41 | 76.459 | −33.071 | −14.926 | 1.00 | 14.01 | A | N |
| ATOM | 542 | CA | GLU | A | 41 | 76.892 | −34.243 | −14.162 | 1.00 | 13.91 | A | C |
| ATOM | 544 | CB | GLU | A | 41 | 78.136 | −33.902 | −13.331 | 1.00 | 14.03 | A | C |
| ATOM | 547 | CG | GLU | A | 41 | 78.963 | −35.108 | −12.883 | 1.00 | 14.30 | A | C |
| ATOM | 550 | CD | GLU | A | 41 | 80.385 | −34.740 | −12.450 | 1.00 | 14.59 | A | C |
| ATOM | 551 | OE1 | GLU | A | 41 | 80.750 | −33.545 | −12.486 | 1.00 | 13.71 | A | O |
| ATOM | 552 | OE2 | GLU | A | 41 | 81.147 | −35.655 | −12.077 | 1.00 | 16.03 | A | O |
| ATOM | 553 | C | GLU | A | 41 | 75.766 | −34.772 | −13.268 | 1.00 | 13.65 | A | C |
| ATOM | 554 | O | GLU | A | 41 | 75.536 | −35.976 | −13.210 | 1.00 | 13.97 | A | O |
| ATOM | 556 | N | VAL | A | 42 | 75.058 | −33.872 | −12.592 | 1.00 | 13.32 | A | N |
| ATOM | 557 | CA | VAL | A | 42 | 73.908 | −34.261 | −11.772 | 1.00 | 13.82 | A | C |
| ATOM | 559 | CB | VAL | A | 42 | 73.337 | −33.065 | −10.980 | 1.00 | 13.98 | A | C |
| ATOM | 561 | CG1 | VAL | A | 42 | 72.097 | −33.481 | −10.190 | 1.00 | 11.81 | A | C |
| ATOM | 565 | CG2 | VAL | A | 42 | 74.399 | −32.489 | −10.054 | 1.00 | 14.38 | A | C |
| ATOM | 569 | C | VAL | A | 42 | 72.795 | −34.852 | −12.638 | 1.00 | 14.41 | A | C |
| ATOM | 570 | O | VAL | A | 42 | 72.145 | −35.826 | −12.252 | 1.00 | 14.02 | A | O |
| ATOM | 572 | N | ARG | A | 43 | 72.581 | −34.250 | −13.806 | 1.00 | 15.17 | A | N |
| ATOM | 573 | CA | ARG | A | 43 | 71.602 | −34.748 | −14.771 | 1.00 | 15.29 | A | C |
| ATOM | 575 | CB | ARG | A | 43 | 71.509 | −33.805 | −15.980 | 1.00 | 15.11 | A | C |
| ATOM | 578 | CG | ARG | A | 43 | 70.642 | −34.310 | −17.123 | 1.00 | 15.92 | A | C |
| ATOM | 581 | CD | ARG | A | 43 | 71.411 | −35.191 | −18.114 | 1.00 | 15.67 | A | C |
| ATOM | 584 | NE | ARG | A | 43 | 70.592 | −35.551 | −19.270 | 1.00 | 16.12 | A | N |
| ATOM | 586 | CZ | ARG | A | 43 | 70.913 | −36.472 | −20.177 | 1.00 | 16.78 | A | C |
| ATOM | 587 | NH1 | ARG | A | 43 | 70.082 | −36.721 | −21.183 | 1.00 | 17.28 | A | N |
| ATOM | 590 | NH2 | ARG | A | 43 | 72.053 | −37.151 | −20.093 | 1.00 | 17.42 | A | N |
| ATOM | 593 | C | ARG | A | 43 | 71.965 | −36.162 | −15.216 | 1.00 | 15.15 | A | C |
| ATOM | 594 | O | ARG | A | 43 | 71.100 | −37.037 | −15.276 | 1.00 | 15.51 | A | O |
| ATOM | 596 | N | ARG | A | 44 | 73.241 | −36.374 | −15.531 | 1.00 | 14.58 | A | N |
| ATOM | 597 | CA | ARG | A | 44 | 73.725 | −37.680 | −15.973 | 1.00 | 14.27 | A | C |
| ATOM | 599 | CB | ARG | A | 44 | 75.239 | −37.638 | −16.204 | 1.00 | 14.13 | A | C |
| ATOM | 602 | CG | ARG | A | 44 | 75.837 | −38.956 | −16.685 | 1.00 | 13.74 | A | C |
| ATOM | 605 | CD | ARG | A | 44 | 77.311 | −38.822 | −17.038 | 1.00 | 12.58 | A | C |
| ATOM | 608 | NE | ARG | A | 44 | 78.167 | −38.729 | −15.858 | 1.00 | 10.73 | A | N |
| ATOM | 610 | CZ | ARG | A | 44 | 79.495 | −38.644 | −15.897 | 1.00 | 10.52 | A | C |
| ATOM | 611 | NH1 | ARG | A | 44 | 80.187 | −38.566 | −14.766 | 1.00 | 10.42 | A | N |
| ATOM | 614 | NH2 | ARG | A | 44 | 80.139 | −38.638 | −17.061 | 1.00 | 11.08 | A | N |
| ATOM | 617 | C | ARG | A | 44 | 73.391 | −38.772 | −14.963 | 1.00 | 14.55 | A | C |
| ATOM | 618 | O | ARG | A | 44 | 72.868 | −39.825 | −15.327 | 1.00 | 14.69 | A | O |
| ATOM | 620 | N | GLU | A | 45 | 73.690 | −38.506 | −13.694 | 1.00 | 14.88 | A | N |
| ATOM | 621 | CA | GLU | A | 45 | 73.533 | −39.502 | −12.633 | 1.00 | 15.12 | A | C |
| ATOM | 623 | CB | GLU | A | 45 | 74.228 | −39.032 | −11.351 | 1.00 | 15.38 | A | C |
| ATOM | 626 | CG | GLU | A | 45 | 75.737 | −38.939 | −11.473 | 1.00 | 15.34 | A | C |
| ATOM | 629 | CD | GLU | A | 45 | 76.367 | −40.280 | −11.758 | 1.00 | 15.55 | A | C |
| ATOM | 630 | OE1 | GLU | A | 45 | 76.236 | −41.183 | −10.906 | 1.00 | 16.23 | A | O |
| ATOM | 631 | OE2 | GLU | A | 45 | 76.982 | −40.433 | −12.835 | 1.00 | 15.50 | A | O |
| ATOM | 632 | C | GLU | A | 45 | 72.074 | −39.843 | −12.337 | 1.00 | 15.09 | A | C |
| ATOM | 633 | O | GLU | A | 45 | 71.771 | −40.973 | −11.951 | 1.00 | 15.45 | A | O |
| ATOM | 635 | N | ILE | A | 46 | 71.180 | −38.870 | −12.506 | 1.00 | 14.76 | A | N |
| ATOM | 636 | CA | ILE | A | 46 | 69.744 | −39.112 | −12.348 | 1.00 | 14.30 | A | C |
| ATOM | 638 | CB | ILE | A | 46 | 68.926 | −37.795 | −12.366 | 1.00 | 14.11 | A | C |
| ATOM | 640 | CG1 | ILE | A | 46 | 69.239 | −36.947 | −11.130 | 1.00 | 13.91 | A | C |
| ATOM | 643 | CD1 | ILE | A | 46 | 68.714 | −35.524 | −11.210 | 1.00 | 11.51 | A | C |
| ATOM | 647 | CG2 | ILE | A | 46 | 67.439 | −38.092 | −12.399 | 1.00 | 13.21 | A | C |
| ATOM | 651 | C | ILE | A | 46 | 69.232 | −40.051 | −13.446 | 1.00 | 14.04 | A | C |
| ATOM | 652 | O | ILE | A | 46 | 68.418 | −40.939 | −13.175 | 1.00 | 13.88 | A | O |
| ATOM | 654 | N | ASN | A | 47 | 69.725 | −39.856 | −14.671 | 1.00 | 13.76 | A | N |
| ATOM | 655 | CA | ASN | A | 47 | 69.287 | −40.643 | −15.834 | 1.00 | 13.67 | A | C |
| ATOM | 657 | CB | ASN | A | 47 | 69.461 | −39.835 | −17.124 | 1.00 | 13.22 | A | C |
| ATOM | 660 | CG | ASN | A | 47 | 68.546 | −38.636 | −17.190 | 1.00 | 12.47 | A | C |
| ATOM | 661 | OD1 | ASN | A | 47 | 67.387 | −38.694 | −16.774 | 1.00 | 12.16 | A | O |
| ATOM | 662 | ND2 | ASN | A | 47 | 69.058 | −37.539 | −17.722 | 1.00 | 13.14 | A | N |
| ATOM | 665 | C | ASN | A | 47 | 69.994 | −41.987 | −15.994 | 1.00 | 13.91 | A | C |
| ATOM | 666 | O | ASN | A | 47 | 69.587 | −42.808 | −16.817 | 1.00 | 13.86 | A | O |
| ATOM | 668 | N | ASN | A | 48 | 71.048 | −42.205 | −15.213 | 1.00 | 14.42 | A | N |
| ATOM | 669 | CA | ASN | A | 48 | 71.827 | −43.441 | −15.274 | 1.00 | 14.74 | A | C |
| ATOM | 671 | CB | ASN | A | 48 | 72.850 | −43.469 | −14.132 | 1.00 | 14.72 | A | C |
| ATOM | 674 | CG | ASN | A | 48 | 73.753 | −44.679 | −14.183 | 1.00 | 13.04 | A | C |
| ATOM | 675 | OD1 | ASN | A | 48 | 74.135 | −45.138 | −15.256 | 1.00 | 11.75 | A | O |

TABLE 8-2-continued

Coordinates for L494P Structure

| | | | | | | | | | | | | |
|---|---|---|---|---|---|---|---|---|---|---|---|---|
| ATOM | 676 | ND2 | ASN | A | 48 | 74.106 | −45.199 | −13.017 | 1.00 | 13.70 | A | N |
| ATOM | 679 | C | ASN | A | 48 | 70.947 | −44.693 | −15.222 | 1.00 | 15.25 | A | C |
| ATOM | 680 | O | ASN | A | 48 | 70.371 | −45.016 | −14.186 | 1.00 | 14.91 | A | O |
| ATOM | 682 | N | GLU | A | 49 | 70.855 | −45.385 | −16.355 | 1.00 | 16.44 | A | N |
| ATOM | 683 | CA | GLU | A | 49 | 70.070 | −46.615 | −16.472 | 1.00 | 17.44 | A | C |
| ATOM | 685 | CB | GLU | A | 49 | 70.073 | −47.113 | −17.924 | 1.00 | 17.86 | A | C |
| ATOM | 688 | CG | GLU | A | 49 | 69.434 | −46.153 | −18.947 | 1.00 | 20.47 | A | C |
| ATOM | 691 | CD | GLU | A | 49 | 67.909 | −46.256 | −19.022 | 1.00 | 23.90 | A | C |
| ATOM | 692 | OE1 | GLU | A | 49 | 67.362 | −47.364 | −18.830 | 1.00 | 26.25 | A | O |
| ATOM | 693 | OE2 | GLU | A | 49 | 67.256 | −45.223 | −19.293 | 1.00 | 24.41 | A | O |
| ATOM | 694 | C | GLU | A | 49 | 70.608 | −47.715 | −15.555 | 1.00 | 17.76 | A | C |
| ATOM | 695 | O | GLU | A | 49 | 69.839 | −48.490 | −14.995 | 1.00 | 17.28 | A | O |
| ATOM | 697 | N | LYS | A | 50 | 71.929 | −47.765 | −15.402 | 1.00 | 18.95 | A | N |
| ATOM | 698 | CA | LYS | A | 50 | 72.596 | −48.784 | −14.591 | 1.00 | 19.93 | A | C |
| ATOM | 700 | CB | LYS | A | 50 | 73.871 | −49.267 | −15.298 | 1.00 | 20.28 | A | C |
| ATOM | 703 | CG | LYS | A | 50 | 73.695 | −49.676 | −16.758 | 1.00 | 21.77 | A | C |
| ATOM | 706 | CD | LYS | A | 50 | 74.932 | −50.420 | −17.276 | 1.00 | 23.08 | A | C |
| ATOM | 709 | CE | LYS | A | 50 | 75.158 | −50.200 | −18.772 | 1.00 | 23.59 | A | C |
| ATOM | 712 | NZ | LYS | A | 50 | 73.974 | −50.577 | −19.593 | 1.00 | 23.30 | A | N |
| ATOM | 716 | C | LYS | A | 50 | 72.955 | −48.250 | −13.200 | 1.00 | 20.51 | A | C |
| ATOM | 717 | O | LYS | A | 50 | 74.120 | −48.286 | −12.796 | 1.00 | 20.59 | A | O |
| ATOM | 719 | N | ALA | A | 51 | 71.958 | −47.758 | −12.470 | 1.00 | 21.42 | A | N |
| ATOM | 720 | CA | ALA | A | 51 | 72.171 | −47.241 | −11.116 | 1.00 | 22.31 | A | C |
| ATOM | 722 | CB | ALA | A | 51 | 71.607 | −45.839 | −10.994 | 1.00 | 22.41 | A | C |
| ATOM | 726 | C | ALA | A | 51 | 71.525 | −48.163 | −10.085 | 1.00 | 23.21 | A | C |
| ATOM | 727 | O | ALA | A | 51 | 70.500 | −48.791 | −10.361 | 1.00 | 23.63 | A | O |
| ATOM | 729 | N | GLU | A | 52 | 72.124 | −48.239 | −8.898 | 1.00 | 23.78 | A | N |
| ATOM | 730 | CA | GLU | A | 52 | 71.577 | −49.056 | −7.816 | 1.00 | 24.30 | A | C |
| ATOM | 732 | CB | GLU | A | 52 | 72.590 | −49.208 | −6.675 | 1.00 | 24.41 | A | C |
| ATOM | 735 | CG | GLU | A | 52 | 72.493 | −50.535 | −5.927 | 1.00 | 26.16 | A | C |
| ATOM | 738 | CD | GLU | A | 52 | 72.854 | −51.746 | −6.787 | 1.00 | 27.22 | A | C |
| ATOM | 739 | OE1 | GLU | A | 52 | 73.411 | −51.571 | −7.894 | 1.00 | 27.13 | A | O |
| ATOM | 740 | OE2 | GLU | A | 52 | 72.580 | −52.881 | −6.345 | 1.00 | 28.02 | A | O |
| ATOM | 741 | C | GLU | A | 52 | 70.296 | −48.394 | −7.320 | 1.00 | 24.56 | A | C |
| ATOM | 742 | O | GLU | A | 52 | 70.241 | −47.171 | −7.194 | 1.00 | 25.07 | A | O |
| ATOM | 744 | N | PHE | A | 53 | 69.272 | −49.199 | −7.049 | 1.00 | 24.66 | A | N |
| ATOM | 745 | CA | PHE | A | 53 | 67.932 | −48.672 | −6.762 | 1.00 | 24.68 | A | C |
| ATOM | 747 | CB | PHE | A | 53 | 66.919 | −49.811 | −6.571 | 1.00 | 25.20 | A | C |
| ATOM | 750 | CG | PHE | A | 53 | 66.487 | −50.467 | −7.862 | 1.00 | 28.10 | A | C |
| ATOM | 751 | CD1 | PHE | A | 53 | 65.998 | −49.700 | −8.920 | 1.00 | 30.01 | A | C |
| ATOM | 753 | CE1 | PHE | A | 53 | 65.592 | −50.296 | −10.112 | 1.00 | 30.91 | A | C |
| ATOM | 755 | CZ | PHE | A | 53 | 65.666 | −51.679 | −10.254 | 1.00 | 32.14 | A | C |
| ATOM | 757 | CE2 | PHE | A | 53 | 66.144 | −52.458 | −9.202 | 1.00 | 31.02 | A | C |
| ATOM | 759 | CD2 | PHE | A | 53 | 66.549 | −51.851 | −8.013 | 1.00 | 29.73 | A | C |
| ATOM | 761 | C | PHE | A | 53 | 67.879 | −47.717 | −5.566 | 1.00 | 23.76 | A | C |
| ATOM | 762 | O | PHE | A | 53 | 67.250 | −46.663 | −5.650 | 1.00 | 23.93 | A | O |
| ATOM | 764 | N | LEU | A | 54 | 68.535 | −48.075 | −4.465 | 1.00 | 22.52 | A | N |
| ATOM | 765 | CA | LEU | A | 54 | 68.557 | −47.206 | −3.286 | 1.00 | 21.36 | A | C |
| ATOM | 767 | CB | LEU | A | 54 | 69.083 | −47.951 | −2.055 | 1.00 | 21.51 | A | C |
| ATOM | 770 | CG | LEU | A | 54 | 68.781 | −47.281 | −0.708 | 1.00 | 21.41 | A | C |
| ATOM | 772 | CD1 | LEU | A | 54 | 67.301 | −47.429 | −0.372 | 1.00 | 20.97 | A | C |
| ATOM | 776 | CD2 | LEU | A | 54 | 69.653 | −47.855 | 0.412 | 1.00 | 19.73 | A | C |
| ATOM | 780 | C | LEU | A | 54 | 69.401 | −45.959 | −3.541 | 1.00 | 20.27 | A | C |
| ATOM | 781 | O | LEU | A | 54 | 69.000 | −44.856 | −3.175 | 1.00 | 20.35 | A | O |
| ATOM | 783 | N | THR | A | 55 | 70.561 | −46.142 | −4.170 | 1.00 | 19.14 | A | N |
| ATOM | 784 | CA | THR | A | 55 | 71.463 | −45.031 | −4.495 | 1.00 | 18.11 | A | C |
| ATOM | 786 | CB | THR | A | 55 | 72.739 | −45.521 | −5.210 | 1.00 | 18.12 | A | C |
| ATOM | 788 | OG1 | THR | A | 55 | 73.383 | −46.521 | −4.412 | 1.00 | 17.71 | A | O |
| ATOM | 790 | CG2 | THR | A | 55 | 73.707 | −44.363 | −5.451 | 1.00 | 17.05 | A | C |
| ATOM | 794 | C | THR | A | 55 | 70.787 | −43.994 | −5.380 | 1.00 | 17.32 | A | C |
| ATOM | 795 | O | THR | A | 55 | 71.003 | −42.798 | −5.210 | 1.00 | 17.16 | A | O |
| ATOM | 797 | N | LEU | A | 56 | 69.975 | −44.457 | −6.327 | 1.00 | 16.99 | A | N |
| ATOM | 798 | CA | LEU | A | 56 | 69.204 | −43.555 | −7.179 | 1.00 | 17.23 | A | C |
| ATOM | 800 | CB | LEU | A | 56 | 68.488 | −44.324 | −8.295 | 1.00 | 17.55 | A | C |
| ATOM | 803 | CG | LEU | A | 56 | 67.539 | −43.518 | −9.196 | 1.00 | 18.41 | A | C |
| ATOM | 805 | CD1 | LEU | A | 56 | 68.246 | −42.308 | −9.796 | 1.00 | 18.81 | A | C |
| ATOM | 809 | CD2 | LEU | A | 56 | 66.954 | −44.398 | −10.296 | 1.00 | 19.59 | A | C |
| ATOM | 813 | C | LEU | A | 56 | 68.190 | −42.785 | −6.343 | 1.00 | 16.79 | A | C |
| ATOM | 814 | O | LEU | A | 56 | 68.100 | −41.559 | −6.443 | 1.00 | 16.92 | A | O |
| ATOM | 816 | N | LEU | A | 57 | 67.436 | −43.511 | −5.520 | 1.00 | 16.16 | A | N |
| ATOM | 817 | CA | LEU | A | 57 | 66.437 | −42.899 | −4.643 | 1.00 | 15.66 | A | C |
| ATOM | 819 | CB | LEU | A | 57 | 65.700 | −43.972 | −3.833 | 1.00 | 15.19 | A | C |
| ATOM | 822 | CG | LEU | A | 57 | 64.765 | −44.889 | −4.625 | 1.00 | 14.21 | A | C |
| ATOM | 824 | CD1 | LEU | A | 57 | 64.334 | −46.067 | −3.767 | 1.00 | 13.60 | A | C |
| ATOM | 828 | CD2 | LEU | A | 57 | 63.552 | −44.133 | −5.151 | 1.00 | 11.60 | A | C |
| ATOM | 832 | C | LEU | A | 57 | 67.055 | −41.859 | −3.701 | 1.00 | 15.52 | A | C |
| ATOM | 833 | O | LEU | A | 57 | 66.458 | −40.809 | −3.453 | 1.00 | 15.41 | A | O |
| ATOM | 835 | N | GLU | A | 58 | 68.254 | −42.147 | −3.197 | 1.00 | 15.21 | A | N |

TABLE 8-2-continued

Coordinates for L494P Structure

| | | | | | | | | | | | | |
|---|---|---|---|---|---|---|---|---|---|---|---|---|
| ATOM | 836 | CA | GLU | A | 58 | 68.940 | −41.238 | −2.274 | 1.00 | 14.75 | A | C |
| ATOM | 838 | CB | GLU | A | 58 | 69.981 | −41.988 | −1.430 | 1.00 | 14.86 | A | C |
| ATOM | 841 | CG | GLU | A | 58 | 69.363 | −42.871 | −0.341 | 1.00 | 15.06 | A | C |
| ATOM | 844 | CD | GLU | A | 58 | 70.385 | −43.442 | 0.633 | 1.00 | 16.98 | A | C |
| ATOM | 845 | OE1 | GLU | A | 58 | 71.547 | −42.981 | 0.644 | 1.00 | 19.17 | A | O |
| ATOM | 846 | OE2 | GLU | A | 58 | 70.020 | −44.360 | 1.398 | 1.00 | 18.53 | A | O |
| ATOM | 847 | C | GLU | A | 58 | 69.575 | −40.035 | −2.975 | 1.00 | 14.11 | A | C |
| ATOM | 848 | O | GLU | A | 58 | 69.657 | −38.959 | −2.382 | 1.00 | 14.43 | A | O |
| ATOM | 850 | N | LEU | A | 59 | 70.020 | −40.202 | −4.221 | 1.00 | 13.22 | A | N |
| ATOM | 851 | CA | LEU | A | 59 | 70.528 | −39.065 | −4.999 | 1.00 | 12.44 | A | C |
| ATOM | 853 | CB | LEU | A | 59 | 71.180 | −39.518 | −6.311 | 1.00 | 12.19 | A | C |
| ATOM | 856 | CG | LEU | A | 59 | 71.677 | −38.393 | −7.235 | 1.00 | 10.80 | A | C |
| ATOM | 858 | CD1 | LEU | A | 59 | 72.780 | −37.589 | −6.572 | 1.00 | 9.85 | A | C |
| ATOM | 862 | CD2 | LEU | A | 59 | 72.154 | −38.949 | −8.566 | 1.00 | 9.48 | A | C |
| ATOM | 866 | C | LEU | A | 59 | 69.390 | −38.100 | −5.298 | 1.00 | 12.08 | A | C |
| ATOM | 867 | O | LEU | A | 59 | 69.549 | −36.889 | −5.164 | 1.00 | 11.53 | A | O |
| ATOM | 869 | N | ILE | A | 60 | 68.249 | −38.649 | −5.706 | 1.00 | 12.13 | A | N |
| ATOM | 870 | CA | ILE | A | 60 | 67.048 | −37.856 | −5.955 | 1.00 | 12.54 | A | C |
| ATOM | 872 | CB | ILE | A | 60 | 65.863 | −38.745 | −6.386 | 1.00 | 12.58 | A | C |
| ATOM | 874 | CG1 | ILE | A | 60 | 66.077 | −39.276 | −7.806 | 1.00 | 12.32 | A | C |
| ATOM | 877 | CD1 | ILE | A | 60 | 65.083 | −40.350 | −8.213 | 1.00 | 9.20 | A | C |
| ATOM | 881 | CG2 | ILE | A | 60 | 64.557 | −37.964 | −6.324 | 1.00 | 13.18 | A | C |
| ATOM | 885 | C | ILE | A | 60 | 66.649 | −37.073 | −4.707 | 1.00 | 13.10 | A | C |
| ATOM | 886 | O | ILE | A | 60 | 66.474 | −35.853 | −4.761 | 1.00 | 13.34 | A | O |
| ATOM | 888 | N | ASP | A | 61 | 66.512 | −37.782 | −3.587 | 1.00 | 13.39 | A | N |
| ATOM | 889 | CA | ASP | A | 61 | 66.154 | −37.162 | −2.310 | 1.00 | 13.31 | A | C |
| ATOM | 891 | CB | ASP | A | 61 | 66.150 | −38.205 | −1.185 | 1.00 | 13.34 | A | C |
| ATOM | 894 | CG | ASP | A | 61 | 65.640 | −37.650 | 0.139 | 1.00 | 13.56 | A | C |
| ATOM | 895 | OD1 | ASP | A | 61 | 64.927 | −36.625 | 0.136 | 1.00 | 12.03 | A | O |
| ATOM | 896 | OD2 | ASP | A | 61 | 65.946 | −38.252 | 1.191 | 1.00 | 15.02 | A | O |
| ATOM | 897 | C | ASP | A | 61 | 67.121 | −36.027 | −1.979 | 1.00 | 13.29 | A | C |
| ATOM | 898 | O | ASP | A | 61 | 66.694 | −34.889 | −1.777 | 1.00 | 13.14 | A | O |
| ATOM | 900 | N | ASN | A | 62 | 68.416 | −36.345 | −1.943 | 1.00 | 13.31 | A | N |
| ATOM | 901 | CA | ASN | A | 62 | 69.463 | −35.346 | −1.704 | 1.00 | 13.68 | A | C |
| ATOM | 903 | CB | ASN | A | 62 | 70.865 | −35.972 | −1.816 | 1.00 | 13.84 | A | C |
| ATOM | 906 | CG | ASN | A | 62 | 71.306 | −36.690 | −0.542 | 1.00 | 13.75 | A | C |
| ATOM | 907 | OD1 | ASN | A | 62 | 70.678 | −36.574 | 0.510 | 1.00 | 11.26 | A | O |
| ATOM | 908 | ND2 | ASN | A | 62 | 72.404 | −37.432 | −0.639 | 1.00 | 14.47 | A | N |
| ATOM | 911 | C | ASN | A | 62 | 69.363 | −34.158 | −2.661 | 1.00 | 14.11 | A | C |
| ATOM | 912 | O | ASN | A | 62 | 69.476 | −33.005 | −2.240 | 1.00 | 14.02 | A | O |
| ATOM | 914 | N | VAL | A | 63 | 69.150 | −34.446 | −3.944 | 1.00 | 14.45 | A | N |
| ATOM | 915 | CA | VAL | A | 63 | 68.998 | −33.400 | −4.957 | 1.00 | 14.74 | A | C |
| ATOM | 917 | CB | VAL | A | 63 | 68.845 | −33.996 | −6.377 | 1.00 | 14.56 | A | C |
| ATOM | 919 | CG1 | VAL | A | 63 | 68.343 | −32.943 | −7.354 | 1.00 | 14.88 | A | C |
| ATOM | 923 | CG2 | VAL | A | 63 | 70.165 | −34.575 | −6.854 | 1.00 | 14.45 | A | C |
| ATOM | 927 | C | VAL | A | 63 | 67.796 | −32.503 | −4.657 | 1.00 | 15.15 | A | C |
| ATOM | 928 | O | VAL | A | 63 | 67.890 | −31.278 | −4.762 | 1.00 | 15.47 | A | O |
| ATOM | 930 | N | GLN | A | 64 | 66.675 | −33.114 | −4.281 | 1.00 | 15.27 | A | N |
| ATOM | 931 | CA | GLN | A | 64 | 65.467 | −32.355 | −3.956 | 1.00 | 15.55 | A | C |
| ATOM | 933 | CB | GLN | A | 64 | 64.254 | −33.283 | −3.802 | 1.00 | 15.45 | A | C |
| ATOM | 936 | CG | GLN | A | 64 | 63.743 | −33.865 | −5.114 | 1.00 | 13.13 | A | C |
| ATOM | 939 | CD | GLN | A | 64 | 62.319 | −34.385 | −5.025 | 1.00 | 10.71 | A | C |
| ATOM | 940 | OE1 | GLN | A | 64 | 61.622 | −34.470 | −6.033 | 1.00 | 10.64 | A | O |
| ATOM | 941 | NE2 | GLN | A | 64 | 61.881 | −34.731 | −3.821 | 1.00 | 8.09 | A | N |
| ATOM | 944 | C | GLN | A | 64 | 65.650 | −31.519 | −2.688 | 1.00 | 15.86 | A | C |
| ATOM | 945 | O | GLN | A | 64 | 65.402 | −30.311 | −2.693 | 1.00 | 16.06 | A | O |
| ATOM | 947 | N | ARG | A | 65 | 66.089 | −32.167 | −1.612 | 1.00 | 15.84 | A | N |
| ATOM | 948 | CA | ARG | A | 65 | 66.241 | −31.506 | −0.313 | 1.00 | 15.98 | A | C |
| ATOM | 950 | CB | ARG | A | 65 | 66.627 | −32.523 | 0.764 | 1.00 | 16.31 | A | C |
| ATOM | 953 | CG | ARG | A | 65 | 65.505 | −33.496 | 1.113 | 1.00 | 18.72 | A | C |
| ATOM | 956 | CD | ARG | A | 65 | 65.879 | −34.400 | 2.279 | 1.00 | 20.75 | A | C |
| ATOM | 959 | NE | ARG | A | 65 | 66.068 | −33.641 | 3.514 | 1.00 | 22.71 | A | N |
| ATOM | 961 | CZ | ARG | A | 65 | 66.575 | −34.133 | 4.642 | 1.00 | 24.75 | A | C |
| ATOM | 962 | NH1 | ARG | A | 65 | 66.956 | −35.405 | 4.721 | 1.00 | 25.07 | A | N |
| ATOM | 965 | NH2 | ARG | A | 65 | 66.703 | −33.343 | 5.704 | 1.00 | 26.41 | A | N |
| ATOM | 968 | C | ARG | A | 65 | 67.253 | −30.361 | −0.342 | 1.00 | 15.53 | A | C |
| ATOM | 969 | O | ARG | A | 65 | 67.039 | −29.331 | 0.297 | 1.00 | 15.14 | A | O |
| ATOM | 971 | N | LEU | A | 66 | 68.338 | −30.536 | −1.099 | 1.00 | 15.13 | A | N |
| ATOM | 972 | CA | LEU | A | 66 | 69.343 | −29.481 | −1.287 | 1.00 | 14.45 | A | C |
| ATOM | 974 | CB | LEU | A | 66 | 70.588 | −30.046 | −1.979 | 1.00 | 14.24 | A | C |
| ATOM | 977 | CG | LEU | A | 66 | 71.505 | −30.909 | −1.108 | 1.00 | 13.57 | A | C |
| ATOM | 979 | CD1 | LEU | A | 66 | 72.413 | −31.781 | −1.961 | 1.00 | 13.45 | A | C |
| ATOM | 983 | CD2 | LEU | A | 66 | 72.329 | −30.036 | −0.178 | 1.00 | 12.36 | A | C |
| ATOM | 987 | C | LEU | A | 66 | 68.807 | −28.271 | −2.073 | 1.00 | 14.56 | A | C |
| ATOM | 988 | O | LEU | A | 66 | 69.544 | −27.313 | −2.332 | 1.00 | 14.45 | A | O |
| ATOM | 990 | N | GLY | A | 67 | 67.533 | −28.330 | −2.459 | 1.00 | 14.51 | A | N |
| ATOM | 991 | CA | GLY | A | 67 | 66.842 | −27.203 | −3.059 | 1.00 | 14.34 | A | C |
| ATOM | 994 | C | GLY | A | 67 | 66.968 | −27.115 | −4.564 | 1.00 | 14.63 | A | C |

TABLE 8-2-continued

Coordinates for L494P Structure

| | | | | | | | | | | | | |
|---|---|---|---|---|---|---|---|---|---|---|---|---|
| ATOM | 995 | O | GLY | A | 67 | 66.621 | −26.093 | −5.152 | 1.00 | 14.83 | A | O |
| ATOM | 997 | N | LEU | A | 68 | 67.448 | −28.191 | −5.189 | 1.00 | 15.09 | A | N |
| ATOM | 998 | CA | LEU | A | 68 | 67.656 | −28.234 | −6.638 | 1.00 | 15.36 | A | C |
| ATOM | 1000 | CB | LEU | A | 68 | 69.035 | −28.828 | −6.950 | 1.00 | 15.11 | A | C |
| ATOM | 1003 | CG | LEU | A | 68 | 70.243 | −28.122 | −6.332 | 1.00 | 14.67 | A | C |
| ATOM | 1005 | CD1 | LEU | A | 68 | 71.533 | −28.793 | −6.779 | 1.00 | 13.80 | A | C |
| ATOM | 1009 | CD2 | LEU | A | 68 | 70.256 | −26.651 | −6.699 | 1.00 | 12.27 | A | C |
| ATOM | 1013 | C | LEU | A | 68 | 66.577 | −29.042 | −7.371 | 1.00 | 15.95 | A | C |
| ATOM | 1014 | O | LEU | A | 68 | 66.679 | −29.258 | −8.578 | 1.00 | 16.42 | A | O |
| ATOM | 1016 | N | GLY | A | 69 | 65.543 | −29.473 | −6.653 | 1.00 | 16.33 | A | N |
| ATOM | 1017 | CA | GLY | A | 69 | 64.496 | −30.320 | −7.228 | 1.00 | 16.45 | A | C |
| ATOM | 1020 | C | GLY | A | 69 | 63.810 | −29.734 | −8.449 | 1.00 | 16.20 | A | C |
| ATOM | 1021 | O | GLY | A | 69 | 63.667 | −30.410 | −9.469 | 1.00 | 16.47 | A | O |
| ATOM | 1023 | N | TYR | A | 70 | 63.392 | −28.474 | −8.340 | 1.00 | 15.95 | A | N |
| ATOM | 1024 | CA | TYR | A | 70 | 62.726 | −27.760 | −9.440 | 1.00 | 15.71 | A | C |
| ATOM | 1026 | CB | TYR | A | 70 | 62.501 | −26.284 | −9.065 | 1.00 | 15.82 | A | C |
| ATOM | 1029 | CG | TYR | A | 70 | 63.755 | −25.424 | −9.114 | 1.00 | 14.12 | A | C |
| ATOM | 1030 | CD1 | TYR | A | 70 | 63.989 | −24.561 | −10.183 | 1.00 | 10.77 | A | C |
| ATOM | 1032 | CE1 | TYR | A | 70 | 65.133 | −23.781 | −10.237 | 1.00 | 10.89 | A | C |
| ATOM | 1034 | CZ | TYR | A | 70 | 66.066 | −23.856 | −9.216 | 1.00 | 11.24 | A | C |
| ATOM | 1035 | OH | TYR | A | 70 | 67.208 | −23.084 | −9.269 | 1.00 | 9.98 | A | O |
| ATOM | 1037 | CE2 | TYR | A | 70 | 65.859 | −24.705 | −8.145 | 1.00 | 11.41 | A | C |
| ATOM | 1039 | CD2 | TYR | A | 70 | 64.709 | −25.485 | −8.100 | 1.00 | 12.70 | A | C |
| ATOM | 1041 | C | TYR | A | 70 | 63.522 | −27.841 | −10.744 | 1.00 | 15.82 | A | C |
| ATOM | 1042 | O | TYR | A | 70 | 62.951 | −27.909 | −11.835 | 1.00 | 15.94 | A | O |
| ATOM | 1044 | N | ARG | A | 71 | 64.844 | −27.839 | −10.607 | 1.00 | 15.72 | A | N |
| ATOM | 1045 | CA | ARG | A | 71 | 65.757 | −27.824 | −11.737 | 1.00 | 15.71 | A | C |
| ATOM | 1047 | CB | ARG | A | 71 | 67.171 | −27.540 | −11.224 | 1.00 | 15.56 | A | C |
| ATOM | 1050 | CG | ARG | A | 71 | 68.175 | −27.150 | −12.286 | 1.00 | 16.84 | A | C |
| ATOM | 1053 | CD | ARG | A | 71 | 69.345 | −26.386 | −11.679 | 1.00 | 17.64 | A | C |
| ATOM | 1056 | NE | ARG | A | 71 | 69.076 | −24.951 | −11.600 | 1.00 | 18.02 | A | N |
| ATOM | 1058 | CZ | ARG | A | 71 | 69.124 | −24.113 | −12.633 | 1.00 | 18.91 | A | C |
| ATOM | 1059 | NH1 | ARG | A | 71 | 68.863 | −22.828 | −12.444 | 1.00 | 20.58 | A | N |
| ATOM | 1062 | NH2 | ARG | A | 71 | 69.428 | −24.546 | −13.856 | 1.00 | 18.44 | A | N |
| ATOM | 1065 | C | ARG | A | 71 | 65.729 | −29.131 | −12.535 | 1.00 | 15.68 | A | C |
| ATOM | 1066 | O | ARG | A | 71 | 65.790 | −29.111 | −13.764 | 1.00 | 15.69 | A | O |
| ATOM | 1068 | N | PHE | A | 72 | 65.625 | −30.260 | −11.838 | 1.00 | 15.70 | A | N |
| ATOM | 1069 | CA | PHE | A | 72 | 65.712 | −31.573 | −12.478 | 1.00 | 15.94 | A | C |
| ATOM | 1071 | CB | PHE | A | 72 | 66.838 | −32.393 | −11.835 | 1.00 | 15.86 | A | C |
| ATOM | 1074 | CG | PHE | A | 72 | 68.197 | −31.764 | −11.949 | 1.00 | 13.92 | A | C |
| ATOM | 1075 | CD1 | PHE | A | 72 | 68.891 | −31.797 | −13.151 | 1.00 | 13.93 | A | C |
| ATOM | 1077 | CE1 | PHE | A | 72 | 70.153 | −31.229 | −13.260 | 1.00 | 13.72 | A | C |
| ATOM | 1079 | CZ | PHE | A | 72 | 70.737 | −30.625 | −12.157 | 1.00 | 13.27 | A | C |
| ATOM | 1081 | CE2 | PHE | A | 72 | 70.057 | −30.590 | −10.951 | 1.00 | 12.76 | A | C |
| ATOM | 1083 | CD2 | PHE | A | 72 | 68.795 | −31.161 | −10.851 | 1.00 | 12.21 | A | C |
| ATOM | 1085 | C | PHE | A | 72 | 64.407 | −32.371 | −12.404 | 1.00 | 16.42 | A | C |
| ATOM | 1086 | O | PHE | A | 72 | 64.439 | −33.601 | −12.348 | 1.00 | 16.51 | A | O |
| ATOM | 1088 | N | GLU | A | 73 | 63.265 | −31.686 | −12.425 | 1.00 | 16.94 | A | N |
| ATOM | 1089 | CA | GLU | A | 73 | 61.967 | −32.365 | −12.315 | 1.00 | 17.43 | A | C |
| ATOM | 1091 | CB | GLU | A | 73 | 60.812 | −31.361 | −12.397 | 1.00 | 17.65 | A | C |
| ATOM | 1094 | CG | GLU | A | 73 | 59.425 | −31.997 | −12.254 | 1.00 | 19.25 | A | C |
| ATOM | 1097 | CD | GLU | A | 73 | 58.291 | −30.983 | −12.251 | 1.00 | 21.29 | A | C |
| ATOM | 1098 | OE1 | GLU | A | 73 | 58.563 | −29.769 | −12.127 | 1.00 | 22.11 | A | O |
| ATOM | 1099 | OE2 | GLU | A | 73 | 57.121 | −31.410 | −12.370 | 1.00 | 21.96 | A | O |
| ATOM | 1100 | C | GLU | A | 73 | 61.793 | −33.454 | −13.379 | 1.00 | 17.47 | A | C |
| ATOM | 1101 | O | GLU | A | 73 | 61.625 | −34.628 | −13.047 | 1.00 | 17.51 | A | O |
| ATOM | 1103 | N | SER | A | 74 | 61.841 | −33.062 | −14.649 | 1.00 | 17.73 | A | N |
| ATOM | 1104 | CA | SER | A | 74 | 61.656 | −34.004 | −15.756 | 1.00 | 18.06 | A | C |
| ATOM | 1106 | CB | SER | A | 74 | 61.792 | −33.293 | −17.103 | 1.00 | 18.17 | A | C |
| ATOM | 1109 | OG | SER | A | 74 | 63.117 | −32.833 | −17.303 | 1.00 | 19.43 | A | O |
| ATOM | 1111 | C | SER | A | 74 | 62.648 | −35.161 | −15.682 | 1.00 | 17.97 | A | C |
| ATOM | 1112 | O | SER | A | 74 | 62.264 | −36.317 | −15.846 | 1.00 | 17.90 | A | O |
| ATOM | 1114 | N | ASP | A | 75 | 63.915 | −34.842 | −15.425 | 1.00 | 18.18 | A | N |
| ATOM | 1115 | CA | ASP | A | 75 | 64.961 | −35.862 | −15.295 | 1.00 | 18.40 | A | C |
| ATOM | 1117 | CB | ASP | A | 75 | 66.344 | −35.224 | −15.112 | 1.00 | 18.40 | A | C |
| ATOM | 1120 | CG | ASP | A | 75 | 66.754 | −34.365 | −16.292 | 1.00 | 18.51 | A | C |
| ATOM | 1121 | OD1 | ASP | A | 75 | 67.526 | −34.847 | −17.144 | 1.00 | 15.74 | A | O |
| ATOM | 1122 | OD2 | ASP | A | 75 | 66.294 | −33.207 | −16.370 | 1.00 | 20.28 | A | O |
| ATOM | 1123 | C | ASP | A | 75 | 64.676 | −36.804 | −14.125 | 1.00 | 18.44 | A | C |
| ATOM | 1124 | O | ASP | A | 75 | 64.923 | −38.008 | −14.221 | 1.00 | 18.88 | A | O |
| ATOM | 1126 | N | ILE | A | 76 | 64.161 | −36.247 | −13.030 | 1.00 | 18.14 | A | N |
| ATOM | 1127 | CA | ILE | A | 76 | 63.789 | −37.033 | −11.854 | 1.00 | 17.84 | A | C |
| ATOM | 1129 | CB | ILE | A | 76 | 63.466 | −36.129 | −10.640 | 1.00 | 17.71 | A | C |
| ATOM | 1131 | CG1 | ILE | A | 76 | 64.758 | −35.575 | −10.035 | 1.00 | 16.61 | A | C |
| ATOM | 1134 | CD1 | ILE | A | 76 | 64.561 | −34.317 | −9.224 | 1.00 | 14.92 | A | C |
| ATOM | 1138 | CG2 | ILE | A | 76 | 62.694 | −36.904 | −9.580 | 1.00 | 17.99 | A | C |
| ATOM | 1142 | C | ILE | A | 76 | 62.594 | −37.930 | −12.160 | 1.00 | 17.97 | A | C |
| ATOM | 1143 | O | ILE | A | 76 | 62.658 | −39.136 | −11.939 | 1.00 | 18.10 | A | O |

TABLE 8-2-continued

Coordinates for L494P Structure

| | | | | | | | | | | | | |
|---|---|---|---|---|---|---|---|---|---|---|---|---|
| ATOM | 1145 | N | ARG | A | 77 | 61.515 | −37.341 | −12.674 | 1.00 | 18.15 | A | N |
| ATOM | 1146 | CA | ARG | A | 77 | 60.331 | −38.107 | −13.077 | 1.00 | 18.64 | A | C |
| ATOM | 1148 | CB | ARG | A | 77 | 59.350 | −37.225 | −13.851 | 1.00 | 18.82 | A | C |
| ATOM | 1151 | CG | ARG | A | 77 | 58.565 | −36.253 | −12.988 | 1.00 | 20.98 | A | C |
| ATOM | 1154 | CD | ARG | A | 77 | 57.624 | −35.398 | −13.835 | 1.00 | 23.38 | A | C |
| ATOM | 1157 | NE | ARG | A | 77 | 56.595 | −36.205 | −14.492 | 1.00 | 24.73 | A | N |
| ATOM | 1159 | CZ | ARG | A | 77 | 55.471 | −36.635 | −13.915 | 1.00 | 25.64 | A | C |
| ATOM | 1160 | NH1 | ARG | A | 77 | 55.192 | −36.346 | −12.645 | 1.00 | 26.60 | A | N |
| ATOM | 1163 | NH2 | ARG | A | 77 | 54.613 | −37.364 | −14.618 | 1.00 | 25.52 | A | N |
| ATOM | 1166 | C | ARG | A | 77 | 60.711 | −39.312 | −13.938 | 1.00 | 18.58 | A | C |
| ATOM | 1167 | O | ARG | A | 77 | 60.240 | −40.427 | −13.706 | 1.00 | 18.61 | A | O |
| ATOM | 1169 | N | GLY | A | 78 | 61.568 | −39.075 | −14.928 | 1.00 | 18.28 | A | N |
| ATOM | 1170 | CA | GLY | A | 78 | 62.057 | −40.134 | −15.802 | 1.00 | 18.20 | A | C |
| ATOM | 1173 | C | GLY | A | 78 | 62.696 | −41.279 | −15.040 | 1.00 | 18.14 | A | C |
| ATOM | 1174 | O | GLY | A | 78 | 62.502 | −42.445 | −15.386 | 1.00 | 18.30 | A | O |
| ATOM | 1176 | N | ALA | A | 79 | 63.458 | −40.944 | −14.001 | 1.00 | 18.02 | A | N |
| ATOM | 1177 | CA | ALA | A | 79 | 64.134 | −41.945 | −13.180 | 1.00 | 18.14 | A | C |
| ATOM | 1179 | CB | ALA | A | 79 | 65.142 | −41.280 | −12.258 | 1.00 | 18.16 | A | C |
| ATOM | 1183 | C | ALA | A | 79 | 63.134 | −42.763 | −12.369 | 1.00 | 18.13 | A | C |
| ATOM | 1184 | O | ALA | A | 79 | 63.227 | −43.991 | −12.308 | 1.00 | 18.34 | A | O |
| ATOM | 1186 | N | LEU | A | 80 | 62.179 | −42.073 | −11.754 | 1.00 | 18.13 | A | N |
| ATOM | 1187 | CA | LEU | A | 80 | 61.136 | −42.727 | −10.969 | 1.00 | 18.20 | A | C |
| ATOM | 1189 | CB | LEU | A | 80 | 60.348 | −41.693 | −10.161 | 1.00 | 17.90 | A | C |
| ATOM | 1192 | CG | LEU | A | 80 | 61.135 | −41.067 | −9.009 | 1.00 | 16.44 | A | C |
| ATOM | 1194 | CD1 | LEU | A | 80 | 60.478 | −39.790 | −8.526 | 1.00 | 15.42 | A | C |
| ATOM | 1198 | CD2 | LEU | A | 80 | 61.285 | −42.059 | −7.871 | 1.00 | 15.55 | A | C |
| ATOM | 1202 | C | LEU | A | 80 | 60.189 | −43.536 | −11.851 | 1.00 | 18.82 | A | C |
| ATOM | 1203 | O | LEU | A | 80 | 59.655 | −44.556 | −11.418 | 1.00 | 18.88 | A | O |
| ATOM | 1205 | N | ASP | A | 81 | 59.982 | −43.083 | −13.084 | 1.00 | 19.44 | A | N |
| ATOM | 1206 | CA | ASP | A | 81 | 59.149 | −43.819 | −14.033 | 1.00 | 20.08 | A | C |
| ATOM | 1208 | CB | ASP | A | 81 | 58.894 | −42.984 | −15.290 | 1.00 | 20.26 | A | C |
| ATOM | 1211 | CG | ASP | A | 81 | 57.690 | −43.464 | −16.067 | 1.00 | 21.37 | A | C |
| ATOM | 1212 | OD1 | ASP | A | 81 | 57.879 | −44.129 | −17.108 | 1.00 | 23.00 | A | O |
| ATOM | 1213 | OD2 | ASP | A | 81 | 56.554 | −43.186 | −15.624 | 1.00 | 22.87 | A | O |
| ATOM | 1214 | C | ASP | A | 81 | 59.810 | −45.149 | −14.406 | 1.00 | 20.30 | A | C |
| ATOM | 1215 | O | ASP | A | 81 | 59.133 | −46.174 | −14.523 | 1.00 | 19.67 | A | O |
| ATOM | 1217 | N | ARG | A | 82 | 61.131 | −45.116 | −14.583 | 1.00 | 20.83 | A | N |
| ATOM | 1218 | CA | ARG | A | 82 | 61.920 | −46.322 | −14.853 | 1.00 | 21.36 | A | C |
| ATOM | 1220 | CB | ARG | A | 82 | 63.315 | −45.951 | −15.375 | 1.00 | 21.67 | A | C |
| ATOM | 1223 | CG | ARG | A | 82 | 63.351 | −45.688 | −16.878 | 1.00 | 23.80 | A | C |
| ATOM | 1226 | CD | ARG | A | 82 | 64.738 | −45.280 | −17.376 | 1.00 | 25.75 | A | C |
| ATOM | 1229 | NE | ARG | A | 82 | 64.961 | −43.834 | −17.262 | 1.00 | 27.68 | A | N |
| ATOM | 1231 | CZ | ARG | A | 82 | 65.707 | −43.227 | −16.335 | 1.00 | 28.28 | A | C |
| ATOM | 1232 | NH1 | ARG | A | 82 | 66.349 | −43.915 | −15.389 | 1.00 | 27.87 | A | N |
| ATOM | 1235 | NH2 | ARG | A | 82 | 65.813 | −41.902 | −16.356 | 1.00 | 27.78 | A | N |
| ATOM | 1238 | C | ARG | A | 82 | 62.038 | −47.229 | −13.623 | 1.00 | 21.47 | A | C |
| ATOM | 1239 | O | ARG | A | 82 | 62.181 | −48.446 | −13.760 | 1.00 | 21.30 | A | O |
| ATOM | 1241 | N | PHE | A | 83 | 61.981 | −46.633 | −12.432 | 1.00 | 21.68 | A | N |
| ATOM | 1242 | CA | PHE | A | 83 | 61.970 | −47.385 | −11.171 | 1.00 | 21.75 | A | C |
| ATOM | 1244 | CB | PHE | A | 83 | 62.026 | −46.418 | −9.981 | 1.00 | 21.95 | A | C |
| ATOM | 1247 | CG | PHE | A | 83 | 62.097 | −47.097 | −8.637 | 1.00 | 21.67 | A | C |
| ATOM | 1248 | CD1 | PHE | A | 83 | 63.190 | −47.877 | −8.301 | 1.00 | 22.11 | A | C |
| ATOM | 1250 | CE1 | PHE | A | 83 | 63.268 | −48.500 | −7.064 | 1.00 | 21.50 | A | C |
| ATOM | 1252 | CZ | PHE | A | 83 | 62.250 | −48.336 | −6.144 | 1.00 | 21.28 | A | C |
| ATOM | 1254 | CE2 | PHE | A | 83 | 61.155 | −47.554 | −6.464 | 1.00 | 21.20 | A | C |
| ATOM | 1256 | CD2 | PHE | A | 83 | 61.082 | −46.936 | −7.704 | 1.00 | 21.17 | A | C |
| ATOM | 1258 | C | PHE | A | 83 | 60.733 | −48.277 | −11.059 | 1.00 | 21.71 | A | C |
| ATOM | 1259 | O | PHE | A | 83 | 60.838 | −49.450 | −10.696 | 1.00 | 21.49 | A | O |
| ATOM | 1261 | N | VAL | A | 84 | 59.567 | −47.708 | −11.365 | 1.00 | 21.86 | A | N |
| ATOM | 1262 | CA | VAL | A | 84 | 58.309 | −48.454 | −11.376 | 1.00 | 21.92 | A | C |
| ATOM | 1264 | CB | VAL | A | 84 | 57.087 | −47.509 | −11.496 | 1.00 | 21.73 | A | C |
| ATOM | 1266 | CG1 | VAL | A | 84 | 55.821 | −48.285 | −11.843 | 1.00 | 21.28 | A | C |
| ATOM | 1270 | CG2 | VAL | A | 84 | 56.898 | −46.731 | −10.209 | 1.00 | 20.78 | A | C |
| ATOM | 1274 | C | VAL | A | 84 | 58.297 | −49.451 | −12.531 | 1.00 | 22.75 | A | C |
| ATOM | 1275 | O | VAL | A | 84 | 58.070 | −50.646 | −12.323 | 1.00 | 22.96 | A | O |
| ATOM | 1277 | N | SER | A | 85 | 58.560 | −48.953 | −13.740 | 1.00 | 23.25 | A | N |
| ATOM | 1278 | CA | SER | A | 85 | 58.542 | −49.777 | −14.959 | 1.00 | 23.36 | A | C |
| ATOM | 1280 | CB | SER | A | 85 | 59.043 | −48.969 | −16.160 | 1.00 | 23.36 | A | C |
| ATOM | 1283 | OG | SER | A | 85 | 58.267 | −47.796 | −16.343 | 1.00 | 23.72 | A | O |
| ATOM | 1285 | C | SER | A | 85 | 59.363 | −51.059 | −14.828 | 1.00 | 23.09 | A | C |
| ATOM | 1286 | O | SER | A | 85 | 58.944 | −52.115 | −15.300 | 1.00 | 22.81 | A | O |
| ATOM | 1288 | N | SER | A | 86 | 60.521 | −50.958 | −14.176 | 1.00 | 23.31 | A | N |
| ATOM | 1289 | CA | SER | A | 86 | 61.421 | −52.099 | −13.992 | 1.00 | 23.83 | A | C |
| ATOM | 1291 | CB | SER | A | 86 | 62.880 | −51.626 | −14.021 | 1.00 | 23.95 | A | C |
| ATOM | 1294 | OG | SER | A | 86 | 63.188 | −50.822 | −12.894 | 1.00 | 24.38 | A | O |
| ATOM | 1296 | C | SER | A | 86 | 61.157 | −52.885 | −12.698 | 1.00 | 24.08 | A | C |
| ATOM | 1297 | O | SER | A | 86 | 61.966 | −53.729 | −12.312 | 1.00 | 24.00 | A | O |
| ATOM | 1299 | N | GLY | A | 87 | 60.037 | −52.604 | −12.032 | 1.00 | 24.44 | A | N |

TABLE 8-2-continued

Coordinates for L494P Structure

| | | | | | | | | | | | | |
|---|---|---|---|---|---|---|---|---|---|---|---|---|
| ATOM | 1300 | CA | GLY | A | 87 | 59.645 | −53.333 | −10.824 | 1.00 | 24.69 | A | C |
| ATOM | 1303 | C | GLY | A | 87 | 60.534 | −53.124 | −9.607 | 1.00 | 24.77 | A | C |
| ATOM | 1304 | O | GLY | A | 87 | 60.542 | −53.951 | −8.693 | 1.00 | 24.93 | A | O |
| ATOM | 1306 | N | GLY | A | 88 | 61.283 | −52.024 | −9.585 | 1.00 | 24.83 | A | N |
| ATOM | 1307 | CA | GLY | A | 88 | 62.142 | −51.701 | −8.449 | 1.00 | 24.84 | A | C |
| ATOM | 1310 | C | GLY | A | 88 | 61.331 | −51.396 | −7.203 | 1.00 | 24.89 | A | C |
| ATOM | 1311 | O | GLY | A | 88 | 61.688 | −51.824 | −6.104 | 1.00 | 24.71 | A | O |
| ATOM | 1313 | N | PHE | A | 89 | 60.235 | −50.657 | −7.386 | 1.00 | 24.99 | A | N |
| ATOM | 1314 | CA | PHE | A | 89 | 59.296 | −50.336 | −6.304 | 1.00 | 24.94 | A | C |
| ATOM | 1316 | CB | PHE | A | 89 | 58.218 | −49.363 | −6.802 | 1.00 | 25.23 | A | C |
| ATOM | 1319 | CG | PHE | A | 89 | 57.181 | −49.012 | −5.769 | 1.00 | 25.50 | A | C |
| ATOM | 1320 | CD1 | PHE | A | 89 | 57.546 | −48.380 | −4.588 | 1.00 | 25.76 | A | C |
| ATOM | 1322 | CE1 | PHE | A | 89 | 56.592 | −48.050 | −3.630 | 1.00 | 26.18 | A | C |
| ATOM | 1324 | CZ | PHE | A | 89 | 55.253 | −48.346 | −3.855 | 1.00 | 27.09 | A | C |
| ATOM | 1326 | CE2 | PHE | A | 89 | 54.874 | −48.971 | −5.033 | 1.00 | 27.63 | A | C |
| ATOM | 1328 | CD2 | PHE | A | 89 | 55.838 | −49.300 | −5.984 | 1.00 | 27.27 | A | C |
| ATOM | 1330 | C | PHE | A | 89 | 58.647 | −51.599 | −5.746 | 1.00 | 24.65 | A | C |
| ATOM | 1331 | O | PHE | A | 89 | 58.438 | −51.709 | −4.538 | 1.00 | 24.51 | A | O |
| ATOM | 1333 | N | ASP | A | 90 | 58.330 | −52.545 | −6.629 | 1.00 | 24.41 | A | N |
| ATOM | 1334 | CA | ASP | A | 90 | 57.825 | −53.851 | −6.207 | 1.00 | 24.29 | A | C |
| ATOM | 1336 | CB | ASP | A | 90 | 57.210 | −54.613 | −7.392 | 1.00 | 24.60 | A | C |
| ATOM | 1339 | CG | ASP | A | 90 | 56.123 | −55.595 | −6.962 | 1.00 | 25.71 | A | C |
| ATOM | 1340 | OD1 | ASP | A | 90 | 55.046 | −55.135 | −6.518 | 1.00 | 24.61 | A | O |
| ATOM | 1341 | OD2 | ASP | A | 90 | 56.341 | −56.822 | −7.078 | 1.00 | 27.27 | A | O |
| ATOM | 1342 | C | ASP | A | 90 | 58.946 | −54.677 | −5.563 | 1.00 | 23.50 | A | C |
| ATOM | 1343 | O | ASP | A | 90 | 58.687 | −55.508 | −4.694 | 1.00 | 23.34 | A | O |
| ATOM | 1345 | N | ALA | A | 91 | 60.185 | −54.439 | −5.992 | 1.00 | 22.93 | A | N |
| ATOM | 1346 | CA | ALA | A | 91 | 61.356 | −55.122 | −5.434 | 1.00 | 22.68 | A | C |
| ATOM | 1348 | CB | ALA | A | 91 | 62.574 | −54.900 | −6.326 | 1.00 | 22.43 | A | C |
| ATOM | 1352 | C | ALA | A | 91 | 61.666 | −54.683 | −3.999 | 1.00 | 22.49 | A | C |
| ATOM | 1353 | O | ALA | A | 91 | 61.957 | −55.520 | −3.142 | 1.00 | 22.56 | A | O |
| ATOM | 1355 | N | VAL | A | 92 | 61.600 | −53.377 | −3.741 | 1.00 | 22.18 | A | N |
| ATOM | 1356 | CA | VAL | A | 92 | 61.948 | −52.834 | −2.421 | 1.00 | 21.87 | A | C |
| ATOM | 1358 | CB | VAL | A | 92 | 62.228 | −51.304 | −2.465 | 1.00 | 22.06 | A | C |
| ATOM | 1360 | CG1 | VAL | A | 92 | 63.296 | −50.983 | −3.507 | 1.00 | 21.68 | A | C |
| ATOM | 1364 | CG2 | VAL | A | 92 | 60.952 | −50.515 | −2.735 | 1.00 | 22.62 | A | C |
| ATOM | 1368 | C | VAL | A | 92 | 60.890 | −53.133 | −1.351 | 1.00 | 21.46 | A | C |
| ATOM | 1369 | O | VAL | A | 92 | 61.237 | −53.335 | −0.189 | 1.00 | 21.07 | A | O |
| ATOM | 1371 | N | THR | A | 93 | 59.614 | −53.173 | −1.738 | 1.00 | 21.50 | A | N |
| ATOM | 1372 | CA | THR | A | 93 | 58.538 | −53.555 | −0.809 | 1.00 | 21.48 | A | C |
| ATOM | 1374 | CB | THR | A | 93 | 57.133 | −53.525 | −1.464 | 1.00 | 21.32 | A | C |
| ATOM | 1376 | OG1 | THR | A | 93 | 57.103 | −54.398 | −2.600 | 1.00 | 20.80 | A | O |
| ATOM | 1378 | CG2 | THR | A | 93 | 56.757 | −52.110 | −1.886 | 1.00 | 20.81 | A | C |
| ATOM | 1382 | C | THR | A | 93 | 58.770 | −54.947 | −0.226 | 1.00 | 21.77 | A | C |
| ATOM | 1383 | O | THR | A | 93 | 58.340 | −55.229 | 0.894 | 1.00 | 22.39 | A | O |
| ATOM | 1385 | N | LYS | A | 94 | 59.447 | −55.807 | −0.987 | 1.00 | 21.47 | A | N |
| ATOM | 1386 | CA | LYS | A | 94 | 59.797 | −57.146 | −0.523 | 1.00 | 21.19 | A | C |
| ATOM | 1388 | CB | LYS | A | 94 | 60.015 | −58.087 | −1.715 | 1.00 | 21.47 | A | C |
| ATOM | 1391 | CG | LYS | A | 94 | 58.821 | −58.222 | −2.660 | 1.00 | 22.94 | A | C |
| ATOM | 1394 | CD | LYS | A | 94 | 57.596 | −58.829 | −1.978 | 1.00 | 24.09 | A | C |
| ATOM | 1397 | CE | LYS | A | 94 | 56.432 | −58.970 | −2.950 | 1.00 | 24.08 | A | C |
| ATOM | 1400 | NZ | LYS | A | 94 | 55.133 | −59.149 | −2.242 | 1.00 | 24.08 | A | N |
| ATOM | 1404 | C | LYS | A | 94 | 61.042 | −57.168 | 0.368 | 1.00 | 20.63 | A | C |
| ATOM | 1405 | O | LYS | A | 94 | 61.150 | −58.036 | 1.233 | 1.00 | 20.30 | A | O |
| ATOM | 1407 | N | THR | A | 95 | 61.969 | −56.225 | 0.167 | 1.00 | 20.41 | A | N |
| ATOM | 1408 | CA | THR | A | 95 | 63.302 | −56.301 | 0.795 | 1.00 | 20.29 | A | C |
| ATOM | 1410 | CB | THR | A | 95 | 64.398 | −56.575 | −0.269 | 1.00 | 20.32 | A | C |
| ATOM | 1412 | OG1 | THR | A | 95 | 64.375 | −55.546 | −1.265 | 1.00 | 20.66 | A | O |
| ATOM | 1414 | CG2 | THR | A | 95 | 64.186 | −57.931 | −0.931 | 1.00 | 20.65 | A | C |
| ATOM | 1418 | C | THR | A | 95 | 63.784 | −55.102 | 1.631 | 1.00 | 19.83 | A | C |
| ATOM | 1419 | O | THR | A | 95 | 64.777 | −55.238 | 2.345 | 1.00 | 19.98 | A | O |
| ATOM | 1421 | N | SER | A | 96 | 63.120 | −53.946 | 1.555 | 1.00 | 19.31 | A | N |
| ATOM | 1422 | CA | SER | A | 96 | 63.620 | −52.739 | 2.247 | 1.00 | 18.82 | A | C |
| ATOM | 1424 | CB | SER | A | 96 | 64.689 | −52.051 | 1.391 | 1.00 | 18.43 | A | C |
| ATOM | 1427 | OG | SER | A | 96 | 65.227 | −50.917 | 2.053 | 1.00 | 17.09 | A | O |
| ATOM | 1429 | C | SER | A | 96 | 62.536 | −51.716 | 2.614 | 1.00 | 18.93 | A | C |
| ATOM | 1430 | O | SER | A | 96 | 61.889 | −51.146 | 1.734 | 1.00 | 19.15 | A | O |
| ATOM | 1432 | N | LEU | A | 97 | 62.364 | −51.474 | 3.916 | 1.00 | 18.65 | A | N |
| ATOM | 1433 | CA | LEU | A | 97 | 61.415 | −50.467 | 4.405 | 1.00 | 18.06 | A | C |
| ATOM | 1435 | CB | LEU | A | 97 | 61.285 | −50.521 | 5.935 | 1.00 | 17.85 | A | C |
| ATOM | 1438 | CG | LEU | A | 97 | 60.459 | −49.416 | 6.612 | 1.00 | 16.18 | A | C |
| ATOM | 1440 | CD1 | LEU | A | 97 | 59.070 | −49.303 | 6.001 | 1.00 | 15.61 | A | C |
| ATOM | 1444 | CD2 | LEU | A | 97 | 60.358 | −49.662 | 8.105 | 1.00 | 13.42 | A | C |
| ATOM | 1448 | C | LEU | A | 97 | 61.852 | −49.076 | 3.982 | 1.00 | 18.03 | A | C |
| ATOM | 1449 | O | LEU | A | 97 | 61.048 | −48.303 | 3.461 | 1.00 | 18.07 | A | O |
| ATOM | 1451 | N | HIS | A | 98 | 63.126 | −48.767 | 4.217 | 1.00 | 18.04 | A | N |
| ATOM | 1452 | CA | HIS | A | 98 | 63.707 | −47.478 | 3.831 | 1.00 | 18.00 | A | C |
| ATOM | 1454 | CB | HIS | A | 98 | 65.214 | −47.475 | 4.101 | 1.00 | 18.04 | A | C |

TABLE 8-2-continued

Coordinates for L494P Structure

| | | | | | | | | | | | | |
|---|---|---|---|---|---|---|---|---|---|---|---|---|
| ATOM | 1457 | CG | HIS | A | 98 | 65.911 | −46.239 | 3.626 | 1.00 | 18.24 | A | C |
| ATOM | 1458 | ND1 | HIS | A | 98 | 65.437 | −44.972 | 3.886 | 1.00 | 18.83 | A | N |
| ATOM | 1460 | CE1 | HIS | A | 98 | 66.252 | −44.080 | 3.351 | 1.00 | 20.11 | A | C |
| ATOM | 1462 | NE2 | HIS | A | 98 | 67.241 | −44.724 | 2.757 | 1.00 | 20.52 | A | N |
| ATOM | 1464 | CD2 | HIS | A | 98 | 67.051 | −46.075 | 2.915 | 1.00 | 19.92 | A | C |
| ATOM | 1466 | C | HIS | A | 98 | 63.437 | −47.172 | 2.360 | 1.00 | 17.56 | A | C |
| ATOM | 1467 | O | HIS | A | 98 | 62.942 | −46.095 | 2.019 | 1.00 | 17.27 | A | O |
| ATOM | 1469 | N | GLY | A | 99 | 63.761 | −48.135 | 1.502 | 1.00 | 17.20 | A | N |
| ATOM | 1470 | CA | GLY | A | 99 | 63.515 | −48.016 | 0.071 | 1.00 | 16.81 | A | C |
| ATOM | 1473 | C | GLY | A | 99 | 62.044 | −47.848 | −0.254 | 1.00 | 16.25 | A | C |
| ATOM | 1474 | O | GLY | A | 99 | 61.689 | −47.056 | −1.122 | 1.00 | 16.14 | A | O |
| ATOM | 1476 | N | THR | A | 100 | 61.192 | −48.592 | 0.449 | 1.00 | 15.87 | A | N |
| ATOM | 1477 | CA | THR | A | 100 | 59.742 | −48.502 | 0.257 | 1.00 | 15.58 | A | C |
| ATOM | 1479 | CB | THR | A | 100 | 59.001 | −49.660 | 0.962 | 1.00 | 15.34 | A | C |
| ATOM | 1481 | OG1 | THR | A | 100 | 59.592 | −50.906 | 0.583 | 1.00 | 14.29 | A | O |
| ATOM | 1483 | CG2 | THR | A | 100 | 57.525 | −49.672 | 0.583 | 1.00 | 14.51 | A | C |
| ATOM | 1487 | C | THR | A | 100 | 59.184 | −47.172 | 0.767 | 1.00 | 15.52 | A | C |
| ATOM | 1488 | O | THR | A | 100 | 58.246 | −46.634 | 0.186 | 1.00 | 15.09 | A | O |
| ATOM | 1490 | N | ALA | A | 101 | 59.768 | −46.652 | 1.846 | 1.00 | 15.65 | A | N |
| ATOM | 1491 | CA | ALA | A | 101 | 59.332 | −45.388 | 2.444 | 1.00 | 15.65 | A | C |
| ATOM | 1493 | CB | ALA | A | 101 | 59.822 | −45.290 | 3.884 | 1.00 | 15.54 | A | C |
| ATOM | 1497 | C | ALA | A | 101 | 59.814 | −44.183 | 1.638 | 1.00 | 15.54 | A | C |
| ATOM | 1498 | O | ALA | A | 101 | 59.057 | −43.237 | 1.409 | 1.00 | 15.42 | A | O |
| ATOM | 1500 | N | LEU | A | 102 | 61.076 | −44.218 | 1.219 | 1.00 | 15.41 | A | N |
| ATOM | 1501 | CA | LEU | A | 102 | 61.648 | −43.146 | 0.408 | 1.00 | 15.42 | A | C |
| ATOM | 1503 | CB | LEU | A | 102 | 63.157 | −43.355 | 0.241 | 1.00 | 15.36 | A | C |
| ATOM | 1506 | CG | LEU | A | 102 | 63.945 | −42.270 | −0.501 | 1.00 | 14.98 | A | C |
| ATOM | 1508 | CD1 | LEU | A | 102 | 63.702 | −40.900 | 0.116 | 1.00 | 15.72 | A | C |
| ATOM | 1512 | CD2 | LEU | A | 102 | 65.430 | −42.604 | −0.499 | 1.00 | 13.41 | A | C |
| ATOM | 1516 | C | LEU | A | 102 | 60.971 | −43.076 | −0.961 | 1.00 | 15.48 | A | C |
| ATOM | 1517 | O | LEU | A | 102 | 60.618 | −41.993 | −1.434 | 1.00 | 15.70 | A | O |
| ATOM | 1519 | N | SER | A | 103 | 60.789 | −44.237 | −1.585 | 1.00 | 15.25 | A | N |
| ATOM | 1520 | CA | SER | A | 103 | 60.193 | −44.320 | −2.919 | 1.00 | 15.14 | A | C |
| ATOM | 1522 | CB | SER | A | 103 | 60.410 | −45.711 | −3.516 | 1.00 | 15.40 | A | C |
| ATOM | 1525 | OG | SER | A | 103 | 59.767 | −46.707 | −2.738 | 1.00 | 16.19 | A | O |
| ATOM | 1527 | C | SER | A | 103 | 58.702 | −44.001 | −2.923 | 1.00 | 14.61 | A | C |
| ATOM | 1528 | O | SER | A | 103 | 58.181 | −43.506 | −3.919 | 1.00 | 14.62 | A | O |
| ATOM | 1530 | N | PHE | A | 104 | 58.019 | −44.307 | −1.822 | 1.00 | 14.22 | A | N |
| ATOM | 1531 | CA | PHE | A | 104 | 56.601 | −43.979 | −1.673 | 1.00 | 13.75 | A | C |
| ATOM | 1533 | CB | PHE | A | 104 | 56.071 | −44.474 | −0.323 | 1.00 | 13.69 | A | C |
| ATOM | 1536 | CG | PHE | A | 104 | 54.603 | −44.227 | −0.113 | 1.00 | 13.93 | A | C |
| ATOM | 1537 | CD1 | PHE | A | 104 | 53.687 | −45.255 | −0.272 | 1.00 | 14.16 | A | C |
| ATOM | 1539 | CE1 | PHE | A | 104 | 52.332 | −45.031 | −0.075 | 1.00 | 15.68 | A | C |
| ATOM | 1541 | CZ | PHE | A | 104 | 51.878 | −43.770 | 0.287 | 1.00 | 15.52 | A | C |
| ATOM | 1543 | CE2 | PHE | A | 104 | 52.780 | −42.737 | 0.450 | 1.00 | 15.16 | A | C |
| ATOM | 1545 | CD2 | PHE | A | 104 | 54.137 | −42.968 | 0.254 | 1.00 | 15.63 | A | C |
| ATOM | 1547 | C | PHE | A | 104 | 56.419 | −42.475 | −1.764 | 1.00 | 13.26 | A | C |
| ATOM | 1548 | O | PHE | A | 104 | 55.580 | −41.984 | −2.517 | 1.00 | 13.35 | A | O |
| ATOM | 1550 | N | ARG | A | 105 | 57.219 | −41.756 | −0.983 | 1.00 | 12.79 | A | N |
| ATOM | 1551 | CA | ARG | A | 105 | 57.129 | −40.305 | −0.889 | 1.00 | 12.24 | A | C |
| ATOM | 1553 | CB | ARG | A | 105 | 58.131 | −39.786 | 0.151 | 1.00 | 12.47 | A | C |
| ATOM | 1556 | CG | ARG | A | 105 | 58.043 | −38.289 | 0.429 | 1.00 | 12.65 | A | C |
| ATOM | 1559 | CD | ARG | A | 105 | 58.675 | −37.930 | 1.765 | 1.00 | 12.12 | A | C |
| ATOM | 1562 | NE | ARG | A | 105 | 60.085 | −38.315 | 1.836 | 1.00 | 12.56 | A | N |
| ATOM | 1564 | CZ | ARG | A | 105 | 61.099 | −37.626 | 1.307 | 1.00 | 12.59 | A | C |
| ATOM | 1565 | NH1 | ARG | A | 105 | 60.889 | −36.492 | 0.641 | 1.00 | 10.93 | A | N |
| ATOM | 1568 | NH2 | ARG | A | 105 | 62.342 | −38.081 | 1.442 | 1.00 | 13.27 | A | N |
| ATOM | 1571 | C | ARG | A | 105 | 57.377 | −39.646 | −2.240 | 1.00 | 11.50 | A | C |
| ATOM | 1572 | O | ARG | A | 105 | 56.522 | −38.911 | −2.739 | 1.00 | 11.41 | A | O |
| ATOM | 1574 | N | LEU | A | 106 | 58.538 | −39.929 | −2.828 | 1.00 | 10.65 | A | N |
| ATOM | 1575 | CA | LEU | A | 106 | 58.960 | −39.289 | −4.077 | 1.00 | 10.07 | A | C |
| ATOM | 1577 | CB | LEU | A | 106 | 60.342 | −39.797 | −4.503 | 1.00 | 9.65 | A | C |
| ATOM | 1580 | CG | LEU | A | 106 | 61.518 | −39.446 | −3.591 | 1.00 | 8.79 | A | C |
| ATOM | 1582 | CD1 | LEU | A | 106 | 62.798 | −40.057 | −4.123 | 1.00 | 7.06 | A | C |
| ATOM | 1586 | CD2 | LEU | A | 106 | 61.665 | −37.943 | −3.455 | 1.00 | 8.58 | A | C |
| ATOM | 1590 | C | LEU | A | 106 | 57.960 | −39.510 | −5.210 | 1.00 | 10.35 | A | C |
| ATOM | 1591 | O | LEU | A | 106 | 57.659 | −38.591 | −5.966 | 1.00 | 9.93 | A | O |
| ATOM | 1593 | N | LEU | A | 107 | 57.448 | −40.731 | −5.322 | 1.00 | 11.25 | A | N |
| ATOM | 1594 | CA | LEU | A | 107 | 56.482 | −41.059 | −6.364 | 1.00 | 11.96 | A | C |
| ATOM | 1596 | CB | LEU | A | 107 | 56.168 | −42.561 | −6.362 | 1.00 | 11.90 | A | C |
| ATOM | 1599 | CG | LEU | A | 107 | 57.282 | −43.462 | −6.910 | 1.00 | 10.93 | A | C |
| ATOM | 1601 | CD1 | LEU | A | 107 | 57.110 | −44.907 | −6.454 | 1.00 | 9.95 | A | C |
| ATOM | 1605 | CD2 | LEU | A | 107 | 57.338 | −43.384 | −8.426 | 1.00 | 9.78 | A | C |
| ATOM | 1609 | C | LEU | A | 107 | 55.211 | −40.227 | −6.190 | 1.00 | 12.95 | A | C |
| ATOM | 1610 | O | LEU | A | 107 | 54.855 | −39.443 | −7.073 | 1.00 | 13.19 | A | O |
| ATOM | 1612 | N | ARG | A | 108 | 54.552 | −40.368 | −5.041 | 1.00 | 13.67 | A | N |
| ATOM | 1613 | CA | ARG | A | 108 | 53.324 | −39.618 | −4.765 | 1.00 | 14.20 | A | C |
| ATOM | 1615 | CB | ARG | A | 108 | 52.790 | −39.925 | −3.364 | 1.00 | 14.17 | A | C |

TABLE 8-2-continued

Coordinates for L494P Structure

| | | | | | | | | | | | | |
|---|---|---|---|---|---|---|---|---|---|---|---|---|
| ATOM | 1618 | CG | ARG | A | 108 | 51.491 | −39.199 | −3.039 | 1.00 | 14.69 | A | C |
| ATOM | 1621 | CD | ARG | A | 108 | 50.825 | −39.745 | −1.794 | 1.00 | 15.20 | A | C |
| ATOM | 1624 | NE | ARG | A | 108 | 50.129 | −41.006 | −2.043 | 1.00 | 15.73 | A | N |
| ATOM | 1626 | CZ | ARG | A | 108 | 49.489 | −41.709 | −1.110 | 1.00 | 16.84 | A | C |
| ATOM | 1627 | NH1 | ARG | A | 108 | 49.452 | −41.284 | 0.152 | 1.00 | 18.23 | A | N |
| ATOM | 1630 | NH2 | ARG | A | 108 | 48.886 | −42.847 | −1.436 | 1.00 | 16.02 | A | N |
| ATOM | 1633 | C | ARG | A | 108 | 53.527 | −38.112 | −4.927 | 1.00 | 14.71 | A | C |
| ATOM | 1634 | O | ARG | A | 108 | 52.645 | −37.421 | −5.434 | 1.00 | 15.28 | A | O |
| ATOM | 1636 | N | GLN | A | 109 | 54.683 | −37.613 | −4.491 | 1.00 | 15.38 | A | N |
| ATOM | 1637 | CA | GLN | A | 109 | 55.061 | −36.209 | −4.704 | 1.00 | 15.97 | A | C |
| ATOM | 1639 | CB | GLN | A | 109 | 56.475 | −35.945 | −4.163 | 1.00 | 15.84 | A | C |
| ATOM | 1642 | CG | GLN | A | 109 | 57.029 | −34.541 | −4.425 | 1.00 | 14.14 | A | C |
| ATOM | 1645 | CD | GLN | A | 109 | 58.523 | −34.431 | −4.153 | 1.00 | 12.90 | A | C |
| ATOM | 1646 | OE1 | GLN | A | 109 | 59.146 | −35.355 | −3.631 | 1.00 | 11.02 | A | O |
| ATOM | 1647 | NE2 | GLN | A | 109 | 59.102 | −33.291 | −4.508 | 1.00 | 12.83 | A | N |
| ATOM | 1650 | C | GLN | A | 109 | 55.000 | −35.856 | −6.190 | 1.00 | 16.80 | A | C |
| ATOM | 1651 | O | GLN | A | 109 | 54.554 | −34.764 | −6.555 | 1.00 | 17.24 | A | O |
| ATOM | 1653 | N | HIS | A | 110 | 55.441 | −36.790 | −7.034 | 1.00 | 17.12 | A | N |
| ATOM | 1654 | CA | HIS | A | 110 | 55.471 | −36.593 | −8.484 | 1.00 | 17.38 | A | C |
| ATOM | 1656 | CB | HIS | A | 110 | 56.786 | −37.139 | −9.056 | 1.00 | 17.33 | A | C |
| ATOM | 1659 | CG | HIS | A | 110 | 57.991 | −36.346 | −8.656 | 1.00 | 16.17 | A | C |
| ATOM | 1660 | ND1 | HIS | A | 110 | 58.171 | −35.032 | −9.032 | 1.00 | 16.90 | A | N |
| ATOM | 1662 | CE1 | HIS | A | 110 | 59.317 | −34.590 | −8.545 | 1.00 | 16.88 | A | C |
| ATOM | 1664 | NE2 | HIS | A | 110 | 59.888 | −35.571 | −7.870 | 1.00 | 15.81 | A | N |
| ATOM | 1666 | CD2 | HIS | A | 110 | 59.080 | −36.681 | −7.926 | 1.00 | 14.86 | A | C |
| ATOM | 1668 | C | HIS | A | 110 | 54.264 | −37.210 | −9.211 | 1.00 | 17.87 | A | C |
| ATOM | 1669 | O | HIS | A | 110 | 54.390 | −37.690 | −10.344 | 1.00 | 17.97 | A | O |
| ATOM | 1671 | N | GLY | A | 111 | 53.101 | −37.208 | −8.557 | 1.00 | 18.23 | A | N |
| ATOM | 1672 | CA | GLY | A | 111 | 51.832 | −37.543 | −9.215 | 1.00 | 18.60 | A | C |
| ATOM | 1675 | C | GLY | A | 111 | 51.538 | −39.016 | −9.464 | 1.00 | 19.18 | A | C |
| ATOM | 1676 | O | GLY | A | 111 | 50.428 | −39.362 | −9.877 | 1.00 | 19.51 | A | O |
| ATOM | 1678 | N | PHE | A | 112 | 52.515 | −39.888 | −9.221 | 1.00 | 19.34 | A | N |
| ATOM | 1679 | CA | PHE | A | 112 | 52.326 | −41.326 | −9.398 | 1.00 | 19.07 | A | C |
| ATOM | 1681 | CB | PHE | A | 112 | 53.663 | −42.064 | −9.292 | 1.00 | 19.21 | A | C |
| ATOM | 1684 | CG | PHE | A | 112 | 54.544 | −41.904 | −10.495 | 1.00 | 20.15 | A | C |
| ATOM | 1685 | CD1 | PHE | A | 112 | 54.129 | −42.360 | −11.740 | 1.00 | 21.80 | A | C |
| ATOM | 1687 | CE1 | PHE | A | 112 | 54.945 | −42.227 | −12.855 | 1.00 | 22.75 | A | C |
| ATOM | 1689 | CZ | PHE | A | 112 | 56.195 | −41.642 | −12.730 | 1.00 | 23.18 | A | C |
| ATOM | 1691 | CE2 | PHE | A | 112 | 56.624 | −41.192 | −11.489 | 1.00 | 22.64 | A | C |
| ATOM | 1693 | CD2 | PHE | A | 112 | 55.800 | −41.326 | −10.380 | 1.00 | 21.27 | A | C |
| ATOM | 1695 | C | PHE | A | 112 | 51.369 | −41.887 | −8.357 | 1.00 | 18.69 | A | C |
| ATOM | 1696 | O | PHE | A | 112 | 51.144 | −41.275 | −7.313 | 1.00 | 18.60 | A | O |
| ATOM | 1698 | N | GLU | A | 113 | 50.817 | −43.060 | −8.645 | 1.00 | 18.61 | A | N |
| ATOM | 1699 | CA | GLU | A | 113 | 49.921 | −43.735 | −7.715 | 1.00 | 18.65 | A | C |
| ATOM | 1701 | CB | GLU | A | 113 | 48.699 | −44.292 | −8.447 | 1.00 | 18.82 | A | C |
| ATOM | 1704 | CG | GLU | A | 113 | 47.633 | −43.241 | −8.709 | 1.00 | 21.49 | A | C |
| ATOM | 1707 | CD | GLU | A | 113 | 46.566 | −43.700 | −9.687 | 1.00 | 25.30 | A | C |
| ATOM | 1708 | OE1 | GLU | A | 113 | 45.849 | −42.829 | −10.227 | 1.00 | 27.79 | A | O |
| ATOM | 1709 | OE2 | GLU | A | 113 | 46.440 | −44.923 | −9.917 | 1.00 | 27.48 | A | O |
| ATOM | 1710 | C | GLU | A | 113 | 50.648 | −44.841 | −6.959 | 1.00 | 18.07 | A | C |
| ATOM | 1711 | O | GLU | A | 113 | 50.854 | −45.939 | −7.483 | 1.00 | 18.36 | A | O |
| ATOM | 1713 | N | VAL | A | 114 | 51.060 | −44.521 | −5.735 | 1.00 | 17.12 | A | N |
| ATOM | 1714 | CA | VAL | A | 114 | 51.481 | −45.524 | −4.765 | 1.00 | 16.39 | A | C |
| ATOM | 1716 | CB | VAL | A | 114 | 52.750 | −45.101 | −4.008 | 1.00 | 15.83 | A | C |
| ATOM | 1718 | CG1 | VAL | A | 114 | 53.919 | −45.005 | −4.964 | 1.00 | 15.16 | A | C |
| ATOM | 1722 | CG2 | VAL | A | 114 | 52.533 | −43.784 | −3.276 | 1.00 | 15.50 | A | C |
| ATOM | 1726 | C | VAL | A | 114 | 50.335 | −45.721 | −3.781 | 1.00 | 16.53 | A | C |
| ATOM | 1727 | O | VAL | A | 114 | 49.538 | −44.810 | −3.572 | 1.00 | 16.32 | A | O |
| ATOM | 1729 | N | SER | A | 115 | 50.247 | −46.912 | −3.194 | 1.00 | 17.04 | A | N |
| ATOM | 1730 | CA | SER | A | 115 | 49.195 | −47.223 | −2.228 | 1.00 | 17.55 | A | C |
| ATOM | 1732 | CB | SER | A | 115 | 48.308 | −48.355 | −2.743 | 1.00 | 17.82 | A | C |
| ATOM | 1735 | OG | SER | A | 115 | 47.197 | −48.552 | −1.884 | 1.00 | 18.67 | A | O |
| ATOM | 1737 | C | SER | A | 115 | 49.781 | −47.609 | −0.876 | 1.00 | 17.69 | A | C |
| ATOM | 1738 | O | SER | A | 115 | 50.899 | −48.124 | −0.795 | 1.00 | 17.50 | A | O |
| ATOM | 1740 | N | GLN | A | 116 | 49.006 | −47.374 | 0.181 | 1.00 | 17.82 | A | N |
| ATOM | 1741 | CA | GLN | A | 116 | 49.454 | −47.623 | 1.555 | 1.00 | 17.95 | A | C |
| ATOM | 1743 | CB | GLN | A | 116 | 48.420 | −47.101 | 2.559 | 1.00 | 17.90 | A | C |
| ATOM | 1746 | CG | GLN | A | 116 | 47.068 | −47.810 | 2.515 | 1.00 | 18.34 | A | C |
| ATOM | 1749 | CD | GLN | A | 116 | 46.133 | −47.374 | 3.628 | 1.00 | 18.56 | A | C |
| ATOM | 1750 | OE1 | GLN | A | 116 | 46.556 | −46.788 | 4.625 | 1.00 | 17.49 | A | O |
| ATOM | 1751 | NE2 | GLN | A | 116 | 44.849 | −47.667 | 3.464 | 1.00 | 20.40 | A | N |
| ATOM | 1754 | C | GLN | A | 116 | 49.769 | −49.092 | 1.862 | 1.00 | 18.13 | A | C |
| ATOM | 1755 | O | GLN | A | 116 | 50.414 | −49.388 | 2.869 | 1.00 | 18.57 | A | O |
| ATOM | 1757 | N | GLU | A | 117 | 49.310 | −50.003 | 1.004 | 1.00 | 17.94 | A | N |
| ATOM | 1758 | CA | GLU | A | 117 | 49.597 | −51.434 | 1.157 | 1.00 | 17.83 | A | C |
| ATOM | 1760 | CB | GLU | A | 117 | 48.454 | −52.279 | 0.566 | 1.00 | 17.98 | A | C |
| ATOM | 1763 | CG | GLU | A | 117 | 48.249 | −52.140 | −0.952 | 1.00 | 19.01 | A | C |
| ATOM | 1766 | CD | GLU | A | 117 | 46.780 | −52.207 | −1.378 | 1.00 | 20.24 | A | C |

TABLE 8-2-continued

Coordinates for L494P Structure

| | | | | | | | | | | | | |
|---|---|---|---|---|---|---|---|---|---|---|---|---|
| ATOM | 1767 | OE1 | GLU | A | 117 | 45.909 | −51.625 | −0.689 | 1.00 | 19.48 | A | O |
| ATOM | 1768 | OE2 | GLU | A | 117 | 46.500 | −52.832 | −2.424 | 1.00 | 20.64 | A | O |
| ATOM | 1769 | C | GLU | A | 117 | 50.956 | −51.847 | 0.566 | 1.00 | 17.49 | A | C |
| ATOM | 1770 | O | GLU | A | 117 | 51.215 | −53.034 | 0.373 | 1.00 | 17.44 | A | O |
| ATOM | 1772 | N | ALA | A | 118 | 51.817 | −50.870 | 0.282 | 1.00 | 17.38 | A | N |
| ATOM | 1773 | CA | ALA | A | 118 | 53.218 | −51.141 | −0.044 | 1.00 | 17.57 | A | C |
| ATOM | 1775 | CB | ALA | A | 118 | 53.836 | −49.962 | −0.770 | 1.00 | 17.88 | A | C |
| ATOM | 1779 | C | ALA | A | 118 | 54.002 | −51.431 | 1.228 | 1.00 | 17.50 | A | C |
| ATOM | 1780 | O | ALA | A | 118 | 55.040 | −52.090 | 1.184 | 1.00 | 17.67 | A | O |
| ATOM | 1782 | N | PHE | A | 119 | 53.498 | −50.929 | 2.354 | 1.00 | 17.52 | A | N |
| ATOM | 1783 | CA | PHE | A | 119 | 54.126 | −51.132 | 3.655 | 1.00 | 17.68 | A | C |
| ATOM | 1785 | CB | PHE | A | 119 | 53.830 | −49.945 | 4.578 | 1.00 | 17.42 | A | C |
| ATOM | 1788 | CG | PHE | A | 119 | 54.301 | −48.622 | 4.038 | 1.00 | 15.73 | A | C |
| ATOM | 1789 | CD1 | PHE | A | 119 | 53.399 | −47.701 | 3.526 | 1.00 | 14.47 | A | C |
| ATOM | 1791 | CE1 | PHE | A | 119 | 53.833 | −46.484 | 3.029 | 1.00 | 15.03 | A | C |
| ATOM | 1793 | CZ | PHE | A | 119 | 55.181 | −46.175 | 3.039 | 1.00 | 15.34 | A | C |
| ATOM | 1795 | CE2 | PHE | A | 119 | 56.091 | −47.088 | 3.544 | 1.00 | 14.74 | A | C |
| ATOM | 1797 | CD2 | PHE | A | 119 | 55.649 | −48.301 | 4.040 | 1.00 | 14.46 | A | C |
| ATOM | 1799 | C | PHE | A | 119 | 53.666 | −52.422 | 4.336 | 1.00 | 18.67 | A | C |
| ATOM | 1800 | O | PHE | A | 119 | 54.193 | −52.782 | 5.390 | 1.00 | 18.41 | A | O |
| ATOM | 1802 | N | SER | A | 120 | 52.693 | −53.112 | 3.735 | 1.00 | 20.10 | A | N |
| ATOM | 1803 | CA | SER | A | 120 | 52.070 | −54.302 | 4.342 | 1.00 | 20.78 | A | C |
| ATOM | 1805 | CB | SER | A | 120 | 50.966 | −54.859 | 3.433 | 1.00 | 20.80 | A | C |
| ATOM | 1808 | OG | SER | A | 120 | 51.505 | −55.402 | 2.240 | 1.00 | 21.10 | A | O |
| ATOM | 1810 | C | SER | A | 120 | 53.062 | −55.417 | 4.679 | 1.00 | 21.20 | A | C |
| ATOM | 1811 | O | SER | A | 120 | 52.863 | −56.152 | 5.645 | 1.00 | 21.27 | A | O |
| ATOM | 1813 | N | GLY | A | 121 | 54.121 | −55.542 | 3.884 | 1.00 | 22.05 | A | N |
| ATOM | 1814 | CA | GLY | A | 121 | 55.175 | −56.517 | 4.156 | 1.00 | 22.98 | A | C |
| ATOM | 1817 | C | GLY | A | 121 | 55.878 | −56.295 | 5.487 | 1.00 | 23.82 | A | C |
| ATOM | 1818 | O | GLY | A | 121 | 56.330 | −57.252 | 6.121 | 1.00 | 23.57 | A | O |
| ATOM | 1820 | N | PHE | A | 122 | 55.946 | −55.034 | 5.918 | 1.00 | 24.93 | A | N |
| ATOM | 1821 | CA | PHE | A | 122 | 56.665 | −54.646 | 7.137 | 1.00 | 25.54 | A | C |
| ATOM | 1823 | CB | PHE | A | 122 | 57.384 | −53.304 | 6.922 | 1.00 | 25.57 | A | C |
| ATOM | 1826 | CG | PHE | A | 122 | 58.118 | −53.209 | 5.610 | 1.00 | 25.40 | A | C |
| ATOM | 1827 | CD1 | PHE | A | 122 | 59.366 | −53.796 | 5.448 | 1.00 | 26.67 | A | C |
| ATOM | 1829 | CE1 | PHE | A | 122 | 60.042 | −53.710 | 4.235 | 1.00 | 26.81 | A | C |
| ATOM | 1831 | CZ | PHE | A | 122 | 59.467 | −53.034 | 3.170 | 1.00 | 26.20 | A | C |
| ATOM | 1833 | CE2 | PHE | A | 122 | 58.221 | −52.443 | 3.322 | 1.00 | 25.77 | A | C |
| ATOM | 1835 | CD2 | PHE | A | 122 | 57.554 | −52.534 | 4.536 | 1.00 | 24.71 | A | C |
| ATOM | 1837 | C | PHE | A | 122 | 55.734 | −54.560 | 8.358 | 1.00 | 26.09 | A | C |
| ATOM | 1838 | O | PHE | A | 122 | 55.717 | −53.553 | 9.074 | 1.00 | 26.28 | A | O |
| ATOM | 1840 | N | LYS | A | 123 | 54.964 | −55.622 | 8.587 | 1.00 | 26.57 | A | N |
| ATOM | 1841 | CA | LYS | A | 123 | 54.072 | −55.719 | 9.745 | 1.00 | 27.02 | A | C |
| ATOM | 1843 | CB | LYS | A | 123 | 52.632 | −55.359 | 9.349 | 1.00 | 27.12 | A | C |
| ATOM | 1846 | CG | LYS | A | 123 | 52.428 | −53.873 | 9.013 | 1.00 | 28.30 | A | C |
| ATOM | 1849 | CD | LYS | A | 123 | 51.208 | −53.615 | 8.116 | 1.00 | 30.27 | A | C |
| ATOM | 1852 | CE | LYS | A | 123 | 49.967 | −53.187 | 8.895 | 1.00 | 30.83 | A | C |
| ATOM | 1855 | NZ | LYS | A | 123 | 50.115 | −51.843 | 9.535 | 1.00 | 30.44 | A | N |
| ATOM | 1859 | C | LYS | A | 123 | 54.142 | −57.139 | 10.313 | 1.00 | 27.21 | A | C |
| ATOM | 1860 | O | LYS | A | 123 | 54.429 | −58.094 | 9.585 | 1.00 | 27.37 | A | O |
| ATOM | 1862 | N | ASP | A | 124 | 53.888 | −57.272 | 11.613 | 1.00 | 27.19 | A | N |
| ATOM | 1863 | CA | ASP | A | 124 | 53.936 | −58.576 | 12.282 | 1.00 | 26.97 | A | C |
| ATOM | 1865 | CB | ASP | A | 124 | 54.208 | −58.395 | 13.790 | 1.00 | 26.80 | A | C |
| ATOM | 1868 | CG | ASP | A | 124 | 53.015 | −57.829 | 14.555 | 1.00 | 26.01 | A | C |
| ATOM | 1869 | OD1 | ASP | A | 124 | 52.076 | −57.288 | 13.930 | 1.00 | 23.03 | A | O |
| ATOM | 1870 | OD2 | ASP | A | 124 | 53.020 | −57.930 | 15.800 | 1.00 | 25.54 | A | O |
| ATOM | 1871 | C | ASP | A | 124 | 52.647 | −59.374 | 12.014 | 1.00 | 27.07 | A | C |
| ATOM | 1872 | O | ASP | A | 124 | 51.904 | −59.059 | 11.079 | 1.00 | 26.95 | A | O |
| ATOM | 1874 | N | GLN | A | 125 | 52.393 | −60.409 | 12.816 | 1.00 | 27.04 | A | N |
| ATOM | 1875 | CA | GLN | A | 125 | 51.141 | −61.169 | 12.730 | 1.00 | 26.85 | A | C |
| ATOM | 1877 | CB | GLN | A | 125 | 51.124 | −62.297 | 13.761 | 1.00 | 26.80 | A | C |
| ATOM | 1880 | CG | GLN | A | 125 | 52.054 | −63.450 | 13.455 | 1.00 | 26.80 | A | C |
| ATOM | 1883 | CD | GLN | A | 125 | 51.830 | −64.626 | 14.386 | 1.00 | 26.65 | A | C |
| ATOM | 1884 | OE1 | GLN | A | 125 | 51.287 | −64.469 | 15.482 | 1.00 | 25.80 | A | O |
| ATOM | 1885 | NE2 | GLN | A | 125 | 52.242 | −65.812 | 13.952 | 1.00 | 26.55 | A | N |
| ATOM | 1888 | C | GLN | A | 125 | 49.908 | −60.293 | 12.956 | 1.00 | 26.80 | A | C |
| ATOM | 1889 | O | GLN | A | 125 | 48.889 | −60.462 | 12.283 | 1.00 | 26.98 | A | O |
| ATOM | 1891 | N | ASN | A | 126 | 50.012 | −59.369 | 13.910 | 1.00 | 26.46 | A | N |
| ATOM | 1892 | CA | ASN | A | 126 | 48.880 | −58.542 | 14.337 | 1.00 | 26.12 | A | C |
| ATOM | 1894 | CB | ASN | A | 126 | 49.113 | −58.030 | 15.762 | 1.00 | 25.97 | A | C |
| ATOM | 1897 | CG | ASN | A | 126 | 48.963 | −59.117 | 16.804 | 1.00 | 25.81 | A | C |
| ATOM | 1898 | OD1 | ASN | A | 126 | 48.186 | −58.979 | 17.748 | 1.00 | 26.53 | A | O |
| ATOM | 1899 | ND2 | ASN | A | 126 | 49.702 | −60.209 | 16.637 | 1.00 | 25.44 | A | N |
| ATOM | 1902 | C | ASN | A | 126 | 48.554 | −57.354 | 13.429 | 1.00 | 26.03 | A | C |
| ATOM | 1903 | O | ASN | A | 126 | 47.496 | −56.744 | 13.575 | 1.00 | 26.32 | A | O |
| ATOM | 1905 | N | GLY | A | 127 | 49.445 | −57.027 | 12.497 | 1.00 | 25.72 | A | N |
| ATOM | 1906 | CA | GLY | A | 127 | 49.262 | −55.850 | 11.646 | 1.00 | 25.62 | A | C |
| ATOM | 1909 | C | GLY | A | 127 | 49.743 | −54.571 | 12.316 | 1.00 | 25.62 | A | C |

TABLE 8-2-continued

Coordinates for L494P Structure

| | | | | | | | | | | | | |
|---|---|---|---|---|---|---|---|---|---|---|---|---|
| ATOM | 1910 | O | GLY | A | 127 | 49.235 | −53.481 | 12.040 | 1.00 | 25.98 | A | O |
| ATOM | 1912 | N | ASN | A | 128 | 50.712 | −54.716 | 13.216 | 1.00 | 25.32 | A | N |
| ATOM | 1913 | CA | ASN | A | 128 | 51.451 | −53.590 | 13.771 | 1.00 | 24.58 | A | C |
| ATOM | 1915 | CB | ASN | A | 128 | 51.410 | −53.617 | 15.298 | 1.00 | 24.48 | A | C |
| ATOM | 1918 | CG | ASN | A | 128 | 49.992 | −53.673 | 15.841 | 1.00 | 24.48 | A | C |
| ATOM | 1919 | OD1 | ASN | A | 128 | 49.100 | −52.975 | 15.355 | 1.00 | 24.27 | A | O |
| ATOM | 1920 | ND2 | ASN | A | 128 | 49.778 | −54.508 | 16.850 | 1.00 | 23.51 | A | N |
| ATOM | 1923 | C | ASN | A | 128 | 52.881 | −53.709 | 13.269 | 1.00 | 24.17 | A | C |
| ATOM | 1924 | O | ASN | A | 128 | 53.380 | −54.819 | 13.064 | 1.00 | 23.94 | A | O |
| ATOM | 1926 | N | PHE | A | 129 | 53.538 | −52.574 | 13.064 | 1.00 | 23.75 | A | N |
| ATOM | 1927 | CA | PHE | A | 129 | 54.868 | −52.567 | 12.453 | 1.00 | 23.39 | A | C |
| ATOM | 1929 | CB | PHE | A | 129 | 55.330 | −51.134 | 12.181 | 1.00 | 23.51 | A | C |
| ATOM | 1932 | CG | PHE | A | 129 | 54.571 | −50.461 | 11.073 | 1.00 | 23.75 | A | C |
| ATOM | 1933 | CD1 | PHE | A | 129 | 53.351 | −49.843 | 11.322 | 1.00 | 23.30 | A | C |
| ATOM | 1935 | CE1 | PHE | A | 129 | 52.645 | −49.226 | 10.300 | 1.00 | 23.78 | A | C |
| ATOM | 1937 | CZ | PHE | A | 129 | 53.157 | −49.223 | 9.011 | 1.00 | 24.34 | A | C |
| ATOM | 1939 | CE2 | PHE | A | 129 | 54.371 | −49.841 | 8.748 | 1.00 | 24.80 | A | C |
| ATOM | 1941 | CD2 | PHE | A | 129 | 55.071 | −50.456 | 9.777 | 1.00 | 24.15 | A | C |
| ATOM | 1943 | C | PHE | A | 129 | 55.881 | −53.315 | 13.320 | 1.00 | 22.72 | A | C |
| ATOM | 1944 | O | PHE | A | 129 | 55.797 | −53.289 | 14.549 | 1.00 | 22.69 | A | O |
| ATOM | 1946 | N | LEU | A | 130 | 56.821 | −53.997 | 12.674 | 1.00 | 21.98 | A | N |
| ATOM | 1947 | CA | LEU | A | 130 | 57.774 | −54.833 | 13.395 | 1.00 | 21.77 | A | C |
| ATOM | 1949 | CB | LEU | A | 130 | 58.741 | −55.532 | 12.430 | 1.00 | 21.51 | A | C |
| ATOM | 1952 | CG | LEU | A | 130 | 58.233 | −56.805 | 11.749 | 1.00 | 20.32 | A | C |
| ATOM | 1954 | CD1 | LEU | A | 130 | 59.185 | −57.238 | 10.642 | 1.00 | 18.63 | A | C |
| ATOM | 1958 | CD2 | LEU | A | 130 | 58.049 | −57.920 | 12.767 | 1.00 | 18.91 | A | C |
| ATOM | 1962 | C | LEU | A | 130 | 58.559 | −54.008 | 14.406 | 1.00 | 21.98 | A | C |
| ATOM | 1963 | O | LEU | A | 130 | 59.271 | −53.079 | 14.033 | 1.00 | 22.04 | A | O |
| ATOM | 1965 | N | GLU | A | 131 | 58.404 | −54.344 | 15.685 | 1.00 | 22.19 | A | N |
| ATOM | 1966 | CA | GLU | A | 131 | 59.208 | −53.755 | 16.756 | 1.00 | 22.55 | A | C |
| ATOM | 1968 | CB | GLU | A | 131 | 59.141 | −54.649 | 18.004 | 1.00 | 22.91 | A | C |
| ATOM | 1971 | CG | GLU | A | 131 | 60.010 | −54.215 | 19.194 | 1.00 | 23.48 | A | C |
| ATOM | 1974 | CD | GLU | A | 131 | 59.514 | −52.953 | 19.885 | 1.00 | 24.94 | A | C |
| ATOM | 1975 | OE1 | GLU | A | 131 | 58.423 | −52.451 | 19.536 | 1.00 | 26.88 | A | O |
| ATOM | 1976 | OE2 | GLU | A | 131 | 60.221 | −52.463 | 20.790 | 1.00 | 25.13 | A | O |
| ATOM | 1977 | C | GLU | A | 131 | 60.659 | −53.593 | 16.307 | 1.00 | 22.63 | A | C |
| ATOM | 1978 | O | GLU | A | 131 | 61.214 | −52.497 | 16.355 | 1.00 | 22.79 | A | O |
| ATOM | 1980 | N | ASN | A | 132 | 61.246 | −54.693 | 15.839 | 1.00 | 22.67 | A | N |
| ATOM | 1981 | CA | ASN | A | 132 | 62.659 | −54.740 | 15.447 | 1.00 | 22.65 | A | C |
| ATOM | 1983 | CB | ASN | A | 132 | 63.069 | −56.179 | 15.101 | 1.00 | 22.74 | A | C |
| ATOM | 1986 | CG | ASN | A | 132 | 62.220 | −56.785 | 13.992 | 1.00 | 24.12 | A | C |
| ATOM | 1987 | OD1 | ASN | A | 132 | 62.359 | −56.433 | 12.818 | 1.00 | 24.57 | A | O |
| ATOM | 1988 | ND2 | ASN | A | 132 | 61.339 | −57.710 | 14.362 | 1.00 | 25.30 | A | N |
| ATOM | 1991 | C | ASN | A | 132 | 63.074 | −53.793 | 14.313 | 1.00 | 22.61 | A | C |
| ATOM | 1992 | O | ASN | A | 132 | 64.266 | −53.662 | 14.034 | 1.00 | 23.15 | A | O |
| ATOM | 1994 | N | LEU | A | 133 | 62.110 | −53.141 | 13.661 | 1.00 | 22.44 | A | N |
| ATOM | 1995 | CA | LEU | A | 133 | 62.421 | −52.087 | 12.682 | 1.00 | 22.59 | A | C |
| ATOM | 1997 | CB | LEU | A | 133 | 61.274 | −51.905 | 11.677 | 1.00 | 22.57 | A | C |
| ATOM | 2000 | CG | LEU | A | 133 | 61.086 | −53.023 | 10.646 | 1.00 | 22.37 | A | C |
| ATOM | 2002 | CD1 | LEU | A | 133 | 59.755 | −52.870 | 9.926 | 1.00 | 20.95 | A | C |
| ATOM | 2006 | CD2 | LEU | A | 133 | 62.236 | −53.049 | 9.647 | 1.00 | 21.48 | A | C |
| ATOM | 2010 | C | LEU | A | 133 | 62.755 | −50.743 | 13.347 | 1.00 | 22.64 | A | C |
| ATOM | 2011 | O | LEU | A | 133 | 63.043 | −49.766 | 12.656 | 1.00 | 22.50 | A | O |
| ATOM | 2013 | N | LYS | A | 134 | 62.710 | −50.695 | 14.679 | 1.00 | 22.83 | A | N |
| ATOM | 2014 | CA | LYS | A | 134 | 63.148 | −49.518 | 15.435 | 1.00 | 22.96 | A | C |
| ATOM | 2016 | CB | LYS | A | 134 | 62.736 | −49.645 | 16.909 | 1.00 | 22.77 | A | C |
| ATOM | 2019 | CG | LYS | A | 134 | 63.555 | −50.675 | 17.698 | 1.00 | 22.69 | A | C |
| ATOM | 2022 | CD | LYS | A | 134 | 62.959 | −50.982 | 19.064 | 1.00 | 21.51 | A | C |
| ATOM | 2025 | CE | LYS | A | 134 | 63.861 | −51.921 | 19.855 | 1.00 | 19.87 | A | C |
| ATOM | 2028 | NZ | LYS | A | 134 | 63.358 | −52.166 | 21.234 | 1.00 | 19.19 | A | N |
| ATOM | 2032 | C | LYS | A | 134 | 64.667 | −49.311 | 15.350 | 1.00 | 23.33 | A | C |
| ATOM | 2033 | O | LYS | A | 134 | 65.152 | −48.189 | 15.500 | 1.00 | 23.47 | A | O |
| ATOM | 2035 | N | GLU | A | 135 | 65.410 | −50.393 | 15.118 | 1.00 | 23.60 | A | N |
| ATOM | 2036 | CA | GLU | A | 135 | 66.874 | −50.347 | 15.129 | 1.00 | 23.76 | A | C |
| ATOM | 2038 | CB | GLU | A | 135 | 67.465 | −51.736 | 15.424 | 1.00 | 23.98 | A | C |
| ATOM | 2041 | CG | GLU | A | 135 | 66.893 | −52.454 | 16.662 | 1.00 | 24.91 | A | C |
| ATOM | 2044 | CD | GLU | A | 135 | 67.236 | −51.779 | 17.991 | 1.00 | 26.21 | A | C |
| ATOM | 2045 | OE1 | GLU | A | 135 | 67.594 | −50.581 | 18.003 | 1.00 | 25.91 | A | O |
| ATOM | 2046 | OE2 | GLU | A | 135 | 67.140 | −52.457 | 19.037 | 1.00 | 26.26 | A | O |
| ATOM | 2047 | C | GLU | A | 135 | 67.461 | −49.797 | 13.826 | 1.00 | 23.56 | A | C |
| ATOM | 2048 | O | GLU | A | 135 | 68.641 | −49.440 | 13.785 | 1.00 | 23.61 | A | O |
| ATOM | 2050 | N | ASP | A | 136 | 66.648 | −49.739 | 12.770 | 1.00 | 23.07 | A | N |
| ATOM | 2051 | CA | ASP | A | 136 | 67.043 | −49.103 | 11.511 | 1.00 | 22.73 | A | C |
| ATOM | 2053 | CB | ASP | A | 136 | 66.509 | −49.903 | 10.315 | 1.00 | 22.88 | A | C |
| ATOM | 2056 | CG | ASP | A | 136 | 67.141 | −49.489 | 8.990 | 1.00 | 23.31 | A | C |
| ATOM | 2057 | OD1 | ASP | A | 136 | 67.675 | −48.364 | 8.882 | 1.00 | 24.29 | A | O |
| ATOM | 2058 | OD2 | ASP | A | 136 | 67.096 | −50.301 | 8.043 | 1.00 | 24.88 | A | O |
| ATOM | 2059 | C | ASP | A | 136 | 66.509 | −47.671 | 11.503 | 1.00 | 22.28 | A | C |

TABLE 8-2-continued

| Coordinates for L494P Structure | | | | | | | | | | | | |
|---|---|---|---|---|---|---|---|---|---|---|---|---|
| ATOM | 2060 | O | ASP | A | 136 | 65.448 | −47.392 | 10.943 | 1.00 | 22.30 | A | O |
| ATOM | 2062 | N | ILE | A | 137 | 67.263 | −46.765 | 12.119 | 1.00 | 21.98 | A | N |
| ATOM | 2063 | CA | ILE | A | 137 | 66.813 | −45.385 | 12.337 | 1.00 | 22.01 | A | C |
| ATOM | 2065 | CB | ILE | A | 137 | 67.780 | −44.618 | 13.279 | 1.00 | 21.91 | A | C |
| ATOM | 2067 | CG1 | ILE | A | 137 | 67.605 | −45.087 | 14.730 | 1.00 | 22.58 | A | C |
| ATOM | 2070 | CD1 | ILE | A | 137 | 68.188 | −46.460 | 15.030 | 1.00 | 22.59 | A | C |
| ATOM | 2074 | CG2 | ILE | A | 137 | 67.539 | −43.117 | 13.210 | 1.00 | 21.61 | A | C |
| ATOM | 2078 | C | ILE | A | 137 | 66.631 | −44.612 | 11.026 | 1.00 | 22.13 | A | C |
| ATOM | 2079 | O | ILE | A | 137 | 65.838 | −43.667 | 10.958 | 1.00 | 21.88 | A | O |
| ATOM | 2081 | N | LYS | A | 138 | 67.362 | −45.025 | 9.992 | 1.00 | 22.24 | A | N |
| ATOM | 2082 | CA | LYS | A | 138 | 67.242 | −44.431 | 8.659 | 1.00 | 21.88 | A | C |
| ATOM | 2084 | CB | LYS | A | 138 | 68.324 | −44.994 | 7.727 | 1.00 | 21.96 | A | C |
| ATOM | 2087 | CG | LYS | A | 138 | 68.724 | −44.056 | 6.601 | 1.00 | 23.45 | A | C |
| ATOM | 2090 | CD | LYS | A | 138 | 69.512 | −44.788 | 5.522 | 1.00 | 25.55 | A | C |
| ATOM | 2093 | CE | LYS | A | 138 | 70.339 | −43.831 | 4.674 | 1.00 | 26.38 | A | C |
| ATOM | 2096 | NZ | LYS | A | 138 | 71.460 | −43.222 | 5.449 | 1.00 | 28.11 | A | N |
| ATOM | 2100 | C | LYS | A | 138 | 65.854 | −44.689 | 8.062 | 1.00 | 21.05 | A | C |
| ATOM | 2101 | O | LYS | A | 138 | 65.277 | −43.812 | 7.416 | 1.00 | 20.86 | A | O |
| ATOM | 2103 | N | ALA | A | 139 | 65.327 | −45.890 | 8.292 | 1.00 | 20.37 | A | N |
| ATOM | 2104 | CA | ALA | A | 139 | 64.023 | −46.291 | 7.760 | 1.00 | 19.96 | A | C |
| ATOM | 2106 | CB | ALA | A | 139 | 63.890 | −47.811 | 7.792 | 1.00 | 19.84 | A | C |
| ATOM | 2110 | C | ALA | A | 139 | 62.856 | −45.639 | 8.510 | 1.00 | 19.48 | A | C |
| ATOM | 2111 | O | ALA | A | 139 | 61.856 | −45.256 | 7.897 | 1.00 | 19.09 | A | O |
| ATOM | 2113 | N | ILE | A | 140 | 62.987 | −45.518 | 9.830 | 1.00 | 18.99 | A | N |
| ATOM | 2114 | CA | ILE | A | 140 | 61.946 | −44.902 | 10.659 | 1.00 | 18.78 | A | C |
| ATOM | 2116 | CB | ILE | A | 140 | 62.266 | −45.017 | 12.166 | 1.00 | 18.67 | A | C |
| ATOM | 2118 | CG1 | ILE | A | 140 | 62.385 | −46.485 | 12.596 | 1.00 | 18.06 | A | C |
| ATOM | 2121 | CD1 | ILE | A | 140 | 61.112 | −47.284 | 12.435 | 1.00 | 18.60 | A | C |
| ATOM | 2125 | CG2 | ILE | A | 140 | 61.194 | −44.314 | 12.995 | 1.00 | 18.20 | A | C |
| ATOM | 2129 | C | ILE | A | 140 | 61.757 | −43.420 | 10.306 | 1.00 | 19.04 | A | C |
| ATOM | 2130 | O | ILE | A | 140 | 60.635 | −42.908 | 10.342 | 1.00 | 19.09 | A | O |
| ATOM | 2132 | N | LEU | A | 141 | 62.859 | −42.741 | 9.977 | 1.00 | 18.82 | A | N |
| ATOM | 2133 | CA | LEU | A | 141 | 62.812 | −41.358 | 9.492 | 1.00 | 18.09 | A | C |
| ATOM | 2135 | CB | LEU | A | 141 | 64.218 | −40.747 | 9.399 | 1.00 | 17.81 | A | C |
| ATOM | 2138 | CG | LEU | A | 141 | 64.684 | −39.929 | 10.604 | 1.00 | 17.40 | A | C |
| ATOM | 2140 | CD1 | LEU | A | 141 | 66.146 | −39.540 | 10.452 | 1.00 | 16.73 | A | C |
| ATOM | 2144 | CD2 | LEU | A | 141 | 63.817 | −38.692 | 10.781 | 1.00 | 16.04 | A | C |
| ATOM | 2148 | C | LEU | A | 141 | 62.129 | −41.282 | 8.132 | 1.00 | 17.94 | A | C |
| ATOM | 2149 | O | LEU | A | 141 | 61.260 | −40.440 | 7.917 | 1.00 | 18.26 | A | O |
| ATOM | 2151 | N | SER | A | 142 | 62.523 | −42.160 | 7.215 | 1.00 | 17.56 | A | N |
| ATOM | 2152 | CA | SER | A | 142 | 61.894 | −42.205 | 5.897 | 1.00 | 17.58 | A | C |
| ATOM | 2154 | CB | SER | A | 142 | 62.563 | −43.246 | 4.998 | 1.00 | 17.71 | A | C |
| ATOM | 2157 | OG | SER | A | 142 | 63.697 | −42.690 | 4.359 | 1.00 | 18.76 | A | O |
| ATOM | 2159 | C | SER | A | 142 | 60.401 | −42.488 | 6.016 | 1.00 | 17.20 | A | C |
| ATOM | 2160 | O | SER | A | 142 | 59.585 | −41.779 | 5.427 | 1.00 | 17.78 | A | O |
| ATOM | 2162 | N | LEU | A | 143 | 60.052 | −43.516 | 6.787 | 1.00 | 16.32 | A | N |
| ATOM | 2163 | CA | LEU | A | 143 | 58.651 | −43.842 | 7.046 | 1.00 | 15.60 | A | C |
| ATOM | 2165 | CB | LEU | A | 143 | 58.534 | −45.084 | 7.940 | 1.00 | 15.48 | A | C |
| ATOM | 2168 | CG | LEU | A | 143 | 57.132 | −45.436 | 8.460 | 1.00 | 14.83 | A | C |
| ATOM | 2170 | CD1 | LEU | A | 143 | 56.099 | −45.438 | 7.342 | 1.00 | 14.92 | A | C |
| ATOM | 2174 | CD2 | LEU | A | 143 | 57.146 | −46.774 | 9.165 | 1.00 | 14.54 | A | C |
| ATOM | 2178 | C | LEU | A | 143 | 57.929 | −42.662 | 7.693 | 1.00 | 15.26 | A | C |
| ATOM | 2179 | O | LEU | A | 143 | 56.819 | −42.316 | 7.292 | 1.00 | 15.30 | A | O |
| ATOM | 2181 | N | TYR | A | 144 | 58.562 | −42.052 | 8.692 | 1.00 | 14.88 | A | N |
| ATOM | 2182 | CA | TYR | A | 144 | 57.996 | −40.882 | 9.359 | 1.00 | 14.72 | A | C |
| ATOM | 2184 | CB | TYR | A | 144 | 58.966 | −40.327 | 10.406 | 1.00 | 14.64 | A | C |
| ATOM | 2187 | CG | TYR | A | 144 | 58.555 | −38.994 | 10.994 | 1.00 | 14.77 | A | C |
| ATOM | 2188 | CD1 | TYR | A | 144 | 57.598 | −38.919 | 12.001 | 1.00 | 15.26 | A | C |
| ATOM | 2190 | CE1 | TYR | A | 144 | 57.220 | −37.698 | 12.548 | 1.00 | 15.65 | A | C |
| ATOM | 2192 | CZ | TYR | A | 144 | 57.807 | −36.534 | 12.091 | 1.00 | 17.33 | A | C |
| ATOM | 2193 | OH | TYR | A | 144 | 57.435 | −35.321 | 12.629 | 1.00 | 19.54 | A | O |
| ATOM | 2195 | CE2 | TYR | A | 144 | 58.761 | −36.583 | 11.090 | 1.00 | 17.47 | A | C |
| ATOM | 2197 | CD2 | TYR | A | 144 | 59.131 | −37.809 | 10.550 | 1.00 | 16.29 | A | C |
| ATOM | 2199 | C | TYR | A | 144 | 57.656 | −39.801 | 8.344 | 1.00 | 14.69 | A | C |
| ATOM | 2200 | O | TYR | A | 144 | 56.554 | −39.263 | 8.354 | 1.00 | 14.53 | A | O |
| ATOM | 2202 | N | GLU | A | 145 | 58.605 | −39.502 | 7.464 | 1.00 | 14.92 | A | N |
| ATOM | 2203 | CA | GLU | A | 145 | 58.428 | −38.457 | 6.458 | 1.00 | 15.34 | A | C |
| ATOM | 2205 | CB | GLU | A | 145 | 59.725 | −38.257 | 5.666 | 1.00 | 15.45 | A | C |
| ATOM | 2208 | CG | GLU | A | 145 | 60.888 | −37.694 | 6.479 | 1.00 | 16.03 | A | C |
| ATOM | 2211 | CD | GLU | A | 145 | 60.742 | −36.220 | 6.815 | 1.00 | 17.46 | A | C |
| ATOM | 2212 | OE1 | GLU | A | 145 | 59.672 | −35.627 | 6.537 | 1.00 | 18.49 | A | O |
| ATOM | 2213 | OE2 | GLU | A | 145 | 61.709 | −35.654 | 7.368 | 1.00 | 17.22 | A | O |
| ATOM | 2214 | C | GLU | A | 145 | 57.277 | −38.759 | 5.493 | 1.00 | 15.41 | A | C |
| ATOM | 2215 | O | GLU | A | 145 | 56.569 | −37.845 | 5.059 | 1.00 | 15.63 | A | O |
| ATOM | 2217 | N | ALA | A | 146 | 57.100 | −40.038 | 5.167 | 1.00 | 15.04 | A | N |
| ATOM | 2218 | CA | ALA | A | 146 | 56.073 | −40.475 | 4.221 | 1.00 | 14.82 | A | C |
| ATOM | 2220 | CB | ALA | A | 146 | 56.363 | −41.894 | 3.752 | 1.00 | 14.97 | A | C |
| ATOM | 2224 | C | ALA | A | 146 | 54.665 | −40.406 | 4.801 | 1.00 | 14.76 | A | C |

TABLE 8-2-continued

Coordinates for L494P Structure

| | | | | | | | | | | | | |
|---|---|---|---|---|---|---|---|---|---|---|---|---|
| ATOM | 2225 | O | ALA | A | 146 | 53.695 | −40.297 | 4.056 | 1.00 | 14.65 | A | O |
| ATOM | 2227 | N | SER | A | 147 | 54.551 | −40.470 | 6.124 | 1.00 | 14.98 | A | N |
| ATOM | 2228 | CA | SER | A | 147 | 53.245 | −40.507 | 6.778 | 1.00 | 15.23 | A | C |
| ATOM | 2230 | CB | SER | A | 147 | 53.401 | −40.795 | 8.271 | 1.00 | 15.04 | A | C |
| ATOM | 2233 | OG | SER | A | 147 | 53.997 | −39.704 | 8.942 | 1.00 | 14.18 | A | O |
| ATOM | 2235 | C | SER | A | 147 | 52.457 | −39.214 | 6.591 | 1.00 | 15.94 | A | C |
| ATOM | 2236 | O | SER | A | 147 | 51.231 | −39.204 | 6.738 | 1.00 | 16.57 | A | O |
| ATOM | 2238 | N | PHE | A | 148 | 53.165 | −38.133 | 6.271 | 1.00 | 16.28 | A | N |
| ATOM | 2239 | CA | PHE | A | 148 | 52.552 | −36.815 | 6.123 | 1.00 | 16.58 | A | C |
| ATOM | 2241 | CB | PHE | A | 148 | 53.581 | −35.727 | 6.416 | 1.00 | 16.42 | A | C |
| ATOM | 2244 | CG | PHE | A | 148 | 53.926 | −35.627 | 7.867 | 1.00 | 17.86 | A | C |
| ATOM | 2245 | CD1 | PHE | A | 148 | 53.239 | −34.753 | 8.694 | 1.00 | 19.24 | A | C |
| ATOM | 2247 | CE1 | PHE | A | 148 | 53.538 | −34.667 | 10.042 | 1.00 | 19.64 | A | C |
| ATOM | 2249 | CZ | PHE | A | 148 | 54.529 | −35.473 | 10.579 | 1.00 | 20.02 | A | C |
| ATOM | 2251 | CE2 | PHE | A | 148 | 55.214 | −36.358 | 9.763 | 1.00 | 19.24 | A | C |
| ATOM | 2253 | CD2 | PHE | A | 148 | 54.905 | −36.435 | 8.416 | 1.00 | 19.02 | A | C |
| ATOM | 2255 | C | PHE | A | 148 | 51.898 | −36.586 | 4.765 | 1.00 | 16.73 | A | C |
| ATOM | 2256 | O | PHE | A | 148 | 51.078 | −35.674 | 4.623 | 1.00 | 17.72 | A | O |
| ATOM | 2258 | N | LEU | A | 149 | 52.241 | −37.416 | 3.780 | 1.00 | 16.12 | A | N |
| ATOM | 2259 | CA | LEU | A | 149 | 51.605 | −37.353 | 2.461 | 1.00 | 15.65 | A | C |
| ATOM | 2261 | CB | LEU | A | 149 | 52.582 | −37.802 | 1.368 | 1.00 | 15.36 | A | C |
| ATOM | 2264 | CG | LEU | A | 149 | 53.836 | −36.939 | 1.206 | 1.00 | 14.18 | A | C |
| ATOM | 2266 | CD1 | LEU | A | 149 | 54.944 | −37.408 | 2.137 | 1.00 | 13.76 | A | C |
| ATOM | 2270 | CD2 | LEU | A | 149 | 54.315 | −36.957 | −0.235 | 1.00 | 14.24 | A | C |
| ATOM | 2274 | C | LEU | A | 149 | 50.328 | −38.200 | 2.405 | 1.00 | 15.63 | A | C |
| ATOM | 2275 | O | LEU | A | 149 | 49.735 | −38.366 | 1.337 | 1.00 | 15.57 | A | O |
| ATOM | 2277 | N | ALA | A | 150 | 49.909 | −38.723 | 3.557 | 1.00 | 15.70 | A | N |
| ATOM | 2278 | CA | ALA | A | 150 | 48.736 | −39.589 | 3.650 | 1.00 | 15.72 | A | C |
| ATOM | 2280 | CB | ALA | A | 150 | 48.563 | −40.070 | 5.086 | 1.00 | 15.67 | A | C |
| ATOM | 2284 | C | ALA | A | 150 | 47.456 | −38.899 | 3.170 | 1.00 | 15.65 | A | C |
| ATOM | 2285 | O | ALA | A | 150 | 47.255 | −37.706 | 3.404 | 1.00 | 15.79 | A | O |
| ATOM | 2287 | N | LEU | A | 151 | 46.606 | −39.665 | 2.491 | 1.00 | 15.19 | A | N |
| ATOM | 2288 | CA | LEU | A | 151 | 45.287 | −39.199 | 2.067 | 1.00 | 14.89 | A | C |
| ATOM | 2290 | CB | LEU | A | 151 | 44.936 | −39.778 | 0.698 | 1.00 | 14.68 | A | C |
| ATOM | 2293 | CG | LEU | A | 151 | 45.733 | −39.223 | −0.478 | 1.00 | 13.02 | A | C |
| ATOM | 2295 | CD1 | LEU | A | 151 | 45.541 | −40.087 | −1.715 | 1.00 | 12.24 | A | C |
| ATOM | 2299 | CD2 | LEU | A | 151 | 45.311 | −37.794 | −0.747 | 1.00 | 12.42 | A | C |
| ATOM | 2303 | C | LEU | A | 151 | 44.241 | −39.629 | 3.087 | 1.00 | 14.91 | A | C |
| ATOM | 2304 | O | LEU | A | 151 | 44.529 | −40.431 | 3.976 | 1.00 | 14.52 | A | O |
| ATOM | 2306 | N | GLU | A | 152 | 43.027 | −39.102 | 2.957 | 1.00 | 15.12 | A | N |
| ATOM | 2307 | CA | GLU | A | 152 | 41.949 | −39.471 | 3.870 | 1.00 | 15.70 | A | C |
| ATOM | 2309 | CB | GLU | A | 152 | 40.662 | −38.692 | 3.572 | 1.00 | 16.17 | A | C |
| ATOM | 2312 | CG | GLU | A | 152 | 40.577 | −37.350 | 4.299 | 1.00 | 18.12 | A | C |
| ATOM | 2315 | CD | GLU | A | 152 | 39.183 | −36.749 | 4.265 | 1.00 | 19.18 | A | C |
| ATOM | 2316 | OE1 | GLU | A | 152 | 38.686 | −36.455 | 3.157 | 1.00 | 20.47 | A | O |
| ATOM | 2317 | OE2 | GLU | A | 152 | 38.589 | −36.566 | 5.349 | 1.00 | 19.32 | A | O |
| ATOM | 2318 | C | GLU | A | 152 | 41.690 | −40.968 | 3.793 | 1.00 | 15.50 | A | C |
| ATOM | 2319 | O | GLU | A | 152 | 41.623 | −41.535 | 2.704 | 1.00 | 15.88 | A | O |
| ATOM | 2321 | N | GLY | A | 153 | 41.575 | −41.602 | 4.957 | 1.00 | 15.25 | A | N |
| ATOM | 2322 | CA | GLY | A | 153 | 41.298 | −43.033 | 5.039 | 1.00 | 14.87 | A | C |
| ATOM | 2325 | C | GLY | A | 153 | 42.512 | −43.935 | 5.003 | 1.00 | 14.62 | A | C |
| ATOM | 2326 | O | GLY | A | 153 | 42.393 | −45.134 | 5.246 | 1.00 | 14.54 | A | O |
| ATOM | 2328 | N | GLU | A | 154 | 43.680 | −43.372 | 4.705 | 1.00 | 14.82 | A | N |
| ATOM | 2329 | CA | GLU | A | 154 | 44.907 | −44.157 | 4.660 | 1.00 | 14.90 | A | C |
| ATOM | 2331 | CB | GLU | A | 154 | 45.957 | −43.488 | 3.769 | 1.00 | 14.85 | A | C |
| ATOM | 2334 | CG | GLU | A | 154 | 45.527 | −43.403 | 2.305 | 1.00 | 15.01 | A | C |
| ATOM | 2337 | CD | GLU | A | 154 | 46.681 | −43.160 | 1.350 | 1.00 | 15.65 | A | C |
| ATOM | 2338 | OE1 | GLU | A | 154 | 46.559 | −43.530 | 0.164 | 1.00 | 13.73 | A | O |
| ATOM | 2339 | OE2 | GLU | A | 154 | 47.712 | −42.599 | 1.779 | 1.00 | 18.73 | A | O |
| ATOM | 2340 | C | GLU | A | 154 | 45.421 | −44.359 | 6.079 | 1.00 | 14.88 | A | C |
| ATOM | 2341 | O | GLU | A | 154 | 46.302 | −43.638 | 6.548 | 1.00 | 15.13 | A | O |
| ATOM | 2343 | N | ASN | A | 155 | 44.848 | −45.354 | 6.750 | 1.00 | 14.65 | A | N |
| ATOM | 2344 | CA | ASN | A | 155 | 45.097 | −45.587 | 8.172 | 1.00 | 14.39 | A | C |
| ATOM | 2346 | CB | ASN | A | 155 | 44.043 | −46.540 | 8.758 | 1.00 | 14.42 | A | C |
| ATOM | 2349 | CG | ASN | A | 155 | 44.069 | −47.915 | 8.115 | 1.00 | 14.05 | A | C |
| ATOM | 2350 | OD1 | ASN | A | 155 | 44.417 | −48.059 | 6.946 | 1.00 | 15.53 | A | O |
| ATOM | 2351 | ND2 | ASN | A | 155 | 43.691 | −48.932 | 8.877 | 1.00 | 14.24 | A | N |
| ATOM | 2354 | C | ASN | A | 155 | 46.499 | −46.101 | 8.492 | 1.00 | 14.15 | A | C |
| ATOM | 2355 | O | ASN | A | 155 | 47.057 | −45.750 | 9.530 | 1.00 | 14.42 | A | O |
| ATOM | 2357 | N | ILE | A | 156 | 47.066 | −46.923 | 7.607 | 1.00 | 13.81 | A | N |
| ATOM | 2358 | CA | ILE | A | 156 | 48.394 | −47.515 | 7.836 | 1.00 | 13.39 | A | C |
| ATOM | 2360 | CB | ILE | A | 156 | 48.774 | −48.549 | 6.731 | 1.00 | 13.45 | A | C |
| ATOM | 2362 | CG1 | ILE | A | 156 | 47.886 | −49.794 | 6.827 | 1.00 | 13.17 | A | C |
| ATOM | 2365 | CD1 | ILE | A | 156 | 48.364 | −50.961 | 5.977 | 1.00 | 12.86 | A | C |
| ATOM | 2369 | CG2 | ILE | A | 156 | 50.234 | −48.965 | 6.847 | 1.00 | 12.55 | A | C |
| ATOM | 2373 | C | ILE | A | 156 | 49.486 | −46.447 | 7.955 | 1.00 | 13.02 | A | C |
| ATOM | 2374 | O | ILE | A | 156 | 50.471 | −46.643 | 8.665 | 1.00 | 12.85 | A | O |
| ATOM | 2376 | N | LEU | A | 157 | 49.304 | −45.319 | 7.275 | 1.00 | 12.90 | A | N |

TABLE 8-2-continued

Coordinates for L494P Structure

| | | | | | | | | | | | | |
|---|---|---|---|---|---|---|---|---|---|---|---|---|
| ATOM | 2377 | CA | LEU | A | 157 | 50.246 | −44.205 | 7.381 | 1.00 | 12.94 | A | C |
| ATOM | 2379 | CB | LEU | A | 157 | 50.114 | −43.261 | 6.182 | 1.00 | 12.67 | A | C |
| ATOM | 2382 | CG | LEU | A | 157 | 50.865 | −43.718 | 4.929 | 1.00 | 11.71 | A | C |
| ATOM | 2384 | CD1 | LEU | A | 157 | 50.470 | −45.129 | 4.540 | 1.00 | 11.58 | A | C |
| ATOM | 2388 | CD2 | LEU | A | 157 | 50.623 | −42.762 | 3.774 | 1.00 | 12.63 | A | C |
| ATOM | 2392 | C | LEU | A | 157 | 50.078 | −43.444 | 8.701 | 1.00 | 13.44 | A | C |
| ATOM | 2393 | O | LEU | A | 157 | 51.068 | −43.039 | 9.308 | 1.00 | 13.49 | A | O |
| ATOM | 2395 | N | ASP | A | 158 | 48.833 | −43.260 | 9.144 | 1.00 | 14.10 | A | N |
| ATOM | 2396 | CA | ASP | A | 158 | 48.551 | −42.626 | 10.442 | 1.00 | 14.43 | A | C |
| ATOM | 2398 | CB | ASP | A | 158 | 47.043 | −42.417 | 10.635 | 1.00 | 14.42 | A | C |
| ATOM | 2401 | CG | ASP | A | 158 | 46.488 | −41.307 | 9.759 | 1.00 | 15.28 | A | C |
| ATOM | 2402 | OD1 | ASP | A | 158 | 47.035 | −40.184 | 9.789 | 1.00 | 14.96 | A | O |
| ATOM | 2403 | OD2 | ASP | A | 158 | 45.494 | −41.555 | 9.045 | 1.00 | 17.78 | A | O |
| ATOM | 2404 | C | ASP | A | 158 | 49.113 | −43.454 | 11.597 | 1.00 | 14.67 | A | C |
| ATOM | 2405 | O | ASP | A | 158 | 49.622 | −42.899 | 12.573 | 1.00 | 14.25 | A | O |
| ATOM | 2407 | N | GLU | A | 159 | 48.999 | −44.778 | 11.476 | 1.00 | 15.29 | A | N |
| ATOM | 2408 | CA | GLU | A | 159 | 49.677 | −45.723 | 12.370 | 1.00 | 15.67 | A | C |
| ATOM | 2410 | CB | GLU | A | 159 | 49.261 | −47.160 | 12.052 | 1.00 | 15.79 | A | C |
| ATOM | 2413 | CG | GLU | A | 159 | 47.811 | −47.499 | 12.324 | 1.00 | 16.58 | A | C |
| ATOM | 2416 | CD | GLU | A | 159 | 47.447 | −48.900 | 11.846 | 1.00 | 18.81 | A | C |
| ATOM | 2417 | OE1 | GLU | A | 159 | 48.362 | −49.720 | 11.591 | 1.00 | 17.33 | A | O |
| ATOM | 2418 | OE2 | GLU | A | 159 | 46.237 | −49.182 | 11.725 | 1.00 | 22.11 | A | O |
| ATOM | 2419 | C | GLU | A | 159 | 51.198 | −45.631 | 12.218 | 1.00 | 15.73 | A | C |
| ATOM | 2420 | O | GLU | A | 159 | 51.934 | −45.685 | 13.205 | 1.00 | 15.90 | A | O |
| ATOM | 2422 | N | ALA | A | 160 | 51.656 | −45.525 | 10.971 | 1.00 | 15.58 | A | N |
| ATOM | 2423 | CA | ALA | A | 160 | 53.082 | −45.445 | 10.660 | 1.00 | 15.31 | A | C |
| ATOM | 2425 | CB | ALA | A | 160 | 53.297 | −45.451 | 9.153 | 1.00 | 15.15 | A | C |
| ATOM | 2429 | C | ALA | A | 160 | 53.726 | −44.210 | 11.276 | 1.00 | 15.28 | A | C |
| ATOM | 2430 | O | ALA | A | 160 | 54.895 | −44.244 | 11.651 | 1.00 | 15.24 | A | O |
| ATOM | 2432 | N | LYS | A | 161 | 52.965 | −43.124 | 11.373 | 1.00 | 15.64 | A | N |
| ATOM | 2433 | CA | LYS | A | 161 | 53.459 | −41.904 | 11.996 | 1.00 | 16.20 | A | C |
| ATOM | 2435 | CB | LYS | A | 161 | 52.467 | −40.748 | 11.813 | 1.00 | 16.58 | A | C |
| ATOM | 2438 | CG | LYS | A | 161 | 53.056 | −39.373 | 12.115 | 1.00 | 17.99 | A | C |
| ATOM | 2441 | CD | LYS | A | 161 | 51.982 | −38.301 | 12.267 | 1.00 | 19.18 | A | C |
| ATOM | 2444 | CE | LYS | A | 161 | 51.280 | −38.008 | 10.956 | 1.00 | 20.22 | A | C |
| ATOM | 2447 | NZ | LYS | A | 161 | 50.469 | −36.762 | 11.043 | 1.00 | 22.18 | A | N |
| ATOM | 2451 | C | LYS | A | 161 | 53.714 | −42.165 | 13.479 | 1.00 | 16.44 | A | C |
| ATOM | 2452 | O | LYS | A | 161 | 54.843 | −42.022 | 13.951 | 1.00 | 16.58 | A | O |
| ATOM | 2454 | N | VAL | A | 162 | 52.671 | −42.579 | 14.197 | 1.00 | 16.53 | A | N |
| ATOM | 2455 | CA | VAL | A | 162 | 52.759 | −42.814 | 15.645 | 1.00 | 16.48 | A | C |
| ATOM | 2457 | CB | VAL | A | 162 | 51.412 | −43.299 | 16.237 | 1.00 | 16.23 | A | C |
| ATOM | 2459 | CG1 | VAL | A | 162 | 51.528 | −43.498 | 17.742 | 1.00 | 16.10 | A | C |
| ATOM | 2463 | CG2 | VAL | A | 162 | 50.302 | −42.307 | 15.923 | 1.00 | 16.13 | A | C |
| ATOM | 2467 | C | VAL | A | 162 | 53.861 | −43.822 | 15.995 | 1.00 | 16.54 | A | C |
| ATOM | 2468 | O | VAL | A | 162 | 54.609 | −43.616 | 16.952 | 1.00 | 16.62 | A | O |
| ATOM | 2470 | N | PHE | A | 163 | 53.955 | −44.899 | 15.215 | 1.00 | 16.67 | A | N |
| ATOM | 2471 | CA | PHE | A | 163 | 55.011 | −45.905 | 15.387 | 1.00 | 16.71 | A | C |
| ATOM | 2473 | CB | PHE | A | 163 | 54.803 | −47.072 | 14.417 | 1.00 | 16.07 | A | C |
| ATOM | 2476 | CG | PHE | A | 163 | 55.907 | −48.094 | 14.446 | 1.00 | 13.86 | A | C |
| ATOM | 2477 | CD1 | PHE | A | 163 | 55.862 | −49.160 | 15.332 | 1.00 | 12.47 | A | C |
| ATOM | 2479 | CE1 | PHE | A | 163 | 56.880 | −50.105 | 15.360 | 1.00 | 11.52 | A | C |
| ATOM | 2481 | CZ | PHE | A | 163 | 57.957 | −49.986 | 14.497 | 1.00 | 10.81 | A | C |
| ATOM | 2483 | CE2 | PHE | A | 163 | 58.014 | −48.928 | 13.610 | 1.00 | 11.67 | A | C |
| ATOM | 2485 | CD2 | PHE | A | 163 | 56.992 | −47.988 | 13.587 | 1.00 | 12.64 | A | C |
| ATOM | 2487 | C | PHE | A | 163 | 56.406 | −45.311 | 15.182 | 1.00 | 17.79 | A | C |
| ATOM | 2488 | O | PHE | A | 163 | 57.368 | −45.724 | 15.838 | 1.00 | 17.93 | A | O |
| ATOM | 2490 | N | ALA | A | 164 | 56.511 | −44.355 | 14.262 | 1.00 | 18.68 | A | N |
| ATOM | 2491 | CA | ALA | A | 164 | 57.782 | −43.701 | 13.968 | 1.00 | 19.35 | A | C |
| ATOM | 2493 | CB | ALA | A | 164 | 57.721 | −43.017 | 12.611 | 1.00 | 19.35 | A | C |
| ATOM | 2497 | C | ALA | A | 164 | 58.149 | −42.697 | 15.060 | 1.00 | 19.82 | A | C |
| ATOM | 2498 | O | ALA | A | 164 | 59.254 | −42.742 | 15.602 | 1.00 | 20.21 | A | O |
| ATOM | 2500 | N | ILE | A | 165 | 57.217 | −41.803 | 15.383 | 1.00 | 20.14 | A | N |
| ATOM | 2501 | CA | ILE | A | 165 | 57.441 | −40.775 | 16.404 | 1.00 | 20.35 | A | C |
| ATOM | 2503 | CB | ILE | A | 165 | 56.150 | −39.959 | 16.698 | 1.00 | 20.49 | A | C |
| ATOM | 2505 | CG1 | ILE | A | 165 | 55.797 | −39.062 | 15.508 | 1.00 | 20.83 | A | C |
| ATOM | 2508 | CD1 | ILE | A | 165 | 54.500 | −38.292 | 15.676 | 1.00 | 21.96 | A | C |
| ATOM | 2512 | CG2 | ILE | A | 165 | 56.325 | −39.092 | 17.939 | 1.00 | 20.43 | A | C |
| ATOM | 2516 | C | ILE | A | 165 | 57.949 | −41.397 | 17.703 | 1.00 | 20.24 | A | C |
| ATOM | 2517 | O | ILE | A | 165 | 59.035 | −41.062 | 18.173 | 1.00 | 19.62 | A | O |
| ATOM | 2519 | N | SER | A | 166 | 57.167 | −42.320 | 18.258 | 1.00 | 20.69 | A | N |
| ATOM | 2520 | CA | SER | A | 166 | 57.470 | −42.919 | 19.560 | 1.00 | 21.20 | A | C |
| ATOM | 2522 | CB | SER | A | 166 | 56.381 | −43.923 | 19.958 | 1.00 | 21.36 | A | C |
| ATOM | 2525 | OG | SER | A | 166 | 56.287 | −44.983 | 19.023 | 1.00 | 21.83 | A | O |
| ATOM | 2527 | C | SER | A | 166 | 58.846 | −43.587 | 19.616 | 1.00 | 21.27 | A | C |
| ATOM | 2528 | O | SER | A | 166 | 59.468 | −43.630 | 20.679 | 1.00 | 21.20 | A | O |
| ATOM | 2530 | N | HIS | A | 167 | 59.314 | −44.102 | 18.480 | 1.00 | 21.52 | A | N |
| ATOM | 2531 | CA | HIS | A | 167 | 60.649 | −44.703 | 18.398 | 1.00 | 21.98 | A | C |
| ATOM | 2533 | CB | HIS | A | 167 | 60.677 | −45.836 | 17.366 | 1.00 | 22.19 | A | C |

TABLE 8-2-continued

Coordinates for L494P Structure

| | | | | | | | | | | | |
|---|---|---|---|---|---|---|---|---|---|---|---|
| ATOM | 2536 | CG | HIS | A | 167 | 60.128 | −47.131 | 17.881 | 1.00 | 23.11 A | C |
| ATOM | 2537 | ND1 | HIS | A | 167 | 58.969 | −47.696 | 17.395 | 1.00 | 23.65 A | N |
| ATOM | 2539 | CE1 | HIS | A | 167 | 58.730 | −48.826 | 18.038 | 1.00 | 24.10 A | C |
| ATOM | 2541 | NE2 | HIS | A | 167 | 59.690 | −49.012 | 18.926 | 1.00 | 23.55 A | N |
| ATOM | 2543 | CD2 | HIS | A | 167 | 60.575 | −47.964 | 18.851 | 1.00 | 23.42 A | C |
| ATOM | 2545 | C | HIS | A | 167 | 61.748 | −43.677 | 18.099 | 1.00 | 22.06 A | C |
| ATOM | 2546 | O | HIS | A | 167 | 62.900 | −43.884 | 18.480 | 1.00 | 21.93 A | O |
| ATOM | 2548 | N | LEU | A | 168 | 61.397 | −42.584 | 17.422 | 1.00 | 22.44 A | N |
| ATOM | 2549 | CA | LEU | A | 168 | 62.342 | −41.486 | 17.174 | 1.00 | 22.76 A | C |
| ATOM | 2551 | CB | LEU | A | 168 | 61.860 | −40.590 | 16.025 | 1.00 | 22.70 A | C |
| ATOM | 2554 | CG | LEU | A | 168 | 61.921 | −41.116 | 14.589 | 1.00 | 22.46 A | C |
| ATOM | 2556 | CD1 | LEU | A | 168 | 61.482 | −40.020 | 13.632 | 1.00 | 22.16 A | C |
| ATOM | 2560 | CD2 | LEU | A | 168 | 63.317 | −41.601 | 14.234 | 1.00 | 23.20 A | C |
| ATOM | 2564 | C | LEU | A | 168 | 62.542 | −40.614 | 18.412 | 1.00 | 23.43 A | C |
| ATOM | 2565 | O | LEU | A | 168 | 63.648 | −40.140 | 18.673 | 1.00 | 23.50 A | O |
| ATOM | 2567 | N | LYS | A | 169 | 61.465 | −40.408 | 19.165 | 1.00 | 24.25 A | N |
| ATOM | 2568 | CA | LYS | A | 169 | 61.446 | −39.435 | 20.259 | 1.00 | 24.95 A | C |
| ATOM | 2570 | CB | LYS | A | 169 | 60.007 | −39.234 | 20.749 | 1.00 | 24.99 A | C |
| ATOM | 2573 | CG | LYS | A | 169 | 59.788 | −37.951 | 21.533 | 1.00 | 26.38 A | C |
| ATOM | 2576 | CD | LYS | A | 169 | 58.329 | −37.522 | 21.493 | 1.00 | 27.59 A | C |
| ATOM | 2579 | CE | LYS | A | 169 | 58.115 | −36.206 | 22.217 | 1.00 | 28.00 A | C |
| ATOM | 2582 | NZ | LYS | A | 169 | 56.702 | −35.756 | 22.113 | 1.00 | 29.00 A | N |
| ATOM | 2586 | C | LYS | A | 169 | 62.353 | −39.802 | 21.438 | 1.00 | 25.45 A | C |
| ATOM | 2587 | O | LYS | A | 169 | 62.861 | −38.917 | 22.128 | 1.00 | 25.46 A | O |
| ATOM | 2589 | N | GLU | A | 170 | 62.560 | −41.097 | 21.661 | 1.00 | 26.28 A | N |
| ATOM | 2590 | CA | GLU | A | 170 | 63.351 | −41.570 | 22.798 | 1.00 | 27.20 A | C |
| ATOM | 2592 | CB | GLU | A | 170 | 62.625 | −42.725 | 23.502 | 1.00 | 27.52 A | C |
| ATOM | 2595 | CG | GLU | A | 170 | 61.178 | −42.416 | 23.892 | 1.00 | 29.00 A | C |
| ATOM | 2598 | CD | GLU | A | 170 | 61.051 | −41.184 | 24.776 | 1.00 | 30.77 A | C |
| ATOM | 2599 | OE1 | GLU | A | 170 | 61.736 | −41.127 | 25.821 | 1.00 | 30.80 A | O |
| ATOM | 2600 | OE2 | GLU | A | 170 | 60.266 | −40.274 | 24.426 | 1.00 | 31.83 A | O |
| ATOM | 2601 | C | GLU | A | 170 | 64.756 | −41.997 | 22.365 | 1.00 | 27.59 A | C |
| ATOM | 2602 | O | GLU | A | 170 | 65.223 | −43.086 | 22.715 | 1.00 | 27.53 A | O |
| ATOM | 2604 | N | LEU | A | 171 | 65.424 | −41.127 | 21.609 | 1.00 | 27.91 A | N |
| ATOM | 2605 | CA | LEU | A | 171 | 66.775 | −41.390 | 21.120 | 1.00 | 28.20 A | C |
| ATOM | 2607 | CB | LEU | A | 171 | 66.784 | −41.495 | 19.594 | 1.00 | 27.90 A | C |
| ATOM | 2610 | CG | LEU | A | 171 | 65.896 | −42.582 | 18.983 | 1.00 | 27.09 A | C |
| ATOM | 2612 | CD1 | LEU | A | 171 | 66.044 | −42.582 | 17.469 | 1.00 | 25.97 A | C |
| ATOM | 2616 | CD2 | LEU | A | 171 | 66.215 | −43.960 | 19.554 | 1.00 | 25.82 A | C |
| ATOM | 2620 | C | LEU | A | 171 | 67.720 | −40.283 | 21.570 | 1.00 | 28.93 A | C |
| ATOM | 2621 | O | LEU | A | 171 | 67.390 | −39.099 | 21.468 | 1.00 | 28.94 A | O |
| ATOM | 2623 | N | SER | A | 172 | 68.895 | −40.680 | 22.060 | 1.00 | 29.73 A | N |
| ATOM | 2624 | CA | SER | A | 172 | 69.882 | −39.745 | 22.605 | 1.00 | 30.12 A | C |
| ATOM | 2626 | CB | SER | A | 172 | 70.465 | −40.293 | 23.905 | 1.00 | 30.03 A | C |
| ATOM | 2629 | OG | SER | A | 172 | 69.435 | −40.707 | 24.783 | 1.00 | 30.49 A | O |
| ATOM | 2631 | C | SER | A | 172 | 71.012 | −39.473 | 21.617 | 1.00 | 30.47 A | C |
| ATOM | 2632 | O | SER | A | 172 | 71.235 | −40.241 | 20.678 | 1.00 | 30.80 A | O |
| ATOM | 2634 | N | GLU | A | 173 | 71.733 | −38.381 | 21.855 | 1.00 | 30.63 A | N |
| ATOM | 2635 | CA | GLU | A | 173 | 72.807 | −37.942 | 20.964 | 1.00 | 30.79 A | C |
| ATOM | 2637 | CB | GLU | A | 173 | 73.199 | −36.492 | 21.287 | 1.00 | 30.90 A | C |
| ATOM | 2640 | CG | GLU | A | 173 | 73.888 | −35.747 | 20.143 | 1.00 | 31.84 A | C |
| ATOM | 2643 | CD | GLU | A | 173 | 73.898 | −34.232 | 20.335 | 1.00 | 33.26 A | C |
| ATOM | 2644 | OE1 | GLU | A | 173 | 72.839 | −33.658 | 20.672 | 1.00 | 33.46 A | O |
| ATOM | 2645 | OE2 | GLU | A | 173 | 74.964 | −33.611 | 20.136 | 1.00 | 34.47 A | O |
| ATOM | 2646 | C | GLU | A | 173 | 74.038 | −38.862 | 21.017 | 1.00 | 30.75 A | C |
| ATOM | 2647 | O | GLU | A | 173 | 74.807 | −38.913 | 20.057 | 1.00 | 30.90 A | O |
| ATOM | 2649 | N | GLU | A | 174 | 74.221 | −39.585 | 22.125 | 1.00 | 30.65 A | N |
| ATOM | 2650 | CA | GLU | A | 174 | 75.338 | −40.532 | 22.262 | 1.00 | 30.58 A | C |
| ATOM | 2652 | CB | GLU | A | 174 | 75.627 | −40.857 | 23.733 | 1.00 | 30.55 A | C |
| ATOM | 2655 | CG | GLU | A | 174 | 75.957 | −39.663 | 24.614 | 1.00 | 30.63 A | C |
| ATOM | 2658 | CD | GLU | A | 174 | 74.768 | −39.198 | 25.430 | 1.00 | 30.50 A | C |
| ATOM | 2659 | OE1 | GLU | A | 174 | 73.749 | −38.804 | 24.825 | 1.00 | 29.37 A | O |
| ATOM | 2660 | OE2 | GLU | A | 174 | 74.852 | −39.230 | 26.675 | 1.00 | 30.66 A | O |
| ATOM | 2661 | C | GLU | A | 174 | 75.073 | −41.847 | 21.530 | 1.00 | 30.62 A | C |
| ATOM | 2662 | O | GLU | A | 174 | 75.991 | −42.432 | 20.948 | 1.00 | 30.96 A | O |
| ATOM | 2664 | N | LYS | A | 175 | 73.822 | −42.308 | 21.575 | 1.00 | 30.19 A | N |
| ATOM | 2665 | CA | LYS | A | 175 | 73.443 | −43.617 | 21.030 | 1.00 | 29.66 A | C |
| ATOM | 2667 | CB | LYS | A | 175 | 71.983 | −43.959 | 21.363 | 1.00 | 29.85 A | C |
| ATOM | 2670 | CG | LYS | A | 175 | 71.603 | −43.849 | 22.838 | 1.00 | 30.60 A | C |
| ATOM | 2673 | CD | LYS | A | 175 | 72.325 | −44.864 | 23.703 | 1.00 | 30.80 A | C |
| ATOM | 2676 | CE | LYS | A | 175 | 71.987 | −44.658 | 25.168 | 1.00 | 30.86 A | C |
| ATOM | 2679 | NZ | LYS | A | 175 | 72.453 | −45.794 | 26.002 | 1.00 | 31.13 A | N |
| ATOM | 2683 | C | LYS | A | 175 | 73.628 | −43.623 | 19.521 | 1.00 | 28.93 A | C |
| ATOM | 2684 | O | LYS | A | 175 | 74.345 | −44.461 | 18.973 | 1.00 | 28.70 A | O |
| ATOM | 2686 | N | ILE | A | 176 | 72.973 | −42.670 | 18.865 | 1.00 | 28.25 A | N |
| ATOM | 2687 | CA | ILE | A | 176 | 73.092 | −42.490 | 17.424 | 1.00 | 27.93 A | C |
| ATOM | 2689 | CB | ILE | A | 176 | 71.735 | −42.112 | 16.764 | 1.00 | 27.94 A | C |
| ATOM | 2691 | CG1 | ILE | A | 176 | 71.039 | −40.966 | 17.514 | 1.00 | 28.01 A | C |

TABLE 8-2-continued

Coordinates for L494P Structure

| | | | | | | | | | | | | |
|---|---|---|---|---|---|---|---|---|---|---|---|---|
| ATOM | 2694 | CD1 | ILE | A | 176 | 69.948 | −40.282 | 16.713 | 1.00 | 27.59 | A | C |
| ATOM | 2698 | CG2 | ILE | A | 176 | 70.822 | −43.325 | 16.716 | 1.00 | 27.61 | A | C |
| ATOM | 2702 | C | ILE | A | 176 | 74.144 | −41.421 | 17.143 | 1.00 | 27.68 | A | C |
| ATOM | 2703 | O | ILE | A | 176 | 74.655 | −40.788 | 18.067 | 1.00 | 27.18 | A | O |
| ATOM | 2705 | N | GLY | A | 177 | 74.473 | −41.237 | 15.868 | 1.00 | 27.66 | A | N |
| ATOM | 2706 | CA | GLY | A | 177 | 75.460 | −40.244 | 15.466 | 1.00 | 27.56 | A | C |
| ATOM | 2709 | C | GLY | A | 177 | 74.987 | −38.831 | 15.744 | 1.00 | 27.45 | A | C |
| ATOM | 2710 | O | GLY | A | 177 | 73.785 | −38.552 | 15.719 | 1.00 | 27.69 | A | O |
| ATOM | 2712 | N | LYS | A | 178 | 75.938 | −37.941 | 16.015 | 1.00 | 27.13 | A | N |
| ATOM | 2713 | CA | LYS | A | 178 | 75.639 | −36.526 | 16.218 | 1.00 | 26.85 | A | C |
| ATOM | 2715 | CB | LYS | A | 178 | 76.934 | −35.721 | 16.371 | 1.00 | 27.05 | A | C |
| ATOM | 2718 | CG | LYS | A | 178 | 76.737 | −34.303 | 16.900 | 1.00 | 27.43 | A | C |
| ATOM | 2721 | CD | LYS | A | 178 | 78.075 | −33.632 | 17.203 | 1.00 | 27.38 | A | C |
| ATOM | 2724 | CE | LYS | A | 178 | 77.917 | −32.490 | 18.197 | 1.00 | 27.26 | A | C |
| ATOM | 2727 | NZ | LYS | A | 178 | 79.230 | −31.954 | 18.642 | 1.00 | 27.88 | A | N |
| ATOM | 2731 | C | LYS | A | 178 | 74.822 | −35.984 | 15.048 | 1.00 | 26.49 | A | C |
| ATOM | 2732 | O | LYS | A | 178 | 73.928 | −35.161 | 15.238 | 1.00 | 26.01 | A | O |
| ATOM | 2734 | N | GLU | A | 179 | 75.130 | −36.465 | 13.843 | 1.00 | 26.38 | A | N |
| ATOM | 2735 | CA | GLU | A | 179 | 74.427 | −36.033 | 12.635 | 1.00 | 26.59 | A | C |
| ATOM | 2737 | CB | GLU | A | 179 | 75.284 | −36.264 | 11.379 | 1.00 | 26.76 | A | C |
| ATOM | 2740 | CG | GLU | A | 179 | 75.652 | −37.715 | 11.067 | 1.00 | 27.14 | A | C |
| ATOM | 2743 | CD | GLU | A | 179 | 76.355 | −37.860 | 9.721 | 1.00 | 27.77 | A | C |
| ATOM | 2744 | OE1 | GLU | A | 179 | 76.641 | −39.008 | 9.321 | 1.00 | 29.07 | A | O |
| ATOM | 2745 | OE2 | GLU | A | 179 | 76.623 | −36.833 | 9.060 | 1.00 | 27.01 | A | O |
| ATOM | 2746 | C | GLU | A | 179 | 73.033 | −36.657 | 12.469 | 1.00 | 26.24 | A | C |
| ATOM | 2747 | O | GLU | A | 179 | 72.139 | −36.021 | 11.903 | 1.00 | 26.60 | A | O |
| ATOM | 2749 | N | LEU | A | 180 | 72.846 | −37.887 | 12.949 | 1.00 | 25.43 | A | N |
| ATOM | 2750 | CA | LEU | A | 180 | 71.525 | −38.531 | 12.901 | 1.00 | 24.84 | A | C |
| ATOM | 2752 | CB | LEU | A | 180 | 71.613 | −40.033 | 13.201 | 1.00 | 24.93 | A | C |
| ATOM | 2755 | CG | LEU | A | 180 | 71.959 | −40.949 | 12.023 | 1.00 | 25.07 | A | C |
| ATOM | 2757 | CD1 | LEU | A | 180 | 72.178 | −42.374 | 12.519 | 1.00 | 24.77 | A | C |
| ATOM | 2761 | CD2 | LEU | A | 180 | 70.874 | −40.911 | 10.949 | 1.00 | 23.22 | A | C |
| ATOM | 2765 | C | LEU | A | 180 | 70.549 | −37.866 | 13.866 | 1.00 | 24.29 | A | C |
| ATOM | 2766 | O | LEU | A | 180 | 69.380 | −37.671 | 13.531 | 1.00 | 24.25 | A | O |
| ATOM | 2768 | N | ALA | A | 181 | 71.031 | −37.522 | 15.058 | 1.00 | 23.73 | A | N |
| ATOM | 2769 | CA | ALA | A | 181 | 70.229 | −36.777 | 16.031 | 1.00 | 23.30 | A | C |
| ATOM | 2771 | CB | ALA | A | 181 | 71.011 | −36.575 | 17.321 | 1.00 | 23.36 | A | C |
| ATOM | 2775 | C | ALA | A | 181 | 69.789 | −35.428 | 15.462 | 1.00 | 22.75 | A | C |
| ATOM | 2776 | O | ALA | A | 181 | 68.650 | −35.010 | 15.655 | 1.00 | 22.37 | A | O |
| ATOM | 2778 | N | GLU | A | 182 | 70.702 | −34.758 | 14.762 | 1.00 | 22.59 | A | N |
| ATOM | 2779 | CA | GLU | A | 182 | 70.399 | −33.493 | 14.088 | 1.00 | 22.35 | A | C |
| ATOM | 2781 | CB | GLU | A | 182 | 71.677 | −32.858 | 13.517 | 1.00 | 22.71 | A | C |
| ATOM | 2784 | CG | GLU | A | 182 | 72.564 | −32.200 | 14.578 | 1.00 | 24.48 | A | C |
| ATOM | 2787 | CD | GLU | A | 182 | 73.892 | −31.690 | 14.031 | 1.00 | 25.90 | A | C |
| ATOM | 2788 | OE1 | GLU | A | 182 | 74.533 | −32.407 | 13.229 | 1.00 | 26.63 | A | O |
| ATOM | 2789 | OE2 | GLU | A | 182 | 74.302 | −30.573 | 14.418 | 1.00 | 25.24 | A | O |
| ATOM | 2790 | C | GLU | A | 182 | 69.371 | −33.694 | 12.980 | 1.00 | 21.48 | A | C |
| ATOM | 2791 | O | GLU | A | 182 | 68.562 | −32.806 | 12.712 | 1.00 | 21.64 | A | O |
| ATOM | 2793 | N | GLN | A | 183 | 69.408 | −34.862 | 12.345 | 1.00 | 20.42 | A | N |
| ATOM | 2794 | CA | GLN | A | 183 | 68.426 | −35.223 | 11.328 | 1.00 | 19.78 | A | C |
| ATOM | 2796 | CB | GLN | A | 183 | 68.890 | −36.458 | 10.548 | 1.00 | 19.69 | A | C |
| ATOM | 2799 | CG | GLN | A | 183 | 68.480 | −36.456 | 9.080 | 1.00 | 20.17 | A | C |
| ATOM | 2802 | CD | GLN | A | 183 | 69.261 | −35.455 | 8.240 | 1.00 | 19.79 | A | C |
| ATOM | 2803 | OE1 | GLN | A | 183 | 68.826 | −35.068 | 7.154 | 1.00 | 18.23 | A | O |
| ATOM | 2804 | NE2 | GLN | A | 183 | 70.419 | −35.035 | 8.737 | 1.00 | 21.56 | A | N |
| ATOM | 2807 | C | GLN | A | 183 | 67.065 | −35.499 | 11.973 | 1.00 | 19.19 | A | C |
| ATOM | 2808 | O | GLN | A | 183 | 66.025 | −35.090 | 11.450 | 1.00 | 18.90 | A | O |
| ATOM | 2810 | N | VAL | A | 184 | 67.084 | −36.194 | 13.108 | 1.00 | 18.65 | A | N |
| ATOM | 2811 | CA | VAL | A | 184 | 65.863 | −36.523 | 13.844 | 1.00 | 18.22 | A | C |
| ATOM | 2813 | CB | VAL | A | 184 | 66.131 | −37.581 | 14.940 | 1.00 | 18.01 | A | C |
| ATOM | 2815 | CG1 | VAL | A | 184 | 66.397 | −38.935 | 14.306 | 1.00 | 17.80 | A | C |
| ATOM | 2819 | CG2 | VAL | A | 184 | 64.960 | −37.673 | 15.903 | 1.00 | 17.60 | A | C |
| ATOM | 2823 | C | VAL | A | 184 | 65.237 | −35.280 | 14.471 | 1.00 | 18.09 | A | C |
| ATOM | 2824 | O | VAL | A | 184 | 64.024 | −35.091 | 14.389 | 1.00 | 18.22 | A | O |
| ATOM | 2826 | N | ASN | A | 185 | 66.066 | −34.443 | 15.094 | 1.00 | 18.01 | A | N |
| ATOM | 2827 | CA | ASN | A | 185 | 65.602 | −33.185 | 15.689 | 1.00 | 18.08 | A | C |
| ATOM | 2829 | CB | ASN | A | 185 | 66.741 | −32.481 | 16.437 | 1.00 | 18.30 | A | C |
| ATOM | 2832 | CG | ASN | A | 185 | 67.082 | −33.151 | 17.759 | 1.00 | 18.99 | A | C |
| ATOM | 2833 | OD1 | ASN | A | 185 | 66.855 | −34.347 | 17.947 | 1.00 | 20.86 | A | O |
| ATOM | 2834 | ND2 | ASN | A | 185 | 67.634 | −32.376 | 18.684 | 1.00 | 19.63 | A | N |
| ATOM | 2837 | C | ASN | A | 185 | 65.010 | −32.239 | 14.646 | 1.00 | 18.07 | A | C |
| ATOM | 2838 | O | ASN | A | 185 | 64.042 | −31.531 | 14.923 | 1.00 | 17.94 | A | O |
| ATOM | 2840 | N | HIS | A | 186 | 65.600 | −32.235 | 13.453 | 1.00 | 18.13 | A | N |
| ATOM | 2841 | CA | HIS | A | 186 | 65.084 | −31.459 | 12.322 | 1.00 | 18.18 | A | C |
| ATOM | 2843 | CB | HIS | A | 186 | 66.104 | −31.468 | 11.180 | 1.00 | 17.97 | A | C |
| ATOM | 2846 | CG | HIS | A | 186 | 65.745 | −30.580 | 10.028 | 1.00 | 16.43 | A | C |
| ATOM | 2847 | ND1 | HIS | A | 186 | 65.727 | −29.205 | 10.126 | 1.00 | 14.28 | A | N |
| ATOM | 2849 | CE1 | HIS | A | 186 | 65.396 | −28.688 | 8.956 | 1.00 | 13.38 | A | C |

TABLE 8-2-continued

| Coordinates for L494P Structure | | | | | | | | | | | | |
|---|---|---|---|---|---|---|---|---|---|---|---|---|
| ATOM | 2851 | NE2 | HIS | A | 186 | 65.205 | −29.678 | 8.102 | 1.00 | 14.26 | A | N |
| ATOM | 2853 | CD2 | HIS | A | 186 | 65.423 | −30.871 | 8.746 | 1.00 | 14.62 | A | C |
| ATOM | 2855 | C | HIS | A | 186 | 63.741 | −32.012 | 11.834 | 1.00 | 18.27 | A | C |
| ATOM | 2856 | O | HIS | A | 186 | 62.784 | −31.261 | 11.657 | 1.00 | 18.39 | A | O |
| ATOM | 2858 | N | ALA | A | 187 | 63.679 | −33.325 | 11.625 | 1.00 | 18.10 | A | N |
| ATOM | 2859 | CA | ALA | A | 187 | 62.454 | −33.979 | 11.159 | 1.00 | 17.75 | A | C |
| ATOM | 2861 | CB | ALA | A | 187 | 62.726 | −35.439 | 10.848 | 1.00 | 17.93 | A | C |
| ATOM | 2865 | C | ALA | A | 187 | 61.315 | −33.859 | 12.173 | 1.00 | 17.45 | A | C |
| ATOM | 2866 | O | ALA | A | 187 | 60.161 | −33.643 | 11.797 | 1.00 | 17.00 | A | O |
| ATOM | 2868 | N | LEU | A | 188 | 61.646 | −33.998 | 13.456 | 1.00 | 17.36 | A | N |
| ATOM | 2869 | CA | LEU | A | 188 | 60.648 | −33.889 | 14.526 | 1.00 | 17.21 | A | C |
| ATOM | 2871 | CB | LEU | A | 188 | 61.154 | −34.531 | 15.826 | 1.00 | 16.89 | A | C |
| ATOM | 2874 | CG | LEU | A | 188 | 61.033 | −36.059 | 15.872 | 1.00 | 16.43 | A | C |
| ATOM | 2876 | CD1 | LEU | A | 188 | 61.936 | −36.663 | 16.933 | 1.00 | 15.33 | A | C |
| ATOM | 2880 | CD2 | LEU | A | 188 | 59.586 | −36.471 | 16.107 | 1.00 | 16.80 | A | C |
| ATOM | 2884 | C | LEU | A | 188 | 60.216 | −32.442 | 14.773 | 1.00 | 17.11 | A | C |
| ATOM | 2885 | O | LEU | A | 188 | 59.104 | −32.205 | 15.245 | 1.00 | 17.54 | A | O |
| ATOM | 2887 | N | GLU | A | 189 | 61.088 | −31.484 | 14.462 | 1.00 | 16.53 | A | N |
| ATOM | 2888 | CA | GLU | A | 189 | 60.711 | −30.071 | 14.493 | 1.00 | 16.03 | A | C |
| ATOM | 2890 | CB | GLU | A | 189 | 61.894 | −29.181 | 14.088 | 1.00 | 16.08 | A | C |
| ATOM | 2893 | CG | GLU | A | 189 | 61.639 | −27.679 | 14.221 | 1.00 | 17.05 | A | C |
| ATOM | 2896 | CD | GLU | A | 189 | 62.570 | −26.845 | 13.357 | 1.00 | 18.24 | A | C |
| ATOM | 2897 | OE1 | GLU | A | 189 | 62.631 | −27.099 | 12.136 | 1.00 | 18.22 | A | O |
| ATOM | 2898 | OE2 | GLU | A | 189 | 63.229 | −25.927 | 13.893 | 1.00 | 18.67 | A | O |
| ATOM | 2899 | C | GLU | A | 189 | 59.554 | −29.859 | 13.527 | 1.00 | 15.30 | A | C |
| ATOM | 2900 | O | GLU | A | 189 | 58.502 | −29.345 | 13.901 | 1.00 | 14.88 | A | O |
| ATOM | 2902 | N | LEU | A | 190 | 59.773 | −30.280 | 12.284 | 1.00 | 14.95 | A | N |
| ATOM | 2903 | CA | LEU | A | 190 | 58.806 | −30.145 | 11.203 | 1.00 | 14.48 | A | C |
| ATOM | 2905 | CB | LEU | A | 190 | 58.730 | −28.685 | 10.740 | 1.00 | 14.32 | A | C |
| ATOM | 2908 | CG | LEU | A | 190 | 57.637 | −28.308 | 9.735 | 1.00 | 13.70 | A | C |
| ATOM | 2910 | CD1 | LEU | A | 190 | 56.257 | −28.398 | 10.377 | 1.00 | 12.88 | A | C |
| ATOM | 2914 | CD2 | LEU | A | 190 | 57.885 | −26.909 | 9.175 | 1.00 | 9.41 | A | C |
| ATOM | 2918 | C | LEU | A | 190 | 59.281 | −31.037 | 10.057 | 1.00 | 14.33 | A | C |
| ATOM | 2919 | O | LEU | A | 190 | 60.460 | −31.011 | 9.711 | 1.00 | 14.00 | A | O |
| ATOM | 2921 | N | PRO | A | 191 | 58.379 | −31.839 | 9.468 | 1.00 | 14.65 | A | N |
| ATOM | 2922 | CA | PRO | A | 191 | 58.827 | −32.779 | 8.437 | 1.00 | 14.74 | A | C |
| ATOM | 2924 | CB | PRO | A | 191 | 57.674 | −33.777 | 8.358 | 1.00 | 14.70 | A | C |
| ATOM | 2927 | CG | PRO | A | 191 | 56.473 | −32.971 | 8.707 | 1.00 | 15.26 | A | C |
| ATOM | 2930 | CD | PRO | A | 191 | 56.918 | −31.887 | 9.655 | 1.00 | 14.91 | A | C |
| ATOM | 2933 | C | PRO | A | 191 | 59.059 | −32.111 | 7.082 | 1.00 | 14.61 | A | C |
| ATOM | 2934 | O | PRO | A | 191 | 58.725 | −30.941 | 6.903 | 1.00 | 15.11 | A | O |
| ATOM | 2935 | N | LEU | A | 192 | 59.624 | −32.860 | 6.142 | 1.00 | 14.26 | A | N |
| ATOM | 2936 | CA | LEU | A | 192 | 59.935 | −32.339 | 4.814 | 1.00 | 13.99 | A | C |
| ATOM | 2938 | CB | LEU | A | 192 | 60.580 | −33.424 | 3.950 | 1.00 | 14.19 | A | C |
| ATOM | 2941 | CG | LEU | A | 192 | 61.980 | −33.866 | 4.391 | 1.00 | 16.27 | A | C |
| ATOM | 2943 | CD1 | LEU | A | 192 | 62.353 | −35.200 | 3.765 | 1.00 | 17.03 | A | C |
| ATOM | 2947 | CD2 | LEU | A | 192 | 63.019 | −32.803 | 4.053 | 1.00 | 17.29 | A | C |
| ATOM | 2951 | C | LEU | A | 192 | 58.688 | −31.817 | 4.122 | 1.00 | 13.36 | A | C |
| ATOM | 2952 | O | LEU | A | 192 | 58.662 | −30.679 | 3.661 | 1.00 | 13.23 | A | O |
| ATOM | 2954 | N | HIS | A | 193 | 57.651 | −32.649 | 4.086 | 1.00 | 13.28 | A | N |
| ATOM | 2955 | CA | HIS | A | 193 | 56.421 | −32.355 | 3.343 | 1.00 | 13.38 | A | C |
| ATOM | 2957 | CB | HIS | A | 193 | 55.449 | −33.537 | 3.458 | 1.00 | 13.14 | A | C |
| ATOM | 2960 | CG | HIS | A | 193 | 54.224 | −33.402 | 2.608 | 1.00 | 12.08 | A | C |
| ATOM | 2961 | ND1 | HIS | A | 193 | 54.279 | −33.279 | 1.237 | 1.00 | 11.82 | A | N |
| ATOM | 2963 | CE1 | HIS | A | 193 | 53.053 | −33.178 | 0.757 | 1.00 | 11.83 | A | C |
| ATOM | 2965 | NE2 | HIS | A | 193 | 52.204 | −33.235 | 1.767 | 1.00 | 9.95 | A | N |
| ATOM | 2967 | CD2 | HIS | A | 193 | 52.910 | −33.375 | 2.936 | 1.00 | 10.22 | A | C |
| ATOM | 2969 | C | HIS | A | 193 | 55.722 | −31.055 | 3.764 | 1.00 | 13.92 | A | C |
| ATOM | 2970 | O | HIS | A | 193 | 54.964 | −30.478 | 2.979 | 1.00 | 13.67 | A | O |
| ATOM | 2972 | N | ARG | A | 194 | 55.971 | −30.598 | 4.989 | 1.00 | 14.56 | A | N |
| ATOM | 2973 | CA | ARG | A | 194 | 55.393 | −29.343 | 5.475 | 1.00 | 15.25 | A | C |
| ATOM | 2975 | CB | ARG | A | 194 | 54.749 | −29.557 | 6.843 | 1.00 | 15.26 | A | C |
| ATOM | 2978 | CG | ARG | A | 194 | 53.625 | −30.571 | 6.824 | 1.00 | 16.11 | A | C |
| ATOM | 2981 | CD | ARG | A | 194 | 52.888 | −30.620 | 8.150 | 1.00 | 18.42 | A | C |
| ATOM | 2984 | NE | ARG | A | 194 | 51.885 | −31.684 | 8.170 | 1.00 | 19.85 | A | N |
| ATOM | 2986 | CZ | ARG | A | 194 | 51.170 | −32.042 | 9.236 | 1.00 | 20.13 | A | C |
| ATOM | 2987 | NH1 | ARG | A | 194 | 51.330 | −31.431 | 10.406 | 1.00 | 21.48 | A | N |
| ATOM | 2990 | NH2 | ARG | A | 194 | 50.288 | −33.028 | 9.132 | 1.00 | 20.98 | A | N |
| ATOM | 2993 | C | ARG | A | 194 | 56.392 | −28.180 | 5.542 | 1.00 | 15.65 | A | C |
| ATOM | 2994 | O | ARG | A | 194 | 55.981 | −27.029 | 5.629 | 1.00 | 16.13 | A | O |
| ATOM | 2996 | N | ARG | A | 195 | 57.691 | −28.468 | 5.501 | 1.00 | 15.83 | A | N |
| ATOM | 2997 | CA | ARG | A | 195 | 58.707 | −27.416 | 5.544 | 1.00 | 15.92 | A | C |
| ATOM | 2999 | CB | ARG | A | 195 | 60.047 | −27.994 | 5.992 | 1.00 | 16.22 | A | C |
| ATOM | 3002 | CG | ARG | A | 195 | 61.069 | −26.938 | 6.388 | 1.00 | 18.02 | A | C |
| ATOM | 3005 | CD | ARG | A | 195 | 62.434 | −27.540 | 6.681 | 1.00 | 18.19 | A | C |
| ATOM | 3008 | NE | ARG | A | 195 | 62.382 | −28.612 | 7.672 | 1.00 | 19.14 | A | N |
| ATOM | 3010 | CZ | ARG | A | 195 | 62.233 | −28.434 | 8.984 | 1.00 | 21.01 | A | C |
| ATOM | 3011 | NH1 | ARG | A | 195 | 62.104 | −27.216 | 9.507 | 1.00 | 20.62 | A | N |

TABLE 8-2-continued

Coordinates for L494P Structure

| | | | | | | | | | | | | |
|---|---|---|---|---|---|---|---|---|---|---|---|---|
| ATOM | 3014 | NH2 | ARG | A | 195 | 62.212 | −29.490 | 9.788 | 1.00 | 22.42 | A | N |
| ATOM | 3017 | C | ARG | A | 195 | 58.866 | −26.768 | 4.171 | 1.00 | 15.95 | A | C |
| ATOM | 3018 | O | ARG | A | 195 | 58.929 | −27.471 | 3.158 | 1.00 | 15.90 | A | O |
| ATOM | 3020 | N | THR | A | 196 | 58.946 | −25.436 | 4.133 | 1.00 | 15.87 | A | N |
| ATOM | 3021 | CA | THR | A | 196 | 59.146 | −24.725 | 2.866 | 1.00 | 15.91 | A | C |
| ATOM | 3023 | CB | THR | A | 196 | 59.126 | −23.183 | 3.019 | 1.00 | 15.61 | A | C |
| ATOM | 3025 | OG1 | THR | A | 196 | 60.106 | −22.770 | 3.979 | 1.00 | 15.28 | A | O |
| ATOM | 3027 | CG2 | THR | A | 196 | 57.757 | −22.700 | 3.452 | 1.00 | 15.63 | A | C |
| ATOM | 3031 | C | THR | A | 196 | 60.468 | −25.151 | 2.236 | 1.00 | 16.35 | A | C |
| ATOM | 3032 | O | THR | A | 196 | 61.379 | −25.611 | 2.928 | 1.00 | 16.39 | A | O |
| ATOM | 3034 | N | GLN | A | 197 | 60.562 | −24.986 | 0.922 | 1.00 | 16.60 | A | N |
| ATOM | 3035 | CA | GLN | A | 197 | 61.675 | −25.537 | 0.147 | 1.00 | 16.65 | A | C |
| ATOM | 3037 | CB | GLN | A | 197 | 61.292 | −25.578 | −1.344 | 1.00 | 16.83 | A | C |
| ATOM | 3040 | CG | GLN | A | 197 | 62.268 | −24.945 | −2.318 | 1.00 | 18.46 | A | C |
| ATOM | 3043 | CD | GLN | A | 197 | 63.359 | −25.875 | −2.795 | 1.00 | 19.11 | A | C |
| ATOM | 3044 | OE1 | GLN | A | 197 | 64.519 | −25.716 | −2.426 | 1.00 | 18.91 | A | O |
| ATOM | 3045 | NE2 | GLN | A | 197 | 62.997 | −26.839 | −3.639 | 1.00 | 19.88 | A | N |
| ATOM | 3048 | C | GLN | A | 197 | 63.023 | −24.834 | 0.399 | 1.00 | 16.45 | A | C |
| ATOM | 3049 | O | GLN | A | 197 | 64.073 | −25.476 | 0.344 | 1.00 | 16.57 | A | O |
| ATOM | 3051 | N | ARG | A | 198 | 62.990 | −23.535 | 0.692 | 1.00 | 16.22 | A | N |
| ATOM | 3052 | CA | ARG | A | 198 | 64.219 | −22.767 | 0.939 | 1.00 | 15.80 | A | C |
| ATOM | 3054 | CB | ARG | A | 198 | 63.960 | −21.270 | 0.758 | 1.00 | 15.86 | A | C |
| ATOM | 3057 | CG | ARG | A | 198 | 63.690 | −20.856 | −0.682 | 1.00 | 16.65 | A | C |
| ATOM | 3060 | CD | ARG | A | 198 | 64.967 | −20.804 | −1.526 | 1.00 | 16.78 | A | C |
| ATOM | 3063 | NE | ARG | A | 198 | 65.295 | −22.072 | −2.175 | 1.00 | 16.13 | A | N |
| ATOM | 3065 | CZ | ARG | A | 198 | 66.289 | −22.234 | −3.048 | 1.00 | 18.48 | A | C |
| ATOM | 3066 | NH1 | ARG | A | 198 | 67.067 | −21.209 | −3.393 | 1.00 | 17.78 | A | N |
| ATOM | 3069 | NH2 | ARG | A | 198 | 66.511 | −23.431 | −3.585 | 1.00 | 19.12 | A | N |
| ATOM | 3072 | C | ARG | A | 198 | 64.819 | −23.027 | 2.324 | 1.00 | 15.17 | A | C |
| ATOM | 3073 | O | ARG | A | 198 | 66.032 | −23.193 | 2.452 | 1.00 | 14.96 | A | O |
| ATOM | 3075 | N | LEU | A | 199 | 63.974 | −23.051 | 3.354 | 1.00 | 14.66 | A | N |
| ATOM | 3076 | CA | LEU | A | 199 | 64.425 | −23.342 | 4.719 | 1.00 | 14.28 | A | C |
| ATOM | 3078 | CB | LEU | A | 199 | 63.290 | −23.155 | 5.738 | 1.00 | 14.42 | A | C |
| ATOM | 3081 | CG | LEU | A | 199 | 62.996 | −21.723 | 6.198 | 1.00 | 13.58 | A | C |
| ATOM | 3083 | CD1 | LEU | A | 199 | 64.225 | −21.108 | 6.838 | 1.00 | 12.91 | A | C |
| ATOM | 3087 | CD2 | LEU | A | 199 | 61.823 | −21.698 | 7.166 | 1.00 | 11.52 | A | C |
| ATOM | 3091 | C | LEU | A | 199 | 64.973 | −24.760 | 4.820 | 1.00 | 13.99 | A | C |
| ATOM | 3092 | O | LEU | A | 199 | 65.941 | −25.007 | 5.542 | 1.00 | 13.43 | A | O |
| ATOM | 3094 | N | GLU | A | 200 | 64.338 | −25.686 | 4.105 | 1.00 | 13.99 | A | N |
| ATOM | 3095 | CA | GLU | A | 200 | 64.840 | −27.052 | 3.993 | 1.00 | 14.04 | A | C |
| ATOM | 3097 | CB | GLU | A | 200 | 63.833 | −27.945 | 3.254 | 1.00 | 14.26 | A | C |
| ATOM | 3100 | CG | GLU | A | 200 | 64.284 | −29.393 | 3.026 | 1.00 | 15.07 | A | C |
| ATOM | 3103 | CD | GLU | A | 200 | 64.864 | −30.053 | 4.267 | 1.00 | 16.59 | A | C |
| ATOM | 3104 | OE1 | GLU | A | 200 | 64.228 | −29.992 | 5.341 | 1.00 | 18.96 | A | O |
| ATOM | 3105 | OE2 | GLU | A | 200 | 65.957 | −30.646 | 4.165 | 1.00 | 16.21 | A | O |
| ATOM | 3106 | C | GLU | A | 200 | 66.176 | −27.051 | 3.263 | 1.00 | 13.82 | A | C |
| ATOM | 3107 | O | GLU | A | 200 | 67.090 | −27.786 | 3.640 | 1.00 | 14.49 | A | O |
| ATOM | 3109 | N | ALA | A | 201 | 66.283 | −26.220 | 2.226 | 1.00 | 13.15 | A | N |
| ATOM | 3110 | CA | ALA | A | 201 | 67.510 | −26.108 | 1.437 | 1.00 | 12.65 | A | C |
| ATOM | 3112 | CB | ALA | A | 201 | 67.272 | −25.238 | 0.221 | 1.00 | 12.47 | A | C |
| ATOM | 3116 | C | ALA | A | 201 | 68.696 | −25.576 | 2.249 | 1.00 | 12.48 | A | C |
| ATOM | 3117 | O | ALA | A | 201 | 69.755 | −26.200 | 2.272 | 1.00 | 12.06 | A | O |
| ATOM | 3119 | N | VAL | A | 202 | 68.515 | −24.439 | 2.922 | 1.00 | 12.67 | A | N |
| ATOM | 3120 | CA | VAL | A | 202 | 69.609 | −23.801 | 3.673 | 1.00 | 12.57 | A | C |
| ATOM | 3122 | CB | VAL | A | 202 | 69.196 | −22.440 | 4.277 | 1.00 | 12.42 | A | C |
| ATOM | 3124 | CG1 | VAL | A | 202 | 68.324 | −22.635 | 5.506 | 1.00 | 12.80 | A | C |
| ATOM | 3128 | CG2 | VAL | A | 202 | 70.426 | −21.626 | 4.635 | 1.00 | 12.02 | A | C |
| ATOM | 3132 | C | VAL | A | 202 | 70.130 | −24.682 | 4.800 | 1.00 | 12.80 | A | C |
| ATOM | 3133 | O | VAL | A | 202 | 71.296 | −24.580 | 5.176 | 1.00 | 12.89 | A | O |
| ATOM | 3135 | N | TRP | A | 203 | 69.261 | −25.537 | 5.336 | 1.00 | 13.26 | A | N |
| ATOM | 3136 | CA | TRP | A | 203 | 69.638 | −26.478 | 6.385 | 1.00 | 13.35 | A | C |
| ATOM | 3138 | CB | TRP | A | 203 | 68.399 | −26.965 | 7.140 | 1.00 | 13.36 | A | C |
| ATOM | 3141 | CG | TRP | A | 203 | 68.720 | −27.817 | 8.329 | 1.00 | 12.25 | A | C |
| ATOM | 3142 | CD1 | TRP | A | 203 | 68.960 | −27.387 | 9.601 | 1.00 | 12.59 | A | C |
| ATOM | 3144 | NE1 | TRP | A | 203 | 69.219 | −28.456 | 10.421 | 1.00 | 11.51 | A | N |
| ATOM | 3146 | CE2 | TRP | A | 203 | 69.152 | −29.607 | 9.683 | 1.00 | 10.81 | A | C |
| ATOM | 3147 | CD2 | TRP | A | 203 | 68.837 | −29.242 | 8.358 | 1.00 | 11.23 | A | C |
| ATOM | 3148 | CE3 | TRP | A | 203 | 68.706 | −30.247 | 7.393 | 1.00 | 12.78 | A | C |
| ATOM | 3150 | CZ3 | TRP | A | 203 | 68.893 | −31.567 | 7.778 | 1.00 | 12.64 | A | C |
| ATOM | 3152 | CH2 | TRP | A | 203 | 69.205 | −31.897 | 9.107 | 1.00 | 11.26 | A | C |
| ATOM | 3154 | CZ2 | TRP | A | 203 | 69.339 | −30.934 | 10.069 | 1.00 | 10.95 | A | C |
| ATOM | 3156 | C | TRP | A | 203 | 70.379 | −27.670 | 5.795 | 1.00 | 13.47 | A | C |
| ATOM | 3157 | O | TRP | A | 203 | 71.515 | −27.954 | 6.183 | 1.00 | 13.39 | A | O |
| ATOM | 3159 | N | SER | A | 204 | 69.730 | −28.355 | 4.852 | 1.00 | 13.61 | A | N |
| ATOM | 3160 | CA | SER | A | 204 | 70.270 | −29.589 | 4.263 | 1.00 | 13.87 | A | C |
| ATOM | 3162 | CB | SER | A | 204 | 69.323 | −30.142 | 3.194 | 1.00 | 13.67 | A | C |
| ATOM | 3165 | OG | SER | A | 204 | 68.234 | −30.819 | 3.792 | 1.00 | 13.52 | A | O |
| ATOM | 3167 | C | SER | A | 204 | 71.666 | −29.407 | 3.674 | 1.00 | 14.22 | A | C |

TABLE 8-2-continued

| Coordinates for L494P Structure | | | | | | | | | | | |
|---|---|---|---|---|---|---|---|---|---|---|---|
| ATOM | 3168 | O | SER | A | 204 | 72.476 | −30.333 | 3.708 | 1.00 | 14.33 A | O |
| ATOM | 3170 | N | ILE | A | 205 | 71.933 | −28.216 | 3.139 | 1.00 | 14.32 A | N |
| ATOM | 3171 | CA | ILE | A | 205 | 73.259 | −27.852 | 2.639 | 1.00 | 14.23 A | C |
| ATOM | 3173 | CB | ILE | A | 205 | 73.234 | −26.458 | 1.967 | 1.00 | 14.07 A | C |
| ATOM | 3175 | CG1 | ILE | A | 205 | 72.473 | −26.517 | 0.643 | 1.00 | 13.44 A | C |
| ATOM | 3178 | CD1 | ILE | A | 205 | 72.074 | −25.161 | 0.117 | 1.00 | 12.73 A | C |
| ATOM | 3182 | CG2 | ILE | A | 205 | 74.647 | −25.947 | 1.718 | 1.00 | 15.49 A | C |
| ATOM | 3186 | C | ILE | A | 205 | 74.292 | −27.845 | 3.769 | 1.00 | 14.47 A | C |
| ATOM | 3187 | O | ILE | A | 205 | 75.347 | −28.479 | 3.663 | 1.00 | 14.24 A | O |
| ATOM | 3189 | N | GLU | A | 206 | 73.975 | −27.126 | 4.846 | 1.00 | 14.66 A | N |
| ATOM | 3190 | CA | GLU | A | 206 | 74.842 | −27.051 | 6.023 | 1.00 | 14.82 A | C |
| ATOM | 3192 | CB | GLU | A | 206 | 74.219 | −26.131 | 7.082 | 1.00 | 15.15 A | C |
| ATOM | 3195 | CG | GLU | A | 206 | 75.064 | −25.916 | 8.346 | 1.00 | 16.59 A | C |
| ATOM | 3198 | CD | GLU | A | 206 | 76.420 | −25.279 | 8.071 | 1.00 | 17.90 A | C |
| ATOM | 3199 | OE1 | GLU | A | 206 | 76.582 | −24.629 | 7.014 | 1.00 | 19.11 A | O |
| ATOM | 3200 | OE2 | GLU | A | 206 | 77.325 | −25.424 | 8.922 | 1.00 | 18.61 A | O |
| ATOM | 3201 | C | GLU | A | 206 | 75.094 | −28.436 | 6.616 | 1.00 | 14.53 A | C |
| ATOM | 3202 | O | GLU | A | 206 | 76.197 | −28.730 | 7.072 | 1.00 | 14.36 A | O |
| ATOM | 3204 | N | ALA | A | 207 | 74.063 | −29.277 | 6.604 | 1.00 | 14.37 A | N |
| ATOM | 3205 | CA | ALA | A | 207 | 74.173 | −30.655 | 7.079 | 1.00 | 14.14 A | C |
| ATOM | 3207 | CB | ALA | A | 207 | 72.785 | −31.266 | 7.234 | 1.00 | 14.13 A | C |
| ATOM | 3211 | C | ALA | A | 207 | 75.015 | −31.514 | 6.141 | 1.00 | 13.78 A | C |
| ATOM | 3212 | O | ALA | A | 207 | 75.898 | −32.248 | 6.585 | 1.00 | 13.22 A | O |
| ATOM | 3214 | N | TYR | A | 208 | 74.733 | −31.410 | 4.845 | 1.00 | 13.95 A | N |
| ATOM | 3215 | CA | TYR | A | 208 | 75.319 | −32.297 | 3.838 | 1.00 | 14.17 A | C |
| ATOM | 3217 | CB | TYR | A | 208 | 74.531 | −32.189 | 2.525 | 1.00 | 14.20 A | C |
| ATOM | 3220 | CG | TYR | A | 208 | 74.881 | −33.219 | 1.471 | 1.00 | 13.85 A | C |
| ATOM | 3221 | CD1 | TYR | A | 208 | 74.401 | −34.523 | 1.557 | 1.00 | 15.48 A | C |
| ATOM | 3223 | CE1 | TYR | A | 208 | 74.710 | −35.472 | 0.583 | 1.00 | 15.09 A | C |
| ATOM | 3225 | CZ | TYR | A | 208 | 75.500 | −35.115 | −0.494 | 1.00 | 13.90 A | C |
| ATOM | 3226 | OH | TYR | A | 208 | 75.811 | −36.045 | −1.458 | 1.00 | 11.21 A | O |
| ATOM | 3228 | CE2 | TYR | A | 208 | 75.984 | −33.823 | −0.604 | 1.00 | 14.12 A | C |
| ATOM | 3230 | CD2 | TYR | A | 208 | 75.670 | −32.882 | 0.375 | 1.00 | 13.38 A | C |
| ATOM | 3232 | C | TYR | A | 208 | 76.804 | −32.031 | 3.588 | 1.00 | 14.31 A | C |
| ATOM | 3233 | O | TYR | A | 208 | 77.515 | −32.918 | 3.120 | 1.00 | 14.93 A | O |
| ATOM | 3235 | N | ARG | A | 209 | 77.276 | −30.825 | 3.892 | 1.00 | 14.14 A | N |
| ATOM | 3236 | CA | ARG | A | 209 | 78.691 | −30.508 | 3.698 | 1.00 | 14.20 A | C |
| ATOM | 3238 | CB | ARG | A | 209 | 78.912 | −28.994 | 3.580 | 1.00 | 14.05 A | C |
| ATOM | 3241 | CG | ARG | A | 209 | 78.753 | −28.202 | 4.872 | 1.00 | 14.18 A | C |
| ATOM | 3244 | CD | ARG | A | 209 | 79.424 | −26.841 | 4.766 | 1.00 | 14.24 A | C |
| ATOM | 3247 | NE | ARG | A | 209 | 78.659 | −25.905 | 3.944 | 1.00 | 13.50 A | N |
| ATOM | 3249 | CZ | ARG | A | 209 | 79.136 | −24.767 | 3.440 | 1.00 | 12.08 A | C |
| ATOM | 3250 | NH1 | ARG | A | 209 | 80.397 | −24.399 | 3.650 | 1.00 | 10.79 A | N |
| ATOM | 3253 | NH2 | ARG | A | 209 | 78.343 | −23.991 | 2.710 | 1.00 | 12.81 A | N |
| ATOM | 3256 | C | ARG | A | 209 | 79.571 | −31.108 | 4.802 | 1.00 | 14.55 A | C |
| ATOM | 3257 | O | ARG | A | 209 | 80.767 | −31.309 | 4.600 | 1.00 | 14.80 A | O |
| ATOM | 3259 | N | LYS | A | 210 | 78.977 | −31.388 | 5.960 | 1.00 | 15.15 A | N |
| ATOM | 3260 | CA | LYS | A | 210 | 79.694 | −32.011 | 7.076 | 1.00 | 15.61 A | C |
| ATOM | 3262 | CB | LYS | A | 210 | 79.018 | −31.669 | 8.406 | 1.00 | 15.61 A | C |
| ATOM | 3265 | CG | LYS | A | 210 | 78.981 | −30.177 | 8.719 | 1.00 | 15.58 A | C |
| ATOM | 3268 | CD | LYS | A | 210 | 78.026 | −29.867 | 9.865 | 1.00 | 15.71 A | C |
| ATOM | 3271 | CE | LYS | A | 210 | 77.856 | −28.368 | 10.057 | 1.00 | 15.97 A | C |
| ATOM | 3274 | NZ | LYS | A | 210 | 76.875 | −28.038 | 11.131 | 1.00 | 15.56 A | N |
| ATOM | 3278 | C | LYS | A | 210 | 79.795 | −33.531 | 6.911 | 1.00 | 16.30 A | C |
| ATOM | 3279 | O | LYS | A | 210 | 80.599 | −34.176 | 7.584 | 1.00 | 16.27 A | O |
| ATOM | 3281 | N | LYS | A | 211 | 78.972 | −34.104 | 6.033 | 1.00 | 17.15 A | N |
| ATOM | 3282 | CA | LYS | A | 211 | 79.141 | −35.496 | 5.628 | 1.00 | 17.96 A | C |
| ATOM | 3284 | CB | LYS | A | 211 | 78.049 | −35.934 | 4.644 | 1.00 | 18.23 A | C |
| ATOM | 3287 | CG | LYS | A | 211 | 76.694 | −36.253 | 5.260 | 1.00 | 19.44 A | C |
| ATOM | 3290 | CD | LYS | A | 211 | 75.846 | −37.071 | 4.282 | 1.00 | 21.73 A | C |
| ATOM | 3293 | CE | LYS | A | 211 | 74.424 | −37.282 | 4.784 | 1.00 | 23.25 A | C |
| ATOM | 3296 | NZ | LYS | A | 211 | 74.388 | −38.036 | 6.071 | 1.00 | 24.71 A | N |
| ATOM | 3300 | C | LYS | A | 211 | 80.499 | −35.635 | 4.952 | 1.00 | 18.46 A | C |
| ATOM | 3301 | O | LYS | A | 211 | 80.739 | −35.015 | 3.915 | 1.00 | 18.58 A | O |
| ATOM | 3303 | N | GLU | A | 212 | 81.383 | −36.442 | 5.534 | 1.00 | 19.08 A | N |
| ATOM | 3304 | CA | GLU | A | 212 | 82.726 | −36.640 | 4.975 | 1.00 | 19.70 A | C |
| ATOM | 3306 | CB | GLU | A | 212 | 83.607 | −37.453 | 5.936 | 1.00 | 20.07 A | C |
| ATOM | 3309 | CG | GLU | A | 212 | 85.113 | −37.304 | 5.683 | 1.00 | 20.44 A | C |
| ATOM | 3312 | CD | GLU | A | 212 | 85.953 | −38.339 | 6.423 | 1.00 | 20.22 A | C |
| ATOM | 3313 | OE1 | GLU | A | 212 | 86.981 | −37.951 | 7.016 | 1.00 | 19.88 A | O |
| ATOM | 3314 | OE2 | GLU | A | 212 | 85.595 | −39.538 | 6.407 | 1.00 | 18.93 A | O |
| ATOM | 3315 | C | GLU | A | 212 | 82.667 | −37.328 | 3.606 | 1.00 | 19.59 A | C |
| ATOM | 3316 | O | GLU | A | 212 | 83.540 | −37.119 | 2.763 | 1.00 | 19.49 A | O |
| ATOM | 3318 | N | ASP | A | 213 | 81.627 | −38.133 | 3.393 | 1.00 | 19.59 A | N |
| ATOM | 3319 | CA | ASP | A | 213 | 81.420 | −38.841 | 2.128 | 1.00 | 19.85 A | C |
| ATOM | 3321 | CB | ASP | A | 213 | 80.904 | −40.262 | 2.404 | 1.00 | 20.37 A | C |
| ATOM | 3324 | CG | ASP | A | 213 | 79.566 | −40.272 | 3.132 | 1.00 | 22.19 A | C |
| ATOM | 3325 | OD1 | ASP | A | 213 | 79.448 | −39.595 | 4.178 | 1.00 | 23.92 A | O |

TABLE 8-2-continued

Coordinates for L494P Structure

| | | | | | | | | | | | | |
|---|---|---|---|---|---|---|---|---|---|---|---|---|
| ATOM | 3326 | OD2 | ASP | A | 213 | 78.636 | −40.959 | 2.660 | 1.00 | 25.96 | A | O |
| ATOM | 3327 | C | ASP | A | 213 | 80.452 | −38.100 | 1.194 | 1.00 | 19.34 | A | C |
| ATOM | 3328 | O | ASP | A | 213 | 79.764 | −38.723 | 0.383 | 1.00 | 19.04 | A | O |
| ATOM | 3330 | N | ALA | A | 214 | 80.412 | −36.773 | 1.299 | 1.00 | 19.11 | A | N |
| ATOM | 3331 | CA | ALA | A | 214 | 79.501 | −35.959 | 0.496 | 1.00 | 19.01 | A | C |
| ATOM | 3333 | CB | ALA | A | 214 | 79.366 | −34.570 | 1.099 | 1.00 | 18.73 | A | C |
| ATOM | 3337 | C | ALA | A | 214 | 79.984 | −35.857 | −0.946 | 1.00 | 19.16 | A | C |
| ATOM | 3338 | O | ALA | A | 214 | 81.188 | −35.779 | −1.198 | 1.00 | 19.39 | A | O |
| ATOM | 3340 | N | ASN | A | 215 | 79.040 | −35.860 | −1.885 | 1.00 | 19.33 | A | N |
| ATOM | 3341 | CA | ASN | A | 215 | 79.354 | −35.675 | −3.302 | 1.00 | 19.51 | A | C |
| ATOM | 3343 | CB | ASN | A | 215 | 78.184 | −36.142 | −4.182 | 1.00 | 19.77 | A | C |
| ATOM | 3346 | CG | ASN | A | 215 | 78.595 | −36.396 | −5.628 | 1.00 | 20.67 | A | C |
| ATOM | 3347 | OD1 | ASN | A | 215 | 78.874 | −35.463 | −6.383 | 1.00 | 22.18 | A | O |
| ATOM | 3348 | ND2 | ASN | A | 215 | 78.623 | −37.666 | −6.019 | 1.00 | 20.55 | A | N |
| ATOM | 3351 | C | ASN | A | 215 | 79.683 | −34.202 | −3.564 | 1.00 | 19.05 | A | C |
| ATOM | 3352 | O | ASN | A | 215 | 78.819 | −33.333 | −3.428 | 1.00 | 19.14 | A | O |
| ATOM | 3354 | N | GLN | A | 216 | 80.934 | −33.932 | −3.932 | 1.00 | 18.33 | A | N |
| ATOM | 3355 | CA | GLN | A | 216 | 81.424 | −32.558 | −4.070 | 1.00 | 17.80 | A | C |
| ATOM | 3357 | CB | GLN | A | 216 | 82.943 | −32.536 | −4.292 | 1.00 | 17.98 | A | C |
| ATOM | 3360 | CG | GLN | A | 216 | 83.771 | −33.244 | −3.213 | 1.00 | 19.00 | A | C |
| ATOM | 3363 | CD | GLN | A | 216 | 83.465 | −32.763 | −1.804 | 1.00 | 19.26 | A | C |
| ATOM | 3364 | OE1 | GLN | A | 216 | 83.323 | −31.565 | −1.560 | 1.00 | 18.93 | A | O |
| ATOM | 3365 | NE2 | GLN | A | 216 | 83.369 | −33.701 | −0.868 | 1.00 | 19.47 | A | N |
| ATOM | 3368 | C | GLN | A | 216 | 80.735 | −31.814 | −5.208 | 1.00 | 17.08 | A | C |
| ATOM | 3369 | O | GLN | A | 216 | 80.432 | −30.627 | −5.080 | 1.00 | 17.09 | A | O |
| ATOM | 3371 | N | VAL | A | 217 | 80.490 | −32.511 | −6.315 | 1.00 | 16.33 | A | N |
| ATOM | 3372 | CA | VAL | A | 217 | 79.826 | −31.912 | −7.474 | 1.00 | 15.80 | A | C |
| ATOM | 3374 | CB | VAL | A | 217 | 79.755 | −32.894 | −8.668 | 1.00 | 15.84 | A | C |
| ATOM | 3376 | CG1 | VAL | A | 217 | 78.935 | −32.298 | −9.809 | 1.00 | 14.63 | A | C |
| ATOM | 3380 | CG2 | VAL | A | 217 | 81.155 | −33.254 | −9.147 | 1.00 | 16.01 | A | C |
| ATOM | 3384 | C | VAL | A | 217 | 78.411 | −31.454 | −7.123 | 1.00 | 15.46 | A | C |
| ATOM | 3385 | O | VAL | A | 217 | 77.999 | −30.355 | −7.500 | 1.00 | 15.60 | A | O |
| ATOM | 3387 | N | LEU | A | 218 | 77.680 | −32.296 | −6.395 | 1.00 | 14.90 | A | N |
| ATOM | 3388 | CA | LEU | A | 218 | 76.300 | −31.998 | −6.009 | 1.00 | 14.22 | A | C |
| ATOM | 3390 | CB | LEU | A | 218 | 75.629 | −33.247 | −5.428 | 1.00 | 13.96 | A | C |
| ATOM | 3393 | CG | LEU | A | 218 | 74.139 | −33.142 | −5.094 | 1.00 | 13.06 | A | C |
| ATOM | 3395 | CD1 | LEU | A | 218 | 73.337 | −32.809 | −6.334 | 1.00 | 12.25 | A | C |
| ATOM | 3399 | CD2 | LEU | A | 218 | 73.641 | −34.437 | −4.469 | 1.00 | 13.26 | A | C |
| ATOM | 3403 | C | LEU | A | 218 | 76.223 | −30.849 | −5.003 | 1.00 | 14.10 | A | C |
| ATOM | 3404 | O | LEU | A | 218 | 75.312 | −30.020 | −5.072 | 1.00 | 14.58 | A | O |
| ATOM | 3406 | N | LEU | A | 219 | 77.176 | −30.810 | −4.071 | 1.00 | 13.33 | A | N |
| ATOM | 3407 | CA | LEU | A | 219 | 77.232 | −29.759 | −3.054 | 1.00 | 12.42 | A | C |
| ATOM | 3409 | CB | LEU | A | 219 | 78.290 | −30.088 | −1.996 | 1.00 | 12.57 | A | C |
| ATOM | 3412 | CG | LEU | A | 219 | 78.579 | −29.028 | −0.926 | 1.00 | 12.20 | A | C |
| ATOM | 3414 | CD1 | LEU | A | 219 | 77.303 | −28.587 | −0.229 | 1.00 | 11.68 | A | C |
| ATOM | 3418 | CD2 | LEU | A | 219 | 79.581 | −29.562 | 0.083 | 1.00 | 11.55 | A | C |
| ATOM | 3422 | C | LEU | A | 219 | 77.548 | −28.415 | −3.687 | 1.00 | 11.77 | A | C |
| ATOM | 3423 | O | LEU | A | 219 | 76.797 | −27.456 | −3.523 | 1.00 | 11.68 | A | O |
| ATOM | 3425 | N | GLU | A | 220 | 78.664 | −28.358 | −4.411 | 1.00 | 11.19 | A | N |
| ATOM | 3426 | CA | GLU | A | 220 | 79.099 | −27.132 | −5.084 | 1.00 | 10.73 | A | C |
| ATOM | 3428 | CB | GLU | A | 220 | 80.281 | −27.414 | −6.019 | 1.00 | 10.70 | A | C |
| ATOM | 3431 | CG | GLU | A | 220 | 80.927 | −26.162 | −6.616 | 1.00 | 11.19 | A | C |
| ATOM | 3434 | CD | GLU | A | 220 | 82.256 | −26.444 | −7.314 | 1.00 | 12.55 | A | C |
| ATOM | 3435 | OE1 | GLU | A | 220 | 82.631 | −27.630 | −7.453 | 1.00 | 13.13 | A | O |
| ATOM | 3436 | OE2 | GLU | A | 220 | 82.929 | −25.473 | −7.724 | 1.00 | 12.14 | A | O |
| ATOM | 3437 | C | GLU | A | 220 | 77.950 | −26.501 | −5.862 | 1.00 | 10.27 | A | C |
| ATOM | 3438 | O | GLU | A | 220 | 77.748 | −25.292 | −5.793 | 1.00 | 10.52 | A | O |
| ATOM | 3440 | N | LEU | A | 221 | 77.194 | −27.325 | −6.584 | 1.00 | 9.55 | A | N |
| ATOM | 3441 | CA | LEU | A | 221 | 76.018 | −26.851 | −7.310 | 1.00 | 9.02 | A | C |
| ATOM | 3443 | CB | LEU | A | 221 | 75.442 | −27.966 | −8.186 | 1.00 | 8.70 | A | C |
| ATOM | 3446 | CG | LEU | A | 221 | 74.258 | −27.599 | −9.086 | 1.00 | 7.05 | A | C |
| ATOM | 3448 | CD1 | LEU | A | 221 | 74.630 | −26.491 | −10.059 | 1.00 | 2.00 | A | C |
| ATOM | 3452 | CD2 | LEU | A | 221 | 73.772 | −28.833 | −9.831 | 1.00 | 6.26 | A | C |
| ATOM | 3456 | C | LEU | A | 221 | 74.948 | −26.343 | −6.347 | 1.00 | 9.08 | A | C |
| ATOM | 3457 | O | LEU | A | 221 | 74.395 | −25.262 | −6.544 | 1.00 | 8.80 | A | O |
| ATOM | 3459 | N | ALA | A | 222 | 74.669 | −27.124 | −5.305 | 1.00 | 9.46 | A | N |
| ATOM | 3460 | CA | ALA | A | 222 | 73.666 | −26.757 | −4.301 | 1.00 | 9.95 | A | C |
| ATOM | 3462 | CB | ALA | A | 222 | 73.633 | −27.794 | −3.181 | 1.00 | 9.71 | A | C |
| ATOM | 3466 | C | ALA | A | 222 | 73.913 | −25.358 | −3.728 | 1.00 | 10.24 | A | C |
| ATOM | 3467 | O | ALA | A | 222 | 72.979 | −24.572 | −3.572 | 1.00 | 10.55 | A | O |
| ATOM | 3469 | N | ILE | A | 223 | 75.173 | −25.055 | −3.430 | 1.00 | 10.52 | A | N |
| ATOM | 3470 | CA | ILE | A | 223 | 75.562 | −23.737 | −2.925 | 1.00 | 10.83 | A | C |
| ATOM | 3472 | CB | ILE | A | 223 | 77.049 | −23.711 | −2.476 | 1.00 | 10.98 | A | C |
| ATOM | 3474 | CG1 | ILE | A | 223 | 77.305 | −24.712 | −1.345 | 1.00 | 11.58 | A | C |
| ATOM | 3477 | CD1 | ILE | A | 223 | 78.778 | −24.910 | −1.045 | 1.00 | 12.62 | A | C |
| ATOM | 3481 | CG2 | ILE | A | 223 | 77.451 | −22.315 | −2.019 | 1.00 | 9.71 | A | C |
| ATOM | 3485 | C | ILE | A | 223 | 75.374 | −22.683 | −4.016 | 1.00 | 11.05 | A | C |
| ATOM | 3486 | O | ILE | A | 223 | 74.722 | −21.656 | −3.800 | 1.00 | 10.83 | A | O |

TABLE 8-2-continued

| Coordinates for L494P Structure | | | | | | | | | | | |
|---|---|---|---|---|---|---|---|---|---|---|---|
| ATOM | 3488 | N | LEU | A | 224 | 75.955 | −22.958 | −5.183 | 1.00 | 11.18 A | N |
| ATOM | 3489 | CA | LEU | A | 224 | 75.918 | −22.044 | −6.328 | 1.00 | 11.07 A | C |
| ATOM | 3491 | CB | LEU | A | 224 | 76.648 | −22.654 | −7.534 | 1.00 | 11.14 A | C |
| ATOM | 3494 | CG | LEU | A | 224 | 78.143 | −22.340 | −7.658 | 1.00 | 11.66 A | C |
| ATOM | 3496 | CD1 | LEU | A | 224 | 78.746 | −23.108 | −8.827 | 1.00 | 11.34 A | C |
| ATOM | 3500 | CD2 | LEU | A | 224 | 78.905 | −22.632 | −6.369 | 1.00 | 11.95 A | C |
| ATOM | 3504 | C | LEU | A | 224 | 74.500 | −21.660 | −6.730 | 1.00 | 10.85 A | C |
| ATOM | 3505 | O | LEU | A | 224 | 74.239 | −20.497 | −7.035 | 1.00 | 10.84 A | O |
| ATOM | 3507 | N | ASP | A | 225 | 73.593 | −22.635 | −6.727 | 1.00 | 10.80 A | N |
| ATOM | 3508 | CA | ASP | A | 225 | 72.207 | −22.395 | −7.125 | 1.00 | 10.89 A | C |
| ATOM | 3510 | CB | ASP | A | 225 | 71.505 | −23.705 | −7.481 | 1.00 | 10.48 A | C |
| ATOM | 3513 | CG | ASP | A | 225 | 70.158 | −23.481 | −8.142 | 1.00 | 9.49 A | C |
| ATOM | 3514 | OD1 | ASP | A | 225 | 69.184 | −23.189 | −7.422 | 1.00 | 10.17 A | O |
| ATOM | 3515 | OD2 | ASP | A | 225 | 70.069 | −23.597 | −9.382 | 1.00 | 8.04 A | O |
| ATOM | 3516 | C | ASP | A | 225 | 71.416 | −21.659 | −6.047 | 1.00 | 11.49 A | C |
| ATOM | 3517 | O | ASP | A | 225 | 70.605 | −20.792 | −6.367 | 1.00 | 11.55 A | O |
| ATOM | 3519 | N | TYR | A | 226 | 71.641 | −22.004 | −4.780 | 1.00 | 12.19 A | N |
| ATOM | 3520 | CA | TYR | A | 226 | 70.963 | −21.320 | −3.676 | 1.00 | 12.94 A | C |
| ATOM | 3522 | CB | TYR | A | 226 | 71.215 | −22.022 | −2.335 | 1.00 | 13.18 A | C |
| ATOM | 3525 | CG | TYR | A | 226 | 70.495 | −21.360 | −1.178 | 1.00 | 13.58 A | C |
| ATOM | 3526 | CD1 | TYR | A | 226 | 69.207 | −21.745 | −0.825 | 1.00 | 15.76 A | C |
| ATOM | 3528 | CE1 | TYR | A | 226 | 68.536 | −21.133 | 0.227 | 1.00 | 17.41 A | C |
| ATOM | 3530 | CZ | TYR | A | 226 | 69.154 | −20.117 | 0.932 | 1.00 | 18.41 A | C |
| ATOM | 3531 | OH | TYR | A | 226 | 68.493 | −19.509 | 1.972 | 1.00 | 18.87 A | O |
| ATOM | 3533 | CE2 | TYR | A | 226 | 70.434 | −19.712 | 0.595 | 1.00 | 16.75 A | C |
| ATOM | 3535 | CD2 | TYR | A | 226 | 71.093 | −20.331 | −0.457 | 1.00 | 14.36 A | C |
| ATOM | 3537 | C | TYR | A | 226 | 71.394 | −19.855 | −3.582 | 1.00 | 13.23 A | C |
| ATOM | 3538 | O | TYR | A | 226 | 70.562 | −18.971 | −3.355 | 1.00 | 13.29 A | O |
| ATOM | 3540 | N | ASN | A | 227 | 72.692 | −19.608 | −3.742 | 1.00 | 13.39 A | N |
| ATOM | 3541 | CA | ASN | A | 227 | 73.221 | −18.246 | −3.718 | 1.00 | 14.03 A | C |
| ATOM | 3543 | CB | ASN | A | 227 | 74.751 | −18.258 | −3.625 | 1.00 | 14.09 A | C |
| ATOM | 3546 | CG | ASN | A | 227 | 75.255 | −18.679 | −2.250 | 1.00 | 14.19 A | C |
| ATOM | 3547 | OD1 | ASN | A | 227 | 74.571 | −18.512 | −1.241 | 1.00 | 14.72 A | O |
| ATOM | 3548 | ND2 | ASN | A | 227 | 76.467 | −19.217 | −2.208 | 1.00 | 15.25 A | N |
| ATOM | 3551 | C | ASN | A | 227 | 72.768 | −17.429 | −4.929 | 1.00 | 14.55 A | C |
| ATOM | 3552 | O | ASN | A | 227 | 72.560 | −16.219 | −4.819 | 1.00 | 14.82 A | O |
| ATOM | 3554 | N | MET | A | 228 | 72.619 | −18.093 | −6.074 | 1.00 | 14.98 A | N |
| ATOM | 3555 | CA | MET | A | 228 | 72.085 | −17.462 | −7.284 | 1.00 | 15.29 A | C |
| ATOM | 3557 | CB | MET | A | 228 | 72.127 | −18.444 | −8.462 | 1.00 | 15.61 A | C |
| ATOM | 3560 | CG | MET | A | 228 | 71.507 | −17.933 | −9.767 | 1.00 | 16.18 A | C |
| ATOM | 3563 | SD | MET | A | 228 | 70.987 | −19.279 | −10.861 | 1.00 | 18.75 A | S |
| ATOM | 3564 | CE | MET | A | 228 | 69.510 | −19.868 | −10.029 | 1.00 | 17.19 A | C |
| ATOM | 3568 | C | MET | A | 228 | 70.650 | −17.009 | −7.049 | 1.00 | 15.29 A | C |
| ATOM | 3569 | O | MET | A | 228 | 70.329 | −15.833 | −7.218 | 1.00 | 15.27 A | O |
| ATOM | 3571 | N | ILE | A | 229 | 69.793 | −17.951 | −6.661 | 1.00 | 15.43 A | N |
| ATOM | 3572 | CA | ILE | A | 229 | 68.385 | −17.655 | −6.413 | 1.00 | 15.53 A | C |
| ATOM | 3574 | CB | ILE | A | 229 | 67.605 | −18.896 | −5.916 | 1.00 | 15.48 A | C |
| ATOM | 3576 | CG1 | ILE | A | 229 | 67.419 | −19.909 | −7.051 | 1.00 | 15.09 A | C |
| ATOM | 3579 | CD1 | ILE | A | 229 | 66.660 | −21.167 | −6.643 | 1.00 | 11.04 A | C |
| ATOM | 3583 | CG2 | ILE | A | 229 | 66.240 | −18.489 | −5.384 | 1.00 | 16.76 A | C |
| ATOM | 3587 | C | ILE | A | 229 | 68.252 | −16.529 | −5.395 | 1.00 | 15.81 A | C |
| ATOM | 3588 | O | ILE | A | 229 | 67.429 | −15.634 | −5.566 | 1.00 | 16.48 A | O |
| ATOM | 3590 | N | GLN | A | 230 | 69.073 | −16.567 | −4.348 | 1.00 | 15.87 A | N |
| ATOM | 3591 | CA | GLN | A | 230 | 69.059 | −15.514 | −3.332 | 1.00 | 15.81 A | C |
| ATOM | 3593 | CB | GLN | A | 230 | 70.046 | −15.817 | −2.199 | 1.00 | 15.91 A | C |
| ATOM | 3596 | CG | GLN | A | 230 | 69.925 | −14.855 | −1.019 | 1.00 | 15.74 A | C |
| ATOM | 3599 | CD | GLN | A | 230 | 70.996 | −15.064 | 0.026 | 1.00 | 15.63 A | C |
| ATOM | 3600 | OE1 | GLN | A | 230 | 71.920 | −14.261 | 0.147 | 1.00 | 17.47 A | O |
| ATOM | 3601 | NE2 | GLN | A | 230 | 70.879 | −16.145 | 0.791 | 1.00 | 14.80 A | N |
| ATOM | 3604 | C | GLN | A | 230 | 69.372 | −14.143 | −3.929 | 1.00 | 15.64 A | C |
| ATOM | 3605 | O | GLN | A | 230 | 68.772 | −13.147 | −3.532 | 1.00 | 15.71 A | O |
| ATOM | 3607 | N | SER | A | 231 | 70.305 | −14.091 | −4.878 | 1.00 | 15.55 A | N |
| ATOM | 3608 | CA | SER | A | 231 | 70.678 | −12.819 | −5.504 | 1.00 | 15.35 A | C |
| ATOM | 3610 | CB | SER | A | 231 | 71.927 | −12.962 | −6.385 | 1.00 | 15.10 A | C |
| ATOM | 3613 | OG | SER | A | 231 | 71.603 | −13.433 | −7.681 | 1.00 | 15.04 A | O |
| ATOM | 3615 | C | SER | A | 231 | 69.511 | −12.251 | −6.308 | 1.00 | 15.24 A | C |
| ATOM | 3616 | O | SER | A | 231 | 69.441 | −11.041 | −6.525 | 1.00 | 15.43 A | O |
| ATOM | 3618 | N | VAL | A | 232 | 68.605 | −13.126 | −6.747 | 1.00 | 15.03 A | N |
| ATOM | 3619 | CA | VAL | A | 232 | 67.343 | −12.692 | −7.341 | 1.00 | 15.37 A | C |
| ATOM | 3621 | CB | VAL | A | 232 | 66.631 | −13.837 | −8.091 | 1.00 | 15.43 A | C |
| ATOM | 3623 | CG1 | VAL | A | 232 | 65.234 | −13.406 | −8.544 | 1.00 | 14.95 A | C |
| ATOM | 3627 | CG2 | VAL | A | 232 | 67.468 | −14.282 | −9.277 | 1.00 | 15.59 A | C |
| ATOM | 3631 | C | VAL | A | 232 | 66.427 | −12.130 | −6.256 | 1.00 | 15.65 A | C |
| ATOM | 3632 | O | VAL | A | 232 | 65.897 | −11.027 | −6.401 | 1.00 | 15.40 A | O |
| ATOM | 3634 | N | TYR | A | 233 | 66.259 | −12.882 | −5.168 | 1.00 | 16.13 A | N |
| ATOM | 3635 | CA | TYR | A | 233 | 65.453 | −12.426 | −4.030 | 1.00 | 16.89 A | C |
| ATOM | 3637 | CB | TYR | A | 233 | 65.588 | −13.370 | −2.825 | 1.00 | 16.70 A | C |
| ATOM | 3640 | CG | TYR | A | 233 | 65.023 | −14.766 | −2.995 | 1.00 | 16.10 A | C |

TABLE 8-2-continued

| Coordinates for L494P Structure | | | | | | | | | | | | |
|---|---|---|---|---|---|---|---|---|---|---|---|---|
| ATOM | 3641 | CD1 | TYR | A | 233 | 64.102 | −15.068 | −4.001 | 1.00 | 17.42 | A | C |
| ATOM | 3643 | CE1 | TYR | A | 233 | 63.584 | −16.348 | −4.137 | 1.00 | 16.75 | A | C |
| ATOM | 3645 | CZ | TYR | A | 233 | 63.969 | −17.336 | −3.253 | 1.00 | 16.03 | A | C |
| ATOM | 3646 | OH | TYR | A | 233 | 63.452 | −18.601 | −3.388 | 1.00 | 17.62 | A | O |
| ATOM | 3648 | CE2 | TYR | A | 233 | 64.868 | −17.060 | −2.241 | 1.00 | 14.85 | A | C |
| ATOM | 3650 | CD2 | TYR | A | 233 | 65.385 | −15.782 | −2.115 | 1.00 | 14.89 | A | C |
| ATOM | 3652 | C | TYR | A | 233 | 65.841 | −11.016 | −3.591 | 1.00 | 17.81 | A | C |
| ATOM | 3653 | O | TYR | A | 233 | 64.977 | −10.199 | −3.267 | 1.00 | 17.90 | A | O |
| ATOM | 3655 | N | GLN | A | 234 | 67.142 | −10.743 | −3.577 | 1.00 | 19.03 | A | N |
| ATOM | 3656 | CA | GLN | A | 234 | 67.656 | −9.424 | −3.212 | 1.00 | 20.11 | A | C |
| ATOM | 3658 | CB | GLN | A | 234 | 69.178 | −9.474 | −3.026 | 1.00 | 20.14 | A | C |
| ATOM | 3661 | CG | GLN | A | 234 | 69.614 | −10.305 | −1.821 | 1.00 | 20.32 | A | C |
| ATOM | 3664 | CD | GLN | A | 234 | 71.113 | −10.522 | −1.755 | 1.00 | 20.42 | A | C |
| ATOM | 3665 | OE1 | GLN | A | 234 | 71.897 | −9.618 | −2.046 | 1.00 | 21.90 | A | O |
| ATOM | 3666 | NE2 | GLN | A | 234 | 71.519 | −11.725 | −1.359 | 1.00 | 19.04 | A | N |
| ATOM | 3669 | C | GLN | A | 234 | 67.273 | −8.370 | −4.251 | 1.00 | 20.93 | A | C |
| ATOM | 3670 | O | GLN | A | 234 | 66.878 | −7.258 | −3.890 | 1.00 | 20.70 | A | O |
| ATOM | 3672 | N | ARG | A | 235 | 67.380 | −8.728 | −5.533 | 1.00 | 21.91 | A | N |
| ATOM | 3673 | CA | ARG | A | 235 | 66.999 | −7.828 | −6.629 | 1.00 | 22.67 | A | C |
| ATOM | 3675 | CB | ARG | A | 235 | 67.476 | −8.369 | −7.989 | 1.00 | 23.14 | A | C |
| ATOM | 3678 | CG | ARG | A | 235 | 67.224 | −7.413 | −9.167 | 1.00 | 24.55 | A | C |
| ATOM | 3681 | CD | ARG | A | 235 | 68.367 | −7.390 | −10.199 | 1.00 | 27.72 | A | C |
| ATOM | 3684 | NE | ARG | A | 235 | 68.169 | −8.321 | −11.317 | 1.00 | 30.54 | A | N |
| ATOM | 3686 | CZ | ARG | A | 235 | 68.777 | −9.502 | −11.474 | 1.00 | 31.20 | A | C |
| ATOM | 3687 | NH1 | ARG | A | 235 | 69.652 | −9.961 | −10.582 | 1.00 | 31.84 | A | N |
| ATOM | 3690 | NH2 | ARG | A | 235 | 68.502 | −10.239 | −12.547 | 1.00 | 30.15 | A | N |
| ATOM | 3693 | C | ARG | A | 235 | 65.489 | −7.586 | −6.647 | 1.00 | 22.58 | A | C |
| ATOM | 3694 | O | ARG | A | 235 | 65.041 | −6.485 | −6.977 | 1.00 | 22.79 | A | O |
| ATOM | 3696 | N | ASP | A | 236 | 64.714 | −8.613 | −6.298 | 1.00 | 22.21 | A | N |
| ATOM | 3697 | CA | ASP | A | 236 | 63.264 | −8.470 | −6.137 | 1.00 | 22.10 | A | C |
| ATOM | 3699 | CB | ASP | A | 236 | 62.602 | −9.827 | −5.858 | 1.00 | 21.87 | A | C |
| ATOM | 3702 | CG | ASP | A | 236 | 62.525 | −10.721 | −7.087 | 1.00 | 21.53 | A | C |
| ATOM | 3703 | OD1 | ASP | A | 236 | 62.684 | −10.224 | −8.222 | 1.00 | 19.56 | A | O |
| ATOM | 3704 | OD2 | ASP | A | 236 | 62.293 | −11.936 | −6.907 | 1.00 | 20.26 | A | O |
| ATOM | 3705 | C | ASP | A | 236 | 62.926 | −7.513 | −4.995 | 1.00 | 22.23 | A | C |
| ATOM | 3706 | O | ASP | A | 236 | 61.997 | −6.712 | −5.107 | 1.00 | 22.26 | A | O |
| ATOM | 3708 | N | LEU | A | 237 | 63.686 | −7.598 | −3.902 | 1.00 | 22.39 | A | N |
| ATOM | 3709 | CA | LEU | A | 237 | 63.391 | −6.829 | −2.693 | 1.00 | 22.41 | A | C |
| ATOM | 3711 | CB | LEU | A | 237 | 64.157 | −7.387 | −1.489 | 1.00 | 22.11 | A | C |
| ATOM | 3714 | CG | LEU | A | 237 | 63.678 | −6.902 | −0.118 | 1.00 | 21.18 | A | C |
| ATOM | 3716 | CD1 | LEU | A | 237 | 62.211 | −7.251 | 0.103 | 1.00 | 20.99 | A | C |
| ATOM | 3720 | CD2 | LEU | A | 237 | 64.532 | −7.497 | 0.986 | 1.00 | 20.81 | A | C |
| ATOM | 3724 | C | LEU | A | 237 | 63.701 | −5.347 | −2.860 | 1.00 | 22.97 | A | C |
| ATOM | 3725 | O | LEU | A | 237 | 62.888 | −4.503 | −2.487 | 1.00 | 23.24 | A | O |
| ATOM | 3727 | N | ARG | A | 238 | 64.870 | −5.032 | −3.414 | 1.00 | 23.56 | A | N |
| ATOM | 3728 | CA | ARG | A | 238 | 65.252 | −3.637 | −3.655 | 1.00 | 23.85 | A | C |
| ATOM | 3730 | CB | ARG | A | 238 | 66.594 | −3.544 | −4.391 | 1.00 | 23.60 | A | C |
| ATOM | 3733 | CG | ARG | A | 238 | 67.798 | −3.930 | −3.546 | 1.00 | 23.92 | A | C |
| ATOM | 3736 | CD | ARG | A | 238 | 69.109 | −3.464 | −4.176 | 1.00 | 25.61 | A | C |
| ATOM | 3739 | NE | ARG | A | 238 | 69.289 | −3.951 | −5.547 | 1.00 | 26.87 | A | N |
| ATOM | 3741 | CZ | ARG | A | 238 | 69.725 | −5.168 | −5.887 | 1.00 | 27.26 | A | C |
| ATOM | 3742 | NH1 | ARG | A | 238 | 70.036 | −6.073 | −4.961 | 1.00 | 27.13 | A | N |
| ATOM | 3745 | NH2 | ARG | A | 238 | 69.847 | −5.487 | −7.172 | 1.00 | 26.94 | A | N |
| ATOM | 3748 | C | ARG | A | 238 | 64.169 | −2.900 | −4.446 | 1.00 | 24.35 | A | C |
| ATOM | 3749 | O | ARG | A | 238 | 63.854 | −1.750 | −4.142 | 1.00 | 24.59 | A | O |
| ATOM | 3751 | N | GLU | A | 239 | 63.600 | −3.575 | −5.445 | 1.00 | 24.73 | A | N |
| ATOM | 3752 | CA | GLU | A | 239 | 62.514 | −3.020 | −6.259 | 1.00 | 25.20 | A | C |
| ATOM | 3754 | CB | GLU | A | 239 | 62.197 | −3.957 | −7.431 | 1.00 | 25.81 | A | C |
| ATOM | 3757 | CG | GLU | A | 239 | 61.161 | −3.414 | −8.425 | 1.00 | 28.50 | A | C |
| ATOM | 3760 | CD | GLU | A | 239 | 60.814 | −4.406 | −9.530 | 1.00 | 31.93 | A | C |
| ATOM | 3761 | OE1 | GLU | A | 239 | 61.344 | −5.542 | −9.512 | 1.00 | 33.54 | A | O |
| ATOM | 3762 | OE2 | GLU | A | 239 | 60.005 | −4.048 | −10.417 | 1.00 | 33.16 | A | O |
| ATOM | 3763 | C | GLU | A | 239 | 61.254 | −2.791 | −5.423 | 1.00 | 24.67 | A | C |
| ATOM | 3764 | O | GLU | A | 239 | 60.556 | −1.788 | −5.596 | 1.00 | 24.49 | A | O |
| ATOM | 3766 | N | THR | A | 240 | 60.966 | −3.730 | −4.528 | 1.00 | 24.08 | A | N |
| ATOM | 3767 | CA | THR | A | 240 | 59.829 | −3.610 | −3.624 | 1.00 | 23.83 | A | C |
| ATOM | 3769 | CB | THR | A | 240 | 59.535 | −4.946 | −2.915 | 1.00 | 23.90 | A | C |
| ATOM | 3771 | OG1 | THR | A | 240 | 59.679 | −6.026 | −3.845 | 1.00 | 24.05 | A | O |
| ATOM | 3773 | CG2 | THR | A | 240 | 58.121 | −4.953 | −2.344 | 1.00 | 24.20 | A | C |
| ATOM | 3777 | C | THR | A | 240 | 60.089 | −2.524 | −2.578 | 1.00 | 23.67 | A | C |
| ATOM | 3778 | O | THR | A | 240 | 59.225 | −1.686 | −2.318 | 1.00 | 23.85 | A | O |
| ATOM | 3780 | N | SER | A | 241 | 61.284 | −2.541 | −1.990 | 1.00 | 23.37 | A | N |
| ATOM | 3781 | CA | SER | A | 241 | 61.684 | −1.535 | −1.003 | 1.00 | 23.30 | A | C |
| ATOM | 3783 | CB | SER | A | 241 | 63.097 | −1.811 | −0.495 | 1.00 | 23.25 | A | C |
| ATOM | 3786 | OG | SER | A | 241 | 63.136 | −3.010 | 0.253 | 1.00 | 24.21 | A | O |
| ATOM | 3788 | C | SER | A | 241 | 61.612 | −0.117 | −1.561 | 1.00 | 23.34 | A | C |
| ATOM | 3789 | O | SER | A | 241 | 61.297 | 0.820 | −0.831 | 1.00 | 23.53 | A | O |
| ATOM | 3791 | N | ARG | A | 242 | 61.912 | 0.040 | −2.847 | 1.00 | 23.51 | A | N |

TABLE 8-2-continued

| Coordinates for L494P Structure | | | | | | | | | | | | |
|---|---|---|---|---|---|---|---|---|---|---|---|---|
| ATOM | 3792 | CA | ARG | A | 242 | 61.754 | 1.334 | −3.509 | 1.00 | 23.66 | A | C |
| ATOM | 3794 | CB | ARG | A | 242 | 62.312 | 1.304 | −4.941 | 1.00 | 23.94 | A | C |
| ATOM | 3797 | CG | ARG | A | 242 | 63.841 | 1.370 | −5.019 | 1.00 | 24.87 | A | C |
| ATOM | 3800 | CD | ARG | A | 242 | 64.335 | 1.973 | −6.333 | 1.00 | 26.38 | A | C |
| ATOM | 3803 | NE | ARG | A | 242 | 64.074 | 1.116 | −7.492 | 1.00 | 28.02 | A | N |
| ATOM | 3805 | CZ | ARG | A | 242 | 64.802 | 0.054 | −7.848 | 1.00 | 27.68 | A | C |
| ATOM | 3806 | NH1 | ARG | A | 242 | 64.462 | −0.643 | −8.928 | 1.00 | 26.86 | A | N |
| ATOM | 3809 | NH2 | ARG | A | 242 | 65.861 | −0.324 | −7.135 | 1.00 | 27.49 | A | N |
| ATOM | 3812 | C | ARG | A | 242 | 60.286 | 1.757 | −3.514 | 1.00 | 23.31 | A | C |
| ATOM | 3813 | O | ARG | A | 242 | 59.976 | 2.920 | −3.264 | 1.00 | 23.30 | A | O |
| ATOM | 3815 | N | TRP | A | 243 | 59.393 | 0.809 | −3.788 | 1.00 | 23.18 | A | N |
| ATOM | 3816 | CA | TRP | A | 243 | 57.949 | 1.072 | −3.768 | 1.00 | 23.23 | A | C |
| ATOM | 3818 | CB | TRP | A | 243 | 57.177 | −0.111 | −4.369 | 1.00 | 23.16 | A | C |
| ATOM | 3821 | CG | TRP | A | 243 | 55.704 | −0.106 | −4.072 | 1.00 | 23.21 | A | C |
| ATOM | 3822 | CD1 | TRP | A | 243 | 54.729 | 0.555 | −4.762 | 1.00 | 23.71 | A | C |
| ATOM | 3824 | NE1 | TRP | A | 243 | 53.499 | 0.317 | −4.193 | 1.00 | 23.58 | A | N |
| ATOM | 3826 | CE2 | TRP | A | 243 | 53.662 | −0.514 | −3.116 | 1.00 | 23.23 | A | C |
| ATOM | 3827 | CD2 | TRP | A | 243 | 55.041 | −0.802 | −3.009 | 1.00 | 23.80 | A | C |
| ATOM | 3828 | CE3 | TRP | A | 243 | 55.478 | −1.639 | −1.973 | 1.00 | 23.02 | A | C |
| ATOM | 3830 | CZ3 | TRP | A | 243 | 54.535 | −2.156 | −1.091 | 1.00 | 22.08 | A | C |
| ATOM | 3832 | CH2 | TRP | A | 243 | 53.171 | −1.849 | −1.224 | 1.00 | 21.07 | A | C |
| ATOM | 3834 | CZ2 | TRP | A | 243 | 52.717 | −1.033 | −2.228 | 1.00 | 22.30 | A | C |
| ATOM | 3836 | C | TRP | A | 243 | 57.440 | 1.364 | −2.353 | 1.00 | 23.29 | A | C |
| ATOM | 3837 | O | TRP | A | 243 | 56.706 | 2.332 | −2.139 | 1.00 | 23.34 | A | O |
| ATOM | 3839 | N | TRP | A | 244 | 57.830 | 0.522 | −1.399 | 1.00 | 23.09 | A | N |
| ATOM | 3840 | CA | TRP | A | 244 | 57.355 | 0.641 | −0.019 | 1.00 | 22.81 | A | C |
| ATOM | 3842 | CB | TRP | A | 244 | 57.907 | −0.507 | 0.834 | 1.00 | 22.28 | A | C |
| ATOM | 3845 | CG | TRP | A | 244 | 57.373 | −0.551 | 2.242 | 1.00 | 21.81 | A | C |
| ATOM | 3846 | CD1 | TRP | A | 244 | 58.102 | −0.486 | 3.393 | 1.00 | 22.74 | A | C |
| ATOM | 3848 | NE1 | TRP | A | 244 | 57.271 | −0.556 | 4.486 | 1.00 | 22.22 | A | N |
| ATOM | 3850 | CE2 | TRP | A | 244 | 55.976 | −0.667 | 4.055 | 1.00 | 21.12 | A | C |
| ATOM | 3851 | CD2 | TRP | A | 244 | 56.000 | −0.666 | 2.645 | 1.00 | 20.57 | A | C |
| ATOM | 3852 | CE3 | TRP | A | 244 | 54.789 | −0.766 | 1.951 | 1.00 | 19.76 | A | C |
| ATOM | 3854 | CZ3 | TRP | A | 244 | 53.610 | −0.863 | 2.675 | 1.00 | 19.15 | A | C |
| ATOM | 3856 | CH2 | TRP | A | 244 | 53.619 | −0.863 | 4.076 | 1.00 | 20.39 | A | C |
| ATOM | 3858 | CZ2 | TRP | A | 244 | 54.789 | −0.764 | 4.784 | 1.00 | 21.06 | A | C |
| ATOM | 3860 | C | TRP | A | 244 | 57.699 | 1.996 | 0.608 | 1.00 | 23.07 | A | C |
| ATOM | 3861 | O | TRP | A | 244 | 56.851 | 2.609 | 1.256 | 1.00 | 23.27 | A | O |
| ATOM | 3863 | N | ARG | A | 245 | 58.930 | 2.467 | 0.408 | 1.00 | 23.23 | A | N |
| ATOM | 3864 | CA | ARG | A | 245 | 59.342 | 3.773 | 0.934 | 1.00 | 23.46 | A | C |
| ATOM | 3866 | CB | ARG | A | 245 | 60.839 | 4.028 | 0.708 | 1.00 | 23.77 | A | C |
| ATOM | 3869 | CG | ARG | A | 245 | 61.769 | 3.206 | 1.596 | 1.00 | 25.08 | A | C |
| ATOM | 3872 | CD | ARG | A | 245 | 63.090 | 3.929 | 1.866 | 1.00 | 28.31 | A | C |
| ATOM | 3875 | NE | ARG | A | 245 | 63.649 | 4.582 | 0.677 | 1.00 | 30.86 | A | N |
| ATOM | 3877 | CZ | ARG | A | 245 | 64.296 | 3.963 | −0.312 | 1.00 | 32.93 | A | C |
| ATOM | 3878 | NH1 | ARG | A | 245 | 64.480 | 2.644 | −0.296 | 1.00 | 33.65 | A | N |
| ATOM | 3881 | NH2 | ARG | A | 245 | 64.760 | 4.671 | −1.338 | 1.00 | 33.03 | A | N |
| ATOM | 3884 | C | ARG | A | 245 | 58.532 | 4.898 | 0.295 | 1.00 | 23.19 | A | C |
| ATOM | 3885 | O | ARG | A | 245 | 58.020 | 5.776 | 0.994 | 1.00 | 23.26 | A | O |
| ATOM | 3887 | N | ARG | A | 246 | 58.426 | 4.860 | −1.032 | 1.00 | 22.85 | A | N |
| ATOM | 3888 | CA | ARG | A | 246 | 57.653 | 5.843 | −1.799 | 1.00 | 22.73 | A | C |
| ATOM | 3890 | CB | ARG | A | 246 | 57.613 | 5.451 | −3.282 | 1.00 | 23.21 | A | C |
| ATOM | 3893 | CG | ARG | A | 246 | 58.727 | 6.068 | −4.126 | 1.00 | 26.50 | A | C |
| ATOM | 3896 | CD | ARG | A | 246 | 58.216 | 7.252 | −4.944 | 1.00 | 30.69 | A | C |
| ATOM | 3899 | NE | ARG | A | 246 | 57.435 | 6.800 | −6.098 | 1.00 | 33.43 | A | N |
| ATOM | 3901 | CZ | ARG | A | 246 | 57.944 | 6.440 | −7.278 | 1.00 | 35.34 | A | C |
| ATOM | 3902 | NH1 | ARG | A | 246 | 59.257 | 6.479 | −7.505 | 1.00 | 35.77 | A | N |
| ATOM | 3905 | NH2 | ARG | A | 246 | 57.129 | 6.038 | −8.249 | 1.00 | 35.70 | A | N |
| ATOM | 3908 | C | ARG | A | 246 | 56.232 | 5.997 | −1.266 | 1.00 | 21.79 | A | C |
| ATOM | 3909 | O | ARG | A | 246 | 55.743 | 7.114 | −1.101 | 1.00 | 21.69 | A | O |
| ATOM | 3911 | N | VAL | A | 247 | 55.579 | 4.870 | −1.000 | 1.00 | 20.96 | A | N |
| ATOM | 3912 | CA | VAL | A | 247 | 54.252 | 4.871 | −0.393 | 1.00 | 20.37 | A | C |
| ATOM | 3914 | CB | VAL | A | 247 | 53.725 | 3.434 | −0.202 | 1.00 | 19.99 | A | C |
| ATOM | 3916 | CG1 | VAL | A | 247 | 53.571 | 2.751 | −1.549 | 1.00 | 19.77 | A | C |
| ATOM | 3920 | CG2 | VAL | A | 247 | 52.400 | 3.433 | 0.549 | 1.00 | 19.80 | A | C |
| ATOM | 3924 | C | VAL | A | 247 | 54.293 | 5.600 | 0.955 | 1.00 | 20.50 | A | C |
| ATOM | 3925 | O | VAL | A | 247 | 53.458 | 6.463 | 1.227 | 1.00 | 19.95 | A | O |
| ATOM | 3927 | N | GLY | A | 248 | 55.275 | 5.247 | 1.783 | 1.00 | 20.89 | A | N |
| ATOM | 3928 | CA | GLY | A | 248 | 55.515 | 5.921 | 3.059 | 1.00 | 21.19 | A | C |
| ATOM | 3931 | C | GLY | A | 248 | 54.386 | 5.801 | 4.067 | 1.00 | 21.62 | A | C |
| ATOM | 3932 | O | GLY | A | 248 | 54.129 | 6.736 | 4.827 | 1.00 | 21.37 | A | O |
| ATOM | 3934 | N | LEU | A | 249 | 53.726 | 4.645 | 4.090 | 1.00 | 22.43 | A | N |
| ATOM | 3935 | CA | LEU | A | 249 | 52.558 | 4.438 | 4.952 | 1.00 | 23.00 | A | C |
| ATOM | 3937 | CB | LEU | A | 249 | 51.685 | 3.290 | 4.421 | 1.00 | 22.92 | A | C |
| ATOM | 3940 | CG | LEU | A | 249 | 50.171 | 3.488 | 4.554 | 1.00 | 22.33 | A | C |
| ATOM | 3942 | CD1 | LEU | A | 249 | 49.692 | 4.615 | 3.649 | 1.00 | 21.36 | A | C |
| ATOM | 3946 | CD2 | LEU | A | 249 | 49.430 | 2.205 | 4.229 | 1.00 | 21.54 | A | C |
| ATOM | 3950 | C | LEU | A | 249 | 52.978 | 4.172 | 6.403 | 1.00 | 23.55 | A | C |

TABLE 8-2-continued

| Coordinates for L494P Structure | | | | | | | | | | | | |
|---|---|---|---|---|---|---|---|---|---|---|---|---|
| ATOM | 3951 | O | LEU | A | 249 | 52.390 | 4.726 | 7.336 | 1.00 | 23.31 | A | O |
| ATOM | 3953 | N | ALA | A | 250 | 53.996 | 3.332 | 6.584 | 1.00 | 24.09 | A | N |
| ATOM | 3954 | CA | ALA | A | 250 | 54.538 | 3.034 | 7.913 | 1.00 | 24.42 | A | C |
| ATOM | 3956 | CB | ALA | A | 250 | 55.713 | 2.072 | 7.798 | 1.00 | 24.82 | A | C |
| ATOM | 3960 | C | ALA | A | 250 | 54.965 | 4.302 | 8.658 | 1.00 | 24.51 | A | C |
| ATOM | 3961 | O | ALA | A | 250 | 54.703 | 4.439 | 9.855 | 1.00 | 24.78 | A | O |
| ATOM | 3963 | N | THR | A | 251 | 55.620 | 5.218 | 7.944 | 1.00 | 24.26 | A | N |
| ATOM | 3964 | CA | THR | A | 251 | 56.070 | 6.486 | 8.520 | 1.00 | 23.84 | A | C |
| ATOM | 3966 | CB | THR | A | 251 | 56.889 | 7.311 | 7.504 | 1.00 | 23.73 | A | C |
| ATOM | 3968 | OG1 | THR | A | 251 | 57.988 | 6.530 | 7.022 | 1.00 | 23.21 | A | O |
| ATOM | 3970 | CG2 | THR | A | 251 | 57.413 | 8.596 | 8.146 | 1.00 | 23.03 | A | C |
| ATOM | 3974 | C | THR | A | 251 | 54.904 | 7.354 | 8.990 | 1.00 | 23.80 | A | C |
| ATOM | 3975 | O | THR | A | 251 | 54.852 | 7.748 | 10.154 | 1.00 | 24.05 | A | O |
| ATOM | 3977 | N | LYS | A | 252 | 53.973 | 7.638 | 8.082 | 1.00 | 23.59 | A | N |
| ATOM | 3978 | CA | LYS | A | 252 | 52.912 | 8.617 | 8.339 | 1.00 | 23.66 | A | C |
| ATOM | 3980 | CB | LYS | A | 252 | 52.238 | 9.041 | 7.025 | 1.00 | 23.72 | A | C |
| ATOM | 3983 | CG | LYS | A | 252 | 53.191 | 9.682 | 5.999 | 1.00 | 24.88 | A | C |
| ATOM | 3986 | CD | LYS | A | 252 | 53.744 | 11.038 | 6.465 | 1.00 | 25.58 | A | C |
| ATOM | 3989 | CE | LYS | A | 252 | 55.000 | 11.436 | 5.698 | 1.00 | 25.21 | A | C |
| ATOM | 3992 | NZ | LYS | A | 252 | 55.739 | 12.535 | 6.380 | 1.00 | 24.66 | A | N |
| ATOM | 3996 | C | LYS | A | 252 | 51.872 | 8.114 | 9.343 | 1.00 | 23.54 | A | C |
| ATOM | 3997 | O | LYS | A | 252 | 51.453 | 8.856 | 10.234 | 1.00 | 23.17 | A | O |
| ATOM | 3999 | N | LEU | A | 253 | 51.461 | 6.858 | 9.200 | 1.00 | 23.95 | A | N |
| ATOM | 4000 | CA | LEU | A | 253 | 50.579 | 6.226 | 10.181 | 1.00 | 24.13 | A | C |
| ATOM | 4002 | CB | LEU | A | 253 | 49.901 | 4.980 | 9.596 | 1.00 | 23.73 | A | C |
| ATOM | 4005 | CG | LEU | A | 253 | 48.663 | 5.213 | 8.724 | 1.00 | 22.61 | A | C |
| ATOM | 4007 | CD1 | LEU | A | 253 | 48.839 | 6.393 | 7.784 | 1.00 | 22.35 | A | C |
| ATOM | 4011 | CD2 | LEU | A | 253 | 48.328 | 3.954 | 7.943 | 1.00 | 23.69 | A | C |
| ATOM | 4015 | C | LEU | A | 253 | 51.404 | 5.863 | 11.414 | 1.00 | 24.78 | A | C |
| ATOM | 4016 | O | LEU | A | 253 | 52.176 | 4.901 | 11.389 | 1.00 | 25.30 | A | O |
| ATOM | 4018 | N | HIS | A | 254 | 51.238 | 6.638 | 12.486 | 1.00 | 24.95 | A | N |
| ATOM | 4019 | CA | HIS | A | 254 | 52.075 | 6.499 | 13.685 | 1.00 | 25.19 | A | C |
| ATOM | 4021 | CB | HIS | A | 254 | 51.757 | 7.594 | 14.714 | 1.00 | 25.53 | A | C |
| ATOM | 4024 | CG | HIS | A | 254 | 51.801 | 8.987 | 14.160 | 1.00 | 26.66 | A | C |
| ATOM | 4025 | ND1 | HIS | A | 254 | 52.813 | 9.434 | 13.337 | 1.00 | 26.59 | A | N |
| ATOM | 4027 | CE1 | HIS | A | 254 | 52.587 | 10.693 | 13.008 | 1.00 | 27.01 | A | C |
| ATOM | 4029 | NE2 | HIS | A | 254 | 51.468 | 11.082 | 13.593 | 1.00 | 27.77 | A | N |
| ATOM | 4031 | CD2 | HIS | A | 254 | 50.958 | 10.036 | 14.322 | 1.00 | 27.37 | A | C |
| ATOM | 4033 | C | HIS | A | 254 | 51.926 | 5.125 | 14.341 | 1.00 | 25.07 | A | C |
| ATOM | 4034 | O | HIS | A | 254 | 52.909 | 4.535 | 14.788 | 1.00 | 25.17 | A | O |
| ATOM | 4036 | N | PHE | A | 255 | 50.694 | 4.627 | 14.391 | 1.00 | 25.01 | A | N |
| ATOM | 4037 | CA | PHE | A | 255 | 50.392 | 3.332 | 15.013 | 1.00 | 25.06 | A | C |
| ATOM | 4039 | CB | PHE | A | 255 | 48.870 | 3.157 | 15.153 | 1.00 | 24.83 | A | C |
| ATOM | 4042 | CG | PHE | A | 255 | 48.151 | 2.999 | 13.837 | 1.00 | 24.67 | A | C |
| ATOM | 4043 | CD1 | PHE | A | 255 | 48.013 | 1.745 | 13.248 | 1.00 | 25.14 | A | C |
| ATOM | 4045 | CE1 | PHE | A | 255 | 47.361 | 1.596 | 12.027 | 1.00 | 24.77 | A | C |
| ATOM | 4047 | CZ | PHE | A | 255 | 46.838 | 2.708 | 11.386 | 1.00 | 25.06 | A | C |
| ATOM | 4049 | CE2 | PHE | A | 255 | 46.970 | 3.965 | 11.963 | 1.00 | 25.14 | A | C |
| ATOM | 4051 | CD2 | PHE | A | 255 | 47.624 | 4.105 | 13.182 | 1.00 | 24.68 | A | C |
| ATOM | 4053 | C | PHE | A | 255 | 50.962 | 2.125 | 14.256 | 1.00 | 25.30 | A | C |
| ATOM | 4054 | O | PHE | A | 255 | 51.288 | 1.106 | 14.869 | 1.00 | 25.15 | A | O |
| ATOM | 4056 | N | ALA | A | 256 | 51.078 | 2.245 | 12.934 | 1.00 | 25.66 | A | N |
| ATOM | 4057 | CA | ALA | A | 256 | 51.252 | 1.084 | 12.055 | 1.00 | 25.87 | A | C |
| ATOM | 4059 | CB | ALA | A | 256 | 50.884 | 1.454 | 10.622 | 1.00 | 25.83 | A | C |
| ATOM | 4063 | C | ALA | A | 256 | 52.651 | 0.468 | 12.095 | 1.00 | 26.20 | A | C |
| ATOM | 4064 | O | ALA | A | 256 | 53.654 | 1.177 | 12.226 | 1.00 | 26.11 | A | O |
| ATOM | 4066 | N | ARG | A | 257 | 52.696 | −0.857 | 11.962 | 1.00 | 26.63 | A | N |
| ATOM | 4067 | CA | ARG | A | 257 | 53.943 | −1.621 | 12.006 | 1.00 | 27.23 | A | C |
| ATOM | 4069 | CB | ARG | A | 257 | 53.705 | −2.990 | 12.643 | 1.00 | 27.59 | A | C |
| ATOM | 4072 | CG | ARG | A | 257 | 53.164 | −2.956 | 14.070 | 1.00 | 29.15 | A | C |
| ATOM | 4075 | CD | ARG | A | 257 | 52.777 | −4.360 | 14.518 | 1.00 | 30.54 | A | C |
| ATOM | 4078 | NE | ARG | A | 257 | 51.707 | −4.906 | 13.678 | 1.00 | 31.05 | A | N |
| ATOM | 4080 | CZ | ARG | A | 257 | 51.478 | −6.201 | 13.463 | 1.00 | 31.20 | A | C |
| ATOM | 4081 | NH1 | ARG | A | 257 | 52.242 | −7.139 | 14.018 | 1.00 | 31.74 | A | N |
| ATOM | 4084 | NH2 | ARG | A | 257 | 50.471 | −6.563 | 12.674 | 1.00 | 31.30 | A | N |
| ATOM | 4087 | C | ARG | A | 257 | 54.516 | −1.828 | 10.608 | 1.00 | 27.05 | A | C |
| ATOM | 4088 | O | ARG | A | 257 | 53.771 | −2.041 | 9.651 | 1.00 | 27.10 | A | O |
| ATOM | 4090 | N | ASP | A | 258 | 55.844 | −1.788 | 10.508 | 1.00 | 26.97 | A | N |
| ATOM | 4091 | CA | ASP | A | 258 | 56.548 | −1.937 | 9.236 | 1.00 | 26.68 | A | C |
| ATOM | 4093 | CB | ASP | A | 258 | 57.713 | −0.945 | 9.169 | 1.00 | 26.49 | A | C |
| ATOM | 4096 | CG | ASP | A | 258 | 58.241 | −0.759 | 7.764 | 1.00 | 26.72 | A | C |
| ATOM | 4097 | OD1 | ASP | A | 258 | 58.470 | −1.768 | 7.065 | 1.00 | 26.55 | A | O |
| ATOM | 4098 | OD2 | ASP | A | 258 | 58.428 | 0.405 | 7.351 | 1.00 | 28.47 | A | O |
| ATOM | 4099 | C | ASP | A | 258 | 57.049 | −3.373 | 9.073 | 1.00 | 26.57 | A | C |
| ATOM | 4100 | O | ASP | A | 258 | 58.058 | −3.759 | 9.667 | 1.00 | 26.72 | A | O |
| ATOM | 4102 | N | ARG | A | 259 | 56.342 | −4.157 | 8.262 | 1.00 | 26.49 | A | N |
| ATOM | 4103 | CA | ARG | A | 259 | 56.655 | −5.575 | 8.073 | 1.00 | 26.58 | A | C |
| ATOM | 4105 | CB | ARG | A | 259 | 55.578 | −6.447 | 8.738 | 1.00 | 27.25 | A | C |

TABLE 8-2-continued

| Coordinates for L494P Structure | | | | | | | | | | | | |
|---|---|---|---|---|---|---|---|---|---|---|---|---|
| ATOM | 4108 | CG | ARG | A | 259 | 55.479 | −6.323 | 10.260 | 1.00 | 28.80 | A | C |
| ATOM | 4111 | CD | ARG | A | 259 | 56.423 | −7.277 | 10.983 | 1.00 | 30.14 | A | C |
| ATOM | 4114 | NE | ARG | A | 259 | 56.188 | −7.278 | 12.428 | 1.00 | 32.18 | A | N |
| ATOM | 4116 | CZ | ARG | A | 259 | 56.604 | −6.335 | 13.275 | 1.00 | 32.94 | A | C |
| ATOM | 4117 | NH1 | ARG | A | 259 | 57.290 | −5.280 | 12.842 | 1.00 | 34.19 | A | N |
| ATOM | 4120 | NH2 | ARG | A | 259 | 56.329 | −6.444 | 14.572 | 1.00 | 32.41 | A | N |
| ATOM | 4123 | C | ARG | A | 259 | 56.758 | −5.934 | 6.588 | 1.00 | 25.53 | A | C |
| ATOM | 4124 | O | ARG | A | 259 | 55.939 | −6.696 | 6.070 | 1.00 | 25.27 | A | O |
| ATOM | 4126 | N | LEU | A | 260 | 57.759 | −5.383 | 5.905 | 1.00 | 24.36 | A | N |
| ATOM | 4127 | CA | LEU | A | 260 | 57.987 | −5.709 | 4.496 | 1.00 | 23.56 | A | C |
| ATOM | 4129 | CB | LEU | A | 260 | 58.444 | −4.482 | 3.705 | 1.00 | 23.49 | A | C |
| ATOM | 4132 | CG | LEU | A | 260 | 58.738 | −4.732 | 2.220 | 1.00 | 22.82 | A | C |
| ATOM | 4134 | CD1 | LEU | A | 260 | 57.541 | −5.359 | 1.522 | 1.00 | 22.27 | A | C |
| ATOM | 4138 | CD2 | LEU | A | 260 | 59.145 | −3.448 | 1.530 | 1.00 | 23.21 | A | C |
| ATOM | 4142 | C | LEU | A | 260 | 59.024 | −6.812 | 4.382 | 1.00 | 22.93 | A | C |
| ATOM | 4143 | O | LEU | A | 260 | 58.782 | −7.834 | 3.736 | 1.00 | 23.24 | A | O |
| ATOM | 4145 | N | ILE | A | 261 | 60.175 | −6.592 | 5.013 | 1.00 | 22.02 | A | N |
| ATOM | 4146 | CA | ILE | A | 261 | 61.239 | −7.595 | 5.083 | 1.00 | 21.34 | A | C |
| ATOM | 4148 | CB | ILE | A | 261 | 62.309 | −7.215 | 6.131 | 1.00 | 21.16 | A | C |
| ATOM | 4150 | CG1 | ILE | A | 261 | 63.001 | −5.893 | 5.765 | 1.00 | 20.68 | A | C |
| ATOM | 4153 | CD1 | ILE | A | 261 | 63.318 | −5.016 | 6.972 | 1.00 | 19.12 | A | C |
| ATOM | 4157 | CG2 | ILE | A | 261 | 63.336 | −8.335 | 6.266 | 1.00 | 20.90 | A | C |
| ATOM | 4161 | C | ILE | A | 261 | 60.644 | −8.943 | 5.477 | 1.00 | 21.18 | A | C |
| ATOM | 4162 | O | ILE | A | 261 | 60.982 | −9.973 | 4.900 | 1.00 | 20.99 | A | O |
| ATOM | 4164 | N | GLU | A | 262 | 59.747 | −8.915 | 6.459 | 1.00 | 21.36 | A | N |
| ATOM | 4165 | CA | GLU | A | 262 | 59.060 | −10.112 | 6.927 | 1.00 | 21.68 | A | C |
| ATOM | 4167 | CB | GLU | A | 262 | 58.375 | −9.849 | 8.276 | 1.00 | 21.72 | A | C |
| ATOM | 4170 | CG | GLU | A | 262 | 59.332 | −9.744 | 9.477 | 1.00 | 21.84 | A | C |
| ATOM | 4173 | CD | GLU | A | 262 | 59.863 | −8.335 | 9.740 | 1.00 | 21.66 | A | C |
| ATOM | 4174 | OE1 | GLU | A | 262 | 59.610 | −7.413 | 8.933 | 1.00 | 21.94 | A | O |
| ATOM | 4175 | OE2 | GLU | A | 262 | 60.540 | −8.150 | 10.772 | 1.00 | 21.41 | A | O |
| ATOM | 4176 | C | GLU | A | 262 | 58.036 | −10.625 | 5.911 | 1.00 | 22.32 | A | C |
| ATOM | 4177 | O | GLU | A | 262 | 57.901 | −11.837 | 5.728 | 1.00 | 23.24 | A | O |
| ATOM | 4179 | N | SER | A | 263 | 57.313 | −9.712 | 5.262 | 1.00 | 22.49 | A | N |
| ATOM | 4180 | CA | SER | A | 263 | 56.288 | −10.094 | 4.277 | 1.00 | 22.31 | A | C |
| ATOM | 4182 | CB | SER | A | 263 | 55.386 | −8.909 | 3.919 | 1.00 | 22.29 | A | C |
| ATOM | 4185 | OG | SER | A | 263 | 54.431 | −8.678 | 4.939 | 1.00 | 22.39 | A | O |
| ATOM | 4187 | C | SER | A | 263 | 56.883 | −10.687 | 3.004 | 1.00 | 22.14 | A | C |
| ATOM | 4188 | O | SER | A | 263 | 56.274 | −11.555 | 2.382 | 1.00 | 22.58 | A | O |
| ATOM | 4190 | N | PHE | A | 264 | 58.059 | −10.214 | 2.606 | 1.00 | 22.01 | A | N |
| ATOM | 4191 | CA | PHE | A | 264 | 58.750 | −10.795 | 1.460 | 1.00 | 22.14 | A | C |
| ATOM | 4193 | CB | PHE | A | 264 | 59.942 | −9.933 | 1.038 | 1.00 | 22.16 | A | C |
| ATOM | 4196 | CG | PHE | A | 264 | 60.511 | −10.311 | −0.297 | 1.00 | 21.05 | A | C |
| ATOM | 4197 | CD1 | PHE | A | 264 | 59.905 | −9.880 | −1.467 | 1.00 | 20.84 | A | C |
| ATOM | 4199 | CE1 | PHE | A | 264 | 60.418 | −10.230 | −2.703 | 1.00 | 21.07 | A | C |
| ATOM | 4201 | CZ | PHE | A | 264 | 61.552 | −11.021 | −2.778 | 1.00 | 22.11 | A | C |
| ATOM | 4203 | CE2 | PHE | A | 264 | 62.164 | −11.460 | −1.615 | 1.00 | 21.87 | A | C |
| ATOM | 4205 | CD2 | PHE | A | 264 | 61.641 | −11.108 | −0.384 | 1.00 | 20.79 | A | C |
| ATOM | 4207 | C | PHE | A | 264 | 59.212 | −12.211 | 1.800 | 1.00 | 22.40 | A | C |
| ATOM | 4208 | O | PHE | A | 264 | 58.950 | −13.149 | 1.042 | 1.00 | 22.39 | A | O |
| ATOM | 4210 | N | TYR | A | 265 | 59.885 | −12.349 | 2.946 | 1.00 | 22.32 | A | N |
| ATOM | 4211 | CA | TYR | A | 265 | 60.319 | −13.651 | 3.472 | 1.00 | 22.09 | A | C |
| ATOM | 4213 | CB | TYR | A | 265 | 60.930 | −13.489 | 4.872 | 1.00 | 22.28 | A | C |
| ATOM | 4216 | CG | TYR | A | 265 | 61.069 | −14.783 | 5.649 | 1.00 | 25.25 | A | C |
| ATOM | 4217 | CD1 | TYR | A | 265 | 62.150 | −15.636 | 5.438 | 1.00 | 27.20 | A | C |
| ATOM | 4219 | CE1 | TYR | A | 265 | 62.281 | −16.826 | 6.149 | 1.00 | 27.66 | A | C |
| ATOM | 4221 | CZ | TYR | A | 265 | 61.322 | −17.173 | 7.084 | 1.00 | 29.34 | A | C |
| ATOM | 4222 | OH | TYR | A | 265 | 61.447 | −18.349 | 7.791 | 1.00 | 32.52 | A | O |
| ATOM | 4224 | CE2 | TYR | A | 265 | 60.238 | −16.344 | 7.314 | 1.00 | 29.12 | A | C |
| ATOM | 4226 | CD2 | TYR | A | 265 | 60.117 | −15.156 | 6.598 | 1.00 | 28.54 | A | C |
| ATOM | 4228 | C | TYR | A | 265 | 59.163 | −14.649 | 3.513 | 1.00 | 21.42 | A | C |
| ATOM | 4229 | O | TYR | A | 265 | 59.334 | −15.821 | 3.175 | 1.00 | 21.62 | A | O |
| ATOM | 4231 | N | TRP | A | 266 | 57.992 | −14.180 | 3.935 | 1.00 | 20.65 | A | N |
| ATOM | 4232 | CA | TRP | A | 266 | 56.774 | −14.980 | 3.860 | 1.00 | 20.27 | A | C |
| ATOM | 4234 | CB | TRP | A | 266 | 55.576 | −14.189 | 4.407 | 1.00 | 20.42 | A | C |
| ATOM | 4237 | CG | TRP | A | 266 | 54.261 | −14.891 | 4.247 | 1.00 | 19.95 | A | C |
| ATOM | 4238 | CD1 | TRP | A | 266 | 53.460 | −14.889 | 3.143 | 1.00 | 19.27 | A | C |
| ATOM | 4240 | NE1 | TRP | A | 266 | 52.339 | −15.648 | 3.368 | 1.00 | 19.44 | A | N |
| ATOM | 4242 | CE2 | TRP | A | 266 | 52.394 | −16.154 | 4.639 | 1.00 | 19.32 | A | C |
| ATOM | 4243 | CD2 | TRP | A | 266 | 53.595 | −15.697 | 5.223 | 1.00 | 19.63 | A | C |
| ATOM | 4244 | CE3 | TRP | A | 266 | 53.895 | −16.075 | 6.537 | 1.00 | 20.02 | A | C |
| ATOM | 4246 | CZ3 | TRP | A | 266 | 53.000 | −16.890 | 7.215 | 1.00 | 20.91 | A | C |
| ATOM | 4248 | CH2 | TRP | A | 266 | 51.812 | −17.331 | 6.604 | 1.00 | 19.64 | A | C |
| ATOM | 4250 | CZ2 | TRP | A | 266 | 51.493 | −16.975 | 5.321 | 1.00 | 18.62 | A | C |
| ATOM | 4252 | C | TRP | A | 266 | 56.509 | −15.411 | 2.416 | 1.00 | 19.60 | A | C |
| ATOM | 4253 | O | TRP | A | 266 | 56.278 | −16.590 | 2.146 | 1.00 | 19.63 | A | O |
| ATOM | 4255 | N | ALA | A | 267 | 56.556 | −14.446 | 1.498 | 1.00 | 18.71 | A | N |
| ATOM | 4256 | CA | ALA | A | 267 | 56.272 | −14.687 | 0.081 | 1.00 | 18.06 | A | C |

TABLE 8-2-continued

Coordinates for L494P Structure

| | | | | | | | | | | | | |
|---|---|---|---|---|---|---|---|---|---|---|---|---|
| ATOM | 4258 | CB | ALA | A | 267 | 56.264 | −13.372 | −0.682 | 1.00 | 18.02 | A | C |
| ATOM | 4262 | C | ALA | A | 267 | 57.241 | −15.669 | −0.581 | 1.00 | 17.64 | A | C |
| ATOM | 4263 | O | ALA | A | 267 | 56.872 | −16.341 | −1.542 | 1.00 | 17.61 | A | O |
| ATOM | 4265 | N | VAL | A | 268 | 58.470 | −15.748 | −0.069 | 1.00 | 17.18 | A | N |
| ATOM | 4266 | CA | VAL | A | 268 | 59.479 | −16.690 | −0.579 | 1.00 | 16.54 | A | C |
| ATOM | 4268 | CB | VAL | A | 268 | 60.872 | −16.405 | 0.039 | 1.00 | 16.49 | A | C |
| ATOM | 4270 | CG1 | VAL | A | 268 | 61.390 | −15.062 | −0.451 | 1.00 | 16.73 | A | C |
| ATOM | 4274 | CG2 | VAL | A | 268 | 61.866 | −17.511 | −0.297 | 1.00 | 16.29 | A | C |
| ATOM | 4278 | C | VAL | A | 268 | 59.080 | −18.154 | −0.340 | 1.00 | 15.77 | A | C |
| ATOM | 4279 | O | VAL | A | 268 | 59.385 | −19.028 | −1.150 | 1.00 | 15.33 | A | O |
| ATOM | 4281 | N | GLY | A | 269 | 58.395 | −18.415 | 0.766 | 1.00 | 15.52 | A | N |
| ATOM | 4282 | CA | GLY | A | 269 | 57.832 | −19.737 | 1.016 | 1.00 | 15.52 | A | C |
| ATOM | 4285 | C | GLY | A | 269 | 56.673 | −20.066 | 0.090 | 1.00 | 15.20 | A | C |
| ATOM | 4286 | O | GLY | A | 269 | 56.391 | −21.237 | −0.160 | 1.00 | 14.64 | A | O |
| ATOM | 4288 | N | VAL | A | 270 | 56.007 | −19.032 | −0.419 | 1.00 | 14.97 | A | N |
| ATOM | 4289 | CA | VAL | A | 270 | 54.835 | −19.200 | −1.280 | 1.00 | 14.94 | A | C |
| ATOM | 4291 | CB | VAL | A | 270 | 53.887 | −17.979 | −1.178 | 1.00 | 14.38 | A | C |
| ATOM | 4293 | CG1 | VAL | A | 270 | 52.554 | −18.286 | −1.826 | 1.00 | 13.66 | A | C |
| ATOM | 4297 | CG2 | VAL | A | 270 | 53.677 | −17.584 | 0.272 | 1.00 | 12.55 | A | C |
| ATOM | 4301 | C | VAL | A | 270 | 55.230 | −19.429 | −2.747 | 1.00 | 15.75 | A | C |
| ATOM | 4302 | O | VAL | A | 270 | 54.475 | −20.036 | −3.508 | 1.00 | 16.17 | A | O |
| ATOM | 4304 | N | ALA | A | 271 | 56.410 | −18.948 | −3.140 | 1.00 | 16.28 | A | N |
| ATOM | 4305 | CA | ALA | A | 271 | 56.906 | −19.120 | −4.510 | 1.00 | 16.56 | A | C |
| ATOM | 4307 | CB | ALA | A | 271 | 56.190 | −18.161 | −5.450 | 1.00 | 16.49 | A | C |
| ATOM | 4311 | C | ALA | A | 271 | 58.429 | −18.926 | −4.586 | 1.00 | 16.90 | A | C |
| ATOM | 4312 | O | ALA | A | 271 | 58.925 | −17.849 | −4.925 | 1.00 | 16.39 | A | O |
| ATOM | 4314 | N | PHE | A | 272 | 59.155 | −19.993 | −4.273 | 1.00 | 17.53 | A | N |
| ATOM | 4315 | CA | PHE | A | 272 | 60.616 | −19.960 | −4.183 | 1.00 | 18.21 | A | C |
| ATOM | 4317 | CB | PHE | A | 272 | 61.119 | −21.181 | −3.416 | 1.00 | 18.52 | A | C |
| ATOM | 4320 | CG | PHE | A | 272 | 61.061 | −22.460 | −4.207 | 1.00 | 19.27 | A | C |
| ATOM | 4321 | CD1 | PHE | A | 272 | 62.180 | −22.915 | −4.894 | 1.00 | 19.23 | A | C |
| ATOM | 4323 | CE1 | PHE | A | 272 | 62.132 | −24.095 | −5.624 | 1.00 | 21.26 | A | C |
| ATOM | 4325 | CZ | PHE | A | 272 | 60.951 | −24.832 | −5.677 | 1.00 | 22.55 | A | C |
| ATOM | 4327 | CE2 | PHE | A | 272 | 59.825 | −24.383 | −4.999 | 1.00 | 21.20 | A | C |
| ATOM | 4329 | CD2 | PHE | A | 272 | 59.885 | −23.204 | −4.271 | 1.00 | 20.42 | A | C |
| ATOM | 4331 | C | PHE | A | 272 | 61.325 | −19.925 | −5.533 | 1.00 | 18.82 | A | C |
| ATOM | 4332 | O | PHE | A | 272 | 62.415 | −19.362 | −5.642 | 1.00 | 19.34 | A | O |
| ATOM | 4334 | N | GLU | A | 273 | 60.728 | −20.554 | −6.545 | 1.00 | 19.20 | A | N |
| ATOM | 4335 | CA | GLU | A | 273 | 61.364 | −20.679 | −7.859 | 1.00 | 19.20 | A | C |
| ATOM | 4337 | CB | GLU | A | 273 | 60.476 | −21.457 | −8.842 | 1.00 | 19.46 | A | C |
| ATOM | 4340 | CG | GLU | A | 273 | 60.093 | −22.880 | −8.399 | 1.00 | 20.71 | A | C |
| ATOM | 4343 | CD | GLU | A | 273 | 58.655 | −23.005 | −7.879 | 1.00 | 22.87 | A | C |
| ATOM | 4344 | OE1 | GLU | A | 273 | 58.171 | −22.086 | −7.178 | 1.00 | 22.37 | A | O |
| ATOM | 4345 | OE2 | GLU | A | 273 | 58.008 | −24.035 | −8.173 | 1.00 | 22.23 | A | O |
| ATOM | 4346 | C | GLU | A | 273 | 61.680 | −19.288 | −8.416 | 1.00 | 18.84 | A | C |
| ATOM | 4347 | O | GLU | A | 273 | 60.846 | −18.388 | −8.333 | 1.00 | 19.02 | A | O |
| ATOM | 4349 | N | PRO | A | 274 | 62.887 | −19.108 | −8.984 | 1.00 | 18.67 | A | N |
| ATOM | 4350 | CA | PRO | A | 274 | 63.353 | −17.773 | −9.375 | 1.00 | 18.87 | A | C |
| ATOM | 4352 | CB | PRO | A | 274 | 64.762 | −18.034 | −9.924 | 1.00 | 18.89 | A | C |
| ATOM | 4355 | CG | PRO | A | 274 | 64.786 | −19.471 | −10.280 | 1.00 | 18.67 | A | C |
| ATOM | 4358 | CD | PRO | A | 274 | 63.861 | −20.157 | −9.335 | 1.00 | 18.65 | A | C |
| ATOM | 4361 | C | PRO | A | 274 | 62.487 | −17.066 | −10.422 | 1.00 | 19.21 | A | C |
| ATOM | 4362 | O | PRO | A | 274 | 62.470 | −15.837 | −10.467 | 1.00 | 19.76 | A | O |
| ATOM | 4363 | N | GLN | A | 275 | 61.771 | −17.829 | −11.243 | 1.00 | 19.37 | A | N |
| ATOM | 4364 | CA | GLN | A | 275 | 60.924 | −17.247 | −12.286 | 1.00 | 19.69 | A | C |
| ATOM | 4366 | CB | GLN | A | 275 | 60.631 | −18.272 | −13.395 | 1.00 | 19.95 | A | C |
| ATOM | 4369 | CG | GLN | A | 275 | 59.739 | −19.459 | −12.995 | 1.00 | 20.88 | A | C |
| ATOM | 4372 | CD | GLN | A | 275 | 60.526 | −20.705 | −12.614 | 1.00 | 21.94 | A | C |
| ATOM | 4373 | OE1 | GLN | A | 275 | 61.655 | −20.620 | −12.130 | 1.00 | 24.29 | A | O |
| ATOM | 4374 | NE2 | GLN | A | 275 | 59.924 | −21.870 | −12.826 | 1.00 | 22.72 | A | N |
| ATOM | 4377 | C | GLN | A | 275 | 59.607 | −16.633 | −11.782 | 1.00 | 19.72 | A | C |
| ATOM | 4378 | O | GLN | A | 275 | 58.905 | −15.991 | −12.562 | 1.00 | 20.27 | A | O |
| ATOM | 4380 | N | TYR | A | 276 | 59.270 | −16.819 | −10.504 | 1.00 | 19.68 | A | N |
| ATOM | 4381 | CA | TYR | A | 276 | 58.020 | −16.279 | −9.942 | 1.00 | 19.96 | A | C |
| ATOM | 4383 | CB | TYR | A | 276 | 57.339 | −17.321 | −9.044 | 1.00 | 20.06 | A | C |
| ATOM | 4386 | CG | TYR | A | 276 | 56.799 | −18.541 | −9.762 | 1.00 | 21.44 | A | C |
| ATOM | 4387 | CD1 | TYR | A | 276 | 55.960 | −18.417 | −10.867 | 1.00 | 21.90 | A | C |
| ATOM | 4389 | CE1 | TYR | A | 276 | 55.455 | −19.537 | −11.516 | 1.00 | 22.01 | A | C |
| ATOM | 4391 | CZ | TYR | A | 276 | 55.773 | −20.800 | −11.051 | 1.00 | 23.26 | A | C |
| ATOM | 4392 | OH | TYR | A | 276 | 55.276 | −21.917 | −11.683 | 1.00 | 24.08 | A | O |
| ATOM | 4394 | CE2 | TYR | A | 276 | 56.592 | −20.949 | −9.946 | 1.00 | 23.34 | A | C |
| ATOM | 4396 | CD2 | TYR | A | 276 | 57.095 | −19.824 | −9.306 | 1.00 | 22.64 | A | C |
| ATOM | 4398 | C | TYR | A | 276 | 58.219 | −14.977 | −9.147 | 1.00 | 19.98 | A | C |
| ATOM | 4399 | O | TYR | A | 276 | 57.639 | −14.802 | −8.072 | 1.00 | 19.72 | A | O |
| ATOM | 4401 | N | SER | A | 277 | 59.021 | −14.059 | −9.682 | 1.00 | 20.07 | A | N |
| ATOM | 4402 | CA | SER | A | 277 | 59.270 | −12.770 | −9.027 | 1.00 | 19.67 | A | C |
| ATOM | 4404 | CB | SER | A | 277 | 60.267 | −11.938 | −9.838 | 1.00 | 19.60 | A | C |
| ATOM | 4407 | OG | SER | A | 277 | 61.513 | −12.603 | −9.956 | 1.00 | 20.14 | A | O |

TABLE 8-2-continued

Coordinates for L494P Structure

| | | | | | | | | | | | | |
|---|---|---|---|---|---|---|---|---|---|---|---|---|
| ATOM | 4409 | C | SER | A | 277 | 57.984 | −11.973 | −8.822 | 1.00 | 19.33 | A | C |
| ATOM | 4410 | O | SER | A | 277 | 57.776 | −11.385 | −7.761 | 1.00 | 19.21 | A | O |
| ATOM | 4412 | N | ASP | A | 278 | 57.123 | −11.959 | −9.835 | 1.00 | 19.20 | A | N |
| ATOM | 4413 | CA | ASP | A | 278 | 55.859 | −11.226 | −9.754 | 1.00 | 19.25 | A | C |
| ATOM | 4415 | CB | ASP | A | 278 | 55.085 | −11.316 | −11.077 | 1.00 | 19.35 | A | C |
| ATOM | 4418 | CG | ASP | A | 278 | 55.629 | −10.380 | −12.143 | 1.00 | 18.93 | A | C |
| ATOM | 4419 | OD1 | ASP | A | 278 | 56.348 | −9.419 | −11.796 | 1.00 | 18.90 | A | O |
| ATOM | 4420 | OD2 | ASP | A | 278 | 55.327 | −10.600 | −13.333 | 1.00 | 18.56 | A | O |
| ATOM | 4421 | C | ASP | A | 278 | 54.979 | −11.716 | −8.606 | 1.00 | 19.13 | A | C |
| ATOM | 4422 | O | ASP | A | 278 | 54.356 | −10.908 | −7.916 | 1.00 | 19.10 | A | O |
| ATOM | 4424 | N | CYS | A | 279 | 54.930 | −13.031 | −8.403 | 1.00 | 18.93 | A | N |
| ATOM | 4425 | CA | CYS | A | 279 | 54.146 | −13.601 | −7.307 | 1.00 | 18.82 | A | C |
| ATOM | 4427 | CB | CYS | A | 279 | 54.090 | −15.129 | −7.401 | 1.00 | 18.89 | A | C |
| ATOM | 4430 | SG | CYS | A | 279 | 52.896 | −15.884 | −6.264 | 1.00 | 18.55 | A | S |
| ATOM | 4432 | C | CYS | A | 279 | 54.716 | −13.185 | −5.956 | 1.00 | 18.54 | A | C |
| ATOM | 4433 | O | CYS | A | 279 | 53.965 | −12.865 | −5.033 | 1.00 | 18.37 | A | O |
| ATOM | 4435 | N | ARG | A | 280 | 56.044 | −13.189 | −5.853 | 1.00 | 18.40 | A | N |
| ATOM | 4436 | CA | ARG | A | 280 | 56.730 | −12.759 | −4.635 | 1.00 | 18.00 | A | C |
| ATOM | 4438 | CB | ARG | A | 280 | 58.239 | −13.013 | −4.735 | 1.00 | 18.28 | A | C |
| ATOM | 4441 | CG | ARG | A | 280 | 58.634 | −14.477 | −4.592 | 1.00 | 18.99 | A | C |
| ATOM | 4444 | CD | ARG | A | 280 | 60.137 | −14.630 | −4.420 | 1.00 | 19.95 | A | C |
| ATOM | 4447 | NE | ARG | A | 280 | 60.867 | −14.212 | −5.615 | 1.00 | 21.16 | A | N |
| ATOM | 4449 | CZ | ARG | A | 280 | 61.053 | −14.964 | −6.700 | 1.00 | 23.15 | A | C |
| ATOM | 4450 | NH1 | ARG | A | 280 | 60.562 | −16.198 | −6.772 | 1.00 | 24.11 | A | N |
| ATOM | 4453 | NH2 | ARG | A | 280 | 61.736 | −14.475 | −7.728 | 1.00 | 24.44 | A | N |
| ATOM | 4456 | C | ARG | A | 280 | 56.464 | −11.285 | −4.344 | 1.00 | 17.11 | A | C |
| ATOM | 4457 | O | ARG | A | 280 | 56.147 | −10.923 | −3.210 | 1.00 | 16.85 | A | O |
| ATOM | 4459 | N | ASN | A | 281 | 56.586 | −10.443 | −5.369 | 1.00 | 16.30 | A | N |
| ATOM | 4460 | CA | ASN | A | 281 | 56.313 | −9.014 | −5.220 | 1.00 | 15.91 | A | C |
| ATOM | 4462 | CB | ASN | A | 281 | 56.684 | −8.244 | −6.493 | 1.00 | 16.20 | A | C |
| ATOM | 4465 | CG | ASN | A | 281 | 58.192 | −8.136 | −6.703 | 1.00 | 17.16 | A | C |
| ATOM | 4466 | OD1 | ASN | A | 281 | 58.988 | −8.551 | −5.858 | 1.00 | 17.08 | A | O |
| ATOM | 4467 | ND2 | ASN | A | 281 | 58.588 | −7.568 | −7.839 | 1.00 | 18.22 | A | N |
| ATOM | 4470 | C | ASN | A | 281 | 54.857 | −8.741 | −4.841 | 1.00 | 15.14 | A | C |
| ATOM | 4471 | O | ASN | A | 281 | 54.595 | −7.924 | −3.964 | 1.00 | 15.32 | A | O |
| ATOM | 4473 | N | SER | A | 282 | 53.920 | −9.432 | −5.491 | 1.00 | 14.30 | A | N |
| ATOM | 4474 | CA | SER | A | 282 | 52.494 | −9.294 | −5.173 | 1.00 | 13.39 | A | C |
| ATOM | 4476 | CB | SER | A | 282 | 51.631 | −10.127 | −6.124 | 1.00 | 13.27 | A | C |
| ATOM | 4479 | OG | SER | A | 282 | 51.539 | −9.524 | −7.400 | 1.00 | 13.30 | A | O |
| ATOM | 4481 | C | SER | A | 282 | 52.202 | −9.701 | −3.731 | 1.00 | 12.98 | A | C |
| ATOM | 4482 | O | SER | A | 282 | 51.743 | −8.880 | −2.933 | 1.00 | 12.94 | A | O |
| ATOM | 4484 | N | VAL | A | 283 | 52.471 | −10.963 | −3.402 | 1.00 | 12.45 | A | N |
| ATOM | 4485 | CA | VAL | A | 283 | 52.241 | −11.475 | −2.050 | 1.00 | 12.34 | A | C |
| ATOM | 4487 | CB | VAL | A | 283 | 52.831 | −12.895 | −1.858 | 1.00 | 12.07 | A | C |
| ATOM | 4489 | CG1 | VAL | A | 283 | 52.867 | −13.272 | −0.387 | 1.00 | 11.16 | A | C |
| ATOM | 4493 | CG2 | VAL | A | 283 | 52.029 | −13.918 | −2.639 | 1.00 | 10.41 | A | C |
| ATOM | 4497 | C | VAL | A | 283 | 52.837 | −10.520 | −1.015 | 1.00 | 12.92 | A | C |
| ATOM | 4498 | O | VAL | A | 283 | 52.173 | −10.150 | −0.048 | 1.00 | 12.86 | A | O |
| ATOM | 4500 | N | ALA | A | 284 | 54.082 | −10.111 | −1.243 | 1.00 | 13.80 | A | N |
| ATOM | 4501 | CA | ALA | A | 284 | 54.772 | −9.179 | −0.351 | 1.00 | 14.74 | A | C |
| ATOM | 4503 | CB | ALA | A | 284 | 56.179 | −8.900 | −0.871 | 1.00 | 14.73 | A | C |
| ATOM | 4507 | C | ALA | A | 284 | 54.006 | −7.864 | −0.172 | 1.00 | 15.30 | A | C |
| ATOM | 4508 | O | ALA | A | 284 | 53.811 | −7.400 | 0.952 | 1.00 | 14.93 | A | O |
| ATOM | 4510 | N | LYS | A | 285 | 53.578 | −7.272 | −1.283 | 1.00 | 16.13 | A | N |
| ATOM | 4511 | CA | LYS | A | 285 | 52.841 | −6.012 | −1.248 | 1.00 | 17.03 | A | C |
| ATOM | 4513 | CB | LYS | A | 285 | 52.562 | −5.503 | −2.668 | 1.00 | 17.14 | A | C |
| ATOM | 4516 | CG | LYS | A | 285 | 53.756 | −4.834 | −3.335 | 1.00 | 18.60 | A | C |
| ATOM | 4519 | CD | LYS | A | 285 | 53.407 | −4.320 | −4.722 | 1.00 | 21.08 | A | C |
| ATOM | 4522 | CE | LYS | A | 285 | 54.618 | −3.718 | −5.417 | 1.00 | 22.65 | A | C |
| ATOM | 4525 | NZ | LYS | A | 285 | 54.341 | −3.399 | −6.848 | 1.00 | 24.04 | A | N |
| ATOM | 4529 | C | LYS | A | 285 | 51.529 | −6.160 | −0.481 | 1.00 | 17.73 | A | C |
| ATOM | 4530 | O | LYS | A | 285 | 51.239 | −5.379 | 0.431 | 1.00 | 17.94 | A | O |
| ATOM | 4532 | N | MET | A | 286 | 50.747 | −7.171 | −0.846 | 1.00 | 18.03 | A | N |
| ATOM | 4533 | CA | MET | A | 286 | 49.426 | −7.367 | −0.253 | 1.00 | 18.01 | A | C |
| ATOM | 4535 | CB | MET | A | 286 | 48.670 | −8.498 | −0.966 | 1.00 | 18.01 | A | C |
| ATOM | 4538 | CG | MET | A | 286 | 48.323 | −8.209 | −2.429 | 1.00 | 17.41 | A | C |
| ATOM | 4541 | SD | MET | A | 286 | 47.631 | −6.560 | −2.713 | 1.00 | 16.92 | A | S |
| ATOM | 4542 | CE | MET | A | 286 | 49.115 | −5.597 | −2.995 | 1.00 | 16.98 | A | C |
| ATOM | 4546 | C | MET | A | 286 | 49.524 | −7.651 | 1.240 | 1.00 | 17.81 | A | C |
| ATOM | 4547 | O | MET | A | 286 | 48.835 | −7.017 | 2.042 | 1.00 | 17.92 | A | O |
| ATOM | 4549 | N | PHE | A | 287 | 50.394 | −8.587 | 1.606 | 1.00 | 17.47 | A | N |
| ATOM | 4550 | CA | PHE | A | 287 | 50.575 | −8.976 | 3.007 | 1.00 | 17.44 | A | C |
| ATOM | 4552 | CB | PHE | A | 287 | 51.516 | −10.186 | 3.094 | 1.00 | 17.98 | A | C |
| ATOM | 4555 | CG | PHE | A | 287 | 51.463 | −10.925 | 4.409 | 1.00 | 20.17 | A | C |
| ATOM | 4556 | CD1 | PHE | A | 287 | 50.248 | −11.252 | 5.004 | 1.00 | 22.99 | A | C |
| ATOM | 4558 | CE1 | PHE | A | 287 | 50.204 | −11.947 | 6.205 | 1.00 | 23.48 | A | C |
| ATOM | 4560 | CZ | PHE | A | 287 | 51.380 | −12.337 | 6.820 | 1.00 | 25.00 | A | C |
| ATOM | 4562 | CE2 | PHE | A | 287 | 52.598 | −12.029 | 6.233 | 1.00 | 25.35 | A | C |

TABLE 8-2-continued

Coordinates for L494P Structure

| | | | | | | | | | | | | |
|---|---|---|---|---|---|---|---|---|---|---|---|---|
| ATOM | 4564 | CD2 | PHE | A | 287 | 52.634 | −11.332 | 5.032 | 1.00 | 23.16 | A | C |
| ATOM | 4566 | C | PHE | A | 287 | 51.096 | −7.818 | 3.871 | 1.00 | 16.40 | A | C |
| ATOM | 4567 | O | PHE | A | 287 | 50.848 | −7.781 | 5.076 | 1.00 | 15.60 | A | O |
| ATOM | 4569 | N | SER | A | 288 | 51.809 | −6.879 | 3.250 | 1.00 | 15.81 | A | N |
| ATOM | 4570 | CA | SER | A | 288 | 52.251 | −5.667 | 3.934 | 1.00 | 15.38 | A | C |
| ATOM | 4572 | CB | SER | A | 288 | 53.333 | −4.945 | 3.131 | 1.00 | 15.38 | A | C |
| ATOM | 4575 | OG | SER | A | 288 | 54.539 | −5.688 | 3.137 | 1.00 | 15.78 | A | O |
| ATOM | 4577 | C | SER | A | 288 | 51.081 | −4.728 | 4.202 | 1.00 | 15.29 | A | C |
| ATOM | 4578 | O | SER | A | 288 | 51.029 | −4.099 | 5.256 | 1.00 | 15.32 | A | O |
| ATOM | 4580 | N | PHE | A | 289 | 50.149 | −4.631 | 3.253 | 1.00 | 15.52 | A | N |
| ATOM | 4581 | CA | PHE | A | 289 | 48.899 | −3.885 | 3.480 | 1.00 | 15.49 | A | C |
| ATOM | 4583 | CB | PHE | A | 289 | 48.121 | −3.650 | 2.176 | 1.00 | 15.43 | A | C |
| ATOM | 4586 | CG | PHE | A | 289 | 48.484 | −2.367 | 1.479 | 1.00 | 15.12 | A | C |
| ATOM | 4587 | CD1 | PHE | A | 289 | 48.164 | −1.144 | 2.049 | 1.00 | 14.80 | A | C |
| ATOM | 4589 | CE1 | PHE | A | 289 | 48.499 | 0.040 | 1.420 | 1.00 | 16.15 | A | C |
| ATOM | 4591 | CZ | PHE | A | 289 | 49.159 | 0.011 | 0.206 | 1.00 | 17.05 | A | C |
| ATOM | 4593 | CE2 | PHE | A | 289 | 49.479 | −1.204 | −0.376 | 1.00 | 17.05 | A | C |
| ATOM | 4595 | CD2 | PHE | A | 289 | 49.144 | −2.383 | 0.261 | 1.00 | 16.16 | A | C |
| ATOM | 4597 | C | PHE | A | 289 | 48.002 | −4.582 | 4.503 | 1.00 | 15.27 | A | C |
| ATOM | 4598 | O | PHE | A | 289 | 47.393 | −3.923 | 5.345 | 1.00 | 15.17 | A | O |
| ATOM | 4600 | N | VAL | A | 290 | 47.935 | −5.910 | 4.431 | 1.00 | 15.14 | A | N |
| ATOM | 4601 | CA | VAL | A | 290 | 47.139 | −6.696 | 5.373 | 1.00 | 15.03 | A | C |
| ATOM | 4603 | CB | VAL | A | 290 | 47.224 | −8.201 | 5.068 | 1.00 | 14.64 | A | C |
| ATOM | 4605 | CG1 | VAL | A | 290 | 46.571 | −9.010 | 6.175 | 1.00 | 14.66 | A | C |
| ATOM | 4609 | CG2 | VAL | A | 290 | 46.562 | −8.497 | 3.739 | 1.00 | 14.94 | A | C |
| ATOM | 4613 | C | VAL | A | 290 | 47.551 | −6.445 | 6.827 | 1.00 | 15.27 | A | C |
| ATOM | 4614 | O | VAL | A | 290 | 46.698 | −6.185 | 7.673 | 1.00 | 15.36 | A | O |
| ATOM | 4616 | N | THR | A | 291 | 48.851 | −6.503 | 7.110 | 1.00 | 15.61 | A | N |
| ATOM | 4617 | CA | THR | A | 291 | 49.340 | −6.286 | 8.477 | 1.00 | 15.61 | A | C |
| ATOM | 4619 | CB | THR | A | 291 | 50.886 | −6.410 | 8.595 | 1.00 | 15.42 | A | C |
| ATOM | 4621 | OG1 | THR | A | 291 | 51.520 | −5.386 | 7.819 | 1.00 | 14.83 | A | O |
| ATOM | 4623 | CG2 | THR | A | 291 | 51.369 | −7.784 | 8.132 | 1.00 | 14.64 | A | C |
| ATOM | 4627 | C | THR | A | 291 | 48.911 | −4.916 | 9.001 | 1.00 | 15.68 | A | C |
| ATOM | 4628 | O | THR | A | 291 | 48.504 | −4.791 | 10.157 | 1.00 | 16.01 | A | O |
| ATOM | 4630 | N | ILE | A | 292 | 48.991 | −3.903 | 8.141 | 1.00 | 15.70 | A | N |
| ATOM | 4631 | CA | ILE | A | 292 | 48.639 | −2.533 | 8.516 | 1.00 | 15.64 | A | C |
| ATOM | 4633 | CB | ILE | A | 292 | 49.192 | −1.505 | 7.500 | 1.00 | 15.68 | A | C |
| ATOM | 4635 | CG1 | ILE | A | 292 | 50.722 | −1.490 | 7.557 | 1.00 | 15.54 | A | C |
| ATOM | 4638 | CD1 | ILE | A | 292 | 51.357 | −0.392 | 6.739 | 1.00 | 16.00 | A | C |
| ATOM | 4642 | CG2 | ILE | A | 292 | 48.639 | −0.108 | 7.780 | 1.00 | 15.12 | A | C |
| ATOM | 4646 | C | ILE | A | 292 | 47.131 | −2.359 | 8.661 | 1.00 | 15.48 | A | C |
| ATOM | 4647 | O | ILE | A | 292 | 46.669 | −1.760 | 9.631 | 1.00 | 15.61 | A | O |
| ATOM | 4649 | N | ILE | A | 293 | 46.367 | −2.885 | 7.708 | 1.00 | 15.26 | A | N |
| ATOM | 4650 | CA | ILE | A | 293 | 44.909 | −2.805 | 7.779 | 1.00 | 15.32 | A | C |
| ATOM | 4652 | CB | ILE | A | 293 | 44.231 | −3.333 | 6.495 | 1.00 | 15.16 | A | C |
| ATOM | 4654 | CG1 | ILE | A | 293 | 44.602 | −2.472 | 5.282 | 1.00 | 15.39 | A | C |
| ATOM | 4657 | CD1 | ILE | A | 293 | 43.968 | −1.107 | 5.275 | 1.00 | 15.43 | A | C |
| ATOM | 4661 | CG2 | ILE | A | 293 | 42.719 | −3.348 | 6.658 | 1.00 | 15.54 | A | C |
| ATOM | 4665 | C | ILE | A | 293 | 44.394 | −3.586 | 8.991 | 1.00 | 15.79 | A | C |
| ATOM | 4666 | O | ILE | A | 293 | 43.465 | −3.144 | 9.664 | 1.00 | 15.61 | A | O |
| ATOM | 4668 | N | ASP | A | 294 | 45.012 | −4.733 | 9.273 | 1.00 | 16.58 | A | N |
| ATOM | 4669 | CA | ASP | A | 294 | 44.653 | −5.541 | 10.445 | 1.00 | 17.14 | A | C |
| ATOM | 4671 | CB | ASP | A | 294 | 45.511 | −6.814 | 10.521 | 1.00 | 17.55 | A | C |
| ATOM | 4674 | CG | ASP | A | 294 | 45.018 | −7.803 | 11.576 | 1.00 | 18.98 | A | C |
| ATOM | 4675 | OD1 | ASP | A | 294 | 43.790 | −7.884 | 11.806 | 1.00 | 20.79 | A | O |
| ATOM | 4676 | OD2 | ASP | A | 294 | 45.861 | −8.513 | 12.169 | 1.00 | 18.90 | A | O |
| ATOM | 4677 | C | ASP | A | 294 | 44.788 | −4.741 | 11.743 | 1.00 | 16.97 | A | C |
| ATOM | 4678 | O | ASP | A | 294 | 43.999 | −4.924 | 12.667 | 1.00 | 17.05 | A | O |
| ATOM | 4680 | N | ASP | A | 295 | 45.781 | −3.857 | 11.808 | 1.00 | 16.76 | A | N |
| ATOM | 4681 | CA | ASP | A | 295 | 45.937 | −2.965 | 12.958 | 1.00 | 16.73 | A | C |
| ATOM | 4683 | CB | ASP | A | 295 | 47.305 | −2.268 | 12.940 | 1.00 | 16.88 | A | C |
| ATOM | 4686 | CG | ASP | A | 295 | 48.461 | −3.220 | 13.210 | 1.00 | 17.30 | A | C |
| ATOM | 4687 | OD1 | ASP | A | 295 | 48.224 | −4.372 | 13.634 | 1.00 | 17.28 | A | O |
| ATOM | 4688 | OD2 | ASP | A | 295 | 49.620 | −2.806 | 12.998 | 1.00 | 18.54 | A | O |
| ATOM | 4689 | C | ASP | A | 295 | 44.825 | −1.915 | 13.018 | 1.00 | 16.43 | A | C |
| ATOM | 4690 | O | ASP | A | 295 | 44.347 | −1.589 | 14.105 | 1.00 | 16.59 | A | O |
| ATOM | 4692 | N | ILE | A | 296 | 44.420 | −1.390 | 11.859 | 1.00 | 15.90 | A | N |
| ATOM | 4693 | CA | ILE | A | 296 | 43.353 | −0.378 | 11.791 | 1.00 | 15.30 | A | C |
| ATOM | 4695 | CB | ILE | A | 296 | 43.100 | 0.114 | 10.346 | 1.00 | 14.79 | A | C |
| ATOM | 4697 | CG1 | ILE | A | 296 | 44.304 | 0.885 | 9.813 | 1.00 | 14.50 | A | C |
| ATOM | 4700 | CD1 | ILE | A | 296 | 44.210 | 1.200 | 8.336 | 1.00 | 13.16 | A | C |
| ATOM | 4704 | CG2 | ILE | A | 296 | 41.886 | 1.022 | 10.295 | 1.00 | 13.81 | A | C |
| ATOM | 4708 | C | ILE | A | 296 | 42.034 | −0.917 | 12.345 | 1.00 | 15.43 | A | C |
| ATOM | 4709 | O | ILE | A | 296 | 41.305 | −0.200 | 13.033 | 1.00 | 15.53 | A | O |
| ATOM | 4711 | N | TYR | A | 297 | 41.736 | −2.178 | 12.040 | 1.00 | 15.29 | A | N |
| ATOM | 4712 | CA | TYR | A | 297 | 40.501 | −2.820 | 12.495 | 1.00 | 15.11 | A | C |
| ATOM | 4714 | CB | TYR | A | 297 | 40.111 | −3.966 | 11.553 | 1.00 | 15.56 | A | C |
| ATOM | 4717 | CG | TYR | A | 297 | 39.399 | −3.528 | 10.288 | 1.00 | 16.05 | A | C |

TABLE 8-2-continued

Coordinates for L494P Structure

| | | | | | | | | | | | | |
|---|---|---|---|---|---|---|---|---|---|---|---|---|
| ATOM | 4718 | CD1 | TYR | A | 297 | 38.010 | −3.476 | 10.235 | 1.00 | 15.95 | A | C |
| ATOM | 4720 | CE1 | TYR | A | 297 | 37.348 | −3.086 | 9.081 | 1.00 | 15.39 | A | C |
| ATOM | 4722 | CZ | TYR | A | 297 | 38.074 | −2.746 | 7.959 | 1.00 | 16.60 | A | C |
| ATOM | 4723 | OH | TYR | A | 297 | 37.414 | −2.357 | 6.817 | 1.00 | 18.35 | A | O |
| ATOM | 4725 | CE2 | TYR | A | 297 | 39.456 | −2.794 | 7.982 | 1.00 | 16.80 | A | C |
| ATOM | 4727 | CD2 | TYR | A | 297 | 40.110 | −3.187 | 9.142 | 1.00 | 16.66 | A | C |
| ATOM | 4729 | C | TYR | A | 297 | 40.601 | −3.343 | 13.928 | 1.00 | 14.50 | A | C |
| ATOM | 4730 | O | TYR | A | 297 | 39.645 | −3.239 | 14.695 | 1.00 | 14.52 | A | O |
| ATOM | 4732 | N | ASP | A | 298 | 41.757 | −3.901 | 14.280 | 1.00 | 14.10 | A | N |
| ATOM | 4733 | CA | ASP | A | 298 | 41.949 | −4.561 | 15.575 | 1.00 | 13.63 | A | C |
| ATOM | 4735 | CB | ASP | A | 298 | 43.212 | −5.434 | 15.531 | 1.00 | 13.70 | A | C |
| ATOM | 4738 | CG | ASP | A | 298 | 43.478 | −6.162 | 16.835 | 1.00 | 13.63 | A | C |
| ATOM | 4739 | OD1 | ASP | A | 298 | 42.511 | −6.539 | 17.530 | 1.00 | 14.13 | A | O |
| ATOM | 4740 | OD2 | ASP | A | 298 | 44.666 | −6.368 | 17.156 | 1.00 | 13.89 | A | O |
| ATOM | 4741 | C | ASP | A | 298 | 42.044 | −3.573 | 16.741 | 1.00 | 13.00 | A | C |
| ATOM | 4742 | O | ASP | A | 298 | 41.295 | −3.681 | 17.710 | 1.00 | 12.88 | A | O |
| ATOM | 4744 | N | VAL | A | 299 | 42.959 | −2.614 | 16.637 | 1.00 | 12.31 | A | N |
| ATOM | 4745 | CA | VAL | A | 299 | 43.312 | −1.760 | 17.774 | 1.00 | 11.67 | A | C |
| ATOM | 4747 | CB | VAL | A | 299 | 44.805 | −1.930 | 18.142 | 1.00 | 11.42 | A | C |
| ATOM | 4749 | CG1 | VAL | A | 299 | 45.071 | −3.349 | 18.602 | 1.00 | 11.41 | A | C |
| ATOM | 4753 | CG2 | VAL | A | 299 | 45.703 | −1.574 | 16.965 | 1.00 | 10.40 | A | C |
| ATOM | 4757 | C | VAL | A | 299 | 43.020 | −0.267 | 17.587 | 1.00 | 11.59 | A | C |
| ATOM | 4758 | O | VAL | A | 299 | 42.551 | 0.385 | 18.524 | 1.00 | 11.49 | A | O |
| ATOM | 4760 | N | TYR | A | 300 | 43.289 | 0.268 | 16.394 | 1.00 | 11.13 | A | N |
| ATOM | 4761 | CA | TYR | A | 300 | 43.330 | 1.722 | 16.189 | 1.00 | 10.45 | A | C |
| ATOM | 4763 | CB | TYR | A | 300 | 44.389 | 2.094 | 15.139 | 1.00 | 9.99 | A | C |
| ATOM | 4766 | CG | TYR | A | 300 | 44.603 | 3.590 | 15.022 | 1.00 | 9.37 | A | C |
| ATOM | 4767 | CD1 | TYR | A | 300 | 45.202 | 4.309 | 16.055 | 1.00 | 9.54 | A | C |
| ATOM | 4769 | CE1 | TYR | A | 300 | 45.389 | 5.686 | 15.966 | 1.00 | 6.83 | A | C |
| ATOM | 4771 | CZ | TYR | A | 300 | 44.970 | 6.358 | 14.840 | 1.00 | 5.23 | A | C |
| ATOM | 4772 | OH | TYR | A | 300 | 45.155 | 7.715 | 14.752 | 1.00 | 3.12 | A | O |
| ATOM | 4774 | CE2 | TYR | A | 300 | 44.373 | 5.672 | 13.800 | 1.00 | 6.82 | A | C |
| ATOM | 4776 | CD2 | TYR | A | 300 | 44.188 | 4.292 | 13.896 | 1.00 | 8.25 | A | C |
| ATOM | 4778 | C | TYR | A | 300 | 41.989 | 2.370 | 15.821 | 1.00 | 10.48 | A | C |
| ATOM | 4779 | O | TYR | A | 300 | 41.675 | 3.448 | 16.317 | 1.00 | 10.25 | A | O |
| ATOM | 4781 | N | GLY | A | 301 | 41.209 | 1.729 | 14.956 | 1.00 | 11.04 | A | N |
| ATOM | 4782 | CA | GLY | A | 301 | 39.992 | 2.347 | 14.415 | 1.00 | 11.50 | A | C |
| ATOM | 4785 | C | GLY | A | 301 | 38.727 | 2.030 | 15.193 | 1.00 | 11.87 | A | C |
| ATOM | 4786 | O | GLY | A | 301 | 38.509 | 0.882 | 15.585 | 1.00 | 11.70 | A | O |
| ATOM | 4788 | N | THR | A | 302 | 37.887 | 3.045 | 15.411 | 1.00 | 12.42 | A | N |
| ATOM | 4789 | CA | THR | A | 302 | 36.572 | 2.829 | 16.024 | 1.00 | 13.04 | A | C |
| ATOM | 4791 | CB | THR | A | 302 | 35.913 | 4.137 | 16.546 | 1.00 | 13.14 | A | C |
| ATOM | 4793 | OG1 | THR | A | 302 | 35.606 | 5.009 | 15.452 | 1.00 | 14.40 | A | O |
| ATOM | 4795 | CG2 | THR | A | 302 | 36.826 | 4.852 | 17.535 | 1.00 | 12.53 | A | C |
| ATOM | 4799 | C | THR | A | 302 | 35.663 | 2.174 | 14.995 | 1.00 | 13.17 | A | C |
| ATOM | 4800 | O | THR | A | 302 | 35.965 | 2.180 | 13.803 | 1.00 | 12.57 | A | O |
| ATOM | 4802 | N | LEU | A | 303 | 34.551 | 1.613 | 15.456 | 1.00 | 13.95 | A | N |
| ATOM | 4803 | CA | LEU | A | 303 | 33.688 | 0.826 | 14.580 | 1.00 | 14.80 | A | C |
| ATOM | 4805 | CB | LEU | A | 303 | 32.567 | 0.138 | 15.375 | 1.00 | 14.99 | A | C |
| ATOM | 4808 | CG | LEU | A | 303 | 32.178 | −1.259 | 14.876 | 1.00 | 15.81 | A | C |
| ATOM | 4810 | CD1 | LEU | A | 303 | 33.326 | −2.239 | 15.080 | 1.00 | 16.28 | A | C |
| ATOM | 4814 | CD2 | LEU | A | 303 | 30.927 | −1.768 | 15.578 | 1.00 | 17.42 | A | C |
| ATOM | 4818 | C | LEU | A | 303 | 33.114 | 1.690 | 13.456 | 1.00 | 15.44 | A | C |
| ATOM | 4819 | O | LEU | A | 303 | 33.109 | 1.275 | 12.295 | 1.00 | 15.80 | A | O |
| ATOM | 4821 | N | ASP | A | 304 | 32.659 | 2.896 | 13.803 | 1.00 | 15.85 | A | N |
| ATOM | 4822 | CA | ASP | A | 304 | 32.105 | 3.840 | 12.823 | 1.00 | 15.89 | A | C |
| ATOM | 4824 | CB | ASP | A | 304 | 31.645 | 5.137 | 13.509 | 1.00 | 16.11 | A | C |
| ATOM | 4827 | CG | ASP | A | 304 | 30.370 | 4.957 | 14.326 | 1.00 | 15.63 | A | C |
| ATOM | 4828 | OD1 | ASP | A | 304 | 29.443 | 4.266 | 13.852 | 1.00 | 13.49 | A | O |
| ATOM | 4829 | OD2 | ASP | A | 304 | 30.291 | 5.522 | 15.439 | 1.00 | 14.30 | A | O |
| ATOM | 4830 | C | ASP | A | 304 | 33.105 | 4.167 | 11.713 | 1.00 | 15.95 | A | C |
| ATOM | 4831 | O | ASP | A | 304 | 32.728 | 4.260 | 10.544 | 1.00 | 16.02 | A | O |
| ATOM | 4833 | N | GLU | A | 305 | 34.373 | 4.338 | 12.085 | 1.00 | 16.25 | A | N |
| ATOM | 4834 | CA | GLU | A | 305 | 35.447 | 4.580 | 11.113 | 1.00 | 16.33 | A | C |
| ATOM | 4836 | CB | GLU | A | 305 | 36.755 | 4.941 | 11.827 | 1.00 | 16.05 | A | C |
| ATOM | 4839 | CG | GLU | A | 305 | 36.716 | 6.292 | 12.527 | 1.00 | 17.49 | A | C |
| ATOM | 4842 | CD | GLU | A | 305 | 37.971 | 6.589 | 13.330 | 1.00 | 19.41 | A | C |
| ATOM | 4843 | OE1 | GLU | A | 305 | 38.649 | 5.636 | 13.773 | 1.00 | 21.25 | A | O |
| ATOM | 4844 | OE2 | GLU | A | 305 | 38.274 | 7.785 | 13.524 | 1.00 | 19.58 | A | O |
| ATOM | 4845 | C | GLU | A | 305 | 35.667 | 3.364 | 10.215 | 1.00 | 16.21 | A | C |
| ATOM | 4846 | O | GLU | A | 305 | 35.798 | 3.499 | 8.996 | 1.00 | 16.05 | A | O |
| ATOM | 4848 | N | LEU | A | 306 | 35.699 | 2.183 | 10.829 | 1.00 | 16.16 | A | N |
| ATOM | 4849 | CA | LEU | A | 306 | 35.911 | 0.930 | 10.107 | 1.00 | 15.88 | A | C |
| ATOM | 4851 | CB | LEU | A | 306 | 36.033 | −0.235 | 11.089 | 1.00 | 15.78 | A | C |
| ATOM | 4854 | CG | LEU | A | 306 | 37.274 | −0.232 | 11.976 | 1.00 | 15.34 | A | C |
| ATOM | 4856 | CD1 | LEU | A | 306 | 37.218 | −1.417 | 12.928 | 1.00 | 16.17 | A | C |
| ATOM | 4860 | CD2 | LEU | A | 306 | 38.541 | −0.256 | 11.134 | 1.00 | 14.22 | A | C |
| ATOM | 4864 | C | LEU | A | 306 | 34.799 | 0.635 | 9.104 | 1.00 | 16.02 | A | C |

TABLE 8-2-continued

Coordinates for L494P Structure

| | | | | | | | | | | | | |
|---|---|---|---|---|---|---|---|---|---|---|---|---|
| ATOM | 4865 | O | LEU | A | 306 | 35.065 | 0.112 | 8.019 | 1.00 | 15.90 | A | O |
| ATOM | 4867 | N | GLU | A | 307 | 33.561 | 0.960 | 9.471 | 1.00 | 16.02 | A | N |
| ATOM | 4868 | CA | GLU | A | 307 | 32.427 | 0.802 | 8.563 | 1.00 | 16.25 | A | C |
| ATOM | 4870 | CB | GLU | A | 307 | 31.130 | 1.274 | 9.224 | 1.00 | 16.45 | A | C |
| ATOM | 4873 | CG | GLU | A | 307 | 30.620 | 0.361 | 10.331 | 1.00 | 17.76 | A | C |
| ATOM | 4876 | CD | GLU | A | 307 | 29.869 | −0.853 | 9.813 | 1.00 | 19.89 | A | C |
| ATOM | 4877 | OE1 | GLU | A | 307 | 29.047 | −1.399 | 10.580 | 1.00 | 22.93 | A | O |
| ATOM | 4878 | OE2 | GLU | A | 307 | 30.093 | −1.262 | 8.653 | 1.00 | 19.71 | A | O |
| ATOM | 4879 | C | GLU | A | 307 | 32.654 | 1.572 | 7.264 | 1.00 | 16.17 | A | C |
| ATOM | 4880 | O | GLU | A | 307 | 32.380 | 1.063 | 6.179 | 1.00 | 16.40 | A | O |
| ATOM | 4882 | N | LEU | A | 308 | 33.163 | 2.795 | 7.383 | 1.00 | 16.07 | A | N |
| ATOM | 4883 | CA | LEU | A | 308 | 33.456 | 3.620 | 6.213 | 1.00 | 15.87 | A | C |
| ATOM | 4885 | CB | LEU | A | 308 | 33.850 | 5.038 | 6.634 | 1.00 | 15.51 | A | C |
| ATOM | 4888 | CG | LEU | A | 308 | 32.759 | 5.841 | 7.341 | 1.00 | 14.36 | A | C |
| ATOM | 4890 | CD1 | LEU | A | 308 | 33.340 | 7.117 | 7.928 | 1.00 | 14.78 | A | C |
| ATOM | 4894 | CD2 | LEU | A | 308 | 31.618 | 6.151 | 6.386 | 1.00 | 12.42 | A | C |
| ATOM | 4898 | C | LEU | A | 308 | 34.559 | 2.995 | 5.359 | 1.00 | 15.95 | A | C |
| ATOM | 4899 | O | LEU | A | 308 | 34.422 | 2.896 | 4.140 | 1.00 | 16.08 | A | O |
| ATOM | 4901 | N | PHE | A | 309 | 35.644 | 2.566 | 5.997 | 1.00 | 15.86 | A | N |
| ATOM | 4902 | CA | PHE | A | 309 | 36.741 | 1.932 | 5.271 | 1.00 | 15.76 | A | C |
| ATOM | 4904 | CB | PHE | A | 309 | 37.879 | 1.539 | 6.213 | 1.00 | 15.23 | A | C |
| ATOM | 4907 | CG | PHE | A | 309 | 39.167 | 1.268 | 5.505 | 1.00 | 12.77 | A | C |
| ATOM | 4908 | CD1 | PHE | A | 309 | 40.023 | 2.308 | 5.187 | 1.00 | 11.18 | A | C |
| ATOM | 4910 | CE1 | PHE | A | 309 | 41.216 | 2.073 | 4.524 | 1.00 | 10.16 | A | C |
| ATOM | 4912 | CZ | PHE | A | 309 | 41.558 | 0.788 | 4.165 | 1.00 | 11.94 | A | C |
| ATOM | 4914 | CE2 | PHE | A | 309 | 40.705 | −0.265 | 4.470 | 1.00 | 12.78 | A | C |
| ATOM | 4916 | CD2 | PHE | A | 309 | 39.515 | −0.019 | 5.136 | 1.00 | 12.55 | A | C |
| ATOM | 4918 | C | PHE | A | 309 | 36.242 | 0.701 | 4.519 | 1.00 | 16.65 | A | C |
| ATOM | 4919 | O | PHE | A | 309 | 36.509 | 0.545 | 3.326 | 1.00 | 16.66 | A | O |
| ATOM | 4921 | N | THR | A | 310 | 35.515 | −0.162 | 5.227 | 1.00 | 17.62 | A | N |
| ATOM | 4922 | CA | THR | A | 310 | 34.879 | −1.337 | 4.626 | 1.00 | 18.17 | A | C |
| ATOM | 4924 | CB | THR | A | 310 | 33.943 | −2.053 | 5.630 | 1.00 | 18.21 | A | C |
| ATOM | 4926 | OG1 | THR | A | 310 | 34.678 | −2.429 | 6.802 | 1.00 | 18.07 | A | O |
| ATOM | 4928 | CG2 | THR | A | 310 | 33.321 | −3.292 | 4.999 | 1.00 | 18.32 | A | C |
| ATOM | 4932 | C | THR | A | 310 | 34.057 | −0.931 | 3.407 | 1.00 | 18.50 | A | C |
| ATOM | 4933 | O | THR | A | 310 | 34.199 | −1.514 | 2.330 | 1.00 | 18.52 | A | O |
| ATOM | 4935 | N | ASP | A | 311 | 33.205 | 0.077 | 3.591 | 1.00 | 18.74 | A | N |
| ATOM | 4936 | CA | ASP | A | 311 | 32.368 | 0.609 | 2.515 | 1.00 | 18.56 | A | C |
| ATOM | 4938 | CB | ASP | A | 311 | 31.415 | 1.684 | 3.053 | 1.00 | 18.73 | A | C |
| ATOM | 4941 | CG | ASP | A | 311 | 30.562 | 2.306 | 1.966 | 1.00 | 19.68 | A | C |
| ATOM | 4942 | OD1 | ASP | A | 311 | 29.867 | 1.552 | 1.252 | 1.00 | 21.03 | A | O |
| ATOM | 4943 | OD2 | ASP | A | 311 | 30.591 | 3.548 | 1.824 | 1.00 | 20.12 | A | O |
| ATOM | 4944 | C | ASP | A | 311 | 33.221 | 1.186 | 1.389 | 1.00 | 17.98 | A | C |
| ATOM | 4945 | O | ASP | A | 311 | 32.919 | 0.981 | 0.218 | 1.00 | 17.81 | A | O |
| ATOM | 4947 | N | ALA | A | 312 | 34.288 | 1.895 | 1.754 | 1.00 | 17.60 | A | N |
| ATOM | 4948 | CA | ALA | A | 312 | 35.207 | 2.487 | 0.779 | 1.00 | 17.18 | A | C |
| ATOM | 4950 | CB | ALA | A | 312 | 36.287 | 3.290 | 1.493 | 1.00 | 17.04 | A | C |
| ATOM | 4954 | C | ALA | A | 312 | 35.840 | 1.431 | −0.132 | 1.00 | 16.89 | A | C |
| ATOM | 4955 | O | ALA | A | 312 | 35.978 | 1.647 | −1.336 | 1.00 | 16.28 | A | O |
| ATOM | 4957 | N | VAL | A | 313 | 36.215 | 0.292 | 0.446 | 1.00 | 17.08 | A | N |
| ATOM | 4958 | CA | VAL | A | 313 | 36.777 | −0.819 | −0.326 | 1.00 | 17.48 | A | C |
| ATOM | 4960 | CB | VAL | A | 313 | 37.595 | −1.779 | 0.572 | 1.00 | 17.54 | A | C |
| ATOM | 4962 | CG1 | VAL | A | 313 | 38.729 | −1.027 | 1.260 | 1.00 | 17.32 | A | C |
| ATOM | 4966 | CG2 | VAL | A | 313 | 38.156 | −2.933 | −0.239 | 1.00 | 17.14 | A | C |
| ATOM | 4970 | C | VAL | A | 313 | 35.686 | −1.598 | −1.076 | 1.00 | 17.77 | A | C |
| ATOM | 4971 | O | VAL | A | 313 | 35.932 | −2.118 | −2.164 | 1.00 | 17.70 | A | O |
| ATOM | 4973 | N | GLU | A | 314 | 34.486 | −1.669 | −0.501 | 1.00 | 18.26 | A | N |
| ATOM | 4974 | CA | GLU | A | 314 | 33.347 | −2.332 | −1.155 | 1.00 | 18.61 | A | C |
| ATOM | 4976 | CB | GLU | A | 314 | 32.125 | −2.376 | −0.229 | 1.00 | 18.86 | A | C |
| ATOM | 4979 | CG | GLU | A | 314 | 32.105 | −3.539 | 0.747 | 1.00 | 20.58 | A | C |
| ATOM | 4982 | CD | GLU | A | 314 | 30.881 | −3.524 | 1.649 | 1.00 | 24.15 | A | C |
| ATOM | 4983 | OE1 | GLU | A | 314 | 30.876 | −4.268 | 2.652 | 1.00 | 28.09 | A | O |
| ATOM | 4984 | OE2 | GLU | A | 314 | 29.923 | −2.771 | 1.361 | 1.00 | 24.84 | A | O |
| ATOM | 4985 | C | GLU | A | 314 | 32.929 | −1.675 | −2.470 | 1.00 | 18.45 | A | C |
| ATOM | 4986 | O | GLU | A | 314 | 32.453 | −2.359 | −3.375 | 1.00 | 18.12 | A | O |
| ATOM | 4988 | N | ARG | A | 315 | 33.089 | −0.355 | −2.563 | 1.00 | 18.81 | A | N |
| ATOM | 4989 | CA | ARG | A | 315 | 32.614 | 0.405 | −3.724 | 1.00 | 19.28 | A | C |
| ATOM | 4991 | CB | ARG | A | 315 | 31.904 | 1.687 | −3.276 | 1.00 | 19.73 | A | C |
| ATOM | 4994 | CG | ARG | A | 315 | 30.876 | 1.469 | −2.149 | 1.00 | 22.35 | A | C |
| ATOM | 4997 | CD | ARG | A | 315 | 29.651 | 2.378 | −2.247 | 1.00 | 25.41 | A | C |
| ATOM | 5000 | NE | ARG | A | 315 | 29.952 | 3.667 | −2.867 | 1.00 | 29.17 | A | N |
| ATOM | 5002 | CZ | ARG | A | 315 | 30.616 | 4.665 | −2.284 | 1.00 | 32.10 | A | C |
| ATOM | 5003 | NH1 | ARG | A | 315 | 30.828 | 5.789 | −2.961 | 1.00 | 33.11 | A | N |
| ATOM | 5006 | NH2 | ARG | A | 315 | 31.072 | 4.555 | −1.038 | 1.00 | 33.08 | A | N |
| ATOM | 5009 | C | ARG | A | 315 | 33.730 | 0.733 | −4.717 | 1.00 | 18.91 | A | C |
| ATOM | 5010 | O | ARG | A | 315 | 33.484 | 0.805 | −5.921 | 1.00 | 18.78 | A | O |
| ATOM | 5012 | N | TRP | A | 316 | 34.944 | 0.936 | −4.209 | 1.00 | 18.94 | A | N |
| ATOM | 5013 | CA | TRP | A | 316 | 36.125 | 1.195 | −5.046 | 1.00 | 18.73 | A | C |

TABLE 8-2-continued

Coordinates for L494P Structure

| | | | | | | | | | | | | |
|---|---|---|---|---|---|---|---|---|---|---|---|---|
| ATOM | 5015 | CB | TRP | A | 316 | 36.366 | 0.014 | −6.002 | 1.00 | 18.53 | A | C |
| ATOM | 5018 | CG | TRP | A | 316 | 37.802 | −0.166 | −6.398 | 1.00 | 17.21 | A | C |
| ATOM | 5019 | CD1 | TRP | A | 316 | 38.330 | −0.036 | −7.649 | 1.00 | 16.88 | A | C |
| ATOM | 5021 | NE1 | TRP | A | 316 | 39.682 | −0.275 | −7.620 | 1.00 | 15.97 | A | N |
| ATOM | 5023 | CE2 | TRP | A | 316 | 40.051 | −0.566 | −6.334 | 1.00 | 15.80 | A | C |
| ATOM | 5024 | CD2 | TRP | A | 316 | 38.891 | −0.507 | −5.537 | 1.00 | 15.21 | A | C |
| ATOM | 5025 | CE3 | TRP | A | 316 | 38.999 | −0.766 | −4.167 | 1.00 | 16.69 | A | C |
| ATOM | 5027 | CZ3 | TRP | A | 316 | 40.245 | −1.073 | −3.643 | 1.00 | 17.30 | A | C |
| ATOM | 5029 | CH2 | TRP | A | 316 | 41.381 | −1.127 | −4.464 | 1.00 | 17.99 | A | C |
| ATOM | 5031 | CZ2 | TRP | A | 316 | 41.305 | −0.873 | −5.808 | 1.00 | 17.57 | A | C |
| ATOM | 5033 | C | TRP | A | 316 | 36.024 | 2.523 | −5.818 | 1.00 | 18.77 | A | C |
| ATOM | 5034 | O | TRP | A | 316 | 36.569 | 2.660 | −6.913 | 1.00 | 18.58 | A | O |
| ATOM | 5036 | N | ASP | A | 317 | 35.334 | 3.497 | −5.229 | 1.00 | 19.02 | A | N |
| ATOM | 5037 | CA | ASP | A | 317 | 35.161 | 4.811 | −5.835 | 1.00 | 19.48 | A | C |
| ATOM | 5039 | CB | ASP | A | 317 | 33.739 | 5.327 | −5.573 | 1.00 | 19.49 | A | C |
| ATOM | 5042 | CG | ASP | A | 317 | 33.471 | 6.694 | −6.199 | 1.00 | 19.09 | A | C |
| ATOM | 5043 | OD1 | ASP | A | 317 | 34.201 | 7.099 | −7.129 | 1.00 | 19.20 | A | O |
| ATOM | 5044 | OD2 | ASP | A | 317 | 32.512 | 7.365 | −5.758 | 1.00 | 17.19 | A | O |
| ATOM | 5045 | C | ASP | A | 317 | 36.202 | 5.767 | −5.253 | 1.00 | 20.22 | A | C |
| ATOM | 5046 | O | ASP | A | 317 | 36.110 | 6.161 | −4.088 | 1.00 | 20.57 | A | O |
| ATOM | 5048 | N | VAL | A | 318 | 37.188 | 6.135 | −6.070 | 1.00 | 20.71 | A | N |
| ATOM | 5049 | CA | VAL | A | 318 | 38.276 | 7.016 | −5.633 | 1.00 | 21.05 | A | C |
| ATOM | 5051 | CB | VAL | A | 318 | 39.423 | 7.038 | −6.666 | 1.00 | 20.76 | A | C |
| ATOM | 5053 | CG1 | VAL | A | 318 | 40.690 | 7.613 | −6.053 | 1.00 | 20.64 | A | C |
| ATOM | 5057 | CG2 | VAL | A | 318 | 39.017 | 7.812 | −7.911 | 1.00 | 20.38 | A | C |
| ATOM | 5061 | C | VAL | A | 318 | 37.818 | 8.456 | −5.370 | 1.00 | 21.99 | A | C |
| ATOM | 5062 | O | VAL | A | 318 | 38.528 | 9.222 | −4.719 | 1.00 | 22.30 | A | O |
| ATOM | 5064 | N | ASN | A | 319 | 36.644 | 8.821 | −5.885 | 1.00 | 22.84 | A | N |
| ATOM | 5065 | CA | ASN | A | 319 | 36.083 | 10.160 | −5.684 | 1.00 | 23.25 | A | C |
| ATOM | 5067 | CB | ASN | A | 319 | 35.177 | 10.539 | −6.862 | 1.00 | 23.24 | A | C |
| ATOM | 5070 | CG | ASN | A | 319 | 35.956 | 10.749 | −8.159 | 1.00 | 23.11 | A | C |
| ATOM | 5071 | OD1 | ASN | A | 319 | 36.802 | 11.643 | −8.255 | 1.00 | 22.22 | A | O |
| ATOM | 5072 | ND2 | ASN | A | 319 | 35.664 | 9.929 | −9.166 | 1.00 | 20.47 | A | N |
| ATOM | 5075 | C | ASN | A | 319 | 35.323 | 10.305 | −4.360 | 1.00 | 24.05 | A | C |
| ATOM | 5076 | O | ASN | A | 319 | 35.057 | 11.425 | −3.924 | 1.00 | 24.48 | A | O |
| ATOM | 5078 | N | ALA | A | 320 | 34.978 | 9.180 | −3.730 | 1.00 | 24.88 | A | N |
| ATOM | 5079 | CA | ALA | A | 320 | 34.347 | 9.180 | −2.399 | 1.00 | 25.38 | A | C |
| ATOM | 5081 | CB | ALA | A | 320 | 33.373 | 8.017 | −2.277 | 1.00 | 25.19 | A | C |
| ATOM | 5085 | C | ALA | A | 320 | 35.380 | 9.127 | −1.261 | 1.00 | 25.94 | A | C |
| ATOM | 5086 | O | ALA | A | 320 | 35.010 | 9.092 | −0.085 | 1.00 | 26.43 | A | O |
| ATOM | 5088 | N | ILE | A | 321 | 36.663 | 9.119 | −1.624 | 1.00 | 26.12 | A | N |
| ATOM | 5089 | CA | ILE | A | 321 | 37.785 | 9.144 | −0.674 | 1.00 | 26.16 | A | C |
| ATOM | 5091 | CB | ILE | A | 321 | 39.124 | 9.356 | −1.440 | 1.00 | 26.28 | A | C |
| ATOM | 5093 | CG1 | ILE | A | 321 | 40.336 | 9.088 | −0.551 | 1.00 | 25.99 | A | C |
| ATOM | 5096 | CD1 | ILE | A | 321 | 41.648 | 9.204 | −1.300 | 1.00 | 25.33 | A | C |
| ATOM | 5100 | CG2 | ILE | A | 321 | 39.204 | 10.767 | −2.021 | 1.00 | 27.21 | A | C |
| ATOM | 5104 | C | ILE | A | 321 | 37.651 | 10.218 | 0.420 | 1.00 | 26.28 | A | C |
| ATOM | 5105 | O | ILE | A | 321 | 38.083 | 10.002 | 1.553 | 1.00 | 26.33 | A | O |
| ATOM | 5107 | N | ASN | A | 322 | 37.046 | 11.361 | 0.078 | 1.00 | 26.31 | A | N |
| ATOM | 5108 | CA | ASN | A | 322 | 36.870 | 12.485 | 1.019 | 1.00 | 26.01 | A | C |
| ATOM | 5110 | CB | ASN | A | 322 | 36.659 | 13.804 | 0.248 | 1.00 | 25.94 | A | C |
| ATOM | 5113 | CG | ASN | A | 322 | 37.960 | 14.409 | −0.261 | 1.00 | 26.56 | A | C |
| ATOM | 5114 | OD1 | ASN | A | 322 | 39.043 | 14.120 | 0.251 | 1.00 | 26.84 | A | O |
| ATOM | 5115 | ND2 | ASN | A | 322 | 37.854 | 15.266 | −1.268 | 1.00 | 27.80 | A | N |
| ATOM | 5118 | C | ASN | A | 322 | 35.751 | 12.310 | 2.062 | 1.00 | 25.35 | A | C |
| ATOM | 5119 | O | ASN | A | 322 | 35.438 | 13.253 | 2.796 | 1.00 | 25.20 | A | O |
| ATOM | 5121 | N | ASP | A | 323 | 35.153 | 11.120 | 2.126 | 1.00 | 24.45 | A | N |
| ATOM | 5122 | CA | ASP | A | 323 | 34.220 | 10.778 | 3.204 | 1.00 | 24.14 | A | C |
| ATOM | 5124 | CB | ASP | A | 323 | 33.119 | 9.836 | 2.692 | 1.00 | 24.89 | A | C |
| ATOM | 5127 | CG | ASP | A | 323 | 32.096 | 10.547 | 1.811 | 1.00 | 26.83 | A | C |
| ATOM | 5128 | OD1 | ASP | A | 323 | 31.426 | 11.480 | 2.306 | 1.00 | 27.88 | A | O |
| ATOM | 5129 | OD2 | ASP | A | 323 | 31.952 | 10.162 | 0.629 | 1.00 | 29.53 | A | O |
| ATOM | 5130 | C | ASP | A | 323 | 34.945 | 10.136 | 4.394 | 1.00 | 22.55 | A | C |
| ATOM | 5131 | O | ASP | A | 323 | 34.408 | 10.098 | 5.504 | 1.00 | 22.17 | A | O |
| ATOM | 5133 | N | LEU | A | 324 | 36.162 | 9.644 | 4.157 | 1.00 | 21.03 | A | N |
| ATOM | 5134 | CA | LEU | A | 324 | 36.939 | 8.936 | 5.178 | 1.00 | 20.05 | A | C |
| ATOM | 5136 | CB | LEU | A | 324 | 37.933 | 7.973 | 4.518 | 1.00 | 19.99 | A | C |
| ATOM | 5139 | CG | LEU | A | 324 | 37.351 | 6.752 | 3.803 | 1.00 | 20.17 | A | C |
| ATOM | 5141 | CD1 | LEU | A | 324 | 38.422 | 6.076 | 2.962 | 1.00 | 20.22 | A | C |
| ATOM | 5145 | CD2 | LEU | A | 324 | 36.747 | 5.771 | 4.797 | 1.00 | 19.25 | A | C |
| ATOM | 5149 | C | LEU | A | 324 | 37.707 | 9.901 | 6.075 | 1.00 | 19.03 | A | C |
| ATOM | 5150 | O | LEU | A | 324 | 37.918 | 11.052 | 5.702 | 1.00 | 18.72 | A | O |
| ATOM | 5152 | N | PRO | A | 325 | 38.130 | 9.429 | 7.263 | 1.00 | 18.44 | A | N |
| ATOM | 5153 | CA | PRO | A | 325 | 39.010 | 10.213 | 8.122 | 1.00 | 18.19 | A | C |
| ATOM | 5155 | CB | PRO | A | 325 | 38.874 | 9.527 | 9.482 | 1.00 | 18.12 | A | C |
| ATOM | 5158 | CG | PRO | A | 325 | 38.558 | 8.121 | 9.159 | 1.00 | 18.05 | A | C |
| ATOM | 5161 | CD | PRO | A | 325 | 37.746 | 8.152 | 7.896 | 1.00 | 18.53 | A | C |
| ATOM | 5164 | C | PRO | A | 325 | 40.458 | 10.173 | 7.630 | 1.00 | 18.23 | A | C |

TABLE 8-2-continued

Coordinates for L494P Structure

| | | | | | | | | | | | | |
|---|---|---|---|---|---|---|---|---|---|---|---|---|
| ATOM | 5165 | O | PRO | A | 325 | 40.863 | 9.215 | 6.973 | 1.00 | 17.90 | A | O |
| ATOM | 5166 | N | ASP | A | 326 | 41.223 | 11.206 | 7.971 | 1.00 | 18.42 | A | N |
| ATOM | 5167 | CA | ASP | A | 326 | 42.555 | 11.441 | 7.400 | 1.00 | 18.51 | A | C |
| ATOM | 5169 | CB | ASP | A | 326 | 43.261 | 12.572 | 8.161 | 1.00 | 18.74 | A | C |
| ATOM | 5172 | CG | ASP | A | 326 | 42.691 | 13.945 | 7.832 | 1.00 | 20.90 | A | C |
| ATOM | 5173 | OD1 | ASP | A | 326 | 42.044 | 14.087 | 6.772 | 1.00 | 23.65 | A | O |
| ATOM | 5174 | OD2 | ASP | A | 326 | 42.891 | 14.886 | 8.632 | 1.00 | 23.58 | A | O |
| ATOM | 5175 | C | ASP | A | 326 | 43.466 | 10.209 | 7.307 | 1.00 | 18.04 | A | C |
| ATOM | 5176 | O | ASP | A | 326 | 44.037 | 9.950 | 6.246 | 1.00 | 18.16 | A | O |
| ATOM | 5178 | N | TYR | A | 327 | 43.605 | 9.453 | 8.393 | 1.00 | 17.28 | A | N |
| ATOM | 5179 | CA | TYR | A | 327 | 44.502 | 8.291 | 8.389 | 1.00 | 16.66 | A | C |
| ATOM | 5181 | CB | TYR | A | 327 | 44.728 | 7.753 | 9.807 | 1.00 | 16.33 | A | C |
| ATOM | 5184 | CG | TYR | A | 327 | 43.607 | 6.900 | 10.353 | 1.00 | 14.83 | A | C |
| ATOM | 5185 | CD1 | TYR | A | 327 | 42.558 | 7.471 | 11.061 | 1.00 | 14.91 | A | C |
| ATOM | 5187 | CE1 | TYR | A | 327 | 41.528 | 6.692 | 11.572 | 1.00 | 15.33 | A | C |
| ATOM | 5189 | CZ | TYR | A | 327 | 41.546 | 5.323 | 11.382 | 1.00 | 15.64 | A | C |
| ATOM | 5190 | OH | TYR | A | 327 | 40.524 | 4.554 | 11.893 | 1.00 | 15.59 | A | O |
| ATOM | 5192 | CE2 | TYR | A | 327 | 42.585 | 4.729 | 10.683 | 1.00 | 14.60 | A | C |
| ATOM | 5194 | CD2 | TYR | A | 327 | 43.607 | 5.518 | 10.176 | 1.00 | 13.91 | A | C |
| ATOM | 5196 | C | TYR | A | 327 | 44.004 | 7.180 | 7.454 | 1.00 | 16.77 | A | C |
| ATOM | 5197 | O | TYR | A | 327 | 44.801 | 6.394 | 6.934 | 1.00 | 16.95 | A | O |
| ATOM | 5199 | N | MET | A | 328 | 42.690 | 7.122 | 7.246 | 1.00 | 16.36 | A | N |
| ATOM | 5200 | CA | MET | A | 328 | 42.100 | 6.171 | 6.307 | 1.00 | 16.03 | A | C |
| ATOM | 5202 | CB | MET | A | 328 | 40.650 | 5.876 | 6.684 | 1.00 | 15.85 | A | C |
| ATOM | 5205 | CG | MET | A | 328 | 40.515 | 5.126 | 7.990 | 1.00 | 15.27 | A | C |
| ATOM | 5208 | SD | MET | A | 328 | 38.824 | 4.621 | 8.325 | 1.00 | 14.96 | A | S |
| ATOM | 5209 | CE | MET | A | 328 | 39.096 | 3.214 | 9.397 | 1.00 | 11.58 | A | C |
| ATOM | 5213 | C | MET | A | 328 | 42.171 | 6.665 | 4.862 | 1.00 | 16.28 | A | C |
| ATOM | 5214 | O | MET | A | 328 | 42.190 | 5.857 | 3.938 | 1.00 | 16.32 | A | O |
| ATOM | 5216 | N | LYS | A | 329 | 42.199 | 7.982 | 4.662 | 1.00 | 16.61 | A | N |
| ATOM | 5217 | CA | LYS | A | 329 | 42.364 | 8.542 | 3.320 | 1.00 | 16.78 | A | C |
| ATOM | 5219 | CB | LYS | A | 329 | 42.319 | 10.076 | 3.338 | 1.00 | 16.88 | A | C |
| ATOM | 5222 | CG | LYS | A | 329 | 40.977 | 10.672 | 3.743 | 1.00 | 19.25 | A | C |
| ATOM | 5225 | CD | LYS | A | 329 | 41.066 | 12.184 | 3.989 | 1.00 | 22.20 | A | C |
| ATOM | 5228 | CE | LYS | A | 329 | 40.917 | 12.990 | 2.701 | 1.00 | 23.60 | A | C |
| ATOM | 5231 | NZ | LYS | A | 329 | 41.054 | 14.461 | 2.934 | 1.00 | 23.47 | A | N |
| ATOM | 5235 | C | LYS | A | 329 | 43.699 | 8.076 | 2.752 | 1.00 | 16.51 | A | C |
| ATOM | 5236 | O | LYS | A | 329 | 43.750 | 7.459 | 1.687 | 1.00 | 16.65 | A | O |
| ATOM | 5238 | N | LEU | A | 330 | 44.770 | 8.355 | 3.492 | 1.00 | 16.06 | A | N |
| ATOM | 5239 | CA | LEU | A | 330 | 46.125 | 7.989 | 3.088 | 1.00 | 15.49 | A | C |
| ATOM | 5241 | CB | LEU | A | 330 | 47.142 | 8.516 | 4.110 | 1.00 | 15.41 | A | C |
| ATOM | 5244 | CG | LEU | A | 330 | 48.628 | 8.299 | 3.810 | 1.00 | 14.76 | A | C |
| ATOM | 5246 | CD1 | LEU | A | 330 | 49.024 | 8.972 | 2.505 | 1.00 | 13.80 | A | C |
| ATOM | 5250 | CD2 | LEU | A | 330 | 49.481 | 8.812 | 4.960 | 1.00 | 13.92 | A | C |
| ATOM | 5254 | C | LEU | A | 330 | 46.283 | 6.478 | 2.927 | 1.00 | 15.10 | A | C |
| ATOM | 5255 | O | LEU | A | 330 | 47.011 | 6.020 | 2.049 | 1.00 | 14.96 | A | O |
| ATOM | 5257 | N | CYS | A | 331 | 45.600 | 5.710 | 3.772 | 1.00 | 14.87 | A | N |
| ATOM | 5258 | CA | CYS | A | 331 | 45.696 | 4.248 | 3.732 | 1.00 | 14.79 | A | C |
| ATOM | 5260 | CB | CYS | A | 331 | 45.193 | 3.642 | 5.047 | 1.00 | 15.05 | A | C |
| ATOM | 5263 | SG | CYS | A | 331 | 45.475 | 1.867 | 5.196 | 1.00 | 16.22 | A | S |
| ATOM | 5265 | C | CYS | A | 331 | 44.919 | 3.661 | 2.552 | 1.00 | 13.61 | A | C |
| ATOM | 5266 | O | CYS | A | 331 | 45.455 | 2.861 | 1.787 | 1.00 | 13.77 | A | O |
| ATOM | 5268 | N | PHE | A | 332 | 43.661 | 4.067 | 2.415 | 1.00 | 12.37 | A | N |
| ATOM | 5269 | CA | PHE | A | 332 | 42.796 | 3.589 | 1.339 | 1.00 | 11.68 | A | C |
| ATOM | 5271 | CB | PHE | A | 332 | 41.430 | 4.282 | 1.415 | 1.00 | 11.85 | A | C |
| ATOM | 5274 | CG | PHE | A | 332 | 40.527 | 3.977 | 0.255 | 1.00 | 10.54 | A | C |
| ATOM | 5275 | CD1 | PHE | A | 332 | 39.892 | 2.752 | 0.163 | 1.00 | 9.36 | A | C |
| ATOM | 5277 | CE1 | PHE | A | 332 | 39.065 | 2.466 | −0.905 | 1.00 | 11.01 | A | C |
| ATOM | 5279 | CZ | PHE | A | 332 | 38.862 | 3.413 | −1.897 | 1.00 | 11.31 | A | C |
| ATOM | 5281 | CE2 | PHE | A | 332 | 39.489 | 4.639 | −1.815 | 1.00 | 9.89 | A | C |
| ATOM | 5283 | CD2 | PHE | A | 332 | 40.315 | 4.917 | −0.744 | 1.00 | 10.03 | A | C |
| ATOM | 5285 | C | PHE | A | 332 | 43.413 | 3.812 | −0.042 | 1.00 | 11.23 | A | C |
| ATOM | 5286 | O | PHE | A | 332 | 43.527 | 2.878 | −0.832 | 1.00 | 11.12 | A | O |
| ATOM | 5288 | N | LEU | A | 333 | 43.808 | 5.051 | −0.322 | 1.00 | 10.61 | A | N |
| ATOM | 5289 | CA | LEU | A | 333 | 44.354 | 5.417 | −1.632 | 1.00 | 10.12 | A | C |
| ATOM | 5291 | CB | LEU | A | 333 | 44.677 | 6.916 | −1.680 | 1.00 | 9.81 | A | C |
| ATOM | 5294 | CG | LEU | A | 333 | 45.111 | 7.515 | −3.022 | 1.00 | 8.38 | A | C |
| ATOM | 5296 | CD1 | LEU | A | 333 | 44.113 | 7.206 | −4.128 | 1.00 | 7.03 | A | C |
| ATOM | 5300 | CD2 | LEU | A | 333 | 45.299 | 9.017 | −2.881 | 1.00 | 5.80 | A | C |
| ATOM | 5304 | C | LEU | A | 333 | 45.598 | 4.605 | −1.978 | 1.00 | 10.21 | A | C |
| ATOM | 5305 | O | LEU | A | 333 | 45.791 | 4.229 | −3.133 | 1.00 | 9.84 | A | O |
| ATOM | 5307 | N | ALA | A | 334 | 46.432 | 4.342 | −0.972 | 1.00 | 10.86 | A | N |
| ATOM | 5308 | CA | ALA | A | 334 | 47.645 | 3.538 | −1.140 | 1.00 | 11.33 | A | C |
| ATOM | 5310 | CB | ALA | A | 334 | 48.442 | 3.504 | 0.155 | 1.00 | 11.25 | A | C |
| ATOM | 5314 | C | ALA | A | 334 | 47.302 | 2.120 | −1.582 | 1.00 | 11.86 | A | C |
| ATOM | 5315 | O | ALA | A | 334 | 47.965 | 1.552 | −2.453 | 1.00 | 11.99 | A | O |
| ATOM | 5317 | N | LEU | A | 335 | 46.273 | 1.552 | −0.961 | 1.00 | 12.36 | A | N |
| ATOM | 5318 | CA | LEU | A | 335 | 45.726 | 0.262 | −1.371 | 1.00 | 12.61 | A | C |

TABLE 8-2-continued

Coordinates for L494P Structure

| | | | | | | | | | | | | |
|---|---|---|---|---|---|---|---|---|---|---|---|---|
| ATOM | 5320 | CB | LEU | A | 335 | 44.651 | −0.193 | −0.375 | 1.00 | 12.56 | A | C |
| ATOM | 5323 | CG | LEU | A | 335 | 43.849 | −1.461 | −0.677 | 1.00 | 12.43 | A | C |
| ATOM | 5325 | CD1 | LEU | A | 335 | 44.764 | −2.659 | −0.871 | 1.00 | 13.39 | A | C |
| ATOM | 5329 | CD2 | LEU | A | 335 | 42.863 | −1.712 | 0.447 | 1.00 | 9.98 | A | C |
| ATOM | 5333 | C | LEU | A | 335 | 45.136 | 0.383 | −2.772 | 1.00 | 12.75 | A | C |
| ATOM | 5334 | O | LEU | A | 335 | 45.446 | −0.411 | −3.655 | 1.00 | 12.66 | A | O |
| ATOM | 5336 | N | TYR | A | 336 | 44.300 | 1.400 | −2.961 | 1.00 | 13.37 | A | N |
| ATOM | 5337 | CA | TYR | A | 336 | 43.602 | 1.636 | −4.225 | 1.00 | 13.86 | A | C |
| ATOM | 5339 | CB | TYR | A | 336 | 42.847 | 2.970 | −4.167 | 1.00 | 14.27 | A | C |
| ATOM | 5342 | CG | TYR | A | 336 | 41.953 | 3.234 | −5.357 | 1.00 | 14.40 | A | C |
| ATOM | 5343 | CD1 | TYR | A | 336 | 40.743 | 2.569 | −5.499 | 1.00 | 14.78 | A | C |
| ATOM | 5345 | CE1 | TYR | A | 336 | 39.916 | 2.810 | −6.586 | 1.00 | 13.90 | A | C |
| ATOM | 5347 | CZ | TYR | A | 336 | 40.293 | 3.725 | −7.545 | 1.00 | 11.73 | A | C |
| ATOM | 5348 | OH | TYR | A | 336 | 39.473 | 3.962 | −8.623 | 1.00 | 8.69 | A | O |
| ATOM | 5350 | CE2 | TYR | A | 336 | 41.488 | 4.405 | −7.423 | 1.00 | 13.24 | A | C |
| ATOM | 5352 | CD2 | TYR | A | 336 | 42.310 | 4.158 | −6.334 | 1.00 | 14.34 | A | C |
| ATOM | 5354 | C | TYR | A | 336 | 44.548 | 1.622 | −5.422 | 1.00 | 13.95 | A | C |
| ATOM | 5355 | O | TYR | A | 336 | 44.305 | 0.907 | −6.397 | 1.00 | 14.01 | A | O |
| ATOM | 5357 | N | ASN | A | 337 | 45.624 | 2.405 | −5.332 | 1.00 | 13.83 | A | N |
| ATOM | 5358 | CA | ASN | A | 337 | 46.605 | 2.519 | −6.416 | 1.00 | 13.77 | A | C |
| ATOM | 5360 | CB | ASN | A | 337 | 47.606 | 3.646 | −6.127 | 1.00 | 13.87 | A | C |
| ATOM | 5363 | CG | ASN | A | 337 | 47.035 | 5.023 | −6.408 | 1.00 | 15.61 | A | C |
| ATOM | 5364 | OD1 | ASN | A | 337 | 46.144 | 5.179 | −7.243 | 1.00 | 19.22 | A | O |
| ATOM | 5365 | ND2 | ASN | A | 337 | 47.557 | 6.035 | −5.719 | 1.00 | 16.23 | A | N |
| ATOM | 5368 | C | ASN | A | 337 | 47.362 | 1.221 | −6.689 | 1.00 | 13.58 | A | C |
| ATOM | 5369 | O | ASN | A | 337 | 47.512 | 0.822 | −7.841 | 1.00 | 13.59 | A | O |
| ATOM | 5371 | N | THR | A | 338 | 47.831 | 0.565 | −5.631 | 1.00 | 13.35 | A | N |
| ATOM | 5372 | CA | THR | A | 338 | 48.600 | −0.674 | −5.770 | 1.00 | 13.08 | A | C |
| ATOM | 5374 | CB | THR | A | 338 | 49.056 | −1.211 | −4.399 | 1.00 | 12.97 | A | C |
| ATOM | 5376 | OG1 | THR | A | 338 | 49.664 | −0.156 | −3.645 | 1.00 | 11.42 | A | O |
| ATOM | 5378 | CG2 | THR | A | 338 | 50.053 | −2.343 | −4.574 | 1.00 | 13.23 | A | C |
| ATOM | 5382 | C | THR | A | 338 | 47.803 | −1.766 | −6.487 | 1.00 | 13.11 | A | C |
| ATOM | 5383 | O | THR | A | 338 | 48.347 | −2.490 | −7.321 | 1.00 | 12.90 | A | O |
| ATOM | 5385 | N | ILE | A | 339 | 46.515 | −1.867 | −6.163 | 1.00 | 13.33 | A | N |
| ATOM | 5386 | CA | ILE | A | 339 | 45.632 | −2.852 | −6.786 | 1.00 | 13.78 | A | C |
| ATOM | 5388 | CB | ILE | A | 339 | 44.286 | −2.979 | −6.033 | 1.00 | 13.62 | A | C |
| ATOM | 5390 | CG1 | ILE | A | 339 | 44.507 | −3.429 | −4.585 | 1.00 | 13.37 | A | C |
| ATOM | 5393 | CD1 | ILE | A | 339 | 45.261 | −4.721 | −4.450 | 1.00 | 11.21 | A | C |
| ATOM | 5397 | CG2 | ILE | A | 339 | 43.364 | −3.962 | −6.740 | 1.00 | 13.25 | A | C |
| ATOM | 5401 | C | ILE | A | 339 | 45.356 | −2.486 | −8.242 | 1.00 | 14.51 | A | C |
| ATOM | 5402 | O | ILE | A | 339 | 45.444 | −3.338 | −9.127 | 1.00 | 14.76 | A | O |
| ATOM | 5404 | N | ASN | A | 340 | 45.025 | −1.220 | −8.485 | 1.00 | 15.03 | A | N |
| ATOM | 5405 | CA | ASN | A | 340 | 44.810 | −0.734 | −9.847 | 1.00 | 15.47 | A | C |
| ATOM | 5407 | CB | ASN | A | 340 | 44.412 | 0.741 | −9.843 | 1.00 | 15.26 | A | C |
| ATOM | 5410 | CG | ASN | A | 340 | 43.012 | 0.971 | −9.315 | 1.00 | 15.69 | A | C |
| ATOM | 5411 | OD1 | ASN | A | 340 | 42.256 | 0.030 | −9.065 | 1.00 | 14.77 | A | O |
| ATOM | 5412 | ND2 | ASN | A | 340 | 42.656 | 2.236 | −9.149 | 1.00 | 17.78 | A | N |
| ATOM | 5415 | C | ASN | A | 340 | 46.030 | −0.918 | −10.745 | 1.00 | 16.40 | A | C |
| ATOM | 5416 | O | ASN | A | 340 | 45.882 | −1.126 | −11.950 | 1.00 | 17.11 | A | O |
| ATOM | 5418 | N | GLU | A | 341 | 47.227 | −0.839 | −10.161 | 1.00 | 16.74 | A | N |
| ATOM | 5419 | CA | GLU | A | 341 | 48.467 | −1.016 | −10.919 | 1.00 | 16.76 | A | C |
| ATOM | 5421 | CB | GLU | A | 341 | 49.645 | −0.371 | −10.193 | 1.00 | 17.38 | A | C |
| ATOM | 5424 | CG | GLU | A | 341 | 49.525 | 1.142 | −10.115 | 1.00 | 20.36 | A | C |
| ATOM | 5427 | CD | GLU | A | 341 | 50.747 | 1.812 | −9.519 | 1.00 | 25.20 | A | C |
| ATOM | 5428 | OE1 | GLU | A | 341 | 51.715 | 1.100 | −9.164 | 1.00 | 27.46 | A | O |
| ATOM | 5429 | OE2 | GLU | A | 341 | 50.731 | 3.061 | −9.411 | 1.00 | 26.48 | A | O |
| ATOM | 5430 | C | GLU | A | 341 | 48.765 | −2.480 | −11.232 | 1.00 | 15.62 | A | C |
| ATOM | 5431 | O | GLU | A | 341 | 49.288 | −2.782 | −12.305 | 1.00 | 15.57 | A | O |
| ATOM | 5433 | N | ILE | A | 342 | 48.439 | −3.390 | −10.316 | 1.00 | 14.59 | A | N |
| ATOM | 5434 | CA | ILE | A | 342 | 48.519 | −4.819 | −10.637 | 1.00 | 14.45 | A | C |
| ATOM | 5436 | CB | ILE | A | 342 | 48.289 | −5.731 | −9.410 | 1.00 | 14.11 | A | C |
| ATOM | 5438 | CG1 | ILE | A | 342 | 49.421 | −5.570 | −8.398 | 1.00 | 14.65 | A | C |
| ATOM | 5441 | CD1 | ILE | A | 342 | 49.239 | −6.395 | −7.145 | 1.00 | 14.72 | A | C |
| ATOM | 5445 | CG2 | ILE | A | 342 | 48.233 | −7.189 | −9.837 | 1.00 | 13.46 | A | C |
| ATOM | 5449 | C | ILE | A | 342 | 47.490 | −5.145 | −11.724 | 1.00 | 14.17 | A | C |
| ATOM | 5450 | O | ILE | A | 342 | 47.784 | −5.884 | −12.668 | 1.00 | 14.44 | A | O |
| ATOM | 5452 | N | ALA | A | 343 | 46.293 | −4.576 | −11.586 | 1.00 | 13.41 | A | N |
| ATOM | 5453 | CA | ALA | A | 343 | 45.229 | −4.730 | −12.577 | 1.00 | 12.37 | A | C |
| ATOM | 5455 | CB | ALA | A | 343 | 43.979 | −3.989 | −12.127 | 1.00 | 12.12 | A | C |
| ATOM | 5459 | C | ALA | A | 343 | 45.671 | −4.234 | −13.952 | 1.00 | 11.86 | A | C |
| ATOM | 5460 | O | ALA | A | 343 | 45.270 | −4.793 | −14.971 | 1.00 | 11.95 | A | O |
| ATOM | 5462 | N | TYR | A | 344 | 46.491 | −3.182 | −13.974 | 1.00 | 11.28 | A | N |
| ATOM | 5463 | CA | TYR | A | 344 | 47.076 | −2.685 | −15.219 | 1.00 | 10.66 | A | C |
| ATOM | 5465 | CB | TYR | A | 344 | 47.703 | −1.298 | −15.027 | 1.00 | 10.43 | A | C |
| ATOM | 5468 | CG | TYR | A | 344 | 48.443 | −0.803 | −16.250 | 1.00 | 8.34 | A | C |
| ATOM | 5469 | CD1 | TYR | A | 344 | 47.782 | −0.096 | −17.248 | 1.00 | 6.31 | A | C |
| ATOM | 5471 | CE1 | TYR | A | 344 | 48.453 | 0.350 | −18.377 | 1.00 | 5.53 | A | C |
| ATOM | 5473 | CZ | TYR | A | 344 | 49.802 | 0.088 | −18.520 | 1.00 | 6.31 | A | C |

TABLE 8-2-continued

Coordinates for L494P Structure

| | | | | | | | | | | | | |
|---|---|---|---|---|---|---|---|---|---|---|---|---|
| ATOM | 5474 | OH | TYR | A | 344 | 50.471 | 0.530 | −19.638 | 1.00 | 4.56 | A | O |
| ATOM | 5476 | CE2 | TYR | A | 344 | 50.482 | −0.614 | −17.542 | 1.00 | 7.74 | A | C |
| ATOM | 5478 | CD2 | TYR | A | 344 | 49.801 | −1.056 | −16.416 | 1.00 | 7.79 | A | C |
| ATOM | 5480 | C | TYR | A | 344 | 48.124 | −3.666 | −15.725 | 1.00 | 10.67 | A | C |
| ATOM | 5481 | O | TYR | A | 344 | 48.084 | −4.078 | −16.881 | 1.00 | 10.32 | A | O |
| ATOM | 5483 | N | ASP | A | 345 | 49.060 | −4.033 | −14.853 | 1.00 | 11.33 | A | N |
| ATOM | 5484 | CA | ASP | A | 345 | 50.108 | −5.004 | −15.192 | 1.00 | 11.99 | A | C |
| ATOM | 5486 | CB | ASP | A | 345 | 50.939 | −5.377 | −13.948 | 1.00 | 12.01 | A | C |
| ATOM | 5489 | CG | ASP | A | 345 | 51.945 | −4.297 | −13.553 | 1.00 | 12.59 | A | C |
| ATOM | 5490 | OD1 | ASP | A | 345 | 52.076 | −3.277 | −14.269 | 1.00 | 11.18 | A | O |
| ATOM | 5491 | OD2 | ASP | A | 345 | 52.615 | −4.483 | −12.513 | 1.00 | 12.55 | A | O |
| ATOM | 5492 | C | ASP | A | 345 | 49.530 | −6.275 | −15.829 | 1.00 | 11.93 | A | C |
| ATOM | 5493 | O | ASP | A | 345 | 50.123 | −6.833 | −16.758 | 1.00 | 11.83 | A | O |
| ATOM | 5495 | N | ASN | A | 346 | 48.378 | −6.722 | −15.329 | 1.00 | 11.62 | A | N |
| ATOM | 5496 | CA | ASN | A | 346 | 47.709 | −7.906 | −15.868 | 1.00 | 11.58 | A | C |
| ATOM | 5498 | CB | ASN | A | 346 | 46.774 | −8.521 | −14.825 | 1.00 | 11.15 | A | C |
| ATOM | 5501 | CG | ASN | A | 346 | 47.516 | −9.376 | −13.819 | 1.00 | 12.26 | A | C |
| ATOM | 5502 | OD1 | ASN | A | 346 | 48.097 | −10.404 | −14.173 | 1.00 | 14.81 | A | O |
| ATOM | 5503 | ND2 | ASN | A | 346 | 47.502 | −8.961 | −12.557 | 1.00 | 12.75 | A | N |
| ATOM | 5506 | C | ASN | A | 346 | 46.956 | −7.634 | −17.171 | 1.00 | 11.92 | A | C |
| ATOM | 5507 | O | ASN | A | 346 | 46.898 | −8.503 | −18.041 | 1.00 | 12.36 | A | O |
| ATOM | 5509 | N | LEU | A | 347 | 46.384 | −6.440 | −17.311 | 1.00 | 11.92 | A | N |
| ATOM | 5510 | CA | LEU | A | 347 | 45.734 | −6.057 | −18.566 | 1.00 | 11.64 | A | C |
| ATOM | 5512 | CB | LEU | A | 347 | 44.961 | −4.740 | −18.413 | 1.00 | 11.58 | A | C |
| ATOM | 5515 | CG | LEU | A | 347 | 44.059 | −4.336 | −19.588 | 1.00 | 10.95 | A | C |
| ATOM | 5517 | CD1 | LEU | A | 347 | 42.907 | −5.312 | −19.745 | 1.00 | 10.27 | A | C |
| ATOM | 5521 | CD2 | LEU | A | 347 | 43.533 | −2.919 | −19.413 | 1.00 | 9.70 | A | C |
| ATOM | 5525 | C | LEU | A | 347 | 46.772 | −5.936 | −19.680 | 1.00 | 11.59 | A | C |
| ATOM | 5526 | O | LEU | A | 347 | 46.514 | −6.330 | −20.814 | 1.00 | 11.64 | A | O |
| ATOM | 5528 | N | LYS | A | 348 | 47.946 | −5.405 | −19.348 | 1.00 | 11.60 | A | N |
| ATOM | 5529 | CA | LYS | A | 348 | 49.022 | −5.244 | −20.321 | 1.00 | 11.67 | A | C |
| ATOM | 5531 | CB | LYS | A | 348 | 50.169 | −4.411 | −19.731 | 1.00 | 11.61 | A | C |
| ATOM | 5534 | CG | LYS | A | 348 | 51.223 | −4.009 | −20.758 | 1.00 | 12.03 | A | C |
| ATOM | 5537 | CD | LYS | A | 348 | 52.290 | −3.072 | −20.194 | 1.00 | 12.25 | A | C |
| ATOM | 5540 | CE | LYS | A | 348 | 53.520 | −3.809 | −19.672 | 1.00 | 12.33 | A | C |
| ATOM | 5543 | NZ | LYS | A | 348 | 53.341 | −4.292 | −18.278 | 1.00 | 14.05 | A | N |
| ATOM | 5547 | C | LYS | A | 348 | 49.558 | −6.595 | −20.794 | 1.00 | 11.72 | A | C |
| ATOM | 5548 | O | LYS | A | 348 | 49.582 | −6.876 | −21.990 | 1.00 | 11.62 | A | O |
| ATOM | 5550 | N | ASP | A | 349 | 49.969 | −7.430 | −19.847 | 1.00 | 12.09 | A | N |
| ATOM | 5551 | CA | ASP | A | 349 | 50.714 | −8.650 | −20.162 | 1.00 | 12.80 | A | C |
| ATOM | 5553 | CB | ASP | A | 349 | 51.664 | −8.986 | −19.006 | 1.00 | 13.12 | A | C |
| ATOM | 5556 | CG | ASP | A | 349 | 52.656 | −7.862 | −18.717 | 1.00 | 14.20 | A | C |
| ATOM | 5557 | OD1 | ASP | A | 349 | 52.969 | −7.085 | −19.650 | 1.00 | 11.97 | A | O |
| ATOM | 5558 | OD2 | ASP | A | 349 | 53.120 | −7.756 | −17.558 | 1.00 | 15.26 | A | O |
| ATOM | 5559 | C | ASP | A | 349 | 49.851 | −9.873 | −20.506 | 1.00 | 12.85 | A | C |
| ATOM | 5560 | O | ASP | A | 349 | 50.365 | −10.840 | −21.071 | 1.00 | 12.41 | A | O |
| ATOM | 5562 | N | LYS | A | 350 | 48.560 | −9.833 | −20.169 | 1.00 | 13.16 | A | N |
| ATOM | 5563 | CA | LYS | A | 350 | 47.635 | −10.942 | −20.471 | 1.00 | 13.31 | A | C |
| ATOM | 5565 | CB | LYS | A | 350 | 47.101 | −11.564 | −19.179 | 1.00 | 13.49 | A | C |
| ATOM | 5568 | CG | LYS | A | 350 | 48.180 | −12.050 | −18.233 | 1.00 | 15.19 | A | C |
| ATOM | 5571 | CD | LYS | A | 350 | 47.570 | −12.759 | −17.044 | 1.00 | 17.31 | A | C |
| ATOM | 5574 | CE | LYS | A | 350 | 48.620 | −13.131 | −16.015 | 1.00 | 17.74 | A | C |
| ATOM | 5577 | NZ | LYS | A | 350 | 47.980 | −13.734 | −14.818 | 1.00 | 17.79 | A | N |
| ATOM | 5581 | C | LYS | A | 350 | 46.451 | −10.554 | −21.358 | 1.00 | 12.84 | A | C |
| ATOM | 5582 | O | LYS | A | 350 | 45.896 | −11.406 | −22.048 | 1.00 | 12.55 | A | O |
| ATOM | 5584 | N | GLY | A | 351 | 46.056 | −9.285 | −21.331 | 1.00 | 13.03 | A | N |
| ATOM | 5585 | CA | GLY | A | 351 | 44.914 | −8.816 | −22.115 | 1.00 | 13.29 | A | C |
| ATOM | 5588 | C | GLY | A | 351 | 43.595 | −9.148 | −21.448 | 1.00 | 13.31 | A | C |
| ATOM | 5589 | O | GLY | A | 351 | 42.623 | −9.491 | −22.116 | 1.00 | 13.20 | A | O |
| ATOM | 5591 | N | GLU | A | 352 | 43.567 | −9.047 | −20.124 | 1.00 | 13.73 | A | N |
| ATOM | 5592 | CA | GLU | A | 352 | 42.388 | −9.384 | −19.342 | 1.00 | 14.52 | A | C |
| ATOM | 5594 | CB | GLU | A | 352 | 42.547 | −10.770 | −18.698 | 1.00 | 14.81 | A | C |
| ATOM | 5597 | CG | GLU | A | 352 | 42.906 | −11.923 | −19.656 | 1.00 | 15.61 | A | C |
| ATOM | 5600 | CD | GLU | A | 352 | 41.735 | −12.422 | −20.503 | 1.00 | 15.97 | A | C |
| ATOM | 5601 | OE1 | GLU | A | 352 | 40.627 | −11.845 | −20.425 | 1.00 | 15.33 | A | O |
| ATOM | 5602 | OE2 | GLU | A | 352 | 41.934 | −13.408 | −21.249 | 1.00 | 14.04 | A | O |
| ATOM | 5603 | C | GLU | A | 352 | 42.187 | −8.335 | −18.249 | 1.00 | 14.94 | A | C |
| ATOM | 5604 | O | GLU | A | 352 | 43.153 | −7.891 | −17.621 | 1.00 | 14.91 | A | O |
| ATOM | 5606 | N | ASN | A | 353 | 40.933 | −7.944 | −18.028 | 1.00 | 15.09 | A | N |
| ATOM | 5607 | CA | ASN | A | 353 | 40.579 | −7.054 | −16.924 | 1.00 | 15.05 | A | C |
| ATOM | 5609 | CB | ASN | A | 353 | 39.393 | −6.167 | −17.315 | 1.00 | 15.19 | A | C |
| ATOM | 5612 | CG | ASN | A | 353 | 39.132 | −5.055 | −16.314 | 1.00 | 14.51 | A | C |
| ATOM | 5613 | OD1 | ASN | A | 353 | 39.523 | −5.135 | −15.151 | 1.00 | 12.06 | A | O |
| ATOM | 5614 | ND2 | ASN | A | 353 | 38.459 | −4.007 | −16.769 | 1.00 | 16.67 | A | N |
| ATOM | 5617 | C | ASN | A | 353 | 40.238 | −7.895 | −15.696 | 1.00 | 14.95 | A | C |
| ATOM | 5618 | O | ASN | A | 353 | 39.198 | −8.554 | −15.662 | 1.00 | 15.14 | A | O |
| ATOM | 5620 | N | ILE | A | 354 | 41.118 | −7.863 | −14.695 | 1.00 | 14.71 | A | N |
| ATOM | 5621 | CA | ILE | A | 354 | 40.940 | −8.652 | −13.472 | 1.00 | 14.50 | A | C |

TABLE 8-2-continued

| Coordinates for L494P Structure | | | | | | | | | | | | |
|---|---|---|---|---|---|---|---|---|---|---|---|---|
| ATOM | 5623 | CB | ILE | A | 354 | 42.138 | −9.614 | −13.238 | 1.00 | 14.70 | A | C |
| ATOM | 5625 | CG1 | ILE | A | 354 | 43.430 | −8.840 | −12.954 | 1.00 | 14.73 | A | C |
| ATOM | 5628 | CD1 | ILE | A | 354 | 44.527 | −9.706 | −12.397 | 1.00 | 13.59 | A | C |
| ATOM | 5632 | CG2 | ILE | A | 354 | 42.333 | −10.530 | −14.441 | 1.00 | 15.18 | A | C |
| ATOM | 5636 | C | ILE | A | 354 | 40.736 | −7.791 | −12.221 | 1.00 | 14.26 | A | C |
| ATOM | 5637 | O | ILE | A | 354 | 40.839 | −8.290 | −11.104 | 1.00 | 14.39 | A | O |
| ATOM | 5639 | N | LEU | A | 355 | 40.440 | −6.507 | −12.401 | 1.00 | 14.54 | A | N |
| ATOM | 5640 | CA | LEU | A | 355 | 40.244 | −5.601 | −11.266 | 1.00 | 14.48 | A | C |
| ATOM | 5642 | CB | LEU | A | 355 | 40.026 | −4.157 | −11.748 | 1.00 | 14.01 | A | C |
| ATOM | 5645 | CG | LEU | A | 355 | 39.868 | −3.068 | −10.679 | 1.00 | 13.56 | A | C |
| ATOM | 5647 | CD1 | LEU | A | 355 | 41.000 | −3.113 | −9.666 | 1.00 | 13.71 | A | C |
| ATOM | 5651 | CD2 | LEU | A | 355 | 39.786 | −1.687 | −11.320 | 1.00 | 12.08 | A | C |
| ATOM | 5655 | C | LEU | A | 355 | 39.103 | −6.042 | −10.335 | 1.00 | 14.97 | A | C |
| ATOM | 5656 | O | LEU | A | 355 | 39.248 | −5.951 | −9.116 | 1.00 | 15.16 | A | O |
| ATOM | 5658 | N | PRO | A | 356 | 37.976 | −6.532 | −10.899 | 1.00 | 15.42 | A | N |
| ATOM | 5659 | CA | PRO | A | 356 | 36.863 | −6.986 | −10.057 | 1.00 | 15.69 | A | C |
| ATOM | 5661 | CB | PRO | A | 356 | 35.785 | −7.372 | −11.079 | 1.00 | 15.69 | A | C |
| ATOM | 5664 | CG | PRO | A | 356 | 36.124 | −6.623 | −12.292 | 1.00 | 15.33 | A | C |
| ATOM | 5667 | CD | PRO | A | 356 | 37.610 | −6.580 | −12.326 | 1.00 | 15.51 | A | C |
| ATOM | 5670 | C | PRO | A | 356 | 37.177 | −8.185 | −9.154 | 1.00 | 15.96 | A | C |
| ATOM | 5671 | O | PRO | A | 356 | 36.545 | −8.342 | −8.107 | 1.00 | 16.29 | A | O |
| ATOM | 5672 | N | TYR | A | 357 | 38.130 | −9.023 | −9.556 | 1.00 | 15.86 | A | N |
| ATOM | 5673 | CA | TYR | A | 357 | 38.504 | −10.198 | −8.762 | 1.00 | 16.04 | A | C |
| ATOM | 5675 | CB | TYR | A | 357 | 39.099 | −11.298 | −9.651 | 1.00 | 16.10 | A | C |
| ATOM | 5678 | CG | TYR | A | 357 | 38.332 | −11.505 | −10.938 | 1.00 | 17.77 | A | C |
| ATOM | 5679 | CD1 | TYR | A | 357 | 36.958 | −11.732 | −10.921 | 1.00 | 18.41 | A | C |
| ATOM | 5681 | CE1 | TYR | A | 357 | 36.244 | −11.912 | −12.099 | 1.00 | 18.01 | A | C |
| ATOM | 5683 | CZ | TYR | A | 357 | 36.905 | −11.864 | −13.311 | 1.00 | 18.22 | A | C |
| ATOM | 5684 | OH | TYR | A | 357 | 36.207 | −12.043 | −14.479 | 1.00 | 19.76 | A | O |
| ATOM | 5686 | CE2 | TYR | A | 357 | 38.269 | −11.641 | −13.356 | 1.00 | 18.63 | A | C |
| ATOM | 5688 | CD2 | TYR | A | 357 | 38.975 | −11.460 | −12.173 | 1.00 | 18.68 | A | C |
| ATOM | 5690 | C | TYR | A | 357 | 39.489 | −9.810 | −7.661 | 1.00 | 15.60 | A | C |
| ATOM | 5691 | O | TYR | A | 357 | 39.448 | −10.361 | −6.562 | 1.00 | 15.71 | A | O |
| ATOM | 5693 | N | LEU | A | 358 | 40.371 | −8.861 | −7.965 | 1.00 | 15.17 | A | N |
| ATOM | 5694 | CA | LEU | A | 358 | 41.318 | −8.345 | −6.983 | 1.00 | 14.66 | A | C |
| ATOM | 5696 | CB | LEU | A | 358 | 42.383 | −7.471 | −7.655 | 1.00 | 14.49 | A | C |
| ATOM | 5699 | CG | LEU | A | 358 | 43.348 | −8.179 | −8.610 | 1.00 | 13.67 | A | C |
| ATOM | 5701 | CD1 | LEU | A | 358 | 44.231 | −7.165 | −9.319 | 1.00 | 13.09 | A | C |
| ATOM | 5705 | CD2 | LEU | A | 358 | 44.198 | −9.197 | −7.873 | 1.00 | 11.60 | A | C |
| ATOM | 5709 | C | LEU | A | 358 | 40.597 | −7.548 | −5.899 | 1.00 | 14.57 | A | C |
| ATOM | 5710 | O | LEU | A | 358 | 40.844 | −7.764 | −4.713 | 1.00 | 15.41 | A | O |
| ATOM | 5712 | N | THR | A | 359 | 39.703 | −6.644 | −6.304 | 1.00 | 13.71 | A | N |
| ATOM | 5713 | CA | THR | A | 359 | 39.002 | −5.768 | −5.354 | 1.00 | 13.19 | A | C |
| ATOM | 5715 | CB | THR | A | 359 | 38.347 | −4.560 | −6.058 | 1.00 | 13.29 | A | C |
| ATOM | 5717 | OG1 | THR | A | 359 | 37.390 | −5.020 | −7.020 | 1.00 | 15.24 | A | O |
| ATOM | 5719 | CG2 | THR | A | 359 | 39.399 | −3.705 | −6.748 | 1.00 | 12.12 | A | C |
| ATOM | 5723 | C | THR | A | 359 | 37.933 | −6.490 | −4.528 | 1.00 | 12.69 | A | C |
| ATOM | 5724 | O | THR | A | 359 | 37.545 | −6.008 | −3.464 | 1.00 | 12.15 | A | O |
| ATOM | 5726 | N | LYS | A | 360 | 37.456 | −7.634 | −5.019 | 1.00 | 12.46 | A | N |
| ATOM | 5727 | CA | LYS | A | 360 | 36.519 | −8.471 | −4.263 | 1.00 | 12.16 | A | C |
| ATOM | 5729 | CB | LYS | A | 360 | 35.845 | −9.498 | −5.180 | 1.00 | 12.44 | A | C |
| ATOM | 5732 | CG | LYS | A | 360 | 34.793 | −10.378 | −4.499 | 1.00 | 13.59 | A | C |
| ATOM | 5735 | CD | LYS | A | 360 | 33.591 | −9.569 | −4.027 | 1.00 | 14.74 | A | C |
| ATOM | 5738 | CE | LYS | A | 360 | 32.450 | −10.472 | −3.579 | 1.00 | 15.45 | A | C |
| ATOM | 5741 | NZ | LYS | A | 360 | 31.179 | −9.724 | −3.364 | 1.00 | 15.06 | A | N |
| ATOM | 5745 | C | LYS | A | 360 | 37.235 | −9.185 | −3.118 | 1.00 | 11.29 | A | C |
| ATOM | 5746 | O | LYS | A | 360 | 36.666 | −9.365 | −2.042 | 1.00 | 11.08 | A | O |
| ATOM | 5748 | N | ALA | A | 361 | 38.476 | −9.598 | −3.359 | 1.00 | 10.61 | A | N |
| ATOM | 5749 | CA | ALA | A | 361 | 39.304 | −10.206 | −2.318 | 1.00 | 10.70 | A | C |
| ATOM | 5751 | CB | ALA | A | 361 | 40.628 | −10.673 | −2.900 | 1.00 | 11.07 | A | C |
| ATOM | 5755 | C | ALA | A | 361 | 39.553 | −9.222 | −1.181 | 1.00 | 10.58 | A | C |
| ATOM | 5756 | O | ALA | A | 361 | 39.661 | −9.619 | −0.019 | 1.00 | 10.13 | A | O |
| ATOM | 5758 | N | TRP | A | 362 | 39.643 | −7.941 | −1.534 | 1.00 | 10.54 | A | N |
| ATOM | 5759 | CA | TRP | A | 362 | 39.859 | −6.868 | −0.568 | 1.00 | 10.37 | A | C |
| ATOM | 5761 | CB | TRP | A | 362 | 40.577 | −5.696 | −1.236 | 1.00 | 9.72 | A | C |
| ATOM | 5764 | CG | TRP | A | 362 | 42.045 | −5.882 | −1.233 | 1.00 | 9.03 | A | C |
| ATOM | 5765 | CD1 | TRP | A | 362 | 42.838 | −6.216 | −2.288 | 1.00 | 9.07 | A | C |
| ATOM | 5767 | NE1 | TRP | A | 362 | 44.147 | −6.312 | −1.883 | 1.00 | 8.13 | A | N |
| ATOM | 5769 | CE2 | TRP | A | 362 | 44.215 | −6.045 | −0.542 | 1.00 | 7.66 | A | C |
| ATOM | 5770 | CD2 | TRP | A | 362 | 42.907 | −5.775 | −0.099 | 1.00 | 7.66 | A | C |
| ATOM | 5771 | CE3 | TRP | A | 362 | 42.699 | −5.472 | 1.250 | 1.00 | 7.22 | A | C |
| ATOM | 5773 | CZ3 | TRP | A | 362 | 43.784 | −5.446 | 2.099 | 1.00 | 7.74 | A | C |
| ATOM | 5775 | CH2 | TRP | A | 362 | 45.076 | −5.718 | 1.629 | 1.00 | 9.54 | A | C |
| ATOM | 5777 | CZ2 | TRP | A | 362 | 45.310 | −6.018 | 0.314 | 1.00 | 9.02 | A | C |
| ATOM | 5779 | C | TRP | A | 362 | 38.570 | −6.394 | 0.099 | 1.00 | 11.16 | A | C |
| ATOM | 5780 | O | TRP | A | 362 | 38.588 | −6.007 | 1.267 | 1.00 | 11.42 | A | O |
| ATOM | 5782 | N | ALA | A | 363 | 37.462 | −6.416 | −0.639 | 1.00 | 11.67 | A | N |
| ATOM | 5783 | CA | ALA | A | 363 | 36.151 | −6.099 | −0.070 | 1.00 | 12.00 | A | C |

TABLE 8-2-continued

Coordinates for L494P Structure

| | | | | | | | | | | | | |
|---|---|---|---|---|---|---|---|---|---|---|---|---|
| ATOM | 5785 | CB | ALA | A | 363 | 35.103 | −5.985 | −1.169 | 1.00 | 11.90 | A | C |
| ATOM | 5789 | C | ALA | A | 363 | 35.738 | −7.162 | 0.941 | 1.00 | 12.69 | A | C |
| ATOM | 5790 | O | ALA | A | 363 | 35.096 | −6.857 | 1.944 | 1.00 | 12.73 | A | O |
| ATOM | 5792 | N | ASP | A | 364 | 36.112 | −8.409 | 0.670 | 1.00 | 13.63 | A | N |
| ATOM | 5793 | CA | ASP | A | 364 | 35.763 | −9.523 | 1.544 | 1.00 | 14.66 | A | C |
| ATOM | 5795 | CB | ASP | A | 364 | 35.734 | −10.838 | 0.754 | 1.00 | 15.17 | A | C |
| ATOM | 5798 | CG | ASP | A | 364 | 34.559 | −10.916 | −0.223 | 1.00 | 17.28 | A | C |
| ATOM | 5799 | OD1 | ASP | A | 364 | 33.578 | −10.155 | −0.061 | 1.00 | 17.21 | A | O |
| ATOM | 5800 | OD2 | ASP | A | 364 | 34.618 | −11.751 | −1.154 | 1.00 | 20.88 | A | O |
| ATOM | 5801 | C | ASP | A | 364 | 36.711 | −9.635 | 2.738 | 1.00 | 14.83 | A | C |
| ATOM | 5802 | O | ASP | A | 364 | 36.275 | −9.968 | 3.841 | 1.00 | 15.19 | A | O |
| ATOM | 5804 | N | LEU | A | 365 | 37.998 | −9.359 | 2.527 | 1.00 | 14.97 | A | N |
| ATOM | 5805 | CA | LEU | A | 365 | 38.978 | −9.400 | 3.620 | 1.00 | 14.98 | A | C |
| ATOM | 5807 | CB | LEU | A | 365 | 40.399 | −9.149 | 3.100 | 1.00 | 14.64 | A | C |
| ATOM | 5810 | CG | LEU | A | 365 | 41.521 | −9.152 | 4.146 | 1.00 | 13.12 | A | C |
| ATOM | 5812 | CD1 | LEU | A | 365 | 41.596 | −10.491 | 4.852 | 1.00 | 12.43 | A | C |
| ATOM | 5816 | CD2 | LEU | A | 365 | 42.861 | −8.812 | 3.514 | 1.00 | 13.28 | A | C |
| ATOM | 5820 | C | LEU | A | 365 | 38.632 | −8.367 | 4.685 | 1.00 | 15.67 | A | C |
| ATOM | 5821 | O | LEU | A | 365 | 38.742 | −8.637 | 5.884 | 1.00 | 16.08 | A | O |
| ATOM | 5823 | N | CYS | A | 366 | 38.216 | −7.187 | 4.234 | 1.00 | 16.03 | A | N |
| ATOM | 5824 | CA | CYS | A | 366 | 37.820 | −6.108 | 5.130 | 1.00 | 16.51 | A | C |
| ATOM | 5826 | CB | CYS | A | 366 | 37.723 | −4.784 | 4.363 | 1.00 | 16.60 | A | C |
| ATOM | 5829 | SG | CYS | A | 366 | 39.333 | −4.159 | 3.767 | 1.00 | 17.69 | A | S |
| ATOM | 5831 | C | CYS | A | 366 | 36.505 | −6.430 | 5.850 | 1.00 | 17.00 | A | C |
| ATOM | 5832 | O | CYS | A | 366 | 36.377 | −6.170 | 7.047 | 1.00 | 17.59 | A | O |
| ATOM | 5834 | N | ASN | A | 367 | 35.541 | −7.008 | 5.132 | 1.00 | 17.21 | A | N |
| ATOM | 5835 | CA | ASN | A | 367 | 34.291 | −7.476 | 5.757 | 1.00 | 17.08 | A | C |
| ATOM | 5837 | CB | ASN | A | 367 | 33.275 | −7.939 | 4.703 | 1.00 | 17.09 | A | C |
| ATOM | 5840 | CG | ASN | A | 367 | 32.260 | −6.863 | 4.354 | 1.00 | 17.63 | A | C |
| ATOM | 5841 | OD1 | ASN | A | 367 | 31.791 | −6.127 | 5.225 | 1.00 | 17.70 | A | O |
| ATOM | 5842 | ND2 | ASN | A | 367 | 31.903 | −6.778 | 3.076 | 1.00 | 17.33 | A | N |
| ATOM | 5845 | C | ASN | A | 367 | 34.514 | −8.590 | 6.782 | 1.00 | 17.07 | A | C |
| ATOM | 5846 | O | ASN | A | 367 | 33.684 | −8.793 | 7.670 | 1.00 | 17.00 | A | O |
| ATOM | 5848 | N | ALA | A | 368 | 35.627 | −9.311 | 6.646 | 1.00 | 16.97 | A | N |
| ATOM | 5849 | CA | ALA | A | 368 | 36.051 | −10.287 | 7.647 | 1.00 | 16.97 | A | C |
| ATOM | 5851 | CB | ALA | A | 368 | 37.167 | −11.156 | 7.093 | 1.00 | 16.96 | A | C |
| ATOM | 5855 | C | ALA | A | 368 | 36.505 | −9.598 | 8.937 | 1.00 | 17.11 | A | C |
| ATOM | 5856 | O | ALA | A | 368 | 36.112 | −10.006 | 10.034 | 1.00 | 16.89 | A | O |
| ATOM | 5858 | N | PHE | A | 369 | 37.332 | −8.559 | 8.798 | 1.00 | 17.06 | A | N |
| ATOM | 5859 | CA | PHE | A | 369 | 37.834 | −7.796 | 9.948 | 1.00 | 17.07 | A | C |
| ATOM | 5861 | CB | PHE | A | 369 | 38.876 | −6.756 | 9.517 | 1.00 | 17.09 | A | C |
| ATOM | 5864 | CG | PHE | A | 369 | 40.163 | −7.336 | 9.004 | 1.00 | 17.47 | A | C |
| ATOM | 5865 | CD1 | PHE | A | 369 | 40.847 | −8.307 | 9.722 | 1.00 | 19.16 | A | C |
| ATOM | 5867 | CE1 | PHE | A | 369 | 42.047 | −8.826 | 9.253 | 1.00 | 19.68 | A | C |
| ATOM | 5869 | CZ | PHE | A | 369 | 42.583 | −8.361 | 8.064 | 1.00 | 19.22 | A | C |
| ATOM | 5871 | CE2 | PHE | A | 369 | 41.917 | −7.383 | 7.347 | 1.00 | 19.11 | A | C |
| ATOM | 5873 | CD2 | PHE | A | 369 | 40.717 | −6.872 | 7.820 | 1.00 | 17.84 | A | C |
| ATOM | 5875 | C | PHE | A | 369 | 36.721 | −7.061 | 10.694 | 1.00 | 17.02 | A | C |
| ATOM | 5876 | O | PHE | A | 369 | 36.748 | −6.961 | 11.924 | 1.00 | 17.17 | A | O |
| ATOM | 5878 | N | LEU | A | 370 | 35.763 | −6.521 | 9.945 | 1.00 | 16.86 | A | N |
| ATOM | 5879 | CA | LEU | A | 370 | 34.624 | −5.827 | 10.543 | 1.00 | 16.90 | A | C |
| ATOM | 5881 | CB | LEU | A | 370 | 33.710 | −5.241 | 9.462 | 1.00 | 17.00 | A | C |
| ATOM | 5884 | CG | LEU | A | 370 | 32.790 | −4.104 | 9.913 | 1.00 | 16.77 | A | C |
| ATOM | 5886 | CD1 | LEU | A | 370 | 33.545 | −2.782 | 9.908 | 1.00 | 17.03 | A | C |
| ATOM | 5890 | CD2 | LEU | A | 370 | 31.557 | −4.011 | 9.027 | 1.00 | 17.46 | A | C |
| ATOM | 5894 | C | LEU | A | 370 | 33.843 | −6.802 | 11.415 | 1.00 | 17.08 | A | C |
| ATOM | 5895 | O | LEU | A | 370 | 33.438 | −6.464 | 12.526 | 1.00 | 16.72 | A | O |
| ATOM | 5897 | N | GLN | A | 371 | 33.651 | −8.016 | 10.899 | 1.00 | 17.46 | A | N |
| ATOM | 5898 | CA | GLN | A | 371 | 32.961 | −9.077 | 11.626 | 1.00 | 17.49 | A | C |
| ATOM | 5900 | CB | GLN | A | 371 | 32.719 | −10.279 | 10.708 | 1.00 | 17.34 | A | C |
| ATOM | 5903 | CG | GLN | A | 371 | 31.916 | −11.410 | 11.344 | 1.00 | 17.48 | A | C |
| ATOM | 5906 | CD | GLN | A | 371 | 30.512 | −10.990 | 11.732 | 1.00 | 17.14 | A | C |
| ATOM | 5907 | OE1 | GLN | A | 371 | 30.267 | −10.572 | 12.863 | 1.00 | 17.53 | A | O |
| ATOM | 5908 | NE2 | GLN | A | 371 | 29.582 | −11.091 | 10.789 | 1.00 | 16.59 | A | N |
| ATOM | 5911 | C | GLN | A | 371 | 33.741 | −9.506 | 12.869 | 1.00 | 17.91 | A | C |
| ATOM | 5912 | O | GLN | A | 371 | 33.140 | −9.800 | 13.901 | 1.00 | 18.11 | A | O |
| ATOM | 5914 | N | GLU | A | 372 | 35.070 | −9.549 | 12.767 | 1.00 | 18.39 | A | N |
| ATOM | 5915 | CA | GLU | A | 372 | 35.926 | −9.854 | 13.921 | 1.00 | 18.81 | A | C |
| ATOM | 5917 | CB | GLU | A | 372 | 37.388 | −10.058 | 13.498 | 1.00 | 19.35 | A | C |
| ATOM | 5920 | CG | GLU | A | 372 | 37.707 | −11.451 | 12.961 | 1.00 | 22.59 | A | C |
| ATOM | 5923 | CD | GLU | A | 372 | 39.205 | −11.722 | 12.862 | 1.00 | 26.48 | A | C |
| ATOM | 5924 | OE1 | GLU | A | 372 | 39.992 | −10.748 | 12.800 | 1.00 | 29.10 | A | O |
| ATOM | 5925 | OE2 | GLU | A | 372 | 39.594 | −12.912 | 12.843 | 1.00 | 27.20 | A | O |
| ATOM | 5926 | C | GLU | A | 372 | 35.854 | −8.752 | 14.976 | 1.00 | 18.32 | A | C |
| ATOM | 5927 | O | GLU | A | 372 | 35.775 | −9.040 | 16.171 | 1.00 | 18.34 | A | O |
| ATOM | 5929 | N | ALA | A | 373 | 35.886 | −7.497 | 14.528 | 1.00 | 17.77 | A | N |
| ATOM | 5930 | CA | ALA | A | 373 | 35.846 | −6.347 | 15.429 | 1.00 | 17.52 | A | C |
| ATOM | 5932 | CB | ALA | A | 373 | 36.239 | −5.085 | 14.685 | 1.00 | 17.47 | A | C |

TABLE 8-2-continued

Coordinates for L494P Structure

| | | | | | | | | | | | |
|---|---|---|---|---|---|---|---|---|---|---|---|
| ATOM | 5936 | C | ALA | A | 373 | 34.472 | −6.171 | 16.083 | 1.00 | 17.59 A | C |
| ATOM | 5937 | O | ALA | A | 373 | 34.383 | −5.819 | 17.259 | 1.00 | 17.52 A | O |
| ATOM | 5939 | N | LYS | A | 374 | 33.408 | −6.416 | 15.319 | 1.00 | 17.66 A | N |
| ATOM | 5940 | CA | LYS | A | 374 | 32.037 | −6.287 | 15.827 | 1.00 | 17.69 A | C |
| ATOM | 5942 | CB | LYS | A | 374 | 31.016 | −6.485 | 14.700 | 1.00 | 17.73 A | C |
| ATOM | 5945 | CG | LYS | A | 374 | 30.781 | −5.244 | 13.848 | 1.00 | 18.61 A | C |
| ATOM | 5948 | CD | LYS | A | 374 | 29.872 | −5.544 | 12.659 | 1.00 | 19.44 A | C |
| ATOM | 5951 | CE | LYS | A | 374 | 29.505 | −4.277 | 11.898 | 1.00 | 18.81 A | C |
| ATOM | 5954 | NZ | LYS | A | 374 | 28.710 | −4.565 | 10.673 | 1.00 | 18.02 A | N |
| ATOM | 5958 | C | LYS | A | 374 | 31.735 | −7.250 | 16.977 | 1.00 | 17.82 A | C |
| ATOM | 5959 | O | LYS | A | 374 | 31.028 | −6.884 | 17.917 | 1.00 | 17.93 A | O |
| ATOM | 5961 | N | TRP | A | 375 | 32.260 | −8.473 | 16.896 | 1.00 | 18.05 A | N |
| ATOM | 5962 | CA | TRP | A | 375 | 32.132 | −9.445 | 17.989 | 1.00 | 18.34 A | C |
| ATOM | 5964 | CB | TRP | A | 375 | 32.660 | −10.824 | 17.575 | 1.00 | 18.28 A | C |
| ATOM | 5967 | CG | TRP | A | 375 | 31.847 | −11.529 | 16.523 | 1.00 | 18.45 A | C |
| ATOM | 5968 | CD1 | TRP | A | 375 | 30.498 | −11.446 | 16.328 | 1.00 | 19.67 A | C |
| ATOM | 5970 | NE1 | TRP | A | 375 | 30.119 | −12.249 | 15.278 | 1.00 | 18.96 A | N |
| ATOM | 5972 | CE2 | TRP | A | 375 | 31.228 | −12.882 | 14.782 | 1.00 | 17.60 A | C |
| ATOM | 5973 | CD2 | TRP | A | 375 | 32.336 | −12.457 | 15.545 | 1.00 | 17.42 A | C |
| ATOM | 5974 | CE3 | TRP | A | 375 | 33.604 | −12.962 | 15.235 | 1.00 | 17.04 A | C |
| ATOM | 5976 | CZ3 | TRP | A | 375 | 33.724 | −13.861 | 14.186 | 1.00 | 17.20 A | C |
| ATOM | 5978 | CH2 | TRP | A | 375 | 32.602 | −14.267 | 13.446 | 1.00 | 17.60 A | C |
| ATOM | 5980 | CZ2 | TRP | A | 375 | 31.350 | −13.790 | 13.728 | 1.00 | 17.78 A | C |
| ATOM | 5982 | C | TRP | A | 375 | 32.883 | −8.983 | 19.241 | 1.00 | 18.75 A | C |
| ATOM | 5983 | O | TRP | A | 375 | 32.402 | −9.171 | 20.362 | 1.00 | 19.03 A | O |
| ATOM | 5985 | N | LEU | A | 376 | 34.062 | −8.392 | 19.041 | 1.00 | 18.64 A | N |
| ATOM | 5986 | CA | LEU | A | 376 | 34.890 | −7.907 | 20.147 | 1.00 | 18.48 A | C |
| ATOM | 5988 | CB | LEU | A | 376 | 36.302 | −7.572 | 19.650 | 1.00 | 18.65 A | C |
| ATOM | 5991 | CG | LEU | A | 376 | 37.413 | −7.399 | 20.697 | 1.00 | 20.28 A | C |
| ATOM | 5993 | CD1 | LEU | A | 376 | 38.775 | −7.749 | 20.098 | 1.00 | 21.89 A | C |
| ATOM | 5997 | CD2 | LEU | A | 376 | 37.437 | −5.986 | 21.285 | 1.00 | 20.91 A | C |
| ATOM | 6001 | C | LEU | A | 376 | 34.257 | −6.693 | 20.834 | 1.00 | 18.28 A | C |
| ATOM | 6002 | O | LEU | A | 376 | 34.401 | −6.525 | 22.046 | 1.00 | 18.58 A | O |
| ATOM | 6004 | N | TYR | A | 377 | 33.559 | −5.857 | 20.065 | 1.00 | 17.92 A | N |
| ATOM | 6005 | CA | TYR | A | 377 | 32.851 | −4.698 | 20.622 | 1.00 | 17.91 A | C |
| ATOM | 6007 | CB | TYR | A | 377 | 32.456 | −3.710 | 19.513 | 1.00 | 18.04 A | C |
| ATOM | 6010 | CG | TYR | A | 377 | 31.758 | −2.460 | 20.019 | 1.00 | 18.20 A | C |
| ATOM | 6011 | CD1 | TYR | A | 377 | 32.450 | −1.505 | 20.762 | 1.00 | 19.47 A | C |
| ATOM | 6013 | CE1 | TYR | A | 377 | 31.817 | −0.357 | 21.234 | 1.00 | 19.90 A | C |
| ATOM | 6015 | CZ | TYR | A | 377 | 30.474 | −0.154 | 20.961 | 1.00 | 20.89 A | C |
| ATOM | 6016 | OH | TYR | A | 377 | 29.846 | 0.980 | 21.429 | 1.00 | 19.22 A | O |
| ATOM | 6018 | CE2 | TYR | A | 377 | 29.763 | −1.090 | 20.223 | 1.00 | 20.13 A | C |
| ATOM | 6020 | CD2 | TYR | A | 377 | 30.409 | −2.234 | 19.756 | 1.00 | 18.66 A | C |
| ATOM | 6022 | C | TYR | A | 377 | 31.607 | −5.126 | 21.408 | 1.00 | 17.54 A | C |
| ATOM | 6023 | O | TYR | A | 377 | 31.403 | −4.696 | 22.546 | 1.00 | 17.43 A | O |
| ATOM | 6025 | N | ASN | A | 378 | 30.792 | −5.984 | 20.797 | 1.00 | 17.04 A | N |
| ATOM | 6026 | CA | ASN | A | 378 | 29.527 | −6.421 | 21.392 | 1.00 | 16.71 A | C |
| ATOM | 6028 | CB | ASN | A | 378 | 28.534 | −6.789 | 20.287 | 1.00 | 16.56 A | C |
| ATOM | 6031 | CG | ASN | A | 378 | 28.283 | −5.644 | 19.323 | 1.00 | 16.15 A | C |
| ATOM | 6032 | OD1 | ASN | A | 378 | 27.985 | −4.526 | 19.735 | 1.00 | 15.51 A | O |
| ATOM | 6033 | ND2 | ASN | A | 378 | 28.405 | −5.920 | 18.031 | 1.00 | 16.34 A | N |
| ATOM | 6036 | C | ASN | A | 378 | 29.675 | −7.599 | 22.356 | 1.00 | 16.69 A | C |
| ATOM | 6037 | O | ASN | A | 378 | 28.687 | −8.058 | 22.932 | 1.00 | 16.54 A | O |
| ATOM | 6039 | N | LYS | A | 379 | 30.905 | −8.083 | 22.528 | 1.00 | 16.67 A | N |
| ATOM | 6040 | CA | LYS | A | 379 | 31.188 | −9.241 | 23.375 | 1.00 | 16.55 A | C |
| ATOM | 6042 | CB | LYS | A | 379 | 31.047 | −8.874 | 24.859 | 1.00 | 16.40 A | C |
| ATOM | 6045 | CG | LYS | A | 379 | 32.158 | −7.964 | 25.348 | 1.00 | 17.12 A | C |
| ATOM | 6048 | CD | LYS | A | 379 | 31.853 | −7.352 | 26.702 | 1.00 | 17.89 A | C |
| ATOM | 6051 | CE | LYS | A | 379 | 33.029 | −6.523 | 27.198 | 1.00 | 18.11 A | C |
| ATOM | 6054 | NZ | LYS | A | 379 | 32.604 | −5.464 | 28.151 | 1.00 | 19.23 A | N |
| ATOM | 6058 | C | LYS | A | 379 | 30.305 | −10.432 | 22.997 | 1.00 | 16.36 A | C |
| ATOM | 6059 | O | LYS | A | 379 | 29.725 | −11.093 | 23.859 | 1.00 | 17.03 A | O |
| ATOM | 6061 | N | SER | A | 380 | 30.214 | −10.691 | 21.695 | 1.00 | 15.82 A | N |
| ATOM | 6062 | CA | SER | A | 380 | 29.447 | −11.818 | 21.179 | 1.00 | 15.44 A | C |
| ATOM | 6064 | CB | SER | A | 380 | 29.261 | −11.686 | 19.667 | 1.00 | 15.30 A | C |
| ATOM | 6067 | OG | SER | A | 380 | 28.738 | −10.414 | 19.326 | 1.00 | 14.16 A | O |
| ATOM | 6069 | C | SER | A | 380 | 30.171 | −13.118 | 21.503 | 1.00 | 15.54 A | C |
| ATOM | 6070 | O | SER | A | 380 | 31.377 | −13.115 | 21.747 | 1.00 | 15.63 A | O |
| ATOM | 6072 | N | THR | A | 381 | 29.433 | −14.226 | 21.504 | 1.00 | 15.71 A | N |
| ATOM | 6073 | CA | THR | A | 381 | 30.004 | −15.538 | 21.812 | 1.00 | 16.14 A | C |
| ATOM | 6075 | CB | THR | A | 381 | 29.483 | −16.076 | 23.173 | 1.00 | 16.44 A | C |
| ATOM | 6077 | OG1 | THR | A | 381 | 28.057 | −16.215 | 23.133 | 1.00 | 17.09 A | O |
| ATOM | 6079 | CG2 | THR | A | 381 | 29.863 | −15.133 | 24.309 | 1.00 | 17.19 A | C |
| ATOM | 6083 | C | THR | A | 381 | 29.694 | −16.539 | 20.696 | 1.00 | 16.10 A | C |
| ATOM | 6084 | O | THR | A | 381 | 29.099 | −17.591 | 20.947 | 1.00 | 16.34 A | O |
| ATOM | 6086 | N | PRO | A | 382 | 30.115 | −16.223 | 19.456 | 1.00 | 16.07 A | N |
| ATOM | 6087 | CA | PRO | A | 382 | 29.789 | −17.060 | 18.297 | 1.00 | 16.17 A | C |
| ATOM | 6089 | CB | PRO | A | 382 | 30.430 | −16.303 | 17.131 | 1.00 | 16.16 A | C |

TABLE 8-2-continued

Coordinates for L494P Structure

| | | | | | | | | | | | | |
|---|---|---|---|---|---|---|---|---|---|---|---|---|
| ATOM | 6092 | CG | PRO | A | 382 | 31.535 | −15.532 | 17.747 | 1.00 | 15.98 | A | C |
| ATOM | 6095 | CD | PRO | A | 382 | 31.022 | −15.120 | 19.086 | 1.00 | 16.01 | A | C |
| ATOM | 6098 | C | PRO | A | 382 | 30.369 | −18.470 | 18.385 | 1.00 | 16.25 | A | C |
| ATOM | 6099 | O | PRO | A | 382 | 31.442 | −18.665 | 18.963 | 1.00 | 16.33 | A | O |
| ATOM | 6100 | N | THR | A | 383 | 29.662 | −19.439 | 17.807 | 1.00 | 16.20 | A | N |
| ATOM | 6101 | CA | THR | A | 383 | 30.120 | −20.828 | 17.800 | 1.00 | 15.92 | A | C |
| ATOM | 6103 | CB | THR | A | 383 | 29.044 | −21.794 | 17.251 | 1.00 | 15.85 | A | C |
| ATOM | 6105 | OG1 | THR | A | 383 | 28.676 | −21.409 | 15.920 | 1.00 | 14.24 | A | O |
| ATOM | 6107 | CG2 | THR | A | 383 | 27.807 | −21.793 | 18.147 | 1.00 | 15.69 | A | C |
| ATOM | 6111 | C | THR | A | 383 | 31.387 | −20.962 | 16.964 | 1.00 | 15.82 | A | C |
| ATOM | 6112 | O | THR | A | 383 | 31.668 | −20.120 | 16.111 | 1.00 | 15.84 | A | O |
| ATOM | 6114 | N | PHE | A | 384 | 32.148 | −22.021 | 17.219 | 1.00 | 15.86 | A | N |
| ATOM | 6115 | CA | PHE | A | 384 | 33.401 | −22.274 | 16.508 | 1.00 | 15.78 | A | C |
| ATOM | 6117 | CB | PHE | A | 384 | 33.909 | −23.687 | 16.812 | 1.00 | 15.96 | A | C |
| ATOM | 6120 | CG | PHE | A | 384 | 35.097 | −24.097 | 15.987 | 1.00 | 15.25 | A | C |
| ATOM | 6121 | CD1 | PHE | A | 384 | 36.337 | −23.510 | 16.195 | 1.00 | 15.45 | A | C |
| ATOM | 6123 | CE1 | PHE | A | 384 | 37.439 | −23.887 | 15.438 | 1.00 | 15.15 | A | C |
| ATOM | 6125 | CZ | PHE | A | 384 | 37.305 | −24.858 | 14.464 | 1.00 | 14.65 | A | C |
| ATOM | 6127 | CE2 | PHE | A | 384 | 36.072 | −25.450 | 14.247 | 1.00 | 14.59 | A | C |
| ATOM | 6129 | CD2 | PHE | A | 384 | 34.977 | −25.070 | 15.007 | 1.00 | 14.05 | A | C |
| ATOM | 6131 | C | PHE | A | 384 | 33.251 | −22.101 | 15.002 | 1.00 | 15.75 | A | C |
| ATOM | 6132 | O | PHE | A | 384 | 34.061 | −21.426 | 14.371 | 1.00 | 15.67 | A | O |
| ATOM | 6134 | N | ASP | A | 385 | 32.206 | −22.704 | 14.439 | 1.00 | 15.83 | A | N |
| ATOM | 6135 | CA | ASP | A | 385 | 31.997 | −22.699 | 12.990 | 1.00 | 15.78 | A | C |
| ATOM | 6137 | CB | ASP | A | 385 | 30.956 | −23.755 | 12.593 | 1.00 | 15.57 | A | C |
| ATOM | 6140 | CG | ASP | A | 385 | 31.473 | −25.179 | 12.750 | 1.00 | 14.28 | A | C |
| ATOM | 6141 | OD1 | ASP | A | 385 | 32.696 | −25.397 | 12.644 | 1.00 | 14.47 | A | O |
| ATOM | 6142 | OD2 | ASP | A | 385 | 30.656 | −26.092 | 12.971 | 1.00 | 13.30 | A | O |
| ATOM | 6143 | C | ASP | A | 385 | 31.618 | −21.329 | 12.420 | 1.00 | 16.22 | A | C |
| ATOM | 6144 | O | ASP | A | 385 | 31.727 | −21.121 | 11.215 | 1.00 | 16.29 | A | O |
| ATOM | 6146 | N | ASP | A | 386 | 31.178 | −20.403 | 13.272 | 1.00 | 17.06 | A | N |
| ATOM | 6147 | CA | ASP | A | 386 | 30.967 | −19.011 | 12.854 | 1.00 | 18.04 | A | C |
| ATOM | 6149 | CB | ASP | A | 386 | 29.900 | −18.310 | 13.711 | 1.00 | 18.36 | A | C |
| ATOM | 6152 | CG | ASP | A | 386 | 28.490 | −18.461 | 13.146 | 1.00 | 19.49 | A | C |
| ATOM | 6153 | OD1 | ASP | A | 386 | 28.242 | −19.410 | 12.369 | 1.00 | 21.38 | A | O |
| ATOM | 6154 | OD2 | ASP | A | 386 | 27.625 | −17.625 | 13.489 | 1.00 | 18.48 | A | O |
| ATOM | 6155 | C | ASP | A | 386 | 32.271 | −18.223 | 12.910 | 1.00 | 18.63 | A | C |
| ATOM | 6156 | O | ASP | A | 386 | 32.644 | −17.582 | 11.930 | 1.00 | 19.56 | A | O |
| ATOM | 6158 | N | TYR | A | 387 | 32.962 | −18.265 | 14.048 | 1.00 | 19.03 | A | N |
| ATOM | 6159 | CA | TYR | A | 387 | 34.237 | −17.556 | 14.182 | 1.00 | 19.44 | A | C |
| ATOM | 6161 | CB | TYR | A | 387 | 34.793 | −17.629 | 15.614 | 1.00 | 19.51 | A | C |
| ATOM | 6164 | CG | TYR | A | 387 | 36.142 | −16.950 | 15.762 | 1.00 | 21.18 | A | C |
| ATOM | 6165 | CD1 | TYR | A | 387 | 36.235 | −15.576 | 15.975 | 1.00 | 22.72 | A | C |
| ATOM | 6167 | CE1 | TYR | A | 387 | 37.476 | −14.945 | 16.095 | 1.00 | 24.66 | A | C |
| ATOM | 6169 | CZ | TYR | A | 387 | 38.641 | −15.695 | 15.996 | 1.00 | 25.02 | A | C |
| ATOM | 6170 | OH | TYR | A | 387 | 39.870 | −15.084 | 16.116 | 1.00 | 24.90 | A | O |
| ATOM | 6172 | CE2 | TYR | A | 387 | 38.573 | −17.060 | 15.778 | 1.00 | 24.35 | A | C |
| ATOM | 6174 | CD2 | TYR | A | 387 | 37.328 | −17.680 | 15.661 | 1.00 | 23.39 | A | C |
| ATOM | 6176 | C | TYR | A | 387 | 35.273 | −18.089 | 13.188 | 1.00 | 19.48 | A | C |
| ATOM | 6177 | O | TYR | A | 387 | 35.892 | −17.311 | 12.462 | 1.00 | 19.69 | A | O |
| ATOM | 6179 | N | PHE | A | 388 | 35.451 | −19.409 | 13.155 | 1.00 | 19.44 | A | N |
| ATOM | 6180 | CA | PHE | A | 388 | 36.464 | −20.016 | 12.293 | 1.00 | 19.32 | A | C |
| ATOM | 6182 | CB | PHE | A | 388 | 36.682 | −21.490 | 12.626 | 1.00 | 19.39 | A | C |
| ATOM | 6185 | CG | PHE | A | 388 | 37.829 | −22.101 | 11.878 | 1.00 | 19.88 | A | C |
| ATOM | 6186 | CD1 | PHE | A | 388 | 39.135 | −21.824 | 12.251 | 1.00 | 19.14 | A | C |
| ATOM | 6188 | CE1 | PHE | A | 388 | 40.201 | −22.370 | 11.559 | 1.00 | 20.10 | A | C |
| ATOM | 6190 | CZ | PHE | A | 388 | 39.969 | −23.199 | 10.470 | 1.00 | 20.36 | A | C |
| ATOM | 6192 | CE2 | PHE | A | 388 | 38.669 | −23.476 | 10.080 | 1.00 | 20.47 | A | C |
| ATOM | 6194 | CD2 | PHE | A | 388 | 37.606 | −22.924 | 10.780 | 1.00 | 20.61 | A | C |
| ATOM | 6196 | C | PHE | A | 388 | 36.131 | −19.869 | 10.813 | 1.00 | 19.22 | A | C |
| ATOM | 6197 | O | PHE | A | 388 | 37.028 | −19.679 | 9.995 | 1.00 | 19.09 | A | O |
| ATOM | 6199 | N | GLY | A | 389 | 34.851 | −19.963 | 10.468 | 1.00 | 19.30 | A | N |
| ATOM | 6200 | CA | GLY | A | 389 | 34.411 | −19.671 | 9.106 | 1.00 | 19.45 | A | C |
| ATOM | 6203 | C | GLY | A | 389 | 34.924 | −18.310 | 8.665 | 1.00 | 19.46 | A | C |
| ATOM | 6204 | O | GLY | A | 389 | 35.561 | −18.186 | 7.616 | 1.00 | 19.53 | A | O |
| ATOM | 6206 | N | ASN | A | 390 | 34.662 | −17.297 | 9.491 | 1.00 | 19.12 | A | N |
| ATOM | 6207 | CA | ASN | A | 390 | 35.119 | −15.931 | 9.238 | 1.00 | 18.83 | A | C |
| ATOM | 6209 | CB | ASN | A | 390 | 34.388 | −14.955 | 10.163 | 1.00 | 18.64 | A | C |
| ATOM | 6212 | CG | ASN | A | 390 | 34.691 | −13.505 | 9.836 | 1.00 | 18.88 | A | C |
| ATOM | 6213 | OD1 | ASN | A | 390 | 34.151 | −12.949 | 8.882 | 1.00 | 20.54 | A | O |
| ATOM | 6214 | ND2 | ASN | A | 390 | 35.561 | −12.887 | 10.627 | 1.00 | 17.01 | A | N |
| ATOM | 6217 | C | ASN | A | 390 | 36.630 | −15.750 | 9.416 | 1.00 | 18.88 | A | C |
| ATOM | 6218 | O | ASN | A | 390 | 37.240 | −14.918 | 8.742 | 1.00 | 19.57 | A | O |
| ATOM | 6220 | N | ALA | A | 391 | 37.225 | −16.525 | 10.322 | 1.00 | 18.39 | A | N |
| ATOM | 6221 | CA | ALA | A | 391 | 38.636 | −16.365 | 10.688 | 1.00 | 17.65 | A | C |
| ATOM | 6223 | CB | ALA | A | 391 | 38.977 | −17.237 | 11.885 | 1.00 | 17.64 | A | C |
| ATOM | 6227 | C | ALA | A | 391 | 39.617 | −16.635 | 9.547 | 1.00 | 17.17 | A | C |
| ATOM | 6228 | O | ALA | A | 391 | 40.541 | −15.849 | 9.349 | 1.00 | 17.37 | A | O |

TABLE 8-2-continued

| Coordinates for L494P Structure | | | | | | | | | | | |
|---|---|---|---|---|---|---|---|---|---|---|---|
| ATOM | 6230 | N | TRP | A | 392 | 39.435 | −17.727 | 8.801 | 1.00 | 16.59 A | N |
| ATOM | 6231 | CA | TRP | A | 392 | 40.381 | −18.048 | 7.718 | 1.00 | 16.35 A | C |
| ATOM | 6233 | CB | TRP | A | 392 | 40.325 | −19.525 | 7.281 | 1.00 | 16.37 A | C |
| ATOM | 6236 | CG | TRP | A | 392 | 39.029 | −20.021 | 6.712 | 1.00 | 17.82 A | C |
| ATOM | 6237 | CD1 | TRP | A | 392 | 38.089 | −20.760 | 7.363 | 1.00 | 20.80 A | C |
| ATOM | 6239 | NE1 | TRP | A | 392 | 37.044 | −21.053 | 6.522 | 1.00 | 21.26 A | N |
| ATOM | 6241 | CE2 | TRP | A | 392 | 37.303 | −20.516 | 5.290 | 1.00 | 19.01 A | C |
| ATOM | 6242 | CD2 | TRP | A | 392 | 38.552 | −19.864 | 5.369 | 1.00 | 18.29 A | C |
| ATOM | 6243 | CE3 | TRP | A | 392 | 39.050 | −19.225 | 4.229 | 1.00 | 18.54 A | C |
| ATOM | 6245 | CZ3 | TRP | A | 392 | 38.297 | −19.258 | 3.066 | 1.00 | 18.44 A | C |
| ATOM | 6247 | CH2 | TRP | A | 392 | 37.060 | −19.914 | 3.021 | 1.00 | 18.84 A | C |
| ATOM | 6249 | CZ2 | TRP | A | 392 | 36.547 | −20.547 | 4.120 | 1.00 | 18.75 A | C |
| ATOM | 6251 | C | TRP | A | 392 | 40.272 | −17.093 | 6.521 | 1.00 | 15.96 A | C |
| ATOM | 6252 | O | TRP | A | 392 | 41.223 | −16.957 | 5.754 | 1.00 | 15.58 A | O |
| ATOM | 6254 | N | LYS | A | 393 | 39.131 | −16.427 | 6.367 | 1.00 | 16.07 A | N |
| ATOM | 6255 | CA | LYS | A | 393 | 39.018 | −15.339 | 5.389 | 1.00 | 16.20 A | C |
| ATOM | 6257 | CB | LYS | A | 393 | 37.556 | −15.051 | 5.034 | 1.00 | 16.58 A | C |
| ATOM | 6260 | CG | LYS | A | 393 | 36.893 | −16.149 | 4.211 | 1.00 | 18.39 A | C |
| ATOM | 6263 | CD | LYS | A | 393 | 35.609 | −15.652 | 3.561 | 1.00 | 21.72 A | C |
| ATOM | 6266 | CE | LYS | A | 393 | 34.704 | −16.803 | 3.139 | 1.00 | 22.15 A | C |
| ATOM | 6269 | NZ | LYS | A | 393 | 34.074 | −17.470 | 4.313 | 1.00 | 22.61 A | N |
| ATOM | 6273 | C | LYS | A | 393 | 39.699 | −14.068 | 5.902 | 1.00 | 15.28 A | C |
| ATOM | 6274 | O | LYS | A | 393 | 40.191 | −13.264 | 5.108 | 1.00 | 15.25 A | O |
| ATOM | 6276 | N | SER | A | 394 | 39.725 | −13.891 | 7.223 | 1.00 | 14.19 A | N |
| ATOM | 6277 | CA | SER | A | 394 | 40.438 | −12.768 | 7.836 | 1.00 | 13.88 A | C |
| ATOM | 6279 | CB | SER | A | 394 | 39.829 | −12.405 | 9.194 | 1.00 | 13.76 A | C |
| ATOM | 6282 | OG | SER | A | 394 | 40.198 | −13.331 | 10.198 | 1.00 | 14.47 A | O |
| ATOM | 6284 | C | SER | A | 394 | 41.938 | −13.043 | 7.987 | 1.00 | 13.51 A | C |
| ATOM | 6285 | O | SER | A | 394 | 42.696 | −12.149 | 8.359 | 1.00 | 13.98 A | O |
| ATOM | 6287 | N | SER | A | 395 | 42.363 | −14.275 | 7.711 | 1.00 | 12.98 A | N |
| ATOM | 6288 | CA | SER | A | 395 | 43.789 | −14.608 | 7.665 | 1.00 | 12.09 A | C |
| ATOM | 6290 | CB | SER | A | 395 | 43.987 | −16.115 | 7.484 | 1.00 | 11.72 A | C |
| ATOM | 6293 | OG | SER | A | 395 | 43.677 | −16.517 | 6.160 | 1.00 | 9.17 A | O |
| ATOM | 6295 | C | SER | A | 395 | 44.479 | −13.873 | 6.520 | 1.00 | 11.88 A | C |
| ATOM | 6296 | O | SER | A | 395 | 45.653 | −13.530 | 6.620 | 1.00 | 12.00 A | O |
| ATOM | 6298 | N | SER | A | 396 | 43.721 | −13.637 | 5.446 | 1.00 | 11.56 A | N |
| ATOM | 6299 | CA | SER | A | 396 | 44.212 | −13.063 | 4.189 | 1.00 | 11.42 A | C |
| ATOM | 6301 | CB | SER | A | 396 | 45.143 | −11.858 | 4.416 | 1.00 | 11.41 A | C |
| ATOM | 6304 | OG | SER | A | 396 | 46.494 | −12.252 | 4.580 | 1.00 | 10.83 A | O |
| ATOM | 6306 | C | SER | A | 396 | 44.887 | −14.131 | 3.325 | 1.00 | 11.35 A | C |
| ATOM | 6307 | O | SER | A | 396 | 45.498 | −13.814 | 2.300 | 1.00 | 11.18 A | O |
| ATOM | 6309 | N | GLY | A | 397 | 44.761 | −15.392 | 3.740 | 1.00 | 11.18 A | N |
| ATOM | 6310 | CA | GLY | A | 397 | 45.257 | −16.523 | 2.966 | 1.00 | 11.19 A | C |
| ATOM | 6313 | C | GLY | A | 397 | 44.591 | −16.607 | 1.605 | 1.00 | 11.20 A | C |
| ATOM | 6314 | O | GLY | A | 397 | 45.270 | −16.806 | 0.596 | 1.00 | 11.77 A | O |
| ATOM | 6316 | N | PRO | A | 398 | 43.254 | −16.458 | 1.565 | 1.00 | 10.58 A | N |
| ATOM | 6317 | CA | PRO | A | 398 | 42.574 | −16.415 | 0.279 | 1.00 | 10.32 A | C |
| ATOM | 6319 | CB | PRO | A | 398 | 41.095 | −16.282 | 0.665 | 1.00 | 10.50 A | C |
| ATOM | 6322 | CG | PRO | A | 398 | 41.013 | −16.848 | 2.032 | 1.00 | 10.24 A | C |
| ATOM | 6325 | CD | PRO | A | 398 | 42.295 | −16.448 | 2.683 | 1.00 | 10.64 A | C |
| ATOM | 6328 | C | PRO | A | 398 | 43.024 | −15.235 | −0.571 | 1.00 | 9.73 A | C |
| ATOM | 6329 | O | PRO | A | 398 | 43.301 | −15.405 | −1.755 | 1.00 | 9.10 A | O |
| ATOM | 6330 | N | LEU | A | 399 | 43.113 | −14.054 | 0.030 | 1.00 | 9.90 A | N |
| ATOM | 6331 | CA | LEU | A | 399 | 43.532 | −12.871 | −0.712 | 1.00 | 10.55 A | C |
| ATOM | 6333 | CB | LEU | A | 399 | 43.538 | −11.626 | 0.179 | 1.00 | 10.41 A | C |
| ATOM | 6336 | CG | LEU | A | 399 | 43.677 | −10.296 | −0.568 | 1.00 | 9.15 A | C |
| ATOM | 6338 | CD1 | LEU | A | 399 | 43.004 | −9.192 | 0.209 | 1.00 | 10.37 A | C |
| ATOM | 6342 | CD2 | LEU | A | 399 | 45.134 | −9.947 | −0.838 | 1.00 | 8.74 A | C |
| ATOM | 6346 | C | LEU | A | 399 | 44.911 | −13.095 | −1.322 | 1.00 | 11.44 A | C |
| ATOM | 6347 | O | LEU | A | 399 | 45.102 | −12.893 | −2.520 | 1.00 | 12.07 A | O |
| ATOM | 6349 | N | GLN | A | 400 | 45.861 | −13.534 | −0.500 | 1.00 | 11.78 A | N |
| ATOM | 6350 | CA | GLN | A | 400 | 47.230 | −13.779 | −0.966 | 1.00 | 12.03 A | C |
| ATOM | 6352 | CB | GLN | A | 400 | 48.106 | −14.301 | 0.176 | 1.00 | 12.44 A | C |
| ATOM | 6355 | CG | GLN | A | 400 | 48.616 | −13.216 | 1.117 | 1.00 | 12.64 A | C |
| ATOM | 6358 | CD | GLN | A | 400 | 49.595 | −13.754 | 2.141 | 1.00 | 11.76 A | C |
| ATOM | 6359 | OE1 | GLN | A | 400 | 50.554 | −14.442 | 1.799 | 1.00 | 11.16 A | O |
| ATOM | 6360 | NE2 | GLN | A | 400 | 49.353 | −13.447 | 3.407 | 1.00 | 12.59 A | N |
| ATOM | 6363 | C | GLN | A | 400 | 47.308 | −14.742 | −2.155 | 1.00 | 11.86 A | C |
| ATOM | 6364 | O | GLN | A | 400 | 48.147 | −14.574 | −3.038 | 1.00 | 11.52 A | O |
| ATOM | 6366 | N | LEU | A | 401 | 46.443 | −15.750 | −2.176 | 1.00 | 12.22 A | N |
| ATOM | 6367 | CA | LEU | A | 401 | 46.442 | −16.721 | −3.269 | 1.00 | 12.76 A | C |
| ATOM | 6369 | CB | LEU | A | 401 | 45.926 | −18.087 | −2.791 | 1.00 | 12.53 A | C |
| ATOM | 6372 | CG | LEU | A | 401 | 46.818 | −18.811 | −1.772 | 1.00 | 11.90 A | C |
| ATOM | 6374 | CD1 | LEU | A | 401 | 46.158 | −20.09 | −1.294 | 1.00 | 13.20 A | C |
| ATOM | 6378 | CD2 | LEU | A | 401 | 48.195 | −19.11 | −2.346 | 1.00 | 9.64 A | C |
| ATOM | 6382 | C | LEU | A | 401 | 45.649 | −16.225 | −4.485 | 1.00 | 13.27 A | C |
| ATOM | 6383 | O | LEU | A | 401 | 45.910 | −16.662 | −5.609 | 1.00 | 13.80 A | O |
| ATOM | 6385 | N | VAL | A | 402 | 44.693 | −15.320 | −4.272 | 1.00 | 13.43 A | N |

TABLE 8-2-continued

Coordinates for L494P Structure

| | | | | | | | | | | | | |
|---|---|---|---|---|---|---|---|---|---|---|---|---|
| ATOM | 6386 | CA | VAL | A | 402 | 43.968 | −14.700 | −5.391 | 1.00 | 13.52 | A | C |
| ATOM | 6388 | CB | VAL | A | 402 | 42.791 | −13.811 | −4.915 | 1.00 | 13.58 | A | C |
| ATOM | 6390 | CG1 | VAL | A | 402 | 41.759 | −14.647 | −4.186 | 1.00 | 14.22 | A | C |
| ATOM | 6394 | CG2 | VAL | A | 402 | 42.146 | −13.090 | −6.093 | 1.00 | 11.75 | A | C |
| ATOM | 6398 | C | VAL | A | 402 | 44.924 | −13.864 | −6.244 | 1.00 | 13.38 | A | C |
| ATOM | 6399 | O | VAL | A | 402 | 44.798 | −13.827 | −7.463 | 1.00 | 13.04 | A | O |
| ATOM | 6401 | N | PHE | A | 403 | 45.880 | −13.207 | −5.594 | 1.00 | 13.34 | A | N |
| ATOM | 6402 | CA | PHE | A | 403 | 46.916 | −12.455 | −6.301 | 1.00 | 13.95 | A | C |
| ATOM | 6404 | CB | PHE | A | 403 | 47.544 | −11.410 | −5.376 | 1.00 | 14.44 | A | C |
| ATOM | 6407 | CG | PHE | A | 403 | 46.673 | −10.206 | −5.155 | 1.00 | 14.69 | A | C |
| ATOM | 6408 | CD1 | PHE | A | 403 | 46.949 | −9.004 | −5.795 | 1.00 | 13.14 | A | C |
| ATOM | 6410 | CE1 | PHE | A | 403 | 46.140 | −7.903 | −5.598 | 1.00 | 13.57 | A | C |
| ATOM | 6412 | CZ | PHE | A | 403 | 45.035 | −7.999 | −4.763 | 1.00 | 14.00 | A | C |
| ATOM | 6414 | CE2 | PHE | A | 403 | 44.749 | −9.191 | −4.128 | 1.00 | 12.73 | A | C |
| ATOM | 6416 | CD2 | PHE | A | 403 | 45.560 | −10.285 | −4.328 | 1.00 | 12.55 | A | C |
| ATOM | 6418 | C | PHE | A | 403 | 47.991 | −13.378 | −6.867 | 1.00 | 13.90 | A | C |
| ATOM | 6419 | O | PHE | A | 403 | 48.496 | −13.154 | −7.971 | 1.00 | 13.60 | A | O |
| ATOM | 6421 | N | ALA | A | 404 | 48.335 | −14.411 | −6.101 | 1.00 | 14.11 | A | N |
| ATOM | 6422 | CA | ALA | A | 404 | 49.301 | −15.419 | −6.533 | 1.00 | 14.01 | A | C |
| ATOM | 6424 | CB | ALA | A | 404 | 49.536 | −16.439 | −5.420 | 1.00 | 14.07 | A | C |
| ATOM | 6428 | C | ALA | A | 404 | 48.850 | −16.123 | −7.813 | 1.00 | 13.46 | A | C |
| ATOM | 6429 | O | ALA | A | 404 | 49.676 | −16.483 | −8.651 | 1.00 | 13.31 | A | O |
| ATOM | 6431 | N | TYR | A | 405 | 47.542 | −16.315 | −7.960 | 1.00 | 13.06 | A | N |
| ATOM | 6432 | CA | TYR | A | 405 | 46.990 | −16.912 | −9.172 | 1.00 | 13.33 | A | C |
| ATOM | 6434 | CB | TYR | A | 405 | 45.458 | −16.967 | −9.110 | 1.00 | 12.98 | A | C |
| ATOM | 6437 | CG | TYR | A | 405 | 44.842 | −17.457 | −10.398 | 1.00 | 11.28 | A | C |
| ATOM | 6438 | CD1 | TYR | A | 405 | 44.849 | −18.808 | −10.721 | 1.00 | 11.80 | A | C |
| ATOM | 6440 | CE1 | TYR | A | 405 | 44.297 | −19.269 | −11.914 | 1.00 | 11.52 | A | C |
| ATOM | 6442 | CZ | TYR | A | 405 | 43.741 | −18.369 | −12.801 | 1.00 | 10.95 | A | C |
| ATOM | 6443 | OH | TYR | A | 405 | 43.199 | −18.819 | −13.980 | 1.00 | 9.66 | A | O |
| ATOM | 6445 | CE2 | TYR | A | 405 | 43.729 | −17.016 | −12.505 | 1.00 | 11.40 | A | C |
| ATOM | 6447 | CD2 | TYR | A | 405 | 44.280 | −16.568 | −11.308 | 1.00 | 10.90 | A | C |
| ATOM | 6449 | C | TYR | A | 405 | 47.424 | −16.133 | −10.411 | 1.00 | 14.22 | A | C |
| ATOM | 6450 | O | TYR | A | 405 | 47.961 | −16.709 | −11.360 | 1.00 | 14.09 | A | O |
| ATOM | 6452 | N | PHE | A | 406 | 47.198 | −14.820 | −10.384 | 1.00 | 15.24 | A | N |
| ATOM | 6453 | CA | PHE | A | 406 | 47.442 | −13.958 | −11.546 | 1.00 | 15.22 | A | C |
| ATOM | 6455 | CB | PHE | A | 406 | 46.733 | −12.613 | −11.377 | 1.00 | 14.88 | A | C |
| ATOM | 6458 | CG | PHE | A | 406 | 45.237 | −12.722 | −11.317 | 1.00 | 13.53 | A | C |
| ATOM | 6459 | CD1 | PHE | A | 406 | 44.504 | −13.009 | −12.458 | 1.00 | 13.38 | A | C |
| ATOM | 6461 | CE1 | PHE | A | 406 | 43.126 | −13.107 | −12.408 | 1.00 | 12.53 | A | C |
| ATOM | 6463 | CZ | PHE | A | 406 | 42.465 | −12.913 | −11.210 | 1.00 | 12.19 | A | C |
| ATOM | 6465 | CE2 | PHE | A | 406 | 43.186 | −12.623 | −10.068 | 1.00 | 11.97 | A | C |
| ATOM | 6467 | CD2 | PHE | A | 406 | 44.563 | −12.528 | −10.126 | 1.00 | 11.83 | A | C |
| ATOM | 6469 | C | PHE | A | 406 | 48.922 | −13.717 | −11.831 | 1.00 | 15.89 | A | C |
| ATOM | 6470 | O | PHE | A | 406 | 49.267 | −13.239 | −12.912 | 1.00 | 16.18 | A | O |
| ATOM | 6472 | N | ALA | A | 407 | 49.789 | −14.025 | −10.868 | 1.00 | 16.30 | A | N |
| ATOM | 6473 | CA | ALA | A | 407 | 51.230 | −13.919 | −11.078 | 1.00 | 16.47 | A | C |
| ATOM | 6475 | CB | ALA | A | 407 | 51.945 | −13.724 | −9.764 | 1.00 | 16.54 | A | C |
| ATOM | 6479 | C | ALA | A | 407 | 51.764 | −15.156 | −11.785 | 1.00 | 17.01 | A | C |
| ATOM | 6480 | O | ALA | A | 407 | 52.403 | −15.039 | −12.828 | 1.00 | 17.63 | A | O |
| ATOM | 6482 | N | VAL | A | 408 | 51.479 | −16.333 | −11.227 | 1.00 | 17.52 | A | N |
| ATOM | 6483 | CA | VAL | A | 408 | 52.125 | −17.582 | −11.661 | 1.00 | 18.18 | A | C |
| ATOM | 6485 | CB | VAL | A | 408 | 52.196 | −18.620 | −10.509 | 1.00 | 18.02 | A | C |
| ATOM | 6487 | CG1 | VAL | A | 408 | 52.962 | −18.048 | −9.323 | 1.00 | 17.51 | A | C |
| ATOM | 6491 | CG2 | VAL | A | 408 | 50.808 | −19.070 | −10.091 | 1.00 | 17.56 | A | C |
| ATOM | 6495 | C | VAL | A | 408 | 51.510 | −18.259 | −12.896 | 1.00 | 19.13 | A | C |
| ATOM | 6496 | O | VAL | A | 408 | 52.226 | −18.899 | −13.665 | 1.00 | 19.26 | A | O |
| ATOM | 6498 | N | VAL | A | 409 | 50.201 | −18.127 | −13.088 | 1.00 | 20.36 | A | N |
| ATOM | 6499 | CA | VAL | A | 409 | 49.523 | −18.799 | −14.203 | 1.00 | 21.49 | A | C |
| ATOM | 6501 | CB | VAL | A | 409 | 48.010 | −18.951 | −13.934 | 1.00 | 21.39 | A | C |
| ATOM | 6503 | CG1 | VAL | A | 409 | 47.353 | −19.765 | −15.036 | 1.00 | 22.15 | A | C |
| ATOM | 6507 | CG2 | VAL | A | 409 | 47.771 | −19.611 | −12.584 | 1.00 | 22.07 | A | C |
| ATOM | 6511 | C | VAL | A | 409 | 49.722 | −18.038 | −15.521 | 1.00 | 22.53 | A | C |
| ATOM | 6512 | O | VAL | A | 409 | 49.629 | −16.808 | −15.547 | 1.00 | 23.27 | A | O |
| ATOM | 6514 | N | GLN | A | 410 | 49.994 | −18.768 | −16.607 | 1.00 | 23.04 | A | N |
| ATOM | 6515 | CA | GLN | A | 410 | 50.117 | −18.159 | −17.940 | 1.00 | 23.44 | A | C |
| ATOM | 6517 | CB | GLN | A | 410 | 50.609 | −19.176 | −18.988 | 1.00 | 23.94 | A | C |
| ATOM | 6520 | CG | GLN | A | 410 | 52.109 | −19.114 | −19.307 | 1.00 | 25.78 | A | C |
| ATOM | 6523 | CD | GLN | A | 410 | 52.465 | −19.825 | −20.619 | 1.00 | 27.06 | A | C |
| ATOM | 6524 | OE1 | GLN | A | 410 | 52.543 | −21.055 | −20.676 | 1.00 | 27.24 | A | O |
| ATOM | 6525 | NE2 | GLN | A | 410 | 52.688 | −19.047 | −21.675 | 1.00 | 25.76 | A | N |
| ATOM | 6528 | C | GLN | A | 410 | 48.782 | −17.546 | −18.378 | 1.00 | 23.54 | A | C |
| ATOM | 6529 | O | GLN | A | 410 | 48.589 | −16.335 | −18.271 | 1.00 | 23.64 | A | O |
| ATOM | 6531 | N | ASN | A | 411 | 47.864 | −18.385 | −18.853 | 1.00 | 23.79 | A | N |
| ATOM | 6532 | CA | ASN | A | 411 | 46.560 | −17.921 | −19.321 | 1.00 | 23.91 | A | C |
| ATOM | 6534 | CB | ASN | A | 411 | 46.095 | −18.734 | −20.535 | 1.00 | 24.06 | A | C |
| ATOM | 6537 | CG | ASN | A | 411 | 46.913 | −18.446 | −21.784 | 1.00 | 24.54 | A | C |
| ATOM | 6538 | OD1 | ASN | A | 411 | 46.413 | −17.859 | −22.745 | 1.00 | 23.89 | A | O |

TABLE 8-2-continued

Coordinates for L494P Structure

| | | | | | | | | | | | | |
|---|---|---|---|---|---|---|---|---|---|---|---|---|
| ATOM | 6539 | ND2 | ASN | A | 411 | 48.178 | −18.858 | −21.775 | 1.00 | 24.71 | A | N |
| ATOM | 6542 | C | ASN | A | 411 | 45.514 | −18.009 | −18.219 | 1.00 | 23.88 | A | C |
| ATOM | 6543 | O | ASN | A | 411 | 45.574 | −18.888 | −17.361 | 1.00 | 23.42 | A | O |
| ATOM | 6545 | N | ILE | A | 412 | 44.547 | −17.098 | −18.267 | 1.00 | 24.33 | A | N |
| ATOM | 6546 | CA | ILE | A | 412 | 43.466 | −17.042 | −17.285 | 1.00 | 24.54 | A | C |
| ATOM | 6548 | CB | ILE | A | 412 | 43.018 | −15.583 | −17.036 | 1.00 | 24.66 | A | C |
| ATOM | 6550 | CG1 | ILE | A | 412 | 44.224 | −14.686 | −16.727 | 1.00 | 24.61 | A | C |
| ATOM | 6553 | CD1 | ILE | A | 412 | 45.133 | −15.218 | −15.646 | 1.00 | 24.33 | A | C |
| ATOM | 6557 | CG2 | ILE | A | 412 | 41.997 | −15.516 | −15.910 | 1.00 | 25.28 | A | C |
| ATOM | 6561 | C | ILE | A | 412 | 42.267 | −17.841 | −17.788 | 1.00 | 24.52 | A | C |
| ATOM | 6562 | O | ILE | A | 412 | 41.795 | −17.612 | −18.901 | 1.00 | 24.75 | A | O |
| ATOM | 6564 | N | LYS | A | 413 | 41.776 | −18.771 | −16.973 | 1.00 | 24.56 | A | N |
| ATOM | 6565 | CA | LYS | A | 413 | 40.589 | −19.552 | −17.323 | 1.00 | 24.82 | A | C |
| ATOM | 6567 | CB | LYS | A | 413 | 40.819 | −21.041 | −17.055 | 1.00 | 25.06 | A | C |
| ATOM | 6570 | CG | LYS | A | 413 | 42.016 | −21.623 | −17.795 | 1.00 | 25.64 | A | C |
| ATOM | 6573 | CD | LYS | A | 413 | 41.849 | −23.112 | −18.064 | 1.00 | 28.37 | A | C |
| ATOM | 6576 | CE | LYS | A | 413 | 42.855 | −23.606 | −19.100 | 1.00 | 30.53 | A | C |
| ATOM | 6579 | NZ | LYS | A | 413 | 42.618 | −25.028 | −19.493 | 1.00 | 30.83 | A | N |
| ATOM | 6583 | C | LYS | A | 413 | 39.389 | −19.053 | −16.530 | 1.00 | 24.68 | A | C |
| ATOM | 6584 | O | LYS | A | 413 | 39.521 | −18.714 | −15.352 | 1.00 | 23.95 | A | O |
| ATOM | 6586 | N | LYS | A | 414 | 38.225 | −19.005 | −17.176 | 1.00 | 25.21 | A | N |
| ATOM | 6587 | CA | LYS | A | 414 | 37.006 | −18.530 | −16.517 | 1.00 | 25.78 | A | C |
| ATOM | 6589 | CB | LYS | A | 414 | 35.845 | −18.387 | −17.509 | 1.00 | 25.92 | A | C |
| ATOM | 6592 | CG | LYS | A | 414 | 34.681 | −17.556 | −16.956 | 1.00 | 27.75 | A | C |
| ATOM | 6595 | CD | LYS | A | 414 | 33.572 | −17.312 | −17.982 | 1.00 | 28.34 | A | C |
| ATOM | 6598 | CE | LYS | A | 414 | 32.817 | −18.588 | −18.334 | 1.00 | 28.85 | A | C |
| ATOM | 6601 | NZ | LYS | A | 414 | 32.295 | −19.301 | −17.133 | 1.00 | 28.73 | A | N |
| ATOM | 6605 | C | LYS | A | 414 | 36.612 | −19.462 | −15.371 | 1.00 | 25.94 | A | C |
| ATOM | 6606 | O | LYS | A | 414 | 36.215 | −18.997 | −14.301 | 1.00 | 26.04 | A | O |
| ATOM | 6608 | N | GLU | A | 415 | 36.734 | −20.771 | −15.598 | 1.00 | 25.93 | A | N |
| ATOM | 6609 | CA | GLU | A | 415 | 36.443 | −21.772 | −14.567 | 1.00 | 25.59 | A | C |
| ATOM | 6611 | CB | GLU | A | 415 | 36.571 | −23.194 | −15.129 | 1.00 | 25.91 | A | C |
| ATOM | 6614 | CG | GLU | A | 415 | 35.980 | −24.278 | −14.212 | 1.00 | 27.72 | A | C |
| ATOM | 6617 | CD | GLU | A | 415 | 36.785 | −25.576 | −14.192 | 1.00 | 29.56 | A | C |
| ATOM | 6618 | OE1 | GLU | A | 415 | 38.035 | −25.519 | −14.216 | 1.00 | 30.42 | A | O |
| ATOM | 6619 | OE2 | GLU | A | 415 | 36.160 | −26.658 | −14.127 | 1.00 | 30.95 | A | O |
| ATOM | 6620 | C | GLU | A | 415 | 37.375 | −21.614 | −13.367 | 1.00 | 24.71 | A | C |
| ATOM | 6621 | O | GLU | A | 415 | 36.925 | −21.641 | −12.221 | 1.00 | 24.35 | A | O |
| ATOM | 6623 | N | GLU | A | 416 | 38.668 | −21.455 | −13.635 | 1.00 | 24.19 | A | N |
| ATOM | 6624 | CA | GLU | A | 416 | 39.653 | −21.259 | −12.574 | 1.00 | 24.24 | A | C |
| ATOM | 6626 | CB | GLU | A | 416 | 41.062 | −21.074 | −13.151 | 1.00 | 24.41 | A | C |
| ATOM | 6629 | CG | GLU | A | 416 | 41.712 | −22.376 | −13.612 | 1.00 | 25.81 | A | C |
| ATOM | 6632 | CD | GLU | A | 416 | 43.177 | −22.214 | −13.985 | 1.00 | 26.72 | A | C |
| ATOM | 6633 | OE1 | GLU | A | 416 | 43.547 | −21.142 | −14.507 | 1.00 | 27.38 | A | O |
| ATOM | 6634 | OE2 | GLU | A | 416 | 43.958 | −23.166 | −13.764 | 1.00 | 26.58 | A | O |
| ATOM | 6635 | C | GLU | A | 416 | 39.291 | −20.077 | −11.673 | 1.00 | 23.98 | A | C |
| ATOM | 6636 | O | GLU | A | 416 | 39.215 | −20.232 | −10.454 | 1.00 | 23.87 | A | O |
| ATOM | 6638 | N | ILE | A | 417 | 39.052 | −18.910 | −12.269 | 1.00 | 23.83 | A | N |
| ATOM | 6639 | CA | ILE | A | 417 | 38.704 | −17.719 | −11.484 | 1.00 | 23.96 | A | C |
| ATOM | 6641 | CB | ILE | A | 417 | 38.800 | −16.395 | −12.301 | 1.00 | 24.26 | A | C |
| ATOM | 6643 | CG1 | ILE | A | 417 | 37.708 | −16.310 | −13.373 | 1.00 | 24.99 | A | C |
| ATOM | 6646 | CD1 | ILE | A | 417 | 37.647 | −14.966 | −14.065 | 1.00 | 24.44 | A | C |
| ATOM | 6650 | CG2 | ILE | A | 417 | 40.185 | −16.249 | −12.925 | 1.00 | 23.85 | A | C |
| ATOM | 6654 | C | ILE | A | 417 | 37.316 | −17.828 | −10.848 | 1.00 | 23.84 | A | C |
| ATOM | 6655 | O | ILE | A | 417 | 37.052 | −17.190 | −9.832 | 1.00 | 23.74 | A | O |
| ATOM | 6657 | N | GLU | A | 418 | 36.438 | −18.631 | −11.448 | 1.00 | 23.87 | A | N |
| ATOM | 6658 | CA | GLU | A | 418 | 35.107 | −18.886 | −10.882 | 1.00 | 24.02 | A | C |
| ATOM | 6660 | CB | GLU | A | 418 | 34.281 | −19.798 | −11.802 | 1.00 | 24.29 | A | C |
| ATOM | 6663 | CG | GLU | A | 418 | 32.821 | −19.382 | −11.980 | 1.00 | 25.56 | A | C |
| ATOM | 6666 | CD | GLU | A | 418 | 32.536 | −18.833 | −13.367 | 1.00 | 27.78 | A | C |
| ATOM | 6667 | OE1 | GLU | A | 418 | 32.836 | −19.536 | −14.358 | 1.00 | 29.63 | A | O |
| ATOM | 6668 | OE2 | GLU | A | 418 | 32.003 | −17.707 | −13.469 | 1.00 | 28.94 | A | O |
| ATOM | 6669 | C | GLU | A | 418 | 35.227 | −19.551 | −9.510 | 1.00 | 23.54 | A | C |
| ATOM | 6670 | O | GLU | A | 418 | 34.483 | −19.225 | −8.585 | 1.00 | 23.37 | A | O |
| ATOM | 6672 | N | ASN | A | 419 | 36.161 | −20.494 | −9.399 | 1.00 | 23.03 | A | N |
| ATOM | 6673 | CA | ASN | A | 419 | 36.414 | −21.200 | −8.144 | 1.00 | 22.72 | A | C |
| ATOM | 6675 | CB | ASN | A | 419 | 37.219 | −22.481 | −8.399 | 1.00 | 22.49 | A | C |
| ATOM | 6678 | CG | ASN | A | 419 | 36.353 | −23.621 | −8.901 | 1.00 | 21.26 | A | C |
| ATOM | 6679 | OD1 | ASN | A | 419 | 35.999 | −24.523 | −8.143 | 1.00 | 20.38 | A | O |
| ATOM | 6680 | ND2 | ASN | A | 419 | 35.994 | −23.577 | −10.176 | 1.00 | 18.71 | A | N |
| ATOM | 6683 | C | ASN | A | 419 | 37.110 | −20.332 | −7.094 | 1.00 | 22.76 | A | C |
| ATOM | 6684 | O | ASN | A | 419 | 36.831 | −20.460 | −5.901 | 1.00 | 22.68 | A | O |
| ATOM | 6686 | N | LEU | A | 420 | 38.007 | −19.450 | −7.535 | 1.00 | 23.02 | A | N |
| ATOM | 6687 | CA | LEU | A | 420 | 38.646 | −18.485 | −6.630 | 1.00 | 23.24 | A | C |
| ATOM | 6689 | CB | LEU | A | 420 | 39.740 | −17.689 | −7.352 | 1.00 | 23.12 | A | C |
| ATOM | 6692 | CG | LEU | A | 420 | 40.950 | −18.465 | −7.878 | 1.00 | 22.58 | A | C |
| ATOM | 6694 | CD1 | LEU | A | 420 | 41.884 | −17.542 | −8.649 | 1.00 | 23.76 | A | C |
| ATOM | 6698 | CD2 | LEU | A | 420 | 41.694 | −19.150 | −6.747 | 1.00 | 21.73 | A | C |

TABLE 8-2-continued

Coordinates for L494P Structure

| | | | | | | | | | | | | |
|---|---|---|---|---|---|---|---|---|---|---|---|---|
| ATOM | 6702 | C | LEU | A | 420 | 37.616 | −17.519 | −6.037 | 1.00 | 23.34 | A | C |
| ATOM | 6703 | O | LEU | A | 420 | 37.698 | −17.159 | −4.862 | 1.00 | 23.29 | A | O |
| ATOM | 6705 | N | GLN | A | 421 | 36.649 | −17.113 | −6.859 | 1.00 | 23.39 | A | N |
| ATOM | 6706 | CA | GLN | A | 421 | 35.555 | −16.240 | −6.426 | 1.00 | 23.61 | A | C |
| ATOM | 6708 | CB | GLN | A | 421 | 34.664 | −15.883 | −7.619 | 1.00 | 23.81 | A | C |
| ATOM | 6711 | CG | GLN | A | 421 | 35.317 | −14.977 | −8.655 | 1.00 | 25.57 | A | C |
| ATOM | 6714 | CD | GLN | A | 421 | 35.021 | −13.508 | −8.426 | 1.00 | 27.53 | A | C |
| ATOM | 6715 | OE1 | GLN | A | 421 | 34.355 | −12.867 | −9.241 | 1.00 | 27.80 | A | O |
| ATOM | 6716 | NE2 | GLN | A | 421 | 35.507 | −12.967 | −7.310 | 1.00 | 28.75 | A | N |
| ATOM | 6719 | C | GLN | A | 421 | 34.687 | −16.871 | −5.336 | 1.00 | 23.75 | A | C |
| ATOM | 6720 | O | GLN | A | 421 | 34.012 | −16.160 | −4.594 | 1.00 | 23.75 | A | O |
| ATOM | 6722 | N | LYS | A | 422 | 34.699 | −18.202 | −5.254 | 1.00 | 24.07 | A | N |
| ATOM | 6723 | CA | LYS | A | 422 | 33.875 | −18.944 | −4.301 | 1.00 | 24.27 | A | C |
| ATOM | 6725 | CB | LYS | A | 422 | 33.053 | −19.995 | −5.060 | 1.00 | 24.49 | A | C |
| ATOM | 6728 | CG | LYS | A | 422 | 32.059 | −19.388 | −6.053 | 1.00 | 26.08 | A | C |
| ATOM | 6731 | CD | LYS | A | 422 | 31.640 | −20.375 | −7.140 | 1.00 | 28.24 | A | C |
| ATOM | 6734 | CE | LYS | A | 422 | 30.776 | −19.693 | −8.205 | 1.00 | 28.90 | A | C |
| ATOM | 6737 | NZ | LYS | A | 422 | 30.279 | −20.642 | −9.246 | 1.00 | 28.82 | A | N |
| ATOM | 6741 | C | LYS | A | 422 | 34.716 | −19.603 | −3.196 | 1.00 | 23.98 | A | C |
| ATOM | 6742 | O | LYS | A | 422 | 34.248 | −20.524 | −2.519 | 1.00 | 23.87 | A | O |
| ATOM | 6744 | N | TYR | A | 423 | 35.942 | −19.107 | −3.005 | 1.00 | 23.57 | A | N |
| ATOM | 6745 | CA | TYR | A | 423 | 36.902 | −19.675 | −2.046 | 1.00 | 23.15 | A | C |
| ATOM | 6747 | CB | TYR | A | 423 | 36.697 | −19.077 | −0.643 | 1.00 | 22.87 | A | C |
| ATOM | 6750 | CG | TYR | A | 423 | 36.761 | −17.559 | −0.637 | 1.00 | 23.55 | A | C |
| ATOM | 6751 | CD1 | TYR | A | 423 | 37.857 | −16.888 | −1.182 | 1.00 | 24.97 | A | C |
| ATOM | 6753 | CE1 | TYR | A | 423 | 37.919 | −15.497 | −1.197 | 1.00 | 24.81 | A | C |
| ATOM | 6755 | CZ | TYR | A | 423 | 36.880 | −14.761 | −0.660 | 1.00 | 24.32 | A | C |
| ATOM | 6756 | OH | TYR | A | 423 | 36.945 | −13.388 | −0.673 | 1.00 | 23.63 | A | O |
| ATOM | 6758 | CE2 | TYR | A | 423 | 35.782 | −15.400 | −0.110 | 1.00 | 23.79 | A | C |
| ATOM | 6760 | CD2 | TYR | A | 423 | 35.726 | −16.794 | −0.102 | 1.00 | 24.22 | A | C |
| ATOM | 6762 | C | TYR | A | 423 | 36.847 | −21.206 | −2.046 | 1.00 | 22.87 | A | C |
| ATOM | 6763 | O | TYR | A | 423 | 36.540 | −21.849 | −1.038 | 1.00 | 23.25 | A | O |
| ATOM | 6765 | N | HIS | A | 424 | 37.144 | −21.765 | −3.214 | 1.00 | 22.22 | A | N |
| ATOM | 6766 | CA | HIS | A | 424 | 37.125 | −23.205 | −3.449 | 1.00 | 21.90 | A | C |
| ATOM | 6768 | CB | HIS | A | 424 | 37.276 | −23.465 | −4.956 | 1.00 | 22.14 | A | C |
| ATOM | 6771 | CG | HIS | A | 424 | 37.467 | −24.904 | −5.320 | 1.00 | 23.25 | A | C |
| ATOM | 6772 | ND1 | HIS | A | 424 | 38.681 | −25.408 | −5.734 | 1.00 | 23.32 | A | N |
| ATOM | 6774 | CE1 | HIS | A | 424 | 38.555 | −26.698 | −5.989 | 1.00 | 23.99 | A | C |
| ATOM | 6776 | NE2 | HIS | A | 424 | 37.303 | −27.049 | −5.758 | 1.00 | 24.51 | A | N |
| ATOM | 6778 | CD2 | HIS | A | 424 | 36.600 | −25.944 | −5.341 | 1.00 | 24.99 | A | C |
| ATOM | 6780 | C | HIS | A | 424 | 38.232 | −23.894 | −2.652 | 1.00 | 21.23 | A | C |
| ATOM | 6781 | O | HIS | A | 424 | 39.226 | −23.266 | −2.293 | 1.00 | 21.22 | A | O |
| ATOM | 6783 | N | ASP | A | 425 | 38.042 | −25.184 | −2.383 | 1.00 | 20.88 | A | N |
| ATOM | 6784 | CA | ASP | A | 425 | 38.963 | −25.991 | −1.561 | 1.00 | 20.94 | A | C |
| ATOM | 6786 | CB | ASP | A | 425 | 38.655 | −27.491 | −1.731 | 1.00 | 21.19 | A | C |
| ATOM | 6789 | CG | ASP | A | 425 | 37.337 | −27.908 | −1.083 | 1.00 | 22.84 | A | C |
| ATOM | 6790 | OD1 | ASP | A | 425 | 36.714 | −27.086 | −0.374 | 1.00 | 27.02 | A | O |
| ATOM | 6791 | OD2 | ASP | A | 425 | 36.923 | −29.070 | −1.284 | 1.00 | 23.18 | A | O |
| ATOM | 6792 | C | ASP | A | 425 | 40.467 | −25.759 | −1.800 | 1.00 | 20.30 | A | C |
| ATOM | 6793 | O | ASP | A | 425 | 41.253 | −25.806 | −0.851 | 1.00 | 20.33 | A | O |
| ATOM | 6795 | N | THR | A | 426 | 40.870 | −25.519 | −3.046 | 1.00 | 19.20 | A | N |
| ATOM | 6796 | CA | THR | A | 426 | 42.295 | −25.401 | −3.366 | 1.00 | 18.17 | A | C |
| ATOM | 6798 | CB | THR | A | 426 | 42.546 | −25.212 | −4.878 | 1.00 | 17.95 | A | C |
| ATOM | 6800 | OG1 | THR | A | 426 | 41.842 | −26.219 | −5.612 | 1.00 | 17.41 | A | O |
| ATOM | 6802 | CG2 | THR | A | 426 | 44.033 | −25.315 | −5.196 | 1.00 | 15.99 | A | C |
| ATOM | 6806 | C | THR | A | 426 | 42.960 | −24.263 | −2.597 | 1.00 | 17.94 | A | C |
| ATOM | 6807 | O | THR | A | 426 | 44.085 | −24.424 | −2.127 | 1.00 | 18.23 | A | O |
| ATOM | 6809 | N | ILE | A | 427 | 42.270 | −23.127 | −2.471 | 1.00 | 17.76 | A | N |
| ATOM | 6810 | CA | ILE | A | 427 | 42.795 | −21.979 | −1.711 | 1.00 | 17.88 | A | C |
| ATOM | 6812 | CB | ILE | A | 427 | 42.699 | −20.642 | −2.499 | 1.00 | 17.38 | A | C |
| ATOM | 6814 | CG1 | ILE | A | 427 | 41.246 | −20.209 | −2.701 | 1.00 | 16.70 | A | C |
| ATOM | 6817 | CD1 | ILE | A | 427 | 41.119 | −18.858 | −3.365 | 1.00 | 16.78 | A | C |
| ATOM | 6821 | CG2 | ILE | A | 427 | 43.415 | −20.755 | −3.836 | 1.00 | 16.09 | A | C |
| ATOM | 6825 | C | ILE | A | 427 | 42.137 | −21.803 | −0.339 | 1.00 | 18.62 | A | C |
| ATOM | 6826 | O | ILE | A | 427 | 42.602 | −20.996 | 0.471 | 1.00 | 19.27 | A | O |
| ATOM | 6828 | N | SER | A | 428 | 41.065 | −22.550 | −0.082 | 1.00 | 18.85 | A | N |
| ATOM | 6829 | CA | SER | A | 428 | 40.426 | −22.561 | 1.233 | 1.00 | 19.03 | A | C |
| ATOM | 6831 | CB | SER | A | 428 | 39.035 | −23.200 | 1.145 | 1.00 | 18.90 | A | C |
| ATOM | 6834 | OG | SER | A | 428 | 38.499 | −23.466 | 2.429 | 1.00 | 19.43 | A | O |
| ATOM | 6836 | C | SER | A | 428 | 41.291 | −23.317 | 2.241 | 1.00 | 19.40 | A | C |
| ATOM | 6837 | O | SER | A | 428 | 41.671 | −22.772 | 3.274 | 1.00 | 19.21 | A | O |
| ATOM | 6839 | N | ARG | A | 429 | 41.614 | −24.566 | 1.914 | 1.00 | 20.31 | A | N |
| ATOM | 6840 | CA | ARG | A | 429 | 42.331 | −25.465 | 2.833 | 1.00 | 20.92 | A | C |
| ATOM | 6842 | CB | ARG | A | 429 | 42.587 | −26.839 | 2.185 | 1.00 | 21.25 | A | C |
| ATOM | 6845 | CG | ARG | A | 429 | 41.326 | −27.586 | 1.733 | 1.00 | 23.47 | A | C |
| ATOM | 6848 | CD | ARG | A | 429 | 40.833 | −28.594 | 2.762 | 1.00 | 26.54 | A | C |
| ATOM | 6851 | NE | ARG | A | 429 | 39.381 | −28.778 | 2.710 | 1.00 | 28.25 | A | N |
| ATOM | 6853 | CZ | ARG | A | 429 | 38.719 | −29.394 | 1.730 | 1.00 | 29.99 | A | C |

TABLE 8-2-continued

Coordinates for L494P Structure

| | | | | | | | | | | | | |
|---|---|---|---|---|---|---|---|---|---|---|---|---|
| ATOM | 6854 | NH1 | ARG | A | 429 | 39.359 | −29.903 | 0.676 | 1.00 | 29.63 | A | N |
| ATOM | 6857 | NH2 | ARG | A | 429 | 37.396 | −29.497 | 1.801 | 1.00 | 30.83 | A | N |
| ATOM | 6860 | C | ARG | A | 429 | 43.649 | −24.871 | 3.347 | 1.00 | 20.52 | A | C |
| ATOM | 6861 | O | ARG | A | 429 | 43.869 | −24.835 | 4.555 | 1.00 | 20.89 | A | O |
| ATOM | 6863 | N | PRO | A | 430 | 44.524 | −24.388 | 2.442 | 1.00 | 19.92 | A | N |
| ATOM | 6864 | CA | PRO | A | 430 | 45.782 | −23.822 | 2.933 | 1.00 | 19.69 | A | C |
| ATOM | 6866 | CB | PRO | A | 430 | 46.451 | −23.278 | 1.664 | 1.00 | 19.80 | A | C |
| ATOM | 6869 | CG | PRO | A | 430 | 45.801 | −23.986 | 0.541 | 1.00 | 19.77 | A | C |
| ATOM | 6872 | CD | PRO | A | 430 | 44.400 | −24.245 | 0.982 | 1.00 | 20.08 | A | C |
| ATOM | 6875 | C | PRO | A | 430 | 45.558 | −22.695 | 3.934 | 1.00 | 19.44 | A | C |
| ATOM | 6876 | O | PRO | A | 430 | 46.314 | −22.573 | 4.898 | 1.00 | 19.69 | A | O |
| ATOM | 6877 | N | SER | A | 431 | 44.520 | −21.891 | 3.701 | 1.00 | 19.05 | A | N |
| ATOM | 6878 | CA | SER | A | 431 | 44.171 | −20.780 | 4.591 | 1.00 | 18.38 | A | C |
| ATOM | 6880 | CB | SER | A | 431 | 43.173 | −19.843 | 3.910 | 1.00 | 18.34 | A | C |
| ATOM | 6883 | OG | SER | A | 431 | 43.653 | −19.431 | 2.639 | 1.00 | 18.28 | A | O |
| ATOM | 6885 | C | SER | A | 431 | 43.610 | −21.273 | 5.925 | 1.00 | 17.67 | A | C |
| ATOM | 6886 | O | SER | A | 431 | 43.797 | −20.621 | 6.954 | 1.00 | 16.78 | A | O |
| ATOM | 6888 | N | HIS | A | 432 | 42.922 | −22.417 | 5.896 | 1.00 | 17.38 | A | N |
| ATOM | 6889 | CA | HIS | A | 432 | 42.501 | −23.105 | 7.121 | 1.00 | 17.22 | A | C |
| ATOM | 6891 | CB | HIS | A | 432 | 41.774 | −24.426 | 6.803 | 1.00 | 17.35 | A | C |
| ATOM | 6894 | CG | HIS | A | 432 | 40.354 | −24.255 | 6.353 | 1.00 | 16.88 | A | C |
| ATOM | 6895 | ND1 | HIS | A | 432 | 39.389 | −25.215 | 6.569 | 1.00 | 16.42 | A | N |
| ATOM | 6897 | CE1 | HIS | A | 432 | 38.237 | −24.799 | 6.074 | 1.00 | 16.45 | A | C |
| ATOM | 6899 | NE2 | HIS | A | 432 | 38.418 | −23.601 | 5.548 | 1.00 | 14.80 | A | N |
| ATOM | 6901 | CD2 | HIS | A | 432 | 39.733 | −23.236 | 5.712 | 1.00 | 16.06 | A | C |
| ATOM | 6903 | C | HIS | A | 432 | 43.723 | −23.383 | 8.002 | 1.00 | 16.93 | A | C |
| ATOM | 6904 | O | HIS | A | 432 | 43.687 | −23.163 | 9.215 | 1.00 | 16.68 | A | O |
| ATOM | 6906 | N | ILE | A | 433 | 44.800 | −23.862 | 7.378 | 1.00 | 16.43 | A | N |
| ATOM | 6907 | CA | ILE | A | 433 | 46.064 | −24.108 | 8.078 | 1.00 | 16.05 | A | C |
| ATOM | 6909 | CB | ILE | A | 433 | 47.080 | −24.877 | 7.189 | 1.00 | 16.29 | A | C |
| ATOM | 6911 | CG1 | ILE | A | 433 | 46.752 | −26.374 | 7.152 | 1.00 | 16.71 | A | C |
| ATOM | 6914 | CD1 | ILE | A | 433 | 45.604 | −26.727 | 6.261 | 1.00 | 15.49 | A | C |
| ATOM | 6918 | CG2 | ILE | A | 433 | 48.505 | −24.683 | 7.704 | 1.00 | 17.15 | A | C |
| ATOM | 6922 | C | ILE | A | 433 | 46.710 | −22.804 | 8.553 | 1.00 | 15.22 | A | C |
| ATOM | 6923 | O | ILE | A | 433 | 47.267 | −22.751 | 9.648 | 1.00 | 15.08 | A | O |
| ATOM | 6925 | N | PHE | A | 434 | 46.631 | −21.765 | 7.725 | 1.00 | 14.47 | A | N |
| ATOM | 6926 | CA | PHE | A | 434 | 47.211 | −20.455 | 8.034 | 1.00 | 14.05 | A | C |
| ATOM | 6928 | CB | PHE | A | 434 | 47.038 | −19.527 | 6.814 | 1.00 | 13.92 | A | C |
| ATOM | 6931 | CG | PHE | A | 434 | 47.583 | −18.117 | 6.985 | 1.00 | 13.80 | A | C |
| ATOM | 6932 | CD1 | PHE | A | 434 | 48.512 | −17.785 | 7.967 | 1.00 | 14.68 | A | C |
| ATOM | 6934 | CE1 | PHE | A | 434 | 48.987 | −16.482 | 8.081 | 1.00 | 13.77 | A | C |
| ATOM | 6936 | CZ | PHE | A | 434 | 48.558 | −15.508 | 7.200 | 1.00 | 12.50 | A | C |
| ATOM | 6938 | CE2 | PHE | A | 434 | 47.654 | −15.829 | 6.213 | 1.00 | 11.41 | A | C |
| ATOM | 6940 | CD2 | PHE | A | 434 | 47.177 | −17.122 | 6.104 | 1.00 | 13.10 | A | C |
| ATOM | 6942 | C | PHE | A | 434 | 46.599 | −19.864 | 9.311 | 1.00 | 13.97 | A | C |
| ATOM | 6943 | O | PHE | A | 434 | 47.325 | −19.429 | 10.208 | 1.00 | 13.34 | A | O |
| ATOM | 6945 | N | ARG | A | 435 | 45.273 | −19.878 | 9.407 | 1.00 | 14.22 | A | N |
| ATOM | 6946 | CA | ARG | A | 435 | 44.594 | −19.371 | 10.603 | 1.00 | 14.37 | A | C |
| ATOM | 6948 | CB | ARG | A | 435 | 43.086 | −19.241 | 10.359 | 1.00 | 14.35 | A | C |
| ATOM | 6951 | CG | ARG | A | 435 | 42.252 | −18.907 | 11.593 | 1.00 | 15.10 | A | C |
| ATOM | 6954 | CD | ARG | A | 435 | 42.754 | −17.675 | 12.337 | 1.00 | 16.05 | A | C |
| ATOM | 6957 | NE | ARG | A | 435 | 42.700 | −16.464 | 11.524 | 1.00 | 17.00 | A | N |
| ATOM | 6959 | CZ | ARG | A | 435 | 43.235 | −15.293 | 11.870 | 1.00 | 18.01 | A | C |
| ATOM | 6960 | NH1 | ARG | A | 435 | 43.888 | −15.153 | 13.020 | 1.00 | 18.43 | A | N |
| ATOM | 6963 | NH2 | ARG | A | 435 | 43.121 | −14.253 | 11.054 | 1.00 | 18.41 | A | N |
| ATOM | 6966 | C | ARG | A | 435 | 44.864 | −20.264 | 11.813 | 1.00 | 14.63 | A | C |
| ATOM | 6967 | O | ARG | A | 435 | 45.259 | −19.774 | 12.870 | 1.00 | 14.88 | A | O |
| ATOM | 6969 | N | LEU | A | 436 | 44.650 | −21.569 | 11.651 | 1.00 | 14.88 | A | N |
| ATOM | 6970 | CA | LEU | A | 436 | 44.874 | −22.531 | 12.735 | 1.00 | 14.69 | A | C |
| ATOM | 6972 | CB | LEU | A | 436 | 44.567 | −23.964 | 12.274 | 1.00 | 14.43 | A | C |
| ATOM | 6975 | CG | LEU | A | 436 | 43.095 | −24.373 | 12.141 | 1.00 | 12.91 | A | C |
| ATOM | 6977 | CD1 | LEU | A | 436 | 42.975 | −25.815 | 11.667 | 1.00 | 9.69 | A | C |
| ATOM | 6981 | CD2 | LEU | A | 436 | 42.353 | −24.194 | 13.454 | 1.00 | 11.60 | A | C |
| ATOM | 6985 | C | LEU | A | 436 | 46.300 | −22.450 | 13.302 | 1.00 | 15.09 | A | C |
| ATOM | 6986 | O | LEU | A | 436 | 46.480 | −22.448 | 14.519 | 1.00 | 15.32 | A | O |
| ATOM | 6988 | N | CYS | A | 437 | 47.303 | −22.375 | 12.429 | 1.00 | 15.32 | A | N |
| ATOM | 6989 | CA | CYS | A | 437 | 48.692 | −22.223 | 12.877 | 1.00 | 15.91 | A | C |
| ATOM | 6991 | CB | CYS | A | 437 | 49.663 | −22.121 | 11.693 | 1.00 | 16.11 | A | C |
| ATOM | 6994 | SG | CYS | A | 437 | 50.204 | −23.702 | 11.009 | 1.00 | 15.22 | A | S |
| ATOM | 6996 | C | CYS | A | 437 | 48.848 | −20.989 | 13.763 | 1.00 | 16.70 | A | C |
| ATOM | 6997 | O | CYS | A | 437 | 49.285 | −21.100 | 14.910 | 1.00 | 17.68 | A | O |
| ATOM | 6999 | N | ASN | A | 438 | 48.485 | −19.825 | 13.224 | 1.00 | 16.73 | A | N |
| ATOM | 7000 | CA | ASN | A | 438 | 48.591 | −18.548 | 13.946 | 1.00 | 16.68 | A | C |
| ATOM | 7002 | CB | ASN | A | 438 | 47.902 | −17.428 | 13.148 | 1.00 | 16.72 | A | C |
| ATOM | 7005 | CG | ASN | A | 438 | 48.141 | −16.036 | 13.733 | 1.00 | 16.65 | A | C |
| ATOM | 7006 | OD1 | ASN | A | 438 | 48.240 | −15.855 | 14.947 | 1.00 | 18.65 | A | O |
| ATOM | 7007 | ND2 | ASN | A | 438 | 48.214 | −15.042 | 12.858 | 1.00 | 16.47 | A | N |
| ATOM | 7010 | C | ASN | A | 438 | 47.993 | −18.634 | 15.349 | 1.00 | 16.53 | A | C |

TABLE 8-2-continued

Coordinates for L494P Structure

| | | | | | | | | | | | | |
|---|---|---|---|---|---|---|---|---|---|---|---|---|
| ATOM | 7011 | O | ASN | A | 438 | 48.666 | −18.340 | 16.343 | 1.00 | 16.47 | A | O |
| ATOM | 7013 | N | ASP | A | 439 | 46.735 | −19.055 | 15.417 | 1.00 | 16.27 | A | N |
| ATOM | 7014 | CA | ASP | A | 439 | 45.992 | −19.076 | 16.672 | 1.00 | 16.30 | A | C |
| ATOM | 7016 | CB | ASP | A | 439 | 44.503 | −19.296 | 16.400 | 1.00 | 16.10 | A | C |
| ATOM | 7019 | CG | ASP | A | 439 | 43.872 | −18.134 | 15.650 | 1.00 | 15.85 | A | C |
| ATOM | 7020 | OD1 | ASP | A | 439 | 44.623 | −17.292 | 15.112 | 1.00 | 14.52 | A | O |
| ATOM | 7021 | OD2 | ASP | A | 439 | 42.626 | −18.059 | 15.598 | 1.00 | 16.49 | A | O |
| ATOM | 7022 | C | ASP | A | 439 | 46.527 | −20.115 | 17.660 | 1.00 | 16.83 | A | C |
| ATOM | 7023 | O | ASP | A | 439 | 46.451 | −19.911 | 18.874 | 1.00 | 17.09 | A | O |
| ATOM | 7025 | N | LEU | A | 440 | 47.067 | −21.219 | 17.145 | 1.00 | 17.06 | A | N |
| ATOM | 7026 | CA | LEU | A | 440 | 47.742 | −22.215 | 17.987 | 1.00 | 17.22 | A | C |
| ATOM | 7028 | CB | LEU | A | 440 | 48.155 | −23.442 | 17.166 | 1.00 | 17.05 | A | C |
| ATOM | 7031 | CG | LEU | A | 440 | 47.100 | −24.537 | 17.019 | 1.00 | 15.68 | A | C |
| ATOM | 7033 | CD1 | LEU | A | 440 | 47.460 | −25.487 | 15.894 | 1.00 | 15.98 | A | C |
| ATOM | 7037 | CD2 | LEU | A | 440 | 46.955 | −25.288 | 18.321 | 1.00 | 15.39 | A | C |
| ATOM | 7041 | C | LEU | A | 440 | 48.972 | −21.625 | 18.680 | 1.00 | 18.01 | A | C |
| ATOM | 7042 | O | LEU | A | 440 | 49.261 | −21.965 | 19.830 | 1.00 | 17.74 | A | O |
| ATOM | 7044 | N | ALA | A | 441 | 49.685 | −20.747 | 17.972 | 1.00 | 18.91 | A | N |
| ATOM | 7045 | CA | ALA | A | 441 | 50.883 | −20.083 | 18.502 | 1.00 | 19.53 | A | C |
| ATOM | 7047 | CB | ALA | A | 441 | 51.622 | −19.360 | 17.384 | 1.00 | 19.65 | A | C |
| ATOM | 7051 | C | ALA | A | 441 | 50.542 | −19.101 | 19.616 | 1.00 | 19.96 | A | C |
| ATOM | 7052 | O | ALA | A | 441 | 51.224 | −19.050 | 20.639 | 1.00 | 19.83 | A | O |
| ATOM | 7054 | N | SER | A | 442 | 49.480 | −18.328 | 19.407 | 1.00 | 20.77 | A | N |
| ATOM | 7055 | CA | SER | A | 442 | 49.015 | −17.350 | 20.387 | 1.00 | 21.70 | A | C |
| ATOM | 7057 | CB | SER | A | 442 | 48.473 | −16.122 | 19.653 | 1.00 | 22.02 | A | C |
| ATOM | 7060 | OG | SER | A | 442 | 47.282 | −16.440 | 18.950 | 1.00 | 22.89 | A | O |
| ATOM | 7062 | C | SER | A | 442 | 47.926 | −17.911 | 21.312 | 1.00 | 22.14 | A | C |
| ATOM | 7063 | O | SER | A | 442 | 47.178 | −17.149 | 21.924 | 1.00 | 22.10 | A | O |
| ATOM | 7065 | N | ALA | A | 443 | 47.845 | −19.236 | 21.422 | 1.00 | 22.95 | A | N |
| ATOM | 7066 | CA | ALA | A | 443 | 46.762 | −19.886 | 22.161 | 1.00 | 23.60 | A | C |
| ATOM | 7068 | CB | ALA | A | 443 | 46.779 | −21.396 | 21.915 | 1.00 | 23.77 | A | C |
| ATOM | 7072 | C | ALA | A | 443 | 46.816 | −19.592 | 23.660 | 1.00 | 24.06 | A | C |
| ATOM | 7073 | O | ALA | A | 443 | 45.974 | −18.857 | 24.177 | 1.00 | 24.06 | A | O |
| ATOM | 7075 | N | SER | A | 444 | 47.813 | −20.151 | 24.344 | 1.00 | 24.55 | A | N |
| ATOM | 7076 | CA | SER | A | 444 | 47.912 | −20.054 | 25.806 | 1.00 | 24.88 | A | C |
| ATOM | 7078 | CB | SER | A | 444 | 49.039 | −20.954 | 26.324 | 1.00 | 24.85 | A | C |
| ATOM | 7081 | OG | SER | A | 444 | 50.274 | −20.624 | 25.714 | 1.00 | 25.18 | A | O |
| ATOM | 7083 | C | SER | A | 444 | 48.119 | −18.625 | 26.320 | 1.00 | 25.16 | A | C |
| ATOM | 7084 | O | SER | A | 444 | 47.749 | −18.315 | 27.456 | 1.00 | 25.37 | A | O |
| ATOM | 7086 | N | ALA | A | 445 | 48.709 | −17.764 | 25.490 | 1.00 | 25.22 | A | N |
| ATOM | 7087 | CA | ALA | A | 445 | 48.924 | −16.363 | 25.854 | 1.00 | 25.09 | A | C |
| ATOM | 7089 | CB | ALA | A | 445 | 49.820 | −15.675 | 24.832 | 1.00 | 25.06 | A | C |
| ATOM | 7093 | C | ALA | A | 445 | 47.598 | −15.622 | 25.971 | 1.00 | 25.09 | A | C |
| ATOM | 7094 | O | ALA | A | 445 | 47.333 | −14.971 | 26.980 | 1.00 | 25.23 | A | O |
| ATOM | 7096 | N | GLU | A | 446 | 46.766 | −15.738 | 24.939 | 1.00 | 25.16 | A | N |
| ATOM | 7097 | CA | GLU | A | 446 | 45.496 | −15.009 | 24.873 | 1.00 | 25.34 | A | C |
| ATOM | 7099 | CB | GLU | A | 446 | 44.976 | −14.984 | 23.430 | 1.00 | 25.42 | A | C |
| ATOM | 7102 | CG | GLU | A | 446 | 45.884 | −14.210 | 22.473 | 1.00 | 26.40 | A | C |
| ATOM | 7105 | CD | GLU | A | 446 | 45.477 | −14.336 | 21.012 | 1.00 | 27.93 | A | C |
| ATOM | 7106 | OE1 | GLU | A | 446 | 44.450 | −14.988 | 20.718 | 1.00 | 28.81 | A | O |
| ATOM | 7107 | OE2 | GLU | A | 446 | 46.191 | −13.776 | 20.153 | 1.00 | 27.41 | A | O |
| ATOM | 7108 | C | GLU | A | 446 | 44.421 | −15.561 | 25.819 | 1.00 | 25.11 | A | C |
| ATOM | 7109 | O | GLU | A | 446 | 43.555 | −14.812 | 26.273 | 1.00 | 24.91 | A | O |
| ATOM | 7111 | N | ILE | A | 447 | 44.482 | −16.859 | 26.115 | 1.00 | 25.06 | A | N |
| ATOM | 7112 | CA | ILE | A | 447 | 43.524 | −17.497 | 27.026 | 1.00 | 25.06 | A | C |
| ATOM | 7114 | CB | ILE | A | 447 | 43.578 | −19.041 | 26.936 | 1.00 | 25.18 | A | C |
| ATOM | 7116 | CG1 | ILE | A | 447 | 43.192 | −19.522 | 25.535 | 1.00 | 25.37 | A | C |
| ATOM | 7119 | CD1 | ILE | A | 447 | 43.705 | −20.915 | 25.217 | 1.00 | 24.89 | A | C |
| ATOM | 7123 | CG2 | ILE | A | 447 | 42.642 | −19.672 | 27.963 | 1.00 | 24.79 | A | C |
| ATOM | 7127 | C | ILE | A | 447 | 43.793 | −17.081 | 28.473 | 1.00 | 25.00 | A | C |
| ATOM | 7128 | O | ILE | A | 447 | 42.862 | −16.762 | 29.216 | 1.00 | 25.06 | A | O |
| ATOM | 7130 | N | ALA | A | 448 | 45.066 | −17.095 | 28.864 | 1.00 | 24.78 | A | N |
| ATOM | 7131 | CA | ALA | A | 448 | 45.479 | −16.656 | 30.198 | 1.00 | 24.75 | A | C |
| ATOM | 7133 | CB | ALA | A | 448 | 46.968 | −16.911 | 30.399 | 1.00 | 24.58 | A | C |
| ATOM | 7137 | C | ALA | A | 448 | 45.156 | −15.177 | 30.439 | 1.00 | 24.85 | A | C |
| ATOM | 7138 | O | ALA | A | 448 | 44.840 | −14.782 | 31.562 | 1.00 | 24.72 | A | O |
| ATOM | 7140 | N | ARG | A | 449 | 45.235 | −14.370 | 29.381 | 1.00 | 25.19 | A | N |
| ATOM | 7141 | CA | ARG | A | 449 | 44.895 | −12.944 | 29.453 | 1.00 | 25.36 | A | C |
| ATOM | 7143 | CB | ARG | A | 449 | 45.514 | −12.181 | 28.272 | 1.00 | 25.38 | A | C |
| ATOM | 7146 | CG | ARG | A | 449 | 47.002 | −11.884 | 28.451 | 1.00 | 25.01 | A | C |
| ATOM | 7149 | CD | ARG | A | 449 | 47.559 | −10.951 | 27.375 | 1.00 | 23.90 | A | C |
| ATOM | 7152 | NE | ARG | A | 449 | 48.127 | −11.685 | 26.242 | 1.00 | 22.76 | A | N |
| ATOM | 7154 | CZ | ARG | A | 449 | 47.765 | −11.558 | 24.963 | 1.00 | 23.10 | A | C |
| ATOM | 7155 | NH1 | ARG | A | 449 | 46.817 | −10.705 | 24.588 | 1.00 | 22.37 | A | N |
| ATOM | 7158 | NH2 | ARG | A | 449 | 48.374 | −12.295 | 24.037 | 1.00 | 24.00 | A | N |
| ATOM | 7161 | C | ARG | A | 449 | 43.382 | −12.686 | 29.517 | 1.00 | 25.70 | A | C |
| ATOM | 7162 | O | ARG | A | 449 | 42.958 | −11.579 | 29.853 | 1.00 | 25.66 | A | O |
| ATOM | 7164 | N | GLY | A | 450 | 42.579 | −13.699 | 29.190 | 1.00 | 26.09 | A | N |

TABLE 8-2-continued

Coordinates for L494P Structure

| | | | | | | | | | | | | |
|---|---|---|---|---|---|---|---|---|---|---|---|---|
| ATOM | 7165 | CA | GLY | A | 450 | 41.121 | −13.619 | 29.310 | 1.00 | 26.27 | A | C |
| ATOM | 7168 | C | GLY | A | 450 | 40.432 | −13.118 | 28.054 | 1.00 | 26.55 | A | C |
| ATOM | 7169 | O | GLY | A | 450 | 39.447 | −12.383 | 28.132 | 1.00 | 26.90 | A | O |
| ATOM | 7171 | N | GLU | A | 451 | 40.949 | −13.523 | 26.895 | 1.00 | 26.64 | A | N |
| ATOM | 7172 | CA | GLU | A | 451 | 40.382 | −13.141 | 25.602 | 1.00 | 26.67 | A | C |
| ATOM | 7174 | CB | GLU | A | 451 | 41.475 | −12.562 | 24.701 | 1.00 | 27.07 | A | C |
| ATOM | 7177 | CG | GLU | A | 451 | 42.137 | −11.307 | 25.255 | 1.00 | 27.64 | A | C |
| ATOM | 7180 | CD | GLU | A | 451 | 43.464 | −11.004 | 24.583 | 1.00 | 29.26 | A | C |
| ATOM | 7181 | OE1 | GLU | A | 451 | 43.516 | −10.980 | 23.333 | 1.00 | 28.51 | A | O |
| ATOM | 7182 | OE2 | GLU | A | 451 | 44.455 | −10.789 | 25.312 | 1.00 | 30.56 | A | O |
| ATOM | 7183 | C | GLU | A | 451 | 39.731 | −14.348 | 24.925 | 1.00 | 26.15 | A | C |
| ATOM | 7184 | O | GLU | A | 451 | 39.901 | −15.485 | 25.369 | 1.00 | 26.18 | A | O |
| ATOM | 7186 | N | THR | A | 452 | 38.986 | −14.089 | 23.853 | 1.00 | 25.51 | A | N |
| ATOM | 7187 | CA | THR | A | 452 | 38.273 | −15.142 | 23.119 | 1.00 | 24.90 | A | C |
| ATOM | 7189 | CB | THR | A | 452 | 36.752 | −15.015 | 23.327 | 1.00 | 24.75 | A | C |
| ATOM | 7191 | OG1 | THR | A | 452 | 36.470 | −14.915 | 24.727 | 1.00 | 24.32 | A | O |
| ATOM | 7193 | CG2 | THR | A | 452 | 36.021 | −16.222 | 22.756 | 1.00 | 24.68 | A | C |
| ATOM | 7197 | C | THR | A | 452 | 38.560 | −15.175 | 21.609 | 1.00 | 24.60 | A | C |
| ATOM | 7198 | O | THR | A | 452 | 38.318 | −16.200 | 20.964 | 1.00 | 24.57 | A | O |
| ATOM | 7200 | N | ALA | A | 453 | 39.066 | −14.073 | 21.049 | 1.00 | 23.97 | A | N |
| ATOM | 7201 | CA | ALA | A | 453 | 39.372 | −13.991 | 19.613 | 1.00 | 23.32 | A | C |
| ATOM | 7203 | CB | ALA | A | 453 | 39.710 | −12.550 | 19.216 | 1.00 | 23.40 | A | C |
| ATOM | 7207 | C | ALA | A | 453 | 40.515 | −14.935 | 19.237 | 1.00 | 22.48 | A | C |
| ATOM | 7208 | O | ALA | A | 453 | 41.639 | −14.504 | 18.962 | 1.00 | 22.66 | A | O |
| ATOM | 7210 | N | ASN | A | 454 | 40.201 | −16.228 | 19.220 | 1.00 | 21.33 | A | N |
| ATOM | 7211 | CA | ASN | A | 454 | 41.191 | −17.281 | 19.038 | 1.00 | 20.43 | A | C |
| ATOM | 7213 | CB | ASN | A | 454 | 42.047 | −17.415 | 20.297 | 1.00 | 20.27 | A | C |
| ATOM | 7216 | CG | ASN | A | 454 | 43.269 | −18.277 | 20.082 | 1.00 | 20.86 | A | C |
| ATOM | 7217 | OD1 | ASN | A | 454 | 43.160 | −19.454 | 19.740 | 1.00 | 22.12 | A | O |
| ATOM | 7218 | ND2 | ASN | A | 454 | 44.445 | −17.697 | 20.294 | 1.00 | 22.69 | A | N |
| ATOM | 7221 | C | ASN | A | 454 | 40.488 | −18.602 | 18.733 | 1.00 | 19.67 | A | C |
| ATOM | 7222 | O | ASN | A | 454 | 39.513 | −18.957 | 19.396 | 1.00 | 19.58 | A | O |
| ATOM | 7224 | N | SER | A | 455 | 40.986 | −19.320 | 17.731 | 1.00 | 18.91 | A | N |
| ATOM | 7225 | CA | SER | A | 455 | 40.347 | −20.549 | 17.264 | 1.00 | 18.58 | A | C |
| ATOM | 7227 | CB | SER | A | 455 | 41.080 | −21.092 | 16.040 | 1.00 | 18.57 | A | C |
| ATOM | 7230 | OG | SER | A | 455 | 41.081 | −20.136 | 14.995 | 1.00 | 18.90 | A | O |
| ATOM | 7232 | C | SER | A | 455 | 40.294 | −21.619 | 18.348 | 1.00 | 18.43 | A | C |
| ATOM | 7233 | O | SER | A | 455 | 39.274 | −22.289 | 18.517 | 1.00 | 18.43 | A | O |
| ATOM | 7235 | N | VAL | A | 456 | 41.395 | −21.765 | 19.081 | 1.00 | 18.24 | A | N |
| ATOM | 7236 | CA | VAL | A | 456 | 41.476 | −22.719 | 20.189 | 1.00 | 17.99 | A | C |
| ATOM | 7238 | CB | VAL | A | 456 | 42.896 | −22.755 | 20.804 | 1.00 | 17.68 | A | C |
| ATOM | 7240 | CG1 | VAL | A | 456 | 43.002 | −23.866 | 21.837 | 1.00 | 17.09 | A | C |
| ATOM | 7244 | CG2 | VAL | A | 456 | 43.950 | −22.931 | 19.720 | 1.00 | 17.17 | A | C |
| ATOM | 7248 | C | VAL | A | 456 | 40.472 | −22.360 | 21.290 | 1.00 | 18.30 | A | C |
| ATOM | 7249 | O | VAL | A | 456 | 39.855 | −23.240 | 21.891 | 1.00 | 18.13 | A | O |
| ATOM | 7251 | N | SER | A | 457 | 40.314 | −21.062 | 21.537 | 1.00 | 18.70 | A | N |
| ATOM | 7252 | CA | SER | A | 457 | 39.420 | −20.564 | 22.579 | 1.00 | 18.75 | A | C |
| ATOM | 7254 | CB | SER | A | 457 | 39.593 | −19.050 | 22.748 | 1.00 | 18.60 | A | C |
| ATOM | 7257 | OG | SER | A | 457 | 38.845 | −18.568 | 23.849 | 1.00 | 19.53 | A | O |
| ATOM | 7259 | C | SER | A | 457 | 37.961 | −20.887 | 22.276 | 1.00 | 18.84 | A | C |
| ATOM | 7260 | O | SER | A | 457 | 37.233 | −21.352 | 23.151 | 1.00 | 19.03 | A | O |
| ATOM | 7262 | N | CYS | A | 458 | 37.540 | −20.641 | 21.038 | 1.00 | 19.02 | A | N |
| ATOM | 7263 | CA | CYS | A | 458 | 36.150 | −20.883 | 20.639 | 1.00 | 19.32 | A | C |
| ATOM | 7265 | CB | CYS | A | 458 | 35.820 | −20.159 | 19.328 | 1.00 | 19.42 | A | C |
| ATOM | 7268 | SG | CYS | A | 458 | 35.508 | −18.389 | 19.544 | 1.00 | 20.53 | A | S |
| ATOM | 7270 | C | CYS | A | 458 | 35.811 | −22.373 | 20.530 | 1.00 | 19.33 | A | C |
| ATOM | 7271 | O | CYS | A | 458 | 34.639 | −22.746 | 20.610 | 1.00 | 19.60 | A | O |
| ATOM | 7273 | N | TYR | A | 459 | 36.827 | −23.218 | 20.355 | 1.00 | 19.09 | A | N |
| ATOM | 7274 | CA | TYR | A | 459 | 36.622 | −24.666 | 20.365 | 1.00 | 18.87 | A | C |
| ATOM | 7276 | CB | TYR | A | 459 | 37.841 | −25.402 | 19.805 | 1.00 | 18.80 | A | C |
| ATOM | 7279 | CG | TYR | A | 459 | 37.543 | −26.809 | 19.320 | 1.00 | 17.90 | A | C |
| ATOM | 7280 | CD1 | TYR | A | 459 | 37.163 | −27.044 | 17.999 | 1.00 | 15.79 | A | C |
| ATOM | 7282 | CE1 | TYR | A | 459 | 36.890 | −28.327 | 17.546 | 1.00 | 15.20 | A | C |
| ATOM | 7284 | CZ | TYR | A | 459 | 36.998 | −29.398 | 18.415 | 1.00 | 16.33 | A | C |
| ATOM | 7285 | OH | TYR | A | 459 | 36.728 | −30.670 | 17.962 | 1.00 | 17.00 | A | O |
| ATOM | 7287 | CE2 | TYR | A | 459 | 37.375 | −29.194 | 19.734 | 1.00 | 16.42 | A | C |
| ATOM | 7289 | CD2 | TYR | A | 459 | 37.646 | −27.903 | 20.179 | 1.00 | 17.05 | A | C |
| ATOM | 7291 | C | TYR | A | 459 | 36.332 | −25.124 | 21.792 | 1.00 | 19.29 | A | C |
| ATOM | 7292 | O | TYR | A | 459 | 35.353 | −25.834 | 22.029 | 1.00 | 19.45 | A | O |
| ATOM | 7294 | N | MET | A | 460 | 37.182 | −24.704 | 22.733 | 1.00 | 19.66 | A | N |
| ATOM | 7295 | CA | MET | A | 460 | 36.959 | −24.942 | 24.166 | 1.00 | 20.09 | A | C |
| ATOM | 7297 | CB | MET | A | 460 | 37.907 | −24.088 | 25.020 | 1.00 | 20.44 | A | C |
| ATOM | 7300 | CG | MET | A | 460 | 39.363 | −24.535 | 25.035 | 1.00 | 21.37 | A | C |
| ATOM | 7303 | SD | MET | A | 460 | 40.403 | −23.446 | 26.040 | 1.00 | 20.41 | A | S |
| ATOM | 7304 | CE | MET | A | 460 | 39.710 | −23.720 | 27.672 | 1.00 | 20.51 | A | C |
| ATOM | 7308 | C | MET | A | 460 | 35.526 | −24.602 | 24.568 | 1.00 | 20.02 | A | C |
| ATOM | 7309 | O | MET | A | 460 | 34.881 | −25.354 | 25.299 | 1.00 | 20.55 | A | O |
| ATOM | 7311 | N | ARG | A | 461 | 35.044 | −23.460 | 24.087 | 1.00 | 19.56 | A | N |

TABLE 8-2-continued

| Coordinates for L494P Structure | | | | | | | | | | | |
|---|---|---|---|---|---|---|---|---|---|---|---|
| ATOM | 7312 | CA | ARG | A | 461 | 33.701 | −22.985 | 24.402 | 1.00 | 19.46 A | C |
| ATOM | 7314 | CB | ARG | A | 461 | 33.576 | −21.506 | 24.032 | 1.00 | 19.44 A | C |
| ATOM | 7317 | CG | ARG | A | 461 | 32.316 | −20.828 | 24.545 | 1.00 | 19.32 A | C |
| ATOM | 7320 | CD | ARG | A | 461 | 32.420 | −19.311 | 24.446 | 1.00 | 20.04 A | C |
| ATOM | 7323 | NE | ARG | A | 461 | 32.757 | −18.860 | 23.095 | 1.00 | 20.53 A | N |
| ATOM | 7325 | CZ | ARG | A | 461 | 32.925 | −17.587 | 22.743 | 1.00 | 21.06 A | C |
| ATOM | 7326 | NH1 | ARG | A | 461 | 32.781 | −16.609 | 23.634 | 1.00 | 20.57 A | N |
| ATOM | 7329 | NH2 | ARG | A | 461 | 33.238 | −17.287 | 21.486 | 1.00 | 22.20 A | N |
| ATOM | 7332 | C | ARG | A | 461 | 32.622 | −23.797 | 23.685 | 1.00 | 19.27 A | C |
| ATOM | 7333 | O | ARG | A | 461 | 31.605 | −24.142 | 24.283 | 1.00 | 19.05 A | O |
| ATOM | 7335 | N | THR | A | 462 | 32.852 | −24.099 | 22.409 | 1.00 | 19.32 A | N |
| ATOM | 7336 | CA | THR | A | 462 | 31.871 | −24.814 | 21.585 | 1.00 | 19.62 A | C |
| ATOM | 7338 | CB | THR | A | 462 | 32.292 | −24.821 | 20.095 | 1.00 | 19.63 A | C |
| ATOM | 7340 | OG1 | THR | A | 462 | 32.065 | −23.524 | 19.532 | 1.00 | 20.66 A | O |
| ATOM | 7342 | CG2 | THR | A | 462 | 31.503 | −25.854 | 19.296 | 1.00 | 20.05 A | C |
| ATOM | 7346 | C | THR | A | 462 | 31.632 | −26.253 | 22.052 | 1.00 | 19.82 A | C |
| ATOM | 7347 | O | THR | A | 462 | 30.487 | −26.719 | 22.084 | 1.00 | 20.00 A | O |
| ATOM | 7349 | N | LYS | A | 463 | 32.710 | −26.948 | 22.413 | 1.00 | 19.62 A | N |
| ATOM | 7350 | CA | LYS | A | 463 | 32.622 | −28.345 | 22.846 | 1.00 | 19.23 A | C |
| ATOM | 7352 | CB | LYS | A | 463 | 33.772 | −29.162 | 22.243 | 1.00 | 19.10 A | C |
| ATOM | 7355 | CG | LYS | A | 463 | 34.023 | −28.923 | 20.754 | 1.00 | 17.85 A | C |
| ATOM | 7358 | CD | LYS | A | 463 | 32.791 | −29.169 | 19.891 | 1.00 | 17.09 A | C |
| ATOM | 7361 | CE | LYS | A | 463 | 33.108 | −28.934 | 18.419 | 1.00 | 17.67 A | C |
| ATOM | 7364 | NZ | LYS | A | 463 | 31.897 | −28.942 | 17.554 | 1.00 | 18.35 A | N |
| ATOM | 7368 | C | LYS | A | 463 | 32.618 | −28.499 | 24.374 | 1.00 | 19.01 A | C |
| ATOM | 7369 | O | LYS | A | 463 | 32.385 | −29.597 | 24.883 | 1.00 | 18.88 A | O |
| ATOM | 7371 | N | GLY | A | 464 | 32.875 | −27.407 | 25.095 | 1.00 | 18.78 A | N |
| ATOM | 7372 | CA | GLY | A | 464 | 32.929 | −27.434 | 26.557 | 1.00 | 18.68 A | C |
| ATOM | 7375 | C | GLY | A | 464 | 34.040 | −28.331 | 27.067 | 1.00 | 18.63 A | C |
| ATOM | 7376 | O | GLY | A | 464 | 33.780 | −29.294 | 27.790 | 1.00 | 18.57 A | O |
| ATOM | 7378 | N | ILE | A | 465 | 35.278 | −28.015 | 26.685 | 1.00 | 18.68 A | N |
| ATOM | 7379 | CA | ILE | A | 465 | 36.439 | −28.853 | 27.006 | 1.00 | 18.82 A | C |
| ATOM | 7381 | CB | ILE | A | 465 | 36.788 | −29.812 | 25.838 | 1.00 | 18.83 A | C |
| ATOM | 7383 | CG1 | ILE | A | 465 | 37.004 | −29.035 | 24.534 | 1.00 | 18.84 A | C |
| ATOM | 7386 | CD1 | ILE | A | 465 | 37.345 | −29.915 | 23.345 | 1.00 | 18.16 A | C |
| ATOM | 7390 | CG2 | ILE | A | 465 | 35.689 | −30.848 | 25.660 | 1.00 | 19.72 A | C |
| ATOM | 7394 | C | ILE | A | 465 | 37.682 | −28.039 | 27.370 | 1.00 | 18.85 A | C |
| ATOM | 7395 | O | ILE | A | 465 | 37.736 | −26.826 | 27.153 | 1.00 | 18.44 A | O |
| ATOM | 7397 | N | SER | A | 466 | 38.676 | −28.731 | 27.920 | 1.00 | 19.23 A | N |
| ATOM | 7398 | CA | SER | A | 466 | 39.912 | −28.108 | 28.384 | 1.00 | 19.68 A | C |
| ATOM | 7400 | CB | SER | A | 466 | 40.667 | −29.071 | 29.304 | 1.00 | 19.87 A | C |
| ATOM | 7403 | OG | SER | A | 466 | 40.980 | −30.278 | 28.628 | 1.00 | 19.96 A | O |
| ATOM | 7405 | C | SER | A | 466 | 40.811 | −27.707 | 27.221 | 1.00 | 20.03 A | C |
| ATOM | 7406 | O | SER | A | 466 | 40.670 | −28.225 | 26.114 | 1.00 | 19.89 A | O |
| ATOM | 7408 | N | GLU | A | 467 | 41.746 | −26.797 | 27.491 | 1.00 | 20.78 A | N |
| ATOM | 7409 | CA | GLU | A | 467 | 42.673 | −26.283 | 26.472 | 1.00 | 21.37 A | C |
| ATOM | 7411 | CB | GLU | A | 467 | 43.576 | −25.189 | 27.062 | 1.00 | 21.42 A | C |
| ATOM | 7414 | CG | GLU | A | 467 | 44.408 | −24.433 | 26.022 | 1.00 | 21.87 A | C |
| ATOM | 7417 | CD | GLU | A | 467 | 45.487 | −23.565 | 26.640 | 1.00 | 22.82 A | C |
| ATOM | 7418 | OE1 | GLU | A | 467 | 45.207 | −22.883 | 27.647 | 1.00 | 23.89 A | O |
| ATOM | 7419 | OE2 | GLU | A | 467 | 46.618 | −23.560 | 26.109 | 1.00 | 23.99 A | O |
| ATOM | 7420 | C | GLU | A | 467 | 43.542 | −27.377 | 25.843 | 1.00 | 21.81 A | C |
| ATOM | 7421 | O | GLU | A | 467 | 43.856 | −27.309 | 24.651 | 1.00 | 22.00 A | O |
| ATOM | 7423 | N | GLU | A | 468 | 43.932 | −28.373 | 26.639 | 1.00 | 21.90 A | N |
| ATOM | 7424 | CA | GLU | A | 468 | 44.772 | −29.466 | 26.142 | 1.00 | 21.88 A | C |
| ATOM | 7426 | CB | GLU | A | 468 | 45.304 | −30.320 | 27.298 | 1.00 | 22.13 A | C |
| ATOM | 7429 | CG | GLU | A | 468 | 46.361 | −31.336 | 26.869 | 1.00 | 23.30 A | C |
| ATOM | 7432 | CD | GLU | A | 468 | 46.846 | −32.207 | 28.012 | 1.00 | 24.29 A | C |
| ATOM | 7433 | OE1 | GLU | A | 468 | 47.560 | −31.688 | 28.898 | 1.00 | 25.02 A | O |
| ATOM | 7434 | OE2 | GLU | A | 468 | 46.526 | −33.416 | 28.015 | 1.00 | 24.63 A | O |
| ATOM | 7435 | C | GLU | A | 468 | 44.022 | −30.345 | 25.137 | 1.00 | 21.46 A | C |
| ATOM | 7436 | O | GLU | A | 468 | 44.577 | −30.710 | 24.099 | 1.00 | 21.21 A | O |
| ATOM | 7438 | N | LEU | A | 469 | 42.771 | −30.685 | 25.450 | 1.00 | 21.18 A | N |
| ATOM | 7439 | CA | LEU | A | 469 | 41.919 | −31.458 | 24.531 | 1.00 | 20.84 A | C |
| ATOM | 7441 | CB | LEU | A | 469 | 40.692 | −32.042 | 25.253 | 1.00 | 21.05 A | C |
| ATOM | 7444 | CG | LEU | A | 469 | 40.856 | −33.409 | 25.932 | 1.00 | 20.32 A | C |
| ATOM | 7446 | CD1 | LEU | A | 469 | 41.842 | −33.328 | 27.086 | 1.00 | 20.20 A | C |
| ATOM | 7450 | CD2 | LEU | A | 469 | 39.508 | −33.940 | 26.415 | 1.00 | 18.12 A | C |
| ATOM | 7454 | C | LEU | A | 469 | 41.463 | −30.616 | 23.335 | 1.00 | 20.25 A | C |
| ATOM | 7455 | O | LEU | A | 469 | 41.262 | −31.149 | 22.243 | 1.00 | 20.27 A | O |
| ATOM | 7457 | N | ALA | A | 470 | 41.295 | −29.312 | 23.550 | 1.00 | 19.59 A | N |
| ATOM | 7458 | CA | ALA | A | 470 | 40.901 | −28.386 | 22.484 | 1.00 | 19.19 A | C |
| ATOM | 7460 | CB | ALA | A | 470 | 40.517 | −27.037 | 23.069 | 1.00 | 18.89 A | C |
| ATOM | 7464 | C | ALA | A | 470 | 42.013 | −28.213 | 21.452 | 1.00 | 19.15 A | C |
| ATOM | 7465 | O | ALA | A | 470 | 41.746 | −28.143 | 20.249 | 1.00 | 19.34 A | O |
| ATOM | 7467 | N | THR | A | 471 | 43.254 | −28.135 | 21.931 | 1.00 | 18.89 A | N |
| ATOM | 7468 | CA | THR | A | 471 | 44.426 | −28.064 | 21.059 | 1.00 | 18.62 A | C |
| ATOM | 7470 | CB | THR | A | 471 | 45.732 | −27.906 | 21.884 | 1.00 | 18.76 A | C |

TABLE 8-2-continued

Coordinates for L494P Structure

| | | | | | | | | | | | | |
|---|---|---|---|---|---|---|---|---|---|---|---|---|
| ATOM | 7472 | OG1 | THR | A | 471 | 45.777 | −26.597 | 22.467 | 1.00 | 19.40 | A | O |
| ATOM | 7474 | CG2 | THR | A | 471 | 46.968 | −28.103 | 21.012 | 1.00 | 18.57 | A | C |
| ATOM | 7478 | C | THR | A | 471 | 44.515 | −29.311 | 20.179 | 1.00 | 18.43 | A | C |
| ATOM | 7479 | O | THR | A | 471 | 44.622 | −29.205 | 18.959 | 1.00 | 18.22 | A | O |
| ATOM | 7481 | N | GLU | A | 472 | 44.446 | −30.484 | 20.807 | 1.00 | 18.49 | A | N |
| ATOM | 7482 | CA | GLU | A | 472 | 44.564 | −31.770 | 20.107 | 1.00 | 18.66 | A | C |
| ATOM | 7484 | CB | GLU | A | 472 | 44.382 | −32.928 | 21.094 | 1.00 | 18.91 | A | C |
| ATOM | 7487 | CG | GLU | A | 472 | 44.713 | −34.306 | 20.517 | 1.00 | 20.49 | A | C |
| ATOM | 7490 | CD | GLU | A | 472 | 44.356 | −35.452 | 21.450 | 1.00 | 21.71 | A | C |
| ATOM | 7491 | OE1 | GLU | A | 472 | 44.795 | −36.589 | 21.175 | 1.00 | 22.68 | A | O |
| ATOM | 7492 | OE2 | GLU | A | 472 | 43.637 | −35.225 | 22.448 | 1.00 | 22.86 | A | O |
| ATOM | 7493 | C | GLU | A | 472 | 43.569 | −31.924 | 18.951 | 1.00 | 18.52 | A | C |
| ATOM | 7494 | O | GLU | A | 472 | 43.896 | −32.510 | 17.917 | 1.00 | 17.98 | A | O |
| ATOM | 7496 | N | SER | A | 473 | 42.356 | −31.410 | 19.133 | 1.00 | 18.86 | A | N |
| ATOM | 7497 | CA | SER | A | 473 | 41.343 | −31.440 | 18.077 | 1.00 | 19.17 | A | C |
| ATOM | 7499 | CB | SER | A | 473 | 39.978 | −31.041 | 18.633 | 1.00 | 18.98 | A | C |
| ATOM | 7502 | OG | SER | A | 473 | 39.616 | −31.871 | 19.723 | 1.00 | 18.35 | A | O |
| ATOM | 7504 | C | SER | A | 473 | 41.727 | −30.519 | 16.917 | 1.00 | 19.64 | A | C |
| ATOM | 7505 | O | SER | A | 473 | 41.518 | −30.862 | 15.749 | 1.00 | 20.03 | A | O |
| ATOM | 7507 | N | VAL | A | 474 | 42.287 | −29.355 | 17.248 | 1.00 | 19.48 | A | N |
| ATOM | 7508 | CA | VAL | A | 474 | 42.797 | −28.424 | 16.240 | 1.00 | 19.38 | A | C |
| ATOM | 7510 | CB | VAL | A | 474 | 43.148 | −27.054 | 16.862 | 1.00 | 19.33 | A | C |
| ATOM | 7512 | CG1 | VAL | A | 474 | 43.833 | −26.152 | 15.844 | 1.00 | 18.11 | A | C |
| ATOM | 7516 | CG2 | VAL | A | 474 | 41.892 | −26.389 | 17.412 | 1.00 | 19.60 | A | C |
| ATOM | 7520 | C | VAL | A | 474 | 44.020 | −29.008 | 15.525 | 1.00 | 19.69 | A | C |
| ATOM | 7521 | O | VAL | A | 474 | 44.175 | −28.829 | 14.315 | 1.00 | 20.15 | A | O |
| ATOM | 7523 | N | MET | A | 475 | 44.873 | −29.714 | 16.268 | 1.00 | 19.66 | A | N |
| ATOM | 7524 | CA | MET | A | 475 | 46.005 | −30.444 | 15.680 | 1.00 | 19.70 | A | C |
| ATOM | 7526 | CB | MET | A | 475 | 46.889 | −31.053 | 16.772 | 1.00 | 20.05 | A | C |
| ATOM | 7529 | CG | MET | A | 475 | 47.604 | −30.045 | 17.650 | 1.00 | 20.04 | A | C |
| ATOM | 7532 | SD | MET | A | 475 | 48.893 | −29.161 | 16.773 | 1.00 | 21.08 | A | S |
| ATOM | 7533 | CE | MET | A | 475 | 50.090 | −28.966 | 18.096 | 1.00 | 21.33 | A | C |
| ATOM | 7537 | C | MET | A | 475 | 45.528 | −31.562 | 14.751 | 1.00 | 19.35 | A | C |
| ATOM | 7538 | O | MET | A | 475 | 46.147 | −31.822 | 13.718 | 1.00 | 19.12 | A | O |
| ATOM | 7540 | N | ASN | A | 476 | 44.441 | −32.230 | 15.136 | 1.00 | 19.22 | A | N |
| ATOM | 7541 | CA | ASN | A | 476 | 43.791 | −33.215 | 14.270 | 1.00 | 19.31 | A | C |
| ATOM | 7543 | CB | ASN | A | 476 | 42.729 | −34.021 | 15.036 | 1.00 | 19.59 | A | C |
| ATOM | 7546 | CG | ASN | A | 476 | 43.330 | −35.106 | 15.920 | 1.00 | 20.46 | A | C |
| ATOM | 7547 | OD1 | ASN | A | 476 | 44.375 | −35.682 | 15.605 | 1.00 | 21.67 | A | O |
| ATOM | 7548 | ND2 | ASN | A | 476 | 42.659 | −35.397 | 17.029 | 1.00 | 19.15 | A | N |
| ATOM | 7551 | C | ASN | A | 476 | 43.147 | −32.565 | 13.050 | 1.00 | 18.81 | A | C |
| ATOM | 7552 | O | ASN | A | 476 | 43.056 | −33.193 | 11.996 | 1.00 | 19.00 | A | O |
| ATOM | 7554 | N | LEU | A | 477 | 42.699 | −31.318 | 13.195 | 1.00 | 18.29 | A | N |
| ATOM | 7555 | CA | LEU | A | 477 | 42.084 | −30.588 | 12.083 | 1.00 | 18.10 | A | C |
| ATOM | 7557 | CB | LEU | A | 477 | 41.349 | −29.331 | 12.568 | 1.00 | 18.33 | A | C |
| ATOM | 7560 | CG | LEU | A | 477 | 40.013 | −29.097 | 11.847 | 1.00 | 19.37 | A | C |
| ATOM | 7562 | CD1 | LEU | A | 477 | 38.911 | −29.923 | 12.515 | 1.00 | 19.86 | A | C |
| ATOM | 7566 | CD2 | LEU | A | 477 | 39.627 | −27.623 | 11.809 | 1.00 | 19.63 | A | C |
| ATOM | 7570 | C | LEU | A | 477 | 43.115 | −30.208 | 11.022 | 1.00 | 17.36 | A | C |
| ATOM | 7571 | O | LEU | A | 477 | 42.808 | −30.206 | 9.834 | 1.00 | 16.65 | A | O |
| ATOM | 7573 | N | ILE | A | 478 | 44.328 | −29.876 | 11.459 | 1.00 | 17.33 | A | N |
| ATOM | 7574 | CA | ILE | A | 478 | 45.438 | −29.615 | 10.540 | 1.00 | 17.10 | A | C |
| ATOM | 7576 | CB | ILE | A | 478 | 46.684 | −29.070 | 11.278 | 1.00 | 16.99 | A | C |
| ATOM | 7578 | CG1 | ILE | A | 478 | 46.479 | −27.597 | 11.646 | 1.00 | 15.91 | A | C |
| ATOM | 7581 | CD1 | ILE | A | 478 | 47.583 | −27.015 | 12.513 | 1.00 | 14.00 | A | C |
| ATOM | 7585 | CG2 | ILE | A | 478 | 47.928 | −29.216 | 10.418 | 1.00 | 16.35 | A | C |
| ATOM | 7589 | C | ILE | A | 478 | 45.797 | −30.895 | 9.796 | 1.00 | 17.29 | A | C |
| ATOM | 7590 | O | ILE | A | 478 | 45.765 | −30.928 | 8.566 | 1.00 | 16.88 | A | O |
| ATOM | 7592 | N | ASP | A | 479 | 46.124 | −31.946 | 10.547 | 1.00 | 17.99 | A | N |
| ATOM | 7593 | CA | ASP | A | 479 | 46.388 | −33.264 | 9.962 | 1.00 | 18.84 | A | C |
| ATOM | 7595 | CB | ASP | A | 479 | 46.434 | −34.355 | 11.047 | 1.00 | 19.10 | A | C |
| ATOM | 7598 | CG | ASP | A | 479 | 47.715 | −34.320 | 11.885 | 1.00 | 20.09 | A | C |
| ATOM | 7599 | OD1 | ASP | A | 479 | 48.759 | −33.837 | 11.398 | 1.00 | 23.06 | A | O |
| ATOM | 7600 | OD2 | ASP | A | 479 | 47.678 | −34.799 | 13.039 | 1.00 | 20.40 | A | O |
| ATOM | 7601 | C | ASP | A | 479 | 45.316 | −33.616 | 8.926 | 1.00 | 19.15 | A | C |
| ATOM | 7602 | O | ASP | A | 479 | 45.633 | −34.020 | 7.807 | 1.00 | 19.09 | A | O |
| ATOM | 7604 | N | GLU | A | 480 | 44.052 | −33.439 | 9.307 | 1.00 | 19.60 | A | N |
| ATOM | 7605 | CA | GLU | A | 480 | 42.914 | −33.728 | 8.431 | 1.00 | 19.98 | A | C |
| ATOM | 7607 | CB | GLU | A | 480 | 41.602 | −33.582 | 9.207 | 1.00 | 19.86 | A | C |
| ATOM | 7610 | CG | GLU | A | 480 | 40.347 | −33.858 | 8.393 | 1.00 | 20.57 | A | C |
| ATOM | 7613 | CD | GLU | A | 480 | 39.126 | −34.088 | 9.268 | 1.00 | 22.39 | A | C |
| ATOM | 7614 | OE1 | GLU | A | 480 | 39.083 | −35.116 | 9.982 | 1.00 | 22.35 | A | O |
| ATOM | 7615 | OE2 | GLU | A | 480 | 38.205 | −33.244 | 9.233 | 1.00 | 22.18 | A | O |
| ATOM | 7616 | C | GLU | A | 480 | 42.885 | −32.835 | 7.190 | 1.00 | 20.39 | A | C |
| ATOM | 7617 | O | GLU | A | 480 | 42.571 | −33.303 | 6.095 | 1.00 | 20.59 | A | O |
| ATOM | 7619 | N | THR | A | 481 | 43.202 | −31.553 | 7.364 | 1.00 | 20.68 | A | N |
| ATOM | 7620 | CA | THR | A | 481 | 43.218 | −30.604 | 6.249 | 1.00 | 20.31 | A | C |
| ATOM | 7622 | CB | THR | A | 481 | 43.298 | −29.143 | 6.737 | 1.00 | 20.04 | A | C |

TABLE 8-2-continued

Coordinates for L494P Structure

| | | | | | | | | | | | | |
|---|---|---|---|---|---|---|---|---|---|---|---|---|
| ATOM | 7624 | OG1 | THR | A | 481 | 42.259 | −28.899 | 7.690 | 1.00 | 20.12 | A | O |
| ATOM | 7626 | CG2 | THR | A | 481 | 43.131 | −28.179 | 5.577 | 1.00 | 19.56 | A | C |
| ATOM | 7630 | C | THR | A | 481 | 44.378 | −30.897 | 5.297 | 1.00 | 20.57 | A | C |
| ATOM | 7631 | O | THR | A | 481 | 44.217 | −30.791 | 4.080 | 1.00 | 21.43 | A | O |
| ATOM | 7633 | N | TRP | A | 482 | 45.537 | −31.268 | 5.846 | 1.00 | 19.91 | A | N |
| ATOM | 7634 | CA | TRP | A | 482 | 46.673 | −31.698 | 5.020 | 1.00 | 19.35 | A | C |
| ATOM | 7636 | CB | TRP | A | 482 | 47.922 | −31.978 | 5.873 | 1.00 | 19.46 | A | C |
| ATOM | 7639 | CG | TRP | A | 482 | 48.839 | −30.798 | 5.995 | 1.00 | 19.49 | A | C |
| ATOM | 7640 | CD1 | TRP | A | 482 | 48.961 | −29.963 | 7.064 | 1.00 | 19.76 | A | C |
| ATOM | 7642 | NE1 | TRP | A | 482 | 49.900 | −28.996 | 6.805 | 1.00 | 18.99 | A | N |
| ATOM | 7644 | CE2 | TRP | A | 482 | 50.403 | −29.191 | 5.547 | 1.00 | 19.41 | A | C |
| ATOM | 7645 | CD2 | TRP | A | 482 | 49.757 | −30.320 | 5.005 | 1.00 | 18.58 | A | C |
| ATOM | 7646 | CE3 | TRP | A | 482 | 50.095 | −30.737 | 3.714 | 1.00 | 18.27 | A | C |
| ATOM | 7648 | CZ3 | TRP | A | 482 | 51.055 | −30.024 | 3.014 | 1.00 | 19.21 | A | C |
| ATOM | 7650 | CH2 | TRP | A | 482 | 51.681 | −28.902 | 3.581 | 1.00 | 20.66 | A | C |
| ATOM | 7652 | CZ2 | TRP | A | 482 | 51.369 | −28.470 | 4.842 | 1.00 | 19.87 | A | C |
| ATOM | 7654 | C | TRP | A | 482 | 46.333 | −32.933 | 4.186 | 1.00 | 18.89 | A | C |
| ATOM | 7655 | O | TRP | A | 482 | 46.780 | −33.055 | 3.048 | 1.00 | 18.56 | A | O |
| ATOM | 7657 | N | LYS | A | 483 | 45.544 | −33.842 | 4.753 | 1.00 | 18.60 | A | N |
| ATOM | 7658 | CA | LYS | A | 483 | 45.126 | −35.045 | 4.034 | 1.00 | 18.61 | A | C |
| ATOM | 7660 | CB | LYS | A | 483 | 44.344 | −35.996 | 4.953 | 1.00 | 18.82 | A | C |
| ATOM | 7663 | CG | LYS | A | 483 | 45.198 | −36.750 | 5.972 | 1.00 | 17.67 | A | C |
| ATOM | 7666 | CD | LYS | A | 483 | 44.331 | −37.423 | 7.032 | 1.00 | 15.32 | A | C |
| ATOM | 7669 | CE | LYS | A | 483 | 45.158 | −38.283 | 7.970 | 1.00 | 13.29 | A | C |
| ATOM | 7672 | NZ | LYS | A | 483 | 44.317 | −38.976 | 8.975 | 1.00 | 11.47 | A | N |
| ATOM | 7676 | C | LYS | A | 483 | 44.288 | −34.699 | 2.803 | 1.00 | 18.60 | A | C |
| ATOM | 7677 | O | LYS | A | 483 | 44.480 | −35.279 | 1.737 | 1.00 | 19.08 | A | O |
| ATOM | 7679 | N | LYS | A | 484 | 43.365 | −33.755 | 2.953 | 1.00 | 18.44 | A | N |
| ATOM | 7680 | CA | LYS | A | 484 | 42.497 | −33.350 | 1.848 | 1.00 | 18.75 | A | C |
| ATOM | 7682 | CB | LYS | A | 484 | 41.273 | −32.596 | 2.375 | 1.00 | 19.23 | A | C |
| ATOM | 7685 | CG | LYS | A | 484 | 40.298 | −33.472 | 3.160 | 1.00 | 20.08 | A | C |
| ATOM | 7688 | CD | LYS | A | 484 | 39.154 | −32.644 | 3.749 | 1.00 | 21.14 | A | C |
| ATOM | 7691 | CE | LYS | A | 484 | 38.400 | −33.410 | 4.825 | 1.00 | 21.14 | A | C |
| ATOM | 7694 | NZ | LYS | A | 484 | 37.453 | −32.542 | 5.575 | 1.00 | 21.03 | A | N |
| ATOM | 7698 | C | LYS | A | 484 | 43.229 | −32.506 | 0.799 | 1.00 | 18.54 | A | C |
| ATOM | 7699 | O | LYS | A | 484 | 42.816 | −32.464 | −0.362 | 1.00 | 18.32 | A | O |
| ATOM | 7701 | N | MET | A | 485 | 44.303 | −31.832 | 1.206 | 1.00 | 18.57 | A | N |
| ATOM | 7702 | CA | MET | A | 485 | 45.123 | −31.055 | 0.271 | 1.00 | 18.64 | A | C |
| ATOM | 7704 | CB | MET | A | 485 | 45.980 | −30.024 | 1.012 | 1.00 | 18.40 | A | C |
| ATOM | 7707 | CG | MET | A | 485 | 45.227 | −28.776 | 1.434 | 1.00 | 18.70 | A | C |
| ATOM | 7710 | SD | MET | A | 485 | 46.323 | −27.453 | 1.994 | 1.00 | 20.00 | A | S |
| ATOM | 7711 | CE | MET | A | 485 | 47.030 | −28.185 | 3.470 | 1.00 | 21.42 | A | C |
| ATOM | 7715 | C | MET | A | 485 | 46.018 | −31.957 | −0.579 | 1.00 | 18.87 | A | C |
| ATOM | 7716 | O | MET | A | 485 | 46.335 | −31.620 | −1.718 | 1.00 | 19.09 | A | O |
| ATOM | 7718 | N | ASN | A | 486 | 46.423 | −33.097 | −0.024 | 1.00 | 19.18 | A | N |
| ATOM | 7719 | CA | ASN | A | 486 | 47.263 | −34.055 | −0.747 | 1.00 | 19.51 | A | C |
| ATOM | 7721 | CB | ASN | A | 486 | 47.949 | −35.011 | 0.234 | 1.00 | 19.57 | A | C |
| ATOM | 7724 | CG | ASN | A | 486 | 48.863 | −34.291 | 1.215 | 1.00 | 18.76 | A | C |
| ATOM | 7725 | OD1 | ASN | A | 486 | 49.319 | −33.176 | 0.955 | 1.00 | 16.76 | A | O |
| ATOM | 7726 | ND2 | ASN | A | 486 | 49.129 | −34.926 | 2.353 | 1.00 | 15.82 | A | N |
| ATOM | 7729 | C | ASN | A | 486 | 46.484 | −34.844 | −1.805 | 1.00 | 19.93 | A | C |
| ATOM | 7730 | O | ASN | A | 486 | 47.079 | −35.465 | −2.686 | 1.00 | 19.71 | A | O |
| ATOM | 7732 | N | LYS | A | 487 | 45.157 | −34.825 | −1.699 | 1.00 | 20.76 | A | N |
| ATOM | 7733 | CA | LYS | A | 487 | 44.270 | −35.350 | −2.740 | 1.00 | 21.38 | A | C |
| ATOM | 7735 | CB | LYS | A | 487 | 42.876 | −35.618 | −2.155 | 1.00 | 21.37 | A | C |
| ATOM | 7738 | CG | LYS | A | 487 | 41.863 | −36.168 | −3.146 | 1.00 | 22.41 | A | C |
| ATOM | 7741 | CD | LYS | A | 487 | 40.657 | −36.762 | −2.429 | 1.00 | 24.55 | A | C |
| ATOM | 7744 | CE | LYS | A | 487 | 39.699 | −37.429 | −3.406 | 1.00 | 25.58 | A | C |
| ATOM | 7747 | NZ | LYS | A | 487 | 38.641 | −38.214 | −2.712 | 1.00 | 25.77 | A | N |
| ATOM | 7751 | C | LYS | A | 487 | 44.173 | −34.357 | −3.902 | 1.00 | 21.61 | A | C |
| ATOM | 7752 | O | LYS | A | 487 | 44.198 | −34.750 | −5.069 | 1.00 | 21.31 | A | O |
| ATOM | 7754 | N | GLU | A | 488 | 44.066 | −33.073 | −3.563 | 1.00 | 22.02 | A | N |
| ATOM | 7755 | CA | GLU | A | 488 | 43.961 | −31.991 | −4.548 | 1.00 | 22.50 | A | C |
| ATOM | 7757 | CB | GLU | A | 488 | 43.814 | −30.642 | −3.829 | 1.00 | 22.80 | A | C |
| ATOM | 7760 | CG | GLU | A | 488 | 43.213 | −29.533 | −4.676 | 1.00 | 23.18 | A | C |
| ATOM | 7763 | CD | GLU | A | 488 | 41.700 | −29.614 | −4.749 | 1.00 | 24.54 | A | C |
| ATOM | 7764 | OE1 | GLU | A | 488 | 41.174 | −30.005 | −5.813 | 1.00 | 26.04 | A | O |
| ATOM | 7765 | OE2 | GLU | A | 488 | 41.037 | −29.300 | −3.736 | 1.00 | 23.72 | A | O |
| ATOM | 7766 | C | GLU | A | 488 | 45.175 | −31.939 | −5.484 | 1.00 | 22.62 | A | C |
| ATOM | 7767 | O | GLU | A | 488 | 45.030 | −31.728 | −6.692 | 1.00 | 22.91 | A | O |
| ATOM | 7769 | N | LYS | A | 489 | 46.364 | −32.126 | −4.914 | 1.00 | 22.30 | A | N |
| ATOM | 7770 | CA | LYS | A | 489 | 47.612 | −32.113 | −5.679 | 1.00 | 22.00 | A | C |
| ATOM | 7772 | CB | LYS | A | 489 | 48.811 | −32.096 | −4.722 | 1.00 | 21.67 | A | C |
| ATOM | 7775 | CG | LYS | A | 489 | 50.184 | −32.043 | −5.393 | 1.00 | 21.43 | A | C |
| ATOM | 7778 | CD | LYS | A | 489 | 50.461 | −30.695 | −6.050 | 1.00 | 20.14 | A | C |
| ATOM | 7781 | CE | LYS | A | 489 | 51.730 | −30.743 | −6.890 | 1.00 | 19.82 | A | C |
| ATOM | 7784 | NZ | LYS | A | 489 | 52.931 | −31.125 | −6.095 | 1.00 | 17.92 | A | N |
| ATOM | 7788 | C | LYS | A | 489 | 47.701 | −33.322 | −6.611 | 1.00 | 22.11 | A | C |

TABLE 8-2-continued

Coordinates for L494P Structure

| | | | | | | | | | | | | |
|---|---|---|---|---|---|---|---|---|---|---|---|---|
| ATOM | 7789 | O | LYS | A | 489 | 48.096 | −33.198 | −7.773 | 1.00 | 21.65 | A | O |
| ATOM | 7791 | N | LEU | A | 490 | 47.327 | −34.488 | −6.093 | 1.00 | 22.42 | A | N |
| ATOM | 7792 | CA | LEU | A | 490 | 47.446 | −35.738 | −6.839 | 1.00 | 22.44 | A | C |
| ATOM | 7794 | CB | LEU | A | 490 | 47.168 | −36.947 | −5.931 | 1.00 | 22.44 | A | C |
| ATOM | 7797 | CG | LEU | A | 490 | 47.979 | −38.212 | −6.227 | 1.00 | 21.83 | A | C |
| ATOM | 7799 | CD1 | LEU | A | 490 | 49.430 | −38.021 | −5.803 | 1.00 | 20.81 | A | C |
| ATOM | 7803 | CD2 | LEU | A | 490 | 47.375 | −39.425 | −5.528 | 1.00 | 22.00 | A | C |
| ATOM | 7807 | C | LEU | A | 490 | 46.513 | −35.751 | −8.049 | 1.00 | 22.61 | A | C |
| ATOM | 7808 | O | LEU | A | 490 | 46.851 | −36.327 | −9.084 | 1.00 | 22.97 | A | O |
| ATOM | 7810 | N | GLY | A | 491 | 45.347 | −35.118 | −7.919 | 1.00 | 22.59 | A | N |
| ATOM | 7811 | CA | GLY | A | 491 | 44.416 | −35.003 | −9.038 | 1.00 | 22.92 | A | C |
| ATOM | 7814 | C | GLY | A | 491 | 43.025 | −34.538 | −8.654 | 1.00 | 23.38 | A | C |
| ATOM | 7815 | O | GLY | A | 491 | 42.667 | −34.519 | −7.479 | 1.00 | 23.58 | A | O |
| ATOM | 7817 | N | GLY | A | 492 | 42.242 | −34.164 | −9.662 | 1.00 | 24.00 | A | N |
| ATOM | 7818 | CA | GLY | A | 492 | 40.868 | −33.719 | −9.464 | 1.00 | 24.68 | A | C |
| ATOM | 7821 | C | GLY | A | 492 | 40.714 | −32.217 | −9.284 | 1.00 | 25.47 | A | C |
| ATOM | 7822 | O | GLY | A | 492 | 39.590 | −31.710 | −9.219 | 1.00 | 26.12 | A | O |
| ATOM | 7824 | N | SER | A | 493 | 41.829 | −31.495 | −9.204 | 1.00 | 25.71 | A | N |
| ATOM | 7825 | CA | SER | A | 493 | 41.777 | −30.049 | −9.019 | 1.00 | 25.75 | A | C |
| ATOM | 7827 | CB | SER | A | 493 | 43.159 | −29.494 | −8.656 | 1.00 | 26.12 | A | C |
| ATOM | 7830 | OG | SER | A | 493 | 43.108 | −28.096 | −8.407 | 1.00 | 25.68 | A | O |
| ATOM | 7832 | C | SER | A | 493 | 41.268 | −29.373 | −10.287 | 1.00 | 25.36 | A | C |
| ATOM | 7833 | O | SER | A | 493 | 41.558 | −29.836 | −11.390 | 1.00 | 25.36 | A | O |
| ATOM | 7835 | N | PRO | A | 494 | 40.493 | −28.285 | −10.134 | 1.00 | 25.03 | A | N |
| ATOM | 7836 | CA | PRO | A | 494 | 40.128 | −27.456 | −11.280 | 1.00 | 24.84 | A | C |
| ATOM | 7838 | CB | PRO | A | 494 | 38.930 | −26.657 | −10.766 | 1.00 | 24.98 | A | C |
| ATOM | 7841 | CG | PRO | A | 494 | 39.143 | −26.559 | −9.306 | 1.00 | 25.14 | A | C |
| ATOM | 7844 | CD | PRO | A | 494 | 39.871 | −27.804 | −8.887 | 1.00 | 25.07 | A | C |
| ATOM | 7847 | C | PRO | A | 494 | 41.269 | −26.525 | −11.699 | 1.00 | 24.33 | A | C |
| ATOM | 7848 | O | PRO | A | 494 | 41.251 | −25.992 | −12.809 | 1.00 | 24.46 | A | O |
| ATOM | 7849 | N | PHE | A | 495 | 42.242 | −26.332 | −10.809 | 1.00 | 23.65 | A | N |
| ATOM | 7850 | CA | PHE | A | 495 | 43.440 | −25.554 | −11.110 | 1.00 | 23.36 | A | C |
| ATOM | 7852 | CB | PHE | A | 495 | 43.903 | −24.783 | −9.872 | 1.00 | 23.58 | A | C |
| ATOM | 7855 | CG | PHE | A | 495 | 42.904 | −23.784 | −9.374 | 1.00 | 23.05 | A | C |
| ATOM | 7856 | CD1 | PHE | A | 495 | 42.977 | −22.457 | −9.760 | 1.00 | 21.76 | A | C |
| ATOM | 7858 | CE1 | PHE | A | 495 | 42.052 | −21.539 | −9.302 | 1.00 | 22.61 | A | C |
| ATOM | 7860 | CZ | PHE | A | 495 | 41.036 | −21.946 | −8.454 | 1.00 | 22.69 | A | C |
| ATOM | 7862 | CE2 | PHE | A | 495 | 40.953 | −23.264 | −8.068 | 1.00 | 23.16 | A | C |
| ATOM | 7864 | CD2 | PHE | A | 495 | 41.883 | −24.175 | −8.525 | 1.00 | 23.51 | A | C |
| ATOM | 7866 | C | PHE | A | 495 | 44.561 | −26.470 | −11.576 | 1.00 | 23.05 | A | C |
| ATOM | 7867 | O | PHE | A | 495 | 44.538 | −27.676 | −11.325 | 1.00 | 22.76 | A | O |
| ATOM | 7869 | N | ALA | A | 496 | 45.545 | −25.886 | −12.253 | 1.00 | 22.91 | A | N |
| ATOM | 7870 | CA | ALA | A | 496 | 46.730 | −26.622 | −12.677 | 1.00 | 22.83 | A | C |
| ATOM | 7872 | CB | ALA | A | 496 | 47.528 | −25.806 | −13.681 | 1.00 | 23.00 | A | C |
| ATOM | 7876 | C | ALA | A | 496 | 47.586 | −26.957 | −11.461 | 1.00 | 22.74 | A | C |
| ATOM | 7877 | O | ALA | A | 496 | 47.573 | −26.229 | −10.469 | 1.00 | 23.03 | A | O |
| ATOM | 7879 | N | LYS | A | 497 | 48.331 | −28.056 | −11.544 | 1.00 | 22.67 | A | N |
| ATOM | 7880 | CA | LYS | A | 497 | 49.160 | −28.523 | −10.424 | 1.00 | 22.50 | A | C |
| ATOM | 7882 | CB | LYS | A | 497 | 49.887 | −29.828 | −10.785 | 1.00 | 22.80 | A | C |
| ATOM | 7885 | CG | LYS | A | 497 | 48.946 | −31.004 | −11.042 | 1.00 | 24.08 | A | C |
| ATOM | 7888 | CD | LYS | A | 497 | 49.679 | −32.344 | −11.050 | 1.00 | 24.82 | A | C |
| ATOM | 7891 | CE | LYS | A | 497 | 48.703 | −33.508 | −11.215 | 1.00 | 24.18 | A | C |
| ATOM | 7894 | NZ | LYS | A | 497 | 49.301 | −34.815 | −10.828 | 1.00 | 23.44 | A | N |
| ATOM | 7898 | C | LYS | A | 497 | 50.161 | −27.474 | −9.917 | 1.00 | 21.54 | A | C |
| ATOM | 7899 | O | LYS | A | 497 | 50.391 | −27.385 | −8.712 | 1.00 | 21.63 | A | O |
| ATOM | 7901 | N | PRO | A | 498 | 50.763 | −26.684 | −10.828 | 1.00 | 20.42 | A | N |
| ATOM | 7902 | CA | PRO | A | 498 | 51.606 | −25.575 | −10.392 | 1.00 | 19.81 | A | C |
| ATOM | 7904 | CB | PRO | A | 498 | 51.853 | −24.807 | −11.689 | 1.00 | 20.02 | A | C |
| ATOM | 7907 | CG | PRO | A | 498 | 51.868 | −25.858 | −12.730 | 1.00 | 20.71 | A | C |
| ATOM | 7910 | CD | PRO | A | 498 | 50.921 | −26.940 | −12.272 | 1.00 | 20.44 | A | C |
| ATOM | 7913 | C | PRO | A | 498 | 50.954 | −24.665 | −9.353 | 1.00 | 19.16 | A | C |
| ATOM | 7914 | O | PRO | A | 498 | 51.549 | −24.416 | −8.304 | 1.00 | 19.10 | A | O |
| ATOM | 7915 | N | PHE | A | 499 | 49.745 | −24.184 | −9.636 | 1.00 | 18.41 | A | N |
| ATOM | 7916 | CA | PHE | A | 499 | 49.067 | −23.259 | −8.725 | 1.00 | 17.71 | A | C |
| ATOM | 7918 | CB | PHE | A | 499 | 47.876 | −22.577 | −9.394 | 1.00 | 17.65 | A | C |
| ATOM | 7921 | CG | PHE | A | 499 | 47.125 | −21.666 | −8.469 | 1.00 | 17.11 | A | C |
| ATOM | 7922 | CD1 | PHE | A | 499 | 47.733 | −20.525 | −7.964 | 1.00 | 15.75 | A | C |
| ATOM | 7924 | CE1 | PHE | A | 499 | 47.059 | −19.686 | −7.097 | 1.00 | 16.82 | A | C |
| ATOM | 7926 | CZ | PHE | A | 499 | 45.760 | −19.985 | −6.715 | 1.00 | 18.26 | A | C |
| ATOM | 7928 | CE2 | PHE | A | 499 | 45.146 | −21.128 | −7.203 | 1.00 | 19.35 | A | C |
| ATOM | 7930 | CD2 | PHE | A | 499 | 45.833 | −21.966 | −8.071 | 1.00 | 18.48 | A | C |
| ATOM | 7932 | C | PHE | A | 499 | 48.594 | −23.918 | −7.432 | 1.00 | 17.27 | A | C |
| ATOM | 7933 | O | PHE | A | 499 | 48.608 | −23.283 | −6.377 | 1.00 | 18.04 | A | O |
| ATOM | 7935 | N | VAL | A | 500 | 48.156 | −25.173 | −7.520 | 1.00 | 16.13 | A | N |
| ATOM | 7936 | CA | VAL | A | 500 | 47.787 | −25.947 | −6.334 | 1.00 | 15.18 | A | C |
| ATOM | 7938 | CB | VAL | A | 500 | 47.344 | −27.381 | −6.710 | 1.00 | 15.13 | A | C |
| ATOM | 7940 | CG1 | VAL | A | 500 | 46.049 | −27.346 | −7.503 | 1.00 | 15.59 | A | C |
| ATOM | 7944 | CG2 | VAL | A | 500 | 47.181 | −28.247 | −5.466 | 1.00 | 15.76 | A | C |

TABLE 8-2-continued

| Coordinates for L494P Structure | | | | | | | | | | | | |
|---|---|---|---|---|---|---|---|---|---|---|---|---|
| ATOM | 7948 | C | VAL | A | 500 | 48.972 | −26.003 | −5.367 | 1.00 | 14.53 | A | C |
| ATOM | 7949 | O | VAL | A | 500 | 48.834 | −25.683 | −4.184 | 1.00 | 14.32 | A | O |
| ATOM | 7951 | N | GLU | A | 501 | 50.134 | −26.391 | −5.893 | 1.00 | 13.78 | A | N |
| ATOM | 7952 | CA | GLU | A | 501 | 51.380 | −26.469 | −5.126 | 1.00 | 13.17 | A | C |
| ATOM | 7954 | CB | GLU | A | 501 | 52.516 | −26.953 | −6.033 | 1.00 | 13.27 | A | C |
| ATOM | 7957 | CG | GLU | A | 501 | 53.883 | −27.124 | −5.355 | 1.00 | 12.99 | A | C |
| ATOM | 7960 | CD | GLU | A | 501 | 53.936 | −28.270 | −4.360 | 1.00 | 10.75 | A | C |
| ATOM | 7961 | OE1 | GLU | A | 501 | 53.035 | −29.135 | −4.365 | 1.00 | 9.48 | A | O |
| ATOM | 7962 | OE2 | GLU | A | 501 | 54.899 | −28.308 | −3.571 | 1.00 | 9.39 | A | O |
| ATOM | 7963 | C | GLU | A | 501 | 51.759 | −25.126 | −4.505 | 1.00 | 13.02 | A | C |
| ATOM | 7964 | O | GLU | A | 501 | 52.309 | −25.083 | −3.403 | 1.00 | 12.70 | A | O |
| ATOM | 7966 | N | THR | A | 502 | 51.479 | −24.037 | −5.218 | 1.00 | 13.13 | A | N |
| ATOM | 7967 | CA | THR | A | 502 | 51.715 | −22.696 | −4.689 | 1.00 | 12.94 | A | C |
| ATOM | 7969 | CB | THR | A | 502 | 51.408 | −21.597 | −5.724 | 1.00 | 12.49 | A | C |
| ATOM | 7971 | OG1 | THR | A | 502 | 51.913 | −21.986 | −7.007 | 1.00 | 12.30 | A | O |
| ATOM | 7973 | CG2 | THR | A | 502 | 52.045 | −20.281 | −5.314 | 1.00 | 11.05 | A | C |
| ATOM | 7977 | C | THR | A | 502 | 50.849 | −22.481 | −3.453 | 1.00 | 13.75 | A | C |
| ATOM | 7978 | O | THR | A | 502 | 51.323 | −21.947 | −2.451 | 1.00 | 14.63 | A | O |
| ATOM | 7980 | N | ALA | A | 503 | 49.587 | −22.912 | −3.526 | 1.00 | 13.85 | A | N |
| ATOM | 7981 | CA | ALA | A | 503 | 48.671 | −22.838 | −2.386 | 1.00 | 13.85 | A | C |
| ATOM | 7983 | CB | ALA | A | 503 | 47.298 | −23.367 | −2.766 | 1.00 | 13.55 | A | C |
| ATOM | 7987 | C | ALA | A | 503 | 49.229 | −23.619 | −1.202 | 1.00 | 14.25 | A | C |
| ATOM | 7988 | O | ALA | A | 503 | 49.414 | −23.068 | −0.115 | 1.00 | 14.42 | A | O |
| ATOM | 7990 | N | ILE | A | 504 | 49.517 | −24.899 | −1.426 | 1.00 | 14.43 | A | N |
| ATOM | 7991 | CA | ILE | A | 504 | 50.082 | −25.762 | −0.385 | 1.00 | 14.49 | A | C |
| ATOM | 7993 | CB | ILE | A | 504 | 50.462 | −27.159 | −0.950 | 1.00 | 14.26 | A | C |
| ATOM | 7995 | CG1 | ILE | A | 504 | 49.197 | −27.968 | −1.258 | 1.00 | 13.75 | A | C |
| ATOM | 7998 | CD1 | ILE | A | 504 | 49.450 | −29.249 | −2.022 | 1.00 | 11.62 | A | C |
| ATOM | 8002 | CG2 | ILE | A | 504 | 51.333 | −27.928 | 0.032 | 1.00 | 13.71 | A | C |
| ATOM | 8006 | C | ILE | A | 504 | 51.293 | −25.097 | 0.278 | 1.00 | 15.04 | A | C |
| ATOM | 8007 | O | ILE | A | 504 | 51.449 | −25.159 | 1.498 | 1.00 | 15.26 | A | O |
| ATOM | 8009 | N | ASN | A | 505 | 52.125 | −24.438 | −0.526 | 1.00 | 15.57 | A | N |
| ATOM | 8010 | CA | ASN | A | 505 | 53.295 | −23.716 | −0.014 | 1.00 | 16.27 | A | C |
| ATOM | 8012 | CB | ASN | A | 505 | 54.117 | −23.135 | −1.175 | 1.00 | 16.20 | A | C |
| ATOM | 8015 | CG | ASN | A | 505 | 54.937 | −24.191 | −1.910 | 1.00 | 16.68 | A | C |
| ATOM | 8016 | OD1 | ASN | A | 505 | 55.408 | −25.164 | −1.317 | 1.00 | 14.13 | A | O |
| ATOM | 8017 | ND2 | ASN | A | 505 | 55.122 | −23.989 | −3.213 | 1.00 | 16.63 | A | N |
| ATOM | 8020 | C | ASN | A | 505 | 52.973 | −22.607 | 1.014 | 1.00 | 16.76 | A | C |
| ATOM | 8021 | O | ASN | A | 505 | 53.840 | −22.239 | 1.811 | 1.00 | 17.12 | A | O |
| ATOM | 8023 | N | LEU | A | 506 | 51.749 | −22.074 | 0.995 | 1.00 | 16.63 | A | N |
| ATOM | 8024 | CA | LEU | A | 506 | 51.303 | −21.135 | 2.034 | 1.00 | 16.26 | A | C |
| ATOM | 8026 | CB | LEU | A | 506 | 49.936 | −20.530 | 1.694 | 1.00 | 16.36 | A | C |
| ATOM | 8029 | CG | LEU | A | 506 | 49.433 | −19.409 | 2.615 | 1.00 | 15.61 | A | C |
| ATOM | 8031 | CD1 | LEU | A | 506 | 50.134 | −18.100 | 2.305 | 1.00 | 16.15 | A | C |
| ATOM | 8035 | CD2 | LEU | A | 506 | 47.930 | −19.241 | 2.488 | 1.00 | 15.78 | A | C |
| ATOM | 8039 | C | LEU | A | 506 | 51.220 | −21.858 | 3.373 | 1.00 | 16.06 | A | C |
| ATOM | 8040 | O | LEU | A | 506 | 51.719 | −21.363 | 4.387 | 1.00 | 15.94 | A | O |
| ATOM | 8042 | N | ALA | A | 507 | 50.582 | −23.028 | 3.367 | 1.00 | 15.76 | A | N |
| ATOM | 8043 | CA | ALA | A | 507 | 50.483 | −23.862 | 4.563 | 1.00 | 15.58 | A | C |
| ATOM | 8045 | CB | ALA | A | 507 | 49.733 | −25.148 | 4.257 | 1.00 | 15.54 | A | C |
| ATOM | 8049 | C | ALA | A | 507 | 51.867 | −24.178 | 5.109 | 1.00 | 15.59 | A | C |
| ATOM | 8050 | O | ALA | A | 507 | 52.095 | −24.098 | 6.316 | 1.00 | 14.90 | A | O |
| ATOM | 8052 | N | ARG | A | 508 | 52.787 | −24.531 | 4.210 | 1.00 | 16.16 | A | N |
| ATOM | 8053 | CA | ARG | A | 508 | 54.174 | −24.806 | 4.585 | 1.00 | 16.29 | A | C |
| ATOM | 8055 | CB | ARG | A | 508 | 55.026 | −25.165 | 3.364 | 1.00 | 16.26 | A | C |
| ATOM | 8058 | CG | ARG | A | 508 | 54.660 | −26.473 | 2.679 | 1.00 | 17.94 | A | C |
| ATOM | 8061 | CD | ARG | A | 508 | 55.608 | −26.763 | 1.521 | 1.00 | 19.98 | A | C |
| ATOM | 8064 | NE | ARG | A | 508 | 54.905 | −27.288 | 0.346 | 1.00 | 21.98 | A | N |
| ATOM | 8066 | CZ | ARG | A | 508 | 54.787 | −28.577 | 0.019 | 1.00 | 22.61 | A | C |
| ATOM | 8067 | NH1 | ARG | A | 508 | 55.324 | −29.538 | 0.767 | 1.00 | 22.88 | A | N |
| ATOM | 8070 | NH2 | ARG | A | 508 | 54.120 | −28.910 | −1.080 | 1.00 | 22.72 | A | N |
| ATOM | 8073 | C | ARG | A | 508 | 54.783 | −23.598 | 5.274 | 1.00 | 16.50 | A | C |
| ATOM | 8074 | O | ARG | A | 508 | 55.366 | −23.724 | 6.347 | 1.00 | 16.45 | A | O |
| ATOM | 8076 | N | GLN | A | 509 | 54.634 | −22.430 | 4.652 | 1.00 | 17.01 | A | N |
| ATOM | 8077 | CA | GLN | A | 509 | 55.139 | −21.180 | 5.218 | 1.00 | 17.44 | A | C |
| ATOM | 8079 | CB | GLN | A | 509 | 54.932 | −20.022 | 4.233 | 1.00 | 17.64 | A | C |
| ATOM | 8082 | CG | GLN | A | 509 | 55.378 | −18.640 | 4.743 | 1.00 | 18.86 | A | C |
| ATOM | 8085 | CD | GLN | A | 509 | 56.866 | −18.559 | 5.059 | 1.00 | 19.80 | A | C |
| ATOM | 8086 | OE1 | GLN | A | 509 | 57.698 | −19.142 | 4.364 | 1.00 | 21.40 | A | O |
| ATOM | 8087 | NE2 | GLN | A | 509 | 57.205 | −17.824 | 6.109 | 1.00 | 20.43 | A | N |
| ATOM | 8090 | C | GLN | A | 509 | 54.489 | −20.856 | 6.566 | 1.00 | 17.62 | A | C |
| ATOM | 8091 | O | GLN | A | 509 | 55.147 | −20.310 | 7.452 | 1.00 | 17.58 | A | O |
| ATOM | 8093 | N | SER | A | 510 | 53.208 | −21.190 | 6.722 | 1.00 | 18.00 | A | N |
| ATOM | 8094 | CA | SER | A | 510 | 52.519 | −20.976 | 7.995 | 1.00 | 18.54 | A | C |
| ATOM | 8096 | CB | SER | A | 510 | 51.036 | −21.331 | 7.892 | 1.00 | 18.47 | A | C |
| ATOM | 8099 | OG | SER | A | 510 | 50.356 | −20.392 | 7.083 | 1.00 | 18.50 | A | O |
| ATOM | 8101 | C | SER | A | 510 | 53.182 | −21.778 | 9.109 | 1.00 | 19.15 | A | C |
| ATOM | 8102 | O | SER | A | 510 | 53.583 | −21.212 | 10.124 | 1.00 | 19.12 | A | O |

TABLE 8-2-continued

Coordinates for L494P Structure

| | | | | | | | | | | | | |
|---|---|---|---|---|---|---|---|---|---|---|---|---|
| ATOM | 8104 | N | HIS | A | 511 | 53.307 | −23.088 | 8.907 | 1.00 | 20.18 | A | N |
| ATOM | 8105 | CA | HIS | A | 511 | 54.032 | −23.956 | 9.844 | 1.00 | 21.08 | A | C |
| ATOM | 8107 | CB | HIS | A | 511 | 54.180 | −25.378 | 9.276 | 1.00 | 20.92 | A | C |
| ATOM | 8110 | CG | HIS | A | 511 | 52.976 | −26.246 | 9.480 | 1.00 | 21.15 | A | C |
| ATOM | 8111 | ND1 | HIS | A | 511 | 52.496 | −26.574 | 10.731 | 1.00 | 23.07 | A | N |
| ATOM | 8113 | CE1 | HIS | A | 511 | 51.438 | −27.355 | 10.605 | 1.00 | 21.16 | A | C |
| ATOM | 8115 | NE2 | HIS | A | 511 | 51.220 | −27.555 | 9.318 | 1.00 | 20.02 | A | N |
| ATOM | 8117 | CD2 | HIS | A | 511 | 52.171 | −26.877 | 8.593 | 1.00 | 20.33 | A | C |
| ATOM | 8119 | C | HIS | A | 511 | 55.422 | −23.394 | 10.176 | 1.00 | 22.01 | A | C |
| ATOM | 8120 | O | HIS | A | 511 | 55.836 | −23.382 | 11.340 | 1.00 | 22.10 | A | O |
| ATOM | 8122 | N | CYS | A | 512 | 56.127 | −22.928 | 9.145 | 1.00 | 22.75 | A | N |
| ATOM | 8123 | CA | CYS | A | 512 | 57.489 | −22.410 | 9.291 | 1.00 | 23.31 | A | C |
| ATOM | 8125 | CB | CYS | A | 512 | 58.162 | −22.308 | 7.918 | 1.00 | 23.29 | A | C |
| ATOM | 8128 | SG | CYS | A | 512 | 58.272 | −23.878 | 7.018 | 1.00 | 23.12 | A | S |
| ATOM | 8130 | C | CYS | A | 512 | 57.560 | −21.048 | 9.997 | 1.00 | 24.05 | A | C |
| ATOM | 8131 | O | CYS | A | 512 | 58.612 | −20.683 | 10.522 | 1.00 | 24.32 | A | O |
| ATOM | 8133 | N | THR | A | 513 | 56.455 | −20.303 | 10.006 | 1.00 | 24.74 | A | N |
| ATOM | 8134 | CA | THR | A | 513 | 56.424 | −18.975 | 10.627 | 1.00 | 25.50 | A | C |
| ATOM | 8136 | CB | THR | A | 513 | 55.556 | −17.982 | 9.806 | 1.00 | 25.40 | A | C |
| ATOM | 8138 | OG1 | THR | A | 513 | 56.349 | −17.410 | 8.760 | 1.00 | 24.78 | A | O |
| ATOM | 8140 | CG2 | THR | A | 513 | 55.027 | −16.856 | 10.681 | 1.00 | 25.88 | A | C |
| ATOM | 8144 | C | THR | A | 513 | 55.948 | −19.012 | 12.082 | 1.00 | 26.41 | A | C |
| ATOM | 8145 | O | THR | A | 513 | 56.535 | −18.347 | 12.940 | 1.00 | 26.85 | A | O |
| ATOM | 8147 | N | TYR | A | 514 | 54.899 | −19.786 | 12.361 | 1.00 | 27.13 | A | N |
| ATOM | 8148 | CA | TYR | A | 514 | 54.304 | −19.828 | 13.703 | 1.00 | 27.65 | A | C |
| ATOM | 8150 | CB | TYR | A | 514 | 52.780 | −19.915 | 13.608 | 1.00 | 27.23 | A | C |
| ATOM | 8153 | CG | TYR | A | 514 | 52.205 | −18.699 | 12.929 | 1.00 | 25.40 | A | C |
| ATOM | 8154 | CD1 | TYR | A | 514 | 52.107 | −17.486 | 13.607 | 1.00 | 24.39 | A | C |
| ATOM | 8156 | CE1 | TYR | A | 514 | 51.598 | −16.355 | 12.985 | 1.00 | 22.46 | A | C |
| ATOM | 8158 | CZ | TYR | A | 514 | 51.196 | −16.428 | 11.667 | 1.00 | 21.99 | A | C |
| ATOM | 8159 | OH | TYR | A | 514 | 50.694 | −15.313 | 11.041 | 1.00 | 21.78 | A | O |
| ATOM | 8161 | CE2 | TYR | A | 514 | 51.297 | −17.618 | 10.969 | 1.00 | 22.62 | A | C |
| ATOM | 8163 | CD2 | TYR | A | 514 | 51.804 | −18.743 | 11.600 | 1.00 | 22.78 | A | C |
| ATOM | 8165 | C | TYR | A | 514 | 54.883 | −20.942 | 14.571 | 1.00 | 29.02 | A | C |
| ATOM | 8166 | O | TYR | A | 514 | 54.290 | −22.013 | 14.724 | 1.00 | 28.90 | A | O |
| ATOM | 8168 | N | HIS | A | 515 | 56.057 | −20.655 | 15.129 | 1.00 | 30.73 | A | N |
| ATOM | 8169 | CA | HIS | A | 515 | 56.761 | −21.538 | 16.063 | 1.00 | 32.06 | A | C |
| ATOM | 8171 | CB | HIS | A | 515 | 58.121 | −21.948 | 15.484 | 1.00 | 32.40 | A | C |
| ATOM | 8174 | CG | HIS | A | 515 | 59.036 | −20.791 | 15.217 | 1.00 | 33.80 | A | C |
| ATOM | 8175 | ND1 | HIS | A | 515 | 59.022 | −20.090 | 14.030 | 1.00 | 34.76 | A | N |
| ATOM | 8177 | CE1 | HIS | A | 515 | 59.920 | −19.122 | 14.081 | 1.00 | 35.38 | A | C |
| ATOM | 8179 | NE2 | HIS | A | 515 | 60.513 | −19.166 | 15.261 | 1.00 | 35.75 | A | N |
| ATOM | 8181 | CD2 | HIS | A | 515 | 59.977 | −20.200 | 15.991 | 1.00 | 34.95 | A | C |
| ATOM | 8183 | C | HIS | A | 515 | 56.966 | −20.796 | 17.389 | 1.00 | 32.51 | A | C |
| ATOM | 8184 | O | HIS | A | 515 | 56.694 | −19.593 | 17.484 | 1.00 | 32.74 | A | O |
| ATOM | 8186 | N | ASN | A | 516 | 57.448 | −21.517 | 18.401 | 1.00 | 32.73 | A | N |
| ATOM | 8187 | CA | ASN | A | 516 | 57.747 | −20.931 | 19.713 | 1.00 | 32.96 | A | C |
| ATOM | 8189 | CB | ASN | A | 516 | 56.625 | −21.237 | 20.715 | 1.00 | 33.20 | A | C |
| ATOM | 8192 | CG | ASN | A | 516 | 55.351 | −20.436 | 20.446 | 1.00 | 33.85 | A | C |
| ATOM | 8193 | OD1 | ASN | A | 516 | 54.596 | −20.730 | 19.512 | 1.00 | 31.44 | A | O |
| ATOM | 8194 | ND2 | ASN | A | 516 | 55.097 | −19.430 | 21.283 | 1.00 | 33.00 | A | N |
| ATOM | 8197 | C | ASN | A | 516 | 59.081 | −21.436 | 20.261 | 1.00 | 32.91 | A | C |
| ATOM | 8198 | O | ASN | A | 516 | 60.121 | −21.308 | 19.611 | 1.00 | 33.04 | A | O |
| ATOM | 8200 | N | THR | A | 521 | 66.548 | −21.132 | 21.796 | 1.00 | 40.70 | A | N |
| ATOM | 8201 | CA | THR | A | 521 | 66.207 | −20.050 | 20.874 | 1.00 | 40.78 | A | C |
| ATOM | 8203 | CB | THR | A | 521 | 66.436 | −20.476 | 19.406 | 1.00 | 40.62 | A | C |
| ATOM | 8205 | OG1 | THR | A | 521 | 67.703 | −21.134 | 19.285 | 1.00 | 39.94 | A | O |
| ATOM | 8207 | CG2 | THR | A | 521 | 66.402 | −19.267 | 18.478 | 1.00 | 40.21 | A | C |
| ATOM | 8211 | C | THR | A | 521 | 64.746 | −19.619 | 21.056 | 1.00 | 41.19 | A | C |
| ATOM | 8212 | O | THR | A | 521 | 63.841 | −20.460 | 21.049 | 1.00 | 41.68 | A | O |
| ATOM | 8214 | N | SER | A | 522 | 64.523 | −18.313 | 21.209 | 1.00 | 41.01 | A | N |
| ATOM | 8215 | CA | SER | A | 522 | 63.182 | −17.767 | 21.453 | 1.00 | 40.95 | A | C |
| ATOM | 8217 | CB | SER | A | 522 | 63.294 | −16.355 | 22.049 | 1.00 | 40.91 | A | C |
| ATOM | 8220 | OG | SER | A | 522 | 63.552 | −15.382 | 21.052 | 1.00 | 40.15 | A | O |
| ATOM | 8222 | C | SER | A | 522 | 62.329 | −17.754 | 20.168 | 1.00 | 41.29 | A | C |
| ATOM | 8223 | O | SER | A | 522 | 62.835 | −18.071 | 19.089 | 1.00 | 41.26 | A | O |
| ATOM | 8225 | N | PRO | A | 523 | 61.026 | −17.409 | 20.282 | 1.00 | 41.67 | A | N |
| ATOM | 8226 | CA | PRO | A | 523 | 60.172 | −17.283 | 19.088 | 1.00 | 41.68 | A | C |
| ATOM | 8228 | CB | PRO | A | 523 | 58.815 | −16.856 | 19.666 | 1.00 | 41.63 | A | C |
| ATOM | 8231 | CG | PRO | A | 523 | 58.807 | −17.408 | 21.044 | 1.00 | 41.77 | A | C |
| ATOM | 8234 | CD | PRO | A | 523 | 60.230 | −17.359 | 21.526 | 1.00 | 41.83 | A | C |
| ATOM | 8237 | C | PRO | A | 523 | 60.679 | −16.274 | 18.041 | 1.00 | 41.69 | A | C |
| ATOM | 8238 | O | PRO | A | 523 | 60.935 | −16.665 | 16.900 | 1.00 | 41.96 | A | O |
| ATOM | 8239 | N | ASP | A | 524 | 60.820 | −15.003 | 18.422 | 1.00 | 41.43 | A | N |
| ATOM | 8240 | CA | ASP | A | 524 | 61.364 | −13.979 | 17.522 | 1.00 | 41.02 | A | C |
| ATOM | 8242 | CB | ASP | A | 524 | 60.602 | −12.652 | 17.664 | 1.00 | 41.31 | A | C |
| ATOM | 8245 | CG | ASP | A | 524 | 60.708 | −11.774 | 16.417 | 1.00 | 42.01 | A | C |
| ATOM | 8246 | OD1 | ASP | A | 524 | 61.842 | −11.469 | 15.989 | 1.00 | 42.29 | A | O |

TABLE 8-2-continued

Coordinates for L494P Structure

| | | | | | | | | | | | | |
|---|---|---|---|---|---|---|---|---|---|---|---|---|
| ATOM | 8247 | OD2 | ASP | A | 524 | 59.655 | −11.387 | 15.865 | 1.00 | 42.57 | A | O |
| ATOM | 8248 | C | ASP | A | 524 | 62.854 | −13.803 | 17.824 | 1.00 | 40.28 | A | C |
| ATOM | 8249 | O | ASP | A | 524 | 63.228 | −13.154 | 18.802 | 1.00 | 40.11 | A | O |
| ATOM | 8251 | N | GLU | A | 525 | 63.681 | −14.371 | 16.946 | 1.00 | 39.60 | A | N |
| ATOM | 8252 | CA | GLU | A | 525 | 65.126 | −14.597 | 17.159 | 1.00 | 39.35 | A | C |
| ATOM | 8254 | CB | GLU | A | 525 | 65.483 | −14.783 | 18.645 | 1.00 | 39.51 | A | C |
| ATOM | 8257 | CG | GLU | A | 525 | 66.978 | −14.944 | 18.955 | 1.00 | 40.12 | A | C |
| ATOM | 8260 | CD | GLU | A | 525 | 67.789 | −13.676 | 18.721 | 1.00 | 41.52 | A | C |
| ATOM | 8261 | OE1 | GLU | A | 525 | 69.013 | −13.799 | 18.496 | 1.00 | 41.73 | A | O |
| ATOM | 8262 | OE2 | GLU | A | 525 | 67.217 | −12.562 | 18.760 | 1.00 | 41.99 | A | O |
| ATOM | 8263 | C | GLU | A | 525 | 65.554 | −15.835 | 16.352 | 1.00 | 38.94 | A | C |
| ATOM | 8264 | O | GLU | A | 525 | 66.736 | −15.994 | 16.020 | 1.00 | 39.49 | A | O |
| ATOM | 8266 | N | LEU | A | 526 | 64.589 | −16.716 | 16.072 | 1.00 | 37.92 | A | N |
| ATOM | 8267 | CA | LEU | A | 526 | 64.740 | −17.769 | 15.068 | 1.00 | 36.89 | A | C |
| ATOM | 8269 | CB | LEU | A | 526 | 64.024 | −19.049 | 15.516 | 1.00 | 36.77 | A | C |
| ATOM | 8272 | CG | LEU | A | 526 | 64.013 | −20.253 | 14.565 | 1.00 | 36.82 | A | C |
| ATOM | 8274 | CD1 | LEU | A | 526 | 63.540 | −21.504 | 15.302 | 1.00 | 35.24 | A | C |
| ATOM | 8278 | CD2 | LEU | A | 526 | 65.382 | −20.492 | 13.935 | 1.00 | 36.63 | A | C |
| ATOM | 8282 | C | LEU | A | 526 | 64.185 | −17.262 | 13.735 | 1.00 | 36.23 | A | C |
| ATOM | 8283 | O | LEU | A | 526 | 64.661 | −17.654 | 12.671 | 1.00 | 36.06 | A | O |
| ATOM | 8285 | N | THR | A | 527 | 63.177 | −16.391 | 13.805 | 1.00 | 35.70 | A | N |
| ATOM | 8286 | CA | THR | A | 527 | 62.713 | −15.630 | 12.643 | 1.00 | 35.26 | A | C |
| ATOM | 8288 | CB | THR | A | 527 | 61.469 | −14.766 | 12.981 | 1.00 | 35.09 | A | C |
| ATOM | 8290 | OG1 | THR | A | 527 | 60.448 | −15.587 | 13.560 | 1.00 | 35.42 | A | O |
| ATOM | 8292 | CG2 | THR | A | 527 | 60.918 | −14.084 | 11.730 | 1.00 | 33.75 | A | C |
| ATOM | 8296 | C | THR | A | 527 | 63.817 | −14.705 | 12.121 | 1.00 | 35.05 | A | C |
| ATOM | 8297 | O | THR | A | 527 | 63.915 | −14.473 | 10.914 | 1.00 | 35.33 | A | O |
| ATOM | 8299 | N | ARG | A | 528 | 64.645 | −14.185 | 13.029 | 1.00 | 34.45 | A | N |
| ATOM | 8300 | CA | ARG | A | 528 | 65.746 | −13.295 | 12.654 | 1.00 | 34.07 | A | C |
| ATOM | 8302 | CB | ARG | A | 528 | 66.399 | −12.684 | 13.897 | 1.00 | 34.21 | A | C |
| ATOM | 8305 | CG | ARG | A | 528 | 67.430 | −11.597 | 13.577 | 1.00 | 35.79 | A | C |
| ATOM | 8308 | CD | ARG | A | 528 | 68.237 | −11.153 | 14.802 | 1.00 | 37.39 | A | C |
| ATOM | 8311 | NE | ARG | A | 528 | 68.738 | −12.271 | 15.607 | 1.00 | 38.17 | A | N |
| ATOM | 8313 | CZ | ARG | A | 528 | 69.715 | −13.105 | 15.245 | 1.00 | 37.53 | A | C |
| ATOM | 8314 | NH1 | ARG | A | 528 | 70.333 | −12.981 | 14.072 | 1.00 | 36.61 | A | N |
| ATOM | 8317 | NH2 | ARG | A | 528 | 70.079 | −14.085 | 16.066 | 1.00 | 37.93 | A | N |
| ATOM | 8320 | C | ARG | A | 528 | 66.801 | −14.024 | 11.819 | 1.00 | 33.31 | A | C |
| ATOM | 8321 | O | ARG | A | 528 | 67.225 | −13.525 | 10.774 | 1.00 | 33.25 | A | O |
| ATOM | 8323 | N | LYS | A | 529 | 67.221 | −15.198 | 12.287 | 1.00 | 32.35 | A | N |
| ATOM | 8324 | CA | LYS | A | 529 | 68.219 | −16.003 | 11.579 | 1.00 | 31.60 | A | C |
| ATOM | 8326 | CB | LYS | A | 529 | 68.676 | −17.186 | 12.439 | 1.00 | 31.66 | A | C |
| ATOM | 8329 | CG | LYS | A | 529 | 69.437 | −16.800 | 13.696 | 1.00 | 31.41 | A | C |
| ATOM | 8332 | CD | LYS | A | 529 | 69.959 | −18.035 | 14.408 | 1.00 | 31.32 | A | C |
| ATOM | 8335 | CE | LYS | A | 529 | 70.798 | −17.669 | 15.617 | 1.00 | 32.31 | A | C |
| ATOM | 8338 | NZ | LYS | A | 529 | 71.369 | −18.876 | 16.276 | 1.00 | 33.65 | A | N |
| ATOM | 8342 | C | LYS | A | 529 | 67.670 | −16.531 | 10.260 | 1.00 | 30.95 | A | C |
| ATOM | 8343 | O | LYS | A | 529 | 68.297 | −16.364 | 9.213 | 1.00 | 30.56 | A | O |
| ATOM | 8345 | N | ARG | A | 530 | 66.501 | −17.170 | 10.329 | 1.00 | 30.64 | A | N |
| ATOM | 8346 | CA | ARG | A | 530 | 65.846 | −17.760 | 9.153 | 1.00 | 30.15 | A | C |
| ATOM | 8348 | CB | ARG | A | 530 | 64.482 | −18.362 | 9.525 | 1.00 | 29.94 | A | C |
| ATOM | 8351 | CG | ARG | A | 530 | 64.561 | −19.726 | 10.225 | 1.00 | 29.01 | A | C |
| ATOM | 8354 | CD | ARG | A | 530 | 63.171 | −20.281 | 10.550 | 1.00 | 27.64 | A | C |
| ATOM | 8357 | NE | ARG | A | 530 | 63.220 | −21.609 | 11.172 | 1.00 | 25.77 | A | N |
| ATOM | 8359 | CZ | ARG | A | 530 | 62.150 | −22.322 | 11.537 | 1.00 | 23.97 | A | C |
| ATOM | 8360 | NH1 | ARG | A | 530 | 60.921 | −21.851 | 11.352 | 1.00 | 22.79 | A | N |
| ATOM | 8363 | NH2 | ARG | A | 530 | 62.307 | −23.518 | 12.092 | 1.00 | 23.31 | A | N |
| ATOM | 8366 | C | ARG | A | 530 | 65.689 | −16.746 | 8.017 | 1.00 | 30.16 | A | C |
| ATOM | 8367 | O | ARG | A | 530 | 65.923 | −17.075 | 6.853 | 1.00 | 30.17 | A | O |
| ATOM | 8369 | N | VAL | A | 531 | 65.304 | −15.518 | 8.360 | 1.00 | 30.09 | A | N |
| ATOM | 8370 | CA | VAL | A | 531 | 65.249 | −14.423 | 7.384 | 1.00 | 29.85 | A | C |
| ATOM | 8372 | CB | VAL | A | 531 | 64.687 | −13.116 | 8.009 | 1.00 | 29.92 | A | C |
| ATOM | 8374 | CG1 | VAL | A | 531 | 65.130 | −11.891 | 7.212 | 1.00 | 29.47 | A | C |
| ATOM | 8378 | CG2 | VAL | A | 531 | 63.166 | −13.183 | 8.090 | 1.00 | 30.50 | A | C |
| ATOM | 8382 | C | VAL | A | 531 | 66.628 | −14.151 | 6.781 | 1.00 | 29.24 | A | C |
| ATOM | 8383 | O | VAL | A | 531 | 66.781 | −14.158 | 5.559 | 1.00 | 29.23 | A | O |
| ATOM | 8385 | N | LEU | A | 532 | 67.623 | −13.925 | 7.639 | 1.00 | 28.50 | A | N |
| ATOM | 8386 | CA | LEU | A | 532 | 68.994 | −13.652 | 7.186 | 1.00 | 28.01 | A | C |
| ATOM | 8388 | CB | LEU | A | 532 | 69.944 | −13.450 | 8.378 | 1.00 | 28.09 | A | C |
| ATOM | 8391 | CG | LEU | A | 532 | 70.095 | −12.013 | 8.894 | 1.00 | 28.78 | A | C |
| ATOM | 8393 | CD1 | LEU | A | 532 | 68.741 | −11.373 | 9.211 | 1.00 | 28.04 | A | C |
| ATOM | 8397 | CD2 | LEU | A | 532 | 71.014 | −11.979 | 10.112 | 1.00 | 28.59 | A | C |
| ATOM | 8401 | C | LEU | A | 532 | 69.533 | −14.754 | 6.272 | 1.00 | 27.20 | A | C |
| ATOM | 8402 | O | LEU | A | 532 | 70.151 | −14.470 | 5.243 | 1.00 | 26.80 | A | O |
| ATOM | 8404 | N | SER | A | 533 | 69.283 | −16.004 | 6.652 | 1.00 | 26.36 | A | N |
| ATOM | 8405 | CA | SER | A | 533 | 69.742 | −17.159 | 5.883 | 1.00 | 25.65 | A | C |
| ATOM | 8407 | CB | SER | A | 533 | 69.573 | −18.437 | 6.705 | 1.00 | 25.79 | A | C |
| ATOM | 8410 | OG | SER | A | 533 | 68.231 | −18.588 | 7.127 | 1.00 | 26.13 | A | O |
| ATOM | 8412 | C | SER | A | 533 | 69.009 | −17.306 | 4.549 | 1.00 | 24.80 | A | C |

TABLE 8-2-continued

Coordinates for L494P Structure

| | | | | | | | | | | | | |
|---|---|---|---|---|---|---|---|---|---|---|---|---|
| ATOM | 8413 | O | SER | A | 533 | 69.589 | −17.786 | 3.573 | 1.00 | 24.87 | A | O |
| ATOM | 8415 | N | VAL | A | 534 | 67.742 | −16.897 | 4.514 | 1.00 | 23.73 | A | N |
| ATOM | 8416 | CA | VAL | A | 534 | 66.930 | −16.993 | 3.299 | 1.00 | 22.78 | A | C |
| ATOM | 8418 | CB | VAL | A | 534 | 65.442 | −17.279 | 3.634 | 1.00 | 22.62 | A | C |
| ATOM | 8420 | CG1 | VAL | A | 534 | 64.574 | −17.176 | 2.393 | 1.00 | 22.83 | A | C |
| ATOM | 8424 | CG2 | VAL | A | 534 | 65.299 | −18.661 | 4.247 | 1.00 | 20.75 | A | C |
| ATOM | 8428 | C | VAL | A | 534 | 67.063 | −15.751 | 2.407 | 1.00 | 22.04 | A | C |
| ATOM | 8429 | O | VAL | A | 534 | 67.186 | −15.880 | 1.188 | 1.00 | 21.64 | A | O |
| ATOM | 8431 | N | ILE | A | 535 | 67.058 | −14.562 | 3.010 | 1.00 | 21.46 | A | N |
| ATOM | 8432 | CA | ILE | A | 535 | 67.090 | −13.304 | 2.249 | 1.00 | 21.12 | A | C |
| ATOM | 8434 | CB | ILE | A | 535 | 66.130 | −12.241 | 2.845 | 1.00 | 21.03 | A | C |
| ATOM | 8436 | CG1 | ILE | A | 535 | 64.702 | −12.782 | 2.954 | 1.00 | 19.56 | A | C |
| ATOM | 8439 | CD1 | ILE | A | 535 | 64.055 | −13.076 | 1.628 | 1.00 | 18.99 | A | C |
| ATOM | 8443 | CG2 | ILE | A | 535 | 66.138 | −10.979 | 1.990 | 1.00 | 20.45 | A | C |
| ATOM | 8447 | C | ILE | A | 535 | 68.488 | −12.678 | 2.122 | 1.00 | 21.08 | A | C |
| ATOM | 8448 | O | ILE | A | 535 | 69.043 | −12.638 | 1.025 | 1.00 | 21.16 | A | O |
| ATOM | 8450 | N | THR | A | 536 | 69.049 | −12.188 | 3.229 | 1.00 | 21.05 | A | N |
| ATOM | 8451 | CA | THR | A | 536 | 70.220 | −11.290 | 3.167 | 1.00 | 21.47 | A | C |
| ATOM | 8453 | CB | THR | A | 536 | 70.259 | −10.315 | 4.373 | 1.00 | 21.61 | A | C |
| ATOM | 8455 | OG1 | THR | A | 536 | 70.381 | −11.053 | 5.593 | 1.00 | 23.10 | A | O |
| ATOM | 8457 | CG2 | THR | A | 536 | 68.993 | −9.465 | 4.422 | 1.00 | 22.21 | A | C |
| ATOM | 8461 | C | THR | A | 536 | 71.587 | −11.983 | 3.039 | 1.00 | 20.97 | A | C |
| ATOM | 8462 | O | THR | A | 536 | 72.308 | −11.747 | 2.069 | 1.00 | 20.73 | A | O |
| ATOM | 8464 | N | GLU | A | 537 | 71.947 | −12.817 | 4.013 | 1.00 | 20.65 | A | N |
| ATOM | 8465 | CA | GLU | A | 537 | 73.259 | −13.474 | 4.017 | 1.00 | 20.51 | A | C |
| ATOM | 8467 | CB | GLU | A | 537 | 73.649 | −13.911 | 5.432 | 1.00 | 20.64 | A | C |
| ATOM | 8470 | CG | GLU | A | 537 | 73.824 | −12.751 | 6.409 | 1.00 | 21.25 | A | C |
| ATOM | 8473 | CD | GLU | A | 537 | 74.728 | −13.076 | 7.590 | 1.00 | 20.98 | A | C |
| ATOM | 8474 | OE1 | GLU | A | 537 | 74.910 | −12.186 | 8.448 | 1.00 | 19.76 | A | O |
| ATOM | 8475 | OE2 | GLU | A | 537 | 75.261 | −14.205 | 7.663 | 1.00 | 20.90 | A | O |
| ATOM | 8476 | C | GLU | A | 537 | 73.294 | −14.689 | 3.088 | 1.00 | 20.36 | A | C |
| ATOM | 8477 | O | GLU | A | 537 | 72.475 | −15.599 | 3.235 | 1.00 | 20.54 | A | O |
| ATOM | 8479 | N | PRO | A | 538 | 74.244 | −14.718 | 2.130 | 1.00 | 20.10 | A | N |
| ATOM | 8480 | CA | PRO | A | 538 | 74.398 | −15.928 | 1.321 | 1.00 | 19.67 | A | C |
| ATOM | 8482 | CB | PRO | A | 538 | 75.354 | −15.495 | 0.198 | 1.00 | 19.39 | A | C |
| ATOM | 8485 | CG | PRO | A | 538 | 75.435 | −14.010 | 0.274 | 1.00 | 19.88 | A | C |
| ATOM | 8488 | CD | PRO | A | 538 | 75.155 | −13.647 | 1.688 | 1.00 | 20.22 | A | C |
| ATOM | 8491 | C | PRO | A | 538 | 75.009 | −17.071 | 2.123 | 1.00 | 19.62 | A | C |
| ATOM | 8492 | O | PRO | A | 538 | 75.449 | −16.868 | 3.256 | 1.00 | 19.61 | A | O |
| ATOM | 8493 | N | ILE | A | 539 | 75.027 | −18.263 | 1.534 | 1.00 | 19.52 | A | N |
| ATOM | 8494 | CA | ILE | A | 539 | 75.661 | −19.422 | 2.154 | 1.00 | 19.35 | A | C |
| ATOM | 8496 | CB | ILE | A | 539 | 75.149 | −20.739 | 1.535 | 1.00 | 19.15 | A | C |
| ATOM | 8498 | CG1 | ILE | A | 539 | 73.656 | −20.902 | 1.813 | 1.00 | 19.17 | A | C |
| ATOM | 8501 | CD1 | ILE | A | 539 | 73.079 | −22.205 | 1.311 | 1.00 | 19.79 | A | C |
| ATOM | 8505 | CG2 | ILE | A | 539 | 75.913 | −21.934 | 2.090 | 1.00 | 19.34 | A | C |
| ATOM | 8509 | C | ILE | A | 539 | 77.173 | −19.326 | 1.977 | 1.00 | 19.38 | A | C |
| ATOM | 8510 | O | ILE | A | 539 | 77.652 | −18.812 | 0.963 | 1.00 | 18.71 | A | O |
| ATOM | 8512 | N | LEU | A | 540 | 77.920 | −19.810 | 2.969 | 1.00 | 19.89 | A | N |
| ATOM | 8513 | CA | LEU | A | 540 | 79.379 | −19.852 | 2.876 | 1.00 | 20.47 | A | C |
| ATOM | 8515 | CB | LEU | A | 540 | 80.001 | −20.467 | 4.139 | 1.00 | 20.46 | A | C |
| ATOM | 8518 | CG | LEU | A | 540 | 79.948 | −19.634 | 5.427 | 1.00 | 20.08 | A | C |
| ATOM | 8520 | CD1 | LEU | A | 540 | 80.419 | −20.457 | 6.618 | 1.00 | 18.44 | A | C |
| ATOM | 8524 | CD2 | LEU | A | 540 | 80.775 | −18.359 | 5.296 | 1.00 | 17.67 | A | C |
| ATOM | 8528 | C | LEU | A | 540 | 79.765 | −20.664 | 1.638 | 1.00 | 20.82 | A | C |
| ATOM | 8529 | O | LEU | A | 540 | 79.241 | −21.761 | 1.438 | 1.00 | 20.93 | A | O |
| ATOM | 8531 | N | PRO | A | 541 | 80.669 | −20.123 | 0.797 | 1.00 | 21.10 | A | N |
| ATOM | 8532 | CA | PRO | A | 541 | 80.960 | −20.737 | −0.501 | 1.00 | 21.17 | A | C |
| ATOM | 8534 | CB | PRO | A | 541 | 81.831 | −19.687 | −1.197 | 1.00 | 20.94 | A | C |
| ATOM | 8537 | CG | PRO | A | 541 | 82.477 | −18.951 | −0.096 | 1.00 | 21.31 | A | C |
| ATOM | 8540 | CD | PRO | A | 541 | 81.484 | −18.917 | 1.024 | 1.00 | 21.15 | A | C |
| ATOM | 8543 | C | PRO | A | 541 | 81.692 | −22.071 | −0.401 | 1.00 | 21.47 | A | C |
| ATOM | 8544 | O | PRO | A | 541 | 82.045 | −22.508 | 0.693 | 1.00 | 21.43 | A | O |
| ATOM | 8545 | N | PHE | A | 542 | 81.915 | −22.701 | −1.550 | 1.00 | 22.16 | A | N |
| ATOM | 8546 | CA | PHE | A | 542 | 82.488 | −24.043 | −1.607 | 1.00 | 22.83 | A | C |
| ATOM | 8548 | CB | PHE | A | 542 | 82.148 | −24.685 | −2.953 | 1.00 | 22.75 | A | C |
| ATOM | 8551 | CG | PHE | A | 542 | 82.651 | −26.095 | −3.102 | 1.00 | 22.87 | A | C |
| ATOM | 8552 | CD1 | PHE | A | 542 | 83.477 | −26.446 | −4.163 | 1.00 | 22.56 | A | C |
| ATOM | 8554 | CE1 | PHE | A | 542 | 83.938 | −27.747 | −4.306 | 1.00 | 21.48 | A | C |
| ATOM | 8556 | CZ | PHE | A | 542 | 83.581 | −28.712 | −3.382 | 1.00 | 21.47 | A | C |
| ATOM | 8558 | CE2 | PHE | A | 542 | 82.760 | −28.376 | −2.316 | 1.00 | 22.09 | A | C |
| ATOM | 8560 | CD2 | PHE | A | 542 | 82.301 | −27.073 | −2.180 | 1.00 | 22.60 | A | C |
| ATOM | 8562 | C | PHE | A | 542 | 84.007 | −24.066 | −1.386 | 1.00 | 23.60 | A | C |
| ATOM | 8563 | O | PHE | A | 542 | 84.750 | −23.309 | −2.017 | 1.00 | 23.24 | A | O |
| ATOM | 8565 | N | GLU | A | 543 | 84.447 | −24.940 | −0.480 | 1.00 | 24.65 | A | N |
| ATOM | 8566 | CA | GLU | A | 543 | 85.867 | −25.238 | −0.264 | 1.00 | 25.63 | A | C |
| ATOM | 8568 | CB | GLU | A | 543 | 86.242 | −25.032 | 1.209 | 1.00 | 25.64 | A | C |
| ATOM | 8571 | CG | GLU | A | 543 | 86.531 | −23.587 | 1.593 | 1.00 | 25.04 | A | C |
| ATOM | 8574 | CD | GLU | A | 543 | 87.219 | −23.462 | 2.945 | 1.00 | 24.31 | A | C |

TABLE 8-2-continued

Coordinates for L494P Structure

| | | | | | | | | | | | | |
|---|---|---|---|---|---|---|---|---|---|---|---|---|
| ATOM | 8575 | OE1 | GLU | A | 543 | 87.195 | −24.433 | 3.733 | 1.00 | 23.03 | A | O |
| ATOM | 8576 | OE2 | GLU | A | 543 | 87.787 | −22.385 | 3.219 | 1.00 | 23.80 | A | O |
| ATOM | 8577 | C | GLU | A | 543 | 86.149 | −26.685 | −0.685 | 1.00 | 26.60 | A | C |
| ATOM | 8578 | O | GLU | A | 543 | 85.244 | −27.387 | −1.132 | 1.00 | 26.93 | A | O |
| ATOM | 8580 | N | ARG | A | 544 | 87.398 | −27.128 | −0.543 | 1.00 | 27.49 | A | N |
| ATOM | 8581 | CA | ARG | A | 544 | 87.790 | −28.496 | −0.904 | 1.00 | 28.18 | A | C |
| ATOM | 8583 | CB | ARG | A | 544 | 88.462 | −28.503 | −2.283 | 1.00 | 28.70 | A | C |
| ATOM | 8586 | CG | ARG | A | 544 | 87.480 | −28.538 | −3.454 | 1.00 | 30.13 | A | C |
| ATOM | 8589 | CD | ARG | A | 544 | 87.958 | −27.689 | −4.627 | 1.00 | 32.27 | A | C |
| ATOM | 8592 | NE | ARG | A | 544 | 87.029 | −27.745 | −5.758 | 1.00 | 34.04 | A | N |
| ATOM | 8594 | CZ | ARG | A | 544 | 86.969 | −26.853 | −6.749 | 1.00 | 35.15 | A | C |
| ATOM | 8595 | NH1 | ARG | A | 544 | 87.785 | −25.801 | −6.780 | 1.00 | 35.93 | A | N |
| ATOM | 8598 | NH2 | ARG | A | 544 | 86.078 | −27.010 | −7.722 | 1.00 | 35.60 | A | N |
| ATOM | 8601 | C | ARG | A | 544 | 88.718 | −29.113 | 0.148 | 1.00 | 28.07 | A | C |
| ATOM | 8602 | O | ARG | A | 544 | 89.936 | −28.927 | 0.113 | 1.00 | 27.79 | A | O |
| ATOM | 8604 | N | SER | B | 6 | 65.194 | 37.534 | 11.490 | 1.00 | 30.93 | B | N |
| ATOM | 8605 | CA | SER | B | 6 | 66.501 | 38.213 | 11.258 | 1.00 | 31.10 | B | C |
| ATOM | 8607 | CB | SER | B | 6 | 67.126 | 38.622 | 12.599 | 1.00 | 31.12 | B | C |
| ATOM | 8610 | OG | SER | B | 6 | 68.384 | 39.251 | 12.418 | 1.00 | 30.48 | B | O |
| ATOM | 8612 | C | SER | B | 6 | 67.433 | 37.305 | 10.437 | 1.00 | 31.29 | B | C |
| ATOM | 8613 | O | SER | B | 6 | 67.056 | 36.867 | 9.347 | 1.00 | 31.44 | B | O |
| ATOM | 8617 | N | ALA | B | 7 | 68.634 | 37.031 | 10.954 | 1.00 | 31.29 | B | N |
| ATOM | 8618 | CA | ALA | B | 7 | 69.633 | 36.190 | 10.276 | 1.00 | 31.27 | B | C |
| ATOM | 8620 | CB | ALA | B | 7 | 70.875 | 36.063 | 11.153 | 1.00 | 31.07 | B | C |
| ATOM | 8624 | C | ALA | B | 7 | 69.128 | 34.792 | 9.894 | 1.00 | 31.29 | B | C |
| ATOM | 8625 | O | ALA | B | 7 | 68.262 | 34.227 | 10.566 | 1.00 | 31.47 | B | O |
| ATOM | 8627 | N | ASN | B | 8 | 69.690 | 34.242 | 8.817 | 1.00 | 31.13 | B | N |
| ATOM | 8628 | CA | ASN | B | 8 | 69.342 | 32.903 | 8.333 | 1.00 | 30.87 | B | C |
| ATOM | 8630 | CB | ASN | B | 8 | 68.536 | 33.009 | 7.033 | 1.00 | 30.78 | B | C |
| ATOM | 8633 | CG | ASN | B | 8 | 68.152 | 31.652 | 6.460 | 1.00 | 30.33 | B | C |
| ATOM | 8634 | OD1 | ASN | B | 8 | 67.997 | 30.671 | 7.187 | 1.00 | 30.31 | B | O |
| ATOM | 8635 | ND2 | ASN | B | 8 | 67.988 | 31.597 | 5.144 | 1.00 | 29.92 | B | N |
| ATOM | 8638 | C | ASN | B | 8 | 70.591 | 32.048 | 8.110 | 1.00 | 30.77 | B | C |
| ATOM | 8639 | O | ASN | B | 8 | 71.467 | 32.411 | 7.324 | 1.00 | 30.68 | B | O |
| ATOM | 8641 | N | TYR | B | 9 | 70.659 | 30.915 | 8.808 | 1.00 | 30.85 | B | N |
| ATOM | 8642 | CA | TYR | B | 9 | 71.782 | 29.980 | 8.700 | 1.00 | 30.90 | B | C |
| ATOM | 8644 | CB | TYR | B | 9 | 72.394 | 29.745 | 10.081 | 1.00 | 30.91 | B | C |
| ATOM | 8647 | CG | TYR | B | 9 | 72.941 | 30.996 | 10.724 | 1.00 | 31.38 | B | C |
| ATOM | 8648 | CD1 | TYR | B | 9 | 74.066 | 31.627 | 10.207 | 1.00 | 31.49 | B | C |
| ATOM | 8650 | CE1 | TYR | B | 9 | 74.577 | 32.772 | 10.792 | 1.00 | 31.53 | B | C |
| ATOM | 8652 | CZ | TYR | B | 9 | 73.963 | 33.302 | 11.915 | 1.00 | 31.18 | B | C |
| ATOM | 8653 | OH | TYR | B | 9 | 74.464 | 34.440 | 12.505 | 1.00 | 31.64 | B | O |
| ATOM | 8655 | CE2 | TYR | B | 9 | 72.845 | 32.694 | 12.449 | 1.00 | 30.98 | B | C |
| ATOM | 8657 | CD2 | TYR | B | 9 | 72.340 | 31.545 | 11.853 | 1.00 | 31.50 | B | C |
| ATOM | 8659 | C | TYR | B | 9 | 71.392 | 28.628 | 8.099 | 1.00 | 30.89 | B | C |
| ATOM | 8660 | O | TYR | B | 9 | 72.244 | 27.749 | 7.954 | 1.00 | 30.84 | B | O |
| ATOM | 8662 | N | GLU | B | 10 | 70.118 | 28.461 | 7.748 | 1.00 | 30.91 | B | N |
| ATOM | 8663 | CA | GLU | B | 10 | 69.619 | 27.177 | 7.254 | 1.00 | 30.96 | B | C |
| ATOM | 8665 | CB | GLU | B | 10 | 68.090 | 27.193 | 7.135 | 1.00 | 31.16 | B | C |
| ATOM | 8668 | CG | GLU | B | 10 | 67.357 | 27.168 | 8.477 | 1.00 | 32.67 | B | C |
| ATOM | 8671 | CD | GLU | B | 10 | 65.997 | 26.478 | 8.404 | 1.00 | 34.80 | B | C |
| ATOM | 8672 | OE1 | GLU | B | 10 | 65.359 | 26.497 | 7.327 | 1.00 | 35.78 | B | O |
| ATOM | 8673 | OE2 | GLU | B | 10 | 65.564 | 25.914 | 9.433 | 1.00 | 34.93 | B | O |
| ATOM | 8674 | C | GLU | B | 10 | 70.237 | 26.801 | 5.905 | 1.00 | 30.57 | B | C |
| ATOM | 8675 | O | GLU | B | 10 | 70.673 | 27.678 | 5.156 | 1.00 | 30.27 | B | O |
| ATOM | 8677 | N | PRO | B | 11 | 70.281 | 25.490 | 5.596 | 1.00 | 30.23 | B | N |
| ATOM | 8678 | CA | PRO | B | 11 | 70.814 | 25.038 | 4.314 | 1.00 | 29.93 | B | C |
| ATOM | 8680 | CB | PRO | B | 11 | 70.985 | 23.528 | 4.519 | 1.00 | 29.85 | B | C |
| ATOM | 8683 | CG | PRO | B | 11 | 69.977 | 23.171 | 5.533 | 1.00 | 29.86 | B | C |
| ATOM | 8686 | CD | PRO | B | 11 | 69.874 | 24.357 | 6.448 | 1.00 | 30.23 | B | C |
| ATOM | 8689 | C | PRO | B | 11 | 69.862 | 25.312 | 3.154 | 1.00 | 29.66 | B | C |
| ATOM | 8690 | O | PRO | B | 11 | 68.641 | 25.250 | 3.325 | 1.00 | 29.68 | B | O |
| ATOM | 8691 | N | ASN | B | 12 | 70.428 | 25.631 | 1.993 | 1.00 | 29.25 | B | N |
| ATOM | 8692 | CA | ASN | B | 12 | 69.672 | 25.660 | 0.747 | 1.00 | 28.94 | B | C |
| ATOM | 8694 | CB | ASN | B | 12 | 70.298 | 26.638 | −0.252 | 1.00 | 29.10 | B | C |
| ATOM | 8697 | CG | ASN | B | 12 | 70.210 | 28.086 | 0.208 | 1.00 | 29.53 | B | C |
| ATOM | 8698 | OD1 | ASN | B | 12 | 69.136 | 28.575 | 0.559 | 1.00 | 31.39 | B | O |
| ATOM | 8699 | ND2 | ASN | B | 12 | 71.342 | 28.782 | 0.196 | 1.00 | 28.62 | B | N |
| ATOM | 8702 | C | ASN | B | 12 | 69.646 | 24.253 | 0.162 | 1.00 | 28.62 | B | C |
| ATOM | 8703 | O | ASN | B | 12 | 70.554 | 23.458 | 0.409 | 1.00 | 28.75 | B | O |
| ATOM | 8705 | N | SER | B | 13 | 68.600 | 23.943 | −0.600 | 1.00 | 28.28 | B | N |
| ATOM | 8706 | CA | SER | B | 13 | 68.467 | 22.629 | −1.238 | 1.00 | 27.84 | B | C |
| ATOM | 8708 | CB | SER | B | 13 | 67.066 | 22.466 | −1.842 | 1.00 | 27.87 | B | C |
| ATOM | 8711 | OG | SER | B | 13 | 66.698 | 23.594 | −2.621 | 1.00 | 27.68 | B | O |
| ATOM | 8713 | C | SER | B | 13 | 69.540 | 22.403 | −2.312 | 1.00 | 27.33 | B | C |
| ATOM | 8714 | O | SER | B | 13 | 69.999 | 21.280 | −2.514 | 1.00 | 27.15 | B | O |
| ATOM | 8716 | N | TRP | B | 14 | 69.941 | 23.480 | −2.982 | 1.00 | 26.98 | B | N |
| ATOM | 8717 | CA | TRP | B | 14 | 70.947 | 23.410 | −4.047 | 1.00 | 27.01 | B | C |

TABLE 8-2-continued

| Coordinates for L494P Structure | | | | | | | | | | | |
|---|---|---|---|---|---|---|---|---|---|---|---|
| ATOM | 8719 | CB | TRP | B | 14 | 70.801 | 24.595 | −5.025 | 1.00 | 27.03 B | C |
| ATOM | 8722 | CG | TRP | B | 14 | 70.521 | 25.947 | −4.396 | 1.00 | 27.01 B | C |
| ATOM | 8723 | CD1 | TRP | B | 14 | 69.295 | 26.521 | −4.199 | 1.00 | 27.14 B | C |
| ATOM | 8725 | NE1 | TRP | B | 14 | 69.435 | 27.754 | −3.612 | 1.00 | 26.54 B | N |
| ATOM | 8727 | CE2 | TRP | B | 14 | 70.768 | 28.009 | −3.426 | 1.00 | 27.41 B | C |
| ATOM | 8728 | CD2 | TRP | B | 14 | 71.485 | 26.892 | −3.911 | 1.00 | 27.68 B | C |
| ATOM | 8729 | CE3 | TRP | B | 14 | 72.884 | 26.902 | −3.834 | 1.00 | 29.36 B | C |
| ATOM | 8731 | CZ3 | TRP | B | 14 | 73.516 | 28.014 | −3.281 | 1.00 | 30.23 B | C |
| ATOM | 8733 | CH2 | TRP | B | 14 | 72.773 | 29.109 | −2.808 | 1.00 | 29.91 B | C |
| ATOM | 8735 | CZ2 | TRP | B | 14 | 71.402 | 29.125 | −2.873 | 1.00 | 28.79 B | C |
| ATOM | 8737 | C | TRP | B | 14 | 72.402 | 23.306 | −3.548 | 1.00 | 27.02 B | C |
| ATOM | 8738 | O | TRP | B | 14 | 73.290 | 22.935 | −4.320 | 1.00 | 26.74 B | O |
| ATOM | 8740 | N | ASP | B | 15 | 72.638 | 23.614 | −2.270 | 1.00 | 26.93 B | N |
| ATOM | 8741 | CA | ASP | B | 15 | 73.999 | 23.688 | −1.705 | 1.00 | 26.86 B | C |
| ATOM | 8743 | CB | ASP | B | 15 | 73.944 | 23.887 | −0.182 | 1.00 | 26.86 B | C |
| ATOM | 8746 | CG | ASP | B | 15 | 73.721 | 25.336 | 0.219 | 1.00 | 26.99 B | C |
| ATOM | 8747 | OD1 | ASP | B | 15 | 73.870 | 26.238 | −0.637 | 1.00 | 24.43 B | O |
| ATOM | 8748 | OD2 | ASP | B | 15 | 73.406 | 25.571 | 1.408 | 1.00 | 27.44 B | O |
| ATOM | 8749 | C | ASP | B | 15 | 74.894 | 22.484 | −2.010 | 1.00 | 26.90 B | C |
| ATOM | 8750 | O | ASP | B | 15 | 74.415 | 21.365 | −2.191 | 1.00 | 26.83 B | O |
| ATOM | 8752 | N | TYR | B | 16 | 76.202 | 22.739 | −2.039 | 1.00 | 27.18 B | N |
| ATOM | 8753 | CA | TYR | B | 16 | 77.202 | 21.717 | −2.361 | 1.00 | 27.47 B | C |
| ATOM | 8755 | CB | TYR | B | 16 | 78.530 | 22.369 | −2.767 | 1.00 | 27.32 B | C |
| ATOM | 8758 | CG | TYR | B | 16 | 78.492 | 23.077 | −4.106 | 1.00 | 25.78 B | C |
| ATOM | 8759 | CD1 | TYR | B | 16 | 78.255 | 22.372 | −5.283 | 1.00 | 24.46 B | C |
| ATOM | 8761 | CE1 | TYR | B | 16 | 78.223 | 23.015 | −6.512 | 1.00 | 23.58 B | C |
| ATOM | 8763 | CZ | TYR | B | 16 | 78.436 | 24.378 | −6.576 | 1.00 | 23.84 B | C |
| ATOM | 8764 | OH | TYR | B | 16 | 78.405 | 25.020 | −7.792 | 1.00 | 23.45 B | O |
| ATOM | 8766 | CE2 | TYR | B | 16 | 78.679 | 25.100 | −5.422 | 1.00 | 24.10 B | C |
| ATOM | 8768 | CD2 | TYR | B | 16 | 78.707 | 24.446 | −4.197 | 1.00 | 24.90 B | C |
| ATOM | 8770 | C | TYR | B | 16 | 77.449 | 20.724 | −1.219 | 1.00 | 28.17 B | C |
| ATOM | 8771 | O | TYR | B | 16 | 77.971 | 19.635 | −1.455 | 1.00 | 28.00 B | O |
| ATOM | 8773 | N | ASP | B | 17 | 77.100 | 21.103 | 0.009 | 1.00 | 28.94 B | N |
| ATOM | 8774 | CA | ASP | B | 17 | 77.182 | 20.189 | 1.153 | 1.00 | 29.33 B | C |
| ATOM | 8776 | CB | ASP | B | 17 | 77.135 | 20.960 | 2.479 | 1.00 | 29.08 B | C |
| ATOM | 8779 | CG | ASP | B | 17 | 78.279 | 21.954 | 2.627 | 1.00 | 28.02 B | C |
| ATOM | 8780 | OD1 | ASP | B | 17 | 78.883 | 22.334 | 1.602 | 1.00 | 26.84 B | O |
| ATOM | 8781 | OD2 | ASP | B | 17 | 78.570 | 22.364 | 3.770 | 1.00 | 26.76 B | O |
| ATOM | 8782 | C | ASP | B | 17 | 76.026 | 19.188 | 1.087 | 1.00 | 30.23 B | C |
| ATOM | 8783 | O | ASP | B | 17 | 76.202 | 17.997 | 1.355 | 1.00 | 30.34 B | O |
| ATOM | 8785 | N | TYR | B | 18 | 74.847 | 19.697 | 0.728 | 1.00 | 31.12 B | N |
| ATOM | 8786 | CA | TYR | B | 18 | 73.640 | 18.888 | 0.552 | 1.00 | 32.00 B | C |
| ATOM | 8788 | CB | TYR | B | 18 | 72.432 | 19.814 | 0.349 | 1.00 | 32.50 B | C |
| ATOM | 8791 | CG | TYR | B | 18 | 71.072 | 19.146 | 0.372 | 1.00 | 34.76 B | C |
| ATOM | 8792 | CD1 | TYR | B | 18 | 70.211 | 19.321 | 1.455 | 1.00 | 37.40 B | C |
| ATOM | 8794 | CE1 | TYR | B | 18 | 68.955 | 18.727 | 1.479 | 1.00 | 38.40 B | C |
| ATOM | 8796 | CZ | TYR | B | 18 | 68.545 | 17.952 | 0.408 | 1.00 | 38.58 B | C |
| ATOM | 8797 | OH | TYR | B | 18 | 67.302 | 17.361 | 0.428 | 1.00 | 39.64 B | O |
| ATOM | 8799 | CE2 | TYR | B | 18 | 69.378 | 17.770 | −0.683 | 1.00 | 37.47 B | C |
| ATOM | 8801 | CD2 | TYR | B | 18 | 70.631 | 18.369 | −0.698 | 1.00 | 35.94 B | C |
| ATOM | 8803 | C | TYR | B | 18 | 73.821 | 17.938 | −0.634 | 1.00 | 32.06 B | C |
| ATOM | 8804 | O | TYR | B | 18 | 73.879 | 16.722 | −0.447 | 1.00 | 32.28 B | O |
| ATOM | 8806 | N | LEU | B | 19 | 73.916 | 18.495 | −1.844 | 1.00 | 31.97 B | N |
| ATOM | 8807 | CA | LEU | B | 19 | 74.291 | 17.725 | −3.033 | 1.00 | 31.81 B | C |
| ATOM | 8809 | CB | LEU | B | 19 | 74.101 | 18.552 | −4.310 | 1.00 | 31.61 B | C |
| ATOM | 8812 | CG | LEU | B | 19 | 72.673 | 18.884 | −4.747 | 1.00 | 31.60 B | C |
| ATOM | 8814 | CD1 | LEU | B | 19 | 72.676 | 20.011 | −5.771 | 1.00 | 29.70 B | C |
| ATOM | 8818 | CD2 | LEU | B | 19 | 71.975 | 17.650 | −5.307 | 1.00 | 32.90 B | C |
| ATOM | 8822 | C | LEU | B | 19 | 75.755 | 17.334 | −2.900 | 1.00 | 32.11 B | C |
| ATOM | 8823 | O | LEU | B | 19 | 76.478 | 17.920 | −2.100 | 1.00 | 32.07 B | O |
| ATOM | 8825 | N | LEU | B | 20 | 76.188 | 16.346 | −3.679 | 1.00 | 32.38 B | N |
| ATOM | 8826 | CA | LEU | B | 20 | 77.580 | 15.881 | −3.655 | 1.00 | 32.60 B | C |
| ATOM | 8828 | CB | LEU | B | 20 | 78.543 | 17.016 | −4.048 | 1.00 | 32.67 B | C |
| ATOM | 8831 | CG | LEU | B | 20 | 78.184 | 17.857 | −5.275 | 1.00 | 32.36 B | C |
| ATOM | 8833 | CD1 | LEU | B | 20 | 79.247 | 18.915 | −5.510 | 1.00 | 31.31 B | C |
| ATOM | 8837 | CD2 | LEU | B | 20 | 78.023 | 16.976 | −6.502 | 1.00 | 32.73 B | C |
| ATOM | 8841 | C | LEU | B | 20 | 77.976 | 15.298 | −2.289 | 1.00 | 32.78 B | C |
| ATOM | 8842 | O | LEU | B | 20 | 78.727 | 15.917 | −1.531 | 1.00 | 32.45 B | O |
| ATOM | 8844 | N | SER | B | 21 | 77.462 | 14.108 | −1.984 | 1.00 | 33.27 B | N |
| ATOM | 8845 | CA | SER | B | 21 | 77.803 | 13.407 | −0.740 | 1.00 | 33.68 B | C |
| ATOM | 8847 | CB | SER | B | 21 | 76.696 | 13.592 | 0.307 | 1.00 | 33.73 B | C |
| ATOM | 8850 | OG | SER | B | 21 | 75.453 | 13.090 | −0.153 | 1.00 | 33.56 B | O |
| ATOM | 8852 | C | SER | B | 21 | 78.067 | 11.916 | −0.981 | 1.00 | 33.90 B | C |
| ATOM | 8853 | O | SER | B | 21 | 77.611 | 11.344 | −1.976 | 1.00 | 33.89 B | O |
| ATOM | 8855 | N | SER | B | 22 | 78.813 | 11.303 | −0.063 | 1.00 | 34.06 B | N |
| ATOM | 8856 | CA | SER | B | 22 | 79.177 | 9.888 | −0.163 | 1.00 | 34.19 B | C |
| ATOM | 8858 | CB | SER | B | 22 | 80.431 | 9.720 | −1.026 | 1.00 | 34.22 B | C |
| ATOM | 8861 | OG | SER | B | 22 | 81.500 | 10.512 | −0.537 | 1.00 | 34.16 B | O |

TABLE 8-2-continued

| Coordinates for L494P Structure | | | | | | | | | | | |
|---|---|---|---|---|---|---|---|---|---|---|---|
| ATOM | 8863 | C | SER | B | 22 | 79.417 | 9.282 | 1.218 | 1.00 | 34.24 B | C |
| ATOM | 8864 | O | SER | B | 22 | 78.552 | 8.598 | 1.766 | 1.00 | 34.40 B | O |
| ATOM | 8866 | N | ILE | B | 28 | 83.096 | 12.126 | −5.219 | 1.00 | 33.03 B | N |
| ATOM | 8867 | CA | ILE | B | 28 | 82.293 | 13.341 | −5.130 | 1.00 | 33.17 B | C |
| ATOM | 8869 | CB | ILE | B | 28 | 80.768 | 13.019 | −5.067 | 1.00 | 33.49 B | C |
| ATOM | 8871 | CG1 | ILE | B | 28 | 80.431 | 11.736 | −5.840 | 1.00 | 33.77 B | C |
| ATOM | 8874 | CD1 | ILE | B | 28 | 78.942 | 11.415 | −5.876 | 1.00 | 33.05 B | C |
| ATOM | 8878 | CG2 | ILE | B | 28 | 79.953 | 14.191 | −5.610 | 1.00 | 33.81 B | C |
| ATOM | 8882 | C | ILE | B | 28 | 82.693 | 14.165 | −3.897 | 1.00 | 33.01 B | C |
| ATOM | 8883 | O | ILE | B | 28 | 81.856 | 14.845 | −3.299 | 1.00 | 33.03 B | O |
| ATOM | 8885 | N | GLU | B | 29 | 83.977 | 14.116 | −3.537 | 1.00 | 32.83 B | N |
| ATOM | 8886 | CA | GLU | B | 29 | 84.462 | 14.714 | −2.288 | 1.00 | 32.67 B | C |
| ATOM | 8888 | CB | GLU | B | 29 | 85.136 | 13.647 | −1.429 | 1.00 | 32.76 B | C |
| ATOM | 8891 | CG | GLU | B | 29 | 84.198 | 12.510 | −1.051 | 1.00 | 33.72 B | C |
| ATOM | 8894 | CD | GLU | B | 29 | 84.786 | 11.574 | −0.012 | 1.00 | 35.62 B | C |
| ATOM | 8895 | OE1 | GLU | B | 29 | 85.447 | 12.061 | 0.932 | 1.00 | 37.99 B | O |
| ATOM | 8896 | OE2 | GLU | B | 29 | 84.579 | 10.348 | −0.136 | 1.00 | 35.42 B | O |
| ATOM | 8897 | C | GLU | B | 29 | 85.407 | 15.895 | −2.516 | 1.00 | 32.29 B | C |
| ATOM | 8898 | O | GLU | B | 29 | 85.093 | 17.019 | −2.125 | 1.00 | 32.51 B | O |
| ATOM | 8900 | N | VAL | B | 30 | 86.559 | 15.650 | −3.138 | 1.00 | 31.62 B | N |
| ATOM | 8901 | CA | VAL | B | 30 | 87.465 | 16.741 | −3.525 | 1.00 | 30.85 B | C |
| ATOM | 8903 | CB | VAL | B | 30 | 88.830 | 16.207 | −4.027 | 1.00 | 30.72 B | C |
| ATOM | 8905 | CG1 | VAL | B | 30 | 89.708 | 17.345 | −4.528 | 1.00 | 30.15 B | C |
| ATOM | 8909 | CG2 | VAL | B | 30 | 89.538 | 15.439 | −2.917 | 1.00 | 30.01 B | C |
| ATOM | 8913 | C | VAL | B | 30 | 86.787 | 17.605 | −4.600 | 1.00 | 30.37 B | C |
| ATOM | 8914 | O | VAL | B | 30 | 87.082 | 18.791 | −4.739 | 1.00 | 30.28 B | O |
| ATOM | 8916 | N | TYR | B | 31 | 85.877 | 16.984 | −5.346 | 1.00 | 29.78 B | N |
| ATOM | 8917 | CA | TYR | B | 31 | 84.969 | 17.674 | −6.262 | 1.00 | 29.51 B | C |
| ATOM | 8919 | CB | TYR | B | 31 | 84.111 | 16.625 | −6.984 | 1.00 | 29.72 B | C |
| ATOM | 8922 | CG | TYR | B | 31 | 83.435 | 17.063 | −8.268 | 1.00 | 30.61 B | C |
| ATOM | 8923 | CD1 | TYR | B | 31 | 84.175 | 17.308 | −9.424 | 1.00 | 30.75 B | C |
| ATOM | 8925 | CE1 | TYR | B | 31 | 83.548 | 17.683 | −10.614 | 1.00 | 31.57 B | C |
| ATOM | 8927 | CZ | TYR | B | 31 | 82.163 | 17.800 | −10.655 | 1.00 | 31.88 B | C |
| ATOM | 8928 | OH | TYR | B | 31 | 81.530 | 18.173 | −11.822 | 1.00 | 30.54 B | O |
| ATOM | 8930 | CE2 | TYR | B | 31 | 81.409 | 17.546 | −9.524 | 1.00 | 31.66 B | C |
| ATOM | 8932 | CD2 | TYR | B | 31 | 82.045 | 17.173 | −8.342 | 1.00 | 32.07 B | C |
| ATOM | 8934 | C | TYR | B | 31 | 84.076 | 18.654 | −5.490 | 1.00 | 28.96 B | C |
| ATOM | 8935 | O | TYR | B | 31 | 83.852 | 19.780 | −5.933 | 1.00 | 29.21 B | O |
| ATOM | 8937 | N | LYS | B | 32 | 83.574 | 18.211 | −4.336 | 1.00 | 28.11 B | N |
| ATOM | 8938 | CA | LYS | B | 32 | 82.742 | 19.037 | −3.446 | 1.00 | 27.18 B | C |
| ATOM | 8940 | CB | LYS | B | 32 | 82.091 | 18.152 | −2.368 | 1.00 | 27.40 B | C |
| ATOM | 8943 | CG | LYS | B | 32 | 81.289 | 18.888 | −1.291 | 1.00 | 27.70 B | C |
| ATOM | 8946 | CD | LYS | B | 32 | 81.011 | 17.982 | −0.088 | 1.00 | 28.13 B | C |
| ATOM | 8949 | CE | LYS | B | 32 | 82.214 | 17.904 | 0.859 | 1.00 | 27.91 B | C |
| ATOM | 8952 | NZ | LYS | B | 32 | 82.132 | 16.766 | 1.823 | 1.00 | 26.03 B | N |
| ATOM | 8956 | C | LYS | B | 32 | 83.549 | 20.159 | −2.788 | 1.00 | 26.03 B | C |
| ATOM | 8957 | O | LYS | B | 32 | 83.099 | 21.305 | −2.740 | 1.00 | 25.99 B | O |
| ATOM | 8959 | N | ASP | B | 33 | 84.731 | 19.820 | −2.274 | 1.00 | 24.80 B | N |
| ATOM | 8960 | CA | ASP | B | 33 | 85.635 | 20.807 | −1.666 | 1.00 | 23.80 B | C |
| ATOM | 8962 | CB | ASP | B | 33 | 86.882 | 20.123 | −1.073 | 1.00 | 23.97 B | C |
| ATOM | 8965 | CG | ASP | B | 33 | 86.603 | 19.412 | 0.252 | 1.00 | 23.84 B | C |
| ATOM | 8966 | OD1 | ASP | B | 33 | 85.444 | 19.021 | 0.506 | 1.00 | 24.89 B | O |
| ATOM | 8967 | OD2 | ASP | B | 33 | 87.557 | 19.238 | 1.041 | 1.00 | 21.93 B | O |
| ATOM | 8968 | C | ASP | B | 33 | 86.074 | 21.887 | −2.664 | 1.00 | 22.53 B | C |
| ATOM | 8969 | O | ASP | B | 33 | 86.377 | 23.012 | −2.270 | 1.00 | 22.50 B | O |
| ATOM | 8971 | N | LYS | B | 34 | 86.111 | 21.537 | −3.949 | 1.00 | 21.23 B | N |
| ATOM | 8972 | CA | LYS | B | 34 | 86.498 | 22.479 | −4.999 | 1.00 | 20.16 B | C |
| ATOM | 8974 | CB | LYS | B | 34 | 86.832 | 21.737 | −6.302 | 1.00 | 20.17 B | C |
| ATOM | 8977 | CG | LYS | B | 34 | 88.013 | 22.319 | −7.068 | 1.00 | 21.10 B | C |
| ATOM | 8980 | CD | LYS | B | 34 | 89.338 | 21.743 | −6.567 | 1.00 | 22.05 B | C |
| ATOM | 8983 | CE | LYS | B | 34 | 90.538 | 22.487 | −7.142 | 1.00 | 22.40 B | C |
| ATOM | 8986 | NZ | LYS | B | 34 | 90.519 | 22.547 | −8.633 | 1.00 | 22.69 B | N |
| ATOM | 8990 | C | LYS | B | 34 | 85.379 | 23.488 | −5.250 | 1.00 | 19.08 B | C |
| ATOM | 8991 | O | LYS | B | 34 | 85.622 | 24.695 | −5.277 | 1.00 | 19.11 B | O |
| ATOM | 8993 | N | ALA | B | 35 | 84.158 | 22.979 | −5.424 | 1.00 | 17.76 B | N |
| ATOM | 8994 | CA | ALA | B | 35 | 82.980 | 23.805 | −5.718 | 1.00 | 16.41 B | C |
| ATOM | 8996 | CB | ALA | B | 35 | 81.743 | 22.927 | −5.847 | 1.00 | 16.25 B | C |
| ATOM | 9000 | C | ALA | B | 35 | 82.745 | 24.878 | −4.663 | 1.00 | 15.50 B | C |
| ATOM | 9001 | O | ALA | B | 35 | 82.464 | 26.028 | −4.996 | 1.00 | 15.11 B | O |
| ATOM | 9003 | N | LYS | B | 36 | 82.857 | 24.491 | −3.395 | 1.00 | 14.95 B | N |
| ATOM | 9004 | CA | LYS | B | 36 | 82.725 | 25.426 | −2.277 | 1.00 | 14.49 B | C |
| ATOM | 9006 | CB | LYS | B | 36 | 82.866 | 24.686 | −0.941 | 1.00 | 14.64 B | C |
| ATOM | 9009 | CG | LYS | B | 36 | 81.721 | 23.724 | −0.624 | 1.00 | 14.95 B | C |
| ATOM | 9012 | CD | LYS | B | 36 | 82.093 | 22.732 | 0.482 | 1.00 | 14.25 B | C |
| ATOM | 9015 | CE | LYS | B | 36 | 82.334 | 23.418 | 1.820 | 1.00 | 12.69 B | C |
| ATOM | 9018 | NZ | LYS | B | 36 | 82.523 | 22.434 | 2.916 | 1.00 | 10.99 B | N |
| ATOM | 9022 | C | LYS | B | 36 | 83.768 | 26.541 | −2.352 | 1.00 | 13.97 B | C |
| ATOM | 9023 | O | LYS | B | 36 | 83.450 | 27.709 | −2.129 | 1.00 | 13.72 B | O |

TABLE 8-2-continued

| Coordinates for L494P Structure | | | | | | | | | | | |
|---|---|---|---|---|---|---|---|---|---|---|---|
| ATOM | 9025 | N | LYS | B | 37 | 85.007 | 26.169 | −2.673 | 1.00 | 13.59 B | N |
| ATOM | 9026 | CA | LYS | B | 37 | 86.120 | 27.119 | −2.735 | 1.00 | 13.44 B | C |
| ATOM | 9028 | CB | LYS | B | 37 | 87.457 | 26.374 | −2.816 | 1.00 | 13.67 B | C |
| ATOM | 9031 | CG | LYS | B | 37 | 88.681 | 27.282 | −2.729 | 1.00 | 15.27 B | C |
| ATOM | 9034 | CD | LYS | B | 37 | 89.950 | 26.502 | −2.393 | 1.00 | 17.27 B | C |
| ATOM | 9037 | CE | LYS | B | 37 | 91.135 | 27.436 | −2.137 | 1.00 | 17.81 B | C |
| ATOM | 9040 | NZ | LYS | B | 37 | 91.454 | 28.302 | −3.312 | 1.00 | 17.07 B | N |
| ATOM | 9044 | C | LYS | B | 37 | 86.000 | 28.100 | −3.902 | 1.00 | 12.83 B | C |
| ATOM | 9045 | O | LYS | B | 37 | 86.455 | 29.241 | −3.800 | 1.00 | 12.97 B | O |
| ATOM | 9047 | N | LEU | B | 38 | 85.398 | 27.655 | −5.003 | 1.00 | 12.14 B | N |
| ATOM | 9048 | CA | LEU | B | 38 | 85.198 | 28.508 | −6.176 | 1.00 | 11.43 B | C |
| ATOM | 9050 | CB | LEU | B | 38 | 85.176 | 27.669 | −7.458 | 1.00 | 11.06 B | C |
| ATOM | 9053 | CG | LEU | B | 38 | 86.459 | 26.883 | −7.758 | 1.00 | 9.62 B | C |
| ATOM | 9055 | CD1 | LEU | B | 38 | 86.310 | 26.057 | −9.026 | 1.00 | 6.76 B | C |
| ATOM | 9059 | CD2 | LEU | B | 38 | 87.657 | 27.812 | −7.867 | 1.00 | 9.21 B | C |
| ATOM | 9063 | C | LEU | B | 38 | 83.922 | 29.348 | −6.052 | 1.00 | 11.28 B | C |
| ATOM | 9064 | O | LEU | B | 38 | 83.926 | 30.532 | −6.388 | 1.00 | 11.03 B | O |
| ATOM | 9066 | N | GLU | B | 39 | 82.839 | 28.738 | −5.570 | 1.00 | 11.37 B | N |
| ATOM | 9067 | CA | GLU | B | 39 | 81.605 | 29.472 | −5.271 | 1.00 | 11.49 B | C |
| ATOM | 9069 | CB | GLU | B | 39 | 80.544 | 28.551 | −4.657 | 1.00 | 11.84 B | C |
| ATOM | 9072 | CG | GLU | B | 39 | 79.181 | 29.229 | −4.440 | 1.00 | 12.44 B | C |
| ATOM | 9075 | CD | GLU | B | 39 | 78.197 | 28.388 | −3.639 | 1.00 | 13.61 B | C |
| ATOM | 9076 | OE1 | GLU | B | 39 | 78.576 | 27.309 | −3.140 | 1.00 | 14.31 B | O |
| ATOM | 9077 | OE2 | GLU | B | 39 | 77.033 | 28.818 | −3.504 | 1.00 | 13.97 B | O |
| ATOM | 9078 | C | GLU | B | 39 | 81.891 | 30.611 | −4.305 | 1.00 | 11.45 B | C |
| ATOM | 9079 | O | GLU | B | 39 | 81.370 | 31.716 | −4.466 | 1.00 | 11.54 B | O |
| ATOM | 9081 | N | ALA | B | 40 | 82.714 | 30.325 | −3.298 | 1.00 | 11.50 B | N |
| ATOM | 9082 | CA | ALA | B | 40 | 83.120 | 31.321 | −2.312 | 1.00 | 11.48 B | C |
| ATOM | 9084 | CB | ALA | B | 40 | 84.038 | 30.689 | −1.278 | 1.00 | 11.52 B | C |
| ATOM | 9088 | C | ALA | B | 40 | 83.815 | 32.506 | −2.972 | 1.00 | 11.57 B | C |
| ATOM | 9089 | O | ALA | B | 40 | 83.515 | 33.661 | −2.665 | 1.00 | 11.32 B | O |
| ATOM | 9091 | N | GLU | B | 41 | 84.734 | 32.210 | −3.886 | 1.00 | 11.81 B | N |
| ATOM | 9092 | CA | GLU | B | 41 | 85.501 | 33.244 | −4.580 | 1.00 | 12.06 B | C |
| ATOM | 9094 | CB | GLU | B | 41 | 86.602 | 32.610 | −5.437 | 1.00 | 12.41 B | C |
| ATOM | 9097 | CG | GLU | B | 41 | 87.698 | 33.583 | −5.862 | 1.00 | 13.10 B | C |
| ATOM | 9100 | CD | GLU | B | 41 | 88.924 | 32.889 | −6.430 | 1.00 | 13.35 B | C |
| ATOM | 9101 | OE1 | GLU | B | 41 | 89.231 | 31.755 | −6.004 | 1.00 | 13.61 B | O |
| ATOM | 9102 | OE2 | GLU | B | 41 | 89.589 | 33.486 | −7.301 | 1.00 | 13.54 B | O |
| ATOM | 9103 | C | GLU | B | 41 | 84.596 | 34.128 | −5.436 | 1.00 | 11.69 B | C |
| ATOM | 9104 | O | GLU | B | 41 | 84.749 | 35.346 | −5.452 | 1.00 | 11.44 B | O |
| ATOM | 9106 | N | VAL | B | 42 | 83.651 | 33.509 | −6.135 | 1.00 | 11.70 B | N |
| ATOM | 9107 | CA | VAL | B | 42 | 82.672 | 34.251 | −6.922 | 1.00 | 11.83 B | C |
| ATOM | 9109 | CB | VAL | B | 42 | 81.728 | 33.305 | −7.695 | 1.00 | 11.85 B | C |
| ATOM | 9111 | CG1 | VAL | B | 42 | 80.650 | 34.095 | −8.419 | 1.00 | 12.24 B | C |
| ATOM | 9115 | CG2 | VAL | B | 42 | 82.513 | 32.460 | −8.682 | 1.00 | 11.42 B | C |
| ATOM | 9119 | C | VAL | B | 42 | 81.849 | 35.162 | −6.015 | 1.00 | 12.05 B | C |
| ATOM | 9120 | O | VAL | B | 42 | 81.692 | 36.348 | −6.299 | 1.00 | 11.93 B | O |
| ATOM | 9122 | N | ARG | B | 43 | 81.343 | 34.602 | −4.918 | 1.00 | 12.55 B | N |
| ATOM | 9123 | CA | ARG | B | 43 | 80.539 | 35.356 | −3.949 | 1.00 | 13.01 B | C |
| ATOM | 9125 | CB | ARG | B | 43 | 80.173 | 34.467 | −2.748 | 1.00 | 13.46 B | C |
| ATOM | 9128 | CG | ARG | B | 43 | 79.342 | 35.153 | −1.654 | 1.00 | 14.25 B | C |
| ATOM | 9131 | CD | ARG | B | 43 | 80.220 | 35.887 | −0.635 | 1.00 | 14.13 B | C |
| ATOM | 9134 | NE | ARG | B | 43 | 79.457 | 36.448 | 0.477 | 1.00 | 13.56 B | N |
| ATOM | 9136 | CZ | ARG | B | 43 | 79.951 | 37.291 | 1.382 | 1.00 | 13.26 B | C |
| ATOM | 9137 | NH1 | ARG | B | 43 | 79.172 | 37.747 | 2.356 | 1.00 | 13.32 B | N |
| ATOM | 9140 | NH2 | ARG | B | 43 | 81.218 | 37.687 | 1.319 | 1.00 | 13.61 B | N |
| ATOM | 9143 | C | ARG | B | 43 | 81.251 | 36.623 | −3.474 | 1.00 | 12.51 B | C |
| ATOM | 9144 | O | ARG | B | 43 | 80.632 | 37.683 | −3.361 | 1.00 | 12.05 B | O |
| ATOM | 9146 | N | ARG | B | 44 | 82.545 | 36.504 | −3.187 | 1.00 | 12.38 B | N |
| ATOM | 9147 | CA | ARG | B | 44 | 83.347 | 37.648 | −2.750 | 1.00 | 12.46 B | C |
| ATOM | 9149 | CB | ARG | B | 44 | 84.807 | 37.236 | −2.537 | 1.00 | 12.38 B | C |
| ATOM | 9152 | CG | ARG | B | 44 | 85.734 | 38.380 | −2.138 | 1.00 | 11.90 B | C |
| ATOM | 9155 | CD | ARG | B | 44 | 87.112 | 37.874 | −1.750 | 1.00 | 10.93 B | C |
| ATOM | 9158 | NE | ARG | B | 44 | 87.798 | 37.229 | −2.866 | 1.00 | 10.06 B | N |
| ATOM | 9160 | CZ | ARG | B | 44 | 89.003 | 36.667 | −2.788 | 1.00 | 10.80 B | C |
| ATOM | 9161 | NH1 | ARG | B | 44 | 89.679 | 36.664 | −1.643 | 1.00 | 12.55 B | N |
| ATOM | 9164 | NH2 | ARG | B | 44 | 89.539 | 36.103 | −3.863 | 1.00 | 10.95 B | N |
| ATOM | 9167 | C | ARG | B | 44 | 83.278 | 38.788 | −3.758 | 1.00 | 12.62 B | C |
| ATOM | 9168 | O | ARG | B | 44 | 83.176 | 39.953 | −3.375 | 1.00 | 12.54 B | O |
| ATOM | 9170 | N | GLU | B | 45 | 83.332 | 38.446 | −5.042 | 1.00 | 12.86 B | N |
| ATOM | 9171 | CA | GLU | B | 45 | 83.303 | 39.448 | −6.102 | 1.00 | 13.14 B | C |
| ATOM | 9173 | CB | GLU | B | 45 | 83.716 | 38.840 | −7.449 | 1.00 | 13.40 B | C |
| ATOM | 9176 | CG | GLU | B | 45 | 85.094 | 38.176 | −7.467 | 1.00 | 13.15 B | C |
| ATOM | 9179 | CD | GLU | B | 45 | 86.197 | 39.066 | −6.930 | 1.00 | 12.52 B | C |
| ATOM | 9180 | OE1 | GLU | B | 45 | 86.171 | 40.286 | −7.197 | 1.00 | 11.65 B | O |
| ATOM | 9181 | OE2 | GLU | B | 45 | 87.094 | 38.542 | −6.239 | 1.00 | 13.46 B | O |
| ATOM | 9182 | C | GLU | B | 45 | 81.930 | 40.100 | −6.227 | 1.00 | 13.07 B | C |
| ATOM | 9183 | O | GLU | B | 45 | 81.837 | 41.308 | −6.424 | 1.00 | 13.24 B | O |

TABLE 8-2-continued

Coordinates for L494P Structure

| | | | | | | | | | | | | |
|---|---|---|---|---|---|---|---|---|---|---|---|---|
| ATOM | 9185 | N | ILE | B | 46 | 80.870 | 39.308 | −6.100 | 1.00 | 13.28 | B | N |
| ATOM | 9186 | CA | ILE | B | 46 | 79.505 | 39.831 | −6.217 | 1.00 | 13.40 | B | C |
| ATOM | 9188 | CB | ILE | B | 46 | 78.450 | 38.696 | −6.262 | 1.00 | 13.25 | B | C |
| ATOM | 9190 | CG1 | ILE | B | 46 | 78.670 | 37.801 | −7.485 | 1.00 | 12.31 | B | C |
| ATOM | 9193 | CD1 | ILE | B | 46 | 77.743 | 36.617 | −7.546 | 1.00 | 11.98 | B | C |
| ATOM | 9197 | CG2 | ILE | B | 46 | 77.044 | 39.270 | −6.318 | 1.00 | 12.44 | B | C |
| ATOM | 9201 | C | ILE | B | 46 | 79.179 | 40.805 | −5.078 | 1.00 | 13.95 | B | C |
| ATOM | 9202 | O | ILE | B | 46 | 78.401 | 41.740 | −5.269 | 1.00 | 13.95 | B | O |
| ATOM | 9204 | N | ASN | B | 47 | 79.788 | 40.589 | −3.910 | 1.00 | 14.71 | B | N |
| ATOM | 9205 | CA | ASN | B | 47 | 79.621 | 41.476 | −2.750 | 1.00 | 15.06 | B | C |
| ATOM | 9207 | CB | ASN | B | 47 | 79.428 | 40.644 | −1.485 | 1.00 | 14.81 | B | C |
| ATOM | 9210 | CG | ASN | B | 47 | 78.236 | 39.728 | −1.579 | 1.00 | 15.52 | B | C |
| ATOM | 9211 | OD1 | ASN | B | 47 | 77.091 | 40.181 | −1.600 | 1.00 | 15.77 | B | O |
| ATOM | 9212 | ND2 | ASN | B | 47 | 78.495 | 38.429 | −1.650 | 1.00 | 17.54 | B | N |
| ATOM | 9215 | C | ASN | B | 47 | 80.779 | 42.460 | −2.552 | 1.00 | 15.58 | B | C |
| ATOM | 9216 | O | ASN | B | 47 | 80.888 | 43.093 | −1.498 | 1.00 | 16.00 | B | O |
| ATOM | 9218 | N | ASN | B | 48 | 81.637 | 42.584 | −3.563 | 1.00 | 15.89 | B | N |
| ATOM | 9219 | CA | ASN | B | 48 | 82.745 | 43.532 | −3.535 | 1.00 | 16.06 | B | C |
| ATOM | 9221 | CB | ASN | B | 48 | 83.744 | 43.202 | −4.650 | 1.00 | 15.90 | B | C |
| ATOM | 9224 | CG | ASN | B | 48 | 84.925 | 44.150 | −4.685 | 1.00 | 15.28 | B | C |
| ATOM | 9225 | OD1 | ASN | B | 48 | 85.262 | 44.783 | −3.686 | 1.00 | 15.43 | B | O |
| ATOM | 9226 | ND2 | ASN | B | 48 | 85.566 | 44.248 | −5.843 | 1.00 | 15.13 | B | N |
| ATOM | 9229 | C | ASN | B | 48 | 82.214 | 44.951 | −3.701 | 1.00 | 16.79 | B | C |
| ATOM | 9230 | O | ASN | B | 48 | 81.838 | 45.349 | −4.806 | 1.00 | 17.02 | B | O |
| ATOM | 9232 | N | GLU | B | 49 | 82.188 | 45.710 | −2.606 | 1.00 | 17.49 | B | N |
| ATOM | 9233 | CA | GLU | B | 49 | 81.592 | 47.053 | −2.612 | 1.00 | 18.37 | B | C |
| ATOM | 9235 | CB | GLU | B | 49 | 81.183 | 47.467 | −1.191 | 1.00 | 18.78 | B | C |
| ATOM | 9238 | CG | GLU | B | 49 | 80.125 | 46.546 | −0.564 | 1.00 | 20.96 | B | C |
| ATOM | 9241 | CD | GLU | B | 49 | 79.341 | 47.187 | 0.583 | 1.00 | 23.15 | B | C |
| ATOM | 9242 | OE1 | GLU | B | 49 | 78.832 | 46.437 | 1.443 | 1.00 | 23.41 | B | O |
| ATOM | 9243 | OE2 | GLU | B | 49 | 79.220 | 48.432 | 0.626 | 1.00 | 25.12 | B | O |
| ATOM | 9244 | C | GLU | B | 49 | 82.484 | 48.132 | −3.245 | 1.00 | 18.48 | B | C |
| ATOM | 9245 | O | GLU | B | 49 | 82.045 | 49.270 | −3.411 | 1.00 | 18.18 | B | O |
| ATOM | 9247 | N | LYS | B | 50 | 83.721 | 47.776 | −3.598 | 1.00 | 18.96 | B | N |
| ATOM | 9248 | CA | LYS | B | 50 | 84.643 | 48.694 | −4.277 | 1.00 | 19.36 | B | C |
| ATOM | 9250 | CB | LYS | B | 50 | 86.002 | 48.704 | −3.569 | 1.00 | 19.39 | B | C |
| ATOM | 9253 | CG | LYS | B | 50 | 85.938 | 48.749 | −2.054 | 1.00 | 19.24 | B | C |
| ATOM | 9256 | CD | LYS | B | 50 | 87.314 | 49.008 | −1.455 | 1.00 | 19.55 | B | C |
| ATOM | 9259 | CE | LYS | B | 50 | 87.442 | 48.400 | −0.069 | 1.00 | 19.73 | B | C |
| ATOM | 9262 | NZ | LYS | B | 50 | 86.280 | 48.740 | 0.792 | 1.00 | 18.94 | B | N |
| ATOM | 9266 | C | LYS | B | 50 | 84.855 | 48.325 | −5.751 | 1.00 | 19.85 | B | C |
| ATOM | 9267 | O | LYS | B | 50 | 85.860 | 48.711 | −6.350 | 1.00 | 19.64 | B | O |
| ATOM | 9269 | N | ALA | B | 51 | 83.914 | 47.585 | −6.335 | 1.00 | 20.78 | B | N |
| ATOM | 9270 | CA | ALA | B | 51 | 84.036 | 47.130 | −7.721 | 1.00 | 21.39 | B | C |
| ATOM | 9272 | CB | ALA | B | 51 | 83.225 | 45.860 | −7.932 | 1.00 | 21.43 | B | C |
| ATOM | 9276 | C | ALA | B | 51 | 83.580 | 48.213 | −8.693 | 1.00 | 21.95 | B | C |
| ATOM | 9277 | O | ALA | B | 51 | 82.643 | 48.956 | −8.402 | 1.00 | 21.95 | B | O |
| ATOM | 9279 | N | GLU | B | 52 | 84.248 | 48.298 | −9.842 | 1.00 | 22.93 | B | N |
| ATOM | 9280 | CA | GLU | B | 52 | 83.864 | 49.240 | −10.899 | 1.00 | 23.64 | B | C |
| ATOM | 9282 | CB | GLU | B | 52 | 84.892 | 49.243 | −12.037 | 1.00 | 23.82 | B | C |
| ATOM | 9285 | CG | GLU | B | 52 | 86.280 | 49.747 | −11.642 | 1.00 | 24.65 | B | C |
| ATOM | 9288 | CD | GLU | B | 52 | 86.415 | 51.257 | −11.745 | 1.00 | 26.37 | B | C |
| ATOM | 9289 | OE1 | GLU | B | 52 | 86.465 | 51.778 | −12.880 | 1.00 | 27.93 | B | O |
| ATOM | 9290 | OE2 | GLU | B | 52 | 86.486 | 51.924 | −10.691 | 1.00 | 27.36 | B | O |
| ATOM | 9291 | C | GLU | B | 52 | 82.498 | 48.824 | −11.427 | 1.00 | 23.98 | B | C |
| ATOM | 9292 | O | GLU | B | 52 | 82.289 | 47.653 | −11.752 | 1.00 | 24.25 | B | O |
| ATOM | 9294 | N | PHE | B | 53 | 81.575 | 49.780 | −11.505 | 1.00 | 24.11 | B | N |
| ATOM | 9295 | CA | PHE | B | 53 | 80.165 | 49.475 | −11.772 | 1.00 | 24.15 | B | C |
| ATOM | 9297 | CB | PHE | B | 53 | 79.315 | 50.749 | −11.715 | 1.00 | 24.51 | B | C |
| ATOM | 9300 | CG | PHE | B | 53 | 79.155 | 51.313 | −10.324 | 1.00 | 27.60 | B | C |
| ATOM | 9301 | CD1 | PHE | B | 53 | 78.559 | 50.556 | −9.315 | 1.00 | 29.48 | B | C |
| ATOM | 9303 | CE1 | PHE | B | 53 | 78.400 | 51.071 | −8.028 | 1.00 | 30.36 | B | C |
| ATOM | 9305 | CZ | PHE | B | 53 | 78.838 | 52.361 | −7.739 | 1.00 | 31.69 | B | C |
| ATOM | 9307 | CE2 | PHE | B | 53 | 79.433 | 53.131 | −8.739 | 1.00 | 31.11 | B | C |
| ATOM | 9309 | CD2 | PHE | B | 53 | 79.586 | 52.606 | −10.024 | 1.00 | 30.30 | B | C |
| ATOM | 9311 | C | PHE | B | 53 | 79.933 | 48.739 | −13.095 | 1.00 | 23.44 | B | C |
| ATOM | 9312 | O | PHE | B | 53 | 79.059 | 47.874 | −13.177 | 1.00 | 23.35 | B | O |
| ATOM | 9314 | N | LEU | B | 54 | 80.715 | 49.073 | −14.120 | 1.00 | 22.51 | B | N |
| ATOM | 9315 | CA | LEU | B | 54 | 80.622 | 48.377 | −15.403 | 1.00 | 21.75 | B | C |
| ATOM | 9317 | CB | LEU | B | 54 | 81.416 | 49.117 | −16.487 | 1.00 | 21.53 | B | C |
| ATOM | 9320 | CG | LEU | B | 54 | 81.023 | 48.812 | −17.936 | 1.00 | 21.05 | B | C |
| ATOM | 9322 | CD1 | LEU | B | 54 | 79.602 | 49.279 | −18.218 | 1.00 | 20.70 | B | C |
| ATOM | 9326 | CD2 | LEU | B | 54 | 81.997 | 49.461 | −18.908 | 1.00 | 19.68 | B | C |
| ATOM | 9330 | C | LEU | B | 54 | 81.110 | 46.928 | −15.267 | 1.00 | 21.34 | B | C |
| ATOM | 9331 | O | LEU | B | 54 | 80.503 | 46.011 | −15.821 | 1.00 | 21.37 | B | O |
| ATOM | 9333 | N | THR | B | 55 | 82.195 | 46.731 | −14.517 | 1.00 | 20.71 | B | N |
| ATOM | 9334 | CA | THR | B | 55 | 82.723 | 45.391 | −14.241 | 1.00 | 20.02 | B | C |
| ATOM | 9336 | CB | THR | B | 55 | 84.090 | 45.459 | −13.528 | 1.00 | 19.67 | B | C |

TABLE 8-2-continued

Coordinates for L494P Structure

| | | | | | | | | | | | | |
|---|---|---|---|---|---|---|---|---|---|---|---|---|
| ATOM | 9338 | OG1 | THR | B | 55 | 84.974 | 46.311 | −14.264 | 1.00 | 18.17 | B | O |
| ATOM | 9340 | CG2 | THR | B | 55 | 84.706 | 44.071 | −13.409 | 1.00 | 19.26 | B | C |
| ATOM | 9344 | C | THR | B | 55 | 81.763 | 44.569 | −13.379 | 1.00 | 19.89 | B | C |
| ATOM | 9345 | O | THR | B | 55 | 81.651 | 43.353 | −13.550 | 1.00 | 19.81 | B | O |
| ATOM | 9347 | N | LEU | B | 56 | 81.077 | 45.242 | −12.456 | 1.00 | 19.76 | B | N |
| ATOM | 9348 | CA | LEU | B | 56 | 80.128 | 44.592 | −11.552 | 1.00 | 19.79 | B | C |
| ATOM | 9350 | CB | LEU | B | 56 | 79.630 | 45.591 | −10.500 | 1.00 | 19.92 | B | C |
| ATOM | 9353 | CG | LEU | B | 56 | 78.637 | 45.086 | −9.449 | 1.00 | 20.73 | B | C |
| ATOM | 9355 | CD1 | LEU | B | 56 | 79.195 | 43.878 | −8.703 | 1.00 | 21.48 | B | C |
| ATOM | 9359 | CD2 | LEU | B | 56 | 78.277 | 46.207 | −8.476 | 1.00 | 21.77 | B | C |
| ATOM | 9363 | C | LEU | B | 56 | 78.941 | 44.014 | −12.316 | 1.00 | 19.43 | B | C |
| ATOM | 9364 | O | LEU | B | 56 | 78.580 | 42.850 | −12.136 | 1.00 | 19.59 | B | O |
| ATOM | 9366 | N | LEU | B | 57 | 78.341 | 44.840 | −13.167 | 1.00 | 18.85 | B | N |
| ATOM | 9367 | CA | LEU | B | 57 | 77.219 | 44.412 | −13.997 | 1.00 | 18.27 | B | C |
| ATOM | 9369 | CB | LEU | B | 57 | 76.672 | 45.590 | −14.808 | 1.00 | 18.24 | B | C |
| ATOM | 9372 | CG | LEU | B | 57 | 76.112 | 46.770 | −14.008 | 1.00 | 18.19 | B | C |
| ATOM | 9374 | CD1 | LEU | B | 57 | 75.894 | 47.973 | −14.912 | 1.00 | 17.75 | B | C |
| ATOM | 9378 | CD2 | LEU | B | 57 | 74.824 | 46.382 | −13.297 | 1.00 | 18.37 | B | C |
| ATOM | 9382 | C | LEU | B | 57 | 77.649 | 43.289 | −14.938 | 1.00 | 17.71 | B | C |
| ATOM | 9383 | O | LEU | B | 57 | 76.922 | 42.311 | −15.114 | 1.00 | 17.47 | B | O |
| ATOM | 9385 | N | GLU | B | 58 | 78.836 | 43.435 | −15.527 | 1.00 | 17.20 | B | N |
| ATOM | 9386 | CA | GLU | B | 58 | 79.386 | 42.429 | −16.440 | 1.00 | 16.77 | B | C |
| ATOM | 9388 | CB | GLU | B | 58 | 80.668 | 42.942 | −17.110 | 1.00 | 16.93 | B | C |
| ATOM | 9391 | CG | GLU | B | 58 | 80.413 | 43.906 | −18.269 | 1.00 | 18.82 | B | C |
| ATOM | 9394 | CD | GLU | B | 58 | 81.688 | 44.351 | −18.983 | 1.00 | 20.53 | B | C |
| ATOM | 9395 | OE1 | GLU | B | 58 | 82.721 | 43.653 | −18.876 | 1.00 | 22.18 | B | O |
| ATOM | 9396 | OE2 | GLU | B | 58 | 81.652 | 45.400 | −19.662 | 1.00 | 20.87 | B | O |
| ATOM | 9397 | C | GLU | B | 58 | 79.655 | 41.080 | −15.764 | 1.00 | 16.01 | B | C |
| ATOM | 9398 | O | GLU | B | 58 | 79.540 | 40.038 | −16.409 | 1.00 | 16.08 | B | O |
| ATOM | 9400 | N | LEU | B | 59 | 80.011 | 41.095 | −14.479 | 1.00 | 14.97 | B | N |
| ATOM | 9401 | CA | LEU | B | 59 | 80.244 | 39.849 | −13.740 | 1.00 | 13.89 | B | C |
| ATOM | 9403 | CB | LEU | B | 59 | 80.915 | 40.117 | −12.387 | 1.00 | 13.50 | B | C |
| ATOM | 9406 | CG | LEU | B | 59 | 81.070 | 38.917 | −11.439 | 1.00 | 11.95 | B | C |
| ATOM | 9408 | CD1 | LEU | B | 59 | 81.657 | 37.699 | −12.142 | 1.00 | 8.96 | B | C |
| ATOM | 9412 | CD2 | LEU | B | 59 | 81.921 | 39.295 | −10.243 | 1.00 | 10.77 | B | C |
| ATOM | 9416 | C | LEU | B | 59 | 78.936 | 39.085 | −13.541 | 1.00 | 13.42 | B | C |
| ATOM | 9417 | O | LEU | B | 59 | 78.852 | 37.904 | −13.877 | 1.00 | 13.89 | B | O |
| ATOM | 9419 | N | ILE | B | 60 | 77.924 | 39.761 | −12.999 | 1.00 | 12.45 | B | N |
| ATOM | 9420 | CA | ILE | B | 60 | 76.607 | 39.148 | −12.804 | 1.00 | 11.69 | B | C |
| ATOM | 9422 | CB | ILE | B | 60 | 75.533 | 40.169 | −12.356 | 1.00 | 11.55 | B | C |
| ATOM | 9424 | CG1 | ILE | B | 60 | 75.861 | 40.758 | −10.982 | 1.00 | 11.14 | B | C |
| ATOM | 9427 | CD1 | ILE | B | 60 | 74.840 | 41.771 | −10.494 | 1.00 | 9.21 | B | C |
| ATOM | 9431 | CG2 | ILE | B | 60 | 74.161 | 39.507 | −12.311 | 1.00 | 10.73 | B | C |
| ATOM | 9435 | C | ILE | B | 60 | 76.139 | 38.535 | −14.114 | 1.00 | 11.60 | B | C |
| ATOM | 9436 | O | ILE | B | 60 | 75.774 | 37.362 | −14.167 | 1.00 | 11.32 | B | O |
| ATOM | 9438 | N | ASP | B | 61 | 76.168 | 39.348 | −15.168 | 1.00 | 11.70 | B | N |
| ATOM | 9439 | CA | ASP | B | 61 | 75.739 | 38.927 | −16.496 | 1.00 | 11.67 | B | C |
| ATOM | 9441 | CB | ASP | B | 61 | 75.996 | 40.041 | −17.517 | 1.00 | 11.58 | B | C |
| ATOM | 9444 | CG | ASP | B | 61 | 75.344 | 39.772 | −18.866 | 1.00 | 11.78 | B | C |
| ATOM | 9445 | OD1 | ASP | B | 61 | 74.350 | 39.015 | −18.922 | 1.00 | 9.94 | B | O |
| ATOM | 9446 | OD2 | ASP | B | 61 | 75.826 | 40.332 | −19.874 | 1.00 | 11.86 | B | O |
| ATOM | 9447 | C | ASP | B | 61 | 76.452 | 37.647 | −16.914 | 1.00 | 11.90 | B | C |
| ATOM | 9448 | O | ASP | B | 61 | 75.823 | 36.740 | −17.444 | 1.00 | 11.79 | B | O |
| ATOM | 9450 | N | ASN | B | 62 | 77.756 | 37.572 | −16.660 | 1.00 | 12.59 | B | N |
| ATOM | 9451 | CA | ASN | B | 62 | 78.515 | 36.345 | −16.917 | 1.00 | 13.39 | B | C |
| ATOM | 9453 | CB | ASN | B | 62 | 80.020 | 36.574 | −16.725 | 1.00 | 13.48 | B | C |
| ATOM | 9456 | CG | ASN | B | 62 | 80.590 | 37.589 | −17.699 | 1.00 | 13.93 | B | C |
| ATOM | 9457 | OD1 | ASN | B | 62 | 80.077 | 37.768 | −18.803 | 1.00 | 13.75 | B | O |
| ATOM | 9458 | ND2 | ASN | B | 62 | 81.660 | 38.263 | −17.290 | 1.00 | 16.15 | B | N |
| ATOM | 9461 | C | ASN | B | 62 | 78.049 | 35.192 | −16.024 | 1.00 | 13.60 | B | C |
| ATOM | 9462 | O | ASN | B | 62 | 77.842 | 34.076 | −16.500 | 1.00 | 13.11 | B | O |
| ATOM | 9464 | N | VAL | B | 63 | 77.873 | 35.473 | −14.735 | 1.00 | 13.89 | B | N |
| ATOM | 9465 | CA | VAL | B | 63 | 77.447 | 34.458 | −13.773 | 1.00 | 14.49 | B | C |
| ATOM | 9467 | CB | VAL | B | 63 | 77.327 | 35.041 | −12.349 | 1.00 | 14.33 | B | C |
| ATOM | 9469 | CG1 | VAL | B | 63 | 76.681 | 34.034 | −11.410 | 1.00 | 14.92 | B | C |
| ATOM | 9473 | CG2 | VAL | B | 63 | 78.693 | 35.452 | −11.829 | 1.00 | 14.73 | B | C |
| ATOM | 9477 | C | VAL | B | 63 | 76.113 | 33.822 | −14.170 | 1.00 | 15.20 | B | C |
| ATOM | 9478 | O | VAL | B | 63 | 75.986 | 32.596 | −14.188 | 1.00 | 15.27 | B | O |
| ATOM | 9480 | N | GLN | B | 64 | 75.129 | 34.658 | −14.490 | 1.00 | 15.80 | B | N |
| ATOM | 9481 | CA | GLN | B | 64 | 73.799 | 34.178 | −14.875 | 1.00 | 16.00 | B | C |
| ATOM | 9483 | CB | GLN | B | 64 | 72.811 | 35.340 | −14.962 | 1.00 | 16.04 | B | C |
| ATOM | 9486 | CG | GLN | B | 64 | 72.518 | 36.000 | −13.630 | 1.00 | 16.27 | B | C |
| ATOM | 9489 | CD | GLN | B | 64 | 71.616 | 37.209 | −13.762 | 1.00 | 16.56 | B | C |
| ATOM | 9490 | OE1 | GLN | B | 64 | 70.631 | 37.339 | −13.035 | 1.00 | 19.83 | B | O |
| ATOM | 9491 | NE2 | GLN | B | 64 | 71.946 | 38.102 | −14.693 | 1.00 | 12.79 | B | N |
| ATOM | 9494 | C | GLN | B | 64 | 73.825 | 33.441 | −16.207 | 1.00 | 16.02 | B | C |
| ATOM | 9495 | O | GLN | B | 64 | 73.141 | 32.434 | −16.375 | 1.00 | 16.54 | B | O |
| ATOM | 9497 | N | ARG | B | 65 | 74.612 | 33.950 | −17.150 | 1.00 | 16.05 | B | N |

TABLE 8-2-continued

Coordinates for L494P Structure

| | | | | | | | | | | | | |
|---|---|---|---|---|---|---|---|---|---|---|---|---|
| ATOM | 9498 | CA | ARG | B | 65 | 74.721 | 33.338 | −18.473 | 1.00 | 16.17 | B | C |
| ATOM | 9500 | CB | ARG | B | 65 | 75.346 | 34.315 | −19.473 | 1.00 | 16.27 | B | C |
| ATOM | 9503 | CG | ARG | B | 65 | 74.403 | 35.458 | −19.834 | 1.00 | 18.62 | B | C |
| ATOM | 9506 | CD | ARG | B | 65 | 74.945 | 36.347 | −20.935 | 1.00 | 19.52 | B | C |
| ATOM | 9509 | NE | ARG | B | 65 | 74.972 | 35.651 | −22.219 | 1.00 | 21.90 | B | N |
| ATOM | 9511 | CZ | ARG | B | 65 | 75.080 | 36.245 | −23.405 | 1.00 | 25.25 | B | C |
| ATOM | 9512 | NH1 | ARG | B | 65 | 75.161 | 37.571 | −23.503 | 1.00 | 26.87 | B | N |
| ATOM | 9515 | NH2 | ARG | B | 65 | 75.099 | 35.504 | −24.509 | 1.00 | 26.60 | B | N |
| ATOM | 9518 | C | ARG | B | 65 | 75.494 | 32.020 | −18.451 | 1.00 | 15.57 | B | C |
| ATOM | 9519 | O | ARG | B | 65 | 75.292 | 31.179 | −19.322 | 1.00 | 16.17 | B | O |
| ATOM | 9521 | N | LEU | B | 66 | 76.361 | 31.838 | −17.454 | 1.00 | 14.50 | B | N |
| ATOM | 9522 | CA | LEU | B | 66 | 77.091 | 30.575 | −17.275 | 1.00 | 13.62 | B | C |
| ATOM | 9524 | CB | LEU | B | 66 | 78.445 | 30.836 | −16.606 | 1.00 | 13.45 | B | C |
| ATOM | 9527 | CG | LEU | B | 66 | 79.441 | 31.662 | −17.429 | 1.00 | 12.05 | B | C |
| ATOM | 9529 | CD1 | LEU | B | 66 | 80.499 | 32.279 | −16.532 | 1.00 | 11.23 | B | C |
| ATOM | 9533 | CD2 | LEU | B | 66 | 80.081 | 30.824 | −18.518 | 1.00 | 9.81 | B | C |
| ATOM | 9537 | C | LEU | B | 66 | 76.283 | 29.546 | −16.468 | 1.00 | 13.36 | B | C |
| ATOM | 9538 | O | LEU | B | 66 | 76.797 | 28.480 | −16.116 | 1.00 | 12.46 | B | O |
| ATOM | 9540 | N | GLY | B | 67 | 75.024 | 29.880 | −16.175 | 1.00 | 13.57 | B | N |
| ATOM | 9541 | CA | GLY | B | 67 | 74.089 | 28.970 | −15.518 | 1.00 | 13.40 | B | C |
| ATOM | 9544 | C | GLY | B | 67 | 74.004 | 29.124 | −14.009 | 1.00 | 13.53 | B | C |
| ATOM | 9545 | O | GLY | B | 67 | 73.192 | 28.456 | −13.367 | 1.00 | 13.68 | B | O |
| ATOM | 9547 | N | LEU | B | 68 | 74.812 | 30.020 | −13.442 | 1.00 | 13.50 | B | N |
| ATOM | 9548 | CA | LEU | B | 68 | 75.000 | 30.092 | −11.988 | 1.00 | 13.46 | B | C |
| ATOM | 9550 | CB | LEU | B | 68 | 76.484 | 30.330 | −11.678 | 1.00 | 13.16 | B | C |
| ATOM | 9553 | CG | LEU | B | 68 | 77.467 | 29.318 | −12.274 | 1.00 | 12.36 | B | C |
| ATOM | 9555 | CD1 | LEU | B | 68 | 78.899 | 29.699 | −11.919 | 1.00 | 11.43 | B | C |
| ATOM | 9559 | CD2 | LEU | B | 68 | 77.152 | 27.905 | −11.803 | 1.00 | 9.64 | B | C |
| ATOM | 9563 | C | LEU | B | 68 | 74.149 | 31.150 | −11.266 | 1.00 | 13.59 | B | C |
| ATOM | 9564 | O | LEU | B | 68 | 74.430 | 31.485 | −10.117 | 1.00 | 13.36 | B | O |
| ATOM | 9566 | N | GLY | B | 69 | 73.105 | 31.658 | −11.916 | 1.00 | 13.93 | B | N |
| ATOM | 9567 | CA | GLY | B | 69 | 72.275 | 32.714 | −11.327 | 1.00 | 14.33 | B | C |
| ATOM | 9570 | C | GLY | B | 69 | 71.461 | 32.277 | −10.117 | 1.00 | 14.49 | B | C |
| ATOM | 9571 | O | GLY | B | 69 | 71.331 | 33.023 | −9.142 | 1.00 | 14.33 | B | O |
| ATOM | 9573 | N | TYR | B | 70 | 70.910 | 31.067 | −10.184 | 1.00 | 14.76 | B | N |
| ATOM | 9574 | CA | TYR | B | 70 | 70.127 | 30.493 | −9.080 | 1.00 | 14.94 | B | C |
| ATOM | 9576 | CB | TYR | B | 70 | 69.535 | 29.136 | −9.493 | 1.00 | 14.57 | B | C |
| ATOM | 9579 | CG | TYR | B | 70 | 70.532 | 27.992 | −9.554 | 1.00 | 12.18 | B | C |
| ATOM | 9580 | CD1 | TYR | B | 70 | 70.607 | 27.053 | −8.530 | 1.00 | 9.68 | B | C |
| ATOM | 9582 | CE1 | TYR | B | 70 | 71.511 | 25.999 | −8.585 | 1.00 | 8.46 | B | C |
| ATOM | 9584 | CZ | TYR | B | 70 | 72.353 | 25.874 | −9.673 | 1.00 | 8.09 | B | C |
| ATOM | 9585 | OH | TYR | B | 70 | 73.251 | 24.837 | −9.733 | 1.00 | 2.16 | B | O |
| ATOM | 9587 | CE2 | TYR | B | 70 | 72.300 | 26.789 | −10.701 | 1.00 | 10.87 | B | C |
| ATOM | 9589 | CD2 | TYR | B | 70 | 71.390 | 27.841 | −10.640 | 1.00 | 12.42 | B | C |
| ATOM | 9591 | C | TYR | B | 70 | 70.929 | 30.328 | −7.783 | 1.00 | 15.65 | B | C |
| ATOM | 9592 | O | TYR | B | 70 | 70.354 | 30.256 | −6.696 | 1.00 | 15.92 | B | O |
| ATOM | 9594 | N | ARG | B | 71 | 72.251 | 30.270 | −7.911 | 1.00 | 16.20 | B | N |
| ATOM | 9595 | CA | ARG | B | 71 | 73.144 | 30.017 | −6.785 | 1.00 | 16.52 | B | C |
| ATOM | 9597 | CB | ARG | B | 71 | 74.387 | 29.275 | −7.292 | 1.00 | 16.53 | B | C |
| ATOM | 9600 | CG | ARG | B | 71 | 75.487 | 29.079 | −6.269 | 1.00 | 18.42 | B | C |
| ATOM | 9603 | CD | ARG | B | 71 | 76.353 | 27.866 | −6.587 | 1.00 | 20.45 | B | C |
| ATOM | 9606 | NE | ARG | B | 71 | 75.889 | 26.669 | −5.880 | 1.00 | 20.38 | B | N |
| ATOM | 9608 | CZ | ARG | B | 71 | 75.159 | 25.689 | −6.412 | 1.00 | 18.95 | B | C |
| ATOM | 9609 | NH1 | ARG | B | 71 | 74.803 | 24.658 | −5.656 | 1.00 | 19.37 | B | N |
| ATOM | 9612 | NH2 | ARG | B | 71 | 74.783 | 25.719 | −7.686 | 1.00 | 18.08 | B | N |
| ATOM | 9615 | C | ARG | B | 71 | 73.536 | 31.290 | −6.029 | 1.00 | 16.71 | B | C |
| ATOM | 9616 | O | ARG | B | 71 | 73.904 | 31.216 | −4.856 | 1.00 | 17.32 | B | O |
| ATOM | 9618 | N | PHE | B | 72 | 73.446 | 32.448 | −6.686 | 1.00 | 16.77 | B | N |
| ATOM | 9619 | CA | PHE | B | 72 | 73.869 | 33.722 | −6.084 | 1.00 | 16.64 | B | C |
| ATOM | 9621 | CB | PHE | B | 72 | 75.080 | 34.285 | −6.839 | 1.00 | 16.18 | B | C |
| ATOM | 9624 | CG | PHE | B | 72 | 76.285 | 33.396 | −6.807 | 1.00 | 14.45 | B | C |
| ATOM | 9625 | CD1 | PHE | B | 72 | 77.151 | 33.422 | −5.726 | 1.00 | 14.72 | B | C |
| ATOM | 9627 | CE1 | PHE | B | 72 | 78.270 | 32.602 | −5.696 | 1.00 | 15.49 | B | C |
| ATOM | 9629 | CZ | PHE | B | 72 | 78.529 | 31.748 | −6.758 | 1.00 | 14.51 | B | C |
| ATOM | 9631 | CE2 | PHE | B | 72 | 77.672 | 31.718 | −7.840 | 1.00 | 12.96 | B | C |
| ATOM | 9633 | CD2 | PHE | B | 72 | 76.559 | 32.540 | −7.861 | 1.00 | 12.86 | B | C |
| ATOM | 9635 | C | PHE | B | 72 | 72.771 | 34.789 | −6.055 | 1.00 | 17.23 | B | C |
| ATOM | 9636 | O | PHE | B | 72 | 73.070 | 35.966 | −5.846 | 1.00 | 17.54 | B | O |
| ATOM | 9638 | N | GLU | B | 73 | 71.511 | 34.392 | −6.241 | 1.00 | 17.68 | B | N |
| ATOM | 9639 | CA | GLU | B | 73 | 70.417 | 35.362 | −6.381 | 1.00 | 17.82 | B | C |
| ATOM | 9641 | CB | GLU | B | 73 | 69.044 | 34.677 | −6.330 | 1.00 | 17.51 | B | C |
| ATOM | 9644 | CG | GLU | B | 73 | 67.872 | 35.639 | −6.556 | 1.00 | 17.32 | B | C |
| ATOM | 9647 | CD | GLU | B | 73 | 66.574 | 34.938 | −6.923 | 1.00 | 18.12 | B | C |
| ATOM | 9648 | OE1 | GLU | B | 73 | 66.536 | 34.246 | −7.964 | 1.00 | 17.38 | B | O |
| ATOM | 9649 | OE2 | GLU | B | 73 | 65.582 | 35.097 | −6.181 | 1.00 | 18.22 | B | O |
| ATOM | 9650 | C | GLU | B | 73 | 70.492 | 36.495 | −5.347 | 1.00 | 18.27 | B | C |
| ATOM | 9651 | O | GLU | B | 73 | 70.561 | 37.666 | −5.720 | 1.00 | 18.56 | B | O |
| ATOM | 9653 | N | SER | B | 74 | 70.503 | 36.156 | −4.061 | 1.00 | 18.44 | B | N |

TABLE 8-2-continued

Coordinates for L494P Structure

| | | | | | | | | | | | | |
|---|---|---|---|---|---|---|---|---|---|---|---|---|
| ATOM | 9654 | CA | SER | B | 74 | 70.518 | 37.184 | −3.016 | 1.00 | 19.13 | B | C |
| ATOM | 9656 | CB | SER | B | 74 | 70.471 | 36.564 | −1.617 | 1.00 | 19.31 | B | C |
| ATOM | 9659 | OG | SER | B | 74 | 71.749 | 36.099 | −1.218 | 1.00 | 20.88 | B | O |
| ATOM | 9661 | C | SER | B | 74 | 71.751 | 38.075 | −3.137 | 1.00 | 19.37 | B | C |
| ATOM | 9662 | O | SER | B | 74 | 71.649 | 39.304 | −3.058 | 1.00 | 19.55 | B | O |
| ATOM | 9664 | N | ASP | B | 75 | 72.910 | 37.448 | −3.330 | 1.00 | 19.39 | B | N |
| ATOM | 9665 | CA | ASP | B | 75 | 74.168 | 38.181 | −3.468 | 1.00 | 19.25 | B | C |
| ATOM | 9667 | CB | ASP | B | 75 | 75.355 | 37.219 | −3.618 | 1.00 | 18.87 | B | C |
| ATOM | 9670 | CG | ASP | B | 75 | 75.559 | 36.340 | −2.387 | 1.00 | 18.85 | B | C |
| ATOM | 9671 | OD1 | ASP | B | 75 | 76.370 | 36.708 | −1.510 | 1.00 | 15.51 | B | O |
| ATOM | 9672 | OD2 | ASP | B | 75 | 74.897 | 35.284 | −2.293 | 1.00 | 19.53 | B | O |
| ATOM | 9673 | C | ASP | B | 75 | 74.090 | 39.139 | −4.656 | 1.00 | 19.33 | B | C |
| ATOM | 9674 | O | ASP | B | 75 | 74.564 | 40.274 | −4.579 | 1.00 | 19.40 | B | O |
| ATOM | 9676 | N | ILE | B | 76 | 73.466 | 38.682 | −5.739 | 1.00 | 19.53 | B | N |
| ATOM | 9677 | CA | ILE | B | 76 | 73.258 | 39.509 | −6.927 | 1.00 | 19.92 | B | C |
| ATOM | 9679 | CB | ILE | B | 76 | 72.762 | 38.664 | −8.128 | 1.00 | 19.83 | B | C |
| ATOM | 9681 | CG1 | ILE | B | 76 | 73.868 | 37.717 | −8.599 | 1.00 | 19.94 | B | C |
| ATOM | 9684 | CD1 | ILE | B | 76 | 73.384 | 36.631 | −9.528 | 1.00 | 21.34 | B | C |
| ATOM | 9688 | CG2 | ILE | B | 76 | 72.335 | 39.560 | −9.283 | 1.00 | 19.40 | B | C |
| ATOM | 9692 | C | ILE | B | 76 | 72.277 | 40.652 | −6.647 | 1.00 | 20.43 | B | C |
| ATOM | 9693 | O | ILE | B | 76 | 72.535 | 41.796 | −7.028 | 1.00 | 20.62 | B | O |
| ATOM | 9695 | N | ARG | B | 77 | 71.165 | 40.342 | −5.977 | 1.00 | 20.78 | B | N |
| ATOM | 9696 | CA | ARG | B | 77 | 70.175 | 41.360 | −5.595 | 1.00 | 21.05 | B | C |
| ATOM | 9698 | CB | ARG | B | 77 | 68.985 | 40.722 | −4.877 | 1.00 | 21.27 | B | C |
| ATOM | 9701 | CG | ARG | B | 77 | 68.098 | 39.864 | −5.760 | 1.00 | 23.04 | B | C |
| ATOM | 9704 | CD | ARG | B | 77 | 67.085 | 39.093 | −4.924 | 1.00 | 25.79 | B | C |
| ATOM | 9707 | NE | ARG | B | 77 | 66.125 | 39.989 | −4.281 | 1.00 | 27.15 | B | N |
| ATOM | 9709 | CZ | ARG | B | 77 | 65.054 | 40.514 | −4.878 | 1.00 | 28.90 | B | C |
| ATOM | 9710 | NH1 | ARG | B | 77 | 64.777 | 40.244 | −6.152 | 1.00 | 29.24 | B | N |
| ATOM | 9713 | NH2 | ARG | B | 77 | 64.251 | 41.320 | −4.193 | 1.00 | 30.29 | B | N |
| ATOM | 9716 | C | ARG | B | 77 | 70.785 | 42.436 | −4.697 | 1.00 | 20.82 | B | C |
| ATOM | 9717 | O | ARG | B | 77 | 70.469 | 43.618 | −4.833 | 1.00 | 20.93 | B | O |
| ATOM | 9719 | N | GLY | B | 78 | 71.653 | 42.016 | −3.780 | 1.00 | 20.58 | B | N |
| ATOM | 9720 | CA | GLY | B | 78 | 72.387 | 42.943 | −2.924 | 1.00 | 20.53 | B | C |
| ATOM | 9723 | C | GLY | B | 78 | 73.409 | 43.788 | −3.670 | 1.00 | 20.38 | B | C |
| ATOM | 9724 | O | GLY | B | 78 | 73.801 | 44.851 | −3.193 | 1.00 | 20.60 | B | O |
| ATOM | 9726 | N | ALA | B | 79 | 73.847 | 43.313 | −4.835 | 1.00 | 20.03 | B | N |
| ATOM | 9727 | CA | ALA | B | 79 | 74.777 | 44.060 | −5.680 | 1.00 | 20.01 | B | C |
| ATOM | 9729 | CB | ALA | B | 79 | 75.425 | 43.132 | −6.694 | 1.00 | 20.01 | B | C |
| ATOM | 9733 | C | ALA | B | 79 | 74.077 | 45.210 | −6.396 | 1.00 | 20.07 | B | C |
| ATOM | 9734 | O | ALA | B | 79 | 74.580 | 46.333 | −6.424 | 1.00 | 19.81 | B | O |
| ATOM | 9736 | N | LEU | B | 80 | 72.918 | 44.921 | −6.981 | 1.00 | 20.65 | B | N |
| ATOM | 9737 | CA | LEU | B | 80 | 72.145 | 45.928 | −7.706 | 1.00 | 21.23 | B | C |
| ATOM | 9739 | CB | LEU | B | 80 | 71.039 | 45.265 | −8.533 | 1.00 | 21.22 | B | C |
| ATOM | 9742 | CG | LEU | B | 80 | 71.509 | 44.313 | −9.637 | 1.00 | 22.04 | B | C |
| ATOM | 9744 | CD1 | LEU | B | 80 | 70.315 | 43.623 | −10.295 | 1.00 | 22.93 | B | C |
| ATOM | 9748 | CD2 | LEU | B | 80 | 72.349 | 45.047 | −10.677 | 1.00 | 21.09 | B | C |
| ATOM | 9752 | C | LEU | B | 80 | 71.538 | 46.967 | −6.764 | 1.00 | 21.81 | B | C |
| ATOM | 9753 | O | LEU | B | 80 | 71.402 | 48.135 | −7.129 | 1.00 | 22.20 | B | O |
| ATOM | 9755 | N | ASP | B | 81 | 71.178 | 46.544 | −5.555 | 1.00 | 22.17 | B | N |
| ATOM | 9756 | CA | ASP | B | 81 | 70.651 | 47.463 | −4.543 | 1.00 | 22.35 | B | C |
| ATOM | 9758 | CB | ASP | B | 81 | 70.188 | 46.692 | −3.303 | 1.00 | 22.43 | B | C |
| ATOM | 9761 | CG | ASP | B | 81 | 69.122 | 47.433 | −2.521 | 1.00 | 23.43 | B | C |
| ATOM | 9762 | OD1 | ASP | B | 81 | 69.403 | 47.854 | −1.377 | 1.00 | 24.99 | B | O |
| ATOM | 9763 | OD2 | ASP | B | 81 | 68.004 | 47.598 | −3.055 | 1.00 | 23.01 | B | O |
| ATOM | 9764 | C | ASP | B | 81 | 71.705 | 48.509 | −4.158 | 1.00 | 22.33 | B | C |
| ATOM | 9765 | O | ASP | B | 81 | 71.374 | 49.658 | −3.862 | 1.00 | 22.00 | B | O |
| ATOM | 9767 | N | ARG | B | 82 | 72.970 | 48.091 | −4.160 | 1.00 | 22.64 | B | N |
| ATOM | 9768 | CA | ARG | B | 82 | 74.110 | 48.997 | −3.992 | 1.00 | 23.00 | B | C |
| ATOM | 9770 | CB | ARG | B | 82 | 75.429 | 48.207 | −3.977 | 1.00 | 23.31 | B | C |
| ATOM | 9773 | CG | ARG | B | 82 | 76.436 | 48.600 | −2.894 | 1.00 | 23.85 | B | C |
| ATOM | 9776 | CD | ARG | B | 82 | 76.608 | 47.462 | −1.902 | 1.00 | 25.49 | B | C |
| ATOM | 9779 | NE | ARG | B | 82 | 77.031 | 46.237 | −2.588 | 1.00 | 27.67 | B | N |
| ATOM | 9781 | CZ | ARG | B | 82 | 76.736 | 44.993 | −2.208 | 1.00 | 28.92 | B | C |
| ATOM | 9782 | NH1 | ARG | B | 82 | 75.999 | 44.755 | −1.125 | 1.00 | 29.74 | B | N |
| ATOM | 9785 | NH2 | ARG | B | 82 | 77.175 | 43.967 | −2.929 | 1.00 | 28.09 | B | N |
| ATOM | 9788 | C | ARG | B | 82 | 74.150 | 49.964 | −5.168 | 1.00 | 22.98 | B | C |
| ATOM | 9789 | O | ARG | B | 82 | 74.309 | 51.174 | −4.997 | 1.00 | 23.04 | B | O |
| ATOM | 9791 | N | PHE | B | 83 | 74.012 | 49.394 | −6.363 | 1.00 | 22.90 | B | N |
| ATOM | 9792 | CA | PHE | B | 83 | 74.097 | 50.131 | −7.620 | 1.00 | 22.96 | B | C |
| ATOM | 9794 | CB | PHE | B | 83 | 73.907 | 49.159 | −8.788 | 1.00 | 22.83 | B | C |
| ATOM | 9797 | CG | PHE | B | 83 | 74.055 | 49.790 | −10.137 | 1.00 | 22.79 | B | C |
| ATOM | 9798 | CD1 | PHE | B | 83 | 75.264 | 50.338 | −10.527 | 1.00 | 22.61 | B | C |
| ATOM | 9800 | CE1 | PHE | B | 83 | 75.411 | 50.916 | −11.776 | 1.00 | 23.30 | B | C |
| ATOM | 9802 | CZ | PHE | B | 83 | 74.340 | 50.941 | −12.656 | 1.00 | 23.91 | B | C |
| ATOM | 9804 | CE2 | PHE | B | 83 | 73.126 | 50.391 | −12.281 | 1.00 | 23.32 | B | C |
| ATOM | 9806 | CD2 | PHE | B | 83 | 72.989 | 49.816 | −11.029 | 1.00 | 23.33 | B | C |
| ATOM | 9808 | C | PHE | B | 83 | 73.081 | 51.269 | −7.701 | 1.00 | 23.09 | B | C |

TABLE 8-2-continued

Coordinates for L494P Structure

| | | | | | | | | | | | | |
|---|---|---|---|---|---|---|---|---|---|---|---|---|
| ATOM | 9809 | O | PHE | B | 83 | 73.424 | 52.381 | −8.102 | 1.00 | 23.19 | B | O |
| ATOM | 9811 | N | VAL | B | 84 | 71.840 | 50.989 | −7.312 | 1.00 | 23.08 | B | N |
| ATOM | 9812 | CA | VAL | B | 84 | 70.778 | 51.996 | −7.336 | 1.00 | 23.11 | B | C |
| ATOM | 9814 | CB | VAL | B | 84 | 69.379 | 51.347 | −7.184 | 1.00 | 23.15 | B | C |
| ATOM | 9816 | CG1 | VAL | B | 84 | 68.319 | 52.402 | −6.884 | 1.00 | 22.64 | B | C |
| ATOM | 9820 | CG2 | VAL | B | 84 | 69.019 | 50.564 | −8.441 | 1.00 | 22.66 | B | C |
| ATOM | 9824 | C | VAL | B | 84 | 70.969 | 53.048 | −6.244 | 1.00 | 23.28 | B | C |
| ATOM | 9825 | O | VAL | B | 84 | 70.892 | 54.248 | −6.513 | 1.00 | 23.33 | B | O |
| ATOM | 9827 | N | SER | B | 85 | 71.223 | 52.590 | −5.020 | 1.00 | 23.59 | B | N |
| ATOM | 9828 | CA | SER | B | 85 | 71.289 | 53.472 | −3.848 | 1.00 | 23.83 | B | C |
| ATOM | 9830 | CB | SER | B | 85 | 71.287 | 52.643 | −2.559 | 1.00 | 24.07 | B | C |
| ATOM | 9833 | OG | SER | B | 85 | 72.375 | 51.733 | −2.529 | 1.00 | 25.24 | B | O |
| ATOM | 9835 | C | SER | B | 85 | 72.493 | 54.417 | −3.851 | 1.00 | 23.55 | B | C |
| ATOM | 9836 | O | SER | B | 85 | 72.401 | 55.534 | −3.342 | 1.00 | 23.23 | B | O |
| ATOM | 9838 | N | SER | B | 86 | 73.612 | 53.973 | −4.425 | 1.00 | 23.60 | B | N |
| ATOM | 9839 | CA | SER | B | 86 | 74.814 | 54.810 | −4.524 | 1.00 | 23.71 | B | C |
| ATOM | 9841 | CB | SER | B | 86 | 76.076 | 53.937 | −4.571 | 1.00 | 23.57 | B | C |
| ATOM | 9844 | OG | SER | B | 86 | 76.163 | 53.204 | −5.781 | 1.00 | 23.18 | B | O |
| ATOM | 9846 | C | SER | B | 86 | 74.784 | 55.748 | −5.738 | 1.00 | 23.94 | B | C |
| ATOM | 9847 | O | SER | B | 86 | 75.764 | 56.444 | −6.007 | 1.00 | 23.67 | B | O |
| ATOM | 9849 | N | GLY | B | 87 | 73.664 | 55.764 | −6.462 | 1.00 | 24.30 | B | N |
| ATOM | 9850 | CA | GLY | B | 87 | 73.511 | 56.602 | −7.648 | 1.00 | 24.62 | B | C |
| ATOM | 9853 | C | GLY | B | 87 | 74.240 | 56.061 | −8.866 | 1.00 | 24.97 | B | C |
| ATOM | 9854 | O | GLY | B | 87 | 74.698 | 56.832 | −9.711 | 1.00 | 25.27 | B | O |
| ATOM | 9856 | N | GLY | B | 88 | 74.350 | 54.737 | −8.960 | 1.00 | 25.14 | B | N |
| ATOM | 9857 | CA | GLY | B | 88 | 75.008 | 54.090 | −10.096 | 1.00 | 25.27 | B | C |
| ATOM | 9860 | C | GLY | B | 88 | 74.123 | 54.077 | −11.330 | 1.00 | 25.47 | B | C |
| ATOM | 9861 | O | GLY | B | 88 | 74.598 | 54.303 | −12.446 | 1.00 | 25.09 | B | O |
| ATOM | 9863 | N | PHE | B | 89 | 72.834 | 53.811 | −11.123 | 1.00 | 25.86 | B | N |
| ATOM | 9864 | CA | PHE | B | 89 | 71.847 | 53.814 | −12.206 | 1.00 | 26.07 | B | C |
| ATOM | 9866 | CB | PHE | B | 89 | 70.486 | 53.334 | −11.688 | 1.00 | 26.21 | B | C |
| ATOM | 9869 | CG | PHE | B | 89 | 69.389 | 53.363 | −12.723 | 1.00 | 26.68 | B | C |
| ATOM | 9870 | CD1 | PHE | B | 89 | 69.523 | 52.660 | −13.915 | 1.00 | 26.40 | B | C |
| ATOM | 9872 | CE1 | PHE | B | 89 | 68.513 | 52.681 | −14.871 | 1.00 | 26.69 | B | C |
| ATOM | 9874 | CZ | PHE | B | 89 | 67.350 | 53.404 | −14.636 | 1.00 | 27.08 | B | C |
| ATOM | 9876 | CE2 | PHE | B | 89 | 67.202 | 54.104 | −13.448 | 1.00 | 27.35 | B | C |
| ATOM | 9878 | CD2 | PHE | B | 89 | 68.217 | 54.080 | −12.498 | 1.00 | 27.23 | B | C |
| ATOM | 9880 | C | PHE | B | 89 | 71.714 | 55.204 | −12.818 | 1.00 | 26.15 | B | C |
| ATOM | 9881 | O | PHE | B | 89 | 71.593 | 55.344 | −14.035 | 1.00 | 26.29 | B | O |
| ATOM | 9883 | N | ASP | B | 90 | 71.741 | 56.224 | −11.964 | 1.00 | 26.08 | B | N |
| ATOM | 9884 | CA | ASP | B | 90 | 71.678 | 57.612 | −12.411 | 1.00 | 26.14 | B | C |
| ATOM | 9886 | CB | ASP | B | 90 | 71.389 | 58.536 | −11.222 | 1.00 | 26.54 | B | C |
| ATOM | 9889 | CG | ASP | B | 90 | 70.904 | 59.914 | −11.651 | 1.00 | 28.73 | B | C |
| ATOM | 9890 | OD1 | ASP | B | 90 | 71.751 | 60.801 | −11.913 | 1.00 | 29.84 | B | O |
| ATOM | 9891 | OD2 | ASP | B | 90 | 69.671 | 60.112 | −11.709 | 1.00 | 31.49 | B | O |
| ATOM | 9892 | C | ASP | B | 90 | 72.971 | 58.042 | −13.113 | 1.00 | 25.74 | B | C |
| ATOM | 9893 | O | ASP | B | 90 | 72.949 | 58.939 | −13.955 | 1.00 | 26.14 | B | O |
| ATOM | 9895 | N | ALA | B | 91 | 74.089 | 57.400 | −12.770 | 1.00 | 25.04 | B | N |
| ATOM | 9896 | CA | ALA | B | 91 | 75.395 | 57.742 | −13.343 | 1.00 | 24.47 | B | C |
| ATOM | 9898 | CB | ALA | B | 91 | 76.517 | 57.190 | −12.470 | 1.00 | 24.49 | B | C |
| ATOM | 9902 | C | ALA | B | 91 | 75.555 | 57.246 | −14.780 | 1.00 | 23.98 | B | C |
| ATOM | 9903 | O | ALA | B | 91 | 75.966 | 58.005 | −15.657 | 1.00 | 23.86 | B | O |
| ATOM | 9905 | N | VAL | B | 92 | 75.231 | 55.976 | −15.016 | 1.00 | 23.68 | B | N |
| ATOM | 9906 | CA | VAL | B | 92 | 75.405 | 55.365 | −16.341 | 1.00 | 23.29 | B | C |
| ATOM | 9908 | CB | VAL | B | 92 | 75.211 | 53.832 | −16.307 | 1.00 | 23.10 | B | C |
| ATOM | 9910 | CG1 | VAL | B | 92 | 76.248 | 53.187 | −15.399 | 1.00 | 22.67 | B | C |
| ATOM | 9914 | CG2 | VAL | B | 92 | 73.795 | 53.473 | −15.868 | 1.00 | 23.29 | B | C |
| ATOM | 9918 | C | VAL | B | 92 | 74.474 | 55.949 | −17.406 | 1.00 | 23.09 | B | C |
| ATOM | 9919 | O | VAL | B | 92 | 74.862 | 56.059 | −18.569 | 1.00 | 23.06 | B | O |
| ATOM | 9921 | N | THR | B | 93 | 73.260 | 56.333 | −17.009 | 1.00 | 22.98 | B | N |
| ATOM | 9922 | CA | THR | B | 93 | 72.277 | 56.894 | −17.948 | 1.00 | 22.80 | B | C |
| ATOM | 9924 | CB | THR | B | 93 | 70.887 | 57.094 | −17.293 | 1.00 | 22.75 | B | C |
| ATOM | 9926 | OG1 | THR | B | 93 | 71.002 | 57.966 | −16.161 | 1.00 | 21.89 | B | O |
| ATOM | 9928 | CG2 | THR | B | 93 | 70.299 | 55.756 | −16.859 | 1.00 | 22.59 | B | C |
| ATOM | 9932 | C | THR | B | 93 | 72.721 | 58.224 | −18.567 | 1.00 | 22.54 | B | C |
| ATOM | 9933 | O | THR | B | 93 | 72.142 | 58.664 | −19.562 | 1.00 | 22.69 | B | O |
| ATOM | 9935 | N | LYS | B | 94 | 73.734 | 58.857 | −17.974 | 1.00 | 22.08 | B | N |
| ATOM | 9936 | CA | LYS | B | 94 | 74.346 | 60.061 | −18.539 | 1.00 | 21.85 | B | C |
| ATOM | 9938 | CB | LYS | B | 94 | 74.849 | 60.989 | −17.422 | 1.00 | 21.89 | B | C |
| ATOM | 9941 | CG | LYS | B | 94 | 73.825 | 61.316 | −16.333 | 1.00 | 22.60 | B | C |
| ATOM | 9944 | CD | LYS | B | 94 | 72.573 | 61.989 | −16.885 | 1.00 | 23.74 | B | C |
| ATOM | 9947 | CE | LYS | B | 94 | 71.570 | 62.282 | −15.779 | 1.00 | 24.01 | B | C |
| ATOM | 9950 | NZ | LYS | B | 94 | 70.262 | 62.747 | −16.319 | 1.00 | 23.58 | B | N |
| ATOM | 9954 | C | LYS | B | 94 | 75.509 | 59.724 | −19.479 | 1.00 | 21.38 | B | C |
| ATOM | 9955 | O | LYS | B | 94 | 75.748 | 60.447 | −20.450 | 1.00 | 21.29 | B | O |
| ATOM | 9957 | N | THR | B | 95 | 76.219 | 58.629 | −19.193 | 1.00 | 20.80 | B | N |
| ATOM | 9958 | CA | THR | B | 95 | 77.463 | 58.288 | −19.898 | 1.00 | 20.16 | B | C |
| ATOM | 9960 | CB | THR | B | 95 | 78.598 | 57.987 | −18.892 | 1.00 | 20.05 | B | C |

TABLE 8-2-continued

| Coordinates for L494P Structure | | | | | | | | | | | |
|---|---|---|---|---|---|---|---|---|---|---|---|
| ATOM | 9962 | OG1 | THR | B | 95 | 78.226 | 56.884 | −18.054 | 1.00 | 19.86 B | O |
| ATOM | 9964 | CG2 | THR | B | 95 | 78.882 | 59.208 | −18.027 | 1.00 | 19.17 B | C |
| ATOM | 9968 | C | THR | B | 95 | 77.337 | 57.110 | −20.880 | 1.00 | 19.76 B | C |
| ATOM | 9969 | O | THR | B | 95 | 77.331 | 57.315 | −22.097 | 1.00 | 19.67 B | O |
| ATOM | 9971 | N | SER | B | 96 | 77.238 | 55.889 | −20.352 | 1.00 | 19.17 B | N |
| ATOM | 9972 | CA | SER | B | 96 | 77.321 | 54.673 | −21.172 | 1.00 | 18.55 B | C |
| ATOM | 9974 | CB | SER | B | 96 | 78.197 | 53.631 | −20.474 | 1.00 | 18.28 B | C |
| ATOM | 9977 | OG | SER | B | 96 | 78.356 | 52.478 | −21.284 | 1.00 | 16.95 B | O |
| ATOM | 9979 | C | SER | B | 96 | 75.957 | 54.055 | −21.474 | 1.00 | 18.37 B | C |
| ATOM | 9980 | O | SER | B | 96 | 75.124 | 53.907 | −20.581 | 1.00 | 18.51 B | O |
| ATOM | 9982 | N | LEU | B | 97 | 75.749 | 53.681 | −22.737 | 1.00 | 18.03 B | N |
| ATOM | 9983 | CA | LEU | B | 97 | 74.538 | 52.970 | −23.156 | 1.00 | 17.63 B | C |
| ATOM | 9985 | CB | LEU | B | 97 | 74.358 | 53.060 | −24.676 | 1.00 | 17.43 B | C |
| ATOM | 9988 | CG | LEU | B | 97 | 73.200 | 52.279 | −25.308 | 1.00 | 16.33 B | C |
| ATOM | 9990 | CD1 | LEU | B | 97 | 71.862 | 52.622 | −24.663 | 1.00 | 14.88 B | C |
| ATOM | 9994 | CD2 | LEU | B | 97 | 73.158 | 52.544 | −26.799 | 1.00 | 15.23 B | C |
| ATOM | 9998 | C | LEU | B | 97 | 74.616 | 51.509 | −22.721 | 1.00 | 17.57 B | C |
| ATOM | 9999 | O | LEU | B | 97 | 73.726 | 51.012 | −22.031 | 1.00 | 17.48 B | O |
| ATOM | 10001 | N | HIS | B | 98 | 75.685 | 50.833 | −23.135 | 1.00 | 17.59 B | N |
| ATOM | 10002 | CA | HIS | B | 98 | 75.953 | 49.450 | −22.732 | 1.00 | 17.51 B | C |
| ATOM | 10004 | CB | HIS | B | 98 | 77.430 | 49.107 | −22.981 | 1.00 | 17.79 B | C |
| ATOM | 10007 | CG | HIS | B | 98 | 77.888 | 47.849 | −22.309 | 1.00 | 18.71 B | C |
| ATOM | 10008 | ND1 | HIS | B | 98 | 77.360 | 46.610 | −22.602 | 1.00 | 20.03 B | N |
| ATOM | 10010 | CE1 | HIS | B | 98 | 77.959 | 45.693 | −21.863 | 1.00 | 20.85 B | C |
| ATOM | 10012 | NE2 | HIS | B | 98 | 78.861 | 46.291 | −21.106 | 1.00 | 20.28 B | N |
| ATOM | 10014 | CD2 | HIS | B | 98 | 78.839 | 47.639 | −21.367 | 1.00 | 19.98 B | C |
| ATOM | 10016 | C | HIS | B | 98 | 75.606 | 49.243 | −21.265 | 1.00 | 17.07 B | C |
| ATOM | 10017 | O | HIS | B | 98 | 74.733 | 48.441 | −20.934 | 1.00 | 17.09 B | O |
| ATOM | 10019 | N | GLY | B | 99 | 76.280 | 49.994 | −20.399 | 1.00 | 16.69 B | N |
| ATOM | 10020 | CA | GLY | B | 99 | 76.080 | 49.903 | −18.956 | 1.00 | 16.27 B | C |
| ATOM | 10023 | C | GLY | B | 99 | 74.644 | 50.107 | −18.510 | 1.00 | 15.82 B | C |
| ATOM | 10024 | O | GLY | B | 99 | 74.218 | 49.516 | −17.518 | 1.00 | 15.84 B | O |
| ATOM | 10026 | N | THR | B | 100 | 73.902 | 50.946 | −19.233 | 1.00 | 15.36 B | N |
| ATOM | 10027 | CA | THR | B | 100 | 72.492 | 51.200 | −18.928 | 1.00 | 15.12 B | |
| ATOM | 10029 | CB | THR | B | 100 | 71.989 | 52.511 | −19.582 | 1.00 | 15.04 B | C |
| ATOM | 10031 | OG1 | THR | B | 100 | 72.701 | 53.626 | −19.034 | 1.00 | 14.95 B | O |
| ATOM | 10033 | CG2 | THR | B | 100 | 70.500 | 52.706 | −19.336 | 1.00 | 14.68 B | C |
| ATOM | 10037 | C | THR | B | 100 | 71.612 | 50.036 | −19.380 | 1.00 | 14.98 B | C |
| ATOM | 10038 | O | THR | B | 100 | 70.745 | 49.587 | −18.636 | 1.00 | 14.55 B | O |
| ATOM | 10040 | N | ALA | B | 101 | 71.846 | 49.552 | −20.596 | 1.00 | 15.35 B | N |
| ATOM | 10041 | CA | ALA | B | 101 | 71.059 | 48.452 | −21.162 | 1.00 | 15.58 B | C |
| ATOM | 10043 | CB | ALA | B | 101 | 71.386 | 48.281 | −22.637 | 1.00 | 15.49 B | C |
| ATOM | 10047 | C | ALA | B | 101 | 71.281 | 47.135 | −20.413 | 1.00 | 15.71 B | C |
| ATOM | 10048 | O | ALA | B | 101 | 70.392 | 46.278 | −20.369 | 1.00 | 16.00 B | O |
| ATOM | 10050 | N | LEU | B | 102 | 72.470 | 46.978 | −19.838 | 1.00 | 15.43 B | N |
| ATOM | 10051 | CA | LEU | B | 102 | 72.788 | 45.817 | −19.011 | 1.00 | 15.11 B | C |
| ATOM | 10053 | CB | LEU | B | 102 | 74.306 | 45.698 | −18.828 | 1.00 | 14.88 B | C |
| ATOM | 10056 | CG | LEU | B | 102 | 74.848 | 44.512 | −18.029 | 1.00 | 13.96 B | C |
| ATOM | 10058 | CD1 | LEU | B | 102 | 74.261 | 43.198 | −18.515 | 1.00 | 13.62 B | C |
| ATOM | 10062 | CD2 | LEU | B | 102 | 76.369 | 44.488 | −18.109 | 1.00 | 13.07 B | C |
| ATOM | 10066 | C | LEU | B | 102 | 72.096 | 45.934 | −17.654 | 1.00 | 15.05 B | C |
| ATOM | 10067 | O | LEU | B | 102 | 71.425 | 45.000 | −17.210 | 1.00 | 15.13 B | O |
| ATOM | 10069 | N | SER | B | 103 | 72.254 | 47.089 | −17.010 | 1.00 | 14.64 B | N |
| ATOM | 10070 | CA | SER | B | 103 | 71.667 | 47.325 | −15.695 | 1.00 | 14.21 B | C |
| ATOM | 10072 | CB | SER | B | 103 | 72.208 | 48.613 | −15.068 | 1.00 | 14.05 B | C |
| ATOM | 10075 | OG | SER | B | 103 | 71.690 | 49.766 | −15.705 | 1.00 | 13.39 B | O |
| ATOM | 10077 | C | SER | B | 103 | 70.148 | 47.383 | −15.764 | 1.00 | 14.45 B | C |
| ATOM | 10078 | O | SER | B | 103 | 69.471 | 46.896 | −14.862 | 1.00 | 15.34 B | O |
| ATOM | 10080 | N | PHE | B | 104 | 69.611 | 47.976 | −16.827 | 1.00 | 14.20 B | N |
| ATOM | 10081 | CA | PHE | B | 104 | 68.163 | 48.010 | −17.017 | 1.00 | 13.83 B | C |
| ATOM | 10083 | CB | PHE | B | 104 | 67.792 | 48.649 | −18.356 | 1.00 | 14.07 B | C |
| ATOM | 10086 | CG | PHE | B | 104 | 66.311 | 48.706 | −18.608 | 1.00 | 14.64 B | C |
| ATOM | 10087 | CD1 | PHE | B | 104 | 65.589 | 49.850 | −18.309 | 1.00 | 15.83 B | C |
| ATOM | 10089 | CE1 | PHE | B | 104 | 64.220 | 49.905 | −18.538 | 1.00 | 16.59 B | C |
| ATOM | 10091 | CZ | PHE | B | 104 | 63.562 | 48.807 | −19.068 | 1.00 | 16.05 B | C |
| ATOM | 10093 | CE2 | PHE | B | 104 | 64.272 | 47.660 | −19.368 | 1.00 | 15.67 B | C |
| ATOM | 10095 | CD2 | PHE | B | 104 | 65.639 | 47.612 | −19.140 | 1.00 | 15.20 B | C |
| ATOM | 10097 | C | PHE | B | 104 | 67.627 | 46.594 | −16.966 | 1.00 | 13.24 B | C |
| ATOM | 10098 | O | PHE | B | 104 | 66.718 | 46.295 | −16.194 | 1.00 | 13.15 B | O |
| ATOM | 10100 | N | ARG | B | 105 | 68.211 | 45.731 | −17.794 | 1.00 | 13.05 B | N |
| ATOM | 10101 | CA | ARG | B | 105 | 67.795 | 44.334 | −17.904 | 1.00 | 13.08 B | C |
| ATOM | 10103 | CB | ARG | B | 105 | 68.620 | 43.617 | −18.977 | 1.00 | 13.37 B | C |
| ATOM | 10106 | CG | ARG | B | 105 | 68.162 | 42.196 | −19.273 | 1.00 | 13.35 B | C |
| ATOM | 10109 | CD | ARG | B | 105 | 68.759 | 41.681 | −20.576 | 1.00 | 12.99 B | C |
| ATOM | 10112 | NE | ARG | B | 105 | 70.219 | 41.615 | −20.518 | 1.00 | 12.68 B | N |
| ATOM | 10114 | CZ | ARG | B | 105 | 70.918 | 40.672 | −19.885 | 1.00 | 10.95 B | C |
| ATOM | 10115 | NH1 | ARG | B | 105 | 70.309 | 39.686 | −19.231 | 1.00 | 9.34 B | N |
| ATOM | 10118 | NH2 | ARG | B | 105 | 72.246 | 40.718 | −19.902 | 1.00 | 10.70 B | N |

TABLE 8-2-continued

Coordinates for L494P Structure

| | | | | | | | | | | | | |
|---|---|---|---|---|---|---|---|---|---|---|---|---|
| ATOM | 10121 | C | ARG | B | 105 | 67.936 | 43.602 | −16.578 | 1.00 | 12.52 | B | C |
| ATOM | 10122 | O | ARG | B | 105 | 66.992 | 42.967 | −16.106 | 1.00 | 12.65 | B | O |
| ATOM | 10124 | N | LEU | B | 106 | 69.119 | 43.697 | −15.983 | 1.00 | 11.82 | B | N |
| ATOM | 10125 | CA | LEU | B | 106 | 69.380 | 43.060 | −14.699 | 1.00 | 11.23 | B | C |
| ATOM | 10127 | CB | LEU | B | 106 | 70.827 | 43.314 | −14.255 | 1.00 | 10.81 | B | C |
| ATOM | 10130 | CG | LEU | B | 106 | 71.911 | 42.650 | −15.109 | 1.00 | 8.27 | B | C |
| ATOM | 10132 | CD1 | LEU | B | 106 | 73.282 | 43.156 | −14.714 | 1.00 | 6.17 | B | C |
| ATOM | 10136 | CD2 | LEU | B | 106 | 71.845 | 41.141 | −14.993 | 1.00 | 6.13 | B | C |
| ATOM | 10140 | C | LEU | B | 106 | 68.395 | 43.548 | −13.635 | 1.00 | 11.04 | B | C |
| ATOM | 10141 | O | LEU | B | 106 | 67.783 | 42.745 | −12.939 | 1.00 | 10.80 | B | O |
| ATOM | 10143 | N | LEU | B | 107 | 68.229 | 44.862 | −13.528 | 1.00 | 11.29 | B | N |
| ATOM | 10144 | CA | LEU | B | 107 | 67.332 | 45.436 | −12.525 | 1.00 | 11.68 | B | C |
| ATOM | 10146 | CB | LEU | B | 107 | 67.324 | 46.967 | −12.603 | 1.00 | 11.63 | B | C |
| ATOM | 10149 | CG | LEU | B | 107 | 68.511 | 47.671 | −11.943 | 1.00 | 10.96 | B | C |
| ATOM | 10151 | CD1 | LEU | B | 107 | 68.589 | 49.129 | −12.377 | 1.00 | 9.53 | B | C |
| ATOM | 10155 | CD2 | LEU | B | 107 | 68.414 | 47.555 | −10.424 | 1.00 | 11.26 | B | C |
| ATOM | 10159 | C | LEU | B | 107 | 65.912 | 44.901 | −12.671 | 1.00 | 11.95 | B | C |
| ATOM | 10160 | O | LEU | B | 107 | 65.323 | 44.423 | −11.700 | 1.00 | 12.00 | B | O |
| ATOM | 10162 | N | ARG | B | 108 | 65.370 | 44.972 | −13.882 | 1.00 | 12.17 | B | N |
| ATOM | 10163 | CA | ARG | B | 108 | 64.004 | 44.516 | −14.122 | 1.00 | 12.61 | B | C |
| ATOM | 10165 | CB | ARG | B | 108 | 63.535 | 44.888 | −15.526 | 1.00 | 12.46 | B | C |
| ATOM | 10168 | CG | ARG | B | 108 | 62.082 | 44.523 | −15.779 | 1.00 | 11.97 | B | C |
| ATOM | 10171 | CD | ARG | B | 108 | 61.486 | 45.308 | −16.924 | 1.00 | 11.34 | B | C |
| ATOM | 10174 | NE | ARG | B | 108 | 61.210 | 46.693 | −16.555 | 1.00 | 10.21 | B | N |
| ATOM | 10176 | CZ | ARG | B | 108 | 60.650 | 47.590 | −17.362 | 1.00 | 10.94 | B | C |
| ATOM | 10177 | NH1 | ARG | B | 108 | 60.296 | 47.265 | −18.603 | 1.00 | 10.42 | B | N |
| ATOM | 10180 | NH2 | ARG | B | 108 | 60.443 | 48.825 | −16.924 | 1.00 | 11.87 | B | N |
| ATOM | 10183 | C | ARG | B | 108 | 63.867 | 43.011 | −13.905 | 1.00 | 13.23 | B | C |
| ATOM | 10184 | O | ARG | B | 108 | 62.876 | 42.554 | −13.338 | 1.00 | 13.51 | B | O |
| ATOM | 10186 | N | GLN | B | 109 | 64.861 | 42.252 | −14.359 | 1.00 | 13.93 | B | N |
| ATOM | 10187 | CA | GLN | B | 109 | 64.893 | 40.802 | −14.148 | 1.00 | 14.40 | B | C |
| ATOM | 10189 | CB | GLN | B | 109 | 66.224 | 40.225 | −14.650 | 1.00 | 14.43 | B | C |
| ATOM | 10192 | CG | GLN | B | 109 | 66.353 | 38.709 | −14.555 | 1.00 | 13.91 | B | C |
| ATOM | 10195 | CD | GLN | B | 109 | 67.800 | 38.247 | −14.560 | 1.00 | 12.71 | B | C |
| ATOM | 10196 | OE1 | GLN | B | 109 | 68.652 | 38.840 | −15.222 | 1.00 | 12.98 | B | O |
| ATOM | 10197 | NE2 | GLN | B | 109 | 68.083 | 37.183 | −13.819 | 1.00 | 12.06 | B | N |
| ATOM | 10200 | C | GLN | B | 109 | 64.695 | 40.461 | −12.670 | 1.00 | 14.82 | B | C |
| ATOM | 10201 | O | GLN | B | 109 | 63.935 | 39.551 | −12.336 | 1.00 | 15.14 | B | O |
| ATOM | 10203 | N | HIS | B | 110 | 65.369 | 41.208 | −11.795 | 1.00 | 15.02 | B | N |
| ATOM | 10204 | CA | HIS | B | 110 | 65.307 | 40.977 | −10.351 | 1.00 | 15.34 | B | C |
| ATOM | 10206 | CB | HIS | B | 110 | 66.702 | 41.147 | −9.732 | 1.00 | 15.49 | B | C |
| ATOM | 10209 | CG | HIS | B | 110 | 67.692 | 40.110 | −10.168 | 1.00 | 14.40 | B | C |
| ATOM | 10210 | ND1 | HIS | B | 110 | 67.790 | 38.876 | −9.563 | 1.00 | 13.44 | B | N |
| ATOM | 10212 | CE1 | HIS | B | 110 | 68.749 | 38.178 | −10.145 | 1.00 | 13.56 | B | C |
| ATOM | 10214 | NE2 | HIS | B | 110 | 69.280 | 38.917 | −11.101 | 1.00 | 11.71 | B | N |
| ATOM | 10216 | CD2 | HIS | B | 110 | 68.639 | 40.130 | −11.135 | 1.00 | 12.93 | B | C |
| ATOM | 10218 | C | HIS | B | 110 | 64.300 | 41.899 | −9.644 | 1.00 | 15.77 | B | C |
| ATOM | 10219 | O | HIS | B | 110 | 64.591 | 42.451 | −8.578 | 1.00 | 15.94 | B | O |
| ATOM | 10221 | N | GLY | B | 111 | 63.127 | 42.075 | −10.248 | 1.00 | 16.02 | B | N |
| ATOM | 10222 | CA | GLY | B | 111 | 61.992 | 42.729 | −9.590 | 1.00 | 16.43 | B | C |
| ATOM | 10225 | C | GLY | B | 111 | 62.109 | 44.199 | −9.205 | 1.00 | 16.88 | B | C |
| ATOM | 10226 | O | GLY | B | 111 | 61.257 | 44.708 | −8.474 | 1.00 | 16.73 | B | O |
| ATOM | 10228 | N | PHE | B | 112 | 63.143 | 44.890 | −9.683 | 1.00 | 17.42 | B | N |
| ATOM | 10229 | CA | PHE | B | 112 | 63.274 | 46.328 | −9.438 | 1.00 | 17.67 | B | C |
| ATOM | 10231 | CB | PHE | B | 112 | 64.722 | 46.798 | −9.597 | 1.00 | 17.98 | B | C |
| ATOM | 10234 | CG | PHE | B | 112 | 65.615 | 46.412 | −8.460 | 1.00 | 19.28 | B | C |
| ATOM | 10235 | CD1 | PHE | B | 112 | 65.605 | 47.143 | −7.281 | 1.00 | 20.60 | B | C |
| ATOM | 10237 | CE1 | PHE | B | 112 | 66.431 | 46.796 | −6.222 | 1.00 | 22.44 | B | C |
| ATOM | 10239 | CZ | PHE | B | 112 | 67.287 | 45.710 | −6.339 | 1.00 | 22.18 | B | C |
| ATOM | 10241 | CE2 | PHE | B | 112 | 67.309 | 44.976 | −7.515 | 1.00 | 21.88 | B | C |
| ATOM | 10243 | CD2 | PHE | B | 112 | 66.477 | 45.329 | −8.569 | 1.00 | 20.40 | B | C |
| ATOM | 10245 | C | PHE | B | 112 | 62.397 | 47.100 | −10.406 | 1.00 | 17.64 | B | C |
| ATOM | 10246 | O | PHE | B | 112 | 62.039 | 46.594 | −11.470 | 1.00 | 17.30 | B | O |
| ATOM | 10248 | N | GLU | B | 113 | 62.053 | 48.329 | −10.036 | 1.00 | 18.13 | B | N |
| ATOM | 10249 | CA | GLU | B | 113 | 61.356 | 49.217 | −10.952 | 1.00 | 18.59 | B | C |
| ATOM | 10251 | CB | GLU | B | 113 | 60.339 | 50.108 | −10.227 | 1.00 | 18.94 | B | C |
| ATOM | 10254 | CG | GLU | B | 113 | 59.591 | 51.062 | −11.178 | 1.00 | 20.95 | B | C |
| ATOM | 10257 | CD | GLU | B | 113 | 58.188 | 51.435 | −10.710 | 1.00 | 22.45 | B | C |
| ATOM | 10258 | OE1 | GLU | B | 113 | 57.949 | 51.484 | −9.485 | 1.00 | 25.01 | B | O |
| ATOM | 10259 | OE2 | GLU | B | 113 | 57.324 | 51.691 | −11.577 | 1.00 | 21.27 | B | O |
| ATOM | 10260 | C | GLU | B | 113 | 62.375 | 50.068 | −11.697 | 1.00 | 18.18 | B | C |
| ATOM | 10261 | O | GLU | B | 113 | 63.150 | 50.806 | −11.085 | 1.00 | 17.81 | B | O |
| ATOM | 10263 | N | VAL | B | 114 | 62.378 | 49.924 | −13.020 | 1.00 | 17.96 | B | N |
| ATOM | 10264 | CA | VAL | B | 114 | 63.109 | 50.814 | −13.915 | 1.00 | 17.72 | B | C |
| ATOM | 10266 | CB | VAL | B | 114 | 64.338 | 50.121 | −14.540 | 1.00 | 17.40 | B | C |
| ATOM | 10268 | CG1 | VAL | B | 114 | 65.341 | 49.766 | −13.458 | 1.00 | 16.56 | B | C |
| ATOM | 10272 | CG2 | VAL | B | 114 | 63.925 | 48.880 | −15.324 | 1.00 | 17.16 | B | C |
| ATOM | 10276 | C | VAL | B | 114 | 62.152 | 51.303 | −15.005 | 1.00 | 17.86 | B | C |

TABLE 8-2-continued

Coordinates for L494P Structure

| | | | | | | | | | | | | |
|---|---|---|---|---|---|---|---|---|---|---|---|---|
| ATOM | 10277 | O | VAL | B | 114 | 61.067 | 50.746 | −15.183 | 1.00 | 17.45 | B | O |
| ATOM | 10279 | N | SER | B | 115 | 62.554 | 52.351 | −15.719 | 1.00 | 18.11 | B | N |
| ATOM | 10280 | CA | SER | B | 115 | 61.695 | 52.993 | −16.713 | 1.00 | 17.98 | B | C |
| ATOM | 10282 | CB | SER | B | 115 | 61.151 | 54.311 | −16.155 | 1.00 | 17.76 | B | C |
| ATOM | 10285 | OG | SER | B | 115 | 60.269 | 54.934 | −17.070 | 1.00 | 17.43 | B | O |
| ATOM | 10287 | C | SER | B | 115 | 62.451 | 53.247 | −18.016 | 1.00 | 18.09 | B | C |
| ATOM | 10288 | O | SER | B | 115 | 63.661 | 53.487 | −18.006 | 1.00 | 18.38 | B | O |
| ATOM | 10290 | N | GLN | B | 116 | 61.724 | 53.199 | −19.132 | 1.00 | 17.77 | B | N |
| ATOM | 10291 | CA | GLN | B | 116 | 62.300 | 53.431 | −20.460 | 1.00 | 17.40 | B | C |
| ATOM | 10293 | CB | GLN | B | 116 | 61.235 | 53.251 | −21.548 | 1.00 | 17.53 | B | C |
| ATOM | 10296 | CG | GLN | B | 116 | 60.133 | 54.317 | −21.543 | 1.00 | 18.28 | B | C |
| ATOM | 10299 | CD | GLN | B | 116 | 58.938 | 53.944 | −22.404 | 1.00 | 17.36 | B | C |
| ATOM | 10300 | OE1 | GLN | B | 116 | 59.065 | 53.210 | −23.385 | 1.00 | 17.59 | B | O |
| ATOM | 10301 | NE2 | GLN | B | 116 | 57.770 | 54.456 | −22.041 | 1.00 | 15.98 | B | N |
| ATOM | 10304 | C | GLN | B | 116 | 62.944 | 54.812 | −20.589 | 1.00 | 17.28 | B | C |
| ATOM | 10305 | O | GLN | B | 116 | 63.751 | 55.035 | −21.488 | 1.00 | 17.66 | B | O |
| ATOM | 10307 | N | GLU | B | 117 | 62.586 | 55.731 | −19.693 | 1.00 | 17.24 | B | N |
| ATOM | 10308 | CA | GLU | B | 117 | 63.225 | 57.050 | −19.625 | 1.00 | 17.35 | B | C |
| ATOM | 10310 | CB | GLU | B | 117 | 62.455 | 57.969 | −18.666 | 1.00 | 17.33 | B | C |
| ATOM | 10313 | CG | GLU | B | 117 | 61.062 | 58.369 | −19.160 | 1.00 | 16.64 | B | C |
| ATOM | 10316 | CD | GLU | B | 117 | 61.092 | 59.306 | −20.364 | 1.00 | 15.94 | B | C |
| ATOM | 10317 | OE1 | GLU | B | 117 | 62.165 | 59.872 | −20.667 | 1.00 | 13.31 | B | O |
| ATOM | 10318 | OE2 | GLU | B | 117 | 60.034 | 59.479 | −21.008 | 1.00 | 15.83 | B | O |
| ATOM | 10319 | C | GLU | B | 117 | 64.706 | 56.987 | −19.218 | 1.00 | 17.41 | B | C |
| ATOM | 10320 | O | GLU | B | 117 | 65.398 | 58.005 | −19.230 | 1.00 | 17.10 | B | O |
| ATOM | 10322 | N | ALA | B | 118 | 65.184 | 55.799 | −18.848 | 1.00 | 17.79 | B | N |
| ATOM | 10323 | CA | ALA | B | 118 | 66.614 | 55.563 | −18.667 | 1.00 | 18.07 | B | C |
| ATOM | 10325 | CB | ALA | B | 118 | 66.852 | 54.162 | −18.121 | 1.00 | 17.97 | B | C |
| ATOM | 10329 | C | ALA | B | 118 | 67.360 | 55.748 | −19.986 | 1.00 | 18.33 | B | C |
| ATOM | 10330 | O | ALA | B | 118 | 68.491 | 56.234 | −20.004 | 1.00 | 18.49 | B | O |
| ATOM | 10332 | N | PHE | B | 119 | 66.711 | 55.369 | −21.085 | 1.00 | 18.76 | B | N |
| ATOM | 10333 | CA | PHE | B | 119 | 67.313 | 55.448 | −22.414 | 1.00 | 19.32 | B | C |
| ATOM | 10335 | CB | PHE | B | 119 | 66.785 | 54.310 | −23.300 | 1.00 | 19.27 | B | C |
| ATOM | 10338 | CG | PHE | B | 119 | 67.039 | 52.933 | −22.742 | 1.00 | 18.34 | B | C |
| ATOM | 10339 | CD1 | PHE | B | 119 | 65.987 | 52.138 | −22.305 | 1.00 | 17.02 | B | C |
| ATOM | 10341 | CE1 | PHE | B | 119 | 66.219 | 50.871 | −21.791 | 1.00 | 17.25 | B | C |
| ATOM | 10343 | CZ | PHE | B | 119 | 67.514 | 50.384 | −21.706 | 1.00 | 17.67 | B | C |
| ATOM | 10345 | CE2 | PHE | B | 119 | 68.574 | 51.166 | −22.137 | 1.00 | 17.65 | B | C |
| ATOM | 10347 | CD2 | PHE | B | 119 | 68.333 | 52.433 | −22.653 | 1.00 | 18.36 | B | C |
| ATOM | 10349 | C | PHE | B | 119 | 67.075 | 56.794 | −23.114 | 1.00 | 20.18 | B | C |
| ATOM | 10350 | O | PHE | B | 119 | 67.387 | 56.933 | −24.298 | 1.00 | 20.87 | B | O |
| ATOM | 10352 | N | SER | B | 120 | 66.537 | 57.781 | −22.396 | 1.00 | 20.76 | B | N |
| ATOM | 10353 | CA | SER | B | 120 | 66.253 | 59.099 | −22.982 | 1.00 | 20.91 | B | C |
| ATOM | 10355 | CB | SER | B | 120 | 65.240 | 59.870 | −22.129 | 1.00 | 20.93 | B | C |
| ATOM | 10358 | OG | SER | B | 120 | 65.837 | 60.372 | −20.944 | 1.00 | 21.26 | B | O |
| ATOM | 10360 | C | SER | B | 120 | 67.515 | 59.945 | −23.177 | 1.00 | 20.98 | B | C |
| ATOM | 10361 | O | SER | B | 120 | 67.497 | 60.912 | −23.937 | 1.00 | 21.13 | B | O |
| ATOM | 10363 | N | GLY | B | 121 | 68.601 | 59.584 | −22.496 | 1.00 | 21.23 | B | N |
| ATOM | 10364 | CA | GLY | B | 121 | 69.884 | 60.267 | −22.667 | 1.00 | 21.73 | B | C |
| ATOM | 10367 | C | GLY | B | 121 | 70.734 | 59.725 | −23.808 | 1.00 | 22.23 | B | C |
| ATOM | 10368 | O | GLY | B | 121 | 71.951 | 59.924 | −23.821 | 1.00 | 21.96 | B | O |
| ATOM | 10370 | N | PHE | B | 122 | 70.098 | 59.038 | −24.762 | 1.00 | 22.81 | B | N |
| ATOM | 10371 | CA | PHE | B | 122 | 70.789 | 58.447 | −25.913 | 1.00 | 23.32 | B | C |
| ATOM | 10373 | CB | PHE | B | 122 | 71.029 | 56.945 | −25.680 | 1.00 | 23.17 | B | C |
| ATOM | 10376 | CG | PHE | B | 122 | 71.721 | 56.627 | −24.382 | 1.00 | 22.98 | B | C |
| ATOM | 10377 | CD1 | PHE | B | 122 | 73.108 | 56.588 | −24.308 | 1.00 | 22.49 | B | C |
| ATOM | 10379 | CE1 | PHE | B | 122 | 73.750 | 56.293 | −23.107 | 1.00 | 22.39 | B | C |
| ATOM | 10381 | CZ | PHE | B | 122 | 73.002 | 56.034 | −21.968 | 1.00 | 22.47 | B | C |
| ATOM | 10383 | CE2 | PHE | B | 122 | 71.617 | 56.067 | −22.030 | 1.00 | 23.14 | B | C |
| ATOM | 10385 | CD2 | PHE | B | 122 | 70.984 | 56.361 | −23.234 | 1.00 | 23.30 | B | C |
| ATOM | 10387 | C | PHE | B | 122 | 69.984 | 58.640 | −27.204 | 1.00 | 23.76 | B | C |
| ATOM | 10388 | O | PHE | B | 122 | 69.948 | 57.751 | −28.056 | 1.00 | 23.82 | B | O |
| ATOM | 10390 | N | LYS | B | 123 | 69.348 | 59.803 | −27.349 | 1.00 | 24.39 | B | N |
| ATOM | 10391 | CA | LYS | B | 123 | 68.464 | 60.075 | −28.490 | 1.00 | 24.99 | B | C |
| ATOM | 10393 | CB | LYS | B | 123 | 66.996 | 59.960 | −28.061 | 1.00 | 25.11 | B | C |
| ATOM | 10396 | CG | LYS | B | 123 | 66.579 | 58.554 | −27.623 | 1.00 | 26.36 | B | C |
| ATOM | 10399 | CD | LYS | B | 123 | 65.256 | 58.547 | −26.858 | 1.00 | 27.49 | B | C |
| ATOM | 10402 | CE | LYS | B | 123 | 64.056 | 58.691 | −27.782 | 1.00 | 28.01 | B | C |
| ATOM | 10405 | NZ | LYS | B | 123 | 63.822 | 57.472 | −28.611 | 1.00 | 28.15 | B | N |
| ATOM | 10409 | C | LYS | B | 123 | 68.728 | 61.456 | −29.106 | 1.00 | 25.23 | B | C |
| ATOM | 10410 | O | LYS | B | 123 | 68.984 | 62.428 | −28.391 | 1.00 | 25.22 | B | O |
| ATOM | 10412 | N | ASP | B | 124 | 68.647 | 61.529 | −30.435 | 1.00 | 25.37 | B | N |
| ATOM | 10413 | CA | ASP | B | 124 | 68.960 | 62.755 | −31.185 | 1.00 | 25.33 | B | C |
| ATOM | 10415 | CB | ASP | B | 124 | 69.203 | 62.423 | −32.673 | 1.00 | 25.38 | B | C |
| ATOM | 10418 | CG | ASP | B | 124 | 67.946 | 61.934 | −33.398 | 1.00 | 24.90 | B | C |
| ATOM | 10419 | OD1 | ASP | B | 124 | 66.838 | 61.988 | −32.824 | 1.00 | 23.59 | B | O |
| ATOM | 10420 | OD2 | ASP | B | 124 | 68.072 | 61.489 | −34.558 | 1.00 | 23.99 | B | O |
| ATOM | 10421 | C | ASP | B | 124 | 67.882 | 63.840 | −31.028 | 1.00 | 25.30 | B | C |

TABLE 8-2-continued

Coordinates for L494P Structure

| | | | | | | | | | | | | |
|---|---|---|---|---|---|---|---|---|---|---|---|---|
| ATOM | 10422 | O | ASP | B | 124 | 66.943 | 63.683 | −30.243 | 1.00 | 25.33 | B | O |
| ATOM | 10424 | N | GLN | B | 125 | 68.032 | 64.938 | −31.770 | 1.00 | 25.13 | B | N |
| ATOM | 10425 | CA | GLN | B | 125 | 67.047 | 66.026 | −31.767 | 1.00 | 25.14 | B | C |
| ATOM | 10427 | CB | GLN | B | 125 | 67.458 | 67.128 | −32.750 | 1.00 | 25.16 | B | C |
| ATOM | 10430 | CG | GLN | B | 125 | 68.471 | 68.123 | −32.187 | 1.00 | 25.92 | B | C |
| ATOM | 10433 | CD | GLN | B | 125 | 67.855 | 69.137 | −31.228 | 1.00 | 25.99 | B | C |
| ATOM | 10434 | OE1 | GLN | B | 125 | 66.688 | 69.032 | −30.849 | 1.00 | 26.31 | B | O |
| ATOM | 10435 | NE2 | GLN | B | 125 | 68.646 | 70.126 | −30.832 | 1.00 | 25.52 | B | N |
| ATOM | 10438 | C | GLN | B | 125 | 65.633 | 65.545 | −32.098 | 1.00 | 25.09 | B | C |
| ATOM | 10439 | O | GLN | B | 125 | 64.675 | 65.901 | −31.409 | 1.00 | 25.17 | B | O |
| ATOM | 10441 | N | ASN | B | 126 | 65.511 | 64.738 | −33.149 | 1.00 | 24.90 | B | N |
| ATOM | 10442 | CA | ASN | B | 126 | 64.213 | 64.199 | −33.567 | 1.00 | 24.53 | B | C |
| ATOM | 10444 | CB | ASN | B | 126 | 64.337 | 63.471 | −34.911 | 1.00 | 24.47 | B | C |
| ATOM | 10447 | CG | ASN | B | 126 | 64.510 | 64.422 | −36.078 | 1.00 | 24.13 | B | C |
| ATOM | 10448 | OD1 | ASN | B | 126 | 65.064 | 65.511 | −35.930 | 1.00 | 23.55 | B | O |
| ATOM | 10449 | ND2 | ASN | B | 126 | 64.033 | 64.015 | −37.249 | 1.00 | 23.27 | B | N |
| ATOM | 10452 | C | ASN | B | 126 | 63.578 | 63.257 | −32.545 | 1.00 | 24.35 | B | C |
| ATOM | 10453 | O | ASN | B | 126 | 62.352 | 63.204 | −32.430 | 1.00 | 24.38 | B | O |
| ATOM | 10455 | N | GLY | B | 127 | 64.411 | 62.524 | −31.808 | 1.00 | 23.98 | B | N |
| ATOM | 10456 | CA | GLY | B | 127 | 63.938 | 61.494 | −30.881 | 1.00 | 23.80 | B | C |
| ATOM | 10459 | C | GLY | B | 127 | 64.216 | 60.076 | −31.357 | 1.00 | 23.59 | B | C |
| ATOM | 10460 | O | GLY | B | 127 | 63.608 | 59.124 | −30.865 | 1.00 | 23.44 | B | O |
| ATOM | 10462 | N | ASN | B | 128 | 65.117 | 59.939 | −32.330 | 1.00 | 23.46 | B | N |
| ATOM | 10463 | CA | ASN | B | 128 | 65.661 | 58.641 | −32.721 | 1.00 | 23.17 | B | C |
| ATOM | 10465 | CB | ASN | B | 128 | 65.918 | 58.577 | −34.232 | 1.00 | 23.19 | B | C |
| ATOM | 10468 | CG | ASN | B | 128 | 64.713 | 59.001 | −35.056 | 1.00 | 22.48 | B | C |
| ATOM | 10469 | OD1 | ASN | B | 128 | 64.149 | 60.075 | −34.846 | 1.00 | 20.86 | B | O |
| ATOM | 10470 | ND2 | ASN | B | 128 | 64.323 | 58.162 | −36.010 | 1.00 | 21.21 | B | N |
| ATOM | 10473 | C | ASN | B | 128 | 66.972 | 58.432 | −31.980 | 1.00 | 22.97 | B | C |
| ATOM | 10474 | O | ASN | B | 128 | 67.583 | 59.394 | −31.515 | 1.00 | 22.71 | B | O |
| ATOM | 10476 | N | PHE | B | 129 | 67.408 | 57.182 | −31.870 | 1.00 | 22.94 | B | N |
| ATOM | 10477 | CA | PHE | B | 129 | 68.691 | 56.885 | −31.234 | 1.00 | 22.94 | B | C |
| ATOM | 10479 | CB | PHE | B | 129 | 68.859 | 55.380 | −31.017 | 1.00 | 23.04 | B | C |
| ATOM | 10482 | CG | PHE | B | 129 | 68.061 | 54.844 | −29.863 | 1.00 | 24.12 | B | C |
| ATOM | 10483 | CD1 | PHE | B | 129 | 66.708 | 54.559 | −30.011 | 1.00 | 25.06 | B | C |
| ATOM | 10485 | CE1 | PHE | B | 129 | 65.965 | 54.066 | −28.946 | 1.00 | 25.61 | B | C |
| ATOM | 10487 | CZ | PHE | B | 129 | 66.575 | 53.850 | −27.718 | 1.00 | 25.88 | B | C |
| ATOM | 10489 | CE2 | PHE | B | 129 | 67.926 | 54.130 | −27.559 | 1.00 | 25.30 | B | C |
| ATOM | 10491 | CD2 | PHE | B | 129 | 68.661 | 54.625 | −28.628 | 1.00 | 24.47 | B | C |
| ATOM | 10493 | C | PHE | B | 129 | 69.827 | 57.432 | −32.091 | 1.00 | 22.78 | B | C |
| ATOM | 10494 | O | PHE | B | 129 | 69.719 | 57.474 | −33.320 | 1.00 | 22.90 | B | O |
| ATOM | 10496 | N | LEU | B | 130 | 70.907 | 57.862 | −31.441 | 1.00 | 22.49 | B | N |
| ATOM | 10497 | CA | LEU | B | 130 | 72.045 | 58.435 | −32.154 | 1.00 | 22.33 | B | C |
| ATOM | 10499 | CB | LEU | B | 130 | 73.095 | 58.980 | −31.178 | 1.00 | 22.14 | B | C |
| ATOM | 10502 | CG | LEU | B | 130 | 72.731 | 60.262 | −30.422 | 1.00 | 21.49 | B | C |
| ATOM | 10504 | CD1 | LEU | B | 130 | 73.833 | 60.628 | −29.442 | 1.00 | 20.84 | B | C |
| ATOM | 10508 | CD2 | LEU | B | 130 | 72.469 | 61.414 | −31.383 | 1.00 | 20.96 | B | C |
| ATOM | 10512 | C | LEU | B | 130 | 72.672 | 57.393 | −33.075 | 1.00 | 22.54 | B | C |
| ATOM | 10513 | O | LEU | B | 130 | 73.072 | 56.320 | −32.626 | 1.00 | 22.34 | B | O |
| ATOM | 10515 | N | GLU | B | 131 | 72.730 | 57.721 | −34.365 | 1.00 | 23.02 | B | N |
| ATOM | 10516 | CA | GLU | B | 131 | 73.337 | 56.863 | −35.387 | 1.00 | 23.37 | B | C |
| ATOM | 10518 | CB | GLU | B | 131 | 73.410 | 57.629 | −36.718 | 1.00 | 23.40 | B | C |
| ATOM | 10521 | CG | GLU | B | 131 | 74.128 | 56.913 | −37.870 | 1.00 | 24.01 | B | C |
| ATOM | 10524 | CD | GLU | B | 131 | 73.300 | 55.813 | −38.517 | 1.00 | 25.54 | B | C |
| ATOM | 10525 | OE1 | GLU | B | 131 | 72.271 | 55.395 | −37.939 | 1.00 | 26.84 | B | O |
| ATOM | 10526 | OE2 | GLU | B | 131 | 73.688 | 55.362 | −39.616 | 1.00 | 26.70 | B | O |
| ATOM | 10527 | C | GLU | B | 131 | 74.732 | 56.388 | −34.976 | 1.00 | 23.61 | B | C |
| ATOM | 10528 | O | GLU | B | 131 | 75.065 | 55.213 | −35.130 | 1.00 | 23.84 | B | O |
| ATOM | 10530 | N | ASN | B | 132 | 75.531 | 57.306 | −34.438 | 1.00 | 23.67 | B | N |
| ATOM | 10531 | CA | ASN | B | 132 | 76.923 | 57.024 | −34.060 | 1.00 | 23.74 | B | C |
| ATOM | 10533 | CB | ASN | B | 132 | 77.674 | 58.343 | −33.806 | 1.00 | 23.96 | B | C |
| ATOM | 10536 | CG | ASN | B | 132 | 76.916 | 59.285 | −32.884 | 1.00 | 24.66 | B | C |
| ATOM | 10537 | OD1 | ASN | B | 132 | 76.613 | 58.945 | −31.739 | 1.00 | 25.44 | B | O |
| ATOM | 10538 | ND2 | ASN | B | 132 | 76.604 | 60.477 | −33.384 | 1.00 | 24.88 | B | N |
| ATOM | 10541 | C | ASN | B | 132 | 77.118 | 56.056 | −32.873 | 1.00 | 23.55 | B | C |
| ATOM | 10542 | O | ASN | B | 132 | 78.253 | 55.791 | −32.469 | 1.00 | 23.42 | B | O |
| ATOM | 10544 | N | LEU | B | 133 | 76.022 | 55.535 | −32.322 | 1.00 | 23.55 | B | N |
| ATOM | 10545 | CA | LEU | B | 133 | 76.087 | 54.480 | −31.303 | 1.00 | 23.52 | B | C |
| ATOM | 10547 | CB | LEU | B | 133 | 74.870 | 54.555 | −30.370 | 1.00 | 23.31 | B | C |
| ATOM | 10550 | CG | LEU | B | 133 | 74.750 | 55.823 | −29.521 | 1.00 | 22.53 | B | C |
| ATOM | 10552 | CD1 | LEU | B | 133 | 73.383 | 55.904 | −28.862 | 1.00 | 20.74 | B | C |
| ATOM | 10556 | CD2 | LEU | B | 133 | 75.857 | 55.886 | −28.477 | 1.00 | 22.10 | B | C |
| ATOM | 10560 | C | LEU | B | 133 | 76.180 | 53.075 | −31.916 | 1.00 | 23.65 | B | C |
| ATOM | 10561 | O | LEU | B | 133 | 76.404 | 52.102 | −31.193 | 1.00 | 23.81 | B | O |
| ATOM | 10563 | N | LYS | B | 134 | 76.011 | 52.970 | −33.237 | 1.00 | 23.51 | B | N |
| ATOM | 10564 | CA | LYS | B | 134 | 76.111 | 51.681 | −33.931 | 1.00 | 23.40 | B | C |
| ATOM | 10566 | CB | LYS | B | 134 | 75.613 | 51.790 | −35.382 | 1.00 | 23.26 | B | C |
| ATOM | 10569 | CG | LYS | B | 134 | 76.593 | 52.452 | −36.356 | 1.00 | 23.29 | B | C |

TABLE 8-2-continued

Coordinates for L494P Structure

| | | | | | | | | | | | | |
|---|---|---|---|---|---|---|---|---|---|---|---|---|
| ATOM | 10572 | CD | LYS | B | 134 | 76.009 | 52.566 | −37.761 | 1.00 | 22.10 | B | C |
| ATOM | 10575 | CE | LYS | B | 134 | 77.047 | 53.064 | −38.759 | 1.00 | 20.46 | B | C |
| ATOM | 10578 | NZ | LYS | B | 134 | 76.503 | 53.139 | −40.141 | 1.00 | 18.74 | B | N |
| ATOM | 10582 | C | LYS | B | 134 | 77.539 | 51.126 | −33.907 | 1.00 | 23.60 | B | C |
| ATOM | 10583 | O | LYS | B | 134 | 77.736 | 49.915 | −34.006 | 1.00 | 23.60 | B | O |
| ATOM | 10585 | N | GLU | B | 135 | 78.525 | 52.014 | −33.780 | 1.00 | 23.90 | B | N |
| ATOM | 10586 | CA | GLU | B | 135 | 79.934 | 51.615 | −33.743 | 1.00 | 24.13 | B | C |
| ATOM | 10588 | CB | GLU | B | 135 | 80.853 | 52.842 | −33.837 | 1.00 | 24.42 | B | C |
| ATOM | 10591 | CG | GLU | B | 135 | 80.740 | 53.633 | −35.149 | 1.00 | 25.24 | B | C |
| ATOM | 10594 | CD | GLU | B | 135 | 81.137 | 52.832 | −36.384 | 1.00 | 25.99 | B | C |
| ATOM | 10595 | OE1 | GLU | B | 135 | 81.957 | 51.895 | −36.266 | 1.00 | 25.85 | B | O |
| ATOM | 10596 | OE2 | GLU | B | 135 | 80.629 | 53.148 | −37.482 | 1.00 | 26.38 | B | O |
| ATOM | 10597 | C | GLU | B | 135 | 80.275 | 50.800 | −32.493 | 1.00 | 23.93 | B | C |
| ATOM | 10598 | O | GLU | B | 135 | 81.150 | 49.934 | −32.542 | 1.00 | 24.05 | B | O |
| ATOM | 10600 | N | ASP | B | 136 | 79.596 | 51.078 | −31.382 | 1.00 | 23.74 | B | N |
| ATOM | 10601 | CA | ASP | B | 136 | 79.752 | 50.270 | −30.172 | 1.00 | 23.80 | B | C |
| ATOM | 10603 | CB | ASP | B | 136 | 79.424 | 51.090 | −28.914 | 1.00 | 23.79 | B | C |
| ATOM | 10606 | CG | ASP | B | 136 | 80.046 | 50.506 | −27.647 | 1.00 | 23.69 | B | C |
| ATOM | 10607 | OD1 | ASP | B | 136 | 80.288 | 49.280 | −27.589 | 1.00 | 22.19 | B | O |
| ATOM | 10608 | OD2 | ASP | B | 136 | 80.295 | 51.282 | −26.701 | 1.00 | 24.10 | B | O |
| ATOM | 10609 | C | ASP | B | 136 | 78.855 | 49.031 | −30.280 | 1.00 | 23.77 | B | C |
| ATOM | 10610 | O | ASP | B | 136 | 77.667 | 49.080 | −29.957 | 1.00 | 23.85 | B | O |
| ATOM | 10612 | N | ILE | B | 137 | 79.438 | 47.927 | −30.743 | 1.00 | 23.58 | B | N |
| ATOM | 10613 | CA | ILE | B | 137 | 78.701 | 46.674 | −30.945 | 1.00 | 23.48 | B | C |
| ATOM | 10615 | CB | ILE | B | 137 | 79.553 | 45.638 | −31.734 | 1.00 | 23.47 | B | C |
| ATOM | 10617 | CG1 | ILE | B | 137 | 79.750 | 46.086 | −33.189 | 1.00 | 23.86 | B | C |
| ATOM | 10620 | CD1 | ILE | B | 137 | 80.947 | 46.990 | −33.413 | 1.00 | 23.96 | B | C |
| ATOM | 10624 | CG2 | ILE | B | 137 | 78.900 | 44.261 | −31.712 | 1.00 | 23.85 | B | C |
| ATOM | 10628 | C | ILE | B | 137 | 78.242 | 46.065 | −29.612 | 1.00 | 23.33 | B | C |
| ATOM | 10629 | O | ILE | B | 137 | 77.241 | 45.344 | −29.559 | 1.00 | 23.33 | B | O |
| ATOM | 10631 | N | LYS | B | 138 | 78.974 | 46.368 | −28.543 | 1.00 | 22.92 | B | N |
| ATOM | 10632 | CA | LYS | B | 138 | 78.647 | 45.884 | −27.202 | 1.00 | 22.45 | B | C |
| ATOM | 10634 | CB | LYS | B | 138 | 79.815 | 46.177 | −26.252 | 1.00 | 22.66 | B | C |
| ATOM | 10637 | CG | LYS | B | 138 | 80.011 | 45.168 | −25.136 | 1.00 | 23.58 | B | C |
| ATOM | 10640 | CD | LYS | B | 138 | 80.951 | 45.726 | −24.063 | 1.00 | 25.04 | B | C |
| ATOM | 10643 | CE | LYS | B | 138 | 81.815 | 44.644 | −23.430 | 1.00 | 25.73 | B | C |
| ATOM | 10646 | NZ | LYS | B | 138 | 82.936 | 44.235 | −24.324 | 1.00 | 25.22 | B | N |
| ATOM | 10650 | C | LYS | B | 138 | 77.364 | 46.542 | −26.673 | 1.00 | 21.59 | B | C |
| ATOM | 10651 | O | LYS | B | 138 | 76.492 | 45.864 | −26.123 | 1.00 | 21.40 | B | O |
| ATOM | 10653 | N | ALA | B | 139 | 77.258 | 47.860 | −26.853 | 1.00 | 20.48 | B | N |
| ATOM | 10654 | CA | ALA | B | 139 | 76.130 | 48.643 | −26.335 | 1.00 | 19.64 | B | C |
| ATOM | 10656 | CB | ALA | B | 139 | 76.479 | 50.125 | −26.324 | 1.00 | 19.54 | B | C |
| ATOM | 10660 | C | ALA | B | 139 | 74.841 | 48.416 | −27.118 | 1.00 | 19.12 | B | C |
| ATOM | 10661 | O | ALA | B | 139 | 73.756 | 48.368 | −26.535 | 1.00 | 19.04 | B | O |
| ATOM | 10663 | N | ILE | B | 140 | 74.961 | 48.292 | −28.437 | 1.00 | 18.59 | B | N |
| ATOM | 10664 | CA | ILE | B | 140 | 73.814 | 47.982 | −29.291 | 1.00 | 18.11 | B | C |
| ATOM | 10666 | CB | ILE | B | 140 | 74.197 | 47.979 | −30.791 | 1.00 | 18.07 | B | C |
| ATOM | 10668 | CG1 | ILE | B | 140 | 74.613 | 49.380 | −31.254 | 1.00 | 18.28 | B | C |
| ATOM | 10671 | CD1 | ILE | B | 140 | 73.475 | 50.378 | −31.350 | 1.00 | 18.35 | B | C |
| ATOM | 10675 | CG2 | ILE | B | 140 | 73.040 | 47.471 | −31.646 | 1.00 | 17.81 | B | C |
| ATOM | 10679 | C | ILE | B | 140 | 73.234 | 46.614 | −28.928 | 1.00 | 17.72 | B | C |
| ATOM | 10680 | O | ILE | B | 140 | 72.017 | 46.443 | −28.889 | 1.00 | 18.01 | B | O |
| ATOM | 10682 | N | LEU | B | 141 | 74.108 | 45.648 | −28.657 | 1.00 | 17.08 | B | N |
| ATOM | 10683 | CA | LEU | B | 141 | 73.674 | 44.295 | −28.331 | 1.00 | 16.61 | B | C |
| ATOM | 10685 | CB | LEU | B | 141 | 74.854 | 43.324 | −28.386 | 1.00 | 16.26 | B | C |
| ATOM | 10688 | CG | LEU | B | 141 | 74.528 | 41.828 | −28.324 | 1.00 | 15.01 | B | C |
| ATOM | 10690 | CD1 | LEU | B | 141 | 73.243 | 41.487 | −29.069 | 1.00 | 13.84 | B | C |
| ATOM | 10694 | CD2 | LEU | B | 141 | 75.696 | 41.020 | −28.873 | 1.00 | 14.21 | B | C |
| ATOM | 10698 | C | LEU | B | 141 | 73.003 | 44.233 | −26.963 | 1.00 | 16.78 | B | C |
| ATOM | 10699 | O | LEU | B | 141 | 71.933 | 43.640 | −26.820 | 1.00 | 17.29 | B | O |
| ATOM | 10701 | N | SER | B | 142 | 73.624 | 44.843 | −25.958 | 1.00 | 16.60 | B | N |
| ATOM | 10702 | CA | SER | B | 142 | 73.015 | 44.911 | −24.627 | 1.00 | 16.64 | B | C |
| ATOM | 10704 | CB | SER | B | 142 | 73.944 | 45.607 | −23.625 | 1.00 | 16.83 | B | C |
| ATOM | 10707 | OG | SER | B | 142 | 74.964 | 44.727 | −23.179 | 1.00 | 16.19 | B | O |
| ATOM | 10709 | C | SER | B | 142 | 71.659 | 45.621 | −24.692 | 1.00 | 16.43 | B | C |
| ATOM | 10710 | O | SER | B | 142 | 70.700 | 45.194 | −24.048 | 1.00 | 16.17 | B | O |
| ATOM | 10712 | N | LEU | B | 143 | 71.589 | 46.697 | −25.474 | 1.00 | 16.32 | B | N |
| ATOM | 10713 | CA | LEU | B | 143 | 70.322 | 47.380 | −25.743 | 1.00 | 16.29 | B | C |
| ATOM | 10715 | CB | LEU | B | 143 | 70.539 | 48.590 | −26.664 | 1.00 | 15.94 | B | C |
| ATOM | 10718 | CG | LEU | B | 143 | 69.296 | 49.191 | −27.331 | 1.00 | 15.20 | B | C |
| ATOM | 10720 | CD1 | LEU | B | 143 | 68.240 | 49.558 | −26.301 | 1.00 | 13.55 | B | C |
| ATOM | 10724 | CD2 | LEU | B | 143 | 69.678 | 50.402 | −28.160 | 1.00 | 15.26 | B | C |
| ATOM | 10728 | C | LEU | B | 143 | 69.312 | 46.415 | −26.365 | 1.00 | 16.70 | B | C |
| ATOM | 10729 | O | LEU | B | 143 | 68.150 | 46.375 | −25.957 | 1.00 | 17.42 | B | O |
| ATOM | 10731 | N | TYR | B | 144 | 69.765 | 45.644 | −27.350 | 1.00 | 16.53 | B | N |
| ATOM | 10732 | CA | TYR | B | 144 | 68.921 | 44.657 | −28.024 | 1.00 | 16.27 | B | C |
| ATOM | 10734 | CB | TYR | B | 144 | 69.718 | 43.942 | −29.118 | 1.00 | 16.16 | B | C |
| ATOM | 10737 | CG | TYR | B | 144 | 69.051 | 42.714 | −29.692 | 1.00 | 15.78 | B | C |

TABLE 8-2-continued

| Coordinates for L494P Structure | | | | | | | | | | | | |
|---|---|---|---|---|---|---|---|---|---|---|---|---|
| ATOM | 10738 | CD1 | TYR | B | 144 | 67.955 | 42.822 | −30.541 | 1.00 | 15.10 | B | C |
| ATOM | 10740 | CE1 | TYR | B | 144 | 67.349 | 41.697 | −31.077 | 1.00 | 14.61 | B | C |
| ATOM | 10742 | CZ | TYR | B | 144 | 67.844 | 40.447 | −30.769 | 1.00 | 15.60 | B | C |
| ATOM | 10743 | OH | TYR | B | 144 | 67.251 | 39.325 | −31.297 | 1.00 | 19.22 | B | O |
| ATOM | 10745 | CE2 | TYR | B | 144 | 68.933 | 40.314 | −29.932 | 1.00 | 16.86 | B | C |
| ATOM | 10747 | CD2 | TYR | B | 144 | 69.531 | 41.444 | −29.401 | 1.00 | 16.55 | B | C |
| ATOM | 10749 | C | TYR | B | 144 | 68.336 | 43.641 | −27.046 | 1.00 | 16.32 | B | C |
| ATOM | 10750 | O | TYR | B | 144 | 67.143 | 43.348 | −27.094 | 1.00 | 16.33 | B | O |
| ATOM | 10752 | N | GLU | B | 145 | 69.178 | 43.116 | −26.159 | 1.00 | 16.42 | B | N |
| ATOM | 10753 | CA | GLU | B | 145 | 68.738 | 42.136 | −25.162 | 1.00 | 16.72 | B | C |
| ATOM | 10755 | CB | GLU | B | 145 | 69.940 | 41.586 | −24.382 | 1.00 | 16.57 | B | C |
| ATOM | 10758 | CG | GLU | B | 145 | 70.940 | 40.787 | −25.221 | 1.00 | 16.50 | B | C |
| ATOM | 10761 | CD | GLU | B | 145 | 70.436 | 39.406 | −25.610 | 1.00 | 16.57 | B | C |
| ATOM | 10762 | OE1 | GLU | B | 145 | 69.275 | 39.069 | −25.290 | 1.00 | 17.83 | B | O |
| ATOM | 10763 | OE2 | GLU | B | 145 | 71.208 | 38.652 | −26.240 | 1.00 | 16.22 | B | O |
| ATOM | 10764 | C | GLU | B | 145 | 67.718 | 42.732 | −24.184 | 1.00 | 16.86 | B | C |
| ATOM | 10765 | O | GLU | B | 145 | 66.768 | 42.055 | −23.773 | 1.00 | 16.50 | B | O |
| ATOM | 10767 | N | ALA | B | 146 | 67.918 | 44.004 | −23.832 | 1.00 | 16.74 | B | N |
| ATOM | 10768 | CA | ALA | B | 146 | 67.088 | 44.687 | −22.838 | 1.00 | 16.36 | B | C |
| ATOM | 10770 | CB | ALA | B | 146 | 67.859 | 45.847 | −22.219 | 1.00 | 15.89 | B | C |
| ATOM | 10774 | C | ALA | B | 146 | 65.760 | 45.187 | −23.402 | 1.00 | 16.26 | B | C |
| ATOM | 10775 | O | ALA | B | 146 | 64.922 | 45.683 | −22.650 | 1.00 | 16.44 | B | O |
| ATOM | 10777 | N | SER | B | 147 | 65.568 | 45.064 | −24.713 | 1.00 | 16.21 | B | N |
| ATOM | 10778 | CA | SER | B | 147 | 64.326 | 45.496 | −25.354 | 1.00 | 16.38 | B | C |
| ATOM | 10780 | CB | SER | B | 147 | 64.536 | 45.662 | −26.862 | 1.00 | 16.51 | B | C |
| ATOM | 10783 | OG | SER | B | 147 | 64.814 | 44.420 | −27.489 | 1.00 | 17.36 | B | O |
| ATOM | 10785 | C | SER | B | 147 | 63.163 | 44.531 | −25.096 | 1.00 | 16.24 | B | C |
| ATOM | 10786 | O | SER | B | 147 | 62.015 | 44.959 | −24.969 | 1.00 | 15.95 | B | O |
| ATOM | 10788 | N | PHE | B | 148 | 63.467 | 43.237 | −25.009 | 1.00 | 16.34 | B | N |
| ATOM | 10789 | CA | PHE | B | 148 | 62.435 | 42.198 | −24.890 | 1.00 | 16.34 | B | C |
| ATOM | 10791 | CB | PHE | B | 148 | 63.026 | 40.816 | −25.190 | 1.00 | 16.30 | B | C |
| ATOM | 10794 | CG | PHE | B | 148 | 63.444 | 40.640 | −26.620 | 1.00 | 17.03 | B | C |
| ATOM | 10795 | CD1 | PHE | B | 148 | 62.570 | 40.093 | −27.548 | 1.00 | 18.20 | B | C |
| ATOM | 10797 | CE1 | PHE | B | 148 | 62.948 | 39.938 | −28.877 | 1.00 | 19.13 | B | C |
| ATOM | 10799 | CZ | PHE | B | 148 | 64.213 | 40.335 | −29.287 | 1.00 | 18.33 | B | C |
| ATOM | 10801 | CE2 | PHE | B | 148 | 65.093 | 40.887 | −28.369 | 1.00 | 17.95 | B | C |
| ATOM | 10803 | CD2 | PHE | B | 148 | 64.705 | 41.039 | −27.044 | 1.00 | 17.59 | B | C |
| ATOM | 10805 | C | PHE | B | 148 | 61.738 | 42.187 | −23.530 | 1.00 | 16.13 | B | C |
| ATOM | 10806 | O | PHE | B | 148 | 60.615 | 41.695 | −23.415 | 1.00 | 15.72 | B | O |
| ATOM | 10808 | N | LEU | B | 149 | 62.391 | 42.750 | −22.514 | 1.00 | 16.32 | B | N |
| ATOM | 10809 | CA | LEU | B | 149 | 61.811 | 42.840 | −21.171 | 1.00 | 16.28 | B | C |
| ATOM | 10811 | CB | LEU | B | 149 | 62.910 | 43.001 | −20.117 | 1.00 | 15.75 | B | C |
| ATOM | 10814 | CG | LEU | B | 149 | 63.883 | 41.829 | −20.010 | 1.00 | 15.12 | B | C |
| ATOM | 10816 | CD1 | LEU | B | 149 | 65.018 | 41.960 | −21.017 | 1.00 | 14.29 | B | C |
| ATOM | 10820 | CD2 | LEU | B | 149 | 64.430 | 41.725 | −18.598 | 1.00 | 15.76 | B | C |
| ATOM | 10824 | C | LEU | B | 149 | 60.816 | 43.995 | −21.049 | 1.00 | 16.79 | B | C |
| ATOM | 10825 | O | LEU | B | 149 | 60.382 | 44.327 | −19.943 | 1.00 | 17.29 | B | O |
| ATOM | 10827 | N | ALA | B | 150 | 60.451 | 44.597 | −22.182 | 1.00 | 16.76 | B | N |
| ATOM | 10828 | CA | ALA | B | 150 | 59.538 | 45.736 | −22.205 | 1.00 | 16.50 | B | C |
| ATOM | 10830 | CB | ALA | B | 150 | 59.404 | 46.271 | −23.627 | 1.00 | 16.43 | B | C |
| ATOM | 10834 | C | ALA | B | 150 | 58.163 | 45.397 | −21.646 | 1.00 | 16.20 | B | C |
| ATOM | 10835 | O | ALA | B | 150 | 57.838 | 44.230 | −21.406 | 1.00 | 15.98 | B | O |
| ATOM | 10837 | N | LEU | B | 151 | 57.368 | 46.440 | −21.437 | 1.00 | 16.11 | B | N |
| ATOM | 10838 | CA | LEU | B | 151 | 55.992 | 46.298 | −20.982 | 1.00 | 16.14 | B | C |
| ATOM | 10840 | CB | LEU | B | 151 | 55.809 | 46.980 | −19.625 | 1.00 | 16.21 | B | C |
| ATOM | 10843 | CG | LEU | B | 151 | 56.718 | 46.502 | −18.488 | 1.00 | 15.32 | B | C |
| ATOM | 10845 | CD1 | LEU | B | 151 | 56.599 | 47.436 | −17.293 | 1.00 | 13.46 | B | C |
| ATOM | 10849 | CD2 | LEU | B | 151 | 56.397 | 45.066 | −18.088 | 1.00 | 13.69 | B | C |
| ATOM | 10853 | C | LEU | B | 151 | 55.044 | 46.910 | −22.008 | 1.00 | 16.00 | B | C |
| ATOM | 10854 | O | LEU | B | 151 | 55.475 | 47.599 | −22.936 | 1.00 | 15.95 | B | O |
| ATOM | 10856 | N | GLU | B | 152 | 53.752 | 46.651 | −21.830 | 1.00 | 15.76 | B | N |
| ATOM | 10857 | CA | GLU | B | 152 | 52.730 | 47.163 | −22.734 | 1.00 | 15.95 | B | C |
| ATOM | 10859 | CB | GLU | B | 152 | 51.356 | 46.595 | −22.363 | 1.00 | 16.09 | B | C |
| ATOM | 10862 | CG | GLU | B | 152 | 50.504 | 46.178 | −23.560 | 1.00 | 17.01 | B | C |
| ATOM | 10865 | CD | GLU | B | 152 | 49.009 | 46.229 | −23.277 | 1.00 | 17.41 | B | C |
| ATOM | 10866 | OE1 | GLU | B | 152 | 48.623 | 46.417 | −22.103 | 1.00 | 17.43 | B | O |
| ATOM | 10867 | OE2 | GLU | B | 152 | 48.216 | 46.086 | −24.233 | 1.00 | 17.21 | B | O |
| ATOM | 10868 | C | GLU | B | 152 | 52.700 | 48.689 | −22.649 | 1.00 | 16.18 | B | C |
| ATOM | 10869 | O | GLU | B | 152 | 52.615 | 49.243 | −21.554 | 1.00 | 16.81 | B | O |
| ATOM | 10871 | N | GLY | B | 153 | 52.789 | 49.362 | −23.795 | 1.00 | 16.13 | B | N |
| ATOM | 10872 | CA | GLY | B | 153 | 52.784 | 50.828 | −23.839 | 1.00 | 15.84 | B | C |
| ATOM | 10875 | C | GLY | B | 153 | 54.164 | 51.469 | −23.884 | 1.00 | 15.69 | B | C |
| ATOM | 10876 | O | GLY | B | 153 | 54.307 | 52.590 | −24.373 | 1.00 | 15.81 | B | O |
| ATOM | 10878 | N | GLU | B | 154 | 55.178 | 50.771 | −23.374 | 1.00 | 15.51 | B | N |
| ATOM | 10879 | CA | GLU | B | 154 | 56.550 | 51.282 | −23.382 | 1.00 | 15.70 | B | C |
| ATOM | 10881 | CB | GLU | B | 154 | 57.448 | 50.439 | −22.467 | 1.00 | 15.97 | B | C |
| ATOM | 10884 | CG | GLU | B | 154 | 57.054 | 50.515 | −20.994 | 1.00 | 16.22 | B | C |
| ATOM | 10887 | CD | GLU | B | 154 | 58.095 | 49.917 | −20.062 | 1.00 | 15.63 | B | C |

TABLE 8-2-continued

Coordinates for L494P Structure

| | | | | | | | | | | | |
|---|---|---|---|---|---|---|---|---|---|---|---|
| ATOM | 10888 | OE1 | GLU | B | 154 | 58.417 | 50.567 | −19.046 | 1.00 | 12.92 B | O |
| ATOM | 10889 | OE2 | GLU | B | 154 | 58.590 | 48.802 | −20.341 | 1.00 | 16.00 B | O |
| ATOM | 10890 | C | GLU | B | 154 | 57.105 | 51.317 | −24.807 | 1.00 | 15.67 B | C |
| ATOM | 10891 | O | GLU | B | 154 | 57.757 | 50.375 | −25.262 | 1.00 | 15.68 B | O |
| ATOM | 10893 | N | ASN | B | 155 | 56.843 | 52.423 | −25.498 | 1.00 | 15.69 B | N |
| ATOM | 10894 | CA | ASN | B | 155 | 57.164 | 52.547 | −26.924 | 1.00 | 15.77 B | C |
| ATOM | 10896 | CB | ASN | B | 155 | 56.417 | 53.741 | −27.552 | 1.00 | 15.68 B | C |
| ATOM | 10899 | CG | ASN | B | 155 | 56.741 | 55.074 | −26.883 | 1.00 | 15.48 B | C |
| ATOM | 10900 | OD1 | ASN | B | 155 | 57.898 | 55.377 | −26.591 | 1.00 | 15.65 B | O |
| ATOM | 10901 | ND2 | ASN | B | 155 | 55.711 | 55.882 | −26.655 | 1.00 | 14.42 B | N |
| ATOM | 10904 | C | ASN | B | 155 | 58.661 | 52.613 | −27.260 | 1.00 | 15.85 B | C |
| ATOM | 10905 | O | ASN | B | 155 | 59.062 | 52.208 | −28.351 | 1.00 | 16.36 B | O |
| ATOM | 10907 | N | ILE | B | 156 | 59.478 | 53.117 | −26.335 | 1.00 | 15.40 B | N |
| ATOM | 10908 | CA | ILE | B | 156 | 60.903 | 53.345 | −26.610 | 1.00 | 14.84 B | C |
| ATOM | 10910 | CB | ILE | B | 156 | 61.565 | 54.261 | −25.548 | 1.00 | 14.77 B | C |
| ATOM | 10912 | CG1 | ILE | B | 156 | 60.846 | 55.612 | −25.479 | 1.00 | 14.33 B | C |
| ATOM | 10915 | CD1 | ILE | B | 156 | 61.588 | 56.669 | −24.686 | 1.00 | 13.21 B | C |
| ATOM | 10919 | CG2 | ILE | B | 156 | 63.038 | 54.486 | −25.870 | 1.00 | 14.12 B | C |
| ATOM | 10923 | C | ILE | B | 156 | 61.690 | 52.037 | −26.718 | 1.00 | 14.66 B | C |
| ATOM | 10924 | O | ILE | B | 156 | 62.621 | 51.939 | −27.516 | 1.00 | 14.69 B | O |
| ATOM | 10926 | N | LEU | B | 157 | 61.319 | 51.038 | −25.922 | 1.00 | 14.65 B | N |
| ATOM | 10927 | CA | LEU | B | 157 | 61.992 | 49.735 | −25.974 | 1.00 | 14.75 B | C |
| ATOM | 10929 | CB | LEU | B | 157 | 61.576 | 48.846 | −24.796 | 1.00 | 14.48 B | C |
| ATOM | 10932 | CG | LEU | B | 157 | 62.394 | 49.043 | −23.516 | 1.00 | 13.97 B | C |
| ATOM | 10934 | CD1 | LEU | B | 157 | 62.541 | 50.515 | −23.164 | 1.00 | 15.30 B | C |
| ATOM | 10938 | CD2 | LEU | B | 157 | 61.766 | 48.288 | −22.364 | 1.00 | 13.93 B | C |
| ATOM | 10942 | C | LEU | B | 157 | 61.744 | 49.022 | −27.306 | 1.00 | 15.28 B | C |
| ATOM | 10943 | O | LEU | B | 157 | 62.644 | 48.368 | −27.832 | 1.00 | 15.56 B | O |
| ATOM | 10945 | N | ASP | B | 158 | 60.536 | 49.158 | −27.849 | 1.00 | 15.69 B | N |
| ATOM | 10946 | CA | ASP | B | 158 | 60.230 | 48.641 | −29.184 | 1.00 | 16.04 B | C |
| ATOM | 10948 | CB | ASP | B | 158 | 58.766 | 48.888 | −29.546 | 1.00 | 16.00 B | C |
| ATOM | 10951 | CG | ASP | B | 158 | 57.807 | 48.095 | −28.682 | 1.00 | 17.24 B | C |
| ATOM | 10952 | OD1 | ASP | B | 158 | 58.224 | 47.607 | −27.609 | 1.00 | 19.56 B | O |
| ATOM | 10953 | OD2 | ASP | B | 158 | 56.630 | 47.963 | −29.081 | 1.00 | 17.24 B | O |
| ATOM | 10954 | C | ASP | B | 158 | 61.127 | 49.307 | −30.222 | 1.00 | 16.55 B | C |
| ATOM | 10955 | O | ASP | B | 158 | 61.746 | 48.625 | −31.041 | 1.00 | 16.41 B | O |
| ATOM | 10957 | N | GLU | B | 159 | 61.192 | 50.640 | −30.171 | 1.00 | 17.24 B | N |
| ATOM | 10958 | CA | GLU | B | 159 | 62.070 | 51.427 | −31.045 | 1.00 | 17.47 B | C |
| ATOM | 10960 | CB | GLU | B | 159 | 61.967 | 52.923 | −30.728 | 1.00 | 17.55 B | C |
| ATOM | 10963 | CG | GLU | B | 159 | 60.630 | 53.563 | −31.057 | 1.00 | 19.36 B | C |
| ATOM | 10966 | CD | GLU | B | 159 | 60.517 | 54.982 | −30.511 | 1.00 | 22.03 B | C |
| ATOM | 10967 | OE1 | GLU | B | 159 | 61.422 | 55.804 | −30.782 | 1.00 | 21.37 B | O |
| ATOM | 10968 | OE2 | GLU | B | 159 | 59.522 | 55.273 | −29.812 | 1.00 | 23.93 B | O |
| ATOM | 10969 | C | GLU | B | 159 | 63.522 | 50.995 | −30.887 | 1.00 | 17.46 B | C |
| ATOM | 10970 | O | GLU | B | 159 | 64.280 | 50.984 | −31.856 | 1.00 | 17.74 B | O |
| ATOM | 10972 | N | ALA | B | 160 | 63.900 | 50.651 | −29.656 | 1.00 | 17.33 B | N |
| ATOM | 10973 | CA | ALA | B | 160 | 65.238 | 50.152 | −29.361 | 1.00 | 17.26 B | C |
| ATOM | 10975 | CB | ALA | B | 160 | 65.405 | 49.946 | −27.866 | 1.00 | 17.19 B | C |
| ATOM | 10979 | C | ALA | B | 160 | 65.517 | 48.852 | −30.105 | 1.00 | 17.27 B | C |
| ATOM | 10980 | O | ALA | B | 160 | 66.602 | 48.671 | −30.658 | 1.00 | 17.36 B | O |
| ATOM | 10982 | N | LYS | B | 161 | 64.534 | 47.955 | −30.121 | 1.00 | 17.28 B | N |
| ATOM | 10983 | CA | LYS | B | 161 | 64.679 | 46.673 | −30.806 | 1.00 | 17.64 B | C |
| ATOM | 10985 | CB | LYS | B | 161 | 63.488 | 45.756 | −30.499 | 1.00 | 17.92 B | C |
| ATOM | 10988 | CG | LYS | B | 161 | 63.630 | 44.332 | −31.034 | 1.00 | 18.60 B | C |
| ATOM | 10991 | CD | LYS | B | 161 | 62.821 | 43.311 | −30.222 | 1.00 | 19.37 B | C |
| ATOM | 10994 | CE | LYS | B | 161 | 61.331 | 43.648 | −30.151 | 1.00 | 19.94 B | C |
| ATOM | 10997 | NZ | LYS | B | 161 | 60.535 | 42.535 | −29.550 | 1.00 | 19.72 B | N |
| ATOM | 11001 | C | LYS | B | 161 | 64.827 | 46.884 | −32.311 | 1.00 | 17.64 B | C |
| ATOM | 11002 | O | LYS | B | 161 | 65.773 | 46.387 | −32.921 | 1.00 | 17.55 B | O |
| ATOM | 11004 | N | VAL | B | 162 | 63.904 | 47.644 | −32.897 | 1.00 | 17.74 B | N |
| ATOM | 11005 | CA | VAL | B | 162 | 63.945 | 47.954 | −34.331 | 1.00 | 17.76 B | C |
| ATOM | 11007 | CB | VAL | B | 162 | 62.713 | 48.788 | −34.770 | 1.00 | 17.61 B | C |
| ATOM | 11009 | CG1 | VAL | B | 162 | 62.847 | 49.240 | −36.220 | 1.00 | 16.32 B | C |
| ATOM | 11013 | CG2 | VAL | B | 162 | 61.435 | 47.983 | −34.579 | 1.00 | 17.55 B | C |
| ATOM | 11017 | C | VAL | B | 162 | 65.231 | 48.697 | −34.713 | 1.00 | 17.95 B | C |
| ATOM | 11018 | O | VAL | B | 162 | 65.733 | 48.540 | −35.829 | 1.00 | 18.42 B | O |
| ATOM | 11020 | N | PHE | B | 163 | 65.760 | 49.491 | −33.783 | 1.00 | 17.79 B | N |
| ATOM | 11021 | CA | PHE | B | 163 | 66.995 | 50.244 | −34.008 | 1.00 | 17.65 B | C |
| ATOM | 11023 | CB | PHE | B | 163 | 67.121 | 51.380 | −32.985 | 1.00 | 17.30 B | C |
| ATOM | 11026 | CG | PHE | B | 163 | 68.412 | 52.132 | −33.073 | 1.00 | 15.04 B | C |
| ATOM | 11027 | CD1 | PHE | B | 163 | 68.578 | 53.138 | −34.008 | 1.00 | 14.91 B | C |
| ATOM | 11029 | CE1 | PHE | B | 163 | 69.773 | 53.832 | −34.095 | 1.00 | 15.53 B | C |
| ATOM | 11031 | CZ | PHE | B | 163 | 70.819 | 53.520 | −33.238 | 1.00 | 14.60 B | C |
| ATOM | 11033 | CE2 | PHE | B | 163 | 70.664 | 52.517 | −32.305 | 1.00 | 13.99 B | C |
| ATOM | 11035 | CD2 | PHE | B | 163 | 69.467 | 51.827 | −32.227 | 1.00 | 13.98 B | C |
| ATOM | 11037 | C | PHE | B | 163 | 68.245 | 49.360 | −33.958 | 1.00 | 18.10 B | C |
| ATOM | 11038 | O | PHE | B | 163 | 69.188 | 49.574 | −34.722 | 1.00 | 18.08 B | O |
| ATOM | 11040 | N | ALA | B | 164 | 68.256 | 48.381 | −33.055 | 1.00 | 18.58 B | N |

TABLE 8-2-continued

Coordinates for L494P Structure

| | | | | | | | | | | | | |
|---|---|---|---|---|---|---|---|---|---|---|---|---|
| ATOM | 11041 | CA | ALA | B | 164 | 69.415 | 47.502 | −32.882 | 1.00 | 18.87 | B | C |
| ATOM | 11043 | CB | ALA | B | 164 | 69.362 | 46.814 | −31.532 | 1.00 | 18.67 | B | C |
| ATOM | 11047 | C | ALA | B | 164 | 69.499 | 46.467 | −33.999 | 1.00 | 19.36 | B | C |
| ATOM | 11048 | O | ALA | B | 164 | 70.548 | 46.304 | −34.616 | 1.00 | 19.42 | B | O |
| ATOM | 11050 | N | ILE | B | 165 | 68.386 | 45.783 | −34.258 | 1.00 | 20.22 | B | N |
| ATOM | 11051 | CA | ILE | B | 165 | 68.322 | 44.739 | −35.290 | 1.00 | 20.91 | B | C |
| ATOM | 11053 | CB | ILE | B | 165 | 66.900 | 44.120 | −35.396 | 1.00 | 21.06 | B | C |
| ATOM | 11055 | CG1 | ILE | B | 165 | 66.529 | 43.370 | −34.114 | 1.00 | 20.91 | B | C |
| ATOM | 11058 | CD1 | ILE | B | 165 | 65.107 | 42.851 | −34.110 | 1.00 | 21.56 | B | C |
| ATOM | 11062 | CG2 | ILE | B | 165 | 66.810 | 43.158 | −36.577 | 1.00 | 21.26 | B | C |
| ATOM | 11066 | C | ILE | B | 165 | 68.732 | 45.267 | −36.668 | 1.00 | 21.49 | B | C |
| ATOM | 11067 | O | ILE | B | 165 | 69.319 | 44.533 | −37.466 | 1.00 | 21.69 | B | O |
| ATOM | 11069 | N | SER | B | 166 | 68.419 | 46.533 | −36.941 | 1.00 | 22.01 | B | N |
| ATOM | 11070 | CA | SER | B | 166 | 68.784 | 47.169 | −38.210 | 1.00 | 22.52 | B | C |
| ATOM | 11072 | CB | SER | B | 166 | 68.144 | 48.560 | −38.322 | 1.00 | 22.55 | B | C |
| ATOM | 11075 | OG | SER | B | 166 | 68.720 | 49.477 | −37.407 | 1.00 | 22.35 | B | O |
| ATOM | 11077 | C | SER | B | 166 | 70.302 | 47.274 | −38.410 | 1.00 | 23.00 | B | C |
| ATOM | 11078 | O | SER | B | 166 | 70.782 | 47.188 | −39.542 | 1.00 | 23.31 | B | O |
| ATOM | 11080 | N | HIS | B | 167 | 71.044 | 47.460 | −37.317 | 1.00 | 23.34 | B | N |
| ATOM | 11081 | CA | HIS | B | 167 | 72.509 | 47.582 | −37.372 | 1.00 | 23.44 | B | C |
| ATOM | 11083 | CB | HIS | B | 167 | 73.004 | 48.652 | −36.387 | 1.00 | 23.48 | B | C |
| ATOM | 11086 | CG | HIS | B | 167 | 72.718 | 50.058 | −36.822 | 1.00 | 24.37 | B | C |
| ATOM | 11087 | ND1 | HIS | B | 167 | 72.058 | 50.966 | −36.022 | 1.00 | 24.84 | B | N |
| ATOM | 11089 | CE1 | HIS | B | 167 | 71.949 | 52.117 | −36.661 | 1.00 | 24.23 | B | C |
| ATOM | 11091 | NE2 | HIS | B | 167 | 72.513 | 51.988 | −37.849 | 1.00 | 24.82 | B | N |
| ATOM | 11093 | CD2 | HIS | B | 167 | 73.001 | 50.710 | −37.974 | 1.00 | 25.08 | B | C |
| ATOM | 11095 | C | HIS | B | 167 | 73.244 | 46.264 | −37.103 | 1.00 | 23.24 | B | C |
| ATOM | 11096 | O | HIS | B | 167 | 74.377 | 46.095 | −37.546 | 1.00 | 23.60 | B | O |
| ATOM | 11098 | N | LEU | B | 168 | 72.605 | 45.340 | −36.387 | 1.00 | 22.97 | B | N |
| ATOM | 11099 | CA | LEU | B | 168 | 73.255 | 44.091 | −35.967 | 1.00 | 22.95 | B | C |
| ATOM | 11101 | CB | LEU | B | 168 | 72.449 | 43.412 | −34.852 | 1.00 | 22.93 | B | C |
| ATOM | 11104 | CG | LEU | B | 168 | 72.509 | 44.048 | −33.460 | 1.00 | 22.05 | B | C |
| ATOM | 11106 | CD1 | LEU | B | 168 | 71.330 | 43.587 | −32.619 | 1.00 | 20.71 | B | C |
| ATOM | 11110 | CD2 | LEU | B | 168 | 73.827 | 43.733 | −32.766 | 1.00 | 20.14 | B | C |
| ATOM | 11114 | C | LEU | B | 168 | 73.462 | 43.089 | −37.103 | 1.00 | 23.36 | B | C |
| ATOM | 11115 | O | LEU | B | 168 | 74.549 | 42.531 | −37.249 | 1.00 | 23.26 | B | O |
| ATOM | 11117 | N | LYS | B | 169 | 72.418 | 42.855 | −37.893 | 1.00 | 24.10 | B | N |
| ATOM | 11118 | CA | LYS | B | 169 | 72.433 | 41.778 | −38.892 | 1.00 | 24.87 | B | C |
| ATOM | 11120 | CB | LYS | B | 169 | 71.002 | 41.350 | −39.249 | 1.00 | 24.93 | B | C |
| ATOM | 11123 | CG | LYS | B | 169 | 70.192 | 42.360 | −40.059 | 1.00 | 25.82 | B | C |
| ATOM | 11126 | CD | LYS | B | 169 | 68.686 | 42.102 | −39.943 | 1.00 | 27.02 | B | C |
| ATOM | 11129 | CE | LYS | B | 169 | 68.291 | 40.714 | −40.452 | 1.00 | 27.94 | B | C |
| ATOM | 11132 | NZ | LYS | B | 169 | 66.823 | 40.466 | −40.352 | 1.00 | 27.64 | B | N |
| ATOM | 11136 | C | LYS | B | 169 | 73.231 | 42.100 | −40.161 | 1.00 | 25.51 | B | C |
| ATOM | 11137 | O | LYS | B | 169 | 73.547 | 41.195 | −40.937 | 1.00 | 25.25 | B | O |
| ATOM | 11139 | N | GLU | B | 170 | 73.564 | 43.376 | −40.361 | 1.00 | 26.58 | B | N |
| ATOM | 11140 | CA | GLU | B | 170 | 74.350 | 43.809 | −41.523 | 1.00 | 27.53 | B | C |
| ATOM | 11142 | CB | GLU | B | 170 | 73.806 | 45.137 | −42.080 | 1.00 | 27.70 | B | C |
| ATOM | 11145 | CG | GLU | B | 170 | 72.272 | 45.219 | −42.233 | 1.00 | 29.32 | B | C |
| ATOM | 11148 | CD | GLU | B | 170 | 71.704 | 44.349 | −43.355 | 1.00 | 30.04 | B | C |
| ATOM | 11149 | OE1 | GLU | B | 170 | 72.480 | 43.674 | −44.065 | 1.00 | 31.89 | B | O |
| ATOM | 11150 | OE2 | GLU | B | 170 | 70.467 | 44.347 | −43.530 | 1.00 | 28.58 | B | O |
| ATOM | 11151 | C | GLU | B | 170 | 75.843 | 43.964 | −41.181 | 1.00 | 27.95 | B | C |
| ATOM | 11152 | O | GLU | B | 170 | 76.540 | 44.784 | −41.792 | 1.00 | 28.24 | B | O |
| ATOM | 11154 | N | LEU | B | 171 | 76.326 | 43.173 | −40.217 | 1.00 | 27.99 | B | N |
| ATOM | 11155 | CA | LEU | B | 171 | 77.729 | 43.208 | −39.791 | 1.00 | 27.86 | B | C |
| ATOM | 11157 | CB | LEU | B | 171 | 77.830 | 43.290 | −38.264 | 1.00 | 27.64 | B | C |
| ATOM | 11160 | CG | LEU | B | 171 | 77.203 | 44.514 | −37.588 | 1.00 | 26.91 | B | C |
| ATOM | 11162 | CD1 | LEU | B | 171 | 77.470 | 44.483 | −36.088 | 1.00 | 24.62 | B | C |
| ATOM | 11166 | CD2 | LEU | B | 171 | 77.709 | 45.818 | −38.197 | 1.00 | 25.86 | B | C |
| ATOM | 11170 | C | LEU | B | 171 | 78.485 | 41.976 | −40.283 | 1.00 | 28.06 | B | C |
| ATOM | 11171 | O | LEU | B | 171 | 77.922 | 40.882 | −40.362 | 1.00 | 27.83 | B | O |
| ATOM | 11173 | N | SER | B | 172 | 79.766 | 42.166 | −40.595 | 1.00 | 28.45 | B | N |
| ATOM | 11174 | CA | SER | B | 172 | 80.616 | 41.104 | −41.136 | 1.00 | 28.64 | B | C |
| ATOM | 11176 | CB | SER | B | 172 | 81.520 | 41.664 | −42.237 | 1.00 | 28.62 | B | C |
| ATOM | 11179 | OG | SER | B | 172 | 82.445 | 40.690 | −42.689 | 1.00 | 28.34 | B | O |
| ATOM | 11181 | C | SER | B | 172 | 81.476 | 40.461 | −40.051 | 1.00 | 28.97 | B | C |
| ATOM | 11182 | O | SER | B | 172 | 81.869 | 41.120 | −39.084 | 1.00 | 28.98 | B | O |
| ATOM | 11184 | N | GLU | B | 173 | 81.778 | 39.176 | −40.232 | 1.00 | 29.33 | B | N |
| ATOM | 11185 | CA | GLU | B | 173 | 82.661 | 38.439 | −39.323 | 1.00 | 29.65 | B | C |
| ATOM | 11187 | CB | GLU | B | 173 | 82.531 | 36.925 | −39.553 | 1.00 | 29.65 | B | C |
| ATOM | 11190 | CG | GLU | B | 173 | 83.188 | 36.059 | −38.471 | 1.00 | 30.47 | B | C |
| ATOM | 11193 | CD | GLU | B | 173 | 82.816 | 34.585 | −38.567 | 1.00 | 31.62 | B | C |
| ATOM | 11194 | OE1 | GLU | B | 173 | 81.610 | 34.271 | −38.670 | 1.00 | 31.50 | B | O |
| ATOM | 11195 | OE2 | GLU | B | 173 | 83.732 | 33.735 | −38.523 | 1.00 | 31.84 | B | O |
| ATOM | 11196 | C | GLU | B | 173 | 84.126 | 38.882 | −39.464 | 1.00 | 29.86 | B | C |
| ATOM | 11197 | O | GLU | B | 173 | 84.962 | 38.534 | −38.630 | 1.00 | 30.01 | B | O |
| ATOM | 11199 | N | GLU | B | 174 | 84.435 | 39.639 | −40.518 | 1.00 | 29.81 | B | N |

TABLE 8-2-continued

Coordinates for L494P Structure

| | | | | | | | | | | | | |
|---|---|---|---|---|---|---|---|---|---|---|---|---|
| ATOM | 11200 | CA | GLU | B | 174 | 85.760 | 40.244 | −40.676 | 1.00 | 29.91 | B | C |
| ATOM | 11202 | CB | GLU | B | 174 | 86.107 | 40.423 | −42.160 | 1.00 | 30.15 | B | C |
| ATOM | 11205 | CG | GLU | B | 174 | 86.698 | 39.179 | −42.809 | 1.00 | 30.29 | B | C |
| ATOM | 11208 | CD | GLU | B | 174 | 86.767 | 39.283 | −44.321 | 1.00 | 29.90 | B | C |
| ATOM | 11209 | OE1 | GLU | B | 174 | 87.889 | 39.316 | −44.868 | 1.00 | 29.26 | B | O |
| ATOM | 11210 | OE2 | GLU | B | 174 | 85.697 | 39.339 | −44.962 | 1.00 | 29.35 | B | O |
| ATOM | 11211 | C | GLU | B | 174 | 85.855 | 41.587 | −39.950 | 1.00 | 29.71 | B | C |
| ATOM | 11212 | O | GLU | B | 174 | 86.787 | 41.810 | −39.175 | 1.00 | 29.67 | B | O |
| ATOM | 11214 | N | LYS | B | 175 | 84.891 | 42.473 | −40.205 | 1.00 | 29.47 | B | N |
| ATOM | 11215 | CA | LYS | B | 175 | 84.867 | 43.811 | −39.595 | 1.00 | 29.30 | B | C |
| ATOM | 11217 | CB | LYS | B | 175 | 83.570 | 44.546 | −39.944 | 1.00 | 29.60 | B | C |
| ATOM | 11220 | CG | LYS | B | 175 | 83.454 | 44.992 | −41.390 | 1.00 | 30.58 | B | C |
| ATOM | 11223 | CD | LYS | B | 175 | 82.079 | 45.598 | −41.651 | 1.00 | 31.84 | B | C |
| ATOM | 11226 | CE | LYS | B | 175 | 81.816 | 45.781 | −43.136 | 1.00 | 32.09 | B | C |
| ATOM | 11229 | NZ | LYS | B | 175 | 80.394 | 46.124 | −43.416 | 1.00 | 32.12 | B | N |
| ATOM | 11233 | C | LYS | B | 175 | 85.001 | 43.754 | −38.076 | 1.00 | 28.77 | B | C |
| ATOM | 11234 | O | LYS | B | 175 | 85.642 | 44.612 | −37.470 | 1.00 | 28.82 | B | O |
| ATOM | 11236 | N | ILE | B | 176 | 84.375 | 42.745 | −37.476 | 1.00 | 28.19 | B | N |
| ATOM | 11237 | CA | ILE | B | 176 | 84.444 | 42.513 | −36.034 | 1.00 | 27.82 | B | C |
| ATOM | 11239 | CB | ILE | B | 176 | 83.105 | 42.841 | −35.331 | 1.00 | 27.95 | B | C |
| ATOM | 11241 | CG1 | ILE | B | 176 | 81.911 | 42.300 | −36.132 | 1.00 | 27.44 | B | C |
| ATOM | 11244 | CD1 | ILE | B | 176 | 80.584 | 42.443 | −35.424 | 1.00 | 26.82 | B | C |
| ATOM | 11248 | CG2 | ILE | B | 176 | 82.971 | 44.346 | −35.137 | 1.00 | 28.50 | B | C |
| ATOM | 11252 | C | ILE | B | 176 | 84.834 | 41.061 | −35.777 | 1.00 | 27.40 | B | C |
| ATOM | 11253 | O | ILE | B | 176 | 84.754 | 40.227 | −36.675 | 1.00 | 27.29 | B | O |
| ATOM | 11255 | N | GLY | B | 177 | 85.249 | 40.767 | −34.548 | 1.00 | 26.94 | B | N |
| ATOM | 11256 | CA | GLY | B | 177 | 85.791 | 39.452 | −34.203 | 1.00 | 26.74 | B | C |
| ATOM | 11259 | C | GLY | B | 177 | 84.867 | 38.276 | −34.467 | 1.00 | 26.46 | B | C |
| ATOM | 11260 | O | GLY | B | 177 | 83.648 | 38.434 | −34.540 | 1.00 | 26.73 | B | O |
| ATOM | 11262 | N | LYS | B | 178 | 85.461 | 37.094 | −34.618 | 1.00 | 26.15 | B | N |
| ATOM | 11263 | CA | LYS | B | 178 | 84.706 | 35.851 | −34.767 | 1.00 | 25.92 | B | C |
| ATOM | 11265 | CB | LYS | B | 178 | 85.657 | 34.667 | −34.967 | 1.00 | 25.77 | B | C |
| ATOM | 11268 | CG | LYS | B | 178 | 84.967 | 33.322 | −35.183 | 1.00 | 25.80 | B | C |
| ATOM | 11271 | CD | LYS | B | 178 | 85.979 | 32.189 | −35.296 | 1.00 | 25.76 | B | C |
| ATOM | 11274 | CE | LYS | B | 178 | 85.347 | 30.924 | −35.863 | 1.00 | 25.07 | B | C |
| ATOM | 11277 | NZ | LYS | B | 178 | 86.333 | 29.818 | −35.998 | 1.00 | 23.38 | B | N |
| ATOM | 11281 | C | LYS | B | 178 | 83.832 | 35.609 | −33.538 | 1.00 | 26.02 | B | C |
| ATOM | 11282 | O | LYS | B | 178 | 82.671 | 35.214 | −33.667 | 1.00 | 26.16 | B | O |
| ATOM | 11284 | N | GLU | B | 179 | 84.393 | 35.850 | −32.353 | 1.00 | 25.87 | B | N |
| ATOM | 11285 | CA | GLU | B | 179 | 83.658 | 35.649 | −31.099 | 1.00 | 25.72 | B | C |
| ATOM | 11287 | CB | GLU | B | 179 | 84.603 | 35.673 | −29.881 | 1.00 | 25.81 | B | C |
| ATOM | 11290 | CG | GLU | B | 179 | 85.277 | 37.014 | −29.571 | 1.00 | 26.23 | B | C |
| ATOM | 11293 | CD | GLU | B | 179 | 86.166 | 36.951 | −28.330 | 1.00 | 26.14 | B | C |
| ATOM | 11294 | OE1 | GLU | B | 179 | 86.250 | 37.961 | −27.601 | 1.00 | 25.98 | B | O |
| ATOM | 11295 | OE2 | GLU | B | 179 | 86.780 | 35.892 | −28.077 | 1.00 | 25.53 | B | O |
| ATOM | 11296 | C | GLU | B | 179 | 82.509 | 36.649 | −30.932 | 1.00 | 25.07 | B | C |
| ATOM | 11297 | O | GLU | B | 179 | 81.457 | 36.298 | −30.397 | 1.00 | 24.79 | B | O |
| ATOM | 11299 | N | LEU | B | 180 | 82.712 | 37.881 | −31.401 | 1.00 | 24.36 | B | N |
| ATOM | 11300 | CA | LEU | B | 180 | 81.663 | 38.904 | −31.370 | 1.00 | 23.69 | B | C |
| ATOM | 11302 | CB | LEU | B | 180 | 82.253 | 40.300 | −31.611 | 1.00 | 23.71 | B | C |
| ATOM | 11305 | CG | LEU | B | 180 | 81.387 | 41.489 | −31.175 | 1.00 | 23.25 | B | C |
| ATOM | 11307 | CD1 | LEU | B | 180 | 81.356 | 41.608 | −29.657 | 1.00 | 22.05 | B | C |
| ATOM | 11311 | CD2 | LEU | B | 180 | 81.892 | 42.785 | −31.800 | 1.00 | 22.07 | B | C |
| ATOM | 11315 | C | LEU | B | 180 | 80.578 | 38.604 | −32.407 | 1.00 | 23.13 | B | C |
| ATOM | 11316 | O | LEU | B | 180 | 79.404 | 38.903 | −32.187 | 1.00 | 22.94 | B | O |
| ATOM | 11318 | N | ALA | B | 181 | 80.980 | 38.015 | −33.533 | 1.00 | 22.63 | B | N |
| ATOM | 11319 | CA | ALA | B | 181 | 80.039 | 37.593 | −34.573 | 1.00 | 22.38 | B | C |
| ATOM | 11321 | CB | ALA | B | 181 | 80.792 | 37.158 | −35.819 | 1.00 | 22.13 | B | C |
| ATOM | 11325 | C | ALA | B | 181 | 79.138 | 36.459 | −34.083 | 1.00 | 22.21 | B | C |
| ATOM | 11326 | O | ALA | B | 181 | 77.935 | 36.451 | −34.347 | 1.00 | 22.14 | B | O |
| ATOM | 11328 | N | GLU | B | 182 | 79.732 | 35.506 | −33.371 | 1.00 | 21.95 | B | N |
| ATOM | 11329 | CA | GLU | B | 182 | 79.000 | 34.349 | −32.857 | 1.00 | 21.66 | B | C |
| ATOM | 11331 | CB | GLU | B | 182 | 79.979 | 33.284 | −32.350 | 1.00 | 21.93 | B | C |
| ATOM | 11334 | CG | GLU | B | 182 | 80.709 | 32.557 | −33.481 | 1.00 | 22.98 | B | C |
| ATOM | 11337 | CD | GLU | B | 182 | 81.913 | 31.751 | −33.016 | 1.00 | 23.56 | B | C |
| ATOM | 11338 | OE1 | GLU | B | 182 | 82.298 | 31.861 | −31.831 | 1.00 | 23.87 | B | O |
| ATOM | 11339 | OE2 | GLU | B | 182 | 82.477 | 31.005 | −33.847 | 1.00 | 22.99 | B | O |
| ATOM | 11340 | C | GLU | B | 182 | 78.003 | 34.731 | −31.762 | 1.00 | 20.94 | B | C |
| ATOM | 11341 | O | GLU | B | 182 | 76.949 | 34.107 | −31.643 | 1.00 | 20.76 | B | O |
| ATOM | 11343 | N | GLN | B | 183 | 78.334 | 35.750 | −30.972 | 1.00 | 20.28 | B | N |
| ATOM | 11344 | CA | GLN | B | 183 | 77.412 | 36.262 | −29.957 | 1.00 | 20.01 | B | C |
| ATOM | 11346 | CB | GLN | B | 183 | 78.130 | 37.187 | −28.968 | 1.00 | 19.95 | B | C |
| ATOM | 11349 | CG | GLN | B | 183 | 79.140 | 36.483 | −28.068 | 1.00 | 20.86 | B | C |
| ATOM | 11352 | CD | GLN | B | 183 | 79.118 | 37.001 | −26.638 | 1.00 | 22.16 | B | C |
| ATOM | 11353 | OE1 | GLN | B | 183 | 79.484 | 38.147 | −26.375 | 1.00 | 22.85 | B | O |
| ATOM | 11354 | NE2 | GLN | B | 183 | 78.689 | 36.153 | −25.707 | 1.00 | 21.77 | B | N |
| ATOM | 11357 | C | GLN | B | 183 | 76.234 | 36.999 | −30.591 | 1.00 | 19.93 | B | C |
| ATOM | 11358 | O | GLN | B | 183 | 75.125 | 36.978 | −30.052 | 1.00 | 19.93 | B | O |

TABLE 8-2-continued

Coordinates for L494P Structure

| | | | | | | | | | | | | |
|---|---|---|---|---|---|---|---|---|---|---|---|---|
| ATOM | 11360 | N | VAL | B | 184 | 76.477 | 37.651 | −31.727 | 1.00 | 19.67 | B | N |
| ATOM | 11361 | CA | VAL | B | 184 | 75.416 | 38.334 | −32.469 | 1.00 | 19.49 | B | C |
| ATOM | 11363 | CB | VAL | B | 184 | 75.991 | 39.266 | −33.553 | 1.00 | 19.50 | B | C |
| ATOM | 11365 | CG1 | VAL | B | 184 | 76.767 | 40.403 | −32.906 | 1.00 | 19.63 | B | C |
| ATOM | 11369 | CG2 | VAL | B | 184 | 74.880 | 39.815 | −34.440 | 1.00 | 19.00 | B | C |
| ATOM | 11373 | C | VAL | B | 184 | 74.464 | 37.325 | −33.111 | 1.00 | 19.48 | B | C |
| ATOM | 11374 | O | VAL | B | 184 | 73.246 | 37.484 | −33.036 | 1.00 | 19.34 | B | O |
| ATOM | 11376 | N | ASN | B | 185 | 75.027 | 36.289 | −33.732 | 1.00 | 19.56 | B | N |
| ATOM | 11377 | CA | ASN | B | 185 | 74.230 | 35.210 | −34.323 | 1.00 | 19.71 | B | C |
| ATOM | 11379 | CB | ASN | B | 185 | 75.115 | 34.272 | −35.153 | 1.00 | 19.76 | B | C |
| ATOM | 11382 | CG | ASN | B | 185 | 75.756 | 34.965 | −36.348 | 1.00 | 20.50 | B | C |
| ATOM | 11383 | OD1 | ASN | B | 185 | 75.392 | 36.085 | −36.706 | 1.00 | 22.61 | B | O |
| ATOM | 11384 | ND2 | ASN | B | 185 | 76.719 | 34.295 | −36.971 | 1.00 | 21.21 | B | N |
| ATOM | 11387 | C | ASN | B | 185 | 73.473 | 34.402 | −33.266 | 1.00 | 19.77 | B | C |
| ATOM | 11388 | O | ASN | B | 185 | 72.386 | 33.891 | −33.533 | 1.00 | 20.02 | B | O |
| ATOM | 11390 | N | HIS | B | 186 | 74.057 | 34.287 | −32.075 | 1.00 | 19.72 | B | N |
| ATOM | 11391 | CA | HIS | B | 186 | 73.404 | 33.628 | −30.942 | 1.00 | 19.80 | B | C |
| ATOM | 11393 | CB | HIS | B | 186 | 74.414 | 33.411 | −29.808 | 1.00 | 19.92 | B | C |
| ATOM | 11396 | CG | HIS | B | 186 | 73.854 | 32.703 | −28.611 | 1.00 | 19.22 | B | C |
| ATOM | 11397 | ND1 | HIS | B | 186 | 73.549 | 31.358 | −28.615 | 1.00 | 19.55 | B | N |
| ATOM | 11399 | CE1 | HIS | B | 186 | 73.091 | 31.010 | −27.426 | 1.00 | 18.27 | B | C |
| ATOM | 11401 | NE2 | HIS | B | 186 | 73.093 | 32.077 | −26.649 | 1.00 | 18.30 | B | N |
| ATOM | 11403 | CD2 | HIS | B | 186 | 73.571 | 33.149 | −27.364 | 1.00 | 18.39 | B | C |
| ATOM | 11405 | C | HIS | B | 186 | 72.225 | 34.464 | −30.448 | 1.00 | 19.84 | B | C |
| ATOM | 11406 | O | HIS | B | 186 | 71.124 | 33.943 | −30.269 | 1.00 | 19.69 | B | O |
| ATOM | 11408 | N | ALA | B | 187 | 72.463 | 35.758 | −30.240 | 1.00 | 19.89 | B | N |
| ATOM | 11409 | CA | ALA | B | 187 | 71.419 | 36.682 | −29.780 | 1.00 | 19.70 | B | C |
| ATOM | 11411 | CB | ALA | B | 187 | 72.029 | 38.022 | −29.387 | 1.00 | 19.58 | B | C |
| ATOM | 11415 | C | ALA | B | 187 | 70.320 | 36.886 | −30.829 | 1.00 | 19.42 | B | C |
| ATOM | 11416 | O | ALA | B | 187 | 69.152 | 37.071 | −30.477 | 1.00 | 19.51 | B | O |
| ATOM | 11418 | N | LEU | B | 188 | 70.693 | 36.853 | −32.109 | 1.00 | 18.76 | B | N |
| ATOM | 11419 | CA | LEU | B | 188 | 69.721 | 36.993 | −33.200 | 1.00 | 18.16 | B | C |
| ATOM | 11421 | CB | LEU | B | 188 | 70.409 | 37.449 | −34.492 | 1.00 | 17.88 | B | C |
| ATOM | 11424 | CG | LEU | B | 188 | 70.820 | 38.925 | −34.496 | 1.00 | 17.28 | B | C |
| ATOM | 11426 | CD1 | LEU | B | 188 | 71.831 | 39.217 | −35.593 | 1.00 | 16.54 | B | C |
| ATOM | 11430 | CD2 | LEU | B | 188 | 69.600 | 39.820 | −34.640 | 1.00 | 15.64 | B | C |
| ATOM | 11434 | C | LEU | B | 188 | 68.916 | 35.711 | −33.436 | 1.00 | 17.88 | B | C |
| ATOM | 11435 | O | LEU | B | 188 | 67.764 | 35.775 | −33.863 | 1.00 | 18.07 | B | O |
| ATOM | 11437 | N | GLU | B | 189 | 69.518 | 34.554 | −33.164 | 1.00 | 17.45 | B | N |
| ATOM | 11438 | CA | GLU | B | 189 | 68.783 | 33.286 | −33.161 | 1.00 | 17.00 | B | C |
| ATOM | 11440 | CB | GLU | B | 189 | 69.717 | 32.116 | −32.830 | 1.00 | 16.79 | B | C |
| ATOM | 11443 | CG | GLU | B | 189 | 69.039 | 30.745 | −32.807 | 1.00 | 16.46 | B | C |
| ATOM | 11446 | CD | GLU | B | 189 | 70.001 | 29.608 | −32.506 | 1.00 | 16.49 | B | C |
| ATOM | 11447 | OE1 | GLU | B | 189 | 70.952 | 29.810 | −31.720 | 1.00 | 17.45 | B | O |
| ATOM | 11448 | OE2 | GLU | B | 189 | 69.802 | 28.502 | −33.051 | 1.00 | 16.29 | B | O |
| ATOM | 11449 | C | GLU | B | 189 | 67.647 | 33.354 | −32.141 | 1.00 | 16.85 | B | C |
| ATOM | 11450 | O | GLU | B | 189 | 66.513 | 32.963 | −32.430 | 1.00 | 16.54 | B | O |
| ATOM | 11452 | N | LEU | B | 190 | 67.973 | 33.852 | −30.949 | 1.00 | 16.84 | B | N |
| ATOM | 11453 | CA | LEU | B | 190 | 67.008 | 34.033 | −29.864 | 1.00 | 16.87 | B | C |
| ATOM | 11455 | CB | LEU | B | 190 | 66.646 | 32.680 | −29.242 | 1.00 | 16.90 | B | C |
| ATOM | 11458 | CG | LEU | B | 190 | 65.420 | 32.614 | −28.326 | 1.00 | 16.89 | B | C |
| ATOM | 11460 | CD1 | LEU | B | 190 | 64.144 | 32.781 | −29.127 | 1.00 | 16.28 | B | C |
| ATOM | 11464 | CD2 | LEU | B | 190 | 65.395 | 31.296 | −27.566 | 1.00 | 17.45 | B | C |
| ATOM | 11468 | C | LEU | B | 190 | 67.637 | 34.940 | −28.801 | 1.00 | 16.77 | B | C |
| ATOM | 11469 | O | LEU | B | 190 | 68.826 | 34.803 | −28.509 | 1.00 | 17.14 | B | O |
| ATOM | 11471 | N | PRO | B | 191 | 66.857 | 35.873 | −28.222 | 1.00 | 16.38 | B | N |
| ATOM | 11472 | CA | PRO | B | 191 | 67.420 | 36.724 | −27.166 | 1.00 | 16.04 | B | C |
| ATOM | 11474 | CB | PRO | B | 191 | 66.391 | 37.848 | −27.040 | 1.00 | 15.95 | B | C |
| ATOM | 11477 | CG | PRO | B | 191 | 65.114 | 37.221 | −27.453 | 1.00 | 16.28 | B | C |
| ATOM | 11480 | CD | PRO | B | 191 | 65.460 | 36.231 | −28.527 | 1.00 | 16.22 | B | C |
| ATOM | 11483 | C | PRO | B | 191 | 67.576 | 35.981 | −25.838 | 1.00 | 15.62 | B | C |
| ATOM | 11484 | O | PRO | B | 191 | 67.046 | 34.884 | −25.682 | 1.00 | 15.70 | B | O |
| ATOM | 11485 | N | LEU | B | 192 | 68.303 | 36.578 | −24.896 | 1.00 | 15.37 | B | N |
| ATOM | 11486 | CA | LEU | B | 192 | 68.515 | 35.973 | −23.578 | 1.00 | 14.71 | B | C |
| ATOM | 11488 | CB | LEU | B | 192 | 69.477 | 36.810 | −22.735 | 1.00 | 14.48 | B | C |
| ATOM | 11491 | CG | LEU | B | 192 | 70.931 | 36.828 | −23.194 | 1.00 | 14.76 | B | C |
| ATOM | 11493 | CD1 | LEU | B | 192 | 71.650 | 38.005 | −22.575 | 1.00 | 16.74 | B | C |
| ATOM | 11497 | CD2 | LEU | B | 192 | 71.627 | 35.526 | −22.840 | 1.00 | 14.51 | B | C |
| ATOM | 11501 | C | LEU | B | 192 | 67.203 | 35.839 | −22.833 | 1.00 | 14.18 | B | C |
| ATOM | 11502 | O | LEU | B | 192 | 66.930 | 34.801 | −22.234 | 1.00 | 14.39 | B | O |
| ATOM | 11504 | N | HIS | B | 193 | 66.388 | 36.889 | −22.891 | 1.00 | 13.57 | B | N |
| ATOM | 11505 | CA | HIS | B | 193 | 65.119 | 36.926 | −22.170 | 1.00 | 13.63 | B | C |
| ATOM | 11507 | CB | HIS | B | 193 | 64.446 | 38.292 | −22.363 | 1.00 | 13.58 | B | C |
| ATOM | 11510 | CG | HIS | B | 193 | 63.202 | 38.477 | −21.548 | 1.00 | 13.03 | B | C |
| ATOM | 11511 | ND1 | HIS | B | 193 | 63.208 | 38.485 | −20.170 | 1.00 | 13.37 | B | N |
| ATOM | 11513 | CE1 | HIS | B | 193 | 61.976 | 38.662 | −19.727 | 1.00 | 13.22 | B | C |
| ATOM | 11515 | NE2 | HIS | B | 193 | 61.171 | 38.773 | −20.769 | 1.00 | 11.40 | B | N |
| ATOM | 11517 | CD2 | HIS | B | 193 | 61.913 | 38.661 | −21.920 | 1.00 | 11.23 | B | C |

TABLE 8-2-continued

Coordinates for L494P Structure

| | | | | | | | | | | | | |
|---|---|---|---|---|---|---|---|---|---|---|---|---|
| ATOM | 11519 | C | HIS | B | 193 | 64.160 | 35.795 | −22.570 | 1.00 | 13.78 | B | C |
| ATOM | 11520 | O | HIS | B | 193 | 63.257 | 35.440 | −21.802 | 1.00 | 13.38 | B | O |
| ATOM | 11522 | N | ARG | B | 194 | 64.365 | 35.224 | −23.756 | 1.00 | 14.17 | B | N |
| ATOM | 11523 | CA | ARG | B | 194 | 63.487 | 34.175 | −24.273 | 1.00 | 14.88 | B | C |
| ATOM | 11525 | CB | ARG | B | 194 | 62.992 | 34.567 | −25.663 | 1.00 | 15.05 | B | C |
| ATOM | 11528 | CG | ARG | B | 194 | 62.208 | 35.872 | −25.689 | 1.00 | 16.31 | B | C |
| ATOM | 11531 | CD | ARG | B | 194 | 61.684 | 36.153 | −27.083 | 1.00 | 18.23 | B | C |
| ATOM | 11534 | NE | ARG | B | 194 | 60.754 | 37.277 | −27.116 | 1.00 | 18.82 | B | N |
| ATOM | 11536 | CZ | ARG | B | 194 | 60.060 | 37.648 | −28.190 | 1.00 | 18.69 | B | C |
| ATOM | 11537 | NH1 | ARG | B | 194 | 60.186 | 36.987 | −29.338 | 1.00 | 19.08 | B | N |
| ATOM | 11540 | NH2 | ARG | B | 194 | 59.235 | 38.687 | −28.117 | 1.00 | 19.19 | B | N |
| ATOM | 11543 | C | ARG | B | 194 | 64.126 | 32.785 | −24.336 | 1.00 | 14.83 | B | C |
| ATOM | 11544 | O | ARG | B | 194 | 63.439 | 31.814 | −24.648 | 1.00 | 15.42 | B | O |
| ATOM | 11546 | N | ARG | B | 195 | 65.421 | 32.681 | −24.042 | 1.00 | 14.50 | B | N |
| ATOM | 11547 | CA | ARG | B | 195 | 66.118 | 31.398 | −24.116 | 1.00 | 14.49 | B | C |
| ATOM | 11549 | CB | ARG | B | 195 | 67.545 | 31.588 | −24.627 | 1.00 | 14.69 | B | C |
| ATOM | 11552 | CG | ARG | B | 195 | 68.145 | 30.336 | −25.240 | 1.00 | 15.98 | B | C |
| ATOM | 11555 | CD | ARG | B | 195 | 69.649 | 30.461 | −25.417 | 1.00 | 17.88 | B | C |
| ATOM | 11558 | NE | ARG | B | 195 | 70.028 | 31.579 | −26.279 | 1.00 | 18.66 | B | N |
| ATOM | 11560 | CZ | ARG | B | 195 | 69.963 | 31.572 | −27.610 | 1.00 | 20.86 | B | C |
| ATOM | 11561 | NH1 | ARG | B | 195 | 69.522 | 30.505 | −28.274 | 1.00 | 21.51 | B | N |
| ATOM | 11564 | NH2 | ARG | B | 195 | 70.344 | 32.646 | −28.289 | 1.00 | 22.00 | B | N |
| ATOM | 11567 | C | ARG | B | 195 | 66.141 | 30.733 | −22.747 | 1.00 | 14.49 | B | C |
| ATOM | 11568 | O | ARG | B | 195 | 66.247 | 31.412 | −21.723 | 1.00 | 14.49 | B | O |
| ATOM | 11570 | N | THR | B | 196 | 66.047 | 29.404 | −22.736 | 1.00 | 14.52 | B | N |
| ATOM | 11571 | CA | THR | B | 196 | 66.036 | 28.641 | −21.490 | 1.00 | 14.61 | B | C |
| ATOM | 11573 | CB | THR | B | 196 | 65.535 | 27.199 | −21.701 | 1.00 | 14.72 | B | C |
| ATOM | 11575 | OG1 | THR | B | 196 | 66.358 | 26.536 | −22.668 | 1.00 | 14.27 | B | O |
| ATOM | 11577 | CG2 | THR | B | 196 | 64.090 | 27.198 | −22.178 | 1.00 | 15.09 | B | C |
| ATOM | 11581 | C | THR | B | 196 | 67.427 | 28.599 | −20.868 | 1.00 | 14.74 | B | C |
| ATOM | 11582 | O | THR | B | 196 | 68.431 | 28.613 | −21.577 | 1.00 | 14.94 | B | O |
| ATOM | 11584 | N | GLN | B | 197 | 67.464 | 28.529 | −19.540 | 1.00 | 14.94 | B | N |
| ATOM | 11585 | CA | GLN | B | 197 | 68.707 | 28.631 | −18.768 | 1.00 | 14.89 | B | C |
| ATOM | 11587 | CB | GLN | B | 197 | 68.415 | 28.398 | −17.273 | 1.00 | 14.86 | B | C |
| ATOM | 11590 | CG | GLN | B | 197 | 69.335 | 29.146 | −16.312 | 1.00 | 13.67 | B | C |
| ATOM | 11593 | CD | GLN | B | 197 | 70.536 | 28.336 | −15.866 | 1.00 | 11.84 | B | C |
| ATOM | 11594 | OE1 | GLN | B | 197 | 71.150 | 27.618 | −16.653 | 1.00 | 11.73 | B | O |
| ATOM | 11595 | NE2 | GLN | B | 197 | 70.885 | 28.460 | −14.596 | 1.00 | 10.93 | B | N |
| ATOM | 11598 | C | GLN | B | 197 | 69.785 | 27.656 | −19.250 | 1.00 | 15.04 | B | C |
| ATOM | 11599 | O | GLN | B | 197 | 70.916 | 28.058 | −19.533 | 1.00 | 14.84 | B | O |
| ATOM | 11601 | N | ARG | B | 198 | 69.421 | 26.380 | −19.353 | 1.00 | 15.25 | B | N |
| ATOM | 11602 | CA | ARG | B | 198 | 70.382 | 25.316 | −19.657 | 1.00 | 15.00 | B | C |
| ATOM | 11604 | CB | ARG | B | 198 | 69.755 | 23.946 | −19.396 | 1.00 | 14.97 | B | C |
| ATOM | 11607 | CG | ARG | B | 198 | 69.439 | 23.673 | −17.932 | 1.00 | 15.36 | B | C |
| ATOM | 11610 | CD | ARG | B | 198 | 70.675 | 23.289 | −17.132 | 1.00 | 15.24 | B | C |
| ATOM | 11613 | NE | ARG | B | 198 | 71.376 | 24.438 | −16.564 | 1.00 | 15.04 | B | N |
| ATOM | 11615 | CZ | ARG | B | 198 | 72.401 | 24.347 | −15.717 | 1.00 | 15.93 | B | C |
| ATOM | 11616 | NH1 | ARG | B | 198 | 72.855 | 23.160 | −15.334 | 1.00 | 16.51 | B | N |
| ATOM | 11619 | NH2 | ARG | B | 198 | 72.977 | 25.447 | −15.248 | 1.00 | 16.24 | B | N |
| ATOM | 11622 | C | ARG | B | 198 | 70.916 | 25.373 | −21.086 | 1.00 | 14.67 | B | C |
| ATOM | 11623 | O | ARG | B | 198 | 72.093 | 25.083 | −21.320 | 1.00 | 14.37 | B | O |
| ATOM | 11625 | N | LEU | B | 199 | 70.055 | 25.726 | −22.038 | 1.00 | 14.51 | B | N |
| ATOM | 11626 | CA | LEU | B | 199 | 70.490 | 25.910 | −23.427 | 1.00 | 14.52 | B | C |
| ATOM | 11628 | CB | LEU | B | 199 | 69.297 | 26.133 | −24.378 | 1.00 | 14.65 | B | C |
| ATOM | 11631 | CG | LEU | B | 199 | 68.606 | 24.925 | −25.037 | 1.00 | 14.01 | B | C |
| ATOM | 11633 | CD1 | LEU | B | 199 | 67.687 | 24.176 | −24.064 | 1.00 | 13.56 | B | C |
| ATOM | 11637 | CD2 | LEU | B | 199 | 69.625 | 23.978 | −25.659 | 1.00 | 12.13 | B | C |
| ATOM | 11641 | C | LEU | B | 199 | 71.458 | 27.091 | −23.512 | 1.00 | 14.39 | B | C |
| ATOM | 11642 | O | LEU | B | 199 | 72.476 | 27.022 | −24.207 | 1.00 | 14.42 | B | O |
| ATOM | 11644 | N | GLU | B | 200 | 71.132 | 28.168 | −22.800 | 1.00 | 13.72 | B | N |
| ATOM | 11645 | CA | GLU | B | 200 | 71.998 | 29.335 | −22.737 | 1.00 | 13.37 | B | C |
| ATOM | 11647 | CB | GLU | B | 200 | 71.312 | 30.473 | −21.969 | 1.00 | 13.42 | B | C |
| ATOM | 11650 | CG | GLU | B | 200 | 72.160 | 31.723 | −21.776 | 1.00 | 13.45 | B | C |
| ATOM | 11653 | CD | GLU | B | 200 | 72.875 | 32.157 | −23.042 | 1.00 | 14.44 | B | C |
| ATOM | 11654 | OE1 | GLU | B | 200 | 72.268 | 32.095 | −24.133 | 1.00 | 14.98 | B | O |
| ATOM | 11655 | OE2 | GLU | B | 200 | 74.049 | 32.561 | −22.945 | 1.00 | 15.44 | B | O |
| ATOM | 11656 | C | GLU | B | 200 | 73.317 | 28.968 | −22.071 | 1.00 | 13.44 | B | C |
| ATOM | 11657 | O | GLU | B | 200 | 74.389 | 29.324 | −22.561 | 1.00 | 13.42 | B | O |
| ATOM | 11659 | N | ALA | B | 201 | 73.229 | 28.248 | −20.959 | 1.00 | 13.64 | B | N |
| ATOM | 11660 | CA | ALA | B | 201 | 74.414 | 27.828 | −20.222 | 1.00 | 14.07 | B | C |
| ATOM | 11662 | CB | ALA | B | 201 | 74.017 | 27.028 | −18.991 | 1.00 | 14.39 | B | C |
| ATOM | 11666 | C | ALA | B | 201 | 75.371 | 27.018 | −21.094 | 1.00 | 14.43 | B | C |
| ATOM | 11667 | O | ALA | B | 201 | 76.564 | 27.319 | −21.144 | 1.00 | 14.77 | B | O |
| ATOM | 11669 | N | VAL | B | 202 | 74.849 | 26.008 | −21.791 | 1.00 | 14.63 | B | N |
| ATOM | 11670 | CA | VAL | B | 202 | 75.691 | 25.119 | −22.602 | 1.00 | 14.73 | B | C |
| ATOM | 11672 | CB | VAL | B | 202 | 74.885 | 23.939 | −23.206 | 1.00 | 14.72 | B | C |
| ATOM | 11674 | CG1 | VAL | B | 202 | 73.980 | 24.415 | −24.333 | 1.00 | 15.60 | B | C |
| ATOM | 11678 | CG2 | VAL | B | 202 | 75.828 | 22.852 | −23.706 | 1.00 | 13.72 | B | C |

TABLE 8-2-continued

Coordinates for L494P Structure

| | | | | | | | | | | | | |
|---|---|---|---|---|---|---|---|---|---|---|---|---|
| ATOM | 11682 | C | VAL | B | 202 | 76.425 | 25.865 | −23.723 | 1.00 | 14.67 | B | C |
| ATOM | 11683 | O | VAL | B | 202 | 77.535 | 25.484 | −24.101 | 1.00 | 14.54 | B | O |
| ATOM | 11685 | N | TRP | B | 203 | 75.809 | 26.926 | −24.238 | 1.00 | 14.66 | B | N |
| ATOM | 11686 | CA | TRP | B | 203 | 76.417 | 27.728 | −25.295 | 1.00 | 14.84 | B | C |
| ATOM | 11688 | CB | TRP | B | 203 | 75.344 | 28.484 | −26.083 | 1.00 | 14.97 | B | C |
| ATOM | 11691 | CG | TRP | B | 203 | 75.916 | 29.258 | −27.217 | 1.00 | 14.08 | B | C |
| ATOM | 11692 | CD1 | TRP | B | 203 | 76.114 | 28.818 | −28.491 | 1.00 | 13.97 | B | C |
| ATOM | 11694 | NE1 | TRP | B | 203 | 76.677 | 29.812 | −29.251 | 1.00 | 14.19 | B | N |
| ATOM | 11696 | CE2 | TRP | B | 203 | 76.860 | 30.919 | −28.465 | 1.00 | 13.10 | B | C |
| ATOM | 11697 | CD2 | TRP | B | 203 | 76.393 | 30.603 | −27.176 | 1.00 | 12.77 | B | C |
| ATOM | 11698 | CE3 | TRP | B | 203 | 76.465 | 31.575 | −26.173 | 1.00 | 13.68 | B | C |
| ATOM | 11700 | CZ3 | TRP | B | 203 | 76.993 | 32.812 | −26.486 | 1.00 | 14.21 | B | C |
| ATOM | 11702 | CH2 | TRP | B | 203 | 77.449 | 33.096 | −27.778 | 1.00 | 14.39 | B | C |
| ATOM | 11704 | CZ2 | TRP | B | 203 | 77.393 | 32.165 | −28.779 | 1.00 | 13.69 | B | C |
| ATOM | 11706 | C | TRP | B | 203 | 77.438 | 28.722 | −24.739 | 1.00 | 15.07 | B | C |
| ATOM | 11707 | O | TRP | B | 203 | 78.578 | 28.779 | −25.211 | 1.00 | 15.56 | B | O |
| ATOM | 11709 | N | SER | B | 204 | 77.018 | 29.507 | −23.749 | 1.00 | 14.73 | B | N |
| ATOM | 11710 | CA | SER | B | 204 | 77.861 | 30.563 | −23.179 | 1.00 | 14.32 | B | C |
| ATOM | 11712 | CB | SER | B | 204 | 77.084 | 31.382 | −22.146 | 1.00 | 14.36 | B | C |
| ATOM | 11715 | OG | SER | B | 204 | 76.240 | 32.322 | −22.781 | 1.00 | 13.68 | B | O |
| ATOM | 11717 | C | SER | B | 204 | 79.149 | 30.044 | −22.549 | 1.00 | 14.07 | B | C |
| ATOM | 11718 | O | SER | B | 204 | 80.164 | 30.735 | −22.583 | 1.00 | 14.22 | B | O |
| ATOM | 11720 | N | ILE | B | 205 | 79.103 | 28.840 | −21.976 | 1.00 | 13.65 | B | N |
| ATOM | 11721 | CA | ILE | B | 205 | 80.286 | 28.223 | −21.365 | 1.00 | 13.54 | B | C |
| ATOM | 11723 | CB | ILE | B | 205 | 79.918 | 26.963 | −20.542 | 1.00 | 13.39 | B | C |
| ATOM | 11725 | CG1 | ILE | B | 205 | 79.225 | 27.367 | −19.241 | 1.00 | 13.19 | B | C |
| ATOM | 11728 | CD1 | ILE | B | 205 | 78.813 | 26.197 | −18.372 | 1.00 | 13.69 | B | C |
| ATOM | 11732 | CG2 | ILE | B | 205 | 81.162 | 26.151 | −20.208 | 1.00 | 13.60 | B | C |
| ATOM | 11736 | C | ILE | B | 205 | 81.352 | 27.870 | −22.410 | 1.00 | 13.51 | B | C |
| ATOM | 11737 | O | ILE | B | 205 | 82.542 | 28.105 | −22.193 | 1.00 | 12.96 | B | O |
| ATOM | 11739 | N | GLU | B | 206 | 80.918 | 27.309 | −23.536 | 1.00 | 13.71 | B | N |
| ATOM | 11740 | CA | GLU | B | 206 | 81.822 | 26.989 | −24.640 | 1.00 | 13.71 | B | C |
| ATOM | 11742 | CB | GLU | B | 206 | 81.084 | 26.164 | −25.706 | 1.00 | 13.88 | B | C |
| ATOM | 11745 | CG | GLU | B | 206 | 81.888 | 25.840 | −26.973 | 1.00 | 15.04 | B | C |
| ATOM | 11748 | CD | GLU | B | 206 | 83.222 | 25.163 | −26.693 | 1.00 | 15.38 | B | C |
| ATOM | 11749 | OE1 | GLU | B | 206 | 83.322 | 24.405 | −25.704 | 1.00 | 15.76 | B | O |
| ATOM | 11750 | OE2 | GLU | B | 206 | 84.172 | 25.387 | −27.474 | 1.00 | 15.99 | B | O |
| ATOM | 11751 | C | GLU | B | 206 | 82.418 | 28.263 | −25.253 | 1.00 | 13.41 | B | C |
| ATOM | 11752 | O | GLU | B | 206 | 83.603 | 28.303 | −25.581 | 1.00 | 12.99 | B | O |
| ATOM | 11754 | N | ALA | B | 207 | 81.592 | 29.297 | −25.397 | 1.00 | 13.13 | B | N |
| ATOM | 11755 | CA | ALA | B | 207 | 82.037 | 30.583 | −25.938 | 1.00 | 12.74 | B | C |
| ATOM | 11757 | CB | ALA | B | 207 | 80.834 | 31.472 | −26.228 | 1.00 | 12.73 | B | C |
| ATOM | 11761 | C | ALA | B | 207 | 83.008 | 31.300 | −24.997 | 1.00 | 12.41 | B | C |
| ATOM | 11762 | O | ALA | B | 207 | 84.012 | 31.856 | −25.441 | 1.00 | 11.95 | B | O |
| ATOM | 11764 | N | TYR | B | 208 | 82.695 | 31.283 | −23.702 | 1.00 | 12.40 | B | N |
| ATOM | 11765 | CA | TYR | B | 208 | 83.506 | 31.947 | −22.674 | 1.00 | 12.38 | B | C |
| ATOM | 11767 | CB | TYR | B | 208 | 82.719 | 32.017 | −21.359 | 1.00 | 12.14 | B | C |
| ATOM | 11770 | CG | TYR | B | 208 | 83.307 | 32.930 | −20.307 | 1.00 | 11.69 | B | C |
| ATOM | 11771 | CD1 | TYR | B | 208 | 83.112 | 34.307 | −20.366 | 1.00 | 12.57 | B | C |
| ATOM | 11773 | CE1 | TYR | B | 208 | 83.640 | 35.152 | −19.398 | 1.00 | 13.17 | B | C |
| ATOM | 11775 | CZ | TYR | B | 208 | 84.367 | 34.620 | −18.349 | 1.00 | 13.50 | B | C |
| ATOM | 11776 | OH | TYR | B | 208 | 84.891 | 35.454 | −17.388 | 1.00 | 14.79 | B | O |
| ATOM | 11778 | CE2 | TYR | B | 208 | 84.568 | 33.254 | −18.262 | 1.00 | 12.55 | B | C |
| ATOM | 11780 | CD2 | TYR | B | 208 | 84.035 | 32.417 | −19.238 | 1.00 | 11.68 | B | C |
| ATOM | 11782 | C | TYR | B | 208 | 84.834 | 31.221 | −22.450 | 1.00 | 12.66 | B | C |
| ATOM | 11783 | O | TYR | B | 208 | 85.840 | 31.841 | −22.109 | 1.00 | 12.19 | B | O |
| ATOM | 11785 | N | ARG | B | 209 | 84.818 | 29.904 | −22.637 | 1.00 | 13.27 | B | N |
| ATOM | 11786 | CA | ARG | B | 209 | 86.020 | 29.073 | −22.563 | 1.00 | 13.72 | B | C |
| ATOM | 11788 | CB | ARG | B | 209 | 85.627 | 27.607 | −22.794 | 1.00 | 13.38 | B | C |
| ATOM | 11791 | CG | ARG | B | 209 | 86.776 | 26.618 | −22.939 | 1.00 | 13.64 | B | C |
| ATOM | 11794 | CD | ARG | B | 209 | 86.308 | 25.339 | −23.618 | 1.00 | 12.76 | B | C |
| ATOM | 11797 | NE | ARG | B | 209 | 85.380 | 24.576 | −22.789 | 1.00 | 8.75 | B | N |
| ATOM | 11799 | CZ | ARG | B | 209 | 85.737 | 23.800 | −21.769 | 1.00 | 7.83 | B | C |
| ATOM | 11800 | NH1 | ARG | B | 209 | 87.014 | 23.671 | −21.418 | 1.00 | 7.53 | B | N |
| ATOM | 11803 | NH2 | ARG | B | 209 | 84.805 | 23.149 | −21.088 | 1.00 | 9.72 | B | N |
| ATOM | 11806 | C | ARG | B | 209 | 87.091 | 29.520 | −23.574 | 1.00 | 14.74 | B | C |
| ATOM | 11807 | O | ARG | B | 209 | 88.291 | 29.385 | −23.317 | 1.00 | 14.87 | B | O |
| ATOM | 11809 | N | LYS | B | 210 | 86.653 | 30.052 | −24.715 | 1.00 | 15.63 | B | N |
| ATOM | 11810 | CA | LYS | B | 210 | 87.566 | 30.517 | −25.763 | 1.00 | 16.08 | B | C |
| ATOM | 11812 | CB | LYS | B | 210 | 86.837 | 30.620 | −27.106 | 1.00 | 16.07 | B | C |
| ATOM | 11815 | CG | LYS | B | 210 | 86.325 | 29.290 | −27.644 | 1.00 | 16.25 | B | C |
| ATOM | 11818 | CD | LYS | B | 210 | 85.403 | 29.498 | −28.838 | 1.00 | 15.92 | B | C |
| ATOM | 11821 | CE | LYS | B | 210 | 84.773 | 28.196 | −29.298 | 1.00 | 15.10 | B | C |
| ATOM | 11824 | NZ | LYS | B | 210 | 83.951 | 28.393 | −30.523 | 1.00 | 14.52 | B | N |
| ATOM | 11828 | C | LYS | B | 210 | 88.218 | 31.861 | −25.437 | 1.00 | 16.75 | B | C |
| ATOM | 11829 | O | LYS | B | 210 | 89.311 | 32.145 | −25.928 | 1.00 | 17.30 | B | O |
| ATOM | 11831 | N | LYS | B | 211 | 87.555 | 32.687 | −24.627 | 1.00 | 17.35 | B | N |
| ATOM | 11832 | CA | LYS | B | 211 | 88.104 | 33.994 | −24.247 | 1.00 | 17.95 | B | C |

TABLE 8-2-continued

Coordinates for L494P Structure

| | | | | | | | | | | | | |
|---|---|---|---|---|---|---|---|---|---|---|---|---|
| ATOM | 11834 | CB | LYS | B | 211 | 87.083 | 34.814 | −23.445 | 1.00 | 18.18 | B | C |
| ATOM | 11837 | CG | LYS | B | 211 | 85.851 | 35.242 | −24.233 | 1.00 | 18.73 | B | C |
| ATOM | 11840 | CD | LYS | B | 211 | 85.015 | 36.254 | −23.458 | 1.00 | 19.41 | B | C |
| ATOM | 11843 | CE | LYS | B | 211 | 83.593 | 36.355 | −24.010 | 1.00 | 20.51 | B | C |
| ATOM | 11846 | NZ | LYS | B | 211 | 83.552 | 36.703 | −25.461 | 1.00 | 20.75 | B | N |
| ATOM | 11850 | C | LYS | B | 211 | 89.388 | 33.830 | −23.431 | 1.00 | 18.28 | B | C |
| ATOM | 11851 | O | LYS | B | 211 | 89.364 | 33.281 | −22.329 | 1.00 | 18.16 | B | O |
| ATOM | 11853 | N | GLU | B | 212 | 90.503 | 34.311 | −23.978 | 1.00 | 18.88 | B | N |
| ATOM | 11854 | CA | GLU | B | 212 | 91.801 | 34.227 | −23.300 | 1.00 | 19.31 | B | C |
| ATOM | 11856 | CB | GLU | B | 212 | 92.933 | 34.639 | −24.248 | 1.00 | 19.39 | B | C |
| ATOM | 11859 | CG | GLU | B | 212 | 94.323 | 34.194 | −23.793 | 1.00 | 19.97 | B | C |
| ATOM | 11862 | CD | GLU | B | 212 | 95.445 | 34.816 | −24.608 | 1.00 | 20.72 | B | C |
| ATOM | 11863 | OE1 | GLU | B | 212 | 95.377 | 36.028 | −24.905 | 1.00 | 21.30 | B | O |
| ATOM | 11864 | OE2 | GLU | B | 212 | 96.407 | 34.093 | −24.941 | 1.00 | 20.66 | B | O |
| ATOM | 11865 | C | GLU | B | 212 | 91.831 | 35.098 | −22.040 | 1.00 | 19.46 | B | C |
| ATOM | 11866 | O | GLU | B | 212 | 92.651 | 34.880 | −21.146 | 1.00 | 19.79 | B | O |
| ATOM | 11868 | N | ASP | B | 213 | 90.932 | 36.078 | −21.979 | 1.00 | 19.22 | B | N |
| ATOM | 11869 | CA | ASP | B | 213 | 90.816 | 36.973 | −20.830 | 1.00 | 19.09 | B | C |
| ATOM | 11871 | CB | ASP | B | 213 | 90.503 | 38.398 | −21.309 | 1.00 | 19.27 | B | C |
| ATOM | 11874 | CG | ASP | B | 213 | 89.263 | 38.464 | −22.186 | 1.00 | 19.40 | B | C |
| ATOM | 11875 | OD1 | ASP | B | 213 | 89.198 | 37.713 | −23.183 | 1.00 | 19.36 | B | O |
| ATOM | 11876 | OD2 | ASP | B | 213 | 88.360 | 39.271 | −21.884 | 1.00 | 21.12 | B | O |
| ATOM | 11877 | C | ASP | B | 213 | 89.750 | 36.516 | −19.828 | 1.00 | 18.88 | B | C |
| ATOM | 11878 | O | ASP | B | 213 | 89.341 | 37.294 | −18.966 | 1.00 | 19.17 | B | O |
| ATOM | 11880 | N | ALA | B | 214 | 89.316 | 35.260 | −19.926 | 1.00 | 18.57 | B | N |
| ATOM | 11881 | CA | ALA | B | 214 | 88.229 | 34.750 | −19.084 | 1.00 | 18.24 | B | C |
| ATOM | 11883 | CB | ALA | B | 214 | 87.574 | 33.549 | −19.740 | 1.00 | 18.18 | B | C |
| ATOM | 11887 | C | ALA | B | 214 | 88.712 | 34.383 | −17.683 | 1.00 | 18.02 | B | C |
| ATOM | 11888 | O | ALA | B | 214 | 89.828 | 33.891 | −17.511 | 1.00 | 17.90 | B | O |
| ATOM | 11890 | N | ASN | B | 215 | 87.857 | 34.627 | −16.690 | 1.00 | 17.91 | B | N |
| ATOM | 11891 | CA | ASN | B | 215 | 88.151 | 34.300 | −15.297 | 1.00 | 17.91 | B | C |
| ATOM | 11893 | CB | ASN | B | 215 | 87.225 | 35.079 | −14.355 | 1.00 | 17.98 | B | C |
| ATOM | 11896 | CG | ASN | B | 215 | 87.530 | 34.835 | −12.882 | 1.00 | 18.96 | B | C |
| ATOM | 11897 | OD1 | ASN | B | 215 | 88.546 | 34.235 | −12.531 | 1.00 | 20.95 | B | O |
| ATOM | 11898 | ND2 | ASN | B | 215 | 86.646 | 35.311 | −12.012 | 1.00 | 20.55 | B | N |
| ATOM | 11901 | C | ASN | B | 215 | 87.989 | 32.801 | −15.079 | 1.00 | 17.88 | B | C |
| ATOM | 11902 | O | ASN | B | 215 | 86.871 | 32.288 | −15.067 | 1.00 | 18.40 | B | O |
| ATOM | 11904 | N | GLN | B | 216 | 89.110 | 32.109 | −14.897 | 1.00 | 17.67 | B | N |
| ATOM | 11905 | CA | GLN | B | 216 | 89.123 | 30.648 | −14.814 | 1.00 | 17.28 | B | C |
| ATOM | 11907 | CB | GLN | B | 216 | 90.559 | 30.125 | −14.732 | 1.00 | 17.40 | B | C |
| ATOM | 11910 | CG | GLN | B | 216 | 91.454 | 30.489 | −15.919 | 1.00 | 18.55 | B | C |
| ATOM | 11913 | CD | GLN | B | 216 | 91.101 | 29.741 | −17.193 | 1.00 | 19.04 | B | C |
| ATOM | 11914 | OE1 | GLN | B | 216 | 90.043 | 29.961 | −17.788 | 1.00 | 19.21 | B | O |
| ATOM | 11915 | NE2 | GLN | B | 216 | 91.999 | 28.863 | −17.628 | 1.00 | 20.05 | B | N |
| ATOM | 11918 | C | GLN | B | 216 | 88.334 | 30.149 | −13.610 | 1.00 | 16.63 | B | C |
| ATOM | 11919 | O | GLN | B | 216 | 87.517 | 29.234 | −13.733 | 1.00 | 16.72 | B | O |
| ATOM | 11921 | N | VAL | B | 217 | 88.583 | 30.759 | −12.453 | 1.00 | 15.82 | B | N |
| ATOM | 11922 | CA | VAL | B | 217 | 87.865 | 30.422 | −11.224 | 1.00 | 15.08 | B | C |
| ATOM | 11924 | CB | VAL | B | 217 | 88.187 | 31.414 | −10.079 | 1.00 | 15.07 | B | C |
| ATOM | 11926 | CG1 | VAL | B | 217 | 87.308 | 31.142 | −8.868 | 1.00 | 14.72 | B | C |
| ATOM | 11930 | CG2 | VAL | B | 217 | 89.660 | 31.324 | −9.694 | 1.00 | 15.15 | B | C |
| ATOM | 11934 | C | VAL | B | 217 | 86.360 | 30.394 | −11.481 | 1.00 | 14.47 | B | C |
| ATOM | 11935 | O | VAL | B | 217 | 85.678 | 29.458 | −11.067 | 1.00 | 14.91 | B | O |
| ATOM | 11937 | N | LEU | B | 218 | 85.852 | 31.405 | −12.180 | 1.00 | 13.50 | B | N |
| ATOM | 11938 | CA | LEU | B | 218 | 84.441 | 31.437 | −12.553 | 1.00 | 12.95 | B | C |
| ATOM | 11940 | CB | LEU | B | 218 | 84.069 | 32.789 | −13.179 | 1.00 | 12.79 | B | C |
| ATOM | 11943 | CG | LEU | B | 218 | 82.617 | 32.980 | −13.641 | 1.00 | 11.49 | B | C |
| ATOM | 11945 | CD1 | LEU | B | 218 | 81.627 | 32.691 | −12.524 | 1.00 | 8.68 | B | C |
| ATOM | 11949 | CD2 | LEU | B | 218 | 82.416 | 34.384 | −14.174 | 1.00 | 10.75 | B | C |
| ATOM | 11953 | C | LEU | B | 218 | 84.110 | 30.301 | −13.517 | 1.00 | 12.90 | B | C |
| ATOM | 11954 | O | LEU | B | 218 | 83.134 | 29.579 | −13.311 | 1.00 | 13.48 | B | O |
| ATOM | 11956 | N | LEU | B | 219 | 84.930 | 30.144 | −14.555 | 1.00 | 12.44 | B | N |
| ATOM | 11957 | CA | LEU | B | 219 | 84.683 | 29.154 | −15.609 | 1.00 | 12.25 | B | C |
| ATOM | 11959 | CB | LEU | B | 219 | 85.739 | 29.272 | −16.715 | 1.00 | 12.47 | B | C |
| ATOM | 11962 | CG | LEU | B | 219 | 85.676 | 28.253 | −17.864 | 1.00 | 13.40 | B | C |
| ATOM | 11964 | CD1 | LEU | B | 219 | 84.303 | 28.247 | −18.520 | 1.00 | 12.39 | B | C |
| ATOM | 11968 | CD2 | LEU | B | 219 | 86.761 | 28.534 | −18.896 | 1.00 | 13.97 | B | C |
| ATOM | 11972 | C | LEU | B | 219 | 84.649 | 27.720 | −15.079 | 1.00 | 11.89 | B | C |
| ATOM | 11973 | O | LEU | B | 219 | 83.772 | 26.938 | −15.451 | 1.00 | 12.23 | B | O |
| ATOM | 11975 | N | GLU | B | 220 | 85.607 | 27.379 | −14.222 | 1.00 | 11.04 | B | N |
| ATOM | 11976 | CA | GLU | B | 220 | 85.691 | 26.034 | −13.648 | 1.00 | 10.39 | B | C |
| ATOM | 11978 | CB | GLU | B | 220 | 86.885 | 25.938 | −12.694 | 1.00 | 10.57 | B | C |
| ATOM | 11981 | CG | GLU | B | 220 | 87.164 | 24.540 | −12.157 | 1.00 | 10.41 | B | C |
| ATOM | 11984 | CD | GLU | B | 220 | 88.415 | 24.484 | −11.300 | 1.00 | 11.88 | B | C |
| ATOM | 11985 | OE1 | GLU | B | 220 | 89.036 | 25.544 | −11.076 | 1.00 | 13.40 | B | O |
| ATOM | 11986 | OE2 | GLU | B | 220 | 88.779 | 23.380 | −10.846 | 1.00 | 13.69 | B | O |
| ATOM | 11987 | C | GLU | B | 220 | 84.401 | 25.682 | −12.913 | 1.00 | 9.41 | B | C |
| ATOM | 11988 | O | GLU | B | 220 | 83.838 | 24.607 | −13.110 | 1.00 | 9.34 | B | O |

TABLE 8-2-continued

Coordinates for L494P Structure

| | | | | | | | | | | | | |
|---|---|---|---|---|---|---|---|---|---|---|---|---|
| ATOM | 11990 | N | LEU | B | 221 | 83.944 | 26.604 | −12.072 | 1.00 | 8.59 | B | N |
| ATOM | 11991 | CA | LEU | B | 221 | 82.689 | 26.452 | −11.338 | 1.00 | 7.91 | B | C |
| ATOM | 11993 | CB | LEU | B | 221 | 82.470 | 27.675 | −10.445 | 1.00 | 7.25 | B | C |
| ATOM | 11996 | CG | LEU | B | 221 | 81.299 | 27.637 | −9.470 | 1.00 | 5.48 | B | C |
| ATOM | 11998 | CD1 | LEU | B | 221 | 81.473 | 26.510 | −8.472 | 1.00 | 2.94 | B | C |
| ATOM | 12002 | CD2 | LEU | B | 221 | 81.180 | 28.974 | −8.765 | 1.00 | 3.79 | B | C |
| ATOM | 12006 | C | LEU | B | 221 | 81.507 | 26.285 | −12.298 | 1.00 | 8.00 | B | C |
| ATOM | 12007 | O | LEU | B | 221 | 80.662 | 25.402 | −12.116 | 1.00 | 7.50 | B | O |
| ATOM | 12009 | N | ALA | B | 222 | 81.464 | 27.141 | −13.316 | 1.00 | 7.90 | B | N |
| ATOM | 12010 | CA | ALA | B | 222 | 80.434 | 27.087 | −14.348 | 1.00 | 8.12 | B | C |
| ATOM | 12012 | CB | ALA | B | 222 | 80.752 | 28.080 | −15.451 | 1.00 | 8.09 | B | C |
| ATOM | 12016 | C | ALA | B | 222 | 80.287 | 25.684 | −14.933 | 1.00 | 8.56 | B | C |
| ATOM | 12017 | O | ALA | B | 222 | 79.171 | 25.191 | −15.104 | 1.00 | 8.85 | B | O |
| ATOM | 12019 | N | ILE | B | 223 | 81.418 | 25.048 | −15.230 | 1.00 | 8.90 | B | N |
| ATOM | 12020 | CA | ILE | B | 223 | 81.428 | 23.699 | −15.793 | 1.00 | 9.10 | B | C |
| ATOM | 12022 | CB | ILE | B | 223 | 82.812 | 23.336 | −16.366 | 1.00 | 9.15 | B | C |
| ATOM | 12024 | CG1 | ILE | B | 223 | 83.153 | 24.241 | −17.550 | 1.00 | 9.69 | B | C |
| ATOM | 12027 | CD1 | ILE | B | 223 | 84.570 | 24.078 | −18.041 | 1.00 | 11.92 | B | C |
| ATOM | 12031 | CG2 | ILE | B | 223 | 82.845 | 21.881 | −16.816 | 1.00 | 8.99 | B | C |
| ATOM | 12035 | C | ILE | B | 223 | 81.030 | 22.657 | −14.750 | 1.00 | 9.24 | B | C |
| ATOM | 12036 | O | ILE | B | 223 | 80.215 | 21.777 | −15.028 | 1.00 | 9.09 | B | O |
| ATOM | 12038 | N | LEU | B | 224 | 81.612 | 22.756 | −13.557 | 1.00 | 9.68 | B | N |
| ATOM | 12039 | CA | LEU | B | 224 | 81.306 | 21.822 | −12.468 | 1.00 | 10.03 | B | C |
| ATOM | 12041 | CB | LEU | B | 224 | 82.114 | 22.156 | −11.208 | 1.00 | 9.46 | B | C |
| ATOM | 12044 | CG | LEU | B | 224 | 83.367 | 21.311 | −10.988 | 1.00 | 9.22 | B | C |
| ATOM | 12046 | CD1 | LEU | B | 224 | 84.199 | 21.177 | −12.262 | 1.00 | 8.16 | B | C |
| ATOM | 12050 | CD2 | LEU | B | 224 | 84.193 | 21.895 | −9.856 | 1.00 | 10.80 | B | C |
| ATOM | 12054 | C | LEU | B | 224 | 79.821 | 21.809 | −12.130 | 1.00 | 10.73 | B | C |
| ATOM | 12055 | O | LEU | B | 224 | 79.209 | 20.742 | −12.032 | 1.00 | 10.93 | B | O |
| ATOM | 12057 | N | ASP | B | 225 | 79.252 | 22.999 | −11.959 | 1.00 | 11.11 | B | N |
| ATOM | 12058 | CA | ASP | B | 225 | 77.860 | 23.124 | −11.556 | 1.00 | 11.25 | B | C |
| ATOM | 12060 | CB | ASP | B | 225 | 77.505 | 24.585 | −11.282 | 1.00 | 11.10 | B | C |
| ATOM | 12063 | CG | ASP | B | 225 | 76.227 | 24.727 | −10.487 | 1.00 | 11.83 | B | C |
| ATOM | 12064 | OD1 | ASP | B | 225 | 75.198 | 25.135 | −11.071 | 1.00 | 10.54 | B | O |
| ATOM | 12065 | OD2 | ASP | B | 225 | 76.248 | 24.405 | −9.280 | 1.00 | 11.82 | B | O |
| ATOM | 12066 | C | ASP | B | 225 | 76.939 | 22.549 | −12.627 | 1.00 | 11.77 | B | C |
| ATOM | 12067 | O | ASP | B | 225 | 76.014 | 21.798 | −12.316 | 1.00 | 11.63 | B | O |
| ATOM | 12069 | N | TYR | B | 226 | 77.209 | 22.891 | −13.885 | 1.00 | 12.20 | B | N |
| ATOM | 12070 | CA | TYR | B | 226 | 76.415 | 22.393 | −15.005 | 1.00 | 12.70 | B | C |
| ATOM | 12072 | CB | TYR | B | 226 | 76.962 | 22.925 | −16.332 | 1.00 | 12.61 | B | C |
| ATOM | 12075 | CG | TYR | B | 226 | 76.133 | 22.538 | −17.541 | 1.00 | 12.38 | B | C |
| ATOM | 12076 | CD1 | TYR | B | 226 | 75.212 | 23.421 | −18.090 | 1.00 | 12.61 | B | C |
| ATOM | 12078 | CE1 | TYR | B | 226 | 74.455 | 23.069 | −19.199 | 1.00 | 13.81 | B | C |
| ATOM | 12080 | CZ | TYR | B | 226 | 74.615 | 21.818 | −19.768 | 1.00 | 13.32 | B | C |
| ATOM | 12081 | OH | TYR | B | 226 | 73.869 | 21.457 | −20.866 | 1.00 | 14.04 | B | O |
| ATOM | 12083 | CE2 | TYR | B | 226 | 75.522 | 20.926 | −19.239 | 1.00 | 11.80 | B | C |
| ATOM | 12085 | CD2 | TYR | B | 226 | 76.274 | 21.287 | −18.135 | 1.00 | 11.70 | B | C |
| ATOM | 12087 | C | TYR | B | 226 | 76.365 | 20.861 | −15.025 | 1.00 | 13.36 | B | C |
| ATOM | 12088 | O | TYR | B | 226 | 75.290 | 20.273 | −15.170 | 1.00 | 14.07 | B | O |
| ATOM | 12090 | N | ASN | B | 227 | 77.527 | 20.225 | −14.882 | 1.00 | 13.50 | B | N |
| ATOM | 12091 | CA | ASN | B | 227 | 77.611 | 18.764 | −14.862 | 1.00 | 13.63 | B | C |
| ATOM | 12093 | CB | ASN | B | 227 | 79.074 | 18.302 | −14.837 | 1.00 | 13.86 | B | C |
| ATOM | 12096 | CG | ASN | B | 227 | 79.789 | 18.524 | −16.161 | 1.00 | 14.25 | B | C |
| ATOM | 12097 | OD1 | ASN | B | 227 | 79.172 | 18.516 | −17.230 | 1.00 | 13.18 | B | O |
| ATOM | 12098 | ND2 | ASN | B | 227 | 81.104 | 18.712 | −16.094 | 1.00 | 12.89 | B | N |
| ATOM | 12101 | C | ASN | B | 227 | 76.866 | 18.166 | −13.673 | 1.00 | 13.81 | B | C |
| ATOM | 12102 | O | ASN | B | 227 | 76.139 | 17.186 | −13.824 | 1.00 | 13.98 | B | O |
| ATOM | 12104 | N | MET | B | 228 | 77.053 | 18.757 | −12.495 | 1.00 | 14.03 | B | N |
| ATOM | 12105 | CA | MET | B | 228 | 76.345 | 18.325 | −11.288 | 1.00 | 14.59 | B | C |
| ATOM | 12107 | CB | MET | B | 228 | 76.698 | 19.234 | −10.107 | 1.00 | 15.31 | B | C |
| ATOM | 12110 | CG | MET | B | 228 | 75.985 | 18.894 | −8.792 | 1.00 | 16.38 | B | C |
| ATOM | 12113 | SD | MET | B | 228 | 75.944 | 20.288 | −7.645 | 1.00 | 18.68 | B | S |
| ATOM | 12114 | CE | MET | B | 228 | 74.714 | 21.327 | −8.435 | 1.00 | 17.56 | B | C |
| ATOM | 12118 | C | MET | B | 228 | 74.835 | 18.345 | −11.507 | 1.00 | 14.50 | B | C |
| ATOM | 12119 | O | MET | B | 228 | 74.136 | 17.402 | −11.138 | 1.00 | 14.64 | B | O |
| ATOM | 12121 | N | ILE | B | 229 | 74.337 | 19.427 | −12.097 | 1.00 | 14.25 | B | N |
| ATOM | 12122 | CA | ILE | B | 229 | 72.916 | 19.538 | −12.398 | 1.00 | 14.20 | B | C |
| ATOM | 12124 | CB | ILE | B | 229 | 72.537 | 20.957 | −12.857 | 1.00 | 14.37 | B | C |
| ATOM | 12126 | CG1 | ILE | B | 229 | 72.802 | 21.973 | −11.741 | 1.00 | 14.47 | B | C |
| ATOM | 12129 | CD1 | ILE | B | 229 | 72.024 | 23.268 | −11.891 | 1.00 | 13.51 | B | C |
| ATOM | 12133 | CG2 | ILE | B | 229 | 71.074 | 21.011 | −13.262 | 1.00 | 15.42 | B | C |
| ATOM | 12137 | C | ILE | B | 229 | 72.528 | 18.523 | −13.470 | 1.00 | 13.75 | B | C |
| ATOM | 12138 | O | ILE | B | 229 | 71.558 | 17.789 | −13.310 | 1.00 | 13.08 | B | O |
| ATOM | 12140 | N | GLN | B | 230 | 73.297 | 18.476 | −14.554 | 1.00 | 14.01 | B | N |
| ATOM | 12141 | CA | GLN | B | 230 | 73.092 | 17.472 | −15.599 | 1.00 | 14.55 | B | C |
| ATOM | 12143 | CB | GLN | B | 230 | 74.216 | 17.535 | −16.640 | 1.00 | 14.49 | B | C |
| ATOM | 12146 | CG | GLN | B | 230 | 74.086 | 16.503 | −17.757 | 1.00 | 13.89 | B | C |
| ATOM | 12149 | CD | GLN | B | 230 | 75.223 | 16.564 | −18.755 | 1.00 | 12.94 | B | C |

TABLE 8-2-continued

Coordinates for L494P Structure

| | | | | | | | | | | | | |
|---|---|---|---|---|---|---|---|---|---|---|---|---|
| ATOM | 12150 | OE1 | GLN | B | 230 | 76.100 | 15.701 | −18.761 | 1.00 | 12.13 | B | O |
| ATOM | 12151 | NE2 | GLN | B | 230 | 75.213 | 17.582 | −19.608 | 1.00 | 10.57 | B | N |
| ATOM | 12154 | C | GLN | B | 230 | 72.996 | 16.052 | −15.026 | 1.00 | 15.29 | B | C |
| ATOM | 12155 | O | GLN | B | 230 | 72.177 | 15.255 | −15.481 | 1.00 | 15.71 | B | O |
| ATOM | 12157 | N | SER | B | 231 | 73.832 | 15.739 | −14.037 | 1.00 | 15.66 | B | N |
| ATOM | 12158 | CA | SER | B | 231 | 73.793 | 14.425 | −13.387 | 1.00 | 15.81 | B | C |
| ATOM | 12160 | CB | SER | B | 231 | 75.004 | 14.227 | −12.468 | 1.00 | 15.73 | B | C |
| ATOM | 12163 | OG | SER | B | 231 | 74.848 | 14.926 | −11.246 | 1.00 | 16.09 | B | O |
| ATOM | 12165 | C | SER | B | 231 | 72.492 | 14.223 | −12.600 | 1.00 | 16.06 | B | C |
| ATOM | 12166 | O | SER | B | 231 | 71.989 | 13.102 | −12.511 | 1.00 | 15.88 | B | O |
| ATOM | 12168 | N | VAL | B | 232 | 71.959 | 15.306 | −12.034 | 1.00 | 16.47 | B | N |
| ATOM | 12169 | CA | VAL | B | 232 | 70.661 | 15.266 | −11.355 | 1.00 | 16.95 | B | C |
| ATOM | 12171 | CB | VAL | B | 232 | 70.343 | 16.593 | −10.607 | 1.00 | 17.13 | B | C |
| ATOM | 12173 | CG1 | VAL | B | 232 | 68.971 | 16.529 | −9.941 | 1.00 | 16.99 | B | C |
| ATOM | 12177 | CG2 | VAL | B | 232 | 71.412 | 16.892 | −9.570 | 1.00 | 18.25 | B | C |
| ATOM | 12181 | C | VAL | B | 232 | 69.543 | 14.957 | −12.355 | 1.00 | 17.08 | B | C |
| ATOM | 12182 | O | VAL | B | 232 | 68.608 | 14.229 | −12.032 | 1.00 | 17.31 | B | O |
| ATOM | 12184 | N | TYR | B | 233 | 69.646 | 15.502 | −13.566 | 1.00 | 17.20 | B | N |
| ATOM | 12185 | CA | TYR | B | 233 | 68.679 | 15.203 | −14.624 | 1.00 | 17.30 | B | C |
| ATOM | 12187 | CB | TYR | B | 233 | 68.880 | 16.109 | −15.842 | 1.00 | 17.15 | B | C |
| ATOM | 12190 | CG | TYR | B | 233 | 68.763 | 17.600 | −15.593 | 1.00 | 16.58 | B | C |
| ATOM | 12191 | CD1 | TYR | B | 233 | 68.056 | 18.113 | −14.502 | 1.00 | 14.97 | B | C |
| ATOM | 12193 | CE1 | TYR | B | 233 | 67.957 | 19.481 | −14.296 | 1.00 | 14.04 | B | C |
| ATOM | 12195 | CZ | TYR | B | 233 | 68.549 | 20.349 | −15.194 | 1.00 | 14.25 | B | C |
| ATOM | 12196 | OH | TYR | B | 233 | 68.461 | 21.706 | −15.012 | 1.00 | 13.90 | B | O |
| ATOM | 12198 | CE2 | TYR | B | 233 | 69.240 | 19.866 | −16.283 | 1.00 | 15.45 | B | C |
| ATOM | 12200 | CD2 | TYR | B | 233 | 69.341 | 18.503 | −16.479 | 1.00 | 16.33 | B | C |
| ATOM | 12202 | C | TYR | B | 233 | 68.782 | 13.750 | −15.077 | 1.00 | 17.89 | B | C |
| ATOM | 12203 | O | TYR | B | 233 | 67.772 | 13.135 | −15.421 | 1.00 | 18.00 | B | O |
| ATOM | 12205 | N | GLN | B | 234 | 70.003 | 13.215 | −15.093 | 1.00 | 18.54 | B | N |
| ATOM | 12206 | CA | GLN | B | 234 | 70.234 | 11.817 | −15.465 | 1.00 | 18.95 | B | C |
| ATOM | 12208 | CB | GLN | B | 234 | 71.730 | 11.535 | −15.644 | 1.00 | 18.86 | B | C |
| ATOM | 12211 | CG | GLN | B | 234 | 72.324 | 12.116 | −16.920 | 1.00 | 18.09 | B | C |
| ATOM | 12214 | CD | GLN | B | 234 | 73.816 | 11.854 | −17.051 | 1.00 | 17.24 | B | C |
| ATOM | 12215 | OE1 | GLN | B | 234 | 74.324 | 10.830 | −16.593 | 1.00 | 17.14 | B | O |
| ATOM | 12216 | NE2 | GLN | B | 234 | 74.524 | 12.779 | −17.686 | 1.00 | 15.08 | B | N |
| ATOM | 12219 | C | GLN | B | 234 | 69.638 | 10.858 | −14.434 | 1.00 | 19.60 | B | C |
| ATOM | 12220 | O | GLN | B | 234 | 69.011 | 9.865 | −14.802 | 1.00 | 19.31 | B | O |
| ATOM | 12222 | N | ARG | B | 235 | 69.837 | 11.156 | −13.151 | 1.00 | 20.61 | B | N |
| ATOM | 12223 | CA | ARG | B | 235 | 69.232 | 10.365 | −12.074 | 1.00 | 21.86 | B | C |
| ATOM | 12225 | CB | ARG | B | 235 | 69.842 | 10.722 | −10.712 | 1.00 | 22.48 | B | C |
| ATOM | 12228 | CG | ARG | B | 235 | 69.357 | 9.837 | −9.562 | 1.00 | 24.72 | B | C |
| ATOM | 12231 | CD | ARG | B | 235 | 70.130 | 10.088 | −8.272 | 1.00 | 28.63 | B | C |
| ATOM | 12234 | NE | ARG | B | 235 | 70.043 | 11.485 | −7.828 | 1.00 | 32.42 | B | N |
| ATOM | 12236 | CZ | ARG | B | 235 | 71.016 | 12.398 | −7.918 | 1.00 | 33.76 | B | C |
| ATOM | 12237 | NH1 | ARG | B | 235 | 72.205 | 12.098 | −8.440 | 1.00 | 34.56 | B | N |
| ATOM | 12240 | NH2 | ARG | B | 235 | 70.799 | 13.633 | −7.472 | 1.00 | 33.57 | B | N |
| ATOM | 12243 | C | ARG | B | 235 | 67.710 | 10.550 | −12.039 | 1.00 | 21.94 | B | C |
| ATOM | 12244 | O | ARG | B | 235 | 66.976 | 9.623 | −11.687 | 1.00 | 22.34 | B | O |
| ATOM | 12246 | N | ASP | B | 236 | 67.244 | 11.745 | −12.393 | 1.00 | 21.69 | B | N |
| ATOM | 12247 | CA | ASP | B | 236 | 65.818 | 11.975 | −12.584 | 1.00 | 21.55 | B | C |
| ATOM | 12249 | CB | ASP | B | 236 | 65.530 | 13.445 | −12.920 | 1.00 | 21.49 | B | C |
| ATOM | 12252 | CG | ASP | B | 236 | 65.742 | 14.384 | −11.737 | 1.00 | 21.70 | B | C |
| ATOM | 12253 | OD1 | ASP | B | 236 | 65.961 | 13.915 | −10.601 | 1.00 | 22.53 | B | O |
| ATOM | 12254 | OD2 | ASP | B | 236 | 65.694 | 15.611 | −11.951 | 1.00 | 20.61 | B | O |
| ATOM | 12255 | C | ASP | B | 236 | 65.324 | 11.086 | −13.719 | 1.00 | 21.53 | B | C |
| ATOM | 12256 | O | ASP | B | 236 | 64.440 | 10.255 | −13.520 | 1.00 | 21.51 | B | O |
| ATOM | 12258 | N | LEU | B | 237 | 65.929 | 11.247 | −14.895 | 1.00 | 21.85 | B | N |
| ATOM | 12259 | CA | LEU | B | 237 | 65.483 | 10.568 | −16.117 | 1.00 | 22.44 | B | C |
| ATOM | 12261 | CB | LEU | B | 237 | 66.369 | 10.963 | −17.307 | 1.00 | 22.59 | B | C |
| ATOM | 12264 | CG | LEU | B | 237 | 65.987 | 10.394 | −18.683 | 1.00 | 22.86 | B | C |
| ATOM | 12266 | CD1 | LEU | B | 237 | 64.591 | 10.840 | −19.099 | 1.00 | 22.39 | B | C |
| ATOM | 12270 | CD2 | LEU | B | 237 | 67.011 | 10.801 | −19.734 | 1.00 | 23.22 | B | C |
| ATOM | 12274 | C | LEU | B | 237 | 65.435 | 9.043 | −16.002 | 1.00 | 22.87 | B | C |
| ATOM | 12275 | O | LEU | B | 237 | 64.508 | 8.421 | −16.518 | 1.00 | 23.17 | B | O |
| ATOM | 12277 | N | ARG | B | 238 | 66.429 | 8.445 | −15.347 | 1.00 | 23.22 | B | N |
| ATOM | 12278 | CA | ARG | B | 238 | 66.465 | 6.986 | −15.167 | 1.00 | 23.20 | B | C |
| ATOM | 12280 | CB | ARG | B | 238 | 67.747 | 6.544 | −14.453 | 1.00 | 23.33 | B | C |
| ATOM | 12283 | CG | ARG | B | 238 | 68.977 | 6.488 | −15.348 | 1.00 | 24.49 | B | C |
| ATOM | 12286 | CD | ARG | B | 238 | 70.111 | 5.717 | −14.683 | 1.00 | 25.92 | B | C |
| ATOM | 12289 | NE | ARG | B | 238 | 70.498 | 6.303 | −13.397 | 1.00 | 27.40 | B | N |
| ATOM | 12291 | CZ | ARG | B | 238 | 71.452 | 7.219 | −13.216 | 1.00 | 27.20 | B | C |
| ATOM | 12292 | NH1 | ARG | B | 238 | 72.161 | 7.693 | −14.239 | 1.00 | 26.98 | B | N |
| ATOM | 12295 | NH2 | ARG | B | 238 | 71.701 | 7.669 | −11.991 | 1.00 | 27.09 | B | N |
| ATOM | 12298 | C | ARG | B | 238 | 65.253 | 6.480 | −14.393 | 1.00 | 23.04 | B | C |
| ATOM | 12299 | O | ARG | B | 238 | 64.725 | 5.416 | −14.697 | 1.00 | 22.74 | B | O |
| ATOM | 12301 | N | GLU | B | 239 | 64.822 | 7.252 | −13.397 | 1.00 | 23.57 | B | N |
| ATOM | 12302 | CA | GLU | B | 239 | 63.645 | 6.916 | −12.592 | 1.00 | 24.22 | B | C |

TABLE 8-2-continued

Coordinates for L494P Structure

| | | | | | | | | | | | | |
|---|---|---|---|---|---|---|---|---|---|---|---|---|
| ATOM | 12304 | CB | GLU | B | 239 | 63.617 | 7.774 | −11.322 | 1.00 | 24.77 | B | C |
| ATOM | 12307 | CG | GLU | B | 239 | 62.618 | 7.317 | −10.265 | 1.00 | 26.77 | B | C |
| ATOM | 12310 | CD | GLU | B | 239 | 62.813 | 8.028 | −8.934 | 1.00 | 29.81 | B | C |
| ATOM | 12311 | OE1 | GLU | B | 239 | 63.910 | 7.911 | −8.348 | 1.00 | 30.83 | B | O |
| ATOM | 12312 | OE2 | GLU | B | 239 | 61.867 | 8.702 | −8.469 | 1.00 | 32.55 | B | O |
| ATOM | 12313 | C | GLU | B | 239 | 62.338 | 7.085 | −13.382 | 1.00 | 23.78 | B | C |
| ATOM | 12314 | O | GLU | B | 239 | 61.406 | 6.293 | −13.224 | 1.00 | 23.75 | B | O |
| ATOM | 12316 | N | THR | B | 240 | 62.271 | 8.115 | −14.222 | 1.00 | 23.31 | B | N |
| ATOM | 12317 | CA | THR | B | 240 | 61.130 | 8.298 | −15.122 | 1.00 | 23.25 | B | C |
| ATOM | 12319 | CB | THR | B | 240 | 61.132 | 9.703 | −15.767 | 1.00 | 23.05 | B | C |
| ATOM | 12321 | OG1 | THR | B | 240 | 61.223 | 10.703 | −14.746 | 1.00 | 22.86 | B | O |
| ATOM | 12323 | CG2 | THR | B | 240 | 59.862 | 9.932 | −16.574 | 1.00 | 22.22 | B | C |
| ATOM | 12327 | C | THR | B | 240 | 61.135 | 7.236 | −16.227 | 1.00 | 23.58 | B | C |
| ATOM | 12328 | O | THR | B | 240 | 60.076 | 6.746 | −16.630 | 1.00 | 23.36 | B | O |
| ATOM | 12330 | N | SER | B | 241 | 62.330 | 6.888 | −16.707 | 1.00 | 23.85 | B | N |
| ATOM | 12331 | CA | SER | B | 241 | 62.500 | 5.878 | −17.758 | 1.00 | 24.00 | B | C |
| ATOM | 12333 | CB | SER | B | 241 | 63.943 | 5.868 | −18.271 | 1.00 | 24.23 | B | C |
| ATOM | 12336 | OG | SER | B | 241 | 64.304 | 7.126 | −18.813 | 1.00 | 25.12 | B | O |
| ATOM | 12338 | C | SER | B | 241 | 62.124 | 4.479 | −17.280 | 1.00 | 24.04 | B | C |
| ATOM | 12339 | O | SER | B | 241 | 61.531 | 3.705 | −18.032 | 1.00 | 23.92 | B | O |
| ATOM | 12341 | N | ARG | B | 242 | 62.483 | 4.151 | −16.039 | 1.00 | 24.20 | B | N |
| ATOM | 12342 | CA | ARG | B | 242 | 62.037 | 2.900 | −15.427 | 1.00 | 24.47 | B | C |
| ATOM | 12344 | CB | ARG | B | 242 | 62.565 | 2.741 | −13.992 | 1.00 | 24.64 | B | C |
| ATOM | 12347 | CG | ARG | B | 242 | 63.977 | 2.149 | −13.889 | 1.00 | 25.62 | B | C |
| ATOM | 12350 | CD | ARG | B | 242 | 64.220 | 1.493 | −12.525 | 1.00 | 25.82 | B | C |
| ATOM | 12353 | NE | ARG | B | 242 | 63.800 | 2.347 | −11.411 | 1.00 | 26.44 | B | N |
| ATOM | 12355 | CZ | ARG | B | 242 | 64.518 | 3.342 | −10.885 | 1.00 | 26.48 | B | C |
| ATOM | 12356 | NH1 | ARG | B | 242 | 64.020 | 4.045 | −9.874 | 1.00 | 25.75 | B | N |
| ATOM | 12359 | NH2 | ARG | B | 242 | 65.725 | 3.644 | −11.356 | 1.00 | 27.75 | B | N |
| ATOM | 12362 | C | ARG | B | 242 | 60.512 | 2.851 | −15.429 | 1.00 | 24.30 | B | C |
| ATOM | 12363 | O | ARG | B | 242 | 59.919 | 1.885 | −15.909 | 1.00 | 24.90 | B | O |
| ATOM | 12365 | N | TRP | B | 243 | 59.887 | 3.903 | −14.906 | 1.00 | 23.61 | B | N |
| ATOM | 12366 | CA | TRP | B | 243 | 58.429 | 4.000 | −14.888 | 1.00 | 22.97 | B | C |
| ATOM | 12368 | CB | TRP | B | 243 | 57.982 | 5.318 | −14.237 | 1.00 | 22.79 | B | C |
| ATOM | 12371 | CG | TRP | B | 243 | 56.531 | 5.655 | −14.463 | 1.00 | 21.51 | B | C |
| ATOM | 12372 | CD1 | TRP | B | 243 | 55.465 | 5.256 | −13.708 | 1.00 | 20.30 | B | C |
| ATOM | 12374 | NE1 | TRP | B | 243 | 54.301 | 5.768 | −14.228 | 1.00 | 19.74 | B | N |
| ATOM | 12376 | CE2 | TRP | B | 243 | 54.599 | 6.513 | −15.339 | 1.00 | 19.29 | B | C |
| ATOM | 12377 | CD2 | TRP | B | 243 | 55.995 | 6.466 | −15.517 | 1.00 | 19.30 | B | C |
| ATOM | 12378 | CE3 | TRP | B | 243 | 56.561 | 7.151 | −16.597 | 1.00 | 18.07 | B | C |
| ATOM | 12380 | CZ3 | TRP | B | 243 | 55.728 | 7.850 | −17.453 | 1.00 | 17.55 | B | C |
| ATOM | 12382 | CH2 | TRP | B | 243 | 54.344 | 7.880 | −17.252 | 1.00 | 17.66 | B | C |
| ATOM | 12384 | CZ2 | TRP | B | 243 | 53.759 | 7.218 | −16.205 | 1.00 | 19.44 | B | C |
| ATOM | 12386 | C | TRP | B | 243 | 57.852 | 3.879 | −16.299 | 1.00 | 22.95 | B | C |
| ATOM | 12387 | O | TRP | B | 243 | 56.882 | 3.151 | −16.515 | 1.00 | 23.06 | B | O |
| ATOM | 12389 | N | TRP | B | 244 | 58.457 | 4.585 | −17.252 | 1.00 | 22.77 | B | N |
| ATOM | 12390 | CA | TRP | B | 244 | 57.944 | 4.624 | −18.624 | 1.00 | 22.56 | B | C |
| ATOM | 12392 | CB | TRP | B | 244 | 58.743 | 5.624 | −19.473 | 1.00 | 22.41 | B | C |
| ATOM | 12395 | CG | TRP | B | 244 | 58.196 | 5.866 | −20.872 | 1.00 | 21.79 | B | C |
| ATOM | 12396 | CD1 | TRP | B | 244 | 58.907 | 5.853 | −22.041 | 1.00 | 21.43 | B | C |
| ATOM | 12398 | NE1 | TRP | B | 244 | 58.078 | 6.124 | −23.105 | 1.00 | 20.15 | B | N |
| ATOM | 12400 | CE2 | TRP | B | 244 | 56.804 | 6.314 | −22.641 | 1.00 | 18.38 | B | C |
| ATOM | 12401 | CD2 | TRP | B | 244 | 56.836 | 6.162 | −21.238 | 1.00 | 19.68 | B | C |
| ATOM | 12402 | CE3 | TRP | B | 244 | 55.644 | 6.312 | −20.517 | 1.00 | 17.93 | B | C |
| ATOM | 12404 | CZ3 | TRP | B | 244 | 54.482 | 6.602 | −21.206 | 1.00 | 16.17 | B | C |
| ATOM | 12406 | CH2 | TRP | B | 244 | 54.483 | 6.745 | −22.599 | 1.00 | 16.40 | B | C |
| ATOM | 12408 | CZ2 | TRP | B | 244 | 55.631 | 6.605 | −23.333 | 1.00 | 16.86 | B | C |
| ATOM | 12410 | C | TRP | B | 244 | 57.951 | 3.241 | −19.268 | 1.00 | 22.60 | B | C |
| ATOM | 12411 | O | TRP | B | 244 | 57.038 | 2.906 | −20.023 | 1.00 | 23.08 | B | O |
| ATOM | 12413 | N | ARG | B | 245 | 58.967 | 2.443 | −18.951 | 1.00 | 22.59 | B | N |
| ATOM | 12414 | CA | ARG | B | 245 | 59.086 | 1.083 | −19.483 | 1.00 | 22.68 | B | C |
| ATOM | 12416 | CB | ARG | B | 245 | 60.484 | 0.511 | −19.208 | 1.00 | 22.97 | B | C |
| ATOM | 12419 | CG | ARG | B | 245 | 61.171 | −0.073 | −20.439 | 1.00 | 24.49 | B | C |
| ATOM | 12422 | CD | ARG | B | 245 | 62.637 | −0.418 | −20.184 | 1.00 | 26.62 | B | C |
| ATOM | 12425 | NE | ARG | B | 245 | 63.364 | 0.675 | −19.532 | 1.00 | 29.64 | B | N |
| ATOM | 12427 | CZ | ARG | B | 245 | 63.829 | 0.665 | −18.278 | 1.00 | 32.38 | B | C |
| ATOM | 12428 | NH1 | ARG | B | 245 | 64.468 | 1.734 | −17.808 | 1.00 | 32.81 | B | N |
| ATOM | 12431 | NH2 | ARG | B | 245 | 63.675 | −0.395 | −17.485 | 1.00 | 32.73 | B | N |
| ATOM | 12434 | C | ARG | B | 245 | 58.011 | 0.172 | −18.885 | 1.00 | 22.31 | B | C |
| ATOM | 12435 | O | ARG | B | 245 | 57.367 | −0.580 | −19.610 | 1.00 | 22.44 | B | O |
| ATOM | 12437 | N | ARG | B | 246 | 57.825 | 0.255 | −17.567 | 1.00 | 22.29 | B | N |
| ATOM | 12438 | CA | ARG | B | 246 | 56.787 | −0.507 | −16.850 | 1.00 | 22.34 | B | C |
| ATOM | 12440 | CB | ARG | B | 246 | 56.771 | −0.127 | −15.363 | 1.00 | 22.79 | B | C |
| ATOM | 12443 | CG | ARG | B | 246 | 57.920 | −0.713 | −14.543 | 1.00 | 25.55 | B | C |
| ATOM | 12446 | CD | ARG | B | 246 | 57.440 | −1.710 | −13.486 | 1.00 | 28.55 | B | C |
| ATOM | 12449 | NE | ARG | B | 246 | 56.772 | −2.885 | −14.050 | 1.00 | 30.25 | B | N |
| ATOM | 12451 | CZ | ARG | B | 246 | 56.294 | −3.902 | −13.330 | 1.00 | 31.54 | B | C |
| ATOM | 12452 | NH1 | ARG | B | 246 | 55.701 | −4.922 | −13.939 | 1.00 | 31.77 | B | N |

TABLE 8-2-continued

Coordinates for L494P Structure

| | | | | | | | | | | | | |
|---|---|---|---|---|---|---|---|---|---|---|---|---|
| ATOM | 12455 | NH2 | ARG | B | 246 | 56.406 | −3.910 | −12.004 | 1.00 | 32.68 | B | N |
| ATOM | 12458 | C | ARG | B | 246 | 55.395 | −0.282 | −17.433 | 1.00 | 21.44 | B | C |
| ATOM | 12459 | O | ARG | B | 246 | 54.664 | −1.236 | −17.698 | 1.00 | 21.29 | B | O |
| ATOM | 12461 | N | VAL | B | 247 | 55.031 | 0.985 | −17.612 | 1.00 | 20.80 | B | N |
| ATOM | 12462 | CA | VAL | B | 247 | 53.776 | 1.340 | −18.268 | 1.00 | 20.16 | B | C |
| ATOM | 12464 | CB | VAL | B | 247 | 53.602 | 2.872 | −18.404 | 1.00 | 19.88 | B | C |
| ATOM | 12466 | CG1 | VAL | B | 247 | 53.749 | 3.555 | −17.056 | 1.00 | 18.27 | B | C |
| ATOM | 12470 | CG2 | VAL | B | 247 | 52.252 | 3.203 | −19.016 | 1.00 | 19.22 | B | C |
| ATOM | 12474 | C | VAL | B | 247 | 53.777 | 0.705 | −19.653 | 1.00 | 20.35 | B | C |
| ATOM | 12475 | O | VAL | B | 247 | 52.834 | 0.012 | −20.024 | 1.00 | 19.91 | B | O |
| ATOM | 12477 | N | GLY | B | 248 | 54.856 | 0.941 | −20.398 | 1.00 | 20.85 | B | N |
| ATOM | 12478 | CA | GLY | B | 248 | 55.099 | 0.287 | −21.684 | 1.00 | 21.09 | B | C |
| ATOM | 12481 | C | GLY | B | 248 | 54.039 | 0.561 | −22.731 | 1.00 | 21.48 | B | C |
| ATOM | 12482 | O | GLY | B | 248 | 53.686 | −0.327 | −23.509 | 1.00 | 21.44 | B | O |
| ATOM | 12484 | N | LEU | B | 249 | 53.539 | 1.792 | −22.763 | 1.00 | 21.90 | B | N |
| ATOM | 12485 | CA | LEU | B | 249 | 52.414 | 2.128 | −23.633 | 1.00 | 22.39 | B | C |
| ATOM | 12487 | CB | LEU | B | 249 | 51.736 | 3.423 | −23.164 | 1.00 | 22.22 | B | C |
| ATOM | 12490 | CG | LEU | B | 249 | 50.264 | 3.619 | −23.549 | 1.00 | 21.67 | B | C |
| ATOM | 12492 | CD1 | LEU | B | 249 | 49.396 | 2.466 | −23.060 | 1.00 | 19.27 | B | C |
| ATOM | 12496 | CD2 | LEU | B | 249 | 49.741 | 4.948 | −23.007 | 1.00 | 21.26 | B | C |
| ATOM | 12500 | C | LEU | B | 249 | 52.844 | 2.229 | −25.102 | 1.00 | 23.09 | B | C |
| ATOM | 12501 | O | LEU | B | 249 | 52.140 | 1.744 | −25.989 | 1.00 | 23.40 | B | O |
| ATOM | 12503 | N | ALA | B | 250 | 54.004 | 2.837 | −25.351 | 1.00 | 23.56 | B | N |
| ATOM | 12504 | CA | ALA | B | 250 | 54.523 | 2.999 | −26.717 | 1.00 | 23.56 | B | C |
| ATOM | 12506 | CB | ALA | B | 250 | 55.778 | 3.867 | −26.708 | 1.00 | 23.75 | B | C |
| ATOM | 12510 | C | ALA | B | 250 | 54.812 | 1.661 | −27.406 | 1.00 | 23.27 | B | C |
| ATOM | 12511 | O | ALA | B | 250 | 54.632 | 1.533 | −28.621 | 1.00 | 22.94 | B | O |
| ATOM | 12513 | N | THR | B | 251 | 55.261 | 0.677 | −26.630 | 1.00 | 23.12 | B | N |
| ATOM | 12514 | CA | THR | B | 251 | 55.528 | −0.665 | −27.151 | 1.00 | 23.11 | B | C |
| ATOM | 12516 | CB | THR | B | 251 | 56.313 | −1.525 | −26.133 | 1.00 | 23.00 | B | C |
| ATOM | 12518 | OG1 | THR | B | 251 | 57.569 | −0.903 | −25.843 | 1.00 | 23.41 | B | O |
| ATOM | 12520 | CG2 | THR | B | 251 | 56.567 | −2.922 | −26.682 | 1.00 | 23.17 | B | C |
| ATOM | 12524 | C | THR | B | 251 | 54.240 | −1.402 | −27.518 | 1.00 | 22.91 | B | C |
| ATOM | 12525 | O | THR | B | 251 | 54.183 | −2.081 | −28.544 | 1.00 | 23.01 | B | O |
| ATOM | 12527 | N | LYS | B | 252 | 53.213 | −1.259 | −26.683 | 1.00 | 22.75 | B | N |
| ATOM | 12528 | CA | LYS | B | 252 | 51.970 | −2.019 | −26.843 | 1.00 | 22.97 | B | C |
| ATOM | 12530 | CB | LYS | B | 252 | 51.347 | −2.303 | −25.473 | 1.00 | 23.14 | B | C |
| ATOM | 12533 | CG | LYS | B | 252 | 52.249 | −3.107 | −24.525 | 1.00 | 23.20 | B | C |
| ATOM | 12536 | CD | LYS | B | 252 | 52.403 | −4.563 | −24.963 | 1.00 | 24.47 | B | C |
| ATOM | 12539 | CE | LYS | B | 252 | 53.339 | −5.338 | −24.041 | 1.00 | 24.49 | B | C |
| ATOM | 12542 | NZ | LYS | B | 252 | 53.670 | −6.689 | −24.576 | 1.00 | 23.12 | B | N |
| ATOM | 12546 | C | LYS | B | 252 | 50.949 | −1.350 | −27.781 | 1.00 | 23.11 | B | C |
| ATOM | 12547 | O | LYS | B | 252 | 50.186 | −2.046 | −28.457 | 1.00 | 23.06 | B | O |
| ATOM | 12549 | N | LEU | B | 253 | 50.931 | −0.017 | −27.821 | 1.00 | 23.21 | B | N |
| ATOM | 12550 | CA | LEU | B | 253 | 50.141 | 0.714 | −28.822 | 1.00 | 23.39 | B | C |
| ATOM | 12552 | CB | LEU | B | 253 | 49.629 | 2.053 | −28.276 | 1.00 | 23.12 | B | C |
| ATOM | 12555 | CG | LEU | B | 253 | 48.187 | 2.044 | −27.757 | 1.00 | 22.22 | B | C |
| ATOM | 12557 | CD1 | LEU | B | 253 | 47.973 | 0.942 | −26.728 | 1.00 | 21.08 | B | C |
| ATOM | 12561 | CD2 | LEU | B | 253 | 47.816 | 3.406 | −27.182 | 1.00 | 19.92 | B | C |
| ATOM | 12565 | C | LEU | B | 253 | 50.979 | 0.927 | −30.085 | 1.00 | 24.12 | B | C |
| ATOM | 12566 | O | LEU | B | 253 | 52.037 | 1.561 | −30.041 | 1.00 | 24.39 | B | O |
| ATOM | 12568 | N | HIS | B | 254 | 50.482 | 0.411 | −31.208 | 1.00 | 24.48 | B | N |
| ATOM | 12569 | CA | HIS | B | 254 | 51.277 | 0.288 | −32.438 | 1.00 | 24.66 | B | C |
| ATOM | 12571 | CB | HIS | B | 254 | 50.733 | −0.854 | −33.312 | 1.00 | 24.99 | B | C |
| ATOM | 12574 | CG | HIS | B | 254 | 50.385 | −2.093 | −32.542 | 1.00 | 26.11 | B | C |
| ATOM | 12575 | ND1 | HIS | B | 254 | 51.328 | −3.020 | −32.152 | 1.00 | 26.40 | B | N |
| ATOM | 12577 | CE1 | HIS | B | 254 | 50.734 | −3.993 | −31.484 | 1.00 | 26.76 | B | C |
| ATOM | 12579 | NE2 | HIS | B | 254 | 49.441 | −3.731 | −31.425 | 1.00 | 27.08 | B | N |
| ATOM | 12581 | CD2 | HIS | B | 254 | 49.196 | −2.548 | −32.079 | 1.00 | 26.88 | B | C |
| ATOM | 12583 | C | HIS | B | 254 | 51.339 | 1.587 | −33.248 | 1.00 | 24.42 | B | C |
| ATOM | 12584 | O | HIS | B | 254 | 52.154 | 1.712 | −34.159 | 1.00 | 24.54 | B | O |
| ATOM | 12586 | N | PHE | B | 255 | 50.478 | 2.543 | −32.911 | 1.00 | 24.49 | B | N |
| ATOM | 12587 | CA | PHE | B | 255 | 50.439 | 3.853 | −33.573 | 1.00 | 24.65 | B | C |
| ATOM | 12589 | CB | PHE | B | 255 | 48.984 | 4.303 | −33.758 | 1.00 | 24.74 | B | C |
| ATOM | 12592 | CG | PHE | B | 255 | 48.292 | 4.626 | −32.464 | 1.00 | 24.93 | B | C |
| ATOM | 12593 | CD1 | PHE | B | 255 | 48.365 | 5.903 | −31.919 | 1.00 | 24.68 | B | C |
| ATOM | 12595 | CE1 | PHE | B | 255 | 47.749 | 6.196 | −30.714 | 1.00 | 25.25 | B | C |
| ATOM | 12597 | CZ | PHE | B | 255 | 47.058 | 5.204 | −30.036 | 1.00 | 25.88 | B | C |
| ATOM | 12599 | CE2 | PHE | B | 255 | 46.985 | 3.925 | −30.566 | 1.00 | 25.92 | B | C |
| ATOM | 12601 | CD2 | PHE | B | 255 | 47.602 | 3.641 | −31.771 | 1.00 | 24.96 | B | C |
| ATOM | 12603 | C | PHE | B | 255 | 51.179 | 4.931 | −32.772 | 1.00 | 24.72 | B | C |
| ATOM | 12604 | O | PHE | B | 255 | 51.506 | 5.988 | −33.312 | 1.00 | 24.47 | B | O |
| ATOM | 12606 | N | ALA | B | 256 | 51.416 | 4.665 | −31.485 | 1.00 | 24.97 | B | N |
| ATOM | 12607 | CA | ALA | B | 256 | 51.924 | 5.675 | −30.551 | 1.00 | 25.20 | B | C |
| ATOM | 12609 | CB | ALA | B | 256 | 51.462 | 5.355 | −29.132 | 1.00 | 24.99 | B | C |
| ATOM | 12613 | C | ALA | B | 256 | 53.451 | 5.822 | −30.590 | 1.00 | 25.60 | B | C |
| ATOM | 12614 | O | ALA | B | 256 | 54.180 | 4.845 | −30.776 | 1.00 | 25.02 | B | O |
| ATOM | 12616 | N | ARG | B | 257 | 53.911 | 7.058 | −30.389 | 1.00 | 26.40 | B | N |

TABLE 8-2-continued

Coordinates for L494P Structure

| | | | | | | | | | | | | |
|---|---|---|---|---|---|---|---|---|---|---|---|---|
| ATOM | 12617 | CA | ARG | B | 257 | 55.329 | 7.410 | −30.453 | 1.00 | 27.04 | B | C |
| ATOM | 12619 | CB | ARG | B | 257 | 55.511 | 8.768 | −31.132 | 1.00 | 27.31 | B | C |
| ATOM | 12622 | CG | ARG | B | 257 | 54.920 | 8.884 | −32.530 | 1.00 | 28.68 | B | C |
| ATOM | 12625 | CD | ARG | B | 257 | 54.737 | 10.347 | −32.907 | 1.00 | 30.49 | B | C |
| ATOM | 12628 | NE | ARG | B | 257 | 53.733 | 10.999 | −32.065 | 1.00 | 31.91 | B | N |
| ATOM | 12630 | CZ | ARG | B | 257 | 53.468 | 12.304 | −32.062 | 1.00 | 31.98 | B | C |
| ATOM | 12631 | NH1 | ARG | B | 257 | 54.132 | 13.134 | −32.860 | 1.00 | 32.59 | B | N |
| ATOM | 12634 | NH2 | ARG | B | 257 | 52.526 | 12.785 | −31.253 | 1.00 | 30.73 | B | N |
| ATOM | 12637 | C | ARG | B | 257 | 55.952 | 7.496 | −29.063 | 1.00 | 27.27 | B | C |
| ATOM | 12638 | O | ARG | B | 257 | 55.380 | 8.103 | −28.153 | 1.00 | 26.70 | B | O |
| ATOM | 12640 | N | ASP | B | 258 | 57.140 | 6.910 | −28.922 | 1.00 | 27.82 | B | N |
| ATOM | 12641 | CA | ASP | B | 258 | 57.907 | 6.973 | −27.680 | 1.00 | 28.09 | B | C |
| ATOM | 12643 | CB | ASP | B | 258 | 58.926 | 5.822 | −27.637 | 1.00 | 28.30 | B | C |
| ATOM | 12646 | CG | ASP | B | 258 | 59.647 | 5.710 | −26.296 | 1.00 | 29.74 | B | C |
| ATOM | 12647 | OD1 | ASP | B | 258 | 59.515 | 6.623 | −25.449 | 1.00 | 31.58 | B | O |
| ATOM | 12648 | OD2 | ASP | B | 258 | 60.350 | 4.696 | −26.088 | 1.00 | 30.24 | B | O |
| ATOM | 12649 | C | ASP | B | 258 | 58.609 | 8.335 | −27.570 | 1.00 | 27.79 | B | C |
| ATOM | 12650 | O | ASP | B | 258 | 59.694 | 8.529 | −28.122 | 1.00 | 27.75 | B | O |
| ATOM | 12652 | N | ARG | B | 259 | 57.977 | 9.269 | −26.859 | 1.00 | 27.57 | B | N |
| ATOM | 12653 | CA | ARG | B | 259 | 58.547 | 10.597 | −26.621 | 1.00 | 27.44 | B | C |
| ATOM | 12655 | CB | ARG | B | 259 | 57.645 | 11.691 | −27.212 | 1.00 | 27.68 | B | C |
| ATOM | 12658 | CG | ARG | B | 259 | 57.598 | 11.737 | −28.736 | 1.00 | 29.41 | B | C |
| ATOM | 12661 | CD | ARG | B | 259 | 58.884 | 12.297 | −29.341 | 1.00 | 30.97 | B | C |
| ATOM | 12664 | NE | ARG | B | 259 | 58.754 | 12.551 | −30.778 | 1.00 | 32.99 | B | N |
| ATOM | 12666 | CZ | ARG | B | 259 | 58.787 | 11.616 | −31.732 | 1.00 | 33.88 | B | C |
| ATOM | 12667 | NH1 | ARG | B | 259 | 58.943 | 10.329 | −31.431 | 1.00 | 34.50 | B | N |
| ATOM | 12670 | NH2 | ARG | B | 259 | 58.657 | 11.972 | −33.008 | 1.00 | 33.20 | B | N |
| ATOM | 12673 | C | ARG | B | 259 | 58.728 | 10.835 | −25.124 | 1.00 | 26.73 | B | C |
| ATOM | 12674 | O | ARG | B | 259 | 57.907 | 11.509 | −24.496 | 1.00 | 27.01 | B | O |
| ATOM | 12676 | N | LEU | B | 260 | 59.792 | 10.270 | −24.553 | 1.00 | 25.66 | B | N |
| ATOM | 12677 | CA | LEU | B | 260 | 60.147 | 10.523 | −23.152 | 1.00 | 24.71 | B | C |
| ATOM | 12679 | CB | LEU | B | 260 | 60.396 | 9.216 | −22.388 | 1.00 | 24.82 | B | C |
| ATOM | 12682 | CG | LEU | B | 260 | 60.711 | 9.346 | −20.887 | 1.00 | 23.56 | B | C |
| ATOM | 12684 | CD1 | LEU | B | 260 | 59.596 | 10.059 | −20.139 | 1.00 | 22.57 | B | C |
| ATOM | 12688 | CD2 | LEU | B | 260 | 60.956 | 7.982 | −20.276 | 1.00 | 22.94 | B | C |
| ATOM | 12692 | C | LEU | B | 260 | 61.381 | 11.411 | −23.075 | 1.00 | 23.72 | B | C |
| ATOM | 12693 | O | LEU | B | 260 | 61.347 | 12.468 | −22.445 | 1.00 | 23.35 | B | O |
| ATOM | 12695 | N | ILE | B | 261 | 62.462 | 10.979 | −23.721 | 1.00 | 22.88 | B | N |
| ATOM | 12696 | CA | ILE | B | 261 | 63.712 | 11.743 | −23.722 | 1.00 | 22.59 | B | C |
| ATOM | 12698 | CB | ILE | B | 261 | 64.773 | 11.162 | −24.691 | 1.00 | 22.38 | B | C |
| ATOM | 12700 | CG1 | ILE | B | 261 | 65.102 | 9.705 | −24.357 | 1.00 | 22.05 | B | C |
| ATOM | 12703 | CD1 | ILE | B | 261 | 66.110 | 9.080 | −25.307 | 1.00 | 21.88 | B | C |
| ATOM | 12707 | CG2 | ILE | B | 261 | 66.056 | 11.987 | −24.628 | 1.00 | 21.66 | B | C |
| ATOM | 12711 | C | ILE | B | 261 | 63.419 | 13.187 | −24.125 | 1.00 | 22.69 | B | C |
| ATOM | 12712 | O | ILE | B | 261 | 63.873 | 14.128 | −23.469 | 1.00 | 22.64 | B | O |
| ATOM | 12714 | N | GLU | B | 262 | 62.641 | 13.341 | −25.196 | 1.00 | 22.88 | B | N |
| ATOM | 12715 | CA | GLU | B | 262 | 62.215 | 14.655 | −25.692 | 1.00 | 22.71 | B | C |
| ATOM | 12717 | CB | GLU | B | 262 | 61.384 | 14.518 | −26.981 | 1.00 | 22.85 | B | C |
| ATOM | 12720 | CG | GLU | B | 262 | 62.176 | 14.081 | −28.228 | 1.00 | 23.29 | B | C |
| ATOM | 12723 | CD | GLU | B | 262 | 62.377 | 12.568 | −28.339 | 1.00 | 23.18 | B | C |
| ATOM | 12724 | OE1 | GLU | B | 262 | 62.069 | 11.832 | −27.375 | 1.00 | 22.88 | B | O |
| ATOM | 12725 | OE2 | GLU | B | 262 | 62.852 | 12.113 | −29.401 | 1.00 | 22.83 | B | O |
| ATOM | 12726 | C | GLU | B | 262 | 61.397 | 15.397 | −24.639 | 1.00 | 22.14 | B | C |
| ATOM | 12727 | O | GLU | B | 262 | 61.659 | 16.565 | −24.346 | 1.00 | 22.04 | B | O |
| ATOM | 12729 | N | SER | B | 263 | 60.408 | 14.709 | −24.073 | 1.00 | 21.51 | B | N |
| ATOM | 12730 | CA | SER | B | 263 | 59.561 | 15.292 | −23.035 | 1.00 | 21.01 | B | C |
| ATOM | 12732 | CB | SER | B | 263 | 58.448 | 14.321 | −22.627 | 1.00 | 20.92 | B | C |
| ATOM | 12735 | OG | SER | B | 263 | 57.396 | 14.332 | −23.577 | 1.00 | 20.64 | B | O |
| ATOM | 12737 | C | SER | B | 263 | 60.356 | 15.721 | −21.806 | 1.00 | 20.77 | B | C |
| ATOM | 12738 | O | SER | B | 263 | 59.996 | 16.691 | −21.146 | 1.00 | 20.59 | B | O |
| ATOM | 12740 | N | PHE | B | 264 | 61.434 | 15.008 | −21.493 | 1.00 | 21.04 | B | N |
| ATOM | 12741 | CA | PHE | B | 264 | 62.253 | 15.380 | −20.346 | 1.00 | 21.42 | B | C |
| ATOM | 12743 | CB | PHE | B | 264 | 63.143 | 14.232 | −19.886 | 1.00 | 21.45 | B | C |
| ATOM | 12746 | CG | PHE | B | 264 | 63.662 | 14.426 | −18.502 | 1.00 | 21.91 | B | C |
| ATOM | 12747 | CD1 | PHE | B | 264 | 62.912 | 14.019 | −17.408 | 1.00 | 22.62 | B | C |
| ATOM | 12749 | CE1 | PHE | B | 264 | 63.373 | 14.220 | −16.122 | 1.00 | 23.76 | B | C |
| ATOM | 12751 | CZ | PHE | B | 264 | 64.591 | 14.848 | −15.920 | 1.00 | 24.45 | B | C |
| ATOM | 12753 | CE2 | PHE | B | 264 | 65.337 | 15.273 | −17.006 | 1.00 | 23.47 | B | C |
| ATOM | 12755 | CD2 | PHE | B | 264 | 64.869 | 15.068 | −18.286 | 1.00 | 22.37 | B | C |
| ATOM | 12757 | C | PHE | B | 264 | 63.107 | 16.609 | −20.639 | 1.00 | 21.80 | B | C |
| ATOM | 12758 | O | PHE | B | 264 | 63.236 | 17.496 | −19.791 | 1.00 | 22.35 | B | O |
| ATOM | 12760 | N | TYR | B | 265 | 63.694 | 16.649 | −21.833 | 1.00 | 21.65 | B | N |
| ATOM | 12761 | CA | TYR | B | 265 | 64.396 | 17.839 | −22.327 | 1.00 | 21.35 | B | C |
| ATOM | 12763 | CB | TYR | B | 265 | 64.916 | 17.585 | −23.747 | 1.00 | 21.73 | B | C |
| ATOM | 12766 | CG | TYR | B | 265 | 65.364 | 18.817 | −24.494 | 1.00 | 22.81 | B | C |
| ATOM | 12767 | CD1 | TYR | B | 265 | 66.617 | 19.372 | −24.267 | 1.00 | 24.34 | B | C |
| ATOM | 12769 | CE1 | TYR | B | 265 | 67.033 | 20.501 | −24.954 | 1.00 | 26.45 | B | C |
| ATOM | 12771 | CZ | TYR | B | 265 | 66.192 | 21.083 | −25.886 | 1.00 | 27.60 | B | C |

TABLE 8-2-continued

Coordinates for L494P Structure

| | | | | | | | | | | | |
|---|---|---|---|---|---|---|---|---|---|---|---|
| ATOM | 12772 | OH | TYR | B | 265 | 66.601 | 22.202 | −26.573 | 1.00 | 30.92 B | O |
| ATOM | 12774 | CE2 | TYR | B | 265 | 64.944 | 20.544 | −26.133 | 1.00 | 26.49 B | C |
| ATOM | 12776 | CD2 | TYR | B | 265 | 64.539 | 19.417 | −25.440 | 1.00 | 24.55 B | C |
| ATOM | 12778 | C | TYR | B | 265 | 63.481 | 19.070 | −22.292 | 1.00 | 20.55 B | C |
| ATOM | 12779 | O | TYR | B | 265 | 63.923 | 20.176 | −21.983 | 1.00 | 20.24 B | O |
| ATOM | 12781 | N | TRP | B | 266 | 62.207 | 18.859 | −22.610 | 1.00 | 20.01 B | N |
| ATOM | 12782 | CA | TRP | B | 266 | 61.183 | 19.894 | −22.484 | 1.00 | 19.27 B | C |
| ATOM | 12784 | CB | TRP | B | 266 | 59.834 | 19.354 | −22.972 | 1.00 | 19.17 B | C |
| ATOM | 12787 | CG | TRP | B | 266 | 58.709 | 20.327 | −22.879 | 1.00 | 19.53 B | C |
| ATOM | 12788 | CD1 | TRP | B | 266 | 57.867 | 20.512 | −21.820 | 1.00 | 19.29 B | C |
| ATOM | 12790 | NE1 | TRP | B | 266 | 56.955 | 21.496 | −22.107 | 1.00 | 18.94 B | N |
| ATOM | 12792 | CE2 | TRP | B | 266 | 57.190 | 21.963 | −23.373 | 1.00 | 20.47 B | C |
| ATOM | 12793 | CD2 | TRP | B | 266 | 58.291 | 21.246 | −23.891 | 1.00 | 21.23 B | C |
| ATOM | 12794 | CE3 | TRP | B | 266 | 58.742 | 21.537 | −25.184 | 1.00 | 22.28 B | C |
| ATOM | 12796 | CZ3 | TRP | B | 266 | 58.087 | 22.520 | −25.911 | 1.00 | 22.69 B | C |
| ATOM | 12798 | CH2 | TRP | B | 266 | 56.996 | 23.218 | −25.367 | 1.00 | 22.30 B | C |
| ATOM | 12800 | CZ2 | TRP | B | 266 | 56.532 | 22.953 | −24.105 | 1.00 | 20.82 B | C |
| ATOM | 12802 | C | TRP | B | 266 | 61.069 | 20.374 | −21.039 | 1.00 | 18.58 B | C |
| ATOM | 12803 | O | TRP | B | 266 | 61.049 | 21.579 | −20.779 | 1.00 | 18.53 B | O |
| ATOM | 12805 | N | ALA | B | 267 | 61.003 | 19.422 | −20.109 | 1.00 | 18.04 B | N |
| ATOM | 12806 | CA | ALA | B | 267 | 60.846 | 19.721 | −18.680 | 1.00 | 17.48 B | C |
| ATOM | 12808 | CB | ALA | B | 267 | 60.644 | 18.432 | −17.888 | 1.00 | 17.29 B | C |
| ATOM | 12812 | C | ALA | B | 267 | 62.024 | 20.507 | −18.111 | 1.00 | 16.68 B | C |
| ATOM | 12813 | O | ALA | B | 267 | 61.834 | 21.408 | −17.294 | 1.00 | 16.12 B | O |
| ATOM | 12815 | N | VAL | B | 268 | 63.233 | 20.169 | −18.556 | 1.00 | 16.04 B | N |
| ATOM | 12816 | CA | VAL | B | 268 | 64.451 | 20.840 | −18.094 | 1.00 | 15.90 B | C |
| ATOM | 12818 | CB | VAL | B | 268 | 65.713 | 20.172 | −18.685 | 1.00 | 15.88 B | C |
| ATOM | 12820 | CG1 | VAL | B | 268 | 65.880 | 18.777 | −18.105 | 1.00 | 16.89 B | C |
| ATOM | 12824 | CG2 | VAL | B | 268 | 66.954 | 21.001 | −18.414 | 1.00 | 14.94 B | C |
| ATOM | 12828 | C | VAL | B | 268 | 64.444 | 22.339 | −18.411 | 1.00 | 15.83 B | C |
| ATOM | 12829 | O | VAL | B | 268 | 65.068 | 23.131 | −17.707 | 1.00 | 15.84 B | O |
| ATOM | 12831 | N | GLY | B | 269 | 63.736 | 22.725 | −19.467 | 1.00 | 16.01 B | N |
| ATOM | 12832 | CA | GLY | B | 269 | 63.520 | 24.136 | −19.768 | 1.00 | 16.02 B | C |
| ATOM | 12835 | C | GLY | B | 269 | 62.558 | 24.781 | −18.788 | 1.00 | 15.89 B | C |
| ATOM | 12836 | O | GLY | B | 269 | 62.710 | 25.952 | −18.440 | 1.00 | 15.72 B | O |
| ATOM | 12838 | N | VAL | B | 270 | 61.570 | 24.009 | −18.341 | 1.00 | 15.89 B | N |
| ATOM | 12839 | CA | VAL | B | 270 | 60.537 | 24.512 | −17.439 | 1.00 | 15.75 B | C |
| ATOM | 12841 | CB | VAL | B | 270 | 59.329 | 23.550 | −17.364 | 1.00 | 15.72 B | C |
| ATOM | 12843 | CG1 | VAL | B | 270 | 58.227 | 24.145 | −16.505 | 1.00 | 15.52 B | C |
| ATOM | 12847 | CG2 | VAL | B | 270 | 58.806 | 23.239 | −18.759 | 1.00 | 15.42 B | C |
| ATOM | 12851 | C | VAL | B | 270 | 61.098 | 24.728 | −16.039 | 1.00 | 15.62 B | C |
| ATOM | 12852 | O | VAL | B | 270 | 60.970 | 25.815 | −15.481 | 1.00 | 15.95 B | O |
| ATOM | 12854 | N | ALA | B | 271 | 61.724 | 23.692 | −15.485 | 1.00 | 15.73 B | N |
| ATOM | 12855 | CA | ALA | B | 271 | 62.301 | 23.756 | −14.140 | 1.00 | 16.08 B | C |
| ATOM | 12857 | CB | ALA | B | 271 | 61.403 | 23.033 | −13.156 | 1.00 | 15.92 B | C |
| ATOM | 12861 | C | ALA | B | 271 | 63.712 | 23.166 | −14.108 | 1.00 | 16.48 B | C |
| ATOM | 12862 | O | ALA | B | 271 | 63.898 | 21.987 | −13.792 | 1.00 | 16.03 B | O |
| ATOM | 12864 | N | PHE | B | 272 | 64.701 | 23.996 | −14.435 | 1.00 | 17.15 B | N |
| ATOM | 12865 | CA | PHE | B | 272 | 66.098 | 23.560 | −14.476 | 1.00 | 17.81 B | C |
| ATOM | 12867 | CB | PHE | B | 272 | 66.968 | 24.549 | −15.268 | 1.00 | 18.10 B | C |
| ATOM | 12870 | CG | PHE | B | 272 | 67.219 | 25.853 | −14.557 | 1.00 | 19.12 B | C |
| ATOM | 12871 | CD1 | PHE | B | 272 | 68.266 | 25.978 | −13.654 | 1.00 | 18.88 B | C |
| ATOM | 12873 | CE1 | PHE | B | 272 | 68.498 | 27.177 | −12.995 | 1.00 | 20.29 B | C |
| ATOM | 12875 | CZ | PHE | B | 272 | 67.688 | 28.273 | −13.242 | 1.00 | 20.78 B | C |
| ATOM | 12877 | CE2 | PHE | B | 272 | 66.645 | 28.166 | −14.146 | 1.00 | 21.63 B | C |
| ATOM | 12879 | CD2 | PHE | B | 272 | 66.414 | 26.960 | −14.799 | 1.00 | 21.22 B | C |
| ATOM | 12881 | C | PHE | B | 272 | 66.681 | 23.371 | −13.082 | 1.00 | 18.23 B | C |
| ATOM | 12882 | O | PHE | B | 272 | 67.510 | 22.486 | −12.871 | 1.00 | 18.10 B | O |
| ATOM | 12884 | N | GLU | B | 273 | 66.246 | 24.206 | −12.138 | 1.00 | 18.89 B | N |
| ATOM | 12885 | CA | GLU | B | 273 | 66.821 | 24.230 | −10.792 | 1.00 | 19.04 B | C |
| ATOM | 12887 | CB | GLU | B | 273 | 66.053 | 25.189 | −9.870 | 1.00 | 19.05 B | C |
| ATOM | 12890 | CG | GLU | B | 273 | 66.068 | 26.665 | −10.295 | 1.00 | 19.59 B | C |
| ATOM | 12893 | CD | GLU | B | 273 | 64.917 | 27.047 | −11.222 | 1.00 | 22.44 B | C |
| ATOM | 12894 | OE1 | GLU | B | 273 | 64.464 | 28.210 | −11.163 | 1.00 | 24.11 B | O |
| ATOM | 12895 | OE2 | GLU | B | 273 | 64.460 | 26.190 | −12.009 | 1.00 | 24.79 B | O |
| ATOM | 12896 | C | GLU | B | 273 | 66.826 | 22.809 | −10.215 | 1.00 | 18.87 B | C |
| ATOM | 12897 | O | GLU | B | 273 | 65.801 | 22.129 | −10.257 | 1.00 | 19.19 B | O |
| ATOM | 12899 | N | PRO | B | 274 | 67.985 | 22.349 | −9.701 | 1.00 | 18.78 B | N |
| ATOM | 12900 | CA | PRO | B | 274 | 68.155 | 20.957 | −9.253 | 1.00 | 18.78 B | C |
| ATOM | 12902 | CB | PRO | B | 274 | 69.478 | 20.999 | −8.479 | 1.00 | 18.81 B | C |
| ATOM | 12905 | CG | PRO | B | 274 | 70.229 | 22.113 | −9.082 | 1.00 | 18.95 B | C |
| ATOM | 12908 | CD | PRO | B | 274 | 69.231 | 23.127 | −9.550 | 1.00 | 18.65 B | C |
| ATOM | 12911 | C | PRO | B | 274 | 67.037 | 20.428 | −8.351 | 1.00 | 18.44 B | C |
| ATOM | 12912 | O | PRO | B | 274 | 66.501 | 19.347 | −8.599 | 1.00 | 18.00 B | O |
| ATOM | 12913 | N | GLN | B | 275 | 66.704 | 21.197 | −7.320 | 1.00 | 18.53 B | N |
| ATOM | 12914 | CA | GLN | B | 275 | 65.679 | 20.831 | −6.339 | 1.00 | 18.90 B | C |
| ATOM | 12916 | CB | GLN | B | 275 | 65.475 | 21.976 | −5.332 | 1.00 | 19.10 B | C |
| ATOM | 12919 | CG | GLN | B | 275 | 65.092 | 23.339 | −5.936 | 1.00 | 19.30 B | C |

TABLE 8-2-continued

Coordinates for L494P Structure

| | | | | | | | | | | | | |
|---|---|---|---|---|---|---|---|---|---|---|---|---|
| ATOM | 12922 | CD | GLN | B | 275 | 66.298 | 24.200 | −6.290 | 1.00 | 19.15 | B | C |
| ATOM | 12923 | OE1 | GLN | B | 275 | 67.237 | 23.734 | −6.933 | 1.00 | 19.04 | B | O |
| ATOM | 12924 | NE2 | GLN | B | 275 | 66.270 | 25.462 | −5.877 | 1.00 | 19.96 | B | N |
| ATOM | 12927 | C | GLN | B | 275 | 64.318 | 20.404 | −6.925 | 1.00 | 19.09 | B | C |
| ATOM | 12928 | O | GLN | B | 275 | 63.643 | 19.549 | −6.347 | 1.00 | 19.14 | B | O |
| ATOM | 12930 | N | TYR | B | 276 | 63.924 | 20.979 | −8.062 | 1.00 | 19.13 | B | N |
| ATOM | 12931 | CA | TYR | B | 276 | 62.625 | 20.672 | −8.679 | 1.00 | 18.93 | B | C |
| ATOM | 12933 | CB | TYR | B | 276 | 62.170 | 21.817 | −9.598 | 1.00 | 18.94 | B | C |
| ATOM | 12936 | CG | TYR | B | 276 | 62.067 | 23.177 | −8.941 | 1.00 | 19.74 | B | C |
| ATOM | 12937 | CD1 | TYR | B | 276 | 61.362 | 23.352 | −7.755 | 1.00 | 20.43 | B | C |
| ATOM | 12939 | CE1 | TYR | B | 276 | 61.263 | 24.600 | −7.159 | 1.00 | 20.81 | B | C |
| ATOM | 12941 | CZ | TYR | B | 276 | 61.858 | 25.692 | −7.759 | 1.00 | 20.24 | B | C |
| ATOM | 12942 | OH | TYR | B | 276 | 61.757 | 26.929 | −7.173 | 1.00 | 23.88 | B | O |
| ATOM | 12944 | CE2 | TYR | B | 276 | 62.551 | 25.550 | −8.942 | 1.00 | 18.69 | B | C |
| ATOM | 12946 | CD2 | TYR | B | 276 | 62.647 | 24.299 | −9.529 | 1.00 | 19.51 | B | C |
| ATOM | 12948 | C | TYR | B | 276 | 62.646 | 19.371 | −9.489 | 1.00 | 18.68 | B | C |
| ATOM | 12949 | O | TYR | B | 276 | 62.344 | 19.376 | −10.681 | 1.00 | 18.82 | B | O |
| ATOM | 12951 | N | SER | B | 277 | 62.983 | 18.256 | −8.848 | 1.00 | 18.35 | B | N |
| ATOM | 12952 | CA | SER | B | 277 | 62.984 | 16.961 | −9.534 | 1.00 | 17.80 | B | C |
| ATOM | 12954 | CB | SER | B | 277 | 63.829 | 15.938 | −8.774 | 1.00 | 17.69 | B | C |
| ATOM | 12957 | OG | SER | B | 277 | 65.212 | 16.219 | −8.923 | 1.00 | 16.37 | B | O |
| ATOM | 12959 | C | SER | B | 277 | 61.558 | 16.449 | −9.743 | 1.00 | 17.75 | B | C |
| ATOM | 12960 | O | SER | B | 277 | 61.257 | 15.869 | −10.783 | 1.00 | 17.82 | B | O |
| ATOM | 12962 | N | ASP | B | 278 | 60.687 | 16.675 | −8.761 | 1.00 | 17.90 | B | N |
| ATOM | 12963 | CA | ASP | B | 278 | 59.267 | 16.323 | −8.881 | 1.00 | 17.97 | B | C |
| ATOM | 12965 | CB | ASP | B | 278 | 58.493 | 16.711 | −7.618 | 1.00 | 18.01 | B | C |
| ATOM | 12968 | CG | ASP | B | 278 | 58.951 | 15.960 | −6.390 | 1.00 | 18.66 | B | C |
| ATOM | 12969 | OD1 | ASP | B | 278 | 59.518 | 14.860 | −6.537 | 1.00 | 22.13 | B | O |
| ATOM | 12970 | OD2 | ASP | B | 278 | 58.740 | 16.473 | −5.271 | 1.00 | 20.36 | B | O |
| ATOM | 12971 | C | ASP | B | 278 | 58.620 | 17.019 | −10.073 | 1.00 | 18.09 | B | C |
| ATOM | 12972 | O | ASP | B | 278 | 57.855 | 16.404 | −10.813 | 1.00 | 18.35 | B | O |
| ATOM | 12974 | N | CYS | B | 279 | 58.919 | 18.303 | −10.246 | 1.00 | 18.18 | B | N |
| ATOM | 12975 | CA | CYS | B | 279 | 58.366 | 19.077 | −11.356 | 1.00 | 18.27 | B | C |
| ATOM | 12977 | CB | CYS | B | 279 | 58.847 | 20.538 | −11.302 | 1.00 | 18.30 | B | C |
| ATOM | 12980 | SG | CYS | B | 279 | 57.937 | 21.699 | −12.374 | 1.00 | 16.99 | B | S |
| ATOM | 12982 | C | CYS | B | 279 | 58.758 | 18.423 | −12.676 | 1.00 | 18.44 | B | C |
| ATOM | 12983 | O | CYS | B | 279 | 57.897 | 18.121 | −13.503 | 1.00 | 18.24 | B | O |
| ATOM | 12985 | N | ARG | B | 280 | 60.055 | 18.178 | −12.846 | 1.00 | 18.78 | B | N |
| ATOM | 12986 | CA | ARG | B | 280 | 60.576 | 17.556 | −14.063 | 1.00 | 18.99 | B | C |
| ATOM | 12988 | CB | ARG | B | 280 | 62.096 | 17.386 | −13.978 | 1.00 | 19.18 | B | C |
| ATOM | 12991 | CG | ARG | B | 280 | 62.866 | 18.702 | −14.057 | 1.00 | 20.22 | B | C |
| ATOM | 12994 | CD | ARG | B | 280 | 64.364 | 18.482 | −14.244 | 1.00 | 20.99 | B | C |
| ATOM | 12997 | NE | ARG | B | 280 | 65.004 | 17.940 | −13.047 | 1.00 | 20.45 | B | N |
| ATOM | 12999 | CZ | ARG | B | 280 | 65.341 | 18.652 | −11.972 | 1.00 | 22.60 | B | C |
| ATOM | 13000 | NH1 | ARG | B | 280 | 65.098 | 19.959 | −11.908 | 1.00 | 22.84 | B | N |
| ATOM | 13003 | NH2 | ARG | B | 280 | 65.923 | 18.046 | −10.942 | 1.00 | 24.41 | B | N |
| ATOM | 13006 | C | ARG | B | 280 | 59.906 | 16.212 | −14.339 | 1.00 | 18.84 | B | C |
| ATOM | 13007 | O | ARG | B | 280 | 59.427 | 15.973 | −15.447 | 1.00 | 19.34 | B | O |
| ATOM | 13009 | N | ASN | B | 281 | 59.852 | 15.352 | −13.326 | 1.00 | 18.40 | B | N |
| ATOM | 13010 | CA | ASN | B | 281 | 59.227 | 14.034 | −13.468 | 1.00 | 18.38 | B | C |
| ATOM | 13012 | CB | ASN | B | 281 | 59.559 | 13.146 | −12.266 | 1.00 | 18.31 | B | C |
| ATOM | 13015 | CG | ASN | B | 281 | 61.055 | 12.921 | −12.103 | 1.00 | 19.38 | B | C |
| ATOM | 13016 | OD1 | ASN | B | 281 | 61.851 | 13.291 | −12.969 | 1.00 | 18.81 | B | O |
| ATOM | 13017 | ND2 | ASN | B | 281 | 61.445 | 12.317 | −10.985 | 1.00 | 21.51 | B | N |
| ATOM | 13020 | C | ASN | B | 281 | 57.710 | 14.109 | −13.672 | 1.00 | 18.30 | B | C |
| ATOM | 13021 | O | ASN | B | 281 | 57.126 | 13.240 | −14.317 | 1.00 | 18.27 | B | O |
| ATOM | 13023 | N | SER | B | 282 | 57.078 | 15.150 | −13.132 | 1.00 | 17.93 | B | N |
| ATOM | 13024 | CA | SER | B | 282 | 55.651 | 15.378 | −13.352 | 1.00 | 17.39 | B | C |
| ATOM | 13026 | CB | SER | B | 282 | 55.106 | 16.395 | −12.340 | 1.00 | 17.68 | B | C |
| ATOM | 13029 | OG | SER | B | 282 | 53.687 | 16.431 | −12.343 | 1.00 | 18.53 | B | O |
| ATOM | 13031 | C | SER | B | 282 | 55.410 | 15.861 | −14.786 | 1.00 | 16.41 | B | C |
| ATOM | 13032 | O | SER | B | 282 | 54.649 | 15.251 | −15.535 | 1.00 | 15.72 | B | O |
| ATOM | 13034 | N | VAL | B | 283 | 56.083 | 16.944 | −15.167 | 1.00 | 15.82 | B | N |
| ATOM | 13035 | CA | VAL | B | 283 | 55.893 | 17.546 | −16.489 | 1.00 | 15.38 | B | C |
| ATOM | 13037 | CB | VAL | B | 283 | 56.678 | 18.871 | −16.635 | 1.00 | 15.03 | B | C |
| ATOM | 13039 | CG1 | VAL | B | 283 | 56.610 | 19.388 | −18.066 | 1.00 | 13.71 | B | C |
| ATOM | 13043 | CG2 | VAL | B | 283 | 56.136 | 19.912 | −15.669 | 1.00 | 13.54 | B | C |
| ATOM | 13047 | C | VAL | B | 283 | 56.289 | 16.584 | −17.607 | 1.00 | 15.75 | B | C |
| ATOM | 13048 | O | VAL | B | 283 | 55.608 | 16.504 | −18.627 | 1.00 | 15.73 | B | O |
| ATOM | 13050 | N | ALA | B | 284 | 57.381 | 15.852 | −17.410 | 1.00 | 16.23 | B | N |
| ATOM | 13051 | CA | ALA | B | 284 | 57.811 | 14.857 | −18.387 | 1.00 | 16.83 | B | C |
| ATOM | 13053 | CB | ALA | B | 284 | 59.098 | 14.185 | −17.939 | 1.00 | 16.69 | B | C |
| ATOM | 13057 | C | ALA | B | 284 | 56.713 | 13.818 | −18.592 | 1.00 | 17.70 | B | C |
| ATOM | 13058 | O | ALA | B | 284 | 56.235 | 13.629 | −19.712 | 1.00 | 17.70 | B | O |
| ATOM | 13060 | N | LYS | B | 285 | 56.311 | 13.170 | −17.497 | 1.00 | 18.64 | B | N |
| ATOM | 13061 | CA | LYS | B | 285 | 55.259 | 12.146 | −17.518 | 1.00 | 18.83 | B | C |
| ATOM | 13063 | CB | LYS | B | 285 | 54.860 | 11.750 | −16.089 | 1.00 | 18.82 | B | C |
| ATOM | 13066 | CG | LYS | B | 285 | 55.795 | 10.749 | −15.431 | 1.00 | 20.25 | B | C |

TABLE 8-2-continued

| Coordinates for L494P Structure | | | | | | | | | | | | |
|---|---|---|---|---|---|---|---|---|---|---|---|---|
| ATOM | 13069 | CD | LYS | B | 285 | 55.419 | 10.498 | −13.974 | 1.00 | 22.25 | B | C |
| ATOM | 13072 | CE | LYS | B | 285 | 56.438 | 9.597 | −13.279 | 1.00 | 23.50 | B | C |
| ATOM | 13075 | NZ | LYS | B | 285 | 56.327 | 9.653 | −11.792 | 1.00 | 23.56 | B | N |
| ATOM | 13079 | C | LYS | B | 285 | 54.015 | 12.604 | −18.274 | 1.00 | 18.88 | B | C |
| ATOM | 13080 | O | LYS | B | 285 | 53.524 | 11.895 | −19.151 | 1.00 | 18.86 | B | O |
| ATOM | 13082 | N | MET | B | 286 | 53.518 | 13.790 | −17.932 | 1.00 | 19.06 | B | N |
| ATOM | 13083 | CA | MET | B | 286 | 52.272 | 14.299 | −18.506 | 1.00 | 19.32 | B | C |
| ATOM | 13085 | CB | MET | B | 286 | 51.853 | 15.601 | −17.818 | 1.00 | 19.40 | B | C |
| ATOM | 13088 | CG | MET | B | 286 | 51.483 | 15.460 | −16.350 | 1.00 | 19.99 | B | C |
| ATOM | 13091 | SD | MET | B | 286 | 50.219 | 14.220 | −16.032 | 1.00 | 21.41 | B | S |
| ATOM | 13092 | CE | MET | B | 286 | 51.231 | 12.784 | −15.666 | 1.00 | 21.45 | B | C |
| ATOM | 13096 | C | MET | B | 286 | 52.379 | 14.535 | −20.010 | 1.00 | 19.39 | B | C |
| ATOM | 13097 | O | MET | B | 286 | 51.486 | 14.152 | −20.769 | 1.00 | 19.62 | B | O |
| ATOM | 13099 | N | PHE | B | 287 | 53.474 | 15.163 | −20.429 | 1.00 | 19.05 | B | N |
| ATOM | 13100 | CA | PHE | B | 287 | 53.684 | 15.501 | −21.835 | 1.00 | 18.49 | B | C |
| ATOM | 13102 | CB | PHE | B | 287 | 54.845 | 16.499 | −21.969 | 1.00 | 18.88 | B | C |
| ATOM | 13105 | CG | PHE | B | 287 | 54.942 | 17.161 | −23.320 | 1.00 | 19.92 | B | C |
| ATOM | 13106 | CD1 | PHE | B | 287 | 53.805 | 17.632 | −23.977 | 1.00 | 20.75 | B | C |
| ATOM | 13108 | CE1 | PHE | B | 287 | 53.899 | 18.243 | −25.217 | 1.00 | 20.58 | B | C |
| ATOM | 13110 | CZ | PHE | B | 287 | 55.136 | 18.405 | −25.812 | 1.00 | 23.37 | B | C |
| ATOM | 13112 | CE2 | PHE | B | 287 | 56.280 | 17.952 | −25.165 | 1.00 | 23.28 | B | C |
| ATOM | 13114 | CD2 | PHE | B | 287 | 56.178 | 17.338 | −23.925 | 1.00 | 21.35 | B | C |
| ATOM | 13116 | C | PHE | B | 287 | 53.919 | 14.250 | −22.690 | 1.00 | 17.56 | B | C |
| ATOM | 13117 | O | PHE | B | 287 | 53.564 | 14.231 | −23.869 | 1.00 | 17.16 | B | O |
| ATOM | 13119 | N | SER | B | 288 | 54.503 | 13.209 | −22.096 | 1.00 | 16.87 | B | N |
| ATOM | 13120 | CA | SER | B | 288 | 54.594 | 11.903 | −22.757 | 1.00 | 16.53 | B | C |
| ATOM | 13122 | CB | SER | B | 288 | 55.368 | 10.891 | −21.904 | 1.00 | 16.55 | B | C |
| ATOM | 13125 | OG | SER | B | 288 | 56.768 | 11.116 | −21.970 | 1.00 | 16.74 | B | O |
| ATOM | 13127 | C | SER | B | 288 | 53.195 | 11.374 | −23.045 | 1.00 | 16.36 | B | C |
| ATOM | 13128 | O | SER | B | 288 | 52.902 | 10.956 | −24.165 | 1.00 | 16.74 | B | O |
| ATOM | 13130 | N | PHE | B | 289 | 52.331 | 11.406 | −22.034 | 1.00 | 16.08 | B | N |
| ATOM | 13131 | CA | PHE | B | 289 | 50.930 | 11.029 | −22.214 | 1.00 | 15.77 | B | C |
| ATOM | 13133 | CB | PHE | B | 289 | 50.171 | 11.038 | −20.878 | 1.00 | 15.73 | B | C |
| ATOM | 13136 | CG | PHE | B | 289 | 50.321 | 9.767 | −20.087 | 1.00 | 16.79 | B | C |
| ATOM | 13137 | CD1 | PHE | B | 289 | 49.832 | 8.564 | −20.585 | 1.00 | 18.35 | B | C |
| ATOM | 13139 | CE1 | PHE | B | 289 | 49.966 | 7.384 | −19.864 | 1.00 | 17.92 | B | C |
| ATOM | 13141 | CZ | PHE | B | 289 | 50.591 | 7.399 | −18.628 | 1.00 | 18.05 | B | C |
| ATOM | 13143 | CE2 | PHE | B | 289 | 51.081 | 8.591 | −18.119 | 1.00 | 18.22 | B | C |
| ATOM | 13145 | CD2 | PHE | B | 289 | 50.943 | 9.768 | −18.846 | 1.00 | 17.63 | B | C |
| ATOM | 13147 | C | PHE | B | 289 | 50.225 | 11.930 | −23.229 | 1.00 | 15.42 | B | C |
| ATOM | 13148 | O | PHE | B | 289 | 49.437 | 11.445 | −24.039 | 1.00 | 15.46 | B | O |
| ATOM | 13150 | N | VAL | B | 290 | 50.517 | 13.230 | −23.193 | 1.00 | 15.19 | B | N |
| ATOM | 13151 | CA | VAL | B | 290 | 49.908 | 14.179 | −24.133 | 1.00 | 14.81 | B | C |
| ATOM | 13153 | CB | VAL | B | 290 | 50.383 | 15.639 | −23.905 | 1.00 | 14.27 | B | C |
| ATOM | 13155 | CG1 | VAL | B | 290 | 49.790 | 16.565 | −24.954 | 1.00 | 11.43 | B | C |
| ATOM | 13159 | CG2 | VAL | B | 290 | 50.002 | 16.118 | −22.521 | 1.00 | 13.72 | B | C |
| ATOM | 13163 | C | VAL | B | 290 | 50.194 | 13.784 | −25.583 | 1.00 | 15.49 | B | C |
| ATOM | 13164 | O | VAL | B | 290 | 49.276 | 13.740 | −26.402 | 1.00 | 15.62 | B | O |
| ATOM | 13166 | N | THR | B | 291 | 51.455 | 13.476 | −25.893 | 1.00 | 15.62 | B | N |
| ATOM | 13167 | CA | THR | B | 291 | 51.838 | 13.155 | −27.273 | 1.00 | 15.90 | B | C |
| ATOM | 13169 | CB | THR | B | 291 | 53.367 | 12.948 | −27.445 | 1.00 | 15.92 | B | C |
| ATOM | 13171 | OG1 | THR | B | 291 | 53.781 | 11.762 | −26.759 | 1.00 | 17.87 | B | O |
| ATOM | 13173 | CG2 | THR | B | 291 | 54.150 | 14.145 | −26.917 | 1.00 | 16.50 | B | C |
| ATOM | 13177 | C | THR | B | 291 | 51.109 | 11.914 | −27.786 | 1.00 | 15.66 | B | C |
| ATOM | 13178 | O | THR | B | 291 | 50.809 | 11.818 | −28.977 | 1.00 | 15.78 | B | O |
| ATOM | 13180 | N | ILE | B | 292 | 50.824 | 10.977 | −26.882 | 1.00 | 15.54 | B | N |
| ATOM | 13181 | CA | ILE | B | 292 | 50.114 | 9.743 | −27.228 | 1.00 | 15.38 | B | C |
| ATOM | 13183 | CB | ILE | B | 292 | 50.331 | 8.650 | −26.160 | 1.00 | 15.32 | B | C |
| ATOM | 13185 | CG1 | ILE | B | 292 | 51.803 | 8.234 | −26.129 | 1.00 | 13.86 | B | C |
| ATOM | 13188 | CD1 | ILE | B | 292 | 52.103 | 7.171 | −25.111 | 1.00 | 13.47 | B | C |
| ATOM | 13192 | CG2 | ILE | B | 292 | 49.446 | 7.434 | −26.437 | 1.00 | 15.16 | B | C |
| ATOM | 13196 | C | ILE | B | 292 | 48.612 | 9.978 | −27.426 | 1.00 | 15.28 | B | C |
| ATOM | 13197 | O | ILE | B | 292 | 48.023 | 9.462 | −28.379 | 1.00 | 15.27 | B | O |
| ATOM | 13199 | N | ILE | B | 293 | 47.997 | 10.749 | −26.531 | 1.00 | 14.89 | B | N |
| ATOM | 13200 | CA | ILE | B | 293 | 46.580 | 11.079 | −26.672 | 1.00 | 14.80 | B | C |
| ATOM | 13202 | CB | ILE | B | 293 | 46.012 | 11.832 | −25.453 | 1.00 | 14.64 | B | C |
| ATOM | 13204 | CG1 | ILE | B | 293 | 46.094 | 10.979 | −24.184 | 1.00 | 14.55 | B | C |
| ATOM | 13207 | CD1 | ILE | B | 293 | 45.101 | 9.846 | −24.144 | 1.00 | 14.32 | B | C |
| ATOM | 13211 | CG2 | ILE | B | 293 | 44.558 | 12.203 | −25.700 | 1.00 | 14.22 | B | C |
| ATOM | 13215 | C | ILE | B | 293 | 46.394 | 11.938 | −27.916 | 1.00 | 15.23 | B | C |
| ATOM | 13216 | O | ILE | B | 293 | 45.466 | 11.724 | −28.691 | 1.00 | 15.35 | B | O |
| ATOM | 13218 | N | ASP | B | 294 | 47.291 | 12.901 | −28.110 | 1.00 | 15.94 | B | N |
| ATOM | 13219 | CA | ASP | B | 294 | 47.273 | 13.739 | −29.313 | 1.00 | 16.55 | B | C |
| ATOM | 13221 | CB | ASP | B | 294 | 48.491 | 14.682 | −29.346 | 1.00 | 17.12 | B | C |
| ATOM | 13224 | CG | ASP | B | 294 | 48.314 | 15.858 | −30.307 | 1.00 | 17.49 | B | C |
| ATOM | 13225 | OD1 | ASP | B | 294 | 47.164 | 16.220 | −30.634 | 1.00 | 17.71 | B | O |
| ATOM | 13226 | OD2 | ASP | B | 294 | 49.342 | 16.437 | −30.720 | 1.00 | 18.55 | B | O |
| ATOM | 13227 | C | ASP | B | 294 | 47.239 | 12.861 | −30.564 | 1.00 | 16.11 | B | C |

TABLE 8-2-continued

Coordinates for L494P Structure

| | | | | | | | | | | | | |
|---|---|---|---|---|---|---|---|---|---|---|---|---|
| ATOM | 13228 | O | ASP | B | 294 | 46.495 | 13.144 | −31.495 | 1.00 | 16.16 | B | O |
| ATOM | 13230 | N | ASP | B | 295 | 48.029 | 11.788 | −30.567 | 1.00 | 15.75 | B | N |
| ATOM | 13231 | CA | ASP | B | 295 | 48.006 | 10.816 | −31.663 | 1.00 | 15.80 | B | C |
| ATOM | 13233 | CB | ASP | B | 295 | 49.092 | 9.750 | −31.481 | 1.00 | 15.85 | B | C |
| ATOM | 13236 | CG | ASP | B | 295 | 50.462 | 10.218 | −31.932 | 1.00 | 15.72 | B | C |
| ATOM | 13237 | OD1 | ASP | B | 295 | 50.570 | 11.306 | −32.536 | 1.00 | 16.90 | B | O |
| ATOM | 13238 | OD2 | ASP | B | 295 | 51.440 | 9.486 | −31.684 | 1.00 | 13.67 | B | O |
| ATOM | 13239 | C | ASP | B | 295 | 46.650 | 10.132 | −31.797 | 1.00 | 15.95 | B | C |
| ATOM | 13240 | O | ASP | B | 295 | 46.149 | 9.960 | −32.911 | 1.00 | 16.24 | B | O |
| ATOM | 13242 | N | ILE | B | 296 | 46.063 | 9.738 | −30.668 | 1.00 | 15.64 | B | N |
| ATOM | 13243 | CA | ILE | B | 296 | 44.754 | 9.080 | −30.674 | 1.00 | 15.06 | B | C |
| ATOM | 13245 | CB | ILE | B | 296 | 44.270 | 8.738 | −29.251 | 1.00 | 14.85 | B | C |
| ATOM | 13247 | CG1 | ILE | B | 296 | 45.067 | 7.558 | −28.699 | 1.00 | 14.95 | B | C |
| ATOM | 13250 | CD1 | ILE | B | 296 | 44.747 | 7.211 | −27.266 | 1.00 | 15.45 | B | C |
| ATOM | 13254 | CG2 | ILE | B | 296 | 42.795 | 8.378 | −29.263 | 1.00 | 15.55 | B | C |
| ATOM | 13258 | C | ILE | B | 296 | 43.696 | 9.932 | −31.365 | 1.00 | 14.52 | B | C |
| ATOM | 13259 | O | ILE | B | 296 | 43.010 | 9.462 | −32.269 | 1.00 | 14.11 | B | O |
| ATOM | 13261 | N | TYR | B | 297 | 43.579 | 11.185 | −30.941 | 1.00 | 14.55 | B | N |
| ATOM | 13262 | CA | TYR | B | 297 | 42.557 | 12.089 | −31.471 | 1.00 | 14.75 | B | C |
| ATOM | 13264 | CB | TYR | B | 297 | 42.392 | 13.311 | −30.558 | 1.00 | 14.65 | B | C |
| ATOM | 13267 | CG | TYR | B | 297 | 41.605 | 13.051 | −29.288 | 1.00 | 13.97 | B | C |
| ATOM | 13268 | CD1 | TYR | B | 297 | 40.311 | 13.543 | −29.132 | 1.00 | 15.04 | B | C |
| ATOM | 13270 | CE1 | TYR | B | 297 | 39.586 | 13.315 | −27.963 | 1.00 | 15.12 | B | C |
| ATOM | 13272 | CZ | TYR | B | 297 | 40.157 | 12.584 | −26.938 | 1.00 | 16.10 | B | C |
| ATOM | 13273 | OH | TYR | B | 297 | 39.452 | 12.349 | −25.781 | 1.00 | 17.13 | B | O |
| ATOM | 13275 | CE2 | TYR | B | 297 | 41.439 | 12.086 | −27.070 | 1.00 | 16.03 | B | C |
| ATOM | 13277 | CD2 | TYR | B | 297 | 42.156 | 12.322 | −28.240 | 1.00 | 15.06 | B | C |
| ATOM | 13279 | C | TYR | B | 297 | 42.869 | 12.545 | −32.898 | 1.00 | 14.81 | B | C |
| ATOM | 13280 | O | TYR | B | 297 | 41.995 | 12.524 | −33.770 | 1.00 | 14.70 | B | O |
| ATOM | 13282 | N | ASP | B | 298 | 44.117 | 12.946 | −33.125 | 1.00 | 14.76 | B | N |
| ATOM | 13283 | CA | ASP | B | 298 | 44.529 | 13.551 | −34.391 | 1.00 | 14.85 | B | C |
| ATOM | 13285 | CB | ASP | B | 298 | 46.011 | 13.965 | −34.327 | 1.00 | 15.56 | B | C |
| ATOM | 13288 | CG | ASP | B | 298 | 46.436 | 14.845 | −35.495 | 1.00 | 16.94 | B | C |
| ATOM | 13289 | OD1 | ASP | B | 298 | 45.717 | 15.822 | −35.798 | 1.00 | 19.66 | B | O |
| ATOM | 13290 | OD2 | ASP | B | 298 | 47.500 | 14.571 | −36.096 | 1.00 | 16.83 | B | O |
| ATOM | 13291 | C | ASP | B | 298 | 44.298 | 12.621 | −35.579 | 1.00 | 13.99 | B | C |
| ATOM | 13292 | O | ASP | B | 298 | 43.653 | 13.011 | −36.552 | 1.00 | 13.35 | B | O |
| ATOM | 13294 | N | VAL | B | 299 | 44.813 | 11.395 | −35.487 | 1.00 | 13.69 | B | N |
| ATOM | 13295 | CA | VAL | B | 299 | 44.819 | 10.467 | −36.629 | 1.00 | 13.50 | B | C |
| ATOM | 13297 | CB | VAL | B | 299 | 46.263 | 10.201 | −37.129 | 1.00 | 13.48 | B | C |
| ATOM | 13299 | CG1 | VAL | B | 299 | 46.901 | 11.491 | −37.614 | 1.00 | 14.14 | B | C |
| ATOM | 13303 | CG2 | VAL | B | 299 | 47.111 | 9.556 | −36.038 | 1.00 | 13.60 | B | C |
| ATOM | 13307 | C | VAL | B | 299 | 44.139 | 9.112 | −36.404 | 1.00 | 12.90 | B | C |
| ATOM | 13308 | O | VAL | B | 299 | 43.543 | 8.574 | −37.336 | 1.00 | 12.78 | B | O |
| ATOM | 13310 | N | TYR | B | 300 | 44.217 | 8.563 | −35.192 | 1.00 | 12.41 | B | N |
| ATOM | 13311 | CA | TYR | B | 300 | 43.884 | 7.149 | −34.976 | 1.00 | 12.41 | B | C |
| ATOM | 13313 | CB | TYR | B | 300 | 44.802 | 6.549 | −33.911 | 1.00 | 12.27 | B | C |
| ATOM | 13316 | CG | TYR | B | 300 | 44.709 | 5.041 | −33.826 | 1.00 | 12.47 | B | C |
| ATOM | 13317 | CD1 | TYR | B | 300 | 45.090 | 4.241 | −34.898 | 1.00 | 11.58 | B | C |
| ATOM | 13319 | CE1 | TYR | B | 300 | 45.005 | 2.858 | −34.831 | 1.00 | 10.77 | B | C |
| ATOM | 13321 | CZ | TYR | B | 300 | 44.535 | 2.258 | −33.681 | 1.00 | 10.71 | B | C |
| ATOM | 13322 | OH | TYR | B | 300 | 44.451 | O.888 | −33.608 | 1.00 | 11.57 | B | O |
| ATOM | 13324 | CE2 | TYR | B | 300 | 44.150 | 3.027 | −32.602 | 1.00 | 13.01 | B | C |
| ATOM | 13326 | CD2 | TYR | B | 300 | 44.237 | 4.415 | −32.679 | 1.00 | 13.92 | B | C |
| ATOM | 13328 | C | TYR | B | 300 | 42.420 | 6.833 | −34.624 | 1.00 | 12.63 | B | C |
| ATOM | 13329 | O | TYR | B | 300 | 41.804 | 5.979 | −35.259 | 1.00 | 12.91 | B | O |
| ATOM | 13331 | N | GLY | B | 301 | 41.869 | 7.496 | −33.614 | 1.00 | 12.74 | B | N |
| ATOM | 13332 | CA | GLY | B | 301 | 40.531 | 7.156 | −33.118 | 1.00 | 12.64 | B | C |
| ATOM | 13335 | C | GLY | B | 301 | 39.382 | 7.678 | −33.966 | 1.00 | 12.49 | B | C |
| ATOM | 13336 | O | GLY | B | 301 | 39.498 | 8.719 | −34.613 | 1.00 | 12.57 | B | O |
| ATOM | 13338 | N | THR | B | 302 | 38.265 | 6.951 | −33.957 | 1.00 | 12.36 | B | N |
| ATOM | 13339 | CA | THR | B | 302 | 37.033 | 7.433 | −34.579 | 1.00 | 12.60 | B | C |
| ATOM | 13341 | CB | THR | B | 302 | 36.010 | 6.307 | −34.834 | 1.00 | 12.31 | B | C |
| ATOM | 13343 | OG1 | THR | B | 302 | 35.511 | 5.810 | −33.587 | 1.00 | 11.75 | B | O |
| ATOM | 13345 | CG2 | THR | B | 302 | 36.631 | 5.171 | −35.624 | 1.00 | 12.44 | B | C |
| ATOM | 13349 | C | THR | B | 302 | 36.391 | 8.449 | −33.653 | 1.00 | 13.44 | B | C |
| ATOM | 13350 | O | THR | B | 302 | 36.764 | 8.556 | −32.487 | 1.00 | 13.63 | B | O |
| ATOM | 13352 | N | LEU | B | 303 | 35.408 | 9.181 | −34.166 | 1.00 | 14.23 | B | N |
| ATOM | 13353 | CA | LEU | B | 303 | 34.732 | 10.205 | −33.373 | 1.00 | 14.47 | B | C |
| ATOM | 13355 | CB | LEU | B | 303 | 33.758 | 11.004 | −34.239 | 1.00 | 14.69 | B | C |
| ATOM | 13358 | CG | LEU | B | 303 | 33.460 | 12.428 | −33.775 | 1.00 | 14.65 | B | C |
| ATOM | 13360 | CD1 | LEU | B | 303 | 34.684 | 13.310 | −33.959 | 1.00 | 13.80 | B | C |
| ATOM | 13364 | CD2 | LEU | B | 303 | 32.268 | 12.988 | −34.544 | 1.00 | 16.81 | B | C |
| ATOM | 13368 | C | LEU | B | 303 | 33.998 | 9.573 | −32.192 | 1.00 | 14.67 | B | C |
| ATOM | 13369 | O | LEU | B | 303 | 34.065 | 10.082 | −31.075 | 1.00 | 14.67 | B | O |
| ATOM | 13371 | N | ASP | B | 304 | 33.311 | 8.460 | −32.449 | 1.00 | 15.27 | B | N |
| ATOM | 13372 | CA | ASP | B | 304 | 32.630 | 7.694 | −31.395 | 1.00 | 15.80 | B | C |
| ATOM | 13374 | CB | ASP | B | 304 | 31.828 | 6.523 | −31.991 | 1.00 | 16.12 | B | C |

TABLE 8-2-continued

Coordinates for L494P Structure

| | | | | | | | | | | | | |
|---|---|---|---|---|---|---|---|---|---|---|---|---|
| ATOM | 13377 | CG | ASP | B | 304 | 30.537 | 6.966 | −32.668 | 1.00 | 16.23 | B | C |
| ATOM | 13378 | OD1 | ASP | B | 304 | 30.252 | 8.183 | −32.707 | 1.00 | 17.00 | B | O |
| ATOM | 13379 | OD2 | ASP | B | 304 | 29.803 | 6.086 | −33.165 | 1.00 | 15.17 | B | O |
| ATOM | 13380 | C | ASP | B | 304 | 33.617 | 7.155 | −30.356 | 1.00 | 15.75 | B | C |
| ATOM | 13381 | O | ASP | B | 304 | 33.332 | 7.168 | −29.154 | 1.00 | 15.68 | B | O |
| ATOM | 13383 | N | GLU | B | 305 | 34.765 | 6.669 | −30.823 | 1.00 | 15.44 | B | N |
| ATOM | 13384 | CA | GLU | B | 305 | 35.823 | 6.207 | −29.926 | 1.00 | 15.31 | B | C |
| ATOM | 13386 | CB | GLU | B | 305 | 36.965 | 5.564 | −30.713 | 1.00 | 15.57 | B | C |
| ATOM | 13389 | CG | GLU | B | 305 | 36.689 | 4.138 | −31.162 | 1.00 | 15.98 | B | C |
| ATOM | 13392 | CD | GLU | B | 305 | 37.800 | 3.581 | −32.027 | 1.00 | 16.46 | B | C |
| ATOM | 13393 | OE1 | GLU | B | 305 | 38.399 | 4.350 | −32.807 | 1.00 | 17.84 | B | O |
| ATOM | 13394 | OE2 | GLU | B | 305 | 38.076 | 2.369 | −31.936 | 1.00 | 17.97 | B | O |
| ATOM | 13395 | C | GLU | B | 305 | 36.366 | 7.357 | −29.088 | 1.00 | 15.04 | B | C |
| ATOM | 13396 | O | GLU | B | 305 | 36.621 | 7.190 | −27.895 | 1.00 | 15.15 | B | O |
| ATOM | 13398 | N | LEU | B | 306 | 36.536 | 8.518 | −29.720 | 1.00 | 14.77 | B | N |
| ATOM | 13399 | CA | LEU | B | 306 | 37.040 | 9.715 | −29.040 | 1.00 | 13.94 | B | C |
| ATOM | 13401 | CB | LEU | B | 306 | 37.447 | 10.778 | −30.064 | 1.00 | 13.32 | B | C |
| ATOM | 13404 | CG | LEU | B | 306 | 38.667 | 10.392 | −30.903 | 1.00 | 11.95 | B | C |
| ATOM | 13406 | CD1 | LEU | B | 306 | 38.892 | 11.372 | −32.041 | 1.00 | 9.49 | B | C |
| ATOM | 13410 | CD2 | LEU | B | 306 | 39.897 | 10.287 | −30.018 | 1.00 | 12.30 | B | C |
| ATOM | 13414 | C | LEU | B | 306 | 36.024 | 10.283 | −28.050 | 1.00 | 14.05 | B | C |
| ATOM | 13415 | O | LEU | B | 306 | 36.405 | 10.817 | −27.007 | 1.00 | 13.84 | B | O |
| ATOM | 13417 | N | GLU | B | 307 | 34.739 | 10.159 | −28.374 | 1.00 | 14.32 | B | N |
| ATOM | 13418 | CA | GLU | B | 307 | 33.672 | 10.542 | −27.448 | 1.00 | 14.91 | B | C |
| ATOM | 13420 | CB | GLU | B | 307 | 32.296 | 10.437 | −28.119 | 1.00 | 15.01 | B | C |
| ATOM | 13423 | CG | GLU | B | 307 | 31.885 | 11.687 | −28.890 | 1.00 | 16.39 | B | C |
| ATOM | 13426 | CD | GLU | B | 307 | 31.587 | 12.875 | −27.985 | 1.00 | 18.17 | B | C |
| ATOM | 13427 | OE1 | GLU | B | 307 | 31.715 | 14.025 | −28.455 | 1.00 | 18.84 | B | O |
| ATOM | 13428 | OE2 | GLU | B | 307 | 31.227 | 12.662 | −26.805 | 1.00 | 19.10 | B | O |
| ATOM | 13429 | C | GLU | B | 307 | 33.695 | 9.709 | −26.164 | 1.00 | 15.05 | B | C |
| ATOM | 13430 | O | GLU | B | 307 | 33.545 | 10.256 | −25.070 | 1.00 | 15.50 | B | O |
| ATOM | 13432 | N | LEU | B | 308 | 33.883 | 8.395 | −26.299 | 1.00 | 14.90 | B | N |
| ATOM | 13433 | CA | LEU | B | 308 | 33.941 | 7.501 | −25.136 | 1.00 | 14.90 | B | C |
| ATOM | 13435 | CB | LEU | B | 308 | 33.975 | 6.027 | −25.562 | 1.00 | 15.03 | B | C |
| ATOM | 13438 | CG | LEU | B | 308 | 32.705 | 5.409 | −26.151 | 1.00 | 15.09 | B | C |
| ATOM | 13440 | CD1 | LEU | B | 308 | 32.922 | 3.918 | −26.391 | 1.00 | 12.37 | B | C |
| ATOM | 13444 | CD2 | LEU | B | 308 | 31.503 | 5.640 | −25.244 | 1.00 | 14.58 | B | C |
| ATOM | 13448 | C | LEU | B | 308 | 35.144 | 7.794 | −24.244 | 1.00 | 14.76 | B | C |
| ATOM | 13449 | O | LEU | B | 308 | 35.047 | 7.693 | −23.023 | 1.00 | 14.83 | B | O |
| ATOM | 13451 | N | PHE | B | 309 | 36.272 | 8.148 | −24.854 | 1.00 | 14.97 | B | N |
| ATOM | 13452 | CA | PHE | B | 309 | 37.482 | 8.481 | −24.102 | 1.00 | 15.23 | B | C |
| ATOM | 13454 | CB | PHE | B | 309 | 38.701 | 8.540 | −25.030 | 1.00 | 14.93 | B | C |
| ATOM | 13457 | CG | PHE | B | 309 | 40.014 | 8.476 | −24.303 | 1.00 | 12.81 | B | C |
| ATOM | 13458 | CD1 | PHE | B | 309 | 40.712 | 7.280 | −24.213 | 1.00 | 10.56 | B | C |
| ATOM | 13460 | CE1 | PHE | B | 309 | 41.919 | 7.212 | −23.537 | 1.00 | 9.68 | B | C |
| ATOM | 13462 | CZ | PHE | B | 309 | 42.440 | 8.345 | −22.941 | 1.00 | 10.55 | B | C |
| ATOM | 13464 | CE2 | PHE | B | 309 | 41.752 | 9.550 | −23.020 | 1.00 | 11.50 | B | C |
| ATOM | 13466 | CD2 | PHE | B | 309 | 40.547 | 9.610 | −23.698 | 1.00 | 11.86 | B | C |
| ATOM | 13468 | C | PHE | B | 309 | 37.318 | 9.815 | −23.361 | 1.00 | 16.02 | B | C |
| ATOM | 13469 | O | PHE | B | 309 | 37.597 | 9.905 | −22.162 | 1.00 | 16.16 | B | O |
| ATOM | 13471 | N | THR | B | 310 | 36.876 | 10.843 | −24.083 | 1.00 | 16.42 | B | N |
| ATOM | 13472 | CA | THR | B | 310 | 36.594 | 12.144 | −23.484 | 1.00 | 16.93 | B | C |
| ATOM | 13474 | CB | THR | B | 310 | 35.941 | 13.101 | −24.499 | 1.00 | 17.11 | B | C |
| ATOM | 13476 | OG1 | THR | B | 310 | 36.753 | 13.182 | −25.676 | 1.00 | 18.04 | B | O |
| ATOM | 13478 | CG2 | THR | B | 310 | 35.775 | 14.490 | −23.898 | 1.00 | 17.27 | B | C |
| ATOM | 13482 | C | THR | B | 310 | 35.645 | 11.970 | −22.306 | 1.00 | 17.22 | B | C |
| ATOM | 13483 | O | THR | B | 310 | 35.893 | 12.475 | −21.213 | 1.00 | 17.31 | B | O |
| ATOM | 13485 | N | ASP | B | 311 | 34.560 | 11.242 | −22.549 | 1.00 | 17.64 | B | N |
| ATOM | 13486 | CA | ASP | B | 311 | 33.559 | 10.957 | −21.529 | 1.00 | 18.02 | B | C |
| ATOM | 13488 | CB | ASP | B | 311 | 32.432 | 10.119 | −22.136 | 1.00 | 17.98 | B | C |
| ATOM | 13491 | CG | ASP | B | 311 | 31.441 | 9.638 | −21.103 | 1.00 | 18.70 | B | C |
| ATOM | 13492 | OD1 | ASP | B | 311 | 30.851 | 10.486 | −20.399 | 1.00 | 19.29 | B | O |
| ATOM | 13493 | OD2 | ASP | B | 311 | 31.251 | 8.407 | −20.997 | 1.00 | 21.03 | B | O |
| ATOM | 13494 | C | ASP | B | 311 | 34.160 | 10.228 | −20.326 | 1.00 | 18.33 | B | C |
| ATOM | 13495 | O | ASP | B | 311 | 33.934 | 10.624 | −19.182 | 1.00 | 18.39 | B | O |
| ATOM | 13497 | N | ALA | B | 312 | 34.925 | 9.170 | −20.597 | 1.00 | 18.50 | B | N |
| ATOM | 13498 | CA | ALA | B | 312 | 35.524 | 8.335 | −19.548 | 1.00 | 18.23 | B | C |
| ATOM | 13500 | CB | ALA | B | 312 | 36.268 | 7.159 | −20.168 | 1.00 | 18.14 | B | C |
| ATOM | 13504 | C | ALA | B | 312 | 36.456 | 9.117 | −18.625 | 1.00 | 18.16 | B | C |
| ATOM | 13505 | O | ALA | B | 312 | 36.513 | 8.845 | −17.426 | 1.00 | 18.48 | B | O |
| ATOM | 13507 | N | VAL | B | 313 | 37.183 | 10.079 | −19.189 | 1.00 | 18.03 | B | N |
| ATOM | 13508 | CA | VAL | B | 313 | 38.050 | 10.960 | −18.405 | 1.00 | 18.31 | B | C |
| ATOM | 13510 | CB | VAL | B | 313 | 38.965 | 11.805 | −19.326 | 1.00 | 18.52 | B | C |
| ATOM | 13512 | CG1 | VAL | B | 313 | 40.105 | 10.946 | −19.870 | 1.00 | 18.57 | B | C |
| ATOM | 13516 | CG2 | VAL | B | 313 | 39.515 | 13.021 | −18.588 | 1.00 | 18.51 | B | C |
| ATOM | 13520 | C | VAL | B | 313 | 37.240 | 11.882 | −17.486 | 1.00 | 18.58 | B | C |
| ATOM | 13521 | O | VAL | B | 313 | 37.553 | 12.016 | −16.303 | 1.00 | 18.04 | B | O |
| ATOM | 13523 | N | GLU | B | 314 | 36.198 | 12.504 | −18.033 | 1.00 | 19.37 | B | N |

TABLE 8-2-continued

Coordinates for L494P Structure

| | | | | | | | | | | | | |
|---|---|---|---|---|---|---|---|---|---|---|---|---|
| ATOM | 13524 | CA | GLU | B | 314 | 35.321 | 13.395 | −17.258 | 1.00 | 20.06 | B | C |
| ATOM | 13526 | CB | GLU | B | 314 | 34.224 | 13.987 | −18.154 | 1.00 | 20.50 | B | C |
| ATOM | 13529 | CG | GLU | B | 314 | 34.697 | 15.089 | −19.102 | 1.00 | 21.76 | B | C |
| ATOM | 13532 | CD | GLU | B | 314 | 33.609 | 15.550 | −20.064 | 1.00 | 23.96 | B | C |
| ATOM | 13533 | OE1 | GLU | B | 314 | 33.914 | 16.363 | −20.962 | 1.00 | 23.97 | B | O |
| ATOM | 13534 | OE2 | GLU | B | 314 | 32.449 | 15.100 | −19.929 | 1.00 | 25.34 | B | O |
| ATOM | 13535 | C | GLU | B | 314 | 34.667 | 12.709 | −16.053 | 1.00 | 19.90 | B | C |
| ATOM | 13536 | O | GLU | B | 314 | 34.342 | 13.369 | −15.068 | 1.00 | 20.36 | B | O |
| ATOM | 13538 | N | ARG | B | 315 | 34.463 | 11.398 | −16.141 | 1.00 | 19.78 | B | N |
| ATOM | 13539 | CA | ARG | B | 315 | 33.863 | 10.626 | −15.054 | 1.00 | 20.09 | B | C |
| ATOM | 13541 | CB | ARG | B | 315 | 33.116 | 9.420 | −15.616 | 1.00 | 20.83 | B | C |
| ATOM | 13544 | CG | ARG | B | 315 | 31.940 | 9.789 | −16.488 | 1.00 | 23.42 | B | C |
| ATOM | 13547 | CD | ARG | B | 315 | 31.282 | 8.560 | −17.080 | 1.00 | 27.26 | B | C |
| ATOM | 13550 | NE | ARG | B | 315 | 30.102 | 8.922 | −17.863 | 1.00 | 32.39 | B | N |
| ATOM | 13552 | CZ | ARG | B | 315 | 28.915 | 9.250 | −17.351 | 1.00 | 35.04 | B | C |
| ATOM | 13553 | NH1 | ARG | B | 315 | 28.712 | 9.262 | −16.035 | 1.00 | 36.54 | B | N |
| ATOM | 13556 | NH2 | ARG | B | 315 | 27.914 | 9.567 | −18.168 | 1.00 | 34.69 | B | N |
| ATOM | 13559 | C | ARG | B | 315 | 34.901 | 10.145 | −14.049 | 1.00 | 19.51 | B | C |
| ATOM | 13560 | O | ARG | B | 315 | 34.642 | 10.126 | −12.845 | 1.00 | 19.73 | B | O |
| ATOM | 13562 | N | TRP | B | 316 | 36.065 | 9.741 | −14.553 | 1.00 | 18.77 | B | N |
| ATOM | 13563 | CA | TRP | B | 316 | 37.150 | 9.218 | −13.725 | 1.00 | 17.72 | B | C |
| ATOM | 13565 | CB | TRP | B | 316 | 37.694 | 10.308 | −12.794 | 1.00 | 17.03 | B | C |
| ATOM | 13568 | CG | TRP | B | 316 | 39.112 | 10.081 | −12.398 | 1.00 | 14.29 | B | C |
| ATOM | 13569 | CD1 | TRP | B | 316 | 39.566 | 9.639 | −11.195 | 1.00 | 13.02 | B | C |
| ATOM | 13571 | NE1 | TRP | B | 316 | 40.934 | 9.547 | −11.211 | 1.00 | 12.01 | B | N |
| ATOM | 13573 | CE2 | TRP | B | 316 | 41.389 | 9.930 | −12.443 | 1.00 | 11.63 | B | C |
| ATOM | 13574 | CD2 | TRP | B | 316 | 40.267 | 10.271 | −13.218 | 1.00 | 12.10 | B | C |
| ATOM | 13575 | CE3 | TRP | B | 316 | 40.462 | 10.702 | −14.533 | 1.00 | 13.74 | B | C |
| ATOM | 13577 | CZ3 | TRP | B | 316 | 41.752 | 10.778 | −15.024 | 1.00 | 13.08 | B | C |
| ATOM | 13579 | CH2 | TRP | B | 316 | 42.848 | 10.432 | −14.228 | 1.00 | 13.51 | B | C |
| ATOM | 13581 | CZ2 | TRP | B | 316 | 42.688 | 10.004 | −12.937 | 1.00 | 13.12 | B | C |
| ATOM | 13583 | C | TRP | B | 316 | 36.678 | 7.995 | −12.940 | 1.00 | 17.90 | B | C |
| ATOM | 13584 | O | TRP | B | 316 | 36.859 | 7.909 | −11.727 | 1.00 | 17.86 | B | O |
| ATOM | 13586 | N | ASP | B | 317 | 36.073 | 7.053 | −13.658 | 1.00 | 18.19 | B | N |
| ATOM | 13587 | CA | ASP | B | 317 | 35.487 | 5.863 | −13.057 | 1.00 | 18.63 | B | C |
| ATOM | 13589 | CB | ASP | B | 317 | 33.983 | 5.825 | −13.354 | 1.00 | 18.49 | B | C |
| ATOM | 13592 | CG | ASP | B | 317 | 33.270 | 4.671 | −12.664 | 1.00 | 18.45 | B | C |
| ATOM | 13593 | OD1 | ASP | B | 317 | 33.789 | 4.140 | −11.659 | 1.00 | 17.90 | B | O |
| ATOM | 13594 | OD2 | ASP | B | 317 | 32.173 | 4.298 | −13.129 | 1.00 | 19.26 | B | O |
| ATOM | 13595 | C | ASP | B | 317 | 36.177 | 4.618 | −13.605 | 1.00 | 19.33 | B | C |
| ATOM | 13596 | O | ASP | B | 317 | 35.899 | 4.186 | −14.723 | 1.00 | 19.83 | B | O |
| ATOM | 13598 | N | VAL | B | 318 | 37.072 | 4.040 | −12.808 | 1.00 | 20.11 | B | N |
| ATOM | 13599 | CA | VAL | B | 318 | 37.836 | 2.857 | −13.222 | 1.00 | 20.65 | B | C |
| ATOM | 13601 | CB | VAL | B | 318 | 38.983 | 2.555 | −12.231 | 1.00 | 20.75 | B | C |
| ATOM | 13603 | CG1 | VAL | B | 318 | 40.006 | 1.618 | −12.859 | 1.00 | 20.37 | B | C |
| ATOM | 13607 | CG2 | VAL | B | 318 | 38.434 | 1.984 | −10.929 | 1.00 | 21.89 | B | C |
| ATOM | 13611 | C | VAL | B | 318 | 36.973 | 1.601 | −13.381 | 1.00 | 21.11 | B | C |
| ATOM | 13612 | O | VAL | B | 318 | 37.433 | 0.607 | −13.938 | 1.00 | 21.49 | B | O |
| ATOM | 13614 | N | ASN | B | 319 | 35.739 | 1.640 | −12.879 | 1.00 | 21.87 | B | N |
| ATOM | 13615 | CA | ASN | B | 319 | 34.769 | 0.561 | −13.103 | 1.00 | 22.19 | B | C |
| ATOM | 13617 | CB | ASN | B | 319 | 33.661 | 0.605 | −12.049 | 1.00 | 22.01 | B | C |
| ATOM | 13620 | CG | ASN | B | 319 | 34.184 | 0.354 | −10.645 | 1.00 | 23.10 | B | C |
| ATOM | 13621 | OD1 | ASN | B | 319 | 34.633 | −0.747 | −10.323 | 1.00 | 24.06 | B | O |
| ATOM | 13622 | ND2 | ASN | B | 319 | 34.126 | 1.379 | −9.801 | 1.00 | 22.91 | B | N |
| ATOM | 13625 | C | ASN | B | 319 | 34.157 | 0.624 | −14.503 | 1.00 | 22.52 | B | C |
| ATOM | 13626 | O | ASN | B | 319 | 33.797 | −0.407 | −15.071 | 1.00 | 22.62 | B | O |
| ATOM | 13628 | N | ALA | B | 320 | 34.057 | 1.833 | −15.057 | 1.00 | 22.93 | B | N |
| ATOM | 13629 | CA | ALA | B | 320 | 33.528 | 2.040 | −16.411 | 1.00 | 23.46 | B | C |
| ATOM | 13631 | CB | ALA | B | 320 | 32.801 | 3.381 | −16.485 | 1.00 | 23.82 | B | C |
| ATOM | 13635 | C | ALA | B | 320 | 34.615 | 1.966 | −17.495 | 1.00 | 23.78 | B | C |
| ATOM | 13636 | O | ALA | B | 320 | 34.456 | 2.528 | −18.579 | 1.00 | 23.85 | B | O |
| ATOM | 13638 | N | ILE | B | 321 | 35.714 | 1.275 | −17.197 | 1.00 | 24.14 | B | N |
| ATOM | 13639 | CA | ILE | B | 321 | 36.796 | 1.063 | −18.159 | 1.00 | 23.92 | B | C |
| ATOM | 13641 | CB | ILE | B | 321 | 38.086 | 0.529 | −17.457 | 1.00 | 24.05 | B | C |
| ATOM | 13643 | CG1 | ILE | B | 321 | 39.279 | 0.540 | −18.416 | 1.00 | 23.88 | B | C |
| ATOM | 13646 | CD1 | ILE | B | 321 | 40.563 | 0.038 | −17.785 | 1.00 | 24.06 | B | C |
| ATOM | 13650 | CG2 | ILE | B | 321 | 37.873 | −0.878 | −16.884 | 1.00 | 23.28 | B | C |
| ATOM | 13654 | C | ILE | B | 321 | 36.356 | 0.103 | −19.267 | 1.00 | 23.68 | B | C |
| ATOM | 13655 | O | ILE | B | 321 | 36.578 | 0.379 | −20.445 | 1.00 | 23.41 | B | O |
| ATOM | 13657 | N | ASN | B | 322 | 35.706 | −0.999 | −18.882 | 1.00 | 23.66 | B | N |
| ATOM | 13658 | CA | ASN | B | 322 | 35.280 | −2.050 | −19.823 | 1.00 | 23.61 | B | C |
| ATOM | 13660 | CB | ASN | B | 322 | 34.503 | −3.165 | −19.093 | 1.00 | 23.73 | B | C |
| ATOM | 13663 | CG | ASN | B | 322 | 35.413 | −4.227 | −18.468 | 1.00 | 23.75 | B | C |
| ATOM | 13664 | OD1 | ASN | B | 322 | 36.561 | −4.414 | −18.877 | 1.00 | 23.33 | B | O |
| ATOM | 13665 | ND2 | ASN | B | 322 | 34.885 | −4.939 | −17.479 | 1.00 | 22.49 | B | N |
| ATOM | 13668 | C | ASN | B | 322 | 34.434 | −1.539 | −20.992 | 1.00 | 23.44 | B | C |
| ATOM | 13669 | O | ASN | B | 322 | 34.330 | −2.207 | −22.021 | 1.00 | 23.62 | B | O |
| ATOM | 13671 | N | ASP | B | 323 | 33.828 | −0.365 | −20.826 | 1.00 | 23.09 | B | N |

TABLE 8-2-continued

Coordinates for L494P Structure

| | | | | | | | | | | | | |
|---|---|---|---|---|---|---|---|---|---|---|---|---|
| ATOM | 13672 | CA | ASP | B | 323 | 33.050 | 0.269 | −21.889 | 1.00 | 22.51 | B | C |
| ATOM | 13674 | CB | ASP | B | 323 | 32.249 | 1.458 | −21.328 | 1.00 | 23.08 | B | C |
| ATOM | 13677 | CG | ASP | B | 323 | 31.293 | 1.056 | −20.201 | 1.00 | 23.77 | B | C |
| ATOM | 13678 | OD1 | ASP | B | 323 | 30.528 | 0.081 | −20.377 | 1.00 | 23.68 | B | O |
| ATOM | 13679 | OD2 | ASP | B | 323 | 31.302 | 1.725 | −19.143 | 1.00 | 23.10 | B | O |
| ATOM | 13680 | C | ASP | B | 323 | 33.937 | 0.740 | −23.051 | 1.00 | 21.15 | B | C |
| ATOM | 13681 | O | ASP | B | 323 | 33.467 | 0.856 | −24.182 | 1.00 | 20.67 | B | O |
| ATOM | 13683 | N | LEU | B | 324 | 35.214 | 1.001 | −22.767 | 1.00 | 20.28 | B | N |
| ATOM | 13684 | CA | LEU | B | 324 | 36.155 | 1.517 | −23.766 | 1.00 | 19.81 | B | C |
| ATOM | 13686 | CB | LEU | B | 324 | 37.278 | 2.299 | −23.075 | 1.00 | 19.75 | B | C |
| ATOM | 13689 | CG | LEU | B | 324 | 36.855 | 3.536 | −22.280 | 1.00 | 19.79 | B | C |
| ATOM | 13691 | CD1 | LEU | B | 324 | 38.033 | 4.107 | −21.504 | 1.00 | 18.72 | B | C |
| ATOM | 13695 | CD2 | LEU | B | 324 | 36.257 | 4.590 | −23.200 | 1.00 | 19.38 | B | C |
| ATOM | 13699 | C | LEU | B | 324 | 36.775 | 0.408 | −24.620 | 1.00 | 19.40 | B | C |
| ATOM | 13700 | O | LEU | B | 324 | 36.895 | −0.731 | −24.164 | 1.00 | 19.28 | B | O |
| ATOM | 13702 | N | PRO | B | 325 | 37.186 | 0.743 | −25.860 | 1.00 | 18.93 | B | N |
| ATOM | 13703 | CA | PRO | B | 325 | 37.864 | −0.226 | −26.720 | 1.00 | 18.63 | B | C |
| ATOM | 13705 | CB | PRO | B | 325 | 37.910 | 0.480 | −28.077 | 1.00 | 18.57 | B | C |
| ATOM | 13708 | CG | PRO | B | 325 | 37.894 | 1.915 | −27.751 | 1.00 | 18.71 | B | C |
| ATOM | 13711 | CD | PRO | B | 325 | 37.036 | 2.048 | −26.528 | 1.00 | 18.93 | B | C |
| ATOM | 13714 | C | PRO | B | 325 | 39.274 | −0.545 | −26.227 | 1.00 | 18.43 | B | C |
| ATOM | 13715 | O | PRO | B | 325 | 39.858 | 0.231 | −25.468 | 1.00 | 17.77 | B | O |
| ATOM | 13716 | N | ASP | B | 326 | 39.808 | −1.676 | −26.678 | 1.00 | 18.61 | B | N |
| ATOM | 13717 | CA | ASP | B | 326 | 41.035 | −2.248 | −26.113 | 1.00 | 18.76 | B | C |
| ATOM | 13719 | CB | ASP | B | 326 | 41.455 | −3.501 | −26.894 | 1.00 | 19.31 | B | C |
| ATOM | 13722 | CG | ASP | B | 326 | 40.570 | −4.708 | −26.599 | 1.00 | 20.22 | B | C |
| ATOM | 13723 | OD1 | ASP | B | 326 | 39.894 | −4.730 | −25.545 | 1.00 | 21.20 | B | O |
| ATOM | 13724 | OD2 | ASP | B | 326 | 40.565 | −5.649 | −27.422 | 1.00 | 21.66 | B | O |
| ATOM | 13725 | C | ASP | B | 326 | 42.211 | −1.277 | −26.015 | 1.00 | 18.24 | B | C |
| ATOM | 13726 | O | ASP | B | 326 | 42.806 | −1.145 | −24.948 | 1.00 | 18.18 | B | O |
| ATOM | 13728 | N | TYR | B | 327 | 42.547 | −0.599 | −27.109 | 1.00 | 17.94 | B | N |
| ATOM | 13729 | CA | TYR | B | 327 | 43.695 | 0.316 | −27.094 | 1.00 | 17.68 | B | C |
| ATOM | 13731 | CB | TYR | B | 327 | 44.061 | 0.800 | −28.506 | 1.00 | 17.63 | B | C |
| ATOM | 13734 | CG | TYR | B | 327 | 43.152 | 1.858 | −29.101 | 1.00 | 17.30 | B | C |
| ATOM | 13735 | CD1 | TYR | B | 327 | 41.980 | 1.506 | −29.768 | 1.00 | 17.77 | B | C |
| ATOM | 13737 | CE1 | TYR | B | 327 | 41.151 | 2.475 | −30.328 | 1.00 | 17.15 | B | C |
| ATOM | 13739 | CZ | TYR | B | 327 | 41.497 | 3.811 | −30.233 | 1.00 | 17.82 | B | C |
| ATOM | 13740 | OH | TYR | B | 327 | 40.684 | 4.774 | −30.783 | 1.00 | 19.10 | B | O |
| ATOM | 13742 | CE2 | TYR | B | 327 | 42.659 | 4.185 | −29.584 | 1.00 | 17.85 | B | C |
| ATOM | 13744 | CD2 | TYR | B | 327 | 43.482 | 3.208 | −29.027 | 1.00 | 17.88 | B | C |
| ATOM | 13746 | C | TYR | B | 327 | 43.474 | 1.497 | −26.149 | 1.00 | 17.55 | B | C |
| ATOM | 13747 | O | TYR | B | 327 | 44.435 | 2.025 | −25.587 | 1.00 | 17.97 | B | O |
| ATOM | 13749 | N | MET | B | 328 | 42.215 | 1.894 | −25.966 | 1.00 | 17.24 | B | N |
| ATOM | 13750 | CA | MET | B | 328 | 41.866 | 2.972 | −25.033 | 1.00 | 16.88 | B | C |
| ATOM | 13752 | CB | MET | B | 328 | 40.511 | 3.582 | −25.390 | 1.00 | 16.72 | B | C |
| ATOM | 13755 | CG | MET | B | 328 | 40.549 | 4.380 | −26.674 | 1.00 | 16.24 | B | C |
| ATOM | 13758 | SD | MET | B | 328 | 39.002 | 5.199 | −27.066 | 1.00 | 13.82 | B | S |
| ATOM | 13759 | CE | MET | B | 328 | 39.582 | 6.357 | −28.303 | 1.00 | 13.73 | B | C |
| ATOM | 13763 | C | MET | B | 328 | 41.865 | 2.507 | −23.578 | 1.00 | 16.65 | B | C |
| ATOM | 13764 | O | MET | B | 328 | 42.227 | 3.274 | −22.688 | 1.00 | 16.22 | B | O |
| ATOM | 13766 | N | LYS | B | 329 | 41.449 | 1.262 | −23.342 | 1.00 | 16.55 | B | N |
| ATOM | 13767 | CA | LYS | B | 329 | 41.524 | 0.661 | −22.008 | 1.00 | 16.67 | B | C |
| ATOM | 13769 | CB | LYS | B | 329 | 41.107 | −0.813 | −22.045 | 1.00 | 17.17 | B | C |
| ATOM | 13772 | CG | LYS | B | 329 | 39.614 | −1.076 | −22.199 | 1.00 | 19.24 | B | C |
| ATOM | 13775 | CD | LYS | B | 329 | 39.370 | −2.516 | −22.662 | 1.00 | 21.98 | B | C |
| ATOM | 13778 | CE | LYS | B | 329 | 38.095 | −3.116 | −22.093 | 1.00 | 23.19 | B | C |
| ATOM | 13781 | NZ | LYS | B | 329 | 37.911 | −4.532 | −22.538 | 1.00 | 24.02 | B | N |
| ATOM | 13785 | C | LYS | B | 329 | 42.946 | 0.754 | −21.469 | 1.00 | 16.07 | B | C |
| ATOM | 13786 | O | LYS | B | 329 | 43.177 | 1.281 | −20.381 | 1.00 | 16.02 | B | O |
| ATOM | 13788 | N | LEU | B | 330 | 43.891 | 0.238 | −22.248 | 1.00 | 15.71 | B | N |
| ATOM | 13789 | CA | LEU | B | 330 | 45.300 | 0.211 | −21.859 | 1.00 | 15.48 | B | C |
| ATOM | 13791 | CB | LEU | B | 330 | 46.118 | −0.574 | −22.889 | 1.00 | 15.59 | B | C |
| ATOM | 13794 | CG | LEU | B | 330 | 47.578 | −0.875 | −22.540 | 1.00 | 15.37 | B | C |
| ATOM | 13796 | CD1 | LEU | B | 330 | 47.655 | −1.862 | −21.387 | 1.00 | 15.91 | B | C |
| ATOM | 13800 | CD2 | LEU | B | 330 | 48.314 | −1.411 | −23.758 | 1.00 | 14.02 | B | C |
| ATOM | 13804 | C | LEU | B | 330 | 45.868 | 1.622 | −21.710 | 1.00 | 15.18 | B | C |
| ATOM | 13805 | O | LEU | B | 330 | 46.670 | 1.876 | −20.812 | 1.00 | 15.28 | B | O |
| ATOM | 13807 | N | CYS | B | 331 | 45.453 | 2.529 | −22.592 | 1.00 | 14.49 | B | N |
| ATOM | 13808 | CA | CYS | B | 331 | 45.875 | 3.929 | −22.525 | 1.00 | 13.98 | B | C |
| ATOM | 13810 | CB | CYS | B | 331 | 45.494 | 4.665 | −23.814 | 1.00 | 14.01 | B | C |
| ATOM | 13813 | SG | CYS | B | 331 | 45.852 | 6.448 | −23.790 | 1.00 | 16.06 | B | S |
| ATOM | 13815 | C | CYS | B | 331 | 45.265 | 4.652 | −21.321 | 1.00 | 13.11 | B | C |
| ATOM | 13816 | O | CYS | B | 331 | 45.969 | 5.344 | −20.581 | 1.00 | 12.31 | B | O |
| ATOM | 13818 | N | PHE | B | 332 | 43.956 | 4.485 | −21.137 | 1.00 | 12.49 | B | N |
| ATOM | 13819 | CA | PHE | B | 332 | 43.220 | 5.171 | −20.074 | 1.00 | 12.12 | B | C |
| ATOM | 13821 | CB | PHE | B | 332 | 41.712 | 4.935 | −20.229 | 1.00 | 11.94 | B | C |
| ATOM | 13824 | CG | PHE | B | 332 | 40.889 | 5.500 | −19.105 | 1.00 | 11.71 | B | C |
| ATOM | 13825 | CD1 | PHE | B | 332 | 40.586 | 6.852 | −19.062 | 1.00 | 11.58 | B | C |

TABLE 8-2-continued

Coordinates for L494P Structure

| | | | | | | | | | | | | |
|---|---|---|---|---|---|---|---|---|---|---|---|---|
| ATOM | 13827 | CE1 | PHE | B | 332 | 39.831 | 7.379 | −18.023 | 1.00 | 12.01 | B | C |
| ATOM | 13829 | CZ | PHE | B | 332 | 39.369 | 6.550 | −17.013 | 1.00 | 11.84 | B | C |
| ATOM | 13831 | CE2 | PHE | B | 332 | 39.665 | 5.199 | −17.044 | 1.00 | 12.39 | B | C |
| ATOM | 13833 | CD2 | PHE | B | 332 | 40.423 | 4.680 | −18.087 | 1.00 | 12.36 | B | C |
| ATOM | 13835 | C | PHE | B | 332 | 43.673 | 4.745 | −18.674 | 1.00 | 12.03 | B | C |
| ATOM | 13836 | O | PHE | B | 332 | 43.919 | 5.593 | −17.812 | 1.00 | 11.73 | B | O |
| ATOM | 13838 | N | LEU | B | 333 | 43.778 | 3.435 | −18.455 | 1.00 | 11.78 | B | N |
| ATOM | 13839 | CA | LEU | B | 333 | 44.160 | 2.893 | −17.144 | 1.00 | 11.25 | B | C |
| ATOM | 13841 | CB | LEU | B | 333 | 43.998 | 1.365 | −17.122 | 1.00 | 10.70 | B | C |
| ATOM | 13844 | CG | LEU | B | 333 | 44.058 | 0.648 | −15.767 | 1.00 | 8.41 | B | C |
| ATOM | 13846 | CD1 | LEU | B | 333 | 43.018 | 1.170 | −14.793 | 1.00 | 5.66 | B | C |
| ATOM | 13850 | CD2 | LEU | B | 333 | 43.874 | −0.840 | −15.966 | 1.00 | 6.27 | B | C |
| ATOM | 13854 | C | LEU | B | 333 | 45.588 | 3.282 | −16.761 | 1.00 | 11.55 | B | C |
| ATOM | 13855 | O | LEU | B | 333 | 45.898 | 3.420 | −15.577 | 1.00 | 11.81 | B | O |
| ATOM | 13857 | N | ALA | B | 334 | 46.449 | 3.462 | −17.762 | 1.00 | 11.79 | B | N |
| ATOM | 13858 | CA | ALA | B | 334 | 47.815 | 3.935 | −17.539 | 1.00 | 11.84 | B | C |
| ATOM | 13860 | CB | ALA | B | 334 | 48.625 | 3.847 | −18.825 | 1.00 | 11.68 | B | C |
| ATOM | 13864 | C | ALA | B | 334 | 47.809 | 5.369 | −17.013 | 1.00 | 12.02 | B | C |
| ATOM | 13865 | O | ALA | B | 334 | 48.401 | 5.660 | −15.975 | 1.00 | 11.95 | B | O |
| ATOM | 13867 | N | LEU | B | 335 | 47.135 | 6.258 | −17.736 | 1.00 | 12.45 | B | N |
| ATOM | 13868 | CA | LEU | B | 335 | 46.991 | 7.648 | −17.311 | 1.00 | 12.66 | B | C |
| ATOM | 13870 | CB | LEU | B | 335 | 46.194 | 8.447 | −18.352 | 1.00 | 12.71 | B | C |
| ATOM | 13873 | CG | LEU | B | 335 | 46.041 | 9.954 | −18.117 | 1.00 | 12.97 | B | C |
| ATOM | 13875 | CD1 | LEU | B | 335 | 47.397 | 10.642 | −18.055 | 1.00 | 13.00 | B | C |
| ATOM | 13879 | CD2 | LEU | B | 335 | 45.178 | 10.572 | −19.202 | 1.00 | 11.60 | B | C |
| ATOM | 13883 | C | LEU | B | 335 | 46.299 | 7.714 | −15.950 | 1.00 | 12.72 | B | C |
| ATOM | 13884 | O | LEU | B | 335 | 46.785 | 8.372 | −15.035 | 1.00 | 12.67 | B | O |
| ATOM | 13886 | N | TYR | B | 336 | 45.176 | 7.013 | −15.826 | 1.00 | 13.04 | B | N |
| ATOM | 13887 | CA | TYR | B | 336 | 44.394 | 6.979 | −14.584 | 1.00 | 13.37 | B | C |
| ATOM | 13889 | CB | TYR | B | 336 | 43.346 | 5.865 | −14.661 | 1.00 | 13.50 | B | C |
| ATOM | 13892 | CG | TYR | B | 336 | 42.316 | 5.877 | −13.556 | 1.00 | 13.69 | B | C |
| ATOM | 13893 | CD1 | TYR | B | 336 | 41.167 | 6.654 | −13.662 | 1.00 | 15.39 | B | C |
| ATOM | 13895 | CE1 | TYR | B | 336 | 40.205 | 6.659 | −12.659 | 1.00 | 15.19 | B | C |
| ATOM | 13897 | CZ | TYR | B | 336 | 40.386 | 5.879 | −11.536 | 1.00 | 13.61 | B | C |
| ATOM | 13898 | OH | TYR | B | 336 | 39.433 | 5.885 | −10.545 | 1.00 | 12.30 | B | O |
| ATOM | 13900 | CE2 | TYR | B | 336 | 41.517 | 5.091 | −11.410 | 1.00 | 13.99 | B | C |
| ATOM | 13902 | CD2 | TYR | B | 336 | 42.472 | 5.091 | −12.420 | 1.00 | 13.11 | B | C |
| ATOM | 13904 | C | TYR | B | 336 | 45.276 | 6.778 | −13.351 | 1.00 | 13.42 | B | C |
| ATOM | 13905 | O | TYR | B | 336 | 45.282 | 7.612 | −12.446 | 1.00 | 13.88 | B | O |
| ATOM | 13907 | N | ASN | B | 337 | 46.026 | 5.678 | −13.336 | 1.00 | 13.13 | B | N |
| ATOM | 13908 | CA | ASN | B | 337 | 46.914 | 5.349 | −12.221 | 1.00 | 12.80 | B | C |
| ATOM | 13910 | CB | ASN | B | 337 | 47.573 | 3.985 | −12.443 | 1.00 | 12.62 | B | C |
| ATOM | 13913 | CG | ASN | B | 337 | 46.576 | 2.842 | −12.446 | 1.00 | 12.42 | B | C |
| ATOM | 13914 | OD1 | ASN | B | 337 | 45.386 | 3.036 | −12.200 | 1.00 | 11.43 | B | O |
| ATOM | 13915 | ND2 | ASN | B | 337 | 47.062 | 1.639 | −12.726 | 1.00 | 12.41 | B | N |
| ATOM | 13918 | C | ASN | B | 337 | 47.997 | 6.404 | −12.020 | 1.00 | 13.00 | B | C |
| ATOM | 13919 | O | ASN | B | 337 | 48.274 | 6.810 | −10.891 | 1.00 | 13.85 | B | O |
| ATOM | 13921 | N | THR | B | 338 | 48.606 | 6.838 | −13.120 | 1.00 | 12.67 | B | N |
| ATOM | 13922 | CA | THR | B | 338 | 49.656 | 7.852 | −13.079 | 1.00 | 12.12 | B | C |
| ATOM | 13924 | CB | THR | B | 338 | 50.137 | 8.222 | −14.498 | 1.00 | 11.99 | B | C |
| ATOM | 13926 | OG1 | THR | B | 338 | 50.664 | 7.057 | −15.145 | 1.00 | 9.18 | B | O |
| ATOM | 13928 | CG2 | THR | B | 338 | 51.207 | 9.303 | −14.444 | 1.00 | 11.84 | B | C |
| ATOM | 13932 | C | THR | B | 338 | 49.161 | 9.111 | −12.384 | 1.00 | 12.48 | B | C |
| ATOM | 13933 | O | THR | B | 338 | 49.859 | 9.671 | −11.540 | 1.00 | 12.39 | B | O |
| ATOM | 13935 | N | ILE | B | 339 | 47.950 | 9.540 | −12.734 | 1.00 | 13.07 | B | N |
| ATOM | 13936 | CA | ILE | B | 339 | 47.373 | 10.759 | −12.172 | 1.00 | 13.52 | B | C |
| ATOM | 13938 | CB | ILE | B | 339 | 46.123 | 11.241 | −12.956 | 1.00 | 13.22 | B | C |
| ATOM | 13940 | CG1 | ILE | B | 339 | 46.443 | 11.474 | −14.438 | 1.00 | 12.90 | B | C |
| ATOM | 13943 | CD1 | ILE | B | 339 | 47.622 | 12.375 | −14.683 | 1.00 | 11.77 | B | C |
| ATOM | 13947 | CG2 | ILE | B | 339 | 45.587 | 12.534 | −12.362 | 1.00 | 12.97 | B | C |
| ATOM | 13951 | C | ILE | B | 339 | 47.018 | 10.561 | −10.697 | 1.00 | 14.03 | B | C |
| ATOM | 13952 | O | ILE | B | 339 | 47.294 | 11.430 | −9.870 | 1.00 | 15.15 | B | O |
| ATOM | 13954 | N | ASN | B | 340 | 46.419 | 9.422 | −10.364 | 1.00 | 13.83 | B | N |
| ATOM | 13955 | CA | ASN | B | 340 | 46.116 | 9.116 | −8.967 | 1.00 | 13.79 | B | C |
| ATOM | 13957 | CB | ASN | B | 340 | 45.287 | 7.837 | −8.852 | 1.00 | 13.39 | B | C |
| ATOM | 13960 | CG | ASN | B | 340 | 43.876 | 8.015 | −9.360 | 1.00 | 12.83 | B | C |
| ATOM | 13961 | OD1 | ASN | B | 340 | 43.552 | 9.024 | −9.987 | 1.00 | 11.69 | B | O |
| ATOM | 13962 | ND2 | ASN | B | 340 | 43.024 | 7.035 | −9.092 | 1.00 | 12.15 | B | N |
| ATOM | 13965 | C | ASN | B | 340 | 47.375 | 8.995 | −8.115 | 1.00 | 14.39 | B | C |
| ATOM | 13966 | O | ASN | B | 340 | 47.356 | 9.331 | −6.933 | 1.00 | 14.92 | B | O |
| ATOM | 13968 | N | GLU | B | 341 | 48.465 | 8.527 | −8.720 | 1.00 | 14.80 | B | N |
| ATOM | 13969 | CA | GLU | B | 341 | 49.731 | 8.361 | −8.006 | 1.00 | 15.19 | B | C |
| ATOM | 13971 | CB | GLU | B | 341 | 50.702 | 7.500 | −8.819 | 1.00 | 15.65 | B | C |
| ATOM | 13974 | CG | GLU | B | 341 | 52.057 | 7.297 | −8.150 | 1.00 | 17.64 | B | C |
| ATOM | 13977 | CD | GLU | B | 341 | 52.785 | 6.076 | −8.668 | 1.00 | 21.06 | B | C |
| ATOM | 13978 | OE1 | GLU | B | 341 | 53.791 | 6.243 | −9.394 | 1.00 | 22.18 | B | O |
| ATOM | 13979 | OE2 | GLU | B | 341 | 52.343 | 4.951 | −8.353 | 1.00 | 23.01 | B | O |
| ATOM | 13980 | C | GLU | B | 341 | 50.376 | 9.704 | −7.652 | 1.00 | 14.68 | B | C |

TABLE 8-2-continued

Coordinates for L494P Structure

| | | | | | | | | | | | | |
|---|---|---|---|---|---|---|---|---|---|---|---|---|
| ATOM | 13981 | O | GLU | B | 341 | 50.952 | 9.848 | −6.573 | 1.00 | 14.72 | B | O |
| ATOM | 13983 | N | ILE | B | 342 | 50.288 | 10.679 | −8.555 | 1.00 | 14.12 | B | N |
| ATOM | 13984 | CA | ILE | B | 342 | 50.753 | 12.035 | −8.253 | 1.00 | 13.72 | B | C |
| ATOM | 13986 | CB | ILE | B | 342 | 50.765 | 12.945 | −9.498 | 1.00 | 13.57 | B | C |
| ATOM | 13988 | CG1 | ILE | B | 342 | 51.775 | 12.434 | −10.526 | 1.00 | 14.64 | B | C |
| ATOM | 13991 | CD1 | ILE | B | 342 | 51.843 | 13.277 | −11.792 | 1.00 | 15.37 | B | C |
| ATOM | 13995 | CG2 | ILE | B | 342 | 51.123 | 14.376 | −9.111 | 1.00 | 13.73 | B | C |
| ATOM | 13999 | C | ILE | B | 342 | 49.858 | 12.654 | −7.179 | 1.00 | 13.24 | B | C |
| ATOM | 14000 | O | ILE | B | 342 | 50.340 | 13.359 | −6.290 | 1.00 | 13.44 | B | O |
| ATOM | 14002 | N | ALA | B | 343 | 48.557 | 12.379 | −7.270 | 1.00 | 12.34 | B | N |
| ATOM | 14003 | CA | ALA | B | 343 | 47.592 | 12.806 | −6.261 | 1.00 | 11.40 | B | C |
| ATOM | 14005 | CB | ALA | B | 343 | 46.197 | 12.362 | −6.654 | 1.00 | 11.24 | B | C |
| ATOM | 14009 | C | ALA | B | 343 | 47.956 | 12.253 | −4.883 | 1.00 | 10.91 | B | C |
| ATOM | 14010 | O | ALA | B | 343 | 47.833 | 12.953 | −3.876 | 1.00 | 10.88 | B | O |
| ATOM | 14012 | N | TYR | B | 344 | 48.409 | 11.001 | −4.851 | 1.00 | 10.38 | B | N |
| ATOM | 14013 | CA | TYR | B | 344 | 48.833 | 10.355 | −3.607 | 1.00 | 10.04 | B | C |
| ATOM | 14015 | CB | TYR | B | 344 | 49.023 | 8.845 | −3.814 | 1.00 | 9.93 | B | C |
| ATOM | 14018 | CG | TYR | B | 344 | 49.475 | 8.118 | −2.569 | 1.00 | 8.21 | B | C |
| ATOM | 14019 | CD1 | TYR | B | 344 | 48.553 | 7.639 | −1.648 | 1.00 | 6.65 | B | C |
| ATOM | 14021 | CE1 | TYR | B | 344 | 48.963 | 6.982 | −0.497 | 1.00 | 6.47 | B | C |
| ATOM | 14023 | CZ | TYR | B | 344 | 50.309 | 6.799 | −0.254 | 1.00 | 6.00 | B | C |
| ATOM | 14024 | OH | TYR | B | 344 | 50.715 | 6.147 | 0.888 | 1.00 | 4.30 | B | O |
| ATOM | 14026 | CE2 | TYR | B | 344 | 51.247 | 7.268 | −1.154 | 1.00 | 7.46 | B | C |
| ATOM | 14028 | CD2 | TYR | B | 344 | 50.827 | 7.924 | −2.304 | 1.00 | 8.03 | B | C |
| ATOM | 14030 | C | TYR | B | 344 | 50.119 | 10.977 | −3.064 | 1.00 | 10.06 | B | C |
| ATOM | 14031 | O | TYR | B | 344 | 50.269 | 11.142 | −1.856 | 1.00 | 10.03 | B | O |
| ATOM | 14033 | N | ASP | B | 345 | 51.047 | 11.310 | −3.957 | 1.00 | 10.36 | B | N |
| ATOM | 14034 | CA | ASP | B | 345 | 52.284 | 11.982 | −3.559 | 1.00 | 10.78 | B | C |
| ATOM | 14036 | CB | ASP | B | 345 | 53.256 | 12.088 | −4.740 | 1.00 | 10.82 | B | C |
| ATOM | 14039 | CG | ASP | B | 345 | 53.868 | 10.755 | −5.123 | 1.00 | 10.93 | B | C |
| ATOM | 14040 | OD1 | ASP | B | 345 | 53.973 | 9.858 | −4.256 | 1.00 | 11.03 | B | O |
| ATOM | 14041 | OD2 | ASP | B | 345 | 54.258 | 10.610 | −6.300 | 1.00 | 12.06 | B | O |
| ATOM | 14042 | C | ASP | B | 345 | 52.011 | 13.377 | −2.999 | 1.00 | 11.16 | B | C |
| ATOM | 14043 | O | ASP | B | 345 | 52.830 | 13.919 | −2.259 | 1.00 | 11.52 | B | O |
| ATOM | 14045 | N | ASN | B | 346 | 50.873 | 13.959 | −3.366 | 1.00 | 11.44 | B | N |
| ATOM | 14046 | CA | ASN | B | 346 | 50.468 | 15.260 | −2.843 | 1.00 | 11.76 | B | C |
| ATOM | 14048 | CB | ASN | B | 346 | 49.615 | 16.005 | −3.872 | 1.00 | 11.96 | B | C |
| ATOM | 14051 | CG | ASN | B | 346 | 50.458 | 16.711 | −4.910 | 1.00 | 13.27 | B | C |
| ATOM | 14052 | OD1 | ASN | B | 346 | 51.086 | 17.729 | −4.618 | 1.00 | 18.45 | B | O |
| ATOM | 14053 | ND2 | ASN | B | 346 | 50.485 | 16.174 | −6.128 | 1.00 | 12.71 | B | N |
| ATOM | 14056 | C | ASN | B | 346 | 49.733 | 15.140 | −1.514 | 1.00 | 11.65 | B | C |
| ATOM | 14057 | O | ASN | B | 346 | 49.944 | 15.953 | −0.612 | 1.00 | 11.65 | B | O |
| ATOM | 14059 | N | LEU | B | 347 | 48.876 | 14.126 | −1.399 | 1.00 | 11.52 | B | N |
| ATOM | 14060 | CA | LEU | B | 347 | 48.164 | 13.847 | −0.150 | 1.00 | 11.25 | B | C |
| ATOM | 14062 | CB | LEU | B | 347 | 47.136 | 12.728 | −0.350 | 1.00 | 10.95 | B | C |
| ATOM | 14065 | CG | LEU | B | 347 | 46.235 | 12.390 | 0.843 | 1.00 | 9.89 | B | C |
| ATOM | 14067 | CD1 | LEU | B | 347 | 45.291 | 13.541 | 1.145 | 1.00 | 9.37 | B | C |
| ATOM | 14071 | CD2 | LEU | B | 347 | 45.457 | 11.109 | 0.585 | 1.00 | 8.58 | B | C |
| ATOM | 14075 | C | LEU | B | 347 | 49.123 | 13.460 | 0.973 | 1.00 | 11.48 | B | C |
| ATOM | 14076 | O | LEU | B | 347 | 48.844 | 13.722 | 2.138 | 1.00 | 11.80 | B | O |
| ATOM | 14078 | N | LYS | B | 348 | 50.245 | 12.833 | 0.628 | 1.00 | 11.67 | B | N |
| ATOM | 14079 | CA | LYS | B | 348 | 51.230 | 12.424 | 1.627 | 1.00 | 11.74 | B | C |
| ATOM | 14081 | CB | LYS | B | 348 | 52.176 | 11.361 | 1.053 | 1.00 | 11.69 | B | C |
| ATOM | 14084 | CG | LYS | B | 348 | 53.032 | 10.658 | 2.104 | 1.00 | 10.78 | B | C |
| ATOM | 14087 | CD | LYS | B | 348 | 53.948 | 9.598 | 1.497 | 1.00 | 9.66 | B | C |
| ATOM | 14090 | CE | LYS | B | 348 | 55.189 | 10.191 | 0.836 | 1.00 | 8.44 | B | C |
| ATOM | 14093 | NZ | LYS | B | 348 | 54.959 | 10.572 | −0.583 | 1.00 | 7.87 | B | N |
| ATOM | 14097 | C | LYS | B | 348 | 52.033 | 13.625 | 2.125 | 1.00 | 11.88 | B | C |
| ATOM | 14098 | O | LYS | B | 348 | 52.147 | 13.851 | 3.330 | 1.00 | 11.65 | B | O |
| ATOM | 14100 | N | ASP | B | 349 | 52.574 | 14.398 | 1.192 | 1.00 | 12.38 | B | N |
| ATOM | 14101 | CA | ASP | B | 349 | 53.508 | 15.469 | 1.532 | 1.00 | 13.33 | B | C |
| ATOM | 14103 | CB | ASP | B | 349 | 54.425 | 15.775 | 0.342 | 1.00 | 13.19 | B | C |
| ATOM | 14106 | CG | ASP | B | 349 | 55.170 | 14.546 | −0.155 | 1.00 | 11.88 | B | C |
| ATOM | 14107 | OD1 | ASP | B | 349 | 55.312 | 13.572 | 0.616 | 1.00 | 7.56 | B | O |
| ATOM | 14108 | OD2 | ASP | B | 349 | 55.610 | 14.556 | −1.324 | 1.00 | 11.49 | B | O |
| ATOM | 14109 | C | ASP | B | 349 | 52.808 | 16.745 | 1.996 | 1.00 | 14.12 | B | C |
| ATOM | 14110 | O | ASP | B | 349 | 53.261 | 17.387 | 2.944 | 1.00 | 14.75 | B | O |
| ATOM | 14112 | N | LYS | B | 350 | 51.711 | 17.107 | 1.335 | 1.00 | 14.58 | B | N |
| ATOM | 14113 | CA | LYS | B | 350 | 51.003 | 18.357 | 1.634 | 1.00 | 15.29 | B | C |
| ATOM | 14115 | CB | LYS | B | 350 | 50.751 | 19.137 | 0.339 | 1.00 | 15.87 | B | C |
| ATOM | 14118 | CG | LYS | B | 350 | 52.035 | 19.487 | −0.411 | 1.00 | 18.40 | B | C |
| ATOM | 14121 | CD | LYS | B | 350 | 51.775 | 20.337 | −1.651 | 1.00 | 20.21 | B | C |
| ATOM | 14124 | CE | LYS | B | 350 | 52.936 | 20.246 | −2.646 | 1.00 | 20.06 | B | C |
| ATOM | 14127 | NZ | LYS | B | 350 | 54.271 | 20.455 | −2.007 | 1.00 | 19.09 | B | N |
| ATOM | 14131 | C | LYS | B | 350 | 49.691 | 18.156 | 2.407 | 1.00 | 14.89 | B | C |
| ATOM | 14132 | O | LYS | B | 350 | 49.227 | 19.073 | 3.088 | 1.00 | 14.72 | B | O |
| ATOM | 14134 | N | GLY | B | 351 | 49.098 | 16.970 | 2.304 | 1.00 | 14.61 | B | N |
| ATOM | 14135 | CA | GLY | B | 351 | 47.889 | 16.645 | 3.060 | 1.00 | 14.57 | B | C |

TABLE 8-2-continued

Coordinates for L494P Structure

| | | | | | | | | | | | | |
|---|---|---|---|---|---|---|---|---|---|---|---|---|
| ATOM | 14138 | C | GLY | B | 351 | 46.615 | 17.209 | 2.463 | 1.00 | 14.52 | B | C |
| ATOM | 14139 | O | GLY | B | 351 | 45.688 | 17.560 | 3.193 | 1.00 | 14.37 | B | O |
| ATOM | 14141 | N | GLU | B | 352 | 46.568 | 17.286 | 1.134 | 1.00 | 14.82 | B | N |
| ATOM | 14142 | CA | GLU | B | 352 | 45.429 | 17.859 | 0.416 | 1.00 | 15.23 | B | C |
| ATOM | 14144 | CB | GLU | B | 352 | 45.789 | 19.240 | −0.144 | 1.00 | 15.22 | B | C |
| ATOM | 14147 | CG | GLU | B | 352 | 46.260 | 20.271 | 0.894 | 1.00 | 15.93 | B | C |
| ATOM | 14150 | CD | GLU | B | 352 | 45.126 | 21.048 | 1.543 | 1.00 | 16.01 | B | C |
| ATOM | 14151 | OE1 | GLU | B | 352 | 43.998 | 20.519 | 1.642 | 1.00 | 17.82 | B | O |
| ATOM | 14152 | OE2 | GLU | B | 352 | 45.372 | 22.198 | 1.962 | 1.00 | 15.28 | B | O |
| ATOM | 14153 | C | GLU | B | 352 | 45.033 | 16.946 | −0.738 | 1.00 | 15.54 | B | C |
| ATOM | 14154 | O | GLU | B | 352 | 45.897 | 16.437 | −1.456 | 1.00 | 15.74 | B | O |
| ATOM | 14156 | N | ASN | B | 353 | 43.730 | 16.738 | −0.914 | 1.00 | 15.72 | B | N |
| ATOM | 14157 | CA | ASN | B | 353 | 43.228 | 15.980 | −2.058 | 1.00 | 15.71 | B | C |
| ATOM | 14159 | CB | ASN | B | 353 | 41.856 | 15.361 | −1.762 | 1.00 | 15.94 | B | C |
| ATOM | 14162 | CG | ASN | B | 353 | 41.403 | 14.388 | −2.847 | 1.00 | 16.62 | B | C |
| ATOM | 14163 | OD1 | ASN | B | 353 | 41.769 | 14.521 | −4.016 | 1.00 | 16.74 | B | O |
| ATOM | 14164 | ND2 | ASN | B | 353 | 40.602 | 13.403 | −2.459 | 1.00 | 17.81 | B | N |
| ATOM | 14167 | C | ASN | B | 353 | 43.148 | 16.888 | −3.277 | 1.00 | 15.38 | B | C |
| ATOM | 14168 | O | ASN | B | 353 | 42.204 | 17.666 | −3.424 | 1.00 | 15.14 | B | O |
| ATOM | 14170 | N | ILE | B | 354 | 44.145 | 16.775 | −4.149 | 1.00 | 15.29 | B | N |
| ATOM | 14171 | CA | ILE | B | 354 | 44.202 | 17.576 | −5.369 | 1.00 | 15.35 | B | C |
| ATOM | 14173 | CB | ILE | B | 354 | 45.608 | 18.197 | −5.558 | 1.00 | 15.18 | B | C |
| ATOM | 14175 | CG1 | ILE | B | 354 | 46.670 | 17.121 | −5.797 | 1.00 | 14.74 | B | C |
| ATOM | 14178 | CD1 | ILE | B | 354 | 47.872 | 17.644 | −6.528 | 1.00 | 14.74 | B | C |
| ATOM | 14182 | CG2 | ILE | B | 354 | 45.982 | 19.020 | −4.343 | 1.00 | 15.14 | B | C |
| ATOM | 14186 | C | ILE | B | 354 | 43.801 | 16.778 | −6.623 | 1.00 | 15.64 | B | C |
| ATOM | 14187 | O | ILE | B | 354 | 44.136 | 17.163 | −7.743 | 1.00 | 15.61 | B | O |
| ATOM | 14189 | N | LEU | B | 355 | 43.077 | 15.676 | −6.437 | 1.00 | 15.92 | B | N |
| ATOM | 14190 | CA | LEU | B | 355 | 42.667 | 14.836 | −7.564 | 1.00 | 15.93 | B | C |
| ATOM | 14192 | CB | LEU | B | 355 | 42.060 | 13.514 | −7.073 | 1.00 | 15.64 | B | C |
| ATOM | 14195 | CG | LEU | B | 355 | 41.802 | 12.439 | −8.136 | 1.00 | 14.69 | B | C |
| ATOM | 14197 | CD1 | LEU | B | 355 | 43.070 | 12.105 | −8.906 | 1.00 | 13.49 | B | C |
| ATOM | 14201 | CD2 | LEU | B | 355 | 41.222 | 11.184 | −7.499 | 1.00 | 14.54 | B | C |
| ATOM | 14205 | C | LEU | B | 355 | 41.698 | 15.550 | −8.517 | 1.00 | 16.22 | B | C |
| ATOM | 14206 | O | LEU | B | 355 | 41.836 | 15.418 | −9.735 | 1.00 | 16.22 | B | O |
| ATOM | 14208 | N | PRO | B | 356 | 40.724 | 16.311 | −7.975 | 1.00 | 16.49 | B | N |
| ATOM | 14209 | CA | PRO | B | 356 | 39.781 | 16.987 | −8.869 | 1.00 | 16.94 | B | C |
| ATOM | 14211 | CB | PRO | B | 356 | 38.843 | 17.727 | −7.906 | 1.00 | 16.89 | B | C |
| ATOM | 14214 | CG | PRO | B | 356 | 38.992 | 17.035 | −6.615 | 1.00 | 16.92 | B | C |
| ATOM | 14217 | CD | PRO | B | 356 | 40.410 | 16.581 | −6.562 | 1.00 | 16.28 | B | C |
| ATOM | 14220 | C | PRO | B | 356 | 40.460 | 17.974 | −9.817 | 1.00 | 17.52 | B | C |
| ATOM | 14221 | O | PRO | B | 356 | 40.087 | 18.046 | −10.987 | 1.00 | 18.27 | B | O |
| ATOM | 14222 | N | TYR | B | 357 | 41.452 | 18.712 | −9.318 | 1.00 | 17.33 | B | N |
| ATOM | 14223 | CA | TYR | B | 357 | 42.179 | 19.690 | −10.138 | 1.00 | 17.07 | B | C |
| ATOM | 14225 | CB | TYR | B | 357 | 43.048 | 20.621 | −9.276 | 1.00 | 16.94 | B | C |
| ATOM | 14228 | CG | TYR | B | 357 | 42.411 | 21.040 | −7.969 | 1.00 | 17.63 | B | C |
| ATOM | 14229 | CD1 | TYR | B | 357 | 41.167 | 21.663 | −7.945 | 1.00 | 19.45 | B | C |
| ATOM | 14231 | CE1 | TYR | B | 357 | 40.575 | 22.042 | −6.742 | 1.00 | 19.39 | B | C |
| ATOM | 14233 | CZ | TYR | B | 357 | 41.234 | 21.798 | −5.551 | 1.00 | 18.35 | B | C |
| ATOM | 14234 | OH | TYR | B | 357 | 40.661 | 22.171 | −4.360 | 1.00 | 19.17 | B | O |
| ATOM | 14236 | CE2 | TYR | B | 357 | 42.470 | 21.183 | −5.550 | 1.00 | 17.99 | B | C |
| ATOM | 14238 | CD2 | TYR | B | 357 | 43.051 | 20.807 | −6.755 | 1.00 | 18.02 | B | C |
| ATOM | 14240 | C | TYR | B | 357 | 43.052 | 18.987 | −11.180 | 1.00 | 16.70 | B | C |
| ATOM | 14241 | O | TYR | B | 357 | 43.176 | 19.463 | −12.308 | 1.00 | 17.02 | B | O |
| ATOM | 14243 | N | LEU | B | 358 | 43.649 | 17.858 | −10.797 | 1.00 | 16.01 | B | N |
| ATOM | 14244 | CA | LEU | B | 358 | 44.510 | 17.088 | −11.699 | 1.00 | 15.44 | B | C |
| ATOM | 14246 | CB | LEU | B | 358 | 45.321 | 16.046 | −10.922 | 1.00 | 15.39 | B | C |
| ATOM | 14249 | CG | LEU | B | 358 | 46.418 | 16.579 | −9.998 | 1.00 | 15.39 | B | C |
| ATOM | 14251 | CD1 | LEU | B | 358 | 46.969 | 15.455 | −9.137 | 1.00 | 16.30 | B | C |
| ATOM | 14255 | CD2 | LEU | B | 358 | 47.531 | 17.241 | −10.791 | 1.00 | 15.02 | B | C |
| ATOM | 14259 | C | LEU | B | 358 | 43.720 | 16.397 | −12.810 | 1.00 | 15.07 | B | C |
| ATOM | 14260 | O | LEU | B | 358 | 44.217 | 16.259 | −13.928 | 1.00 | 14.92 | B | O |
| ATOM | 14262 | N | THR | B | 359 | 42.502 | 15.956 | −12.501 | 1.00 | 14.50 | B | N |
| ATOM | 14263 | CA | THR | B | 359 | 41.643 | 15.320 | −13.501 | 1.00 | 14.14 | B | C |
| ATOM | 14265 | CB | THR | B | 359 | 40.620 | 14.372 | −12.857 | 1.00 | 14.08 | B | C |
| ATOM | 14267 | OG1 | THR | B | 359 | 39.832 | 15.087 | −11.896 | 1.00 | 13.76 | B | O |
| ATOM | 14269 | CG2 | THR | B | 359 | 41.334 | 13.219 | −12.179 | 1.00 | 13.80 | B | C |
| ATOM | 14273 | C | THR | B | 359 | 40.904 | 16.350 | −14.349 | 1.00 | 13.91 | B | C |
| ATOM | 14274 | O | THR | B | 359 | 40.619 | 16.097 | −15.519 | 1.00 | 13.91 | B | O |
| ATOM | 14276 | N | LYS | B | 360 | 40.595 | 17.505 | −13.761 | 1.00 | 13.68 | B | N |
| ATOM | 14277 | CA | LYS | B | 360 | 39.919 | 18.583 | −14.487 | 1.00 | 13.73 | B | C |
| ATOM | 14279 | CB | LYS | B | 360 | 39.565 | 19.742 | −13.541 | 1.00 | 14.11 | B | C |
| ATOM | 14282 | CG | LYS | B | 360 | 38.670 | 20.824 | −14.147 | 1.00 | 15.76 | B | C |
| ATOM | 14285 | CD | LYS | B | 360 | 37.240 | 20.337 | −14.337 | 1.00 | 17.92 | B | C |
| ATOM | 14288 | CE | LYS | B | 360 | 36.414 | 21.340 | −15.130 | 1.00 | 19.80 | B | C |
| ATOM | 14291 | NZ | LYS | B | 360 | 35.031 | 20.844 | −15.397 | 1.00 | 21.13 | B | N |
| ATOM | 14295 | C | LYS | B | 360 | 40.785 | 19.080 | −15.646 | 1.00 | 13.04 | B | C |
| ATOM | 14296 | O | LYS | B | 360 | 40.277 | 19.341 | −16.738 | 1.00 | 12.64 | B | O |

TABLE 8-2-continued

Coordinates for L494P Structure

| | | | | | | | | | | | | |
|---|---|---|---|---|---|---|---|---|---|---|---|---|
| ATOM | 14298 | N | ALA | B | 361 | 42.089 | 19.200 | −15.400 | 1.00 | 12.50 | B | N |
| ATOM | 14299 | CA | ALA | B | 361 | 43.043 | 19.582 | −16.436 | 1.00 | 12.11 | B | C |
| ATOM | 14301 | CB | ALA | B | 361 | 44.430 | 19.730 | −15.850 | 1.00 | 11.80 | B | C |
| ATOM | 14305 | C | ALA | B | 361 | 43.056 | 18.556 | −17.562 | 1.00 | 12.30 | B | C |
| ATOM | 14306 | O | ALA | B | 361 | 43.047 | 18.925 | −18.738 | 1.00 | 12.61 | B | O |
| ATOM | 14308 | N | TRP | B | 362 | 43.066 | 17.274 | −17.198 | 1.00 | 12.41 | B | N |
| ATOM | 14309 | CA | TRP | B | 362 | 43.062 | 16.187 | −18.184 | 1.00 | 12.60 | B | C |
| ATOM | 14311 | CB | TRP | B | 362 | 43.484 | 14.860 | −17.545 | 1.00 | 12.31 | B | C |
| ATOM | 14314 | CG | TRP | B | 362 | 44.957 | 14.676 | −17.578 | 1.00 | 12.74 | B | C |
| ATOM | 14315 | CD1 | TRP | B | 362 | 45.823 | 14.737 | −16.524 | 1.00 | 13.49 | B | C |
| ATOM | 14317 | NE1 | TRP | B | 362 | 47.110 | 14.535 | −16.958 | 1.00 | 12.06 | B | N |
| ATOM | 14319 | CE2 | TRP | B | 362 | 47.093 | 14.347 | −18.315 | 1.00 | 11.96 | B | C |
| ATOM | 14320 | CD2 | TRP | B | 362 | 45.751 | 14.432 | −18.737 | 1.00 | 11.61 | B | C |
| ATOM | 14321 | CE3 | TRP | B | 362 | 45.459 | 14.278 | −20.094 | 1.00 | 11.70 | B | C |
| ATOM | 14323 | CZ3 | TRP | B | 362 | 46.499 | 14.042 | −20.975 | 1.00 | 12.47 | B | C |
| ATOM | 14325 | CH2 | TRP | B | 362 | 47.824 | 13.960 | −20.525 | 1.00 | 12.99 | B | C |
| ATOM | 14327 | CZ2 | TRP | B | 362 | 48.140 | 14.110 | −19.201 | 1.00 | 12.91 | B | C |
| ATOM | 14329 | C | TRP | B | 362 | 41.725 | 16.024 | −18.904 | 1.00 | 13.17 | B | C |
| ATOM | 14330 | O | TRP | B | 362 | 41.682 | 15.459 | −19.997 | 1.00 | 13.14 | B | O |
| ATOM | 14332 | N | ALA | B | 363 | 40.646 | 16.510 | −18.289 | 1.00 | 13.48 | B | N |
| ATOM | 14333 | CA | ALA | B | 363 | 39.325 | 16.500 | −18.915 | 1.00 | 13.34 | B | C |
| ATOM | 14335 | CB | ALA | B | 363 | 38.235 | 16.626 | −17.862 | 1.00 | 13.16 | B | C |
| ATOM | 14339 | C | ALA | B | 363 | 39.214 | 17.625 | −19.940 | 1.00 | 13.54 | B | C |
| ATOM | 14340 | O | ALA | B | 363 | 38.772 | 17.398 | −21.066 | 1.00 | 13.89 | B | O |
| ATOM | 14342 | N | ASP | B | 364 | 39.626 | 18.831 | −19.553 | 1.00 | 13.59 | B | N |
| ATOM | 14343 | CA | ASP | B | 364 | 39.577 | 19.995 | −20.447 | 1.00 | 13.61 | B | C |
| ATOM | 14345 | CB | ASP | B | 364 | 39.922 | 21.277 | −19.683 | 1.00 | 13.78 | B | C |
| ATOM | 14348 | CG | ASP | B | 364 | 38.894 | 21.626 | −18.616 | 1.00 | 16.18 | B | C |
| ATOM | 14349 | OD1 | ASP | B | 364 | 38.028 | 20.775 | −18.311 | 1.00 | 19.21 | B | O |
| ATOM | 14350 | OD2 | ASP | B | 364 | 38.957 | 22.753 | −18.077 | 1.00 | 17.35 | B | O |
| ATOM | 14351 | C | ASP | B | 364 | 40.503 | 19.861 | −21.666 | 1.00 | 13.27 | B | C |
| ATOM | 14352 | O | ASP | B | 364 | 40.219 | 20.435 | −22.721 | 1.00 | 12.94 | B | O |
| ATOM | 14354 | N | LEU | B | 365 | 41.601 | 19.116 | −21.521 | 1.00 | 12.55 | B | N |
| ATOM | 14355 | CA | LEU | B | 365 | 42.537 | 18.901 | −22.627 | 1.00 | 11.93 | B | C |
| ATOM | 14357 | CB | LEU | B | 365 | 43.893 | 18.407 | −22.108 | 1.00 | 11.48 | B | C |
| ATOM | 14360 | CG | LEU | B | 365 | 44.991 | 18.096 | −23.139 | 1.00 | 9.74 | B | C |
| ATOM | 14362 | CD1 | LEU | B | 365 | 45.213 | 19.237 | −24.114 | 1.00 | 7.44 | B | C |
| ATOM | 14366 | CD2 | LEU | B | 365 | 46.293 | 17.754 | −22.438 | 1.00 | 7.19 | B | C |
| ATOM | 14370 | C | LEU | B | 365 | 41.968 | 17.917 | −23.643 | 1.00 | 12.31 | B | C |
| ATOM | 14371 | O | LEU | B | 365 | 42.123 | 18.103 | −24.848 | 1.00 | 12.10 | B | O |
| ATOM | 14373 | N | CYS | B | 366 | 41.312 | 16.870 | −23.156 | 1.00 | 13.31 | B | N |
| ATOM | 14374 | CA | CYS | B | 366 | 40.674 | 15.889 | −24.034 | 1.00 | 14.41 | B | C |
| ATOM | 14376 | CB | CYS | B | 366 | 40.246 | 14.655 | −23.240 | 1.00 | 14.50 | B | C |
| ATOM | 14379 | SG | CYS | B | 366 | 41.629 | 13.759 | −22.500 | 1.00 | 14.66 | B | S |
| ATOM | 14381 | C | CYS | B | 366 | 39.475 | 16.505 | −24.756 | 1.00 | 15.14 | B | C |
| ATOM | 14382 | O | CYS | B | 366 | 39.314 | 16.319 | −25.966 | 1.00 | 15.49 | B | O |
| ATOM | 14384 | N | ASN | B | 367 | 38.641 | 17.229 | −24.005 | 1.00 | 15.16 | B | N |
| ATOM | 14385 | CA | ASN | B | 367 | 37.579 | 18.057 | −24.585 | 1.00 | 14.89 | B | C |
| ATOM | 14387 | CB | ASN | B | 367 | 36.875 | 18.893 | −23.502 | 1.00 | 14.96 | B | C |
| ATOM | 14390 | CG | ASN | B | 367 | 35.727 | 18.155 | −22.831 | 1.00 | 14.43 | B | C |
| ATOM | 14391 | OD1 | ASN | B | 367 | 34.815 | 17.660 | −23.495 | 1.00 | 13.51 | B | O |
| ATOM | 14392 | ND2 | ASN | B | 367 | 35.751 | 18.110 | −21.503 | 1.00 | 13.11 | B | N |
| ATOM | 14395 | C | ASN | B | 367 | 38.139 | 19.000 | −25.648 | 1.00 | 15.02 | B | C |
| ATOM | 14396 | O | ASN | B | 367 | 37.520 | 19.203 | −26.691 | 1.00 | 14.98 | B | O |
| ATOM | 14398 | N | ALA | B | 368 | 39.309 | 19.574 | −25.368 | 1.00 | 15.27 | B | N |
| ATOM | 14399 | CA | ALA | B | 368 | 39.981 | 20.480 | −26.303 | 1.00 | 15.42 | B | C |
| ATOM | 14401 | CB | ALA | B | 368 | 41.197 | 21.126 | −25.646 | 1.00 | 15.49 | B | C |
| ATOM | 14405 | C | ALA | B | 368 | 40.394 | 19.763 | −27.583 | 1.00 | 15.38 | B | C |
| ATOM | 14406 | O | ALA | B | 368 | 40.305 | 20.335 | −28.672 | 1.00 | 14.84 | B | O |
| ATOM | 14408 | N | PHE | B | 369 | 40.850 | 18.517 | −27.444 | 1.00 | 15.74 | B | N |
| ATOM | 14409 | CA | PHE | B | 369 | 41.198 | 17.689 | −28.600 | 1.00 | 15.84 | B | C |
| ATOM | 14411 | CB | PHE | B | 369 | 41.926 | 16.405 | −28.175 | 1.00 | 15.87 | B | C |
| ATOM | 14414 | CG | PHE | B | 369 | 43.362 | 16.608 | −27.751 | 1.00 | 16.19 | B | C |
| ATOM | 14415 | CD1 | PHE | B | 369 | 44.261 | 17.284 | −28.565 | 1.00 | 17.44 | B | C |
| ATOM | 14417 | CE1 | PHE | B | 369 | 45.589 | 17.449 | −28.175 | 1.00 | 17.59 | B | C |
| ATOM | 14419 | CZ | PHE | B | 369 | 46.031 | 16.919 | −26.978 | 1.00 | 14.90 | B | C |
| ATOM | 14421 | CE2 | PHE | B | 369 | 45.152 | 16.230 | −26.169 | 1.00 | 14.93 | B | C |
| ATOM | 14423 | CD2 | PHE | B | 369 | 43.828 | 16.069 | −26.558 | 1.00 | 16.05 | B | C |
| ATOM | 14425 | C | PHE | B | 369 | 39.953 | 17.313 | −29.402 | 1.00 | 15.56 | B | C |
| ATOM | 14426 | O | PHE | B | 369 | 39.951 | 17.391 | −30.628 | 1.00 | 15.57 | B | O |
| ATOM | 14428 | N | LEU | B | 370 | 38.898 | 16.904 | −28.705 | 1.00 | 15.73 | B | N |
| ATOM | 14429 | CA | LEU | B | 370 | 37.660 | 16.472 | −29.358 | 1.00 | 16.24 | B | C |
| ATOM | 14431 | CB | LEU | B | 370 | 36.587 | 16.157 | −28.302 | 1.00 | 16.24 | B | C |
| ATOM | 14434 | CG | LEU | B | 370 | 35.468 | 15.179 | −28.670 | 1.00 | 15.94 | B | C |
| ATOM | 14436 | CD1 | LEU | B | 370 | 36.027 | 13.860 | −29.180 | 1.00 | 15.36 | B | C |
| ATOM | 14440 | CD2 | LEU | B | 370 | 34.569 | 14.943 | −27.466 | 1.00 | 15.13 | B | C |
| ATOM | 14444 | C | LEU | B | 370 | 37.167 | 17.547 | −30.328 | 1.00 | 16.58 | B | C |
| ATOM | 14445 | O | LEU | B | 370 | 36.894 | 17.269 | −31.496 | 1.00 | 16.08 | B | O |

TABLE 8-2-continued

Coordinates for L494P Structure

| | | | | | | | | | | | | |
|---|---|---|---|---|---|---|---|---|---|---|---|---|
| ATOM | 14447 | N | GLN | B | 371 | 37.087 | 18.776 | −29.828 | 1.00 | 17.63 | B | N |
| ATOM | 14448 | CA | GLN | B | 371 | 36.713 | 19.947 | −30.624 | 1.00 | 18.39 | B | C |
| ATOM | 14450 | CB | GLN | B | 371 | 36.835 | 21.212 | −29.761 | 1.00 | 18.47 | B | C |
| ATOM | 14453 | CG | GLN | B | 371 | 36.465 | 22.509 | −30.455 | 1.00 | 18.40 | B | C |
| ATOM | 14456 | CD | GLN | B | 371 | 35.014 | 22.546 | −30.854 | 1.00 | 19.71 | B | C |
| ATOM | 14457 | OE1 | GLN | B | 371 | 34.657 | 22.160 | −31.965 | 1.00 | 21.51 | B | O |
| ATOM | 14458 | NE2 | GLN | B | 371 | 34.161 | 22.995 | −29.942 | 1.00 | 21.78 | B | N |
| ATOM | 14461 | C | GLN | B | 371 | 37.557 | 20.098 | −31.899 | 1.00 | 19.05 | B | C |
| ATOM | 14462 | O | GLN | B | 371 | 37.033 | 20.494 | −32.943 | 1.00 | 19.37 | B | O |
| ATOM | 14464 | N | GLU | B | 372 | 38.857 | 19.803 | −31.804 | 1.00 | 19.25 | B | N |
| ATOM | 14465 | CA | GLU | B | 372 | 39.748 | 19.811 | −32.974 | 1.00 | 19.20 | B | C |
| ATOM | 14467 | CB | GLU | B | 372 | 41.226 | 19.689 | −32.562 | 1.00 | 19.45 | B | C |
| ATOM | 14470 | CG | GLU | B | 372 | 41.877 | 20.997 | −32.107 | 1.00 | 21.69 | B | C |
| ATOM | 14473 | CD | GLU | B | 372 | 43.356 | 20.840 | −31.747 | 1.00 | 24.43 | B | C |
| ATOM | 14474 | OE1 | GLU | B | 372 | 43.861 | 19.695 | −31.711 | 1.00 | 25.03 | B | O |
| ATOM | 14475 | OE2 | GLU | B | 372 | 44.017 | 21.870 | −31.498 | 1.00 | 25.72 | B | O |
| ATOM | 14476 | C | GLU | B | 372 | 39.391 | 18.682 | −33.941 | 1.00 | 18.59 | B | C |
| ATOM | 14477 | O | GLU | B | 372 | 39.372 | 18.883 | −35.158 | 1.00 | 18.34 | B | O |
| ATOM | 14479 | N | ALA | B | 373 | 39.108 | 17.502 | −33.391 | 1.00 | 18.19 | B | N |
| ATOM | 14480 | CA | ALA | B | 373 | 38.762 | 16.331 | −34.195 | 1.00 | 17.99 | B | C |
| ATOM | 14482 | CB | ALA | B | 373 | 38.816 | 15.070 | −33.345 | 1.00 | 17.85 | B | C |
| ATOM | 14486 | C | ALA | B | 373 | 37.386 | 16.472 | −34.844 | 1.00 | 17.94 | B | C |
| ATOM | 14487 | O | ALA | B | 373 | 37.146 | 15.920 | −35.916 | 1.00 | 18.34 | B | O |
| ATOM | 14489 | N | LYS | B | 374 | 36.486 | 17.205 | −34.193 | 1.00 | 17.70 | B | N |
| ATOM | 14490 | CA | LYS | B | 374 | 35.146 | 17.438 | −34.736 | 1.00 | 17.42 | B | C |
| ATOM | 14492 | CB | LYS | B | 374 | 34.195 | 17.945 | −33.647 | 1.00 | 17.54 | B | C |
| ATOM | 14495 | CG | LYS | B | 374 | 33.700 | 16.869 | −32.696 | 1.00 | 16.57 | B | C |
| ATOM | 14498 | CD | LYS | B | 374 | 32.755 | 17.459 | −31.667 | 1.00 | 16.38 | B | C |
| ATOM | 14501 | CE | LYS | B | 374 | 32.149 | 16.392 | −30.780 | 1.00 | 16.46 | B | C |
| ATOM | 14504 | NZ | LYS | B | 374 | 31.306 | 16.977 | −29.704 | 1.00 | 15.25 | B | N |
| ATOM | 14508 | C | LYS | B | 374 | 35.174 | 18.425 | −35.900 | 1.00 | 17.26 | B | C |
| ATOM | 14509 | O | LYS | B | 374 | 34.513 | 18.208 | −36.915 | 1.00 | 17.43 | B | O |
| ATOM | 14511 | N | TRP | B | 375 | 35.934 | 19.509 | −35.750 | 1.00 | 17.18 | B | N |
| ATOM | 14512 | CA | TRP | B | 375 | 36.105 | 20.483 | −36.832 | 1.00 | 17.31 | B | C |
| ATOM | 14514 | CB | TRP | B | 375 | 36.949 | 21.681 | −36.372 | 1.00 | 17.16 | B | C |
| ATOM | 14517 | CG | TRP | B | 375 | 36.259 | 22.614 | −35.404 | 1.00 | 17.13 | B | C |
| ATOM | 14518 | CD1 | TRP | B | 375 | 34.916 | 22.857 | −35.304 | 1.00 | 17.41 | B | C |
| ATOM | 14520 | NE1 | TRP | B | 375 | 34.674 | 23.782 | −34.315 | 1.00 | 17.36 | B | N |
| ATOM | 14522 | CE2 | TRP | B | 375 | 35.868 | 24.171 | −33.767 | 1.00 | 17.07 | B | C |
| ATOM | 14523 | CD2 | TRP | B | 375 | 36.891 | 23.458 | −34.429 | 1.00 | 16.95 | B | C |
| ATOM | 14524 | CE3 | TRP | B | 375 | 38.221 | 23.677 | −34.049 | 1.00 | 15.71 | B | C |
| ATOM | 14526 | CZ3 | TRP | B | 375 | 38.484 | 24.587 | −33.029 | 1.00 | 15.41 | B | C |
| ATOM | 14528 | CH2 | TRP | B | 375 | 37.444 | 25.278 | −32.389 | 1.00 | 16.22 | B | C |
| ATOM | 14530 | CZ2 | TRP | B | 375 | 36.133 | 25.084 | −32.741 | 1.00 | 16.57 | B | C |
| ATOM | 14532 | C | TRP | B | 375 | 36.750 | 19.842 | −38.066 | 1.00 | 17.41 | B | C |
| ATOM | 14533 | O | TRP | B | 375 | 36.502 | 20.269 | −39.198 | 1.00 | 17.35 | B | O |
| ATOM | 14535 | N | LEU | B | 376 | 37.570 | 18.818 | −37.840 | 1.00 | 17.35 | B | N |
| ATOM | 14536 | CA | LEU | B | 376 | 38.231 | 18.100 | −38.923 | 1.00 | 17.23 | B | C |
| ATOM | 14538 | CB | LEU | B | 376 | 39.425 | 17.302 | −38.391 | 1.00 | 17.49 | B | C |
| ATOM | 14541 | CG | LEU | B | 376 | 40.555 | 17.070 | −39.395 | 1.00 | 18.22 | B | C |
| ATOM | 14543 | CD1 | LEU | B | 376 | 41.433 | 18.312 | −39.485 | 1.00 | 19.63 | B | C |
| ATOM | 14547 | CD2 | LEU | B | 376 | 41.383 | 15.849 | −39.012 | 1.00 | 19.32 | B | C |
| ATOM | 14551 | C | LEU | B | 376 | 37.248 | 17.167 | −39.627 | 1.00 | 16.88 | B | C |
| ATOM | 14552 | O | LEU | B | 376 | 37.183 | 17.143 | −40.854 | 1.00 | 17.11 | B | O |
| ATOM | 14554 | N | TYR | B | 377 | 36.486 | 16.402 | −38.849 | 1.00 | 16.77 | B | N |
| ATOM | 14555 | CA | TYR | B | 377 | 35.499 | 15.476 | −39.412 | 1.00 | 17.06 | B | C |
| ATOM | 14557 | CB | TYR | B | 377 | 34.930 | 14.547 | −38.327 | 1.00 | 17.15 | B | C |
| ATOM | 14560 | CG | TYR | B | 377 | 33.854 | 13.587 | −38.814 | 1.00 | 17.58 | B | C |
| ATOM | 14561 | CD1 | TYR | B | 377 | 34.187 | 12.403 | −39.475 | 1.00 | 17.98 | B | C |
| ATOM | 14563 | CE1 | TYR | B | 377 | 33.200 | 11.520 | −39.920 | 1.00 | 17.11 | B | C |
| ATOM | 14565 | CZ | TYR | B | 377 | 31.865 | 11.820 | −39.701 | 1.00 | 17.79 | B | C |
| ATOM | 14566 | OH | TYR | B | 377 | 30.880 | 10.962 | −40.133 | 1.00 | 15.15 | B | O |
| ATOM | 14568 | CE2 | TYR | B | 377 | 31.511 | 12.987 | −39.047 | 1.00 | 19.01 | B | C |
| ATOM | 14570 | CD2 | TYR | B | 377 | 32.504 | 13.862 | −38.608 | 1.00 | 18.51 | B | C |
| ATOM | 14572 | C | TYR | B | 377 | 34.365 | 16.223 | −40.116 | 1.00 | 16.88 | B | C |
| ATOM | 14573 | O | TYR | B | 377 | 33.846 | 15.748 | −41.126 | 1.00 | 17.51 | B | O |
| ATOM | 14575 | N | ASN | B | 378 | 33.996 | 17.390 | −39.590 | 1.00 | 16.33 | B | N |
| ATOM | 14576 | CA | ASN | B | 378 | 32.891 | 18.178 | −40.140 | 1.00 | 16.09 | B | C |
| ATOM | 14578 | CB | ASN | B | 378 | 32.095 | 18.824 | −38.999 | 1.00 | 16.18 | B | C |
| ATOM | 14581 | CG | ASN | B | 378 | 31.487 | 17.797 | −38.053 | 1.00 | 15.67 | B | C |
| ATOM | 14582 | OD1 | ASN | B | 378 | 30.872 | 16.821 | −38.486 | 1.00 | 14.58 | B | O |
| ATOM | 14583 | ND2 | ASN | B | 378 | 31.651 | 18.021 | −36.755 | 1.00 | 13.56 | B | N |
| ATOM | 14586 | C | ASN | B | 378 | 33.333 | 19.252 | −41.141 | 1.00 | 15.94 | B | C |
| ATOM | 14587 | O | ASN | B | 378 | 32.503 | 20.019 | −41.630 | 1.00 | 15.56 | B | O |
| ATOM | 14589 | N | LYS | B | 379 | 34.632 | 19.300 | −41.444 | 1.00 | 16.13 | B | N |
| ATOM | 14590 | CA | LYS | B | 379 | 35.208 | 20.300 | −42.358 | 1.00 | 16.30 | B | C |
| ATOM | 14592 | CB | LYS | B | 379 | 34.699 | 20.087 | −43.797 | 1.00 | 16.31 | B | C |
| ATOM | 14595 | CG | LYS | B | 379 | 35.509 | 19.101 | −44.626 | 1.00 | 17.12 | B | C |

TABLE 8-2-continued

Coordinates for L494P Structure

| | | | | | | | | | | | |
|---|---|---|---|---|---|---|---|---|---|---|---|
| ATOM | 14598 | CD | LYS | B | 379 | 35.221 | 19.295 | −46.113 | 1.00 | 18.17 B | C |
| ATOM | 14601 | CE | LYS | B | 379 | 35.889 | 18.233 | −46.973 | 1.00 | 20.00 B | C |
| ATOM | 14604 | NZ | LYS | B | 379 | 35.188 | 16.917 | −46.903 | 1.00 | 20.73 B | N |
| ATOM | 14608 | C | LYS | B | 379 | 34.963 | 21.756 | −41.922 | 1.00 | 16.29 B | C |
| ATOM | 14609 | O | LYS | B | 379 | 34.987 | 22.669 | −42.751 | 1.00 | 16.86 B | O |
| ATOM | 14611 | N | SER | B | 380 | 34.755 | 21.978 | −40.625 | 1.00 | 15.76 B | N |
| ATOM | 14612 | CA | SER | B | 380 | 34.443 | 23.312 | −40.119 | 1.00 | 15.29 B | C |
| ATOM | 14614 | CB | SER | B | 380 | 34.179 | 23.266 | −38.614 | 1.00 | 15.44 B | C |
| ATOM | 14617 | OG | SER | B | 380 | 33.129 | 22.367 | −38.305 | 1.00 | 15.59 B | O |
| ATOM | 14619 | C | SER | B | 380 | 35.580 | 24.284 | −40.417 | 1.00 | 14.99 B | C |
| ATOM | 14620 | O | SER | B | 380 | 36.743 | 23.885 | −40.479 | 1.00 | 14.56 B | O |
| ATOM | 14622 | N | THR | B | 381 | 35.231 | 25.557 | −40.600 | 1.00 | 14.97 B | N |
| ATOM | 14623 | CA | THR | B | 381 | 36.196 | 26.607 | −40.939 | 1.00 | 14.59 B | C |
| ATOM | 14625 | CB | THR | B | 381 | 35.976 | 27.102 | −42.383 | 1.00 | 14.34 B | C |
| ATOM | 14627 | OG1 | THR | B | 381 | 34.623 | 27.544 | −42.533 | 1.00 | 13.29 B | O |
| ATOM | 14629 | CG2 | THR | B | 381 | 36.243 | 25.984 | −43.376 | 1.00 | 14.48 B | C |
| ATOM | 14633 | C | THR | B | 381 | 36.079 | 27.788 | −39.969 | 1.00 | 14.43 B | C |
| ATOM | 14634 | O | THR | B | 381 | 35.732 | 28.900 | −40.379 | 1.00 | 14.36 B | O |
| ATOM | 14636 | N | PRO | B | 382 | 36.379 | 27.551 | −38.676 | 1.00 | 14.16 B | N |
| ATOM | 14637 | CA | PRO | B | 382 | 36.183 | 28.563 | −37.635 | 1.00 | 14.13 B | C |
| ATOM | 14639 | CB | PRO | B | 382 | 36.455 | 27.790 | −36.336 | 1.00 | 14.03 B | C |
| ATOM | 14642 | CG | PRO | B | 382 | 37.313 | 26.672 | −36.731 | 1.00 | 13.70 B | C |
| ATOM | 14645 | CD | PRO | B | 382 | 36.876 | 26.285 | −38.107 | 1.00 | 13.99 B | C |
| ATOM | 14648 | C | PRO | B | 382 | 37.114 | 29.768 | −37.731 | 1.00 | 13.68 B | C |
| ATOM | 14649 | O | PRO | B | 382 | 38.166 | 29.702 | −38.368 | 1.00 | 13.57 B | O |
| ATOM | 14650 | N | THR | B | 383 | 36.709 | 30.857 | −37.082 | 1.00 | 13.56 B | N |
| ATOM | 14651 | CA | THR | B | 383 | 37.507 | 32.075 | −37.022 | 1.00 | 13.70 B | C |
| ATOM | 14653 | CB | THR | B | 383 | 36.758 | 33.208 | −36.285 | 1.00 | 13.82 B | C |
| ATOM | 14655 | OG1 | THR | B | 383 | 36.295 | 32.735 | −35.013 | 1.00 | 13.66 B | O |
| ATOM | 14657 | CG2 | THR | B | 383 | 35.571 | 33.691 | −37.103 | 1.00 | 13.85 B | C |
| ATOM | 14661 | C | THR | B | 383 | 38.809 | 31.809 | −36.289 | 1.00 | 13.73 B | C |
| ATOM | 14662 | O | THR | B | 383 | 38.962 | 30.774 | −35.645 | 1.00 | 14.13 B | O |
| ATOM | 14664 | N | PHE | B | 384 | 39.744 | 32.747 | −36.387 | 1.00 | 13.93 B | N |
| ATOM | 14665 | CA | PHE | B | 384 | 41.013 | 32.645 | −35.668 | 1.00 | 13.87 B | C |
| ATOM | 14667 | CB | PHE | B | 384 | 41.974 | 33.752 | −36.117 | 1.00 | 13.82 B | C |
| ATOM | 14670 | CG | PHE | B | 384 | 43.181 | 33.906 | −35.237 | 1.00 | 14.42 B | C |
| ATOM | 14671 | CD1 | PHE | B | 384 | 44.302 | 33.112 | −35.428 | 1.00 | 15.39 B | C |
| ATOM | 14673 | CE1 | PHE | B | 384 | 45.421 | 33.253 | −34.613 | 1.00 | 15.72 B | C |
| ATOM | 14675 | CZ | PHE | B | 384 | 45.423 | 34.201 | −33.597 | 1.00 | 16.47 B | C |
| ATOM | 14677 | CE2 | PHE | B | 384 | 44.307 | 35.002 | −33.398 | 1.00 | 15.83 B | C |
| ATOM | 14679 | CD2 | PHE | B | 384 | 43.195 | 34.851 | −34.215 | 1.00 | 15.61 B | C |
| ATOM | 14681 | C | PHE | B | 384 | 40.803 | 32.697 | −34.155 | 1.00 | 13.83 B | C |
| ATOM | 14682 | O | PHE | B | 384 | 41.562 | 32.086 | −33.407 | 1.00 | 13.69 B | O |
| ATOM | 14684 | N | ASP | B | 385 | 39.773 | 33.419 | −33.714 | 1.00 | 14.28 B | N |
| ATOM | 14685 | CA | ASP | B | 385 | 39.461 | 33.546 | −32.286 | 1.00 | 14.69 B | C |
| ATOM | 14687 | CB | ASP | B | 385 | 38.335 | 34.564 | −32.067 | 1.00 | 14.68 B | C |
| ATOM | 14690 | CG | ASP | B | 385 | 38.758 | 35.989 | −32.377 | 1.00 | 14.29 B | C |
| ATOM | 14691 | OD1 | ASP | B | 385 | 39.916 | 36.198 | −32.801 | 1.00 | 12.29 B | O |
| ATOM | 14692 | OD2 | ASP | B | 385 | 37.922 | 36.901 | −32.194 | 1.00 | 13.65 B | O |
| ATOM | 14693 | C | ASP | B | 385 | 39.072 | 32.212 | −31.647 | 1.00 | 14.95 B | C |
| ATOM | 14694 | O | ASP | B | 385 | 39.558 | 31.872 | −30.565 | 1.00 | 15.03 B | O |
| ATOM | 14696 | N | ASP | B | 386 | 38.199 | 31.463 | −32.315 | 1.00 | 15.10 B | N |
| ATOM | 14697 | CA | ASP | B | 386 | 37.756 | 30.164 | −31.807 | 1.00 | 15.21 B | C |
| ATOM | 14699 | CB | ASP | B | 386 | 36.562 | 29.635 | −32.608 | 1.00 | 14.89 B | C |
| ATOM | 14702 | CG | ASP | B | 386 | 35.352 | 30.537 | −32.518 | 1.00 | 13.79 B | C |
| ATOM | 14703 | OD1 | ASP | B | 386 | 35.359 | 31.469 | −31.688 | 1.00 | 11.65 B | O |
| ATOM | 14704 | OD2 | ASP | B | 386 | 34.395 | 30.312 | −33.284 | 1.00 | 13.99 B | O |
| ATOM | 14705 | C | ASP | B | 386 | 38.881 | 29.141 | −31.845 | 1.00 | 15.56 B | C |
| ATOM | 14706 | O | ASP | B | 386 | 39.175 | 28.506 | −30.831 | 1.00 | 15.59 B | O |
| ATOM | 14708 | N | TYR | B | 387 | 39.509 | 28.987 | −33.010 | 1.00 | 16.18 B | N |
| ATOM | 14709 | CA | TYR | B | 387 | 40.535 | 27.961 | −33.190 | 1.00 | 17.16 B | C |
| ATOM | 14711 | CB | TYR | B | 387 | 41.021 | 27.871 | −34.639 | 1.00 | 17.34 B | C |
| ATOM | 14714 | CG | TYR | B | 387 | 42.013 | 26.745 | −34.840 | 1.00 | 19.17 B | C |
| ATOM | 14715 | CD1 | TYR | B | 387 | 41.602 | 25.419 | −34.781 | 1.00 | 22.10 B | C |
| ATOM | 14717 | CE1 | TYR | B | 387 | 42.503 | 24.374 | −34.945 | 1.00 | 25.04 B | C |
| ATOM | 14719 | CZ | TYR | B | 387 | 43.839 | 24.650 | −35.170 | 1.00 | 26.53 B | C |
| ATOM | 14720 | OH | TYR | B | 387 | 44.731 | 23.609 | −35.338 | 1.00 | 27.53 B | O |
| ATOM | 14722 | CE2 | TYR | B | 387 | 44.278 | 25.965 | −35.225 | 1.00 | 25.30 B | C |
| ATOM | 14724 | CD2 | TYR | B | 387 | 43.363 | 27.004 | −35.055 | 1.00 | 22.56 B | C |
| ATOM | 14726 | C | TYR | B | 387 | 41.729 | 28.180 | −32.272 | 1.00 | 17.41 B | C |
| ATOM | 14727 | O | TYR | B | 387 | 42.241 | 27.224 | −31.689 | 1.00 | 18.04 B | O |
| ATOM | 14729 | N | PHE | B | 388 | 42.177 | 29.426 | −32.147 | 1.00 | 17.25 B | N |
| ATOM | 14730 | CA | PHE | B | 388 | 43.255 | 29.726 | −31.218 | 1.00 | 17.19 B | C |
| ATOM | 14732 | CB | PHE | B | 388 | 43.803 | 31.135 | −31.406 | 1.00 | 16.75 B | C |
| ATOM | 14735 | CG | PHE | B | 388 | 45.047 | 31.387 | −30.617 | 1.00 | 16.33 B | C |
| ATOM | 14736 | CD1 | PHE | B | 388 | 46.244 | 30.796 | −30.994 | 1.00 | 16.78 B | C |
| ATOM | 14738 | CE1 | PHE | B | 388 | 47.401 | 31.006 | −30.265 | 1.00 | 16.25 B | C |
| ATOM | 14740 | CZ | PHE | B | 388 | 47.369 | 31.808 | −29.137 | 1.00 | 16.41 B | C |

TABLE 8-2-continued

Coordinates for L494P Structure

| | | | | | | | | | | | | |
|---|---|---|---|---|---|---|---|---|---|---|---|---|
| ATOM | 14742 | CE2 | PHE | B | 388 | 46.175 | 32.396 | −28.742 | 1.00 | 16.15 | B | C |
| ATOM | 14744 | CD2 | PHE | B | 388 | 45.021 | 32.179 | −29.479 | 1.00 | 16.35 | B | C |
| ATOM | 14746 | C | PHE | B | 388 | 42.778 | 29.539 | −29.783 | 1.00 | 17.91 | B | C |
| ATOM | 14747 | O | PHE | B | 388 | 43.468 | 28.913 | −28.979 | 1.00 | 18.31 | B | O |
| ATOM | 14749 | N | GLY | B | 389 | 41.590 | 30.062 | −29.475 | 1.00 | 18.30 | B | N |
| ATOM | 14750 | CA | GLY | B | 389 | 40.982 | 29.902 | −28.151 | 1.00 | 18.22 | B | C |
| ATOM | 14753 | C | GLY | B | 389 | 41.074 | 28.480 | −27.625 | 1.00 | 18.15 | B | C |
| ATOM | 14754 | O | GLY | B | 389 | 41.426 | 28.262 | −26.465 | 1.00 | 18.35 | B | O |
| ATOM | 14756 | N | ASN | B | 390 | 40.760 | 27.516 | −28.487 | 1.00 | 17.78 | B | N |
| ATOM | 14757 | CA | ASN | B | 390 | 40.865 | 26.097 | −28.154 | 1.00 | 17.52 | B | C |
| ATOM | 14759 | CB | ASN | B | 390 | 39.912 | 25.286 | −29.037 | 1.00 | 17.50 | B | C |
| ATOM | 14762 | CG | ASN | B | 390 | 39.703 | 23.875 | −28.529 | 1.00 | 17.13 | B | C |
| ATOM | 14763 | OD1 | ASN | B | 390 | 39.294 | 23.673 | −27.386 | 1.00 | 16.19 | B | O |
| ATOM | 14764 | ND2 | ASN | B | 390 | 39.977 | 22.890 | −29.377 | 1.00 | 16.14 | B | N |
| ATOM | 14767 | C | ASN | B | 390 | 42.289 | 25.559 | −28.324 | 1.00 | 17.35 | B | C |
| ATOM | 14768 | O | ASN | B | 390 | 42.689 | 24.616 | −27.637 | 1.00 | 16.87 | B | O |
| ATOM | 14770 | N | ALA | B | 391 | 43.041 | 26.160 | −29.246 | 1.00 | 17.15 | B | N |
| ATOM | 14771 | CA | ALA | B | 391 | 44.367 | 25.670 | −29.628 | 1.00 | 16.79 | B | C |
| ATOM | 14773 | CB | ALA | B | 391 | 44.874 | 26.414 | −30.850 | 1.00 | 16.54 | B | C |
| ATOM | 14777 | C | ALA | B | 391 | 45.402 | 25.737 | −28.507 | 1.00 | 16.67 | B | C |
| ATOM | 14778 | O | ALA | B | 391 | 46.229 | 24.834 | −28.386 | 1.00 | 17.01 | B | O |
| ATOM | 14780 | N | TRP | B | 392 | 45.378 | 26.795 | −27.700 | 1.00 | 16.56 | B | N |
| ATOM | 14781 | CA | TRP | B | 392 | 46.324 | 26.891 | −26.585 | 1.00 | 16.79 | B | C |
| ATOM | 14783 | CB | TRP | B | 392 | 46.551 | 28.339 | −26.114 | 1.00 | 16.90 | B | C |
| ATOM | 14786 | CG | TRP | B | 392 | 45.347 | 29.101 | −25.644 | 1.00 | 16.82 | B | C |
| ATOM | 14787 | CD1 | TRP | B | 392 | 44.616 | 29.993 | −26.368 | 1.00 | 17.86 | B | C |
| ATOM | 14789 | NE1 | TRP | B | 392 | 43.604 | 30.516 | −25.601 | 1.00 | 19.26 | B | N |
| ATOM | 14791 | CE2 | TRP | B | 392 | 43.675 | 29.974 | −24.346 | 1.00 | 19.44 | B | C |
| ATOM | 14792 | CD2 | TRP | B | 392 | 44.770 | 29.082 | −24.333 | 1.00 | 18.34 | B | C |
| ATOM | 14793 | CE3 | TRP | B | 392 | 45.061 | 28.389 | −23.152 | 1.00 | 20.35 | B | C |
| ATOM | 14795 | CZ3 | TRP | B | 392 | 44.259 | 28.606 | −22.035 | 1.00 | 20.88 | B | C |
| ATOM | 14797 | CH2 | TRP | B | 392 | 43.177 | 29.500 | −22.082 | 1.00 | 20.79 | B | C |
| ATOM | 14799 | CZ2 | TRP | B | 392 | 42.870 | 30.192 | −23.224 | 1.00 | 20.30 | B | C |
| ATOM | 14801 | C | TRP | B | 392 | 45.952 | 25.973 | −25.420 | 1.00 | 17.05 | B | C |
| ATOM | 14802 | O | TRP | B | 392 | 46.818 | 25.598 | −24.635 | 1.00 | 17.62 | B | O |
| ATOM | 14804 | N | LYS | B | 393 | 44.682 | 25.596 | −25.310 | 1.00 | 17.13 | B | N |
| ATOM | 14805 | CA | LYS | B | 393 | 44.297 | 24.524 | −24.390 | 1.00 | 17.62 | B | C |
| ATOM | 14807 | CB | LYS | B | 393 | 42.771 | 24.422 | −24.242 | 1.00 | 18.17 | B | C |
| ATOM | 14810 | CG | LYS | B | 393 | 42.149 | 25.470 | −23.336 | 1.00 | 19.49 | B | C |
| ATOM | 14813 | CD | LYS | B | 393 | 40.637 | 25.300 | −23.251 | 1.00 | 20.92 | B | C |
| ATOM | 14816 | CE | LYS | B | 393 | 39.987 | 26.436 | −22.472 | 1.00 | 22.85 | B | C |
| ATOM | 14819 | NZ | LYS | B | 393 | 40.242 | 27.775 | −23.089 | 1.00 | 23.75 | B | N |
| ATOM | 14823 | C | LYS | B | 393 | 44.855 | 23.190 | −24.891 | 1.00 | 17.26 | B | C |
| ATOM | 14824 | O | LYS | B | 393 | 45.466 | 22.438 | −24.130 | 1.00 | 17.57 | B | O |
| ATOM | 14826 | N | SER | B | 394 | 44.655 | 22.917 | −26.181 | 1.00 | 16.47 | B | N |
| ATOM | 14827 | CA | SER | B | 394 | 45.061 | 21.644 | −26.782 | 1.00 | 15.87 | B | C |
| ATOM | 14829 | CB | SER | B | 394 | 44.438 | 21.474 | −28.173 | 1.00 | 16.34 | B | C |
| ATOM | 14832 | OG | SER | B | 394 | 45.053 | 22.324 | −29.128 | 1.00 | 17.96 | B | O |
| ATOM | 14834 | C | SER | B | 394 | 46.573 | 21.488 | −26.882 | 1.00 | 14.74 | B | C |
| ATOM | 14835 | O | SER | B | 394 | 47.064 | 20.395 | −27.163 | 1.00 | 14.87 | B | O |
| ATOM | 14837 | N | SER | B | 395 | 47.306 | 22.581 | −26.674 | 1.00 | 13.73 | B | N |
| ATOM | 14838 | CA | SER | B | 395 | 48.768 | 22.536 | −26.627 | 1.00 | 12.86 | B | C |
| ATOM | 14840 | CB | SER | B | 395 | 49.347 | 23.953 | −26.514 | 1.00 | 12.97 | B | C |
| ATOM | 14843 | OG | SER | B | 395 | 49.165 | 24.500 | −25.216 | 1.00 | 10.58 | B | O |
| ATOM | 14845 | C | SER | B | 395 | 49.263 | 21.677 | −25.460 | 1.00 | 12.10 | B | C |
| ATOM | 14846 | O | SER | B | 395 | 50.306 | 21.037 | −25.563 | 1.00 | 12.00 | B | O |
| ATOM | 14848 | N | SER | B | 396 | 48.478 | 21.661 | −24.379 | 1.00 | 11.22 | B | N |
| ATOM | 14849 | CA | SER | B | 396 | 48.812 | 21.023 | −23.096 | 1.00 | 10.50 | B | C |
| ATOM | 14851 | CB | SER | B | 396 | 49.589 | 19.704 | −23.259 | 1.00 | 10.20 | B | C |
| ATOM | 14854 | OG | SER | B | 396 | 50.988 | 19.921 | −23.297 | 1.00 | 8.38 | B | O |
| ATOM | 14856 | C | SER | B | 396 | 49.576 | 21.997 | −22.197 | 1.00 | 10.26 | B | C |
| ATOM | 14857 | O | SER | B | 396 | 50.076 | 21.611 | −21.138 | 1.00 | 9.66 | B | O |
| ATOM | 14859 | N | GLY | B | 397 | 49.637 | 23.260 | −22.623 | 1.00 | 9.98 | B | N |
| ATOM | 14860 | CA | GLY | B | 397 | 50.327 | 24.315 | −21.889 | 1.00 | 9.92 | B | C |
| ATOM | 14863 | C | GLY | B | 397 | 49.710 | 24.631 | −20.538 | 1.00 | 9.97 | B | C |
| ATOM | 14864 | O | GLY | B | 397 | 50.433 | 24.872 | −19.576 | 1.00 | 10.10 | B | O |
| ATOM | 14866 | N | PRO | B | 398 | 48.368 | 24.665 | −20.462 | 1.00 | 10.22 | B | N |
| ATOM | 14867 | CA | PRO | B | 398 | 47.702 | 24.796 | −19.167 | 1.00 | 10.28 | B | C |
| ATOM | 14869 | CB | PRO | B | 398 | 46.239 | 25.041 | −19.547 | 1.00 | 10.17 | B | C |
| ATOM | 14872 | CG | PRO | B | 398 | 46.294 | 25.597 | −20.918 | 1.00 | 10.28 | B | C |
| ATOM | 14875 | CD | PRO | B | 398 | 47.428 | 24.886 | −21.573 | 1.00 | 10.52 | B | C |
| ATOM | 14878 | C | PRO | B | 398 | 47.834 | 23.548 | −18.292 | 1.00 | 10.37 | B | C |
| ATOM | 14879 | O | PRO | B | 398 | 48.153 | 23.664 | −17.105 | 1.00 | 9.87 | B | O |
| ATOM | 14880 | N | LEU | B | 399 | 47.594 | 22.372 | −18.872 | 1.00 | 10.74 | B | N |
| ATOM | 14881 | CA | LEU | B | 399 | 47.682 | 21.120 | −18.118 | 1.00 | 10.74 | B | C |
| ATOM | 14883 | CB | LEU | B | 399 | 47.255 | 19.920 | −18.965 | 1.00 | 10.40 | B | C |
| ATOM | 14886 | CG | LEU | B | 399 | 47.118 | 18.589 | −18.212 | 1.00 | 8.78 | B | C |
| ATOM | 14888 | CD1 | LEU | B | 399 | 46.277 | 17.619 | −19.010 | 1.00 | 9.68 | B | C |

TABLE 8-2-continued

Coordinates for L494P Structure

| | | | | | | | | | | | | |
|---|---|---|---|---|---|---|---|---|---|---|---|---|
| ATOM | 14892 | CD2 | LEU | B | 399 | 48.466 | 17.965 | −17.903 | 1.00 | 8.42 | B | C |
| ATOM | 14896 | C | LEU | B | 399 | 49.093 | 20.911 | −17.587 | 1.00 | 11.26 | B | C |
| ATOM | 14897 | O | LEU | B | 399 | 49.267 | 20.586 | −16.411 | 1.00 | 12.26 | B | O |
| ATOM | 14899 | N | GLN | B | 400 | 50.095 | 21.095 | −18.443 | 1.00 | 10.88 | B | N |
| ATOM | 14900 | CA | GLN | B | 400 | 51.482 | 20.980 | −18.000 | 1.00 | 10.85 | B | C |
| ATOM | 14902 | CB | GLN | B | 400 | 52.459 | 21.371 | −19.109 | 1.00 | 10.68 | B | C |
| ATOM | 14905 | CG | GLN | B | 400 | 52.718 | 20.268 | −20.118 | 1.00 | 10.94 | B | C |
| ATOM | 14908 | CD | GLN | B | 400 | 53.840 | 20.605 | −21.075 | 1.00 | 10.14 | B | C |
| ATOM | 14909 | OE1 | GLN | B | 400 | 54.874 | 21.143 | −20.674 | 1.00 | 8.70 | B | O |
| ATOM | 14910 | NE2 | GLN | B | 400 | 53.650 | 20.279 | −22.347 | 1.00 | 10.31 | B | N |
| ATOM | 14913 | C | GLN | B | 400 | 51.726 | 21.844 | −16.768 | 1.00 | 11.14 | B | C |
| ATOM | 14914 | O | GLN | B | 400 | 52.241 | 21.358 | −15.761 | 1.00 | 11.47 | B | O |
| ATOM | 14916 | N | LEU | B | 401 | 51.329 | 23.114 | −16.845 | 1.00 | 11.14 | B | N |
| ATOM | 14917 | CA | LEU | B | 401 | 51.568 | 24.065 | −15.759 | 1.00 | 11.06 | B | C |
| ATOM | 14919 | CB | LEU | B | 401 | 51.299 | 25.498 | −16.221 | 1.00 | 10.61 | B | C |
| ATOM | 14922 | CG | LEU | B | 401 | 52.308 | 26.063 | −17.224 | 1.00 | 11.73 | B | C |
| ATOM | 14924 | CD1 | LEU | B | 401 | 52.040 | 27.539 | −17.482 | 1.00 | 12.66 | B | C |
| ATOM | 14928 | CD2 | LEU | B | 401 | 53.736 | 25.867 | −16.738 | 1.00 | 15.02 | B | C |
| ATOM | 14932 | C | LEU | B | 401 | 50.761 | 23.747 | −14.499 | 1.00 | 11.70 | B | C |
| ATOM | 14933 | O | LEU | B | 401 | 51.333 | 23.653 | −13.412 | 1.00 | 12.09 | B | O |
| ATOM | 14935 | N | VAL | B | 402 | 49.448 | 23.559 | −14.633 | 1.00 | 12.08 | B | N |
| ATOM | 14936 | CA | VAL | B | 402 | 48.625 | 23.148 | −13.485 | 1.00 | 12.19 | B | C |
| ATOM | 14938 | CB | VAL | B | 402 | 47.230 | 22.621 | −13.907 | 1.00 | 12.09 | B | C |
| ATOM | 14940 | CG1 | VAL | B | 402 | 46.393 | 23.736 | −14.500 | 1.00 | 11.45 | B | C |
| ATOM | 14944 | CG2 | VAL | B | 402 | 46.508 | 21.992 | −12.715 | 1.00 | 10.48 | B | C |
| ATOM | 14948 | C | VAL | B | 402 | 49.343 | 22.055 | −12.691 | 1.00 | 12.73 | B | C |
| ATOM | 14949 | O | VAL | B | 402 | 49.364 | 22.090 | −11.463 | 1.00 | 13.03 | B | O |
| ATOM | 14951 | N | PHE | B | 403 | 49.931 | 21.096 | −13.406 | 1.00 | 12.77 | B | N |
| ATOM | 14952 | CA | PHE | B | 403 | 50.689 | 20.009 | −12.789 | 1.00 | 12.83 | B | C |
| ATOM | 14954 | CB | PHE | B | 403 | 51.004 | 18.918 | −13.818 | 1.00 | 13.10 | B | C |
| ATOM | 14957 | CG | PHE | B | 403 | 50.038 | 17.776 | −13.798 | 1.00 | 13.23 | B | C |
| ATOM | 14958 | CD1 | PHE | B | 403 | 50.267 | 16.676 | −12.985 | 1.00 | 12.90 | B | C |
| ATOM | 14960 | CE1 | PHE | B | 403 | 49.379 | 15.618 | −12.959 | 1.00 | 14.26 | B | C |
| ATOM | 14962 | CZ | PHE | B | 403 | 48.241 | 15.653 | −13.749 | 1.00 | 15.62 | B | C |
| ATOM | 14964 | CE2 | PHE | B | 403 | 48.004 | 16.745 | −14.567 | 1.00 | 15.30 | B | C |
| ATOM | 14966 | CD2 | PHE | B | 403 | 48.899 | 17.800 | −14.586 | 1.00 | 14.00 | B | C |
| ATOM | 14968 | C | PHE | B | 403 | 51.985 | 20.487 | −12.142 | 1.00 | 12.73 | B | C |
| ATOM | 14969 | O | PHE | B | 403 | 52.337 | 20.036 | −11.051 | 1.00 | 12.37 | B | O |
| ATOM | 14971 | N | ALA | B | 404 | 52.695 | 21.383 | −12.824 | 1.00 | 12.86 | B | N |
| ATOM | 14972 | CA | ALA | B | 404 | 53.958 | 21.925 | −12.317 | 1.00 | 12.97 | B | C |
| ATOM | 14974 | CB | ALA | B | 404 | 54.659 | 22.744 | −13.395 | 1.00 | 12.54 | B | C |
| ATOM | 14978 | C | ALA | B | 404 | 53.750 | 22.771 | −11.062 | 1.00 | 13.43 | B | C |
| ATOM | 14979 | O | ALA | B | 404 | 54.665 | 22.906 | −10.247 | 1.00 | 13.75 | B | O |
| ATOM | 14981 | N | TYR | B | 405 | 52.549 | 23.332 | −10.915 | 1.00 | 13.71 | B | N |
| ATOM | 14982 | CA | TYR | B | 405 | 52.200 | 24.148 | −9.750 | 1.00 | 13.86 | B | C |
| ATOM | 14984 | CB | TYR | B | 405 | 50.762 | 24.667 | −9.872 | 1.00 | 13.79 | B | C |
| ATOM | 14987 | CG | TYR | B | 405 | 50.254 | 25.335 | −8.618 | 1.00 | 13.21 | B | C |
| ATOM | 14988 | CD1 | TYR | B | 405 | 50.594 | 26.652 | −8.323 | 1.00 | 12.79 | B | C |
| ATOM | 14990 | CE1 | TYR | B | 405 | 50.136 | 27.270 | −7.170 | 1.00 | 11.81 | B | C |
| ATOM | 14992 | CZ | TYR | B | 405 | 49.332 | 26.565 | −6.298 | 1.00 | 12.37 | B | C |
| ATOM | 14993 | OH | TYR | B | 405 | 48.878 | 27.167 | −5.154 | 1.00 | 12.04 | B | O |
| ATOM | 14995 | CE2 | TYR | B | 405 | 48.983 | 25.251 | −6.566 | 1.00 | 12.72 | B | C |
| ATOM | 14997 | CD2 | TYR | B | 405 | 49.444 | 24.645 | −7.720 | 1.00 | 12.42 | B | C |
| ATOM | 14999 | C | TYR | B | 405 | 52.357 | 23.371 | −8.446 | 1.00 | 14.17 | B | C |
| ATOM | 15000 | O | TYR | B | 405 | 53.016 | 23.836 | −7.515 | 1.00 | 14.28 | B | O |
| ATOM | 15002 | N | PHE | B | 406 | 51.753 | 22.186 | −8.391 | 1.00 | 14.49 | B | N |
| ATOM | 15003 | CA | PHE | B | 406 | 51.802 | 21.342 | −7.193 | 1.00 | 14.68 | B | C |
| ATOM | 15005 | CB | PHE | B | 406 | 50.791 | 20.197 | −7.298 | 1.00 | 14.37 | B | C |
| ATOM | 15008 | CG | PHE | B | 406 | 49.360 | 20.654 | −7.391 | 1.00 | 13.87 | B | C |
| ATOM | 15009 | CD1 | PHE | B | 406 | 48.612 | 20.883 | −6.246 | 1.00 | 13.63 | B | C |
| ATOM | 15011 | CE1 | PHE | B | 406 | 47.290 | 21.297 | −6.334 | 1.00 | 12.80 | B | C |
| ATOM | 15013 | CZ | PHE | B | 406 | 46.705 | 21.484 | −7.573 | 1.00 | 11.76 | B | C |
| ATOM | 15015 | CE2 | PHE | B | 406 | 47.440 | 21.257 | −8.720 | 1.00 | 12.46 | B | C |
| ATOM | 15017 | CD2 | PHE | B | 406 | 48.758 | 20.843 | −8.626 | 1.00 | 13.06 | B | C |
| ATOM | 15019 | C | PHE | B | 406 | 53.202 | 20.774 | −6.955 | 1.00 | 15.00 | B | C |
| ATOM | 15020 | O | PHE | B | 406 | 53.542 | 20.387 | −5.837 | 1.00 | 14.79 | B | O |
| ATOM | 15022 | N | ALA | B | 407 | 54.001 | 20.725 | −8.015 | 1.00 | 15.76 | B | N |
| ATOM | 15023 | CA | ALA | B | 407 | 55.372 | 20.243 | −7.940 | 1.00 | 16.63 | B | C |
| ATOM | 15025 | CB | ALA | B | 407 | 55.849 | 19.847 | −9.323 | 1.00 | 16.82 | B | C |
| ATOM | 15029 | C | ALA | B | 407 | 56.327 | 21.270 | −7.338 | 1.00 | 17.61 | B | C |
| ATOM | 15030 | O | ALA | B | 407 | 57.348 | 20.889 | −6.761 | 1.00 | 17.54 | B | O |
| ATOM | 15032 | N | VAL | B | 408 | 56.005 | 22.558 | −7.485 | 1.00 | 18.76 | B | N |
| ATOM | 15033 | CA | VAL | B | 408 | 56.896 | 23.644 | −7.041 | 1.00 | 19.68 | B | C |
| ATOM | 15035 | CB | VAL | B | 408 | 57.122 | 24.709 | −8.151 | 1.00 | 19.56 | B | C |
| ATOM | 15037 | CG1 | VAL | B | 408 | 57.867 | 24.099 | −9.326 | 1.00 | 20.05 | B | C |
| ATOM | 15041 | CG2 | VAL | B | 408 | 55.809 | 25.326 | −8.608 | 1.00 | 19.46 | B | C |
| ATOM | 15045 | C | VAL | B | 408 | 56.422 | 24.343 | −5.765 | 1.00 | 20.58 | B | C |
| ATOM | 15046 | O | VAL | B | 408 | 57.217 | 24.560 | −4.850 | 1.00 | 20.87 | B | O |

TABLE 8-2-continued

| Coordinates for L494P Structure | | | | | | | | | | | |
|---|---|---|---|---|---|---|---|---|---|---|---|
| ATOM | 15048 | N | VAL | B | 409 | 55.137 | 24.686 | −5.700 | 1.00 | 21.60 B | N |
| ATOM | 15049 | CA | VAL | B | 409 | 54.589 | 25.416 | −4.556 | 1.00 | 22.34 B | C |
| ATOM | 15051 | CB | VAL | B | 409 | 53.202 | 26.016 | −4.877 | 1.00 | 22.39 B | C |
| ATOM | 15053 | CG1 | VAL | B | 409 | 52.600 | 26.674 | −3.640 | 1.00 | 23.44 B | C |
| ATOM | 15057 | CG2 | VAL | B | 409 | 53.306 | 27.019 | −6.015 | 1.00 | 22.32 B | C |
| ATOM | 15061 | C | VAL | B | 409 | 54.464 | 24.492 | −3.346 | 1.00 | 22.94 B | C |
| ATOM | 15062 | O | VAL | B | 409 | 53.760 | 23.483 | −3.411 | 1.00 | 23.20 B | O |
| ATOM | 15064 | N | GLN | B | 410 | 55.146 | 24.841 | −2.254 | 1.00 | 23.53 B | N |
| ATOM | 15065 | CA | GLN | B | 410 | 55.110 | 24.046 | −1.021 | 1.00 | 24.19 B | C |
| ATOM | 15067 | CB | GLN | B | 410 | 56.199 | 24.501 | −0.038 | 1.00 | 24.35 B | C |
| ATOM | 15070 | CG | GLN | B | 410 | 57.580 | 23.913 | −0.322 | 1.00 | 25.13 B | C |
| ATOM | 15073 | CD | GLN | B | 410 | 58.700 | 24.597 | 0.458 | 1.00 | 26.32 B | C |
| ATOM | 15074 | OE1 | GLN | B | 410 | 58.471 | 25.217 | 1.500 | 1.00 | 26.11 B | O |
| ATOM | 15075 | NE2 | GLN | B | 410 | 59.923 | 24.479 | −0.047 | 1.00 | 26.55 B | N |
| ATOM | 15078 | C | GLN | B | 410 | 53.736 | 24.119 | −0.354 | 1.00 | 24.67 B | C |
| ATOM | 15079 | O | GLN | B | 410 | 53.107 | 23.087 | −0.098 | 1.00 | 24.94 B | O |
| ATOM | 15081 | N | ASN | B | 411 | 53.282 | 25.340 | −0.077 | 1.00 | 24.76 B | N |
| ATOM | 15082 | CA | ASN | B | 411 | 51.964 | 25.568 | 0.515 | 1.00 | 24.87 B | C |
| ATOM | 15084 | CB | ASN | B | 411 | 52.044 | 26.607 | 1.639 | 1.00 | 24.93 B | C |
| ATOM | 15087 | CG | ASN | B | 411 | 52.557 | 26.022 | 2.944 | 1.00 | 25.27 B | C |
| ATOM | 15088 | OD1 | ASN | B | 411 | 52.140 | 26.439 | 4.027 | 1.00 | 25.02 B | O |
| ATOM | 15089 | ND2 | ASN | B | 411 | 53.458 | 25.050 | 2.850 | 1.00 | 24.79 B | N |
| ATOM | 15092 | C | ASN | B | 411 | 50.967 | 26.024 | −0.543 | 1.00 | 24.92 B | C |
| ATOM | 15093 | O | ASN | B | 411 | 50.950 | 27.198 | −0.924 | 1.00 | 25.20 B | O |
| ATOM | 15095 | N | ILE | B | 412 | 50.145 | 25.091 | −1.017 | 1.00 | 24.78 B | N |
| ATOM | 15096 | CA | ILE | B | 412 | 49.102 | 25.407 | −1.996 | 1.00 | 24.69 B | C |
| ATOM | 15098 | CB | ILE | B | 412 | 48.471 | 24.130 | −2.625 | 1.00 | 24.72 B | C |
| ATOM | 15100 | CG1 | ILE | B | 412 | 47.696 | 23.311 | −1.585 | 1.00 | 24.16 B | C |
| ATOM | 15103 | CD1 | ILE | B | 412 | 47.342 | 21.919 | −2.059 | 1.00 | 23.73 B | C |
| ATOM | 15107 | CG2 | ILE | B | 412 | 49.546 | 23.272 | −3.289 | 1.00 | 25.19 B | C |
| ATOM | 15111 | C | ILE | B | 412 | 48.015 | 26.260 | −1.350 | 1.00 | 24.62 B | C |
| ATOM | 15112 | O | ILE | B | 412 | 47.701 | 26.086 | −0.176 | 1.00 | 24.66 B | O |
| ATOM | 15114 | N | LYS | B | 413 | 47.457 | 27.187 | −2.121 | 1.00 | 24.99 B | N |
| ATOM | 15115 | CA | LYS | B | 413 | 46.396 | 28.065 | −1.635 | 1.00 | 25.75 B | C |
| ATOM | 15117 | CB | LYS | B | 413 | 46.871 | 29.520 | −1.653 | 1.00 | 25.95 B | C |
| ATOM | 15120 | CG | LYS | B | 413 | 48.243 | 29.716 | −1.015 | 1.00 | 28.01 B | C |
| ATOM | 15123 | CD | LYS | B | 413 | 48.538 | 31.179 | −0.705 | 1.00 | 30.48 B | C |
| ATOM | 15126 | CE | LYS | B | 413 | 49.825 | 31.320 | 0.103 | 1.00 | 31.81 B | C |
| ATOM | 15129 | NZ | LYS | B | 413 | 50.059 | 32.715 | 0.570 | 1.00 | 32.42 B | N |
| ATOM | 15133 | C | LYS | B | 413 | 45.152 | 27.892 | −2.505 | 1.00 | 25.95 B | C |
| ATOM | 15134 | O | LYS | B | 413 | 45.254 | 27.868 | −3.735 | 1.00 | 26.19 B | O |
| ATOM | 15136 | N | LYS | B | 414 | 43.983 | 27.762 | −1.874 | 1.00 | 25.87 B | N |
| ATOM | 15137 | CA | LYS | B | 414 | 42.731 | 27.596 | −2.619 | 1.00 | 25.83 B | C |
| ATOM | 15139 | CB | LYS | B | 414 | 41.512 | 27.515 | −1.691 | 1.00 | 26.36 B | C |
| ATOM | 15142 | CG | LYS | B | 414 | 40.168 | 27.499 | −2.450 | 1.00 | 27.62 B | C |
| ATOM | 15145 | CD | LYS | B | 414 | 38.978 | 27.133 | −1.562 | 1.00 | 28.07 B | C |
| ATOM | 15148 | CE | LYS | B | 414 | 38.690 | 28.200 | −0.508 | 1.00 | 28.15 B | C |
| ATOM | 15151 | NZ | LYS | B | 414 | 38.573 | 29.575 | −1.081 | 1.00 | 27.51 B | N |
| ATOM | 15155 | C | LYS | B | 414 | 42.547 | 28.730 | −3.622 | 1.00 | 25.45 B | C |
| ATOM | 15156 | O | LYS | B | 414 | 42.039 | 28.512 | −4.721 | 1.00 | 25.62 B | O |
| ATOM | 15158 | N | GLU | B | 415 | 42.958 | 29.936 | −3.235 | 1.00 | 24.98 B | N |
| ATOM | 15159 | CA | GLU | B | 415 | 42.926 | 31.092 | −4.133 | 1.00 | 24.62 B | C |
| ATOM | 15161 | CB | GLU | B | 415 | 43.333 | 32.377 | −3.388 | 1.00 | 24.74 B | C |
| ATOM | 15164 | CG | GLU | B | 415 | 44.180 | 33.364 | −4.212 | 1.00 | 25.93 B | C |
| ATOM | 15167 | CD | GLU | B | 415 | 43.994 | 34.813 | −3.804 | 1.00 | 26.17 B | C |
| ATOM | 15168 | OE1 | GLU | B | 415 | 43.609 | 35.076 | −2.646 | 1.00 | 28.18 B | O |
| ATOM | 15169 | OE2 | GLU | B | 415 | 44.241 | 35.695 | −4.655 | 1.00 | 26.04 B | O |
| ATOM | 15170 | C | GLU | B | 415 | 43.788 | 30.877 | −5.386 | 1.00 | 23.90 B | C |
| ATOM | 15171 | O | GLU | B | 415 | 43.367 | 31.210 | −6.495 | 1.00 | 23.91 B | O |
| ATOM | 15173 | N | GLU | B | 416 | 44.986 | 30.326 | −5.209 | 1.00 | 23.17 B | N |
| ATOM | 15174 | CA | GLU | B | 416 | 45.878 | 30.058 | −6.338 | 1.00 | 22.78 B | C |
| ATOM | 15176 | CB | GLU | B | 416 | 47.261 | 29.608 | −5.855 | 1.00 | 23.14 B | C |
| ATOM | 15179 | CG | GLU | B | 416 | 48.181 | 30.755 | −5.454 | 1.00 | 23.54 B | C |
| ATOM | 15182 | CD | GLU | B | 416 | 49.543 | 30.288 | −4.962 | 1.00 | 24.77 B | C |
| ATOM | 15183 | OE1 | GLU | B | 416 | 49.646 | 29.171 | −4.411 | 1.00 | 24.46 B | O |
| ATOM | 15184 | OE2 | GLU | B | 416 | 50.518 | 31.050 | −5.120 | 1.00 | 26.91 B | O |
| ATOM | 15185 | C | GLU | B | 416 | 45.285 | 29.017 | −7.284 | 1.00 | 22.07 B | C |
| ATOM | 15186 | O | GLU | B | 416 | 45.196 | 29.253 | −8.490 | 1.00 | 21.50 B | O |
| ATOM | 15188 | N | ILE | B | 417 | 44.874 | 27.875 | −6.737 | 1.00 | 21.72 B | N |
| ATOM | 15189 | CA | ILE | B | 417 | 44.253 | 26.822 | −7.551 | 1.00 | 22.01 B | C |
| ATOM | 15191 | CB | ILE | B | 417 | 44.108 | 25.472 | −6.790 | 1.00 | 22.11 B | C |
| ATOM | 15193 | CG1 | ILE | B | 417 | 43.194 | 25.610 | −5.576 | 1.00 | 22.41 B | C |
| ATOM | 15196 | CD1 | ILE | B | 417 | 43.202 | 24.395 | −4.674 | 1.00 | 23.93 B | C |
| ATOM | 15200 | CG2 | ILE | B | 417 | 45.473 | 24.951 | −6.362 | 1.00 | 22.61 B | C |
| ATOM | 15204 | C | ILE | B | 417 | 42.898 | 27.249 | −8.132 | 1.00 | 22.01 B | C |
| ATOM | 15205 | O | ILE | B | 417 | 42.449 | 26.680 | −9.127 | 1.00 | 21.57 B | O |
| ATOM | 15207 | N | GLU | B | 418 | 42.256 | 28.241 | −7.512 | 1.00 | 22.40 B | N |
| ATOM | 15208 | CA | GLU | B | 418 | 41.029 | 28.841 | −8.064 | 1.00 | 22.66 B | C |

TABLE 8-2-continued

| Coordinates for L494P Structure | | | | | | | | | | | |
|---|---|---|---|---|---|---|---|---|---|---|---|
| ATOM | 15210 | CB | GLU | B | 418 | 40.379 | 29.814 | −7.068 | 1.00 | 22.95 B | C |
| ATOM | 15213 | CG | GLU | B | 418 | 39.241 | 29.216 | −6.250 | 1.00 | 24.26 B | C |
| ATOM | 15216 | CD | GLU | B | 418 | 38.507 | 30.261 | −5.428 | 1.00 | 26.39 B | C |
| ATOM | 15217 | OE1 | GLU | B | 418 | 39.152 | 31.244 | −5.003 | 1.00 | 26.91 B | O |
| ATOM | 15218 | OE2 | GLU | B | 418 | 37.287 | 30.099 | −5.207 | 1.00 | 27.64 B | O |
| ATOM | 15219 | C | GLU | B | 418 | 41.288 | 29.568 | −9.384 | 1.00 | 22.19 B | C |
| ATOM | 15220 | O | GLU | B | 418 | 40.467 | 29.507 | −10.302 | 1.00 | 22.03 B | O |
| ATOM | 15222 | N | ASN | B | 419 | 42.419 | 30.263 | −9.468 | 1.00 | 21.74 B | N |
| ATOM | 15223 | CA | ASN | B | 419 | 42.819 | 30.931 | −10.704 | 1.00 | 21.85 B | C |
| ATOM | 15225 | CB | ASN | B | 419 | 43.803 | 32.069 | −10.409 | 1.00 | 21.97 B | C |
| ATOM | 15228 | CG | ASN | B | 419 | 43.112 | 33.305 | −9.840 | 1.00 | 22.96 B | C |
| ATOM | 15229 | OD1 | ASN | B | 419 | 42.276 | 33.922 | −10.503 | 1.00 | 24.59 B | O |
| ATOM | 15230 | ND2 | ASN | B | 419 | 43.462 | 33.670 | −8.609 | 1.00 | 22.29 B | N |
| ATOM | 15233 | C | ASN | B | 419 | 43.392 | 29.954 | −11.739 | 1.00 | 21.82 B | C |
| ATOM | 15234 | O | ASN | B | 419 | 43.309 | 30.208 | −12.942 | 1.00 | 21.68 B | O |
| ATOM | 15236 | N | LEU | B | 420 | 43.961 | 28.840 | −11.271 | 1.00 | 21.94 B | N |
| ATOM | 15237 | CA | LEU | B | 420 | 44.408 | 27.760 | −12.166 | 1.00 | 21.70 B | C |
| ATOM | 15239 | CB | LEU | B | 420 | 45.147 | 26.654 | −11.400 | 1.00 | 21.08 B | C |
| ATOM | 15242 | CG | LEU | B | 420 | 46.618 | 26.901 | −11.057 | 1.00 | 20.18 B | C |
| ATOM | 15244 | CD1 | LEU | B | 420 | 47.124 | 25.869 | −10.057 | 1.00 | 18.62 B | C |
| ATOM | 15248 | CD2 | LEU | B | 420 | 47.477 | 26.901 | −12.313 | 1.00 | 17.37 B | C |
| ATOM | 15252 | C | LEU | B | 420 | 43.228 | 27.145 | −12.903 | 1.00 | 22.21 B | C |
| ATOM | 15253 | O | LEU | B | 420 | 43.283 | 26.956 | −14.118 | 1.00 | 22.19 B | O |
| ATOM | 15255 | N | GLN | B | 421 | 42.166 | 26.832 | −12.160 | 1.00 | 22.92 B | N |
| ATOM | 15256 | CA | GLN | B | 421 | 40.958 | 26.240 | −12.739 | 1.00 | 23.57 B | C |
| ATOM | 15258 | CB | GLN | B | 421 | 39.911 | 25.943 | −11.656 | 1.00 | 24.09 B | C |
| ATOM | 15261 | CG | GLN | B | 421 | 40.296 | 24.803 | −10.706 | 1.00 | 26.83 B | C |
| ATOM | 15264 | CD | GLN | B | 421 | 39.112 | 23.933 | −10.302 | 1.00 | 29.79 B | C |
| ATOM | 15265 | OE1 | GLN | B | 421 | 39.061 | 22.742 | −10.627 | 1.00 | 31.64 B | O |
| ATOM | 15266 | NE2 | GLN | B | 421 | 38.151 | 24.525 | −9.597 | 1.00 | 29.87 B | N |
| ATOM | 15269 | C | GLN | B | 421 | 40.351 | 27.135 | −13.812 | 1.00 | 23.57 B | C |
| ATOM | 15270 | O | GLN | B | 421 | 39.842 | 26.637 | −14.815 | 1.00 | 23.53 B | O |
| ATOM | 15272 | N | LYS | B | 422 | 40.430 | 28.451 | −13.605 | 1.00 | 24.03 B | N |
| ATOM | 15273 | CA | LYS | B | 422 | 39.860 | 29.436 | −14.534 | 1.00 | 24.54 B | C |
| ATOM | 15275 | CB | LYS | B | 422 | 39.330 | 30.643 | −13.747 | 1.00 | 24.69 B | C |
| ATOM | 15278 | CG | LYS | B | 422 | 38.068 | 30.312 | −12.950 | 1.00 | 27.40 B | C |
| ATOM | 15281 | CD | LYS | B | 422 | 37.853 | 31.231 | −11.748 | 1.00 | 30.16 B | C |
| ATOM | 15284 | CE | LYS | B | 422 | 36.737 | 30.695 | −10.844 | 1.00 | 30.51 B | C |
| ATOM | 15287 | NZ | LYS | B | 422 | 36.523 | 31.525 | −9.621 | 1.00 | 30.84 B | N |
| ATOM | 15291 | C | LYS | B | 422 | 40.832 | 29.882 | −15.638 | 1.00 | 24.42 B | C |
| ATOM | 15292 | O | LYS | B | 422 | 40.546 | 30.833 | −16.366 | 1.00 | 24.81 B | O |
| ATOM | 15294 | N | TYR | B | 423 | 41.960 | 29.182 | −15.770 | 1.00 | 24.16 B | N |
| ATOM | 15295 | CA | TYR | B | 423 | 42.965 | 29.458 | −16.803 | 1.00 | 23.64 B | C |
| ATOM | 15297 | CB | TYR | B | 423 | 42.480 | 28.982 | −18.182 | 1.00 | 23.69 B | C |
| ATOM | 15300 | CG | TYR | B | 423 | 42.338 | 27.472 | −18.292 | 1.00 | 24.59 B | C |
| ATOM | 15301 | CD1 | TYR | B | 423 | 43.353 | 26.622 | −17.849 | 1.00 | 25.56 B | C |
| ATOM | 15303 | CE1 | TYR | B | 423 | 43.233 | 25.243 | −17.942 | 1.00 | 25.98 B | C |
| ATOM | 15305 | CZ | TYR | B | 423 | 42.096 | 24.691 | −18.492 | 1.00 | 26.45 B | C |
| ATOM | 15306 | OH | TYR | B | 423 | 41.994 | 23.323 | −18.576 | 1.00 | 26.60 B | O |
| ATOM | 15308 | CE2 | TYR | B | 423 | 41.073 | 25.506 | −18.948 | 1.00 | 26.05 B | C |
| ATOM | 15310 | CD2 | TYR | B | 423 | 41.200 | 26.892 | −18.848 | 1.00 | 25.18 B | C |
| ATOM | 15312 | C | TYR | B | 423 | 43.372 | 30.927 | −16.826 | 1.00 | 23.30 B | C |
| ATOM | 15313 | O | TYR | B | 423 | 43.079 | 31.657 | −17.773 | 1.00 | 23.79 B | O |
| ATOM | 15315 | N | HIS | B | 424 | 44.058 | 31.333 | −15.762 | 1.00 | 22.79 B | N |
| ATOM | 15316 | CA | HIS | B | 424 | 44.483 | 32.715 | −15.553 | 1.00 | 22.25 B | C |
| ATOM | 15318 | CB | HIS | B | 424 | 44.798 | 32.915 | −14.065 | 1.00 | 22.47 B | C |
| ATOM | 15321 | CG | HIS | B | 424 | 45.182 | 34.313 | −13.699 | 1.00 | 23.17 B | C |
| ATOM | 15322 | ND1 | HIS | B | 424 | 46.491 | 34.738 | −13.664 | 1.00 | 22.23 B | N |
| ATOM | 15324 | CE1 | HIS | B | 424 | 46.531 | 36.009 | −13.308 | 1.00 | 22.45 B | C |
| ATOM | 15326 | NE2 | HIS | B | 424 | 45.294 | 36.424 | −13.106 | 1.00 | 23.39 B | N |
| ATOM | 15328 | CD2 | HIS | B | 424 | 44.430 | 35.381 | −13.342 | 1.00 | 23.99 B | C |
| ATOM | 15330 | C | HIS | B | 424 | 45.701 | 33.058 | −16.415 | 1.00 | 21.56 B | C |
| ATOM | 15331 | O | HIS | B | 424 | 46.434 | 32.167 | −16.845 | 1.00 | 21.55 B | O |
| ATOM | 15333 | N | ASP | B | 425 | 45.898 | 34.354 | −16.659 | 1.00 | 21.01 B | N |
| ATOM | 15334 | CA | ASP | B | 425 | 47.006 | 34.875 | −17.482 | 1.00 | 20.76 B | C |
| ATOM | 15336 | CB | ASP | B | 425 | 47.157 | 36.385 | −17.267 | 1.00 | 20.81 B | C |
| ATOM | 15339 | CG | ASP | B | 425 | 45.982 | 37.171 | −17.801 | 1.00 | 21.95 B | C |
| ATOM | 15340 | OD1 | ASP | B | 425 | 45.764 | 37.140 | −19.030 | 1.00 | 23.03 B | O |
| ATOM | 15341 | OD2 | ASP | B | 425 | 45.281 | 37.822 | −16.994 | 1.00 | 22.61 B | O |
| ATOM | 15342 | C | ASP | B | 425 | 48.365 | 34.217 | −17.228 | 1.00 | 20.21 B | C |
| ATOM | 15343 | O | ASP | B | 425 | 49.082 | 33.880 | −18.172 | 1.00 | 20.00 B | O |
| ATOM | 15345 | N | THR | B | 426 | 48.711 | 34.052 | −15.952 | 1.00 | 19.50 B | N |
| ATOM | 15346 | CA | THR | B | 426 | 50.011 | 33.510 | −15.545 | 1.00 | 18.64 B | C |
| ATOM | 15348 | CB | THR | B | 426 | 50.061 | 33.267 | −14.021 | 1.00 | 18.27 B | C |
| ATOM | 15350 | OG1 | THR | B | 426 | 50.051 | 34.525 | −13.335 | 1.00 | 17.93 B | O |
| ATOM | 15352 | CG2 | THR | B | 426 | 51.313 | 32.502 | −13.632 | 1.00 | 17.94 B | C |
| ATOM | 15356 | C | THR | B | 426 | 50.362 | 32.216 | −16.278 | 1.00 | 18.30 B | C |
| ATOM | 15357 | O | THR | B | 426 | 51.519 | 32.012 | −16.657 | 1.00 | 18.29 B | O |

TABLE 8-2-continued

Coordinates for L494P Structure

| | | | | | | | | | | | | |
|---|---|---|---|---|---|---|---|---|---|---|---|---|
| ATOM | 15359 | N | ILE | B | 427 | 49.364 | 31.355 | −16.479 | 1.00 | 17.83 | B | N |
| ATOM | 15360 | CA | ILE | B | 427 | 49.556 | 30.106 | −17.222 | 1.00 | 17.71 | B | C |
| ATOM | 15362 | CB | ILE | B | 427 | 48.948 | 28.885 | −16.472 | 1.00 | 17.30 | B | C |
| ATOM | 15364 | CG1 | ILE | B | 427 | 47.417 | 28.906 | −16.489 | 1.00 | 16.67 | B | C |
| ATOM | 15367 | CD1 | ILE | B | 427 | 46.803 | 27.717 | −15.792 | 1.00 | 15.11 | B | C |
| ATOM | 15371 | CG2 | ILE | B | 427 | 49.449 | 28.846 | −15.039 | 1.00 | 16.16 | B | C |
| ATOM | 15375 | C | ILE | B | 427 | 49.025 | 30.172 | −18.663 | 1.00 | 18.09 | B | C |
| ATOM | 15376 | O | ILE | B | 427 | 49.557 | 29.498 | −19.547 | 1.00 | 17.89 | B | O |
| ATOM | 15378 | N | SER | B | 428 | 47.997 | 30.985 | −18.904 | 1.00 | 18.49 | B | N |
| ATOM | 15379 | CA | SER | B | 428 | 47.379 | 31.056 | −20.232 | 1.00 | 18.89 | B | C |
| ATOM | 15381 | CB | SER | B | 428 | 46.036 | 31.794 | −20.180 | 1.00 | 19.00 | B | C |
| ATOM | 15384 | OG | SER | B | 428 | 46.211 | 33.200 | −20.223 | 1.00 | 19.67 | B | O |
| ATOM | 15386 | C | SER | B | 428 | 48.296 | 31.721 | −21.255 | 1.00 | 19.28 | B | C |
| ATOM | 15387 | O | SER | B | 428 | 48.416 | 31.245 | −22.382 | 1.00 | 19.91 | B | O |
| ATOM | 15389 | N | ARG | B | 429 | 48.940 | 32.818 | −20.858 | 1.00 | 19.47 | B | N |
| ATOM | 15390 | CA | ARG | B | 429 | 49.798 | 33.597 | −21.763 | 1.00 | 19.36 | B | C |
| ATOM | 15392 | CB | ARG | B | 429 | 50.349 | 34.838 | −21.056 | 1.00 | 19.70 | B | C |
| ATOM | 15395 | CG | ARG | B | 429 | 49.283 | 35.843 | −20.642 | 1.00 | 22.63 | B | C |
| ATOM | 15398 | CD | ARG | B | 429 | 49.315 | 37.104 | −21.490 | 1.00 | 25.32 | B | C |
| ATOM | 15401 | NE | ARG | B | 429 | 48.208 | 38.001 | −21.157 | 1.00 | 26.37 | B | N |
| ATOM | 15403 | CZ | ARG | B | 429 | 47.010 | 37.998 | −21.745 | 1.00 | 27.17 | B | C |
| ATOM | 15404 | NH1 | ARG | B | 429 | 46.725 | 37.144 | −22.725 | 1.00 | 26.90 | B | N |
| ATOM | 15407 | NH2 | ARG | B | 429 | 46.084 | 38.865 | −21.349 | 1.00 | 28.32 | B | N |
| ATOM | 15410 | C | ARG | B | 429 | 50.948 | 32.784 | −22.364 | 1.00 | 18.47 | B | C |
| ATOM | 15411 | O | ARG | B | 429 | 51.117 | 32.783 | −23.577 | 1.00 | 17.94 | B | O |
| ATOM | 15413 | N | PRO | B | 430 | 51.742 | 32.087 | −21.528 | 1.00 | 18.01 | B | N |
| ATOM | 15414 | CA | PRO | B | 430 | 52.794 | 31.255 | −22.123 | 1.00 | 17.76 | B | C |
| ATOM | 15416 | CB | PRO | B | 430 | 53.597 | 30.774 | −20.909 | 1.00 | 17.79 | B | C |
| ATOM | 15419 | CG | PRO | B | 430 | 52.661 | 30.880 | −19.766 | 1.00 | 18.19 | B | C |
| ATOM | 15422 | CD | PRO | B | 430 | 51.791 | 32.058 | −20.056 | 1.00 | 17.89 | B | C |
| ATOM | 15425 | C | PRO | B | 430 | 52.255 | 30.068 | −22.933 | 1.00 | 17.32 | B | C |
| ATOM | 15426 | O | PRO | B | 430 | 52.989 | 29.504 | −23.746 | 1.00 | 17.56 | B | O |
| ATOM | 15427 | N | SER | B | 431 | 50.996 | 29.693 | −22.710 | 1.00 | 16.49 | B | N |
| ATOM | 15428 | CA | SER | B | 431 | 50.328 | 28.702 | −23.554 | 1.00 | 16.00 | B | C |
| ATOM | 15430 | CB | SER | B | 431 | 49.131 | 28.086 | −22.830 | 1.00 | 15.98 | B | C |
| ATOM | 15433 | OG | SER | B | 431 | 49.521 | 27.553 | −21.578 | 1.00 | 15.79 | B | O |
| ATOM | 15435 | C | SER | B | 431 | 49.896 | 29.310 | −24.895 | 1.00 | 15.50 | B | C |
| ATOM | 15436 | O | SER | B | 431 | 49.769 | 28.595 | −25.890 | 1.00 | 15.19 | B | O |
| ATOM | 15438 | N | HIS | B | 432 | 49.662 | 30.623 | −24.919 | 1.00 | 15.14 | B | N |
| ATOM | 15439 | CA | HIS | B | 432 | 49.510 | 31.350 | −26.183 | 1.00 | 14.91 | B | C |
| ATOM | 15441 | CB | HIS | B | 432 | 49.203 | 32.841 | −25.952 | 1.00 | 14.78 | B | C |
| ATOM | 15444 | CG | HIS | B | 432 | 47.812 | 33.122 | −25.471 | 1.00 | 14.57 | B | C |
| ATOM | 15445 | ND1 | HIS | B | 432 | 47.099 | 32.248 | −24.679 | 1.00 | 15.65 | B | N |
| ATOM | 15447 | CE1 | HIS | B | 432 | 45.914 | 32.766 | −24.408 | 1.00 | 14.74 | B | C |
| ATOM | 15449 | NE2 | HIS | B | 432 | 45.836 | 33.951 | −24.985 | 1.00 | 13.39 | B | N |
| ATOM | 15451 | CD2 | HIS | B | 432 | 47.013 | 34.200 | −25.650 | 1.00 | 14.77 | B | C |
| ATOM | 15453 | C | HIS | B | 432 | 50.807 | 31.224 | −26.984 | 1.00 | 14.58 | B | C |
| ATOM | 15454 | O | HIS | B | 432 | 50.786 | 30.909 | −28.172 | 1.00 | 14.38 | B | O |
| ATOM | 15456 | N | ILE | B | 433 | 51.931 | 31.455 | −26.307 | 1.00 | 14.30 | B | N |
| ATOM | 15457 | CA | ILE | B | 433 | 53.258 | 31.391 | −26.919 | 1.00 | 13.69 | B | C |
| ATOM | 15459 | CB | ILE | B | 433 | 54.357 | 31.939 | −25.968 | 1.00 | 13.55 | B | C |
| ATOM | 15461 | CG1 | ILE | B | 433 | 54.064 | 33.386 | −25.550 | 1.00 | 13.14 | B | C |
| ATOM | 15464 | CD1 | ILE | B | 433 | 54.088 | 34.380 | −26.682 | 1.00 | 11.73 | B | C |
| ATOM | 15468 | CG2 | ILE | B | 433 | 55.734 | 31.857 | −26.623 | 1.00 | 13.05 | B | C |
| ATOM | 15472 | C | ILE | B | 433 | 53.627 | 29.958 | −27.303 | 1.00 | 13.75 | B | C |
| ATOM | 15473 | O | ILE | B | 433 | 54.393 | 29.743 | −28.240 | 1.00 | 14.58 | B | O |
| ATOM | 15475 | N | PHE | B | 434 | 53.088 | 28.982 | −26.578 | 1.00 | 13.11 | B | N |
| ATOM | 15476 | CA | PHE | B | 434 | 53.363 | 27.570 | −26.851 | 1.00 | 12.79 | B | C |
| ATOM | 15478 | CB | PHE | B | 434 | 52.916 | 26.726 | −25.648 | 1.00 | 12.75 | B | C |
| ATOM | 15481 | CG | PHE | B | 434 | 53.066 | 25.231 | −25.822 | 1.00 | 13.16 | B | C |
| ATOM | 15482 | CD1 | PHE | B | 434 | 53.915 | 24.668 | −26.771 | 1.00 | 13.37 | B | C |
| ATOM | 15484 | CE1 | PHE | B | 434 | 54.026 | 23.285 | −26.894 | 1.00 | 13.68 | B | C |
| ATOM | 15486 | CZ | PHE | B | 434 | 53.311 | 22.454 | −26.049 | 1.00 | 12.83 | B | C |
| ATOM | 15488 | CE2 | PHE | B | 434 | 52.482 | 23.002 | −25.092 | 1.00 | 13.60 | B | C |
| ATOM | 15490 | CD2 | PHE | B | 434 | 52.367 | 24.379 | −24.978 | 1.00 | 14.39 | B | C |
| ATOM | 15492 | C | PHE | B | 434 | 52.689 | 27.132 | −28.153 | 1.00 | 12.75 | B | C |
| ATOM | 15493 | O | PHE | B | 434 | 53.341 | 26.578 | −29.036 | 1.00 | 12.94 | B | O |
| ATOM | 15495 | N | ARG | B | 435 | 51.397 | 27.409 | −28.278 | 1.00 | 12.65 | B | N |
| ATOM | 15496 | CA | ARG | B | 435 | 50.647 | 27.077 | −29.490 | 1.00 | 12.43 | B | C |
| ATOM | 15498 | CB | ARG | B | 435 | 49.146 | 27.269 | −29.238 | 1.00 | 12.62 | B | C |
| ATOM | 15501 | CG | ARG | B | 435 | 48.244 | 27.150 | −30.463 | 1.00 | 13.62 | B | C |
| ATOM | 15504 | CD | ARG | B | 435 | 48.426 | 25.839 | −31.211 | 1.00 | 15.01 | B | C |
| ATOM | 15507 | NE | ARG | B | 435 | 48.056 | 24.675 | −30.411 | 1.00 | 15.74 | B | N |
| ATOM | 15509 | CZ | ARG | B | 435 | 48.332 | 23.415 | −30.739 | 1.00 | 17.48 | B | C |
| ATOM | 15510 | NH1 | ARG | B | 435 | 48.997 | 23.124 | −31.856 | 1.00 | 18.48 | B | N |
| ATOM | 15513 | NH2 | ARG | B | 435 | 47.948 | 22.434 | −29.936 | 1.00 | 18.57 | B | N |
| ATOM | 15516 | C | ARG | B | 435 | 51.098 | 27.898 | −30.708 | 1.00 | 12.48 | B | C |
| ATOM | 15517 | O | ARG | B | 435 | 51.168 | 27.370 | −31.817 | 1.00 | 12.61 | B | O |

TABLE 8-2-continued

Coordinates for L494P Structure

| | | | | | | | | | | | | |
|---|---|---|---|---|---|---|---|---|---|---|---|---|
| ATOM | 15519 | N | LEU | B | 436 | 51.401 | 29.180 | −30.504 | 1.00 | 12.45 | B | N |
| ATOM | 15520 | CA | LEU | B | 436 | 51.812 | 30.060 | −31.606 | 1.00 | 12.32 | B | C |
| ATOM | 15522 | CB | LEU | B | 436 | 51.884 | 31.521 | −31.153 | 1.00 | 12.22 | B | C |
| ATOM | 15525 | CG | LEU | B | 436 | 50.576 | 32.303 | −31.063 | 1.00 | 11.85 | B | C |
| ATOM | 15527 | CD1 | LEU | B | 436 | 50.876 | 33.761 | −30.737 | 1.00 | 12.49 | B | C |
| ATOM | 15531 | CD2 | LEU | B | 436 | 49.782 | 32.196 | −32.351 | 1.00 | 11.29 | B | C |
| ATOM | 15535 | C | LEU | B | 436 | 53.153 | 29.669 | −32.225 | 1.00 | 12.83 | B | C |
| ATOM | 15536 | O | LEU | B | 436 | 53.335 | 29.800 | −33.433 | 1.00 | 12.98 | B | O |
| ATOM | 15538 | N | CYS | B | 437 | 54.093 | 29.214 | −31.402 | 1.00 | 13.39 | B | N |
| ATOM | 15539 | CA | CYS | B | 437 | 55.387 | 28.759 | −31.903 | 1.00 | 13.88 | B | C |
| ATOM | 15541 | CB | CYS | B | 437 | 56.381 | 28.581 | −30.753 | 1.00 | 13.94 | B | C |
| ATOM | 15544 | SG | CYS | B | 437 | 56.826 | 30.125 | −29.910 | 1.00 | 15.60 | B | S |
| ATOM | 15546 | C | CYS | B | 437 | 55.219 | 27.449 | −32.668 | 1.00 | 14.16 | B | C |
| ATOM | 15547 | O | CYS | B | 437 | 55.625 | 27.343 | −33.825 | 1.00 | 14.34 | B | O |
| ATOM | 15549 | N | ASN | B | 438 | 54.602 | 26.466 | −32.014 | 1.00 | 14.40 | B | N |
| ATOM | 15550 | CA | ASN | B | 438 | 54.336 | 25.156 | −32.612 | 1.00 | 14.88 | B | C |
| ATOM | 15552 | CB | ASN | B | 438 | 53.450 | 24.324 | −31.674 | 1.00 | 15.18 | B | C |
| ATOM | 15555 | CG | ASN | B | 438 | 52.919 | 23.050 | −32.324 | 1.00 | 16.21 | B | C |
| ATOM | 15556 | OD1 | ASN | B | 438 | 51.766 | 22.669 | −32.104 | 1.00 | 17.51 | B | O |
| ATOM | 15557 | ND2 | ASN | B | 438 | 53.754 | 22.387 | −33.122 | 1.00 | 16.34 | B | N |
| ATOM | 15560 | C | ASN | B | 438 | 53.687 | 25.252 | −33.991 | 1.00 | 14.99 | B | C |
| ATOM | 15561 | O | ASN | B | 438 | 54.140 | 24.613 | −34.941 | 1.00 | 15.21 | B | O |
| ATOM | 15563 | N | ASP | B | 439 | 52.623 | 26.042 | −34.091 | 1.00 | 15.13 | B | N |
| ATOM | 15564 | CA | ASP | B | 439 | 51.912 | 26.202 | −35.358 | 1.00 | 15.33 | B | C |
| ATOM | 15566 | CB | ASP | B | 439 | 50.546 | 26.880 | −35.147 | 1.00 | 15.20 | B | C |
| ATOM | 15569 | CG | ASP | B | 439 | 49.512 | 25.946 | −34.501 | 1.00 | 14.78 | B | C |
| ATOM | 15570 | OD1 | ASP | B | 439 | 49.909 | 24.940 | −33.876 | 1.00 | 13.59 | B | O |
| ATOM | 15571 | OD2 | ASP | B | 439 | 48.295 | 26.218 | −34.619 | 1.00 | 13.26 | B | O |
| ATOM | 15572 | C | ASP | B | 439 | 52.767 | 26.968 | −36.374 | 1.00 | 15.73 | B | C |
| ATOM | 15573 | O | ASP | B | 439 | 52.689 | 26.698 | −37.574 | 1.00 | 15.79 | B | O |
| ATOM | 15575 | N | LEU | B | 440 | 53.587 | 27.904 | −35.892 | 1.00 | 16.14 | B | N |
| ATOM | 15576 | CA | LEU | B | 440 | 54.514 | 28.640 | −36.761 | 1.00 | 16.51 | B | C |
| ATOM | 15578 | CB | LEU | B | 440 | 55.158 | 29.824 | −36.031 | 1.00 | 16.13 | B | C |
| ATOM | 15581 | CG | LEU | B | 440 | 54.414 | 31.156 | −36.092 | 1.00 | 15.62 | B | C |
| ATOM | 15583 | CD1 | LEU | B | 440 | 55.083 | 32.170 | −35.174 | 1.00 | 15.61 | B | C |
| ATOM | 15587 | CD2 | LEU | B | 440 | 54.358 | 31.676 | −37.520 | 1.00 | 14.42 | B | C |
| ATOM | 15591 | C | LEU | B | 440 | 55.611 | 27.737 | −37.316 | 1.00 | 17.37 | B | C |
| ATOM | 15592 | O | LEU | B | 440 | 56.085 | 27.949 | −38.432 | 1.00 | 18.00 | B | O |
| ATOM | 15594 | N | ALA | B | 441 | 56.017 | 26.742 | −36.534 | 1.00 | 18.07 | B | N |
| ATOM | 15595 | CA | ALA | B | 441 | 57.053 | 25.804 | −36.962 | 1.00 | 18.79 | B | C |
| ATOM | 15597 | CB | ALA | B | 441 | 57.436 | 24.880 | −35.814 | 1.00 | 18.94 | B | C |
| ATOM | 15601 | C | ALA | B | 441 | 56.608 | 24.984 | −38.173 | 1.00 | 19.39 | B | C |
| ATOM | 15602 | O | ALA | B | 441 | 57.367 | 24.821 | −39.130 | 1.00 | 19.34 | B | O |
| ATOM | 15604 | N | SER | B | 442 | 55.372 | 24.488 | −38.129 | 1.00 | 20.04 | B | N |
| ATOM | 15605 | CA | SER | B | 442 | 54.835 | 23.620 | −39.178 | 1.00 | 20.72 | B | C |
| ATOM | 15607 | CB | SER | B | 442 | 54.010 | 22.503 | −38.537 | 1.00 | 20.68 | B | C |
| ATOM | 15610 | OG | SER | B | 442 | 52.872 | 23.030 | −37.876 | 1.00 | 21.27 | B | O |
| ATOM | 15612 | C | SER | B | 442 | 53.970 | 24.359 | −40.208 | 1.00 | 21.39 | B | C |
| ATOM | 15613 | O | SER | B | 442 | 53.341 | 23.722 | −41.055 | 1.00 | 21.51 | B | O |
| ATOM | 15615 | N | ALA | B | 443 | 53.953 | 25.690 | −40.147 | 1.00 | 22.14 | B | N |
| ATOM | 15616 | CA | ALA | B | 443 | 53.036 | 26.503 | −40.957 | 1.00 | 22.64 | B | C |
| ATOM | 15618 | CB | ALA | B | 443 | 53.249 | 27.988 | −40.666 | 1.00 | 22.67 | B | C |
| ATOM | 15622 | C | ALA | B | 443 | 53.139 | 26.241 | −42.463 | 1.00 | 22.85 | B | C |
| ATOM | 15623 | O | ALA | B | 443 | 52.206 | 25.712 | −43.068 | 1.00 | 22.40 | B | O |
| ATOM | 15625 | N | SER | B | 444 | 54.274 | 26.603 | −43.056 | 1.00 | 23.46 | B | N |
| ATOM | 15626 | CA | SER | B | 444 | 54.460 | 26.513 | −44.509 | 1.00 | 24.13 | B | C |
| ATOM | 15628 | CB | SER | B | 444 | 55.851 | 27.015 | −44.903 | 1.00 | 24.32 | B | C |
| ATOM | 15631 | OG | SER | B | 444 | 56.864 | 26.161 | −44.398 | 1.00 | 25.37 | B | O |
| ATOM | 15633 | C | SER | B | 444 | 54.251 | 25.097 | −45.053 | 1.00 | 24.33 | B | C |
| ATOM | 15634 | O | SER | B | 444 | 53.795 | 24.925 | −46.184 | 1.00 | 24.33 | B | O |
| ATOM | 15636 | N | ALA | B | 445 | 54.595 | 24.093 | −44.249 | 1.00 | 24.60 | B | N |
| ATOM | 15637 | CA | ALA | B | 445 | 54.375 | 22.696 | −44.615 | 1.00 | 24.55 | B | C |
| ATOM | 15639 | CB | ALA | B | 445 | 55.038 | 21.770 | −43.601 | 1.00 | 24.40 | B | C |
| ATOM | 15643 | C | ALA | B | 445 | 52.881 | 22.400 | −44.706 | 1.00 | 24.64 | B | C |
| ATOM | 15644 | O | ALA | B | 445 | 52.380 | 22.032 | −45.767 | 1.00 | 24.53 | B | O |
| ATOM | 15646 | N | GLU | B | 446 | 52.176 | 22.587 | −43.593 | 1.00 | 24.83 | B | N |
| ATOM | 15647 | CA | GLU | B | 446 | 50.743 | 22.289 | −43.516 | 1.00 | 25.12 | B | C |
| ATOM | 15649 | CB | GLU | B | 446 | 50.230 | 22.457 | −42.075 | 1.00 | 25.24 | B | C |
| ATOM | 15652 | CG | GLU | B | 446 | 50.805 | 21.427 | −41.088 | 1.00 | 26.42 | B | C |
| ATOM | 15655 | CD | GLU | B | 446 | 50.271 | 21.565 | −39.660 | 1.00 | 27.29 | B | C |
| ATOM | 15656 | OE1 | GLU | B | 446 | 49.633 | 22.589 | −39.336 | 1.00 | 29.11 | B | O |
| ATOM | 15657 | OE2 | GLU | B | 446 | 50.500 | 20.638 | −38.853 | 1.00 | 26.37 | B | O |
| ATOM | 15658 | C | GLU | B | 446 | 49.912 | 23.137 | −44.488 | 1.00 | 25.03 | B | C |
| ATOM | 15659 | O | GLU | B | 446 | 48.903 | 22.667 | −45.013 | 1.00 | 25.21 | B | O |
| ATOM | 15661 | N | ILE | B | 447 | 50.343 | 24.373 | −44.734 | 1.00 | 24.84 | B | N |
| ATOM | 15662 | CA | ILE | B | 447 | 49.633 | 25.274 | −45.647 | 1.00 | 24.77 | B | C |
| ATOM | 15664 | CB | ILE | B | 447 | 50.218 | 26.709 | −45.600 | 1.00 | 24.76 | B | C |
| ATOM | 15666 | CG1 | ILE | B | 447 | 49.850 | 27.386 | −44.276 | 1.00 | 24.75 | B | C |

TABLE 8-2-continued

Coordinates for L494P Structure

| | | | | | | | | | | | |
|---|---|---|---|---|---|---|---|---|---|---|---|
| ATOM | 15669 | CD1 | ILE | B | 447 | 50.783 | 28.510 | −43.879 | 1.00 | 24.00 B | C |
| ATOM | 15673 | CG2 | ILE | B | 447 | 49.706 | 27.547 | −46.771 | 1.00 | 23.20 B | C |
| ATOM | 15677 | C | ILE | B | 447 | 49.653 | 24.752 | −47.085 | 1.00 | 25.09 B | C |
| ATOM | 15678 | O | ILE | B | 447 | 48.612 | 24.699 | −47.742 | 1.00 | 25.20 B | O |
| ATOM | 15680 | N | ALA | B | 448 | 50.835 | 24.358 | −47.560 | 1.00 | 25.30 B | N |
| ATOM | 15681 | CA | ALA | B | 448 | 51.005 | 23.871 | −48.935 | 1.00 | 25.10 B | C |
| ATOM | 15683 | CB | ALA | B | 448 | 52.485 | 23.792 | −49.294 | 1.00 | 24.84 B | C |
| ATOM | 15687 | C | ALA | B | 448 | 50.323 | 22.521 | −49.183 | 1.00 | 25.08 B | C |
| ATOM | 15688 | O | ALA | B | 448 | 50.005 | 22.192 | −50.324 | 1.00 | 25.19 B | O |
| ATOM | 15690 | N | ARG | B | 449 | 50.106 | 21.745 | −48.121 | 1.00 | 25.21 B | N |
| ATOM | 15691 | CA | ARG | B | 449 | 49.342 | 20.495 | −48.214 | 1.00 | 25.32 B | C |
| ATOM | 15693 | CB | ARG | B | 449 | 49.540 | 19.636 | −46.964 | 1.00 | 25.46 B | C |
| ATOM | 15696 | CG | ARG | B | 449 | 50.959 | 19.185 | −46.680 | 1.00 | 25.13 B | C |
| ATOM | 15699 | CD | ARG | B | 449 | 50.986 | 18.373 | −45.391 | 1.00 | 24.41 B | C |
| ATOM | 15702 | NE | ARG | B | 449 | 52.221 | 18.551 | −44.632 | 1.00 | 24.69 B | N |
| ATOM | 15704 | CZ | ARG | B | 449 | 52.395 | 18.161 | −43.368 | 1.00 | 24.86 B | C |
| ATOM | 15705 | NH1 | ARG | B | 449 | 51.412 | 17.563 | −42.698 | 1.00 | 25.32 B | N |
| ATOM | 15708 | NH2 | ARG | B | 449 | 53.561 | 18.372 | −42.765 | 1.00 | 24.17 B | N |
| ATOM | 15711 | C | ARG | B | 449 | 47.843 | 20.749 | −48.357 | 1.00 | 25.44 B | C |
| ATOM | 15712 | O | ARG | B | 449 | 47.103 | 19.868 | −48.793 | 1.00 | 25.60 B | O |
| ATOM | 15714 | N | GLY | B | 450 | 47.399 | 21.940 | −47.961 | 1.00 | 25.52 B | N |
| ATOM | 15715 | CA | GLY | B | 450 | 45.978 | 22.269 | −47.919 | 1.00 | 25.45 B | C |
| ATOM | 15718 | C | GLY | B | 450 | 45.347 | 21.972 | −46.568 | 1.00 | 25.40 B | C |
| ATOM | 15719 | O | GLY | B | 450 | 44.125 | 21.849 | −46.471 | 1.00 | 25.56 B | O |
| ATOM | 15721 | N | GLU | B | 451 | 46.171 | 21.852 | −45.525 | 1.00 | 25.17 B | N |
| ATOM | 15722 | CA | GLU | B | 451 | 45.666 | 21.675 | −44.162 | 1.00 | 25.18 B | C |
| ATOM | 15724 | CB | GLU | B | 451 | 46.685 | 20.956 | −43.271 | 1.00 | 25.44 B | C |
| ATOM | 15727 | CG | GLU | B | 451 | 46.811 | 19.460 | −43.546 | 1.00 | 26.78 B | C |
| ATOM | 15730 | CD | GLU | B | 451 | 47.637 | 18.724 | −42.496 | 1.00 | 28.97 B | C |
| ATOM | 15731 | OE1 | GLU | B | 451 | 47.800 | 19.2 | −41.368 | 1.00 | 30.01 B | O |
| ATOM | 15732 | OE2 | GLU | B | 451 | 48.122 | 17.6 | −42.799 | 1.00 | 30.31 B | O |
| ATOM | 15733 | C | GLU | B | 451 | 45.308 | 23.029 | −43.551 | 1.00 | 24.68 B | C |
| ATOM | 15734 | O | GLU | B | 451 | 46.039 | 24.007 | −43.716 | 1.00 | 24.69 B | O |
| ATOM | 15736 | N | THR | B | 452 | 44.179 | 23.069 | −42.845 | 1.00 | 24.05 B | N |
| ATOM | 15737 | CA | THR | B | 452 | 43.680 | 24.299 | −42.223 | 1.00 | 23.13 B | C |
| ATOM | 15739 | CB | THR | B | 452 | 42.176 | 24.536 | −42.552 | 1.00 | 23.21 B | C |
| ATOM | 15741 | OG1 | THR | B | 452 | 41.494 | 23.281 | −42.679 | 1.00 | 22.65 B | O |
| ATOM | 15743 | CG2 | THR | B | 452 | 42.023 | 25.322 | −43.850 | 1.00 | 22.06 B | C |
| ATOM | 15747 | C | THR | B | 452 | 43.878 | 24.338 | −40.702 | 1.00 | 22.26 B | C |
| ATOM | 15748 | O | THR | B | 452 | 43.816 | 25.416 | −40.107 | 1.00 | 22.08 B | O |
| ATOM | 15750 | N | ALA | B | 453 | 44.119 | 23.182 | −40.078 | 1.00 | 21.27 B | N |
| ATOM | 15751 | CA | ALA | B | 453 | 44.318 | 23.105 | −38.624 | 1.00 | 20.51 B | C |
| ATOM | 15753 | CB | ALA | B | 453 | 44.174 | 21.670 | −38.137 | 1.00 | 20.50 B | C |
| ATOM | 15757 | C | ALA | B | 453 | 45.680 | 23.674 | −38.222 | 1.00 | 20.10 B | C |
| ATOM | 15758 | O | ALA | B | 453 | 46.590 | 22.946 | −37.816 | 1.00 | 20.31 B | O |
| ATOM | 15760 | N | ASN | B | 454 | 45.793 | 24.992 | −38.343 | 1.00 | 19.21 B | N |
| ATOM | 15761 | CA | ASN | B | 454 | 46.991 | 25.736 | −37.982 | 1.00 | 17.99 B | C |
| ATOM | 15763 | CB | ASN | B | 454 | 48.020 | 25.682 | −39.117 | 1.00 | 17.83 B | C |
| ATOM | 15766 | CG | ASN | B | 454 | 49.386 | 26.230 | −38.709 | 1.00 | 17.61 B | C |
| ATOM | 15767 | OD1 | ASN | B | 454 | 49.581 | 27.442 | −38.617 | 1.00 | 17.15 B | O |
| ATOM | 15768 | ND2 | ASN | B | 454 | 50.341 | 25.334 | −38.485 | 1.00 | 16.02 B | N |
| ATOM | 15771 | C | ASN | B | 454 | 46.555 | 27.168 | −37.705 | 1.00 | 17.02 B | C |
| ATOM | 15772 | O | ASN | B | 454 | 45.631 | 27.671 | −38.343 | 1.00 | 16.92 B | O |
| ATOM | 15774 | N | SER | B | 455 | 47.198 | 27.816 | −36.743 | 1.00 | 16.17 B | N |
| ATOM | 15775 | CA | SER | B | 455 | 46.830 | 29.178 | −36.373 | 1.00 | 15.49 B | C |
| ATOM | 15777 | CB | SER | B | 455 | 47.504 | 29.571 | −35.061 | 1.00 | 15.49 B | C |
| ATOM | 15780 | OG | SER | B | 455 | 47.026 | 28.759 | −34.002 | 1.00 | 15.01 B | O |
| ATOM | 15782 | C | SER | B | 455 | 47.165 | 30.177 | −37.482 | 1.00 | 15.01 B | C |
| ATOM | 15783 | O | SER | B | 455 | 46.369 | 31.068 | −37.780 | 1.00 | 14.87 B | O |
| ATOM | 15785 | N | VAL | B | 456 | 48.331 | 30.015 | −38.104 | 1.00 | 14.62 B | N |
| ATOM | 15786 | CA | VAL | B | 456 | 48.729 | 30.885 | −39.214 | 1.00 | 14.23 B | C |
| ATOM | 15788 | CB | VAL | B | 456 | 50.186 | 30.623 | −39.660 | 1.00 | 13.71 B | C |
| ATOM | 15790 | CG1 | VAL | B | 456 | 50.564 | 31.530 | −40.820 | 1.00 | 12.75 B | C |
| ATOM | 15794 | CG2 | VAL | B | 456 | 51.140 | 30.836 | −38.498 | 1.00 | 12.43 B | C |
| ATOM | 15798 | C | VAL | B | 456 | 47.769 | 30.725 | −40.399 | 1.00 | 14.74 B | C |
| ATOM | 15799 | O | VAL | B | 456 | 47.520 | 31.682 | −41.133 | 1.00 | 15.01 B | O |
| ATOM | 15801 | N | SER | B | 457 | 47.228 | 29.521 | −40.573 | 1.00 | 15.08 B | N |
| ATOM | 15802 | CA | SER | B | 457 | 46.194 | 29.275 | −41.579 | 1.00 | 15.28 B | C |
| ATOM | 15804 | CB | SER | B | 457 | 45.918 | 27.775 | −41.728 | 1.00 | 15.22 B | C |
| ATOM | 15807 | OG | SER | B | 457 | 44.712 | 27.543 | −42.437 | 1.00 | 15.09 B | O |
| ATOM | 15809 | C | SER | B | 457 | 44.902 | 30.009 | −41.227 | 1.00 | 15.53 B | C |
| ATOM | 15810 | O | SER | B | 457 | 44.311 | 30.663 | −42.082 | 1.00 | 15.71 B | O |
| ATOM | 15812 | N | CYS | B | 458 | 44.469 | 29.893 | −39.973 | 1.00 | 15.80 B | N |
| ATOM | 15813 | CA | CYS | B | 458 | 43.245 | 30.559 | −39.515 | 1.00 | 16.11 B | C |
| ATOM | 15815 | CB | CYS | B | 458 | 42.912 | 30.183 | −38.070 | 1.00 | 15.87 B | C |
| ATOM | 15818 | SG | CYS | B | 458 | 42.128 | 28.572 | −37.880 | 1.00 | 18.08 B | S |
| ATOM | 15820 | C | CYS | B | 458 | 43.354 | 32.072 | −39.628 | 1.00 | 16.21 B | C |
| ATOM | 15821 | O | CYS | B | 458 | 42.379 | 32.744 | −39.968 | 1.00 | 17.07 B | O |

TABLE 8-2-continued

Coordinates for L494P Structure

| | | | | | | | | | | | | |
|---|---|---|---|---|---|---|---|---|---|---|---|---|
| ATOM | 15823 | N | TYR | B | 459 | 44.539 | 32.602 | −39.342 | 1.00 | 15.90 | B | N |
| ATOM | 15824 | CA | TYR | B | 459 | 44.771 | 34.039 | −39.424 | 1.00 | 15.53 | B | C |
| ATOM | 15826 | CB | TYR | B | 459 | 46.084 | 34.420 | −38.727 | 1.00 | 15.20 | B | C |
| ATOM | 15829 | CG | TYR | B | 459 | 46.116 | 35.848 | −38.221 | 1.00 | 13.77 | B | C |
| ATOM | 15830 | CD1 | TYR | B | 459 | 45.880 | 36.142 | −36.880 | 1.00 | 11.99 | B | C |
| ATOM | 15832 | CE1 | TYR | B | 459 | 45.906 | 37.452 | −36.416 | 1.00 | 10.67 | B | C |
| ATOM | 15834 | CZ | TYR | B | 459 | 46.170 | 38.483 | −37.298 | 1.00 | 10.73 | B | C |
| ATOM | 15835 | OH | TYR | B | 459 | 46.202 | 39.785 | −36.855 | 1.00 | 12.04 | B | O |
| ATOM | 15837 | CE2 | TYR | B | 459 | 46.406 | 38.216 | −38.630 | 1.00 | 11.92 | B | C |
| ATOM | 15839 | CD2 | TYR | B | 459 | 46.376 | 36.906 | −39.086 | 1.00 | 13.04 | B | C |
| ATOM | 15841 | C | TYR | B | 459 | 44.765 | 34.507 | −40.884 | 1.00 | 15.64 | B | C |
| ATOM | 15842 | O | TYR | B | 459 | 44.354 | 35.630 | −41.171 | 1.00 | 15.37 | B | O |
| ATOM | 15844 | N | MET | B | 460 | 45.209 | 33.646 | −41.798 | 1.00 | 16.17 | B | N |
| ATOM | 15845 | CA | MET | B | 460 | 45.137 | 33.935 | −43.234 | 1.00 | 17.10 | B | C |
| ATOM | 15847 | CB | MET | B | 460 | 45.871 | 32.865 | −44.049 | 1.00 | 17.68 | B | C |
| ATOM | 15850 | CG | MET | B | 460 | 47.381 | 33.004 | −44.070 | 1.00 | 20.00 | B | C |
| ATOM | 15853 | SD | MET | B | 460 | 48.194 | 31.536 | −44.746 | 1.00 | 24.41 | B | S |
| ATOM | 15854 | CE | MET | B | 460 | 47.441 | 31.432 | −46.371 | 1.00 | 21.79 | B | C |
| ATOM | 15858 | C | MET | B | 460 | 43.690 | 34.021 | −43.726 | 1.00 | 17.18 | B | C |
| ATOM | 15859 | O | MET | B | 460 | 43.328 | 34.962 | −44.434 | 1.00 | 17.43 | B | O |
| ATOM | 15861 | N | ARG | B | 461 | 42.877 | 33.031 | −43.359 | 1.00 | 17.00 | B | N |
| ATOM | 15862 | CA | ARG | B | 461 | 41.472 | 32.966 | −43.784 | 1.00 | 16.70 | B | C |
| ATOM | 15864 | CB | ARG | B | 461 | 40.848 | 31.623 | −43.399 | 1.00 | 16.92 | B | C |
| ATOM | 15867 | CG | ARG | B | 461 | 41.012 | 30.525 | −44.433 | 1.00 | 17.73 | B | C |
| ATOM | 15870 | CD | ARG | B | 461 | 40.488 | 29.211 | −43.879 | 1.00 | 19.18 | B | C |
| ATOM | 15873 | NE | ARG | B | 461 | 41.337 | 28.716 | −42.794 | 1.00 | 19.69 | B | N |
| ATOM | 15875 | CZ | ARG | B | 461 | 40.942 | 27.907 | −41.810 | 1.00 | 20.75 | B | C |
| ATOM | 15876 | NH1 | ARG | B | 461 | 39.687 | 27.474 | −41.729 | 1.00 | 20.89 | B | N |
| ATOM | 15879 | NH2 | ARG | B | 461 | 41.819 | 27.534 | −40.886 | 1.00 | 22.40 | B | N |
| ATOM | 15882 | C | ARG | B | 461 | 40.621 | 34.079 | −43.186 | 1.00 | 16.22 | B | C |
| ATOM | 15883 | O | ARG | B | 461 | 39.803 | 34.683 | −43.879 | 1.00 | 16.34 | B | O |
| ATOM | 15885 | N | THR | B | 462 | 40.807 | 34.330 | −41.895 | 1.00 | 15.74 | B | N |
| ATOM | 15886 | CA | THR | B | 462 | 40.008 | 35.317 | −41.181 | 1.00 | 15.73 | B | C |
| ATOM | 15888 | CB | THR | B | 462 | 40.255 | 35.228 | −39.672 | 1.00 | 15.53 | B | C |
| ATOM | 15890 | OG1 | THR | B | 462 | 39.962 | 33.900 | −39.224 | 1.00 | 15.96 | B | O |
| ATOM | 15892 | CG2 | THR | B | 462 | 39.379 | 36.217 | −38.924 | 1.00 | 16.51 | B | C |
| ATOM | 15896 | C | THR | B | 462 | 40.261 | 36.749 | −41.649 | 1.00 | 15.94 | B | C |
| ATOM | 15897 | O | THR | B | 462 | 39.322 | 37.532 | −41.801 | 1.00 | 16.24 | B | O |
| ATOM | 15899 | N | LYS | B | 463 | 41.527 | 37.084 | −41.876 | 1.00 | 15.98 | B | N |
| ATOM | 15900 | CA | LYS | B | 463 | 41.906 | 38.423 | −42.316 | 1.00 | 16.21 | B | C |
| ATOM | 15902 | CB | LYS | B | 463 | 43.232 | 38.827 | −41.672 | 1.00 | 16.41 | B | C |
| ATOM | 15905 | CG | LYS | B | 463 | 43.165 | 38.978 | −40.152 | 1.00 | 16.93 | B | C |
| ATOM | 15908 | CD | LYS | B | 463 | 42.539 | 40.306 | −39.738 | 1.00 | 16.56 | B | C |
| ATOM | 15911 | CE | LYS | B | 463 | 42.716 | 40.567 | −38.251 | 1.00 | 16.16 | B | C |
| ATOM | 15914 | NZ | LYS | B | 463 | 42.453 | 41.992 | −37.910 | 1.00 | 15.98 | B | N |
| ATOM | 15918 | C | LYS | B | 463 | 42.010 | 38.525 | −43.838 | 1.00 | 16.35 | B | C |
| ATOM | 15919 | O | LYS | B | 463 | 42.119 | 39.628 | −44.379 | 1.00 | 16.35 | B | O |
| ATOM | 15921 | N | GLY | B | 464 | 41.977 | 37.381 | −44.520 | 1.00 | 16.54 | B | N |
| ATOM | 15922 | CA | GLY | B | 464 | 42.063 | 37.340 | −45.978 | 1.00 | 16.78 | B | C |
| ATOM | 15925 | C | GLY | B | 464 | 43.348 | 37.955 | −46.500 | 1.00 | 17.14 | B | C |
| ATOM | 15926 | O | GLY | B | 464 | 43.316 | 38.779 | −47.415 | 1.00 | 17.35 | B | O |
| ATOM | 15928 | N | ILE | B | 465 | 44.477 | 37.550 | −45.917 | 1.00 | 17.39 | B | N |
| ATOM | 15929 | CA | ILE | B | 465 | 45.789 | 38.112 | −46.265 | 1.00 | 17.68 | B | C |
| ATOM | 15931 | CB | ILE | B | 465 | 46.356 | 39.000 | −45.122 | 1.00 | 17.52 | B | C |
| ATOM | 15933 | CG1 | ILE | B | 465 | 46.503 | 38.208 | −43.818 | 1.00 | 16.22 | B | C |
| ATOM | 15936 | CD1 | ILE | B | 465 | 47.122 | 39.001 | −42.698 | 1.00 | 13.96 | B | C |
| ATOM | 15940 | CG2 | ILE | B | 465 | 45.457 | 40.206 | −44.901 | 1.00 | 18.60 | B | C |
| ATOM | 15944 | C | ILE | B | 465 | 46.802 | 37.022 | −46.626 | 1.00 | 18.16 | B | C |
| ATOM | 15945 | O | ILE | B | 465 | 46.529 | 35.831 | −46.464 | 1.00 | 18.09 | B | O |
| ATOM | 15947 | N | SER | B | 466 | 47.966 | 37.448 | −47.118 | 1.00 | 18.79 | B | N |
| ATOM | 15948 | CA | SER | B | 466 | 49.035 | 36.535 | −47.538 | 1.00 | 19.13 | B | C |
| ATOM | 15950 | CB | SER | B | 466 | 50.103 | 37.303 | −48.318 | 1.00 | 19.18 | B | C |
| ATOM | 15953 | OG | SER | B | 466 | 50.799 | 38.203 | −47.471 | 1.00 | 18.23 | B | O |
| ATOM | 15955 | C | SER | B | 466 | 49.694 | 35.843 | −46.349 | 1.00 | 19.60 | B | C |
| ATOM | 15956 | O | SER | B | 466 | 49.741 | 36.401 | −45.251 | 1.00 | 19.64 | B | O |
| ATOM | 15958 | N | GLU | B | 467 | 50.216 | 34.637 | −46.581 | 1.00 | 20.01 | B | N |
| ATOM | 15959 | CA | GLU | B | 467 | 50.903 | 33.862 | −45.535 | 1.00 | 20.44 | B | C |
| ATOM | 15961 | CB | GLU | B | 467 | 51.440 | 32.541 | −46.106 | 1.00 | 20.58 | B | C |
| ATOM | 15964 | CG | GLU | B | 467 | 52.180 | 31.664 | −45.086 | 1.00 | 20.96 | B | C |
| ATOM | 15967 | CD | GLU | B | 467 | 52.735 | 30.383 | −45.685 | 1.00 | 21.70 | B | C |
| ATOM | 15968 | OE1 | GLU | B | 467 | 52.053 | 29.765 | −46.530 | 1.00 | 22.54 | B | O |
| ATOM | 15969 | OE2 | GLU | B | 467 | 53.854 | 29.984 | −45.296 | 1.00 | 22.39 | B | O |
| ATOM | 15970 | C | GLU | B | 467 | 52.047 | 34.650 | −44.895 | 1.00 | 20.53 | B | C |
| ATOM | 15971 | O | GLU | B | 467 | 52.293 | 34.541 | −43.692 | 1.00 | 20.25 | B | O |
| ATOM | 15973 | N | GLU | B | 468 | 52.744 | 35.432 | −45.714 | 1.00 | 20.89 | B | N |
| ATOM | 15974 | CA | GLU | B | 468 | 53.826 | 36.295 | −45.253 | 1.00 | 21.16 | B | C |
| ATOM | 15976 | CB | GLU | B | 468 | 54.438 | 37.025 | −46.451 | 1.00 | 21.39 | B | C |
| ATOM | 15979 | CG | GLU | B | 468 | 55.709 | 37.807 | −46.150 | 1.00 | 22.77 | B | C |

TABLE 8-2-continued

Coordinates for L494P Structure

| | | | | | | | | | | | | |
|---|---|---|---|---|---|---|---|---|---|---|---|---|
| ATOM | 15982 | CD | GLU | B | 468 | 56.147 | 38.680 | −47.317 | 1.00 | 25.04 | B | C |
| ATOM | 15983 | OE1 | GLU | B | 468 | 55.474 | 38.657 | −48.373 | 1.00 | 26.20 | B | O |
| ATOM | 15984 | OE2 | GLU | B | 468 | 57.164 | 39.393 | −47.179 | 1.00 | 26.28 | B | O |
| ATOM | 15985 | C | GLU | B | 468 | 53.330 | 37.316 | −44.225 | 1.00 | 20.91 | B | C |
| ATOM | 15986 | O | GLU | B | 468 | 53.981 | 37.540 | −43.203 | 1.00 | 21.14 | B | O |
| ATOM | 15988 | N | LEU | B | 469 | 52.179 | 37.925 | −44.507 | 1.00 | 20.46 | B | N |
| ATOM | 15989 | CA | LEU | B | 469 | 51.607 | 38.964 | −43.642 | 1.00 | 19.85 | B | C |
| ATOM | 15991 | CB | LEU | B | 469 | 50.616 | 39.833 | −44.433 | 1.00 | 19.93 | B | C |
| ATOM | 15994 | CG | LEU | B | 469 | 50.541 | 41.325 | −44.088 | 1.00 | 19.46 | B | C |
| ATOM | 15996 | CD1 | LEU | B | 469 | 49.630 | 42.035 | −45.081 | 1.00 | 19.01 | B | C |
| ATOM | 16000 | CD2 | LEU | B | 469 | 50.071 | 41.572 | −42.657 | 1.00 | 18.30 | B | C |
| ATOM | 16004 | C | LEU | B | 469 | 50.923 | 38.353 | −42.412 | 1.00 | 19.10 | B | C |
| ATOM | 16005 | O | LEU | B | 469 | 50.888 | 38.969 | −41.349 | 1.00 | 18.73 | B | O |
| ATOM | 16007 | N | ALA | B | 470 | 50.374 | 37.149 | −42.565 | 1.00 | 18.69 | B | N |
| ATOM | 16008 | CA | ALA | B | 470 | 49.770 | 36.427 | −41.443 | 1.00 | 18.30 | B | C |
| ATOM | 16010 | CB | ALA | B | 470 | 48.984 | 35.221 | −41.945 | 1.00 | 18.19 | B | C |
| ATOM | 16014 | C | ALA | B | 470 | 50.835 | 35.987 | −40.441 | 1.00 | 17.77 | B | C |
| ATOM | 16015 | O | ALA | B | 470 | 50.624 | 36.070 | −39.230 | 1.00 | 17.14 | B | O |
| ATOM | 16017 | N | THR | B | 471 | 51.970 | 35.517 | −40.961 | 1.00 | 17.77 | B | N |
| ATOM | 16018 | CA | THR | B | 471 | 53.128 | 35.137 | −40.141 | 1.00 | 17.92 | B | C |
| ATOM | 16020 | CB | THR | B | 471 | 54.264 | 34.553 | −41.009 | 1.00 | 17.78 | B | C |
| ATOM | 16022 | OG1 | THR | B | 471 | 53.940 | 33.208 | −41.381 | 1.00 | 18.24 | B | O |
| ATOM | 16024 | CG2 | THR | B | 471 | 55.586 | 34.559 | −40.261 | 1.00 | 17.26 | B | C |
| ATOM | 16028 | C | THR | B | 471 | 53.670 | 36.319 | −39.337 | 1.00 | 18.26 | B | C |
| ATOM | 16029 | O | THR | B | 471 | 54.011 | 36.171 | −38.164 | 1.00 | 18.51 | B | O |
| ATOM | 16031 | N | GLU | B | 472 | 53.747 | 37.483 | −39.979 | 1.00 | 18.50 | B | N |
| ATOM | 16032 | CA | GLU | B | 472 | 54.144 | 38.730 | −39.322 | 1.00 | 18.54 | B | C |
| ATOM | 16034 | CB | GLU | B | 472 | 54.078 | 39.882 | −40.333 | 1.00 | 18.66 | B | C |
| ATOM | 16037 | CG | GLU | B | 472 | 54.483 | 41.252 | −39.797 | 1.00 | 19.75 | B | C |
| ATOM | 16040 | CD | GLU | B | 472 | 54.306 | 42.361 | −40.825 | 1.00 | 20.71 | B | C |
| ATOM | 16041 | OE1 | GLU | B | 472 | 53.611 | 42.146 | −41.843 | 1.00 | 18.97 | B | O |
| ATOM | 16042 | OE2 | GLU | B | 472 | 54.864 | 43.457 | −40.610 | 1.00 | 22.53 | B | O |
| ATOM | 16043 | C | GLU | B | 472 | 53.255 | 39.043 | −38.112 | 1.00 | 18.37 | B | C |
| ATOM | 16044 | O | GLU | B | 472 | 53.753 | 39.376 | −37.036 | 1.00 | 18.21 | B | O |
| ATOM | 16046 | N | SER | B | 473 | 51.941 | 38.931 | −38.299 | 1.00 | 18.41 | B | N |
| ATOM | 16047 | CA | SER | B | 473 | 50.970 | 39.247 | −37.248 | 1.00 | 18.17 | B | C |
| ATOM | 16049 | CB | SER | B | 473 | 49.548 | 39.246 | −37.813 | 1.00 | 17.98 | B | C |
| ATOM | 16052 | OG | SER | B | 473 | 49.382 | 40.280 | −38.766 | 1.00 | 17.49 | B | O |
| ATOM | 16054 | C | SER | B | 473 | 51.058 | 38.289 | −36.061 | 1.00 | 18.17 | B | C |
| ATOM | 16055 | O | SER | B | 473 | 50.892 | 38.704 | −34.913 | 1.00 | 18.49 | B | O |
| ATOM | 16057 | N | VAL | B | 474 | 51.314 | 37.013 | −36.339 | 1.00 | 17.87 | B | N |
| ATOM | 16058 | CA | VAL | B | 474 | 51.508 | 36.026 | −35.278 | 1.00 | 17.81 | B | C |
| ATOM | 16060 | CB | VAL | B | 474 | 51.578 | 34.583 | −35.835 | 1.00 | 17.80 | B | C |
| ATOM | 16062 | CG1 | VAL | B | 474 | 51.912 | 33.591 | −34.727 | 1.00 | 16.61 | B | C |
| ATOM | 16066 | CG2 | VAL | B | 474 | 50.261 | 34.205 | −36.504 | 1.00 | 16.90 | B | C |
| ATOM | 16070 | C | VAL | B | 474 | 52.769 | 36.341 | −34.469 | 1.00 | 18.13 | B | C |
| ATOM | 16071 | O | VAL | B | 474 | 52.783 | 36.165 | −33.253 | 1.00 | 18.18 | B | O |
| ATOM | 16073 | N | MET | B | 475 | 53.817 | 36.817 | −35.139 | 1.00 | 18.76 | B | N |
| ATOM | 16074 | CA | MET | B | 475 | 55.033 | 37.248 | −34.443 | 1.00 | 19.47 | B | C |
| ATOM | 16076 | CB | MET | B | 475 | 56.131 | 37.658 | −35.433 | 1.00 | 19.73 | B | C |
| ATOM | 16079 | CG | MET | B | 475 | 56.654 | 36.537 | −36.319 | 1.00 | 20.45 | B | C |
| ATOM | 16082 | SD | MET | B | 475 | 57.699 | 35.349 | −35.460 | 1.00 | 23.17 | B | S |
| ATOM | 16083 | CE | MET | B | 475 | 58.311 | 34.392 | −36.849 | 1.00 | 21.35 | B | C |
| ATOM | 16087 | C | MET | B | 475 | 54.718 | 38.423 | −33.517 | 1.00 | 19.81 | B | C |
| ATOM | 16088 | O | MET | B | 475 | 55.195 | 38.471 | −32.383 | 1.00 | 19.66 | B | O |
| ATOM | 16090 | N | ASN | B | 476 | 53.912 | 39.363 | −34.009 | 1.00 | 20.14 | B | N |
| ATOM | 16091 | CA | ASN | B | 476 | 53.483 | 40.518 | −33.216 | 1.00 | 20.47 | B | C |
| ATOM | 16093 | CB | ASN | B | 476 | 52.766 | 41.543 | −34.102 | 1.00 | 20.65 | B | C |
| ATOM | 16096 | CG | ASN | B | 476 | 53.699 | 42.205 | −35.101 | 1.00 | 21.93 | B | C |
| ATOM | 16097 | OD1 | ASN | B | 476 | 54.734 | 42.757 | −34.726 | 1.00 | 24.56 | B | O |
| ATOM | 16098 | ND2 | ASN | B | 476 | 53.333 | 42.160 | −36.379 | 1.00 | 22.45 | B | N |
| ATOM | 16101 | C | ASN | B | 476 | 52.581 | 40.123 | −32.044 | 1.00 | 20.49 | B | C |
| ATOM | 16102 | O | ASN | B | 476 | 52.541 | 40.815 | −31.025 | 1.00 | 20.89 | B | O |
| ATOM | 16104 | N | LEU | B | 477 | 51.862 | 39.014 | −32.195 | 1.00 | 20.27 | B | N |
| ATOM | 16105 | CA | LEU | B | 477 | 51.019 | 38.481 | −31.123 | 1.00 | 19.90 | B | C |
| ATOM | 16107 | CB | LEU | B | 477 | 50.030 | 37.446 | −31.674 | 1.00 | 19.84 | B | C |
| ATOM | 16110 | CG | LEU | B | 477 | 48.636 | 37.462 | −31.046 | 1.00 | 19.42 | B | C |
| ATOM | 16112 | CD1 | LEU | B | 477 | 47.908 | 38.751 | −31.411 | 1.00 | 18.74 | B | C |
| ATOM | 16116 | CD2 | LEU | B | 477 | 47.841 | 36.247 | −31.494 | 1.00 | 18.32 | B | C |
| ATOM | 16120 | C | LEU | B | 477 | 51.877 | 37.863 | −30.013 | 1.00 | 19.60 | B | C |
| ATOM | 16121 | O | LEU | B | 477 | 51.480 | 37.864 | −28.845 | 1.00 | 19.36 | B | O |
| ATOM | 16123 | N | ILE | B | 478 | 53.045 | 37.335 | −30.386 | 1.00 | 19.33 | B | N |
| ATOM | 16124 | CA | ILE | B | 478 | 54.028 | 36.846 | −29.414 | 1.00 | 18.77 | B | C |
| ATOM | 16126 | CB | ILE | B | 478 | 55.159 | 36.038 | −30.092 | 1.00 | 18.25 | B | C |
| ATOM | 16128 | CG1 | ILE | B | 478 | 54.626 | 34.686 | −30.568 | 1.00 | 17.56 | B | C |
| ATOM | 16131 | CD1 | ILE | B | 478 | 55.694 | 33.767 | −31.126 | 1.00 | 17.90 | B | C |
| ATOM | 16135 | CG2 | ILE | B | 478 | 56.321 | 35.832 | −29.135 | 1.00 | 16.88 | B | C |
| ATOM | 16139 | C | ILE | B | 478 | 54.631 | 38.007 | −28.622 | 1.00 | 19.04 | B | C |

TABLE 8-2-continued

Coordinates for L494P Structure

| | | | | | | | | | | | | |
|---|---|---|---|---|---|---|---|---|---|---|---|---|
| ATOM | 16140 | O | ILE | B | 478 | 54.677 | 37.962 | −27.393 | 1.00 | 19.14 | B | O |
| ATOM | 16142 | N | ASP | B | 479 | 55.088 | 39.040 | −29.331 | 1.00 | 19.19 | B | N |
| ATOM | 16143 | CA | ASP | B | 479 | 55.605 | 40.255 | −28.694 | 1.00 | 19.30 | B | C |
| ATOM | 16145 | CB | ASP | B | 479 | 55.884 | 41.345 | −29.739 | 1.00 | 19.38 | B | C |
| ATOM | 16148 | CG | ASP | B | 479 | 57.121 | 41.061 | −30.580 | 1.00 | 19.94 | B | C |
| ATOM | 16149 | OD1 | ASP | B | 479 | 57.589 | 39.903 | −30.603 | 1.00 | 22.59 | B | O |
| ATOM | 16150 | OD2 | ASP | B | 479 | 57.625 | 42.004 | −31.228 | 1.00 | 19.87 | B | O |
| ATOM | 16151 | C | ASP | B | 479 | 54.625 | 40.792 | −27.649 | 1.00 | 19.52 | B | C |
| ATOM | 16152 | O | ASP | B | 479 | 55.007 | 41.051 | −26.506 | 1.00 | 19.57 | B | O |
| ATOM | 16154 | N | GLU | B | 480 | 53.362 | 40.940 | −28.044 | 1.00 | 19.62 | B | N |
| ATOM | 16155 | CA | GLU | B | 480 | 52.332 | 41.489 | −27.156 | 1.00 | 19.69 | B | C |
| ATOM | 16157 | CB | GLU | B | 480 | 51.053 | 41.813 | −27.939 | 1.00 | 19.64 | B | C |
| ATOM | 16160 | CG | GLU | B | 480 | 51.154 | 43.076 | −28.785 | 1.00 | 20.42 | B | C |
| ATOM | 16163 | CD | GLU | B | 480 | 51.566 | 44.302 | −27.976 | 1.00 | 21.42 | B | C |
| ATOM | 16164 | OE1 | GLU | B | 480 | 52.363 | 45.113 | −28.490 | 1.00 | 21.49 | B | O |
| ATOM | 16165 | OE2 | GLU | B | 480 | 51.104 | 44.448 | −26.823 | 1.00 | 21.89 | B | O |
| ATOM | 16166 | C | GLU | B | 480 | 52.004 | 40.588 | −25.966 | 1.00 | 19.49 | B | C |
| ATOM | 16167 | O | GLU | B | 480 | 51.663 | 41.085 | −24.889 | 1.00 | 19.09 | B | O |
| ATOM | 16169 | N | THR | B | 481 | 52.102 | 39.274 | −26.165 | 1.00 | 19.48 | B | N |
| ATOM | 16170 | CA | THR | B | 481 | 51.921 | 38.308 | −25.077 | 1.00 | 19.19 | B | C |
| ATOM | 16172 | CB | THR | B | 481 | 51.751 | 36.871 | −25.609 | 1.00 | 18.82 | B | C |
| ATOM | 16174 | OG1 | THR | B | 481 | 50.430 | 36.713 | −26.142 | 1.00 | 17.25 | B | O |
| ATOM | 16176 | CG2 | THR | B | 481 | 51.964 | 35.856 | −24.497 | 1.00 | 18.35 | B | C |
| ATOM | 16180 | C | THR | B | 481 | 53.093 | 38.359 | −24.092 | 1.00 | 19.61 | B | C |
| ATOM | 16181 | O | THR | B | 481 | 52.883 | 38.329 | −22.877 | 1.00 | 20.16 | B | O |
| ATOM | 16183 | N | TRP | B | 482 | 54.318 | 38.438 | −24.613 | 1.00 | 19.27 | B | N |
| ATOM | 16184 | CA | TRP | B | 482 | 55.503 | 38.600 | −23.763 | 1.00 | 19.03 | B | C |
| ATOM | 16186 | CB | TRP | B | 482 | 56.805 | 38.542 | −24.581 | 1.00 | 19.10 | B | C |
| ATOM | 16189 | CG | TRP | B | 482 | 57.389 | 37.164 | −24.652 | 1.00 | 19.78 | B | C |
| ATOM | 16190 | CD1 | TRP | B | 482 | 57.235 | 36.257 | −25.660 | 1.00 | 20.32 | B | C |
| ATOM | 16192 | NE1 | TRP | B | 482 | 57.906 | 35.097 | −25.360 | 1.00 | 20.19 | B | N |
| ATOM | 16194 | CE2 | TRP | B | 482 | 58.509 | 35.235 | −24.137 | 1.00 | 20.96 | B | C |
| ATOM | 16195 | CD2 | TRP | B | 482 | 58.203 | 36.526 | −23.660 | 1.00 | 20.92 | B | C |
| ATOM | 16196 | CE3 | TRP | B | 482 | 58.704 | 36.921 | −22.413 | 1.00 | 20.54 | B | C |
| ATOM | 16198 | CZ3 | TRP | B | 482 | 59.485 | 36.024 | −21.694 | 1.00 | 19.83 | B | C |
| ATOM | 16200 | CH2 | TRP | B | 482 | 59.775 | 34.750 | −22.197 | 1.00 | 18.86 | B | C |
| ATOM | 16202 | CZ2 | TRP | B | 482 | 59.300 | 34.336 | −23.413 | 1.00 | 19.97 | B | C |
| ATOM | 16204 | C | TRP | B | 482 | 55.439 | 39.896 | −22.960 | 1.00 | 18.96 | B | C |
| ATOM | 16205 | O | TRP | B | 482 | 55.892 | 39.935 | −21.818 | 1.00 | 18.99 | B | O |
| ATOM | 16207 | N | LYS | B | 483 | 54.871 | 40.945 | −23.553 | 1.00 | 18.84 | B | N |
| ATOM | 16208 | CA | LYS | B | 483 | 54.711 | 42.228 | −22.860 | 1.00 | 18.72 | B | C |
| ATOM | 16210 | CB | LYS | B | 483 | 54.188 | 43.306 | −23.818 | 1.00 | 18.58 | B | C |
| ATOM | 16213 | CG | LYS | B | 483 | 55.251 | 43.895 | −24.728 | 1.00 | 16.71 | B | C |
| ATOM | 16216 | CD | LYS | B | 483 | 54.670 | 44.960 | −25.639 | 1.00 | 14.83 | B | C |
| ATOM | 16219 | CE | LYS | B | 483 | 55.692 | 45.441 | −26.649 | 1.00 | 13.58 | B | C |
| ATOM | 16222 | NZ | LYS | B | 483 | 55.245 | 46.679 | −27.324 | 1.00 | 11.34 | B | N |
| ATOM | 16226 | C | LYS | B | 483 | 53.790 | 42.123 | −21.640 | 1.00 | 18.92 | B | C |
| ATOM | 16227 | O | LYS | B | 483 | 53.982 | 42.829 | −20.648 | 1.00 | 19.09 | B | O |
| ATOM | 16229 | N | LYS | B | 484 | 52.799 | 41.241 | −21.717 | 1.00 | 18.99 | B | N |
| ATOM | 16230 | CA | LYS | B | 484 | 51.861 | 41.039 | −20.615 | 1.00 | 19.49 | B | C |
| ATOM | 16232 | CB | LYS | B | 484 | 50.477 | 40.674 | −21.160 | 1.00 | 19.74 | B | C |
| ATOM | 16235 | CG | LYS | B | 484 | 49.839 | 41.803 | −21.979 | 1.00 | 20.77 | B | C |
| ATOM | 16238 | CD | LYS | B | 484 | 48.609 | 41.336 | −22.749 | 1.00 | 21.69 | B | C |
| ATOM | 16241 | CE | LYS | B | 484 | 48.153 | 42.369 | −23.775 | 1.00 | 21.40 | B | C |
| ATOM | 16244 | NZ | LYS | B | 484 | 47.244 | 41.774 | −24.798 | 1.00 | 21.11 | B | N |
| ATOM | 16248 | C | LYS | B | 484 | 52.368 | 39.992 | −19.614 | 1.00 | 19.34 | B | C |
| ATOM | 16249 | O | LYS | B | 484 | 52.050 | 40.061 | −18.427 | 1.00 | 19.45 | B | O |
| ATOM | 16251 | N | MET | B | 485 | 53.157 | 39.031 | −20.089 | 1.00 | 19.18 | B | N |
| ATOM | 16252 | CA | MET | B | 485 | 53.822 | 38.075 | −19.199 | 1.00 | 19.15 | B | C |
| ATOM | 16254 | CB | MET | B | 485 | 54.469 | 36.941 | −19.992 | 1.00 | 18.98 | B | C |
| ATOM | 16257 | CG | MET | B | 485 | 53.499 | 35.902 | −20.500 | 1.00 | 18.28 | B | C |
| ATOM | 16260 | SD | MET | B | 485 | 54.363 | 34.436 | −21.072 | 1.00 | 16.65 | B | S |
| ATOM | 16261 | CE | MET | B | 485 | 55.425 | 35.132 | −22.337 | 1.00 | 16.32 | B | C |
| ATOM | 16265 | C | MET | B | 485 | 54.897 | 38.750 | −18.353 | 1.00 | 19.51 | B | C |
| ATOM | 16266 | O | MET | B | 485 | 55.082 | 38.397 | −17.190 | 1.00 | 19.86 | B | O |
| ATOM | 16268 | N | ASN | B | 486 | 55.615 | 39.700 | −18.949 | 1.00 | 19.82 | B | N |
| ATOM | 16269 | CA | ASN | B | 486 | 56.642 | 40.457 | −18.234 | 1.00 | 20.17 | B | C |
| ATOM | 16271 | CB | ASN | B | 486 | 57.353 | 41.434 | −19.175 | 1.00 | 20.23 | B | C |
| ATOM | 16274 | CG | ASN | B | 486 | 58.260 | 40.739 | −20.174 | 1.00 | 20.22 | B | C |
| ATOM | 16275 | OD1 | ASN | B | 486 | 58.679 | 39.597 | −19.968 | 1.00 | 18.04 | B | O |
| ATOM | 16276 | ND2 | ASN | B | 486 | 58.570 | 41.432 | −21.267 | 1.00 | 18.35 | B | N |
| ATOM | 16279 | C | ASN | B | 486 | 56.073 | 41.225 | −17.046 | 1.00 | 20.79 | B | C |
| ATOM | 16280 | O | ASN | B | 486 | 56.712 | 41.302 | −15.994 | 1.00 | 20.97 | B | O |
| ATOM | 16282 | N | LYS | B | 487 | 54.878 | 41.792 | −17.221 | 1.00 | 21.29 | B | N |
| ATOM | 16283 | CA | LYS | B | 487 | 54.199 | 42.524 | −16.147 | 1.00 | 21.50 | B | C |
| ATOM | 16285 | CB | LYS | B | 487 | 52.967 | 43.266 | −16.678 | 1.00 | 21.48 | B | C |
| ATOM | 16288 | CG | LYS | B | 487 | 52.281 | 44.137 | −15.630 | 1.00 | 22.59 | B | C |
| ATOM | 16291 | CD | LYS | B | 487 | 51.063 | 44.853 | −16.184 | 1.00 | 25.14 | B | C |

TABLE 8-2-continued

| Coordinates for L494P Structure | | | | | | | | | | | |
|---|---|---|---|---|---|---|---|---|---|---|---|
| ATOM | 16294 | CE | LYS | B | 487 | 50.218 | 45.453 | −15.064 | 1.00 | 26.24 B | C |
| ATOM | 16297 | NZ | LYS | B | 487 | 48.974 | 46.098 | −15.571 | 1.00 | 27.02 B | N |
| ATOM | 16301 | C | LYS | B | 487 | 53.789 | 41.596 | −15.005 | 1.00 | 21.42 B | C |
| ATOM | 16302 | O | LYS | B | 487 | 53.830 | 41.990 | −13.841 | 1.00 | 21.42 B | O |
| ATOM | 16304 | N | GLU | B | 488 | 53.397 | 40.371 | −15.346 | 1.00 | 21.59 B | N |
| ATOM | 16305 | CA | GLU | B | 488 | 52.999 | 39.373 | −14.350 | 1.00 | 21.83 B | C |
| ATOM | 16307 | CB | GLU | B | 488 | 52.583 | 38.064 | −15.035 | 1.00 | 21.81 B | C |
| ATOM | 16310 | CG | GLU | B | 488 | 51.557 | 37.253 | −14.256 | 1.00 | 21.26 B | C |
| ATOM | 16313 | CD | GLU | B | 488 | 50.179 | 37.886 | −14.273 | 1.00 | 19.11 B | C |
| ATOM | 16314 | OE1 | GLU | B | 488 | 49.566 | 38.007 | −13.191 | 1.00 | 20.01 B | O |
| ATOM | 16315 | OE2 | GLU | B | 488 | 49.713 | 38.270 | −15.365 | 1.00 | 14.89 B | O |
| ATOM | 16316 | C | GLU | B | 488 | 54.134 | 39.104 | −13.359 | 1.00 | 22.01 B | C |
| ATOM | 16317 | O | GLU | B | 488 | 53.948 | 39.212 | −12.145 | 1.00 | 22.27 B | O |
| ATOM | 16319 | N | LYS | B | 489 | 55.308 | 38.772 | −13.894 | 1.00 | 21.89 B | N |
| ATOM | 16320 | CA | LYS | B | 489 | 56.502 | 38.503 | −13.087 | 1.00 | 21.65 B | C |
| ATOM | 16322 | CB | LYS | B | 489 | 57.658 | 38.066 | −13.995 | 1.00 | 21.41 B | C |
| ATOM | 16325 | CG | LYS | B | 489 | 58.974 | 37.757 | −13.282 | 1.00 | 20.79 B | C |
| ATOM | 16328 | CD | LYS | B | 489 | 58.858 | 36.558 | −12.349 | 1.00 | 19.77 B | C |
| ATOM | 16331 | CE | LYS | B | 489 | 60.160 | 36.303 | −11.605 | 1.00 | 19.39 B | C |
| ATOM | 16334 | NZ | LYS | B | 489 | 61.314 | 36.125 | −12.527 | 1.00 | 18.60 B | N |
| ATOM | 16338 | C | LYS | B | 489 | 56.932 | 39.715 | −12.260 | 1.00 | 21.80 B | C |
| ATOM | 16339 | O | LYS | B | 489 | 57.425 | 39.566 | −11.140 | 1.00 | 21.96 B | O |
| ATOM | 16341 | N | LEU | B | 490 | 56.749 | 40.908 | −12.820 | 1.00 | 21.81 B | N |
| ATOM | 16342 | CA | LEU | B | 490 | 57.145 | 42.143 | −12.149 | 1.00 | 21.84 B | C |
| ATOM | 16344 | CB | LEU | B | 490 | 56.972 | 43.349 | −13.084 | 1.00 | 21.72 B | C |
| ATOM | 16347 | CG | LEU | B | 490 | 58.111 | 44.369 | −13.049 | 1.00 | 21.17 B | C |
| ATOM | 16349 | CD1 | LEU | B | 490 | 59.318 | 43.812 | −13.782 | 1.00 | 20.00 B | C |
| ATOM | 16353 | CD2 | LEU | B | 490 | 57.681 | 45.699 | −13.651 | 1.00 | 20.57 B | C |
| ATOM | 16357 | C | LEU | B | 490 | 56.322 | 42.338 | −10.878 | 1.00 | 22.21 B | C |
| ATOM | 16358 | O | LEU | B | 490 | 56.868 | 42.627 | −9.812 | 1.00 | 22.30 B | O |
| ATOM | 16360 | N | GLY | B | 491 | 55.009 | 42.163 | −11.001 | 1.00 | 22.57 B | N |
| ATOM | 16361 | CA | GLY | B | 491 | 54.092 | 42.349 | −9.881 | 1.00 | 22.97 B | C |
| ATOM | 16364 | C | GLY | B | 491 | 52.644 | 42.326 | −10.332 | 1.00 | 23.45 B | C |
| ATOM | 16365 | O | GLY | B | 491 | 52.356 | 42.365 | −11.528 | 1.00 | 23.60 B | O |
| ATOM | 16367 | N | GLY | B | 492 | 51.727 | 42.281 | −9.372 | 1.00 | 23.88 B | N |
| ATOM | 16368 | CA | GLY | B | 492 | 50.315 | 42.067 | −9.672 | 1.00 | 24.35 B | C |
| ATOM | 16371 | C | GLY | B | 492 | 50.083 | 40.618 | −10.053 | 1.00 | 24.84 B | C |
| ATOM | 16372 | O | GLY | B | 492 | 49.210 | 40.308 | −10.867 | 1.00 | 24.78 B | O |
| ATOM | 16374 | N | SER | B | 493 | 50.882 | 39.734 | −9.456 | 1.00 | 25.52 B | N |
| ATOM | 16375 | CA | SER | B | 493 | 50.805 | 38.298 | −9.698 | 1.00 | 25.67 B | C |
| ATOM | 16377 | CB | SER | B | 493 | 52.214 | 37.695 | −9.775 | 1.00 | 25.87 B | C |
| ATOM | 16380 | OG | SER | B | 493 | 53.048 | 38.173 | −8.728 | 1.00 | 24.83 B | O |
| ATOM | 16382 | C | SER | B | 493 | 50.030 | 37.628 | −8.569 | 1.00 | 25.46 B | C |
| ATOM | 16383 | O | SER | B | 493 | 50.479 | 37.651 | −7.421 | 1.00 | 25.26 B | O |
| ATOM | 16385 | N | PRO | B | 494 | 48.869 | 37.023 | −8.886 | 1.00 | 25.33 B | N |
| ATOM | 16386 | CA | PRO | B | 494 | 48.148 | 36.286 | −7.852 | 1.00 | 25.35 B | C |
| ATOM | 16388 | CB | PRO | B | 494 | 46.819 | 35.943 | −8.526 | 1.00 | 25.40 B | C |
| ATOM | 16391 | CG | PRO | B | 494 | 47.149 | 35.847 | −9.962 | 1.00 | 25.73 B | C |
| ATOM | 16394 | CD | PRO | B | 494 | 48.261 | 36.834 | −10.216 | 1.00 | 25.52 B | C |
| ATOM | 16397 | C | PRO | B | 494 | 48.903 | 35.017 | −7.446 | 1.00 | 25.19 B | C |
| ATOM | 16398 | O | PRO | B | 494 | 48.708 | 34.513 | −6.337 | 1.00 | 25.71 B | O |
| ATOM | 16399 | N | PHE | B | 495 | 49.754 | 34.518 | −8.345 | 1.00 | 24.45 B | N |
| ATOM | 16400 | CA | PHE | B | 495 | 50.663 | 33.413 | −8.048 | 1.00 | 23.68 B | C |
| ATOM | 16402 | CB | PHE | B | 495 | 50.894 | 32.569 | −9.303 | 1.00 | 23.86 B | C |
| ATOM | 16405 | CG | PHE | B | 495 | 49.660 | 31.879 | −9.802 | 1.00 | 23.56 B | C |
| ATOM | 16406 | CD1 | PHE | B | 495 | 49.294 | 30.640 | −9.296 | 1.00 | 23.17 B | C |
| ATOM | 16408 | CE1 | PHE | B | 495 | 48.154 | 29.998 | −9.745 | 1.00 | 22.12 B | C |
| ATOM | 16410 | CZ | PHE | B | 495 | 47.361 | 30.592 | −10.713 | 1.00 | 21.69 B | C |
| ATOM | 16412 | CE2 | PHE | B | 495 | 47.715 | 31.829 | −11.227 | 1.00 | 22.40 B | C |
| ATOM | 16414 | CD2 | PHE | B | 495 | 48.860 | 32.466 | −10.770 | 1.00 | 22.45 B | C |
| ATOM | 16416 | C | PHE | B | 495 | 52.005 | 33.919 | −7.523 | 1.00 | 22.88 B | C |
| ATOM | 16417 | O | PHE | B | 495 | 52.295 | 35.118 | −7.564 | 1.00 | 22.31 B | O |
| ATOM | 16419 | N | ALA | B | 496 | 52.816 | 32.988 | −7.031 | 1.00 | 22.48 B | N |
| ATOM | 16420 | CA | ALA | B | 496 | 54.155 | 33.297 | −6.542 | 1.00 | 22.48 B | C |
| ATOM | 16422 | CB | ALA | B | 496 | 54.680 | 32.144 | −5.697 | 1.00 | 22.42 B | C |
| ATOM | 16426 | C | ALA | B | 496 | 55.093 | 33.563 | −7.716 | 1.00 | 22.53 B | C |
| ATOM | 16427 | O | ALA | B | 496 | 54.948 | 32.954 | −8.778 | 1.00 | 22.92 B | O |
| ATOM | 16429 | N | LYS | B | 497 | 56.056 | 34.463 | −7.521 | 1.00 | 22.29 B | N |
| ATOM | 16430 | CA | LYS | B | 497 | 57.052 | 34.778 | −8.557 | 1.00 | 21.94 B | C |
| ATOM | 16432 | CB | LYS | B | 497 | 58.007 | 35.884 | −8.084 | 1.00 | 22.07 B | C |
| ATOM | 16435 | CG | LYS | B | 497 | 57.334 | 37.237 | −7.920 | 1.00 | 23.65 B | C |
| ATOM | 16438 | CD | LYS | B | 497 | 58.343 | 38.366 | −7.815 | 1.00 | 24.78 B | C |
| ATOM | 16441 | CE | LYS | B | 497 | 57.645 | 39.702 | −7.616 | 1.00 | 25.70 B | C |
| ATOM | 16444 | NZ | LYS | B | 497 | 58.598 | 40.846 | −7.649 | 1.00 | 26.30 B | N |
| ATOM | 16448 | C | LYS | B | 497 | 57.849 | 33.552 | −9.035 | 1.00 | 21.17 B | C |
| ATOM | 16449 | O | LYS | B | 497 | 58.182 | 33.465 | −10.220 | 1.00 | 20.85 B | O |
| ATOM | 16451 | N | PRO | B | 498 | 58.169 | 32.613 | −8.120 | 1.00 | 20.40 B | N |
| ATOM | 16452 | CA | PRO | B | 498 | 58.746 | 31.335 | −8.539 | 1.00 | 19.76 B | C |

TABLE 8-2-continued

Coordinates for L494P Structure

| | | | | | | | | | | | |
|---|---|---|---|---|---|---|---|---|---|---|---|
| ATOM | 16454 | CB | PRO | B | 498 | 58.843 | 30.555 | −7.228 | 1.00 | 20.02 B | C |
| ATOM | 16457 | CG | PRO | B | 498 | 59.067 | 31.596 | −6.208 | 1.00 | 20.28 B | C |
| ATOM | 16460 | CD | PRO | B | 498 | 58.282 | 32.797 | −6.659 | 1.00 | 20.41 B | C |
| ATOM | 16463 | C | PRO | B | 498 | 57.892 | 30.572 | −9.551 | 1.00 | 19.04 B | C |
| ATOM | 16464 | O | PRO | B | 498 | 58.429 | 30.080 | −10.543 | 1.00 | 18.97 B | O |
| ATOM | 16465 | N | PHE | B | 499 | 56.584 | 30.478 | −9.308 | 1.00 | 18.00 B | N |
| ATOM | 16466 | CA | PHE | B | 499 | 55.679 | 29.806 | −10.247 | 1.00 | 17.28 B | C |
| ATOM | 16468 | CB | PHE | B | 499 | 54.339 | 29.476 | −9.595 | 1.00 | 17.32 B | C |
| ATOM | 16471 | CG | PHE | B | 499 | 53.370 | 28.806 | −10.530 | 1.00 | 17.69 B | C |
| ATOM | 16472 | CD1 | PHE | B | 499 | 53.589 | 27.497 | −10.951 | 1.00 | 17.29 B | C |
| ATOM | 16474 | CE1 | PHE | B | 499 | 52.705 | 26.871 | −11.823 | 1.00 | 16.85 B | C |
| ATOM | 16476 | CZ | PHE | B | 499 | 51.587 | 27.557 | −12.288 | 1.00 | 16.84 B | C |
| ATOM | 16478 | CE2 | PHE | B | 499 | 51.362 | 28.868 | −11.880 | 1.00 | 17.65 B | C |
| ATOM | 16480 | CD2 | PHE | B | 499 | 52.252 | 29.486 | −11.006 | 1.00 | 17.32 B | C |
| ATOM | 16482 | C | PHE | B | 499 | 55.432 | 30.634 | −11.505 | 1.00 | 16.84 B | C |
| ATOM | 16483 | O | PHE | B | 499 | 55.363 | 30.086 | −12.605 | 1.00 | 16.87 B | O |
| ATOM | 16485 | N | VAL | B | 500 | 55.287 | 31.947 | −11.338 | 1.00 | 16.41 B | N |
| ATOM | 16486 | CA | VAL | B | 500 | 55.142 | 32.861 | −12.474 | 1.00 | 16.20 B | C |
| ATOM | 16488 | CB | VAL | B | 500 | 54.925 | 34.317 | −12.010 | 1.00 | 16.36 B | C |
| ATOM | 16490 | CG1 | VAL | B | 500 | 53.606 | 34.442 | −11.264 | 1.00 | 17.18 B | C |
| ATOM | 16494 | CG2 | VAL | B | 500 | 54.957 | 35.280 | −13.191 | 1.00 | 16.91 B | C |
| ATOM | 16498 | C | VAL | B | 500 | 56.363 | 32.793 | −13.394 | 1.00 | 15.82 B | C |
| ATOM | 16499 | O | VAL | B | 500 | 56.243 | 32.992 | −14.600 | 1.00 | 15.97 B | O |
| ATOM | 16501 | N | GLU | B | 501 | 57.531 | 32.509 | −12.822 | 1.00 | 15.50 B | N |
| ATOM | 16502 | CA | GLU | B | 501 | 58.734 | 32.258 | −13.615 | 1.00 | 15.59 B | C |
| ATOM | 16504 | CB | GLU | B | 501 | 60.003 | 32.453 | −12.769 | 1.00 | 15.69 B | C |
| ATOM | 16507 | CG | GLU | B | 501 | 61.332 | 32.376 | −13.545 | 1.00 | 15.01 B | C |
| ATOM | 16510 | CD | GLU | B | 501 | 61.554 | 33.531 | −14.526 | 1.00 | 16.71 B | C |
| ATOM | 16511 | OE1 | GLU | B | 501 | 60.739 | 34.482 | −14.571 | 1.00 | 14.60 B | O |
| ATOM | 16512 | OE2 | GLU | B | 501 | 62.564 | 33.485 | −15.261 | 1.00 | 18.19 B | O |
| ATOM | 16513 | C | GLU | B | 501 | 58.704 | 30.854 | −14.231 | 1.00 | 15.47 B | C |
| ATOM | 16514 | O | GLU | B | 501 | 59.123 | 30.677 | −15.375 | 1.00 | 16.14 B | O |
| ATOM | 16516 | N | THR | B | 502 | 58.217 | 29.862 | −13.484 | 1.00 | 14.76 B | N |
| ATOM | 16517 | CA | THR | B | 502 | 58.104 | 28.497 | −14.010 | 1.00 | 14.28 B | C |
| ATOM | 16519 | CB | THR | B | 502 | 57.531 | 27.499 | −12.973 | 1.00 | 14.03 B | C |
| ATOM | 16521 | OG1 | THR | B | 502 | 58.190 | 27.660 | −11.715 | 1.00 | 13.78 B | O |
| ATOM | 16523 | CG2 | THR | B | 502 | 57.721 | 26.070 | −13.449 | 1.00 | 12.78 B | C |
| ATOM | 16527 | C | THR | B | 502 | 57.210 | 28.464 | −15.246 | 1.00 | 14.49 B | C |
| ATOM | 16528 | O | THR | B | 502 | 57.505 | 27.760 | −16.207 | 1.00 | 14.67 B | O |
| ATOM | 16530 | N | ALA | B | 503 | 56.119 | 29.227 | −15.215 | 1.00 | 14.64 B | N |
| ATOM | 16531 | CA | ALA | B | 503 | 55.206 | 29.306 | −16.354 | 1.00 | 14.82 B | C |
| ATOM | 16533 | CB | ALA | B | 503 | 53.932 | 30.048 | −15.973 | 1.00 | 14.76 B | C |
| ATOM | 16537 | C | ALA | B | 503 | 55.890 | 29.989 | −17.534 | 1.00 | 14.83 B | C |
| ATOM | 16538 | O | ALA | B | 503 | 55.970 | 29.425 | −18.623 | 1.00 | 14.59 B | O |
| ATOM | 16540 | N | ILE | B | 504 | 56.404 | 31.194 | −17.307 | 1.00 | 14.79 B | N |
| ATOM | 16541 | CA | ILE | B | 504 | 57.111 | 31.936 | −18.350 | 1.00 | 15.23 B | C |
| ATOM | 16543 | CB | ILE | B | 504 | 57.747 | 33.233 | −17.790 | 1.00 | 15.36 B | C |
| ATOM | 16545 | CG1 | ILE | B | 504 | 56.654 | 34.265 | −17.483 | 1.00 | 15.16 B | C |
| ATOM | 16548 | CD1 | ILE | B | 504 | 57.127 | 35.440 | −16.656 | 1.00 | 12.30 B | C |
| ATOM | 16552 | CG2 | ILE | B | 504 | 58.740 | 33.834 | −18.782 | 1.00 | 15.13 B | C |
| ATOM | 16556 | C | ILE | B | 504 | 58.174 | 31.065 | −19.032 | 1.00 | 15.91 B | C |
| ATOM | 16557 | O | ILE | B | 504 | 58.417 | 31.207 | −20.231 | 1.00 | 16.25 B | O |
| ATOM | 16559 | N | ASN | B | 505 | 58.787 | 30.155 | −18.273 | 1.00 | 16.36 B | N |
| ATOM | 16560 | CA | ASN | B | 505 | 59.760 | 29.208 | −18.829 | 1.00 | 16.52 B | C |
| ATOM | 16562 | CB | ASN | B | 505 | 60.447 | 28.408 | −17.710 | 1.00 | 16.46 B | C |
| ATOM | 16565 | CG | ASN | B | 505 | 61.425 | 29.249 | −16.892 | 1.00 | 16.04 B | C |
| ATOM | 16566 | OD1 | ASN | B | 505 | 62.149 | 30.091 | −17.427 | 1.00 | 13.66 B | O |
| ATOM | 16567 | ND2 | ASN | B | 505 | 61.456 | 29.008 | −15.586 | 1.00 | 16.62 B | N |
| ATOM | 16570 | C | ASN | B | 505 | 59.169 | 28.251 | −19.876 | 1.00 | 16.61 B | C |
| ATOM | 16571 | O | ASN | B | 505 | 59.891 | 27.786 | −20.761 | 1.00 | 16.48 B | O |
| ATOM | 16573 | N | LEU | B | 506 | 57.872 | 27.955 | −19.774 | 1.00 | 16.86 B | N |
| ATOM | 16574 | CA | LEU | B | 506 | 57.171 | 27.184 | −20.810 | 1.00 | 17.30 B | C |
| ATOM | 16576 | CB | LEU | B | 506 | 55.726 | 26.888 | −20.401 | 1.00 | 17.57 B | C |
| ATOM | 16579 | CG | LEU | B | 506 | 54.836 | 26.191 | −21.440 | 1.00 | 18.47 B | C |
| ATOM | 16581 | CD1 | LEU | B | 506 | 55.184 | 24.719 | −21.542 | 1.00 | 19.77 B | C |
| ATOM | 16585 | CD2 | LEU | B | 506 | 53.370 | 26.364 | −21.073 | 1.00 | 20.68 B | C |
| ATOM | 16589 | C | LEU | B | 506 | 57.177 | 27.946 | −22.130 | 1.00 | 17.50 B | C |
| ATOM | 16590 | O | LEU | B | 506 | 57.340 | 27.351 | −23.195 | 1.00 | 17.72 B | O |
| ATOM | 16592 | N | ALA | B | 507 | 56.985 | 29.261 | −22.054 | 1.00 | 17.77 B | N |
| ATOM | 16593 | CA | ALA | B | 507 | 57.067 | 30.120 | −23.233 | 1.00 | 17.80 B | C |
| ATOM | 16595 | CB | ALA | B | 507 | 56.635 | 31.536 | −22.893 | 1.00 | 17.84 B | C |
| ATOM | 16599 | C | ALA | B | 507 | 58.483 | 30.117 | −23.796 | 1.00 | 17.61 B | C |
| ATOM | 16600 | O | ALA | B | 507 | 58.671 | 29.989 | −25.003 | 1.00 | 17.76 B | O |
| ATOM | 16602 | N | ARG | B | 508 | 59.472 | 30.246 | −22.913 | 1.00 | 17.60 B | N |
| ATOM | 16603 | CA | ARG | B | 508 | 60.880 | 30.193 | −23.309 | 1.00 | 17.71 B | C |
| ATOM | 16605 | CB | ARG | B | 508 | 61.803 | 30.386 | −22.100 | 1.00 | 17.79 B | C |
| ATOM | 16608 | CG | ARG | B | 508 | 61.746 | 31.773 | −21.487 | 1.00 | 18.73 B | C |
| ATOM | 16611 | CD | ARG | B | 508 | 62.939 | 32.043 | −20.582 | 1.00 | 19.55 B | C |

TABLE 8-2-continued

| Coordinates for L494P Structure | | | | | | | | | | | |
|---|---|---|---|---|---|---|---|---|---|---|---|
| ATOM | 16614 | NE | ARG | B | 508 | 62.905 | 33.398 | −20.024 | 1.00 | 19.83 B | N |
| ATOM | 16616 | CZ | ARG | B | 508 | 62.358 | 33.739 | −18.857 | 1.00 | 19.59 B | C |
| ATOM | 16617 | NH1 | ARG | B | 508 | 61.781 | 32.831 | −18.073 | 1.00 | 19.68 B | N |
| ATOM | 16620 | NH2 | ARG | B | 508 | 62.391 | 35.009 | −18.468 | 1.00 | 19.69 B | N |
| ATOM | 16623 | C | ARG | B | 508 | 61.212 | 28.870 | −23.984 | 1.00 | 17.74 B | C |
| ATOM | 16624 | O | ARG | B | 508 | 61.822 | 28.855 | −25.052 | 1.00 | 17.57 B | O |
| ATOM | 16626 | N | GLN | B | 509 | 60.806 | 27.767 | −23.355 | 1.00 | 17.87 B | N |
| ATOM | 16627 | CA | GLN | B | 509 | 61.065 | 26.428 | −23.889 | 1.00 | 18.05 B | C |
| ATOM | 16629 | CB | GLN | B | 509 | 60.600 | 25.353 | −22.901 | 1.00 | 17.84 B | C |
| ATOM | 16632 | CG | GLN | B | 509 | 60.772 | 23.904 | −23.383 | 1.00 | 17.66 B | C |
| ATOM | 16635 | CD | GLN | B | 509 | 62.217 | 23.521 | −23.658 | 1.00 | 16.78 B | C |
| ATOM | 16636 | OE1 | GLN | B | 509 | 63.150 | 24.156 | −23.170 | 1.00 | 17.45 B | O |
| ATOM | 16637 | NE2 | GLN | B | 509 | 62.404 | 22.471 | −24.442 | 1.00 | 16.89 B | N |
| ATOM | 16640 | C | GLN | B | 509 | 60.396 | 26.220 | −25.248 | 1.00 | 18.61 B | C |
| ATOM | 16641 | O | GLN | B | 509 | 60.959 | 25.561 | −26.124 | 1.00 | 18.92 B | O |
| ATOM | 16643 | N | SER | B | 510 | 59.202 | 26.782 | −25.423 | 1.00 | 18.83 B | N |
| ATOM | 16644 | CA | SER | B | 510 | 58.498 | 26.692 | −26.700 | 1.00 | 18.95 B | C |
| ATOM | 16646 | CB | SER | B | 510 | 57.109 | 27.323 | −26.603 | 1.00 | 18.82 B | C |
| ATOM | 16649 | OG | SER | B | 510 | 56.264 | 26.533 | −25.788 | 1.00 | 19.00 B | O |
| ATOM | 16651 | C | SER | B | 510 | 59.292 | 27.337 | −27.832 | 1.00 | 19.16 B | C |
| ATOM | 16652 | O | SER | B | 510 | 59.232 | 26.882 | −28.968 | 1.00 | 19.43 B | O |
| ATOM | 16654 | N | HIS | B | 511 | 60.041 | 28.390 | −27.526 | 1.00 | 19.42 B | N |
| ATOM | 16655 | CA | HIS | B | 511 | 60.889 | 29.022 | −28.531 | 1.00 | 20.02 B | C |
| ATOM | 16657 | CB | HIS | B | 511 | 61.405 | 30.380 | −28.041 | 1.00 | 20.11 B | C |
| ATOM | 16660 | CG | HIS | B | 511 | 60.395 | 31.479 | −28.143 | 1.00 | 17.99 B | C |
| ATOM | 16661 | ND1 | HIS | B | 511 | 60.065 | 32.074 | −29.341 | 1.00 | 17.74 B | N |
| ATOM | 16663 | CE1 | HIS | B | 511 | 59.155 | 33.006 | −29.131 | 1.00 | 18.27 B | C |
| ATOM | 16665 | NE2 | HIS | B | 511 | 58.883 | 33.038 | −27.839 | 1.00 | 17.55 B | N |
| ATOM | 16667 | CD2 | HIS | B | 511 | 59.645 | 32.092 | −27.199 | 1.00 | 16.35 B | C |
| ATOM | 16669 | C | HIS | B | 511 | 62.058 | 28.118 | −28.933 | 1.00 | 20.72 B | C |
| ATOM | 16670 | O | HIS | B | 511 | 62.345 | 27.955 | −30.121 | 1.00 | 20.84 B | O |
| ATOM | 16672 | N | CYS | B | 512 | 62.712 | 27.519 | −27.943 | 1.00 | 21.38 B | N |
| ATOM | 16673 | CA | CYS | B | 512 | 63.904 | 26.704 | −28.187 | 1.00 | 22.20 B | C |
| ATOM | 16675 | CB | CYS | B | 512 | 64.715 | 26.569 | −26.894 | 1.00 | 22.42 B | C |
| ATOM | 16678 | SG | CYS | B | 512 | 65.118 | 28.158 | −26.116 | 1.00 | 23.55 B | S |
| ATOM | 16680 | C | CYS | B | 512 | 63.604 | 25.313 | −28.765 | 1.00 | 22.44 B | C |
| ATOM | 16681 | O | CYS | B | 512 | 64.520 | 24.628 | −29.223 | 1.00 | 22.16 B | O |
| ATOM | 16683 | N | THR | B | 513 | 62.337 | 24.898 | −28.740 | 1.00 | 23.12 B | N |
| ATOM | 16684 | CA | THR | B | 513 | 61.931 | 23.599 | −29.287 | 1.00 | 24.06 B | C |
| ATOM | 16686 | CB | THR | B | 513 | 60.899 | 22.897 | −28.371 | 1.00 | 24.30 B | C |
| ATOM | 16688 | OG1 | THR | B | 513 | 61.262 | 23.083 | −26.999 | 1.00 | 25.60 B | O |
| ATOM | 16690 | CG2 | THR | B | 513 | 60.832 | 21.401 | −28.671 | 1.00 | 24.35 B | C |
| ATOM | 16694 | C | THR | B | 513 | 61.340 | 23.706 | −30.700 | 1.00 | 24.58 B | C |
| ATOM | 16695 | O | THR | B | 513 | 61.194 | 22.695 | −31.386 | 1.00 | 24.46 B | O |
| ATOM | 16697 | N | TYR | B | 514 | 61.003 | 24.921 | −31.132 | 1.00 | 25.51 B | N |
| ATOM | 16698 | CA | TYR | B | 514 | 60.432 | 25.139 | −32.463 | 1.00 | 26.21 B | C |
| ATOM | 16700 | CB | TYR | B | 514 | 58.968 | 25.573 | −32.348 | 1.00 | 25.89 B | C |
| ATOM | 16703 | CG | TYR | B | 514 | 58.098 | 24.497 | −31.729 | 1.00 | 24.88 B | C |
| ATOM | 16704 | CD1 | TYR | B | 514 | 57.783 | 23.342 | −32.437 | 1.00 | 25.24 B | C |
| ATOM | 16706 | CE1 | TYR | B | 514 | 56.994 | 22.346 | −31.874 | 1.00 | 24.68 B | C |
| ATOM | 16708 | CZ | TYR | B | 514 | 56.514 | 22.499 | −30.589 | 1.00 | 23.33 B | C |
| ATOM | 16709 | OH | TYR | B | 514 | 55.733 | 21.511 | −30.037 | 1.00 | 24.82 B | O |
| ATOM | 16711 | CE2 | TYR | B | 514 | 56.816 | 23.634 | −29.863 | 1.00 | 22.23 B | C |
| ATOM | 16713 | CD2 | TYR | B | 514 | 57.606 | 24.622 | −30.432 | 1.00 | 23.14 B | C |
| ATOM | 16715 | C | TYR | B | 514 | 61.268 | 26.142 | −33.264 | 1.00 | 27.31 B | C |
| ATOM | 16716 | O | TYR | B | 514 | 61.143 | 27.358 | −33.107 | 1.00 | 27.40 B | O |
| ATOM | 16718 | N | HIS | B | 515 | 62.124 | 25.595 | −34.122 | 1.00 | 28.61 B | N |
| ATOM | 16719 | CA | HIS | B | 515 | 63.102 | 26.361 | −34.893 | 1.00 | 30.06 B | C |
| ATOM | 16721 | CB | HIS | B | 515 | 64.492 | 26.228 | −34.242 | 1.00 | 30.62 B | C |
| ATOM | 16724 | CG | HIS | B | 515 | 64.870 | 24.815 | −33.904 | 1.00 | 32.08 B | C |
| ATOM | 16725 | ND1 | HIS | B | 515 | 64.776 | 24.306 | −32.626 | 1.00 | 31.97 B | N |
| ATOM | 16727 | CE1 | HIS | B | 515 | 65.159 | 23.042 | −32.629 | 1.00 | 32.68 B | C |
| ATOM | 16729 | NE2 | HIS | B | 515 | 65.492 | 22.710 | −33.863 | 1.00 | 34.16 B | N |
| ATOM | 16731 | CD2 | HIS | B | 515 | 65.320 | 23.801 | −34.681 | 1.00 | 33.51 B | C |
| ATOM | 16733 | C | HIS | B | 515 | 63.106 | 25.831 | −36.333 | 1.00 | 30.55 B | C |
| ATOM | 16734 | O | HIS | B | 515 | 62.201 | 25.084 | −36.717 | 1.00 | 30.83 B | O |
| ATOM | 16736 | N | ASN | B | 516 | 64.098 | 26.233 | −37.129 | 1.00 | 30.79 B | N |
| ATOM | 16737 | CA | ASN | B | 516 | 64.294 | 25.687 | −38.474 | 1.00 | 30.94 B | C |
| ATOM | 16739 | CB | ASN | B | 516 | 63.524 | 26.513 | −39.512 | 1.00 | 31.24 B | C |
| ATOM | 16742 | CG | ASN | B | 516 | 62.034 | 26.182 | −39.546 | 1.00 | 32.16 B | C |
| ATOM | 16743 | OD1 | ASN | B | 516 | 61.642 | 25.024 | −39.703 | 1.00 | 31.94 B | O |
| ATOM | 16744 | ND2 | ASN | B | 516 | 61.198 | 27.207 | −39.410 | 1.00 | 33.17 B | N |
| ATOM | 16747 | C | ASN | B | 516 | 65.774 | 25.639 | −38.839 | 1.00 | 30.76 B | C |
| ATOM | 16748 | O | ASN | B | 516 | 66.617 | 25.303 | −38.007 | 1.00 | 30.70 B | O |
| ATOM | 16750 | N | THR | B | 521 | 72.475 | 22.115 | −40.233 | 1.00 | 39.09 B | N |
| ATOM | 16751 | CA | THR | B | 521 | 71.640 | 21.708 | −39.109 | 1.00 | 39.22 B | C |
| ATOM | 16753 | CB | THR | B | 521 | 71.978 | 22.514 | −37.832 | 1.00 | 39.15 B | C |
| ATOM | 16755 | OG1 | THR | B | 521 | 73.375 | 22.401 | −37.542 | 1.00 | 39.43 B | O |

TABLE 8-2-continued

Coordinates for L494P Structure

| | | | | | | | | | | | |
|---|---|---|---|---|---|---|---|---|---|---|---|
| ATOM | 16757 | CG2 | THR | B | 521 | 71.181 | 22.001 | −36.647 | 1.00 | 38.86 B | C |
| ATOM | 16761 | C | THR | B | 521 | 70.152 | 21.875 | −39.426 | 1.00 | 39.42 B | C |
| ATOM | 16762 | O | THR | B | 521 | 69.595 | 22.965 | −39.281 | 1.00 | 39.63 B | O |
| ATOM | 16764 | N | SER | B | 522 | 69.519 | 20.787 | −39.860 | 1.00 | 39.51 B | N |
| ATOM | 16765 | CA | SER | B | 522 | 68.067 | 20.756 | −40.065 | 1.00 | 39.64 B | C |
| ATOM | 16767 | CB | SER | B | 522 | 67.675 | 19.512 | −40.881 | 1.00 | 39.62 B | C |
| ATOM | 16770 | OG | SER | B | 522 | 68.247 | 18.334 | −40.340 | 1.00 | 39.80 B | O |
| ATOM | 16772 | C | SER | B | 522 | 67.354 | 20.780 | −38.702 | 1.00 | 39.74 B | C |
| ATOM | 16773 | O | SER | B | 522 | 68.014 | 20.665 | −37.666 | 1.00 | 39.55 B | O |
| ATOM | 16775 | N | PRO | B | 523 | 66.013 | 20.952 | −38.691 | 1.00 | 40.10 B | N |
| ATOM | 16776 | CA | PRO | B | 523 | 65.277 | 20.965 | −37.414 | 1.00 | 40.09 B | C |
| ATOM | 16778 | CB | PRO | B | 523 | 63.811 | 21.075 | −37.849 | 1.00 | 40.16 B | C |
| ATOM | 16781 | CG | PRO | B | 523 | 63.856 | 21.703 | −39.192 | 1.00 | 40.42 B | C |
| ATOM | 16784 | CD | PRO | B | 523 | 65.125 | 21.234 | −39.836 | 1.00 | 40.33 B | C |
| ATOM | 16787 | C | PRO | B | 523 | 65.498 | 19.703 | −36.572 | 1.00 | 40.04 B | C |
| ATOM | 16788 | O | PRO | B | 523 | 65.670 | 19.800 | −35.353 | 1.00 | 39.93 B | O |
| ATOM | 16789 | N | ASP | B | 524 | 65.479 | 18.538 | −37.222 | 1.00 | 39.90 B | N |
| ATOM | 16790 | CA | ASP | B | 524 | 65.886 | 17.277 | −36.593 | 1.00 | 39.64 B | C |
| ATOM | 16792 | CB | ASP | B | 524 | 65.136 | 16.081 | −37.198 | 1.00 | 39.95 B | C |
| ATOM | 16795 | CG | ASP | B | 524 | 63.726 | 15.926 | −36.655 | 1.00 | 40.66 B | C |
| ATOM | 16796 | OD1 | ASP | B | 524 | 63.491 | 16.229 | −35.465 | 1.00 | 40.38 B | O |
| ATOM | 16797 | OD2 | ASP | B | 524 | 62.851 | 15.477 | −37.425 | 1.00 | 42.77 B | O |
| ATOM | 16798 | C | ASP | B | 524 | 67.386 | 17.083 | −36.782 | 1.00 | 38.91 B | C |
| ATOM | 16799 | O | ASP | B | 524 | 67.812 | 16.471 | −37.759 | 1.00 | 39.00 B | O |
| ATOM | 16801 | N | GLU | B | 525 | 68.159 | 17.608 | −35.830 | 1.00 | 38.15 B | N |
| ATOM | 16802 | CA | GLU | B | 525 | 69.642 | 17.592 | −35.810 | 1.00 | 37.66 B | C |
| ATOM | 16804 | CB | GLU | B | 525 | 70.297 | 17.569 | −37.206 | 1.00 | 37.71 B | C |
| ATOM | 16807 | CG | GLU | B | 525 | 70.620 | 16.153 | −37.724 | 1.00 | 37.79 B | C |
| ATOM | 16810 | CD | GLU | B | 525 | 71.981 | 16.048 | −38.386 | 1.00 | 38.25 B | C |
| ATOM | 16811 | OE1 | GLU | B | 525 | 72.955 | 16.625 | −37.857 | 1.00 | 39.00 B | O |
| ATOM | 16812 | OE2 | GLU | B | 525 | 72.080 | 15.370 | −39.430 | 1.00 | 38.77 B | O |
| ATOM | 16813 | C | GLU | B | 525 | 70.191 | 18.771 | −34.994 | 1.00 | 36.95 B | C |
| ATOM | 16814 | O | GLU | B | 525 | 71.317 | 18.714 | −34.499 | 1.00 | 37.04 B | O |
| ATOM | 16816 | N | LEU | B | 526 | 69.407 | 19.842 | −34.880 | 1.00 | 36.09 B | N |
| ATOM | 16817 | CA | LEU | B | 526 | 69.625 | 20.840 | −33.837 | 1.00 | 35.33 B | C |
| ATOM | 16819 | CB | LEU | B | 526 | 68.900 | 22.150 | −34.161 | 1.00 | 35.12 B | C |
| ATOM | 16822 | CG | LEU | B | 526 | 69.334 | 23.384 | −33.364 | 1.00 | 34.90 B | C |
| ATOM | 16824 | CD1 | LEU | B | 526 | 68.442 | 24.568 | −33.694 | 1.00 | 34.94 B | C |
| ATOM | 16828 | CD2 | LEU | B | 526 | 70.793 | 23.730 | −33.630 | 1.00 | 36.14 B | C |
| ATOM | 16832 | C | LEU | B | 526 | 69.105 | 20.252 | −32.527 | 1.00 | 34.83 B | C |
| ATOM | 16833 | O | LEU | B | 526 | 69.770 | 20.327 | −31.496 | 1.00 | 34.87 B | O |
| ATOM | 16835 | N | THR | B | 527 | 67.913 | 19.660 | −32.586 | 1.00 | 34.52 B | N |
| ATOM | 16836 | CA | THR | B | 527 | 67.303 | 18.996 | −31.434 | 1.00 | 34.28 B | C |
| ATOM | 16838 | CB | THR | B | 527 | 65.908 | 18.433 | −31.788 | 1.00 | 34.07 B | C |
| ATOM | 16840 | OG1 | THR | B | 527 | 65.038 | 19.509 | −32.164 | 1.00 | 33.57 B | O |
| ATOM | 16842 | CG2 | THR | B | 527 | 65.306 | 17.682 | −30.606 | 1.00 | 33.37 B | C |
| ATOM | 16846 | C | THR | B | 527 | 68.179 | 17.857 | −30.916 | 1.00 | 34.29 B | C |
| ATOM | 16847 | O | THR | B | 527 | 68.451 | 17.771 | −29.716 | 1.00 | 34.38 B | O |
| ATOM | 16849 | N | ARG | B | 528 | 68.617 | 16.992 | −31.829 | 1.00 | 34.09 B | N |
| ATOM | 16850 | CA | ARG | B | 528 | 69.465 | 15.850 | −31.485 | 1.00 | 34.07 B | C |
| ATOM | 16852 | CB | ARG | B | 528 | 69.933 | 15.138 | −32.760 | 1.00 | 34.30 B | C |
| ATOM | 16855 | CG | ARG | B | 528 | 70.746 | 13.869 | −32.528 | 1.00 | 35.25 B | C |
| ATOM | 16858 | CD | ARG | B | 528 | 71.215 | 13.264 | −33.849 | 1.00 | 36.66 B | C |
| ATOM | 16861 | NE | ARG | B | 528 | 72.244 | 14.073 | −34.513 | 1.00 | 37.15 B | N |
| ATOM | 16863 | CZ | ARG | B | 528 | 73.534 | 14.113 | −34.169 | 1.00 | 36.44 B | C |
| ATOM | 16864 | NH1 | ARG | B | 528 | 73.996 | 13.397 | −33.146 | 1.00 | 35.92 B | N |
| ATOM | 16867 | NH2 | ARG | B | 528 | 74.373 | 14.884 | −34.854 | 1.00 | 35.81 B | N |
| ATOM | 16870 | C | ARG | B | 528 | 70.673 | 16.287 | −30.655 | 1.00 | 33.89 B | C |
| ATOM | 16871 | O | ARG | B | 528 | 70.950 | 15.705 | −29.606 | 1.00 | 34.34 B | O |
| ATOM | 16873 | N | LYS | B | 529 | 71.378 | 17.313 | −31.127 | 1.00 | 33.28 B | N |
| ATOM | 16874 | CA | LYS | B | 529 | 72.566 | 17.824 | −30.436 | 1.00 | 32.69 B | C |
| ATOM | 16876 | CB | LYS | B | 529 | 73.298 | 18.863 | −31.294 | 1.00 | 32.75 B | C |
| ATOM | 16879 | CG | LYS | B | 529 | 74.085 | 18.275 | −32.452 | 1.00 | 32.66 B | C |
| ATOM | 16882 | CD | LYS | B | 529 | 74.956 | 19.327 | −33.120 | 1.00 | 32.31 B | C |
| ATOM | 16885 | CE | LYS | B | 529 | 75.829 | 18.711 | −34.200 | 1.00 | 32.91 B | C |
| ATOM | 16888 | NZ | LYS | B | 529 | 76.857 | 19.660 | −34.708 | 1.00 | 33.59 B | N |
| ATOM | 16892 | C | LYS | B | 529 | 72.225 | 18.436 | −29.079 | 1.00 | 32.13 B | C |
| ATOM | 16893 | O | LYS | B | 529 | 72.916 | 18.182 | −28.091 | 1.00 | 32.37 B | O |
| ATOM | 16895 | N | ARG | B | 530 | 71.165 | 19.241 | −29.037 | 1.00 | 31.27 B | N |
| ATOM | 16896 | CA | ARG | B | 530 | 70.759 | 19.913 | −27.800 | 1.00 | 30.74 B | C |
| ATOM | 16898 | CB | ARG | B | 530 | 69.629 | 20.912 | −28.070 | 1.00 | 30.66 B | C |
| ATOM | 16901 | CG | ARG | B | 530 | 70.095 | 22.182 | −28.768 | 1.00 | 30.10 B | C |
| ATOM | 16904 | CD | ARG | B | 530 | 68.926 | 23.081 | −29.131 | 1.00 | 28.52 B | C |
| ATOM | 16907 | NE | ARG | B | 530 | 69.370 | 24.383 | −29.626 | 1.00 | 26.96 B | N |
| ATOM | 16909 | CZ | ARG | B | 530 | 68.554 | 25.374 | −29.982 | 1.00 | 26.60 B | C |
| ATOM | 16910 | NH1 | ARG | B | 530 | 67.234 | 25.224 | −29.904 | 1.00 | 26.51 B | N |
| ATOM | 16913 | NH2 | ARG | B | 530 | 69.059 | 26.524 | −30.420 | 1.00 | 26.25 B | N |
| ATOM | 16916 | C | ARG | B | 530 | 70.346 | 18.918 | −26.716 | 1.00 | 30.41 B | C |

TABLE 8-2-continued

Coordinates for L494P Structure

| | | | | | | | | | | | | |
|---|---|---|---|---|---|---|---|---|---|---|---|---|
| ATOM | 16917 | O | ARG | B | 530 | 70.684 | 19.097 | −25.546 | 1.00 | 30.43 | B | O |
| ATOM | 16919 | N | VAL | B | 531 | 69.626 | 17.871 | −27.110 | 1.00 | 30.03 | B | N |
| ATOM | 16920 | CA | VAL | B | 531 | 69.278 | 16.784 | −26.191 | 1.00 | 29.78 | B | C |
| ATOM | 16922 | CB | VAL | B | 531 | 68.275 | 15.782 | −26.834 | 1.00 | 30.01 | B | C |
| ATOM | 16924 | CG1 | VAL | B | 531 | 68.603 | 14.335 | −26.458 | 1.00 | 30.16 | B | C |
| ATOM | 16928 | CG2 | VAL | B | 531 | 66.841 | 16.141 | −26.447 | 1.00 | 29.98 | B | C |
| ATOM | 16932 | C | VAL | B | 531 | 70.530 | 16.052 | −25.694 | 1.00 | 29.45 | B | C |
| ATOM | 16933 | O | VAL | B | 531 | 70.578 | 15.616 | −24.543 | 1.00 | 29.37 | B | O |
| ATOM | 16935 | N | LEU | B | 532 | 71.536 | 15.927 | −26.559 | 1.00 | 29.15 | B | N |
| ATOM | 16936 | CA | LEU | B | 532 | 72.822 | 15.331 | −26.167 | 1.00 | 28.66 | B | C |
| ATOM | 16938 | CB | LEU | B | 532 | 73.687 | 14.993 | −27.391 | 1.00 | 28.54 | B | C |
| ATOM | 16941 | CG | LEU | B | 532 | 73.627 | 13.537 | −27.858 | 1.00 | 29.13 | B | C |
| ATOM | 16943 | CD1 | LEU | B | 532 | 72.216 | 13.153 | −28.293 | 1.00 | 29.00 | B | C |
| ATOM | 16947 | CD2 | LEU | B | 532 | 74.630 | 13.293 | −28.983 | 1.00 | 29.97 | B | C |
| ATOM | 16951 | C | LEU | B | 532 | 73.602 | 16.232 | −25.208 | 1.00 | 28.00 | B | C |
| ATOM | 16952 | O | LEU | B | 532 | 74.158 | 15.751 | −24.220 | 1.00 | 28.07 | B | O |
| ATOM | 16954 | N | SER | B | 533 | 73.632 | 17.532 | −25.500 | 1.00 | 26.92 | B | N |
| ATOM | 16955 | CA | SER | B | 533 | 74.369 | 18.495 | −24.679 | 1.00 | 26.09 | B | C |
| ATOM | 16957 | CB | SER | B | 533 | 74.469 | 19.844 | −25.392 | 1.00 | 26.14 | B | C |
| ATOM | 16960 | OG | SER | B | 533 | 73.243 | 20.553 | −25.320 | 1.00 | 26.63 | B | O |
| ATOM | 16962 | C | SER | B | 533 | 73.722 | 18.697 | −23.311 | 1.00 | 25.29 | B | C |
| ATOM | 16963 | O | SER | B | 533 | 74.420 | 18.822 | −22.303 | 1.00 | 25.77 | B | O |
| ATOM | 16965 | N | VAL | B | 534 | 72.392 | 18.729 | −23.284 | 1.00 | 24.07 | B | N |
| ATOM | 16966 | CA | VAL | B | 534 | 71.643 | 19.035 | −22.065 | 1.00 | 23.05 | B | C |
| ATOM | 16968 | CB | VAL | B | 534 | 70.265 | 19.652 | −22.401 | 1.00 | 22.97 | B | C |
| ATOM | 16970 | CG1 | VAL | B | 534 | 69.412 | 19.793 | −21.152 | 1.00 | 23.85 | B | C |
| ATOM | 16974 | CG2 | VAL | B | 534 | 70.448 | 21.003 | −23.069 | 1.00 | 21.88 | B | C |
| ATOM | 16978 | C | VAL | B | 534 | 71.462 | 17.820 | −21.153 | 1.00 | 22.17 | B | C |
| ATOM | 16979 | O | VAL | B | 534 | 71.657 | 17.926 | −19.942 | 1.00 | 21.94 | B | O |
| ATOM | 16981 | N | ILE | B | 535 | 71.098 | 16.674 | −21.728 | 1.00 | 21.59 | B | N |
| ATOM | 16982 | CA | ILE | B | 535 | 70.783 | 15.471 | −20.938 | 1.00 | 20.91 | B | C |
| ATOM | 16984 | CB | ILE | B | 535 | 69.589 | 14.673 | −21.539 | 1.00 | 20.66 | B | C |
| ATOM | 16986 | CG1 | ILE | B | 535 | 68.343 | 15.558 | −21.675 | 1.00 | 19.60 | B | C |
| ATOM | 16989 | CD1 | ILE | B | 535 | 67.826 | 16.119 | −20.364 | 1.00 | 17.67 | B | C |
| ATOM | 16993 | CG2 | ILE | B | 535 | 69.271 | 13.457 | −20.680 | 1.00 | 19.45 | B | C |
| ATOM | 16997 | C | ILE | B | 535 | 71.972 | 14.519 | −20.762 | 1.00 | 20.28 | B | C |
| ATOM | 16998 | O | ILE | B | 535 | 72.342 | 14.203 | −19.633 | 1.00 | 19.52 | B | O |
| ATOM | 17000 | N | THR | B | 536 | 72.561 | 14.061 | −21.866 | 1.00 | 20.21 | B | N |
| ATOM | 17001 | CA | THR | B | 536 | 73.580 | 13.003 | −21.806 | 1.00 | 20.57 | B | C |
| ATOM | 17003 | CB | THR | B | 536 | 73.444 | 12.009 | −22.988 | 1.00 | 20.61 | B | C |
| ATOM | 17005 | OG1 | THR | B | 536 | 73.670 | 12.688 | −24.229 | 1.00 | 21.12 | B | O |
| ATOM | 17007 | CG2 | THR | B | 536 | 72.058 | 11.372 | −22.996 | 1.00 | 20.40 | B | C |
| ATOM | 17011 | C | THR | B | 536 | 75.025 | 13.520 | −21.730 | 1.00 | 20.49 | B | C |
| ATOM | 17012 | O | THR | B | 536 | 75.658 | 13.438 | −20.677 | 1.00 | 20.27 | B | O |
| ATOM | 17014 | N | GLU | B | 537 | 75.541 | 14.045 | −22.838 | 1.00 | 20.64 | B | N |
| ATOM | 17015 | CA | GLU | B | 537 | 76.956 | 14.423 | −22.932 | 1.00 | 21.04 | B | C |
| ATOM | 17017 | CB | GLU | B | 537 | 77.330 | 14.745 | −24.384 | 1.00 | 21.51 | B | C |
| ATOM | 17020 | CG | GLU | B | 537 | 77.292 | 13.537 | −25.324 | 1.00 | 22.54 | B | C |
| ATOM | 17023 | CD | GLU | B | 537 | 77.568 | 13.898 | −26.780 | 1.00 | 23.27 | B | C |
| ATOM | 17024 | OE1 | GLU | B | 537 | 78.095 | 13.035 | −27.516 | 1.00 | 21.98 | B | O |
| ATOM | 17025 | OE2 | GLU | B | 537 | 77.257 | 15.038 | −27.189 | 1.00 | 24.15 | B | O |
| ATOM | 17026 | C | GLU | B | 537 | 77.311 | 15.617 | −22.031 | 1.00 | 20.83 | B | C |
| ATOM | 17027 | O | GLU | B | 537 | 76.737 | 16.700 | −22.187 | 1.00 | 20.87 | B | O |
| ATOM | 17029 | N | PRO | B | 538 | 78.272 | 15.433 | −21.099 | 1.00 | 20.36 | B | N |
| ATOM | 17030 | CA | PRO | B | 538 | 78.649 | 16.551 | −20.233 | 1.00 | 19.96 | B | C |
| ATOM | 17032 | CB | PRO | B | 538 | 79.456 | 15.883 | −19.104 | 1.00 | 19.93 | B | C |
| ATOM | 17035 | CG | PRO | B | 538 | 79.623 | 14.441 | −19.482 | 1.00 | 19.71 | B | C |
| ATOM | 17038 | CD | PRO | B | 538 | 79.135 | 14.258 | −20.878 | 1.00 | 20.30 | B | C |
| ATOM | 17041 | C | PRO | B | 538 | 79.501 | 17.592 | −20.943 | 1.00 | 19.59 | B | C |
| ATOM | 17042 | O | PRO | B | 538 | 79.934 | 17.380 | −22.077 | 1.00 | 19.30 | B | O |
| ATOM | 17043 | N | ILE | B | 539 | 79.728 | 18.715 | −20.272 | 1.00 | 19.52 | B | N |
| ATOM | 17044 | CA | ILE | B | 539 | 80.663 | 19.715 | −20.763 | 1.00 | 20.00 | B | C |
| ATOM | 17046 | CB | ILE | B | 539 | 80.524 | 21.056 | −20.008 | 1.00 | 20.22 | B | C |
| ATOM | 17048 | CG1 | ILE | B | 539 | 79.134 | 21.656 | −20.230 | 1.00 | 19.71 | B | C |
| ATOM | 17051 | CD1 | ILE | B | 539 | 78.919 | 22.967 | −19.510 | 1.00 | 19.23 | B | C |
| ATOM | 17055 | CG2 | ILE | B | 539 | 81.594 | 22.051 | −20.464 | 1.00 | 19.98 | B | C |
| ATOM | 17059 | C | ILE | B | 539 | 82.072 | 19.168 | −20.569 | 1.00 | 20.32 | B | C |
| ATOM | 17060 | O | ILE | B | 539 | 82.372 | 18.577 | −19.530 | 1.00 | 20.46 | B | O |
| ATOM | 17062 | N | LEU | B | 540 | 82.928 | 19.353 | −21.569 | 1.00 | 20.70 | B | N |
| ATOM | 17063 | CA | LEU | B | 540 | 84.317 | 18.904 | −21.480 | 1.00 | 21.15 | B | C |
| ATOM | 17065 | CB | LEU | B | 540 | 85.103 | 19.328 | −22.725 | 1.00 | 21.14 | B | C |
| ATOM | 17068 | CG | LEU | B | 540 | 84.665 | 18.725 | −24.065 | 1.00 | 20.69 | B | C |
| ATOM | 17070 | CD1 | LEU | B | 540 | 85.271 | 19.506 | −25.229 | 1.00 | 19.34 | B | C |
| ATOM | 17074 | CD2 | LEU | B | 540 | 85.032 | 17.246 | −24.140 | 1.00 | 17.98 | B | C |
| ATOM | 17078 | C | LEU | B | 540 | 84.957 | 19.510 | −20.230 | 1.00 | 21.63 | B | C |
| ATOM | 17079 | O | LEU | B | 540 | 84.734 | 20.687 | −19.939 | 1.00 | 22.38 | B | O |
| ATOM | 17081 | N | PRO | B | 541 | 85.746 | 18.716 | −19.481 | 1.00 | 21.69 | B | N |
| ATOM | 17082 | CA | PRO | B | 541 | 86.321 | 19.215 | −18.224 | 1.00 | 21.85 | B | C |

TABLE 8-2-continued

| Coordinates for L494P Structure | | | | | | | | | | | | |
|---|---|---|---|---|---|---|---|---|---|---|---|---|
| ATOM | 17084 | CB | PRO | B | 541 | 87.149 | 18.027 | −17.712 | 1.00 | 21.79 | B | C |
| ATOM | 17087 | CG | PRO | B | 541 | 87.361 | 17.154 | −18.895 | 1.00 | 22.13 | B | C |
| ATOM | 17090 | CD | PRO | B | 541 | 86.153 | 17.327 | −19.754 | 1.00 | 21.68 | B | C |
| ATOM | 17093 | C | PRO | B | 541 | 87.205 | 20.452 | −18.389 | 1.00 | 22.14 | B | C |
| ATOM | 17094 | O | PRO | B | 541 | 87.704 | 20.723 | −19.480 | 1.00 | 22.12 | B | O |
| ATOM | 17095 | N | PHE | B | 542 | 87.385 | 21.191 | −17.298 | 1.00 | 22.72 | B | N |
| ATOM | 17096 | CA | PHE | B | 542 | 88.184 | 22.414 | −17.305 | 1.00 | 23.32 | B | C |
| ATOM | 17098 | CB | PHE | B | 542 | 87.783 | 23.298 | −16.120 | 1.00 | 23.32 | B | C |
| ATOM | 17101 | CG | PHE | B | 542 | 88.756 | 24.402 | −15.833 | 1.00 | 24.16 | B | C |
| ATOM | 17102 | CD1 | PHE | B | 542 | 89.494 | 24.409 | −14.654 | 1.00 | 24.68 | B | C |
| ATOM | 17104 | CE1 | PHE | B | 542 | 90.398 | 25.425 | −14.389 | 1.00 | 24.06 | B | C |
| ATOM | 17106 | CZ | PHE | B | 542 | 90.580 | 26.443 | −15.309 | 1.00 | 24.14 | B | C |
| ATOM | 17108 | CE2 | PHE | B | 542 | 89.853 | 26.444 | −16.491 | 1.00 | 24.52 | B | C |
| ATOM | 17110 | CD2 | PHE | B | 542 | 88.949 | 25.426 | −16.748 | 1.00 | 24.49 | B | C |
| ATOM | 17112 | C | PHE | B | 542 | 89.688 | 22.104 | −17.261 | 1.00 | 23.94 | B | C |
| ATOM | 17113 | O | PHE | B | 542 | 90.167 | 21.469 | −16.320 | 1.00 | 23.65 | B | O |
| ATOM | 17115 | N | GLU | B | 543 | 90.421 | 22.563 | −18.279 | 1.00 | 24.84 | B | N |
| ATOM | 17116 | CA | GLU | B | 543 | 91.874 | 22.344 | −18.380 | 1.00 | 25.76 | B | C |
| ATOM | 17118 | CB | GLU | B | 543 | 92.235 | 21.696 | −19.728 | 1.00 | 25.79 | B | C |
| ATOM | 17121 | CG | GLU | B | 543 | 92.464 | 20.182 | −19.672 | 1.00 | 25.69 | B | C |
| ATOM | 17124 | CD | GLU | B | 543 | 93.330 | 19.661 | −20.818 | 1.00 | 25.14 | B | C |
| ATOM | 17125 | OE1 | GLU | B | 543 | 93.398 | 20.313 | −21.883 | 1.00 | 24.79 | B | O |
| ATOM | 17126 | OE2 | GLU | B | 543 | 93.945 | 18.587 | −20.650 | 1.00 | 23.90 | B | O |
| ATOM | 17127 | C | GLU | B | 543 | 92.683 | 23.634 | −18.213 | 1.00 | 26.66 | B | C |
| ATOM | 17128 | O | GLU | B | 543 | 92.137 | 24.738 | −18.259 | 1.00 | 26.93 | B | O |
| ATOM | 17130 | N | ARG | B | 544 | 93.992 | 23.470 | −18.017 | 1.00 | 27.44 | B | N |
| ATOM | 17131 | CA | ARG | B | 544 | 94.937 | 24.585 | −17.945 | 1.00 | 28.02 | B | C |
| ATOM | 17133 | CB | ARG | B | 544 | 95.430 | 24.787 | −16.509 | 1.00 | 28.24 | B | C |
| ATOM | 17136 | CG | ARG | B | 544 | 94.332 | 25.114 | −15.508 | 1.00 | 29.37 | B | C |
| ATOM | 17139 | CD | ARG | B | 544 | 94.881 | 25.278 | −14.094 | 1.00 | 31.23 | B | C |
| ATOM | 17142 | NE | ARG | B | 544 | 93.858 | 25.011 | −13.080 | 1.00 | 33.21 | B | N |
| ATOM | 17144 | CZ | ARG | B | 544 | 93.577 | 23.811 | −12.563 | 1.00 | 34.35 | B | C |
| ATOM | 17145 | NH1 | ARG | B | 544 | 94.242 | 22.720 | −12.943 | 1.00 | 34.25 | B | N |
| ATOM | 17148 | NH2 | ARG | B | 544 | 92.616 | 23.700 | −11.649 | 1.00 | 34.18 | B | N |
| ATOM | 17151 | C | ARG | B | 544 | 96.124 | 24.303 | −18.862 | 1.00 | 28.26 | B | C |
| ATOM | 17152 | O | ARG | B | 544 | 96.881 | 25.207 | −19.220 | 1.00 | 28.64 | B | O |
| ATOM | 17154 | O | HOH | C | 1 | 49.400 | −35.729 | 6.838 | 1.00 | 2.00 | | O |
| ATOM | 17157 | O | HOH | C | 2 | 77.843 | −36.939 | −9.130 | 1.00 | 2.00 | | O |
| ATOM | 17160 | O | HOH | C | 3 | 55.726 | −22.590 | −6.230 | 1.00 | 19.51 | | O |
| ATOM | 17163 | O | HOH | C | 4 | 37.476 | −22.187 | −17.999 | 1.00 | 2.00 | | O |

Example 9

Expression and Purification of IspS-T536F

Expression of 6×His-Tagged IspS-T536F

N-terminally 6×His-tagged IspS-T536F was expressed and purified from strain DW363. The growth procedure is suitable for histidine tagged enzymes expressed in BL21 (λDE3)pLysS cells. A 10 ml overnight culture was prepared for each 1 L of planned growth. The appropriate antibiotics (50 mg/ml kanamycin, 50 mg/ml chloramphenicol) were added to 10 ml of LB medium in a 25 ml flask which was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1 L day culture was inoculated with 10 ml of overnight culture and grown at 30-37° C. with shaking at ~220 rpm until the $OD_{600}$ reached ~0.4-0.6. Day cultures were then induced with 400 μM IPTG and allowed to continue growing at 30° C. with shaking at 220 rpm for ~5-6 hours. Cells were then harvested by centrifugation at 10,000×g for 10 min, 4° C. Following Harvest, cells were used directly or stored at −80° C. until ready to process.

Purification of 6×His-Tagged IspS-T536F

For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 40-50 ml of lysis buffer was used per 1 L of cell pellet. Cells were then incubated on ice for approximately 30 min. The cell suspension was then lysed fully by passing 2-3 times through a french pressure cell (large french press cell at 1200 psi/High setting) until lysate started to look clear. A sample of the lysate was saved for activity assay and gel analysis (~100 μl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 μl).

The clarified lysate was run over HisTrap HP columns (GE healthcare) using a gradient from 0-100% Ni buffer B. Following loading of the lysate on the column, the column was washed with Ni wash buffer (50 mM $NaH_2PO_4$, 300 mm NaCl, 20 mM imidazole, ph 8.0). The his-tagged IspS was then eluted from the column using a gradient from 0-100% Ni elution buffer (50 mM $NaH_2PO_4$, 300 mM NaCl, 500 mM imidazole, ph 8.0) and fractions containing the his-tagged IspS were collected. The column was then washed with Ni stripping buffer (20 mM NaH2PO4, 0.5 m NaCl, 50 mM EDTA, ph 7.4). Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a Hi Prep 26/10 Desalting column (GE healthcare) packed with Sephadex G25 resin. The G-25 buffer consisted of 50 mM HEPES, 50 mM NaCl, and 1 mM DTT, pH 7.4. Fractions were then analyzed and concentrated. The samples were then stored at −80° C.

TEV Cleavage (IspS-T536F from Strains DW363)

Strain DW363 is described in Example 6. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (which is also tagged), and impurities. The Ni column pass though and washes were analyzed using SDS-PAGE gel (NUPAGE, Invitrogen; FIG. 54) and DMAPP activity assays. Samples containing pure enzyme were pooled and desalted into 50 mM NaCl pH 7.4 buffer containing 1 mM DTT and stored at −80° C.

Expression Levels of IspS Variants

Small Scale Expression of 6×His-Tagged IspS Variants

N-terminally 6×His-tagged wild type IspS, IspS-L494P, and IspS-T536F were expressed and purified from strains MD09-167, DW399, and DW363, respectively. The growth procedure is suitable for histidine tagged enzymes expressed in BL21(λDE3)pLysS cells. A 3 ml of overnight culture was prepared for each 100 mL of planned growth. The appropriate antibiotics (50 mg/ml kanamycin, 25 mg/ml chloramphenicol) were added to 3 ml of LB medium in a 10 ml glass tube and was inoculated with 1 colony from a fresh plate of cells or directly from glycerol frozen cell stock. Cultures were grown at 30° C. overnight with shaking at ~220 rpm. Day cultures were prepared in 100 mL of LB medium with appropriate antibiotics for each culture. Each 100 mL day culture was inoculated with 50 μl of overnight culture and grown at 37° C. with shaking at ~220 rpm until the $OD_{600}$ reached ~0.4-0.6. Day cultures were then induced with 400 μM IPTG and allowed to continue growing at 30° C. with shaking at 220 rpm for ~5-6 hours. Cells were then harvested by centrifugation at 10,000×g for 10 min, 4° C. Following Harvest, cells were used directly or stored at −80° C. until ready to process.

Purification of 6×His-Tagged IspS Variants Expressed in Small Scale

For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 3 ml of lysis buffer was used per 5 mL of cell pellet. Cells were then incubated on ice for approximately 30 min. The cell suspension was then lysed fully by passing 2-3 times through a french pressure cell (small french press cell at 850 psi/Low setting) until lysate started to look clear. A sample of the lysate was saved for activity assay and gel analysis (~100 μl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 μl).

A 20 mL disposable column containing 0.5 mL Ni Sepharose 6 Fast Flow resin (Amersham) was pre equilibrated with 10 mL of Ni wash buffer. Protein in the clarified lysate was added to the column and shaken gently for 60 min at 4° C. in order to bind the tagged protein. The protein was then eluted with 2.5 mL Ni elution buffer. A sample of the eluate was saved for activity assay and gel analysis (~100 μl).

To buffer exchange the protein into a buffer suitable for protein assays and storage, a PD-10 column (GE Healthcare) was equilibrated with 25 mL PD-10 buffer (50 mM HEPES, 0.05 M NaCl, pH 7.4). Protein was loaded onto the PD-10 column and eluted with 3.5 mL of PD-10 buffer. The eluate was then analyzed by absorbance at 280 nm and SDS-PAGE gel and the samples were stored at −80° C.

Analysis of the yield of purified wild type IspS compared to IspS-L494P, and IspS-T536F suggests that both IspS-L494P and IspS-T536F are expressed at higher levels than the wild type protein (Table 9, FIG. 55).

Differential Scanning Calorimetry

Excessive heat capacity curves were measured using an ultrasensitive scanning high-throughput microcalorimeter, VP-Cap DSC (MicroCal, Inc., Northampton, Mass.). The standard procedure for Differential Scanning calorimetry (DSC) measurements and the theory of the technique is previously published (Freire, E. (1995) Differential Scanning calorimetry *Methods. Mol. Biol.* 41, 191-218). Approximately 500 μL of 0.5 mg/ml IspS (from strain MD09-167) or variant IspS-L494P (from strain DW399) and IspS-T536F (from strain DW363) (in the absence or presence of 5 mM sodium pyrophosphate) were scanned over a 30-100° C. temperature range. The same sample was then re-scanned to check the reversibility of the process. For IspS the thermal unfolding process was irreversible. The buffer used was 50 mM HEPES, 5 mM $MgCl_2$, pH 7.4, with and without 5 mM sodium pyrophosphate. Sodium pyrophosphate was included for its ability to function as a substrate analog. A 200° C./hr scan rate was used to minimize any artifacts that may result from aggregation. The thermal midpoint (Tm) of the DSC curves was used as an indicator of the thermal stability. The thermal melting curves and the melting points for the wild type IspS and variants are shown in FIGS. 56 (buffer only) and 57 (with 5 mM sodium pyrophosphate).

The thermal unfolding for the IspS variants IspS-L494P and IspS-T536F in buffer demonstrates a considerable increase in the melting points for the variants when compared to that for the wild type. In buffer alone, the wild type IspS has a thermal melting point of 58.3° C. while the Tm's for IspS-L494P and IspS-T536F are 60.4° C. and 62.1° C., respectively. Thus, the substitution of L494 with P results in an increase in the Tm of 2.1° C., and the substitution of T536 with F results in an increase in the Tm of 3.8° C.

In the presence of sodium pyrophosphate, the wild type IspS and IspS variants all exhibit a decrease in melting point compared to analysis in buffer alone. When wild type IspS and the variants were thermally-unfolded in the presence of 5 mM sodium pyrophosphate, wild type IspS has a thermal melting point of 54.7° C., while the Tm's for IspS-L494P and IspS-T536F are 57.0° C. and 59.4° C., respectively. Thus, the substitution of L494 with P results in an increase in the Tm of 2.3° C., and the substitution of T536 with F results in an increase in the Tm of 4.7° C. The change in the shape of the DSC traces in the presence of substrate analog and the decrease in the Tm for the proteins could be the result of aggregation or represent a structure or conformational change of the protein upon complexation of the substrate analog. In addition, there is an exothermic peak. Nonetheless, the changes in the Tm's are fairly consistent with those for buffer alone.

Isoprene Synthase Activity vs Temperature

The activity of wild type IspS and variants IspS-L494P and IspS-T536F was measured across a spectrum of temperatures. Individual DMAPP assays were performed at 5° C. intervals from 25° C. to 80° C. by incubating the vials in a pre-heated water bath.

Isoprene Synthase DMAPP Assay

The following reaction mixture was used for the DMAPP assay: 25 μL purified protein, 5 μL MgCl2 (1 M), 5 μL DMAPP (100 mM), and 65 μL 100 mM Tris pH 8, 100 mM NaCl for a total volume of 100 μL. The reaction is performed at the specified temperature for 15 minutes in a gas tight 1.8 mL GC tube. Reactions are terminated by the addition of 100 μL 500 mM EDTA (pH 8). The amount of isoprene produced was measured by GC/MS.

The analysis was performed using an Agilent 6890 GC/MS system interfaced with a CTC Analytics CombiPAL autosampler operating in headspace mode. An Agilent HP-5MS GC/MS column (30 m×0.25 mm; 0.25 μm film thickness) was used for separation of analytes. The sampler was set up to inject 500 μL of headspace gas. The GC/MS method utilized helium as the carrier gas at a flow of 1 ml/min. The injection port was held at 250° C. with a split ratio of 50:1. The oven temperature was held at 37° C. for the 2 min duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 μg/L to 200 μg/L. The limit of detection was estimated to be 50-100 ng/L using this method.

The temperature activity ratios for wild type IspS and variants IspS-L494P and IspS-T536F are plotted in FIG. 58. The IspS-T536F variant shifts the curve both upwards and to the right, suggesting that it has increased activity and thermostability as compared to wild type IspS and IspS-L494P. The activity and thermostability benefits of the T536F variant may be attributable to the replacement of a polar amino acid residue (threonine) with a large, hydrophobic residue (phenylalanine). FIG. 59 shows that at the 536 position, hydrophobic residues such as isoleucine, valine, and phenylalanine are common to many terpene synthase enzymes. It is therefore possible that the T536F mutation serves to remove polarity and introduce a more hydrophobic local region, and this change leads to the observed benefits in catalytic efficiency.

TABLE 9

Relative yield of purified IspS-L494P and IspS-T536F compared to wild type IspS

| Protein | Relative Yield |
|---|---|
| Wild type IspS | 1 |
| IspS-L494P | 1.3 |
| IspS-T536F | 1.9 |

We claim:

1. An isolated host cell comprising an isoprene synthase variant produced by:

a) identifying hydrophobic amino acid residues on the surface of isoprene synthase based on the three dimensional structure of *P. alba* isoprene synthase;

b) introducing one or more amino acid substitutions in the surface amino acids of said isoprene synthase to produce an isoprene synthase variant; and c) identifying said isoprene synthase variants with substitutions that improve activity, expression or stability of the isoprene synthase, wherein said isoprene synthase variant comprises one or more amino acid substitutions at a hydrophobic surface amino acid position corresponding to a hydrophobic surface amino acid position of SEQ ID NO: 45 selected from the group I28, V30, L130, G153, L469, L303 and L494; and wherein said isoprene synthase variant has improved activity, expression or stability of the isoprene synthase compared to an isoprene synthase without said one or more amino acid substitutions.

2. An isolated host cell comprising an isoprene synthase variant, wherein the isoprene synthase variant comprises one or more amino acid substitutions at a hydrophobic surface amino acid position corresponding to a hydrophobic surface amino acid position of SEQ ID NO: 45 selected from the group I28, V30, L130, G153, L469, L303 and L494 and wherein said isoprene synthase variant has improved activity, expression and/or stability as compared to an isoprene synthase without said one or more amino acid substitutions.

3. The isolated host cell of claim 2 wherein the variant comprises one or more substitutions selected from the group consisting of: I28W, I28T, I28R, I28Y, V30K, L130W, L130K, L130S, L130Y, L130R, L130V, L130I, L130E, L130D, G153K, G153H, G153L, G153W, L303I, L469A, L469Q, L494P, L494C, L494I, L494V, L494S, L494G, and L494D.

4. The isolated host cell of claim 2, wherein the cell is a gram-positive bacterial cell, gram-negative bacterial cell, filamentous fungal cell, or yeast cell.

5. The isolated host cell of claim 4, wherein the bacterial cell is selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells.

6. The host cell of claim 4 wherein the cell is selected from the group consisting of *Escherichia* sp. (*E. coli*), *Saccharomyces* sp. (*S. cerevisiae*), *Panteoa* sp. (*P. citrea*), *Bacillus* sp. (*B. subtilis*), *Yarrowia* sp. (*Y. lipolytica*), and *Trichoderma* (*T. reesei*).

7. The isolated host cell of claim 2, wherein the host cell further comprises a heterologous or native nucleic acid encoding an isopentenyl-diphosphate delta-isomerase (IDI) polypeptide and/or a heterologous or native nucleic acid encoding a 1-Deoxyxylulose-5-phosphate synthase (DXS) polypeptide, optionally in combination with the native 1-deoxy-D-xylulose-5-phosphate (DXP) pathway.

8. The isolated host cell of claim 2, wherein the host cell further comprises one or more nucleic acids encoding an IDI polypeptide and a DXS polypeptide.

9. The isolated host cell of claim 2, wherein the host cell comprises one vector encoding the isoprene synthase variant, the IDI polypeptide, and the DXS polypeptide.

10. The isolated host cell of claim 9 wherein the host cell further comprises a heterologous nucleic acid encoding a mevalonate (MVA) pathway polypeptide selected from the group consisting of an MVA pathway polypeptide from *Saccharomyces cerevisiae* and *Enterococcus faecalis*.

11. The isolated host cell of claim 2 wherein the host cell further comprises one or more nucleic acids encoding an MVA pathway polypeptide and a DXS polypeptide and wherein one vector encodes the isoprene synthase variant, the MVA pathway polypeptide, and the DXS polypeptide.

12. The isolated host cell of claim 2 wherein the host cell further comprises one or more nucleic acids encoding a DXS polypeptide, an IDI polypeptide, or one or more of the rest of the DXP pathway polypeptides, and a MVA pathway polypeptide.

13. The isolated host cell of claim 2, wherein the host cell further comprises one or more heterologous nucleic acid(s) encoding an MVA pathway polypeptide.

14. The isolated host cell of claim 13, wherein the host cell further comprises one or more nucleic acids encoding an IDI polypeptide.

15. A method of producing isoprene, comprising: (a) providing a host cell of any one of claims 1, 2 and 3-14; and (b) culturing the host cell under conditions suitable for producing isoprene.

* * * * *

SEQUENCE LISTING

```
<160> NUMBER OF SEQ ID NOS: 112

<210> SEQ ID NO 1
<211> LENGTH: 4352
<212> TYPE: DNA
<213> ORGANISM: Artificial Sequence
<220> FEATURE:
<223> OTHER INFORMATION: Synthetic Construct

<400> SEQUENCE: 1

tagaaaaact catcgagcat caaatgaaac tgcaatttat tcatatcagg attatcaata     60

ccatattttt gaaaaagccg tttctgtaat gaaggagaaa actcaccgag gcagttccat    120

aggatggcaa gatcctggta tcggtctgcg attccgactc gtccaacatc aatacaacct    180

attaatttcc cctcgtcaaa aataaggtta tcaagtgaga aatcaccatg agtgacgact    240

gaatccggtg agaatggcaa aagtttatgc atttctttcc agacttgttc aacaggccag    300

ccattacgct cgtcatcaaa atcactcgca tcaaccaaac cgttattcat tcgtgattgc    360

gcctgagcga ggcgaaatac gcgatcgctg ttaaaaggac aattacaaac aggaatcgag    420

tgcaaccggc gcaggaacac tgccagcgca tcaacaatat tttcacctga atcaggatat    480

tcttctaata cctggaacgc tgtttttccg gggatcgcag tggtgagtaa ccatgcatca    540

tcaggagtac ggataaaatg cttgatggtc ggaagtggca taaattccgt cagccagttt    600

agtctgacca tctcatctgt aacatcattg gcaacgctac ctttgccatg tttcagaaac    660

aactctggcg catcgggctt cccatacaag cgatagattg tcgcacctga ttgcccgaca    720

ttatcgcgag cccatttata cccatataaa tcagcatcca tgttggaatt taatcgcggc    780

ctcgacgttt cccgttgaat atggctcata ttcttccttt ttcaatatta ttgaagcatt    840

tatcagggtt attgtctcat gagcggatac atatttgaat gtatttagaa aaataaacaa    900

ataggggtca gtgttacaac caattaacca attctgaaca ttatcgcgag cccatttata    960

cctgaatatg gctcataaca ccccttgttt gcctggcggc agtagcgcgg tggtcccacc   1020

tgaccccatg ccgaactcag aagtgaaacg ccgtagcgcc gatggtagtg tggggactcc   1080
```

-continued

```
ccatgcgaga gtagggaact gccaggcatc aaataaaacg aaaggctcag tcgaaagact   1140
gggcctttcg cccgggctaa ttagggggtg tcgccctttc gattgacgct gcagttagac   1200
atacatcagc tggttaatcg ggaaagggtc aatcagcagc agtttgatgc ggttttcagt   1260
cgcgtagtct gggcgaccca gaccatcgcc atactggtag gtgcagtggg aaacacgtgc   1320
catgttaact gcgatttcca tgaacgcttt aggcagcagg gtggagtcgc taacgcgttc   1380
acgattcatc tttttccatt cggcgtcgat cagtttacgc agttcttcgc gggcctgttc   1440
ctcgctggta ccatcgtttt cgtgcatgta gctaatgata gaattggtag tctcgccacg   1500
ttccagctcc gccgcagagg tggccagatc gttgcacagg cggaagataa cgcagctaga   1560
acgcaccaga ccatggaagt cggtcaggga acgcagcgcg tggtcggaga tgtcttcctg   1620
ctgctggcat acggaaaagt aagacggcgc cagcagcgct acaccggagg aggaaacgct   1680
ggcgttttcc aggtacttgg agaaagccgg gataattttg ttgttggacc atttcgcctc   1740
ttgcagaaag gctttgcaca gttcacgcca gcttttcgtc agataggaca ggttgttatg   1800
acctttctct ttcagaatag aataggacgt gtcgttaacg gtgttgtaca gtgccaggaa   1860
acacagtttc atatagtccg gcagggtgtt aatagcgtta acgtcccagc gctctacagc   1920
atcggtgaac agttgcagtt cgtccagagt gccataaacg tcatacacgt catcgatgat   1980
cgtcaccaga ccaaacattt tagtaacagc tttgcgacat tcaccaaact gcgggtctgg   2040
cgccataccc agtgcccaga aataaacttc catcaggcgg tcgcgtacaa aatccagttt   2100
gctagccagg cccatctcgg tccaccagcg ggacagatct tgcagctctt tctggtgcag   2160
ggtctgtacc atgttaaaat ccagcttcgc cagctccagc agcagctggt gatgcggttc   2220
tttcggttcg tatttatcca ggaaccaacg tgcctccaga cggtgcagac gctggtgata   2280
tggcagttcc agggcgtggc tcacttgttc tgcaaccttg gtattaatgc cttctttcag   2340
gttgttcttc aggtgggtga tggaaaaggt acgcgcctcc tccagcaggt tctcaccctc   2400
gaaacccagg taagacgctt catacaggct cagcaggcct tggacgtcac ctttcagttc   2460
accgctgaaa ccaccttctt tatccttgaa acgctcaaaa acatcctgag aaacctcgaa   2520
accgtgctga cgcagcagac ggaaagacag agcggttgcg tgcaggtcag atttgttctt   2580
tttgttttcg tccagcagta cgatgttttc cagggcttta atgatgtctt tttcaaattt   2640
gtaggtcaga cccaggcgct gcacatcgtc gatcagctcc agcagggaca gcggctgggt   2700
gtctacacgg ttgatcatgc agcgaacttc ttcctccagt ttggtcgctt tctcctccag   2760
cttttccact ttcaggtcgt tctccaggga ttgcaggaat tcgaaattcc acaggtttgg   2820
ctgatagttt gcggaacgac gggaattatg ctcggtaatc tgagtaaatt gagaagaggt   2880
cgcacacatg ttcagcgaca agggcgacac aaaatttatt ctaaatgcat aataaatact   2940
gataacatct tatagtttgt attatatttt gtattatcgt tgacatgtat aattttgata   3000
tcaaaaactg attttccctt tattattttc gagatttatt ttcttaattc tctttaacaa   3060
actagaaata ttgtatatac aaaaaatcat aaataataga tgaatagttt aattataggt   3120
gttcatcaat cgaaaaagca acgtatctta tttaaagtgc gttgcttttt tctcatttat   3180
aaggttaaat aattctcata tatcaagcaa agtgacaggc gcccttaaat attctgacaa   3240
atgctctttc cctaaactcc ccccataaaa aaacccgccg aagcgggttt ttacgttatt   3300
tgcggattaa cgattactcg ttatcagaac cgcccagggg gcccgagctt aagactggcc   3360
gtcgttttac aacacagaaa gagtttgtag aaacgcaaaa aggccatccg tcaggggcct   3420
tctgcttagt ttgatgcctg gcagttccct actctcgcct tccgcttcct cgctcactga   3480
```

```
ctcgctgcgc tcggtcgttc ggctgcggcg agcggtatca gctcactcaa aggcggtaat   3540

acggttatcc acagaatcag gggataacgc aggaaagaac atgtgagcaa aaggccagca   3600

aaaggccagg aaccgtaaaa aggccgcgtt gctggcgttt ttccataggc tccgcccccc   3660

tgacgagcat cacaaaaatc gacgctcaag tcagaggtgg cgaaacccga caggactata   3720

aagataccag gcgtttcccc ctggaagctc cctcgtgcgc tctcctgttc cgaccctgcc   3780

gcttaccgga tacctgtccg cctttctccc ttcgggaagc gtggcgcttt ctcatagctc   3840

acgctgtagg tatctcagtt cggtgtaggt cgttcgctcc aagctgggct gtgtgcacga   3900

accccccgtt cagcccgacc gctgcgcctt atccggtaac tatcgtcttg agtccaaccc   3960

ggtaagacac gacttatcgc cactggcagc agccactggt aacaggatta gcagagcgag   4020

gtatgtaggc ggtgctacag agttcttgaa gtggtgggct aactacggct acactagaag   4080

aacagtattt ggtatctgcg ctctgctgaa gccagttacc ttcggaaaaa gagttggtag   4140

ctcttgatcc ggcaaacaaa ccaccgctgg tagcggtggt ttttttgttt gcaagcagca   4200

gattacgcgc agaaaaaaag gatctcaaga agatcctttg atcttttcta cggggtctga   4260

cgctcagtgg aacgacgcgc gcgtaactca cgttaaggga ttttggtcat gagcttgcgc   4320

cgtcccgtca agtcagcgta atgctctgct tt                                 4352
```

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2

```
gtttgacagc ttatcatcga ctgcacggtg caccaatgct tctggcgtca ggcagccatc     60

ggaagctgtg gtatggctgt gcaggtcgta aatcactgca taattcgtgt cgctcaaggc    120

gcactcccgt tctggataat gtttttttgcg ccgacatcat aacggttctg gcaaatattc    180

tgaaatgagc tgttgacaat taatcatccg gctcgtataa tgtgtggaat tgtgagcgga    240

taacaatttc acacaggaaa cagcgccgct gagaaaaagc gaagcggcac tgctctttaa    300

caatttatca gacaatctgt gtgggcactc gaccggaatt atcgattaac tttattatta    360

aaaattaaag aggtatatat taatgtatcg attaaataag gaggaataaa ccatgtgtgc    420

gacctcttct caatttactc agattaccga gcataattcc cgtcgttccg caaactatca    480

gccaaacctg tggaatttcg aattcctgca atccctggag aacgacctga aagtggaaaa    540

gctggaggag aaagcgacca aactggagga agaagttcgc tgcatgatca accgtgtaga    600

cacccagccg ctgtccctgc tggagctgat cgacgatgtg cagcgcctgg gtctgaccta    660

caaatttgaa aaagacatca ttaaagccct ggaaaacatc gtactgctgg acgaaaacaa    720

aaagaacaaa tctgacctgc acgcaaccgc tctgtctttc cgtctgctgc gtcagcacgg    780

tttcgaggtt tctcaggatg tttttgagcg tttcaaggat aaagaaggtg gtttcagcgg    840

tgaactgaaa ggtgacgtcc aaggcctgct gagcctgtat gaagcgtctt acctgggttt    900

cgagggtgag aacctgctgg aggaggcgcg taccttttcc atcacccacc tgaagaacaa    960

cctgaaagaa ggcattaata ccaaggttgc agaacaagtg agccacgccc tggaactgcc   1020

atatcaccag cgtctgcacc gtctggaggc acgttggttc ctggataaat acgaaccgaa   1080

agaaccgcat caccagctgc tgctggagct ggcgaagctg gattttaaca tggtacagac   1140

cctgcaccag aaagagctgc aagatctgtc ccgctggtgg accgagatgg gcctggctag   1200
```

-continued caaactggat tttgtacgcg accgcctgat ggaagtttat ttctgggcac tgggtatggc 1260
gccagacccg cagtttggtg aatgtcgcaa agctgttact aaaatgtttg gtctggtgac 1320
gatcatcgat gacgtgtatg acgtttatgg cactctggac gaactgcaac tgttcaccga 1380
tgctgtagag cgctgggacg ttaacgctat taacaccctg ccggactata tgaaactgtg 1440
tttcctggca ctgtacaaca ccgttaacga cacgtcctat tctattctga aagagaaagg 1500
tcataacaac ctgtcctatc tgacgaaaag ctggcgtgaa ctgtgcaaag cctttctgca 1560
agaggcgaaa tggtccaaca acaaaattat cccggctttc tccaagtacc tggaaaacgc 1620
cagcgtttcc tcctccggtg tagcgctgct ggcgccgtct tacttttccg tatgccagca 1680
gcaggaagac atctccgacc acgcgctgcg ttccctgacc gacttccatg gtctggtgcg 1740
ttctagctgc gttatcttcc gcctgtgcaa cgatctggcc acctctgcgg cggagctgga 1800
acgtggcgag actaccaatt ctatcattag ctacatgcac gaaaacgatg gtaccagcga 1860
ggaacaggcc cgcgaagaac tgcgtaaact gatcgacgcc gaatggaaaa agatgaatcg 1920
tgaacgcgtt agcgactcca ccctgctgcc taaagcgttc atggaaatcg cagttaacat 1980
ggcacgtgtt tcccactgca cctaccagta tggcgatggt ctgggtcgcc cagactacgc 2040
gactgaaaac cgcatcaaac tgctgctgat tgaccctttc ccgattaacc agctgatgta 2100
tgtctaactg cagctggtac catatgggaa ttcgaagctt tctagaacaa aaactcatct 2160
cagaagagga tctgaatagc gccgtcgacc atcatcatca tcatcattga gtttaaacgg 2220
tctccagctt ggctgttttg gcggatgaga gaagattttc agcctgatac agattaaatc 2280
agaacgcaga agcggtctga taaaacagaa tttgcctggc ggcagtagcg cggtggtccc 2340
acctgacccc atgccgaact cagaagtgaa acgccgtagc gccgatggta gtgtggggtc 2400
tccccatgcg agagtaggga actgccaggc atcaaataaa acgaaaggct cagtcgaaag 2460
actgggcctt tcgttttatc tgttgtttgt cggtgaacgc tctcctgagt aggacaaatc 2520
cgccgggagc ggatttgaac gttgcgaagc aacggcccgg agggtggcgg gcaggacgcc 2580
cgccataaac tgccaggcat caaattaagc agaaggccat cctgacggat ggcctttttg 2640
cgtttctaca aactcttttt gtttattttt ctaaatacat tcaaatatgt atccgctcat 2700
gagacaataa ccctgataaa tgcttcaata atattgaaaa aggaagagta tgagtattca 2760
acatttccgt gtcgccctta ttcccttttt tgcggcattt tgccttcctg tttttgctca 2820
cccagaaacg ctggtgaaag taaaagatgc tgaagatcag ttgggtgcac gagtgggtta 2880
catcgaactg gatctcaaca gcggtaagat ccttgagagt tttcgccccg aagaacgttt 2940
tccaatgatg agcactttta aagttctgct atgtggcgcg gtattatccc gtgttgacgc 3000
cgggcaagag caactcggtc gccgcataca ctattctcag aatgacttgg ttgagtactc 3060
accagtcaca gaaaagcatc ttacggatgg catgacagta agagaattat gcagtgctgc 3120
cataaccatg agtgataaca ctgcggccaa cttacttctg acaacgatcg gaggaccgaa 3180
ggagctaacc gcttttttgc acaacatggg ggatcatgta actcgccttg atcgttggga 3240
accggagctg aatgaagcca taccaaacga cgagcgtgac accacgatgc ctgtagcaat 3300
ggcaacaacg ttgcgcaaac tattaactgg cgaactactt actctagctt cccggcaaca 3360
attaatagac tggatggagg cggataaagt tgcaggacca cttctgcgct cggcccttcc 3420
ggctggctgg tttattgctg ataaatctgg agccggtgag cgtgggtctc gcggtatcat 3480
tgcagcactg gggccagatg gtaagccctc ccgtatcgta gttatctaca cgacggggag 3540
tcaggcaact atggatgaac gaaatagaca gatcgctgag ataggtgcct cactgattaa 3600

-continued

```
gcattggtaa ctgtcagacc aagtttactc atatatactt tagattgatt taaaacttca   3660
tttttaattt aaaaggatct aggtgaagat cctttttgat aatctcatga ccaaaatccc   3720
ttaacgtgag ttttcgttcc actgagcgtc agaccccgta gaaaagatca aaggatcttc   3780
ttgagatcct ttttttctgc gcgtaatctg ctgcttgcaa acaaaaaaac caccgctacc   3840
agcggtggtt tgtttgccgg atcaagagct accaactctt tttccgaagg taactggctt   3900
cagcagagcg cagataccaa atactgtcct tctagtgtag ccgtagttag gccaccactt   3960
caagaactct gtagcaccgc ctacatacct cgctctgcta atcctgttac cagtggctgc   4020
tgccagtggc gataagtcgt gtcttaccgg gttggactca agacgatagt taccggataa   4080
ggcgcagcgg tcgggctgaa cggggggttc gtgcacacag cccagcttgg agcgaacgac   4140
ctacaccgaa ctgagatacc tacagcgtga gctatgagaa agcgccacgc ttcccgaagg   4200
gagaaaggcg gacaggtatc cggtaagcgg cagggtcgga acaggagagc gcacgaggga   4260
gcttccaggg ggaaacgcct ggtatcttta tagtcctgtc gggtttcgcc acctctgact   4320
tgagcgtcga tttttgtgat gctcgtcagg ggggcggagc ctatggaaaa acgccagcaa   4380
cgcggccttt ttacggttcc tggccttttg ctggcctttt gctcacatgt tctttcctgc   4440
gttatcccct gattctgtgg ataaccgtat taccgccttt gagtgagctg ataccgctcg   4500
ccgcagccga acgaccgagc gcagcgagtc agtgagcgag gaagcggaag agcgcctgat   4560
gcggtatttt ctccttacgc atctgtgcgg tatttcacac cgcatatggt gcactctcag   4620
tacaatctgc tctgatgccg catagttaag ccagtataca ctccgctatc gctacgtgac   4680
tgggtcatgg ctgcgccccg acacccgcca acacccgctg acgcgccctg acgggcttgt   4740
ctgctcccgg catccgctta cagacaagct gtgaccgtct ccgggagctg catgtgtcag   4800
aggttttcac cgtcatcacc gaaacgcgcg aggcagcaga tcaattcgcg cgcgaaggcg   4860
aagcggcatg catttacgtt gacaccatcg aatggtgcaa aacctttcgc ggtatggcat   4920
gatagcgccc ggaagagagt caattcaggg tggtgaatgt gaaaccagta acgttatacg   4980
atgtcgcaga gtatgccggt gtctcttatc agaccgtttc ccgcgtggtg aaccaggcca   5040
gccacgtttc tgcgaaaacg cgggaaaaag tggaagcggc gatggcggag ctgaattaca   5100
ttcccaaccg cgtggcacaa caactggcgg gcaaacagtc gttgctgatt ggcgttgcca   5160
cctccagtct ggccctgcac gcgccgtcgc aaattgtcgc ggcgattaaa tctcgcgccg   5220
atcaactggg tgccagcgtg gtggtgtcga tggtagaacg aagcggcgtc gaagcctgta   5280
aagcggcggt gcacaatctt ctcgcgcaac gcgtcagtgg gctgatcatt aactatccgc   5340
tggatgacca ggatgccatt gctgtggaag ctgcctgcac taatgttccg gcgttatttc   5400
ttgatgtctc tgaccagaca cccatcaaca gtattatttt ctcccatgaa gacggtacgc   5460
gactgggcgt ggagcatctg gtcgcattgg gtcaccagca aatcgcgctg ttagcgggcc   5520
cattaagttc tgtctcggcg cgtctgcgtc tggctggctg gcataaatat ctcactcgca   5580
atcaaattca gccgatagcg gaacgggaag gcgactggag tgccatgtcc ggttttcaac   5640
aaaccatgca aatgctgaat gagggcatcg ttcccactgc gatgctggtt gccaacgatc   5700
agatggcgct gggcgcaatg cgcgccatta ccgagtccgg gctgcgcgtt ggtgcggata   5760
tctcggtagt gggatacgac gataccgaag acagctcatg ttatatcccg ccgtcaacca   5820
ccatcaaaca ggattttcgc ctgctggggc aaaccagcgt ggaccgcttg ctgcaactct   5880
ctcagggcca ggcggtgaag ggcaatcagc tgttgcccgt ctcactggtg aaaagaaaaa   5940
ccaccctggc gcccaatacg caaaccgcct ctccccgcgc gttggccgat tcattaatgc   6000
```

agctggcacg acaggtttcc cgactggaaa gcgggcagtg agcgcaacgc aattaatgtg 6060
agttagcgcg aattgatctg 6080

<210> SEQ ID NO 3
<211> LENGTH: 6646
<212> TYPE: DNA
<213> ORGANISM: Artificial Sequence
<220> FEATURE:
<223> OTHER INFORMATION: Synthetic Construct

<400> SEQUENCE: 3
ccgacaccat cgaatggtgc aaaacctttc gcggtatggc atgatagcgc ccggaagaga 60
gtcaattcag ggtggtgaat gtgaaaccag taacgttata cgatgtcgca gagtatgccg 120
gtgtctctta tcagaccgtt tcccgcgtgg tgaaccaggc cagccacgtt tctgcgaaaa 180
cgcgggaaaa agtggaagcg gcgatggcgg agctgaatta cattcccaac cgcgtggcac 240
aacaactggc gggcaaacag tcgttgctga ttggcgttgc cacctccagt ctggccctgc 300
acgcgccgtc gcaaattgtc gcggcgatta aatctcgcgc cgatcaactg ggtgccagcg 360
tggtggtgtc gatggtagaa cgaagcggcg tcgaagcctg taaagcggcg gtgcacaatc 420
ttctcgcgca acgcgtcagt gggctgatca ttaactatcc gctggatgac caggatgcca 480
ttgctgtgga agctgcctgc actaatgttc cggcgttatt tcttgatgtc tctgaccaga 540
cacccatcaa cagtattatt ttctcccatg aagacggtac gcgactgggc gtggagcatc 600
tggtcgcatt gggtcaccag caaatcgcgc tgttagcggg cccattaagt tctgtctcgg 660
cgcgtctgcg tctggctggc tggcataaat atctcactcg caatcaaatt cagccgatag 720
cggaacggga aggcgactgg agtgccatgt ccggttttca acaaaccatg caaatgctga 780
atgagggcat cgttcccact gcgatgctgg ttgccaacga tcagatggcg ctgggcgcaa 840
tgcgcgccat taccgagtcc gggctgcgcg ttggtgcgga tatctcggta gtgggatacg 900
acgataccga agacagctca tgttatatcc cgccgttaac caccatcaaa caggattttc 960
gcctgctggg gcaaaccagc gtggaccgct tgctgcaact ctctcagggc caggcggtga 1020
agggcaatca gctgttgccc gtctcactgg tgaaaagaaa aaccaccctg gcgcccaata 1080
cgcaaaccgc ctctccccgc gcgttggccg attcattaat gcagctggca cgacaggttt 1140
cccgactgga aagcgggcag tgagcgcaac gcaattaatg taagttagct cactcattag 1200
gcacaattct catgtttgac agcttatcat cgactgcacg gtgcaccaat gcttctggcg 1260
tcaggcagcc atcggaagct gtggtatggc tgtgcaggtc gtaaatcact gcataattcg 1320
tgtcgctcaa ggcgcactcc cgttctggat aatgtttttt gcgccgacat cataacggtt 1380
ctggcaaata ttctgaaatg agctgttgac aattaatcat cggctcgtat aatgtgtgga 1440
attgtgagcg gataacaatt tcacacagga aacagccagt ccgtttaggt gttttcacga 1500
gcacttcacc aacaaggacc atagcatatg aaaatcgaag aaggtaaact ggtaatctgg 1560
attaacggcg ataaaggcta taacggtctc gctgaagtcg gtaagaaatt cgagaaagat 1620
accggaatta aagtcaccgt tgagcatccg gataaactgg aagagaaatt cccacaggtt 1680
gcggcaactg gcgatggccc tgacattatc ttctgggcac acgaccgctt tggtggctac 1740
gctcaatctg gcctgttggc tgaaatcacc ccggacaaag cgttccagga caagctgtat 1800
ccgtttacct gggatgccgt acgttacaac ggcaagctga ttgcttaccc gatcgctgtt 1860
gaagcgttat cgctgattta taacaaagat ctgctgccga acccgccaaa aacctgggaa 1920
gagatcccgg cgctggataa agaactgaaa gcgaaaggta agagcgcgct gatgttcaac 1980

-continued

```
ctgcaagaac cgtacttcac ctggccgctg attgctgctg acgggggtta tgcgttcaag   2040
tatgaaaacg gcaagtacga cattaaagac gtgggcgtgg ataacgctgg cgcgaaagcg   2100
ggtctgacct tcctggttga cctgattaaa aacaaacaca tgaatgcaga caccgattac   2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggtgaaag atccgcggat tgccgccact atggaaaacg cccagaaagg tgaaatcatg   2520
ccgaacatcc cgcagatgtc cgctttctgg tatgccgtgc gtactgcggt gatcaacgcc   2580
gccagcggtc gtcagactgt cgatgaagcc ctgaaagacg cgcagactaa ttcgagctcg   2640
aacaacaaca acaataacaa taacaacaac ctcgggatcg agggaaggat ttcagaattc   2700
ggatcctcta gagtcgacct gcaggcaagc ttggcactgg ccgtcgtttt acaacgtcgt   2760
gactgggaaa accctggcgt tacccaactt aatcgccttg cagcacatcc ccctttcgcc   2820
agctggcgta atagcgaaga ggcccgcacc gatcgccctt cccaacagtt gcgcagcctg   2880
aatggcgaat ggcagcttgg ctgttttggc ggatgagata agattttcag cctgatacag   2940
attaaatcag aacgcagaag cggtctgata aaacagaatt tgcctggcgg cagtagcgcg   3000
gtggtcccac ctgaccccat gccgaactca gaagtgaaac gccgtagcgc cgatggtagt   3060
gtggggtctc cccatgcgag agtagggaac tgccaggcat caaataaaac gaaaggctca   3120
gtcgaaagac tgggcctttc gttttatctg ttgtttgtcg gtgaacgctc tcctgagtag   3180
gacaaatccg ccgggagcgg atttgaacgt tgcgaagcaa cggcccggag ggtggcgggc   3240
aggacgcccg ccataaactg ccaggcatca aattaagcag aaggccatcc tgacggatgg   3300
cctttttgcg tttctacaaa ctctttttgt ttatttttct aaatacattc aaatatgtat   3360
ccgctcatga gacaataacc ctgataaatg cttcaataat attgaaaaag gaagagtatg   3420
agtattcaac atttccgtgt cgcccttatt cccttttttg cggcattttg ccttcctgtt   3480
tttgctcacc cagaaacgct ggtgaaagta aaagatgctg aagatcagtt gggtgcacga   3540
gtgggttaca tcgaactgga tctcaacagc ggtaagatcc ttgagagttt tcgccccgaa   3600
gaacgttctc caatgatgag cacttttaaa gttctgctat gtggcgcggt attatcccgt   3660
gttgacgccg ggcaagagca actcggtcgc cgcatacact attctcagaa tgacttggtt   3720
gagtactcac cagtcacaga aaagcatctt acggatggca tgacagtaag agaattatgc   3780
agtgctgcca taaccatgag tgataacact gcggccaact tacttctgac aacgatcgga   3840
ggaccgaagg agctaaccgc ttttttgcac aacatggggg atcatgtaac tcgccttgat   3900
cgttgggaac cggagctgaa tgaagccata ccaaacgacg agcgtgacac cacgatgcct   3960
gtagcaatgg caacaacgtt gcgcaaacta ttaactggcg aactacttac tctagcttcc   4020
cggcaacaat taatagactg gatggaggcg gataaagttg caggaccact tctgcgctcg   4080
gcccttccgg ctggctggtt tattgctgat aaatctggag ccggtgagcg tgggtctcgc   4140
ggtatcattg cagcactggg gccagatggt aagccctccc gtatcgtagt tatctacacg   4200
acggggagtc aggcaactat ggatgaacga aatagacaga tcgctgagat aggtgcctca   4260
ctgattaagc attggtaact gtcagaccaa gtttactcat atatacttta gattgattta   4320
ccccggttga taatcagaaa agccccaaaa acaggaagat tgtataagca aatatttaaa   4380
```

-continued

```
ttgtaaacgt taatattttg ttaaaattcg cgttaaattt ttgttaaatc agctcatttt   4440
ttaaccaata ggccgaaatc ggcaaaatcc cttataaatc aaaagaatag accgagatag   4500
ggttgagtgt tgttccagtt tggaacaaga gtccactatt aaagaacgtg gactccaacg   4560
tcaaagggcg aaaaaccgtc tatcagggcg atggcccact acgtgaacca tcacccaaat   4620
caagtttttt ggggtcgagg tgccgtaaag cactaaatcg gaaccctaaa gggagccccc   4680
gatttagagc ttgacgggga aagccggcga acgtggcgag aaaggaaggg aagaaagcga   4740
aaggagcggg cgctagggcg ctggcaagtg tagcggtcac gctgcgcgta accaccacac   4800
ccgccgcgct taatgcgccg ctacagggcg cgtaaaagga tctaggtgaa gatccttttt   4860
gataatctca tgaccaaaat cccttaacgt gagttttcgt tccactgagc gtcagacccc   4920
gtagaaaaga tcaaaggatc ttcttgagat cctttttttc tgcgcgtaat ctgctgcttg   4980
caaacaaaaa aaccaccgct accagcggtg gtttgtttgc cggatcaaga gctaccaact   5040
ctttttccga aggtaactgg cttcagcaga gcgcagatac caaatactgt ccttctagtg   5100
tagccgtagt taggccacca cttcaagaac tctgtagcac cgcctacata cctcgctctg   5160
ctaatcctgt taccagtggc tgctgccagt ggcgataagt cgtgtcttac cgggttggac   5220
tcaagacgat agttaccgga taaggcgcag cggtcgggct gaacgggggg ttcgtgcaca   5280
cagcccagct tggagcgaac gacctacacc gaactgagat acctacagcg tgagctatga   5340
gaaagcgcca cgcttcccga agggagaaag gcggacaggt atccggtaag cggcagggtc   5400
ggaacaggag agcgcacgag ggagcttcca gggggaaacg cctggtatct ttatagtcct   5460
gtcgggtttc gccacctctg acttgagcgt cgatttttgt gatgctcgtc aggggggcgg   5520
agcctatgga aaaacgccag caacgcggcc tttttacggt tcctggcctt ttgctggcct   5580
tttgctcaca tgttctttcc tgcgttatcc cctgattctg tggataaccg tattaccgcc   5640
tttgagtgag ctgataccgc tcgccgcagc cgaacgaccg agcgcagcga gtcagtgagc   5700
gaggaagcgg aagagcgcct gatgcggtat tttctcctta cgcatctgtg cggtatttca   5760
caccgcatat atggtgcact ctcagtacaa tctgctctga tgccgcatag ttaagccagt   5820
atacactccg ctatcgctac gtgactgggt catggctgcg ccccgacacc cgccaacacc   5880
cgctgacgcg ccctgacggg cttgtctgct cccggcatcc gcttacagac aagctgtgac   5940
cgtctccggg agctgcatgt gtcagaggtt ttcaccgtca tcaccgaaac gcgcgaggca   6000
gctgcggtaa agctcatcag cgtggtcgtg cagcgattca cagatgtctg cctgttcatc   6060
cgcgtccagc tcgttgagtt tctccagaag cgttaatgtc tggcttctga taaagcgggc   6120
catgttaagg gcggtttttt cctgtttggt cactgatgcc tccgtgtaag ggggatttct   6180
gttcatgggg gtaatgatac cgatgaaacg agagaggatg ctcacgatac gggttactga   6240
tgatgaacat gcccggttac tggaacgttg tgagggtaaa caactggcgg tatggatgcg   6300
gcgggaccag agaaaaatca ctcagggtca atgccagcgc ttcgttaata cagatgtagg   6360
tgttccacag ggtagccagc agcatcctgc gatgcagatc cggaacataa tggtgcaggg   6420
cgctgacttc cgcgtttcca gactttacga aacacggaaa ccgaagacca ttcatgttgt   6480
tgctcaggtc gcagacgttt tgcagcagca gtcgcttcac gttcgctcgc gtatcggtga   6540
ttcattctgc taaccagtaa ggcaaccccg ccagcctagc cgggtcctca acgacaggag   6600
cacgatcatg cgcacccgtg gccaggaccc aacgctgccc gaaatt                  6646
```

<210> SEQ ID NO 4
<211> LENGTH: 8310

<212> TYPE: DNA
<213> ORGANISM: Artificial Sequence
<220> FEATURE:
<223> OTHER INFORMATION: Synthetic Construct

<400> SEQUENCE: 4
ccgacaccat cgaatggtgc aaaacctttc gcggtatggc atgatagcgc ccggaagaga 60
gtcaattcag ggtggtgaat gtgaaaccag taacgttata cgatgtcgca gagtatgccg 120
gtgtctctta tcagaccgtt tcccgcgtgg tgaaccaggc cagccacgtt tctgcgaaaa 180
cgcgggaaaa agtggaagcg gcgatggcgg agctgaatta cattcccaac cgcgtggcac 240
aacaactggc gggcaaacag tcgttgctga ttggcgttgc cacctccagt ctggccctgc 300
acgcgccgtc gcaaattgtc gcggcgatta aatctcgcgc cgatcaactg ggtgccagcg 360
tggtggtgtc gatggtagaa cgaagcggcg tcgaagcctg taaagcggcg gtgcacaatc 420
ttctcgcgca acgcgtcagt gggctgatca ttaactatcc gctggatgac caggatgcca 480
ttgctgtgga agctgcctgc actaatgttc cggcgttatt tcttgatgtc tctgaccaga 540
cacccatcaa cagtattatt ttctcccatg aagacggtac gcgactgggc gtggagcatc 600
tggtcgcatt gggtcaccag caaatcgcgc tgttagcggg cccattaagt tctgtctcgg 660
cgcgtctgcg tctggctggc tggcataaat atctcactcg caatcaaatt cagccgatag 720
cggaacggga aggcgactgg agtgccatgt ccggttttca acaaaccatg caaatgctga 780
atgagggcat cgttcccact gcgatgctgg ttgccaacga tcagatggcg ctgggcgcaa 840
tgcgcgccat taccgagtcc gggctgcgcg ttggtgcgga tatctcggta gtgggatacg 900
acgataccga agacagctca tgttatatcc cgccgttaac caccatcaaa caggattttc 960
gcctgctggg gcaaaccagc gtggaccgct tgctgcaact ctctcagggc caggcggtga 1020
agggcaatca gctgttgccc gtctcactgg tgaaaagaaa aaccaccctg gcgcccaata 1080
cgcaaaccgc ctctccccgc gcgttggccg attcattaat gcagctggca cgacaggttt 1140
cccgactgga aagcgggcag tgagcgcaac gcaattaatg taagttagct cactcattag 1200
gcacaattct catgtttgac agcttatcat cgactgcacg gtgcaccaat gcttctggcg 1260
tcaggcagcc atcggaagct gtggtatggc tgtgcaggtc gtaaatcact gcataattcg 1320
tgtcgctcaa ggcgcactcc cgttctggat aatgtttttt gcgccgacat cataacggtt 1380
ctggcaaata ttctgaaatg agctgttgac aattaatcat cggctcgtat aatgtgtgga 1440
attgtgagcg gataacaatt tcacacagga aacagccagt ccgtttaggt gttttcacga 1500
gcacttcacc aacaaggacc atagcatatg aaaatcgaag aaggtaaact ggtaatctgg 1560
attaacggcg ataaaggcta taacggtctc gctgaagtcg gtaagaaatt cgagaaagat 1620
accggaatta aagtcaccgt tgagcatccg gataaactgg aagagaaatt cccacaggtt 1680
gcggcaactg gcgatggccc tgacattatc ttctgggcac acgaccgctt tggtggctac 1740
gctcaatctg gcctgttggc tgaaatcacc ccggacaaag cgttccagga caagctgtat 1800
ccgtttacct gggatgccgt acgttacaac ggcaagctga ttgcttaccc gatcgctgtt 1860
gaagcgttat cgctgattta taacaaagat ctgctgccga acccgccaaa aacctgggaa 1920
gagatcccgg cgctggataa agaactgaaa gcgaaaggta agagcgcgct gatgttcaac 1980
ctgcaagaac cgtacttcac ctggccgctg attgctgctg acgggggtta tgcgttcaag 2040
tatgaaaacg gcaagtacga cattaaagac gtgggcgtgg ataacgctgg cgcgaaagcg 2100
ggtctgacct tcctggttga cctgattaaa aacaaacaca tgaatgcaga caccgattac 2160
tccatcgcag aagctgcctt taataaaggc gaaacagcga tgaccatcaa cggcccgtgg 2220

-continued

```
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggtgaaag atccgcggat tgccgccact atggaaaacg cccagaaagg tgaaatcatg   2520
ccgaacatcc cgcagatgtc cgctttctgg tatgccgtgc gtactgcggt gatcaacgcc   2580
gccagcggtc gtcagactgt cgatgaagcc ctgaaagacg cgcagactaa ttcgagctcg   2640
aacaacaaca acaataacaa taacaacaac ctcgggatcg agggaaggat ttcagaattc   2700
tgtgcgacct cttctcaatt tactcagatt accgagcata attcccgtcg ttccgcaaac   2760
tatcagccaa acctgtggaa tttcgaattc ctgcaatccc tggagaacga cctgaaagtg   2820
gaaaagctgg aggagaaagc gaccaaactg gaggaagaag ttcgctgcat gatcaaccgt   2880
gtagacaccc agccgctgtc cctgctggag ctgatcgacg atgtgcagcg cctgggtctg   2940
acctacaaat ttgaaaaaga catcattaaa gccctggaaa acatcgtact gctggacgaa   3000
aacaaaaaga acaaatctga cctgcacgca accgctctgt ctttccgtct gctgcgtcag   3060
cacggtttcg aggtttctca ggatgttttt gagcgtttca aggataaaga aggtggtttc   3120
agcggtgaac tgaaaggtga cgtccaaggc ctgctgagcc tgtatgaagc gtcttacctg   3180
ggtttcgagg gtgagaacct gctggaggag gcgcgtacct tttccatcac ccacctgaag   3240
aacaacctga aagaaggcat taataccaag gttgcagaac aagtgagcca cgccctggaa   3300
ctgccatatc accagcgtct gcaccgtctg gaggcacgtt ggttcctgga taaatacgaa   3360
ccgaaagaac cgcatcacca gctgctgctg gagctggcga agctggattt taacatggta   3420
cagaccctgc accagaaaga gctgcaagat ctgtcccgct ggtggaccga gatgggcctg   3480
gctagcaaac tggattttgt acgcgaccgc ctgatggaag tttatttctg ggcactgggt   3540
atggcgccag acccgcagtt tggtgaatgt cgcaaagctg ttactaaaat gtttggtctg   3600
gtgacgatca tcgatgacgt gtatgacgtt tatggcactc tggacgaact gcaactgttc   3660
accgatgctg tagagcgctg ggacgttaac gctattaaca ccctgccgga ctatatgaaa   3720
ctgtgtttcc tggcactgta caacaccgtt aacgacacgt cctattctat tctgaaagag   3780
aaaggtcata acaacctgtc ctatctgacg aaaagctggc gtgaactgtg caaagccttt   3840
ctgcaagagg cgaaatggtc caacaacaaa attatcccgg ctttctccaa gtacctggaa   3900
aacgccagcg tttcctcctc cggtgtagcg ctgctggcgc cgtcttactt ttccgtatgc   3960
cagcagcagg aagacatctc cgaccacgcg ctgcgttccc tgaccgactt ccatggtctg   4020
gtgcgttcta gctgcgttat cttccgcctg tgcaacgatc tggccacctc tgcggcggag   4080
ctggaacgtg gcgagactac caattctatc attagctaca tgcacgaaaa cgatggtacc   4140
agcgaggaac aggcccgcga agaactgcgt aaactgatcg acgccgaatg gaaaaagatg   4200
aatcgtgaac gcgttagcga ctccaccctg ctgcctaaag cgttcatgga aatcgcagtt   4260
aacatggcac gtgtttccca ctgcacctac cagtatggcg atggtctggg tcgcccagac   4320
tacgcgactg aaaaccgcat caaactgctg ctgattgacc ctttcccgat taaccagctg   4380
atgtatgtct aagcttggca ctggccgtcg ttttacaacg tcgtgactgg gaaaaccctg   4440
gcgttaccca acttaatcgc cttgcagcac atcccccttt cgccagctgg cgtaatagcg   4500
aagaggcccg caccgatcgc ccttcccaac agttgcgcag cctgaatggc gaatggcagc   4560
ttggctgttt tggcggatga gataagattt tcagcctgat acagattaaa tcagaacgca   4620
```

gaagcggtct gataaaacag aatttgcctg gcggcagtag cgcggtggtc ccacctgacc 4680
ccatgccgaa ctcagaagtg aaacgccgta gcgccgatgg tagtgtgggg tctccccatg 4740
cgagagtagg gaactgccag gcatcaaata aaacgaaagg ctcagtcgaa agactgggcc 4800
tttcgtttta tctgttgttt gtcggtgaac gctctcctga gtaggacaaa tccgccggga 4860
gcggatttga acgttgcgaa gcaacggccc ggagggtggc gggcaggacg cccgccataa 4920
actgccaggc atcaaattaa gcagaaggcc atcctgacgg atggcctttt tgcgtttcta 4980
caaactcttt ttgtttattt ttctaaatac attcaaatat gtatccgctc atgagacaat 5040
aaccctgata aatgcttcaa taatattgaa aaaggaagag tatgagtatt caacatttcc 5100
gtgtcgccct tattcccttt tttgcggcat tttgccttcc tgtttttgct cacccagaaa 5160
cgctggtgaa agtaaaagat gctgaagatc agttgggtgc acgagtgggt tacatcgaac 5220
tggatctcaa cagcggtaag atccttgaga gttttcgccc cgaagaacgt tctccaatga 5280
tgagcacttt taaagttctg ctatgtggcg cggtattatc ccgtgttgac gccgggcaag 5340
agcaactcgg tcgccgcata cactattctc agaatgactt ggttgagtac tcaccagtca 5400
cagaaaagca tcttacggat ggcatgacag taagagaatt atgcagtgct gccataacca 5460
tgagtgataa cactgcggcc aacttacttc tgacaacgat cggaggaccg aaggagctaa 5520
ccgctttttt gcacaacatg ggggatcatg taactcgcct tgatcgttgg gaaccggagc 5580
tgaatgaagc cataccaaac gacgagcgtg acaccacgat gcctgtagca atggcaacaa 5640
cgttgcgcaa actattaact ggcgaactac ttactctagc ttcccggcaa caattaatag 5700
actggatgga ggcggataaa gttgcaggac cacttctgcg ctcggccctt ccggctggct 5760
ggtttattgc tgataaatct ggagccggtg agcgtgggtc tcgcggtatc attgcagcac 5820
tggggccaga tggtaagccc tcccgtatcg tagttatcta cacgacgggg agtcaggcaa 5880
ctatggatga acgaaataga cagatcgctg agataggtgc ctcactgatt aagcattggt 5940
aactgtcaga ccaagtttac tcatatatac tttagattga tttaccccgg ttgataatca 6000
gaaaagcccc aaaaacagga agattgtata agcaaatatt taaattgtaa acgttaatat 6060
tttgttaaaa ttcgcgttaa atttttgtta aatcagctca ttttttaacc aataggccga 6120
aatcggcaaa atcccttata aatcaaaaga atagaccgag atagggttga gtgttgttcc 6180
agtttggaac aagagtccac tattaaagaa cgtggactcc aacgtcaaag ggcgaaaaac 6240
cgtctatcag ggcgatggcc cactacgtga accatcaccc aaatcaagtt ttttggggtc 6300
gaggtgccgt aaagcactaa atcggaaccc taaagggagc ccccgattta gagcttgacg 6360
gggaaagccg gcgaacgtgg cgagaaagga agggaagaaa gcgaaaggag cgggcgctag 6420
ggcgctggca agtgtagcgg tcacgctgcg cgtaaccacc acacccgccg cgcttaatgc 6480
gccgctacag ggcgcgtaaa aggatctagg tgaagatcct ttttgataat ctcatgacca 6540
aaatccctta acgtgagttt tcgttccact gagcgtcaga ccccgtagaa aagatcaaag 6600
gatcttcttg agatcctttt tttctgcgcg taatctgctg cttgcaaaca aaaaaaccac 6660
cgctaccagc ggtggtttgt ttgccggatc aagagctacc aactcttttt ccgaaggtaa 6720
ctggcttcag cagagcgcag ataccaaata ctgtccttct agtgtagccg tagttaggcc 6780
accacttcaa gaactctgta gcaccgccta catacctcgc tctgctaatc ctgttaccag 6840
tggctgctgc cagtggcgat aagtcgtgtc ttaccgggtt ggactcaaga cgatagttac 6900
cggataaggc gcagcggtcg ggctgaacgg ggggttcgtg cacacagccc agcttggagc 6960
gaacgaccta caccgaactg agatacctac agcgtgagct atgagaaagc gccacgcttc 7020

```
ccgaagggag aaaggcggac aggtatccgg taagcggcag ggtcggaaca ggagagcgca   7080

cgagggagct tccaggggga aacgcctggt atctttatag tcctgtcggg tttcgccacc   7140

tctgacttga gcgtcgattt ttgtgatgct cgtcaggggg gcggagccta tggaaaaacg   7200

ccagcaacgc ggccttttta cggttcctgg ccttttgctg gccttttgct cacatgttct   7260

ttcctgcgtt atcccctgat tctgtggata accgtattac cgcctttgag tgagctgata   7320

ccgctcgccg cagccgaacg accgagcgca gcgagtcagt gagcgaggaa gcggaagagc   7380

gcctgatgcg gtattttctc cttacgcatc tgtgcggtat ttcacaccgc atatatggtg   7440

cactctcagt acaatctgct ctgatgccgc atagttaagc cagtatacac tccgctatcg   7500

ctacgtgact gggtcatggc tgcgccccga cacccgccaa cacccgctga cgcgccctga   7560

cgggcttgtc tgctcccggc atccgcttac agacaagctg tgaccgtctc cgggagctgc   7620

atgtgtcaga ggttttcacc gtcatcaccg aaacgcgcga ggcagctgcg gtaaagctca   7680

tcagcgtggt cgtgcagcga ttcacagatg tctgcctgtt catccgcgtc cagctcgttg   7740

agtttctcca gaagcgttaa tgtctggctt ctgataaagc gggccatgtt aagggcggtt   7800

ttttcctgtt tggtcactga tgcctccgtg taagggggat ttctgttcat gggggtaatg   7860

ataccgatga aacgagagag gatgctcacg atacgggtta ctgatgatga acatgcccgg   7920

ttactggaac gttgtgaggg taaacaactg gcggtatgga tgcggcggga ccagagaaaa   7980

atcactcagg gtcaatgcca gcgcttcgtt aatacagatg taggtgttcc acagggtagc   8040

cagcagcatc ctgcgatgca gatccggaac ataatggtgc agggcgctga cttccgcgtt   8100

tccagacttt acgaaacacg gaaaccgaag accattcatg ttgttgctca ggtcgcagac   8160

gttttgcagc agcagtcgct tcacgttcgc tcgcgtatcg gtgattcatt ctgctaacca   8220

gtaaggcaac cccgccagcc tagccgggtc ctcaacgaca ggagcacgat catgcgcacc   8280

cgtggccagg acccaacgct gcccgaaatt                                    8310
```

<210> SEQ ID NO 5
<211> LENGTH: 560
<212> TYPE: PRT
<213> ORGANISM: Populus tremuloides

<400> SEQUENCE: 5

```
Met Arg Cys Ser Val Ser Thr Glu Asn Val Ser Phe Ser Glu Thr Glu
 1               5                  10                  15

Thr Glu Thr Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val His Lys
        35                  40                  45

Asp Lys Ala Lys Lys Leu Glu Ala Glu Val Arg Arg Glu Ile Asn Asn
    50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Arg Ala Leu
                85                  90                  95

Asp Arg Phe Val Ser Ser Gly Gly Phe Asp Gly Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140
```

-continued

```
Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Ser His Ala Leu Glu Leu Pro Leu
        195                 200                 205

His Arg Arg Thr Gln Arg Leu Glu Ala Val Trp Ser Ile Glu Ala Tyr
    210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
    290                 295                 300

Phe Val Thr Ile Ile Asp Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                325                 330                 335

Ile Asn Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Asp Lys Gly Glu
        355                 360                 365

Asn Ile Leu Pro Tyr Leu Thr Lys Ala Trp Ala Asp Leu Cys Asn Ala
    370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Ser Gly Pro Leu Gln
                405                 410                 415

Leu Ile Phe Ala Tyr Phe Ala Val Val Gln Asn Ile Lys Lys Glu Glu
            420                 425                 430

Ile Glu Asn Leu Gln Lys Tyr His Asp Ile Ile Ser Arg Pro Ser His
        435                 440                 445

Ile Phe Arg Leu Cys Asn Asp Leu Ala Ser Ala Ser Ala Glu Ile Ala
    450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
            500                 505                 510

Lys Pro Phe Val Glu Thr Ala Ile Asn Leu Ala Arg Gln Ser His Cys
        515                 520                 525

Thr Tyr His Asn Gly Asp Ala His Thr Ser Pro Asp Glu Leu Thr Arg
    530                 535                 540

Lys Arg Val Leu Ser Val Ile Thr Glu Pro Ile Leu Pro Phe Glu Arg
545                 550                 555                 560
```

<210> SEQ ID NO 6

<211> LENGTH: 6957
<212> TYPE: DNA
<213> ORGANISM: Artificial Sequence
<220> FEATURE:
<223> OTHER INFORMATION: Synthetic Construct

<400> SEQUENCE: 6
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560
gtggtttgtt tgccggatca agagctacca actctttttc cgaaggtaac tggcttcagc 1620
agagcgcaga taccaaatac tgtccttcta gtgtagccgt agttaggcca ccacttcaag 1680
aactctgtag caccgcctac atacctcgct ctgctaatcc tgttaccagt ggctgctgcc 1740
agtggcgata agtcgtgtct taccgggttg gactcaagac gatagttacc ggataaggcg 1800
cagcggtcgg gctgaacggg gggttcgtgc acacagccca gcttggagcg aacgacctac 1860
accgaactga gatacctaca gcgtgagcta tgagaaagcg ccacgcttcc cgaagggaga 1920
aaggcggaca ggtatccggt aagcggcagg gtcggaacag gagagcgcac gagggagctt 1980
ccagggggaa acgcctggta tctttatagt cctgtcgggt ttcgccacct ctgacttgag 2040
cgtcgatttt tgtgatgctc gtcagggggg cggagcctat ggaaaaacgc cagcaacgcg 2100
gcctttttac ggttcctggc cttttgctgg ccttttgctc acatgttctt tcctgcgtta 2160

```
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
```

-continued

```
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcgttgt agcgtgtcca ccgaaaatgt   5100
gtctttctct gaaactgaaa ccgaaacgcg tcgttctgcg aactacgaac ctaacagctg   5160
ggactatgat tacctgctgt cctccgacac ggacgagtcc atcgaagtac acaaagacaa   5220
agcgaaaaag ctggaagccg aagttcgtcg cgagattaat aacgaaaaag cagaatttct   5280
gaccctgctg gaactgattg acaacgtcca gcgcctgggc ctgggttacc gtttcgagtc   5340
tgatatccgt cgtgcgctgg atcgcttcgt ttcctccggc ggcttcgatg gcgtaaccaa   5400
gacttccctg cacggtacgg cactgtcttt ccgtctgctg cgtcaacacg gttttgaggt   5460
ttctcaggaa gcgttcagcg gcttcaaaga ccaaaacggc aacttcctgg agaacctgaa   5520
ggaagatatc aaagctatcc tgagcctgta cgaggccagc ttcctggctc tggaaggcga   5580
aaacatcctg gacgaggcga aggttttcgc aatctctcat ctgaaagaac tgtctgaaga   5640
aaagatcggt aaagagctgg cagaacaggt gtcccatgca ctggaactgc cactgcatcg   5700
ccgtactcag cgtctggaag cagtatggtc tatcgaggcc taccgtaaaa aggaggacgc   5760
gaaccaggtt ctgctggagc tggcaattct ggattacaac atgatccagt ctgtatacca   5820
gcgtgatctg cgtgaaacgt cccgttggtg gcgtcgtgtg ggtctggcga ccaaactgca   5880
ctttgctcgt gaccgcctga ttgagagctt ctactgggcc gtgggtgtag cattcgaacc   5940
gcaatactcc gactgccgta actccgtcgc aaaaatgttt tctttcgtaa ccattatcga   6000
cgatatctac gatgtatacg gcaccctgga cgaactggag ctgtttactg atgcagttga   6060
gcgttgggac gtaaacgcca tcaacgacct gccggattac atgaaactgt gctttctggc   6120
tctgtataac actattaacg aaatcgccta cgacaacctg aaagataaag gtgagaacat   6180
cctgccgtat ctgaccaaag cctgggctga cctgtgcaac gctttcctgc aagaagccaa   6240
gtggctgtac aacaaatcta ctccgacctt tgacgactac ttcggcaacg catggaaatc   6300
ctcttctggc ccgctgcaac tgatcttcgc ttacttcgct gtcgtgcaga acattaaaaa   6360
ggaagagatc gaaaacctgc aaaaatacca tgacatcatc tctcgtcctt cccatatctt   6420
ccgtctgtgc aatgacctgg ctagcgcgtc tgcggaaatt gcgcgtggtg aaaccgcaaa   6480
tagcgtttct tgttacatgc gcactaaagg tatctccgaa gaactggcta ccgaaagcgt   6540
gatgaatctg atcgatgaaa cctggaaaaa gatgaacaag gaaaaactgg gtggtagcct   6600
gttcgcgaaa ccgttcgtgg aaaccgcgat caacctggca cgtcaatctc actgcactta   6660
tcataacggc gacgcgcata cctctccgga tgagctgacc cgcaaacgcg ttctgtctgt   6720
aatcactgaa ccgattctgc cgtttgaacg ctaaggatcc gaattcgagc tccgtcgaca   6780
agcttgcggc cgcactcgag caccaccacc accaccactg agatccggct gctaacaaag   6840
cccgaaagga agctgagttg gctgctgcca ccgctgagca ataactagca taacccettg   6900
gggcctctaa acgggtcttg aggggttttt tgctgaaagg aggaactata tccggat      6957
```

<210> SEQ ID NO 7
<211> LENGTH: 560
<212> TYPE: PRT
<213> ORGANISM: Populus trichocarpa

<400> SEQUENCE: 7

```
Met Arg Cys Ser Val Ser Thr Glu Asn Val Ser Phe Thr Glu Thr Glu
 1               5                  10                  15

Thr Glu Thr Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val Tyr Lys
        35                  40                  45

Asp Lys Ala Lys Lys Leu Glu Ala Glu Val Arg Arg Glu Ile Asn Asn
    50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Arg Ala Leu
                85                  90                  95

Asp Arg Phe Val Ser Ser Gly Gly Phe Asp Ala Val Thr Lys Thr Ser
            100                 105                 110

Leu His Ala Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Asp Leu Ala Glu Gln Val Asn His Ala Leu Glu Leu Pro Leu
        195                 200                 205

His Arg Arg Thr Gln Arg Leu Glu Ala Val Leu Ser Ile Glu Ala Tyr
    210                 215                 220

Arg Lys Lys Glu Asp Ala Asp Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
    290                 295                 300

Phe Val Thr Ile Ile Asp Asp Ile Tyr Asp Val Tyr Gly Thr Leu Asp
305                 310                 315                 320

Glu Leu Glu Leu Phe Thr Asn Ala Val Glu Arg Trp Asp Val Asn Ala
                325                 330                 335

Ile Asp Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Glu Lys Gly Glu
        355                 360                 365

Asn Ile Leu Pro Tyr Leu Thr Lys Ala Trp Ala Asp Leu Cys Asn Ala
    370                 375                 380
```

-continued

```
Phe Leu Gln Glu Ala Lys Trp Leu Tyr Asn Lys Ser Thr Pro Thr Phe
385                 390                 395                 400

Asp Glu Tyr Phe Gly Asn Ala Trp Lys Ser Ser Ser Gly Pro Leu Gln
                405                 410                 415

Leu Val Phe Ala Tyr Phe Ala Val Val Gln Asn Ile Lys Lys Glu Glu
            420                 425                 430

Ile Glu Asn Leu Gln Lys Tyr His Asp Ile Ile Ser Arg Pro Ser His
        435                 440                 445

Ile Phe Arg Leu Cys Asn Asp Leu Ala Ser Ala Ser Ala Glu Ile Ala
    450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
            500                 505                 510

Lys Pro Phe Val Glu Thr Ala Ile Asn Leu Ala Arg Gln Ser His Cys
        515                 520                 525

Thr Tyr His Asn Gly Asp Ala His Thr Ser Pro Asp Glu Leu Thr Arg
    530                 535                 540

Lys Arg Val Leu Ser Val Ile Thr Glu Pro Ile Leu Pro Phe Glu Arg
545                 550                 555                 560
```

<210> SEQ ID NO 8
<211> LENGTH: 6963
<212> TYPE: DNA
<213> ORGANISM: Artificial Sequence
<220> FEATURE:
<223> OTHER INFORMATION: Synthetic Construct

<400> SEQUENCE: 8

```
tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420

acaaaaattt aacgcgaatt ttaacaaaat attaacgttt acaatttcag gtggcacttt    480

tcggggaaat gtgcgcggaa cccctatttg tttatttttc taaatacatt caaatatgta    540

tccgctcatg aattaattct tagaaaaact catcgagcat caaatgaaac tgcaatttat    600

tcatatcagg attatcaata ccatattttt gaaaaagccg tttctgtaat gaaggagaaa    660

actcaccgag gcagttccat aggatggcaa gatcctggta tcggtctgcg attccgactc    720

gtccaacatc aatacaacct attaatttcc cctcgtcaaa aataaggtta tcaagtgaga    780

aatcaccatg agtgacgact gaatccggtg agaatggcaa aagtttatgc atttctttcc    840

agacttgttc aacaggccag ccattacgct cgtcatcaaa atcactcgca tcaaccaaac    900

cgttattcat tcgtgattgc gcctgagcga gacgaaatac gcgatcgctg ttaaaaggac    960

aattacaaac aggaatcgaa tgcaaccggc gcaggaacac tgccagcgca tcaacaatat   1020

tttcacctga atcaggatat tcttctaata cctggaatgc tgttttcccg gggatcgcag   1080

tggtgagtaa ccatgcatca tcaggagtac ggataaaatg cttgatggtc ggaagaggca   1140
```

-continued

```
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggg taatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
```

-continued

```
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcatatg cgttgtagcg tgtccaccga   5100
aaatgtgtct ttcaccgaaa ctgaaaccga aacgcgtcgt tctgcgaact acgaacctaa   5160
cagctgggac tatgattacc tgctgtcctc cgacacggac gagtccatcg aagtatacaa   5220
agacaaagcg aaaaagctgg aagccgaagt tcgtcgcgag attaataacg aaaaagcaga   5280
atttctgacc ctgctggaac tgattgacaa cgtccagcgc ctgggcctgg gttaccgttt   5340
cgagtctgat atccgtcgtg cgctggatcg cttcgtttcc tccggcggct tcgatgcggt   5400
aaccaagact tccctgcacg cgacggcact gtctttccgt ctgctgcgtc aacacggttt   5460
tgaggtttct caggaagcgt tcagcggctt caaagaccaa aacggcaact tcctggagaa   5520
cctgaaggaa gatatcaaag ctatcctgag cctgtacgag gccagcttcc tggctctgga   5580
aggcgaaaac atcctggacg aggcgaaggt tttcgcaatc tctcatctga aagaactgtc   5640
tgaagaaaag atcggtaaag atctggcaga acaggtgaac catgcactgg aactgccact   5700
gcatcgccgt actcagcgtc tggaagcagt actgtctatc gaggcctacc gtaaaaagga   5760
ggacgcggat caggttctgc tggagctggc aattctggat tacaacatga tccagtctgt   5820
ataccagcgt gatctgcgtg aaacgtcccg ttggtggcgt cgtgtgggtc tggcgaccaa   5880
actgcacttt gctcgtgacc gcctgattga gagcttctac tgggccgtgg gtgtagcatt   5940
```

```
cgaaccgcaa tactccgact gccgtaactc cgtcgcaaaa atgttttctt tcgtaaccat   6000

tatcgacgat atctacgatg tatacggcac cctggacgaa ctggagctgt ttactaacgc   6060

agttgagcgt tgggacgtaa acgccatcga cgatctgccg gattacatga aactgtgctt   6120

tctggctctg tataacacta ttaacgaaat cgcctacgac aacctgaaag aaaaaggtga   6180

gaacatcctg ccgtatctga ccaaagcctg ggctgacctg tgcaacgctt tcctgcaaga   6240

agccaagtgg ctgtacaaca aatctactcc gacctttgac gaatacttcg gcaacgcatg   6300

gaaatcctct tctggcccgc tgcaactggt gttcgcttac ttcgctgtcg tgcagaacat   6360

taaaaaggaa gagatcgaaa acctgcaaaa ataccatgac atcatctctc gtccttccca   6420

tatcttccgt ctgtgcaatg acctggctag cgcgtctgcg gaaattgcgc gtggtgaaac   6480

cgcaaatagc gtttcttgtt acatgcgcac taaaggtatc tccgaagaac tggctaccga   6540

aagcgtgatg aatctgatcg atgaaacctg gaaaaagatg aacaaggaaa aactgggtgg   6600

tagcctgttc gcgaaaccgt tcgtggaaac cgcgatcaac ctggcacgtc aatctcactg   6660

cacttatcat aacggcgacg cgcatacctc tccggatgag ctgacccgca aacgcgttct   6720

gtctgtaatc actgaaccga ttctgccgtt tgaacgctaa ggatccgaat tcgagctccg   6780

tcgacaagct tgcggccgca ctcgagcacc accaccacca ccactgagat ccggctgcta   6840

acaaagcccg aaaggaagct gagttggctg ctgccaccgc tgagcaataa ctagcataac   6900

cccttggggc ctctaaacgg gtcttgaggg gttttttgct gaaaggagga actatatccg   6960

gat                                                                 6963
```

```
<210> SEQ ID NO 9
<211> LENGTH: 578
<212> TYPE: PRT
<213> ORGANISM: Artificial Sequence
<220> FEATURE:
<223> OTHER INFORMATION: Synthetic Construct

<400> SEQUENCE: 9

Met Arg Gly Ser His His His His His His Gly Met Ala Ser Met Thr
 1               5                  10                  15

Gly Gly Gln Gln Met Gly Arg Asp Leu Tyr Asp Asp Asp Asp Lys Asp
            20                  25                  30

His Pro Phe Thr Met Arg Arg Ser Ala Asn Tyr Glu Pro Asn Ser Trp
        35                  40                  45

Asp Tyr Asp Tyr Leu Leu Ser Ser Asp Thr Asp Glu Ser Ile Glu Val
    50                  55                  60

Tyr Lys Asp Lys Ala Lys Lys Leu Glu Ala Glu Val Arg Arg Glu Ile
65                  70                  75                  80

Asn Asn Glu Lys Ala Glu Phe Leu Thr Leu Leu Glu Leu Ile Asp Asn
                85                  90                  95

Val Gln Arg Leu Gly Leu Gly Tyr Arg Phe Glu Ser Asp Ile Arg Gly
            100                 105                 110

Ala Leu Asp Arg Phe Val Ser Ser Gly Gly Phe Asp Ala Val Thr Lys
        115                 120                 125

Thr Ser Leu His Gly Thr Ala Leu Ser Phe Arg Leu Leu Arg Gln His
    130                 135                 140

Gly Phe Glu Val Ser Gln Glu Ala Phe Ser Gly Phe Lys Asp Gln Asn
145                 150                 155                 160

Gly Asn Phe Leu Glu Asn Leu Lys Glu Asp Ile Lys Ala Ile Leu Ser
                165                 170                 175
```

```
Leu Tyr Glu Ala Ser Phe Leu Ala Leu Glu Gly Glu Asn Ile Leu Asp
            180                 185                 190

Glu Ala Lys Val Phe Ala Ile Ser His Leu Lys Glu Leu Ser Glu Glu
        195                 200                 205

Lys Ile Gly Lys Glu Leu Ala Glu Gln Val Asn His Ala Leu Glu Leu
    210                 215                 220

Pro Leu His Arg Arg Thr Gln Arg Leu Glu Ala Val Trp Ser Ile Glu
225                 230                 235                 240

Ala Tyr Arg Lys Lys Glu Asp Ala Asn Gln Val Leu Leu Glu Leu Ala
                245                 250                 255

Ile Leu Asp Tyr Asn Met Ile Gln Ser Val Tyr Gln Arg Asp Leu Arg
            260                 265                 270

Glu Thr Ser Arg Trp Trp Arg Arg Val Gly Leu Ala Thr Lys Leu His
        275                 280                 285

Phe Ala Arg Asp Arg Leu Ile Glu Ser Phe Tyr Trp Ala Val Gly Val
    290                 295                 300

Ala Phe Glu Pro Gln Tyr Ser Asp Cys Arg Asn Ser Val Ala Lys Met
305                 310                 315                 320

Phe Ser Phe Val Thr Ile Ile Asp Asp Ile Tyr Asp Val Tyr Gly Thr
                325                 330                 335

Leu Asp Glu Leu Glu Leu Phe Thr Asp Ala Val Glu Arg Trp Asp Val
            340                 345                 350

Asn Ala Ile Asn Asp Leu Pro Asp Tyr Met Lys Leu Cys Phe Leu Ala
        355                 360                 365

Leu Tyr Asn Thr Ile Asn Glu Ile Ala Tyr Asp Asn Leu Lys Asp Lys
    370                 375                 380

Gly Glu Asn Ile Leu Pro Tyr Leu Thr Lys Ala Trp Ala Asp Leu Cys
385                 390                 395                 400

Asn Ala Phe Leu Gln Glu Ala Lys Trp Leu Tyr Asn Lys Ser Thr Pro
                405                 410                 415

Thr Phe Asp Asp Tyr Phe Gly Asn Ala Trp Lys Ser Ser Ser Gly Pro
            420                 425                 430

Leu Gln Leu Val Phe Ala Tyr Phe Ala Val Val Gln Asn Ile Lys Lys
        435                 440                 445

Glu Glu Ile Glu Asn Leu Gln Lys Tyr His Asp Thr Ile Ser Arg Pro
    450                 455                 460

Ser His Ile Phe Arg Leu Cys Asn Asp Leu Ala Ser Ala Ser Ala Glu
465                 470                 475                 480

Ile Ala Arg Gly Glu Thr Ala Asn Ser Val Ser Cys Tyr Met Arg Thr
                485                 490                 495

Lys Gly Ile Ser Glu Glu Leu Ala Thr Glu Ser Val Met Asn Leu Ile
            500                 505                 510

Asp Glu Thr Trp Lys Lys Met Asn Lys Glu Lys Leu Gly Gly Ser Leu
        515                 520                 525

Phe Ala Lys Pro Phe Val Glu Thr Ala Ile Asn Leu Ala Arg Gln Ser
    530                 535                 540

His Cys Thr Tyr His Asn Gly Asp Ala His Thr Ser Pro Asp Glu Leu
545                 550                 555                 560

Thr Arg Lys Arg Val Leu Ser Val Ile Thr Glu Pro Ile Leu Pro Phe
                565                 570                 575

Glu Arg
```

<210> SEQ ID NO 10
<211> LENGTH: 7370

<212> TYPE: DNA
<213> ORGANISM: Artificial Sequence
<220> FEATURE:
<223> OTHER INFORMATION: Synthetic Construct

<400> SEQUENCE: 10

```
aagggcgagc tcaacgatcc ggctgctaac aaagcccgaa aggaagctga gttggctgct     60
gccaccgctg agcaataact agcataaccc cttggggcct ctaaacgggt cttgaggagt    120
tttttgctga aaggaggaac tatatccgga tatcccgcaa gaggcccggc agtaccggca    180
taaccaagcc tatgcctaca gcatccaggg tgacggtgcc gaggatgacg atgagcgcat    240
tgttagattt catacacggt gcctgactgc gttagcaatt taactgtgat aaactaccgc    300
attaaagctt atcgatgata agctgtcaaa catgagaatt aattcttgaa gacgaaaggg    360
cctcgtgata cgcctatttt tataggttaa tgtcatgata ataatggttt cttagacgtc    420
aggtggcact tttcggggaa atgtgcgcgg aacccctatt tgtttatttt tctaaataca    480
ttcaaatatg tatccgctca tgagacaata accctgataa atgcttcaat aatattgaaa    540
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcaggggc gcccggttct ttttgtcaag accgacctgt ccggtgccct    720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc tttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
```

-continued

```
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact tccgcgtttc cagactttac   3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg gcgcctacaa   3480
tccatgccaa cccgttccat gtgctcgccg aggcggcata aatcgccgtg acgatcagcg   3540
gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
gcgctgccgg cacctgtcct acgagttgca tgataaagaa gacagtcata agtgcggcga   3960
cgatagtcat gccccgcgcc caccggaagg agctgactgg gttgaaggct ctcaagggca   4020
tcggtcgaga tcccggtgcc taatgagtga gctaacttac attaattgcg ttgcgctcac   4080
tgcccgcttt ccagtcggga aacctgtcgt gccagctgca ttaatgaatc ggccaacgcg   4140
cggggagagg cggtttgcgt attgggcgcc agggtggttt ttcttttcac cagtgagacg   4200
ggcaacagct gattgccctt caccgcctgg ccctgagaga gttgcagcaa gcggtccacg   4260
ctggtttgcc ccagcaggcg aaaatcctgt ttgatggtgg ttaacggcgg gatataacat   4320
gagctgtctt cggtatcgtc gtatcccact accgagatat ccgcaccaac gcgcagcccg   4380
gactcggtaa tggcgcgcat tgcgcccagc gccatctgat cgttggcaac cagcatcgca   4440
gtgggaacga tgccctcatt cagcatttgc atggtttgtt gaaaaccgga catggcactc   4500
cagtcgcctt cccgttccgc tatcggctga atttgattgc gagtgagata tttatgccag   4560
ccagccagac gcagacgcgc cgagacagaa cttaatgggc ccgctaacag cgcgatttgc   4620
```

```
tggtgaccca atgcgaccag atgctccacg cccagtcgcg taccgtcttc atgggagaaa   4680
ataatactgt tgatgggtgt ctggtcagag acatcaagaa ataacgccgg aacattagtg   4740
caggcagctt ccacagcaat ggcatcctgg tcatccagcg gatagttaat gatcagccca   4800
ctgacgcgtt gcgcgagaag attgtgcacc gccgctttac aggcttcgac gccgcttcgt   4860
tctaccatcg acaccaccac gctggcaccc agttgatcgg cgcgagattt aatcgccgcg   4920
acaatttgcg acggcgcgtg cagggccaga ctggaggtgg caacgccaat cagcaacgac   4980
tgtttgcccg ccagttgttg tgccacgcgg ttgggaatgt aattcagctc cgccatcgcc   5040
gcttccactt tttcccgcgt tttcgcagaa acgtggctgg cctggttcac cacgcgggaa   5100
acggtctgat aagagacacc ggcatactct gcgacatcgt ataacgttac tggtttcaca   5160
ttcaccaccc tgaattgact ctcttccggg cgctatcatg ccataccgcg aaaggttttg   5220
cgccattcga tggtgtccgg gatctcgacg ctctccctta tgcgactcct gcattaggaa   5280
gcagcccagt agtaggttga ggccgttgag caccgccgcc gcaaggaatg gtgcatgcaa   5340
ggagatggcg cccaacagtc ccccggccac ggggcctgcc accataccca cgccgaaaca   5400
agcgctcatg agcccgaagt ggcgagcccg atcttcccca tcggtgatgt cggcgatata   5460
ggcgccagca accgcacctg tggcgccggt gatgccggcc acgatgcgtc cggcgtagag   5520
gatcgagatc tcgatcccgc gaaattaata cgactcacta taggggaatt gtgagcggat   5580
aacaattccc ctctagaaat aattttgttt aactttaaga aggagatata catatgcggg   5640
gttctcatca tcatcatcat catggtatgg ctagcatgac tggtggacag caaatgggtc   5700
gggatctgta cgacgatgac gataaggatc atcccttcac catgcgtcgt tctgcgaact   5760
acgaacctaa cagctgggac tatgattacc tgctgtcctc cgacacggac gagtccatcg   5820
aagtatacaa agacaaagcg aaaaagctgg aagccgaagt tcgtcgcgag attaataacg   5880
aaaaagcaga atttctgacc ctgctggaac tgattgacaa cgtccagcgc ctgggcctgg   5940
gttaccgttt cgagtctgat atccgtggtg cgctggatcg cttcgtttcc tccggcggct   6000
tcgatgcggt aaccaagact tccctgcacg gtacggcact gtctttccgt ctgctgcgtc   6060
aacacggttt tgaggtttct caggaagcgt tcagcggctt caaagaccaa aacggcaact   6120
tcctggagaa cctgaaggaa gatatcaaag ctatcctgag cctgtacgag gccagcttcc   6180
tggctctgga aggcgaaaac atcctggacg aggcgaaggt tttcgcaatc tctcatctga   6240
aagaactgtc tgaagaaaag atcggtaaag agctggcaga acaggtgaac catgcactgg   6300
aactgccact gcatcgccgt actcagcgtc tggaagcagt atggtctatc gaggcctacc   6360
gtaaaaagga ggacgcgaat caggttctgc tggagctggc aattctggat tacaacatga   6420
tccagtctgt ataccagcgt gatctgcgtg aaacgtcccg ttggtggcgt cgtgtgggtc   6480
tggcgaccaa actgcacttt gctcgtgacc gcctgattga gagcttctac tgggccgtgg   6540
gtgtagcatt cgaaccgcaa tactccgact gccgtaactc cgtcgcaaaa atgttttctt   6600
tcgtaaccat tatcgacgat atctacgatg tatacggcac cctggacgaa ctggagctgt   6660
ttactgatgc agttgagcgt tgggacgtaa acgccatcaa cgacctgccg gattacatga   6720
aactgtgctt tctggctctg tataacacta ttaacgaaat cgcctacgac aacctgaaag   6780
ataaaggtga gaacatcctg ccgtatctga ccaaagcctg ggctgacctg tgcaacgctt   6840
tcctgcaaga agccaagtgg ctgtacaaca aatctactcc gacctttgac gactacttcg   6900
gcaacgcatg gaaatcctct tctggcccgc tgcaactggt gttcgcttac ttcgctgtcg   6960
tgcagaacat taaaaaggaa gagatcgaaa acctgcaaaa ataccatgac accatctctc   7020
```

-continued

```
gtccttccca tatcttccgt ctgtgcaatg acctggctag cgcgtctgcg gaaattgcgc   7080

gtggtgaaac cgcaaatagc gtttcttgtt acatgcgcac taaaggtatc tccgaagaac   7140

tggctaccga aagcgtgatg aatctgatcg atgaaacctg gaaaaagatg aacaaggaaa   7200

aactgggtgg tagcctgttc gcgaaaccgt tcgtggaaac cgcgatcaac ctggcacgtc   7260

aatctcactg cacttatcat aacggcgacg cgcatacctc tccggatgag ctgacccgca   7320

aacgcgttct gtctgtaatc actgaaccga ttctgccgtt tgaacgctaa               7370


<210> SEQ ID NO 11
<211> LENGTH: 578
<212> TYPE: PRT
<213> ORGANISM: Populus tremuloides

<400> SEQUENCE: 11

Met Arg Gly Ser His His His His His His Gly Met Ala Ser Met Thr
 1               5                  10                  15

Gly Gly Gln Gln Met Gly Arg Asp Leu Tyr Asp Asp Asp Asp Lys Asp
            20                  25                  30

His Pro Phe Thr Met Arg Arg Ser Ala Asn Tyr Glu Pro Asn Ser Trp
        35                  40                  45

Asp Tyr Asp Tyr Leu Leu Ser Ser Asp Thr Asp Glu Ser Ile Glu Val
    50                  55                  60

His Lys Asp Lys Ala Lys Lys Leu Glu Ala Glu Val Arg Arg Glu Ile
65                  70                  75                  80

Asn Asn Glu Lys Ala Glu Phe Leu Thr Leu Leu Glu Leu Ile Asp Asn
                85                  90                  95

Val Gln Arg Leu Gly Leu Gly Tyr Arg Phe Glu Ser Asp Ile Arg Arg
            100                 105                 110

Ala Leu Asp Arg Phe Val Ser Ser Gly Gly Phe Asp Gly Val Thr Lys
        115                 120                 125

Thr Ser Leu His Gly Thr Ala Leu Ser Phe Arg Leu Leu Arg Gln His
    130                 135                 140

Gly Phe Glu Val Ser Gln Glu Ala Phe Ser Gly Phe Lys Asp Gln Asn
145                 150                 155                 160

Gly Asn Phe Leu Glu Asn Leu Lys Glu Asp Ile Lys Ala Ile Leu Ser
                165                 170                 175

Leu Tyr Glu Ala Ser Phe Leu Ala Leu Glu Gly Glu Asn Ile Leu Asp
            180                 185                 190

Glu Ala Lys Val Phe Ala Ile Ser His Leu Lys Glu Leu Ser Glu Glu
        195                 200                 205

Lys Ile Gly Lys Glu Leu Ala Glu Gln Val Ser His Ala Leu Glu Leu
    210                 215                 220

Pro Leu His Arg Arg Thr Gln Arg Leu Glu Ala Val Trp Ser Ile Glu
225                 230                 235                 240

Ala Tyr Arg Lys Lys Glu Asp Ala Asn Gln Val Leu Leu Glu Leu Ala
                245                 250                 255

Ile Leu Asp Tyr Asn Met Ile Gln Ser Val Tyr Gln Arg Asp Leu Arg
            260                 265                 270

Glu Thr Ser Arg Trp Trp Arg Arg Val Gly Leu Ala Thr Lys Leu His
        275                 280                 285

Phe Ala Arg Asp Arg Leu Ile Glu Ser Phe Tyr Trp Ala Val Gly Val
    290                 295                 300

Ala Phe Glu Pro Gln Tyr Ser Asp Cys Arg Asn Ser Val Ala Lys Met
305                 310                 315                 320
```

```
Phe Ser Phe Val Thr Ile Ile Asp Asp Ile Tyr Asp Val Tyr Gly Thr
                325                 330                 335

Leu Asp Glu Leu Glu Leu Phe Thr Asp Ala Val Glu Arg Trp Asp Val
            340                 345                 350

Asn Ala Ile Asn Asp Leu Pro Asp Tyr Met Lys Leu Cys Phe Leu Ala
        355                 360                 365

Leu Tyr Asn Thr Ile Asn Glu Ile Ala Tyr Asp Asn Leu Lys Asp Lys
    370                 375                 380

Gly Glu Asn Ile Leu Pro Tyr Leu Thr Lys Ala Trp Ala Asp Leu Cys
385                 390                 395                 400

Asn Ala Phe Leu Gln Glu Ala Lys Trp Leu Tyr Asn Lys Ser Thr Pro
                405                 410                 415

Thr Phe Asp Asp Tyr Phe Gly Asn Ala Trp Lys Ser Ser Ser Gly Pro
            420                 425                 430

Leu Gln Leu Ile Phe Ala Tyr Phe Ala Val Val Gln Asn Ile Lys Lys
        435                 440                 445

Glu Glu Ile Glu Asn Leu Gln Lys Tyr His Asp Ile Ile Ser Arg Pro
    450                 455                 460

Ser His Ile Phe Arg Leu Cys Asn Asp Leu Ala Ser Ala Ser Ala Glu
465                 470                 475                 480

Ile Ala Arg Gly Glu Thr Ala Asn Ser Val Ser Cys Tyr Met Arg Thr
                485                 490                 495

Lys Gly Ile Ser Glu Glu Leu Ala Thr Glu Ser Val Met Asn Leu Ile
            500                 505                 510

Asp Glu Thr Trp Lys Lys Met Asn Lys Glu Lys Leu Gly Gly Ser Leu
        515                 520                 525

Phe Ala Lys Pro Phe Val Glu Thr Ala Ile Asn Leu Ala Arg Gln Ser
    530                 535                 540

His Cys Thr Tyr His Asn Gly Asp Ala His Thr Ser Pro Asp Glu Leu
545                 550                 555                 560

Thr Arg Lys Arg Val Leu Ser Val Ile Thr Glu Pro Ile Leu Pro Phe
                565                 570                 575

Glu Arg
```

<210> SEQ ID NO 12
<211> LENGTH: 7370
<212> TYPE: DNA
<213> ORGANISM: Artificial Sequence
<220> FEATURE:
<223> OTHER INFORMATION: Synthetic Construct

<400> SEQUENCE: 12

```
cgtcgttctg cgaactacga acctaacagc tgggactatg attacctgct gtcctccgac      60

acggacgagt ccatcgaagt acacaaagac aaagcgaaaa agctggaagc cgaagttcgt     120

cgcgagatta ataacgaaaa agcagaattt ctgaccctgc tggaactgat tgacaacgtc     180

cagcgcctgg gcctgggtta ccgtttcgag tctgatatcc gtcgtgcgct ggatcgcttc     240

gtttcctccg gcggcttcga tggcgtaacc aagacttccc tgcacggtac ggcactgtct     300

ttccgtctgc tgcgtcaaca cggttttgag gtttctcagg aagcgttcag cggcttcaaa     360

gaccaaaacg gcaacttcct ggagaacctg aaggaagata tcaaagctat cctgagcctg     420

tacgaggcca gcttcctggc tctggaaggc gaaaacatcc tggacgaggc gaaggttttc     480

gcaatctctc atctgaaaga actgtctgaa gaaaagatcg gtaaagagct ggcagaacag     540

gtgtcccatg cactggaact gccactgcat cgccgtactc agcgtctgga agcagtatgg     600
```

-continued

```
tctatcgagg cctaccgtaa aaaggaggac gcgaaccagg ttctgctgga gctggcaatt    660
ctggattaca acatgatcca gtctgtatac cagcgtgatc tgcgtgaaac gtcccgttgg    720
tggcgtcgtg tgggtctggc gaccaaactg cactttgctc gtgaccgcct gattgagagc    780
ttctactggg ccgtgggtgt agcattcgaa ccgcaatact ccgactgccg taactccgtc    840
gcaaaaatgt tttctttcgt aaccattatc gacgatatct acgatgtata cggcaccctg    900
gacgaactgg agctgtttac tgatgcagtt gagcgttggg acgtaaacgc catcaacgac    960
ctgccggatt acatgaaact gtgctttctg gctctgtata acactattaa cgaaatcgcc   1020
tacgacaacc tgaaagataa aggtgagaac atcctgccgt atctgaccaa agcctgggct   1080
gacctgtgca acgctttcct gcaagaagcc aagtggctgt acaacaaatc tactccgacc   1140
tttgacgact acttcggcaa cgcatggaaa tcctcttctg gcccgctgca actgatcttc   1200
gcttacttcg ctgtcgtgca gaacattaaa aaggaagaga tcgaaaacct gcaaaaatac   1260
catgacatca tctctcgtcc ttcccatatc ttccgtctgt gcaatgacct ggctagcgcg   1320
tctgcggaaa ttgcgcgtgg tgaaaccgca aatagcgttt cttgttacat gcgcactaaa   1380
ggtatctccg aagaactggc taccgaaagc gtgatgaatc tgatcgatga aacctggaaa   1440
aagatgaaca aggaaaaact gggtggtagc ctgttcgcga aaccgttcgt ggaaaccgcg   1500
atcaacctgg cacgtcaatc tcactgcact tatcataacg gcgacgcgca tacctctccg   1560
gatgagctga cccgcaaacg cgttctgtct gtaatcactg aaccgattct gccgtttgaa   1620
cgctaaaagg gcgagctcaa cgatccggct gctaacaaag cccgaaagga agctgagttg   1680
gctgctgcca ccgctgagca ataactagca taaccccttg gggcctctaa acgggtcttg   1740
aggagttttt tgctgaaagg aggaactata tccggatatc ccgcaagagg cccggcagta   1800
ccggcataac caagcctatg cctacagcat ccagggtgac ggtgccgagg atgacgatga   1860
gcgcattgtt agatttcata cacggtgcct gactgcgtta gcaatttaac tgtgataaac   1920
taccgcatta aagcttatcg atgataagct gtcaaacatg agaattaatt cttgaagacg   1980
aaagggcctc gtgatacgcc tatttttata ggttaatgtc atgataataa tggtttctta   2040
gacgtcaggt ggcacttttc ggggaaatgt gcgcggaacc cctatttgtt tatttttcta   2100
aatacattca aatatgtatc cgctcatgag acaataaccc tgataaatgc ttcaataata   2160
ttgaaaaagg aagagtatga ttgaacaaga tggattgcac gcaggttctc cggccgcttg   2220
ggtggagagg ctattcggct atgactgggc acaactgaca atcggctgct ctgatgccgc   2280
cgtgttccgg ctgtcagcgc aggggcgccc ggttcttttt gtcaagaccg acctgtccgg   2340
tgccctgaat gaactgcagg acgaggcagc gcggctatcg tggctggcca cgacgggcgt   2400
tccttgcgca gctgtgctcg acgttgtcac tgaagcggga agggactggc tgctattggg   2460
cgaagtgccg gggcaggatc tcctgtcatc tcaccttgct cctgccgaga aagtatccat   2520
catggctgat gcaatgcggc ggctgcatac gcttgatccg gctacctgcc cattcgacca   2580
ccaagcgaaa catcgcatcg agcgggcacg tactcggatg gaagccggtc ttgtcgatca   2640
ggatgatctg gacgaagagc atcaggggct cgcgccagcc gaactgttcg ccaggctcaa   2700
ggcgcgcatg cccgacggcg aggatctcgt cgtgacacat ggcgatgcct gcttgccgaa   2760
tatcatggtg gaaaatggcc gcttttctgg attcatcgac tgtggccggc tgggtgtggc   2820
ggaccgctat caggacatag cgttggctac ccgtgatatt gctgaagagc ttggcggcga   2880
atgggctgac cgcttcctcg tgctttacgg tatcgccgct cccgattcgc agcgcatcgc   2940
cttctatcgc cttcttgacg agttcttctg agcgggactc tggggttcga aatgaccgac   3000
```

-continued

```
caagcgacgc ctaactgtca gaccaagttt actcatatat actttagatt gatttaaaac   3060
ttcattttta atttaaaagg atctaggtga agatcctttt tgataatctc atgaccaaaa   3120
tcccttaacg tgagttttcg ttccactgag cgtcagaccc cgtagaaaag atcaaaggat   3180
cttcttgaga tccttttttt ctgcgcgtaa tctgctgctt gcaaacaaaa aaaccaccgc   3240
taccagcggt ggtttgtttg ccggatcaag agctaccaac tctttttccg aaggtaactg   3300
gcttcagcag agcgcagata ccaaatactg tccttctagt gtagccgtag ttaggccacc   3360
acttcaagaa ctctgtagca ccgcctacat acctcgctct gctaatcctg ttaccagtgg   3420
ctgctgccag tggcgataag tcgtgtctta ccgggttgga ctcaagacga tagttaccgg   3480
ataaggcgca gcggtcgggc tgaacggggg gttcgtgcac acagcccagc ttggagcgaa   3540
cgacctacac cgaactgaga tacctacagc gtgagctatg agaaagcgcc acgcttcccg   3600
aagggagaaa ggcggacagg tatccggtaa gcggcagggt cggaacagga gagcgcacga   3660
gggagcttcc agggggaaac gcctggtatc tttatagtcc tgtcgggttt cgccacctct   3720
gacttgagcg tcgatttttg tgatgctcgt caggggggcg gagcctatgg aaaaacgcca   3780
gcaacgcggc ctttttacgg ttcctggcct tttgctggcc ttttgctcac atgttctttc   3840
ctgcgttatc ccctgattct gtggataacc gtattaccgc ctttgagtga gctgataccg   3900
ctcgccgcag ccgaacgacc gagcgcagcg agtcagtgag cgaggaagcg gaagagcgcc   3960
tgatgcggta ttttctcctt acgcatctgt gcggtatttc acaccgcaat ggtgcactct   4020
cagtacaatc tgctctgatg ccgcatagtt aagccagtat acactccgct atcgctacgt   4080
gactgggtca tggctgcgcc ccgacacccg ccaacacccg ctgacgcgcc ctgacgggct   4140
tgtctgctcc cggcatccgc ttacagacaa gctgtgaccg tctccgggag ctgcatgtgt   4200
cagaggtttt caccgtcatc accgaaacgc gcgaggcagc tgcggtaaag ctcatcagcg   4260
tggtcgtgaa gcgattcaca gatgtctgcc tgttcatccg cgtccagctc gttgagtttc   4320
tccagaagcg ttaatgtctg gcttctgata aagcgggcca tgttaagggc ggttttttcc   4380
tgtttggtca ctgatgcctc cgtgtaaggg ggatttctgt tcatgggggt aatgataccg   4440
atgaaacgag agaggatgct cacgatacgg gttactgatg atgaacatgc ccggttactg   4500
gaacgttgtg agggtaaaca actggcggta tggatgcggc gggaccagag aaaaatcact   4560
cagggtcaat gccagcgctt cgttaataca gatgtaggtg ttccacaggg tagccagcag   4620
catcctgcga tgcagatccg gaacataatg gtgcagggcg ctgacttccg cgtttccaga   4680
ctttacgaaa cacggaaacc gaagaccatt catgttgttg ctcaggtcgc agacgttttg   4740
cagcagcagt cgcttcacgt tcgctcgcgt atcggtgatt cattctgcta accagtaagg   4800
caaccccgcc agcctagccg ggtcctcaac gacaggagca cgatcatgcg cacccgtggc   4860
caggacccaa cgctgcccga gatgcgccgc gtgcggctgc tggagatggc ggacgcgatg   4920
gatatgttct gccaagggtt ggtttgcgca ttcacagttc tccgcaagaa ttgattggct   4980
ccaattcttg gagtggtgaa tccgttagcg aggtgccgcc ggcttccatt caggtcgagg   5040
tggcccggct ccatgcaccg cgacgcaacg cggggaggca gacaaggtat agggcggcgc   5100
ctacaatcca tgccaacccg ttccatgtgc tcgccgaggc ggcataaatc gccgtgacga   5160
tcagcggtcc aatgatcgaa gttaggctgg taagagccgc gagcgatcct tgaagctgtc   5220
cctgatggtc gtcatctacc tgcctggaca gcatggcctg caacgcgggc atcccgatgc   5280
cgccggaagc gagaagaatc ataatgggga aggccatcca gcctcgcgtc gcgaacgcca   5340
gcaagacgta gcccagcgcg tcggccgcca tgccggcgat aatggcctgc ttctcgccga   5400
```

-continued

```
aacgtttggt ggcgggacca gtgacgaagg cttgagcgag ggcgtgcaag attccgaata   5460
ccgcaagcga caggccgatc atcgtcgcgc tccagcgaaa gcggtcctcg ccgaaaatga   5520
cccagagcgc tgccggcacc tgtcctacga gttgcatgat aaagaagaca gtcataagtg   5580
cggcgacgat agtcatgccc cgcgcccacc ggaaggagct gactgggttg aaggctctca   5640
agggcatcgg tcgagatccc ggtgcctaat gagtgagcta acttacatta attgcgttgc   5700
gctcactgcc cgctttccag tcgggaaacc tgtcgtgcca gctgcattaa tgaatcggcc   5760
aacgcgcggg gagaggcggt ttgcgtattg ggcgccaggg tggtttttct tttcaccagt   5820
gagacgggca acagctgatt gcccttcacc gcctggccct gagagagttg cagcaagcgg   5880
tccacgctgg tttgccccag caggcgaaaa tcctgtttga tggtggttaa cggcgggata   5940
taacatgagc tgtcttcggt atcgtcgtat cccactaccg agatatccgc accaacgcgc   6000
agcccggact cggtaatggc gcgcattgcg cccagcgcca tctgatcgtt ggcaaccagc   6060
atcgcagtgg gaacgatgcc ctcattcagc atttgcatgg tttgttgaaa accggacatg   6120
gcactccagt cgccttcccg ttccgctatc ggctgaattt gattgcgagt gagatattta   6180
tgccagccag ccagacgcag acgcgccgag acagaactta atgggcccgc taacagcgcg   6240
atttgctggt gacccaatgc gaccagatgc tccacgccca gtcgcgtacc gtcttcatgg   6300
gagaaaataa tactgttgat gggtgtctgg tcagagacat caagaaataa cgccggaaca   6360
ttagtgcagg cagcttccac agcaatggca tcctggtcat ccagcggata gttaatgatc   6420
agcccactga cgcgttgcgc gagaagattg tgcaccgccg ctttacaggc ttcgacgccg   6480
cttcgttcta ccatcgacac caccacgctg gcacccagtt gatcggcgcg agatttaatc   6540
gccgcgacaa tttgcgacgg cgcgtgcagg gccagactgg aggtggcaac gccaatcagc   6600
aacgactgtt tgcccgccag ttgttgtgcc acgcggttgg gaatgtaatt cagctccgcc   6660
atcgccgctt ccactttttc ccgcgttttc gcagaaacgt ggctggcctg gttcaccacg   6720
cgggaaacgg tctgataaga gacaccggca tactctgcga catcgtataa cgttactggt   6780
ttcacattca ccaccctgaa ttgactctct tccgggcgct atcatgccat accgcgaaag   6840
gttttgcgcc attcgatggt gtccgggatc tcgacgctct cccttatgcg actcctgcat   6900
taggaagcag cccagtagta ggttgaggcc gttgagcacc gccgccgcaa ggaatggtgc   6960
atgcaaggag atggcgccca acagtccccc ggccacgggg cctgccacca tacccacgcc   7020
gaaacaagcg ctcatgagcc cgaagtggcg agcccgatct tccccatcgg tgatgtcggc   7080
gatataggcg ccagcaaccg cacctgtggc gccggtgatg ccggccacga tgcgtccggc   7140
gtagaggatc gagatctcga tcccgcgaaa ttaatacgac tcactatagg ggaattgtga   7200
gcggataaca attcccctct agaaataatt ttgtttaact ttaagaagga gatatacata   7260
tgcggggttc tcatcatcat catcatcatg gtatggctag catgactggt ggacagcaaa   7320
tgggtcggga tctgtacgac gatgacgata aggatcatcc cttcaccatg              7370
```

<210> SEQ ID NO 13
<211> LENGTH: 578
<212> TYPE: PRT
<213> ORGANISM: Artificial Sequence
<220> FEATURE:
<223> OTHER INFORMATION: Synthetic Construct

<400> SEQUENCE: 13

```
Met Arg Gly Ser His His His His His His Gly Met Ala Ser Met Thr
 1               5                  10                  15
```

```
Gly Gly Gln Gln Met Gly Arg Asp Leu Tyr Asp Asp Asp Asp Lys Asp
            20                  25                  30

His Pro Phe Thr Met Arg Arg Ser Ala Asn Tyr Glu Pro Asn Ser Trp
        35                  40                  45

Asp Tyr Asp Tyr Leu Leu Ser Ser Asp Thr Asp Glu Ser Ile Glu Val
    50                  55                  60

Tyr Lys Asp Lys Ala Lys Lys Leu Glu Ala Glu Val Arg Arg Glu Ile
65                  70                  75                  80

Asn Asn Glu Lys Ala Glu Phe Leu Thr Leu Leu Glu Leu Ile Asp Asn
                85                  90                  95

Val Gln Arg Leu Gly Leu Gly Tyr Arg Phe Glu Ser Asp Ile Arg Arg
            100                 105                 110

Ala Leu Asp Arg Phe Val Ser Ser Gly Gly Phe Asp Ala Val Thr Lys
        115                 120                 125

Thr Ser Leu His Ala Thr Ala Leu Ser Phe Arg Leu Leu Arg Gln His
    130                 135                 140

Gly Phe Glu Val Ser Gln Glu Ala Phe Ser Gly Phe Lys Asp Gln Asn
145                 150                 155                 160

Gly Asn Phe Leu Glu Asn Leu Lys Glu Asp Ile Lys Ala Ile Leu Ser
                165                 170                 175

Leu Tyr Glu Ala Ser Phe Leu Ala Leu Glu Gly Glu Asn Ile Leu Asp
            180                 185                 190

Glu Ala Lys Val Phe Ala Ile Ser His Leu Lys Glu Leu Ser Glu Glu
        195                 200                 205

Lys Ile Gly Lys Asp Leu Ala Glu Gln Val Asn His Ala Leu Glu Leu
    210                 215                 220

Pro Leu His Arg Arg Thr Gln Arg Leu Glu Ala Val Leu Ser Ile Glu
225                 230                 235                 240

Ala Tyr Arg Lys Lys Glu Asp Ala Asp Gln Val Leu Leu Glu Leu Ala
                245                 250                 255

Ile Leu Asp Tyr Asn Met Ile Gln Ser Val Tyr Gln Arg Asp Leu Arg
            260                 265                 270

Glu Thr Ser Arg Trp Trp Arg Arg Val Gly Leu Ala Thr Lys Leu His
        275                 280                 285

Phe Ala Arg Asp Arg Leu Ile Glu Ser Phe Tyr Trp Ala Val Gly Val
    290                 295                 300

Ala Phe Glu Pro Gln Tyr Ser Asp Cys Arg Asn Ser Val Ala Lys Met
305                 310                 315                 320

Phe Ser Phe Val Thr Ile Ile Asp Asp Ile Tyr Asp Val Tyr Gly Thr
                325                 330                 335

Leu Asp Glu Leu Glu Leu Phe Thr Asn Ala Val Glu Arg Trp Asp Val
            340                 345                 350

Asn Ala Ile Asp Asp Leu Pro Asp Tyr Met Lys Leu Cys Phe Leu Ala
        355                 360                 365

Leu Tyr Asn Thr Ile Asn Glu Ile Ala Tyr Asp Asn Leu Lys Glu Lys
    370                 375                 380

Gly Glu Asn Ile Leu Pro Tyr Leu Thr Lys Ala Trp Ala Asp Leu Cys
385                 390                 395                 400

Asn Ala Phe Leu Gln Glu Ala Lys Trp Leu Tyr Asn Lys Ser Thr Pro
                405                 410                 415

Thr Phe Asp Glu Tyr Phe Gly Asn Ala Trp Lys Ser Ser Ser Gly Pro
            420                 425                 430

Leu Gln Leu Val Phe Ala Tyr Phe Ala Val Val Gln Asn Ile Lys Lys
        435                 440                 445
```

```
Glu Glu Ile Glu Asn Leu Gln Lys Tyr His Asp Ile Ile Ser Arg Pro
    450                 455                 460

Ser His Ile Phe Arg Leu Cys Asn Asp Leu Ala Ser Ala Ser Ala Glu
465                 470                 475                 480

Ile Ala Arg Gly Glu Thr Ala Asn Ser Val Ser Cys Tyr Met Arg Thr
                485                 490                 495

Lys Gly Ile Ser Glu Glu Leu Ala Thr Glu Ser Val Met Asn Leu Ile
            500                 505                 510

Asp Glu Thr Trp Lys Lys Met Asn Lys Glu Lys Leu Gly Gly Ser Leu
        515                 520                 525

Phe Ala Lys Pro Phe Val Glu Thr Ala Ile Asn Leu Ala Arg Gln Ser
    530                 535                 540

His Cys Thr Tyr His Asn Gly Asp Ala His Thr Ser Pro Asp Glu Leu
545                 550                 555                 560

Thr Arg Lys Arg Val Leu Ser Val Ile Thr Glu Pro Ile Leu Pro Phe
                565                 570                 575

Glu Arg
```

<210> SEQ ID NO 14
<211> LENGTH: 7370
<212> TYPE: DNA
<213> ORGANISM: Artificial Sequence
<220> FEATURE:
<223> OTHER INFORMATION: Synthetic Construct

<400> SEQUENCE: 14

```
cgtcgttctg cgaactacga acctaacagc tgggactatg attacctgct gtcctccgac     60

acggacgagt ccatcgaagt atacaaagac aaagcgaaaa agctggaagc cgaagttcgt    120

cgcgagatta ataacgaaaa agcagaattt ctgaccctgc tggaactgat tgacaacgtc    180

cagcgcctgg gcctgggtta ccgtttcgag tctgatatcc gtcgtgcgct ggatcgcttc    240

gtttcctccg gcggcttcga tgcggtaacc aagacttccc tgcacgcgac ggcactgtct    300

ttccgtctgc tgcgtcaaca cggttttgag gtttctcagg aagcgttcag cggcttcaaa    360

gaccaaaacg gcaacttcct ggagaacctg aaggaagata tcaaagctat cctgagcctg    420

tacgaggcca gcttcctggc tctggaaggc gaaaacatcc tggacgaggc gaaggttttc    480

gcaatctctc atctgaaaga actgtctgaa gaaaagatcg gtaaagatct ggcagaacag    540

gtgaaccatg cactggaact gccactgcat cgccgtactc agcgtctgga agcagtactg    600

tctatcgagg cctaccgtaa aaaggaggac gcggatcagg ttctgctgga gctggcaatt    660

ctggattaca acatgatcca gtctgtatac cagcgtgatc tgcgtgaaac gtcccgttgg    720

tggcgtcgtg tgggtctggc gaccaaactg cactttgctc gtgaccgcct gattgagagc    780

ttctactggg ccgtgggtgt agcattcgaa ccgcaatact ccgactgccg taactccgtc    840

gcaaaaatgt tttctttcgt aaccattatc gacgatatct acgatgtata cggcaccctg    900

gacgaactgg agctgtttac taacgcagtt gagcgttggg acgtaaacgc catcgacgat    960

ctgccggatt acatgaaact gtgctttctg gctctgtata acactattaa cgaaatcgcc   1020

tacgacaacc tgaaagaaaa aggtgagaac atcctgccgt atctgaccaa agcctgggct   1080

gacctgtgca acgctttcct gcaagaagcc aagtggctgt acaacaaatc tactccgacc   1140

tttgacgaat acttcggcaa cgcatggaaa tcctcttctg gcccgctgca actggtgttc   1200

gcttacttcg ctgtcgtgca gaacattaaa aaggaagaga tcgaaaacct gcaaaaatac   1260

catgacatca tctctcgtcc ttcccatatc ttccgtctgt gcaatgacct ggctagcgcg   1320
```

tctgcggaaa ttgcgcgtgg tgaaaccgca aatagcgttt cttgttacat gcgcactaaa 1380
ggtatctccg aagaactggc taccgaaagc gtgatgaatc tgatcgatga aacctggaaa 1440
aagatgaaca aggaaaaact gggtggtagc ctgttcgcga aaccgttcgt ggaaaccgcg 1500
atcaacctgg cacgtcaatc tcactgcact tatcataacg gcgacgcgca tacctctccg 1560
gatgagctga cccgcaaacg cgttctgtct gtaatcactg aaccgattct gccgtttgaa 1620
cgctaaaagg gcgagctcaa cgatccggct gctaacaaag cccgaaagga agctgagttg 1680
gctgctgcca ccgctgagca ataactagca taaccccttg gggcctctaa acgggtcttg 1740
aggagttttt tgctgaaagg aggaactata tccggatatc ccgcaagagg cccggcagta 1800
ccggcataac caagcctatg cctacagcat ccagggtgac ggtgccgagg atgacgatga 1860
gcgcattgtt agatttcata cacggtgcct gactgcgtta gcaatttaac tgtgataaac 1920
taccgcatta aagcttatcg atgataagct gtcaaacatg agaattaatt cttgaagacg 1980
aaagggcctc gtgatacgcc tatttttata ggttaatgtc atgataataa tggtttctta 2040
gacgtcaggt ggcacttttc ggggaaatgt gcgcggaacc cctatttgtt tatttttcta 2100
aatacattca aatatgtatc cgctcatgag acaataaccc tgataaatgc ttcaataata 2160
ttgaaaaagg aagagtatga ttgaacaaga tggattgcac gcaggttctc cggccgcttg 2220
ggtggagagg ctattcggct atgactgggc acaactgaca atcggctgct ctgatgccgc 2280
cgtgttccgg ctgtcagcgc aggggcgccc ggttcttttt gtcaagaccg acctgtccgg 2340
tgccctgaat gaactgcagg acgaggcagc gcggctatcg tggctggcca cgacgggcgt 2400
tccttgcgca gctgtgctcg acgttgtcac tgaagcggga agggactggc tgctattggg 2460
cgaagtgccg gggcaggatc tcctgtcatc tcaccttgct cctgccgaga aagtatccat 2520
catggctgat gcaatgcggc ggctgcatac gcttgatccg gctacctgcc cattcgacca 2580
ccaagcgaaa catcgcatcg agcgggcacg tactcggatg gaagccggtc ttgtcgatca 2640
ggatgatctg gacgaagagc atcaggggct cgcgccagcc gaactgttcg ccaggctcaa 2700
ggcgcgcatg cccgacggcg aggatctcgt cgtgacacat ggcgatgcct gcttgccgaa 2760
tatcatggtg gaaaatggcc gcttttctgg attcatcgac tgtggccggc tgggtgtggc 2820
ggaccgctat caggacatag cgttggctac ccgtgatatt gctgaagagc ttggcggcga 2880
atgggctgac cgcttcctcg tgctttacgg tatcgccgct cccgattcgc agcgcatcgc 2940
cttctatcgc cttcttgacg agttcttctg agcgggactc tggggttcga aatgaccgac 3000
caagcgacgc ctaactgtca gaccaagttt actcatatat actttagatt gatttaaaac 3060
ttcattttta atttaaaagg atctaggtga agatcctttt tgataatctc atgaccaaaa 3120
tcccttaacg tgagttttcg ttccactgag cgtcagaccc cgtagaaaag atcaaaggat 3180
cttcttgaga tccttttttt ctgcgcgtaa tctgctgctt gcaaacaaaa aaaccaccgc 3240
taccagcggt ggtttgtttg ccggatcaag agctaccaac tctttttccg aaggtaactg 3300
gcttcagcag agcgcagata ccaaatactg tccttctagt gtagccgtag ttaggccacc 3360
acttcaagaa ctctgtagca ccgcctacat acctcgctct gctaatcctg ttaccagtgg 3420
ctgctgccag tggcgataag tcgtgtctta ccgggttgga ctcaagacga tagttaccgg 3480
ataaggcgca gcggtcgggc tgaacggggg gttcgtgcac acagcccagc ttggagcgaa 3540
cgacctacac cgaactgaga tacctacagc gtgagctatg agaaagcgcc acgcttcccg 3600
aagggagaaa ggcggacagg tatccggtaa gcggcagggt cggaacagga gagcgcacga 3660
gggagcttcc agggggaaac gcctggtatc tttatagtcc tgtcgggttt cgccacctct 3720

```
gacttgagcg tcgatttttg tgatgctcgt caggggggcg gagcctatgg aaaaacgcca   3780
gcaacgcggc ctttttacgg ttcctggcct tttgctggcc ttttgctcac atgttctttc   3840
ctgcgttatc ccctgattct gtggataacc gtattaccgc ctttgagtga gctgataccg   3900
ctcgccgcag ccgaacgacc gagcgcagcg agtcagtgag cgaggaagcg gaagagcgcc   3960
tgatgcggta ttttctcctt acgcatctgt gcggtatttc acaccgcaat ggtgcactct   4020
cagtacaatc tgctctgatg ccgcatagtt aagccagtat acactccgct atcgctacgt   4080
gactgggtca tggctgcgcc ccgacacccg ccaacacccg ctgacgcgcc ctgacgggct   4140
tgtctgctcc cggcatccgc ttacagacaa gctgtgaccg tctccgggag ctgcatgtgt   4200
cagaggtttt caccgtcatc accgaaacgc gcgaggcagc tgcggtaaag ctcatcagcg   4260
tggtcgtgaa gcgattcaca gatgtctgcc tgttcatccg cgtccagctc gttgagtttc   4320
tccagaagcg ttaatgtctg gcttctgata aagcgggcca tgttaagggc ggttttttcc   4380
tgtttggtca ctgatgcctc cgtgtaaggg ggatttctgt tcatgggggt aatgataccg   4440
atgaaacgag agaggatgct cacgatacgg gttactgatg atgaacatgc ccggttactg   4500
gaacgttgtg agggtaaaca actggcggta tggatgcggc gggaccagag aaaaatcact   4560
cagggtcaat gccagcgctt cgttaataca gatgtaggtg ttccacaggg tagccagcag   4620
catcctgcga tgcagatccg gaacataatg gtgcagggcg ctgacttccg cgtttccaga   4680
ctttacgaaa cacggaaacc gaagaccatt catgttgttg ctcaggtcgc agacgttttg   4740
cagcagcagt cgcttcacgt tcgctcgcgt atcggtgatt cattctgcta accagtaagg   4800
caaccccgcc agcctagccg ggtcctcaac gacaggagca cgatcatgcg cacccgtggc   4860
caggacccaa cgctgcccga gatgcgccgc gtgcggctgc tggagatggc ggacgcgatg   4920
gatatgttct gccaagggtt ggtttgcgca ttcacagttc tccgcaagaa ttgattggct   4980
ccaattcttg gagtggtgaa tccgttagcg aggtgccgcc ggcttccatt caggtcgagg   5040
tggcccggct ccatgcaccg cgacgcaacg cggggaggca gacaaggtat agggcggcgc   5100
ctacaatcca tgccaacccg ttccatgtgc tcgccgaggc ggcataaatc gccgtgacga   5160
tcagcggtcc aatgatcgaa gttaggctgg taagagccgc gagcgatcct tgaagctgtc   5220
cctgatggtc gtcatctacc tgcctggaca gcatggcctg caacgcgggc atcccgatgc   5280
cgccggaagc gagaagaatc ataatgggga aggccatcca gcctcgcgtc gcgaacgcca   5340
gcaagacgta gcccagcgcg tcggccgcca tgccggcgat aatggcctgc ttctcgccga   5400
aacgtttggt ggcgggacca gtgacgaagg cttgagcgag ggcgtgcaag attccgaata   5460
ccgcaagcga caggccgatc atcgtcgcgc tccagcgaaa gcggtcctcg ccgaaaatga   5520
cccagagcgc tgccggcacc tgtcctacga gttgcatgat aaagaagaca gtcataagtg   5580
cggcgacgat agtcatgccc cgcgcccacc ggaaggagct gactgggttg aaggctctca   5640
agggcatcgg tcgagatccc ggtgcctaat gagtgagcta acttacatta attgcgttgc   5700
gctcactgcc cgctttccag tcgggaaacc tgtcgtgcca gctgcattaa tgaatcggcc   5760
aacgcgcggg gagaggcggt ttgcgtattg ggcgccaggg tggtttttct tttcaccagt   5820
gagacgggca acagctgatt gcccttcacc gcctggccct gagagagttg cagcaagcgg   5880
tccacgctgg tttgccccag caggcgaaaa tcctgtttga tggtggttaa cggcgggata   5940
taacatgagc tgtcttcggt atcgtcgtat cccactaccg agatatccgc accaacgcgc   6000
agcccggact cggtaatggc gcgcattgcg cccagcgcca tctgatcgtt ggcaaccagc   6060
atcgcagtgg gaacgatgcc ctcattcagc atttgcatgg tttgttgaaa accggacatg   6120
```

gcactccagt cgccttcccg ttccgctatc ggctgaattt gattgcgagt gagatattta 6180
tgccagccag ccagacgcag acgcgccgag acagaactta atgggcccgc taacagcgcg 6240
atttgctggt gacccaatgc gaccagatgc tccacgccca gtcgcgtacc gtcttcatgg 6300
gagaaaataa tactgttgat gggtgtctgg tcagagacat caagaaataa cgccggaaca 6360
ttagtgcagg cagcttccac agcaatggca tcctggtcat ccagcggata gttaatgatc 6420
agcccactga cgcgttgcgc gagaagattg tgcaccgccg ctttacaggc ttcgacgccg 6480
cttcgttcta ccatcgacac caccacgctg gcacccagtt gatcggcgcg agatttaatc 6540
gccgcgacaa tttgcgacgg cgcgtgcagg gccagactgg aggtggcaac gccaatcagc 6600
aacgactgtt tgcccgccag ttgttgtgcc acgcggttgg gaatgtaatt cagctccgcc 6660
atcgccgctt ccactttttc ccgcgttttc gcagaaacgt ggctggcctg gttcaccacg 6720
cgggaaacgg tctgataaga gacaccggca tactctgcga catcgtataa cgttactggt 6780
ttcacattca ccaccctgaa ttgactctct tccgggcgct atcatgccat accgcgaaag 6840
gttttgcgcc attcgatggt gtccgggatc tcgacgctct cccttatgcg actcctgcat 6900
taggaagcag cccagtagta ggttgaggcc gttgagcacc gccgccgcaa ggaatggtgc 6960
atgcaaggag atggcgccca acagtccccc ggccacgggg cctgccacca tacccacgcc 7020
gaaacaagcg ctcatgagcc cgaagtggcg agcccgatct tccccatcgg tgatgtcggc 7080
gatataggcg ccagcaaccg cacctgtggc gccggtgatg ccggccacga tgcgtccggc 7140
gtagaggatc gagatctcga tcccgcgaaa ttaatacgac tcactatagg ggaattgtga 7200
gcggataaca attcccctct agaaataatt ttgtttaact ttaagaagga gatatacata 7260
tgcggggttc tcatcatcat catcatcatg gtatggctag catgactggt ggacagcaaa 7320
tgggtcggga tctgtacgac gatgacgata aggatcatcc cttcaccatg 7370

<210> SEQ ID NO 15
<211> LENGTH: 7424
<212> TYPE: DNA
<213> ORGANISM: Artificial Sequence
<220> FEATURE:
<223> OTHER INFORMATION: Synthetic Construct

<400> SEQUENCE: 15
aagggcgagc tcaacgatcc ggctgctaac aaagcccgaa aggaagctga gttggctgct 60
gccaccgctg agcaataact agcataaccc cttggggcct ctaaacgggt cttgaggagt 120
tttttgctga aaggaggaac tatatccgga tatcccgcaa gaggcccggc agtaccggca 180
taaccaagcc tatgcctaca gcatccaggg tgacggtgcc gaggatgacg atgagcgcat 240
tgttagattt catacacggt gcctgactgc gttagcaatt taactgtgat aaactaccgc 300
attaaagctt atcgatgata agctgtcaaa catgagaatt aattcttgaa gacgaaaggg 360
cctcgtgata cgcctatttt tataggttaa tgtcatgata ataatggttt cttagacgtc 420
aggtggcact tttcggggaa atgtgcgcgg aacccctatt tgtttatttt tctaaataca 480
ttcaaatatg tatccgctca tgagacaata accctgataa atgcttcaat aatattgaaa 540
aaggaagagt atgattgaac aagatggatt gcacgcaggt tctccggccg cttgggtgga 600
gaggctattc ggctatgact gggcacaact gacaatcggc tgctctgatg ccgccgtgtt 660
ccggctgtca gcgcaggggc gcccggttct ttttgtcaag accgacctgt ccggtgccct 720
gaatgaactg caggacgagg cagcgcggct atcgtggctg gccacgacgg gcgttccttg 780
cgcagctgtg ctcgacgttg tcactgaagc gggaagggac tggctgctat tgggcgaagt 840

-continued

```
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc tttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact tccgcgtttc cagactttac   3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
```

-continued

```
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg gcgcctacaa   3480
tccatgccaa cccgttccat gtgctcgccg aggcggcata aatcgccgtg acgatcagcg   3540
gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
gcgctgccgg cacctgtcct acgagttgca tgataaagaa gacagtcata agtgcggcga   3960
cgatagtcat gccccgcgcc caccggaagg agctgactgg gttgaaggct ctcaagggca   4020
tcggtcgaga tcccggtgcc taatgagtga gctaacttac attaattgcg ttgcgctcac   4080
tgcccgcttt ccagtcggga aacctgtcgt gccagctgca ttaatgaatc ggccaacgcg   4140
cggggagagg cggtttgcgt attgggcgcc agggtggttt ttcttttcac cagtgagacg   4200
ggcaacagct gattgccctt caccgcctgg ccctgagaga gttgcagcaa gcggtccacg   4260
ctggtttgcc ccagcaggcg aaaatcctgt ttgatggtgg ttaacggcgg gatataacat   4320
gagctgtctt cggtatcgtc gtatcccact accgagatat ccgcaccaac gcgcagcccg   4380
gactcggtaa tggcgcgcat tgcgcccagc gccatctgat cgttggcaac cagcatcgca   4440
gtgggaacga tgccctcatt cagcatttgc atggtttgtt gaaaaccgga catggcactc   4500
cagtcgcctt cccgttccgc tatcggctga atttgattgc gagtgagata tttatgccag   4560
ccagccagac gcagacgcgc cgagacagaa cttaatgggc ccgctaacag cgcgatttgc   4620
tggtgaccca atgcgaccag atgctccacg cccagtcgcg taccgtcttc atgggagaaa   4680
ataatactgt tgatgggtgt ctggtcagag acatcaagaa ataacgccgg aacattagtg   4740
caggcagctt ccacagcaat ggcatcctgg tcatccagcg gatagttaat gatcagccca   4800
ctgacgcgtt gcgcgagaag attgtgcacc gccgctttac aggcttcgac gccgcttcgt   4860
tctaccatcg acaccaccac gctggcaccc agttgatcgg cgcgagattt aatcgccgcg   4920
acaatttgcg acggcgcgtg cagggccaga ctggaggtgg caacgccaat cagcaacgac   4980
tgtttgcccg ccagttgttg tgccacgcgg ttgggaatgt aattcagctc cgccatcgcc   5040
gcttccactt tttcccgcgt tttcgcagaa acgtggctgg cctggttcac cacgcgggaa   5100
acggtctgat aagagacacc ggcatactct gcgacatcgt ataacgttac tggtttcaca   5160
ttcaccaccc tgaattgact ctcttccggg cgctatcatg ccataccgcg aaaggttttg   5220
cgccattcga tggtgtccgg gatctcgacg ctctccctta tgcgactcct gcattaggaa   5280
gcagcccagt agtaggttga ggccgttgag caccgccgcc gcaaggaatg gtgcatgcaa   5340
ggagatggcg cccaacagtc ccccggccac ggggcctgcc accataccca cgccgaaaca   5400
agcgctcatg agcccgaagt ggcgagcccg atcttcccca tcggtgatgt cggcgatata   5460
ggcgccagca accgcacctg tggcgccggt gatgccggcc acgatgcgtc cggcgtagag   5520
gatcgagatc tcgatcccgc gaaattaata cgactcacta taggggaatt gtgagcggat   5580
aacaattccc ctctagaaat aattttgttt aactttaaga aggagatata catatgcggg   5640
```

gttctcatca tcatcatcat catggtatgg ctagcatgac tggtggacag caaatgggtc 5700
gggatctgta cgacgatgac gataaggatc atcccttcac catgcgttgt agcgtgtcca 5760
ccgaaaatgt gtctttcacc gaaactgaaa ccgaagctcg tcgttctgcg aactacgaac 5820
ctaacagctg ggactatgat tacctgctgt cctccgacac ggacgagtcc atcgaagtat 5880
acaaagacaa agcgaaaaag ctggaagccg aagttcgtcg cgagattaat aacgaaaaag 5940
cagaatttct gaccctgctg gaactgattg acaacgtcca gcgcctgggc ctgggttacc 6000
gtttcgagtc tgatatccgt ggtgcgctgg atcgcttcgt ttcctccggc ggcttcgatg 6060
cggtaaccaa gacttccctg cacggtacgg cactgtcttt ccgtctgctg cgtcaacacg 6120
gttttgaggt ttctcaggaa gcgttcagcg gcttcaaaga ccaaaacggc aacttcctgg 6180
agaacctgaa ggaagatatc aaagctatcc tgagcctgta cgaggccagc ttcctggctc 6240
tggaaggcga aaacatcctg gacgaggcga aggttttcgc aatctctcat ctgaaagaac 6300
tgtctgaaga aaagatcggt aaagagctgg cagaacaggt gaaccatgca ctggaactgc 6360
cactgcatcg ccgtactcag cgtctggaag cagtatggtc tatcgaggcc taccgtaaaa 6420
aggaggacgc gaatcaggtt ctgctggagc tggcaattct ggattacaac atgatccagt 6480
ctgtatacca gcgtgatctg cgtgaaacgt cccgttggtg gcgtcgtgtg ggtctggcga 6540
ccaaactgca ctttgctcgt gaccgcctga ttgagagctt ctactgggcc gtgggtgtag 6600
cattcgaacc gcaatactcc gactgccgta actccgtcgc aaaaatgttt tctttcgtaa 6660
ccattatcga cgatatctac gatgtatacg gcaccctgga cgaactggag ctgtttactg 6720
atgcagttga gcgttgggac gtaaacgcca tcaacgacct gccggattac atgaaactgt 6780
gctttctggc tctgtataac actattaacg aaatcgccta cgacaacctg aaagataaag 6840
gtgagaacat cctgccgtat ctgaccaaag cctgggctga cctgtgcaac gctttcctgc 6900
aagaagccaa gtggctgtac aacaaatcta ctccgacctt tgacgactac ttcggcaacg 6960
catggaaatc ctcttctggc ccgctgcaac tggtgttcgc ttacttcgct gtcgtgcaga 7020
acattaaaaa ggaagagatc gaaaacctgc aaaaatacca tgacaccatc tctcgtcctt 7080
cccatatctt ccgtctgtgc aatgacctgg ctagcgcgtc tgcggaaatt gcgcgtggtg 7140
aaaccgcaaa tagcgtttct tgttacatgc gcactaaagg tatctccgaa gaactggcta 7200
ccgaaagcgt gatgaatctg atcgatgaaa cctggaaaaa gatgaacaag gaaaaactgg 7260
gtggtagcct gttcgcgaaa ccgttcgtgg aaaccgcgat caacctggca cgtcaatctc 7320
actgcactta tcataacggc gacgcgcata cctctccgga tgagctgacc cgcaaacgcg 7380
ttctgtctgt aatcactgaa ccgattctgc cgtttgaacg ctaa 7424

<210> SEQ ID NO 16
<211> LENGTH: 560
<212> TYPE: PRT
<213> ORGANISM: Populus alba

<400> SEQUENCE: 16

Met Arg Cys Ser Val Ser Thr Glu Asn Val Ser Phe Thr Glu Thr Glu
1 5 10 15

Thr Glu Ala Arg Arg Ser Ala Asn Tyr Glu Pro Asn Ser Trp Asp Tyr
20 25 30

Asp Tyr Leu Leu Ser Ser Asp Thr Asp Glu Ser Ile Glu Val Tyr Lys
35 40 45

Asp Lys Ala Lys Lys Leu Glu Ala Glu Val Arg Arg Glu Ile Asn Asn
50 55 60

```
Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Gly Ala Leu
                85                  90                  95

Asp Arg Phe Val Ser Ser Gly Gly Phe Asp Ala Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Asn His Ala Leu Glu Leu Pro Leu
        195                 200                 205

His Arg Arg Thr Gln Arg Leu Glu Ala Val Trp Ser Ile Glu Ala Tyr
    210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
    290                 295                 300

Phe Val Thr Ile Ile Asp Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                325                 330                 335

Ile Asn Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Asp Lys Gly Glu
        355                 360                 365

Asn Ile Leu Pro Tyr Leu Thr Lys Ala Trp Ala Asp Leu Cys Asn Ala
    370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Ser Gly Pro Leu Gln
                405                 410                 415

Leu Val Phe Ala Tyr Phe Ala Val Val Gln Asn Ile Lys Lys Glu Glu
            420                 425                 430

Ile Glu Asn Leu Gln Lys Tyr His Asp Thr Ile Ser Arg Pro Ser His
        435                 440                 445

Ile Phe Arg Leu Cys Asn Asp Leu Ala Ser Ala Ser Ala Glu Ile Ala
    450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
```

-continued

```
                485                 490                 495

Thr Trp Lys Lys Met Asn Lys Glu Lys Leu Gly Gly Ser Leu Phe Ala
            500                 505                 510

Lys Pro Phe Val Glu Thr Ala Ile Asn Leu Ala Arg Gln Ser His Cys
        515                 520                 525

Thr Tyr His Asn Gly Asp Ala His Thr Ser Pro Asp Glu Leu Thr Arg
    530                 535                 540

Lys Arg Val Leu Ser Val Ile Thr Glu Pro Ile Leu Pro Phe Glu Arg
545                 550                 555                 560


<210> SEQ ID NO 17
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 17

tggcgaatgg gacgcgccct gtagcggcgc attaagcgcg gcgggtgtgg tggttacgcg      60

cagcgtgacc gctacacttg ccagcgccct agcgcccgct cctttcgctt tcttcccttc     120

ctttctcgcc acgttcgccg gctttccccg tcaagctcta aatcgggggc tccctttagg     180

gttccgattt agtgctttac ggcacctcga ccccaaaaaa cttgattagg gtgatggttc     240

acgtagtggg ccatcgccct gatagacggt ttttcgccct ttgacgttgg agtccacgtt     300

ctttaatagt ggactcttgt tccaaactgg aacaacactc aaccctatct cggtctattc     360

ttttgattta taagggattt tgccgatttc ggcctattgg ttaaaaaatg agctgattta     420

acaaaaattt aacgcgaatt ttaacaaaat attaacgttt acaatttcag gtggcacttt     480

tcggggaaat gtgcgcggaa cccctatttg tttatttttc taaatacatt caaatatgta     540

tccgctcatg aattaattct tagaaaaact catcgagcat caaatgaaac tgcaatttat     600

tcatatcagg attatcaata ccatattttt gaaaaagccg tttctgtaat gaaggagaaa     660

actcaccgag gcagttccat aggatggcaa gatcctggta tcggtctgcg attccgactc     720

gtccaacatc aatacaacct attaatttcc cctcgtcaaa aataaggtta tcaagtgaga     780

aatcaccatg agtgacgact gaatccggtg agaatggcaa aagtttatgc atttctttcc     840

agacttgttc aacaggccag ccattacgct cgtcatcaaa atcactcgca tcaaccaaac     900

cgttattcat tcgtgattgc gcctgagcga gacgaaatac gcgatcgctg ttaaaaggac     960

aattacaaac aggaatcgaa tgcaaccggc gcaggaacac tgccagcgca tcaacaatat    1020

tttcacctga atcaggatat tcttctaata cctggaatgc tgttttcccg gggatcgcag    1080

tggtgagtaa ccatgcatca tcaggagtac ggataaaatg cttgatggtc ggaagaggca    1140

taaattccgt cagccagttt agtctgacca tctcatctgt aacatcattg gcaacgctac    1200

ctttgccatg tttcagaaac aactctggcg catcgggctt cccatacaat cgatagattg    1260

tcgcacctga ttgcccgaca ttatcgcgag cccatttata cccatataaa tcagcatcca    1320

tgttggaatt taatcgcggc ctagagcaag acgtttcccg ttgaatatgg ctcataacac    1380

cccttgtatt actgtttatg taagcagaca gttttattgt tcatgaccaa aatcccttaa    1440

cgtgagtttt cgttccactg agcgtcagac cccgtagaaa agatcaaagg atcttcttga    1500

gatccttttt ttctgcgcgt aatctgctgc ttgcaaacaa aaaaaccacc gctaccagcg    1560

gtggtttgtt tgccggatca agagctacca actctttttc cgaaggtaac tggcttcagc    1620

agagcgcaga taccaaatac tgtccttcta gtgtagccgt agttaggcca ccacttcaag    1680
```

-continued

```
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggtaatga taccgatgaa    2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
```

-continued

```
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcgttgt agcgtgtcca ccgaaaatgt   5100
gtctttcacc gaaactgaaa ccgaagctcg tcgttctgcg aactacgaac ctaacagctg   5160
ggactatgat tacctgctgt cctccgacac ggacgagtcc atcgaagtat acaaagacaa   5220
agcgaaaaag ctggaagccg aagttcgtcg cgagattaat aacgaaaaag cagaatttct   5280
gaccctgctg gaactgattg acaacgtcca gcgcctgggc ctgggttacc gtttcgagtc   5340
tgatatccgt ggtgcgctgg atcgcttcgt ttcctccggc ggcttcgatg cggtaaccaa   5400
gacttccctg cacggtacgg cactgtcttt ccgtctgctg cgtcaacacg gttttgaggt   5460
ttctcaggaa gcgttcagcg gcttcaaaga ccaaaacggc aacttcctgg agaacctgaa   5520
ggaagatatc aaagctatcc tgagcctgta cgaggccagc ttcctggctc tggaaggcga   5580
aaacatcctg gacgaggcga aggttttcgc aatctctcat ctgaaagaac tgtctgaaga   5640
aaagatcggt aaagagctgg cagaacaggt gaaccatgca ctggaactgc cactgcatcg   5700
ccgtactcag cgtctggaag cagtatggtc tatcgaggcc taccgtaaaa aggaggacgc   5760
gaatcaggtt ctgctggagc tggcaattct ggattacaac atgatccagt ctgtatacca   5820
gcgtgatctg cgtgaaacgt cccgttggtg gcgtcgtgtg ggtctggcga ccaaactgca   5880
ctttgctcgt gaccgcctga ttgagagctt ctactgggcc gtgggtgtag cattcgaacc   5940
gcaatactcc gactgccgta actccgtcgc aaaaatgttt tctttcgtaa ccattatcga   6000
cgatatctac gatgtatacg gcaccctgga cgaactggag ctgtttactg atgcagttga   6060
gcgttgggac gtaaacgcca tcaacgacct gccggattac atgaaactgt gctttctggc   6120
tctgtataac actattaacg aaatcgccta cgacaacctg aaagataaag gtgagaacat   6180
cctgccgtat ctgaccaaag cctgggctga cctgtgcaac gctttcctgc aagaagccaa   6240
gtggctgtac aacaaatcta ctccgacctt tgacgactac ttcggcaacg catggaaatc   6300
ctcttctggc ccgctgcaac tggtgttcgc ttacttcgct gtcgtgcaga acattaaaaa   6360
ggaagagatc gaaaacctgc aaaaatacca tgacaccatc tctcgtcctt cccatatctt   6420
ccgtctgtgc aatgacctgg ctagcgcgtc tgcggaaatt gcgcgtggtg aaaccgcaaa   6480
```

-continued

```
tagcgtttct tgttacatgc gcactaaagg tatctccgaa gaactggcta ccgaaagcgt   6540

gatgaatctg atcgatgaaa cctggaaaaa gatgaacaag gaaaaactgg gtggtagcct   6600

gttcgcgaaa ccgttcgtgg aaaccgcgat caacctggca cgtcaatctc actgcactta   6660

tcataacggc gacgcgcata cctctccgga tgagctgacc cgcaaacgcg ttctgtctgt   6720

aatcactgaa ccgattctgc cgtttgaacg ctaaggatcc gaattcgagc tccgtcgaca   6780

agcttgcggc cgcactcgag caccaccacc accaccactg agatccggct gctaacaaag   6840

cccgaaagga agctgagttg gctgctgcca ccgctgagca ataactagca taaccccttg   6900

gggcctctaa acgggtcttg aggggttttt tgctgaaagg aggaactata tccggat      6957
```

<210> SEQ ID NO 18
<211> LENGTH: 559
<212> TYPE: PRT
<213> ORGANISM: Artificial Sequence
<220> FEATURE:
<223> OTHER INFORMATION: Synthetic Construct

<400> SEQUENCE: 18

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285
```

```
Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 19
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 19

```
tggcgaatgg gacgcgccct gtagcggcgc attaagcgcg gcgggtgtgg tggttacgcg      60

cagcgtgacc gctacacttg ccagcgccct agcgcccgct cctttcgctt tcttcccttc     120

ctttctcgcc acgttcgccg gctttccccg tcaagctcta aatcgggggc tccctttagg     180

gttccgattt agtgctttac ggcacctcga ccccaaaaaa cttgattagg gtgatggttc     240

acgtagtggg ccatcgccct gatagacggt ttttcgccct ttgacgttgg agtccacgtt     300

ctttaatagt ggactcttgt tccaaactgg aacaacactc aaccctatct cggtctattc     360

ttttgattta taagggattt tgccgatttc ggcctattgg ttaaaaaatg agctgattta     420

acaaaaattt aacgcgaatt ttaacaaaat attaacgttt acaatttcag gtggcacttt     480

tcggggaaat gtgcgcggaa cccctatttg tttatttttc taaatacatt caaatatgta     540

tccgctcatg aattaattct tagaaaaact catcgagcat caaatgaaac tgcaatttat     600
```

-continued

```
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggggtaatga taccgatgaa  2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
```

-continued cgaaacacgg aaaccgaaga ccattcatgt tgttgctcag gtcgcagacg ttttgcagca 3060
gcagtcgctt cacgttcgct cgcgtatcgg tgattcattc tgctaaccag taaggcaacc 3120
ccgccagcct agccgggtcc tcaacgacag gagcacgatc atgcgcaccc gtggggccgc 3180
catgccggcg ataatggcct gcttctcgcc gaaacgtttg gtggcgggac cagtgacgaa 3240
ggcttgagcg agggcgtgca agattccgaa taccgcaagc gacaggccga tcatcgtcgc 3300
gctccagcga aagcggtcct cgccgaaaat gacccagagc gctgccggca cctgtcctac 3360
gagttgcatg ataaagaaga cagtcataag tgcggcgacg atagtcatgc cccgcgccca 3420
ccggaaggag ctgactgggt tgaaggctct caagggcatc ggtcgagatc ccggtgccta 3480
atgagtgagc taacttacat taattgcgtt gcgctcactg cccgctttcc agtcgggaaa 3540
cctgtcgtgc cagctgcatt aatgaatcgg ccaacgcgcg gggagaggcg gtttgcgtat 3600
tgggcgccag ggtggttttt cttttcacca gtgagacggg caacagctga ttgcccttca 3660
ccgcctggcc ctgagagagt tgcagcaagc ggtccacgct ggtttgcccc agcaggcgaa 3720
aatcctgttt gatggtggtt aacggcggga tataacatga gctgtcttcg gtatcgtcgt 3780
atcccactac cgagatatcc gcaccaacgc gcagcccgga ctcggtaatg gcgcgcattg 3840
cgcccagcgc catctgatcg ttggcaacca gcatcgcagt gggaacgatg ccctcattca 3900
gcatttgcat ggtttgttga aaaccggaca tggcactcca gtcgccttcc cgttccgcta 3960
tcggctgaat ttgattgcga gtgagatatt tatgccagcc agccagacgc agacgcgccg 4020
agacagaact taatgggccc gctaacagcg cgatttgctg gtgacccaat gcgaccagat 4080
gctccacgcc cagtcgcgta ccgtcttcat gggagaaaat aatactgttg atgggtgtct 4140
ggtcagagac atcaagaaat aacgccggaa cattagtgca ggcagcttcc acagcaatgg 4200
catcctggtc atccagcgga tagttaatga tcagcccact gacgcgttgc gcgagaagat 4260
tgtgcaccgc cgctttacag gcttcgacgc cgcttcgttc taccatcgac accaccacgc 4320
tggcacccag ttgatcggcg cgagatttaa tcgccgcgac aatttgcgac ggcgcgtgca 4380
gggccagact ggaggtggca acgccaatca gcaacgactg tttgcccgcc agttgttgtg 4440
ccacgcggtt gggaatgtaa ttcagctccg ccatcgccgc ttccactttt tcccgcgttt 4500
tcgcagaaac gtggctggcc tggttcacca cgcgggaaac ggtctgataa gagacaccgg 4560
catactctgc gacatcgtat aacgttactg gtttcacatt caccaccctg aattgactct 4620
cttccgggcg ctatcatgcc ataccgcgaa aggttttgcg ccattcgatg gtgtccggga 4680
tctcgacgct ctcccttatg cgactcctgc attaggaagc agcccagtag taggttgagg 4740
ccgttgagca ccgccgccgc aaggaatggt gcatgcaagg agatggcgcc caacagtccc 4800
ccggccacgg ggcctgccac catacccacg ccgaaacaag cgctcatgag cccgaagtgg 4860
cgagcccgat cttccccatc ggtgatgtcg gcgatatagg cgccagcaac cgcacctgtg 4920
gcgccggtga tgccggccac gatgcgtccg gcgtagagga tcgagatctc gatcccgcga 4980
aattaatacg actcactata ggggaattgt gagcggataa caattcccct ctagaaataa 5040
ttttgtttaa ctttaagaag gagatataca tatggaagct cgtcgttctg cgaactacga 5100
acctaacagc tgggactatg attacctgct gtcctccgac acggacgagt ccatcgaagt 5160
atacaaagac aaagcgaaaa agctggaagc cgaagttcgt cgcgagatta ataacgaaaa 5220
agcagaattt ctgaccctgc tggaactgat tgacaacgtc cagcgcctgg gcctgggtta 5280
ccgtttcgag tctgatatcc gtggtgcgct ggatcgcttc gtttcctccg gcggcttcga 5340
tgcggtaacc aagacttccc tgcacggtac ggcactgtct ttccgtctgc tgcgtcaaca 5400

-continued

```
cggttttgag gtttctcagg aagcgttcag cggcttcaaa gaccaaaacg gcaacttcct   5460

ggagaacctg aaggaagata tcaaagctat cctgagcctg tacgaggcca gcttcctggc   5520

tctggaaggc gaaaacatcc tggacgaggc gaaggttttc gcaatctctc atctgaaaga   5580

actgtctgaa gaaaagatcg gtaaagagct ggcagaacag gtgaaccatg cactggaact   5640

gccactgcat cgccgtactc agcgtctgga agcagtatgg tctatcgagg cctaccgtaa   5700

aaaggaggac gcgaatcagg ttctgctgga gctggcaatt ctggattaca acatgatcca   5760

gtctgtatac cagcgtgatc tgcgtgaaac gtcccgttgg tggcgtcgtg tgggtctggc   5820

gaccaaactg cactttgctc gtgaccgcct gattgagagc ttctactggg ccgtgggtgt   5880

agcattcgaa ccgcaatact ccgactgccg taactccgtc gcaaaaatgt ttctttcgt   5940

aaccattatc gacgatatct acgatgtata cggcaccctg gacgaactgg agctgtttac   6000

tgatgcagtt gagcgttggg acgtaaacgc catcaacgac ctgccggatt acatgaaact   6060

gtgctttctg gctctgtata acactattaa cgaaatcgcc tacgacaacc tgaaagataa   6120

aggtgagaac atcctgccgt atctgaccaa agcctgggct gacctgtgca acgctttcct   6180

gcaagaagcc aagtggctgt acaacaaatc tactccgacc tttgacgact acttcggcaa   6240

cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccgca aatagcgttt cttgttacat gcgcactaaa ggtatctccg aagaactggc   6480

taccgaaagc gtgatgaatc tgatcgatga aacctggaaa aagatgaaca aggaaaaact   6540

gggtggtagc ctgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatcactg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

```
<210> SEQ ID NO 20
<211> LENGTH: 575
<212> TYPE: PRT
<213> ORGANISM: Artificial Sequence
<220> FEATURE:
<223> OTHER INFORMATION: Synthetic Construct

<400> SEQUENCE: 20

Met Arg Cys Ser Val Ser Thr Glu Asn Val Ser Phe Thr Glu Thr Glu
1               5                   10                  15

Thr Glu Ala Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val Tyr Lys
        35                  40                  45

Asp Lys Ala Lys Lys Leu Glu Ala Glu Val Arg Arg Glu Ile Asn Asn
    50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Gly Ala Leu
                85                  90                  95

Asp Arg Phe Val Ser Ser Gly Gly Phe Asp Ala Val Thr Lys Thr Ser
```

-continued

```
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Asn His Ala Leu Glu Leu Pro Leu
        195                 200                 205

His Arg Arg Thr Gln Arg Leu Glu Ala Val Trp Ser Ile Glu Ala Tyr
    210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
    290                 295                 300

Phe Val Thr Ile Ile Asp Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                325                 330                 335

Ile Asn Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Asp Lys Gly Glu
        355                 360                 365

Asn Ile Leu Pro Tyr Leu Thr Lys Ala Trp Ala Asp Leu Cys Asn Ala
    370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Ser Gly Pro Leu Gln
                405                 410                 415

Leu Val Phe Ala Tyr Phe Ala Val Val Gln Asn Ile Lys Lys Glu Glu
            420                 425                 430

Ile Glu Asn Leu Gln Lys Tyr His Asp Thr Ile Ser Arg Pro Ser His
        435                 440                 445

Ile Phe Arg Leu Cys Asn Asp Leu Ala Ser Ala Ser Ala Glu Ile Ala
    450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
            500                 505                 510

Lys Pro Phe Val Glu Thr Ala Ile Asn Leu Ala Arg Gln Ser His Cys
        515                 520                 525
```

-continued

```
Thr Tyr His Asn Gly Asp Ala His Thr Ser Pro Asp Glu Leu Thr Arg
    530                 535                 540

Lys Arg Val Leu Ser Val Ile Thr Glu Pro Ile Leu Pro Phe Glu Arg
545                 550                 555                 560

Glu Asn Leu Tyr Phe Gln Gly Leu Glu His His His His His His
                565                 570                 575


<210> SEQ ID NO 21
<211> LENGTH: 6935
<212> TYPE: DNA
<213> ORGANISM: Artificial Sequence
<220> FEATURE:
<223> OTHER INFORMATION: Synthetic Construct

<400> SEQUENCE: 21

tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420

acaaaaattt aacgcgaatt ttaacaaaat attaacgttt acaatttcag gtggcacttt    480

tcggggaaat gtgcgcggaa cccctatttg tttatttttc taaatacatt caaatatgta    540

tccgctcatg aattaattct tagaaaaact catcgagcat caaatgaaac tgcaatttat    600

tcatatcagg attatcaata ccatattttt gaaaaagccg tttctgtaat gaaggagaaa    660

actcaccgag gcagttccat aggatggcaa gatcctggta tcggtctgcg attccgactc    720

gtccaacatc aatacaacct attaatttcc cctcgtcaaa aataaggtta tcaagtgaga    780

aatcaccatg agtgacgact gaatccggtg agaatggcaa aagtttatgc atttctttcc    840

agacttgttc aacaggccag ccattacgct cgtcatcaaa atcactcgca tcaaccaaac    900

cgttattcat tcgtgattgc gcctgagcga gacgaaatac gcgatcgctg ttaaaaggac    960

aattacaaac aggaatcgaa tgcaaccggc gcaggaacac tgccagcgca tcaacaatat   1020

tttcacctga atcaggatat tcttctaata cctggaatgc tgttttcccg gggatcgcag   1080

tggtgagtaa ccatgcatca tcaggagtac ggataaaatg cttgatggtc ggaagaggca   1140

taaattccgt cagccagttt agtctgacca tctcatctgt aacatcattg gcaacgctac   1200

ctttgccatg tttcagaaac aactctggcg catcgggctt cccatacaat cgatagattg   1260

tcgcacctga ttgcccgaca ttatcgcgag cccatttata cccatataaa tcagcatcca   1320

tgttggaatt taatcgcggc ctagagcaag acgtttcccg ttgaatatgg ctcataacac   1380

cccttgtatt actgtttatg taagcagaca gttttattgt tcatgaccaa aatcccttaa   1440

cgtgagtttt cgttccactg agcgtcagac cccgtagaaa agatcaaagg atcttcttga   1500

gatccttttt ttctgcgcgt aatctgctgc ttgcaaacaa aaaaaccacc gctaccagcg   1560

gtggtttgtt tgccggatca agagctacca actctttttc cgaaggtaac tggcttcagc   1620

agagcgcaga taccaaatac tgtccttcta gtgtagccgt agttaggcca ccacttcaag   1680

aactctgtag caccgcctac atacctcgct ctgctaatcc tgttaccagt ggctgctgcc   1740

agtggcgata agtcgtgtct taccgggttg gactcaagac gatagttacc ggataaggcg   1800

cagcggtcgg gctgaacggg gggttcgtgc acacagccca gcttggagcg aacgacctac   1860
```

-continued

```
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggghtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
```

-continued

```
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcgttgt agcgtgtcca ccgaaaatgt   5100
gtctttcacc gaaactgaaa ccgaagctcg tcgttctgcg aactacgaac ctaacagctg   5160
ggactatgat tacctgctgt cctccgacac ggacgagtcc atcgaagtat acaaagacaa   5220
agcgaaaaag ctggaagccg aagttcgtcg cgagattaat aacgaaaaag cagaatttct   5280
gaccctgctg gaactgattg acaacgtcca gcgcctgggc ctgggttacc gtttcgagtc   5340
tgatatccgt ggtgcgctgg atcgcttcgt ttcctccggc ggcttcgatg cggtaaccaa   5400
gacttccctg cacggtacgg cactgtcttt ccgtctgctg cgtcaacacg gttttgaggt   5460
ttctcaggaa gcgttcagcg gcttcaaaga ccaaaacggc aacttcctgg agaacctgaa   5520
ggaagatatc aaagctatcc tgagcctgta cgaggccagc ttcctggctc tggaaggcga   5580
aaacatcctg gacgaggcga aggttttcgc aatctctcat ctgaaagaac tgtctgaaga   5640
aaagatcggt aaagagctgg cagaacaggt gaaccatgca ctggaactgc cactgcatcg   5700
ccgtactcag cgtctggaag cagtatggtc tatcgaggcc taccgtaaaa aggaggacgc   5760
gaatcaggtt ctgctggagc tggcaattct ggattacaac atgatccagt ctgtatacca   5820
gcgtgatctg cgtgaaacgt cccgttggtg gcgtcgtgtg ggtctggcga ccaaactgca   5880
ctttgctcgt gaccgcctga ttgagagctt ctactgggcc gtgggtgtag cattcgaacc   5940
gcaatactcc gactgccgta actccgtcgc aaaaatgttt tctttcgtaa ccattatcga   6000
cgatatctac gatgtatacg gcaccctgga cgaactggag ctgtttactg atgcagttga   6060
gcgttgggac gtaaacgcca tcaacgacct gccggattac atgaaactgt gctttctggc   6120
tctgtataac actattaacg aaatcgccta cgacaacctg aaagataaag gtgagaacat   6180
cctgccgtat ctgaccaaag cctgggctga cctgtgcaac gctttcctgc aagaagccaa   6240
gtggctgtac aacaaatcta ctccgacctt tgacgactac ttcggcaacg catggaaatc   6300
ctcttctggc ccgctgcaac tggtgttcgc ttacttcgct gtcgtgcaga acattaaaaa   6360
ggaagagatc gaaaacctgc aaaaatacca tgacaccatc tctcgtcctt cccatatctt   6420
ccgtctgtgc aatgacctgg ctagcgcgtc tgcggaaatt gcgcgtggtg aaaccgcaaa   6480
tagcgtttct tgttacatgc gcactaaagg tatctccgaa gaactggcta ccgaaagcgt   6540
gatgaatctg atcgatgaaa cctggaaaaa gatgaacaag gaaaaactgg gtggtagcct   6600
gttcgcgaaa ccgttcgtgg aaaccgcgat caacctggca cgtcaatctc actgcactta   6660
```

```
tcataacggc gacgcgcata cctctccgga tgagctgacc cgcaaacgcg ttctgtctgt   6720

aatcactgaa ccgattctgc cgtttgaacg cgaaaacctg tattttcagg gcctcgagca   6780

ccaccaccac caccactgag atccggctgc taacaaagcc cgaaaggaag ctgagttggc   6840

tgctgccacc gctgagcaat aactagcata accccttggg gcctctaaac gggtcttgag   6900

gggttttttg ctgaaaggag gaactatatc cggat                              6935


<210> SEQ ID NO 22
<211> LENGTH: 23
<212> TYPE: DNA
<213> ORGANISM: Artificial Sequence
<220> FEATURE:
<223> OTHER INFORMATION: Synthetic Construct

<400> SEQUENCE: 22

cggtgaactg aaaggtgacg tcc                                             23


<210> SEQ ID NO 23
<211> LENGTH: 25
<212> TYPE: DNA
<213> ORGANISM: Artificial Sequence
<220> FEATURE:
<223> OTHER INFORMATION: Synthetic Construct

<400> SEQUENCE: 23

ggacgttaac gctattaaca ccctg                                           25


<210> SEQ ID NO 24
<211> LENGTH: 22
<212> TYPE: DNA
<213> ORGANISM: Artificial Sequence
<220> FEATURE:
<223> OTHER INFORMATION: Synthetic Construct

<400> SEQUENCE: 24

cacatcgtcg atcagctcca gc                                              22


<210> SEQ ID NO 25
<211> LENGTH: 24
<212> TYPE: DNA
<213> ORGANISM: Artificial Sequence
<220> FEATURE:
<223> OTHER INFORMATION: Synthetic Construct

<400> SEQUENCE: 25

ggtcgtcaga ctgtcgatga agcc                                            24


<210> SEQ ID NO 26
<211> LENGTH: 39
<212> TYPE: DNA
<213> ORGANISM: Artificial Sequence
<220> FEATURE:
<223> OTHER INFORMATION: Synthetic Construct

<400> SEQUENCE: 26

gcttatgaat tctgtgcgac ctcttctcaa tttactcag                            39


<210> SEQ ID NO 27
<211> LENGTH: 38
<212> TYPE: DNA
<213> ORGANISM: Artificial Sequence
<220> FEATURE:
<223> OTHER INFORMATION: Synthetic Construct

<400> SEQUENCE: 27
```

gcttataagc ttagacatac atcagctggt taatcggg 38

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
ctcctccagc aggttctcac c 21

<210> SEQ ID NO 29
<211> LENGTH: 23
<212> TYPE: DNA
<213> ORGANISM: Artificial Sequence
<220> FEATURE:
<223> OTHER INFORMATION: Synthetic Construct

<400> SEQUENCE: 29
caccatgcgt tgtagcgtgt cca 23

<210> SEQ ID NO 30
<211> LENGTH: 52
<212> TYPE: DNA
<213> ORGANISM: Artificial Sequence
<220> FEATURE:
<223> OTHER INFORMATION: Synthetic Construct

<400> SEQUENCE: 30
gggcccgttt aaactttaac tagactctgc agttagcgtt caaacggcag aa 52

<210> SEQ ID NO 31
<211> LENGTH: 25
<212> TYPE: DNA
<213> ORGANISM: Artificial Sequence
<220> FEATURE:
<223> OTHER INFORMATION: Synthetic Construct

<400> SEQUENCE: 31
caccatgcgt cgttctgcga actac 25

<210> SEQ ID NO 32
<211> LENGTH: 26
<212> TYPE: DNA
<213> ORGANISM: Artificial Sequence
<220> FEATURE:
<223> OTHER INFORMATION: Synthetic Construct

<400> SEQUENCE: 32
gcaccatgcg tcgttctgcg aactac 26

<210> SEQ ID NO 33
<211> LENGTH: 37
<212> TYPE: DNA
<213> ORGANISM: Artificial Sequence
<220> FEATURE:
<223> OTHER INFORMATION: Synthetic Construct

<400> SEQUENCE: 33
gatcgaaggg cgatcgtgtc acagtctggc gaaaccg 37

<210> SEQ ID NO 34
<211> LENGTH: 43
<212> TYPE: DNA
<213> ORGANISM: Artificial Sequence
<220> FEATURE:
<223> OTHER INFORMATION: Synthetic Construct

<400> SEQUENCE: 34
ctgaattctg cagatatctg tttttccact cttcgttcac ttt 43

<210> SEQ ID NO 35
<211> LENGTH: 33
<212> TYPE: DNA
<213> ORGANISM: Artificial Sequence
<220> FEATURE:
<223> OTHER INFORMATION: Synthetic Construct

<400> SEQUENCE: 35
tctagagggc ccaagaaaaa tgccccgctt acg 33

<210> SEQ ID NO 36
<211> LENGTH: 111
<212> TYPE: DNA
<213> ORGANISM: Artificial Sequence
<220> FEATURE:
<223> OTHER INFORMATION: Synthetic Construct

<400> SEQUENCE: 36
gatcgcggcc gcgcccttga cgatgccaca tcctgagcaa ataattcaac cactaattgt 60
gagcggataa cacaaggagg aaacagctat gtcattaccg ttcttaactt c 111

<210> SEQ ID NO 37
<211> LENGTH: 75
<212> TYPE: DNA
<213> ORGANISM: Artificial Sequence
<220> FEATURE:
<223> OTHER INFORMATION: Synthetic Construct

<400> SEQUENCE: 37
gatcgggccc caagaaaaaa ggcacgtcat ctgacgtgcc ttttttattt gtagacgcgt 60
tgttatagca ttcta 75

<210> SEQ ID NO 38
<211> LENGTH: 81
<212> TYPE: DNA
<213> ORGANISM: Artificial Sequence
<220> FEATURE:
<223> OTHER INFORMATION: Synthetic Construct

<400> SEQUENCE: 38
aaagtagccg aagatgacgg tttgtcacat ggagttggca ggatgtttga ttaaaagcaa 60
ttaaccctca ctaaagggcg g 81

<210> SEQ ID NO 39
<211> LENGTH: 160
<212> TYPE: DNA
<213> ORGANISM: Artificial Sequence
<220> FEATURE:
<223> OTHER INFORMATION: Synthetic Construct

<400> SEQUENCE: 39
agagtgttca ccaaaaataa taacctttcc cggtgcagaa gttaagaacg gtaatgacat 60
agctgtttcc tccttgtgtt atccgctcac aattagtggt tgaattattt gctcaggatg 120
tggcatcgtc aagggctaat acgactcact atagggctcg 160

<210> SEQ ID NO 40
<211> LENGTH: 14

<212> TYPE: PRT
<213> ORGANISM: Artificial Sequence
<220> FEATURE:
<223> OTHER INFORMATION: Synthetic Construct

<400> SEQUENCE: 40

```
Ser Ala Ser Ala Glu Ile Ala Arg Gly Glu Thr Ala Asn Ser
 1               5                  10
```

<210> SEQ ID NO 41
<211> LENGTH: 13
<212> TYPE: PRT
<213> ORGANISM: Artificial Sequence
<220> FEATURE:
<223> OTHER INFORMATION: Synthetic Construct

<400> SEQUENCE: 41

```
Tyr His Asn Gly Asp Ala His Thr Ser Pro Asp Glu Leu
 1               5                  10
```

<210> SEQ ID NO 42
<211> LENGTH: 564
<212> TYPE: PRT
<213> ORGANISM: Peuraria lobata

<400> SEQUENCE: 42

```
Met Cys Ala Thr Ser Ser Gln Phe Thr Gln Ile Thr Glu His Asn Ser
 1               5                  10                  15

Arg Arg Ser Ala Asn Tyr Gln Pro Asn Leu Trp Asn Phe Glu Phe Leu
            20                  25                  30

Gln Ser Leu Glu Asn Asp Leu Lys Val Glu Lys Leu Glu Glu Lys Ala
        35                  40                  45

Thr Lys Leu Glu Glu Glu Val Arg Cys Met Ile Asn Arg Val Asp Thr
    50                  55                  60

Gln Pro Leu Ser Leu Leu Glu Leu Ile Asp Asp Val Gln Arg Leu Gly
65                  70                  75                  80

Leu Thr Tyr Lys Phe Glu Lys Asp Ile Ile Lys Ala Leu Glu Asn Ile
                85                  90                  95

Val Leu Leu Asp Glu Asn Lys Lys Asn Lys Ser Asp Leu His Ala Thr
            100                 105                 110

Ala Leu Ser Phe Arg Leu Leu Arg Gln His Gly Phe Glu Val Ser Gln
        115                 120                 125

Asp Val Phe Glu Arg Phe Lys Asp Lys Glu Gly Gly Phe Ser Gly Glu
    130                 135                 140

Leu Lys Gly Asp Val Gln Gly Leu Leu Ser Leu Tyr Glu Ala Ser Tyr
145                 150                 155                 160

Leu Gly Phe Glu Gly Glu Asn Leu Leu Glu Glu Ala Arg Thr Phe Ser
                165                 170                 175

Ile Thr His Leu Lys Asn Asn Leu Lys Glu Gly Ile Asn Thr Lys Val
            180                 185                 190

Ala Glu Gln Val Ser His Ala Leu Glu Leu Pro Tyr His Gln Arg Leu
        195                 200                 205

His Arg Leu Glu Ala Arg Trp Phe Leu Asp Lys Tyr Glu Pro Lys Glu
    210                 215                 220

Pro His His Gln Leu Leu Leu Glu Leu Ala Lys Leu Asp Phe Asn Met
225                 230                 235                 240

Val Gln Thr Leu His Gln Lys Glu Leu Gln Asp Leu Ser Arg Trp Trp
                245                 250                 255

Thr Glu Met Gly Leu Ala Ser Lys Leu Asp Phe Val Arg Asp Arg Leu
```

```
            260                 265                 270

Met Glu Val Tyr Phe Trp Ala Leu Gly Met Ala Pro Asp Pro Gln Phe
        275                 280                 285

Gly Glu Cys Arg Lys Ala Val Thr Lys Met Phe Gly Leu Val Thr Ile
    290                 295                 300

Ile Asp Asp Val Tyr Asp Val Tyr Gly Thr Leu Asp Glu Leu Gln Leu
305                 310                 315                 320

Phe Thr Asp Ala Val Glu Arg Trp Asp Val Asn Ala Ile Asn Thr Leu
                325                 330                 335

Pro Asp Tyr Met Lys Leu Cys Phe Leu Ala Leu Tyr Asn Thr Val Asn
            340                 345                 350

Asp Thr Ser Tyr Ser Ile Leu Lys Glu Lys Gly His Asn Asn Leu Ser
        355                 360                 365

Tyr Leu Thr Lys Ser Trp Arg Glu Leu Cys Lys Ala Phe Leu Gln Glu
    370                 375                 380

Ala Lys Trp Ser Asn Asn Lys Ile Ile Pro Ala Phe Ser Lys Tyr Leu
385                 390                 395                 400

Glu Asn Ala Ser Val Ser Ser Ser Gly Val Ala Leu Leu Ala Pro Ser
                405                 410                 415

Tyr Phe Ser Val Cys Gln Gln Gln Glu Asp Ile Ser Asp His Ala Leu
            420                 425                 430

Arg Ser Leu Thr Asp Phe His Gly Leu Val Arg Ser Ser Cys Val Ile
        435                 440                 445

Phe Arg Leu Cys Asn Asp Leu Ala Thr Ser Ala Ala Glu Leu Glu Arg
    450                 455                 460

Gly Glu Thr Thr Asn Ser Ile Ile Ser Tyr Met His Glu Asn Asp Gly
465                 470                 475                 480

Thr Ser Glu Glu Gln Ala Arg Glu Glu Leu Arg Lys Leu Ile Asp Ala
                485                 490                 495

Glu Trp Lys Lys Met Asn Arg Glu Arg Val Ser Asp Ser Thr Leu Leu
            500                 505                 510

Pro Lys Ala Phe Met Glu Ile Ala Val Asn Met Ala Arg Val Ser His
        515                 520                 525

Cys Thr Tyr Gln Tyr Gly Asp Gly Leu Gly Arg Pro Asp Tyr Ala Thr
    530                 535                 540

Glu Asn Arg Ile Lys Leu Leu Leu Ile Asp Pro Phe Pro Ile Asn Gln
545                 550                 555                 560

Leu Met Tyr Val


<210> SEQ ID NO 43
<211> LENGTH: 559
<212> TYPE: PRT
<213> ORGANISM: Populus alba x tremuloides

<400> SEQUENCE: 43

Met Cys Ser Val Ser Thr Glu Asn Val Ser Phe Thr Glu Thr Glu Thr
 1               5                  10                  15

Glu Ala Arg Arg Ser Ala Asn Tyr Glu Pro Asn Ser Trp Asp Tyr Asp
            20                  25                  30

Phe Leu Leu Ser Ser Asp Thr Asp Glu Ser Ile Glu Val Tyr Lys Asp
        35                  40                  45

Lys Ala Lys Lys Leu Glu Ala Glu Val Arg Arg Glu Ile Asn Asn Glu
    50                  55                  60

Lys Ala Glu Phe Leu Thr Leu Leu Glu Leu Ile Asp Asn Val Gln Arg
65                  70                  75                  80
```

```
Leu Gly Leu Gly Tyr Arg Phe Glu Ser Asp Ile Arg Arg Ala Leu Asp
                85                  90                  95

Arg Phe Val Ser Ser Gly Gly Phe Asp Gly Val Thr Lys Thr Ser Leu
            100                 105                 110

His Ala Thr Ala Leu Ser Phe Arg Leu Leu Arg Gln His Gly Phe Glu
        115                 120                 125

Val Ser Gln Glu Ala Phe Ser Gly Phe Lys Asp Gln Asn Gly Asn Phe
    130                 135                 140

Leu Glu Asn Leu Lys Glu Asp Thr Lys Ala Ile Leu Ser Leu Tyr Glu
145                 150                 155                 160

Ala Ser Phe Leu Ala Leu Glu Gly Glu Asn Ile Leu Asp Glu Ala Arg
                165                 170                 175

Val Phe Ala Ile Ser His Leu Lys Glu Leu Ser Glu Glu Lys Ile Gly
            180                 185                 190

Lys Glu Leu Ala Glu Gln Val Asn His Ala Leu Glu Leu Pro Leu His
        195                 200                 205

Arg Arg Thr Gln Arg Leu Glu Ala Val Trp Ser Ile Glu Ala Tyr Arg
    210                 215                 220

Lys Lys Glu Asp Ala Asn Gln Val Leu Leu Glu Leu Ala Ile Leu Asp
225                 230                 235                 240

Tyr Asn Met Ile Gln Ser Val Tyr Gln Arg Asp Leu Arg Glu Thr Ser
                245                 250                 255

Arg Trp Trp Arg Arg Val Gly Leu Ala Thr Lys Leu His Phe Ala Lys
            260                 265                 270

Asp Arg Leu Ile Glu Ser Phe Tyr Trp Ala Val Gly Val Ala Phe Glu
        275                 280                 285

Pro Gln Tyr Ser Asp Cys Arg Asn Ser Val Ala Lys Met Phe Ser Phe
    290                 295                 300

Val Thr Ile Ile Asp Asp Ile Tyr Asp Val Tyr Gly Thr Leu Asp Glu
305                 310                 315                 320

Leu Glu Leu Phe Thr Asp Ala Val Glu Arg Trp Asp Val Asn Ala Ile
                325                 330                 335

Asn Asp Leu Pro Asp Tyr Met Lys Leu Cys Phe Leu Ala Leu Tyr Asn
            340                 345                 350

Thr Ile Asn Glu Ile Ala Tyr Asp Asn Leu Lys Asp Lys Gly Glu Asn
        355                 360                 365

Ile Leu Pro Tyr Leu Thr Lys Ala Trp Ala Asp Leu Cys Asn Ala Phe
    370                 375                 380

Leu Gln Glu Ala Lys Trp Leu Tyr Asn Lys Ser Thr Pro Thr Phe Asp
385                 390                 395                 400

Asp Tyr Phe Gly Asn Ala Trp Lys Ser Ser Ser Gly Pro Leu Gln Leu
                405                 410                 415

Ile Phe Ala Tyr Phe Ala Val Val Gln Asn Ile Lys Lys Glu Glu Ile
            420                 425                 430

Glu Asn Leu Gln Lys Tyr His Asp Ile Ile Ser Arg Pro Ser His Ile
        435                 440                 445

Phe Arg Leu Cys Asn Asp Leu Ala Ser Ala Ser Ala Glu Ile Ala Arg
    450                 455                 460

Gly Glu Thr Ala Asn Ser Val Ser Cys Tyr Met Arg Thr Lys Gly Ile
465                 470                 475                 480

Ser Glu Glu Leu Ala Thr Glu Ser Val Met Asn Leu Ile Asp Glu Thr
                485                 490                 495

Cys Lys Lys Met Asn Lys Glu Lys Leu Gly Gly Ser Leu Phe Ala Lys
```

-continued

```
            500                 505                 510

Pro Phe Val Glu Thr Ala Ile Asn Leu Ala Arg Gln Ser His Cys Thr
        515                 520                 525

Tyr His Asn Gly Asp Ala His Thr Ser Pro Asp Glu Leu Thr Arg Lys
    530                 535                 540

Arg Val Leu Ser Val Ile Thr Glu Pro Ile Leu Pro Phe Glu Arg
545                 550                 555


<210> SEQ ID NO 44
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 44

tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420

acaaaaattt aacgcgaatt ttaacaaaat attaacgttt acaatttcag gtggcacttt    480

tcggggaaat gtgcgcggaa cccctatttg tttatttttc taaatacatt caaatatgta    540

tccgctcatg aattaattct tagaaaaact catcgagcat caaatgaaac tgcaatttat    600

tcatatcagg attatcaata ccatattttt gaaaaagccg tttctgtaat gaaggagaaa    660

actcaccgag gcagttccat aggatggcaa gatcctggta tcggtctgcg attccgactc    720

gtccaacatc aatacaacct attaatttcc cctcgtcaaa aataaggtta tcaagtgaga    780

aatcaccatg agtgacgact gaatccggtg agaatggcaa aagtttatgc atttctttcc    840

agacttgttc aacaggccag ccattacgct cgtcatcaaa atcactcgca tcaaccaaac    900

cgttattcat tcgtgattgc gcctgagcga gacgaaatac gcgatcgctg ttaaaaggac    960

aattacaaac aggaatcgaa tgcaaccggc gcaggaacac tgccagcgca tcaacaatat   1020

tttcacctga atcaggatat tcttctaata cctggaatgc tgttttcccg gggatcgcag   1080

tggtgagtaa ccatgcatca tcaggagtac ggataaaatg cttgatggtc ggaagaggca   1140

taaattccgt cagccagttt agtctgacca tctcatctgt aacatcattg gcaacgctac   1200

ctttgccatg tttcagaaac aactctggcg catcgggctt cccatacaat cgatagattg   1260

tcgcacctga ttgcccgaca ttatcgcgag cccatttata cccatataaa tcagcatcca   1320

tgttggaatt taatcgcggc ctagagcaag acgtttcccg ttgaatatgg ctcataacac   1380

cccttgtatt actgtttatg taagcagaca gttttattgt tcatgaccaa aatcccttaa   1440

cgtgagtttt cgttccactg agcgtcagac cccgtagaaa agatcaaagg atcttcttga   1500

gatccttttt ttctgcgcgt aatctgctgc ttgcaaacaa aaaaaccacc gctaccagcg   1560

gtggtttgtt tgccggatca agagctacca actctttttc cgaaggtaac tggcttcagc   1620

agagcgcaga taccaaatac tgtccttcta gtgtagccgt agttaggcca ccacttcaag   1680

aactctgtag caccgcctac atacctcgct ctgctaatcc tgttaccagt ggctgctgcc   1740

agtggcgata agtcgtgtct taccgggttg gactcaagac gatagttacc ggataaggcg   1800
```

```
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
```

-continued

```
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagca cgtcgctctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
tgaaaccgca aatagcgttt cttgttacat gcgcactaaa ggtatctccg aagaactggc   6480
taccgaaagc gtgatgaatc tgatcgatga aacctggaaa aagatgaaca aggaaaaact   6540
gggtggtagc ctgttcgcga aaccgttcgt ggaaaccgcg atcaacctgg cacgtcaatc   6600
```

```
tcactgcact tatcataacg gcgacgcgca tacctctccg gatgagctga cccgcaaacg   6660

cgttctgtct gtaatcactg aaccgattct gccgtttgaa cgctaaggat ccgaattcga   6720

gctccgtcga caagcttgcg gccgcactcg agcaccacca ccaccaccac tgagatccgg   6780

ctgctaacaa agcccgaaag gaagctgagt tggctgctgc caccgctgag caataactag   6840

cataacccct tggggcctct aaacgggtct tgaggggttt tttgctgaaa ggaggaacta   6900

tatccggat                                                           6909


<210> SEQ ID NO 45
<211> LENGTH: 544
<212> TYPE: PRT
<213> ORGANISM: Populus alba

<400> SEQUENCE: 45

Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320
```

```
Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540
```

<210> SEQ ID NO 46
<211> LENGTH: 47
<212> TYPE: DNA
<213> ORGANISM: Artificial Sequence
<220> FEATURE:
<223> OTHER INFORMATION: Synthetic Construct

<400> SEQUENCE: 46
ggagatatac atatggaagc acgtcgctct gcgaactacg aacctaa 47

<210> SEQ ID NO 47
<211> LENGTH: 47
<212> TYPE: DNA
<213> ORGANISM: Artificial Sequence
<220> FEATURE:
<223> OTHER INFORMATION: Synthetic Construct

<400> SEQUENCE: 47
ttaggttcgt agttcgcaga gcgacgtgct tccatatgta tatctcc 47

<210> SEQ ID NO 48
<211> LENGTH: 20
<212> TYPE: DNA
<213> ORGANISM: Artificial Sequence
<220> FEATURE:
<223> OTHER INFORMATION: Synthetic Construct

<400> SEQUENCE: 48
taatacgact cactataggg 20

<210> SEQ ID NO 49
<211> LENGTH: 19
<212> TYPE: DNA
<213> ORGANISM: Artificial Sequence
<220> FEATURE:
<223> OTHER INFORMATION: Synthetic Construct

<400> SEQUENCE: 49
gctagttatt gctcagcgg 19

<210> SEQ ID NO 50
<211> LENGTH: 22
<212> TYPE: DNA
<213> ORGANISM: Artificial Sequence
<220> FEATURE:
<223> OTHER INFORMATION: Synthetic Construct

<400> SEQUENCE: 50
gcactgtctt tccgtctgct gc 22

<210> SEQ ID NO 51
<211> LENGTH: 20
<212> TYPE: DNA
<213> ORGANISM: Artificial Sequence
<220> FEATURE:
<223> OTHER INFORMATION: Synthetic Construct

<400> SEQUENCE: 51
cttcggcaac gcatggaaat 20

<210> SEQ ID NO 52
<211> LENGTH: 20
<212> TYPE: DNA
<213> ORGANISM: Artificial Sequence
<220> FEATURE:
<223> OTHER INFORMATION: Synthetic Construct

<400> SEQUENCE: 52
ctcgtacagg ctcaggatag 20

<210> SEQ ID NO 53
<211> LENGTH: 20
<212> TYPE: DNA
<213> ORGANISM: Artificial Sequence
<220> FEATURE:
<223> OTHER INFORMATION: Synthetic Construct

<400> SEQUENCE: 53
ttacgtccca acgctcaact 20

<210> SEQ ID NO 54
<211> LENGTH: 36
<212> TYPE: DNA
<213> ORGANISM: Artificial Sequence
<220> FEATURE:
<223> OTHER INFORMATION: Synthetic Construct

<400> SEQUENCE: 54
gcgcgtggtg aaaccaacaa tagcgtttct tgttac 36

<210> SEQ ID NO 55
<211> LENGTH: 41
<212> TYPE: DNA
<213> ORGANISM: Artificial Sequence
<220> FEATURE:
<223> OTHER INFORMATION: Synthetic Construct

<400> SEQUENCE: 55
agatgaacaa ggaaaaactg agtggtagcc tgttcgcgaa a 41

<210> SEQ ID NO 56
<211> LENGTH: 37
<212> TYPE: DNA
<213> ORGANISM: Artificial Sequence
<220> FEATURE:
<223> OTHER INFORMATION: Synthetic Construct

<400> SEQUENCE: 56
gaaaaactgg gtggtagccc gttcgcgaaa ccgttcg 37

<210> SEQ ID NO 57
<211> LENGTH: 37
<212> TYPE: DNA
<213> ORGANISM: Artificial Sequence
<220> FEATURE:
<223> OTHER INFORMATION: Synthetic Construct

<400> SEQUENCE: 57
gttctgtctg taatctgcga accgattctg ccgtttg 37

<210> SEQ ID NO 58
<211> LENGTH: 44
<212> TYPE: DNA
<213> ORGANISM: Artificial Sequence
<220> FEATURE:
<223> OTHER INFORMATION: Synthetic Construct

<400> SEQUENCE: 58
gaacaaggaa aaactgagtg gtagcccgtt cgcgaaaccg ttcg 44

<210> SEQ ID NO 59
<211> LENGTH: 31
<212> TYPE: DNA
<213> ORGANISM: Artificial Sequence
<220> FEATURE:
<223> OTHER INFORMATION: Synthetic Construct

<400> SEQUENCE: 59
gaaaaactga gtggtagcct gttcgcgaaa c 31

<210> SEQ ID NO 60
<211> LENGTH: 31
<212> TYPE: DNA
<213> ORGANISM: Artificial Sequence
<220> FEATURE:
<223> OTHER INFORMATION: Synthetic Construct

<400> SEQUENCE: 60
aggctaccac tcagtttttc cttgttcatc t 31

<210> SEQ ID NO 61
<211> LENGTH: 37
<212> TYPE: DNA
<213> ORGANISM: Artificial Sequence
<220> FEATURE:
<223> OTHER INFORMATION: Synthetic Construct

<400> SEQUENCE: 61
gttctgtctg taatctttga accgattctg ccgtttg 37

<210> SEQ ID NO 62
<211> LENGTH: 29
<212> TYPE: DNA
<213> ORGANISM: Artificial Sequence
<220> FEATURE:
<223> OTHER INFORMATION: Synthetic Construct

<400> SEQUENCE: 62
cggttcaaag attacagaca gaacgcgtt 29

<210> SEQ ID NO 63
<211> LENGTH: 559
<212> TYPE: PRT
<213> ORGANISM: Artificial Sequence
<220> FEATURE:
<223> OTHER INFORMATION: Synthetic Construct

<400> SEQUENCE: 63

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335
```

```
Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 64
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 64

```
tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420

acaaaaattt aacgcgaatt ttaacaaaat attaacgttt acaatttcag gtggcacttt    480

tcggggaaat gtgcgcggaa cccctatttg tttatttttc taaatacatt caaatatgta    540

tccgctcatg aattaattct tagaaaaact catcgagcat caaatgaaac tgcaatttat    600

tcatatcagg attatcaata ccatattttt gaaaaagccg tttctgtaat gaaggagaaa    660

actcaccgag gcagttccat aggatggcaa gatcctggta tcggtctgcg attccgactc    720

gtccaacatc aatacaacct attaatttcc cctcgtcaaa aataaggtta tcaagtgaga    780

aatcaccatg agtgacgact gaatccggtg agaatggcaa aagtttatgc atttctttcc    840
```

-continued

```
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
```

-continued

```
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
```

-continued

```
gccactgcat cgccgtactc agcgtctgga agcagtatgg tctatcgagg cctaccgtaa   5700

aaaggaggac gcgaatcagg ttctgctgga gctggcaatt ctggattaca acatgatcca   5760

gtctgtatac cagcgtgatc tgcgtgaaac gtcccgttgg tggcgtcgtg tgggtctggc   5820

gaccaaactg cactttgctc gtgaccgcct gattgagagc ttctactggg ccgtgggtgt   5880

agcattcgaa ccgcaatact ccgactgccg taactccgtc gcaaaaatgt tttctttcgt   5940

aaccattatc gacgatatct acgatgtata cggcaccctg gacgaactgg agctgtttac   6000

tgatgcagtt gagcgttggg acgtaaacgc catcaacgac ctgccggatt acatgaaact   6060

gtgctttctg gctctgtata acactattaa cgaaatcgcc tacgacaacc tgaaagataa   6120

aggtgagaac atcctgccgt atctgaccaa agcctgggct gacctgtgca acgctttcct   6180

gcaagaagcc aagtggctgt acaacaaatc tactccgacc tttgacgact acttcggcaa   6240

cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccgca aatagcgttt cttgttacat gcgcactaaa ggtatctccg aagaactggc   6480

taccgaaagc gtgatgaatc tgatcgatga aacctggaaa aagatgaaca aggaaaaact   6540

gggtggtagc ctgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatcactg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

<210> SEQ ID NO 65
<211> LENGTH: 559
<212> TYPE: PRT
<213> ORGANISM: Artificial Sequence
<220> FEATURE:
<223> OTHER INFORMATION: Synthetic Construct

<400> SEQUENCE: 65

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
```

```
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Asn Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

Glu Asn Leu Tyr Phe Gln Gly Leu Glu His His His His His His
545                 550                 555

<210> SEQ ID NO 66
<211> LENGTH: 6887
```

<212> TYPE: DNA
<213> ORGANISM: Artificial Sequence
<220> FEATURE:
<223> OTHER INFORMATION: Synthetic Construct

<400> SEQUENCE: 66
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560
gtggtttgtt tgccggatca agagctacca actctttttc cgaaggtaac tggcttcagc 1620
agagcgcaga taccaaatac tgtccttcta gtgtagccgt agttaggcca ccacttcaag 1680
aactctgtag caccgcctac atacctcgct ctgctaatcc tgttaccagt ggctgctgcc 1740
agtggcgata agtcgtgtct taccgggttg gactcaagac gatagttacc ggataaggcg 1800
cagcggtcgg gctgaacggg gggttcgtgc acacagccca gcttggagcg aacgacctac 1860
accgaactga gatacctaca gcgtgagcta tgagaaagcg ccacgcttcc cgaagggaga 1920
aaggcggaca ggtatccggt aagcggcagg gtcggaacag gagagcgcac gagggagctt 1980
ccagggggaa acgcctggta tctttatagt cctgtcgggt ttcgccacct ctgacttgag 2040
cgtcgatttt tgtgatgctc gtcagggggg cggagcctat ggaaaaacgc cagcaacgcg 2100
gcctttttac ggttcctggc cttttgctgg ccttttgctc acatgttctt tcctgcgtta 2160
tcccctgatt ctgtggataa ccgtattacc gcctttgagt gagctgatac cgctcgccgc 2220

```
agccgaacga ccgagcgcag cgagtcagtg agcgaggaag cggaagagcg cctgatgcgg    2280

tattttctcc ttacgcatct gtgcggtatt tcacaccgca tatatggtgc actctcagta    2340

caatctgctc tgatgccgca tagttaagcc agtatacact ccgctatcgc tacgtgactg    2400

ggtcatggct gcgccccgac acccgccaac acccgctgac gcgccctgac gggcttgtct    2460

gctcccggca tccgcttaca gacaagctgt gaccgtctcc gggagctgca tgtgtcagag    2520

gttttcaccg tcatcaccga aacgcgcgag gcagctgcgg taaagctcat cagcgtggtc    2580

gtgaagcgat tcacagatgt ctgcctgttc atccgcgtcc agctcgttga gtttctccag    2640

aagcgttaat gtctggcttc tgataaagcg ggccatgtta agggcggttt tttcctgttt    2700

ggtcactgat gcctccgtgt aagggggatt tctgttcatg ggggtaatga taccgatgaa    2760

acgagagagg atgctcacga tacgggttac tgatgatgaa catgcccggt tactggaacg    2820

ttgtgagggt aaacaactgg cggtatggat gcggcgggac cagagaaaaa tcactcaggg    2880

tcaatgccag cgcttcgtta atacagatgt aggtgttcca cagggtagcc agcagcatcc    2940

tgcgatgcag atccggaaca taatggtgca gggcgctgac ttccgcgttt ccagacttta    3000

cgaaacacgg aaaccgaaga ccattcatgt tgttgctcag gtcgcagacg ttttgcagca    3060

gcagtcgctt cacgttcgct cgcgtatcgg tgattcattc tgctaaccag taaggcaacc    3120

ccgccagcct agccgggtcc tcaacgacag gagcacgatc atgcgcaccc gtggggccgc    3180

catgccggcg ataatggcct gcttctcgcc gaaacgtttg gtggcgggac cagtgacgaa    3240

ggcttgagcg agggcgtgca agattccgaa taccgcaagc gacaggccga tcatcgtcgc    3300

gctccagcga aagcggtcct cgccgaaaat gacccagagc gctgccggca cctgtcctac    3360

gagttgcatg ataaagaaga cagtcataag tgcggcgacg atagtcatgc cccgcgccca    3420

ccggaaggag ctgactgggt tgaaggctct caagggcatc ggtcgagatc ccggtgccta    3480

atgagtgagc taacttacat taattgcgtt gcgctcactg cccgctttcc agtcgggaaa    3540

cctgtcgtgc cagctgcatt aatgaatcgg ccaacgcgcg gggagaggcg gtttgcgtat    3600

tgggcgccag ggtggttttt cttttcacca gtgagacggg caacagctga ttgcccttca    3660

ccgcctggcc ctgagagagt tgcagcaagc ggtccacgct ggtttgcccc agcaggcgaa    3720

aatcctgttt gatggtggtt aacggcggga tataacatga gctgtcttcg gtatcgtcgt    3780

atcccactac cgagatatcc gcaccaacgc gcagcccgga ctcggtaatg gcgcgcattg    3840

cgcccagcgc catctgatcg ttggcaacca gcatcgcagt gggaacgatg ccctcattca    3900

gcatttgcat ggtttgttga aaaccggaca tggcactcca gtcgccttcc cgttccgcta    3960

tcggctgaat ttgattgcga gtgagatatt tatgccagcc agccagacgc agacgcgccg    4020

agacagaact taatgggccc gctaacagcg cgatttgctg gtgacccaat gcgaccagat    4080

gctccacgcc cagtcgcgta ccgtcttcat gggagaaaat aatactgttg atgggtgtct    4140

ggtcagagac atcaagaaat aacgccggaa cattagtgca ggcagcttcc acagcaatgg    4200

catcctggtc atccagcgga tagttaatga tcagcccact gacgcgttgc gcgagaagat    4260

tgtgcaccgc cgctttacag gcttcgacgc cgcttcgttc taccatcgac accaccacgc    4320

tggcacccag ttgatcggcg cgagatttaa tcgccgcgac aatttgcgac ggcgcgtgca    4380

gggccagact ggaggtggca acgccaatca gcaacgactg tttgcccgcc agttgttgtg    4440

ccacgcggtt gggaatgtaa ttcagctccg ccatcgccgc ttccactttt tcccgcgttt    4500

tcgcagaaac gtggctggcc tggttcacca cgcgggaaac ggtctgataa gagacaccgg    4560

catactctgc gacatcgtat aacgttactg gtttcacatt caccaccctg aattgactct    4620
```

-continued

```
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
tgaaaccaac aatagcgttt cttgttacat gcgcactaaa ggtatctccg aagaactggc   6480
taccgaaagc gtgatgaatc tgatcgatga aacctggaaa aagatgaaca aggaaaaact   6540
gggtggtagc ctgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatcactg aaccgattct gccgtttgaa cgcgaaaacc tgtattttca   6720
gggcctcgag caccaccacc accaccactg agatccggct gctaacaaag cccgaaagga   6780
agctgagttg gctgctgcca ccgctgagca ataactagca taaccccttg gggcctctaa   6840
acgggtcttg aggggttttt tgctgaaagg aggaactata tccggat                 6887
```

<210> SEQ ID NO 67
<211> LENGTH: 559

```
<212> TYPE: PRT
<213> ORGANISM: Artificial Sequence
<220> FEATURE:
<223> OTHER INFORMATION: Synthetic Construct

<400> SEQUENCE: 67

Met Glu Ala Arg Arg Ser Ala Asn Tyr Glu Pro Asn Ser Trp Asp Tyr
 1               5                   10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
```

```
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Ser Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 68
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 68

```
tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420

acaaaaattt aacgcgaatt ttaacaaaat attaacgttt acaatttcag gtggcacttt    480

tcggggaaat gtgcgcggaa cccctatttg tttatttttc taaatacatt caaatatgta    540

tccgctcatg aattaattct tagaaaaact catcgagcat caaatgaaac tgcaatttat    600

tcatatcagg attatcaata ccatattttt gaaaaagccg tttctgtaat gaaggagaaa    660

actcaccgag gcagttccat aggatggcaa gatcctggta tcggtctgcg attccgactc    720

gtccaacatc aatacaacct attaatttcc cctcgtcaaa aataaggtta tcaagtgaga    780

aatcaccatg agtgacgact gaatccggtg agaatggcaa aagtttatgc atttctttcc    840

agacttgttc aacaggccag ccattacgct cgtcatcaaa atcactcgca tcaaccaaac    900

cgttattcat tcgtgattgc gcctgagcga gacgaaatac gcgatcgctg ttaaaaggac    960

aattacaaac aggaatcgaa tgcaaccggc gcaggaacac tgccagcgca tcaacaatat   1020

tttcacctga atcaggatat tcttctaata cctggaatgc tgttttcccg gggatcgcag   1080

tggtgagtaa ccatgcatca tcaggagtac ggataaaatg cttgatggtc ggaagaggca   1140
```

-continued

```
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
```

-continued

```
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
```

-continued

```
aaccattatc gacgatatct acgatgtata cggcaccctg gacgaactgg agctgtttac   6000

tgatgcagtt gagcgttggg acgtaaacgc catcaacgac ctgccggatt acatgaaact   6060

gtgctttctg gctctgtata acactattaa cgaaatcgcc tacgacaacc tgaaagataa   6120

aggtgagaac atcctgccgt atctgaccaa agcctgggct gacctgtgca acgctttcct   6180

gcaagaagcc aagtggctgt acaacaaatc tactccgacc tttgacgact acttcggcaa   6240

cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccgca aatagcgttt cttgttacat gcgcactaaa ggtatctccg aagaactggc   6480

taccgaaagc gtgatgaatc tgatcgatga aacctggaaa aagatgaaca aggaaaaact   6540

gagtggtagc ctgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatcactg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                6887
```

<210> SEQ ID NO 69
<211> LENGTH: 559
<212> TYPE: PRT
<213> ORGANISM: Artificial Sequence
<220> FEATURE:
<223> OTHER INFORMATION: Synthetic Construct

<400> SEQUENCE: 69

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205
```

```
Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Pro Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

Glu Asn Leu Tyr Phe Gln Gly Leu Glu His His His His His His
545                 550                 555

<210> SEQ ID NO 70
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 70

tggcgaatgg gacgcgccct gtagcggcgc attaagcgcg gcgggtgtgg tggttacgcg      60

cagcgtgacc gctacacttg ccagcgccct agcgcccgct cctttcgctt tcttcccttc     120
```

```
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
```

-continued gttttcaccg tcatcaccga aacgcgcgag gcagctgcgg taaagctcat cagcgtggtc 2580
gtgaagcgat tcacagatgt ctgcctgttc atccgcgtcc agctcgttga gtttctccag 2640
aagcgttaat gtctggcttc tgataaagcg ggccatgtta agggcggttt tttcctgttt 2700
ggtcactgat gcctccgtgt aagggggatt tctgttcatg gggtaatga taccgatgaa 2760 acgagagagg atgctcacga tacgggttac tgatgatgaa catgcccggt tactggaacg 2820
ttgtgagggt aaacaactgg cggtatggat gcggcgggac cagagaaaaa tcactcaggg 2880
tcaatgccag cgcttcgtta atacagatgt aggtgttcca cagggtagcc agcagcatcc 2940
tgcgatgcag atccggaaca taatggtgca gggcgctgac ttccgcgttt ccagacttta 3000
cgaaacacgg aaaccgaaga ccattcatgt tgttgctcag gtcgcagacg ttttgcagca 3060
gcagtcgctt cacgttcgct cgcgtatcgg tgattcattc tgctaaccag taaggcaacc 3120
ccgccagcct agccgggtcc tcaacgacag gagcacgatc atgcgcaccc gtggggccgc 3180
catgccggcg ataatggcct gcttctcgcc gaaacgtttg gtggcgggac cagtgacgaa 3240
ggcttgagcg agggcgtgca agattccgaa taccgcaagc gacaggccga tcatcgtcgc 3300
gctccagcga aagcggtcct cgccgaaaat gacccagagc gctgccggca cctgtcctac 3360
gagttgcatg ataaagaaga cagtcataag tgcggcgacg atagtcatgc cccgcgccca 3420
ccggaaggag ctgactgggt tgaaggctct caagggcatc ggtcgagatc ccggtgccta 3480
atgagtgagc taacttacat taattgcgtt gcgctcactg cccgctttcc agtcgggaaa 3540
cctgtcgtgc cagctgcatt aatgaatcgg ccaacgcgcg gggagaggcg gtttgcgtat 3600
tgggcgccag ggtggttttt cttttcacca gtgagacggg caacagctga ttgcccttca 3660
ccgcctggcc ctgagagagt tgcagcaagc ggtccacgct ggtttgcccc agcaggcgaa 3720
aatcctgttt gatggtggtt aacggcggga tataacatga gctgtcttcg gtatcgtcgt 3780
atcccactac cgagatatcc gcaccaacgc gcagcccgga ctcggtaatg gcgcgcattg 3840
cgcccagcgc catctgatcg ttggcaacca gcatcgcagt gggaacgatg ccctcattca 3900
gcatttgcat ggtttgttga aaaccggaca tggcactcca gtcgccttcc cgttccgcta 3960
tcggctgaat ttgattgcga gtgagatatt tatgccagcc agccagacgc agacgcgccg 4020
agacagaact taatgggccc gctaacagcg cgatttgctg gtgacccaat gcgaccagat 4080
gctccacgcc cagtcgcgta ccgtcttcat gggagaaaat aatactgttg atgggtgtct 4140
ggtcagagac atcaagaaat aacgccggaa cattagtgca ggcagcttcc acagcaatgg 4200
catcctggtc atccagcgga tagttaatga tcagcccact gacgcgttgc gcgagaagat 4260
tgtgcaccgc cgctttacag gcttcgacgc cgcttcgttc taccatcgac accaccacgc 4320
tggcacccag ttgatcggcg cgagatttaa tcgccgcgac aatttgcgac ggcgcgtgca 4380
gggccagact ggaggtggca acgccaatca gcaacgactg tttgcccgcc agttgttgtg 4440
ccacgcggtt gggaatgtaa ttcagctccg ccatcgccgc ttccactttt tcccgcgttt 4500
tcgcagaaac gtggctggcc tggttcacca cgcgggaaac ggtctgataa gagacaccgg 4560
catactctgc gacatcgtat aacgttactg gtttcacatt caccaccctg aattgactct 4620
cttccgggcg ctatcatgcc ataccgcgaa aggttttgcg ccattcgatg gtgtccggga 4680
tctcgacgct ctcccttatg cgactcctgc attaggaagc agcccagtag taggttgagg 4740
ccgttgagca ccgccgccgc aaggaatggt gcatgcaagg agatggcgcc caacagtccc 4800
ccggccacgg ggcctgccac catacccacg ccgaaacaag cgctcatgag cccgaagtgg 4860
cgagcccgat cttccccatc ggtgatgtcg gcgatatagg cgccagcaac cgcacctgtg 4920

-continued

```
gcgccggtga tgccggccac gatgcgtccg gcgtagagga tcgagatctc gatcccgcga   4980

aattaatacg actcactata ggggaattgt gagcggataa caattcccct ctagaaataa   5040

ttttgtttaa ctttaagaag gagatataca tatggaagct cgtcgttctg cgaactacga   5100

acctaacagc tgggactatg attacctgct gtcctccgac acggacgagt ccatcgaagt   5160

atacaaagac aaagcgaaaa agctggaagc cgaagttcgt cgcgagatta ataacgaaaa   5220

agcagaattt ctgaccctgc tggaactgat tgacaacgtc cagcgcctgg gcctgggtta   5280

ccgtttcgag tctgatatcc gtggtgcgct ggatcgcttc gtttcctccg gcggcttcga   5340

tgcggtaacc aagacttccc tgcacggtac ggcactgtct ttccgtctgc tgcgtcaaca   5400

cggttttgag gtttctcagg aagcgttcag cggcttcaaa gaccaaaacg gcaacttcct   5460

ggagaacctg aaggaagata tcaaagctat cctgagcctg tacgaggcca gcttcctggc   5520

tctggaaggc gaaaacatcc tggacgaggc gaaggttttc gcaatctctc atctgaaaga   5580

actgtctgaa gaaaagatcg gtaaagagct ggcagaacag gtgaaccatg cactggaact   5640

gccactgcat cgccgtactc agcgtctgga agcagtatgg tctatcgagg cctaccgtaa   5700

aaaggaggac gcgaatcagg ttctgctgga gctggcaatt ctggattaca acatgatcca   5760

gtctgtatac cagcgtgatc tgcgtgaaac gtcccgttgg tggcgtcgtg tgggtctggc   5820

gaccaaactg cactttgctc gtgaccgcct gattgagagc ttctactggg ccgtgggtgt   5880

agcattcgaa ccgcaatact ccgactgccg taactccgtc gcaaaaatgt tttctttcgt   5940

aaccattatc gacgatatct acgatgtata cggcaccctg gacgaactgg agctgtttac   6000

tgatgcagtt gagcgttggg acgtaaacgc catcaacgac ctgccggatt acatgaaact   6060

gtgctttctg gctctgtata acactattaa cgaaatcgcc tacgacaacc tgaaagataa   6120

aggtgagaac atcctgccgt atctgaccaa agcctgggct gacctgtgca acgctttcct   6180

gcaagaagcc aagtggctgt acaacaaatc tactccgacc tttgacgact acttcggcaa   6240

cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccgca aatagcgttt cttgttacat gcgcactaaa ggtatctccg aagaactggc   6480

taccgaaagc gtgatgaatc tgatcgatga aacctggaaa aagatgaaca aggaaaaact   6540

gggtggtagc ccgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatcactg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

<210> SEQ ID NO 71
<211> LENGTH: 559
<212> TYPE: PRT
<213> ORGANISM: Artificial Sequence
<220> FEATURE:
<223> OTHER INFORMATION: Synthetic Construct

<400> SEQUENCE: 71

```
Met Glu Ala Arg Arg Ser Ala Asn Tyr Glu Pro Asn Ser Trp Asp Tyr
 1               5                  10                  15
```

-continued

```
Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445
```

```
Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Cys Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 72
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 72

```
tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420

acaaaaattt aacgcgaatt ttaacaaaat attaacgttt acaatttcag gtggcacttt    480

tcggggaaat gtgcgcggaa cccctatttg tttatttttc taaatacatt caaatatgta    540

tccgctcatg aattaattct tagaaaaact catcgagcat caaatgaaac tgcaatttat    600

tcatatcagg attatcaata ccatattttt gaaaaagccg tttctgtaat gaaggagaaa    660

actcaccgag gcagttccat aggatggcaa gatcctggta tcggtctgcg attccgactc    720

gtccaacatc aatacaacct attaatttcc cctcgtcaaa aataaggtta tcaagtgaga    780

aatcaccatg agtgacgact gaatccggtg agaatggcaa aagtttatgc atttctttcc    840

agacttgttc aacaggccag ccattacgct cgtcatcaaa atcactcgca tcaaccaaac    900

cgttattcat tcgtgattgc gcctgagcga gacgaaatac gcgatcgctg ttaaaaggac    960

aattacaaac aggaatcgaa tgcaaccggc gcaggaacac tgccagcgca tcaacaatat   1020

tttcacctga atcaggatat tcttctaata cctggaatgc tgttttcccg gggatcgcag   1080

tggtgagtaa ccatgcatca tcaggagtac ggataaaatg cttgatggtc ggaagaggca   1140

taaattccgt cagccagttt agtctgacca tctcatctgt aacatcattg gcaacgctac   1200

ctttgccatg tttcagaaac aactctggcg catcgggctt cccatacaat cgatagattg   1260

tcgcacctga ttgcccgaca ttatcgcgag cccatttata cccatataaa tcagcatcca   1320

tgttggaatt taatcgcggc ctagagcaag acgtttcccg ttgaatatgg ctcataacac   1380

cccttgtatt actgtttatg taagcagaca gttttattgt tcatgaccaa aatcccttaa   1440
```

-continued

```
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
```

-continued

```
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
```

```
cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccgca aatagcgttt cttgttacat gcgcactaaa ggtatctccg aagaactggc   6480

taccgaaagc gtgatgaatc tgatcgatga aacctggaaa aagatgaaca aggaaaaact   6540

gggtggtagc ctgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatctgcg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

<210> SEQ ID NO 73
<211> LENGTH: 559
<212> TYPE: PRT
<213> ORGANISM: Artificial Sequence
<220> FEATURE:
<223> OTHER INFORMATION: Synthetic Construct

<400> SEQUENCE: 73

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255
```

```
Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Asn Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Ser Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 74
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 74

```
tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420
```

```
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
```

-continued

```
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
```

```
agcagaattt ctgaccctgc tggaactgat tgacaacgtc cagcgcctgg gcctgggtta   5280

ccgtttcgag tctgatatcc gtggtgcgct ggatcgcttc gtttcctccg gcggcttcga   5340

tgcggtaacc aagacttccc tgcacggtac ggcactgtct ttccgtctgc tgcgtcaaca   5400

cggttttgag gtttctcagg aagcgttcag cggcttcaaa gaccaaaacg gcaacttcct   5460

ggagaacctg aaggaagata tcaaagctat cctgagcctg tacgaggcca gcttcctggc   5520

tctggaaggc gaaaacatcc tggacgaggc gaaggttttc gcaatctctc atctgaaaga   5580

actgtctgaa gaaaagatcg gtaaagagct ggcagaacag gtgaaccatg cactggaact   5640

gccactgcat cgccgtactc agcgtctgga agcagtatgg tctatcgagg cctaccgtaa   5700

aaaggaggac gcgaatcagg ttctgctgga gctggcaatt ctggattaca acatgatcca   5760

gtctgtatac cagcgtgatc tgcgtgaaac gtcccgttgg tggcgtcgtg tgggtctggc   5820

gaccaaactg cactttgctc gtgaccgcct gattgagagc ttctactggg ccgtgggtgt   5880

agcattcgaa ccgcaatact ccgactgccg taactccgtc gcaaaaatgt tttctttcgt   5940

aaccattatc gacgatatct acgatgtata cggcaccctg gacgaactgg agctgtttac   6000

tgatgcagtt gagcgttggg acgtaaacgc catcaacgac ctgccggatt acatgaaact   6060

gtgctttctg gctctgtata acactattaa cgaaatcgcc tacgacaacc tgaaagataa   6120

aggtgagaac atcctgccgt atctgaccaa agcctgggct gacctgtgca acgctttcct   6180

gcaagaagcc aagtggctgt acaacaaatc tactccgacc tttgacgact acttcggcaa   6240

cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccaac aatagcgttt cttgttacat gcgcactaaa ggtatctccg aagaactggc   6480

taccgaaagc gtgatgaatc tgatcgatga aacctggaaa aagatgaaca aggaaaaact   6540

gagtggtagc ctgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatcactg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

<210> SEQ ID NO 75
<211> LENGTH: 559
<212> TYPE: PRT
<213> ORGANISM: Artificial Sequence
<220> FEATURE:
<223> OTHER INFORMATION: Synthetic Construct

<400> SEQUENCE: 75

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
```

```
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Asn Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Pro Phe Ala
                485                 490                 495
```

```
Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

Glu Asn Leu Tyr Phe Gln Gly Leu Glu His His His His His His
545                 550                 555


<210> SEQ ID NO 76
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 76

tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420

acaaaaattt aacgcgaatt ttaacaaaat attaacgttt acaatttcag gtggcacttt    480

tcggggaaat gtgcgcggaa cccctatttg tttatttttc taaatacatt caaatatgta    540

tccgctcatg aattaattct tagaaaaact catcgagcat caaatgaaac tgcaatttat    600

tcatatcagg attatcaata ccatattttt gaaaaagccg tttctgtaat gaaggagaaa    660

actcaccgag gcagttccat aggatggcaa gatcctggta tcggtctgcg attccgactc    720

gtccaacatc aatacaacct attaatttcc cctcgtcaaa aataaggtta tcaagtgaga    780

aatcaccatg agtgacgact gaatccggtg agaatggcaa aagtttatgc atttctttcc    840

agacttgttc aacaggccag ccattacgct cgtcatcaaa atcactcgca tcaaccaaac    900

cgttattcat tcgtgattgc gcctgagcga gacgaaatac gcgatcgctg ttaaaaggac    960

aattacaaac aggaatcgaa tgcaaccggc gcaggaacac tgccagcgca tcaacaatat   1020

tttcacctga atcaggatat tcttctaata cctggaatgc tgttttcccg gggatcgcag   1080

tggtgagtaa ccatgcatca tcaggagtac ggataaaatg cttgatggtc ggaagaggca   1140

taaattccgt cagccagttt agtctgacca tctcatctgt aacatcattg gcaacgctac   1200

ctttgccatg tttcagaaac aactctggcg catcgggctt cccatacaat cgatagattg   1260

tcgcacctga ttgcccgaca ttatcgcgag cccatttata cccatataaa tcagcatcca   1320

tgttggaatt taatcgcggc ctagagcaag acgtttcccg ttgaatatgg ctcataacac   1380

cccttgtatt actgtttatg taagcagaca gttttattgt tcatgaccaa aatcccttaa   1440

cgtgagtttt cgttccactg agcgtcagac cccgtagaaa agatcaaagg atcttcttga   1500

gatccttttt ttctgcgcgt aatctgctgc ttgcaaacaa aaaaaccacc gctaccagcg   1560

gtggtttgtt tgccggatca agagctacca actctttttc cgaaggtaac tggcttcagc   1620

agagcgcaga taccaaatac tgtccttcta gtgtagccgt agttaggcca ccacttcaag   1680

aactctgtag caccgcctac atacctcgct ctgctaatcc tgttaccagt ggctgctgcc   1740
```

-continued

```
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
```

-continued

```
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
tgaaaccaac aatagcgttt cttgttacat gcgcactaaa ggtatctccg aagaactggc   6480
taccgaaagc gtgatgaatc tgatcgatga aacctggaaa aagatgaaca aggaaaaact   6540
```

```
gggtggtagc ccgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatcactg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

<210> SEQ ID NO 77
<211> LENGTH: 559
<212> TYPE: PRT
<213> ORGANISM: Artificial Sequence
<220> FEATURE:
<223> OTHER INFORMATION: Synthetic Construct

<400> SEQUENCE: 77

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
```

```
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Asn Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Cys Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 78
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 78

```
tggcgaatgg gacgcgccct gtagcggcgc attaagcgcg gcgggtgtgg tggttacgcg      60

cagcgtgacc gctacacttg ccagcgccct agcgcccgct cctttcgctt tcttcccttc     120

ctttctcgcc acgttcgccg gctttccccg tcaagctcta aatcgggggc tccctttagg     180

gttccgattt agtgctttac ggcacctcga ccccaaaaaa cttgattagg gtgatggttc     240

acgtagtggg ccatcgccct gatagacggt ttttcgccct ttgacgttgg agtccacgtt     300

ctttaatagt ggactcttgt tccaaactgg aacaacactc aaccctatct cggtctattc     360

ttttgattta taagggattt tgccgatttc ggcctattgg ttaaaaaatg agctgattta     420

acaaaaattt aacgcgaatt ttaacaaaat attaacgttt acaatttcag gtggcacttt     480

tcggggaaat gtgcgcggaa cccctatttg tttatttttc taaatacatt caaatatgta     540

tccgctcatg aattaattct tagaaaaact catcgagcat caaatgaaac tgcaatttat     600

tcatatcagg attatcaata ccatattttt gaaaaagccg tttctgtaat gaaggagaaa     660

actcaccgag gcagttccat aggatggcaa gatcctggta tcggtctgcg attccgactc     720
```

-continued

```
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
```

```
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
```

```
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt ttctttcgt    5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
tgaaaccaac aatagcgttt cttgttacat gcgcactaaa ggtatctccg aagaactggc   6480
taccgaaagc gtgatgaatc tgatcgatga aacctggaaa aagatgaaca aggaaaaact   6540
gggtggtagc ctgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatctgcg aaccgattct gccgtttgaa cgcgaaaacc tgtattttca   6720
gggcctcgag caccaccacc accaccactg agatccggct gctaacaaag cccgaaagga   6780
agctgagttg gctgctgcca ccgctgagca ataactagca taaccccttg ggcctctaa    6840
acgggtcttg aggggttttt tgctgaaagg aggaactata tccggat                 6887
```

```
<210> SEQ ID NO 79
<211> LENGTH: 559
<212> TYPE: PRT
<213> ORGANISM: Artificial Sequence
<220> FEATURE:
<223> OTHER INFORMATION: Synthetic Construct

<400> SEQUENCE: 79

Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125
```

```
Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Asn Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Ser Gly Ser Pro Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

Glu Asn Leu Tyr Phe Gln Gly Leu Glu His His His His His His
```

-continued 545 550 555

<210> SEQ ID NO 80
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 80
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560
gtggtttgtt tgccggatca agagctacca actctttttc cgaaggtaac tggcttcagc 1620
agagcgcaga taccaaatac tgtccttcta gtgtagccgt agttaggcca ccacttcaag 1680
aactctgtag caccgcctac atacctcgct ctgctaatcc tgttaccagt ggctgctgcc 1740
agtggcgata agtcgtgtct taccgggttg gactcaagac gatagttacc ggataaggcg 1800
cagcggtcgg gctgaacggg gggttcgtgc acacagccca gcttggagcg aacgacctac 1860
accgaactga gatacctaca gcgtgagcta tgagaaagcg ccacgcttcc cgaagggaga 1920
aaggcggaca ggtatccggt aagcggcagg gtcggaacag gagagcgcac gagggagctt 1980
ccagggggaa acgcctggta tctttatagt cctgtcgggt ttcgccacct ctgacttgag 2040

-continued cgtcgatttt tgtgatgctc gtcagggggg cggagcctat ggaaaaacgc cagcaacgcg 2100
gcctttttac ggttcctggc cttttgctgg ccttttgctc acatgttctt tcctgcgtta 2160
tcccctgatt ctgtggataa ccgtattacc gcctttgagt gagctgatac cgctcgccgc 2220
agccgaacga ccgagcgcag cgagtcagtg agcgaggaag cggaagagcg cctgatgcgg 2280
tattttctcc ttacgcatct gtgcggtatt tcacaccgca tatatggtgc actctcagta 2340
caatctgctc tgatgccgca tagttaagcc agtatacact ccgctatcgc tacgtgactg 2400
ggtcatggct gcgccccgac acccgccaac acccgctgac gcgccctgac gggcttgtct 2460
gctcccggca tccgcttaca gacaagctgt gaccgtctcc gggagctgca tgtgtcagag 2520
gttttcaccg tcatcaccga aacgcgcgag gcagctgcgg taaagctcat cagcgtggtc 2580
gtgaagcgat tcacagatgt ctgcctgttc atccgcgtcc agctcgttga gtttctccag 2640
aagcgttaat gtctggcttc tgataaagcg ggccatgtta agggcggttt tttcctgttt 2700
ggtcactgat gcctccgtgt aagggggatt tctgttcatg gggtaatga taccgatgaa 2760
acgagagagg atgctcacga tacgggttac tgatgatgaa catgcccggt tactggaacg 2820
ttgtgagggt aaacaactgg cggtatggat gcggcgggac cagagaaaaa tcactcaggg 2880
tcaatgccag cgcttcgtta atacagatgt aggtgttcca cagggtagcc agcagcatcc 2940
tgcgatgcag atccggaaca taatggtgca gggcgctgac ttccgcgttt ccagacttta 3000
cgaaacacgg aaaccgaaga ccattcatgt tgttgctcag gtcgcagacg ttttgcagca 3060
gcagtcgctt cacgttcgct cgcgtatcgg tgattcattc tgctaaccag taaggcaacc 3120
ccgccagcct agccgggtcc tcaacgacag gagcacgatc atgcgcaccc gtggggccgc 3180
catgccggcg ataatggcct gcttctcgcc gaaacgtttg gtggcgggac cagtgacgaa 3240
ggcttgagcg agggcgtgca agattccgaa taccgcaagc gacaggccga tcatcgtcgc 3300
gctccagcga aagcggtcct cgccgaaaat gacccagagc gctgccggca cctgtcctac 3360
gagttgcatg ataaagaaga cagtcataag tgcggcgacg atagtcatgc cccgcgccca 3420
ccggaaggag ctgactgggt tgaaggctct caagggcatc ggtcgagatc ccggtgccta 3480
atgagtgagc taacttacat taattgcgtt gcgctcactg cccgctttcc agtcgggaaa 3540
cctgtcgtgc cagctgcatt aatgaatcgg ccaacgcgcg gggagaggcg gtttgcgtat 3600
tgggcgccag ggtggttttt cttttcacca gtgagacggg caacagctga ttgcccttca 3660
ccgcctggcc ctgagagagt tgcagcaagc ggtccacgct ggtttgcccc agcaggcgaa 3720
aatcctgttt gatggtggtt aacggcggga tataacatga gctgtcttcg gtatcgtcgt 3780
atcccactac cgagatatcc gcaccaacgc gcagcccgga ctcggtaatg gcgcgcattg 3840
cgcccagcgc catctgatcg ttggcaacca gcatcgcagt gggaacgatg ccctcattca 3900
gcatttgcat ggtttgttga aaaccggaca tggcactcca gtcgccttcc cgttccgcta 3960
tcggctgaat ttgattgcga gtgagatatt tatgccagcc agccagacgc agacgcgccg 4020
agacagaact taatgggccc gctaacagcg cgatttgctg gtgacccaat gcgaccagat 4080
gctccacgcc cagtcgcgta ccgtcttcat gggagaaaat aatactgttg atgggtgtct 4140
ggtcagagac atcaagaaat aacgccggaa cattagtgca ggcagcttcc acagcaatgg 4200
catcctggtc atccagcgga tagttaatga tcagcccact gacgcgttgc gcgagaagat 4260
tgtgcaccgc cgctttacag gcttcgacgc cgcttcgttc taccatcgac accaccacgc 4320
tggcacccag ttgatcggcg cgagatttaa tcgccgcgac aatttgcgac ggcgcgtgca 4380
gggccagact ggaggtggca acgccaatca gcaacgactg tttgcccgcc agttgttgtg 4440

```
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt ttctctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
tgaaaccaac aatagcgttt cttgttacat gcgcactaaa ggtatctccg aagaactggc   6480
taccgaaagc gtgatgaatc tgatcgatga aacctggaaa aagatgaaca aggaaaaact   6540
gagtggtagc ccgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatcactg aaccgattct gccgtttgaa cgcgaaaacc tgtattttca   6720
gggcctcgag caccaccacc accaccactg agatccggct gctaacaaag cccgaaagga   6780
agctgagttg gctgctgcca ccgctgagca ataactagca taaccccttg gggcctctaa   6840
```

acgggtcttg aggggttttt tgctgaaagg aggaactata tccggat 6887

<210> SEQ ID NO 81
<211> LENGTH: 559
<212> TYPE: PRT
<213> ORGANISM: Artificial Sequence
<220> FEATURE:
<223> OTHER INFORMATION: Synthetic Construct

<400> SEQUENCE: 81

Met Glu Ala Arg Arg Ser Ala Asn Tyr Glu Pro Asn Ser Trp Asp Tyr
1 5 10 15

Asp Tyr Leu Leu Ser Ser Asp Thr Asp Glu Ser Ile Glu Val Tyr Lys
20 25 30

Asp Lys Ala Lys Lys Leu Glu Ala Glu Val Arg Arg Glu Ile Asn Asn
35 40 45

Glu Lys Ala Glu Phe Leu Thr Leu Leu Glu Leu Ile Asp Asn Val Gln
50 55 60

Arg Leu Gly Leu Gly Tyr Arg Phe Glu Ser Asp Ile Arg Gly Ala Leu
65 70 75 80

Asp Arg Phe Val Ser Ser Gly Gly Phe Asp Ala Val Thr Lys Thr Ser
85 90 95

Leu His Gly Thr Ala Leu Ser Phe Arg Leu Leu Arg Gln His Gly Phe
100 105 110

Glu Val Ser Gln Glu Ala Phe Ser Gly Phe Lys Asp Gln Asn Gly Asn
115 120 125

Phe Leu Glu Asn Leu Lys Glu Asp Ile Lys Ala Ile Leu Ser Leu Tyr
130 135 140

Glu Ala Ser Phe Leu Ala Leu Glu Gly Glu Asn Ile Leu Asp Glu Ala
145 150 155 160

Lys Val Phe Ala Ile Ser His Leu Lys Glu Leu Ser Glu Glu Lys Ile
165 170 175

Gly Lys Glu Leu Ala Glu Gln Val Asn His Ala Leu Glu Leu Pro Leu
180 185 190

His Arg Arg Thr Gln Arg Leu Glu Ala Val Trp Ser Ile Glu Ala Tyr
195 200 205

Arg Lys Lys Glu Asp Ala Asn Gln Val Leu Leu Glu Leu Ala Ile Leu
210 215 220

Asp Tyr Asn Met Ile Gln Ser Val Tyr Gln Arg Asp Leu Arg Glu Thr
225 230 235 240

Ser Arg Trp Trp Arg Arg Val Gly Leu Ala Thr Lys Leu His Phe Ala
245 250 255

Arg Asp Arg Leu Ile Glu Ser Phe Tyr Trp Ala Val Gly Val Ala Phe
260 265 270

Glu Pro Gln Tyr Ser Asp Cys Arg Asn Ser Val Ala Lys Met Phe Ser
275 280 285

Phe Val Thr Ile Ile Asp Asp Ile Tyr Asp Val Tyr Gly Thr Leu Asp
290 295 300

Glu Leu Glu Leu Phe Thr Asp Ala Val Glu Arg Trp Asp Val Asn Ala
305 310 315 320

Ile Asn Asp Leu Pro Asp Tyr Met Lys Leu Cys Phe Leu Ala Leu Tyr
325 330 335

Asn Thr Ile Asn Glu Ile Ala Tyr Asp Asn Leu Lys Asp Lys Gly Glu
340 345 350

Asn Ile Leu Pro Tyr Leu Thr Lys Ala Trp Ala Asp Leu Cys Asn Ala
355 360 365

```
Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Asn Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Ser Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Cys Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 82
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 82

```
tggcgaatgg gacgcgccct gtagcggcgc attaagcgcg gcgggtgtgg tggttacgcg      60

cagcgtgacc gctacacttg ccagcgccct agcgcccgct cctttcgctt tcttcccttc     120

ctttctcgcc acgttcgccg gctttccccg tcaagctcta aatcgggggc tccctttagg     180

gttccgattt agtgctttac ggcacctcga ccccaaaaaa cttgattagg gtgatggttc     240

acgtagtggg ccatcgccct gatagacggt ttttcgccct ttgacgttgg agtccacgtt     300

ctttaatagt ggactcttgt tccaaactgg aacaacactc aaccctatct cggtctattc     360

ttttgattta taagggattt tgccgatttc ggcctattgg ttaaaaaatg agctgattta     420

acaaaaattt aacgcgaatt ttaacaaaat attaacgttt acaatttcag gtggcacttt     480

tcggggaaat gtgcgcggaa cccctatttg tttatttttc taaatacatt caaatatgta     540

tccgctcatg aattaattct tagaaaaact catcgagcat caaatgaaac tgcaatttat     600

tcatatcagg attatcaata ccatattttt gaaaaagccg tttctgtaat gaaggagaaa     660

actcaccgag gcagttccat aggatggcaa gatcctggta tcggtctgcg attccgactc     720

gtccaacatc aatacaacct attaatttcc cctcgtcaaa aataaggtta tcaagtgaga     780

aatcaccatg agtgacgact gaatccggtg agaatggcaa aagtttatgc atttctttcc     840

agacttgttc aacaggccag ccattacgct cgtcatcaaa atcactcgca tcaaccaaac     900

cgttattcat tcgtgattgc gcctgagcga gacgaaatac gcgatcgctg ttaaaaggac     960

aattacaaac aggaatcgaa tgcaaccggc gcaggaacac tgccagcgca tcaacaatat    1020
```

-continued

```
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
```

-continued

```
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
```

```
gaccaaactg cactttgctc gtgaccgcct gattgagagc ttctactggg ccgtgggtgt   5880

agcattcgaa ccgcaatact ccgactgccg taactccgtc gcaaaaatgt ttttctttcgt   5940

aaccattatc gacgatatct acgatgtata cggcaccctg gacgaactgg agctgtttac   6000

tgatgcagtt gagcgttggg acgtaaacgc catcaacgac ctgccggatt acatgaaact   6060

gtgctttctg gctctgtata acactattaa cgaaatcgcc tacgacaacc tgaaagataa   6120

aggtgagaac atcctgccgt atctgaccaa agcctgggct gacctgtgca acgctttcct   6180

gcaagaagcc aagtggctgt acaacaaatc tactccgacc tttgacgact acttcggcaa   6240

cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccaac aatagcgttt cttgttacat gcgcactaaa ggtatctccg aagaactggc   6480

taccgaaagc gtgatgaatc tgatcgatga aacctggaaa aagatgaaca aggaaaaact   6540

gagtggtagc ctgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatctgcg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887

<210> SEQ ID NO 83
<211> LENGTH: 559
<212> TYPE: PRT
<213> ORGANISM: Artificial Sequence
<220> FEATURE:
<223> OTHER INFORMATION: Synthetic Construct

<400> SEQUENCE: 83

Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175
```

```
Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Asn Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Pro Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Cys Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 84
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 84

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
```

```
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
```

```
ccgttgagca ccgccgccgc aaggaatggt gcatgcaagg agatggcgcc caacagtccc   4800

ccggccacgg ggcctgccac catacccacg ccgaaacaag cgctcatgag cccgaagtgg   4860

cgagcccgat cttccccatc ggtgatgtcg gcgatatagg cgccagcaac cgcacctgtg   4920

gcgccggtga tgccggccac gatgcgtccg gcgtagagga tcgagatctc gatcccgcga   4980

aattaatacg actcactata ggggaattgt gagcggataa caattcccct ctagaaataa   5040

ttttgtttaa ctttaagaag gagatataca tatggaagct cgtcgttctg cgaactacga   5100

acctaacagc tgggactatg attacctgct gtcctccgac acggacgagt ccatcgaagt   5160

atacaaagac aaagcgaaaa agctggaagc cgaagttcgt cgcgagatta ataacgaaaa   5220

agcagaattt ctgaccctgc tggaactgat tgacaacgtc cagcgcctgg gcctgggtta   5280

ccgtttcgag tctgatatcc gtggtgcgct ggatcgcttc gtttcctccg gcggcttcga   5340

tgcggtaacc aagacttccc tgcacggtac ggcactgtct ttccgtctgc tgcgtcaaca   5400

cggttttgag gtttctcagg aagcgttcag cggcttcaaa gaccaaaacg gcaacttcct   5460

ggagaacctg aaggaagata tcaaagctat cctgagcctg tacgaggcca gcttcctggc   5520

tctggaaggc gaaaacatcc tggacgaggc gaaggttttc gcaatctctc atctgaaaga   5580

actgtctgaa gaaaagatcg gtaaagagct ggcagaacag gtgaaccatg cactggaact   5640

gccactgcat cgccgtactc agcgtctgga agcagtatgg tctatcgagg cctaccgtaa   5700

aaaggaggac gcgaatcagg ttctgctgga gctggcaatt ctggattaca acatgatcca   5760

gtctgtatac cagcgtgatc tgcgtgaaac gtcccgttgg tggcgtcgtg tgggtctggc   5820

gaccaaactg cactttgctc gtgaccgcct gattgagagc ttctactggg ccgtgggtgt   5880

agcattcgaa ccgcaatact ccgactgccg taactccgtc gcaaaaatgt tttctttcgt   5940

aaccattatc gacgatatct acgatgtata cggcaccctg gacgaactgg agctgtttac   6000

tgatgcagtt gagcgttggg acgtaaacgc catcaacgac ctgccggatt acatgaaact   6060

gtgctttctg gctctgtata acactattaa cgaaatcgcc tacgacaacc tgaaagataa   6120

aggtgagaac atcctgccgt atctgaccaa agcctgggct gacctgtgca acgctttcct   6180

gcaagaagcc aagtggctgt acaacaaatc tactccgacc tttgacgact acttcggcaa   6240

cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccaac aatagcgttt cttgttacat gcgcactaaa ggtatctccg aagaactggc   6480

taccgaaagc gtgatgaatc tgatcgatga aacctggaaa aagatgaaca aggaaaaact   6540

gggtggtagc ccgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatctgcg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

<210> SEQ ID NO 85
<211> LENGTH: 559
<212> TYPE: PRT
<213> ORGANISM: Artificial Sequence
<220> FEATURE:
<223> OTHER INFORMATION: Synthetic Construct

<400> SEQUENCE: 85

```
Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415
```

```
Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Asn Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Ser Gly Ser Pro Phe Ala
            485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Cys Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 86
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 86

```
tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420

acaaaaattt aacgcgaatt ttaacaaaat attaacgttt acaatttcag gtggcacttt    480

tcggggaaat gtgcgcggaa cccctatttg tttatttttc taaatacatt caaatatgta    540

tccgctcatg aattaattct tagaaaaact catcgagcat caaatgaaac tgcaatttat    600

tcatatcagg attatcaata ccatattttt gaaaaagccg tttctgtaat gaaggagaaa    660

actcaccgag gcagttccat aggatggcaa gatcctggta tcggtctgcg attccgactc    720

gtccaacatc aatacaacct attaatttcc cctcgtcaaa aataaggtta tcaagtgaga    780

aatcaccatg agtgacgact gaatccggtg agaatggcaa aagtttatgc atttctttcc    840

agacttgttc aacaggccag ccattacgct cgtcatcaaa atcactcgca tcaaccaaac    900

cgttattcat tcgtgattgc gcctgagcga gacgaaatac gcgatcgctg ttaaaaggac    960

aattacaaac aggaatcgaa tgcaaccggc gcaggaacac tgccagcgca tcaacaatat   1020

tttcacctga atcaggatat tcttctaata cctggaatgc tgttttcccg gggatcgcag   1080

tggtgagtaa ccatgcatca tcaggagtac ggataaaatg cttgatggtc ggaagaggca   1140

taaattccgt cagccagttt agtctgacca tctcatctgt aacatcattg gcaacgctac   1200

ctttgccatg tttcagaaac aactctggcg catcgggctt cccatacaat cgatagattg   1260

tcgcacctga ttgcccgaca ttatcgcgag cccatttata cccatataaa tcagcatcca   1320
```

```
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
```

-continued

```
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
```

```
aggtgagaac atcctgccgt atctgaccaa agcctgggct gacctgtgca acgctttcct   6180

gcaagaagcc aagtggctgt acaacaaatc tactccgacc tttgacgact acttcggcaa   6240

cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccaac aatagcgttt cttgttacat gcgcactaaa ggtatctccg aagaactggc   6480

taccgaaagc gtgatgaatc tgatcgatga aacctggaaa aagatgaaca aggaaaaact   6540

gagtggtagc ccgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatctgcg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

```
<210> SEQ ID NO 87
<211> LENGTH: 559
<212> TYPE: PRT
<213> ORGANISM: Artificial Sequence
<220> FEATURE:
<223> OTHER INFORMATION: Synthetic Construct

<400> SEQUENCE: 87

Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
```

-continued

```
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Ser Gly Ser Pro Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 88
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 88

```
tggcgaatgg gacgcgccct gtagcggcgc attaagcgcg gcgggtgtgg tggttacgcg      60

cagcgtgacc gctacacttg ccagcgccct agcgcccgct cctttcgctt tcttcccttc     120

ctttctcgcc acgttcgccg gctttccccg tcaagctcta aatcgggggc tccctttagg     180

gttccgattt agtgctttac ggcacctcga ccccaaaaaa cttgattagg gtgatggttc     240
```

-continued

```
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
```

-continued

```
aagcgttaat gtctggcttc tgataaagcg ggccatgtta agggcggttt tttcctgttt   2700
ggtcactgat gcctccgtgt aagggggatt tctgttcatg gggtaatga taccgatgaa    2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
```

```
ttttgtttaa ctttaagaag gagatataca tatggaagct cgtcgttctg cgaactacga   5100

acctaacagc tgggactatg attacctgct gtcctccgac acggacgagt ccatcgaagt   5160

atacaaagac aaagcgaaaa agctggaagc cgaagttcgt cgcgagatta ataacgaaaa   5220

agcagaattt ctgaccctgc tggaactgat tgacaacgtc cagcgcctgg gcctgggtta   5280

ccgtttcgag tctgatatcc gtggtgcgct ggatcgcttc gtttcctccg gcggcttcga   5340

tgcggtaacc aagacttccc tgcacggtac ggcactgtct ttccgtctgc tgcgtcaaca   5400

cggttttgag gtttctcagg aagcgttcag cggcttcaaa gaccaaaacg gcaacttcct   5460

ggagaacctg aaggaagata tcaaagctat cctgagcctg tacgaggcca gcttcctggc   5520

tctggaaggc gaaaacatcc tggacgaggc gaaggttttc gcaatctctc atctgaaaga   5580

actgtctgaa gaaaagatcg gtaaagagct ggcagaacag gtgaaccatg cactggaact   5640

gccactgcat cgccgtactc agcgtctgga agcagtatgg tctatcgagg cctaccgtaa   5700

aaaggaggac gcgaatcagg ttctgctgga gctggcaatt ctggattaca acatgatcca   5760

gtctgtatac cagcgtgatc tgcgtgaaac gtcccgttgg tggcgtcgtg tgggtctggc   5820

gaccaaactg cactttgctc gtgaccgcct gattgagagc ttctactggg ccgtgggtgt   5880

agcattcgaa ccgcaatact ccgactgccg taactccgtc gcaaaaatgt tttctttcgt   5940

aaccattatc gacgatatct acgatgtata cggcaccctg gacgaactgg agctgtttac   6000

tgatgcagtt gagcgttggg acgtaaacgc catcaacgac ctgccggatt acatgaaact   6060

gtgctttctg gctctgtata acactattaa cgaaatcgcc tacgacaacc tgaaagataa   6120

aggtgagaac atcctgccgt atctgaccaa agcctgggct gacctgtgca acgctttcct   6180

gcaagaagcc aagtggctgt acaacaaatc tactccgacc tttgacgact acttcggcaa   6240

cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccgca aatagcgttt cttgttacat gcgcactaaa ggtatctccg aagaactggc   6480

taccgaaagc gtgatgaatc tgatcgatga aacctggaaa aagatgaaca aggaaaaact   6540

gagtggtagc ccgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatcactg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

<210> SEQ ID NO 89
<211> LENGTH: 559
<212> TYPE: PRT
<213> ORGANISM: Artificial Sequence
<220> FEATURE:
<223> OTHER INFORMATION: Synthetic Construct

<400> SEQUENCE: 89

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45
```

```
Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
```

```
465                 470                 475                 480

Thr Trp Lys Lys Met Asn Lys Glu Lys Leu Ser Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Cys Glu Pro Ile Leu Pro Phe Glu Arg
    530                 535                 540

Glu Asn Leu Tyr Phe Gln Gly Leu Glu His His His His His His
545                 550                 555


<210> SEQ ID NO 90
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 90

tggcgaatgg gacgcgccct gtagcggcgc attaagcgcg gcgggtgtgg tggttacgcg      60

cagcgtgacc gctacacttg ccagcgccct agcgcccgct cctttcgctt tcttcccttc     120

ctttctcgcc acgttcgccg gctttccccg tcaagctcta aatcgggggc tccctttagg     180

gttccgattt agtgctttac ggcacctcga ccccaaaaaa cttgattagg gtgatggttc     240

acgtagtggg ccatcgccct gatagacggt ttttcgccct ttgacgttgg agtccacgtt     300

ctttaatagt ggactcttgt tccaaactgg aacaacactc aaccctatct cggtctattc     360

ttttgattta taagggattt tgccgatttc ggcctattgg ttaaaaaatg agctgattta     420

acaaaaattt aacgcgaatt ttaacaaaat attaacgttt acaatttcag gtggcacttt     480

tcggggaaat gtgcgcggaa cccctatttg tttatttttc taaatacatt caaatatgta     540

tccgctcatg aattaattct tagaaaaact catcgagcat caaatgaaac tgcaatttat     600

tcatatcagg attatcaata ccatattttt gaaaaagccg tttctgtaat gaaggagaaa     660

actcaccgag gcagttccat aggatggcaa gatcctggta tcggtctgcg attccgactc     720

gtccaacatc aatacaacct attaatttcc cctcgtcaaa aataaggtta tcaagtgaga     780

aatcaccatg agtgacgact gaatccggtg agaatggcaa aagtttatgc atttctttcc     840

agacttgttc aacaggccag ccattacgct cgtcatcaaa atcactcgca tcaaccaaac     900

cgttattcat tcgtgattgc gcctgagcga gacgaaatac gcgatcgctg ttaaaaggac     960

aattacaaac aggaatcgaa tgcaaccggc gcaggaacac tgccagcgca tcaacaatat    1020

tttcacctga atcaggatat tcttctaata cctggaatgc tgttttcccg gggatcgcag    1080

tggtgagtaa ccatgcatca tcaggagtac ggataaaatg cttgatggtc ggaagaggca    1140

taaattccgt cagccagttt agtctgacca tctcatctgt aacatcattg gcaacgctac    1200

ctttgccatg tttcagaaac aactctggcg catcgggctt cccatacaat cgatagattg    1260

tcgcacctga ttgcccgaca ttatcgcgag cccatttata cccatataaa tcagcatcca    1320

tgttggaatt taatcgcggc ctagagcaag acgtttcccg ttgaatatgg ctcataacac    1380

cccttgtatt actgtttatg taagcagaca gttttattgt tcatgaccaa aatcccttaa    1440

cgtgagtttt cgttccactg agcgtcagac cccgtagaaa agatcaaagg atcttcttga    1500

gatccttttt ttctgcgcgt aatctgctgc ttgcaaacaa aaaaaccacc gctaccagcg    1560

gtggtttgtt tgccggatca agagctacca actctttttc cgaaggtaac tggcttcagc    1620
```

-continued

```
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
```

```
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
```

```
tgaaaccgca aatagcgttt cttgttacat gcgcactaaa ggtatctccg aagaactggc   6480

taccgaaagc gtgatgaatc tgatcgatga aacctggaaa aagatgaaca aggaaaaact   6540

gagtggtagc ctgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatctgcg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

<210> SEQ ID NO 91
<211> LENGTH: 559
<212> TYPE: PRT
<213> ORGANISM: Artificial Sequence
<220> FEATURE:
<223> OTHER INFORMATION: Synthetic Construct

<400> SEQUENCE: 91

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285
```

-continued

```
Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Ser Gly Ser Pro Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Cys Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 92
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 92

```
tggcgaatgg gacgcgccct gtagcggcgc attaagcgcg gcgggtgtgg tggttacgcg      60

cagcgtgacc gctacacttg ccagcgccct agcgcccgct cctttcgctt tcttcccttc     120

ctttctcgcc acgttcgccg gctttccccg tcaagctcta aatcgggggc tccctttagg     180

gttccgattt agtgctttac ggcacctcga ccccaaaaaa cttgattagg gtgatggttc     240

acgtagtggg ccatcgccct gatagacggt ttttcgccct ttgacgttgg agtccacgtt     300

ctttaatagt ggactcttgt tccaaactgg aacaacactc aaccctatct cggtctattc     360

ttttgattta taagggattt tgccgatttc ggcctattgg ttaaaaaatg agctgattta     420

acaaaaattt aacgcgaatt ttaacaaaat attaacgttt acaatttcag gtggcacttt     480

tcggggaaat gtgcgcggaa cccctatttg tttatttttc taaatacatt caaatatgta     540
```

-continued

```
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
```

-continued

```
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
```

-continued

```
tgcggtaacc aagacttccc tgcacggtac ggcactgtct ttccgtctgc tgcgtcaaca   5400

cggttttgag gtttctcagg aagcgttcag cggcttcaaa gaccaaaacg gcaacttcct   5460

ggagaacctg aaggaagata tcaaagctat cctgagcctg tacgaggcca gcttcctggc   5520

tctggaaggc gaaaacatcc tggacgaggc gaaggttttc gcaatctctc atctgaaaga   5580

actgtctgaa gaaaagatcg gtaaagagct ggcagaacag gtgaaccatg cactggaact   5640

gccactgcat cgccgtactc agcgtctgga agcagtatgg tctatcgagg cctaccgtaa   5700

aaaggaggac gcgaatcagg ttctgctgga gctggcaatt ctggattaca acatgatcca   5760

gtctgtatac cagcgtgatc tgcgtgaaac gtcccgttgg tggcgtcgtg tgggtctggc   5820

gaccaaactg cactttgctc gtgaccgcct gattgagagc ttctactggg ccgtgggtgt   5880

agcattcgaa ccgcaatact ccgactgccg taactccgtc gcaaaaatgt tttctttcgt   5940

aaccattatc gacgatatct acgatgtata cggcaccctg gacgaactgg agctgtttac   6000

tgatgcagtt gagcgttggg acgtaaacgc catcaacgac ctgccggatt acatgaaact   6060

gtgctttctg gctctgtata acactattaa cgaaatcgcc tacgacaacc tgaaagataa   6120

aggtgagaac atcctgccgt atctgaccaa agcctgggct gacctgtgca acgctttcct   6180

gcaagaagcc aagtggctgt acaacaaatc tactccgacc tttgacgact acttcggcaa   6240

cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccgca aatagcgttt cttgttacat gcgcactaaa ggtatctccg aagaactggc   6480

taccgaaagc gtgatgaatc tgatcgatga aacctggaaa aagatgaaca aggaaaaact   6540

gagtggtagc ccgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatctgcg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

<210> SEQ ID NO 93
<211> LENGTH: 559
<212> TYPE: PRT
<213> ORGANISM: Artificial Sequence
<220> FEATURE:
<223> OTHER INFORMATION: Synthetic Construct

<400> SEQUENCE: 93

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95
```

```
Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Pro Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525
```

-continued

Lys Arg Val Leu Ser Val Ile Cys Glu Pro Ile Leu Pro Phe Glu Arg
530 535 540

Glu Asn Leu Tyr Phe Gln Gly Leu Glu His His His His His His
545 550 555

<210> SEQ ID NO 94
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 94
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560
gtggtttgtt tgccggatca agagctacca actctttttc cgaaggtaac tggcttcagc 1620
agagcgcaga taccaaatac tgtccttcta gtgtagccgt agttaggcca ccacttcaag 1680
aactctgtag caccgcctac atacctcgct ctgctaatcc tgttaccagt ggctgctgcc 1740
agtggcgata agtcgtgtct taccgggttg gactcaagac gatagttacc ggataaggcg 1800
cagcggtcgg gctgaacggg gggttcgtgc acacagccca gcttggagcg aacgacctac 1860
accgaactga gatacctaca gcgtgagcta tgagaaagcg ccacgcttcc cgaagggaga 1920

-continued

```
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
```

-continued

```
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
tgaaaccgca aatagcgttt cttgttacat gcgcactaaa ggtatctccg aagaactggc   6480
taccgaaagc gtgatgaatc tgatcgatga aacctggaaa aagatgaaca aggaaaaact   6540
gggtggtagc ccgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatctgcg aaccgattct gccgtttgaa cgcgaaaacc tgtattttca   6720
```

gggcctcgag caccaccacc accaccactg agatccggct gctaacaaag cccgaaagga 6780
agctgagttg gctgctgcca ccgctgagca ataactagca taaccccttg gggcctctaa 6840
acgggtcttg aggggttttt tgctgaaagg aggaactata tccggat 6887

<210> SEQ ID NO 95
<211> LENGTH: 559
<212> TYPE: PRT
<213> ORGANISM: Artificial Sequence
<220> FEATURE:
<223> OTHER INFORMATION: Synthetic Construct

<400> SEQUENCE: 95

Met Glu Ala Arg Arg Ser Ala Asn Tyr Glu Pro Asn Ser Trp Asp Tyr
1 5 10 15

Asp Tyr Leu Leu Ser Ser Asp Thr Asp Glu Ser Ile Glu Val Tyr Lys
20 25 30

Asp Lys Ala Lys Lys Leu Glu Ala Glu Val Arg Arg Glu Ile Asn Asn
35 40 45

Glu Lys Ala Glu Phe Leu Thr Leu Leu Glu Leu Ile Asp Asn Val Gln
50 55 60

Arg Leu Gly Leu Gly Tyr Arg Phe Glu Ser Asp Ile Arg Gly Ala Leu
65 70 75 80

Asp Arg Phe Val Ser Ser Gly Gly Phe Asp Ala Val Thr Lys Thr Ser
85 90 95

Leu His Gly Thr Ala Leu Ser Phe Arg Leu Leu Arg Gln His Gly Phe
100 105 110

Glu Val Ser Gln Glu Ala Phe Ser Gly Phe Lys Asp Gln Asn Gly Asn
115 120 125

Phe Leu Glu Asn Leu Lys Glu Asp Ile Lys Ala Ile Leu Ser Leu Tyr
130 135 140

Glu Ala Ser Phe Leu Ala Leu Glu Gly Glu Asn Ile Leu Asp Glu Ala
145 150 155 160

Lys Val Phe Ala Ile Ser His Leu Lys Glu Leu Ser Glu Glu Lys Ile
165 170 175

Gly Lys Glu Leu Ala Glu Gln Val Asn His Ala Leu Glu Leu Pro Leu
180 185 190

His Arg Arg Thr Gln Arg Leu Glu Ala Val Trp Ser Ile Glu Ala Tyr
195 200 205

Arg Lys Lys Glu Asp Ala Asn Gln Val Leu Leu Glu Leu Ala Ile Leu
210 215 220

Asp Tyr Asn Met Ile Gln Ser Val Tyr Gln Arg Asp Leu Arg Glu Thr
225 230 235 240

Ser Arg Trp Trp Arg Arg Val Gly Leu Ala Thr Lys Leu His Phe Ala
245 250 255

Arg Asp Arg Leu Ile Glu Ser Phe Tyr Trp Ala Val Gly Val Ala Phe
260 265 270

Glu Pro Gln Tyr Ser Asp Cys Arg Asn Ser Val Ala Lys Met Phe Ser
275 280 285

Phe Val Thr Ile Ile Asp Asp Ile Tyr Asp Val Tyr Gly Thr Leu Asp
290 295 300

Glu Leu Glu Leu Phe Thr Asp Ala Val Glu Arg Trp Asp Val Asn Ala
305 310 315 320

Ile Asn Asp Leu Pro Asp Tyr Met Lys Leu Cys Phe Leu Ala Leu Tyr
325 330 335

```
Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Phe Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 96
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 96

```
tggcgaatgg gacgcgccct gtagcggcgc attaagcgcg gcgggtgtgg tggttacgcg      60

cagcgtgacc gctacacttg ccagcgccct agcgcccgct cctttcgctt tcttcccttc     120

ctttctcgcc acgttcgccg gctttccccg tcaagctcta aatcgggggc tccctttagg     180

gttccgattt agtgctttac ggcacctcga ccccaaaaaa cttgattagg gtgatggttc     240

acgtagtggg ccatcgccct gatagacggt ttttcgccct ttgacgttgg agtccacgtt     300

ctttaatagt ggactcttgt tccaaactgg aacaacactc aaccctatct cggtctattc     360

ttttgattta taagggattt tgccgatttc ggcctattgg ttaaaaaatg agctgattta     420

acaaaaattt aacgcgaatt ttaacaaaat attaacgttt acaatttcag gtggcacttt     480

tcggggaaat gtgcgcggaa cccctatttg tttatttttc taaatacatt caaatatgta     540

tccgctcatg aattaattct tagaaaaact catcgagcat caaatgaaac tgcaatttat     600

tcatatcagg attatcaata ccatattttt gaaaaagccg tttctgtaat gaaggagaaa     660

actcaccgag gcagttccat aggatggcaa gatcctggta tcggtctgcg attccgactc     720

gtccaacatc aatacaacct attaatttcc cctcgtcaaa aataaggtta tcaagtgaga     780

aatcaccatg agtgacgact gaatccggtg agaatggcaa aagtttatgc atttctttcc     840
```

-continued agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560
gtggtttgtt tgccggatca agagctacca actctttttc cgaaggtaac tggcttcagc 1620
agagcgcaga taccaaatac tgtccttcta gtgtagccgt agttaggcca ccacttcaag 1680
aactctgtag caccgcctac atacctcgct ctgctaatcc tgttaccagt ggctgctgcc 1740
agtggcgata agtcgtgtct taccgggttg gactcaagac gatagttacc ggataaggcg 1800
cagcggtcgg gctgaacggg gggttcgtgc acacagccca gcttggagcg aacgacctac 1860
accgaactga gatacctaca gcgtgagcta tgagaaagcg ccacgcttcc cgaagggaga 1920
aaggcggaca ggtatccggt aagcggcagg gtcggaacag gagagcgcac gagggagctt 1980
ccagggggaa acgcctggta tctttatagt cctgtcgggt ttcgccacct ctgacttgag 2040
cgtcgatttt tgtgatgctc gtcagggggg cggagcctat ggaaaaacgc cagcaacgcg 2100
gcctttttac ggttcctggc cttttgctgg ccttttgctc acatgttctt tcctgcgtta 2160
tcccctgatt ctgtggataa ccgtattacc gcctttgagt gagctgatac cgctcgccgc 2220
agccgaacga ccgagcgcag cgagtcagtg agcgaggaag cggaagagcg cctgatgcgg 2280
tattttctcc ttacgcatct gtgcggtatt tcacaccgca tatatggtgc actctcagta 2340
caatctgctc tgatgccgca tagttaagcc agtatacact ccgctatcgc tacgtgactg 2400
ggtcatggct gcgccccgac acccgccaac acccgctgac gcgccctgac gggcttgtct 2460
gctcccggca tccgcttaca gacaagctgt gaccgtctcc gggagctgca tgtgtcagag 2520
gttttcaccg tcatcaccga aacgcgcgag gcagctgcgg taaagctcat cagcgtggtc 2580
gtgaagcgat tcacagatgt ctgcctgttc atccgcgtcc agctcgttga gtttctccag 2640
aagcgttaat gtctggcttc tgataaagcg ggccatgtta agggcggttt tttcctgttt 2700
ggtcactgat gcctccgtgt aagggggatt tctgttcatg gggg taatga taccgatgaa 2760
acgagagagg atgctcacga tacgggttac tgatgatgaa catgcccggt tactggaacg 2820
ttgtgagggt aaacaactgg cggtatggat gcggcgggac cagagaaaaa tcactcaggg 2880
tcaatgccag cgcttcgtta atacagatgt aggtgttcca cagggtagcc agcagcatcc 2940
tgcgatgcag atccggaaca taatggtgca gggcgctgac ttccgcgttt ccagacttta 3000
cgaaacacgg aaaccgaaga ccattcatgt tgttgctcag gtcgcagacg ttttgcagca 3060
gcagtcgctt cacgttcgct cgcgtatcgg tgattcattc tgctaaccag taaggcaacc 3120
ccgccagcct agccgggtcc tcaacgacag gagcacgatc atgcgcaccc gtggggccgc 3180
catgccggcg ataatggcct gcttctcgcc gaaacgtttg gtggcgggac cagtgacgaa 3240

-continued

```
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
```

-continued

```
gccactgcat cgccgtactc agcgtctgga agcagtatgg tctatcgagg cctaccgtaa   5700

aaaggaggac gcgaatcagg ttctgctgga gctggcaatt ctggattaca acatgatcca   5760

gtctgtatac cagcgtgatc tgcgtgaaac gtcccgttgg tggcgtcgtg tgggtctggc   5820

gaccaaactg cactttgctc gtgaccgcct gattgagagc ttctactggg ccgtgggtgt   5880

agcattcgaa ccgcaatact ccgactgccg taactccgtc gcaaaaatgt tttctttcgt   5940

aaccattatc gacgatatct acgatgtata cggcaccctg gacgaactgg agctgtttac   6000

tgatgcagtt gagcgttggg acgtaaacgc catcaacgac ctgccggatt acatgaaact   6060

gtgctttctg gctctgtata acactattaa cgaaatcgcc tacgacaacc tgaaagataa   6120

aggtgagaac atcctgccgt atctgaccaa agcctgggct gacctgtgca acgctttcct   6180

gcaagaagcc aagtggctgt acaacaaatc tactccgacc tttgacgact acttcggcaa   6240

cgcatggaaa tcctcttctg gcccgctgca actggtgttc gcttacttcg ctgtcgtgca   6300

gaacattaaa aaggaagaga tcgaaaacct gcaaaaatac catgacacca tctctcgtcc   6360

ttcccatatc ttccgtctgt gcaatgacct ggctagcgcg tctgcggaaa ttgcgcgtgg   6420

tgaaaccgca aatagcgttt cttgttacat gcgcactaaa ggtatctccg aagaactggc   6480

taccgaaagc gtgatgaatc tgatcgatga aacctggaaa aagatgaaca aggaaaaact   6540

gggtggtagc ctgttcgcga aaccgttcgt ggaaaccgcg atcaacctgg cacgtcaatc   6600

tcactgcact tatcataacg gcgacgcgca tacctctccg gatgagctga cccgcaaacg   6660

cgttctgtct gtaatctttg aaccgattct gccgtttgaa cgcgaaaacc tgtattttca   6720

gggcctcgag caccaccacc accaccactg agatccggct gctaacaaag cccgaaagga   6780

agctgagttg gctgctgcca ccgctgagca ataactagca taaccccttg gggcctctaa   6840

acgggtcttg aggggttttt tgctgaaagg aggaactata tccggat                 6887
```

<210> SEQ ID NO 97
<211> LENGTH: 559
<212> TYPE: PRT
<213> ORGANISM: Artificial Sequence
<220> FEATURE:
<223> OTHER INFORMATION: Synthetic Construct

<400> SEQUENCE: 97

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
```

-continued

```
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Pro Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Phe Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 98
<211> LENGTH: 6887

<212> TYPE: DNA
<213> ORGANISM: Artificial Sequence
<220> FEATURE:
<223> OTHER INFORMATION: Synthetic Construct

<400> SEQUENCE: 98
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560
gtggtttgtt tgccggatca agagctacca actctttttc cgaaggtaac tggcttcagc 1620
agagcgcaga taccaaatac tgtccttcta gtgtagccgt agttaggcca ccacttcaag 1680
aactctgtag caccgcctac atacctcgct ctgctaatcc tgttaccagt ggctgctgcc 1740
agtggcgata agtcgtgtct taccgggttg gactcaagac gatagttacc ggataaggcg 1800
cagcggtcgg gctgaacggg gggttcgtgc acacagccca gcttggagcg aacgacctac 1860
accgaactga gatacctaca gcgtgagcta tgagaaagcg ccacgcttcc cgaagggaga 1920
aaggcggaca ggtatccggt aagcggcagg gtcggaacag gagagcgcac gagggagctt 1980
ccagggggaa acgcctggta tctttatagt cctgtcgggt ttcgccacct ctgacttgag 2040
cgtcgatttt tgtgatgctc gtcagggggg cggagcctat ggaaaaacgc cagcaacgcg 2100
gcctttttac ggttcctggc cttttgctgg ccttttgctc acatgttctt tcctgcgtta 2160
tcccctgatt ctgtggataa ccgtattacc gcctttgagt gagctgatac cgctcgccgc 2220

-continued

```
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
```

```
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
tgaaaccgca aatagcgttt cttgttacat gcgcactaaa ggtatctccg aagaactggc   6480
taccgaaagc gtgatgaatc tgatcgatga aacctggaaa aagatgaaca aggaaaaact   6540
gggtggtagc ccgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatctttg aaccgattct gccgtttgaa cgcgaaaacc tgtattttca   6720
gggcctcgag caccaccacc accaccactg agatccggct gctaacaaag cccgaaagga   6780
agctgagttg gctgctgcca ccgctgagca ataactagca taaccccttg gggcctctaa   6840
acgggtcttg aggggttttt tgctgaaagg aggaactata tccggat                 6887
```

<210> SEQ ID NO 99
<211> LENGTH: 89

<212> TYPE: PRT
<213> ORGANISM: Artificial Sequence
<220> FEATURE:
<223> OTHER INFORMATION: Synthetic Construct

<400> SEQUENCE: 99

Ala Asn Ser Val Ser Cys Tyr Met Arg Thr Lys Gly Ile Ser Glu Glu
1 5 10 15

Leu Ala Thr Glu Ser Val Met Asn Leu Ile Asp Glu Thr Trp Lys Lys
20 25 30

Met Asn Lys Glu Lys Leu Gly Gly Ser Leu Phe Ala Lys Pro Phe Val
35 40 45

Glu Thr Ala Ile Asn Leu Ala Arg Gln Ser His Cys Thr Tyr His Asn
50 55 60

Gly Asp Ala His Thr Ser Pro Asp Glu Leu Thr Arg Lys Arg Val Leu
65 70 75 80

Ser Val Ile Thr Glu Pro Ile Leu Pro
85

<210> SEQ ID NO 100
<211> LENGTH: 89
<212> TYPE: PRT
<213> ORGANISM: Artificial Sequence
<220> FEATURE:
<223> OTHER INFORMATION: Synthetic Construct

<400> SEQUENCE: 100

Ala Asn Ser Val Ser Cys Tyr Met Arg Thr Lys Gly Ile Ser Glu Glu
1 5 10 15

Leu Ala Thr Glu Ser Val Met Asn Leu Ile Asp Glu Thr Trp Lys Lys
20 25 30

Met Asn Lys Glu Lys Leu Gly Gly Ser Leu Phe Ala Lys Pro Phe Val
35 40 45

Glu Thr Ala Ile Asn Leu Ala Arg Gln Ser His Cys Thr Tyr His Asn
50 55 60

Gly Asp Ala His Thr Ser Pro Asp Glu Leu Thr Arg Lys Arg Val Leu
65 70 75 80

Ser Val Ile Thr Glu Pro Ile Leu Pro
85

<210> SEQ ID NO 101
<211> LENGTH: 89
<212> TYPE: PRT
<213> ORGANISM: Artificial Sequence
<220> FEATURE:
<223> OTHER INFORMATION: Synthetic Construct

<400> SEQUENCE: 101

Ala Asn Ser Val Ser Cys Tyr Met Arg Thr Lys Gly Ile Ser Glu Glu
1 5 10 15

Leu Ala Thr Glu Ser Val Met Asn Leu Ile Asp Glu Thr Trp Lys Lys
20 25 30

Met Asn Lys Glu Lys Leu Gly Gly Ser Leu Phe Ala Lys Pro Phe Val
35 40 45

Glu Thr Ala Ile Asn Leu Ala Arg Gln Ser His Cys Thr Tyr His Asn
50 55 60

Gly Asp Ala His Thr Ser Pro Asp Glu Leu Thr Arg Lys Arg Val Leu
65 70 75 80

Ser Val Ile Thr Glu Pro Ile Leu Pro
85

<210> SEQ ID NO 102
<211> LENGTH: 89
<212> TYPE: PRT
<213> ORGANISM: Artificial Sequence
<220> FEATURE:
<223> OTHER INFORMATION: Synthetic Construct

<400> SEQUENCE: 102

```
Ala Asn Ser Val Ser Cys Tyr Met Arg Thr Lys Gly Ile Ser Glu Glu
 1               5                  10                  15

Leu Ala Thr Glu Ser Val Met Asn Leu Ile Asp Glu Thr Trp Lys Lys
            20                  25                  30

Met Asn Lys Glu Lys Leu Gly Gly Ser Leu Phe Ala Lys Pro Phe Val
        35                  40                  45

Glu Thr Ala Ile Asn Leu Ala Arg Gln Ser His Cys Thr Tyr His Asn
    50                  55                  60

Gly Asp Ala His Thr Ser Pro Asp Glu Leu Thr Arg Lys Arg Val Leu
65                  70                  75                  80

Ser Val Ile Thr Glu Pro Ile Leu Pro
                85
```

<210> SEQ ID NO 103
<211> LENGTH: 89
<212> TYPE: PRT
<213> ORGANISM: Artificial Sequence
<220> FEATURE:
<223> OTHER INFORMATION: Synthetic Construct

<400> SEQUENCE: 103

```
Ala Asn Ser Val Ser Cys Tyr Met Arg Thr Lys Gly Ile Ser Glu Glu
 1               5                  10                  15

Leu Ala Thr Glu Ser Val Met Asn Leu Ile Asp Glu Thr Cys Lys Lys
            20                  25                  30

Met Asn Lys Glu Lys Leu Gly Gly Ser Leu Phe Ala Lys Pro Phe Val
        35                  40                  45

Glu Thr Ala Ile Asn Leu Ala Arg Gln Ser His Cys Thr Tyr His Asn
    50                  55                  60

Gly Asp Ala His Thr Ser Pro Asp Glu Leu Thr Arg Lys Arg Val Leu
65                  70                  75                  80

Ser Val Ile Thr Glu Pro Ile Leu Pro
                85
```

<210> SEQ ID NO 104
<211> LENGTH: 91
<212> TYPE: PRT
<213> ORGANISM: Artificial Sequence
<220> FEATURE:
<223> OTHER INFORMATION: Synthetic Construct

<400> SEQUENCE: 104

```
Thr Asn Ser Ile Ile Ser Tyr Met His Glu Asn Asp Gly Thr Ser Glu
 1               5                  10                  15

Glu Gln Ala Arg Glu Glu Leu Arg Lys Leu Ile Asp Ala Glu Trp Lys
            20                  25                  30

Lys Met Asn Arg Glu Arg Val Ser Asp Ser Thr Leu Leu Pro Lys Ala
        35                  40                  45

Phe Met Glu Ile Ala Val Asn Met Ala Arg Val Ser His Cys Thr Tyr
    50                  55                  60

Gln Tyr Gly Asp Gly Leu Gly Arg Pro Asp Tyr Ala Thr Glu Asn Arg
```

```
65                  70                  75                  80

Ile Lys Leu Leu Leu Ile Asp Pro Phe Pro Ile
                85                  90


<210> SEQ ID NO 105
<211> LENGTH: 89
<212> TYPE: PRT
<213> ORGANISM: Artificial Sequence
<220> FEATURE:
<223> OTHER INFORMATION: Synthetic Construct

<400> SEQUENCE: 105

Pro Lys Ser Leu Gln Cys Tyr Met Ser Asp Tyr Asn Ala Ser Glu Ala
 1               5                  10                  15

Glu Ala Arg Lys His Val Lys Trp Leu Ile Ala Glu Val Trp Lys Lys
            20                  25                  30

Met Asn Ala Glu Arg Val Ser Lys Asp Ser Pro Phe Gly Lys Asp Phe
        35                  40                  45

Ile Gly Cys Ala Val Asp Leu Gly Arg Met Ala Gln Leu Met Tyr His
    50                  55                  60

Asn Gly Asp Gly His Gly Thr Gln His Pro Ile Ile His Gln Gln Met
65                  70                  75                  80

Thr Arg Thr Leu Phe Glu Pro Phe Ala
                85


<210> SEQ ID NO 106
<211> LENGTH: 88
<212> TYPE: PRT
<213> ORGANISM: Artificial Sequence
<220> FEATURE:
<223> OTHER INFORMATION: Synthetic Construct

<400> SEQUENCE: 106

Pro Lys Thr Ile Gln Cys Tyr Met Lys Glu Thr Asn Ala Ser Glu Glu
 1               5                  10                  15

Glu Ala Val Glu His Val Lys Phe Leu Ile Arg Glu Ala Trp Lys Asp
            20                  25                  30

Met Asn Thr Ala Ile Ala Ala Gly Tyr Pro Phe Pro Asp Gly Met Val
        35                  40                  45

Ala Gly Ala Ala Asn Ile Gly Arg Val Ala Gln Phe Ile Tyr Leu His
    50                  55                  60

Gly Asp Gly Phe Gly Val Gln His Ser Lys Thr Tyr Glu His Ile Ala
65                  70                  75                  80

Gly Leu Leu Phe Glu Pro Tyr Ala
                85


<210> SEQ ID NO 107
<211> LENGTH: 89
<212> TYPE: PRT
<213> ORGANISM: Artificial Sequence
<220> FEATURE:
<223> OTHER INFORMATION: Synthetic Construct

<400> SEQUENCE: 107

Pro Lys Ala Ile Gln Cys Tyr Met Asn Glu Thr Gly Ala Ser Glu Glu
 1               5                  10                  15

Asp Ala Arg Glu Tyr Ile Lys Tyr Leu Ile Ser Ala Thr Trp Lys Lys
            20                  25                  30

Met Asn Glu Asp Arg Val Ala Ser Ser Pro Phe Ser His Ile Phe Ile
        35                  40                  45
```

-continued

```
Glu Ile Ala Leu Asn Leu Ala Arg Met Ala Gln Cys Met Tyr Gln His
    50                  55                  60

Gly Asp Gly His Gly His Gly Asn His Glu Thr Lys Asp Arg Ile Leu
65                  70                  75                  80

Ser Leu Leu Ile Gln Pro Ile Pro Leu
                85
```

<210> SEQ ID NO 108
<211> LENGTH: 90
<212> TYPE: PRT
<213> ORGANISM: Artificial Sequence
<220> FEATURE:
<223> OTHER INFORMATION: Synthetic Construct

<400> SEQUENCE: 108

```
Ala Thr Gly Ile Glu Cys Cys Met Arg Asp Tyr Gly Ile Ser Thr Lys
 1               5                  10                  15

Glu Ala Met Ala Lys Phe Gln Asn Met Ala Glu Thr Ala Trp Lys Asp
            20                  25                  30

Ile Asn Glu Gly Leu Leu Arg Pro Thr Pro Val Ser Thr Glu Phe Leu
        35                  40                  45

Thr Pro Ile Leu Asn Leu Ala Arg Ile Val Glu Val Thr Tyr Ile His
    50                  55                  60

Asn Leu Asp Gly Tyr Thr His Pro Glu Lys Val Leu Lys Pro His Ile
65                  70                  75                  80

Ile Asn Leu Leu Val Asp Ser Ile Lys Ile
                85                  90
```

<210> SEQ ID NO 109
<211> LENGTH: 86
<212> TYPE: PRT
<213> ORGANISM: Artificial Sequence
<220> FEATURE:
<223> OTHER INFORMATION: Synthetic Construct

<400> SEQUENCE: 109

```
Thr Asn Ser Ile Arg Cys Phe Met Glu Lys Gly Ile Ser Glu Leu Glu
 1               5                  10                  15

Ala Arg Glu Cys Val Lys Glu Glu Ile Asp Thr Ala Trp Lys Lys Met
            20                  25                  30

Asn Lys Tyr Met Val Asp Arg Ser Thr Phe Asn Ser Phe Val Arg Met
        35                  40                  45

Thr Tyr Asn Leu Ala Arg Met Ala His Cys Val Tyr Asp Gly Asp Ala
    50                  55                  60

Ile Gly Ser Pro Asp Asp Leu Ser Trp Asn Arg Val His Ser Leu Ile
65                  70                  75                  80

Ile Lys Pro Ile Ser Pro
                85
```

<210> SEQ ID NO 110
<211> LENGTH: 89
<212> TYPE: PRT
<213> ORGANISM: Artificial Sequence
<220> FEATURE:
<223> OTHER INFORMATION: Synthetic Construct

<400> SEQUENCE: 110

```
Thr Asn Ser Ile Leu Cys Tyr Met Arg Glu Lys Gly Phe Ser Glu Ser
 1               5                  10                  15

Glu Ala Arg Lys Gln Val Ile Glu Gln Ile Asp Thr Ala Trp Arg Gln
            20                  25                  30
```

-continued

```
Met Asn Lys Tyr Met Val Asp His Ser Thr Phe Asn Arg Ser Phe Met
        35                  40                  45

Gln Met Thr Tyr Asn Leu Ala Arg Met Ala His Cys Val Tyr Gln Asp
    50                  55                  60

Gly Asp Ala Ile Gly Ala Pro Asp Asp Gln Ser Trp Asn Arg Val His
65                  70                  75                  80

Ser Leu Ile Ile Lys Pro Val Ser Leu
                85
```

<210> SEQ ID NO 111
<211> LENGTH: 91
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 91
<223> OTHER INFORMATION: x=unknown

<400> SEQUENCE: 111

```
Ala Asn Ser Ile Ser Cys Tyr Met Gly Gln Thr Gly Val Ser Glu Glu
 1               5                  10                  15

Asp Ala Arg Glu His Met Lys Ile Leu Ile Asp Glu Ser Trp Lys Lys
            20                  25                  30

Met Asn Lys Val Arg Glu Met Asp Ser Asp Ser Pro Phe Ala Lys Pro
        35                  40                  45

Phe Val Glu Thr Ala Ile Asn Leu Ala Arg Ile Ala Gln Cys Thr Tyr
    50                  55                  60

Gln Thr Gly Asp Ser His Gly Ala Pro Asp Ala Arg Ser Lys Lys Arg
65                  70                  75                  80

Val Leu Ser Leu Ile Val Glu Pro Ile Pro Xaa
                85                  90
```

<210> SEQ ID NO 112
<211> LENGTH: 88
<212> TYPE: PRT
<213> ORGANISM: Artificial Sequence
<220> FEATURE:
<223> OTHER INFORMATION: Synthetic Construct

<400> SEQUENCE: 112

```
Ala Asn Ser Ile Ile Cys Tyr Met Asn Glu Asn Gly Val Ser Glu Glu
 1               5                  10                  15

Val Ala Tyr Lys His Ile Gln Asn Leu Leu Asp Gln Thr Trp Lys Lys
            20                  25                  30

Met Asn Lys Asp Arg Val Ile Asn Ser Pro Ser Ser Lys Tyr Phe Ser
        35                  40                  45

Glu Thr Ile Ile Asn Leu Ala Arg Ile Ser His Cys Thr Tyr Gln Tyr
    50                  55                  60

Gly Asp Gly His Gly Ala Pro Asp Thr Leu Ala Lys Asn Arg Ile Lys
65                  70                  75                  80

Ala Leu Ile Leu Glu Pro Ile Asn
                85
```